US008410248B2

(12) United States Patent
Rosen et al.

(10) Patent No.: US 8,410,248 B2

(45) Date of Patent: Apr. 2, 2013

(54) HWBAO62 POLYPEPTIDES

(75) Inventors: Craig A. Rosen, Pasadena, MD (US); Steven M. Ruben, Brookeville, MD (US)

(73) Assignee: Human Genome Sciences Inc., Rockville, MD (US)

( * ) Notice: Subject to any disclaimer, the term of this patent is extended or adjusted under 35 U.S.C. 154(b) by 0 days.

(21) Appl. No.: 12/753,401

(22) Filed: Apr. 2, 2010

(65) Prior Publication Data

US 2010/0255574 A1 Oct. 7, 2010

Related U.S. Application Data

(60) Continuation-in-part of application No. 12/136,548, filed on Jun. 10, 2008, now abandoned, which is a division of application No. 11/781,665, filed on Jul. 23, 2007, now abandoned, which is a continuation of application No. 10/994,608, filed on Nov. 23, 2004, (Continued)

(51) Int. Cl.
*C07K 14/435* (2006.01)
*C07K 14/00* (2006.01)

(52) U.S. Cl. ......................... 530/350; 530/300; 435/325

(58) Field of Classification Search ........................ None
See application file for complete search history.

(56) References Cited

U.S. PATENT DOCUMENTS

| | | | |
|---|---|---|---|
| 4,923,813 | A | 5/1990 | Hecht et al. |
| 5,001,225 | A | 3/1991 | Taylor |
| 5,011,912 | A | 4/1991 | Hopp et al. |
| 5,118,617 | A | 6/1992 | Ortega et al. |
| 5,194,596 | A | 3/1993 | Tischer et al. |
| 5,350,836 | A | 9/1994 | Kopchick et al. |
| 5,536,637 | A | 7/1996 | Jacobs |
| 5,744,355 | A | 4/1998 | Weinshilboum et al. |
| 6,569,992 | B1 | 5/2003 | LaFleur et al. |
| 6,812,339 | B1 | 11/2004 | Venter et al. |
| 6,924,356 | B2 | 8/2005 | Ruben et al. |
| 7,368,531 | B2 | 5/2008 | Rosen et al. |
| 7,411,051 | B2 | 8/2008 | Rosen et al. |
| 2002/0173635 | A1 | 11/2002 | Jacobs et al. |
| 2003/0073129 | A1 | 4/2003 | Baker et al. |
| 2005/0009085 | A1 | 1/2005 | LaFleur et al. |
| 2005/0079537 | A1 | 4/2005 | LaFleur |
| 2005/0153335 | A1 | 7/2005 | LaFleur |
| 2006/0223088 | A1 | 10/2006 | Rosen et al. |
| 2006/0281095 | A1 | 12/2006 | LaFleur |
| 2007/0154918 | A1 | 7/2007 | LaFleur et al. |
| 2007/0202496 | A1 | 8/2007 | Beretta |
| 2007/0224663 | A1 | 9/2007 | Rosen et al. |
| 2009/0088555 | A1 | 4/2009 | LaFleur et al. |

FOREIGN PATENT DOCUMENTS

| | | | |
|---|---|---|---|
| EP | 0 607 054 | | 7/1994 |
| EP | 1 130 094 | A2 | 9/2001 |
| WO | WO-91/04328 | | 4/1991 |
| WO | WO-97/07198 | | 2/1997 |
| WO | WO-97/39122 | | 10/1997 |
| WO | WO-97/40069 | | 10/1997 |
| WO | WO-98/45437 | A2 | 10/1998 |
| WO | WO-99/40100 | | 8/1999 |
| WO | WO-00/00610 | A2 | 1/2000 |
| WO | WO-00/12708 | A2 | 3/2000 |
| WO | WO-01/53312 | A1 | 7/2001 |
| WO | WO-01/53486 | A1 | 7/2001 |
| WO | WO-01/77290 | | 10/2001 |

OTHER PUBLICATIONS

GenBank Accession No. AI761909, NCI-CGAP www.ncbi.nlm.nih.gov/ncicgap (Jun. 24, 1999).
GenBank Accession No. AI283077, NCI-CGAP www.ncbi.nlm.nih.gov/ncicgap (Jan. 29, 1999).
GenBank Accession No. AA910871, NCI-CGAP www.ncbi.nlm.nih.gov/ncicgap (Apr. 13, 1998).
GenBank Accession No. AA179892, Hillier et al. (Dec. 31, 1996).
GenBank Accession No. AI751270, Jia et al. (Jun. 22, 1999).
GenBank Accession No. AA180424, Hillier et al. (Dec. 31, 1996).
GenBank Accession No. AA169699, Hillier et al. (Dec. 20, 1996).
GenBank Accession No. AA282527, NCI-CGAP www.ncbi.nlm.nih.gov/ncicgap (Aug. 13, 1997).
GenBank Accession No. AA169226, Hillier et al. (Dec. 20, 1996).
GenBank Accession No. AA744012, NCI-CGAP www.ncbi.nlm.nih.gov/ncicgap (Jan. 23, 1998).
GenBank Accession No. AA630387, Hillier et al. (Mar. 6, 1998).
GenBank Accession No. AA806038, NCI-CGAP www.ncbi.nlm.nih.gov/ncicgap (Feb. 19, 1998).
GenBank Accession No. AI185702, NCI-CGAP www.ncbi.nlm.nih.gov/ncicgap (Oct. 29, 1998).
GenBank Accession No. R69144, Hillier et al. (Jun. 1, 1995).
GenBank Accession No. R69260, Hillier et al. (Aug. 4, 1997).
GenBank Accession No. AA332623, Adams et al. (Apr. 21, 1997).
GenBank Accession No. AA744320, NCI-CGAP www.ncbi.nlm.nih.gov/ncicgap (Jan. 23, 1998).

(Continued)

*Primary Examiner* — Christine J Saoud
*Assistant Examiner* — Jon M Lockard
(74) *Attorney, Agent, or Firm* — Joseph Schuller; William T. Han

(57) ABSTRACT

The present invention relates to human secreted polypeptides, and isolated nucleic acid molecules encoding said polypeptides, useful for diagnosing and treating diseases, disorders, and/or conditions (such as immune, cardiovascular, cancer, and other proliferative diseases, disorders, and/or conditions) related to said human secreted proteins. Antibodies that bind these polypeptides are also encompassed by the present invention. Also encompassed by the invention are vectors, host cells, and recombinant and synthetic methods for producing said polynucleotides, polypeptides, and/or antibodies. The invention further encompasses screening methods for identifying agonists and antagonists of polynucleotides and polypeptides of the invention. The present invention further encompasses methods and compositions for inhibiting or enhancing the production and function of the polypeptides of the present invention. The invention further relates to diagnostic and therapeutic methods useful for diagnosing and treating diseases, disorders, and/or conditions related to these novel human secreted proteins.

10 Claims, 26 Drawing Sheets

Related U.S. Application Data

(60) now abandoned, which is a division of application No. 10/105,299, filed on Mar. 26, 2002, now Pat. No. 7,368,527, which is a continuation-in-part of application No. 09/950,082, filed on Sep. 12, 2001, now abandoned, and a continuation-in-part of application No. PCT/US00/06043, filed on Mar. 9, 2000, and a continuation-in-part of application No. PCT/US00/06012, filed on Mar. 9, 2000, and a continuation-in-part of application No. PCT/US00/06058, filed on Mar. 9, 2000, and a continuation-in-part of application No. PCT/US00/06044, filed on Mar. 9, 2000, and a continuation-in-part of application No. PCT/US00/06059, filed on Mar. 9, 2000, and a continuation-in-part of application No. PCT/US00/06042, filed on Mar. 9, 2000, and a continuation-in-part of application No. PCT/US00/06014, filed on Mar. 9, 2000, and a continuation-in-part of application No. PCT/US00/06013, filed on Mar. 9, 2000, and a continuation-in-part of application No. PCT/US00/06049, filed on Mar. 9, 2000, and a continuation-in-part of application No. PCT/US00/06057, filed on Mar. 9, 2000, and a continuation-in-part of application No. PCT/US00/06824, filed on Mar. 16, 2000, and a continuation-in-part of application No. PCT/US00/06765, filed on Mar. 16, 2000, and a continuation-in-part of application No. PCT/US00/06792, filed on Mar. 16, 2000, and a continuation-in-part of application No. PCT/US00/06830, filed on Mar. 16, 2000, and a continuation-in-part of application No. PCT/US00/06782, filed on Mar. 16, 2000, and a continuation-in-part of application No. PCT/US00/06822, filed on Mar. 16, 2000, and a continuation-in-part of application No. PCT/US00/06791, filed on Mar. 16, 2000, and a continuation-in-part of application No. PCT/US00/06828, filed on Mar. 16, 2000, and a continuation-in-part of application No. PCT/US00/06823, filed on Jun. 16, 2000, and a continuation-in-part of application No. PCT/US00/06781, filed on Mar. 16, 2000, and a continuation-in-part of application No. PCT/US00/07505, filed on Mar. 22, 2000, and a continuation-in-part of application No. PCT/US00/07440, filed on Mar. 22, 2000, and a continuation-in-part of application No. PCT/US00/07506, filed on Mar. 22, 2000, and a continuation-in-part of application No. PCT/US00/07507, filed on Mar. 22, 2000, and a continuation-in-part of application No. PCT/US00/07535, filed on Mar. 22, 2000, and a continuation-in-part of application No. PCT/US00/07525, filed on Mar. 22, 2000, and a continuation-in-part of application No. PCT/US00/07534, filed on Mar. 22, 2000, and a continuation-in-part of application No. PCT/US00/07483, filed on Mar. 22, 2000, and a continuation-in-part of application No. PCT/US00/07526, filed on Mar. 22, 2000, and a continuation-in-part of application No. PCT/US00/07527, filed on Mar. 22, 2000, and a continuation-in-part of application No. PCT/US00/07661, filed on Mar. 23, 2000, and a continuation-in-part of application No. PCT/US00/07579, filed on Mar. 23, 2000, and a continuation-in-part of application No. PCT/US00/07723, filed on Mar. 23, 2000, and a continuation-in-part of application No. PCT/US00/07724, filed on Mar. 23, 2000, and a continuation-in-part of application No. PCT/US00/14929, filed on Jun. 1, 2000, and a continuation-in-part of application No. PCT/US00/07722, filed on Mar. 23, 2000, and a continuation-in-part of application No. PCT/US00/07578, filed on Mar. 23, 2000, and a continuation-in-part of application No. PCT/US00/07726, filed on Mar. 23, 2000, and a continuation-in-part of application No. PCT/US00/07677, filed on Mar. 23, 2000, and a continuation-in-part of application No. PCT/US00/07725, filed on Mar. 23, 2000, and a continuation-in-part of application No. PCT/US00/09070, filed on Apr. 6, 2000, and a continuation-in-part of application No. PCT/US00/08982, filed on Apr. 6, 2000, and a continuation-in-part of application No. PCT/US00/08983, filed on Apr. 6, 2000, and a continuation-in-part of application No. PCT/US00/09067, filed on Apr. 6, 2000, and a continuation-in-part of application No. PCT/US00/09066, filed on Apr. 6, 2000, and a continuation-in-part of application No. PCT/US00/09068, filed on Apr. 6, 2000, and a continuation-in-part of application No. PCT/US00/08981, filed on Apr. 6, 2000, and a continuation-in-part of application No. PCT/US00/08980, filed on Apr. 6, 2000, and a continuation-in-part of application No. PCT/US00/09071, filed on Apr. 6, 2000, and a continuation-in-part of application No. PCT/US00/09069, filed on Apr. 6, 2000, and a continuation-in-part of application No. PCT/US00/15136, filed on Jun. 1, 2000, and a continuation-in-part of application No. PCT/US00/14926, filed on Jun. 1, 2000, and a continuation-in-part of application No. PCT/US00/14963, filed on Jun. 1, 2000, and a continuation-in-part of application No. PCT/US00/15135, filed on Jun. 1, 2000, and a continuation-in-part of application No. PCT/US00/14934, filed on Jun. 1, 2000, and a continuation-in-part of application No. PCT/US00/14933, filed on Jun. 1, 2000, and a continuation-in-part of application No. PCT/US00/15137, filed on Jun. 1, 2000, and a continuation-in-part of application No. PCT/US00/14928, filed on Jun. 1, 2000, and a continuation-in-part of application No. PCT/US00/14973, filed on Jun. 1, 2000, and a continuation-in-part of application No. PCT/US00/14964, filed on Jun. 1, 2000, and a continuation-in-part of application No. PCT/US00/26376, filed on Sep. 26, 2000, and a continuation-in-part of application No. PCT/US00/26371, filed on Sep. 26, 2000, and a continuation-in-part of application No.

PCT/US00/26324, filed on Sep. 26, 2000, and a continuation-in-part of application No. PCT/US00/26323, filed on Sep. 26, 2000, and a continuation-in-part of application No. PCT/US00/26337, filed on Sep. 26, 2000, and a continuation-in-part of application No. PCT/US01/13318, filed on Apr. 26, 2001, said application No. 10/105,299 is a continuation-in-part of application No. 09/950,083, filed on Sep. 12, 2001, now abandoned, and a continuation-in-part of application No. PCT/US00/06043, and a continuation-in-part of application No. PCT/US00/06012, and a continuation-in-part of application No. PCT/US00/06058, and a continuation-in-part of application No. PCT/US00/06044, and a continuation-in-part of application No. PCT/US00/06059, and a continuation-in-part of application No. PCT/US00/06042, and a continuation-in-part of application No. PCT/US00/06014, and a continuation-in-part of application No. PCT/US00/06013, and a continuation-in-part of application No. PCT/US00/06049, and a continuation-in-part of application No. PCT/US00/06057, and a continuation-in-part of application No. PCT/US00/06824, and a continuation-in-part of application No. PCT/US00/06765, and a continuation-in-part of application No. PCT/US00/06792, and a continuation-in-part of application No. PCT/US00/06830, and a continuation-in-part of application No. PCT/US00/06782, and a continuation-in-part of application No. PCT/US00/06822, and a continuation-in-part of application No. PCT/US00/06791, and a continuation-in-part of application No. PCT/US00/06828, and a continuation-in-part of application No. PCT/US00/06823, and a continuation-in-part of application No. PCT/US00/06781, and a continuation-in-part of application No. PCT/US00/07505, and a continuation-in-part of application No. PCT/US00/07440, and a continuation-in-part of application No. PCT/US00/07506, and a continuation-in-part of application No. PCT/US00/07507, and a continuation-in-part of application No. PCT/US00/07535, and a continuation-in-part of application No. PCT/US00/07525, and a continuation-in-part of application No. PCT/US00/07534, and a continuation-in-part of application No. PCT/US00/07483, and a continuation-in-part of application No. PCT/US00/07526, and a continuation-in-part of application No. PCT/US00/07527, and a continuation-in-part of application No. PCT/US00/07661, and a continuation-in-part of application No. PCT/US00/07579, and a continuation-in-part of application No. PCT/US00/07723, and a continuation-in-part of application No. PCT/US00/07724, and a continuation-in-part of application No. PCT/US00/14929, and a continuation-in-part of application No. PCT/US00/07722, and a continuation-in-part of application No. PCT/US00/07578, and a continuation-in-part of application No. PCT/US00/07726, and a continuation-in-part of application No. PCT/US00/07677, and a continuation-in-part of application No. PCT/US00/07725, and a continuation-in-part of application No. PCT/US00/09070, and a continuation-in-part of application No. PCT/US00/08982, and a continuation-in-part of application No. PCT/US00/08983, and a continuation-in-part of application No. PCT/US00/09067, and a continuation-in-part of application No. PCT/US00/09066, and a continuation-in-part of application No. PCT/US00/09068, and a continuation-in-part of application No. PCT/US00/08981, and a continuation-in-part of application No. PCT/US00/08980, and a continuation-in-part of application No. PCT/US00/09071, and a continuation-in-part of application No. PCT/US00/09069, and a continuation-in-part of application No. PCT/US00/15136, and a continuation-in-part of application No. PCT/US00/14926, and a continuation-in-part of application No. PCT/US00/14963, and a continuation-in-part of application No. PCT/US00/15135, and a continuation-in-part of application No. PCT/US00/14934, and a continuation-in-part of application No. PCT/US00/14933, and a continuation-in-part of application No. PCT/US00/15137, and a continuation-in-part of application No. PCT/US00/14928, and a continuation-in-part of application No. PCT/US00/14973, and a continuation-in-part of application No. PCT/US00/14964, and a continuation-in-part of application No. PCT/US00/26376, and a continuation-in-part of application No. PCT/US00/26371, and a continuation-in-part of application No. PCT/US00/26324, and a continuation-in-part of application No. PCT/US00/26323, and a continuation-in-part of application No. PCT/US00/26337, and a continuation-in-part of application No. PCT/US01/13318, application No. 12/753,401, which is a continuation-in-part of application No. 11/366,486, filed on Mar. 3, 2006, which is a continuation-in-part of application No. 10/664,358, filed on Sep. 20, 2003, which is a continuation-in-part of application No. PCT/US02/09785, filed on Mar. 19, 2002, which is a continuation-in-part of application No. 10/100,683, filed on Mar. 19, 2002, which is a continuation-in-part of application No. 09/981,876, filed on Oct. 19, 2001, which is a division of application No. 09/621,011, filed on Jul. 20, 2000, which is a continuation of application No. 09/148,545, filed on Sep. 4, 1998, said application No. 10/100,683 is a continuation-in-part of application No. PCT/US98/04482, filed on Mar. 6, 1998, which is a continuation-in-part of application No. 09/621,011, which is a continuation of application No. 09/148,545, which is a continuation-in-part of application No. PCT/US98/04482, said application No. 10/100,683 is a continuation-in-part of application No. 09/148,545, said application No. 10/100,683 is a continuation-in-part of application No.

PCT/US98/04482, which is a continuation-in-part of application No. 09/882,171, filed on Jun. 18, 2001, which is a continuation of application No. 09/809,391, filed on Mar. 16, 2001, which is a continuation-in-part of application No. 09/149,476, filed on Sep. 8, 1998, which is a continuation-in-part of application No. PCT/US98/04493, filed on Mar. 6, 1998, said application No. 10/100,683 is a continuation-in-part of application No. 09/809,391, which is a continuation-in-part of application No. 09/149,476, filed on Sep. 8, 1998, which is a continuation-in-part of application No. PCT/US98/04493, said application No. 10/100,683 is a continuation-in-part of application No. 09/149,476, which is a continuation-in-part of application No. PCT/US98/04493, said application No. 10/100,683 is a continuation-in-part of application No. PCT/US98/04493, said application No. 10/100,683 is a continuation-in-part of application No. 09/852,659, filed on May 11, 2001, which is a continuation-in-part of application No. 09/152,060, filed on Sep. 11, 1998, which is a continuation-in-part of application No. PCT/US98/04858, filed on Mar. 12, 1998, said application No. 10/058,993 is a continuation-in-part of application No. 09/853,161, filed on May 11, 2001, which is a continuation of application No. 09/152,060, filed on Sep. 11, 1998, which is a continuation-in-part of application No. PCT/US98/04858, said application No. 10/058,993 is a continuation-in-part of application No. 09/852,797, filed on May 11, 2001, which is a continuation-in-part of application No. 09/152,060, which is a continuation-in-part of application No. PCT/US98/04858, which is a continuation-in-part of application No. 09/852,659, which is a continuation-in-part of application No. 09/152,060, which is a continuation-in-part of application No. PCT/US98/04858, said application No. 10/100,683 is a continuation-in-part of application No. 09/853,161, which is a continuation-in-part of application No. 09/152,060, which is a continuation-in-part of application No. PCT/US98/04858, said application No. 10/100,683 is a continuation-in-part of application No. 09/852,797, which is a continuation-in-part of application No. 09/152,060, which is a continuation-in-part of application No. PCT/US98/04858, said application No. 10/100,683 is a continuation-in-part of application No. 09/152,060, and a continuation-in-part of application No. PCT/US98/04858, said application No. 10/100,683 is a continuation-in-part of application No. PCT/US98/04858, and a continuation-in-part of application No. 10/059,395, filed on Jan. 31, 2002, which is a division of application No. 09/966,262, filed on Oct. 1, 2001, which is a continuation of application No. 09/154,707, filed on Sep. 17, 1998, which is a continuation-in-part of application No. PCT/US98/05311, filed on Mar. 19, 1998, said application No. 10/100,683 is a continuation-in-part of application No. 09/984,245, filed on Oct. 29, 2001, which is a division of application No. 09/154,707, which is a continuation-in-part of application No. PCT/US98/05311, said application No. 10/100,683 is a continuation of application No. 09/983,966, which is a division of application No. 09/154,707, which is a continuation-in-part of application No. PCT/US98/05311, said application No. 10/100,683 is a continuation-in-part of application No. 09/966,262, which is a continuation of application No. 09/154,707, which is a continuation-in-part of application No. PCT/US98/05311, said application No. 10/100,683 is a continuation-in-part of application No. 09/154,707, which is a continuation-in-part of application No. PCT/US98/05311, said application No. 10/100,683 is a continuation-in-part of application No. PCT/US98/05311, and a continuation-in-part of application No. 09/814,122, filed on Mar. 22, 2001, which is a continuation of application No. 09/577,145, filed on May 24, 2000, which is a continuation of application No. 09/166,780, filed on Oct. 6, 1998, which is a continuation-in-part of application No. PCT/US98/06801, filed on Apr. 7, 1998, said application No. 10/100,683 is a continuation-in-part of application No. PCT/US98/06801, and a continuation-in-part of application No. PCT/US98/10868, filed on May 28, 1998, and a continuation-in-part of application No. PCT/US98/11422, filed on Jun. 4, 1998, and a continuation-in-part of application No. PCT/US01/05614, filed on Feb. 21, 2001, and a continuation-in-part of application No. PCT/US98/12125, filed on Jun. 11, 1998, and a continuation-in-part of application No. 09/627,081, filed on Jul. 27, 2000, which is a continuation of application No. 09/213,365, filed on Dec. 17, 1998, which is a continuation-in-part of application No. PCT/US98/13608, filed on Jun. 30, 1998, said application No. 10/100,683 is a continuation-in-part of application No. PCT/US98/13608, and a continuation-in-part of application No. 09/984,490, filed on Oct. 30, 2001, which is a continuation-in-part of application No. 09/227,357, filed on Jan. 8, 1999, which is a continuation-in-part of application No. PCT/US98/13684, filed on Jul. 7, 1998, said application No. 10/100,683 is a continuation-in-part of application No. 09/983,802, filed on Oct. 25, 2001, which is a continuation of application No. 09/227,357, which is a continuation-in-part of application No. PCT/US98/13684, said application No. 10/100,683 is a continuation-in-part of application No. 09/973,278, filed on Oct. 10, 2001, which is a continuation-in-part of application No. 09/227,357, which is a continuation-in-part of application No. PCT/US98/13684, said application No. 10/100,683 is a continuation-in-part of application No. PCT/US98/13684, said application No. 10/100,683 is a continuation-in-part of application No. 09/776,724, filed on Feb. 6, 2001, which is a continuation-in-part of application No. 09/669,688, filed on Sep. 26, 2000, which is a continuation-in-part of application No. PCT/CT98/14613, filed on Jul. 15, 1998, said application No. 10/100,683 is a continuation-in-part of application No. 09/669,688, which is a continuation of application No. 09/229,982, which is a continuation-in-part of application No. PCT/US98/14613, said application No. 10/100,683 is a continuation-in-part of application No. 09/229,982, which is a continuation-in-part of application No. PCT/US98/14613, filed on Jul. 15, 1998, which is a continuation-in-part of application No. 09/820,649, filed on Mar. 30, 2001, which is a continuation of application No. 09/666,984, filed on Sep. 21, 2000, which is a continuation of application No. 09/236,557, filed on Jan. 26, 1999, which is a continuation-in-part of application No. PCT/US98/15949, filed on Jul. 29, 1998, said application No. 10/100,683 is a continuation-in-part of application No. PCT/US98/15949, and a continuation-in-part of application No. 09/969,730, filed on Oct. 4, 2001, which is a continuation-in-part of application No. 09/774,639, filed on Feb. 1, 2001, which is a continuation of application No. 09/244,112, filed on Feb. 4, 1999, which is a continuation-in-part of application No. PCT/US98/16235, filed on Aug. 4, 1998, said application No. 10/100,683 is a continuation-in-part of application No. 09/774,639, which is a continuation of application No. 09/244,112, which is a continuation-in-part of application No. PCT/US98/16235, said application No. 10/100,683 is a continuation-in-part of application No. 09/969,730, and a continuation-in-part of application No. PCT/US98/16235, and a continuation-in-part of application No. 09/716,128, filed on Nov. 17, 2000, which is a continuation of application No. 09/251,329, filed on Feb. 17, 1999, which is a continuation-in-part of application No. PCT/US98/17044, filed on Aug. 18, 1998, said application No. 10/100,683 is a continuation-in-part of application No. PCT/US98/17044, and a continuation-in-part of application No. 09/729,835, filed on Dec. 6, 2000, which is a division of application No. 09/257,197, filed on Feb. 25, 1999, which is a continuation-in-part of application No. PCT/US98/17709, filed on Aug. 27, 1998, said application No. 10/100,683 is a continuation-in-part of application No. 09/257,179, which is a continuation-in-part of application No. PCT/US98/17709, said application No. 10/100,683 is a continuation-in-part of application No. PCT/US98/17709, and a continuation-in-part of application No. 10/047,021, filed on Jan. 17, 2002, which is a continuation-in-part of application No. 09/722,329, filed on Nov. 28, 2000, which is a continuation of application No. 09/262,109, filed on Mar. 4, 1999, which is a continuation-in-part of application No. PCT/US98/18360, filed on Sep. 3, 1998, said application No. 10/100,683 is a continuation-in-part of application No. 09/722,329, which is a continuation of application No. 09/262,109, which is a continuation-in-part of application No. PCT/US98/18360, said application No. 10/100,683 is a continuation-in-part of application No. PCT/US02/01109, filed on Jan. 17, 2002, and a continuation-in-part of application No. PCT/US98/18360, and a continuation-in-part of application No. 09/281,976, filed on Mar. 31, 1999, which is a continuation-in-part of application No. PCT/US98/20775, filed on Oct. 1, 1998, said application No. 10/100,683 is a continuation-in-part of application No. PCT/US98/20775, and a continuation-in-part of application No. 09/984,429, filed on Oct. 30, 2001, which is a continuation-in-part of application No. 09/288,143, filed on Apr. 8, 1999, which is a continuation-in-part of application No. PCT/US98/21142, filed on Oct. 8, 1998, said application No. 10/100,683 is a continuation-in-part of application No. 09/288,143, which is a continuation-in-part of application No. PCT/US98/21142, said application No. 10/100,683 is a continuation-in-part of application No. PCT/US98/21142, and a continuation-in-part of application No. 09/296,622, filed on Apr. 23, 1999, which is a continuation-in-part of application No. PCT/US98/22376, filed on Oct. 23, 1998, said application No. 10/100,683 is a continuation-in-part of application No. PCT/US98/22376, and a continuation-in-part of application No. 09/974,879, filed on Oct. 12, 2001, which is a continuation-in-part of application No. 09/818,683, which is a continuation of application No. 09/305,736, filed on May 5, 1999, which is a continuation-in-part of application No. PCT/US98/23435, filed on Nov. 4, 1998, said application No. 10/100,683 is a continuation-in-part of application No. 09/818,683, which is a continuation of application No. 09/305,736, which is a continuation-in-part of application No. PCT/US98/23435, said application No. 10/100,683 is a continuation-in-part of application No. 09/305,736, which is a continuation-in-part of application No. PCT/US98/23435, said application No. 10/100,683 is a continuation-in-part of application No. PCT/US98/23435, which is a continuation-in-part of application No. 09/334,595, filed on Jun. 17, 1999, which is a continuation-in-part of application No. PCT/US98/27059, filed on Dec. 17, 1998, said application No. 10/100,683 is a continuation-in-part of application No. PCT/US98/27059, and a continuation-in-part of application No. 09/938,671, filed on Aug. 27, 2001, which is a continuation of application No. 09/739,907, filed on Dec. 20, 2000, which is a continuation of application No. 09/348,457, filed on Jul. 7, 1999, which is a continuation-in-part of application No. PCT/US99/00108, filed on Jan. 6, 1999, said application No. 10/100,683 is a continuation-in-part of application No. 09/739,907, which is a continuation of application No. 09/348,457, which is a continuation-in-part of application No. PCT/US99/00108, said application No. 10/100,683 is a continuation-in-part of application No. 09/348,457, which is a continuation-in-part of application No. PCT/US99/00108, said application No. 10/100,683 is a continuation-in-part of application No. PCT/US99/00108, and a continuation-in-part of application No. 09/949,925, filed on Sep. 12, 2001, which is a continuation-in-part of application No. PCT/US99/01621, filed on Jan. 27, 1999, and a continuation-in-part of application No. 09/363,044, filed on Jul. 29, 1999, which is a continuation-in-part of application No. PCT/US99/01621, said application No. 10/100,683 is a continuation-in-part of application No. 09/912,153, filed on Mar. 21, 2001, which is a continuation of application No. 09/363,044, which is a continuation-in-part of application No. PCT/US99/01621, which is a continuation-in-part of application No. 09/363,044, which is a continuation-in-part of application No. PCT/US99/01621, said application No. 10/100,683 is a continuation-in-part of application No. PCT/US99/01621, and a continuation-in-part of application No. 10/062,548, filed on Feb. 5, 2002, which is a continuation of application No. 09/369,247, filed on Aug. 5, 1999, which is a continuation-in-part of application No. PCT/US99/02293, filed on Feb. 4, 1999, said application No. 10/100,683 is a continuation-in-part of application No. 09/369,247, which is a continuation-in-part of application No. PCT/US99/02293, said application No. 10/100,683 is a continuation-in-part of application No. PCT/US99/02293, said application No. 10/100,683 is a continuation-in-part of application No. 09/716,129, filed on Nov. 17, 2000, which is a continuation-in-part of application No. PCT/US99/03939, filed on Feb. 24, 1999, which is a continuation-in-part of application No. 09/382,572, filed on Aug. 25, 1999, which is a continuation-in-part of application No. PCT/US99/03939, filed on Feb. 24, 1999, said application No. 10/100,683 is a continuation-in-part of application No. PCT/US99/03939, and a continuation-in-part of application No. 09/798,889, filed on Mar. 6, 2001, which is a continuation of application No. 09/393,022, filed on Sep. 9, 1999, which is a continuation-in-part of application No. PCT/US99/05721, filed on Mar. 11, 1999, said application No. 10/100,683 is a continuation-in-part of application No. PCT/US99/05721, and a continuation-in-part of application No. 09/397,945, filed on Sep. 17, 1999, which is a continuation-in-part of application No. PCT/US99/05804, filed on Mar. 18, 1999, said application No. 10/100,683 is a continuation-in-part of application No. PCT/US99/05804, and a continuation-in-part of application No. 09/948,783, filed on Sep. 10, 2001, which is a continuation-in-part of application No. 09/892,877, filed on Jun. 28, 2001, which is a continuation of application No. 09/437,658, filed on Nov. 10, 1999, which is a continuation-in-part of application No. PCT/US99/09847, filed on May 6, 1999, said application No. 10/100,683 is a continuation-in-part of application No. 09/982,877, which is a continuation of application No. 09/437,658, which is a continuation-in-part of application No. PCT/US99/09847, said application No. 10/100,683 is a continuation-in-part of application No. PCT/US99/09847, and a continuation-in-part of application No. 10/050,873, filed on Jan. 18, 2002, which is a continuation-in-part of application No. 09/461,325, filed on Dec. 14, 1999, which is a continuation-in-part of application No. PCT/US99/13418, filed on Jun. 15, 1999, said application No. 10/100,683 is a continuation-in-part of application No. 10/012,542, filed on Dec. 12, 2001, which is a division of application No. 09/461,325, filed on Dec. 14, 1999, which is a continuation-in-part of application No. PCT/US99/13418, said application No. 10/100,683 is a continuation-in-part of application No. 09/461,325, which is a continuation-in-part of application No. PCT/US99/13418, said application No. 10/100,683 is a continuation-in-part of application No. PCT/US99/13418, and a continuation-in-part of application No. 09/984,271, filed on Oct. 29, 2001, which is a division of application No. 09/482,273, filed on Jan. 13, 2000, which is a continuation-in-part of application No. PCT/US99/15849, filed on Jul. 14, 1999, said application No. 10/100,683 is a continuation-in-part of application No. 09/984,276, filed on Oct. 29, 2001, which is a division of application No. 09/482,273, which is a continuation-in-part of application No. PCT/US99/15849, said application No. 10/100,683 is a continuation-in-part of application No. 09/482,273, which is a continuation-in-part of application No. PCT/US99/15849, said application No. 10/100,683 is a continuation-in-part of application No. PCT/US99/15849, and a continuation-in-part of application No. PCT/US01/29871, filed on Sep. 24, 2001, which is a continuation-in-part of application No. PCT/US01/00911, filed on Jan. 12, 2001, said application No. 10/100,683 is a continuation-in-part of application No. PCT/US01/00911, which is a continuation-in-part of application No. 09/482,273, said application No. 10/100,683 is a continuation-in-part of application No. 09/489,847, filed on Jan. 24, 2000, which is a continuation-in-part of application No. PCT/US99/17130, filed on Jul. 29, 1999, said application No. 10/100,683 is a continuation-in-part of application No. PCT/US99/17130, and a continuation-in-part of application No. 10/054,988, filed on Jan. 25, 2002, which is a continuation of application No. 09/904,615, filed on Jul. 16, 2001, which is a continuation of application No. 09/739,254, filed on Dec. 19, 2000, which is a continuation of application No. 09/511,554, filed on Feb. 23, 2000, which is a continuation-in-part of application No. PCT/US99/19330, filed on Aug. 24, 1999, said application No. 10/100,683 is a continuation-in-part of application No. 09/904,615, which is a continuation of application No. 09/739,254, which is a continuation of application No. 09/511,554, which is a continuation-in-part of application No. PCT/US99/19330, said application No. 10/100,683 is a continuation-in-part of application No. PCT/US99/19330, and a continuation-in-part of application No. 09/820,893, filed on Mar. 30, 2001, which is a continuation of application No. 09/531,119, filed on Mar. 20, 2000, which is a continuation-in-part of application No. PCT/US99/22012, filed on Sep. 22, 1999, said application No. 10/100,683 is a continuation-in-part of application No. PCT/US99/22012, and a continuation-in-part of application No. 09/948,820, filed on Sep. 10, 2001, which is a continuation of application No. 09/545,391, filed on May 5, 2000, which is a continuation-in-part of application No. PCT/US99/26409, filed on Nov. 9, 1999, said application No. 10/100,683 is a continuation-in-part of application No. 09/565,391, which is a continuation-in-part of application No. PCT/US99/26409, said application No. 10/100,683 is a continuation-in-part of application No. PCT/US99/26409, and a continuation-in-part of application No. 09/895,298, filed on Jul. 2, 2001, which is a continuation of application No. 09/591,316, filed on Jun. 9, 2000, which is a continuation-in-part of application No. PCT/US99/29950, filed on Dec. 16, 1999, said application No. 10/100,683 is a continuation-in-part of application No. PCT/US99/29950, and a continuation-in-part of application No. 09/985,153, filed on Nov. 1, 2001, which is a continuation of application No. 09/618,150, filed on Jul. 17, 2000, which is a continuation-in-part of application No. PCT/US00/00903, filed on Jan. 18, 2000, said application No. 10/100,683 is a continuation-in-part of application No.

PCT/US00/00903, and a continuation-in-part of application No. 09/997,131, filed on Nov. 30, 2001, which is a continuation of application No. 09/628,508, filed on Jul. 28, 2000, which is a continuation-in-part of application No. PCT/US00/03062, filed on Feb. 8, 2000, said application No. 10/100,683 is a continuation-in-part of application No. PCT/US00/03062, filed on Feb. 8, 2000, and a continuation-in-part of application No. 10/050,882, filed on Jan. 18, 2002, which is a continuation of application No. 09/661,453, filed on Sep. 13, 2000, which is a continuation-in-part of application No. PCT/US00/06783, filed on Mar. 16, 2000, which is a continuation of application No. 10/100,683, which is a continuation-in-part of application No. 09/661,453, filed on Sep. 13, 2000, which is a continuation-in-part of application No. PCT/US00/06783, said application No. 10/100,683 is a continuation-in-part of application No. PCT/US00/06783, and a continuation-in-part of application No. 10/050,704, filed on Jan. 18, 2002, which is a continuation of application No. 09/684,524, filed on Oct. 10, 2000, which is a continuation-in-part of application No. PCT/US00/08979, filed on Apr. 6, 2000, said application No. 10/100,683 is a continuation-in-part of application No. 09/684,524, which is a continuation-in-part of application No. PCT/US00/08979, said application No. 10/100,683 is a continuation-in-part of application No. PCT/US00/08979, and a continuation-in-part of application No. 10/042,141, filed on Jan. 11, 2002, which is a continuation of application No. 09/726,643, filed on Dec. 1, 2000, which is a continuation-in-part of application No. PCT/US00/15187, filed on Jun. 2, 2000, said application No. 10/100,683 is a continuation-in-part of application No. 09/726,643, which is a continuation-in-part of application No. PCT/US00/15187, said application No. 10/100,683 is a continuation-in-part of application No. PCT/US00/15187, and a continuation-in-part of application No. 09/756,168, filed on Jan. 9, 2001, which is a continuation-in-part of application No. PCT/US00/19735, filed on Jul. 23, 1999, said application No. 10/100,683 is a continuation-in-part of application No. PCT/US00/19735, and a continuation-in-part of application No. 10/060,255, filed on Feb. 1, 2002, which is a continuation of application No. 09/781,417, filed on Feb. 13, 2001, which is a continuation-in-part of application No. PCT/US00/22325, filed on Aug. 16, 2000, said application No. 10/100,683 is a continuation-in-part of application No. 09/781,417, which is a continuation-in-part of application No. PCT/US00/22325, said application No. 10/100,683 is a continuation-in-part of application No. PCT/US00/22325, and a continuation-in-part of application No. 09/789,561, filed on Feb. 22, 2001, which is a continuation-in-part of application No. PCT/US00/24008, filed on Aug. 31, 2000, said application No. 10/100,683 is a continuation-in-part of application No. PCT/US00/24008, and a continuation-in-part of application No. 09/800,729, filed on Mar. 8, 2001, which is a continuation-in-part of application No. PCT/US00/26013, filed on Sep. 22, 2000, said application No. 10/100,683 is a continuation-in-part of application No. PCT/US00/26013, and a continuation-in-part of application No. 09/832,129, filed on Apr. 11, 2001, which is a continuation-in-part of application No. PCT/US00/28664, filed on Oct. 17, 2000, said application No. 10/100,683 is a continuation-in-part of application No. PCT/US00/28664, and a continuation-in-part of application No. PCT/US00/29363, filed on Oct. 25, 2000, said application No. 10/100,683 is a continuation-in-part of application No. PCT/US00/29360, filed on Oct. 25, 2000, and a continuation-in-part of application No. PCT/US00/29362, filed on Oct. 25, 2000, and a continuation-in-part of application No. PCT/US00/29365, filed on Oct. 25, 2000, and a continuation-in-part of application No. PCT/US00/29364, filed on Oct. 25, 2000, and a continuation-in-part of application No. PCT/US00/30040, filed on Nov. 1, 2000, and a continuation-in-part of application No. PCT/US00/30037, filed on Nov. 1, 2000, and a continuation-in-part of application No. PCT/US00/30045, filed on Nov. 1, 2000, and a continuation-in-part of application No. PCT/US00/30036, filed on Nov. 1, 2000, and a continuation-in-part of application No. PCT/US00/30039, filed on Nov. 1, 2000, and a continuation-in-part of application No. PCT/US00/30654, filed on Nov. 8, 2000, and a continuation-in-part of application No. PCT/US00/30628, filed on Nov. 8, 2000, and a continuation-in-part of application No. PCT/US00/30653, filed on Nov. 8, 2000, and a continuation-in-part of application No. PCT/US00/30629, filed on Nov. 8, 2000, and a continuation-in-part of application No. PCT/US00/30679, filed on Nov. 8, 2000, and a continuation-in-part of application No. PCT/US00/30674, filed on Nov. 8, 2000, and a continuation-in-part of application No. PCT/US00/31162, filed on Nov. 15, 2000, and a continuation-in-part of application No. PCT/US00/31282, filed on Nov. 15, 2000, and a continuation-in-part of application No. PCT/US00/30657, filed on Nov. 8, 2000, and a continuation-in-part of application No. PCT/US01/01396, filed on Jan. 17, 2001, and a continuation-in-part of application No. PCT/US01/01387, filed on Jan. 17, 2001, and a continuation-in-part of application No. PCT/US01/01567, filed on Jan. 17, 2001, and a continuation-in-part of application No. PCT/US01/01431, filed on Jan. 17, 2001, which is a continuation-in-part of application No. 09/915,582, filed on Jul. 27, 2001, said application No. 10/100,683 is a continuation-in-part of application No. PCT/US01/01432, filed on Jan. 17, 2001, and a continuation-in-part of application No. PCT/US01/00544, filed on Jan. 9, 2001, and a continuation-in-part of application No. PCT/US01/01435, filed on Jan. 17, 2001, and a continuation-in-part of application No. PCT/US01/01386, filed on Jan. 17, 2001, and a continuation-in-part of application No. PCT/US01/01565, filed on Jan. 17, 2001, and a continuation-in-part of application No.

PCT/US01/01394, filed on Jan. 17, 2001, and a continuation-in-part of application No. PCT/US01/01434, filed on Jan. 17, 2001, and a continuation-in-part of application No. PCT/US01/01397, filed on Jan. 17, 2001, and a continuation-in-part of application No. PCT/US01/01385, filed on Jan. 17, 2001, and a continuation-in-part of application No. PCT/US01/01384, filed on Jan. 17, 2001, and a continuation-in-part of application No. PCT/US01/01383, filed on Jan. 17, 2001, and a continuation-in-part of application No. PCT/US02/05064, filed on Feb. 21, 2002, and a continuation-in-part of application No. PCT/US02/05301, filed on Feb. 21, 2002, application No. 12/753,401, which is a continuation-in-part of application No. 11/687,755, filed on Mar. 19, 2007, which is a division of application No. 10/644,356, filed on Sep. 20, 2003, which is a continuation-in-part of application No. PCT/US02/08123, filed on Mar. 19, 2002, which is a continuation-in-part of application No. 10/100,683, said application No. 10/664,356 is a continuation-in-part of application No. 10/100,683, said application No. 10/100,683 is a continuation-in-part of application No. 09/981,876, filed on Oct. 19, 2001, which is a division of application No. 09/621,011, filed on Jul. 20, 2000, which is a continuation of application No. 09/148,545, filed on Sep. 4, 1998, which is a continuation-in-part of application No. PCT/US98/04482, filed on Mar. 6, 1998, said application No. 10/100,683 is a continuation-in-part of application No. 09/621,011, which is a continuation of application No. 09/148,545, which is a continuation-in-part of application No. PCT/US98/04482, said application No. 10/100,683 is a continuation-in-part of application No. 09/148,545, which is a continuation-in-part of application No. PCT/US98/04482, said application No. 10/100,683 is a continuation-in-part of application No. PCT/US98/04482, and a continuation-in-part of application No. 09/882,171, filed on Jun. 18, 2001, which is a continuation of application No. 09/809,391, filed on Mar. 16, 2001, which is a continuation-in-part of application No. 09/149,476, filed on Sep. 8, 1998, which is a continuation-in-part of application No. PCT/US98/04493, filed on Mar. 6, 1998, said application No. 10/100,683 is a continuation-in-part of application No. 09/809,391, which is a continuation-in-part of application No. 09/149,476, which is a continuation-in-part of application No. PCT/US98/04493, said application No. 10/100,683 is a continuation-in-part of application No. 09/149,476, which is a continuation-in-part of application No. PCT/US98/04493, said application No. 10/100,683 is a continuation-in-part of application No. PCT/US98/04493, and a continuation-in-part of application No. 10/058,993, filed on Jan. 30, 2002, which is a continuation-in-part of application No. 09/852,659, filed on May 11, 2001, which is a continuation-in-part of application No. 09/152,060, filed on Sep. 11, 1998, which is a continuation-in-part of application No. PCT/US98/04858, filed on Mar. 12, 1998, said application No. 10/058,993 is a continuation-in-part of application No. 09/853,161, filed on May 11, 2001, which is a continuation-in-part of application No. 09/152,060, which is a continuation-in-part of application No. PCT/US98/04858, said application No. 10/058,993 is a continuation-in-part of application No. 09/852,797, filed on May 11, 2001, which is a continuation-in-part of application No. 09/152,060, which is a continuation-in-part of application No. PCT/US98/04858, said application No. 10/100,683 is a continuation-in-part of application No. 09/852,659, which is a continuation-in-part of application No. 09/152,060, which is a continuation-in-part of application No. PCT/US98/04858, said application No. 10/100,683 is a continuation-in-part of application No. 09/853,161, which is a continuation-in-part of application No. 09/152,060, which is a continuation-in-part of application No. PCT/US98/04858, said application No. 10/100,683 is a continuation-in-part of application No. 09/852,797, which is a continuation-in-part of application No. 09/152,060, which is a continuation-in-part of application No. PCT/US98/04858, said application No. 10/100,683 is a continuation-in-part of application No. 09/152,060, which is a continuation-in-part of application No. PCT/US98/04858, said application No. 10/100,683 is a continuation-in-part of application No. PCT/US98/04858, and a continuation-in-part of application No. 10/100,683, which is a continuation-in-part of application No. 10/059,395, filed on Jan. 31, 2002, which is a division of application No. 09/966,262, filed on Oct. 1, 2001, which is a continuation of application No. 09/154,707, filed on Sep. 17, 1998, which is a continuation-in-part of application No. PCT/US98/05311, filed on Mar. 19, 1998, said application No. 10/100,683 is a continuation-in-part of application No. 09/984,245, filed on Oct. 29, 2001, which is a division of application No. 09/154,707, filed on Sep. 17, 1998, which is a continuation-in-part of application No. PCT/US98/05311, said application No. 10/100,683 is a continuation-in-part of application No. 09/983,966, filed on Oct. 26, 2001, which is a division of application No. 09/154,707, which is a continuation-in-part of application No. PCT/US98/05311, said application No. 10/100,683 is a continuation-in-part of application No. 09/966,262, which is a continuation of application No. 09/154,707, which is a continuation-in-part of application No. PCT/US98/05311, said application No. 10/100,683 is a continuation-in-part of application No. 09/154,707, which is a continuation-in-part of application No. PCT/US98/05311, said application No. 10/100,683 is a continuation-in-part of application No. PCT/US98/05311, and a continuation-in-part of application No. 09/814,122, filed on Mar. 22, 2001, which is a continuation of application No. 09/577,145, filed on May 24, 2000, which is a continuation of application No. 09/166,780, filed on Oct. 6, 1998, which is a continuation-in-part of application No. PCT/US98/06801, filed on Apr. 7, 1998, said application No. 10/100,683 is a continuation-in-part of application No. PCT/US98/06801, and a continuation-in-part of application No. PCT/US98/10868, filed on May 28, 1998, and a continuation-in-part of application No. PCT/US98/11422, filed on Jun. 4, 1998, and a continuation-in-part of application No. PCT/US01/05614, filed on Feb. 21, 2001, and a continuation-in-part of application No. PCT/US98/12125, filed on Jun. 11, 1998, and a continuation-in-part of application No. 09/627,081, filed on Jul. 27, 2000, which is a continuation of application No. 09/213,365, filed on Dec. 17, 1998, which is a continuation-in-part of application No. PCT/US98/13608, filed on Jun. 30, 1998, said application No. 10/100,683 is a continuation-in-part of application No. PCT/US98/13608, and a continuation-in-part of application No. 09/984,490, filed on Oct. 30, 2001, which is a division of application No. 09/227,357, filed on Jan. 8, 1999, which is a continuation-in-part of application No. PCT/US98/13684, filed on Jul. 7, 1998, said application No. 10/100,683 is a continuation-in-part of application No. 09/983,802, filed on Oct. 25, 2001, which is a continuation of application No. 09/227,357, which is a continuation-in-part of application No. PCT/US98/13684, said application No. 10/100,683 is a continuation-in-part of application No. 09/973,278, filed on Oct. 10, 2001, which is a continuation-in-part of application No. 09/227,357, filed on Jan. 8, 1999, which is a continuation-in-part of application No. PCT/US98/13684, said application No. 10/100,683 is a continuation-in-part of application No. PCT/US98/13684, and a continuation-in-part of application No. 09/776,724, filed on Feb. 6, 2001, which is a continuation-in-part of application No. 09/669,688, filed on Sep. 26, 2000, which is a continuation of application No. 09/229,982, filed on Jan. 14, 1999, which is a continuation-in-part of application No. PCT/US98/14613, filed on Jul. 15, 1998, said application No. 10/100,683 is a continuation-in-part of application No. 09/669,688, which is a continuation of application No. 09/299,982, which is a continuation-in-part of application No. PCT/US98/14613, which is a continuation of application No. 10/100,683, which is a continuation-in-part of application No. 09/229,982, which is a continuation-in-part of application No. PCT/US98/14613, said application No. 10/100,683 is a continuation-in-part of application No. PCT/US98/14613, and a continuation-in-part of application No. 09/820,649, filed on Mar. 30, 2001, which is a continuation of application No. 09/666,984, filed on Sep. 21, 2000, which is a continuation of application No. 09/236,557, filed on Jan. 26, 1999, which is a continuation-in-part of application No. PCT/US98/15949, filed on Jul. 29, 1998, said application No. 10/100,683 is a continuation-in-part of application No. PCT/US98/15949, filed on Jul. 29, 1998, and a continuation-in-part of application No. 09/969,730, filed on Oct. 4, 2001, which is a continuation-in-part of application No. 09/774,639, filed on Feb. 1, 2001, which is a continuation of application No. 09/244,112, filed on Feb. 4, 1999, which is a continuation-in-part of application No. PCT/US98/16235, filed on Aug. 4, 1998, said application No. 10/100,683 is a continuation-in-part of application No. 09/774,639, filed on Feb. 1, 2001, which is a continuation of application No. 09/244,112, filed on Feb. 4, 1999, which is a continuation-in-part of application No. PCT/US98/16235, said application No. 10/100,683 is a continuation-in-part of application No. 09/969,730, filed on Oct. 4, 2001, and a continuation-in-part of application No. PCT/US98/16235, filed on Aug. 4, 1998, said application No. 10/100,683 is a continuation-in-part of application No. 09/716,128, filed on Nov. 17, 2000, which is a continuation of application No. 09/251,329, filed on Feb. 17, 1999, which is a continuation-in-part of application No. PCT/US98/17044, filed on Aug. 18, 1998, said application No. 10/100,683 is a continuation-in-part of application No. PCT/US98/17044, and a continuation-in-part of application No. 09/729,835, filed on Dec. 6, 2000, which is a division of application No. 09/257,179, filed on Feb. 25, 1999, which is a continuation-in-part of application No. PCT/US98/17709, filed on Aug. 27, 1998, said application No. 10/100,683 is a continuation-in-part of application No. 09/257,179, which is a continuation-in-part of application No. PCT/US98/17709, said application No. 10/100,683 is a continuation-in-part of application No. PCT/US98/17709, and a continuation-in-part of application No. 10/047,021, filed on Jan. 17, 2002, which is a continuation-in-part of application No. 09/722,329, filed on Nov. 28, 2000, which is a continuation of application No. 09/262,109, filed on Mar. 4, 1999, which is a continuation-in-part of application No. PCT/US98/18360, filed on Sep. 3, 1998, said application No. 10/100,683 is a continuation-in-part of application No. 09/722,329, which is a continuation of application No. 09/262,109, which is a continuation-in-part of application No. PCT/US98/18360, said application No. 10/100,683 is a continuation-in-part of application No. PCT/US02/01109, filed on Jan. 17, 2002, and a continuation-in-part of application No. PCT/US98/18360, and a continuation-in-part of application No. 09/281,976, filed on Mar. 31, 1999, which is a continuation-in-part of application No. PCT/US98/20775, filed on Oct. 1, 1998, said application No. 10/100,683 is a continuation-in-part of application No. PCT/US98/20775, and a continuation-in-part of application No. 09/984,429, filed on Oct. 30, 2001, which is a continuation-in-part of application No. 09/288,143, filed on Apr. 8, 1999, which is a continuation-in-part of application No. PCT/US98/21142, filed on Oct. 8, 1998, said application No. 10/100,683 is a continuation-in-part of application No. 09/288,143, which is a continuation-in-part of application No. PCT/US98/21142, said application No. 10/100,683 is a continuation-in-part of application No. PCT/US98/21142, and a continuation-in-part of application No. 09/296,622, filed on Apr. 23, 1999, which is a continuation-in-part of application No. PCT/US98/22376, filed on Oct. 23, 1998, said application No. 10/100,683 is a continuation-in-part of application No. PCT/US98/22376, and a continuation-in-part of application No. 09/974,879, filed on Oct. 12, 2001, which is a continuation-in-part of application No. 09/818,683, filed on Mar. 28, 2001, which is a continuation-in-part of application No. 09/305,736, filed on May 5, 1999, which is a continuation-in-part of application No. PCT/US98/23435, filed on Nov. 4, 1998, said application No. 10/100,683 is a continuation-in-part of application No. 09/818,683, which is a continuation of application No. 09/305,736, which is a continuation-in-part of application No. PCT/US98/23435, said application No. 10/100,683 is a continuation-in-part of application No. 09/305,736, which is a continuation-in-part of application No. PCT/US98/23435, said application No. 10/100,683 is a continuation-in-part of application No. PCT/US98/23435, and a continuation-in-part of application No. 09/334,595, filed on Jun. 17, 1999, which is a continuation-in-part of application No. PCT/US98/27059, filed on Dec. 17, 1998, said application No. 10/100,683 is a continuation-in-part of application No. PCT/US98/27059, and a continuation-in-part of application No. 09/938,671, filed on Aug. 27, 2001, which is a continuation of application No. 09/739,907, filed on Dec. 20, 2000, which is a continuation of application No. 09/348,457, filed on Jul. 7, 1999, which is a continuation-in-part of application No. PCT/US99/00108, filed on Jan. 6, 1999, said application No. 10/100,683 is a continuation-in-part of application No. 09/739,907, which is a continuation of application No. 09/348,457, which is a continuation-in-part of application No. PCT/US99/00108, said application No. 10/100,683 is a continuation-in-part of application No. 09/348,457, filed on Jul. 7, 1999, which is a continuation-in-part of application No. PCT/US99/00108, said application No. 10/100,683 is a continuation-in-part of application No. PCT/US99/00108, and a continuation-in-part of application No. 09/949,925, filed on Sep. 12, 2001, which is a continuation-in-part of application No. PCT/US99/01621, filed on Jan. 27, 1999, and a continuation-in-part of application No. 09/363,044, filed on Jul. 29, 1999, which is a continuation-in-part of application No. PCT/US99/01621, said application No. 10/100,683 is a continuation-in-part of application No. 09/813,153, filed on Mar. 21, 2001, which is a continuation of application No. 09/363,044, filed on Jul. 29, 1999, which is a continuation-in-part of application No. PCT/US99/01621, said application No. 10/100,683 is a continuation-in-part of application No. 09/363,044, which is a continuation-in-part of application No. PCT/US99/01621, said application No. 10/100,683 is a continuation-in-part of application No. PCT/US99/01621, and a continuation-in-part of application No. 10/062,548, filed on Feb. 5, 2002, which is a continuation of application No. 09/369,247, filed on Aug. 5, 1999, which is a continuation-in-part of application No. PCT/US99/02293, filed on Feb. 4, 1999, said application No. 10/100,683 is a continuation-in-part of application No. 09/369,247, which is a continuation-in-part of application No. PCT/US99/02293, said application No. 10/100,683 is a continuation-in-part of application No. PCT/US99/02293, and a continuation-in-part of application No. 09/716,129, filed on Nov. 17, 2000, which is a continuation-in-part of application No. PCT/US99/03939, filed on Feb. 24, 1999, which is a continuation of application No. 09/382,572, filed on Aug. 25, 1999, which is a continuation-in-part of application No. PCT/US99/03939, said application No. 10/100,683 is a continuation-in-part of application No. PCT/US99/03939, and a continuation-in-part of application No. 09/798,889, filed on Mar. 6, 2001, which is a continuation of application No. 09/393,022, filed on Sep. 9, 1999, which is a continuation-in-part of application No. PCT/US99/05721, filed on Mar. 11, 1999, said application No. 10/100,683 is a continuation-in-part of application No. PCT/US99/05721, and a continuation-in-part of application No. 09/397,945, filed on Sep. 17, 1999, which is a continuation-in-part of application No. PCT/US99/05804, filed on Mar. 18, 1999, said application No. 10/100,683 is a continuation-in-part of application No. PCT/US99/05804, and a continuation-in-part of application No. 09/948,783, filed on Sep. 10, 2001, which is a continuation-in-part of application No. 09/892,877, filed on Jun. 28, 2001, which is a continuation of application No. 09/437,658, filed on Nov. 10, 1999, which is a continuation-in-part of application No. PCT/US99/09847, filed on May 6, 1999, said application No. 10/100,683 is a continuation-in-part of application No. 09/892,877, which is a continuation of application No. 09/437,658, which is a continuation-in-part of application No. PCT/US99/09847, said application No. 10/100,683 is a continuation-in-part of application No. PCT/US99/09847, and a continuation-in-part of application No. 10/050,873, filed on Jan. 18, 2002, which is a continuation-in-part of application No. 09/461,325, filed on Dec. 14, 1999, which is a continuation-in-part of application No. PCT/US99/13418, filed on Jun. 15, 1999, said application No. 10/100,683 is a continuation-in-part of application No. 10/012,542, filed on Dec. 12, 2001, which is a division of application No. 09/461,325, which is a continuation-in-part of application No. PCT/US99/13418, said application No. 10/100,683 is a continuation-in-part of application No. 09/461,325, which is a continuation-in-part of application No. PCT/US99/13418, said application No. 10/100,683 is a continuation-in-part of application No. PCT/US99/13418, and a continuation-in-part of application No. 09/984,271, filed on Oct. 29, 2001, which is a division of application No. 09/482,273, filed on Jan. 13, 2000, which is a continuation-in-part of application No. PCT/US99/15849, filed on Jul. 14, 1999, said application No. 10/100,683 is a continuation-in-part of application No. 09/984,276, filed on Oct. 29, 2001, which is a division of application No. 09/482,273, which is a continuation-in-part of application No. PCT/US99/15849, said application No. 10/100,683 is a continuation-in-part of application No. 09/482,273, which is a continuation-in-part of application No. PCT/US99/15849, said application No. 10/100,683 is a continuation-in-part of application No. PCT/US99/15849, and a continuation-in-part of application No. PCT/US01/29871, filed on Sep. 24, 2001, which is a continuation-in-part of application No. PCT/US01/00911, filed on Jan. 12, 2001, said application No. 10/100,683 is a continuation-in-part of application No. PCT/US01/00911, which is a continuation-in-part of application No. 09/482,273, said application No. 10/100,683 is a continuation-in-part of application No. 09/489,847, filed on Jan. 24, 2000, which is a continuation-in-part of application No. PCT/US99/17130, filed on Jul. 29, 1999, said application No. 10/100,683 is a continuation-in-part of application No. PCT/US99/17130, and a continuation-in-part of application No. 10/054,988, filed on Jan. 25, 2002, which is a continuation of application No. 09/904,615, filed on Jul. 16, 2001, which is a continuation of application No. 09/739,254, filed on Dec. 19, 2000, which is a continuation of application No. 09/511,554, filed on Feb. 23, 2000, which is a continuation-in-part of application No. PCT/US99/19330, filed on Aug. 24, 1999, said application No. 10/100,683 is a continuation-in-part of application No. 09/904,615, which is a continuation of application No. 09/739,254, which is a continuation of application No. 09/511,554, which is a continuation-in-part of application No. PCT/US99/19330, and a continuation-in-part of application No. 10/100,683, which is a continuation-in-part of application No. PCT/US99/19330, and a continuation-in-part of application No. 09/820,893, filed on Mar. 30, 2001, which is a continuation of application No. 09/531,119, filed on Mar. 20, 2000, which is a continuation-in-part of application No. PCT/US99/22012, filed on Sep. 22, 1999, said application No. 10/100,683 is a continuation-in-part of application No. PCT/US99/22012, and a continuation-in-part of application No. 09/948,820, filed on Sep. 10, 2001, which is a continuation of application No. 09/565,391, filed on May 5, 2000, which is a continuation-in-part of application No. PCT/US99/26409, filed on Nov. 9, 1999, said application No. 10/100,683 is a continuation-in-part of application No. 09/565,391, which is a continuation-in-part of application No. PCT/US99/26409, said application No. 10/100,683 is a continuation-in-part of application No. PCT/US99/26409, and a continuation-in-part of application No. 09/895,298, filed on Jul. 2, 2001, which is a continuation of application No. 09/591,316, filed on Jun. 9, 2000, which is a continuation-in-part of application No. PCT/US99/29950, filed on Dec. 16, 1999, said application No. 10/100,683 is a continuation-in-part of application No. PCT/US99/29950, and a continuation-in-part of application No. 09/985,153, filed on Nov. 1, 2001, which is a continuation of application No. 09/618,150, filed on Jul. 17, 2000, which is a continuation-in-part of application No. PCT/US00/00903, filed on Jan. 18, 2000, said application No. 10/100,683 is a continuation-in-part of application No. PCT/US99/00903, and a continuation-in-part of application No. 09/997,131, filed on Nov. 30, 2001, which is a continuation of application No. 09/628,508, filed on Jul. 28, 2000, which is a continuation-in-part of application No. PCT/US00/03062, filed on Feb. 8, 2000, said application No. 10/100,683 is a continuation-in-part of application No. PCT/US00/03062, and a continuation-in-part of application No. 10/050,882, filed on Jan. 18, 2002, which is a continuation of application No. 09/661,453, filed on Sep. 13, 2000, which is a continuation-in-part of application No. PCT/US00/06783, filed on Mar. 16, 2000, said application No. 10/100,683 is a continuation-in-part of application No. 09/661,453, filed on Sep. 13, 2000, which is a continuation-in-part of application No. PCT/US00/06783, said application No. 10/100,683 is a continuation-in-part of application No. PCT/US00/06783, and a continuation-in-part of application No. 10/050,704, filed on Jan. 18, 2002, which is a continuation of application No. 09/684,524, filed on Oct. 10, 2000, which is a continuation-in-part of application No. PCT/US00/08979, filed on Apr. 6, 2000, said application No. 10/100,683 is a continuation-in-part of application No. 09/684,524, which is a continuation-in-part of application No. PCT/US00/08979, said application No. 10/100,683 is a continuation-in-part of application No. PCT/US00/08979, and a continuation-in-part of application No. 10/042,141, filed on Jan. 11, 2002, which is a continuation of application No. 09/726,643, filed on Dec. 1, 2000, which is a continuation-in-part of application No. PCT/US00/15187, filed on Jun. 2, 2000, said application No. 10/100,683 is a continuation-in-part of application No. 09/726,643, which is a continuation-in-part of application No. PCT/US00/15187, said application No. 10/100,683 is a continuation-in-part of application No. PCT/US00/15187, and a continuation-in-part of application No. 09/756,168, filed on Jan. 9, 2001, which is a continuation-in-part of application No. PCT/US00/19735, filed on Jul. 23, 1999, said application No. 10/100,683 is a continuation-in-part of application No. PCT/US00/19735, and a continuation-in-part of application No. 10/060,255, filed on Feb. 1, 2002, which is a continuation of application No. 09/781,417, filed on Feb. 13, 2001, which is a continuation-in-part of application No. PCT/US00/22325, filed on Aug. 16, 2000, said application No. 10/100,683 is a continuation-in-part of application No. 09/781,417, which is a continuation-in-part of application No. PCT/US00/22325, said application No. 10/100,683 is a continuation-in-part of application No. PCT/US00/22325, and a continuation-in-part of application No. 09/789,561, filed on Feb. 22, 2001, which is a continuation-in-part of application No. PCT/US00/24008, filed on Aug. 31, 2000, said application No. 10/100,683 is a continuation-in-part of application No. PCT/US00/24008, and a continuation-in-part of application No. 09/800,729, filed on Mar. 8, 2001, which is a continuation-in-part of application No. PCT/US00/26013, filed on Sep. 22, 2000, said application No. 10/100,683 is a continuation-in-part of application No. PCT/US00/26013, and a continuation-in-part of application No. 09/832,129, filed on Apr. 11, 2001, which is a continuation-in-part of application No. PCT/US00/28664, filed on Oct. 17, 2000, said application No. 10/100,683 is a continuation-in-part of application No. PCT/US00/28664, and a continuation-in-part of application No. PCT/US00/29363, and a continuation-in-part of application No. PCT/US00/29360, filed on Oct. 25, 2000, and a continuation-in-part of application No. PCT/US00/29362, filed on Oct. 25, 2000, and a continuation-in-part of application No. PCT/US00/29365, filed on Oct. 25, 2000, said application No. PCT/US00/29364 is a continuation of application No. PCT/US00/30040, filed on Nov. 1, 2000, and a continuation-in-part of application No. PCT/US00/30037, filed on Nov. 1, 2000, and a continuation-in-part of application No. PCT/US00/30045, filed on Nov. 1, 2000, and a continuation-in-part of application No. PCT/US00/30036, filed on Nov. 1, 2000, and a continuation-in-part of application No. PCT/US00/30039, filed on Nov. 1, 2000, and a continuation-in-part of application No. PCT/US00/30654, filed on Nov. 8, 2000, and a continuation-in-part of application No. PCT/US00/30628, filed on Nov. 8, 2000, and a continuation-in-part of application No. PCT/US00/30653, filed on Nov. 8, 2000, and a continuation-in-part of application No. PCT/US00/30629, filed on Nov. 8, 2000, and a continuation-in-part of application No. PCT/US00/30679, filed on Nov. 8, 2000, and a continuation-in-part of application No. PCT/US00/30674, filed on Nov. 8, 2000, and a continuation-in-part of application No. PCT/US00/31162, filed on Nov. 15, 2000, and a continuation-in-part of application No. PCT/US00/31282, filed on Nov. 15, 2000, and a continuation-in-part of application No. PCT/US00/30657, filed on Nov. 8, 2000, and a continuation-in-part of application No. PCT/US01/01396, filed on Jan. 17, 2001, and a continuation-in-part of application No. PCT/US01/01387, filed on Jan. 17, 2001, and a continuation-in-part of application No. PCT/US01/01567, filed on Jan. 17, 2001, and a continuation-in-part of application No. PCT/US01/01431, filed on Jan. 17, 2001, which is a continuation-in-part of application No. 09/915,582, filed on Jul. 27, 2001, said application No. 10/100,683 is a continuation-in-part of application No. PCT/US01/00544, filed on Jan. 9, 2001, and a continuation-in-part of application No. PCT/US01/01435, filed on Jan. 17, 2001, and a continuation-in-part of application No. PCT/US01/01386, filed on Jan. 17, 2001, and a continuation-in-part of application No. PCT/US01/01565, filed on Jan. 17, 2001, and a continuation-in-part of application No. PCT/US01/01394, filed on Jan. 17, 2001, and a continuation-in-part of application No. PCT/US01/01434, filed on Jan. 17, 2001, and a continuation-in-part of application No. PCT/US01/01397, filed on Jan. 17, 2001, and a continuation-in-part of application No. PCT/US01/01385, filed on Jan. 17, 2001, and a continuation-in-part of application No. PCT/US01/01384, filed on Jan. 17, 2001, and a continuation-in-part of application No. PCT/US01/01383, filed on Jan. 17, 2001, and a continuation-in-part of application No. PCT/US02/05064, filed on Feb. 21, 2002, and a continuation-in-part of application No. PCT/US02/05301, filed on Feb. 21, 2002, application No. 12/753,401, which is a continuation-in-part of application No. 12/198,817, filed on Aug. 26, 2008, which is a division of application No. 11/346,470, filed on Feb. 3, 2006, which is a continuation-in-part of application No. 10/472,532, filed as application No. PCT/US02/08278 on Mar. 19, 2002, said application No. 11/346,470 is a continuation-in-part of application No. 10/100,683, said application No. 11/346,470 is a continuation-in-part of application No. 10/100,683, which is a continuation-in-part of application No. 09/981,876, filed on Oct. 19, 2001, which is a division of application No. 09/621,011, filed on Jul. 20, 2000, which is a continuation of application No. 09/148,545, filed on Sep. 4, 1998, which is a continuation-in-part of application No. PCT/US98/04482, filed on Mar. 6, 1998, said application No. 10/100,683 is a continuation-in-part of application No. 09/621,011, filed on Jul. 20, 2000, which is a continuation of application No. 09/148,545, which is a continuation-in-part of application No. PCT/US98/04482, said application No. 10/100,683 is a continuation-in-part of application No. 09/148,545, which is a continuation-in-part of application No. PCT/US98/04482, said application No. 10/100,683 is a continuation-in-part of application No. PCT/US98/04482, and a continuation-in-part of application No. 09/882,171, filed on Jun. 18, 2001, which is a continuation of application No. 09/809,391, filed on Mar. 16, 2001, which is a continuation-in-part of application No. 09/149,476, filed on Sep. 8, 1998, which is a continuation-in-part of application No. PCT/US98/04493, filed on Mar. 6, 1998, said application No. 10/100,683 is a continuation-in-part of application No. 09/809,391, which is a continuation-in-part of application No. 09/149,476, which is a continuation-in-part of application No. PCT/US98/04493, said application No. 10/100,683 is a continuation-in-part of application No. 09/149,476, which is a continuation-in-part of application No. PCT/US98/04493, said application No. 10/100,683 is a continuation-in-part of application No. PCT/US98/04493, and a continuation-in-part of application No. 09/882,171, which is a continuation of application No. 09/809,391, filed on Mar. 16, 2001, which is a continuation-in-part of application No. 09/149,476, which is a continuation-in-part of application No. PCT/US98/04493, filed on Mar. 6, 1998, said application No. 10/100,683 is a continuation-in-part of application No. 09/809,391, which is a continuation-in-part of application No. 09/149,476, which is a continuation-in-part of application No. PCT/US98/04493, said application No. 10/100,683 is a continuation-in-part of application No. 09/149,476, which is a continuation-in-part of application No. PCT/US98/04493, said application No. 10/100,683 is a continuation-in-part of application No. PCT/US98/04493, and a continuation-in-part of application No. 10/058,993, which is a continuation-in-part of application No. 09/852,659, filed on May 11, 2001, which is a continuation-in-part of application No. 09/152,060, filed on Sep. 11, 1998, which is a continuation-in-part of application No. PCT/US98/04858, filed on Mar. 12, 1998, said application No. 10/058,993 is a continuation-in-part of application No. 09/853,161, filed on May 11, 2001, which is a continuation-in-part of application No. 09/152,060, which is a continuation-in-part of application No. PCT/US98/04858, said application No. 10/058,993 is a continuation-in-part of application No. 09/852,797, filed on May 11, 2001, which is a continuation-in-part of application No. 09/152,060, which is a continuation-in-part of application No.

PCT/US98/04858, said application No. 10/100,683 is a continuation-in-part of application No. 09/852,659, which is a continuation-in-part of application No. 09/152,060, which is a continuation-in-part of application No. PCT/US98/04858, said application No. 10/100,683 is a continuation-in-part of application No. 09/853,161, which is a continuation-in-part of application No. 09/152,060, which is a continuation-in-part of application No. PCT/US98/04858, said application No. 10/100,683 is a continuation-in-part of application No. 09/852,797, which is a continuation-in-part of application No. 09/152,060, which is a continuation-in-part of application No. PCT/US98/04858, said application No. 10/100,683 is a continuation-in-part of application No. 09/152,060, which is a continuation-in-part of application No. PCT/US98/04858, said application No. 10/100,683 is a continuation-in-part of application No. PCT/US98/04858, and a continuation-in-part of application No. 10/059,395, filed on Jan. 31, 2002, which is a division of application No. 09/966,262, filed on Oct. 1, 2001, which is a continuation of application No. 09/154,707, filed on Sep. 17, 1998, which is a continuation-in-part of application No. PCT/US98/05311, filed on Mar. 19, 1998, said application No. 10/100,683 is a continuation-in-part of application No. 09/984,245, filed on Oct. 29, 2001, which is a division of application No. 09/154,707, which is a continuation-in-part of application No. PCT/US98/05311, said application No. 10/100,683 is a continuation-in-part of application No. 09/983,966, filed on Oct. 26, 2001, which is a division of application No. 09/154,707, which is a continuation-in-part of application No. PCT/US98/05311, said application No. 10/100,683 is a continuation-in-part of application No. 09/966,262, filed on Oct. 1, 2001, which is a continuation of application No. 09/154,707, which is a continuation-in-part of application No. PCT/US98/05311, said application No. 10/100,683 is a continuation-in-part of application No. 09/154,707, which is a continuation-in-part of application No. PCT/US98/05311, said application No. 10/100,683 is a continuation-in-part of application No. PCT/US98/05311, and a continuation-in-part of application No. 09/814,122, filed on Mar. 22, 2001, which is a continuation of application No. 09/577,145, filed on May 24, 2000, which is a continuation of application No. 09/166,780, filed on Oct. 6, 1998, which is a continuation-in-part of application No. PCT/US98/06801, filed on Apr. 7, 1998, said application No. 10/100,683 is a continuation-in-part of application No. PCT/US98/06801, and a continuation-in-part of application No. PCT/US98/10868, filed on May 28, 1998, and a continuation-in-part of application No. PCT/US98/11422, filed on Jun. 4, 1998, and a continuation-in-part of application No. PCT/US01/05614, filed on Feb. 21, 2001, and a continuation-in-part of application No. PCT/US98/12125, filed on Jun. 11, 1998, and a continuation-in-part of application No. 09/627,081, filed on Jul. 27, 2000, which is a continuation of application No. 09/213,365, filed on Dec. 17, 1998, which is a continuation-in-part of application No. PCT/US98/13608, filed on Jun. 30, 1998, which is a continuation-in-part of application No. PCT/US98/13608, said application No. 10/100,683 is a continuation-in-part of application No. 09/984,490, filed on Oct. 30, 2001, which is a division of application No. 09/227,357, filed on Jan. 8, 1999, which is a continuation-in-part of application No. PCT/US98/13684, filed on Jul. 7, 1998, said application No. 10/100,683 is a continuation-in-part of application No. 09/983,802, filed on Oct. 25, 2001, which is a continuation of application No. 09/227,357, which is a continuation-in-part of application No. PCT/US98/13684, said application No. 10/100,683 is a continuation-in-part of application No. 09/973,278, filed on Oct. 10, 2001, which is a continuation-in-part of application No. 09/227,357, which is a continuation-in-part of application No. PCT/US98/13684, said application No. 10/100,683 is a continuation-in-part of application No. PCT/US98/13684, and a continuation-in-part of application No. 09/776,724, filed on Feb. 6, 2001, which is a continuation-in-part of application No. 09/669,688, filed on Sep. 26, 2000, which is a continuation of application No. 09/229,982, filed on Jan. 14, 1999, which is a continuation-in-part of application No. PCT/US98/14613, filed on Jul. 15, 1998, said application No. 10/100,683 is a continuation-in-part of application No. 09/669,688, which is a continuation of application No. 09/229,982, which is a continuation-in-part of application No. PCT/US98/14613, said application No. 10/100,683 is a continuation-in-part of application No. 09/229,982, which is a continuation-in-part of application No. PCT/US98/14613, said application No. 10/100,683 is a continuation-in-part of application No. PCT/US98/14613, and a continuation-in-part of application No. 09/820,649, filed on Mar. 30, 2001, which is a continuation of application No. 09/666,984, filed on Sep. 21, 2000, which is a continuation-in-part of application No. 09/236,557, filed on Jan. 26, 1999, which is a continuation-in-part of application No. PCT/US98/15949, filed on Jul. 29, 1998, said application No. 10/100,683 is a continuation-in-part of application No. PCT/US98/15949, and a continuation-in-part of application No. 09/969,730, filed on Oct. 4, 2001, which is a continuation-in-part of application No. 09/774,639, filed on Feb. 1, 2001, which is a continuation of application No. 09/244,112, filed on Feb. 4, 1999, which is a continuation-in-part of application No. PCT/US98/16235, filed on Aug. 4, 1998, said application No. 10/100,683 is a continuation-in-part of application No. 09/774,639, which is a continuation of application No. 09/244,112, which is a continuation-in-part of application No. PCT/US98/16235, said application No. 10/100,683 is a continuation-in-part of application No. 09/969,730, filed on Oct. 4, 2001, and a continuation-in-part of application No. PCT/US98/16235, and a continuation-in-part of application No. 09/716,128, filed on Nov. 17, 2000, which is a continuation of application No. 09/251,329, filed on Feb. 17, 1999, which is a continuation-in-part of application No. PCT/US98/17044, filed on Aug. 18, 1998, said application No. 10/100,683 is a continuation-in-part of application No. PCT/US98/17044, and a continuation-in-part of application No. 09/729,835, filed on Dec. 6, 2000, which is a division of application No. 09/257,179, filed on Feb. 25, 1999, which is a continuation-in-part of application No. PCT/US98/17709, filed on Aug. 27, 1998, said application No. 10/100,683 is a continuation-in-part of application No. 09/257,179, which is a continuation-in-part of application No. PCT/US98/17709, said application No. 10/100,683 is a continuation-in-part of application No. PCT/US98/17709, and a continuation-in-part of application No. 10/047,021, filed on Jan. 17, 2002, which is a continuation-in-part of application No. 09/722,329, filed on Nov. 28, 2000, which is a continuation of application No. 09/262,109, filed on Mar. 4, 1999, which is a continuation-in-part of application No. PCT/US98/18360, filed on Sep. 3, 1998, said application No. 10/100,683 is a continuation-in-part of application No. 09/722,329, which is a continuation of application No. 09/262,109, which is a continuation-in-part of application No. PCT/US98/18360, said application No. 10/100,683 is a continuation-in-part of application No. PCT/US02/01109, filed on Jan. 17, 2002, and a continuation-in-part of application No. PCT/US98/18360, and a continuation-in-part of application No. 09/281,976, filed on Mar. 31, 1999, which is a continuation-in-part of application No. PCT/US98/20775, filed on Oct. 1, 1998, said application No. 10/100,683 is a continuation-in-part of application No. PCT/US98/20775, and a continuation-in-part of application No. 09/984,429, filed on Oct. 30, 2001, which is a continuation-in-part of application No. 09/288,143, filed on Apr. 8, 1999, which is a continuation-in-part of application No. PCT/US98/21142, filed on Oct. 8, 1998, said application No. 10/100,683 is a continuation-in-part of application No. 09/288,143, filed on Apr. 8, 1999, which is a continuation-in-part of application No. PCT/US98/21142, said application No. 10/100,683 is a continuation-in-part of application No. PCT/US98/21142, and a continuation-in-part of application No. 09/296,622, filed on Apr. 23, 1999, which is a continuation-in-part of application No. PCT/US98/22376, filed on Oct. 23, 1998, said application No. 10/100,683 is a continuation-in-part of application No. PCT/US98/22376, and a continuation-in-part of application No. 09/974,879, filed on Oct. 12, 2001, which is a continuation-in-part of application No. 09/818,683, which is a continuation of application No. 09/305,736, filed on May 5, 1999, which is a continuation-in-part of application No. PCT/US98/23435, filed on Nov. 4, 1998, said application No. 10/100,683 is a continuation-in-part of application No. 09/818,683, which is a continuation of application No. 09/305,736, which is a continuation-in-part of application No. PCT/US98/23435, said application No. 10/100,683 is a continuation-in-part of application No. 09/305,736, which is a continuation-in-part of application No. PCT/US98/23435, said application No. 10/100,683 is a continuation-in-part of application No. PCT/US98/23435, and a continuation-in-part of application No. 09/334,595, filed on Jun. 17, 1999, which is a continuation-in-part of application No. PCT/US98/27059, filed on Dec. 17, 1998, said application No. 10/100,683 is a continuation-in-part of application No. PCT/US98/27059, and a continuation-in-part of application No. 09/938,671, filed on Aug. 27, 2001, which is a continuation of application No. 09/739,907, filed on Dec. 20, 2000, which is a continuation of application No. 09/348,457, filed on Jul. 7, 1999, which is a continuation-in-part of application No. PCT/US99/00108, filed on Jan. 6, 1999, said application No. 10/100,683 is a continuation-in-part of application No. 09/739,907, which is a continuation of application No. 09/348,457, which is a continuation-in-part of application No. PCT/US99/00108, said application No. 10/100,683 is a continuation-in-part of application No. 09/348,457, which is a continuation-in-part of application No. PCT/US99/00108, said application No. 10/100,683 is a continuation-in-part of application No. PCT/US99/00108, and a continuation-in-part of application No. 09/949,925, filed on Sep. 12, 2001, which is a continuation-in-part of application No. PCT/US99/01621, filed on Jan. 27, 1999, and a continuation-in-part of application No. 09/363,044, filed on Jul. 29, 1999, which is a continuation-in-part of application No. PCT/US99/01621, said application No. 10/100,683 is a continuation-in-part of application No. 09/813,153, filed on Mar. 21, 2001, which is a continuation-in-part of application No. 09/363,044, filed on Jul. 29, 1999, which is a continuation-in-part of application No. PCT/US99/01621, said application No. 10/100,683 is a continuation-in-part of application No. 09/363,044, which is a continuation-in-part of application No. PCT/US99/01621, said application No. 10/100,683 is a continuation-in-part of application No. PCT/US99/01621, and a continuation-in-part of application No. 10/062,548, filed on Feb. 5, 2002, which is a continuation of application No. 09/369,247, filed on Aug. 5, 1999, which is a continuation-in-part of application No. PCT/US99/02293, filed on Feb. 4, 1999, said application No. 10/100,683 is a continuation-in-part of application No. 09/369,247, which is a continuation-in-part of application No. PCT/US99/02293, said application No. 10/100,683 is a continuation-in-part of application No. PCT/US99/02293, and a continuation-in-part of application No. 09/716,129, filed on Nov. 17, 2000, which is a continuation-in-part of application No. PCT/US99/03939, filed on Feb. 24, 1999, which is a continuation of application No. 09/382,572, filed on Aug. 25, 1999, which is a continuation-in-part of application No. PCT/US99/03939, said application No. 10/100,683 is a continuation-in-part of application No. PCT/US99/03939, and a continuation-in-part of application No. 09/798,889, filed on Mar. 6, 2001, which is a continuation of application No. 09/393,022, filed on Sep. 9, 1999, which is a continuation-in-part of application No. PCT/US99/05721, filed on Mar. 11, 1999, and a continuation-in-part of application No. 10/100,683, which is a continuation-in-part of application No. PCT/US99/05721, and a continuation-in-part of application No. 09/397,945, filed on Sep. 17, 1999, which is a continuation-in-part of application No. PCT/US99/05804, filed on Mar. 18, 1999, said application No. 10/100,683 is a continuation-in-part of application No.

PCT/US99/05804, and a continuation-in-part of application No. 09/948,783, filed on Sep. 10, 2001, which is a continuation-in-part of application No. 09/892,877, filed on Jun. 28, 2001, which is a continuation of application No. 09/437,658, filed on Nov. 10, 1999, which is a continuation-in-part of application No. PCT/US99/09847, filed on May 6, 1999, said application No. 10/100,683 is a continuation-in-part of application No. 09/982,877, which is a continuation of application No. 09/437,658, which is a continuation-in-part of application No. PCT/US99/09847, said application No. 10/100,683 is a continuation-in-part of application No. PCT/US99/09847, and a continuation-in-part of application No. 10/050,873, filed on Jan. 18, 2002, which is a continuation-in-part of application No. 09/461,325, filed on Dec. 14, 1999, which is a continuation-in-part of application No. PCT/US99/13418, filed on Jun. 15, 1999, said application No. 10/100,683 is a continuation-in-part of application No. 10/012,542, filed on Dec. 12, 2001, which is a division of application No. 09/461,325, which is a continuation-in-part of application No. PCT/US99/13418, said application No. 10/100,683 is a continuation-in-part of application No. 09/461,325, which is a continuation-in-part of application No. PCT/US99/13418, said application No. 10/100,683 is a continuation-in-part of application No. PCT/US99/13418, and a continuation-in-part of application No. 09/461,325, which is a continuation-in-part of application No. PCT/US99/13418, said application No. 10/100,683 is a continuation-in-part of application No. 10/012,542, filed on Dec. 12, 2001, which is a division of application No. 09/461,325, which is a continuation-in-part of application No. PCT/US99/13418, said application No. 10/100,683 is a continuation-in-part of application No. 09/461,325, which is a continuation-in-part of application No. PCT/US99/13418, said application No. 10/100,683 is a continuation-in-part of application No. PCT/US99/13418, and a continuation-in-part of application No. 09/984,271, filed on Oct. 29, 2001, which is a division of application No. 09/482,273, filed on Jan. 13, 2000, which is a continuation-in-part of application No. PCT/US99/15849, filed on Jul. 14, 1999, said application No. 10/100,683 is a continuation-in-part of application No. 09/984,276, filed on Oct. 29, 2001, which is a division of application No. 09/482,273, which is a continuation-in-part of application No. PCT/US99/15849, said application No. 10/100,683 is a continuation-in-part of application No. 09/482,273, which is a continuation-in-part of application No. PCT/US99/15849, said application No. 10/100,683 is a continuation-in-part of application No. PCT/US99/15849, and a continuation-in-part of application No. PCT/US01/29871, filed on Sep. 24, 2001, which is a continuation-in-part of application No. PCT/US01/00911, filed on Jan. 12, 2001, said application No. 10/100,683 is a continuation-in-part of application No. PCT/US01/00911, which is a continuation-in-part of application No. 09/482,273, said application No. 10/100,683 is a continuation-in-part of application No. 09/489,847, filed on Jan. 24, 2000, which is a continuation-in-part of application No. PCT/US99/17130, filed on Jul. 29, 1999, said application No. 10/100,683 is a continuation-in-part of application No. PCT/US99/17130, and a continuation-in-part of application No. 10/054,988, filed on Jan. 25, 2002, which is a continuation of application No. 09/904,615, filed on Jul. 16, 2001, which is a continuation of application No. 09/739,254, filed on Dec. 19, 2000, which is a continuation of application No. 09/511,554, filed on Feb. 23, 2000, which is a continuation-in-part of application No. PCT/US99/19330, filed on Aug. 24, 1999, said application No. 10/100,683 is a continuation-in-part of application No. 09/904,615, which is a continuation of application No. 09/739,254, which is a continuation of application No. 09/511,554, which is a continuation-in-part of application No. PCT/US99/19330, said application No. 10/100,683 is a continuation-in-part of application No. PCT/US99/19330, and a continuation-in-part of application No. 09/820,893, filed on Mar. 30, 2001, which is a continuation of application No. 09/531,119, filed on Mar. 20, 2000, which is a continuation-in-part of application No. PCT/US99/22012, filed on Sep. 22, 1999, said application No. 10/100,683 is a continuation-in-part of application No. PCT/US99/22012, and a continuation-in-part of application No. 09/948,820, filed on Sep. 10, 2001, which is a continuation of application No. 09/565,391, filed on May 5, 2000, which is a continuation-in-part of application No. PCT/US99/26409, filed on Nov. 9, 1999, said application No. 10/100,683 is a continuation-in-part of application No. 09/565,391, which is a continuation-in-part of application No. PCT/US99/26409, said application No. 10/100,683 is a continuation-in-part of application No. PCT/US99/26409, and a continuation-in-part of application No. 09/895,298, filed on Jul. 2, 2001, which is a continuation of application No. 09/591,316, filed on Jun. 9, 2000, which is a continuation-in-part of application No. PCT/US99/29950, filed on Dec. 16, 1999, said application No. 10/100,683 is a continuation-in-part of application No. PCT/US99/29950, and a continuation-in-part of application No. 09/985,153, filed on Nov. 1, 2001, which is a continuation of application No. 09/618,150, filed on Jul. 17, 2000, which is a continuation-in-part of application No. PCT/US00/00903, filed on Jan. 18, 2000, said application No. 10/100,683 is a continuation-in-part of application No. PCT/US00/00903, and a continuation-in-part of application No. 09/997,131, filed on Nov. 30, 2001, which is a continuation of application No. 09/628,508, filed on Jul. 28, 2000, which is a continuation-in-part of application No. PCT/US00/03062, filed on Feb. 8, 2000, said application No. 10/100,683 is a continuation-in-part of application No. PCT/US00/06062, and a continuation-in-part of application No. 10/050,882, filed on Jan. 18, 2002, which is a continuation of application No. 09/661,453, filed on Sep. 13, 2000, which is a continuation-in-part of application No. PCT/US00/06783, filed on Mar. 16, 2000, said application No. 10/100,683 is a continuation-in-part of application No. 09/661,453, which is a continuation-in-part of application No.

PCT/US00/06783, said application No. 10/100,683 is a continuation-in-part of application No. PCT/US00/06783, and a continuation-in-part of application No. 10/050,704, filed on Jan. 18, 2002, which is a continuation of application No. 09/684,524, filed on Oct. 10, 2000, which is a continuation-in-part of application No. PCT/US00/08979, filed on Apr. 6, 2000, said application No. 10/100,683 is a continuation-in-part of application No. 09/684,524, which is a continuation-in-part of application No. PCT/US00/08979, said application No. 10/100,683 is a continuation-in-part of application No. PCT/US00/08979, and a continuation-in-part of application No. 10/042,141, filed on Jan. 11, 2002, which is a continuation of application No. 09/726,643, filed on Dec. 1, 2000, which is a continuation-in-part of application No. PCT/US00/15187, filed on Jun. 2, 2000, said application No. 10/100,683 is a continuation-in-part of application No. 09/726,643, which is a continuation-in-part of application No. PCT/US00/15187, said application No. 10/100,683 is a continuation-in-part of application No. PCT/US00/15187, said application No. 10/100,683 is a continuation-in-part of application No. 09/756,168, filed on Jan. 9, 2001, which is a continuation-in-part of application No. PCT/US00/19735, filed on Jul. 23, 1999, said application No. 10/100,683 is a continuation-in-part of application No. PCT/US00/19735, and a continuation-in-part of application No. 10/060,255, filed on Feb. 1, 2002, which is a continuation of application No. 09/781,417, filed on Feb. 13, 2001, which is a continuation-in-part of application No. PCT/US00/22325, filed on Aug. 16, 2000, said application No. 10/100,683 is a continuation-in-part of application No. 09/781,417, which is a continuation-in-part of application No. PCT/US00/22325, said application No. 10/100,683 is a continuation-in-part of application No. PCT/US00/22325, and a continuation-in-part of application No. 09/789,561, filed on Feb. 22, 2001, which is a continuation-in-part of application No. PCT/US00/24008, filed on Aug. 31, 2000, said application No. 10/100,683 is a continuation-in-part of application No. PCT/US00/24008, and a continuation-in-part of application No. 09/800,729, filed on Mar. 8, 2001, which is a continuation-in-part of application No. PCT/US00/26013, filed on Sep. 22, 2000, said application No. 10/100,683 is a continuation-in-part of application No. PCT/US00/26013, and a continuation-in-part of application No. 09/832,129, filed on Apr. 11, 2001, which is a continuation-in-part of application No. PCT/US00/28664, filed on Oct. 17, 2000, said application No. 10/100,683 is a continuation-in-part of application No. PCT/US00/28664, and a continuation-in-part of application No. PCT/US00/29363, filed on Oct. 25, 2000, and a continuation-in-part of application No. PCT/US00/29360, filed on Oct. 25, 2000, and a continuation-in-part of application No. PCT/US00/29362, filed on Oct. 25, 2000, and a continuation-in-part of application No. PCT/US00/29365, filed on Oct. 25, 2000, and a continuation-in-part of application No. PCT/US00/29364, filed on Oct. 25, 2000, and a continuation-in-part of application No. PCT/US00/30040, filed on Nov. 1, 2000, and a continuation-in-part of application No. PCT/US00/30037, filed on Nov. 1, 2000, and a continuation-in-part of application No. PCT/US00/30045, filed on Nov. 1, 2000, and a continuation-in-part of application No. PCT/US00/30036, filed on Nov. 1, 2000, and a continuation-in-part of application No. PCT/US00/30039, filed on Nov. 1, 2000, and a continuation-in-part of application No. PCT/US00/30654, filed on Nov. 8, 2000, and a continuation-in-part of application No. PCT/US00/30628, filed on Nov. 8, 2000, and a continuation-in-part of application No. PCT/US00/30653, filed on Nov. 8, 2000, and a continuation-in-part of application No. PCT/US00/30629, filed on Nov. 8, 2000, and a continuation-in-part of application No. PCT/US00/30679, filed on Nov. 8, 2000, and a continuation-in-part of application No. PCT/US00/30674, filed on Nov. 8, 2000, and a continuation-in-part of application No. PCT/US00/31162, filed on Nov. 15, 2000, and a continuation-in-part of application No. PCT/US00/31282, filed on Nov. 15, 2000, and a continuation-in-part of application No. PCT/US00/30657, filed on Nov. 8, 2000, and a continuation-in-part of application No. PCT/US01/01396, filed on Jan. 17, 2001, and a continuation-in-part of application No. PCT/US01/01387, filed on Jan. 17, 2001, and a continuation-in-part of application No. PCT/US01/01567, filed on Jan. 17, 2001, and a continuation-in-part of application No. PCT/US01/01431, filed on Jan. 17, 2001, which is a continuation-in-part of application No. 09/915,582, filed on Jul. 27, 2001, said application No. 10/100,683 is a continuation-in-part of application No. PCT/US01/01432, filed on Jan. 17, 2001, and a continuation-in-part of application No. PCT/US01/00544, filed on Jan. 9, 2001, and a continuation-in-part of application No. PCT/US01/01435, filed on Jan. 17, 2001, and a continuation-in-part of application No. PCT/US01/01386, filed on Jan. 17, 2001, and a continuation-in-part of application No. PCT/US01/01565, filed on Jan. 17, 2001, and a continuation-in-part of application No. PCT/US01/01394, filed on Jan. 17, 2001, and a continuation-in-part of application No. PCT/US01/01434, filed on Jan. 17, 2001, and a continuation-in-part of application No. PCT/US01/01397, filed on Jan. 17, 2001, and a continuation-in-part of application No. PCT/US01/01385, filed on Jan. 17, 2001, and a continuation-in-part of application No. PCT/US01/01384, filed on Jan. 17, 2001, and a continuation-in-part of application No. PCT/US01/01383, filed on Jan. 17, 2001, and a continuation-in-part of application No. PCT/US02/05064, filed on Feb. 21, 2002, and a continuation-in-part of application No. PCT/US02/05301, filed on Feb. 21, 2002, application No. 12/753,401, which is a continuation-in-part of application No. 11/689,173, filed on Mar. 21, 2007, which is a continuation of application No. 11/001,793, filed on Dec. 2, 2001, which is a division of application No. 10/100,683, filed on Mar. 19, 2002, which is a continuation-in-part of application No. 09/981,876, filed on Oct. 19, 2001, which is a division of application No. 09/621,011, filed on Jul. 20, 2000, which is a continuation of application No. 09/148,545, filed on Sep. 4, 1998, which is a continuation-in-part of application No. PCT/US98/04482, filed on Mar. 6, 1998, said application No. 10/100,683 is a continuation-in-part of application No. 09/621,011, which is a continuation of application No. 09/148,545, which is a continuation-in-part of application No. PCT/US98/04482, said application No. 10/100,683 is a continuation-in-part of application No. 09/148,545, which is a continuation-in-part of application No. PCT/US98/04482, said application No. 10/100,683 is a continuation-in-part of application No. PCT/US98/04482, and a continuation-in-part of application No. 09/882,171, filed on Jun. 18, 2001, which is a continuation of application No. 09/809,391, filed on Mar. 16, 2001, which is a continuation-in-part of application No. 09/149,476, filed on Sep. 8, 1998, which is a continuation-in-part of application No. PCT/US98/04493, filed on Mar. 6, 1998, said application No. 10/100,683 is a continuation-in-part of application No. 09/809,391, which is a continuation-in-part of application No. 09/149,476, which is a continuation-in-part of application No. PCT/US98/04493, said application No. 10/100,683 is a continuation-in-part of application No. 09/149,476, which is a continuation-in-part of application No. PCT/US98/04493, said application No. 10/100,683 is a continuation-in-part of application No. PCT/US98/04493, and a continuation-in-part of application No. 10/058,993, filed on Jan. 30, 2002, which is a continuation-in-part of application No. 09/852,659, filed on May 11, 2001, which is a continuation-in-part of application No. 09/152,060, filed on Sep. 11, 1998, which is a continuation-in-part of application No. PCT/US98/04858, filed on Mar. 12, 1998, said application No. 10/058,993 is a continuation-in-part of application No. 09/853,161, filed on May 11, 2001, which is a continuation-in-part of application No. 09/152,060, filed on Sep. 11, 1998, which is a continuation-in-part of application No. PCT/US98/04858, filed on Mar. 12, 1998, said application No. 10/058,993 is a continuation-in-part of application No. 09/852,797, which is a continuation-in-part of application No. 09/152,060, which is a continuation-in-part of application No. PCT/US98/04858, said application No. 10/100,683 is a continuation-in-part of application No. 09/852,659, which is a continuation-in-part of application No. 09/152,060, which is a continuation-in-part of application No. PCT/US98/04858, said application No. 10/100,683 is a continuation-in-part of application No. 09/853,161, which is a continuation-in-part of application No. 09/152,060, which is a continuation-in-part of application No. PCT/US98/04858, said application No. 10/100,683 is a continuation-in-part of application No. 09/852,797, which is a continuation-in-part of application No. 09/152,060, which is a continuation-in-part of application No. PCT/US98/04858, said application No. 10/100,683 is a continuation-in-part of application No. 09/152,060, which is a continuation-in-part of application No. PCT/US98/04858, said application No. 10/100,683 is a continuation-in-part of application No. PCT/US98/04858, and a continuation-in-part of application No. 10/059,395, filed on Jan. 31, 2002, which is a division of application No. 09/966,262, filed on Oct. 1, 2001, which is a continuation of application No. 09/154,707, which is a continuation-in-part of application No. PCT/US98/05311, filed on Mar. 19, 1998, said application No. 10/100,683 is a continuation-in-part of application No. 09/984,245, filed on Oct. 29, 2001, which is a division of application No. 09/154,707, which is a continuation-in-part of application No. PCT/US98/05311, said application No. 10/100,683 is a continuation-in-part of application No. 09/983,966, filed on Oct. 26, 2001, which is a division of application No. 09/154,707, which is a continuation-in-part of application No. PCT/US98/05311, said application No. 10/100,683 is a continuation-in-part of application No. 09/966,262, which is a continuation of application No. 09/154,707, which is a continuation-in-part of application No. PCT/US98/05311, said application No. 10/100,683 is a continuation-in-part of application No. 09/154,707, which is a continuation-in-part of application No. PCT/US98/05311, application No. 10/100,683, which is a continuation-in-part of application No. PCT/US98/05311, and a continuation-in-part of application No. 09/814,122, filed on Mar. 22, 2001, which is a continuation of application No. 09/577,145, filed on May 24, 2000, which is a continuation of application No. 09/166,780, filed on Oct. 6, 1998, which is a continuation-in-part of application No. PCT/US98/06801, filed on Apr. 7, 1998, said application No. 10/100,683 is a continuation-in-part of application No. PCT/US98/06801, and a continuation-in-part of application No. PCT/US98/10868, filed on May 28, 1998, and a continuation-in-part of application No. PCT/US98/11422, filed on Jun. 4, 1998, and a continuation-in-part of application No. PCT/US01/05614, filed on Feb. 21, 2001, and a continuation-in-part of application No. PCT/US98/12125, filed on Jun. 11, 1998, and a continuation-in-part of application No. 09/627,081, filed on Jul. 27, 2000, which is a continuation of application No. 09/213,365, filed on Dec. 17, 1998, which is a continuation-in-part of application No. PCT/US98/13608, filed on Jun. 30, 1998, said application No. 10/100,683 is a continuation-in-part of application No. PCT/US98/13608, and a continuation-in-part of application No. 09/984,490, filed on Oct. 30, 2001, which is a division of application No. 09/227,357, filed on Jan. 8, 1999, which is a continuation-in-part of application No. PCT/US98/13684, filed on Jul. 7, 1998, said application No. 10/100,683 is a continuation-in-part of application No. 09/983,802, filed on Oct. 25, 2001, which is a continuation of application No. 09/227,357, which is a continuation-in-part of application No. PCT/US98/13684, said application No. 10/100,683 is a continuation-in-part of application No. 09/973,278, filed on Oct. 10, 2001, which is a continuation-in-part of application No. 09/277,357, filed on Jan. 8, 1999, which is a continuation-in-part of application No. PCT/US98/13684, said application No. 10/100,683 is a continuation-in-part of application No. PCT/US98/13684, and a continuation-in-part of application No. 09/776,724, filed on Feb. 6, 2001, which is a continuation-in-part of application No. 09/669,688, filed on Sep. 26, 2000, which is a continuation of application No. 09/299,982, filed on Jan. 14, 1999, which is a continuation-in-part of application No. PCT/US98/14613, filed on Jul. 15, 1998, said application No. 10/100,683 is a continuation-in-part of application No. 09/669,688, which is a continuation of application No. 09/229,982, which is a continuation-in-part of application No. PCT/US98/14613, said application No. 10/100,683 is a continuation-in-part of application No. 09/229,982, which is a continuation-in-part of application No. PCT/US98/14613, said application No. 10/100,683 is a continuation-in-part of application No. PCT/US98/14613, and a continuation-in-part of application No. 09/820,649, filed on Mar. 30, 2001, which is a continuation of application No. 09/666,984, filed on Sep. 21, 2000, which is a continuation of application No. 09/236,557, filed on Jan. 26, 1999, which is a continuation-in-part of application No. PCT/US98/15949, filed on Jul. 29, 1998, said application No. 10/100,683 is a continuation-in-part of application No. PCT/US98/15949, and a continuation-in-part of application No. 09/969,730, filed on Oct. 4, 2001, which is a continuation-in-part of application No. 09/774,639, filed on Feb. 1, 2001, which is a continuation of application No. 09/244,112, filed on Feb. 4, 1999, which is a continuation-in-part of application No. PCT/US98/16235, filed on Aug. 4, 1998, which is a continuation-in-part of application No. 09/774,639, which is a continuation of application No. 09/244,112, which is a continuation-in-part of application No. PCT/US98/16235, said application No. 10/100,683 is a continuation-in-part of application No. 09/969,730, filed on Oct. 4, 2001, and a continuation-in-part of application No. PCT/US98/16235, and a continuation-in-part of application No. 09/716,128, filed on Nov. 17, 2000, which is a continuation of application No. 09/251,329, filed on Feb. 17, 1999, which is a continuation-in-part of application No. PCT/US98/17044, filed on Aug. 18, 1998, said application No. 10/100,683 is a continuation-in-part of application No. PCT/US98/17044, and a continuation-in-part of application No. 09/729,835, filed on Dec. 6, 2000, which is a division of application No. 09/257,179, filed on Feb. 25, 1999, which is a continuation-in-part of application No. PCT/US98/17709, filed on Aug. 27, 1998, said application No. 10/100,683 is a continuation-in-part of application No. 09/257,179, which is a continuation-in-part of application No. PCT/US98/17709, said application No. 10/100,683 is a continuation-in-part of application No. PCT/US98/17709, and a continuation-in-part of application No. 10/047,021, filed on Jan. 17, 2002, which is a continuation-in-part of application No. 09/722,329, filed on Nov. 28, 2000, which is a continuation of application No. 09/262,109, filed on Mar. 4, 1999, which is a continuation-in-part of application No. PCT/US98/18360, filed on Sep. 3, 1998, said application No. 10/100,683 is a continuation-in-part of application No. 09/722,329, which is a continuation of application No. 09/262,109, which is a continuation-in-part of application No. PCT/US98/18360, said application No. 10/100,683 is a continuation-in-part of application No. PCT/US02/01109, filed on Jan. 17, 2002, and a continuation-in-part of application No. 09/281,976, filed on Mar. 31, 1999, which is a continuation-in-part of application No. PCT/US98/20775, filed on Oct. 1, 1998, said application No. 10/100,683 is a continuation-in-part of application No. PCT/US98/20775, filed on Oct. 1, 1998, and a continuation-in-part of application No. 09/984,429, filed on Oct. 30, 2001, which is a continuation-in-part of application No. 09/288,143, filed on Apr. 8, 1999, which is a continuation-in-part of application No. PCT/US98/21142, filed on Oct. 8, 1998, said application No. 10/100,683 is a continuation-in-part of application No. 09/288,143, which is a continuation-in-part of application No. PCT/US98/21142, said application No. 10/100,683 is a continuation-in-part of application No. PCT/US98/21142, and a continuation-in-part of application No. 09/296,622, filed on Apr. 23, 1999, which is a continuation-in-part of application No. PCT/US98/22376, filed on Oct. 23, 1998, said application No. 10/100,683 is a continuation-in-part of application No. PCT/US98/22376, and a continuation-in-part of application No. 09/974,879, filed on Oct. 12, 2001, which is a continuation-in-part of application No. 09/818,683, filed on Mar. 28, 2001, which is a continuation of application No. 09/305,736, filed on May 5, 1999, which is a continuation-in-part of application No. PCT/US98/23435, filed on Nov. 4, 1998, said application No. 10/100,683 is a continuation-in-part of application No. 09/818,683, which is a continuation of application No. 09/305,736, filed on May 5, 1999, which is a continuation-in-part of application No. PCT/US98/23435, said application No. 10/100,683 is a continuation-in-part of application No. 09/305,736, which is a continuation-in-part of application No. PCT/US98/23435, said application No. 10/100,683 is a continuation-in-part of application No. PCT/US98/23435, and a continuation-in-part of application No. 09/334,595, filed on Jun. 17, 1999, which is a continuation-in-part of application No. PCT/US98/27059, filed on Dec. 17, 1998, said application No. 10/100,683 is a continuation-in-part of application No. PCT/US98/27059, and a continuation-in-part of application No. 09/938,671, filed on Aug. 27, 2001, which is a continuation of application No. 09/739,907, filed on Dec. 20, 2000, which is a continuation of application No. 09/348,457, filed on Jul. 7, 1999, which is a continuation-in-part of application No. PCT/US99/00108, filed on Jan. 6, 1999, said application No. 10/100,683 is a continuation-in-part of application No. 09/739,907, which is a continuation of application No. 09/348,457, which is a continuation-in-part of application No. PCT/US99/00108, said application No. 10/100,683 is a continuation-in-part of application No. 09/348,457, which is a continuation-in-part of application No.

PCT/US99/00108, said application No. 10/100,683 is a continuation-in-part of application No. 09/348,457, which is a continuation-in-part of application No. PCT/US99/00108, said application No. 10/100,683 is a continuation-in-part of application No. PCT/US99/00108, and a continuation-in-part of application No. 09/949,925, filed on Sep. 12, 2001, which is a continuation-in-part of application No. PCT/US99/01621, filed on Jan. 27, 1999, and a continuation-in-part of application No. 09/363,044, filed on Jul. 29, 1999, which is a continuation-in-part of application No. PCT/US99/01621, said application No. 10/100,683 is a continuation-in-part of application No. 09/813,153, filed on Mar. 21, 2001, which is a continuation of application No. 09/363,044, which is a continuation-in-part of application No. PCT/US99/01621, said application No. 10/100,683 is a continuation-in-part of application No. 09/363,044, which is a continuation-in-part of application No. PCT/US99/01621, said application No. 10/100,683 is a continuation-in-part of application No. PCT/US99/01621, and a continuation-in-part of application No. 10/062,548, filed on Feb. 5, 2002, which is a continuation of application No. 09/369,247, filed on Aug. 5, 1999, which is a continuation-in-part of application No. PCT/US99/02293, filed on Feb. 4, 1999, said application No. 10/100,683 is a continuation-in-part of application No. 09/369,247, which is a continuation-in-part of application No. PCT/US99/02293, said application No. 10/100,683 is a continuation-in-part of application No. PCT/US99/02293, and a continuation-in-part of application No. 09/716,129, filed on Nov. 17, 2000, which is a continuation-in-part of application No. PCT/US99/03939, filed on Feb. 24, 1999, which is a continuation of application No. 09/382,572, filed on Aug. 25, 1999, which is a continuation-in-part of application No. PCT/US99/03939, said application No. 10/100,683 is a continuation-in-part of application No. PCT/US99/03939, and a continuation-in-part of application No. 09/798,889, filed on Mar. 6, 2001, which is a continuation of application No. 09/393,022, filed on Sep. 9, 1999, which is a continuation-in-part of application No. PCT/US99/05721, filed on Mar. 11, 1999, said application No. 10/100,683 is a continuation-in-part of application No. PCT/US99/05721, and a continuation-in-part of application No. 09/397,945, filed on Sep. 17, 1999, which is a continuation-in-part of application No. PCT/US99/05804, filed on Mar. 18, 1999, said application No. 10/100,683 is a continuation-in-part of application No. PCT/US99/05804, and a continuation-in-part of application No. 09/948,783, filed on Sep. 10, 2001, which is a continuation-in-part of application No. 09/892,877, filed on Jun. 28, 2001, which is a continuation of application No. 09/437,658, filed on Nov. 10, 1999, which is a continuation-in-part of application No. PCT/US99/09847, filed on May 6, 1999, said application No. 10/100,683 is a continuation-in-part of application No. 09/892,877, which is a continuation of application No. 09/437,658, which is a continuation-in-part of application No. PCT/US99/09847, said application No. 10/100,683 is a continuation-in-part of application No. PCT/US99/09847, and a continuation-in-part of application No. 10/050,873, filed on Jan. 18, 2002, which is a continuation-in-part of application No. 09/461,325, filed on Dec. 14, 1999, which is a continuation-in-part of application No. PCT/US99/13418, filed on Jun. 15, 1999, said application No. 10/100,683 is a continuation-in-part of application No. 10/012,542, filed on Dec. 12, 2001, and a division of application No. 09/461,325, which is a continuation-in-part of application No. PCT/US99/13418, said application No. 10/100,683 is a continuation-in-part of application No. 09/461,325, which is a continuation-in-part of application No. PCT/US99/13418, said application No. 10/100,683 is a continuation-in-part of application No. PCT/US99/13418, and a continuation-in-part of application No. 09/984,271, filed on Oct. 29, 2001, which is a division of application No. 09/482,273, filed on Jan. 13, 2000, which is a continuation-in-part of application No. PCT/US99/15849, filed on Jul. 14, 1999, said application No. 10/100,683 is a continuation-in-part of application No. 09/984,276, filed on Oct. 29, 2001, which is a division of application No. 09/482,273, filed on Jan. 13, 2000, which is a continuation-in-part of application No. PCT/US99/15849, said application No. 10/100,683 is a continuation-in-part of application No. 09/482,273, which is a continuation-in-part of application No. PCT/US99/15849, said application No. 10/100,683 is a continuation-in-part of application No. PCT/US99/15849, and a continuation-in-part of application No. PCT/US01/29871, filed on Sep. 24, 2001, which is a continuation-in-part of application No. PCT/US01/00911, filed on Jan. 12, 2001, said application No. 10/100,683 is a continuation-in-part of application No. PCT/US01/00911, filed on Jan. 12, 2001, which is a continuation-in-part of application No. 09/482,273, said application No. 10/100,683 is a continuation-in-part of application No. 09/489,847, filed on Jan. 24, 2000, which is a continuation-in-part of application No. PCT/US99/17130, filed on Jul. 29, 1999, said application No. 10/100,683 is a continuation-in-part of application No. PCT/US99/17130, and a continuation-in-part of application No. 10/054,988, filed on Jan. 25, 2002, which is a continuation of application No. 09/904,615, filed on Jul. 16, 2001, which is a continuation of application No. 09/739,254, filed on Dec. 19, 2000, which is a continuation of application No. 09/511,554, filed on Feb. 23, 2000, which is a continuation-in-part of application No. PCT/US99/19330, filed on Aug. 24, 1999, said application No. 10/100,683 is a continuation-in-part of application No. 09/904,615, which is a continuation of application No. 09/739,254, which is a continuation of application No. 09/511,554, which is a continuation-in-part of application No. PCT/US99/19330, said application No. 10/100,683 is a continuation-in-part of application No. PCT/US99/19330, and a continuation-in-part of application No. 09/820,893, filed on Mar. 30, 2001, which is a continuation of application No. 09/531,119, filed on Mar. 20, 2000, which is a continuation-in-part of application No. PCT/US99/22012, filed on Sep. 22, 1999, said application No. 10/100,683 is a continuation-in-part of application No. PCT/US99/22012, and a continuation-in-part of application No. 09/948,820, filed on Sep. 10, 2001, which is a continuation of application No. 09/565,391, filed on May 5, 2000, which is a continuation-in-part of application No. PCT/US99/26409, filed on Nov. 9, 1999, said application No. 10/100,683 is a continuation-in-part of application No. 09/565,391, which is a continuation-in-part of application No. PCT/US99/26409, said application No. 10/100,683 is a continuation-in-part of application No. PCT/US99/26409, and a continuation-in-part of application No. 09/895,298, filed on Jul. 2, 2001, which is a continuation of application No. 09/591,316, filed on Jun. 9, 2000, which is a continuation-in-part of application No. PCT/US99/29950, filed on Dec. 16, 1999, said application No. 10/100,683 is a continuation-in-part of application No. PCT/US99/29950, and a continuation-in-part of application No. 09/985,153, filed on Nov. 1, 2001, which is a continuation of application No. 09/618,150, filed on Jul. 17, 2000, which is a continuation-in-part of application No. PCT/US00/00903, filed on Jan. 18, 2000, said application No. 10/100,683 is a continuation-in-part of application No. PCT/US00/00903, and a continuation-in-part of application No. 09/977,131, filed on Nov. 30, 2001, which is a continuation of application No. 09/628,508, filed on Jul. 28, 2000, which is a continuation-in-part of application No. PCT/US00/03062, filed on Feb. 8, 2000, said application No. 10/100,683 is a continuation-in-part of application No. PCT/US00/03062, and a continuation-in-part of application No. 09/997,131, which is a continuation of application No. 09/628,508, which is a continuation-in-part of application No. PCT/US00/03062, said application No. 10/100,683 is a continuation-in-part of application No. PCT/US00/03062, and a continuation-in-part of application No. 10/050,882, filed on Jan. 18, 2002, which is a continuation of application No. 09/661,453, filed on Sep. 13, 2000, which is a continuation-in-part of application No. PCT/US00/06783, filed on Mar. 16, 2000, said application No. 10/100,683 is a continuation-in-part of application No. 09/661,453, which is a continuation-in-part of application No. PCT/US00/06783, said application No. 10/100,683 is a continuation-in-part of application No. PCT/US00/06783, and a continuation-in-part of application No. 10/050,704, filed on Jan. 18, 2002, which is a continuation of application No. 09/684,524, filed on Oct. 10, 2000, which is a continuation-in-part of application No. PCT/US00/08979, filed on Apr. 6, 2000, said application No. 10/100,683 is a continuation-in-part of application No. 09/684,524, which is a continuation-in-part of application No. PCT/US00/08979, said application No. 10/100,683 is a continuation-in-part of application No. PCT/US00/08979, and a continuation-in-part of application No. 10/042,141, filed on Jan. 11, 2002, which is a continuation of application No. 09/726,643, filed on Dec. 1, 2000, which is a continuation-in-part of application No. PCT/US00/15187, filed on Jun. 2, 2000, said application No. 10/100,683 is a continuation-in-part of application No. 09/726,643, which is a continuation-in-part of application No. PCT/US00/15187, said application No. 10/100,683 is a continuation-in-part of application No. PCT/US00/15187, and a continuation-in-part of application No. 09/756,168, filed on Jan. 9, 2001, which is a continuation-in-part of application No. PCT/US00/19735, filed on Jul. 23, 1999, said application No. 10/100,683 is a continuation-in-part of application No. PCT/US00/19735, and a continuation-in-part of application No. 10/060,255, filed on Feb. 1, 2002, which is a continuation of application No. 09/781,417, filed on Feb. 13, 2001, which is a continuation-in-part of application No. PCT/US00/22325, filed on Aug. 16, 2000, said application No. 10/100,683 is a continuation-in-part of application No. 09/781,417, which is a continuation-in-part of application No. PCT/US00/22325, said application No. 10/100,683 is a continuation-in-part of application No. PCT/US00/22325, and a continuation-in-part of application No. 09/789,561, filed on Feb. 22, 2001, which is a continuation-in-part of application No. PCT/US00/24008, filed on Aug. 31, 2000, said application No. 10/100,683 is a continuation-in-part of application No. PCT/US00/24008, and a continuation-in-part of application No. 09/800,729, filed on Mar. 8, 2001, which is a continuation-in-part of application No. PCT/US00/26013, filed on Sep. 22, 2000, said application No. 10/100,683 is a continuation-in-part of application No. PCT/US00/26013, and a continuation-in-part of application No. 09/832,129, filed on Apr. 11, 2001, which is a continuation-in-part of application No. PCT/US00/28664, filed on Oct. 17, 2000, said application No. 10/100,683 is a continuation-in-part of application No. PCT/US00/28664, and a continuation-in-part of application No. PCT/US00/29363, filed on Oct. 25, 2000, and a continuation-in-part of application No. PCT/US00/29360, filed on Oct. 25, 2000, and a continuation-in-part of application No. PCT/US00/29362, filed on Oct. 25, 2000, and a continuation-in-part of application No. PCT/US00/29365, filed on Oct. 25, 2000, and a continuation-in-part of application No. PCT/US00/29364, filed on Oct. 25, 2000, and a continuation-in-part of application No. PCT/US00/30040, filed on Nov. 1, 2000, and a continuation-in-part of application No. PCT/US00/30037, filed on Nov. 1, 2000, and a continuation-in-part of application No. PCT/US00/30045, filed on Nov. 1, 2000, and a continuation-in-part of application No. PCT/US00/30036, filed on Nov. 1, 2000, and a continuation-in-part of application No. PCT/US00/30039, filed on Nov. 1, 2000, and a continuation-in-part of application No. PCT/US00/30654, filed on Nov. 8, 2000, and a continuation-in-part of application No. PCT/US00/30628, filed on Nov. 8, 2000, and a continuation-in-part of application No. PCT/US00/30653, filed on Nov. 8, 2000, and a continuation-in-part of application No. PCT/US00/30629, filed on Nov. 8, 2000, and a continuation-in-part of application No. PCT/US00/30679, filed on Nov. 8, 2000, and a continuation-in-part of application No.

PCT/US00/30674, filed on Nov. 8, 2000, and a continuation-in-part of application No. PCT/US00/31162, filed on Nov. 15, 2000, and a continuation-in-part of application No. PCT/US00/31282, filed on Nov. 15, 2000, and a continuation-in-part of application No. PCT/US00/30657, filed on Nov. 8, 2000, and a continuation-in-part of application No. PCT/US01/01396, filed on Jan. 17, 2001, and a continuation-in-part of application No. PCT/US01/01387, filed on Jan. 17, 2001, and a continuation-in-part of application No. PCT/US01/01567, filed on Jan. 17, 2001, and a continuation-in-part of application No. PCT/US01/01431, filed on Jan. 17, 2001, which is a continuation-in-part of application No. 09/915,582, filed on Jul. 27, 2001, said application No. 10/100,683 is a continuation-in-part of application No. PCT/US01/01432, filed on Jan. 17, 2001, and a continuation-in-part of application No. PCT/US01/00544, filed on Jan. 9, 2001, and a continuation-in-part of application No. PCT/US01/01435, filed on Jan. 17, 2001, and a continuation-in-part of application No. PCT/US01/01386, filed on Jan. 17, 2001, and a continuation-in-part of application No. PCT/US01/01565, filed on Jan. 17, 2001, and a continuation-in-part of application No. PCT/US01/01394, filed on Jan. 17, 2001, and a continuation-in-part of application No. PCT/US01/01434, filed on Jan. 17, 2001, and a continuation-in-part of application No. PCT/US01/01397, filed on Jan. 17, 2001, and a continuation-in-part of application No. PCT/US01/01385, filed on Jan. 17, 2001, and a continuation-in-part of application No. PCT/US01/01384, filed on Jan. 17, 2001, and a continuation-in-part of application No. PCT/US01/01383, filed on Jan. 17, 2001, and a continuation-in-part of application No. PCT/US02/05064, filed on Feb. 21, 2002, and a continuation-in-part of application No. PCT/US02/05301, filed on Feb. 21, 2002, said application No. 12/753,401 is a continuation-in-part of application No. 11/968,925, filed on Jan. 3, 2008, which is a division of application No. 10/644,765, filed on Aug. 21, 2003, which is a continuation of application No. PCT/US02/05301, application No. 12/753,401, which is a continuation-in-part of application No. 12/538,668, filed on Aug. 10, 2009, which is a continuation of application No. 11/240,769, filed on Oct. 3, 2005, which is a continuation of application No. 09/997,131, filed on Nov. 30, 2001, which is a continuation of application No. 09/628,508, filed on Jul. 28, 2000, which is a continuation-in-part of application No. PCT/US00/03062, filed on Feb. 8, 2000, said application No. 12/753,401 is a continuation-in-part of application No. 11/777,133, filed on Jul. 12, 2007, which is a continuation of application No. 11/229,769, filed on Sep. 20, 2005, which is a continuation of application No. 10/233,453, filed on Sep. 4, 2002, which is a division of application No. 09/489,847, filed on Jan. 24, 2000, which is a continuation-in-part of application No. PCT/US99/17130, filed on Jul. 29, 1999, application No. 12/753,401, which is a continuation-in-part of application No. 12/268,263, filed on Nov. 10, 2008, which is a division of application No. 11/375,555, filed on Mar. 15, 2006, which is a continuation-in-part of application No. 10/103,295, filed on Mar. 22, 2002, which is a continuation-in-part of application No. PCT/US01/00911, filed on Jan. 12, 2001, and a continuation-in-part of application No. PCT/US01/29871, filed on Sep. 24, 2001, and a continuation-in-part of application No. 09/482,273, filed on Jan. 13, 2000, which is a continuation-in-part of application No. PCT/US99/15849, filed on Jul. 14, 1999, application No. 12/753,401, which is a continuation-in-part of application No. 11/760,578, filed on Jun. 8, 2007, which is a continuation of application No. 10/886,642, filed on Jul. 9, 2004, which is a continuation of application No. 10/050,873, filed on Jan. 18, 2002, which is a continuation-in-part of application No. 09/461,325, filed on Dec. 14, 1999, which is a continuation-in-part of application No. PCT/US99/13418, filed on Jun. 15, 1999, application No. 12/753,401, which is a continuation-in-part of application No. 12/274,626, filed on Nov. 20, 2008, which is a division of application No. 11/608,978, filed on Dec. 11, 2006, which is a continuation of application No. 10/918,446, filed on Aug. 16, 2004, which is a division of application No. 10/062,548, filed on Feb. 5, 2002, which is a continuation of application No. 09/369,247, filed on Aug. 5, 1999, which is a continuation-in-part of application No. PCT/US99/02293, filed on Feb. 4, 1999, application No. 12/753,401, which is a continuation-in-part of application No. 11/780,874, filed on Jul. 20, 2007, which is a continuation of application No. 10/935,098, filed on Sep. 8, 2004, which is a continuation of application No. 09/938,671, filed on Aug. 27, 2001, which is a continuation of application No. 09/739,907, filed on Dec. 20, 2000, which is a continuation of application No. 09/348,457, filed on Jul. 7, 1999, application No. 12/753,401, which is a continuation-in-part of application No. 12/325,800, filed on Dec. 1, 2008, which is a division of application No. 11/565,909, filed on Dec. 1, 2006, which is a division of application No. 10/970,493, filed on Oct. 22, 2004, which is a continuation of application No. 10/047,021, filed on Jan. 17, 2002, which is a continuation-in-part of application No. 09/722,329, filed on Nov. 28, 2000, which is a continuation of application No. 09/262,109, filed on Mar. 4, 1999, which is a continuation-in-part of application No. PCT/US98/18360, filed on Sep. 3, 1998, application No. 12/753,401, which is a continuation-in-part of application No. 11/735,351, filed on Apr. 13, 2007, which is a continuation of application No. 10/866,878, filed on Jun. 15, 2004, which is a division of application No. 09/973,278, filed on Oct. 10, 2001, which is a continuation-in-part of application No. 09/227,357, filed on Jan. 8, 1999, which is a continuation-in-part of application No. PCT/US98/13684, filed on Jul. 7, 1998, application No. 12/753,401, which is a continuation-in-part of application No. 11/759,448, filed on Jun. 7, 2007, which is a continuation of application No. 11/229,770, filed on Sep. 20, 2005, which is a continuation of application No. 09/933,767, filed on Aug. 22, 2001, which is a continuation-in-part of application No. PCT/US01/05614, filed on Feb. 21, 2001, and a continuation-in-part of application No. 09/205,258, filed on Dec. 4, 1998, which is a continuation-in-part of application No. PCT/US98/11422, filed on Jun. 4, 1998, application No. 12/753,401, which is a continuation-in-part of application No. 12/324,825, filed on Nov. 26, 2008, which is a continuation of application No. 11/226,657, filed on Sep. 15, 2005, said application No. 10/062,831 is a division of application No. 09/690,454, filed on Oct. 18, 2000, which is a continuation of application No. 09/189,144, filed on Nov. 10, 1998, which is a continuation-in-part of application No. PCT/US98/10868, filed on May 28, 1998, application No. 12/753,401, which is a continuation-in-part of application No. 11/801,040, filed on May 7, 2007, which is a continuation of application No. 11/226,657, filed on Sep. 15, 2005, which is a division of application No. 10/062,831, filed on Feb. 5, 2002, which is a division of application No. 09/690,454, filed on Oct. 18, 2000, which is a continuation of application No. 09/189,144, filed on Nov. 10, 1998, which is a continuation-in-part of application No. PCT/US98/10868, filed on May 28, 1998, application No. 12/753,401, which is a continuation-in-part of application No. 11/744,695, filed on May 4, 2007, which is a continuation of application No. 10/951,993, filed on Sep. 29, 2004, which is a division of application No. 10/058,993, filed on Jan. 30, 2002, which is a continuation-in-part of application No. 09/852,659, filed on May 11, 2001, which is a continuation-in-part of application No. 09/152,060, filed on Sep. 11, 1998, said application No. 10/058,993 is a continuation-in-part of application No. 09/852,797, filed on May 11, 2001, which is a continuation-in-part of application No. 09/152,060, filed on Sep. 11, 1998, said application No. 10/058,993 is a continuation-in-part of application No. 09/853,161, filed on May 11, 2001, which is a continuation-in-part of application No. 09/152,060, filed on Sep. 11, 1998, said application No. 10/058,993 is a continuation-in-part of application No. 09/152,060, which is a continuation-in-part of application No. PCT/US98/04858, filed on Mar. 12, 1998, application No. 12/753,401, which is a continuation-in-part of application No. 11/745,580, filed on May 8, 2007, which is a continuation of application No. 11/114,947, filed on Jun. 6, 2005, which is a continuation-in-part of application No. 10/164,861, filed on Jun. 10, 2002, which is a division of application No. 09/149,476, filed on Sep. 8, 1998, which is a continuation-in-part of application No. PCT/US98/04493, filed on Mar. 6, 1998, said application No. 11/144,947 is a continuation of application No. 09/882,171, filed on Jun. 18, 2001, which is a continuation of application No. 09/809,391, filed on Mar. 16, 2001, application No. 12/753,401, which is a continuation-in-part of application No. 12/264,040, filed on Nov. 3, 2008, which is a division of application No. 11/246,999, filed on Oct. 11, 2005, which is a division of application No. 09/984,130, filed on Oct. 29, 2001, which is a continuation-in-part of application No. 09/836,353, filed on Apr. 18, 2001, which is a continuation-in-part of application No. PCT/US99/25031, filed on Oct. 27, 1999.

(60) Provisional application No. 60/278,650, filed on Mar. 27, 2001, provisional application No. 60/167,061, filed on Nov. 23, 1999, provisional application No. 60/124,146, filed on Mar. 12, 1999, provisional application No. 60/166,989, filed on Nov. 23, 1999, provisional application No. 60/124,093, filed on Mar. 12, 1999, provisional application No. 60/168,654, filed on Dec. 3, 1999, provisional application No. 60/124,145, filed on Mar. 12, 1999, provisional application No. 60/168,661, filed on Dec. 3, 1999, provisional application No. 60/124,099, filed on Mar. 12, 1999, provisional application No. 60/168,622, filed on Dec. 3, 1999, provisional application No. 60/124,096, filed on Mar. 12, 1999, provisional application No. 60/168,663, filed on Dec. 3, 1999, provisional application No. 60/124,143, filed on Mar. 12, 1999, provisional application No. 60/168,665, filed on Dec. 3, 1999, provisional application No. 60/138,598, filed on Jun. 11, 1999, provisional application No. 60/124,095, filed on Mar. 12, 1999, provisional application No. 60/168,662, filed on Dec. 3, 1999, provisional application No. 60/138,626, filed on Jun. 11, 1999, provisional application No. 60/125,360, filed on Mar. 19, 1999, provisional application No. 60/168,667, filed on Dec. 3, 1999, provisional application No. 60/138,574, filed on Jun. 11, 1999, provisional application No. 60/124,144, filed on Mar. 12, 1999, provisional application No. 60/168,666, filed on Dec. 3, 1999, provisional application No. 60/138,597, filed on Jun. 11, 1999, provisional application No. 60/124,142, filed on Mar. 12, 1999, provisional application No. 60/168,664, filed on Dec. 3, 1999, provisional application No. 60/125,359, filed on Mar. 19, 1999, provisional application No. 60/169,906, filed on Dec. 10, 1999, provisional application No. 60/126,051, filed on Mar. 23, 1999, provisional application No. 60/169,980, filed on Dec. 10, 1999, provisional application No. 60/125,362, filed on Mar. 19, 1999, provisional application No. 60/169,910, filed on Dec. 10, 1999, provisional application No. 60/125,361, filed on Mar. 19, 1999, provisional application No. 60/169,936, filed on Dec. 10, 1999, provisional application No. 60/125,812, filed on Mar. 23, 1999, provisional application No. 60/169,916, filed on Dec. 10, 1999, provisional application No. 60/126,054, filed on Mar. 23, 1999, provisional application No. 60/169,946, filed on Dec. 10, 1999, provisional application No. 60/125,815, filed on Mar. 23, 1999, provisional application No. 60/169,616, filed on Dec. 8, 1999, provisional application No. 60/125,358, filed on Mar. 19, 1999, provisional application No. 60/169,623, filed on Dec. 8, 1999, provisional application No. 60/125,364, filed on Mar. 19, 1999, provisional application No. 60/169,617, filed on Dec. 8, 1999, provisional application No. 60/125,363, filed on Mar. 19, 1999, provisional application No. 60/172,410, filed on Dec. 17, 1999, provisional application No. 60/126,502, filed on Mar. 26, 1999, provisional application No. 60/172,409, filed on Dec. 17, 1999, provisional application No. 60/126,503, filed on Mar. 26, 1999, provisional application No. 60/172,412, filed on Dec. 17, 1999, provisional application No. 60/126,505, filed on Mar. 26, 1999, provisional application No. 60/172,408, filed on Dec. 17, 1999, provisional application No. 60/126,594, filed on Mar. 26, 1999, provisional application No. 60/172,413, filed on Dec. 17, 1999, provisional application No. 60/126,511, filed on Mar. 26, 1999, provisional application No. 60/171,549, filed on Dec. 22, 1999, provisional application No. 60/126,595, filed on Mar. 26, 1999, provisional application No. 60/171,504, filed on Dec. 22, 1999, provisional application No. 60/126,598, filed on Mar. 26, 1999, provisional application No. 60/171,552, filed on Dec. 22, 1999, provisional application No. 60/126,596, filed on Mar. 26, 1999, provisional application No. 60/171,550, filed on Dec. 22, 1999, provisional application No. 60/126,600, filed on Mar. 26, 1999, provisional application No. 60/171,551, filed on Dec. 22, 1999, provisional application No. 60/126,501, filed on Mar. 26, 1999, provisional application No. 60/174,847, filed on Jan. 7, 2000, provisional application No. 60/126,504, filed on Mar. 26, 1999, provisional application No. 60/174,853, filed on Jan. 7, 2000, provisional application No. 60/126,509, filed on Mar. 26, 1999, provisional application No. 60/174,852, filed on Jan. 7, 2000, provisional application No. 60/126,506, filed on Mar. 26, 1999, provisional application No. 60/174,850, filed on Jan. 7, 2000, provisional application No. 60/126,510, filed on Mar. 26, 1999, provisional application No. 60/174,851, filed on Jan. 7, 2000, provisional application No. 60/138,573, filed on Jun. 11, 1999, provisional application No. 60/174,871, filed on Jan. 7, 2000, provisional application No. 60/126,508, filed on Mar. 26, 1999, provisional application No. 60/174,872, filed on Jan. 7, 2000, provisional application No. 60/126,507, filed on Mar. 26, 1999, provisional application No. 60/174,877, filed on Jan. 7, 2000, provisional application No. 60/126,597, filed on Mar. 26, 1999, provisional application No. 60/176,064, filed on Jan. 14, 2000, provisional application No. 60/154,373, filed on Sep. 17, 1999, provisional application No. 60/126,601, filed on Mar. 26, 1999, provisional application No. 60/176,063, filed on Jan. 14, 2000, provisional application No. 60/126,602, filed on Mar. 26, 1999, provisional application No. 60/176,052, filed on Jan. 14, 2000, provisional application No. 60/128,695, filed on Apr. 9, 1999, provisional application No. 60/176,069, filed on Jan. 14, 2000, provisional application No. 60/128,696, filed on Apr. 9, 1999, provisional application No. 60/176,068, filed on Jan. 14, 2000, provisional application No. 60/128,703, filed on Apr. 9, 1999, provisional application No. 60/176,929, filed on Jan. 20, 2000, provisional application No. 60/128,697, filed on Apr. 9, 1999, provisional application No. 60/176,926, filed on Jan. 20, 2000, provisional application No. 60/128,698, filed on Apr. 9, 1999, provisional application No. 60/177,050, filed on Jan. 20, 2000, provisional application No. 60/128,699, filed on Apr. 9, 1999, provisional application No. 60/177,166, filed on Jan. 20, 2000, provisional application No. 60/128,701, filed on Apr. 9, 1999, provisional application No. 60/176,930, filed on Jan. 20, 2000, provisional application No. 60/128,700, filed on Apr. 9, 1999, provisional application No. 60/176,931, filed on Jan. 20, 2000, provisional application No. 60/128,694, filed on Apr. 9, 1999, provisional application No. 60/177,049, filed on Jan. 20, 2000, provisional application No. 60/128,702, filed on Apr. 9, 1999, provisional application No. 60/138,629, filed on Jun. 11, 1999, provisional application No. 60/138,628, filed on Jun. 11, 1999, provisional application No. 60/138,631, filed on Jun. 11, 1999, provisional application No. 60/138,632, filed on Jun. 11, 1999, provisional application No. 60/138,599, filed on Jun. 11, 1999, provisional application No. 60/138,572, filed on Jun. 11, 1999, provisional application No. 60/138,625, filed on Jun. 11, 1999, provisional application No. 60/138,633, filed on Jun. 11, 1999, provisional application No. 60/138,630, filed on Jun. 11, 1999, provisional application No. 60/138,627, filed on Jun. 11, 1999, provisional application No. 60/155,808, filed on Sep. 27, 1999, provisional application No. 60/155,804, filed on Sep. 27, 1999, provisional application No. 60/155,807, filed on Sep. 27, 1999, provisional application No. 60/155,805, filed on Sep. 27, 1999, provisional application No. 60/155,806, filed on Sep. 27, 1999, provisional application No. 60/212,142, filed on Jun. 16, 2000, provisional application No. 60/201,194, filed on May 2, 2000, provisional application No. 60/167,061, filed on Nov. 23, 1999, provisional application No. 60/124,146, filed on Mar. 12, 1999, provisional application No. 60/166,989, filed on Nov. 23, 1999, provisional application No. 60/124,093, filed on Mar. 12, 1999, provisional application No. 60/168,654, filed on Dec. 3, 1999, provisional application No. 60/124,145, filed on Mar. 12, 1999, provisional application No. 60/168,661, filed on Dec. 3, 1999, provisional application No. 60/124,099, filed on Mar. 12, 1999, provisional application No. 60/168,622, filed on Dec. 3, 1999, provisional application No. 60/124,096, filed on Mar. 12, 1999, provisional application No. 60/168,663, filed on Dec. 3, 1999, provisional application No. 60/124,143, filed on Mar. 12, 1999, provisional application No. 60/168,665, filed on Dec. 3, 1999, provisional application No. 60/138,598, filed on Jun. 11, 1999, provisional application No. 60/124,095, filed on Mar. 12, 1999, provisional application No. 60/168,662, filed on Dec. 3, 1999, provisional application No. 60/138,626, filed on Jun. 11, 1999, provisional application No. 60/125,360, filed on Mar. 19, 1999, provisional application No. 60/168,667, filed on Dec. 3, 1999, provisional application No. 60/138,574, filed on Jun. 11, 1999, provisional application No. 60/124,144, filed on Mar. 12, 1999, provisional application No. 60/168,666, filed on Dec. 3, 1999, provisional application No. 60/138,597, filed on Jun. 11, 1999, provisional application No. 60/124,142, filed on Mar. 12, 1999, provisional application No. 60/168,664, filed on Dec. 3, 1999, provisional application No. 60/125,359, filed on Mar. 19, 1999, provisional application No. 60/169,906, filed on Dec. 10, 1999, provisional application No. 60/126,051, filed on Mar. 23, 1999, provisional application No. 60/169,980, filed on Dec. 10, 1999, provisional application No. 60/125,362, filed on Mar. 19, 1999, provisional application No. 60/169,910, filed on Dec. 10, 1999, provisional application No. 60/125,361, filed on Mar. 19, 1999, provisional application No. 60/169,936, filed on Dec. 10, 1999, provisional application No. 60/125,812, filed on Mar. 23, 1999, provisional application No. 60/169,916, filed on Dec. 10, 1999, provisional application No. 60/126,054, filed on Mar. 23, 1999, provisional application No. 60/169,946, filed on Dec. 10, 1999, provisional application No. 60/125,815, filed on Mar. 23, 1999, provisional application No. 60/169,616, filed on Dec. 8, 1999, provisional application No. 60/125,358, filed on Mar. 19, 1999, provisional application No. 60/169,623, filed on Dec. 8, 1999, provisional application No. 60/125,364, filed on Mar. 19, 1999, provisional application No. 60/169,617, filed on Dec. 8, 1999, provisional application No. 60/125,363, filed on Mar. 19, 1999, provisional application No. 60/172,410, filed on Dec. 17, 1999, provisional application No. 60/126,502, filed on Mar. 26, 1999, provisional application No. 60/172,409, filed on Dec. 17, 1999, provisional application No. 60/126,503, filed on Mar. 26, 1999, provisional application No. 60/172,412, filed on Dec. 17, 1999, provisional application No. 60/126,505, filed on Mar. 26, 1999, provisional application No. 60/172,408, filed on Dec. 17, 1999, provisional application No. 60/126,594, filed on Mar. 26, 1999, provisional application No. 60/172,413, filed on Dec. 17, 1999, provisional application No. 60/126,511, filed on Mar. 26, 1999, provisional application No. 60/171,549, filed on Dec. 22, 1999, provisional application No. 60/126,595, filed on Mar. 26, 1999, provisional application No. 60/171,504, filed on Dec. 22, 1999, provisional application No. 60/126,598, filed on Mar. 26, 1999, provisional application No. 60/171,552, filed on Dec. 22, 1999, provisional application No. 60/126,596, filed on Mar. 26, 1999, provisional application No. 60/171,550, filed on Dec. 22, 1999, provisional application No. 60/126,600, filed on Mar. 26, 1999, provisional application No. 60/171,551, filed on Dec. 22, 1999, provisional application No. 60/126,501, filed on Mar. 26, 1999, provisional application No. 60/174,847, filed on Jan. 7, 2000, provisional application No. 60/126,504, filed on Mar. 26, 1999, provisional application No. 60/174,853, filed on Jan. 7, 2000, provisional application No. 60/126,509, filed on Mar. 26, 1999, provisional application No. 60/174,852, filed on Jan. 7, 2000, provisional application No. 60/126,506, filed on Mar. 26, 1999, provisional application No. 60/174,850, filed on Jan. 7, 2000, provisional application No. 60/126,510, filed on Mar. 26, 1999, provisional application No. 60/174,851, filed on Jan. 7, 2000, provisional application No. 60/138,573, filed on Jun. 11, 1999, provisional application No. 60/174,871, filed on Jan. 7, 2000, provisional application No. 60/126,508, filed on Mar. 26, 1999, provisional application No. 60/174,872, filed on Jan. 7, 2000, provisional application No. 60/126,507, filed on Mar. 26, 1999, provisional application No. 60/174,877, filed on Jan. 7, 2000, provisional application No. 60/126,597, filed on Mar. 26, 1999, provisional application No. 60/176,064, filed on Jan. 14, 2000, provisional application No. 60/154,373, filed on Sep. 17, 1999, provisional application No. 60/126,601, filed on Mar. 26, 1999, provisional application No. 60/176,063, filed on Jan. 14, 2000, provisional application No. 60/126,602, filed on Mar. 26, 1999, provisional application No. 60/176,052, filed on Jan. 14, 2000, provisional application No. 60/128,695, filed on Apr. 9, 1999, provisional application No. 60/176,069, filed on Jan. 14, 2000, provisional application No. 60/128,696, filed on Apr. 9, 1999, provisional application No. 60/176,068, filed on Jan. 14, 2000, provisional application No. 60/128,703, filed on Apr. 9, 1999, provisional application No. 60/176,929, filed on Jan. 20, 2000, provisional application No. 60/128,697, filed on Apr. 9, 1999, provisional application No. 60/176,926, filed on Jan. 20, 2000, provisional application No. 60/128,698, filed on Apr. 9, 1999, provisional application No. 60/177,050, filed on Jan. 20, 2000, provisional application No. 60/128,699, filed on Apr. 9, 1999, provisional application No. 60/177,166, filed on Jan. 20, 2000, provisional application No. 60/128,701, filed on Apr. 9, 1999, provisional application No. 60/176,930, filed on Jan. 20, 2000, provisional application No. 60/128,700, filed on Apr. 9, 1999, provisional application No. 60/176,931, filed on Jan. 20, 2000, provisional application No. 60/128,694, filed on Apr. 9, 1999, provisional application No. 60/177,049, filed on Jan. 20, 2000, provisional application No. 60/128,702, filed on Apr. 9, 1999, provisional application No. 60/138,629, filed on Jun. 11, 1999, provisional application No. 60/138,628, filed on Jun. 11, 1999, provisional application No. 60/138,631, filed on Jun. 11, 1999, provisional application No. 60/138,632, filed on Jun. 11, 1999, provisional application No. 60/138,599, filed on Jun. 11, 1999, provisional application No. 60/138,572, filed on Jun. 11, 1999, provisional application No. 60/138,625, filed on Jun. 11, 1999, provisional application No. 60/138,633, filed on Jun. 11, 1999, provisional application No. 60/138,630, filed on Jun. 11, 1999, provisional application No. 60/138,627, filed on Jun. 11, 1999, provisional application No. 60/155,808, filed on Sep. 27, 1999, provisional application No. 60/155,804, filed on Sep. 27, 1999, provisional application No. 60/155,807, filed on Sep. 27, 1999, provisional application No. 60/155,805, filed on Sep. 27, 1999, provisional application No. 60/155,806, filed on Sep. 27, 1999, provisional application No. 60/212,142, filed on Jun. 16, 2000, provisional application No. 60/201,194, filed on May 2, 2000, provisional application No. 60/277,340, filed on Mar. 21, 2001, provisional application No. 60/306,171, filed on Jul. 19, 2001, provisional application No. 60/331,287, filed on Nov. 13, 2001, provisional application No. 60/040,162, filed on Mar. 7, 1997, provisional application No. 60/040,333, filed on Mar. 7, 1997, provisional application No. 60/038,621, filed on Mar. 7, 1997, provisional application No. 60/040,161, filed on Mar. 7, 1997, provisional application No. 60/040,626, filed on Mar. 7, 1997, provisional application No. 60/040,334, filed on Mar. 7, 1997, provisional application No. 60/040,336, filed on Mar. 7, 1997, provisional application No. 60/040,163, filed on Mar. 7, 1997, provisional application No. 60/047,615, filed on May 23, 1997, provisional application No. 60/047,600, filed on May 23, 1997, provisional application No. 60/047,597, filed on May 23, 1997, provisional application No. 60/047,502, filed on May 23, 1997, provisional application No. 60/047,633, filed on May 23, 1997, provisional application No. 60/047,583, filed on May 23, 1997, provisional application No. 60/047,617, filed on May 23, 1997, provisional application No. 60/047,618, filed on May 23, 1997, provisional application No. 60/047,503, filed on May 23, 1997, provisional application No. 60/047,592, filed on May 23, 1997, provisional application No. 60/047,581, filed on May 23, 1997, provisional application No. 60/047,584, filed on May 23, 1997, provisional application No. 60/047,500, filed on May 23, 1997, provisional application No. 60/047,587, filed on May 23, 1997, provisional application No. 60/047,492, filed on May 23, 1997, provisional application No. 60/047,598, filed on May 23, 1997, provisional application No. 60/047,613, filed on May 23, 1997, provisional application No. 60/047,582, filed on May 23, 1997, provisional application No. 60/047,596, filed on May 23, 1997, provisional application No. 60/047,612, filed on May 23, 1997, provisional application No. 60/047,632, filed on May 23, 1997, provisional application No. 60/047,601, filed on May 23, 1997, provisional application No. 60/043,580, filed on Apr. 11, 1997, provisional application No. 60/043,568, filed on Apr. 11, 1997, provisional application No. 60/043,314, filed on Apr. 11, 1997, provisional application No. 60/043,659, filed on Apr. 11, 1997, provisional application No. 60/043,311, filed on Apr. 11, 1997, provisional application No. 60/043,671, filed on Apr. 11, 1997, provisional application No. 60/043,674, filed on Apr. 11, 1997, provisional application No. 60/043,669, filed on Apr. 11, 1997, provisional application No. 60/043,312, filed on Apr. 11, 1997, provisional application No. 60/043,313, filed on Apr. 11, 1997, provisional application No. 60/043,672, filed on Apr. 11, 1997, provisional application No. 60/043,315, filed on Apr. 11, 1997, provisional application No. 60/048,974, filed on Jun. 6, 1997, provisional application No. 60/056,886, filed on Aug. 22, 1997, provisional application No. 60/056,877, filed on Aug. 22, 1997, provisional application No. 60/056,889, filed on Aug. 22, 1997, provisional application No. 60/056,893, filed on Aug. 22, 1997, provisional application No. 60/056,630, filed on Aug. 22, 1997, provisional application No. 60/056,878, filed on Aug. 22, 1997, provisional application No. 60/056,662, filed on Aug. 22, 1997, provisional application No. 60/056,872, filed on Aug. 22, 1997, provisional application No. 60/056,882, filed on Aug. 22, 1997, provisional application No. 60/056,637, filed on Aug. 22, 1997, provisional application No. 60/056,903, filed on Aug. 22, 1997, provisional application No. 60/056,888, filed on Aug. 22, 1997, provisional application No. 60/056,879, filed on Aug. 22, 1997, provisional application No. 60/056,880, filed on Aug. 22, 1997, provisional application No. 60/056,894, filed on Aug. 22, 1997, provisional application No. 60/056,911, filed on Aug. 22, 1997, provisional application No. 60/056,636, filed on Aug. 22, 1997, provisional application No. 60/056,874, filed on Aug. 22, 1997, provisional application No. 60/056,910, filed on Aug. 22, 1997, provisional application No. 60/056,864, filed on Aug. 22, 1997, provisional application No. 60/056,631, filed on Aug. 22, 1997, provisional application No. 60/056,845, filed on Aug. 22, 1997, provisional application No. 60/056,892, filed on Aug. 22, 1997, provisional application No. 60/047,595, filed on May 23, 1997, provisional application No. 60/057,761, filed on Sep. 5, 1997, provisional application No. 60/047,599, filed on May 23, 1997, provisional application No. 60/047,588, filed on May 23, 1997, provisional application No. 60/047,585, filed on May 23, 1997, provisional application No. 60/047,586, filed on May 23, 1997, provisional application No. 60/047,590, filed on May 23, 1997, provisional application No. 60/047,594, filed on May 23, 1997, provisional application No. 60/047,589, filed on May 23, 1997, provisional application No. 60/047,593, filed on May 23, 1997, provisional application No. 60/047,614, filed on May 23, 1997, provisional application No. 60/043,578, filed on Apr. 11, 1997, provisional application No. 60/043,576, filed on Apr. 11, 1997, provisional application No. 60/047,501, filed on May 23, 1997, provisional application No. 60/043,670, filed on Apr. 11, 1997, provisional application No. 60/056,632, filed on Aug. 22, 1997, provisional application No. 60/056,664, filed on Aug. 22, 1997, provisional application No. 60/056,876, filed on Aug. 22, 1997, provisional application No. 60/056,881, filed on Aug. 22, 1997, provisional application No. 60/056,909, filed on Aug. 22, 1997, provisional application No. 60/056,875, filed on Aug. 22, 1997, provisional application No. 60/056,862, filed on Aug. 22, 1997, provisional application No. 60/056,887, filed on Aug. 22, 1997, provisional application No. 60/056,908, filed on Aug. 22, 1997, provisional application No. 60/048,964, filed on Jun. 6, 1997, provisional application No. 60/057,650, filed on Sep. 5, 1997, provisional application No. 60/056,884, filed on Aug. 22, 1997, provisional application No. 60/190,068, filed on Mar. 17, 2000, provisional application No. 60/057,669, filed on Sep. 5, 1997, provisional application No. 60/049,610, filed on Mar. 13, 1997, provisional application No. 60/061,060, filed on Oct. 2, 1997, provisional application No. 60/051,926, filed on Jul. 8, 1997, provisional application No. 60/052,874, filed on Jul. 16, 1997, provisional application No. 60/058,785, filed on Sep. 12, 1997, provisional application No. 60/055,724, filed on Aug. 18, 1997, provisional application No. 60/265,583, filed on Feb. 2, 2001, provisional application No. 60/040,762, filed on Mar. 14, 1997, provisional application No. 60/040,710, filed on Mar. 14, 1997, provisional application No. 60/050,934, filed on May 30, 1997, provisional application No. 60/048,100, filed on May 30, 1997, provisional application No. 60/048,357, filed on May 30, 1997, provisional application No. 60/048,189, filed on May 30, 1997, provisional application No. 60/057,765, filed on Sep. 5, 1997, provisional application No. 60/048,970, filed on Jun. 6, 1997, provisional application No. 60/068,368, filed on Dec. 19, 1997, provisional application No. 60/041,277, filed on Mar. 21, 1997, provisional application No. 60/042,344, filed on Mar. 21, 1997, provisional application No. 60/041,276, filed on Mar. 21, 1997, provisional application No. 60/041,281, filed on Mar. 21, 1997, provisional application No. 60/048,094, filed on May 30, 1997, provisional application No. 60/048,350, filed on May 30, 1997, provisional application No. 60/048,188, filed on May 30, 1997, provisional application No. 60/048,135, filed on May 30, 1997, provisional application No. 60/050,937, filed on May 30, 1997, provisional application No. 60/048,187, filed on May 30, 1997, provisional application No. 60/048,099, filed on May 30, 1997, provisional application No. 60/048,352, filed on May 30, 1997, provisional application No. 60/048,186, filed on May 30, 1997, provisional application No. 60/048,069, filed on May 30, 1997, provisional application No. 60/048,095, filed on May 30, 1997, provisional application No. 60/048,131, filed on May 30, 1997, provisional application No. 60/048,096, filed on May 30, 1997, provisional application No. 60/048,355, filed on May 30, 1997, provisional application No. 60/048,160, filed on May 30, 1997, provisional application No. 60/048,351, filed on May 30, 1997, provisional application No. 60/048,154, filed on May 30, 1997, provisional application No. 60/054,804, filed on Aug. 5, 1997, provisional application No. 60/056,370, filed on Aug. 19, 1997, provisional application No. 60/060,862, filed on Oct. 2, 1997, provisional application No. 60/042,726, filed on Apr. 8, 1997, provisional application No. 60/042,727, filed on Apr. 8, 1997, provisional application No. 60/042,728, filed on Apr. 8, 1997, provisional application No. 60/042,754, filed on Apr. 8, 1997, provisional application No. 60/042,825, filed on Apr. 8, 1997, provisional application No. 60/048,068, filed on May 30, 1997, provisional application No. 60/048,070, filed on May 30, 1997, provisional application No. 60/048,184, filed on May 30, 1997, provisional application No. 60/044,039, filed on May 30, 1997, provisional application No. 60/048,093, filed on May 30, 1997, provisional application No. 60/048,190, filed on May 30, 1997, provisional application No. 60/050,935, filed on May 30, 1997, provisional application No. 60/048,101, filed on May 30, 1997, provisional application No. 60/048,356, filed on May 30, 1997, provisional application No. 60/056,250, filed on Aug. 29, 1997, provisional application No. 60/056,296, filed on Aug. 29, 1997, provisional application No. 60/056,293, filed on Aug. 29, 1997, provisional application No. 60/048,885, filed on Jun. 6, 1997, provisional application No. 60/049,375, filed on Jun. 6, 1997, provisional application No. 60/048,881, filed on Jun. 6, 1997, provisional application No. 60/048,880, filed on Jun. 6, 1997, provisional application No. 60/048,896, filed on Jun. 6, 1997, provisional application No. 60/049,020, filed on Jun. 6, 1997, provisional application No. 60/048,876, filed on Jun. 6, 1997, provisional application No. 60/048,895, filed on Jun. 6, 1997, provisional application No. 60/048,884, filed on Jun. 6, 1997, provisional application No. 60/048,894, filed on Jun. 6, 1997, provisional application No. 60/048,971, filed on Jun. 6, 1997, provisional application No. 60/048,964, filed on Jun. 6, 1997, provisional application No. 60/048,882, filed on Jun. 6, 1997, provisional application No. 60/048,899, filed on Jun. 6, 1997, provisional application No. 60/048,893, filed on Jun. 6, 1997, provisional application No. 60/048,900, filed on Jun. 6, 1997, provisional application No. 60/048,901, filed on Jun. 6, 1997, provisional application No. 60/048,892, filed on Jun. 6, 1997, provisional application No. 60/048,915, filed on Jun. 6, 1997, provisional application No. 60/049,019, filed on Jun. 6, 1997, provisional application No. 60/048,970, filed on Jun. 6, 1997, provisional application No. 60/048,972, filed on Jun. 6, 1997, provisional application No. 60/048,916, filed on Jun. 6, 1997, provisional application No. 60/049,373, filed on Jun. 6, 1997, provisional application No. 60/048,875, filed on Jun. 6, 1997, provisional application No. 60/049,374, filed on Jun. 6, 1997, provisional application No. 60/048,917, filed on Jun. 6, 1997, provisional application No. 60/048,949, filed on Jun. 6, 1997, provisional application No. 60/048,974, filed on Jun. 6, 1997, provisional application No. 60/048,883, filed on Jun. 6, 1997, provisional application No. 60/048,897, filed on Jun. 6, 1997, provisional application No. 60/048,898, filed on Jun. 6, 1997, provisional application No. 60/048,962, filed on Jun. 6, 1997, provisional application No. 60/048,963, filed on Jun. 6, 1997, provisional application No. 60/048,877, filed on Jun. 6, 1997, provisional application No. 60/048,878, filed on Jun. 6, 1997, provisional application No. 60/057,645, filed on Sep. 5, 1997, provisional application No. 60/057,642, filed on Sep. 5, 1997, provisional application No. 60/057,668, filed on Sep. 5, 1997, provisional application No. 60/057,635, filed on Sep. 5, 1997, provisional application No. 60/057,627, filed on Sep. 5, 1997, provisional application No. 60/057,667, filed on Sep. 5, 1997, provisional application No. 60/057,666, filed on Sep. 5, 1997, provisional application No. 60/057,764, filed on Sep. 5, 1997, provisional application No. 60/057,643, filed on Sep. 5, 1997, provisional application No. 60/057,769, filed on Sep. 5, 1997, provisional application No. 60/057,763, filed on Sep. 5, 1997, provisional application No. 60/057,650, filed on Sep. 5, 1997, provisional application No. 60/057,584, filed on Sep. 5, 1997, provisional application No. 60/057,647, filed on Sep. 5, 1997, provisional application No. 60/057,661, filed on Sep. 5, 1997, provisional application No. 60/057,662, filed on Sep. 5, 1997, provisional application No. 60/057,646, filed on Sep. 5, 1997, provisional application No. 60/057,654, filed on Sep. 5, 1997, provisional application No. 60/057,651, filed on Sep. 5, 1997, provisional application No. 60/057,644, filed on Sep. 5, 1997, provisional application No. 60/057,765, filed on Sep. 5, 1997, provisional application No. 60/057,762, filed on Sep. 5, 1997, provisional application No. 60/057,775, filed on Sep. 5, 1997, provisional application No. 60/057,648, filed on Sep. 5, 1997, provisional application No. 60/057,774, filed on Sep. 5, 1997, provisional application No. 60/057,649, filed on Sep. 5, 1997, provisional application No. 60/057,770, filed on Sep. 5, 1997, provisional application No. 60/057,771, filed on Sep. 5, 1997, provisional application No. 60/057,761, filed on Sep. 5, 1997, provisional application No. 60/057,760, filed on Sep. 5, 1997, provisional application No. 60/057,776, filed on Sep. 5, 1997, provisional application No. 60/057,778, filed on Sep. 5, 1997, provisional application No. 60/057,629, filed on Sep. 5, 1997, provisional application No. 60/057,628, filed on Sep. 5, 1997, provisional application No. 60/057,777, filed on Sep. 5, 1997, provisional application No. 60/057,634, filed on Sep. 5, 1997, provisional application No. 60/070,923, filed on Dec. 18, 1997, provisional application No. 60/184,836, filed on Feb. 24, 2000, provisional application No. 60/193,170, filed on Mar. 29, 2000, provisional application No. 60/049,547, filed on Jun. 13, 1997, provisional application No. 60/049,548, filed on Jun. 13, 1997, provisional application No. 60/049,549, filed on Jun. 13, 1997, provisional application No. 60/049,550, filed on Jun. 13, 1997, provisional application No. 60/049,566, filed on Jun. 13, 1997, provisional application No. 60/049,606, filed on Jun. 13, 1997, provisional application No. 60/049,607, filed on Jun. 13, 1997, provisional application No. 60/049,608, filed on Jun. 13, 1997, provisional application No. 60/049,609, filed on Jun. 13, 1997, provisional application No. 60/049,610, filed on Jun. 13, 1997, provisional application No. 60/049,611, filed on Jun. 13, 1997, provisional application No. 60/050,901, filed on Jun. 13, 1997, provisional application No. 60/052,989, filed on Jun. 13, 1997, provisional application No. 60/051,919, filed on Jul. 8, 1997, provisional application No. 60/055,984, filed on Aug. 18, 1997, provisional application No. 60/058,665, filed on Sep. 12, 1997, provisional application No. 60/058,668, filed on Sep. 12, 1997, provisional application No. 60/058,669, filed on Sep. 12, 1997, provisional application No. 60/058,750, filed on Sep. 12, 1997, provisional application No. 60/058,971, filed on Sep. 12, 1997, provisional application No. 60/058,972, filed on Sep. 12, 1997, provisional application No. 60/058,975, filed on Sep. 12, 1997, provisional application No. 60/060,834, filed on Oct. 2, 1997, provisional application No. 60/060,841, filed on Oct. 2, 1997, provisional application No. 60/060,844, filed on Oct. 2, 1997, provisional application No. 60/060,865, filed on Oct. 2, 1997, provisional application No. 60/061,059, filed on Oct. 2, 1997, provisional application No. 60/061,060, filed on Oct. 2, 1997, provisional application No. 60/051,480, filed on Jul. 1, 1997, provisional application No. 60/051,381, filed on Jul. 1, 1997, provisional application No. 60/058,663, filed on Sep. 12, 1997, provisional application No. 60/058,598, filed on Sep. 12, 1997, provisional application No. 60/239,899, filed on Oct. 13, 2000, provisional application No. 60/051,926, filed on Jul. 8, 1997, provisional application No. 60/052,793, filed on Jul. 8, 1997, provisional application No. 60/051,925, filed on Jul. 8, 1997, provisional application No. 60/051,929, filed on Jul. 8, 1997, provisional application No. 60/052,803, filed on Jul. 8, 1997, provisional application No. 60/052,732, filed on Jul. 8, 1997, provisional application No. 60/051,931, filed on Jul. 8, 1997, provisional application No. 60/051,932, filed on Jul. 8, 1997, provisional application No. 60/051,916, filed on Jul. 8, 1997, provisional application No. 60/051,930, filed on Jul. 8, 1997, provisional application No. 60/051,918, filed on Jul. 8, 1997, provisional application No. 60/051,920, filed on Jul. 8, 1997, provisional application No. 60/052,733, filed on Jul. 8, 1997, provisional application No. 60/052,795, filed on Jul. 8, 1997, provisional application No. 60/051,919, filed on Jul. 8, 1997, provisional application No. 60/051,928, filed on Jul. 8, 1997, provisional application No. 60/055,722, filed on Aug. 18, 1997, provisional application No. 60/055,723, filed on Aug. 18, 1997, provisional application No. 60/055,948, filed on Aug. 18, 1997, provisional application No. 60/055,949, filed on Aug. 18, 1997, provisional application No. 60/055,953, filed on Aug. 18, 1997, provisional application No. 60/055,950, filed on Aug. 18, 1997, provisional application No. 60/055,947, filed on Aug. 18, 1997, provisional application No. 60/055,964, filed on Aug. 18, 1997, provisional application No. 60/056,360, filed on Aug. 18, 1997, provisional application No. 60/055,684, filed on Aug. 18, 1997, provisional application No. 60/055,984, filed on Aug. 18, 1997, provisional application No. 60/055,954, filed on Aug. 18, 1997, provisional application No. 60/058,785, filed on Sep. 12, 1997, provisional application No. 60/058,664, filed on Sep. 12, 1997, provisional application No. 60/058,660, filed on Sep. 12, 1997, provisional application No. 60/058,661, filed on Sep. 12, 1997, provisional application No. 60/180,909, filed on Feb. 8, 2000, provisional application No. 60/052,661, filed on Jul. 16, 1997, provisional application No. 60/052,872, filed on Jul. 16, 1997, provisional application No. 60/052,871, filed on Jul. 16, 1997, provisional application No. 60/052,874, filed on Jul. 16, 1997, provisional application No. 60/052,873, filed on Jul. 16, 1997, provisional application No. 60/052,870, filed on Jul. 16, 1997, provisional application No. 60/052,875, filed on Jul. 16, 1997, provisional application No. 60/053,440, filed on Jul. 22, 1997, provisional application No. 60/053,441, filed on Jul. 22, 1997, provisional application No. 60/053,442, filed on Jul. 22, 1997, provisional application No. 60/056,359, filed on Aug. 18, 1997, provisional application No. 60/055,725, filed on Aug. 18, 1997, provisional application No. 60/055,985, filed on Aug. 18, 1997, provisional application No. 60/055,952, filed on Aug. 18, 1997, provisional application No. 60/055,989, filed on Aug. 18, 1997, provisional application No. 60/056,361, filed on Aug. 18, 1997, provisional application No. 60/055,726, filed on Aug. 18, 1997, provisional application No. 60/055,724, filed on Aug. 18, 1997, provisional application No. 60/055,946, filed on Aug. 18, 1997, provisional application No. 60/055,683, filed on Aug. 18, 1997, provisional application No. 60/295,558, filed on Jun. 5, 2001, provisional application No. 60/054,212, filed on Jul. 30, 1997, provisional application No. 60/054,209, filed on Jul. 30, 1997, provisional application No. 60/054,234, filed on Jul. 30, 1997, provisional application No. 60/054,218, filed on Jul. 30, 1997, provisional application No. 60/054,214, filed on Jul. 30, 1997, provisional application No. 60/054,236, filed on Jul. 30, 1997, provisional application No. 60/054,215, filed on Jul. 30, 1997, provisional application No. 60/054,211, filed on Jul. 30, 1997, provisional application No. 60/054,217, filed on Jul. 30, 1997, provisional application No. 60/054,213, filed on Jul. 30, 1997, provisional application No. 60/055,968, filed on Aug.

18, 1997, provisional application No. 60/055,969, filed on Aug. 18, 1997, provisional application No. 60/055,972, filed on Aug. 18, 1997, provisional application No. 60/056,561, filed on Aug. 19, 1997, provisional application No. 60/056,534, filed on Aug. 19, 1997, provisional application No. 60/056,729, filed on Aug. 19, 1997, provisional application No. 60/056,543, filed on Aug. 19, 1997, provisional application No. 60/056,727, filed on Aug. 19, 1997, provisional application No. 60/056,554, filed on Aug. 19, 1997, provisional application No. 60/056,730, filed on Aug. 19, 1997, provisional application No. 60/238,291, filed on Oct. 6, 2000, provisional application No. 60/055,386, filed on Aug. 8, 1997, provisional application No. 60/054,807, filed on Aug. 5, 1997, provisional application No. 60/055,312, filed on Aug. 5, 1997, provisional application No. 60/055,309, filed on Aug. 5, 1997, provisional application No. 60/054,798, filed on Aug. 5, 1997, provisional application No. 60/055,310, filed on Aug. 5, 1997, provisional application No. 60/054,806, filed on Aug. 5, 1997, provisional application No. 60/054,809, filed on Aug. 5, 1997, provisional application No. 60/054,804, filed on Aug. 5, 1997, provisional application No. 60/054,803, filed on Aug. 5, 1997, provisional application No. 60/054,808, filed on Aug. 5, 1997, provisional application No. 60/055,311, filed on Aug. 5, 1997, provisional application No. 60/055,986, filed on Aug. 18, 1997, provisional application No. 60/055,970, filed on Aug. 18, 1997, provisional application No. 60/056,563, filed on Aug. 19, 1997, provisional application No. 60/056,557, filed on Aug. 19, 1997, provisional application No. 60/056,731, filed on Aug. 19, 1997, provisional application No. 60/056,365, filed on Aug. 19, 1997, provisional application No. 60/056,367, filed on Aug. 19, 1997, provisional application No. 60/056,370, filed on Aug. 19, 1997, provisional application No. 60/056,364, filed on Aug. 19, 1997, provisional application No. 60/056,366, filed on Aug. 19, 1997, provisional application No. 60/056,732, filed on Aug. 19, 1997, provisional application No. 60/056,371, filed on Aug. 19, 1997, provisional application No. 60/056,555, filed on Aug. 19, 1997, provisional application No. 60/056,556, filed on Aug. 19, 1997, provisional application No. 60/056,535, filed on Aug. 19, 1997, provisional application No. 60/056,629, filed on Aug. 19, 1997, provisional application No. 60/056,369, filed on Aug. 19, 1997, provisional application No. 60/056,628, filed on Aug. 19, 1997, provisional application No. 60/056,728, filed on Aug. 19, 1997, provisional application No. 60/056,368, filed on Aug. 19, 1997, provisional application No. 60/056,726, filed on Aug. 19, 1997, provisional application No. 60/089,510, filed on Jun. 16, 1998, provisional application No. 60/092,956, filed on Jul. 15, 1998, provisional application No. 60/056,270, filed on Aug. 29, 1997, provisional application No. 60/056,271, filed on Aug. 29, 1997, provisional application No. 60/056,247, filed on Aug. 29, 1997, provisional application No. 60/056,073, filed on Aug. 29, 1997, provisional application No. 60/262,066, filed on Jan. 18, 2001, provisional application No. 60/057,626, filed on Sep. 5, 1997, provisional application No. 60/057,663, filed on Sep. 5, 1997, provisional application No. 60/057,669, filed on Sep. 5, 1997, provisional application No. 60/058,667, filed on Sep. 12, 1997, provisional application No. 60/058,974, filed on Sep. 12, 1997, provisional application No. 60/058,973, filed on Sep. 12, 1997, provisional application No. 60/058,666, filed on Sep. 12, 1997, provisional application No. 60/090,112, filed on Jun. 22, 1998, provisional application No. 60/060,837, filed on Oct. 2, 1997, provisional application No. 60/060,862, filed on Oct. 2, 1997, provisional application No. 60/060,839, filed on Oct. 2, 1997, provisional application No. 60/060,866, filed on Oct. 2, 1997, provisional application No. 60/060,843, filed on Oct. 2, 1997, provisional application No. 60/060,836, filed on Oct. 2, 1997, provisional application No. 60/060,838, filed on Oct. 2, 1997, provisional application No. 60/060,874, filed on Oct. 2, 1997, provisional application No. 60/060,833, filed on Oct. 2, 1997, provisional application No. 60/060,884, filed on Oct. 2, 1997, provisional application No. 60/060,880, filed on Oct. 2, 1997, provisional application No. 60/244,591, filed on Nov. 1, 2000, provisional application No. 60/061,463, filed on Oct. 9, 1997, provisional application No. 60/061,529, filed on Oct. 9, 1997, provisional application No. 60/071,498, filed on Oct. 9, 1997, provisional application No. 60/061,527, filed on Oct. 9, 1997, provisional application No. 60/061,536, filed on Oct. 9, 1997, provisional application No. 60/061,532, filed on Oct. 9, 1997, provisional application No. 60/063,099, filed on Oct. 24, 1997, provisional application No. 60/063,088, filed on Oct. 24, 1997, provisional application No. 60/063,100, filed on Oct. 24, 1997, provisional application No. 60/063,387, filed on Oct. 24, 1997, provisional application No. 60/063,148, filed on Oct. 24, 1997, provisional application No. 60/063,386, filed on Oct. 24, 1997, provisional application No. 60/062,784, filed on Oct. 24, 1997, provisional application No. 60/063,091, filed on Oct. 24, 1997, provisional application No. 60/063,090, filed on Oct. 24, 1997, provisional application No. 60/063,089, filed on Oct. 24, 1997, provisional application No. 60/063,092, filed on Oct. 24, 1997, provisional application No. 60/063,111, filed on Oct. 24, 1997, provisional application No. 60/063,101, filed on Oct. 24, 1997, provisional application No. 60/063,109, filed on Oct. 24, 1997, provisional application No. 60/063,110, filed on Oct. 24, 1997, provisional application No. 60/063,098, filed on Oct. 24, 1997, provisional application No. 60/063,097, filed on Oct. 24, 1997, provisional application No. 60/239,893, filed on Oct. 13, 2000, provisional application No. 60/064,911, filed on Nov. 7, 1997, provisional application No. 60/064,912, filed on Nov. 7, 1997, provisional application No. 60/064,983, filed on Nov. 7, 1997, provisional application No. 60/064,900, filed on Nov. 7, 1997, provisional application No. 60/064,988, filed on Nov. 7, 1997, provisional application No. 60/064,987, filed on Nov. 7, 1997, provisional application No. 60/064,908, filed on Nov. 7, 1997, provisional application No. 60/064,984, filed on Nov. 7, 1997, provisional application No. 60/064,985, filed on Nov. 7, 1997, provisional application No. 60/066,094, filed on Nov.

17, 1997, provisional application No. 60/066,100, filed on Nov. 17, 1997, provisional application No. 60/066,089, filed on Nov. 17, 1997, provisional application No. 60/066,095, filed on Nov. 17, 1997, provisional application No. 60/066,090, filed on Nov. 17, 1997, provisional application No. 60/070,923, filed on Dec. 18, 1997, provisional application No. 60/068,007, filed on Dec. 18, 1997, provisional application No. 60/068,057, filed on Dec. 18, 1997, provisional application No. 60/068,006, filed on Dec. 18, 1997, provisional application No. 60/068,369, filed on Dec. 19, 1997, provisional application No. 60/068,367, filed on Dec. 19, 1997, provisional application No. 60/068,368, filed on Dec. 19, 1997, provisional application No. 60/068,169, filed on Dec. 19, 1997, provisional application No. 60/068,053, filed on Dec. 18, 1997, provisional application No. 60/068,064, filed on Dec. 18, 1997, provisional application No. 60/068,054, filed on Dec. 18, 1997, provisional application No. 60/068,008, filed on Dec. 18, 1997, provisional application No. 60/068,365, filed on Dec. 19, 1997, provisional application No. 60/070,704, filed on Jan. 7, 1998, provisional application No. 60/070,658, filed on Jan. 7, 1998, provisional application No. 60/070,692, filed on Jan. 7, 1998, provisional application No. 60/070,657, filed on Jan. 7, 1998, provisional application No. 60/232,150, filed on Sep. 12, 2000, provisional application No. 60/073,170, filed on Jan. 30, 1998, provisional application No. 60/073,167, filed on Jan. 30, 1998, provisional application No. 60/073,165, filed on Jan. 30, 1998, provisional application No. 60/073,164, filed on Jan. 30, 1998, provisional application No. 60/073,162, filed on Jan. 30, 1998, provisional application No. 60/073,161, filed on Jan. 30, 1998, provisional application No. 60/073,160, filed on Jan. 30, 1998, provisional application No. 60/073,159, filed on Jan. 30, 1998, provisional application No. 60/074,118, filed on Feb. 9, 1998, provisional application No. 60/074,157, filed on Feb. 9, 1998, provisional application No. 60/074,037, filed on Feb. 9, 1998, provisional application No. 60/074,141, filed on Feb. 9, 1998, provisional application No. 60/074,341, filed on Feb. 9, 1998, provisional application No. 60/076,053, filed on Feb. 26, 1998, provisional application No. 60/076,051, filed on Feb. 26, 1998, provisional application No. 60/076,054, filed on Feb. 26, 1998, provisional application No. 60/076,052, filed on Feb. 26, 1998, provisional application No. 60/076,057, filed on Feb. 26, 1998, provisional application No. 60/077,714, filed on Mar. 12, 1998, provisional application No. 60/077,686, filed on Mar. 12, 1998, provisional application No. 60/077,687, filed on Mar. 12, 1998, provisional application No. 60/077,696, filed on Mar. 12, 1998, provisional application No. 60/078,566, filed on Mar. 19, 1998, provisional application No. 60/078,576, filed on Mar. 19, 1998, provisional application No. 60/078,573, filed on Mar. 19, 1998, provisional application No. 60/078,574, filed on Mar. 19, 1998, provisional application No. 60/078,579, filed on Mar. 19, 1998, provisional application No. 60/080,314, filed on Apr. 1, 1998, provisional application No. 60/080,312, filed on Apr. 1, 1998, provisional application No. 60/078,578, filed on Mar. 19, 1998, provisional application No. 60/078,581, filed on Mar. 19, 1998, provisional application No. 60/078,577, filed on Mar. 19, 1998, provisional application No. 60/078,563, filed on Mar. 19, 1998, provisional application No. 60/080,313, filed on Apr. 1, 1998, provisional application No. 60/231,846, filed on Sep. 11, 2000, provisional application No. 60/085,093, filed on May 12, 1998, provisional application No. 60/085,094, filed on May 12, 1998, provisional application No. 60/085,105, filed on May 12, 1998, provisional application No. 60/085,180, filed on May 12, 1998, provisional application No. 60/085,927, filed on May 18, 1998, provisional application No. 60/085,906, filed on May 18, 1998, provisional application No. 60/085,920, filed on May 18, 1998, provisional application No. 60/085,924, filed on May 18, 1998, provisional application No. 60/085,922, filed on May 18, 1998, provisional application No. 60/085,923, filed on May 18, 1998, provisional application No. 60/085,921, filed on May 18, 1998, provisional application No. 60/085,925, filed on May 18, 1998, provisional application No. 60/085,928, filed on May 18, 1998, provisional application No. 60/263,681, filed on Jan. 24, 2001, provisional application No. 60/263,230, filed on Jan. 23, 2001, provisional application No. 60/089,507, filed on Jun. 16, 1998, provisional application No. 60/089,508, filed on Jun. 16, 1998, provisional application No. 60/089,509, filed on Jun. 16, 1998, provisional application No. 60/089,510, filed on Jun. 16, 1998, provisional application No. 60/090,112, filed on Jun. 22, 1998, provisional application No. 60/090,113, filed on Jun. 22, 1998, provisional application No. 60/092,921, filed on Jul. 15, 1998, provisional application No. 60/092,922, filed on Jul. 15, 1998, provisional application No. 60/092,956, filed on Jul. 15, 1998, provisional application No. 60/234,925, filed on Sep. 25, 2000, provisional application No. 60/350,898, filed on Jan. 25, 2002, provisional application No. 60/094,657, filed on Jul. 30, 1998, provisional application No. 60/095,486, filed on Aug. 5, 1998, provisional application No. 60/096,319, filed on Aug. 12, 1998, provisional application No. 60/095,454, filed on Aug. 6, 1998, provisional application No. 60/095,455, filed on Aug. 6, 1998, provisional application No. 60/097,917, filed on Aug. 25, 1998, provisional application No. 60/098,634, filed on Aug. 31, 1998, provisional application No. 60/101,546, filed on Sep. 23, 1998, provisional application No. 60/102,895, filed on Oct. 2, 1998, provisional application No. 60/108,207, filed on Nov. 12, 1998, provisional application No. 60/113,006, filed on Dec. 18, 1998, provisional application No. 60/112,809, filed on Dec. 17, 1998, provisional application No. 60/116,330, filed on Jan. 19, 1999, provisional application No. 60/119,468, filed on Feb. 10, 1999, provisional application No. 60/125,055, filed on Mar. 18, 1999, provisional application No. 60/128,693, filed on Apr. 9, 1999, provisional application No. 60/130,991, filed on Apr. 26, 1999, provisional application No. 60/137,725, filed on Jun. 7, 1999, provisional application No. 60/145,220, filed on Jul. 23, 1999, provisional application No. 60/149,182, filed on Aug. 17, 1999, provisional application No. 60/152,315, filed on Sep.

3, 1999, provisional application No. 60/152,317, filed on Sep. 3, 1999, provisional application No. 60/155,709, filed on Sep. 24, 1999, provisional application No. 60/163,085, filed on Nov. 2, 1999, provisional application No. 60/172,411, filed on Dec. 17, 1999, provisional application No. 60/215,139, filed on Jun. 30, 2000, provisional application No. 60/162,239, filed on Oct. 29, 1999, provisional application No. 60/215,138, filed on Jun. 30, 2000, provisional application No. 60/162,211, filed on Oct. 29, 1999, provisional application No. 60/215,131, filed on Jun. 30, 2000, provisional application No. 60/162,240, filed on Oct. 29, 1999, provisional application No. 60/219,666, filed on Jul. 21, 2000, provisional application No. 60/162,237, filed on Oct. 29, 1999, provisional application No. 60/215,134, filed on Jun. 30, 2000, provisional application No. 60/162,238, filed on Oct. 29, 1999, provisional application No. 60/215,130, filed on Jun. 30, 2000, provisional application No. 60/163,580, filed on Nov. 5, 1999, provisional application No. 60/215,137, filed on Jun. 30, 2000, provisional application No. 60/163,577, filed on Nov. 5, 1999, provisional application No. 60/215,133, filed on Jun. 30, 2000, provisional application No. 60/163,581, filed on Nov. 5, 1999, provisional application No. 60/221,366, filed on Jul. 27, 2000, provisional application No. 60/163,576, filed on Nov. 5, 1999, provisional application No. 60/221,367, filed on Jul. 27, 2000, provisional application No. 60/195,296, filed on Apr. 7, 2000, provisional application No. 60/164,344, filed on Nov. 9, 1999, provisional application No. 60/221,142, filed on Jul. 27, 2000, provisional application No. 60/164,835, filed on Nov. 12, 1999, provisional application No. 60/215,140, filed on Jun. 30, 2000, provisional application No. 60/164,744, filed on Nov. 12, 1999, provisional application No. 60/221,193, filed on Jul. 27, 2000, provisional application No. 60/164,735, filed on Nov. 12, 1999, provisional application No. 60/222,904, filed on Aug. 3, 2000, provisional application No. 60/164,825, filed on Nov. 12, 1999, provisional application No. 60/224,007, filed on Aug. 4, 2000, provisional application No. 60/164,834, filed on Nov. 12, 1999, provisional application No. 60/215,128, filed on Jun. 30, 2000, provisional application No. 60/164,750, filed on Nov. 12, 1999, provisional application No. 60/215,136, filed on Jun. 30, 2000, provisional application No. 60/166,415, filed on Nov. 19, 1999, provisional application No. 60/219,665, filed on Jul. 21, 2000, provisional application No. 60/166,414, filed on Nov. 19, 1999, provisional application No. 60/215,132, filed on Jun. 30, 2000, provisional application No. 60/164,731, filed on Nov. 12, 1999, provisional application No. 60/256,968, filed on Dec. 21, 2000, provisional application No. 60/226,280, filed on Aug. 18, 2000, provisional application No. 60/259,803, filed on Jan. 5, 2001, provisional application No. 60/226,380, filed on Aug. 18, 2000, provisional application No. 60/228,084, filed on Aug. 28, 2000, provisional application No. 60/231,968, filed on Sep. 12, 2000, provisional application No. 60/236,326, filed on Sep. 29, 2000, provisional application No. 60/234,211, filed on Sep. 20, 2000, provisional application No. 60/226,282, filed on Aug. 18, 2000, provisional application No. 60/232,104, filed on Sep. 12, 2000, provisional application No. 60/234,210, filed on Sep. 20, 2000, provisional application No. 60/259,805, filed on Jan. 5, 2001, provisional application No. 60/226,278, filed on Aug. 18, 2000, provisional application No. 60/259,678, filed on Jan. 5, 2001, provisional application No. 60/226,279, filed on Aug. 18, 2000, provisional application No. 60/226,281, filed on Aug. 18, 2000, provisional application No. 60/231,969, filed on Sep. 12, 2000, provisional application No. 60/259,516, filed on Jan. 4, 2001, provisional application No. 60/228,086, filed on Aug. 28, 2000, provisional application No. 60/259,804, filed on Jan. 5, 2001, provisional application No. 60/228,083, filed on Aug. 28, 2000, provisional application No. 60/304,444, filed on Jul. 12, 2001, provisional application No. 60/270,658, filed on Feb. 23, 2001, provisional application No. 60/304,417, filed on Jul. 12, 2001, provisional application No. 60/270,625, filed on Feb. 23, 2001, provisional application No. 60/304,121, filed on Jul. 11, 2001, provisional application No. 60/295,869, filed on Jun. 6, 2001, provisional application No. 60/325,209, filed on Sep. 28, 2001, provisional application No. 60/311,085, filed on Aug. 10, 2001, provisional application No. 60/330,629, filed on Oct. 26, 2001, provisional application No. 60/331,046, filed on Nov. 7, 2001, provisional application No. 60/358,554, filed on Feb. 22, 2002, provisional application No. 60/358,714, filed on Feb. 25, 2002.

OTHER PUBLICATIONS

GenBank Accession No. AA282635, NCI-CGAP www.ncbi.nlm.nih.gov/ncicgap (Aug. 13, 1997).
GenBank Accession No. AI625888, NCI-CGAP www.ncbi.nlm.nih.gov/ncicgap (Apr. 22, 1999).
GenBank Accession No. AA044588, Hillier et al. (May 11, 1997).
GenBank Accession No. AA968997, NCI-CGAP www.ncbi.nlm.nih.gov/ncicgap (Jul. 7, 1998).
GenBank Accession No. AA196702, Hillier et al. (Jan. 22, 1997).
GenBank Accession No. AI847620, Bonaldo et al. (Jul. 15, 1999).
GenBank Accession No. AA248976, Liew (Mar. 11, 1997).
GenBank Accession No. AA463820, Hillier et al. (Jun. 10, 1997).
GenBank Accession No. AA442426, Hillier et al. (Jun. 2, 1997).
GenBank Accession No. AA555076, NCI-CGAP www.ncbi.nlm.nih.gov/ncicgap (Sep. 5, 1997).
GenBank Accession No. AA642074, NCI-CGAP www.ncbi.nlm.nih.gov/ncicgap (Oct. 27, 1997).
GenBank Accession No. N71600, Hillier et al. (Apr. 2, 1996).
GenBank Accession No. N32595, Hillier et al. (Jan. 10, 1996).
GenBank Accession No. AA442570, Hillier et al. (Jun. 2, 1997).
GenBank Accession No. AA639694, NCI-CGAP www.ncbi.nlm.nih.gov/ncicgap (Oct. 23, 1997).
GenBank Accession No. AA338949, Adams et al. (Apr. 21, 1997).
GenBank Accession No. AA552323, NCI-CGAP www.ncbi.nlm.nih.gov/ncicgap (Sep. 5, 1997).
GenBank Accession No. R71665, Hillier et al. (created Jun. 5, 1995; updated Mar. 4, 2000).
GenBank Accession No. AA099406, Hillier et al. (created Oct. 29, 1996; updated Mar. 3, 2000).
GenBank Accession No. R71697, Hillier et al. (created Jun. 5, 1995; updated Mar. 4, 2000).
GenBank Accession No. AA099467, Hillier et al. (created Oct. 29, 1996; updated Mar. 3, 2000).
European Search Report for Application No. EP 05 00 4792 completed Jun. 13, 2005.
Alberts et al., *Molecular Biology of the Cell*, 3rd Ed., p. 465 (1994).

Brennan et al., "Cytokine production in culture by cells isolated from the synovial membrane," *J. Autoimmunity*, 2(suppl.):177-186 (Jun. 1989).
Carrère et al., "Immunoreactive pancreatic Reg protein in sera from cystic fibrosis patients with and without pancreatic insufficiency," *Gut.*, 44(4):545-551 (Apr. 1999).
Eriksson et al., "Insulin resistance in type 2 (non-insulin-dependent) diabetic patients and their relatives is not associated with a defect in the expression of the insulin-responsive glucose transporter (GLUT-4) gene in human skeletal muscle," *Diabetologia.*, 35(2):143-47 (Feb. 1992)).
Fu et al., "Translational regulation of human p53 gene expression," *EMBO J.*, 15(16):4392-4401 (Aug. 15, 1996).
Guo et al., "Induction profile of rat organic anion transporting polypeptide 2 (oatp2) by prototypical drug-metabolizing enzyme inducers that activate gene expression through ligand-activated transcription factor pathways," *J. Pharmacol. Exp. Ther.*, 300(1):206-212 (Jan. 2002).
Gura, T., "Systems for identifying new drugs are often faulty," *Science*, 278:1041-1042 (Nov. 7, 1997).
Hell et al., "Hodgkin cells accumulate mRNA for bcl-2," *Laboratory Investigation*, 73(4):492-496 (Oct. 1995).
Jang et al., "An examination of the effects of hypoxia, acidosis, and glucose starvation on the expression of metastasis-associated genes in murine tumor cells," *Clinical Exp. Metastasis*, 15(5):469-483(Sep. 1997).
McClean et al., "Evidence of post-translational regulation of P-glycoprotein associated with the expression of a distinctive multiple drug-resistant phenotype in Chinese hamster ovary cells", *Eur. J. of Cancer*, 29A:2243-2248 (1993).
Shantz et al., "Translational regulation of ornithine decarboxylase and other enzymes of the polyamine pathway", *Int. J. of Biochem. and Cell Biol.*, 31:107-122 (1999).
Powell et al., "Expression of cytochrome P4502E1 in human liver: assessment by mRNA, genotype and phenotype," *Pharmacogenetics*, 8:411-421 (1998).
Vallejo et al., "Evidence of tissue-specific, post-transcriptional regulation of NRF-2 expression," *Biochimie*, 82(12):1129-1133 (Dec. 2000).
White et al., "Antibody-targeted immunotherapy for treatment of malignancy," *Ann. Rev. Med.*, 52:125-145 (2001).
Zimmer, D.B., "Examination of the calcium-modulated protein S100 alpha and its target proteins in adult and developing skeletal muscle," *Cell Motility and the Cytoskeleton*, 20:325-337 (1991).
Bowie et al., "Deciphering the message in protein sequences: tolerance to amino acid substitutions," *Science*, 247(4948):1306-1310 (Mar. 16, 1990).
Boyd, N. F., The Basic Science of Oncology, McGraw-Hill, Inc., p. 379 (1992).
Burgess et al., "Possible dissociation of the heparin-binding and mitogenic activities of heparin-binding (acidic fibroblast) growth factor-1 from its receptor-binding activities by site-directed mutagenesis of a single lysine residue," *J Cell Bio.*, 111(5 Pt. 1):2129-2138 (Nov. 1990).
GenBank Accession No. AA366394/EST77338, Adams et al. (Apr. 21, 1997).
Greenbaum et al., "Comparing protein abundance and mRNA expression levels on a genomic scale," *Genome Biology*, 4(9):117.1-117.8 (2003).
Jansen et al., "Translational control of gene expression," *Pediatric Res.*, 37(6):681-686 (Jun. 1995).
Lazar et al., "Transforming growth factor alpha: mutation of aspartic acid 47 and leucine 48 results in different biological activities," *Molecular and Cellular Biology*, 8(3):1247-1252 (Mar. 1988).
Sambrook et al., A Laboratory Manual, $2^{nd}$ Ed., Sambrook, et al., Eds., Cold Spring Harbor Laboratory Press, p. 8.6-8.7 (1989).
Scott et al., "The Pendred syndrome gene encodes a chloride-iodide transport protein," *Nat. Genet.*, 21(4):440-443 (Apr. 1999).
Database Genseq, Accession No. AEL28498, also referred to as Sequence Alignment reference "U" by the Examiner in a Notice of References Office Action dated Jan. 11, 2007 in U.S. Appl. No. 11/002,756.
Anderson et al., "A comparison of selected mRNA and protein abundances in human liver," *Electrophoresis*, 18(3-4):533-537 (Mar.-Apr. 1997).
Gygi et al., "Correlation between protein and mRNA abundance in yeast," *Mol. Cell. Biol.*, 19(3):1720-1730 (Mar. 1999).
Anisowicz et al., "A Novel Protease Homolog Differentially Expressed in Breast and Ovarian Cancer," *Mol. Med.*, 2(5):624-636 (Sep. 1996).
Barton et al., "Protein sequence alignment and database scanning", Protein Structure Prediction, A Practical Approach, IRL Press at Oxford University Press, Oxford, UK, pp. 31-63 (1996).
Clark et al. "The potential role for prolactin-inducible protein (PIP) as a marker of human breast cancer micrometastasis" *Brit. J. Cancer*, 81(6):1002-1008 (1999).
desJardins et al, "Prediction of enzyme classification from protein sequence without the use of sequence similarity," *Amer. Assoc. Artific. Intell.* pp. 92-99 (1997).
Everett et al., "Pendred Syndrome is Caused by Mutations in a Putative Sulphate Transporter Gene (PDS)," *Nat. Genet.*, 17:411-422 (1997).
Ferrari et al., "Prospective Analysis of Prostate-Specific Markers in Pelvic Lymph Nodes of Patients With High-Risk Prostate Cancer" *J. Natl. Cancer Inst.*, 89(20):1498-1504 (Oct. 15, 1997).
George et al., "Current Methods in Sequence Comparison and Analysis", Macromolecular Sequencing and Synthesis, Selected Methods and Applications, D.H. Schlesinger (ed.) Alan R. Liss, Inc., New York, NY, pp. 127-149 (1988).
Hammond et al., "Issues and Barriers to Development of Clinically Useful Tumor Markers: A Development Pathway Proposal," *Semin. Oncol.*, 29(3):213-221 (2002).
Haynes et al., "Proteome analysis: Biological assay or data archive?" *Electrophoresis*, 19:1862-1871 (1998).
Holm, L., "Unification of protein families," *Curr. Opin. Struct. Biol.*, 8:372-379 (1998).
Jacobs et al., "A Novel Method for Isolating Eukaryotic cDNA Clones Encoding Secreted Proteins", *J. Cell. Biochem. Suppl.* abstract No. C1-207 (1995).
Jacobs et al., "A genetic selection for isolating cDNAs encoding secreted proteins," *Gene*, 198:289-296 (1997).
Kaufman et al., "Transgenic analysis of a 100-kb human B-globulin cluster-containing DNA fragment propagated as a bacterial artificial chromosome," *Blood* 94(9):3178-3184 (1999).
Ngo et al., "Computational Complexity, Protein Structure Prediction, and the Levinthal Paradox," in Merz and Le Grand (Eds.), The Protein Folding Problem and Tertiary Structure Prediction, Birkhauser Boston, pp. 491-495 (1994).
Palù et al., "In pursuit of new developments for gene therapy of human diseases," *J. Biotech.* 68:1-13 (1999).
Pennica et al., "*WISP* genes are members of the connective tissue growth factor family that are up-regulated in Wnt-1-transformed cells and aberrantly expressed in human colon tumors," *Proc. Natl. Acad. Sci. USA*, 95:14717-14722 (Dec. 1998).
Phillips, A.J., "The challenge of gene therapy and DNA delivery," *J. Pharm. Pharmacol.*, 53:1169-1174 (2001).
Roget's International Thesaurus, Third Ed., Thomas Y. Crowell Co., 1962, p. 65.
Seffernick et al., "Melamine Deaminase and Atrazine Chlorohydrolase: 98 Percent Identical but Functionally Different," *J. Bacteriol.*, 183(8):2405-2410 (Apr. 2001).
Suzuki et al., An Introduction to Genetic Analysis, Third Edition, W.H. Freeman and Company, New York, NY, pp. 421-423 (1986).
Vukicevic et al., "Induction of nephrogenic mesenchyme by osteogenic protein 1 (bone morphogenetic protein 7)," *Proc. Natl. Acad. Sci. USA*, 93:9021-9026 (Aug. 1996).
Wang et al., "Rapid analysis of gene expression (RAGE) facilitates universal expression profiling," *Nucl. Acids Res.*, 27(23):4609-4618 (1999).
Wells, J.A., "Additivity of Mutational Effects in Proteins," *Biochemistry*, 29(37):8509-8517 (1990).
Witkowski et al., "Conversion of Beta-Ketoacyl Synthase to a Malonyl Decarboxylase by Replacement of the Active-Site Cysteine with Glutamine," *Biochemistry*, 38:11643-11650 (1999).

"Blood Dendritic Cell Enumeration" Kit Insert. Miltenyi Biotec. (May 27, 2008).

Caillou et al., "Expression of Reduced Nicotinamide Adenine Dinucleotide Phosphate Oxidase (*ThoX, LNOX, Duox*) Genes and Proteins in Human Thyroid Tissues," *J. Clin. Endocrinol. Metab*., 86(7):3351-3358 (Jul. 2001).

Fu et al., "Dynamics of DNA-tracking by two sliding-clamp proteins," *EMBO J*., 15(16): 4414-4422 (Aug. 15, 1996).

Hurchla et al., "B and T Lymphocyte Attenuator Exhibits Structural and Expression Polymorphisms and Is Highly Induced in Anergic $CD4^+$ T Cells," *J. Immunol*., 174:3377-3385 (2005).

Maida et al., "Ovarian endometrioid adenocarcinoma with ectopic production of alpha-fetoprotein," *Gynecol. Oncol*., 71(1):133-136 (Oct. 1998).

Old, R.W. and Primrose, Principles of Gene Manipulation, An Introduction to Genetic Engineering, Blackwell Scientific Publications, Osney Mead, Oxford, pp. 122-123 (1989).

Truong et al., "Combined Coinhibitory and Costimulatory Modulation with Anti-BTLA and CTLA4Ig Facilitates Tolerance in Murine Islet Allografts," *Am. J. Transplant*., 7:2663-2674 (2007).

Yerushalmi et al., "ERGL, a novel gene related to ERGIC-53 that is highly expressed in normal and neoplastic prostate and several other tissues," *Gene*, 265(1-2):55-60 (Mar. 7, 2001).

Steinman, R. "The dendritic cell system and its role in immunogenicity" *Annu. Rev. Immunol*. 9:271-296 (1991).

Requirement for Restriction issued in U.S. Appl. No. 11/002,755 dated Sep. 11, 2006.

Non-Final Rejection issued in U.S. Appl. No. 11/002,755 dated May 15, 2007.

Final Rejection issued in U.S. Appl. No. 11/002,755 dated Nov. 28, 2007.

Requirement for Restriction issued in U.S. Appl. No. 11/002,755 dated Aug. 11, 2008.

Final Rejection issued in U.S. Appl. No. 11/002,755 dated Jan. 30, 2009.

```
  1  GGCACGAGGTGCACAGGAAGGATGAGGAAGACCAGGCTCTGGGGGCTGCTGTGGATGCTC   60
  1                      M  R  K  T  R  L  W  G  L  L  W  M  L    13

 61  TTTGTCTCAGAACTCCGAGCTGCAACTAAATTAACTGAGGAAAAGTATGAACTGAAAGAG  120
 14  F  V  S  E  L  R  A  A  T  K  L  T  E  E  K  Y  E  L  K  E    33

121  GGGCAGACCCTGGATGTGAAATGTGACTACACGCTAGAGAAGTTTGCCAGCAGCCAGAAA  180
 34  G  Q  T  L  D  V  K  C  D  Y  T  L  E  K  F  A  S  S  Q  K    53

181  GCTTGGCAGATAATAAGGGACGGAGAGATGCCCAAGACCCTGGCATGCACAGAGAGGCCT  240
 54  A  W  Q  I  I  R  D  G  E  M  P  K  T  L  A  C  T  E  R  P    73

241  TCAAAGAATTCCCATCCAGTCCAAGTGGGGAGGATCATACTAGAAGACTACCATGATCAT  300
 74  S  K  N  S  H  P  V  Q  V  G  R  I  I  L  E  D  Y  H  D  H    93

301  GGTTTACTGCGCGTCCGAATGGTCAACCTTCAAGTGGAAGATTCTGGACTGTATCAGTGT  360
 94  G  L  L  R  V  R  M  V  N  L  Q  V  E  D  S  G  L  Y  Q  C   113

361  GTGATCTACCAGCCTCCCAAGGAGCCTCACATGCTGTTCGATCGCATCCGCTTGGTGGTG  420
114  V  I  Y  Q  P  P  K  E  P  H  M  L  F  D  R  I  R  L  V  V   133

421  ACCAAGGGTTTTTCAGGGACCCCTGGCTCCAATGAGAATTCTACCCAGAATGTGTATAAG  480
134  T  K  G  F  S  G  T  P  G  S  N  E  N  S  T  Q  N  V  Y  K   153

481  ATTCCTCCTACCACCACTAAGGCCTTGTGCCCACTCTATACCAGCCCCAGAACTGTGACC  540
154  I  P  P  T  T  T  K  A  L  C  P  L  Y  T  S  P  R  T  V  T   173

541  CAAGCTCCACCCAAGTCAACTGCCGATGTCTCCACTCCTGACTCTGAAATCAACCTTACA  600
174  Q  A  P  P  K  S  T  A  D  V  S  T  P  D  S  E  I  N  L  T   193

601  AATGTGACAGATATCATCAGGGTTCCGGTGTTCAACATTGTCATTCTCCTGGCTGGTGGA  660
194  N  V  T  D  I  I  R  V  P  V  F  N  I  V  I  L  L  A  G  G   213

661  TTCCTGAGTAAGAGCCTGGTCTTCTCTGTCCTGTTTGCTGTCACGCTGAGGTCATTTGTA  720
214  F  L  S  K  S  L  V  F  S  V  L  F  A  V  T  L  R  S  F  V   233

721  CCCTAGGCCCACGAACCCACGAGAATGTCCTCTGACTTCCAGCCACATCCATCTGGCAGT  780
234  P  *                                                         235

781  TGTGCCAAGGGAGGAGGGAGGAGGTAAAAGGCAGGGAGTTAATAACATGAATTAAATCTG  840

841  TAATCACCAGCTAAAAAAAAAAAAAAAAAA  870
```

FIG. 1

```
1 CGCCTGGCAC CATGAGGACG CCTGGGCCTC TGCCTGTGCT GCTGCTGCTC CTGGCGGGAG 60
1            M  R  T   P  G  P   L  P  V  L   L  L  L   L  A  G  16

61 CCCCCGCCGC GCGGCCCACT CCCCCGACCT GCTACTCCCG CATGCGGGCC CTGAGCCAGG 120
17 A  P  A  A   R  P  T   P  P  T   C  Y  S  R   M  R  A   L  S  Q  36

121 AGATCACCCG CGACTTCAAC CTCCTGCAGG TCTCGGAGCC CTCGGAGCCA TGTGTGAGAT 180
37 E  I  T  R   D  F  N   L  L  Q   V  S  E  P   S  E  P   C  V  R  56

181 ACCTGCCCAG GCTGTACCTG GACATACACA ATTACTGTGT GCTGGACAAG CTGCGGGACT 240
57 Y  L  P  R   L  Y  L   D  I  H   N  Y  C  V   L  D  K   L  R  D  76

241 TTGTGGCCTC GCCCCCGTGT TGGAAAGTGG CCCAGGTAGA TTCCTTGAAG GACAAAGCAC 300
77 F  V  A  S   P  P  C   W  K  V   A  Q  V  D   S  L  K   D  K  A  96

301 GGAAGCTGTA CACCATCATG AACTCGTTCT GCAGGAGAGA TTTGGTATTC CTGTTGGATG 360
97 R  K  L  Y   T  I  M   N  S  F   C  R  R  D   L  V  F   L  L  D  116

361 ACTGCAATGC CTTGGAATAC CCAATCCCAG TGACTACGGT CCTGCCAGAT CGTCAGCGCT 420
117 D  C  N  A   L  E  Y   P  I  P   V  T  T  V   L  P  D   R  Q  R  136

421 AAGGGAACTG AGACCAGAGA AAGAACCCAA GAGAACTAAA GTTATGTCAG CTACCCAGAC 480
```

FIG. 3A

```
481 TTAATGGGCC AGAGCCATGA CCCTCACAGG TCTTGTGTTA GTTGTATCTG AAACTGTTAT 540

541 GTATCTCTCT ACCTTCTGGA AAACAGGGCT GGTATTCCTA CCCNGGAACC TCCTTTGAGC 600

601 ATAGAGTTAG CAACCATGCT TCTCATTCCC TTGACTCATG TCTTGCCAGG ATGGTTAGAT 660

661 ACACAGCATG TTGATTTGGT CACCTAAAAA GAAGAAAAGG ACTAACAAGC TTCACTTTTA 720

721 TGAACAACTA TTTTGAGAAC ATGCACAATA GTATGTTTTT ATTACTGGTT TAATGGAGTA 780

781 ATGGTACTTT TATTCTTTCT TGATAGAAAC CTGCTTACAT TTAACCAAGC TTCTATTATG 840

841 CCTTTTTCTA ACACAGACTT TCTTCACTGT CTTTCATTTA AAAAGAAATT AATGCTCTTA 900

901 AGATATATAT TTTAYGTAGT GCTGACAGGA CCCACTCTTT CATTGAAAGG TGATGAAAAT 960

961 CAAATAAAGA ATCTCTTCAC ATGARAAAAA AAAAAA 996
```

FIG. 3B

```
  1 GTGTGCCGGA TTTGGTTAGC TGAGCCCACC GAGAGGCGCC TGCAGGATGA AAGCTCTCTG 60
  1                                                  M   K  A  L  C 5

 61 TCTCCTCCTC CTCCCTGTCC TGGGGCTGTT GGTGTCTAGC AAGACCCTGT GCTCCATGGA 120
  6  L  L  L   L  P  V   L  G  L  L   V  S  S   K  T  L   C  S  M  E 25

121 AGAAGCCATC AATGAGAGGA TCCAGGAGGT CGCCGGCTCC CTAATATTTA GGGCAATAAG 180
 26  E  A  I   N  E  R   I  Q  E  V   A  G  S   L  I  F   R  A  I  S 45

181 CAGCATTGGC CTGGAGTGCC AGAGCGTCAC CTCCAGGGGG GACCTGGCTA CTTGCCCCCG 240
 46  S  I  G   L  E  C   Q  S  V  T   S  R  G   D  L  A   T  C  P  R 65

241 AGGCTTCGCC GTCACCGGCT GCACTTGTGG CTCCGCCTGT GGCTCGTGGG ATGTGCGCGC 300
 66  G  F  A   V  T  G   C  T  C  G   S  A  C   G  S  W   D  V  R  A 85

301 CGAGACCACA TGTCACTGCC AGTGCGCGGG CATGGACTGG ACCGGAGCGC GCTGCTGTCG 360
 86  E  T  T   C  H  C   Q  C  A  G   M  D  W   T  G  A   R  C  C  R 105

361 TGTGCAGCCC TGAGGTCGCG CGCAGTGGCA ACAGCGCGGG CGGAGGCGGC TCCAGGTCCG 420
106  V  Q  P   *                                                     108

421 GAGGGTTGCG GGGGAGCTGG AAATAAACCT GGAGATGATG ATGATGATGA TGATGGAAAA 480

481 AAAAAAAAAA AAAAAAAAAA AAAAAAAAAA AAAAAAAAAA AAAAAAAAAA AAAAAAAAAA 540

541 AAAAAAAAAA AAA 553
```

FIG. 5

```
                .          .          .          .          .
  1 GGCACGAGGT CCCCGACGCG CCCCGCCCAA CCCCTACGAT GAAGAGGGCG 50
  1                                              M  K  R  A  4
                .          .          .          .          .
 51 TCCGCTGGAG GGAGCCGGCT GCTGGCATGG GTGCTGTGGC TGCAGGCCTG 100
  5 S  A  G  G   S  R  L   L  A  W   V  L  W  L   Q  A  W  21
                .          .          .          .          .
101 GCAGGTGGCA GCCCCATGCC CAGGTGCCTG CGTATGCTAC AATGAGCCCA 150
 22  Q  V  A   A  P  C  P   G  A  C   V  C  Y   N  E  P  K 38
                .          .          .          .          .
151 AGGTGACGAC AAGCTGCCCC CAGCAGGGCC TGCAGGCTGT GCCCGTGGGC 200
 39  V  T  T   S  C  P   Q  Q  G  L   Q  A  V   P  V  G  54
                .          .          .          .          .
201 ATCCCTGCTG CCAGCCAGCG CATCTTCCTG CACGGCAACC GCATCTCGCA 250
 55 I  P  A  A   S  Q  R   I  F  L   H  G  N  R   I  S  H  71
                .          .          .          .          .
251 TGTGCCAGCT GCCAGCTTCC GTGCCTGCCG CAACCTCACC ATCCTGTGGC 300
 72  V  P  A   A  S  F  R   A  C  R   N  L  T   I  L  W  L 88
                .          .          .          .          .
301 TGCACTCGAA TGTGCTGGCC CGAATTGATG CGGCTGCCTT CACTGGCCTG 350
 89  H  S  N   V  L  A   R  I  D  A   A  A  F   T  G  L  104
                .          .          .          .          .
351 GCCCTCCTGG AGCAGCTGGA CCTCAGCGAT AATGCACAGC TCCGGTCTGT 400
105 A  L  L  E   Q  L  D   L  S  D   N  A  Q  L   R  S  V  121
                .          .          .          .          .
401 GGACCCTGCC ACATTCCACG GCCTGGGCCG CCTACACACG CTGCACCTGG 450
122  D  P  A   T  F  H  G   L  G  R   L  H  T   L  H  L  D 138
                .          .          .          .          .
451 ACCGCTGCGG CCTGCAGGAG CTGGGCCCGG GGCTGTTCCG CGGCCTGGCT 500
139  R  C  G   L  Q  E   L  G  P  G   L  F  R   G  L  A  154
                .          .          .          .          .
501 GCCCTGCAGT ACCTCTACCT GCAGGACAAC GCGCTGCAGG CACTGCCTGA 550
155 A  L  Q  Y   L  Y  L   Q  D  N   A  L  Q  A   L  P  D  171
                .          .          .          .          .
551 TGACACCTTC CGCGACCTGG GCAACCTCAC ACACCTCTTC CTGCACGGCA 600
172  D  T  F   R  D  L  G   N  L  T   H  L  F   L  H  G  N 188
```

FIG. 7A

```
601 ACCGCATCTC CAGCGTGCCC GAGCGCGCCT TCCGTGGGCT GCACAGCCTC 650
189  R  I  S   S  V  P   E  R  A  F   R  G  L   H  S  L  204

651 GACCGTCTCC TACTGCACCA GAACCGCGTG GCCCATGTGC ACCCGCATGC 700
205 D  R  L  L   L  H  Q   N  R  V   A  H  V  H   P  H  A 221

701 CTTCCGTGAC CTTGGCCGCC TCATGACACT CTATCTGTTT GCCAACAATC 750
222  F  R  D   L  G  R  L   M  T  L   Y  L  F   A  N  N  L 238

751 TATCAGCGCT GCCCACTGAG GCCCTGGCCC CCCTGCGTGC CCTGCAGTAC 800
239  S  A  L   P  T  E   A  L  A  P   L  R  A   L  Q  Y  254

801 CTGAGGCTCA ACGACAACCC CTGGGTGTGT GACTGCCGGG CACGCCCACT 850
255 L  R  L  N   D  N  P   W  V  C   D  C  R  A   R  P  L 271

851 CTGGGCCTGG CTGCAGAAGT TCCGCGGCTC CTCCTCCGAG GTGCCCTGCA 900
272  W  A  W   L  Q  K  F   R  G  S   S  S  E   V  P  C  S 288

901 GCCTCCCGCA ACGCCTGGCT GGCCGTGACC TCAAACGCCT AGCTGCCAAT 950
289  L  P  Q   R  L  A   G  R  D  L   K  R  L   A  A  N  304

951 GACCTGCAGG GCTGCGCTGT GGCCACCGGC CCTTACCATC CCATCTGGAC 1000
305 D  L  Q  G   C  A  V   A  T  G   P  Y  H  P   I  W  T 321

1001 CGGCAGGGCC ACCGATGAGG AGCCGCTGGG GCTTCCCAAG TGCTGCCAGC 1050
322  G  R  A   T  D  E  E   P  L  G   L  P  K   C  C  Q  P 338

1051 CAGATGCCGC TGACAAGGCC TCAGTACTGG AGCCTGGAAG ACCAGCTTCG 1100
339  D  A  A   D  K  A   S  V  L  E   P  G  R   P  A  S  354

1101 GCAGGCAATG CGCTGAAGGG ACGCGTGCCG CCCGGTGACA GCCCGCCGGG 1150
355 A  G  N  A   L  K  G   R  V  P   P  G  D  S   P  P  G 371

1151 CAACGGCTCT GGCCCACGGC ACATCAATGA CTCACCCTTT GGGACTCTGC 1200
372  N  G  S   G  P  R  H   I  N  D   S  P  F   G  T  L  P 388
```

FIG. 7B

```
1201 CTGGCTCTGC TGAGCCCCCG GCTCACTGCA GTGCGGCCCG AGGGCTCCGA 1250
 389  G  S  A   E  P  P   A  H  C  S   A  A  R   G  L  R   404

1251 GCCACCAGGT TCCCCACTTC GGGCCCTCGC CGGAGGCCAG GCTGTTCACG 1300
 405 A  T  R  F   P  T  S   G  P  R   R  R  P  G   C  S  R  421

1301 CAAGAACCGC ACCCGCAGCC ACTGCCGTCT GGGCCAGGCA GGCAGCGGGG 1350
 422  K  N  R   T  R  S  H   C  R  L   G  Q  A   G  S  G  G 438

1351 GTGGCGGGAC TGGTGACTCA GAAGGCTCAG GTGCCCTACC CAGCCTCACC 1400
 439  G  G  T   G  D  S   E  G  S  G   A  L  P   S  L  T   454

1401 TGCAGCCTCA CCCCCCTGGG CCTGGCGCTG GTGCTGTGGA CAGTGCTTGG 1450
 455 C  S  L  T   P  L  G   L  A  L   V  L  W  T   V  L  G  471

1451 GCCCTGCTGA CCCCCAGCGG ACACAAGAGC GTGCTCAGCA GCCAGGTGTG 1500
 472  P  C  *                                               473

1501 TGTACATACG GGGTCTCTCT CCACGCCGCC AAGCCAGCCG GGCGGCCGAC 1550

1551 CCGTGGGGCA GGCCAGGCCA GGTCCTCCCT GATGGACGCC TGCCGCCCGC 1600

1601 CACCCCCATC TCCACCCCAT CATGTTTACA GGGTTCGGCG GCAGCGTTTG 1650

1651 TTCCAGAACG CCGCCTCCCA CCCAGATCGC GGTATATAGA GATATGCATT 1700

1701 TTATTTTACT TGTGTAAAAA TATCGGACGA CGTGGAATAA AGAGCTCTTT 1750

1751 TCTTAAAAAA AAAAAAAAAA AACTCGA 1777
```

FIG. 7C

```
  1  GGTCGACGGTATCGATAAGCTTGATATCGAATTCCTGCAACAGTTCTTGGAAACCCACTC   60

 61  GAGAGGGCCACGCCTCCATTCACCAGGCCACGCATCACAAGAGGCAACACCAGGAGCCAA  120

121  CATGAGCTCGGGGACTGAACTGCTGTGGCCCGGAGCAGCGCTGCTGGTGCTGTTGGGGGT  180
  1   M  S  S  G  T  E  L  L  W  P  G  A  A  L  L  V  L  L  G  V   20

181  GGCAGCCAGTCTGTGTGTGCGCTGCTCACGCCCAGGTGCAAAGAGGTCAGAGAAAATCTA  240
 21   A  A  S  L  C  V  R  C  S  R  P  G  A  K  R  S  E  K  I  Y   40

241  CCAGCAGAGAAGTCTGCGTGAGGACCAACAGAGCTTTACGGGGTCCCGGACCTACTCCTT  300
 41   Q  Q  R  S  L  R  E  D  Q  Q  S  F  T  G  S  R  T  Y  S  L   60

301  GGTCGGGCAGGCATGGCCAGGACCCCTGGCGGACATGGCACCCACAAGGAAGGACAAGCT  360
 61   V  G  Q  A  W  P  G  P  L  A  D  M  A  P  T  R  K  D  K  L   80

361  GTTGCAATTCTACCCCAGCCTGGAGGATCCAGCATCTTCCAGGTACCAGAACTTCAGCAA  420
 81   L  Q  F  Y  P  S  L  E  D  P  A  S  S  R  Y  Q  N  F  S  K  100

421  AGGAAGCAGACACGGGTCGGAGGAAGCCTACATAGACCCCATTGCCATGGAGTATTACAA  480
101   G  S  R  H  G  S  E  E  A  Y  I  D  P  I  A  M  E  Y  Y  N  120

481  CTGGGGGCGGTTCTCGAAGCCCCCAGAAGATGATGATGCCAATTCCTACGAGAATGTGCT  540
121   W  G  R  F  S  K  P  P  E  D  D  D  A  N  S  Y  E  N  V  L  140

541  CATTTGCAAGCAGAAAACCACAGAGACAGGTGCCCAGCAGGAGGGCATAGGTGGCCTCTG  600
141   I  C  K  Q  K  T  T  E  T  G  A  Q  Q  E  G  I  G  G  L  C  160

601  CAGAGGGGACCTCAGCCTGTCACTGGCCCTGAAGACTGGCCCCACTTCTGGTCTCTGTCC  660
161   R  G  D  L  S  L  S  L  A  L  K  T  G  P  T  S  G  L  C  P  180

661  CTCTGCCTCCCCGGAAGAAGATGAAGGAATCTGAGGATTATCAGAACTTCAGCATTCCAT  720
181   S  A  S  P  E  E  D  E  G  I  *                               191

721  CCATTCAGTGGCGCGAGTCCAGGAAGGTCATGGGGCAACTCCAGAGAAGAAAGCATCCCC  780

781  TGGCCCGGTGGGAAGCCCAGACGAGGAGGACGGGGAACCGGATTACGTGAATGGGGAGGT  840

841  GGCAGCCACAGAAGCCTAGGGCAGACCAAGAAGAAAGGAGCCAAGGCAAAGAGGGACCAC  900
```

FIG. 9A

```
 901  TGTGCTCATGGACCCATCGCTGCCTTCCAAGGACCATTTCCCAGAGCTACTCAACTTTTA   960
 961  AGCCCCTGCCATGGTTGCTCCTGGAAGGAGAACCAGCCACCCTGAGGACCACCTGGCCAT  1020
1021  GCGTGCACAGCCTGGGAAAAGACAGTTACTCACGGGAGCTGCAGGCCCCGTCACCAAGCC  1080
1081  CTCTCCCGACCCAGGCTTTGTGGGGCAGGCACCTGGTACCAAGGGTAACCCGGCTCCTGG  1140
1141  TATGGACGGATGCGCAGGATTTAGGATAAGCTGTCACCCAGTCCCCATAACAAAACCACT  1200
1201  GTCCAACACTGGTATCTGTGTTCTTTTGTGCTATGAATTTGGATTCCTAATTGCTATTGT  1260
1261  TGGTTGCTGGGGTTTTAAATGATTGATAAGCTTGTACAGTTAACTTATAGAGGGGGAGCC  1320
1321  ATATTTAACATTCTGGATTTCAGAGTAGAGATTTCTGTGTTGTCTCCTAGAAAGCATTAC  1380
1381  ATGTAGTTTATTTCAGCATCCTTGTTGGGTGGGGCCCTGGCTCTCTTCCCCTTTGGTGGG  1440
1441  ACCTCCCCTTTCTTTGGGCTTCAGTTCACTCAGGAAGAAATGAGGCTGTCGCCATCTTTA  1500
1501  TGTGCTTCCAGTGGAAATGTCACTTGCTACAGACAATAGTGCATGAGAGTCTAGAGAAGT  1560
1561  AGTGACCAGAACAGGGCAGAGTAGGTCCCCTCCATGGCCCTGAATCCTCCTCTGCTCCAG  1620
1621  GGCTGGCCTCTGCAGAGCTGATTAAACAGTGTTGTGACTGTCTCATGGGAAGAGCTGGGG  1680
1681  CCCAGAGGGACCTTGAGTCAGAAATGTTGCCAGAAAAAGTATCTCCTCCAACCAAAACAT  1740
1741  CTCAATAAAACCATTTTAGTTGAAAAAAAAAAAAAAAAAAAAAAAAAAAAAAAAAAA  1797
```

FIG. 9B

```
  1  GCCGCGCCGAGGAGGCTGCCGCTCTGGCTTGCCGCCCCCCGCCGCCGCTGCACACCGGAC   60

 61  CCAGCCGCCGTGCCGCGGGCCATGGACCTGCCCAGGGGCCTGGTGGTGGCCTGGGCGCTC  120
  1                       M  D  L  P  R  G  L  V  V  A  W  A  L    13

121  AGCCTGTGGCCAGGGTTCACGGACACCTTCAACATGGACACCAGGAAGCCCCGGGTCATC  180
 14  S  L  W  P  G  F  T  D  T  F  N  M  D  T  R  K  P  R  V  I    33

181  CCTGGCTCCAGGACCGCCTTCTTTGGCTACACAGTGCAGCAGCACGACATCAGTGGCAAT  240
 34  P  G  S  R  T  A  F  F  G  Y  T  V  Q  Q  H  D  I  S  G  N    53

241  AAGTGGCTGGTCGTGGGCGCCCCACTGGAAACCAATGGCTACCAGAAGACGGGAGACGTG  300
 54  K  W  L  V  V  G  A  P  L  E  T  N  G  Y  Q  K  T  G  D  V    73

301  TACAAGTGTCCAGTGATCCACGGGAACTGCACCAAACTCAACCTGGGAAGGGTCACCCTG  360
 74  Y  K  C  P  V  I  H  G  N  C  T  K  L  N  L  G  R  V  T  L    93

361  TCCAACGTGTCCGAGCGGAAAGACAACATGCGCCTCGGCCTTAGTCTCGCCACCAACCCC  420
 94  S  N  V  S  E  R  K  D  N  M  R  L  G  L  S  L  A  T  N  P   113

421  AAGGACAACAGCTTCCTGGCCTGCAGCCCCCTCTGGTCTCATGAGTGTGGGAGCTCCTAC  480
114  K  D  N  S  F  L  A  C  S  P  L  W  S  H  E  C  G  S  S  Y   133

481  TACACCACAGGGATGTGTTCAAGAGTCAACTCCAACTTCAGGTTCTCCAAGACCGTGGCC  540
134  Y  T  T  G  M  C  S  R  V  N  S  N  F  R  F  S  K  T  V  A   153

541  CCAGCTCTCCAAAGGTGCCAGACCTACATGGACATCGTCATTGTCCTGGATGGCTCCAAC  600
154  P  A  L  Q  R  C  Q  T  Y  M  D  I  V  I  V  L  D  G  S  N   173

601  AGCATCTACCCCTGGGTGGAGGTTCAGCACTTCCTCATCAACATCCTGAAAAAGTTTTAC  660
174  S  I  Y  P  W  V  E  V  Q  H  F  L  I  N  I  L  K  K  F  Y   193

661  ATTGGCCCAGGGCAGATCCAGGTTGGAGTTGTGCAGTATGGCGAAGATGTGGTGCATGAG  720
194  I  G  P  G  Q  I  Q  V  G  V  V  Q  Y  G  E  D  V  V  H  E   213

721  TTTCACCTCAATGACTACAGGTCTGTAAAAGATGTGGTGGAAGCTGCCAGCCACATTGAG  780
214  F  H  L  N  D  Y  R  S  V  K  D  V  V  E  A  A  S  H  I  E   233

781  CAGAGAGGAGGAACAGAGACCCGGACGGCATTTGGCATTGAATTTGCACGCTCAGAGGCT  840
234  Q  R  G  G  T  E  T  R  T  A  F  G  I  E  F  A  R  S  E  A   253
```

FIG. 11A

```
 841  TTCCAGAAGGGTGGAAGGAAAGGAGCCAAGAAGGTGATGATTGTCATCACAGATGGGGAG   900
 254  F  Q  K  G  G  R  K  G  A  K  K  V  M  I  V  I  T  D  G  E    273

 901  TCCCACGACAGCCCAGACCTGGAGAAGGTGATCCAGCAAAGCGAAAGAGACAACGTAACA   960
 274  S  H  D  S  P  D  L  E  K  V  I  Q  Q  S  E  R  D  N  V  T    293

 961  AGATATGCGGTGGCCGTCCTGGGCTACTACAACCGCAGGGGGATCAATCCAGAAACTTTT  1020
 294  R  Y  A  V  A  V  L  G  Y  Y  N  R  R  G  I  N  P  E  T  F    313

1021  CTAAATGAAATCAAATACATCGCCAGTGACCCTGATGACAAGCACTTCTTCAATGTCACT  1080
 314  L  N  E  I  K  Y  I  A  S  D  P  D  D  K  H  F  F  N  V  T    333

1081  GATGAGGCTGCCTTGAAGGACATTGTCGATGCCCTGGGGGACAGAATCTTCAGCCTGGAA  1140
 334  D  E  A  A  L  K  D  I  V  D  A  L  G  D  R  I  F  S  L  E    353

1141  GGCACCAACAAGAACGAGACCTCCTTTGGGCTGGAGATGTCACAGACGGGCTTTTCCTCG  1200
 354  G  T  N  K  N  E  T  S  F  G  L  E  M  S  Q  T  G  F  S  S    373

1201  CACGTGGTGGAGGATGGGGTTCTGCTGGGAGCCGTCGGTGCCTATGACTGGAATGGAGCT  1260
 374  H  V  V  E  D  G  V  L  L  G  A  V  G  A  Y  D  W  N  G  A    393

1261  GTGCTAAAGGAGACGAGTGCCGGGAAGGTCATTCCTCTCCGCGAGTCCTACCTGAAAGAG  1320
 394  V  L  K  E  T  S  A  G  K  V  I  P  L  R  E  S  Y  L  K  E    413

1321  TTCCCCGAGGAGCTCAAGAACCATGGTGCATACCTGGGGTACACAGTCACATCGGTCGTG  1380
 414  F  P  E  E  L  K  N  H  G  A  Y  L  G  Y  T  V  T  S  V  V    433

1381  TCCTCCAGGCAGGGGCGAGTGTACGTGGCCGGAGCCCCCCGGTTCAACCACACGGGCAAG  1440
 434  S  S  R  Q  G  R  V  Y  V  A  G  A  P  R  F  N  H  T  G  K    453

1441  GTCATCCTGTTCACCATGCACAACAACCGGAGCCTCACCATCCACCAGGCTATGCGGGGC  1500
 454  V  I  L  F  T  M  H  N  N  R  S  L  T  I  H  Q  A  M  R  G    473

1501  CAGCAGATAGGCTCTTACTTTGGGAGTGAAATCACCTCGGTGGACATCGACGGCGACGGC  1560
 474  Q  Q  I  G  S  Y  F  G  S  E  I  T  S  V  D  I  D  G  D  G    493

1561  GTGACTGATGTCCTGCTGGTGGGCGCACCCATGTACTTCAACGAGGGCCGTGAGCGAGGC  1620
 494  V  T  D  V  L  L  V  G  A  P  M  Y  F  N  E  G  R  E  R  G    513

1621  AAGGTGTACGTCTATGAGCTGAGACAGAACCGGTTTGTTTATAACGGAACGCTAAAGGAT  1680
 514  K  V  Y  V  Y  E  L  R  Q  N  R  F  V  Y  N  G  T  L  K  D    533
```

FIG. 11B

```
1681  TCACACAGTTACCAGAATGCCCGATTTGGGTCCTCCATTGCCTCAGTTCGAGACCTCAAC  1740
 534  S  H  S  Y  Q  N  A  R  F  G  S  S  I  A  S  V  R  D  L  N   553

1741  CAGGATTCCTACAATGACGTGGTGGTGGGAGCCCCCCTGGAGGACAACCACGCAGGAGCC  1800
 554  Q  D  S  Y  N  D  V  V  V  G  A  P  L  E  D  N  H  A  G  A   573

1801  ATCTACATCTTCCACGGCTTCCGAGGCAGCATCCTGAAGACACCTAAGCAGAGAATCACA  1860
 574  I  Y  I  F  H  G  F  R  G  S  I  L  K  T  P  K  Q  R  I  T   593

1861  GCCTCAGAGCTGGCTACCGGCCTCCAGTATTTTGGCTGCAGCATCCACGGGCAATTGGAC  1920
 594  A  S  E  L  A  T  G  L  Q  Y  F  G  C  S  I  H  G  Q  L  D   613

1921  CTCAATGAGGATGGGCTCATCGACCTGGCAGTGGGAGCCCTTGGCAACGCTGTGATTCTG  1980
 614  L  N  E  D  G  L  I  D  L  A  V  G  A  L  G  N  A  V  I  L   633

1981  TGGTCCCGCCCAGTGGTTCAGATCAATGCCAGCCTCCACTTTGAGCCATCCAAGATCAAC  2040
 634  W  S  R  P  V  V  Q  I  N  A  S  L  H  F  E  P  S  K  I  N   653

2041  ATCTTCCACAGAGACTGCAAGCGCAGTGGCAGGGATGCCACCTGCCTGGCCGCCTTCCTC  2100
 654  I  F  H  R  D  C  K  R  S  G  R  D  A  T  C  L  A  A  F  L   673

2101  TGCTTCACGCCCATCTTCCTGGCACCCCATTTCCAAACAACAACTGTTGGCATCAGATAC  2160
 674  C  F  T  P  I  F  L  A  P  H  F  Q  T  T  T  V  G  I  R  Y   693

2161  AACGCCACCATGGATGAGAGGCGGTATACACCGAGGGCCCACCTGGACGAGGGCGGGGAC  2220
 694  N  A  T  M  D  E  R  R  Y  T  P  R  A  H  L  D  E  G  G  D   713

2221  CGATTCACCAACAGAGCCGTACTGCTCTCCTCCGGCCAGGAGCTCTGTGAGCGGATCAAC  2280
 714  R  F  T  N  R  A  V  L  L  S  S  G  Q  E  L  C  E  R  I  N   733

2281  TTCCATGTCCTGGACACTGCTGACTACGTGAAGCCAGTGACCTTCTCAGTCGAGTATTCC  2340
 734  F  H  V  L  D  T  A  D  Y  V  K  P  V  T  F  S  V  E  Y  S   753

2341  CTGGAGGACCCTGACCATGGCCCCATGCTGGACGACGGCTGGCCCACCACTCTCAGAGTC  2400
 754  L  E  D  P  D  H  G  P  M  L  D  D  G  W  P  T  T  L  R  V   773

2401  TCGGTGCCCTTCTGGAACGGCTGCAATGAGGATGAGCACTGTGTCCCTGACCTTGTGTTG  2460
 774  S  V  P  F  W  N  G  C  N  E  D  E  H  C  V  P  D  L  V  L   793

2461  GATGCCCGGAGTGACCTGCCCACGGCCATGGAGTACTGCCAGAGGGTGCTGAGGAAGCCT  2520
 794  D  A  R  S  D  L  P  T  A  M  E  Y  C  Q  R  V  L  R  K  P   813
```

FIG. 11C

```
2521  GCGCAGGACTGCTCCGCATACACGCTGTCCTTCGACACCACAGTCTTCATCATAGAGAGC  2580
 814  A  Q  D  C  S  A  Y  T  L  S  F  D  T  T  V  F  I  I  E  S   833

2581  ACACGCCAGCGAGTGGCGGTGGAGGCCACACTGGAGAACAGGGGCGAGAACGCCTACAGC  2640
 834  T  R  Q  R  V  A  V  E  A  T  L  E  N  R  G  E  N  A  Y  S   853

2641  ACGGTCCTAAATATCTCGCAGTCAGCAAACCTGCAGTTTGCCAGCTTGATCCAGAAGGAG  2700
 854  T  V  L  N  I  S  Q  S  A  N  L  Q  F  A  S  L  I  Q  K  E   873

2701  GACTCAGACGGTAGCATTGAGTGTGTGAACGAGGAGAGGAGGCTCCAGAAGCAAGTCTGC  2760
 874  D  S  D  G  S  I  E  C  V  N  E  E  R  R  L  Q  K  Q  V  C   893

2761  AACGTCAGCTATCCCTTCTTCCGGGCCAAGGCCAAGGTGGCTTTCCGTCTTGATTTTGAG  2820
 894  N  V  S  Y  P  F  F  R  A  K  A  K  V  A  F  R  L  D  F  E   913

2821  TTCAGCAAATCCATCTTCCTACACCACCTGGAGATCGAGCTCGCTGCAGGCAGTGACAGT  2880
 914  F  S  K  S  I  F  L  H  H  L  E  I  E  L  A  A  G  S  D  S   933

2881  AATGAGCGGGACAGCACCAAGGAAGACAACGTGGCCCCCTTACGCTTCCACCTCAAATAC  2940
 934  N  E  R  D  S  T  K  E  D  N  V  A  P  L  R  F  H  L  K  Y   953

2941  GAGGCTGACGTCCTCTTCACCAGGAGCAGCAGCCTGAGCCACTACGAGGTCAAGCTCAAC  3000
 954  E  A  D  V  L  F  T  R  S  S  S  L  S  H  Y  E  V  K  L  N   973

3001  AGCTCGCTGGAGAGATACGATGGTATCGGGCCTCCCTTCAGCTGCATCTTCAGGATCCAG  3060
 974  S  S  L  E  R  Y  D  G  I  G  P  P  F  S  C  I  F  R  I  Q   993

3061  AACTTGGGCTTGTTCCCCATCCACGGGATTATGATGAAGATCACCATTCCCATCGCCACC  3120
 994  N  L  G  L  F  P  I  H  G  I  M  M  K  I  T  I  P  I  A  T  1013

3121  AGGAGCGGCAACCGCCTACTGAAGCTGAGGGACTTCCTCACGGACGAGGTAGCGAACACG  3180
1014  R  S  G  N  R  L  L  K  L  R  D  F  L  T  D  E  V  A  N  T  1033

3181  TCCTGTAACATCTGGGGCAATAGCACTGAGTACCGGCCCACCCCAGTGGAGGAAGACTTG  3240
1034  S  C  N  I  W  G  N  S  T  E  Y  R  P  T  P  V  E  E  D  L  1053

3241  CGTCGTGCTCCACAGCTGAATCACAGCAACTCTGATGTCGTCTCCATCAACTGCAATATA  3300
1054  R  R  A  P  Q  L  N  H  S  N  S  D  V  V  S  I  N  C  N  I  1073

3301  CGGCTGGTCCCCAACCAGGAAATCAATTTCCATCTACTGGGCAACCTGTGGTTGAGGTCC  3360
1074  R  L  V  P  N  Q  E  I  N  F  H  L  L  G  N  L  W  L  R  S  1093
```

FIG. 11D

```
3361 CTAAAAGCACTCAAGTACAAATCCATGAAAATCATGGTCAACGCAGCCTTGCAGAGGCAG 3420
1094 L K A L K Y K S M K I M V N A A L Q R Q 1113

3421 TTCCACAGCCCCTTCATCTTCCGTGAGGAGGATCCCAGCCGCCAGATCGTGTTTGAGATC 3480
1114 F H S P F I F R E E D P S R Q I V F E I 1133

3481 TCCAAGCAAGAGGACTGGCAGGTCCCCATCTGGATCATTGTAGGCAGCACCCTGGGGGGC 3540
1134 S K Q E D W Q V P I W I I V G S T L G G 1153

3541 CTCCTACTGCTGGCCCTGCTGGTCCTGGCACTGTGGAAGCTCGGCTTCTTTAGAAGTGCC 3600
1154 L L L L A L L V L A L W K L G F F R S A 1173

3601 AGGCGCAGGAGGGAGCCTGGTCTGGACCCCACCCCCAAAGTGCTGGAGTGAGGCTCCAGA 3660
1174 R R R R E P G L D P T P K V L E * 1190

3661 GGAGACTTTGAGTTGATGGGGGCCAGGACACCAGTCCAGGTAGTGTTGAGACCCAGGCCT 3720

3721 GTGGCCCCACCGAGCTGGAGCGGAGAGGAAGCCAGCTGGCTTTGCACTTGACCTCATCTC 3780

3781 CCGAGCAATGGCGCCTGCTCCCTCCAGAATGGAACTCAAGCTGGTTTTAAGTGGAACTGC 3840

3841 CCTACTGGGAGACTGGGACACCTTTAACACAGACCCCTAGGGATTTAAAGGGACACCCCT 3900

3901 ACACACACCCAGGCCCACGCCAAGGCCTCCCTCAGGCTCTGTGGAGGGCATTTGCTGCCC 3960

3961 CAGCTACTAAGGTGCTAGGAATTCGTAATCATCCCCATCCTCCAGAGAAACCCAGGGAGG 4020

4021 AAGACTGTAAATACGAACCCAATCTGCACACTCCAGGCCTCTAGTTCCAGAAGGATCCAA 4080

4081 GACAAAACAGATCTGAATTCTGCCCTTTTCTCTCACCCATCCCACCCCTCCATTGGCTCC 4140

4141 CAAGTCACACCCACTCCCTTCCCCATAGATAGGCCCCTGGGGCTCCCGAAGAATGAACCC 4200

4201 AAGAGCAAGGGCTTGATGGTGACAGCTGCAAGCCAGGGATGAAGAAAGACTCTGAGATGT 4260

4261 GGAGACTGATGGCCAGGCAAGTGGGACCAGGATACTGGACGCTGTCCTGAGATGAGAGGT 4320

4321 AGCCGGGCTCTGCACCCACGTGCATTCACATTGACCGCAACTCACACATTCCCCCACCAG 4380
```

FIG. 11E

```
4381  CTGCAGCCCCTTGCTCTCAGCTGCCAACCCTCCCGGGTCACTTTTGTTCCCAGGTACCTC   4440

4441  ATGGGAAGCATGTGGATGACACAATCCCTGGGGCTGTGCATTCCCACGTCTTCTTGCTGC   4500

4501  AGCCTGCCCCTAGACATGGACGCACCGGCCTGGCTGCAGCTGGGCAGCAGGGGTAGGGGT   4560

4561  AGGGAGCCTCCCCTCCCTGTATCACCCCCTCCCTACACACACACACACACACACACACAC   4620

4621  ACACTGCCTCCCATCCTTCCCTCATGCCCGCCAGTGCACAGGGAAGGGCTTGGCCAGCGC   4680

4681  TGTTGAGGGGTCCCCTCTGGAATGCACTGAATAAAGCACGTGCAAGGACTCCCGGAGCCT   4740

4741  GTGCAGCCTTGGTGGCAAATATCTCATCTGCCGGCCCCCAGGACAAGTGGTATGACCAGT   4800

4801  GATAATGCCCCAAGGACAAGGGGCGTGCCTGGCGCCCAGTGGAGTAATTTATGCCTTAGT   4860

4861  CTTGTTTTGAGGTAGAAATGCAAGGGGGACACATGAAAGGCATCAGTCCCCCTGTGCATA   4920

4921  GTACGACCTTTACTGTCGTATTTTTGAAAAATTAAAAATACAGTGTTTAAAAACAAAAAA   4980

4981  AAAAAAAAAAAAAAA   4995
```

FIG. 11F

```
                   10        20        30        40
  1   MDLPRGLVVAWALSLWPGFTDTFNMDTRKPRVIPGSRTAF  HOHBY69.aa
  1   ----------------------FNVDVKNSMTFSGPVEDM  gi|346210

                   50        60        70        80
 41   FGYTVQQHDISGNKWLVVGAPLETNGYQKTGDVYKCPVIH  HOHBY69.aa
 19   FGYTVQQYENEEGKWVLIGSPLVGQPKNRTGDVYKCPVGR  gi|346210

                   90       100       110       120
 81   GN---CTKLNLG-RVTLSNVSERKDNMRLGLSLATNPKDN  HOHBY69.aa
 59   GESLPCVKLDLPVNTSIPNVTEVKENMTFGSTLVTNPNG-  gi|346210

                  130       140       150       160
117   SFLACSPLWSHECGSSYYTTGMCSRVNSNFRFSKTVAPAL  HOHBY69.aa
 98   GFLACGPLYAYRCGHLHYTTGICSDVSPTFQVVNSIAP-V  gi|346210

                  170       180       190       200
157   QRCQTYMDIVIVLDGSNSIYPWVEVQHFLINILKKFYIGP  HOHBY69.aa
137   QECSTQLDIVIVLDGSNSIYPWDSVTAFLNDLLKRMDIGP  gi|346210

                  210       220       230       240
197   GQIQVGVVQYGEDVVHEFHLNDYRSVKDVVEAASHIEQRG  HOHBY69.aa
177   KQTQVGIVQYGENVTHEFNLNKYSSTEEVLVAAKKIVQRG  gi|346210
```

FIG. 12A

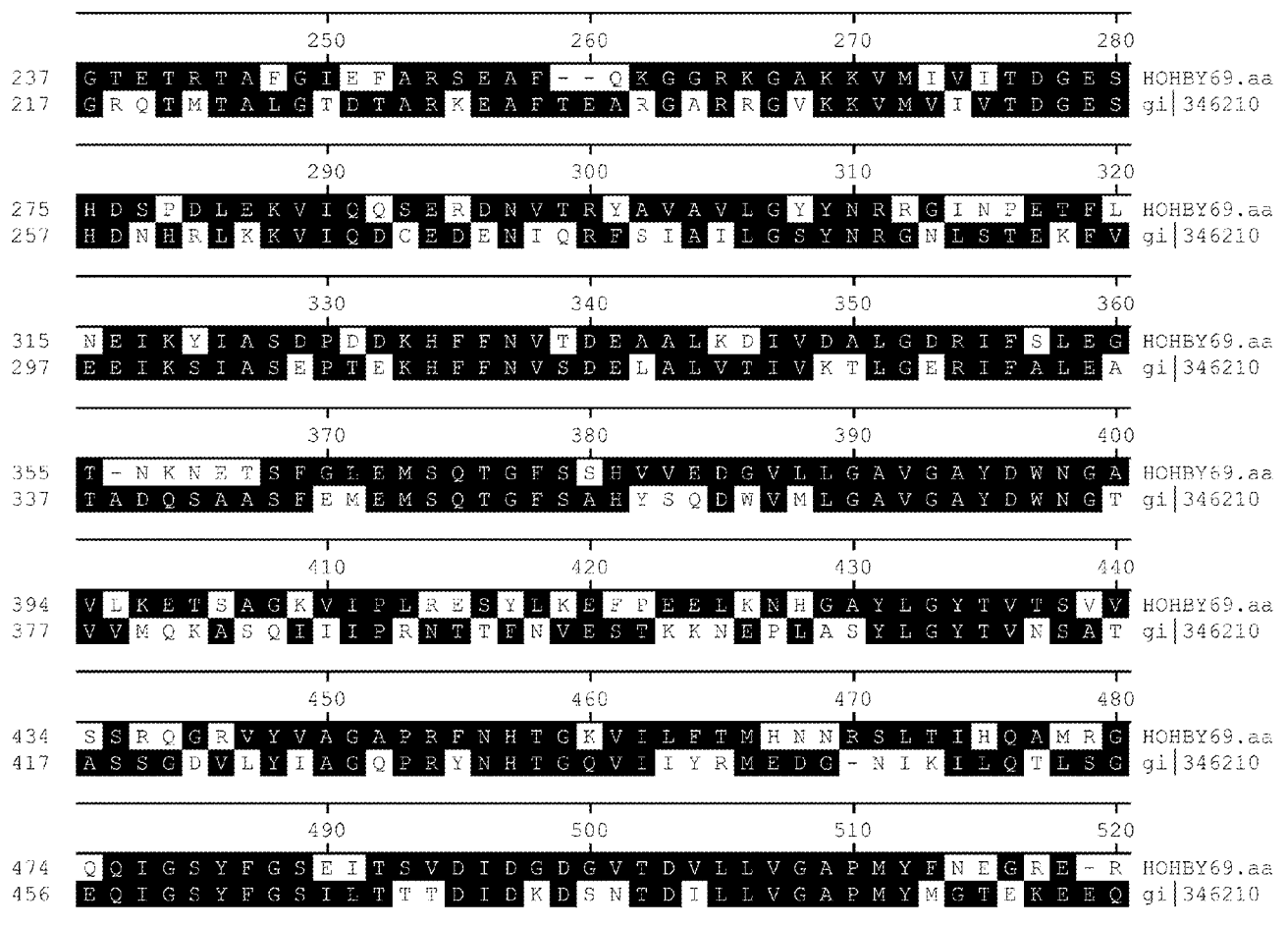

```
                         250       260       270       280
237 GTETRTAFGIEFARSEAF--QKGGRKGAKKVMIVITDGES HOHBY69.aa
217 GRQTMTALGTDTARKEAFTEARGARRGVKKVMVIVTDGES gi|346210

                         290       300       310       320
275 HDSPDLEKVIQQSERDNVTRYAVAVLGYYNRRGINPETFL HOHBY69.aa
257 HDNHRLKKVIQDCEDENIQRFSIAILGSYNRGNLSTEKFV gi|346210

                         330       340       350       360
315 NEIKYIASDPDDKHFFNVTDEAALKDIVDALGDRIFSLEG HOHBY69.aa
297 EEIKSIASEPTEKHFFNVSDELALVTIVKTLGERIFALEA gi|346210

                         370       380       390       400
355 T-NKNETSFGLEMSQTGFSSHVVEDGVLLGAVGAYDWNGA HOHBY69.aa
337 TADQSAASFEMEMSQTGFSAHYSQDWVMLGAVGAYDWNGT gi|346210

                         410       420       430       440
394 VLKETSAGKVIPLRESYLKEFPEELKNHGAYLGYTVTSVV HOHBY69.aa
377 VVMQKASQIIIPRNTTFNVESTKKNEPLASYLGYTVNSAT gi|346210

                         450       460       470       480
434 SSRQGRVYVAGAPRFNHTGKVILFTMHNNRSLTIHQAMRG HOHBY69.aa
417 ASSGDVLYIAGQPRYNHTGQVIIYRMEDG-NIKILQTLSG gi|346210

                         490       500       510       520
474 QQIGSYFGSEITSVDIDGDGVTDVLLVGAPMYFNEGRE-R HOHBY69.aa
456 EQIGSYFGSILTTTDIDKDSNTDILLVGAPMYMGTEKEEQ gi|346210
```

FIG. 12B

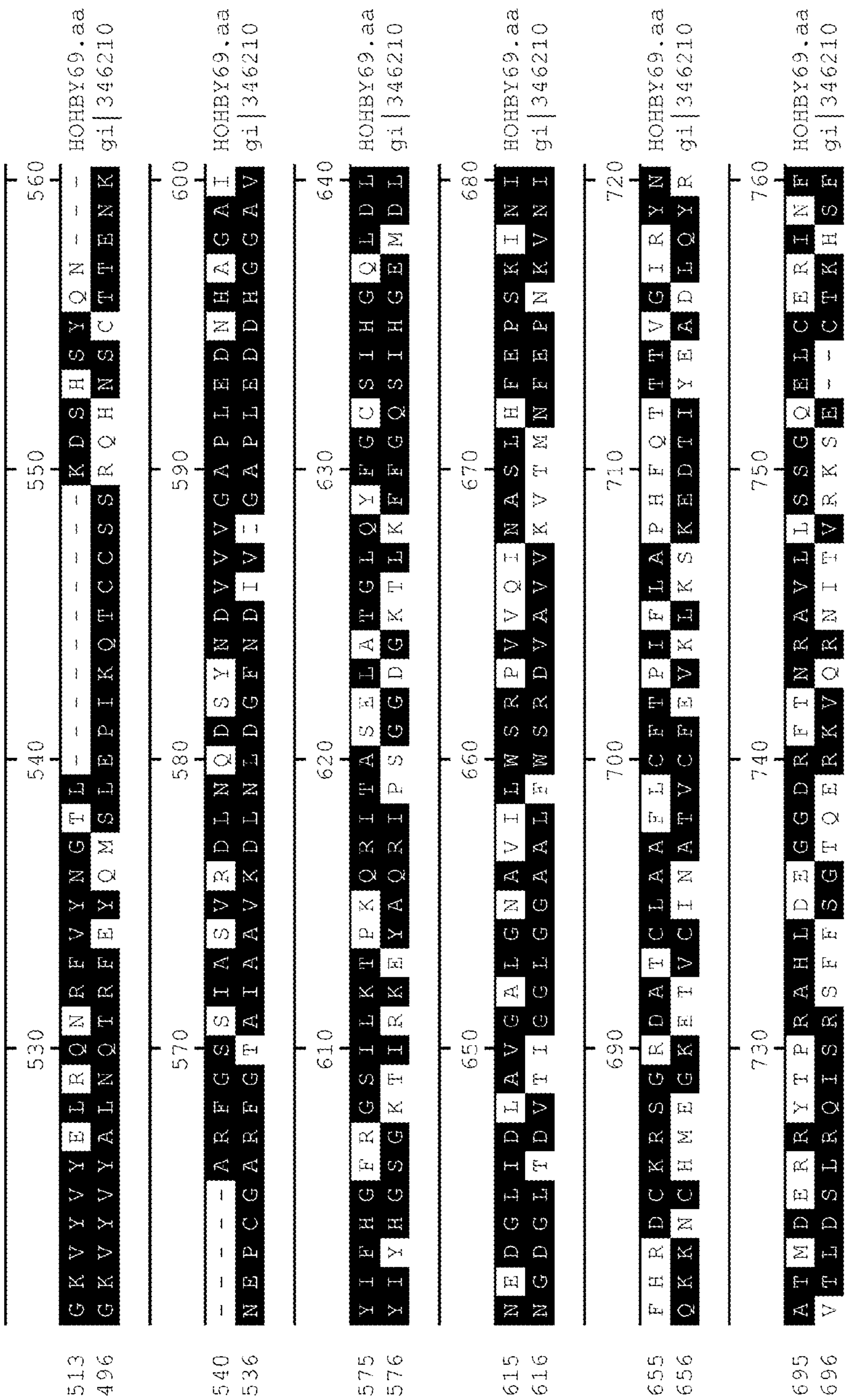

FIG. 12C

```
        530              540              550              560
513  GKVYYELRQNREVYNGTL----KDSHSYQN------           HOHBY69.aa
496  GKVYYYALNQTRFEYQMSLEPIKQTCCSSRQHNSCTTENK        gi|346210

        570              580              590              600
540  ------AREFGSSIASVRDLNQDSYNDVVVGAPLEDNHAGAI       HOHBY69.aa
536  NEPCGAREGTAIAAVKDLNLDGENDIV-GAPLEDDHGGAV        gi|346210

        610              620              630              640
575  YIFHGFRGSILKTPKQRITASELATGLQYFGCSIHGQLDL        HOHBY69.aa
576  YIYHGSGKTIRKEYAQRIPSGGDGTLKFFGQSIHGEMDL         gi|346210

        650              660              670              680
615  NEDGLIDLAVGALGNAVILWSRPVQINASLHFEPSKINI         HOHBY69.aa
616  NGDGLTDVTIGGLGGAALFWSRDVAVVKVTMNFEPNKVNI        gi|346210

        690              700              710              720
655  FHRDCKRSGRDATCLAAFLCFTPIFLAPHFQTTVGIRYN         HOHBY69.aa
656  QKKNCHMEGKETVCINATVCFEVKLKSKEDTIYEADLQYR        gi|346210

        730              740              750              760
695  ATMDERRYTPRAHLDEGGDRFTNRAVLLSSGQELCERINF        HOHBY69.aa
696  VTLDSLRQISRSFESGTQERKVQRNITVRKSE-CTKHSF         gi|346210
```

```
                 1050      1060      1070      1080
1007 ITIPIATRSGNRLLKLRDFLTDEVANTSCNIWGNS----T HOHBY69.aa
976  ISFPNMTSNGYPVLYPTGLSSSENANCRPHIFEDPFSINS gi|346210

                 1090      1100      1110      1120
1043 EYRPTPVEEDLRRAPQLNHSNSDVVSINCNIRLVPNQEIN HOHBY69.aa
1016 GKKMTTSTDHLKRGTILDCNTCKFATITCNLTSSDISQVN gi|346210

                 1130      1140      1150      1160
1083 FHLLGNLWLRSLKALKYKSMKIMVNAALQRQFHSPFIFRE HOHBY69.aa
1056 VSLI--LWKPTFIKSYFSSLNLTIRGELRSE-NASLVLSS gi|346210

                 1170      1180      1190      1200
1123 EDPSRQIVFEISKQE-DWQVPIWIIVGSTLGGLLLLALLV HOHBY69.aa
1093 SNQKRELAIQISKDGLPGRVPLWVILLSAFAGLLLLMLLI gi|346210

                 1210      1220
1162 LALWKLGFFRSARRRREPGLDPTPKVLE.            HOHBY69.aa
1133 LALWKIGFFKRPLKKK----------MEK            gi|346210
```

Decoration 'Decoration #1': Shade (with solid black) residues that match the Consensus exactly.

FIG. 12E

SEQUENCE LISTING

```
<160> NUMBER OF SEQ ID NOS: 256

<210> SEQ ID NO 1
<211> LENGTH: 902
<212> TYPE: DNA
<213> ORGANISM: Homo sapiens
<220> FEATURE:
<221> NAME/KEY: misc_feature
<222> LOCATION: (870)
<223> OTHER INFORMATION: n equals a,t,g, or c
<220> FEATURE:
<221> NAME/KEY: misc_feature
<222> LOCATION: (874)
<223> OTHER INFORMATION: n equals a,t,g, or c
<220> FEATURE:
<221> NAME/KEY: misc_feature
<222> LOCATION: (878)
<223> OTHER INFORMATION: n equals a,t,g, or c

<400> SEQUENCE: 1

ggcagagcca caggaaggat gaggaagacc aggctctggg ggctgctgtg gatgctcttt     60

gtctcagaac tccgagctgc aactaaatta actgaggaaa agtatgaact gaaagagggg    120

cagaccctgg atgtgaaatg tgactacacg ctagagaagt ttgccagcag ccagaaagct    180

tggcagataa taagggacgg agagatgccc aagaccctgg catgcacaga gaggccttca    240

aagaattccc atccagtcca agtggggagg atcatactag aagactacca tgatcatggt    300

ttactgcgcg tccgaatggt caaccttcaa gtggaagatt ctggactgta tcagtgtgtg    360

atctaccagc ctcccaagga gcctcacatg ctgttcgatc gcatccgctt ggtggtgacc    420

aagggttttt cagggacccc tggctccaat gagaattcta cccagaatgt gtataagatt    480

cctcctacca ccactaaggc cttgtgccca ctctatacca gccccagaac tgtgacccaa    540

gctccaccca agtcaactgc cgatgtctcc actcctgact ctgaaatcaa ccttacaaat    600

gtgacagata tcatcagggt tccggtgttc aacattgtca ttctcctggc tggtggattc    660

ctgagtaaga gcctggtctt ctctgtcctg tttgctgtca cgctgaggtc atttgtaccc    720

taggcccacg aacccacgag aatgtcctct gacttccagc cacatccatc tggcagttgt    780
```

```
gccaagggag gagggaggag gtaaaaggca gggagttaat aacatgaatt aaatctgtaa    840

tcaccrgcta aaaaaaaaaa aaaaaaaacn cgancctngg ttttcagctc catcagctcc    900

tt                                                                   902


<210> SEQ ID NO 2
<211> LENGTH: 234
<212> TYPE: PRT
<213> ORGANISM: Homo sapiens

<400> SEQUENCE: 2

Met Arg Lys Thr Arg Leu Trp Gly Leu Leu Trp Met Leu Phe Val Ser
  1               5                  10                  15

Glu Leu Arg Ala Ala Thr Lys Leu Thr Glu Glu Lys Tyr Glu Leu Lys
             20                  25                  30

Glu Gly Gln Thr Leu Asp Val Lys Cys Asp Tyr Thr Leu Glu Lys Phe
         35                  40                  45

Ala Ser Ser Gln Lys Ala Trp Gln Ile Ile Arg Asp Gly Glu Met Pro
     50                  55                  60

Lys Thr Leu Ala Cys Thr Glu Arg Pro Ser Lys Asn Ser His Pro Val
 65                  70                  75                  80

Gln Val Gly Arg Ile Ile Leu Glu Asp Tyr His Asp His Gly Leu Leu
                 85                  90                  95

Arg Val Arg Met Val Asn Leu Gln Val Glu Asp Ser Gly Leu Tyr Gln
            100                 105                 110

Cys Val Ile Tyr Gln Pro Pro Lys Glu Pro His Met Leu Phe Asp Arg
        115                 120                 125

Ile Arg Leu Val Val Thr Lys Gly Phe Ser Gly Thr Pro Gly Ser Asn
    130                 135                 140

Glu Asn Ser Thr Gln Asn Val Tyr Lys Ile Pro Pro Thr Thr Thr Lys
145                 150                 155                 160

Ala Leu Cys Pro Leu Tyr Thr Ser Pro Arg Thr Val Thr Gln Ala Pro
                165                 170                 175

Pro Lys Ser Thr Ala Asp Val Ser Thr Pro Asp Ser Glu Ile Asn Leu
            180                 185                 190

Thr Asn Val Thr Asp Ile Ile Arg Val Pro Val Phe Asn Ile Val Ile
        195                 200                 205

Leu Leu Ala Gly Gly Phe Leu Ser Lys Ser Leu Val Phe Ser Val Leu
    210                 215                 220

Phe Ala Val Thr Leu Arg Ser Phe Val Pro
225                 230


<210> SEQ ID NO 3
<211> LENGTH: 16
<212> TYPE: PRT
<213> ORGANISM: Homo sapiens

<400> SEQUENCE: 3

Ile Arg Val Pro Val Phe Asn Ile Val Ile Leu Leu Ala Gly Gly Phe
  1               5                  10                  15


<210> SEQ ID NO 4
<211> LENGTH: 198
<212> TYPE: PRT
<213> ORGANISM: Homo sapiens

<400> SEQUENCE: 4

Met Arg Lys Thr Arg Leu Trp Gly Leu Leu Trp Met Leu Phe Val Ser
```

-continued

```
  1               5                  10                  15

Glu Leu Arg Ala Ala Thr Lys Leu Thr Glu Glu Lys Tyr Glu Leu Lys
             20                  25                  30

Glu Gly Gln Thr Leu Asp Val Lys Cys Asp Tyr Thr Leu Glu Lys Phe
         35                  40                  45

Ala Ser Ser Gln Lys Ala Trp Gln Ile Ile Arg Asp Gly Glu Met Pro
     50                  55                  60

Lys Thr Leu Ala Cys Thr Glu Arg Pro Ser Lys Asn Ser His Pro Val
 65                  70                  75                  80

Gln Val Gly Arg Ile Ile Leu Glu Asp Tyr His Asp His Gly Leu Leu
                 85                  90                  95

Arg Val Arg Met Val Asn Leu Gln Val Glu Asp Ser Gly Leu Tyr Gln
            100                 105                 110

Cys Val Ile Tyr Gln Pro Pro Lys Glu Pro His Met Leu Phe Asp Arg
        115                 120                 125

Ile Arg Leu Val Val Thr Lys Gly Phe Ser Gly Thr Pro Gly Ser Asn
    130                 135                 140

Glu Asn Ser Thr Gln Asn Val Tyr Lys Ile Pro Pro Thr Thr Thr Lys
145                 150                 155                 160

Ala Leu Cys Pro Leu Tyr Thr Ser Pro Arg Thr Val Thr Gln Ala Pro
                165                 170                 175

Pro Lys Ser Thr Ala Asp Val Ser Thr Pro Asp Ser Glu Ile Asn Leu
            180                 185                 190

Thr Asn Val Thr Asp Ile
        195


<210> SEQ ID NO 5
<211> LENGTH: 172
<212> TYPE: PRT
<213> ORGANISM: Homo sapiens

<400> SEQUENCE: 5

Glu Lys Tyr Glu Leu Lys Glu Gly Gln Thr Leu Asp Val Lys Cys Asp
  1               5                  10                  15

Tyr Thr Leu Glu Lys Phe Ala Ser Ser Gln Lys Ala Trp Gln Ile Ile
             20                  25                  30

Arg Asp Gly Glu Met Pro Lys Thr Leu Ala Cys Thr Glu Arg Pro Ser
         35                  40                  45

Lys Asn Ser His Pro Val Gln Val Gly Arg Ile Ile Leu Glu Asp Tyr
     50                  55                  60

His Asp His Gly Leu Leu Arg Val Arg Met Val Asn Leu Gln Val Glu
 65                  70                  75                  80

Asp Ser Gly Leu Tyr Gln Cys Val Ile Tyr Gln Pro Pro Lys Glu Pro
                 85                  90                  95

His Met Leu Phe Asp Arg Ile Arg Leu Val Val Thr Lys Gly Phe Ser
            100                 105                 110

Gly Thr Pro Gly Ser Asn Glu Asn Ser Thr Gln Asn Val Tyr Lys Ile
        115                 120                 125

Pro Pro Thr Thr Thr Lys Ala Leu Cys Pro Leu Tyr Thr Ser Pro Arg
    130                 135                 140

Thr Val Thr Gln Ala Pro Pro Lys Ser Thr Ala Asp Val Ser Thr Pro
145                 150                 155                 160

Asp Ser Glu Ile Asn Leu Thr Asn Val Thr Asp Ile
                165                 170
```

<210> SEQ ID NO 6
<211> LENGTH: 26
<212> TYPE: PRT
<213> ORGANISM: Homo sapiens

<400> SEQUENCE: 6

Met Arg Lys Thr Arg Leu Trp Gly Leu Leu Trp Met Leu Phe Val Ser
1 5 10 15

Glu Leu Arg Ala Ala Thr Lys Leu Thr Glu
20 25

<210> SEQ ID NO 7
<211> LENGTH: 1923
<212> TYPE: DNA
<213> ORGANISM: Homo sapiens
<220> FEATURE:
<221> NAME/KEY: misc_feature
<222> LOCATION: (1900)
<223> OTHER INFORMATION: n equals a,t,g, or c

<400> SEQUENCE: 7
acccgctccg ctccgctccg ctcggccccg cgccgcccgt caacatgatc cgctgcggcc 60
tggcctgcga gcgctgccgc tggatcctgc ccctgctcct actcagcgcc atcgccttcg 120
acatcatcgc gctggccggc cgcggctggt tgcagtctag cgaccacggc cagacgtcct 180
cgctgtggtg gaaatgctcc caagagggcg gcggcagcgg gtcctacgag gagggctgtc 240
agagcctcat ggagtacgcg tggggtagag cagcggctgc catgctcttc tgtggcttca 300
tcatcctggt gatctgtttc atcctctcct tcttcgccct ctgtggaccc cagatgcttg 360
tcttcctgag agtgattgga ggtctccttg ccttggctgc tgtgttccag atcatctccc 420
tggtaattta ccccgtgaag tacacccaga ccttcaccct tcatgccaac cstgctgtca 480
cttacatcta taactgggcc tacggctttg ggtgggcagc cacgattatc ctgatyggct 540
gtgccttctt cttctgctgc ctccccaact acgaagatga ccttctgggc aatgccaagc 600
ccaggtactt ctacacatct gcctaacttg ggaatgaatg tgggagaaaa tcgctgctgc 660
tgagatggac tccagaagaa gaaactgttt ctccaggcga ctttgaaccc attttttggc 720
agtgttcata ttattaaact agtcaaaaat gctaaaataa tttgggagaa aatatttttt 780
aagtagtgtt atagtttcat gtttatcttt tattatgttt tgtgaagttg tgtcttttca 840
ctaattacct atactatgcc aatatttcct tatatctatc cataacattt atactacatt 900
tgtaagagaa tatgcacgtg aaacttaaca ctttataagg taaaaatgag gtttccaaga 960
tttaataatc tgatcaagtt cttgttattt ccaaatagaa tggactcggt ctgttaaggg 1020
ctaaggagaa gaggaagata aggttaaaag ttgttaatga ccaaacattc taaaagaaat 1080
gcaaaaaaaa agtttatttt caagccttcg aactatttaa ggaaagcaaa atcatttcct 1140
aaatgcatat catttgtgag aatttctcat taatatcctg aatcattcat ttcagctaag 1200
gcttcatgtt gactcgatat gtcatctagg aaagtactat ttcatggtcc aaacctgttg 1260
ccatagttgg taaggctttc ctttaagtgt gaaatattta gatgaaattt tctcttttaa 1320
agttctttat agggttaggg tgtgggaaaa tgctatatta ataaatctgt agtgttttgt 1380
gtttatatgt tcagaaccag agtagactgg attgaaagat ggactgggtc taatttatca 1440
tgactgatag atctggttaa gttgtgtagt aaagcattag gagggtcatt cttgtcacaa 1500
aagtgccact aaaacagcct caggagaata aatgacttgc ttttctaaat ctcaggttta 1560
tctgggctct atcatataga caggcttctg atagtttgca actgtaagca gaaacctaca 1620
tatagttaaa atcctggtct ttcttggtaa acagatttta aatgtctgat ataaaacatg 1680

```
ccacaggaga attcggggat ttgagtttct ctgaatagca tatatatgat gcatcggata   1740

ggtcattatg attttttacc atttcgactt acataatgaa aaccaattca ttttaaatat   1800

cagattatta ttttgtaagt tgtggaaaaa gctaattgta gttttcatta tgaagttttc   1860

ccaataaacc aggtattcta aaaaaaaaaa aaaaaaactn gaggggggc ccggtaccca   1920

att                                                                 1923
```

<210> SEQ ID NO 8
<211> LENGTH: 193
<212> TYPE: PRT
<213> ORGANISM: Homo sapiens
<220> FEATURE:
<221> NAME/KEY: SITE
<222> LOCATION: (143)
<223> OTHER INFORMATION: Xaa equals any of the naturally occurring
L-amino acids

<400> SEQUENCE: 8

```
Met Ile Arg Cys Gly Leu Ala Cys Glu Arg Cys Arg Trp Ile Leu Pro
  1               5                  10                  15

Leu Leu Leu Leu Ser Ala Ile Ala Phe Asp Ile Ile Ala Leu Ala Gly
             20                  25                  30

Arg Gly Trp Leu Gln Ser Ser Asp His Gly Gln Thr Ser Ser Leu Trp
         35                  40                  45

Trp Lys Cys Ser Gln Glu Gly Gly Gly Ser Gly Ser Tyr Glu Glu Gly
     50                  55                  60

Cys Gln Ser Leu Met Glu Tyr Ala Trp Gly Arg Ala Ala Ala Ala Met
 65                  70                  75                  80

Leu Phe Cys Gly Phe Ile Ile Leu Val Ile Cys Phe Ile Leu Ser Phe
                 85                  90                  95

Phe Ala Leu Cys Gly Pro Gln Met Leu Val Phe Leu Arg Val Ile Gly
            100                 105                 110

Gly Leu Leu Ala Leu Ala Ala Val Phe Gln Ile Ile Ser Leu Val Ile
        115                 120                 125

Tyr Pro Val Lys Tyr Thr Gln Thr Phe Thr Leu His Ala Asn Xaa Ala
    130                 135                 140

Val Thr Tyr Ile Tyr Asn Trp Ala Tyr Gly Phe Gly Trp Ala Ala Thr
145                 150                 155                 160

Ile Ile Leu Ile Gly Cys Ala Phe Phe Phe Cys Cys Leu Pro Asn Tyr
                165                 170                 175

Glu Asp Asp Leu Leu Gly Asn Ala Lys Pro Arg Tyr Phe Tyr Thr Ser
            180                 185                 190

Ala
```

<210> SEQ ID NO 9
<211> LENGTH: 1022
<212> TYPE: DNA
<213> ORGANISM: Homo sapiens

<400> SEQUENCE: 9

```
cgctcctgcc gccgggaccc tcgacctcct cagagcagcc ggctgccgcc ccgggaagat     60

ggcgaggagg agccgccacc gcctcctcct gctgctgctg cgctacctgg tggtcgccct    120

gggctatcat aaggcctatg ggttttctgc cccaaaagac caacaagtag tcacagcagt    180

agwgtaccaa gaggctattt tagcctgcaa aaccccaaag aagactgttt sctccagatt    240

agagtggaag aaactgggtc ggagtgtctc ctttgtctac tatcaacaga ctcttcaagg    300
```

```
tgattttaaa aatcgagctg agatgataga tttcaatatc cggatcaaaa atgtgacaag    360

aagtgatgcg gggaaatatc gttgtgaagt tagtgcccca tctgagcaag gccaaaacct    420

ggaagaggat acagtcactc tggaagtatt agtggctcca gcagttccat catgtgaagt    480

accctcttct gctctgagtg gaactgtggt agagctacga tgtcaagaca aagaagggaa    540

tccagctcct gaatacacat ggtttaagga tggcatccgt ttgctagaaa atcccagact    600

tggctcccaa agcaccaaca gctcatacac aatgaataca aaaactggaa ctctgcaatt    660

taatactgtt tccaaactgg acactggaga atattcctgt gaagcccgca attctgttgg    720

atatcgcagg tgtcctggga aacgaatgca agtagatgat ctcaacataa gtggcatcat    780

agcagccgta gtagttgtgg ccttagtgat ttccgtttgt ggccttggtg tatgctatgc    840

tcagaggaaa ggctactttt caaaagaaac ctccttccag aagagtaatt cttcatctaa    900

agccacgaca atgagtgaaa atgatttcaa gcacacaaaa tcctttataa tttaaagact    960

ccactttaga gatacaccaa agccaccgtt gttacacaag ttattaaact attataaaac   1020

tc                                                                  1022


<210> SEQ ID NO 10
<211> LENGTH: 298
<212> TYPE: PRT
<213> ORGANISM: Homo sapiens
<220> FEATURE:
<221> NAME/KEY: SITE
<222> LOCATION: (42)
<223> OTHER INFORMATION: Xaa equals any amino acid
<220> FEATURE:
<221> NAME/KEY: SITE
<222> LOCATION: (58)
<223> OTHER INFORMATION: Xaa equals any amino acid

<400> SEQUENCE: 10

Met Ala Arg Arg Ser Arg His Arg Leu Leu Leu Leu Leu Leu Arg Tyr
  1               5                  10                  15

Leu Val Val Ala Leu Gly Tyr His Lys Ala Tyr Gly Phe Ser Ala Pro
             20                  25                  30

Lys Asp Gln Gln Val Val Thr Ala Val Xaa Tyr Gln Glu Ala Ile Leu
         35                  40                  45

Ala Cys Lys Thr Pro Lys Lys Thr Val Xaa Ser Arg Leu Glu Trp Lys
     50                  55                  60

Lys Leu Gly Arg Ser Val Ser Phe Val Tyr Tyr Gln Gln Thr Leu Gln
 65                  70                  75                  80

Gly Asp Phe Lys Asn Arg Ala Glu Met Ile Asp Phe Asn Ile Arg Ile
                 85                  90                  95

Lys Asn Val Thr Arg Ser Asp Ala Gly Lys Tyr Arg Cys Glu Val Ser
            100                 105                 110

Ala Pro Ser Glu Gln Gly Gln Asn Leu Glu Glu Asp Thr Val Thr Leu
        115                 120                 125

Glu Val Leu Val Ala Pro Ala Val Pro Ser Cys Glu Val Pro Ser Ser
    130                 135                 140

Ala Leu Ser Gly Thr Val Val Glu Leu Arg Cys Gln Asp Lys Glu Gly
145                 150                 155                 160

Asn Pro Ala Pro Glu Tyr Thr Trp Phe Lys Asp Gly Ile Arg Leu Leu
                165                 170                 175

Glu Asn Pro Arg Leu Gly Ser Gln Ser Thr Asn Ser Ser Tyr Thr Met
            180                 185                 190

Asn Thr Lys Thr Gly Thr Leu Gln Phe Asn Thr Val Ser Lys Leu Asp
        195                 200                 205
```

-continued

```
Thr Gly Glu Tyr Ser Cys Glu Ala Arg Asn Ser Val Gly Tyr Arg Arg
    210                 215                 220

Cys Pro Gly Lys Arg Met Gln Val Asp Asp Leu Asn Ile Ser Gly Ile
225                 230                 235                 240

Ile Ala Ala Val Val Val Val Ala Leu Val Ile Ser Val Cys Gly Leu
                245                 250                 255

Gly Val Cys Tyr Ala Gln Arg Lys Gly Tyr Phe Ser Lys Glu Thr Ser
            260                 265                 270

Phe Gln Lys Ser Asn Ser Ser Ser Lys Ala Thr Thr Met Ser Glu Asn
        275                 280                 285

Asp Phe Lys His Thr Lys Ser Phe Ile Ile
    290                 295


<210> SEQ ID NO 11
<211> LENGTH: 1041
<212> TYPE: DNA
<213> ORGANISM: Homo sapiens

<400> SEQUENCE: 11

tcgacccacg cgtccgccca cgcgtccgcc cacgcgtccg ggcgcaggac gtgcactatg      60

gctcggggct cgctgcgccg gttgctgcgg ctcctcgtgc tggggctctg gctggcgttg     120

ctgcgctccg tggccgggga gcaagcgcca ggcaccgccc cctgctcccg cggcagctcc     180

tggagcgcgg acctggacaa gtgcatggac tgcgcgtctt gcagggcgcg accgcacagc     240

gacttctgcc tgggctgcgc tgcagcacct cctgccccct tccggctgct ttggcccatc     300

cttgggggcg ctctgagcct gaccttcgtg ctggggctgc tttctggctt tttggtctgg     360

agacgatgcc gcagagagag aagttcacca cccccataga ggagaccggc ggagagggct     420

gcccagctgt ggcgctgatc cagtgacaat gtgccccctg ccagccgggg ctcgcccact     480

catcattcat tcatccattc tagagccagt ctctgcctcc cagacgcggc gggagcaagc     540

tcctccaacc acaagggggg tggggggcgg tgaatcacct cygaggcctg ggcccagggt     600

tcaggggaac ttccaaggtg tctggttgcc ctgcctctgg ctccagaaca gaaagggagc     660

ctcacgctgg ctcacacaaa acagctgaca ctgactaagg aactgcagca tttgcacagg     720

ggagggggt gccctccttc ctagaggccc tgggggccag gctgacttgg ggggcagact      780

tgacactagg ccccactcac tcagatgtcc tgaaattcca ccacgggggt caccctgggg     840

ggttagggac ctatttttaa cactaggggg ctggcccact aggagggctg gccctaagat     900

acagaccccc ccaactcccc aaagcgggga ggagatattt attttgggga gagtttggag     960

gggagggaga atttattaat aaaagaatct ttaactttaa aaaaaaaaaa aaaaaagggc    1020

ggccgctcta gaggatccct c                                              1041


<210> SEQ ID NO 12
<211> LENGTH: 113
<212> TYPE: PRT
<213> ORGANISM: Homo sapiens

<400> SEQUENCE: 12

Met Ala Arg Gly Ser Leu Arg Arg Leu Leu Arg Leu Leu Val Leu Gly
  1               5                  10                  15

Leu Trp Leu Ala Leu Leu Arg Ser Val Ala Gly Glu Gln Ala Pro Gly
            20                  25                  30

Thr Ala Pro Cys Ser Arg Gly Ser Ser Trp Ser Ala Asp Leu Asp Lys
        35                  40                  45
```

```
Cys Met Asp Cys Ala Ser Cys Arg Ala Arg Pro His Ser Asp Phe Cys
     50                  55                  60

Leu Gly Cys Ala Ala Ala Pro Pro Ala Pro Phe Arg Leu Leu Trp Pro
 65                  70                  75                  80

Ile Leu Gly Gly Ala Leu Ser Leu Thr Phe Val Leu Gly Leu Leu Ser
                 85                  90                  95

Gly Phe Leu Val Trp Arg Arg Cys Arg Arg Glu Arg Ser Ser Pro Pro
            100                 105                 110

Pro


<210> SEQ ID NO 13
<211> LENGTH: 1052
<212> TYPE: DNA
<213> ORGANISM: Homo sapiens

<400> SEQUENCE: 13

tcgacccacg cgtccgccca cgcgtccgcc cacgcgtccg ggcgggcgca ggacgtgcac      60

tatggctcgg ggctcgctgc gccggttgct gcggctcctc gtgctggggc tctggctggc     120

gttgctgcgc tccgtggccg gggagcaagc gccaggcacc gccccctgct cccgcggcag     180

ctcctggagc gcggacctgg acaagtgcat ggactgcagc acctcctgcc cccttccggc     240

tgctttggcc catccttggg ggcgctctga gcctgacctt cgtgctgggg ctgctttctg     300

gctttttggt ctggagacga tgccgcagag agagaagttc accaccccca tagaggagac     360

cggcggagag ggctgcccag ctgtggcgct gatccagtga caatgtgccc cctgccagcc     420

ggggctcgcc cactcatcat tcattcatcc attctagagc cagtctctgc ctcccagacg     480

cggcgggagc caagctcctc caaccacaag gggggtgggg ggcggtgaat cacctctgag     540

gcctgggccc agggttcagg ggaaccttcc aaggtgtctg gttgccctgc ctctggctcc     600

agaacagaaa gggagcctca cgctggctca cacaaaacag ctgacactga ctaaggaact     660

gcagcatttg cacaggggag ggggtgccct ccttcctaga ggccctgggg gccaggctga     720

cttgggggc agacttgaca ctaggcccca ctcactcaga tgtcctgaaa ttccaccacg     780

ggggtcaccc tggggggtta gggacctatt tttaacacta gggggctggc ccactaggag     840

ggctggccct aagatacaga cccccccaac tccccaaagc ggggaggaga tatttatttt     900

ggggagagtt tggaggggag ggtggggggg gggaaaaaaa aataaaaaaa aaaattttta     960

atttttaaaa aaaaaaaaaa aaaaaaaaaa aaaaaaaaaa aaaaaaaaaa aaaaaaaaaa    1020

aaaaaaaaaa aaaaaaaaaa aaaaaaaaaa aa                                  1052


<210> SEQ ID NO 14
<211> LENGTH: 112
<212> TYPE: PRT
<213> ORGANISM: Homo sapiens

<400> SEQUENCE: 14

Met Ala Arg Gly Ser Leu Arg Arg Leu Leu Arg Leu Leu Val Leu Gly
  1               5                  10                  15

Leu Trp Leu Ala Leu Leu Arg Ser Val Ala Gly Glu Gln Ala Pro Gly
             20                  25                  30

Thr Ala Pro Cys Ser Arg Gly Ser Ser Trp Ser Ala Asp Leu Asp Lys
         35                  40                  45

Cys Met Asp Cys Ser Thr Ser Cys Pro Leu Pro Ala Ala Leu Ala His
     50                  55                  60

Pro Trp Gly Arg Ser Glu Pro Asp Leu Arg Ala Gly Ala Ala Phe Trp
 65                  70                  75                  80
```

```
Leu Phe Gly Leu Glu Thr Met Pro Gln Arg Glu Lys Phe Thr Thr Pro
                85                  90                  95

Ile Glu Glu Thr Gly Gly Glu Gly Cys Pro Ala Val Ala Leu Ile Gln
            100                 105                 110


<210> SEQ ID NO 15
<211> LENGTH: 1000
<212> TYPE: DNA
<213> ORGANISM: Homo sapiens

<400> SEQUENCE: 15

agcggcgggc gcaggacgtg cactatggct cggggctcgc tgcgccggtt gctgcggctc      60

ctcgtgctgg ggctctggct ggcgttgctg cgctccgtgg ccggggagca agcgccaggc     120

accgcccccct gctcccgcgg cagctcctgg agcgcggacc tggacaagtg catggactgc    180

gcgtcttgca gggcgcgacc gcacagcgac ttctgcctgg gctgcgctgc agcacctcct     240

gccccccttcc ggctgctttg gcccatcctt gggggcgctc tgagcctgac cttcgtgctg    300

gggctgcttt ctggcttttt ggtctggaga cgatgccgca ggagagagaa gttcaccacc     360

cccatagagg agaccggcgg agagggctgc ccagctgtgg cgctgatcca gtgacaatgt     420

gccccctgcc agccggggct cgcccactca tcattcattc atccattcta gagccagtct     480

ctgcctccca gacgcggcgg gagccaagct cctccaacca caagggggggt gggggggcggt    540

gaatcacctc tgaggcctgg gcccagggtt caggggaacc ttccaaggtg tctggttgcc     600

ctgcctctgg ctccagaaca gaaagggagc ctcacgctgg ctcacacaaa acagctgaca     660

ctgactaagg aactgcagca tttgcacagg ggagggggggt gccctccttc ctagaggccc    720

tgggggccag gctgacttgg ggggcagact tgacactagg ccccactcac tcagatgtcc     780

tgaaattcca ccacgggggt caccctgggg ggttagggac ctatttttaa cactaggggg     840

ctggcccact aggagggctg gccctaagat acagaccccc ccaactcccc aaagcgggga     900

ggagatattt attttgggga gagtttggag gggagggaga atttattaat aaaagaatct     960

ttaactttaa aaaaaaaaaa aaaaactcga gggggggccc                          1000


<210> SEQ ID NO 16
<211> LENGTH: 129
<212> TYPE: PRT
<213> ORGANISM: Homo sapiens

<400> SEQUENCE: 16

Met Ala Arg Gly Ser Leu Arg Arg Leu Leu Arg Leu Leu Val Leu Gly
  1               5                  10                  15

Leu Trp Leu Ala Leu Leu Arg Ser Val Ala Gly Glu Gln Ala Pro Gly
            20                  25                  30

Thr Ala Pro Cys Ser Arg Gly Ser Ser Trp Ser Ala Asp Leu Asp Lys
        35                  40                  45

Cys Met Asp Cys Ala Ser Cys Arg Ala Arg Pro His Ser Asp Phe Cys
     50                  55                  60

Leu Gly Cys Ala Ala Ala Pro Pro Ala Pro Phe Arg Leu Leu Trp Pro
 65                  70                  75                  80

Ile Leu Gly Gly Ala Leu Ser Leu Thr Phe Val Leu Gly Leu Leu Ser
                85                  90                  95

Gly Phe Leu Val Trp Arg Arg Cys Arg Arg Arg Glu Lys Phe Thr Thr
            100                 105                 110

Pro Ile Glu Glu Thr Gly Gly Glu Gly Cys Pro Ala Val Ala Leu Ile
        115                 120                 125
```

Gln

<210> SEQ ID NO 17
<211> LENGTH: 1037
<212> TYPE: DNA
<213> ORGANISM: Homo sapiens
<220> FEATURE:
<221> NAME/KEY: misc_feature
<222> LOCATION: (936)..(936)
<223> OTHER INFORMATION: n equals a,t,g, or c
<220> FEATURE:
<221> NAME/KEY: misc_feature
<222> LOCATION: (946)..(946)
<223> OTHER INFORMATION: n equals a,t,g, or c
<220> FEATURE:
<221> NAME/KEY: misc_feature
<222> LOCATION: (951)..(951)
<223> OTHER INFORMATION: n equals a,t,g, or c

<400> SEQUENCE: 17

```
ccggtccgga attcccgggt cgacccacgc gtccgggcgg gcgcaggacg tgcactatgg     60

ctcggggctc gctgcgccgg ttgctgcggc tcctcgtgct ggggctctgg ctggcgttgc    120

tgcgctccgt ggccggggag caagcgccag gcaccgcccc ctgctcccgc ggcagctcct    180

ggagcgcgga cctggacaag tgcatggact gcagcacctc ctgcccccctt ccggctgctt    240

tggcccatcc ttgggggcgc tctgagcctg accttcgtgc tggggctgct ttctggcttt    300

ttggtctgga gacgatgccg caggagagag aagttcacca cccccataga ggagaccggc    360

ggagagggct gcccagctgt ggcgctgatc cagtgacaat gtgcccccctg ccagccgggg    420

ctcgcccact catcattcat tcatccattc tagagccagt ctctgcctcc cagacgcggc    480

gggagccaag ctcctccaac cacaaggggg gtggggggcg gtgaatcacc tctgaggcct    540

gggcccaggg ttcaggggaa ccttccaagg tgtctggttg ccctgcctct ggctccagaa    600

cagaaaggga gcctcacgct ggctcacaca aaacagctga cactgactaa ggaactgcag    660

catttgcaca ggggaagggg gtgccctcct tcctagaggc cctgggggcc aggctgactt    720

gggggcaga cttgacacta ggccccactc actcagatgt cctgaaattc caccacgggg    780

gtcaccctgg ggggttaggg acctattttt aacactaggg ggctggccca ctaggagggc    840

tggccctaag atacagaccc ccccaactcc ccaaagcggg ggggggatat ttattttggg    900

gagagtttgg aggggagggg gatttttttt ttaaangatt ttttantttt naaaaaaaaa    960

aaaaaaaaaa aaaaaaaaaa aaaaaaaaaa aaaaaaaaaa aaaaaaaaaa aaaaaaaaaa   1020

aaaaaaaaaa aaaaaaa                                                  1037
```

<210> SEQ ID NO 18
<211> LENGTH: 155
<212> TYPE: PRT
<213> ORGANISM: Homo sapiens

<400> SEQUENCE: 18

```
Met Ala Arg Gly Ser Leu Arg Arg Leu Leu Arg Leu Leu Val Leu Gly
  1               5                  10                  15

Leu Trp Leu Ala Leu Leu Arg Ser Val Ala Gly Glu Gln Ala Pro Gly
            20                  25                  30

Thr Ala Pro Cys Ser Arg Gly Ser Ser Trp Ser Ala Asp Leu Asp Lys
        35                  40                  45

Cys Met Asp Cys Ser Thr Ser Cys Pro Leu Pro Ala Ala Leu Ala His
    50                  55                  60

Pro Trp Gly Arg Ser Glu Pro Asp Leu Arg Ala Gly Ala Ala Phe Trp
```

```
 65                  70                  75                  80

Leu Phe Gly Leu Glu Thr Met Pro Gln Glu Arg Glu Val His His Pro
                85                  90                  95

His Arg Gly Asp Arg Arg Arg Gly Leu Pro Ser Cys Gly Ala Asp Pro
            100                 105                 110

Val Thr Met Cys Pro Leu Pro Ala Gly Ala Arg Pro Leu Ile Ile His
        115                 120                 125

Ser Ser Ile Leu Glu Pro Val Ser Ala Ser Gln Thr Arg Arg Glu Pro
    130                 135                 140

Ser Ser Ser Asn His Lys Gly Gly Gly Gly Arg
145                 150                 155


<210> SEQ ID NO 19
<211> LENGTH: 155
<212> TYPE: PRT
<213> ORGANISM: Homo sapiens

<400> SEQUENCE: 19

Met Ala Arg Gly Ser Leu Arg Arg Leu Leu Arg Leu Leu Val Leu Gly
  1               5                  10                  15

Leu Trp Leu Ala Leu Leu Arg Ser Val Ala Gly Glu Gln Ala Pro Gly
            20                  25                  30

Thr Ala Pro Cys Ser Arg Gly Ser Ser Trp Ser Ala Asp Leu Asp Lys
        35                  40                  45

Cys Met Asp Cys Ser Thr Ser Cys Pro Leu Pro Ala Ala Leu Ala His
     50                  55                  60

Pro Trp Gly Arg Ser Glu Pro Asp Leu Arg Ala Gly Ala Ala Phe Trp
 65                  70                  75                  80

Leu Phe Gly Leu Glu Thr Met Pro Gln Glu Arg Glu Val His His Pro
                85                  90                  95

His Arg Gly Asp Arg Arg Arg Gly Leu Pro Ser Cys Gly Ala Asp Pro
            100                 105                 110

Val Thr Met Cys Pro Leu Pro Ala Gly Ala Arg Pro Leu Ile Ile His
        115                 120                 125

Ser Ser Ile Leu Glu Pro Val Ser Ala Ser Gln Thr Arg Arg Glu Pro
    130                 135                 140

Ser Ser Ser Asn His Lys Gly Gly Gly Gly Arg
145                 150                 155


<210> SEQ ID NO 20
<211> LENGTH: 996
<212> TYPE: DNA
<213> ORGANISM: Homo sapiens
<220> FEATURE:
<221> NAME/KEY: misc_feature
<222> LOCATION: (584)..(584)
<223> OTHER INFORMATION: n equals a,t,g, or c

<400> SEQUENCE: 20

cgcctggcac catgaggacg cctgggcctc tgcctgtgct gctgctgctc ctggcgggag      60

cccccgccgc gcggcccact cccccgacct gctactcccg catgcgggcc ctgagccagg     120

agatcacccg cgacttcaac ctcctgcagg tctcggagcc ctcggagcca tgtgtgagat     180

acctgcccag gctgtacctg gacatacaca attactgtgt gctggacaag ctgcgggact     240

ttgtggcctc gcccccgtgt tggaaagtgg cccaggtaga ttccttgaag gacaaagcac     300

ggaagctgta caccatcatg aactcgttct gcaggagaga tttggtattc ctgttggatg     360

actgcaatgc cttggaatac ccaatcccag tgactacggt cctgccagat cgtcagcgct     420
```

```
aagggaactg agaccagaga aagaacccaa gagaactaaa gttatgtcag ctacccagac    480

ttaatgggcc agagccatga ccctcacagg tcttgtgtta gttgtatctg aaactgttat    540

gtatctctct accttctgga aaacagggct ggtattccta cccnggaacc tcctttgagc    600

atagagttag caaccatgct tctcattccc ttgactcatg tcttgccagg atggttagat    660

acacagcatg ttgatttggt cacctaaaaa gaagaaaagg actaacaagc ttcactttta    720

tgaacaacta ttttgagaac atgcacaata gtatgttttt attactggtt taatggagta    780

atggtacttt tattctttct tgatagaaac ctgcttacat ttaaccaagc ttctattatg    840

ccttttttcta acacagactt tcttcactgt ctttcattta aaaagaaatt aatgctctta   900

agatatatat tttaygtagt gctgacagga cccactcttt cattgaaagg tgatgaaaat    960

caaataaaga atctcttcac atgaraaaaa aaaaaa                              996
```

<210> SEQ ID NO 21
<211> LENGTH: 136
<212> TYPE: PRT
<213> ORGANISM: Homo sapiens

<400> SEQUENCE: 21

```
Met Arg Thr Pro Gly Pro Leu Pro Val Leu Leu Leu Leu Leu Ala Gly
1               5                   10                  15

Ala Pro Ala Ala Arg Pro Thr Pro Pro Thr Cys Tyr Ser Arg Met Arg
            20                  25                  30

Ala Leu Ser Gln Glu Ile Thr Arg Asp Phe Asn Leu Leu Gln Val Ser
        35                  40                  45

Glu Pro Ser Glu Pro Cys Val Arg Tyr Leu Pro Arg Leu Tyr Leu Asp
    50                  55                  60

Ile His Asn Tyr Cys Val Leu Asp Lys Leu Arg Asp Phe Val Ala Ser
65                  70                  75                  80

Pro Pro Cys Trp Lys Val Ala Gln Val Asp Ser Leu Lys Asp Lys Ala
                85                  90                  95

Arg Lys Leu Tyr Thr Ile Met Asn Ser Phe Cys Arg Arg Asp Leu Val
            100                 105                 110

Phe Leu Leu Asp Asp Cys Asn Ala Leu Glu Tyr Pro Ile Pro Val Thr
        115                 120                 125

Thr Val Leu Pro Asp Arg Gln Arg
    130                 135
```

<210> SEQ ID NO 22
<211> LENGTH: 1092
<212> TYPE: DNA
<213> ORGANISM: Homo sapiens

<400> SEQUENCE: 22

```
ggccgctcta gaactagtgg atcccccggg ctgcaggatt cggcacgagc gcctggcacc     60

atgaggacgc ctgggcctct gcccgtgctg ctgctgctcc tggcgggagc cccgccgcg    120

cggcccactc ccccgacctg ctactcccgc atgcgggccc tgagccagga gatcacccgc    180

gacttcaacc tcctgcaggt ctcggagccc tcggagccat gtgtgagata cctgcccagg    240

ctgtacctgg acatacacaa ttactgtgtg ctggacaagc tgcgggactt tgtggcctcg    300

cccccgtgtt ggaaagtggc ccaggtagat tccttgaagg acaaagcacg gaagctgtac    360

accatcatga actcgttctg caggagagat ttggtattcc tgttggatga ctgcaatgcc    420

ttggaatacc caatcccagt gactacggtc ctgccagatc gtcagcgcta agggaactga    480
```

-continued

```
gaccagagaa agaacccaag agaactaaag ttatgtcagc tacccagact taatgggcca    540

gagccatgac cctcacaggt cttgtgttag ttgtatctga aactgttatg tatctctcta    600

ccttctggaa aacagggctg gtattcctac ccaggaacct cctttgagca tagagttagc    660

aaccatgctt ctcattccct tgactcatgt cttgccagga tggttagata cacagcatgt    720

tgatttggtc actaaaaaga agaaaaggac taacaagctt cacttttatg aacaactatt    780

ttgagaacat gcacaatagt atgtttttat tactggttta atggagtaat ggtactttta    840

ttctttcttg atagaaacct gcttacattt aaccaagctt ctattatgcc tttttctaac    900

acagactttc ttcactgtct ttcatttaaa aagaaattaa tgctcttaag atatatattt    960

tacgtagtgc tgacaggacc cactctttca ttgaaaggtg atgaaaatca aataaagaat   1020

ctcttcacat gagaaaaaaa aaaaaaaaaa aaaaaaaaaa aaaaaaaaaa ctcgaggggg   1080

ggcccggtac cc                                                       1092


<210> SEQ ID NO 23
<211> LENGTH: 136
<212> TYPE: PRT
<213> ORGANISM: Homo sapiens

<400> SEQUENCE: 23

Met Arg Thr Pro Gly Pro Leu Pro Val Leu Leu Leu Leu Leu Ala Gly
1               5                   10                  15

Ala Pro Ala Ala Arg Pro Thr Pro Pro Thr Cys Tyr Ser Arg Met Arg
            20                  25                  30

Ala Leu Ser Gln Glu Ile Thr Arg Asp Phe Asn Leu Leu Gln Val Ser
        35                  40                  45

Glu Pro Ser Glu Pro Cys Val Arg Tyr Leu Pro Arg Leu Tyr Leu Asp
    50                  55                  60

Ile His Asn Tyr Cys Val Leu Asp Lys Leu Arg Asp Phe Val Ala Ser
65                  70                  75                  80

Pro Pro Cys Trp Lys Val Ala Gln Val Asp Ser Leu Lys Asp Lys Ala
                85                  90                  95

Arg Lys Leu Tyr Thr Ile Met Asn Ser Phe Cys Arg Arg Asp Leu Val
            100                 105                 110

Phe Leu Leu Asp Asp Cys Asn Ala Leu Glu Tyr Pro Ile Pro Val Thr
        115                 120                 125

Thr Val Leu Pro Asp Arg Gln Arg
    130                 135


<210> SEQ ID NO 24
<211> LENGTH: 86
<212> TYPE: PRT
<213> ORGANISM: Homo sapiens

<400> SEQUENCE: 24

Thr Thr Ile Leu Arg Thr Cys Thr Ile Val Cys Phe Tyr Tyr Trp Phe
1               5                   10                  15

Asn Gly Val Met Val Leu Leu Phe Phe Leu Asp Arg Asn Leu Leu Thr
            20                  25                  30

Phe Asn Gln Ala Ser Ile Met Pro Phe Ser Asn Thr Asp Phe Leu His
        35                  40                  45

Cys Leu Ser Phe Lys Lys Lys Leu Met Leu Leu Arg Tyr Ile Phe Tyr
    50                  55                  60

Val Val Leu Thr Gly Pro Thr Leu Ser Leu Lys Gly Asp Glu Asn Gln
65                  70                  75                  80
```

```
Ile Lys Asn Leu Phe Thr
                 85

<210> SEQ ID NO 25
<211> LENGTH: 23
<212> TYPE: PRT
<213> ORGANISM: Homo sapiens

<400> SEQUENCE: 25

Ile Val Cys Phe Tyr Tyr Trp Phe Asn Gly Val Met Val Leu Leu Phe
 1               5                  10                  15

Phe Leu Asp Arg Asn Leu Leu
            20

<210> SEQ ID NO 26
<211> LENGTH: 24
<212> TYPE: PRT
<213> ORGANISM: Homo sapiens

<400> SEQUENCE: 26

Leu Leu Arg Tyr Ile Phe Tyr Val Val Leu Thr Gly Pro Thr Leu Ser
 1               5                  10                  15

Leu Lys Gly Asp Glu Asn Gln Ile
            20

<210> SEQ ID NO 27
<211> LENGTH: 112
<212> TYPE: PRT
<213> ORGANISM: Homo sapiens

<400> SEQUENCE: 27

Pro Thr Cys Tyr Ser Arg Met Arg Ala Leu Ser Gln Glu Ile Thr Arg
 1               5                  10                  15

Asp Phe Asn Leu Leu Gln Val Ser Glu Pro Ser Glu Pro Cys Val Arg
                20                  25                  30

Tyr Leu Pro Arg Leu Tyr Leu Asp Ile His Asn Tyr Cys Val Leu Asp
            35                  40                  45

Lys Leu Arg Asp Phe Val Ala Ser Pro Pro Cys Trp Lys Val Ala Gln
     50                  55                  60

Val Asp Ser Leu Lys Asp Lys Ala Arg Lys Leu Tyr Thr Ile Met Asn
 65                  70                  75                  80

Ser Phe Cys Arg Arg Asp Leu Val Phe Leu Leu Asp Asp Cys Asn Ala
                 85                  90                  95

Leu Glu Tyr Pro Ile Pro Val Thr Thr Val Leu Pro Asp Arg Gln Arg
                100                 105                 110

<210> SEQ ID NO 28
<211> LENGTH: 1705
<212> TYPE: DNA
<213> ORGANISM: Homo sapiens
<220> FEATURE:
<221> NAME/KEY: misc_feature
<222> LOCATION: (724)..(724)
<223> OTHER INFORMATION: n equals a,t,g, or c

<400> SEQUENCE: 28

aattcggcak agggcagctg tcggctggaa ggaactggtc tgctcacact tgctggcttg    60

cgcatcagga ctggctttat ctcctgactc acggtgcaaa ggtgcactct gcgaacgtta   120

agtccgtccc cagcgcttgg aatcctacgg cccccacagc cggatcccct cagccttcca   180

ggtcctcaac tcccgyggac gctgaacaat ggcctccatg gggctacagg taatgggcat   240
```

```
cgcgctggcc gtcctgggct ggctggccgt catgctgtgc tgcgcgctgc ccatgtggcg    300

cgtgacggcc ttcatcggca gcaacattgt cacctcgcag accatctggg agggcctatg    360

gatgaactgc gtggtgcaga gcaccggcca gatgcagtgc aaggtgtacg actcgctgct    420

ggcactgccg caggacctgc aggcggcccg cgccctcgtc atcatcagca tcatcgtggc    480

tgctctgggc gtgctgctgt ccgtggtggg gggcaagtgt accaactgcc tggaggatga    540

aagcgccaag gccaagacca tgatcgtggc gggcgtggtg ttcctgttgg ccggccttat    600

ggtgatagtg ccggtgtcct ggacggccca caacatcatc caagacttct acaatccgct    660

ggtggcctcc gggcagaagc gggagatggg tgcctcgctc tacgtcggct gggccgcctc    720

cggnctgctg ctccttggcg gggggctgct ttgctgcaac tgtccacccc gcacagacaa    780

gccttactcc gccaagtatt ctgctgcccg ctctgctgct gccagcaact acgtgtaagg    840

tgccacggct ccactctgtt cctctctgct ttgttcttcc ctggactgag ctcagcgcag    900

gctgtgaccc caggagggcc ctgccacggg ccactggctg ctggggactg gggactgggc    960

agagactgag ccaggcagga aggcagcagc cttcagcctc tctggcccac tcggacaact   1020

tcccaaggcc gcctcctgct agcaagaaca gagtccaccc tcctctggat attggggagg   1080

gacggaagtg acagggtgtg gtggtggagt ggggagctgg cttctgctgg ccaggatggc   1140

ttaaccctga ctttgggatc tgcctgcatc ggtgttggcc actgtcccca tttacatttt   1200

ccccactctg tctgcctgca tctcctctgt tgcgggtagg ccttgatatc acctctggga   1260

ctgtgccttg ctcaccgaaa cccgcgccca ggagtatggc tgaggccttg cccacccacc   1320

tgcctgggaa gtgcagagtg gatggacggg tttagagggg aggggcgaag gtgctgtaaa   1380

caggtttggg cagtggtggg ggagggggcc agagaggcgg ctcaggttgc ccagctctgt   1440

ggcctcagga ctctctgcct cacccgcttc agcccagggc ccctggagac tgatcccctc   1500

tgagtcctct gccccttcca aggacactaa tgagcctggg agggtggcag ggaggagggg   1560

acagcttcac ccttggaagt cctggggttt ttcctcttcc ttctttgtgg tttctgtttt   1620

gtaatttaag aagagctatt catcactgta attattatta ttttctacaa taaatgggac   1680

ctgtgcacag graaaaaaaa aaaag                                         1705
```

<210> SEQ ID NO 29
<211> LENGTH: 201
<212> TYPE: PRT
<213> ORGANISM: Homo sapiens

<400> SEQUENCE: 29

```
Met Gly Ile Ala Leu Ala Val Leu Gly Trp Leu Ala Val Met Leu Cys
  1               5                  10                  15

Cys Ala Leu Pro Met Trp Arg Val Thr Ala Phe Ile Gly Ser Asn Ile
             20                  25                  30

Val Thr Ser Gln Thr Ile Trp Glu Gly Leu Trp Met Asn Cys Val Val
         35                  40                  45

Gln Ser Thr Gly Gln Met Gln Cys Lys Val Tyr Asp Ser Leu Leu Ala
     50                  55                  60

Leu Pro Gln Asp Leu Gln Ala Ala Arg Ala Leu Val Ile Ile Ser Ile
 65                  70                  75                  80

Ile Val Ala Ala Leu Gly Val Leu Leu Ser Val Val Gly Gly Lys Cys
                 85                  90                  95

Thr Asn Cys Leu Glu Asp Glu Ser Ala Lys Ala Lys Thr Met Ile Val
            100                 105                 110

Ala Gly Val Val Phe Leu Leu Ala Gly Leu Met Val Ile Val Pro Val
```

```
        115                 120                 125

Ser Trp Thr Ala His Asn Ile Ile Gln Asp Phe Tyr Asn Pro Leu Val
    130                 135                 140

Ala Ser Gly Gln Lys Arg Glu Met Gly Ala Ser Leu Tyr Val Gly Trp
145                 150                 155                 160

Ala Ala Ser Gly Leu Leu Leu Leu Gly Gly Gly Leu Leu Cys Cys Asn
                165                 170                 175

Cys Pro Pro Arg Thr Asp Lys Pro Tyr Ser Ala Lys Tyr Ser Ala Ala
            180                 185                 190

Arg Ser Ala Ala Ala Ser Asn Tyr Val
        195                 200


<210> SEQ ID NO 30
<211> LENGTH: 9
<212> TYPE: PRT
<213> ORGANISM: Homo sapiens

<400> SEQUENCE: 30

Thr Met Ala Ser Met Gly Leu Gln Val
  1               5


<210> SEQ ID NO 31
<211> LENGTH: 167
<212> TYPE: PRT
<213> ORGANISM: Homo sapiens

<400> SEQUENCE: 31

Lys Ser Trp Met Met Leu Trp Ala Val Gln Asp Thr Gly Thr Ile Thr
  1               5                  10                  15

Ile Arg Pro Ala Asn Arg Asn Thr Thr Pro Ala Thr Ile Met Val Leu
             20                  25                  30

Ala Leu Ala Leu Ser Ser Ser Arg Gln Leu Val His Leu Pro Pro Thr
         35                  40                  45

Thr Asp Ser Ser Thr Pro Arg Ala Ala Thr Met Met Leu Met Met Thr
     50                  55                  60

Arg Ala Arg Ala Ala Cys Arg Ser Cys Gly Ser Ala Ser Ser Glu Ser
 65                  70                  75                  80

Tyr Thr Leu His Cys Ile Trp Pro Val Leu Cys Thr Thr Gln Phe Ile
                 85                  90                  95

His Arg Pro Ser Gln Met Val Cys Glu Val Thr Met Leu Leu Pro Met
            100                 105                 110

Lys Ala Val Thr Arg His Met Gly Ser Ala Gln His Ser Met Thr Ala
        115                 120                 125

Ser Gln Pro Arg Thr Ala Ser Ala Met Pro Ile Thr Cys Ser Pro Met
    130                 135                 140

Glu Ala Ile Val Gln Arg Pro Arg Glu Leu Arg Thr Trp Lys Ala Glu
145                 150                 155                 160

Gly Ile Arg Leu Trp Gly Pro
                165


<210> SEQ ID NO 32
<211> LENGTH: 28
<212> TYPE: PRT
<213> ORGANISM: Homo sapiens

<400> SEQUENCE: 32

Leu Gln Val Met Gly Ile Ala Leu Ala Val Leu Gly Trp Leu Ala Val
  1               5                  10                  15
```

```
Met Leu Cys Cys Ala Leu Pro Met Trp Arg Val Thr
            20                  25


<210> SEQ ID NO 33
<211> LENGTH: 22
<212> TYPE: PRT
<213> ORGANISM: Homo sapiens

<400> SEQUENCE: 33

Ser Asn Ile Val Thr Ser Gln Thr Ile Trp Glu Gly Leu Trp Met Asn
  1               5                  10                  15

Cys Val Val Gln Ser Thr
            20


<210> SEQ ID NO 34
<211> LENGTH: 18
<212> TYPE: PRT
<213> ORGANISM: Homo sapiens

<400> SEQUENCE: 34

Gln Met Gln Cys Lys Val Tyr Asp Ser Leu Leu Ala Leu Pro Gln Asp
  1               5                  10                  15

Leu Gln


<210> SEQ ID NO 35
<211> LENGTH: 18
<212> TYPE: PRT
<213> ORGANISM: Homo sapiens

<400> SEQUENCE: 35

Lys Cys Thr Asn Cys Leu Glu Asp Glu Ser Ala Lys Ala Lys Thr Met
  1               5                  10                  15

Ile Val


<210> SEQ ID NO 36
<211> LENGTH: 32
<212> TYPE: PRT
<213> ORGANISM: Homo sapiens

<400> SEQUENCE: 36

Gly Val Val Phe Leu Leu Ala Gly Leu Met Val Ile Val Pro Val Ser
  1               5                  10                  15

Trp Thr Ala His Asn Ile Ile Gln Asp Phe Tyr Asn Pro Leu Val Ala
            20                  25                  30


<210> SEQ ID NO 37
<211> LENGTH: 12
<212> TYPE: PRT
<213> ORGANISM: Homo sapiens

<400> SEQUENCE: 37

Cys Cys Asn Cys Pro Pro Arg Thr Asp Lys Pro Tyr
  1               5                  10


<210> SEQ ID NO 38
<211> LENGTH: 1288
<212> TYPE: DNA
<213> ORGANISM: Homo sapiens
<220> FEATURE:
<221> NAME/KEY: misc_feature
<222> LOCATION: (1286)..(1286)
<223> OTHER INFORMATION: n equals a,t,g, or c

<400> SEQUENCE: 38
```

-continued

```
ggcgcgcggg tgaaaggcgc attgatgcag cctgcggcgg cctcggagcg cggcggasca     60

gacgctgacc acgttcctct cctcggtctc ctccgcctcc agctccgcgc tgcccggcag    120

ccgggagcca tgcgacccca gggccccgcc gcctccccgc agcggctccg cggcctcctg    180

ctgctcctgc tgctgcagct gcccgcgccg tcgagcgcct ctgagatccc caaggggaag    240

caaaaggcgc atccggcaga gggaggtggt ggacctgtat aatggaatgt gcttacaagg    300

gccagcagga gtgcctggtc gagacgggag ccctggggcc aatggcattc cgggtacacc    360

tgggatccca ggtcgggatg gattcaaagg agaaaagggg gaatgtctga gggaaagctt    420

tgaggagtcc tggacaccca actacaagca gtgttcatgg agttcattga attatggcat    480

agatcttggg aaaattgcgg agtgtacatt tacaaagatg cgttcaaata gtgctctaag    540

agttttgttc agtggctcac ttcggctaaa atgcagaaat gcatgctgtc agcgttggta    600

tttcacattc aatggagctg aatgttcagg acctcttccc attgaagcta taatttattt    660

ggaccaagga agccctgaaa tgaattcaac aattaatatt catcgcactt cttctgtgga    720

aggactttgt gaaggaattg gtgctggatt agtggatgtt gctatctggg ttggcacttg    780

ttcagattac ccaaaaggag atgcttctac tggatggaat tcagtttctc gcatcattat    840

tgaagaacta ccaaaataaa tgctttaatt ttcatttgct acctcttttt ttattatgcc    900

ttggaatggt tcacttaaat gacattttaa ataagtttat gtatacatct gaatgaaaag    960

caaagctaaa tatgtttaca gaccaaagtg tgatttcaca tgtttttaaa tctagcatta   1020

ttcattttgc ttcaatcaaa agtggtttca atattttttt tagttggtta gaatactttc   1080

ttcatagtca cattctctca acctataatt tgggaatatt gttgtggtct tttgtttttt   1140

ctcttagtat agcattttta aaaaaatata aaagctacca atctttgtac aatttgtaaa   1200

tgttaagaat ttttttata tctgttaaat aaaaattatt tccmacaacc ttaaaaaaaa    1260

aaaaaaaaaa aaaaaaaaaa aaaaaanaa                                     1288
```

<210> SEQ ID NO 39
<211> LENGTH: 16
<212> TYPE: PRT
<213> ORGANISM: Homo sapiens

<400> SEQUENCE: 39

```
Met Gln Lys Cys Met Leu Ser Ala Leu Val Phe His Ile Gln Trp Ser
  1               5                  10                  15
```

<210> SEQ ID NO 40
<211> LENGTH: 276
<212> TYPE: PRT
<213> ORGANISM: Homo sapiens
<220> FEATURE:
<221> NAME/KEY: SITE
<222> LOCATION: (10)
<223> OTHER INFORMATION: Xaa equals any of the naturally occurring
      L-amino acids

<400> SEQUENCE: 40

```
Ser Leu Arg Arg Pro Arg Ser Ala Ala Xaa Gln Thr Leu Thr Thr Phe
  1               5                  10                  15

Leu Ser Ser Val Ser Ser Ala Ser Ser Ser Ala Leu Pro Gly Ser Arg
             20                  25                  30

Glu Pro Cys Asp Pro Arg Ala Pro Pro Pro Pro Arg Ser Gly Ser Ala
         35                  40                  45

Ala Ser Cys Cys Ser Cys Cys Cys Ser Cys Pro Arg Arg Arg Ala Pro
     50                  55                  60
```

```
Leu Arg Ser Pro Arg Gly Ser Lys Arg Arg Ile Arg Gln Arg Glu Val
 65                  70                  75                  80

Val Asp Leu Tyr Asn Gly Met Cys Leu Gln Gly Pro Ala Gly Val Pro
                 85                  90                  95

Gly Arg Asp Gly Ser Pro Gly Ala Asn Gly Ile Pro Gly Thr Pro Gly
            100                 105                 110

Ile Pro Gly Arg Asp Gly Phe Lys Gly Glu Lys Gly Glu Cys Leu Arg
        115                 120                 125

Glu Ser Phe Glu Glu Ser Trp Thr Pro Asn Tyr Lys Gln Cys Ser Trp
    130                 135                 140

Ser Ser Leu Asn Tyr Gly Ile Asp Leu Gly Lys Ile Ala Glu Cys Thr
145                 150                 155                 160

Phe Thr Lys Met Arg Ser Asn Ser Ala Leu Arg Val Leu Phe Ser Gly
                165                 170                 175

Ser Leu Arg Leu Lys Cys Arg Asn Ala Cys Cys Gln Arg Trp Tyr Phe
            180                 185                 190

Thr Phe Asn Gly Ala Glu Cys Ser Gly Pro Leu Pro Ile Glu Ala Ile
        195                 200                 205

Ile Tyr Leu Asp Gln Gly Ser Pro Glu Met Asn Ser Thr Ile Asn Ile
    210                 215                 220

His Arg Thr Ser Ser Val Glu Gly Leu Cys Glu Gly Ile Gly Ala Gly
225                 230                 235                 240

Leu Val Asp Val Ala Ile Trp Val Gly Thr Cys Ser Asp Tyr Pro Lys
                245                 250                 255

Gly Asp Ala Ser Thr Gly Trp Asn Ser Val Ser Arg Ile Ile Ile Glu
            260                 265                 270

Glu Leu Pro Lys
        275


<210> SEQ ID NO 41
<211> LENGTH: 61
<212> TYPE: PRT
<213> ORGANISM: Homo sapiens
<220> FEATURE:
<221> NAME/KEY: SITE
<222> LOCATION: (10)
<223> OTHER INFORMATION: Xaa equals any of the naturally occurring
      L-amino acids

<400> SEQUENCE: 41

Ser Leu Arg Arg Pro Arg Ser Ala Ala Xaa Gln Thr Leu Thr Thr Phe
  1               5                  10                  15

Leu Ser Ser Val Ser Ser Ala Ser Ser Ser Ala Leu Pro Gly Ser Arg
             20                  25                  30

Glu Pro Cys Asp Pro Arg Ala Pro Pro Pro Pro Arg Ser Gly Ser Ala
         35                  40                  45

Ala Ser Cys Cys Ser Cys Cys Cys Ser Cys Pro Arg Arg
     50                  55                  60


<210> SEQ ID NO 42
<211> LENGTH: 52
<212> TYPE: PRT
<213> ORGANISM: Homo sapiens

<400> SEQUENCE: 42

Arg Ala Pro Leu Arg Ser Pro Arg Gly Ser Lys Arg Arg Ile Arg Gln
  1               5                  10                  15

Arg Glu Val Val Asp Leu Tyr Asn Gly Met Cys Leu Gln Gly Pro Ala
             20                  25                  30
```

```
Gly Val Pro Gly Arg Asp Gly Ser Pro Gly Ala Asn Gly Ile Pro Gly
         35                  40                  45

Thr Pro Gly Ile
     50


<210> SEQ ID NO 43
<211> LENGTH: 52
<212> TYPE: PRT
<213> ORGANISM: Homo sapiens

<400> SEQUENCE: 43

Thr Pro Gly Ile Pro Gly Arg Asp Gly Phe Lys Gly Glu Lys Gly Glu
  1               5                  10                  15

Cys Leu Arg Glu Ser Phe Glu Glu Ser Trp Thr Pro Asn Tyr Lys Gln
             20                  25                  30

Cys Ser Trp Ser Ser Leu Asn Tyr Gly Ile Asp Leu Gly Lys Ile Ala
         35                  40                  45

Glu Cys Thr Phe
     50


<210> SEQ ID NO 44
<211> LENGTH: 66
<212> TYPE: PRT
<213> ORGANISM: Homo sapiens

<400> SEQUENCE: 44

Phe Thr Lys Met Arg Ser Asn Ser Ala Leu Arg Val Leu Phe Ser Gly
  1               5                  10                  15

Ser Leu Arg Leu Lys Cys Arg Asn Ala Cys Cys Gln Arg Trp Tyr Phe
             20                  25                  30

Thr Phe Asn Gly Ala Glu Cys Ser Gly Pro Leu Pro Ile Glu Ala Ile
         35                  40                  45

Ile Tyr Leu Asp Gln Gly Ser Pro Glu Met Asn Ser Thr Ile Asn Ile
     50                  55                  60

His Arg
65


<210> SEQ ID NO 45
<211> LENGTH: 51
<212> TYPE: PRT
<213> ORGANISM: Homo sapiens

<400> SEQUENCE: 45

Arg Thr Ser Ser Val Glu Gly Leu Cys Glu Gly Ile Gly Ala Gly Leu
  1               5                  10                  15

Val Asp Val Ala Ile Trp Val Gly Thr Cys Ser Asp Tyr Pro Lys Gly
             20                  25                  30

Asp Ala Ser Thr Gly Trp Asn Ser Val Ser Arg Ile Ile Ile Glu Glu
         35                  40                  45

Leu Pro Lys
     50


<210> SEQ ID NO 46
<211> LENGTH: 941
<212> TYPE: DNA
<213> ORGANISM: Homo sapiens

<400> SEQUENCE: 46

ggcacgagcc tggacgcagc agccaccgcc gcgtccctct ctccacgagg ctgccggctt      60
```

```
aggaccccca gctccgacat gtcgccctct ggtcgcctgt gtcttctcac catcgttggc    120

ctgattctcc ccaccagagg acagacgttg aaagatacca cgtccagttc ttcagcagac    180

tcaactatca tggacattca ggtcccgaca cgagccccag atgcagtcta cacagaactc    240

cagcccacct ctccaacccc aacctggcct gctgatgaaa caccacaacc ccagacccag    300

acccagcaac tggaaggaac ggatgggcct ctagtgacag atccagagac acacaagagc    360

accaaagcag ctcatcccac tgatgacacc acgacgctct ctgagagacc atccccaagc    420

acagacgtcc agacagaccc ccagaccctc aagccatctg gttttcatga ggatgacccc    480

ttcttctatg atgaacacac cctccggaaa cgggggctgt tggtcgcagc tgtgctgttc    540

atcacaggca tcatcatcct caccagtggc aagtgcaggc agctgtcccg gttatgccgg    600

aatcattgca ggtgagtcca tcagaaacag gagctgacaa ccygctgggc acccgaagac    660

caagccccct gccagctcac cgtgcccagc ctcctgcatc ccctcgaaga gcctggccag    720

agagggaaga cacagatgat gaagctggag ccagggctgc cggtccgagt ctcctacctc    780

ccccaaccct gcccgcccct gaaggctacc tggcgccttg gggctgtcc ctcaagttat    840

ctcctctgyt aagacaaaaa gtaaagcact gtggtctttg caaaaaaaaa aaaaaaaaaa    900

aaaaaaaaaa aaaaaaaaaa aaaaaaaaaa aaaaaactcg a                        941
```

<210> SEQ ID NO 47
<211> LENGTH: 178
<212> TYPE: PRT
<213> ORGANISM: Homo sapiens

<400> SEQUENCE: 47

```
Met Ser Pro Ser Gly Arg Leu Cys Leu Leu Thr Ile Val Gly Leu Ile
  1               5                  10                  15

Leu Pro Thr Arg Gly Gln Thr Leu Lys Asp Thr Thr Ser Ser Ser Ser
             20                  25                  30

Ala Asp Ser Thr Ile Met Asp Ile Gln Val Pro Thr Arg Ala Pro Asp
         35                  40                  45

Ala Val Tyr Thr Glu Leu Gln Pro Thr Ser Pro Thr Pro Thr Trp Pro
     50                  55                  60

Ala Asp Glu Thr Pro Gln Pro Gln Thr Gln Thr Gln Gln Leu Glu Gly
65                  70                  75                  80

Thr Asp Gly Pro Leu Val Thr Asp Pro Glu Thr His Lys Ser Thr Lys
                85                  90                  95

Ala Ala His Pro Thr Asp Asp Thr Thr Thr Leu Ser Glu Arg Pro Ser
            100                 105                 110

Pro Ser Thr Asp Val Gln Thr Asp Pro Gln Thr Leu Lys Pro Ser Gly
        115                 120                 125

Phe His Glu Asp Asp Pro Phe Phe Tyr Asp Glu His Thr Leu Arg Lys
    130                 135                 140

Arg Gly Leu Leu Val Ala Ala Val Leu Phe Ile Thr Gly Ile Ile Ile
145                 150                 155                 160

Leu Thr Ser Gly Lys Cys Arg Gln Leu Ser Arg Leu Cys Arg Asn His
                165                 170                 175

Cys Arg
```

<210> SEQ ID NO 48
<211> LENGTH: 736
<212> TYPE: DNA
<213> ORGANISM: Homo sapiens
<220> FEATURE:
<221> NAME/KEY: misc_feature
<222> LOCATION: (1)..(1)
<223> OTHER INFORMATION: n equals a,t,g, or c
<220> FEATURE:
<221> NAME/KEY: misc_feature
<222> LOCATION: (541)..(541)
<223> OTHER INFORMATION: n equals a,t,g, or c
<220> FEATURE:
<221> NAME/KEY: misc_feature
<222> LOCATION: (594)..(594)
<223> OTHER INFORMATION: n equals a,t,g, or c

<400> SEQUENCE: 48
ncgcagcagc caccgccgcg tccctctctc cacgaggctg ccggcttagg acccccagct 60
ccgaccatcg cctggtccca cagatgtcgc cctctggtcg cctgtgtctt ctcaccatcg 120
ttggcctgat tctccccacc agaggacaga cgttgaaaga taccacgtcc agttcttcag 180
cagacgcaac tatcatggac attcaggtcc cgacacgagc cccagatgca gtctacacag 240
aactccagcc cacctctcca accccaacct ggcctgctga tgaaacacca caaccccaga 300
cccagaccca gcaactggaa ggaacggatg ggcctctagt gacatatcca gagacacaca 360
agagcaccaa agcagctcat cccactgatg acaccacgac gctctctgag agaccatccc 420
caagcacaga cgtccagaca gacccccaga ccctcaagcc atctggtttt catgaggatg 480
accccttctt ctatgatgaa cacaccctcc ggaaacgggg gctgttggtc gcagctgtgc 540
ntgttcatca cagggcttat tattcttcac cagttggcaa gtgcagggca gctnttcccg 600
gttattgccg gaattcgttt gcaggttgag ttccattcag gaaacaggga gctttacaaa 660
cctgttgggg cacccgaagg aaccaggccc cttggccagg tttaacgtgg cccagtcttc 720
ctggcattcc cttcga 736

<210> SEQ ID NO 49
<211> LENGTH: 181
<212> TYPE: PRT
<213> ORGANISM: Homo sapiens
<220> FEATURE:
<221> NAME/KEY: SITE
<222> LOCATION: (153)
<223> OTHER INFORMATION: Xaa equals any amino acid
<220> FEATURE:
<221> NAME/KEY: SITE
<222> LOCATION: (171)
<223> OTHER INFORMATION: Xaa equals any amino acid

<400> SEQUENCE: 49

Met Ser Pro Ser Gly Arg Leu Cys Leu Leu Thr Ile Val Gly Leu Ile
1 5 10 15

Leu Pro Thr Arg Gly Gln Thr Leu Lys Asp Thr Thr Ser Ser Ser Ser
20 25 30

Ala Asp Ala Thr Ile Met Asp Ile Gln Val Pro Thr Arg Ala Pro Asp
35 40 45

Ala Val Tyr Thr Glu Leu Gln Pro Thr Ser Pro Thr Pro Thr Trp Pro
50 55 60

Ala Asp Glu Thr Pro Gln Pro Gln Thr Gln Thr Gln Gln Leu Glu Gly
65 70 75 80

Thr Asp Gly Pro Leu Val Thr Tyr Pro Glu Thr His Lys Ser Thr Lys
85 90 95

Ala Ala His Pro Thr Asp Asp Thr Thr Thr Leu Ser Glu Arg Pro Ser
100 105 110

Pro Ser Thr Asp Val Gln Thr Asp Pro Gln Thr Leu Lys Pro Ser Gly
115 120 125

Phe His Glu Asp Asp Pro Phe Phe Tyr Asp Glu His Thr Leu Arg Lys

```
    130                 135                 140

Arg Gly Leu Leu Val Ala Ala Val Xaa Val His His Arg Ala Tyr Tyr
145                 150                 155                 160

Ser Ser Pro Val Gly Lys Cys Arg Ala Ala Xaa Pro Gly Tyr Cys Arg
                165                 170                 175

Asn Ser Phe Ala Gly
            180


<210> SEQ ID NO 50
<211> LENGTH: 864
<212> TYPE: DNA
<213> ORGANISM: Homo sapiens
<220> FEATURE:
<221> NAME/KEY: misc_feature
<222> LOCATION: (28)..(28)
<223> OTHER INFORMATION: n equals a,t,g, or c
<220> FEATURE:
<221> NAME/KEY: misc_feature
<222> LOCATION: (706)..(706)
<223> OTHER INFORMATION: n equals a,t,g, or c
<220> FEATURE:
<221> NAME/KEY: misc_feature
<222> LOCATION: (745)..(745)
<223> OTHER INFORMATION: n equals a,t,g, or c
<220> FEATURE:
<221> NAME/KEY: misc_feature
<222> LOCATION: (748)..(748)
<223> OTHER INFORMATION: n equals a,t,g, or c
<220> FEATURE:
<221> NAME/KEY: misc_feature
<222> LOCATION: (757)..(757)
<223> OTHER INFORMATION: n equals a,t,g, or c
<220> FEATURE:
<221> NAME/KEY: misc_feature
<222> LOCATION: (765)..(765)
<223> OTHER INFORMATION: n equals a,t,g, or c
<220> FEATURE:
<221> NAME/KEY: misc_feature
<222> LOCATION: (772)..(772)
<223> OTHER INFORMATION: n equals a,t,g, or c
<220> FEATURE:
<221> NAME/KEY: misc_feature
<222> LOCATION: (781)..(781)
<223> OTHER INFORMATION: n equals a,t,g, or c
<220> FEATURE:
<221> NAME/KEY: misc_feature
<222> LOCATION: (813)..(813)
<223> OTHER INFORMATION: n equals a,t,g, or c
<220> FEATURE:
<221> NAME/KEY: misc_feature
<222> LOCATION: (840)..(840)
<223> OTHER INFORMATION: n equals a,t,g, or c
<220> FEATURE:
<221> NAME/KEY: misc_feature
<222> LOCATION: (842)..(842)
<223> OTHER INFORMATION: n equals a,t,g, or c

<400> SEQUENCE: 50

gagaagacga cagaagggta cggctgcnag aagacgacag aaggggaccc tccgcctgga      60

cgcagcagcc accgccgcgt ccctctctcc acgaggctgc cggcttagga cccccagctc     120

cgacatgtcg ccctctggtc gcctgtgtct tctcaccatc gttggcctga ttctccccac     180

cagaggacag acgttgaaag ataccacgtc cagttcttca gcagactcaa ctatcatgga     240

cattcaggtc ccgacacgag ccccagatgc agtctacaca gaactccagc ccacctctcc     300

aaccccaacc tggcctgctg atgaaacacc acaaccccag acccagaccc agcaactgga     360

aggaacggat gggcctctag tgacagatcc agagacacac aagagcacca aagcagctca     420

tcccactgat gacaccacga cgctctctga gagaccatcc ccaagcacag acgtccagac     480

agacccccag accctcaagc catctggttt tcatgaggat gacccettct tctatgatga     540
```

```
acacaccctc cggaaacggg ggctgttggt cgcagctgtg ctgttcatca caggcatcat    600

catcctcacc agtggcaagt gcaggcagct gtcccggtat gccggaatca ttggaggtga    660

gtccatcaga aacaggagct gacaacctgc tgggcacccc gaagancaaa gccccctggc    720

agcttaccgg gcccaagcct ctggnatncc cttgaanagc ctggncagag angggaagac    780

nccgatgatg aacttggacc cagggttgcc ggncccaggg ctcctacttc cccaaacctn    840

gnccggccct tgaaggttac ctgg                                           864
```

<210> SEQ ID NO 51
<211> LENGTH: 185
<212> TYPE: PRT
<213> ORGANISM: Homo sapiens

<400> SEQUENCE: 51

```
Met Ser Pro Ser Gly Arg Leu Cys Leu Leu Thr Ile Val Gly Leu Ile
  1               5                  10                  15

Leu Pro Thr Arg Gly Gln Thr Leu Lys Asp Thr Thr Ser Ser Ser Ser
             20                  25                  30

Ala Asp Ser Thr Ile Met Asp Ile Gln Val Pro Thr Arg Ala Pro Asp
         35                  40                  45

Ala Val Tyr Thr Glu Leu Gln Pro Thr Ser Pro Thr Pro Thr Trp Pro
     50                  55                  60

Ala Asp Glu Thr Pro Gln Pro Gln Thr Gln Thr Gln Gln Leu Glu Gly
 65                  70                  75                  80

Thr Asp Gly Pro Leu Val Thr Asp Pro Glu Thr His Lys Ser Thr Lys
                 85                  90                  95

Ala Ala His Pro Thr Asp Asp Thr Thr Thr Leu Ser Glu Arg Pro Ser
            100                 105                 110

Pro Ser Thr Asp Val Gln Thr Asp Pro Gln Thr Leu Lys Pro Ser Gly
        115                 120                 125

Phe His Glu Asp Asp Pro Phe Phe Tyr Asp Glu His Thr Leu Arg Lys
    130                 135                 140

Arg Gly Leu Leu Val Ala Ala Val Leu Phe Ile Thr Gly Ile Ile Ile
145                 150                 155                 160

Leu Thr Ser Gly Lys Cys Arg Gln Leu Ser Arg Tyr Ala Gly Ile Ile
                165                 170                 175

Gly Gly Glu Ser Ile Arg Asn Arg Ser
            180                 185
```

<210> SEQ ID NO 52
<211> LENGTH: 26
<212> TYPE: PRT
<213> ORGANISM: Homo sapiens

<400> SEQUENCE: 52

```
Gly Thr Ser Leu Asp Ala Ala Ala Thr Ala Ala Ser Leu Ser Pro Arg
  1               5                  10                  15

Gly Cys Arg Leu Arg Thr Pro Ser Ser Asp
             20                  25
```

<210> SEQ ID NO 53
<211> LENGTH: 99
<212> TYPE: PRT
<213> ORGANISM: Homo sapiens

<400> SEQUENCE: 53

```
Gln Ile Gln Arg His Thr Arg Ala Pro Lys Gln Leu Ile Pro Leu Met
```

-continued

```
  1               5                   10                  15

Thr Pro Arg Arg Ser Leu Arg Asp His Pro Gln Ala Gln Thr Ser Arg
             20                  25                  30

Gln Thr Pro Arg Pro Ser Ser His Leu Val Phe Met Arg Met Thr Pro
         35                  40                  45

Ser Ser Met Met Asn Thr Pro Ser Gly Asn Gly Gly Cys Trp Ser Gln
     50                  55                  60

Leu Cys Cys Ser Ser Gln Ala Ser Ser Ser Ser Pro Val Ala Ser Ala
 65                  70                  75                  80

Gly Ser Cys Pro Gly Tyr Ala Gly Ile Ile Ala Gly Glu Ser Ile Arg
                 85                  90                  95

Asn Arg Ser


<210> SEQ ID NO 54
<211> LENGTH: 27
<212> TYPE: PRT
<213> ORGANISM: Homo sapiens

<400> SEQUENCE: 54

Pro Arg Arg Ser Leu Arg Asp His Pro Gln Ala Gln Thr Ser Arg Gln
  1               5                  10                  15

Thr Pro Arg Pro Ser Ser His Leu Val Phe Met
             20                  25


<210> SEQ ID NO 55
<211> LENGTH: 129
<212> TYPE: PRT
<213> ORGANISM: Homo sapiens
<220> FEATURE:
<221> NAME/KEY: SITE
<222> LOCATION: (50)
<223> OTHER INFORMATION: Xaa equals any of the naturally occurring
      L-amino acids

<400> SEQUENCE: 55

Thr His Pro Pro Glu Thr Gly Ala Val Gly Arg Ser Cys Ala Val His
  1               5                  10                  15

His Arg His His His Pro His Gln Trp Gln Val Gln Ala Ala Val Pro
             20                  25                  30

Val Met Pro Glu Ser Leu Gln Val Ser Pro Ser Glu Thr Gly Ala Asp
         35                  40                  45

Asn Xaa Leu Gly Thr Arg Arg Pro Ser Pro Leu Pro Ala His Arg Ala
     50                  55                  60

Gln Pro Pro Ala Ser Pro Arg Arg Ala Trp Pro Glu Arg Glu Asp Thr
 65                  70                  75                  80

Asp Asp Glu Ala Gly Ala Arg Ala Ala Gly Pro Ser Leu Leu Pro Pro
                 85                  90                  95

Pro Thr Leu Pro Ala Pro Glu Gly Tyr Leu Ala Pro Trp Gly Leu Ser
            100                 105                 110

Leu Lys Leu Ser Pro Leu Leu Arg Gln Lys Val Lys His Cys Gly Leu
        115                 120                 125

Cys


<210> SEQ ID NO 56
<211> LENGTH: 36
<212> TYPE: PRT
<213> ORGANISM: Homo sapiens
<220> FEATURE:
<221> NAME/KEY: SITE
<222> LOCATION: (16)
```

```
<223> OTHER INFORMATION: Xaa equals any of the naturally occurring
      L-amino acids

<400> SEQUENCE: 56

Pro Glu Ser Leu Gln Val Ser Pro Ser Glu Thr Gly Ala Asp Asn Xaa
  1               5                  10                  15

Leu Gly Thr Arg Arg Pro Ser Pro Leu Pro Ala His Arg Ala Gln Pro
             20                  25                  30

Pro Ala Ser Pro
         35


<210> SEQ ID NO 57
<211> LENGTH: 79
<212> TYPE: PRT
<213> ORGANISM: Homo sapiens

<400> SEQUENCE: 57

Gly Thr Ala Pro Lys Ala Pro Gly Ser Leu Gln Gly Arg Ala Gly Leu
  1               5                  10                  15

Gly Glu Val Gly Asp Ser Asp Arg Gln Pro Trp Leu Gln Leu His His
             20                  25                  30

Leu Cys Leu Pro Ser Leu Ala Arg Leu Phe Glu Gly Met Gln Glu Ala
         35                  40                  45

Gly His Gly Glu Leu Ala Gly Gly Leu Val Phe Gly Cys Pro Ala Gly
     50                  55                  60

Cys Gln Leu Leu Phe Leu Met Asp Ser Pro Ala Met Ile Pro Ala
 65                  70                  75


<210> SEQ ID NO 58
<211> LENGTH: 34
<212> TYPE: PRT
<213> ORGANISM: Homo sapiens

<400> SEQUENCE: 58

Gly Glu Val Gly Asp Ser Asp Arg Gln Pro Trp Leu Gln Leu His His
  1               5                  10                  15

Leu Cys Leu Pro Ser Leu Ala Arg Leu Phe Glu Gly Met Gln Glu Ala
             20                  25                  30

Gly His


<210> SEQ ID NO 59
<211> LENGTH: 86
<212> TYPE: PRT
<213> ORGANISM: Homo sapiens

<400> SEQUENCE: 59

Gly Ser Gly Gly Leu Ser Gly Arg Leu Cys Leu Gly Met Val Ser Gln
  1               5                  10                  15

Arg Ala Ser Trp Cys His Gln Trp Asp Glu Leu Leu Trp Cys Ser Cys
             20                  25                  30

Val Ser Leu Asp Leu Ser Leu Glu Ala His Pro Phe Leu Pro Val Ala
         35                  40                  45

Gly Ser Gly Ser Gly Val Val Val Phe His Gln Gln Ala Arg Leu Gly
     50                  55                  60

Leu Glu Arg Trp Ala Gly Val Leu Cys Arg Leu His Leu Gly Leu Val
 65                  70                  75                  80

Ser Gly Pro Glu Cys Pro
                 85
```

<210> SEQ ID NO 60
<211> LENGTH: 41
<212> TYPE: PRT
<213> ORGANISM: Homo sapiens

<400> SEQUENCE: 60

```
Gln Trp Asp Glu Leu Leu Trp Cys Ser Cys Val Ser Leu Asp Leu Ser
  1               5                  10                  15

Leu Glu Ala His Pro Phe Leu Pro Val Ala Gly Ser Gly Ser Gly Val
             20                  25                  30

Val Val Phe His Gln Gln Ala Arg Leu
         35                  40
```

<210> SEQ ID NO 61
<211> LENGTH: 1292
<212> TYPE: DNA
<213> ORGANISM: Homo sapiens

<400> SEQUENCE: 61

```
gctgccttgc tccacacctg gtcaggggag agaggggaaa gccaagggaa gggacctaac     60

tgaaaacaaa caagctggga gaagcaggaa tctgcgctcg ggttccgcag atgcagaggt    120

tgaggtggct gcgggactgg aagtcatcgg gcagaggtct cacagcarcc aaggaacctg    180

gggcccgctc ctccccctc caggccatga ggattctgca gttaatcctg cttgctctgg     240

caacagggct tgtaggggga gagaccagga tcatcaaggg gttcgagtgc aagcctcact    300

cccagccctg gcaggcagcc ctgttcgaga agacgcggct actctgtggg gcgacgctca    360

tcgcccccag atggctcctg acagcagccc actgcctcaa gccccgctac atagttcacc    420

tggggcagca caacctccag aaggaggagg gctgtgagca gacccggaca gccactgagt    480

ccttccccca ccccggcttc aacaacagcc tccccaacaa agaccaccgc aatgacatca    540

tgctggtgaa gatggcatcg ccagtctcca tcacctgggc tgtgcgaccc ctcaccctct    600

cctcacgctg tgtcactgct ggcaccagct gyctcatttc cggctggggc agcacgtcca    660

gcccccagtt acgcctgcct cacaccttgc gatgcgccaa catcaccatc attgagcacc    720

agaagtgtga gaacgcctac cccggcaaca tcacagacac catggtgtgt gccagcgtgc    780

aggaaggggg caaggactcc tgccagggtg actccggggg ccctctggtc tgtaaccagt    840

ctcttcaagg cattatctcc tggggccagg atccgtgtgc gatcacccga aagcctggtg    900

tctacacgaa agtctgcaaa tatgtggact ggatccagga gacgatgaag aacaattaga    960

ctggacccac ccaccacags ccatcaccct ccatttccac ttggtgtttg gttcctgttc   1020

actctgttaa taagaaaccc taagccaaga ccctctacga acattctttg ggcctcctgg   1080

actacaggag atgctgtcac ttaataatca acctggggtt cgaaatcagt gagacctgga   1140

ttcaaattct gccttgaaat attgtgactc tgggaatgac aacacctggt ttgttctctg   1200

ttgtatcccc agccccaaag acagctcctg gccatatatc aaggtttcaa taaatatttg   1260

ctaaatgaaa aaraaaaaaa aaaaaaactc ga                                  1292
```

<210> SEQ ID NO 62
<211> LENGTH: 250
<212> TYPE: PRT
<213> ORGANISM: Homo sapiens

<400> SEQUENCE: 62

```
Met Arg Ile Leu Gln Leu Ile Leu Leu Ala Leu Ala Thr Gly Leu Val
  1               5                  10                  15

Gly Gly Glu Thr Arg Ile Ile Lys Gly Phe Glu Cys Lys Pro His Ser
```

```
            20                  25                  30

Gln Pro Trp Gln Ala Ala Leu Phe Glu Lys Thr Arg Leu Leu Cys Gly
        35                  40                  45

Ala Thr Leu Ile Ala Pro Arg Trp Leu Leu Thr Ala Ala His Cys Leu
    50                  55                  60

Lys Pro Arg Tyr Ile Val His Leu Gly Gln His Asn Leu Gln Lys Glu
65                  70                  75                  80

Glu Gly Cys Glu Gln Thr Arg Thr Ala Thr Glu Ser Phe Pro His Pro
                85                  90                  95

Gly Phe Asn Asn Ser Leu Pro Asn Lys Asp His Arg Asn Asp Ile Met
            100                 105                 110

Leu Val Lys Met Ala Ser Pro Val Ser Ile Thr Trp Ala Val Arg Pro
        115                 120                 125

Leu Thr Leu Ser Ser Arg Cys Val Thr Ala Gly Thr Ser Cys Leu Ile
    130                 135                 140

Ser Gly Trp Gly Ser Thr Ser Ser Pro Gln Leu Arg Leu Pro His Thr
145                 150                 155                 160

Leu Arg Cys Ala Asn Ile Thr Ile Ile Glu His Gln Lys Cys Glu Asn
                165                 170                 175

Ala Tyr Pro Gly Asn Ile Thr Asp Thr Met Val Cys Ala Ser Val Gln
            180                 185                 190

Glu Gly Gly Lys Asp Ser Cys Gln Gly Asp Ser Gly Gly Pro Leu Val
        195                 200                 205

Cys Asn Gln Ser Leu Gln Gly Ile Ile Ser Trp Gly Gln Asp Pro Cys
    210                 215                 220

Ala Ile Thr Arg Lys Pro Gly Val Tyr Thr Lys Val Cys Lys Tyr Val
225                 230                 235                 240

Asp Trp Ile Gln Glu Thr Met Lys Asn Asn
                245                 250


<210> SEQ ID NO 63
<211> LENGTH: 1146
<212> TYPE: DNA
<213> ORGANISM: Homo sapiens
<220> FEATURE:
<221> NAME/KEY: misc_feature
<222> LOCATION: (20)..(20)
<223> OTHER INFORMATION: n equals a,t,g, or c
<220> FEATURE:
<221> NAME/KEY: misc_feature
<222> LOCATION: (35)..(37)
<223> OTHER INFORMATION: n equals a,t,g, or c

<400> SEQUENCE: 63

aaaaaaaacc caggggaacn ttgggggccg ctttnnnttc cccctccagg ccattgggga     60

attcttcaag ttaatcctgc tttgctcttg gccaacaggg cttgtagggg ggagagaccc    120

aggatcatca aggggttcga gtgcaagcct cactcccagc cctggcaggc agccctgttc    180

gagaagacgc ggctactctg tggggcgacg ctcatcgccc ccagatggct cctgacagca    240

gcccactgcc tcaagccccg ctacatagtt cacctggggc agcacaacct ccagaaggag    300

gagggctgtg agcagacccg gacagccact gagtccttcc cccaccccgg cttcaacaac    360

agcctcccca acaaagacca ccgcaatgac atcatgctgg tgaagatggc atcgccagtc    420

tccatcacct gggctgtgcg acccctcacc ctctcctcac gctgtgtcac tgctggcacc    480

agctgyctca tttccggctg gggcagmacg tccagccccc agttacgcct gcctcacacc    540

ttgsgatgcg ccaacatcac catcattgag caccagaagt gtgagaacgc ctaccccggc    600
```

```
aacatcacag acaccatggt gtgtgccagc gtgcaggaag ggggcaagga ctcctgccag    660

ggtgactccg ggggccctct ggtctgtaac cagtctcttc aaggcattat ctcctggggc    720

caggatccgt gtgcgatcac ccgaaagcct ggtgtctaca cgaaagtctg caaatatgtg    780

gactggatcc aggagacgat gaagaacaat tagactggac ccacccacca cagcccatca    840

ccctccattt ccacttggtg tttggttcct gttcactctg ttaataagaa accctaagcc    900

aagaccctct acgaacattc tttgggcctc ctggactaca ggagatgctg tcacttaata    960

atcaacctgg ggttcgaaat cagtgagacc tggattcaaa ttctgccttg aaatattgtg   1020

actctgggaa tgacaacacc tggtttgttc tctgttgtat ccccagcccc aaagacagct   1080

cctggccata tatcaaggtt tcaataaata tttgctaaat gaaaaaraaa aaaaaaaaaa   1140

actcga                                                              1146
```

<210> SEQ ID NO 64
<211> LENGTH: 53
<212> TYPE: PRT
<213> ORGANISM: Homo sapiens

<400> SEQUENCE: 64

```
Ile Leu Leu Cys Ser Trp Pro Thr Gly Leu Val Gly Gly Arg Asp Pro
  1               5                  10                  15

Gly Ser Ser Arg Gly Ser Ser Ala Ser Leu Thr Pro Ser Pro Gly Arg
             20                  25                  30

Gln Pro Cys Ser Arg Arg Arg Gly Tyr Ser Val Gly Arg Arg Ser Ser
         35                  40                  45

Pro Pro Asp Gly Ser
     50
```

<210> SEQ ID NO 65
<211> LENGTH: 1146
<212> TYPE: DNA
<213> ORGANISM: Homo sapiens
<220> FEATURE:
<221> NAME/KEY: misc_feature
<222> LOCATION: (20)
<223> OTHER INFORMATION: n equals a,t,g, or c
<220> FEATURE:
<221> NAME/KEY: misc_feature
<222> LOCATION: (35)
<223> OTHER INFORMATION: n equals a,t,g, or c
<220> FEATURE:
<221> NAME/KEY: misc_feature
<222> LOCATION: (36)
<223> OTHER INFORMATION: n equals a,t,g, or c
<220> FEATURE:
<221> NAME/KEY: misc_feature
<222> LOCATION: (37)
<223> OTHER INFORMATION: n equals a,t,g, or c

<400> SEQUENCE: 65

```
aaaaaaaacc caggggaacn ttgggggccg ctttnnnttc cccctccagg ccattgggga     60

attcttcaag ttaatcctgc tttgctcttg gccaacaggg cttgtagggg ggagagaccc    120

aggatcatca aggggttcga gtgcaagcct cactcccagc cctggcaggc agccctgttc    180

gagaagacgc ggctactctg tggggcgacg ctcatcgccc ccagatggct cctgacagca    240

gcccactgcc tcaagccccg ctacatagtt cacctggggc agcacaacct ccagaaggag    300

gagggctgtg agcagacccg gacagccact gagtccttcc cccaccccgg cttcaacaac    360

agcctcccca acaaagacca ccgcaatgac atcatgctgg tgaagatggc atcgccagtc    420

tccatcacct gggctgtgcg acccctcacc ctctcctcac gctgtgtcac tgctggcacc    480
```

-continued

```
agctgyctca tttccggctg gggcagmacg tccagccccc agttacgcct gcctcacacc    540

ttgsgatgcg ccaacatcac catcattgag caccagaagt gtgagaacgc ctaccccggc    600

aacatcacag acaccatggt gtgtgccagc gtgcaggaag gggcaagga ctcctgccag    660

ggtgactccg gggccctct ggtctgtaac cagtctcttc aaggcattat ctcctggggc    720

caggatccgt gtgcgatcac ccgaaagcct ggtgtctaca cgaaagtctg caaatatgtg    780

gactggatcc aggagacgat gaagaacaat tagactggac ccacccacca cagcccatca    840

ccctccattt ccacttggtg tttggttcct gttcactctg ttaataagaa accctaagcc    900

aagaccctct acgaacattc tttgggcctc ctggactaca ggagatgctg tcacttaata    960

atcaacctgg ggttcgaaat cagtgagacc tggattcaaa ttctgccttg aaatattgtg   1020

actctgggaa tgacaacacc tggtttgttc tctgttgtat ccccagcccc aaagacagct   1080

cctggccata tatcaaggtt tcaataaata tttgctaaat gaaaaaraaa aaaaaaaaaa   1140

actcga                                                              1146


<210> SEQ ID NO 66
<211> LENGTH: 54
<212> TYPE: PRT
<213> ORGANISM: Homo sapiens
<220> FEATURE:
<221> NAME/KEY: SITE
<222> LOCATION: (54)
<223> OTHER INFORMATION: Xaa equals stop translation

<400> SEQUENCE: 66

Ile Leu Leu Cys Ser Trp Pro Thr Gly Leu Val Gly Gly Arg Asp Pro
  1               5                  10                  15

Gly Ser Ser Arg Gly Ser Ser Ala Ser Leu Thr Pro Ser Pro Gly Arg
             20                  25                  30

Gln Pro Cys Ser Arg Arg Arg Gly Tyr Ser Val Gly Arg Arg Ser Ser
         35                  40                  45

Pro Pro Asp Gly Ser Xaa
     50


<210> SEQ ID NO 67
<211> LENGTH: 246
<212> TYPE: PRT
<213> ORGANISM: Homo sapiens

<400> SEQUENCE: 67

Met Arg Ile Leu Gln Leu Ile Leu Leu Ala Leu Ala Thr Gly Leu Val
  1               5                  10                  15

Gly Gly Glu Thr Arg Ile Ile Lys Gly Phe Glu Cys Lys Leu His Ser
             20                  25                  30

Gln Pro Trp Gln Ala Ala Leu Phe Glu Lys Thr Arg Leu Leu Cys Gly
         35                  40                  45

Ala Thr Leu Ile Ala Pro Arg Trp Leu Leu Thr Ala Ala His Cys Leu
     50                  55                  60

Lys Pro Arg Tyr Ile Val His Leu Gly Gln His Asn Leu Gln Lys Glu
 65                  70                  75                  80

Glu Gly Cys Glu Gln Thr Arg Thr Ala Thr Glu Ser Phe Pro His Pro
                 85                  90                  95

Gly Phe Asn Asn Ser Leu Pro Asn Lys Asp His Arg Asn Asp Ile Met
            100                 105                 110

Leu Val Lys Met Ala Ser Pro Val Ser Ile Thr Trp Ala Val Arg Pro
        115                 120                 125
```

```
Leu Thr Leu Ser Ser Arg Cys Val Thr Ala Gly Thr Ser Cys Ser Phe
    130                 135                 140

Pro Ala Gly Ala Ala Arg Pro Asp Pro Ser Tyr Ala Cys Leu Thr Pro
145                 150                 155                 160

Cys Asp Ala Pro Thr Ser Pro Ser Leu Ser Thr Arg Ser Val Arg Thr
                165                 170                 175

Pro Thr Pro Ala Thr Ser Gln Thr Pro Trp Cys Val Pro Ala Cys Arg
            180                 185                 190

Lys Gly Ala Arg Thr Pro Ala Arg Val Thr Pro Gly Ala Leu Trp Ser
        195                 200                 205

Val Thr Ser Leu Phe Lys Ala Leu Ser Pro Gly Ala Arg Ile Arg Val
    210                 215                 220

Arg Ser Pro Glu Ser Leu Val Ser Thr Arg Lys Ser Ala Asn Met Trp
225                 230                 235                 240

Thr Gly Ser Arg Arg Arg
                245


<210> SEQ ID NO 68
<211> LENGTH: 228
<212> TYPE: PRT
<213> ORGANISM: Homo sapiens

<400> SEQUENCE: 68

Glu Thr Arg Ile Ile Lys Gly Phe Glu Cys Lys Leu His Ser Gln Pro
  1               5                  10                  15

Trp Gln Ala Ala Leu Phe Glu Lys Thr Arg Leu Leu Cys Gly Ala Thr
             20                  25                  30

Leu Ile Ala Pro Arg Trp Leu Leu Thr Ala Ala His Cys Leu Lys Pro
         35                  40                  45

Arg Tyr Ile Val His Leu Gly Gln His Asn Leu Gln Lys Glu Glu Gly
     50                  55                  60

Cys Glu Gln Thr Arg Thr Ala Thr Glu Ser Phe Pro His Pro Gly Phe
 65                  70                  75                  80

Asn Asn Ser Leu Pro Asn Lys Asp His Arg Asn Asp Ile Met Leu Val
                 85                  90                  95

Lys Met Ala Ser Pro Val Ser Ile Thr Trp Ala Val Arg Pro Leu Thr
            100                 105                 110

Leu Ser Ser Arg Cys Val Thr Ala Gly Thr Ser Cys Ser Phe Pro Ala
        115                 120                 125

Gly Ala Ala Arg Pro Asp Pro Ser Tyr Ala Cys Leu Thr Pro Cys Asp
    130                 135                 140

Ala Pro Thr Ser Pro Ser Leu Ser Thr Arg Ser Val Arg Thr Pro Thr
145                 150                 155                 160

Pro Ala Thr Ser Gln Thr Pro Trp Cys Val Pro Ala Cys Arg Lys Gly
                165                 170                 175

Ala Arg Thr Pro Ala Arg Val Thr Pro Gly Ala Leu Trp Ser Val Thr
            180                 185                 190

Ser Leu Phe Lys Ala Leu Ser Pro Gly Ala Arg Ile Arg Val Arg Ser
        195                 200                 205

Pro Glu Ser Leu Val Ser Thr Arg Lys Ser Ala Asn Met Trp Thr Gly
    210                 215                 220

Ser Arg Arg Arg
225


<210> SEQ ID NO 69
<211> LENGTH: 74
```

<212> TYPE: PRT
<213> ORGANISM: Homo sapiens

<400> SEQUENCE: 69

```
Cys Lys Leu His Ser Gln Pro Trp Gln Ala Ala Leu Phe Glu Lys Thr
  1               5                  10                  15

Arg Leu Leu Cys Gly Ala Thr Leu Ile Ala Pro Arg Trp Leu Leu Thr
             20                  25                  30

Ala Ala His Cys Leu Lys Pro Arg Tyr Ile Val His Leu Gly Gln His
         35                  40                  45

Asn Leu Gln Lys Glu Glu Gly Cys Glu Gln Thr Arg Thr Ala Thr Glu
     50                  55                  60

Ser Phe Pro His Pro Gly Phe Asn Asn Ser
 65                  70
```

<210> SEQ ID NO 70
<211> LENGTH: 1974
<212> TYPE: DNA
<213> ORGANISM: Homo sapiens

<400> SEQUENCE: 70

```
gaattcggca cgaggctgag ggagctgcag cgcagcagag tatctgacgg cgccaggttg     60

cgtaggtgcg gcacgaggag ttttcccggc agcgaggagg tcctgagcag catggcccgg    120

aggagcgcct tccctgccgc cgcgctctgg ctctggagca tcctcctgtg cctgctggca    180

ctgcgggcgg aggccgggcc gccgcaggag gagagcctgt acctatggat cgatgctcac    240

caggcaagag tactcatagg atttgaagaa gatatcctga ttgtttcaga ggggaaaatg    300

gcacctttta cacatgattt cagaaaagcg caacagagaa tgccagctat tcctgtcaat    360

atccattcca tgaattttac ctggcaagct gcagggcagg cagaatactt ctatgaattc    420

ctgtccttgc gctccctgga taaaggcatc atggcagatc caaccgtcaa tgtccctctg    480

ctgggaacag tgcctcacaa ggcatcagtt gttcaagttg gtttcccatg tcttggaaaa    540

caggatgggg tggcagcatt tgaagtggat gtgattgtta tgaattctga aggcaacacc    600

attctccaaa cacctcaaaa tgctatcttc tttaaaacat gtcaacaagc tgagtgccca    660

ggcgggtgcc gaaatggagg cttttgtaat gaaagacgca tctgcgagtg tcctgatggg    720

ttccacggac ctcactgtga gaaagccctt tgtaccccac gatgtatgaa tggtggactt    780

tgtgtgactc ctggtttctg catctgccca cctggattct atggagtgaa ctgtgacaaa    840

gcaaactgct caaccacctg ctttaatgga gggacctgtt tctaccctgg aaaatgtatt    900

tsccctccag gactagaggg agagcagtgt gaaatcagca aatgcccaca accctgtcga    960

aatggaggta aatgcattgg taaaagcaaa tgtaagtktt ccaaaggtta ccagggagac   1020

ctctgttcaa agcctgtctg cgagcctggc tgtggtgcac atggaacctg ccatgaaccc   1080

aacaaatgcc aatgtcaaga aggttggcat ggaagacact gcaataaaag gtacgaagcc   1140

agcctcatac atgccctgag gccagcaggc gcccagctca ggcagcacac gccttcactt   1200

aaaaaggccg aggagcggcg ggatccacct gaatccaatt acatctggtg aactccgaca   1260

tctgaaacgt tttaagttac accaagttca tagcctttgt taacctttca tgtgttgaat   1320

gttcaaataa tgttcattac acttaagaat actggcctga attttattag cttcattata   1380

aatcactgag ctgatattta ctcttccttt taagttttct aagtacgtct gtagcatgat   1440

ggtatagatt ttcttgtttc agtgctttgg gacagatttt atattatgtc aattgatcag   1500

gttaaaattt tcagtgtgta gttggcagat attttcaaaa ttacaatgca tttatggtgt   1560
```

```
ctgggggcag gggaacatca gaaaggttaa attgggcaaa aatgcgtaag tcacaagaat   1620

ttggatggtg cagttaatgt tgaagttaca gcatttcaga ttttattgtc agatatttag   1680

atgtttgtta catttttaaa aattgctctt aatttttaaa ctctcaatac aatatatttt   1740

gaccttacca ttattccaga gattcagtat taaaaaaaaa aaaattacac tgtggtagtg   1800

gcatttaaac aatataatat attctaaaca caatgaaata gggaatataa tgtatgaact   1860

ttttgcattg gcttgaagca atataatata ttgtaaacaa aacacagctc ttacctaata   1920

aacattttat actgtttgta tgtataaaat aaaggtgctg ctttagtttt ctga         1974
```

```
<210> SEQ ID NO 71
<211> LENGTH: 380
<212> TYPE: PRT
<213> ORGANISM: Homo sapiens
<220> FEATURE:
<221> NAME/KEY: SITE
<222> LOCATION: (264)
<223> OTHER INFORMATION: Xaa equals any of the naturally occurring
      L-amino acids
<220> FEATURE:
<221> NAME/KEY: SITE
<222> LOCATION: (296)
<223> OTHER INFORMATION: Xaa equals any of the naturally occurring
      L-amino acids
<220> FEATURE:
<221> NAME/KEY: SITE
<222> LOCATION: (380)
<223> OTHER INFORMATION: Xaa equals stop translation

<400> SEQUENCE: 71

Met Ala Arg Arg Ser Ala Phe Pro Ala Ala Ala Leu Trp Leu Trp Ser
  1               5                  10                  15

Ile Leu Leu Cys Leu Leu Ala Leu Arg Ala Glu Ala Gly Pro Pro Gln
             20                  25                  30

Glu Glu Ser Leu Tyr Leu Trp Ile Asp Ala His Gln Ala Arg Val Leu
         35                  40                  45

Ile Gly Phe Glu Glu Asp Ile Leu Ile Val Ser Glu Gly Lys Met Ala
     50                  55                  60

Pro Phe Thr His Asp Phe Arg Lys Ala Gln Gln Arg Met Pro Ala Ile
 65                  70                  75                  80

Pro Val Asn Ile His Ser Met Asn Phe Thr Trp Gln Ala Ala Gly Gln
                 85                  90                  95

Ala Glu Tyr Phe Tyr Glu Phe Leu Ser Leu Arg Ser Leu Asp Lys Gly
            100                 105                 110

Ile Met Ala Asp Pro Thr Val Asn Val Pro Leu Leu Gly Thr Val Pro
        115                 120                 125

His Lys Ala Ser Val Val Gln Val Gly Phe Pro Cys Leu Gly Lys Gln
    130                 135                 140

Asp Gly Val Ala Ala Phe Glu Val Asp Val Ile Val Met Asn Ser Glu
145                 150                 155                 160

Gly Asn Thr Ile Leu Gln Thr Pro Gln Asn Ala Ile Phe Phe Lys Thr
                165                 170                 175

Cys Gln Gln Ala Glu Cys Pro Gly Gly Cys Arg Asn Gly Gly Phe Cys
            180                 185                 190

Asn Glu Arg Arg Ile Cys Glu Cys Pro Asp Gly Phe His Gly Pro His
        195                 200                 205

Cys Glu Lys Ala Leu Cys Thr Pro Arg Cys Met Asn Gly Gly Leu Cys
    210                 215                 220

Val Thr Pro Gly Phe Cys Ile Cys Pro Pro Gly Phe Tyr Gly Val Asn
225                 230                 235                 240
```

```
Cys Asp Lys Ala Asn Cys Ser Thr Thr Cys Phe Asn Gly Gly Thr Cys
                245                 250                 255

Phe Tyr Pro Gly Lys Cys Ile Xaa Pro Pro Gly Leu Glu Gly Glu Gln
            260                 265                 270

Cys Glu Ile Ser Lys Cys Pro Gln Pro Cys Arg Asn Gly Gly Lys Cys
        275                 280                 285

Ile Gly Lys Ser Lys Cys Lys Xaa Ser Lys Gly Tyr Gln Gly Asp Leu
    290                 295                 300

Cys Ser Lys Pro Val Cys Glu Pro Gly Cys Gly Ala His Gly Thr Cys
305                 310                 315                 320

His Glu Pro Asn Lys Cys Gln Cys Gln Glu Gly Trp His Gly Arg His
                325                 330                 335

Cys Asn Lys Arg Tyr Glu Ala Ser Leu Ile His Ala Leu Arg Pro Ala
            340                 345                 350

Gly Ala Gln Leu Arg Gln His Thr Pro Ser Leu Lys Lys Ala Glu Glu
        355                 360                 365

Arg Arg Asp Pro Pro Glu Ser Asn Tyr Ile Trp Xaa
    370                 375                 380
```

<210> SEQ ID NO 72
<211> LENGTH: 1789
<212> TYPE: DNA
<213> ORGANISM: Homo sapiens

<400> SEQUENCE: 72

```
gaattcggca cgaggctgag ggagctgcag cgcagcagag tatctgacgg cgccaggttg     60

cgtaggtgcg gcacgaggag ttttcccggc agcgaggagg tcctgagcag catggcccgg    120

aggagcgcct tccctgccgc cgcgctctgg ctctggagca tcctcctgtg cctgctggca    180

ctgcgggcgg aggccgggcc gccgcaggag gagagcctgt acctatggat cgatgctcac    240

caggcaagag tactcatagg atttgaagaa gatatcctga ttgtttcaga ggggaaaatg    300

gcacctttta cacatgattt cagaaaagcg caacagagaa tgccagctat tcctgtcaat    360

atccattcca tgaattttac ctggcaagct gcagggcagg cagaatactt ctatgaattc    420

ctgtccttgc gctccctgga taaaggcatc atggcagatc caaccgtcaa tgtccctctg    480

ctgggaacag tgcctcacaa ggcatcagtt gttcaagttg gtttcccatg tcttggaaaa    540

caggatgggg tggcagcatt tgaagtggat gtgattgtta tgaattctga aggcaacacc    600

attctccaaa cacctcaaaa tgctatcttc tttaaaacat gtcaacaagc tgagtgccca    660

ggcgggtgcc gaaatggagg cttttgtaat gaaagacgca tctgcgagtg tcctgatggg    720

ttccacggac ctcactgtga gaaagccctt tgtaccccac gatgtatgaa tggtggactt    780

tgtgtgactc ctggtttctg catctgccca cctggattct atggagtgaa ctgtgacaaa    840

gcaaactgct caaccacctg ctttaatgga gggacctgtt tctaccctgg aaaatgtatt    900

tgccctccag gactagaggg agagcagtgt gaaatcagca aatgcccaca accctgtcga    960

aatggaggta aatgcattgg taaaagcaaa tgtaagtgtt ccaaaggtta ccagggagac   1020

ctctgttcaa agcctgtctg cgagcctggc tgtggtgcac atggaacctg ccatgaaccc   1080

aacaaatgcc aatgtcaaga aggttggcat ggaagacact gcaataaaag gtacgaagcc   1140

agcctcatac atgccctgag gccagcaggc gcccagctca ggcagcacac gccttcactt   1200

aaaaaggccg aggagcggcg ggatccacct gaatccaatt acatctggtg aactccgaca   1260

tctgaaacgt tttaagttac accaagttca tagcctttgt taacctttca tgtgttgaat   1320
```

-continued

```
gttcaaataa tgttcattac acttaagaat actggcctga attttattag cttcattata   1380

aatcactgag ctgatattta ctcttccttt taagttttct aagtacgtct gtagcatgat   1440

ggtatagatt ttcttgtttc agtgctttgg gacagatttt atattatgtc aattgatcag   1500

gttaaaattt tcagtgtgta gttggcagat attttcaaaa ttacaatgca tttatggtgt   1560

ctgggggcag gggaacatca gaaaggttaa attgggcaaa aatgcgtaag tcacaagaat   1620

ttggatggtg cagttaatgt tgaagttaca gcatttcaga ttttattgtc agatatttag   1680

atgtttgtta catttttaaa aattgctctt aatttttaaa ctctcaatac aatatatttt   1740

gaccttacca ttattccaga gattcagtat taaaaaaaaa aaaaaaaaa               1789
```

<210> SEQ ID NO 73
<211> LENGTH: 379
<212> TYPE: PRT
<213> ORGANISM: Homo sapiens

<400> SEQUENCE: 73

```
Met Ala Arg Arg Ser Ala Phe Pro Ala Ala Ala Leu Trp Leu Trp Ser
  1               5                  10                  15

Ile Leu Leu Cys Leu Leu Ala Leu Arg Ala Glu Ala Gly Pro Pro Gln
             20                  25                  30

Glu Glu Ser Leu Tyr Leu Trp Ile Asp Ala His Gln Ala Arg Val Leu
         35                  40                  45

Ile Gly Phe Glu Glu Asp Ile Leu Ile Val Ser Glu Gly Lys Met Ala
     50                  55                  60

Pro Phe Thr His Asp Phe Arg Lys Ala Gln Gln Arg Met Pro Ala Ile
 65                  70                  75                  80

Pro Val Asn Ile His Ser Met Asn Phe Thr Trp Gln Ala Ala Gly Gln
                 85                  90                  95

Ala Glu Tyr Phe Tyr Glu Phe Leu Ser Leu Arg Ser Leu Asp Lys Gly
            100                 105                 110

Ile Met Ala Asp Pro Thr Val Asn Val Pro Leu Leu Gly Thr Val Pro
        115                 120                 125

His Lys Ala Ser Val Val Gln Val Gly Phe Pro Cys Leu Gly Lys Gln
    130                 135                 140

Asp Gly Val Ala Ala Phe Glu Val Asp Val Ile Val Met Asn Ser Glu
145                 150                 155                 160

Gly Asn Thr Ile Leu Gln Thr Pro Gln Asn Ala Ile Phe Phe Lys Thr
                165                 170                 175

Cys Gln Gln Ala Glu Cys Pro Gly Gly Cys Arg Asn Gly Gly Phe Cys
            180                 185                 190

Asn Glu Arg Arg Ile Cys Glu Cys Pro Asp Gly Phe His Gly Pro His
        195                 200                 205

Cys Glu Lys Ala Leu Cys Thr Pro Arg Cys Met Asn Gly Gly Leu Cys
    210                 215                 220

Val Thr Pro Gly Phe Cys Ile Cys Pro Pro Gly Phe Tyr Gly Val Asn
225                 230                 235                 240

Cys Asp Lys Ala Asn Cys Ser Thr Thr Cys Phe Asn Gly Gly Thr Cys
                245                 250                 255

Phe Tyr Pro Gly Lys Cys Ile Cys Pro Pro Gly Leu Glu Gly Glu Gln
            260                 265                 270

Cys Glu Ile Ser Lys Cys Pro Gln Pro Cys Arg Asn Gly Gly Lys Cys
        275                 280                 285

Ile Gly Lys Ser Lys Cys Lys Cys Ser Lys Gly Tyr Gln Gly Asp Leu
    290                 295                 300
```

```
Cys Ser Lys Pro Val Cys Glu Pro Gly Cys Gly Ala His Gly Thr Cys
305                 310                 315                 320

His Glu Pro Asn Lys Cys Gln Cys Gln Glu Gly Trp His Gly Arg His
                325                 330                 335

Cys Asn Lys Arg Tyr Glu Ala Ser Leu Ile His Ala Leu Arg Pro Ala
            340                 345                 350

Gly Ala Gln Leu Arg Gln His Thr Pro Ser Leu Lys Lys Ala Glu Glu
        355                 360                 365

Arg Arg Asp Pro Pro Glu Ser Asn Tyr Ile Trp
    370                 375


<210> SEQ ID NO 74
<211> LENGTH: 1974
<212> TYPE: DNA
<213> ORGANISM: Homo sapiens

<400> SEQUENCE: 74

gaattcggca cgaggctgag ggagctgcag cgcagcagag tatctgacgg cgccaggttg     60

cgtaggtgcg gcacgaggag ttttcccggc agcgaggagg tcctgagcag catggcccgg    120

aggagcgcct tccctgccgc cgcgctctgg ctctggagca tcctcctgtg cctgctggca    180

ctgcgggcgg aggccgggcc gccgcaggag gagagcctgt acctatggat cgatgctcac    240

caggcaagag tactcatagg atttgaagaa gatatcctga ttgtttcaga ggggaaaatg    300

gcacctttta cacatgattt cagaaaagcg caacagagaa tgccagctat tcctgtcaat    360

atccattcca tgaattttac ctggcaagct gcagggcagg cagaatactt ctatgaattc    420

ctgtccttgc gctccctgga taaaggcatc atggcagatc caaccgtcaa tgtccctctg    480

ctgggaacag tgcctcacaa ggcatcagtt gttcaagttg gtttcccatg tcttggaaaa    540

caggatgggg tggcagcatt tgaagtggat gtgattgtta tgaattctga aggcaacacc    600

attctccaaa cacctcaaaa tgctatcttc tttaaaacat gtcaacaagc tgagtgccca    660

ggcgggtgcc gaaatggagg cttttgtaat gaaagacgca tctgcgagtg tcctgatggg    720

ttccacggac ctcactgtga gaaagccctt tgtaccccac gatgtatgaa tggtggactt    780

tgtgtgactc ctggtttctg catctgccca cctggattct atggagtgaa ctgtgacaaa    840

gcaaactgct caaccacctg ctttaatgga gggacctgtt tctaccctgg aaaatgtatt    900

tsccctccag gactagaggg agagcagtgt gaaatcagca aatgcccaca accctgtcga    960

aatggaggta aatgcattgg taaaagcaaa tgtaagtktt ccaaaggtta ccagggagac   1020

ctctgttcaa agcctgtctg cgagcctggc tgtggtgcac atggaacctg ccatgaaccc   1080

aacaaatgcc aatgtcaaga aggttggcat ggaagacact gcaataaaag gtacgaagcc   1140

agcctcatac atgccctgag gccagcaggc gcccagctca ggcagcacac gccttcactt   1200

aaaaaggccg aggagcggcg ggatccacct gaatccaatt acatctggtg aactccgaca   1260

tctgaaacgt tttaagttac accaagttca tagcctttgt taacctttca tgtgttgaat   1320

gttcaaataa tgttcattac acttaagaat actggcctga attttattag cttcattata   1380

aatcactgag ctgatattta ctcttccttt taagttttct aagtacgtct gtagcatgat   1440

ggtatagatt ttcttgtttc agtgctttgg gacagatttt atattatgtc aattgatcag   1500

gttaaaattt tcagtgtgta gttggcagat attttcaaaa ttacaatgca tttatggtgt   1560

ctgggggcag gggaacatca gaaaggttaa attgggcaaa aatgcgtaag tcacaagaat   1620

ttggatggtg cagttaatgt tgaagttaca gcatttcaga ttttattgtc agatatttag   1680
```

-continued

```
atgtttgtta catttttaaa aattgctctt aatttttaaa ctctcaatac aatatatttt   1740

gaccttacca ttattccaga gattcagtat taaaaaaaaa aaaattacac tgtggtagtg   1800

gcatttaaac aatataatat attctaaaca caatgaaata gggaatataa tgtatgaact   1860

ttttgcattg gcttgaagca atataatata ttgtaaacaa aacacagctc ttacctaata   1920

aacattttat actgtttgta tgtataaaat aaaggtgctg ctttagtttt ctga         1974


<210> SEQ ID NO 75
<211> LENGTH: 379
<212> TYPE: PRT
<213> ORGANISM: Homo sapiens
<220> FEATURE:
<221> NAME/KEY: SITE
<222> LOCATION: (264)
<223> OTHER INFORMATION: Xaa equals any amino acid
<220> FEATURE:
<221> NAME/KEY: SITE
<222> LOCATION: (296)
<223> OTHER INFORMATION: Xaa equals any amino acid

<400> SEQUENCE: 75

Met Ala Arg Arg Ser Ala Phe Pro Ala Ala Ala Leu Trp Leu Trp Ser
  1               5                  10                  15

Ile Leu Leu Cys Leu Leu Ala Leu Arg Ala Glu Ala Gly Pro Pro Gln
             20                  25                  30

Glu Glu Ser Leu Tyr Leu Trp Ile Asp Ala His Gln Ala Arg Val Leu
         35                  40                  45

Ile Gly Phe Glu Glu Asp Ile Leu Ile Val Ser Glu Gly Lys Met Ala
     50                  55                  60

Pro Phe Thr His Asp Phe Arg Lys Ala Gln Gln Arg Met Pro Ala Ile
 65                  70                  75                  80

Pro Val Asn Ile His Ser Met Asn Phe Thr Trp Gln Ala Ala Gly Gln
                 85                  90                  95

Ala Glu Tyr Phe Tyr Glu Phe Leu Ser Leu Arg Ser Leu Asp Lys Gly
            100                 105                 110

Ile Met Ala Asp Pro Thr Val Asn Val Pro Leu Leu Gly Thr Val Pro
        115                 120                 125

His Lys Ala Ser Val Val Gln Val Gly Phe Pro Cys Leu Gly Lys Gln
    130                 135                 140

Asp Gly Val Ala Ala Phe Glu Val Asp Val Ile Val Met Asn Ser Glu
145                 150                 155                 160

Gly Asn Thr Ile Leu Gln Thr Pro Gln Asn Ala Ile Phe Phe Lys Thr
                165                 170                 175

Cys Gln Gln Ala Glu Cys Pro Gly Gly Cys Arg Asn Gly Gly Phe Cys
            180                 185                 190

Asn Glu Arg Arg Ile Cys Glu Cys Pro Asp Gly Phe His Gly Pro His
        195                 200                 205

Cys Glu Lys Ala Leu Cys Thr Pro Arg Cys Met Asn Gly Gly Leu Cys
    210                 215                 220

Val Thr Pro Gly Phe Cys Ile Cys Pro Pro Gly Phe Tyr Gly Val Asn
225                 230                 235                 240

Cys Asp Lys Ala Asn Cys Ser Thr Thr Cys Phe Asn Gly Gly Thr Cys
                245                 250                 255

Phe Tyr Pro Gly Lys Cys Ile Xaa Pro Pro Gly Leu Glu Gly Glu Gln
            260                 265                 270

Cys Glu Ile Ser Lys Cys Pro Gln Pro Cys Arg Asn Gly Gly Lys Cys
        275                 280                 285
```

```
Ile Gly Lys Ser Lys Cys Lys Xaa Ser Lys Gly Tyr Gln Gly Asp Leu
    290                 295                 300

Cys Ser Lys Pro Val Cys Glu Pro Gly Cys Gly Ala His Gly Thr Cys
305                 310                 315                 320

His Glu Pro Asn Lys Cys Gln Cys Gln Glu Gly Trp His Gly Arg His
                325                 330                 335

Cys Asn Lys Arg Tyr Glu Ala Ser Leu Ile His Ala Leu Arg Pro Ala
            340                 345                 350

Gly Ala Gln Leu Arg Gln His Thr Pro Ser Leu Lys Lys Ala Glu Glu
        355                 360                 365

Arg Arg Asp Pro Pro Glu Ser Asn Tyr Ile Trp
    370                 375


<210> SEQ ID NO 76
<211> LENGTH: 613
<212> TYPE: DNA
<213> ORGANISM: Homo sapiens
<220> FEATURE:
<221> NAME/KEY: misc_feature
<222> LOCATION: (25)..(25)
<223> OTHER INFORMATION: n equals a,t,g, or c

<400> SEQUENCE: 76

gaattcggca cgagcgggac gcggntgaag atagcctgcg gagtgtccgg gcggaacacg      60

gttgcagcac tcccagtaga ccaggagctc cgggaggcag ggccggcccc acgtcctctg     120

cgcaccaccc tgagttggat cctctgtgcg ccacccctga gttggatcca gggctagctg     180

ctgttgacct ccccactccc acgctgccct cctgcctgca gccatgacgc ccctgctcac     240

cctgatcctg gtggtcctca tgggcttacc tctggcccag gccttggact gccacgtgtg     300

tgcctacaac ggagacaact gcttcaaccc catgcgctgc ccggctatgg ttgcctactg     360

catgaccacg cgcacctact acacccccac caggatgaag gtcagtaagt cctgcgtgcc     420

ccgctgcttc gagactgtgt atgatggcta ctccaagcac gcgtccacca cctcctgctg     480

ccagtacgac ctctgcaacg gcaccggcct tgccaccccg gccaccctgg ccctggcccc     540

catcctcctg gccaccctct ggggtctcct ctaaagcccc cgaggcagac ccactcaaga     600

acaaagctct cga                                                        613


<210> SEQ ID NO 77
<211> LENGTH: 116
<212> TYPE: PRT
<213> ORGANISM: Homo sapiens

<400> SEQUENCE: 77

Met Thr Pro Leu Leu Thr Leu Ile Leu Val Val Leu Met Gly Leu Pro
  1               5                  10                  15

Leu Ala Gln Ala Leu Asp Cys His Val Cys Ala Tyr Asn Gly Asp Asn
            20                  25                  30

Cys Phe Asn Pro Met Arg Cys Pro Ala Met Val Ala Tyr Cys Met Thr
        35                  40                  45

Thr Arg Thr Tyr Tyr Thr Pro Thr Arg Met Lys Val Ser Lys Ser Cys
     50                  55                  60

Val Pro Arg Cys Phe Glu Thr Val Tyr Asp Gly Tyr Ser Lys His Ala
 65                  70                  75                  80

Ser Thr Thr Ser Cys Cys Gln Tyr Asp Leu Cys Asn Gly Thr Gly Leu
                85                  90                  95

Ala Thr Pro Ala Thr Leu Ala Leu Ala Pro Ile Leu Leu Ala Thr Leu
            100                 105                 110
```

Trp Gly Leu Leu
115

<210> SEQ ID NO 78
<211> LENGTH: 613
<212> TYPE: DNA
<213> ORGANISM: Homo sapiens
<220> FEATURE:
<221> NAME/KEY: misc_feature
<222> LOCATION: (25)..(25)
<223> OTHER INFORMATION: n equals a,t,g, or c

<400> SEQUENCE: 78
gaattcggca cgagcgggac gcggntgaag atagcctgcg gagtgtccgg gcggaacacg 60
gttgcagcac tcccagtaga ccaggagctc cgggaggcag ggccggcccc acgtcctctg 120
cgcaccaccc tgagttggat cctctgtgcg ccacccctga gttggatcca gggctagctg 180
ctgttgacct ccccactccc acgctgccct cctgcctgca gccatgacgc ccctgctcac 240
cctgatcctg gtggtcctca tgggcttacc tctggcccag gccttggact gccacgtgtg 300
tgcctacaac ggagacaact gcttcaaccc catgcgctgc ccggctatgg ttgcctactg 360
catgaccacg cgcacctact acacccccac caggatgaag gtcagtaagt cctgcgtgcc 420
ccgctgcttc gagactgtgt atgatggcta ctccaagcac gcgtccacca cctcctgctg 480
ccagtacgac ctctgcaacg gcaccggcct tgccaccccg gccaccctgg ccctggcccc 540
catcctcctg gccaccctct ggggtctcct ctaaagcccc cgaggcagac ccactcaaga 600
acaaagctct cga 613

<210> SEQ ID NO 79
<211> LENGTH: 116
<212> TYPE: PRT
<213> ORGANISM: Homo sapiens

<400> SEQUENCE: 79

Met Thr Pro Leu Leu Thr Leu Ile Leu Val Val Leu Met Gly Leu Pro
1 5 10 15

Leu Ala Gln Ala Leu Asp Cys His Val Cys Ala Tyr Asn Gly Asp Asn
20 25 30

Cys Phe Asn Pro Met Arg Cys Pro Ala Met Val Ala Tyr Cys Met Thr
35 40 45

Thr Arg Thr Tyr Tyr Thr Pro Thr Arg Met Lys Val Ser Lys Ser Cys
50 55 60

Val Pro Arg Cys Phe Glu Thr Val Tyr Asp Gly Tyr Ser Lys His Ala
65 70 75 80

Ser Thr Thr Ser Cys Cys Gln Tyr Asp Leu Cys Asn Gly Thr Gly Leu
85 90 95

Ala Thr Pro Ala Thr Leu Ala Leu Ala Pro Ile Leu Leu Ala Thr Leu
100 105 110

Trp Gly Leu Leu
115

<210> SEQ ID NO 80
<211> LENGTH: 57
<212> TYPE: PRT
<213> ORGANISM: Homo sapiens

<400> SEQUENCE: 80

Met Met Ala Thr Pro Ser Thr Arg Pro Pro Pro Ala Ala Ser Thr
1 5 10 15

```
Thr Ser Ala Thr Ala Pro Ala Leu Pro Pro Arg Pro Pro Trp Pro Trp
             20                  25                  30

Pro Pro Ser Ser Trp Pro Pro Ser Gly Val Ser Ser Lys Ala Pro Glu
        35                  40                  45

Ala Asp Pro Leu Lys Asn Lys Ala Leu
    50                  55


<210> SEQ ID NO 81
<211> LENGTH: 76
<212> TYPE: PRT
<213> ORGANISM: Homo sapiens

<400> SEQUENCE: 81

Leu Leu Leu Thr Ser Pro Leu Pro Arg Cys Pro Pro Ala Cys Ser His
  1               5                  10                  15

Asp Ala Pro Ala His Pro Asp Pro Gly Gly Pro His Gly Leu Thr Ser
             20                  25                  30

Gly Pro Gly Leu Gly Leu Pro Arg Val Cys Leu Gln Arg Arg Gln Leu
        35                  40                  45

Leu Gln Pro His Ala Leu Pro Gly Tyr Gly Cys Leu Leu His Asp His
    50                  55                  60

Ala His Leu Leu His Pro His Gln Asp Glu Gly Gln
 65                  70                  75


<210> SEQ ID NO 82
<211> LENGTH: 56
<212> TYPE: PRT
<213> ORGANISM: Homo sapiens

<400> SEQUENCE: 82

Trp Leu Leu Gln Ala Arg Val His His Leu Leu Leu Pro Val Arg Pro
  1               5                  10                  15

Leu Gln Arg His Arg Pro Cys His Pro Gly His Pro Gly Pro Gly Pro
             20                  25                  30

His Pro Pro Gly His Pro Leu Gly Ser Pro Leu Lys Pro Pro Arg Gln
        35                  40                  45

Thr His Ser Arg Thr Lys Leu Ser
    50                  55


<210> SEQ ID NO 83
<211> LENGTH: 697
<212> TYPE: DNA
<213> ORGANISM: Homo sapiens
<220> FEATURE:
<221> NAME/KEY: misc_feature
<222> LOCATION: (19)..(19)
<223> OTHER INFORMATION: n equals a,t,g, or c
<220> FEATURE:
<221> NAME/KEY: misc_feature
<222> LOCATION: (50)..(50)
<223> OTHER INFORMATION: n equals a,t,g, or c
<220> FEATURE:
<221> NAME/KEY: misc_feature
<222> LOCATION: (57)..(57)
<223> OTHER INFORMATION: n equals a,t,g, or c
<220> FEATURE:
<221> NAME/KEY: misc_feature
<222> LOCATION: (662)..(662)
<223> OTHER INFORMATION: n equals a,t,g, or c
<220> FEATURE:
<221> NAME/KEY: misc_feature
<222> LOCATION: (680)..(680)
<223> OTHER INFORMATION: n equals a,t,g, or c
<220> FEATURE:
<221> NAME/KEY: misc_feature
```

<222> LOCATION: (690)..(690)
<223> OTHER INFORMATION: n equals a,t,g, or c

<400> SEQUENCE: 83

```
aagaaaatta ccctcactna aaaaaaacaa aaactaaaag ctcgcacgcn tgcaggnacg     60

acactagtgg atccaaagaa ttcggcacga ggccacatcc caccggccct tacactgtgg    120

tgtccagcag catccggctt catgggggga cttgaaccct gcagcaggct cctgctcctg    180

cctctcctgc tggctgtagg tctccgtcct gtccaggccc aggcccagag cgattgcagt    240

tgctctacgg tgagcccggg cgtgctggca gggatcgtga tgggagacct ggtgctgaca    300

gtgctcattg ccctggccgt gtacttcctg ggccggctgg tccctcgggg gcgagggggct    360

gcggaggcga cccggaaaca gcgtatcact gagaccgagt cgccttatca ggagctccag    420

ggtcagaggt cggatgtcta cagcgacctc aacacacaga ggccgtatta caaatgagcc    480

cgaatcatga cagtcagcaa catgatacct ggatccagcc attcctgaag cccaccctgc    540

acctcattcc aactcctacc gcgatacaga cccacagagt gccatccctg agagaccaga    600

ccgctcccca atactctcct aaaataaaca tgaagcacaa aaaaaaaaaa aaaaaaaact    660

cngggggggg gcccggttan ccaatttggn cctaaag                             697
```

<210> SEQ ID NO 84
<211> LENGTH: 111
<212> TYPE: PRT
<213> ORGANISM: Homo sapiens

<400> SEQUENCE: 84

```
Met Gly Gly Leu Glu Pro Cys Ser Arg Leu Leu Leu Leu Pro Leu Leu
  1               5                  10                  15

Leu Ala Val Gly Leu Arg Pro Val Gln Ala Gln Ala Gln Ser Asp Cys
             20                  25                  30

Ser Cys Ser Thr Val Ser Pro Gly Val Leu Ala Gly Ile Val Met Gly
         35                  40                  45

Asp Leu Val Leu Thr Val Leu Ile Ala Leu Ala Val Tyr Phe Leu Gly
     50                  55                  60

Arg Leu Val Pro Arg Gly Arg Gly Ala Ala Glu Ala Thr Arg Lys Gln
 65                  70                  75                  80

Arg Ile Thr Glu Thr Glu Ser Pro Tyr Gln Glu Leu Gln Gly Gln Arg
                 85                  90                  95

Ser Asp Val Tyr Ser Asp Leu Asn Thr Gln Arg Pro Tyr Tyr Lys
            100                 105                 110
```

<210> SEQ ID NO 85
<211> LENGTH: 24
<212> TYPE: PRT
<213> ORGANISM: Homo sapiens

<400> SEQUENCE: 85

```
Val Leu Ala Gly Ile Val Met Gly Asp Leu Val Leu Thr Val Leu Ile
  1               5                  10                  15

Ala Leu Ala Val Tyr Phe Leu Gly
             20
```

<210> SEQ ID NO 86
<211> LENGTH: 14
<212> TYPE: PRT
<213> ORGANISM: Homo sapiens

<400> SEQUENCE: 86

Gln Ala Gln Ser Asp Cys Ser Cys Ser Thr Val Ser Pro Gly
1 5 10

<210> SEQ ID NO 87
<211> LENGTH: 24
<212> TYPE: PRT
<213> ORGANISM: Homo sapiens

<400> SEQUENCE: 87

Val Leu Ala Gly Ile Val Met Gly Asp Leu Val Leu Thr Val Leu Ile
1 5 10 15

Ala Leu Ala Val Tyr Phe Leu Gly
20

<210> SEQ ID NO 88
<211> LENGTH: 37
<212> TYPE: PRT
<213> ORGANISM: Homo sapiens

<400> SEQUENCE: 88

Val Pro Arg Gly Arg Gly Ala Ala Glu Ala Thr Arg Lys Gln Arg Ile
1 5 10 15

Thr Glu Thr Glu Ser Pro Tyr Gln Glu Leu Gln Gly Gln Arg Ser Asp
20 25 30

Val Tyr Ser Asp Leu
35

<210> SEQ ID NO 89
<211> LENGTH: 22
<212> TYPE: PRT
<213> ORGANISM: Homo sapiens

<400> SEQUENCE: 89

Glu Thr Glu Ser Pro Tyr Gln Glu Leu Gln Gly Gln Arg Ser Asp Val
1 5 10 15

Tyr Ser Asp Leu Asn Thr
20

<210> SEQ ID NO 90
<211> LENGTH: 1140
<212> TYPE: DNA
<213> ORGANISM: Homo sapiens

<400> SEQUENCE: 90
ctaggagcct cctaatgcag tgttctgcac agtcctgggg actgactgac tgaatcacac 60
ctctggggct gggggctgct gacatgtgtg cctttccttg gctgcttctt ctcctgctgc 120
tccaggargg cagccaaagg agactctgga gatggtgtgg atccgaggaa gtggttgcgg 180
tccttcagga gtccatcagc ctccccctgg aaataccacc agatgaagag gttgagaaca 240
tcatctggtc ctctcacaaa agtcttgcca ctgtggtgcc agggaaagag ggacatccag 300
ctaccatcat ggtgaccaat ccacactacc agggccaagt gagcttcctg gaccccarct 360
attccctgca tatcagcaat ctgagctggg aggattcagg gctttaccaa gctcaagtca 420
acctgagaac atcccagatc tctaccatgc agcagtacaa tctatgtgtc taccgatggc 480
tgtcagagdc cccasatcac tgtgaacttt gagagttctg gggaaggtgc ctgcagtatg 540
tccctggtgt gctctgtgga graaggcagg catggatatg acctacagct ggctctcccg 600
gggggatagc acttatacat tccatgaagg ccctgtcctc agcacatcct ggaggccggg 660
ggacagtgcc ctctcctaca cctgcagagc caacaacccc atcagcaacg tcagttcttg 720

```
ccccatccct gatgggccct tctatgcaga tcctaactat gcttctgaga agccttcaac    780

agccttctgc ctcctggcca agggattgct catcttcttg ctcttggtaa ttctggccat    840

gggactctgg gtcatccgag tccagaaaag acacaaaatg ccaaggatga agaaactcat    900

gagaaacaga atgaaattga ggaaggaggc aaagcctggc tccagccctg cctgactgct    960

ccttgggaac cccagtcctg agcttggttt cttcccagca cccagagaat ccttcctcag   1020

ctctcttctt tccaggggaa ggaggtgctc aggggtgggt atccagagag ccatacttct   1080

gagggaagac tggctggcaa taaagtcaaa ttaagtgacc accaaaaaaa aaaaaaaaaa   1140
```

```
<210> SEQ ID NO 91
<211> LENGTH: 142
<212> TYPE: PRT
<213> ORGANISM: Homo sapiens
<220> FEATURE:
<221> NAME/KEY: SITE
<222> LOCATION: (92)
<223> OTHER INFORMATION: Xaa equals any of the naturally occurring
      L-amino acids
<220> FEATURE:
<221> NAME/KEY: SITE
<222> LOCATION: (136)
<223> OTHER INFORMATION: Xaa equals any of the naturally occurring
      L-amino acids
<220> FEATURE:
<221> NAME/KEY: SITE
<222> LOCATION: (138)
<223> OTHER INFORMATION: Xaa equals any of the naturally occurring
      L-amino acids

<400> SEQUENCE: 91

Met Cys Ala Phe Pro Trp Leu Leu Leu Leu Leu Leu Leu Gln Glu Gly
  1               5                  10                  15

Ser Gln Arg Arg Leu Trp Arg Trp Cys Gly Ser Glu Glu Val Val Ala
             20                  25                  30

Val Leu Gln Glu Ser Ile Ser Leu Pro Leu Glu Ile Pro Pro Asp Glu
         35                  40                  45

Glu Val Glu Asn Ile Ile Trp Ser Ser His Lys Ser Leu Ala Thr Val
     50                  55                  60

Val Pro Gly Lys Glu Gly His Pro Ala Thr Ile Met Val Thr Asn Pro
 65                  70                  75                  80

His Tyr Gln Gly Gln Val Ser Phe Leu Asp Pro Xaa Tyr Ser Leu His
                 85                  90                  95

Ile Ser Asn Leu Ser Trp Glu Asp Ser Gly Leu Tyr Gln Ala Gln Val
            100                 105                 110

Asn Leu Arg Thr Ser Gln Ile Ser Thr Met Gln Gln Tyr Asn Leu Cys
        115                 120                 125

Val Tyr Arg Trp Leu Ser Glu Xaa Pro Xaa His Cys Glu Leu
    130                 135                 140


<210> SEQ ID NO 92
<211> LENGTH: 1147
<212> TYPE: DNA
<213> ORGANISM: Homo sapiens

<400> SEQUENCE: 92

ggcacgagct aggagcctcc taatgcagtc ttctgcacag tcctggggac tgactgactg     60

aatcacacct ctggggctgg gggctgctga catgtgtgcc tttccttggc tgcttcttct    120

cctgctgctc caggagggca gccaaaggag actctggaga tggtgtggat ccgaggaagt    180

ggttgcggtc cttcaggagt ccatcagcct ccccctggaa ataccaccag atgaagaggt    240
```

```
tgagaacatc atctggtcct ctcacaaaag tcttgccact gtggtgccag ggaaagaggg    300

acatccagct accatcatgg tgaccaatcc acactaccag ggccaagtga gcttcctgga    360

ccccagctat tccctgcata tcagcaatct gagctgggag gattcagggc ttttaccaag    420

ctcaagtcaa cctgagaaca tcccagatct ctaccatgca gcagtacaat ctatgtgtct    480

accgatggct gtcagagccc cagatcactg tgaactttga gagttctggg gaaggtgcct    540

gcagtatgtc cctggtgtgc tctgtggaga aggcaggcat ggatatgacc tacagctggc    600

tctcccgggg ggatagcact tatacattcc atgaaggccc tgtcctcagc acatcctgga    660

ggccggggga cagtgccctc tcctacacct gcagagccaa caaccccatc agcaacgtca    720

gttcttgccc catccctgat gggcccttct atgcagatcc taactatgct tctgagaagc    780

cttcaacagc cttctgcctc ctggccaagg gattgctcat cttcttgctc ttggtaattc    840

tggccatggg actctgggtc atccgagtcc agaaaagaca caaaatgcca aggatgaaga    900

aactcatgag aaacagaatg aaattgagga aggaggcaaa gcctggctcc agccctgcct    960

gactgctcct tgggaacccc agtcctgagc ttggtttctt cccagcaccc agagaatcct   1020

tcctcagctc tcttctttcc aggggaagga ggtgctcagg ggtgggtatc cagagagcca   1080

tacttctgag ggaagactgg ctggcaataa agtcaaatta agtgaccacc aaaaaaaaaa   1140

aaaaaaa                                                             1147
```

<210> SEQ ID NO 93
<211> LENGTH: 142
<212> TYPE: PRT
<213> ORGANISM: Homo sapiens

<400> SEQUENCE: 93

```
Met Cys Ala Phe Pro Trp Leu Leu Leu Leu Leu Leu Leu Gln Glu Gly
  1               5                  10                  15

Ser Gln Arg Arg Leu Trp Arg Trp Cys Gly Ser Glu Glu Val Val Ala
             20                  25                  30

Val Leu Gln Glu Ser Ile Ser Leu Pro Leu Glu Ile Pro Pro Asp Glu
         35                  40                  45

Glu Val Glu Asn Ile Ile Trp Ser Ser His Lys Ser Leu Ala Thr Val
     50                  55                  60

Val Pro Gly Lys Glu Gly His Pro Ala Thr Ile Met Val Thr Asn Pro
 65                  70                  75                  80

His Tyr Gln Gly Gln Val Ser Phe Leu Asp Pro Ser Tyr Ser Leu His
                 85                  90                  95

Ile Ser Asn Leu Ser Trp Glu Asp Ser Gly Leu Leu Pro Ser Ser Ser
            100                 105                 110

Gln Pro Glu Asn Ile Pro Asp Leu Tyr His Ala Ala Val Gln Ser Met
        115                 120                 125

Cys Leu Pro Met Ala Val Arg Ala Pro Asp His Cys Glu Leu
    130                 135                 140
```

<210> SEQ ID NO 94
<211> LENGTH: 1140
<212> TYPE: DNA
<213> ORGANISM: Homo sapiens

<400> SEQUENCE: 94

```
ctaggagcct cctaatgcag tgttctgcac agtcctgggg actgactgac tgaatcacac     60

ctctggggct gggggctgct gacatgtgtg cctttccttg gctgcttctt ctcctgctgc    120

tccaggargg cagccaaagg agactctgga gatggtgtgg atccgaggaa gtggttgcgg    180
```

```
tccttcagga gtccatcagc ctccccctgg aaataccacc agatgaagag gttgagaaca    240

tcatctggtc ctctcacaaa agtcttgcca ctgtggtgcc agggaaagag ggacatccag    300

ctaccatcat ggtgaccaat ccacactacc agggccaagt gagcttcctg gaccccarct    360

attccctgca tatcagcaat ctgagctggg aggattcagg gctttaccaa gctcaagtca    420

acctgagaac atcccagatc tctaccatgc agcagtacaa tctatgtgtc taccgatggc    480

tgtcagagdc cccasatcac tgtgaacttt gagagttctg ggaaggtgc ctgcagtatg    540

tccctggtgt gctctgtgga graaggcagg catggatatg acctacagct ggctctcccg    600

gggggatagc acttatacat tccatgaagg ccctgtcctc agcacatcct ggaggccggg    660

ggacagtgcc ctctcctaca cctgcagagc caacaacccc atcagcaacg tcagttcttg    720

ccccatccct gatgggccct tctatgcaga tcctaactat gcttctgaga agccttcaac    780

agccttctgc ctcctggcca agggattgct catcttcttg ctcttggtaa ttctggccat    840

gggactctgg gtcatccgag tccagaaaag acacaaaatg ccaaggatga agaaactcat    900

gagaaacaga atgaaattga ggaaggaggc aaagcctggc tccagccctg cctgactgct    960

ccttgggaac cccagtcctg agcttggttt cttcccagca cccagagaat ccttcctcag   1020

ctctcttctt tccaggggaa ggaggtgctc aggggtgggt atccagagag ccatacttct   1080

gagggaagac tggctggcaa taaagtcaaa ttaagtgacc accaaaaaaa aaaaaaaaaa   1140
```

<210> SEQ ID NO 95
<211> LENGTH: 142
<212> TYPE: PRT
<213> ORGANISM: Homo sapiens
<220> FEATURE:
<221> NAME/KEY: SITE
<222> LOCATION: (92)
<223> OTHER INFORMATION: Xaa equals any amino acid
<220> FEATURE:
<221> NAME/KEY: SITE
<222> LOCATION: (136)
<223> OTHER INFORMATION: Xaa equals any amino acid
<220> FEATURE:
<221> NAME/KEY: SITE
<222> LOCATION: (138)
<223> OTHER INFORMATION: Xaa equals any amino acid

<400> SEQUENCE: 95

```
Met Cys Ala Phe Pro Trp Leu Leu Leu Leu Leu Leu Leu Gln Glu Gly
  1               5                  10                  15

Ser Gln Arg Arg Leu Trp Arg Trp Cys Gly Ser Glu Glu Val Val Ala
             20                  25                  30

Val Leu Gln Glu Ser Ile Ser Leu Pro Leu Glu Ile Pro Pro Asp Glu
         35                  40                  45

Glu Val Glu Asn Ile Ile Trp Ser Ser His Lys Ser Leu Ala Thr Val
     50                  55                  60

Val Pro Gly Lys Glu Gly His Pro Ala Thr Ile Met Val Thr Asn Pro
 65                  70                  75                  80

His Tyr Gln Gly Gln Val Ser Phe Leu Asp Pro Xaa Tyr Ser Leu His
                 85                  90                  95

Ile Ser Asn Leu Ser Trp Glu Asp Ser Gly Leu Tyr Gln Ala Gln Val
            100                 105                 110

Asn Leu Arg Thr Ser Gln Ile Ser Thr Met Gln Gln Tyr Asn Leu Cys
        115                 120                 125

Val Tyr Arg Trp Leu Ser Glu Xaa Pro Xaa His Cys Glu Leu
    130                 135                 140
```

<210> SEQ ID NO 96
<211> LENGTH: 10
<212> TYPE: PRT
<213> ORGANISM: Homo sapiens

<400> SEQUENCE: 96

Ile Thr Pro Leu Gly Leu Gly Ala Ala Asp
1 5 10

<210> SEQ ID NO 97
<211> LENGTH: 149
<212> TYPE: PRT
<213> ORGANISM: Homo sapiens

<400> SEQUENCE: 97

Thr Leu Arg Val Leu Gly Lys Val Pro Ala Val Cys Pro Trp Cys Ala
1 5 10 15

Leu Trp Arg Lys Ala Gly Met Asp Met Thr Tyr Ser Trp Leu Ser Arg
20 25 30

Gly Asp Ser Thr Tyr Thr Phe His Glu Gly Pro Val Leu Ser Thr Ser
35 40 45

Trp Arg Pro Gly Asp Ser Ala Leu Ser Tyr Thr Cys Arg Ala Asn Asn
50 55 60

Pro Ile Ser Asn Val Ser Ser Cys Pro Ile Pro Asp Gly Pro Phe Tyr
65 70 75 80

Ala Asp Pro Asn Tyr Ala Ser Glu Lys Pro Ser Thr Ala Phe Cys Leu
85 90 95

Leu Ala Lys Gly Leu Leu Ile Phe Leu Leu Leu Val Ile Leu Ala Met
100 105 110

Gly Leu Trp Val Ile Arg Val Gln Lys Arg His Lys Met Pro Arg Met
115 120 125

Lys Lys Leu Met Arg Asn Arg Met Lys Leu Arg Lys Glu Ala Lys Pro
130 135 140

Gly Ser Ser Pro Ala
145

<210> SEQ ID NO 98
<211> LENGTH: 21
<212> TYPE: PRT
<213> ORGANISM: Homo sapiens

<400> SEQUENCE: 98

Ala Val Cys Pro Trp Cys Ala Leu Trp Arg Lys Ala Gly Met Asp Met
1 5 10 15

Thr Tyr Ser Trp Leu
20

<210> SEQ ID NO 99
<211> LENGTH: 24
<212> TYPE: PRT
<213> ORGANISM: Homo sapiens

<400> SEQUENCE: 99

Pro Gly Asp Ser Ala Leu Ser Tyr Thr Cys Arg Ala Asn Asn Pro Ile
1 5 10 15

Ser Asn Val Ser Ser Cys Pro Ile
20

<210> SEQ ID NO 100
<211> LENGTH: 24

```
<212> TYPE: PRT
<213> ORGANISM: Homo sapiens

<400> SEQUENCE: 100

Tyr Ala Ser Glu Lys Pro Ser Thr Ala Phe Cys Leu Leu Ala Lys Gly
 1               5                  10                  15

Leu Leu Ile Phe Leu Leu Leu Val
            20

<210> SEQ ID NO 101
<211> LENGTH: 26
<212> TYPE: PRT
<213> ORGANISM: Homo sapiens

<400> SEQUENCE: 101

Gln Lys Arg His Lys Met Pro Arg Met Lys Lys Leu Met Arg Asn Arg
 1               5                  10                  15

Met Lys Leu Arg Lys Glu Ala Lys Pro Gly
            20                  25

<210> SEQ ID NO 102
<211> LENGTH: 553
<212> TYPE: DNA
<213> ORGANISM: Homo sapiens

<400> SEQUENCE: 102

gtgtgccgga tttggttagc tgagcccacc gagaggcgcc tgcaggatga aagctctctg      60
tctcctcctc ctccctgtcc tggggctgtt ggtgtctagc aagaccctgt gctccatgga     120
agaagccatc aatgagagga tccaggaggt cgccggctcc ctaatattta gggcaataag     180
cagcattggc ctggagtgcc agagcgtcac ctccaggggg gacctggcta cttgcccccg     240
aggcttcgcc gtcaccggct gcacttgtgg ctccgcctgt ggctcgtggg atgtgcgcgc     300
cgagaccaca tgtcactgcc agtgcgcggg catggactgg accggagcgc gctgctgtcg     360
tgtgcagccc tgaggtcgcg cgcagtggca acagcgcggg cggaggcggc tccaggtccg     420
gagggttgcg ggggagctgg aaataaacct ggagatgatg atgatgatga tgatggaaaa     480
aaaaaaaaaa aaaaaaaaaa aaaaaaaaaa aaaaaaaaaa aaaaaaaaaa aaaaaaaaaa     540
aaaaaaaaaa aaa                                                        553

<210> SEQ ID NO 103
<211> LENGTH: 108
<212> TYPE: PRT
<213> ORGANISM: Homo sapiens

<400> SEQUENCE: 103

Met Lys Ala Leu Cys Leu Leu Leu Leu Pro Val Leu Gly Leu Leu Val
 1               5                  10                  15

Ser Ser Lys Thr Leu Cys Ser Met Glu Glu Ala Ile Asn Glu Arg Ile
            20                  25                  30

Gln Glu Val Ala Gly Ser Leu Ile Phe Arg Ala Ile Ser Ser Ile Gly
        35                  40                  45

Leu Glu Cys Gln Ser Val Thr Ser Arg Gly Asp Leu Ala Thr Cys Pro
    50                  55                  60

Arg Gly Phe Ala Val Thr Gly Cys Thr Cys Gly Ser Ala Cys Gly Ser
65                  70                  75                  80

Trp Asp Val Arg Ala Glu Thr Thr Cys His Cys Gln Cys Ala Gly Met
                85                  90                  95

Asp Trp Thr Gly Ala Arg Cys Cys Arg Val Gln Pro
            100                 105
```

100 105

<210> SEQ ID NO 104
<211> LENGTH: 575
<212> TYPE: DNA
<213> ORGANISM: Homo sapiens

<400> SEQUENCE: 104
ggcacgagtg caggaattcg tgtgccggat ttggttagct gagcccaccg agaggcgcct 60
gcaggatgaa agctctctgt ctcctcctcc tccctgtcct ggggctgttg gtgtctagca 120
agaccctgtg ctccatggaa gaagccatca atgagaggat ccaggaggtc gccggctccc 180
taatatttag ggcaataagc agcattggcc tggagtgcca gagcgtcacc tccagggggg 240
acctggctac ttgcccccga ggcttcgccg tcaccggctg cacttgtggc tccgcctgtg 300
gctcgtggga tgtgcgcgcc gagaccacat gtcactgcca gtgcgcgggc atggactgga 360
ccggagcgcg ctgctgtcgt gtgcagccct gaggtcgcgc gcagcgcgtg cacagcgcgg 420
gcggaggcgg ctccaggtcc ggaggggttg cgggggagct ggaaataaac ctggagatga 480
tgatgatgat gatgatggaa aaaaaaaaaa aaaaaaaaaa aaaaaaaaaa aaaaaaaaaa 540
aaaaaaaaaa aaaaaaaaaa aaaaaaaaaa aaaaa 575

<210> SEQ ID NO 105
<211> LENGTH: 108
<212> TYPE: PRT
<213> ORGANISM: Homo sapiens

<400> SEQUENCE: 105

Met Lys Ala Leu Cys Leu Leu Leu Leu Pro Val Leu Gly Leu Leu Val
1 5 10 15

Ser Ser Lys Thr Leu Cys Ser Met Glu Glu Ala Ile Asn Glu Arg Ile
20 25 30

Gln Glu Val Ala Gly Ser Leu Ile Phe Arg Ala Ile Ser Ser Ile Gly
35 40 45

Leu Glu Cys Gln Ser Val Thr Ser Arg Gly Asp Leu Ala Thr Cys Pro
50 55 60

Arg Gly Phe Ala Val Thr Gly Cys Thr Cys Gly Ser Ala Cys Gly Ser
65 70 75 80

Trp Asp Val Arg Ala Glu Thr Thr Cys His Cys Gln Cys Ala Gly Met
85 90 95

Asp Trp Thr Gly Ala Arg Cys Cys Arg Val Gln Pro
100 105

<210> SEQ ID NO 106
<211> LENGTH: 9
<212> TYPE: PRT
<213> ORGANISM: Homo sapiens

<400> SEQUENCE: 106

Leu Ser Pro Pro Arg Gly Ala Cys Arg
1 5

<210> SEQ ID NO 107
<211> LENGTH: 1346
<212> TYPE: DNA
<213> ORGANISM: Homo sapiens
<220> FEATURE:
<221> NAME/KEY: misc_feature
<222> LOCATION: (637)..(637)
<223> OTHER INFORMATION: n equals a,t,g, or c
<220> FEATURE:

<221> NAME/KEY: misc_feature
<222> LOCATION: (850)..(850)
<223> OTHER INFORMATION: n equals a,t,g, or c

<400> SEQUENCE: 107

```
ggtcgaccca cgcgtccgct gagagtagcc atgggctctg gaggagacag cctcctgggg     60

ggcaggggtt ccctgcctct gctgctcctg ctcatcatgg gaggcatggc tcaggactcc    120

ccgccccaga tcttagtcca cccccaggac cagctgttcc agggccctgg ccctgccagg    180

atgagctgcc gagcctcagg ccagccacct cccaccatcc gctggttgct gaatgggcag    240

cccctgagca tggtgccccc agacccacac cacctcctgc ctgatgggac ccttctgctg    300

ctacagcccc ctgcccgggg acatgcccac gatggccagg ccctgtccac agacctgggt    360

gtctacacat gtgaggccag caaccggctt ggcacggcag tcagcagagg cgctcggctg    420

tctgtggctg tcctccggga ggatttccag atccagcctc gggacatggt ggctgtggtg    480

ggtgagcagt ttactctgga atgtgggccg ccctggggcc acccagagcc cacagtctca    540

tggtggaaag atgggaaacc cctggccctc cagcccggaa ggcacacagt gtccgggggg    600

tccctgctga tggcaagagc agagaagagt gacgaangga cctacatgtg tgtggccacc    660

aacagcgcag gacacaggga gagccgcgca gcccgggttt ccatccagga gccccaggac    720

tacacggagc ctgtggagct tctggctgtg cgaattcagc tggaaaatgt gacactsctg    780

aacccggatc ctgcagargg ccccaagcct agaccggcgg tgtggctcar ctggaargtc    840

agtggccctn tgcgcctgcc caatcttaca cggccttgtt caggacccag actgccccgg    900

gaggccaggg agctccgtgg gcagaggagg aacacaggat aaaaatggaa gttctcaata    960

aaaagaagat gtattgggaa agaaaactac aaacttttac caaggaatgg cctgtttcct   1020

catttaaccg gccctttccc aattcgccct aagactttgg gggtggctct cttgtaatta   1080

atctgtgttg gcaaagaatg tctggaacat ggacttggcg gtcagtaacc tgtaacagag   1140

ctacaactag gaaaattaga gtggtagtag tcacttattt aagaattcat tcaggtaaac   1200

agctgcaccc tctgtacccc ttaagtggca aagaagctgt tatagtcttc tgaaaattat   1260

cactatgagt gctataattc tgaatataat gtctcttaat tagaattcat acaagaacca   1320

aaaaaaaaaa aaaaaaaagg gcggcc                                        1346
```

<210> SEQ ID NO 108
<211> LENGTH: 303
<212> TYPE: PRT
<213> ORGANISM: Homo sapiens
<220> FEATURE:
<221> NAME/KEY: SITE
<222> LOCATION: (203)
<223> OTHER INFORMATION: Xaa equals any amino acid
<220> FEATURE:
<221> NAME/KEY: SITE
<222> LOCATION: (267)
<223> OTHER INFORMATION: Xaa equals any amino acid
<220> FEATURE:
<221> NAME/KEY: SITE
<222> LOCATION: (274)
<223> OTHER INFORMATION: Xaa equals any amino acid

<400> SEQUENCE: 108

```
Met Gly Ser Gly Gly Asp Ser Leu Leu Gly Gly Arg Gly Ser Leu Pro
  1               5                  10                  15

Leu Leu Leu Leu Leu Ile Met Gly Gly Met Ala Gln Asp Ser Pro Pro
             20                  25                  30

Gln Ile Leu Val His Pro Gln Asp Gln Leu Phe Gln Gly Pro Gly Pro
         35                  40                  45
```

```
Ala Arg Met Ser Cys Arg Ala Ser Gly Gln Pro Pro Pro Thr Ile Arg
    50                  55                  60

Trp Leu Leu Asn Gly Gln Pro Leu Ser Met Val Pro Pro Asp Pro His
65                  70                  75                  80

His Leu Leu Pro Asp Gly Thr Leu Leu Leu Leu Gln Pro Pro Ala Arg
                85                  90                  95

Gly His Ala His Asp Gly Gln Ala Leu Ser Thr Asp Leu Gly Val Tyr
            100                 105                 110

Thr Cys Glu Ala Ser Asn Arg Leu Gly Thr Ala Val Ser Arg Gly Ala
        115                 120                 125

Arg Leu Ser Val Ala Val Leu Arg Glu Asp Phe Gln Ile Gln Pro Arg
    130                 135                 140

Asp Met Val Ala Val Val Gly Glu Gln Phe Thr Leu Glu Cys Gly Pro
145                 150                 155                 160

Pro Trp Gly His Pro Glu Pro Thr Val Ser Trp Trp Lys Asp Gly Lys
                165                 170                 175

Pro Leu Ala Leu Gln Pro Gly Arg His Thr Val Ser Gly Gly Ser Leu
            180                 185                 190

Leu Met Ala Arg Ala Glu Lys Ser Asp Glu Xaa Thr Tyr Met Cys Val
        195                 200                 205

Ala Thr Asn Ser Ala Gly His Arg Glu Ser Arg Ala Ala Arg Val Ser
    210                 215                 220

Ile Gln Glu Pro Gln Asp Tyr Thr Glu Pro Val Glu Leu Leu Ala Val
225                 230                 235                 240

Arg Ile Gln Leu Glu Asn Val Thr Leu Leu Asn Pro Asp Pro Ala Glu
                245                 250                 255

Gly Pro Lys Pro Arg Pro Ala Val Trp Leu Xaa Trp Lys Val Ser Gly
            260                 265                 270

Pro Xaa Arg Leu Pro Asn Leu Thr Arg Pro Cys Ser Gly Pro Arg Leu
        275                 280                 285

Pro Arg Glu Ala Arg Glu Leu Arg Gly Gln Arg Arg Asn Thr Gly
    290                 295                 300
```

<210> SEQ ID NO 109
<211> LENGTH: 1332
<212> TYPE: DNA
<213> ORGANISM: Homo sapiens

<400> SEQUENCE: 109

```
ccacgcgtcc gctgagagta gccatgggct ctggaggaga cagcctcctg gggggcaggg      60

gttccctgcc tctgctgctc ctgctcatca tgggaggcat ggctcaggac tccccgcccc     120

agatcttagt ccacccccag gaccagctgt tccagggccc tggccctgcc aggatgagct     180

gccgagcctc aggccagcca cctcccacca tccgctggtt gctgaatggg cagcccctga     240

gcatggtgcc cccagaccca caccacctcc tgcctgatgg gacccttctg ctgctacagc     300

cccctgcccg gggacatgcc cacgatggcc aggccctgtc cacagacctg ggtgtctaca     360

catgtgaggc cagcaaccgg cttggcacgg cagtcagcag aggcgctcgg ctgtctgtgg     420

ctgtcctccg ggaggatttc cagatccagc ctcgggacat ggtggctgtg gtgggtgagc     480

agtttactct ggaatgtggg ccgccctggg gccacccaga gcccacagtc tcatggtgga     540

aagatgggaa acccctggcc ctccagcccg gaaggcacac agtgtccggg gggtccctgc     600

tgatggcaag agcagagaag agtgacgaag ggacctacat gtgtgtggcc accaacagcg     660

caggacacag ggagagccgc gcagcccggg tttccatcca ggagccccag gactacacgg     720
```

-continued

```
agcctgtgga gcttctggct gtgcgaattc agctggaaaa tgtgacactg ctgaacccgg    780

atcctgcaga gggccccaag cctagaccgg gggtgtggct cagctggaag gtcagtggcc    840

ctgctgcgcc tgcccaatct tacacggcct tgttcaggac ccagactgcc ccgggaggcc    900

agggagctcc gtgggcagag gaggaacaca ggataaaaat ggaagttctc aataaaaaga    960

agatgtattg ggaaagaaaa ctacaaactt ttaccaagga atggcctgtt tcctcattta   1020

accggccctt tcccaattcg ccctaagact ttgggggtgg ctctcttgta attaatctgt   1080

gttggcaaag aatgtctgga acatggactt ggcggtcagt aacctgtaac agagctacaa   1140

ctaggaaaat tagagtggta gtagtcactt atttaagaat tcattcaggt aaacagctgc   1200

accctctgta ccccttaagt ggcaaagaag ctgttatagt cttctgaaaa ttatcactat   1260

gagtgctata attctgaata taatgtctct taattagaat tcatacaaga accaaaaaaa   1320

aaaaaaaaaa aa                                                       1332
```

<210> SEQ ID NO 110
<211> LENGTH: 340
<212> TYPE: PRT
<213> ORGANISM: Homo sapiens

<400> SEQUENCE: 110

```
Met Gly Ser Gly Gly Asp Ser Leu Leu Gly Gly Arg Gly Ser Leu Pro
1               5                   10                  15

Leu Leu Leu Leu Leu Ile Met Gly Gly Met Ala Gln Asp Ser Pro Pro
            20                  25                  30

Gln Ile Leu Val His Pro Gln Asp Gln Leu Phe Gln Gly Pro Gly Pro
        35                  40                  45

Ala Arg Met Ser Cys Arg Ala Ser Gly Gln Pro Pro Pro Thr Ile Arg
    50                  55                  60

Trp Leu Leu Asn Gly Gln Pro Leu Ser Met Val Pro Pro Asp Pro His
65                  70                  75                  80

His Leu Leu Pro Asp Gly Thr Leu Leu Leu Leu Gln Pro Pro Ala Arg
                85                  90                  95

Gly His Ala His Asp Gly Gln Ala Leu Ser Thr Asp Leu Gly Val Tyr
            100                 105                 110

Thr Cys Glu Ala Ser Asn Arg Leu Gly Thr Ala Val Ser Arg Gly Ala
        115                 120                 125

Arg Leu Ser Val Ala Val Leu Arg Glu Asp Phe Gln Ile Gln Pro Arg
    130                 135                 140

Asp Met Val Ala Val Val Gly Glu Gln Phe Thr Leu Glu Cys Gly Pro
145                 150                 155                 160

Pro Trp Gly His Pro Glu Pro Thr Val Ser Trp Trp Lys Asp Gly Lys
                165                 170                 175

Pro Leu Ala Leu Gln Pro Gly Arg His Thr Val Ser Gly Gly Ser Leu
            180                 185                 190

Leu Met Ala Arg Ala Glu Lys Ser Asp Glu Gly Thr Tyr Met Cys Val
        195                 200                 205

Ala Thr Asn Ser Ala Gly His Arg Glu Ser Arg Ala Ala Arg Val Ser
    210                 215                 220

Ile Gln Glu Pro Gln Asp Tyr Thr Glu Pro Val Glu Leu Leu Ala Val
225                 230                 235                 240

Arg Ile Gln Leu Glu Asn Val Thr Leu Leu Asn Pro Asp Pro Ala Glu
                245                 250                 255

Gly Pro Lys Pro Arg Pro Gly Val Trp Leu Ser Trp Lys Val Ser Gly
```

```
        260                 265                 270

Pro Ala Ala Pro Ala Gln Ser Tyr Thr Ala Leu Phe Arg Thr Gln Thr
    275                 280                 285

Ala Pro Gly Gly Gln Gly Ala Pro Trp Ala Glu Glu Glu His Arg Ile
    290                 295                 300

Lys Met Glu Val Leu Asn Lys Lys Lys Met Tyr Trp Glu Arg Lys Leu
305                 310                 315                 320

Gln Thr Phe Thr Lys Glu Trp Pro Val Ser Ser Phe Asn Arg Pro Phe
                325                 330                 335

Pro Asn Ser Pro
            340


<210> SEQ ID NO 111
<211> LENGTH: 10
<212> TYPE: PRT
<213> ORGANISM: Homo sapiens

<400> SEQUENCE: 111

Gly Arg Pro Thr Arg Pro Leu Arg Val Ala
1               5                   10


<210> SEQ ID NO 112
<211> LENGTH: 120
<212> TYPE: PRT
<213> ORGANISM: Homo sapiens

<400> SEQUENCE: 112

Ala Trp Cys Pro Gln Thr His Thr Thr Ser Cys Leu Met Gly Pro Phe
  1               5                  10                  15

Cys Cys Tyr Ser Pro Leu Pro Gly Asp Met Pro Thr Met Ala Arg Pro
             20                  25                  30

Cys Pro Gln Thr Trp Val Ser Thr His Val Arg Pro Ala Thr Gly Leu
         35                  40                  45

Ala Arg Gln Ser Ala Glu Ala Leu Gly Cys Leu Trp Leu Ser Ser Gly
     50                  55                  60

Arg Ile Ser Arg Ser Ser Leu Gly Thr Trp Trp Leu Trp Trp Val Ser
 65                  70                  75                  80

Ser Leu Leu Trp Asn Val Gly Arg Pro Gly Ala Thr Gln Ser Pro Gln
                 85                  90                  95

Ser His Gly Gly Lys Met Gly Asn Pro Trp Pro Ser Ser Pro Glu Gly
            100                 105                 110

Thr Gln Cys Pro Gly Gly Pro Cys
        115                 120


<210> SEQ ID NO 113
<211> LENGTH: 25
<212> TYPE: PRT
<213> ORGANISM: Homo sapiens

<400> SEQUENCE: 113

Cys Cys Tyr Ser Pro Leu Pro Gly Asp Met Pro Thr Met Ala Arg Pro
  1               5                  10                  15

Cys Pro Gln Thr Trp Val Ser Thr His
             20                  25


<210> SEQ ID NO 114
<211> LENGTH: 18
<212> TYPE: PRT
<213> ORGANISM: Homo sapiens
```

-continued

<400> SEQUENCE: 114

Ala Leu Gly Cys Leu Trp Leu Ser Ser Gly Arg Ile Ser Arg Ser Ser
1 5 10 15

Leu Gly

<210> SEQ ID NO 115
<211> LENGTH: 28
<212> TYPE: PRT
<213> ORGANISM: Homo sapiens

<400> SEQUENCE: 115

Trp Asn Val Gly Arg Pro Gly Ala Thr Gln Ser Pro Gln Ser His Gly
1 5 10 15

Gly Lys Met Gly Asn Pro Trp Pro Ser Ser Pro Glu
20 25

<210> SEQ ID NO 116
<211> LENGTH: 571
<212> TYPE: DNA
<213> ORGANISM: Homo sapiens

<400> SEQUENCE: 116
ggcacgagtc aaccgtcaaa atgtccaaag aacctctcat tctctggctg atgattgagt 60
tttggtggct ttacctgaca ccagtcactt cagagactgt tgtgacggag gttttgggtc 120
accgggtgac tttgccctgt ctgtactcat cctggtctca caacagcaac agcatgtgct 180
gggggaaaga ccagtgcccc tactccggtt gcaaggaggc gctcatccgc actgatggaa 240
tgagggtgac ctcaagaaag tcagcaaaat atagacttca ggggactatc ccgagaggtg 300
atgtctcctt gaccatctta aaccccagtg aaagtgacag cggtgtgtac tgctgccgca 360
tagaagtgcc tggctggttc aacgatgtaa agataaacgt gcgcctgaat ctacagagag 420
cctcaacaac cacgcacaga acagcaacca ccaccacacg cagaacaaca acaacaagcc 480
ccaccaccac ccgacaaatg acaacaaccc cagctgcact tccaacaacc aaaaaaaaaa 540
aaaaaaaaaa aaaaaaaaaa aaaaaaaaaa a 571

<210> SEQ ID NO 117
<211> LENGTH: 183
<212> TYPE: PRT
<213> ORGANISM: Homo sapiens

<400> SEQUENCE: 117

Met Ser Lys Glu Pro Leu Ile Leu Trp Leu Met Ile Glu Phe Trp Trp
1 5 10 15

Leu Tyr Leu Thr Pro Val Thr Ser Glu Thr Val Val Thr Glu Val Leu
20 25 30

Gly His Arg Val Thr Leu Pro Cys Leu Tyr Ser Ser Trp Ser His Asn
35 40 45

Ser Asn Ser Met Cys Trp Gly Lys Asp Gln Cys Pro Tyr Ser Gly Cys
50 55 60

Lys Glu Ala Leu Ile Arg Thr Asp Gly Met Arg Val Thr Ser Arg Lys
65 70 75 80

Ser Ala Lys Tyr Arg Leu Gln Gly Thr Ile Pro Arg Gly Asp Val Ser
85 90 95

Leu Thr Ile Leu Asn Pro Ser Glu Ser Asp Ser Gly Val Tyr Cys Cys
100 105 110

Arg Ile Glu Val Pro Gly Trp Phe Asn Asp Val Lys Ile Asn Val Arg
115 120 125

```
Leu Asn Leu Gln Arg Ala Ser Thr Thr Thr His Arg Thr Ala Thr Thr
    130                 135                 140

Thr Thr Arg Arg Thr Thr Thr Thr Ser Pro Thr Thr Thr Arg Gln Met
145                 150                 155                 160

Thr Thr Thr Pro Ala Ala Leu Pro Thr Thr Lys Lys Lys Lys Lys Lys
                165                 170                 175

Lys Lys Lys Lys Lys Lys Lys
            180
```

<210> SEQ ID NO 118
<211> LENGTH: 1282
<212> TYPE: DNA
<213> ORGANISM: Homo sapiens

<400> SEQUENCE: 118

```
ggcacgagct gggtccggtc aaccgtcaaa atgtccaaag aacctctcat tctctggctg     60

atgattgagt tttggtggct ttacctgaca ccagtcactt cagagactgt tgtgacggag    120

gttttgggtc accgggtgac tttgccctgt ctgtactcat cctggtctca caacagcaac    180

agcatgtgct gggggaaaga ccagtgcccc tactccggtt gcaaggaggc gctcatccgc    240

actgatggaa tgagggtgac ctcaagaaag tcagcaaaat atagacttca ggggactatc    300

ccgagaggtg atgtctcctt gaccatctta aaccccagtg aaagtgacag cggtgtgtac    360

tgctgccgca tagaagtgcc tggctggttc aacgatgtaa agataaacgt gcgcctgaat    420

ctacagagag cctcaacaac cacgcacaga acagcaacca ccaccacacg cagaacaaca    480

acaacaagcc ccaccaccac ccgacaaatg acaacaaccc cagctgcact tccaacaaca    540

gtcgtgacca cacccgatct cacaaccgga acaccactcc agatgacaac cattgccgtc    600

ttcacaacag caaacacgtg cctttcacta accccaagca cccttccgga ggaagccaca    660

ggtcttctga ctcccgagcc ttctaaggaa gggcccatcc tcactgcaga atcagaaact    720

gtcctcccca gtgattcctg gagtagtgct gagtctactt ctgctgacac tgtcctgctg    780

acatccaaag agtccaaagt ttgggatctc ccatcaacat cccacgtgtc aatgtggaaa    840

acgagtgatt ctgtgtcttc tcctcagcct ggagcatctg atacagcagt tcctgagcag    900

aacaaaaacaa caaaaacagg acagatggat ggaataccca tgtcaatgaa gaatgaaatg    960

cccatctccc aactactgat gatcatcgcc ccctccttgg gatttgtgct cttcgcattg   1020

tttgtggcgt ttctcctgag agggaaactc atggaaacct attgttcgca gaaacacaca   1080

aggctagact acattggaga tagtaaaaat gtcctcaatg acgtgcagca tggaagggaa   1140

gacgaagacg gcctttttac cctctaacaa cgcagtagca tgttagattg aggatggggg   1200

catgacactc cagtgtcaaa ataagtctta gtagatttcc ttgtttcata aaaaagactc   1260

acttaaaaaa aaaaaaaaaa aa                                            1282
```

<210> SEQ ID NO 119
<211> LENGTH: 378
<212> TYPE: PRT
<213> ORGANISM: Homo sapiens

<400> SEQUENCE: 119

```
Met Ser Lys Glu Pro Leu Ile Leu Trp Leu Met Ile Glu Phe Trp Trp
  1               5                  10                  15

Leu Tyr Leu Thr Pro Val Thr Ser Glu Thr Val Val Thr Glu Val Leu
             20                  25                  30

Gly His Arg Val Thr Leu Pro Cys Leu Tyr Ser Ser Trp Ser His Asn
```

```
        35                  40                  45

Ser Asn Ser Met Cys Trp Gly Lys Asp Gln Cys Pro Tyr Ser Gly Cys
     50                  55                  60

Lys Glu Ala Leu Ile Arg Thr Asp Gly Met Arg Val Thr Ser Arg Lys
 65                  70                  75                  80

Ser Ala Lys Tyr Arg Leu Gln Gly Thr Ile Pro Arg Gly Asp Val Ser
                 85                  90                  95

Leu Thr Ile Leu Asn Pro Ser Glu Ser Asp Ser Gly Val Tyr Cys Cys
            100                 105                 110

Arg Ile Glu Val Pro Gly Trp Phe Asn Asp Val Lys Ile Asn Val Arg
        115                 120                 125

Leu Asn Leu Gln Arg Ala Ser Thr Thr Thr His Arg Thr Ala Thr Thr
    130                 135                 140

Thr Thr Arg Arg Thr Thr Thr Thr Ser Pro Thr Thr Thr Arg Gln Met
145                 150                 155                 160

Thr Thr Thr Pro Ala Ala Leu Pro Thr Thr Val Val Thr Thr Pro Asp
                165                 170                 175

Leu Thr Thr Gly Thr Pro Leu Gln Met Thr Thr Ile Ala Val Phe Thr
            180                 185                 190

Thr Ala Asn Thr Cys Leu Ser Leu Thr Pro Ser Thr Leu Pro Glu Glu
        195                 200                 205

Ala Thr Gly Leu Leu Thr Pro Glu Pro Ser Lys Glu Gly Pro Ile Leu
    210                 215                 220

Thr Ala Glu Ser Glu Thr Val Leu Pro Ser Asp Ser Trp Ser Ser Ala
225                 230                 235                 240

Glu Ser Thr Ser Ala Asp Thr Val Leu Leu Thr Ser Lys Glu Ser Lys
                245                 250                 255

Val Trp Asp Leu Pro Ser Thr Ser His Val Ser Met Trp Lys Thr Ser
            260                 265                 270

Asp Ser Val Ser Ser Pro Gln Pro Gly Ala Ser Asp Thr Ala Val Pro
        275                 280                 285

Glu Gln Asn Lys Thr Thr Lys Thr Gly Gln Met Asp Gly Ile Pro Met
    290                 295                 300

Ser Met Lys Asn Glu Met Pro Ile Ser Gln Leu Leu Met Ile Ile Ala
305                 310                 315                 320

Pro Ser Leu Gly Phe Val Leu Phe Ala Leu Phe Val Ala Phe Leu Leu
                325                 330                 335

Arg Gly Lys Leu Met Glu Thr Tyr Cys Ser Gln Lys His Thr Arg Leu
            340                 345                 350

Asp Tyr Ile Gly Asp Ser Lys Asn Val Leu Asn Asp Val Gln His Gly
        355                 360                 365

Arg Glu Asp Glu Asp Gly Leu Phe Thr Leu
    370                 375


<210> SEQ ID NO 120
<211> LENGTH: 1240
<212> TYPE: DNA
<213> ORGANISM: Homo sapiens
<220> FEATURE:
<221> NAME/KEY: misc_feature
<222> LOCATION: (1)..(1)
<223> OTHER INFORMATION: n equals a,t,g, or c

<400> SEQUENCE: 120

nctgggtccg gtcaaccgtc aaaatgtcca aagaacctct cattctctgg ctgatgattg      60

agttttggtg gctttacctg acaccagtca cttcagagac tgttgtgacg gaggttttgg     120
```

-continued

```
gtcaccgggt gactttgccc tgtctgtact catcctggtc tcacaacagc aacagcatgt    180

gctgggggaa agaccagtgc ccctactccg gttgcaagga ggcgctcatc cgcactgatg    240

gaatgagggt gacctcaaga aagtcagcaa aatatagact tcaggggact atcccgagag    300

gtgatgtctc cttgaccatc ttaaacccca gtgaaagtga cagcggtgtg tactgctgcc    360

gcatagaagt gcctggctgg ttcaacgatg taaagataaa cgtgcgcctg aatctacaga    420

gagcctcaac aaccacgcac agaacagcaa ccaccaccac acgcagaaca acaacaacaa    480

gccccaccac cacccgacaa atgacaacaa ccccagctgc acttccaaca acagtcgtga    540

ccacacccga tctcacaacc ggaacaccac tccagatgac aaccattgcc gtcttcacaa    600

cagcaaacac gtgcctttca ctaaccccaa gcacccttcc ggaggaagcc acaggtcttc    660

tgactcccga gccttctaag gaagggccca tcctcactgc agaatcagaa actgtcctcc    720

ccagtgattc ctggagtagt gctgagtcta cttctgctga cactgtcctg ctgacatcca    780

aagagtccaa agtttgggat ctcccatcaa catcccacgt gtcaatgtgg aaaacgagtg    840

attctgtgtc ttctcctcag cctggagcat ctgatacagc agttcctgag cagaacaaaa    900

caacaaaaac aggacagatg gatggaatac ccatgtcaat gaagaatgaa atgcccatct    960

cccaactact gatgatcatc gccccctcct tgggatttgt gctcttcgca ttgtttgtgg   1020

cgtttctcct gagagggaaa ctcatggaaa cctattgttc gcagaaacac acaaggctag   1080

actacattgg agatagtaaa aatgtcctca atgacgtgca gcatggaagg gaagacgaag   1140

acggcctttt taccctctaa caacgcagta gcatgttaga ttgaggatgg gggcatgaca   1200

ctccagtgtc aaaataagtc ttagtagatt tccttgtttc                         1240


<210> SEQ ID NO 121
<211> LENGTH: 378
<212> TYPE: PRT
<213> ORGANISM: Homo sapiens

<400> SEQUENCE: 121

Met Ser Lys Glu Pro Leu Ile Leu Trp Leu Met Ile Glu Phe Trp Trp
  1               5                  10                  15

Leu Tyr Leu Thr Pro Val Thr Ser Glu Thr Val Val Thr Glu Val Leu
             20                  25                  30

Gly His Arg Val Thr Leu Pro Cys Leu Tyr Ser Ser Trp Ser His Asn
         35                  40                  45

Ser Asn Ser Met Cys Trp Gly Lys Asp Gln Cys Pro Tyr Ser Gly Cys
     50                  55                  60

Lys Glu Ala Leu Ile Arg Thr Asp Gly Met Arg Val Thr Ser Arg Lys
 65                  70                  75                  80

Ser Ala Lys Tyr Arg Leu Gln Gly Thr Ile Pro Arg Gly Asp Val Ser
                 85                  90                  95

Leu Thr Ile Leu Asn Pro Ser Glu Ser Asp Ser Gly Val Tyr Cys Cys
            100                 105                 110

Arg Ile Glu Val Pro Gly Trp Phe Asn Asp Val Lys Ile Asn Val Arg
        115                 120                 125

Leu Asn Leu Gln Arg Ala Ser Thr Thr Thr His Arg Thr Ala Thr Thr
    130                 135                 140

Thr Thr Arg Arg Thr Thr Thr Thr Ser Pro Thr Thr Thr Arg Gln Met
145                 150                 155                 160

Thr Thr Thr Pro Ala Ala Leu Pro Thr Thr Val Val Thr Thr Pro Asp
                165                 170                 175
```

-continued

```
Leu Thr Thr Gly Thr Pro Leu Gln Met Thr Thr Ile Ala Val Phe Thr
            180                 185                 190

Thr Ala Asn Thr Cys Leu Ser Leu Thr Pro Ser Thr Leu Pro Glu Glu
        195                 200                 205

Ala Thr Gly Leu Leu Thr Pro Glu Pro Ser Lys Glu Gly Pro Ile Leu
    210                 215                 220

Thr Ala Glu Ser Glu Thr Val Leu Pro Ser Asp Ser Trp Ser Ser Ala
225                 230                 235                 240

Glu Ser Thr Ser Ala Asp Thr Val Leu Leu Thr Ser Lys Glu Ser Lys
                245                 250                 255

Val Trp Asp Leu Pro Ser Thr Ser His Val Ser Met Trp Lys Thr Ser
            260                 265                 270

Asp Ser Val Ser Ser Pro Gln Pro Gly Ala Ser Asp Thr Ala Val Pro
        275                 280                 285

Glu Gln Asn Lys Thr Thr Lys Thr Gly Gln Met Asp Gly Ile Pro Met
    290                 295                 300

Ser Met Lys Asn Glu Met Pro Ile Ser Gln Leu Leu Met Ile Ile Ala
305                 310                 315                 320

Pro Ser Leu Gly Phe Val Leu Phe Ala Leu Phe Val Ala Phe Leu Leu
                325                 330                 335

Arg Gly Lys Leu Met Glu Thr Tyr Cys Ser Gln Lys His Thr Arg Leu
            340                 345                 350

Asp Tyr Ile Gly Asp Ser Lys Asn Val Leu Asn Asp Val Gln His Gly
        355                 360                 365

Arg Glu Asp Glu Asp Gly Leu Phe Thr Leu
    370                 375
```

<210> SEQ ID NO 122
<211> LENGTH: 6
<212> TYPE: PRT
<213> ORGANISM: Homo sapiens

<400> SEQUENCE: 122

```
His Glu Ser Thr Val Lys
1               5
```

<210> SEQ ID NO 123
<211> LENGTH: 1590
<212> TYPE: DNA
<213> ORGANISM: Homo sapiens

<400> SEQUENCE: 123

```
ttttttttt tttgtttaaa tgatacaact taattttatt aggacagacg ctggcggcca      60

ccagaagttt gagcctcttt ggtagcagga ggctggaaga aaggacagaa gtagctctgg     120

ctgtgatggg gatcttactg ggcctgctac tcctggggca cctaacagtg gacacttatg     180

gccgtcccat cctggaagtg ccagagagtg taacaggacc ttggaaaggg gatgtgaatc     240

ttccctgcac ctatgacccc ctgcaaggct acacccaagt cttggtgaag tggctggtac     300

aacgtggctc agaccctgtc accatctttc tacgtgactc ttctggagac catatccagc     360

aggcaaagta ccagggccgc ctgcatgtga gccacaaggt tccaggagat gtatccctcc     420

aattgagcac cctggagatg gatgaccgga gccactacac gtgtgaagtc acctggcaga     480

ctcctgatgg caaccaagtc gtgagagata agattactga gctccgtgtc cagaaacact     540

cctcaaagct actcaagacc aagactgagg cacctacaac catgacatac cccttgaaag     600

caacatctac agtgaagcag tcctgggact ggaccactga catggatggc taccttggag     660
```

-continued

```
agaccagtgc tgggccagga aagagcctgc ctgtctttgc catcatcctc atcatctcct    720

tgtgctgtat ggtggttttt accatggcct atatcatgct ctgtcggaag acatccccaac   780

aagagcatgt ctacgaagca gccagggcac atgccagaga ggccaacgac tctggagaaa    840

ccatgagggt ggccatcttc gcaagtggct gctccagtga tgagccaact tcccagaatc    900

tgggcaacaa ctactctgat gagccctgca taggacagga gtaccagatc atcgcccaga    960

tcaatggcaa ctacgcccgc ctgctggaca cagttcctct ggattatgag tttctggcca   1020

ctgagggcaa aagtgtctgt taaaaatgcc ccattaggcc aggatctgct gacataattg   1080

cctagtcagt ccttgccttc tgcatggcct tcttccctgc tacctctctt cctggatagc   1140

ccaaagtgtc cgcctaccaa cactggagcc gctgggagtc actggctttg ccctggaatt   1200

tgccagatgc atctcaagta agccagctgc tggatttggc tctgggccct tctagtatct   1260

ctgccggggg cttctggtac tcctctctaa ataccagagg gaagatgccc atagcactag   1320

gacttggtca tcatgcctac agacactatt caactttggc atcttgccac cagaagaccc   1380

gagggaggct cagctctgcc agctcagagg accagctata tccaggatca tttctctttc   1440

ttcagggcca gacagctttt aattgaaatt gttatttcac aggccagggt tcagttctgc   1500

tcctccacta taagtctaat gttctgactc tctcctggtg ctcaataaat atctaatcat   1560

aacagcaaaa aaaaaaaaaa aaaactcgag                                    1590
```

<210> SEQ ID NO 124
<211> LENGTH: 305
<212> TYPE: PRT
<213> ORGANISM: Homo sapiens

<400> SEQUENCE: 124

```
Met Gly Ile Leu Leu Gly Leu Leu Leu Leu Gly His Leu Thr Val Asp
  1               5                  10                  15

Thr Tyr Gly Arg Pro Ile Leu Glu Val Pro Glu Ser Val Thr Gly Pro
             20                  25                  30

Trp Lys Gly Asp Val Asn Leu Pro Cys Thr Tyr Asp Pro Leu Gln Gly
         35                  40                  45

Tyr Thr Gln Val Leu Val Lys Trp Leu Val Gln Arg Gly Ser Asp Pro
     50                  55                  60

Val Thr Ile Phe Leu Arg Asp Ser Ser Gly Asp His Ile Gln Gln Ala
 65                  70                  75                  80

Lys Tyr Gln Gly Arg Leu His Val Ser His Lys Val Pro Gly Asp Val
                 85                  90                  95

Ser Leu Gln Leu Ser Thr Leu Glu Met Asp Asp Arg Ser His Tyr Thr
            100                 105                 110

Cys Glu Val Thr Trp Gln Thr Pro Asp Gly Asn Gln Val Val Arg Asp
        115                 120                 125

Lys Ile Thr Glu Leu Arg Val Gln Lys His Ser Ser Lys Leu Leu Lys
    130                 135                 140

Thr Lys Thr Glu Ala Pro Thr Thr Met Thr Tyr Pro Leu Lys Ala Thr
145                 150                 155                 160

Ser Thr Val Lys Gln Ser Trp Asp Trp Thr Thr Asp Met Asp Gly Tyr
                165                 170                 175

Leu Gly Glu Thr Ser Ala Gly Pro Gly Lys Ser Leu Pro Val Phe Ala
            180                 185                 190

Ile Ile Leu Ile Ile Ser Leu Cys Cys Met Val Val Phe Thr Met Ala
        195                 200                 205

Tyr Ile Met Leu Cys Arg Lys Thr Ser Gln Gln Glu His Val Tyr Glu
```

-continued

```
    210                 215                 220

Ala Ala Arg Ala His Ala Arg Glu Ala Asn Asp Ser Gly Glu Thr Met
225                 230                 235                 240

Arg Val Ala Ile Phe Ala Ser Gly Cys Ser Ser Asp Glu Pro Thr Ser
                245                 250                 255

Gln Asn Leu Gly Asn Asn Tyr Ser Asp Glu Pro Cys Ile Gly Gln Glu
            260                 265                 270

Tyr Gln Ile Ile Ala Gln Ile Asn Gly Asn Tyr Ala Arg Leu Leu Asp
        275                 280                 285

Thr Val Pro Leu Asp Tyr Glu Phe Leu Ala Thr Glu Gly Lys Ser Val
    290                 295                 300

Cys
305
```

<210> SEQ ID NO 125
<211> LENGTH: 1782
<212> TYPE: DNA
<213> ORGANISM: Homo sapiens

<400> SEQUENCE: 125

```
tgccgagcct ctttggtagc aggaggctgg aagaaaggac agaagtagct ctggctgtga     60

tggggatctt actgggcctg ctactcctgg ggcacctaac agtggacact tatggccgtc    120

ccatcctgga agtgccagag agtgtaacag gaccttggaa aggggatgtg aatcttccct    180

gcacctatga ccccctgcaa ggctacaccc aagtcttggt gaagtggctg gtacaacgtg    240

gctcagaccc tgtcaccatc tttctacgtg actcttctgg agaccatatc cagcaggcaa    300

agtaccaggg ccgcctgcat gtgagccaca aggttccagg agatgtatcc ctccaattga    360

gcaccctgga gatggatgac cggagccact acacgtgtga agtcacctgg cagactcctg    420

atggcaacca agtcgtgaga gataagatta ctgagctccg tgtccagaaa ctctctgtct    480

ccaagcccac agtgacaact ggcagcggtt atggcttcac ggtgccccag ggaatgagga    540

ttagccttca atgccaggct cggggttctc ctcccatcag ttatatttgg tataagcaac    600

agactaataa ccaggaaccc atcaaagtag caaccctaag taccttactc ttcaagcctg    660

cggtgatagc cgactcaggc tcctatttct gcactgccaa gggccaggtt ggctctgagc    720

agcacagcga cattgtgaag tttgtggtca aagactcctc aaagctactc aagaccaaga    780

ctgaggcacc tacaaccatg acatacccct tgaaagcaac atctacagtg aagcagtcct    840

gggactggac cactgacatg gatggctacc ttggagagac cagtgctggg ccaggaaaga    900

gcctgcctgt ctttgccatc atcctcatca tctccttgtg ctgtatggtg gtttttacca    960

tggcctatat catgctctgt cggaagacat cccaacaaga gcatgtctac gaagcagcca   1020

gggcacatgc cagagaggcc aacgactctg gagaaaccat gagggtggcc atcttcgcaa   1080

gtggctgctc cagtgatgag ccaacttccc agaatctggg caacaactac tctgatgagc   1140

cctgcatagg acaggagtac cagatcatcg cccagatcaa tggcaactac gcccgcctgc   1200

tggacacagt tcctctggat tatgagtttc tggccactga gggcaaaagt gtctgttaaa   1260

aatgccccat taggccagga tctgctgaca taattgccta gtcagtcctt gccttctgca   1320

tggccttctt ccctgctacc tctcttcctg gatagcccaa agtgtccgcc taccaacact   1380

ggagccgctg ggagtcactg gctttgccct ggaatttgcc agatgcatct caagtaagcc   1440

agctgctgga tttggctctg ggcccttcta gtatctctgc cgggggcttc tggtactcct   1500

ctctaaatac cagagggaag atgcccatag cactaggact tggtcatcat gcctacagac   1560
```

actattcaac tttggcatct tgccaccaga agacccgagg gaggctcagc tctgccagct 1620
cagaggacca gctatatcca ggatcatttc tctttcttca gggccagaca gcttttaatt 1680
gaaattgtta tttcacaggc cagggttcag ttctgctcct ccactataag tctaatgttc 1740
tgactctctc ctggtgctca ataaatatct aatcataaca gc 1782

<210> SEQ ID NO 126
<211> LENGTH: 399
<212> TYPE: PRT
<213> ORGANISM: Homo sapiens

<400> SEQUENCE: 126

Met Gly Ile Leu Leu Gly Leu Leu Leu Leu Gly His Leu Thr Val Asp
1 5 10 15

Thr Tyr Gly Arg Pro Ile Leu Glu Val Pro Glu Ser Val Thr Gly Pro
20 25 30

Trp Lys Gly Asp Val Asn Leu Pro Cys Thr Tyr Asp Pro Leu Gln Gly
35 40 45

Tyr Thr Gln Val Leu Val Lys Trp Leu Val Gln Arg Gly Ser Asp Pro
50 55 60

Val Thr Ile Phe Leu Arg Asp Ser Ser Gly Asp His Ile Gln Gln Ala
65 70 75 80

Lys Tyr Gln Gly Arg Leu His Val Ser His Lys Val Pro Gly Asp Val
85 90 95

Ser Leu Gln Leu Ser Thr Leu Glu Met Asp Asp Arg Ser His Tyr Thr
100 105 110

Cys Glu Val Thr Trp Gln Thr Pro Asp Gly Asn Gln Val Val Arg Asp
115 120 125

Lys Ile Thr Glu Leu Arg Val Gln Lys Leu Ser Val Ser Lys Pro Thr
130 135 140

Val Thr Thr Gly Ser Gly Tyr Gly Phe Thr Val Pro Gln Gly Met Arg
145 150 155 160

Ile Ser Leu Gln Cys Gln Ala Arg Gly Ser Pro Pro Ile Ser Tyr Ile
165 170 175

Trp Tyr Lys Gln Gln Thr Asn Asn Gln Glu Pro Ile Lys Val Ala Thr
180 185 190

Leu Ser Thr Leu Leu Phe Lys Pro Ala Val Ile Ala Asp Ser Gly Ser
195 200 205

Tyr Phe Cys Thr Ala Lys Gly Gln Val Gly Ser Glu Gln His Ser Asp
210 215 220

Ile Val Lys Phe Val Val Lys Asp Ser Ser Lys Leu Leu Lys Thr Lys
225 230 235 240

Thr Glu Ala Pro Thr Thr Met Thr Tyr Pro Leu Lys Ala Thr Ser Thr
245 250 255

Val Lys Gln Ser Trp Asp Trp Thr Thr Asp Met Asp Gly Tyr Leu Gly
260 265 270

Glu Thr Ser Ala Gly Pro Gly Lys Ser Leu Pro Val Phe Ala Ile Ile
275 280 285

Leu Ile Ile Ser Leu Cys Cys Met Val Val Phe Thr Met Ala Tyr Ile
290 295 300

Met Leu Cys Arg Lys Thr Ser Gln Gln Glu His Val Tyr Glu Ala Ala
305 310 315 320

Arg Ala His Ala Arg Glu Ala Asn Asp Ser Gly Glu Thr Met Arg Val
325 330 335

Ala Ile Phe Ala Ser Gly Cys Ser Ser Asp Glu Pro Thr Ser Gln Asn

-continued

```
            340                 345                 350

Leu Gly Asn Asn Tyr Ser Asp Glu Pro Cys Ile Gly Gln Glu Tyr Gln
        355                 360                 365

Ile Ile Ala Gln Ile Asn Gly Asn Tyr Ala Arg Leu Leu Asp Thr Val
    370                 375                 380

Pro Leu Asp Tyr Glu Phe Leu Ala Thr Glu Gly Lys Ser Val Cys
385                 390                 395


<210> SEQ ID NO 127
<211> LENGTH: 1903
<212> TYPE: DNA
<213> ORGANISM: Homo sapiens

<400> SEQUENCE: 127

saacaaagcc ttctacttga gcagtttttc catcactgat atgtgcagga aatgaagaca     60

ttgcctgcca tgcttggaac tgggaaatta ttttgggtct tcttcttaat cccatatctg    120

gacatctgga acatccatgg gaaagaatca tgtgatgtac agctttatat aaagagacaa    180

tctgaacact ccatcttagc aggagatccc tttgaactag aatgccctgt gaaatactgt    240

gctaacaggc ctcatgtgac ttggtgcaag ctcaatggaa caacatgtgt aaaacttgaa    300

gatagacaaa caagttggaa ggaagagaag aacatttcat ttttcattct acattttgaa    360

ccagtgcttc ctaatgacaa tgggtcatac cgctgttctg caaattttca gtctaatctc    420

attgaaagcc actcaacaac tctttatgtg acaggtgagt tctcaacacc tagaccatct    480

gatatttttc ttataatgtt tccaggaaga ggggggttca gtttctcaag tgattatgtt    540

agaaagccaa ctcctatagc acatctgaaa tctgctacac ctcacagatt gttatgtgcc    600

agtgtgtaca tatgtgtgtg tatgtgtgcg tttgaggtga gtgagataga ggagagtaga    660

gaaatagata gtaaaagtta ttgtttttga ctttagggat tataaaattt atttgataag    720

tccaaaagta gaccactgaa atattgaaaa aattataaag tgaataccta tagttgcgaa    780

tagctctgtg attgcttgtc cttctttgtt gttttttttt tctcttttc ccatttttct    840

cttctttact tttgttcatt acaatttctt gaagttatgt ttgtggtgct taggcaatta    900

aacacttctt aatagttcac agtttgttta gaggaaaaac agcaaacaac taactgactt    960

cctagtgatt ttctgggaat attcagagct tcatctctct tccctgttcc ccgaaagagg   1020

cctttaatat gctttgacaa ctgaggaagg acagatagaa gttaagcttg gggaaaccaa   1080

gctgaataaa acatgaaaaa atacataggg ggggagtagg taagagtaaa aaatacttgg   1140

tttataaaaa ttttatagcc aacatcatat tcaatggtga aaggcttaga gctttccccc   1200

taagaacagg aacaagacat ggatccttgc ttttgccatt tccatttaac attaaactga   1260

aaattctagc cagagcaaac aggcaagaac aagaaataaa agatatctaa cttagaaaaa   1320

aagaagtaaa actttattca cagatggcat gaacttatgt gtagaaaaat tcttaaaaat   1380

ttgtttaaaa ctattaaagc taatacatga atttagcaat tccacatgat acaggatcaa   1440

cacacaaaaa tcagtgatat ttctatacac tagcaataaa caatccacaa agaaaattaa   1500

ggaaacagtt ccatttacaa tagcatcaaa atgaataaaa tatttaagta caaatttaac   1560

caaagaggta taagagttgt acactgaaca aagaaagcat ggctgaaaga aattcaagaa   1620

tatgtaaata aatgcaaaga cattctgtat tcatggactg aaagatgtaa tattgtaaag   1680

atagcaatat tccccaaggt gatctacaga ttcaatgcag ttccactaaa atcctaacag   1740

ctttttgttg ctattgcaga aataaaaaag ctgatcctaa aattcacatt gagttgcaac   1800

agacccagaa ttgccaaaac aatcttgaaa aagaacaaaa ctgaagctaa gacttcccta   1860
```

```
tttcaaaact tactacaaaa tgacagttaa aaaaaaaaaa aaa                  1903


<210> SEQ ID NO 128
<211> LENGTH: 212
<212> TYPE: PRT
<213> ORGANISM: Homo sapiens

<400> SEQUENCE: 128

Met Lys Thr Leu Pro Ala Met Leu Gly Thr Gly Lys Leu Phe Trp Val
  1               5                  10                  15

Phe Phe Leu Ile Pro Tyr Leu Asp Ile Trp Asn Ile His Gly Lys Glu
             20                  25                  30

Ser Cys Asp Val Gln Leu Tyr Ile Lys Arg Gln Ser Glu His Ser Ile
         35                  40                  45

Leu Ala Gly Asp Pro Phe Glu Leu Glu Cys Pro Val Lys Tyr Cys Ala
     50                  55                  60

Asn Arg Pro His Val Thr Trp Cys Lys Leu Asn Gly Thr Thr Cys Val
 65                  70                  75                  80

Lys Leu Glu Asp Arg Gln Thr Ser Trp Lys Glu Glu Lys Asn Ile Ser
                 85                  90                  95

Phe Phe Ile Leu His Phe Glu Pro Val Leu Pro Asn Asp Asn Gly Ser
            100                 105                 110

Tyr Arg Cys Ser Ala Asn Phe Gln Ser Asn Leu Ile Glu Ser His Ser
        115                 120                 125

Thr Thr Leu Tyr Val Thr Gly Glu Phe Ser Thr Pro Arg Pro Ser Asp
    130                 135                 140

Ile Phe Leu Ile Met Phe Pro Gly Arg Gly Gly Phe Ser Phe Ser Ser
145                 150                 155                 160

Asp Tyr Val Arg Lys Pro Thr Pro Ile Ala His Leu Lys Ser Ala Thr
                165                 170                 175

Pro His Arg Leu Leu Cys Ala Ser Val Tyr Ile Cys Val Cys Met Cys
            180                 185                 190

Ala Phe Glu Val Ser Glu Ile Glu Glu Ser Arg Glu Ile Asp Ser Lys
        195                 200                 205

Ser Tyr Cys Phe
210


<210> SEQ ID NO 129
<211> LENGTH: 1940
<212> TYPE: DNA
<213> ORGANISM: Homo sapiens
<220> FEATURE:
<221> NAME/KEY: misc_feature
<222> LOCATION: (5)..(5)
<223> OTHER INFORMATION: n equals a,t,g, or c
<220> FEATURE:
<221> NAME/KEY: misc_feature
<222> LOCATION: (1573)..(1573)
<223> OTHER INFORMATION: n equals a,t,g, or c

<400> SEQUENCE: 129

tcganccacg cgtccgcgga cgctgggcgc aacaaagcct tctacttgag cagtttttcc      60

atcactgata tgtgcaggaa atgaagacat tgcctgccat gcttggaact gggaaattat     120

tttgggtctt cttcttaatc ccatatctgg acatctggaa catccatggg aaagaatcat     180

gtgatgtaca gctttatata aagagacaat ctgaacactc catcttagca ggagatccct     240

ttgaactaga atgccctgtg aaatactgtg ctaacaggcc tcatgtgact tggtgcaagc     300

tcaatggaac aacatgtgta aaacttgaag atagacaaac aagttggaag aagagaagaa     360
```

```
catttcattt ttcatctacr ytttgaacca gtgcttccta atgacaatgg gtcataccgc    420
tgttctgcaa attttcagtc taatctcatt gaaagccact caacaactct ttatgtgaca    480
ggtgagttct caacacctag accatctgat atttttctta taatgtttcc aggaagaggg    540
gggttcagtt tctcaagtga ttatgttaga aagccaactc ctatagcaca tctgaaatct    600
gctacacctc acagattgtt atgtgccagt gtgtacatat gtgtgtgtat gtgtgcgttt    660
gargtgagtg agatagagga gagtagakaa atagatagta aaagttattg tttttgactt    720
tagggattat aaaatttatt tgataagtcc aaaagtagac cactgaaata ttgaaaaaat    780
tataaagtga atacctatag ttgcgaatag ctctgtgatt gcttgtcctt ctttgttgtt    840
tttttttct cttttccca tttttctctt ctttactttt gttcattaca atttcttgaa    900
gttatgtttg tggtgcttag gcaattaaac acttcttaat agttcacagt ttgtttagag    960
gaaaaacagc aaacaactaa ctgacttcct agtgattttc tgggaatatt cagagyttca   1020
tctytyttcc ctgttccccg aaagaggcct ttaatatgct ttgacaactg aggaaggaca   1080
gatagaagtt aagcttgggg aaaccaagct gaataaaaca tgaaaaaata catagggggg   1140
gagtaggtaa gagtaaaaaa tacttggttt ataaaaattt tatagccaac atcatattca   1200
atggtgaaag gcttagagct ttccccctaa gaacaggaac aagacatgga tccttgcttt   1260
tgccatttcc atttaacatt aaactgaaaa ttctagccag agcaaacagg caagaacaag   1320
aaataaaaga tatctaactt agaaaaaaag aagtaaaact ttattcacag atggcatgaa   1380
cttatgtgta gaaaaattct taaaaatttg tttaaaacta ttaaagctaa tacatgaatt   1440
tagcaattcc acatgataca ggatcaacac acmaaaatca gtgatatttc tatacactag   1500
caataaacaa tccacaaaga aaattaagga aacagttcca tttacaatag catcaaaatg   1560
aataaaatat ttnagtacaa atttaaccaa agaggtataa gagttgtaca ctgaacaaag   1620
aaagcatggc tgaaagaaat tcaagaatat gtaaataaat gcaaagacat tctgtattca   1680
tggactgaaa gatgtaatat tgtaaagata gcaatattcc ccaaggtgat ctacagattc   1740
aatgcagttc cactaaaatc ctaacagctt tttgttgcta ttgcagaaat aaaaaagctg   1800
atcctaaaat tcacattgag ttgcaacaga cccagaattg ccaaaacaat cttgaaaaag   1860
aacaaaactg aagctaagac ttccctattt caaaacttac tacaaaatga cagttaaaaa   1920
aaaaaaaaaa gggcggccgc                                                1940
```

<210> SEQ ID NO 130
<211> LENGTH: 101
<212> TYPE: PRT
<213> ORGANISM: Homo sapiens
<220> FEATURE:
<221> NAME/KEY: SITE
<222> LOCATION: (101)
<223> OTHER INFORMATION: Xaa equals any amino acid

<400> SEQUENCE: 130

```
Met Lys Thr Leu Pro Ala Met Leu Gly Thr Gly Lys Leu Phe Trp Val
  1               5                  10                  15

Phe Phe Leu Ile Pro Tyr Leu Asp Ile Trp Asn Ile His Gly Lys Glu
             20                  25                  30

Ser Cys Asp Val Gln Leu Tyr Ile Lys Arg Gln Ser Glu His Ser Ile
         35                  40                  45

Leu Ala Gly Asp Pro Phe Glu Leu Glu Cys Pro Val Lys Tyr Cys Ala
     50                  55                  60

Asn Arg Pro His Val Thr Trp Cys Lys Leu Asn Gly Thr Thr Cys Val
```

-continued

```
 65                  70                  75                  80

Lys Leu Glu Asp Arg Gln Thr Ser Trp Lys Lys Arg Arg Thr Phe His
                85                  90                  95

Phe Ser Ser Thr Xaa
            100


<210> SEQ ID NO 131
<211> LENGTH: 1445
<212> TYPE: DNA
<213> ORGANISM: Homo sapiens

<400> SEQUENCE: 131

ggaaggctgc aggaccagga ccgaaaaagg actaggaggc tgggatcagc aacaactggg     60

gaaggccaag gaagactgac ctgaggggaa aggagaaact ggggaggtga ggtctactac    120

tcaacaggat attcttcaag gaaaatgaac cccacactag gcctggccat tttctggct     180

gttctcctca cggtgaaagg tcttctaaag ccgagcttct caccaaggaa ttataaagct    240

ttgagcgagg tccaaggatg gaagcaaagg atggcagcca aggagcttgc aaggcagaac    300

atggacttag gctttaagct gctcaagaag ctggcctttt acaaccctgg caggaacatc    360

ttcctatccc ccttgagcat ctctacagct ttctccatgc tgtgcctggg tgcccaggac    420

agcaccctgg acgagatcaa gcaggggttc aacttcagaa agatgccaga aaaagatctt    480

catgagggct tccattacat catccacgag ctgacccaga agacccagga cctcaaactg    540

agcattggga acacgctgtt cattgaccag aggctgcagc cacagcgtaa gtttttggaa    600

gatgccaaga acttttacag tgccgaaacc atccttacca actttcagaa tttggaaatg    660

gctcagaagc agatcaatga ctttatcagt caaaaaaccc atgggaaaat taacaacctg    720

atcgagaata tagaccccgg cactgtgatg cttcttgcaa attatatttt ctttcgagcc    780

aggtggaaac atgagtttga tccaaatgta actaaagagg aagatttctt tctggagaaa    840

aacagttcag tcaaggtgcc catgatgttc cgtagtggca tataccaagt tggctatgac    900

gataagctct cttgcaccat cctggaaata ccctaccaga aaaatatcac agccatcttc    960

atccttcctg atgagggcaa gctgaagcac ttggagaagg gattgcaggt ggacactttc   1020

tccagatgga aaacattact gtcacgcagg gtcgtagacg tgtctgtacc cagactccac   1080

atgacgggca ccttcgacct gaagaagact ctctcctaca taggtgtctc caaaatcttt   1140

gaggaacatg gtgatctcac caagatcgcc cctcatcgca gcctgaaagt gggcgaggct   1200

gtgcacaagg ctgagctgaa gatggatgag aggggtacgg aaggggccgc tggcaccgga   1260

gcacagactc tgcccatgga gacaccactc gtcgtcaaga tagacaaacc ctatctgctg   1320

ctgatttaca gcgagaaaat accttccgtg ctcttcctgg gaaagattgt taaccctatt   1380

ggaaaataaa ggagaattcc tgcttgccac agaccccgaa aaaaaaaaaa aaaaagggcg   1440

gccgc                                                               1445


<210> SEQ ID NO 132
<211> LENGTH: 414
<212> TYPE: PRT
<213> ORGANISM: Homo sapiens

<400> SEQUENCE: 132

Met Asn Pro Thr Leu Gly Leu Ala Ile Phe Leu Ala Val Leu Leu Thr
  1               5                  10                  15

Val Lys Gly Leu Leu Lys Pro Ser Phe Ser Pro Arg Asn Tyr Lys Ala
             20                  25                  30
```

-continued

```
Leu Ser Glu Val Gln Gly Trp Lys Gln Arg Met Ala Ala Lys Glu Leu
        35                  40                  45

Ala Arg Gln Asn Met Asp Leu Gly Phe Lys Leu Leu Lys Lys Leu Ala
    50                  55                  60

Phe Tyr Asn Pro Gly Arg Asn Ile Phe Leu Ser Pro Leu Ser Ile Ser
65                  70                  75                  80

Thr Ala Phe Ser Met Leu Cys Leu Gly Ala Gln Asp Ser Thr Leu Asp
                85                  90                  95

Glu Ile Lys Gln Gly Phe Asn Phe Arg Lys Met Pro Glu Lys Asp Leu
            100                 105                 110

His Glu Gly Phe His Tyr Ile Ile His Glu Leu Thr Gln Lys Thr Gln
        115                 120                 125

Asp Leu Lys Leu Ser Ile Gly Asn Thr Leu Phe Ile Asp Gln Arg Leu
    130                 135                 140

Gln Pro Gln Arg Lys Phe Leu Glu Asp Ala Lys Asn Phe Tyr Ser Ala
145                 150                 155                 160

Glu Thr Ile Leu Thr Asn Phe Gln Asn Leu Glu Met Ala Gln Lys Gln
                165                 170                 175

Ile Asn Asp Phe Ile Ser Gln Lys Thr His Gly Lys Ile Asn Asn Leu
            180                 185                 190

Ile Glu Asn Ile Asp Pro Gly Thr Val Met Leu Leu Ala Asn Tyr Ile
        195                 200                 205

Phe Phe Arg Ala Arg Trp Lys His Glu Phe Asp Pro Asn Val Thr Lys
    210                 215                 220

Glu Glu Asp Phe Phe Leu Glu Lys Asn Ser Ser Val Lys Val Pro Met
225                 230                 235                 240

Met Phe Arg Ser Gly Ile Tyr Gln Val Gly Tyr Asp Asp Lys Leu Ser
                245                 250                 255

Cys Thr Ile Leu Glu Ile Pro Tyr Gln Lys Asn Ile Thr Ala Ile Phe
            260                 265                 270

Ile Leu Pro Asp Glu Gly Lys Leu Lys His Leu Glu Lys Gly Leu Gln
        275                 280                 285

Val Asp Thr Phe Ser Arg Trp Lys Thr Leu Leu Ser Arg Arg Val Val
    290                 295                 300

Asp Val Ser Val Pro Arg Leu His Met Thr Gly Thr Phe Asp Leu Lys
305                 310                 315                 320

Lys Thr Leu Ser Tyr Ile Gly Val Ser Lys Ile Phe Glu Glu His Gly
                325                 330                 335

Asp Leu Thr Lys Ile Ala Pro His Arg Ser Leu Lys Val Gly Glu Ala
            340                 345                 350

Val His Lys Ala Glu Leu Lys Met Asp Glu Arg Gly Thr Glu Gly Ala
        355                 360                 365

Ala Gly Thr Gly Ala Gln Thr Leu Pro Met Glu Thr Pro Leu Val Val
    370                 375                 380

Lys Ile Asp Lys Pro Tyr Leu Leu Leu Ile Tyr Ser Glu Lys Ile Pro
385                 390                 395                 400

Ser Val Leu Phe Leu Gly Lys Ile Val Asn Pro Ile Gly Lys
                405                 410
```

<210> SEQ ID NO 133
<211> LENGTH: 20
<212> TYPE: PRT
<213> ORGANISM: Homo sapiens

<400> SEQUENCE: 133

```
Gly Glu Arg Arg Asn Trp Gly Gly Glu Val Tyr Tyr Ser Thr Gly Tyr
  1               5                  10                  15

Ser Ser Arg Lys
             20
```

<210> SEQ ID NO 134
<211> LENGTH: 1777
<212> TYPE: DNA
<213> ORGANISM: Homo sapiens

<400> SEQUENCE: 134

```
ggcacgaggt ccccgacgcg ccccgcccaa cccctacgat gaagagggcg tccgctggag     60

ggagccggct gctggcatgg gtgctgtggc tgcaggcctg gcaggtggca gccccatgcc    120

caggtgcctg cgtatgctac aatgagccca aggtgacgac aagctgcccc cagcagggcc    180

tgcaggctgt gcccgtgggc atccctgctg ccagccagcg catcttcctg cacggcaacc    240

gcatctcgca tgtgccagct gccagcttcc gtgcctgccg caacctcacc atcctgtggc    300

tgcactcgaa tgtgctggcc cgaattgatg cggctgcctt cactggcctg gccctcctgg    360

agcagctgga cctcagcgat aatgcacagc tccggtctgt ggaccctgcc acattccacg    420

gcctgggccg cctacacacg ctgcacctgg accgctgcgg cctgcaggag ctgggcccgg    480

ggctgttccg cggcctggct gccctgcagt acctctacct gcaggacaac gcgctgcagg    540

cactgcctga tgacaccttc cgcgacctgg gcaacctcac acacctcttc ctgcacggca    600

accgcatctc cagcgtgccc gagcgcgcct tccgtgggct gcacagcctc gaccgtctcc    660

tactgcacca gaaccgcgtg gcccatgtgc acccgcatgc cttccgtgac cttggccgcc    720

tcatgacact ctatctgttt gccaacaatc tatcagcgct gcccactgag gccctggccc    780

ccctgcgtgc cctgcagtac ctgaggctca acgacaaccc ctgggtgtgt gactgccggg    840

cacgcccact ctgggcctgg ctgcagaagt tccgcggctc ctcctccgag gtgccctgca    900

gcctcccgca acgcctggct ggccgtgacc tcaaacgcct agctgccaat gacctgcagg    960

gctgcgctgt ggccaccggc ccttaccatc ccatctggac cggcagggcc accgatgagg   1020

agccgctggg gcttcccaag tgctgccagc cagatgccgc tgacaaggcc tcagtactgg   1080

agcctggaag accagcttcg gcaggcaatg cgctgaaggg acgcgtgccg cccggtgaca   1140

gcccgccggg caacggctct ggcccacggc acatcaatga ctcacccttt gggactctgc   1200

ctggctctgc tgagcccccg gctcactgca gtgcggcccg agggctccga gccaccaggt   1260

tccccacttc gggccctcgc cggaggccag gctgttcacg caagaaccgc acccgcagcc   1320

actgccgtct gggccaggca ggcagcgggg gtggcgggac tggtgactca gaaggctcag   1380

gtgccctacc cagcctcacc tgcagcctca ccccccctggg cctggcgctg gtgctgtgga   1440

cagtgcttgg gccctgctga cccccagcgg acacaagagc gtgctcagca gccaggtgtg   1500

tgtacatacg gggtctctct ccacgccgcc aagccagccg ggcggccgac ccgtggggca   1560

ggccaggcca ggtcctccct gatggacgcc tgccgcccgc cacccccatc tccaccccat   1620

catgtttaca gggttcggcg gcagcgtttg ttccagaacg ccgcctccca cccagatcgc   1680

ggtatataga gatatgcatt ttattttact tgtgtaaaaa tatcggacga cgtggaataa   1740

agagctcttt tcttaaaaaa aaaaaaaaaa aactcga                            1777
```

<210> SEQ ID NO 135
<211> LENGTH: 473
<212> TYPE: PRT
<213> ORGANISM: Homo sapiens

<400> SEQUENCE: 135

```
Met Lys Arg Ala Ser Ala Gly Gly Ser Arg Leu Leu Ala Trp Val Leu
  1               5                  10                  15

Trp Leu Gln Ala Trp Gln Val Ala Ala Pro Cys Pro Gly Ala Cys Val
             20                  25                  30

Cys Tyr Asn Glu Pro Lys Val Thr Thr Ser Cys Pro Gln Gln Gly Leu
         35                  40                  45

Gln Ala Val Pro Val Gly Ile Pro Ala Ala Ser Gln Arg Ile Phe Leu
     50                  55                  60

His Gly Asn Arg Ile Ser His Val Pro Ala Ala Ser Phe Arg Ala Cys
 65                  70                  75                  80

Arg Asn Leu Thr Ile Leu Trp Leu His Ser Asn Val Leu Ala Arg Ile
                 85                  90                  95

Asp Ala Ala Ala Phe Thr Gly Leu Ala Leu Leu Glu Gln Leu Asp Leu
            100                 105                 110

Ser Asp Asn Ala Gln Leu Arg Ser Val Asp Pro Ala Thr Phe His Gly
        115                 120                 125

Leu Gly Arg Leu His Thr Leu His Leu Asp Arg Cys Gly Leu Gln Glu
    130                 135                 140

Leu Gly Pro Gly Leu Phe Arg Gly Leu Ala Ala Leu Gln Tyr Leu Tyr
145                 150                 155                 160

Leu Gln Asp Asn Ala Leu Gln Ala Leu Pro Asp Asp Thr Phe Arg Asp
                165                 170                 175

Leu Gly Asn Leu Thr His Leu Phe Leu His Gly Asn Arg Ile Ser Ser
            180                 185                 190

Val Pro Glu Arg Ala Phe Arg Gly Leu His Ser Leu Asp Arg Leu Leu
        195                 200                 205

Leu His Gln Asn Arg Val Ala His Val His Pro His Ala Phe Arg Asp
    210                 215                 220

Leu Gly Arg Leu Met Thr Leu Tyr Leu Phe Ala Asn Asn Leu Ser Ala
225                 230                 235                 240

Leu Pro Thr Glu Ala Leu Ala Pro Leu Arg Ala Leu Gln Tyr Leu Arg
                245                 250                 255

Leu Asn Asp Asn Pro Trp Val Cys Asp Cys Arg Ala Arg Pro Leu Trp
            260                 265                 270

Ala Trp Leu Gln Lys Phe Arg Gly Ser Ser Ser Glu Val Pro Cys Ser
        275                 280                 285

Leu Pro Gln Arg Leu Ala Gly Arg Asp Leu Lys Arg Leu Ala Ala Asn
    290                 295                 300

Asp Leu Gln Gly Cys Ala Val Ala Thr Gly Pro Tyr His Pro Ile Trp
305                 310                 315                 320

Thr Gly Arg Ala Thr Asp Glu Glu Pro Leu Gly Leu Pro Lys Cys Cys
                325                 330                 335

Gln Pro Asp Ala Ala Asp Lys Ala Ser Val Leu Glu Pro Gly Arg Pro
            340                 345                 350

Ala Ser Ala Gly Asn Ala Leu Lys Gly Arg Val Pro Pro Gly Asp Ser
        355                 360                 365

Pro Pro Gly Asn Gly Ser Gly Pro Arg His Ile Asn Asp Ser Pro Phe
    370                 375                 380

Gly Thr Leu Pro Gly Ser Ala Glu Pro Pro Ala His Cys Ser Ala Ala
385                 390                 395                 400

Arg Gly Leu Arg Ala Thr Arg Phe Pro Thr Ser Gly Pro Arg Arg Arg
                405                 410                 415
```

```
Pro Gly Cys Ser Arg Lys Asn Arg Thr Arg Ser His Cys Arg Leu Gly
            420                 425                 430

Gln Ala Gly Ser Gly Gly Gly Gly Thr Gly Asp Ser Glu Gly Ser Gly
        435                 440                 445

Ala Leu Pro Ser Leu Thr Cys Ser Leu Thr Pro Leu Gly Leu Ala Leu
    450                 455                 460

Val Leu Trp Thr Val Leu Gly Pro Cys
465                 470


<210> SEQ ID NO 136
<211> LENGTH: 1774
<212> TYPE: DNA
<213> ORGANISM: Homo sapiens

<400> SEQUENCE: 136

ggcacgaggt ccccgacgcg ccccgcccaa cccctacgat gaagagggcg tccgctggag     60

ggagccggct gctggcatgg gtgctgtggc tgcaggcctg gcaggtggca gccccatgcc    120

caggtgcctg cgtatgctac aatgagccca aggtgacgac aagctgcccc cagcagggcc    180

tgcaggctgt gcccgtgggc atccctgctg ccagccagcg catcttcctg cacggcaacc    240

gcatctcgca tgtgccagct gccagcttcc gtgcctgccg caacctcacc atcctgtggc    300

tgcactcgaa tgtgctggcc cgaattgatg cggctgcctt cactggcctg gccctcctgg    360

agcagctgga cctcagcgat aatgcacagc tccggtctgt ggaccctgcc acattccacg    420

gcctgggccg cctacacacg ctgcacctgg accgctgcgg cctgcaggag ctgggcccgg    480

ggctgttccg cggcctggct gccctgcagt acctctacct gcaggacaac gcgctgcagg    540

cactgcctga tgacaccttc cgcgacctgg gcaacctcac acacctcttc ctgcacggca    600

accgcatctc cagcgtgccc gagcgcgcct tccgtgggct gcacagcctc gaccgtctcc    660

tactgcacca gaaccgcgtg gcccatgtgc acccgcatgc cttccgtgac cttggccgcc    720

tcatgacact ctatctgttt gccaacaatc tatcagcgct gcccactgag gccctggccc    780

ccctgcgtgc cctgcagtac ctgaggctca acgacaaccc ctgggtgtgt gactgccggg    840

cacgcccact ctgggcctgg ctgcagaagt tccgcggctc ctcctccgag gtgccctgca    900

gcctcccgca acgcctggct ggccgtgacc tcaaacgcct agctgccaat gacctgcagg    960

gctgcgctgt ggccaccggc ccttaccatc ccatctggac cggcagggcc accgatgagg   1020

agccgctggg gcttcccaag tgctgccagc cagatgccgc tgacaaggcc tcagtactgg   1080

agcctggaag accagcttcg gcaggcaatg cgctgaaggg acgcgtgccg cccggtgaca   1140

gcccgccggg aaacggtttt tggcccaagg gaacattaat gacttaccct tttgggactc   1200

tgcctggtct tgctgagccc ccggttagtg cattgcggcc cgagggctcc gagccaccag   1260

gttccccact tcgggccctt cgccggaggc caggctgttc acgcaagaac cgcacccgca   1320

gccatgccgt ctgggccagg caggcagcgg gggtggcggg actggtgact cagaaggctc   1380

aggtgcccta cccagcctca cctgcagcct cacccccctg ggcctggcgc tggtgctgtg   1440

gacagtgctt gggccctgct gacccccagc ggacacaaga gcgtgctcag cagccaggtg   1500

tgtgtacata cggggtctct ctccacgccg ccaagccagc cgggcggccg acccgtgggg   1560

caggccaggc caggtcctcc ctgatggacg cctgccgccc gccacccccca tctccacccc   1620

atcatgttta cagggttcgg cggcagcgtt tgttccagaa cgccgcctcc cacccagatc   1680

gcggtatata gagatatgca ttttatttta cttgtgtaaa aatatcggac gacgtggaat   1740

aaagagctct tttcttaaaa aaaaaaaaaa aaaa                                1774
```

<210> SEQ ID NO 137
<211> LENGTH: 550
<212> TYPE: PRT
<213> ORGANISM: Homo sapiens

<400> SEQUENCE: 137

Met Lys Arg Ala Ser Ala Gly Gly Ser Arg Leu Leu Ala Trp Val Leu
1 5 10 15

Trp Leu Gln Ala Trp Gln Val Ala Ala Pro Cys Pro Gly Ala Cys Val
20 25 30

Cys Tyr Asn Glu Pro Lys Val Thr Thr Ser Cys Pro Gln Gln Gly Leu
35 40 45

Gln Ala Val Pro Val Gly Ile Pro Ala Ala Ser Gln Arg Ile Phe Leu
50 55 60

His Gly Asn Arg Ile Ser His Val Pro Ala Ala Ser Phe Arg Ala Cys
65 70 75 80

Arg Asn Leu Thr Ile Leu Trp Leu His Ser Asn Val Leu Ala Arg Ile
85 90 95

Asp Ala Ala Ala Phe Thr Gly Leu Ala Leu Leu Glu Gln Leu Asp Leu
100 105 110

Ser Asp Asn Ala Gln Leu Arg Ser Val Asp Pro Ala Thr Phe His Gly
115 120 125

Leu Gly Arg Leu His Thr Leu His Leu Asp Arg Cys Gly Leu Gln Glu
130 135 140

Leu Gly Pro Gly Leu Phe Arg Gly Leu Ala Ala Leu Gln Tyr Leu Tyr
145 150 155 160

Leu Gln Asp Asn Ala Leu Gln Ala Leu Pro Asp Asp Thr Phe Arg Asp
165 170 175

Leu Gly Asn Leu Thr His Leu Phe Leu His Gly Asn Arg Ile Ser Ser
180 185 190

Val Pro Glu Arg Ala Phe Arg Gly Leu His Ser Leu Asp Arg Leu Leu
195 200 205

Leu His Gln Asn Arg Val Ala His Val His Pro His Ala Phe Arg Asp
210 215 220

Leu Gly Arg Leu Met Thr Leu Tyr Leu Phe Ala Asn Asn Leu Ser Ala
225 230 235 240

Leu Pro Thr Glu Ala Leu Ala Pro Leu Arg Ala Leu Gln Tyr Leu Arg
245 250 255

Leu Asn Asp Asn Pro Trp Val Cys Asp Cys Arg Ala Arg Pro Leu Trp
260 265 270

Ala Trp Leu Gln Lys Phe Arg Gly Ser Ser Ser Glu Val Pro Cys Ser
275 280 285

Leu Pro Gln Arg Leu Ala Gly Arg Asp Leu Lys Arg Leu Ala Ala Asn
290 295 300

Asp Leu Gln Gly Cys Ala Val Ala Thr Gly Pro Tyr His Pro Ile Trp
305 310 315 320

Thr Gly Arg Ala Thr Asp Glu Glu Pro Leu Gly Leu Pro Lys Cys Cys
325 330 335

Gln Pro Asp Ala Ala Asp Lys Ala Ser Val Leu Glu Pro Gly Arg Pro
340 345 350

Ala Ser Ala Gly Asn Ala Leu Lys Gly Arg Val Pro Pro Gly Asp Ser
355 360 365

Pro Pro Gly Asn Gly Phe Trp Pro Lys Gly Thr Leu Met Thr Tyr Pro
370 375 380

```
Phe Gly Thr Leu Pro Gly Leu Ala Glu Pro Pro Val Ser Ala Leu Arg
385                 390                 395                 400

Pro Glu Gly Ser Glu Pro Pro Gly Ser Pro Leu Arg Ala Leu Arg Arg
                405                 410                 415

Arg Pro Gly Cys Ser Arg Lys Asn Arg Thr Arg Ser His Ala Val Trp
            420                 425                 430

Ala Arg Gln Ala Ala Gly Val Ala Gly Leu Val Thr Gln Lys Ala Gln
        435                 440                 445

Val Pro Tyr Pro Ala Ser Pro Ala Ala Ser Pro Pro Trp Ala Trp Arg
    450                 455                 460

Trp Cys Cys Gly Gln Cys Leu Gly Pro Ala Asp Pro Gln Arg Thr Gln
465                 470                 475                 480

Glu Arg Ala Gln Gln Pro Gly Val Cys Thr Tyr Gly Val Ser Leu His
                485                 490                 495

Ala Ala Lys Pro Ala Gly Arg Pro Thr Arg Gly Ala Gly Gln Ala Arg
            500                 505                 510

Ser Ser Leu Met Asp Ala Cys Arg Pro Pro Pro Pro Ser Pro Pro His
        515                 520                 525

His Val Tyr Arg Val Arg Arg Gln Arg Leu Phe Gln Asn Ala Ala Ser
    530                 535                 540

His Pro Asp Arg Gly Ile
545                 550


<210> SEQ ID NO 138
<211> LENGTH: 1777
<212> TYPE: DNA
<213> ORGANISM: Homo sapiens

<400> SEQUENCE: 138

ggcacgaggt ccccgacgcg ccccgcccaa cccctacgat gaagagggcg tccgctggag     60

ggagccggct gctggcatgg gtgctgtggc tgcaggcctg gcaggtggca gccccatgcc    120

caggtgcctg cgtatgctac aatgagccca aggtgacgac aagctgcccc cagcagggcc    180

tgcaggctgt gcccgtgggc atccctgctg ccagccagcg catcttcctg cacggcaacc    240

gcatctcgca tgtgccagct gccagcttcc gtgcctgccg caacctcacc atcctgtggc    300

tgcactcgaa tgtgctggcc cgaattgatg cggctgcctt cactggcctg gccctcctgg    360

agcagctgga cctcagcgat aatgcacagc tccggtctgt ggaccctgcc acattccacg    420

gcctgggccg cctacacacg gtgcacctgg accgctgcgg cctgcaggag ctgggcccgg    480

ggctgttccg cggcctggct gccctgcagt acctctacct gcaggacaac gcgctgcagg    540

cactgcctga tgacaccttc cgcgacctgg gcaacctcac acacctcttc ctgcacggca    600

accgcatctc cagcgtgccc gagcgcgcct tccgtgggct gcacagcctc gaccgtctcc    660

tactgcacca gaaccgcgtg gcccatgtgc acccgcatgc cttccgtgac cttggccgcc    720

tcatgacact ctatctgttt gccaacaatc tatcagcgct gcccactgag gccctggccc    780

ccctgcgtgc cctgcaatac ctgaggctca acgacaaccc ctgggtgtgt gactgccggg    840

cacgcccact ctgggcctgg ctgcagaagt tccgcggctc ctcctccgag gtgccctgca    900

gcctcccgca acgcctggct ggccgtgacc tcaaacgcct agctgccaat gacctgcagg    960

gctgcgctgt ggccaccggc ccttaccatc ccatctggac cggcagggcc accgatgagg   1020

agccgctggg gcttcccaag tgctgccagc cagatgccgc tgacaaggcc tcagtactgg   1080

agcctggaag accagcttcg gcaggcaatg cgctgaaggg accgcgtgcc ggccggggac   1140

aggcccggcg ggaaacggtt tttggcccaa gggaacatta atgacttacc cttttgggac   1200
```

```
tctgcctggt tttggtgagc ccccggttac ttgcagtgcg gcccgaggga tccgagccac   1260

caggttcccc acttcgggcc cttcgccgga ggccaggctg ttcacgcaag aaccgcaccc   1320

gcagccatgc cgtctgggcc aggcaggcag cgggggtggc gggactggtg actcagaagg   1380

ctcaggtgcc ctacccagcc tcacctgcag cctcaccccc ctgggcctgg cgctggtgct   1440

gtggacagtg cttgggccct gctgaccccc agcggacaca agagcgtgct cagcagccag   1500

gtgtgtgtac atacggggtc tctctccacg ccgccaagcc agccgggcgg ccgacccgtg   1560

gggcaggcca ggccaggtcc tccctgatgg acgcctgccg cccgccaccc ccatctccac   1620

cccatcatgt ttacagggtt cggcggcagc gtttgttcca gaacgccgcc tcccacccag   1680

atcgcggtat atagagatat gcattttatt ttacttgtgt aaaaatatcg gacgacgtgg   1740

aataaagagc tcttttctta aaaaaaaaaa aaaaaaa                            1777
```

<210> SEQ ID NO 139
<211> LENGTH: 380
<212> TYPE: PRT
<213> ORGANISM: Homo sapiens

<400> SEQUENCE: 139

```
Met Lys Arg Ala Ser Ala Gly Gly Ser Arg Leu Leu Ala Trp Val Leu
  1               5                  10                  15

Trp Leu Gln Ala Trp Gln Val Ala Ala Pro Cys Pro Gly Ala Cys Val
             20                  25                  30

Cys Tyr Asn Glu Pro Lys Val Thr Thr Ser Cys Pro Gln Gln Gly Leu
         35                  40                  45

Gln Ala Val Pro Val Gly Ile Pro Ala Ala Ser Gln Arg Ile Phe Leu
     50                  55                  60

His Gly Asn Arg Ile Ser His Val Pro Ala Ala Ser Phe Arg Ala Cys
 65                  70                  75                  80

Arg Asn Leu Thr Ile Leu Trp Leu His Ser Asn Val Leu Ala Arg Ile
                 85                  90                  95

Asp Ala Ala Ala Phe Thr Gly Leu Ala Leu Leu Glu Gln Leu Asp Leu
            100                 105                 110

Ser Asp Asn Ala Gln Leu Arg Ser Val Asp Pro Ala Thr Phe His Gly
        115                 120                 125

Leu Gly Arg Leu His Thr Val His Leu Asp Arg Cys Gly Leu Gln Glu
    130                 135                 140

Leu Gly Pro Gly Leu Phe Arg Gly Leu Ala Ala Leu Gln Tyr Leu Tyr
145                 150                 155                 160

Leu Gln Asp Asn Ala Leu Gln Ala Leu Pro Asp Asp Thr Phe Arg Asp
                165                 170                 175

Leu Gly Asn Leu Thr His Leu Phe Leu His Gly Asn Arg Ile Ser Ser
            180                 185                 190

Val Pro Glu Arg Ala Phe Arg Gly Leu His Ser Leu Asp Arg Leu Leu
        195                 200                 205

Leu His Gln Asn Arg Val Ala His Val His Pro His Ala Phe Arg Asp
    210                 215                 220

Leu Gly Arg Leu Met Thr Leu Tyr Leu Phe Ala Asn Asn Leu Ser Ala
225                 230                 235                 240

Leu Pro Thr Glu Ala Leu Ala Pro Leu Arg Ala Leu Gln Tyr Leu Arg
                245                 250                 255

Leu Asn Asp Asn Pro Trp Val Cys Asp Cys Arg Ala Arg Pro Leu Trp
            260                 265                 270
```

```
Ala Trp Leu Gln Lys Phe Arg Gly Ser Ser Ser Glu Val Pro Cys Ser
        275                 280                 285

Leu Pro Gln Arg Leu Ala Gly Arg Asp Leu Lys Arg Leu Ala Ala Asn
    290                 295                 300

Asp Leu Gln Gly Cys Ala Val Ala Thr Gly Pro Tyr His Pro Ile Trp
305                 310                 315                 320

Thr Gly Arg Ala Thr Asp Glu Glu Pro Leu Gly Leu Pro Lys Cys Cys
                325                 330                 335

Gln Pro Asp Ala Ala Asp Lys Ala Ser Val Leu Glu Pro Gly Arg Pro
            340                 345                 350

Ala Ser Ala Gly Asn Ala Leu Lys Gly Pro Arg Ala Gly Arg Gly Gln
        355                 360                 365

Ala Arg Arg Glu Thr Val Phe Gly Pro Arg Glu His
    370                 375                 380


<210> SEQ ID NO 140
<211> LENGTH: 380
<212> TYPE: PRT
<213> ORGANISM: Homo sapiens

<400> SEQUENCE: 140

Met Lys Arg Ala Ser Ala Gly Gly Ser Arg Leu Leu Ala Trp Val Leu
  1               5                  10                  15

Trp Leu Gln Ala Trp Gln Val Ala Ala Pro Cys Pro Gly Ala Cys Val
            20                  25                  30

Cys Tyr Asn Glu Pro Lys Val Thr Thr Ser Cys Pro Gln Gln Gly Leu
        35                  40                  45

Gln Ala Val Pro Val Gly Ile Pro Ala Ala Ser Gln Arg Ile Phe Leu
     50                  55                  60

His Gly Asn Arg Ile Ser His Val Pro Ala Ala Ser Phe Arg Ala Cys
 65                  70                  75                  80

Arg Asn Leu Thr Ile Leu Trp Leu His Ser Asn Val Leu Ala Arg Ile
                85                  90                  95

Asp Ala Ala Ala Phe Thr Gly Leu Ala Leu Leu Glu Gln Leu Asp Leu
            100                 105                 110

Ser Asp Asn Ala Gln Leu Arg Ser Val Asp Pro Ala Thr Phe His Gly
        115                 120                 125

Leu Gly Arg Leu His Thr Val His Leu Asp Arg Cys Gly Leu Gln Glu
    130                 135                 140

Leu Gly Pro Gly Leu Phe Arg Gly Leu Ala Ala Leu Gln Tyr Leu Tyr
145                 150                 155                 160

Leu Gln Asp Asn Ala Leu Gln Ala Leu Pro Asp Asp Thr Phe Arg Asp
                165                 170                 175

Leu Gly Asn Leu Thr His Leu Phe Leu His Gly Asn Arg Ile Ser Ser
            180                 185                 190

Val Pro Glu Arg Ala Phe Arg Gly Leu His Ser Leu Asp Arg Leu Leu
        195                 200                 205

Leu His Gln Asn Arg Val Ala His Val His Pro His Ala Phe Arg Asp
    210                 215                 220

Leu Gly Arg Leu Met Thr Leu Tyr Leu Phe Ala Asn Asn Leu Ser Ala
225                 230                 235                 240

Leu Pro Thr Glu Ala Leu Ala Pro Leu Arg Ala Leu Gln Tyr Leu Arg
                245                 250                 255

Leu Asn Asp Asn Pro Trp Val Cys Asp Cys Arg Ala Arg Pro Leu Trp
            260                 265                 270
```

Ala Trp Leu Gln Lys Phe Arg Gly Ser Ser Ser Glu Val Pro Cys Ser
275 280 285

Leu Pro Gln Arg Leu Ala Gly Arg Asp Leu Lys Arg Leu Ala Ala Asn
290 295 300

Asp Leu Gln Gly Cys Ala Val Ala Thr Gly Pro Tyr His Pro Ile Trp
305 310 315 320

Thr Gly Arg Ala Thr Asp Glu Glu Pro Leu Gly Leu Pro Lys Cys Cys
325 330 335

Gln Pro Asp Ala Ala Asp Lys Ala Ser Val Leu Glu Pro Gly Arg Pro
340 345 350

Ala Ser Ala Gly Asn Ala Leu Lys Gly Pro Arg Ala Gly Arg Gly Gln
355 360 365

Ala Arg Arg Glu Thr Val Phe Gly Pro Arg Glu His
370 375 380

<210> SEQ ID NO 141
<211> LENGTH: 12
<212> TYPE: PRT
<213> ORGANISM: Homo sapiens

<400> SEQUENCE: 141

Phe His Gly Leu Gly Arg Leu His Thr Val His Leu
1 5 10

<210> SEQ ID NO 142
<211> LENGTH: 21
<212> TYPE: PRT
<213> ORGANISM: Homo sapiens

<400> SEQUENCE: 142

Ala Ala Phe Thr Gly Leu Ala Leu Leu Glu Gln Leu Asp Leu Ser Asp
1 5 10 15

Asn Ala Gln Leu Arg
20

<210> SEQ ID NO 143
<211> LENGTH: 12
<212> TYPE: PRT
<213> ORGANISM: Homo sapiens

<400> SEQUENCE: 143

His Glu Val Pro Asp Ala Pro Arg Pro Thr Pro Thr
1 5 10

<210> SEQ ID NO 144
<211> LENGTH: 9
<212> TYPE: PRT
<213> ORGANISM: Homo sapiens

<400> SEQUENCE: 144

Ala Phe Arg Gly Leu His Ser Leu Asp
1 5

<210> SEQ ID NO 145
<211> LENGTH: 22
<212> TYPE: PRT
<213> ORGANISM: Homo sapiens

<400> SEQUENCE: 145

Ser Gln Arg Ile Phe Leu His Gly Asn Arg Ile Ser His Val Pro Ala
1 5 10 15

Ala Ser Phe Arg Ala Cys

20

<210> SEQ ID NO 146
<211> LENGTH: 22
<212> TYPE: PRT
<213> ORGANISM: Homo sapiens

<400> SEQUENCE: 146

Leu Thr Ile Leu Trp Leu His Ser Asn Val Leu Ala Arg Ile Asp Ala
1 5 10 15

Ala Ala Phe Thr Gly Leu
20

<210> SEQ ID NO 147
<211> LENGTH: 23
<212> TYPE: PRT
<213> ORGANISM: Homo sapiens

<400> SEQUENCE: 147

Leu Glu Gln Leu Asp Leu Ser Asp Asn Ala Gln Leu Arg Ser Val Asp
1 5 10 15

Pro Ala Thr Phe His Gly Leu
20

<210> SEQ ID NO 148
<211> LENGTH: 22
<212> TYPE: PRT
<213> ORGANISM: Homo sapiens

<400> SEQUENCE: 148

Leu His Thr Leu His Leu Asp Arg Cys Gly Leu Gln Glu Leu Gly Pro
1 5 10 15

Gly Leu Phe Arg Gly Leu
20

<210> SEQ ID NO 149
<211> LENGTH: 22
<212> TYPE: PRT
<213> ORGANISM: Homo sapiens

<400> SEQUENCE: 149

Leu Gln Tyr Leu Tyr Leu Gln Asp Asn Ala Leu Gln Ala Leu Pro Asp
1 5 10 15

Asp Thr Phe Arg Asp Leu
20

<210> SEQ ID NO 150
<211> LENGTH: 22
<212> TYPE: PRT
<213> ORGANISM: Homo sapiens

<400> SEQUENCE: 150

Leu Thr His Leu Phe Leu His Gly Asn Arg Ile Ser Ser Val Pro Glu
1 5 10 15

Arg Ala Phe Arg Gly Leu
20

<210> SEQ ID NO 151
<211> LENGTH: 22
<212> TYPE: PRT
<213> ORGANISM: Homo sapiens

<400> SEQUENCE: 151

```
Leu Asp Arg Leu Leu Leu His Gln Asn Arg Val Ala His Val His Pro
  1               5                  10                  15

His Ala Phe Arg Asp Leu
             20


<210> SEQ ID NO 152
<211> LENGTH: 22
<212> TYPE: PRT
<213> ORGANISM: Homo sapiens

<400> SEQUENCE: 152

Leu Met Thr Leu Tyr Leu Phe Ala Asn Asn Leu Ser Ala Leu Pro Thr
  1               5                  10                  15

Glu Ala Leu Ala Pro Leu
             20


<210> SEQ ID NO 153
<211> LENGTH: 13
<212> TYPE: PRT
<213> ORGANISM: Homo sapiens

<400> SEQUENCE: 153

Ala His Cys Ser Ala Ala Arg Gly Leu Arg Ala Thr Arg
  1               5                  10


<210> SEQ ID NO 154
<211> LENGTH: 15
<212> TYPE: PRT
<213> ORGANISM: Homo sapiens

<400> SEQUENCE: 154

Pro Ala His Cys Ser Ala Ala Arg Gly Leu Arg Ala Thr Arg Phe
  1               5                  10                  15


<210> SEQ ID NO 155
<211> LENGTH: 23
<212> TYPE: PRT
<213> ORGANISM: Homo sapiens

<400> SEQUENCE: 155

Pro Ser Leu Thr Cys Ser Leu Thr Pro Leu Gly Leu Ala Leu Val Leu
  1               5                  10                  15

Trp Thr Val Leu Gly Pro Cys
             20


<210> SEQ ID NO 156
<211> LENGTH: 21
<212> TYPE: PRT
<213> ORGANISM: Homo sapiens

<400> SEQUENCE: 156

Leu Pro Ser Leu Thr Cys Ser Leu Thr Pro Leu Gly Leu Ala Leu Val
  1               5                  10                  15

Leu Trp Thr Val Leu
             20


<210> SEQ ID NO 157
<211> LENGTH: 24
<212> TYPE: PRT
<213> ORGANISM: Homo sapiens

<400> SEQUENCE: 157

Leu Pro Ser Leu Thr Cys Ser Leu Thr Pro Leu Gly Leu Ala Leu Val
  1               5                  10                  15
```

```
Leu Trp Thr Val Leu Gly Pro Cys
            20


<210> SEQ ID NO 158
<211> LENGTH: 14
<212> TYPE: PRT
<213> ORGANISM: Homo sapiens

<400> SEQUENCE: 158

Cys Arg Asn Leu Thr Ile Leu Trp Leu His Ser Asn Val Leu
  1               5                  10


<210> SEQ ID NO 159
<211> LENGTH: 1797
<212> TYPE: DNA
<213> ORGANISM: Homo sapiens

<400> SEQUENCE: 159

ggtcgacggt atcgataagc ttgatatcga attcctgcaa cagttcttgg aaacccactc     60

gagagggcca cgcctccatt caccaggcca cgcatcacaa gaggcaacac caggagccaa    120

catgagctcg gggactgaac tgctgtggcc cggagcagcg ctgctggtgc tgttgggggt    180

ggcagccagt ctgtgtgtgc gctgctcacg cccaggtgca aagaggtcag agaaaatcta    240

ccagcagaga agtctgcgtg aggaccaaca gagctttacg gggtcccgga cctactcctt    300

ggtcgggcag gcatggccag gacccctggc ggacatggca cccacaagga aggacaagct    360

gttgcaattc taccccagcc tggaggatcc agcatcttcc aggtaccaga acttcagcaa    420

aggaagcaga cacgggtcgg aggaagccta catagacccc attgccatgg agtattacaa    480

ctgggggcgg ttctcgaagc ccccagaaga tgatgatgcc aattcctacg agaatgtgct    540

catttgcaag cagaaaacca cagagacagg tgcccagcag gagggcatag gtggcctctg    600

cagaggggac ctcagcctgt cactggccct gaagactggc cccacttctg gtctctgtcc    660

ctctgcctcc ccggaagaag atgaaggaat ctgaggatta tcagaacttc agcattccat    720

ccattcagtg gcgcgagtcc aggaaggtca tggggcaact ccagagaaga aagcatcccc    780

tggcccggtg ggaagcccag acgaggagga cggggaaccg gattacgtga atggggaggt    840

ggcagccaca gaagcctagg gcagaccaag aagaaaggag ccaaggcaaa gagggaccac    900

tgtgctcatg gacccatcgc tgccttccaa ggaccatttc ccagagctac tcaactttta    960

agcccctgcc atggttgctc ctggaaggag aaccagccac cctgaggacc acctggccat   1020

gcgtgcacag cctgggaaaa gacagttact cacgggagct gcaggccccg tcaccaagcc   1080

ctctcccgac ccaggctttg tggggcaggc acctggtacc aagggtaacc cggctcctgg   1140

tatggacgga tgcgcaggat ttaggataag ctgtcaccca gtccccataa caaaaccact   1200

gtccaacact ggtatctgtg ttcttttgtg ctatgaattt ggattcctaa ttgctattgt   1260

tggttgctgg ggttttaaat gattgataag cttgtacagt taacttatag agggggagcc   1320

atatttaaca ttctggattt cagagtagag atttctgtgt tgtctcctag aaagcattac   1380

atgtagttta tttcagcatc cttgttgggt ggggccctgg ctctcttccc ctttggtggg   1440

acctcccctt tctttgggct tcagttcact caggaagaaa tgaggctgtc gccatcttta   1500

tgtgcttcca gtggaaatgt cacttgctac agacaatagt gcatgagagt ctagagaagt   1560

agtgaccaga acagggcaga gtaggtcccc tccatggccc tgaatcctcc tctgctccag   1620

ggctggcctc tgcagagctg attaaacagt gttgtgactg tctcatggga agagctgggg   1680

cccagaggga ccttgagtca gaaatgttgc cagaaaaagt atctcctcca accaaaacat   1740
```

ctcaataaaa ccattttagt tgaaaaaaaa aaaaaaaaaa aaaaaaaaaa aaaaaaa 1797

<210> SEQ ID NO 160
<211> LENGTH: 190
<212> TYPE: PRT
<213> ORGANISM: Homo sapiens

<400> SEQUENCE: 160

Met Ser Ser Gly Thr Glu Leu Leu Trp Pro Gly Ala Ala Leu Leu Val
1 5 10 15

Leu Leu Gly Val Ala Ala Ser Leu Cys Val Arg Cys Ser Arg Pro Gly
20 25 30

Ala Lys Arg Ser Glu Lys Ile Tyr Gln Gln Arg Ser Leu Arg Glu Asp
35 40 45

Gln Gln Ser Phe Thr Gly Ser Arg Thr Tyr Ser Leu Val Gly Gln Ala
50 55 60

Trp Pro Gly Pro Leu Ala Asp Met Ala Pro Thr Arg Lys Asp Lys Leu
65 70 75 80

Leu Gln Phe Tyr Pro Ser Leu Glu Asp Pro Ala Ser Ser Arg Tyr Gln
85 90 95

Asn Phe Ser Lys Gly Ser Arg His Gly Ser Glu Glu Ala Tyr Ile Asp
100 105 110

Pro Ile Ala Met Glu Tyr Tyr Asn Trp Gly Arg Phe Ser Lys Pro Pro
115 120 125

Glu Asp Asp Asp Ala Asn Ser Tyr Glu Asn Val Leu Ile Cys Lys Gln
130 135 140

Lys Thr Thr Glu Thr Gly Ala Gln Gln Glu Gly Ile Gly Gly Leu Cys
145 150 155 160

Arg Gly Asp Leu Ser Leu Ser Leu Ala Leu Lys Thr Gly Pro Thr Ser
165 170 175

Gly Leu Cys Pro Ser Ala Ser Pro Glu Glu Asp Glu Gly Ile
180 185 190

<210> SEQ ID NO 161
<211> LENGTH: 1773
<212> TYPE: DNA
<213> ORGANISM: Homo sapiens

<400> SEQUENCE: 161
cccggggttg gcatcagctt gggcaggtgt gcgggctcat tggggcggcc gtggtgagga 60
accctggact ctcagcatca caagaggcaa caccaggagc caacatgagc tcggggactg 120
aactgctgtg gcccggagca gcgctgctgg tgctgttggg ggtggcagcc agtctgtgtg 180
tgcgctgctc acgcccaggt gcaaagaggt cagagaaaat ctaccagcag agaagtctgc 240
gtgaggacca acagagcttt acggggtccc ggacctactc cttggtcggg caggcatggc 300
caggacccct ggcggacatg gcacccacaa ggaaggacaa gctgttgcaa ttctacccca 360
gcctggagga tccagcatct tccaggtacc agaacttcag caaaggaagc agacacgggt 420
cggaggaagc ctacatagac cccattgcca tggagtatta caactggggg cggttctcga 480
agcccccaga agatgatgat gccaattcct acgagaatgt gctcatttgc aagcagaaaa 540
ccacagagac aggtgcccag caggagggca taggtggcct ctgcagaggg gacctcagcc 600
tgtcactggc cctgaagact ggccccactt ctggtctctg tccctctgcc tccccggaag 660
aagatgagga atctgaggat tatcagaact cagcatccat ccatcagtgg cgcgagtcca 720
ggaaggtcat ggggcaactc cagagagaag catcccctgg cccggtggga agcccagacg 780

-continued

```
aggaggacgg ggaaccggat tacgtgaatg gggaggtggc agccacagaa gcctagggca    840

gaccaagaag aaaggagcca aggcaaagag ggaccactgt gctcatggac ccatcgctgc    900

cttccaagga ccatttccca gagctactca acttttaagc cctgccatgg gttgctcctg    960

gaaggagaac cagccaccct gaggaccacc tggccatgcg tgcacagcct gggaaaagac   1020

agttactcac gggagctgca ggcccgtcac caagccctct cccgacccag gctttgtggg   1080

gcaggcacct ggtaccaagg gtaacccggc tcctggtatg gacggatgcg caggatttag   1140

gataagctgt cacccagtcc ccataacaaa accactgtcc aacactggta tctgtgttct   1200

tttgtgctat gaatttggat tcctaattgc tattgttggt tgctggggtt ttaaatgatt   1260

gataagcttg tacagttaac ttatagaggg ggagccatat ttaacattct ggatttcaga   1320

gtagagattt ctgtgttgtc tcctagaaag cattacatgt agtttatttc agcatccttg   1380

ttgggtgggg ccctggctct cttccccttt ggtgggacct ccccttctt tgggcttcag   1440

ttcactcagg aagaaatgag gctgtcgcca tctttatgtg cttccagtgg aaatgtcact   1500

tgctacagac aatagtgcat gagagtctag agaagtagtg accagaacag ggcagagtag   1560

gtcccctcca tggccctgaa tcctcctctg ctccagggct ggcctctgca gagctgatta   1620

aacagtgttg tgactgtctc atgggaagag ctggggccca gagggacctt gagtcagaaa   1680

tgttgccaga aaaagtatct cctccaacca aaacatctca ataaaaccat tttagttgaa   1740

aaaaaaaaaa aaaaaaaaaa aaaaaaaaaa aaa                                1773
```

<210> SEQ ID NO 162
<211> LENGTH: 243
<212> TYPE: PRT
<213> ORGANISM: Homo sapiens

<400> SEQUENCE: 162

```
Met Ser Ser Gly Thr Glu Leu Leu Trp Pro Gly Ala Ala Leu Leu Val
  1               5                  10                  15

Leu Leu Gly Val Ala Ala Ser Leu Cys Val Arg Cys Ser Arg Pro Gly
             20                  25                  30

Ala Lys Arg Ser Glu Lys Ile Tyr Gln Gln Arg Ser Leu Arg Glu Asp
         35                  40                  45

Gln Gln Ser Phe Thr Gly Ser Arg Thr Tyr Ser Leu Val Gly Gln Ala
     50                  55                  60

Trp Pro Gly Pro Leu Ala Asp Met Ala Pro Thr Arg Lys Asp Lys Leu
 65                  70                  75                  80

Leu Gln Phe Tyr Pro Ser Leu Glu Asp Pro Ala Ser Ser Arg Tyr Gln
                 85                  90                  95

Asn Phe Ser Lys Gly Ser Arg His Gly Ser Glu Glu Ala Tyr Ile Asp
            100                 105                 110

Pro Ile Ala Met Glu Tyr Tyr Asn Trp Gly Arg Phe Ser Lys Pro Pro
        115                 120                 125

Glu Asp Asp Asp Ala Asn Ser Tyr Glu Asn Val Leu Ile Cys Lys Gln
    130                 135                 140

Lys Thr Thr Glu Thr Gly Ala Gln Gln Glu Gly Ile Gly Gly Leu Cys
145                 150                 155                 160

Arg Gly Asp Leu Ser Leu Ser Leu Ala Leu Lys Thr Gly Pro Thr Ser
                165                 170                 175

Gly Leu Cys Pro Ser Ala Ser Pro Glu Glu Asp Glu Glu Ser Glu Asp
            180                 185                 190

Tyr Gln Asn Ser Ala Ser Ile His Gln Trp Arg Glu Ser Arg Lys Val
```

```
        195                 200                 205

Met Gly Gln Leu Gln Arg Glu Ala Ser Pro Gly Pro Val Gly Ser Pro
    210                 215                 220

Asp Glu Glu Asp Gly Glu Pro Asp Tyr Val Asn Gly Glu Val Ala Ala
225                 230                 235                 240

Thr Glu Ala


<210> SEQ ID NO 163
<211> LENGTH: 230
<212> TYPE: PRT
<213> ORGANISM: Homo sapiens

<400> SEQUENCE: 163

Val Asp Gly Ile Asp Lys Leu Asp Ile Glu Phe Leu Gln Gln Phe Leu
  1               5                  10                  15

Glu Thr His Ser Arg Gly Pro Arg Leu His Ser Pro Gly His Ala Ser
             20                  25                  30

Gln Glu Ala Thr Pro Gly Ala Asn Met Ser Ser Gly Thr Glu Leu Leu
         35                  40                  45

Trp Pro Gly Ala Ala Leu Leu Val Leu Leu Gly Val Ala Ala Ser Leu
     50                  55                  60

Cys Val Arg Cys Ser Arg Pro Gly Ala Lys Arg Ser Glu Lys Ile Tyr
 65                  70                  75                  80

Gln Gln Arg Ser Leu Arg Glu Asp Gln Gln Ser Phe Thr Gly Ser Arg
                 85                  90                  95

Thr Tyr Ser Leu Val Gly Gln Ala Trp Pro Gly Pro Leu Ala Asp Met
            100                 105                 110

Ala Pro Thr Arg Lys Asp Lys Leu Leu Gln Phe Tyr Pro Ser Leu Glu
        115                 120                 125

Asp Pro Ala Ser Ser Arg Tyr Gln Asn Phe Ser Lys Gly Ser Arg His
    130                 135                 140

Gly Ser Glu Glu Ala Tyr Ile Asp Pro Ile Ala Met Glu Tyr Tyr Asn
145                 150                 155                 160

Trp Gly Arg Phe Ser Lys Pro Pro Glu Asp Asp Asp Ala Asn Ser Tyr
                165                 170                 175

Glu Asn Val Leu Ile Cys Lys Gln Lys Thr Thr Glu Thr Gly Ala Gln
            180                 185                 190

Gln Glu Gly Ile Gly Gly Leu Cys Arg Gly Asp Leu Ser Leu Ser Leu
        195                 200                 205

Ala Leu Lys Thr Gly Pro Thr Ser Gly Leu Cys Pro Ser Ala Ser Pro
    210                 215                 220

Glu Glu Asp Glu Gly Ile
225                 230


<210> SEQ ID NO 164
<211> LENGTH: 25
<212> TYPE: PRT
<213> ORGANISM: Homo sapiens

<400> SEQUENCE: 164

Ala Ser Ser Arg Tyr Gln Asn Phe Ser Lys Gly Ser Arg His Gly Ser
  1               5                  10                  15

Glu Glu Ala Tyr Ile Asp Pro Ile Ala
             20                  25


<210> SEQ ID NO 165
<211> LENGTH: 21
```

<212> TYPE: PRT
<213> ORGANISM: Homo sapiens

<400> SEQUENCE: 165

```
Met Glu Tyr Tyr Asn Trp Gly Arg Phe Ser Lys Pro Pro Glu Asp Asp
  1               5                  10                  15

Asp Ala Asn Ser Tyr
             20
```

<210> SEQ ID NO 166
<211> LENGTH: 27
<212> TYPE: PRT
<213> ORGANISM: Homo sapiens

<400> SEQUENCE: 166

```
Glu Asn Val Leu Ile Cys Lys Gln Lys Thr Thr Glu Thr Gly Ala Gln
  1               5                  10                  15

Gln Glu Gly Ile Gly Gly Leu Cys Arg Gly Asp
             20                  25
```

<210> SEQ ID NO 167
<211> LENGTH: 68
<212> TYPE: PRT
<213> ORGANISM: Homo sapiens

<400> SEQUENCE: 167

```
Val Arg Cys Ser Arg Pro Gly Ala Lys Arg Ser Glu Lys Ile Tyr Gln
  1               5                  10                  15

Gln Arg Ser Leu Arg Glu Asp Gln Gln Ser Phe Thr Gly Ser Arg Thr
             20                  25                  30

Tyr Ser Leu Val Gly Gln Ala Trp Pro Gly Pro Leu Ala Asp Met Ala
         35                  40                  45

Pro Thr Arg Lys Asp Lys Leu Leu Gln Phe Tyr Pro Ser Leu Glu Asp
     50                  55                  60

Pro Ala Ser Ser
 65
```

<210> SEQ ID NO 168
<211> LENGTH: 27
<212> TYPE: PRT
<213> ORGANISM: Homo sapiens

<400> SEQUENCE: 168

```
Leu Ser Leu Ser Leu Ala Leu Lys Thr Gly Pro Thr Ser Gly Leu Cys
  1               5                  10                  15

Pro Ser Ala Ser Pro Glu Glu Asp Glu Gly Ile
             20                  25
```

<210> SEQ ID NO 169
<211> LENGTH: 2209
<212> TYPE: DNA
<213> ORGANISM: Homo sapiens

<400> SEQUENCE: 169

```
gagctgcgcc gggcttgggc gcctggggcc gccgctcccc accgtcgttt tccccaccga      60

ggccgaggcg tcccggagtc atggccggcc tgaactgcgg ggtctctatc gcactgctag     120

gggttctgct gctgggtgcg gcgcgcctgc cgcgcggggc agaagctttt gagattgctc     180

tgccacgaga aagcaacatt acagttctca taaagctggg gaccccgact ctgctggcaa     240

aaccctgtta catcgtcatt tctaaaagac atataaccat gttgtccatc aagtctggag     300
```

```
aaagaatagt ctttaccttt agctgccaga gtcctgagaa tcactttgtc atagagatcc    360

agaaaaatat tgactgtatg tcaggcccat gtccttttgg ggaggttcag cttcagccct    420

cgacatcgtt gttgcctacc ctcaacagaa ctttcatctg ggatgtcaaa gctcataaga    480

gcatcggttt agagctgcag ttttccatcc ctcgcctgag gcagatcggt ccgggtgaga    540

gctgcccaga cggagtcact cactccatca gcggccgaat cgatgccacc gtggtcagga    600

ttggaacctt ctgcagcaat ggcactgtgt cccggatcaa gatgcawgaa ggagtgaaaa    660

tggccttaca cctcccatgg ttccacccca gaaatgtctc cggcttcagc attgcaaacc    720

gctcatctat aaaacgtctg tgcatcatcg agtctgtgtt tgagggtgaa ggctcagcaa    780

ccctgatgtc tgccaactac ccagaaggct tccctgagga tgagctcatg acgtggcagt    840

ttgtcgttcc tgcacacctg cgggccagcg tctccttcct caacttcaac ctctccaact    900

gtragaggaa ggaggagcgg gttgaatact acatcccggg ctccaccacc aaccccgagg    960

tgttcaagct ggaggacaag cagcctggga acatggcggg gaacttcaac ctctctctgc   1020

aaggctgtga ccaagatgcc caaagtccag ggatcctccg gctgcagttc caagttttgg   1080

tccaacatcc acaaaatgaa agcaataaaa tctacgtggt tgacttgagt aatgagcgag   1140

ccatgtcact caccatcgag ccacggcccg tcaaacagag ccgcaagttt gtccctggct   1200

gtttcgtgtg tctagaatct cggacctgca gtagcaacct caccctgaca tctggctcca   1260

aacacaaaat ctccttcctt tgtgatgatc tgacacgtct gtggatgaat gtggaaaaam   1320

ccataagytg cacagaccac cggtactgcc aaaggaaatc ctactcacty caggtgccca   1380

gtgacatcct ycamctgcct gtggagctgc atgacttctc ctggaagctg ctggtgccca   1440

aggacaggct cagcctggtg ctggtgccag cccagaagct gcagcagcat acacacgaga   1500

agccctgcaa caccagcttc agctacctcg tggccagtgc catacccagc caggacctgt   1560

acttcggctc cttctgcccg ggaggctcta tcaagcagat ccaggtgaag cagaacatct   1620

cggtgaccct tcgcaccttt gcccccagct tccgacaaga ggcctccagg cagggtctga   1680

cggtgtcctt tataccttat ttcaaagagg aaggcgtttt cacggtgacc cctgacacaa   1740

aaagcaaggt ctacctgagg acccccaact gggaccgggg cctgccatcc ctcacctctg   1800

tgtcctggaa catcagcgtg cccagagacc aggtggcctg cctgactttc tttaaggagc   1860

ggagcggcgt ggtctgccag acagggcgcg cattcatgat catccaggag cagcggaccc   1920

gggctgagga gatcttcagc ctggacgagg atgtgctccc caagccaagc ttccaccatc   1980

acagcttctg ggtcaacatc tytaaytgma gccccacgag cggcaagcag ctagacctgc   2040

tcttctcggt gacacttacc ccaaggactg tggacttgac tgtcatcctc atcgcagcgg   2100

tgggaggtgg agtcttactg ctgtctgccc tcgggctcat catttgctgt gtgaaaaaaa   2160

aaaaaarama aacaaggggc cccgctgtgg gtatctacaa tggcaacat                2209
```

<210> SEQ ID NO 170
<211> LENGTH: 709
<212> TYPE: PRT
<213> ORGANISM: Homo sapiens
<220> FEATURE:
<221> NAME/KEY: SITE
<222> LOCATION: (189)
<223> OTHER INFORMATION: Xaa equals any amino acid
<220> FEATURE:
<221> NAME/KEY: SITE
<222> LOCATION: (275)
<223> OTHER INFORMATION: Xaa equals any amino acid
<220> FEATURE:
<221> NAME/KEY: SITE
<222> LOCATION: (414)

<223> OTHER INFORMATION: Xaa equals any amino acid
<220> FEATURE:
<221> NAME/KEY: SITE
<222> LOCATION: (438)
<223> OTHER INFORMATION: Xaa equals any amino acid
<220> FEATURE:
<221> NAME/KEY: SITE
<222> LOCATION: (641)
<223> OTHER INFORMATION: Xaa equals any amino acid
<220> FEATURE:
<221> NAME/KEY: SITE
<222> LOCATION: (643)
<223> OTHER INFORMATION: Xaa equals any amino acid
<220> FEATURE:
<221> NAME/KEY: SITE
<222> LOCATION: (696)
<223> OTHER INFORMATION: Xaa equals any amino acid
<220> FEATURE:
<221> NAME/KEY: SITE
<222> LOCATION: (697)
<223> OTHER INFORMATION: Xaa equals any amino acid

<400> SEQUENCE: 170

```
Met Ala Gly Leu Asn Cys Gly Val Ser Ile Ala Leu Leu Gly Val Leu
  1               5                  10                  15

Leu Leu Gly Ala Ala Arg Leu Pro Arg Gly Ala Glu Ala Phe Glu Ile
             20                  25                  30

Ala Leu Pro Arg Glu Ser Asn Ile Thr Val Leu Ile Lys Leu Gly Thr
         35                  40                  45

Pro Thr Leu Leu Ala Lys Pro Cys Tyr Ile Val Ile Ser Lys Arg His
     50                  55                  60

Ile Thr Met Leu Ser Ile Lys Ser Gly Glu Arg Ile Val Phe Thr Phe
 65                  70                  75                  80

Ser Cys Gln Ser Pro Glu Asn His Phe Val Ile Glu Ile Gln Lys Asn
                 85                  90                  95

Ile Asp Cys Met Ser Gly Pro Cys Pro Phe Gly Glu Val Gln Leu Gln
            100                 105                 110

Pro Ser Thr Ser Leu Leu Pro Thr Leu Asn Arg Thr Phe Ile Trp Asp
        115                 120                 125

Val Lys Ala His Lys Ser Ile Gly Leu Glu Leu Gln Phe Ser Ile Pro
    130                 135                 140

Arg Leu Arg Gln Ile Gly Pro Gly Glu Ser Cys Pro Asp Gly Val Thr
145                 150                 155                 160

His Ser Ile Ser Gly Arg Ile Asp Ala Thr Val Val Arg Ile Gly Thr
                165                 170                 175

Phe Cys Ser Asn Gly Thr Val Ser Arg Ile Lys Met Xaa Glu Gly Val
            180                 185                 190

Lys Met Ala Leu His Leu Pro Trp Phe His Pro Arg Asn Val Ser Gly
        195                 200                 205

Phe Ser Ile Ala Asn Arg Ser Ser Ile Lys Arg Leu Cys Ile Ile Glu
    210                 215                 220

Ser Val Phe Glu Gly Glu Gly Ser Ala Thr Leu Met Ser Ala Asn Tyr
225                 230                 235                 240

Pro Glu Gly Phe Pro Glu Asp Glu Leu Met Thr Trp Gln Phe Val Val
                245                 250                 255

Pro Ala His Leu Arg Ala Ser Val Ser Phe Leu Asn Phe Asn Leu Ser
            260                 265                 270

Asn Cys Xaa Arg Lys Glu Glu Arg Val Glu Tyr Tyr Ile Pro Gly Ser
        275                 280                 285

Thr Thr Asn Pro Glu Val Phe Lys Leu Glu Asp Lys Gln Pro Gly Asn
    290                 295                 300
```

```
Met Ala Gly Asn Phe Asn Leu Ser Leu Gln Gly Cys Asp Gln Asp Ala
305                 310                 315                 320

Gln Ser Pro Gly Ile Leu Arg Leu Gln Phe Gln Val Leu Val Gln His
                325                 330                 335

Pro Gln Asn Glu Ser Asn Lys Ile Tyr Val Val Asp Leu Ser Asn Glu
            340                 345                 350

Arg Ala Met Ser Leu Thr Ile Glu Pro Arg Pro Val Lys Gln Ser Arg
        355                 360                 365

Lys Phe Val Pro Gly Cys Phe Val Cys Leu Glu Ser Arg Thr Cys Ser
    370                 375                 380

Ser Asn Leu Thr Leu Thr Ser Gly Ser Lys His Lys Ile Ser Phe Leu
385                 390                 395                 400

Cys Asp Asp Leu Thr Arg Leu Trp Met Asn Val Glu Lys Xaa Ile Ser
                405                 410                 415

Cys Thr Asp His Arg Tyr Cys Gln Arg Lys Ser Tyr Ser Leu Gln Val
            420                 425                 430

Pro Ser Asp Ile Leu Xaa Leu Pro Val Glu Leu His Asp Phe Ser Trp
        435                 440                 445

Lys Leu Leu Val Pro Lys Asp Arg Leu Ser Leu Val Leu Val Pro Ala
    450                 455                 460

Gln Lys Leu Gln Gln His Thr His Glu Lys Pro Cys Asn Thr Ser Phe
465                 470                 475                 480

Ser Tyr Leu Val Ala Ser Ala Ile Pro Ser Gln Asp Leu Tyr Phe Gly
                485                 490                 495

Ser Phe Cys Pro Gly Gly Ser Ile Lys Gln Ile Gln Val Lys Gln Asn
            500                 505                 510

Ile Ser Val Thr Leu Arg Thr Phe Ala Pro Ser Phe Arg Gln Glu Ala
        515                 520                 525

Ser Arg Gln Gly Leu Thr Val Ser Phe Ile Pro Tyr Phe Lys Glu Glu
    530                 535                 540

Gly Val Phe Thr Val Thr Pro Asp Thr Lys Ser Lys Val Tyr Leu Arg
545                 550                 555                 560

Thr Pro Asn Trp Asp Arg Gly Leu Pro Ser Leu Thr Ser Val Ser Trp
                565                 570                 575

Asn Ile Ser Val Pro Arg Asp Gln Val Ala Cys Leu Thr Phe Phe Lys
            580                 585                 590

Glu Arg Ser Gly Val Val Cys Gln Thr Gly Arg Ala Phe Met Ile Ile
        595                 600                 605

Gln Glu Gln Arg Thr Arg Ala Glu Glu Ile Phe Ser Leu Asp Glu Asp
    610                 615                 620

Val Leu Pro Lys Pro Ser Phe His His His Ser Phe Trp Val Asn Ile
625                 630                 635                 640

Xaa Asn Xaa Ser Pro Thr Ser Gly Lys Gln Leu Asp Leu Leu Phe Ser
                645                 650                 655

Val Thr Leu Thr Pro Arg Thr Val Asp Leu Thr Val Ile Leu Ile Ala
            660                 665                 670

Ala Val Gly Gly Gly Val Leu Leu Leu Ser Ala Leu Gly Leu Ile Ile
        675                 680                 685

Cys Cys Val Lys Lys Lys Lys Xaa Xaa Thr Arg Gly Pro Ala Val Gly
    690                 695                 700

Ile Tyr Asn Gly Asn
705
```

<210> SEQ ID NO 171
<211> LENGTH: 159
<212> TYPE: PRT
<213> ORGANISM: Homo sapiens

<400> SEQUENCE: 171

```
Phe Glu Ile Ala Leu Pro Arg Glu Ser Asn Ile Thr Val Leu Ile Lys
  1               5                  10                  15

Leu Gly Thr Pro Thr Leu Leu Ala Lys Pro Cys Tyr Ile Val Ile Ser
             20                  25                  30

Lys Arg His Ile Thr Met Leu Ser Ile Lys Ser Gly Glu Arg Ile Val
         35                  40                  45

Phe Thr Phe Ser Cys Gln Ser Pro Glu Asn His Phe Val Ile Glu Ile
     50                  55                  60

Gln Lys Asn Ile Asp Cys Met Ser Gly Pro Cys Pro Phe Gly Glu Val
 65                  70                  75                  80

Gln Leu Gln Pro Ser Thr Ser Leu Leu Pro Thr Leu Asn Arg Thr Phe
                 85                  90                  95

Ile Trp Asp Val Lys Ala His Lys Ser Ile Gly Leu Glu Leu Gln Phe
            100                 105                 110

Ser Ile Pro Arg Leu Arg Gln Ile Gly Pro Gly Glu Ser Cys Pro Asp
        115                 120                 125

Gly Val Thr His Ser Ile Ser Gly Arg Ile Asp Ala Thr Val Val Arg
    130                 135                 140

Ile Gly Thr Phe Cys Ser Asn Gly Thr Val Ser Arg Ile Lys Met
145                 150                 155
```

<210> SEQ ID NO 172
<211> LENGTH: 414
<212> TYPE: PRT
<213> ORGANISM: Homo sapiens

<400> SEQUENCE: 172

```
Met Ala Gly Leu Asn Cys Gly Val Ser Ile Ala Leu Leu Gly Val Leu
  1               5                  10                  15

Leu Leu Gly Ala Ala Arg Leu Pro Arg Gly Ala Glu Ala Phe Glu Ile
             20                  25                  30

Ala Leu Pro Arg Glu Ser Asn Ile Thr Val Leu Ile Lys Leu Gly Thr
         35                  40                  45

Pro Thr Leu Leu Ala Lys Pro Cys Tyr Ile Val Ile Ser Lys Arg His
     50                  55                  60

Ile Thr Met Leu Ser Ile Lys Ser Gly Glu Arg Ile Val Phe Thr Phe
 65                  70                  75                  80

Ser Cys Gln Ser Pro Glu Asn His Phe Val Ile Glu Ile Gln Lys Asn
                 85                  90                  95

Ile Asp Cys Met Ser Gly Pro Cys Pro Phe Gly Glu Val Gln Leu Gln
            100                 105                 110

Pro Ser Thr Ser Leu Leu Pro Thr Leu Asn Arg Thr Phe Ile Trp Asp
        115                 120                 125

Val Lys Ala His Lys Ser Ile Gly Leu Glu Leu Gln Phe Ser Ile Pro
    130                 135                 140

Arg Leu Arg Gln Ile Gly Pro Gly Glu Ser Cys Pro Asp Gly Val Thr
145                 150                 155                 160

His Ser Ile Ser Gly Arg Ile Asp Ala Thr Val Val Arg Ile Gly Thr
                165                 170                 175

Phe Cys Ser Asn Gly Thr Val Ser Arg Ile Lys Met Gln Glu Gly Val
            180                 185                 190
```

```
Lys Met Ala Leu His Leu Pro Trp Phe His Pro Arg Asn Val Ser Gly
        195                 200                 205

Phe Ser Ile Ala Asn Arg Ser Ser Ile Lys Arg Leu Cys Ile Ile Glu
    210                 215                 220

Ser Val Phe Glu Gly Glu Gly Ser Ala Thr Leu Met Ser Ala Asn Tyr
225                 230                 235                 240

Pro Glu Gly Phe Pro Glu Asp Glu Leu Met Thr Trp Gln Phe Val Val
                245                 250                 255

Pro Ala His Leu Arg Ala Ser Val Ser Phe Leu Asn Phe Asn Leu Ser
            260                 265                 270

Asn Cys Glu Arg Lys Glu Glu Arg Val Glu Tyr Tyr Ile Pro Gly Ser
        275                 280                 285

Thr Thr Asn Pro Glu Val Phe Lys Leu Glu Asp Lys Gln Pro Gly Asn
    290                 295                 300

Met Ala Gly Asn Phe Asn Leu Ser Leu Gln Gly Cys Asp Gln Asp Ala
305                 310                 315                 320

Gln Ser Pro Gly Ile Leu Arg Leu Gln Phe Gln Val Leu Val Gln His
                325                 330                 335

Pro Gln Asn Glu Ser Asn Lys Ile Tyr Val Val Asp Leu Ser Asn Glu
            340                 345                 350

Arg Ala Met Ser Leu Thr Ile Glu Pro Arg Pro Val Lys Gln Ser Arg
        355                 360                 365

Lys Phe Val Pro Gly Cys Phe Val Cys Leu Glu Ser Arg Thr Cys Ser
    370                 375                 380

Ser Asn Leu Thr Leu Thr Ser Gly Ser Lys His Lys Ile Ser Phe Leu
385                 390                 395                 400

Cys Asp Asp Leu Thr Arg Leu Trp Met Asn Val Glu Lys Pro
                405                 410
```

```
<210> SEQ ID NO 173
<211> LENGTH: 443
<212> TYPE: PRT
<213> ORGANISM: Homo sapiens

<400> SEQUENCE: 173

Gly Thr Arg Ala Ala Pro Gly Leu Gly Ala Trp Gly Arg Arg Ser Pro
  1               5                  10                  15

Pro Ser Phe Ser Pro Pro Arg Pro Arg Arg Pro Gly Val Met Ala Gly
             20                  25                  30

Leu Asn Cys Gly Val Ser Ile Ala Leu Leu Gly Val Leu Leu Leu Gly
         35                  40                  45

Ala Ala Arg Leu Pro Arg Gly Ala Glu Ala Phe Glu Ile Ala Leu Pro
     50                  55                  60

Arg Glu Ser Asn Ile Thr Val Leu Ile Lys Leu Gly Thr Pro Thr Leu
 65                  70                  75                  80

Leu Ala Lys Pro Cys Tyr Ile Val Ile Ser Lys Arg His Ile Thr Met
                 85                  90                  95

Leu Ser Ile Lys Ser Gly Glu Arg Ile Val Phe Thr Phe Ser Cys Gln
            100                 105                 110

Ser Pro Glu Asn His Phe Val Ile Glu Ile Gln Lys Asn Ile Asp Cys
        115                 120                 125

Met Ser Gly Pro Cys Pro Phe Gly Glu Val Gln Leu Gln Pro Ser Thr
    130                 135                 140

Ser Leu Leu Pro Thr Leu Asn Arg Thr Phe Ile Trp Asp Val Lys Ala
145                 150                 155                 160
```

```
His Lys Ser Ile Gly Leu Glu Leu Gln Phe Ser Ile Pro Arg Leu Arg
                165                 170                 175

Gln Ile Gly Pro Gly Glu Ser Cys Pro Asp Gly Val Thr His Ser Ile
            180                 185                 190

Ser Gly Arg Ile Asp Ala Thr Val Val Arg Ile Gly Thr Phe Cys Ser
        195                 200                 205

Asn Gly Thr Val Ser Arg Ile Lys Met Gln Glu Gly Val Lys Met Ala
    210                 215                 220

Leu His Leu Pro Trp Phe His Pro Arg Asn Val Ser Gly Phe Ser Ile
225                 230                 235                 240

Ala Asn Arg Ser Ser Ile Lys Arg Leu Cys Ile Ile Glu Ser Val Phe
                245                 250                 255

Glu Gly Glu Gly Ser Ala Thr Leu Met Ser Ala Asn Tyr Pro Glu Gly
            260                 265                 270

Phe Pro Glu Asp Glu Leu Met Thr Trp Gln Phe Val Val Pro Ala His
        275                 280                 285

Leu Arg Ala Ser Val Ser Phe Leu Asn Phe Asn Leu Ser Asn Cys Glu
    290                 295                 300

Arg Lys Glu Glu Arg Val Glu Tyr Tyr Ile Pro Gly Ser Thr Thr Asn
305                 310                 315                 320

Pro Glu Val Phe Lys Leu Glu Asp Lys Gln Pro Gly Asn Met Ala Gly
                325                 330                 335

Asn Phe Asn Leu Ser Leu Gln Gly Cys Asp Gln Asp Ala Gln Ser Pro
            340                 345                 350

Gly Ile Leu Arg Leu Gln Phe Gln Val Leu Val Gln His Pro Gln Asn
        355                 360                 365

Glu Ser Asn Lys Ile Tyr Val Val Asp Leu Ser Asn Glu Arg Ala Met
    370                 375                 380

Ser Leu Thr Ile Glu Pro Arg Pro Val Lys Gln Ser Arg Lys Phe Val
385                 390                 395                 400

Pro Gly Cys Phe Val Cys Leu Glu Ser Arg Thr Cys Ser Ser Asn Leu
                405                 410                 415

Thr Leu Thr Ser Gly Ser Lys His Lys Ile Ser Phe Leu Cys Asp Asp
            420                 425                 430

Leu Thr Arg Leu Trp Met Asn Val Glu Lys Pro
        435                 440
```

<210> SEQ ID NO 174
<211> LENGTH: 3798
<212> TYPE: DNA
<213> ORGANISM: Homo sapiens

<400> SEQUENCE: 174

```
ccacgcgtcc ggggcttcat acaggaaatc tattgctgtg tcaagttcca gagaaaagct      60

tctgttcgtc caagttacta accaggctaa accacataga cgtgaaggaa ggggctagaa     120

ggaagggagt gccccactgt tgatggggta agaggatcct gtactgagaa gttgaccaga     180

gagggtctca ccatgcgcac agttccttct gtaccagtgt ggaggaaaag tactgagtga     240

agggcagaaa aagagaaaac agaaatgctc tgcccttgga gaactgctaa cctagggcta     300

ctgttgattt tgactatctt cttagtggcc gaagcggagg gtgctgctca accaaacaac     360

tcattaatgc tgcaaactag caaggagaat catgctttag cttcaagcag tttatgtatg     420

gatgaaaaac agattacaca gaactactcg aaagtactcg cagaagttaa cacttcatgg     480

cctgtaaaga tggctacaaa tgctgtgctt tgttgccctc ctatcgcatt aagaaatttg     540
```

-continued

```
atcataataa catgggaaat aatcctgaga ggccagcctt cctgcacaaa agcctacaag    600
aaagaaacaa atgagaccaa ggaaaccaac tgtactgatg agagaataac ctgggtctcc    660
agacctgatc agaattcgga ccttcagatt cgtaccgtgg ccatcactca tgacgggtat    720
tacagatgca taatggtaac acctgatggg aatttccatc gtggatatca cctccaagtg    780
ttagttacac ctgaagtgac cctgtttcaa aacaggaata gaactgcagt atgcaaggca    840
gttgcaggga agccagctgc gcatatctcc tggatcccag agggcgattg tgccactaag    900
caagaatact ggagcaatgg cacagtgact gttaagagta catgccactg ggaggtccac    960
aatgtgtcta ccgtgaactg ccacgtctcc catttgactg gcaacaagag tctgtacata   1020
gagctacttc ctgttccagg tgccaaaaaa tcagcaaaat tatatattcc atatatcatc   1080
cttactatta ttattttgac catcgtggga ttcatttggt tgttgaaagt caatggctgc   1140
agaaaatata aattgaataa aacagaatct actccagttg ttgaggagga tgaaatgcag   1200
ccctatgcca gctacacaga gaagaacaat cctctctatg atactacaaa caaggtgaag   1260
gcatctgagg cattacaaag tgaagttgac acagacctcc atactttata agttgttgga   1320
ctctagtacc aagaaacaac aacaaacgag atacattata attactgtct gattttctta   1380
cagttctaga atgaagactt atattgaaat taggttttcc aaggttctta gaagacattt   1440
taatggattc tcattcatac ccttgtataa ttggaatttt tgattcttag ctgctaccag   1500
ctagttctct gaagaactga tgttattaca aagaaaatac atgcccatga ccaaatattc   1560
aaattgtgca ggacagtaaa taatgaaaac caaatttcct caagaaataa ctgaagaagg   1620
agcaagtgtg aacagtttct tgtgtatcct ttcagaatat tttaatgtac atatgacatg   1680
tgtatatgcc tatggtatat gtgtcaattt atgtgtcccc ttacatatac atgcacatat   1740
ctttgtcaag gcaccagtgg gaacaataca ctgcattact gttctataca tatgaaaacc   1800
taataatata agtcttagag atcattttat atcatgacaa gtagagctac ctcattcttt   1860
ttaatggtta tataaaattc cattgtatag ttatatcatt atttaattaa aaacaaccct   1920
aatgatggat atttagattc ttttaagttt tgtttatttc ttttaagttt tgtttgtggt   1980
ataaacaata ccacatagaa tgtttcttgt gcatatatct ctttgttttt gagtatatct   2040
gtaggataac tttcttgagt ggaattgtca ggtcaaaggg tttgtgcatt ttactattga   2100
tatatatgtt aaattgtgtc aaatatatat gtcaaattcc ctccaacatt gtttaaatgt   2160
gcctttccct aaatttctat tttaataact gtactattcc tgcttctaca gttgccactt   2220
tctcttttta atcaaccaga ttaaatatga tgtgagatta taataagaat tatactattt   2280
aataaaaatg gatttatatt tttggtcatg tttgtaagag agtgaatgca cgtgtgagaa   2340
cattagcttc ttctgaactc attatatctc cacagaggtg ttgatacttg atgcctaaca   2400
gttttgcaga tgtgctacat tggaattgtg tatttttatg gtgtacattc tattgtgata   2460
tatttattga ataattaatg tctattgacc atataagtgg cgaaaaaatgc accatagagg  2520
acatggggta tttatttaca aactatgagc tacataataa gcaagtggcc atgggatggc   2580
atgaccctcc cctccatatt tttgtggagc aaaatattgg caatgtttat gtaaatcatt   2640
gttaatatca tgaaattatt tttaattaaa aacataagtc tatttgctcc atagcagaaa   2700
aaacatgaga agtttttttca tcatgataga aattgaaaca aaatatattc attcttcaat  2760
cataccatct gagattttta agacagctat tttgtcttat aagtatattt ttctccctct   2820
agacatttca gttactatgg attttgtcct caaagggacc tttagtctat tttggatgta   2880
aagctaatct aatgacactt ggcacatgat attttgatca agccattttg acttgaccaa   2940
```

```
aaagcagtgt ccattaggtt tctgcatata aatattacca agcaatgttc acaatagaca   3000

tcattacact gtccttgaaa tttattaatt cttcatccaa ccctggttga gctgaggctc   3060

atagttaggt tcaagactat ctgtttaaat attactgaaa aacaaagtaa gacagtacta   3120

tgcttacctc ttaacttgat aatgtcaaaa caggcatgtt aaatgacatc atagaaaaga   3180

cttcaagata atttatagaa gttaaattat attgtacaga aaataattgt atgaaaatct   3240

ctactatggg gctggaacat ggttgaacat tagaatgata taaaaaatta tatatattct   3300

ccaaatccac gctagacctg tcaaattaga gaatctagag attagacctg gcgtgtcagc   3360

aaggtcatcc aggaagcaga ggctgagacg gagttaggtg tgattactta catagtcgat   3420

tacattttac aaataacatt ttatatgtct catttactgt gctttctccc catcccattt   3480

tgtatctttt cctttgcttt gctagatttg tcaattttct ctctctttct gtctctctct   3540

ctttcaatat ctctaataat ttgaaagtaa ttcatcataa ctaaatatct attggggtta   3600

tgcttcactt acaaacttct gaaaacggct ttactgagat ataattgata tatttaagtg   3660

tacagtttgt taaattttgc acatatttaa aatgtggact ttggtaaatg ttgacatagt   3720

tttacatctg tgaaaccatc agcataatca agataataaa cttgtccatc accccccaaa   3780

aaaaaaaaaa aaaaaaa                                                  3798
```

<210> SEQ ID NO 175
<211> LENGTH: 348
<212> TYPE: PRT
<213> ORGANISM: Homo sapiens

<400> SEQUENCE: 175

```
Met Leu Cys Pro Trp Arg Thr Ala Asn Leu Gly Leu Leu Leu Ile Leu
  1               5                  10                  15

Thr Ile Phe Leu Val Ala Glu Ala Glu Gly Ala Ala Gln Pro Asn Asn
             20                  25                  30

Ser Leu Met Leu Gln Thr Ser Lys Glu Asn His Ala Leu Ala Ser Ser
         35                  40                  45

Ser Leu Cys Met Asp Glu Lys Gln Ile Thr Gln Asn Tyr Ser Lys Val
     50                  55                  60

Leu Ala Glu Val Asn Thr Ser Trp Pro Val Lys Met Ala Thr Asn Ala
 65                  70                  75                  80

Val Leu Cys Cys Pro Pro Ile Ala Leu Arg Asn Leu Ile Ile Ile Thr
                 85                  90                  95

Trp Glu Ile Ile Leu Arg Gly Gln Pro Ser Cys Thr Lys Ala Tyr Lys
            100                 105                 110

Lys Glu Thr Asn Glu Thr Lys Glu Thr Asn Cys Thr Asp Glu Arg Ile
        115                 120                 125

Thr Trp Val Ser Arg Pro Asp Gln Asn Ser Asp Leu Gln Ile Arg Thr
    130                 135                 140

Val Ala Ile Thr His Asp Gly Tyr Tyr Arg Cys Ile Met Val Thr Pro
145                 150                 155                 160

Asp Gly Asn Phe His Arg Gly Tyr His Leu Gln Val Leu Val Thr Pro
                165                 170                 175

Glu Val Thr Leu Phe Gln Asn Arg Asn Arg Thr Ala Val Cys Lys Ala
            180                 185                 190

Val Ala Gly Lys Pro Ala Ala His Ile Ser Trp Ile Pro Glu Gly Asp
        195                 200                 205

Cys Ala Thr Lys Gln Glu Tyr Trp Ser Asn Gly Thr Val Thr Val Lys
    210                 215                 220
```

```
Ser Thr Cys His Trp Glu Val His Asn Val Ser Thr Val Asn Cys His
225                 230                 235                 240

Val Ser His Leu Thr Gly Asn Lys Ser Leu Tyr Ile Glu Leu Leu Pro
                245                 250                 255

Val Pro Gly Ala Lys Lys Ser Ala Lys Leu Tyr Ile Pro Tyr Ile Ile
            260                 265                 270

Leu Thr Ile Ile Ile Leu Thr Ile Val Gly Phe Ile Trp Leu Leu Lys
        275                 280                 285

Val Asn Gly Cys Arg Lys Tyr Lys Leu Asn Lys Thr Glu Ser Thr Pro
    290                 295                 300

Val Val Glu Glu Asp Glu Met Gln Pro Tyr Ala Ser Tyr Thr Glu Lys
305                 310                 315                 320

Asn Asn Pro Leu Tyr Asp Thr Thr Asn Lys Val Lys Ala Ser Glu Ala
                325                 330                 335

Leu Gln Ser Glu Val Asp Thr Asp Leu His Thr Leu
            340                 345


<210> SEQ ID NO 176
<211> LENGTH: 3793
<212> TYPE: DNA
<213> ORGANISM: Homo sapiens
<220> FEATURE:
<221> NAME/KEY: misc_feature
<222> LOCATION: (1102)..(1102)
<223> OTHER INFORMATION: n equals a,t,g, or c
<220> FEATURE:
<221> NAME/KEY: misc_feature
<222> LOCATION: (1132)..(1132)
<223> OTHER INFORMATION: n equals a,t,g, or c
<220> FEATURE:
<221> NAME/KEY: misc_feature
<222> LOCATION: (1199)..(1199)
<223> OTHER INFORMATION: n equals a,t,g, or c
<220> FEATURE:
<221> NAME/KEY: misc_feature
<222> LOCATION: (1228)..(1229)
<223> OTHER INFORMATION: n equals a,t,g, or c
<220> FEATURE:
<221> NAME/KEY: misc_feature
<222> LOCATION: (1231)..(1231)
<223> OTHER INFORMATION: n equals a,t,g, or c
<220> FEATURE:
<221> NAME/KEY: misc_feature
<222> LOCATION: (3176)..(3176)
<223> OTHER INFORMATION: n equals a,t,g, or c

<400> SEQUENCE: 176

ggggcttcat acaggaaatc tattgctgtg tcaagttcca gagaaaagct tctgttcgtc      60

caagttacta accaggctaa accacataga cgtgaaggaa ggggctagaa ggaagggagt     120

gccccactgt tgatggggta agaggatcct gtactgagaa gttgaccaga gagggtctca     180

ccatgcgcac agttccttct gtaccagtgt ggaggaaaag tactgagtga agggcagaaa     240

aagagaaaac agaaatgctc tgcccttgga gaactgctaa cctagggcta ctgttgattt     300

tgactatctt cttagtggcc gaagcggagg gtgctgctca accaaacaac tcattaatgc     360

tgcaaactag caaggagaat catgctttag cttcaagcag tttatgtatg gatgaaaaac     420

agattacaca gaactactcg aaagtactcg cagaagttaa cacttcatgg cctgtaaaga     480

tggctacaaa tgctgtgctt tgttgccctc ctatcgcatt aagaaatttg atcataataa     540

catgggaaat aatcctgaga ggccagcctt cctgcacaaa agcctacaag aaagaaacaa     600

atgagaccaa ggaaaccaac tgtactgatg agagaataac ctgggtctcc agacctgatc     660

agaattcgga ccttcagatt cgtaccgtgg ccatcactca tgacgggtat tacagatgca     720
```

-continued

```
taatggtaac acctgatggg aatttccatc gtggatatca cctccaagtg ttagttacac    780
ctgaagtgac cctgtttcaa aacaggaata gaactgcagt atgcaaggca gttgcaggga    840
agccagctgc gcatatctcc tggatcccag agggcgattg tgccactaag caagaatact    900
ggagcaatgg cacagtgact gttaagagta catgccactg ggaggtccac aatgtgtcta    960
ccgtgaactg ccacgtctcc catttgactg gcaacaagag tctgtacata gagctacttc   1020
ctgttccagg tgccaaaaaa tcatcaaaat tatatattcc atatatcatc cttactatta   1080
ttattttgac catcgtggga tncatttggt tgttgaaagt caatggctgc anaaaatata   1140
aattgaataa accagaatct actccagttg ttgaggagga tgaaatgcag ccctatgcnt   1200
tttacacaga gaagaacaat cctctctnng ntactacaaa caaggtgaag gcatctgagg   1260
cattacaaag tgaagttgac acagacctcc atactttata agttgttgga ctctagtacc   1320
aagaaacaac aacaaacgag atacattata attactgtct gattttctta cagttctaga   1380
atgaagactt atattgaaat taggttttcc aaggttctta gaagacattt taatggattc   1440
tcattcatac ccttgtataa ttggaatttt tgattcttag ctgctaccag ctagttctct   1500
gaagaactga tgttattaca aagaaaatac atgcccatga ccaaatattc aaattgtgca   1560
ggacagtaaa taatgaaaac caaatttcct caagaaataa ctgaagaagg agcaagtgtg   1620
aacagtttct tgtgtatcct ttcagaatat tttaatgtac atatgacatg tgtatatgcc   1680
tatggtatat gtgtcaattt atgtgtcccc ttacatatac catgcaccct atctttgtca   1740
aggcaccagt gggaacaata cactgcatta ctgttctata catatgaaaa cctaataata   1800
taagtcttag agatcatttt atatcatgac aagtagagct acctcattct ttttaatggt   1860
tatataaaat tccattgtat agttatatca ttatttaatt aaaaacaacc ctaatgatgg   1920
atatttagat tcttttaagt tttgtttatt tcttttaagt tttgtttgtg gtataaacaa   1980
taccacatag aatgtttctt gtgcatatat ctctttgttt ttgagtatat ctgtaggata   2040
actttcttga gtggaattgt caggtcaaag ggtttgtgca ttttactatt gatatatatg   2100
ttaaattgtg tcaaatatat atgtcaaatt ccctccaaca ttgtttaaat gtgcctttcc   2160
ctaaatttct attttaataa ctgtactatt cctgcttcta cagttgccac tttctctttt   2220
taatcaacca gattaaatat gatgtgagat tataataaga attatactat ttaataaaaa   2280
tggatttata tttttggtca tgtttgtaag agagtgaatg cacgtgtgag aacattagct   2340
tcttctgaac tcattatatc tccacagagg tgttgatact tgatgcctaa cagttttgca   2400
gatgtgctac attggaattg tgtattttta tggtgtacat tctattgtga tatatttatt   2460
gaataattaa tgtctattga ccatataagt ggcgaaaaat gcaccataga ggacatgggg   2520
tatttattta caaactatga gctacataat aagcaagtgg ccatgggatg gcatgaccct   2580
cccctccata tttttgtgga gcaaaatatt ggcaatgttt atgtaaatca ttgttaatat   2640
catgaaatta tttttaatta aaaacataag tctatttgct ccatagcaga aaaaacatga   2700
gaagtttttt catcatgata gaaattgaaa caaaatatat tcattcttca atcataccat   2760
ctgagatttt taagacagct attttgtctt ataagtatat ttttctccct ctagacattt   2820
cagttactat ggattttgtc ctcaaaggga cytttagtct aattttggga tgtaaagcta   2880
atcttaatga cacttggcac atgatatttt gatcaagcca ttttgacttg accaaaaagc   2940
agtgtccatt aggtttctgc atataaatat taccaagcaa tgttcacaat agacatcatt   3000
acactgtcct tgaaatttat taattcttca tccaaccctg gttgagctga ggctcatagt   3060
taggttcaag actatctgtt taaatattac tgaaaaacaa agtaagacag tactatgctt   3120
```

```
acctcttaac ttgataatgt caaaccaggc atgttaaatg acatcataga aaaganttca   3180

agataattta tagaagttaa attatattgt acagaaaata attgtatgaa aatctctact   3240

atggggctgg aacatggttg aacattagaa tgatataaaa aattatatat attctccaaa   3300

tccacgctag acctgtcaaa ttagagaatc tagagattag acctggcgtg tcagcaaggt   3360

catccaggaa gcagaggctg agacggagtt aggtgtgatt acttacatag tcgattacat   3420

tttacaaata acattttata tgtctcattt actgtgcttt ctccccatcc cattttgtat   3480

cttttccttt gctttgctag atttgtcaat tttctctctc tttctgtctc tctctctttc   3540

aatatctcta ataatttgaa agtaattcat cataactaaa tatctattgg ggttatgctt   3600

cacttacaaa cttctgaaaa cggctttact gagatataat tgatatattt aagtgtacag   3660

tttgttaaat tttgcacata tttaaaatgt ggactttggt aaatgttgac atagttttac   3720

atctgtgaaa ccatcagcat aatcaagata ataaacttgt ccatcacccc ccaaaaaaaa   3780

aaaaaaaaaa aaa                                                      3793
```

<210> SEQ ID NO 177
<211> LENGTH: 348
<212> TYPE: PRT
<213> ORGANISM: Homo sapiens
<220> FEATURE:
<221> NAME/KEY: SITE
<222> LOCATION: (283)
<223> OTHER INFORMATION: Xaa equals any amino acid
<220> FEATURE:
<221> NAME/KEY: SITE
<222> LOCATION: (293)
<223> OTHER INFORMATION: Xaa equals any amino acid
<220> FEATURE:
<221> NAME/KEY: SITE
<222> LOCATION: (325)
<223> OTHER INFORMATION: Xaa equals any amino acid
<220> FEATURE:
<221> NAME/KEY: SITE
<222> LOCATION: (326)
<223> OTHER INFORMATION: Xaa equals any amino acid

<400> SEQUENCE: 177

```
Met Leu Cys Pro Trp Arg Thr Ala Asn Leu Gly Leu Leu Leu Ile Leu
  1               5                  10                  15

Thr Ile Phe Leu Val Ala Glu Ala Glu Gly Ala Ala Gln Pro Asn Asn
             20                  25                  30

Ser Leu Met Leu Gln Thr Ser Lys Glu Asn His Ala Leu Ala Ser Ser
         35                  40                  45

Ser Leu Cys Met Asp Glu Lys Gln Ile Thr Gln Asn Tyr Ser Lys Val
     50                  55                  60

Leu Ala Glu Val Asn Thr Ser Trp Pro Val Lys Met Ala Thr Asn Ala
 65                  70                  75                  80

Val Leu Cys Cys Pro Pro Ile Ala Leu Arg Asn Leu Ile Ile Ile Thr
                 85                  90                  95

Trp Glu Ile Ile Leu Arg Gly Gln Pro Ser Cys Thr Lys Ala Tyr Lys
            100                 105                 110

Lys Glu Thr Asn Glu Thr Lys Glu Thr Asn Cys Thr Asp Glu Arg Ile
        115                 120                 125

Thr Trp Val Ser Arg Pro Asp Gln Asn Ser Asp Leu Gln Ile Arg Thr
    130                 135                 140

Val Ala Ile Thr His Asp Gly Tyr Tyr Arg Cys Ile Met Val Thr Pro
145                 150                 155                 160

Asp Gly Asn Phe His Arg Gly Tyr His Leu Gln Val Leu Val Thr Pro
```

```
                165                 170                 175

Glu Val Thr Leu Phe Gln Asn Arg Asn Arg Thr Ala Val Cys Lys Ala
            180                 185                 190

Val Ala Gly Lys Pro Ala Ala His Ile Ser Trp Ile Pro Glu Gly Asp
        195                 200                 205

Cys Ala Thr Lys Gln Glu Tyr Trp Ser Asn Gly Thr Val Thr Val Lys
    210                 215                 220

Ser Thr Cys His Trp Glu Val His Asn Val Ser Thr Val Asn Cys His
225                 230                 235                 240

Val Ser His Leu Thr Gly Asn Lys Ser Leu Tyr Ile Glu Leu Leu Pro
                245                 250                 255

Val Pro Gly Ala Lys Lys Ser Ser Lys Leu Tyr Ile Pro Tyr Ile Ile
            260                 265                 270

Leu Thr Ile Ile Ile Leu Thr Ile Val Gly Xaa Ile Trp Leu Leu Lys
        275                 280                 285

Val Asn Gly Cys Xaa Lys Tyr Lys Leu Asn Lys Pro Glu Ser Thr Pro
    290                 295                 300

Val Val Glu Glu Asp Glu Met Gln Pro Tyr Ala Phe Tyr Thr Glu Lys
305                 310                 315                 320

Asn Asn Pro Leu Xaa Xaa Thr Thr Asn Lys Val Lys Ala Ser Glu Ala
                325                 330                 335

Leu Gln Ser Glu Val Asp Thr Asp Leu His Thr Leu
            340                 345


<210> SEQ ID NO 178
<211> LENGTH: 348
<212> TYPE: PRT
<213> ORGANISM: Homo sapiens
<220> FEATURE:
<221> NAME/KEY: SITE
<222> LOCATION: (283)
<223> OTHER INFORMATION: Xaa equals any of the naturally occurring
      L-amino acids
<220> FEATURE:
<221> NAME/KEY: SITE
<222> LOCATION: (293)
<223> OTHER INFORMATION: Xaa equals any of the naturally occurring
      L-amino acids
<220> FEATURE:
<221> NAME/KEY: SITE
<222> LOCATION: (325)
<223> OTHER INFORMATION: Xaa equals any of the naturally occurring
      L-amino acids
<220> FEATURE:
<221> NAME/KEY: SITE
<222> LOCATION: (326)
<223> OTHER INFORMATION: Xaa equals any of the naturally occurring
      L-amino acids

<400> SEQUENCE: 178

Met Leu Cys Pro Trp Arg Thr Ala Asn Leu Gly Leu Leu Leu Ile Leu
  1               5                  10                  15

Thr Ile Phe Leu Val Ala Glu Ala Glu Gly Ala Ala Gln Pro Asn Asn
             20                  25                  30

Ser Leu Met Leu Gln Thr Ser Lys Glu Asn His Ala Leu Ala Ser Ser
         35                  40                  45

Ser Leu Cys Met Asp Glu Lys Gln Ile Thr Gln Asn Tyr Ser Lys Val
     50                  55                  60

Leu Ala Glu Val Asn Thr Ser Trp Pro Val Lys Met Ala Thr Asn Ala
 65                  70                  75                  80

Val Leu Cys Cys Pro Pro Ile Ala Leu Arg Asn Leu Ile Ile Ile Thr
                 85                  90                  95
```

```
Trp Glu Ile Ile Leu Arg Gly Gln Pro Ser Cys Thr Lys Ala Tyr Lys
            100                 105                 110

Lys Glu Thr Asn Glu Thr Lys Glu Thr Asn Cys Thr Asp Glu Arg Ile
        115                 120                 125

Thr Trp Val Ser Arg Pro Asp Gln Asn Ser Asp Leu Gln Ile Arg Thr
    130                 135                 140

Val Ala Ile Thr His Asp Gly Tyr Tyr Arg Cys Ile Met Val Thr Pro
145                 150                 155                 160

Asp Gly Asn Phe His Arg Gly Tyr His Leu Gln Val Leu Val Thr Pro
                165                 170                 175

Glu Val Thr Leu Phe Gln Asn Arg Asn Arg Thr Ala Val Cys Lys Ala
            180                 185                 190

Val Ala Gly Lys Pro Ala Ala His Ile Ser Trp Ile Pro Glu Gly Asp
        195                 200                 205

Cys Ala Thr Lys Gln Glu Tyr Trp Ser Asn Gly Thr Val Thr Val Lys
    210                 215                 220

Ser Thr Cys His Trp Glu Val His Asn Val Ser Thr Val Asn Cys His
225                 230                 235                 240

Val Ser His Leu Thr Gly Asn Lys Ser Leu Tyr Ile Glu Leu Leu Pro
                245                 250                 255

Val Pro Gly Ala Lys Lys Ser Ser Lys Leu Tyr Ile Pro Tyr Ile Ile
            260                 265                 270

Leu Thr Ile Ile Ile Leu Thr Ile Val Gly Xaa Ile Trp Leu Leu Lys
        275                 280                 285

Val Asn Gly Cys Xaa Lys Tyr Lys Leu Asn Lys Pro Glu Ser Thr Pro
    290                 295                 300

Val Val Glu Glu Asp Glu Met Gln Pro Tyr Ala Phe Tyr Thr Glu Lys
305                 310                 315                 320

Asn Asn Pro Leu Xaa Xaa Thr Thr Asn Lys Val Lys Ala Ser Glu Ala
                325                 330                 335

Leu Gln Ser Glu Val Asp Thr Asp Leu His Thr Leu
            340                 345
```

<210> SEQ ID NO 179
<211> LENGTH: 1796
<212> TYPE: DNA
<213> ORGANISM: Homo sapiens

<400> SEQUENCE: 179

```
ggaaggagga agttcaaggg cgagartrag taccagcaga aggctgggag tctgtagttt      60

gttcctgctg ccaggctcca ctgaggggaa cggggacctg tctgaagaga agatgcccct     120

gctgacactc tacctgctcc tcttctggct ctcaggctac tccattgcca ctcaaatcac     180

cggtccaaca acagtgaatg gcttggagcg gggctccttg accgtgcagt gtgtttacag     240

atcaggctgg gagacctact tgaagtggtg gtgtcgagga gctatttggc gtgactgcaa     300

gatccttgtt aaaaccagtg ggtcagagca ggaggtgaag agggaccggg tgtccatcaa     360

ggacaatcag aaaaaccgca cgttcactgt gaccatggag gatctcatga aaactgatgc     420

tgacacttac tggtgtggaa ttgagaaaac tggaaatgac cttggggtca cagttcaagt     480

gaccattgac ccagcaccag tcacccaaga agaaactagc agctccccaa ctctgaccgg     540

ccaccacttg gacaacaggc acaagctcct gaagctcagt gtcctcctgc ccctcatctt     600

caccatattk ytgytgcttt tggtggccgc ctcactcttg gcttggagga tgatgaagta     660

ccagcagaaa gcagccggga tgtccccaga gcaggtactg cagcccctgg agggcgacct     720
```

-continued

```
ctgctatgca gacctgaccc tgcagctggc cggaacctcc ccgcgaaagg ctaccacgaa    780
gctttcctct gcccaggttg accaggtgga agtggaatat gtcaccatgg cttccttgcc    840
gaaggaggac atttcctatg catctctgac cttgggtgct gaggatcagg aaccgaccta    900
ctgcaacatg ggccamctca gtagccamct ycccggcagg ggccctgagg agcccacgga    960
atacagcacc atcagcaggc cttagcctgc actccaggct ccttcttgga ccccaggctg   1020
tgagcacact cctgcctcat cgaccgtctg ccccctgctc ccctcatcag gaccaacccg   1080
gggactggtg cctctgcctg atcagccagc attgccccta gctctgggtt gggcttgggg   1140
ccaagtctca gggggcttct aggagttggg gttttctaaa cgtcccctcc tctctacata   1200
gttgaggagg gggctaggga tatgctctgg ggctttcatg ggaatgatga agatgataat   1260
gagaaaaatg ttatcattat tatcatgaag taccattatc ataatacaat gaacctttat   1320
ttattgccta ccacatgtta tgggctgaat aatggccccc aaagatatct gtgtcctaat   1380
cctcagaact tgtgactgtt accttctgtg gcagaaaggg acagtgcaga tgtatgtaag   1440
ttaaggactt tgagatagag aggttattct tgctgattca ggtgggccca aaatatcacc   1500
acaagggtcc tcataagaaa gaggccagaa ggtcaaagag gtagagacaa agtgatgatg   1560
gaagtggacg tgggtgtgac gtgagcaggg gccatgaatg ccgcagcctt cagatgccag   1620
aaagggaaag gaatggattc ccctgcctgg agcctccaaa agaaaccagc cctgcccacg   1680
ccttgacttg agcccattga aactgatctt gagctcctgg cctccagaat tgcaggagaa   1740
taaatttgtg ttgtttttaa tgaaaaaaaa aaaaaaaaaa aaaaaagggc ggccgc       1796
```

```
<210> SEQ ID NO 180
<211> LENGTH: 290
<212> TYPE: PRT
<213> ORGANISM: Homo sapiens
<220> FEATURE:
<221> NAME/KEY: SITE
<222> LOCATION: (166)
<223> OTHER INFORMATION: Xaa equals any amino acid
<220> FEATURE:
<221> NAME/KEY: SITE
<222> LOCATION: (268)
<223> OTHER INFORMATION: Xaa equals any amino acid
<220> FEATURE:
<221> NAME/KEY: SITE
<222> LOCATION: (272)
<223> OTHER INFORMATION: Xaa equals any amino acid

<400> SEQUENCE: 180

Met Pro Leu Leu Thr Leu Tyr Leu Leu Leu Phe Trp Leu Ser Gly Tyr
  1               5                  10                  15

Ser Ile Ala Thr Gln Ile Thr Gly Pro Thr Thr Val Asn Gly Leu Glu
             20                  25                  30

Arg Gly Ser Leu Thr Val Gln Cys Val Tyr Arg Ser Gly Trp Glu Thr
         35                  40                  45

Tyr Leu Lys Trp Trp Cys Arg Gly Ala Ile Trp Arg Asp Cys Lys Ile
     50                  55                  60

Leu Val Lys Thr Ser Gly Ser Glu Gln Glu Val Lys Arg Asp Arg Val
 65                  70                  75                  80

Ser Ile Lys Asp Asn Gln Lys Asn Arg Thr Phe Thr Val Thr Met Glu
                 85                  90                  95

Asp Leu Met Lys Thr Asp Ala Asp Thr Tyr Trp Cys Gly Ile Glu Lys
            100                 105                 110

Thr Gly Asn Asp Leu Gly Val Thr Val Gln Val Thr Ile Asp Pro Ala
        115                 120                 125
```

-continued

Pro Val Thr Gln Glu Glu Thr Ser Ser Ser Pro Thr Leu Thr Gly His
    130                 135                 140

His Leu Asp Asn Arg His Lys Leu Leu Lys Leu Ser Val Leu Leu Pro
145                 150                 155                 160

Leu Ile Phe Thr Ile Xaa Leu Leu Leu Leu Val Ala Ala Ser Leu Leu
                165                 170                 175

Ala Trp Arg Met Met Lys Tyr Gln Gln Lys Ala Ala Gly Met Ser Pro
            180                 185                 190

Glu Gln Val Leu Gln Pro Leu Glu Gly Asp Leu Cys Tyr Ala Asp Leu
        195                 200                 205

Thr Leu Gln Leu Ala Gly Thr Ser Pro Arg Lys Ala Thr Thr Lys Leu
    210                 215                 220

Ser Ser Ala Gln Val Asp Gln Val Glu Val Glu Tyr Val Thr Met Ala
225                 230                 235                 240

Ser Leu Pro Lys Glu Asp Ile Ser Tyr Ala Ser Leu Thr Leu Gly Ala
                245                 250                 255

Glu Asp Gln Glu Pro Thr Tyr Cys Asn Met Gly Xaa Leu Ser Ser Xaa
            260                 265                 270

Leu Pro Gly Arg Gly Pro Glu Glu Pro Thr Glu Tyr Ser Thr Ile Ser
        275                 280                 285

Arg Pro
    290

<210> SEQ ID NO 181
<211> LENGTH: 37
<212> TYPE: PRT
<213> ORGANISM: Homo sapiens
<220> FEATURE:
<221> NAME/KEY: SITE
<222> LOCATION: (9)
<223> OTHER INFORMATION: Xaa equals any of the naturally occurring
      L-amino acids

<400> SEQUENCE: 181

Glu Gly Gly Ser Ser Arg Ala Arg Xaa Ser Thr Ser Arg Arg Leu Gly
  1               5                  10                  15

Val Cys Ser Leu Phe Leu Leu Pro Gly Ser Thr Glu Gly Asn Gly Asp
            20                  25                  30

Leu Ser Glu Glu Lys
        35

<210> SEQ ID NO 182
<211> LENGTH: 2738
<212> TYPE: DNA
<213> ORGANISM: Homo sapiens

<400> SEQUENCE: 182
gggtcgaccc acgcgtccga ggcatctcta ggtaccatcc ctgacctggt cctcatgctg 60
ccgaggctgt tgctgttgat ctgtgctcca ctctgtgaac ctgccggggt ccctgtcgct 120
gatgtgagct tggagactca gcccccagga ggacaggtga tggagggaga caggctggtc 180
ctcatctgct cagttgctat gggcacagga gacatcacct tcctttggta caaaggggct 240
gtaggtttaa accttcagtc aaagacccag cgttcactga cagcagagta tgagattcct 300
tcagtgaggg agagtgatgc tgagcaatat tactgtgtag ctgaaaatgg ctatggtccc 360
agccccagtg ggctggtgag catcactgtc agaatcccgg tgtctcgccc aatcctcatg 420
ctcagggctc ccagggccca ggctgcagtg gaggatgtgc tggagcttca ctgtgaggcc 480

```
ctgagaggct ctcctccgat cctgtactgg ttttatcacg aggatatcac cctggggagc    540
aggtcggccc cctctggagg aggagcctcc ttcaaccttt ccctgactga agaacattct    600
ggaaactact cctgtgaggc caacaatggc ctgggggccc agcgcagtga ggcggtgaca    660
ctcaacttca caggaagacg ttcagccagg gatccactca ggagccttcc cagccctcta    720
ccccaagagt tcacctacct caactcacct accccagggc agctacagcc tatatatgaa    780
aatgtgaatg ttgtaagtgg ggatgaggtt tattcactgg cgtactataa ccagccggag    840
caggaatcag tagcagcaga aaccctgggg acacatatgg aggacaaggt ttccttagac    900
atctattcca ggctgaggaa agcaaacatt acagatgtgg actatgaaga tgctatgtaa    960
ggttatggaa gattctgctc tttgaaaacc atccatgacc ccaagcctca ggcctgatat   1020
gttcttcaga gatcctgggg cattagcttt ccagtatacc tcttctggat gccattctcc   1080
atggcactat tccttcatct actgtgaagt gaagttggcg cagccctgaa gaaactacct   1140
aggagaacta atagacacag gagtgacagg gactttgtta tcagaaccag attcctgccg   1200
gctcctttga aaacaggtca tattgtgctc ttctgtttac aagaggaaac aagatggaat   1260
aaaagaaatt gggatcttgg gttggaggga cagtgaagct tagagcacat gaactcaagg   1320
ttagtgactc tgcaggactt cacagagaga gctgtgccca tcattcagtc caagtgcttt   1380
ctctgcccag acagcacaga actccagccc cgctacttac atggatcatc gagtttccac   1440
ctaaaatatg attctattta ttttgagtca ctgttaccaa attagaacta aaacaaagtt   1500
acataaaaag ttattgtgac tccacttaat tttagtgacg tatttttgta tatataggcc   1560
aacctatacc acatccaaaa ttatgtatct attacagccc ctagaagctt tataaataca   1620
gtgtgtcttc ttttattcac aaaatttttg aaatcgtggt aatatggttt gaaacctgta   1680
tcttaattat ttttttttta aattgagaca gggtctcact ctgtcactca atctggaatg   1740
cagtggcaca atcttgcctc actgcaacgc ctgcctctca ggctcaagca aacctctcac   1800
ctcagcctgc tgagtagctg ggactacagg cacatgccac caaacttggc catttttttgt  1860
cttacgtaga gacaagattt caccgttttg cccaggctgg tctcaaactc ctgggctcaa   1920
gcaatgtatt gaattttaaa ataaccaggc actcactctt atgaattaat aaacatttgg   1980
aggtatataa agtaaaaagt taaagtcttt cctgtaagtt aacacaaatg ttaactattg   2040
ttaaaaactt tacaggtagc tctctagata tttttctatt tttgtatgta tacttatgca   2100
tacatgtaag tatataaaca tttagaagtg tacctatcta acaaactatt atgaaatact   2160
ttcaaatctg taaatagatc tattatacta ttttaaaagt ctctatagta gtgtgttata   2220
tagataaatc ataacttttt tcttttttta ttgtagtaaa tatgcacaac ataaaattga   2280
tcattttaac catttttaag tgtacaattc agtggcatta agtactatca taatatattt   2340
taatccttct catcactggt ggacattaag gagactctca aaaaattcat attataaaaa   2400
caaagttcaa acaaatgtct ttgtactagc atattatggc actcctgctg gattatctga   2460
aggataaatt tgtaaatcta gtattgctag attatgcata ttaaatattc ttgttaaata   2520
gtcttcaatg tctctcaggt aaggctgtat caatttatat cttcaccaac aacgtctggg   2580
aaatcagttt gtggggtgta ttacttagtt ttcacattgc taataaagac atatccaaga   2640
ctgggaaaaa aaaaaaaaaa aaaaaaaaaa aaaaaaaaaa aagggcggcc gctctagagg   2700
atccctcgag ggcccaagc ttacgcgtgc atgcgacg                             2738
```

<210> SEQ ID NO 183
<211> LENGTH: 301
<212> TYPE: PRT

<213> ORGANISM: Homo sapiens

<400> SEQUENCE: 183

```
Met Leu Pro Arg Leu Leu Leu Leu Ile Cys Ala Pro Leu Cys Glu Pro
  1               5                  10                  15

Ala Gly Val Pro Val Ala Asp Val Ser Leu Glu Thr Gln Pro Pro Gly
             20                  25                  30

Gly Gln Val Met Glu Gly Asp Arg Leu Val Leu Ile Cys Ser Val Ala
         35                  40                  45

Met Gly Thr Gly Asp Ile Thr Phe Leu Trp Tyr Lys Gly Ala Val Gly
     50                  55                  60

Leu Asn Leu Gln Ser Lys Thr Gln Arg Ser Leu Thr Ala Glu Tyr Glu
 65                  70                  75                  80

Ile Pro Ser Val Arg Glu Ser Asp Ala Glu Gln Tyr Tyr Cys Val Ala
                 85                  90                  95

Glu Asn Gly Tyr Gly Pro Ser Pro Ser Gly Leu Val Ser Ile Thr Val
            100                 105                 110

Arg Ile Pro Val Ser Arg Pro Ile Leu Met Leu Arg Ala Pro Arg Ala
        115                 120                 125

Gln Ala Ala Val Glu Asp Val Leu Glu Leu His Cys Glu Ala Leu Arg
    130                 135                 140

Gly Ser Pro Pro Ile Leu Tyr Trp Phe Tyr His Glu Asp Ile Thr Leu
145                 150                 155                 160

Gly Ser Arg Ser Ala Pro Ser Gly Gly Gly Ala Ser Phe Asn Leu Ser
                165                 170                 175

Leu Thr Glu Glu His Ser Gly Asn Tyr Ser Cys Glu Ala Asn Asn Gly
            180                 185                 190

Leu Gly Ala Gln Arg Ser Glu Ala Val Thr Leu Asn Phe Thr Gly Arg
        195                 200                 205

Arg Ser Ala Arg Asp Pro Leu Arg Ser Leu Pro Ser Pro Leu Pro Gln
    210                 215                 220

Glu Phe Thr Tyr Leu Asn Ser Pro Thr Pro Gly Gln Leu Gln Pro Ile
225                 230                 235                 240

Tyr Glu Asn Val Asn Val Val Ser Gly Asp Glu Val Tyr Ser Leu Ala
                245                 250                 255

Tyr Tyr Asn Gln Pro Glu Gln Glu Ser Val Ala Ala Glu Thr Leu Gly
            260                 265                 270

Thr His Met Glu Asp Lys Val Ser Leu Asp Ile Tyr Ser Arg Leu Arg
        275                 280                 285

Lys Ala Asn Ile Thr Asp Val Asp Tyr Glu Asp Ala Met
    290                 295                 300
```

<210> SEQ ID NO 184
<211> LENGTH: 729
<212> TYPE: DNA
<213> ORGANISM: Homo sapiens

<400> SEQUENCE: 184

```
tctgaggtgc attctttttt tgatgagagg catctctagg taccatccct gacctggtcc      60

tcatgctgcc gaggctgttg ctgttgatct gtgctccact ctgtgaacct gccggggtcc     120

ctgtcgctga tgtgagcttg gagactcakc ccccakgagg acaggtgatg gagggagaca     180

ggctggtcct catctgctca gttgctatgg gcacaggaga catcaccttc ctttggtaca     240

aaggggctgt aggtttaaac cttcagtcaa agacccagcg ttcactgaca gcagagtatg     300

agattccttc agtgagggag agtgatgctg agcaatatta ctgtgtagct gaaaatggct     360
```

```
atggtcccag ccccagtggg ctggtgagca tcactgtcag aatcccggtg tctcgcccaa    420

tcctcatgct cagggctccc agggcccagg ctgcagtgga ggatgtgctg gagcttcact    480

gtgaggccct gagaggctct cctccratcc tgtactggtt ttatcacgag gatatcaccc    540

tggggagcag gtcggccccc tctggaggag gagcctcctt caacctttcc ctgactgaag    600

aacattctgg aaactactcc tgtgaggcca acaagtgcct gggggcccag cgcagtgagg    660

cggkgacact caacttcaca gtgcctactg ggccagaag caatcatctt acctcaggag    720

tcattgagg                                                            729
```

```
<210> SEQ ID NO 185
<211> LENGTH: 222
<212> TYPE: PRT
<213> ORGANISM: Homo sapiens
<220> FEATURE:
<221> NAME/KEY: SITE
<222> LOCATION: (29)
<223> OTHER INFORMATION: Xaa equals any of the naturally occurring
      L-amino acids
<220> FEATURE:
<221> NAME/KEY: SITE
<222> LOCATION: (32)
<223> OTHER INFORMATION: Xaa equals any of the naturally occurring
      L-amino acids
<220> FEATURE:
<221> NAME/KEY: SITE
<222> LOCATION: (201)
<223> OTHER INFORMATION: Xaa equals any of the naturally occurring
      L-amino acids

<400> SEQUENCE: 185

Met Leu Pro Arg Leu Leu Leu Leu Ile Cys Ala Pro Leu Cys Glu Pro
  1               5                  10                  15

Ala Gly Val Pro Val Ala Asp Val Ser Leu Glu Thr Xaa Pro Pro Xaa
             20                  25                  30

Gly Gln Val Met Glu Gly Asp Arg Leu Val Leu Ile Cys Ser Val Ala
         35                  40                  45

Met Gly Thr Gly Asp Ile Thr Phe Leu Trp Tyr Lys Gly Ala Val Gly
     50                  55                  60

Leu Asn Leu Gln Ser Lys Thr Gln Arg Ser Leu Thr Ala Glu Tyr Glu
 65                  70                  75                  80

Ile Pro Ser Val Arg Glu Ser Asp Ala Glu Gln Tyr Tyr Cys Val Ala
                 85                  90                  95

Glu Asn Gly Tyr Gly Pro Ser Pro Ser Gly Leu Val Ser Ile Thr Val
            100                 105                 110

Arg Ile Pro Val Ser Arg Pro Ile Leu Met Leu Arg Ala Pro Arg Ala
        115                 120                 125

Gln Ala Ala Val Glu Asp Val Leu Glu Leu His Cys Glu Ala Leu Arg
    130                 135                 140

Gly Ser Pro Pro Ile Leu Tyr Trp Phe Tyr His Glu Asp Ile Thr Leu
145                 150                 155                 160

Gly Ser Arg Ser Ala Pro Ser Gly Gly Gly Ala Ser Phe Asn Leu Ser
                165                 170                 175

Leu Thr Glu Glu His Ser Gly Asn Tyr Ser Cys Glu Ala Asn Lys Cys
            180                 185                 190

Leu Gly Ala Gln Arg Ser Glu Ala Xaa Thr Leu Asn Phe Thr Val Pro
        195                 200                 205

Thr Gly Ala Arg Ser Asn His Leu Thr Ser Gly Val Ile Glu
    210                 215                 220
```

<210> SEQ ID NO 186
<211> LENGTH: 4995
<212> TYPE: DNA
<213> ORGANISM: Homo sapiens

<400> SEQUENCE: 186
gccgcgccga ggaggctgcc gctctggctt gccgcccccc gccgccgctg cacaccggac 60
ccagccgccg tgccgcgggc catggacctg cccaggggcc tggtggtggc ctgggcgctc 120
agcctgtggc cagggttcac ggacaccttc aacatggaca ccaggaagcc ccgggtcatc 180
cctggctcca ggaccgcctt ctttggctac acagtgcagc agcacgacat cagtggcaat 240
aagtggctgg tcgtgggcgc ccccactggaa accaatggct accagaagac gggagacgtg 300
tacaagtgtc cagtgatcca cgggaactgc accaaactca acctgggaag ggtcaccctg 360
tccaacgtgt ccgagcggaa agacaacatg cgcctcggcc ttagtctcgc caccaacccc 420
aaggacaaca gcttcctggc ctgcagcccc ctctggtctc atgagtgtgg gagctcctac 480
tacaccacag ggatgtgttc aagagtcaac tccaacttca ggttctccaa gaccgtggcc 540
ccagctctcc aaaggtgcca gacctacatg gacatcgtca ttgtcctgga tggctccaac 600
agcatctacc cctgggtgga ggttcagcac ttcctcatca acatcctgaa aaagttttac 660
attggcccag ggcagatcca ggttggagtt gtgcagtatg gcgaagatgt ggtgcatgag 720
tttcacctca atgactacag gtctgtaaaa gatgtggtgg aagctgccag ccacattgag 780
cagagaggag gaacagagac ccggacggca tttggcattg aatttgcacg ctcagaggct 840
ttccagaagg gtggaaggaa aggagccaag aaggtgatga ttgtcatcac agatggggag 900
tcccacgaca gcccagacct ggagaaggtg atccagcaaa gcgaaagaga caacgtaaca 960
agatatgcgg tggccgtcct gggctactac aaccgcaggg ggatcaatcc agaaactttt 1020
ctaaatgaaa tcaaatacat cgccagtgac cctgatgaca agcacttctt caatgtcact 1080
gatgaggctg ccttgaagga cattgtcgat gccctggggg acagaatctt cagcctggaa 1140
ggcaccaaca agaacgagac ctcctttggg ctggagatgt cacagacggg cttttcctcg 1200
cacgtggtgg aggatggggt tctgctggga gccgtcggtg cctatgactg gaatggagct 1260
gtgctaaagg agacgagtgc cgggaaggtc attcctctcc gcgagtccta cctgaaagag 1320
ttccccgagg agctcaagaa ccatggtgca tacctggggt acacagtcac atcggtcgtg 1380
tcctccaggc aggggcgagt gtacgtggcc ggagcccccc ggttcaacca cacgggcaag 1440
gtcatcctgt tcaccatgca caacaaccgg agcctcacca tccaccaggc tatgcggggc 1500
cagcagatag gctcttactt tgggagtgaa atcacctcgg tggacatcga cggcgacggc 1560
gtgactgatg tcctgctggt gggcgcaccc atgtacttca acgagggccg tgagcgaggc 1620
aaggtgtacg tctatgagct gagacagaac cggtttgttt ataacggaac gctaaaggat 1680
tcacacagtt accagaatgc ccgatttggg tcctccattg cctcagttcg agacctcaac 1740
caggattcct acaatgacgt ggtggtggga gccccccctgg aggacaacca cgcaggagcc 1800
atctacatct tccacggctt ccgaggcagc atcctgaaga cacctaagca gagaatcaca 1860
gcctcagagc tggctaccgg cctccagtat tttggctgca gcatccacgg gcaattggac 1920
ctcaatgagg atgggctcat cgacctggca gtgggagccc ttggcaacgc tgtgattctg 1980
tggtcccgcc cagtggttca gatcaatgcc agcctccact ttgagccatc caagatcaac 2040
atcttccaca gagactgcaa gcgcagtggc agggatgcca cctgcctggc cgccttcctc 2100
tgcttcacgc ccatcttcct ggcaccccat ttccaaacaa caactgttgg catcagatac 2160

```
aacgccacca tggatgagag gcggtataca ccgagggccc acctggacga gggcggggac   2220
cgattcacca acagagccgt actgctctcc tccggccagg agctctgtga gcggatcaac   2280
ttccatgtcc tggacactgc tgactacgtg aagccagtga ccttctcagt cgagtattcc   2340
ctggaggacc ctgaccatgg ccccatgctg gacgacggct ggcccaccac tctcagagtc   2400
tcggtgccct tctggaacgg ctgcaatgag gatgagcact gtgtccctga ccttgtgttg   2460
gatgcccgga gtgacctgcc cacggccatg gagtactgcc agagggtgct gaggaagcct   2520
gcgcaggact gctccgcata cacgctgtcc ttcgacacca cagtcttcat catagagagc   2580
acacgccagc gagtggcggt ggaggccaca ctggagaaca ggggcgagaa cgcctacagc   2640
acggtcctaa atatctcgca gtcagcaaac ctgcagtttg ccagcttgat ccagaaggag   2700
gactcagacg gtagcattga gtgtgtgaac gaggagagga ggctccagaa gcaagtctgc   2760
aacgtcagct atcccttctt ccgggccaag gccaaggtgg ctttccgtct tgattttgag   2820
ttcagcaaat ccatcttcct acaccacctg gagatcgagc tcgctgcagg cagtgacagt   2880
aatgagcggg acagcaccaa ggaagacaac gtggcccccct tacgcttcca cctcaaatac   2940
gaggctgacg tcctcttcac caggagcagc agcctgagcc actacgaggt caagctcaac   3000
agctcgctgg agagatacga tggtatcggg cctcccttca gctgcatctt caggatccag   3060
aacttgggct tgttccccat ccacgggatt atgatgaaga tcaccattcc catcgccacc   3120
aggagcggca accgcctact gaagctgagg gacttcctca cggacgaggt agcgaacacg   3180
tcctgtaaca tctggggcaa tagcactgag taccggccca ccccagtgga ggaagacttg   3240
cgtcgtgctc cacagctgaa tcacagcaac tctgatgtcg tctccatcaa ctgcaatata   3300
cggctggtcc ccaaccagga aatcaatttc catctactgg ggaacctgtg gttgaggtcc   3360
ctaaaagcac tcaagtacaa atccatgaaa atcatggtca acgcagcctt gcagaggcag   3420
ttccacagcc ccttcatctt ccgtgaggag gatcccagcc gccagatcgt gtttgagatc   3480
tccaagcaag aggactggca ggtccccatc tggatcattg taggcagcac cctgggggggc   3540
ctcctactgc tggccctgct ggtcctggca ctgtggaagc tcggcttctt tagaagtgcc   3600
aggcgcagga gggagcctgg tctggacccc acccccaaag tgctggagtg aggctccaga   3660
ggagactttg agttgatggg ggccaggaca ccagtccagg tagtgttgag acccaggcct   3720
gtggccccac cgagctggag cggagaggaa gccagctggc tttgcacttg acctcatctc   3780
ccgagcaatg gcgcctgctc cctccagaat ggaactcaag ctggttttaa gtggaactgc   3840
cctactggga gactgggaca cctttaacac agacccctag ggatttaaag ggacacccct   3900
acacacaccc aggcccacgc caaggcctcc ctcaggctct gtggagggca tttgctgccc   3960
cagctactaa ggtgctagga attcgtaatc atccccatcc tccagagaaa cccagggagg   4020
aagactgtaa atacgaaccc aatctgcaca ctccaggcct ctagttccag aaggatccaa   4080
gacaaaacag atctgaattc tgccctttc tctcacccat cccacccctc cattggctcc   4140
caagtcacac ccactccctt ccccatagat aggcccctgg ggctcccgaa gaatgaaccc   4200
aagagcaagg gcttgatggt gacagctgca agccagggat gaagaaagac tctgagatgt   4260
ggagactgat ggccaggcaa gtgggaccag gatactggac gctgtcctga gatgagaggt   4320
agccgggctc tgcacccacg tgcattcaca ttgaccgcaa ctcacacatt cccccaccag   4380
ctgcagcccc ttgctctcag ctgccaaccc tcccgggtca cttttgttcc caggtacctc   4440
atgggaagca tgtggatgac acaatccctg gggctgtgca ttcccacgtc ttcttgctgc   4500
agcctgcccc tagacatgga cgcaccggcc tggctgcagc tgggcagcag gggtaggggt   4560
```

-continued

```
agggagcctc ccctccctgt atcacccccct ccctacacac acacacacac acacacacac   4620

acactgcctc ccatccttcc ctcatgcccg ccagtgcaca gggaagggct tggccagcgc   4680

tgttgagggg tcccctctgg aatgcactga ataaagcacg tgcaaggact cccggagcct   4740

gtgcagcctt ggtggcaaat atctcatctg ccggccccca ggacaagtgg tatgaccagt   4800

gataatgccc caaggacaag gggcgtgcct ggcgcccagt ggagtaattt atgccttagt   4860

cttgttttga ggtagaaatg caagggggac acatgaaagg catcagtccc cctgtgcata   4920

gtacgacctt tactgtcgta tttttgaaaa attaaaaata cagtgtttaa aaacaaaaaa   4980

aaaaaaaaaa aaaaa                                                      4995


<210> SEQ ID NO 187
<211> LENGTH: 1189
<212> TYPE: PRT
<213> ORGANISM: Homo sapiens

<400> SEQUENCE: 187

Met Asp Leu Pro Arg Gly Leu Val Val Ala Trp Ala Leu Ser Leu Trp
1               5                   10                  15

Pro Gly Phe Thr Asp Thr Phe Asn Met Asp Thr Arg Lys Pro Arg Val
            20                  25                  30

Ile Pro Gly Ser Arg Thr Ala Phe Phe Gly Tyr Thr Val Gln Gln His
        35                  40                  45

Asp Ile Ser Gly Asn Lys Trp Leu Val Val Gly Ala Pro Leu Glu Thr
    50                  55                  60

Asn Gly Tyr Gln Lys Thr Gly Asp Val Tyr Lys Cys Pro Val Ile His
65                  70                  75                  80

Gly Asn Cys Thr Lys Leu Asn Leu Gly Arg Val Thr Leu Ser Asn Val
                85                  90                  95

Ser Glu Arg Lys Asp Asn Met Arg Leu Gly Leu Ser Leu Ala Thr Asn
            100                 105                 110

Pro Lys Asp Asn Ser Phe Leu Ala Cys Ser Pro Leu Trp Ser His Glu
        115                 120                 125

Cys Gly Ser Ser Tyr Tyr Thr Thr Gly Met Cys Ser Arg Val Asn Ser
    130                 135                 140

Asn Phe Arg Phe Ser Lys Thr Val Ala Pro Ala Leu Gln Arg Cys Gln
145                 150                 155                 160

Thr Tyr Met Asp Ile Val Ile Val Leu Asp Gly Ser Asn Ser Ile Tyr
                165                 170                 175

Pro Trp Val Glu Val Gln His Phe Leu Ile Asn Ile Leu Lys Lys Phe
            180                 185                 190

Tyr Ile Gly Pro Gly Gln Ile Gln Val Gly Val Val Gln Tyr Gly Glu
        195                 200                 205

Asp Val Val His Glu Phe His Leu Asn Asp Tyr Arg Ser Val Lys Asp
    210                 215                 220

Val Val Glu Ala Ala Ser His Ile Glu Gln Arg Gly Gly Thr Glu Thr
225                 230                 235                 240

Arg Thr Ala Phe Gly Ile Glu Phe Ala Arg Ser Glu Ala Phe Gln Lys
                245                 250                 255

Gly Gly Arg Lys Gly Ala Lys Lys Val Met Ile Val Ile Thr Asp Gly
            260                 265                 270

Glu Ser His Asp Ser Pro Asp Leu Glu Lys Val Ile Gln Gln Ser Glu
        275                 280                 285

Arg Asp Asn Val Thr Arg Tyr Ala Val Ala Val Leu Gly Tyr Tyr Asn
    290                 295                 300
```

```
Arg Arg Gly Ile Asn Pro Glu Thr Phe Leu Asn Glu Ile Lys Tyr Ile
305                 310                 315                 320

Ala Ser Asp Pro Asp Asp Lys His Phe Phe Asn Val Thr Asp Glu Ala
                325                 330                 335

Ala Leu Lys Asp Ile Val Asp Ala Leu Gly Asp Arg Ile Phe Ser Leu
            340                 345                 350

Glu Gly Thr Asn Lys Asn Glu Thr Ser Phe Gly Leu Glu Met Ser Gln
        355                 360                 365

Thr Gly Phe Ser Ser His Val Val Glu Asp Gly Val Leu Leu Gly Ala
    370                 375                 380

Val Gly Ala Tyr Asp Trp Asn Gly Ala Val Leu Lys Glu Thr Ser Ala
385                 390                 395                 400

Gly Lys Val Ile Pro Leu Arg Glu Ser Tyr Leu Lys Glu Phe Pro Glu
                405                 410                 415

Glu Leu Lys Asn His Gly Ala Tyr Leu Gly Tyr Thr Val Thr Ser Val
            420                 425                 430

Val Ser Ser Arg Gln Gly Arg Val Tyr Val Ala Gly Ala Pro Arg Phe
        435                 440                 445

Asn His Thr Gly Lys Val Ile Leu Phe Thr Met His Asn Asn Arg Ser
    450                 455                 460

Leu Thr Ile His Gln Ala Met Arg Gly Gln Gln Ile Gly Ser Tyr Phe
465                 470                 475                 480

Gly Ser Glu Ile Thr Ser Val Asp Ile Asp Gly Asp Gly Val Thr Asp
                485                 490                 495

Val Leu Leu Val Gly Ala Pro Met Tyr Phe Asn Glu Gly Arg Glu Arg
            500                 505                 510

Gly Lys Val Tyr Val Tyr Glu Leu Arg Gln Asn Arg Phe Val Tyr Asn
        515                 520                 525

Gly Thr Leu Lys Asp Ser His Ser Tyr Gln Asn Ala Arg Phe Gly Ser
    530                 535                 540

Ser Ile Ala Ser Val Arg Asp Leu Asn Gln Asp Ser Tyr Asn Asp Val
545                 550                 555                 560

Val Val Gly Ala Pro Leu Glu Asp Asn His Ala Gly Ala Ile Tyr Ile
                565                 570                 575

Phe His Gly Phe Arg Gly Ser Ile Leu Lys Thr Pro Lys Gln Arg Ile
            580                 585                 590

Thr Ala Ser Glu Leu Ala Thr Gly Leu Gln Tyr Phe Gly Cys Ser Ile
        595                 600                 605

His Gly Gln Leu Asp Leu Asn Glu Asp Gly Leu Ile Asp Leu Ala Val
    610                 615                 620

Gly Ala Leu Gly Asn Ala Val Ile Leu Trp Ser Arg Pro Val Val Gln
625                 630                 635                 640

Ile Asn Ala Ser Leu His Phe Glu Pro Ser Lys Ile Asn Ile Phe His
                645                 650                 655

Arg Asp Cys Lys Arg Ser Gly Arg Asp Ala Thr Cys Leu Ala Ala Phe
            660                 665                 670

Leu Cys Phe Thr Pro Ile Phe Leu Ala Pro His Phe Gln Thr Thr Thr
        675                 680                 685

Val Gly Ile Arg Tyr Asn Ala Thr Met Asp Glu Arg Arg Tyr Thr Pro
    690                 695                 700

Arg Ala His Leu Asp Glu Gly Gly Asp Arg Phe Thr Asn Arg Ala Val
705                 710                 715                 720

Leu Leu Ser Ser Gly Gln Glu Leu Cys Glu Arg Ile Asn Phe His Val
```

-continued

```
                725                 730                 735

Leu Asp Thr Ala Asp Tyr Val Lys Pro Val Thr Phe Ser Val Glu Tyr
            740                 745                 750

Ser Leu Glu Asp Pro Asp His Gly Pro Met Leu Asp Asp Gly Trp Pro
        755                 760                 765

Thr Thr Leu Arg Val Ser Val Pro Phe Trp Asn Gly Cys Asn Glu Asp
    770                 775                 780

Glu His Cys Val Pro Asp Leu Val Leu Asp Ala Arg Ser Asp Leu Pro
785                 790                 795                 800

Thr Ala Met Glu Tyr Cys Gln Arg Val Leu Arg Lys Pro Ala Gln Asp
                805                 810                 815

Cys Ser Ala Tyr Thr Leu Ser Phe Asp Thr Thr Val Phe Ile Ile Glu
            820                 825                 830

Ser Thr Arg Gln Arg Val Ala Val Glu Ala Thr Leu Glu Asn Arg Gly
        835                 840                 845

Glu Asn Ala Tyr Ser Thr Val Leu Asn Ile Ser Gln Ser Ala Asn Leu
    850                 855                 860

Gln Phe Ala Ser Leu Ile Gln Lys Glu Asp Ser Asp Gly Ser Ile Glu
865                 870                 875                 880

Cys Val Asn Glu Glu Arg Arg Leu Gln Lys Gln Val Cys Asn Val Ser
                885                 890                 895

Tyr Pro Phe Phe Arg Ala Lys Ala Lys Val Ala Phe Arg Leu Asp Phe
            900                 905                 910

Glu Phe Ser Lys Ser Ile Phe Leu His His Leu Glu Ile Glu Leu Ala
        915                 920                 925

Ala Gly Ser Asp Ser Asn Glu Arg Asp Ser Thr Lys Glu Asp Asn Val
    930                 935                 940

Ala Pro Leu Arg Phe His Leu Lys Tyr Glu Ala Asp Val Leu Phe Thr
945                 950                 955                 960

Arg Ser Ser Ser Leu Ser His Tyr Glu Val Lys Leu Asn Ser Ser Leu
                965                 970                 975

Glu Arg Tyr Asp Gly Ile Gly Pro Pro Phe Ser Cys Ile Phe Arg Ile
            980                 985                 990

Gln Asn Leu Gly Leu Phe Pro Ile  His Gly Ile Met Met  Lys Ile Thr
        995                 1000                 1005

Ile Pro  Ile Ala Thr Arg Ser  Gly Asn Arg Leu Leu  Lys Leu Arg Asp
    1010                 1015                 1020

Phe  Leu Thr Asp Glu Val  Ala Asn Thr Ser Cys  Asn Ile Trp Gly Asn
1025                 1030                 1035                 1040

Ser Thr Glu Tyr Arg  Pro Thr Pro Val Glu  Glu Asp Leu Arg Arg  Ala
                1045                 1050                 1055

Pro Gln Leu Asn  His Ser Asn Ser Asp  Val Val Ser Ile Asn  Cys Asn
            1060                 1065                 1070

Ile Arg Leu  Val Pro Asn Gln Glu  Ile Asn Phe His Leu  Leu Gly Asn
        1075                 1080                 1085

Leu Trp  Leu Arg Ser Leu Lys  Ala Leu Lys Tyr Lys  Ser Met Lys Ile
    1090                 1095                 1100

Met  Val Asn Ala Ala Leu  Gln Arg Gln Phe His  Ser Pro Phe Ile Phe
1105                 1110                 1115                 1120

Arg Glu Glu Asp Pro  Ser Arg Gln Ile Val  Phe Glu Ile Ser Lys  Gln
                1125                 1130                 1135

Glu Asp Trp Gln  Val Pro Ile Trp Ile  Ile Val Gly Ser Thr  Leu Gly
            1140                 1145                 1150
```

```
Gly Leu Leu  Leu Leu Ala Leu Leu  Val Leu Ala Leu Trp  Lys Leu Gly
        1155                1160                1165

Phe Phe  Arg Ser Ala Arg Arg  Arg Arg Glu Pro Gly  Leu Asp Pro Thr
    1170                1175                1180

Pro  Lys Val Leu Glu
1185
```

<210> SEQ ID NO 188
<211> LENGTH: 4631
<212> TYPE: DNA
<213> ORGANISM: Homo sapiens

<400> SEQUENCE: 188

```
ccgccgcgcc gaggaggctg ccgctctggc ttgccgcccc ccgccgccgc tgcacaccgg     60

acccagccgc cgtgccgcgg gccatggacc tgcccagggg cctggtggtg gcctgggcgc    120

tcagcctgtg gccagggttc acggacacct tcaacatgga caccaggaag ccccgggtca    180

tccctggctc caggaccgcc ttctttggct acacagtgca gcagcacgac atcagtggca    240

ataagtggct ggtcgtgggc gccccactgg aaaccaatgg ctaccagaag acgggagacg    300

tgtacaagtg tccagtgatc cacgggaact gcaccaaact caacctggga agggtcaccc    360

tgtccaacgt gtccgagcgg aaagacaaca tgcgcctcgg ccttagtctc gccaccaacc    420

ccaaggacaa cagcttcctg gcctgcagcc ccctctggtc tcatgagtgt gggagctcct    480

actacaccac agggatgtgt tcaagagtca actccaactt caggttctcc aagaccgtgg    540

ccccagctct ccaaaggtgc cagacctaca tggacatcgt cattgtcctg gatggctcca    600

acagcatcta cccctgggtg gaggttcagc acttcctcat caacatcctg aaaaagtttt    660

acattggccc agggcagatc caggttggag ttgtgcagta tggcgaagat gtggtgcatg    720

agtttcacct caatgactac aggtctgtaa aagatgtggt ggaagctgcc agccacattg    780

agcagagagg aggaacagag acccggacgg catttggcat tgaatttgca cgctcagagg    840

ctttccagaa gggtggaagg aaaggagcca agaaggtgat gattgtcatc acagatgggg    900

agtcccacga cagcccagac ctggagaagg tgatccagca aagcgaaaga gacaacgtaa    960

caagatatgc ggtggccgtc ctgggctact acaaccgcag ggggatcaat ccagaaactt   1020

ttctaaatga aatcaaatac atcgccagtg accctgatga caagcacttc ttcaatgtca   1080

ctgatgaggc tgccttgaag gacattgtcg atgccctggg ggacagaatc ttcagcctgg   1140

aaggcaccaa caagaacgag acctcctttg ggctggagat gtcacagacg ggcttttcct   1200

cgcacgtggt ggaggatggg gttctgctgg gagccgtcgg tgcctatgac tggaatggag   1260

ctgtgctaaa ggagacgagt gccgggaagg tcattcctct ccgcgagtcc tacctgaaag   1320

agttccccga ggagctcaag aaccatggtg catacctggg gtacacagtc acatcggtcg   1380

tgtcctccag gcaggggcga gtgtacgtgg ccggagcccc ccggttcaac cacacgggca   1440

aggtcatcct gttcaccatg cacaacaacc ggagcctcac catccaccag gctatgcggg   1500

gccagcagat aggctcttac tttgggagtg aaatcacctc ggtggacatc gacggcgacg   1560

gcgtgactga tgtcctgctg gtgggcgcac ccatgtactt caacgagggc cgtgagcgag   1620

gcaaggtgta cgtctatgag ctgagacaga accggtttgt ttataacgga acgctaaagg   1680

attcacacag ttaccagaat gcccgatttg ggtcctccat tgcctcagtt cgagacctca   1740

accaggattc ctacaatgac gtggtggtgg gagccccccct ggaggacaac cacgcaggag   1800

ccatctacat cttccacggc ttccgaggca gcatcctgaa gacacctaag cagagaatca   1860

cagcctcaga gctggctacc ggcctccagt attttggctg cagcatccac gggcaattgg   1920
```

```
acctcaatga ggatgggctc atcgacctgg cagtgggagc ccttggcaac gctgtgattc   1980
tgtggtcccg cccagtggtt cagatcaatg ccagcctcca ctttgagcca tccaagatca   2040
acatcttcca cagagactgc aagcgcagtg gcagggatgc cacctgcctg gccgccttcc   2100
tctgcttcac gcccatcttc ctggcacccc atttccaaac aacaactgtt ggcatcagat   2160
acaacgccac catggatgag aagcggtata caccgagggc ccacctggac gaaggcgggg   2220
accgattcac caacagagcc gtactgctct cctccggcca ggagctctgt gagcggatca   2280
acttccatgt cctggacact gctgactacg tgaagccagt gaccttctca gtcgagtatt   2340
ccctggagga ccctgaccat ggccccatgc tggacgacgg ctggcccacc actctcagag   2400
tctcggtgcc cttctggaac ggctgcaatg aggatgagca ctgtgtccct gaccttgtgt   2460
tggatgcccg gagtgacctg cccacggcca tggagtactg ccagagggtg ctgaggaagc   2520
ctgcgcagga ctgctccgca tacacgctgt ccttcgacac cacagtcttc atcatagaga   2580
gcacacgcca gcgagtggcg gtggaggcca cactggagaa caggggcgag aacgcctaca   2640
gcacggtcct aaatatctcg cagtcagcaa acctgcagtt tgccagcttg atccagaagg   2700
aggactcaga cggtagcatt gagtgtgtga acgaggagag gaggctccag aagcaagtct   2760
gcaacgtcag ctatcccttc ttccgggcca aggccaaggt ggctttccgt cttgattttg   2820
agttcagcaa atccatcttc ctacaccacc tggagatcga gctcgctgca ggcagtgaca   2880
gtaatgagcg ggacagcacc aaggaagaca acgtggcccc cttacgcttc cacctcaaat   2940
acgaagctga cgtcctcttc accaggagca gcagcctgag ccactacgag gtcaagctca   3000
acagctcgct ggagagatac gatggtatcg ggcctccctt cagctgcatc ttcaggatcc   3060
agaacttggg cttgttcccc atccacggga ttatgatgaa gatcaccatt cccatcgcca   3120
ccaggagcgg caaccgccta ctgaagctga gggacttcct cacggacgag ggcgaacacg   3180
tcctgtaaca tctggggcaa tagcactgag taccggccca ccccagtgga ggaagacttg   3240
cgtcgtgctc cacagctgaa tcacagcaac tctgatgtcg tctccatcaa ctgcaatata   3300
cggctggtcc ccaaccagga aatcaatttc catctactgg ggaacctgtg gttgaggtcc   3360
gtaaaagcac tcaagtacaa atccatgaaa atcatggtca acgcagcgtt gcagaggcag   3420
ttccacagcc ccttcatctt ccgtgaggag gatcccagcc gccagatcgt gtttgagatc   3480
tccaagcaag aggactggca ggtccccatc tggatcattg taggcagcac cctgggggc   3540
ctcctactgc tggccctgct ggtcctggca ctgtggaagc tcggcttctt tagaagtgcc   3600
aggcgcagga gggagcctgg tctggacccc acccccaaag tgctggagtg aggctccaga   3660
ggagactttg agttgatggg ggccagacac cagtccaggt agtgttgaga cccaggcctg   3720
tggccccacc gagctggagc ggagaggaag ccagctggct ttgcacttga cctcatctcc   3780
cgagcaatgg cgcctgctcc ctccagaatg gaactcaagc tggttttaag tggaactgcc   3840
ctactgggag actgggacac ctttaacaca gacccctagg gatttaaagg gacaccccta   3900
cacacaccca ggcccacgcc aaggcctccc tcaggctctg tggagggcat ttgctgcccc   3960
agctactaag gtgctaggaa ttcgtaatca tccccatcct ccagagaaac ccagggagga   4020
agactgtaaa tacgaaccca atctgcacac tccaggcctc tagttccaga aggatccaag   4080
acaaaacaga tctgaattct gccctttttct ctcacccatc ccacccctcc attggctccc   4140
aagtcacacc cactcccttc cccatagata ggcccctggg gctcccgaag atgaacccaa   4200
gagcaagggc ttgatggtga cagctgcaag ccagggatga agaaagactc tgagatgtgg   4260
agactgatgg ccaggcaagt gggaccagga tactggacgc tgtcctgaga tgagaggtag   4320
```

```
ccgggctctg cacccacgtg cattcacatt gaccgcaact cacacattcc cccaccagct   4380

gcagcccctt gctctcagct gccaaccctc ccgggtcact tttgttccca ggtacctcat   4440

gggaagcatg tggatgacac aatccctggg gctgtgcatt cccacgtctt cttgctgcag   4500

cctgccccta gacatggacg caccggcctg gctgcagctg ggcagcaggg gtaggggtag   4560

ggagcctccc ctccctgtat cacccccctcc ctacacgtcg acgcggccgc gaattcccgg   4620

gtcgacgagc t                                                        4631
```

<210> SEQ ID NO 189
<211> LENGTH: 1034
<212> TYPE: PRT
<213> ORGANISM: Homo sapiens

<400> SEQUENCE: 189

```
Met Asp Leu Pro Arg Gly Leu Val Val Ala Trp Ala Leu Ser Leu Trp
  1               5                  10                  15

Pro Gly Phe Thr Asp Thr Phe Asn Met Asp Thr Arg Lys Pro Arg Val
             20                  25                  30

Ile Pro Gly Ser Arg Thr Ala Phe Phe Gly Tyr Thr Val Gln Gln His
         35                  40                  45

Asp Ile Ser Gly Asn Lys Trp Leu Val Val Gly Ala Pro Leu Glu Thr
     50                  55                  60

Asn Gly Tyr Gln Lys Thr Gly Asp Val Tyr Lys Cys Pro Val Ile His
 65                  70                  75                  80

Gly Asn Cys Thr Lys Leu Asn Leu Gly Arg Val Thr Leu Ser Asn Val
                 85                  90                  95

Ser Glu Arg Lys Asp Asn Met Arg Leu Gly Leu Ser Leu Ala Thr Asn
            100                 105                 110

Pro Lys Asp Asn Ser Phe Leu Ala Cys Ser Pro Leu Trp Ser His Glu
        115                 120                 125

Cys Gly Ser Ser Tyr Tyr Thr Thr Gly Met Cys Ser Arg Val Asn Ser
    130                 135                 140

Asn Phe Arg Phe Ser Lys Thr Val Ala Pro Ala Leu Gln Arg Cys Gln
145                 150                 155                 160

Thr Tyr Met Asp Ile Val Ile Val Leu Asp Gly Ser Asn Ser Ile Tyr
                165                 170                 175

Pro Trp Val Glu Val Gln His Phe Leu Ile Asn Ile Leu Lys Lys Phe
            180                 185                 190

Tyr Ile Gly Pro Gly Gln Ile Gln Val Gly Val Val Gln Tyr Gly Glu
        195                 200                 205

Asp Val Val His Glu Phe His Leu Asn Asp Tyr Arg Ser Val Lys Asp
    210                 215                 220

Val Val Glu Ala Ala Ser His Ile Glu Gln Arg Gly Gly Thr Glu Thr
225                 230                 235                 240

Arg Thr Ala Phe Gly Ile Glu Phe Ala Arg Ser Glu Ala Phe Gln Lys
                245                 250                 255

Gly Gly Arg Lys Gly Ala Lys Lys Val Met Ile Val Ile Thr Asp Gly
            260                 265                 270

Glu Ser His Asp Ser Pro Asp Leu Glu Lys Val Ile Gln Gln Ser Glu
        275                 280                 285

Arg Asp Asn Val Thr Arg Tyr Ala Val Ala Val Leu Gly Tyr Tyr Asn
    290                 295                 300

Arg Arg Gly Ile Asn Pro Glu Thr Phe Leu Asn Glu Ile Lys Tyr Ile
305                 310                 315                 320
```

```
Ala Ser Asp Pro Asp Asp Lys His Phe Phe Asn Val Thr Asp Glu Ala
                325                 330                 335

Ala Leu Lys Asp Ile Val Asp Ala Leu Gly Asp Arg Ile Phe Ser Leu
            340                 345                 350

Glu Gly Thr Asn Lys Asn Glu Thr Ser Phe Gly Leu Glu Met Ser Gln
        355                 360                 365

Thr Gly Phe Ser Ser His Val Val Glu Asp Gly Val Leu Leu Gly Ala
    370                 375                 380

Val Gly Ala Tyr Asp Trp Asn Gly Ala Val Leu Lys Glu Thr Ser Ala
385                 390                 395                 400

Gly Lys Val Ile Pro Leu Arg Glu Ser Tyr Leu Lys Glu Phe Pro Glu
                405                 410                 415

Glu Leu Lys Asn His Gly Ala Tyr Leu Gly Tyr Thr Val Thr Ser Val
            420                 425                 430

Val Ser Ser Arg Gln Gly Arg Val Tyr Val Ala Gly Ala Pro Arg Phe
        435                 440                 445

Asn His Thr Gly Lys Val Ile Leu Phe Thr Met His Asn Asn Arg Ser
    450                 455                 460

Leu Thr Ile His Gln Ala Met Arg Gly Gln Gln Ile Gly Ser Tyr Phe
465                 470                 475                 480

Gly Ser Glu Ile Thr Ser Val Asp Ile Asp Gly Asp Gly Val Thr Asp
                485                 490                 495

Val Leu Leu Val Gly Ala Pro Met Tyr Phe Asn Glu Gly Arg Glu Arg
            500                 505                 510

Gly Lys Val Tyr Val Tyr Glu Leu Arg Gln Asn Arg Phe Val Tyr Asn
        515                 520                 525

Gly Thr Leu Lys Asp Ser His Ser Tyr Gln Asn Ala Arg Phe Gly Ser
    530                 535                 540

Ser Ile Ala Ser Val Arg Asp Leu Asn Gln Asp Ser Tyr Asn Asp Val
545                 550                 555                 560

Val Val Gly Ala Pro Leu Glu Asp Asn His Ala Gly Ala Ile Tyr Ile
                565                 570                 575

Phe His Gly Phe Arg Gly Ser Ile Leu Lys Thr Pro Lys Gln Arg Ile
            580                 585                 590

Thr Ala Ser Glu Leu Ala Thr Gly Leu Gln Tyr Phe Gly Cys Ser Ile
        595                 600                 605

His Gly Gln Leu Asp Leu Asn Glu Asp Gly Leu Ile Asp Leu Ala Val
    610                 615                 620

Gly Ala Leu Gly Asn Ala Val Ile Leu Trp Ser Arg Pro Val Val Gln
625                 630                 635                 640

Ile Asn Ala Ser Leu His Phe Glu Pro Ser Lys Ile Asn Ile Phe His
                645                 650                 655

Arg Asp Cys Lys Arg Ser Gly Arg Asp Ala Thr Cys Leu Ala Ala Phe
            660                 665                 670

Leu Cys Phe Thr Pro Ile Phe Leu Ala Pro His Phe Gln Thr Thr Thr
        675                 680                 685

Val Gly Ile Arg Tyr Asn Ala Thr Met Asp Glu Lys Arg Tyr Thr Pro
    690                 695                 700

Arg Ala His Leu Asp Glu Gly Gly Asp Arg Phe Thr Asn Arg Ala Val
705                 710                 715                 720

Leu Leu Ser Ser Gly Gln Glu Leu Cys Glu Arg Ile Asn Phe His Val
                725                 730                 735

Leu Asp Thr Ala Asp Tyr Val Lys Pro Val Thr Phe Ser Val Glu Tyr
```

```
            740                 745                 750

Ser Leu Glu Asp Pro Asp His Gly Pro Met Leu Asp Asp Gly Trp Pro
        755                 760                 765

Thr Thr Leu Arg Val Ser Val Pro Phe Trp Asn Gly Cys Asn Glu Asp
    770                 775                 780

Glu His Cys Val Pro Asp Leu Val Leu Asp Ala Arg Ser Asp Leu Pro
785                 790                 795                 800

Thr Ala Met Glu Tyr Cys Gln Arg Val Leu Arg Lys Pro Ala Gln Asp
                805                 810                 815

Cys Ser Ala Tyr Thr Leu Ser Phe Asp Thr Thr Val Phe Ile Ile Glu
            820                 825                 830

Ser Thr Arg Gln Arg Val Ala Val Glu Ala Thr Leu Glu Asn Arg Gly
        835                 840                 845

Glu Asn Ala Tyr Ser Thr Val Leu Asn Ile Ser Gln Ser Ala Asn Leu
    850                 855                 860

Gln Phe Ala Ser Leu Ile Gln Lys Glu Asp Ser Asp Gly Ser Ile Glu
865                 870                 875                 880

Cys Val Asn Glu Glu Arg Arg Leu Gln Lys Gln Val Cys Asn Val Ser
                885                 890                 895

Tyr Pro Phe Phe Arg Ala Lys Ala Lys Val Ala Phe Arg Leu Asp Phe
            900                 905                 910

Glu Phe Ser Lys Ser Ile Phe Leu His His Leu Glu Ile Glu Leu Ala
        915                 920                 925

Ala Gly Ser Asp Ser Asn Glu Arg Asp Ser Thr Lys Glu Asp Asn Val
    930                 935                 940

Ala Pro Leu Arg Phe His Leu Lys Tyr Glu Ala Asp Val Leu Phe Thr
945                 950                 955                 960

Arg Ser Ser Ser Leu Ser His Tyr Glu Val Lys Leu Asn Ser Ser Leu
                965                 970                 975

Glu Arg Tyr Asp Gly Ile Gly Pro Pro Phe Ser Cys Ile Phe Arg Ile
            980                 985                 990

Gln Asn Leu Gly Leu Phe Pro Ile  His Gly Ile Met Met  Lys Ile Thr
        995                 1000                1005

Ile Pro  Ile Ala Thr Arg Ser  Gly Asn Arg Leu Leu  Lys Leu Arg Asp
    1010                1015                1020

Phe  Leu Thr Asp Glu Gly  Glu His Val Leu
1025                1030


<210> SEQ ID NO 190
<211> LENGTH: 33
<212> TYPE: PRT
<213> ORGANISM: Homo sapiens

<400> SEQUENCE: 190

Thr Asn Gly Tyr Gln Lys Thr Gly Asp Val Tyr Lys Cys Pro Val Ile
  1               5                  10                  15

His Gly Asn Cys Thr Lys Leu Asn Leu Gly Arg Val Thr Leu Ser Asn
             20                  25                  30

Val


<210> SEQ ID NO 191
<211> LENGTH: 1151
<212> TYPE: PRT
<213> ORGANISM: Homo sapiens

<400> SEQUENCE: 191
```

-continued

```
Phe Asn Val Asp Val Lys Asn Ser Met Thr Phe Ser Gly Pro Val Glu
 1               5                  10                  15

Asp Met Phe Gly Tyr Thr Val Gln Gln Tyr Glu Asn Glu Glu Gly Lys
            20                  25                  30

Trp Val Leu Ile Gly Ser Pro Leu Val Gly Gln Pro Lys Asn Arg Thr
        35                  40                  45

Gly Asp Val Tyr Lys Cys Pro Val Gly Arg Gly Glu Ser Leu Pro Cys
    50                  55                  60

Val Lys Leu Asp Leu Pro Val Asn Thr Ser Ile Pro Asn Val Thr Glu
65                  70                  75                  80

Val Lys Glu Asn Met Thr Phe Gly Ser Thr Leu Val Thr Asn Pro Asn
                85                  90                  95

Gly Gly Phe Leu Ala Cys Gly Pro Leu Tyr Ala Tyr Arg Cys Gly His
            100                 105                 110

Leu His Tyr Thr Thr Gly Ile Cys Ser Asp Val Ser Pro Thr Phe Gln
        115                 120                 125

Val Val Asn Ser Ile Ala Pro Val Gln Glu Cys Ser Thr Gln Leu Asp
    130                 135                 140

Ile Val Ile Val Leu Asp Gly Ser Asn Ser Ile Tyr Pro Trp Asp Ser
145                 150                 155                 160

Val Thr Ala Phe Leu Asn Asp Leu Leu Lys Arg Met Asp Ile Gly Pro
                165                 170                 175

Lys Gln Thr Gln Val Gly Ile Val Gln Tyr Gly Glu Asn Val Thr His
            180                 185                 190

Glu Phe Asn Leu Asn Lys Tyr Ser Ser Thr Glu Glu Val Leu Val Ala
        195                 200                 205

Ala Lys Lys Ile Val Gln Arg Gly Gly Arg Gln Thr Met Thr Ala Leu
    210                 215                 220

Gly Thr Asp Thr Ala Arg Lys Glu Ala Phe Thr Glu Ala Arg Gly Ala
225                 230                 235                 240

Arg Arg Gly Val Lys Lys Val Met Val Ile Val Thr Asp Gly Glu Ser
                245                 250                 255

His Asp Asn His Arg Leu Lys Lys Val Ile Gln Asp Cys Glu Asp Glu
            260                 265                 270

Asn Ile Gln Arg Phe Ser Ile Ala Ile Leu Gly Ser Tyr Asn Arg Gly
        275                 280                 285

Asn Leu Ser Thr Glu Lys Phe Val Glu Glu Ile Lys Ser Ile Ala Ser
    290                 295                 300

Glu Pro Thr Glu Lys His Phe Phe Asn Val Ser Asp Glu Leu Ala Leu
305                 310                 315                 320

Val Thr Ile Val Lys Thr Leu Gly Glu Arg Ile Phe Ala Leu Glu Ala
                325                 330                 335

Thr Ala Asp Gln Ser Ala Ala Ser Phe Glu Met Glu Met Ser Gln Thr
            340                 345                 350

Gly Phe Ser Ala His Tyr Ser Gln Asp Trp Val Met Leu Gly Ala Val
        355                 360                 365

Gly Ala Tyr Asp Trp Asn Gly Thr Val Val Met Gln Lys Ala Ser Gln
    370                 375                 380

Ile Ile Ile Pro Arg Asn Thr Thr Phe Asn Val Glu Ser Thr Lys Lys
385                 390                 395                 400

Asn Glu Pro Leu Ala Ser Tyr Leu Gly Tyr Thr Val Asn Ser Ala Thr
                405                 410                 415

Ala Ser Ser Gly Asp Val Leu Tyr Ile Ala Gly Gln Pro Arg Tyr Asn
            420                 425                 430
```

```
His Thr Gly Gln Val Ile Ile Tyr Arg Met Glu Asp Gly Asn Ile Lys
        435                 440                 445

Ile Leu Gln Thr Leu Ser Gly Glu Gln Ile Gly Ser Tyr Phe Gly Ser
    450                 455                 460

Ile Leu Thr Thr Thr Asp Ile Asp Lys Asp Ser Asn Thr Asp Ile Leu
465                 470                 475                 480

Leu Val Gly Ala Pro Met Tyr Met Gly Thr Glu Lys Glu Glu Gln Gly
                485                 490                 495

Lys Val Tyr Val Tyr Ala Leu Asn Gln Thr Arg Phe Glu Tyr Gln Met
            500                 505                 510

Ser Leu Glu Pro Ile Lys Gln Thr Cys Cys Ser Ser Arg Gln His Asn
        515                 520                 525

Ser Cys Thr Thr Glu Asn Lys Asn Glu Pro Cys Gly Ala Arg Phe Gly
    530                 535                 540

Thr Ala Ile Ala Ala Val Lys Asp Leu Asn Leu Asp Gly Phe Asn Asp
545                 550                 555                 560

Ile Val Ile Gly Ala Pro Leu Glu Asp Asp His Gly Gly Ala Val Tyr
                565                 570                 575

Ile Tyr His Gly Ser Gly Lys Thr Ile Arg Lys Glu Tyr Ala Gln Arg
            580                 585                 590

Ile Pro Ser Gly Gly Asp Gly Lys Thr Leu Lys Phe Phe Gly Gln Ser
        595                 600                 605

Ile His Gly Glu Met Asp Leu Asn Gly Asp Gly Leu Thr Asp Val Thr
    610                 615                 620

Ile Gly Gly Leu Gly Gly Ala Ala Leu Phe Trp Ser Arg Asp Val Ala
625                 630                 635                 640

Val Val Lys Val Thr Met Asn Phe Glu Pro Asn Lys Val Asn Ile Gln
                645                 650                 655

Lys Lys Asn Cys His Met Glu Gly Lys Glu Thr Val Cys Ile Asn Ala
            660                 665                 670

Thr Val Cys Phe Glu Val Lys Leu Lys Ser Lys Glu Asp Thr Ile Tyr
        675                 680                 685

Glu Ala Asp Leu Gln Tyr Arg Val Thr Leu Asp Ser Leu Arg Gln Ile
    690                 695                 700

Ser Arg Ser Phe Phe Ser Gly Thr Gln Glu Arg Lys Val Gln Arg Asn
705                 710                 715                 720

Ile Thr Val Arg Lys Ser Glu Cys Thr Lys His Ser Phe Tyr Met Leu
                725                 730                 735

Asp Lys His Asp Phe Gln Asp Ser Val Arg Ile Thr Leu Asp Phe Asn
            740                 745                 750

Leu Thr Asp Pro Glu Asn Gly Pro Val Leu Asp Asp Ser Leu Pro Asn
        755                 760                 765

Ser Val His Glu Tyr Ile Pro Phe Ala Lys Asp Cys Gly Asn Lys Glu
    770                 775                 780

Lys Cys Ile Ser Asp Leu Ser Leu His Val Ala Thr Thr Glu Lys Asp
785                 790                 795                 800

Leu Leu Ile Val Arg Ser Gln Asn Asp Lys Phe Asn Val Ser Leu Thr
                805                 810                 815

Val Lys Asn Thr Lys Asp Ser Ala Tyr Asn Thr Arg Thr Ile Val His
            820                 825                 830

Tyr Ser Pro Asn Leu Val Phe Ser Gly Ile Glu Ala Ile Gln Lys Asp
        835                 840                 845

Ser Cys Glu Ser Asn His Asn Ile Thr Cys Lys Val Gly Tyr Pro Phe
```

```
    850                 855                 860

Leu Arg Arg Gly Glu Met Val Thr Phe Lys Ile Leu Phe Gln Phe Asn
865                 870                 875                 880

Thr Ser Tyr Leu Met Glu Asn Val Thr Ile Tyr Leu Ser Ala Thr Ser
                885                 890                 895

Asp Ser Glu Glu Pro Pro Glu Thr Leu Ser Asp Asn Val Val Asn Ile
            900                 905                 910

Ser Ile Pro Val Lys Tyr Glu Val Gly Leu Gln Phe Tyr Ser Ser Ala
        915                 920                 925

Ser Glu Tyr His Ile Ser Ile Ala Ala Asn Glu Thr Val Pro Glu Val
    930                 935                 940

Ile Asn Ser Thr Glu Asp Ile Gly Asn Glu Ile Asn Ile Phe Tyr Leu
945                 950                 955                 960

Ile Arg Lys Ser Gly Ser Phe Pro Met Pro Glu Leu Lys Leu Ser Ile
                965                 970                 975

Ser Phe Pro Asn Met Thr Ser Asn Gly Tyr Pro Val Leu Tyr Pro Thr
            980                 985                 990

Gly Leu Ser Ser Ser Glu Asn Ala  Asn Cys Arg Pro His  Ile Phe Glu
        995                 1000                1005

Asp Pro  Phe Ser Ile Asn Ser  Gly Lys Lys Met Thr  Thr Ser Thr Asp
    1010                1015                1020

His  Leu Lys Arg Gly Thr  Ile Leu Asp Cys Asn  Thr Cys Lys Phe Ala
1025                1030                1035                1040

Thr Ile Thr Cys Asn  Leu Thr Ser Ser Asp  Ile Ser Gln Val Asn  Val
                1045                1050                1055

Ser Leu Ile Leu  Trp Lys Pro Thr Phe  Ile Lys Ser Tyr Phe  Ser Ser
            1060                1065                1070

Leu Asn Leu  Thr Ile Arg Gly Glu  Leu Arg Ser Glu Asn  Ala Ser Leu
        1075                1080                1085

Val Leu  Ser Ser Ser Asn Gln  Lys Arg Glu Leu Ala  Ile Gln Ile Ser
    1090                1095                1100

Lys  Asp Gly Leu Pro Gly  Arg Val Pro Leu Trp  Val Ile Leu Leu Ser
1105                1110                1115                1120

Ala Phe Ala Gly Leu  Leu Leu Leu Met Leu  Leu Ile Leu Ala Leu  Trp
                1125                1130                1135

Lys Ile Gly Phe  Phe Lys Arg Pro Leu  Lys Lys Lys Met Glu  Lys
            1140                1145                1150
```

<210> SEQ ID NO 192
<211> LENGTH: 389
<212> TYPE: DNA
<213> ORGANISM: Homo sapiens
<220> FEATURE:
<221> NAME/KEY: misc_feature
<222> LOCATION: (256)
<223> OTHER INFORMATION: n equals a,t,g, or c
<220> FEATURE:
<221> NAME/KEY: misc_feature
<222> LOCATION: (279)
<223> OTHER INFORMATION: n equals a,t,g, or c
<220> FEATURE:
<221> NAME/KEY: misc_feature
<222> LOCATION: (302)
<223> OTHER INFORMATION: n equals a,t,g, or c
<220> FEATURE:
<221> NAME/KEY: misc_feature
<222> LOCATION: (310)
<223> OTHER INFORMATION: n equals a,t,g, or c
<220> FEATURE:
<221> NAME/KEY: misc_feature
<222> LOCATION: (347)

<223> OTHER INFORMATION: n equals a,t,g, or c
<220> FEATURE:
<221> NAME/KEY: misc_feature
<222> LOCATION: (349)
<223> OTHER INFORMATION: n equals a,t,g, or c
<220> FEATURE:
<221> NAME/KEY: misc_feature
<222> LOCATION: (382)
<223> OTHER INFORMATION: n equals a,t,g, or c

<400> SEQUENCE: 192

```
gcctccagta ttttggctgc agcatccacg ggcaattggt acctcaatga gggatgggct     60

catcgacctg gcagtgggag cccttggcaa cgctgtgatt ctgtggtccc gcccagtggt    120

tcagatcaat gccagcctcc actttgagcc atccaagatc aacatcttcc acagagactg    180

caagcgcagt ggcagggatg ccacctgcct ggccgccttc ctctgcttca cgcccatctt    240

cctggcaccc catttncaaa caacaactgt tggcatcana tacaacgcca ccatgggatg    300

anaggcggtn tacaccgagg gcccacctgg acaaggcggg gaccgantna caacagaacc    360

gtactggttt tcttcggcca gnaacttgt                                      389
```

<210> SEQ ID NO 193
<211> LENGTH: 491
<212> TYPE: DNA
<213> ORGANISM: Homo sapiens
<220> FEATURE:
<221> NAME/KEY: misc_feature
<222> LOCATION: (11)
<223> OTHER INFORMATION: n equals a,t,g, or c
<220> FEATURE:
<221> NAME/KEY: misc_feature
<222> LOCATION: (212)
<223> OTHER INFORMATION: n equals a,t,g, or c
<220> FEATURE:
<221> NAME/KEY: misc_feature
<222> LOCATION: (268)
<223> OTHER INFORMATION: n equals a,t,g, or c
<220> FEATURE:
<221> NAME/KEY: misc_feature
<222> LOCATION: (274)
<223> OTHER INFORMATION: n equals a,t,g, or c
<220> FEATURE:
<221> NAME/KEY: misc_feature
<222> LOCATION: (290)
<223> OTHER INFORMATION: n equals a,t,g, or c
<220> FEATURE:
<221> NAME/KEY: misc_feature
<222> LOCATION: (297)
<223> OTHER INFORMATION: n equals a,t,g, or c
<220> FEATURE:
<221> NAME/KEY: misc_feature
<222> LOCATION: (317)
<223> OTHER INFORMATION: n equals a,t,g, or c
<220> FEATURE:
<221> NAME/KEY: misc_feature
<222> LOCATION: (355)
<223> OTHER INFORMATION: n equals a,t,g, or c
<220> FEATURE:
<221> NAME/KEY: misc_feature
<222> LOCATION: (381)
<223> OTHER INFORMATION: n equals a,t,g, or c
<220> FEATURE:
<221> NAME/KEY: misc_feature
<222> LOCATION: (384)
<223> OTHER INFORMATION: n equals a,t,g, or c
<220> FEATURE:
<221> NAME/KEY: misc_feature
<222> LOCATION: (398)
<223> OTHER INFORMATION: n equals a,t,g, or c
<220> FEATURE:
<221> NAME/KEY: misc_feature
<222> LOCATION: (400)
<223> OTHER INFORMATION: n equals a,t,g, or c
<220> FEATURE:

<221> NAME/KEY: misc_feature
<222> LOCATION: (404)
<223> OTHER INFORMATION: n equals a,t,g, or c
<220> FEATURE:
<221> NAME/KEY: misc_feature
<222> LOCATION: (405)
<223> OTHER INFORMATION: n equals a,t,g, or c
<220> FEATURE:
<221> NAME/KEY: misc_feature
<222> LOCATION: (407)
<223> OTHER INFORMATION: n equals a,t,g, or c
<220> FEATURE:
<221> NAME/KEY: misc_feature
<222> LOCATION: (413)
<223> OTHER INFORMATION: n equals a,t,g, or c
<220> FEATURE:
<221> NAME/KEY: misc_feature
<222> LOCATION: (414)
<223> OTHER INFORMATION: n equals a,t,g, or c
<220> FEATURE:
<221> NAME/KEY: misc_feature
<222> LOCATION: (415)
<223> OTHER INFORMATION: n equals a,t,g, or c
<220> FEATURE:
<221> NAME/KEY: misc_feature
<222> LOCATION: (434)
<223> OTHER INFORMATION: n equals a,t,g, or c
<220> FEATURE:
<221> NAME/KEY: misc_feature
<222> LOCATION: (438)
<223> OTHER INFORMATION: n equals a,t,g, or c
<220> FEATURE:
<221> NAME/KEY: misc_feature
<222> LOCATION: (443)
<223> OTHER INFORMATION: n equals a,t,g, or c
<220> FEATURE:
<221> NAME/KEY: misc_feature
<222> LOCATION: (462)
<223> OTHER INFORMATION: n equals a,t,g, or c
<220> FEATURE:
<221> NAME/KEY: misc_feature
<222> LOCATION: (465)
<223> OTHER INFORMATION: n equals a,t,g, or c
<220> FEATURE:
<221> NAME/KEY: misc_feature
<222> LOCATION: (466)
<223> OTHER INFORMATION: n equals a,t,g, or c
<220> FEATURE:
<221> NAME/KEY: misc_feature
<222> LOCATION: (467)
<223> OTHER INFORMATION: n equals a,t,g, or c
<220> FEATURE:
<221> NAME/KEY: misc_feature
<222> LOCATION: (482)
<223> OTHER INFORMATION: n equals a,t,g, or c
<220> FEATURE:
<221> NAME/KEY: misc_feature
<222> LOCATION: (483)
<223> OTHER INFORMATION: n equals a,t,g, or c

<400> SEQUENCE: 193
gaattcggca naggcagaca ctgctccttg ggtagccata actgtgtccc cactttccag 60
ggtgccagac ctacatggac atcgtcattg tcctggatgg gtccaacagc atctacccct 120
gggtgggggt tcagcacttc ctcatcaaca tcctgaaaaa gttttacatt ggcccagggc 180
agatccaggt tggagttgtg cagtatggcg angatgtggt gcatgagttt cacctcaatg 240
actacaggtc tgtaaaagat gtggtggnag ctgncagcca cattgagccn gagaggnggg 300
acagagaccc ggacggnatt tggcattgga atttggcacg gttaaaaaaa aagtngggcc 360
aaaaaaattt tttttgggtc ncanatgctt ttgtagtnan tccnntnggc ttnnnaacaa 420
atttccccaa attnggtncc ctngggccat atttttttat tnccnnnaat tttggggttt 480
gnntgggtca a 491

<210> SEQ ID NO 194
<211> LENGTH: 340
<212> TYPE: DNA
<213> ORGANISM: Homo sapiens
<220> FEATURE:
<221> NAME/KEY: misc_feature
<222> LOCATION: (5)
<223> OTHER INFORMATION: n equals a,t,g, or c
<220> FEATURE:
<221> NAME/KEY: misc_feature
<222> LOCATION: (188)
<223> OTHER INFORMATION: n equals a,t,g, or c
<220> FEATURE:
<221> NAME/KEY: misc_feature
<222> LOCATION: (251)
<223> OTHER INFORMATION: n equals a,t,g, or c
<220> FEATURE:
<221> NAME/KEY: misc_feature
<222> LOCATION: (292)
<223> OTHER INFORMATION: n equals a,t,g, or c
<220> FEATURE:
<221> NAME/KEY: misc_feature
<222> LOCATION: (308)
<223> OTHER INFORMATION: n equals a,t,g, or c
<220> FEATURE:
<221> NAME/KEY: misc_feature
<222> LOCATION: (312)
<223> OTHER INFORMATION: n equals a,t,g, or c
<220> FEATURE:
<221> NAME/KEY: misc_feature
<222> LOCATION: (327)
<223> OTHER INFORMATION: n equals a,t,g, or c

<400> SEQUENCE: 194
ggcanaggag taaatgagcg ggacagcacc aaggaagaca acgtggcccc cttacgcttc 60
cacctcaaat acgaggctga cgtcctcttc accaggagca gcagcctgag ccactacgaa 120
ggtcaagctc aacagctcgc tggagagata cgatggtatc gggcctccct tcagctgcat 180
cttcaggntc cagaacttgg gcttgttccc catccacggg atgatggatg gaagatcacc 240
attcccatcg ncaccaggag cggcaaccgc cttactgaag ttgagggact tnctcaagga 300
cgaggcgnac angtcctgta aacattnggg gcaatagcat 340

<210> SEQ ID NO 195
<211> LENGTH: 356
<212> TYPE: DNA
<213> ORGANISM: Homo sapiens
<220> FEATURE:
<221> NAME/KEY: misc_feature
<222> LOCATION: (5)
<223> OTHER INFORMATION: n equals a,t,g, or c
<220> FEATURE:
<221> NAME/KEY: misc_feature
<222> LOCATION: (9)
<223> OTHER INFORMATION: n equals a,t,g, or c
<220> FEATURE:
<221> NAME/KEY: misc_feature
<222> LOCATION: (84)
<223> OTHER INFORMATION: n equals a,t,g, or c
<220> FEATURE:
<221> NAME/KEY: misc_feature
<222> LOCATION: (298)
<223> OTHER INFORMATION: n equals a,t,g, or c
<220> FEATURE:
<221> NAME/KEY: misc_feature
<222> LOCATION: (311)
<223> OTHER INFORMATION: n equals a,t,g, or c
<220> FEATURE:
<221> NAME/KEY: misc_feature
<222> LOCATION: (312)
<223> OTHER INFORMATION: n equals a,t,g, or c
<220> FEATURE:
<221> NAME/KEY: misc_feature
<222> LOCATION: (336)

<223> OTHER INFORMATION: n equals a,t,g, or c
<220> FEATURE:
<221> NAME/KEY: misc_feature
<222> LOCATION: (339)
<223> OTHER INFORMATION: n equals a,t,g, or c
<220> FEATURE:
<221> NAME/KEY: misc_feature
<222> LOCATION: (342)
<223> OTHER INFORMATION: n equals a,t,g, or c
<220> FEATURE:
<221> NAME/KEY: misc_feature
<222> LOCATION: (343)
<223> OTHER INFORMATION: n equals a,t,g, or c

<400> SEQUENCE: 195
ggcanaggng aaatcaattt ccatctactg gggaacctgt ggttgaggtc cctaaaagca 60
ctcaagtaca gatccatgaa aatnatggtc aacgcagcct tgcagaggca ggttgcacag 120
ccccttcatc ttccgtgaag gaggtatccc agccgccaga tcgtgtttga gaatctccaa 180
gcaagaggac tggcaggtcc ccatctggat cattgtaggc agcaccctgg ggggcctcct 240
actgctggcc ctgctggttc ctgggcactg tgggaagctt cggtttcttt aagaagtntc 300
caggtcgcag nnggggtagc ctggttctgg gacccnaanc cnnaaaattg ctgggt 356

<210> SEQ ID NO 196
<211> LENGTH: 262
<212> TYPE: DNA
<213> ORGANISM: Homo sapiens
<220> FEATURE:
<221> NAME/KEY: misc_feature
<222> LOCATION: (76)
<223> OTHER INFORMATION: n equals a,t,g, or c
<220> FEATURE:
<221> NAME/KEY: misc_feature
<222> LOCATION: (216)
<223> OTHER INFORMATION: n equals a,t,g, or c
<220> FEATURE:
<221> NAME/KEY: misc_feature
<222> LOCATION: (234)
<223> OTHER INFORMATION: n equals a,t,g, or c
<220> FEATURE:
<221> NAME/KEY: misc_feature
<222> LOCATION: (248)
<223> OTHER INFORMATION: n equals a,t,g, or c
<220> FEATURE:
<221> NAME/KEY: misc_feature
<222> LOCATION: (257)
<223> OTHER INFORMATION: n equals a,t,g, or c
<220> FEATURE:
<221> NAME/KEY: misc_feature
<222> LOCATION: (259)
<223> OTHER INFORMATION: n equals a,t,g, or c

<400> SEQUENCE: 196
ctgcacaccg gacccagccg ccgtgccgcg ggccatggta cctgcccagg ggcctggtgg 60
tggcctgggc gctcancctg tggccagggt tcacggacac cttcaacatg gtacaccagg 120
aagccccggg tcatccctgg ctccaggacc gccttctttg gctacacagt gcagcagcac 180
gacatcagtg gcaataagtg gctggtcctt ggggcncccc actggaaacc aatngctaca 240
aaaaaaangg aaaactntnc aa 262

<210> SEQ ID NO 197
<211> LENGTH: 327
<212> TYPE: DNA
<213> ORGANISM: Homo sapiens
<220> FEATURE:
<221> NAME/KEY: misc_feature
<222> LOCATION: (7)
<223> OTHER INFORMATION: n equals a,t,g, or c
<220> FEATURE:

<221> NAME/KEY: misc_feature
<222> LOCATION: (33)
<223> OTHER INFORMATION: n equals a,t,g, or c
<220> FEATURE:
<221> NAME/KEY: misc_feature
<222> LOCATION: (47)
<223> OTHER INFORMATION: n equals a,t,g, or c
<220> FEATURE:
<221> NAME/KEY: misc_feature
<222> LOCATION: (55)
<223> OTHER INFORMATION: n equals a,t,g, or c
<220> FEATURE:
<221> NAME/KEY: misc_feature
<222> LOCATION: (67)
<223> OTHER INFORMATION: n equals a,t,g, or c
<220> FEATURE:
<221> NAME/KEY: misc_feature
<222> LOCATION: (98)
<223> OTHER INFORMATION: n equals a,t,g, or c
<220> FEATURE:
<221> NAME/KEY: misc_feature
<222> LOCATION: (153)
<223> OTHER INFORMATION: n equals a,t,g, or c
<220> FEATURE:
<221> NAME/KEY: misc_feature
<222> LOCATION: (186)
<223> OTHER INFORMATION: n equals a,t,g, or c
<220> FEATURE:
<221> NAME/KEY: misc_feature
<222> LOCATION: (259)
<223> OTHER INFORMATION: n equals a,t,g, or c
<220> FEATURE:
<221> NAME/KEY: misc_feature
<222> LOCATION: (283)
<223> OTHER INFORMATION: n equals a,t,g, or c
<220> FEATURE:
<221> NAME/KEY: misc_feature
<222> LOCATION: (293)
<223> OTHER INFORMATION: n equals a,t,g, or c
<220> FEATURE:
<221> NAME/KEY: misc_feature
<222> LOCATION: (316)
<223> OTHER INFORMATION: n equals a,t,g, or c
<220> FEATURE:
<221> NAME/KEY: misc_feature
<222> LOCATION: (326)
<223> OTHER INFORMATION: n equals a,t,g, or c

<400> SEQUENCE: 197
ggcagancta cagcacggtc ctaaatatct cgnagtcagc aaacctncag tttcnagctt 60
aatccanaag gaggactcaa acggtagcat tgagtgtntg aacgaggaga ggaggctcca 120
gaagcaagtt tgcaacgtca gctatccctt ctnccgggcc aaggccaagg tggctttccg 180
tcttgnattt taagttcagc aaatccatct tcctacacca cctggagatc gagcctcgct 240
gcagcagtga cagtaatgng atgaggggtt agccggggtt tgnacccaag tgnatttcac 300
attggccgga aatttnaaaa tttccnc 327

<210> SEQ ID NO 198
<211> LENGTH: 301
<212> TYPE: DNA
<213> ORGANISM: Homo sapiens
<220> FEATURE:
<221> NAME/KEY: misc_feature
<222> LOCATION: (71)
<223> OTHER INFORMATION: n equals a,t,g, or c
<220> FEATURE:
<221> NAME/KEY: misc_feature
<222> LOCATION: (72)
<223> OTHER INFORMATION: n equals a,t,g, or c
<220> FEATURE:
<221> NAME/KEY: misc_feature
<222> LOCATION: (90)
<223> OTHER INFORMATION: n equals a,t,g, or c
<220> FEATURE:

<221> NAME/KEY: misc_feature
<222> LOCATION: (194)
<223> OTHER INFORMATION: n equals a,t,g, or c
<220> FEATURE:
<221> NAME/KEY: misc_feature
<222> LOCATION: (212)
<223> OTHER INFORMATION: n equals a,t,g, or c
<220> FEATURE:
<221> NAME/KEY: misc_feature
<222> LOCATION: (241)
<223> OTHER INFORMATION: n equals a,t,g, or c
<220> FEATURE:
<221> NAME/KEY: misc_feature
<222> LOCATION: (245)
<223> OTHER INFORMATION: n equals a,t,g, or c
<220> FEATURE:
<221> NAME/KEY: misc_feature
<222> LOCATION: (268)
<223> OTHER INFORMATION: n equals a,t,g, or c
<220> FEATURE:
<221> NAME/KEY: misc_feature
<222> LOCATION: (275)
<223> OTHER INFORMATION: n equals a,t,g, or c
<220> FEATURE:
<221> NAME/KEY: misc_feature
<222> LOCATION: (290)
<223> OTHER INFORMATION: n equals a,t,g, or c
<220> FEATURE:
<221> NAME/KEY: misc_feature
<222> LOCATION: (296)
<223> OTHER INFORMATION: n equals a,t,g, or c

<400> SEQUENCE: 198
cccatagata ggcccctggg gctcctgaaa gaatgaaccc aagagcaagg gcttaatggt 60
aacagctgca nnaagggaat gaagaaagan tctaagaatg tggagactga tggccaggca 120
agtgggacca ggatactgaa cgctgtcctg aagaatgaga aggtagccgg gctctgcacc 180
cacgtgcatt gcanattgaa ccgcaactga anacattccc ccaccagctg cagccccttg 240
ntctncagtt gccaaccctc ccgggtgnaa ttttnttccc aggtaccttn atgggnaagc 300
a 301

<210> SEQ ID NO 199
<211> LENGTH: 478
<212> TYPE: DNA
<213> ORGANISM: Homo sapiens
<220> FEATURE:
<221> NAME/KEY: misc_feature
<222> LOCATION: (96)
<223> OTHER INFORMATION: n equals a,t,g, or c
<220> FEATURE:
<221> NAME/KEY: misc_feature
<222> LOCATION: (285)
<223> OTHER INFORMATION: n equals a,t,g, or c
<220> FEATURE:
<221> NAME/KEY: misc_feature
<222> LOCATION: (359)
<223> OTHER INFORMATION: n equals a,t,g, or c
<220> FEATURE:
<221> NAME/KEY: misc_feature
<222> LOCATION: (387)
<223> OTHER INFORMATION: n equals a,t,g, or c
<220> FEATURE:
<221> NAME/KEY: misc_feature
<222> LOCATION: (407)
<223> OTHER INFORMATION: n equals a,t,g, or c
<220> FEATURE:
<221> NAME/KEY: misc_feature
<222> LOCATION: (433)
<223> OTHER INFORMATION: n equals a,t,g, or c
<220> FEATURE:
<221> NAME/KEY: misc_feature
<222> LOCATION: (452)
<223> OTHER INFORMATION: n equals a,t,g, or c
<220> FEATURE:

<221> NAME/KEY: misc_feature
<222> LOCATION: (469)
<223> OTHER INFORMATION: n equals a,t,g, or c

<400> SEQUENCE: 199
ggcacagtgg ccgtgggcag gtcactccgg gcatccaaca caaggtcagg gacacagtgc 60
tcatcctcat tgcagccgtt ccagaagggc acctgngcca gggagagcca ggtgtgggca 120
gctgggtagg gacccgcagc ccctcgccct caatgtacac cagctctgtc tccaccacac 180
tagacatggg ctggctttcc tgcactgtcc ccagacacca cactgctctg tcttgtgctt 240
ttccatagat gcttccctct ttaaaacgat gctcaaagct tcagntcctc ctggctcccc 300
tccagtttca tgaatggagc tgatggcaca gaacccccaa ccccattcaa ccagcagang 360
gttctggttc aacatttatt gatcaanaat gtgtgtgggg caagggnttg gtaatggggg 420
ttacaaaaca agnaagttgg cagttttggc cntcagttca aggggaaant ggtgtttg 478

<210> SEQ ID NO 200
<211> LENGTH: 224
<212> TYPE: DNA
<213> ORGANISM: Homo sapiens
<220> FEATURE:
<221> NAME/KEY: misc_feature
<222> LOCATION: (12)
<223> OTHER INFORMATION: n equals a,t,g, or c
<220> FEATURE:
<221> NAME/KEY: misc_feature
<222> LOCATION: (21)
<223> OTHER INFORMATION: n equals a,t,g, or c
<220> FEATURE:
<221> NAME/KEY: misc_feature
<222> LOCATION: (49)
<223> OTHER INFORMATION: n equals a,t,g, or c
<220> FEATURE:
<221> NAME/KEY: misc_feature
<222> LOCATION: (66)
<223> OTHER INFORMATION: n equals a,t,g, or c
<220> FEATURE:
<221> NAME/KEY: misc_feature
<222> LOCATION: (176)
<223> OTHER INFORMATION: n equals a,t,g, or c
<220> FEATURE:
<221> NAME/KEY: misc_feature
<222> LOCATION: (184)
<223> OTHER INFORMATION: n equals a,t,g, or c
<220> FEATURE:
<221> NAME/KEY: misc_feature
<222> LOCATION: (197)
<223> OTHER INFORMATION: n equals a,t,g, or c
<220> FEATURE:
<221> NAME/KEY: misc_feature
<222> LOCATION: (212)
<223> OTHER INFORMATION: n equals a,t,g, or c
<220> FEATURE:
<221> NAME/KEY: misc_feature
<222> LOCATION: (221)
<223> OTHER INFORMATION: n equals a,t,g, or c

<400> SEQUENCE: 200
ctattgcccc anatgttaca ngacgtgttc gcctcgtccg tgtaggaant ccctcagctt 60
cagtangcgg ttgccgctcc tggtggcgag ggaatggtga atcttcatca tcatcccgtg 120
gtatggggaa caaacccaag ttctggatcc tgaaaaatca actgaaagga aggccnatac 180
atcntatctc tccaacnaac tgttggcttg anctcctaat ngtt 224

<210> SEQ ID NO 201
<211> LENGTH: 126
<212> TYPE: DNA
<213> ORGANISM: Homo sapiens
<220> FEATURE:

<221> NAME/KEY: misc_feature
<222> LOCATION: (72)
<223> OTHER INFORMATION: n equals a,t,g, or c

<400> SEQUENCE: 201
ggcacgagct gacatctctc tgtcactctg ttgcaggcac caacaagaac gagacctcct 60
ttgggctgtg gnagtcacag acgggctttt cctcgcacgt ggtggaggta tgtggtggag 120
gtacgg 126

<210> SEQ ID NO 202
<211> LENGTH: 2184
<212> TYPE: DNA
<213> ORGANISM: Homo sapiens

<400> SEQUENCE: 202
ccacgcgtcc gggcctgcct ctccactcag agggacatca gctcaagagc aatcacacaa 60
ccccagagaa gaaatccaaa cctcaccttc tgttgctgct tctctactat cttatgggtg 120
cttgactggc tctcccaagc ctgctgtcct gcagcctcac tgcctgtgtc cttttctcag 180
gcagtgtgct ggcgttccat gcgacgtggc tgtgcagtgc tgggagccct ggggctgctg 240
gccggtgcag gtgttggctc atggctccta gtgctgtatc tgtgtcctgc tgcctctcag 300
cccatttccg ggaccttgca ggatgaggag ataactttga gctgctcaga ggccagcgct 360
gaggaagctc tgctccctgc acttcccaaa acagtatctt tcagaataaa cagcgaagac 420
ttcttgctgg aagcgcaagt gagggatcag ccacgctggc tcctggtctg ccatgagggc 480
tggagccccg ccctggggct gcagatctgc tggagccttg ggcatctcag actcactcac 540
cacaagggag taaacctcac tgacatcaaa ctcaacagtt cccaggagtt tgctcagctc 600
tctcctagac tgggaggctt cctggaggag gcgtggcagc ccaggaacaa ctgcacttct 660
ggtcaagttg tttccctcag atgctctgag tgtggagcga ggcccctggc ttcccggata 720
gttggtgggc agtctgtggc tcctgggcgc tggccgtggc aggccagcgt ggccctgggc 780
ttccggcaca cgtgtggggg ctctgtgcta gcgccacgct gggtggtgac tgctgcacat 840
tgtatgcaca gtttcaggct ggcccgcctg tccagctggc gggttcatgc ggggctggtc 900
agccacagtg ccgtcaggcc ccaccaaggg gctctggtgg agaggattat cccacacccc 960
ctctacagtg cccagaatca tgactacgac gtcgccctcc tgaggctcca gaccgctctc 1020
aacttctcag acactgtggg cgctgtgtgc ctgccggcca aggaacagca ttttccgaag 1080
ggctcgcggt gctgggtgtc tggctggggc cacacccacc ctagccatac ttacagctcg 1140
gatatgctcc aggacacggt ggtgcccttg ttcagcactc agctctgcaa cagctcttgc 1200
gtgtacagcg gagccctcac cccccgcatg ctttgcgctg gctacctgga cggaagggct 1260
gatgcatgcc agggagatag cgggggcccc ctagtgtgcc cagatgggga cacatggcgc 1320
ctagtggggg tggtcagctg gggcgtggc tgcgcagagc ccaatcaccc aggtgtctac 1380
gccaaggtag ctgagtttct ggactggatc catgacactg ctcaggactc cctcctctga 1440
gtcctgctgt ttcctccagt ctcactgcac accactgcct catgcttcct ggggcctcca 1500
gcagctccac taatggagga gaggcagtag cctccgacac agaacgcatg gacctcctac 1560
tactgtgtgt gaggaacagt cactacccac tggccagcca cccagccaac aggtctctcc 1620
tcttgggcct gatttcagag tcctctttct cactagagac tcaatgacag aagagaggct 1680
gggacttggt tgggcatgct gtggttgctg agggatgagg gggaggagag aggtaggagc 1740
tggagatgaa gaggctgcta gaagcagcag gaagcctgcc cttctgcctt ttcccttccc 1800

-continued

```
tgcccctgtg tgagtctttt gggagggtgc tgggaggtgc cccccgtccc accttttttcc   1860

tgtgctctag gtgggctaag tgcctcccta gaggactcca tggctgagag gctcctgggc   1920

agatggggtc aaggctgggc cagcccagat gaagcctatg ggagtcagga ccctctccac   1980

tctccctctc cactcccctt cctgttctca cctggctgtg gctggccctg tgtggggtgg   2040

gtacactgga aaacaagaag gttggagttg gtctaggaca ttggttttaa atgacagttc   2100

tgtgaactgg tccaaggagt tctgttatta aagtgatata tggtcttggt ccaaaaaaaa   2160

aaaaaaaaaa aaaaaaaaaa aaaa                                           2184


<210> SEQ ID NO 203
<211> LENGTH: 413
<212> TYPE: PRT
<213> ORGANISM: Homo sapiens

<400> SEQUENCE: 203

Met Arg Arg Gly Cys Ala Val Leu Gly Ala Leu Gly Leu Leu Ala Gly
1               5                   10                  15

Ala Gly Val Gly Ser Trp Leu Leu Val Leu Tyr Leu Cys Pro Ala Ala
            20                  25                  30

Ser Gln Pro Ile Ser Gly Thr Leu Gln Asp Glu Glu Ile Thr Leu Ser
        35                  40                  45

Cys Ser Glu Ala Ser Ala Glu Glu Ala Leu Leu Pro Ala Leu Pro Lys
    50                  55                  60

Thr Val Ser Phe Arg Ile Asn Ser Glu Asp Phe Leu Leu Glu Ala Gln
65                  70                  75                  80

Val Arg Asp Gln Pro Arg Trp Leu Leu Val Cys His Glu Gly Trp Ser
                85                  90                  95

Pro Ala Leu Gly Leu Gln Ile Cys Trp Ser Leu Gly His Leu Arg Leu
            100                 105                 110

Thr His His Lys Gly Val Asn Leu Thr Asp Ile Lys Leu Asn Ser Ser
        115                 120                 125

Gln Glu Phe Ala Gln Leu Ser Pro Arg Leu Gly Gly Phe Leu Glu Glu
    130                 135                 140

Ala Trp Gln Pro Arg Asn Asn Cys Thr Ser Gly Gln Val Val Ser Leu
145                 150                 155                 160

Arg Cys Ser Glu Cys Gly Ala Arg Pro Leu Ala Ser Arg Ile Val Gly
                165                 170                 175

Gly Gln Ser Val Ala Pro Gly Arg Trp Pro Trp Gln Ala Ser Val Ala
            180                 185                 190

Leu Gly Phe Arg His Thr Cys Gly Gly Ser Val Leu Ala Pro Arg Trp
        195                 200                 205

Val Val Thr Ala Ala His Cys Met His Ser Phe Arg Leu Ala Arg Leu
    210                 215                 220

Ser Ser Trp Arg Val His Ala Gly Leu Val Ser His Ser Ala Val Arg
225                 230                 235                 240

Pro His Gln Gly Ala Leu Val Glu Arg Ile Ile Pro His Pro Leu Tyr
                245                 250                 255

Ser Ala Gln Asn His Asp Tyr Asp Val Ala Leu Leu Arg Leu Gln Thr
            260                 265                 270

Ala Leu Asn Phe Ser Asp Thr Val Gly Ala Val Cys Leu Pro Ala Lys
        275                 280                 285

Glu Gln His Phe Pro Lys Gly Ser Arg Cys Trp Val Ser Gly Trp Gly
    290                 295                 300

His Thr His Pro Ser His Thr Tyr Ser Ser Asp Met Leu Gln Asp Thr
```

-continued

```
305                 310                 315                 320

Val Val Pro Leu Phe Ser Thr Gln Leu Cys Asn Ser Ser Cys Val Tyr
                325                 330                 335

Ser Gly Ala Leu Thr Pro Arg Met Leu Cys Ala Gly Tyr Leu Asp Gly
            340                 345                 350

Arg Ala Asp Ala Cys Gln Gly Asp Ser Gly Gly Pro Leu Val Cys Pro
        355                 360                 365

Asp Gly Asp Thr Trp Arg Leu Val Gly Val Val Ser Trp Gly Arg Gly
    370                 375                 380

Cys Ala Glu Pro Asn His Pro Gly Val Tyr Ala Lys Val Ala Glu Phe
385                 390                 395                 400

Leu Asp Trp Ile His Asp Thr Ala Gln Asp Ser Leu Leu
                405                 410


<210> SEQ ID NO 204
<211> LENGTH: 2190
<212> TYPE: DNA
<213> ORGANISM: Homo sapiens

<400> SEQUENCE: 204

tcgacccacg cgtccgggcc tgcctctcca ctcagaggga catcagctca agagcaatca     60

cacaacccca gagaagaaat ccaaacctca ccttctgttg ctgcttctct actatcttat    120

gggtgcttga ctggctctcc caagcctgct gtcctgcagc ctcactgcct gtgtcctttt    180

ctcaggcagt gtgctggcgt tccatgcgac gtggctgtgc agtgctggga gccctggggc    240

tgctggccgg tgcaggtgtt ggctcatggc tcctagtgct gtatctgtgt cctgctgcct    300

ctcagcccat ttccgggacc ttgcaggatg aggagataac tttgagctgc tcagaggcca    360

gcgctgagga agctctgctc cctgcacttc ccaaaacagt atctttcaga ataaacagcg    420

aagacttctt gctggaagcg caagtgaggg atcagccacg ctggctcctg gtctgccatg    480

agggctggag ccccgccctg ggctgcagga tctgctggag ccttgggcat ctcagactca    540

ctcaccacaa gggagtaaac ctcactgaca tcaaactcaa cagttcccag gagtttgctc    600

agctctctcc tagactggga ggcttcctgg aggaggcgtg gcagcccagg aacaactgca    660

cttctggtca agttgtttcc ctcagatgct ctgagtgtgg agcgaggccc ctggcttccc    720

ggatagttgg tgggcagtct gtggctcctg ggcgctggcc gtggcaggcc agcgtggccc    780

tgggcttccg gcacacgtgt gggggctctg tgctagcgcc acgctgggtg gtgactgctg    840

cacattgtat gcacagtttc aggctggccc gcctgtccag ctggcgggtt catgcggggc    900

tggtcagcca cagtgccgtc aggccccacc aaggggctct ggtggagagg attatcccac    960

accccctcta cagtgcccag aatcatgact acgacgtcgc cctcctgagg ctccagaccg   1020

ctctcaactt ctcagacact gtgggcgctg tgtgcctgcc ggccaaggaa cagcattttc   1080

cgaagggctc gcggtgctgg gtgtctggct ggggccacac ccaccctagc catacttaca   1140

gctcggatat gctccaggac acggtggtgc ccttgttcag cactcagctc tgcaacagct   1200

cttgcgtgta cagcggagcc ctcacccccc gcatgctttg cgctggctac ctggacggaa   1260

gggctgatgc atgccaggga gatagcgggg gccccctagt gtgcccagat ggggacacat   1320

ggcgcctagt gggggtggtc agctgggggc gtggctgcgc agagcccaat cacccaggtg   1380

tctacgccaa ggtagctgag tttctggact ggatccatga cactgctcag gactccctcc   1440

tctgagtcct gctgtttcct ccagtctcac tgcacaccac tgcctcatgc ttcctggggc   1500

ctccagcagc tccactaatg gaggagaggc agtagcttcc gacacagaac gcatggacct   1560
```

cctactactg tgtgtgagga acagtcacta cccactggcc agccacccag ccaacaggtc 1620
tctcctcttg ggccctgatt tcagagtcct ctttctcact agagactcaa tgacagaaga 1680
gaggctggga cttggttggg catgctgtgg ttgatgaggg atgaggggga ggagagaggt 1740
aggagctgga gatgaagagg ctgctagaag cagcaggaag cctgcccttc tgccctctcc 1800
cttccctgcc cctgtgtgag tcttttggga gggtgctggg aggtgccccc cgtcccacct 1860
ttttcctgtg ctctaggtgg gctaagtgcc tccctagagg actccatggc tgagaggctc 1920
ctgggcagat ggggtcaagg ctgggccagc ccagatgaag cctatgggag tcaggaccct 1980
ctccactctc cctctccact cccettcctg ttctcacctg gctgtggctg gccctgtgtg 2040
gggtgggtac actggaaaac aagaaggttg gagttggtct aggacattgg ttttaaatga 2100
cagttctgtg aactggtcca aggagttctg ttattaaagt gatatatggt cttggtccaa 2160
aaaaaaaaaa aaaaaaaaaa aaaaaaaaaa 2190

<210> SEQ ID NO 205
<211> LENGTH: 413
<212> TYPE: PRT
<213> ORGANISM: Homo sapiens

<400> SEQUENCE: 205

Met Arg Arg Gly Cys Ala Val Leu Gly Ala Leu Gly Leu Leu Ala Gly
1 5 10 15

Ala Gly Val Gly Ser Trp Leu Leu Val Leu Tyr Leu Cys Pro Ala Ala
20 25 30

Ser Gln Pro Ile Ser Gly Thr Leu Gln Asp Glu Glu Ile Thr Leu Ser
35 40 45

Cys Ser Glu Ala Ser Ala Glu Glu Ala Leu Leu Pro Ala Leu Pro Lys
50 55 60

Thr Val Ser Phe Arg Ile Asn Ser Glu Asp Phe Leu Leu Glu Ala Gln
65 70 75 80

Val Arg Asp Gln Pro Arg Trp Leu Leu Val Cys His Glu Gly Trp Ser
85 90 95

Pro Ala Leu Gly Leu Gln Ile Cys Trp Ser Leu Gly His Leu Arg Leu
100 105 110

Thr His His Lys Gly Val Asn Leu Thr Asp Ile Lys Leu Asn Ser Ser
115 120 125

Gln Glu Phe Ala Gln Leu Ser Pro Arg Leu Gly Gly Phe Leu Glu Glu
130 135 140

Ala Trp Gln Pro Arg Asn Asn Cys Thr Ser Gly Gln Val Val Ser Leu
145 150 155 160

Arg Cys Ser Glu Cys Gly Ala Arg Pro Leu Ala Ser Arg Ile Val Gly
165 170 175

Gly Gln Ser Val Ala Pro Gly Arg Trp Pro Trp Gln Ala Ser Val Ala
180 185 190

Leu Gly Phe Arg His Thr Cys Gly Gly Ser Val Leu Ala Pro Arg Trp
195 200 205

Val Val Thr Ala Ala His Cys Met His Ser Phe Arg Leu Ala Arg Leu
210 215 220

Ser Ser Trp Arg Val His Ala Gly Leu Val Ser His Ser Ala Val Arg
225 230 235 240

Pro His Gln Gly Ala Leu Val Glu Arg Ile Ile Pro His Pro Leu Tyr
245 250 255

Ser Ala Gln Asn His Asp Tyr Asp Val Ala Leu Leu Arg Leu Gln Thr
260 265 270

```
Ala Leu Asn Phe Ser Asp Thr Val Gly Ala Val Cys Leu Pro Ala Lys
        275                 280                 285

Glu Gln His Phe Pro Lys Gly Ser Arg Cys Trp Val Ser Gly Trp Gly
    290                 295                 300

His Thr His Pro Ser His Thr Tyr Ser Ser Asp Met Leu Gln Asp Thr
305                 310                 315                 320

Val Val Pro Leu Phe Ser Thr Gln Leu Cys Asn Ser Ser Cys Val Tyr
                325                 330                 335

Ser Gly Ala Leu Thr Pro Arg Met Leu Cys Ala Gly Tyr Leu Asp Gly
            340                 345                 350

Arg Ala Asp Ala Cys Gln Gly Asp Ser Gly Gly Pro Leu Val Cys Pro
        355                 360                 365

Asp Gly Asp Thr Trp Arg Leu Val Gly Val Val Ser Trp Gly Arg Gly
    370                 375                 380

Cys Ala Glu Pro Asn His Pro Gly Val Tyr Ala Lys Val Ala Glu Phe
385                 390                 395                 400

Leu Asp Trp Ile His Asp Thr Ala Gln Asp Ser Leu Leu
                405                 410


<210> SEQ ID NO 206
<211> LENGTH: 1364
<212> TYPE: DNA
<213> ORGANISM: Homo sapiens

<400> SEQUENCE: 206

cggcacgagg cgaagaagaa tctgaggaaa cctgctgctt tcacagagga aggcatttgc      60

tggctttccc aaggcaagaa caatgaaaac aaagtcatga ggagttctct ctacctcaaa     120

tgaaggccgc agctcctgct caagctattt tggcagtctg agagaacagt acattctgaa     180

ccacattgac gcagggagca tgggtatctg gacctcaggc actgatatct tcctaagtct     240

ttgggagatt tacgtgtctc caagaagccc cggatggatg gactttatcc agcatttggg     300

agtttgctgt ttggttgctc ttatttcagt gggcctcctg tctgtggccg cctgctggtt     360

tctgccatca atcatagcgg ccgctgcctc ctggattatc acgtgtgttc tgctgtgttg     420

ctccaagcat gcacgatgtt ttattcttct tgtctttctc tcttgtggcc tgcgtgaagg     480

caggaatgct ttgattgcag ctggcacagg gatcgtcatc ttgggacacg tagaaaatat     540

ttttcacaac tttaaaggtc tcctagatgg tatgacttgc aacctaaggg caaagagctt     600

ttccatacat ttttccactt tgaaaaaata tattgaggca attcagtgga tttatggcct     660

tgccactcca ctaagtgtat ttgatgacct tgtttcttgg aaccagaccc tggcagtctc     720

tcttttcagt cccagccatg tcctggaggc acagctaaat gacagcaaag gggaagtcct     780

gagcgtcttg taccagatgg caacaaccac agaggtgttg tcctccctgg gtcagaagct     840

acttgccttt gcagggcttt cgctcgtcct gcttggcact ggcctcttca tgaagcgatt     900

tttgggccct tgtggttgga agtatgaaaa catctacatc accagacaat ttgttcagtt     960

tgatgaaagg gagagacatc aacagaggcc ctgtgtgctc ccgctgaata aggaggaaag    1020

gaggaagtat gtcatcatcc cgactttctg gccgactcct aaagaaagga aaaacctggg    1080

gctgtttttc ctccccatac ttatccatct ctgcatctgg gtgctgwttg cagctgtaga    1140

ttatctgctg tatcggctca ttttctcagt gagcaagcag tttcaaagct tgccagggtt    1200

tgaggttcac ttgaaactgc acggagagaa acaaggaact caagatatta tccatgattc    1260

ttcctttaat atatctgtgt ttgaacccaa ctgtatccca aaaccctggc aagctttgaa    1320
```

-continued

```
actgcttgct cactgagaaa atgagccgat acagcagata atct                  1364


<210> SEQ ID NO 207
<211> LENGTH: 352
<212> TYPE: PRT
<213> ORGANISM: Homo sapiens
<220> FEATURE:
<221> NAME/KEY: SITE
<222> LOCATION: (284)
<223> OTHER INFORMATION: Xaa equals any amino acid

<400> SEQUENCE: 207

Met Asp Phe Ile Gln His Leu Gly Val Cys Cys Leu Val Ala Leu Ile
  1               5                  10                  15

Ser Val Gly Leu Leu Ser Val Ala Ala Cys Trp Phe Leu Pro Ser Ile
             20                  25                  30

Ile Ala Ala Ala Ala Ser Trp Ile Ile Thr Cys Val Leu Leu Cys Cys
         35                  40                  45

Ser Lys His Ala Arg Cys Phe Ile Leu Leu Val Phe Leu Ser Cys Gly
     50                  55                  60

Leu Arg Glu Gly Arg Asn Ala Leu Ile Ala Ala Gly Thr Gly Ile Val
 65                  70                  75                  80

Ile Leu Gly His Val Glu Asn Ile Phe His Asn Phe Lys Gly Leu Leu
                 85                  90                  95

Asp Gly Met Thr Cys Asn Leu Arg Ala Lys Ser Phe Ser Ile His Phe
            100                 105                 110

Pro Leu Leu Lys Lys Tyr Ile Glu Ala Ile Gln Trp Ile Tyr Gly Leu
        115                 120                 125

Ala Thr Pro Leu Ser Val Phe Asp Asp Leu Val Ser Trp Asn Gln Thr
    130                 135                 140

Leu Ala Val Ser Leu Phe Ser Pro Ser His Val Leu Glu Ala Gln Leu
145                 150                 155                 160

Asn Asp Ser Lys Gly Glu Val Leu Ser Val Leu Tyr Gln Met Ala Thr
                165                 170                 175

Thr Thr Glu Val Leu Ser Ser Leu Gly Gln Lys Leu Leu Ala Phe Ala
            180                 185                 190

Gly Leu Ser Leu Val Leu Leu Gly Thr Gly Leu Phe Met Lys Arg Phe
        195                 200                 205

Leu Gly Pro Cys Gly Trp Lys Tyr Glu Asn Ile Tyr Ile Thr Arg Gln
    210                 215                 220

Phe Val Gln Phe Asp Glu Arg Glu Arg His Gln Gln Arg Pro Cys Val
225                 230                 235                 240

Leu Pro Leu Asn Lys Glu Glu Arg Arg Lys Tyr Val Ile Ile Pro Thr
                245                 250                 255

Phe Trp Pro Thr Pro Lys Glu Arg Lys Asn Leu Gly Leu Phe Phe Leu
            260                 265                 270

Pro Ile Leu Ile His Leu Cys Ile Trp Val Leu Xaa Ala Ala Val Asp
        275                 280                 285

Tyr Leu Leu Tyr Arg Leu Ile Phe Ser Val Ser Lys Gln Phe Gln Ser
    290                 295                 300

Leu Pro Gly Phe Glu Val His Leu Lys Leu His Gly Glu Lys Gln Gly
305                 310                 315                 320

Thr Gln Asp Ile Ile His Asp Ser Ser Phe Asn Ile Ser Val Phe Glu
                325                 330                 335

Pro Asn Cys Ile Pro Lys Pro Trp Gln Ala Leu Lys Leu Leu Ala His
            340                 345                 350
```

<210> SEQ ID NO 208
<211> LENGTH: 1583
<212> TYPE: DNA
<213> ORGANISM: Homo sapiens

<400> SEQUENCE: 208
attcggcacg aggaaacctg ctgctttcac agaggaaggc atttgctggc tttcccaagg 60
caagaacaat gaaaacaaag tcatgaggag ttctctctac ctcaaatgaa ggccgcagct 120
cctgctcaag ctattttggc agtctgagag aacagtacat tctgaaccac attgacgcag 180
ggagcatggg tatctggacc tcaggcactg atatcttcct aagtctttgg gagatttacg 240
tgtctccaag aagccccgga tggatggact ttatccagca tttgggagtt tgctgtttgg 300
ttgctcttat ttcagtgggc ctcctgtctg tggccgcctg ctggtttctg ccatcaatca 360
tagcggccgc tgcctcctgg attatcacgt gtgttctgct gtgttgctcc aagcatgcac 420
gatgttttat tcttcttgtc tttctctctt gtggcctgcg tgaaggcagg aatgctttga 480
ttgcagctgg cacagggatc gtcatcttgg gacacgtaga aaatattttt cacaacttta 540
aaggtctcct agatggtatg acttgcaacc taagggcaaa gagcttttcc atacattttc 600
cacttttgaa aaaatatatt gaggcaattc agtggattta tggccttgcc actccactaa 660
gtgtatttga tgaccttgtt tcttggaacc agaccctggc agtctctctt ttcagtccca 720
gccatgtcct ggaggcacag ctaaatgaca gcaaagggga agtcctgagc gtcttgtacc 780
agatggcaac aaccacagag gtgttgtcct ccctgggtca gaagctactt gcctttgcag 840
ggctttcgct cgtcctgctt ggcactggcc tcttcatgaa gcgatttttg ggcccttgtg 900
gttggaagta tgaaaacatc tacatcacca gacaatttgt tcagtttgat gaaagggaga 960
gacatcaaca gaggccctgt gtgctcccgc tgaataagga ggaaaggagg aaattcattt 1020
ctggcttcca gtcctgaaaa tgattaggaa gaagcaaatg gacatggcaa gtgcagacaa 1080
gtcatgagag accccgacta ctcctcagcc acatcgcacc aacaattctc ttcaggtcta 1140
ggatggcagt cactattcat gccggataat agagaactat gtgacgcagt cctctcagga 1200
gtctgagttt acagagccaa cttgcagcac ctggttatgc ctcctttcat ctcaaagcca 1260
aagagctgcc aggtaaatgg ttatgtggtc tatgttccaa acaaaccaca tgatcttgcc 1320
tgtgtcacaa tgtaacaaga ctctagctgg gtcccctggt gatgagtttc agcatagaat 1380
aatgttcaag gaaaagaaaa cgaaaacagt ttaaatctct accacagcct cacaagcaaa 1440
tgctaagggg aacatacatg taaaaagcca gcaaactatc ttcaaactct tccgtcctta 1500
atgtcttcca tggctattgc ccccacaatg gtctcttttc tccctgctcc cttattaaag 1560
aactctttct gaaaaaaaaa aaa 1583

<210> SEQ ID NO 209
<211> LENGTH: 257
<212> TYPE: PRT
<213> ORGANISM: Homo sapiens

<400> SEQUENCE: 209

Met Asp Phe Ile Gln His Leu Gly Val Cys Cys Leu Val Ala Leu Ile
1               5                   10                  15

Ser Val Gly Leu Leu Ser Val Ala Ala Cys Trp Phe Leu Pro Ser Ile
            20                  25                  30

Ile Ala Ala Ala Ala Ser Trp Ile Ile Thr Cys Val Leu Leu Cys Cys
        35                  40                  45

Ser Lys His Ala Arg Cys Phe Ile Leu Leu Val Phe Leu Ser Cys Gly

```
    50                  55                  60

Leu Arg Glu Gly Arg Asn Ala Leu Ile Ala Ala Gly Thr Gly Ile Val
 65                  70                  75                  80

Ile Leu Gly His Val Glu Asn Ile Phe His Asn Phe Lys Gly Leu Leu
                 85                  90                  95

Asp Gly Met Thr Cys Asn Leu Arg Ala Lys Ser Phe Ser Ile His Phe
            100                 105                 110

Pro Leu Leu Lys Lys Tyr Ile Glu Ala Ile Gln Trp Ile Tyr Gly Leu
        115                 120                 125

Ala Thr Pro Leu Ser Val Phe Asp Asp Leu Val Ser Trp Asn Gln Thr
    130                 135                 140

Leu Ala Val Ser Leu Phe Ser Pro Ser His Val Leu Glu Ala Gln Leu
145                 150                 155                 160

Asn Asp Ser Lys Gly Glu Val Leu Ser Val Leu Tyr Gln Met Ala Thr
                165                 170                 175

Thr Thr Glu Val Leu Ser Ser Leu Gly Gln Lys Leu Leu Ala Phe Ala
            180                 185                 190

Gly Leu Ser Leu Val Leu Leu Gly Thr Gly Leu Phe Met Lys Arg Phe
        195                 200                 205

Leu Gly Pro Cys Gly Trp Lys Tyr Glu Asn Ile Tyr Ile Thr Arg Gln
    210                 215                 220

Phe Val Gln Phe Asp Glu Arg Glu Arg His Gln Gln Arg Pro Cys Val
225                 230                 235                 240

Leu Pro Leu Asn Lys Glu Glu Arg Arg Lys Phe Ile Ser Gly Phe Gln
                245                 250                 255

Ser


<210> SEQ ID NO 210
<211> LENGTH: 1444
<212> TYPE: DNA
<213> ORGANISM: Homo sapiens

<400> SEQUENCE: 210

gaattcggca cgaggaagaa tctgagagaa acctgacgca gggagcatgg gtatctggac      60

ctcaggcact gatatcttcc taagtctttg ggagatttac gtgtctccaa gaagccccgg     120

atggatggac tttatccagc atttgggagt ttgctgtttg gttgctctta tttcagtggg     180

cctcctgtct gtggccgcct gctggtttct gccatcaatc atagcggccg ctgcctcctg     240

gattatcacg tgtgttctgc tgtgttgctc caagcatgca cgatgtttta ttcttcttgt     300

ctttctctct tgtggcctgc gtgaaggcag gaatgctttg attgcagctg gcacagggat     360

cgtcatcttg ggacacgtag aaaatatttt tcacaacttt aaaggtctcc tagatggtat     420

gacttgcaac ctaagggcaa agagcttttc catacatttt ccacttttga aaaaatatat     480

tgaggcaatt cagtggattt atggccttgc cactccacta agtgtatttg atgaccttgt     540

ttcttggaac cagaccctgg cagtctctct tttcagtccc agccatgtcc tggaggcaca     600

gctaaatgac agcaaagggg aagtcctgag cgtcttgtac cagatggcaa caaccacaga     660

ggtgttgtcc tccctgggtc agaagctact tgcctttgca gggctttcgc tcgtcctgct     720

tggcactggc ctcttcatga agcgattttt gggcccttgt ggttggaagt atgaaaacat     780

ctacatcacc agacaatttg ttcagtttga tgaaagggag agacatcaac agaggccctg     840

tgtgctcccg ctgaataagg aggaaaggag gaaattcatt tctggcttcc agtcctgaaa     900

atgattagga agaagcaaat ggacatggca agtgcagaca agtcatgaga gaccccgact     960
```

```
actcctcagc cacatcgcac caacaattct cttcaggtct aggatggcag tcactattca   1020

tgccggataa tagagaacta tgtgacgcag tcctctcagg agtctgagtt tacagagcca   1080

acttgcagca cctggttatg cctcctttca tctcaaagcc aaagagctgc caggtaaatg   1140

gttatgtggt ctatgttcca aacaaaccac atgatcttgc ctgtgtcaca atgtaacaag   1200

actctagctg ggtcccctgg tgatgagttt cagcatagaa taatgttcaa ggaaaagaaa   1260

acgaaaacag tttaaatctc taccacagcc tcacaagcaa atgctaaggg gaacatacat   1320

gtaaaaagcc agcaaactat cttcaaactc ttccgtcctt aatgtcttcc atggctattg   1380

cccccacaat ggtctctttt ctccctgctc ccttattaaa gaactctttc tgaaaaaaaa   1440

aaaa                                                                1444


<210> SEQ ID NO 211
<211> LENGTH: 257
<212> TYPE: PRT
<213> ORGANISM: Homo sapiens

<400> SEQUENCE: 211

Met Asp Phe Ile Gln His Leu Gly Val Cys Cys Leu Val Ala Leu Ile
  1               5                  10                  15

Ser Val Gly Leu Leu Ser Val Ala Ala Cys Trp Phe Leu Pro Ser Ile
             20                  25                  30

Ile Ala Ala Ala Ala Ser Trp Ile Ile Thr Cys Val Leu Leu Cys Cys
         35                  40                  45

Ser Lys His Ala Arg Cys Phe Ile Leu Leu Val Phe Leu Ser Cys Gly
     50                  55                  60

Leu Arg Glu Gly Arg Asn Ala Leu Ile Ala Ala Gly Thr Gly Ile Val
 65                  70                  75                  80

Ile Leu Gly His Val Glu Asn Ile Phe His Asn Phe Lys Gly Leu Leu
                 85                  90                  95

Asp Gly Met Thr Cys Asn Leu Arg Ala Lys Ser Phe Ser Ile His Phe
            100                 105                 110

Pro Leu Leu Lys Lys Tyr Ile Glu Ala Ile Gln Trp Ile Tyr Gly Leu
        115                 120                 125

Ala Thr Pro Leu Ser Val Phe Asp Asp Leu Val Ser Trp Asn Gln Thr
    130                 135                 140

Leu Ala Val Ser Leu Phe Ser Pro Ser His Val Leu Glu Ala Gln Leu
145                 150                 155                 160

Asn Asp Ser Lys Gly Glu Val Leu Ser Val Leu Tyr Gln Met Ala Thr
                165                 170                 175

Thr Thr Glu Val Leu Ser Ser Leu Gly Gln Lys Leu Leu Ala Phe Ala
            180                 185                 190

Gly Leu Ser Leu Val Leu Leu Gly Thr Gly Leu Phe Met Lys Arg Phe
        195                 200                 205

Leu Gly Pro Cys Gly Trp Lys Tyr Glu Asn Ile Tyr Ile Thr Arg Gln
    210                 215                 220

Phe Val Gln Phe Asp Glu Arg Glu Arg His Gln Gln Arg Pro Cys Val
225                 230                 235                 240

Leu Pro Leu Asn Lys Glu Glu Arg Arg Lys Phe Ile Ser Gly Phe Gln
                245                 250                 255

Ser


<210> SEQ ID NO 212
<211> LENGTH: 1444
<212> TYPE: DNA
```

-continued

<213> ORGANISM: Homo sapiens

<400> SEQUENCE: 212

```
gaattcggca cgaggaagaa tctgagagaa acctgacgca gggagcatgg gtatctggac     60
ctcaggcact gatatcttcc taagtctttg ggagatttac gtgtctccaa gaagccccgg    120
atggatggac tttatccagc atttgggagt ttgctgtttg gttgctctta tttcagtggg    180
cctcctgtct gtggccgcct gctggtttct gccatcaatc atagcggccg ctgcctcctg    240
gattatcacg tgtgttctgc tgtgttgctc caagcatgca cgatgtttta ttcttcttgt    300
ctttctctct tgtggcctgc gtgaaggcag gaatgctttg attgcagctg gcacagggat    360
cgtcatcttg ggacacgtag aaaatatttt tcacaacttt aaaggtctcc tagatggtat    420
gacttgcaac ctaagggcaa agagcttttc catacatttt ccacttttga aaaaatatat    480
tgaggcaatt cagtggattt atggccttgc cactccacta agtgtatttg atgaccttgt    540
ttcttggaac cagaccctgg cagtctctct tttcagtccc agccatgtcc tggaggcaca    600
gctaaatgac agcaaagggg aagtcctgag cgtcttgtac cagatggcaa caaccacaga    660
ggtgttgtcc tccctgggtc agaagctact tgcctttgca gggctttcgc tcgtcctgct    720
tggcactggc ctcttcatga agcgattttt gggcccttgt ggttggaagt atgaaaacat    780
ctacatcacc agacaatttg ttcagtttga tgaaagggag agacatcaac agaggccctg    840
tgtgctcccg ctgaataagg aggaaaggag gaaattcatt tctggcttcc agtcctgaaa    900
atgattagga agaagcaaat ggacatggca agtgcagaca agtcatgaga gaccccgact    960
actcctcagc cacatcgcac caacaattct cttcaggtct aggatggcag tcactattca   1020
tgccggataa tagagaacta tgtgacgcag tcctctcagg agtctgagtt tacagagcca   1080
acttgcagca cctggttatg cctcctttca tctcaaagcc aaagagctgc caggtaaatg   1140
gttatgtggt ctatgttcca aacaaaccac atgatcttgc ctgtgtcaca atgtaacaag   1200
actctagctg ggtcccctgg tgatgagttt cagcatagaa taatgttcaa ggaaaagaaa   1260
acgaaaacag tttaaatctc taccacagcc tcacaagcaa atgctaaggg gaacatacat   1320
gtaaaaagcc agcaaactat cttcaaactc ttccgtcctt aatgtcttcc atggctattg   1380
cccccacaat ggtctctttt ctccctgctc ccttattaaa gaactctttc tgaaaaaaaa   1440
aaaa                                                                1444
```

<210> SEQ ID NO 213
<211> LENGTH: 257
<212> TYPE: PRT
<213> ORGANISM: Homo sapiens

<400> SEQUENCE: 213

```
Met Asp Phe Ile Gln His Leu Gly Val Cys Cys Leu Val Ala Leu Ile
  1               5                  10                  15

Ser Val Gly Leu Leu Ser Val Ala Ala Cys Trp Phe Leu Pro Ser Ile
             20                  25                  30

Ile Ala Ala Ala Ala Ser Trp Ile Ile Thr Cys Val Leu Leu Cys Cys
         35                  40                  45

Ser Lys His Ala Arg Cys Phe Ile Leu Leu Val Phe Leu Ser Cys Gly
     50                  55                  60

Leu Arg Glu Gly Arg Asn Ala Leu Ile Ala Ala Gly Thr Gly Ile Val
 65                  70                  75                  80

Ile Leu Gly His Val Glu Asn Ile Phe His Asn Phe Lys Gly Leu Leu
                 85                  90                  95
```

```
Asp Gly Met Thr Cys Asn Leu Arg Ala Lys Ser Phe Ser Ile His Phe
            100                 105                 110

Pro Leu Leu Lys Lys Tyr Ile Glu Ala Ile Gln Trp Ile Tyr Gly Leu
        115                 120                 125

Ala Thr Pro Leu Ser Val Phe Asp Asp Leu Val Ser Trp Asn Gln Thr
    130                 135                 140

Leu Ala Val Ser Leu Phe Ser Pro Ser His Val Leu Glu Ala Gln Leu
145                 150                 155                 160

Asn Asp Ser Lys Gly Glu Val Leu Ser Val Leu Tyr Gln Met Ala Thr
                165                 170                 175

Thr Thr Glu Val Leu Ser Ser Leu Gly Gln Lys Leu Leu Ala Phe Ala
            180                 185                 190

Gly Leu Ser Leu Val Leu Leu Gly Thr Gly Leu Phe Met Lys Arg Phe
        195                 200                 205

Leu Gly Pro Cys Gly Trp Lys Tyr Glu Asn Ile Tyr Ile Thr Arg Gln
    210                 215                 220

Phe Val Gln Phe Asp Glu Arg Glu Arg His Gln Gln Arg Pro Cys Val
225                 230                 235                 240

Leu Pro Leu Asn Lys Glu Glu Arg Arg Lys Phe Ile Ser Gly Phe Gln
                245                 250                 255

Ser


<210> SEQ ID NO 214
<211> LENGTH: 1892
<212> TYPE: DNA
<213> ORGANISM: Homo sapiens

<400> SEQUENCE: 214

attcggcacg aggaaacctg ctgctttcac agaggaaggc atttgctggc tttcccaagg      60

caagaacaat gaaaacaaag tcatgaggag ttctctctac ctcaaatgaa ggccgcagct     120

cctgctcaag ctattttggc agtctgagag aacagtacat tctgaaccac attgacgcag     180

ggagcatggg tatctggacc tcaggcactg atatcttcct aagtctttgg gagatttacg     240

tgtctccaag aagccccgga tggatggact ttatccagca tttgggagtt tgctgtttgg     300

ttgctcttat ttcagtgggc ctcctgtctg tggccgcctg ctggtttctg ccatcaatca     360

tagcggccgc tgcctcctgg attatcacgt gtgttctgct gtgttgctcc aagcatgcac     420

gatgttttat tcttcttgtc tttctctctt gtggcctgcg tgaaggcagg aatgctttga     480

ttgcagctgg cacagggatc gtcatcttgg gacacgtaga aaatattttt cacaacttta     540

aaggtctcct agatggtatg acttgcaacc taagggcaaa gagcttttcc atacattttc     600

cacttttgaa aaaatatatt gaggcaattc agtggattta tggccttgcc actccactaa     660

gtgtatttga tgaccttgtt tcttggaacc agaccctggc agtctctctt ttcagtccca     720

gccatgtcct ggaggcacag ctaaatgaca gcaaagggga agtcctgagc gtcttgtacc     780

agatggcaac aaccacagag gtgttgtcct ccctgggtca gaagctactt gcctttgcag     840

ggctttcgct cgtcctgctt ggcactggcc tcttcatgaa gcgatttttg ggcccttgtg     900

gttggaagta tgaaaacatc tacatcacca gacaatttgt tcagtttgat gaaagggaga     960

gacatcaaca gaggccctgt atgctcccgc tgaataagga ggaaaggagg aaaaacaagg    1020

aactcaagat attatccatg attcttcctt taatatatct gtgtttgaac ccaactgtat    1080

cccaaaacca aaattccttc tatctgagac ctgggttcct ctcagtgtta ttcttttgat    1140

attagtgatg ctgggactgt tgtcctctat ccttatgcaa cttaaaatcc tggtgtcagc    1200
```

```
atctttctac cccagcgtgg agaggaagcg catccaatat ctgcatgcaa agctgcttaa   1260

aaaaagatca aagcagccgc tgggagaagt caaaagacgg ctgagtctct atcttacaaa   1320

gattcatttc tggcttccag tcctgaaaat gattaggaag aagcaaatgg acatggcaag   1380

tgcagacaag tcatgagaga ccccgactac tcctcagcca catcgcacca acaattctct   1440

tcaggtctag gatggcagtc actattcatg ccggataata gagaactatg tgacgcagtc   1500

ctctcaggag tctgagttta cagagccaac ttgcagcacc tggttatgcc tcctttcatc   1560

tcaaagccaa agagctgcca ggtaaatggt tatgtggtct atgttccaaa caaaccacat   1620

gatcttgcct gtgtcacaat gtaacaagac tctagctggg tcccctggtg atgagtttca   1680

gcatagaata atgttcaagg aaaagaaaac gaaaacagtt taaatctcta ccacagcctc   1740

acaagcaaat gctaagggga acatacatgt aaaaagccag caaactatct tcaaactctt   1800

ccgtccttaa tgtcttccat ggctattgcc cccacaatgg tctcttttct ccctgctccc   1860

ttattaaaga actctttctg aaaaaaaaaa aa                                 1892


<210> SEQ ID NO 215
<211> LENGTH: 291
<212> TYPE: PRT
<213> ORGANISM: Homo sapiens

<400> SEQUENCE: 215

Met Asp Phe Ile Gln His Leu Gly Val Cys Cys Leu Val Ala Leu Ile
1               5                   10                  15

Ser Val Gly Leu Leu Ser Val Ala Ala Cys Trp Phe Leu Pro Ser Ile
            20                  25                  30

Ile Ala Ala Ala Ala Ser Trp Ile Ile Thr Cys Val Leu Leu Cys Cys
        35                  40                  45

Ser Lys His Ala Arg Cys Phe Ile Leu Leu Val Phe Leu Ser Cys Gly
    50                  55                  60

Leu Arg Glu Gly Arg Asn Ala Leu Ile Ala Ala Gly Thr Gly Ile Val
65                  70                  75                  80

Ile Leu Gly His Val Glu Asn Ile Phe His Asn Phe Lys Gly Leu Leu
                85                  90                  95

Asp Gly Met Thr Cys Asn Leu Arg Ala Lys Ser Phe Ser Ile His Phe
            100                 105                 110

Pro Leu Leu Lys Lys Tyr Ile Glu Ala Ile Gln Trp Ile Tyr Gly Leu
        115                 120                 125

Ala Thr Pro Leu Ser Val Phe Asp Asp Leu Val Ser Trp Asn Gln Thr
    130                 135                 140

Leu Ala Val Ser Leu Phe Ser Pro Ser His Val Leu Glu Ala Gln Leu
145                 150                 155                 160

Asn Asp Ser Lys Gly Glu Val Leu Ser Val Leu Tyr Gln Met Ala Thr
                165                 170                 175

Thr Thr Glu Val Leu Ser Ser Leu Gly Gln Lys Leu Leu Ala Phe Ala
            180                 185                 190

Gly Leu Ser Leu Val Leu Leu Gly Thr Gly Leu Phe Met Lys Arg Phe
        195                 200                 205

Leu Gly Pro Cys Gly Trp Lys Tyr Glu Asn Ile Tyr Ile Thr Arg Gln
    210                 215                 220

Phe Val Gln Phe Asp Glu Arg Glu Arg His Gln Gln Arg Pro Cys Met
225                 230                 235                 240

Leu Pro Leu Asn Lys Glu Glu Arg Arg Lys Asn Lys Glu Leu Lys Ile
                245                 250                 255
```

```
Leu Ser Met Ile Leu Pro Leu Ile Tyr Leu Cys Leu Asn Pro Thr Val
            260                 265                 270

Ser Gln Asn Gln Asn Ser Phe Tyr Leu Arg Pro Gly Phe Leu Ser Val
        275                 280                 285

Leu Phe Phe
    290


<210> SEQ ID NO 216
<211> LENGTH: 1439
<212> TYPE: DNA
<213> ORGANISM: Homo sapiens
<220> FEATURE:
<221> NAME/KEY: misc_feature
<222> LOCATION: (1281)..(1281)
<223> OTHER INFORMATION: n equals a,t,g, or c

<400> SEQUENCE: 216

gaattcggca cgaggaagaa tctgagagaa acctgacgca gggagcatgg gtatctggac     60

ctcaggcact gatatcttcc taagtctttg ggagatttac gtgtctccaa gaagccccgg    120

atggatggac tttatccagc atttgggagt ttgctgtttg gttgctctta tttcagtggg    180

cctcctgtct gtggccgcct gctggtttct gccatcaatc atagcggccg ctgcctcctg    240

gattatcacg tgtgttctgc tgtgttgctc caagcatgca cgatgtttta ttcttcttgt    300

ctttctctct tgtggcctgc gtgaaggcag gaatgctttg attgcagctg gsacagggat    360

cgtcatcttg ggacacgtag aaaatatttt tcacaacttt aaaggtcycc tagatggtat    420

racttgcaac ctaagggcaa agagcttttc catacatttt ccactttkga aaaaatatat    480

tgaggcaatt cagtggattt atggccttgc cactccacta agtgtatytg atgaccttgt    540

ttcttggaac cagaccctgg cagtctctct tttcagtccc agccatgtcc tggaggcaca    600

gcyaaatgac agcaaagggg aagtcctgag cgtcttgtac cagatggcaa caaccacaga    660

ggtgttgtcc tcccctgggt cagaagctac ttgcctttgc agggctttcg ctcgtcctgc    720

ttggcactgg cctcttcatg aagcgatttt tgggcccttg tggttggaag tatgaaaaca    780

tctacatcac cagacaattt gttcagtttg atgaaaggga gagacatcaa cagaggccct    840

gtgtgctccc gctgaataag gaggaaagga ggaaattcat ttctggcttc cagtcctgaa    900

aatgattagg aagaagcaaa tggacatggc ragygcagac aagtcatgag agaccccgac    960

tactcctcag ccacatcgca ccaacaattc tcttcaggtc taggatggca gtcactattc   1020

atgccggata atagagaact atgtgacgca gtcctctcag gagtctgagt ttacagagcc   1080

aacttgcagc acctggttat gcctcctttc atctcaaagc caaagagctg ccaggtaaat   1140

ggttatgtgg tctatgttcc aaacaaacca catgatcttg cctgtgtcac aatgtaacaa   1200

gactctagct gggtcccctg gtgatgagtt tcagcataga ataatgttca aggaaaagaa   1260

aacgaaaaca gtttaaatyt ntaccacagc ctcacaagca aatgctaagg ggaacataca   1320

tgtaaaaagc cagcaaacta tcttcaaact cttccgtcct taatgtcttc catggctatt   1380

gcccccacaa tggtctcttt tctccctgct cccttattaa agaactcttt ctgaaaccg    1439


<210> SEQ ID NO 217
<211> LENGTH: 242
<212> TYPE: PRT
<213> ORGANISM: Homo sapiens
<220> FEATURE:
<221> NAME/KEY: SITE
<222> LOCATION: (121)
<223> OTHER INFORMATION: Xaa equals any amino acid
<220> FEATURE:
<221> NAME/KEY: SITE
```

<222> LOCATION: (125)
<223> OTHER INFORMATION: Xaa equals any amino acid
<220> FEATURE:
<221> NAME/KEY: SITE
<222> LOCATION: (141)
<223> OTHER INFORMATION: Xaa equals any amino acid
<220> FEATURE:
<221> NAME/KEY: SITE
<222> LOCATION: (161)
<223> OTHER INFORMATION: Xaa equals any amino acid
<220> FEATURE:
<221> NAME/KEY: SITE
<222> LOCATION: (186)
<223> OTHER INFORMATION: Xaa equals any amino acid

<400> SEQUENCE: 217

```
Met Gly Ile Trp Thr Ser Gly Thr Asp Ile Phe Leu Ser Leu Trp Glu
  1               5                  10                  15

Ile Tyr Val Ser Pro Arg Ser Pro Gly Trp Met Asp Phe Ile Gln His
             20                  25                  30

Leu Gly Val Cys Cys Leu Val Ala Leu Ile Ser Val Gly Leu Leu Ser
         35                  40                  45

Val Ala Ala Cys Trp Phe Leu Pro Ser Ile Ile Ala Ala Ala Ala Ser
     50                  55                  60

Trp Ile Ile Thr Cys Val Leu Leu Cys Cys Ser Lys His Ala Arg Cys
 65                  70                  75                  80

Phe Ile Leu Leu Val Phe Leu Ser Cys Gly Leu Arg Glu Gly Arg Asn
                 85                  90                  95

Ala Leu Ile Ala Ala Gly Thr Gly Ile Val Ile Leu Gly His Val Glu
            100                 105                 110

Asn Ile Phe His Asn Phe Lys Gly Xaa Leu Asp Gly Xaa Thr Cys Asn
        115                 120                 125

Leu Arg Ala Lys Ser Phe Ser Ile His Phe Pro Leu Xaa Lys Lys Tyr
    130                 135                 140

Ile Glu Ala Ile Gln Trp Ile Tyr Gly Leu Ala Thr Pro Leu Ser Val
145                 150                 155                 160

Xaa Asp Asp Leu Val Ser Trp Asn Gln Thr Leu Ala Val Ser Leu Phe
                165                 170                 175

Ser Pro Ser His Val Leu Glu Ala Gln Xaa Asn Asp Ser Lys Gly Glu
            180                 185                 190

Val Leu Ser Val Leu Tyr Gln Met Ala Thr Thr Thr Glu Val Leu Ser
        195                 200                 205

Ser Pro Gly Ser Glu Ala Thr Cys Leu Cys Arg Ala Phe Ala Arg Pro
    210                 215                 220

Ala Trp His Trp Pro Leu His Glu Ala Ile Phe Gly Pro Leu Trp Leu
225                 230                 235                 240

Glu Val
```

<210> SEQ ID NO 218
<211> LENGTH: 991
<212> TYPE: DNA
<213> ORGANISM: Homo sapiens

<400> SEQUENCE: 218

```
aaattcggca cagctgagag gagacacaag gagcagcccg caagcaccaa gtgagaggca      60

tgaagttaca gtgtgtttcc ctttggctcc tgggtacaat actgatattg tgctcagtag     120

acaaccacgg tctcaggaga tgtctgattt ccacagacat gcaccatata gaagagagtt     180

tccaagaaat caaaagagcc atccaagcta aggacacctt cccaaatgtc actatcctgt     240
```

```
ccacattgga gactctgcag atcattaagc ccttagatgt gtgctgcgtg accaagaacc    300

tcctggcgtt ctacgtggac agggtgttca aggatcatca ggagccaaac cccaaaatct    360

tgagaaaaat cagcagcatt gccaactctt tcctctacat gcagaaaact ctgcggcaat    420

gtcaggaaca gaggcagtgt cactgcaggc aggaagccac caatgccacc agagtcatcc    480

atgacaacta tgatcagctg gaggtccacg ctgctgccat taaatccctg ggagagctcg    540

acgtctttct agcctggatt aataagaatc atgaagtaat gtcctcagct tgatgacaag    600

gaacctgtat agtgatccag ggatgaacac cccctgtgcg gtttactgtg ggagacagcc    660

caccttgaag gggaaggaga tggggaaggc cccttgcagc tgaaagtccc actggctggc    720

ctcaggctgt cttattccgc ttgaaaatag ccaaaaagtc tactgtggta tttgtaataa    780

actctatctg ctgaaagggc ctgcaggcca tcctgggagt aaagggctgc cttcccatct    840

aatttattgt gaagtcatat agtccatgtc tgtgatgtga gccaagtgat atcctgtagt    900

acacattgta ctgagtggtt tttctgaata aattccatat tttacctaaa aaaaaaaaaa    960

aaaaactcga ggggggggcc cgtacccaatt t                                  991
```

```
<210> SEQ ID NO 219
<211> LENGTH: 178
<212> TYPE: PRT
<213> ORGANISM: Homo sapiens
<220> FEATURE:
<221> NAME/KEY: SITE
<222> LOCATION: (178)
<223> OTHER INFORMATION: Xaa equals stop translation

<400> SEQUENCE: 219

Met Lys Leu Gln Cys Val Ser Leu Trp Leu Leu Gly Thr Ile Leu Ile
  1               5                  10                  15

Leu Cys Ser Val Asp Asn His Gly Leu Arg Arg Cys Leu Ile Ser Thr
             20                  25                  30

Asp Met His His Ile Glu Glu Ser Phe Gln Glu Ile Lys Arg Ala Ile
         35                  40                  45

Gln Ala Lys Asp Thr Phe Pro Asn Val Thr Ile Leu Ser Thr Leu Glu
     50                  55                  60

Thr Leu Gln Ile Ile Lys Pro Leu Asp Val Cys Cys Val Thr Lys Asn
 65                  70                  75                  80

Leu Leu Ala Phe Tyr Val Asp Arg Val Phe Lys Asp His Gln Glu Pro
                 85                  90                  95

Asn Pro Lys Ile Leu Arg Lys Ile Ser Ser Ile Ala Asn Ser Phe Leu
            100                 105                 110

Tyr Met Gln Lys Thr Leu Arg Gln Cys Gln Glu Gln Arg Gln Cys His
        115                 120                 125

Cys Arg Gln Glu Ala Thr Asn Ala Thr Arg Val Ile His Asp Asn Tyr
    130                 135                 140

Asp Gln Leu Glu Val His Ala Ala Ala Ile Lys Ser Leu Gly Glu Leu
145                 150                 155                 160

Asp Val Phe Leu Ala Trp Ile Asn Lys Asn His Glu Val Met Ser Ser
                165                 170                 175

Ala Xaa


<210> SEQ ID NO 220
<211> LENGTH: 2416
<212> TYPE: DNA
<213> ORGANISM: Homo sapiens

<400> SEQUENCE: 220
```

```
tcaatttcca ttaactcaga tcagccattg tgattcacca tttgtcaggc tctcaggttt     60
aacaaaacct actatcacca tcatccttca acagccacag tctgaattga gccaacattt    120
ttttttcttt gagaaagaag tggactgggg cacaactttt agtctgaggg gagctagtgg    180
aaatctagac aatagaagtc atcgatagca gcttttcctc aaatgtgtga ctcctcaggg    240
gctaaactgc tcttagctta gaattatgct ttactagaga tctagcagat aagtgggtta    300
atcactacca tcctgtaact agttatatag cttccagaca tgagggagac atcaaacagg    360
gatggaagca accccaagga tatgcaagaa gggcatgatg aaccccccttc cctctggcag    420
gagaacaagg ccaaccaagg gacagactgg aaagcactta gatgtttaag gaggagaaag    480
gggaagcttt gaccagtcct tgccttttgc caagttcagc cagttctccg ctgcttgcaa    540
cctctagcgc agtaacattt gcagaattgc agattttccc ccagatacta ggaggaaagg    600
gactttgggg ggtggggaag gggtcgtggt gttttaaaag cataagttac ctgtttgcac    660
tgttttaaga taggaaaaaa aaatagtggg caaggtgaac atcagacgta aatttgtgtg    720
tttttatttt gtcatgctct tgaaaatgtt tgaccatttg tagtatacac agtgaaactt    780
gattctctgt tgcataaaac actatatttt tttggaaatg ttactgtcca aaagcctctt    840
ccctcccttt ccttttccta tgtacttcct tcatacttgc tttactgatc agccaggcaa    900
tagccatcca agagctagag catgaaacag ggccctttcc aagtaggctc tgggtgtcct    960
aagccagcgt gtgccctctg gtttagtgag tgtaatagag tccctggcac ctttctttgc   1020
aaatgaggct aacagaccag actgcagcaa gttatcagat tcctcaatca gatgcactag   1080
gagtgaggag cccagggatg gagggggttc ctgaagtatt gcagttggct gtagtagctg   1140
agttcttttc catgttaccg aaactgtagc cagttacagt ttactcagga aaacggtaga   1200
tcaattcagc catggtagtg ctggttggca gggattggta acggagagaa ctgctcatca   1260
gccaaaactc aagccttgcc ttttaggagg ccaccagcag agggacttgg tcctccttgt   1320
ctggtacttg tgtacatgcc ggtgacctga ggactccact cacactggcg agcaaaaagg   1380
gagcagtgat tctcttttct ctccccaccc cctgcccttt gttaccaaca ccagtttccc   1440
agggggtaca tgagtttctg aatttttaaa aaatgttttt ggtttggttt ttctggggac   1500
tgataagtgc tttaagcaat gtccataccc cgtcaagact cccagcttag tcattttctt   1560
gtatttttct gttcacagta tttgtgtgtg tgcttgtttt ggcagctcat tttggctgta   1620
ttatatattg agtgatgaat tgatcctctt ttttccctaa gggatatgaa ttgtttttct   1680
tgtgttatat tctgcttgtg aatagctgga gcaaacctgg ggctgacacg cgtaagstag   1740
ggctgcaaar cgagaagaga gccggtggag tgtacttgtc cctgacaggc tgacctacct   1800
gagtctctga gcttttcagt ccaaatcttt gcaaggctca aaatgccaca gaacctctcc   1860
tcttctcccc actccccatg gcagggaccg gaccatccct acatgcaaca tgctgttcct   1920
ccagcccctc ccattgccat ggcaaaacag gtacctttgg ggcatggggg cattacatgg   1980
gatgcttgtg taatcgacca cctagccttc tctctcccct cccgtcctcc cccagaatca   2040
cttcctagga cacccgagct gcttgcccag ggtcctgttt ccctgctaac tccagagaag   2100
catcccaggg ctttgtgaca gtctctaatt cccttccctt ctcgttaaga atcatattgt   2160
atagtagctt tcagaccata cagtattcat tgggttactc ctattattat caagtagctg   2220
gaattgtgaa ggtcggagta gttagatctt tagcttttat tccttatttt tttgtattac   2280
tctccatgtg tataaattat tgatcatgtt gctggctttt ataaactcta agcgaaggag   2340
gagcactgcc tcagcctttg cacatggtaa tgaagcactg tttttaaata aaagrgrgaa   2400
```

mcmccaaaaa aaaaaa 2416

<210> SEQ ID NO 221
<211> LENGTH: 25
<212> TYPE: PRT
<213> ORGANISM: Homo sapiens

<400> SEQUENCE: 221

Met Phe Leu Val Trp Phe Phe Trp Gly Leu Ile Ser Ala Leu Ser Asn
1 5 10 15

Val His Thr Pro Ser Arg Leu Pro Ala
20 25

<210> SEQ ID NO 222
<211> LENGTH: 985
<212> TYPE: DNA
<213> ORGANISM: Homo sapiens

<400> SEQUENCE: 222
ggcacgagcg gcgccacgag gcggccggac ccgcagcccc gatgctgctg acgctggccg 60
ggggcgcgct cttcttcccg gggctcttcg cgctctgcac ctgggcgctg cgccgctccc 120
agcccggatg gagccgcacc gactgcgtga tgatcagcac caggctggtt tcctcggtgc 180
acgccgtgct ggccaccggc tcggggatcg tcatcattcg ctcctgcgac gacgtgatca 240
ccggcaggca ctggcttgcc cgggaatatg tgtggtttct gattccatac atgatctatg 300
actcgtacgc catgtacctc tgtgaatggt gccgaaccag agaccagaac cgtgcgccct 360
ccctcactct tcgaaacttc ctaagtcgaa accgcctcat gatcacacat catgcggtca 420
ttctctttgt ccttgtgcca gtcgcacaga ggctccgggg agaccttggg gacttctttg 480
tcggctgcat cttcacggca gaactgagca ctccgtttgt gtcgctgggc agggttctga 540
ttcagctaaa gcagcagcac acccttctgt acaaggtgaa tggaatcctc acgctggcca 600
ccttcctttc ctgccggatc cttctcttcc ccttcatgta ctggtcctat ggccgccagc 660
agggactaag cctgctccaa gtacccttca gcatcccatt ctactgcaac gtggccaatg 720
ccttcctcgt agctcctcag atctactggt tctgtctgct gtgcaggaag gcagtccggc 780
tctttgacac tccccaagcc aaaaaggatg gctaaatgct cctgggagtc aggcgcagcc 840
tcacaccagc tgcctcctcc actcagcatt ccatggacca aattgtgccc tgggtagcct 900
cagactttgg gtattgataa gccgatggat ttgagttttt ctaaagaata ttcatattac 960
ctccttaaaa aaaaaaaaaa aaaaa 985

<210> SEQ ID NO 223
<211> LENGTH: 257
<212> TYPE: PRT
<213> ORGANISM: Homo sapiens

<400> SEQUENCE: 223

Met Leu Leu Thr Leu Ala Gly Gly Ala Leu Phe Phe Pro Gly Leu Phe
1 5 10 15

Ala Leu Cys Thr Trp Ala Leu Arg Arg Ser Gln Pro Gly Trp Ser Arg
20 25 30

Thr Asp Cys Val Met Ile Ser Thr Arg Leu Val Ser Ser Val His Ala
35 40 45

Val Leu Ala Thr Gly Ser Gly Ile Val Ile Ile Arg Ser Cys Asp Asp
50 55 60

Val Ile Thr Gly Arg His Trp Leu Ala Arg Glu Tyr Val Trp Phe Leu

-continued

```
 65                  70                  75                  80

Ile Pro Tyr Met Ile Tyr Asp Ser Tyr Ala Met Tyr Leu Cys Glu Trp
                85                  90                  95

Cys Arg Thr Arg Asp Gln Asn Arg Ala Pro Ser Leu Thr Leu Arg Asn
            100                 105                 110

Phe Leu Ser Arg Asn Arg Leu Met Ile Thr His His Ala Val Ile Leu
        115                 120                 125

Phe Val Leu Val Pro Val Ala Gln Arg Leu Arg Gly Asp Leu Gly Asp
    130                 135                 140

Phe Phe Val Gly Cys Ile Phe Thr Ala Glu Leu Ser Thr Pro Phe Val
145                 150                 155                 160

Ser Leu Gly Arg Val Leu Ile Gln Leu Lys Gln Gln His Thr Leu Leu
                165                 170                 175

Tyr Lys Val Asn Gly Ile Leu Thr Leu Ala Thr Phe Leu Ser Cys Arg
            180                 185                 190

Ile Leu Leu Phe Pro Phe Met Tyr Trp Ser Tyr Gly Arg Gln Gln Gly
        195                 200                 205

Leu Ser Leu Leu Gln Val Pro Phe Ser Ile Pro Phe Tyr Cys Asn Val
    210                 215                 220

Ala Asn Ala Phe Leu Val Ala Pro Gln Ile Tyr Trp Phe Cys Leu Leu
225                 230                 235                 240

Cys Arg Lys Ala Val Arg Leu Phe Asp Thr Pro Gln Ala Lys Lys Asp
                245                 250                 255

Gly
```

<210> SEQ ID NO 224
<211> LENGTH: 2406
<212> TYPE: DNA
<213> ORGANISM: Homo sapiens

<400> SEQUENCE: 224

```
ccacgcgtcc ggaatgaaca acttttcttc tcttgaatat atcttaacgc caaattttga     60

gtgctttttt gttacccatc ctcatatgtc ccagctggaa agaatcctgg gttggagcta    120

ctgcatgttg attgttttgt tttcctttt ggctgttcat tttggtggct actataagga    180

aatctaacac aaacagcaac tgttttttgt tgtttacttt tgcatcttta cttgtggagc    240

tgtggcaagt cctcatatca aatacagaac atgatcttcc tcctgctaat gttgagcctg    300

gaattgcagc ttcaccagat agcagcttta ttcacagtga cagtccctaa ggaactgtac    360

ataatagagc atggcagcaa tgtgaccctg gaatgcaact ttgacactgg aagtcatgtg    420

aaccttggag caataacagc cagtttgcaa aaggtggaaa atgatacatc cccacaccgt    480

gaaagagcca ctttgctgga ggagcagctg cccctaggga aggcctcgtt ccacatacct    540

caagtccaag tgagggacga aggacagtac caatgcataa tcatctatgg ggtcgcctgg    600

gactacaagt acctgactct gaaagtcaaa gcttcctaca ggaaaataaa cactcacatc    660

ctaaaggttc cagaaacaga tgaggtagag ctcacctgcc aggctacagg ttatcctctg    720

gcagaagtat cctggccaaa cgtcagcgtt cctgccaaca ccagccactc caggaccccct    780

gaaggcctct accaggtcac cagtgttctg cgcctaaagc cacccccctgg cagaaacttc    840

agctgtgtgt tctggaatac tcacgtgagg gaacttactt tggccagcat tgaccttcaa    900

agtcagatgg aacccaggac ccatccaact tggctgcttc acattttcat cccctcctgc    960

atcattgctt tcattttcat agccacagtg atagccctaa gaaaacaact ctgtcaaaag   1020

ctgtattctt caaaagacac aacaaaaaga cctgtcacca caacaaagag ggaagtgaac   1080
```

```
agtgctgtga atctgaacct gtggtcttgg gagccagggt gacctgatat gacatctaaa   1140
gaagcttctg gactctgaac aagaattcgg tggcctgcag agcttgccat ttgcactttt   1200
caaatgcctt tggatgaccc agcactttaa tctgaaacct gcaacaagac tagccaacac   1260
ctggccatga aacttgcccc ttcactgatc tggactcacc tctggagcct atggctttaa   1320
gcaagcacta ctgcacttta cagaattacc ccactggatc ctggacccac agaattcctt   1380
caggatcctt cttgctgcca gactgaaagc aaaaggaatt atttcccctc aagttttcta   1440
agtgatttcc aaaagcagag gtgtgtggaa atttccagta acagaaacag atgggttgcc   1500
aatagagtta ttttttatct atagcttcct ctgggtacta gaagaggcta ttgagactat   1560
gagctcacag acagggcttc gcacaaactc aaatcataat tgacatgttt tatggattac   1620
tggaatcttg atagcataat gaagttgttc taattaacag agagcattta aatatacact   1680
aagtgcacaa attgtggagt aaagtcatca agctctgttt ttgaggtcta agtcacaaag   1740
catttgtttt aacctgtaat ggcaccatgt ttaatggtgg tttttttttt gaactacatc   1800
tttcctttaa aaattattgg tttcttttta tttgttttta ccttagaaat caattatata   1860
cagtcaaaaa tatttgatat gctcatacgt tgtatctgca gcaatttcag ataagtagct   1920
aaaatggcca aagccccaaa ctaagcctcc ttttctggcc ctcaatatga ctttaaattt   1980
gacttttcag tgcctcagtt tgcacatctg taatacagca atgctaagta gtcaaggcct   2040
ttgataattg gcactatgga aatcctgcaa gatcccacta catatgtgtg gagcagaagg   2100
gtaactcggc tacagtaaca gcttaatttt gttaaatttg ttctttatac tggagccatg   2160
aagctcagag cattagctga cccttgaact attcaaatgg gcacattagc tagtataaca   2220
gacttacata ggtgggccta aagcaagctc cttaactgag caaaatttgg ggcttatgag   2280
aatgaaaggg tgtgaaattg actaacagac aaatcataca tctcagtttc tcaattctca   2340
tgtaaatcag agaatgcctt taaagaataa aactcaattg ttattcttca aaaaaaaaaa   2400
aaaaaa                                                              2406
```

<210> SEQ ID NO 225
<211> LENGTH: 283
<212> TYPE: PRT
<213> ORGANISM: Homo sapiens

<400> SEQUENCE: 225

```
Met Ile Phe Leu Leu Leu Met Leu Ser Leu Glu Leu Gln Leu His Gln
  1               5                  10                  15

Ile Ala Ala Leu Phe Thr Val Thr Val Pro Lys Glu Leu Tyr Ile Ile
             20                  25                  30

Glu His Gly Ser Asn Val Thr Leu Glu Cys Asn Phe Asp Thr Gly Ser
         35                  40                  45

His Val Asn Leu Gly Ala Ile Thr Ala Ser Leu Gln Lys Val Glu Asn
     50                  55                  60

Asp Thr Ser Pro His Arg Glu Arg Ala Thr Leu Leu Glu Glu Gln Leu
 65                  70                  75                  80

Pro Leu Gly Lys Ala Ser Phe His Ile Pro Gln Val Gln Val Arg Asp
                 85                  90                  95

Glu Gly Gln Tyr Gln Cys Ile Ile Ile Tyr Gly Val Ala Trp Asp Tyr
            100                 105                 110

Lys Tyr Leu Thr Leu Lys Val Lys Ala Ser Tyr Arg Lys Ile Asn Thr
        115                 120                 125

His Ile Leu Lys Val Pro Glu Thr Asp Glu Val Glu Leu Thr Cys Gln
```

```
    130                 135                 140

Ala Thr Gly Tyr Pro Leu Ala Glu Val Ser Trp Pro Asn Val Ser Val
145                 150                 155                 160

Pro Ala Asn Thr Ser His Ser Arg Thr Pro Glu Gly Leu Tyr Gln Val
                165                 170                 175

Thr Ser Val Leu Arg Leu Lys Pro Pro Pro Gly Arg Asn Phe Ser Cys
            180                 185                 190

Val Phe Trp Asn Thr His Val Arg Glu Leu Thr Leu Ala Ser Ile Asp
        195                 200                 205

Leu Gln Ser Gln Met Glu Pro Arg Thr His Pro Thr Trp Leu Leu His
    210                 215                 220

Ile Phe Ile Pro Ser Cys Ile Ile Ala Phe Ile Phe Ile Ala Thr Val
225                 230                 235                 240

Ile Ala Leu Arg Lys Gln Leu Cys Gln Lys Leu Tyr Ser Ser Lys Asp
                245                 250                 255

Thr Thr Lys Arg Pro Val Thr Thr Thr Lys Arg Glu Val Asn Ser Ala
            260                 265                 270

Val Asn Leu Asn Leu Trp Ser Trp Glu Pro Gly
        275                 280


<210> SEQ ID NO 226
<211> LENGTH: 1675
<212> TYPE: DNA
<213> ORGANISM: Homo sapiens
<220> FEATURE:
<221> NAME/KEY: misc_feature
<222> LOCATION: (1549)..(1549)
<223> OTHER INFORMATION: n equals a,t,g, or c

<400> SEQUENCE: 226

gtacgacyca ctatagggwg agagctatga cgtcgcatgc acgcgtaasc ttgggcccct     60

cgagggatcc tctagagcgg ccgccctttt tttttttttt tttgaagaat aacaattgag    120

ttttattctt taaaggcatt ctctgattta catgagaatt gagaaactga gatgtatgat    180

ttgtctgtta gtcaatttca caccctttca ttctcataag ccccaaattt tgctcagtta    240

aggagcttgc tttaggccca cctatgtaag tctgttatac tagctaatgt gcccatttga    300

atagttcaag ggtcagctaa tgctctgagc ttcatggctc cagtataaag aacaaattta    360

acaaaattaa gctgttactg tagccgagtt acccttctgc tccacacata tgtagtggga    420

tcttgcagga tttccatagt gccaattatc aaaggccttg actacttagc attgctgtat    480

tacagatgtg caaactgagg cactgaaaag tcaaatttaa agtcatattg agggccagaa    540

aaggaggctt agtttggggc tttggccatt ttagctactt atctgaaatt gctgcagata    600

caacgtatga gcatatcaaa tatttttgac tgtatataat tgatttctaa ggtaaaaaca    660

aataaaaaga aaccaataat ttttaaagga aagatgtagt tcaaaaaaaa aaccaccatt    720

aaacatggtg ccattacagg ttaaaacaaa tgctttgtga cttagacctc aaaaacagag    780

cttgatgact ttactccaca atttgtgcac ttagtgtata tttaaatgct ctctgttaat    840

tagaacaact tcattatgct atcaagattc cagtaatcca taaaacatgt caattatgat    900

ttgagtttgt gcgaagccct gtctgtgagc tcatagtctc aatagcctct tctagtaccc    960

agaggaagct atagataaaa aataactcta ttggcaaccc atctgtttct gttactggaa   1020

atttccacac acctctgctt ttggaaatca cttagaaaac ttgaggggaa ataattcctt   1080

ttgctttcag tctggcagca agaaggatcc tgaaggaatt ctgtgggtcc aggatccagt   1140

ggggtaattc tgtaaagtgc agtagtgctt gcttaaagcc ataggctcca gaggtgagtc   1200
```

cagatcagtg aaggggcaag tttcatggcc aggtgttggc tagtcttgtt gcaggtttca 1260
gattaaagtg ctgggtcatc caaaggcatt tgaaaagtgc aaatggcaag ctctgcaggc 1320
caccgaattc ttgttcagag tccagaagct tctttagatg tcatatcagg tcaccctggc 1380
tcccaagacc acaggttcag atagcactgt tcacttccct ctttgttgtg gtgacaggtc 1440
tttttgttgt gtcttttgaa gaatacagct tttgacagag ttgttttctt agggctrtca 1500
ckgkggctat gaaaatgaaa gcaatgatgc aggaggggat gaaaatgtna agcagccaag 1560
ttggatgggt cctgggttcc atctgacttt gaaggtcaat gctggccaaa gtaagttccc 1620
tcacgtgagt attccagaac acacagctga agtttctgcc agggggtggc tttag 1675

<210> SEQ ID NO 227
<211> LENGTH: 23
<212> TYPE: PRT
<213> ORGANISM: Homo sapiens

<400> SEQUENCE: 227

Leu Phe Leu Leu Leu Glu Ile Ser Thr His Leu Cys Phe Trp Lys Ser
1 5 10 15

Leu Arg Lys Leu Glu Gly Lys
20

<210> SEQ ID NO 228
<211> LENGTH: 786
<212> TYPE: DNA
<213> ORGANISM: Homo sapiens
<220> FEATURE:
<221> NAME/KEY: misc_feature
<222> LOCATION: (754)..(754)
<223> OTHER INFORMATION: n equals a,t,g, or c
<220> FEATURE:
<221> NAME/KEY: misc_feature
<222> LOCATION: (778)..(778)
<223> OTHER INFORMATION: n equals a,t,g, or c

<400> SEQUENCE: 228
ggaatgaaca acttttcttc tcttgaatat atcttaacgc caaattttga gtgctttttt 60
gttacccatc ctcatatgtc ccagctggaa agaatcctgg gttggagcta ctgcatgttg 120
attgttttgt ttttcctttt ggctgttcat tttggtggct actataagga aatctaacac 180
aaacagcaac tgttttttgt tgtttacttt tgcatcttta cttgtggagc tgtggcaagt 240
cctcatatca aatacagaac atgatcttcc tcctgctaat gttgagcctg gaattgcagc 300
ttcaccagat agcagcttta ttcacagtga cagtccctaa ggaactgtac ataatagagc 360
atggcagcaa tgtgaccctg gaatgcaact ttgacactgg aagtcatgtg aaccttggag 420
caataacagc cagtttgcaa aaggtggaaa atgatacatc cccacaccgt gaaagagcca 480
ctttgctgga ggagcagctg cccctaggga aggcctcgtt cccatmcctc aagtycaagt 540
gagggacgaa ggacagtacc aatgcataat catctatggg gtcgcctggg actacaagta 600
cctgactctg aaagtcaaag cttcctacag gaaaataaac actcacatcc taaaggttcc 660
agaaacagat gaggtagagc tcacctgcca ggctacaggt tatcctctgg cagaagtatc 720
ctggccaaac gtcagcgttc ctgccaacac cagncactcc aggacccctg aaggcctnta 780
ccaggt 786

<210> SEQ ID NO 229
<211> LENGTH: 93
<212> TYPE: PRT
<213> ORGANISM: Homo sapiens
<220> FEATURE:
<221> NAME/KEY: SITE
<222> LOCATION: (89)
<223> OTHER INFORMATION: Xaa equals any amino acid
<220> FEATURE:
<221> NAME/KEY: SITE
<222> LOCATION: (92)
<223> OTHER INFORMATION: Xaa equals any amino acid

<400> SEQUENCE: 229

```
Met Ile Phe Leu Leu Leu Met Leu Ser Leu Glu Leu Gln Leu His Gln
  1               5                  10                  15

Ile Ala Ala Leu Phe Thr Val Thr Val Pro Lys Glu Leu Tyr Ile Ile
             20                  25                  30

Glu His Gly Ser Asn Val Thr Leu Glu Cys Asn Phe Asp Thr Gly Ser
         35                  40                  45

His Val Asn Leu Gly Ala Ile Thr Ala Ser Leu Gln Lys Val Glu Asn
     50                  55                  60

Asp Thr Ser Pro His Arg Glu Arg Ala Thr Leu Leu Glu Glu Gln Leu
 65                  70                  75                  80

Pro Leu Gly Lys Ala Ser Phe Pro Xaa Leu Lys Xaa Lys
                 85                  90
```

<210> SEQ ID NO 230
<211> LENGTH: 1671
<212> TYPE: DNA
<213> ORGANISM: Homo sapiens

<400> SEQUENCE: 230

```
ttttttttt ttttttttt tttttaaat gataataatt gatttatttt catcttattc     60

cttgagaatt ttcacagctt attttttcca gatcaagttg tgatacctat ttgtatgcac    120

aaatcaaaca aaaatccata ccaacttccc agtgaggtct ttcagatgct ataggattaa    180

ttttctttct tacctcacca cataaatatg ctcaaaacat ctctctgttt tcatgaaata    240

tcgtcatcat catcttagtt ccattacaaa ttatggtgct gcattagcca caaagctatt    300

catggggtat tggttgtgat tctaacttct tttcaaagaa ctatatacta tacatattgt    360

atggtgcttt tgagaattca cgattttggt gtttcacatc tagtggtgtt attacatttt    420

tcccctggta attccaccca cctaaatgga atatattttg ccactctgtg tatacctagt    480

atgtaacttg ttcagtaagt tcagatatat gcacttaact gggggattct aagctacttc    540

cccaataaaa accaatattt tctttccctc tcctttatga gttataaaac actttccctc    600

cccttcttct tttatttagt ttatatgcca gagatttttc tgctctaggg atgaaaatgg    660

aagaccaggg aagaaagttg atgaaataga gatgattcaa agatcggaaa tattttatcc    720

tcactcgata taaagtaaat tattttttct cttttccaat aaccatcatt tcccttgatc    780

ttggaatcat tcaaaaccta gccactgagt cctgtacaaa ctaatgtgct gtctcaagat    840

gagaagaaac atgaaatatt ggtagctgta cagattgtac tagtctgatt atatttacag    900

ttatgagata ccgcaaattt aagaatgcca attttttctc atcactgagt atttattata    960

tataacaaat acatgggaca ggaaaaacta tattgtgtga tataaatagt ttatttacat   1020

tacagaaaaa acatcaagac aatgtatact atttcaaata tatccataca taatcaaata   1080

tagctgtagt acatgttttc attggtgtag attaccacaa atgcaaggca acatgtgtag   1140

atctcttgtc ttattctttt gtctataata ctgtattgtg tagtccaagc tctcggtagt   1200

ccagcccact gtgaaacatg ctccctttag aattaacctc gtggacgctc ttgttgtatt   1260

gtctgaactg tagtgccctg tattttgctt ctgtctgtga attctgttgc ttctggggca   1320
```

```
tttccttgtg atgcagagga ccaccacaca gatgacagca atctgaattg ttccaatcac   1380

agctgcgatt aagacatact gaaatcgtac aggaccggga acaacgtata gaacactgta   1440

gtcctttttt tcacagtgtt gtccagtata accagcatca cacctgcaag atggctcctg   1500

catattgata gaatgctcac ccttcccatg catgcagaag ccattgtaat gttccggaca   1560

aggtatgtgg tgttctctgg cactttcttc taatttgtta gcattctctg cataatctgt   1620

tcttgcataa tgcccatctt cagacttagt agttgtagtt gtgctcgtgc c            1671


<210> SEQ ID NO 231
<211> LENGTH: 35
<212> TYPE: PRT
<213> ORGANISM: Homo sapiens

<400> SEQUENCE: 231

Pro Leu Glu Leu Thr Ser Trp Thr Leu Leu Leu Tyr Cys Leu Asn Cys
  1               5                  10                  15

Ser Ala Leu Tyr Phe Ala Ser Val Cys Glu Phe Cys Cys Phe Trp Gly
             20                  25                  30

Ile Ser Leu
         35


<210> SEQ ID NO 232
<211> LENGTH: 1189
<212> TYPE: DNA
<213> ORGANISM: Homo sapiens

<400> SEQUENCE: 232

gcgtccgctg ggctggaaca gcacagaacc cacagggctg ccgtccacac tctcccggtc     60

agagtcctgg gaccacatgg ggacgctgcc atggcttctt gccttcttca ttctgggtct    120

ccaggcttgg gatactccca ccatcgtctc ccgcaaggag tggggggcaa gaccgctcgc    180

ctgcagggcc ctgctgaccc tgcctgtggc ctacatcatc acagaccagc tcccagggat    240

gcagtgccag cagcagagcg tttgcagcca gatgctgcgg gggttgcagt cccattccgt    300

ctacaccata ggctggtgcg acgtggcgta caacttcctg gttggggatg atggcagggt    360

gtatgaaggt gttggctgga acatccaagg cttgcacacc cagggctaca acaacatttc    420

cctgggcatc gccttctttg gcaataagat aagcagcagt cccagccctg ctgccttatc    480

agctgcagag ggtctgatct cctatgccat ccagaagggt cacctgtcgc ccaggtatat    540

tcagccactt cttctgaaag aagagacctg cctggaccct caacatccag tgatgcccag    600

gaaggtttgc cccaacatca tcaaacgatc tgcttgggaa gccagagaga cacactgccc    660

taaaatgaac ctcccagcca aatatgtcat catcatccac accgctggca caagctgcac    720

tgtatccaca gactgccaga ctgtcgtccg aaacatacag tcctttcaca tggacacacg    780

gaacttttgt gacattggat atcaataagg ccaggcgtgg cggcgattac gtctgtaatc    840

ccaggacttt gggaggccaa ggcgggcaga tcacttcagg ccaggaattc aagagcagcc    900

tggccaatat ggcgaaactc tgtctctact gaaaacaaac aaacaaacaa acaaacaaac    960

aaagaaacaa caaaaattag ccgggtgtgg tggcacacgc ctgtagtccc agctactcag   1020

gaggctgagg cataagaatt gcttgaaccc tggaggcgga ggttgcagtg agctgagatt   1080

gggccaccgc actccagtct gggagacaga gtgagactgt ctcaaaacaa caacaaaaaa   1140

atccctaaca taatctcaaa aaaaaaaaaa aaaaaaaaaa aaaaaaaaa               1189


<210> SEQ ID NO 233
```

<211> LENGTH: 243
<212> TYPE: PRT
<213> ORGANISM: Homo sapiens

<400> SEQUENCE: 233

```
Met Gly Thr Leu Pro Trp Leu Leu Ala Phe Phe Ile Leu Gly Leu Gln
  1               5                  10                  15

Ala Trp Asp Thr Pro Thr Ile Val Ser Arg Lys Glu Trp Gly Ala Arg
             20                  25                  30

Pro Leu Ala Cys Arg Ala Leu Leu Thr Leu Pro Val Ala Tyr Ile Ile
         35                  40                  45

Thr Asp Gln Leu Pro Gly Met Gln Cys Gln Gln Gln Ser Val Cys Ser
     50                  55                  60

Gln Met Leu Arg Gly Leu Gln Ser His Ser Val Tyr Thr Ile Gly Trp
 65                  70                  75                  80

Cys Asp Val Ala Tyr Asn Phe Leu Val Gly Asp Asp Gly Arg Val Tyr
                 85                  90                  95

Glu Gly Val Gly Trp Asn Ile Gln Gly Leu His Thr Gln Gly Tyr Asn
            100                 105                 110

Asn Ile Ser Leu Gly Ile Ala Phe Phe Gly Asn Lys Ile Ser Ser Ser
        115                 120                 125

Pro Ser Pro Ala Ala Leu Ser Ala Ala Glu Gly Leu Ile Ser Tyr Ala
    130                 135                 140

Ile Gln Lys Gly His Leu Ser Pro Arg Tyr Ile Gln Pro Leu Leu Leu
145                 150                 155                 160

Lys Glu Glu Thr Cys Leu Asp Pro Gln His Pro Val Met Pro Arg Lys
                165                 170                 175

Val Cys Pro Asn Ile Ile Lys Arg Ser Ala Trp Glu Ala Arg Glu Thr
            180                 185                 190

His Cys Pro Lys Met Asn Leu Pro Ala Lys Tyr Val Ile Ile Ile His
        195                 200                 205

Thr Ala Gly Thr Ser Cys Thr Val Ser Thr Asp Cys Gln Thr Val Val
    210                 215                 220

Arg Asn Ile Gln Ser Phe His Met Asp Thr Arg Asn Phe Cys Asp Ile
225                 230                 235                 240

Gly Tyr Gln
```

<210> SEQ ID NO 234
<211> LENGTH: 1191
<212> TYPE: DNA
<213> ORGANISM: Homo sapiens

<400> SEQUENCE: 234

```
gctgggctgg aacacaagar cccacagggc tgccgtccac actctcccgg tcagagtcct      60

gggaccacat ggggacgctg ccatggcttc ttgccttctt cattctgggt ctccaggctt     120

gggatactcc caccatcgtc tcccgcaagg agtggggggc aagaccgctc gcctgcaggg     180

ccctgctgac cctgcctgtg gcctacatca tcacagacca gctcccaggg atgcagtgcc     240

agcagcagag cgtttgcagc cagatgctgc gggggttgca gtcccattcc gtctacacca     300

taggctggtg cgacgtggcg tacaacttcc tggttgggga tgatggcagg gtgtatgaag     360

gtgttggctg gaacatccaa ggcttgcaca cccagggcta caacaacatt tccctgggca     420

tcgccttctt tggcaataag ataagcagca gtcccagccc tgctgcctta tcagctgcag     480

agggtctgat ctcctatgcc atccagaagg gtcacctgtc gcccaggtat attcagccac     540

ttcttctgaa agaagagacc tgcctggacc ctcaacatcc agtgatgccc agraaggttt     600
```

gccccaacat catcaaacga tctgcttggg aagccagaga gacacactgc cctaaaatga 660
acctcccagc caaatatgtc atcatcatcc acaccgctgg cacaagctgc actgtatcca 720
cagactgcca gactgtcgtc cgaaacatac agtcctttca catggacaca cggaactttt 780
gtgacattgg atatcaataa ggccaggcgt ggcggcgatt acgtctgtaa tcccaggact 840
ttgggaggcc aaggcgggca gatcacttca ggccaggaat tcaagagcag cctggccaat 900
atggcgaaac tctgtctcta ctgaaaacaa acaaacaaac aaacaaacaa acaaagaaac 960
aacaaaaatt agccgggtgt ggtggcacac gcctgtagtc ccagctactc aggaggctga 1020
ggcataagaa ttgcttgaac cctggaggcg gaggttgcag tgagctgaga ttgggccacc 1080
gcactccagt ctgggagaca gagtgagact gtctcaaaac aacaacaaaa aaatccctaa 1140
cataatctca aaaaaaaaaa aaaaaaaaaa aaaaaaaaaa agggcggccg c 1191

<210> SEQ ID NO 235
<211> LENGTH: 243
<212> TYPE: PRT
<213> ORGANISM: Homo sapiens

<400> SEQUENCE: 235

Met Gly Thr Leu Pro Trp Leu Leu Ala Phe Phe Ile Leu Gly Leu Gln
1 5 10 15

Ala Trp Asp Thr Pro Thr Ile Val Ser Arg Lys Glu Trp Gly Ala Arg
20 25 30

Pro Leu Ala Cys Arg Ala Leu Leu Thr Leu Pro Val Ala Tyr Ile Ile
35 40 45

Thr Asp Gln Leu Pro Gly Met Gln Cys Gln Gln Gln Ser Val Cys Ser
50 55 60

Gln Met Leu Arg Gly Leu Gln Ser His Ser Val Tyr Thr Ile Gly Trp
65 70 75 80

Cys Asp Val Ala Tyr Asn Phe Leu Val Gly Asp Asp Gly Arg Val Tyr
85 90 95

Glu Gly Val Gly Trp Asn Ile Gln Gly Leu His Thr Gln Gly Tyr Asn
100 105 110

Asn Ile Ser Leu Gly Ile Ala Phe Phe Gly Asn Lys Ile Ser Ser Ser
115 120 125

Pro Ser Pro Ala Ala Leu Ser Ala Ala Glu Gly Leu Ile Ser Tyr Ala
130 135 140

Ile Gln Lys Gly His Leu Ser Pro Arg Tyr Ile Gln Pro Leu Leu Leu
145 150 155 160

Lys Glu Glu Thr Cys Leu Asp Pro Gln His Pro Val Met Pro Arg Lys
165 170 175

Val Cys Pro Asn Ile Ile Lys Arg Ser Ala Trp Glu Ala Arg Glu Thr
180 185 190

His Cys Pro Lys Met Asn Leu Pro Ala Lys Tyr Val Ile Ile Ile His
195 200 205

Thr Ala Gly Thr Ser Cys Thr Val Ser Thr Asp Cys Gln Thr Val Val
210 215 220

Arg Asn Ile Gln Ser Phe His Met Asp Thr Arg Asn Phe Cys Asp Ile
225 230 235 240

Gly Tyr Gln

<210> SEQ ID NO 236
<211> LENGTH: 733
<212> TYPE: DNA

<213> ORGANISM: Homo sapiens

<400> SEQUENCE: 236
gggatccgga gcccaaatct tctgacaaaa ctcacacatg cccaccgtgc ccagcacctg 60
aattcgaggg tgcaccgtca gtcttcctct tcccccaaa acccaaggac accctcatga 120
tctcccggac tcctgaggtc acatgcgtgg tggtggacgt aagccacgaa gaccctgagg 180
tcaagttcaa ctggtacgtg gacggcgtgg aggtgcataa tgccaagaca aagccgcggg 240
aggagcagta caacagcacg taccgtgtgg tcagcgtcct caccgtcctg caccaggact 300
ggctgaatgg caaggagtac aagtgcaagg tctccaacaa agccctccca acccccatcg 360
agaaaaccat ctccaaagcc aaagggcagc cccgagaacc acaggtgtac accctgcccc 420
catcccggga tgagctgacc aagaaccagg tcagcctgac ctgcctggtc aaaggcttct 480
atccaagcga catcgccgtg gagtgggaga gcaatgggca gccggagaac aactacaaga 540
ccacgcctcc cgtgctggac tccgacggct ccttcttcct ctacagcaag ctcaccgtgg 600
acaagagcag gtggcagcag gggaacgtct tctcatgctc cgtgatgcat gaggctctgc 660
acaaccacta cacgcagaag agcctctccc tgtctccggg taaatgagtg cgacggccgc 720
gactctagag gat 733

<210> SEQ ID NO 237
<211> LENGTH: 5
<212> TYPE: PRT
<213> ORGANISM: Homo sapiens
<220> FEATURE:
<221> NAME/KEY: SITE
<222> LOCATION: (3)
<223> OTHER INFORMATION: Xaa equals any of the twenty naturally occuring
L-amino acids

<400> SEQUENCE: 237

Trp Ser Xaa Trp Ser
1 5

<210> SEQ ID NO 238
<211> LENGTH: 86
<212> TYPE: DNA
<213> ORGANISM: Artificial Sequence
<220> FEATURE:
<221> NAME/KEY: primer_bind
<223> OTHER INFORMATION: Synthetic sequence with 4 tandem copies of the
GAS binding site found in the IRF1 promoter (Rothman et al.,
Immunity 1:457-468 (1994)), 18 nucleotides complementary to the
SV40 early promoter, and a Xho I restriction site.

<400> SEQUENCE: 238
gcgcctcgag atttccccga aatctagatt tccccgaaat gatttccccg aaatgatttc 60
cccgaaatat ctgccatctc aattag 86

<210> SEQ ID NO 239
<211> LENGTH: 27
<212> TYPE: DNA
<213> ORGANISM: Artificial Sequence
<220> FEATURE:
<221> NAME/KEY: primer_bind
<223> OTHER INFORMATION: Synthetic sequence complementary to the SV40
promter; includes a Hind III restriction site.

<400> SEQUENCE: 239
gcggcaagct tttgcaaag cctaggc 27

<210> SEQ ID NO 240

<211> LENGTH: 271
<212> TYPE: DNA
<213> ORGANISM: Artificial Sequence
<220> FEATURE:
<221> NAME/KEY: protein_bind
<223> OTHER INFORMATION: Synthetic promoter for use in biological assays; includes GAS binding sites found in the IRF1 promoter (Rothman et al., Immunity 1:457-468 (1994)).

<400> SEQUENCE: 240
ctcgagattt ccccgaaatc tagatttccc cgaaatgatt tccccgaaat gatttccccg 60
aaatatctgc catctcaatt agtcagcaac catagtcccg cccctaactc cgcccatccc 120
gcccctaact ccgcccagtt ccgcccattc tccgccccat ggctgactaa ttttttttat 180
ttatgcagag gccgaggccg cctcggcctc tgagctattc cagaagtagt gaggaggctt 240
ttttggaggc ctaggctttt gcaaaaagct t 271

<210> SEQ ID NO 241
<211> LENGTH: 32
<212> TYPE: DNA
<213> ORGANISM: Artificial Sequence
<220> FEATURE:
<221> NAME/KEY: primer_bind
<223> OTHER INFORMATION: Synthetic primer complementary to human genomic EGR-1 promoter sequence (Sakamoto et al., Oncogene 6:867-871 (1991)); includes a Xho I restriction site.

<400> SEQUENCE: 241
gcgctcgagg gatgacagcg atagaacccc gg 32

<210> SEQ ID NO 242
<211> LENGTH: 31
<212> TYPE: DNA
<213> ORGANISM: Artificial Sequence
<220> FEATURE:
<221> NAME/KEY: primer_bind
<223> OTHER INFORMATION: Synthetic primer complementary to human genomic EGR-1 promoter sequence (Sakamoto et al., Oncogene 6:867-871 (1991)); includes a Hind III restriction site.

<400> SEQUENCE: 242
gcgaagcttc gcgactcccc ggatccgcct c 31

<210> SEQ ID NO 243
<211> LENGTH: 12
<212> TYPE: DNA
<213> ORGANISM: Homo sapiens

<400> SEQUENCE: 243
ggggactttc cc 12

<210> SEQ ID NO 244
<211> LENGTH: 73
<212> TYPE: DNA
<213> ORGANISM: Artificial Sequence
<220> FEATURE:
<221> NAME/KEY: primer_bind
<223> OTHER INFORMATION: Synthetic primer with 4 tandem copies of the NF-KB binding site (GGGGACTTTCCC), 18 nucleotides complementary to the 5' end of the SV40 early promoter sequence, and a XhoI restriction site.

<400> SEQUENCE: 244
gcggcctcga ggggactttc ccggggactt tccggggact ttccgggact ttccatcctg 60
ccatctcaat tag 73

<210> SEQ ID NO 245
<211> LENGTH: 256
<212> TYPE: DNA
<213> ORGANISM: Artificial Sequence
<220> FEATURE:
<221> NAME/KEY: protein_bind
<223> OTHER INFORMATION: Synthetic promoter for use in biological assays; includes NF-KB binding sites.

<400> SEQUENCE: 245
ctcgagggga ctttcccggg gactttccgg ggactttccg ggactttcca tctgccatct 60
caattagtca gcaaccatag tcccgcccct aactccgccc atcccgcccc taactccgcc 120
cagttccgcc cattctccgc cccatggctg actaattttt tttatttatg cagaggccga 180
ggccgcctcg gcctctgagc tattccagaa gtagtgagga ggcttttttg gaggcctagg 240
cttttgcaaa aagctt 256

<210> SEQ ID NO 246
<211> LENGTH: 46
<212> TYPE: PRT
<213> ORGANISM: Homo sapiens

<400> SEQUENCE: 246

Gly Leu Cys Met Val His Ser Leu Leu Thr Ser Ser Leu Gly Gly Arg
1 5 10 15

Cys Cys Asn Tyr Pro Tyr Ile Ala Asp Lys Asp Ile Glu Thr Glu Val
20 25 30

Lys Pro Pro Ser Gln Gly His Thr Trp His Leu His Cys Ser
35 40 45

<210> SEQ ID NO 247
<211> LENGTH: 5431
<212> TYPE: DNA
<213> ORGANISM: Homo sapiens

<400> SEQUENCE: 247
gggctggctg ctgtcagaac ctaggccctc ccctgccttg ctccacacct ggtcagggga 60
gagaggggag gaaagccaag ggaagggacc taactgaaaa caaacaagct gggagaagca 120
ggaatctgcg ctcgggttcc gcagatgcag aggttgaggt ggctgcggga ctggaagtca 180
tcgggcagag gtctcacagc agccagtaag tgaacagctg gactcgggct gcctgggcgg 240
cagggagaag cgggcagggg aagggtcagc agaggagcga ggccccagag gagccctggg 300
gtggagcaca gccaagggct ctgttccctt tcctggactc ggcttccaca ggccctgacc 360
tgcctccccc accctccggt cctgcccctg tgcctggcag cagccccacc tgtgtgacat 420
cccagcacac ccccccctctc cttgcaaagg agaagggagc ggcctagggg aggccagggg 480
cccacctggg ctggggctgt ggagagggag tggctgggac gggaggaaaa agagagacgg 540
agattagatg gaagaagagg gatttcaaga caaattgcca gagatgcagt cagagagact 600
gactgagaga cacaaagata gaaggaatta gagaaagggc cacacagagc cagacagaga 660
gagaagagtg gagatggaga cagggacgag gacagagaaa ggcagacaga cacataggga 720
cagaaagaga aaaatcacac aaagtcagaa ttactgaatg acagggaatg acacatagaa 780
cgagacacag attcagagac tcagggcagg gaaaggaagg ctgcagacag acagacagac 840
agagggaggc tgagacacag ggagaagagg ggcttggaga ggtggcacag gcaggcagcc 900
agtgcctcag aggcctccgg ggagggccct cacacacacc ccgccccggg gcattaaggc 960
agggcttgga ggccagtcat cctgggcccg cccagggccg ccccccctgcc agcccgcctg 1020

-continued

```
cctggtgcct ggcacctggc gctccaaccc agcctacctg ctgtagctgc cgccactgcc   1080
gtctccgccg ccactgggcc cccagagccc cagccccaga gcctgtgagt ccaggaggaa   1140
agggaagctg cccctccccg tccaggtgtc agccctcccc aaggacacct gtcccactcg   1200
ggcacccatt tctccctctg ctctgtcctt ctctgcttgg gtgggggttc ctggcctctc   1260
tctacacctc tcacctccga tggctgtccg cagcctcagt tacctctaat ctccatggct   1320
tcagctgctg agctggccct ctgctcccac ccccgctggc cagggcagcg gagggcactg   1380
gccctcccct cgaccagccc cgcccagctt tgcttggctg tccttcaaaa gggcaggggt   1440
ttggcggaca gggcttcagc aagccgggtg atgggggtcc cagacattgt ctggggctga   1500
gcccccctact ccccctccagc agacctcaaa ggctccatat cgctctgctg cgaagacaat   1560
gaaaaagggg tggctacgga acggtgtctg gttccccttg tccttccacc ccaagctgct   1620
ggggcctggc cagctctcaa ggcaagaagg aaaacatcct ctgacatgtg ccggggaggt   1680
cccatggctg acttgaacag ggccgaacca tggcttgaca gctcaaagcc cctcccaacg   1740
acttccacat ggttcttggt atctcggaag cttctagctg tgaccaggcc ctctccaagg   1800
ccaccctaga cacctaagat atattttaag tgtttggaga tctgagtgct gtgagaaaca   1860
ggggatttcc ccaaccttgt ttctcccaag tggggagcgg gagcaggtga gggagagagg   1920
agagggcatg agccagcccc cccctcccga tttccccgta aagtgatgcg gccccatgtc   1980
cctccttgtt cccagaggaa cctggggccc gctcctcccc cctccaggcc atgaggattc   2040
tgcagttaat cctgcttgct ctggcaacag gtacgcaggg gatgggggca gggcaggatc   2100
ctccctcttg aatctctggg atcccctaac cctctgtgtc tggacagtga cagggctgat   2160
tccaaattac agaacaaccc ataaggcacc tgaactggag cagtggtcat gagggcctgg   2220
atgcccttct agataatccc tttaaatgcc aaaggaggag aggtcaaggg ggtcgtaaag   2280
ggtcccgtgg aggggctgag gaagctggag ttgggggagc agtcactcaa agcgcccagg   2340
acaggggcta ctgaccaacc agtatggaag tatttccttt tttttttttc ccagagacaa   2400
agtcttgctc tattgtccag gctggagtgc cgtggtgcca acacggctca ctgcagtctt   2460
gacttcccgg gcttaagtga tccttaagcc atctcagctt ccccggtagc tgggaccaca   2520
ggcacctgcc accaagccag gctaattgtt taattgtttg tagagatggg ggaggaggtc   2580
tcactatgtt tgcctaggct gatctagaac tcctgggctc aagtaatcct cccaccttag   2640
cctctcaaag tgctgggatt acaggcatga gccactgcat ttgaccttat ggaagtattt   2700
tcatccttta atacccgacc ccagcatcca gggcaaccca gagggacacc agaccagggc   2760
ccagaccacc cactctcttt ctctcctccc cacccccatt tctgggagtc ctcctggtct   2820
accacctctc cttcctgagc cccttctttt gctctcaccc cctccagggc ttgtaggggg   2880
agagaccagg atcatcaagg ggttcgagtg caagcctcac tcccagccct ggcaggcagc   2940
cctgttcgag aagacgcggc tactctgtgg ggcgacgctc atcgccccca gatggctcct   3000
gacagcagcc cactgcctca agccgtgggt gcgggggctg gggcggtgcc ggggtggggg   3060
gctgggaatg gggagatgga tggagagaag ctcagggata ggggtgctgg taaggggatt   3120
agagatgggg atgggtagtg tcagcaaggt tgatgggctc gagttggtat tgaaggtggg   3180
gggatgaatg gggttgggat ggggctatgg ctgggaaggg ggcttcggtg ggagacgtgg   3240
aagaggttgg aagcagagcg atgtttcttc atcctcaaag gtgtcactca cctctcccac   3300
ccatgtctcc cccgaccttt cctcctccaa ctactgtctc tcccacctca gccgctacat   3360
agttcacctg gggcagcaca acctccagaa ggaggagggc tgtgagcaga cccggacagc   3420
```

-continued

```
cactgagtcc ttcccccacc ccggcttcaa caacagcctc cccaacaaag accaccgcaa   3480

tgacatcatg ctggtgaaga tggcatcgcc agtctccatc acctgggctg tgcgacccct   3540

caccctctcc tcacgctgtg tcactgctgg caccagctgc ctcatttccg gctggggcag   3600

cacgtccagc cccccagtgta ggagcaccag aggggaacct ggcagggggt ggtgaggagg   3660

gagtggtcag gattgtggaa gggttcaggg catcagagat gcggttcaca gtgacgatgt   3720

gggataagtt gagaggatgt gtggaaaacg tcaggatagg ggggtgggga caaaagttgg   3780

ggccttggag tcagacggac gggatatgca atcatacatc cataacctcc tggttgtaag   3840

accttaggca agcagcttca cctctctgaa tcttgatttt cttctctata aaatgagaat   3900

gattataccc acctgtcagg attggattag agataatgta tatcaagcaa ctgacataaa   3960

tcatttattg gatagcaggc tgggcaccgt ggctcacgcc tgtaatccca gcactttggg   4020

aggccgaggt gggaagatca cctgaggtca ggactttgat accagcctgg ccaacgtggt   4080

gaaatcccat ctctactaaa aatgtgaaaa ttagttgggc gtggttgtgt gcgcctgtaa   4140

tcccagctac tcgggaggtt gaggcaggag aatcgcttaa acttgggaga cggaggttgc   4200

agtgagccaa gatcacgcca ctgcactcca gcctgggcaa cagagcaaga ctctgtctcg   4260

aaaaaaaaaa aaaaaaagct ggatagcatt gctgttgcta ttgttacaag aagagaggtg   4320

agttggctgc gtctaaggac agggattccc ccaggggcgg gatcacagca agcactgcat   4380

taggggaggt ggcagggggc tcattcccac agcccctcac gctgtttcca cagtacgcct   4440

gcctcacacc ttgcgatgcg ccaacatcac catcattgag caccagaagt gtgagaacgc   4500

ctaccccggc aacatcacag acaccatggt gtgtgccagc gtgcaggaag gggcaagga    4560

ctcctgccag gtcagtgtgg tctccaacca cagccccatc cccatcccca gcttcaatga   4620

catctttacc gacatccaca atttcatccc caacctcaac ccgccgaccc ctgcaactcc   4680

caatccatct cttcccctgt tcccgtttct gacctcagca caaacttcag ctccatcccc   4740

gtttccacac catttccagc tccaaccatc cccaaactcg tttttgagcc taaccccatc   4800

ctttatccca cccataatcc cagctttatc gctaaaccta tcacctttcc cagtgcctac   4860

ccatcctgtc tcggccccac tcctaagcac cgtccccacc tcctccctgg ctaacaccat   4920

gctcaacgct ttctctgacc gacattctct ctccccgtgc ccagggtgac tccgggggcc   4980

ctctggtctg taaccagtct cttcaaggca ttatctcctg gggccaggat ccgtgtgcga   5040

tcacccgaaa gcctggtgtc tacacgaaag tctgcaaata tgtggactgg atccaggaga   5100

cgatgaagaa caattagact ggacccaccc accacagccc atcaccctcc atttccactt   5160

ggtgtttggt tcctgttcac tctgttaata agaaacccta agccaagacc ctctacgaac   5220

attctttggg cctcctggac tacaggagat gctgtcactt aataatcaac ctggggttcg   5280

aaatcagtga gacctggatt caaattctgc cttgaaatat tgtgactctg ggaatgacaa   5340

cacctggttt gttctctgtt gtatccccag ccccaaagac agctcctggc catatatcaa   5400

ggtttcaata aatatttgct aaatgagtga a                                  5431
```

<210> SEQ ID NO 248
<211> LENGTH: 5791
<212> TYPE: DNA
<213> ORGANISM: Homo sapiens

<400> SEQUENCE: 248

```
ggacggagag atagcagcga cgaggacagg ccaaacagtg acagccacgt agaggatctg     60

gcagacaaag agacaaggtg agaaggaggt aggcgactgc caatgaggga gtgacacaca    120
```

-continued

```
ggggagcagg tagagagagg acaagcaggt catccccttg gtgaccttca aagagaagca    180
gagagggcag aggtgggggg cacagggaaa gggtgacctc tgagattccc cttttccccc    240
agactttgga agtgacccac catggggctc agcatctttt tgctcctgtg tgttcttggt    300
gagttctccc ggagcaggga gagggcagga ctgcgactgg atcccttcac ccccatgagg    360
aggccccacc accctcccca tctcagctct ggcccccagc ctggtggtga ggaggagagg    420
ggctttctct gtgcctccat ttacctgcag ctctcagggt actgctcacc tcggtctccc    480
ctattttttg atccctcttc ccttctgtcc ctctctgaat ctctgtctct ccatttccct    540
cctatgtgta agcatctttc tccctgggtg tctttgatgt ttcatggtct ttttctatca    600
ctgggtctct ctctctttct ctctctttct cgtctctctt tctcctctct ctctcctgcc    660
tgtttctctc tctcactctg tgtgtctctc catctctgta tcttttcttc ctctctctga    720
cccatgcccc tgtctgtctc cagggctcag ccaggcagcc acaccgaaga ttttcaatgg    780
cactgagtgt gggcgtaact cacagccgtg gcaggtgggg ctgtttgagg gcaccagcct    840
gcgctgcggg ggtgtcctta ttgaccacag gtgggtcctc acagcggctc actgcagcgg    900
caggtaagtc ccttcctggg gtgggcgaag ggaggactat gggaaggcaa gcgctggggg    960
taggatcaca agggagggtg gtgcccactg ggaagaagct gatcctgcaa caagagagtc   1020
tgaggttaga ccaggagtgg aacttcctta gcagtgggcc tggggtggtg ctgggcaggg   1080
tgaggtatgt tgggtggagg gccggggagg gtcctggaac ctgccctcct gcctctccca   1140
ttcctgcatg taccctttct ttcctatatg acatctgcca ctcaccccag ccattccttg   1200
acccagtctg ggcccggggc ccaggtctca cccaagctct ttttcttttt cttttttta   1260
ttttttgag acagggtctc gctctgtcgc ccaggctgct gtgcaatggc gtgatcacag   1320
ctcactgctg tctctgcctc ccaggttcaa gtgattctcc tgccccagcc tcctgagtag   1380
ctgggattac aggcacccgc caccatgccc agctaatttt tgtatttttt gtagagacag   1440
ggttttgcca tgttggccag gctggtctcg aactcctggc ctcaaatgac ctgcccgtct   1500
tggcctccca aagtgctggg attacaggtg tgagccactg cacccggcca acatgaccca   1560
aactctttgt gcaacttcag aatctatgcc tggcacctct ctgggcctca gtagactgat   1620
gttctggaat tttttcttt ttctttcttt ttttttttt ttggagacag agtcttgctc   1680
tttctgtcat ccaagctgga gtgcagtgat gctatcttgg ctcactacag cctcaaccac   1740
ctgggctcaa gtgatcctca cacctcagcc tcccaaggag ctaagactac aggcctgcgc   1800
caccacacct ggctaatttt taaatttttt ttgtagagac agggttttgc tatgttaccc   1860
aggctggtct caaactcctc agctcaagca atcttcctgc cttgacctcc caaagtgctg   1920
ggattacagg catgagccac tgtgcctggc ctggaacttt ttttgtgaaa ggggagatca   1980
gatgcaaaga aacagagact cagggagaga gagggccagc agcaggatgc agagaggcca   2040
ttcatcaacc cactcgttca atcatgaacc cactcgtcca cgcatgagca tggagggcac   2100
atgctccgtg ccaggcggtg ggaataaggc agtgaacaag gtccactgat gtccctgcct   2160
tcatgggctt caccagccga gagaatcaga aagagaggcc tggcgcggtg gctcacacct   2220
gtaatcccag cactttggga ggccgaggcg ggcggatcac ttgaggtcag gagtttgaga   2280
ccagcctgac acacatggtg aaaccttatc tctactaaaa atacaaaaat tagctgggca   2340
tggtggcatg cttctgtaat cccagctact tgggaggctg aggcaggtga attgcttgaa   2400
cctgggaggt ggaggttgta gtgagccaag atggtgccac tgcactccag cctgggcgac   2460
agagcgagac tcggtcttga aaaaaaaaaa aaaaaaaaaa aggagagaga gagacacaga   2520
```

-continued

```
tgcagggaca tggtaggaga aacagggaac acccaagatg gaaagagggt gatggaggtt   2580
gggaataaga gcctgtaaga gagactcgga gaatgagagt tgcgggtgag aggacagaca   2640
gtgaggggca gaacagtggg gagcggcagg agcgcctgag tgtccgtgga ggggtgcaag   2700
gtgggggact gcgtgcctgc cacccgctca gccgtcgcca ccggcagcag gtactgggtg   2760
cgcctggggg aacacagcct cagccagctc gactggaccg agcagatccg gcacagcggc   2820
ttctctgtga cccatcccgg ctacctggga gcctcgacga gccacgagca cgacctccgg   2880
ctgctgcggc tgcgcctgcc cgtccgcgta accagcagcg ttcaacccct gcccctgccc   2940
aatgactgtg caaccgctgg caccgagtgc cacgtctcag gctggggcat caccaaccac   3000
ccacggagta aggggcccag ggccaggggt caggggtcag gatgggtaca agtctgggat   3060
gcagggcgag aggtcgaatc atgacacctc agaggaagga tgggtaaagg gtcagggtgt   3120
gggatgggac atcaggatca tggtttgggg tcagagatta tggtggattg gggtcttggg   3180
agccaaaggg gttaaaggac tggtatgaa gtcagggatc agaggtcaga ggtcagagtg   3240
tgtcagaggt catcacactg gagcaaaagg catatatata tatatatgta tgtataggat   3300
atgggcattg tgggtcatgg gtctggggtt agaggtcacc gtagaattaa ggtcatggga   3360
tccagaggtt gtacaatctg gtcaaaatct gaggatggaa attgggattc tatccaaaat   3420
cacatatctg agattggagg tcatagcgtt tggggtgtgg ggcccgaagt ttggggtcat   3480
ggaggctggg gcccaataaa ctaggatcag gggacactgg cgttggaagc agtgaggttt   3540
ggaagatgca gagctgaggt tggaggttaa ggtaaagaca gggacatggg gtcaggagac   3600
agaagatatg agatcaagct gggatcataa ggtaataaga cagaaggtca aagatcacag   3660
tagctggcat tgaagagggt caggtctgga ttcgttgtct ctgacgctgg agagacaaga   3720
aagttcttga gttatgccac tcaaagtcaa atgtcaaaga tcaaagagac cgtcaatcat   3780
ctggggtcat gattcatatg aaattaagtc ataaatatgt aacttggagg tttcgggatt   3840
gtagtacagg tcggtgaggg gcaggggtat tgacatggat gggccacatc cagggaagag   3900
ggacgtggcc tcaaagtggg gagatttagg ggaccctgca gcacgcatgt tctctctcca   3960
gacccattcc cggatctgct ccagtgcctc aacctctcca tcgtctccca tgccacctgc   4020
catggtgtgt atcccgggag aatcacgagc aacatggtgt gtgcaggcgg cgtcccgggg   4080
caggatgcct gccaggtgag ccagtgcagg cagcgtgcgt ggtcaccagg acaggaagtg   4140
aaggggaggg gctggaagca ggaggggaac tgatggagga tgaatcaggg aaaggggatg   4200
ctgcagagag acggggtcaa aaaggaaggg agaggctggt tacggaggct cacacctgta   4260
atcccagcac tttgggaggc cgaggcgggc ggatcacttg aggtcaggag ttcaagacaa   4320
gcctggccaa cacggtgaga ctctgaatct actaaaaata ccagaattag ccgggggtgg   4380
tggtgcaagc ctgtggcccc agctacttgg aaggctgagg caggagaatc gcttgatccc   4440
gggaggcgga ggttgcagtg agctgagatc acgccactgc actccagcct gggcgacaga   4500
gccagactct gtctcaaaac aaaataatta ataataataa taataataat aataataata   4560
atggaggaga ggcccaggat aagggaggga gagagacagg gagtaaaagg gaggaccggg   4620
gaatggagga gggggagggg cagggagaga gagggaggaa gggaacagag aaggaaagat   4680
ggggcagggg ttacagagag agacagcaaa acagacggag aggactggga gcccagacag   4740
ggaaccagct gtttctgggg ctctaagtct ttcccatacc atcctccagt tggtgctgtc   4800
ccagactgag agagatttga ggatggcggt ctctcccctc attggtcagg gccccagcca   4860
ttgtccttga gagaactctg tgcttttgat ggagtcctgc ccaccttccc tgggattggt   4920
```

-continued

```
cattttttgat ggcactctct cccctcattg gtcagaaccc caggcattgt ccttgagaga   4980

acctctatcc tttatggagt cccaccctcc tcccctggga ttggtcattg ataatagtgt   5040

tctctctcct cattggtcag ggccccagcc attgtccttg agagaatgct cgactcttta   5100

tgttgtcttg acagcctccc ctgagattgg tcattaatga ctgtgctctc tctcctcatt   5160

ggtcagggcc ccagccattg tccttgagag aacctctgtc ctttatggag ttccaccctt   5220

cttccctggg attggcccct agagacagtg gttcttctct tttggttagc cattgccatt   5280

gtcctccggg aaagtgatta tactcttttg tctaatgacc agacttggag ccctccccaa   5340

ggcccaggac tgggttgaag ggttggggag gaaaacagaa ataagatgtc tcccttgttc   5400

agacagtact tctcttccct tccagggtga ttctgggggc cccctggtgt gtgggggagt   5460

ccttcaaggt ctggtgtcct gggggtctgt ggggccctgt ggacaagatg gcatccctgg   5520

agtctacacc tatatttgca agtatgtgga ctggatccgg atgatcatga ggaacaactg   5580

acctgtttcc tccacctcca cccccacccc ttaacttggg taccccctctg gccctcagag   5640

caccaatatc tcctccatca cttcccctag ctccactctt gttggcctgg gaacttcttg   5700

gaactttaac tcctgccagc ccttctaaga cccacgagcg gggtgagaga agtgtgcaat   5760

agtctggaat aaatataaat gaaggagggg c                                  5791
```

<210> SEQ ID NO 249
<211> LENGTH: 3109
<212> TYPE: DNA
<213> ORGANISM: Homo sapiens
<220> FEATURE:
<221> NAME/KEY: misc_feature
<222> LOCATION: (984)..(984)
<223> OTHER INFORMATION: n equals a,t,g, or c

<400> SEQUENCE: 249

```
ggggagatat agatgtttat aagatcaaat gatcacagca acataggaat tacccagaga     60

gagctagggc agaatatcct gggagccaaa taacaggata gggaatgttc tacgagttcg    120

gggcatgcag tacgtgcggg gacctggggc gggtaggaag tcttgaaaga cttcatttag    180

gaagtgggat ttgggctgag tttggtggat ggcatcatga gtcagtgagt aaactgtcat    240

gacaatcagg atctgaaaga gaactaagag agccatgata catagggagg ggcttagtga    300

ggacagagga cgtcagaggg ctgtagtcag gggaaaatta tttccctttt ctcaggacca    360

tcagtcaggc tctttgtgtc taggagcctc ctaatgcagt cttctgcaca gtcctgggga    420

ctgactgact gaatcacacc tctggggctg ggggctgctg acatgtgtgc ctttccttgg    480

ctgcttcttc tcctgctgct ccaggagggt gagtgaagct gccagctcgt gcacaggaat    540

gtcccctaca cctctgttcc cctgccccac tgggtctggg ccagtaagac cctttcttag    600

gggttgaatg tgtcagctct tctggagtta caaggagtag ggtgtgtggc ttcagggcag    660

gaccgagaga cacctgggga tatggaagaa agagcaatcc caagatggca aaggagaagg    720

taaaacttgg agggtgaagg gacagatgga agcaaactcc tgttaggtgc ttaactcagg    780

gaaaggggaa atctagagtc agaagcagca gctggagaac aggatttagt gtgagagtca    840

tagaagctgc ccagctgaga ttacgctact ctggcagctc cactgccagg ttcagcagcc    900

cagagacagc agctgggttg tttgcttctc ttttcttcct gcataggcag ccaaaggaga    960

ctctggagat ggtgtggatc gagngaagtg gttgcggtcc ttcaggagtc catcagcctc   1020

ccccttggaa ataccaccag atgaagaggt tgagaacatc atctggtcct ctcacaaaag   1080

tcttgccact gtggtgccag ggaaagaggg acatccagct accatcatgg tgaccaatcc   1140
```

acactaccag ggccaagtga gcttcctgga ccccagctat tccctgcata tcagcaatct 1200
gagctgggag gattcagggc tttaccaagc tcaagtcaac ctgagaacat cccagatctc 1260
taccatgcag cagtacaatc tatgtgtcta ccgtgagttt aggctgggaa ccataaagct 1320
ggttttgggg gctcttctga gcttctcaca ccatggagtg ggcgtctcag gacttggggt 1380
tatggtttga ggggctagaa ctggaggcag actgtctcca atctagatac tatgattgag 1440
tgtgcccaat ccacctgttg tatctgaacc gcagcaacag gcggagtgac ctggagcaag 1500
gaggctgtcc gatgcagtgg cagggatcag gggcttcatg tacagatcct gtaggggct 1560 tttctcttcc agtgaaattg tgttctgggg atgaacacca cctacattct tgagcctttt 1620
atttccctgt gtgatgaggg ctactaatga gtatcttctc tttacttgaa cccaaatttc 1680
ttcttagtgt ctgtcacact gcatctacct tgaagcttga agggacactg attaaaatgt 1740
aaatgcccct gagaggggtg ataatatttc atgggatcaa ggagacagaa tggggtttgg 1800
aggaaggtag agtacaaaag taagagagag aatacgtaaa ggggaggtgg aagatgccaa 1860
aggcagctct gtcttccttg acagttgcct tggggacctt gaaaccacag gttttatggt 1920
ggttgggttt gtttgctttt gcctatttgt tgtttaggtg caggggctgt caaggggtag 1980
cattagtacc ccaggtttga ggagcttagg aaaacagacc caatccctga ttgtttagag 2040
ggtctttgtg tttccccttc atccaggatg gctgtcagag ccccagatca ctgtgaactt 2100
tgagagttct ggggaaggtg cctgcagtat gtccctggtg tgctctgtgg agaaggcagg 2160
catggatatg acctacagct ggctctcccg gggggatagc acttatacat tccatgaagg 2220
ccctgtcctc agcacatcct ggaggccggg ggacagtgcc ctctcctaca cctgcagagc 2280
caacaacccc atcagcaacg tcagttcttg ccccatccct gatgggccct tctatgcagg 2340
taccagaacc cctgagacac cccctgagct catgaaagat agtgcctaga ggcaccatct 2400
ccctccccca gctcttccca agagagccca gggaattcag aagctaaccc cctcccatgg 2460
aggcttgaca cctggattgg agaggagacc ctccgttttt ctagtgcccc caacttccaa 2520
aggtcttttc ttttctcttg cttggcttca gaatgattcc tagatctcag ttcctgagct 2580
tctgtgcata gaatatattt ccagagacac ttgcaagggg acttcaactg attgtgaact 2640
tgagacccct tcatgaaatt tgggtaggag tctgcccaaa tcttaacccc aaccctacca 2700
ctgatgggcc ctttcctcct ttcttccacc ccagatccta actatgcttc tgagaagcct 2760
tcaacagcct tctgcctcct ggccaaggga ttgctcatct tcttgctctt ggtaattctg 2820
gccatgggac tctgggtcat ccgagtccag aaaagacaca aaatgccaag gatgaagaaa 2880
ctcatgagaa acagaatgaa attgaggaag gaggcaaagc ctggctccag ccctgcctga 2940
ctgctccttg ggaaccccag tcctgagctt ggtttcttcc cagcacccag agaatccttc 3000
ctcagctctc ttctttccag ggaaggaggg tgctcagggg tgggtatcca gagagccata 3060
cttctgaggg aagactggct ggcaataaag tcaaattaag tgaccacaa 3109

<210> SEQ ID NO 250
<211> LENGTH: 104
<212> TYPE: DNA
<213> ORGANISM: Homo sapiens

<400> SEQUENCE: 250
atttttgtat ttttagtaga gacggggttt caccatgttg gccaggctgg tctcaaactc 60
ctgacctcag gtgatctgcc tgcctcggcc tcccaaagtg ctgg 104

<210> SEQ ID NO 251

<211> LENGTH: 3097
<212> TYPE: DNA
<213> ORGANISM: Homo sapiens

<400> SEQUENCE: 251
tttagggtag aagaaaaggt tttatttttc tttctcacat tggaaaaaat gaaaactttc 60
ggacccatga aattttatta cattttgcca aaaacagaac caataacata agtattcaaa 120
gttatgtaaa gataattatt taatatgaac attatgatgg tgagagggac cacggagcaa 180
ggggctgcct tgcaggcctg ccttccagct ttgctacagg gaccagaagc gggagctgag 240
cgcaggggag gcaggcggag gccatgggca gcgaggcggg tgcgccaaag ggcgccagtt 300
ccggagctgc tgggcctggg ctgcaggagg gcggagctgg ggccgcaagg ctggtgccgg 360
ccgacaaacg acgcggcgcg ggcgagtggg cggaggcggc tgcggggaag gctgggctgc 420
cgcgggacgc ggtgaagata gcctgcggag tgtccgggct gaacacgtga gtctgagggt 480
cgccagggaa tcactgcgtg gctgcctctg tgtcggagat ccagatgcct ggactggcct 540
cggggtccca gcgcttgccc ggcgagccgg cggtccgggg acgggtccgg gccgaggcct 600
gcggtgaact cggctcggcg ggtgcccagg aggcgggtcc ggggcggggc ctgcggtgaa 660
ctcggctcgg cgggtgccca ggaggcgggt ccggggcggg gcctgcggtg aactcggctc 720
ggcgggtgcc caggaggcgg gtccggggcg gggcctgcgg tgaactcggc tcggcgggtg 780
cccaggaggc ggggcagggg cggggcctgc agtgagcgcg gcttggtgag tagcccagga 840
ggcgggtccg gggcggggcc tgcggtgagc tcggctcggg gggttgctca ggaggtgggg 900
ccggggcagg cctggggcgg ggcctgcggt gagctcgcgc tgggcgggct gttccggggg 960
cgggactggg ctgggcctgc ggtgagcatc aggcgatgcg gcacgggtgc tgcgggacac 1020
acagacacgc ctacgattag actcaggcag gcacctaccg gcgagcggcc gcgggtgact 1080
cccaggcgcg gcggtacctc acggtggtga aggtcacagg tgaggtcacc ctgatagtcc 1140
cgctcgcgcc gagagccctc ccctcgacct gggaccgcag tgtttggggc ggggctctcc 1200
gtgagggggt tgggaagctc gaagccgcag gcctgactct ggcctttggc atcctggggt 1260
tggcctgggc aaatgtgtcg tgagagacgg atttgttgtt ctcgggaagg cgtaagttta 1320
atttagtcct ccaggacgga gaccgagggc cgagtatccc ggcaggggta ggagagccgt 1380
aatcctaccc ccacctcccc actgtaaacc tctttccaga gagggcattc ccgttccaaa 1440
caccagaccc agccggggaa atgcttcttc ttgtctggcc caagtgccct cctgggaggg 1500
gctcaaaatg cattcccccc aagctgggca cagctcatcc ctgctgggga gcttctgcag 1560
tggccgagga ctcagacaac cctaaccagg gctctggagg tcttctggaa gaaggaaccc 1620
caagtaggga caccccagga gcagagagga ggggaacagc gagaagagac ccagcttttg 1680
ggcccagtcc tgccatggcc agccatccgg cccccagggc cctgcttggg atggggctgc 1740
agaccacctc ccatgggacc tctgcaccaa ccatcccctg ggtaaaatcc ttgtttaggc 1800
ctggtattta aggcccctct gcccatccct actccttctc tagcactgcc cctcatcctc 1860
cccccatctc tcctccatcc agcgctacag gctgttttga gcttttgcag gtgctggtct 1920
ctgattgaaa tgtcctgatc tcttctccct tcttgtccca tcccaagtgt ctcctcctcc 1980
aggaaacctt ccctgacacc cactgagtta ggtggcccct ctgcccacca tcatccctgc 2040
ccaggccccc atgggtcctt caggcccagt actgaccacc tgtctttgcc acctgctgtg 2100
cagggttgca gcactcccag tagaccagga gctccgggag gcagggccgg ccccacgtcc 2160
tctgcgcacc accctgagtt ggatcctctg tgcgccacct gagttggatc cagggctagc 2220

-continued tgctgttgac ctccccactc ccacgctgcc ctcctgcctg cagccatgac gcccctgctc 2280
accctgatcc tggtggtcct catgggctta cctctgggta agatggacaa aggacagagg 2340
gatgggcaga cccactttga gggcagatgg gctgacagta gggaaggagg ctagaattcc 2400
cagcgacaac ccctccttct agccccctgc cccggggaag gtgacgggct gggggcctga 2460
tgggctggag gaggggcctc tcatgttctg tgaccccgt tcccttcccg cccatctgcc 2520
aaccccagcc caggccttgg actgccacgt gtgtgcctac aacggagaca actgcttcaa 2580
ccccatgcgc tggcggggta tggttgccta ctgcatgacc acgcgcacct gtgagtctgg 2640
gggccctgcg tggccctgcc tggggagcac gaaggggagg ttctgccctg cccctgagca 2700
tgcgggggtc ctgaggaagg aggctctcct gttcccggat cctgtctggg agctccaggc 2760
tgaggggccc tgccctgatg gctgtggatg ctggggtggg gccagctggg tctcctgccc 2820
ctcttagcgg agctggctca ccgccccgcc cctctgcaga ctacaccccc accaggatga 2880
aggtcagtaa gtcctgcgtg ccccgctgct tcgagactgt gtatgatggc tactccaagc 2940
acgcgtccac caccctcctg ctgccagtac gacctttgca acggcaccgg ccttgccacc 3000
ccggccaccc tggccctggc ccccatcctc ctggccaccc tctggggtct cctctaaagc 3060
ccccgaggca gacccactca agaacaaagc tctcgag 3097

<210> SEQ ID NO 252
<211> LENGTH: 391
<212> TYPE: DNA
<213> ORGANISM: Homo sapiens

<400> SEQUENCE: 252
gcggctctgc ctcagcaggc cccagggccc ccgaagtcac agaagctttt tcgggtccag 60
caaggggtgt gtgtcctctc agtcaaaccc cttgacgttt cccacccccct cacggggagg 120 gcaccaggcc tgaagctggc aggagctagg gccatgctat atttggtggg tcctggacgc 180
tgacccggcc agcgctattc tgggcaggga gggaaagggg cagagcaggt ggtcccccga 240
gtcctggtcc ccaaccacag caggacccag ccgagcaagg caaaagacgc aggactgggg 300
gatgcgcgca caggctgggg gttgggagca gcctggggcc ggcgcgggcc tgggcgtggg 360
aaggcggagc atgccaccct ctcgtggccg t 391

<210> SEQ ID NO 253
<211> LENGTH: 101
<212> TYPE: DNA
<213> ORGANISM: Homo sapiens

<400> SEQUENCE: 253
aggctggagt gcagtggtgc aatcttggct cacggcaacc tctgcctccg ggttcaagt 60 gattctcctg cctcagtctt ccgagtagct gggattacag g 101

<210> SEQ ID NO 254
<211> LENGTH: 101
<212> TYPE: DNA
<213> ORGANISM: Homo sapiens

<400> SEQUENCE: 254
aggctggagt gcagtggtgc aatcttggct cacggcaacc tctgcctccg ggttcaagt 60 gattctcctg cctcagtctt ccgagtagct gggattacag g 101

<210> SEQ ID NO 255
<211> LENGTH: 10427
<212> TYPE: DNA

<213> ORGANISM: Homo sapiens

<400> SEQUENCE: 255

```
atggacttgc cagtttcaaa agtttcctga agtctgaatt cagtgaggaa aaccttgagt     60
tctggattgc ctgtgaggat tacaagaaga tcaagtcccc tgccaagatg gctgagaagg    120
caaagcaaat ttatgaagaa ttcattcaaa cggaggctcc taaagaggtt ggtctctggg    180
taggtgggtc agttaagggc agctcattag ctctcaggaa ggatttacat ctgagacaca    240
gacctcccgt tgggagccaa aggctattcc tatttgtgag tcgaccacct tattaagcac    300
ctattgagta caaaggcaga gcaacatggt caagtatata tgaacaatcc tgttcagacc    360
gctttctagt tttatgggtc tcacctccac taacctccag tggagatcat accaatgtga    420
aatcttgcat gaattgttga gtctctgtga acctcatttc ttcctttgtg aaaataagaa    480
taatggagac tactttatgg agatgttgtg aggattaaat taaatagtgg gtgtaaaaac    540
ttatacaggt tgaacatctc tgatctgaaa attcaaaatt cagaatgcct caaagtctga    600
aactttttca gcaccatgat gccacaagtg gaaaattcca ctgacctctt gtgataggtc    660
tcagtcaaaa tacagccaaa actttttttca tgcccaaaat tattaaaaat attacataaa    720
attaccttca tgttatatgt ataggtatat atgacacata aatgaacttt gtgtttagac    780
ttgggtctca tattaagata tcttatctca ttatgtatat gtaaatattt caaaatctca    840
aaaaattcaa gatctgaaac atttctggtc ccaagcattc cagataagtg atgttcaacc    900
agtgtattat tcctttctct cactgctatg aagaaatacc aaagacttgg taatttataa    960
aggaaagagg tttaattgac tcacagttcc gcatggatgg ggagacctca ggaaacttac   1020
aatccagaca gaaggcacct cttcacaggg tggcaggaga gagaataaaa gtggagtgaa   1080
gggggaagcc ccttataaaa ccatcagatc tcgtgagaac tcactatcac aagaacagta   1140
taagggaaac tgcccccatg attcaattat tgccacctgg tcctgccctt gacatgtggg   1200
aattattatg atttaaggtg agatttgggt ggggacacag agccaaacta tatcaaccag   1260
tatctcagtg tccgaactga ttaatgccta atgagtattt ctataacttt tctttgtttt   1320
tctttccatt cccatttcta gtctttcctt taaacacctc tcttttttttg tcctttctac   1380
tcttctttat cctttatttc cccacttgga cttttccatt tacactgtac ttgggacaat   1440
ggtatattta ctcatgaaaa tcaaaatatt acaagaaaac agtgttagag atgttgaaag   1500
ccaatatacc actgattgac tattaaagcc cagatttttg ttgatttcaa agaaactttg   1560
gggaagttga tctgcttttt tctttgttat ttataaaacc acattgaaag cctattgtgg   1620
aattcaggat ggccacagca agccctgttc atcatggtat ggtcaggtta ctctaatttc   1680
acttgtttct tttaatccag tctggaaagt aaatgtttca tcaaggtttg gagtcaagca   1740
cggaggtgat ctgggcaagc cttgttgagt aggcagaaat ctacttaaga tgtttgagag   1800
agaaaaactc ccaaatatcc cttctctacc acagatgctc tagactcctg gagttccacc   1860
attagatatg tatttcttta gttatgagtt accctaaatg tgtttgagtg gatggacaaa   1920
ttatgtacct tgatactagt agatgtgctt cctccatgac acagggttgg aggttaggag   1980
tatgagaatg tacagtactg tgggtcaaag ccacgaaaat gaaaaggtgc tagaaagaat   2040
ctagatttaa gtttgatgtg gatattaatc ttgaaattct ctccagatca ccccttcttc   2100
tcctcaacct ccaccctaag cacatatgtt agctctaccc tacttctgtt accatttgtg   2160
ctgggccatc ctttcttctg tcagcatgtt atttctctgt atatattgac aagaagatta   2220
atttaacatt aaattggaca tgtatttccc catttcaaag gattctctga cttaccttcc   2280
```

-continued

```
tatcaacttg acttcctctt cacagaattc taagatttgc tgaaatacct acaaatagta   2340
gaaacccact cagataattg ttagttactc tgagctctgg gaaaacatta ttggttatta   2400
tgaaaatatg agacattaac ctaaaatata attttaaaat aaacaatacc atggctagct   2460
gagttatagg gacaaataaa ttgtggtcac tagttgaaag actaattaaa atagccttgc   2520
ccttcattct aaatgatcta tgcttatgca agagtacaat agtatacatt agacccaaat   2580
acaggcatcc caggattatg tagaataatg atcctgagct gggtattaga gagaatgtga   2640
atcctactcc tagcacataa aaagctttca agaaatattt ttgagatgaa agcatgaaaa   2700
tatccaactt cagacattct tagatgtggg actttgggca agtctctagc taaagctctc   2760
taatcctcag ttcttttaac tgtaaccatc ttgtgtatat gtatgtgcac ctgaagtatg   2820
ttaagtcata gcttttatta cttaaaaaat tctccaactt ttgtattttg atgtaaatat   2880
ttactattta attttgatga aattgaccta tataagacct agattaccca ggcaaatagt   2940
aatctgaatt ttgttgctct gaatactcac ctcaactctt taatacaaga aactgactga   3000
gagatacaat ggtaaaaatt ggaattaaat ttaaacaaga gaaatggcca tgtggaagtc   3060
aataagtaga taatttatac attgcaaatt atcatttgac catatttgaa attaatgaaa   3120
tgatattgtt tctggataac taaacagata aatatgtatc agaatgactt attaaagaag   3180
gcttaagcac ataaaaatac caagagaaat agctgctatt tgctggtgga tactatgtcc   3240
tagagggttt taaatacatc actcctttaa aaaataagat taggagctac ttttataatt   3300
tttagaaact caatcatttg gaataagcct gtctaccaag ctcagtacag atatatactt   3360
aatataagag aaggaagaag cattgctttc agtgtggcgg gaagaataat agactgagaa   3420
tggagaaatc tatgttatag tctcacctct aatccacact agctgtttgt gggcatgtaa   3480
cctgacctct ttgaggtctt cacatttaaa ggcagacatt ggacttcatc aactctgacg   3540
ctgatcccaa ttctgacaat ctgatcttcc aacaggcctg cataaagtac attgacccct   3600
ttcacctctg gaaaatctta atgtagctca acgcccttca tcctagactt tgaagcacag   3660
ctcagtcctg ctgtctgttc tgacctggct ccccagggaa tcatgcattt tgtctccaac   3720
tctaactaat agctgcttca taattctctg agcccaaaga gctctattca gtaccaaaaa   3780
cctctaacag cccaggagag acccaaaacc tttatcagtg tttcaattca caaccatagg   3840
ctgatttgga ttctatttct gtcttgttta cactcaaaat ccttaaaaac cattaaatcg   3900
tacaacatgg agtataaaga ttcctttaaa ctcatagtca gccaagttca aataggctgt   3960
accttgtaca actccagagg aaccattcac gtagacccta gtatggttgc aatgtagtgg   4020
ccctgcactc aggacatgta agccacagtg catcccagtg ctggagtcta ctggttaaaa   4080
ggctgggctc tggagccaca tcactggatt tctgaatctt ctctctacca ttaatgaact   4140
ttgagtaaat catgtaacat ttctgtgcat ctgtttcctc aactgtaaaa tgtagacagc   4200
agcatctatt atacctcata gagttataag attaaatgag ttcatccgtg caaagtgcct   4260
ggcaccgacc gagcactcaa taaatgttaa ttgctgttag ctgttttcat tattattctg   4320
tcagaatgac tgtttcctgg tttgtttttg gaaagaacaa gttttcttgt tcttctggag   4380
ccatgcaaaa ggtcctggat ccccagacag aatttacttc tctctgttca attcctccaa   4440
tagacgtgaa accaaatgtt gtgttagaat tttaaaatta ggcaccaggg ccggacgcgg   4500
tggctcacac ctgtaatccc agcactttgg gaggccgagg caggcagatc acctgaggtc   4560
aggagttcga gaccagcctc accaatgtgg caaaaccccg tctctatcaa aagtacaaaa   4620
attagcccgg cgtggtggca catgcctgta acccagctag ttgggaggct cgggcagaag   4680
```

```
aatcacttga acccggaagg cagaggttgc agtgaaccaa atggcgccac tgcactccag   4740
cctgcctgag tgacagaact agactctatc caacaaaaaa aaaaaaaaaa aaaaaagaaa   4800
aaaaagaaaa agaaaaaagc accaggacac ctggattcaa attctgattc tctagattca   4860
aatacactta tcagttctgt gatcttgggg aagccactta accttctgca tatacatatt   4920
tttttctata aaaggaaaga atcattctta ggattgttgt caaggattaa ataagtaatg   4980
tgtgtgttag cttctatggg aggtctgaca cctggtgggt gtctaatacc ggttggatgc   5040
atctgttgga acatcagctg ccttatccca tcgcctataa agtgagaagt gacatgtctc   5100
agtttttaat gactttcctc ccctcttatg ttttattgat gagaaattcc acctccctct   5160
tcacccctca tcaaattcta taacttaggc ttatgtagtg accctgtttc ctggcccaca   5220
ggtgaatatt gaccacttca ctaaggacat cacaatgaag aacctggtgg aaccttccct   5280
gagcagcttt gacatggccc agaaaagaat ccatgccctg atggaaaagg attctctgcc   5340
tcgctttgtg cgctctgagt tttatcagga gttaatcaag tagtaattta gccaggctat   5400
gaaatcatcc tgtgagttat ttcctccata ataaccctgc atttcccatt aatctacata   5460
tcttcccaca gcagctttgc tcagtgatac ccacatggga aaaatcccag gggatgttgc   5520
ttactctttt tgcccacact gctttggata cttatctact gtccgaaggc cttctttccc   5580
cactcaattc ttcctgccct gttattaatt aagatatctt cagcttgtag tcagacacaa   5640
tcagaatcac agaaaaatcc tgcctaaggc aaagaaatat aagacaagac tatgatatca   5700
atgaatgtgg gttaagtaat agatttccag ctaaattggt ctaaaaaaga atattaagtg   5760
tggacagacc tatttcaaag gagcttaatt gatctcactt gttttagttc tgatccaggg   5820
agatcacccc tctaattatt tctgaacttg gttaataaaa gtttataaga tttttatgaa   5880
gcagccactg tatgatattt taagcaaata tgttatttaa aatattgatc cttcccttgg   5940
accaccttca tgttagttgg gtattataaa taagagatac aaccatgaat atattatgtt   6000
tatacaaaat caatctgaac acaattcata aagatttctc ttttatacct tcctcactgg   6060
ccccctccac ctgcccatag tcaccaaatt ctgttttaaa tcaatgacct aagatcaaca   6120
atgaagtatt ttataaatgt atttatgctg ctagactgtg ggtcaaatgt ttccattttc   6180
aaattattta gaattcttat gagtttaaaa tttgtaaatt tctaaatcca atcatgtaaa   6240
atgaaactgt tgctccattg gagtagtctc ccacctaaat atcaagatgg ctatatgcta   6300
aaaagagaaa atatggtcaa gtctaaaatg gctaattgtc ctatgatgct attatcatag   6360
actaatgaca tttatcttca aaacaccaaa ttgtctttag aaaaattaat gtgattacag   6420
gtagaggcct tctaggtgag acacttttaa ggtacactgc attttgcaaa aaaaaaaaaa   6480
aaaagtaatc ttttagcaac cccagtattc cttcactatt tcgcttcctg cattagcaaa   6540
ttttacttac agtcaaaagt gcagatttat actcctgacg tgtctcattc acagctaaat   6600
aataggccat aggacttttg gtaggtttaa acttttaatt ctgtatttca tgattataag   6660
tcttgctaga attttttcta atctttagta gatttgatta aataatgatt cacagaattt   6720
agtaacagaa tcaaactaag ccatgtatga gggtaatcga gatgaggata ttaactcaaa   6780
agaaataggg tgatttttaa aggattaata aaattctgaa atgttaagta gaagattaca   6840
ttgtctagtc ttgtatttcc tccttctgtt gctctctttc attcacacac tctcagtttc   6900
tcatatttgt agctcattta tttggttatt tcctaagaat attgaaagtg aagcaactat   6960
gtgactgtat tcttcaggta aacactgact gcgcttgttg gattttccct atttttgtga   7020
cttcaagaat aatatgccct gctgaataca tgccatttca cattctgaaa ctgggtagag   7080
```

-continued

```
tggttgggtg ttctgccaac aattgctagt ggtgtgaatt cattcatatt tgccagtatt   7140
gctcacttca aagaaactcc ttcatcaagc agtccagagc taggccagat caatgctaca   7200
atcatgaagt tctcattgca tgcaattgtg taggattgac aaggaactca gataaaaatt   7260
tccagggtgc acttccagaa ccagcttcaa catatgtcta cattgccccc aagttaataa   7320
agtgccaacc ctttactctc tcatacagcc agaaatgtta gaaatccaaa atcttggtgc   7380
attatttttt cataaacgct aaaacatttg aagaaacaat ttaattattt aaaattcaag   7440
tattttattc acattatttg caatatccaa atgtttaaaa attcccagat aattaactag   7500
ctattacaga tctcacctag agggttgatg ttatgaagac tccagtggac tgtactcaca   7560
aattgactgg acaccctatg aaagtgggta gacctctcag cggaaaataa gaagggcttt   7620
tacctacagg gcaggacagg gtcccatgag agcagttctg tggagatata aaaagaatgg   7680
aagaaggaat gccttatagt gatattgtga cattatatct atatatctac atatatctat   7740
ctatctatat ctacatctat ataatcttac atttaaaatt gtattcctac acatattaga   7800
aactcttcta ataaatgaag taaaaaaatt aaaaagaata caaatattcc agccccaaat   7860
gagaaatcaa acatattaaa attgttcaag aaaatttctt tgaacacttt tgaaagtttt   7920
tggaaactta gaaaagaggg aaaaaaatcc agtgttacta gtaatttcca tggtaataca   7980
gataaaatac attcttttaa ttctgggaaa ttagaaaaag tggggtgatc tttccaggaa   8040
aaacatgtgt aacatctgct tatcactcca gctccctcct cctcctcctc tccacgttcc   8100
cttgagtaaa tgtctgggaa agcatgaagc ttgatgcaag aaccctgttg tactggcgtt   8160
ttcctcccct gtgaaaacgt aactactgtt gggagtgaat tgaggatgta gaaaggtggt   8220
ggaaccaaat tgtggtcaat ggaaatagga gaatatggtt ctcactcttg agaaaaaaac   8280
ctaagattag cccaggtagt tgcctgtaac ttcagttttt ctgcctgggt ttgatatagt   8340
ttagggttgg ggttagatta agatctaaat tacatcagga caaagagaca gactattaac   8400
tccacagtta attaaggacg tatgttccat gtttatttgt taaagcagtg tgaatagcct   8460
tcaagcatgt gaataatctt ccatcttccc cgccacacat acacacacac actttttgtt   8520
tctttcaggt agacaccttt taaaatgcag aactaactga ggcatttcag taactttgct   8580
ttcaaatcaa taaagtcaaa tgtatggaaa cattttgtgc cctactctcc ataccccgtg   8640
tactcaaatt ctctactgta tgaattatgc tttaagtaga attcagtgcc aaggagaact   8700
tggtgaaata aattatttta attttttttt tatcctttac aaagccatgg attttatttg   8760
gttgatgtgt gctctgtaca caagccattt caataggatg gagctgttaa ttattttcca   8820
aagagtaata gacatgcaaa agtttcaata aaaactgggc cattaacaaa taaattaata   8880
aactaataag cattcccttc taggtttttg ccaaactgcc tatccaataa caaatttgag   8940
aatcgttgaa aaagctagtt atatttcaga gaaatgattt tcattattga aactgttctc   9000
cctagcaggc cattttccct ttttcctggg agtttagcaa gtttaggaga gaatagtcat   9060
gaaaagaaag ggaagaaagg ggagaaggga agaggttaaa aagtaagtgc tcagacctat   9120
gaacgtaatc cctttgctag aaatatttaa gagcagctca gcttggttga aactgagttt   9180
tgtcatcttc catatttgca ggaaggtatt ttctgacttg caatgcagct agatgtaaaa   9240
ttttatttta tcatcctaga aagccttgac tagaaaaatg aataaatatt gagggtttcc   9300
tgtccatatc tggcttgcat gtgccagaaa gcagagaata gaaaatgtaa tctccaacat   9360
ccaagcatcg aaacccaagg ggtaggcaat tctatgtagg ttttggacat gaagtttggt   9420
gcatcttggt ttatgctggc tcaactgcta ttaaacctct ctggcttata gtctcttcat   9480
```

-continued tctattagac aagcacgtat cgaacacttg cttcgcacaa ggctctttag ttaacaattt 9540
agcagctact gtttgtgtta aacacacttt tcaccaaata ggttctgagg caaacgagag 9600
caatgactat ttaaagaaag gctttcccag catcacttac acatcccaaa actaaaaaga 9660
tcaactcttc caactgagaa aagactcctg gctttgaatg gaaacttaca gcagagagtc 9720
acaggccacg gcaacaacaa cgacaacaac aaacatttgg aatattattc tcaactcacg 9780
ttttaataat acatcttatt atttttctag tagagaaact acaaatcagc ctcttcaaca 9840
tttatataca gtttaataag cctcttgcaa gttacttgtt ctctcacctg aggtattttt 9900
ttcctcccca ccttgcccct gttcctccct tcctcttctc cctttgcaag aggaaatatt 9960
taacatattt gggtccaact tcaataatgt aataattaat acattaaaag catttaactt 10020
cctttctaga aaaatgcaca ggctaaggca tagacaaaac aaagagaaat gctgagaaat 10080
ttgccactgg agacaagcaa tctgaataaa tatttgccaa aagttctttt tatgtcatat 10140
agtgtcagga tttgaaggag ctattttttt ttaatgttgc aactagcaac tcatcttcgg 10200
aagacacagc caggagaatg aagtagaagt gaaaggttta taaatccatt tgtaagcatt 10260
tatcccatat attttaaatt caagaaaaat tgtgtttatc tttagaattt tgtattcaat 10320
actttatgta ctatgtgact catgcttctg gataaataaa gcaccaaata tgtatctgta 10380
accacaatca cacatattat attaaatata tatctatata acagcct 10427

<210> SEQ ID NO 256
<211> LENGTH: 19859
<212> TYPE: DNA
<213> ORGANISM: Homo sapiens

<400> SEQUENCE: 256
agacttgaac tgactcattt cactagaatt tgttactgaa catggttgtt tttgtttctg 60
ttaggcgttt agatgccaac catattacct cagtccccga ggacagtttt gaaggacttg 120
ttcagttacg gcatctgtgg ctggatgaca acagcttgac ggaggtgcct gtgcaccccc 180
tcagcaatct gcccacccta caggcgctga ccctggctct caacaagatc tcaagcatcc 240
ctgactttgc atttaccaac ctttcaagcc tggtagttct gtaagtatct atccctttta 300
attccatata tttgtgttaa ttggggtaca aaaacagatt tcttctgaca gattattatc 360
aaggcatctc gctgaatatg ctcctgagta gttagtgctt tgggagctgc ttttgtacaa 420
tattaaacag aataggataa tttaaaacat taccagctga tgataattgt tgaatctccc 480
taagacaaat gaccagttat aatcatgaga agaaattggg tcattcagca cacacttata 540
cagcttttac gtgtgtccca gcagcgtatt caatgttaaa agaagggaag tcatttcgag 600
gtgtccatag aagttagtcc cagggatatt tcgtgttttc cacttgttca gagagtatgt 660
gatgcagtgt gtttttaatc ttccaagaca taacaaaata gtgcttcttt taaaatctgt 720
tggagatctc actggtgtaa actacacact tcctccacac cattaccctc atgtcctcag 780
taagagagct catcaaattt ttcttcatat atttaagagc taatcaaaac tttattttga 840
tatgaataaa tattaatctt ccatgtatgt accatatttc cactaaagat actttctctt 900
tccatgaggt agtctatgtt tagtgagtct gtgcagtgta catagcaaga gataactatc 960
caatgtcact tgttttctgt ggtcaacaga aaactgttta gctgtttagc tgttgatatg 1020
tttagctaca tcattccttt acacaccaac tcagacatat aaaacaatga taatagttgc 1080
caatgggaga tggaaaagtc attttatgct ttttttcccc cttaggcatc ttcataacaa 1140
taaaattaga agcctgagtc aacactgttt tgatggacta gataacctgg agaccttgta 1200

```
agtatattca tattttgggc aactgcattg tgatattgaa agtataattt tatacttcac   1260
tgcagaaaaa gaaaaaaata ttggccttaa gttcagctcc ttattaattc actttgatac   1320
tggattaaat tcttgctatc aaataaccta attatgaata ctaatctaag tccatggcta   1380
aaaatggcaa agtgtgaatt gcatattttc cccaaagaa tacacattca aaacagctca    1440
atctacaaag atttatacct ttccagaaat gttggttttg ttaaatgtat gacagttttg   1500
gaagttagaa agttctaaaa tgaattctgg atagtgttat tttttccatg atctcagttg   1560
ccttctaatt gttaacactg ggtttgaata ctatatctgc ttttacaagt aacaaatgaa   1620
gattttatat tctgctatga tacttttgtt gttgtttcca cgagctaaag tgtttgagac   1680
ctctggctgt ttcaactgta cattgcacca ctatataagt aaaaggcatt gtgtagctgt   1740
gtataattga gaataggata tttatttttg ttcttttagc ctatattagt tgcctttatt   1800
gccttcattc aaagataatg taatttttgc tgttgtgatg agtaaatgat tcagagaagg   1860
tcccaattac atgggtgagt aaaacctgat tagaatgctc agggtatgta gtattttatt   1920
tgactgaatt ttctggttaa ctgtcaatta atgagaagac ttaaaatctt ttaggactct   1980
attatttcac ttttctatct aaattagagg ataggaaaca tcaatggata tatgaaagtt   2040
gaaaatcttg tagaggatag ttccaaactc agatctcctt tgctaagtgt gtgagttcta   2100
gtgttataaa taaaagattg aataggtttc ctaatcctaa gctgtgtaca ctatttcaat   2160
tatgttaaaa ttaaacctct tcccagttaa atttttattt gccattgttt cttctctgtt   2220
acaaaaagga aaaggaaacc aaaataggtc tcaaaggagc tgagctttta attttatttt   2280
actttcattc tgaaatcaat catgcaaatc gtatgccagt gtgctcttta tgttaaaaga   2340
aattaaactt taaacactct cagaactaag actttttagt acagatcact atggcttgtc   2400
tttctcctaa ctaatgtaaa attcccaata attcataact tgtatgagga caacagttgt   2460
gtgaatctac cctggtcctt ctgattattt tttattttt tatttttat ttttttgag       2520
acagagtctc gctttgtcac caggctggag tgcagtggca tgatctcggc tcactgcaac   2580
ctccgtctcc caggttcaag agattctcct gtctcagctt ccttagtagc tgggactaca   2640
ggcatgtgcc accatgccct gctaattttg gtatttttag tagagatggg ttttcactat   2700
gttggccagg atggtctcga tctcttgacc tcatgatctg cccgcctcag cctcccaaag   2760
tgctgggatt acaggcatga accactgtgc ctggcctcct tctgattatt tttatctcag   2820
gtcatcacgc tgatggtgga actgaggtca gctgctctta taccagaatt tcaggaagcc   2880
actgtgaact ccaaatggaa acctcagttt cacgctgtca tttacaaatg gatattcaat   2940
gaattatatt ctagaatgaa ttttcagaga aataccattc agatgattta tgtatttaat   3000
gcatcagtaa tacatgattc tgaaaattat ttgaacttgt aagtttcttg acctaaaaac   3060
atcatggaag aagaatgatt tctctctatt cattattgta agaaaaggtg taaattcagt   3120
taaactccta catggtttg aatgacgata tggttgataa agaaagatta ccatacagag    3180
gatatgattt aaaaaaatac ttgtctgtaa caaaatgcct tatgaattat gaccactatt   3240
taatattttg atatatttc acccatttt ttctagagac ttgaattata ataacttggg     3300
ggaatttcct caggctatta aagcccttcc tagccttaaa gagctgtgag tattgcttca   3360
ttctctttat gtcttcatat ccctgaaact caccatttaa tgttccaaca atgggatttt   3420
agaacatctt gttccattac gtatatccat aatacatgca cacaaacaca caaataatca   3480
taaagttgga ttgtgttcga tgacagagac aattttgagt atagattgat gtatagggtt   3540
agatgctggt aaaacaagaa ggcctgatat acagcgtctg cctttaagga gcttgtagtc   3600
```

-continued

```
ttagtcttac tggggaaact gatcatgtta agacagacag ctgtttctag gtagaaataa   3660
atgctgaatg aataggataa ataaatcatt ctggaagaat acctaattga agtttggagt   3720
tactgcagaa aacatcacca aaaggaagga gtttgaccag acttgaaaga acaaaaatat   3780
ttaaacacag gaatgaggga gcatttttgt ttttattttt tttttgatt gtttgtatgt   3840
tttgagacgg agtctcactc tgtcgcccag gctggagtgt cacggtgcag tggcatgatc   3900
acagctcact gcagccttga cctcccaggc tcaggtgatc ctcccatctt agcttcctgg   3960
gtagctggga ctgcaggcat gcaccaccac gcccagctaa ttgttaaatt ttttctagag   4020
atagggtttc atcatgttgc ccatgctggt ctcaaactcc tgggctcaag tgatcccctc   4080
agaatgctgg gattacaggc gtgagccact gtgccctgcc tgagggaaca ttctggacgt   4140
cgggtttgtc atgggtagag ttagtgactg tatatggcac aacagggact gtgtgtcatg   4200
agctagttga tggttaacat tctaagatgc attgccaaga ggctaaatac aggctacagt   4260
gagagagatt ttgaggttag aacacctgtt tctcatggtc taaagctttt ttttatgatg   4320
aagcaacaga taaatgcata tgagggatct gatagatacc aagctaagca gtgggttaaa   4380
aaagaattag gtatgatact gaaaaagata aaataaaatt aaaatttgag atttcctatg   4440
cttttgaaaa ttttcatgta gtcattatca gttgtatttt atataatgct gaacagcagt   4500
agatacttgg gttttatttc gcaagaggat aatgcatttc aaaatacttt tctcctatct   4560
ttctagagga tttcatagta attctatttc tgttatccct gatggagcat ttgatggtaa   4620
tccactctta agaactatgt aagtattttt gaaagtttct tttaatgtat aattatgtga   4680
agctgtgtcc gtacaatgcc aaacaccctg ataaagaatg agaagtcagg attttagata   4740
tatgtacatt gtgaacatag agttaatatt agagtgcttg tgaacatatg aaaattttac   4800
ttttttgga tattttcaca gacatttgta tgataatcct ctgtcttttg tggggaactc   4860
agcatttcac aatttatctg atcttcattc cctgtaagta tgtgaattta aaaacaaacc   4920
tggatattta tacagttgtt ttagtggaaa acaagaattt attactggaa ctccagaaaa   4980
caaaatcttt aaaatttttt tctcccttgg gcagaattta taattgttct tatttttgtg   5040
aatactttgc cacattatca tactttcaag tacattcaag agatgaaact agttttattt   5100
ttagttatag ttgcactgta attttaaact gtttaaaaca taaaatatga aaaaaaattt   5160
aaaaattacc ttgtctttct caatttcata aagagtcatt cgtggtgcaa gcatggtgca   5220
gcagttcccc aatcttacag gaactgtcca cctggaaagt ctgtaagtaa ggccctttga   5280
agaggggttg tataaagata acactactgg actgctagca gggtgccagg gtcttttagt   5340
gacaatgatg ggtttatgtt gattcctccg gtttcccttt gtatatatca tgcatggaga   5400
agaatatatt gggtatgggg tcagtgagct taggcagagt agagccgatt atgtggataa   5460
gatctgaaag gttcacagaa aatacaaggc agtaacaaag tgccaaatta gaagcagtgc   5520
tttcagaatt tagaagtggg ggcattcgat gtagactatc acagaaggct tcacggagga   5580
ggtagaaggt ttgaatactg tcaggtttcc cagagctgag tgtttaattt aaggcaggat   5640
tagtaaaact ggaaatacca aaagtattct cagagatagc atatagatga gcaaatatag   5700
ctagaattgc atgtttataa tagaatgggg atggtatgga gaaatcggag aattgtttgg   5760
tattagactt tgaaatgaca agctttgaac gttgcacatt tggttgtggc agtttcccag   5820
tgagtggtct gtgcatgagt ttacaggtgc acttaagatc ttgatgacct cagccctcca   5880
gacagtcagt tggggcctga ggcagctagg acctctagcc acaggagtct tactgcagcg   5940
tgccatttaa atgttacaat ggtcacatgt gacaagatat tttttaaaaa agaatttggg   6000
```

```
aagcactgag gtaaggagtt taaacttgac tcttaaggca gttggaggtg ttgagaatgt   6060
ttaagcaggt aatgtgagga gggtaaggag aaagagacta gagatgggga gaacagtgag   6120
gcggctgtgg gaatagtcta cctgaccaga tgaacacatt gaattatgac agctccaggt   6180
ctttaatcca tcactggatt tgcaccagga caaatagcat ggtctgtctg agagtcctct   6240
atccctctct gcctcacttc actctttttc tgaaagaatt agatgctaga aacacaacag   6300
aggaagaaat aacaggaact ggtgatagac tacagaaggg aggggaataa gagaacattt   6360
tcgaatgctg agccagtttg actgaaagaa aagacagaaa caagatttgg gggcagaatg   6420
caagttggtt tcaaaggtct tgggtgtaag aaggtgacaa cttgcaatta actgtgatca   6480
gactgtgtga ctgtagatta gtgttttcct cctggtccat gtgggaaatc aagcccagta   6540
tcaacatcta atgtcacaag tgtttttgag ttactgtgaa gatgatatca gaattggggt   6600
tcagttcacc ttcttgcatg tctaacttta tggaataatt aggccatggg atgtatagaa   6660
tctagtccat atgtaaatat gtgagcactt attctatatg ggaataaatt ttgcttacta   6720
tcttgagttg aattatttct tacatgaata atgtttttcc gcaggacttt gacaggtaca   6780
aagataagca gcatacctaa taatttgtgt caagaacaaa agatgcttag gactttgtaa   6840
gttggattct tcttcccttc ccctcatacc ttttgattat atattcacac atgttcaatt   6900
ttattttaag gatctacttt cataaggtgg ttttgaggta taattacttc ttagttgttg   6960
taaaggagca gatatttgag tcatctccag ggtgggtaat gtgcatttga attaggtttt   7020
agggttttga atatatcata tacttgtgac tttattttga acaaagtaaa accaagatag   7080
gttctttctt catttttct catcctgctc tttgtcttta ttctagtttc tccaggggta   7140
tctctcctca tagtctcctt ctttcatctg cagcctaagc agagcctaac tctttattca   7200
gtctggaatg aactaaagct tgtcgctttc taaaaacttt aggctgacct agaaactaaa   7260
agtaaataaa ggatgtaaaa atgtctccag aataaacgat taagttatta agttgttaat   7320
aagtactcag tggcaggaga tagtaacaaa ataaatgact gattgattaa gcaagtaaag   7380
tcacacatcc acttaacaat aggaatacat tctaagaaat gtgtcatggg gcaattttgt   7440
cattgtgtga aaatcataga gtatgcttac acaaacctcg gtggtttctt ctacacacct   7500
gggctatatg atataatctg ttactcctag cctacaaacc tgtacagcat aatactgtac   7560
tgaatactgt aggcagttgt aacataatag taaatatttg tatatctaaa catagaaaag   7620
ttggagcaga aatatggtat tatactctta tgggaccata tcattgtata tggtgtctgt   7680
cattgaccaa aactgttatt tgggtcatga ctataattta gtgatgtagt ggtgtatcaa   7740
acttaaacat aatgatcact gttgaggaaa aactgcagtg ggactgaaag ttaactagtt   7800
ctggtgtttg atgtaatata actgtttttt aaaatgttga taagcatacc atttctctta   7860
gagcttttca acaaaagaac atataagtta tttatgggat aaacaatatt gaaaaaatac   7920
aaatttttaa accgtataaa tacaaattta aaaaaatgta gctttaccac ttaaatttta   7980
tatattttgt atatttttct atatttgcct atttaatttt atatatttat gttatgtact   8040
ttatatatat actttataga aatgtatttt tacatatatt agtgtctatg ctcaacaata   8100
tattcttgaa ctttatcaat cttaggctta ttgtatcact gaggtatttg agaagctgac   8160
aagtcttagg aaaaaagact tgtttttctt attcaggcat atctctttat tacttatctt   8220
agctctgctt tcaacgcttc tgagtaccac tcttttaata taatactctg ataacatagc   8280
attaatttgt taatttccat tgttttaagg gacttgtctt acaataatat aagagacctt   8340
ccaagtttta atggttgcca tgctctggaa gaaatgtgag ttggtctttg acttattcct   8400
```

-continued

```
tttgttgtgg tgtattgtta gtttgttgag catttcgtat ttttaataga tggctttaat   8460
agtaagaaat tagaaattcc tgtaatcaga tgttcccata aataacatgt caaattgaac   8520
cagatgtgtt catgcaacca gcatgtatta ggcacttagc tatcaggcat cccatgaaac   8580
gctatgcggg ggggagttgg aagttagtgt atatttaaaa gaaatagaag acaaaaactt   8640
gtccagctat tgagggaaac cagacatgaa tgccagttcc catcatgtcc tgtgttgcac   8700
agctctggtg gaagctggtt gggagatggg aagggggagg cattaattct cccattttaa   8760
ctctatgtag tcctgtaact ttattcctac ggtatttgtc atagttgtgt tgtcttggtt   8820
ccttttctcc ctgcatcatc ttccttctct tatgcctgag tggggttgat gggggaattt   8880
agatagcata ccagttaatt cccagtataa tatgggatga aataccaatt agtctctttc   8940
attttataga tgagaaaagg gcaattctct ttcaacaaga tcactgttac ataagaatag   9000
ttatttaaat ttagaaaaaa ctcaactaag aaatgttata atgttatttt tcaaaataga   9060
aagtaacttt tttcttttc tctatccctt tctctttcct cctcctcctg ttctcttctt   9120
tgtctttgtc ttcgtcttct ttcttcttct ttttttattt agttctttac agcgtaatca   9180
aatctaccaa ataaaggaag gcacctttca aggcctgata tctctaagga ttctgtaagt   9240
ttgtctatga ttattaaaga caataaattt tttccaaact atgttaatat gttgttatga   9300
tttccatgtt actagatata cttaaagata taattttaat ttcagcctga acaacgtggt   9360
gaaaccccat ctctactaaa tacaaaaaat tagccgggca tagtggtgca tgcctgtaat   9420
cccagctact cgggaggctg aggcaggaga atcgcttgaa ccctggaggt ggagattgca   9480
gtgagctgag attgtgccat tgcactccag gctgaaaaag aagagtgaaa ctccgtctca   9540
aaaaaaaaaa aaaaagatat aatttgtgtt caataaatat tatttttaga ctttacctaa   9600
aatattattt tagacattgc aagattttta gacttgcaac tttataaata atctttcaat   9660
attttttact ttagctaatt gtacattggc aagtagaaaa atgtgtaatg tgtataactg   9720
aagtgatgta gcttgtttgt tttcaagtta taatagtgag gtttgccaat tcattagggc   9780
aagggtaggc agactacagc ccatgggcca catccagcct gcttcctggt ttatcaatta   9840
agtttaattg aacactgcca ggcctttatt attaaagtgc cgtctaaagc tgctctcacc   9900
ccactatagc agaattgagt agttgcagcg gagagtatat gactcacaaa ggtgaaaata   9960
tttactatct ggccttctac agaagaagtt tgctgacccc tgcactggag tatctatcat  10020
gacaaataga gttcataagc cacagaagca cttacttaaa aaatcatttg tatttgacta  10080
catatttgtt ccaggtactc tcataagcac ttgggaatat agaggtgact gagacaaacc  10140
ttgccactca ctatcttcct agaactttag cacagaaaca tagtacacta aattaatgaa  10200
catttttctt ttctttttct tttttttttt tttttgagac agggtctctc actcttgtcg  10260
ctcaggctag aatgcagtgg tgtaatcaca gctcactgca tcctccaacg cctgagctca  10320
aacaatcctc ctgcctcaac ctcctgaata gctgagggac tacaggtgca caccacaatc  10380
tccagctaat tttttctttt tttttttttt tggtagagat ggggtctccc tatgttgccc  10440
aggcttgtct caaacacctg agctcaagtg atccacccac cttggcctcc caaagtgttt  10500
ggattacagg tgtgagccac cttgcccagc acaacatttt tctattatag aaaaagtttg  10560
aaaaattgat agtgaatgaa attacatata ttgaatacag ttttttagta tatccccttt  10620
aagaaatatg acatgtactc tactagaaac tatttaattg gtagttgggt tgctggatca  10680
tctcaagttg tggactaact ttgtgtaagc ctgggcagtc atagggaaga agactggctc  10740
ctagttgcca tcacttttag aaactgataa gtgacactaa gaagctggtc ttttcgtgat  10800
```

```
ttggaaccaa gtgtgttgag tttccttgtt atctaggaaa tatgtctcag aatgaattta  10860
ctcaatgttt aaatttcctt taaggttcag tgtaagtgtg tttgtagatt atttctgttt  10920
tattaattct ataatatcag aatttctcag ggtgtgttcc tgaatacgga gctggctgta  10980
ctgttgatgc aatttttata tcgtgcttag gaaaagaagg gtatctgcag ccctcctgga  11040
atgctcttgt ttgcatattg attgtttgtc ttctctcggg gccttatcac taacctttga  11100
gaaggcaaac aatacgaagt ctgtttttat tttcagcttt ttcagaaact gagcttttcc  11160
tcactgagtt agcagtacca aaggttatat catatcattt atatgtttga attggtatca  11220
gaatgataaa gtgggaaaat tcacacctgt tttgaaacag atgccagcta gaattactgc  11280
tgtacagaac atattccaag aaatagattg ttgtgaagga gaggcattca acataaacat  11340
gaaaaaatat tgctggccaa gattgaagat ctttgttatc ttatcagcga tattgtgtta  11400
ctacctctaa ttctaaagta tagtctaagt aagtggcatt ctgagtgttt atttgaaaga  11460
ttaacatgtt actcttataa ttgcagagat ctgagtagaa acctgataca tgaaattcac  11520
agtagagctt ttgccacact tgggccaata actaacctgt aagtggatga ttatgcagta  11580
atgtcatgaa agtagtaact agtgctatag aaacatctgt tttaacattg tcgaatcaaa  11640
atatttttct gtttagttat tcccttgtat aaatgctaag ctgtatttat agtaaaagtc  11700
ttcttaaacg gcaagataca tgctagaact ataattttag caccccact tgaacttcat  11760
cttagggatc taatatttat gatgttaata cgtgtacaga tgtttttatg tgatttatat  11820
attgggcatt aacttgaagt ctcattcata ttttagagat gtaagtttca atgaattaac  11880
ttcctttcct acggaaggcc tgaatgggct aaatcaactg aaacttgtgg gcaacttcaa  11940
gctgaaagaa gccttagcag caaaagactt tgttaacctc aggtgtgttt ttgcttattt  12000
ttcttttttg ttgaagttat ggtaggctcc aaaattacag agtgtcctgg tttttgctc  12060
tggttctcag attttctgat aggctataat ttaagggtgt tttctacgtc agtctttgca  12120
aatttggtga aaaatagaat atgaacatta ttccacagtc tttaagaatg tgaactggag  12180
cccttgatgg cctcaaagag ataatacagc tattcaccag aatggttttt taatacagtg  12240
gacttttcat tagcaataag atggcagaaa ccatgtaaat gtgaacctgc agaaaacaat  12300
gctataatac ttcatgaagg ttttagagtt atgggggact gcattaaata taatagagag  12360
tattgttacg aggccgagcg tggtggctcg cacctgtaat cccagtactt tggggaaggc  12420
caaggtgggc tgatcacttg acaccagcag ttcaagacca gcctgggcaa catgctgaga  12480
ccctgtctct acaaaaaata taaaagttag ctggatgtgg tggcacgtgc ctgtagtccc  12540
agctacttgg gaggctgaaa tgggaggatc acttcagcct gggagttcta ggctgcactg  12600
agctgtgatt gcgccattac actatagcct gggtgacagg gcaagaccct gtctctaaaa  12660
aaaagagaga gaatattatt gttggagaag agaataaata ttttcattac atttatttaa  12720
accaagtaaa tatatttaat ggtataaagt cacaaatgac ctggggcatt aattttaagt  12780
gaaactatca gtttcgtatg ataaattgtg catagttaat acatttataa aaggagtcat  12840
aagatattac tttaaattac agtactgctg ttaaatttta aacagtttga tttacatcca  12900
actgttaaga gagatcttat agaaagggag aaagtctcgt tgtcatctga taccagagct  12960
gttttcacag atgaggaaac tgaggcccag agaggatgaa cgaccagcct aaagcacatg  13020
acagatcttt ctgactccta ggctgaggtt ttcaaagttt aaaatacttt tacaaaacaa  13080
aaccataact gcggagttgc tgttcagtgt agattttaca actttttttt ccaggtcttt  13140
atcagtacca tatgcttatc agtgctgtgc attttggggt tgtgactctt atgcaaattt  13200
```

-continued

```
aaacacagaa gataacagcc tccaggacca cagtgtggca caggagaaag gcaagtgcat  13260
gagtttcaaa aaatagaaca ctcctttaag gcattgatta aagttcctgt tattataatt  13320
actttgtgaa tgatcaatag gaaatctgtg agaaaaatgg cattgtctgg ccaggtgtga  13380
tggctcatgc ctgtaatctc agcacttagg gaggccaagg cgggagggtc atttgaggct  13440
aagagttcga gaccagcctg ggcaacaaag tgagactctc tctatataaa aaattttaaa  13500
actagctgag tgtagtggca tgtgcctgta ttccccacta cttgggagac tgaggtggga  13560
gaatcctttg agcggagccc aggagttcaa ggttgcagtg agctatgatt gtgccaatgc  13620
attccagact gggcaacaga gcaagacctt gtctctaaaa aaaaccaaaa ccaaaaaaaa  13680
caatggcatt cactatgcta ccagcatctt taatatgtta ttgaaccttc tataaggaga  13740
actcacactt atatacagag aaaattgcag gaaaatatgg ttcttttgag ttgcataagg  13800
ttttaattaa acatgctttg tgttatatgt tcaggtactg ctgatgcagc aaatgtcaca  13860
agcactcttg aaaatgaaga acatagtcaa ataattatcc attgtacacc ttcaacaggt  13920
atgcctggcc tattttttca cagttaccca tgttaaacaa acattaggca aatatatcta  13980
aatgtcctgg gtatagatgt gatttctgta atagggatgg tactagagga tcctgtgagg  14040
ccttctgatt ttgtgctttg cgtaccagcc agcagcttag gaatttttttg cagaatctca  14100
ggcccagacc tactgaatca gaatctgcat gttaacaagc tcccccaggt gaaggttgta  14160
cacgttagaa tttcagaggc actttcttaa tgctccttta actctgggac taattctgta  14220
agttagtagt ctatgcagat tgtatgtgtg tgcttaatgt agccttgcct ttccttattt  14280
cccctcattt acttcattga acttcgtagt cttgggaaag ttattaaact gataccacat  14340
atttggtcat gattgtcata gtctgcctaa tctactagag aagatgtatt tataatttta  14400
ctgtaaaagg aaggcttaaa tattttagtc aaattgtgtg ctacaaagta gattcctttg  14460
ttggtataat atcacaggat aatctggaca ttaattttat gactcagaat tataagtatt  14520
atggattcac tagtgattgc tgctgaattg tgagcttctt aaggggctgc gtatgtattt  14580
tatgaatact ttcttttgta gagaataagc tctaagttac tagataagtg aatgcagttg  14640
gcaagaatca tctaagtgta tgtaatttat tttattgtgt gttagtgtct atattaattt  14700
ttaaaggttg gggtgcagct tgcttacttg tctcactgga gttcatgtgc cagagaatgt  14760
acataaagaa ctgatgatcc aatgagaagg gaacaggttt attaaagggg gggctggact  14820
tcaacatgca gcgtttccat ttcttccacc ccaaatgtaa acttggagat tggccaggag  14880
gaaagctggt ctgagctcat ctccttgggc tgccatgggg atgaaatgca ggcctgcctc  14940
cccctactca gctgtagtaa cacacagaca ctgatgtgct tgctgcagaa gcaggaagtg  15000
gaggagagct gggatccttc tgttagcacc agaggaggca gcaggcttcc aaagacaggg  15060
acggtggagg ctgcttccca ggctttttttg gaaaagtaac ctttctcacc cataaaaggg  15120
ttctcaaaag gtatcctatt ctctcaggta gatgagctac ccctccttcc atgaaggatg  15180
agtttagata acagagataa aggtgataac gagctttctc ttagcacttc ctgaaggggg  15240
aatagaaagg aaatttaaaa taagagtttc ttgtattatt tggaagcctg ataaatgatg  15300
cagaactggc ttttgaggtc tgtgaatatc ttaacaattt aaaacatttt attggatatg  15360
tcattttcat gaaagttcat aaaacatgtt ttttagacag ttgtaataca tagttttctt  15420
gtgtttcata gtcaaaatct tgtttttctt ttctaatttt tcagtaaaac agttgtaatt  15480
tgtgtcataa ctagcatgtc aaagtcagtt actggaacat ggagttcagc gactgaatga  15540
gttcttgcaa tgctagtttg tattatgtag gattttattg tacatagctt tgtatgaata  15600
```

-continued

```
gttaacatca ccgaggtgta gtcctagcta tattatctta ctgaatggcc tttgtcagtt  15660
tctttgaaat atcagtttct ctggatgaaa aatggggata attatactgt cttaacctgc  15720
ttcatcaggt tgcttttgaa agtcataaga aaatatataa aaaatatgtg tagatacata  15780
catatacata catgattata aagtatattg gggctagaaa ggaagaagaa aagggagcta  15840
atatttattg aagtctaact atatatccag catcctgctt agttccttat gtgtataatt  15900
ttacttaagc tgcacaactg tatgaaacag gcattattat ccacaagtga gaaaatgaat  15960
acaggttaaa atttatacaa ttttaagttg ctttcttaag gtaagaatag caagttatga  16020
accatctcat tccagaccct cagtcatcaa atacctctta tgccctagat attgtgctat  16080
gtaaattagc ttagatgcaa gaaaaaatga aaaatttcat ctaaatatca ctctttatca  16140
aatatttaat aaaagaaata tttatagcct taccaaatat ttaataaaat aaattaaagt  16200
cagtttattt ttaaaatagc ctggtccatg accaaaatat cttagaacta gtaatcagtt  16260
cagttttgtt caagtagaga gcagatttaa ttagtctata tcattagttt ttctatcaag  16320
ccatatcatt ttctaaattg ttttctaagt tatcttttat ttctctctct ctgtgtgtgt  16380
tttttttagg tgcttttaag ccctgtgaat atttactggg aagctggatg attcgtctta  16440
ctgtgtggtt cattttcttg gttgcattat ttttcaacct gcttgttatt ttaacaacat  16500
ttgcatcttg tacatcactg ccttcgtcca aattgtttat aggcttgatt tctgtgtcta  16560
acttattcat gggaatctat actggcatcc taacttttct tgatgctgtg tcctggggca  16620
gattcgctga atttggcatt tggtgggaaa ctggcagtgg ctgcaaagta gctgggtttc  16680
ttgcagtttt ctcctcagaa agtgccatat ttttattaat gctagcaact gtcgaaagaa  16740
gcttatctgc aaaagatata atgaaaaatg ggaagagcaa tcatctcaaa cagttccggg  16800
ttgctgccct tttggctttc ctaggtgcta cagtagcagg ctgttttccc cttttccata  16860
gaggggaata ttctgcatca cccctttgtt tgccatttcc tacaggtgaa acgccatcat  16920
taggattcac tgtaacgtta gtgctattaa actcactagc atttttatta atggccgtta  16980
tctacactaa actatactgc aacttggaaa aagaggacct ctcagaaaac tcacaatcta  17040
gcatgattaa gcatgtcgct tggctaatct tcaccaattg catctttttc tgccctgtgg  17100
cgtttttttc atttgcacca ttgatcactg caatctctat cagccccgaa ataatgaagt  17160
ctgttactct gatatttttt ccattgcctg cttgcctgaa tccagtcctg tatgttttct  17220
tcaacccaaa gtttaaagaa gactggaagt tactgaagcg acgtgttacc aagaaaagtg  17280
gatcagtttc agtttccatc agtagccaag gtggttgtct ggaacaggat ttctactacg  17340
actgtggcat gtactcacat ttgcagggca acctgactgt ttgcgactgc tgcgaatcgt  17400
ttcttttaac aaagccagta tcatgcaaac acttgataaa atcacacagc tgtcctgcat  17460
tggcagtggc ttcttgccaa agacctgagg gctactggtc cgactgtggc acacagtcgg  17520
cccactctga ttatgcagat gaagaagatt cctttgtctc agacagttct gaccaggtgc  17580
aggcctgtgg acgagcctgc ttctaccaga gtagaggatt ccctttggtg cgctatgctt  17640
acaatctacc aagagttaaa gactgaacta ctgtgtgtgt aaccgtttcc cccgtcaacc  17700
aaaatcagtg tttatagagt gaaccctatt ctcatctttc atctgggaag cacttctgta  17760
atcactgcct ggtgtcactt agaagaagga gaggtggcag tttatttctc aaaccagtca  17820
ttttcaaaga acaggtgcct aaattataaa ttggtgaaaa atgcaatgtc caagcaatgt  17880
atgatctgtt tgaaacaaat atatgacttg aaaaggatct taggtgtagt agagcaatat  17940
aatgttagtt ttttctgatc cataagaagc aaatttatac ctatttgtgt attaagcaca  18000
```

-continued

```
agataaagaa cagctgttaa tattttttaa aaatctattt taaaatgtga ttttctataa  18060
ctgaagaaaa tatcttgcta attttaccta atgtttcatc cttaatctca ggacaactta  18120
ctgcagggcc aaaaaaggga ctgtcccagc tagaactgtg agagtataca taggcattac  18180
tttattatgt tttcacttgc catccttgac ataagagaac tataaatttt gtttaagcaa  18240
tttataaatc taaaacctga agatgttttt aaaacaatat taacagctgt taggttaaaa  18300
aaatagctgg acatttgttt tcagtcatta tacattgctt tggtccaatc agtaattttt  18360
tcttaagtgt tttgtgatta cactactaga aaaaaagtaa aaggctaatt gctgtgtggg  18420
tttagtcgat ttggctaaac tactaactaa tgtgggggtt taatagtatc tgagggattt  18480
ggtggcttca tgtaatgttc tcattaatga atacttccta atatcgttgg ctctactaat  18540
attttccaat ttgctgggat gtcacctagc aatagcttgg attatataga aagtaaactg  18600
tggtcaatac ttgcatttaa ttagacgaaa cggggagtaa ttatgacacg aagtacttat  18660
gtttatttct tagtgagctg gattatcttg aacctgtgct attaaatgga aatttccata  18720
catcttcccc atactatttt ttataaaaga gcctattcaa tagctcagag gttgaactct  18780
ggttaaacaa gataatatgt tattaataaa aatagaagaa gaaagaataa agcttagtcc  18840
tgtgtcttta aaaattaaaa attttacttg attcccatct atgggcttta gacctattac  18900
tgggtggagt cttaaagtta taattgttca atatgttttt tgaacagtgt gctaaatcaa  18960
tagcaaaccc actgccatat tagttattct gaatatacta aaaaaatcca gctagattgc  19020
agtttaataa ttaaactgta catactgtgc atataatgaa tttttatctt atgtaaatta  19080
tttttagaac acaagttggg aaatgtggct tctgttcatt tcgtttaatt aaagctacct  19140
cctaaactat agtggctgcc agtagcagac tgttaaattg tggtttatat actttttgca  19200
ttgtaaatag tctttgttgt acattgtcag tgtaataaaa acagaatctt tgtatatcaa  19260
aatcatgtag tttgtataaa atgtgggaag gatttattta cagtgtgttg taattttgta  19320
aggccaacta tttacaagtt ttaaaaattg ctatcatgta tatttacaca tctgataaat  19380
attaaatcat aacttggtaa gaaactccta attaaaaggt tttttccaaa attcaggtta  19440
ttgaaaactt ttcattttat tcatttaaaa actagaataa cagatatata aaagtgttaa  19500
tctttgtgct atatggtatg aaatacaata ttgtactcag tgttttgaat tattaaagtt  19560
tctagaaagc aatctatttt gccttaattt aaaactaggt atattaatga atttagtttt  19620
aaagtaagca aattaaatat ttgtaagtgg acagtattag aagaaatgtt ggaagtaacc  19680
attagaaaac actattttga tatttatttg taaacatata agaacatttt gctgaaactt  19740
agaaataagg ttttatccta agtctgaact atactcatgg aaaacagatt atgaaatttc  19800
agaaaaacca ttgattcaat ctttatctaa aaagcaaatg attaaaaaat ctgcatgat   19859
```

HWBAO62 POLYPEPTIDES

CROSS-REFERENCE TO RELATED APPLICATIONS

This application is a continuation-in-part of U.S. application Ser. No. 12/136,548, filed Jun. 10, 2008, which is a divisional of U.S. application Ser. No. 11/781,665, filed Jul. 23, 2007, which is a continuation of U.S. application Ser. No. 10/994,608, filed Nov. 23, 2004, which is a divisional of U.S. application Ser. No. 10/105,299, filed Mar. 26, 2002, which claims the benefit of U.S. Provisional Application No. 60/278,650, filed Mar. 27, 2001; U.S. application Ser. No. 10/105,299 is a continuation-in-part of U.S. application Ser. No. 09/950,082, filed Sep. 12, 2001; U.S. application Ser. No. 09/950,082 is a continuation-in-part of International Application No. PCT/US00/06043, filed Mar. 9, 2000, which claims the benefit of U.S. Provisional Application Nos. 60/167,061, filed Nov. 23, 1999, and 60/124,146, filed Mar. 12, 1999; U.S. application Ser. No. 09/950,082 is a continuation-in-part of International Application No. PCT/US00/06012, filed Mar. 9, 2000, which claims the benefit of U.S. Provisional Application Nos. 60/166,989, filed Nov. 23, 1999, and 60/124,093, filed Mar. 12, 1999; U.S. application Ser. No. 09/950,082 is a continuation-in-part of International Application No. PCT/US00/06058, filed Mar. 9, 2000, which claims the benefit of U.S. Provisional Application Nos. 60/168,654, filed Dec. 3, 1999, and 60/124,145, filed Mar. 12, 1999; U.S. application Ser. No. 09/950,082 is a continuation-in-part of International Application No. PCT/US00/06044, filed Mar. 9, 2000, which claims the benefit of U.S. Provisional Application Nos. 60/168,661, filed Dec. 3, 1999, and 60/124,099, filed Mar. 12, 1999; U.S. application Ser. No. 09/950,082 is a continuation-in-part of International Application No. PCT/US00/06059, filed Mar. 9, 2000, which claims the benefit of U.S. Provisional Application Nos. 60/168,622, filed Dec. 3, 1999, and 60/124,096, filed Mar. 12, 1999; U.S. application Ser. No. 09/950,082 is a continuation-in-part of International Application No. PCT/US00/06042, filed Mar. 9, 2000, which claims the benefit of U.S. Provisional Application Nos. 60/168,663, filed Dec. 3, 1999, and 60/124,143, filed Mar. 12, 1999; U.S. application Ser. No. 09/950,082 is a continuation-in-part of International Application No. PCT/US00/06014, filed Mar. 9, 2000, which claims the benefit of U.S. Provisional Application Nos. 60/168,665, filed Dec. 3, 1999, 60/138,598, filed Jun. 11, 1999, and 60/124,095, filed Mar. 12, 1999; U.S. application Ser. No. 09/950,082 is a continuation-in-part of International Application No. PCT/US00/06013, filed Mar. 9, 2000, which claims the benefit of U.S. Provisional Application Nos. 60/168,662, filed Dec. 3, 1999, 60/138,626, filed Jun. 11, 1999, and 60/125,360, filed Mar. 19, 1999; U.S. application Ser. No. 09/950,082 is a continuation-in-part of International Application No. PCT/US00/06049, filed Mar. 9, 2000, which claims the benefit of U.S. Provisional Application Nos. 60/168,667, filed Dec. 3, 1999, 60/138,574, filed Jun. 11, 1999, and 60/124,144, filed Mar. 12, 1999; U.S. application Ser. No. 09/950,082 is a continuation-in-part of International Application No. PCT/US00/06057, filed Mar. 9, 2000, which claims the benefit of U.S. Provisional Application Nos. 60/168,666, filed Dec. 3, 1999, 60/138,597, filed Jun. 11, 1999, and 60/124,142, filed Mar. 12, 1999; U.S. application Ser. No. 09/950,082 is a continuation-in-part of International Application No. PCT/US00/06824, filed Mar. 16, 2000, which claims the benefit of U.S. Provisional Application Nos. 60/168,664, filed Dec. 3, 1999, and 60/125,359, filed Mar. 19, 1999; U.S. application Ser. No. 09/950,082 is a continuation-in-part of International Application No. PCT/US00/06765, filed Mar. 16, 2000, which claims the benefit of U.S. Provisional Application Nos. 60/169,906, filed Dec. 10, 1999, and 60/126,051, filed Mar. 23, 1999; U.S. application Ser. No. 09/950,082 is a continuation-in-part of International Application No. PCT/US00/06792, filed Mar. 16, 2000, which claims the benefit of U.S. Provisional Application Nos. 60/169,980, filed Dec. 10, 1999, and 60/125,362, filed Mar. 19, 1999; U.S. application Ser. No. 09/950,082 is a continuation-in-part of International Application No. PCT/US00/06830, filed Mar. 16, 2000, which claims the benefit of U.S. Provisional Application Nos. 60/169,910, filed Dec. 10, 1999, and 60/125,361, filed Mar. 19, 1999; U.S. application Ser. No. 09/950,082 is a continuation-in-part of International Application No. PCT/US00/06782, filed Mar. 16, 2000, which claims the benefit of U.S. Provisional Application Nos. 60/169,936, filed Dec. 10, 1999, and 60/125,812, filed Mar. 23, 1999; U.S. application Ser. No. 09/950,082 is a continuation-in-part of International Application No. PCT/US00/06822, filed Mar. 16, 2000, which claims the benefit of U.S. Provisional Application Nos. 60/169,916, filed Dec. 10, 1999, and 60/126,054, filed Mar. 23, 1999; U.S. application Ser. No. 09/950,082 is a continuation-in-part of International Application No. PCT/US00/06791, filed Mar. 16, 2000, which claims the benefit of U.S. Provisional Application Nos. 60/169,946, filed Dec. 10, 1999, and 60/125,815, filed Mar. 23, 1999; U.S. application Ser. No. 09/950,082 is a continuation-in-part of International Application No. PCT/US00/06828, filed Mar. 16, 2000, which claims the benefit of U.S. Provisional Application Nos. 60/169,616, filed Dec. 8, 1999, and 60/125,358, filed Mar. 19, 1999; U.S. application Ser. No. 09/950,082 is a continuation-in-part of International Application No. PCT/US00/06823, filed Mar. 16, 2000, which claims the benefit of U.S. Provisional Application Nos. 60/169,623, filed Dec. 8, 1999, and 60/125,364, filed Mar. 19, 1999; U.S. application Ser. No. 09/950,082 is a continuation-in-part of International Application No. PCT/US00/06781, filed Mar. 16, 2000, which claims the benefit of U.S. Provisional Application Nos. 60/169,617, filed Dec. 8, 1999, and 60/125,363, filed Mar. 19, 1999; U.S. application Ser. No. 09/950,082 is a continuation-in-part of International Application No. PCT/US00/07505, filed Mar. 22, 2000, which claims the benefit of U.S. Provisional Application Nos. 60/172,410, filed Dec. 17, 1999, and 60/126,502, filed Mar. 26, 1999; U.S. application Ser. No. 09/950,082 is a continuation-in-part of International Application No. PCT/US00/07440, filed Mar. 22, 2000, which claims the benefit of U.S. Provisional Application Nos. 60/172,409, filed Dec. 17, 1999, and 60/126,503, filed Mar. 26, 1999; U.S. application Ser. No. 09/950,082 is a continuation-in-part of International Application No. PCT/US00/07506, filed Mar. 22, 2000, which claims the benefit of U.S. Provisional Application Nos. 60/172,412, filed Dec. 17, 1999, and 60/126,505, filed Mar. 26, 1999; U.S. application Ser. No. 09/950,082 is a continuation-in-part of International Application No. PCT/US00/07507, filed Mar. 22, 2000, which claims the benefit of U.S. Provisional Application Nos. 60/172,408, filed Dec. 17, 1999, and 60/126,594, filed Mar. 26, 1999; U.S. application Ser. No. 09/950,082 is a continuation-in-part of International Application No. PCT/US00/07535, filed Mar. 22, 2000, which claims the benefit of U.S. Provisional Application Nos. 60/172,413, filed Dec. 17, 1999, and 60/126,511, filed Mar. 26, 1999; U.S. application Ser. No. 09/950,082 is a continuation-in-part of International Application No. PCT/US00/07525, filed Mar. 22, 2000, which claims the benefit of U.S. Provisional Application Nos. 60/171,549, filed Dec. 22, 1999, and 60/126,595, filed Mar. 26, 1999; U.S. application Ser. No. 09/950,082 is a continuation-in-part of International Application No. PCT/US00/07534, filed Mar. 22, 2000, which claims the benefit of U.S. Provisional Application Nos. 60/171,504, filed Dec. 22, 1999, and 60/126,598, filed Mar. 26, 1999; U.S. application Ser. No. 09/950,082 is a continuation-in-part of International Application No. PCT/US00/07483, filed Mar. 22, 2000, which claims the benefit of U.S. Provisional Application Nos. 60/171,552, filed Dec. 22, 1999, and 60/126,596, filed Mar. 26, 1999; U.S. application Ser. No. 09/950,082 is a continuation-in-part of International Application No. PCT/US00/07526, filed Mar. 22, 2000, which claims the benefit of U.S. Provisional Application Nos. 60/171,550, filed Dec. 22, 1999, and 60/126,600, filed Mar. 26, 1999; U.S. application Ser. No. 09/950,082 is a continuation-in-part of International Application No. PCT/US00/07527, filed Mar. 22, 2000, which claims the benefit of U.S. Provisional Application Nos. 60/171,551, filed Dec. 22, 1999, and 60/126,501, filed Mar. 26, 1999; U.S. application Ser. No. 09/950,082 is a continuation-in-part of International Application No. PCT/US00/07661, filed Mar. 23, 2000, which claims the benefit of U.S. Provisional Application Nos. 60/174,847, filed Jan. 7, 2000, and 60/126,504, filed Mar. 26, 1999; U.S. application Ser. No. 09/950,082 is a continuation-in-part of International Application No. PCT/US00/07579, filed Mar. 23, 2000, which claims the benefit of U.S. Provisional Application Nos. 60/174,853, filed Jan. 7, 2000, and 60/126,509, filed Mar. 26, 1999; U.S. application Ser. No. 09/950,082 is a continuation-in-part of International Application No. PCT/US00/07723, filed Mar. 23, 2000, which claims the benefit of U.S. Provisional Application Nos. 60/174,852, filed Jan. 7, 2000, and 60/126,506, filed Mar. 26, 1999; U.S. application Ser. No. 09/950,082 is a continuation-in-part of International Application No. PCT/US00/07724, filed Mar. 23, 2000, which claims the benefit of U.S. Provisional Application Nos. 60/174,850, filed Jan. 7, 2000, and 60/126,510, filed Mar. 26, 1999; U.S. application Ser. No. 09/950,082 is a continuation-in-part of International Application No. PCT/US00/14929, filed Jun. 1, 2000, which claims the benefit of U.S. Provisional Application Nos. 60/174,851, filed Jan. 7, 2000, and 60/138,573, filed Jun. 11, 1999; U.S. application Ser. No. 09/950,082 is a continuation-in-part of International Application No. PCT/US00/07722, filed Mar. 23, 2000, which claims the benefit of U.S. Provisional Application Nos. 60/174,871, filed Jan. 7, 2000, and 60/126,508, filed Mar. 26, 1999; U.S. application Ser. No. 09/950,082 is a continuation-in-part of International Application No. PCT/US00/07578, filed Mar. 23, 2000, which claims the benefit of U.S. Provisional Application Nos. 60/174,872, filed Jan. 7, 2000, and 60/126,507, filed Mar. 26, 1999; U.S. application Ser. No. 09/950,082 is a continuation-in-part of International Application No. PCT/US00/07726, filed Mar. 23, 2000, which claims the benefit of U.S. Provisional Application Nos. 60/174,877, filed Jan. 7, 2000, and 60/126,597, filed Mar. 26, 1999; U.S. application Ser. No. 09/950,082 is a continuation-in-part of International Application No. PCT/US00/07677, filed Mar. 23, 2000, which claims the benefit of U.S. Provisional Application Nos. 60/176,064, filed Jan. 14, 2000, 60/154,373, filed Sep. 17, 1999, and 60/126,601, filed Mar. 26, 1999; U.S. application Ser. No. 09/950,082 is a continuation-in-part of International Application No. PCT/US00/07725, filed Mar. 23, 2000, which claims the benefit of U.S. Provisional Application Nos. 60/176,063, filed Jan. 14, 2000, and 60/126,602, filed Mar. 26, 1999; U.S. application Ser. No. 09/950,082 is a continuation-in-part of International Application No. PCT/US00/09070, filed Apr. 6, 2000, which claims the benefit of U.S. Provisional Application Nos. 60/176,052, filed Jan. 14, 2000, and 60/128,695, filed Apr. 9, 1999; U.S. application Ser. No. 09/950,082 is a continuation-in-part of International Application No. PCT/US00/08982, filed Apr. 6, 2000, which claims the benefit of U.S. Provisional Application Nos. 60/176,069, filed Jan. 14, 2000, and 60/128,696, filed Apr. 9, 1999; U.S. application Ser. No. 09/950,082 is a continuation-in-part of International Application No. PCT/US00/08983, filed Apr. 6, 2000, which claims the benefit of U.S. Provisional Application Nos. 60/176,068, filed Jan. 14, 2000, and 60/128,703, filed Apr. 9, 1999; U.S. application Ser. No. 09/950,082 is a continuation-in-part of International Application No. PCT/US00/09067, filed Apr. 6, 2000, which claims the benefit of U.S. Provisional Application Nos. 60/176,929, filed Jan. 20, 2000, and 60/128,697, filed Apr. 9, 1999; U.S. application Ser. No. 09/950,082 is a continuation-in-part of International Application No. PCT/US00/09066, filed Apr. 6, 2000, which claims the benefit of U.S. Provisional Application Nos. 60/176,926, filed Jan. 20, 2000, and 60/128,698, filed Apr. 9, 1999; U.S. application Ser. No. 09/950,082 is a continuation-in-part of International Application No. PCT/US00/09068, filed Apr. 6, 2000, which claims the benefit of U.S. Provisional Application Nos. 60/177,050, filed Jan. 20, 2000, and 60/128,699, filed Apr. 9, 1999; U.S. application Ser. No. 09/950,082 is a continuation-in-part of International Application No. PCT/US00/08981, filed Apr. 6, 2000, which claims the benefit of U.S. Provisional Application Nos. 60/177,166, filed Jan. 20, 2000, and 60/128,701, filed Apr. 9, 1999; U.S. application Ser. No. 09/950,082 is a continuation-in-part of International Application No. PCT/US00/08980, filed Apr. 6, 2000, which claims the benefit of U.S. Provisional Application Nos. 60/176,930, filed Jan. 20, 2000, and 60/128,700, filed Apr. 9, 1999; U.S. application Ser. No. 09/950,082 is a continuation-in-part of International Application No. PCT/US00/09071, filed Apr. 6, 2000, which claims the benefit of U.S. Provisional Application Nos. 60/176,931, filed Jan. 20, 2000, and 60/128,694, filed Apr. 9, 1999; U.S. application Ser. No. 09/950,082 is a continuation-in-part of International Application No. PCT/US00/09069, filed Apr. 6, 2000, which claims the benefit of U.S. Provisional Application Nos. 60/177,049, filed Jan. 20, 2000, and 60/128,702, filed Apr. 9, 1999; U.S. application Ser. No. 09/950,082 is a continuation-in-part of International Application No. PCT/US00/15136, filed Jun. 1, 2000, which claims the benefit of U.S. Provisional Application No. 60/138,629, filed Jun. 11, 1999; U.S. application Ser. No. 09/950,082 is a continuation-in-part of International Application No. PCT/US00/14926, filed Jun. 1, 2000, which claims the benefit of U.S. Provisional Application No. 60/138,628, filed Jun. 11, 1999; U.S. application Ser. No. 09/950,082 is a continuation-in-part of International Application No. PCT/US00/14963, filed Jun. 1, 2000, which claims the benefit of U.S. Provisional Application No. 60/138,631, filed Jun. 11, 1999; U.S. application Ser. No. 09/950,082 is a continuation-in-part of International Application No. PCT/US00/15135, filed Jun. 1, 2000, which claims the benefit of U.S. Provisional Application No. 60/138,632, filed Jun. 11, 1999; U.S. application Ser. No. 09/950,082 is a continuation-in-part of International Application No. PCT/US00/14934, filed Jun. 1, 2000, which claims the benefit of U.S. Provisional Application No. 60/138,599, filed Jun. 11, 1999; U.S. application Ser. No. 09/950,082 is a continuation-in-part of International Application No. PCT/US00/14933, filed Jun. 1, 2000, which claims the benefit of U.S. Provisional Application No. 60/138,572, filed Jun. 11, 1999; U.S. application Ser. No. 09/950,082 is a continuation-in-part of International Application No. PCT/US00/15137, filed Jun. 1, 2000, which claims the benefit of U.S. Provisional Application No. 60/138,625, filed Jun. 11, 1999; U.S. application Ser. No. 09/950,082 is a continuation-in-part of International Application No. PCT/US00/14928, filed Jun. 1, 2000, which claims the benefit of U.S. Provisional Application No. 60/138,633, filed Jun. 11, 1999; U.S. application Ser. No. 09/950,082 is a continuation-in-part of International Application No. PCT/US00/14973, filed Jun. 1, 2000, which claims the benefit of U.S. Provisional Application No. 60/138,630, filed Jun. 11, 1999; U.S. application Ser. No. 09/950,082 is a continuation-in-part of International Application No. PCT/US00/14964, filed Jun. 1, 2000, which claims the benefit of U.S. Provisional Application No. 60/138,627, filed Jun. 11, 1999; U.S. application Ser. No. 09/950,082 is a continuation-in-part of International Application No. PCT/US00/26376, filed Sep. 26, 2000, which claims the benefit of U.S. Provisional Application No. 60/155,808, filed Sep. 27, 1999; U.S. application Ser. No. 09/950,082 is a continuation-in-part of International Application No. PCT/US00/26371, filed Sep. 26, 2000, which claims the benefit of U.S. Provisional Application No. 60/155,804, filed Sep. 27, 1999; U.S. application Ser. No. 09/950,082 is a continuation-in-part of International Application No. PCT/US00/26324, filed Sep. 26, 2000, which claims the benefit of U.S. Provisional Application No. 60/155,807, filed Sep. 27, 1999; U.S. application Ser. No. 09/950,082 is a continuation-in-part of International Application No. PCT/US00/26323, filed Sep. 26, 2000, which claims the benefit of U.S. Provisional Application No. 60/155,805, filed Sep. 27, 1999; U.S. application Ser. No. 09/950,082 is a continuation-in-part of International Application No. PCT/US00/26337, filed Sep. 26, 2000, which claims the benefit of U.S. Provisional Application No. 60/155,806, filed Sep. 27, 1999; U.S. application Ser. No. 09/950,082 is a continuation-in-part of International Application No. PCT/US01/13318, filed Apr. 26, 2001, which claims the benefit of U.S. Provisional Application Nos. 60/212,142, filed Jun. 16, 2000, and 60/201,194, filed May 2, 2000; U.S. application Ser. No. 10/105,299 is a continuation-in-part of U.S. application Ser. No. 09/950,083, filed Sep. 12, 2001; U.S. application Ser. No. 09/950,083 is a continuation-in-part of International Application No. PCT/US00/06043, filed Mar. 9, 2000, which claims the benefit of U.S. Provisional Application Nos. 60/167,061, filed Nov. 23, 1999, and 60/124,146, filed Mar. 12, 1999; U.S. application Ser. No. 09/950,083 is a continuation-in-part of International Application No. PCT/US00/06012, filed Mar. 9, 2000, which claims the benefit of U.S. Provisional Application Nos. 60/166,989, filed Nov. 23, 1999, and 60/124,093, filed Mar. 12, 1999; U.S. application Ser. No. 09/950,083 is a continuation-in-part of International Application No. PCT/US00/06058, filed Mar. 9, 2000, which claims the benefit of U.S. Provisional Application Nos. 60/168,654, filed Dec. 3, 1999, and 60/124,145, filed Mar. 12, 1999; U.S. application Ser. No. 09/950,083 is a continuation-in-part of International Application No. PCT/US00/06044, filed Mar. 9, 2000, which claims the benefit of U.S. Provisional Application Nos. 60/168,661, filed Dec. 3, 1999, and 60/124,099, filed Mar. 12, 1999; U.S. application Ser. No. 09/950,083 is a continuation-in-part of International Application No. PCT/US00/06059, filed Mar. 9, 2000, which claims the benefit of U.S. Provisional Application Nos. 60/168,622, filed Dec. 3, 1999, and 60/124,096, filed Mar. 12, 1999; U.S. application Ser. No. 09/950,083 is a continuation-in-part of International Application No. PCT/US00/06042, filed Mar. 9, 2000, which claims the benefit of U.S. Provisional Application Nos. 60/168,663, filed Dec. 3, 1999, and 60/124,143, filed Mar. 12, 1999; U.S. application Ser. No. 09/950,083 is a continuation-in-part of International Application No. PCT/US00/06014, filed Mar. 9, 2000, which claims the benefit of U.S. Provisional Application Nos. 60/168,665, filed Dec. 3, 1999, 60/138,598, filed Jun. 11, 1999, and 60/124,095, filed Mar. 12, 1999; U.S. application Ser. No. 09/950,083 is a continuation-in-part of International Application No. PCT/US00/06013, filed Mar. 9, 2000, which claims the benefit of U.S. Provisional Application Nos. 60/168,662, filed Dec. 3, 1999, 60/138,626, filed Jun. 11, 1999, and 60/125,360, filed Mar. 19, 1999; U.S. application Ser. No. 09/950,083 is a continuation-in-part of International Application No. PCT/US00/06049, filed Mar. 9, 2000, which claims the benefit of U.S. Provisional Application Nos. 60/168,667, filed Dec. 3, 1999, 60/138,574, filed Jun. 11, 1999, and 60/124,144, filed Mar. 12, 1999; U.S. application Ser. No. 09/950,083 is a continuation-in-part of International Application No. PCT/US00/06057, filed Mar. 9, 2000, which claims the benefit of U.S. Provisional Application Nos. 60/168,666, filed Dec. 3, 1999, 60/138,597, filed Jun. 11, 1999, and 60/124,142, filed Mar. 12, 1999; U.S. application Ser. No. 09/950,083 is a continuation-in-part of International Application No. PCT/US00/06824, filed Mar. 16, 2000, which claims the benefit of U.S. Provisional Application Nos. 60/168,664, filed Dec. 3, 1999, and 60/125,359, filed Mar. 19, 1999; U.S. application Ser. No. 09/950,083 is a continuation-in-part of International Application No. PCT/US00/06765, filed Mar. 16, 2000, which claims the benefit of U.S. Provisional Application Nos. 60/169,906, filed Dec. 10, 1999, and 60/126,051, filed Mar. 23, 1999; U.S. application Ser. No. 09/950,083 is a continuation-in-part of International Application No. PCT/US00/06792, filed Mar. 16, 2000, which claims the benefit of U.S. Provisional Application Nos. 60/169,980, filed Dec. 10, 1999, and 60/125,362, filed Mar. 19, 1999; U.S. application Ser. No. 09/950,083 is a continuation-in-part of International Application No. PCT/US00/06830, filed Mar. 16, 2000, which claims the benefit of U.S. Provisional Application Nos. 60/169,910, filed Dec. 10, 1999, and 60/125,361, filed Mar. 19, 1999; U.S. application Ser. No. 09/950,083 is a continuation-in-part of International Application No. PCT/US00/06782, filed Mar. 16, 2000, which claims the benefit of U.S. Provisional Application Nos. 60/169,936, filed Dec. 10, 1999, and 60/125,812, filed Mar. 23, 1999; U.S. application Ser. No. 09/950,083 is a continuation-in-part of International Application No. PCT/US00/06822, filed Mar. 16, 2000, which claims the benefit of U.S. Provisional Application Nos. 60/169,916, filed Dec. 10, 1999, and 60/126,054, filed Mar. 23, 1999; U.S. application Ser. No. 09/950,083 is a continuation-in-part of International Application No. PCT/US00/06791, filed Mar. 16, 2000, which claims the benefit of U.S. Provisional Application Nos. 60/169,946, filed Dec. 10, 1999, and 60/125,815, filed Mar. 23, 1999; U.S. application Ser. No. 09/950,083 is a continuation-in-part of International Application No. PCT/US00/06828, filed Mar. 16, 2000, which claims the benefit of U.S. Provisional Application Nos. 60/169,616, filed Dec. 8, 1999, and 60/125,358, filed Mar. 19, 1999; U.S. application Ser. No. 09/950,083 is a continuation-in-part of International Application No. PCT/US00/06823, filed Mar. 16, 2000, which claims the benefit of U.S. Provisional Application Nos. 60/169,623, filed Dec. 8, 1999, and 60/125,364, filed Mar. 19, 1999; U.S. application Ser. No. 09/950,083 is a continuation-in-part of International Application No. PCT/US00/06781, filed Mar. 16, 2000, which claims the benefit of U.S. Provisional Application Nos. 60/169,617, filed Dec. 8, 1999, and 60/125,363, filed Mar. 19, 1999; U.S. application Ser. No. 09/950,083 is a continuation-in-part of International Application No. PCT/US00/07505, filed Mar. 22, 2000, which claims the benefit of U.S. Provisional Application Nos. 60/172,410, filed Dec. 17, 1999, and 60/126,502, filed Mar. 26, 1999; U.S. application Ser. No. 09/950,083 is a continuation-in-part of International Application No. PCT/US00/07440, filed Mar. 22, 2000, which claims the benefit of U.S. Provisional Application Nos. 60/172,409, filed Dec. 17, 1999, and 60/126,503, filed Mar. 26, 1999; U.S. application Ser. No. 09/950,083 is a continuation-in-part of International Application No. PCT/US00/07506, filed Mar. 22, 2000, which claims the benefit of U.S. Provisional Application Nos. 60/172,412, filed Dec. 17, 1999, and 60/126,505, filed Mar. 26, 1999; U.S. application Ser. No. 09/950,083 is a continuation-in-part of International Application No. PCT/US00/07507, filed Mar. 22, 2000, which claims the benefit of U.S. Provisional Application Nos. 60/172,408, filed Dec. 17, 1999, and 60/126,594, filed Mar. 26, 1999; U.S. application Ser. No. 09/950,083 is a continuation-in-part of International Application No. PCT/US00/07535, filed Mar. 22, 2000, which claims the benefit of U.S. Provisional Application Nos. 60/172,413, filed Dec. 17, 1999, and 60/126,511, filed Mar. 26, 1999; U.S. application Ser. No. 09/950,083 is a continuation-in-part of International Application No. PCT/US00/07525, filed Mar. 22, 2000, which claims the benefit of U.S. Provisional Application Nos. 60/171,549, filed Dec. 22, 1999, and 60/126,595, filed Mar. 26, 1999; U.S. application Ser. No. 09/950,083 is a continuation-in-part of International Application No. PCT/US00/07534, filed Mar. 22, 2000, which claims the benefit of U.S. Provisional Application Nos. 60/171,504, filed Dec. 22, 1999, and 60/126,598, filed Mar. 26, 1999; U.S. application Ser. No. 09/950,083 is a continuation-in-part of International Application No. PCT/US00/07483, filed Mar. 22, 2000, which claims the benefit of U.S. Provisional Application Nos. 60/171,552, filed Dec. 22, 1999, and 60/126,596, filed Mar. 26, 1999; U.S. application Ser. No. 09/950,083 is a continuation-in-part of International Application No. PCT/US00/07526, filed Mar. 22, 2000, which claims the benefit of U.S. Provisional Application Nos. 60/171,550, filed Dec. 22, 1999, and 60/126,600, filed Mar. 26, 1999; U.S. application Ser. No. 09/950,083 is a continuation-in-part of International Application No. PCT/US00/07527, filed Mar. 22, 2000, which claims the benefit of U.S. Provisional Application Nos. 60/171,551, filed Dec. 22, 1999, and 60/126,501, filed Mar. 26, 1999; U.S. application Ser. No. 09/950,083 is a continuation-in-part of International Application No. PCT/US00/07661, filed Mar. 23, 2000, which claims the benefit of U.S. Provisional Application Nos. 60/174,847, filed Jan. 7, 2000, and 60/126,504, filed Mar. 26, 1999; U.S. application Ser. No. 09/950,083 is a continuation-in-part of International Application No. PCT/US00/07579, filed Mar. 23, 2000, which claims the benefit of U.S. Provisional Application Nos. 60/174,853, filed Jan. 7, 2000, and 60/126,509, filed Mar. 26, 1999; U.S. application Ser. No. 09/950,083 is a continuation-in-part of International Application No. PCT/US00/07723, filed Mar. 23, 2000, which claims the benefit of U.S. Provisional Application Nos. 60/174,852, filed Jan. 7, 2000, and 60/126,506, filed Mar. 26, 1999; U.S. application Ser. No. 09/950,083 is a continuation-in-part of International Application No. PCT/US00/07724, filed Mar. 23, 2000, which claims the benefit of U.S. Provisional Application Nos. 60/174,850, filed Jan. 7, 2000, and 60/126,510, filed Mar. 26, 1999; U.S. application Ser. No. 09/950,083 is a continuation-in-part of International Application No. PCT/US00/14929, filed Jun. 1, 2000, which claims the benefit of U.S. Provisional Application Nos. 60/174,851, filed Jan. 7, 2000, and 60/138,573, filed Jun. 11, 1999; U.S. application Ser. No. 09/950,083 is a continuation-in-part of International Application No. PCT/US00/07722, filed Mar. 23, 2000, which claims the benefit of U.S. Provisional Application Nos. 60/174,871, filed Jan. 7, 2000, and 60/126,508, filed Mar. 26, 1999; U.S. application Ser. No. 09/950,083 is a continuation-in-part of International Application No. PCT/US00/07578, filed Mar. 23, 2000, which claims the benefit of U.S. Provisional Application Nos. 60/174,872, filed Jan. 7, 2000, and 60/126,507, filed Mar. 26, 1999; U.S. application Ser. No. 09/950,083 is a continuation-in-part of International Application No. PCT/US00/07726, filed Mar. 23, 2000, which claims the benefit of U.S. Provisional Application Nos. 60/174,877, filed Jan. 7, 2000, and 60/126,597, filed Mar. 26, 1999; U.S. application Ser. No. 09/950,083 is a continuation-in-part of International Application No. PCT/US00/07677, filed Mar. 23, 2000, which claims the benefit of U.S. Provisional Application Nos. 60/176,064, filed Jan. 14, 2000, 60/154,373, filed Sep. 17, 1999, and 60/126,601, filed Mar. 26, 1999; U.S. application Ser. No. 09/950,083 is a continuation-in-part of International Application No. PCT/US00/07725, filed Mar. 23, 2000, which claims the benefit of U.S. Provisional Application Nos. 60/176,063, filed Jan. 14, 2000, and 60/126,602, filed Mar. 26, 1999; U.S. application Ser. No. 09/950,083 is a continuation-in-part of International Application No. PCT/US00/09070, filed Apr. 6, 2000, which claims the benefit of U.S. Provisional Application Nos. 60/176,052, filed Jan. 14, 2000, and 60/128,695, filed Apr. 9, 1999; U.S. application Ser. No. 09/950,083 is a continuation-in-part of International Application No. PCT/US00/08982, filed Apr. 6, 2000, which claims the benefit of U.S. Provisional Application Nos. 60/176,069, filed Jan. 14, 2000, and 60/128,696, filed Apr. 9, 1999; U.S. application Ser. No. 09/950,083 is a continuation-in-part of International Application No. PCT/US00/08983, filed Apr. 6, 2000, which claims the benefit of U.S. Provisional Application Nos. 60/176,068, filed Jan. 14, 2000, and 60/128,703, filed Apr. 9, 1999; U.S. application Ser. No. 09/950,083 is a continuation-in-part of International Application No. PCT/US00/09067, filed Apr. 6, 2000, which claims the benefit of U.S. Provisional Application Nos. 60/176,929, filed Jan. 20, 2000, and 60/128,697, filed Apr. 9, 1999; U.S. application Ser. No. 09/950,083 is a continuation-in-part of International Application No. PCT/US00/09066, filed Apr. 6, 2000, which claims the benefit of U.S. Provisional Application Nos. 60/176,926, filed Jan. 20, 2000, and 60/128,698, filed Apr. 9, 1999; U.S. application Ser. No. 09/950,083 is a continuation-in-part of International Application No. PCT/US00/09068, filed Apr. 6, 2000, which claims the benefit of U.S. Provisional Application Nos. 60/177,050, filed Jan. 20, 2000, and 60/128,699, filed Apr. 9, 1999; U.S. application Ser. No. 09/950,083 is a continuation-in-part of International Application No. PCT/US00/08981, filed Apr. 6, 2000, which claims the benefit of U.S. Provisional Application Nos. 60/177,166, filed Jan. 20, 2000, and 60/128,701, filed Apr. 9, 1999; U.S. application Ser. No. 09/950,083 is a continuation-in-part of International Application No. PCT/US00/08980, filed Apr. 6, 2000, which claims the benefit of U.S. Provisional Application Nos. 60/176,930, filed Jan. 20, 2000, and 60/128,700, filed Apr. 9, 1999; U.S. application Ser. No. 09/950,083 is a continuation-in-part of International Application No. PCT/US00/09071, filed Apr. 6, 2000, which claims the benefit of U.S. Provisional Application Nos. 60/176,931, filed Jan. 20, 2000, and 60/128,694, filed Apr. 9, 1999; U.S. application Ser. No. 09/950,083 is a continuation-in-part of International Application No. PCT/US00/09069, filed Apr. 6, 2000, which claims the benefit of U.S. Provisional Application Nos. 60/177,049, filed Jan. 20, 2000, and 60/128,702, filed Apr. 9, 1999; U.S. application Ser. No.

09/950,083 is a continuation-in-part of International Application No. PCT/US00/15136, filed Jun. 1, 2000, which claims the benefit of U.S. Provisional Application No. 60/138,629, filed Jun. 11, 1999; U.S. application Ser. No. 09/950,083 is a continuation-in-part of International Application No. PCT/US00/14926, filed Jun. 1, 2000, which claims the benefit of U.S. Provisional Application No. 60/138,628, filed Jun. 11, 1999; U.S. application Ser. No. 09/950,083 is a continuation-in-part of International Application No. PCT/US00/14963, filed Jun. 1, 2000, which claims the benefit of U.S. Provisional Application No. 60/138,631, filed Jun. 11, 1999; U.S. application Ser. No. 09/950,083 is a continuation-in-part of International Application No. PCT/US00/15135, filed Jun. 1, 2000, which claims the benefit of U.S. Provisional Application No. 60/138,632, filed Jun. 11, 1999; U.S. application Ser. No. 09/950,083 is a continuation-in-part of International Application No. PCT/US00/14934, filed Jun. 1, 2000, which claims the benefit of U.S. Provisional Application No. 60/138,599, filed Jun. 11, 1999; U.S. application Ser. No. 09/950,083 is a continuation-in-part of International Application No. PCT/US00/14933, filed Jun. 1, 2000, which claims the benefit of U.S. Provisional Application No. 60/138,572, filed Jun. 11, 1999; U.S. application Ser. No. 09/950,083 is a continuation-in-part of International Application No. PCT/US00/15137, filed Jun. 1, 2000, which claims the benefit of U.S. Provisional Application No. 60/138,625, filed Jun. 11, 1999; U.S. application Ser. No. 09/950,083 is a continuation-in-part of International Application No. PCT/US00/14928, filed Jun. 1, 2000, which claims the benefit of U.S. Provisional Application No. 60/138,633, filed Jun. 11, 1999; U.S. application Ser. No. 09/950,083 is a continuation-in-part of International Application No. PCT/US00/14973, filed Jun. 1, 2000, which claims the benefit of U.S. Provisional Application No. 60/, 138,630, filed Jun. 11, 1999; U.S. application Ser. No. 09/950,083 is a continuation-in-part of International Application No. PCT/US00/14964, filed Jun. 1, 2000, which claims the benefit of U.S. Provisional Application No. 60/138,627, filed Jun. 11, 1999; U.S. application Ser. No. 09/950,083 is a continuation-in-part of International Application No. PCT/US00/26376, filed Sep. 26, 2000, which claims the benefit of U.S. Provisional Application No. 60/155,808, filed Sep. 27, 1999; U.S. application Ser. No. 09/950,083 is a continuation-in-part of International Application No. PCT/US00/26371, filed Sep. 26, 2000, which claims the benefit of U.S. Provisional Application No. 60/155,804, filed Sep. 27, 1999; U.S. application Ser. No. 09/950,083 is a continuation-in-part of International Application No. PCT/US00/26324, filed Sep. 26, 2000, which claims the benefit of U.S. Provisional Application No. 60/155,807, filed Sep. 27, 1999; U.S. application Ser. No. 09/950,083 is a continuation-in-part of International Application No. PCT/US00/26323, filed Sep. 26, 2000, which claims the benefit of U.S. Provisional Application No. 60/155,805, filed Sep. 27, 1999; U.S. application Ser. No. 09/950,083 is a continuation-in-part of International Application No. PCT/US00/26337, filed Sep. 26, 2000, which claims the benefit of U.S. Provisional Application No. 60/155,806, filed Sep. 27, 1999; U.S. application Ser. No. 09/950,083 is a continuation-in-part of International Application No. PCT/US01/13318, filed Apr. 26, 2001, which claims the benefit of U.S. Provisional Application Nos. 60/212,142, filed Jun. 16, 2000, and 60/201,194, filed May 2, 2000. This application is a continuation-in-part of U.S. application Ser. No. 11/366,486, filed Mar. 3, 2006, which is a continuation-in-part of 10/664,358, filed Sep. 20, 2003, which is a continuation-in-part of International Application No. PCT/US02/09785, filed Sep. 20, 2003; International Application No. PCT/US02/09785 is a continuation-in-part of U.S. application Ser. No. 10/100,683, filed Mar. 19, 2002, which claims the benefit of U.S. Provisional Application Nos. 60/277,340, filed Mar. 21, 2001, 60/306,171, filed Jul. 19, 2001, and 60/331,287, filed Nov. 13, 2001; U.S. application Ser. No. 10/100,683 is a continuation-in-part of U.S. application Ser. No. 09/981,876, filed Oct. 19, 2001, which is a divisional of U.S. application Ser. No. 09/621,011, filed Jul. 20, 2000, which is a continuation of U.S. application Ser. No. 09/148,545, filed Sep. 4, 1998, which is a continuation-in-part of International Application No. PCT/US98/04482, filed Mar. 6, 1998; U.S. application Ser. No. 10/100,683 is a continuation-in-part of U.S. application Ser. No. 09/621,011, filed Jul. 20, 2000, which is a continuation of U.S. application Ser. No. 09/148,545, filed Sep. 4, 1998, which is a continuation-in-part of International Application No. PCT/US98/04482, filed Mar. 6, 1998; U.S. application Ser. No. 10/100,683 is a continuation-in-part of U.S. application Ser. No. 09/148,545, filed Sep. 4, 1998, which is a continuation-in-part of International Application No. PCT/US98/04482, filed Mar. 6, 1998; U.S. application Ser. No. 10/100,683 is a continuation-in-part of International Application No. PCT/US98/04482, filed Mar. 6, 1998, which claims the benefit of U.S. Provisional Application Nos. 60/040,162, filed Mar. 7, 1997, 60/040,333, filed Mar. 7, 1997, 60/038,621, filed Mar. 7, 1997, 60/040,161, filed Mar. 7, 1997, 60/040,626, filed Mar. 7, 1997, 60/040,334, filed Mar. 7, 1997, 60/040,336, filed Mar. 7, 1997, 60/040,163, filed Mar. 7, 1997, 60/047,615, filed May 23, 1997, 60/047,600, filed May 23, 1997, 60/047,597, filed May 23, 1997, 60/047,502, filed May 23, 1997, 60/047,633, filed May 23, 1997, 60/047,583, filed May 23, 1997, 60/047,617, filed May 23, 1997, 60/047,618, filed May 23, 1997, 60/047,503, filed May 23, 1997, 60/047,592, filed May 23, 1997, 60/047,581, filed May 23, 1997, 60/047,584, filed May 23, 1997, 60/047,500, filed May 23, 1997, 60/047,587, filed May 23, 1997, 60/047,492, filed May 23, 1997, 60/047,598, filed May 23, 1997, 60/047,613, filed May 23, 1997, 60/047,582, filed May 23, 1997, 60/047,596, filed May 23, 1997, 60/047,612, filed May 23, 1997, 60/047,632, filed May 23, 1997, 60/047,601, filed May 23, 1997, 60/043,580, filed Apr. 11, 1997, 60/043,568, filed Apr. 11, 1997, 60/043,314, filed Apr. 11, 1997, 60/043,569, filed Apr. 11, 1997, 60/043,311, filed Apr. 11, 1997, 60/043,671, filed Apr. 11, 1997, 60/043,674, filed Apr. 11, 1997, 60/043,669, filed Apr. 11, 1997, 60/043,312, filed Apr. 11, 1997, 60/043,313, filed Apr. 11, 1997, 60/043,672, filed Apr. 11, 1997, 60/043,315, filed Apr. 11, 1997, 60/048,974, filed Jun. 6, 1997, 60/056,886, filed Aug. 22, 1997, 60/056,877, filed Aug. 22, 1997, 60/056,889, filed Aug. 22, 1997, 60/056,893, filed Aug. 22, 1997, 60/056,630, filed Aug. 22, 1997, 60/056,878, filed Aug. 22, 1997, 60/056,662, filed Aug. 22, 1997, 60/056,872, filed Aug. 22, 1997, 60/056,882, filed Aug. 22, 1997, 60/056,637, filed Aug. 22, 1997, 60/056,903, filed Aug. 22, 1997, 60/056,888, filed Aug. 22, 1997, 60/056,879, filed Aug. 22, 1997, 60/056,880, filed Aug. 22, 1997, 60/056,894, filed Aug. 22, 1997, 60/056,911, filed Aug. 22, 1997, 60/056,636, filed Aug. 22, 1997, 60/056,874, filed Aug. 22, 1997, 60/056,910, filed Aug. 22, 1997, 60/056,864, filed Aug. 22, 1997, 60/056,631, filed Aug. 22, 1997, 60/056,845, filed Aug. 22, 1997, 60/056,892, filed Aug. 22, 1997, 60/047,595, filed May 23, 1997, 60/057,761, filed Sep. 5, 1997, 60/047,599, filed May 23, 1997, 60/047,588, filed May 23, 1997, 60/047,585, filed May 23, 1997, 60/047,586, filed May 23, 1997, 60/047,590, filed May 23, 1997, 60/047,594, filed May 23, 1997, 60/047,589, filed May 23, 1997, 60/047,593, filed May 23, 1997, 60/047,614, filed May 23, 1997, 60/043,578, filed Apr. 11, 1997, 60/043,576, filed Apr. 11, 1997, 60/047,501, filed May 23, 1997, 60/043,670, filed Apr. 11, 1997, 60/056,632, filed Aug. 22, 1997, 60/056,664, filed Aug. 22, 1997, 60/056,876, filed Aug. 22, 1997, 60/056,881, filed Aug. 22, 1997, 60/056,909, filed Aug. 22, 1997, 60/056,875, filed Aug. 22, 1997, 60/056,862, filed Aug. 22, 1997, 60/056,887, filed Aug. 22, 1997, 60/056,908, filed Aug. 22, 1997, 60/048,964, filed Jun. 6, 1997, 60/057,650, filed Sep. 5, 1997, and 60/056,884, filed Aug. 22, 1997; U.S. application Ser. No. 10/100,683 is a continuation-in-part of U.S. application Ser. No. 09/882,171, filed Jun. 18, 2001, which claims the benefit of U.S. Provisional Application No. 60/190,068, filed Mar. 17, 2000; U.S. application Ser. No. 09/882,171 is a continuation of U.S. application Ser. No. 09/809,391, filed Mar. 16, 2001, which is a continuation-in-part of U.S. application Ser. No. 09/149,476, filed Sep. 8, 1998, which is a continuation-in-part of International Application No. PCT/US98/04493, filed Mar. 6, 1998; U.S. application Ser. No. 10/100,683 is a continuation-in-part of U.S. application Ser. No. 09/809,391, filed Mar. 16, 2001, which claims the benefit of U.S. Provisional Application No. 60/190,068, filed Mar. 17, 2000; U.S. application Ser. No. 09/809,391 is a continuation-in-part of U.S. application Ser. No. 09/149,476, filed Sep. 8, 1998, which is a continuation-in-part of International Application No. PCT/US98/04493, filed Mar. 6, 1998; U.S. application Ser. No. 10/100,683 is a continuation-in-part of U.S. application Ser. No. 09/149,476, filed Sep. 8, 1998, which is a continuation-in-part of International Application No. PCT/US98/04493, filed Mar. 6, 1998; U.S. application Ser. No. 10/100,683 is a continuation-in-part of International Application No. PCT/US98/04493, filed Mar. 6, 1998, which claims the benefit of U.S. Provisional Application Nos. 60/040,161, filed Mar. 7, 1997, 60/040,162, filed Mar. 7, 1997, 60/040,333, filed Mar. 7, 1997, 60/038,621, filed Mar. 7, 1997, 60/040,626, filed Mar. 7, 1997, 60/040,334, filed Mar. 7, 1997, 60/040,336, filed Mar. 7, 1997, 60/040,163, filed Mar. 7, 1997, 60/047,600, filed May 23, 1997, 60/047,615, filed May 23, 1997, 60/047,597, filed May 23, 1997, 60/047,502, filed May 23, 1997, 60/047,633, filed May 23, 1997, 60/047,583, filed May 23, 1997, 60/047,617, filed May 23, 1997, 60/047,618, filed May 23, 1997, 60/047,503, filed May 23, 1997, 60/047,592, filed May 23, 1997, 60/047,581, filed May 23, 1997, 60/047,584, filed May 23, 1997, 60/047,500, filed May 23, 1997, 60/047,587, filed May 23, 1997, 60/047,492, filed May 23, 1997, 60/047,598, filed May 23, 1997, 60/047,613, filed May 23, 1997, 60/047,582, filed May 23, 1997, 60/047,596, filed May 23, 1997, 60/047,612, filed May 23, 1997, 60/047,632, filed May 23, 1997, 60/047,601, filed May 23, 1997, 60/043,580, filed Apr. 11, 1997, 60/043,568, filed Apr. 11, 1997, 60/043,314, filed Apr. 11, 1997, 60/043,569, filed Apr. 11, 1997, 60/043,311, filed Apr. 11, 1997, 60/043,671, filed Apr. 11, 1997, 60/043,674, filed Apr. 11, 1997, 60/043,669, filed Apr. 11, 1997, 60/043,312, filed Apr. 11, 1997, 60/043,313, filed Apr. 11, 1997, 60/043,672, filed Apr. 11, 1997, 60/043,315, filed Apr. 11, 1997, 60/048,974, filed Jun. 6, 1997, 60/056,886, filed Aug. 22, 1997, 60/056,877, filed Aug. 22, 1997, 60/056,889, filed Aug. 22, 1997, 60/056,893, filed Aug. 22, 1997, 60/056,630, filed Aug. 22, 1997, 60/056,878, filed Aug. 22, 1997, 60/056,662, filed Aug. 22, 1997, 60/056,872, filed Aug. 22, 1997, 60/056,882, filed Aug. 22, 1997, 60/056,637, filed Aug. 22, 1997, 60/056,903, filed Aug. 22, 1997, 60/056,888, filed Aug. 22, 1997, 60/056,879, filed Aug. 22, 1997, 60/056,880, filed Aug. 22, 1997, 60/056,894, filed Aug. 22, 1997, 60/056,911, filed Aug. 22, 1997, 60/056,636, filed Aug. 22, 1997, 60/056,874, filed Aug. 22, 1997, 60/056,910, filed Aug. 22, 1997, 60/056,864, filed Aug. 22, 1997, 60/056,631, filed Aug. 22, 1997, 60/056,845, filed Aug. 22, 1997, 60/056,892, filed Aug. 22, 1997, 60/057,761, filed Sep. 5, 1997, 60/047,595, filed May 23, 1997, 60/047,599, filed May 23, 1997, 60/047,588, filed May 23, 1997, 60/047,585, filed May 23, 1997, 60/047,586, filed May 23, 1997, 60/047,590, filed May 23, 1997, 60/047,594, filed May 23, 1997, 60/047,589, filed May 23, 1997, 60/047,593, filed May 23, 1997, 60/047,614, filed May 23, 1997, 60/043,578, filed Apr. 11, 1997, 60/043,576, filed Apr. 11, 1997, 60/047,501, filed May 23, 1997, 60/043,670, filed Apr. 11, 1997, 60/056,632, filed Aug. 22, 1997, 60/056,664, filed Aug. 22, 1997, 60/056,876, filed Aug. 22, 1997, 60/056,881, filed Aug. 22, 1997, 60/056,909, filed Aug. 22, 1997, 60/056,875, filed Aug. 22, 1997, 60/056,862, filed Aug. 22, 1997, 60/056,887, filed Aug. 22, 1997, 60/056,908, filed Aug. 22, 1997, 60/048,964, filed Jun. 6, 1997, 60/057,650, filed Sep. 5, 1997, 60/056,884, filed Aug. 22, 1997, 60/057,669, filed Sep. 5, 1997, 60/049,610, filed Jun. 13, 1997, 60/061,060, filed Oct. 2, 1997, 60/051,926, filed Jul. 8, 1997, 60/052,874, filed Jul. 16, 1997, 60/058,785, filed Sep. 12, 1997, and 60/055,724, filed Aug. 18, 1997; U.S. application Ser. No. 10/100,683 is a continuation-in-part of U.S. application Ser. No. 10/058,993, filed Jan. 30, 2002, which claims the benefit of U.S. Provisional Application No. 60/265,583, filed Feb. 2, 2001; U.S. application Ser. No. 10/058,993 is a continuation-in-part of U.S. application Ser. No. 09/852,659, filed May 11, 2001, which is a continuation-in-part of U.S. application Ser. No. 09/152,060, filed Sep. 11, 1998, which is a continuation-in-part of International Application No. PCT/US98/04858, filed Mar. 12, 1998; U.S. application Ser. No. 10/058,993 is a continuation-in-part of U.S. application Ser. No. 09/853,161, filed May 11, 2001, which is a continuation-in-part of U.S. application Ser. No. 09/152,060, filed Sep. 11, 1998, which is a continuation-in-part of International Application No. PCT/US98/04858, filed Mar. 12, 1998; U.S. application Ser. No. 10/058,993 is a continuation-in-part of U.S. application Ser. No. 09/852,797, filed May 11, 2001, which is a continuation-in-part of U.S. application Ser. No. 09/152,060, filed Sep. 11, 1998, which is a continuation-in-part of International Application No. PCT/US98/04858, filed Mar. 12, 1998; U.S. application Ser. No. 10/100,683 is a continuation-in-part of U.S. application Ser. No. 09/852,659, filed May 11, 2001, which claims the benefit of U.S. Provisional Application No. 60/265,583, filed Feb. 2, 2001; U.S. application Ser. No. 09/852,659 is a continuation-in-part of U.S. application Ser. No. 09/152,060, filed Sep. 11, 1998, which is a continuation-in-part of International Application No. PCT/US98/04858, filed Mar. 12, 1998; U.S. application Ser. No. 10/100,683 is a continuation-in-part of U.S. application Ser. No. 09/853,161, filed May 11, 2001, which claims the benefit of U.S. Provisional Application No. 60/265,583, filed Feb. 2, 2001; U.S. application Ser. No. 09/853,161 is a continuation-in-part of U.S. application Ser. No. 09/152,060, filed Sep. 11, 1998, which is a continuation-in-part of International Application No. PCT/US98/04858, filed Mar. 12, 1998; U.S. application Ser. No. 10/100,683 is a continuation-in-part of U.S. application Ser. No. 09/852,797, filed May 11, 2001, which claims the benefit of U.S. Provisional Application No. 60/265,583, filed Feb. 2, 2001; U.S. application Ser. No. 09/852,797 is a continuation-in-part of U.S. application Ser. No. 09/152,060, filed Sep. 11, 1998, which is a continuation-in-part of International Application No. PCT/US98/04858, filed Mar. 12, 1998; U.S. application Ser. No. 10/100,683 is a continuation-in-part of U.S. application Ser. No. 09/152,060, filed Sep. 11, 1998, which is a continuation-in-part of International Application No. PCT/US98/04858, filed Mar. 12, 1998; U.S. application Ser. No. 10/100,683 is a continuation-in-part of International Application No. PCT/US98/04858, filed Mar. 12, 1998, which claims the benefit of U.S. Provisional Application Nos. 60/040,762, filed Mar. 14, 1997, 60/040,710, filed Mar. 14, 1997, 60/050,934, filed May 30, 1997, 60/048,100, filed May 30, 1997, 60/048,357, filed May 30, 1997, 60/048,189, filed May 30, 1997, 60/057,765, filed Sep. 5, 1997, 60/048,970, filed Jun. 6, 1997, and 60/068,368, filed Dec. 19, 1997; U.S. application Ser. No. 10/100,683 is a continuation-in-part of U.S. application Ser. No. 10/059,395, filed Jan. 31, 2002, which is a divisional of U.S. application Ser. No. 09/966,262, filed Oct. 1, 2001, which is a continuation of U.S. application Ser. No. 09/154,707, filed Sep. 17, 1998, which is a continuation-in-part of International Application No. PCT/US98/05311, filed Mar. 19, 1998; U.S. application Ser. No. 10/100,683 is a continuation-in-part of U.S. application Ser. No. 09/984,245, filed Oct. 29, 2001, which is a divisional of U.S. application Ser. No. 09/154,707, filed Sep. 17, 1998, which is a continuation-in-part of International Application No. PCT/US98/05311, filed Mar. 19, 1998; U.S. application Ser. No. 10/100,683 is a continuation-in-part of U.S. application Ser. No. 09/983,966, filed Oct. 26, 2001, which is a divisional of U.S. application Ser. No. 09/154,707, filed Sep. 17, 1998, which is a continuation-in-part of International Application No. PCT/US98/05311, filed Mar. 19, 1998; U.S. application Ser. No. 10/100,683 is a continuation-in-part of U.S. application Ser. No. 09/966,262, filed Oct. 1, 2001, which is a continuation of U.S. application Ser. No. 09/154,707, filed Sep. 17, 1998, which is a continuation-in-part of International Application No. PCT/US98/05311, filed Mar. 19, 1998; U.S. application Ser. No. 10/100,683 is a continuation-in-part of U.S. application Ser. No. 09/154,707, filed Sep. 17, 1998, which is a continuation-in-part of International Application No. PCT/US98/05311, filed Mar. 19, 1998; U.S. application Ser. No. 10/100,683 is a continuation-in-part of International Application No. PCT/US98/05311, filed Mar. 19, 1998, which claims the benefit of U.S. Provisional Application Nos. 60/041,277, filed Mar. 21, 1997, 60/042,344, filed Mar. 21, 1997, 60/041,276, filed Mar. 21, 1997, 60/041,281, filed Mar. 21, 1997, 60/048,094, filed May 30, 1997, 60/048,350, filed May 30, 1997, 60/048,188, filed May 30, 1997, 60/048,135, filed May 30, 1997, 60/050,937, filed May 30, 1997, 60/048,187, filed May 30, 1997, 60/048,099, filed May 30, 1997, 60/048,352, filed May 30, 1997, 60/048,186, filed May 30, 1997, 60/048,069, filed May 30, 1997, 60/048,095, filed May 30, 1997, 60/048,131, filed May 30, 1997, 60/048,096, filed May 30, 1997, 60/048,355, filed May 30, 1997, 60/048,160, filed May 30, 1997, 60/048,351, filed May 30, 1997, 60/048,154, filed May 30, 1997, 60/054,804, filed Aug. 5, 1997, 60/056,370, filed Aug. 19, 1997, and 60/060,862, filed Oct. 2, 1997; U.S. application Ser. No. 10/100,683 is a continuation-in-part of U.S. application Ser. No. 09/814,122, filed Mar. 22, 2001, which is a continuation of U.S. application Ser. No. 09/577,145, filed May 24, 2000, which is a continuation of U.S. application Ser. No. 09/166,780, filed Oct. 6, 1998, which is a continuation-in-part of International Application No. PCT/US98/06801, filed Apr. 7, 1998; U.S. application Ser. No. 10/100,683 is a continuation-in-part of International Application No. PCT/US98/06801, filed Apr. 7, 1998, which claims the benefit of U.S. Provisional Application Nos. 60/042,726, filed Apr. 8, 1997, 60/042,727, filed Apr. 8, 1997, 60/042,728, filed Apr. 8, 1997, 60/042,754, filed Apr. 8, 1997, 60/042,825, filed Apr. 8, 1997, 60/048,068, filed May 30, 1997, 60/048,070, filed May 30, 1997, and 60/048,184, filed May 30, 1997; U.S. application Ser. No. 10/100,683 is a continuation-in-part of International Application No. PCT/US98/06801, filed Apr. 7, 1998, which claims the benefit of U.S. Provisional Application Nos. 60/042,726, filed Apr. 8, 1997, 60/042,727, filed Apr. 8, 1997, 60/042,728, filed Apr. 8, 1997, 60/042,754, filed Apr. 8, 1997, 60/042,825, filed Apr. 8, 1997, 60/048,068, filed May 30, 1997, 60/048,070, filed May 30, 1997, and 60/048,184, filed May 30, 1997; U.S. application Ser. No. 10/100,683 is a continuation-in-part of International Application No. PCT/US98/10868, filed May 28, 1998, which claims the benefit of U.S. Provisional Application Nos. 60/044,039, filed May 30, 1997, 60/048,093, filed May 30, 1997, 60/048,190, filed May 30, 1997, 60/050,935, filed May 30, 1997, 60/048,101, filed May 30, 1997, 60/048,356, filed May 30, 1997, 60/056,250, filed Aug. 29, 1997, 60/056,296, filed Aug. 29, 1997, and 60/056,293, filed Aug. 29, 1997; U.S. application Ser. No. 10/100,683 is a continuation-in-part of International Application No. PCT/US98/11422, filed Jun. 4, 1998, which claims the benefit of U.S. Provisional Application Nos. 60/048,885, filed Jun. 6, 1997, 60/049,375, filed Jun. 6, 1997, 60/048,881, filed Jun. 6, 1997, 60/048,880, filed Jun. 6, 1997, 60/048,896, filed Jun. 6, 1997, 60/049,020, filed Jun. 6, 1997, 60/048,876, filed Jun. 6, 1997, 60/048,895, filed Jun. 6, 1997, 60/048,884, filed Jun. 6, 1997, 60/048,894, filed Jun. 6, 1997, 60/048,971, filed Jun. 6, 1997, 60/048,964, filed Jun. 6, 1997, 60/048,882, filed Jun. 6, 1997, 60/048,899, filed Jun. 6, 1997, 60/048,893, filed Jun. 6, 1997, 60/048,900, filed Jun. 6, 1997, 60/048,901, filed Jun. 6, 1997, 60/048,892, filed Jun. 6, 1997, 60/048,915, filed Jun. 6, 1997, 60/049,019, filed Jun. 6, 1997, 60/048,970, filed Jun. 6, 1997, 60/048,972, filed Jun. 6, 1997, 60/048,916, filed Jun. 6, 1997, 60/049,373, filed Jun. 6, 1997, 60/048,875, filed Jun. 6, 1997, 60/049,374, filed Jun. 6, 1997, 60/048,917, filed Jun. 6, 1997, 60/048,949, filed Jun. 6, 1997, 60/048,974, filed Jun. 6, 1997, 60/048,883, filed Jun. 6, 1997, 60/048,897, filed Jun. 6, 1997, 60/048,898, filed Jun. 6, 1997, 60/048,962, filed Jun. 6, 1997, 60/048,963, filed Jun. 6, 1997, 60/048,877, filed Jun. 6, 1997, 60/048,878, filed Jun. 6, 1997, 60/057,645, filed Sep. 5, 1997, 60/057,642, filed Sep. 5, 1997, 60/057,668, filed Sep. 5, 1997, 60/057,635, filed Sep. 5, 1997, 60/057,627, filed Sep. 5, 1997, 60/057,667, filed Sep. 5, 1997, 60/057,666, filed Sep. 5, 1997, 60/057,764, filed Sep. 5, 1997, 60/057,643, filed Sep. 5, 1997, 60/057,769, filed Sep. 5, 1997, 60/057,763, filed Sep. 5, 1997, 60/057,650, filed Sep. 5, 1997, 60/057,584, filed Sep. 5, 1997, 60/057,647, filed Sep. 5, 1997, 60/057,661, filed Sep. 5, 1997, 60/057,662, filed Sep. 5, 1997, 60/057,646, filed Sep. 5, 1997, 60/057,654, filed Sep. 5, 1997, 60/057,651, filed Sep. 5, 1997, 60/057,644, filed Sep. 5, 1997, 60/057,765, filed Sep. 5, 1997, 60/057,762, filed Sep. 5, 1997, 60/057,775, filed Sep. 5, 1997, 60/057,648, filed Sep. 5, 1997, 60/057,774, filed Sep. 5, 1997, 60/057,649, filed Sep. 5, 1997, 60/057,770, filed Sep. 5, 1997, 60/057,771, filed Sep. 5, 1997, 60/057,761, filed Sep. 5, 1997, 60/057,760, filed Sep. 5, 1997, 60/057,776, filed Sep. 5, 1997, 60/057,778, filed Sep. 5, 1997, 60/057,629, filed Sep. 5, 1997, 60/057,628, filed Sep. 5, 1997, 60/057,777, filed Sep. 5, 1997, 60/057,634, filed Sep. 5, 1997, and 60/070,923, filed Dec. 18, 1997; U.S. application Ser. No. 10/100,683 is a continuation-in-part of International Application No. PCT/US01/05614, filed Feb. 21, 2001, which claims the benefit of U.S. Provisional Application Nos. 60/184,836, filed Feb. 24, 2000, and 60/193,170, filed Mar. 29, 2000; U.S. application Ser. No. 10/100,683 is a continuation-in-part of International Application No. PCT/US98/12125, filed Jun. 11, 1998, which claims the benefit of U.S. Provisional Application Nos. 60/049,547, filed Jun. 13, 1997, 60/049,548, filed Jun. 13, 1997, 60/049,549, filed Jun. 13, 1997, 60/049,550, filed Jun. 13, 1997, 60/049,566, filed Jun. 13, 1997, 60/049,606, filed Jun. 13, 1997, 60/049,607, filed Jun. 13, 1997, 60/049,608, filed Jun. 13, 1997, 60/049,609, filed Jun. 13, 1997, 60/049,610, filed Jun. 13, 1997, 60/049,611, filed Jun. 13, 1997, 60/050,901, filed Jun. 13, 1997, 60/052,989, filed Jun. 13, 1997, 60/051,919, filed Jul.

8, 1997, 60/055,984, filed Aug. 18, 1997, 60/058,665, filed Sep. 12, 1997, 60/058,668, filed Sep. 12, 1997, 60/058,669, filed Sep. 12, 1997, 60/058,750, filed Sep. 12, 1997, 60/058,971, filed Sep. 12, 1997, 60/058,972, filed Sep. 12, 1997, 60/058,975, filed Sep. 12, 1997, 60/060,834, filed Oct. 2, 1997, 60/060,841, filed Oct. 2, 1997, 60/060,844, filed Oct. 2, 1997, 60/060,865, filed Oct. 2, 1997, 60/061,059, filed Oct. 2, 1997, and 60/061,060, filed Oct. 2, 1997; U.S. application Ser. No. 10/100,683 is a continuation-in-part of U.S. application Ser. No. 09/627,081, filed Jul. 27, 2000, which is a continuation of U.S. application Ser. No. 09/213,365, filed Dec. 17, 1998, which is a continuation-in-part of International Application No. PCT/US98/13608, filed Jun. 30, 1998; U.S. application Ser. No. 10/100,683 is a continuation-in-part of International Application No. PCT/US98/13608, filed Jun. 30, 1998, which claims the benefit of U.S. Provisional Application Nos. 60/051,480, filed Jul. 1, 1997, 60/051,381, filed Jul. 1, 1997, 60/058,663, filed Sep. 12, 1997, and 60/058,598, filed Sep. 12, 1997; U.S. application Ser. No. 10/100,683 is a continuation-in-part of U.S. application Ser. No. 09/984,490, filed Oct. 30, 2001, which is a divisional of U.S. application Ser. No. 09/227,357, filed Jan. 8, 1999, which is a continuation-in-part of International Application No. PCT/US98/13684, filed Jul. 7, 1998; U.S. application Ser. No. 10/100,683 is a continuation-in-part of U.S. application Ser. No. 09/983,802, filed Oct. 25, 2001, which is a continuation of U.S. application Ser. No. 09/227,357, filed Jan. 8, 1999, which is a continuation-in-part of International Application No. PCT/US98/13684, filed Jul. 7, 1998; U.S. application Ser. No. 10/100,683 is a continuation-in-part of U.S. application Ser. No. 09/973,278, filed Oct. 10, 2001, which claims the benefit of U.S. Provisional Application No. 60/239,899, filed Oct. 13, 2000; U.S. application Ser. No. 09/973,278 is a continuation-in-part of U.S. application Ser. No. 09/227,357, filed Jan. 8, 1999, which is a continuation-in-part of International Application No. PCT/US98/13684, filed Jul. 7, 1998; U.S. application Ser. No. 10/100,683 is a continuation-in-part of International Application No. PCT/US98/13684, filed Jul. 7, 1998, which claims the benefit of U.S. Provisional Application Nos. 60/051,926, filed Jul. 8, 1997, 60/052,793, filed Jul. 8, 1997, 60/051,925, filed Jul. 8, 1997, 60/051,929, filed Jul. 8, 1997, 60/052,803, filed Jul. 8, 1997, 60/052,732, filed Jul. 8, 1997, 60/051,931, filed Jul. 8, 1997, 60/051,932, filed Jul. 8, 1997, 60/051,916, filed Jul. 8, 1997, 60/051,930, filed Jul. 8, 1997, 60/051,918, filed Jul. 8, 1997, 60/051,920, filed Jul. 8, 1997, 60/052,733, filed Jul. 8, 1997, 60/052,795, filed Jul. 8, 1997, 60/051,919, filed Jul. 8, 1997, 60/051,928, filed Jul. 8, 1997, 60/055,722, filed Aug. 18, 1997, 60/055,723, filed Aug. 18, 1997, 60/055,948, filed Aug. 18, 1997, 60/055,949, filed Aug. 18, 1997, 60/055,953, filed Aug. 18, 1997, 60/055,950, filed Aug. 18, 1997, 60/055,947, filed Aug. 18, 1997, 60/055,964, filed Aug. 18, 1997, 60/056,360, filed Aug. 18, 1997, 60/055,684, filed Aug. 18, 1997, 60/055,984, filed Aug. 18, 1997, 60/055,954, filed Aug. 18, 1997, 60/058,785, filed Sep. 12, 1997, 60/058,664, filed Sep. 12, 1997, 60/058,660, filed Sep. 12, 1997, and 60/058,661, filed Sep. 12, 1997; U.S. application Ser. No. 10/100,683 is a continuation-in-part of U.S. application Ser. No. 09/776,724, filed Feb. 6, 2001, which claims the benefit of U.S. Provisional Application No. 60/180,909, filed Feb. 8, 2000; U.S. application Ser. No. 09/776,724 is a continuation-in-part of U.S. application Ser. No. 09/669,688, filed Sep. 26, 2000, which is a continuation of U.S. application Ser. No. 09/229,982, filed Jan. 14, 1999, which is a continuation-in-part of International Application No. PCT/US98/14613, filed Jul. 15, 1998; U.S. application Ser. No. 10/100,683 is a continuation-in-part of U.S. application Ser. No. 09/669,688, filed Sep. 26, 2000, which is a continuation of U.S. application Ser. No. 09/229,982, filed Jan. 14, 1999, which is a continuation-in-part of International Application No. PCT/US98/14613, filed Jul. 15, 1998; U.S. application Ser. No. 10/100,683 is a continuation-in-part of U.S. application Ser. No. 09/229,982, filed Jan. 14, 1999, which is a continuation-in-part of International Application No. PCT/US98/14613, filed Jul. 15, 1998; U.S. application Ser. No. 10/100,683 is a continuation-in-part of International Application No. PCT/US98/14613, filed Jul. 15, 1998, which claims the benefit of U.S. Provisional Application Nos. 60/052,661, filed Jul. 16, 1997, 60/052,872, filed Jul. 16, 1997, 60/052,871, filed Jul. 16, 1997, 60/052,874, filed Jul. 16, 1997, 60/052,873, filed Jul. 16, 1997, 60/052,870, filed Jul. 16, 1997, 60/052,875, filed Jul. 16, 1997, 60/053,440, filed Jul. 22, 1997, 60/053,441, filed Jul. 22, 1997, 60/053,442, filed Jul. 22, 1997, 60/056,359, filed Aug. 18, 1997, 60/055,725, filed Aug. 18, 1997, 60/055,985, filed Aug. 18, 1997, 60/055,952, filed Aug. 18, 1997, 60/055,989, filed Aug. 18, 1997, 60/056,361, filed Aug. 18, 1997, 60/055,726, filed Aug. 18, 1997, 60/055,724, filed Aug. 18, 1997, 60/055,946, filed Aug. 18, 1997, and 60/055,683, filed Aug. 18, 1997; U.S. application Ser. No. 10/100,683 claims the benefit of U.S. Provisional Application No. 60/295,558, filed Jun. 5, 2001; U.S. application Ser. No. 10/100,683 is a continuation-in-part of U.S. application Ser. No. 09/820,649, filed Mar. 30, 2001, which is a continuation of U.S. application Ser. No. 09/666,984, filed Sep. 21, 2000, which is a continuation of U.S. application Ser. No. 09/236,557, filed Jan. 26, 1999, which is a continuation-in-part of International Application No. PCT/US98/15949, filed Jul. 29, 1998; U.S. application Ser. No. 10/100,683 is a continuation-in-part of International Application No. PCT/US98/15949, filed Jul. 29, 1998, which claims the benefit of U.S. Provisional Application Nos. 60/054,212, filed Jul. 30, 1997, 60/054,209, filed Jul. 30, 1997, 60/054,234, filed Jul. 30, 1997, 60/054,218, filed Jul. 30, 1997, 60/054,214, filed Jul. 30, 1997, 60/054,236, filed Jul. 30, 1997, 60/054,215, filed Jul. 30, 1997, 60/054,211, filed Jul. 30, 1997, 60/054,217, filed Jul. 30, 1997, 60/054,213, filed Jul. 30, 1997, 60/055,968, filed Aug. 18, 1997, 60/055,969, filed Aug. 18, 1997, 60/055,972, filed Aug. 18, 1997, 60/056,561, filed Aug. 19, 1997, 60/056,534, filed Aug. 19, 1997, 60/056,729, filed Aug. 19, 1997, 60/056,543, filed Aug. 19, 1997, 60/056,727, filed Aug. 19, 1997, 60/056,554, filed Aug. 19, 1997, and 60/056,730, filed Aug. 19, 1997; U.S. application Ser. No. 10/100,683 is a continuation-in-part of U.S. application Ser. No. 09/969,730, filed Oct. 4, 2001, which is a continuation-in-part of U.S. application Ser. No. 09/774,639, filed Feb. 1, 2001, which is a continuation of U.S. application Ser. No. 09/244,112, filed Feb. 4, 1999, which is a continuation-in-part of International Application No. PCT/US98/16235, filed Aug. 4, 1998; U.S. application Ser. No. 10/100,683 is a continuation-in-part of U.S. application Ser. No. 09/774,639, filed Feb. 1, 2001, which is a continuation of U.S. application Ser. No. 09/244,112, filed Feb. 4, 1999, which is a continuation-in-part of International Application No. PCT/US98/16235, filed Aug. 4, 1998; U.S. application Ser. No. 10/100,683 is a continuation-in-part of U.S. application Ser. No. 09/969,730, filed Oct. 4, 2001, which claims the benefit of U.S. Provisional Application No. 60/238,291, filed Oct. 6, 2000; U.S. application Ser. No. 10/100,683 is a continuation-in-part of International Application No. PCT/US98/16235, filed Aug. 4, 1998, which claims the benefit of U.S. Provisional Application Nos. 60/055,386, filed Aug. 5, 1997, 60/054,807, filed Aug. 5, 1997, 60/055,312, filed Aug. 5, 1997, 60/055,309, filed Aug. 5, 1997, 60/054,798, filed Aug. 5, 1997, 60/055,310, filed Aug. 5, 1997, 60/054,806, filed Aug. 5, 1997, 60/054,809, filed Aug. 5, 1997, 60/054, 804, filed Aug. 5, 1997, 60/054,803, filed Aug. 5, 1997, 60/054,808, filed Aug. 5, 1997, 60/055,311, filed Aug. 5, 1997, 60/055,986, filed Aug. 18, 1997, 60/055,970, filed Aug. 18, 1997, 60/056,563, filed Aug. 19, 1997, 60/056,557, filed Aug. 19, 1997, 60/056,731, filed Aug. 19, 1997, 60/056,365, filed Aug. 19, 1997, 60/056,367, filed Aug. 19, 1997, 60/056,370, filed Aug. 19, 1997, 60/056,364, filed Aug. 19, 1997, 60/056,366, filed Aug. 19, 1997, 60/056,732, filed Aug. 19, 1997, and 60/056,371, filed Aug. 19, 1997; U.S. application Ser. No. 10/100,683 is a continuation-in-part of U.S. application Ser. No. 09/716,128, filed Nov. 17, 2000, which is a continuation of U.S. application Ser. No. 09/251,329, filed Feb. 17, 1999, which is a continuation-in-part of International Application No. PCT/US98/17044, filed Aug. 18, 1998; U.S. application Ser. No. 10/100,683 is a continuation-in-part of International Application No. PCT/US98/17044, filed Aug. 18, 1998, which claims the benefit of U.S. Provisional Application Nos. 60/056,555, filed Aug. 19, 1997, 60/056,556, filed Aug. 19, 1997, 60/056,535, filed Aug. 19, 1997, 60/056,629, filed Aug. 19, 1997, 60/056,369, filed Aug. 19, 1997, 60/056,628, filed Aug. 19, 1997, 60/056,728, filed Aug. 19, 1997, 60/056,368, filed Aug. 19, 1997, 60/056,726, filed Aug. 19, 1997, 60/089,510, filed Jun. 16, 1998, and 60/092,956, filed Jul. 15, 1998; U.S. application Ser. No. 10/100,683 is a continuation-in-part of U.S. application Ser. No. 09/729,835, filed Dec. 6, 2000, which is a divisional of U.S. application Ser. No. 09/257,179, filed Feb. 25, 1999, which is a continuation-in-part of International Application No. PCT/US98/17709, filed Aug. 27, 1998; U.S. application Ser. No. 10/100,683 is a continuation-in-part of U.S. application Ser. No. 09/257,179, filed Feb. 25, 1999, which is a continuation-in-part of International Application No. PCT/US98/17709, filed Aug. 27, 1998; U.S. application Ser. No. 10/100,683 is a continuation-in-part of International Application No. PCT/US98/17709, filed Aug. 27, 1998, which claims the benefit of U.S. Provisional Application Nos. 60/056,270, filed Aug. 29, 1997, 60/056,271, filed Aug. 29, 1997, 60/056,247, filed Aug. 29, 1997, and 60/056,073, filed Aug. 29, 1997; U.S. application Ser. No. 10/100,683 is a continuation-in-part of U.S. application Ser. No. 10/047,021, filed Jan. 17, 2002, which is a continuation-in-part of U.S. application Ser. No. 09/722,329, filed Nov. 28, 2000, which is a continuation of U.S. application Ser. No. 09/262,109, filed Mar. 4, 1999, which is a continuation-in-part of International Application No. PCT/US98/18360, filed Sep. 3, 1998; U.S. application Ser. No. 10/100,683 is a continuation-in-part of U.S. application Ser. No. 09/722,329, filed Nov. 28, 2000, which is a continuation of U.S. application Ser. No. 09/262,109, filed Mar. 4, 1999, which is a continuation-in-part of International Application No. PCT/US98/18360, filed Sep. 3, 1998; U.S. application Ser. No. 10/100,683 is a continuation-in-part of International Application No. PCT/US02/01109, filed Jan. 17, 2002, which claims the benefit of U.S. Provisional Application No. 60/262,066, filed Jan. 18, 2001; U.S. application Ser. No. 10/100,683 is a continuation-in-part of International Application No. PCT/US98/18360, filed Sep. 3, 1998, which claims the benefit of U.S. Provisional Application Nos. 60/057,626, filed Sep. 5, 1997, 60/057,663, filed Sep. 5, 1997, 60/057,669, filed Sep. 5, 1997, 60/058,667, filed Sep. 12, 1997, 60/058,974, filed Sep. 12, 1997, 60/058,973, filed Sep. 12, 1997, 60/058,666, filed Sep. 12, 1997, and 60/090,112, filed Jun. 22, 1998; U.S. application Ser. No. 10/100,683 is a continuation-in-part of U.S. application Ser. No. 09/281,976, filed Mar. 31, 1999, which is a continuation-in-part of International Application No. PCT/US98/20775, filed Oct. 1, 1998; U.S. application Ser. No. 10/100,683 is a continuation-in-part of International Application No. PCT/US98/20775, filed Oct. 1, 1998, which claims the benefit of U.S. Provisional Application Nos. 60/060,837, filed Oct. 2, 1997, 60/060,862, filed Oct. 2, 1997, 60/060,839, filed Oct. 2, 1997, 60/060,866, filed Oct. 2, 1997, 60/060,843, filed Oct. 2, 1997, 60/060,836, filed Oct. 2, 1997, 60/060,838, filed Oct. 2, 1997, 60/060,874, filed Oct. 2, 1997, 60/060,833, filed Oct. 2, 1997, 60/060,884, filed Oct. 2, 1997, and 60/060,880, filed Oct. 2, 1997; U.S. application Ser. No. 10/100,683 is a continuation-in-part of U.S. application Ser. No. 09/984,429, filed Oct. 30, 2001, which claims the benefit of U.S. Provisional Application No. 60/244,591, filed Nov. 1, 2000; U.S. application Ser. No. 09/984,429 is a continuation-in-part of U.S. application Ser. No. 09/288,143, filed Apr. 8, 1999, which is a continuation-in-part of International Application No. PCT/US98/21142, filed Oct. 8, 1998; U.S. application Ser. No. 10/100,683 claims the benefit of U.S. Provisional Application No. 60/244,591, filed Nov. 1, 2000; U.S. application Ser. No. 10/100,683 is a continuation-in-part of U.S. application Ser. No. 09/288,143, filed Apr. 8, 1999, which is a continuation-in-part of International Application No. PCT/US98/21142, filed Oct. 8, 1998; U.S. application Ser. No. 10/100,683 is a continuation-in-part of International Application No. PCT/US98/21142, filed Oct. 8, 1998, which claims the benefit of U.S. Provisional Application Nos. 60/061,463, filed Oct. 9, 1997, 60/061,529, filed Oct. 9, 1997, 60/071,498, filed Oct. 9, 1997, 60/061,527, filed Oct. 9, 1997, 60/061,536, filed Oct. 9, 1997, and 60/061,532, filed Oct., 9, 1997; U.S. application Ser. No. 10/100,683 is a continuation-in-part of U.S. application Ser. No. 09/296,622, filed Apr. 23, 1999, which is a continuation-in-part of International Application No. PCT/US98/22376, filed Oct. 23, 1998; U.S. application Ser. No. 10/100,683 is a continuation-in-part of International Application No. PCT/US98/22376, filed Oct. 23, 1998, which claims the benefit of U.S. Provisional Application Nos. 60/063,099, filed Oct. 24, 1997, 60/063,088, filed Oct. 24, 1997, 60/063,100, filed Oct. 24, 1997, 60/063,387, filed Oct. 24, 1997, 60/063,148, filed Oct. 24, 1997, 60/063,386, filed Oct. 24, 1997, 60/062,784, filed Oct. 24, 1997, 60/063,091, filed Oct. 24, 1997, 60/063,090, filed Oct. 24, 1997, 60/063,089, filed Oct. 24, 1997, 60/063,092, filed Oct. 24, 1997, 60/063,111, filed Oct. 24, 1997, 60/063,101, filed Oct. 24, 1997, 60/063,109, filed Oct. 24, 1997, 60/063,110, filed Oct. 24, 1997, 60/063,098, filed Oct. 24, 1997, and 60/063,097, filed Oct. 24, 1997; U.S. application Ser. No. 10/100,683 is a continuation-in-part of U.S. application Ser. No. 09/974,879, filed Oct. 12, 2001, which claims the benefit of U.S. Provisional Application No. 60/239,893, filed Oct. 13, 2000; U.S. application Ser. No. 09/974,879 is a continuation-in-part of U.S. application Ser. No. 09/818,683, filed Mar. 28, 2001, which is a continuation of U.S. application Ser. No. 09/305,736, filed May 5, 1999, which is a continuation-in-part of International Application No. PCT/US98/23435, filed Nov. 4, 1998; U.S. application Ser. No. 10/100,683 is a continuation-in-part of U.S. application Ser. No. 09/818,683, filed Mar. 28, 2001, which is a continuation of U.S. application Ser. No. 09/305,736, filed May 5, 1999, which is a continuation-in-part of International Application No. PCT/US98/23435, filed Nov. 4, 1998; U.S. application Ser. No. 10/100,683 is a continuation-in-part of U.S. application Ser. No. 09/305,736, filed May 5, 1999, which is a continuation-in-part of International Application No. PCT/US98/23435, filed Nov. 4, 1998; U.S. application Ser. No. 10/100,683 is a continuation-in-part of International Application No. PCT/US98/23435, filed Nov. 4, 1998, which claims the benefit of U.S. Provisional Application Nos. 60/064,911, filed Nov. 7, 1997, 60/064,912, filed Nov. 7, 1997, 60/064,983, filed Nov. 7, 1997, 60/064,900, filed Nov. 7, 1997, 60/064,988, filed Nov. 7, 1997, 60/064,987, filed Nov. 7, 1997, 60/064,908, filed Nov. 7, 1997, 60/064,984, filed Nov. 7, 1997, 60/064,985, filed Nov. 7, 1997, 60/066,094, filed Nov. 17, 1997, 60/066,100, filed Nov. 17, 1997, 60/066,089, filed Nov. 17, 1997, 60/066,095, filed Nov. 17, 1997, and 60/066,090, filed Nov. 17, 1997; U.S. application Ser. No. 10/100,683 is a continuation-in-part of U.S. application Ser. No. 09/334,595, filed Jun. 17, 1999, which is a continuation-in-part of International Application No. PCT/US98/27059, filed Dec. 17, 1998; U.S. application Ser. No. 10/100,683 is a continuation-in-part of International Application No. PCT/US98/27059, filed Dec. 17, 1998, which claims the benefit of U.S. Provisional Application Nos. 60/070,923, filed Dec. 18, 1997, 60/068,007, filed Dec. 18, 1997, 60/068,057, filed Dec. 18, 1997, 60/068,006, filed Dec. 18, 1997, 60/068,369, filed Dec. 19, 1997, 60/068,367, filed Dec. 19, 1997, 60/068,368, filed Dec. 19, 1997, 60/068,169, filed Dec. 19, 1997, 60/068,053, filed Dec. 18, 1997, 60/068,064, filed Dec. 18, 1997, 60/068,054, filed Dec. 18, 1997, 60/068,008, filed Dec. 18, 1997, and 60/068,365, filed Dec. 19, 1997; U.S. application Ser. No. 10/100,683 is a continuation-in-part of U.S. application Ser. No. 09/938,671, filed Aug. 27, 2001, which is a continuation of U.S. application Ser. No. 09/739,907, filed Dec. 20, 2000, which is a continuation of U.S. application Ser. No. 09/348,457, filed Jul. 7, 1999, which is a continuation-in-part of International Application No. PCT/US99/00108, filed Jan. 6, 1999; U.S. application Ser. No. 10/100,683 is a continuation-in-part of U.S. application Ser. No. 09/739,907, filed Dec. 20, 2000, which is a continuation of U.S. application Ser. No. 09/348,457, filed Jul. 7, 1999, which is a continuation-in-part of International Application No. PCT/US99/00108, filed Jan. 6, 1999; U.S. application Ser. No. 10/100,683 is a continuation-in-part of U.S. application Ser. No. 09/348,457, filed Jul. 7, 1999, which is a continuation-in-part of International Application No. PCT/US99/00108, filed Jan. 6, 1999; U.S. application Ser. No. 10/100,683 is a continuation-in-part of International Application No. PCT/US99/00108, filed Jan. 6, 1999, which claims the benefit of U.S. Provisional Application Nos. 60/070,704, filed Jan. 7, 1998, 60/070,658, filed Jan. 7, 1998, 60/070,692, filed Jan. 7, 1998, and 60/070,657, filed Jan. 7, 1998; U.S. application Ser. No. 10/100,683 is a continuation-in-part of U.S. application Ser. No. 09/949,925, filed Sep. 12, 2001, which claims the benefit of U.S. Provisional Application No. 60/232,150, filed Sep. 12, 2000; U.S. application Ser. No. 09/949,925 is a continuation-in-part of International Application No. PCT/US99/01621, filed Jan. 27, 1999; U.S. application Ser. No. 09/949,925 is a continuation-in-part of U.S. application Ser. No. 09/363,044, filed Jul. 29, 1999, which is a continuation-in-part of International Application No. PCT/US99/01621, filed Jan. 27, 1999; U.S. application Ser. No. 10/100,683 is a continuation-in-part of U.S. application Ser. No. 09/813,153, filed Mar. 21, 2001, which is a continuation of U.S. application Ser. No. 09/363,044, filed Jul. 29, 1999, which is a continuation-in-part of International Application No. PCT/US99/01621, filed Jan. 27, 1999; U.S. application Ser. No. 10/100,683 is a continuation-in-part of U.S. application Ser. No. 09/363,044, filed Jul. 29, 1999, which is a continuation-in-part of International Application No. PCT/US99/01621, filed Jan. 27, 1999; U.S. application Ser. No. 10/100,683 is a continuation-in-part of International Application No. PCT/US99/01621, filed Jan. 27, 1999, which claims the benefit of U.S. Provisional Application Nos. 60/073,170, filed Jan. 30, 1998, 60/073,167, filed Jan. 30, 1998, 60/073,165, filed Jan. 30, 1998, 60/073,164, filed Jan. 30, 1998, 60/073,162, filed Jan. 30, 1998, 60/073,161, filed Jan. 30, 1998, 60/073,160, filed Jan. 30, 1998, and 60/073,159, filed Jan. 30, 1998; U.S. application Ser. No. 10/100,683 is a continuation-in-part of U.S. application Ser. No. 10/062,548, filed Feb. 5, 2002, which is a continuation of U.S. application Ser. No. 09/369,247, filed Aug. 5, 1999; U.S. application Ser. No. 09/369,247 is a continuation-in-part of International Application No. PCT/US99/02293, filed Feb. 4, 1999; U.S. application Ser. No. 10/100,683 is a continuation-in-part of U.S. application Ser. No. 09/369,247, filed Aug. 5, 1999; U.S. application Ser. No. 09/369,247 is a continuation-in-part of International Application No. PCT/US99/02293, filed Feb. 4, 1999; U.S. application Ser. No. 10/100,683 is a continuation-in-part of International Application No. PCT/US99/02293, filed Feb. 4, 1999, which claims the benefit of U.S. Provisional Application Nos. 60/074,118, filed Feb. 9, 1998, 60/074,157, filed Feb. 9, 1998, 60/074,037, filed Feb. 9, 1998, 60/074,141, filed Feb. 9, 1998, and 60/074,341, filed Feb. 9, 1998; U.S. application Ser. No. 10/100,683 is a continuation-in-part of U.S. application Ser. No. 09/716,129, filed Nov. 17, 2000, which is a continuation-in-part of International Application No. PCT/US99/03939, filed Feb. 24, 1999; U.S. application Ser. No. 09/716,129 is a continuation of U.S. application Ser. No. 09/382,572, filed Aug. 25, 1999, which is a continuation-in-part of International Application No. PCT/US99/03939, filed Feb. 24, 1999; U.S. application Ser. No. 10/100,683 is a continuation-in-part of International Application No. PCT/US99/03939, filed Feb. 24, 1999, which claims the benefit of U.S. Provisional Application Nos. 60/076,053, filed Feb. 26, 1998, 60/076,051, filed Feb. 26, 1998, 60/076,054, filed Feb. 26, 1998, 60/076,052, filed Feb. 26, 1998, and 60/076,057, filed Feb. 26, 1998; U.S. application Ser. No. 10/100,683 is a continuation-in-part of U.S. application Ser. No. 09/798,889, filed Mar. 6, 2001, which is a continuation of U.S. application Ser. No. 09/393,022, filed Sep. 9, 1999, which is a continuation-in-part of International Application No. PCT/US99/05721, filed Mar. 11, 1999; U.S. application Ser. No. 10/100,683 is a continuation-in-part of International Application No. PCT/US99/05721, filed Mar. 11, 1999, which claims the benefit of U.S. Provisional Application Nos. 60/077,714, filed Mar. 12, 1998, 60/077,686, filed Mar. 12, 1998, 60/077,687, filed Mar. 12, 1998, and 60/077,696, filed Mar. 12, 1998; U.S. application Ser. No. 10/100,683 is a continuation-in-part of U.S. application Ser. No. 09/397,945, filed Sep. 17, 1999, which is a continuation-in-part of International Application No. PCT/US99/05804, filed Mar. 18, 1999; U.S. application Ser. No. 10/100,683 is a continuation-in-part of International Application No. PCT/US99/05804, filed Mar. 18, 1999, which claims the benefit of U.S. Provisional Application Nos. 60/078,566, filed Mar. 19, 1998, 60/078,576, filed Mar. 19, 1998, 60/078,573, filed Mar. 19, 1998, 60/078,574, filed Mar. 19, 1998, 60/078,579, filed Mar. 19, 1998, 60/080,314, filed Apr. 1, 1998, 60/080,312, filed Apr. 1, 1998, 60/078,578, filed Mar. 19, 1998, 60/078,581, filed Mar. 19, 1998, 60/078,577, filed Mar. 19, 1998, 60/078,563, filed Mar. 19, 1998, and 60/080,313, filed Apr. 1, 1998; U.S. application Ser. No. 10/100,683 is a continuation-in-part of U.S. application Ser. No. 09/948,783, filed Sep. 10, 2001, which claims the benefit of U.S. Provisional Application No. 60/231,846, filed Sep. 11, 2000; U.S. application Ser. No. 09/948,783 is a continuation-in-part of U.S. application Ser. No. 09/892,877, filed Jun. 28, 2001, which is a continuation of U.S. application Ser. No. 09/437,658, filed Nov. 10, 1999, which is a continuation-in-part of International Application No. PCT/US99/09847, filed May 6, 1999; U.S. application Ser. No. 10/100,683 is a continuation-in-part of U.S. application Ser. No. 09/892,877, filed Jun. 28, 2001, which is a continuation of U.S. application Ser. No. 09/437,658, filed Nov. 10, 1999, which is a continuation-in-part of International Application No. PCT/US99/09847, filed May 6, 1999;

U.S. application Ser. No. 10/100,683 is a continuation-in-part of International Application No. PCT/US99/09847, filed May 6, 1999, which claims the benefit of U.S. Provisional Application Nos. 60/085,093, filed May 12, 1998, 60/085,094, filed May 12, 1998, 60/085,105, filed May 12, 1998, 60/085,180, filed May 12, 1998, 60/085,927, filed May 18, 1998, 60/085,906, filed May 18, 1998, 60/085,920, filed May 18, 1998, 60/085,924, filed May 18, 1998, 60/085,922, filed May 18, 1998, 60/085,923, filed May 18, 1998, 60/085,921, filed May 18, 1998, 60/085,925, filed May 18, 1998, and 60/085,928, filed May 18, 1998; U.S. application Ser. No. 10/100,683 is a continuation-in-part of U.S. application Ser. No. 10/050,873, filed Jan. 18, 2002, which claims the benefit of U.S. Provisional Application Nos. 60/263,681, filed Jan. 24, 2001, and 60/263,230, filed Jan. 23, 2001; U.S. application Ser. No. 10/050,873 is a continuation-in-part of U.S. application Ser. No. 09/461,325, filed Dec. 14, 1999, which is a continuation-in-part of International Application No. PCT/US99/13418, filed Jun. 15, 1999; U.S. application Ser. No. 10/100,683 is a continuation-in-part of U.S. application Ser. No. 10/012,542, filed Dec. 12, 2001, which is a divisional of U.S. application Ser. No. 09/461,325, filed Dec. 14, 1999, which is a continuation-in-part of International Application No. PCT/US99/13418, filed Jun. 15, 1999; U.S. application Ser. No. 10/100,683 is a continuation-in-part of U.S. application Ser. No. 09/461,325, filed Dec. 14, 1999, which is a continuation-in-part of International Application No. PCT/US99/13418, filed Jun. 15, 1999; U.S. application Ser. No. 10/100,683 is a continuation-in-part of International Application No. PCT/US99/13418, filed Jun. 15, 1999, which claims the benefit of U.S. Provisional Application Nos. 60/089,507, filed Jun. 16, 1998, 60/089,508, filed Jun. 16, 1998, 60/089,509, filed Jun. 16, 1998, 60/089,510, filed Jun. 16, 1998, 60/090,112, filed Jun. 22, 1998, and 60/090,113, filed Jun. 22, 1998; U.S. application Ser. No. 10/100,683 is a continuation-in-part of U.S. application Ser. No. 09/984,271, filed Oct. 29, 2001, which is a divisional of U.S. application Ser. No. 09/482,273, filed Jan. 13, 2000, which is a continuation-in-part of International Application No. PCT/US99/15849, filed Jul. 14, 1999; U.S. application Ser. No. 10/100,683 is a continuation-in-part of U.S. application Ser. No. 09/984,276, filed Oct. 29, 2001, which is a divisional of U.S. application Ser. No. 09/482,273, filed Jan. 13, 2000, which is a continuation-in-part of International Application No. PCT/US99/15849, filed Jul. 14, 1999; U.S. application Ser. No. 10/100,683 is a continuation-in-part of U.S. application Ser. No. 09/482,273, filed Jan. 13, 2000, which is a continuation-in-part of International Application No. PCT/US99/15849, filed Jul. 14, 1999; U.S. application Ser. No. 10/100,683 is a continuation-in-part of International Application No. PCT/US99/15849, filed Jul. 14, 1999, which claims the benefit of U.S. Provisional Application Nos. 60/092,921, filed Jul. 15, 1998, 60/092,922, filed Jul. 15, 1998, and 60/092,956, filed Jul. 15, 1998; U.S. application Ser. No. 10/100,683 is a continuation-in-part of International Application No. PCT/US01/29871, filed Sep. 24, 2001, which claims the benefit of U.S. Provisional Application No. 60/234,925, filed Sep. 25, 2000; International Application No. PCT/US01/29871 is a continuation-in-part of International Application No. PCT/US01/00911, filed Jan. 12, 2001; U.S. application Ser. No. 10/100,683 is a continuation-in-part of International Application No. PCT/US01/00911, filed Jan. 12, 2001, which is a continuation-in-part of U.S. application Ser. No. 09/482,273, filed Jan. 13, 2000; U.S. application Ser. No. 10/100,683 claims the benefit of U.S. Provisional Application No. 60/350,898, filed Jan. 25, 2002; U.S. application Ser. No. 10/100,683 is a continuation-in-part of U.S. application Ser. No. 09/489,847, filed Jan. 24, 2000, which is a continuation-in-part of International Application No. PCT/US99/17130, filed Jul. 29, 1999; U.S. application Ser. No. 10/100,683 is a continuation-in-part of International Application No. PCT/US99/17130, filed Jul. 29, 1999, which claims the benefit of U.S. Provisional Application Nos. 60/094,657, filed Jul. 30, 1998, 60/095,486, filed Aug. 5, 1998, 60/096,319, filed Aug. 12, 1998, 60/095,454, filed Aug. 6, 1998, and 60/095,455, filed Aug. 6, 1998; U.S. application Ser. No. 10/100,683 is a continuation-in-part of U.S. application Ser. No. 10/054,988, filed Jan. 25, 2002, which is a continuation of U.S. application Ser. No. 09/904,615, filed Jul. 16, 2001, which is a continuation of U.S. application Ser. No. 09/739,254, filed Dec. 19, 2000, which is a continuation of U.S. application Ser. No. 09/511,554, filed Feb. 23, 2000, which is a continuation-in-part of International Application No. PCT/US99/19330, filed Aug. 24, 1999; U.S. application Ser. No. 10/100,683 is a continuation-in-part of U.S. application Ser. No. 09/904,615, filed Jul. 16, 2001, which is a continuation of U.S. application Ser. No. 09/739,254, filed Dec. 19, 2000, which is a continuation of U.S. application Ser. No. 09/511,554, filed Feb. 23, 2000, which is a continuation-in-part of International Application No. PCT/US99/19330, filed Aug. 24, 1999; U.S. application Ser. No. 10/100,683 is a continuation-in-part of International Application No. PCT/US99/19330, filed Aug. 24, 1999, which claims the benefit of U.S. Provisional Application Nos. 60/097,917, filed Aug. 25, 1998, and 60/098,634, filed Aug. 31, 1998; U.S. application Ser. No. 10/100,683 is a continuation-in-part of U.S. application Ser. No. 09/820,893, filed Mar. 30, 2001, which is a continuation of U.S. application Ser. No. 09/531,119, filed Mar. 20, 2000, which is a continuation-in-part of International Application No. PCT/US99/22012, filed Sep. 22, 1999; U.S. application Ser. No. 10/100,683 is a continuation-in-part of International Application No. PCT/US99/22012, filed Sep. 22, 1999, which claims the benefit of U.S. Provisional Application Nos. 60/101,546, filed Sep. 23, 1998, and 60/102,895, filed Oct. 2, 1998; U.S. application Ser. No. 10/100,683 is a continuation-in-part of U.S. application Ser. No. 09/948,820, filed Sep. 10, 2001, which is a continuation of U.S. application Ser. No. 09/565,391, filed May 5, 2000, which is a continuation-in-part of International Application No. PCT/US99/26409, filed Nov. 9, 1999; U.S. application Ser. No. 10/100,683 is a continuation-in-part of U.S. application Ser. No. 09/565,391, filed May 5, 2000, which is a continuation-in-part of International Application No. PCT/US99/26409, filed Nov. 9, 1999; U.S. application Ser. No. 10/100,683 is a continuation-in-part of International Application No. PCT/US99/26409, filed Nov. 9, 1999, which claims the benefit of U.S. Provisional Application No. 60/108,207, filed Nov. 12, 1998; U.S. application Ser. No. 10/100,683 is a continuation-in-part of U.S. application Ser. No. 09/895,298, filed Jul. 2, 2001, which is a continuation of U.S. application Ser. No. 09/591,316, filed Jun. 9, 2000, which is a continuation-in-part of International Application No. PCT/US99/29950, filed Dec. 16, 1999; U.S. application Ser. No. 10/100,683 is a continuation-in-part of International Application No. PCT/US99/29950, filed Dec. 16, 1999, which claims the benefit of U.S. Provisional Application Nos. 60/113,006, filed Dec. 18, 1998, and 60/112,809, filed Dec. 17, 1998; U.S. application Ser. No. 10/100,683 is a continuation-in-part of U.S. application Ser. No. 09/985,153, filed Nov. 1, 2001, which is a continuation of U.S. application Ser. No. 09/618,150, filed Jul. 17, 2000, which is a continuation-in-part of International Application No. PCT/US00/00903, filed Jan. 18, 2000; U.S. application Ser. No. 10/100,683 is a continuation-in-part of International Application No. PCT/US00/00903, filed Jan. 18, 2000, which claims the benefit of U.S. Provisional Application No. 60/116,330, filed Jan. 19, 1999; U.S. application Ser. No. 10/100,683 is a continuation-in-part of U.S. application Ser. No. 09/997,131, filed Nov. 30, 2001, which is a continuation of U.S. application Ser. No. 09/628,508, filed Jul. 28, 2000, which is a continuation-in-part of International Application No. PCT/US00/03062, filed Feb. 8, 2000; U.S. application Ser. No. 10/100,683 is a continuation-in-part of International Application No. PCT/US00/03062, filed Feb. 8, 2000, which claims the benefit of U.S. Provisional Application No. 60/119,468, filed Feb. 10, 1999; U.S. application Ser. No. 10/100,683 is a continuation-in-part of U.S. application Ser. No. 10/050,882, filed Jan. 18, 2002, which is a continuation of U.S. application Ser. No. 09/661,453, filed Sep. 13, 2000, which is a continuation-in-part of International Application No. PCT/US00/06783, filed Mar. 16, 2000; U.S. application Ser. No. 10/100,683 is a continuation-in-part of U.S. application Ser. No. 09/661,453, filed Sep. 13, 2000, which is a continuation-in-part of International Application No. PCT/US00/06783, filed Mar. 16, 2000; U.S. application Ser. No. 10/100,683 is a continuation-in-part of International Application No. PCT/US00/06783, filed Mar. 16, 2000, which claims the benefit of U.S. Provisional Application No. 60/125,055, filed Mar. 18, 1999; U.S. application Ser. No. 10/100,683 is a continuation-in-part of U.S. application Ser. No. 10/050,704, filed Jan. 18, 2002, which is a continuation of U.S. application Ser. No. 09/684,524, filed Oct. 10, 2000, which is a continuation-in-part of International Application No. PCT/US00/08979, filed Apr. 6, 2000; U.S. application Ser. No. 10/100,683 is a continuation-in-part of U.S. application Ser. No. 09/684,524, filed Oct. 10, 2000, which is a continuation-in-part of International Application No. PCT/US00/08979, filed Apr. 6, 2000; U.S. application Ser. No. 10/100,683 is a continuation-in-part of International Application No. PCT/US00/08979, filed Apr. 6, 2000, which claims the benefit of U.S. Provisional Application Nos. 60/128,693, filed Apr. 9, 1999, and 60/130,991, filed Apr. 26, 1999; U.S. application Ser. No. 10/100,683 is a continuation-in-part of U.S. application Ser. No. 10/042,141, filed Jan. 11, 2002, which is a continuation of U.S. application Ser. No. 09/726,643, filed Dec. 1, 2000, which is a continuation-in-part of International Application No. PCT/US00/15187, filed Jun. 2, 2000; U.S. application Ser. No. 10/100,683 is a continuation-in-part of U.S. application Ser. No. 09/726,643, filed Dec. 1, 2000, which is a continuation-in-part of International Application No. PCT/US00/15187, filed Jun. 2, 2000; U.S. application Ser. No. 10/100,683 is a continuation-in-part of International Application No. PCT/US00/15187, filed Jun. 2, 2000, which claims the benefit of U.S. Provisional Application No. 60/137,725, filed Jun. 7, 1999; U.S. application Ser. No. 10/100,683 is a continuation-in-part of U.S. application Ser. No. 09/756,168, filed Jan. 9, 2001, which is a continuation-in-part of International Application No. PCT/US00/19735, filed Jul. 23, 1999; U.S. application Ser. No. 10/100,683 is a continuation-in-part of International Application No. PCT/US00/19735, filed Jul. 20, 2000, which claims the benefit of U.S. Provisional Application No. 60/145,220, filed Jul. 23, 1999; U.S. application Ser. No. 10/100,683 is a continuation-in-part of U.S. application Ser. No. 10/060,255, filed Feb. 1, 2002, which is a continuation of U.S. application Ser. No. 09/781,417, filed Feb. 13, 2001, which is a continuation-in-part of International Application No. PCT/US00/22325, filed Aug. 16, 2000; U.S. application Ser. No. 10/100,683 is a continuation-in-part of U.S. application Ser. No. 09/781,417, filed Feb. 13, 2001, which is a continuation-in-part of International Application No. PCT/US00/22325, filed Aug. 16, 2000; U.S. application Ser. No. 10/100,683 is a continuation-in-part of International Application No. PCT/US00/22325, filed Aug. 16, 2000, which claims the benefit of U.S. Provisional Application No. 60/149,182, filed Aug. 17, 1999; U.S. application Ser. No. 10/100,683 is a continuation-in-part of U.S. application Ser. No. 09/789,561, filed Feb. 22, 2001, which is a continuation-in-part of International Application No. PCT/US00/24008, filed Aug. 31, 2000; U.S. application Ser. No. 10/100,683 is a continuation-in-part of International Application No. PCT/US00/24008, filed Aug. 31, 2000, which claims the benefit of U.S. Provisional Application Nos. 60/152,315, filed Sep. 3, 1999, and 60/152,317, filed Sep. 3, 1999; U.S. application Ser. No. 10/100,683 is a continuation-in-part of U.S. application Ser. No. 09/800,729, filed Mar. 8, 2001, which is a continuation-in-part of International Application No. PCT/US00/26013, filed Sep. 22, 2000; U.S. application Ser. No. 10/100,683 is a continuation-in-part of International Application No. PCT/US00/26013, filed Sep. 22, 2000, which claims the benefit of U.S. Provisional Application No. 60/155,709, filed Sep. 24, 1999; U.S. application Ser. No. 10/100,683 is a continuation-in-part of U.S. application Ser. No. 09/832,129, filed Apr. 11, 2001, which is a continuation-in-part of International Application No. PCT/US00/28664, filed Oct. 17, 2000; U.S. application Ser. No. 10/100,683 is a continuation-in-part of International Application No. PCT/US00/28664, filed Oct. 17, 2000, which claims the benefit of U.S. Provisional Application Nos. 60/163,085, filed Nov. 2, 1999, and 60/172,411, filed Dec. 17, 1999; U.S. application Ser. No. 10/100,683 is a continuation-in-part of International Application No. PCT/US00/29363, filed Oct. 25, 2000, which claims the benefit of U.S. Provisional Application Nos. 60/215,139, filed Jun. 30, 2000, and 60/162,239, filed Oct. 29, 1999; U.S. application Ser. No. 10/100,683 is a continuation-in-part of International Application No. PCT/US00/29360, filed Oct. 25, 2000, which claims the benefit of U.S. Provisional Application Nos. 60/215,138, filed Jun. 30, 2000, and 60/162,211, filed Oct. 29, 1999; U.S. application Ser. No. 10/100,683 is a continuation-in-part of International Application No. PCT/US00/29362, filed Oct. 25, 2000, which claims the benefit of U.S. Provisional Application Nos. 60/215,131, filed Jun. 30, 2000, and 60/162,240, filed Oct. 29, 1999; U.S. application Ser. No. 10/100,683 is a continuation-in-part of International Application No. PCT/US00/29365, filed Oct. 25, 2000, which claims the benefit of U.S. Provisional Application Nos. 60/219,666, filed Jul. 21, 2000, and 60/162,237, filed Oct. 29, 1999; U.S. application Ser. No. 10/100,683 is a continuation-in-part of International Application No. PCT/US00/29364, filed Oct. 25, 2000, which claims the benefit of U.S. Provisional Application Nos. 60/215,134, filed Jun. 30, 2000, and 60/162,238, filed Oct. 29, 1999; U.S. application Ser. No. 10/100,683 is a continuation-in-part of International Application No. PCT/US00/30040, filed Nov. 1, 2000, which claims the benefit of U.S. Provisional Application Nos. 60/215,130, filed Jun. 30, 2000, and 60/163,580, filed Nov. 5, 1999; U.S. application Ser. No. 10/100,683 is a continuation-in-part of International Application No. PCT/US00/30037, filed Nov. 1, 2000, which claims the benefit of U.S. Provisional Application Nos. 60/215,137, filed Jun. 30, 2000, and 60/163,577, filed Nov. 5, 1999; U.S. application Ser. No. 10/100,683 is a continuation-in-part of International Application No. PCT/US00/30045, filed Nov. 1, 2000, which claims the benefit of U.S. Provisional Application Nos. 60/215,133, filed Jun. 30, 2000, and 60/163,581, filed Nov. 5, 1999; U.S. application Ser. No. 10/100,683 is a continuation-in-part of International Application No. PCT/US00/30036, filed Nov. 1, 2000, which claims the benefit of U.S. Provisional Application Nos. 60/221,366, filed Jul. 27, 2000, and 60/163,576, filed Nov. 5, 1999; U.S. application Ser. No. 10/100,683 is a continuation-in-part of International Application No. PCT/US00/30039, filed Nov. 1, 2000, which claims the benefit of U.S. Provisional Application Nos. 60/221,367, filed Jul. 27, 2000, 60/195,296, filed Apr. 7, 2000, and 60/164,344, filed Nov. 9, 1999; U.S. application Ser. No. 10/100,683 is a continuation-in-part of International Application No. PCT/US00/30654, filed Nov. 8, 2000, which claims the benefit of U.S. Provisional Application Nos. 60/221,142, filed Jul. 27, 2000, and 60/164,835, filed Nov. 12, 1999; U.S. application Ser. No. 10/100,683 is a continuation-in-part of International Application No. PCT/US00/30628, filed Nov. 8, 2000, which claims the benefit of U.S. Provisional Application Nos. 60/215,140, filed Jun. 30, 2000, and 60/164,744, filed Nov. 12, 1999; U.S. application Ser. No. 10/100,683 is a continuation-in-part of International Application No. PCT/US00/30653, filed Nov. 8, 2000, which claims the benefit of U.S. Provisional Application Nos. 60/221,193, filed Jul. 27, 2000, and 60/164,735, filed Nov. 12, 1999; U.S. application Ser. No. 10/100,683 is a continuation-in-part of International Application No. PCT/US00/30629, filed Nov. 8, 2000, which claims the benefit of U.S. Provisional Application Nos. 60/222,904, filed Aug. 3, 2000, and 60/164,825, filed Nov. 12, 1999; U.S. application Ser. No. 10/100,683 is a continuation-in-part of International Application No. PCT/US00/30679, filed Nov. 8, 2000, which claims the benefit of U.S. Provisional Application Nos. 60/224,007, filed Aug. 4, 2000, and 60/164,834, filed Nov. 12, 1999; U.S. application Ser. No. 10/100,683 is a continuation-in-part of International Application No. PCT/US00/30674, filed Nov. 8, 2000, which claims the benefit of U.S. Provisional Application Nos. 60/215,128, filed Jun. 30, 2000, and 60/164,750, filed Nov. 12, 1999; U.S. application Ser. No. 10/100,683 is a continuation-in-part of International Application No. PCT/US00/31162, filed Nov. 15, 2000; U.S. Provisional Application No. 60/215,136 claims the benefit of U.S. Provisional Application Nos. 60/215,136, filed Jun. 30, 2000, which claims the benefit of U.S. Provisional Application No. 60/166,415, filed Nov. 19, 1999; U.S. application Ser. No. 10/100,683 is a continuation-in-part of International Application No. PCT/US00/31282, filed Nov. 15, 2000, which claims the benefit of U.S. Provisional Application Nos. 60/219,665, filed Jul. 21, 2000, and 60/166,414, filed Nov. 19, 1999; U.S. application Ser. No. 10/100,683 is a continuation-in-part of International Application No. PCT/US00/30657, filed Nov. 8, 2000, which claims the benefit of U.S. Provisional Application Nos. 60/215,132, filed Jun. 30, 2000, and 60/164,731, filed Nov. 12, 1999; U.S. application Ser. No. 10/100,683 is a continuation-in-part of International Application No. PCT/US01/01396, filed Jan. 17, 2001; U.S. Provisional Application No. 60/256,968 claims the benefit of U.S. Provisional Application Nos. 60/256,968, filed Dec. 21, 2000, which claims the benefit of U.S. Provisional Application No. 60/226,280, filed Aug. 18, 2000; U.S. application Ser. No. 10/100,683 is a continuation-in-part of International Application No. PCT/US01/01387, filed Jan. 17, 2001; U.S. Provisional Application No. 60/259,803 claims the benefit of U.S. Provisional Application Nos. 60/259,803, filed Jan. 5, 2001, which claims the benefit of U.S. Provisional Application No. 60/226,380, filed Aug. 18, 2000; U.S. application Ser. No. 10/100,683 is a continuation-in-part of International Application No. PCT/US01/01567, filed Jan. 17, 2001, which claims the benefit of U.S. Provisional Application No. 60/228,084, filed Aug. 28, 2000; U.S. application Ser. No. 10/100,683 is a continuation-in-part of International Application No. PCT/US01/01431, filed Jan. 17, 2001, which claims the benefit of U.S. Provisional Application No. 60/231,968, filed Sep. 12, 2000; International Application No. PCMS01/01431 is a continuation-in-part of U.S. application Ser. No. 09/915,582, filed Jul. 27, 2001; U.S. application Ser. No. 10/100,683 is a continuation-in-part of International Application No. PCT/US01/01432, filed Jan. 17, 2001, which claims the benefit of U.S. Provisional Application No. 60/236,326, filed Sep. 29, 2000; U.S. application Ser. No. 10/100,683 is a continuation-in-part of International Application No. PCT/US01/00544, filed Jan. 9, 2001, which claims the benefit of U.S. Provisional Application No. 60/234,211, filed Sep. 20, 2000; U.S. application Ser. No. 10/100,683 is a continuation-in-part of International Application No. PCT/US01/01435, filed Jan. 17, 2001, which claims the benefit of U.S. Provisional Application No. 60/226,282, filed Aug. 18, 2000; U.S. application Ser. No. 10/100,683 is a continuation-in-part of International Application No. PCT/US01/01386, filed Jan. 17, 2001, which claims the benefit of U.S. Provisional Application No. 60/232,104, filed Sep. 12, 2000; U.S. application Ser. No. 10/100,683 is a continuation-in-part of International Application No. PCT/US01/01565, filed Jan. 17, 2001, which claims the benefit of U.S. Provisional Application No. 60/234,210, filed Sep. 20, 2000; U.S. application Ser. No. 10/100,683 is a continuation-in-part of International Application No. PCT/US01/01394, filed Jan. 17, 2001, which claims the benefit of U.S. Provisional Application Nos. 60/259,805, filed Jan. 5, 2001, and 60/226,278, filed Aug. 18, 2000; U.S. application Ser. No. 10/100,683 is a continuation-in-part of International Application No. PCT/US01/01434, filed Jan. 17, 2001, which claims the benefit of U.S. Provisional Application Nos. 60/259,678, filed Jan. 5, 2001, and 60/226,279, filed Aug. 18, 2000; U.S. application Ser. No. 10/100,683 is a continuation-in-part of International Application No. PCT/US01/01397, filed Jan. 17, 2001, which claims the benefit of U.S. Provisional Application No. 60/226,281, filed Aug. 18, 2000; U.S. application Ser. No. 10/100,683 is a continuation-in-part of International Application No. PCT/US01/01385, filed Jan. 17, 2001, which claims the benefit of U.S. Provisional Application No. 60/231,969, filed Sep. 12, 2000; U.S. application Ser. No. 10/100,683 is a continuation-in-part of International Application No. PCT/US01/01384, filed Jan. 17, 2001, which claims the benefit of U.S. Provisional Application Nos. 60/259,516, filed Jan. 4, 2001, and 60/228,086, filed Aug. 28, 2000; U.S. application Ser. No. 10/100,683 is a continuation-in-part of International Application No. PCT/US01/01383, filed Jan. 17, 2001, which claims the benefit of U.S. Provisional Application Nos. 60/259,804, filed Jan. 5, 2001, and 60/228,083, filed Aug. 28, 2000; U.S. application Ser. No. 10/100,683 is a continuation-in-part of International Application No. PCT/US02/05064, filed Feb. 21, 2002, which claims the benefit of U.S. Provisional Application Nos. 60/304,444, filed Jul. 12, 2001, and 60/270,658, filed Feb. 23, 2001; U.S. application Ser. No. 10/100,683 is a continuation-in-part of International Application No. PCT/US02/05301, filed Feb. 21, 2002, which claims the benefit of U.S. Provisional Application Nos. 60/304,417, filed Jul. 12, 2001, and 60/270,625, filed Feb. 23, 2001; U.S. application Ser. No. 10/100,683 claims the benefit of U.S. Provisional Application Nos. 60/304,121, filed Jul. 11, 2001, 60/295,869, filed Jun. 6, 2001, 60/325,209, filed Sep. 28, 2001, 60/311,085, filed Aug. 10, 2001, 60/330,629, filed Oct. 26, 2001, 60/331,046, filed Nov. 7, 2001, 60/358,554, filed Feb. 22, 2002, and 60/358,714, filed Feb. 25, 2002. This application is a continuation-in-part of U.S. application Ser. No. 11/687,755, filed Mar. 19, 2007, which is a divisional of U.S. patent application Ser. No. 10/664,356, filed Sep. 20, 2003, which is a continuation-in-part of PCT/US02/08123, filed Mar. 19, 2002, which is a continuation-in-part of U.S. application Ser. No. 10/100,683, filed Mar. 19, 2002, which claims the benefit of U.S. Provisional Application Nos. 60/277,340, filed Mar. 21, 2001, 60/306,171, filed Jul. 19, 2001, and 60/331,287, filed Nov. 13, 2001; U.S. application Ser. No. 10/100,683 is a continuation-in-part of U.S. application Ser. No. 09/981,876, filed Oct. 19, 2001, which is a divisional of U.S. application Ser. No. 09/621,011, filed Jul. 20, 2000, which is a continuation of U.S. application Ser. No. 09/148,545, filed Sep. 4, 1998, which is a continuation-in-part of International Application No. PCT/US98/04482, filed Mar. 6, 1998; U.S. application Ser. No. 10/100,683 is a continuation-in-part of U.S. application Ser. No. 09/621,011, filed Jul. 20, 2000, which is a continuation of U.S. application Ser. No. 09/148,545, filed Sep. 4, 1998, which is a continuation-in-part of International Application No. PCT/US98/04482, filed Mar. 6, 1998; U.S. application Ser. No. 10/100,683 is a continuation-in-part of U.S. application Ser. No. 09/148,545, filed Sep. 4, 1998, which is a continuation-in-part of International Application No. PCT/US98/04482, filed Mar. 6, 1998; U.S. application Ser. No. 10/100,683 is a continuation-in-part of International Application No. PCT/US98/04482, filed Mar. 6, 1998, which claims the benefit of U.S. Provisional Application Nos. 60/040,162, filed Mar. 7, 1997, 60/040,333, filed Mar. 7, 1997, 60/038,621, filed Mar. 7, 1997, 60/040,161, filed Mar. 7, 1997, 60/040,626, filed Mar. 7, 1997, 60/040,334, filed Mar. 7, 1997, 60/040,336, filed Mar. 7, 1997, 60/040,163, filed Mar. 7, 1997, 60/047,615, filed May 23, 1997, 60/047,600, filed May 23, 1997, 60/047,597, filed May 23, 1997, 60/047,502, filed May 23, 1997, 60/047,633, filed May 23, 1997, 60/047,583, filed May 23, 1997, 60/047,617, filed May 23, 1997, 60/047,618, filed May 23, 1997, 60/047,503, filed May 23, 1997, 60/047,592, filed May 23, 1997, 60/047,581, filed May 23, 1997, 60/047,584, filed May 23, 1997, 60/047,500, filed May 23, 1997, 60/047,587, filed May 23, 1997, 60/047,492, filed May 23, 1997, 60/047,598, filed May 23, 1997, 60/047,613, filed May 23, 1997, 60/047,582, filed May 23, 1997, 60/047,596, filed May 23, 1997, 60/047,612, filed May 23, 1997, 60/047,632, filed May 23, 1997, 60/047,601, filed May 23, 1997, 60/043,580, filed Apr. 11, 1997, 60/043,568, filed Apr. 11, 1997, 60/043,314, filed Apr. 11, 1997, 60/043,569, filed Apr. 11, 1997, 60/043,311, filed Apr. 11, 1997, 60/043,671, filed Apr. 11, 1997, 60/043,674, filed Apr. 11, 1997, 60/043,669, filed Apr. 11, 1997, 60/043,312, filed Apr. 11, 1997, 60/043,313, filed Apr. 11, 1997, 60/043,672, filed Apr. 11, 1997, 60/043,315, filed Apr. 11, 1997, 60/048,974, filed Jun. 6, 1997, 60/056,886, filed Aug. 22, 1997, 60/056,877, filed Aug. 22, 1997, 60/056,889, filed Aug. 22, 1997, 60/056,893, filed Aug. 22, 1997, 60/056,630, filed Aug. 22, 1997, 60/056,878, filed Aug. 22, 1997, 60/056,662, filed Aug. 22, 1997, 60/056,872, filed Aug. 22, 1997, 60/056,882, filed Aug. 22, 1997, 60/056,637, filed Aug. 22, 1997, 60/056,903, filed Aug. 22, 1997, 60/056,888, filed Aug. 22, 1997, 60/056,879, filed Aug. 22, 1997, 60/056,880, filed Aug. 22, 1997, 60/056,894, filed Aug. 22, 1997, 60/056,911, filed Aug. 22, 1997, 60/056,636, filed Aug. 22, 1997, 60/056,874, filed Aug. 22, 1997, 60/056,910, filed Aug. 22, 1997, 60/056,864, filed Aug. 22, 1997, 60/056,631, filed Aug. 22, 1997, 60/056,845, filed Aug. 22, 1997, 60/056,892, filed Aug. 22, 1997, 60/047,595, filed May 23, 1997, 60/057,761, filed Sep. 5, 1997, 60/047,599, filed May 23, 1997, 60/047,588, filed May 23, 1997, 60/047,585, filed May 23, 1997, 60/047,586, filed May 23, 1997, 60/047,590, filed May 23, 1997, 60/047,594, filed May 23, 1997, 60/047,589, filed May 23, 1997, 60/047,593, filed May 23, 1997, 60/047,614, filed May 23, 1997, 60/043,578, filed Apr. 11, 1997, 60/043,576, filed Apr. 11, 1997, 60/047,501, filed May 23, 1997, 60/043,670, filed Apr. 11, 1997, 60/056,632, filed Aug. 22, 1997, 60/056,664, filed Aug. 22, 1997, 60/056,876, filed Aug. 22, 1997, 60/056,881, filed Aug. 22, 1997, 60/056,909, filed Aug. 22, 1997, 60/056,875, filed Aug. 22, 1997, 60/056,862, filed Aug. 22, 1997, 60/056,887, filed Aug. 22, 1997, 60/056,908, filed Aug. 22, 1997, 60/048,964, filed Jun. 6, 1997, 60/057,650, filed Sep. 5, 1997, and 60/056,884, filed Aug. 22, 1997; U.S. application Ser. No. 10/100,683 is a continuation-in-part of U.S. application Ser. No. 09/882,171, filed Jun. 18, 2001, which claims the benefit of U.S. Provisional Application No. 60/190,068, filed Mar. 17, 2000; U.S. application Ser. No. 09/882,171 is a continuation of U.S. application Ser. No. 09/809,391, filed Mar. 16, 2001, which is a continuation-in-part of U.S. application Ser. No. 09/149,476, filed Sep. 8, 1998, which is a continuation-in-part of International Application No. PCT/US98/04493, filed Mar. 6, 1998; U.S. application Ser. No. 10/100,683 is a continuation-in-part of U.S. application Ser. No. 09/809,391, filed Mar. 16, 2001, which claims the benefit of U.S. Provisional Application No. 60/190,068, filed Mar. 17, 2000; U.S. application Ser. No. 09/809,391 is a continuation-in-part of U.S. application Ser. No. 09/149,476, filed Sep. 8, 1998, which is a continuation-in-part of International Application No. PCT/US98/04493, filed Mar. 6, 1998; U.S. application Ser. No. 10/100,683 is a continuation-in-part of U.S. application Ser. No. 09/149,476, filed Sep. 8, 1998, which is a continuation-in-part of International Application No. PCT/US98/04493, filed Mar. 6, 1998; U.S. application Ser. No. 10/100,683 is a continuation-in-part of International Application No. PCT/US98/04493, filed Mar. 6, 1998, which claims the benefit of U.S. Provisional Application Nos. 60/040,161, filed Mar. 7, 1997, 60/040,162, filed Mar. 7, 1997, 60/040,333, filed Mar. 7, 1997, 60/038,621, filed Mar. 7, 1997, 60/040,626, filed Mar. 7, 1997, 60/040,334, filed Mar. 7, 1997, 60/040,336, filed Mar. 7, 1997, 60/040,163, filed Mar. 7, 1997, 60/047,600, filed May 23, 1997, 60/047,615, filed May 23, 1997, 60/047,597, filed May 23, 1997, 60/047,502, filed May 23, 1997, 60/047,633, filed May 23, 1997, 60/047,583, filed May 23, 1997, 60/047,617, filed May 23, 1997, 60/047,618, filed May 23, 1997, 60/047,503, filed May 23, 1997, 60/047,592, filed May 23, 1997, 60/047,581, filed May 23, 1997, 60/047,584, filed May 23, 1997, 60/047,500, filed May 23, 1997, 60/047,587, filed May 23, 1997, 60/047,492, filed May 23, 1997, 60/047,598, filed May 23, 1997, 60/047,613, filed May 23, 1997, 60/047,582, filed May 23, 1997, 60/047,596, filed May 23, 1997, 60/047,612, filed May 23, 1997, 60/047,632, filed May 23, 1997, 60/047,601, filed May 23, 1997, 60/043,580, filed Apr. 11, 1997, 60/043,568, filed Apr. 11, 1997, 60/043,314, filed Apr. 11, 1997, 60/043,569, filed Apr. 11, 1997, 60/043,311, filed Apr. 11, 1997, 60/043,671, filed Apr. 11, 1997, 60/043,674, filed Apr. 11, 1997, 60/043,669, filed Apr. 11, 1997, 60/043,312, filed Apr. 11, 1997, 60/043,313, filed Apr. 11, 1997, 60/043,672, filed Apr. 11, 1997, 60/043,315, filed Apr. 11, 1997, 60/048,974, filed Jun. 6, 1997, 60/056,886, filed Aug. 22, 1997, 60/056,877, filed Aug. 22, 1997, 60/056,889, filed Aug. 22, 1997, 60/056,893, filed Aug. 22, 1997, 60/056,630, filed Aug. 22, 1997, 60/056,878, filed Aug. 22, 1997, 60/056,662, filed Aug. 22, 1997, 60/056,872, filed Aug. 22, 1997, 60/056,882, filed Aug. 22, 1997, 60/056,637, filed Aug. 22, 1997, 60/056,903, filed Aug. 22, 1997, 60/056,888, filed Aug. 22, 1997, 60/056,879, filed Aug. 22, 1997, 60/056,880, filed Aug. 22, 1997, 60/056,894, filed Aug. 22, 1997, 60/056,911, filed Aug. 22, 1997, 60/056,636, filed Aug. 22, 1997, 60/056,874, filed Aug. 22, 1997, 60/056,910, filed Aug. 22, 1997, 60/056,864, filed Aug. 22, 1997, 60/056,631, filed Aug. 22, 1997, 60/056,845, filed Aug. 22, 1997, 60/056,892, filed Aug. 22, 1997, 60/057,761, filed Sep. 5, 1997, 60/047,595, filed May 23, 1997, 60/047,599, filed May 23, 1997, 60/047,588, filed May 23, 1997, 60/047,585, filed May 23, 1997, 60/047,586, filed May 23, 1997, 60/047,590, filed May 23, 1997, 60/047,594, filed May 23, 1997, 60/047,589, filed May 23, 1997, 60/047,593, filed May 23, 1997, 60/047,614, filed May 23, 1997, 60/043,578, filed Apr. 11, 1997, 60/043,576, filed Apr. 11, 1997, 60/047,501, filed May 23, 1997, 60/043,670, filed Apr. 11, 1997, 60/056,632, filed Aug. 22, 1997, 60/056,664, filed Aug. 22, 1997, 60/056,876, filed Aug. 22, 1997, 60/056,881, filed Aug. 22, 1997, 60/056,909, filed Aug. 22, 1997, 60/056,875, filed Aug. 22, 1997, 60/056,862, filed Aug. 22, 1997, 60/056,887, filed Aug. 22, 1997, 60/056,908, filed Aug. 22, 1997, 60/048,964, filed Jun. 6, 1997, 60/057,650, filed Sep. 5, 1997, 60/056,884, filed Aug. 22, 1997, 60/057,669, filed Sep. 5, 1997, 60/049,610, filed Jun. 13, 1997, 60/061,060, filed Oct. 2, 1997, 60/051,926, filed Jul. 8, 1997, 60/052,874, filed Jul. 16, 1997, 60/058,785, filed Sep. 12, 1997, and 60/055,724, filed Aug. 18, 1997; U.S. application Ser. No. 10/100,683 is a continuation-in-part of U.S. application Ser. No. 10/058,993, filed Jan. 30, 2002, which claims the benefit of U.S. Provisional Application No. 60/265,583, filed Feb. 2, 2001; U.S. application Ser. No. 10/058,993 is a continuation-in-part of U.S. application Ser. No. 09/852,659, filed May 11, 2001, which is a continuation-in-part of U.S. application Ser. No. 09/152,060, filed Sep. 11, 1998, which is a continuation-in-part of International Application No. PCT/US98/04858, filed Mar. 12, 1998; U.S. application Ser. No. 10/058,993 is a continuation-in-part of U.S. application Ser. No. 09/853,161, filed May 11, 2001, which is a continuation-in-part of U.S. application Ser. No. 09/152,060, filed Sep. 11, 1998, which is a continuation-in-part of International Application No. PCT/US98/04858, filed Mar. 12, 1998; U.S. application Ser. No. 10/058,993 is a continuation-in-part of U.S. application Ser. No. 09/852,797, filed May 11, 2001, which is a continuation-in-part of U.S. application Ser. No. 09/152,060, filed Sep. 11, 1998, which is a continuation-in-part of International Application No. PCT/US98/04858, filed Mar. 12, 1998; U.S. application Ser. No. 10/100,683 is a continuation-in-part of U.S. application Ser. No. 09/852,659, filed May 11, 2001, which claims the benefit of U.S. Provisional Application No. 60/265,583, filed Feb. 2, 2001; U.S. application Ser. No. 09/852,659 is a continuation-in-part of U.S. application Ser. No. 09/152,060, filed Sep. 11, 1998, which is a continuation-in-part of International Application No. PCT/US98/04858, filed Mar. 12, 1998; U.S. application Ser. No. 10/100,683 is a continuation-in-part of U.S. application Ser. No. 09/853,161, filed May 11, 2001, which claims the benefit of U.S. Provisional Application No. 60/265,583, filed Feb. 2, 2001; U.S. application Ser. No. 09/853,161 is a continuation-in-part of U.S. application Ser. No. 09/152,060, filed Sep. 11, 1998, which is a continuation-in-part of International Application No. PCT/US98/04858, filed Mar. 12, 1998; U.S. application Ser. No. 10/100,683 is a continuation-in-part of U.S. application Ser. No. 09/852,797, filed May 11, 2001, which claims the benefit of U.S. Provisional Application No. 60/265,583, filed Feb. 2, 2001; U.S. application Ser. No. 09/852,797 is a continuation-in-part of U.S. application Ser. No. 09/152,060, filed Sep. 11, 1998, which is a continuation-in-part of International Application No. PCT/US98/04858, filed Mar. 12, 1998; U.S. application Ser. No. 10/100,683 is a continuation-in-part of U.S. application Ser. No. 09/152,060, filed Sep. 11, 1998, which is a continuation-in-part of International Application No. PCT/US98/04858, filed Mar. 12, 1998; U.S. application Ser. No. 10/100,683 is a continuation-in-part of International Application No. PCT/US98/04858, filed Mar. 12, 1998, which claims the benefit of U.S. Provisional Application Nos. 60/040,762, filed Mar. 14, 1997, 60/040,710, filed Mar. 14, 1997, 60/050,934, filed May 30, 1997, 60/048,100, filed May 30, 1997, 60/048,357, filed May 30, 1997, 60/048,189, filed May 30, 1997, 60/057,765, filed Sep. 5, 1997, 60/048,970, filed Jun. 6, 1997, and 60/068,368, filed Dec. 19, 1997; U.S. application Ser. No. 10/100,683 is a continuation-in-part of U.S. application Ser. No. 10/059,395, filed Jan. 31, 2002, which is a divisional of U.S. application Ser. No. 09/966,262, filed Oct. 1, 2001, which is a continuation of U.S. application Ser. No. 09/154,707, filed Sep. 17, 1998, which is a continuation-in-part of International Application No. PCT/US98/05311, filed Mar. 19, 1998; U.S. application Ser. No. 10/100,683 is a continuation-in-part of U.S. application Ser. No. 09/984,245, filed Oct. 29, 2001, which is a divisional of U.S. application Ser. No. 09/154,707, filed Sep. 17, 1998, which is a continuation-in-part of International Application No. PCT/US98/05311, filed Mar. 19, 1998; U.S. application Ser. No. 10/100,683 is a continuation-in-part of U.S. application Ser. No. 09/983,966, filed Oct. 26, 2001, which is a divisional of U.S. application Ser. No. 09/154,707, filed Sep. 17, 1998, which is a continuation-in-part of International Application No. PCT/US98/05311, filed Mar. 19, 1998; U.S. application Ser. No. 10/100,683 is a continuation-in-part of U.S. application Ser. No. 09/966,262, filed Oct. 1, 2001, which is a continuation of U.S. application Ser. No. 09/154,707, filed Sep. 17, 1998, which is a continuation-in-part of International Application No. PCT/US98/05311, filed Mar. 19, 1998; U.S. application Ser. No. 10/100,683 is a continuation-in-part of U.S. application Ser. No. 09/154,707, filed Sep. 17, 1998, which is a continuation-in-part of International Application No. PCT/US98/05311, filed Mar. 19, 1998; U.S. application Ser. No. 10/100,683 is a continuation-in-part of International Application No. PCT/US98/05311, filed Mar. 19, 1998, which claims the benefit of U.S. Provisional Application Nos. 60/041,277, filed Mar. 21, 1997, 60/042,344, filed Mar. 21, 1997, 60/041,276, filed Mar. 21, 1997, 60/041,281, filed Mar. 21, 1997, 60/048,094, filed May 30, 1997, 60/048,350, filed May 30, 1997, 60/048,188, filed May 30, 1997, 60/048,135, filed May 30, 1997, 60/050,937, filed May 30, 1997, 60/048,187, filed May 30, 1997, 60/048,099, filed May 30, 1997, 60/048,352, filed May 30, 1997, 60/048,186, filed May 30, 1997, 60/048,069, filed May 30, 1997, 60/048,095, filed May 30, 1997, 60/048,131, filed May 30, 1997, 60/048,096, filed May 30, 1997, 60/048,355, filed May 30, 1997, 60/048,160, filed May 30, 1997, 60/048,351, filed May 30, 1997, 60/048,154, filed May 30, 1997, 60/054,804, filed Aug. 5, 1997, 60/056,370, filed Aug. 19, 1997, and 60/060,862, filed Oct. 2, 1997; U.S. application Ser. No. 10/100,683 is a continuation-in-part of U.S. application Ser. No. 09/814,122, filed Mar. 22, 2001, which is a continuation of U.S. application Ser. No. 09/577,145, filed May 24, 2000, which is a continuation of U.S. application Ser. No. 09/166,780, filed Oct. 6, 1998, which is a continuation-in-part of International Application No. PCT/US98/06801, filed Apr. 7, 1998; U.S. application Ser. No. 10/100,683 is a continuation-in-part of International Application No. PCT/US98/06801, filed Apr. 7, 1998, which claims the benefit of U.S. Provisional Application Nos. 60/042,726, filed Apr. 8, 1997, 60/042,727, filed Apr. 8, 1997, 60/042,728, filed Apr. 8, 1997, 60/042,754, filed Apr. 8, 1997, 60/042,825, filed Apr. 8, 1997, 60/048,068, filed May 30, 1997, 60/048,070, filed May 30, 1997, and 60/048,184, filed May 30, 1997; U.S. application Ser. No. 10/100,683 is a continuation-in-part of International Application No. PCT/US98/06801, filed Apr. 7, 1998, which claims the benefit of U.S. Provisional Application Nos. 60/042,726, filed Apr. 8, 1997, 60/042,727, filed Apr. 8, 1997, 60/042,728, filed Apr. 8, 1997, 60/042,754, filed Apr. 8, 1997, 60/042,825, filed Apr. 8, 1997, 60/048,068, filed May 30, 1997, 60/048,070, filed May 30, 1997, and 60/048,184, filed May 30, 1997; U.S. application Ser. No. 10/100,683 is a continuation-in-part of International Application No. PCT/US98/10868, filed May 28, 1998, which claims the benefit of U.S. Provisional Application Nos. 60/044,039, filed May 30, 1997, 60/048,093, filed May 30, 1997, 60/048,190, filed May 30, 1997, 60/050,935, filed May 30, 1997, 60/048,101, filed May 30, 1997, 60/048,356, filed May 30, 1997, 60/056,250, filed Aug. 29, 1997, 60/056,296, filed Aug. 29, 1997, and 60/056,293, filed Aug. 29, 1997; U.S. application Ser. No. 10/100,683 is a continuation-in-part of International Application No. PCT/US98/11422, filed Jun. 4, 1998, which claims the benefit of U.S. Provisional Application Nos. 60/048,885, filed Jun. 6, 1997, 60/049,375, filed Jun. 6, 1997, 60/048,881, filed Jun. 6, 1997, 60/048,880, filed Jun. 6, 1997, 60/048,896, filed Jun. 6, 1997, 60/049,020, filed Jun. 6, 1997, 60/048,876, filed Jun. 6, 1997, 60/048,895, filed Jun. 6, 1997, 60/048,884, filed Jun. 6, 1997, 60/048,894, filed Jun. 6, 1997, 60/048,971, filed Jun. 6, 1997, 60/048,964, filed Jun. 6, 1997, 60/048,882, filed Jun. 6, 1997, 60/048,899, filed Jun. 6, 1997, 60/048,893, filed Jun. 6, 1997, 60/048,900, filed Jun. 6, 1997, 60/048,901, filed Jun. 6, 1997, 60/048,892, filed Jun. 6, 1997, 60/048,915, filed Jun. 6, 1997, 60/049,019, filed Jun. 6, 1997, 60/048,970, filed Jun. 6, 1997, 60/048,972, filed Jun. 6, 1997, 60/048,916, filed Jun. 6, 1997, 60/049,373, filed Jun. 6, 1997, 60/048,875, filed Jun. 6, 1997, 60/049,374, filed Jun. 6, 1997, 60/048,917, filed Jun. 6, 1997, 60/048,949, filed Jun. 6, 1997, 60/048,974, filed Jun. 6, 1997, 60/048,883, filed Jun. 6, 1997, 60/048,897, filed Jun. 6, 1997, 60/048,898, filed Jun. 6, 1997, 60/048,962, filed Jun. 6, 1997, 60/048,963, filed Jun. 6, 1997, 60/048,877, filed Jun. 6, 1997, 60/048,878, filed Jun. 6, 1997, 60/057,645, filed Sep. 5, 1997, 60/057,642, filed Sep. 5, 1997, 60/057,668, filed Sep. 5, 1997, 60/057,635, filed Sep. 5, 1997, 60/057,627, filed Sep. 5, 1997, 60/057,667, filed Sep. 5, 1997, 60/057,666, filed Sep. 5, 1997, 60/057,764, filed Sep. 5, 1997, 60/057,643, filed Sep. 5, 1997, 60/057,769, filed Sep. 5, 1997, 60/057,763, filed Sep. 5, 1997, 60/057,650, filed Sep. 5, 1997, 60/057,584, filed Sep. 5, 1997, 60/057,647, filed Sep. 5, 1997, 60/057,661, filed Sep. 5, 1997, 60/057,662, filed Sep. 5, 1997, 60/057,646, filed Sep. 5, 1997, 60/057,654, filed Sep. 5, 1997, 60/057,651, filed Sep. 5, 1997, 60/057,644, filed Sep. 5, 1997, 60/057,765, filed Sep. 5, 1997, 60/057,762, filed Sep. 5, 1997, 60/057,775, filed Sep. 5, 1997, 60/057,648, filed Sep. 5, 1997, 60/057,774, filed Sep. 5, 1997, 60/057,649, filed Sep. 5, 1997, 60/057,770, filed Sep. 5, 1997, 60/057,771, filed Sep. 5, 1997, 60/057,761, filed Sep. 5, 1997, 60/057,760, filed Sep. 5, 1997, 60/057,776, filed Sep. 5, 1997, 60/057,778, filed Sep. 5, 1997, 60/057,629, filed Sep. 5, 1997, 60/057,628, filed Sep. 5, 1997, 60/057,777, filed Sep. 5, 1997, 60/057,634, filed Sep. 5, 1997, and 60/070,923, filed Dec. 18, 1997; U.S. application Ser. No. 10/100,683 is a continuation-in-part of International Application No. PCT/US01/05614, filed Feb. 21, 2001, which claims the benefit of U.S. Provisional Application Nos. 60/184,836, filed Feb. 24, 2000, and 60/193,170, filed Mar. 29, 2000; U.S. application Ser. No. 10/100,683 is a continuation-in-part of International Application No. PCT/US98/12125, filed Jun. 11, 1998, which claims the benefit of U.S. Provisional Application Nos. 60/049,547, filed Jun. 13, 1997, 60/049,548, filed Jun. 13, 1997, 60/049,549, filed Jun. 13, 1997, 60/049,550, filed Jun. 13, 1997, 60/049,566, filed Jun. 13, 1997, 60/049,606, filed Jun. 13, 1997, 60/049,607, filed Jun. 13, 1997, 60/049,608, filed Jun. 13, 1997, 60/049,609, filed Jun. 13, 1997, 60/049,610, filed Jun. 13, 1997, 60/049,611, filed Jun. 13, 1997, 60/050,901, filed Jun. 13, 1997, 60/052,989, filed Jun. 13, 1997, 60/051,919, filed Jul. 8, 1997, 60/055,984, filed Aug. 18, 1997, 60/058,665, filed Sep. 12, 1997, 60/058,668, filed Sep. 12, 1997, 60/058,669, filed Sep. 12, 1997, 60/058,750, filed Sep. 12, 1997, 60/058,971, filed Sep. 12, 1997, 60/058,972, filed Sep. 12, 1997, 60/058,975, filed Sep. 12, 1997, 60/060,834, filed Oct. 2, 1997, 60/060,841, filed Oct. 2, 1997, 60/060,844, filed Oct. 2, 1997, 60/060,865, filed Oct. 2, 1997, 60/061,059, filed Oct. 2, 1997, and 60/061,060, filed Oct. 2, 1997; U.S. application Ser. No. 10/100,683 is a continuation-in-part of U.S. application Ser. No. 09/627,081, filed Jul. 27, 2000, which is a continuation of U.S. application Ser. No. 09/213,365, filed Dec. 17, 1998, which is a continuation-in-part of International Application No. PCT/US98/13608, filed Jun. 30, 1998; U.S. application Ser. No. 10/100,683 is a continuation-in-part of International Application No. PCT/US98/13608, filed Jun. 30, 1998, which claims the benefit of U.S. Provisional Application Nos. 60/051,480, filed Jul. 1, 1997, 60/051,381, filed Jul. 1, 1997, 60/058,663, filed Sep. 12, 1997, and 60/058,598, filed Sep. 12, 1997; U.S. application Ser. No. 10/100,683 is a continuation-in-part of U.S. application Ser. No. 09/984,490, filed Oct. 30, 2001, which is a divisional of U.S. application Ser. No. 09/227,357, filed Jan. 8, 1999, which is a continuation-in-part of International Application No. PCT/US98/13684, filed Jul. 7, 1998; U.S. application Ser. No. 10/100,683 is a continuation-in-part of U.S. application Ser. No. 09/983,802, filed Oct. 25, 2001, which is a continuation of U.S. application Ser. No. 09/227,357, filed Jan. 8, 1999, which is a continuation-in-part of International Application No. PCT/US98/13684, filed Jul. 7, 1998; U.S. application Ser. No. 10/100,683 is a continuation-in-part of U.S. application Ser. No. 09/973,278, filed Oct. 10, 2001, which claims the benefit of U.S. Provisional Application No. 60/239,899, filed Oct. 13, 2000; U.S. application Ser. No. 09/973,278 is a continuation-in-part of U.S. application Ser. No. 09/227,357, filed Jan. 8, 1999, which is a continuation-in-part of International Application No. PCT/US98/13684, filed Jul. 7, 1998; U.S. application Ser. No. 10/100,683 is a continuation-in-part of International Application No. PCT/US98/13684, filed Jul. 7, 1998, which claims the benefit of U.S. Provisional Application Nos. 60/051,926, filed Jul. 8, 1997, 60/052,793, filed Jul. 8, 1997, 60/051,925, filed Jul. 8, 1997, 60/051,929, filed Jul. 8, 1997, 60/052,803, filed Jul. 8, 1997, 60/052,732, filed Jul. 8, 1997, 60/051,931, filed Jul. 8, 1997, 60/051,932, filed Jul. 8, 1997, 60/051,916, filed Jul. 8, 1997, 60/051,930, filed Jul. 8, 1997, 60/051,918, filed Jul. 8, 1997, 60/051,920, filed Jul. 8, 1997, 60/052,733, filed Jul. 8, 1997, 60/052,795, filed Jul. 8, 1997, 60/051,919, filed Jul. 8, 1997, 60/051,928, filed Jul. 8, 1997, 60/055,722, filed Aug. 18, 1997, 60/055,723, filed Aug. 18, 1997, 60/055,948, filed Aug. 18, 1997, 60/055,949, filed Aug. 18, 1997, 60/055,953, filed Aug. 18, 1997, 60/055,950, filed Aug. 18, 1997, 60/055,947, filed Aug. 18, 1997, 60/055,964, filed Aug. 18, 1997, 60/056,360, filed Aug. 18, 1997, 60/055,684, filed Aug. 18, 1997, 60/055,984, filed Aug. 18, 1997, 60/055,954, filed Aug. 18, 1997, 60/058,785, filed Sep. 12, 1997, 60/058,664, filed Sep. 12, 1997, 60/058,660, filed Sep. 12, 1997, and 60/058,661, filed Sep. 12, 1997; U.S. application Ser. No. 10/100,683 is a continuation-in-part of U.S. application Ser. No. 09/776,724, filed Feb. 6, 2001, which claims the benefit of U.S. Provisional Application No. 60/180,909, filed Feb. 8, 2000; U.S. application Ser. No. 09/776,724 is a continuation-in-part of U.S. application Ser. No. 09/669,688, filed Sep. 26, 2000, which is a continuation of U.S. application Ser. No. 09/229,982, filed Jan. 14, 1999, which is a continuation-in-part of International Application No. PCT/US98/14613, filed Jul. 15, 1998; U.S. application Ser. No. 10/100,683 is a continuation-in-part of U.S. application Ser. No. 09/669,688, filed Sep. 26, 2000, which is a continuation of U.S. application Ser. No. 09/229,982, filed Jan. 14, 1999, which is a continuation-in-part of International Application No. PCT/US98/14613, filed Jul. 15, 1998; U.S. application Ser. No. 10/100,683 is a continuation-in-part of U.S. application Ser. No. 09/229,982, filed Jan. 14, 1999, which is a continuation-in-part of International Application No. PCT/US98/14613, filed Jul. 15, 1998; U.S. application Ser. No. 10/100,683 is a continuation-in-part of International Application No. PCT/US98/14613, filed Jul. 15, 1998, which claims the benefit of U.S. Provisional Application Nos. 60/052,661, filed Jul. 16, 1997, 60/052,872, filed Jul. 16, 1997, 60/052,871, filed Jul. 16, 1997, 60/052,874, filed Jul. 16, 1997, 60/052,873, filed Jul. 16, 1997, 60/052,870, filed Jul. 16, 1997, 60/052,875, filed Jul. 16, 1997, 60/053,440, filed Jul. 22, 1997, 60/053,441, filed Jul. 22, 1997, 60/053,442, filed Jul. 22, 1997, 60/056,359, filed Aug. 18, 1997, 60/055,725, filed Aug. 18, 1997, 60/055,985, filed Aug. 18, 1997, 60/055,952, filed Aug. 18, 1997, 60/055,989, filed Aug. 18, 1997, 60/056,361, filed Aug. 18, 1997, 60/055,726, filed Aug. 18, 1997, 60/055,724, filed Aug. 18, 1997, 60/055,946, filed Aug. 18, 1997, and 60/055,683, filed Aug. 18, 1997; U.S. application Ser. No. 10/100,683 claims the benefit of U.S. Provisional Application No. 60/295,558, filed Jun. 5, 2001; U.S. application Ser. No. 10/100,683 is a continuation-in-part of U.S. application Ser. No. 09/820,649, filed Mar. 30, 2001, which is a continuation of U.S. application Ser. No. 09/666,984, filed Sep. 21, 2000, which is a continuation of U.S. application Ser. No. 09/236,557, filed Jan. 26, 1999, which is a continuation-in-part of International Application No. PCT/US98/15949, filed Jul. 29, 1998; U.S. application Ser. No. 10/100,683 is a continuation-in-part of International Application No. PCT/US98/15949, filed Jul. 29, 1998, which claims the benefit of U.S. Provisional Application Nos. 60/054,212, filed Jul. 30, 1997, 60/054,209, filed Jul. 30, 1997, 60/054,234, filed Jul. 30, 1997, 60/054,218, filed Jul. 30, 1997, 60/054,214, filed Jul. 30, 1997, 60/054,236, filed Jul. 30, 1997, 60/054,215, filed Jul. 30, 1997, 60/054,211, filed Jul. 30, 1997, 60/054,217, filed Jul. 30, 1997, 60/054,213, filed Jul. 30, 1997, 60/055,968, filed Aug. 18, 1997, 60/055,969, filed Aug. 18, 1997, 60/055,972, filed Aug. 18, 1997, 60/056,561, filed Aug. 19, 1997, 60/056,534, filed Aug. 19, 1997, 60/056,729, filed Aug. 19, 1997, 60/056,543, filed Aug. 19, 1997, 60/056,727, filed Aug. 19, 1997, 60/056,554, filed Aug. 19, 1997, and 60/056,730, filed Aug. 19, 1997; U.S. application Ser. No. 10/100,683 is a continuation-in-part of U.S. application Ser. No. 09/969,730, filed Oct. 4, 2001, which is a continuation-in-part of U.S. application Ser. No. 09/774,639, filed Feb. 1, 2001, which is a continuation of U.S. application Ser. No. 09/244,112, filed Feb. 4, 1999, which is a continuation-in-part of International Application No. PCT/US98/16235, filed Aug. 4, 1998; U.S. application Ser. No. 10/100,683 is a continuation-in-part of U.S. application Ser. No. 09/774,639, filed Feb. 1, 2001, which is a continuation of U.S. application Ser. No. 09/244,112, filed Feb. 4, 1999, which is a continuation-in-part of International Application No. PCT/US98/16235, filed Aug. 4, 1998; U.S. application Ser. No. 10/100,683 is a continuation-in-part of U.S. application Ser. No. 09/969,730, filed Oct. 4, 2001, which claims the benefit of U.S. Provisional Application No. 60/238,291, filed Oct. 6, 2000; U.S. application Ser. No. 10/100,683 is a continuation-in-part of International Application No. PCT/US98/16235, filed Aug. 4, 1998, which claims the benefit of U.S. Provisional Application Nos. 60/055,386, filed Aug. 5, 1997, 60/054,807, filed Aug. 5, 1997, 60/055,312, filed Aug. 5, 1997, 60/055,309, filed Aug. 5, 1997, 60/054,798, filed Aug. 5, 1997, 60/055,310, filed Aug. 5, 1997, 60/054,806, filed Aug. 5, 1997, 60/054,809, filed Aug. 5, 1997, 60/054,804, filed Aug. 5, 1997, 60/054,803, filed Aug. 5, 1997, 60/054,808, filed Aug. 5, 1997, 60/055,311, filed Aug. 5, 1997, 60/055,986, filed Aug. 18, 1997, 60/055,970, filed Aug. 18, 1997, 60/056,563, filed Aug. 19, 1997, 60/056,557, filed Aug. 19, 1997, 60/056,731, filed Aug. 19, 1997, 60/056,365, filed Aug. 19, 1997, 60/056,367, filed Aug. 19, 1997, 60/056,370, filed Aug. 19, 1997, 60/056,364, filed Aug. 19, 1997, 60/056,366, filed Aug. 19, 1997, 60/056,732, filed Aug. 19, 1997, and 60/056,371, filed Aug. 19, 1997; U.S. application Ser. No. 10/100,683 is a continuation-in-part of U.S. application Ser. No. 09/716,128, filed Nov. 17, 2000, which is a continuation of U.S. application Ser. No. 09/251,329, filed Feb. 17, 1999, which is a continuation-in-part of International Application No. PCT/US98/17044, filed Aug. 18, 1998; U.S. application Ser. No. 10/100,683 is a continuation-in-part of International Application No. PCT/US98/17044, filed Aug. 18, 1998, which claims the benefit of U.S. Provisional Application Nos. 60/056,555, filed Aug. 19, 1997, 60/056,556, filed Aug. 19, 1997, 60/056,535, filed Aug. 19, 1997, 60/056,629, filed Aug. 19, 1997, 60/056,369, filed Aug. 19, 1997, 60/056,628, filed Aug. 19, 1997, 60/056,728, filed Aug. 19, 1997, 60/056,368, filed Aug. 19, 1997, 60/056,726, filed Aug. 19, 1997, 60/089,510, filed Jun. 16, 1998, and 60/092,956, filed Jul. 15, 1998; U.S. application Ser. No. 10/100,683 is a continuation-in-part of U.S. application Ser. No. 09/729,835, filed Dec. 6, 2000, which is a divisional of U.S. application Ser. No. 09/257,179, filed Feb. 25, 1999, which is a continuation-in-part of International Application No. PCT/US98/17709, filed Aug. 27, 1998; U.S. application Ser. No. 10/100,683 is a continuation-in-part of U.S. application Ser. No. 09/257,179, filed Feb. 25, 1999, which is a continuation-in-part of International Application No. PCT/US98/17709, filed Aug. 27, 1998; U.S. application Ser. No. 10/100,683 is a continuation-in-part of International Application No. PCT/US98/17709, filed Aug. 27, 1998, which claims the benefit of U.S. Provisional Application Nos. 60/056,270, filed Aug. 29, 1997, 60/056,271, filed Aug. 29, 1997, 60/056,247, filed Aug. 29, 1997, and 60/056,073, filed Aug. 29, 1997; U.S. application Ser. No. 10/100,683 is a continuation-in-part of U.S. application Ser. No. 10/047,021, filed Jan. 17, 2002, which is a continuation-in-part of U.S. application Ser. No. 09/722,329, filed Nov. 28, 2000, which is a continuation of U.S. application Ser. No. 09/262,109, filed Mar. 4, 1999, which is a continuation-in-part of International Application No. PCT/US98/18360, filed Sep. 3, 1998; U.S. application Ser. No. 10/100,683 is a continuation-in-part of U.S. application Ser. No. 09/722,329, filed Nov. 28, 2000, which is a continuation of U.S. application Ser. No. 09/262,109, filed Mar. 4, 1999, which is a continuation-in-part of International Application No. PCT/US98/18360, filed Sep. 3, 1998; U.S. application Ser. No. 10/100,683 is a continuation-in-part of International Application No. PCT/US02/01109, filed Jan. 17, 2002, which claims the benefit of U.S. Provisional Application No. 60/262,066, filed Jan. 18, 2001; U.S. application Ser. No. 10/100,683 is a continuation-in-part of International Application No. PCT/US98/18360, filed Sep. 3, 1998, which claims the benefit of U.S. Provisional Application Nos. 60/057,626, filed Sep. 5, 1997, 60/057,663, filed Sep. 5, 1997, 60/057,669, filed Sep. 5, 1997, 60/058,667, filed Sep. 12, 1997, 60/058,974, filed Sep. 12, 1997, 60/058,973, filed Sep. 12, 1997, 60/058,666, filed Sep. 12, 1997, and 60/090,112, filed Jun. 22, 1998; U.S. application Ser. No. 10/100,683 is a continuation-in-part of U.S. application Ser. No. 09/281,976, filed Mar. 31, 1999, which is a continuation-in-part of International Application No. PCT/US98/20775, filed Oct. 1, 1998; U.S. application Ser. No. 10/100,683 is a continuation-in-part of International Application No. PCT/US98/20775, filed Oct. 1, 1998, which claims the benefit of U.S. Provisional Application Nos. 60/060,837, filed Oct. 2, 1997, 60/060,862, filed Oct. 2, 1997, 60/060,839, filed Oct. 2, 1997, 60/060,866, filed Oct. 2, 1997, 60/060,843, filed Oct. 2, 1997, 60/060,836, filed Oct. 2, 1997, 60/060,838, filed Oct. 2, 1997, 60/060,874, filed Oct. 2, 1997, 60/060,833, filed Oct. 2, 1997, 60/060,884, filed Oct. 2, 1997, and 60/060,880, filed Oct. 2, 1997; U.S. application Ser. No. 10/100,683 is a continuation-in-part of U.S. application Ser. No. 09/984,429, filed Oct. 30, 2001, which claims the benefit of U.S. Provisional Application No. 60/244,591, filed Nov. 1, 2000; U.S. application Ser. No. 09/984,429 is a continuation-in-part of U.S. application Ser. No. 09/288,143, filed Apr. 8, 1999, which is a continuation-in-part of International Application No. PCT/US98/21142, filed Oct. 8, 1998; U.S. application Ser. No. 10/100,683 claims the benefit of U.S. Provisional Application No. 60/244,591, filed Nov. 1, 2000; U.S. application Ser. No. 10/100,683 is a continuation-in-part of U.S. application Ser. No. 09/288,143, filed Apr. 8, 1999, which is a continuation-in-part of International Application No. PCT/US98/21142, filed Oct. 8, 1998; U.S. application Ser. No. 10/100,683 is a continuation-in-part of International Application No. PCT/US98/21142, filed Oct. 8, 1998, which claims the benefit of U.S. Provisional Application Nos. 60/061,463, filed Oct. 9, 1997, 60/061,529, filed Oct. 9, 1997, 60/071,498, filed Oct. 9, 1997, 60/061,527, filed Oct. 9, 1997, 60/061,536, filed Oct. 9, 1997, and 60/061,532, filed Oct. 9, 1997; U.S. application Ser. No. 10/100,683 is a continuation-in-part of U.S. application Ser. No. 09/296,622, filed Apr. 23, 1999, which is a continuation-in-part of International Application No. PCT/US98/22376, filed Oct. 23, 1998; U.S. application Ser. No. 10/100,683 is a continuation-in-part of International Application No. PCT/US98/22376, filed Oct. 23, 1998, which claims the benefit of U.S. Provisional Application Nos. 60/063,099, filed Oct. 24, 1997, 60/063,088, filed Oct. 24, 1997, 60/063,100, filed Oct. 24, 1997, 60/063,387, filed Oct. 24, 1997, 60/063,148, filed Oct. 24, 1997, 60/063,386, filed Oct. 24, 1997, 60/062,784, filed Oct. 24, 1997, 60/063,091, filed Oct. 24, 1997, 60/063,090, filed Oct. 24, 1997, 60/063,089, filed Oct. 24, 1997, 60/063,092, filed Oct. 24, 1997, 60/063,111, filed Oct. 24, 1997, 60/063,101, filed Oct. 24, 1997, 60/063,109, filed Oct. 24, 1997, 60/063,110, filed Oct. 24, 1997, 60/063,098, filed Oct. 24, 1997, and 60/063,097, filed Oct. 24, 1997; U.S. application Ser. No. 10/100,683 is a continuation-in-part of U.S. application Ser. No. 09/974,879, filed Oct. 12, 2001, which claims the benefit of U.S. Provisional Application No. 60/239,893, filed Oct. 13, 2000; U.S. application Ser. No. 09/974,879 is a continuation-in-part of U.S. application Ser. No. 09/818,683, filed Mar. 28, 2001, which is a continuation of U.S. application Ser. No. 09/305,736, filed May 5, 1999, which is a continuation-in-part of International Application No. PCT/US98/23435, filed Nov. 4, 1998; U.S. application Ser. No. 10/100,683 is a continuation-in-part of U.S. application Ser. No. 09/818,683, filed Mar. 28, 2001, which is a continuation of U.S. application Ser. No. 09/305,736, filed May 5, 1999, which is a continuation-in-part of International Application No. PCT/US98/23435, filed Nov. 4, 1998; U.S. application Ser. No. 10/100,683 is a continuation-in-part of U.S. application Ser. No. 09/305,736, filed May 5, 1999, which is a continuation-in-part of International Application No. PCT/US98/23435, filed Nov. 4, 1998; U.S. application Ser. No. 10/100,683 is a continuation-in-part of International Application No. PCT/US98/23435, filed Nov. 4, 1998, which claims the benefit of U.S. Provisional Application Nos. 60/064,911, filed Nov. 7, 1997, 60/064,912, filed Nov. 7, 1997, 60/064,983, filed Nov. 7, 1997, 60/064,900, filed Nov. 7, 1997, 60/064,988, filed Nov. 7, 1997, 60/064,987, filed Nov. 7, 1997, 60/064,908, filed Nov. 7, 1997, 60/064,984, filed Nov. 7, 1997, 60/064,985, filed Nov. 7, 1997, 60/066,094, filed Nov. 17, 1997, 60/066,100, filed Nov. 17, 1997, 60/066,089, filed Nov. 17, 1997, 60/066,095, filed Nov. 17, 1997, and 60/066,090, filed Nov. 17, 1997; U.S. application Ser. No. 10/100,683 is a continuation-in-part of U.S. application Ser. No. 09/334,595, filed Jun. 17, 1999, which is a continuation-in-part of International Application No. PCT/US98/27059, filed Dec. 17, 1998; U.S. application Ser. No. 10/100,683 is a continuation-in-part of International Application No. PCT/US98/27059, filed Dec. 17, 1998, which claims the benefit of U.S. Provisional Application Nos. 60/070,923, filed Dec. 18, 1997, 60/068,007, filed Dec. 18, 1997, 60/068,057, filed Dec. 18, 1997, 60/068,006, filed Dec. 18, 1997, 60/068,369, filed Dec. 19, 1997, 60/068,367, filed Dec. 19, 1997, 60/068,368, filed Dec. 19, 1997, 60/068,169, filed Dec. 19, 1997, 60/068,053, filed Dec. 18, 1997, 60/068,064, filed Dec. 18, 1997, 60/068,054, filed Dec. 18, 1997, 60/068,008, filed Dec. 18, 1997, and 60/068,365, filed Dec. 19, 1997; U.S. application Ser. No. 10/100,683 is a continuation-in-part of U.S. application Ser. No. 09/938,671, filed Aug. 27, 2001, which is a continuation of U.S. application Ser. No. 09/739,907, filed Dec. 20, 2000, which is a continuation of U.S. application Ser. No. 09/348,457, filed Jul. 7, 1999, which is a continuation-in-part of International Application No. PCT/US99/00108, filed Jan. 6, 1999; U.S. application Ser. No. 10/100,683 is a continuation-in-part of U.S. application Ser. No. 09/739,907, filed Dec. 20, 2000, which is a continuation of U.S. application Ser. No. 09/348,457, filed Jul. 7, 1999, which is a continuation-in-part of International Application No. PCT/US99/00108, filed Jan. 6, 1999; U.S. application Ser. No. 10/100,683 is a continuation-in-part of U.S. application Ser. No. 09/348,457, filed Jul. 7, 1999, which is a continuation-in-part of International Application No. PCT/US99/00108, filed Jan. 6, 1999; U.S. application Ser. No. 10/100,683 is a continuation-in-part of International Application No. PCT/US99/00108, filed Jan. 6, 1999, which claims the benefit of U.S. Provisional Application Nos. 60/070,704, filed Jan. 7, 1998, 60/070,658, filed Jan. 7, 1998, 60/070,692, filed Jan. 7, 1998, and 60/070,657, filed Jan. 7, 1998; U.S. application Ser. No. 10/100,683 is a continuation-in-part of U.S. application Ser. No. 09/949,925, filed Sep. 12, 2001, which claims the benefit of U.S. Provisional Application No. 60/232,150, filed Sep. 12, 2000; U.S. application Ser. No. 09/949,925 is a continuation-in-part of International Application No. PCT/US99/01621, filed Jan. 27, 1999; U.S. application Ser. No. 09/949,925 is a continuation-in-part of U.S. application Ser. No. 09/363,044, filed Jul. 29, 1999, which is a continuation-in-part of International Application No. PCT/US99/01621, filed Jan. 27, 1999; U.S. application Ser. No. 10/100,683 is a continuation-in-part of U.S. application Ser. No. 09/813,153, filed Mar. 21, 2001, which is a continuation of U.S. application Ser. No. 09/363,044, filed Jul. 29, 1999, which is a continuation-in-part of International Application No. PCT/US99/01621, filed Jan. 27, 1999; U.S. application Ser. No. 10/100,683 is a continuation-in-part of U.S. application Ser. No. 09/363,044, filed Jul. 29, 1999, which is a continuation-in-part of International Application No. PCT/US99/01621, filed Jan. 27, 1999; U.S. application Ser. No. 10/100,683 is a continuation-in-part of International Application No. PCT/US99/01621, filed Jan. 27, 1999, which claims the benefit of U.S. Provisional Application Nos. 60/073,170, filed Jan. 30, 1998, 60/073,167, filed Jan. 30, 1998, 60/073,165, filed Jan. 30, 1998, 60/073,164, filed Jan. 30, 1998, 60/073,162, filed Jan. 30, 1998, 60/073,161, filed Jan. 30, 1998, 60/073,160, filed Jan. 30, 1998, and 60/073,159, filed Jan. 30, 1998; U.S. application Ser. No. 10/100,683 is a continuation-in-part of U.S. application Ser. No. 10/062,548, filed Feb. 5, 2002, which is a continuation of U.S. application Ser. No. 09/369,247, filed Aug. 5, 1999; U.S. application Ser. No. 09/369,247 is a continuation-in-part of International Application No. PCT/US99/02293, filed Feb. 4, 1999; U.S. application Ser. No. 10/100,683 is a continuation-in-part of U.S. application Ser. No. 09/369,247, filed Aug. 5, 1999; U.S. application Ser. No. 09/369,247 is a continuation-in-part of International Application No. PCT/US99/02293, filed Feb. 4, 1999; U.S. application Ser. No. 10/100,683 is a continuation-in-part of International Application No. PCT/US99/02293, filed Feb. 4, 1999, which claims the benefit of U.S. Provisional Application Nos. 60/074,118, filed Feb. 9, 1998, 60/074,157, filed Feb. 9, 1998, 60/074,037, filed Feb. 9, 1998, 60/074,141, filed Feb. 9, 1998, and 60/074,341, filed Feb. 9, 1998; U.S. application Ser. No. 10/100,683 is a continuation-in-part of U.S. application Ser. No. 09/716,129, filed Nov. 17, 2000, which is a continuation-in-part of International Application No. PCT/US99/03939, filed Feb. 24, 1999; U.S. application Ser. No. 09/716,129 is a continuation of U.S. application Ser. No. 09/382,572, filed Aug. 25, 1999, which is a continuation-in-part of International Application No. PCT/US99/03939, filed Feb. 24, 1999; U.S. application Ser. No. 10/100,683 is a continuation-in-part of International Application No. PCT/US99/03939, filed Feb. 24, 1999, which claims the benefit of U.S. Provisional Application Nos. 60/076,053, filed Feb. 26, 1998, 60/076,051, filed Feb. 26, 1998, 60/076,054, filed Feb. 26, 1998, 60/076,052, filed Feb. 26, 1998, and 60/076,057, filed Feb. 26, 1998; U.S. application Ser. No. 10/100,683 is a continuation-in-part of U.S. application Ser. No. 09/798,889, filed Mar. 6, 2001, which is a continuation of U.S. application Ser. No. 09/393,022, filed Sep. 9, 1999, which is a continuation-in-part of International Application No. PCT/US99/05721, filed Mar. 11, 1999; U.S. application Ser. No. 10/100,683 is a continuation-in-part of International Application No. PCT/US99/05721, filed Mar. 11, 1999, which claims the benefit of U.S. Provisional Application Nos. 60/077,714, filed Mar. 12, 1998, 60/077,686, filed Mar. 12, 1998, 60/077,687, filed Mar. 12, 1998, and 60/077,696, filed Mar. 12, 1998; U.S. application Ser. No. 10/100,683 is a continuation-in-part of U.S. application Ser. No. 09/397,945, filed Sep. 17, 1999, which is a continuation-in-part of International Application No. PCT/US99/05804, filed Mar. 18, 1999; U.S. application Ser. No. 10/100,683 is a continuation-in-part of International Application No. PCT/US99/05804, filed Mar. 18, 1999, which claims the benefit of U.S. Provisional Application Nos. 60/078,566, filed Mar. 19, 1998, 60/078,576, filed Mar. 19, 1998, 60/078,573, filed Mar. 19, 1998, 60/078,574, filed Mar. 19, 1998, 60/078,579, filed Mar. 19, 1998, 60/080,314, filed Apr. 1, 1998, 60/080,312, filed Apr. 1, 1998, 60/078,578, filed Mar. 19, 1998, 60/078,581, filed Mar. 19, 1998, 60/078,577, filed Mar. 19, 1998, 60/078,563, filed Mar. 19, 1998, and 60/080,313, filed Apr. 1, 1998; U.S. application Ser. No. 10/100,683 is a continuation-in-part of U.S. application Ser. No. 09/948,783, filed Sep. 10, 2001, which claims the benefit of U.S. Provisional Application No. 60/231,846, filed Sep. 11, 2000; U.S. application Ser. No. 09/948,783 is a continuation-in-part of U.S. application Ser. No. 09/892,877, filed Jun. 28, 2001, which is a continuation of U.S. application Ser. No. 09/437,658, filed Nov. 10, 1999, which is a continuation-in-part of International Application No. PCT/US99/09847, filed May 6, 1999; U.S. application Ser. No. 10/100,683 is a continuation-in-part of U.S. application Ser. No. 09/892,877, filed Jun. 28, 2001, which is a continuation of U.S. application Ser. No. 09/437,658, filed Nov. 10, 1999, which is a continuation-in-part of International Application No. PCT/US99/09847, filed May 6, 1999; U.S. application Ser. No. 10/100,683 is a continuation-in-part of International Application No. PCT/US99/09847, filed May 6, 1999, which claims the benefit of U.S. Provisional Application Nos. 60/085,093, filed May 12, 1998, 60/085,094, filed May 12, 1998, 60/085,105, filed May 12, 1998, 60/085,180, filed May 12, 1998, 60/085,927, filed May 18, 1998, 60/085,906, filed May 18, 1998, 60/085,920, filed May 18, 1998, 60/085,924, filed May 18, 1998, 60/085,922, filed May 18, 1998, 60/085,923, filed May 18, 1998, 60/085,921, filed May 18, 1998, 60/085,925, filed May 18, 1998, and 60/085,928, filed May 18, 1998; U.S. application Ser. No. 10/100,683 is a continuation-in-part of U.S. application Ser. No. 10/050,873, filed Jan. 18, 2002, which claims the benefit of U.S. Provisional Application Nos. 60/263,681, filed Jan. 24, 2001, and 60/263,230, filed Jan. 23, 2001; U.S. application Ser. No. 10/050,873 is a continuation-in-part of U.S. application Ser. No. 09/461,325, filed Dec. 14, 1999, which is a continuation-in-part of International Application No. PCT/US99/13418, filed Jun. 15, 1999; U.S. application Ser. No. 10/100,683 is a continuation-in-part of U.S. application Ser. No. 10/012,542, filed Dec. 12, 2001, which is a divisional of U.S. application Ser. No. 09/461,325, filed Dec. 14, 1999, which is a continuation-in-part of International Application No. PCT/US99/13418, filed Jun. 15, 1999; U.S. application Ser. No. 10/100,683 is a continuation-in-part of U.S. application Ser. No. 09/461,325, filed Dec. 14, 1999, which is a continuation-in-part of International Application No. PCT/US99/13418, filed Jun. 15, 1999; U.S. application Ser. No. 10/100,683 is a continuation-in-part of International Application No. PCT/US99/13418, filed Jun. 15, 1999, which claims the benefit of U.S. Provisional Application Nos. 60/089,507, filed Jun. 16, 1998, 60/089,508, filed Jun. 16, 1998, 60/089,509, filed Jun. 16, 1998, 60/089,510, filed Jun. 16, 1998, 60/090,112, filed Jun. 22, 1998, and 60/090,113, filed Jun. 22, 1998; U.S. application Ser. No. 10/100,683 is a continuation-in-part of U.S. application Ser. No. 09/984,271, filed Oct. 29, 2001, which is a divisional of U.S. application Ser. No. 09/482,273, filed Jan. 13, 2000, which is a continuation-in-part of International Application No. PCT/11S99/15849, filed Jul. 14, 1999; U.S. application Ser. No. 10/100,683 is a continuation-in-part of U.S. application Ser. No. 09/984,276, filed Oct. 29, 2001, which is a divisional of U.S. application Ser. No. 09/482,273, filed Jan. 13, 2000, which is a continuation-in-part of International Application No. PCT/US99/15849, filed Jul. 14, 1999; U.S. application Ser. No. 10/100,683 is a continuation-in-part of U.S. application Ser. No. 09/482,273, filed Jan. 13, 2000, which is a continuation-in-part of International Application No. PCT/US99/15849, filed Jul. 14, 1999; U.S. application Ser. No. 10/100,683 is a continuation-in-part of International Application No. PCT/US99/15849, filed Jul. 14, 1999, which claims the benefit of U.S. Provisional Application Nos. 60/092,921, filed Jul. 15, 1998, 60/092,922, filed Jul. 15, 1998, and 60/092,956, filed Jul. 15, 1998; U.S. application Ser. No. 10/100,683 is a continuation-in-part of International Application No. PCT/US01/29871, filed Sep. 24, 2001, which claims the benefit of U.S. Provisional Application No. 60/234,925, filed Sep. 25, 2000; International Application No. PCT/US01/29871 is a continuation-in-part of International Application No. PCT/US01/00911, filed Jan. 12, 2001; U.S. application Ser. No. 10/100,683 is a continuation-in-part of International Application No. PCT/US01/00911, filed Jan. 12, 2001, which is a continuation-in-part of U.S. application Ser. No. 09/482,273, filed Jan. 13, 2000; U.S. application Ser. No. 10/100,683 claims the benefit of U.S. Provisional Application No. 60/350,898, filed Jan. 25, 2002; U.S. application Ser. No. 10/100,683 is a continuation-in-part of U.S. application Ser. No. 09/489,847, filed Jan. 24, 2000, which is a continuation-in-part of International Application No. PCT/US99/17130, filed Jul. 29, 1999; U.S. application Ser. No. 10/100,683 is a continuation-in-part of International Application No. PCT/US99/17130, filed Jul. 29, 1999, which claims the benefit of U.S. Provisional Application Nos. 60/094,657, filed Jul. 30, 1998, 60/095,486, filed Aug. 5, 1998, 60/096,319, filed Aug. 12, 1998, 60/095,454, filed Aug. 6, 1998, and 60/095,455, filed Aug. 6, 1998; U.S. application Ser. No. 10/100,683 is a continuation-in-part of U.S. application Ser. No. 10/054,988, filed Jan. 25, 2002, which is a continuation of U.S. application Ser. No. 09/904,615, filed Jul. 16, 2001, which is a continuation of U.S. application Ser. No. 09/739,254, filed Dec. 19, 2000, which is a continuation of U.S. application Ser. No. 09/511,554, filed Feb. 23, 2000, which is a continuation-in-part of International Application No. PCT/US99/19330, filed Aug. 24, 1999; U.S. application Ser. No. 10/100,683 is a continuation-in-part of U.S. application Ser. No. 09/904,615, filed Jul. 16, 2001, which is a continuation of U.S. application Ser. No. 09/739,254, filed Dec. 19, 2000, which is a continuation of U.S. application Ser. No. 09/511,554, filed Feb. 23, 2000, which is a continuation-in-part of International Application No. PCT/US99/19330, filed Aug. 24, 1999; U.S. application Ser. No. 10/100,683 is a continuation-in-part of International Application No. PCT/US99/19330, filed Aug. 24, 1999, which claims the benefit of U.S. Provisional Application Nos. 60/097,917, filed Aug. 25, 1998, and 60/098,634, filed Aug. 31, 1998; U.S. application Ser. No. 10/100,683 is a continuation-in-part of U.S. application Ser. No. 09/820,893, filed Mar. 30, 2001, which is a continuation of U.S. application Ser. No. 09/531,119, filed Mar. 20, 2000, which is a continuation-in-part of International Application No. PCT/US99/22012, filed Sep. 22, 1999; U.S. application Ser. No. 10/100,683 is a continuation-in-part of International Application No. PCT/US99/22012, filed Sep. 22, 1999, which claims the benefit of U.S. Provisional Application Nos. 60/101,546, filed Sep. 23, 1998, and 60/102,895, filed Oct. 2, 1998; U.S. application Ser. No. 10/100,683 is a continuation-in-part of U.S. application Ser. No. 09/948,820, filed Sep. 10, 2001, which is a continuation of U.S. application Ser. No. 09/565,391, filed May 5, 2000, which is a continuation-in-part of International Application No. PCT/US99/26409, filed Nov. 9, 1999; U.S. application Ser. No. 10/100,683 is a continuation-in-part of U.S. application Ser. No. 09/565,391, filed May 5, 2000, which is a continuation-in-part of International Application No. PCT/US99/26409, filed Nov. 9, 1999; U.S. application Ser. No. 10/100,683 is a continuation-in-part of International Application No. PCT/US99/26409, filed Nov. 9, 1999, which claims the benefit of U.S. Provisional Application No. 60/108,207, filed Nov. 12, 1998; U.S. application Ser. No. 10/100,683 is a continuation-in-part of U.S. application Ser. No. 09/895,298, filed Jul. 2, 2001, which is a continuation of U.S. application Ser. No. 09/591,316, filed Jun. 9, 2000, which is a continuation-in-part of International Application No. PCT/US99/29950, filed Dec. 16, 1999; U.S. application Ser. No. 10/100,683 is a continuation-in-part of International Application No. PCT/US99/29950, filed Dec. 16, 1999, which claims the benefit of U.S. Provisional Application Nos. 60/113,006, filed Dec. 18, 1998, and 60/112,809, filed Dec. 17, 1998; U.S. application Ser. No. 10/100,683 is a continuation-in-part of U.S. application Ser. No. 09/985,153, filed Nov. 1, 2001, which is a continuation of U.S. application Ser. No. 09/618,150, filed Jul. 17, 2000, which is a continuation-in-part of International Application No. PCT/US00/00903, filed Jan. 18, 2000; U.S. application Ser. No. 10/100,683 is a continuation-in-part of International Application No. PCT/US00/00903, filed Jan. 18, 2000, which claims the benefit of U.S. Provisional Application No. 60/116,330, filed Jan. 19, 1999; U.S. application Ser. No. 10/100,683 is a continuation-in-part of U.S. application Ser. No. 09/997,131, filed Nov. 30, 2001, which is a continuation of U.S. application Ser. No. 09/628,508, filed Jul. 28, 2000, which is a continuation-in-part of International Application No. PCT/US00/03062, filed Feb. 8, 2000; U.S. application Ser. No. 10/100,683 is a continuation-in-part of International Application No. PCT/US00/03062, filed Feb. 8, 2000, which claims the benefit of U.S. Provisional Application No. 60/119,468, filed Feb. 10, 1999; U.S. application Ser. No. 10/100,683 is a continuation-in-part of U.S. application Ser. No. 10/050,882, filed Jan. 18, 2002, which is a continuation of U.S. application Ser. No. 09/661,453, filed Sep. 13, 2000, which is a continuation-in-part of International Application No. PCT/US00/06783, filed Mar. 16, 2000; U.S. application Ser. No. 10/100,683 is a continuation-in-part of U.S. application Ser. No. 09/661,453, filed Sep. 13, 2000, which is a continuation-in-part of International Application No. PCT/US00/06783, filed Mar. 16, 2000; U.S. application Ser. No. 10/100,683 is a continuation-in-part of International Application No. PCT/US00/06783, filed Mar. 16, 2000, which claims the benefit of U.S. Provisional Application No. 60/125,055, filed Mar. 18, 1999; U.S. application Ser. No. 10/100,683 is a continuation-in-part of U.S. application Ser. No. 10/050,704, filed Jan. 18, 2002, which is a continuation of U.S. application Ser. No. 09/684,524, filed Oct. 10, 2000, which is a continuation-in-part of International Application No. PCT/US00/08979, filed Apr. 6, 2000; U.S. application Ser. No. 10/100,683 is a continuation-in-part of U.S. application Ser. No. 09/684,524, filed Oct. 10, 2000, which is a continuation-in-part of International Application No. PCT/US00/08979, filed Apr. 6, 2000; U.S. application Ser. No. 10/100,683 is a continuation-in-part of International Application No. PCT/US00/08979, filed Apr. 6, 2000, which claims the benefit of U.S. Provisional Application Nos. 60/128,693, filed Apr. 9, 1999, and 60/130,991, filed Apr. 26, 1999; U.S. application Ser. No. 10/100,683 is a continuation-in-part of U.S. application Ser. No. 10/042,141, filed Jan. 11, 2002, which is a continuation of U.S. application Ser. No. 09/726,643, filed Dec. 1, 2000, which is a continuation-in-part of International Application No. PCT/US00/15187, filed Jun. 2, 2000; U.S. application Ser. No. 10/100,683 is a continuation-in-part of U.S. application Ser. No. 09/726,643, filed Dec. 1, 2000, which is a continuation-in-part of International Application No. PCT/US00/15187, filed Jun. 2, 2000; U.S. application Ser. No. 10/100,683 is a continuation-in-part of International Application No. PCT/US00/15187, filed Jun. 2, 2000, which claims the benefit of U.S. Provisional Application No. 60/137,725, filed Jun. 7, 1999; U.S. application Ser. No. 10/100,683 is a continuation-in-part of U.S. application Ser. No. 09/756,168, filed Jan. 9, 2001, which is a continuation-in-part of International Application No. PCT/US00/19735, filed Jul. 23, 1999; U.S. application Ser. No. 10/100,683 is a continuation-in-part of International Application No. PCT/US00/19735, filed Jul. 20, 2000, which claims the benefit of U.S. Provisional Application No. 60/145,220, filed Jul. 23, 1999; U.S. application Ser. No. 10/100,683 is a continuation-in-part of U.S. application Ser. No. 10/060,255, filed Feb. 1, 2002, which is a continuation of U.S. application Ser. No. 09/781,417, filed Feb. 13, 2001, which is a continuation-in-part of International Application No. PCT/US00/22325, filed Aug. 16, 2000; U.S. application Ser. No. 10/100,683 is a continuation-in-part of U.S. application Ser. No. 09/781,417, filed Feb. 13, 2001, which is a continuation-in-part of International Application No. PCT/US00/22325, filed Aug. 16, 2000; U.S. application Ser. No. 10/100,683 is a continuation-in-part of International Application No. PCT/US00/22325, filed Aug. 16, 2000, which claims the benefit of U.S. Provisional Application No. 60/149,182, filed Aug. 17, 1999; U.S. application Ser. No. 10/100,683 is a continuation-in-part of U.S. application Ser. No. 09/789,561, filed Feb. 22, 2001, which is a continuation-in-part of International Application No. PCT/US00/24008, filed Aug. 31, 2000; U.S. application Ser. No. 10/100,683 is a continuation-in-part of International Application No. PCT/US00/24008, filed Aug. 31, 2000, which claims the benefit of U.S. Provisional Application Nos. 60/152,315, filed Sep. 3, 1999, and 60/152,317, filed Sep. 3, 1999; U.S. application Ser. No. 10/100,683 is a continuation-in-part of U.S. application Ser. No. 09/800,729, filed Mar. 8, 2001, which is a continuation-in-part of International Application No. PCT/US00/26013, filed Sep. 22, 2000; U.S. application Ser. No. 10/100,683 is a continuation-in-part of International Application No. PCT/US00/26013, filed Sep. 22, 2000, which claims the benefit of U.S. Provisional Application No. 60/155,709, filed Sep. 24, 1999; U.S. application Ser. No. 10/100,683 is a continuation-in-part of U.S. application Ser. No. 09/832,129, filed Apr. 11, 2001, which is a continuation-in-part of International Application No. PCT/US00/28664, filed Oct. 17, 2000; U.S. application Ser. No. 10/100,683 is a continuation-in-part of International Application No. PCT/US00/28664, filed Oct. 17, 2000, which claims the benefit of U.S. Provisional Application Nos. 60/163,085, filed Nov. 2, 1999, and 60/172,411, filed Dec. 17, 1999; U.S. application Ser. No. 10/100,683 is a continuation-in-part of International Application No. PCT/US00/29363, filed Oct. 25, 2000, which claims the benefit of U.S. Provisional Application Nos. 60/215,139, filed Jun. 30, 2000, and 60/162,239, filed Oct. 29, 1999; U.S. application Ser. No. 10/100,683 is a continuation-in-part of International Application No. PCT/US00/29360, filed Oct. 25, 2000, which claims the benefit of U.S. Provisional Application Nos. 60/215,138, filed Jun. 30, 2000, and 60/162,211, filed Oct. 29, 1999; U.S. application Ser. No. 10/100,683 is a continuation-in-part of International Application No. PCT/US00/29362, filed Oct. 25, 2000, which claims the benefit of U.S. Provisional Application Nos. 60/215,131, filed Jun. 30, 2000, and 60/162,240, filed Oct. 29, 1999; U.S. application Ser. No. 10/100,683 is a continuation-in-part of International Application No. PCT/US00/29365, filed Oct. 25, 2000, which claims the benefit of U.S. Provisional Application Nos. 60/219,666, filed Jul. 21, 2000, and 60/162,237, filed Oct. 29, 1999; U.S. application Ser. No. 10/100,683 is a continuation-in-part of International Application No. PCT/US00/29364, filed Oct. 25, 2000, which claims the benefit of U.S. Provisional Application Nos. 60/215,134, filed Jun. 30, 2000, and 60/162,238, filed Oct. 29, 1999; U.S. application Ser. No. 10/100,683 is a continuation-in-part of International Application No. PCT/US00/30040, filed Nov. 1, 2000, which claims the benefit of U.S. Provisional Application Nos. 60/215,130, filed Jun. 30, 2000, and 60/163,580, filed Nov. 5, 1999; U.S. application Ser. No. 10/100,683 is a continuation-in-part of International Application No. PCT/US00/30037, filed Nov. 1, 2000, which claims the benefit of U.S. Provisional Application Nos. 60/215,137, filed Jun. 30, 2000, and 60/163,577, filed Nov. 5, 1999; U.S. application Ser. No. 10/100,683 is a continuation-in-part of International Application No. PCT/US00/30045, filed Nov. 1, 2000, which claims the benefit of U.S. Provisional Application Nos. 60/215,133, filed Jun. 30, 2000, and 60/163,581, filed Nov. 5, 1999; U.S. application Ser. No. 10/100,683 is a continuation-in-part of International Application No. PCT/US00/30036, filed Nov. 1, 2000, which claims the benefit of U.S. Provisional Application Nos. 60/221,366, filed Jul. 27, 2000, and 60/163,576, filed Nov. 5, 1999; U.S. application Ser. No. 10/100,683 is a continuation-in-part of International Application No. PCT/US00/30039, filed Nov. 1, 2000, which claims the benefit of U.S. Provisional Application Nos. 60/221,367, filed Jul. 27, 2000, 60/195,296, filed Apr. 7, 2000, and 60/164,344, filed Nov. 9, 1999; U.S. application Ser. No. 10/100,683 is a continuation-in-part of International Application No. PCT/US00/30654, filed Nov. 8, 2000, which claims the benefit of U.S. Provisional Application Nos. 60/221,142, filed Jul. 27, 2000, and 60/164,835, filed Nov. 12, 1999; U.S. application Ser. No. 10/100,683 is a continuation-in-part of International Application No. PCT/US00/30628, filed Nov. 8, 2000, which claims the benefit of U.S. Provisional Application Nos. 60/215,140, filed Jun. 30, 2000, and 60/164,744, filed Nov. 12, 1999; U.S. application Ser. No. 10/100,683 is a continuation-in-part of International Application No. PCT/US00/30653, filed Nov. 8, 2000, which claims the benefit of U.S. Provisional Application Nos. 60/221,193, filed Jul. 27, 2000, and 60/164,735, filed Nov. 12, 1999; U.S. application Ser. No. 10/100,683 is a continuation-in-part of International Application No. PCT/US00/30629, filed Nov. 8, 2000, which claims the benefit of U.S. Provisional Application Nos. 60/222,904, filed Aug. 3, 2000, and 60/164,825, filed Nov. 12, 1999; U.S. application Ser. No. 10/100,683 is a continuation-in-part of International Application No. PCT/US00/30679, filed Nov. 8, 2000, which claims the benefit of U.S. Provisional Application Nos. 60/224,007, filed Aug. 4, 2000, and 60/164,834, filed Nov. 12, 1999; U.S. application Ser. No. 10/100,683 is a continuation-in-part of International Application No. PCT/US00/30674, filed Nov. 8, 2000, which claims the benefit of U.S. Provisional Application Nos. 60/215,128, filed Jun. 30, 2000, and 60/164,750, filed Nov. 12, 1999; U.S. application Ser. No. 10/100,683 is a continuation-in-part of International Application No. PCT/US00/31162, filed Nov. 15, 2000; U.S. Provisional Application No. 60/215,136 claims the benefit of U.S. Provisional Application Nos. 60/215,136, filed Jun. 30, 2000, which claims the benefit of U.S. Provisional Application No. 60/166,415, filed Nov. 19, 1999; U.S. application Ser. No. 10/100,683 is a continuation-in-part of International Application No. PCT/US00/31282, filed Nov. 15, 2000, which claims the benefit of U.S. Provisional Application Nos. 60/219,665, filed Jul. 21, 2000, and 60/166,414, filed Nov. 19, 1999; U.S. application Ser. No. 10/100,683 is a continuation-in-part of International Application No. PCT/US00/30657, filed Nov. 8, 2000, which claims the benefit of U.S. Provisional Application Nos. 60/215,132, filed Jun. 30, 2000, and 60/164,731, filed Nov. 12, 1999; U.S. application Ser. No. 10/100,683 is a continuation-in-part of International Application No. PCT/US01/01396, filed Jan. 17, 2001; U.S. Provisional Application No. 60/256,968 claims the benefit of U.S. Provisional Application Nos. 60/256,968, filed Dec. 21, 2000, which claims the benefit of U.S. Provisional Application No. 60/226,280, filed Aug. 18, 2000; U.S. application Ser. No. 10/100,683 is a continuation-in-part of International Application No. PCT/US01/01387, filed Jan. 17, 2001; U.S. Provisional Application No. 60/259,803 claims the benefit of U.S. Provisional Application Nos. 60/259,803, filed Jan. 5, 2001, which claims the benefit of U.S. Provisional Application No. 60/226,380, filed Aug. 18, 2000; U.S. application Ser. No. 10/100,683 is a continuation-in-part of International Application No. PCT/US01/01567, filed Jan. 17, 2001, which claims the benefit of U.S. Provisional Application No. 60/228,084, filed Aug. 28, 2000; U.S. application Ser. No. 10/100,683 is a continuation-in-part of International Application No. PCT/US01/01431, filed Jan. 17, 2001, which claims the benefit of U.S. Provisional Application No. 60/231,968, filed Sep. 12, 2000; International Application No. PCT/US01/01431 is a continuation-in-part of U.S. application Ser. No. 09/915,582, filed Jul. 27, 2001; U.S. application Ser. No. 10/100,683 is a continuation-in-part of International Application No. PCT/US01/01432, filed Jan. 17, 2001, which claims the benefit of U.S. Provisional Application No. 60/236,326, filed Sep. 29, 2000; U.S. application Ser. No. 10/100,683 is a continuation-in-part of International Application No. PCT/US01/00544, filed Jan. 9, 2001, which claims the benefit of U.S. Provisional Application No. 60/234,211, filed Sep. 20, 2000; U.S. application Ser. No. 10/100,683 is a continuation-in-part of International Application No. PCT/US01/01435, filed Jan. 17, 2001, which claims the benefit of U.S. Provisional Application No. 60/226,282, filed Aug. 18, 2000; U.S. application Ser. No. 10/100,683 is a continuation-in-part of International Application No. PCT/US01/01386, filed Jan. 17, 2001, which claims the benefit of U.S. Provisional Application No. 60/232,104, filed Sep. 12, 2000; U.S. application Ser. No. 10/100,683 is a continuation-in-part of International Application No. PCT/US01/01565, filed Jan. 17, 2001, which claims the benefit of U.S. Provisional Application No. 60/234,210, filed Sep. 20, 2000; U.S. application Ser. No. 10/100,683 is a continuation-in-part of International Application No. PCT/US01/01394, filed Jan. 17, 2001, which claims the benefit of U.S. Provisional Application Nos. 60/259,805, filed Jan. 5, 2001, and 60/226,278, filed Aug. 18, 2000; U.S. application Ser. No. 10/100,683 is a continuation-in-part of International Application No. PCT/US01/01434, filed Jan. 17, 2001, which claims the benefit of U.S. Provisional Application Nos. 60/259,678, filed Jan. 5, 2001, and 60/226,279, filed Aug. 18, 2000; U.S. application Ser. No. 10/100,683 is a continuation-in-part of International Application No. PCT/US01/01397, filed Jan. 17, 2001, which claims the benefit of U.S. Provisional Application No. 60/226,281, filed Aug. 18, 2000; U.S. application Ser. No. 10/100,683 is a continuation-in-part of International Application No. PCT/US01/01385, filed Jan. 17, 2001, which claims the benefit of U.S. Provisional Application No. 60/231,969, filed Sep. 12, 2000; U.S. application Ser. No. 10/100,683 is a continuation-in-part of International Application No. PCT/US01/01384, filed Jan. 17, 2001, which claims the benefit of U.S. Provisional Application Nos. 60/259,516, filed Jan. 4, 2001, and 60/228,086, filed Aug. 28, 2000; U.S. application Ser. No. 10/100,683 is a continuation-in-part of International Application No. PCT/US01/01383, filed Jan. 17, 2001, which claims the benefit of U.S. Provisional Application Nos. 60/259,804, filed Jan. 5, 2001, and 60/228,083, filed Aug. 28, 2000; U.S. application Ser. No. 10/100,683 is a continuation-in-part of International Application No. PCT/US02/05064, filed Feb. 21, 2002, which claims the benefit of U.S. Provisional Application Nos. 60/304,444, filed Jul. 12, 2001, and 60/270,658, filed Feb. 23, 2001; U.S. application Ser. No. 10/100,683 is a continuation-in-part of International Application No. PCT/US02/05301, filed Feb. 21, 2002, which claims the benefit of U.S. Provisional Application Nos. 60/304,417, filed Jul. 12, 2001, and 60/270,625, filed Feb. 23, 2001; U.S. application Ser. No. 10/100,683 claims the benefit of U.S. Provisional Application Nos. 60/304,121, filed Jul. 11, 2001, 60/295,869, filed Jun. 6, 2001, 60/325,209, filed Sep. 28, 2001, 60/311,085, filed Aug. 10, 2001, 60/330,629, filed Oct. 26, 2001, 60/331,046, filed Nov. 7, 2001, 60/358,554, filed Feb. 22, 2002, and 60/358,714, filed Feb. 25, 2002. This application is a continuation-in-part of U.S. application Ser. No. 12/198,817, filed Aug. 26, 2008, which is a divisional of U.S. application Ser. No. 11/346,470, filed Feb. 3, 2006, which is a continuation-in-part of U.S. application Ser. No. 10/472,532, filed Sep. 20, 2003 and accorded a National Stage filing date of Jun. 23, 2004, now abandoned, which is the 35 U.S.C. §371 National Stage of PCT/US02/08278, filed Mar. 19, 2002, which in turn claims benefit of U.S. patent application Ser. No. 10/100,683 (now U.S. Pat. No. 7,368,531, issued May 6, 2008). U.S. application Ser. No. 11/346,470 is also a continuation-in-part of U.S. patent application Ser. No. 10/100,683, filed Mar. 19, 2002, which claims the benefit of U.S. Provisional Application Nos. 60/277,340, filed Mar. 21, 2001, 60/306,171, filed Jul. 19, 2001, and 60/331,287, filed Nov. 13, 2001; U.S. application Ser. No. 10/100,683 is a continuation-in-part of U.S. application Ser. No. 09/981,876, filed Oct. 19, 2001, which is a divisional of U.S. application Ser. No. 09/621,011, filed Jul. 20, 2000, which is a continuation of U.S. application Ser. No. 09/148,545, filed Sep. 4, 1998, which is a continuation-in-part of International Application No. PCT/US98/04482, filed Mar. 6, 1998; U.S. application Ser. No. 10/100,683 is a continuation-in-part of U.S. application Ser. No. 09/621,011, filed Jul. 20, 2000, which is a continuation of U.S. application Ser. No. 09/148,545, filed Sep. 4, 1998, which is a continuation-in-part of International Application No. PCT/US98/04482, filed Mar. 6, 1998; U.S. application Ser. No. 10/100,683 is a continuation-in-part of U.S. application Ser. No. 09/148,545, filed Sep. 4, 1998, which is a continuation-in-part of International Application No. PCT/US98/04482, filed Mar. 6, 1998; U.S. application Ser. No. 10/100,683 is a continuation-in-part of International Application No. PCT/US98/04482, filed Mar. 6, 1998, which claims the benefit of U.S. Provisional Application Nos. 60/040,162, filed Mar. 7, 1997, 60/040,333, filed Mar. 7, 1997, 60/038,621, filed Mar. 7, 1997, 60/040,161, filed Mar. 7, 1997, 60/040,626, filed Mar. 7, 1997, 60/040,334, filed Mar. 7, 1997, 60/040,336, filed Mar. 7, 1997, 60/040,163, filed Mar. 7, 1997, 60/047,615, filed May 23, 1997, 60/047,600, filed May 23, 1997, 60/047,597, filed May 23, 1997, 60/047,502, filed May 23, 1997, 60/047,633, filed May 23, 1997, 60/047,583, filed May 23, 1997, 60/047,617, filed May 23, 1997, 60/047,618, filed May 23, 1997, 60/047,503, filed May 23, 1997, 60/047,592, filed May 23, 1997, 60/047,581, filed May 23, 1997, 60/047,584, filed May 23, 1997, 60/047,500, filed May 23, 1997, 60/047,587, filed May 23, 1997, 60/047,492, filed May 23, 1997, 60/047,598, filed May 23, 1997, 60/047,613, filed May 23, 1997, 60/047,582, filed May 23, 1997, 60/047,596, filed May 23, 1997, 60/047,612, filed May 23, 1997, 60/047,632, filed May 23, 1997, 60/047,601, filed May 23, 1997, 60/043,580, filed Apr. 11, 1997, 60/043,568, filed Apr. 11, 1997, 60/043,314, filed Apr. 11, 1997, 60/043,569, filed Apr. 11, 1997, 60/043,311, filed Apr. 11, 1997, 60/043,671, filed Apr. 11, 1997, 60/043,674, filed Apr. 11, 1997, 60/043,669, filed Apr. 11, 1997, 60/043,312, filed Apr. 11, 1997, 60/043,313, filed Apr. 11, 1997, 60/043,672, filed Apr. 11, 1997, 60/043,315, filed Apr. 11, 1997, 60/048,974, filed Jun. 6, 1997, 60/056,886, filed Aug. 22, 1997, 60/056,877, filed Aug. 22, 1997, 60/056,889, filed Aug. 22, 1997, 60/056,893, filed Aug. 22, 1997, 60/056,630, filed Aug. 22, 1997, 60/056,878, filed Aug. 22, 1997, 60/056,662, filed Aug. 22, 1997, 60/056,872, filed Aug. 22, 1997, 60/056,882, filed Aug. 22, 1997, 60/056,637, filed Aug. 22, 1997, 60/056,903, filed Aug. 22, 1997, 60/056,888, filed Aug. 22, 1997, 60/056,879, filed Aug. 22, 1997, 60/056,880, filed Aug. 22, 1997, 60/056,894, filed Aug. 22, 1997, 60/056,911, filed Aug. 22, 1997, 60/056,636, filed Aug. 22, 1997, 60/056,874, filed Aug. 22, 1997, 60/056,910, filed Aug. 22, 1997, 60/056,864, filed Aug. 22, 1997, 60/056,631, filed Aug. 22, 1997, 60/056,845, filed Aug. 22, 1997, 60/056,892, filed Aug. 22, 1997, 60/047,595, filed May 23, 1997, 60/057,761, filed Sep. 5, 1997, 60/047,599, filed May 23, 1997, 60/047,588, filed May 23, 1997, 60/047,585, filed May 23, 1997, 60/047,586, filed May 23, 1997, 60/047,590, filed May 23, 1997, 60/047,594, filed May 23, 1997, 60/047,589, filed May 23, 1997, 60/047,593, filed May 23, 1997, 60/047,614, filed May 23, 1997, 60/043,578, filed Apr. 11, 1997, 60/043,576, filed Apr. 11, 1997, 60/047,501, filed May 23, 1997, 60/043,670, filed Apr. 11, 1997, 60/056,632, filed Aug. 22, 1997, 60/056,664, filed Aug. 22, 1997, 60/056,876, filed Aug. 22, 1997, 60/056,881, filed Aug. 22, 1997, 60/056,909, filed Aug. 22, 1997, 60/056,875, filed Aug. 22, 1997, 60/056,862, filed Aug. 22, 1997, 60/056,887, filed Aug. 22, 1997, 60/056,908, filed Aug. 22, 1997, 60/048,964, filed Jun. 6, 1997, 60/057,650, filed Sep. 5, 1997, and 60/056,884, filed Aug. 22, 1997; U.S. application Ser. No. 10/100,683 is a continuation-in-part of U.S. application Ser. No. 09/882,171, filed Jun. 18, 2001, which claims the benefit of U.S. Provisional Application No. 60/190,068, filed Mar. 17, 2000; U.S. application Ser. No. 09/882,171 is a continuation of U.S. application Ser. No. 09/809,391, filed Mar. 16, 2001, which is a continuation-in-part of U.S. application Ser. No. 09/149,476, filed Sep. 8, 1998, which is a continuation-in-part of International Application No. PCT/US98/04493, filed Mar. 6, 1998; U.S. application Ser. No. 10/100,683 is a continuation-in-part of U.S. application Ser. No. 09/809,391, filed Mar. 16, 2001, which claims the benefit of U.S. Provisional Application No. 60/190,068, filed Mar. 17, 2000; U.S. application Ser. No. 09/809,391 is a continuation-in-part of U.S. application Ser. No. 09/149,476, filed Sep. 8, 1998, which is a continuation-in-part of International Application No. PCT/US98/04493, filed Mar. 6, 1998; U.S. application Ser. No. 10/100,683 is a continuation-in-part of U.S. application Ser. No. 09/149,476, filed Sep. 8, 1998, which is a continuation-in-part of International Application No. PCT/US98/04493, filed Mar. 6, 1998; U.S. application Ser. No. 10/100,683 is a continuation-in-part of International Application No. PCT/US98/04493, filed Mar. 6, 1998, which claims the benefit of U.S. Provisional Application Nos. 60/040,161, filed Mar. 7, 1997, 60/040,162, filed Mar. 7, 1997, 60/040,333, filed Mar. 7, 1997, 60/038,621, filed Mar. 7, 1997, 60/040,626, filed Mar. 7, 1997, 60/040,334, filed Mar. 7, 1997, 60/040,336, filed Mar. 7, 1997, 60/040,163, filed Mar. 7, 1997, 60/047,600, filed May 23, 1997, 60/047,615, filed May 23, 1997, 60/047,597, filed May 23, 1997, 60/047,502, filed May 23, 1997, 60/047,633, filed May 23, 1997, 60/047,583, filed May 23, 1997, 60/047,617, filed May 23, 1997, 60/047,618, filed May 23, 1997, 60/047,503, filed May 23, 1997, 60/047,592, filed May 23, 1997, 60/047,581, filed May 23, 1997, 60/047,584, filed May 23, 1997, 60/047,500, filed May 23, 1997, 60/047,587, filed May 23, 1997, 60/047,492, filed May 23, 1997, 60/047,598, filed May 23, 1997, 60/047,613, filed May 23, 1997, 60/047,582, filed May 23, 1997, 60/047,596, filed May 23, 1997, 60/047,612, filed May 23, 1997, 60/047,632, filed May 23, 1997, 60/047,601, filed May 23, 1997, 60/043,580, filed Apr. 11, 1997, 60/043,568, filed Apr. 11, 1997, 60/043,314, filed Apr. 11, 1997, 60/043,569, filed Apr. 11, 1997, 60/043,311, filed Apr. 11, 1997, 60/043,671, filed Apr. 11, 1997, 60/043,674, filed Apr. 11, 1997, 60/043,669, filed Apr. 11, 1997, 60/043,312, filed Apr. 11, 1997, 60/043,313, filed Apr. 11, 1997, 60/043,672, filed Apr. 11, 1997, 60/043,315, filed Apr. 11, 1997, 60/048,974, filed Jun. 6, 1997, 60/056,886, filed Aug. 22, 1997, 60/056,877, filed Aug. 22, 1997, 60/056,889, filed Aug. 22, 1997, 60/056,893, filed Aug. 22, 1997, 60/056,630, filed Aug. 22, 1997, 60/056,878, filed Aug. 22, 1997, 60/056,662, filed Aug. 22, 1997, 60/056,872, filed Aug. 22, 1997, 60/056,882, filed Aug. 22, 1997, 60/056,637, filed Aug. 22, 1997, 60/056,903, filed Aug. 22, 1997, 60/056,888, filed Aug. 22, 1997, 60/056,879, filed Aug. 22, 1997, 60/056,880, filed Aug. 22, 1997, 60/056,894, filed Aug. 22, 1997, 60/056,911, filed Aug. 22, 1997, 60/056,636, filed Aug. 22, 1997, 60/056,874, filed Aug. 22, 1997, 60/056,910, filed Aug. 22, 1997, 60/056,864, filed Aug. 22, 1997, 60/056,631, filed Aug. 22, 1997, 60/056,845, filed Aug. 22, 1997, 60/056,892, filed Aug. 22, 1997, 60/057,761, filed Sep. 5, 1997, 60/047,595, filed May 23, 1997, 60/047,599, filed May 23, 1997, 60/047,588, filed May 23, 1997, 60/047,585, filed May 23, 1997, 60/047,586, filed May 23, 1997, 60/047,590, filed May 23, 1997, 60/047,594, filed May 23, 1997, 60/047,589, filed May 23, 1997, 60/047,593, filed May 23, 1997, 60/047,614, filed May 23, 1997, 60/043,578, filed Apr. 11, 1997, 60/043,576, filed Apr. 11, 1997, 60/047,501, filed May 23, 1997, 60/043,670, filed Apr. 11, 1997, 60/056,632, filed Aug. 22, 1997, 60/056,664, filed Aug. 22, 1997, 60/056,876, filed Aug. 22, 1997, 60/056,881, filed Aug. 22, 1997, 60/056,909, filed Aug. 22, 1997, 60/056,875, filed Aug. 22, 1997, 60/056,862, filed Aug. 22, 1997, 60/056,887, filed Aug. 22, 1997, 60/056,908, filed Aug. 22, 1997, 60/048,964, filed Jun. 6, 1997, 60/057,650, filed Sep. 5, 1997, 60/056,884, filed Aug. 22, 1997, 60/057,669, filed Sep. 5, 1997, 60/049,610, filed Jun. 13, 1997, 60/061,060, filed Oct. 2, 1997, 60/051,926, filed Jul. 8, 1997, 60/052,874, filed Jul. 16, 1997, 60/058,785, filed Sep. 12, 1997, and 60/055,724, filed Aug. 18, 1997; U.S. application Ser. No. 10/100,683 is a continuation-in-part of U.S. application Ser. No. 10/058,993, filed Jan. 30, 2002, which claims the benefit of U.S. Provisional Application No. 60/265,583, filed Feb. 2, 2001; U.S. application Ser. No. 10/058,993 is a continuation-in-part of U.S. application Ser. No. 09/852,659, filed May 11, 2001, which is a continuation-in-part of U.S. application Ser. No. 09/152,060, filed Sep. 11, 1998, which is a continuation-in-part of International Application No. PCT/US98/04858, filed Mar. 12, 1998; U.S. application Ser. No. 10/058,993 is a continuation-in-part of U.S. application Ser. No. 09/853,161, filed May 11, 2001, which is a continuation-in-part of U.S. application Ser. No. 09/152,060, filed Sep. 11, 1998, which is a continuation-in-part of International Application No. PCT/US98/04858, filed Mar. 12, 1998; U.S. application Ser. No. 10/058,993 is a continuation-in-part of U.S. application Ser. No. 09/852,797, filed May 11, 2001, which is a continuation-in-part of U.S. application Ser. No. 09/152,060, filed Sep. 11, 1998, which is a continuation-in-part of International Application No. PCT/US98/04858, filed Mar. 12, 1998; U.S. application Ser. No. 10/100,683 is a continuation-in-part of U.S. application Ser. No. 09/852,659, filed May 11, 2001, which claims the benefit of U.S. Provisional Application No. 60/265,583, filed Feb. 2, 2001; U.S. application Ser. No. 09/852,659 is a continuation-in-part of U.S. application Ser. No. 09/152,060, filed Sep. 11, 1998, which is a continuation-in-part of International Application No. PCT/US98/04858, filed Mar. 12, 1998; U.S. application Ser. No. 10/100,683 is a continuation-in-part of U.S. application Ser. No. 09/853,161, filed May 11, 2001, which claims the benefit of U.S. Provisional Application No. 60/265,583, filed Feb. 2, 2001; U.S. application Ser. No. 09/853,161 is a continuation-in-part of U.S. application Ser. No. 09/152,060, filed Sep. 11, 1998, which is a continuation-in-part of International Application No. PCT/US98/04858, filed Mar. 12, 1998; U.S. application Ser. No. 10/100,683 is a continuation-in-part of U.S. application Ser. No. 09/852,797, filed May 11, 2001, which claims the benefit of U.S. Provisional Application No. 60/265,583, filed Feb. 2, 2001; U.S. application Ser. No. 09/852,797 is a continuation-in-part of U.S. application Ser. No. 09/152,060, filed Sep. 11, 1998, which is a continuation-in-part of International Application No. PCT/US98/04858, filed Mar. 12, 1998; U.S. application Ser. No. 10/100,683 is a continuation-in-part of U.S. application Ser. No. 09/152,060, filed Sep. 11, 1998, which is a continuation-in-part of International Application No. PCT/US98/04858, filed Mar. 12, 1998; U.S. application Ser. No. 10/100,683 is a continuation-in-part of International Application No. PCT/US98/04858, filed Mar. 12, 1998, which claims the benefit of U.S. Provisional Application Nos. 60/040,762, filed Mar. 14, 1997, 60/040,710, filed Mar. 14, 1997, 60/050,934, filed May 30, 1997, 60/048,100, filed May 30, 1997, 60/048,357, filed May 30, 1997, 60/048,189, filed May 30, 1997, 60/057,765, filed Sep. 5, 1997, 60/048,970, filed Jun. 6, 1997, and 60/068,368, filed Dec. 19, 1997; U.S. application Ser. No. 10/100,683 is a continuation-in-part of U.S. application Ser. No. 10/059,395, filed Jan. 31, 2002, which is a divisional of U.S. application Ser. No. 09/966,262, filed Oct. 1, 2001, which is a continuation of U.S. application Ser. No. 09/154,707, filed Sep. 17, 1998, which is a continuation-in-part of International Application No. PCT/US98/05311, filed Mar. 19, 1998; U.S. application Ser. No. 10/100,683 is a continuation-in-part of U.S. application Ser. No. 09/984,245, filed Oct. 29, 2001, which is a divisional of U.S. application Ser. No. 09/154,707, filed Sep. 17, 1998, which is a continuation-in-part of International Application No. PCT/US98/05311, filed Mar. 19, 1998; U.S. application Ser. No. 10/100,683 is a continuation-in-part of U.S. application Ser. No. 09/983,966, filed Oct. 26, 2001, which is a divisional of U.S. application Ser. No. 09/154,707, filed Sep. 17, 1998, which is a continuation-in-part of International Application No. PCT/US98/05311, filed Mar. 19, 1998; U.S. application Ser. No. 10/100,683 is a continuation-in-part of U.S. application Ser. No. 09/966,262, filed Oct. 1, 2001, which is a continuation of U.S. application Ser. No. 09/154,707, filed Sep. 17, 1998, which is a continuation-in-part of International Application No. PCT/US98/05311, filed Mar. 19, 1998; U.S. application Ser. No. 10/100,683 is a continuation-in-part of U.S. application Ser. No. 09/154,707, filed Sep. 17, 1998, which is a continuation-in-part of International Application No. PCT/US98/05311, filed Mar. 19, 1998; U.S. application Ser. No. 10/100,683 is a continuation-in-part of International Application No. PCT/US98/05311, filed Mar. 19, 1998, which claims the benefit of U.S. Provisional Application Nos. 60/041,277, filed Mar. 21, 1997, 60/042,344, filed Mar. 21, 1997, 60/041,276, filed Mar. 21, 1997, 60/041,281, filed Mar. 21, 1997, 60/048,094, filed May 30, 1997, 60/048,350, filed May 30, 1997, 60/048,188, filed May 30, 1997, 60/048,135, filed May 30, 1997, 60/050,937, filed May 30, 1997, 60/048,187, filed May 30, 1997, 60/048,099, filed May 30, 1997, 60/048,352, filed May 30, 1997, 60/048,186, filed May 30, 1997, 60/048,069, filed May 30, 1997, 60/048,095, filed May 30, 1997, 60/048,131, filed May 30, 1997, 60/048,096, filed May 30, 1997, 60/048,355, filed May 30, 1997, 60/048,160, filed May 30, 1997, 60/048,351, filed May 30, 1997, 60/048,154, filed May 30, 1997, 60/054,804, filed Aug. 5, 1997, 60/056,370, filed Aug. 19, 1997, and 60/060,862, filed Oct. 2, 1997; U.S. application Ser. No. 10/100,683 is a continuation-in-part of U.S. application Ser. No. 09/814,122, filed Mar. 22, 2001, which is a continuation of U.S. application Ser. No. 09/577,145, filed May 24, 2000, which is a continuation of U.S. application Ser. No. 09/166,780, filed Oct. 6, 1998, which is a continuation-in-part of International Application No. PCT/US98/06801, filed Apr. 7, 1998; U.S. application Ser. No. 10/100,683 is a continuation-in-part of International Application No. PCT/US98/06801, filed Apr. 7, 1998, which claims the benefit of U.S. Provisional Application Nos. 60/042,726, filed Apr. 8, 1997, 60/042,727, filed Apr. 8, 1997, 60/042,728, filed Apr. 8, 1997, 60/042,754, filed Apr. 8, 1997, 60/042,825, filed Apr. 8, 1997, 60/048,068, filed May 30, 1997, 60/048,070, filed May 30, 1997, and 60/048,184, filed May 30, 1997; U.S. application Ser. No. 10/100,683 is a continuation-in-part of International Application No. PCT/US98/06801, filed Apr. 7, 1998, which claims the benefit of U.S. Provisional Application Nos. 60/042,726, filed Apr. 8, 1997, 60/042,727, filed Apr. 8, 1997, 60/042,728, filed Apr. 8, 1997, 60/042,754, filed Apr. 8, 1997, 60/042,825, filed Apr. 8, 1997, 60/048,068, filed May 30, 1997, 60/048,070, filed May 30, 1997, and 60/048,184, filed May 30, 1997; U.S. application Ser. No. 10/100,683 is a continuation-in-part of International Application No. PCT/US98/10868, filed May 28, 1998, which claims the benefit of U.S. Provisional Application Nos. 60/044,039, filed May 30, 1997, 60/048,093, filed May 30, 1997, 60/048,190, filed May 30, 1997, 60/050,935, filed May 30, 1997, 60/048,101, filed May 30, 1997, 60/048,356, filed May 30, 1997, 60/056,250, filed Aug. 29, 1997, 60/056,296, filed Aug. 29, 1997, and 60/056,293, filed Aug. 29, 1997; U.S. application Ser. No. 10/100,683 is a continuation-in-part of International Application No. PCT/US98/11422, filed Jun. 4, 1998, which claims the benefit of U.S. Provisional Application Nos. 60/048,885, filed Jun. 6, 1997, 60/049,375, filed Jun. 6, 1997, 60/048,881, filed Jun. 6, 1997, 60/048,880, filed Jun. 6, 1997, 60/048,896, filed Jun. 6, 1997, 60/049,020, filed Jun. 6, 1997, 60/048,876, filed Jun. 6, 1997, 60/048,895, filed Jun. 6, 1997, 60/048,884, filed Jun. 6, 1997, 60/048,894, filed Jun. 6, 1997, 60/048,971, filed Jun. 6, 1997, 60/048,964, filed Jun. 6, 1997, 60/048,882, filed Jun. 6, 1997, 60/048,899, filed Jun. 6, 1997, 60/048,893, filed Jun. 6, 1997, 60/048,900, filed Jun. 6, 1997, 60/048,901, filed Jun. 6, 1997, 60/048,892, filed Jun. 6, 1997, 60/048,915, filed Jun. 6, 1997, 60/049,019, filed Jun. 6, 1997, 60/048,970, filed Jun. 6, 1997, 60/048,972, filed Jun. 6, 1997, 60/048,916, filed Jun. 6, 1997, 60/049,373, filed Jun. 6, 1997, 60/048,875, filed Jun. 6, 1997, 60/049,374, filed Jun. 6, 1997, 60/048,917, filed Jun. 6, 1997, 60/048,949, filed Jun. 6, 1997, 60/048,974, filed Jun. 6, 1997, 60/048,883, filed Jun. 6, 1997, 60/048,897, filed Jun. 6, 1997, 60/048,898, filed Jun. 6, 1997, 60/048,962, filed Jun. 6, 1997, 60/048,963, filed Jun. 6, 1997, 60/048,877, filed Jun. 6, 1997, 60/048,878, filed Jun. 6, 1997, 60/057,645, filed Sep. 5, 1997, 60/057,642, filed Sep. 5, 1997, 60/057,668, filed Sep. 5, 1997, 60/057,635, filed Sep. 5, 1997, 60/057,627, filed Sep. 5, 1997, 60/057,667, filed Sep. 5, 1997, 60/057,666, filed Sep. 5, 1997, 60/057,764, filed Sep. 5, 1997, 60/057,643, filed Sep. 5, 1997, 60/057,769, filed Sep. 5, 1997, 60/057,763, filed Sep. 5, 1997, 60/057,650, filed Sep. 5, 1997, 60/057,584, filed Sep. 5, 1997, 60/057,647, filed Sep. 5, 1997, 60/057,661, filed Sep. 5, 1997, 60/057,662, filed Sep. 5, 1997, 60/057,646, filed Sep. 5, 1997, 60/057,654, filed Sep. 5, 1997, 60/057,651, filed Sep. 5, 1997, 60/057,644, filed Sep. 5, 1997, 60/057,765, filed Sep. 5, 1997, 60/057,762, filed Sep. 5, 1997, 60/057,775, filed Sep. 5, 1997, 60/057,648, filed Sep. 5, 1997, 60/057,774, filed Sep. 5, 1997, 60/057,649, filed Sep. 5, 1997, 60/057,770, filed Sep. 5, 1997, 60/057,771, filed Sep. 5, 1997, 60/057,761, filed Sep. 5, 1997, 60/057,760, filed Sep. 5, 1997, 60/057,776, filed Sep. 5, 1997, 60/057,778, filed Sep. 5, 1997, 60/057,629, filed Sep. 5, 1997, 60/057,628, filed Sep. 5, 1997, 60/057,777, filed Sep. 5, 1997, 60/057,634, filed Sep. 5, 1997, and 60/070,923, filed Dec. 18, 1997; U.S. application Ser. No. 10/100,683 is a continuation-in-part of International Application No. PCT/US01/05614, filed Feb. 21, 2001, which claims the benefit of U.S. Provisional Application Nos. 60/184,836, filed Feb. 24, 2000, and 60/193,170, filed Mar. 29, 2000; U.S. application Ser. No. 10/100,683 is a continuation-in-part of International Application No. PCT/US98/12125, filed Jun. 11, 1998, which claims the benefit of U.S. Provisional Application Nos. 60/049,547, filed Jun. 13, 1997, 60/049,548, filed Jun. 13, 1997, 60/049,549, filed Jun. 13, 1997, 60/049,550, filed Jun. 13, 1997, 60/049,566, filed Jun. 13, 1997, 60/049,606, filed Jun. 13, 1997, 60/049,607, filed Jun. 13, 1997, 60/049,608, filed Jun. 13, 1997, 60/049,609, filed Jun. 13, 1997, 60/049,610, filed Jun. 13, 1997, 60/049,611, filed Jun. 13, 1997, 60/050,901, filed Jun. 13, 1997, 60/052,989, filed Jun. 13, 1997, 60/051,919, filed Jul. 8, 1997, 60/055,984, filed Aug. 18, 1997, 60/058,665, filed Sep. 12, 1997, 60/058,668, filed Sep. 12, 1997, 60/058,669, filed Sep. 12, 1997, 60/058,750, filed Sep. 12, 1997, 60/058,971, filed Sep. 12, 1997, 60/058,972, filed Sep. 12, 1997, 60/058,975, filed Sep. 12, 1997, 60/060,834, filed Oct. 2, 1997, 60/060,841, filed Oct. 2, 1997, 60/060,844, filed Oct. 2, 1997, 60/060,865, filed Oct. 2, 1997, 60/061,059, filed Oct. 2, 1997, and 60/061,060, filed Oct. 2, 1997; U.S. application Ser. No. 10/100,683 is a continuation-in-part of U.S. application Ser. No. 09/627,081, filed Jul. 27, 2000, which is a continuation of U.S. application Ser. No. 09/213,365, filed Dec. 17, 1998, which is a continuation-in-part of International Application No. PCT/US98/13608, filed Jun. 30, 1998; U.S. application Ser. No. 10/100,683 is a continuation-in-part of International Application No. PCT/US98/13608, filed Jun. 30, 1998, which claims the benefit of U.S. Provisional Application Nos. 60/051,480, filed Jul. 1, 1997, 60/051,381, filed Jul. 1, 1997, 60/058,663, filed Sep. 12, 1997, and 60/058,598, filed Sep. 12, 1997; U.S. application Ser. No. 10/100,683 is a continuation-in-part of U.S. application Ser. No. 09/984,490, filed Oct. 30, 2001, which is a divisional of U.S. application Ser. No. 09/227,357, filed Jan. 8, 1999, which is a continuation-in-part of International Application No. PCT/US98/13684, filed Jul. 7, 1998; U.S. application Ser. No. 10/100,683 is a continuation-in-part of U.S. application Ser. No. 09/983,802, filed Oct. 25, 2001, which is a continuation of U.S. application Ser. No. 09/227,357, filed Jan. 8, 1999, which is a continuation-in-part of International Application No. PCT/US98/13684, filed Jul. 7, 1998; U.S. application Ser. No. 10/100,683 is a continuation-in-part of U.S. application Ser. No. 09/973,278, filed Oct. 10, 2001, which claims the benefit of U.S. Provisional Application No. 60/239,899, filed Oct. 13, 2000; U.S. application Ser. No. 09/973,278 is a continuation-in-part of U.S. application Ser. No. 09/227,357, filed Jan. 8, 1999, which is a continuation-in-part of International Application No. PCT/US98/13684, filed Jul. 7, 1998; U.S. application Ser. No. 10/100,683 is a continuation-in-part of International Application No. PCT/US98/13684, filed Jul. 7, 1998, which claims the benefit of U.S. Provisional Application Nos. 60/051,926, filed Jul. 8, 1997, 60/052,793, filed Jul. 8, 1997, 60/051,925, filed Jul. 8, 1997, 60/051,929, filed Jul. 8, 1997, 60/052,803, filed Jul. 8, 1997, 60/052,732, filed Jul. 8, 1997, 60/051,931, filed Jul. 8, 1997, 60/051,932, filed Jul. 8, 1997, 60/051,916, filed Jul. 8, 1997, 60/051,930, filed Jul. 8, 1997, 60/051,918, filed Jul. 8, 1997, 60/051,920, filed Jul. 8, 1997, 60/052,733, filed Jul. 8, 1997, 60/052,795, filed Jul. 8, 1997, 60/051,919, filed Jul. 8, 1997, 60/051,928, filed Jul. 8, 1997, 60/055,722, filed Aug. 18, 1997, 60/055,723, filed Aug. 18, 1997, 60/055,948, filed Aug. 18, 1997, 60/055,949, filed Aug. 18, 1997, 60/055,953, filed Aug. 18, 1997, 60/055,950, filed Aug. 18, 1997, 60/055,947, filed Aug. 18, 1997, 60/055,964, filed Aug. 18, 1997, 60/056,360, filed Aug. 18, 1997, 60/055,684, filed Aug. 18, 1997, 60/055,984, filed Aug. 18, 1997, 60/055,954, filed Aug. 18, 1997, 60/058,785, filed Sep. 12, 1997, 60/058,664, filed Sep. 12, 1997, 60/058,660, filed Sep. 12, 1997, and 60/058,661, filed Sep. 12, 1997; U.S. application Ser. No. 10/100,683 is a continuation-in-part of U.S. application Ser. No. 09/776,724, filed Feb. 6, 2001, which claims the benefit of U.S. Provisional Application No. 60/180,909, filed Feb. 8, 2000; U.S. application Ser. No. 09/776,724 is a continuation-in-part of U.S. application Ser. No. 09/669,688, filed Sep. 26, 2000, which is a continuation of U.S. application Ser. No. 09/229,982, filed Jan. 14, 1999, which is a continuation-in-part of International Application No. PCT/US98/14613, filed Jul. 15, 1998; U.S. application Ser. No. 10/100,683 is a continuation-in-part of U.S. application Ser. No. 09/669,688, filed Sep. 26, 2000, which is a continuation of U.S. application Ser. No. 09/229,982, filed Jan. 14, 1999, which is a continuation-in-part of International Application No. PCT/US98/14613, filed Jul. 15, 1998; U.S. application Ser. No. 10/100,683 is a continuation-in-part of U.S. application Ser. No. 09/229,982, filed Jan. 14, 1999, which is a continuation-in-part of International Application No. PCT/US98/14613, filed Jul. 15, 1998; U.S. application Ser. No. 10/100,683 is a continuation-in-part of International Application No. PCT/US98/14613, filed Jul. 15, 1998, which claims the benefit of U.S. Provisional Application Nos. 60/052,661, filed Jul. 16, 1997, 60/052,872, filed Jul. 16, 1997, 60/052,871, filed Jul. 16, 1997, 60/052,874, filed Jul. 16, 1997, 60/052,873, filed Jul. 16, 1997, 60/052,870, filed Jul. 16, 1997, 60/052,875, filed Jul. 16, 1997, 60/053,440, filed Jul. 22, 1997, 60/053,441, filed Jul. 22, 1997, 60/053,442, filed Jul. 22, 1997, 60/056,359, filed Aug. 18, 1997, 60/055,725, filed Aug. 18, 1997, 60/055,985, filed Aug. 18, 1997, 60/055,952, filed Aug. 18, 1997, 60/055,989, filed Aug. 18, 1997, 60/056,361, filed Aug. 18, 1997, 60/055,726, filed Aug. 18, 1997, 60/055,724, filed Aug. 18, 1997, 60/055,946, filed Aug. 18, 1997, and 60/055,683, filed Aug. 18, 1997; U.S. application Ser. No. 10/100,683 claims the benefit of U.S. Provisional Application No. 60/295,558, filed Jun. 5, 2001; U.S. application Ser. No. 10/100,683 is a continuation-in-part of U.S. application Ser. No. 09/820,649, filed Mar. 30, 2001, which is a continuation of U.S. application Ser. No. 09/666,984, filed Sep. 21, 2000, which is a continuation of U.S. application Ser. No. 09/236,557, filed Jan. 26, 1999, which is a continuation-in-part of International Application No. PCT/US98/15949, filed Jul. 29, 1998; U.S. application Ser. No. 10/100,683 is a continuation-in-part of International Application No. PCT/US98/15949, filed Jul. 29, 1998, which claims the benefit of U.S. Provisional Application Nos. 60/054,212, filed Jul. 30, 1997, 60/054,209, filed Jul. 30, 1997, 60/054,234, filed Jul. 30, 1997, 60/054,218, filed Jul. 30, 1997, 60/054,214, filed Jul. 30, 1997, 60/054,236, filed Jul. 30, 1997, 60/054,215, filed Jul. 30, 1997, 60/054,211, filed Jul. 30, 1997, 60/054,217, filed Jul. 30, 1997, 60/054,213, filed Jul. 30, 1997, 60/055,968, filed Aug. 18, 1997, 60/055,969, filed Aug. 18, 1997, 60/055,972, filed Aug. 18, 1997, 60/056,561, filed Aug. 19, 1997, 60/056,534, filed Aug. 19, 1997, 60/056,729, filed Aug. 19, 1997, 60/056,543, filed Aug. 19, 1997, 60/056,727, filed Aug. 19, 1997, 60/056,554, filed Aug. 19, 1997, and 60/056,730, filed Aug. 19, 1997; U.S. application Ser. No. 10/100,683 is a continuation-in-part of U.S. application Ser. No. 09/969,730, filed Oct. 4, 2001, which is a continuation-in-part of U.S. application Ser. No. 09/774,639, filed Feb. 1, 2001, which is a continuation of U.S. application Ser. No. 09/244,112, filed Feb. 4, 1999, which is a continuation-in-part of International Application No. PCT/US98/16235, filed Aug. 4, 1998; U.S. application Ser. No. 10/100,683 is a continuation-in-part of U.S. application Ser. No. 09/774,639, filed Feb. 1, 2001, which is a continuation of U.S. application Ser. No. 09/244,112, filed Feb. 4, 1999, which is a continuation-in-part of International Application No. PCT/US98/16235, filed Aug. 4, 1998; U.S. application Ser. No. 10/100,683 is a continuation-in-part of U.S. application Ser. No. 09/969,730, filed Oct. 4, 2001, which claims the benefit of U.S. Provisional Application No. 60/238,291, filed Oct. 6, 2000; U.S. application Ser. No. 10/100,683 is a continuation-in-part of International Application No. PCT/US98/16235, filed Aug. 4, 1998, which claims the benefit of U.S. Provisional Application Nos. 60/055,386, filed Aug. 5, 1997, 60/054,807, filed Aug. 5, 1997, 60/055,312, filed Aug. 5, 1997, 60/055,309, filed Aug. 5, 1997, 60/054,798, filed Aug. 5, 1997, 60/055, 310, filed Aug. 5, 1997, 60/054,806, filed Aug. 5, 1997, 60/054,809, filed Aug. 5, 1997, 60/054,804, filed Aug. 5, 1997, 60/054,803, filed Aug. 5, 1997, 60/054,808, filed Aug. 5, 1997, 60/055,311, filed Aug. 5, 1997, 60/055,986, filed Aug. 18, 1997, 60/055,970, filed Aug. 18, 1997, 60/056,563, filed Aug. 19, 1997, 60/056,557, filed Aug. 19, 1997, 60/056,731, filed Aug. 19, 1997, 60/056,365, filed Aug. 19, 1997, 60/056,367, filed Aug. 19, 1997, 60/056,370, filed Aug. 19, 1997, 60/056,364, filed Aug. 19, 1997, 60/056,366, filed Aug. 19, 1997, 60/056,732, filed Aug. 19, 1997, and 60/056,371, filed Aug. 19, 1997; U.S. application Ser. No. 10/100,683 is a continuation-in-part of U.S. application Ser. No. 09/716,128, filed Nov. 17, 2000, which is a continuation of U.S. application Ser. No. 09/251,329, filed Feb. 17, 1999, which is a continuation-in-part of International Application No. PCT/US98/17044, filed Aug. 18, 1998; U.S. application Ser. No. 10/100,683 is a continuation-in-part of International Application No. PCT/US98/17044, filed Aug. 18, 1998, which claims the benefit of U.S. Provisional Application Nos. 60/056,555, filed Aug. 19, 1997, 60/056,556, filed Aug. 19, 1997, 60/056,535, filed Aug. 19, 1997, 60/056,629, filed Aug. 19, 1997, 60/056,369, filed Aug. 19, 1997, 60/056,628, filed Aug. 19, 1997, 60/056,728, filed Aug. 19, 1997, 60/056,368, filed Aug. 19, 1997, 60/056,726, filed Aug. 19, 1997, 60/089,510, filed Jun. 16, 1998, and 60/092,956, filed Jul. 15, 1998; U.S. application Ser. No. 10/100,683 is a continuation-in-part of U.S. application Ser. No. 09/729,835, filed Dec. 6, 2000, which is a divisional of U.S. application Ser. No. 09/257,179, filed Feb. 25, 1999, which is a continuation-in-part of International Application No. PCT/US98/17709, filed Aug. 27, 1998; U.S. application Ser. No. 10/100,683 is a continuation-in-part of U.S. application Ser. No. 09/257,179, filed Feb. 25, 1999, which is a continuation-in-part of International Application No. PCT/US98/17709, filed Aug. 27, 1998; U.S. application Ser. No. 10/100,683 is a continuation-in-part of International Application No. PCT/US98/17709, filed Aug. 27, 1998, which claims the benefit of U.S. Provisional Application Nos. 60/056,270, filed Aug. 29, 1997, 60/056,271, filed Aug. 29, 1997, 60/056,247, filed Aug. 29, 1997, and 60/056,073, filed Aug. 29, 1997; U.S. application Ser. No. 10/100,683 is a continuation-in-part of U.S. application Ser. No. 10/047,021, filed Jan. 17, 2002, which is a continuation-in-part of U.S. application Ser. No. 09/722,329, filed Nov. 28, 2000, which is a continuation of U.S. application Ser. No. 09/262,109, filed Mar. 4, 1999, which is a continuation-in-part of International Application No. PCT/US98/18360, filed Sep. 3, 1998; U.S. application Ser. No. 10/100,683 is a continuation-in-part of U.S. application Ser. No. 09/722,329, filed Nov. 28, 2000, which is a continuation of U.S. application Ser. No. 09/262,109, filed Mar. 4, 1999, which is a continuation-in-part of International Application No. PCT/US98/18360, filed Sep. 3, 1998; U.S. application Ser. No. 10/100,683 is a continuation-in-part of International Application No. PCT/US02/01109, filed Jan. 17, 2002, which claims the benefit of U.S. Provisional Application No. 60/262,066, filed Jan. 18, 2001; U.S. application Ser. No. 10/100,683 is a continuation-in-part of International Application No. PCT/US98/18360, filed Sep. 3, 1998, which claims the benefit of U.S. Provisional Application Nos. 60/057,626, filed Sep. 5, 1997, 60/057,663, filed Sep. 5, 1997, 60/057,669, filed Sep. 5, 1997, 60/058,667, filed Sep. 12, 1997, 60/058,974, filed Sep. 12, 1997, 60/058,973, filed Sep. 12, 1997, 60/058,666, filed Sep. 12, 1997, and 60/090,112, filed Jun. 22, 1998; U.S. application Ser. No. 10/100,683 is a continuation-in-part of U.S. application Ser. No. 09/281,976, filed Mar. 31, 1999, which is a continuation-in-part of International Application No. PCT/US98/20775, filed Oct. 1, 1998; U.S. application Ser. No. 10/100,683 is a continuation-in-part of International Application No. PCT/US98/20775, filed Oct. 1, 1998, which claims the benefit of U.S. Provisional Application Nos. 60/060,837, filed Oct. 2, 1997, 60/060,862, filed Oct. 2, 1997, 60/060,839, filed Oct. 2, 1997, 60/060,866, filed Oct. 2, 1997, 60/060,843, filed Oct. 2, 1997, 60/060,836, filed Oct. 2, 1997, 60/060,838, filed Oct. 2, 1997, 60/060,874, filed Oct. 2, 1997, 60/060,833, filed Oct. 2, 1997, 60/060,884, filed Oct. 2, 1997, and 60/060,880, filed Oct. 2, 1997; U.S. application Ser. No. 10/100,683 is a continuation-in-part of U.S. application Ser. No. 09/984,429, filed Oct. 30, 2001, which claims the benefit of U.S. Provisional Application No. 60/244,591, filed Nov. 1, 2000; U.S. application Ser. No. 09/984,429 is a continuation-in-part of U.S. application Ser. No. 09/288,143, filed Apr. 8, 1999, which is a continuation-in-part of International Application No. PCT/US98/21142, filed Oct. 8, 1998; U.S. application Ser. No. 10/100,683 claims the benefit of U.S. Provisional Application No. 60/244,591, filed Nov. 1, 2000; U.S. application Ser. No. 10/100,683 is a continuation-in-part of U.S. application Ser. No. 09/288,143, filed Apr. 8, 1999, which is a continuation-in-part of International Application No. PCT/US98/21142, filed Oct. 8, 1998; U.S. application Ser. No. 10/100,683 is a continuation-in-part of International Application No. PCT/US98/21142, filed Oct. 8, 1998, which claims the benefit of U.S. Provisional Application Nos. 60/061,463, filed Oct. 9, 1997, 60/061,529, filed Oct. 9, 1997, 60/071,498, filed Oct. 9, 1997, 60/061,527, filed Oct. 9, 1997, 60/061,536, filed Oct. 9, 1997, and 60/061,532, filed Oct. 9, 1997; U.S. application Ser. No. 10/100,683 is a continuation-in-part of U.S. application Ser. No. 09/296,622, filed Apr. 23, 1999, which is a continuation-in-part of International Application No. PCT/US98/22376, filed Oct. 23, 1998; U.S. application Ser. No. 10/100,683 is a continuation-in-part of International Application No. PCT/US98/22376, filed Oct. 23, 1998, which claims the benefit of U.S. Provisional Application Nos. 60/063,099, filed Oct. 24, 1997, 60/063,088, filed Oct. 24, 1997, 60/063,100, filed Oct. 24, 1997, 60/063,387, filed Oct. 24, 1997, 60/063,148, filed Oct. 24, 1997, 60/063,386, filed Oct. 24, 1997, 60/062,784, filed Oct. 24, 1997, 60/063,091, filed Oct. 24, 1997, 60/063,090, filed Oct. 24, 1997, 60/063,089, filed Oct. 24, 1997, 60/063,092, filed Oct. 24, 1997, 60/063,111, filed Oct. 24, 1997, 60/063,101, filed Oct. 24, 1997, 60/063,109, filed Oct. 24, 1997, 60/063,110, filed Oct. 24, 1997, 60/063,098, filed Oct. 24, 1997, and 60/063,097, filed Oct. 24, 1997; U.S. application Ser. No. 10/100,683 is a continuation-in-part of U.S. application Ser. No. 09/974,879, filed Oct. 12, 2001, which claims the benefit of U.S. Provisional Application No. 60/239,893, filed Oct. 13, 2000; U.S. application Ser. No. 09/974,879 is a continuation-in-part of U.S. application Ser. No. 09/818,683, filed Mar. 28, 2001, which is a continuation of U.S. application Ser. No. 09/305,736, filed May 5, 1999, which is a continuation-in-part of International Application No. PCT/US98/23435, filed Nov. 4, 1998; U.S. application Ser. No. 10/100,683 is a continuation-in-part of U.S. application Ser. No. 09/818,683, filed Mar. 28, 2001, which is a continuation of U.S. application Ser. No. 09/305,736, filed May 5, 1999, which is a continuation-in-part of International Application No. PCT/US98/23435, filed Nov. 4, 1998; U.S. application Ser. No. 10/100,683 is a continuation-in-part of U.S. application Ser. No. 09/305,736, filed May 5, 1999, which is a continuation-in-part of International Application No. PCT/US98/23435, filed Nov. 4, 1998; U.S. application Ser. No. 10/100,683 is a continuation-in-part of International Application No. PCT/US98/23435, filed Nov. 4, 1998, which claims the benefit of U.S. Provisional Application Nos. 60/064,911, filed Nov. 7, 1997, 60/064,912, filed Nov. 7, 1997, 60/064,983, filed Nov. 7, 1997, 60/064,900, filed Nov. 7, 1997, 60/064,988, filed Nov. 7, 1997, 60/064,987, filed Nov. 7, 1997, 60/064,908, filed Nov. 7, 1997, 60/064,984, filed Nov. 7, 1997, 60/064,985, filed Nov. 7, 1997, 60/066,094, filed Nov. 17, 1997, 60/066,100, filed Nov. 17, 1997, 60/066,089, filed Nov. 17, 1997, 60/066,095, filed Nov. 17, 1997, and 60/066,090, filed Nov. 17, 1997; U.S. application Ser. No. 10/100,683 is a continuation-in-part of U.S. application Ser. No. 09/334,595, filed Jun. 17, 1999, which is a continuation-in-part of International Application No. PCT/US98/27059, filed Dec. 17, 1998; U.S. application Ser. No. 10/100,683 is a continuation-in-part of International Application No. PCT/US98/27059, filed Dec. 17, 1998, which claims the benefit of U.S. Provisional Application Nos. 60/070,923, filed Dec. 18, 1997, 60/068,007, filed Dec. 18, 1997, 60/068,057, filed Dec. 18, 1997, 60/068,006, filed Dec. 18, 1997, 60/068,369, filed Dec. 19, 1997, 60/068,367, filed Dec. 19, 1997, 60/068,368, filed Dec. 19, 1997, 60/068,169, filed Dec. 19, 1997, 60/068,053, filed Dec. 18, 1997, 60/068,064, filed Dec. 18, 1997, 60/068,054, filed Dec. 18, 1997, 60/068,008, filed Dec. 18, 1997, and 60/068,365, filed Dec. 19, 1997; U.S. application Ser. No. 10/100,683 is a continuation-in-part of U.S. application Ser. No. 09/938,671, filed Aug. 27, 2001, which is a continuation of U.S. application Ser. No. 09/739,907, filed Dec. 20, 2000, which is a continuation of U.S. application Ser. No. 09/348,457, filed Jul. 7, 1999, which is a continuation-in-part of International Application No. PCT/US99/00108, filed Jan. 6, 1999; U.S. application Ser. No. 10/100,683 is a continuation-in-part of U.S. application Ser. No. 09/739,907, filed Dec. 20, 2000, which is a continuation of U.S. application Ser. No. 09/348,457, filed Jul. 7, 1999, which is a continuation-in-part of International Application No. PCT/US99/00108, filed Jan. 6, 1999; U.S. application Ser. No. 10/100,683 is a continuation-in-part of U.S. application Ser. No. 09/348,457, filed Jul. 7, 1999, which is a continuation-in-part of International Application No. PCT/US99/00108, filed Jan. 6, 1999; U.S. application Ser. No. 10/100,683 is a continuation-in-part of International Application No. PCT/US99/00108, filed Jan. 6, 1999, which claims the benefit of U.S. Provisional Application Nos. 60/070,704, filed Jan. 7, 1998, 60/070,658, filed Jan. 7, 1998, 60/070,692, filed Jan. 7, 1998, and 60/070,657, filed Jan. 7, 1998; U.S. application Ser. No. 10/100,683 is a continuation-in-part of U.S. application Ser. No. 09/949,925, filed Sep. 12, 2001, which claims the benefit of U.S. Provisional Application No. 60/232,150, filed Sep. 12, 2000; U.S. application Ser. No. 09/949,925 is a continuation-in-part of International Application No. PCT/US99/01621, filed Jan. 27, 1999; U.S. application Ser. No. 09/949,925 is a continuation-in-part of U.S. application Ser. No. 09/363,044, filed Jul. 29, 1999, which is a continuation-in-part of International Application No. PCT/US99/01621, filed Jan. 27, 1999; U.S. application Ser. No. 10/100,683 is a continuation-in-part of U.S. application Ser. No. 09/813,153, filed Mar. 21, 2001, which is a continuation of U.S. application Ser. No. 09/363,044, filed Jul. 29, 1999, which is a continuation-in-part of International Application No. PCT/US99/01621, filed Jan. 27, 1999; U.S. application Ser. No. 10/100,683 is a continuation-in-part of U.S. application Ser. No. 09/363,044, filed Jul. 29, 1999, which is a continuation-in-part of International Application No. PCT/US99/01621, filed Jan. 27, 1999; U.S. application Ser. No. 10/100,683 is a continuation-in-part of International Application No. PCT/US99/01621, filed Jan. 27, 1999, which claims the benefit of U.S. Provisional Application Nos. 60/073,170, filed Jan. 30, 1998, 60/073,167, filed Jan. 30, 1998, 60/073,165, filed Jan. 30, 1998, 60/073,164, filed Jan. 30, 1998, 60/073,162, filed Jan. 30, 1998, 60/073,161, filed Jan. 30, 1998, 60/073,160, filed Jan. 30, 1998, and 60/073,159, filed Jan. 30, 1998; U.S. application Ser. No. 10/100,683 is a continuation-in-part of U.S. application Ser. No. 10/062,548, filed Feb. 5, 2002, which is a continuation of U.S. application Ser. No. 09/369,247, filed Aug. 5, 1999; U.S. application Ser. No. 09/369,247 is a continuation-in-part of International Application No. PCT/US99/02293, filed Feb. 4, 1999; U.S. application Ser. No. 10/100,683 is a continuation-in-part of U.S. application Ser. No. 09/369,247, filed Aug. 5, 1999; U.S. application Ser. No. 09/369,247 is a continuation-in-part of International Application No. PCT/US99/02293, filed Feb. 4, 1999; U.S. application Ser. No. 10/100,683 is a continuation-in-part of International Application No. PCT/US99/02293, filed Feb. 4, 1999, which claims the benefit of U.S. Provisional Application Nos. 60/074,118, filed Feb. 9, 1998, 60/074,157, filed Feb. 9, 1998, 60/074,037, filed Feb. 9, 1998, 60/074,141, filed Feb. 9, 1998, and 60/074,341, filed Feb. 9, 1998; U.S. application Ser. No. 10/100,683 is a continuation-in-part of U.S. application Ser. No. 09/716,129, filed Nov. 17, 2000, which is a continuation-in-part of International Application No. PCT/US99/03939, filed Feb. 24, 1999; U.S. application Ser. No. 09/716,129 is a continuation of U.S. application Ser. No. 09/382,572, filed Aug. 25, 1999, which is a continuation-in-part of International Application No. PCT/US99/03939, filed Feb. 24, 1999; U.S. application Ser. No. 10/100,683 is a continuation-in-part of International Application No. PCT/US99/03939, filed Feb. 24, 1999, which claims the benefit of U.S. Provisional Application Nos. 60/076,053, filed Feb. 26, 1998, 60/076,051, filed Feb. 26, 1998, 60/076,054, filed Feb. 26, 1998, 60/076,052, filed Feb. 26, 1998, and 60/076,057, filed Feb. 26, 1998; U.S. application Ser. No. 10/100,683 is a continuation-in-part of U.S. application Ser. No. 09/798,889, filed Mar. 6, 2001, which is a continuation of U.S. application Ser. No. 09/393,022, filed Sep. 9, 1999, which is a continuation-in-part of International Application No. PCT/US99/05721, filed Mar. 11, 1999; U.S. application Ser. No. 10/100,683 is a continuation-in-part of International Application No. PCT/US99/05721, filed Mar. 11, 1999, which claims the benefit of U.S. Provisional Application Nos. 60/077,714, filed Mar. 12, 1998, 60/077,686, filed Mar. 12, 1998, 60/077,687, filed Mar. 12, 1998, and 60/077,696, filed Mar. 12, 1998; U.S. application Ser. No. 10/100,683 is a continuation-in-part of U.S. application Ser. No. 09/397,945, filed Sep. 17, 1999, which is a continuation-in-part of International Application No. PCT/US99/05804, filed Mar. 18, 1999; U.S. application Ser. No. 10/100,683 is a continuation-in-part of International Application No. PCT/US99/05804, filed Mar. 18, 1999, which claims the benefit of U.S. Provisional Application Nos. 60/078,566, filed Mar. 19, 1998, 60/078,576, filed Mar. 19, 1998, 60/078,573, filed Mar. 19, 1998, 60/078,574, filed Mar. 19, 1998, 60/078,579, filed Mar. 19, 1998, 60/080,314, filed Apr. 1, 1998, 60/080,312, filed Apr. 1, 1998, 60/078,578, filed Mar. 19, 1998, 60/078,581, filed Mar. 19, 1998, 60/078,577, filed Mar. 19, 1998, 60/078,563, filed Mar. 19, 1998, and 60/080,313, filed Apr. 1, 1998; U.S. application Ser. No. 10/100,683 is a continuation-in-part of U.S. application Ser. No. 09/948,783, filed Sep. 10, 2001, which claims the benefit of U.S. Provisional Application No. 60/231,846, filed Sep. 11, 2000; U.S. application Ser. No. 09/948,783 is a continuation-in-part of U.S. application Ser. No. 09/892,877, filed Jun. 28, 2001, which is a continuation of U.S. application Ser. No. 09/437,658, filed Nov. 10, 1999, which is a continuation-in-part of International Application No. PCT/US99/09847, filed May 6, 1999; U.S. application Ser. No. 10/100,683 is a continuation-in-part of U.S. application Ser. No. 09/892,877, filed Jun. 28, 2001, which is a continuation of U.S. application Ser. No. 09/437,658, filed Nov. 10, 1999, which is a continuation-in-part of International Application No. PCT/US99/09847, filed May 6, 1999; U.S. application Ser. No. 10/100,683 is a continuation-in-part of International Application No. PCT/US99/09847, filed May 6, 1999, which claims the benefit of U.S. Provisional Application Nos. 60/085,093, filed May 12, 1998, 60/085,094, filed May 12, 1998, 60/085,105, filed May 12, 1998, 60/085,180, filed May 12, 1998, 60/085,927, filed May 18, 1998, 60/085,906, filed May 18, 1998, 60/085,920, filed May 18, 1998, 60/085,924, filed May 18, 1998, 60/085,922, filed May 18, 1998, 60/085,923, filed May 18, 1998, 60/085,921, filed May 18, 1998, 60/085,925, filed May 18, 1998, and 60/085,928, filed May 18, 1998; U.S. application Ser. No. 10/100,683 is a continuation-in-part of U.S. application Ser. No. 10/050,873, filed Jan. 18, 2002, which claims the benefit of U.S. Provisional Application Nos. 60/263,681, filed Jan. 24, 2001, and 60/263,230, filed Jan. 23, 2001; U.S. application Ser. No. 10/050,873 is a continuation-in-part of U.S. application Ser. No. 09/461,325, filed Dec. 14, 1999, which is a continuation-in-part of International Application No. PCT/US99/13418, filed Jun. 15, 1999; U.S. application Ser. No. 10/100,683 is a continuation-in-part of U.S. application Ser. No. 10/012,542, filed Dec. 12, 2001, which is a divisional of U.S. application Ser. No. 09/461,325, filed Dec. 14, 1999, which is a continuation-in-part of International Application No. PCT/US99/13418, filed Jun. 15, 1999; U.S. application Ser. No. 10/100,683 is a continuation-in-part of U.S. application Ser. No. 09/461,325, filed Dec. 14, 1999, which is a continuation-in-part of International Application No. PCT/US99/13418, filed Jun. 15, 1999; U.S. application Ser. No. 10/100,683 is a continuation-in-part of International Application No. PCT/US99/13418, filed Jun. 15, 1999, which claims the benefit of U.S. Provisional Application Nos. 60/089,507, filed Jun. 16, 1998, 60/089,508, filed Jun. 16, 1998, 60/089,509, filed Jun. 16, 1998, 60/089,510, filed Jun. 16, 1998, 60/090,112, filed Jun. 22, 1998, and 60/090,113, filed Jun. 22, 1998; U.S. application Ser. No. 10/100,683 is a continuation-in-part of U.S. application Ser. No. 09/984,271, filed Oct. 29, 2001, which is a divisional of U.S. application Ser. No. 09/482,273, filed Jan. 13, 2000, which is a continuation-in-part of International Application No. PCT/US99/15849, filed Jul. 14, 1999; U.S. application Ser. No. 10/100,683 is a continuation-in-part of U.S. application Ser. No. 09/984,276, filed Oct. 29, 2001, which is a divisional of U.S. application Ser. No. 09/482,273, filed Jan. 13, 2000, which is a continuation-in-part of International Application No. PCT/US99/15849, filed Jul. 14, 1999; U.S. application Ser. No. 10/100,683 is a continuation-in-part of U.S. application Ser. No. 09/482,273, filed Jan. 13, 2000, which is a continuation-in-part of International Application No. PCT/US99/15849, filed Jul. 14, 1999; U.S. application Ser. No. 10/100,683 is a continuation-in-part of International Application No. PCT/US99/15849, filed Jul. 14, 1999, which claims the benefit of U.S. Provisional Application Nos. 60/092,921, filed Jul. 15, 1998, 60/092,922, filed Jul. 15, 1998, and 60/092,956, filed Jul. 15, 1998; U.S. application Ser. No. 10/100,683 is a continuation-in-part of International Application No. PCT/US01/29871, filed Sep. 24, 2001, which claims the benefit of U.S. Provisional Application No. 60/234,925, filed Sep. 25, 2000; International Application No. PCT/US01/29871 is a continuation-in-part of International Application No. PCT/US01/00911, filed Jan. 12, 2001; U.S. application Ser. No. 10/100,683 is a continuation-in-part of International Application No. PCT/US01/00911, filed Jan. 12, 2001, which is a continuation-in-part of U.S. application Ser. No. 09/482,273, filed Jan. 13, 2000; U.S. application Ser. No. 10/100,683 claims the benefit of U.S. Provisional Application No. 60/350,898, filed Jan. 25, 2002; U.S. application Ser. No. 10/100,683 is a continuation-in-part of U.S. application Ser. No. 09/489,847, filed Jan. 24, 2000, which is a continuation-in-part of International Application No. PCT/US99/17130, filed Jul. 29, 1999; U.S. application Ser. No. 10/100,683 is a continuation-in-part of International Application No. PCT/US99/17130, filed Jul. 29, 1999, which claims the benefit of U.S. Provisional Application Nos. 60/094,657, filed Jul. 30, 1998, 60/095,486, filed Aug. 5, 1998, 60/096,319, filed Aug. 12, 1998, 60/095,454, filed Aug. 6, 1998, and 60/095,455, filed Aug. 6, 1998; U.S. application Ser. No. 10/100,683 is a continuation-in-part of U.S. application Ser. No. 10/054,988, filed Jan. 25, 2002, which is a continuation of U.S. application Ser. No. 09/904,615, filed Jul. 16, 2001, which is a continuation of U.S. application Ser. No. 09/739,254, filed Dec. 19, 2000, which is a continuation of U.S. application Ser. No. 09/511,554, filed Feb. 23, 2000, which is a continuation-in-part of International Application No. PCT/US99/19330, filed Aug. 24, 1999; U.S. application Ser. No. 10/100,683 is a continuation-in-part of U.S. application Ser. No. 09/904,615, filed Jul. 16, 2001, which is a continuation of U.S. application Ser. No. 09/739,254, filed Dec. 19, 2000, which is a continuation of U.S. application Ser. No. 09/511,554, filed Feb. 23, 2000, which is a continuation-in-part of International Application No. PCT/US99/19330, filed Aug. 24, 1999; U.S. application Ser. No. 10/100,683 is a continuation-in-part of International Application No. PCT/US99/19330, filed Aug. 24, 1999, which claims the benefit of U.S. Provisional Application Nos. 60/097,917, filed Aug. 25, 1998, and 60/098,634, filed Aug. 31, 1998; U.S. application Ser. No. 10/100,683 is a continuation-in-part of U.S. application Ser. No. 09/820,893, filed Mar. 30, 2001, which is a continuation of U.S. application Ser. No. 09/531,119, filed Mar. 20, 2000, which is a continuation-in-part of International Application No. PCT/US99/22012, filed Sep. 22, 1999; U.S. application Ser. No. 10/100,683 is a continuation-in-part of International Application No. PCT/US99/22012, filed Sep. 22, 1999, which claims the benefit of U.S. Provisional Application Nos. 60/101,546, filed Sep. 23, 1998, and 60/102,895, filed Oct. 2, 1998; U.S. application Ser. No. 10/100,683 is a continuation-in-part of U.S. application Ser. No. 09/948,820, filed Sep. 10, 2001, which is a continuation of U.S. application Ser. No. 09/565,391, filed May 5, 2000, which is a continuation-in-part of International Application No. PCT/US99/26409, filed Nov. 9, 1999; U.S. application Ser. No. 10/100,683 is a continuation-in-part of U.S. application Ser. No. 09/565,391, filed May 5, 2000, which is a continuation-in-part of International Application No. PCT/US99/26409, filed Nov. 9, 1999; U.S. application Ser. No. 10/100,683 is a continuation-in-part of International Application No. PCT/US99/26409, filed Nov. 9, 1999, which claims the benefit of U.S. Provisional Application No. 60/108,207, filed Nov. 12, 1998; U.S. application Ser. No. 10/100,683 is a continuation-in-part of U.S. application Ser. No. 09/895,298, filed Jul. 2, 2001, which is a continuation of U.S. application Ser. No. 09/591,316, filed Jun. 9, 2000, which is a continuation-in-part of International Application No. PCT/US99/29950, filed Dec. 16, 1999; U.S. application Ser. No. 10/100,683 is a continuation-in-part of International Application No. PCT/US99/29950, filed Dec. 16, 1999, which claims the benefit of U.S. Provisional Application Nos. 60/113,006, filed Dec. 18, 1998, and 60/112,809, filed Dec. 17, 1998; U.S. application Ser. No. 10/100,683 is a continuation-in-part of U.S. application Ser. No. 09/985,153, filed Nov. 1, 2001, which is a continuation of U.S. application Ser. No. 09/618,150, filed Jul. 17, 2000, which is a continuation-in-part of International Application No. PCT/US00/00903, filed Jan. 18, 2000; U.S. application Ser. No. 10/100, 683 is a continuation-in-part of International Application No. PCT/US00/00903, filed Jan. 18, 2000, which claims the benefit of U.S. Provisional Application No. 60/116,330, filed Jan. 19, 1999; U.S. application Ser. No. 10/100,683 is a continuation-in-part of U.S. application Ser. No. 09/997,131, filed Nov. 30, 2001, which is a continuation of U.S. application Ser. No. 09/628,508, filed Jul. 28, 2000, which is a continuation-in-part of International Application No. PCT/US00/03062, filed Feb. 8, 2000; U.S. application Ser. No. 10/100,683 is a continuation-in-part of International Application No. PCT/US00/03062, filed Feb. 8, 2000, which claims the benefit of U.S. Provisional Application No. 60/119,468, filed Feb. 10, 1999; U.S. application Ser. No. 10/100,683 is a continuation-in-part of U.S. application Ser. No. 10/050,882, filed Jan. 18, 2002, which is a continuation of U.S. application Ser. No. 09/661,453, filed Sep. 13, 2000, which is a continuation-in-part of International Application No. PCT/US00/06783, filed Mar. 16, 2000; U.S. application Ser. No. 10/100,683 is a continuation-in-part of U.S. application Ser. No. 09/661,453, filed Sep. 13, 2000, which is a continuation-in-part of International Application No. PCT/US00/06783, filed Mar. 16, 2000; U.S. application Ser. No. 10/100,683 is a continuation-in-part of International Application No. PCT/US00/06783, filed Mar. 16, 2000, which claims the benefit of U.S. Provisional Application No. 60/125,055, filed Mar. 18, 1999; U.S. application Ser. No. 10/100,683 is a continuation-in-part of U.S. application Ser. No. 10/050,704, filed Jan. 18, 2002, which is a continuation of U.S. application Ser. No. 09/684,524, filed Oct. 10, 2000, which is a continuation-in-part of International Application No. PCT/US00/08979, filed Apr. 6, 2000; U.S. application Ser. No. 10/100,683 is a continuation-in-part of U.S. application Ser. No. 09/684,524, filed Oct. 10, 2000, which is a continuation-in-part of International Application No. PCT/US00/08979, filed Apr. 6, 2000; U.S. application Ser. No. 10/100,683 is a continuation-in-part of International Application No. PCT/US00/08979, filed Apr. 6, 2000, which claims the benefit of U.S. Provisional Application Nos. 60/128,693, filed Apr. 9, 1999, and 60/130,991, filed Apr. 26, 1999; U.S. application Ser. No. 10/100,683 is a continuation-in-part of U.S. application Ser. No. 10/042,141, filed Jan. 11, 2002, which is a continuation of U.S. application Ser. No. 09/726,643, filed Dec. 1, 2000, which is a continuation-in-part of International Application No. PCT/US00/15187, filed Jun. 2, 2000; U.S. application Ser. No. 10/100,683 is a continuation-in-part of U.S. application Ser. No. 09/726,643, filed Dec. 1, 2000, which is a continuation-in-part of International Application No. PCT/US00/15187, filed Jun. 2, 2000; U.S. application Ser. No. 10/100,683 is a continuation-in-part of International Application No. PCT/US00/15187, filed Jun. 2, 2000, which claims the benefit of U.S. Provisional Application No. 60/137,725, filed Jun. 7, 1999; U.S. application Ser. No. 10/100,683 is a continuation-in-part of U.S. application Ser. No. 09/756,168, filed Jan. 9, 2001, which is a continuation-in-part of International Application No. PCT/US00/19735, filed Jul. 23, 1999; U.S. application Ser. No. 10/100,683 is a continuation-in-part of International Application No. PCT/US00/19735, filed Jul. 20, 2000, which claims the benefit of U.S. Provisional Application No. 60/145,220, filed Jul. 23, 1999; U.S. application Ser. No. 10/100,683 is a continuation-in-part of U.S. application Ser. No. 10/060,255, filed Feb. 1, 2002, which is a continuation of U.S. application Ser. No. 09/781,417, filed Feb. 13, 2001, which is a continuation-in-part of International Application No. PCT/US00/22325, filed Aug. 16, 2000; U.S. application Ser. No. 10/100,683 is a continuation-in-part of U.S. application Ser. No. 09/781,417, filed Feb. 13, 2001, which is a continuation-in-part of International Application No. PCT/US00/22325, filed Aug. 16, 2000; U.S. application Ser. No. 10/100,683 is a continuation-in-part of International Application No. PCT/US00/22325, filed Aug. 16, 2000, which claims the benefit of U.S. Provisional Application No. 60/149,182, filed Aug. 17, 1999; U.S. application Ser. No. 10/100,683 is a continuation-in-part of U.S. application Ser. No. 09/789,561, filed Feb. 22, 2001, which is a continuation-in-part of International Application No. PCT/US00/24008, filed Aug. 31, 2000; U.S. application Ser. No. 10/100,683 is a continuation-in-part of International Application No. PCT/US00/24008, filed Aug. 31, 2000, which claims the benefit of U.S. Provisional Application Nos. 60/152,315, filed Sep. 3, 1999, and 60/152,317, filed Sep. 3, 1999; U.S. application Ser. No. 10/100,683 is a continuation-in-part of U.S. application Ser. No. 09/800,729, filed Mar. 8, 2001, which is a continuation-in-part of International Application No. PCT/US00/26013, filed Sep. 22, 2000; U.S. application Ser. No. 10/100,683 is a continuation-in-part of International Application No. PCT/US00/26013, filed Sep. 22, 2000, which claims the benefit of U.S. Provisional Application No. 60/155,709, filed Sep. 24, 1999; U.S. application Ser. No. 10/100,683 is a continuation-in-part of U.S. application Ser. No. 09/832,129, filed Apr. 11, 2001, which is a continuation-in-part of International Application No. PCT/US00/28664, filed Oct. 17, 2000; U.S. application Ser. No. 10/100,683 is a continuation-in-part of International Application No. PCT/US00/28664, filed Oct. 17, 2000, which claims the benefit of U.S. Provisional Application Nos. 60/163,085, filed Nov. 2, 1999, and 60/172,411, filed Dec. 17, 1999; U.S. application Ser. No. 10/100,683 is a continuation-in-part of International Application No. PCT/US00/29363, filed Oct. 25, 2000, which claims the benefit of U.S. Provisional Application Nos. 60/215,139, filed Jun. 30, 2000, and 60/162,239, filed Oct. 29, 1999; U.S. application Ser. No. 10/100,683 is a continuation-in-part of International Application No. PCT/US00/29360, filed Oct. 25, 2000, which claims the benefit of U.S. Provisional Application Nos. 60/215,138, filed Jun. 30, 2000, and 60/162,211, filed Oct. 29, 1999; U.S. application Ser. No. 10/100,683 is a continuation-in-part of International Application No. PCT/US00/29362, filed Oct. 25, 2000, which claims the benefit of U.S. Provisional Application Nos. 60/215,131, filed Jun. 30, 2000, and 60/162,240, filed Oct. 29, 1999; U.S. application Ser. No. 10/100,683 is a continuation-in-part of International Application No. PCT/US00/29365, filed Oct. 25, 2000, which claims the benefit of U.S. Provisional Application Nos. 60/219,666, filed Jul. 21, 2000, and 60/162,237, filed Oct. 29, 1999; U.S. application Ser. No. 10/100,683 is a continuation-in-part of International Application No. PCT/US00/29364, filed Oct. 25, 2000, which claims the benefit of U.S. Provisional Application Nos. 60/215,134, filed Jun. 30, 2000, and 60/162,238, filed Oct. 29, 1999; U.S. application Ser. No. 10/100,683 is a continuation-in-part of International Application No. PCT/US00/30040, filed Nov. 1, 2000, which claims the benefit of U.S. Provisional Application Nos. 60/215,130, filed Jun. 30, 2000, and 60/163,580, filed Nov. 5, 1999; U.S. application Ser. No. 10/100,683 is a continuation-in-part of International Application No. PCT/US00/30037, filed Nov. 1, 2000, which claims the benefit of U.S. Provisional Application Nos. 60/215,137, filed Jun. 30, 2000, and 60/163,577, filed Nov. 5, 1999; U.S. application Ser. No. 10/100,683 is a continuation-in-part of International Application No. PCT/US00/30045, filed Nov. 1, 2000, which claims the benefit of U.S. Provisional Application Nos. 60/215,133, filed Jun. 30, 2000, and 60/163,581, filed Nov. 5, 1999; U.S. application Ser. No. 10/100,683 is a continuation-in-part of International Application No. PCT/US00/30036, filed Nov. 1, 2000, which claims the benefit of U.S. Provisional Application Nos. 60/221,366, filed Jul. 27, 2000, and 60/163,576, filed Nov. 5, 1999; U.S. application Ser. No. 10/100,683 is a continuation-in-part of International Application No. PCT/US00/30039, filed Nov. 1, 2000, which claims the benefit of U.S. Provisional Application Nos. 60/221,367, filed Jul. 27, 2000, 60/195,296, filed Apr. 7, 2000, and 60/164,344, filed Nov. 9, 1999; U.S. application Ser. No. 10/100,683 is a continuation-in-part of International Application No. PCT/US00/30654, filed Nov. 8, 2000, which claims the benefit of U.S. Provisional Application Nos. 60/221,142, filed Jul. 27, 2000, and 60/164,835, filed Nov. 12, 1999; U.S. application Ser. No. 10/100,683 is a continuation-in-part of International Application No. PCT/US00/30628, filed Nov. 8, 2000, which claims the benefit of U.S. Provisional Application Nos. 60/215,140, filed Jun. 30, 2000, and 60/164,744, filed Nov. 12, 1999; U.S. application Ser. No. 10/100,683 is a continuation-in-part of International Application No. PCT/US00/30653, filed Nov. 8, 2000, which claims the benefit of U.S. Provisional Application Nos. 60/221,193, filed Jul. 27, 2000, and 60/164,735, filed Nov. 12, 1999; U.S. application Ser. No. 10/100,683 is a continuation-in-part of International Application No. PCT/US00/30629, filed Nov. 8, 2000, which claims the benefit of U.S. Provisional Application Nos. 60/222,904, filed Aug. 3, 2000, and 60/164,825, filed Nov. 12, 1999; U.S. application Ser. No. 10/100,683 is a continuation-in-part of International Application No. PCT/US00/30679, filed Nov. 8, 2000, which claims the benefit of U.S. Provisional Application Nos. 60/224,007, filed Aug. 4, 2000, and 60/164,834, filed Nov. 12, 1999; U.S. application Ser. No. 10/100,683 is a continuation-in-part of International Application No. PCT/US00/30674, filed Nov. 8, 2000, which claims the benefit of U.S. Provisional Application Nos. 60/215,128, filed Jun. 30, 2000, and 60/164,750, filed Nov. 12, 1999; U.S. application Ser. No. 10/100,683 is a continuation-in-part of International Application No. PCT/US00/31162, filed Nov. 15, 2000; U.S. Provisional Application No. 60/215,136 claims the benefit of U.S. Provisional Application Nos. 60/215,136, filed Jun. 30, 2000, which claims the benefit of U.S. Provisional Application No. 60/166,415, filed Nov. 19, 1999; U.S. application Ser. No. 10/100,683 is a continuation-in-part of International Application No. PCT/US00/31282, filed Nov. 15, 2000, which claims the benefit of U.S. Provisional Application Nos. 60/219,665, filed Jul. 21, 2000, and 60/166,414, filed Nov. 19, 1999; U.S. application Ser. No. 10/100,683 is a continuation-in-part of International Application No. PCT/US00/30657, filed Nov. 8, 2000, which claims the benefit of U.S. Provisional Application Nos. 60/215,132, filed Jun. 30, 2000, and 60/164,731, filed Nov. 12, 1999; U.S. application Ser. No. 10/100,683 is a continuation-in-part of International Application No. PCT/US01/01396, filed Jan. 17, 2001; U.S. Provisional Application No. 60/256,968 claims the benefit of U.S. Provisional Application Nos. 60/256,968, filed Dec. 21, 2000, which claims the benefit of U.S. Provisional Application No. 60/226,280, filed Aug. 18, 2000; U.S. application Ser. No. 10/100,683 is a continuation-in-part of International Application No. PCT/US01/01387, filed Jan. 17, 2001; U.S. Provisional Application No. 60/259,803 claims the benefit of U.S. Provisional Application Nos. 60/259,803, filed Jan. 5, 2001, which claims the benefit of U.S. Provisional Application No. 60/226,380, filed Aug. 18, 2000; U.S. application Ser. No. 10/100,683 is a continuation-in-part of International Application No. PCT/US01/01567, filed Jan. 17, 2001, which claims the benefit of U.S. Provisional Application No. 60/228,084, filed Aug. 28, 2000; U.S. application Ser. No. 10/100,683 is a continuation-in-part of International Application No. PCT/US01/01431, filed Jan. 17, 2001, which claims the benefit of U.S. Provisional Application No. 60/231,968, filed Sep. 12, 2000; International Application No. PCT/US01/01431 is a continuation-in-part of U.S. application Ser. No. 09/915,582, filed Jul. 27, 2001; U.S. application Ser. No. 10/100,683 is a continuation-in-part of International Application No. PCT/US01/01432, filed Jan. 17, 2001, which claims the benefit of U.S. Provisional Application No. 60/236,326, filed Sep. 29, 2000; U.S. application Ser. No. 10/100,683 is a continuation-in-part of International Application No. PCT/US01/00544, filed Jan. 9, 2001, which claims the benefit of U.S. Provisional Application No. 60/234,211, filed Sep. 20, 2000; U.S. application Ser. No. 10/100,683 is a continuation-in-part of International Application No. PCT/US01/01435, filed Jan. 17, 2001, which claims the benefit of U.S. Provisional Application No. 60/226,282, filed Aug. 18, 2000; U.S. application Ser. No. 10/100,683 is a continuation-in-part of International Application No. PCT/US01/01386, filed Jan. 17, 2001, which claims the benefit of U.S. Provisional Application No. 60/232,104, filed Sep. 12, 2000; U.S. application Ser. No. 10/100,683 is a continuation-in-part of International Application No. PCT/US01/01565, filed Jan. 17, 2001, which claims the benefit of U.S. Provisional Application No. 60/234,210, filed Sep. 20, 2000; U.S. application Ser. No. 10/100,683 is a continuation-in-part of International Application No. PCT/US01/01394, filed Jan. 17, 2001, which claims the benefit of U.S. Provisional Application Nos. 60/259,805, filed Jan. 5, 2001, and 60/226,278, filed Aug. 18, 2000; U.S. application Ser. No. 10/100,683 is a continuation-in-part of International Application No. PCT/US01/01434, filed Jan. 17, 2001, which claims the benefit of U.S. Provisional Application Nos. 60/259,678, filed Jan. 5, 2001, and 60/226,279, filed Aug. 18, 2000; U.S. application Ser. No. 10/100,683 is a continuation-in-part of International Application No. PCT/US01/01397, filed Jan. 17, 2001, which claims the benefit of U.S. Provisional Application No. 60/226,281, filed Aug. 18, 2000; U.S. application Ser. No. 10/100,683 is a continuation-in-part of International Application No. PCT/US01/01385, filed Jan. 17, 2001, which claims the benefit of U.S. Provisional Application No. 60/231,969, filed Sep. 12, 2000; U.S. application Ser. No. 10/100,683 is a continuation-in-part of International Application No. PCT/US01/01384, filed Jan. 17, 2001, which claims the benefit of U.S. Provisional Application Nos. 60/259,516, filed Jan. 4, 2001, and 60/228,086, filed Aug. 28, 2000; U.S. application Ser. No. 10/100,683 is a continuation-in-part of International Application No. PCT/US01/01383, filed Jan. 17, 2001, which claims the benefit of U.S. Provisional Application Nos. 60/259,804, filed Jan. 5, 2001, and 60/228,083, filed Aug. 28, 2000; U.S. application Ser. No. 10/100,683 is a continuation-in-part of International Application No. PCT/US02/05064, filed Feb. 21, 2002, which claims the benefit of U.S. Provisional Application Nos. 60/304,444, filed Jul. 12, 2001, and 60/270,658, filed Feb. 23, 2001; U.S. application Ser. No. 10/100,683 is a continuation-in-part of International Application No. PCT/US02/05301, filed Feb. 21, 2002, which claims the benefit of U.S. Provisional Application Nos. 60/304,417, filed Jul. 12, 2001, and 60/270,625, filed Feb. 23, 2001; U.S. application Ser. No. 10/100,683 claims the benefit of U.S. Provisional Application Nos. 60/304,121, filed Jul. 11, 2001, 60/295,869, filed Jun. 6, 2001, 60/325,209, filed Sep. 28, 2001, 60/311,085, filed Aug. 10, 2001, 60/330,629, filed Oct. 26, 2001, 60/331,046, filed Nov. 7, 2001, 60/358,554, filed Feb. 22, 2002, and 60/358,714, filed Feb. 25, 2002. This application is a continuation-in-part of U.S. application Ser. No. 11/689,173, filed Mar. 21, 2007, which is a continuation of U.S. application Ser. No.

11/001,793, filed Dec. 2, 2004, which is a divisional of U.S. application Ser. No. 10/100,683, filed Mar. 19, 2002, which claims the benefit of U.S. Provisional Application Nos. 60/277,340, filed Mar. 21, 2001, 60/306,171, filed Jul. 19, 2001, and 60/331,287, filed Nov. 13, 2001; U.S. application Ser. No. 10/100,683 is a continuation-in-part of U.S. application Ser. No. 09/981,876, filed Oct. 19, 2001, which is a divisional of U.S. application Ser. No. 09/621,011, filed Jul. 20, 2000, which is a continuation of U.S. application Ser. No. 09/148,545, filed Sep. 4, 1998, which is a continuation-in-part of International Application No. PCT/US98/04482, filed Mar. 6, 1998; U.S. application Ser. No. 10/100,683 is a continuation-in-part of U.S. application Ser. No. 09/621,011, filed Jul. 20, 2000, which is a continuation of U.S. application Ser. No. 09/148,545, filed Sep. 4, 1998, which is a continuation-in-part of International Application No. PCT/US98/04482, filed Mar. 6, 1998; U.S. application Ser. No. 10/100,683 is a continuation-in-part of U.S. application Ser. No. 09/148,545, filed Sep. 4, 1998, which is a continuation-in-part of International Application No. PCT/US98/04482, filed Mar. 6, 1998; U.S. application Ser. No. 10/100,683 is a continuation-in-part of International Application No. PCT/US98/04482, filed Mar. 6, 1998, which claims the benefit of U.S. Provisional Application Nos. 60/040,162, filed Mar. 7, 1997, 60/040,333, filed Mar. 7, 1997, 60/038,621, filed Mar. 7, 1997, 60/040,161, filed Mar. 7, 1997, 60/040,626, filed Mar. 7, 1997, 60/040,334, filed Mar. 7, 1997, 60/040,336, filed Mar. 7, 1997, 60/040,163, filed Mar. 7, 1997, 60/047,615, filed May 23, 1997, 60/047,600, filed May 23, 1997, 60/047,597, filed May 23, 1997, 60/047,502, filed May 23, 1997, 60/047,633, filed May 23, 1997, 60/047,583, filed May 23, 1997, 60/047,617, filed May 23, 1997, 60/047,618, filed May 23, 1997, 60/047,503, filed May 23, 1997, 60/047,592, filed May 23, 1997, 60/047,581, filed May 23, 1997, 60/047,584, filed May 23, 1997, 60/047,500, filed May 23, 1997, 60/047,587, filed May 23, 1997, 60/047,492, filed May 23, 1997, 60/047,598, filed May 23, 1997, 60/047,613, filed May 23, 1997, 60/047,582, filed May 23, 1997, 60/047,596, filed May 23, 1997, 60/047,612, filed May 23, 1997, 60/047,632, filed May 23, 1997, 60/047,601, filed May 23, 1997, 60/043,580, filed Apr. 11, 1997, 60/043,568, filed Apr. 11, 1997, 60/043,314, filed Apr. 11, 1997, 60/043,569, filed Apr. 11, 1997, 60/043,311, filed Apr. 11, 1997, 60/043,671, filed Apr. 11, 1997, 60/043,674, filed Apr. 11, 1997, 60/043,669, filed Apr. 11, 1997, 60/043,312, filed Apr. 11, 1997, 60/043,313, filed Apr. 11, 1997, 60/043,672, filed Apr. 11, 1997, 60/043,315, filed Apr. 11, 1997, 60/048,974, filed Jun. 6, 1997, 60/056,886, filed Aug. 22, 1997, 60/056,877, filed Aug. 22, 1997, 60/056,889, filed Aug. 22, 1997, 60/056,893, filed Aug. 22, 1997, 60/056,630, filed Aug. 22, 1997, 60/056,878, filed Aug. 22, 1997, 60/056,662, filed Aug. 22, 1997, 60/056,872, filed Aug. 22, 1997, 60/056,882, filed Aug. 22, 1997, 60/056,637, filed Aug. 22, 1997, 60/056,903, filed Aug. 22, 1997, 60/056,888, filed Aug. 22, 1997, 60/056,879, filed Aug. 22, 1997, 60/056,880, filed Aug. 22, 1997, 60/056,894, filed Aug. 22, 1997, 60/056,911, filed Aug. 22, 1997, 60/056,636, filed Aug. 22, 1997, 60/056,874, filed Aug. 22, 1997, 60/056,910, filed Aug. 22, 1997, 60/056,864, filed Aug. 22, 1997, 60/056,631, filed Aug. 22, 1997, 60/056,845, filed Aug. 22, 1997, 60/056,892, filed Aug. 22, 1997, 60/047,595, filed May 23, 1997, 60/057,761, filed Sep. 5, 1997, 60/047,599, filed May 23, 1997, 60/047,588, filed May 23, 1997, 60/047,585, filed May 23, 1997, 60/047,586, filed May 23, 1997, 60/047,590, filed May 23, 1997, 60/047,594, filed May 23, 1997, 60/047,589, filed May 23, 1997, 60/047,593, filed May 23, 1997, 60/047,614, filed May 23, 1997, 60/043,578, filed Apr. 11, 1997, 60/043,576, filed Apr. 11, 1997, 60/047,501, filed May 23, 1997, 60/043,670, filed Apr. 11, 1997, 60/056,632, filed Aug. 22, 1997, 60/056,664, filed Aug. 22, 1997, 60/056,876, filed Aug. 22, 1997, 60/056,881, filed Aug. 22, 1997, 60/056,909, filed Aug. 22, 1997, 60/056,875, filed Aug. 22, 1997, 60/056,862, filed Aug. 22, 1997, 60/056,887, filed Aug. 22, 1997, 60/056,908, filed Aug. 22, 1997, 60/048,964, filed Jun. 6, 1997, 60/057,650, filed Sep. 5, 1997, and 60/056,884, filed Aug. 22, 1997; U.S. application Ser. No. 10/100,683 is a continuation-in-part of U.S. application Ser. No. 09/882,171, filed Jun. 18, 2001, which is a continuation of U.S. application Ser. No. 09/809,391, filed Mar. 16, 2001, which is a continuation-in-part of U.S. application Ser. No. 09/149,476, filed Sep. 8, 1998, which is a continuation-in-part of International Application No. PCT/US98/04493, filed Mar. 6, 1998; U.S. application Ser. No. 10/100,683 is a continuation-in-part of U.S. application Ser. No. 09/809,391, filed Mar. 16, 2001, which claims the benefit of U.S. Provisional Application No. 60/190,068, filed Mar. 17, 2000; U.S. application Ser. No. 09/809,391 is a continuation-in-part of U.S. application Ser. No. 09/149,476, filed Sep. 8, 1998, which is a continuation-in-part of International Application No. PCT/US98/04493, filed Mar. 6, 1998; U.S. application Ser. No. 10/100,683 is a continuation-in-part of U.S. application Ser. No. 09/149,476, filed Sep. 8, 1998, which is a continuation-in-part of International Application No. PCT/US98/04493, filed Mar. 6, 1998; U.S. application Ser. No. 10/100,683 is a continuation-in-part of International Application No. PCT/US98/04493, filed Mar. 6, 1998; U.S. application Ser. No. 10/100,683 claims the benefit of U.S. Provisional Application No. 60/040,161, filed Mar. 7, 1997; International Application No. PCT/US98/04493 claims the benefit of U.S. Provisional Application Nos. 60/040,162, filed Mar. 7, 1997, 60/040,333, filed Mar. 7, 1997, 60/038,621, filed Mar. 7, 1997, 60/040,626, filed Mar. 7, 1997, 60/040,334, filed Mar. 7, 1997, 60/040,336, filed Mar. 7, 1997, 60/040,163, filed Mar. 7, 1997, 60/047,600, filed May 23, 1997, 60/047,615, filed May 23, 1997, 60/047,597, filed May 23, 1997, 60/047,502, filed May 23, 1997, 60/047,633, filed May 23, 1997, 60/047,583, filed May 23, 1997, 60/047,617, filed May 23, 1997, 60/047,618, filed May 23, 1997, 60/047,503, filed May 23, 1997, 60/047,592, filed May 23, 1997, 60/047,581, filed May 23, 1997, 60/047,584, filed May 23, 1997, 60/047,500, filed May 23, 1997, 60/047,587, filed May 23, 1997, 60/047,492, filed May 23, 1997, 60/047,598, filed May 23, 1997, 60/047,613, filed May 23, 1997, 60/047,582, filed May 23, 1997, 60/047,596, filed May 23, 1997, 60/047,612, filed May 23, 1997, 60/047,632, filed May 23, 1997, 60/047,601, filed May 23, 1997, 60/043,580, filed Apr. 11, 1997, 60/043,568, filed Apr. 11, 1997, 60/043,314, filed Apr. 11, 1997, 60/043,569, filed Apr. 11, 1997, 60/043,311, filed Apr. 11, 1997, 60/043,671, filed Apr. 11, 1997, 60/043,674, filed Apr. 11, 1997, 60/043,669, filed Apr. 11, 1997, 60/043,312, filed Apr. 11, 1997, 60/043,313, filed Apr. 11, 1997, 60/043,672, filed Apr. 11, 1997, 60/043,315, filed Apr. 11, 1997, 60/048,974, filed Jun. 6, 1997, 60/056,886, filed Aug. 22, 1997, 60/056,877, filed Aug. 22, 1997, 60/056,889, filed Aug. 22, 1997, 60/056,893, filed Aug. 22, 1997, 60/056,630, filed Aug. 22, 1997, 60/056,878, filed Aug. 22, 1997, 60/056,662, filed Aug. 22, 1997, 60/056,872, filed Aug. 22, 1997, 60/056,882, filed Aug. 22, 1997, 60/056,637, filed Aug. 22, 1997, 60/056,903, filed Aug. 22, 1997, 60/056,888, filed Aug. 22, 1997, 60/056,879, filed Aug. 22, 1997, 60/056,880, filed Aug. 22, 1997, 60/056,894, filed Aug. 22, 1997, 60/056,911, filed Aug. 22, 1997, 60/056,636, filed Aug. 22, 1997, 60/056,874, filed Aug. 22, 1997, 60/056,910, filed Aug. 22, 1997, 60/056,864, filed Aug. 22, 1997, 60/056,631, filed Aug. 22, 1997, 60/056,845, filed Aug. 22, 1997, 60/056,892, filed Aug. 22, 1997, 60/057,761, filed Sep. 5, 1997, 60/047,595, filed May 23, 1997, 60/047,599, filed May 23, 1997, 60/047,588, filed May 23, 1997, 60/047,585, filed May 23, 1997, 60/047,586, filed May 23, 1997, 60/047,590, filed May 23, 1997, 60/047,594, filed May 23, 1997, 60/047,589, filed May 23, 1997, 60/047,593, filed May 23, 1997, 60/047,614, filed May 23, 1997, 60/043,578, filed Apr. 11, 1997, 60/043,576, filed Apr. 11, 1997, 60/047,501, filed May 23, 1997, 60/043,670, filed Apr. 11, 1997, 60/056,632, filed Aug. 22, 1997, 60/056,664, filed Aug. 22, 1997, 60/056,876, filed Aug. 22, 1997, 60/056,881, filed Aug. 22, 1997, 60/056,909, filed Aug. 22, 1997, 60/056,875, filed Aug. 22, 1997, 60/056,862, filed Aug. 22, 1997, 60/056,887, filed Aug. 22, 1997, 60/056,908, filed Aug. 22, 1997, 60/048,964, filed Jun. 6, 1997, 60/057,650, filed Sep. 5, 1997, 60/056,884, filed Aug. 22, 1997, 60/057,669, filed Sep. 5, 1997, 60/049,610, filed Jun. 13, 1997, 60/061,060, filed Oct. 2, 1997, 60/051,926, filed Jul. 8, 1997, 60/052,874, filed Jul. 16, 1997, 60/058,785, filed Sep. 12, 1997, and 60/055,724, filed Aug. 18, 1997; U.S. application Ser. No. 10/100,683 is a continuation-in-part of U.S. application Ser. No. 10/058,993, filed Jan. 30, 2002, which claims the benefit of U.S. Provisional Application No. 60/265,583, filed Feb. 2, 2001; U.S. application Ser. No. 10/058,993 is a continuation-in-part of U.S. application Ser. No. 09/852,659, filed May 11, 2001, which is a continuation-in-part of U.S. application Ser. No. 09/152,060, filed Sep. 11, 1998, which is a continuation-in-part of International Application No. PCT/US98/04858, filed Mar. 12, 1998; U.S. application Ser. No. 10/058,993 is a continuation-in-part of U.S. application Ser. No. 09/853,161, filed May 11, 2001, which is a continuation-in-part of U.S. application Ser. No. 09/152,060, filed Sep. 11, 1998, which is a continuation-in-part of International Application No. PCT/US98/04858, filed Mar. 12, 1998; U.S. application Ser. No. 10/058,993 is a continuation-in-part of U.S. application Ser. No. 09/852,797, filed May 11, 2001, which is a continuation-in-part of U.S. application Ser. No. 09/152,060, filed Sep. 11, 1998, which is a continuation-in-part of International Application No. PCT/US98/04858, filed Mar. 12, 1998; U.S. application Ser. No. 10/100,683 is a continuation-in-part of U.S. application Ser. No. 09/852,659, filed May 11, 2001, which claims the benefit of U.S. Provisional Application No. 60/265,583, filed Feb. 2, 2001; U.S. application Ser. No. 09/852,659 is a continuation-in-part of U.S. application Ser. No. 09/152,060, filed Sep. 11, 1998, which is a continuation-in-part of International Application No. PCT/US98/04858, filed Mar. 12, 1998; U.S. application Ser. No. 10/100,683 is a continuation-in-part of U.S. application Ser. No. 09/853,161, filed May 11, 2001, which claims the benefit of U.S. Provisional Application No. 60/265,583, filed Feb. 2, 2001; U.S. application Ser. No. 09/853,161 is a continuation-in-part of U.S. application Ser. No. 09/152,060, filed Sep. 11, 1998, which is a continuation-in-part of International Application No. PCT/US98/04858, filed Mar. 12, 1998; U.S. application Ser. No. 10/100,683 is a continuation-in-part of U.S. application Ser. No. 09/852,797, filed May 11, 2001, which claims the benefit of U.S. Provisional Application No. 60/265,583, filed Feb. 2, 2001; U.S. application Ser. No. 09/852,797 is a continuation-in-part of U.S. application Ser. No. 09/152,060, filed Sep. 11, 1998, which is a continuation-in-part of International Application No. PCT/US98/04858, filed Mar. 12, 1998; U.S. application Ser. No. 10/100,683 is a continuation-in-part of U.S. application Ser. No. 09/152,060, filed Sep. 11, 1998, which is a continuation-in-part of International Application No. PCT/US98/04858, filed Mar. 12, 1998; U.S. application Ser. No. 10/100,683 is a continuation-in-part of International Application No. PCT/US98/04858, filed Mar. 12, 1998, which claims the benefit of U.S. Provisional Application Nos. 60/040,762, filed Mar. 14, 1997, 60/040,710, filed Mar. 14, 1997, 60/050,934, filed May 30, 1997, 60/048,100, filed May 30, 1997, 60/048,357, filed May 30, 1997, 60/048,189, filed May 30, 1997, 60/057,765, filed Sep. 5, 1997, 60/048,970, filed Jun. 6, 1997, and 60/068,368, filed Dec. 19, 1997; U.S. application Ser. No. 10/100,683 is a continuation-in-part of U.S. application Ser. No. 10/059,395, filed Jan. 31, 2002, which is a divisional of U.S. application Ser. No. 09/966,262, filed Oct. 1, 2001, which is a continuation of U.S. application Ser. No. 09/154,707, filed Sep. 17, 1998, which is a continuation-in-part of International Application No. PCT/US98/05311, filed Mar. 19, 1998; U.S. application Ser. No. 10/100,683 is a continuation-in-part of U.S. application Ser. No. 09/984,245, filed Oct. 29, 2001, which is a divisional of U.S. application Ser. No. 09/154,707, filed Sep. 17, 1998, which is a continuation-in-part of International Application No. PCT/US98/05311, filed Mar. 19, 1998; U.S. application Ser. No. 10/100,683 is a continuation-in-part of U.S. application Ser. No. 09/983,966, filed Oct. 26, 2001, which is a divisional of U.S. application Ser. No. 09/154,707, filed Sep. 17, 1998, which is a continuation-in-part of International Application No. PCT/US98/05311, filed Mar. 19, 1998; U.S. application Ser. No. 10/100,683 is a continuation-in-part of U.S. application Ser. No. 09/966,262, filed Oct. 1, 2001, which is a continuation of U.S. application Ser. No. 09/154,707, filed Sep. 17, 1998, which is a continuation-in-part of International Application No. PCT/US98/05311, filed Mar. 19, 1998; U.S. application Ser. No. 10/100,683 is a continuation-in-part of U.S. application Ser. No. 09/154,707, filed Sep. 17, 1998, which is a continuation-in-part of International Application No. PCT/US98/05311, filed Mar. 19, 1998; U.S. application Ser. No. 10/100,683 is a continuation-in-part of International Application No. PCT/US98/05311, filed Mar. 19, 1998, which claims the benefit of U.S. Provisional Application Nos. 60/041,277, filed Mar. 21, 1997, 60/042,344, filed Mar. 21, 1997, 60/041,276, filed Mar. 21, 1997, 60/041,281, filed Mar. 21, 1997, 60/048,094, filed May 30, 1997, 60/048,350, filed May 30, 1997, 60/048,188, filed May 30, 1997, 60/048,135, filed May 30, 1997, 60/050,937, filed May 30, 1997, 60/048,187, filed May 30, 1997, 60/048,099, filed May 30, 1997, 60/048,352, filed May 30, 1997, 60/048,186, filed May 30, 1997, 60/048,069, filed May 30, 1997, 60/048,095, filed May 30, 1997, 60/048,131, filed May 30, 1997, 60/048,096, filed May 30, 1997, 60/048,355, filed May 30, 1997, 60/048,160, filed May 30, 1997, 60/048,351, filed May 30, 1997, 60/048,154, filed May 30, 1997, 60/054,804, filed Aug. 5, 1997, 60/056,370, filed Aug. 19, 1997, and 60/060,862, filed Oct. 2, 1997; U.S. application Ser. No. 10/100,683 is a continuation-in-part of U.S. application Ser. No. 09/814,122, filed Mar. 22, 2001, which is a continuation of U.S. application Ser. No. 09/577,145, filed May 24, 2000, which is a continuation of U.S. application Ser. No. 09/166,780, filed Oct. 6, 1998, which is a continuation-in-part of International Application No. PCT/US98/06801, filed Apr. 7, 1998; U.S. application Ser. No. 10/100,683 is a continuation-in-part of International Application No. PCT/US98/06801, filed Apr. 7, 1998, which claims the benefit of U.S. Provisional Application Nos. 60/042,726, filed Apr. 8, 1997, 60/042,727, filed Apr. 8, 1997, 60/042,728, filed Apr. 8, 1997, 60/042,754, filed Apr. 8, 1997, 60/042,825, filed Apr. 8, 1997, 60/048,068, filed May 30, 1997, 60/048,070, filed May 30, 1997, and 60/048,184, filed May 30, 1997; U.S. application Ser. No. 10/100,683 is a continuation-in-part of International Application No. PCT/US98/06801, filed Apr. 7, 1998, which claims the benefit of U.S. Provisional Application Nos. 60/042,726, filed Apr. 8, 1997, 60/042,727, filed Apr. 8, 1997, 60/042,728, filed Apr. 8, 1997, 60/042,754, filed Apr. 8, 1997, 60/042,825, filed Apr. 8, 1997, 60/048,068, filed May 30, 1997, 60/048,070, filed May 30, 1997, and 60/048,184, filed May 30, 1997; U.S. application Ser. No. 10/100,683 is a continuation-in-part of International Application No. PCT/US98/10868, filed May 28, 1998, which claims the benefit of U.S. Provisional Application Nos. 60/044,039, filed May 30, 1997, 60/048,093, filed May 30, 1997, 60/048,190, filed May 30, 1997, 60/050,935, filed May 30, 1997, 60/048,101, filed May 30, 1997, 60/048,356, filed May 30, 1997, 60/056,250, filed Aug. 29, 1997, 60/056,296, filed Aug. 29, 1997, and 60/056,293, filed Aug. 29, 1997; U.S. application Ser. No. 10/100,683 is a continuation-in-part of International Application No. PCT/US98/11422, filed Jun. 4, 1998, which claims the benefit of U.S. Provisional Application Nos. 60/048,885, filed Jun. 6, 1997, 60/049,375, filed Jun. 6, 1997, 60/048,881, filed Jun. 6, 1997, 60/048,880, filed Jun. 6, 1997, 60/048,896, filed Jun. 6, 1997, 60/049,020, filed Jun. 6, 1997, 60/048,876, filed Jun. 6, 1997, 60/048,895, filed Jun. 6, 1997, 60/048,884, filed Jun. 6, 1997, 60/048,894, filed Jun. 6, 1997, 60/048,971, filed Jun. 6, 1997, 60/048,964, filed Jun. 6, 1997, 60/048,882, filed Jun. 6, 1997, 60/048,899, filed Jun. 6, 1997, 60/048,893, filed Jun. 6, 1997, 60/048,900, filed Jun. 6, 1997, 60/048,901, filed Jun. 6, 1997, 60/048,892, filed Jun. 6, 1997, 60/048,915, filed Jun. 6, 1997, 60/049,019, filed Jun. 6, 1997, 60/048,970, filed Jun. 6, 1997, 60/048,972, filed Jun. 6, 1997, 60/048,916, filed Jun. 6, 1997, 60/049,373, filed Jun. 6, 1997, 60/048,875, filed Jun. 6, 1997, 60/049,374, filed Jun. 6, 1997, 60/048,917, filed Jun. 6, 1997, 60/048,949, filed Jun. 6, 1997, 60/048,974, filed Jun. 6, 1997, 60/048,883, filed Jun. 6, 1997, 60/048,897, filed Jun. 6, 1997, 60/048,898, filed Jun. 6, 1997, 60/048,962, filed Jun. 6, 1997, 60/048,963, filed Jun. 6, 1997, 60/048,877, filed Jun. 6, 1997, 60/048,878, filed Jun. 6, 1997, 60/057,645, filed Sep. 5, 1997, 60/057,642, filed Sep. 5, 1997, 60/057,668, filed Sep. 5, 1997, 60/057,635, filed Sep. 5, 1997, 60/057,627, filed Sep. 5, 1997, 60/057,667, filed Sep. 5, 1997, 60/057,666, filed Sep. 5, 1997, 60/057,764, filed Sep. 5, 1997, 60/057,643, filed Sep. 5, 1997, 60/057,769, filed Sep. 5, 1997, 60/057,763, filed Sep. 5, 1997, 60/057,650, filed Sep. 5, 1997, 60/057,584, filed Sep. 5, 1997, 60/057,647, filed Sep. 5, 1997, 60/057,661, filed Sep. 5, 1997, 60/057,662, filed Sep. 5, 1997, 60/057,646, filed Sep. 5, 1997, 60/057,654, filed Sep. 5, 1997, 60/057,651, filed Sep. 5, 1997, 60/057,644, filed Sep. 5, 1997, 60/057,765, filed Sep. 5, 1997, 60/057,762, filed Sep. 5, 1997, 60/057,775, filed Sep. 5, 1997, 60/057,648, filed Sep. 5, 1997, 60/057,774, filed Sep. 5, 1997, 60/057,649, filed Sep. 5, 1997, 60/057,770, filed Sep. 5, 1997, 60/057,771, filed Sep. 5, 1997, 60/057,761, filed Sep. 5, 1997, 60/057,760, filed Sep. 5, 1997, 60/057,776, filed Sep. 5, 1997, 60/057,778, filed Sep. 5, 1997, 60/057,629, filed Sep. 5, 1997, 60/057,628, filed Sep. 5, 1997, 60/057,777, filed Sep. 5, 1997, 60/057,634, filed Sep. 5, 1997, and 60/070,923, filed Dec. 18, 1997; U.S. application Ser. No. 10/100,683 is a continuation-in-part of International Application No. PCT/US01/05614, filed Feb. 21, 2001, which claims the benefit of U.S. Provisional Application Nos. 60/184,836, filed Feb. 24, 2000, and 60/193,170, filed Mar. 29, 2000; U.S. application Ser. No. 10/100,683 is a continuation-in-part of International Application No. PCT/US98/12125, filed Jun. 11, 1998, which claims the benefit of U.S. Provisional Application Nos. 60/049,547, filed Jun. 13, 1997, 60/049,548, filed Jun. 13, 1997, 60/049,549, filed Jun. 13, 1997, 60/049,550, filed Jun. 13, 1997, 60/049,566, filed Jun. 13, 1997, 60/049,606, filed Jun. 13, 1997, 60/049,607, filed Jun. 13, 1997, 60/049,608, filed Jun. 13, 1997, 60/049,609, filed Jun. 13, 1997, 60/049,610, filed Jun. 13, 1997, 60/049,611, filed Jun. 13, 1997, 60/050,901, filed Jun. 13, 1997, 60/052,989, filed Jun. 13, 1997, 60/051,919, filed Jul. 8, 1997, 60/055,984, filed Aug. 18, 1997, 60/058,665, filed Sep. 12, 1997, 60/058,668, filed Sep. 12, 1997, 60/058,669, filed Sep. 12, 1997, 60/058,750, filed Sep. 12, 1997, 60/058,971, filed Sep. 12, 1997, 60/058,972, filed Sep. 12, 1997, 60/058,975, filed Sep. 12, 1997, 60/060,834, filed Oct. 2, 1997, 60/060,841, filed Oct. 2, 1997, 60/060,844, filed Oct. 2, 1997, 60/060,865, filed Oct. 2, 1997, 60/061,059, filed Oct. 2, 1997, and 60/061,060, filed Oct. 2, 1997; U.S. application Ser. No. 10/100,683 is a continuation-in-part of U.S. application Ser. No. 09/627,081, filed Jul. 27, 2000, which is a continuation of U.S. application Ser. No. 09/213,365, filed Dec. 17, 1998, which is a continuation-in-part of International Application No. PCT/US98/13608, filed Jun. 30, 1998; U.S. application Ser. No. 10/100,683 is a continuation-in-part of International Application No. PCT/US98/13608, filed Jun. 30, 1998, which claims the benefit of U.S. Provisional Application Nos. 60/051,480, filed Jul. 1, 1997, 60/051,381, filed Jul. 1, 1997, 60/058,663, filed Sep. 12, 1997, and 60/058,598, filed Sep. 12, 1997; U.S. application Ser. No. 10/100,683 is a continuation-in-part of U.S. application Ser. No. 09/984,490, filed Oct. 30, 2001, which is a divisional of U.S. application Ser. No. 09/227,357, filed Jan. 8, 1999, which is a continuation-in-part of International Application No. PCT/US98/13684, filed Jul. 7, 1998; U.S. application Ser. No. 10/100,683 is a continuation-in-part of U.S. application Ser. No. 09/983,802, filed Oct. 25, 2001, which is a continuation of U.S. application Ser. No. 09/227,357, filed Jan. 8, 1999, which is a continuation-in-part of International Application No. PCT/US98/13684, filed Jul. 7, 1998; U.S. application Ser. No. 10/100,683 is a continuation-in-part of U.S. application Ser. No. 09/973,278, filed Oct. 10, 2001, which claims the benefit of U.S. Provisional Application No. 60/239,899, filed Oct. 13, 2000; U.S. application Ser. No. 09/973,278 is a continuation-in-part of U.S. application Ser. No. 09/227,357, filed Jan. 8, 1999, which is a continuation-in-part of International Application No. PCT/US98/13684, filed Jul. 7, 1998; U.S. application Ser. No. 10/100,683 is a continuation-in-part of International Application No. PCT/US98/13684, filed Jul. 7, 1998, which claims the benefit of U.S. Provisional Application Nos. 60/051,926, filed Jul. 8, 1997, 60/052,793, filed Jul. 8, 1997, 60/051,925, filed Jul. 8, 1997, 60/051,929, filed Jul. 8, 1997, 60/052,803, filed Jul. 8, 1997, 60/052,732, filed Jul. 8, 1997, 60/051,931, filed Jul. 8, 1997, 60/051,932, filed Jul. 8, 1997, 60/051,916, filed Jul. 8, 1997, 60/051,930, filed Jul. 8, 1997, 60/051,918, filed Jul. 8, 1997, 60/051,920, filed Jul. 8, 1997, 60/052,733, filed Jul. 8, 1997, 60/052,795, filed Jul. 8, 1997, 60/051,919, filed Jul. 8, 1997, 60/051,928, filed Jul. 8, 1997, 60/055,722, filed Aug. 18, 1997, 60/055,723, filed Aug. 18, 1997, 60/055,948, filed Aug. 18, 1997, 60/055,949, filed Aug. 18, 1997, 60/055,953, filed Aug. 18, 1997, 60/055,950, filed Aug. 18, 1997, 60/055,947, filed Aug. 18, 1997, 60/055,964, filed Aug. 18, 1997, 60/056,360, filed Aug. 18, 1997, 60/055,684, filed Aug. 18, 1997, 60/055,984, filed Aug. 18, 1997, 60/055,954, filed Aug. 18, 1997, 60/058,785, filed Sep. 12, 1997, 60/058,664, filed Sep. 12, 1997, 60/058,660, filed Sep. 12, 1997, and 60/058,661, filed Sep. 12, 1997; U.S. application Ser. No. 10/100,683 is a continuation-in-part of U.S. application Ser. No. 09/776,724, filed Feb. 6, 2001, which claims the benefit of U.S. Provisional Application No. 60/180,909, filed Feb. 8, 2000; U.S. application Ser. No. 09/776,724 is a continuation-in-part of U.S. application Ser. No. 09/669,688, filed Sep. 26, 2000, which is a continuation of U.S. application Ser. No. 09/229,982, filed Jan. 14, 1999, which is a continuation-in-part of International Application No. PCT/US98/14613, filed Jul. 15, 1998; U.S. application Ser. No. 10/100,683 is a continuation-in-part of U.S. application Ser. No. 09/669,688, filed Sep. 26, 2000, which is a continuation of U.S. application Ser. No. 09/229,982, filed Jan. 14, 1999, which is a continuation-in-part of International Application No. PCT/US98/14613, filed Jul. 15, 1998; U.S. application Ser. No. 10/100,683 is a continuation-in-part of U.S. application Ser. No. 09/229,982, filed Jan. 14, 1999, which is a continuation-in-part of International Application No. PCT/US98/14613, filed Jul. 15, 1998; U.S. application Ser. No. 10/100,683 is a continuation-in-part of International Application No. PCT/US98/14613, filed Jul. 15, 1998, which claims the benefit of U.S. Provisional Application Nos. 60/052,661, filed Jul. 16, 1997, 60/052,872, filed Jul. 16, 1997, 60/052,871, filed Jul. 16, 1997, 60/052,874, filed Jul. 16, 1997, 60/052,873, filed Jul. 16, 1997, 60/052,870, filed Jul. 16, 1997, 60/052,875, filed Jul. 16, 1997, 60/053,440, filed Jul. 22, 1997, 60/053,441, filed Jul. 22, 1997, 60/053,442, filed Jul. 22, 1997, 60/056,359, filed Aug. 18, 1997, 60/055,725, filed Aug. 18, 1997, 60/055,985, filed Aug. 18, 1997, 60/055,952, filed Aug. 18, 1997, 60/055,989, filed Aug. 18, 1997, 60/056,361, filed Aug. 18, 1997, 60/055,726, filed Aug. 18, 1997, 60/055,724, filed Aug. 18, 1997, 60/055,946, filed Aug. 18, 1997, and 60/055,683, filed Aug. 18, 1997; U.S. application Ser. No. 10/100,683 claims the benefit of U.S. Provisional Application No. 60/295,558, filed Jun. 5, 2001; U.S. application Ser. No. 10/100,683 is a continuation-in-part of U.S. application Ser. No. 09/820,649, filed Mar. 30, 2001, which is a continuation of U.S. application Ser. No. 09/666,984, filed Sep. 21, 2000, which is a continuation of U.S. application Ser. No. 09/236,557, filed Jan. 26, 1999, which is a continuation-in-part of International Application No. PCT/US98/15949, filed Jul. 29, 1998; U.S. application Ser. No. 10/100,683 is a continuation-in-part of International Application No. PCT/US98/15949, filed Jul. 29, 1998, which claims the benefit of U.S. Provisional Application Nos. 60/054,212, filed Jul. 30, 1997, 60/054,209, filed Jul. 30, 1997, 60/054,234, filed Jul. 30, 1997, 60/054,218, filed Jul. 30, 1997, 60/054,214, filed Jul. 30, 1997, 60/054,236, filed Jul. 30, 1997, 60/054,215, filed Jul. 30, 1997, 60/054,211, filed Jul. 30, 1997, 60/054,217, filed Jul. 30, 1997, 60/054,213, filed Jul. 30, 1997, 60/055,968, filed Aug. 18, 1997, 60/055,969, filed Aug. 18, 1997, 60/055,972, filed Aug. 18, 1997, 60/056,561, filed Aug. 19, 1997, 60/056,534, filed Aug. 19, 1997, 60/056,729, filed Aug. 19, 1997, 60/056,543, filed Aug. 19, 1997, 60/056,727, filed Aug. 19, 1997, 60/056,554, filed Aug. 19, 1997, and 60/056,730, filed Aug. 19, 1997; U.S. application Ser. No. 10/100,683 is a continuation-in-part of U.S. application Ser. No. 09/969,730, filed Oct. 4, 2001, which is a continuation-in-part of U.S. application Ser. No. 09/774,639, filed Feb. 1, 2001, which is a continuation of U.S. application Ser. No. 09/244,112, filed Feb. 4, 1999, which is a continuation-in-part of International Application No. PCT/US98/16235, filed Aug. 4, 1998; U.S. application Ser. No. 10/100,683 is a continuation-in-part of U.S. application Ser. No. 09/774,639, filed Feb. 1, 2001, which is a continuation of U.S. application Ser. No. 09/244,112, filed Feb. 4, 1999, which is a continuation-in-part of International Application No. PCT/US98/16235, filed Aug. 4, 1998; U.S. application Ser. No. 10/100,683 is a continuation-in-part of U.S. application Ser. No. 09/969,730, filed Oct. 4, 2001, which claims the benefit of U.S. Provisional Application No. 60/238,291, filed Oct. 6, 2000; U.S. application Ser. No. 10/100,683 is a continuation-in-part of International Application No. PCT/US98/16235, filed Aug. 4, 1998, which claims the benefit of U.S. Provisional Application Nos. 60/055,386, filed Aug. 5, 1997, 60/054,807, filed Aug. 5, 1997, 60/055,312, filed Aug. 5, 1997, 60/055,309, filed Aug. 5, 1997, 60/054,798, filed Aug. 5, 1997, 60/055,310, filed Aug. 5, 1997, 60/054,806, filed Aug. 5, 1997, 60/054,809, filed Aug. 5, 1997, 60/054,804, filed Aug. 5, 1997, 60/054,803, filed Aug. 5, 1997, 60/054,808, filed Aug. 5, 1997, 60/055,311, filed Aug. 5, 1997, 60/055,986, filed Aug. 18, 1997, 60/055,970, filed Aug. 18, 1997, 60/056,563, filed Aug. 19, 1997, 60/056,557, filed Aug. 19, 1997, 60/056,731, filed Aug. 19, 1997, 60/056,365, filed Aug. 19, 1997, 60/056,367, filed Aug. 19, 1997, 60/056,370, filed Aug. 19, 1997, 60/056,364, filed Aug. 19, 1997, 60/056,366, filed Aug. 19, 1997, 60/056,732, filed Aug. 19, 1997, and 60/056,371, filed Aug. 19, 1997; U.S. application Ser. No. 10/100,683 is a continuation-in-part of U.S. application Ser. No. 09/716,128, filed Nov. 17, 2000, which is a continuation of U.S. application Ser. No. 09/251,329, filed Feb. 17, 1999, which is a continuation-in-part of International Application No. PCT/US98/17044, filed Aug. 18, 1998; U.S. application Ser. No. 10/100,683 is a continuation-in-part of International Application No. PCT/US98/17044, filed Aug. 18, 1998, which claims the benefit of U.S. Provisional Application Nos. 60/056,555, filed Aug. 19, 1997, 60/056,556, filed Aug. 19, 1997, 60/056,535, filed Aug. 19, 1997, 60/056,629, filed Aug. 19, 1997, 60/056,369, filed Aug. 19, 1997, 60/056,628, filed Aug. 19, 1997, 60/056,728, filed Aug. 19, 1997, 60/056,368, filed Aug. 19, 1997, 60/056,726, filed Aug. 19, 1997, 60/089,510, filed Jun. 16, 1998, and 60/092,956, filed Jul. 15, 1998; U.S. application Ser. No. 10/100,683 is a continuation-in-part of U.S. application Ser. No. 09/729,835, filed Dec. 6, 2000, which is a divisional of U.S. application Ser. No. 09/257,179, filed Feb. 25, 1999, which is a continuation-in-part of International Application No. PCT/US98/17709, filed Aug. 27, 1998; U.S. application Ser. No. 10/100,683 is a continuation-in-part of U.S. application Ser. No. 09/257,179, filed Feb. 25, 1999, which is a continuation-in-part of International Application No. PCT/US98/17709, filed Aug. 27, 1998; U.S. application Ser. No. 10/100,683 is a continuation-in-part of International Application No. PCT/US98/17709, filed Aug. 27, 1998, which claims the benefit of U.S. Provisional Application Nos. 60/056,270, filed Aug. 29, 1997, 60/056,271, filed Aug. 29, 1997, 60/056,247, filed Aug. 29, 1997, and 60/056,073, filed Aug. 29, 1997; U.S. application Ser. No. 10/100,683 is a continuation-in-part of U.S. application Ser. No. 10/047,021, filed Jan. 17, 2002, which is a continuation-in-part of U.S. application Ser. No. 09/722,329, filed Nov. 28, 2000, which is a continuation of U.S. application Ser. No. 09/262,109, filed Mar. 4, 1999, which is a continuation-in-part of International Application No. PCT/US98/18360, filed Sep. 3, 1998; U.S. application Ser. No. 10/100,683 is a continuation-in-part of U.S. application Ser. No. 09/722,329, filed Nov. 28, 2000, which is a continuation of U.S. application Ser. No. 09/262,109, filed Mar. 4, 1999, which is a continuation-in-part of International Application No. PCT/US98/18360, filed Sep. 3, 1998; U.S. application Ser. No. 10/100,683 is a continuation-in-part of International Application No. PCT/US02/01109, filed Jan. 17, 2002, which claims the benefit of U.S. Provisional Application No. 60/262,066, filed Jan. 18, 2001; U.S. application Ser. No. 10/100,683 is a continuation-in-part of International Application No. PCT/US98/18360, filed Sep. 3, 1998, which claims the benefit of U.S. Provisional Application Nos. 60/057,626, filed Sep. 5, 1997, 60/057,663, filed Sep. 5, 1997, 60/057,669, filed Sep. 5, 1997, 60/058,667, filed Sep. 12, 1997, 60/058,974, filed Sep. 12, 1997, 60/058,973, filed Sep. 12, 1997, 60/058,666, filed Sep. 12, 1997, and 60/090,112, filed Jun. 22, 1998; U.S. application Ser. No. 10/100,683 is a continuation-in-part of U.S. application Ser. No. 09/281,976, filed Mar. 31, 1999, which is a continuation-in-part of International Application No. PCT/US98/20775, filed Oct. 1, 1998; U.S. application Ser. No. 10/100,683 is a continuation-in-part of International Application No. PCT/US98/20775, filed Oct. 1, 1998, which claims the benefit of U.S. Provisional Application Nos. 60/060,837, filed Oct. 2, 1997, 60/060,862, filed Oct. 2, 1997, 60/060,839, filed Oct. 2, 1997, 60/060,866, filed Oct. 2, 1997, 60/060,843, filed Oct. 2, 1997, 60/060,836, filed Oct. 2, 1997, 60/060,838, filed Oct. 2, 1997, 60/060,874, filed Oct. 2, 1997, 60/060,833, filed Oct. 2, 1997, 60/060,884, filed Oct. 2, 1997, and 60/060,880, filed Oct. 2, 1997; U.S. application Ser. No. 10/100,683 is a continuation-in-part of U.S. application Ser. No. 09/984,429, filed Oct. 30, 2001, which claims the benefit of U.S. Provisional Application No. 60/244,591, filed Nov. 1, 2000; U.S. application Ser. No. 09/984,429 is a continuation-in-part of U.S. application Ser. No. 09/288,143, filed Apr. 8, 1999, which is a continuation-in-part of International Application No. PCT/US98/21142, filed Oct. 8, 1998; U.S. application Ser. No. 10/100,683 claims the benefit of U.S. Provisional Application No. 60/244,591, filed Nov. 1, 2000; U.S. application Ser. No. 10/100,683 is a continuation-in-part of U.S. application Ser. No. 09/288,143, filed Apr. 8, 1999, which is a continuation-in-part of International Application No. PCT/US98/21142, filed Oct. 8, 1998; U.S. application Ser. No. 10/100,683 is a continuation-in-part of International Application No. PCT/US98/21142, filed Oct. 8, 1998, which claims the benefit of U.S. Provisional Application Nos. 60/061,463, filed Oct. 9, 1997, 60/061,529, filed Oct. 9, 1997, 60/071,498, filed Oct. 9, 1997, 60/061,527, filed Oct. 9, 1997, 60/061,536, filed Oct. 9, 1997, and 60/061,532, filed Oct. 9, 1997; U.S. application Ser. No. 10/100,683 is a continuation-in-part of U.S. application Ser. No. 09/296,622, filed Apr. 23, 1999, which is a continuation-in-part of International Application No. PCT/US98/22376, filed Oct. 23, 1998; U.S. application Ser. No. 10/100,683 is a continuation-in-part of International Application No. PCT/US98/22376, filed Oct. 23, 1998, which claims the benefit of U.S. Provisional Application Nos. 60/063,099, filed Oct. 24, 1997, 60/063,088, filed Oct. 24, 1997, 60/063,100, filed Oct. 24, 1997, 60/063,387, filed Oct. 24, 1997, 60/063,148, filed Oct. 24, 1997, 60/063,386, filed Oct. 24, 1997, 60/062,784, filed Oct. 24, 1997, 60/063,091, filed Oct. 24, 1997, 60/063,090, filed Oct. 24, 1997, 60/063,089, filed Oct. 24, 1997, 60/063,092, filed Oct. 24, 1997, 60/063,111, filed Oct. 24, 1997, 60/063,101, filed Oct. 24, 1997, 60/063,109, filed Oct. 24, 1997, 60/063,110, filed Oct. 24, 1997, 60/063,098, filed Oct. 24, 1997, and 60/063,097, filed Oct. 24, 1997; U.S. application Ser. No. 10/100,683 is a continuation-in-part of U.S. application Ser. No. 09/974,879, filed Oct. 12, 2001, which claims the benefit of U.S. Provisional Application No. 60/239,893, filed Oct. 13, 2000; U.S. application Ser. No. 09/974,879 is a continuation-in-part of U.S. application Ser. No. 09/818,683, filed Mar. 28, 2001, which is a continuation of U.S. application Ser. No. 09/305,736, filed May 5, 1999, which is a continuation-in-part of International Application No. PCT/US98/23435, filed Nov. 4, 1998; U.S. application Ser. No. 10/100,683 is a continuation-in-part of U.S. application Ser. No. 09/818,683, filed Mar. 28, 2001, which is a continuation of U.S. application Ser. No. 09/305,736, filed May 5, 1999, which is a continuation-in-part of International Application No. PCT/US98/23435, filed Nov. 4, 1998; U.S. application Ser. No. 10/100,683 is a continuation-in-part of U.S. application Ser. No. 09/305,736, filed May 5, 1999, which is a continuation-in-part of International Application No. PCT/US98/23435, filed Nov. 4, 1998; U.S. application Ser. No. 10/100,683 is a continuation-in-part of International Application No. PCT/US98/23435, filed Nov. 4, 1998, which claims the benefit of U.S. Provisional Application Nos. 60/064,911, filed Nov. 7, 1997, 60/064,912, filed Nov. 7, 1997, 60/064,983, filed Nov. 7, 1997, 60/064,900, filed Nov. 7, 1997, 60/064,988, filed Nov. 7, 1997, 60/064,987, filed Nov. 7, 1997, 60/064,908, filed Nov. 7, 1997, 60/064,984, filed Nov. 7, 1997, 60/064,985, filed Nov. 7, 1997, 60/066,094, filed Nov. 17, 1997, 60/066,100, filed Nov. 17, 1997, 60/066,089, filed Nov. 17, 1997, 60/066,095, filed Nov. 17, 1997, and 60/066,090, filed Nov. 17, 1997; U.S. application Ser. No. 10/100,683 is a continuation-in-part of U.S. application Ser. No. 09/334,595, filed Jun. 17, 1999, which is a continuation-in-part of International Application No. PCT/US98/27059, filed Dec. 17, 1998; U.S. application Ser. No. 10/100,683 is a continuation-in-part of International Application No. PCT/US98/27059, filed Dec. 17, 1998, which claims the benefit of U.S. Provisional Application Nos. 60/070,923, filed Dec. 18, 1997, 60/068,007, filed Dec. 18, 1997, 60/068,057, filed Dec. 18, 1997, 60/068,006, filed Dec. 18, 1997, 60/068,369, filed Dec. 19, 1997, 60/068,367, filed Dec. 19, 1997, 60/068,368, filed Dec. 19, 1997, 60/068,169, filed Dec. 19, 1997, 60/068,053, filed Dec. 18, 1997, 60/068,064, filed Dec. 18, 1997, 60/068,054, filed Dec. 18, 1997, 60/068,008, filed Dec. 18, 1997, and 60/068,365, filed Dec. 19, 1997; U.S. application Ser. No. 10/100,683 is a continuation-in-part of U.S. application Ser. No. 09/938,671, filed Aug. 27, 2001, which is a continuation of U.S. application Ser. No. 09/739,907, filed Dec. 20, 2000, which is a continuation of U.S. application Ser. No. 09/348,457, filed Jul. 7, 1999, which is a continuation-in-part of International Application No. PCT/US99/00108, filed Jan. 6, 1999; U.S. application Ser. No. 10/100,683 is a continuation-in-part of U.S. application Ser. No. 09/739,907, filed Dec. 20, 2000, which is a continuation of U.S. application Ser. No. 09/348,457, filed Jul. 7, 1999, which is a continuation-in-part of International Application No. PCT/US99/00108, filed Jan. 6, 1999; U.S. application Ser. No. 10/100,683 is a continuation-in-part of U.S. application Ser. No. 09/348,457, filed Jul. 7, 1999, which is a continuation-in-part of International Application No. PCT/US99/00108, filed Jan. 6, 1999; U.S. application Ser. No. 10/100,683 is a continuation-in-part of International Application No. PCT/US99/00108, filed Jan. 6, 1999, which claims the benefit of U.S. Provisional Application Nos. 60/070,704, filed Jan. 7, 1998, 60/070,658, filed Jan. 7, 1998, 60/070,692, filed Jan. 7, 1998, and 60/070,657, filed Jan. 7, 1998; U.S. application Ser. No. 10/100,683 is a continuation-in-part of U.S. application Ser. No. 09/949,925, filed Sep. 12, 2001, which claims the benefit of U.S. Provisional Application No. 60/232,150, filed Sep. 12, 2000; U.S. application Ser. No. 09/949,925 is a continuation-in-part of International Application No. PCT/US99/01621, filed Jan. 27, 1999; U.S. application Ser. No. 09/949,925 is a continuation-in-part of U.S. application Ser. No. 09/363,044, filed Jul. 29, 1999, which is a continuation-in-part of International Application No. PCT/US99/01621, filed Jan. 27, 1999; U.S. application Ser. No. 10/100,683 is a continuation-in-part of U.S. application Ser. No. 09/813,153, filed Mar. 21, 2001, which is a continuation of U.S. application Ser. No. 09/363,044, filed Jul. 29, 1999, which is a continuation-in-part of International Application No. PCT/US99/01621, filed Jan. 27, 1999; U.S. application Ser. No. 10/100,683 is a continuation-in-part of U.S. application Ser. No. 09/363,044, filed Jul. 29, 1999, which is a continuation-in-part of International Application No. PCT/US99/01621, filed Jan. 27, 1999; U.S. application Ser. No. 10/100,683 is a continuation-in-part of International Application No. PCT/US99/01621, filed Jan. 27, 1999, which claims the benefit of U.S. Provisional Application Nos. 60/073,170, filed Jan. 30, 1998, 60/073,167, filed Jan. 30, 1998, 60/073,165, filed Jan. 30, 1998, 60/073,164, filed Jan. 30, 1998, 60/073,162, filed Jan. 30, 1998, 60/073,161, filed Jan. 30, 1998, 60/073,160, filed Jan. 30, 1998, and 60/073,159, filed Jan. 30, 1998; U.S. application Ser. No. 10/100,683 is a continuation-in-part of U.S. application Ser. No. 10/062,548, filed Feb. 5, 2002, which is a continuation of U.S. application Ser. No. 09/369,247, filed Aug. 5, 1999; U.S. application Ser. No. 09/369,247 is a continuation-in-part of International Application No. PCT/US99/02293, filed Feb. 4, 1999; U.S. application Ser. No. 10/100,683 is a continuation-in-part of U.S. application Ser. No. 09/369,247, filed Aug. 5, 1999; U.S. application Ser. No. 09/369,247 is a continuation-in-part of International Application No. PCT/US99/02293, filed Feb. 4, 1999; U.S. application Ser. No. 10/100,683 is a continuation-in-part of International Application No. PCT/US99/02293, filed Feb. 4, 1999, which claims the benefit of U.S. Provisional Application Nos. 60/074,118, filed Feb. 9, 1998, 60/074,157, filed Feb. 9, 1998, 60/074,037, filed Feb. 9, 1998, 60/074,141, filed Feb. 9, 1998, and 60/074,341, filed Feb. 9, 1998; U.S. application Ser. No. 10/100,683 is a continuation-in-part of U.S. application Ser. No. 09/716,129, filed Nov. 17, 2000, which is a continuation-in-part of International Application No. PCT/US99/03939, filed Feb. 24, 1999; U.S. application Ser. No. 09/716,129 is a continuation of U.S. application Ser. No. 09/382,572, filed Aug. 25, 1999, which is a continuation-in-part of International Application No. PCT/US99/03939, filed Feb. 24, 1999; U.S. application Ser. No. 10/100,683 is a continuation-in-part of International Application No. PCT/US99/03939, filed Feb. 24, 1999, which claims the benefit of U.S. Provisional Application Nos. 60/076,053, filed Feb. 26, 1998, 60/076,051, filed Feb. 26, 1998, 60/076,054, filed Feb. 26, 1998, 60/076,052, filed Feb. 26, 1998, and 60/076,057, filed Feb. 26, 1998; U.S. application Ser. No. 10/100,683 is a continuation-in-part of U.S. application Ser. No. 09/798,889, filed Mar. 6, 2001, which is a continuation of U.S. application Ser. No. 09/393,022, filed Sep. 9, 1999, which is a continuation-in-part of International Application No. PCT/US99/05721, filed Mar. 11, 1999; U.S. application Ser. No. 10/100,683 is a continuation-in-part of International Application No. PCT/US99/05721, filed Mar. 11, 1999, which claims the benefit of U.S. Provisional Application Nos. 60/077,714, filed Mar. 12, 1998, 60/077,686, filed Mar. 12, 1998, 60/077,687, filed Mar. 12, 1998, and 60/077,696, filed Mar. 12, 1998; U.S. application Ser. No. 10/100,683 is a continuation-in-part of U.S. application Ser. No. 09/397,945, filed Sep. 17, 1999, which is a continuation-in-part of International Application No. PCT/US99/05804, filed Mar. 18, 1999; U.S. application Ser. No. 10/100,683 is a continuation-in-part of International Application No. PCT/US99/05804, filed Mar. 18, 1999, which claims the benefit of U.S. Provisional Application Nos. 60/078,566, filed Mar. 19, 1998, 60/078,576, filed Mar. 19, 1998, 60/078,573, filed Mar. 19, 1998, 60/078,574, filed Mar. 19, 1998, 60/078,579, filed Mar. 19, 1998, 60/080,314, filed Apr. 1, 1998, 60/080,312, filed Apr. 1, 1998, 60/078,578, filed Mar. 19, 1998, 60/078,581, filed Mar. 19, 1998, 60/078,577, filed Mar. 19, 1998, 60/078,563, filed Mar. 19, 1998, and 60/080,313, filed Apr. 1, 1998; U.S. application Ser. No. 10/100,683 is a continuation-in-part of U.S. application Ser. No. 09/948,783, filed Sep. 10, 2001, which claims the benefit of U.S. Provisional Application No. 60/231,846, filed Sep. 11, 2000; U.S. application Ser. No. 09/948,783 is a continuation-in-part of U.S. application Ser. No. 09/892,877, filed Jun. 28, 2001, which is a continuation of U.S. application Ser. No. 09/437,658, filed Nov. 10, 1999, which is a continuation-in-part of International Application No. PCT/US99/09847, filed May 6, 1999; U.S. application Ser. No. 10/100,683 is a continuation-in-part of U.S. application Ser. No. 09/892,877, filed Jun. 28, 2001, which is a continuation of U.S. application Ser. No. 09/437,658, filed Nov. 10, 1999, which is a continuation-in-part of International Application No. PCT/US99/09847, filed May 6, 1999; U.S. application Ser. No. 10/100,683 is a continuation-in-part of International Application No. PCT/US99/09847, filed May 6, 1999, which claims the benefit of U.S. Provisional Application Nos. 60/085,093, filed May 12, 1998, 60/085,094, filed May 12, 1998, 60/085,105, filed May 12, 1998, 60/085,180, filed May 12, 1998, 60/085,927, filed May 18, 1998, 60/085,906, filed May 18, 1998, 60/085,920, filed May 18, 1998, 60/085,924, filed May 18, 1998, 60/085,922, filed May 18, 1998, 60/085,923, filed May 18, 1998, 60/085,921, filed May 18, 1998, 60/085,925, filed May 18, 1998, and 60/085,928, filed May 18, 1998; U.S. application Ser. No. 10/100,683 is a continuation-in-part of U.S. application Ser. No. 10/050,873, filed Jan. 18, 2002, which claims the benefit of U.S. Provisional Application Nos. 60/263,681, filed Jan. 24, 2001, and 60/263,230, filed Jan. 23, 2001; U.S. application Ser. No. 10/050,873 is a continuation-in-part of U.S. application Ser. No. 09/461,325, filed Dec. 14, 1999, which is a continuation-in-part of International Application No. PCT/US99/13418, filed Jun. 15, 1999; U.S. application Ser. No. 10/100,683 is a continuation-in-part of U.S. application Ser. No. 10/012,542, filed Dec. 12, 2001, which is a divisional of U.S. application Ser. No. 09/461,325, filed Dec. 14, 1999, which is a continuation-in-part of International Application No. PCT/US99/13418, filed Jun. 15, 1999; U.S. application Ser. No. 10/100,683 is a continuation-in-part of U.S. application Ser. No. 09/461,325, filed Dec. 14, 1999, which is a continuation-in-part of International Application No. PCT/US99/13418, filed Jun. 15, 1999; U.S. application Ser. No. 10/100,683 is a continuation-in-part of International Application No. PCT/US99/13418, filed Jun. 15, 1999, which claims the benefit of U.S. Provisional Application Nos. 60/089,507, filed Jun. 16, 1998, 60/089,508, filed Jun. 16, 1998, 60/089,509, filed Jun. 16, 1998, 60/089,510, filed Jun. 16, 1998, 60/090,112, filed Jun. 22, 1998, and 60/090,113, filed Jun. 22, 1998; U.S. application Ser. No. 10/100,683 is a continuation-in-part of U.S. application Ser. No. 09/984,271, filed Oct. 29, 2001, which is a divisional of U.S. application Ser. No. 09/482,273, filed Jan. 13, 2000, which is a continuation-in-part of International Application No. PCT/US99/15849, filed Jul. 14, 1999; U.S. application Ser. No. 10/100,683 is a continuation-in-part of U.S. application Ser. No. 09/984,276, filed Oct. 29, 2001, which is a divisional of U.S. application Ser. No. 09/482,273, filed Jan. 13, 2000, which is a continuation-in-part of International Application No. PCT/US99/15849, filed Jul. 14, 1999; U.S. application Ser. No. 10/100,683 is a continuation-in-part of U.S. application Ser. No. 09/482,273, filed Jan. 13, 2000, which is a continuation-in-part of International Application No. PCT/US99/15849, filed Jul. 14, 1999; U.S. application Ser. No. 10/100,683 is a continuation-in-part of International Application No. PCT/US99/15849, filed Jul. 14, 1999, which claims the benefit of U.S. Provisional Application Nos. 60/092,921, filed Jul. 15, 1998, 60/092,922, filed Jul. 15, 1998, and 60/092,956, filed Jul. 15, 1998; U.S. application Ser. No. 10/100,683 is a continuation-in-part of International Application No. PCT/US01/29871, filed Sep. 24, 2001, which claims the benefit of U.S. Provisional Application No. 60/234,925, filed Sep. 25, 2000; International Application No. PCT/US01/29871 is a continuation-in-part of International Application No. PCT/US01/00911, filed Jan. 12, 2001; U.S. application Ser. No. 10/100,683 is a continuation-in-part of International Application No. PCT/US01/00911, filed Jan. 12, 2001, which is a continuation-in-part of U.S. application Ser. No. 09/482,273, filed Jan. 13, 2000; U.S. application Ser. No. 10/100,683 claims the benefit of U.S. Provisional Application No. 60/350,898, filed Jan. 25, 2002; U.S. application Ser. No. 10/100,683 is a continuation-in-part of U.S. application Ser. No. 09/489,847, filed Jan. 24, 2000, which is a continuation-in-part of International Application No. PCT/US99/17130, filed Jul. 29, 1999; U.S. application Ser. No. 10/100,683 is a continuation-in-part of International Application No. PCT/US99/17130, filed Jul. 29, 1999, which claims the benefit of U.S. Provisional Application Nos. 60/094,657, filed Jul. 30, 1998, 60/095,486, filed Aug. 5, 1998, 60/096,319, filed Aug. 12, 1998, 60/095,454, filed Aug. 6, 1998, and 60/095,455, filed Aug. 6, 1998; U.S. application Ser. No. 10/100,683 is a continuation-in-part of U.S. application Ser. No. 10/054,988, filed Jan. 25, 2002, which is a continuation of U.S. application Ser. No. 09/904,615, filed Jul. 16, 2001, which is a continuation of U.S. application Ser. No. 09/739,254, filed Dec. 19, 2000, which is a continuation of U.S. application Ser. No. 09/511,554, filed Feb. 23, 2000, which is a continuation-in-part of International Application No. PCT/US99/19330, filed Aug. 24, 1999; U.S. application Ser. No. 10/100,683 is a continuation-in-part of U.S. application Ser. No. 09/904,615, filed Jul. 16, 2001, which is a continuation of U.S. application Ser. No. 09/739,254, filed Dec. 19, 2000, which is a continuation of U.S. application Ser. No. 09/511,554, filed Feb. 23, 2000, which is a continuation-in-part of International Application No. PCT/US99/19330, filed Aug. 24, 1999; U.S. application Ser. No. 10/100,683 is a continuation-in-part of International Application No. PCT/US99/19330, filed Aug. 24, 1999, which claims the benefit of U.S. Provisional Application Nos. 60/097,917, filed Aug. 25, 1998, and 60/098,634, filed Aug. 31, 1998; U.S. application Ser. No. 10/100,683 is a continuation-in-part of U.S. application Ser. No. 09/820,893, filed Mar. 30, 2001, which is a continuation of U.S. application Ser. No. 09/531,119, filed Mar. 20, 2000, which is a continuation-in-part of International Application No. PCT/US99/22012, filed Sep. 22, 1999; U.S. application Ser. No. 10/100,683 is a continuation-in-part of International Application No. PCT/US99/22012, filed Sep. 22, 1999, which claims the benefit of U.S. Provisional Application Nos. 60/101,546, filed Sep. 23, 1998, and 60/102,895, filed Oct. 2, 1998; U.S. application Ser. No. 10/100,683 is a continuation-in-part of U.S. application Ser. No. 09/948,820, filed Sep. 10, 2001, which is a continuation of U.S. application Ser. No. 09/565,391, filed May 5, 2000, which is a continuation-in-part of International Application No. PCT/US99/26409, filed Nov. 9, 1999; U.S. application Ser. No. 10/100,683 is a continuation-in-part of U.S. application Ser. No. 09/565,391, filed May 5, 2000, which is a continuation-in-part of International Application No. PCT/US99/26409, filed Nov. 9, 1999; U.S. application Ser. No. 10/100,683 is a continuation-in-part of International Application No. PCT/US99/26409, filed Nov. 9, 1999, which claims the benefit of U.S. Provisional Application No. 60/108,207, filed Nov. 12, 1998; U.S. application Ser. No. 10/100,683 is a continuation-in-part of U.S. application Ser. No. 09/895,298, filed Jul. 2, 2001, which is a continuation of U.S. application Ser. No. 09/591,316, filed Jun. 9, 2000, which is a continuation-in-part of International Application No. PCT/US99/29950, filed Dec. 16, 1999; U.S. application Ser. No. 10/100,683 is a continuation-in-part of International Application No. PCT/US99/29950, filed Dec. 16, 1999, which claims the benefit of U.S. Provisional Application Nos. 60/113,006, filed Dec. 18, 1998, and 60/112,809, filed Dec. 17, 1998; U.S. application Ser. No. 10/100,683 is a continuation-in-part of U.S. application Ser. No. 09/985,153, filed Nov. 1, 2001, which is a continuation of U.S. application Ser. No. 09/618,150, filed Jul. 17, 2000, which is a continuation-in-part of International Application No. PCT/US00/00903, filed Jan. 18, 2000; U.S. application Ser. No. 10/100,683 is a continuation-in-part of International Application No. PCT/US00/00903, filed Jan. 18, 2000, which claims the benefit of U.S. Provisional Application No. 60/116,330, filed Jan. 19, 1999; U.S. application Ser. No. 10/100,683 is a continuation-in-part of U.S. application Ser. No. 09/997,131, filed Nov. 30, 2001, which is a continuation of U.S. application Ser. No. 09/628,508, filed Jul. 28, 2000, which is a continuation-in-part of International Application No. PCT/US00/03062, filed Feb. 8, 2000; U.S. application Ser. No. 10/100,683 is a continuation-in-part of International Application No. PCT/US00/03062, filed Feb. 8, 2000, which claims the benefit of U.S. Provisional Application No. 60/119,468, filed Feb. 10, 1999; U.S. application Ser. No. 10/100,683 is a continuation-in-part of U.S. application Ser. No. 10/050,882, filed Jan. 18, 2002, which is a continuation of U.S. application Ser. No. 09/661,453, filed Sep. 13, 2000, which is a continuation-in-part of International Application No. PCT/US00/06783, filed Mar. 16, 2000; U.S. application Ser. No. 10/100,683 is a continuation-in-part of U.S. application Ser. No. 09/661,453, filed Sep. 13, 2000, which is a continuation-in-part of International Application No. PCT/US00/06783, filed Mar. 16, 2000; U.S. application Ser. No. 10/100,683 is a continuation-in-part of International Application No. PCT/US00/06783, filed Mar. 16, 2000, which claims the benefit of U.S. Provisional Application No. 60/125,055, filed Mar. 18, 1999; U.S. application Ser. No. 10/100,683 is a continuation-in-part of U.S. application Ser. No. 10/050,704, filed Jan. 18, 2002, which is a continuation of U.S. application Ser. No. 09/684,524, filed Oct. 10, 2000, which is a continuation-in-part of International Application No. PCT/US00/08979, filed Apr. 6, 2000; U.S. application Ser. No. 10/100,683 is a continuation-in-part of U.S. application Ser. No. 09/684,524, filed Oct. 10, 2000, which is a continuation-in-part of International Application No. PCT/US00/08979, filed Apr. 6, 2000; U.S. application Ser. No. 10/100,683 is a continuation-in-part of International Application No. PCT/US00/08979, filed Apr. 6, 2000, which claims the benefit of U.S. Provisional Application Nos. 60/128,693, filed Apr. 9, 1999, and 60/130,991, filed Apr. 26, 1999; U.S. application Ser. No. 10/100,683 is a continuation-in-part of U.S. application Ser. No. 10/042,141, filed Jan. 11, 2002, which is a continuation of U.S. application Ser. No. 09/726,643, filed Dec. 1, 2000, which is a continuation-in-part of International Application No. PCT/US00/15187, filed Jun. 2, 2000; U.S. application Ser. No. 10/100,683 is a continuation-in-part of U.S. application Ser. No. 09/726,643, filed Dec. 1, 2000, which is a continuation-in-part of International Application No. PCT/US00/15187, filed Jun. 2, 2000; U.S. application Ser. No. 10/100,683 is a continuation-in-part of International Application No. PCT/US00/15187, filed Jun. 2, 2000, which claims the benefit of U.S. Provisional Application No. 60/137,725, filed Jun. 7, 1999; U.S. application Ser. No. 10/100,683 is a continuation-in-part of U.S. application Ser. No. 09/756,168, filed Jan. 9, 2001, which is a continuation-in-part of International Application No. PCT/US00/19735, filed Jul. 23, 1999; U.S. application Ser. No. 10/100,683 is a continuation-in-part of International Application No. PCT/US00/19735, filed Jul. 20, 2000, which claims the benefit of U.S. Provisional Application No. 60/145,220, filed Jul. 23, 1999; U.S. application Ser. No. 10/100,683 is a continuation-in-part of U.S. application Ser. No. 10/060,255, filed Feb. 1, 2002, which is a continuation of U.S. application Ser. No. 09/781,417, filed Feb. 13, 2001, which is a continuation-in-part of International Application No. PCT/US00/22325, filed Aug. 16, 2000; U.S. application Ser. No. 10/100,683 is a continuation-in-part of U.S. application Ser. No. 09/781,417, filed Feb. 13, 2001, which is a continuation-in-part of International Application No. PCT/US00/22325, filed Aug. 16, 2000; U.S. application Ser. No. 10/100,683 is a continuation-in-part of International Application No. PCT/US00/22325, filed Aug. 16, 2000, which claims the benefit of U.S. Provisional Application No. 60/149,182, filed Aug. 17, 1999; U.S. application Ser. No. 10/100,683 is a continuation-in-part of U.S. application Ser. No. 09/789,561, filed Feb. 22, 2001, which is a continuation-in-part of International Application No. PCT/US00/24008, filed Aug. 31, 2000; U.S. application Ser. No. 10/100,683 is a continuation-in-part of International Application No. PCT/US00/24008, filed Aug. 31, 2000, which claims the benefit of U.S. Provisional Application Nos. 60/152,315, filed Sep. 3, 1999, and 60/152,317, filed Sep. 3, 1999; U.S. application Ser. No. 10/100,683 is a continuation-in-part of U.S. application Ser. No. 09/800,729, filed Mar. 8, 2001, which is a continuation-in-part of International Application No. PCT/US00/26013, filed Sep. 22, 2000; U.S. application Ser. No. 10/100,683 is a continuation-in-part of International Application No. PCT/US00/26013, filed Sep. 22, 2000, which claims the benefit of U.S. Provisional Application No. 60/155,709, filed Sep. 24, 1999; U.S. application Ser. No. 10/100,683 is a continuation-in-part of U.S. application Ser. No. 09/832,129, filed Apr. 11, 2001, which is a continuation-in-part of International Application No. PCT/US00/28664, filed Oct. 17, 2000; U.S. application Ser. No. 10/100,683 is a continuation-in-part of International Application No. PCT/US00/28664, filed Oct. 17, 2000, which claims the benefit of U.S. Provisional Application Nos. 60/163,085, filed Nov. 2, 1999, and 60/172,411, filed Dec. 17, 1999; U.S. application Ser. No. 10/100,683 is a continuation-in-part of International Application No. US00/29363, filed Oct. 25, 2000, which claims the benefit of U.S. Provisional Application Nos. 60/215,139, filed Jun. 30, 2000, and 60/162,239, filed Oct. 29, 1999; U.S. application Ser. No. 10/100,683 is a continuation-in-part of International Application No. US00/29360, filed Oct. 25, 2000, which claims the benefit of U.S. Provisional Application Nos. 60/215,138, filed Jun. 30, 2000, and 60/162,211, filed Oct. 29, 1999; U.S. application Ser. No. 10/100,683 is a continuation-in-part of International Application No. US00/29362, filed Oct. 25, 2000, which claims the benefit of U.S. Provisional Application Nos. 60/215,131, filed Jun. 30, 2000, and 60/162,240, filed Oct. 29, 1999; U.S. application Ser. No. 10/100,683 is a continuation-in-part of International Application No. US00/29365, filed Oct. 25, 2000, which claims the benefit of U.S. Provisional Application Nos. 60/219,666, filed Jul. 21, 2000, and 60/162,237, filed Oct. 29, 1999; U.S. application Ser. No. 10/100,683 is a continuation-in-part of International Application No. US00/29364, filed Oct. 25, 2000, which claims the benefit of U.S. Provisional Application Nos. 60/215,134, filed Jun. 30, 2000, and 60/162,238, filed Oct. 29, 1999; U.S. application Ser. No. 10/100,683 is a continuation-in-part of International Application No. US00/30040, filed Nov. 1, 2000, which claims the benefit of U.S. Provisional Application Nos. 60/215,130, filed Jun. 30, 2000, and 60/163,580, filed Nov. 5, 1999; U.S. application Ser. No. 10/100,683 is a continuation-in-part of International Application No. US00/30037, filed Nov. 1, 2000, which claims the benefit of U.S. Provisional Application Nos. 60/215,137, filed Jun. 30, 2000, and 60/163,577, filed Nov. 5, 1999; U.S. application Ser. No. 10/100,683 is a continuation-in-part of International Application No. US00/30045, filed Nov. 1, 2000, which claims the benefit of U.S. Provisional Application Nos. 60/215,133, filed Jun. 30, 2000, and 60/163,581, filed Nov. 5, 1999; U.S. application Ser. No. 10/100,683 is a continuation-in-part of International Application No. US00/30036, filed Nov. 1, 2000, which claims the benefit of U.S. Provisional Application Nos. 60/221,366, filed Jul. 27, 2000, and 60/163,576, filed Nov. 5, 1999; U.S. application Ser. No. 10/100,683 is a continuation-in-part of International Application No. US00/30039, filed Nov. 1, 2000, which claims the benefit of U.S. Provisional Application Nos. 60/221,367, filed Jul. 27, 2000, 60/195,296, filed Apr. 7, 2000, and 60/164,344, filed Nov. 9, 1999; U.S. application Ser. No. 10/100,683 is a continuation-in-part of International Application No. US00/30654, filed Nov. 8, 2000, which claims the benefit of U.S. Provisional Application Nos. 60/221,142, filed Jul. 27, 2000, and 60/164,835, filed Nov. 12, 1999; U.S. application Ser. No. 10/100,683 is a continuation-in-part of International Application No. US00/30628, filed Nov. 8, 2000, which claims the benefit of U.S. Provisional Application Nos. 60/215,140, filed Jun. 30, 2000, and 60/164,744, filed Nov. 12, 1999; U.S. application Ser. No. 10/100,683 is a continuation-in-part of International Application No. US00/30653, filed Nov. 8, 2000, which claims the benefit of U.S. Provisional Application Nos. 60/221,193, filed Jul. 27, 2000, and 60/164,735, filed Nov. 12, 1999; U.S. application Ser. No. 10/100,683 is a continuation-in-part of International Application No. US00/30629, filed Nov. 8, 2000, which claims the benefit of U.S. Provisional Application Nos. 60/222,904, filed Aug. 3, 2000, and 60/164,825, filed Nov. 12, 1999; U.S. application Ser. No. 10/100,683 is a continuation-in-part of International Application No. US00/30679, filed Nov. 8, 2000, which claims the benefit of U.S. Provisional Application Nos. 60/224,007, filed Aug. 4, 2000, and 60/164,834, filed Nov. 12, 1999; U.S. application Ser. No. 10/100,683 is a continuation-in-part of International Application No. US00/30674, filed Nov. 8, 2000, which claims the benefit of U.S. Provisional Application Nos. 60/215,128, filed Jun. 30, 2000, and 60/164,750, filed Nov. 12, 1999; U.S. application Ser. No. 10/100,683 is a continuation-in-part of International Application No. US00/31162, filed Nov. 15, 2000; U.S. Provisional Application No. 60/215,136 claims the benefit of U.S. Provisional Application Nos. 60/215,136, filed Jun. 30, 2000, which claims the benefit of U.S. Provisional Application No. 60/166,415, filed Nov. 19, 1999; U.S. application Ser. No. 10/100,683 is a continuation-in-part of International Application No. US00/31282, filed Nov. 15, 2000, which claims the benefit of U.S. Provisional Application Nos. 60/219,665, filed Jul. 21, 2000, and 60/166,414, filed Nov. 19, 1999; U.S. application Ser. No. 10/100,683 is a continuation-in-part of International Application No. US00/30657, filed Nov. 8, 2000, which claims the benefit of U.S. Provisional Application Nos. 60/215,132, filed Jun. 30, 2000, and 60/164,731, filed Nov. 12, 1999; U.S. application Ser. No. 10/100,683 is a continuation-in-part of International Application No. US01/01396, filed Jan. 17, 2001; U.S. Provisional Application No. 60/256,968 claims the benefit of U.S. Provisional Application Nos. 60/256,968, filed Dec. 21, 2000, which claims the benefit of U.S. Provisional Application No. 60/226,280, filed Aug. 18, 2000; U.S. application Ser. No. 10/100,683 is a continuation-in-part of International Application No. US01/01387, filed Jan. 17, 2001; U.S. Provisional Application No. 60/259,803 claims the benefit of U.S. Provisional Application Nos. 60/259,803, filed Jan. 5, 2001, which claims the benefit of U.S. Provisional Application No. 60/226,380, filed Aug. 18, 2000; U.S. application Ser. No. 10/100,683 is a continuation-in-part of International Application No. US01/01567, filed Jan. 17, 2001, which claims the benefit of U.S. Provisional Application No. 60/228,084, filed Aug. 28, 2000; U.S. application Ser. No. 10/100,683 is a continuation-in-part of International Application No. US01/01431, filed Jan. 17, 2001, which claims the benefit of U.S. Provisional Application No. 60/231,968, filed Sep. 12, 2000; International Application No. US01/01431 is a continuation-in-part of U.S. application Ser. No. 09/915,582, filed Jul. 27, 2001; U.S. application Ser. No. 10/100,683 is a continuation-in-part of International Application No. US01/01432, filed Jan. 17, 2001, which claims the benefit of U.S. Provisional Application No. 60/236,326, filed Sep. 29, 2000; U.S. application Ser. No. 10/100,683 is a continuation-in-part of International Application No. US01/00544, filed Jan. 9, 2001, which claims the benefit of U.S. Provisional Application No. 60/234,211, filed Sep. 20, 2000; U.S. application Ser. No. 10/100,683 is a continuation-in-part of International Application No. US01/01435, filed Jan. 17, 2001, which claims the benefit of U.S. Provisional Application No. 60/226,282, filed Aug. 18, 2000; U.S. application Ser. No. 10/100,683 is a continuation-in-part of International Application No. US01/01386, filed Jan. 17, 2001, which claims the benefit of U.S. Provisional Application No. 60/232,104, filed Sep. 12, 2000; U.S. application Ser. No. 10/100,683 is a continuation-in-part of International Application No. US01/01565, filed Jan. 17, 2001, which claims the benefit of U.S. Provisional Application No. 60/234,210, filed Sep. 20, 2000; U.S. application Ser. No. 10/100,683 is a continuation-in-part of International Application No. US01/01394, filed Jan. 17, 2001, which claims the benefit of U.S. Provisional Application Nos. 60/259,805, filed Jan. 5, 2001, and 60/226,278, filed Aug. 18, 2000; U.S. application Ser. No. 10/100,683 is a continuation-in-part of International Application No. US01/01434, filed Jan. 17, 2001, which claims the benefit of U.S. Provisional Application Nos. 60/259,678, filed Jan. 5, 2001, and 60/226,279, filed Aug. 18, 2000; U.S. application Ser. No. 10/100,683 is a continuation-in-part of International Application No. US01/01397, filed Jan. 17, 2001, which claims the benefit of U.S. Provisional Application No. 60/226,281, filed Aug. 18, 2000; U.S. application Ser. No. 10/100,683 is a continuation-in-part of International Application No. US01/01385, filed Jan. 17, 2001, which claims the benefit of U.S. Provisional Application No. 60/231,969, filed Sep. 12, 2000; U.S. application Ser. No. 10/100,683 is a continuation-in-part of International Application No. US01/01384, filed Jan. 17, 2001, which claims the benefit of U.S. Provisional Application Nos. 60/259,516, filed Jan. 4, 2001, and 60/228,086, filed Aug. 28, 2000; U.S. application Ser. No. 10/100,683 is a continuation-in-part of International Application No. US01/01383, filed Jan. 17, 2001, which claims the benefit of U.S. Provisional Application Nos. 60/259,804, filed Jan. 5, 2001, and 60/228,083, filed Aug. 28, 2000; U.S. application Ser. No. 10/100,683 is a continuation-in-part of International Application No. PCT/US02/05064, filed Feb. 21, 2002, which claims the benefit of U.S. Provisional Application Nos. 60/304,444, filed Jul. 12, 2001, and 60/270,658, filed Feb. 23, 2001; U.S. application Ser. No. 10/100,683 is a continuation-in-part of International Application No. PCT/US02/05301, filed Feb. 21, 2002, which claims the benefit of U.S. Provisional Application Nos. 60/304,417, filed Jul. 12, 2001, and 60/270,625, filed Feb. 23, 2001; U.S. application Ser. No. 10/100,683 claims the benefit of U.S. Provisional Application Nos. 60/304,121, filed Jul. 11, 2001, 60/295,869, filed Jun. 6, 2001, 60/325,209, filed Sep. 28, 2001, 60/311,085, filed Aug. 10, 2001, 60/330,629, filed Oct. 26, 2001, 60/331,046, filed Nov. 7, 2001, 60/358,554, filed Feb. 22, 2002, and 60/358,714, filed Feb. 25, 2002. This application is a continuation-in-part of U.S. application Ser. No. 11/968,925, filed Jan. 3, 2008, which is a divisional of 10/644,765, filed Aug. 21, 2003, which is a continuation of International Application No. PCT/US02/05301, filed Feb. 21, 2002, which in turn claims benefit under 35 U.S.C. §119(e) based on U.S. Provisional Application Nos. 60/270,625 and 60/304,417, filed Feb. 23, 2001 and Jul. 12, 2001, respectively. This application is a continuation-in-part of U.S. application Ser. No. 12/538,668, filed Aug. 10, 2009, which is a continuation of U.S. application Ser. No. 11/240,769, filed Oct. 3, 2005, which is a continuation application of U.S. application Ser. No. 09/997,131, filed Nov. 30, 2001, now abandoned, which is a continuation application of U.S. application Ser. No. 09/628,508, filed Jul. 28, 2000, now abandoned, which is a continuation-in-part of PCT International Application Serial No. PCT/US00/03062, filed Feb. 8, 2000, which claims benefit under 35 U.S.C. §119(e) based on U.S. Provisional Application No. 60/119,468 filed Feb. 10, 1999. This application is a continuation-in-part of U.S. application Ser. No. 11/777,133, filed Jul. 12, 2007, which is a continuation of U.S. application Ser. No. 11/229,769, filed Sep. 20, 2005, which is a continuation of U.S. application Ser. No. 10/233,453, filed Sep. 4, 2002, which is a divisional of U.S. application Ser. No. 09/489,847 filed Jan. 24, 2000, which is a continuation-in-part of International Application No. PCT/US99/17130 filed Jul. 29, 1999, which claims benefit under 35 U.S.C. §119(e) based on U.S. Provisional Applications Nos. 60/094,657, filed Jul. 30, 1998, 60/095,486, filed Aug. 5, 1998, 60/096,319, filed Aug. 12, 1998, 60/095,454, filed Aug. 6, 1998, and 60/095,455, filed Aug. 6, 1998. This application is a continuation-in-part of U.S. application Ser. No. 12/268,263, filed Nov. 10, 2008, which is a divisional of U.S. application Ser. No. 11/375,555, filed Mar. 15, 2006, which is a continuation-in-part of application Ser. No. 10/103,295, filed Mar. 22, 2002 (now U.S. Pat. No. 7,091,315, issued Aug. 15, 2006), which is a continuation-in-part of International Application No. PCT/US01/29871, filed Sep. 24, 2001, which claims benefit under 35 U.S.C. §119(e) of U.S. Provisional Application No. 60/234,925, filed Sep. 25, 2000; application Ser. No. 10/103,295 is also a continuation-in-part of International Application No. PCT/US01/00911, filed Jan. 12, 2001 (now abandoned); application Ser. No. 10/103,295 is also a continuation-in-part of U.S. application Ser. No. 09/482,273, filed Jan. 13, 2000 (now U.S. Pat. No. 6,534,631, issued Mar. 18, 2003), which is a continuation-in-part of International Application No. PCT/US99/15849, filed Jul. 14, 1999, which claims benefit under 35 U.S.C. §119(e) of U.S. Provisional Application Nos. 60/092,921, 60/092,922, and 60/092,956, all of which were filed on Jul. 15, 1998. This application is a continuation-in-part of U.S. application Ser. No. 11/760,578, filed Jun. 8, 2007, which is a continuation of U.S. application Ser. No. 10/886,642, filed Jul. 9, 2004, which is a continuation of U.S. application Ser. No. 10/050,873, filed Jan. 18, 2002, which claims benefit under 35 U.S.C. §119(e) of U.S. Provisional Application Nos. 60/263,230, filed on Jan. 23, 2001, and 60/263,681, filed on Jan. 24, 2001; said U.S. application Ser. No. 10/050,873 is also a continuation-in-part of U.S. patent application Ser. No. 09/461,325, filed on Dec. 14, 1999, now U.S. Pat. No. 6,475,753, which is a continuation-in-part of International Patent Application No: PCT/US99/13418, filed on Jun. 15, 1999, which claims benefit under 35 U.S.C. §119(e) of U.S. Provisional Application Nos. 60/089,507, 60/089,508, 60/089,509, 60/089,510, each of which was filed on Jun. 16, 1998, and 60/090,112 and 60/090,113, each of which was filed on Jun. 22, 1998. This application is a continuation-in-part of U.S. application Ser. No. 12/274,626, filed Nov. 20, 2008, which is a divisional of U.S. application Ser. No. 11/608,978, filed Dec. 11, 2006, which is a continuation of U.S. application Ser. No. 10/918,446, filed Aug. 16, 2004, which is a divisional of U.S. application Ser. No. 10/062,548, filed Feb. 5, 2002 (now U.S. Pat. No. 6,924,356, issued Aug. 2, 2005), which is a continuation of U.S. application Ser. No. 09/369,247, filed Aug. 5, 1999 (now U.S. Pat. No. 6,569,992, issued May 27, 2003), which is a continuation-in-part of International Application PCT/US99/02293, filed Feb. 4, 1999, which is a non-provisional of, and claims benefit under 35 U.S.C. §119(e) to, U.S. Provisional Applications 60/074,118, filed Feb. 9, 1998, 60/074,157, filed Feb. 9, 1998, 60/074,037, filed Feb. 9, 1998, 60/074,141, filed Feb. 9, 1998, and 60/074,341, filed Feb. 9, 1998. This application is a continuation-in-part of U.S. application Ser. No. 11/780,874, filed Jul. 20, 2007, which is a continuation of U.S. patent application Ser. No. 10/935,098, filed Sep. 8, 2004, which is a continuation of U.S. patent application Ser. No. 09/938,671, filed Aug. 27, 2001, which is a continuation of U.S. patent application Ser. No. 09/739,907, filed Dec. 20, 2000 (now abandoned), which is a continuation of U.S. patent application Ser. No. 09/348,457, filed Jul. 7, 1999 (now abandoned), which is a continuation-in-part of International Application No. PCT/US99/00108, filed Jan. 6, 1999, which claims benefit under 35 U.S.C. §119(e) based on U.S. Provisional Application Nos. 60/070,704, filed Jan. 7, 1998; 60/070,658, filed Jan. 7, 1998; 60/070,692, filed Jan. 7, 1998; and 60/070,657, filed Jan. 7, 1998. This application is a continuation-in-part of U.S. application Ser. No. 12/325,800, filed Dec. 1, 2008, which is a divisional of U.S. application Ser. No. 11/565,909, filed Dec. 1, 2006, which is a divisional of U.S. application Ser. No. 10/970,493, filed on Oct. 22, 2004 (now U.S. Pat. No. 7,163,797, issued Jan. 16, 2007), which is a continuation of U.S. application Ser. No. 10/047,021, filed on Jan. 17, 2002 (now abandoned), which claims benefit under 35 U.S.C. §119 (e) of U.S. Provisional Application No. 60/262,066, filed on Jan. 18, 2001; U.S. application Ser. No. 10/047,021 is also a continuation-in-part of U.S. application Ser. No. 09/722,329, filed on Nov. 28, 2000 (now abandoned), which is a continuation of U.S. application Ser. No. 09/262,109, filed on Mar. 4, 1999 (now abandoned), which is a continuation-in-part of International Application PCT/US98/18360, filed on Sep. 3, 1998, which claims benefit under 35 U.S.C. §119(e) of U.S. Provisional Application Nos. 60/057,626; 60/057,663; 60/057,669, filed on Sep. 5, 1997; 60/058,666; 60/058,667; 60/058,973; 60/058,974, filed on Sep. 12, 1997; and, 60/090, 112, filed on Jun. 22, 1998. This application is a continuation-in-part of U.S. application Ser. No. 11/735,351, filed Apr. 13, 2007, which is a continuation of U.S. application Ser. No. 10/866,878, filed Jun. 15, 2004, which is a divisional of U.S. application Ser. No. 09/973,278, filed Oct. 10, 2001, which claims benefit under 35 U.S.C. §119(e) of U.S. Provisional Application No. 60/239,899, filed Oct. 13, 2000; U.S. application Ser. No. 09/973,278 is also a continuation-in-part of U.S. application Ser. No. 09/227,357, filed Jan. 8, 1999, which is a continuation-in-part of International Application No. PCT/US98/13684, filed Jul. 7, 1998, which claims benefit under 35 U.S.C. §119(e) based on U.S. Provisional Applications 60/051,926; 60/052,793; 60/051,925; 60/051,929; 60/052,803; 60/052,732; 60/051,931; 60/051,932; 60/051, 916; 60/051,930; 60/051,918; 60/051,920; 60/052,733; 60/052,795; 60/051,919; 60/051,928 (each of which was filed Jul. 8, 1997); and; 60/055,722; 60/055,723; 60/055,948; 60/055,949; 60/055,953; 60/055,950; 60/055,947; 60/055, 964; 60/056,360; 60/055,684; 60/055,984; 60/055,954 (each of which was filed Aug. 18, 1997); and; 60/058,785; 60/058, 664; 60/058,660; 60/058,661 (each of which was filed Sep. 12, 1997). This application is a continuation-in-part of U.S. application Ser. No. 11/759,448, filed Jun. 7, 2007, which is a continuation of U.S. application Ser. No. 11/229,770, filed Sep. 20, 2005 (abandoned), which is a continuation of U.S. application Ser. No. 09/933,767, filed Aug. 22, 2001 (abandoned), which is a continuation-in-part of International Application No. PCT/US01/05614, filed Feb. 21, 2001, which claims benefit under 35 U.S.C. §119(e) based on U.S. Provisional Patent Application Ser. Nos. 60/184,836, filed Feb. 24, 2000 and 60/193,170, filed Mar. 29, 2000. application Ser. No. 09/933,767 is a continuation-in-part of U.S. patent application Ser. No. 09/205,258, filed Dec. 4, 1998 (now U.S. Pat. No. 6,525,174), which is a continuation-in-part of International Patent Application No. PCT/US98/11422, filed Jun. 4, 1998, which claims benefit under 35 U.S.C. §119(e) based on U.S. Provisional Applications 60/048,885; 60/049,375; 60/048,881; 60/048,880; 60/048, 896; 60/049,020; 60/048,876; 60/048,895; 60/048,884; 60/048,894; 60/048,971; 60/048,964; 60/048,882; 60/048, 899; 60/048,893; 60/048,900; 60/048,901; 60/048,892; 60/048,915; 60/049,019; 60/048,970; 60/048,972; 60/048, 916; 60/049,373; 60/048,875; 60/049,374; 60/048,917; 60/048,949; 60/048,974; 60/048,883; 60/048,897; 60/048, 898; 60/048,962; 60/048,963; 60/048,877; 60/048,878, all filed Jun. 6, 1997, and 60/057,645; 60/057,642; 60/057,668; 60/057,635; 60/057,627; 60/057,667; 60/057,666; 60/057, 764; 60/057,643; 60/057,769; 60/057,763; 60/057,650; 60/057,584; 60/057,647; 60/057,661; 60/057,662; 60/057, 646; 60/057,654; 60/057,651; 60/057,644; 60/057,765; 60/057,762; 60/057,775; 60/057,648; 60/057,774; 60/057, 649; 60/057,770; 60/057,771; 60/057,761; 60/057,760; 60/057,776; 60/057,778; 60/057,629; 60/057,628; 60/057, 777; 60/057,634, all filed Sep. 5, 1997, and 60/070,923, filed Dec. 18, 1997. This application in a continuation-in-part of U.S. application Ser. No. 12/324,825, filed Nov. 26, 2008, which is a continuation of U.S. application Ser. No. 11/226, 657, filed Sep. 15, 2005, which is a divisional of U.S. application Ser. No. 10/062,831, filed Feb. 5, 2002, (now U.S. Pat. No. 7,001,992, issued Feb. 21, 2006), which is a divisional of U.S. application Ser. No. 09/690,454, filed Oct. 18, 2000 (now U.S. Pat. No. 6,531,447, issued Mar. 11, 2003), which is a continuation of U.S. application Ser. No. 09/189,144, filed Nov. 10, 1998 (now abandoned), which is a continuation-in-part of international Application No. PCT/US98/10868, filed May 28, 1998, which claims benefit under 35 U.S.C. §119(e) of U.S. Provisional Applications: 60/044,039; 60/048,093; 60/048,190; 60/050,935; 60/048,101; 60/048,356 (each filed May 30, 1997); and 60/056,250; 60/056,296; 60/056,293 (each filed Aug. 29, 1997). This application in a continuation-in-part of U.S. application Ser. No. 11/801,040, filed May 7, 2007, which is a divisional of U.S. application Ser. No. 10/062,831, filed Feb. 5, 2002, which is a divisional of U.S. application Ser. No. 09/690,454, filed Oct. 18, 2000 (now U.S. Pat. No. 6,531,447, issued Mar. 11, 2003), which is a continuation of U.S. application Ser. No. 09/189,144 filed Nov. 10, 1998 (now abandoned), which is a continuation-in-part of International Application No. PCT/US98/10868, filed May 28, 1998, which claims benefit under 35 U.S.C. §119(e) of U.S. Provisional Applications: 60/044,039; 60/048,093; 60/048,190; 60/050,935; 60/048,101; 60/048,356 (each filed May 30, 1997); and, 60/056,250; 60/056,296; 60/056,293 (each filed Aug. 29, 1997). This application in a continuation-in-part of U.S. application Ser. No. 11/744,695, filed May 4, 2007, which is a continuation of U.S. application Ser. No. 10/951,993 filed on Sep. 29, 2004, which is a divisional of U.S. application Ser. No. 10/058,993 filed on Jan. 30, 2002, which is a non-provisional of, and claims benefit under 35 U.S.C. §119(e) based on, U.S. Provisional Application No. 60/265,583 filed on Feb. 2, 2001; which is also a continuation-in-part, and claims priority under 35 U.S.C. §120, of U.S. application Ser. Nos. 09/852,659, 09/852,797, and 09/853,161 filed on May 11, 2001, each of which claim benefit under 35 U.S.C. §119(e) based on U.S. Provisional Application No. 60/265,583 filed on Feb. 2, 2001, and each of which is a continuation-in-part, and claim priority under 35 U.S.C. §120, of U.S. application Ser. No. 09/152,060 filed on Sep. 11, 1998, which is a continuation-in-part, and claims priority under 35 U.S.C. §120, of International Application PCT/US98/04858 filed on Mar. 12, 1998, which claims benefit under 35 U.S.C. §119(e) based on U.S. Provisional Applications 60/040,710 and 60/040,762 (filed on Mar. 14, 1997), 60/050,934, 60/048,100, 60/048,189 and 60/048,357 (filed on May 30, 1997), 60/048,970 (filed on Jun. 6, 1997), 60/057,765 (filed on Sep. 5, 1997), and 60/068,368 (filed on Dec. 19, 1997); and U.S. application Ser. No. 10/951,993 is also a continuation-in-part, and claims priority under 35 U.S.C. §120, of U.S. application Ser. No. 09/152,060 filed on Sep. 11, 1998, which is a continuation-in-part, and claims priority under 35 U.S.C. §120, of International Application PCT/US98/04858 filed on Mar. 12, 1998, which claims benefit under 35 U.S.C. §119(e) based on U.S. Provisional Applications 60/040,710 and 60/040,762 (filed on Mar. 14, 1997), 60/050,934, 60/048,100, 60/048,189 and 60/048,357 (filed on May 30, 1997), 60/048,970 (filed on Jun. 6, 1997), 60/057,765 (filed on Sep. 5, 1997), and 60/068,368 (filed on Dec. 19, 1997). This application is a continuation-in-part of U.S. application Ser. No. 11/745,580, filed May 8, 2007, which is a continuation of U.S. application Ser. No. 11/144,947, filed Jun. 6, 2005, which is a continuation of U.S. application Ser. No. 09/882,171, filed Jun. 18, 2001, which is a continuation application of U.S. application Ser. No. 09/809,391, filed Mar. 16, 2001, now abandoned, which claims benefit under 35 U.S.C. §119(e) of U.S. Provisional Application No. 60/190,068, filed Mar. 17, 2000; U.S. application Ser. No. 11/144,947 is a continuation-in-part of U.S. application Ser. No. 10/164,861, filed Jun. 10, 2002, which is a divisional of U.S. application Ser. No. 09/149,476, filed Sep. 8, 1998, (now issued U.S. Pat. No. 6,420,526, issued on Jul. 16, 2002), which is a continuation-in-part of PCT International Application No. PCT/US98/04493, filed Mar. 6, 1998 which claims benefit under 35 U.S.C. §119(e) based on the following U.S. Provisional Applications 60/040,162; 60/040,333; 60/038,621; 60/040,626; 60/040,334; 60/040,336; 60/040,163; (each filed Mar. 7, 1997); and, 60/047,600; 60/047,615; 60/047,597; 60/047,502; 60/047,633; 60/047,583; 60/047,617; 60/047,618; 60/047,503; 60/047,592; 60/047,581; 60/047,584; 60/047,500; 60/047,587; 60/047,492; 60/047,598; 60/047,613; 60/047,582; 60/047,596; 60/047,612; 60/047,632; 60/047,601, (each filed May 23, 1997); and, 60/043,580; 60/043,568; 60/043,314; 60/043,569; 60/043,311; 60/043,671; 60/043,674; 60/043,669; 60/043,312; 60/043,313; 60/043,672; 60/043,315, (each filed Apr. 11, 1997); and, 60/048,974, (filed Jun. 6, 1997); and, 60/056,886; 60/056,877; 60/056,889; 60/056,893; 60/056,630; 60/056,878; 60/056,662; 60/056,872; 60/056,882; 60/056,637; 60/056,903; 60/056,888; 60/056,879; 60/056,880; 60/056,894; 60/056,911; 60/056,636; 60/056,874; 60/056,910; 60/056,864; 60/056,631; 60/056,845, 60/056,892, (each filed Aug. 22, 1997); and 60/057,761, (filed Sep. 5, 1997); and, 60/047,595; 60/047,599; 60/047,588; 60/047,585; 60/047,586; 60/047,590; 60/047,594; 60/047,589; 60/047,593; 60/047,614, (each filed May 23, 1997); and, 60/043,578, 60/043,576 (each filed Apr. 11, 1997); and, 60/047,501, (filed May 23, 1997); and, 60/043,670, (filed Apr. 11, 1997); and, 60/056,632; 60/056,664; 60/056,876; 60/056,881; 60/056,909; 60/056,875; 60/056,862; 60/056,887; 60/056,908, (each filed Aug. 22, 1997); and, 60/048,964, (filed Jun. 6, 1997); and, 60/057,650, (filed Sep. 5, 1997); and, 60/056,884, (filed Aug. 22, 1997); and, 60/057,669, (filed Sep. 5, 1997); and, 60/049,610, (filed Jun. 13, 1997); and, 60/061,060, (filed Oct. 2, 1997); and, 60/051,926, (filed Jul. 8, 1997); and, 60/052,874, (filed Jul. 16, 1997); and, 60/058,785, (filed Sep. 12, 1997); and, 60/055,724, (filed Aug. 18, 1997); and, 60/040,161, (filed Mar. 7, 1997). This application is a continuation-in-part of U.S. application Ser. No. 12/264,040, filed Nov. 3, 2008, which is a divisional of U.S. application Ser. No. 11/246,999, filed Oct. 11, 2005, which is a divisional of U.S. application Ser. No. 09/984,130, filed Oct. 29, 2001 (now abandoned), which claims benefit under 35 U.S.C. §119(e) of U.S. Provisional Application No. 60/243,792, filed on Oct. 30, 2000, and which is also a continuation-in-part of U.S. application Ser. No. 09/836,353, filed Apr. 18, 2001, (now abandoned), which claims benefit under 35 U.S.C. §119(e) of U.S. Provisional Application No. 60/198,407, filed Apr. 19, 2000, and which is a continuation-in-part of PCT International Application No. PCT/US99/25031 (published in English), filed Oct. 27, 1999, which claims benefit under 35 U.S.C. §119(e) of U.S. Provisional Application No. 60/105,971, filed Oct. 28, 1998. Each of the above referenced patents and patent applications is hereby incorporated by reference herein in its entirety.

REFERENCE TO SEQUENCE LISTING AS TEXT FILE

This application refers to a "Sequence Listing" listed below, which is provided as a text file. The text file contains a document entitled "PS960_SeqList.txt" (473,508 bytes, created Apr. 2, 2010), which is hereby incorporated by reference in its entirety.

FIELD OF THE INVENTION

The present invention relates to novel proteins/polypeptides (such as human secreted proteins/polypeptides), and isolated nucleic acid molecules encoding said proteins/polypeptides, useful for detecting, preventing, diagnosing, prognosticating, treating, and/or ameliorating diseases and disorders related to said proteins/polypeptides (relatedness may be by direct or indirect association, by cause, by consequence, or by effect on said diseases and disorders), such as immune, cardiovascular, cancer, and other proliferative disorders and diseases. Antibodies that bind these polypeptides are also encompassed by the present invention. Also encompassed by the invention are vectors, host cells, and recombinant and synthetic methods for producing said polynucleotides, polypeptides, and/or antibodies. The invention further encompasses screening methods for identifying agonists and antagonists of polynucleotides and polypeptides of the invention. The present invention further encompasses methods and compositions for inhibiting or enhancing the production and function of the polypeptides of the present invention. The invention further relates to diagnostic and therapeutic methods useful for diagnosing and treating diseases, disorders, and/or conditions related to these novel human secreted proteins.

BACKGROUND OF THE INVENTION

Unlike bacterium, which exist as a single compartment surrounded by a membrane, human cells and other eukaryotes are subdivided by membranes into many functionally distinct compartments. Each membrane-bounded compartment, or organelle, contains different proteins essential for the function of the organelle. The cell uses "sorting signals," which are amino acid motifs located within the protein, to target proteins to particular cellular organelles.

One type of sorting signal, called a signal sequence, a signal peptide, or a leader sequence, directs a class of proteins to an organelle called the endoplasmic reticulum (ER). The ER separates the membrane-bounded proteins from all other types of proteins. Once localized to the ER, both groups of proteins can be further directed to another organelle called the Golgi apparatus. Here, the Golgi distributes the proteins to vesicles, including secretory vesicles, the cell membrane, lysosomes, and the other organelles.

Proteins targeted to the ER by a signal sequence can be released into the extracellular space as a secreted protein. For example, vesicles containing secreted proteins can fuse with the cell membrane and release their contents into the extracellular space—a process called exocytosis. Exocytosis can occur constitutively or after receipt of a triggering signal. In the latter case, the proteins are stored in secretory vesicles (or secretory granules) until exocytosis is triggered. Similarly, proteins residing on the cell membrane can also be secreted into the extracellular space by proteolytic cleavage of a "linker" holding the protein to the membrane.

Thus there exists a clear need for identifying and using novel secreted polynucleotides and polypeptides. Identification and sequencing of human genes is a major goal of modern scientific research. For example, by identifying genes and determining their sequences, scientists have been able to make large quantities of valuable human "gene products." These include human insulin, interferon, Factor VIII, tumor necrosis factor, human growth hormone, tissue plasminogen activator, erythropoietin, and numerous other compounds. Thus, in light of the pervasive role of secreted proteins in human physiology, a need exists for identifying and characterizing novel human secreted proteins and the genes that encode them. This knowledge will allow one to detect, to treat, and to prevent medical diseases, disorders, and/or conditions by using secreted proteins or the genes that encode them. Additionally, knowledge of gene sequences can provide the key to treatment or cure of genetic diseases (such as muscular dystrophy and cystic fibrosis).

Immune-Related Polynucleotides and Polypeptides

The immune system is an intricate network of cells, tissues and soluble molecules that function to protect the body from invasion by foreign substances and pathogens. The major cells of the immune system are lymphocytes, including B cells and T cells, and myeloid cells, including basophils, eosinophils, neutrophils, mast cells, monocytes, macrophages and dendritic cells. In addition to these cellular components of the immune system, soluble molecules—such as antibodies, complement proteins, and cytokines—circulate in lymph and blood plasma, and play important roles in immunity.

The immune system can be subdivided into the acquired and innate immune systems. The cells of the innate immune system (e.g., neutrophils, eosinophils, basophils, mast cells) are not antigen specific and their action is not enhanced by repeated exposure to the same antigen. The cells of the acquired immune system (B and T cells) are antigen specific. Repeated exposure of B and T cells to an antigen results in improved immune responses (memory responses) produced by these cell types. The cells and products of the acquired immune system can recruit components of the innate system to mount a focused immune response. For a more extensive review of the immune system, see *Fundamental Immunology,* 4th edition, Ed. William Paul, Lippincott-Raven Pub. (1998).

An immune response is seldom carried out by a single cell type, but rather requires the coordinated efforts of several cell types. In order to coordinate an immune response, it is necessary that cells of the immune system communicate with each other and with other cells of the body. Communication between cells may be made by cell-cell contact, between membrane bound molecules on each cell, or by the interaction of soluble components of the immune system with cellular receptors. Signaling between cell types may have one or more of a variety of consequences, including activation, proliferation, differentiation, and apoptosis. Activation and differentiation of immune cells may result in the expression or secretion of polypeptides, or other molecules, which in turn affect the function of other cells and/or molecules of the immune system.

Molecules which stimulate or suppress immune system function are known as immunomodulators. These molecules, which include endogenous proteins (e.g., cytokines, cytokine receptors, and intracellular signal transduction molecules), molecules derived from microorganisms, and synthetic agents, may exert their modulatory effects at one or more stages of the immune response, such as antigen recognition, stimulation of cytokine production and release, and/or activation/differentiation of lymphocytes and myeloid cells. Immunomodulators may enhance (immunoprophylaxis, immunostimulation), restore (immunosubstitution, immunorestoration) or suppress (immunosuppression, immunodeviation) immunological functions or activities.

Immunomodulatory compounds have many important applications in clinical practice. For example, immunosuppressing agents (which attenuate or prevent unwanted immune responses) can be used to prevent tissue rejection during organ transplantation, to prevent Rh hemolytic disease of the newborn, or to treat autoimmune disorders. A mechanism of action common to many immunosuppressants is the inhibition of T cell activation and/or differentiation. Antilymphocyte antibodies have also been used to attenuate immune system functions. Currently-used immunosuppressive agents can produce a number of side effects which limit their use. Among the most serious secondary effects include kidney and liver toxicity, increased risk of infection, hyperglycemia, neoplasia, and osteoporosis (see, e.g., Freeman, Clin. Biochem. 24(1):9-14 (1991); Mitchison, Dig. Dis. 11(2):78-101 (1993)).

Immunostimulants, which enhance the activity of immune cells and molecules, comprise another class of immunomodulatory agents with important clinical applications. Such applications include, for example, the treatment of immunodeficiency disorders (e.g. AIDS and severe combined immunodeficiency), chronic infectious diseases (e.g. viral hepatitis, papillomavirus, and herpesvirus), and cancer. An important class of endogenous immunostimulants is the cytokines. These soluble signaling molecules are produced by a number of cell types, and are critical to the regulation of the immune response. Immunostimulatory mechanisms can include proliferation, differentiation and/or activation of immune cells or progenitors of immune cells. For example, interleukin-2 (IL-2) binds to IL-2 receptors on T lymphocytes and induces proliferation and differentiation. Another cytokine, interferon alpha, stimulates the immune system through a variety of mechanisms, including activation of macrophages, T lymphocytes, and natural killer cells. Interferon alpha also induces the expression of antiviral proteins (see Chapter 50, *The Pharmacological Basis of Therapeutics,* $9^{th}$ Edition, Eds. Hardman, Limbird, Molinoff, Ruddon, and Gilman, McGraw Hill (1996)). Limitations of current immunostimulant therapies include anaphylaxis, pulmonary edema, and renal toxicity, to name a few.

The discovery of new human immune related polynucleotides, the polypeptides encoded by them, and antibodies that immunospecifically bind these polypeptides, satisfies a need in the art by providing new compositions which are useful in the diagnosis, treatment, prevention and/or prognosis of disorders of the immune system, including, but not limited to, autoimmune disorders (e.g., systemic lupus erythematosus, rheumatoid arthritis, idiopathic thrombocytopenic purpura and multiple sclerosis), immunodeficiencies (e.g., X-linked agammaglobulinemia, severe combined immunodeficiency, Wiskott-Aldrich syndrome, and ataxia telangiectasia), chronic infections (e.g., HIV, viral hepatitis, and herpesvirus), and neoplastic disorders. See, e.g. "Immune Activity" section infra. Additionally, immune related molecules would be useful as agents to boost immune responsiveness to pathogens or to suppress immune reactions, for example as is necessary in conjunction with organ transplantation.

Cardiovascular-Related Polynucleotides and Polypeptides

The cardiovascular system is a component of a complex physiological network involved in maintaining the oxygen and nutrient supply to tissues of the body. The heart is the anatomical and functional centerpiece of the cardiovascular system. Weighing only 250-350 grams (less than a pound), the heart is one of our strongest and hardest working organs. It is composed of innervated muscle tissue with unique properties; e.g., it can pace itself in contraction. The main center of rhythm regulation is the sinoatrial (SA) node. Certain cardiac cells repeatedly fire impulses that trigger heart contractions. These autorhythmic cells have two important functions. One is to act as a pacemaker (set the pace for the entire heart), and the other is to form a conduction system, the route for conducting impulses throughout the heart muscle. This conduction system controls the pattern of blood flow through the heart.

The heart pumps at least five quarts of blood through a full circuit of the body every minute. The heart consists of two pumps, side by side. The pump on the right side moves blood to the lungs, where waste gases, such as carbon dioxide, are removed and oxygen is added. Freshly oxygenated blood returns to the pump on the left side, which moves it out into the rest of the body. Blood flows away from the heart to the lungs or to the rest of your body, though blood vessels called arteries. Arteries branch extensively, each branch become smaller, forming blood vessels called arterioles. Arterioles also become repeatedly smaller and smaller until they are tiny vessels called capillaries. Throughout the arteries and smaller vessels that stem from them, the blood delivers nutrients and oxygen to the tissues and picks up waste. This task is completed in the capillaries. As the blood moves on through the capillaries the blood vessels gradually become larger, eventually becoming veins. Veins ultimately carry blood back to the heart. The cycle then begins again.

Disorders of the cardiovascular system are many and varied, killing more Americans each year than any other category of disorders. For example, damage to the conduction system leads to arrhythmia, an irregular beating of the heart. If left untreated, the heart becomes unable to effectively pump blood, frequently leading to permanent heart damage and/or cardiac arrest.

One of the most prevalent conditions in industrialized countries today is atherosclerosis. Atherosclerosis is the buildup of fatty deposits in the intima of large and medium-sized arteries. The buildup of deposits narrowing of the arteries, reducing or potentially blocking the ability of blood to flow through the arteries. Untreated, atherosclerosis typically results in cardiac arrest and, frequently, death.

Clearly, the discovery of new human cardiovascular-associated polynucleotides, the polypeptides encoded by them, and antibodies that immunospecifically bind these polypeptides, satisfies a need in the art by providing new compositions which are useful in the diagnosis, treatment, prevention and/or prognosis of cardiovascular disorders.

Cardiovascular disorders include, but are not limited to, stroke, cardiovascular abnormalities, such as arterio-arterial fistula, arteriovenous fistula, cerebral arteriovenous malformations, congenital heart defects, pulmonary atresia, and Scimitar Syndrome. Congenital heart defects include, but are not limited to, aortic coarctation, cor triatriatum, coronary vessel anomalies, crisscross heart, dextrocardia, patent ductus arteriosus, Ebstein's anomaly, Eisenmenger complex, hypoplastic left heart syndrome, levocardia, tetralogy of fallot, transposition of great vessels, double outlet right ventricle, tricuspid atresia, persistent truncus arteriosus, and heart septal defects, such as aortopulmonary septal defect, endocardial cushion defects, Lutembacher's Syndrome, trilogy of Fallot, ventricular heart septal defects.

Cardiovascular disorders also include, but are not limited to, heart disease, such as arrhythmias, carcinoid heart disease, high cardiac output, low cardiac output, cardiac tamponade, endocarditis (including bacterial), heart aneurysm, cardiac arrest, congestive heart failure, congestive cardiomyopathy, paroxysmal dyspnea, cardiac edema, heart hypertrophy, congestive cardiomyopathy, left ventricular hypertrophy, right ventricular hypertrophy, post-infarction heart rupture, ventricular septal rupture, heart valve diseases, myocardial diseases, myocardial ischemia, pericardial effusion, pericarditis (including constrictive and tuberculous), pneumopericardium, postpericardiotomy syndrome, pulmonary heart disease, rheumatic heart disease, ventricular dysfunction, hyperemia, cardiovascular pregnancy complications, Scimitar Syndrome, cardiovascular syphilis, and cardiovascular tuberculosis.

Arrhythmias include, but are not limited to, sinus arrhythmia, atrial fibrillation, atrial flutter, bradycardia, extrasystole, Adams-Stokes Syndrome, bundle-branch block, sinoatrial block, long QT syndrome, parasystole, Lown-Ganong-Levine Syndrome, Mahaim-type pre-excitation syndrome, Wolff-Parkinson-White syndrome, sick sinus syndrome, tachycardias, and ventricular fibrillation. Tachycardias include paroxysmal tachycardia, supraventricular tachycardia, accelerated idioventricular rhythm, atrioventricular nodal reentry tachycardia, ectopic atrial tachycardia, ectopic junctional tachycardia, sinoatrial nodal reentry tachycardia, sinus tachycardia, Torsades de Pointes, and ventricular tachycardia.

Heart valve diseases include, but are not limited to, aortic valve insufficiency, aortic valve stenosis, hear murmurs, aortic valve prolapse, mitral valve prolapse, tricuspid valve prolapse, mitral valve insufficiency, mitral valve stenosis, pulmonary atresia, pulmonary valve insufficiency, pulmonary valve stenosis, tricuspid atresia, tricuspid valve insufficiency, and tricuspid valve stenosis.

Myocardial diseases include, but are not limited to, alcoholic cardiomyopathy, congestive cardiomyopathy, hypertrophic cardiomyopathy, aortic subvalvular stenosis, pulmonary subvalvular stenosis, restrictive cardiomyopathy, Chagas cardiomyopathy, endocardial fibroelastosis, endomyocardial fibrosis, Kearns Syndrome, myocardial reperfusion injury, and myocarditis.

Myocardial ischemias include, but are not limited to, coronary disease, such as angina pectoris, coronary aneurysm, coronary arteriosclerosis, coronary thrombosis, coronary vasospasm, myocardial infarction and myocardial stunning.

Cardiovascular diseases also include vascular diseases such as aneurysms, angiodysplasia, angiomatosis, bacillary angiomatosis, Hippel-Lindau Disease, Klippel-Trenaunay-Weber Syndrome, Sturge-Weber Syndrome, angioneurotic edema, aortic diseases, Takayasu's Arteritis, aortitis, Leriche's Syndrome, arterial occlusive diseases, arteritis, enarteritis, polyarteritis nodosa, cerebrovascular disorders, diabetic angiopathies, diabetic retinopathy, embolisms, thrombosis, erythromelalgia, hemorrhoids, hepatic veno-occlusive disease, hypertension, hypotension, ischemia, peripheral vascular diseases, phlebitis, pulmonary veno-occlusive disease, Raynaud's disease, CREST syndrome, retinal vein occlusion, Scimitar syndrome, superior vena cava syndrome, telangiectasia, atacia telangiectasia, hereditary hemorrhagic telangiectasia, varicocele, varicose veins, varicose ulcer, vasculitis, and venous insufficiency.

Aneurysms include, but are not limited to, dissecting aneurysms, false aneurysms, infected aneurysms, ruptured aneurysms, aortic aneurysms, cerebral aneurysms, coronary aneurysms, heart aneurysms, and iliac aneurysms.

Arterial occlusive diseases include, but are not limited to, arteriosclerosis, intermittent claudication, carotid stenosis, fibromuscular dysplasias, mesenteric vascular occlusion, Moyamoya disease, renal artery obstruction, retinal artery occlusion, and thromboangiitis obliterans.

Cerebrovascular disorders include, but are not limited to, carotid artery diseases, cerebral amyloid angiopathy, cerebral aneurysm, cerebral anoxia, cerebral arteriosclerosis, cerebral arteriovenous malformation, cerebral artery diseases, cerebral embolism and thrombosis, carotid artery thrombosis, sinus thrombosis, Wallenberg's syndrome, cerebral hemorrhage, epidural hematoma, subdural hematoma, subaraxhnoid hemorrhage, cerebral infarction, cerebral ischemia (including transient), subclavian steal syndrome, periventricular leukomalacia, vascular headache, cluster headache, migraine, and vertebrobasilar insufficiency.

Embolisms include, but are not limited to, air embolisms, amniotic fluid embolisms, cholesterol embolisms, blue toe syndrome, fat embolisms, pulmonary embolisms, and thromoboembolisms. Thrombosis include, but are not limited to, coronary thrombosis, hepatic vein thrombosis, retinal vein occlusion, carotid artery thrombosis, sinus thrombosis, Wallenberg's syndrome, and thrombophlebitis.

Ischemic disorders include, but are not limited to, cerebral ischemia, ischemic colitis, compartment syndromes, anterior compartment syndrome, myocardial ischemia, reperfusion injuries, and peripheral limb ischemia. Vasculitis includes, but is not limited to, aortitis, arteritis, Behcet's Syndrome, Churg-Strauss Syndrome, mucocutaneous lymph node syndrome, thromboangiitis obliterans, hypersensitivity vasculitis, Schoenlein-Henoch purpura, allergic cutaneous vasculitis, and Wegener's granulomatosis.

Cancer and Hyperproliferative-Related Polynucleotides and Polypeptides

Cancer and other hyperproliferative disorders are a diverse group of disorders and diseases sharing one characteristic in common; all result from uncontrolled cell proliferation. The human body is composed of many different cell types, e.g. liver cells, muscle cells, brain cells, etc. Normally, these cells grow and divide to produce more cells only as the body needs them (e.g. to regenerate blood cells or replace epithelial cells lining the stomach). Sometimes, however, cells begin to divide unchecked even though new cells are not needed. These extra cells accumulate and form a mass of tissue, called a tumor. Although each of the over 200 cell types in the body can potentially become cancerous, some cell types become cancerous at relatively high rates while many other cell types rarely become cancerous.

Tumors are either benign or malignant. Benign tumors are not cancerous; they can usually be removed, they do not spread to other parts of the body and, they rarely threaten life. Malignant tumors, however, are cancerous. Cells in malignant tumors can invade and damage nearby or distant tissues and organs. The spread of cancerous cells is called metastasis. Malignant (or metastatic) cells can invade adjacent organs by proliferating directly from the primary tumor. Additionally, malignant cells can also metastasize to distant organs by breaking away from the primary tumor, entering the bloodstream or lymphatic system, and settling down in a new organ or tissue to produce a secondary tumor. The origin of secondary tumors is established by comparing cells comprising these tumors to cells in the original (primary) tumor.

In contrast to solid organ cancers (such as cancer in the liver, lung, and brain) cancer can also develop in blood-forming cells. These cancers are referred to as leukemias or lymphomas. Leukemia refers to cancer of blood forming cells such as red blood cells, platelets, and plasma cells. Lymphomas are a subset of leukemias, primarily involving white blood cells, in which the cancerous cells originated in, or are associated with, the lymph system and lymph organs (e.g. T-lymphocytes in the lymph nodes, spleen, or thymus).

In 1999 over 1.1 million people were newly diagnosed with 23 different types of cancer. The vast majority of these cases (~75%) involved cancers of the prostate, breast, lung, colon, or urinary tract, or non-Hodgkin's lymphoma. Among the most fatal cancers are pancreatic, liver, esophageal, lung, stomach, and brain cancers, having up to 96% mortality rates depending on the specific cancer. In all, some 23 different types of cancer are expected to kill over 86,000 people each year.

Most cancers are treated with one or a combination therapies consisting of surgery, radiation therapy, chemotherapy, hormone therapy, and/or biological therapy. These five therapeutic modes are either local or systemic treatment strategies. Local treatments affect cancer cells in the tumor and immediately adjacent areas (for example, surgical tumor removal is a local treatment as are most radiation treatments). In contrast, systemic treatments travel through the bloodstream, and reach cancer and other cells all over the body. Chemotherapy, hormone therapy, and biological therapy are examples of systemic treatments.

Whether systemic or local, it is often difficult or impossible to protect healthy cells from the harmful effects of cancer treatment; healthy cells and tissues are inevitably damaged in the process of treating the cancerous cells. Damage and disruption of the normal functioning of healthy cells and tissues often produces the undesirable side effects experienced by patients undergoing cancer treatment.

Recombinant polypeptides and polynucleotides derived from naturally occurring molecules, as well as antibodies specifically targeted to these molecules, used alone or in conjunction with other existing therapies, hold great promise as improved therapeutic agents for the treatment of neoplastic disorders. Currently, most biological therapy can be classified as immunotherapy because these treatments often use naturally occurring molecules to assist the body's immune system in fighting the disease or in protecting the body from side effects of other cancer treatment(s). Among the most commonly used compounds in biological therapies are proteins called cytokines (e.g. interferons, interleukins, and colony stimulating factors) and monoclonal antibodies (targeted to particular cancer cells). Side effects caused by these commonly used biological therapies range from flu-like symptoms (chills, fever, muscle aches, weakness, loss of appetite, nausea, vomiting, and diarrhea) to rashes, swelling, easy bruising, or bleeding.

The discovery of human secreted proteins associated with initiation, progression, characterization, and/or distinction of neoplastic diseases (including antibodies that immunospecifically bind these polypeptides), satisfies a need in the art by providing new compositions useful in the detection, prevention, diagnosis, treatment, prevention, prognosis, and treatment of hyperproliferative disorders.

BRIEF DESCRIPTION OF THE DRAWINGS

FIG. 1 shows the nucleotide (SEQ ID NO:1) and deduced amino acid sequence (SEQ ID NO:2) corresponding to Gene No: 1.

Figure 2:
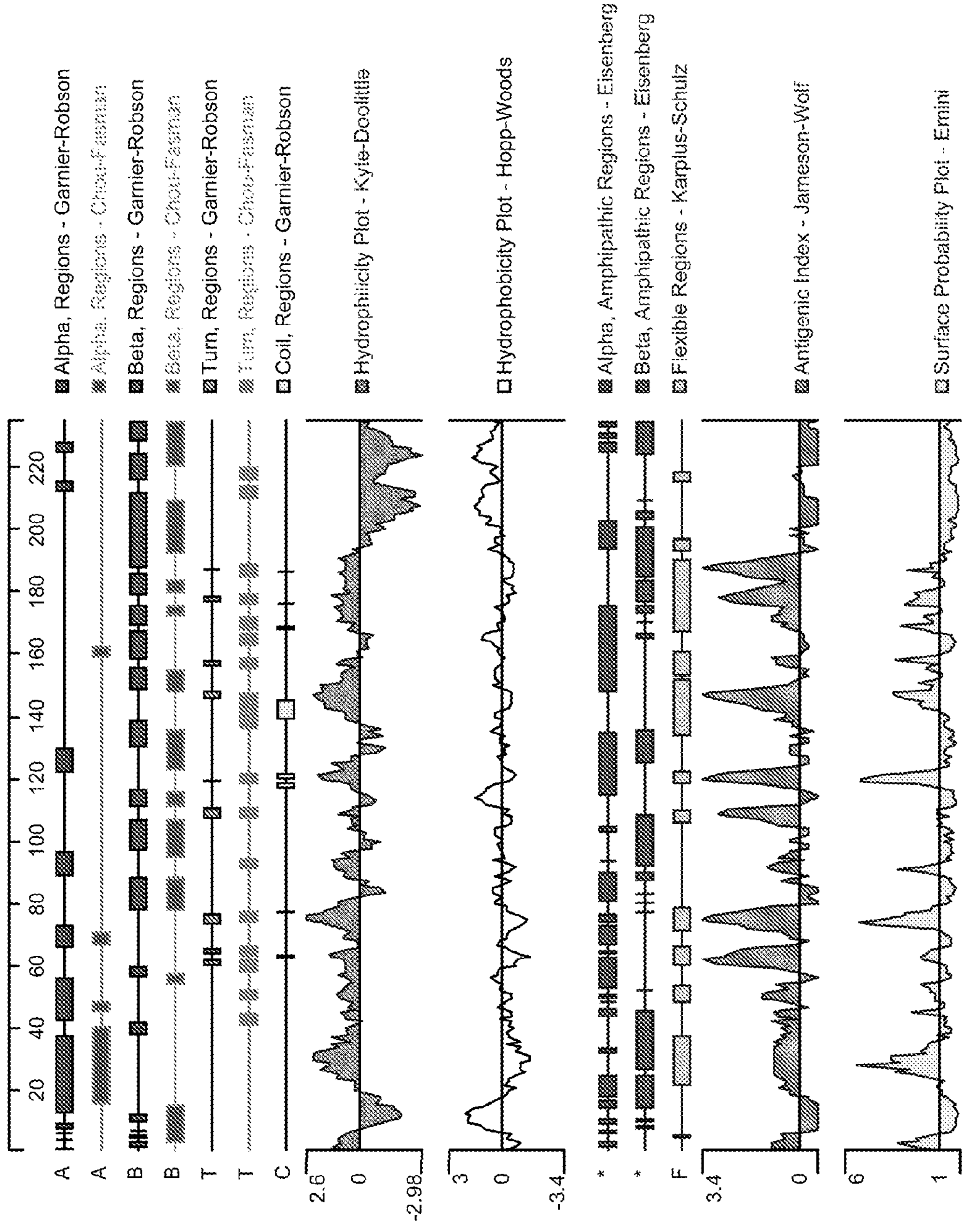
FIG. 2 shows an analysis of the amino acid sequence (SEQ ID NO:2). Alpha, beta, turn and coil regions; hydrophilicity and hydrophobicity; amphipathic regions; flexible regions; antigenic index and surface probability are shown, and all were generated using the default settings of the recited computer algorithms. In the "Antigenic Index or Jameson-Wolf" graph, the positive peaks indicate locations of the highly antigenic regions of the protein, i.e., regions from which epitope-bearing peptides of the invention can be obtained. Polypeptides comprising, or alternatively consisting of, domains defined by these graphs are contemplated by the present invention, as are polynucleotides encoding these polypeptides.

The data presented in FIG. 2 are also represented in tabular form in Table 8. The columns are labeled with the headings "Res", "Position", and Roman Numerals I-XIV. The column headings refer to the following features of the amino acid sequence presented in FIG. 2, and Table 8: "Res": amino acid residue of SEQ ID NO:2 and FIG. 1; "Position": position of the corresponding residue within SEQ ID NO:2 and FIG. 1; I: Alpha, Regions—Garnier-Robson; II: Alpha, Regions—Chou-Fasman; III: Beta, Regions—Garnier-Robson; IV: Beta, Regions—Chou-Fasman; V: Turn, Regions—Garnier-Robson; VI: Turn, Regions—Chou-Fasman; VII: Coil, Regions—Garnier-Robson; VIII: Hydrophilicity Plot—Kyte-Doolittle; IX: Hydrophobicity Plot—Hopp-Woods; X: Alpha, Amphipathic Regions—Eisenberg; XI: Beta, Amphipathic Regions—Eisenberg; XII: Flexible Regions—Karplus-Schulz; XIII: Antigenic Index—Jameson-Wolf; and XIV: Surface Probability Plot—Emini.

FIGS. 3A-3B show the Gene No: 5 nucleotide (SEQ ID NO:20) and deduced amino acid sequence (SEQ ID NO:21) corresponding to this gene.

Figure 4:
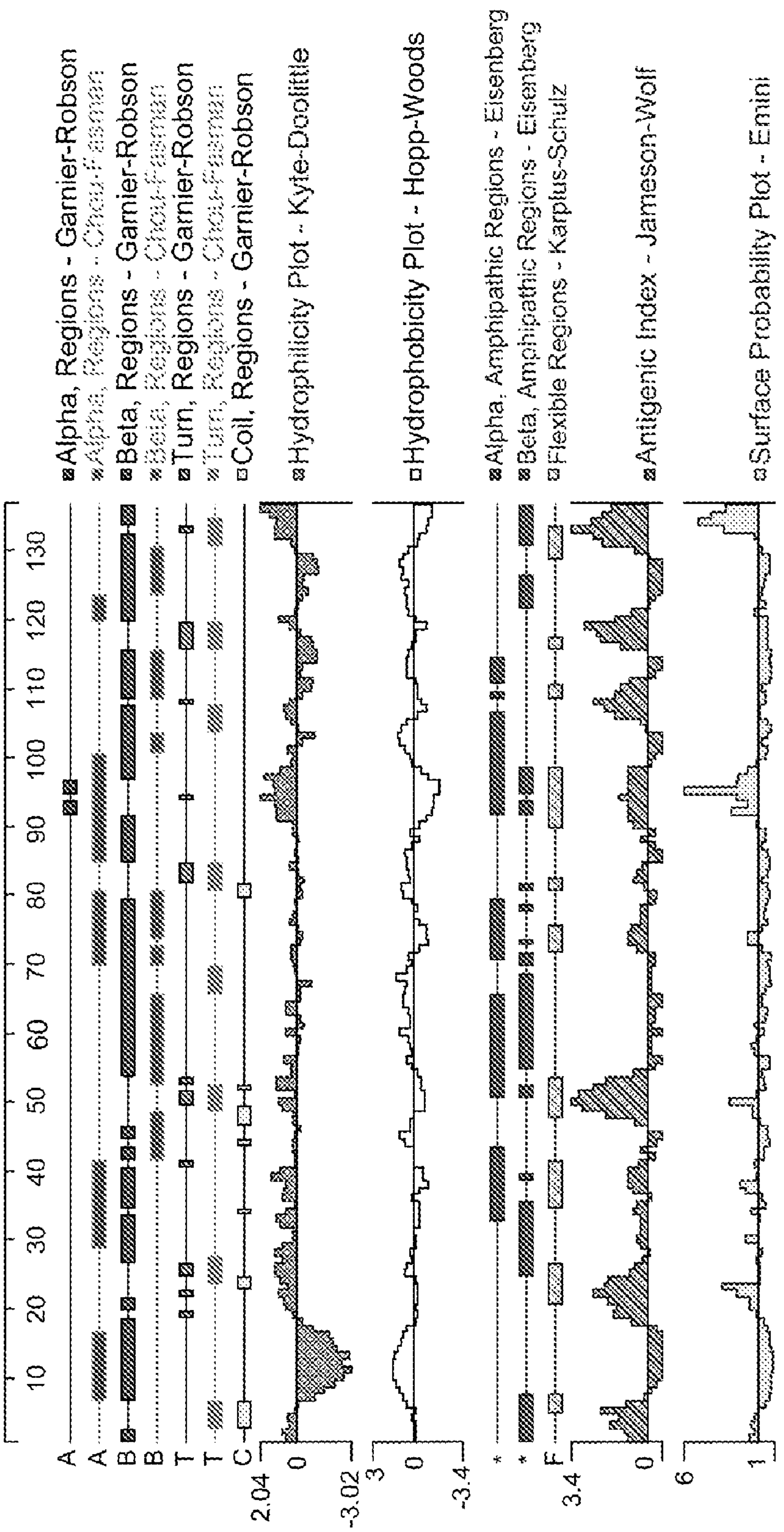

FIG. 4 shows an analysis of the amino acid sequence (SEQ ID NO:21). Alpha, beta, turn and coil regions; hydrophilicity and hydrophobicity; amphipathic regions; flexible regions; antigenic index and surface probability are shown, and all were generated using the default settings of the recited computer algorithms. In the "Antigenic Index or Jameson-Wolf" graph, the positive peaks indicate locations of the highly antigenic regions of the protein, i.e., regions from which epitope-bearing peptides of the invention can be obtained. Polypeptides comprising, or alternatively consisting of, domains defined by these graphs are contemplated by the present invention, as are polynucleotides encoding these polypeptides FIG. 5 shows the nucleotide (SEQ ID NO:102) and deduced amino acid sequence (SEQ ID NO:103) corresponding to Gene No: 14.

Figure 6:
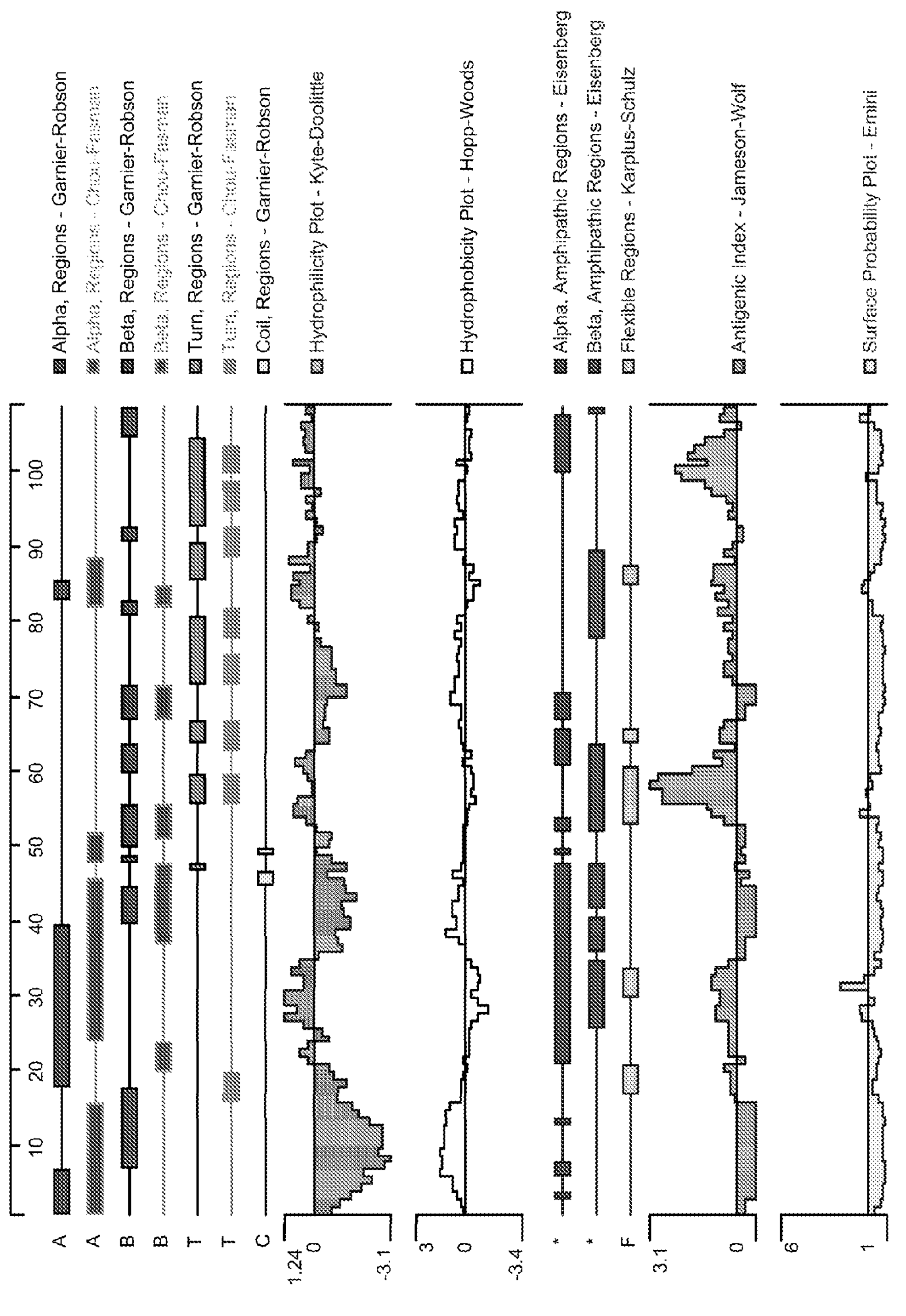

FIG. 6 shows an analysis of the amino acid sequence (SEQ ID NO:103). Alpha, beta, turn and coil regions; hydrophilicity and hydrophobicity; amphipathic regions; flexible regions; antigenic index and surface probability are shown, and all were generated using the default settings of the recited computer algorithms. In the "Antigenic Index or Jameson-Wolf" graph, the positive peaks indicate locations of the highly antigenic regions of the protein, i.e., regions from which epitope-bearing peptides of the invention can be obtained. Polypeptides comprising, or alternatively consisting of, domains defined by these graphs are contemplated by the present invention, as are polynucleotides encoding these polypeptides.

FIGS. 7A-C show the nucleotide sequence (SEQ ID NO:134) and the deduced amino acid sequence (SEQ ID NO:135) of the HCEJQ69 cDNA (Gene No: 20).

Figure 8:
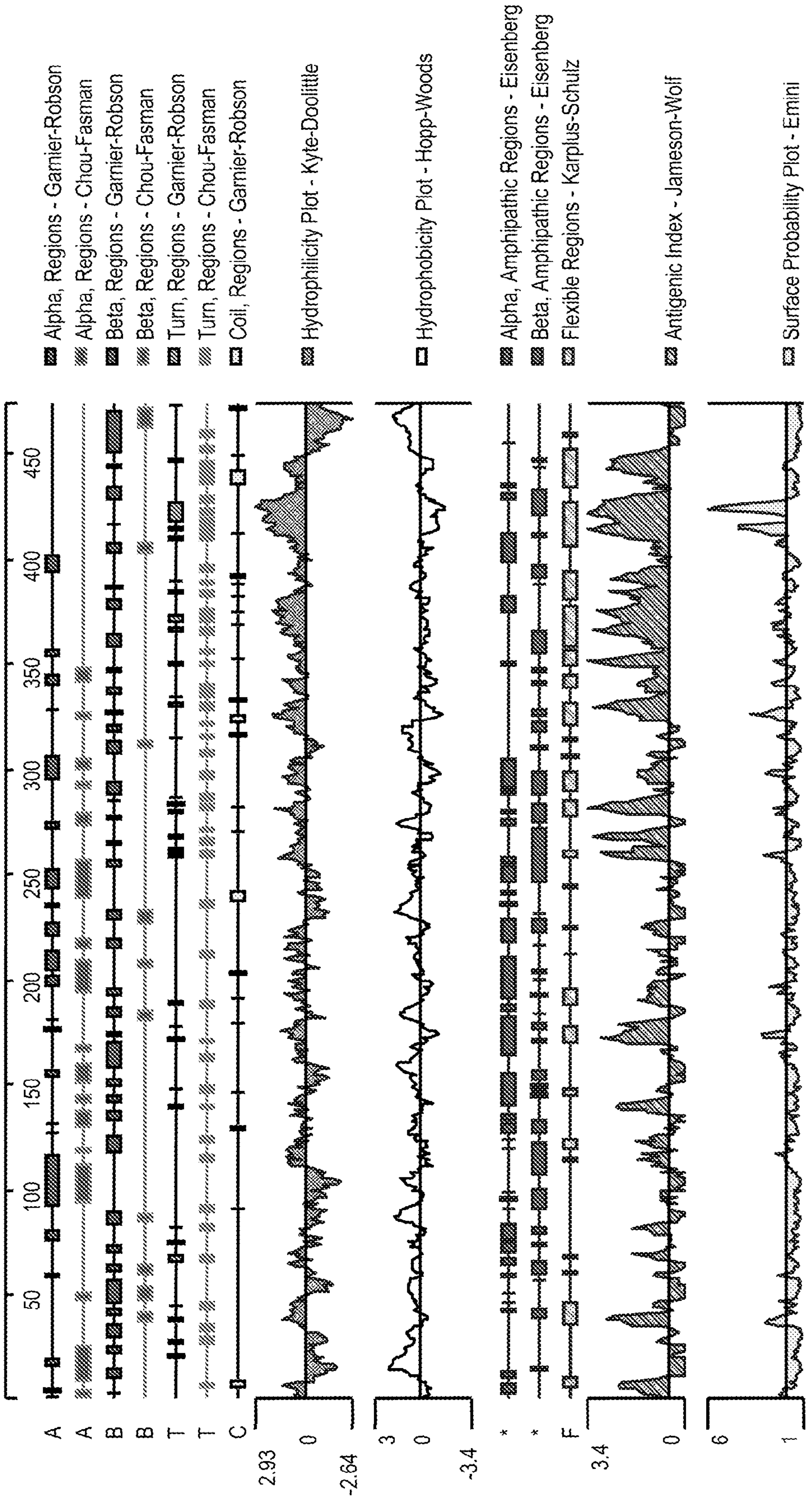

FIG. 8 shows an analysis of the amino acid sequence (SEQ ID NO:135). Alpha, beta, turn and coil regions; hydrophilicity and hydrophobicity; amphipathic regions; flexible regions; antigenic index and surface probability are shown, and all were generated using the default settings of the recited computer algorithms. In the "Antigenic Index or Jameson-Wolf" graph, the positive peaks indicate locations of the highly antigenic regions of the protein, i.e., regions from which epitope-bearing peptides of the invention can be obtained. Polypeptides comprising, or alternatively consisting of, domains defined by these graphs are contemplated by the present invention, as are polynucleotides encoding these polypeptides.

The data presented in FIG. 8 are also represented in tabular form in Table 9. The columns are labeled with the headings "Res", "Position", and Roman Numerals I-XIV. The column headings refer to the following features of the amino acid sequence presented in FIG. 8, and Table 9: "Res": amino acid residue of SEQ ID NO:135 and FIGS. 7A-7C; "Position": position of the corresponding residue within SEQ ID NO:135 and FIGS. 7A-7C; I: Alpha, Regions—Garnier-Robson; II: Alpha, Regions—Chou-Fasman; III: Beta, Regions—Garnier-Robson; IV: Beta, Regions—Chou-Fasman; V: Turn, Regions—Garnier-Robson; VI: Turn, Regions—Chou-Fasman; VII: Coil, Regions—Garnier-Robson; VIII: Hydrophilicity Plot—Kyte-Doolittle; IX: Hydrophobicity Plot—Hopp-Woods; X: Alpha, Amphipathic Regions—Eisenberg; XI: Beta, Amphipathic Regions—Eisenberg; XII: Flexible Regions—Karplus-Schulz; XIII: Antigenic Index—Jameson-Wolf; and XIV: Surface Probability Plot—Emini.

FIGS. 9A-B show the nucleotide (SEQ ID NO:159) and deduced amino acid sequence (SEQ ID NO:160) of this polypeptide.

Figure 10:
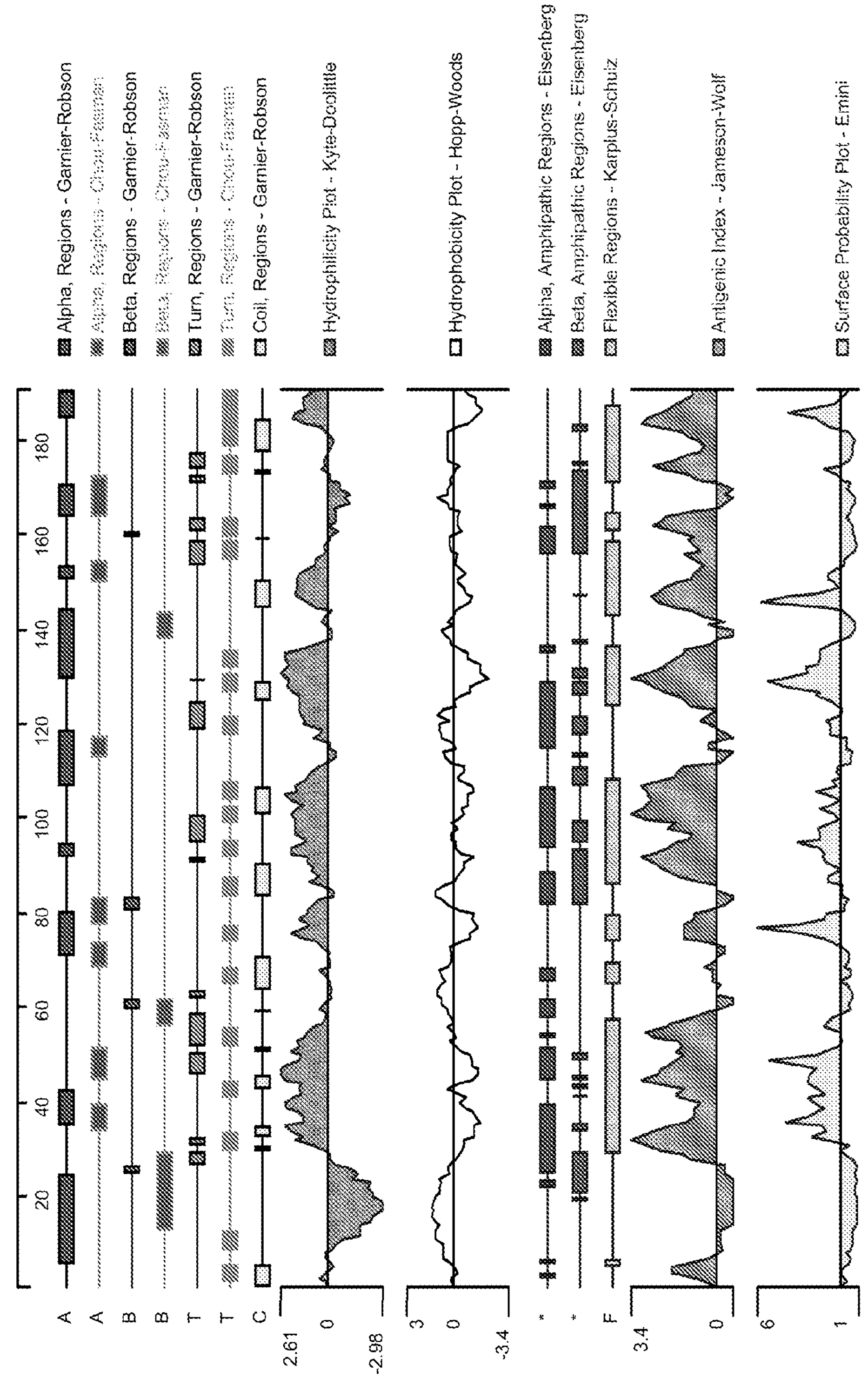
Figure 12D:
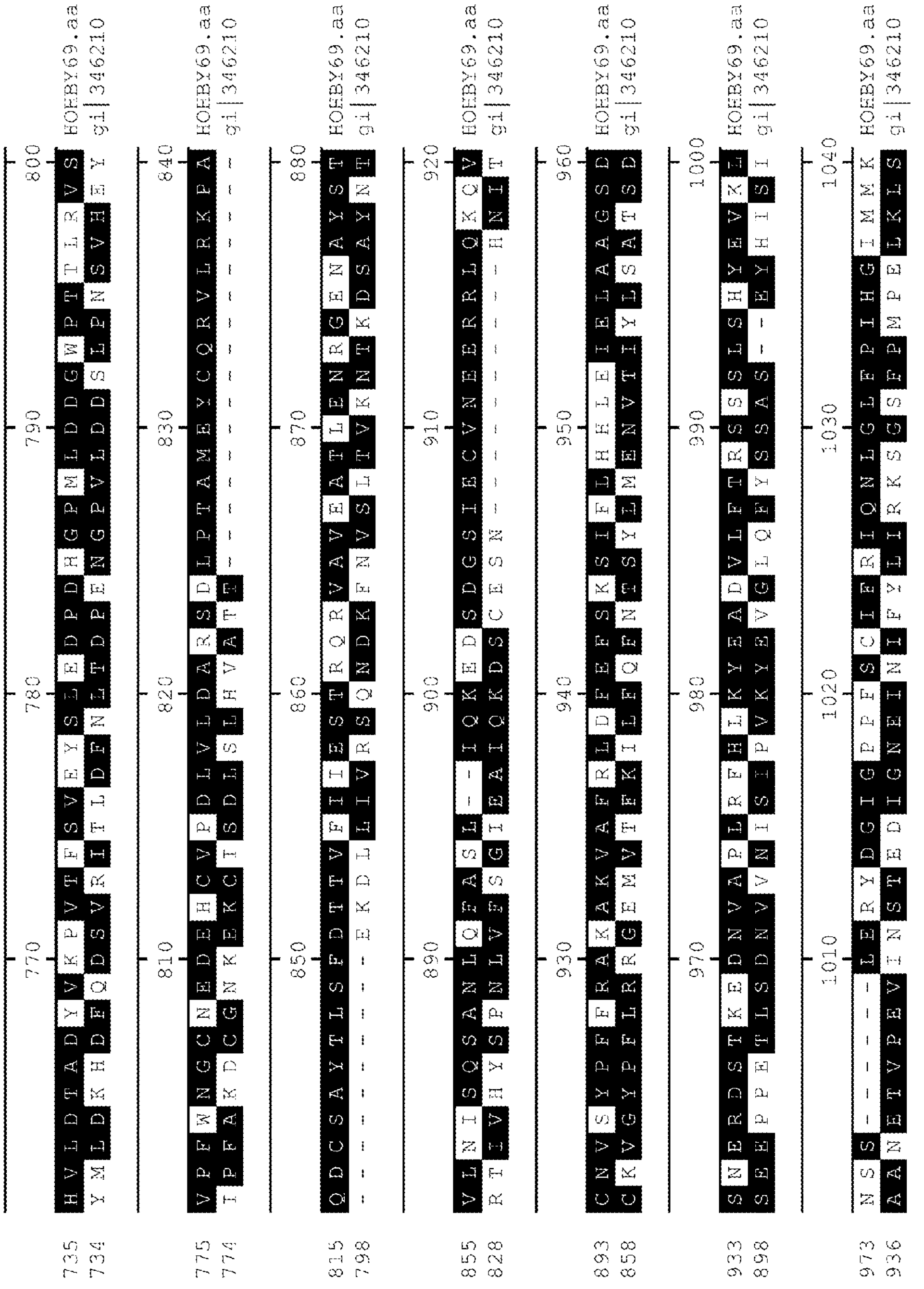

FIG. 10 shows an analysis of the amino acid sequence (SEQ ID NO:160). Alpha, beta, turn and coil regions; hydrophilicity and hydrophobicity; amphipathic regions; flexible regions; antigenic index and surface probability are shown, and all were generated using the default settings. In the "Antigenic Index or Jameson-Wolf" graph, the positive peaks indicate locations of the highly antigenic regions of the protein, i.e., regions from which epitope-bearing peptides of the invention can be obtained.

FIGS. 11A-F show the nucleotide (SEQ ID NO:186) and deduced amino acid sequence (SEQ ID NO:187) of all. Predicted amino acids from about 1 to about 22 constitute the predicted signal peptide (amino acid residues from about 1 to about 22 in SEQ ID NO:187) and are represented by the underlined amino acid regions; amino acids from about 666 to about 682, and/or amino acids from about 1145 to about 1161 constitute the predicted transmembrane domains (amino acids from about 666 to about 682, and/or amino acids from about 1145 to about 1161 in SEQ ID NO:187) and are represented by the double underlined amino acids; and amino acids from about 64 to about 96 constitute the predicted immunoglobulin and major histocompatibility complex protein domain (amino acids from about 64 to about 96 in SEQ ID NO:187) and are represented by the bold amino acids.

FIGS. 12A-E show the regions of similarity between the amino acid sequences of the integrin alpha 11 subunit (all) protein (SEQ ID NO:187) and the human integrin alpha 1 subunit (SEQ ID NO:189).

Figure 13:
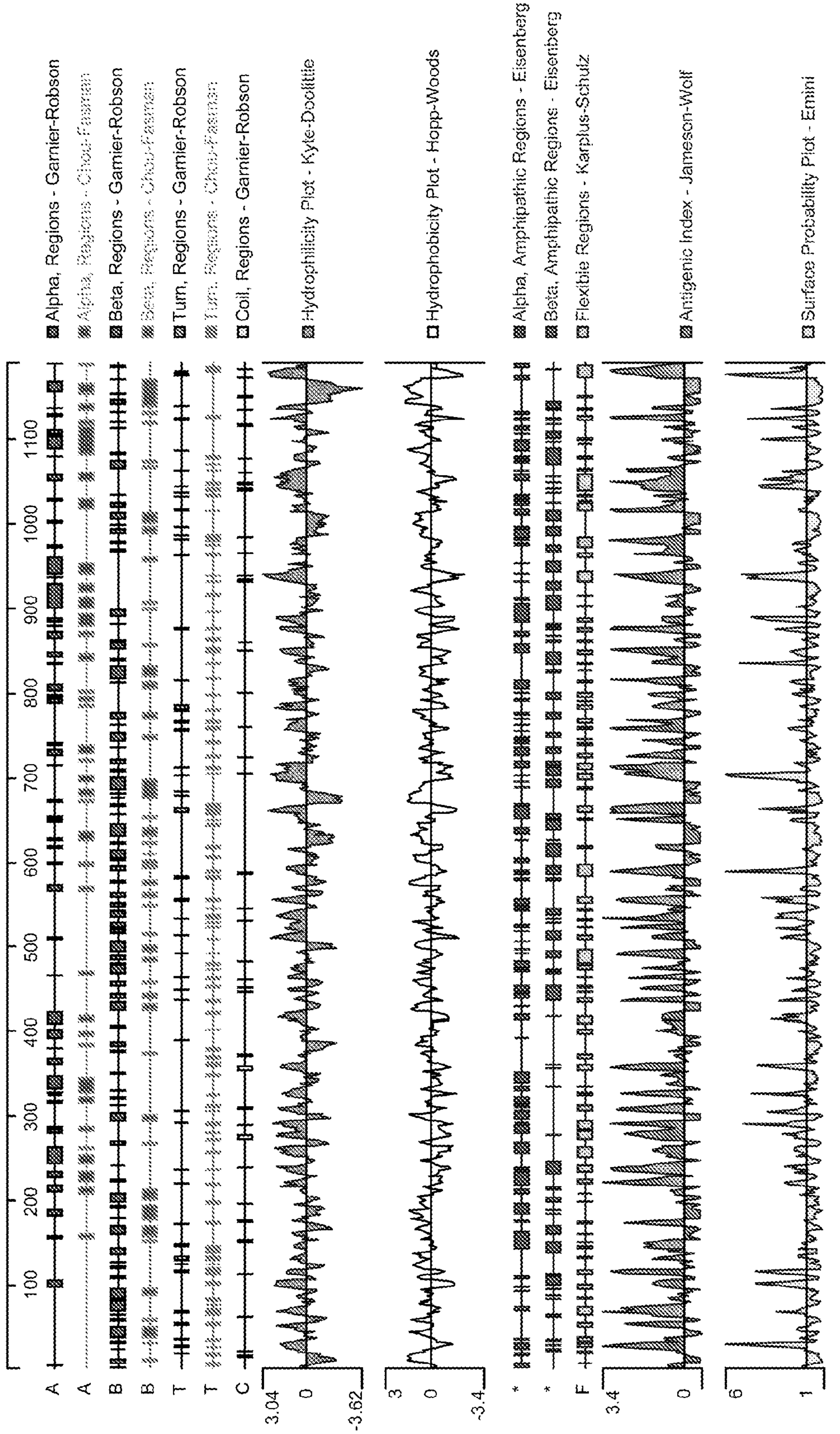

FIG. 13 shows an analysis of the integrin alpha 11 subunit (all) amino acid sequence. Alpha, beta, turn and coil regions; hydrophilicity and hydrophobicity; amphipathic regions; flexible regions; antigenic index and surface probability are shown.

SUMMARY OF THE INVENTION

The present invention relates to novel secreted proteins/polypeptides (such as human proteins/polypeptides). More specifically, isolated nucleic acid molecules are provided encoding novel secreted polypeptides. Novel polypeptides and antibodies that bind to these polypeptides are provided. Also provided are vectors, host cells, and recombinant and synthetic methods for producing human polynucleotides, polypeptides, and/or antibodies. The invention further relates to diagnostic and therapeutic methods useful for detecting, preventing, diagnosing, prognosticating, treating, and/or ameliorating diseases and disorders related to said proteins/polypeptides (relatedness may be by direct or indirect association, or by cause, consequence, or effect on said diseases and disorders), such as immune, cardiovascular, cancer, and other proliferative disorders and diseases. The invention further relates to screening methods for identifying agonists and antagonists of polynucleotides and polypeptides of the invention. The present invention further relates to methods and/or compositions for inhibiting or enhancing the production and function of the polypeptides of the present invention.

DETAILED DESCRIPTION

Polynucleotides and Polypeptides of the Invention

Features of Protein Encoded by Gene No: 1

For purposes of this application, this gene and its corresponding translation product are known as the B7-H5 gene and B7-H5 protein. This protein is believed to reside as a cell-surface molecule, and the transmembrane domain of this protein is believed to embody the following preferred amino acid residues:

(SEQ ID NO: 3)
IRVPVFNIVILLAGGF.

Polynucleotides encoding these polypeptides are also encompassed by the invention, as are antibodies that bind one or more of these peptides. The B7-H5 gene shares sequence homology with members of the B7 family of ligands (i.e., B7-1 (See Genbank Accession 507873)). These proteins and their corresponding receptors play vital roles in the growth, differentiation and death of T cells. For example, some members of this family (i.e., B7-H1) are involved in costimulation of the T cell response, as well as inducing increased cytokine production. Therefore, antagonists such as antibodies or small molecules directed against the B7-H5 gene are useful for treating T cell mediated immune system disorders. The gene encoding the disclosed cDNA is thought to reside on chromosome 6. Accordingly, polynucleotides related to this invention have uses, such as, for example, as a marker in linkage analysis for chromosome 6.

It has been discovered that this gene is expressed in activated neutrophils and activated T cells, and to a lesser extent in monocytes and heart tissue.

Preferred polypeptides of the present invention comprise, or alternatively consist of, one, two, three, four, five, six, seven or all seven of the immunogenic epitopes of the extracellular portion of the B7-H5 protein shown in SEQ ID NO:2 as residues: Leu-24 to Gln-35, Arg-59 to Pro-64, Glu-71 to His-78, Asp-89 to Gly-94, Pro-141 to Val-151, Thr-167 to Val-172, Ala-175 to Thr-180. Polynucleotides encoding these polypeptides are also encompassed by the invention, as are antibodies that bind one or more of these peptides.

In additional nonexclusive embodiments, polypeptides of the invention comprise, or alternatively consist of, one or more of the following amino acid sequences: 1.) The extracellular domain of the B7-H5 protein:

MRKTRLWGLLWMLFVSELRAATKLTEEKYELKEGQTLDVKCDYTLEKFA
SSQKAWQIIRDGEMPKTLACTERPSKNSHPVQVGRIILEDYHDHGLLRV
RMVNLQVEDSGLYQCVIYQPPKEPHMLFDRIRLVVTKGFSGTPGSNENS
TQNVYKIPPTTTKALCPLYTSPRTVTQAPPKSTADVSTPDSEINLTNVT
DI (SEQ ID NO: 4),

2.) The mature extracellular domain of the B7-H5 protein:

EKYELKEGQTLDVKCDYTLEKFASSQKAWQIIRDGEMPKTLACTERPSK
NSHPVQVGRIILEDYHDHGLLRVRMVNLQVEDSGLYQCVIYQPPKEPHM
LFDRIRLVVTKGFSGTPGSNENSTQNVYKIPPTTTKALCPLYTSPRTVT
QAPPKSTADVSTPDSEINLTNVTDI (SEQ ID NO: 5), and/or 3.) The leader sequence of the B7-H5 protein:

MRKTRLWGLLWMLFVSELRAATKLTE (SEQ ID NO: 6).

Polynucleotides encoding these polypeptides are also encompassed by the invention, as are antibodies that bind one or more of these polypeptides.

Also preferred are polypeptides comprising, or alternatively consisting of, fragments of the mature extracellular portion of the B7-H5 protein demonstrating functional activity (SEQ ID NO:5). Polynucleotides encoding these polypeptides are also encompassed by the invention. By functional activity is meant, a polypeptide fragment capable of displaying one or more known functional activities associated with the full-length (complete) B7-H5 protein. Such functional activities include, but are not limited to, biological activity (e.g., T cell costimulatory activity, ability to bind ICOS, and ability to induce or inhibit cytokine production), antigenicity [ability to bind (or compete with a B7-H5 polypeptide for binding) to an anti-B7-H5 antibody], immunogenicity (ability to generate antibody which binds to a B7-H5 polypeptide), ability to form multimers with B7-H5 polypeptides of the invention, and ability to bind to a receptor or ligand for a B7-H5 polypeptide.

FIG. 1 shows the nucleotide (SEQ ID NO:1) and deduced amino acid sequence (SEQ ID NO:2) corresponding to this gene.

FIG. 2 shows an analysis of the amino acid sequence (SEQ ID NO:2). Alpha, beta, turn and coil regions; hydrophilicity and hydrophobicity; amphipathic regions; flexible regions; antigenic index and surface probability are shown, and all were generated using the default settings of the recited computer algorithms. In the "Antigenic Index or Jameson-Wolf" graph, the positive peaks indicate locations of the highly antigenic regions of the protein, i.e., regions from which epitope-bearing peptides of the invention can be obtained. Polypeptides comprising, or alternatively consisting of, domains defined by these graphs are contemplated by the present invention, as are polynucleotides encoding these polypeptides.

The data presented in FIG. 2 are also represented in tabular form in Table 8. The columns are labeled with the headings "Res", "Position", and Roman Numerals I-XIV. The column headings refer to the following features of the amino acid sequence presented in FIG. 2, and Table 8: "Res": amino acid residue of SEQ ID NO:2 and FIG. 1; "Position": position of the corresponding residue within SEQ ID NO:2 and FIG. 1; I: Alpha, Regions—Garnier-Robson; II: Alpha, Regions—Chou-Fasman; III: Beta, Regions—Garnier-Robson; IV: Beta, Regions—Chou-Fasman; V: Turn, Regions—Garnier-Robson; VI: Turn, Regions—Chou-Fasman; VII: Coil, Regions—Garnier-Robson; VIII: Hydrophilicity Plot—Kyte-Doolittle; IX: Hydrophobicity Plot—Hopp-Woods; X: Alpha, Amphipathic Regions—Eisenberg; XI: Beta, Amphipathic Regions—Eisenberg; XII: Flexible Regions—Karplus-Schulz; XIII: Antigenic Index—Jameson-Wolf; and XIV: Surface Probability Plot—Emini.

Preferred embodiments of the invention in this regard include fragments that comprise, or alternatively consisting of, one or more of the following regions: alpha-helix and alpha-helix forming regions ("alpha-regions"), beta-sheet and beta-sheet forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, flexible regions, surface-forming regions and high antigenic index regions. The data representing the structural or functional attributes of the protein set forth in FIG. 2 and/or Table 8, as described above, was generated using the various modules and algorithms of the DNA*STAR set on default parameters. In a preferred embodiment, the data presented in columns VIII, IX, XIII, and XIV of Table 8 can be used to determine regions of the protein which exhibit a high degree of potential for antigenicity. Regions of high antigenicity are determined from the data presented in columns VIII, IX, XIII, and/or XIV by choosing values which represent regions of the polypeptide which are likely to be exposed on the surface of the polypeptide in an environment in which antigen recognition may occur in the process of initiation of an immune response.

Certain preferred regions in these regards are set out in FIG. 2, but may, as shown in Table 8, be represented or identified by using tabular representations of the data presented in FIG. 2. The DNA*STAR computer algorithm used to generate FIG. 2 (set on the original default parameters) was used to present the data in FIG. 2 in a tabular format (See Table 8). The tabular format of the data in FIG. 2 is used to easily determine specific boundaries of a preferred region.

The present invention is further directed to fragments of the polynucleotide sequences described herein. By a fragment of, for example, the polynucleotide sequence of a deposited cDNA or the nucleotide sequence shown in SEQ ID NO:1, is intended polynucleotide fragments at least about 15 nt, and more preferably at least about 20 nt, at least about 25 nt, still more preferably at least about 30 nt, at least about 35 nt, and even more preferably, at least about 40 nt in length, at least about 45 nt in length, at least about 50 nt in length, at least about 60 nt in length, at least about 70 nt in length, at least about 80 nt in length, at least about 90 nt in length, at least about 100 nt in length, at least about 125 nt in length, at least about 150 nt in length, at least about 175 nt in length, which are useful as diagnostic probes and primers as discussed herein. Of course, larger fragments 200-1500 nt in length are also useful according to the present invention, as are fragments corresponding to most, if not all, of the nucleotide sequence of a deposited cDNA or as shown in SEQ ID NO:1. By a fragment at least 20 nt in length, for example, is intended fragments which include 20 or more contiguous bases from the nucleotide sequence of a deposited cDNA or the nucleotide sequence as shown in SEQ ID NO:1. In this context "about" includes the particularly recited size, an sizes larger or smaller by several (5, 4, 3, 2, or 1) nucleotides, at either terminus or at both termini. Representative examples of polynucleotide fragments of the invention include, for example, fragments that comprise, or alternatively, consist of, a sequence from about nucleotide 1 to about 50, from about 51 to about 100, from about 101 to about 150, from about 151 to about 200, from about 201 to about 250, from about 251 to about 300, from about 301 to about 350, from about 351 to about 400, from about 401 to about 450, from about 451 to about 500, and from about 501 to about 550, and from about 551 to about 600, from about 601 to about 650, from about 651 to about 700, from about 701 to about 750, from about 751 to about 800, and from about 801 to about 860, of SEQ ID NO:1, or the complementary strand thereto, or the cDNA contained in a deposited clone. In this context "about" includes the particularly recited ranges, and ranges larger or smaller by several (5, 4, 3, 2, or 1) nucleotides, at either terminus or at both termini. In additional embodiments, the polynucleotides of the invention encode functional attributes of the corresponding protein.

Preferred polypeptide fragments of the invention comprise, or alternatively consist of, the secreted protein having a continuous series of deleted residues from the amino or the carboxy terminus, or both. Particularly, N-terminal deletions of the polypeptide can be described by the general formula m−234 where m is an integer from 2 to 228, where m corresponds to the position of the amino acid residue identified in SEQ ID NO:2. More in particular, the invention provides polynucleotides encoding polypeptides comprising, or alternatively consisting of, an amino acid sequence selected from the group: R-2 to P-234; K-3 to P-234; T-4 to P-234; R-5 to P-234; L-6 to P-234; W-7 to P-234; G-8 to P-234; L-9 to P-234; L-10 to P-234; W-11 to P-234; M-12 to P-234; L-13 to P-234; F-14 to P-234; V-15 to P-234; S-16 to P-234; E-17 to P-234; L-18 to P-234; R-19 to P-234; A-20 to P-234; A-21 to P-234; T-22 to P-234; K-23 to P-234; L-24 to P-234; T-25 to P-234; E-26 to P-234; E-27 to P-234; K-28 to P-234; Y-29 to P-234; E-30 to P-234; L-31 to P-234; K-32 to P-234; E-33 to P-234; G-34 to P-234; Q-35 to P-234; T-36 to P-234; L-37 to P-234; D-38 to P-234; V-39 to P-234; K-40 to P-234; C-41 to P-234; D-42 to P-234; Y-43 to P-234; T-44 to P-234; L-45 to P-234; E-46 to P-234; K-47 to P-234; F-48 to P-234; A-49 to P-234; S-50 to P-234; S-51 to P-234; Q-52 to P-234; K-53 to P-234; A-54 to P-234; W-55 to P-234; Q-56 to P-234; I-57 to P-234; I-58 to P-234; R-59 to P-234; D-60 to P-234; G-61 to P-234; E-62 to P-234; M-63 to P-234; P-64 to P-234; K-65 to P-234; T-66 to P-234; L-67 to P-234; A-68 to P-234; C-69 to P-234; T-70 to P-234; E-71 to P-234; R-72 to P-234; P-73 to P-234; S-74 to P-234; K-75 to P-234; N-76 to P-234; S-77 to P-234; H-78 to P-234; P-79 to P-234; V-80 to P-234; Q-81 to P-234; V-82 to P-234; G-83 to P-234; R-84 to P-234; I-85 to P-234; I-86 to P-234; L-87 to P-234; E-88 to P-234; D-89 to P-234; Y-90 to P-234; H-91 to P-234; D-92 to P-234; H-93 to P-234; G-94 to P-234; L-95 to P-234; L-96 to P-234; R-97 to P-234; V-98 to P-234; R-99 to P-234; M-100 to P-234; V-101 to P-234; N-102 to P-234; L-103 to P-234; Q-104 to P-234; V-105 to P-234; E-106 to P-234; D-107 to P-234; S-108 to P-234; G-109 to P-234; L-110 to P-234; Y-111 to P-234; Q-112 to P-234; C-113 to P-234; V-114 to P-234; I-115 to P-234; Y-116 to P-234; Q-117 to P-234; P-118 to P-234;

P-119 to P-234; K-120 to P-234; E-121 to P-234; P-122 to P-234; H-123 to P-234; M-124 to P-234; L-125 to P-234; F-126 to P-234; D-127 to P-234; R-128 to P-234; I-129 to P-234; R-130 to P-234; L-131 to P-234; V-132 to P-234; V-133 to P-234; T-134 to P-234; K-135 to P-234; G-136 to P-234; F-137 to P-234; S-138 to P-234; G-139 to P-234; T-140 to P-234; P-141 to P-234; G-142 to P-234; S-143 to P-234; N-144 to P-234; E-145 to P-234; N-146 to P-234; S-147 to P-234; T-148 to P-234; Q-149 to P-234; N-150 to P-234; V-151 to P-234; Y-152 to P-234; K-153 to P-234; I-154 to P-234; P-155 to P-234; P-156 to P-234; T-157 to P-234; T-158 to P-234; T-159 to P-234; K-160 to P-234; A-161 to P-234; L-162 to P-234; C-163 to P-234; P-164 to P-234; L-165 to P-234; Y-166 to P-234; T-167 to P-234; S-168 to P-234; P-169 to P-234; R-170 to P-234; T-171 to P-234; V-172 to P-234; T-173 to P-234; Q-174 to P-234; A-175 to P-234; P-176 to P-234; P-177 to P-234; K-178 to P-234; S-179 to P-234; T-180 to P-234; A-181 to P-234; D-182 to P-234; V-183 to P-234; S-184 to P-234; T-185 to P-234; P-186 to P-234; D-187 to P-234; S-188 to P-234; E-189 to P-234; I-190 to P-234; N-191 to P-234; L-192 to P-234; T-193 to P-234; N-194 to P-234; V-195 to P-234; T-196 to P-234; D-197 to P-234; I-198 to P-234; I-199 to P-234; R-200 to P-234; V-201 to P-234; P-202 to P-234; V-203 to P-234; F-204 to P-234; N-205 to P-234; I-206 to P-234; V-207 to P-234; I-208 to P-234; L-209 to P-234; L-210 to P-234; A-211 to P-234; G-212 to P-234; G-213 to P-234; F-214 to P-234; L-215 to P-234; S-216 to P-234; K-217 to P-234; S-218 to P-234; L-219 to P-234; V-220 to P-234; F-221 to P-234; S-222 to P-234; V-223 to P-234; L-224 to P-234; F-225 to P-234; A-226 to P-234; V-227 to P-234; T-228 to P-234; and/or L-229 to P-234 of SEQ ID NO:2. Polypeptides encoded by these polynucleotides are also encompassed by the invention.

Additionally, the invention provides polynucleotides encoding polypeptides comprising, or alternatively consisting of, an amino acid sequence selected from the following group of C-terminal deletions: M-1 to V-233; M-1 to F-232; M-1 to S-231; M-1 to R-230; M-1 to L-229; M-1 to T-228; M-1 to V-227; M-1 to A-226; M-1 to F-225; M-1 to L-224; M-1 to V-223; M-1 to S-222; M-1 to F-221; M-1 to V-220; M-1 to L-219; M-1 to S-218; M-1 to K-217; M-1 to S-216; M-1 to L-215; M-1 to F-214; M-1 to G-213; M-1 to G-212; M-1 to A-211; M-1 to L-210; M-1 to L-209; M-1 to I-208; M-1 to V-207; M-1 to I-206; M-1 to N-205; M-1 to F-204; M-1 to V-203; M-1 to P-202; M-1 to V-201; M-1 to R-200; M-1 to I-199; M-1 to I-198; M-1 to D-197; M-1 to T-196; M-1 to V-195; M-1 to N-194; M-1 to T-193; M-1 to L-192; M-1 to N-191; M-1 to I-190; M-1 to E-189; M-1 to S-188; M-1 to D-187; M-1 to P-186; M-1 to T-185; M-1 to S-184; M-1 to V-183; M-1 to D-182; M-1 to A-181; M-1 to T-180; M-1 to S-179; M-1 to K-178; M-1 to P-177; M-1 to P-176; M-1 to A-175; M-1 to Q-174; M-1 to T-173; M-1 to V-172; M-1 to T-171; M-1 to R-170; M-1 to P-169; M-1 to S-168; M-1 to T-167; M-1 to Y-166; M-1 to L-165; M-1 to P-164; M-1 to C-163; M-1 to L-162; M-1 to A-161; M-1 to K-160; M-1 to T-159; M-1 to T-158; M-1 to T-157; M-1 to P-156; M-1 to P-155; M-1 to I-154; M-1 to K-153; M-1 to Y-152; M-1 to V-151; M-1 to N-150; M-1 to Q-149; M-1 to T-148; M-1 to S-147; M-1 to N-146; M-1 to E-145; M-1 to N-144; M-1 to S-143; M-1 to G-142; M-1 to P-141; M-1 to T-140; M-1 to G-139; M-1 to S-138; M-1 to F-137; M-1 to G-136; M-1 to K-135; M-1 to T-134; M-1 to V-133; M-1 to V-132; M-1 to L-131; M-1 to R-130; M-1 to I-129; M-1 to R-128; M-1 to D-127; M-1 to F-126; M-1 to L-125; M-1 to M-124; M-1 to H-123; M-1 to P-122; M-1 to E-121; M-1 to K-120; M-1 to P-119; M-1 to P-118; M-1 to Q-117; M-1 to Y-116; M-1 to I-115; M-1 to V-114; M-1 to C-113; M-1 to Q-112; M-1 to Y-111; M-1 to L-110; M-1 to G-109; M-1 to S-108; M-1 to D-107; M-1 to E-106; M-1 to V-105; M-1 to Q-104; M-1 to L-103; M-1 to N-102; M-1 to V-101; M-1 to M-100; M-1 to R-99; M-1 to V-98; M-1 to R-97; M-1 to L-96; M-1 to L-95; M-1 to G-94; M-1 to H-93; M-1 to D-92; M-1 to H-91; M-1 to Y-90; M-1 to D-89; M-1 to E-88; M-1 to L-87; M-1 to I-86; M-1 to I-85; M-1 to R-84; M-1 to G-83; M-1 to V-82; M-1 to Q-81; M-1 to V-80; M-1 to P-79; M-1 to H-78; M-1 to S-77; M-1 to N-76; M-1 to K-75; M-1 to S-74; M-1 to P-73; M-1 to R-72; M-1 to E-71; M-1 to T-70; M-1 to C-69; M-1 to A-68; M-1 to L-67; M-1 to T-66; M-1 to K-65; M-1 to P-64; M-1 to M-63; M-1 to E-62; M-1 to G-61; M-1 to D-60; M-1 to R-59; M-1 to I-58; M-1 to I-57; M-1 to Q-56; M-1 to W-55; M-1 to A-54; M-1 to K-53; M-1 to Q-52; M-1 to S-51; M-1 to S-50; M-1 to A-49; M-1 to F-48; M-1 to K-47; M-1 to E-46; M-1 to L-45; M-1 to T-44; M-1 to Y-43; M-1 to D-42; M-1 to C-41; M-1 to K-40; M-1 to V-39; M-1 to D-38; M-1 to L-37; M-1 to T-36; M-1 to Q-35; M-1 to G-34; M-1 to E-33; M-1 to K-32; M-1 to L-31; M-1 to E-30; M-1 to Y-29; M-1 to K-28; M-1 to E-27; M-1 to E-26; M-1 to T-25; M-1 to L-24; M-1 to K-23; M-1 to T-22; M-1 to A-21; M-1 to A-20; M-1 to R-19; M-1 to L-18; M-1 to E-17; M-1 to S-16; M-1 to V-15; M-1 to F-14; M-1 to L-13; M-1 to M-12; M-1 to W-11; M-1 to L-10; M-1 to L-9; M-1 to G-8; and/or M-1 to W-7; of SEQ ID NO:2. Polypeptides encoded by these polynucleotides are also encompassed by the invention.

Also as mentioned above, even if deletion of one or more amino acids from the C-terminus of a protein results in modification of loss of one or more biological functions of the protein (e.g., ability to inhibit the Mixed Lymphocyte Reaction), other functional activities (e.g., biological activities, ability to multimerize, ability to bind ligand, ability to generate antibodies, ability to bind antibodies) may still be retained. For example, the ability of the shortened polypeptide to induce and/or bind to antibodies which recognize the complete or mature forms of the polypeptide generally will be retained when less than the majority of the residues of the complete or mature polypeptide are removed from the C-terminus. Whether a particular polypeptide lacking C-terminal residues of a complete polypeptide retains such immunologic activities can readily be determined by routine methods described herein and otherwise known in the art. It is not unlikely that a polypeptide with a large number of deleted C-terminal amino acid residues may retain some biological or immunogenic activities. In fact, peptides composed of as few as six amino acid residues may often evoke an immune response. Accordingly, the present invention further provides polypeptides having one or more residues deleted from the carboxy terminus of the amino acid sequence of the polypeptide shown in FIG. 1 (SEQ ID NO:2), as described by the general formula 1–n, where n is an integer from 6 to 228, where n corresponds to the position of the amino acid residue identified in SEQ ID NO:2.

More in particular, the invention provides polynucleotides encoding polypeptides comprising, or alternatively consisting of, an amino acid sequence selected from the group of N-terminal deletions of the mature extracellular portion of the B7-H5 protein (SEQ ID NO:5): K-28 to I-198; Y-29 to I-198; E-30 to I-198; L-31 to I-198; K-32 to I-198; E-33 to I-198; G-34 to I-198; Q-35 to I-198; T-36 to I-198; L-37 to I-198; D-38 to I-198; V-39 to I-198; K-40 to I-198; C-41 to I-198; D-42 to I-198; Y-43 to I-198; T-44 to I-198; L-45 to I-198; E-46 to I-198; K-47 to I-198; F-48 to I-198; A-49 to I-198; S-50 to I-198; S-51 to I-198; Q-52 to I-198; K-53 to I-198; A-54 to I-198; W-55 to I-198; Q-56 to I-198; I-57 to I-198; I-58 to I-198; R-59 to I-198; D-60 to I-198; G-61 to I-198;

E-62 to I-198; M-63 to I-198; P-64 to I-198; K-65 to I-198; T-66 to I-198; L-67 to I-198; A-68 to I-198; C-69 to I-198; T-70 to I-198; E-71 to I-198; R-72 to I-198; P-73 to I-198; S-74 to I-198; K-75 to I-198; N-76 to I-198; S-77 to I-198; H-78 to I-198; P-79 to I-198; V-80 to I-198; Q-81 to I-198; V-82 to I-198; G-83 to I-198; R-84 to I-198; I-85 to I-198; I-86 to I-198; L-87 to I-198; E-88 to I-198; D-89 to I-198; Y-90 to I-198; H-91 to I-198; D-92 to I-198; H-93 to I-198; G-94 to I-198; L-95 to I-198; L-96 to I-198; R-97 to I-198; V-98 to I-198; R-99 to I-198; M-100 to I-198; V-101 to I-198; N-102 to I-198; L-103 to I-198; Q-104 to I-198; V-105 to I-198; E-106 to I-198; D-107 to I-198; S-108 to I-198; G-109 to I-198; L-110 to I-198; Y-111 to I-198; Q-112 to I-198; C-113 to I-198; V-114 to I-198; I-115 to I-198; Y-116 to I-198; Q-117 to I-198; P-118 to I-198; P-119 to I-198; K-120 to I-198; E-121 to I-198; P-122 to I-198; H-123 to I-198; M-124 to I-198; L-125 to I-198; F-126 to I-198; D-127 to I-198; R-128 to I-198; I-129 to I-198; R-130 to I-198; L-131 to I-198; V-132 to I-198; V-133 to I-198; T-134 to I-198; K-135 to I-198; G-136 to I-198; F-137 to I-198; S-138 to I-198; G-139 to I-198; T-140 to I-198; P-141 to I-198; G-142 to I-198; S-143 to I-198; N-144 to I-198; E-145 to I-198; N-146 to I-198; S-147 to I-198; T-148 to I-198; Q-149 to I-198; N-150 to I-198; V-151 to I-198; Y-152 to I-198; K-153 to I-198; I-154 to I-198; P-155 to I-198; P-156 to I-198; T-157 to I-198; T-158 to I-198; T-159 to I-198; K-160 to I-198; A-161 to I-198; L-162 to I-198; C-163 to I-198; P-164 to I-198; L-165 to I-198; Y-166 to I-198; T-167 to I-198; S-168 to I-198; P-169 to I-198; R-170 to I-198; T-171 to I-198; V-172 to I-198; T-173 to I-198; Q-174 to I-198; A-175 to I-198; P-176 to I-198; P-177 to I-198; K-178 to I-198; S-179 to I-198; T-180 to I-198; A-181 to I-198; D-182 to I-198; V-183 to I-198; S-184 to I-198; T-185 to I-198; P-186 to I-198; D-187 to I-198; S-188 to I-198; E-189 to I-198; I-190 to I-198; N-191 to I-198; L-192 to I-198; T-193 to I-198; and/or K-23 to A-29 of SEQ ID NO:2. Polypeptides encoded by these polynucleotides are also encompassed by the invention.

Additionally, the invention provides polynucleotides encoding polypeptides comprising, or alternatively consisting of, an amino acid sequence selected from the group of C-terminal deletions of the mature extracellular portion of the B7-H5 protein (SEQ ID NO:5): E-27 to D-197; E-27 to T-196; E-27 to V-195; E-27 to N-194; E-27 to T-193; E-27 to L-192; E-27 to N-191; E-27 to I-190; E-27 to E-189; E-27 to S-188; E-27 to D-187; E-27 to P-186; E-27 to T-185; E-27 to S-184; E-27 to V-183; E-27 to D-182; E-27 to A-181; E-27 to T-180; E-27 to S-179; E-27 to K-178; E-27 to P-177; E-27 to P-176; E-27 to A-175; E-27 to Q-174; E-27 to T-173; E-27 to V-172; E-27 to T-171; E-27 to R-170; E-27 to P-169; E-27 to S-168; E-27 to T-167; E-27 to Y-166; E-27 to L-165; E-27 to P-164; E-27 to C-163; E-27 to L-162; E-27 to A-161; E-27 to K-160; E-27 to T-159; E-27 to T-158; E-27 to T-157; E-27 to P-156; E-27 to P-155; E-27 to I-154; E-27 to K-153; E-27 to Y-152; E-27 to V-151; E-27 to N-150; E-27 to Q-149; E-27 to T-148; E-27 to S-147; E-27 to N-146; E-27 to E-145; E-27 to N-144; E-27 to S-143; E-27 to G-142; E-27 to P-141; E-27 to T-140; E-27 to G-139; E-27 to S-138; E-27 to F-137; E-27 to G-136; E-27 to K-135; E-27 to T-134; E-27 to V-133; E-27 to V-132; E-27 to L-131; E-27 to R-130; E-27 to I-129; E-27 to R-128; E-27 to D-127; E-27 to F-126; E-27 to L-125; E-27 to M-124; E-27 to H-123; E-27 to P-122; E-27 to E-121; E-27 to K-120; E-27 to P-119; E-27 to P-118; E-27 to Q-117; E-27 to Y-116; E-27 to I-115; E-27 to V-114; E-27 to C-113; E-27 to Q-112; E-27 to Y-111; E-27 to L-110; E-27 to G-109; E-27 to S-108; E-27 to D-107; E-27 to E-106; E-27 to V-105; E-27 to Q-104; E-27 to L-103; E-27 to N-102; E-27 to V-101; E-27 to M-100; E-27 to R-99; E-27 to V-98; E-27 to R-97; E-27 to L-96; E-27 to L-95; E-27 to G-94; E-27 to H-93; E-27 to D-92; E-27 to H-91; E-27 to Y-90; E-27 to D-89; E-27 to E-88; E-27 to L-87; E-27 to I-86; E-27 to I-85; E-27 to R-84; E-27 to G-83; E-27 to V-82; E-27 to Q-81; E-27 to V-80; E-27 to P-79; E-27 to H-78; E-27 to S-77; E-27 to N-76; E-27 to K-75; E-27 to S-74; E-27 to P-73; E-27 to R-72; E-27 to E-71; E-27 to T-70; E-27 to C-69; E-27 to A-68; E-27 to L-67; E-27 to T-66; E-27 to K-65; E-27 to P-64; E-27 to M-63; E-27 to E-62; E-27 to G-61; E-27 to D-60; E-27 to R-59; E-27 to I-58; E-27 to I-57; E-27 to Q-56; E-27 to W-55; E-27 to A-54; E-27 to K-53; E-27 to Q-52; E-27 to S-51; E-27 to S-50; E-27 to A-49; E-27 to F-48; E-27 to K-47; E-27 to E-46; E-27 to L-45; E-27 to T-44; E-27 to Y-43; E-27 to D-42; E-27 to C-41; E-27 to K-40; E-27 to V-39; E-27 to D-38; E-27 to L-37; E-27 to T-36; E-27 to Q-35; E-27 to G-34; and/or E-27 to E-33 of SEQ ID NO:2. Polypeptides encoded by these polynucleotides are also encompassed by the invention.

In addition, any of the above listed N- or C-terminal deletions can be combined to produce a N- and C-terminal deleted polypeptide. The invention also provides polypeptides comprising, or alternatively consisting of, one or more amino acids deleted from both the amino and the carboxyl termini, which may be described generally as having residues m-n of SEQ ID NO:2, where n and m are integers as described above. Polynucleotides encoding these polypeptides are also encompassed by the invention.

The present invention is also directed to proteins containing polypeptides at least 80%, 85%, 90%, 92%, 93%, 94%, 95%, 96%, 97%, 98% or 99% identical to a polypeptide sequence set forth herein as m-n. In preferred embodiments, the application is directed to proteins containing polypeptides at least 80%, 85%, 90%, 95%, 96%, 97%, 98% or 99% identical to polypeptides having the amino acid sequence of the specific N- and C-terminal deletions recited herein. Polynucleotides encoding these polypeptides are also encompassed by the invention.

Also included are polynucleotide sequences encoding a polypeptide consisting of a portion of the complete amino acid sequence encoded by a cDNA clone contained in ATCC Deposit Nos. 97903 and/or 209049, where this portion excludes any integer of amino acid residues from 1 to about 228 amino acids from the amino terminus of the complete amino acid sequence encoded by a cDNA clone contained in ATCC Deposit Nos. 97903 and/or 209049, or any integer of amino acid residues from 1 to about 228 amino acids from the carboxy terminus, or any combination of the above amino terminal and carboxy terminal deletions, of the complete amino acid sequence encoded by the cDNA clone contained in ATCC Deposit Nos. 97903 and/or 209049. Polypeptides encoded by these polynucleotides also are encompassed by the invention.

As described herein or otherwise known in the art, the polynucleotides of the invention have uses that include, but are not limited to, serving as probes or primers in chromosome identification, chromosome mapping, and linkage analysis.

Polynucleotides and polypeptides of the invention are useful as reagents for differential identification of immune system tissue(s) or cell type(s) present in a biological sample and for diagnosis of diseases and conditions which include, but are not limited to, diseases and/or disorders involving immune system activation, stimulation and/or surveillance, particularly involving T cells and/or neutrophils. Similarly, polypeptides and antibodies directed to these polypeptides are useful in providing immunological probes for differential identification of the tissue(s) or cell type(s). Particularly contemplated are the use of antibodies directed against the extracellular portion of this protein which act as antagonists for the activity of the B7-H5 protein. Such antagonistic antibodies would be useful for the prevention and/or inhibition of such biological activities as are disclosed herein (e.g. T cell modulated activities).

For a number of disorders of the above tissues or cells, particularly of the immune system, expression of this gene at significantly higher or lower levels may be routinely detected in certain tissues or cell types (e.g., immune, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in immune cells (e.g., T-cells, neutrophils), and the homology to members of the B7 family of ligands, indicates that the polynucleotides and polypeptides corresponding to this gene are useful for the diagnosis, detection and/or treatment of diseases and/or disorders involving immune system activation, stimulation and/or surveillance, particularly as relating to T cells and/or neutrophils. In particular, the translation product of the B7-H5 gene may be involved in the costimulation of T cells, binding to ICOS, and/or may play a role in modulation of the expression of particular cytokines. Representative uses are also described in the “Immune Activity” section below and elsewhere herein.

More generally, the tissue distribution in immune system cells indicates that this gene product may be involved in the regulation of cytokine production, antigen presentation, or other processes that may also suggest a usefulness in the treatment of cancer (e.g. by boosting immune responses). Since the gene is expressed in cells of lymphoid origin, the gene or protein, as well as, antibodies directed against the protein may show utility as a tumor marker and/or immunotherapy targets for the above listed tissues. Therefore it may be also used as an agent for immunological disorders including arthritis, asthma, immune deficiency diseases such as AIDS, leukemia, rheumatoid arthritis, inflammatory bowel disease, sepsis, acne, and psoriasis. In addition, this gene product may have commercial utility in the expansion of stem cells and committed progenitors of various blood lineages, and in the differentiation and/or proliferation of various cell types. Protein, as well as, antibodies directed against the protein may show utility as a tumor marker and/or immunotherapy targets for the above listed tissues.

Furthermore, the protein may also be used to determine biological activity, to raise antibodies, as tissue markers, to isolate cognate ligands or receptors, to identify agents that modulate their interactions, in addition to its use as a nutritional supplement.

Many polynucleotide sequences, such as EST sequences, are publicly available and accessible through sequence databases. Some of these sequences are related to SEQ ID NO:1 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 888 of SEQ ID NO:1, b is an integer of 15 to 902, where both a and b correspond to the positions of nucleotide residues shown in SEQ ID NO:1, and where b is greater than or equal to a+14.

Features of Protein Encoded by Gene No: 2

This gene is expressed primarily in placenta and several tumors of various tissue origin and to a lesser extent in normal tissues including liver, lung, brain, and skin, Therefore, polynucleotides and polypeptides of the invention are useful as reagents for differential identification of the tissue(s) or cell type(s) present in a biological sample and for diagnosis of cancers of all kinds. Similarly, polypeptides and antibodies directed to these polypeptides are useful in providing immunological probes for differential identification of the tissue(s) or cell type(s). For a number of disorders of the above tissues or cells, particularly of the central nervous system, respiratory system and skin, expression of this gene at significantly higher or lower levels may be routinely detected in certain tissues and cell types (e.g., liver, lung, brain and other tissues of the nervous system, and skin, and cancerous and wounded tissues) or bodily fluids (e.g., serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

The high expression of this gene in multiple tumors indicates that the protein product of the clone may be involved in cell growth control and therefore would be useful for treatment of certain cancers. Likewise molecules developed to block the activity of the protein product of this clone could be used to block its potential role in tumor growth promotion.

This gene is believed to reside on chromosome 6. Polynucleotides related to this gene are believed, therefore, to be useful in linkage analysis for chromosome 6.

Preferred epitopes include those comprising a sequence shown in SEQ ID NO:8 as residues: Gln-37 to Gln-43, Cys-51 to Cys-65.

Many polynucleotide sequences, such as EST sequences, are publicly available and accessible through sequence databases. Some of these sequences are related to SEQ ID NO:7 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 1909 of SEQ ID NO:7, b is an integer of 15 to 1923, where both a and b correspond to the positions of nucleotide residues shown in SEQ ID NO:7, and where the b is greater than or equal to a+14.

Features of Protein Encoded by Gene No: 3

The translation product of this gene shares sequence homology with CpG islands genes which are short stretches of DNA containing a high density of non-methylated CpG dinucleotides, predominantly associated with coding regions. As CpG islands overlap with approximately 60% of human genes, the CpG island library can be used to isolate full-length cDNAs and to place genes on genomic maps. The translation product also shares distant homology with the A33 protein, which is a transmembrane protein and a member of the immunoglobulin superfamily.

This gene is expressed primarily in the testes and to a lesser extent in the lung, tonsils, placenta, and rhabdomyosarcoma.

Therefore, polynucleotides and polypeptides of the invention are useful as reagents for differential identification of the tissue(s) or cell type(s) present in a biological sample and for diagnosis of diseases and conditions which include, but are not limited to, diseases related to the testes, lung, tonsils, placenta, and tumors. Similarly, polypeptides and antibodies directed to these polypeptides are useful in providing immunological probes for differential identification of the tissue(s) or cell type(s). For a number of disorders of the above tissues or cells, particularly of the diseases related to the testes, lung, tonsils, placenta, and tumors, expression of this gene at significantly higher or lower levels may be routinely detected in certain tissues or cell types (e.g., testes and other reproductive tissue, lung, tonsils, placenta, and striated muscle, and cancerous and wounded tissues) or bodily fluids (e.g., seminal fluid, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder. Preferred epitopes include those comprising a sequence shown in SEQ ID NO:10 as residues: Met-1 to His-7.

The tissue distribution indicates that polynucleotides and polypeptides corresponding to the gene are useful for diagnosis and treatment of diseases related to the testes, lung, tonsils, placenta, and tumors. More specifically, the tissue distribution indicates that the protein product of this clone is useful for the treatment and diagnosis of conditions concerning proper testicular function (e.g. endocrine function, sperm maturation). Therefore, this gene product is useful in the treatment of male infertility and/or impotence. This gene product is also useful in assays designed to identify binding agents as such agents (antagonists) are useful as male contraceptive agents. Similarly, the protein is believed to by useful in the treatment and/or diagnosis of testicular cancer. The testes are also a site of active gene expression of transcripts that may be expressed, particularly at low levels, in other tissues of the body. Therefore, this gene product may be expressed in other specific tissues or organs where it may play related functional roles in other processes, such as hematopoiesis, inflammation, bone formation, and kidney function, to name a few possible target indications. Protein, as well as, antibodies directed against the protein may show utility as a tumor marker and/or immunotherapy targets for the above listed tissues.

Features of Protein Encoded by Gene No: 4

When tested against Jurkat T cells, supernatants removed from cells containing this gene activated the GAS assay. Thus, it is likely that this gene activates T cells through the Jak-STAT signal transduction pathway. The gamma activating sequence (GAS) is a promoter element found upstream of many genes which are involved in the Jak-STAT pathway. The Jak-STAT pathway is a large, signal transduction pathway involved in the differentiation and proliferation of cells. Therefore, activation of the Jak-STAT pathway, reflected by the binding of the GAS element, can be used to indicate proteins involved in the proliferation and differentiation of cells.

A preferred polypeptide variant of the invention comprises the following amino acid sequence:

MARGSLRRLLRLLVLGLWLALLRSVAGEQAPGTAPCSRGSSWSADLDKC

MDCSTSCPLPAALAHPWGRSEPDLRAGAAFWLFGLETMPQEREVHHPHR

GDRRRGLPSCGADPVTMCPLPAGARPLIIHSSILEPVSASQTRREPSSS

NHKGGGGR (SEQ ID NO: 19).

Polynucleotides encoding these polypeptides are also provided.

The gene encoding the disclosed cDNA is believed to reside on chromosome 16. Accordingly, polynucleotides related to this invention are useful as a marker in linkage analysis for chromosome 16. This gene is expressed primarily in tumor growth factor or lipopolysaccharide treated bone marrow stroma, epitheloid sarcoma, umbilical vein endothelial cells, in keratinocytes, and to a lesser extent, in other tissues including endothelial cells and placenta.

Therefore, polynucleotides and polypeptides of the invention are useful as reagents for differential identification of the tissue(s) or cell type(s) present in a biological sample and for diagnosis of diseases and conditions which include, but are not limited to, hematopoiesis or immune disorders including integumentary or vascular disorders, particularly impaired wound healing and autoimmune disorders. Similarly, polypeptides and antibodies directed to these polypeptides are useful in providing immunological probes for differential identification of the tissue(s) or cell type(s). For a number of disorders of the above tissues or cells, particularly of the skin and/or hematopoietic, integumentary, or immune systems, expression of this gene at significantly higher or lower levels may be routinely detected in certain tissues or cell types (e.g. hematopoietic, immune, integumentary, endothelial, and/or cancerous and wounded tissues) or bodily fluids (e.g., lymph, serum, plasma, urine, synovial fluid and/or spinal fluid) or another tissue or cell sample taken from an individual having such a disorder, relative to the standard gene expression level, i.e., the expression level in healthy tissue or bodily fluid from an individual not having the disorder.

Preferred polypeptides of the present invention comprise immunogenic epitopes including those comprising a sequence shown in SEQ ID NOs: 14 and 12 as residues: Pro-35 to Trp-42, Ala-53 to Asp-62, Pro-65 to Asp-72, Thr-86 to Phe-93, Ile-97 to Glu-103, and Arg-103 to Pro-113. Polynucleotides encoding said polypeptides are also provided.

The tissue distribution in tumor growth factor or lipopolysaccharide treated bone marrow stroma, epitheloid sarcoma, and umbilical vein endothelial cells; and activation of the Jak-Stat promoter element in immune cells, specifically Jurkat T-cells, indicates that polynucleotides and polypeptides corresponding to this gene are useful for the diagnosis, prevention, and/or treatment of a variety of immune system disorders. Representative uses are described in the "Immune Activity" and "Infectious Disease" sections below, in Examples 17, 42, 44, 45, 47, 49, 50, and 51, and elsewhere herein. Briefly, the expression of this gene product indicates a role in regulating the proliferation; survival; differentiation; and/or activation of hematopoietic cell lineages, including blood stem cells. This gene product may be involved in the regulation of cytokine production, antigen presentation, or other processes suggesting a usefulness in the treatment of cancer (e.g., by boosting immune responses).

Since the gene is expressed in cells of lymphoid origin, the natural gene product may be involved in immune functions. Therefore it may be also used as an agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, systemic lupus erythematosis, drug induced hemolytic anemia, rheumatoid arthritis, Sjogren's disease, scleroderma and tissues.

The tissue distribution in keratinocytes indicates that the protein products of this gene are useful for the treatment of wound healing deficiency and skin disorders, including congenital disorders (i.e. nevi, moles, freckles, Mongolian spots, hemangiomas, port-wine syndrome), integumentary tumors (i.e. keratoses, Bowen's disease, basal cell carcinoma, squamous cell carcinoma, malignant melanoma, Paget's disease, mycosis fungoides, and Kaposi's sarcoma), injuries and inflammation of the skin (i.e. wounds, rashes, prickly heat disorder, psoriasis, dermatitis), atherosclerosis, uticaria, eczema, photosensitivity, autoimmune disorders (i.e. lupus erythematosus, vitiligo, dermatomyositis, morphea, scleroderma, pemphigoid, and pemphigus), keloids, striae, erythema, petechiae, purpura, and xanthelasma. Moreover, such disorders may predispose increased susceptibility to viral and bacterial infections of the skin (i.e. cold sores, warts, chickenpox, molluscum contagiosum, herpes zoster, boils, cellulitis, erysipelas, impetigo, tinea, athletes foot, and ringworm). Moreover, expression within endothelial cells and pancreatic tissues indicates that the protein product of this gene may be useful in the treatment and/or prevention of a variety of vascular disorders, particularly those involving highly vascularized tissues, which include, but are not limited to, embolism, aneurysm, stroke, atherosclerosis, and microvascular disease. Protein, as well as, antibodies directed against the protein may show utility as a tumor marker and/or immunotherapy targets for the above listed tissues.

Moreover, the protein may represent a secreted factor that influences the differentiation or behavior of other blood cells, or that recruits hematopoietic cells to sites of injury. In addition, this gene product may have commercial utility in the expansion of stem cells and committed progenitors of various blood lineages, and in the differentiation and/or proliferation of various cell types. The secreted protein can be used to determine biological activity, to raise antibodies, as tissue markers, to isolate cognate ligands or receptors, to identify agents that modulate their interactions and as nutritional supplements. It may also have a very wide range of biological activities although no evidence for any is provided in the specification. Typical of these are cytokine, cell proliferation/differentiation modulating activity or induction of other cytokines; immunostimulating/immunosuppressant activities (e.g., for treating human immunodeficiency-virus infection, cancer, autoimmune diseases and allergy); regulation of haematopoiesis (e.g., for treating anaemia or as adjunct to chemotherapy); stimulation of growth of bone, cartilage, tendons, ligaments and/or nerves (e.g., for treating wounds, stimulation of follicle stimulating hormone (for control of fertility); chemotactic and chemokinetic activities (e.g., for treating infections, tumours); haemostatic or thrombolytic activity (e.g., for treating haemophilia, cardiac infarction etc.); anti-inflammatory activity (e.g., for treating septic shock, Crohn's disease); as antimicrobials; for treating psoriasis or other hyperproliferative disease; for regulation of metabolism, behaviour, and many others. Also contemplated is the use of the corresponding nucleic acid in gene therapy procedures. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NOs: 11 and 13 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1027 of SEQ ID NO:11 or 1 to 1038 of SEQ ID NO:13, b is an integer of 15 to 1041 of SEQ ID NO:11 or 15 to 1052 of SEQ ID NO:13, where both a and b correspond to the positions of nucleotide residues shown in SEQ ID NOs: 11 and 13, and where b is greater than or equal to a+14.

Features of Protein Encoded by Gene No: 5

In a specific embodiment, polypeptides of the invention, comprise or alternatively consist of, one or more of the following amino acid sequences:

```
TTILRTCTIVCFYYWFNGVMVLLFFLDRNLLTFNQASIMPFSNTDFLHC
LSFKKKLMLLRYIFYVVLTGPTLSLKGDENQIKNLFT (SEQ ID NO:
24), IVCFYYWFNGVMVLLFFLDRNLL (SEQ ID NO: 25),
and/or LLRYIFYVVLTGPTLSLKGDENQI (SEQ ID NO: 26).
```

Polynucleotides encoding these polypeptides are also encompassed by the invention as are antibodies that bind one or more of these polypeptides. Moreover, fragments and variants of these polypeptides (such as, for example, fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides, or the complement thereof) are encompassed by the invention. Antibodies that bind polypeptides of the invention are also encompassed by the invention. Polynucleotides encoding these polypeptides are also encompassed by the invention.

Also preferred are polypeptides, comprising or alternatively consisting of, the mature polypeptide which is predicted to consist of residues:

```
PTCYSRMRALSQEITRDFNLLQVSEPSEPCVRYLPRLYLDIHNYCVLDK
LRDFVASPPCWKVAQVDSLKDKARKLYTIMNSFCRRDLVFLLDDCNALE
YPIPVTTVLPDRQR (SEQ ID NO: 27)
```

of the foregoing sequence (SEQ ID NO:21), and biologically active fragments of the mature polypeptide (e.g., fragments that induce hematopoiesis). Polynucleotides encoding these polypeptides are also encompassed by the invention. Moreover, fragments and variants of these polypeptides (such as, for example, fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides, or the complement thereof) are encompassed by the invention. Antibodies that bind polypeptides of the invention are also encompassed by the invention. Polynucleotides encoding these polypeptides are also encompassed by the invention.

FIGS. 3A-B show the nucleotide (SEQ ID NO:20) and deduced amino acid sequence (SEQ ID NO:21) corresponding to this gene.

FIG. 4 shows an analysis of the amino acid sequence (SEQ ID NO:21). Alpha, beta, turn and coil regions; hydrophilicity and hydrophobicity; amphipathic regions; flexible regions; antigenic index and surface probability are shown, and all were generated using the default settings of the recited computer algorithms. In the "Antigenic Index or Jameson Wolf" graph, the positive peaks indicate locations of the highly antigenic regions of the protein, i.e., regions from which epitope-bearing peptides of the invention can be obtained. Polypeptides comprising, or alternatively consisting of, domains defined by these graphs are contemplated by the present invention, as are polynucleotides encoding these polypeptides.

The data presented in FIG. 4 are also represented in tabular form in Table 10. The columns are labeled with the headings "Res", "Position", and Roman Numerals I XIV. The column headings refer to the following features of the amino acid sequence presented in FIG. 4, and Table 10: "Res": amino acid residue of SEQ ID NO:21 and FIGS. 3A-B; "Position": position of the corresponding residue within SEQ ID NO:21 and FIGS. 3A-B; I: Alpha, Regions Garnier Robson; II: Alpha, Regions Chou Fasman; III: Beta, Regions Garnier Robson; IV: Beta, Regions Chou Fasman; V: Turn, Regions Garnier Robson; VI: Turn, Regions Chou Fasman; VII: Coil, Regions Garnier Robson; VIII: Hydrophilicity Plot Kyte Doolittle; IX: Hydrophobicity Plot Hopp Woods; X: Alpha, Amphipathic Regions Eisenberg; XI: Beta, Amphipathic Regions Eisenberg; XII: Flexible Regions Karplus Schulz; XIII: Antigenic Index Jameson Wolf; and XIV: Surface Probability Plot Emini.

Preferred embodiments of the invention in this regard include fragments that comprise, or alternatively consisting of, one or more of the following regions: alpha-helix and alpha-helix forming regions ("alpha-regions"), beta-sheet and beta-sheet forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, flexible regions, surface-forming regions and high antigenic index regions. The data representing the structural or functional attributes of the protein set forth in FIGS. 3A-B and/or Table 10, as described above, was generated using the various modules and algorithms of the DNA*STAR set on default parameters. In a preferred embodiment, the data presented in columns VIII, IX, XIII, and XIV of Table 10 can be used to determine regions of the protein which exhibit a high degree of potential for antigenicity. Regions of high antigenicity are determined from the data presented in columns VIII, IX, XIII, and/or XIV by choosing values which represent regions of the polypeptide which are likely to be exposed on the surface of the polypeptide in an environment in which antigen recognition may occur in the process of initiation of an immune response.

Certain preferred regions in these regards are set out in FIGS. 3A-B, but may, as shown in Table 10, be represented or identified by using tabular representations of the data presented in FIG. 4 The DNA*STAR computer algorithm used to generate FIG. 4 set on the original default parameters) was used to present the data in FIG. 4 in a tabular format (See Table 10). The tabular format of the data in FIG. 4 is used to easily determine specific boundaries of a preferred region.

The present invention is further directed to fragments of the polynucleotide sequences described herein. By a fragment of, for example, the polynucleotide sequence of a deposited cDNA or the nucleotide sequence shown in SEQ ID NO:20, is intended polynucleotide fragments at least about 15 nt, and more preferably at least about 20 nt, at least about 25 nt, still more preferably at least about 30 nt, at least about 35 nt, and even more preferably, at least about 40 nt in length, at least about 45 nt in length, at least about 50 nt in length, at least about 60 nt in length, at least about 70 nt in length, at least about 80 nt in length, at least about 90 nt in length, at least about 100 nt in length, at least about 125 nt in length, at least about 150 nt in length, at least about 175 nt in length, which are useful as diagnostic probes and primers as discussed herein. Of course, larger fragments 200-500 nt in length are also useful according to the present invention, as are fragments corresponding to most, if not all, of the nucleotide sequence of a deposited cDNA or as shown in SEQ ID NO:20. By a fragment at least 20 nt in length, for example, is intended fragments which include 20 or more contiguous bases from the nucleotide sequence of a deposited cDNA or the nucleotide sequence as shown in SEQ ID NO:20. In this context "about" includes the particularly recited size, an sizes larger or smaller by several (5, 4, 3, 2, or 1) nucleotides, at either terminus or at both termini. Representative examples of polynucleotide fragments of the invention include, for example, fragments that comprise, or alternatively, consist of, a sequence from about nucleotide 1 to about 50, from about 51 to about 100, from about 101 to about 150, from about 151 to about 200, from about 201 to about 250, from about 251 to about 300, from about 301 to about 350, from about 351 to about 400, from about 401 to about 450, from about 451 to about 500, and from about 501 to about 550, and from about 551 to about 600, from about 601 to about 650, from about 651 to about 700, from about 701 to about 750, from about 751 to about 800, from about 801 to about 850, from about 851 to about 900, from about 901 to about 950, or from about 951 to about 985 of SEQ ID NO:20, or the complementary strand thereto, or the cDNA contained in a deposited clone. In this context "about" includes the particularly recited ranges, and ranges larger or smaller by several (5, 4, 3, 2, or 1) nucleotides, at either terminus or at both termini. In additional embodiments, the polynucleotides of the invention encode functional attributes of the corresponding protein.

Preferred polypeptide fragments of the invention comprise, or alternatively consist of, the secreted protein having a continuous series of deleted residues from the amino or the carboxyl terminus, or both. Particularly, N-terminal deletions of the polypeptide can be described by the general formula m−136 where m is an integer from 2 to 136, where m corresponds to the position of the amino acid residue identified in SEQ ID NO:21. More in particular, the invention provides polynucleotides encoding polypeptides comprising, or alternatively consisting of, an amino acid sequence selected from the group: R-2 to R-136; T-3 to R-136; P-4 to R-136; G-5 to R-136; P-6 to R-136; L-7 to R-136; P-8 to R-136; V-9 to R-136; L-10 to R-136; L-11 to R-136; L-12 to R-136; L-13 to R-136; L-14 to R-136; A-15 to R-136; G-16 to R-136; A-17 to R-136; P-18 to R-136; A-19 to R-136; A-20 to R-136; R-21 to R-136; P-22 to R-136; T-23 to R-136; P-24 to R-136; P-25 to R-136; T-26 to R-136; C-27 to R-136; Y-28 to R-136; S-29 to R-136; R-30 to R-136; M-31 to R-136; R-32 to R-136; A-33 to R-136; L-34 to R-136; S-35 to R-136; Q-36 to R-136; E-37 to R-136; I-38 to R-136; T-39 to R-136; R-40 to R-136; D-41 to R-136; F-42 to R-136; N-43 to R-136; L-44 to R-136; L-45 to R-136; Q-46 to R-136; V-47 to R-136; S-48 to R-136; E-49 to R-136; P-50 to R-136; S-51 to R-136; E-52 to R-136; P-53 to R-136; C-54 to R-136; V-55 to R-136; R-56 to R-136; Y-57 to R-136; L-58 to R-136; P-59 to R-136; R-60 to R-136; L-61 to R-136; Y-62 to R-136; L-63 to R-136; D-64 to R-136; I-65 to R-136; H-66 to R-136; N-67 to R-136; Y-68 to R-136; C-69 to R-136; V-70 to R-136; L-71 to R-136; D-72 to R-136; K-73 to R-136; L-74 to R-136; R-75 to R-136; D-76 to R-136; F-77 to R-136; V-78 to R-136; A-79 to R-136; S-80 to R-136; P-81 to R-136; P-82 to R-136; C-83 to R-136; W-84 to R-136; K-85 to R-136; V-86 to R-136; A-87 to R-136; Q-88 to R-136; V-89 to R-136; D-90 to R-136; S-91 to R-136; L-92 to R-136; K-93 to R-136; D-94 to R-136; K-95 to R-136; A-96 to R-136; R-97 to R-136; K-98 to R-136; L-99 to R-136; Y-100 to R-136; T-101 to R-136; I-102 to R-136; M-103 to R-136; N-104 to R-136; S-105 to R-136; F-106 to R-136; C-107 to R-136; R-108 to R-136; R-109 to R-136; D-110 to R-136; L-111 to R-136; V-112 to R-136; F-113 to R-136; L-114 to R-136;

L-115 to R-136; D-116 to R-136; D-117 to R-136; C-118 to R-136; N-119 to R-136; A-120 to R-136; L-121 to R-136; E-122 to R-136; Y-123 to R-136; P-124 to R-136; I-125 to R-136; P-126 to R-136; V-127 to R-136; T-128 to R-136; T-129 to R-136; V-130 to R-136; and L-131 to R-136 of SEQ ID NO:21. Polypeptides encoded by these polynucleotides are also encompassed by the invention. Moreover, fragments and variants of these polypeptides (such as, for example, fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides, or the complement thereof) are encompassed by the invention. Antibodies that bind polypeptides of the invention are also encompassed by the invention. Polynucleotides encoding these polypeptides are also encompassed by the invention.

Also as mentioned above, even if deletion of one or more amino acids from the C terminus of a protein results in modification or loss of one or more biological functions of the protein (e.g., ability to induce hematopoiesis), other functional activities (e.g., biological activities, ability to multimerize, ability to bind receptors, ability to activate receptors, ability to bind and block receptor activation, ability to inhibit receptor activation without binding (e.g., as a dominant negative inhibitor of oligomeric complexes), ability to generate antibodies, ability to bind antibodies) may still be retained. For example the ability of the shortened polypeptide to induce and/or bind to antibodies which recognize the complete or mature forms of the polypeptide generally will be retained when less than the majority of the residues of the complete or mature polypeptide are removed from the C terminus. Whether a particular polypeptide lacking C terminal residues of a complete polypeptide retains such immunologic activities can readily be determined by routine methods described herein and otherwise known in the art. It is not unlikely that a polypeptide with a large number of deleted C terminal amino acid residues may retain some biological or immunogenic activities. In fact, peptides composed of as few as six amino acid residues may often evoke an immune response.

Accordingly, the present invention further provides polypeptides having one or more residues deleted from the carboxyl terminus of the amino acid sequence of the polypeptide shown in FIGS. 3A-B (SEQ ID NO:21), as described by the general formula 1-n, where n is an integer from 6 to 135, where n corresponds to the position of the amino acid residue identified in SEQ ID NO:21. More in particular, the invention provides polynucleotides encoding polypeptides comprising, or alternatively consisting of, an amino acid sequence selected from the group: M-1 to Q-135; M-1 to R-134; M-1 to D-133; M-1 to P-132; M-1 to L-131; M-1 to V-130; M-1 to T-129; M-1 to T-128; M-1 to V-127; M-1 to P-126; M-1 to I-125; M-1 to P-124; M-1 to Y-123; M-1 to E-122; M-1 to L-121; M-1 to A-120; M-1 to N-119; M-1 to C-118; M-1 to D-117; M-1 to D-116; M-1 to L-115; M-1 to L-114; M-1 to F-113; M-1 to V-112; M-1 to L-111; M-1 to D-110; M-1 to R-109; M-1 to R-108; M-1 to C-107; M-1 to F-106; M-1 to S-105; M-1 to N-104; M-1 to M-103; M-1 to I-102; M-1 to T-101; M-1 to Y-100; M-1 to L-99; M-1 to K-98; M-1 to R-97; M-1 to A-96; M-1 to K-95; M-1 to D-94; M-1 to K-93; M-1 to L-92; M-1 to S-91; M-1 to D-90; M-1 to V-89; M-1 to Q-88; M-1 to A-87; M-1 to V-86; M-1 to K-85; M-1 to W-84; M-1 to C-83; M-1 to P-82; M-1 to P-81; M-1 to S-80; M-1 to A-79; M-1 to V-78; M-1 to F-77; M-1 to D-76; M-1 to R-75; M-1 to L-74; M-1 to K-73; M-1 to D-72; M-1 to L-71; M-1 to V-70; M-1 to C-69; M-1 to Y-68; M-1 to N-67; M-1 to H-66; M-1 to I-65; M-1 to D-64; M-1 to L-63; M-1 to Y-62; M-1 to L-61; M-1 to R-60; M-1 to P-59; M-1 to L-58; M-1 to Y-57; M-1 to R-56; M-1 to V-55; M-1 to C-54; M-1 to P-53; M-1 to E-52; M-1 to S-51; M-1 to P-50; M-1 to E-49; M-1 to S-48; M-1 to V-47; M-1 to Q-46; M-1 to L-45; M-1 to L-44; M-1 to N-43; M-1 to F-42; M-1 to D-41; M-1 to R-40; M-1 to T-39; M-1 to I-38; M-1 to E-37; M-1 to Q-36; M-1 to S-35; M-1 to L-34; M-1 to A-33; M-1 to R-32; M-1 to M-31; M-1 to R-30; M-1 to S-29; M-1 to Y-28; M-1 to C-27; M-1 to T-26; M-1 to P-25; M-1 to P-24; M-1 to T-23; M-1 to P-22; M-1 to R-21; M-1 to A-20; M-1 to A-19; M-1 to P-18; M-1 to A-17; M-1 to G-16; M-1 to A-15; M-1 to L-14; M-1 to L-13; M-1 to L-12; M-1 to L-11; M-1 to L-10; M-1 to V-9; M-1 to P-8; and M-1 to L-7 of SEQ ID NO:21. Polypeptides encoded by these polynucleotides are also encompassed by the invention. Moreover, fragments and variants of these polypeptides (such as, for example, fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides, or the complement thereof) are encompassed by the invention. Antibodies that bind polypeptides of the invention are also encompassed by the invention. Polynucleotides encoding these polypeptides are also encompassed by the invention.

In addition, any of the above listed N- or C-terminal deletions can be combined to produce a N- and C-terminal deleted polypeptide. The invention also provides polypeptides comprising, or alternatively consisting of, one or more amino acids deleted from both the amino and the carboxyl termini, which may be described generally as having residues m-n of SEQ ID NO:21, where n and m are integers as described above. More in particular, the invention provides polynucleotides encoding polypeptides comprising, or alternatively consisting of, an amino acid sequence selected from the group: M-1 to A-15; R-2 to G-16; T-3 to A-17; P-4 to P-18; G-5 to A-19; P-6 to A-20; L-7 to R-21; P-8 to P-22; V-9 to T-23; L-10 to P-24; L-11 to P-25; L-12 to T-26; L-13 to C-27; L-14 to Y-28; A-15 to S-29; G-16 to R-30; A-17 to M-31; P-18 to R-32; A-19 to A-33; A-20 to L-34; R-21 to S-35; P-22 to Q-36; T-23 to E-37; P-24 to I-38; P-25 to T-39; T-26 to R-40; C-27 to D-41; Y-28 to F-42; S-29 to N-43; R-30 to L-44; M-31 to L-45; R-32 to Q-46; A-33 to V-47; L-34 to S-48; S-35 to E-49; Q-36 to P-50; E-37 to S-51; I-38 to E-52; T-39 to P-53; R-40 to C-54; D-41 to V-55; F-42 to R-56; N-43 to Y-57; L-44 to L-58; L-45 to P-59; Q-46 to R-60; V-47 to L-61; S-48 to Y-62; E-49 to L-63; P-50 to D-64; S-51 to I-65; E-52 to H-66; P-53 to N-67; C-54 to Y-68; V-55 to C-69; R-56 to V-70; Y-57 to L-71; L-58 to D-72; P-59 to K-73; R-60 to L-74; L-61 to R-75; Y-62 to D-76; L-63 to F-77; D-64 to V-78; I-65 to A-79; H-66 to S-80; N-67 to P-81; Y-68 to P-82; C-69 to C-83; V-70 to W-84; L-71 to K-85; D-72 to V-86; K-73 to A-87; L-74 to Q-88; R-75 to V-89; D-76 to D-90; F-77 to S-91; V-78 to L-92; A-79 to K-93; S-80 to D-94; P-81 to K-95; P-82 to A-96; C-83 to R-97; W-84 to K-98; K-85 to L-99; V-86 to Y-100; A-87 to T-101; Q-88 to I-102; V-89 to M-103; D-90 to N-104; S-91 to S-105; L-92 to F-106; K-93 to C-107; D-94 to R-108; K-95 to R-109; A-96 to D-110; R-97 to L-111; K-98 to V-112; L-99 to F-113; Y-100 to L-114; T-101 to L-115; I-102 to D-116; M-103 to D-117; N-104 to C-118; S-105 to N-119; F-106 to A-120; C-107 to L-121; R-108 to E-122; R-109 to Y-123; D-110 to P-124; L-111 to I-125; V-112 to P-126; F-113 to V-127; L-114 to T-128; L-115 to T-129; D-116 to V-130; D-117 to L-131; C-118 to P-132; N-119 to D-133; A-120 to R-134; L-121 to Q-135; and E-122 to R-136 of SEQ ID NO:21. Polynucleotides encoding these polypeptides are also encompassed by the invention. Moreover, fragments and variants of these polypeptides (such as, for example, fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides, or the complement thereof) are encompassed by the invention. Antibodies that bind polypeptides of the invention are also encompassed by the invention. Polynucleotides encoding these polypeptides are also encompassed by the invention.

The present invention is also directed to proteins containing polypeptides at least 80%, 85%, 90%, 92%, 93%, 94%, 95%, 96%, 97%, 98% or 99% identical to a polypeptide sequence set forth herein as m-n. In preferred embodiments, the application is directed to proteins containing polypeptides at least 80%, 85%, 90%, 95%, 96%, 97%, 98% or 99% identical to polypeptides having the amino acid sequence of the specific N and C terminal deletions recited herein. Polynucleotides encoding these polypeptides are also encompassed by the invention.

Also included are polynucleotide sequences encoding a polypeptide consisting of a portion of the complete amino acid sequence encoded by a cDNA clone contained in ATCC Deposit No. 97975 (deposited Apr. 4, 1997) and ATCC Deposit No. 209081 (deposited May 29, 1997), where this portion excludes any integer of amino acid residues from 1 to about 606 (end of protein minus six) amino acids from the amino terminus of the complete amino acid sequence encoded by a cDNA clone contained in ATCC Deposit No. 97975 and 209081, or any integer of amino acid residues from 6 to about 612 amino acids from the carboxyl terminus, or any combination of the above amino terminal and carboxyl terminal deletions, of the complete amino acid sequence encoded by the cDNA clone contained in ATCC Deposit No. 97975 and 209081. Polypeptides encoded by these polynucleotides also are encompassed by the invention. Moreover, fragments and variants of these polypeptides (such as, for example, fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides, or the complement thereof) are encompassed by the invention. Antibodies that bind polypeptides of the invention are also encompassed by the invention. Polynucleotides encoding these polypeptides are also encompassed by the invention.

The gene encoding the disclosed cDNA is believed to reside on chromosome 4. Accordingly, polynucleotides related to this invention have uses that include, but are not limited to, serving as probes or primers in chromosome identification, chromosome mapping, and linkage analysis for chromosome 4.

This gene is expressed primarily in fetal liver and fetal spleen.

Polynucleotides and polypeptides of the invention are useful as reagents for differential identification of the tissue(s) or cell type(s) present in a biological sample and for diagnosis of diseases and conditions which include, but are not limited to, hematopoietic, immunological, developmental, and/or hepatic disorders. Similarly, polypeptides and antibodies directed to these polypeptides are useful in providing immunological probes for differential identification of the tissue(s) or cell type(s). For a number of disorders of the above tissues or cells, particularly of the immune and hematopoetic systems, expression of this gene at significantly higher or lower levels may be routinely detected in certain tissues or cell types (e.g., hematopoietic, immune, hepatic, developmental, and cancerous and wounded tissues) or bodily fluids (e.g., lymph, amniotic fluid, bile, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. For example, polynucleotides and polypeptides of the invention, polynucleotide and polypeptide fragments, and polynucleotide and polypeptide variants, and antibodies directed to these polypeptides are useful for identifying, selecting, targeting and/or stimulating proliferation of hematopoietic stem cells (a.k.a., hematopoietic progenitor cells).

Cytokines typically exert their respective biochemical and physiological effects by binding to specific receptor molecules. Receptor binding then stimulates specific signal transduction pathways (Kishimoto, T., et al., Cell 76:253 262 (1994)). The specific interactions of cytokines with their receptors are often the primary regulators of a wide variety of cellular processes including activation, proliferation, and differentiation (Arai, K. I, et al., Ann. Rev. Biochem. 59:783 836 (1990); Paul, W. E. and Seder, R. A., Cell 76:241 251 (1994)).

The polynucleotides and polypeptides of this invention may be useful for the diagnosis and treatment of a variety of immune system and hematopoietic disorders, pathologies, and/or deficiencies. For example, this gene and/or gene product may play a role in regulating the proliferation; survival; differentiation; and/or activation of hematopoietic cell lineages, including blood stem cells. Furthermore, polypeptides of this invention may be involved in the regulation of cytokine production, antigen presentation, or other processes useful for treatment of cancer, particularly leukemia (e.g., by boosting immune responses, suppressing hyperproliferative activity, or enhancing recovery of healthy hematopoietic cell populations during or following chemotherapy). Moreover, the polynucleotides and polypeptides of this invention, as well as antibodies against the polypeptides of this invention, may be useful for treating immunological and hematopoietic disorders; such as for examples, arthritis, asthma, immunodeficiency diseases (e.g. AIDS), leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, demyelination, systemic lupus erythematosis, drug induced hemolytic anemia, rheumatoid arthritis, Sjogren's disease, and scleroderma. Moreover, the polypeptide of this invention represents a secreted factor that is likely to have activity in stimulating the differentiation of blood cells, or recruiting immune and hematopoietic cells to sites of injury. Thus, this polypeptide is thought to be useful in the expansion of stem cells and committed progenitors of various blood lineages, and in the differentiation and/or proliferation of various cell types.

Preferred polypeptides of the present invention comprise, or alternatively consist of, one or more of the immunogenic epitopes shown in SEQ ID NO:21 as residues: Met-1 to Leu-7, Pro-18 to Cys-27, Ser-29 to Ser-35, Glu-37 to Asp-41, Gln-46 to Cys-54, Asp-72 to Val-78, Pro-81 to Trp-84, Ser-91 to Lys-98, Asn-104 to Leu-111, Asp-116 to Leu-121, and Val-130 to Arg-136. Polynucleotides encoding said polypeptides are also encompassed by the invention. Antibodies that bind said epitopes or other polypeptides of the invention are also encompassed.

The tissue distribution of this gene in fetal liver and spleen indicates that the gene could be important for the treatment or detection of immune or hematopoietic disorders including arthritis, leukemia, and immunodeficiency diseases. Moreover, the protein product of this gene is useful for the treatment and diagnosis of hematopoetic related disorders such as anemia, pancytopenia, leukopenia, thrombocytopenia or leukemia since stromal cells are important in the production of cells of hematopoietic lineages. The uses include bone marrow cell ex vivo culture, bone marrow transplantation, bone marrow reconstitution, radiotherapy or chemotherapy of neoplasia. The gene product may also be involved in lymphopoiesis, therefore, it can be used in immune disorders such as infection, inflammation, allergy, immunodeficiency etc. In addition, this gene product may have commercial utility in the expansion of stem cells and committed progenitors of various blood lineages, and in the differentiation and/or proliferation of various cell types. Moreover, expression within fetal tissue indicates that this protein may play a role in the regulation of cellular division, and may show utility in the diagnosis and treatment of cancer and other proliferative disorders. Similarly, developmental tissues rely on decisions involving cell differentiation and/or apoptosis in pattern formation. Thus, this protein may also be involved in apoptosis or tissue differentiation and could again be useful in cancer therapy. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:20 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 982 of SEQ ID NO:20, b is an integer of 15 to 996, where both a and b correspond to the positions of nucleotide residues shown in SEQ ID NO:20, and where b is greater than or equal to a+14.

Features of Protein Encoded by Gene No: 6

The translation product of this gene is homologous to the *Clostridium perfringens* enterotoxin (CPE) receptor gene product and shares sequence homology with a human ORF specific to prostate and a glycoprotein specific to oligodendrocytes, both of which are tissue specific proteins. See e.g., Katahira et al. J. Cell Biol. 136(6):1239-1247 (1997). PMID: 9087440; UI: 97242441.

In specific embodiments, polypeptides of the invention comprise, or alternatively consist of, the following amino acid sequences:

TMASMGLQV(SEQ ID NO: 30), KSWMMLWAVQDTGTITIRPANR NTTPATIMVLALALSSSRQLVHLPPTTDSSTPRAATMMLMMTRARAAC RSCGSASSESYTLHCIWPVLCTTQFIHRPSQMVCEVTMLLPMKAVTRH MGSAQHSMTASQPRTASAMPITCSPMEAIVQRPRELRTWKAEGIRLWG P(SEQ ID NO: 31), LQVMGIALAVLGWLAVMLCCALPMWRVT (SEQ ID NO: 32), SNIVTSQTIWEGLWMNCVVQST(SEQ ID NO: 33), QMQCKVYDSLLALPQDLQ (SEQ ID NO: 34), KCT NCLEDESAKAKTMIV(SEQ ID NO: 35), GVVFLLAGLMVIVPVS WTAHNIIQDFYNPLVA (SEQ ID NO: 36), and/or CCNCPPR -continued

TDKPY (SEQ ID NO: 37).

Moreover, fragments and variants of these polypeptides (such as, for example, fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides) are encompassed by the invention. Antibodies that bind polypeptides of the invention are also encompassed by the invention. Polynucleotides encoding these polypeptides are also encompassed by the invention.

The gene encoding the disclosed cDNA is believed to reside on chromosome 7. Accordingly, polynucleotides related to this invention are useful as a marker in linkage analysis for chromosome 7.

This gene is expressed primarily in pancreas tumor and ulcerative colitis, and to a lesser extent in several tumors and normal tissues.

Polynucleotides and polypeptides of the invention are useful as reagents for differential identification of the tissue(s) or cell type(s) present in a biological sample and for diagnosis of diseases and conditions which include, but are not limited to, metabolic, gastrointestinal, or proliferative disorders, such as pancreatic disorders, ulcerative colitis, tumors and food poisoning. Similarly, polypeptides and antibodies directed to these polypeptides are useful in providing immunological probes for differential identification of the tissue(s) or cell type(s). For a number of disorders of the above tissues or cells, particularly of the digestive system or tumorigenic system, expression of this gene at significantly higher or lower levels may be routinely detected in certain tissues or cell types (e.g., metabolic, gastrointestinal, pancreatic, and cancerous and wounded tissues) or bodily fluids (e.g., lymph, bile, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Predicted epitopes include those comprising a sequence shown in SEQ ID NO:29 as residues: Gly-147 to Met-152, Cys-177 to Lys-188.

The tissue distribution in pancreas, combined with the homology to a prostate and oligodendrocyte-specific protein, indicates that the protein product of this gene is useful as a marker for the diagnosis or treatment of disorders in pancreas, ulcerative colitis, and tumors. Furthermore, identity to the human receptor for *Clostridium perfringenes* enterotoxin indicates that the soluble portion of this receptor could be used in the treatment of food poisoning associated with *Clostridia perfringens* by blocking the activity of the perfringens enterotoxin. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:28 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1691 of SEQ ID NO:28, b is an integer of 15 to 1705, where both a and b correspond to the positions of nucleotide residues shown in SEQ ID NO:28, and where b is greater than or equal to a+14.

Features of Protein Encoded by Gene No: 7

The translation product of this gene shares sequence homology with alpha 3 type IX collagen, which is thought to be important in hyaline cartilage formation via its ability to uptake inorganic sulfate by cells (See Genbank Accession No. gi|975657).

In specific embodiments, polypeptides of the invention comprise, or alternatively consists of, an amino acid sequence selected from the group:

(SEQ ID NO: 40)
SLRRPRSAAXQTLTTFLSSVSSASSSALPGSREPCDPRAPPPPRSGSAAS
CCSCCCSCPRRRAPLRSPRGSKRRIRQREVVDLYNGMCLQGPAGVPGRDG
SPGANGIPGTPGIPGRDGFKGEKGECLRESFEESWTPNYKQCSWSSLNYG
IDLGKIAECTFTKMRSNSALRVLFSGSLRLKCRNACCQRWYFTFNGAECS
GPLPIEAIIYLDQGSPEMNSTINIHRTSSVEGLCEGIGAGLVDVAIWVGT
CSDYPKGDASTGWNSVSRIIIEELPK, (SEQ ID NO: 41)
SLRRPRSAAXQTLTTFLSSVSSASSSALPGSREPCDPRAPPPPRSGSAAS
CCSCCCSCPRR, (SEQ ID NO: 42)
RAPLRSPRGSKRRIRQREVVDLYNGMCLQGPAGVPGRDGSPGANGIPGTP
GI, (SEQ ID NO: 43)
TPGIPGRDGFKGEKGECLRESFEESWTPNYKQCSWSSLNYGIDLGKIAEC
TF, (SEQ ID NO: 44)
FTKMRSNSALRVLFSGSLRLKCRNACCQRWYFTFNGAECSGPLPIEAIIY
LDQGSPEMNSTINIHR,
and/or (SEQ ID NO: 45)
RTSSVEGLCEGIGAGLVDVAIWVGTCSDYPKGDASTGWNSVSRIIIEELP
K.

Moreover, fragments and variants of these polypeptides (such as, for example, fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides) are encompassed by the invention. Antibodies that bind polypeptides of the invention are also encompassed by the invention. Polynucleotides encoding these polypeptides are also encompassed by the invention.

This gene is expressed primarily in smooth muscle, and to a lesser extent in synovial tissue.

Polynucleotides and polypeptides of the invention are useful as reagents for differential identification of the tissue(s) or cell type(s) present in a biological sample and for diagnosis of diseases and conditions which include, but are not limited to, dwarfism, spinal deformation, and specific joint abnormalities as well as chondrodysplasias, i.e. spondyloepiphyseal dysplasia congenita, familial osteoarthritis, Atelosteogenesis type II, metaphyseal chondrodysplasia type Schmid and autoimmune disorders. Similarly, polypeptides and antibodies directed to these polypeptides are useful in providing immunological probes for differential identification of the tissue(s) or cell type(s). For a number of disorders of the above tissues or cells, particularly of the skeletal system, expression of this gene at significantly higher or lower levels may be routinely detected in certain tissues or cell types (e.g. muscle, synovial tissues, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in smooth muscle, and homology to alpha 3 type IX collagen indicates that the protein product of this gene is useful for the treatment and diagnosis of diseases associated with the mutation in this gene which leads to the many different types of chondrodysplasias. By the use of this product, the abnormal growth and development of bones of the limbs and spine could be detected or treated in utero, since the protein or polypeptides thereof could affect epithelial cells early in development, and later the chondrocytes of the developing craniofacial structure. In addition, the expression of this gene product in synovium would suggest a role in the detection and treatment of disorders and conditions affecting the skeletal system, in particular osteoporosis as well as disorders afflicting connective tissues (e.g. arthritis, trauma, tendonitis, chrondomalacia and inflammation), such as in the diagnosis or treatment of various autoimmune disorders such as rheumatoid arthritis, lupus, scleroderma, and dermatomyositis as well as dwarfism, spinal deformation, and specific joint abnormalities as well as chondrodysplasias (i.e. spondyloepiphyseal dysplasia congenita, familial osteoarthritis, Atelosteogenesis type II, metaphyseal chondrodysplasia type Schmid). Moreover, the expression within smooth muscle indicates t that polynucleotides and polypeptides corresponding to this gene are useful for the treatment, detection, and/or prevention of a variety of vascular disorders, which include, but are not limited to, atherosclerosis, embolism, stroke, aneurysm, or microvascular disease. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:38 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1274 of SEQ ID NO:38, b is an integer of 15 to 1288, where both a and b correspond to the positions of nucleotide residues shown in SEQ ID NO:38, and where b is greater than or equal to a+14.

Features of Protein Encoded by Gene No: 8

The translation product of this gene shares sequence homology with both the RIC and MAT8 proteins (mouse), which are thought to be important in regulating chloride conductance in cells by modulating the response mediated by cAMP and protein kinase C to extracellular signals.

In specific embodiments, polypeptides of the invention comprise, or alternatively consist of, the following amino acid sequences:

GTSLDAAATAASLSPRGCRLRTPSSD (SEQ ID NO: 52), QIQRH
TRAPKQLIPLMTPRRSLRDHPQAQTSRQTPRPSSHLVFMRMTPSSMMNT
PSGNGGCWSQLCCSSQASSSSPVASAGSCPGYAGIIAGESIRNRS
(SEQ ID NO: 53), PRRSLRDHPQAQTSRQTPRPSSHLVFM (SEQ

-continued

ID NO: 54), THPPETGAVGRSCAVHHRHHHPHQWQVQAAVPVMPESLQVSPSETGADNXLGTRRPSPLPAHRAQPPASPRRAWPEREDTDDEAGARAAGPSLLPPPTLPAPEGYLAPWGLSLKLSPLLRQKVKHCGLC (SEQ ID NO: 55), PESLQVSPSETGADNXLGTRRPSPLPAHRAQPPASP (SEQ ID NO: 56), GTAPKAPGSLQGRAGLGEVGDSDRQPWLQLHHLCLPSLARLFEGMQEAGHGELAGGLVFGCPAGCQLLFLMDSPAMIPA (SEQ ID NO: 57), GEVGDSDRQPWLQLHHLCLPSLARLFEGMQEAGH (SEQ ID NO: 58), GSGGLSGRLCLGMVSQRASWCHQWDELLWCSCVSLDLSLEAHPFLPVAGSGSGVVVFHQQARLGLERWAGVLCRLHLGLVSGPECP (SEQ ID NO: 59), and/or QWDELLWCSCVSLDLSLEAHPFLPVAGSGSGVVVFHQQARL (SEQ ID NO: 60).

Moreover, fragments and variants of these polypeptides (such as, for example, fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides) are encompassed by the invention. Antibodies that bind polypeptides of the invention are also encompassed by the invention. Polynucleotides encoding these polypeptides are also encompassed by the invention.

The gene encoding the disclosed cDNA is believed to reside on chromosome 19. Accordingly, polynucleotides related to this invention are useful as a marker in linkage analysis for chromosome 19.

This gene is expressed primarily in amniotic cells and hematopoietic cells including macrophages, neutrophils, T cells, TNF induced aortic endothelium, and to a lesser extent in testes, TNF induced epithelial cells, and smooth muscle.

Polynucleotides and polypeptides of the invention are useful as reagents for differential identification of the tissue(s) or cell type(s) present in a biological sample and for diagnosis of diseases and conditions which include, but are not limited to, immune or hematopoietic disorders, particularly inflammatory responses mediated by T cells, macrophages, and/or neutrophils, particularly those involving TNF, and also cancer. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., immune, hematopoietic, developmental, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Predicted epitopes include those comprising a sequence shown in SEQ ID NO:47 as residues: Thr-19 to Ala-33, Leu-54 to Asp-82, Pro-89 to Ala-97, Pro-100 to Lys-125, Ser-127 to Phe-135, Gly-164 to Leu-169, Cys-173 to Arg-178.

The tissue distribution in hematopoietic cells, combined with the homology to the RIC and mat-8 genes, indicates that the protein product of this gene is useful for modifying inflammatory responses to cytokines such as TNF, and thus modifying the duration and/or severity of inflammation. Polynucleotides and polypeptides derived from this gene are thought to be useful in the diagnosis and treatment of cancer. The protein product of this gene is useful for the treatment and diagnosis of hematopoetic related disorders such as anemia, pancytopenia, leukopenia, thrombocytopenia or leukemia, since stromal cells are important in the production of cells of hematopoietic lineages. The uses include bone marrow cell ex vivo culture, bone marrow transplantation, bone marrow reconstitution, radiotherapy or chemotherapy of neoplasia. The gene product may also be involved in lymphopoiesis, therefore, it can be used in immune disorders such as infection, inflammation, allergy, immunodeficiency etc. In addition, this gene product may have commercial utility in the expansion of stem cells and committed progenitors of various blood lineages, and in the differentiation and/or proliferation of various cell types. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:46 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 927 of SEQ ID NO:46, b is an integer of 15 to 941, where both a and b correspond to the positions of nucleotide residues shown in SEQ ID NO:46, and where b is greater than or equal to a+14.

Features of Protein Encoded by Gene No: 9

In specific embodiments, polypeptides of the invention comprise, or alternatively consists of, an amino acid sequence selected from the group:

MRILQLILLALATGLVGGETRIIKGFECKLHSQPWQAALFEKTRLLCGATLIAPRWLLTAAHCLKPRYIVHLGQHNLQKEEGCEQTRTATESFPHPGFNNSLPNKDHRNDIMLVKMASPVSITWAVRPLTLSSRCVTAGTSCSFPAGAARPDPSYACLTPCDAPTSPSLSTRSVRTPTPATSQTPWCVPACRKGARTPARVTPGALWSVTSLFKALSPGARIRVRSPESLVSTRKSANMWTGSRRR (SEQ ID NO: 67); ETRIIKGFECKLHSQPWQAALFEKTRLLCGATLIAPRWLLTAAHCLKPRYIVHLGQHNLQKEEGCEQTRTATESFPHPGFNNSLPNKDHRNDIMLVKMASPVSITWAVRPLTLSSRCVTAGTSCSFPAGAARPDPSYACLTPCDAPTSPSLSTRSVRTPTPATSQTPWCVPACRKGARTPARVTPGALWSVTSLFKALSPGARIRVRSPESLVSTRKSANMWTGSRRR (SEQ ID NO: 68); and/or CKLHSQPWQAALFEKTRLLCGATLIAPRWLLTAAHCLKPRYIVHLGQHNLQKEEGCEQTRTATESFPHPGFNNS (SEQ ID NO: 69).

Moreover, fragments and variants of these polypeptides (such as, for example, fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides) are encompassed by the invention. Antibodies that bind polypeptides of the invention are also encompassed by the invention. Polynucleotides encoding these polypeptides are also encompassed by the invention.

The translation product of this gene shares sequence homology with neuropsin, a novel serine protease, which is thought to be important in modulating extracellular signaling pathways in the brain. Owing to the structural similarity to other serine proteases, the protein products of this gene are expected to have serine protease activity which may be assayed by methods known in the art and described elsewhere herein. Moreover, this protein has been shown to also have homology to PSA (prostate specific antigen). PSA is a serum marker for prostate cancer and it is a member of the kallikrein family. The members of the kallikrein family are secreted serine proteases and some of them are good tissue specific markers. This new member of the kallikrein family has been detected twice in endometrial tumor cDNA library and therefore is a good candidate as a serum marker for endometrial tumor.

This gene is expressed primarily in endometrial tumor, and to a lesser extent, in colon cancer, benign hypertrophic prostate, and thymus.

Polynucleotides and polypeptides of the invention are useful as reagents for differential identification of the tissue(s) or cell type(s) present in a biological sample and for diagnosis of diseases and conditions which include, but are not limited to, reproductive, immune, or endocrine disorders, particularly cancers of the endometrium or colon and benign hypertrophy of the prostate. Similarly, polypeptides and antibodies directed to these polypeptides are useful in providing immunological probes for differential identification of the tissue(s) or cell type(s). For a number of disorders of the above tissues or cells, particularly of the urogenital or reproductive systems, expression of this gene at significantly higher or lower levels may be routinely detected in certain tissues or cell types (e.g., reproductive, immune, endocrine, gastrointestinal, and cancerous and wounded tissues) or bodily fluids (e.g., lymph, serum, seminal fluid, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Predicted epitopes include those comprising a sequence shown in SEQ ID NO:62 as residues: Glu-27 to Trp-35, Leu-77 to Ala-89, Pro-96 to Asn-109, Ser-149 to Arg-156, Gln-172 to Ile-182, Glu-193 to Gly-204, Glu-245 to Asn-250.

The tissue distribution in proliferative reproductive tissues, combined with the homology to serine proteases indicates that the protein product of this gene is useful for diagnosing, treating, and/or preventing hyperproliferative disorders such as cancer of the endometrium or colon and hyperplasia of the prostate. Similarly, expression within cellular sources marked by proliferating cells indicates that this protein may play a role in the regulation of cellular division, and may show utility in the diagnosis and treatment of cancer and other proliferative disorders. Similarly, developmental tissues rely on decisions involving cell differentiation and/or apoptosis in pattern formation. Thus this protein may also be involved in apoptosis or tissue differentiation and could again be useful in cancer therapy. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:61 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a−b, where a is any integer between 1 to 1278 of SEQ ID NO:61, b is an integer of 15 to 1292, where both a and b correspond to the positions of nucleotide residues shown in SEQ ID NO:61, and where b is greater than or equal to a+14.

Features of Protein Encoded by Gene No: 10

The translation product of this gene shares sequence homology with tenascin, which is thought to be important in development. The translation product of this gene is believed to be a ligand of the fibroblast growth factor family. FGF ligand activity is known in the art and can be assayed by methods known in the art and disclosed elsewhere herein.

Northern analysis indicates that a 2.5 kb band is expressed in brain and lung. It has also been discovered that this gene is expressed in endometrial tumor, synovial sarcoma, pancreas tumor, fetal lung, retinal, and immune tissues (e.g., bone marrow)

Polynucleotides and polypeptides of the invention are useful as reagents for differential identification of the tissue(s) or cell type(s) present in a biological sample and for diagnosis of diseases and conditions which include, but are not limited to, cancers, growth disorders of the brain and lung. Similarly, polypeptides and antibodies directed to these polypeptides are useful in providing immunological probes for differential identification of the tissue(s) or cell type(s). For a number of disorders of the above tissues or cells, particularly of the cancer tissues, brain, lung, expression of this gene at significantly higher or lower levels may be routinely detected in certain tissues or cell types (e.g. brain, lung, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Predicted epitopes include those comprising a sequence shown in SEQ ID NO:71 as residues: Gly-29 to Glu-34, Arg-71 to Arg-76, Thr-176 to Cys-182, Gly-184 to Glu-199. As a preferred embodiment, antibodies that bind said epitopes are encompassed by the invention and may be useful as a cancer diagnostic and/or an agonist/antagonist of the polypeptides of the invention.

Fragments and variants of the polypeptide encoded by this gene (such as, for example, fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides, or the complement thereof) are encompassed by the invention). Antibodies that bind polypeptides of the invention are also encompassed by the invention. Polynucleotides encoding these polypeptides are also encompassed by the invention. Antibodies that bind polypeptides of the invention would be useful as a cancer diagnostic.

Preferred polypeptide fragments of the invention comprise, or alternatively consist of, the secreted protein having a continuous series of deleted residues from the amino or the carboxy terminus, or both. Particularly, N-terminal deletions of the polypeptide can be described by the general formula m−379 where m is an integer from 2 to 371, where m corresponds to the position of the amino acid residue identified in SEQ ID NO:71. More in particular, the invention provides polynucleotides encoding polypeptides comprising, or alternatively consisting of, an amino acid sequence selected from the group: A-2 to W-379; R-3 to W-379; R-4 to W-379; S-5 to W-379; A-6 to W-379; F-7 to W-379; P-8 to W-379; A-9 to W-379; A-10 to W-379; A-11 to W-379; L-12 to W-379; W-13 to W-379; L-14 to W-379; W-15 to W-379; S-16 to W-379; I-17 to W-379; L-18 to W-379; L-19 to W-379; C-20 to W-379; L-21 to W-379; L-22 to W-379; A-23 to W-379; L-24 to W-379; R-25 to W-379; A-26 to W-379; E-27 to W-379; A-28 to W-379; G-29 to W-379; P-30 to W-379; P-31 to W-379; Q-32 to W-379; E-33 to W-379; E-34 to W-379; S-35 to W-379; L-36 to W-379; Y-37 to W-379; L-38 to W-379; W-39 to W-379; I-40 to W-379; D-41 to W-379; A-42 to W-379; H-43 to W-379; Q-44 to W-379; A-45 to W-379; R-46 to W-379; V-47 to W-379; L-48 to W-379; I-49 to W-379; G-50 to W-379; F-51 to W-379; E-52 to W-379; E-53 to W-379; D-54 to W-379; I-55 to W-379; L-56 to W-379; I-57 to W-379; V-58 to W-379; S-59 to W-379; E-60 to W-379; G-61 to W-379; K-62 to W-379; M-63 to W-379; A-64 to W-379; P-65 to W-379; F-66 to W-379; T-67 to W-379; H-68 to W-379; D-69 to W-379; F-70 to W-379; R-71 to W-379; K-72 to W-379; A-73 to W-379; Q-74 to W-379; Q-75 to W-379; R-76 to W-379; M-77 to W-379; P-78 to W-379; A-79 to W-379; I-80 to W-379; P-81 to W-379; V-82 to W-379; N-83 to W-379; I-84 to W-379; H-85 to W-379; S-86 to W-379; M-87 to W-379; N-88 to W-379; F-89 to W-379; T-90 to W-379; W-91 to W-379; Q-92 to W-379; A-93 to W-379; A-94 to W-379; G-95 to W-379; Q-96 to W-379; A-97 to W-379; E-98 to W-379; Y-99 to W-379; F-100 to W-379; Y-101 to W-379; E-102 to W-379; F-103 to W-379; L-104 to W-379; S-105 to W-379; L-106 to W-379; R-107 to W-379; S-108 to W-379; L-109 to W-379; D-110 to W-379; K-111 to W-379; G-112 to W-379; I-113 to W-379; M-114 to W-379; A-115 to W-379; D-116 to W-379; P-117 to W-379; T-118 to W-379; V-119 to W-379; N-120 to W-379; V-121 to W-379; P-122 to W-379; L-123 to W-379; L-124 to W-379; G-125 to W-379; T-126 to W-379; V-127 to W-379; P-128 to W-379; H-129 to W-379; K-130 to W-379; A-131 to W-379; S-132 to W-379; V-133 to W-379; V-134 to W-379; Q-135 to W-379; V-136 to W-379; G-137 to W-379; F-138 to W-379; P-139 to W-379; C-140 to W-379; L-141 to W-379; G-142 to W-379; K-143 to W-379; Q-144 to W-379; D-145 to W-379; G-146 to W-379; V-147 to W-379; A-148 to W-379; A-149 to W-379; F-150 to W-379; E-151 to W-379; V-152 to W-379; D-153 to W-379; V-154 to W-379; I-155 to W-379; V-156 to W-379; M-157 to W-379; N-158 to W-379; S-159 to W-379; E-160 to W-379; G-161 to W-379; N-162 to W-379; T-163 to W-379; I-164 to W-379; L-165 to W-379; Q-166 to W-379; T-167 to W-379; P-168 to W-379; Q-169 to W-379; N-170 to W-379; A-171 to W-379; I-172 to W-379; F-173 to W-379; F-174 to W-379; K-175 to W-379; T-176 to W-379; C-177 to W-379; Q-178 to W-379; Q-179 to W-379; A-180 to W-379; E-181 to W-379; C-182 to W-379; P-183 to W-379; G-184 to W-379; G-185 to W-379; C-186 to W-379; R-187 to W-379; N-188 to W-379; G-189 to W-379; G-190 to W-379; F-191 to W-379; C-192 to W-379; N-193 to W-379; E-194 to W-379; R-195 to W-379; R-196 to W-379; I-197 to W-379; C-198 to W-379; E-199 to W-379; C-200 to W-379; P-201 to W-379; D-202 to W-379; G-203 to W-379; F-204 to W-379; H-205 to W-379; G-206 to W-379; P-207 to W-379; H-208 to W-379; C-209 to W-379; E-210 to W-379; K-211 to W-379; A-212 to W-379; L-213 to W-379; C-214 to W-379; T-215 to W-379; P-216 to W-379; R-217 to W-379; C-218 to W-379; M-219 to W-379; N-220 to W-379; G-221 to W-379; G-222 to W-379; L-223 to W-379; C-224 to W-379; V-225 to W-379; T-226 to W-379; P-227 to W-379; G-228 to W-379; F-229 to W-379; C-230 to W-379; I-231 to W-379; C-232 to W-379; P-233 to W-379; P-234 to W-379; G-235 to W-379; F-236 to W-379; Y-237 to W-379; G-238 to W-379; V-239 to W-379; N-240 to W-379; C-241 to W-379; D-242 to W-379; K-243 to W-379; A-244 to W-379; N-245 to W-379; C-246 to W-379; S-247 to W-379; T-248 to W-379; T-249 to W-379; C-250 to W-379; F-251 to W-379; N-252 to W-379; G-253 to W-379; G-254 to W-379; T-255 to W-379; C-256 to W-379; F-257 to W-379; Y-258 to W-379; P-259 to W-379; G-260 to W-379; K-261 to W-379; C-262 to W-379; I-263 to W-379; C-264 to W-379; P-265 to W-379; P-266 to W-379; G-267 to W-379; L-268 to W-379; E-269 to W-379; G-270 to W-379; E-271 to W-379; Q-272 to W-379; C-273 to W-379; E-274 to W-379; I-275 to W-379; S-276 to W-379; K-277 to W-379; C-278 to W-379; P-279 to W-379; Q-280 to W-379; P-281 to W-379; C-282 to W-379; R-283 to W-379; N-284 to W-379; G-285 to W-379; G-286 to W-379; K-287 to W-379; C-288 to W-379; I-289 to W-379; G-290 to W-379; K-291 to W-379; S-292 to W-379; K-293 to W-379; C-294 to W-379; K-295 to W-379; C-296 to W-379; S-297 to W-379; K-298 to W-379; G-299 to W-379; Y-300 to W-379; Q-301 to W-379; G-302 to W-379; D-303 to W-379; L-304 to W-379; C-305 to W-379; S-306 to W-379; K-307 to W-379; P-308 to W-379; V-309 to W-379; C-310 to W-379; E-311 to W-379; P-312 to W-379; G-313 to W-379; C-314 to W-379; G-315 to W-379; A-316 to W-379; H-317 to W-379; G-318 to W-379; T-319 to W-379; C-320 to W-379; H-321 to W-379; E-322 to W-379; P-323 to W-379; N-324 to W-379; K-325 to W-379; C-326 to W-379; Q-327 to W-379; C-328 to W-379; Q-329 to W-379; E-330 to W-379; G-331 to W-379; W-332 to W-379; H-333 to W-379; G-334 to W-379; R-335 to W-379; H-336 to W-379; C-337 to W-379; N-338 to W-379; K-339 to W-379; R-340 to W-379; Y-341 to W-379; E-342 to W-379; A-343 to W-379; S-344 to W-379; L-345 to W-379; I-346 to W-379; H-347 to W-379; A-348 to W-379; L-349 to W-379; R-350 to W-379; P-351 to W-379; A-352 to W-379; G-353 to W-379; A-354 to W-379; Q-355 to W-379; L-356 to W-379; R-357 to W-379; Q-358 to W-379; H-359 to W-379; T-360 to W-379; P-361 to W-379; S-362 to W-379; L-363 to W-379; K-364 to W-379; K-365 to W-379; A-366 to W-379; E-367 to W-379; E-368 to W-379; R-369 to W-379; R-370 to W-379; D-371 to W-379; P-372 to W-379; P-373 to W-379; and E-374 to W-379 of SEQ ID NO:71. Polypeptides encoded by these polynucleotides are also encompassed by the invention. Moreover, fragments and variants of these polypeptides (such as, for example, fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides, or the complement thereof) are encompassed by the invention. Antibodies that bind polypeptides of the invention are also encompassed by the invention. Polynucleotides encoding these polypeptides are also encompassed by the invention.

Also as mentioned above, even if deletion of one or more amino acids from the C terminus of a protein results in modification of loss of one or more biological functions of the protein, other functional activities (e.g., biological activities, ability to multimerize, ability to bind ligand, ability to generate antibodies, ability to bind antibodies) may still be retained. For example the ability of the shortened polypeptide to induce and/or bind to antibodies which recognize the complete or mature forms of the polypeptide generally will be retained when less than the majority of the residues of the complete or mature polypeptide are removed from the C terminus. Whether a particular polypeptide lacking C terminal residues of a complete polypeptide retains such immunologic activities can readily be determined by routine methods described herein and otherwise known in the art. It is not unlikely that a polypeptide with a large number of deleted C terminal amino acid residues may retain some biological or immunogenic activities. In fact, peptides composed of as few as six amino acid residues may often evoke an immune response.

Accordingly, the present invention further provides polypeptides having one or more residues deleted from the carboxy terminus of the amino acid sequence of the polypeptide shown in SEQ ID NO:71, as described by the general formula 1–n, where n is an integer from 6 to 378, where n corresponds to the position of the amino acid residue identified in SEQ ID NO:71. More in particular, the invention provides polynucleotides encoding polypeptides comprising, or alternatively consisting of, an amino acid sequence selected from the group: M-1 to I-378; M-1 to Y-377; M-1 to N-376; M-1 to S-375; M-1 to E-374; M-1 to P-373; M-1 to P-372; M-1 to D-371; M-1 to R-370; M-1 to R-369; M-1 to E-368; M-1 to E-367; M-1 to A-366; M-1 to K-365; M-1 to K-364; M-1 to L-363; M-1 to S-362; M-1 to P-361; M-1 to T-360; M-1 to H-359; M-1 to Q-358; M-1 to R-357; M-1 to L-356; M-1 to Q-355; M-1 to A-354; M-1 to G-353; M-1 to A-352; M-1 to P-351; M-1 to R-350; M-1 to L-349; M-1 to A-348; M-1 to H-347; M-1 to I-346; M-1 to L-345; M-1 to S-344; M-1 to A-343; M-1 to E-342; M-1 to Y-341; M-1 to R-340; M-1 to K-339; M-1 to N-338; M-1 to C-337; M-1 to H-336; M-1 to R-335; M-1 to G-334; M-1 to H-333; M-1 to W-332; M-1 to G-331; M-1 to E-330; M-1 to Q-329; M-1 to C-328; M-1 to Q-327; M-1 to C-326; M-1 to K-325; M-1 to N-324; M-1 to P-323; M-1 to E-322; M-1 to H-321; M-1 to C-320; M-1 to T-319; M-1 to G-318; M-1 to H-317; M-1 to A-316; M-1 to G-315; M-1 to C-314; M-1 to G-313; M-1 to P-312; M-1 to E-311; M-1 to C-310; M-1 to V-309; M-1 to P-308; M-1 to K-307; M-1 to S-306; M-1 to C-305; M-1 to L-304; M-1 to D-303; M-1 to G-302; M-1 to Q-301; M-1 to Y-300; M-1 to G-299; M-1 to K-298; M-1 to S-297; M-1 to C-296; M-1 to K-295; M-1 to C-294; M-1 to K-293; M-1 to S-292; M-1 to K-291; M-1 to G-290; M-1 to I-289; M-1 to C-288; M-1 to K-287; M-1 to G-286; M-1 to G-285; M-1 to N-284; M-1 to R-283; M-1 to C-282; M-1 to P-281; M-1 to Q-280; M-1 to P-279; M-1 to C-278; M-1 to K-277; M-1 to S-276; M-1 to I-275; M-1 to E-274; M-1 to C-273; M-1 to Q-272; M-1 to E-271; M-1 to G-270; M-1 to E-269; M-1 to L-268; M-1 to G-267; M-1 to P-266; M-1 to P-265; M-1 to C-264; M-1 to I-263; M-1 to C-262; M-1 to K-261; M-1 to G-260; M-1 to P-259; M-1 to Y-258; M-1 to F-257; M-1 to C-256; M-1 to T-255; M-1 to G-254; M-1 to G-253; M-1 to N-252; M-1 to F-251; M-1 to C-250; M-1 to T-249; M-1 to T-248; M-1 to S-247; M-1 to C-246; M-1 to N-245; M-1 to A-244; M-1 to K-243; M-1 to D-242; M-1 to C-241; M-1 to N-240; M-1 to V-239; M-1 to G-238; M-1 to Y-237; M-1 to F-236; M-1 to G-235; M-1 to P-234; M-1 to P-233; M-1 to C-232; M-1 to I-231; M-1 to C-230; M-1 to F-229; M-1 to G-228; M-1 to P-227; M-1 to T-226; M-1 to V-225; M-1 to C-224; M-1 to L-223; M-1 to G-222; M-1 to G-221; M-1 to N-220; M-1 to M-219; M-1 to C-218; M-1 to R-217; M-1 to P-216; M-1 to T-215; M-1 to C-214; M-1 to L-213; M-1 to A-212; M-1 to K-211; M-1 to E-210; M-1 to C-209; M-1 to H-208; M-1 to P-207; M-1 to G-206; M-1 to H-205; M-1 to F-204; M-1 to G-203; M-1 to D-202; M-1 to P-201; M-1 to C-200; M-1 to E-199; M-1 to C-198; M-1 to I-197; M-1 to R-196; M-1 to R-195; M-1 to E-194; M-1 to N-193; M-1 to C-192; M-1 to F-191; M-1 to G-190; M-1 to G-189; M-1 to N-188; M-1 to R-187; M-1 to C-186; M-1 to G-185; M-1 to G-184; M-1 to P-183; M-1 to C-182; M-1 to E-181; M-1 to A-180; M-1 to Q-179; M-1 to Q-178; M-1 to C-177; M-1 to T-176; M-1 to K-175; M-1 to F-174; M-1 to F-173; M-1 to I-172; M-1 to A-171; M-1 to N-170; M-1 to Q-169; M-1 to P-168; M-1 to T-167; M-1 to Q-166; M-1 to L-165; M-1 to I-164; M-1 to T-163; M-1 to N-162; M-1 to G-161; M-1 to E-160; M-1 to S-159; M-1 to N-158; M-1 to M-157; M-1 to V-156; M-1 to I-155; M-1 to V-154; M-1 to D-153; M-1 to V-152; M-1 to E-151; M-1 to F-150; M-1 to A-149; M-1 to A-148; M-1 to V-147; M-1 to G-146; M-1 to D-145; M-1 to Q-144; M-1 to K-143; M-1 to G-142; M-1 to L-141; M-1 to C-140; M-1 to P-139; M-1 to F-138; M-1 to G-137; M-1 to V-136; M-1 to Q-135; M-1 to V-134; M-1 to V-133; M-1 to S-132; M-1 to A-131; M-1 to K-130; M-1 to H-129; M-1 to P-128; M-1 to V-127; M-1 to T-126; M-1 to G-125; M-1 to L-124; M-1 to L-123; M-1 to P-122; M-1 to V-121; M-1 to N-120; M-1 to V-119; M-1 to T-118; M-1 to P-117; M-1 to D-116; M-1 to A-115; M-1 to M-114; M-1 to I-113; M-1 to G-112; M-1 to K-111; M-1 to D-110; M-1 to L-109; M-1 to S-108; M-1 to R-107; M-1 to L-106; M-1 to S-105; M-1 to L-104; M-1 to F-103; M-1 to E-102; M-1 to Y-101; M-1 to F-100; M-1 to Y-99; M-1 to E-98; M-1 to A-97; M-1 to Q-96; M-1 to G-95; M-1 to A-94; M-1 to A-93; M-1 to Q-92; M-1 to W-91; M-1 to T-90; M-1 to F-89; M-1 to N-88; M-1 to M-87; M-1 to S-86; M-1 to H-85; M-1 to I-84; M-1 to N-83; M-1 to V-82; M-1 to P-81; M-1 to I-80; M-1 to A-79; M-1 to P-78; M-1 to M-77; M-1 to R-76; M-1 to Q-75; M-1 to Q-74; M-1 to A-73; M-1 to K-72; M-1 to R-71; M-1 to F-70; M-1 to D-69; M-1 to H-68; M-1 to T-67; M-1 to F-66; M-1 to P-65; M-1 to A-64; M-1 to M-63; M-1 to K-62; M-1 to G-61; M-1 to E-60; M-1 to S-59; M-1 to V-58; M-1 to I-57; M-1 to L-56; M-1 to I-55; M-1 to D-54; M-1 to E-53; M-1 to E-52; M-1 to F-51; M-1 to G-50; M-1 to I-49; M-1 to L-48; M-1 to V-47; M-1 to R-46; M-1 to A-45; M-1 to Q-44; M-1 to H-43; M-1 to A-42; M-1 to D-41; M-1 to I-40; M-1 to W-39; M-1 to L-38; M-1 to Y-37; M-1 to L-36; M-1 to S-35; M-1 to E-34; M-1 to E-33; M-1 to Q-32; M-1 to P-31; M-1 to P-30; M-1 to G-29; M-1 to A-28; M-1 to E-27; M-1 to A-26; M-1 to R-25; M-1 to L-24; M-1 to A-23; M-1 to L-22; M-1 to L-21; M-1 to C-20; M-1 to L-19; M-1 to L-18; M-1 to I-17; M-1 to S-16; M-1 to W-15; M-1 to L-14; M-1 to W-13; M-1 to L-12; M-1 to A-11; M-1 to A-10; M-1 to A-9; M-1 to P-8; M-1 to F-7; and M-1 to A-6 of SEQ ID NO:71. Polypeptides encoded by these polynucleotides are also encompassed by the invention. Moreover, fragments and variants of these polypeptides (such as, for example, fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides, or the complement thereof) are encompassed by the invention. Antibodies that bind polypeptides of the invention are also encompassed by the invention. Polynucleotides encoding these polypeptides are also encompassed by the invention.

The tissue distribution in brain and lung, combined with the homology to tenascin indicates that the protein product of this gene is useful for diagnosis and treatment of cancers. Alternatively, given the tissue distribution indicated by Northern analysis, the translation product of this gene is thought to be a growth factor functioning in the brain and lung that may be useful in treating neurodegeneration and lung disorder. For example, the protein product of this gene is useful for the detection and treatment of disorders associated with developing lungs, particularly in premature infants where the lungs are the last tissues to develop. Furthermore, the tissue distribution indicates that the protein product of this gene is useful for the diagnosis and intervention of lung tumors, since the gene may be involved in the regulation of cell division. Additionally, expression in the brain indicates that it may be involved in neuronal survival; synapse formation; conductance; neural differentiation, etc. Such involvement may impact many processes, such as learning and cognition. It may also be useful in the treatment of such neurodegenerative disorders as schizophrenia; ALS; or Alzheimer's.

Polynucleotides and polypeptides corresponding to this gene are useful for the treatment and diagnosis of hematopoietic related disorders such as anemia, pancytopenia, leukopenia, thrombocytopenia or leukemia since stromal cells are important in the production of cells of hematopoietic lineages. Representative uses are described in the "Immune Activity" and "Infectious Disease" sections below, in Examples 17, 42, 44, 45, 47, 49, 50, and 51, and elsewhere herein. Briefly, the uses include bone marrow cell ex-vivo culture, bone marrow transplantation, bone marrow reconstitution, radiotherapy or chemotherapy of neoplasia. The gene product may also be involved in lymphopoiesis, therefore, it can be used in immune disorders such as infection, inflammation, allergy, immunodeficiency etc. In addition, this gene product may have commercial utility in the expansion of stem cells and committed progenitors of various blood lineages, and in the differentiation and/or proliferation of various cell types.

Protein, as well as, antibodies directed against the protein may show utility as a tissue-specific marker and/or immunotherapy target for the above listed tissues.

Many polynucleotide sequences, such as EST sequences, are publicly available and accessible through sequence databases. Some of these sequences are related to SEQ ID NO:70 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1960 of SEQ ID NO:70, b is an integer of 15 to 1974, where both a and b correspond to the positions of nucleotide residues shown in SEQ ID NO:70, and where b is greater than or equal to a+14.

Features of Protein Encoded by Gene No: 11

The translation product of this gene shares sequence homology with human squamous cell E48 antigen which is thought to be important in self-recognition and immune function.

In specific embodiments, polypeptides of the invention comprise, or alternatively consist of, an amino acid sequence selected from the group:

```
                                    (SEQ ID NO: 80)
MMATPSTRPPPPAASTTSATAPALPPRPPWPWPPSSWPPSGVSSKAPEAD
PLKNKALID;

                                    (SEQ ID NO: 81)
LLLTSPLPRCPPACSHDAPAHPDPGGPHGLTSGPGLGLPRVCLQRRQLLQ
PHALPGYGCLLHDHAHLLHPHQDEGQ;
and/or

                                    (SEQ ID NO: 82)
WLLQARVHHLLLPVRPLQRHRPCHPGHPGPGPHPPGHPLGSPLKPPRQTH
SRTKLS.
```

Moreover, fragments and variants of these polypeptides (such as, for example, fragments as described herein, polypeptides at least 80%, 85%, 90%, 95%, 96%, 97%, 98%, 99%, or 100% identical to these polypeptides, or polypeptides encoded by a polynucleotide which hybridizes, under stringent conditions, to the polynucleotide encoding these polypeptides) are encompassed by the invention. Antibodies that bind polypeptides of the invention and polynucleotides encoding these polypeptides are also encompassed by the invention.

When tested against K562 leukemia cell lines, supernatants removed from cells containing this gene activated the ISRE assay. Thus, it is likely that this gene activates leukemia cells through the Jak-STAT signal transduction pathway. The interferon-sensitive response element is a promoter element found upstream of many genes which are involved in the Jak-STAT pathway. The Jak-STAT pathway is a large, signal transduction pathway involved in the differentiation and proliferation of cells. Therefore, activation of the Jak-STAT pathway, reflected by the binding of the ISRE element, can be used to indicate proteins involved in the proliferation and differentiation of cells.

This gene is expressed primarily in adult brain, and to a lesser extent in fetal lung.

Polynucleotides and polypeptides of the invention would be useful as reagents for differential identification of the tissue(s) or cell type(s) present in a biological sample and for diagnosis of diseases and conditions which include, but are not limited to, autoimmune disorders. Similarly, polypeptides and antibodies directed to these polypeptides would be useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., immune, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise, or alternatively consist of one, two or all three of the immunogenic epitopes shown in SEQ ID NO:77 as residues: Tyr-28 to Phe-34, Thr-54 to Val-60, Tyr-73 to Thr-82. Polynucleotides encoding said polypeptides are encompassed by the invention.

The tissue distribution and homology to human squamous cell E48 antigen indicates that polynucleotides and polypeptides corresponding to this gene would be useful for study, diagnosis, detection, prevention and/or treatment of autoimmune diseases and disorders, such as lupus, transplant rejection, allergic reactions, and arthritis. Protein, as well as, antibodies directed against the protein may show utility as a tissue-specific marker and/or immunotherapy target for the above listed tissues.

Many polynucleotide sequences, such as EST sequences, are publicly available and accessible through sequence databases. Some of these sequences are related to SEQ ID NO:76 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 599 of SEQ ID NO:76, b is an integer of 15 to 613, where both a and b correspond to the positions of nucleotide residues shown in SEQ ID NO:76, and where b is greater than or equal to a+14.

Features of Protein Encoded by Gene No: 12

The gene encoding the disclosed cDNA is thought to reside on chromosome 19. Accordingly, polynucleotides related to this invention would be useful as a marker in linkage analysis for chromosome 19.

The translation product of this gene is a transmembrane protein that forms disulfide-bonded homodimers and contains a motif in its cytoplasmic domain (located at the carboxy terminus of the protein relative to the transmembrane domain) that functions as an adaptor for associating protein complexes involved in triggering cellular activation. The transmembrane domain is predicted to consist of the amino acid sequence:

VLAGIVMGDLVLTVLIALAVYFLG (SEQ ID NO: 85).

In specific embodiments, polypeptides of the invention comprise, or alternatively consist of, an amino acid sequence selected from the group:

QAQSDCSCSTVSPG (SEQ ID NO: 86), VLAGIVMGDLVLTVLIALAVYFLG (SEQ ID NO: 87), VPRGRGAAEATRKQRITETESPYQELQGQRSDVYSDL(SEQ ID NO: 88), and/or ETESPYQELQGQRSDVYSDLNT (SEQ ID NO: 89).

Moreover, fragments and variants of these polypeptides (such as, for example, fragments as described herein, polypeptides at least 80%, 85%, 90%, 95%, 96%, 97%, 98%, 99%, or 100% identical to these polypeptides, or polypeptides encoded by a polynucleotide which hybridizes, under stringent conditions, to the polynucleotide encoding these polypeptides) are encompassed by the invention. Antibodies that bind polypeptides of the invention and polynucleotides encoding these polypeptides are also encompassed by the invention.

This gene is expressed primarily in macrophage, and to a lesser extent in primary dendritic cells and neutrophils.

Polynucleotides and polypeptides of the invention would be useful as reagents for differential identification of the tissue(s) or cell type(s) present in a biological sample and for diagnosis of diseases and conditions which include, but are not limited to, immunologically mediated disorders. Similarly, polypeptides and antibodies directed to these polypeptides would be useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types and cell types (e.g., blood cells, and cells and tissue of the immune system, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise, or alternatively consist of one or both of the immunogenic epitopes shown in SEQ ID NO:84 as residues: Ala-28 to Ser-33, Ala-76 to Lys-111. Polynucleotides encoding said polypeptides are encompassed by the invention.

The tissue distribution in immune tissues indicates that polynucleotides and polypeptides corresponding to this gene would be useful for the diagnosis, treatment, and/or prevention of immune disorders including: leukemias, lymphomas, auto-immunities, immunodeficiencies (e.g., AIDS), immuno-suppressive conditions (transplantation) and hematopoietic disorders. Furthermore, expression of this gene product in macrophage and primary dendritic cells also strongly indicates a role for this protein in immune function and immune surveillance. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:83 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 683 of SEQ ID NO:83, b is an integer of 15 to 697, where both a and b correspond to the positions of nucleotide residues shown in SEQ ID NO:83, and where b is greater than or equal to a+14.

Features of Protein Encoded by Gene No: 13

The protein product of this gene was found to have homology to the human CD84 protein which, as a novel member of the Ig superfamily, is thought to play an important role in the modulation of the immune response. The present invention appears to encode a novel full-length CD84 homolog and is highly enriched, if not specific, for activated T cells.

In specific embodiments, polypeptides of the invention comprise, or alternatively consist of, an amino acid sequence selected from the group:

ITPLGLGAAD (SEQ ID NO: 96), TLRVLGKVPAVCPWCALWRKAGMDMTYSWLSRGDSTYTFHEGPVLSTSWRPGDSALSYTCRANNPISNVSSCPIPDGPFYADPNYASEKPSTAFCLLAKGLLIFLLLVILAMGLWVIRVQKRHKMPRMKKLMRNRMKLRKEAKPGSSPA (SEQ ID NO: 97), AVCPWCALWRKAGMDMTYSWL (SEQ ID NO: 98), PGDSALSYTCRANNPISNVSSCPI (SEQ ID NO: 99), YASEKPSTAFCLLAKGLLIFLLLV (SEQ ID NO: 100), and/or QKRHKMPRMKKLMRNRMKLRKEAKPG (SEQ ID NO: 101).

Moreover, fragments and variants of these polypeptides (such as, for example, fragments as described herein, polypeptides at least 80%, 85%, 90%, 95%, 96%, 97%, 98%, 99%, or 100% identical to these polypeptides, or polypeptides encoded by a polynucleotide which hybridizes, under stringent conditions, to the polynucleotide encoding these polypeptides) are encompassed by the invention. Antibodies that bind polypeptides of the invention and polynucleotides encoding these polypeptides are also encompassed by the invention.

This gene is expressed primarily in human activated T-Cells.

Polynucleotides and polypeptides of the invention would be useful as reagents for differential identification of the tissue(s) or cell type(s) present in a biological sample and for diagnosis of diseases and conditions which include, but are not limited to, immunodeficiencies, inflammatory conditions, infections, and other immune or hematopoietic disorders. Similarly, polypeptides and antibodies directed to these polypeptides would be useful in providing immunological probes for differential identification of the tissue(s) or cell type(s). For a number of disorders of the above tissues or cells, particularly of the disorders of the immune system, expression of this gene at significantly higher or lower levels may be routinely detected in certain tissues or cell types (e.g., immune, hematopoietic, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise, or alternatively consist of one or both of the immunogenic epitopes shown in SEQ ID NO:91 as residues: Glu-15 to Arg-23, Asn-79 to Gly-84. Polynucleotides encoding said polypeptides are encompassed by the invention.

The tissue distribution in activated T-cells indicates that polynucleotides and polypeptides corresponding to this gene would be useful for the detection, diagnosis, treatment, and/or prevention of a variety of immune system disorders. Expression of this gene product in T-cells indicates a role in the regulation of the proliferation; survival; differentiation; and/or activation of potentially all hematopoietic cell lineages, including blood stem cells. This gene product may be involved in the regulation of cytokine production, antigen presentation, or other processes that may also indicate a usefulness in the treatment of cancer (e.g., by boosting immune responses). Since the gene is expressed in cells of lymphoid origin, the natural gene product may be involved in immune functions. Therefore it may be also used as an agent for immunological disorders including arthritis, asthma, immune deficiency diseases such as AIDS, and leukemia. Protein, as well as, antibodies directed against the protein may show utility as a tumor marker and/or immunotherapy targets for the above listed tumors and tissues. In addition, this gene product may have commercial utility in the expansion of stem cells and committed progenitors of various blood lineages, and in the differentiation and/or proliferation of various cell types. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:90 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 1126 of SEQ ID NO:90, b is an integer of 15 to 1140, where both a and b correspond to the positions of nucleotide residues shown in SEQ ID NO:90, and where b is greater than or equal to a+14.

Features of Protein Encoded by Gene No: 14

Preferred polypeptides of the present invention comprise, or alternatively consist of, one or more of the immunogenic epitopes shown in SEQ ID NO:103 as residues: Val-54 to Asp-59, Thr-55 to Leu-60 and Trp-98 to Cys-104. Polynucleotides encoding said polypeptides are also encompassed by the invention. In a specific embodiment, antibodies that bind said epitopes or other polypeptides of the invention are also encompassed by the invention.

In a specific embodiment, polypeptides of the invention, comprise or alternatively consist of, the following amino acid sequences:

LSPPRGACR (SEQ ID NO: 106).

Polynucleotides encoding these polypeptides are also encompassed by the invention as are antibodies that bind one or more of these polypeptides. Moreover, fragments and variants of these polypeptides (such as, for example, fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides, or the complement thereof) are encompassed by the invention. Antibodies that bind polypeptides of the invention are also encompassed by the invention. Polynucleotides encoding these polypeptides are also encompassed by the invention.

Also preferred are polypeptides, comprising or alternatively consisting of, the mature polypeptide which is predicted to consist of residues 23-108 of the foregoing sequence (SEQ ID NO:103), and biologically active fragments of the mature polypeptide. Polynucleotides encoding these polypeptides are also encompassed by the invention. Moreover, fragments and variants of these polypeptides (such as, for example, fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides, or the complement thereof) are encompassed by the invention. Antibodies that bind polypeptides of the invention are also encompassed by the invention. Polynucleotides encoding these polypeptides are also encompassed by the invention.

FIG. 5 show the nucleotide (SEQ ID NO:102) and deduced amino acid sequence (SEQ ID NO:103) corresponding to this gene.

FIG. 6 shows an analysis of the amino acid sequence (SEQ ID NO:103). Alpha, beta, turn and coil regions; hydrophilicity and hydrophobicity; amphipathic regions; flexible regions; antigenic index and surface probability are shown, and all were generated using the default settings of the recited computer algorithms. In the "Antigenic Index or Jameson Wolf" graph, the positive peaks indicate locations of the highly antigenic regions of the protein, i.e., regions from which epitope-bearing peptides of the invention can be obtained. Polypeptides comprising, or alternatively consisting of, domains defined by these graphs are contemplated by the present invention, as are polynucleotides encoding these polypeptides.

The data presented in FIG. 6 are also represented in tabular form in Table 11. The columns are labeled with the headings "Res", "Position", and Roman Numerals I XIV. The column headings refer to the following features of the amino acid sequence presented in FIG. 6, and Table 11: "Res": amino acid residue of SEQ ID NO:103 and FIG. 5; "Position": position of the corresponding residue within SEQ ID NO:103 and FIG. 5; I: Alpha, Regions Garnier Robson; II: Alpha, Regions Chou Fasman; III: Beta, Regions Garnier Robson; IV: Beta, Regions Chou Fasman; V: Turn, Regions Garnier Robson; VI: Turn, Regions Chou Fasman; VII: Coil, Regions Garnier Robson; VIII: Hydrophilicity Plot Kyte Doolittle; IX: Hydrophobicity Plot Hopp Woods; X: Alpha, Amphipathic Regions Eisenberg; XI: Beta, Amphipathic Regions Eisenberg; XII: Flexible Regions Karplus Schulz; XIII: Antigenic Index Jameson Wolf; and XIV: Surface Probability Plot Emini.

Preferred embodiments of the invention in this regard include fragments that comprise, or alternatively consisting of, one or more of the following regions: alpha-helix and alpha-helix forming regions ("alpha-regions"), beta-sheet and beta-sheet forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, flexible regions, surface-forming regions and high antigenic index regions. The data representing the structural or functional attributes of the protein set forth in FIG. 6 and/or Table 11, as described above, was generated using the various modules and algorithms of the DNA*STAR set on default parameters. In a preferred embodiment, the data presented in columns VIII, IX, XIII, and XIV of Table 11 can be used to determine regions of the protein which exhibit a high degree of potential for antigenicity. Regions of high antigenicity are determined from the data presented in columns VIII, IX, XIII, and/or XIV by choosing values which represent regions of the polypeptide which are likely to be exposed on the surface of the polypeptide in an environment in which antigen recognition may occur in the process of initiation of an immune response.

Certain preferred regions in these regards are set out in FIG. 6, but may, as shown in Table 11, be represented or identified by using tabular representations of the data presented in FIG. 6. The DNA*STAR computer algorithm used to generate FIG. 6 (set on the original default parameters) was used to present the data in FIG. 6 in a tabular format (See Table 11). The tabular format of the data in FIG. 6 is used to easily determine specific boundaries of a preferred region.

The present invention is further directed to fragments of the polynucleotide sequences described herein. By a fragment of, for example, the polynucleotide sequence of a deposited cDNA or the nucleotide sequence shown in SEQ ID NO:102, is intended polynucleotide fragments at least about 15 nt, and more preferably at least about 20 nt, at least about 25 nt, still more preferably at least about 30 nt, at least about 35 nt, and even more preferably, at least about 40 nt in length, at least about 45 nt in length, at least about 50 nt in length, at least about 60 nt in length, at least about 70 nt in length, at least about 80 nt in length, at least about 90 nt in length, at least about 100 nt in length, at least about 125 nt in length, at least about 150 nt in length, at least about 175 nt in length, which are useful as diagnostic probes and primers as discussed herein. Of course, larger fragments 200-1500 nt in length are also useful according to the present invention, as are fragments corresponding to most, if not all, of the nucleotide sequence of a deposited cDNA or as shown in SEQ ID NO:102. By a fragment at least 20 nt in length, for example, is intended fragments which include 20 or more contiguous bases from the nucleotide sequence of a deposited cDNA or the nucleotide sequence as shown in SEQ ID NO:102. In this context "about" includes the particularly recited size, an sizes larger or smaller by several (5, 4, 3, 2, or 1) nucleotides, at either terminus or at both termini. Representative examples of polynucleotide fragments of the invention include, for example, fragments that comprise, or alternatively, consist of, a sequence from about nucleotide 1 to about 50, from about 51 to about 100, from about 101 to about 150, from about 151 to about 200, from about 201 to about 250, from about 251 to about 300, from about 301 to about 350, from about 351 to about 400, from about 401 to about 450, from about 451 to about 500, and from about 501 to about 553 of SEQ ID NO:102, or the complementary strand thereto, or the cDNA contained in a deposited clone. In this context "about" includes the particularly recited ranges, and ranges larger or smaller by several (5, 4, 3, 2, or 1) nucleotides, at either terminus or at both termini. In additional embodiments, the polynucleotides of the invention encode functional attributes of the corresponding protein.

Preferred polypeptide fragments of the invention comprise, or alternatively consist of, the secreted protein having a continuous series of deleted residues from the amino or the carboxy terminus, or both. Particularly, N-terminal deletions of the polypeptide can be described by the general formula m−108 where m is an integer from 2 to 102, where m corresponds to the position of the amino acid residue identified in SEQ ID NO:103. More in particular, the invention provides polynucleotides encoding polypeptides comprising, or alternatively consisting of, an amino acid sequence selected from the group: K-2 to P-108; A-3 to P-108; L-4 to P-108; C-5 to P-108; L-6 to P-108; L-7 to P-108; L-8 to P-108; L-9 to P-108; P-10 to P-108; V-11 to P-108; L-12 to P-108; G-13 to P-108; L-14 to P-108; L-15 to P-108; V-16 to P-108; S-17 to P-108; S-18 to P-108; K-19 to P-108; T-20 to P-108; L-21 to P-108; C-22 to P-108; S-23 to P-108; M-24 to P-108; E-25 to P-108; E-26 to P-108; A-27 to P-108; I-28 to P-108; N-29 to P-108; E-30 to P-108; R-31 to P-108; I-32 to P-108; Q-33 to P-108; E-34 to P-108; V-35 to P-108; A-36 to P-108; G-37 to P-108; S-38 to P-108; L-39 to P-108; I-40 to P-108; F-41 to P-108; R-42 to P-108; A-43 to P-108; I-44 to P-108; S-45 to P-108; S-46 to P-108; I-47 to P-108; G-48 to P-108; L-49 to P-108; E-50 to P-108; C-51 to P-108; Q-52 to P-108; S-53 to P-108; V-54 to P-108; T-55 to P-108; S-56 to P-108; R-57 to P-108; G-58 to P-108; D-59 to P-108; L-60 to P-108; A-61 to P-108; T-62 to P-108; C-63 to P-108; P-64 to P-108; R-65 to P-108; G-66 to P-108; F-67 to P-108; A-68 to P-108; V-69 to P-108; T-70 to P-108; G-71 to P-108; C-72 to P-108; T-73 to P-108; C-74 to P-108; G-75 to P-108; S-76 to P-108; A-77 to P-108; C-78 to P-108; G-79 to P-108; S-80 to P-108; W-81 to P-108; D-82 to P-108; V-83 to P-108; R-84 to P-108; A-85 to P-108; E-86 to P-108; T-87 to P-108; T-88 to P-108; C-89 to P-108; H-90 to P-108; C-91 to P-108; Q-92 to P-108; C-93 to P-108; A-94 to P-108; G-95 to P-108; M-96 to P-108; D-97 to P-108; W-98 to P-108; T-99 to P-108; G-100 to P-108; A-101 to P-108; R-102 to P-108; and C-103 to P-108 of SEQ ID NO:103. Polypeptides encoded by these polynucleotides are also encompassed by the invention. Moreover, fragments and variants of these polypeptides (such as, for example, fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides, or the complement thereof) are encompassed by the invention. Antibodies that bind polypeptides of the invention are also encompassed by the invention. Polynucleotides encoding these polypeptides are also encompassed by the invention.

Also as mentioned above, even if deletion of one or more amino acids from the C terminus of a protein results in modification of loss of one or more biological functions of the protein, other functional activities (e.g., biological activities, ability to multimerize, ability to bind ligand, ability to generate antibodies, ability to bind antibodies) may still be retained. For example the ability of the shortened polypeptide to induce and/or bind to antibodies which recognize the complete or mature forms of the polypeptide generally will be retained when less than the majority of the residues of the complete or mature polypeptide are removed from the C terminus. Whether a particular polypeptide lacking C terminal residues of a complete polypeptide retains such immunologic activities can readily be determined by routine methods described herein and otherwise known in the art. It is not unlikely that a polypeptide with a large number of deleted C terminal amino acid residues may retain some biological or immunogenic activities. In fact, peptides composed of as few as six amino acid residues may often evoke an immune response. Accordingly, the present invention further provides polypeptides having one or more residues deleted from the carboxy terminus of the amino acid sequence of the polypeptide shown in FIG. 5 (SEQ ID NO:103), as described by the general formula 1–n, where n is an integer from 6 to 107, where n corresponds to the position of the amino acid residue identified in SEQ ID NO:103. More in particular, the invention provides polynucleotides encoding polypeptides comprising, or alternatively consisting of, an amino acid sequence selected from the group: M-1 to Q-107; M-1 to V-106; M-1 to R-105; M-1 to C-104; M-1 to C-103; M-1 to R-102; M-1 to A-101; M-1 to G-100; M-1 to T-99; M-1 to W-98; M-1 to D-97; M-1 to M-96; M-1 to G-95; M-1 to A-94; M-1 to C-93; M-1 to Q-92; M-1 to C-91; M-1 to H-90; M-1 to C-89; M-1 to T-88; M-1 to T-87; M-1 to E-86; M-1 to A-85; M-1 to R-84; M-1 to V-83; M-1 to D-82; M-1 to W-81; M-1 to S-80; M-1 to G-79; M-1 to C-78; M-1 to A-77; M-1 to S-76; M-1 to G-75; M-1 to C-74; M-1 to T-73; M-1 to C-72; M-1 to G-71; M-1 to T-70; M-1 to V-69; M-1 to A-68; M-1 to F-67; M-1 to G-66; M-1 to R-65; M-1 to P-64; M-1 to C-63; M-1 to T-62; M-1 to A-61; M-1 to L-60; M-1 to D-59; M-1 to G-58; M-1 to R-57; M-1 to S-56; M-1 to T-55; M-1 to V-54; M-1 to S-53; M-1 to Q-52; M-1 to C-51; M-1 to E-50; M-1 to L-49; M-1 to G-48; M-1 to I-47; M-1 to S-46; M-1 to S-45; M-1 to I-44; M-1 to A-43; M-1 to R-42; M-1 to F-41; M-1 to I-40; M-1 to L-39; M-1 to S-38; M-1 to G-37; M-1 to A-36; M-1 to V-35; M-1 to E-34; M-1 to Q-33; M-1 to I-32; M-1 to R-31; M-1 to E-30; M-1 to N-29; M-1 to I-28; M-1 to A-27; M-1 to E-26; M-1 to E-25; M-1 to M-24; M-1 to S-23; M-1 to C-22; M-1 to L-21; M-1 to T-20; M-1 to K-19; M-1 to S-18; M-1 to S-17; M-1 to V-16; M-1 to L-15; M-1 to L-14; M-1 to G-13; M-1 to L-12; M-1 to V-11; M-1 to P-10; M-1 to L-9; M-1 to L-8; M-1 to L-7; and M-1 to L-6; of SEQ ID NO:103. Polypeptides encoded by these polynucleotides are also encompassed by the invention. Moreover, fragments and variants of these polypeptides (such as, for example, fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides, or the complement thereof) are encompassed by the invention. Antibodies that bind polypeptides of the invention are also encompassed by the invention. Polynucleotides encoding these polypeptides are also encompassed by the invention.

In addition, any of the above listed N- or C-terminal deletions can be combined to produce a N- and C-terminal deleted polypeptide. The invention also provides polypeptides comprising, or alternatively consisting of, one or more amino acids deleted from both the amino and the carboxyl termini, which may be described generally as having residues m-n of SEQ ID NO:103, where n and m are integers as described above.

Also included are polynucleotide sequences encoding a polypeptide consisting of a portion of the complete amino acid sequence encoded by a cDNA clone contained in ATCC™ Deposit No. 209215, where this portion excludes any integer of amino acid residues from 1 to about 102 amino acids from the amino terminus of the complete amino acid sequence encoded by a cDNA clone contained in ATCC™ Deposit No. 209215, or any integer of amino acid residues from 6 to about 108 amino acids from the carboxy terminus, or any combination of the above amino terminal and carboxy terminal deletions, of the complete amino acid sequence encoded by the cDNA clone contained in ATCC™ Deposit No. 209215. Polypeptides encoded by these polynucleotides also are encompassed by the invention. Moreover, fragments and variants of these polypeptides (such as, for example, fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides, or the complement thereof) are encompassed by the invention. Antibodies that bind polypeptides of the invention are also encompassed by the invention. Polynucleotides encoding these polypeptides are also encompassed by the invention.

Additional preferred polypeptide fragments of the invention comprise, or alternatively consist of, an amino acid sequence selected from the group: M-1 to L-15; K-2 to V-16; A-3 to S-17; L-4 to S-18; C-5 to K-19; L-6 to T-20; L-7 to L-21; L-8 to C-22; L-9 to S-23; P-10 to M-24; V-11 to E-25; L-12 to E-26; G-13 to A-27; L-14 to I-28; L-15 to N-29; V-16 to E-30; S-17 to R-31; S-18 to I-32; K-19 to Q-33; T-20 to E-34; L-21 to V-35; C-22 to A-36; S-23 to G-37; M-24 to S-38; E-25 to L-39; E-26 to I-40; A-27 to F-41; I-28 to R-42; N-29 to A-43; E-30 to I-44; R-31 to S-45; I-32 to S-46; Q-33 to I-47; E-34 to G-48; V-35 to L-49; A-36 to E-50; G-37 to C-51; S-38 to Q-52; L-39 to S-53; I-40 to V-54; F-41 to T-55; R-42 to S-56; A-43 to R-57; I-44 to G-58; S-45 to D-59; S-46 to L-60; I-47 to A-61; G-48 to T-62; L-49 to C-63; E-50 to P-64; C-51 to R-65; Q-52 to G-66; S-53 to F-67; V-54 to A-68; T-55 to V-69; S-56 to T-70; R-57 to G-71; G-58 to C-72; D-59 to T-73; L-60 to C-74; A-61 to G-75; T-62 to S-76; C-63 to A-77; P-64 to C-78; R-65 to G-79; G-66 to S-80; F-67 to W-81; A-68 to D-82; V-69 to V-83; T-70 to R-84; G-71 to A-85; C-72 to E-86; T-73 to T-87; C-74 to T-88; G-75 to C-89; S-76 to H-90; A-77 to C-91; C-78 to Q-92; G-79 to C-93; S-80 to A-94; W-81 to G-95; D-82 to M-96; V-83 to D-97; R-84 to W-98; A-85 to T-99; E-86 to G-100; T-87 to A-101; T-88 to R-102; C-89 to C-103; H-90 to C-104; C-91 to R-105; Q-92 to V-106; C-93 to Q-107; and A-94 to P-108 of SEQ ID NO:103. Moreover, fragments and variants of these polypeptides (such as, for example, fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides, or the complement thereof) are encompassed by the invention. Antibodies that bind polypeptides of the invention are also encompassed by the invention. Polynucleotides encoding these polypeptides are also encompassed by the invention.

As described herein or otherwise known in the art, the polynucleotides of the invention have uses that include, but are not limited to, serving as probes or primers in chromosome identification, chromosome mapping, and linkage analysis.

This gene is expressed primarily in placenta and in some immune tissues and cells of the immune system (e.g., Jurkat T cell lines, and normal bone marrow).

Polynucleotides and polypeptides of the invention are useful as reagents for differential identification of the tissue(s) or cell type(s) present in a biological sample and for diagnosis of diseases and conditions which include, but are not limited to, fetal deficiencies, pre-natal disorders, and vascular diseases and conditions. Similarly, polypeptides and antibodies directed to these polypeptides are useful in providing immunological probes for differential identification of the tissue(s) or cell type(s). For a number of disorders of the above tissues or cells, particularly of the reproductive system, expression of this gene at significantly higher or lower levels may be routinely detected in certain tissues or cell types (e.g., developmental, proliferating, vascular, and cancerous and wounded tissues) or bodily fluids (e.g., lymph, amniotic fluid, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in placenta indicates that polynucleotides and polypeptides corresponding to this gene are useful for the treatment and diagnosis of developmental anomalies, fetal deficiencies, reproductive disfunction or pre-natal disorders. Moreover, the protein is useful in the detection, treatment, and/or prevention of a variety of vascular disorders and conditions, which include, but are not limited to microvascular disease, vascular leak syndrome, aneurysm, stroke, embolism, thrombosis, coronary artery disease, arteriosclerosis, and/or atherosclerosis. Protein, as well as, antibodies directed against the protein may show utility as a tumor marker and/or immunotherapy targets for the above listed tissues.

The tissue distribution of the expression of this gene indicates that polynucleotides and polypeptides corresponding to this gene (as well as antibodies raised against those polypeptides) are useful for the diagnosis and treatment of diseases and disorders associated with the immune system, including, but not limited to, allergy, asthma, graft rejection, systemic lupus erythematosus (SLE), rheumatoid arthritis (RA) and other autoimmune conditions, infections, AIDS, chronic variable immune deficiency (CVID) and other immune deficiency syndromes, respiratory distress syndrome and inflammation, neoplasms of the immune/hematopoetic system including leukemias, lymphomas and other proliferative disorders such as multiple myeloma, Hodgkin's and non-Hodgkin's lymphoma, and myelodysplastic syndromes. The polynucleotides and/or polypeptides corresponding to this gene (and/or antibodies raised against those polypeptides) may also be useful for stimulating the immune response to bolster the immune response to diseases such as cancer or infection.

Furthermore, the protein may also be used to determine unknown biological activities, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Polynucleotides or polypeptides of the invention and/or agonists and/or antagonists thereof, are used to treat, prevent, and/or diagnose diseases and disorders of the endocrine system.

In specific embodiments, the polynucleotides and/or polypeptides corresponding to this gene and/or agonists or antagonists of those polypeptides (including antibodies) as well as fragments and variants of those polynucleotides, polypeptides agonists and antagonists, may be used to diagnose, prognose or monitor vascular diseases. In other specific embodiments, the polynucleotides and/or polypeptides corresponding to this gene and/or agonists or antagonists of those polypeptides (including antibodies) as well as fragments and variants of those polynucleotides, polypeptides agonists and antagonists, may be used to treat, prevent, or ameliorate vascular diseases In other preferred embodiments, the polynucleotides and/or polypeptides corresponding to this gene and/or agonists or antagonists of those polypeptides (including antibodies) as well as fragments and variants of those polynucleotides, polypeptides agonists and antagonists, may be used to diagnose, prognose or monitor diseases and disorders associated with aberrant glucose metabolism or glucose uptake into cells. In other specific embodiments, the polynucleotides and/or polypeptides corresponding to this gene and/or agonists or antagonists of those polypeptides (including antibodies) as well as fragments and variants of those polynucleotides, polypeptides agonists and antagonists, may be used to treat, prevent, or ameliorate diseases and disorders associated with aberrant glucose metabolism or glucose uptake into cells.

It is believed that increased expression of this gene, at either the RNA or protein level, is increased in individuals (or a subset of individuals) that either have a predisposition to develop or have already developed type II diabetes mellitus (non-insulin dependent diabetes). Thus, the polynucleotides and/or polypeptides corresponding to this gene and/or agonists or antagonists of those polypeptides (including antibodies) as well as fragments and variants of those polynucleotides, polypeptides agonists and antagonists, may be used to diagnose, prognose, and/or monitor individuals with type II diabetes mellitus or individuals with a predisposition to develop type II diabetes mellitus.

By "agonist," is meant any substance that enhances the function of the polynucleotides or polypeptides of the invention. Classes of molecules that can function as agonists include, but are not limited to, small molecules, antibodies (including fragments or variants thereof, such as Fab fragments, Fab'2 fragments and scFvs), and peptidomimetics. By "antagonist," is meant any substance that diminishes or abolishes the function of the polynucleotides or polypeptides of the invention. Classes of molecules that can function as antagonists include, but are not limited to, small molecules, antibodies (including fragments or variants thereof, such as Fab fragments, Fab'2 fragments and scFvs) antisense polynucleotides, ribozymes, and peptidomimetics.

A biological sample of persons afflicted with type II diabetes mellitus is believed to be characterized by high levels of expression of this gene when compared to that observed in individuals not having type II diabetes mellitus. Thus, polynucleotides and/or polypeptides of the invention, and/or agonists or antagonists thereof, may be used according to the methods of the invention in the diagnosis and/or prognosis of individuals with type II diabetes mellitus, a subset of individuals with type II diabetes mellitus, and/or individuals or a subset of individuals with a predisposition to develop type II diabetes mellitus. For example, a biological sample obtained from a person suspected of being afflicted with type II diabetes mellitus, "the subject," may be analyzed for the relative expression level(s) of polynucleotides and/or polypeptides of the invention. The expression level(s) of one or more of these molecules of the invention is (are) then compared to the expression level(s) of the same molecules of the invention as expressed in a person known not to be afflicted with rheumatoid arthritis. An increase in the expression level(s) of this gene in samples obtained from the subject compared to the control suggests that the subject is afflicted with type II diabetes mellitus or a subset thereof.

In another embodiment, the polynucleotides and/or polypeptides corresponding to this gene and/or antagonists thereof (especially neutralizing or antagonistic antibodies)

may be used to treat, prevent, and/or ameliorate type II diabetes. Additionally, in other embodiments, the polynucleotides and/or polypeptides corresponding to this gene and/or anatgonists thereof (especially neutralizing or antagonistic antibodies) may be used to treat, prevent, or ameliorate conditions associated with type II diabetes mellitus, including, but not limited to, seizures, mental confusion, drowsiness, nonketotic hyperglycemic-hyperosmolar coma, cardiovascular disease (e.g., heart disease, atherosclerosis, microvascular disease, hypertension, stroke, and other diseases and disorders as described in the "Cardiovascular Disorders" section below), dyslipidemia, kidney disease (e.g., renal failure, nephropathy other diseases and disorders as described in the "Renal Disorders" section below), nerve damage, neuropathy, vision impairment (e.g., diabetic retinopathy and blindness), ulcers and impaired wound healing, infections (e.g., infectious diseases and disorders as described in the "Infectious Diseases" section below, especially of the urinary tract and skin), carpal tunnel syndrome and Dupuytren's contracture.

In other embodiments, the polynucleotides and/or polypeptides corresponding to this gene and/or agonists or antagonists thereof are administered to an animal, preferably a mammal, and most preferably a human, in order to regulate the animal's weight. In specific embodiments the polynucleotides and/or polypeptides corresponding to this gene and/or agonists or antagonists thereof are administered to an animal, preferably a mammal, and most preferably a human, in order to control the animal's weight by modulating a biochemical pathway involving insulin. In still other embodiments the polynucleotides and/or polypeptides corresponding to this gene and/or agonists or antagonists thereof are administered to an animal, preferably a mammal, and most preferably a human, in order to control the animal's weight by modulating a biochemical pathway involving insulin-like growth factor.

In a preferred embodiment, the polynucleotides and/or polypeptides corresponding to this gene and/or agonists or antagonists thereof are administered to an animal, preferably a mammal, and most preferably a human, in order to treat weight disorders, including but not limited to, obesity, cachexia, wasting disease, anorexia, and bulimia.

In other embodiments, the polynucleotides and/or polypeptides corresponding to this gene and/or agonists or antagonists thereof are useful for the treatment, prevention or amelioration of neurodegenerative disorders including, but not limited to, Alzheimer's disease, Parkinson's disease, Huntington's disease, amylotrophic lateral sclerosis and the like, as well as spinocerebellar degenerations, and other neurological diseases and disorders as described in the "Neural Activity and Neurological Activity diseases" section below.

In another embodiment, compositions of the invention (comprising polynucleotides, polypeptides of the invention, agonists and/or antagonists thereof (including antibodies) as well as fragments and variants of the polynucleotides, polypeptides of the invention, agonists and/or antagonists of the invention) are used in combination with anti-diabetic drugs. In a specific embodiment, compositions of the invention are administered in combination with thiazolidinediones (TZDs) including, but not limited to, rosiglitazone, pioglitazone, and troglitazone. In another specific embodiment, compositions of the invention are used in combination with oral hypoglycemic sulfonylurea drugs including, but not limited to, acarbose, acetohexamide, chlorpropamide, glimepiride, glipizide, glyburide, metformin, tolazamide, and/or tolbutamide. In still other embodiments, compositions of the invention are administered in combination with one or more of the following: a biguanide antidiabetic agent, a glitazone antidiabetic agent, and a sulfonylurea antidiabetic agent.

Features of Protein Encoded by Gene No: 15

The translation product of this gene shares sequence homology with *drosophila* peroxidasin which is thought to be important in extracellular matrix architecture. Moreover, the protein has homology to receptor-linked protein tyrosine phosphatases, which play important roles in inflammatory diseases and immune disorders. When tested against Jurkat T-cell lines, supernatants removed from cells containing this gene activated the GAS pathway. Thus, it is likely that this gene activates T-cells through the Jaks-STAT signal transduction pathway. GAS is a promoter element found upstream in many genes which are involved in the Jaks-STAT pathway. The Jaks-STAT pathway is a large, signal transduction pathway involved in the differentiation and proliferation of cells. Therefore, activation of the Jaks-STAT pathway, reflected by the binding of the GAS element, can be used to indicate proteins involved in the proliferation and differentiation of cells.

In specific embodiments, polypeptides of the invention comprise the following amino acid sequence:

```
                                        (SEQ ID NO: 111)
GRPTRPLRVA,

                                        (SEQ ID NO: 112)
AWCPQTHTTSCLMGPFCCYSPLPGDMPTMARPCPQTWVSTHVRPATGLARQ

SAEALGCLWLSSGRISRSSLGTWWLWWVSSLLWNVGRPGATQSPQSHGGKM

GNPWPSSPEGTQCPGGPC,

                                        (SEQ ID NO: 113)
CCYSPLPGDMPTMARPCPQTWVSTH,

                                        (SEQ ID NO: 114)
ALGCLWLSSGRISRSSLG,
and/or

                                        (SEQ ID NO: 115)
WNVGRPGATQSPQSHGGKMGNPWPSSPE.
```

Polynucleotides encoding these polypeptides are also encompassed by the invention.

This gene is expressed primarily in umbilical vein and to a lesser extent in endothelial and brain cells.

Therefore, polynucleotides and polypeptides of the invention are useful as reagents for differential identification of the tissue(s) or cell type(s) present in a biological sample and for diagnosis of diseases and conditions which include, but are not limited to, immune, developmental and growth diseases and/or disorders. Similarly, polypeptides and antibodies directed to these polypeptides are useful in providing immunological probes for differential identification of the tissue(s) or cell type(s). For a number of disorders of the above tissues or cells, particularly of fetal tissues, expression of this gene at significantly higher or lower levels may be routinely detected in certain tissues or cell types (e.g., immune, hematopoietic, neural, cancerous and wounded tissues) or bodily fluids (e.g. lymph, amniotic fluid, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO:108 as residues: Ala-55 to Thr-62, His-164 to Gly-175, Ala-197 to Glu-202.

The tissue distribution in umbilical vein cells, and homology to peroxidasin and receptor-linked protein tyrosine phosphatases indicates that polynucleotides and polypeptides corresponding to this gene are useful for the study, diagnosis, and treatment of various fetal developmental and growth disorders involving the formation of extracellular matrix. Alternatively, the tissue distribution indicates that polynucleotides and polypeptides corresponding to this gene are useful for the diagnosis and treatment of a variety of immune system disorders. Activation of the GAS pathway by the gene product indicates a role in the regulation of the proliferation; survival; differentiation; and/or activation of potentially all hematopoietic cell lineages, including blood stem cells.

This gene product may be involved in the regulation of cytokine production, antigen presentation, or other processes that may also suggest a usefulness in the treatment of cancer (e.g. by boosting immune responses). Since the gene product demonstrates activity with regard to the GAS pathway, the natural gene product may be involved in immune functions. Therefore it may be also used as an agent for immunological disorders including arthritis, asthma, immune deficiency diseases such as AIDS, leukemia, rheumatoid arthritis, inflammatory bowel disease, sepsis, acne, and psoriasis, and tissues. In addition, this gene product may have commercial utility in the expansion of stem cells and committed progenitors of various blood lineages, and in the differentiation and/or proliferation of various cell types. Protein is useful in modulating the immune response to proliferative and vascular cells and tissues, particularly those having aberrant phenotypes. Protein, as well as, antibodies directed against the protein may show utility as a tumor marker and/or immunotherapy targets for the above listed tissues.

Features of Protein Encoded by Gene No: 16

The translation product of this gene shares sequence homology with the kidney injury molecule-1 of *Rattus norvegicus* which is thought to play an important role in the restoration of the morphological integrity and function to postischemic kidney (See Genbank Accession No. gi|2665892 (AF035963)). Polynucleotides and polypeptides of the present invention are useful to promote growth of new tissue and survival of damaged tissue. Recombinant polypeptides of the present invention can be expressed in prokaryotic and eukaryotic host cells using a claimed process. Soluble variants fused to a toxin, imagable compound or radionuclide, and IgG fusion proteins are also claimed.

Polynucleotides and polypeptides of the present invention or an agonist, can be used to treat renal disease and to promote the growth of new tissue or the survival of damaged tissue, generally in conditions where the binding of specific ligand to the present invention stimulates cell growth, maintains cellular differentiation or reduces apoptosis, e.g. in cases of renal failure, nephritis, kidney transplants, toxic or hypoxic injury. A monoclonal antibody specific for polynucleotides and polypeptides of the present invention can be used to treat renal disease, e.g. where binding of the invention to a ligand results in neoplasia, loss of cellular function, susceptibility to apoptosis or promotion of inflammation, deliver imaging agents to the cells expressing the present invention in vivo or in vitro and measure the concentration of the present invention by immunoassay. Damage/regeneration of renal cells can be determined by measuring the present invention, particularly to diagnose or monitor the progress of disease or therapy. The tumour cells expressing the present invention can be inhibited by treatment with a fusion protein comprising a ligand of the present invention or MAb with a toxin or radionuclide, and tumour cells that express the present invention ligand can be inhibited with similarly tagged polypeptides of the present invention or anti-present invention ligand antibody.

Preferred polypeptides of the invention comprise the following amino acid sequence:

```
                                        (SEQ ID NO: 122)
HESTVK.
```

Polynucleotides encoding these polypeptides are also provided.

This gene is expressed primarily in infant brain and fetal liver, and to a lesser extent in neoplastic cell lines and endocrine organs.

Therefore, polynucleotides and polypeptides of the invention are useful as reagents for differential identification of the tissue(s) or cell type(s) present in a biological sample and for diagnosis of diseases and conditions, which include, but are not limited to, immune, neural, endocrine, and growth disorders. Similarly, polypeptides and antibodies directed to these polypeptides are useful in providing immunological probes for differential identification of the tissue(s) or cell type(s). For a number of disorders of the above tissues or cells, particularly of the immune and endocrine systems, expression of this gene at significantly higher or lower levels is routinely detected in certain tissues or cell types (e.g., immune, neural, endocrine, growth, and cancerous and wounded tissues) or bodily fluids (e.g., lymph, serum, plasma, urine, amniotic fluid, bile, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise immunogenic epitopes shown in SEQ ID NO:117 as residues: Ser-44 to Ser-51, Cys-53 to Cys-64, Val-76 to Lys-83, Pro-102 to Gly-108, Arg-133 to Thr-162, Thr-169 to Lys-183. Polynucleotides encoding said polypeptides are also provided.

The tissue distribution in fetal liver and infant brain indicates that polynucleotides and polypeptides corresponding to this gene are useful for study and treatment of immune and developmental conditions. Moreover, the expression within infant and fetal tissues and other cellular sources marked by proliferating cells indicates this protein may play a role in the regulation of cellular division, and may show utility in the diagnosis and treatment of cancer and other proliferative disorders. Representative uses are described in the "Immune Activity" and "Infectious Disease" sections below, in Examples 17, 42, 44, 45, 47, 49, 50, and 51, and elsewhere herein. Similarly, developmental tissues rely on decisions involving cell differentiation and/or apoptosis in pattern formation. Thus this protein may also be involved in apoptosis or tissue differentiation and could again be useful in cancer therapy. Alternatively, the protein product of this gene could be used in the treatment and/or detection of kidney diseases including renal failure, nephritus, renal tubular acidosis, proteinuria, pyuria, edema, pyelonephritis, hydronephritis, nephrotic syndrome, crush syndrome, glomerulonephritis, hematuria, renal colic and kidney stones, in addition to Wilm's Tumor Disease, and congenital kidney abnormalities such as horseshoe kidney, polycystic kidney, and Falconi's syndrome. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:116 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 557 of SEQ ID NO:116, b is an integer of 15 to 571, where both a and b correspond to the positions of nucleotide residues shown in SEQ ID NO:116, and where b is greater than or equal to a+14.

Features of Protein Encoded by Gene No: 17

The translation product of this gene shares some sequence homology with various chains of the T-cell receptor, which are important in signalling between different cells of the immune system.

The gene encoding the disclosed cDNA is thought to reside on the X chromosome. Accordingly, polynucleotides related to this invention are useful as a marker in linkage analysis for the X chromosome.

This gene is expressed primarily in placental tissue, and to a lesser extent in activated monocytes and dendritic cells.

Therefore, polynucleotides and polypeptides of the invention are useful as reagents for differential identification of the tissue(s) or cell type(s) present in a biological sample and for diagnosis of diseases and conditions which include, but are not limited to, immune disorders and reproductive disorders, particularly pregnancy-associated disorders. Similarly, polypeptides and antibodies directed to these polypeptides are useful in providing immunological probes for differential identification of the tissue(s) or cell type(s). For a number of disorders of the above tissues or cells, particularly of the immune system and female reproductive system, expression of this gene at significantly higher or lower levels is routinely detected in certain tissues or cell types (e.g., immune, reproductive, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred polypeptides of the present invention comprise immunogenic epitopes shown in SEQ ID NO:124 as residues: Val-29 to Val-37, Asp-71 to His-76, Gln-78 to Gly-84, Met-105 to His-110, Trp-117 to Gly-122, Gln-136 to Lys-141, Leu-143 to Ala-149, Thr-162 to Asp-174, Ser-181 to Lys-186, Arg-214 to Glu-220, Glu-232 to Glu-238, Cys-249 to Asp-265. Polynucleotides encoding said polypeptides are also provided.

The tissue distribution in dendritic cells, activated monocytes and placental tissue (a tissue rich in hematopoeitic cells), and its homology to the T-cell receptor, indicates that polynucleotides and polypeptides corresponding to this gene are useful in the treatment, prophylaxis and/or diagnosis of immune and autoimmune diseases, such as lupus, transplant rejection, allergic reactions, arthritis, asthma, immunodeficiency diseases, leukemia, and AIDS. Its expression predominantly in hematopoietic cells also indicates that the gene could be important for the treatment and/or detection of hematopoietic disorders such as graft versus host reaction, graft versus host disease, transplant rejection, myelogenous leukemia, bone marrow fibrosis, and myeloproliferative disease. The protein could also be used to enhance or protect the proliferation, differentiation, and functional activation of hematopoietic progenitor cells such as bone marrow cells, which could be useful for cancer patients undergoing chemotherapy or patients undergoing bone marrow transplantation.

The protein may also be useful as a means to increase the proliferation of peripheral blood leukocytes, which could be useful in the combat of a range of hematopoietic disorders including immunodeficiency diseases, leukemia, and septicemia. In addition, expression in placenta indicates the gene or the protein encoded by this gene could be useful in the treatment, prophylaxis and/or diagnosis of placentitis, placenta previa, pregnancy disease, and miscarriage. Specific expression within the placenta indicates that this gene product may play a role in the proper establishment and maintenance of placental function. Alternately, this gene product is produced by the placenta and then transported to the embryo, where it may play a crucial role in the development and/or survival of the developing embryo or fetus. Expression of this gene product in a vascular-rich tissue such as the placenta also indicates that this gene product is produced more generally in endothelial cells or within the circulation. In such instances, it may play more generalized roles in vascular function, such as in angiogenesis. It may also be produced in the vasculature and have effects on other cells within the circulation, such as hematopoietic cells. It may serve to promote the proliferation, survival, activation, and/or differentiation of hematopoietic cells, as well as other cells throughout the body. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:123 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1576 of SEQ ID NO:123, b is an integer of 15 to 1590, where both a and b correspond to the positions of nucleotide residues shown in SEQ ID NO:123, and where b is greater than or equal to a+14.

Features of Protein Encoded by Gene No: 18

This gene is expressed primarily in adipose tissue and dendritic cells.

Therefore, polynucleotides and polypeptides of the invention are useful as reagents for differential identification of the tissue(s) or cell type(s) present in a biological sample and for diagnosis of diseases and conditions which include, but are not limited to, metabolic and immune disorders or diseases, particularly obesity. Similarly, polypeptides and antibodies directed to these polypeptides are useful in providing immunological probes for differential identification of the tissue(s) or cell type(s). For a number of disorders of the above tissues or cells, particularly of the immune, metabolic and digestive systems, expression of this gene at significantly higher or lower levels is routinely detected in certain tissues or cell types (e.g., immune, metabolic, digestive, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred polypeptides of the present invention comprise immunogenic epitopes shown in SEQ ID NO:128 as residues: Ile-40 to Glu-45, Cys-63 to Val-69, Glu-83 to Asn-94, Pro-107 to Cys-115, Phe-137 to Ser-143, Ser-159 to Thr-167, Glu-200 to Tyr-210. Polynucleotides encoding said polypeptides are also provided.

The tissue distribution in primarily adipose tissue indicates that polynucleotides and polypeptides corresponding to this gene are useful for the treatment, diagnosis and/or prophylaxis of obesity related disorders. In addition, expression in dendritic cells indicates a potential role in the treatment, diagnosis and/or prophylaxis of immune and autoimmune disorders such as lupus, transplant rejection, allergic reactions, arthritis, asthma, immunodeficiency diseases, leukemia, and AIDS. The tissue distribution in adipose tissue indicates that polynucleotides and polypeptides corresponding to this gene are useful for the treatment of obesity and other metabolic and endocrine conditions or disorders. Furthermore, the protein product of this gene may show utility in ameliorating conditions which occur secondary to aberrant fatty-acid metabolism (e.g. aberrant myelin sheath development), either directly or indirectly. Expression of this gene product in dendritic cells indicates a role in the regulation of the proliferation; survival; differentiation; and/or activation of potentially all hematopoietic cell lineages, including blood stem cells. This gene product is involved in the regulation of cytokine production, antigen presentation, or other processes that may also suggest a usefulness in the treatment of cancer (e.g. by boosting immune responses).

Since the gene is expressed in cells of lymphoid origin, the gene or protein, as well as, antibodies directed against the protein may show utility as a tumor marker and/or immunotherapy targets for the above listed tissues. Therefore it is also used as an agent for immunological disorders including arthritis, asthma, immune deficiency diseases such as AIDS, leukemia, rheumatoid arthritis, inflammatory bowel disease, sepsis, acne, and psoriasis. In addition, this gene product may have commercial utility in the expansion of stem cells and committed progenitors of various blood lineages, and in the differentiation and/or proliferation of various cell types. Expression of this gene product in dendritic cells also strongly indicates a role for this protein in immune function and immune surveillance. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:127 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1889 of SEQ ID NO:127, b is an integer of 15 to 1903, where both a and b correspond to the positions of nucleotide residues shown in SEQ ID NO:127, and where b is greater than or equal to a+14.

Features of Protein Encoded by Gene No: 19

The translation product of this gene shares sequence homology with alpha-1 antitrypsin (See Genebank accession no. gnl|PID|d1021080 and BAA20264; all references available through this accession are hereby incorporated by reference herein). Alpha-1-antitrypsin is an important plasma protease inhibitor affecting a wide variety of serine proteases involved in coagulation, fibrinolysis and kinen generation.

In specific embodiments, polypeptides of the invention comprise, or alternatively consists of, the following amino acid sequence:

(SEQ ID NO: 133)
GERRNWGGEVYYSTGYSSRK.

Moreover, fragments and variants of this polypeptide (such as, for example, fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding this polypeptide are encompassed by the invention. Antibodies that bind polypeptides of the invention are also encompassed by the invention. Polynucleotides encoding said polypeptides are also encompassed by the invention.

The polypeptide of this gene has been determined to have a transmembrane domain at about amino acid position 22-414 of the amino acid sequence referenced in Table 1A for this gene. Moreover, a cytoplasmic tail encompassing amino acids 5-21 of this protein has also been determined. Based upon these characteristics, it is believed that the protein product of this gene shares structural features to type Ib membrane proteins.

This gene is expressed in healing groin wound and to a lesser extent in some other tissues.

Polynucleotides and polypeptides of the invention are useful as reagents for differential identification of the tissue(s) or cell type(s) present in a biological sample and for diagnosis of diseases and conditions which include, but are not limited to, wound healing disorders. Similarly, polypeptides and antibodies directed to these polypeptides are useful in providing immunological probes for differential identification of the tissue(s) or cell type(s). For a number of disorders of the above tissues or cells, particularly of the healing groin wound, expression of this gene at significantly higher or lower levels may be routinely detected in certain tissues or cell types (e.g., healing, regenerative, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred polypeptides of the present invention comprise, or alternatively consist of, one or more immunogenic epitopes shown in SEQ ID NO:132 as residues: Phe-25 to Tyr-30, Gln-37 to Arg-42, Lys-106 to Leu-112, Leu-123 to Leu-130, Gln-142 to Phe-150, Gln-183 to Lys-188, Asp-219 to Glu-226, Lys-359 to Glu-366. Polynucleotides encoding said polypeptides are also encompassed by the invention.

The tissue distribution in healing groin wound and homology to alpha-1 antitrypsin indicates that polynucleotides and polypeptides corresponding to this gene are useful for diagnosis and therapeutic treatment of wound healing disorders. In addition, since healing wounds have transcriptional environments similar to developing tissues, the translation product of this gene may be useful for the diagnosis and treatment of cancer and other proliferative disorders.

Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Features of Protein Encoded by Gene No: 20

This gene is expressed in cerebellum and ovarian cancer.

Preferred polypeptides of the present invention comprise, or alternatively consist of, one or more of the immunogenic epitopes shown in SEQ ID NO:135 as residues: Thr-41 to Gly-47, Pro-170 to Asp-176, Leu-257 to Trp-262, Gln-276 to Ser-283, Arg-323 to Leu-330, Pro-409 to Ser-427, Gly 440 to Ala-449, Arg-323 to Gly-331, Glu-348 to Ser 354, Arg-256 to Trp-262, Phe 278 to Val 285, Arg 362 to Gly 385. Preferred polypeptides of the present invention comprise immunogenic epitopes shown in SEQ ID NO:140 as residues: Thr-41 to Gly-47, Pro-170 to Asp-176, Leu-257 to Trp-262, Gln-276 to Ser-283, Arg-323 to Leu-330, Pro-362 to Val-374. Polynucleotides encoding said polypeptides are also encompassed by the invention. Antibodies that bind said epitopes or other polypeptides of the invention are also encompassed.

In a specific embodiment, polypeptides of the invention, comprise or alternatively consist of, an amino acid sequence selected from the group:

```
                              (SEQ ID NO: 141)
FHGLGRLHTVHL,

                              (SEQ ID NO: 142)
AAFTGLALLEQLDLSDNAQLR,

                              (SEQ ID NO: 143)
HEVPDAPRPTPT,
and/or

                              (SEQ ID NO: 144)
AFRGLHSLD.
```

Polynucleotides encoding these polypeptides are also encompassed by the invention as are antibodies that bind one or more of these polypeptides. Moreover, fragments and variants of these polypeptides (such as, for example, fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides, or the complement thereof) are encompassed by the invention. Antibodies that bind polypeptides of the invention are also encompassed by the invention. Polynucleotides encoding these polypeptides are also encompassed by the invention.

Also preferred are polypeptides, comprising or alternatively consisting of, the mature polypeptide which is predicted to consist of residues 27-473 of the foregoing sequence (SEQ ID NO:135), and biologically active fragments of the mature polypeptide (e.g., fragments that prevent neural/neuronal damage and/or spinal cord injury). Polynucleotides encoding these polypeptides are also encompassed by the invention. Moreover, fragments and variants of these polypeptides (such as, for example, fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides, or the complement thereof) are encompassed by the invention. Antibodies that bind polypeptides of the invention are also encompassed by the invention. Polynucleotides encoding these polypeptides are also encompassed by the invention.

In a nonexclusive specific embodiment, polypeptides of the invention, comprise or alternatively consist of, one or more of the following amino acid sequences and biologically active fragments thereof (e.g., fragments that prevent neural/neuronal damage and/or spinal cord injury):

```
                              (SEQ ID NO: 145)
SQRIFLHGNRISHVPAASFRAC,

                              (SEQ ID NO: 146)
LTILWLHSNVLARIDAAAFTGL,

                              (SEQ ID NO: 147)
LEQLDLSDNAQLRSVDPATFHGL,

                              (SEQ ID NO: 148)
LHTLHLDRCGLQELGPGLFRGL,

                              (SEQ ID NO: 149)
LQYLYLQDNALQALPDDTFRDL,

                              (SEQ ID NO: 150)
LTHLFLHGNRISSVPERAFRGL,

                              (SEQ ID NO: 151)
LDRLLLHQNRVAHVHPHAFRDL,

                              (SEQ ID NO: 152)
LMTLYLFANNLSALPTEALAPL,

                              (SEQ ID NO: 153)
AHCSAARGLRATR,

                              (SEQ ID NO: 154)
PAHCSAARGLRATRF,

                              (SEQ ID NO: 155)
PSLTCSLTPLGLALVLWTVLGPC,

                              (SEQ ID NO: 156)
LPSLTCSLTPLGLALVLWTVL,

                              (SEQ ID NO: 157)
LPSLTCSLTPLGLALVLWTVLGPC,
and

                              (SEQ ID NO: 158)
CRNLTILWLHSNVL.
```

Polynucleotides encoding these polypeptides are also encompassed by the invention as are antibodies that bind one or more of these polypeptides. Moreover, fragments and variants of these polypeptides (such as, for example, fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides, or the complement thereof) are encompassed by the invention. Antibodies that bind polypeptides of the invention are also encompassed by the invention. Polynucleotides encoding these polypeptides are also encompassed by the invention.

In a further embodiment of the invention, a Fc region of an immunoglobulin (e.g., IgG Fc) molecule is fused to one, two, three, four, five, six, seven, eight, nine, ten, eleven, twelve, thirteen, or all fourteen of the polypeptide(s) selected from the group consisting of:

```
                              (SEQ ID NO: 145)
SQRIFLHGNRISHVPAASFRAC,

                              (SEQ ID NO: 146)
LTILWLHSNVLARIDAAAFTGL,
```

-continued (SEQ ID NO: 147)
LEQLDLSDNAQLRSVDPATFHGL, (SEQ ID NO: 148)
LHTLHLDRCGLQELGPGLFRGL, (SEQ ID NO: 149)
LQYLYLQDNALQALPDDTFRDL, (SEQ ID NO: 150)
LTHLFLHGNRISSVPERAFRGL, (SEQ ID NO: 151)
LDRLLLHQNRVAHVHPHAFRDL, (SEQ ID NO: 152)
LMTLYLFANNLSALPTEALAPL, (SEQ ID NO: 153)
AHCSAARGLRATR, (SEQ ID NO: 154)
PAHCSAARGLRATRF, (SEQ ID NO: 155)
PSLTCSLTPLGLALVLWTVLGPC, (SEQ ID NO: 156)
LPSLTCSLTPLGLALVLWTVL, (SEQ ID NO: 157)
LPSLTCSLTPLGLALVLWTVLGPC,
and (SEQ ID NO: 158)
CRNLTILWLHSNVL.

Moreover, fragments and variants of these polypeptides (such as, for example, fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides, or the complement thereof) are encompassed by the invention. Antibodies that bind polypeptides of the invention are also encompassed by the invention. Polynucleotides encoding these polypeptides are also encompassed by the invention.

In additional embodiments, proteins comprising fragments or variants of a polypeptide of SEQ ID NO:135 (such as, for example, fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides, or the complement there of) are fused to an Fc region of an immunoglobulin that bind the 66-amino acid extracellular loop of Nogo-A (See Genbank Accession CAB99248; GrandPre, T., et al., Nature, 403, pp. 439-444 (2000). Polynucleotides encoding these polypeptides are also encompassed by the invention, as are antibodies that bind one or more of these polypeptides.

Thus, the fragment, derivative or analog of the polypeptide of FIGS. 7A-C (SEQ ID NO:135), or that encoded by the deposited cDNA plasmid, may be (i) one in which one or more of the amino acid residues are substituted with a conserved or non conserved amino acid residue (preferably a conserved amino acid residue) and such substituted amino acid residue may or may not be one encoded by the genetic code, or (ii) one in which one or more of the amino acid residues includes a substituent group, or (iii) one in which the extracellular domain of the polypeptide is fused with another compound, such as a compound to increase the half life of the polypeptide (for example, polyethylene glycol), or (iv) one in which the additional amino acids are fused to the extracellular domain of the polypeptide, such as an IgG Fc fusion region peptide or leader or secretory sequence or a sequence which is employed for purification of the extracellular domain of the polypeptide or a proprotein sequence. Such fragments, derivatives and analogs are deemed to be within the scope of those skilled in the art from the teachings herein.

The present invention further includes compositions comprising the polypeptides of the present invention fused or conjugated to antibody domains other than the variable regions. For example, the polypeptides of the present invention may be fused or conjugated to an antibody Fc region, or portion thereof. The antibody portion fused to a polypeptide of the present invention may comprise the constant region, hinge region, CH1 domain, CH2 domain, and CH3 domain or any combination of whole domains or portions thereof. The polypeptides may also be fused or conjugated to the above antibody portions to form multimers. For example, Fc portions fused to the polypeptides of the present invention can form dimers through disulfide bonding between the Fc portions. Higher multimeric forms can be made by fusing the polypeptides to portions of IgA and IgM. Methods for fusing or conjugating the polypeptides of the present invention to antibody portions are known in the art. See, e.g., U.S. Pat. Nos. 5,336,603; 5,622,929; 5,359,046; 5,349,053; 5,447,851; 5,112,946; EP 307,434; EP 367,166; PCT publications WO 96/04388; WO 91/06570; Ashkenazi et al., Proc. Natl. Acad. Sci. USA 88:10535-10539 (1991); Zheng et al., J. Immunol. 154:5590-5600 (1995); and Vil et al., Proc. Natl. Acad. Sci. USA 89:11337-11341 (1992) (said references incorporated by reference in their entireties).

As one of skill in the art will appreciate, and as discussed above, the polypeptides of the present invention (e.g., those comprising an immunogenic or antigenic epitope) can be fused to heterologous polypeptide sequences. For example, polypeptides of the present invention (including fragments or variants thereof), may be fused with the constant domain of immunoglobulins (IgA, IgE, IgG, IgM), or portions thereof (CH1, CH2, CH3, or any combination thereof and portions thereof, resulting in chimeric polypeptides. By way of another non-limiting example, polypeptides and/or antibodies of the present invention (including fragments or variants thereof) may be fused with albumin (including but not limited to recombinant human serum albumin or fragments or variants thereof (see, e.g., U.S. Pat. No. 5,876,969, issued Mar. 2, 1999, EP Patent 0 413 622, and U.S. Pat. No. 5,766,883, issued Jun. 16, 1998, herein incorporated by reference in their entirety)). In a preferred embodiment, polypeptides and/or antibodies of the present invention (including fragments or variants thereof) are fused with the mature form of human serum albumin (i.e., amino acids 1-585 of human serum albumin as shown in FIGS. 1 and 2 of EP Patent 0 322 094) which is herein incorporated by reference in its entirety. In another preferred embodiment, polypeptides and/or antibodies of the present invention (including fragments or variants thereof) are fused with polypeptide fragments comprising, or alternatively consisting of, amino acid residues 1-z of human serum albumin, where z is an integer from 369 to 419, as described in U.S. Pat. No. 5,766,883 herein incorporated by reference in its entirety. Polypeptides and/or antibodies of the present invention (including fragments or variants thereof) may be fused to either the N- or C-terminal end of the heterologous protein (e.g., immunoglobulin Fc polypeptide or human serum albumin polypeptide). Polynucleotides encoding fusion proteins of the invention are also encompassed by the invention.

Such fusion proteins as those described above may facilitate purification and may increase half-life in vivo. This has been shown for chimeric proteins consisting of the first two domains of the human CD4-polypeptide and various domains of the constant regions of the heavy or light chains of mammalian immunoglobulins. See, e.g., EP 394,827; Traunecker et al., Nature, 331:84-86 (1988). Enhanced delivery of an antigen across the epithelial barrier to the immune system has been demonstrated for antigens (e.g., insulin) conjugated to an FcRn binding partner such as IgG or Fc fragments (see, e.g., PCT Publications WO 96/22024 and WO 99/04813). IgG Fusion proteins that have a disulfide-linked dimeric structure due to the IgG portion desulfide bonds have also been found to be more efficient in binding and neutralizing other molecules than monomeric polypeptides or fragments thereof alone. See, e.g., Fountoulakis et al., J. Biochem., 270:3958-3964 (1995). Nucleic acids encoding the above epitopes can also be recombined with a gene of interest as an epitope tag (e.g., the hemagglutinin (ìHAî) tag or flag tag) to aid in detection and purification of the expressed polypeptide. For example, a system described by Janknecht et al. allows for the ready purification of non-denatured fusion proteins expressed in human cell lines (Janknecht et al., 1991, Proc. Natl. Acad. Sci. USA 88:8972-897). In this system, the gene of interest is subcloned into a vaccinia recombination plasmid such that the open reading frame of the gene is translationally fused to an amino-terminal tag consisting of six histidine residues. The tag serves as a matrix binding domain for the fusion protein. Extracts from cells infected with the recombinant vaccinia virus are loaded onto Ni2+ nitriloacetic acid-agarose column and histidine-tagged proteins can be selectively eluted with imidazole-containing buffers.

FIGS. 7A-C show the nucleotide (SEQ ID NO:134) and deduced amino acid sequence (SEQ ID NO:135) corresponding to this gene.

FIG. 8 shows an analysis of the amino acid sequence (SEQ ID NO:135). Alpha, beta, turn and coil regions; hydrophilicity and hydrophobicity; amphipathic regions; flexible regions; antigenic index and surface probability are shown, and all were generated using the default settings of the recited computer algorithms. In the "Antigenic Index or Jameson Wolf" graph, the positive peaks indicate locations of the highly antigenic regions of the protein, i.e., regions from which epitope-bearing peptides of the invention can be obtained. Polypeptides comprising, or alternatively consisting of, domains defined by these graphs are contemplated by the present invention, as are polynucleotides encoding these polypeptides.

The data presented in FIG. 8 are also represented in tabular form in Table 9. The columns are labeled with the headings "Res", "Position", and Roman Numerals I XIV. The column headings refer to the following features of the amino acid sequence presented in FIG. 8, and Table 9: "Res": amino acid residue of SEQ ID NO:135 and FIGS. 7A-C; "Position": position of the corresponding residue within SEQ ID NO:135 and FIGS. 7A-C; I: Alpha, Regions Garnier Robson; II: Alpha, Regions Chou Fasman; III: Beta, Regions Garnier Robson; IV: Beta, Regions Chou Fasman; V: Turn, Regions Garnier Robson; VI: Turn, Regions Chou Fasman; VII: Coil, Regions Garnier Robson; VIII: Hydrophilicity Plot Kyte Doolittle; IX: Hydrophobicity Plot Hopp Woods; X: Alpha, Amphipathic Regions Eisenberg; XI: Beta, Amphipathic Regions Eisenberg; XII: Flexible Regions Karplus Schulz; XIII: Antigenic Index Jameson Wolf; and XIV: Surface Probability Plot Emini.

Preferred embodiments of the invention in this regard include fragments that comprise, or alternatively consisting of, one or more of the following regions: alpha-helix and alpha-helix forming regions ("alpha-regions"), beta-sheet and beta-sheet forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, flexible regions, surface-forming regions and high antigenic index regions. The data representing the structural or functional attributes of the protein set forth in FIG. 8 and/or Table 9, as described above, was generated using the various modules and algorithms of the DNA*STAR set on default parameters. In a preferred embodiment, the data presented in columns VIII, IX, XIII, and XIV of Table 9 can be used to determine regions of the protein which exhibit a high degree of potential for antigenicity. Regions of high antigenicity are determined from the data presented in columns VIII, IX, XIII, and/or XIV by choosing values which represent regions of the polypeptide which are likely to be exposed on the surface of the polypeptide in an environment in which antigen recognition may occur in the process of initiation of an immune response.

Certain preferred regions in these regards are set out in FIG. 8, but may, as shown in Table 9, be represented or identified by using tabular representations of the data presented in FIG. 8. The DNA*STAR computer algorithm used to generate FIG. 8 (set on the original default parameters) was used to present the data in FIG. 8 in a tabular format (See Table 9). The tabular format of the data in FIG. 8 is used to easily determine specific boundaries of a preferred region.

The present invention is further directed to fragments of the polynucleotide sequences described herein. By a fragment of, for example, the polynucleotide sequence of a deposited cDNA or the nucleotide sequence shown in SEQ ID NO:134, is intended polynucleotide fragments at least about 15 nt, and more preferably at least about 20 nt, at least about 25 nt, still more preferably at least about 30 nt, at least about 35 nt, and even more preferably, at least about 40 nt in length, at least about 45 nt in length, at least about 50 nt in length, at least about 60 nt in length, at least about 70 nt in length, at least about 80 nt in length, at least about 90 nt in length, at least about 100 nt in length, at least about 125 nt in length, at least about 150 nt in length, at least about 175 nt in length, which are useful as diagnostic probes and primers as discussed herein. Of course, larger fragments 200-1500 nt in length are also useful according to the present invention, as are fragments corresponding to most, if not all, of the nucleotide sequence of a deposited cDNA or as shown in SEQ ID NO:134. By a fragment at least 20 nt in length, for example, is intended fragments which include 20 or more contiguous bases from the nucleotide sequence of a deposited cDNA or the nucleotide sequence as shown in SEQ ID NO:134. In this context "about" includes the particularly recited size, an sizes larger or smaller by several (5, 4, 3, 2, or 1) nucleotides, at either terminus or at both termini. Representative examples of polynucleotide fragments of the invention include, for example, fragments that comprise, or alternatively, consist of, a sequence from about nucleotide 1 to about 50, from about 51 to about 100, from about 101 to about 150, from about 151 to about 200, from about 201 to about 250, from about 251 to about 300, from about 301 to about 350, from about 351 to about 400, from about 401 to about 450, from about 451 to about 500, and from about 501 to about 550, and from about 551 to about 600, from about 601 to about 650, from about 651 to about 700, from about 701 to about 750, from about 751 to about 800, from about 801 to about 850, from about 851 to about 900, from about 901 to about 950, from about 951 to about 1000, from about 1001 to about 1050, from about 1051 to about 1100, from about 1101 to about 1150 from about 1151 to about 1200, from about 1201 to about 1250, from about 1251 to about 1300, from about 1301 to about 1350, from about 1351 to about 1400, from about 1401 to about 1450, and from about 1451 to about 1500, from about 1501 to about 1550, from about 1551 to about 1600, from about 1601 to about 1650 from about 1651 to about 1700, from about 1701 to about 1750, from about 1751 to about 1777 of SEQ ID NO:134, or the complementary strand thereto, or the cDNA contained in a deposited clone. In this context "about" includes the particularly recited ranges, and ranges larger or smaller by several (5, 4, 3, 2, or 1) nucleotides, at either terminus or at both termini. In additional embodiments, the polynucleotides of the invention encode functional attributes of the corresponding protein.

Preferred polypeptide fragments of the invention comprise, or alternatively consist of, the secreted protein having a continuous series of deleted residues from the amino or the carboxy terminus, or both. Particularly, N-terminal deletions of the polypeptide can be described by the general formula m−473 where m is an integer from 2 to 467, where m corresponds to the position of the amino acid residue identified in SEQ ID NO:135. More in particular, the invention provides polynucleotides encoding polypeptides comprising, or alternatively consisting of, an amino acid sequence selected from the group: K-2 to C-473; R-3 to C-473; A-4 to C-473; S-5 to C-473; A-6 to C-473; G-7 to C-473; G-8 to C-473; S-9 to C-473; R-10 to C-473; L-11 to C-473; L-12 to C-473; A-13 to C-473; W-14 to C-473; V-15 to C-473; L-16 to C-473; W-17 to C-473; L-18 to C-473; Q-19 to C-473; A-20 to C-473; W-21 to C-473; Q-22 to C-473; V-23 to C-473; A-24 to C-473; A-25 to C-473; P-26 to C-473; C-27 to C-473; P-28 to C-473; G-29 to C-473; A-30 to C-473; C-31 to C-473; V-32 to C-473; C-33 to C-473; Y-34 to C-473; N-35 to C-473; E-36 to C-473; P-37 to C-473; K-38 to C-473; V-39 to C-473; T-40 to C-473; T-41 to C-473; S-42 to C-473; C-43 to C-473; P-44 to C-473; Q-45 to C-473; Q-46 to C-473; G-47 to C-473; L-48 to C-473; Q-49 to C-473; A-50 to C-473; V-51 to C-473; P-52 to C-473; V-53 to C-473; G-54 to C-473; I-55 to C-473; P-56 to C-473; A-57 to C-473; A-58 to C-473; S-59 to C-473; Q-60 to C-473; R-61 to C-473; I-62 to C-473; F-63 to C-473; L-64 to C-473; H-65 to C-473; G-66 to C-473; N-67 to C-473; R-68 to C-473; I-69 to C-473; S-70 to C-473; H-71 to C-473; V-72 to C-473; P-73 to C-473; A-74 to C-473; A-75 to C-473; S-76 to C-473; F-77 to C-473; R-78 to C-473; A-79 to C-473; C-80 to C-473; R-81 to C-473; N-82 to C-473; L-83 to C-473; T-84 to C-473; I-85 to C-473; L-86 to C-473; W-87 to C-473; L-88 to C-473; H-89 to C-473; S-90 to C-473; N-91 to C-473; V-92 to C-473; L-93 to C-473; A-94 to C-473; R-95 to C-473; I-96 to C-473; D-97 to C-473; A-98 to C-473; A-99 to C-473; A-100 to C-473; F-101 to C-473; T-102 to C-473; G-103 to C-473; L-104 to C-473; A-105 to C-473; L-106 to C-473; L-107 to C-473; E-108 to C-473; Q-109 to C-473; L-110 to C-473; D-111 to C-473; L-112 to C-473; S-113 to C-473; D-114 to C-473; N-115 to C-473; A-116 to C-473; Q-117 to C-473; L-118 to C-473; R-119 to C-473; S-120 to C-473; V-121 to C-473; D-122 to C-473; P-123 to C-473; A-124 to C-473; T-125 to C-473; F-126 to C-473; H-127 to C-473; G-128 to C-473; L-129 to C-473; G-130 to C-473; R-131 to C-473; L-132 to C-473; H-133 to C-473; T-134 to C-473; L-135 to C-473; H-136 to C-473; L-137 to C-473; D-138 to C-473; R-139 to C-473; C-140 to C-473; G-141 to C-473; L-142 to C-473; Q-143 to C-473; E-144 to C-473; L-145 to C-473; G-146 to C-473; P-147 to C-473; G-148 to C-473; L-149 to C-473; F-150 to C-473; R-151 to C-473; G-152 to C-473; L-153 to C-473; A-154 to C-473; A-155 to C-473; L-156 to C-473; Q-157 to C-473; Y-158 to C-473; L-159 to C-473; Y-160 to C-473; L-161 to C-473; Q-162 to C-473; D-163 to C-473; N-164 to C-473; A-165 to C-473; L-166 to C-473; Q-167 to C-473; A-168 to C-473; L-169 to C-473; P-170 to C-473; D-171 to C-473; D-172 to C-473; T-173 to C-473; F-174 to C-473; R-175 to C-473; D-176 to C-473; L-177 to C-473; G-178 to C-473; N-179 to C-473; L-180 to C-473; T-181 to C-473; H-182 to C-473; L-183 to C-473; F-184 to C-473; L-185 to C-473; H-186 to C-473; G-187 to C-473; N-188 to C-473; R-189 to C-473; I-190 to C-473; S-191 to C-473; S-192 to C-473; V-193 to C-473; P-194 to C-473; E-195 to C-473; R-196 to C-473; A-197 to C-473; F-198 to C-473; R-199 to C-473; G-200 to C-473; L-201 to C-473; H-202 to C-473; S-203 to C-473; L-204 to C-473; D-205 to C-473; R-206 to C-473; L-207 to C-473; L-208 to C-473; L-209 to C-473; H-210 to C-473; Q-211 to C-473; N-212 to C-473; R-213 to C-473; V-214 to C-473; A-215 to C-473; H-216 to C-473; V-217 to C-473; H-218 to C-473; P-219 to C-473; H-220 to C-473; A-221 to C-473; F-222 to C-473; R-223 to C-473; D-224 to C-473; L-225 to C-473; G-226 to C-473; R-227 to C-473; L-228 to C-473; M-229 to C-473; T-230 to C-473; L-231 to C-473; Y-232 to C-473; L-233 to C-473; F-234 to C-473; A-235 to C-473; N-236 to C-473; N-237 to C-473; L-238 to C-473; S-239 to C-473; A-240 to C-473; L-241 to C-473; P-242 to C-473; T-243 to C-473; E-244 to C-473; A-245 to C-473; L-246 to C-473; A-247 to C-473; P-248 to C-473; L-249 to C-473; R-250 to C-473; A-251 to C-473; L-252 to C-473; Q-253 to C-473; Y-254 to C-473; L-255 to C-473; R-256 to C-473; L-257 to C-473; N-258 to C-473; D-259 to C-473; N-260 to C-473; P-261 to C-473; W-262 to C-473; V-263 to C-473; C-264 to C-473; D-265 to C-473; C-266 to C-473; R-267 to C-473; A-268 to C-473; R-269 to C-473; P-270 to C-473; L-271 to C-473; W-272 to C-473; A-273 to C-473; W-274 to C-473; L-275 to C-473; Q-276 to C-473; K-277 to C-473; F-278 to C-473; R-279 to C-473; G-280 to C-473; S-281 to C-473; S-282 to C-473; S-283 to C-473; E-284 to C-473; V-285 to C-473; P-286 to C-473; C-287 to C-473; S-288 to C-473; L-289 to C-473; P-290 to C-473; Q-291 to C-473; R-292 to C-473; L-293 to C-473; A-294 to C-473; G-295 to C-473; R-296 to C-473; D-297 to C-473; L-298 to C-473; K-299 to C-473; R-300 to C-473; L-301 to C-473; A-302 to C-473; A-303 to C-473; N-304 to C-473; D-305 to C-473; L-306 to C-473; Q-307 to C-473; G-308 to C-473; C-309 to C-473; A-310 to C-473; V-311 to C-473; A-312 to C-473; T-313 to C-473; G-314 to C-473; P-315 to C-473; Y-316 to C-473; H-317 to C-473; P-318 to C-473; I-319 to C-473; W-320 to C-473; T-321 to C-473; G-322 to C-473; R-323 to C-473; A-324 to C-473; T-325 to C-473; D-326 to C-473; E-327 to C-473; E-328 to C-473; P-329 to C-473; L-330 to C-473; G-331 to C-473; L-332 to C-473; P-333 to C-473; K-334 to C-473; C-335 to C-473; C-336 to C-473; Q-337 to C-473; P-338 to C-473; D-339 to C-473; A-340 to C-473; A-341 to C-473; D-342 to C-473; K-343 to C-473; A-344 to C-473; S-345 to C-473; V-346 to C-473; L-347 to C-473; E-348 to C-473; P-349 to C-473; G-350 to C-473; R-351 to C-473; P-352 to C-473; A-353 to C-473; S-354 to C-473; A-355 to C-473; G-356 to C-473; N-357 to C-473; A-358 to C-473; L-359 to C-473; K-360 to C-473; G-361 to C-473; R-362 to C-473; V-363 to C-473; P-364 to C-473; P-365 to C-473; G-366 to C-473; D-367 to C-473; S-368 to C-473; P-369 to C-473; P-370 to C-473; G-371 to C-473; N-372 to C-473; G-373 to C-473; S-374 to C-473; G-375 to C-473; P-376 to C-473; R-377 to C-473; H-378 to C-473; I-379 to C-473; N-380 to C-473; D-381 to C-473; S-382 to C-473; P-383 to C-473; F-384 to C-473; G-385 to C-473; T-386 to C-473; L-387 to C-473; P-388 to C-473; G-389 to C-473; S-390 to C-473; A-391 to C-473; E-392 to C-473; P-393 to C-473;

P-394 to C-473; A-395 to C-473; H-396 to C-473; C-397 to C-473; S-398 to C-473; A-399 to C-473; A-400 to C-473; R-401 to C-473; G-402 to C-473; L-403 to C-473; R-404 to C-473; A-405 to C-473; T-406 to C-473; R-407 to C-473; F-408 to C-473; P-409 to C-473; T-410 to C-473; S-411 to C-473; G-412 to C-473; P-413 to C-473; R-414 to C-473; R-415 to C-473; R-416 to C-473; P-417 to C-473; G-418 to C-473; C-419 to C-473; S-420 to C-473; R-421 to C-473; K-422 to C-473; N-423 to C-473; R-424 to C-473; T-425 to C-473; R-426 to C-473; S-427 to C-473; H-428 to C-473; C-429 to C-473; R-430 to C-473; L-431 to C-473; G-432 to C-473; Q-433 to C-473; A-434 to C-473; G-435 to C-473; S-436 to C-473; G-437 to C-473; G-438 to C-473; G-439 to C-473; G-440 to C-473; T-441 to C-473; G-442 to C-473; D-443 to C-473; S-444 to C-473; E-445 to C-473; G-446 to C-473; S-447 to C-473; G-448 to C-473; A-449 to C-473; L-450 to C-473; P-451 to C-473; S-452 to C-473; L-453 to C-473; T-454 to C-473; C-455 to C-473; S-456 to C-473; L-457 to C-473; T-458 to C-473; P-459 to C-473; L-460 to C-473; G-461 to C-473; L-462 to C-473; A-463 to C-473; L-464 to C-473; V-465 to C-473; L-466 to C-473; W-467 to C-473; and T-468 to C-473 of SEQ ID NO:135. Polypeptides encoded by these polynucleotides are also encompassed by the invention. Moreover, fragments and variants of these polypeptides (such as, for example, fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides, or the complement thereof) are encompassed by the invention. Antibodies that bind polypeptides of the invention are also encompassed by the invention. Polynucleotides encoding these polypeptides are also encompassed by the invention.

Also as mentioned above, even if deletion of one or more amino acids from the C terminus of a protein results in modification of loss of one or more biological functions of the protein (e.g., modulation of neurite growth, including, but not limited to, inhibitory activity and/or antiinflammatory activity), other functional activities (e.g., biological activities, ability to multimerize, ability to bind ligand, ability to generate antibodies, ability to bind antibodies) may still be retained. For example the ability of the shortened polypeptide to induce and/or bind to antibodies which recognize the complete or mature forms of the polypeptide generally will be retained when less than the majority of the residues of the complete or mature polypeptide are removed from the C terminus. Whether a particular polypeptide lacking C terminal residues of a complete polypeptide retains such immunologic activities can readily be determined by routine methods described herein and otherwise known in the art. It is not unlikely that a polypeptide with a large number of deleted C terminal amino acid residues may retain some biological or immunogenic activities. In fact, peptides composed of as few as six amino acid residues may often evoke an immune response.

Accordingly, the present invention further provides polypeptides having one or more residues deleted from the carboxy terminus of the amino acid sequence of the polypeptide shown in FIGS. 7A-C (SEQ ID NO:135), as described by the general formula 1-n, where n is an integer from 6 to 472, where n corresponds to the position of the amino acid residue identified in SEQ ID NO:135. More in particular, the invention provides polynucleotides encoding polypeptides comprising, or alternatively consisting of, an amino acid sequence selected from the group: M-1 to P-472; M-1 to G-471; M-1 to L-470; M-1 to V-469; M-1 to T-468; M-1 to W-467; M-1 to L-466; M-1 to V-465; M-1 to L-464; M-1 to A-463; M-1 to L-462; M-1 to G-461; M-1 to L-460; M-1 to P-459; M-1 to T-458; M-1 to L-457; M-1 to S-456; M-1 to C-455; M-1 to T-454; M-1 to L-453; M-1 to S-452; M-1 to P-451; M-1 to L-450; M-1 to A-449; M-1 to G-448; M-1 to S-447; M-1 to G-446; M-1 to E-445; M-1 to S-444; M-1 to D-443; M-1 to G-442; M-1 to T-441; M-1 to G-440; M-1 to G-439; M-1 to G-438; M-1 to G-437; M-1 to S-436; M-1 to G-435; M-1 to A-434; M-1 to Q-433; M-1 to G-432; M-1 to L-431; M-1 to R-430; M-1 to C-429; M-1 to H-428; M-1 to S-427; M-1 to R-426; M-1 to T-425; M-1 to R-424; M-1 to N-423; M-1 to K-422; M-1 to R-421; M-1 to S-420; M-1 to C-419; M-1 to G-418; M-1 to P-417; M-1 to R-416; M-1 to R-415; M-1 to R-414; M-1 to P-413; M-1 to G-412; M-1 to S-411; M-1 to T-410; M-1 to P-409; M-1 to F-408; M-1 to R-407; M-1 to T-406; M-1 to A-405; M-1 to R-404; M-1 to L-403; M-1 to G-402; M-1 to R-401; M-1 to A-400; M-1 to A-399; M-1 to S-398; M-1 to C-397; M-1 to H-396; M-1 to A-395; M-1 to P-394; M-1 to P-393; M-1 to E-392; M-1 to A-391; M-1 to S-390; M-1 to G-389; M-1 to P-388; M-1 to L-387; M-1 to T-386; M-1 to G-385; M-1 to F-384; M-1 to P-383; M-1 to S-382; M-1 to D-381; M-1 to N-380; M-1 to I-379; M-1 to H-378; M-1 to R-377; M-1 to P-376; M-1 to G-375; M-1 to S-374; M-1 to G-373; M-1 to N-372; M-1 to G-371; M-1 to P-370; M-1 to P-369; M-1 to S-368; M-1 to D-367; M-1 to G-366; M-1 to P-365; M-1 to P-364; M-1 to V-363; M-1 to R-362; M-1 to G-361; M-1 to K-360; M-1 to L-359; M-1 to A-358; M-1 to N-357; M-1 to G-356; M-1 to A-355; M-1 to S-354; M-1 to A-353; M-1 to P-352; M-1 to R-351; M-1 to G-350; M-1 to P-349; M-1 to E-348; M-1 to L-347; M-1 to V-346; M-1 to S-345; M-1 to A-344; M-1 to K-343; M-1 to D-342; M-1 to A-341; M-1 to A-340; M-1 to D-339; M-1 to P-338; M-1 to Q-337; M-1 to C-336; M-1 to C-335; M-1 to K-334; M-1 to P-333; M-1 to L-332; M-1 to G-331; M-1 to L-330; M-1 to P-329; M-1 to E-328; M-1 to E-327; M-1 to D-326; M-1 to T-325; M-1 to A-324; M-1 to R-323; M-1 to G-322; M-1 to T-321; M-1 to W-320; M-1 to I-319; M-1 to P-318; M-1 to H-317; M-1 to Y-316; M-1 to P-315; M-1 to G-314; M-1 to T-313; M-1 to A-312; M-1 to V-311; M-1 to A-310; M-1 to C-309; M-1 to G-308; M-1 to Q-307; M-1 to L-306; M-1 to D-305; M-1 to N-304; M-1 to A-303; M-1 to A-302; M-1 to L-301; M-1 to R-300; M-1 to K-299; M-1 to L-298; M-1 to D-297; M-1 to R-296; M-1 to G-295; M-1 to A-294; M-1 to L-293; M-1 to R-292; M-1 to Q-291; M-1 to P-290; M-1 to L-289; M-1 to S-288; M-1 to C-287; M-1 to P-286; M-1 to V-285; M-1 to E-284; M-1 to S-283; M-1 to S-282; M-1 to S-281; M-1 to G-280; M-1 to R-279; M-1 to F-278; M-1 to K-277; M-1 to Q-276; M-1 to L-275; M-1 to W-274; M-1 to A-273; M-1 to W-272; M-1 to L-271; M-1 to P-270; M-1 to R-269; M-1 to A-268; M-1 to R-267; M-1 to C-266; M-1 to D-265; M-1 to C-264; M-1 to V-263; M-1 to W-262; M-1 to P-261; M-1 to N-260; M-1 to D-259; M-1 to N-258; M-1 to L-257; M-1 to R-256; M-1 to L-255; M-1 to Y-254; M-1 to Q-253; M-1 to L-252; M-1 to A-251; M-1 to R-250; M-1 to L-249; M-1 to P-248; M-1 to A-247; M-1 to L-246; M-1 to A-245; M-1 to E-244; M-1 to T-243; M-1 to P-242; M-1 to L-241; M-1 to A-240; M-1 to S-239; M-1 to L-238; M-1 to N-237; M-1 to N-236; M-1 to A-235; M-1 to F-234; M-1 to L-233; M-1 to Y-232; M-1 to L-231; M-1 to T-230; M-1 to M-229; M-1 to L-228; M-1 to R-227; M-1 to G-226; M-1 to L-225; M-1 to D-224; M-1 to R-223; M-1 to F-222; M-1 to A-221; M-1 to H-220; M-1 to P-219; M-1 to H-218; M-1 to V-217; M-1 to H-216; M-1 to A-215; M-1 to V-214; M-1 to R-213; M-1 to N-212; M-1 to Q-211; M-1 to H-210; M-1 to L-209; M-1 to L-208; M-1 to L-207; M-1 to R-206; M-1 to D-205; M-1 to L-204; M-1 to S-203; M-1 to H-202; M-1 to L-201; M-1 to G-200; M-1 to R-199; M-1 to F-198; M-1 to A-197; M-1 to R-196; M-1 to E-195; M-1 to P-194; M-1 to V-193; M-1 to S-192; M-1 to S-191; M-1 to I-190; M-1 to R-189; M-1 to N-188; M-1 to G-187; M-1 to H-186; M-1 to L-185; M-1 to F-184; M-1 to L-183; M-1 to H-182; M-1 to T-181; M-1 to L-180; M-1 to N-179; M-1 to G-178; M-1 to L-177; M-1 to D-176; M-1 to R-175; M-1 to F-174; M-1 to T-173; M-1 to D-172; M-1 to D-171; M-1 to P-170; M-1 to L-169; M-1 to A-168; M-1 to Q-167; M-1 to L-166; M-1 to A-165; M-1 to N-164; M-1 to D-163; M-1 to Q-162; M-1 to L-161; M-1 to Y-160; M-1 to L-159; M-1 to Y-158; M-1 to Q-157; M-1 to L-156; M-1 to A-155; M-1 to A-154; M-1 to L-153; M-1 to G-152; M-1 to R-151; M-1 to F-150; M-1 to L-149; M-1 to G-148; M-1 to P-147; M-1 to G-146; M-1 to L-145; M-1 to E-144; M-1 to Q-143; M-1 to L-142; M-1 to G-141; M-1 to C-140; M-1 to R-139; M-1 to D-138; M-1 to L-137; M-1 to H-136; M-1 to L-135; M-1 to T-134; M-1 to H-133; M-1 to L-132; M-1 to R-131; M-1 to G-130; M-1 to L-129; M-1 to G-128; M-1 to H-127; M-1 to F-126; M-1 to T-125; M-1 to A-124; M-1 to P-123; M-1 to D-122; M-1 to V-121; M-1 to S-120; M-1 to R-119; M-1 to L-118; M-1 to Q-117; M-1 to A-116; M-1 to N-115; M-1 to D-114; M-1 to S-113; M-1 to L-112; M-1 to D-111; M-1 to L-110; M-1 to Q-109; M-1 to E-108; M-1 to L-107; M-1 to L-106; M-1 to A-105; M-1 to L-104; M-1 to G-103; M-1 to T-102; M-1 to F-101; M-1 to A-100; M-1 to A-99; M-1 to A-98; M-1 to D-97; M-1 to I-96; M-1 to R-95; M-1 to A-94; M-1 to L-93; M-1 to V-92; M-1 to N-91; M-1 to S-90; M-1 to H-89; M-1 to L-88; M-1 to W-87; M-1 to L-86; M-1 to I-85; M-1 to T-84; M-1 to L-83; M-1 to N-82; M-1 to R-81; M-1 to C-80; M-1 to A-79; M-1 to R-78; M-1 to F-77; M-1 to S-76; M-1 to A-75; M-1 to A-74; M-1 to P-73; M-1 to V-72; M-1 to H-71; M-1 to S-70; M-1 to I-69; M-1 to R-68; M-1 to N-67; M-1 to G-66; M-1 to H-65; M-1 to L-64; M-1 to F-63; M-1 to I-62; M-1 to R-61; M-1 to Q-60; M-1 to S-59; M-1 to A-58; M-1 to A-57; M-1 to P-56; M-1 to I-55; M-1 to G-54; M-1 to V-53; M-1 to P-52; M-1 to V-51; M-1 to A-50; M-1 to Q-49; M-1 to L-48; M-1 to G-47; M-1 to Q-46; M-1 to Q-45; M-1 to P-44; M-1 to C-43; M-1 to S-42; M-1 to T-41; M-1 to T-40; M-1 to V-39; M-1 to K-38; M-1 to P-37; M-1 to E-36; M-1 to N-35; M-1 to Y-34; M-1 to C-33; M-1 to V-32; M-1 to C-31; M-1 to A-30; M-1 to G-29; M-1 to P-28; M-1 to C-27; M-1 to P-26; M-1 to A-25; M-1 to A-24; M-1 to V-23; M-1 to Q-22; M-1 to W-21; M-1 to A-20; M-1 to Q-19; M-1 to L-18; M-1 to W-17; M-1 to L-16; M-1 to V-15; M-1 to W-14; M-1 to A-13; M-1 to L-12; M-1 to L-11; M-1 to R-10; M-1 to S-9; M-1 to G-8; M-1 to G-7; and M-1 to A-6 of SEQ ID NO:135. Polypeptides encoded by these polynucleotides are also encompassed by the invention. Moreover, fragments and variants of these polypeptides (such as, for example, fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides, or the complement thereof) are encompassed by the invention. Antibodies that bind polypeptides of the invention are also encompassed by the invention. Polynucleotides encoding these polypeptides are also encompassed by the invention.

In addition, any of the above listed N- or C-terminal deletions can be combined to produce a N- and C-terminal deleted polypeptide. The invention also provides polypeptides comprising, or alternatively consisting of, one or more amino acids deleted from both the amino and the carboxyl termini, which may be described generally as having residues m-n of SEQ ID NO:135, where n and m are integers as described above. More in particular, the invention provides polynucleotides encoding polypeptides comprising, or alternatively consisting of, an amino acid sequence selected from the group: M-1 to V-15; K-2 to L-16; R-3 to W-17; A-4 to L-18; S-5 to Q-19; A-6 to A-20; G-7 to W-21; G-8 to Q-22; S-9 to V-23; R-10 to A-24; L-11 to A-25; L-12 to P-26; A-13 to C-27; W-14 to P-28; V-15 to G-29; L-16 to A-30; W-17 to C-31; L-18 to V-32; Q-19 to C-33; A-20 to Y-34; W-21 to N-35; Q-22 to E-36; V-23 to P-37; A-24 to K-38; A-25 to V-39; P-26 to T-40; C-27 to T-41; P-28 to S-42; G-29 to C-43; A-30 to P-44; C-31 to Q-45; V-32 to Q-46; C-33 to G-47; Y-34 to L-48; N-35 to Q-49; E-36 to A-50; P-37 to V-51; K-38 to P-52; V-39 to V-53; T-40 to G-54; T-41 to I-55; S-42 to P-56; C-43 to A-57; P-44 to A-58; Q-45 to S-59; Q-46 to Q-60; G-47 to R-61; L-48 to I-62; Q-49 to F-63; A-50 to L-64; V-51 to H-65; P-52 to G-66; V-53 to N-67; G-54 to R-68; I-55 to I-69; P-56 to S-70; A-57 to H-71; A-58 to V-72; S-59 to P-73; Q-60 to A-74; R-61 to A-75; I-62 to S-76; F-63 to F-77; L-64 to R-78; H-65 to A-79; G-66 to C-80; N-67 to R-81; R-68 to N-82; I-69 to L-83; S-70 to T-84; H-71 to I-85; V-72 to L-86; P-73 to W-87; A-74 to L-88; A-75 to H-89; S-76 to S-90; F-77 to N-91; R-78 to V-92; A-79 to L-93; C-80 to A-94; R-81 to R-95; N-82 to I-96; L-83 to D-97; T-84 to A-98; I-85 to A-99; L-86 to A-100; W-87 to F-101; L-88 to T-102; H-89 to G-103; S-90 to L-104; N-91 to A-105; V-92 to L-106; L-93 to L-107; A-94 to E-108; R-95 to Q-109; I-96 to L-110; D-97 to D-111; A-98 to L-112; A-99 to S-113; A-100 to D-114; F-101 to N-115; T-102 to A-116; G-103 to Q-117; L-104 to L-118; A-105 to R-119; L-106 to S-120; L-107 to V-121; E-108 to D-122; Q-109 to P-123; L-110 to A-124; D-111 to T-125; L-112 to F-126; S-113 to H-127; D-114 to G-128; N-115 to L-129; A-116 to G-130; Q-117 to R-131; L-118 to L-132; R-119 to H-133; S-120 to T-134; V-121 to L-135; D-122 to H-136; P-123 to L-137; A-124 to D-138; T-125 to R-139; F-126 to C-140; H-127 to G-141; G-128 to L-142; L-129 to Q-143; G-130 to E-144; R-131 to L-145; L-132 to G-146; H-133 to P-147; T-134 to G-148; L-135 to L-149; H-136 to F-150; L-137 to R-151; D-138 to G-152; R-139 to L-153; C-140 to A-154; G-141 to A-155; L-142 to L-156; Q-143 to Q-157; E-144 to Y-158; L-145 to L-159; G-146 to Y-160; P-147 to L-161; G-148 to Q-162; L-149 to D-163; F-150 to N-164; R-151 to A-165; G-152 to L-166; L-153 to Q-167; A-154 to A-168; A-155 to L-169; L-156 to P-170; Q-157 to D-171; Y-158 to D-172; L-159 to T-173; Y-160 to F-174; L-161 to R-175; Q-162 to D-176; D-163 to L-177; N-164 to G-178; A-165 to N-179; L-166 to L-180; Q-167 to T-181; A-168 to H-182; L-169 to L-183; P-170 to F-184; D-171 to L-185; D-172 to H-186; T-173 to G-187; F-174 to N-188; R-175 to R-189; D-176 to I-190; L-177 to S-191; G-178 to S-192; N-179 to V-193; L-180 to P-194; T-181 to E-195; H-182 to R-196; L-183 to A-197; F-184 to F-198; L-185 to R-199; H-186 to G-200; G-187 to L-201; N-188 to H-202; R-189 to S-203; I-190 to L-204; S-191 to D-205; S-192 to R-206; V-193 to L-207; P-194 to L-208; E-195 to L-209; R-196 to H-210; A-197 to Q-211; F-198 to N-212; R-199 to R-213; G-200 to V-214; L-201 to A-215; H-202 to H-216; S-203 to V-217; L-204 to H-218; D-205 to P-219; R-206 to H-220; L-207 to A-221; L-208 to F-222; L-209 to R-223; H-210 to D-224; Q-211 to L-225; N-212 to G-226; R-213 to R-227; V-214 to L-228; A-215 to M-229; H-216 to T-230; V-217 to L-231; H-218 to Y-232; P-219 to L-233; H-220 to F-234; A-221 to A-235; F-222 to N-236; R-223 to N-237; D-224 to L-238; L-225 to S-239; G-226 to A-240; R-227 to L-241; L-228 to P-242; M-229 to T-243; T-230 to E-244; L-231 to A-245; Y-232 to L-246; L-233 to A-247; F-234 to P-248; A-235 to L-249; N-236 to R-250; N-237 to A-251; L-238 to L-252; S-239 to Q-253; A-240 to Y-254; L-241 to L-255; P-242 to R-256; T-243 to L-257; E-244 to N-258; A-245 to D-259; L-246 to N-260; A-247 to P-261; P-248 to W-262; L-249 to V-263; R-250 to C-264; A-251 to D-265; L-252 to C-266; Q-253 to R-267; Y-254 to A-268; L-255 to R-269; R-256 to P-270; L-257 to L-271; N-258 to W-272; D-259 to A-273; N-260 to W-274; P-261 to L-275; W-262 to Q-276; V-263 to K-277; C-264 to F-278; D-265 to R-279; C-266 to G-280; R-267 to S-281; A-268 to S-282; R-269 to S-283; P-270 to E-284; L-271 to V-285; W-272 to P-286; A-273 to C-287; W-274 to S-288; L-275 to L-289; Q-276 to P-290; K-277 to Q-291; F-278 to R-292; R-279 to L-293; G-280 to A-294; S-281 to G-295; S-282 to R-296; S-283 to D-297; E-284 to L-298; V-285 to K-299; P-286 to R-300; C-287 to L-301; S-288 to A-302; L-289 to A-303; P-290 to N-304; Q-291 to D-305; R-292 to L-306; L-293 to Q-307; A-294 to G-308; G-295 to C-309; R-296 to A-310; D-297 to V-311; L-298 to A-312; K-299 to T-313; R-300 to G-314; L-301 to P-315; A-302 to Y-316; A-303 to H-317; N-304 to P-318; D-305 to I-319; L-306 to W-320; Q-307 to T-321; G-308 to G-322; C-309 to R-323; A-310 to A-324; V-311 to T-325; A-312 to D-326; T-313 to E-327; G-314 to E-328; P-315 to P-329; Y-316 to L-330; H-317 to G-331; P-318 to L-332; I-319 to P-333; W-320 to K-334; T-321 to C-335; G-322 to C-336; R-323 to Q-337; A-324 to P-338; T-325 to D-339; D-326 to A-340; E-327 to A-341; E-328 to D-342; P-329 to K-343; L-330 to A-344; G-331 to S-345; L-332 to V-346; P-333 to L-347; K-334 to E-348; C-335 to P-349; C-336 to G-350; Q-337 to R-351; P-338 to P-352; D-339 to A-353; A-340 to S-354; A-341 to A-355; D-342 to G-356; K-343 to N-357; A-344 to A-358; S-345 to L-359; V-346 to K-360; L-347 to G-361; E-348 to R-362; P-349 to V-363; G-350 to P-364; R-351 to P-365; P-352 to G-366; A-353 to D-367; S-354 to S-368; A-355 to P-369; G-356 to P-370; N-357 to G-371; A-358 to N-372; L-359 to G-373; K-360 to S-374; G-361 to G-375; R-362 to P-376; V-363 to R-377; P-364 to H-378; P-365 to I-379; G-366 to N-380; D-367 to D-381; S-368 to S-382; P-369 to P-383; P-370 to F-384; G-371 to G-385; N-372 to T-386; G-373 to L-387; S-374 to P-388; G-375 to G-389; P-376 to S-390; R-377 to A-391; H-378 to E-392; I-379 to P-393; N-380 to P-394; D-381 to A-395; S-382 to H-396; P-383 to C-397; F-384 to S-398; G-385 to A-399; T-386 to A-400; L-387 to R-401; P-388 to G-402; G-389 to L-403; S-390 to R-404; A-391 to A-405; E-392 to T-406; P-393 to R-407; P-394 to F-408; A-395 to P-409; H-396 to T-410; C-397 to S-411; S-398 to G-412; A-399 to P-413; A-400 to R-414; R-401 to R-415; G-402 to R-416; L-403 to P-417; R-404 to G-418; A-405 to C-419; T-406 to S-420; R-407 to R-421; F-408 to K-422; P-409 to N-423; T-410 to R-424; S-411 to T-425; G-412 to R-426; P-413 to S-427; R-414 to H-428; R-415 to C-429; R-416 to R-430; P-417 to L-431; G-418 to G-432; C-419 to Q-433; S-420 to A-434; R-421 to G-435; K-422 to S-436; N-423 to G-437; R-424 to G-438; T-425 to G-439; R-426 to G-440; S-427 to T-441; H-428 to G-442; C-429 to D-443; R-430 to S-444; L-431 to E-445; G-432 to G-446; Q-433 to S-447; A-434 to G-448; G-435 to A-449; S-436 to L-450; G-437 to P-451; G-438 to S-452; G-439 to L-453; G-440 to T-454; T-441 to C-455; G-442 to S-456; D-443 to L-457; S-444 to T-458; E-445 to P-459; G-446 to L-460; S-447 to G-461; G-448 to L-462; A-449 to A-463; L-450 to L-464; P-451 to V-465; S-452 to L-466; L-453 to W-467; T-454 to T-468; C-455 to V-469; S-456 to L-470; L-457 to G-471; T-458 to P-472; and P-459 to C-473 of SEQ ID NO:135. Polynucleotides encoding these polypeptides are also encompassed by the invention. Moreover, fragments and variants of these polypeptides (such as, for example, fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides, or the complement thereof) are encompassed by the invention. Antibodies that bind polypeptides of the invention are also encompassed by the invention. Polynucleotides encoding these polypeptides are also encompassed by the invention.

The present invention is also directed to proteins containing polypeptides at least 80%, 85%, 90%, 92%, 93%, 94%, 95%, 96%, 97%, 98% or 99% identical to a polypeptide sequence set forth herein as m-n. In preferred embodiments, the application is directed to proteins containing polypeptides at least 80%, 85%, 90%, 95%, 96%, 97%, 98% or 99% identical to polypeptides having the amino acid sequence of the specific N and C terminal deletions recited herein. Polynucleotides encoding these polypeptides are also encompassed by the invention.

Also included are polynucleotide sequences encoding a polypeptide consisting of a portion of the complete amino acid sequence encoded by a cDNA clone contained in ATCC Deposit No. 209782, where this portion excludes any integer of amino acid residues from 1 to about 467 amino acids from the amino terminus of the complete amino acid sequence encoded by a cDNA clone contained in ATCC Deposit No. 209782, or any integer of amino acid residues from 6 to about 473 amino acids from the carboxy terminus, or any combination of the above amino terminal and carboxy terminal deletions, of the complete amino acid sequence encoded by the cDNA clone contained in ATCC Deposit No. 209782. Polypeptides encoded by these polynucleotides also are encompassed by the invention. Moreover, fragments and variants of these polypeptides (such as, for example, fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides, or the complement thereof) are encompassed by the invention. Antibodies that bind polypeptides of the invention are also encompassed by the invention. Polynucleotides encoding these polypeptides are also encompassed by the invention.

The translation product of this gene shares sequence homology with ALS (Acid Labile Subunit of Insulin-Like Growth Factor) which is thought to be important in the regulation of IGF availability. As such, it is likely that the product of this gene is involved in the regulation of various proliferation-dependent cellular processes that may be attributable to cancer progression (See Genbank Accession No. gi|184808; all references available through this accession are hereby incorporated by reference herein).

The gene encoding the disclosed cDNA is believed to reside on chromosome 22. Accordingly, polynucleotides related to this invention are useful as a marker in linkage analysis for chromosome 22.

As described herein or otherwise known in the art, the polynucleotides of the invention have uses that include, but are not limited to, serving as probes or primers in chromosome identification, chromosome mapping, and linkage analysis.

Polynucleotides and polypeptides of the invention are useful as reagents for differential identification of the tissue(s) or cell type(s) present in a biological sample and for diagnosis of diseases and conditions which include, but are not limited to, neurodegenerative diseases, growth deficiencies, osteoporosis, catabolic disorders, diabetes, ovarian cancer, neuronal injury spinal injury, post-spinal trauma neurite outgrowth, inflammation, and neuronal injury, and disorders of the central and peripheral nervous system. Similarly, polypeptides and antibodies directed to these polypeptides are useful in providing immunological probes for differential identification of the tissue(s) or cell type(s). For a number of disorders of the above tissues or cells, particularly of the nervous system and other peripheral tissues, expression of this gene at significantly higher or lower levels may be routinely detected in certain tissues or cell types (e.g., neural, neuronal, proliferating, and/or other tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution cerebellum and homology to ALS (Acid Labile Subunit of Insulin-Like Growth Factor) indicates that polynucleotides and polypeptides corresponding to this gene are useful for the treatment and diagnosis of a variety of metabolic disorders, growth deficiencies, osteoporosis, catabolic disorders (including AIDS) and diabetes. Nearly all of the insulin-like growth factor (IGF) in the circulation is bound in a heterotrimeric complex composed of IGF, IGF-binding protein-3, and the acid-labile subunit (ALS). The protein product of this gene therefore may afford the ability to potentiate the biological actions of IGF or similar growth factors and cytokines. Studies which demonstrate the beneficial effect of IGF-I in amyotrophic lateral-sclerosis, would suggest a role in this disease as well. Alternatively, the tissue distribution in cancerous ovarian tissue indicates polynucleotides and polypeptides corresponding to this gene are useful for the treatment, diagnosis, and/or prevention of various skin disorders. Furthermore, the protein may also be used to determine biological activity, raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Polynucleotides or polypeptides of the invention and/or agonists and/or antagonists thereof, are used to treat, prevent, and/or diagnose diseases and disorders of the nervous system.

In specific embodiments, the polynucleotides and/or polypeptides corresponding to this gene and/or agonists or antagonists of those polypeptides (including antibodies) as well as fragments and variants of those polynucleotides, polypeptides agonists and antagonists, may be used to diagnose, prognose or monitor neurological diseases, neural injury, and/or spinal cord injury. In other specific embodiments, the polynucleotides and/or polypeptides corresponding to this gene and/or agonists or antagonists of those polypeptides (including antibodies) as well as fragments and variants of those polynucleotides, polypeptides agonists and antagonists, may be used to treat, prevent, or ameliorate neurological disease, neural injury, and/or spinal cord injury.

In other preferred embodiments, the polynucleotides and/or polypeptides corresponding to this gene and/or agonists or antagonists of those polypeptides (including antibodies) as well as fragments and variants of those polynucleotides, polypeptides agonists and antagonists, may be used to diagnose, prognose or monitor diseases and disorders associated with aberrant neurite outgrowth.

By "agonist," is meant any substance that enhances the function of the polynucleotides or polypeptides of the invention. Classes of molecules that can function as agonists include, but are not limited to, small molecules, antibodies (including fragments or variants thereof, such as Fab fragments, Fab'2 fragments and scFvs), and peptidomimetics. By "antagonist," is meant any substance that diminishes or abolishes the function of the polynucleotides or polypeptides of the invention. Classes of molecules that can function as antagonists include, but are not limited to, small molecules, antibodies (including fragments or variants thereof, such as Fab fragments, Fab'2 fragments and scFvs) antisense polynucleotides, ribozymes, and peptidomimetics.

In another embodiment, the polynucleotides and/or polypeptides corresponding to this gene and/or antagonists thereof (especially neutralizing or antagonistic antibodies) may be used to treat, prevent, and/or ameliorate neurological disease, neural injury, and/or spinal cord injury. Additionally, in other embodiments, the polynucleotides and/or polypeptides corresponding to this gene and/or anatgonists thereof (especially neutralizing or antagonistic antibodies) may be used to treat, prevent, or ameliorate conditions associated with ameliorate neurological disease, neural injury, and/or spinal cord injury, including, but not limited to, Alzheimer's disease, Parkinson's disease, Huntington's disease, amylotrophic lateral sclerosis and the like, as well as spinocerebellar degenerations, and other neurological diseases and disorders as described in the "Neural Activity and Neurological Activity diseases" section below, In a preferred embodiment, the polynucleotides and/or polypeptides corresponding to this gene and/or antagonists thereof (especially neutralizing or antagonistic antibodies) may be used to treat, prevent, and/or ameliorate neural injury, and/or spinal cord injury following spinal cord and neural trauma. For example, neural outgrowth and inflammation. Additionally, in other embodiments, the polynucleotides and/or polypeptides corresponding to this gene and/or anatgonists thereof (especially neutralizing or antagonistic antibodies) may be used to treat, prevent, or ameliorate conditions associated with ameliorate neurological disease, neural injury, and/or spinal cord injury, including, but not limited to, Alzheimer's disease, Parkinson's disease, Huntington's disease, amylotrophic lateral sclerosis and the like, as well as spinocerebellar degenerations, and other neurological diseases and disorders as described in the "Neural Activity and Neurological Activity diseases" section below.

In another embodiment, compositions of the invention i.e., Therapeutics (comprising polynucleotides, polypeptides of the invention, agonists and/or antagonists thereof (including antibodies) as well as fragments and variants of the polynucleotides, polypeptides of the invention, agonists and/or antagonists of the invention) are used in combination with antiinflammatory drugs (e.g., as described herein) and/or drugs used to treat spinal cord injury, neural injury, or neurological disease.

In certain embodiments, the Therapeutics of the invention are administered in combination with agents used to treat psychiatric disorders. Psychiatric drugs that may be administered with the Therapeutics of the invention include, but are not limited to, antipsychotic agents (e.g., chlorpromazine, chlorprothixene, clozapine, fluphenazine, haloperidol, loxapine, mesoridazine, molindone, olanzapine, perphenazine, pimozide, quetiapine, risperidone, thioridazine, thiothixene, trifluoperazine, and triflupromazine), antimanic agents (e.g., carbamazepine, divalproex sodium, lithium carbonate, and lithium citrate), antidepressants (e.g., amitriptyline, amoxapine, bupropion, citalopram, clomipramine, desipramine, doxepin, fluvoxamine, fluoxetine, imipramine, isocarboxazid, maprotiline, mirtazapine, nefazodone, nortriptyline, paroxetine, phenelzine, protriptyline, sertraline, tranylcypromine, trazodone, trimipramine, and venlafaxine), antianxiety agents (e.g., alprazolam, buspirone, chlordiazepoxide, clorazepate, diazepam, halazepam, lorazepam, oxazepam, and prazepam), and stimulants (e.g., d-amphetamine, methylphenidate, and pemoline).

In other embodiments, the Therapeutics of the invention are administered in combination with agents used to treat neurological disorders. Neurological agents that may be administered with the Therapeutics of the invention include, but are not limited to, antiepileptic agents (e.g., carbamazepine, clonazepam, ethosuximide, phenobarbital, phenyloin, primidone, valproic acid, divalproex sodium, felbamate, gabapentin, lamotrigine, levetiracetam, oxcarbazepine, tiagabine, topiramate, zonisamide, diazepam, lorazepam, and clonazepam), antiparkinsonian agents (e.g., levodopa/carbidopa, selegiline, amantadine, bromocriptine, pergolide, ropinirole, pramipexole, benztropine; biperiden; ethopropazine; procyclidine; trihexyphenidyl, tolcapone), and ALS therapeutics (e.g. riluzole).

The polynucleotides, polypeptides and agonists or antagonists of the invention may also be used for the diagnosis and/or treatment of diseases, disorders, damage or injury of the brain and/or nervous system. Nervous system disorders that can be treated with the compositions of the invention (e.g., polypeptides, polynucleotides, and/or agonists or antagonists), include, but are not limited to, nervous system injuries, and diseases or disorders which result in either a disconnection of axons, a diminution or degeneration of neurons, or demyelination. Nervous system lesions which may be treated in a patient (including human and non-human mammalian patients) according to the methods of the invention, include but are not limited to, the following lesions of either the central (including spinal cord, brain) or peripheral nervous systems: (1) ischemic lesions, in which a lack of oxygen in a portion of the nervous system results in neuronal injury or death, including cerebral infarction or ischemia, or spinal cord infarction or ischemia; (2) traumatic lesions, including lesions caused by physical injury or associated with surgery, for example, lesions which sever a portion of the nervous system, or compression injuries; (3) malignant lesions, in which a portion of the nervous system is destroyed or injured by malignant tissue which is either a nervous system associated malignancy or a malignancy derived from non-nervous system tissue; (4) infectious lesions, in which a portion of the nervous system is destroyed or injured as a result of infection, for example, by an abscess or associated with infection by human immunodeficiency virus, herpes zoster, or herpes simplex virus or with Lyme disease, tuberculosis, or syphilis; (5) degenerative lesions, in which a portion of the nervous system is destroyed or injured as a result of a degenerative process including but not limited to, degeneration associated with Parkinson's disease, Alzheimer's disease, Huntington's chorea, or amyotrophic lateral sclerosis (ALS); (6) lesions associated with nutritional diseases or disorders, in which a portion of the nervous system is destroyed or injured by a nutritional disorder or disorder of metabolism including, but not limited to, vitamin B12 deficiency, folic acid deficiency, Wernicke disease, tobacco-alcohol amblyopia, Marchiafava-Bignami disease (primary degeneration of the corpus callosum), and alcoholic cerebellar degeneration; (7) neurological lesions associated with systemic diseases including, but not limited to, diabetes (diabetic neuropathy, Bell's palsy), systemic lupus erythematosus, carcinoma, or sarcoidosis; (8) lesions caused by toxic substances including alcohol, lead, or particular neurotoxins; and (9) demyelinated lesions in which a portion of the nervous system is destroyed or injured by a demyelinating disease including, but not limited to, multiple sclerosis, human immunodeficiency virus-associated myelopathy, transverse myelopathy or various etiologies, progressive multifocal leukoencephalopathy, and central pontine myelinolysis.

Additional neurologic diseases which can be treated or detected with polynucleotides, polypeptides, agonists, and/or antagonists of the present invention include nerve compression syndromes such as carpal tunnel syndrome, tarsal tunnel syndrome, thoracic outlet syndrome such as cervical rib syndrome, ulnar nerve compression syndrome, neuralgia such as causalgia, cervico-brachial neuralgia, facial neuralgia and trigeminal neuralgia, neuritis such as experimental allergic neuritis, optic neuritis, polyneuritis, polyradiculoneuritis and radiculities such as polyradiculitis, hereditary motor and sensory neuropathies such as Charcot-Marie Disease, Hereditary Optic Atrophy, Refsum's Disease, Hereditary Spastic Paraplegia and Werdnig-Hoffmann Disease, Hereditary Sensory and Autonomic Neuropathies which include Congenital Analgesia and Familial Dysautonomia, POEMS Syndrome, Sciatica, Gustatory Sweating and Tetany).

Additional diseases which can be treated or detected with polynucleotides, polypeptides, agonists, and/or antagonists of the present invention include, but are not limited to neoplastic disease of the CNS e.g. glioma, glioblastoma, medulloblastoma, craniopharyngioma, ependymoma, pinealoma, haemangioblastoma, acoustic neuroma, oligodendroglioma, menangioma, neuroblastoma or retinoblastoma and degenerative nerve diseases e.g. Alzheimer's and Parkinson's diseases. Representative uses are described in the "Regeneration" and "Hyperproliferative Disorders" sections below, in Examples 28, 30, 31, 32, 40, 42, and 46, and elsewhere herein. Therapeutics can be used to treat or prevent hyperproliferative or benign dysproliferative disorders e.g. psoriasis and tissue hypertrophy. Ribozymes or antisense nucleic acids can be used to inhibit production of the polypeptides of the invention, to induce regeneration of neurons or to promote structural plasticity of the CNS in disorders where neurite growth, regeneration or maintenance are deficient or desired. The animal models can be used in diagnostic and screening methods for predisposition to disorders and to screen for or test molecules which can treat or prevent disorders or diseases of the CNS.

Furthermore, the protein may also be used to determine biological activity, raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Features of Protein Encoded by Gene No: 21

This gene is expressed primarily in bone marrow, CD34 positive cells, and immune cells, including, neutrophils, T-cells, B-cells, macrophages, monocytes, and dendritic cells and to a lesser extent in brain and tonsils.

In one embodiments, polypeptides comprising the amino acid sequence of the open reading frame upstream of the predicted signal peptide are contemplated by the present invention. Specifically, polypeptides of the invention may comprise, or alternatively consist of the following amino acid sequence:

```
                                        (SEQ ID NO: 163)
VDGIDKLDIEFLQQFLETHSRGPRLHSPGHASQEATPGANMSSGTELLWP

GAALLVLLGVAASLCVRCSRPGAKRSEKIYQQRSLREDQQSFTGSRTYSL

VGQAWPGPLADMAPTRKDKLLQFYPSLEDPASSRYQNFSKGSRHGSEEAY
```

-continued

IDPIAMEYYNWGRFSKPPEDDDANSYENVLICKQKTTETGAQQEGIGGLC

RGDLSLSLALKTGPTSGLCPSASPEEDEGI.

Polynucleotides encoding these polypeptides are also encompassed by the invention. Moreover, fragments and variants of these polypeptides (such as, for example, fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides, or the complement thereof) are encompassed by the invention. Antibodies that bind polypeptides of the invention are also encompassed by the invention. Polynucleotides encoding these polypeptides are also encompassed by the invention.

Preferred polypeptide fragments may comprise or alternatively consist of one, two, three, four or more of the following amino acid sequence:

(SEQ ID NO: 164)
ASSRYQNFSKGSRHGSEEAYIDPIA, (SEQ ID NO: 165)
MEYYNWGRFSKPPEDDDANSY, (SEQ ID NO: 166)
ENVLICKQKTTETGAQQEGIGGLCRGD, (SEQ ID NO: 167)
VRCSRPGAKRSEKIYQQRSLREDQQSFTGSRTYSLVGQAWPGPLADMAPTR

KDKLLQFYPSLEDPASS
and (SEQ ID NO: 168)
LSLSLALKTGPTSGLCPSASPEEDEGI.

Polynucleotides encoding these polypeptide fragments (SEQ ID NOs: 164, 165, 166, 167, and/or 168), polynucleotides that hybridize to the complementary strand of these polynucleotides (e.g., under the hybridization conditions described herein) are encompassed by the invention, as are the polypeptides encoded by these hybridizing polynucleotides. Moreover, fragments and variants of these polypeptides (such as, for example, fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides, or the complement thereof) are encompassed by the invention. Antibodies that bind polypeptides of the invention are also encompassed by the invention. Polynucleotides encoding these polypeptides are also encompassed by the invention.

Preferred polypeptides of the present invention comprise, or alternatively consist of one, two, three, four, five, or more of the immunogenic epitopes shown in SEQ ID NO:160 as residues: Ser-29 to Thr-57, Pro-74 to Lys-79, Pro-85 to Glu-107, Tyr-118 to Tyr-136, Gln-144 to Gln-152, Ala-182 to Glu-188. Polynucleotides encoding these polypeptides are also encompassed by the invention.

Also preferred are polypeptides comprising the mature polypeptide which is predicted to consist of residues 26-190 of the foregoing sequence (SEQ ID NO:160), and biologically active fragments of the mature polypeptide (e.g., fragments that stimulate the proliferation of bone marrow CD34+ cells).

FIGS. 9A-B show the nucleotide (SEQ ID NO:159) and deduced amino acid sequence (SEQ ID NO:160) of this polypeptide.

FIG. 10 shows an analysis of the amino acid sequence (SEQ ID NO:160). Alpha, beta, turn and coil regions; hydrophilicity and hydrophobicity; amphipathic regions; flexible regions; antigenic index and surface probability are shown, and all were generated using the default settings. In the "Antigenic Index or Jameson Wolf" graph, the positive peaks indicate locations of the highly antigenic regions of the protein, i.e., regions from which epitope-bearing peptides of the invention can be obtained. The domains defined by these graphs are contemplated by the present invention.

The data presented in FIG. 10 are also represented in tabular form in Table 12. The columns are labeled with the headings "Res", "Position", and Roman Numerals I XIV. The column headings refer to the following features of the amino acid sequence presented in FIG. 10, and Table 12: "Res": amino acid residue of SEQ ID NO:160 and FIGS. 9A-B; "Position": position of the corresponding residue within SEQ ID NO:160 and FIGS. 9A-B; I: Alpha, Regions Garnier Robson; II: Alpha, Regions Chou Fasman; III: Beta, Regions Garnier Robson; IV: Beta, Regions Chou Fasman; V: Turn, Regions Garnier Robson; VI: Turn, Regions Chou Fasman; VII: Coil, Regions Garnier Robson; VIII: Hydrophilicity Plot Kyte Doolittle; IX: Hydrophobicity Plot Hopp Woods; X: Alpha, Amphipathic Regions Eisenberg; XI: Beta, Amphipathic Regions Eisenberg; XII: Flexible Regions Karplus Schulz; XIII: Antigenic Index Jameson Wolf; and XIV: Surface Probability Plot Emini.

Preferred embodiments of the invention in this regard include fragments that comprise alpha-helix and alpha-helix forming regions ("alpha-regions"), beta-sheet and beta-sheet forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, flexible regions, surface-forming regions and high antigenic index regions. The data representing the structural or functional attributes of the protein set forth in FIG. 10 and/or Table 12, as described above, was generated using the various modules and algorithms of the DNA*STAR set on default parameters. In a preferred embodiment, the data presented in columns VIII, IX, XIII, and XIV of Table 12 can be used to determine regions of the protein which exhibit a high degree of potential for antigenicity. Regions of high antigenicity are determined from the data presented in columns VIII, IX, XIII, and/or XIV by choosing values which represent regions of the polypeptide which are likely to be exposed on the surface of the polypeptide in an environment in which antigen recognition may occur in the process of initiation of an immune response.

Certain preferred regions in these regards are set out in FIG. 10, but may, as shown in Table 12, be represented or identified by using tabular representations of the data presented in FIG. 10. The DNA*STAR computer algorithm used to generate FIG. 10 (set on the original default parameters) was used to present the data in FIG. 10 in a tabular format (See Table 12). The tabular format of the data in FIG. 10 is used to easily determine specific boundaries of a preferred region. The above-mentioned preferred regions set out in FIG. 10 and in Table 12 include, but are not limited to, regions of the aforementioned types identified by analysis of the amino acid sequence set out in FIGS. 9A-B (SEQ ID NO:160). As set out in FIG. 10 and in Table 12, such preferred regions include Garnier-Robson alpha-regions, beta-regions, turn-regions, and coil-regions, Chou-Fasman alpha-regions, beta-regions, and turn-regions, Kyte-Doolittle hydrophilic regions and Hopp-Woods hydrophobic regions, Eisenberg alpha- and beta-amphipathic regions, Karplus-Schulz flexible regions, Jameson-Wolf regions of high antigenic index and Emini surface-forming regions.

The present invention is further directed to fragments of the isolated nucleic acid molecules described herein. By a fragment of an isolated DNA molecule having the nucleotide sequence of the deposited cDNA or the nucleotide sequence shown in SEQ ID NO:159 is intended DNA fragments at least about 15 nt, and more preferably at least about 20 nt, still more preferably at least about 30 nt, and even more preferably, at least about 40 nt in length which are useful as diagnostic probes and primers as discussed herein. Of course, larger fragments 50-1500 nt in length are also useful according to the present invention, as are fragments corresponding to most, if not all, of the nucleotide sequence of the deposited cDNA or as shown in SEQ ID NO:159. By a fragment at least 20 nt in length, for example, is intended fragments which include 20 or more contiguous bases from the nucleotide sequence of the deposited cDNA or the nucleotide sequence as shown in SEQ ID NO:159. In this context "about" includes the particularly recited size, larger or smaller by several (5, 4, 3, 2, or 1) nucleotides, at either terminus or at both termini. Representative examples of polynucleotide fragments of the invention include, for example, fragments that comprise, or alternatively, consist of, a sequence from about nucleotide 1 to about 50, from about 51 to about 100, from about 101 to about 150, from about 151 to about 200, from about 201 to about 250, from about 251 to about 300, from about 301 to about 350, from about 351 to about 400, from about 401 to about 450, from about 451 to about 500, and from about 501 to about 550, and from about 551 to about 600, and from about 601 to about 650, and from about 651 to about 700, and from about 701 to about 750, and from about 751 to about 800, and from about 801 to about 850, and from about 851 to about 900, and from about 901 to about 950, and from about 951 to about 1000, and from about 1001 to about 1050, and from about and from about 1051 to about 1100, and from about 1101 to about 1150, and from about 1151 to about 1200, and from about 1201 to about 1250, and from about 1251 to about 1300, and from about 1301 to about 1350, and from about 1351 to about 1400, and from about 1401 to about 1450, and from about 1451 to about 1500, and from about 1501 to about 1551, and from about 1551 to about 1600, and from about 1601 to about 1650, and from about 1651 to about 1700, and from about 1701 to about 1750, and from about 1751 to about 1797 of SEQ ID NO:159, or the complementary strand thereto, or the cDNA contained in the deposited gene. In this context "about" includes the particularly recited ranges, larger or smaller by several (5, 4, 3, 2, or 1) nucleotides, at either terminus or at both termini. In additional embodiments, the polynucleotides of the invention encode functional attributes of the corresponding protein.

Preferred polypeptide fragments include the secreted protein as well as the mature form. Further preferred polypeptide fragments include the secreted protein or the mature form having a continuous series of deleted residues from the amino or the carboxy terminus, or both. For example, any number of amino acids, ranging from 1-60, can be deleted from the amino terminus of either the secreted polypeptide or the mature form. Similarly, any number of amino acids, ranging from 1-30, can be deleted from the carboxy terminus of the secreted protein or mature form. Furthermore, any combination of the above amino and carboxy terminus deletions are preferred. Similarly, polynucleotides encoding these polypeptide fragments are also preferred.

Preferably, the polynucleotide fragments of the invention encode a polypeptide which demonstrates a functional activity. By a polypeptide demonstrating a "functional activity" is meant to be a polypeptide capable of displaying one or more known functional activities associated with a full-length (complete) or mature-form of the protein. Such functional activities include, but are not limited to, biological activity (e.g., ability to regulate (e.g., stimulate) hematopoiesis in vitro or in vivo), antigenicity, and immunogenicity. The functional activity of polypeptides of the invention, and fragments, variants derivatives, and analogs thereof, can be assayed by various methods described herein.

In addition, assays described herein and otherwise known in the art may routinely be applied to measure biological activity of polypeptides and fragments of the invention, variants derivatives and analogs thereof (e.g., to regulate (e.g., to stimulate or inhibit) hematopoiesis in vitro or in vivo). For example, techniques known in the art (such as for example assaying for thymidine incorporation), may be applied or routinely modified to assay for the ability of the compositions of the invention to inhibit proliferation of hematopoietic cells. Other methods will be known to the skilled artisan and are within the scope of the invention.

Even if deletion of one or more amino acids from the N-terminus of a protein results in modification of loss of one or more biological functions of the protein, other functional activities (e.g., biological activities, ability to multimerize, etc.) may still be retained. For example, the ability of shortened muteins to induce and/or bind to antibodies which recognize the complete or mature forms of the polypeptides generally will be retained when less than the majority of the residues of the complete or mature polypeptide are removed from the N-terminus. Whether a particular polypeptide lacking N-terminal residues of a complete polypeptide retains such immunologic activities can readily be determined by routine methods described herein and otherwise known in the art. It is not unlikely that a mutein with a large number of deleted N-terminal amino acid residues may retain some biological or immunogenic activities. In fact, peptides composed of as few as six amino acid residues may often evoke an immune response.

Accordingly, the present invention further provides polypeptides having one or more residues deleted from the amino terminus of the amino acid sequence shown in FIGS. 9A-B (i.e., SEQ ID NO:159), up to the Glu residue at position number 185 and polynucleotides encoding such polypeptides.

Particularly, N-terminal deletions of the polypeptide can be described by the general formula m−190, where m is an integer from 2 to 184, where m corresponds to the position of the amino acid residue identified in SEQ ID NO:160. More in particular, the invention provides polynucleotides encoding polypeptides comprising, or alternatively consisting of, an amino acid sequence selected from the group: V-26 to I-190; R-27 to I-190; C-28 to I-190; S-29 to I-190; R-30 to I-190; P-31 to I-190; G-32 to I-190; A-33 to I-190; K-34 to I-190; R-35 to I-190; S-36 to I-190; E-37 to I-190; K-38 to I-190; I-39 to I-190; Y-40 to I-190; Q-41 to I-190; Q-42 to I-190; R-43 to I-190; S-44 to I-190; L-45 to I-190; R-46 to I-190; E-47 to I-190; D-48 to I-190; Q-49 to I-190; Q-50 to I-190; S-51 to I-190; F-52 to I-190; T-53 to I-190; G-54 to I-190; S-55 to I-190; R-56 to I-190; T-57 to I-190; Y-58 to I-190; S-59 to I-190; L-60 to I-190; V-61 to I-190; G-62 to I-190; Q-63 to I-190; A-64 to I-190; W-65 to I-190; P-66 to I-190; G-67 to I-190; P-68 to I-190; L-69 to I-190; A-70 to I-190; D-71 to I-190; M-72 to I-190; A-73 to I-190; P-74 to I-190; T-75 to I-190; R-76 to I-190; K-77 to I-190; D-78 to I-190; K-79 to I-190; L-80 to I-190; L-81 to I-190; Q-82 to I-190; F-83 to I-190; Y-84 to I-190; P-85 to I-190; S-86 to I-190;

L-87 to I-190; E-88 to I-190; D-89 to I-190; P-90 to I-190; A-91 to I-190; S-92 to I-190; S-93 to I-190; R-94 to I-190; Y-95 to I-190; Q-96 to I-190; N-97 to I-190; F-98 to I-190; S-99 to I-190; K-100 to I-190; G-101 to I-190; S-102 to I-190; R-103 to I-190; H-104 to I-190; G-105 to I-190; S-106 to I-190; E-107 to I-190; E-108 to I-190; A-109 to I-190; Y-110 to I-190; I-111 to I-190; D-112 to I-190; P-113 to I-190; I-114 to I-190; A-115 to I-190; M-116 to I-190; E-117 to I-190; Y-118 to I-190; Y-119 to I-190; N-120 to I-190; W-121 to I-190; G-122 to I-190; R-123 to I-190; F-124 to I-190; S-125 to I-190; K-126 to I-190; P-127 to I-190; P-128 to I-190; E-129 to I-190; D-130 to I-190; D-131 to I-190; D-132 to I-190; A-133 to I-190; N-134 to I-190; S-135 to I-190; Y-136 to I-190; E-137 to I-190; N-138 to I-190; V-139 to I-190; L-140 to I-190; I-141 to I-190; C-142 to I-190; K-143 to I-190; Q-144 to I-190; K-145 to I-190; T-146 to I-190; T-147 to I-190; E-148 to I-190; T-149 to I-190; G-150 to I-190; A-151 to I-190; Q-152 to I-190; Q-153 to I-190; E-154 to I-190; G-155 to I-190; I-156 to I-190; G-157 to I-190; G-158 to I-190; L-159 to I-190; C-160 to I-190; R-161 to I-190; G-162 to I-190; D-163 to I-190; L-164 to I-190; S-165 to I-190; L-166 to I-190; S-167 to I-190; L-168 to I-190; A-169 to I-190; L-170 to I-190; K-171 to I-190; T-172 to I-190; G-173 to I-190; P-174 to I-190; T-175 to I-190; S-176 to I-190; G-177 to I-190; L-178 to I-190; C-179 to I-190; P-180 to I-190; S-181 to I-190; A-182 to I-190; S-183 to I-190; P-184 to I-190; and E-185 to I-190, of SEQ ID NO:160. Polypeptides encoding these polynucleotides are also encompassed by the invention. Moreover, fragments and variants of these polypeptides (such as, for example, fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides, or the complement thereof) are encompassed by the invention. Antibodies that bind polypeptides of the invention are also encompassed by the invention. Polynucleotides encoding these polypeptides are also encompassed by the invention.

Also as mentioned above, even if deletion of one or more amino acids from the C terminus of a protein results in modification of loss of one or more biological functions of the protein, other functional activities (e.g., biological activities, ability to multimerize, ability to bind ligand) may still be retained. For example the ability of the shortened mutein to induce and/or bind to antibodies which recognize the complete or mature forms of the polypeptide generally will be retained when less than the majority of the residues of the complete or mature polypeptide are removed from the C terminus. Whether a particular polypeptide lacking C terminal residues of a complete polypeptide retains such immunologic activities can readily be determined by routine methods described herein and otherwise known in the art. It is not unlikely that an mutein with a large number of deleted C terminal amino acid residues may retain some biological or immunogenic activities. In fact, peptides composed of as few as six amino acid residues may often evoke an immune response.

Accordingly, the present invention further provides polypeptides having one or more residues deleted from the carboxy terminus of the amino acid sequence of the polypeptide shown in FIGS. 9A-B (SEQ ID NO:160), as described by the general formula 1–n, where n is an integer from 6 to 184 where n corresponds to the position of amino acid residue identified in SEQ ID NO:160. More in particular, the invention provides polynucleotides encoding polypeptides comprising, or alternatively consisting of, an amino acid sequence selected from the group: V-26 to G-189; V-26 to E-188; V-26 to D-187; V-26 to E-186; V-26 to E-185; V-26 to P-184; V-26 to S-183; V-26 to A-182; V-26 to S-181; V-26 to P-180; V-26 to C-179; V-26 to L-178; V-26 to G-177; V-26 to S-176; V-26 to T-175; V-26 to P-174; V-26 to G-173; V-26 to T-172; V-26 to K-171; V-26 to L-170; V-26 to A-169; V-26 to L-168; V-26 to S-167; V-26 to L-166; V-26 to S-165; V-26 to L-164; V-26 to D-163; V-26 to G-162; V-26 to R-161; V-26 to C-160; V-26 to L-159; V-26 to G-158; V-26 to G-157; V-26 to I-156; V-26 to G-155; V-26 to E-154; V-26 to Q-153; V-26 to Q-152; V-26 to A-151; V-26 to G-150; V-26 to T-149; V-26 to E-148; V-26 to T-147; V-26 to T-146; V-26 to K-145; V-26 to Q-144; V-26 to K-143; V-26 to C-142; V-26 to I-141; V-26 to L-140; V-26 to V-139; V-26 to N-138; V-26 to E-137; V-26 to Y-136; V-26 to S-135; V-26 to N-134; V-26 to A-133; V-26 to D-132; V-26 to D-131; V-26 to D-130; V-26 to E-129; V-26 to P-128; V-26 to P-127; V-26 to K-126; V-26 to S-125; V-26 to F-124; V-26 to R-123; V-26 to G-122; V-26 to W-121; V-26 to N-120; V-26 to Y-119; V-26 to Y-118; V-26 to E-117; V-26 to M-116; V-26 to A-115; V-26 to I-114; V-26 to P-113; V-26 to D-112; V-26 to I-111; V-26 to Y-110; V-26 to A-109; V-26 to E-108; V-26 to E-107; V-26 to S-106; V-26 to G-105; V-26 to H-104; V-26 to R-103; V-26 to S-102; V-26 to G-101; V-26 to K-100; V-26 to S-99; V-26 to F-98; V-26 to N-97; V-26 to Q-96; V-26 to Y-95; V-26 to R-94; V-26 to S-93; V-26 to S-92; V-26 to A-91; V-26 to P-90; V-26 to D-89; V-26 to E-88; V-26 to L-87; V-26 to S-86; V-26 to P-85; V-26 to Y-84; V-26 to F-83; V-26 to Q-82; V-26 to L-81; V-26 to L-80; V-26 to K-79; V-26 to D-78; V-26 to K-77; V-26 to R-76; V-26 to T-75; V-26 to P-74; V-26 to A-73; V-26 to M-72; V-26 to D-71; V-26 to A-70; V-26 to L-69; V-26 to P-68; V-26 to G-67; V-26 to P-66; V-26 to W-65; V-26 to A-64; V-26 to Q-63; V-26 to G-62; V-26 to V-61; V-26 to L-60; V-26 to S-59; V-26 to Y-58; V-26 to T-57; V-26 to R-56; V-26 to S-55; V-26 to G-54; V-26 to T-53; V-26 to F-52; V-26 to S-51; V-26 to Q-50; V-26 to Q-49; V-26 to D-48; V-26 to E-47; V-26 to R-46; V-26 to L-45; V-26 to S-44; V-26 to R-43; V-26 to Q-42; V-26 to Q-41; V-26 to Y-40; V-26 to I-39; V-26 to K-38; V-26 to E-37; V-26 to S-36; V-26 to R-35; V-26 to K-34; V-26 to A-33; V-26 to G-32; and V-26 to P-31 of SEQ ID NO:160. Polypeptides encoding these polynucleotides are also encompassed by the invention. Moreover, fragments and variants of these polypeptides (such as, for example, fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides, or the complement thereof) are encompassed by the invention. Antibodies that bind polypeptides of the invention are also encompassed by the invention. Polynucleotides encoding these polypeptides are also encompassed by the invention.

In addition, any of the above listed N- or C-terminal deletions can be combined to produce a N- and C-terminal deleted polypeptide. The invention also provides polypeptides having one or more amino acids deleted from both the amino and the carboxyl termini, which may be described generally as having residues m-n of SEQ ID NO:160, where n and m are integers as described above. Polynucleotides encoding these polypeptides are also encompassed by the invention.

Also included are a nucleotide sequence encoding a polypeptide consisting of a portion of the complete amino acid sequence encoded by the cDNA clone contained in ATCC™ Deposit No. 209889, where this portion excludes any integer of amino acid residues from 1 to about 184 amino acids from the amino terminus of the complete amino acid sequence encoded by the cDNA clone contained in ATCC™ Deposit No. 209889, or any integer of amino acid residues from 1 to about 190 amino acids from the carboxy terminus, or any combination of the above amino terminal and carboxy terminal deletions, of the complete amino acid sequence encoded by the cDNA clone contained in ATCC™ Deposit No. 209889. Polynucleotides encoding all of the above deletion mutant polypeptide forms also are provided.

The present application is also directed to proteins containing polypeptides at least 90%, 92%, 93%, 94%, 95%, 96%, 97%, 98% or 99% identical to the polypeptide sequence set forth herein m-n. In preferred embodiments, the application is directed to proteins containing polypeptides at least 90%, 95%, 96%, 97%, 98% or 99% identical to polypeptides having the amino acid sequence of the specific N and C terminal deletions recited herein. Polynucleotides encoding these polypeptides are also encompassed by the invention.

Polynucleotides and polypeptides of the invention are useful as reagents for differential identification of the tissue(s) or cell type(s) present in a biological sample and for diagnosis of diseases and conditions which include, but are not limited to, disorders affecting the immune and hematopoietic systems, particularly hematopoiesis. Similarly, polypeptides and antibodies directed to these polypeptides are useful in providing immunological probes for differential identification of the tissue(s) or cell type(s). For a number of disorders of the above tissues or cells, particularly of the immune system and hematopoeitic system, expression of this gene at significantly higher or lower levels may be routinely detected in certain tissues or cell types (e.g., immune, hematopoietic, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

This gene has been found to stimulate the proliferation of bone marrow CD34+ cells. This assay which is described in Example 52 herein is based on the ability of human CD34+ to proliferate in presence of hematopoietic growth factors and evaluates the ability of the polypeptides of the invention, and agonists and antagonists thereof, to stimulate or inhibit this proliferation.

The tissue distribution in immune and hematopoietic cells and tissues and the ability to stimulate the proliferation of bone marrow CD34+ cells indicates that polynucleotides and polypeptides corresponding to this gene are useful for the diagnosis and treatment of disorders affecting the immune system and hematopoiesis. Representative uses are described in the “Immune Activity” and “Infectious Disease” sections below, in Examples 17, 42, 44, 45, 47, 49, 50, and 51 and elsewhere herein. Briefly, the expression of this gene product indicates a role in regulating the proliferation; survival; differentiation; and/or activation of hematopoietic cell lineages, including blood stem cells. Moreover, the protein represents a secreted factor that influences the differentiation or behavior of other blood cells, or that recruits hematopoietic cells to sites of injury. Thus, this gene product is thought to be useful in the expansion of stem cells and committed progenitors of various blood lineages, and in the differentiation and/or proliferation of various cell types.

The polynucleotides and/or polypeptides of the invention and/or agonists and/or antagonists thereof, can also be employed to inhibit the proliferation and differentiation of hematopoietic cells and therefore may be employed to protect bone marrow stem cells from chemotherapeutic agents during chemotherapy. This antiproliferative effect may allow administration of higher doses of chemotherapeutic agents and, therefore, more effective chemotherapeutic treatment.

The polynucleotides and/or polypeptides of the invention and/or agonists and/or antagonists thereof, may also be employed for the expansion of immature hematopoietic progenitor cells, for example, granulocytes, macrophages or monocytes, by temporarily preventing their differentiation. These bone marrow cells may be cultured in vitro. Thus, polynucleotides and/or polypeptides of the invention, or agonists or antagonists thereof, may be useful as a modulator of hematopoietic stem cells in vitro for the purpose of bone marrow transplantation and/or gene therapy. Since stem cells are rare and are most useful for introducing genes into for gene therapy, polynucleotides and/or polypeptides of the invention can be used to isolate enriched populations of stem cells. Stem cells can be enriched by culturing cells in the presence of cytotoxins, such as 5-Fu, which kills rapidly dividing cells, where as the stem cells will be protected by polynucleotides and/or polypeptides of the invention. These stem cells can be returned to a bone marrow transplant patient or can then be used for transfection of the desired gene for gene therapy. In addition, this gene can be injected into animals which results in the release of stem cells from the bone marrow of the animal into the peripheral blood. These stem cells can be isolated for the purpose of autologous bone marrow transplantation or manipulation for gene therapy. After the patient has finished chemotherapy or radiation treatment, the isolated stem cells can be returned to the patient.

Polynucleotides and polypeptides corresponding to this gene are useful for the treatment and diagnosis of hematopoietic related disorders such as anemia, pancytopenia, leukopenia, thrombocytopenia or leukemia since stromal cells are important in the production of cells of hematopoietic lineages. The uses include bone marrow cell ex-vivo culture, bone marrow transplantation, bone marrow reconstitution, radiotherapy or chemotherapy of neoplasia.

This gene product may also be involved in the regulation of cytokine production, antigen presentation, or other processes suggesting a usefulness in the treatment of cancer (e.g. by boosting immune responses). Since the gene is expressed in cells of lymphoid origin, the natural gene product is involved in immune functions. Therefore it is also useful as an agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, systemic lupus erythematosis, drug induced hemolytic anemia, rheumatoid arthritis, Sjogren’s disease, and scleroderma.

This gene may also have a very wide range of biological activities. Representative uses are described in the “Chemotaxis” and “Binding Activity” sections below, in Examples 31, 42, 44, 45, 46, 47, 49, 50, and 51, and elsewhere herein. Briefly, the protein may possess the following activities: cytokine, cell proliferation/differentiation modulating activity or induction of other cytokines; immunostimulating/immunosuppressant activities (e.g. for treating human immunodeficiency virus infection, cancer, autoimmune diseases and allergy); regulation of hematopoiesis (e.g. for treating anemia or as adjunct to chemotherapy); stimulation or growth of bone, cartilage, tendons, ligaments and/or nerves (e.g. for treating wounds, stimulation of follicle stimulating hormone (for control of fertility); chemotactic and chemokinetic activities (e.g. for treating infections, tumors); hemostatic or thrombolytic activity (e.g. for treating hemophilia, cardiac infarction etc.); anti-inflammatory activity (e.g. for treating septic shock, Crohn's disease); as antimicrobials; for treating psoriasis or other hyperproliferative diseases; for regulation of metabolism, and behavior. Also contemplated is the use of the corresponding nucleic acid in gene therapy procedures. Based upon the proteins immune cell specific message distribution, it may be involved in many aspects of the immune response, especially its initial stages, inflammation, allograft rejection, infectious disease response etc. It is frequently found in the hematopoietic cell cDNA libraries. Thus, this factor could be involved in the control of hematopoietic cell proliferation, differentiation, and function. Based on this one can postulate its use in the management of anemias, leukemias, neutropenia, thrombocytopenia, autoimmune diseases, blood tissue engraftment, and poikilothromerythromatosis. Furthermore, the protein may also be used to determine biological activity, raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

The gene encoding the disclosed cDNA is believed to reside on chromosome 7. Accordingly, polynucleotides related to this invention are useful as a marker in linkage analysis for chromosome 7.

Features of Protein Encoded by Gene No: 22

Preferred polypeptides of the invention comprise the following amino acid sequences:

(SEQ ID NO: 171)
FEIALPRESNITVLIKLGTPTLLAKPCYIVISKRHITMLSIKSGERIVFTF

SCQSPENHFVIEIQKNIDCMSGPCPFGEVQLQPSTSLLPTLNRTFIWDVKA

HKSIGLELQFSIPRLRQIGPGESCPDGVTHSISGRIDATVVRIGTFCSNGT

VSRIKM, (SEQ ID NO: 172)
MAGLNCGVSIALLGVLLLGAARLPRGAEAFEIALPRESNITVLIKLGTPTL

LAKPCYIVISKRHITMLSIKSGERIVFTFSCQSPENHFVIEIQKNIDCMSG

PCPFGEVQLQPSTSLLPTLNRTFIWDVKAHKSIGLELQFSIPRLRQIGPGE

SCPDGVTHSISGRIDATVVRIGTFCSNGTVSRIKMQEGVKMALHLPWFHPR

NVSGFSIANRSSIKRLCIIESVFEGEGSATLMSANYPEGFPEDELMTWQFV

VPAHLRASVSFLNFNLSNCERKEERVEYYIPGSTTNPEVFKLEDKQPGNMA

GNFNLSLQGCDQDAQSPGILRLQFQVLVQHPQNESNKIYVVDLSNERAMSL

TIEPRPVKQSRKFVPGCFVCLESRTCSSNLTLTSGSKHKISFLCDDLTRLW

MNVEKP and/or (SEQ ID NO: 173)
GTRAAPGLGAWGRRSPPSFSPPRPRRPGVMAGLNCGVSIALLGVLLLGAAR

LPRGAEAFEIALPRESNITVLIKLGTPTLLAKPCYIVISKRHITMLSIKSG

ERIVFTFSCQSPENHFVIEIQKNIDCMSGPCPFGEVQLQPSTSLLPTLNRT

FIWDVKAHKSIGLELQFSIPRLRQIGPGESCPDGVTHSISGRIDATVVRIG

TFCSNGTVSRIKMQEGVKMALHLPWFHPRNVSGFSIANRSSIKRLCIIESV

FEGEGSATLMSANYPEGFPEDELMTWQFVVPAHLRASVSFLNFNLSNCERK

EERVEYYIPGSTTNPEVFKLEDKQPGNMAGNFNLSLQGCDQDAQSPGILRL

-continued

QFQVLVQHPQNESNKIYVVDLSNERAMSLTIEPRPVKQSRKFVPGCFVCLE

SRTCSSNLTLTSGSKHKISFLCDDLTRLWMNVEKP.

Polynucleotides encoding these polypeptides are also provided.

This gene is expressed primarily in placenta, and to a lesser extent in, prostate and ovary.

Therefore, polynucleotides and polypeptides of the invention are useful as reagents for differential identification of the tissue(s) or cell type(s) present in a biological sample and for diagnosis of diseases and conditions which include, but are not limited to, male and female infertility, and associated disorders of the reproductive system. Similarly, polypeptides and antibodies directed to these polypeptides are useful in providing immunological probes for differential identification of the tissue(s) or cell type(s). For a number of disorders of the above tissues or cells, particularly of the reproductive system, expression of this gene at significantly higher or lower levels may be routinely detected in certain tissues or cell types (e.g., reproductive, or cancerous and wounded tissues) or bodily fluids (e.g., lymph, amniotic fluid, seminal fluid, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution of this gene in the prostate, placenta and ovary indicates that polynucleotides and polypeptides corresponding to this gene are useful for treatment, prevention, and/or diagnosis of male or female infertility, endocrine disorders, fetal deficiencies, ovarian failure, amenorrhea, ovarian cancer, benign prostate hyperplasia and prostate cancer. Similarly, the tissue distribution indicates that polynucleotides and polypeptides corresponding to this gene are useful for the diagnosis and treatment of cancer and other proliferative disorders. Expression within placental tissue and other cellular sources marked by proliferating cells indicates that this protein may play a role in the regulation of cellular division. Similarly, embryonic development also involves decisions involving cell differentiation and/or apoptosis in pattern formation. Thus, this protein may also be involved in apoptosis or tissue differentiation and could again be useful in cancer therapy. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:169 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 2195 of SEQ ID NO:169, b is an integer of 15 to 2209, where both a and b correspond to the positions of nucleotide residues shown in SEQ ID NO:169, and where b is greater than or equal to a+14.

Features of Protein Encoded by Gene No: 23

The translation product of this gene was found to be homologous to cell surface adhesion molecule (CAM) proteins. Based on the sequence similarity, the translation product of this gene is expected to share at least some biological activities with CAM proteins. Such activities are known in the art, some of which are described elsewhere herein. A preferred polypeptide variant of the invention comprises the following amino acid sequence:

(SEQ ID NO: 178)
MLCPWRTANLGLLLILTIFLVAEAEGAAQPNNSLMLQTSKENHALASSSL

CMDEKQITQNYSKVLAEVNTSWPVKMATNAVLCCPPIALRNLIIITWEII

LRGQPSCTKAYKKETNETKETNCTDERITWVSRPDQNSDLQIRTVAITHD

GYYRCIMVTPDGNFHRGYHLQVLVTPEVTLFQNRNRTAVCKAVAGKPAAH

ISWIPEGDCATKQEYWSNGTVTVKSTCHWEVHNVSTVNCHVSHLTGNKSL

YIELLPVPGAKKSSKLYIPYIILTIIILTIVGXIWLLKVNGCXKYKLNKP

ESTPVVEEDEMQPYAFYTEKNNPLXXTTNKVKASEALQSEVDTDLHTL.

Polynucleotides encoding these polypeptides are also provided.

The polypeptide of this gene has been determined to have a transmembrane domain at about amino acid position 271-287 of the amino acid sequence referenced in Table 1A for this gene. Moreover, a cytoplasmic tail encompassing amino acids 288 to 348 of this protein has also been determined. Based upon these characteristics, it is believed that the protein product of this gene shares structural features to type Ia membrane proteins.

This gene is expressed primarily in dendritic cells.

Therefore, polynucleotides and polypeptides of the invention are useful as reagents for differential identification of the tissue(s) or cell type(s) present in a biological sample and for diagnosis of diseases and conditions which include, but are not limited to, immunodeficiency, tumor necrosis, infection, lymphomas, auto-immunities, cancer, metastasis, wound healing, inflammation, anemias (leukemia) and other hematopoeitic disorders. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., immune, hematopoietic, and cancerous and wounded tissues) or bodily fluids (e.g., serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise immunogenic epitopes shown in SEQ ID NO:175 as residues: Asp-53 to Tyr-61, Pro-105 to Ile-128, Arg-133 to Leu-140, Gln-182 to Ala-188, Pro-205 to Asn-218, Gly-259 to Ala-264, Asn-290 to Ser-302, Glu-307 to Tyr-314, Tyr-317 to Lys-332. Polynucleotides encoding said polypeptides are also provided.

The tissue distribution in dendritic cells indicates that polynucleotides and polypeptides corresponding to this gene are useful for the diagnosis and treatment of immune disorders including: leukemias, lymphomas, auto-immunities, immunodeficiencies (e.g. AIDS), immuno-suppressive conditions (transplantation) and hematopoeitic disorders. In addition this gene product may be applicable in conditions of general microbial infection, inflammation or cancer. Representative uses are described in the "Immune Activity" and "Infectious Disease" sections below, in Examples 17, 42, 44, 45, 47, 49, 50, and 51, and elsewhere herein. Briefly, the expression of this gene product indicates a role in regulating the proliferation; survival; differentiation; and/or activation of hematopoietic cell lineages, including blood stem cells. This gene product is involved in the regulation of cytokine production, antigen presentation, or other processes suggesting a usefulness in the treatment of cancer (e.g. by boosting immune responses). Since the gene is expressed in cells of lymphoid origin, the natural gene product is involved in immune functions. Therefore it is also useful as an agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, systemic lupus erythematosis, drug induced hemolytic anemia, rheumatoid arthritis, Sjogren's disease, and scleroderma.

Moreover, the protein may represent a secreted factor that influences the differentiation or behavior of other blood cells, or that recruits hematopoietic cells to sites of injury. Thus, this gene product is thought to be useful in the expansion of stem cells and committed progenitors of various blood lineages, and in the differentiation and/or proliferation of various cell types. Furthermore, the protein may also be used to determine biological activity, raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:174 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 3784 of SEQ ID NO:174, b is an integer of 15 to 3798, where both a and b correspond to the positions of nucleotide residues shown in SEQ ID NO:174, and where b is greater than or equal to a+14.

Features of Protein Encoded by Gene No: 24

The translation product of this gene shares sequence homology with CMRF-35 antigen [*Homo sapiens*] (See, e.g., Genbank accession number AAD01646 and CAA46948; all references available through these accessions are hereby incorporated by reference herein), which is thought to be important as a cell membrane antigen present on the surface of monocytes, neutrophils, a proportion of peripheral blood T and B lymphocytes and lymphocytic cell lines.

The translation product of this gene also shares sequence homology with PIGR-1 protein (see, e.g., Genseq accession number W99070 which is a member of the Immunoglobulin (Ig) superfamily). All references available through this Genseq accession are hereby incorporated by reference herein. Based on the sequence similarity, the translation product of this clone is expected to share at least some biological activities with proteins of the Immunoglobulin superfamily such as, for example, PIGR-1 and CMRF-35 Ag. Such activities are known in the art, some of which are described elsewhere herein.

In specific embodiments, polypeptides of the invention comprise, or alternatively consist of, the following amino acid sequence:

(SEQ ID NO: 181)
EGGSSRARXSTSRRLGVCSLFLLPGSTEGNGDLSEEK.

Moreover, fragments and variants of these polypeptides (such as, for example, fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides, or the complement thereof) are encompassed by the invention. Antibodies that bind polypeptides of the invention are also encompassed by the invention. Polynucleotides encoding these polypeptides are also encompassed by the invention.

The polypeptide of this gene has been determined to have a transmembrane domain at about amino acid position 157-173 of the amino acid sequence referenced in Table 1A for this gene. Moreover, a cytoplasmic tail encompassing amino acids 174-290 of this protein has also been determined. Based upon these characteristics, it is believed that the protein product of this gene shares structural features to type Ia membrane proteins.

This gene is expressed primarily in eosinophils, and to a lesser extent in dendritic cells and activated monocytes.

Polynucleotides and polypeptides of the invention are useful as reagents for differential identification of the tissue(s) or cell type(s) present in a biological sample and for diagnosis of diseases and conditions which include, but are not limited to, immune disorders. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., immune, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred polypeptides of the present invention comprise, or alternatively consist of one, two, three, or all four, of the immunogenic epitopes shown in SEQ ID NO:180 as residues: Ser-69 to Arg-79, Ile-82 to Arg-89, Pro-129 to Ser-137, Leu-146 to Lys-151. Polynucleotides encoding said polypeptides are also encompassed by the invention.

The tissue distribution in eosinophils, monocytes, and dendritic cells, and the homology to CMRF-35 antigen, indicates that polynucleotides and polypeptides corresponding to this gene are useful for the diagnosis and/or treatment of immune disorders. Representative uses are described in the "Immune Activity" and "Infectious Disease" sections below, in Examples 17, 42, 44, 45, 47, 49, 50, and 51, and elsewhere herein. Expression of this gene product in eosinophils, monocytes, and dendritic cells also strongly indicates a role for this protein in immune function and immune surveillance. This gene product may be involved in the regulation of cytokine production, antigen presentation, or other processes that may also suggest a usefulness in the treatment of cancer (e.g., by boosting immune responses). Since the gene is expressed in cells of lymphoid origin, the gene or protein, as well as, antibodies directed against the protein may show utility as a tumor marker and/or immunotherapy targets for the above listed tissues. Therefore it may be also used as an agent for immunological disorders including arthritis, asthma, immune deficiency diseases such as AIDS, leukemia, rheumatoid arthritis, systemic lupus erythematosus, inflammatory bowel disease, sepsis, acne, and psoriasis. In addition, this gene product may have commercial utility in the expansion of stem cells and committed progenitors of various blood lineages, and in the differentiation and/or proliferation of various cell types. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:179 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 1782 of SEQ ID NO:179, b is an integer of 15 to 1796, where both a and b correspond to the positions of nucleotide residues shown in SEQ ID NO:179, and where b is greater than or equal to a+14.

Features of Protein Encoded by Gene No: 25

This gene is expressed in the following tissues/cDNA libraries: B Cell lymphoma; pBMC stimulated w/ poly I/C; B-cells (unstimulated); NCI_CGAP_GCB1.

The tissue distribution indicates polynucleotides and polypeptides corresponding to this gene, as well as antibodies against those polypeptides, may be useful for the diagnosis, prevention, and/or treatment of immune system disorders; particularly immune cell proliferative disorders (e.g. leukemia), autoimmune disorders, and immunodeficiencies (including immunodeficiencies caused by genetic factors, microbial pathogens (e.g. HIV), chemotherapy, and radiation). See "Immune Activity" section, infra. The tissue distribution also indicates polynucleotides and polypeptides corresponding to this gene, as well as antibodies against those polypeptides, may be useful for the diagnosis, prevention, and/or treatment of cancer and other hyperproliferative disorders (e.g., see "Hyperproliferative Disorders" section, infra).

Features of Protein Encoded by Gene No: 26

This invention relates to newly identified polynucleotides, polypeptides encoded by such polynucleotides, the use of such polynucleotides and polypeptides, as well as the production of such polynucleotides and polypeptides. The polypeptide of the present invention has been putatively identified as a human integrin alpha 11 homolog derived from a human osteoblast II cDNA library. More particularly, the polypeptide of the present invention has been putatively identified as a human integrin alpha 11-subunit homolog, sometimes hereafter referred to as "integrin alpha 11", "integrin alpha 11-subunit", "a11", "A11-subunit", and/or "Integrin all-subunit". The invention also relates to inhibiting the action of such polypeptides. The integrins are a large family of cell adhesion molecules consisting of noncovalently associated ab heterodimers.

We have cloned and sequenced a novel human integrin α-subunit cDNA, designated a11. The all cDNA encodes a protein with a 22 amino acid signal peptide, a large 1120 residue extracellular domain that contains an I-domain of 207 residues and is linked by a transmembrane domain to a short cytoplasmic domain of 24 amino acids. The deduced all protein shows the typical structural features of integrin a-subunits and is similar to a distinct group of a-subunits from collagen-binding integrins. However, it differs from most integrin a-chains by an incompletely preserved cytoplasmic GFFKR motif.

The human ITGA11 gene was located to bands q22.3-23 on chromosome 15, and its transcripts were found predominantly in bone, cartilage as well as in cardiac and skeletal muscle. Expression of the 5.5 kilobase all mRNA was also detectable in ovary and small intestine.

All vertebrate cells express members of the integrin family of cell adhesion molecules, which mediate cellular adhesion to other cells and extracellular subtratum, cell migration and participate in important physiologic processes from signal transduction to cell proliferation and differentiation (Hynes, 92; Springer, 92).

Integrins are structurally homologous heterodimeric type-I membrane glycoproteins formed by the noncovalent association of one of eight b-subunits with one of the 17 different a-subunits described to date, resulting in at least 22 different ab complexes. Their binding specificities for cellular and extracellular ligands are determined by both subunits and are dynamically regulated in a cell-type-specific mode by the cellular environment as well as by the developmental and activation state of the cell (Diamond and Springer, 94). In integrin a-subunits, the aminoterminal region of the large extracellular domain consists of a seven-fold repeated structure which is predicted to fold into a b-propeller domain (Corbi et al., 1987; Springer, 1997). The three or four C-terminal repeats contain putative divalent cation binding motifs that are thought to be important for ligand binding and subunit association (Diamond and Springer, 94). The a1, a2, a 10, aD, aE, aL, aM and aX-subunits contain an approximately 200 amino acid I-domain inserted between the second and third repeat that is not present in other a-chains (Larson et al., 1989). Several isolated I-domains have been shown to independently bind the ligands of the parent integrin heterodimer (Kamata and Takada, 1994; Randi and Hogg, 1994). The a3, a5-8, aIIb and aV-subunits are proteolytically processed at a conserved site into disulphide-linked heavy and light chains, while the a4-subunit is cleaved at a more aminoterminal site into two fragments that remain noncovalently associated (Hemler et al., 90). Additional a-subunit variants are generated by alternative splicing of primary transcripts (Ziober et al., 93; Delwel et al., 95; Leung et al., 98).

The extracellular domains of a-integrin subunits are connected by a single spanning transmembrane domain to short, diverse cytoplasmic domains whose only conserved feature is a membrane-proximal KXGFF(K/R)R motif (Sastry and Horwitz, 1993). The cytoplasmic domains have been implicated in the cell-type-specific modulation of integrin affinity states (Williams et al., 1994).

The polypeptide of the present invention has been putatively identified as a member of the integrin family and has been termed integrin alpha 11 subunit ("a11"). This identification has been made as a result of amino acid sequence homology to the human integrin alpha 1 subunit (See Genbank Accession No. gi|346210).

FIGS. 11A-F show the nucleotide (SEQ ID NO:186) and deduced amino acid sequence (SEQ ID NO:187) of a11. Predicted amino acids from about 1 to about 22 constitute the predicted signal peptide (amino acid residues from about 1 to about 22 in SEQ ID NO:187) and are represented by the underlined amino acid regions; amino acids from about 666 to about 682, and/or amino acids from about 1145 to about 1161 constitute the predicted transmembrane domains (amino acids from about 666 to about 682, and/or amino acids from about 1145 to about 1161 in SEQ ID NO:187) and are represented by the double underlined amino acids; and amino acids from about 64 to about 96 constitute the predicted immunoglobulin and major histocompatibility complex protein domain (amino acids from about 64 to about 96 in SEQ ID NO:187) and are represented by the bold amino acids.

FIGS. 12A-E shows the regions of similarity between the amino acid sequences of the integrin alpha 11 subunit (a11) protein (SEQ ID NO:187) and the human integrin alpha 1 subunit (SEQ ID NO:191).

FIG. 13 shows an analysis of the integrin alpha 11 subunit (a11) amino acid sequence. Alpha, beta, turn and coil regions; hydrophilicity and hydrophobicity; amphipathic regions; flexible regions; antigenic index and surface probability are shown.

Its translation product has homology to the characteristic immunoglobulin and major histocompatibility complex protein domain of integrin family members. As shown in FIGS. 11A-F, a11 has transmembrane domains (the transmembrane domains comprise amino acids 666-682 and/or 1145-1161 of SEQ ID NO:187; which correspond to amino acids 666-682 and/or 1145-1161 of FIGS. 11A-F) with strong conservation between other members of the integrin family. The polynucleotide contains an open reading frame encoding the a11 polypeptide of 1189 amino acids. The present invention exhibits a high degree of homology at the amino acid level to the human integrin alpha 1 subunit (as shown in FIGS. 12A-E).

Preferred polypeptides of the invention comprise, or alternatively consist of, the following amino acid sequence:

(SEQ ID NO: 190)
TNGYQKTGDVYKCPVIHGNCTKLNLGRVTLSNV.

Polynucleotides encoding these polypeptides are also encompassed by the invention, as are antibodies that bind one or more of these polypeptides. Moreover, fragments and variants of these polypeptides (e.g., fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides, or the complement thereof) are encompassed by the invention. Antibodies that bind these fragments and variants of the invention are also encompassed by the invention. Polynucleotides encoding these fragments and variants are also encompassed by the invention.

Preferred polypeptides of the present invention comprise, or alternatively consist of, one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, or all thirty-three of the immunogenic epitopes shown in SEQ ID NO:187 as residues: Phe-23 to Arg-31, Leu-62 to Asp-72, Val-96 to Asp-101, Thr-111 to Asn-116, Glu-128 to Thr-135, Val-142 to Ser-149, Asn-217 to Val-222, Glu-233 to Arg-241, Gly-272 to Leu-280, Gln-286 to Thr-293, Tyr-303 to Ile-308, Gly-354 to Thr-360, Glu-408 to Lys-419, Glu-508 to Lys-514, Arg-521 to Val-526, Gly-529 to Phe-542, Asp-551 to Tyr-557, Thr-587 to Thr-593, His-656 to Asp-665, Met-697 to Arg-705, Asp-709 to Thr-716, Glu-755 to Gly-760, Asn-779 to His-786, Leu-810 to Asp-816, Leu-844 to Ala-851, Gln-871 to Gly-877, Glu-884 to Gln-889, Ser-931 to Asn-943, Ser-974 to Ile-982, Gly-1039 to Gln-1058, Arg-1121 to Arg-1127, Ser-1134 to Trp-1139, and/or Ser-1172 to Pro-1183. Polynucleotides encoding these polypeptides are also encompassed by the invention, as are antibodies that bind one or more of these polypeptides. Moreover, fragments and variants of these polypeptides (e.g., fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides, or the complement thereof) are encompassed by the invention. Antibodies that bind these fragments and variants of the invention are also encompassed by the invention. Polynucleotides encoding these fragments and variants are also encompassed by the invention.

The present invention provides isolated nucleic acid molecules comprising a polynucleotide encoding the a11 polypeptide having the amino acid sequence shown in FIGS. 11A-F (SEQ ID NO:187). The nucleotide sequence shown in FIGS. 11A-F (SEQ ID NO:186) was obtained by sequencing a cloned cDNA (HOHBY69), which was deposited on November 17 at the American Type Culture Collection, and given Accession Number 203484.

The present invention is further directed to fragments of the isolated nucleic acid molecules described herein. By a fragment of an isolated DNA molecule having the nucleotide sequence of the deposited cDNA or the nucleotide sequence shown in SEQ ID NO:186 is intended DNA fragments at least about 15 nt, and more preferably at least about 20 nt, still more preferably at least about 30 nt, and even more preferably, at least about 40 nt in length which are useful as diagnostic probes and primers as discussed herein. Of course, larger fragments 50-1500 nt in length are also useful according to the present invention, as are fragments corresponding to most, if not all, of the nucleotide sequence of the deposited cDNA or as shown in SEQ ID NO:186. By a fragment at least 20 nt in length, for example, is intended fragments which include 20 or more contiguous bases from the nucleotide sequence of the deposited cDNA or the nucleotide sequence as shown in SEQ ID NO:186. In this context "about" includes the particularly recited size, larger or smaller by several (5, 4, 3, 2, or 1) nucleotides, at either terminus or at both termini. Representative examples of a11 polynucleotide fragments of the invention include, for example, fragments that comprise, or alternatively, consist of, a sequence from about nucleotide 1 to about 50, from about 51 to about 100, from about 101 to about 150, from about 151 to about 200, from about 201 to about 250, from about 251 to about 300, from about 301 to about 350, from about 351 to about 400, from about 401 to about 450, from about 451 to about 500, from about 501 to about 550, from about 551 to about 600, from about 601 to about 650, from about 651 to about 700, from about 701 to about 750, from about 751 to about 800, from about 801 to about 850, from about 851 to about 900, from about 901 to about 950, from about 951 to about 1000, from about 1001 to about 1050, from about 1051 to about 1100, from about 1101 to about 1150, from about 1151 to about 1200, from about 1201 to about 1250, from about 1251 to about 1300, from about 1301 to about 1350, from about 1351 to about 1400, from about 1401 to about 1450, from about 1451 to about 1500, from about 1501 to about 1550, from about 1551 to about 1600, from about 1601 to about 1650, from about 1651 to about 1700, from about 1701 to about 1750, from about 1751 to about 1800, from about 1801 to about 1850, from about 1851 to about 1900, from about 1901 to about 1950, from about 1951 to about 2000, from about 2001 to about 2050, from about 2051 to about 2100, from about 2101 to about 2150, from about 2151 to about 2200, from about 2201 to about 2250, from about 2251 to about 2300, from about 2301 to about 2350, from about 2351 to about 2400, from about 2401 to about 2450, from about 2451 to about 2500, from about 2501 to about 2550, from about 2551 to about 2600, from about 2601 to about 2650, from about 2651 to about 2700, from about 2701 to about 2750, from about 2751 to about 2800, from about 2801 to about 2850, from about 2851 to about 2900, from about 2901 to about 2950, from about 2951 to about 3000, from about 3001 to about 3050, from about 3051 to about 3100, from about 3101 to about 3150, from about 3151 to about 3200, from about 3201 to about 3250, from about 3251 to about 3300, from about 3301 to about 3350, from about 3351 to about 3400, from about 3401 to about 3450, from about 3451 to about 3500, from about 3501 to about 3550, from about 3551 to about 3600, from about 3601 to about 3650, from about 3651 to about 3700, from about 3701 to about 3750, from about 3751 to about 3800, from about 3801 to about 3850, from about 3851 to about 3900, from about 3901 to about 3950, from about 3951 to about 4000, from about 4001 to about 4050, from about 4051 to about 4100, from about 4101 to about 4150, from about 4151 to about 4200, from about 4201 to about 4250, from about 4251 to about 4300, from about 4301 to about 4350, from about 4351 to about 4400, from about 4401 to about 4450, from about 4451 to about 4500, from about 4501 to about 4550, from about 4551 to about 4600, from about 4601 to about 4650, from about 4651 to about 4700, from about 4701 to about 4750, from about 4751 to about 4800, from about 4801 to about 4850, from about 4851 to about 4900, from about 4901 to about 4950, from about 4951 to about 4995, from about, from about 1 to about 236, from about 144 to about 188, from about 231 to about 276 of SEQ ID NO:186, or the complementary strand thereto, or the cDNA contained in the deposited gene. In this context "about" includes the particularly recited ranges, larger or smaller by several (5, 4, 3, 2, or 1) nucleotides, at either terminus or at both termini.

Preferred nucleic acid fragments of the present invention include nucleic acid molecules encoding a member selected from the group: a polypeptide comprising or alternatively, consisting of, any one of the transmembrane domains (amino acid residues from about 666 to about 682 and/or 1145 to about 1161 in FIGS. 11A-F (amino acids from about 666 to about 682 and/or 1145 to about 1161 in SEQ ID NO:187), in addition to the immunoglobulin and major histocompatibility complex protein domain (amino acid residues from about 64 to about 96 in FIGS. 11A-F (amino acids from about 64 to about 96 in SEQ ID NO:187). Since the location of these domains have been predicted by computer analysis, one of ordinary skill would appreciate that the amino acid residues constituting these domains may vary slightly (e.g., by about 1 to 15 amino acid residues) depending on the criteria used to define each domain. In additional embodiments, the polynucleotides of the invention encode functional attributes of a11.

Preferred embodiments of the invention in this regard include fragments that comprise alpha-helix and alpha-helix forming regions ("alpha-regions"), beta-sheet and beta-sheet forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, flexible regions, surface-forming regions and high antigenic index regions of the present invention.

The data representing the structural or functional attributes of all set forth in FIG. 13 and/or Table 13, as described above, was generated using the various modules and algorithms of the DNA*STAR set on default parameters. In a preferred embodiment, the data presented in columns VIII, IX, XIII, and XIV of Table 13 can be used to determine regions of all which exhibit a high degree of potential for antigenicity. Regions of high antigenicity are determined from the data presented in columns VIII, IX, XIII, and/or XIV by choosing values which represent regions of the polypeptide which are likely to be exposed on the surface of the polypeptide in an environment in which antigen recognition may occur in the process of initiation of an immune response.

Certain preferred regions in these regards are set out in FIG. 13, but may, as shown in Table 13, be represented or identified by using tabular representations of the data presented in FIG. 13. The DNA*STAR computer algorithm used to generate FIG. 13 (set on the original default parameters) was used to present the data in FIG. 13 in a tabular format (See Table 13). The tabular format of the data in FIG. 13 is used to easily determine specific boundaries of a preferred region. The above-mentioned preferred regions set out in FIG. 13 and in Table 13 include, but are not limited to, regions of the aforementioned types identified by analysis of the amino acid sequence set out in FIGS. 11A-F. As set out in FIG. 13 and in Table 13, such preferred regions include Garnier-Robson alpha-regions, beta-regions, turn-regions, and coil-regions, Chou-Fasman alpha-regions, beta-regions, and turn-regions, Kyte-Doolittle hydrophilic regions and Hopp-Woods hydrophobic regions, Eisenberg alpha- and beta-amphipathic regions, Karplus-Schulz flexible regions, Jameson-Wolf regions of high antigenic index and Emini surface-forming regions. Even if deletion of one or more amino acids from the N-terminus of a protein results in modification of loss of one or more biological functions of the protein, other functional activities (e.g., biological activities, ability to multimerize, etc.) may still be retained. For example, the ability of shortened all muteins to induce and/or bind to antibodies which recognize the complete or mature forms of the polypeptides generally will be retained when less than the majority of the residues of the complete or mature polypeptide are removed from the N-terminus. Whether a particular polypeptide lacking N-terminal residues of a complete polypeptide retains such immunologic activities can readily be determined by routine methods described herein and otherwise known in the art. It is not unlikely that an all mutein with a large number of deleted N-terminal amino acid residues may retain some biological or immunogenic activities. In fact, peptides composed of as few as six all amino acid residues may often evoke an immune response.

Accordingly, the present invention further provides polypeptides having one or more residues deleted from the amino terminus of the all amino acid sequence shown in FIGS. 11A-F, up to the threonine residue at position number 1184 and polynucleotides encoding such polypeptides. In particular, the present invention provides polypeptides comprising the amino acid sequence of residues n1-1189 of FIGS. 11A-F, where n1 is an integer from 2 to 1184 corresponding to the position of the amino acid residue in FIGS. 11A-F (which is identical to the sequence shown as SEQ ID NO:187). In another embodiment, N-terminal deletions of the all polypeptide can be described by the general formula n2–1189, where n2 is a number from 2 to 1184, corresponding to the position of amino acid identified in FIGS. 11A-F. N-terminal deletions of the a11 polypeptide of the invention shown as SEQ ID NO:187 include polypeptides comprising the amino acid sequence of residues: N-terminal deletions of the a11 polypeptide of the invention shown as SEQ ID NO:187 include polypeptides comprising the amino acid sequence of residues: D-2 to E-1189; L-3 to E-1189; P-4 to E-1189; R-5 to E-1189; G-6 to E-1189; L-7 to E-1189; V-8 to E-1189; V-9 to E-1189; A-10 to E-1189; W-11 to E-1189; A-12 to E-1189; L-13 to E-1189; S-14 to E-1189; L-15 to E-1189; W-16 to E-1189; P-17 to E-1189; G-18 to E-1189; F-19 to E-1189; T-20 to E-1189; D-21 to E-1189; T-22 to E-1189; F-23 to E-1189; N-24 to E-1189; M-25 to E-1189; D-26 to E-1189; T-27 to E-1189; R-28 to E-1189; K-29 to E-1189; P-30 to E-1189; R-31 to E-1189; V-32 to E-1189; I-33 to E-1189; P-34 to E-1189; G-35 to E-1189; S-36 to E-1189; R-37 to E-1189; T-38 to E-1189; A-39 to E-1189; F-40 to E-1189; F-41 to E-1189; G-42 to E-1189; Y-43 to E-1189; T-44 to E-1189; V-45 to E-1189; Q-46 to E-1189; Q-47 to E-1189; H-48 to E-1189; D-49 to E-1189; I-50 to E-1189; S-51 to E-1189; G-52 to E-1189; N-53 to E-1189; K-54 to E-1189; W-55 to E-1189; L-56 to E-1189; V-57 to E-1189; V-58 to E-1189; G-59 to E-1189; A-60 to E-1189; P-61 to E-1189; L-62 to E-1189; E-63 to E-1189; T-64 to E-1189; N-65 to E-1189; G-66 to E-1189; Y-67 to E-1189; Q-68 to E-1189; K-69 to E-1189; T-70 to E-1189; G-71 to E-1189; D-72 to E-1189; V-73 to E-1189; Y-74 to E-1189; K-75 to E-1189; C-76 to E-1189; P-77 to E-1189; V-78 to E-1189; I-79 to E-1189; H-80 to E-1189; G-81 to E-1189; N-82 to E-1189; C-83 to E-1189; T-84 to E-1189; K-85 to E-1189; L-86 to E-1189; N-87 to E-1189; L-88 to E-1189; G-89 to E-1189; R-90 to E-1189; V-91 to E-1189; T-92 to E-1189; L-93 to E-1189; S-94 to E-1189; N-95 to E-1189; V-96 to E-1189; S-97 to E-1189; E-98 to E-1189; R-99 to E-1189; K-100 to E-1189; D-101 to E-1189; N-102 to E-1189; M-103 to E-1189; R-104 to E-1189; L-105 to E-1189; G-106 to E-1189; L-107 to E-1189; S-108 to E-1189; L-109 to E-1189; A-110 to E-1189; T-111 to E-1189; N-112 to E-1189; P-113 to E-1189; K-114 to E-1189; D-115 to E-1189; N-116 to E-1189; S-117 to E-1189; F-118 to E-1189; L-119 to E-1189; A-120 to E-1189; C-121 to E-1189; S-122 to E-1189; P-123 to E-1189; L-124 to E-1189; W-125 to E-1189; S-126 to E-1189; H-127 to E-1189; E-128 to E-1189; C-129 to E-1189; G-130 to E-1189; S-131 to E-1189; S-132 to E-1189; Y-133 to E-1189; Y-134 to E-1189; T-135 to E-1189; T-136 to E-1189; G-137 to E-1189; M-138 to E-1189; C-139 to E-1189; S-140 to E-1189; R-141 to E-1189; V-142 to E-1189; N-143 to E-1189; S-144 to E-1189; N-145 to E-1189; F-146 to E-1189; R-147 to E-1189; F-148 to E-1189; S-149 to E-1189; K-150 to E-1189; T-151 to E-1189; V-152 to E-1189; A-153 to E-1189; P-154 to E-1189; A-155 to E-1189; L-156 to E-1189; Q-157 to E-1189; R-158 to E-1189; C-159 to E-1189; Q-160 to E-1189; T-161 to E-1189; Y-162 to E-1189; M-163 to E-1189; D-164 to E-1189; I-165 to E-1189; V-166 to E-1189; I-167 to E-1189; V-168 to E-1189; L-169 to E-1189; D-170 to E-1189; G-171 to E-1189; S-172 to E-1189; N-173 to E-1189; S-174 to E-1189; I-175 to E-1189; Y-176 to E-1189; P-177 to E-1189; W-178 to E-1189; V-179 to E-1189; E-180 to E-1189; V-181 to E-1189; Q-182 to E-1189; H-183 to E-1189; F-184 to E-1189; L-185 to E-1189; I-186 to E-1189; N-187 to E-1189; I-188 to E-1189; L-189 to E-1189; K-190 to E-1189; K-191 to E-1189; F-192 to E-1189; Y-193 to E-1189; I-194 to E-1189; G-195 to E-1189; P-196 to E-1189; G-197 to E-1189; Q-198 to E-1189; I-199 to E-1189; Q-200 to E-1189; V-201 to E-1189; G-202 to E-1189; V-203 to E-1189; V-204 to E-1189; Q-205 to E-1189; Y-206 to E-1189; G-207 to E-1189; E-208 to E-1189; D-209 to E-1189; V-210 to E-1189; V-211 to E-1189; H-212 to E-1189; E-213 to E-1189; F-214 to E-1189; H-215 to E-1189; L-216 to E-1189; N-217 to E-1189; D-218 to E-1189; Y-219 to E-1189; R-220 to E-1189; S-221 to E-1189; V-222 to E-1189; K-223 to E-1189; D-224 to E-1189; V-225 to E-1189; V-226 to E-1189; E-227 to E-1189; A-228 to E-1189; A-229 to E-1189; S-230 to E-1189; H-231 to E-1189; I-232 to E-1189; E-233 to E-1189; Q-234 to E-1189; R-235 to E-1189; G-236 to E-1189; G-237 to E-1189; T-238 to E-1189; E-239 to E-1189; T-240 to E-1189; R-241 to E-1189; T-242 to E-1189; A-243 to E-1189; F-244 to E-1189; G-245 to E-1189; I-246 to E-1189; E-247 to E-1189; F-248 to E-1189; A-249 to E-1189; R-250 to E-1189; S-251 to E-1189; E-252 to E-1189; A-253 to E-1189; F-254 to E-1189; Q-255 to E-1189; K-256 to E-1189; G-257 to E-1189; G-258 to E-1189; R-259 to E-1189; K-260 to E-1189; G-261 to E-1189; A-262 to E-1189; K-263 to E-1189; K-264 to E-1189; V-265 to E-1189; M-266 to E-1189; I-267 to E-1189; V-268 to E-1189; I-269 to E-1189; T-270 to E-1189; D-271 to E-1189; G-272 to E-1189; E-273 to E-1189; S-274 to E-1189; H-275 to E-1189; D-276 to E-1189; S-277 to E-1189; P-278 to E-1189; D-279 to E-1189; L-280 to E-1189; E-281 to E-1189; K-282 to E-1189; V-283 to E-1189; I-284 to E-1189; Q-285 to E-1189; Q-286 to E-1189; S-287 to E-1189; E-288 to E-1189; R-289 to E-1189; D-290 to E-1189; N-291 to E-1189; V-292 to E-1189; T-293 to E-1189; R-294 to E-1189; Y-295 to E-1189; A-296 to E-1189; V-297 to E-1189; A-298 to E-1189; V-299 to E-1189; L-300 to E-1189; G-301 to E-1189; Y-302 to E-1189; Y-303 to E-1189; N-304 to E-1189; R-305 to E-1189; R-306 to E-1189; G-307 to E-1189; I-308 to E-1189; N-309 to E-1189; P-310 to E-1189; E-311 to E-1189; T-312 to E-1189; F-313 to E-1189; L-314 to E-1189; N-315 to E-1189; E-316 to E-1189; I-317 to E-1189; K-318 to E-1189; Y-319 to E-1189; I-320 to E-1189; A-321 to E-1189; S-322 to E-1189; D-323 to E-1189; P-324 to E-1189; D-325 to E-1189; D-326 to E-1189; K-327 to E-1189; H-328 to E-1189; F-329 to E-1189; F-330 to E-1189; N-331 to E-1189; V-332 to E-1189; T-333 to E-1189; D-334 to E-1189; E-335 to E-1189; A-336 to E-1189; A-337 to E-1189; L-338 to E-1189; K-339 to E-1189; D-340 to E-1189; I-341 to E-1189; V-342 to E-1189; D-343 to E-1189; A-344 to E-1189; L-345 to E-1189; G-346 to E-1189; D-347 to E-1189; R-348 to E-1189; I-349 to E-1189; F-350 to E-1189; S-351 to E-1189; L-352 to E-1189; E-353 to E-1189; G-354 to E-1189; T-355 to E-1189; N-356 to E-1189; K-357 to E-1189; N-358 to E-1189; E-359 to E-1189; T-360 to E-1189; S-361 to E-1189; F-362 to E-1189; G-363 to E-1189; L-364 to E-1189; E-365 to E-1189; M-366 to E-1189; S-367 to E-1189; Q-368 to E-1189; T-369 to E-1189; G-370 to E-1189; F-371 to E-1189; S-372 to E-1189; S-373 to E-1189; H-374 to E-1189; V-375 to E-1189; V-376 to E-1189; E-377 to E-1189; D-378 to E-1189; G-379 to E-1189; V-380 to E-1189; L-381 to E-1189; L-382 to E-1189; G-383 to E-1189; A-384 to E-1189; V-385 to E-1189; G-386 to E-1189; A-387 to E-1189; Y-388 to E-1189; D-389 to E-1189; W-390 to E-1189; N-391 to E-1189; G-392 to E-1189; A-393 to E-1189; V-394 to E-1189; L-395 to E-1189; K-396 to E-1189; E-397 to E-1189; T-398 to E-1189; S-399 to E-1189; A-400 to E-1189; G-401 to E-1189; K-402 to E-1189; V-403 to E-1189; I-404 to E-1189; P-405 to E-1189; L-406 to E-1189; R-407 to E-1189; E-408 to E-1189; S-409 to E-1189; Y-410 to E-1189; L-411 to E-1189; K-412 to E-1189; E-413 to E-1189; F-414 to E-1189; P-415 to E-1189; E-416 to E-1189; E-417 to E-1189; L-418 to E-1189; K-419 to E-1189; N-420 to E-1189; H-421 to E-1189; G-422 to E-1189; A-423 to E-1189; Y-424 to E-1189; L-425 to E-1189; G-426 to E-1189; Y-427 to E-1189; T-428 to E-1189; V-429 to E-1189; T-430 to E-1189; S-431 to E-1189; V-432 to E-1189; V-433 to E-1189; S-434 to E-1189; S-435 to E-1189; R-436 to E-1189; Q-437 to E-1189; G-438 to E-1189; R-439 to E-1189; V-440 to E-1189; Y-441 to E-1189; V-442 to E-1189; A-443 to E-1189; G-444 to E-1189; A-445 to E-1189; P-446 to E-1189; R-447 to E-1189; F-448 to E-1189; N-449 to E-1189; H-450 to E-1189; T-451 to E-1189; G-452 to E-1189; K-453 to E-1189; V-454 to E-1189; I-455 to E-1189; L-456 to E-1189; F-457 to E-1189; T-458 to E-1189; M-459 to E-1189; H-460 to E-1189; N-461 to E-1189; N-462 to E-1189; R-463 to E-1189; S-464 to E-1189; L-465 to E-1189; T-466 to E-1189; I-467 to E-1189; H-468 to E-1189; Q-469 to E-1189; A-470 to E-1189; M-471 to E-1189; R-472 to E-1189; G-473 to E-1189; Q-474 to E-1189; Q-475 to E-1189; I-476 to E-1189; G-477 to E-1189; S-478 to E-1189; Y-479 to E-1189; F-480 to E-1189; G-481 to E-1189; S-482 to E-1189; E-483 to E-1189; I-484 to E-1189; T-485 to E-1189; S-486 to E-1189; V-487 to E-1189; D-488 to E-1189; I-489 to E-1189; D-490 to E-1189; G-491 to E-1189; D-492 to E-1189; G-493 to E-1189; V-494 to E-1189; T-495 to E-1189; D-496 to E-1189; V-497 to E-1189; L-498 to E-1189; L-499 to E-1189; V-500 to E-1189; G-501 to E-1189; A-502 to E-1189; P-503 to E-1189; M-504 to E-1189; Y-505 to E-1189; F-506 to E-1189; N-507 to E-1189; E-508 to E-1189; G-509 to E-1189; R-510 to E-1189; E-511 to E-1189; R-512 to E-1189; G-513 to E-1189; K-514 to E-1189; V-515 to E-1189; Y-516 to E-1189; V-517 to E-1189; Y-518 to E-1189; E-519 to E-1189; L-520 to E-1189; R-521 to E-1189; Q-522 to E-1189; N-523 to E-1189; R-524 to E-1189; F-525 to E-1189; V-526 to E-1189; Y-527 to E-1189; N-528 to E-1189; G-529 to E-1189; T-530 to E-1189; L-531 to E-1189; K-532 to E-1189; D-533 to E-1189; S-534 to E-1189; H-535 to E-1189; S-536 to E-1189; Y-537 to E-1189; Q-538 to E-1189; N-539 to E-1189; A-540 to E-1189; R-541 to E-1189; F-542 to E-1189; G-543 to E-1189; S-544 to E-1189; S-545 to E-1189; I-546 to E-1189; A-547 to E-1189; S-548 to E-1189; V-549 to E-1189; R-550 to E-1189; D-551 to E-1189; L-552 to E-1189; N-553 to E-1189; Q-554 to E-1189; D-555 to E-1189; S-556 to E-1189; Y-557 to E-1189; N-558 to E-1189; D-559 to E-1189; V-560 to E-1189; V-561 to E-1189; V-562 to E-1189; G-563 to E-1189; A-564 to E-1189; P-565 to E-1189; L-566 to E-1189; E-567 to E-1189; D-568 to E-1189; N-569 to E-1189; H-570 to E-1189; A-571 to E-1189; G-572 to E-1189; A-573 to E-1189; I-574 to E-1189; Y-575 to E-1189; I-576 to E-1189; F-577 to E-1189; H-578 to E-1189; G-579 to E-1189; F-580 to E-1189; R-581 to E-1189; G-582 to E-1189; S-583 to E-1189; I-584 to E-1189; L-585 to E-1189; K-586 to E-1189; T-587 to E-1189; P-588 to E-1189; K-589 to E-1189; Q-590 to E-1189; R-591 to E-1189; I-592 to E-1189; T-593 to E-1189; A-594 to E-1189; S-595 to E-1189; E-596 to E-1189; L-597 to E-1189; A-598 to E-1189; T-599 to E-1189; G-600 to E-1189; L-601 to E-1189; Q-602 to E-1189; Y-603 to E-1189; F-604 to E-1189; G-605 to E-1189; C-606 to E-1189; S-607 to E-1189; I-608 to E-1189; H-609 to E-1189; G-610 to E-1189; Q-611 to E-1189; L-612 to E-1189; D-613 to E-1189; L-614 to E-1189; N-615 to E-1189; E-616 to E-1189; D-617 to E-1189; G-618 to E-1189; L-619 to E-1189; I-620 to E-1189; D-621 to E-1189; L-622 to E-1189; A-623 to E-1189; V-624 to E-1189; G-625 to E-1189; A-626 to E-1189; L-627 to E-1189; G-628 to E-1189; N-629 to E-1189; A-630 to E-1189; V-631 to E-1189; I-632 to E-1189; L-633 to E-1189; W-634 to E-1189; S-635 to E-1189; R-636 to E-1189; P-637 to E-1189; V-638 to E-1189; V-639 to E-1189; Q-640 to E-1189; I-641 to E-1189; N-642 to E-1189; A-643 to E-1189;

S-644 to E-1189; L-645 to E-1189; H-646 to E-1189; F-647 to E-1189; E-648 to E-1189; P-649 to E-1189; S-650 to E-1189; K-651 to E-1189; I-652 to E-1189; N-653 to E-1189; I-654 to E-1189; F-655 to E-1189; H-656 to E-1189; R-657 to E-1189; D-658 to E-1189; C-659 to E-1189; K-660 to E-1189; R-661 to E-1189; S-662 to E-1189; G-663 to E-1189; R-664 to E-1189; D-665 to E-1189; A-666 to E-1189; T-667 to E-1189; C-668 to E-1189; L-669 to E-1189; A-670 to E-1189; A-671 to E-1189; F-672 to E-1189; L-673 to E-1189; C-674 to E-1189; F-675 to E-1189; T-676 to E-1189; P-677 to E-1189; I-678 to E-1189; F-679 to E-1189; L-680 to E-1189; A-681 to E-1189; P-682 to E-1189; H-683 to E-1189; F-684 to E-1189; Q-685 to E-1189; T-686 to E-1189; T-687 to E-1189; T-688 to E-1189; V-689 to E-1189; G-690 to E-1189; I-691 to E-1189; R-692 to E-1189; Y-693 to E-1189; N-694 to E-1189; A-695 to E-1189; T-696 to E-1189; M-697 to E-1189; D-698 to E-1189; E-699 to E-1189; R-700 to E-1189; R-701 to E-1189; Y-702 to E-1189; T-703 to E-1189; P-704 to E-1189; R-705 to E-1189; A-706 to E-1189; H-707 to E-1189; L-708 to E-1189; D-709 to E-1189; E-710 to E-1189; G-711 to E-1189; G-712 to E-1189; D-713 to E-1189; R-714 to E-1189; F-715 to E-1189; T-716 to E-1189; N-717 to E-1189; R-718 to E-1189; A-719 to E-1189; V-720 to E-1189; L-721 to E-1189; L-722 to E-1189; S-723 to E-1189; S-724 to E-1189; G-725 to E-1189; Q-726 to E-1189; E-727 to E-1189; L-728 to E-1189; C-729 to E-1189; E-730 to E-1189; R-731 to E-1189; I-732 to E-1189; N-733 to E-1189; F-734 to E-1189; H-735 to E-1189; V-736 to E-1189; L-737 to E-1189; D-738 to E-1189; T-739 to E-1189; A-740 to E-1189; D-741 to E-1189; Y-742 to E-1189; V-743 to E-1189; K-744 to E-1189; P-745 to E-1189; V-746 to E-1189; T-747 to E-1189; F-748 to E-1189; S-749 to E-1189; V-750 to E-1189; E-751 to E-1189; Y-752 to E-1189; S-753 to E-1189; L-754 to E-1189; E-755 to E-1189; D-756 to E-1189; P-757 to E-1189; D-758 to E-1189; H-759 to E-1189; G-760 to E-1189; P-761 to E-1189; M-762 to E-1189; L-763 to E-1189; D-764 to E-1189; D-765 to E-1189; G-766 to E-1189; W-767 to E-1189; P-768 to E-1189; T-769 to E-1189; T-770 to E-1189; L-771 to E-1189; R-772 to E-1189; V-773 to E-1189; S-774 to E-1189; V-775 to E-1189; P-776 to E-1189; F-777 to E-1189; W-778 to E-1189; N-779 to E-1189; G-780 to E-1189; C-781 to E-1189; N-782 to E-1189; E-783 to E-1189; D-784 to E-1189; E-785 to E-1189; H-786 to E-1189; C-787 to E-1189; V-788 to E-1189; P-789 to E-1189; D-790 to E-1189; L-791 to E-1189; V-792 to E-1189; L-793 to E-1189; D-794 to E-1189; A-795 to E-1189; R-796 to E-1189; S-797 to E-1189; D-798 to E-1189; L-799 to E-1189; P-800 to E-1189; T-801 to E-1189; A-802 to E-1189; M-803 to E-1189; E-804 to E-1189; Y-805 to E-1189; C-806 to E-1189; Q-807 to E-1189; R-808 to E-1189; V-809 to E-1189; L-810 to E-1189; R-811 to E-1189; K-812 to E-1189; P-813 to E-1189; A-814 to E-1189; Q-815 to E-1189; D-816 to E-1189; C-817 to E-1189; S-818 to E-1189; A-819 to E-1189; Y-820 to E-1189; T-821 to E-1189; L-822 to E-1189; S-823 to E-1189; F-824 to E-1189; D-825 to E-1189; T-826 to E-1189; T-827 to E-1189; V-828 to E-1189; F-829 to E-1189; I-830 to E-1189; I-831 to E-1189; E-832 to E-1189; S-833 to E-1189; T-834 to E-1189; R-835 to E-1189; Q-836 to E-1189; R-837 to E-1189; V-838 to E-1189; A-839 to E-1189; V-840 to E-1189; E-841 to E-1189; A-842 to E-1189; T-843 to E-1189; L-844 to E-1189; E-845 to E-1189; N-846 to E-1189; R-847 to E-1189; G-848 to E-1189; E-849 to E-1189; N-850 to E-1189; A-851 to E-1189; Y-852 to E-1189; S-853 to E-1189; T-854 to E-1189; V-855 to E-1189; L-856 to E-1189; N-857 to E-1189; I-858 to E-1189; S-859 to E-1189; Q-860 to E-1189; S-861 to E-1189; A-862 to E-1189; N-863 to E-1189; L-864 to E-1189; Q-865 to E-1189; F-866 to E-1189; A-867 to E-1189; S-868 to E-1189; L-869 to E-1189; I-870 to E-1189; Q-871 to E-1189; K-872 to E-1189; E-873 to E-1189; D-874 to E-1189; S-875 to E-1189; D-876 to E-1189; G-877 to E-1189; S-878 to E-1189; I-879 to E-1189; E-880 to E-1189; C-881 to E-1189; V-882 to E-1189; N-883 to E-1189; E-884 to E-1189; E-885 to E-1189; R-886 to E-1189; R-887 to E-1189; L-888 to E-1189; Q-889 to E-1189; K-890 to E-1189; Q-891 to E-1189; V-892 to E-1189; C-893 to E-1189; N-894 to E-1189; V-895 to E-1189; S-896 to E-1189; Y-897 to E-1189; P-898 to E-1189; F-899 to E-1189; F-900 to E-1189; R-901 to E-1189; A-902 to E-1189; K-903 to E-1189; A-904 to E-1189; K-905 to E-1189; V-906 to E-1189; A-907 to E-1189; F-908 to E-1189; R-909 to E-1189; L-910 to E-1189; D-911 to E-1189; F-912 to E-1189; E-913 to E-1189; F-914 to E-1189; S-915 to E-1189; K-916 to E-1189; S-917 to E-1189; I-918 to E-1189; F-919 to E-1189; L-920 to E-1189; H-921 to E-1189; H-922 to E-1189; L-923 to E-1189; E-924 to E-1189; I-925 to E-1189; E-926 to E-1189; L-927 to E-1189; A-928 to E-1189; A-929 to E-1189; G-930 to E-1189; S-931 to E-1189; D-932 to E-1189; S-933 to E-1189; N-934 to E-1189; E-935 to E-1189; R-936 to E-1189; D-937 to E-1189; S-938 to E-1189; T-939 to E-1189; K-940 to E-1189; E-941 to E-1189; D-942 to E-1189; N-943 to E-1189; V-944 to E-1189; A-945 to E-1189; P-946 to E-1189; L-947 to E-1189; R-948 to E-1189; F-949 to E-1189; H-950 to E-1189; L-951 to E-1189; K-952 to E-1189; Y-953 to E-1189; E-954 to E-1189; A-955 to E-1189; D-956 to E-1189; V-957 to E-1189; L-958 to E-1189; F-959 to E-1189; T-960 to E-1189; R-961 to E-1189; S-962 to E-1189; S-963 to E-1189; S-964 to E-1189; L-965 to E-1189; S-966 to E-1189; H-967 to E-1189; Y-968 to E-1189; E-969 to E-1189; V-970 to E-1189; K-971 to E-1189; L-972 to E-1189; N-973 to E-1189; S-974 to E-1189; S-975 to E-1189; L-976 to E-1189; E-977 to E-1189; R-978 to E-1189; Y-979 to E-1189; D-980 to E-1189; G-981 to E-1189; I-982 to E-1189; G-983 to E-1189; P-984 to E-1189; P-985 to E-1189; F-986 to E-1189; S-987 to E-1189; C-988 to E-1189; I-989 to E-1189; F-990 to E-1189; R-991 to E-1189; I-992 to E-1189; Q-993 to E-1189; N-994 to E-1189; L-995 to E-1189; G-996 to E-1189; L-997 to E-1189; F-998 to E-1189; P-999 to E-1189; I-1000 to E-1189; H-1001 to E-1189; G-1002 to E-1189; I-1003 to E-1189; M-1004 to E-1189; M-1005 to E-1189; K-1006 to E-1189; I-1007 to E-1189; T-1008 to E-1189; I-1009 to E-1189; P-1010 to E-1189; I-1011 to E-1189; A-1012 to E-1189; T-1013 to E-1189; R-1014 to E-1189; S-1015 to E-1189; G-1016 to E-1189; N-1017 to E-1189; R-1018 to E-1189; L-1019 to E-1189; L-1020 to E-1189; K-1021 to E-1189; L-1022 to E-1189; R-1023 to E-1189; D-1024 to E-1189; F-1025 to E-1189; L-1026 to E-1189; T-1027 to E-1189; D-1028 to E-1189; E-1029 to E-1189; V-1030 to E-1189; A-1031 to E-1189; N-1032 to E-1189; T-1033 to E-1189; S-1034 to E-1189; C-1035 to E-1189; N-1036 to E-1189; I-1037 to E-1189; W-1038 to E-1189; G-1039 to E-1189; N-1040 to E-1189; S-1041 to E-1189; T-1042 to E-1189; E-1043 to E-1189; Y-1044 to E-1189; R-1045 to E-1189; P-1046 to E-1189; T-1047 to E-1189; P-1048 to E-1189; V-1049 to E-1189; E-1050 to E-1189; E-1051 to E-1189; D-1052 to E-1189; L-1053 to E-1189; R-1054 to E-1189; R-1055 to E-1189; A-1056 to E-1189; P-1057 to E-1189; Q-1058 to E-1189; L-1059 to E-1189; N-1060 to E-1189; H-1061 to E-1189; S-1062 to E-1189; N-1063 to E-1189; S-1064 to E-1189; D-1065 to E-1189; V-1066 to E-1189; V-1067 to E-1189; S-1068 to E-1189; I-1069 to E-1189; N-1070 to E-1189; C-1071 to E-1189; N-1072 to E-1189; I-1073 to E-1189; R-1074 to E-1189; L-1075 to E-1189; V-1076 to E-1189; P-1077 to E-1189; N-1078 to

E-1189; Q-1079 to E-1189; E-1080 to E-1189; I-1081 to E-1189; N-1082 to E-1189; F-1083 to E-1189; H-1084 to E-1189; L-1085 to E-1189; L-1086 to E-1189; G-1087 to E-1189; N-1088 to E-1189; L-1089 to E-1189; W-1090 to E-1189; L-1091 to E-1189; R-1092 to E-1189; S-1093 to E-1189; L-1094 to E-1189; K-1095 to E-1189; A-1096 to E-1189; L-1097 to E-1189; K-1098 to E-1189; Y-1099 to E-1189; K-1100 to E-1189; S-1101 to E-1189; M-1102 to E-1189; K-1103 to E-1189; I-1104 to E-1189; M-1105 to E-1189; V-1106 to E-1189; N-1107 to E-1189; A-1108 to E-1189; A-1109 to E-1189; L-1110 to E-1189; Q-1111 to E-1189; R-1112 to E-1189; Q-1113 to E-1189; F-1114 to E-1189; H-1115 to E-1189; S-1116 to E-1189; P-1117 to E-1189; F-1118 to E-1189; I-1119 to E-1189; F-1120 to E-1189; R-1121 to E-1189; E-1122 to E-1189; E-1123 to E-1189; D-1124 to E-1189; P-1125 to E-1189; S-1126 to E-1189; R-1127 to E-1189; Q-1128 to E-1189; I-1129 to E-1189; V-1130 to E-1189; F-1131 to E-1189; E-1132 to E-1189; I-1133 to E-1189; S-1134 to E-1189; K-1135 to E-1189; Q-1136 to E-1189; E-1137 to E-1189; D-1138 to E-1189; W-1139 to E-1189; Q-1140 to E-1189; V-1141 to E-1189; P-1142 to E-1189; I-1143 to E-1189; W-1144 to E-1189; I-1145 to E-1189; I-1146 to E-1189; V-1147 to E-1189; G-1148 to E-1189; S-1149 to E-1189; T-1150 to E-1189; L-1151 to E-1189; G-1152 to E-1189; G-1153 to E-1189; L-1154 to E-1189; L-1155 to E-1189; L-1156 to E-1189; L-1157 to E-1189; A-1158 to E-1189; L-1159 to E-1189; L-1160 to E-1189; V-1161 to E-1189; L-1162 to E-1189; A-1163 to E-1189; L-1164 to E-1189; W-1165 to E-1189; K-1166 to E-1189; L-1167 to E-1189; G-1168 to E-1189; F-1169 to E-1189; F-1170 to E-1189; R-1171 to E-1189; S-1172 to E-1189; A-1173 to E-1189; R-1174 to E-1189; R-1175 to E-1189; R-1176 to E-1189; R-1177 to E-1189; E-1178 to E-1189; P-1179 to E-1189; G-1180 to E-1189; L-1181 to E-1189; D-1182 to E-1189; P-1183 to E-1189; T-1184 to E-1189; of SEQ ID NO:187. Polynucleotides encoding these polypeptides are also encompassed by the invention, as are antibodies that bind one or more of these polypeptides. Moreover, fragments and variants of these polypeptides (e.g., fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides, or the complement thereof) are encompassed by the invention. Antibodies that bind these fragments and variants of the invention are also encompassed by the invention. Polynucleotides encoding these fragments and variants are also encompassed by the invention.

Also as mentioned above, even if deletion of one or more amino acids from the C-terminus of a protein results in modification or loss of one or more biological functions of the protein, other functional activities (e.g., biological activities (e.g., ability to illicit mitogenic activity, induce differentiation of normal or malignant cells, ability to multimerize, etc.) may still be retained. For example the ability of the shortened all mutein to induce and/or bind to antibodies which recognize the complete or mature forms of the polypeptide generally will be retained when less than the majority of the residues of the complete or mature polypeptide are removed from the C-terminus. Whether a particular polypeptide lacking C-terminal residues of a complete polypeptide retains such immunologic activities can readily be determined by routine methods described herein and otherwise known in the art. It is not unlikely that an all mutein with a large number of deleted C-terminal amino acid residues may retain some biological or immunogenic activities. In fact, peptides composed of as few as six all amino acid residues may often evoke an immune response.

Accordingly, the present invention further provides polypeptides having one or more residues deleted from the carboxy terminus of the amino acid sequence of the a11 polypeptide shown in FIGS. 11A-F, up to the glycine residue at position number 6, and polynucleotides encoding such polypeptides. In particular, the present invention provides polypeptides comprising the amino acid sequence of residues 1-m1 of FIGS. 11A-F, where m1 is an integer from 6 to 1189 corresponding to the position of the amino acid residue in FIGS. 11A-F. Moreover, the invention provides polynucleotides encoding polypeptides comprising, or alternatively consisting of, the amino acid sequence of C-terminal deletions of the a11 polypeptide of the invention shown as SEQ ID NO:187 include polypeptides comprising the amino acid sequence of residues: M-1 to L-1188; M-1 to V-1187; M-1 to K-1186; M-1 to P-1185; M-1 to T-1184; M-1 to P-1183; M-1 to D-1182; M-1 to L-1181; M-1 to G-1180; M-1 to P-1179; M-1 to E-1178; M-1 to R-1177; M-1 to R-1176; M-1 to R-1175; M-1 to R-1174; M-1 to A-1173; M-1 to S-1172; M-1 to R-1171; M-1 to F-1170; M-1 to F-1169; M-1 to G-1168; M-1 to L-1167; M-1 to K-1166; M-1 to W-1165; M-1 to L-1164; M-1 to A-1163; M-1 to L-1162; M-1 to V-1161; M-1 to L-1160; M-1 to L-1159; M-1 to A-1158; M-1 to L-1157; M-1 to L-1156; M-1 to L-1155; M-1 to L-1154; M-1 to G-1153; M-1 to G-1152; M-1 to L-1151; M-1 to T-1150; M-1 to S-1149; M-1 to G-1148; M-1 to V-1147; M-1 to I-1146; M-1 to I-1145; M-1 to W-1144; M-1 to I-1143; M-1 to P-1142; M-1 to V-1141; M-1 to Q-1140; M-1 to W-1139; M-1 to D-1138; M-1 to E-1137; M-1 to Q-1136; M-1 to K-1135; M-1 to S-1134; M-1 to I-1133; M-1 to E-1132; M-1 to F-1131; M-1 to V-1130; M-1 to I-1129; M-1 to Q-1128; M-1 to R-1127; M-1 to S-1126; M-1 to P-1125; M-1 to D-1124; M-1 to E-1123; M-1 to E-1122; M-1 to R-1121; M-1 to F-1120; M-1 to I-1119; M-1 to F-1118; M-1 to P-1117; M-1 to S-1116; M-1 to H-1115; M-1 to F-1114; M-1 to Q-1113; M-1 to R-1112; M-1 to Q-1111; M-1 to L-1110; M-1 to A-1109; M-1 to A-1108; M-1 to N-1107; M-1 to V-1106; M-1 to M-1105; M-1 to I-1104; M-1 to K-1103; M-1 to M-1102; M-1 to S-1101; M-1 to K-1100; M-1 to Y-1099; M-1 to K-1098; M-1 to L-1097; M-1 to A-1096; M-1 to K-1095; M-1 to L-1094; M-1 to S-1093; M-1 to R-1092; M-1 to L-1091; M-1 to W-1090; M-1 to L-1089; M-1 to N-1088; M-1 to G-1087; M-1 to L-1086; M-1 to L-1085; M-1 to H-1084; M-1 to F-1083; M-1 to N-1082; M-1 to I-1081; M-1 to E-1080; M-1 to Q-1079; M-1 to N-1078; M-1 to P-1077; M-1 to V-1076; M-1 to L-1075; M-1 to R-1074; M-1 to I-1073; M-1 to N-1072; M-1 to C-1071; M-1 to N-1070; M-1 to I-1069; M-1 to S-1068; M-1 to V-1067; M-1 to V-1066; M-1 to D-1065; M-1 to S-1064; M-1 to N-1063; M-1 to S-1062; M-1 to H-1061; M-1 to N-1060; M-1 to L-1059; M-1 to Q-1058; M-1 to P-1057; M-1 to A-1056; M-1 to R-1055; M-1 to R-1054; M-1 to L-1053; M-1 to D-1052; M-1 to E-1051; M-1 to E-1050; M-1 to V-1049; M-1 to P-1048; M-1 to T-1047; M-1 to P-1046; M-1 to R-1045; M-1 to Y-1044; M-1 to E-1043; M-1 to T-1042; M-1 to S-1041; M-1 to N-1040; M-1 to G-1039; M-1 to W-1038; M-1 to I-1037; M-1 to N-1036; M-1 to C-1035; M-1 to S-1034; M-1 to T-1033; M-1 to N-1032; M-1 to A-1031; M-1 to V-1030; M-1 to E-1029; M-1 to D-1028; M-1 to T-1027; M-1 to L-1026; M-1 to F-1025; M-1 to D-1024; M-1 to R-1023; M-1 to L-1022; M-1 to K-1021; M-1 to L-1020; M-1 to L-1019; M-1 to R-1018; M-1 to N-1017; M-1 to G-1016; M-1 to S-1015; M-1 to R-1014; M-1 to T-1013; M-1 to A-1012; M-1 to I-1011; M-1 to P-1010; M-1 to I-1009; M-1 to T-1008; M-1 to I-1007; M-1 to K-1006; M-1 to M-1005; M-1 to M-1004; M-1 to I-1003; M-1 to G-1002; M-1 to H-1001; M-1 to I-1000; M-1 to P-999; M-1 to F-998; M-1 to L-997; M-1 to G-996; M-1 to L-995; M-1 to N-994; M-1 to Q-993; M-1 to I-992; M-1 to R-991; M-1 to F-990; M-1 to I-989; M-1 to C-988; M-1 to S-987; M-1 to F-986; M-1 to P-985; M-1 to P-984; M-1 to G-983; M-1 to I-982; M-1 to G-981; M-1 to D-980; M-1 to Y-979; M-1 to R-978; M-1 to E-977; M-1 to L-976; M-1 to S-975; M-1 to S-974; M-1 to N-973; M-1 to L-972; M-1 to K-971; M-1 to V-970; M-1 to E-969; M-1 to Y-968; M-1 to H-967; M-1 to S-966; M-1 to L-965; M-1 to S-964; M-1 to S-963; M-1 to S-962; M-1 to R-961; M-1 to T-960; M-1 to F-959; M-1 to L-958; M-1 to V-957; M-1 to D-956; M-1 to A-955; M-1 to E-954; M-1 to Y-953; M-1 to K-952; M-1 to L-951; M-1 to H-950; M-1 to F-949; M-1 to R-948; M-1 to L-947; M-1 to P-946; M-1 to A-945; M-1 to V-944; M-1 to N-943; M-1 to D-942; M-1 to E-941; M-1 to K-940; M-1 to T-939; M-1 to S-938; M-1 to D-937; M-1 to R-936; M-1 to E-935; M-1 to N-934; M-1 to S-933; M-1 to D-932; M-1 to S-931; M-1 to G-930; M-1 to A-929; M-1 to A-928; M-1 to L-927; M-1 to E-926; M-1 to I-925; M-1 to E-924; M-1 to L-923; M-1 to H-922; M-1 to H-921; M-1 to L-920; M-1 to F-919; M-1 to I-918; M-1 to S-917; M-1 to K-916; M-1 to S-915; M-1 to F-914; M-1 to E-913; M-1 to F-912; M-1 to D-911; M-1 to L-910; M-1 to R-909; M-1 to F-908; M-1 to A-907; M-1 to V-906; M-1 to K-905; M-1 to A-904; M-1 to K-903; M-1 to A-902; M-1 to R-901; M-1 to F-900; M-1 to F-899; M-1 to P-898; M-1 to Y-897; M-1 to S-896; M-1 to V-895; M-1 to N-894; M-1 to C-893; M-1 to V-892; M-1 to Q-891; M-1 to K-890; M-1 to Q-889; M-1 to L-888; M-1 to R-887; M-1 to R-886; M-1 to E-885; M-1 to E-884; M-1 to N-883; M-1 to V-882; M-1 to C-881; M-1 to E-880; M-1 to I-879; M-1 to S-878; M-1 to G-877; M-1 to D-876; M-1 to S-875; M-1 to D-874; M-1 to E-873; M-1 to K-872; M-1 to Q-871; M-1 to I-870; M-1 to L-869; M-1 to S-868; M-1 to A-867; M-1 to F-866; M-1 to Q-865; M-1 to L-864; M-1 to N-863; M-1 to A-862; M-1 to S-861; M-1 to Q-860; M-1 to S-859; M-1 to I-858; M-1 to N-857; M-1 to L-856; M-1 to V-855; M-1 to T-854; M-1 to S-853; M-1 to Y-852; M-1 to A-851; M-1 to N-850; M-1 to E-849; M-1 to G-848; M-1 to R-847; M-1 to N-846; M-1 to E-845; M-1 to L-844; M-1 to T-843; M-1 to A-842; M-1 to E-841; M-1 to V-840; M-1 to A-839; M-1 to V-838; M-1 to R-837; M-1 to Q-836; M-1 to R-835; M-1 to T-834; M-1 to S-833; M-1 to E-832; M-1 to I-831; M-1 to I-830; M-1 to F-829; M-1 to V-828; M-1 to T-827; M-1 to T-826; M-1 to D-825; M-1 to F-824; M-1 to S-823; M-1 to L-822; M-1 to T-821; M-1 to Y-820; M-1 to A-819; M-1 to S-818; M-1 to C-817; M-1 to D-816; M-1 to Q-815; M-1 to A-814; M-1 to P-813; M-1 to K-812; M-1 to R-811; M-1 to L-810; M-1 to V-809; M-1 to R-808; M-1 to Q-807; M-1 to C-806; M-1 to Y-805; M-1 to E-804; M-1 to M-803; M-1 to A-802; M-1 to T-801; M-1 to P-800; M-1 to L-799; M-1 to D-798; M-1 to S-797; M-1 to R-796; M-1 to A-795; M-1 to D-794; M-1 to L-793; M-1 to V-792; M-1 to L-791; M-1 to D-790; M-1 to P-789; M-1 to V-788; M-1 to C-787; M-1 to H-786; M-1 to E-785; M-1 to D-784; M-1 to E-783; M-1 to N-782; M-1 to C-781; M-1 to G-780; M-1 to N-779; M-1 to W-778; M-1 to F-777; M-1 to P-776; M-1 to V-775; M-1 to S-774; M-1 to V-773; M-1 to R-772; M-1 to L-771; M-1 to T-770; M-1 to T-769; M-1 to P-768; M-1 to W-767; M-1 to G-766; M-1 to D-765; M-1 to D-764; M-1 to L-763; M-1 to M-762; M-1 to P-761; M-1 to G-760; M-1 to H-759; M-1 to D-758; M-1 to P-757; M-1 to D-756; M-1 to E-755; M-1 to L-754; M-1 to S-753; M-1 to Y-752; M-1 to E-751; M-1 to V-750; M-1 to S-749; M-1 to F-748; M-1 to T-747; M-1 to V-746; M-1 to P-745; M-1 to K-744; M-1 to V-743; M-1 to Y-742; M-1 to D-741; M-1 to A-740; M-1 to T-739; M-1 to D-738; M-1 to L-737; M-1 to V-736; M-1 to H-735; M-1 to F-734; M-1 to N-733; M-1 to I-732; M-1 to R-731; M-1 to E-730; M-1 to C-729; M-1 to L-728; M-1 to E-727; M-1 to Q-726; M-1 to G-725; M-1 to S-724; M-1 to S-723; M-1 to L-722; M-1 to L-721; M-1 to V-720; M-1 to A-719; M-1 to R-718; M-1 to N-717; M-1 to T-716; M-1 to F-715; M-1 to R-714; M-1 to D-713; M-1 to G-712; M-1 to G-711; M-1 to E-710; M-1 to D-709; M-1 to L-708; M-1 to H-707; M-1 to A-706; M-1 to R-705; M-1 to P-704; M-1 to T-703; M-1 to Y-702; M-1 to R-701; M-1 to R-700; M-1 to E-699; M-1 to D-698; M-1 to M-697; M-1 to T-696; M-1 to A-695; M-1 to N-694; M-1 to Y-693; M-1 to R-692; M-1 to I-691; M-1 to G-690; M-1 to V-689; M-1 to T-688; M-1 to T-687; M-1 to T-686; M-1 to Q-685; M-1 to F-684; M-1 to H-683; M-1 to P-682; M-1 to A-681; M-1 to L-680; M-1 to F-679; M-1 to I-678; M-1 to P-677; M-1 to T-676; M-1 to F-675; M-1 to C-674; M-1 to L-673; M-1 to F-672; M-1 to A-671; M-1 to A-670; M-1 to L-669; M-1 to C-668; M-1 to T-667; M-1 to A-666; M-1 to D-665; M-1 to R-664; M-1 to G-663; M-1 to S-662; M-1 to R-661; M-1 to K-660; M-1 to C-659; M-1 to D-658; M-1 to R-657; M-1 to H-656; M-1 to F-655; M-1 to I-654; M-1 to N-653; M-1 to I-652; M-1 to K-651; M-1 to S-650; M-1 to P-649; M-1 to E-648; M-1 to F-647; M-1 to H-646; M-1 to L-645; M-1 to S-644; M-1 to A-643; M-1 to N-642; M-1 to I-641; M-1 to Q-640; M-1 to V-639; M-1 to V-638; M-1 to P-637; M-1 to R-636; M-1 to S-635; M-1 to W-634; M-1 to L-633; M-1 to I-632; M-1 to V-631; M-1 to A-630; M-1 to N-629; M-1 to G-628; M-1 to L-627; M-1 to A-626; M-1 to G-625; M-1 to V-624; M-1 to A-623; M-1 to L-622; M-1 to D-621; M-1 to I-620; M-1 to L-619; M-1 to G-618; M-1 to D-617; M-1 to E-616; M-1 to N-615; M-1 to L-614; M-1 to D-613; M-1 to L-612; M-1 to Q-611; M-1 to G-610; M-1 to H-609; M-1 to I-608; M-1 to S-607; M-1 to C-606; M-1 to G-605; M-1 to F-604; M-1 to Y-603; M-1 to Q-602; M-1 to L-601; M-1 to G-600; M-1 to T-599; M-1 to A-598; M-1 to L-597; M-1 to E-596; M-1 to S-595; M-1 to A-594; M-1 to T-593; M-1 to I-592; M-1 to R-591; M-1 to Q-590; M-1 to K-589; M-1 to P-588; M-1 to T-587; M-1 to K-586; M-1 to L-585; M-1 to I-584; M-1 to S-583; M-1 to G-582; M-1 to R-581; M-1 to F-580; M-1 to G-579; M-1 to H-578; M-1 to F-577; M-1 to I-576; M-1 to Y-575; M-1 to I-574; M-1 to A-573; M-1 to G-572; M-1 to A-571; M-1 to H-570; M-1 to N-569; M-1 to D-568; M-1 to E-567; M-1 to L-566; M-1 to P-565; M-1 to A-564; M-1 to G-563; M-1 to V-562; M-1 to V-561; M-1 to V-560; M-1 to D-559; M-1 to N-558; M-1 to Y-557; M-1 to S-556; M-1 to D-555; M-1 to Q-554; M-1 to N-553; M-1 to L-552; M-1 to D-551; M-1 to R-550; M-1 to V-549; M-1 to S-548; M-1 to A-547; M-1 to I-546; M-1 to S-545; M-1 to S-544; M-1 to G-543; M-1 to F-542; M-1 to R-541; M-1 to A-540; M-1 to N-539; M-1 to Q-538; M-1 to Y-537; M-1 to S-536; M-1 to H-535; M-1 to S-534; M-1 to D-533; M-1 to K-532; M-1 to L-531; M-1 to T-530; M-1 to G-529; M-1 to N-528; M-1 to Y-527; M-1 to V-526; M-1 to F-525; M-1 to R-524; M-1 to N-523; M-1 to Q-522; M-1 to R-521; M-1 to L-520; M-1 to E-519; M-1 to Y-518; M-1 to V-517; M-1 to Y-516; M-1 to V-515; M-1 to K-514; M-1 to G-513; M-1 to R-512; M-1 to E-511; M-1 to R-510; M-1 to G-509; M-1 to E-508; M-1 to N-507; M-1 to F-506; M-1 to Y-505; M-1 to M-504; M-1 to P-503; M-1 to A-502; M-1 to G-501; M-1 to V-500; M-1 to L-499; M-1 to L-498; M-1 to V-497; M-1 to D-496; M-1 to T-495; M-1 to V-494; M-1 to G-493; M-1 to D-492; M-1 to G-491; M-1 to D-490; M-1 to I-489; M-1 to D-488; M-1 to V-487; M-1 to S-486; M-1 to T-485; M-1 to I-484; M-1 to E-483; M-1 to S-482; M-1 to G-481; M-1 to F-480; M-1 to Y-479; M-1 to S-478; M-1 to G-477; M-1 to I-476; M-1 to Q-475; M-1 to Q-474; M-1 to G-473; M-1 to R-472; M-1 to M-471; M-1 to A-470; M-1 to Q-469; M-1 to H-468; M-1 to I-467; M-1 to T-466; M-1 to L-465; M-1 to S-464; M-1 to R-463; M-1 to N-462; M-1 to N-461; M-1 to H-460; M-1 to M-459; M-1 to T-458; M-1 to F-457; M-1 to L-456; M-1 to I-455; M-1 to V-454; M-1 to K-453; M-1 to G-452; M-1 to T-451; M-1 to H-450; M-1 to N-449; M-1 to F-448; M-1 to R-447; M-1 to P-446; M-1 to A-445; M-1 to G-444; M-1 to A-443; M-1 to V-442; M-1 to Y-441; M-1 to V-440; M-1 to R-439; M-1 to G-438; M-1 to Q-437; M-1 to R-436; M-1 to S-435; M-1 to S-434; M-1 to V-433; M-1 to V-432; M-1 to S-431; M-1 to T-430; M-1 to V-429; M-1 to T-428; M-1 to Y-427; M-1 to G-426; M-1 to L-425; M-1 to Y-424; M-1 to A-423; M-1 to G-422; M-1 to H-421; M-1 to N-420; M-1 to K-419; M-1 to L-418; M-1 to E-417; M-1 to E-416; M-1 to P-415; M-1 to F-414; M-1 to E-413; M-1 to K-412; M-1 to L-411; M-1 to Y-410; M-1 to S-409; M-1 to E-408; M-1 to R-407; M-1 to L-406; M-1 to P-405; M-1 to I-404; M-1 to V-403; M-1 to K-402; M-1 to G-401; M-1 to A-400; M-1 to S-399; M-1 to T-398; M-1 to E-397; M-1 to K-396; M-1 to L-395; M-1 to V-394; M-1 to A-393; M-1 to G-392; M-1 to N-391; M-1 to W-390; M-1 to D-389; M-1 to Y-388; M-1 to A-387; M-1 to G-386; M-1 to V-385; M-1 to A-384; M-1 to G-383; M-1 to L-382; M-1 to L-381; M-1 to V-380; M-1 to G-379; M-1 to D-378; M-1 to E-377; M-1 to V-376; M-1 to V-375; M-1 to H-374; M-1 to S-373; M-1 to S-372; M-1 to F-371; M-1 to G-370; M-1 to T-369; M-1 to Q-368; M-1 to S-367; M-1 to M-366; M-1 to E-365; M-1 to L-364; M-1 to G-363; M-1 to F-362; M-1 to S-361; M-1 to T-360; M-1 to E-359; M-1 to N-358; M-1 to K-357; M-1 to N-356; M-1 to T-355; M-1 to G-354; M-1 to E-353; M-1 to L-352; M-1 to S-351; M-1 to F-350; M-1 to I-349; M-1 to R-348; M-1 to D-347; M-1 to G-346; M-1 to L-345; M-1 to A-344; M-1 to D-343; M-1 to V-342; M-1 to I-341; M-1 to D-340; M-1 to K-339; M-1 to L-338; M-1 to A-337; M-1 to A-336; M-1 to E-335; M-1 to D-334; M-1 to T-333; M-1 to V-332; M-1 to N-331; M-1 to F-330; M-1 to F-329; M-1 to H-328; M-1 to K-327; M-1 to D-326; M-1 to D-325; M-1 to P-324; M-1 to D-323; M-1 to S-322; M-1 to A-321; M-1 to I-320; M-1 to Y-319; M-1 to K-318; M-1 to I-317; M-1 to E-316; M-1 to N-315; M-1 to L-314; M-1 to F-313; M-1 to T-312; M-1 to E-311; M-1 to P-310; M-1 to N-309; M-1 to I-308; M-1 to G-307; M-1 to R-306; M-1 to R-305; M-1 to N-304; M-1 to Y-303; M-1 to Y-302; M-1 to G-301; M-1 to L-300; M-1 to V-299; M-1 to A-298; M-1 to V-297; M-1 to A-296; M-1 to Y-295; M-1 to R-294; M-1 to T-293; M-1 to V-292; M-1 to N-291; M-1 to D-290; M-1 to R-289; M-1 to E-288; M-1 to S-287; M-1 to Q-286; M-1 to Q-285; M-1 to I-284; M-1 to V-283; M-1 to K-282; M-1 to E-281; M-1 to L-280; M-1 to D-279; M-1 to P-278; M-1 to S-277; M-1 to D-276; M-1 to H-275; M-1 to S-274; M-1 to E-273; M-1 to G-272; M-1 to D-271; M-1 to T-270; M-1 to I-269; M-1 to V-268; M-1 to I-267; M-1 to M-266; M-1 to V-265; M-1 to K-264; M-1 to K-263; M-1 to A-262; M-1 to G-261; M-1 to K-260; M-1 to R-259; M-1 to G-258; M-1 to G-257; M-1 to K-256; M-1 to Q-255; M-1 to F-254; M-1 to A-253; M-1 to E-252; M-1 to S-251; M-1 to R-250; M-1 to A-249; M-1 to F-248; M-1 to E-247; M-1 to I-246; M-1 to G-245; M-1 to F-244; M-1 to A-243; M-1 to T-242; M-1 to R-241; M-1 to T-240; M-1 to E-239; M-1 to T-238; M-1 to G-237; M-1 to G-236; M-1 to R-235; M-1 to Q-234; M-1 to E-233; M-1 to I-232; M-1 to H-231; M-1 to S-230; M-1 to A-229; M-1 to A-228; M-1 to E-227; M-1 to V-226; M-1 to V-225; M-1 to D-224; M-1 to K-223; M-1 to V-222; M-1 to S-221; M-1 to R-220; M-1 to Y-219; M-1 to D-218; M-1 to N-217; M-1 to L-216; M-1 to H-215; M-1 to F-214; M-1 to E-213; M-1 to H-212; M-1 to V-211; M-1 to V-210; M-1 to D-209; M-1 to E-208; M-1 to G-207; M-1 to Y-206; M-1 to Q-205; M-1 to V-204; M-1 to V-203; M-1 to G-202; M-1 to V-201; M-1 to Q-200; M-1 to I-199; M-1 to Q-198; M-1 to G-197; M-1 to P-196; M-1 to G-195; M-1 to I-194; M-1 to Y-193; M-1 to F-192; M-1 to K-191; M-1 to K-190; M-1 to L-189; M-1 to I-188; M-1 to N-187; M-1 to I-186; M-1 to L-185; M-1 to F-184; M-1 to H-183; M-1 to Q-182; M-1 to V-181; M-1 to E-180; M-1 to V-179; M-1 to W-178; M-1 to P-177; M-1 to Y-176; M-1 to I-175; M-1 to S-174; M-1 to N-173; M-1 to S-172; M-1 to G-171; M-1 to D-170; M-1 to L-169; M-1 to V-168; M-1 to I-167; M-1 to V-166; M-1 to I-165; M-1 to D-164; M-1 to M-163; M-1 to Y-162; M-1 to T-161; M-1 to Q-160; M-1 to C-159; M-1 to R-158; M-1 to Q-157; M-1 to L-156; M-1 to A-155; M-1 to P-154; M-1 to A-153; M-1 to V-152; M-1 to T-151; M-1 to K-150; M-1 to S-149; M-1 to F-148; M-1 to R-147; M-1 to F-146; M-1 to N-145; M-1 to S-144; M-1 to N-143; M-1 to V-142; M-1 to R-141; M-1 to S-140; M-1 to C-139; M-1 to M-138; M-1 to G-137; M-1 to T-136; M-1 to T-135; M-1 to Y-134; M-1 to Y-133; M-1 to S-132; M-1 to S-131; M-1 to G-130; M-1 to C-129; M-1 to E-128; M-1 to H-127; M-1 to S-126; M-1 to W-125; M-1 to L-124; M-1 to P-123; M-1 to S-122; M-1 to C-121; M-1 to A-120; M-1 to L-119; M-1 to F-118; M-1 to S-117; M-1 to N-116; M-1 to D-115; M-1 to K-114; M-1 to P-113; M-1 to N-112; M-1 to T-111; M-1 to A-110; M-1 to L-109; M-1 to S-108; M-1 to L-107; M-1 to G-106; M-1 to L-105; M-1 to R-104; M-1 to M-103; M-1 to N-102; M-1 to D-101; M-1 to K-100; M-1 to R-99; M-1 to E-98; M-1 to S-97; M-1 to V-96; M-1 to N-95; M-1 to S-94; M-1 to L-93; M-1 to T-92; M-1 to V-91; M-1 to R-90; M-1 to G-89; M-1 to L-88; M-1 to N-87; M-1 to L-86; M-1 to K-85; M-1 to T-84; M-1 to C-83; M-1 to N-82; M-1 to G-81; M-1 to H-80; M-1 to I-79; M-1 to V-78; M-1 to P-77; M-1 to C-76; M-1 to K-75; M-1 to Y-74; M-1 to V-73; M-1 to D-72; M-1 to G-71; M-1 to T-70; M-1 to K-69; M-1 to Q-68; M-1 to Y-67; M-1 to G-66; M-1 to N-65; M-1 to T-64; M-1 to E-63; M-1 to L-62; M-1 to P-61; M-1 to A-60; M-1 to G-59; M-1 to V-58; M-1 to V-57; M-1 to L-56; M-1 to W-55; M-1 to K-54; M-1 to N-53; M-1 to G-52; M-1 to S-51; M-1 to I-50; M-1 to D-49; M-1 to H-48; M-1 to Q-47; M-1 to Q-46; M-1 to V-45; M-1 to T-44; M-1 to Y-43; M-1 to G-42; M-1 to F-41; M-1 to F-40; M-1 to A-39; M-1 to T-38; M-1 to R-37; M-1 to S-36; M-1 to G-35; M-1 to P-34; M-1 to I-33; M-1 to V-32; M-1 to R-31; M-1 to P-30; M-1 to K-29; M-1 to R-28; M-1 to T-27; M-1 to D-26; M-1 to M-25; M-1 to N-24; M-1 to F-23; M-1 to T-22; M-1 to D-21; M-1 to T-20; M-1 to F-19; M-1 to G-18; M-1 to P-17; M-1 to W-16; M-1 to L-15; M-1 to S-14; M-1 to L-13; M-1 to A-12; M-1 to W-11; M-1 to A-10; M-1 to V-9; M-1 to V-8; M-1 to L-7; M-1 to G-6; of SEQ ID NO:187. Polynucleotides encoding these polypeptides are also encompassed by the invention, as are antibodies that bind one or more of these polypeptides. Moreover, fragments and variants of these polypeptides (e.g., fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides, or the complement thereof) are encompassed by the invention. Antibodies that bind these fragments and variants of the invention are also encompassed by the invention. Polynucleotides encoding these fragments and variants are also encompassed by the invention.

In addition, the invention provides nucleic acid molecules having nucleotide sequences related to extensive portions of SEQ ID NO:186 which have been determined from the following related cDNA genes:

HEEAB54R, (SEQ ID NO: 192)

HRDAF83R, (SEQ ID NO: 193)

HOUBC62R, (SEQ ID NO: 194)

HCDBI19R, (SEQ ID NO: 195)

HOHCU94R, (SEQ ID NO: 196)

HOACC13R, (SEQ ID NO: 197)

HCDAP21R (SEQ ID NO: 198)
and

HNHHA34R, (SEQ ID NO: 199)

HOHEA75R, (SEQ ID NO: 200)
and

HNGEL59R. (SEQ ID NO: 201)

A polynucleotide encoding a polypeptide of the present invention is obtained from human ovary, small intestine, fetal heart, fetal brain, large intestine, osteoblasts, human trabecular bone cells, mesangial cells, adipocytes, osteosarcoma, chondrosarcoma, breast cancer cells, and bone marrow tissues and cells. The polynucleotide of this invention was discovered in a human osteoblast II cDNA library.

Based on the sequence similarity to the human integrin alpha 1 subunit, translation product of this gene is expected to share at least some biological activities with integrin proteins, and specifically the integrin alpha 1 protein. Such activities are known in the art, some of which are described elsewhere herein.

Specifically, polynucleotides and polypeptides of the invention, including antibodies, are also useful for modulating the differentiation of normal and malignant cells, modulating the proliferation and/or differentiation of cancer and neoplastic cells, and modulating the immune response. Polynucleotides and polypeptides of the invention may represent a diagnostic marker for hematopoietic and immune diseases and/or disorders. The full-length protein should be a secreted protein, based upon homology to the integrin family. Therefore, it is secreted into serum, urine, or feces and thus the levels is assayable from patient samples. Assuming specific expression levels are reflective of the presence of immune disorders, this protein would provide a convenient diagnostic for early detection. In addition, expression of this gene product may also be linked to the progression of immune diseases, and therefore may itself actually represent a therapeutic or therapeutic target for the treatment of cancer.

Polynucleotides and polypeptides of the invention may play an important role in the pathogenesis of human cancers and cellular transformation, particularly those of the immune and hematopoietic systems. Polynucleotides and polypeptides of the invention may also be involved in the pathogenesis of developmental abnormalities based upon its potential effects on proliferation and differentiation of cells and tissue cell types. Due to the potential proliferating and differentiating activity of said polynucleotides and polypeptides, the invention is useful as a therapeutic agent in inducing tissue regeneration, for treating inflammatory conditions (e.g., inflammatory bowel syndrome, diverticulitis, etc.). Moreover, the invention is useful in modulating the immune response to aberrant polypeptides, as may exist in rapidly proliferating cells and tissue cell types, particularly in adenocarcinoma cells, and other cancers.

Alternatively, the expression within cellular sources marked by proliferating cells indicates this protein may play a role in the regulation of cellular division, and may show utility in the diagnosis, treatment, and/or prevention of developmental diseases and disorders, including cancer, and other proliferative conditions. Representative uses are described in the "Hyperproliferative Disorders" and "Regeneration" sections below and elsewhere herein. Briefly, developmental tissues rely on decisions involving cell differentiation and/or apoptosis in pattern formation.

Dysregulation of apoptosis can result in inappropriate suppression of cell death, as occurs in the development of some cancers, or in failure to control the extent of cell death, as is believed to occur in acquired immunodeficiency and certain neurodegenerative disorders, such as spinal muscular atrophy (SMA).

Alternatively, this gene product is involved in the pattern of cellular proliferation that accompanies early embryogenesis. Thus, aberrant expression of this gene product in tissues—particularly adult tissues—may correlate with patterns of abnormal cellular proliferation, such as found in various cancers. Because of potential roles in proliferation and differentiation, this gene product may have applications in the adult for tissue regeneration and the treatment of cancers. It may also act as a morphogen to control cell and tissue type specification. Therefore, the polynucleotides and polypeptides of the present invention are useful in treating, detecting, and/or preventing said disorders and conditions, in addition to other types of degenerative conditions. Thus, this protein may modulate apoptosis or tissue differentiation and is useful in the detection, treatment, and/or prevention of degenerative or proliferative conditions and diseases. The protein is useful in modulating the immune response to aberrant polypeptides, as may exist in proliferating and cancerous cells and tissues. The protein can also be used to gain new insight into the regulation of cellular growth and proliferation. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

This gene is expressed almost exclusively in osteoblasts, human trabecular bone cells, mesangial cells, adipocytes, and to a lesser extent in osteosarcoma, chondrosarcoma, breast cancer cells, and bone marrow.

Therefore, polynucleotides and polypeptides of the invention, including antibodies, are useful as reagents for differential identification of the tissue(s) or cell type(s) present in a biological sample and for diagnosis of the following diseases and conditions which include, but are not limited to, disorders of the skeletal system, connective tissues, and immune and hematopoietic diseases and/or disorders. Similarly, polypeptides and antibodies directed to these polypeptides are useful to provide immunological probes for differential identification of the tissue(s) or cell type(s). For a number of disorders of the above tissues or cells, particularly of the connective tissue and skeletal system, expression of this gene at significantly higher or lower levels is detected in certain tissues or cell types (e.g. immune, hematopoietic, skeletal, bone, cartilage, developmental, reproductive, secretory, and cancerous and wounded tissues) or bodily fluids or cell types (e.g., lymph, serum, plasma, urine, synovial fluid or spinal fluid) or another tissue or cell sample taken from an individual having such a disorder, relative to the standard gene expression level, i.e., the expression level in healthy tissue from an individual not having the disorder.

The tissue distribution in osteoblasts and homology to integrin alpha subunit 10 indicates that the protein products of this gene are useful for the treatment of disorders and conditions affecting the skeletal system, in particular osteoporosis as well as disorders afflicting connective tissues (e.g., arthritis, trauma, tendonitis, chrondomalacia and inflammation), such as in the diagnosis and treatment of various autoimmune disorders such as rheumatoid arthritis, lupus, scleroderma, and dermatomyositis as well as dwarfism, spinal deformation, and specific joint abnormalities as well as chondrodysplasias (i.e., spondyloepiphyseal dysplasia congenita, familial osteoarthritis, Atelosteogenesis type II, metaphyseal chondrodysplasia type Schmid). polynucleotides and polypeptides corresponding to this gene are useful for the treatment and diagnosis of hematopoietic related disorders such as anemia, pancytopenia, leukopenia, thrombocytopenia or leukemia since stromal cells are important in the production of cells of hematopoietic lineages. Such a use is consistent with the observed homology to integrin family members, in conjunction with the tissue distribution in bone marrow cells.

Integrins play pivotal roles in cell migration, inflammation, proliferation, and cellular infiltration. Thus, the present invention is expected to share at least some of these activities. Representative uses are described in the "Immune Activity" and "infectious disease" sections below, in Examples 17, 42, 44, 45, 47, 49, 50, and 51, and elsewhere herein. Briefly, the uses include bone marrow cell ex-vivo culture, bone marrow transplantation, bone marrow reconstitution, radiotherapy or chemotherapy of neoplasia. The gene product may also be involved in lymphopoiesis, therefore, it can be used in immune disorders such as infection, inflammation, allergy, immunodeficiency etc. In addition, this gene product may have commercial utility in the expansion of stem cells and committed progenitors of various blood lineages, and in the differentiation and/or proliferation of various cell types. Based upon the tissue distribution of this protein, antagonists directed against this protein is useful in blocking the activity of this protein. Accordingly, preferred are antibodies which specifically bind a portion of the translation product of this gene.

Also provided is a kit for detecting tumors in which expression of this protein occurs. Such a kit comprises in one embodiment an antibody specific for the translation product of this gene bound to a solid support. Also provided is a method of detecting these tumors in an individual which comprises a step of contacting an antibody specific for the translation product of this gene to a bodily fluid from the individual, preferably serum, and ascertaining whether antibody binds to an antigen found in the bodily fluid. Preferably the antibody is bound to a solid support and the bodily fluid is serum. The above embodiments, as well as other treatments and diagnostic tests (kits and methods), are more particularly described elsewhere herein.

Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:186 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 4981 of SEQ ID NO:186, b is an integer of 15 to 4995, where both a and b correspond to the positions of nucleotide residues shown in SEQ ID NO:186, and where b is greater than or equal to a+14.

Tables

Description of Table 1A

Table 1A summarizes information concerning certain polynucleotides and polypeptides of the invention. The first column provides the gene number in the application for each clone identifier. The second column provides a unique clone identifier, "cDNA Clone ID", for a cDNA clone related to each contig sequence disclosed in Table 1A. The cDNA Clones identified in the second column were deposited as indicated in the third column (i.e. by ATCC™ Deposit No: Z and deposit date). Some of the deposits contain multiple different clones corresponding to the same gene. In the fourth column, "Vector" refers to the type of vector contained in the corresponding cDNA Clone identified in the second column. In the fifth column, the nucleotide sequence identified as "NT SEQ ID NO:X" was assembled from partially homologous ("overlapping") sequences obtained from the corresponding cDNA clone identified in the second column and, in some cases, from additional related cDNA clones. The overlapping sequences were assembled into a single contiguous sequence of high redundancy (usually three to five overlapping sequences at each nucleotide position), resulting in a final sequence identified as SEQ ID NO:X. In the sixth column, "Total NT Seq." refers to the total number of nucleotides in the contig sequence identified as SEQ ID NO:X." The deposited clone may contain all or most of these sequences, reflected by the nucleotide position indicated as "5' NT of Clone Seq." (seventh column) and the "3' NT of Clone Seq." (eighth column) of SEQ ID NO:X. In the ninth column, the nucleotide position of SEQ ID NO:X of the putative start codon (methionine) is identified as "5' NT of Start Codon." Similarly, in column ten, the nucleotide position of SEQ ID NO:X of the predicted signal sequence is identified as "5' NT of First AA of Signal Pep." In the eleventh column, the translated amino acid sequence, beginning with the methionine, is identified as "AA SEQ ID NO:Y," although other reading frames can also be routinely translated using known molecular biology techniques. The polypeptides produced by these alternative open reading frames are specifically contemplated by the present invention.

In the twelfth and thirteenth columns of Table 1A, the first and last amino acid position of SEQ ID NO:Y of the predicted signal peptide is identified as "First AA of Sig Pep" and "Last AA of Sig Pep." In the fourteenth column, the predicted first amino acid position of SEQ ID NO:Y of the secreted portion is identified as "Predicted First AA of Secreted Portion". The amino acid position of SEQ ID NO:Y of the last amino acid encoded by the open reading frame is identified in the fifteenth column as "Last AA of ORF".

SEQ ID NO:X (where X may be any of the polynucleotide sequences disclosed in the sequence listing) and the translated SEQ ID NO:Y (where Y may be any of the polypeptide sequences disclosed in the sequence listing) are sufficiently accurate and otherwise suitable for a variety of uses well known in the art and described further below. For instance, SEQ ID NO:X is useful for designing nucleic acid hybridization probes that will detect nucleic acid sequences contained in SEQ ID NO:X or the cDNA contained in the deposited clone. These probes will also hybridize to nucleic acid molecules in biological samples, thereby enabling a variety of forensic and diagnostic methods of the invention. Similarly, polypeptides identified from SEQ ID NO:Y may be used, for example, to generate antibodies which bind specifically to proteins containing the polypeptides and the secreted proteins encoded by the cDNA clones identified in Table 1A and/or elsewhere herein.

Nevertheless, DNA sequences generated by sequencing reactions can contain sequencing errors. The errors exist as misidentified nucleotides, or as insertions or deletions of nucleotides in the generated DNA sequence. The erroneously inserted or deleted nucleotides cause frame shifts in the reading frames of the predicted amino acid sequence. In these cases, the predicted amino acid sequence diverges from the actual amino acid sequence, even though the generated DNA sequence may be greater than 99.9% identical to the actual DNA sequence (for example, one base insertion or deletion in an open reading frame of over 1000 bases).

Accordingly, for those applications requiring precision in the nucleotide sequence or the amino acid sequence, the present invention provides not only the generated nucleotide sequence identified as SEQ ID NO:X, and the predicted translated amino acid sequence identified as SEQ ID NO:Y, but also a sample of plasmid DNA containing a human cDNA of the invention deposited with the ATCC™, as set forth in Table 1A. The nucleotide sequence of each deposited plasmid can readily be determined by sequencing the deposited plasmid in accordance with known methods The predicted amino acid sequence can then be verified from such deposits. Moreover, the amino acid sequence of the protein encoded by a particular plasmid can also be directly determined by peptide sequencing or by expressing the protein in a suitable host cell containing the deposited human cDNA, collecting the protein, and determining its sequence.

Also provided in Table 1A is the name of the vector which contains the cDNA plasmid. Each vector is routinely used in the art. The following additional information is provided for convenience.

Vectors Lambda Zap (U.S. Pat. Nos. 5,128,256 and 5,286,636), Uni-Zap XR (U.S. Pat. Nos. 5,128,256 and 5,286,636), Zap Express (U.S. Pat. Nos. 5,128,256 and 5,286,636), pBLUESCRIPT™ (pBS) (Short, J. M. et al., *Nucleic Acids Res.* 16:7583-7600 (1988); Alting-Mees, M. A. and Short, J. M., *Nucleic Acids Res.* 17:9494 (1989)) and pBK (Alting-Mees, M. A. et al., *Strategies* 5:58-61 (1992)) are commercially available from STRATAGENE™ Cloning Systems, Inc., 11011 N. Torrey Pines Road, La Jolla, Calif., 92037. pBS contains an ampicillin resistance gene and pBK contains a neomycin resistance gene. Phagemid pBS may be excised from the Lambda Zap and Uni-Zap XR vectors, and phagemid pBK may be excised from the Zap Express vector. Both phagemids may be transformed into *E. coli* strain XL-1 Blue, also available from STRATAGENE™.

Vectors pSport1, pCMVSport 1.0, pCMVSport 2.0 and pCMVSport 3.0, were obtained from LIFE TECHNOLOGIES™, Inc., P.O. Box 6009, Gaithersburg, Md. 20897. All Sport vectors contain an ampicillin resistance gene and may be transformed into *E. coli* strain DH10B, also available from LIFE TECHNOLOGIES™. See, for instance, Gruber, C. E., et al., *Focus* 15:59 (1993). Vector lafmid BA (Bento Soares, Columbia University, New York, N.Y.) contains an ampicillin resistance gene and can be transformed into *E. coli* strain XL-1 Blue. Vector pCR®2.1, which is available from Invitrogen, 1600 Faraday Avenue, Carlsbad, Calif. 92008, contains an ampicillin resistance gene and may be transformed into *E. coli* strain DH10B, available from LIFE TECHNOLOGIES™. See, for instance, Clark, J. M., *Nuc. Acids Res.* 16:9677-9686 (1988) and Mead, D. et al., *Bio/Technology* 9: (1991).

The present invention also relates to the genes corresponding to SEQ ID NO:X, SEQ ID NO:Y, and/or a deposited cDNA (cDNA Clone ID). The corresponding gene can be isolated in accordance with known methods using the sequence information disclosed herein. Such methods include, but are not limited to, preparing probes or primers from the disclosed sequence and identifying or amplifying the corresponding gene from appropriate sources of genomic material.

Also provided in the present invention are allelic variants, orthologs, and/or species homologs. Procedures known in the art can be used to obtain full-length genes, allelic variants, splice variants, full-length coding portions, orthologs, and/or species homologs of genes corresponding to SEQ ID NO:X and SEQ ID NO:Y using information from the sequences disclosed herein or the clones deposited with the ATCC™. For example, allelic variants and/or species homologs may be isolated and identified by making suitable probes or primers from the sequences provided herein and screening a suitable nucleic acid source for allelic variants and/or the desired homologue.

The present invention provides a polynucleotide comprising, or alternatively consisting of, the nucleic acid sequence of SEQ ID NO:X and/or a cDNA contained in ATCC™ Deposit No:Z. The present invention also provides a polypeptide comprising, or alternatively, consisting of, the polypeptide sequence of SEQ ID NO:Y, a polypeptide encoded by SEQ ID NO:X, and/or a polypeptide encoded by a cDNA contained in ATCC™ Deposit No:Z. Polynucleotides encoding a polypeptide comprising, or alternatively consisting of the polypeptide sequence of SEQ ID NO:Y, a polypeptide encoded by SEQ ID NO:X and/or a polypeptide encoded by the cDNA contained in ATCC™ Deposit No:Z, are also encompassed by the invention. The present invention further encompasses a polynucleotide comprising, or alternatively consisting of the complement of the nucleic acid sequence of SEQ ID NO:X, and/or the complement of the coding strand of the cDNA contained in ATCC™ Deposit No:Z.

Description of Tables 1B.1 and 1B.2

Tables 1B.1 and 1B.2 summarize some of the polynucleotides encompassed by the invention (including cDNA clones related to the sequences (Clone ID:), contig sequences (contig identifier (Contig ID:) and contig nucleotide sequence identifiers (SEQ ID NO:X)) and further summarizes certain characteristics of these polynucleotides and the polypeptides encoded thereby. The first column of Tables 1B.1 and 1B.2 provide the gene numbers in the application for each clone identifier. The second column of Tables 1B.1 and 1B.2 provide unique clone identifiers, “cDNA Clone ID”, for cDNA clones related to each contig sequence disclosed in Table 1A and/or Tables 1B.1 and 1B.2. The third column of Tables 1B.1 and 1B.2 provide unique contig identifiers, “Contig ID:” for each of the contig sequences disclosed in these tables. The fourth column of Tables 1B.1 and 1B.2 provide the sequence identifiers, “SEQ ID NO:X”, for each of the contig sequences disclosed in Table 1A and/or Tables 1B.1 and 1B.2. Table 1B.1

The fifth column of Table 1B.1, "ORF (From-To)", provides the location (i.e., nucleotide position numbers) within the polynucleotide sequence of SEQ ID NO:X that delineates the preferred open reading frame (ORF) that encodes the amino acid sequence shown in the sequence listing and referenced in Table 1B.1 as SEQ ID NO:Y (column 6). Column 7 of Table 1B.1 lists residues comprising predicted epitopes contained in the polypeptides encoded by each of the preferred ORFs (SEQ ID NO:Y). Identification of potential immunogenic regions was performed according to the method of Jameson and Wolf (CABIOS, 4; 181-186 (1988)); specifically, the Genetics Computer Group (GCG) implementation of this algorithm, embodied in the program PEPTIDESTRUCTURE (Wisconsin Package v10.0, Genetics Computer Group (GCG), Madison, Wis.). This method returns a measure of the probability that a given residue is found on the surface of the protein. Regions where the antigenic index score is greater than 0.9 over at least 6 amino acids are indicated in Table 1B.1 as "Predicted Epitopes". In particular embodiments, polypeptides of the invention comprise, or alternatively consist of, one, two, three, four, five or more of the predicted epitopes described in Table 1B.1. It will be appreciated that depending on the analytical criteria used to predict antigenic determinants, the exact address of the determinant may vary slightly. Column 8 of Table 1B.1 ("Cytologic Band") provides the chromosomal location of polynucleotides corresponding to SEQ ID NO:X. Chromosomal location was determined by finding exact matches to EST and cDNA sequences contained in the NCBI (National Center for Biotechnology Information) UniGene database. Given a presumptive chromosomal location, disease locus association was determined by comparison with the Morbid Map, derived from OMIM™ ("Online Mendelian Inheritance in Man," McKusick-Nathans Institute for Genetic Medicine, Johns Hopkins University (Baltimore, Md.) and National Center for Biotechnology Information, National Library of Medicine (Bethesda, Md.) 2000 (world wide web at ncbi.nlm.nih.gov/omim/). If the putative chromosomal location of the Query overlaps with the chromosomal location of a Morbid Map entry, an OMIM identification number is disclosed in Table 1B.1, column 9 labeled "OMIM Disease Reference(s)". Table 5 is a key to the OMIM reference identification numbers (Table 5, column 1), and provides a description of the associated disease in Table 5, column 2.

Table 1B.2

Column 5 of Table 1B.2, "Tissue Distribution" shows the expression profile of tissue, cells, and/or cell line libraries which express the polynucleotides of the invention. The first code number shown in Table 1B.2 column 5 (preceding the colon), represents the tissue/cell source identifier code corresponding to the key provided in Table 4. Expression of these polynucleotides was not observed in the other tissues and/or cell libraries tested. The second number in column 5 (following the colon), represents the number of times a sequence corresponding to the reference polynucleotide sequence (e.g., SEQ ID NO:X) was identified in the corresponding tissue/cell source. Those tissue/cell source identifier codes in which the first two letters are "AR" designate information generated using DNA array technology. Utilizing this technology, cDNAs were amplified by PCR and then transferred, in duplicate, onto the array. Gene expression was assayed through hybridization of first strand cDNA probes to the DNA array. cDNA probes were generated from total RNA extracted from a variety of different tissues and cell lines. Probe synthesis was performed in the presence of $^{33}$P dCTP, using oligo(dT) to prime reverse transcription. After hybridization, high stringency washing conditions were employed to remove non-specific hybrids from the array. The remaining signal, emanating from each gene target, was measured using a Phosphorimager. Gene expression was reported as Phosphor Stimulating Luminescence (PSL) which reflects the level of phosphor signal generated from the probe hybridized to each of the gene targets represented on the array. A local background signal subtraction was performed before the total signal generated from each array was used to normalize gene expression between the different hybridizations. The value presented after "[array code]:" represents the mean of the duplicate values, following background subtraction and probe normalization. One of skill in the art could routinely use this information to identify normal and/or diseased tissue(s) which show a predominant expression pattern of the corresponding polynucleotide of the invention or to identify polynucleotides which show predominant and/or specific tissue and/or cell expression.

Description of Table 1C

Table 1C summarizes additional polynucleotides encompassed by the invention (including cDNA clones related to the sequences (Clone ID:), contig sequences (contig identifier (Contig ID:) contig nucleotide sequence identifiers (SEQ ID NO:X)), and genomic sequences (SEQ ID NO:B). The first column provides a unique clone identifier, "Clone ID:", for a cDNA clone related to each contig sequence. The second column provides the sequence identifier, "SEQ ID NO:X", for each contig sequence. The third column provides a unique contig identifier, "Contig ID:" for each contig sequence. The fourth column, provides a BAC identifier "BAC ID NO:A" for the BAC clone referenced in the corresponding row of the table. The fifth column provides the nucleotide sequence identifier, "SEQ ID NO:B" for a fragment of the BAC clone identified in column four of the corresponding row of the table. The sixth column, "Exon From-To", provides the location (i.e., nucleotide position numbers) within the polynucleotide sequence of SEQ ID NO:B which delineate certain polynucleotides of the invention that are also exemplary members of polynucleotide sequences that encode polypeptides of the invention (e.g., polypeptides containing amino acid sequences encoded by the polynucleotide sequences delineated in column six, and fragments and variants thereof). Table 1C in priority Application No. PCT/US02/09785, filed Mar. 19, 2002, which corresponds to Publication No. WO02/95010, published Nov. 28, 2002 (e.g., pages 228 to 235 of Publication No. WO02/95010) is incorporated by reference herein in its entirety.

Description of Tables 1D, 1E, 1E.1 and 1E.2

Table 1D: In preferred embodiments, the present invention encompasses a method of detecting, preventing, diagnosing, prognosticating, treating, and/or ameliorating a disease or disorder listed as listed in the "Preferred Indications" column of Table 1D, column 3; comprising administering to a patient (in which such detection, prevention, treatment, and/or amelioration is desired) a protein, nucleic acid, or antibody of the invention (or fragment or variant thereof) represented by, for example, Table 1A or 1D (in the same row as the disease or disorder to be treated is listed in the "Preferred Indications" column of Tables 1D) in an amount effective to detect, prevent, diagnose, prognosticate, treat, or ameliorate the disease or disorder. In preferred embodiments, the present invention encompasses a method of detecting, preventing, diagnosing, prognosticating, treating, and/or ameliorating a disease or disorder (such as an immune, cardiovascular, cancer, or other proliferative disease or disorder), comprising administering to a patient in which such treatment, prevention, or amelioration is desired a protein, nucleic acid, or antibody of the invention (or fragment or variant thereof) represented by Tables 1A, 1B.1, 1B.2, and 1C, in an amount effective to detect, prevent, diagnose, prognosticate, treat, and/or ameliorate the disease or disorder.

As indicated in Table 1D, the polynucleotides, polypeptides, agonists, or antagonists of the present invention (including antibodies) can be used in assays to test for one or more biological activities. If these polynucleotides and polypeptides do exhibit activity in a particular assay, it is likely that these molecules may be involved in the diseases associated with the biological activity. Thus, the polynucleotides or polypeptides, or agonists or antagonists thereof (including antibodies) could be used to prevent, treat, or ameliorate the associated disease.

The present invention encompasses methods of detecting, preventing, diagnosing, prognosticating, treating, and/or ameliorating a disease or disorder. In preferred embodiments, the present invention encompasses a method of detecting, diagnosing, treating, preventing, or ameliorating a disease or disorder listed in the "Preferred Indications" column of Table 1D; comprising administering to a patient in which such treatment, prevention, or amelioration is desired a protein, nucleic acid, or antibody of the invention (or fragment or variant thereof) in an amount effective to treat, prevent, diagnose, or ameliorate the disease or disorder. The first and second columns of Table 1D show the "Gene No." and "cDNA Clone ID No.", respectively, indicating certain nucleic acids and proteins (or antibodies against the same) of the invention (including polynucleotide, polypeptide, and antibody fragments or variants thereof) that may be used in detecting, preventing, diagnosing, prognosticating, treating, and/or ameliorating the disease(s) or disorder(s) indicated in the corresponding row in Column 3 of Table 1D.

In another embodiment, the present invention also encompasses methods of preventing, treating, diagnosing, or ameliorating a disease or disorder listed in the "Preferred Indications" column of Table 1D; comprising administering to a patient combinations of the proteins, nucleic acids, or antibodies of the invention (or fragments or variants thereof), sharing similar indications as shown in the corresponding rows in Column 3 of Table 1D.

The "Preferred Indication" column describes diseases, disorders, and/or conditions that may be treated, prevented, diagnosed, or ameliorated by a protein, nucleic acid, or antibody of the invention (or fragment or variant thereof).

The recitation of "Cancer" in the "Preferred Indication" column indicates that the corresponding nucleic acid and protein, or antibody against the same, of the invention (or fragment or variant thereof) may be used for example, to diagnose, treat, prevent, and/or ameliorate diseases and/or disorders relating to neoplastic diseases (e.g., leukemias, cancers, and/or as described below under "Hyperproliferative Disorders").

In specific embodiments, a protein, nucleic acid, or antibody of the invention (or fragment or variant thereof) having a "Cancer" recitation in the "Preferred Indication" column of Table 1D may be used for example, to diagnose, treat, prevent, and/or ameliorate a neoplasm located in a tissue selected from the group consisting of: colon, abdomen, bone, breast, digestive system, liver, pancreas, prostate, peritoneum, lung, blood (e.g., leukemia), endocrine glands (adrenal, parathyroid, pituitary, testicles, ovary, thymus, thyroid), uterus, eye, head and neck, nervous (central and peripheral), lymphatic system, pelvic, skin, soft tissue, spleen, thoracic, and urogenital.

In specific embodiments, a protein, nucleic acid, or antibody of the invention (or fragment or variant thereof) having a "Cancer" recitation in the "Preferred Indication" column of Table 1D, may be used for example, to diagnose, treat, prevent, and/or ameliorate a pre-neoplastic condition, selected from the group consisting of: hyperplasia (e.g., endometrial hyperplasia and/or as described in the section entitled "Hyperproliferative Disorders"), metaplasia (e.g., connective tissue metaplasia, atypical metaplasia, and/or as described in the section entitled "Hyperproliferative Disorders"), and/or dysplasia (e.g., cervical dysplasia, and bronchopulmonary dysplasia).

In another specific embodiment, a protein, nucleic acid, or antibody of the invention (or fragment or variant thereof) having a "Cancer" recitation in the "Preferred Indication" column of Table 1D, may be used for example, to diagnose, treat, prevent, and/or ameliorate a benign dysproliferative disorder selected from the group consisting of: benign tumors, fibrocystic conditions, tissue hypertrophy, and/or as described in the section entitled "Hyperproliferative Disorders".

The recitation of "Immune/Hematopoietic" in the "Preferred Indication" column indicates that the corresponding nucleic acid and protein, or antibody against the same, of the invention (or fragment or variant thereof), may be used for example, to diagnose, treat, prevent, and/or ameliorate diseases and/or disorders relating to neoplastic diseases (e.g., as described below under "Hyperproliferative Disorders"), blood disorders (e.g., as described below under "Immune Activity" "Cardiovascular Disorders" and/or "Blood-Related Disorders"), and infections (e.g., as described below under "Infectious Disease").

In specific embodiments, a protein, nucleic acid, or antibody of the invention (or fragment or variant thereof) having the "Immune/Hematopoietic" recitation in the "Preferred Indication" column of Table 1D, may be used for example, to diagnose, treat, prevent, and/or ameliorate a disease or disorder selected from the group consisting of: anemia, pancytopenia, leukopenia, thrombocytopenia, leukemias, Hodgkin's disease, non-Hodgkin's lymphoma, acute lymphocytic anemia (ALL), plasmacytomas, multiple myeloma, Burkitt's lymphoma, arthritis, asthma, AIDS, autoimmune disease, rheumatoid arthritis, granulomatous disease, immune deficiency, inflammatory bowel disease, sepsis, neutropenia, neutrophilia, psoriasis, immune reactions to transplanted organs and tissues, systemic lupus erythematosis, hemophilia, hypercoagulation, diabetes mellitus, endocarditis, meningitis, Lyme Disease, and allergies.

The recitation of "Reproductive" in the "Preferred Indication" column indicates that the corresponding nucleic acid and protein, or antibody against the same, of the invention (or fragment or variant thereof), may be used for example, to diagnose, treat, prevent, and/or ameliorate diseases and/or disorders relating to neoplastic diseases (e.g., as described below under "Hyperproliferative Disorders"), and disorders of the reproductive system (e.g., as described below under "Reproductive System Disorders").

In specific embodiments, a protein, nucleic acid, or antibody of the invention (or fragment or variant thereof) having a "Reproductive" recitation in the "Preferred Indication" column of Table 1D, may be used for example, to diagnose, treat, prevent, and/or ameliorate a disease or disorder selected from the group consisting of: cryptorchism, prostatitis, inguinal hernia, varicocele, leydig cell tumors, verrucous carcinoma, prostatitis, malacoplakia, Peyronie's disease, penile carcinoma, squamous cell hyperplasia, dysmenorrhea, ovarian adenocarcinoma, Turner's syndrome, mucopurulent cervicitis, Sertoli-leydig tumors, ovarian cancer, uterine cancer, pelvic inflammatory disease, testicular cancer, prostate cancer, Klinefelter's syndrome, Young's syndrome, premature ejaculation, diabetes mellitus, cystic fibrosis, Kartagener's syndrome, testicular atrophy, testicular feminization, anorchia, ectopic testis, epididymitis, orchitis, gonorrhea, syphilis, testicular torsion, vasitis nodosa, germ cell tumors, stromal tumors, dysmenorrhea, retroverted uterus, endometriosis, fibroids, adenomyosis, anovulatory bleeding, amenorrhea, Cushing's syndrome, hydatidiform moles, Asherman's syndrome, premature menopause, precocious puberty, uterine polyps, dysfunctional uterine bleeding, cervicitis, chronic cervicitis, mucopurulent cervicitis, cervical dysplasia, cervical polyps, Nabothian cysts, cervical erosion, cervical incompetence, cervical neoplasms, pseudohermaphroditism, and premenstrual syndrome.

The recitation of "Musculoskeletal" in the "Preferred Indication" column indicates that the corresponding nucleic acid and protein, or antibody against the same, of the invention (or fragment or variant thereof), may be used for example, to diagnose, treat, prevent, and/or ameliorate diseases and/or disorders relating to neoplastic diseases (e.g., as described below under "Hyperproliferative Disorders"), and disorders of the immune system (e.g., as described below under "Immune Activity").

In specific embodiments, a protein, nucleic acid, or antibody of the invention (or fragment or variant thereof) having a "Musculoskeletal" recitation in the "Preferred Indication" column of Table 1D, may be used for example, to diagnose, treat, prevent, and/or ameliorate a disease or disorder selected from the group consisting of: bone cancers (e.g., osteochondromas, benign chondromas, chondroblastoma, chondromyxoid fibromas, osteoid osteomas, giant cell tumors, multiple myeloma, osteosarcomas), Paget's Disease, rheumatoid arthritis, systemic lupus erythematosus, osteomyelitis, Lyme Disease, gout, bursitis, tendonitis, osteoporosis, osteoarthritis, muscular dystrophy, mitochondrial myopathy, cachexia, and multiple sclerosis.

The recitation of "Cardiovascular" in the "Preferred Indication" column indicates that the corresponding nucleic acid and protein, or antibody against the same, of the invention (or fragment or variant thereof), may be used for example, to diagnose, treat, prevent, and/or ameliorate diseases and/or disorders relating to neoplastic diseases (e.g., as described below under "Hyperproliferative Disorders"), and disorders of the cardiovascular system (e.g., as described below under "Cardiovascular Disorders").

In specific embodiments, a protein, nucleic acid, or antibody of the invention (or fragment or variant thereof) having a "Cardiovascular" recitation in the "Preferred Indication" column of Table 1D, may be used for example, to diagnose, treat, prevent, and/or ameliorate a disease or disorder selected from the group consisting of: myxomas, fibromas, rhabdomyomas, cardiovascular abnormalities (e.g., congenital heart defects, cerebral arteriovenous malformations, septal defects), heart disease (e.g., heart failure, congestive heart disease, arrhythmia, tachycardia, fibrillation, pericardial Disease, endocarditis), cardiac arrest, heart valve disease (e.g., stenosis, regurgitation, prolapse), vascular disease (e.g., hypertension, coronary artery disease, angina, aneurysm, arteriosclerosis, peripheral vascular disease), hyponatremia, hypernatremia, hypokalemia, and hyperkalemia.

The recitation of "Mixed Fetal" in the "Preferred Indication" column indicates that the corresponding nucleic acid and protein, or antibody against the same, of the invention (or fragment or variant thereof), may be used for example, to diagnose, treat, prevent, and/or ameliorate diseases and/or disorders relating to neoplastic diseases (e.g., as described below under "Hyperproliferative Disorders").

In specific embodiments, a protein, nucleic acid, or antibody of the invention (or fragment or variant thereof) having a "Mixed Fetal" recitation in the "Preferred Indication" column of Table 1D, may be used for example, to diagnose, treat, prevent, and/or ameliorate a disease or disorder selected from the group consisting of: spina bifida, hydranencephaly, neurofibromatosis, fetal alcohol syndrome, diabetes mellitus, PKU, Down's syndrome, Patau syndrome, Edwards syndrome, Turner syndrome, Apert syndrome, Carpenter syndrome, Conradi syndrome, Crouzon syndrome, cutis laxa, Cornelia de Lange syndrome, Ellis-van Creveld syndrome, Holt-Oram syndrome, Kartagener syndrome, Meckel-Gruber syndrome, Noonan syndrome, Pallister-Hall syndrome, Rubinstein-Taybi syndrome, Scimitar syndrome, Smith-Lemli-Opitz syndrome, thromocytopenia-absent radius (TAR) syndrome, Treacher Collins syndrome, Williams syndrome, Hirschsprung's disease, Meckel's diverticulum, polycystic kidney disease, Turner's syndrome, and gonadal dysgenesis, Klippel-Feil syndrome, Ostogenesis imperfecta, muscular dystrophy, Tay-Sachs disease, Wilm's tumor, neuroblastoma, and retinoblastoma.

The recitation of "Excretory" in the "Preferred Indication" column indicates that the corresponding nucleic acid and protein, or antibody against the same, of the invention (or fragment or variant thereof), may be used for example, to diagnose, treat, prevent, and/or ameliorate diseases and/or disorders relating to neoplastic diseases (e.g., as described below under "Hyperproliferative Disorders") and renal disorders (e.g., as described below under "Renal Disorders").

In specific embodiments, a protein, nucleic acid, or antibody of the invention (or fragment or variant thereof) having a "Excretory" recitation in the "Preferred Indication" column of Table 1D, may be used for example, to diagnose, treat, prevent, and/or ameliorate a disease or disorder selected from the group consisting of: bladder cancer, prostate cancer, benign prostatic hyperplasia, bladder disorders (e.g., urinary incontinence, urinary retention, urinary obstruction, urinary tract Infections, interstitial cystitis, prostatitis, neurogenic bladder, hematuria), renal disorders (e.g., hydronephrosis, proteinuria, renal failure, pyelonephritis, urolithiasis, reflux nephropathy, and unilateral obstructive uropathy).

The recitation of "Neural/Sensory" in the "Preferred Indication" column indicates that the corresponding nucleic acid and protein, or antibody against the same, of the invention (or fragment or variant thereof), may be used for example, to diagnose, treat, prevent, and/or ameliorate diseases and/or disorders relating to neoplastic diseases (e.g., as described below under "Hyperproliferative Disorders") and diseases or disorders of the nervous system (e.g., as described below under "Neural Activity and Neurological Diseases").

In specific embodiments, a protein, nucleic acid, or antibody of the invention (or fragment or variant thereof) having a "Neural/Sensory" recitation in the "Preferred Indication" column of Table 1D, may be used for example, to diagnose, treat, prevent, and/or ameliorate a disease or disorder selected from the group consisting of: brain cancer (e.g., brain stem glioma, brain tumors, central nervous system (Primary) lymphoma, central nervous system lymphoma, cerebellar astrocytoma, and cerebral astrocytoma, neurodegenerative disorders (e.g., Alzheimer's Disease, Creutzfeldt-Jakob Disease, Parkinson's Disease, and Idiopathic Presenile Dementia), encephalomyelitis, cerebral malaria, meningitis, metabolic brain diseases (e.g., phenylketonuria and pyruvate carboxylase deficiency), cerebellar ataxia, ataxia telangiectasia, and AIDS Dementia Complex, schizophrenia, attention deficit disorder, hyperactive attention deficit disorder, autism, and obsessive compulsive disorders.

The recitation of "Respiratory" in the "Preferred Indication" column indicates that the corresponding nucleic acid and protein, or antibody against the same, of the invention (or fragment or variant thereof), may be used for example, to diagnose, treat, prevent, and/or ameliorate diseases and/or disorders relating to neoplastic diseases (e.g., as described below under "Hyperproliferative Disorders") and diseases or disorders of the respiratory system (e.g., as described below under "Respiratory Disorders").

In specific embodiments, a protein, nucleic acid, or antibody of the invention (or fragment or variant thereof) having a "Respiratory" recitation in the "Preferred Indication" column of Table 1D, may be used for example, to diagnose, treat, prevent, and/or ameliorate a disease or disorder selected from the group consisting of: cancers of the respiratory system such as larynx cancer, pharynx cancer, trachea cancer, epiglottis cancer, lung cancer, squamous cell carcinomas, small cell (oat cell) carcinomas, large cell carcinomas, and adenocarcinomas. Allergic reactions, cystic fibrosis, sarcoidosis, histiocytosis X, infiltrative lung diseases (e.g., pulmonary fibrosis and lymphoid interstitial pneumonia), obstructive airway diseases (e.g., asthma, emphysema, chronic or acute bronchitis), occupational lung diseases (e.g., silicosis and asbestosis), pneumonia, and pleurisy.

The recitation of "Endocrine" in the "Preferred Indication" column indicates that the corresponding nucleic acid and protein, or antibody against the same, of the invention (or fragment or variant thereof), may be used for example, to diagnose, treat, prevent, and/or ameliorate diseases and/or disorders relating to neoplastic diseases (e.g., as described below under "Hyperproliferative Disorders") and diseases or disorders of the respiratory system (e.g., as described below under "Respiratory Disorders"), renal disorders (e.g., as described below under "Renal Disorders"), and disorders of the endocrine system (e.g., as described below under "Endocrine Disorders".

In specific embodiments, a protein, nucleic acid, or antibody of the invention (or fragment or variant thereof) having an "Endocrine" recitation in the "Preferred Indication" column of Table 1D, may be used for example, to diagnose, treat, prevent, and/or ameliorate a disease or disorder selected from the group consisting of: cancers of endocrine tissues and organs (e.g., cancers of the hypothalamus, pituitary gland, thyroid gland, parathyroid glands, pancreas, adrenal glands, ovaries, and testes), diabetes (e.g., diabetes insipidus, type I and type II diabetes mellitus), obesity, disorders related to pituitary glands (e.g., hyperpituitarism, hypopituitarism, and pituitary dwarfism), hypothyroidism, hyperthyroidism, goiter, reproductive disorders (e.g. male and female infertility), disorders related to adrenal glands (e.g., Addison's Disease, corticosteroid deficiency, and Cushing's Syndrome), kidney cancer (e.g., hypernephroma, transitional cell cancer, and Wilm's tumor), diabetic nephropathy, interstitial nephritis, polycystic kidney disease, glomerulonephritis (e.g., IgM mesangial proliferative glomerulonephritis and glomerulonephritis caused by autoimmune disorders; such as Goodpasture's syndrome), and nephrocalcinosis.

The recitation of "Digestive" in the "Preferred Indication" column indicates that the corresponding nucleic acid and protein, or antibody against the same, of the invention (or fragment or variant thereof), may be used for example, to diagnose, treat, prevent, and/or ameliorate diseases and/or disorders relating to neoplastic diseases (e.g., as described below under "Hyperproliferative Disorders") and diseases or disorders of the gastrointestinal system (e.g., as described below under "Gastrointestinal Disorders".

In specific embodiments, a protein, nucleic acid, or antibody of the invention (or fragment or variant thereof) having a "Digestive" recitation in the "Preferred Indication" column of Table 1D, may be used for example, to diagnose, treat, prevent, and/or ameliorate a disease or disorder selected from the group consisting of: ulcerative colitis, appendicitis, Crohn's disease, hepatitis, hepatic encephalopathy, portal hypertension, cholelithiasis, cancer of the digestive system (e.g., biliary tract cancer, stomach cancer, colon cancer, gastric cancer, pancreatic cancer, cancer of the bile duct, tumors of the colon (e.g., polyps or cancers), and cirrhosis), pancreatitis, ulcerative disease, pyloric stenosis, gastroenteritis, gastritis, gastric atropy, benign tumors of the duodenum, distension, irritable bowel syndrome, malabsorption, congenital disorders of the small intestine, bacterial and parasitic infection, megacolon, Hirschsprung's disease, aganglionic megacolon, acquired megacolon, colitis, anorectal disorders (e.g., anal fistulas, hemorrhoids), congenital disorders of the liver (e.g., Wilson's disease, hemochromatosis, cystic fibrosis, biliary atresia, and alpha1-antitrypsin deficiency), portal hypertension, cholelithiasis, and jaundice.

The recitation of "Connective/Epithelial" in the "Preferred Indication" column indicates that the corresponding nucleic acid and protein, or antibody against the same, of the invention (or fragment or variant thereof), may be used for example, to diagnose, treat, prevent, and/or ameliorate diseases and/or disorders relating to neoplastic diseases (e.g., as described below under "Hyperproliferative Disorders"), cellular and genetic abnormalities (e.g., as described below under "Diseases at the Cellular Level"), angiogenesis (e.g., as described below under "Anti-Angiogenesis Activity"), and or to promote or inhibit regeneration (e.g., as described below under "Regeneration"), and wound healing (e.g., as described below under "Wound Healing and Epithelial Cell Proliferation").

In specific embodiments, a protein, nucleic acid, or antibody of the invention (or fragment or variant thereof) having a "Connective/Epithelial" recitation in the "Preferred Indication" column of Table 1D, may be used for example, to diagnose, treat, prevent, and/or ameliorate a disease or disorder selected from the group consisting of: connective tissue metaplasia, mixed connective tissue disease, focal epithelial hyperplasia, epithelial metaplasia, mucoepithelial dysplasia, graft v. host disease, polymyositis, cystic hyperplasia, cerebral dysplasia, tissue hypertrophy, Alzheimer's disease, lymphoproliferative disorder, Waldenstron's macroglobulinemia, Crohn's disease, pernicious anemia, idiopathic Addison's disease, glomerulonephritis, bullous pemphigoid, Sjogren's syndrome, diabetes mellitus, cystic fibrosis, osteoblastoma, osteoclastoma, osteosarcoma, chondrosarcoma, osteoporosis, osteocarthritis, periodontal disease, wound healing, relapsing polychondritis, vasculitis, polyarteritis nodosa, Wegener's granulomatosis, cellulitis, rheumatoid arthritis, psoriatic arthritis, discoid lupus erythematosus, systemic lupus erythematosus, scleroderma, CREST syndrome, Sjogren's syndrome, polymyositis, dermatomyositis, mixed connective tissue disease, relapsing polychondritis, vasculitis, Henoch-Schonlein syndrome, erythema nodosum, polyarteritis nodosa, temporal (giant cell) arteritis, Takayasu's arteritis, Wegener's granulomatosis, Reiter's syndrome, Behcet's syndrome, ankylosing spondylitis, cellulitis, keloids, Ehler Danlos syndrome, Marfan syndrome, pseudoxantoma elasticum, osteogenese imperfecta, chondrodysplasias, epidermolysis bullosa, Alport syndrome, and cutis laxa.

Table 1E provides information related to biological activities and preferred indications for polynucleotides and polypeptides of the invention (including antibodies, agonists, and/or antagonists thereof). Table 1E also provides information related to assays which may be used to test polynucleotides and polypeptides of the invention (including antibodies, agonists, and/or antagonists thereof) for the corresponding biological activities. The first column ("Gene No.") provides the gene number in the application for each clone identifier. The second column ("cDNA Clone ID:") provides the unique clone identifier for each clone as previously described and indicated in Tables 1A, 1B.1, 1B.2, 1C, and 1D. The third column ("AA SEQ ID NO:Y") indicates the Sequence Listing SEQ ID Number for polypeptide sequences encoded by the corresponding cDNA clones (also as indicated in Tables 1A and 1B.1). The fourth column ("Biological Activity") indicates a biological activity corresponding to the indicated polypeptides (or polynucleotides encoding said polypeptides). The fifth column ("Exemplary Activity Assay") further describes the corresponding biological activity and provides information pertaining to the various types of assays which may be performed to test, demonstrate, or quantify the corresponding biological activity. The sixth column ("Preferred Indications") describes particular embodiments of the invention and indications (e.g. pathologies, diseases, disorders, abnormalities, etc.) for which polynucleotides and polypeptides of the invention (including antibodies, agonists, and/or antagonists thereof) may be used in detecting, preventing, diagnosing, prognosticating, treating, and/or ameliorating.

Tables 1E.1 and 1E.2 provide information related to biological activities for polynucleotides and polypeptides of the invention (including antibodies, agonists, and/or antagonists thereof). Tables 1E.2 also provide information related to assays which may be used to test polynucleotides and polypeptides of the invention (including antibodies, agonists, and/or antagonists thereof) for the corresponding biological activities. The first column of Table 1E.1 ("Gene No.") provides the gene number in the application for each clone identifier. The second column of Table 1E.1 ("cDNA Clone ID:") provides the unique clone identifier for each clone as previously described and indicated in Tables 1A, 1B.1, 1B.2, and 1C. The third column of Table 1E.1 ("AA SEQ ID NO:Y") indicates the Sequence Listing SEQ ID Number for polypeptide sequences encoded by the corresponding cDNA clones (also as indicated in Tables 1A and 1B.1). The fourth column of Table 1E.1 ("Biological Activity") indicates a biological activity corresponding to the indicated polypeptides (or polynucleotides encoding said polypeptides).

In Table 1E.2, each of the biological activities of Table 1E.1 are listed by "Biological Activity Number" and the corresponding "Biological Activity" and are followed by an "Exemplary Activity Assay" column and a "Preferred Indication" column; however, for some biological activities no "Exemplary Activity Assay" or "Preferred Indication" is given. The "Exemplary Activity Assay" column describes the biological activity listed in the column that precedes it and also provides information pertaining to the various types of assays which may be performed to test, demonstrate, or quantify the corresponding biological activity. The "Preferred Indication" column also refers to the biological activity listed in the preceding column and describes disease(s) or disorder(s) that may be detected, diagnosed, prevented, treated, or ameliorated by the nucleic acids and proteins (or antibodies against the same) of the invention (including polynucleotide, polypeptide, and antibody fragments or variants thereof).

Tables 1E, 1E.1, and 1E.2 describe the use of FMAT technology, inter alia, for testing or demonstrating various biological activities. Fluorometric microvolume assay technology (FMAT) is a fluorescence-based system that provides a means to perform nonradioactive cell- and bead-based assays to detect activation of cell signal transduction pathways. This technology was designed specifically for ligand binding and immunological assays. Using this technology, fluorescent cells or beads at the bottom of the well are detected as localized areas of concentrated fluorescence using a data processing system. Unbound fluorophore comprising the background signal is ignored, allowing for a wide variety of homogeneous assays. FMAT technology may be used for peptide ligand binding assays, immunofluorescence, apoptosis, cytotoxicity, and bead-based immunocapture assays. See, Miraglia S et. al., "Homogeneous cell and bead based assays for high throughput screening using fluorometric microvolume assay technology," Journal of Biomolecular Screening; 4:193-204 (1999). In particular, FMAT technology may be used to test, confirm, and/or identify the ability of polypeptides (including polypeptide fragments and variants) to activate signal transduction pathways. For example, FMAT technology may be used to test, confirm, and/or identify the ability of polypeptides to upregulate production of immunomodulatory proteins (such as, for example, interleukins, GM-CSF, Rantes, and Tumor Necrosis factors, as well as other cellular regulators (e.g. insulin)).

Tables 1E, 1E.1, and 1E.2 also describe the use of kinase assays for testing, demonstrating, or quantifying biological activity. In this regard, the phosphorylation and de-phosphorylation of specific amino acid residues (e.g. Tyrosine, Serine, Threonine) on cell-signal transduction proteins provides a fast, reversible means for activation and de-activation of cellular signal transduction pathways. Moreover, cell signal transduction via phosphorylation/de-phosphorylation is crucial to the regulation of a wide variety of cellular processes (e.g. proliferation, differentiation, migration, apoptosis, etc.). Accordingly, kinase assays provide a powerful tool useful for testing, confirming, and/or identifying polypeptides (including polypeptide fragments and variants) that mediate cell signal transduction events via protein phosphorylation. See e.g., Forrer, P., Tamaskovic R., and Jaussi, R. "Enzyme-Linked Immunosorbent Assay for Measurement of JNK, ERK, and p38 Kinase Activities" Biol. Chem. 379(8-9): 1101-1110 (1998).

Description of Table 1F

Polynucleotides encoding polypeptides of the present invention can be used in assays to test for one or more biological activities. One such biological activity which may be tested includes the ability of polynucleotides and polypeptides of the invention to stimulate up-regulation or down-regulation of expression of particular genes and proteins. Hence, if polynucleotides and polypeptides of the present invention exhibit activity in altering particular gene and protein expression patterns, it is likely that these polynucleotides and polypeptides of the present invention may be involved in, or capable of effecting changes in, diseases associated with the altered gene and protein expression profiles. Hence, polynucleotides, polypeptides, or antibodies of the present invention could be used to treat said associated diseases.

TaqMan® assays may be performed to assess the ability of polynucleotides (and polypeptides they encode) to alter the expression pattern of particular "target" genes. TaqMan® reactions are performed to evaluate the ability of a test agent to induce or repress expression of specific genes in different cell types. TaqMan® gene expression quantification assays ("TaqMan® assays") are well known to, and routinely performed by, those of ordinary skill in the art. TaqMan® assays are performed in a two step reverse transcription/polymerase chain reaction (RT-PCR). In the first (RT) step, cDNA is reverse transcribed from total RNA samples using random hexamer primers. In the second (PCR) step, PCR products are synthesized from the cDNA using gene specific primers.

To quantify gene expression the TaqMan® PCR reaction exploits the 5' nuclease activity of AmpliTaq Gold® DNA Polymerase to cleave a TaqMan® probe (distinct from the primers) during PCR. The TaqMan® probe contains a reporter dye at the 5'-end of the probe and a quencher dye at the 3' end of the probe. When the probe is intact, the proximity of the reporter dye to the quencher dye results in suppression of the reporter fluorescence. During PCR, if the target of interest is present, the probe specifically anneals between the forward and reverse primer sites. AmpliTaq Gold® DNA Polymerase then cleaves the probe between the reporter and quencher when the probe hybridizes to the target, resulting in increased fluorescence of the reporter (see FIG. 2). Accumulation of PCR products is detected directly by monitoring the increase in fluorescence of the reporter dye.

After the probe fragments are displaced from the target, polymerization of the strand continues. The 3'-end of the probe is blocked to prevent extension of the probe during PCR. This process occurs in every cycle and does not interfere with the exponential accumulation of product. The increase in fluorescence signal is detected only if the target sequence is complementary to the probe and is amplified during PCR. Because of these requirements, any nonspecific amplification is not detected.

For test sample preparation, vector controls or constructs containing the coding sequence for the gene of interest are transfected into cells, such as for example 293T cells, and supernatants collected after 48 hours. For cell treatment and RNA isolation, multiple primary human cells or human cell lines are used; such cells may include but are not limited to, Normal Human Dermal Fibroblasts, Aortic Smooth Muscle, Human Umbilical Vein Endothelial Cells, HepG2, Daudi, Jurkat, U937, Caco, and THP-1 cell lines. Cells are plated in growth media and growth is arrested by culturing without media change for 3 days, or by switching cells to low serum media and incubating overnight. Cells are treated for 1, 6, or 24 hours with either vector control supernatant or sample supernatant (or purified/partially purified protein preparations in buffer). Total RNA is isolated; for example, by using TRIZOL™ extraction or by using the Ambion RNAqueous™-4PCR RNA isolation system. Expression levels of multiple genes are analyzed using TaqMan®, and expression in the test sample is compared to control vector samples to identify genes induced or repressed. Each of the above described techniques are well known to, and routinely performed by, those of ordinary skill in the art.

Table 1F indicates particular disease classes and preferred indications for which polynucleotides, polypeptides, or antibodies of the present invention may be used in detecting, diagnosing, preventing, treating and/or ameliorating said diseases and disorders based on "target" gene expression patterns which may be up- or down-regulated by polynucleotides (and the encoded polypeptides) corresponding to each indicated cDNA Clone ID (shown in Table 1F, Column 2).

Thus, in preferred embodiments, the present invention encompasses a method of detecting, diagnosing, preventing, treating, and/or ameliorating a disease or disorder listed in the "Disease Class" and/or "Preferred Indication" columns of Table 1F; comprising administering to a patient in which such detection, diagnosis, prevention, or treatment is desired a protein, nucleic acid, or antibody of the invention (or fragment or variant thereof) in an amount effective to detect, diagnose, prevent, treat, or ameliorate the disease or disorder. The first and second columns of Table 1F show the "Gene No." and "cDNA Clone ID No.", respectively, indicating certain nucleic acids and proteins (or antibodies against the same) of the invention (including polynucleotide, polypeptide, and antibody fragments or variants thereof) that may be used in detecting, diagnosing, preventing, treating, or ameliorating the disease(s) or disorder(s) indicated in the corresponding row in the "Disease Class" or "Preferred Indication" Columns of Table 1F.

In another embodiment, the present invention also encompasses methods of detecting, diagnosing, preventing, treating, or ameliorating a disease or disorder listed in the "Disease Class" or "Preferred Indication" Columns of Table 1F; comprising administering to a patient combinations of the proteins, nucleic acids, or antibodies of the invention (or fragments or variants thereof), sharing similar indications as shown in the corresponding rows in the "Disease Class" or "Preferred Indication" Columns of Table 1F.

The "Disease Class" Column of Table 1F provides a categorized descriptive heading for diseases, disorders, and/or conditions (more fully described below) that may be detected, diagnosed, prevented, treated, or ameliorated by a protein, nucleic acid, or antibody of the invention (or fragment or variant thereof).

The "Preferred Indication" Column of Table 1F describes diseases, disorders, and/or conditions that may be detected, diagnosed, prevented, treated, or ameliorated by a protein, nucleic acid, or antibody of the invention (or fragment or variant thereof).

The "Cell Line" and "Exemplary Targets" Columns of Table 1F indicate particular cell lines and target genes, respectively, which may show altered gene expression patterns (i.e., up- or down-regulation of the indicated target gene) in TaqMan® assays, performed as described above, utilizing polynucleotides of the cDNA Clone ID shown in the corresponding row. Alteration of expression patterns of the indicated "Exemplary Target" genes is correlated with a particular "Disease Class" and/or "Preferred Indication" as shown in the corresponding row under the respective column headings.

The "Exemplary Accessions" Column indicates GenBank Accessions (available online through the National Center for Biotechnology Information (NCBI) at the world wide web at ncbi.nlm.nih.gov/) which correspond to the "Exemplary Targets" shown in the adjacent row.

The recitation of "Cancer" in the "Disease Class" Column indicates that the corresponding nucleic acid and protein, or antibody against the same, of the invention (or fragment or variant thereof) may be used for example, to detect, diagnose, prevent, treat, and/or ameliorate neoplastic diseases and/or disorders (e.g., leukemias, cancers, etc., as described below under "Hyperproliferative Disorders").

The recitation of "Immune" in the "Disease Class" column indicates that the corresponding nucleic acid and protein, or antibody against the same, of the invention (or fragment or variant thereof), may be used for example, to detect, diagnose, prevent, treat, and/or ameliorate diseases and/or disorders relating to neoplastic diseases (e.g., as described below under "Hyperproliferative Disorders"), blood disorders (e.g., as described below under "Immune Activity" "Cardiovascular Disorders" and/or "Blood-Related Disorders"), and infections (e.g., as described below under "Infectious Disease").

The recitation of "Angiogenesis" in the "Disease Class" column indicates that the corresponding nucleic acid and protein, or antibody against the same, of the invention (or fragment or variant thereof), may be used for example, to detect, diagnose, treat, prevent, and/or ameliorate diseases and/or disorders relating to neoplastic diseases (e.g., as described below under "Hyperproliferative Disorders"), diseases and/or disorders of the cardiovascular system (e.g., as described below under "Cardiovascular Disorders"), diseases and/or disorders involving cellular and genetic abnormalities (e.g., as described below under "Diseases at the Cellular Level"), diseases and/or disorders involving angiogenesis (e.g., as described below under "Anti-Angiogenesis Activity"), to promote or inhibit cell or tissue regeneration (e.g., as described below under "Regeneration"), or to promote wound healing (e.g., as described below under "Wound Healing and Epithelial Cell Proliferation"). Highly preferred indications include diagnosis, prevention, treatment, and/or amelioration of diseases and disorders involving angiogenesis, wound healing, neoplasia (particularly including, but not limited to, tumor metastases), and cardiovascular diseases and disorders; as described herein under the headings "Hyperproliferative Disorders," "Regeneration," "Anti-Angiogenesis Activity," "Diseases at the Cellular Level," and "Wound Healing and Epithelial Cell Proliferation."

The recitation of "Diabetes" in the "Disease Class" column indicates that the corresponding nucleic acid and protein, or antibody against the same, of the invention (or fragment or variant thereof), may be used for example, to detect, diagnose, treat, prevent, and/or ameliorate diabetes (including diabetes mellitus types I and II), as well as diseases and/or disorders associated with, or consequential to, diabetes (e.g. as described below under "Endocrine Disorders," "Renal Disorders," and "Gastrointestinal Disorders").

Description of Table 2

Table 2 summarizes homology and features of some of the polypeptides of the invention. The first column provides a unique clone identifier, "Clone ID:", corresponding to a cDNA clone disclosed in Tables 1A, 1B.1, and/or 1B.2. The second column provides the unique contig identifier, "Contig ID:" corresponding to contigs in Tables 1B.1 and 1B.2 and allowing for correlation with the information in Tables 1B.1 and 1B.2. The third column provides the sequence identifier, "SEQ ID NO:X", for the contig polynucleotide sequence. The fourth column provides the analysis method by which the homology/identity disclosed in the Table was determined. Comparisons were made between polypeptides encoded by the polynucleotides of the invention and either a non-redundant protein database (herein referred to as "NR"), or a database of protein families (herein referred to as "PFAM") as further described below. The fifth column provides a description of the PFAM/NR hit having a significant match to a polypeptide of the invention. Column six provides the accession number of the PFAM/NR hit disclosed in the fifth column. Column seven, "Score/Percent Identity", provides a quality score or the percent identity, of the hit disclosed in columns five and six. Columns 8 and 9, "NT From" and "NT To" respectively, delineate the polynucleotides in "SEQ ID NO:X" that encode a polypeptide having a significant match to the PFAM/NR database as disclosed in the fifth and sixth columns. In specific embodiments polypeptides of the invention comprise, or alternatively consist of, an amino acid sequence encoded by a polynucleotide in SEQ ID NO:X as delineated in columns 8 and 9, or fragments or variants thereof.

Description of Table 3

Table 3 provides polynucleotide sequences that may be disclaimed according to certain embodiments of the invention. The first column provides a unique clone identifier, "cDNA Clone ID", for a cDNA clone related to contig sequences disclosed in Tables 1B.1 and 1B.2. The second column provides the sequence identifier, "SEQ ID NO:X", for contig sequences disclosed in Tables 1A, 1B.1, and/or 1B.2. The third column provides the unique contig identifier, "Contig ID:", for contigs disclosed in Tables 1B.1 and 1B.2. In specific embodiments of the invention, for each "Contig ID" listed in the third column of Table 3, preferably excluded are one or more polynucleotides comprising, or alternatively consisting of, SEQ ID NO:X referenced in the second column of Table 3 and described by the general formula of a–b, whereas a and b are uniquely defined integers determined for the corresponding SEQ ID NO:X referred to in column 2 of Table 3. The fourth column provides a range of values for the unique integer 'a' where 'a' is any integer between 1 and the final nucleotide minus 15 of SEQ ID NO:X, and the fifth column provides a range of values for the unique integer 'b' where 'b' is any integer between 15 and the final nucleotide of SEQ ID NO:X, where both a and b correspond to the positions of nucleotide residues shown in SEQ ID NO:X, and where b is greater than or equal to a+14. In certain embodiments, preferably excluded from the invention are at least one, two, three, four, or more of the polynucleotide sequence(s) having the accession number(s) disclosed in the sixth column of Table 3 (including for example, published sequence in connection with a particular BAC clone). In further embodiments, preferably excluded from the invention are at least five, ten, or more of the polynucleotide sequence(s) having the accession number(s) disclosed in the sixth column of this Table (including for example, published sequence in connection with a particular BAC clone). In further embodiments, preferably excluded from the invention are the specific polynucleotide sequence(s) contained in the clones corresponding to at least one, two, three, four, or more of the available material having the accession numbers identified in the sixth column of Table 3 (including for example, the actual sequence contained in an identified BAC clone). In further embodiments, preferably excluded from the invention are the specific polynucleotide sequence(s) contained in the clones corresponding to at least five, ten, or more of the available material having the accession numbers identified in the sixth column of Table 3 (including for example, the actual sequence contained in an identified BAC clone). In no way is this listing meant to encompass all of the sequences which may be excluded by the general formula, it is just a representative example. All references available through these accessions are hereby incorporated by reference in their entirety.

Description of Table 4

Table 4 provides a key to the tissue/cell source identifier code disclosed in Table 1B.2, column 5. Column 1 provides the tissue/cell source identifier code disclosed in Table 1B.2, column 5. Columns 2-5 provide a description of the tissue or cell source. Note that "Description" and "Tissue" sources (i.e. columns 2 and 3) having the prefix "a_" indicates organs, tissues, or cells derived from "adult" sources. Codes corresponding to diseased tissues are indicated in column 6 with the word "disease." The use of the word "disease" in column 6 is non-limiting. The tissue or cell source may be specific (e.g. a neoplasm), or may be disease-associated (e.g., a tissue sample from a normal portion of a diseased organ). Furthermore, tissues and/or cells lacking the "disease" designation may still be derived from sources directly or indirectly involved in a disease state or disorder, and therefore may have a further utility in that disease state or disorder. In numerous cases where the tissue/cell source is a library, column 7 identifies the vector used to generate the library.

Description of Table 5

Table 5 provides a key to the OMIM reference identification numbers disclosed in Table 1B.1, column 9. OMIM reference identification numbers (column 1) were derived from Online Mendelian Inheritance in Man (Online Mendelian Inheritance in Man, OMIM. McKusick-Nathans Institute for Genetic Medicine, Johns Hopkins University (Baltimore, Md.) and National Center for Biotechnology Information, National Library of Medicine, (Bethesda, Md.) 2000 (world wide web at ncbi.nlm.nih.gov/omim/). Column 2 provides diseases associated with the cytologic band disclosed in Table 1B.1, column 8 as determined using the Morbid Map database.

Description of Table 6

Table 6 summarizes some of the ATCC™ Deposits, Deposit dates, and ATCC™ designation numbers of deposits made with the ATCC™ in connection with the present application. These deposits were made in addition to those described in Table 1A.

Description of Table 7

Table 7 shows the cDNA libraries sequenced, and ATCC™ designation numbers and vector information relating to these cDNA libraries.

The first column shows the first four letters indicating the Library from which each library clone was derived. The second column indicates the catalogued tissue description for the corresponding libraries. The third column indicates the vector containing the corresponding clones. The fourth column shows the ATCC™ deposit designation for each library clone as indicated by the deposit information in Table 6.

Definitions

The following definitions are provided to facilitate understanding of certain terms used throughout this specification.

In the present invention, "isolated" refers to material removed from its original environment (e.g., the natural environment if it is naturally occurring), and thus is altered "by the hand of man" from its natural state. For example, an isolated polynucleotide could be part of a vector or a composition of matter, or could be contained within a cell, and still be "isolated" because that vector, composition of matter, or particular cell is not the original environment of the polynucleotide. The term "isolated" does not refer to genomic or cDNA libraries, whole cell total or mRNA preparations, genomic DNA preparations (including those separated by electrophoresis and transferred onto blots), sheared whole cell genomic DNA preparations or other compositions where the art demonstrates no distinguishing features of the polynucleotide/sequences of the present invention.

In the present invention, a "secreted" protein refers to those proteins capable of being directed to the ER, secretory vesicles, or the extracellular space as a result of a signal sequence, as well as those proteins released into the extracellular space without necessarily containing a signal sequence. If the secreted protein is released into the extracellular space, the secreted protein can undergo extracellular processing to produce a "mature" protein. Release into the extracellular space can occur by many mechanisms, including exocytosis and proteolytic cleavage.

As used herein, a "polynucleotide" refers to a molecule having a nucleic acid sequence encoding SEQ ID NO:Y or a fragment or variant thereof (e.g., the polypeptide delineated in columns fourteen and fifteen of Table 1A); a nucleic acid sequence contained in SEQ ID NO:X (as described in column 5 of Table 1A and/or column 4 of Tables 1B.1 and 1B.2) or the complement thereof a cDNA sequence contained in Clone ID: (as described in column 2 of Table 1A and/or Tables 1B.1 and 1B.2 and contained within a library deposited with the ATCC™); a nucleotide sequence encoding the polypeptide encoded by a nucleotide sequence in SEQ ID NO:B as defined in column 6 (EXON From-To) of Table 1C or a fragment or variant thereof or a nucleotide coding sequence in SEQ ID NO:B as defined in column 6 of Table 1C or the complement thereof. For example, the polynucleotide can contain the nucleotide sequence of the full length cDNA sequence, including the 5' and 3' untranslated sequences, the coding region (with or without a natural or artificial signal sequence), the protein coding region as well as fragments, epitopes, domains, and variants of the nucleic acid sequence. Moreover, as used herein, a "polypeptide" refers to a molecule having an amino acid sequence encoded by a polynucleotide of the invention as broadly defined (obviously excluding poly-Phenylalanine or poly-Lysine peptide sequences which result from translation of a polyA tail of a sequence corresponding to a cDNA).

In the present invention, "SEQ ID NO:X" was often generated by overlapping sequences contained in multiple clones (contig analysis). A representative clone containing all or most of the sequence for SEQ ID NO:X is deposited at Human Genome Sciences, Inc. (HGS) in a catalogued and archived library. As shown, for example, in column 2 of Tables 1B.1 and 1B.2, each clone is identified by a cDNA Clone ID (identifier generally referred to herein as Clone ID:). Each Clone ID is unique to an individual clone and the Clone ID is all the information needed to retrieve a given clone from the HGS library. Table 7 provides a list of the deposited cDNA libraries. One can use the Clone ID: to determine the library source by reference to Tables 6 and 7. Table 7 lists the deposited cDNA libraries by name and links each library to an ATCC™ Deposit. Library names contain four characters, for example, "HTWE." The name of a cDNA clone (Clone ID) isolated from that library begins with the same four characters, for example "HTWEP07". As mentioned below, Tables 1A, 1B.1 and 1B.2 correlate the Clone ID names with SEQ ID NO:X. Thus, starting with an SEQ ID NO:X, one can use Tables 1A, 1B.1, 1B.2, 6, and 7 to determine the corresponding Clone ID, which library it came from and which ATCC™ deposit the library is contained in. Furthermore, it is possible to retrieve a given cDNA clone from the source library by techniques known in the art and described elsewhere herein. The ATCC™ is located at 10801 University Boulevard, Manassas, Va. 20110-2209, USA. The ATCC™ deposits were made pursuant to the terms of the Budapest Treaty on the international recognition of the deposit of microorganisms for the purposes of patent procedure.

In specific embodiments, the polynucleotides of the invention are at least 15, at least 30, at least 50, at least 100, at least 125, at least 500, or at least 1000 continuous nucleotides but are less than or equal to 300 kb, 200 kb, 100 kb, 50 kb, 15 kb, 10 kb, 7.5 kb, 5 kb, 2.5 kb, 2.0 kb, or 1 kb, in length. In a further embodiment, polynucleotides of the invention comprise a portion of the coding sequences, as disclosed herein, but do not comprise all or a portion of any intron. In another embodiment, the polynucleotides comprising coding sequences do not contain coding sequences of a genomic flanking gene (i.e., 5' or 3' to the gene of interest in the genome). In other embodiments, the polynucleotides of the invention do not contain the coding sequence of more than 1000, 500, 250, 100, 50, 25, 20, 15, 10, 5, 4, 3, 2, or 1 genomic flanking gene(s).

A "polynucleotide" of the present invention also includes those polynucleotides capable of hybridizing, under stringent hybridization conditions, to sequences contained in SEQ ID NO:X, or the complement thereof (e.g., the complement of any one, two, three, four, or more of the polynucleotide fragments described herein), the polynucleotide sequence delineated in columns 7 and 8 of Table 1A or the complement thereof, the polynucleotide sequence delineated in columns 8 and 9 of Table 2 or the complement thereof, and/or cDNA sequences contained in Clone ID: (e.g., the complement of any one, two, three, four, or more of the polynucleotide fragments, or the cDNA clone within the pool of cDNA clones deposited with the ATCC™, described herein), and/or the polynucleotide sequence delineated in column 6 of Table 1C or the complement thereof. "Stringent hybridization conditions" refers to an overnight incubation at 42 degree C. in a solution comprising 50% formamide, 5×SSC (750 mM NaCl, 75 mM trisodium citrate), 50 mM sodium phosphate (pH 7.6), 5×Denhardt's solution, 10% dextran sulfate, and 20 μg/ml denatured, sheared salmon sperm DNA, followed by washing the filters in 0.1×SSC at about 65 degree C.

Also contemplated are nucleic acid molecules that hybridize to the polynucleotides of the present invention at lower stringency hybridization conditions. Changes in the stringency of hybridization and signal detection are primarily accomplished through the manipulation of formamide concentration (lower percentages of formamide result in lowered stringency); salt conditions, or temperature. For example, lower stringency conditions include an overnight incubation at 37 degree C. in a solution comprising 6×SSPE (20× SSPE=3M NaCl; 0.2M $NaH_2PO_4$; 0.02M EDTA, pH 7.4), 0.5% SDS, 30% formamide, 100 μg/ml salmon sperm blocking DNA; followed by washes at 50 degree C. with 1×SSPE, 0.1% SDS. In addition, to achieve even lower stringency, washes performed following stringent hybridization can be done at higher salt concentrations (e.g. 5×SSC).

Note that variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility.

Of course, a polynucleotide which hybridizes only to polyA+ sequences (such as any 3' terminal polyA+ tract of a cDNA shown in the sequence listing), or to a complementary stretch of T (or U) residues, would not be included in the definition of "polynucleotide," since such a polynucleotide would hybridize to any nucleic acid molecule containing a poly (A) stretch or the complement thereof (e.g., practically any double-stranded cDNA clone generated using oligo dT as a primer).

The polynucleotide of the present invention can be composed of any polyribonucleotide or polydeoxyribonucleotide, which may be unmodified RNA or DNA or modified RNA or DNA. For example, polynucleotides can be composed of single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, the polynucleotide can be composed of triple-stranded regions comprising RNA or DNA or both RNA and DNA. A polynucleotide may also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

In specific embodiments, the polynucleotides of the invention are at least 15, at least 30, at least 50, at least 100, at least 125, at least 500, or at least 1000 continuous nucleotides but are less than or equal to 300 kb, 200 kb, 100 kb, 50 kb, 15 kb, 10 kb, 7.5 kb, 5 kb, 2.5 kb, 2.0 kb, or 1 kb, in length. In a further embodiment, polynucleotides of the invention comprise a portion of the coding sequences, as disclosed herein, but do not comprise all or a portion of any intron. In another embodiment, the polynucleotides comprising coding sequences do not contain coding sequences of a genomic flanking gene (i.e., 5' or 3' to the gene of interest in the genome). In other embodiments, the polynucleotides of the invention do not contain the coding sequence of more than 1000, 500, 250, 100, 50, 25, 20, 15, 10, 5, 4, 3, 2, or 1 genomic flanking gene(s).

The polypeptide of the present invention can be composed of amino acids joined to each other by peptide bonds or modified peptide bonds, i.e., peptide isosteres, and may contain amino acids other than the 20 gene-encoded amino acids. The polypeptides may be modified by either natural processes, such as posttranslational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched, for example, as a result of ubiquitination, and they may be cyclic, with or without branching. Cyclic, branched, and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, PROTEINS—STRUCTURE AND MOLECULAR PROPERTIES, 2nd Ed., T. E. Creighton, W. H. Freeman and Company, New York (1993); POSTTRANSLATIONAL COVALENT MODIFICATION OF PROTEINS, B. C. Johnson, Ed., Academic Press, New York, pgs. 1-12 (1983); Seifter et al., Meth. Enzymol. 182: 626-646 (1990); Rattan et al., Ann. N.Y. Acad. Sci. 663:48-62 (1992)).

"SEQ ID NO:X" refers to a polynucleotide sequence described, for example, in Tables 1A, 1B.1, 1B.2, 1C, 2, and/or 3, while "SEQ ID NO:Y" refers to a polypeptide sequence described in, for example, column 11 of Table 1A; column 6 of Table 1B.1; and/or column 3 of Table 1E or 1E.1. SEQ ID NO:X is identified by an integer specified in, for example, column 5 of Table 1A; column 4 of Table 1B.1 or 1B.2; column 2 of Table 1C; column 3 of Table 2; and/or column 2 of Table 3. The polypeptide sequence SEQ ID NO:Y is a translated open reading frame (ORF) encoded by polynucleotide SEQ ID NO:X. "Clone ID:" refers to a cDNA clone described in, for example, column 2 of Tables 1A, 1B.1, 1B.2, 1D, 1E, 1E.1, and/or 1F; and/or column 1 of Table 1C, 2, and/or 3.

"A polypeptide having functional activity" refers to a polypeptide capable of displaying one or more known functional activities associated with a full-length (complete) protein. Such functional activities include, but are not limited to, biological activity (e.g. activity useful in treating, preventing and/or ameliorating diseases and disorders such as immune, cardiovascular, cancer, and other proliferative diseases and disorders), antigenicity (ability to bind [or compete with a polypeptide for binding] to an anti-polypeptide antibody), immunogenicity (ability to generate antibody which binds to a specific polypeptide of the invention), ability to form multimers with polypeptides of the invention, and ability to bind to a receptor or ligand for a polypeptide.

The polypeptides of the invention can be assayed for functional activity (e.g. biological activity) using or routinely modifying assays known in the art, as well as assays described herein. Specifically, one of skill in the art may routinely assay secreted polypeptides (including fragments, variants, derivatives, and analogs) of the invention for activity using assays as described in the examples section below.

"A polypeptide having biological activity" refers to a polypeptide exhibiting activity similar to, but not necessarily identical to, an activity of a polypeptide of the present invention, including mature forms, as measured in a particular biological assay, with or without dose dependency. In the case where dose dependency does exist, it need not be identical to that of the polypeptide, but rather substantially similar to the dose-dependence in a given activity as compared to the polypeptide of the present invention (i.e., the candidate polypeptide will exhibit greater activity or not more than about 25-fold less and, preferably, not more than about tenfold less activity, and most preferably, not more than about three-fold less activity relative to the polypeptide of the present invention).

Tables

Table 1A

Table 1A summarizes information concerning certain polynucleotides and polypeptides of the invention. The first column provides the gene number in the application for each clone identifier. The second column provides a unique clone identifier, "Clone ID:", for a cDNA clone related to each contig sequence disclosed in Table 1A. Third column, the cDNA Clones identified in the second column were deposited as indicated in the third column (i.e. by ATCC™ Deposit No:Z and deposit date). Some of the deposits contain multiple different clones corresponding to the same gene. In the fourth column, "Vector" refers to the type of vector contained in the corresponding cDNA Clone identified in the second column. In the fifth column, the nucleotide sequence identified as "NT SEQ ID NO:X" was assembled from partially homologous ("overlapping") sequences obtained from the corresponding cDNA clone identified in the second column and, in some cases, from additional related cDNA clones. The overlapping sequences were assembled into a single contiguous sequence of high redundancy (usually three to five overlapping sequences at each nucleotide position), resulting in a final sequence identified as SEQ ID NO:X. In the sixth column, "Total NT Seq." refers to the total number of nucleotides in the contig sequence identified as SEQ ID NO:X." The deposited clone may contain all or most of these sequences, reflected by the nucleotide position indicated as "5' NT of Clone Seq." (seventh column) and the "3' NT of Clone Seq." (eighth column) of SEQ ID NO:X. In the ninth column, the nucleotide position of SEQ ID NO:X of the putative start codon (methionine) is identified as "5' NT of Start Codon." Similarly, in column ten, the nucleotide position of SEQ ID NO:X of the predicted signal sequence is identified as "5' NT of First AA of Signal Pep." In the eleventh column, the translated amino acid sequence, beginning with the methionine, is identified as "AA SEQ ID NO:Y," although other reading frames can also be routinely translated using known molecular biology techniques. The polypeptides produced by these alternative open reading frames are specifically contemplated by the present invention.

In the twelfth and thirteenth columns of Table 1A, the first and last amino acid position of SEQ ID NO:Y of the predicted signal peptide is identified as "First AA of Sig Pep" and "Last AA of Sig Pep." In the fourteenth column, the predicted first amino acid position of SEQ ID NO:Y of the secreted portion is identified as "Predicted First AA of Secreted Portion". The amino acid position of SEQ ID NO:Y of the last amino acid encoded by the open reading frame is identified in the fifteenth column as "Last AA of ORF".

SEQ ID NO:X (where X may be any of the polynucleotide sequences disclosed in the sequence listing) and the translated SEQ ID NO:Y (where Y may be any of the polypeptide sequences disclosed in the sequence listing) are sufficiently accurate and otherwise suitable for a variety of uses well known in the art and described further below. For instance, SEQ ID NO:X is useful for designing nucleic acid hybridization probes that will detect nucleic acid sequences contained in SEQ ID NO:X or the cDNA contained in the deposited clone. These probes will also hybridize to nucleic acid molecules in biological samples, thereby enabling a variety of forensic and diagnostic methods of the invention. Similarly, polypeptides identified from SEQ ID NO:Y may be used, for example, to generate antibodies which bind specifically to proteins containing the polypeptides and the secreted proteins encoded by the cDNA clones identified in Table 1A and/or elsewhere herein.

Nevertheless, DNA sequences generated by sequencing reactions can contain sequencing errors. The errors exist as misidentified nucleotides, or as insertions or deletions of nucleotides in the generated DNA sequence. The erroneously inserted or deleted nucleotides cause frame shifts in the reading frames of the predicted amino acid sequence. In these cases, the predicted amino acid sequence diverges from the actual amino acid sequence, even though the generated DNA sequence may be greater than 99.9% identical to the actual DNA sequence (for example, one base insertion or deletion in an open reading frame of over 1000 bases).

Accordingly, for those applications requiring precision in the nucleotide sequence or the amino acid sequence, the present invention provides not only the generated nucleotide sequence identified as SEQ ID NO:X, and the predicted translated amino acid sequence identified as SEQ ID NO:Y, but also a sample of plasmid DNA containing a human cDNA of the invention deposited with the ATCC™, as set forth in Table 1A. The nucleotide sequence of each deposited plasmid can readily be determined by sequencing the deposited plasmid in accordance with known methods The predicted amino acid sequence can then be verified from such deposits. Moreover, the amino acid sequence of the protein encoded by a particular plasmid can also be directly determined by peptide sequencing or by expressing the protein in a suitable host cell containing the deposited human cDNA, collecting the protein, and determining its sequence.

Also provided in Table 1A is the name of the vector which contains the cDNA plasmid. Each vector is routinely used in the art. The following additional information is provided for convenience.

Vectors Lambda Zap (U.S. Pat. Nos. 5,128,256 and 5,286,636), Uni-Zap XR (U.S. Pat. Nos. 5,128,256 and 5,286,636), Zap Express (U.S. Pat. Nos. 5,128,256 and 5,286,636), pBLUESCRIPT™ (pBS) (Short, J. M. et al., *Nucleic Acids Res.* 16:7583-7600 (1988); Alting-Mees, M. A. and Short, J. M., *Nucleic Acids Res.* 17:9494 (1989)) and pBK (Alting-Mees, M. A. et al., *Strategies* 5:58-61 (1992)) are commercially available from STRATAGENE™ Cloning Systems, Inc., 11011 N. Torrey Pines Road, La Jolla, Calif., 92037. pBS contains an ampicillin resistance gene and pBK contains a neomycin resistance gene. Phagemid pBS may be excised from the Lambda Zap and Uni-Zap XR vectors, and phagemid pBK may be excised from the Zap Express vector. Both phagemids may be transformed into *E. coli* strain XL-1 Blue, also available from STRATAGENE™.

Vectors pSport1, pCMVSport 1.0, pCMVSport 2.0 and pCMVSport 3.0, were obtained from LIFE TECHNOLOGIES™, Inc., P.O. Box 6009, Gaithersburg, Md. 20897. All Sport vectors contain an ampicillin resistance gene and may be transformed into *E. coli* strain DH10B, also available from LIFE TECHNOLOGIES™. See, for instance, Gruber, C. E., et al., *Focus* 15:59 (1993). Vector lafmid BA (Bento Soares, Columbia University, New York, N.Y.) contains an ampicillin resistance gene and can be transformed into *E. coli* strain XL-1 Blue. Vector pCR®2.1, which is available from Invitrogen, 1600 Faraday Avenue, Carlsbad, Calif. 92008, contains an ampicillin resistance gene and may be transformed into *E. coli* strain DH10B, available from LIFE TECHNOLOGIES™. See, for instance, Clark, J. M., *Nuc. Acids Res.* 16:9677-9686 (1988) and Mead, D. et al., *Bio/Technology* 9: (1991).

The present invention also relates to the genes corresponding to SEQ ID NO:X, SEQ ID NO:Y, and/or a deposited cDNA (cDNA Clone ID). The corresponding gene can be isolated in accordance with known methods using the sequence information disclosed herein. Such methods include, but are not limited to, preparing probes or primers from the disclosed sequence and identifying or amplifying the corresponding gene from appropriate sources of genomic material.

Also provided in the present invention are allelic variants, orthologs, and/or species homologs. Procedures known in the art can be used to obtain full-length genes, allelic variants, splice variants, full-length coding portions, orthologs, and/or species homologs of genes corresponding to SEQ ID NO:X and SEQ ID NO:Y using information from the sequences disclosed herein or the clones deposited with the ATCC™. For example, allelic variants and/or species homologs may be isolated and identified by making suitable probes or primers from the sequences provided herein and screening a suitable nucleic acid source for allelic variants and/or the desired homologue.

The present invention provides a polynucleotide comprising, or alternatively consisting of, the nucleic acid sequence of SEQ ID NO:X and/or a cDNA contained in ATCC™ Deposit No:Z. The present invention also provides a polypeptide comprising, or alternatively, consisting of, the polypeptide sequence of SEQ ID NO:Y, a polypeptide encoded by SEQ ID NO:X, and/or a polypeptide encoded by a cDNA contained in ATCC™ Deposit No:Z. Polynucleotides encoding a polypeptide comprising, or alternatively consisting of the polypeptide sequence of SEQ ID NO:Y, a polypeptide encoded by SEQ ID NO:X and/or a polypeptide encoded by the cDNA contained in ATCC™ Deposit No:Z, are also encompassed by the invention. The present invention further encompasses a polynucleotide comprising, or alternatively consisting of the complement of the nucleic acid sequence of SEQ ID NO:X, and/or the complement of the coding strand of the cDNA contained in ATCC™ Deposit No:Z.

TABLE 1A

| Gene No. | cDNA Clone ID | ATCC ™ Deposit No: Z and Date | Vector | NT SEQ ID NO: X | Total NT Seq. | 5' NT of Clone Seq. | 3' NT of Clone Seq. | 5' NT of Start Codon | 5' NT of First AA of Signal Pep | AA SEQ ID NO: Y | First AA of Sig Pep | Last AA of Sig Pep | First AA of Secreted Portion | Last AA of ORF |
|---|---|---|---|---|---|---|---|---|---|---|---|---|---|---|
| 1 | HNFIP24 | 97903<br>Feb. 26, 1997<br>209049<br>May 15, 1997 | pBluescript ™ | 1 | 902 | 46 | 816 | 19 | 19 | 2 | 1 | 26 | 27 | 234 |
| 2 | HETBY74 | 97904<br>Feb. 26, 1997<br>209050<br>May 15, 1997 | Uni-ZAP XR | 7 | 1923 | 30 | 1923 | 45 | 45 | 8 | 1 | 33 | 34 | 193 |
| 3 | HTEEB42 | 97922<br>Mar. 7, 1997<br>209070<br>May 22, 1997 | Uni-ZAP XR | 9 | 1022 | 20 | 1022 | 59 | 59 | 10 | 1 | 22 | 23 | 298 |
| 4 | HEMCM42 | 97978<br>Mar. 27, 1997<br>209075<br>May 22, 1997 | Uni-ZAP XR | 11 | 1041 | 48 | 1007 | 58 | 58 | 12 | 1 | 29 | 30 | 113 |
| 4 | HEQCC55 | 209965<br>Jun. 11, 1998 | pCMVSport 3.0 | 13 | 1052 | 30 | 1052 | 62 | 62 | 14 | 1 | 27 | 28 | 112 |
| 4 | HEQCC55 | 209965<br>Jun. 11, 1998 | pCMVSport 3.0 | 15 | 1000 | 1 | 1000 | 25 | 25 | 16 | 1 | 27 | 28 | 129 |
| 4 | HEMCM42 | 97978<br>Mar. 27, 1997<br>209075<br>May 22, 1997 | Uni-ZAP XR | 15 | 1000 | 1 | 1000 | 25 | 25 | 16 | 1 | 27 | 28 | 129 |
| 4 | HEQCC55 | 209965<br>Jun. 11, 1998 | pCMVSport 3.0 | 17 | 1037 | 1 | 1037 | 57 | 57 | 18 | 1 | 27 | 28 | 155 |
| 5 | HEMAE80 | 97975<br>Apr. 4, 1997<br>209081<br>May 29, 1997 | Uni-ZAP XR | 20 | 996 | 1 | 945 | 12 | 12 | 21 | 1 | 24 | 25 | 136 |

TABLE 1A-continued

| Gene No. | cDNA Clone ID | ATCC ™ Deposit No: Z and Date | Vector | NT SEQ ID NO: X | Total NT Seq. | 5' NT of Clone Seq. | 3' NT of Clone Seq. | 5' NT of Start Codon | 5' NT of First AA of Signal Pep | AA SEQ ID NO: Y | First AA of Sig Pep | Last AA of Sig Pep | First AA of Secreted Portion | Last AA of ORF |
|---|---|---|---|---|---|---|---|---|---|---|---|---|---|---|
| 5 | HEMAE80 | 97975<br>Apr. 4, 1997<br>209081<br>May 29, 1997 | Uni-ZAP XR | 22 | 1092 | 1 | 1092 | 61 | 61 | 23 | 1 | 24 | 25 | 136 |
| 6 | HRDFB85 | 97977<br>Apr. 4, 1997<br>209082<br>May 29, 1997 | Uni-ZAP XR | 28 | 1705 | 23 | 1697 | 233 | 233 | 29 | 1 | 21 | 22 | 201 |
| 7 | HDTAW95 | 209007<br>Apr. 28, 1997<br>209083<br>May 29, 1997 | pCMVSport 2.0 | 38 | 1288 | 412 | 1288 | 571 | 571 | 39 | 1 | | | 16 |
| 8 | HEMCV19 | 209010<br>Apr. 28, 1997<br>209085<br>May 29, 1997 | Uni-ZAP XR | 46 | 941 | 33 | 931 | 79 | 79 | 47 | 1 | 23 | 24 | 178 |
| 8 | HEMCV19 | 209010<br>Apr. 28, 1997<br>209085<br>May 29, 1997 | Uni-ZAP XR | 48 | 736 | 1 | 736 | 84 | 84 | 49 | 1 | 22 | 23 | 181 |
| 8 | HEMCV19 | 209010<br>Apr. 28, 1997<br>209085<br>May 29, 1997 | Uni-ZAP XR | 50 | 864 | 1 | 864 | 125 | 125 | 51 | 1 | 21 | 22 | 185 |
| 9 | HETBX14 | 209010<br>Apr. 28, 1997<br>209085<br>May 29, 1997 | Uni-ZAP XR | 61 | 1292 | 303 | 1292 | 207 | 207 | 62 | 1 | 18 | 19 | 250 |
| 9 | HETBX14 | 209010<br>Apr. 28, 1997<br>209085<br>May 29, 1997 | Uni-ZAP XR | 63 | 1146 | 157 | 1146 | | 74 | 64 | 1 | 13 | 14 | 53 |
| 9 | HETBX14 | 209010<br>Apr. 28, 1997<br>209085<br>May 29, 1997 | Uni-ZAP XR | 65 | 1146 | 157 | 1146 | | 74 | 66 | 1 | 14 | 15 | 53 |
| 10 | HLHSK94 | 209011<br>Apr. 28, 1997 | pBluescript ™ | 70 | 1974 | 1 | 1794 | 112 | 112 | 71 | 1 | 26 | 27 | 379 |
| 10 | HLHSK94 | 209011<br>Apr. 28, 1997 | pBluescript | 72 | 1789 | 1 | 1789 | 112 | 112 | 73 | 1 | 25 | 26 | 379 |
| 10 | HLHSK94 | 209011<br>Apr. 28, 1997 | pBluescript | 74 | 1974 | 1 | 1794 | 112 | 112 | 75 | 1 | 25 | 26 | 379 |
| 11 | HLHFP03 | 209126<br>Jun. 19, 1997 | Uni-ZAP XR | 76 | 613 | 1 | 613 | 224 | 224 | 77 | 1 | 20 | 21 | 116 |
| 11 | HLHFP03 | 209126<br>Jun. 19, 1997 | Uni-ZAP XR | 78 | 613 | 1 | 613 | 224 | 224 | 79 | 1 | 19 | 20 | 116 |
| 12 | HHTLF25 | 209125<br>Jun. 19, 1997 | ZAP Express | 83 | 697 | 1 | 661 | 142 | 142 | 84 | 1 | 26 | 27 | 111 |
| 13 | HTADX17 | 209124<br>Jun. 19, 1997 | Uni-ZAP XR | 90 | 1140 | 22 | 1140 | 84 | 84 | 91 | 1 | 24 | 25 | 142 |
| 13 | HTADX17 | 209124<br>Jun. 19, 1997 | Uni-ZAP XR | 92 | 1147 | 0 | 1148 | 92 | 92 | 93 | 1 | 23 | 24 | 142 |
| 13 | HTADX17 | 209124<br>Jun. 19, 1997 | Uni-ZAP XR | 94 | 1140 | 22 | 1140 | 84 | 84 | 95 | 1 | 19 | 20 | 142 |
| 14 | HJACG02 | 209215<br>Aug. 21, 1997 | pBluescript SK− | 102 | 553 | 1 | 553 | 47 | 47 | 103 | 1 | 23 | 24 | 108 |
| 14 | HJACG02 | 209215<br>Aug. 21, 1997 | pBluescript SK− | 104 | 575 | 1 | 575 | 66 | 66 | 105 | 1 | 22 | 23 | 108 |
| 15 | HKGAJ54 | 209224<br>Aug. 28, 1997 | pSport1 | 107 | 1346 | 1 | 1346 | 31 | 31 | 108 | 1 | 27 | 28 | 303 |
| 15 | HKGAJ54 | 209224<br>Aug. 28, 1997 | pSport1 | 109 | 1332 | 1 | 1332 | 24 | 24 | 110 | 1 | 27 | 28 | 340 |
| 16 | HSVAK93 | 209563<br>Dec. 18, 1997 | Uni-ZAP XR | 116 | 571 | 1 | 571 | 21 | 21 | 117 | 1 | 24 | 25 | 183 |
| 16 | HE8CH92 | 209580<br>Jan. 14, 1998 | Uni-ZAP XR | 118 | 1282 | 1 | 1282 | 31 | 31 | 119 | 1 | 24 | 25 | 378 |
| 16 | HSVAK93 | 209563<br>Dec. 18, 1997 | Uni-ZAP XR | 120 | 1240 | 1 | 1240 | 24 | 24 | 121 | 1 | 24 | 25 | 378 |
| 17 | HSDEK49 | 209603<br>Jan. 29, 1998 | Uni-ZAP XR | 123 | 1590 | 96 | 1590 | 126 | 126 | 124 | 1 | 21 | 22 | 305 |
| 17 | HSDEK49 | 209603<br>Jan. 29, 1998 | Uni-ZAP XR | 125 | 1782 | 1 | 1782 | 60 | 60 | 126 | 1 | 19 | 20 | 399 |

TABLE 1A-continued

| Gene No. | cDNA Clone ID | ATCC ™ Deposit No: Z and Date | Vector | NT SEQ ID NO: X | Total NT Seq. | 5' NT of Clone Seq. | 3' NT of Clone Seq. | 5' NT of Start Codon | 5' NT of First AA of Signal Pep | AA SEQ ID NO: Y | First AA of Sig Pep | Last AA of Sig Pep | First AA of Secreted Portion | Last AA of ORF |
|---|---|---|---|---|---|---|---|---|---|---|---|---|---|---|
| 18 | HWBAO62 | 209603 Jan. 29, 1998 | pCMVSport 3.0 | 127 | 1903 | 1 | 1903 | 52 | 52 | 128 | 1 | 30 | 31 | 212 |
| 18 | HWBAO62 | 209603 Jan. 29, 1998 | pCMVSport 3.0 | 129 | 1940 | 1 | 1940 | 81 | 81 | 130 | 1 | 30 | 31 | 101 |
| 19 | HWHGU54 | 209782 Apr. 20, 1998 | pCMVSport 3.0 | 131 | 1445 | 1 | 1445 | 145 | 145 | 132 | 1 | 19 | 20 | 414 |
| 20 | HCEJQ69 | 209782 Apr. 20, 1998 | Uni-ZAP XR | 134 | 1777 | 1 | 1777 | 39 | 39 | 135 | 1 | 26 | 27 | 473 |
| 20 | HCEJQ69 | 209782 Apr. 20, 1998 | Uni-ZAP XR | 136 | 1774 | 1 | 1774 | 39 | 39 | 137 | 1 | 26 | 27 | 550 |
| 20 | HCEJQ69 | 209782 Apr. 20, 1998 | Uni-ZAP XR | 138 | 1777 | 1 | 1777 | 39 | 39 | 139 | 1 | 26 | 27 | 380 |
| 21 | HT5GJ57 | 209889, May 22, 1998 | UNI-ZAP ™ XR | 159 | 1797 | 92 | 1797 | 122 | 122 | 160 | 1 | 25 | 26 | 190 |
| 21 | HT5GJ57 | 209889 May 22, 1998 | Uni-ZAP XR | 161 | 1773 | 1 | 1773 | 105 | 105 | 162 | 1 | 25 | 26 | 243 |
| 22 | HPIBX03 | 209965 Jun. 11, 1998 | Uni-ZAP XR | 169 | 2209 | 1 | 2178 | 81 | 81 | 170 | 1 | 29 | 30 | 709 |
| 23 | HDPBO81 | 203070 Jul. 27, 1998 | pCMVSport 3.0 | 174 | 3798 | 1 | 3798 | 265 | 265 | 175 | 1 | 26 | 27 | 348 |
| 23 | HDPBO81 | 203070 Jul. 27, 1998 | pCMVSport 3.0 | 176 | 3793 | 1 | 3793 | 255 | 255 | 177 | 1 | 26 | 27 | 348 |
| 24 | HWBFY57 | 203648 Feb. 9, 1999 | pCMVSport 3.0 | 179 | 1796 | 1 | 1796 | 113 | 113 | 180 | 1 | 19 | 20 | 290 |
| 25 | HYABV21 | PTA-3105 Feb. 23, 2001 | pCMVSport 3.0 | 182 | 2738 | 1 | 2738 | 55 | 55 | 183 | 1 | 16 | 17 | 301 |
| 25 | HYABV21 | PTA-3105 Feb. 23, 2001 | pCMVSport 3.0 | 184 | 729 | 28 | 729 | 63 | 63 | 185 | 1 | 16 | 17 | 222 |
| 26 | HOHBY69 | 203331 Oct. 8, 1998 | pCMVSport 2.0 | 186 | 4995 | 1 | 4995 | 82 | 82 | 187 | 1 | 22 | 23 | 1189 |
| 26 | HOHBY69 | 203331 Oct. 8, 1998 | pCMVSport 2.0 | 188 | 4631 | 1 | 4631 | 84 | 84 | 189 | 1 | 22 | 23 | 1034 |
| 27 | HDHMA45 | 203331 Oct. 8, 1998 | pCMVSport 2.0 | 202 | 2184 | 1 | 2184 | 199 | 199 | 203 | 1 | 33 | 34 | 413 |
| 27 | HDHMA45 | 203331 Oct. 8, 1998 | pCMVSport 2.0 | 204 | 2190 | 1 | 2190 | 204 | 204 | 205 | 1 | 33 | 34 | 413 |
| 28 | HMADJ14 | PTA-622 Sep. 2, 1999 | Uni-ZAP XR | 206 | 1364 | 15 | 1364 | 278 | 278 | 207 | 1 | 68 | 69 | 352 |
| 28 | HMADJ14 | PTA-622 Sep. 2, 1999 | Uni-ZAP XR | 208 | 1583 | 1 | 1583 | 264 | 264 | 209 | 1 | 25 | 26 | 257 |
| 28 | HMADJ14 | PTA-622 Sep. 2, 1999 | Uni-ZAP XR | 210 | 1444 | 91 | 1444 | 125 | 125 | 211 | 1 | 25 | 26 | 257 |
| 28 | HMADJ14 | 203979 Apr. 29, 1999 | Uni-ZAP XR | 212 | 1444 | 91 | 1444 | 125 | 125 | 213 | 1 | 25 | 26 | 257 |
| 28 | HMADJ14 | PTA-622 Sep. 2, 1999 | Uni-ZAP XR | 214 | 1892 | 1 | 1891 | 264 | 264 | 215 | 1 | 25 | 26 | 291 |
| 28 | HMADJ14 | PTA-622 Sep. 2, 1999 | Uni-ZAP XR | 216 | 1439 | 1 | 1439 | 47 | 47 | 217 | 1 | 1 | 2 | 242 |
| 29 | HEAAL31 | 97903 Feb. 26, 1997 209049 May 15, 1997 | Uni-ZAP XR | 218 | 991 | 374 | 970 | 60 | 60 | 219 | 1 | 24 | 25 | 177 |
| 29 | HEAAL31 | 97903 Feb. 26, 1997 209049 May 15, 1997 | Uni-ZAP XR | 220 | 2416 | 1387 | 2413 | 1473 | 1473 | 221 | 1 | 18 | 19 | 25 |
| 30 | HEMFA84 | 203499 Dec. 1, 1998 | Uni-ZAP XR | 222 | 985 | 1 | 985 | 42 | 42 | 223 | 1 | 17 | 18 | 257 |
| 31 | HDPPA04 | PTA-867 Oct. 26, 1999 | pCMVSport 3.0 | 224 | 2406 | 1 | 2406 | 271 | 271 | 225 | 1 | 19 | 20 | 283 |
| 31 | HDPPA04 | PTA-867 Oct. 26, 1999 | pCMVSport 3.0 | 226 | 1675 | 1 | 1613 | | 1003 | 227 | 1 | 11 | 12 | 23 |
| 31 | HDPPA04 | PTA-867 Oct. 26, 1999 | pCMVSport 3.0 | 228 | 786 | 1 | 786 | 261 | 261 | 229 | 1 | 19 | 20 | 93 |
| 32 | HE2OA95 | 203960 Apr. 26, 1999 | Uni-ZAP XR | 230 | 1671 | 1 | 1671 | | 1224 | 231 | 1 | 9 | 10 | 35 |
| 33 | HKABZ65 | 209683 Mar. 20, 1998 | pCMVSport 2.0 | 232 | 1189 | 1 | 1189 | 77 | 77 | 233 | 1 | 17 | 18 | 243 |
| 33 | HKABZ65 | 209683 Mar. 20, 1998 | pCMVSport 2.0 | 234 | 1191 | 1 | 1191 | 69 | 69 | 235 | 1 | 17 | 18 | 243 |

Tables 1B.1 and 1B.2

The first column in Tables 1B.1 and 1B.2 provides the gene number in the application corresponding to the clone identifier. The second column in Tables 1B.1 and 1B.2 provides a unique "Clone ID:" for the cDNA clone related to each contig sequence disclosed in Tables 1B.1 and 1B.2. This clone ID references the cDNA clone which contains at least the 5' most sequence of the assembled contig and at least a portion of SEQ ID NO:X was determined by directly sequencing the referenced clone. The referenced clone may have more sequence than described in the sequence listing or the clone may have less. In the vast majority of cases, however, the clone is believed to encode a full-length polypeptide. In the case where a clone is not full-length, a full-length cDNA can be obtained by methods described elsewhere herein. The third column in Tables 1B.1 and 1B.2 provides a unique "Contig ID" identification for each contig sequence. The fourth column in Tables 1B.1 and 1B.2 provides the "SEQ ID NO:" identifier for each of the contig polynucleotide sequences disclosed in Tables 1B.1 and 1B.2.

Table 1B.1

The fifth column in Table 1B.1, "ORF (From-To)", provides the location (i.e., nucleotide position numbers) within the polynucleotide sequence "SEQ ID NO:X" that delineate the preferred open reading frame (ORF) shown in the sequence listing and referenced in Table 1B.1, column 6, as SEQ ID NO:Y. Where the nucleotide position number "To" is lower than the nucleotide position number "From", the preferred ORF is the reverse complement of the referenced polynucleotide sequence. The sixth column in Table 1B.1 provides the corresponding SEQ ID NO:Y for the polypeptide sequence encoded by the preferred ORF delineated in column 5. In one embodiment, the invention provides an amino acid sequence comprising, or alternatively consisting of, a polypeptide encoded by the portion of SEQ ID NO:X delineated by "ORF (From-To)". Also provided are polynucleotides encoding such amino acid sequences and the complementary strand thereto. Column 7 in Table 1B.1 lists residues comprising epitopes contained in the polypeptides encoded by the preferred ORF (SEQ ID NO:Y), as predicted using the algorithm of Jameson and Wolf, (1988) Comp. Appl. Biosci. 4:181-186. The Jameson-Wolf antigenic analysis was performed using the computer program PROTEAN (Version 3.11 for the Power MacIntosh, DNASTAR, Inc., 1228 South Park Street Madison, Wis.). In specific embodiments, polypeptides of the invention comprise, or alternatively consist of, at least one, two, three, four, five or more of the predicted epitopes as described in Table 1B.1. It will be appreciated that depending on the analytical criteria used to predict antigenic determinants, the exact address of the determinant may vary slightly.

Column 8 in Table 1B.1 ("Cytologic Band") provides a chromosomal map location for certain polynucleotides of the invention (e.g., polynucleotides corresponding to SEQ ID NO:X). Chromosomal location was determined by finding exact matches to EST and cDNA sequences contained in the NCBI (National Center for Biotechnology Information) UniGene database. Each sequence in the UniGene database is assigned to a "cluster"; all of the ESTs, cDNAs, and STSs in a cluster are believed to be derived from a single gene. Chromosomal mapping data is often available for one or more sequence(s) in a UniGene cluster; this data (if consistent) is then applied to the cluster as a whole. Thus, it is possible to infer the chromosomal location of a new polynucleotide sequence by determining its identity with a mapped UniGene cluster.

A modified version of the computer program BLASTN (Altshul, et al., J. Mol. Biol. 215:403-410 (1990), and Gish, and States, Nat. Genet. 3:266-272) (1993) was used to search the UniGene database for EST or cDNA sequences that contain exact or near-exact matches to a polynucleotide sequence of the invention (the 'Query'). A sequence from the UniGene database (the 'Subject') was said to be an exact match if it contained a segment of 50 nucleotides in length such that 48 of those nucleotides were in the same order as found in the Query sequence. If all of the matches that met this criteria were in the same UniGene cluster, and mapping data was available for this cluster, it is indicated in Table 1B.1 under the heading "Cytologic Band". Where a cluster had been further localized to a distinct cytologic band, that band is disclosed; where no banding information was available, but the gene had been localized to a single chromosome, the chromosome is disclosed.

Once a presumptive chromosomal location was determined for a polynucleotide of the invention, an associated disease locus was identified by comparison with a database of diseases which have been experimentally associated with genetic loci. The database used was the Morbid Map, derived from OMIM™ ("Online Mendelian Inheritance in Man"; McKusick-Nathans Institute for Genetic Medicine, Johns Hopkins University (Baltimore, Md.) and National Center for Biotechnology Information, National Library of Medicine (Bethesda, Md.) 2000; world wide web at ncbi.nlm.nih.gov/omim/). If the putative chromosomal location of a polynucleotide of the invention (Query sequence) was associated with a disease in the Morbid Map database, an OMIM reference identification number was noted in column 9, Table 1B.1, labeled "OMIM Disease Reference(s). Table 5 is a key to the OMIM reference identification numbers (Table 5, column 1), and provides a description of the associated disease in Table 5, column 2.

Table 1B.2

Column 5, in Table 1B.2, provides an expression profile and library code:count for each of the contig sequences (SEQ ID NO:X) disclosed in Table 1B.2, which can routinely be combined with the information provided in Table 4 and used to determine the tissues, cells, and/or cell line libraries which predominantly express the polynucleotides of the invention. The first number in Table 1B.2, column 5 (preceding the colon), represents the tissue/cell source identifier code corresponding to the code and description provided in Table 4. The second number in column 5 (following the colon) represents the number of times a sequence corresponding to the reference polynucleotide sequence was identified in the corresponding tissue/cell source. Those tissue/cell source identifier codes in which the first two letters are "AR" designate information generated using DNA array technology. Utilizing this technology, cDNAs were amplified by PCR and then transferred, in duplicate, onto the array. Gene expression was assayed through hybridization of first strand cDNA probes to the DNA array. cDNA probes were generated from total RNA extracted from a variety of different tissues and cell lines. Probe synthesis was performed in the presence of $^{33}P$ dCTP, using oligo (dT) to prime reverse transcription. After hybridization, high stringency washing conditions were employed to remove non-specific hybrids from the array. The remaining signal, emanating from each gene target, was measured using a Phosphorimager. Gene expression was reported as Phosphor Stimulating Luminescence (PSL) which reflects the level of phosphor signal generated from the probe hybridized to each of the gene targets represented on the array. A local background signal subtraction was performed before the total signal generated from each array was used to normalize gene expression between the different hybridizations. The value presented after “[array code]:” represents the mean of the duplicate values, following background subtraction and probe normalization. One of skill in the art could routinely use this information to identify normal and/or diseased tissue(s) which show a predominant expression pattern of the corresponding polynucleotide of the invention or to identify polynucleotides which show predominant and/or specific tissue and/or cell expression.

TABLE 1B.1

| Gene No: | cDNA Clone ID | Contig ID: | SEQ ID NO: X | ORF (From-To) | AA SEQ ID NO: Y | Predicted Epitopes | Cytologic Band | OMIM Disease Reference(s) |
|---|---|---|---|---|---|---|---|---|
| 3 | HTEEB42 | 206980 | 9 | 59-952 | 10 | Met-1 to His-7. | 21q21.2 | |
| 4 | HEMCM42 | 407085 | 11 | 58-399 | 12 | Pro-35 to Trp-42, Ala-53 to Asp-62, Arg-103 to Pro-113. | | |
| 4 | HEMCM42 | 1352150 | 15 | 25-411 | 16 | Pro-35 to Trp-42, Ala-53 to Asp-62, Arg-103 to Phe-110, Ile-114 to Glu-120. | | |
| 4 | HEQCC55 | 884824 | 13 | 62-397 | 14 | Pro-35 to Trp-42, Pro-65 to Asp-72, Thr-86 to Phe-93, Ile-97 to Glu-103. | | |
| 4 | HEQCC55 | 1352368 | 15 | 25-411 | 16 | Pro-35 to Trp-42, Ala-53 to Asp-62, Arg-103 to Phe-110, Ile-114 to Glu-120. | 16p13.3 | 141750, 141800, 141800, 141800, 141800, 141850, 141850, 141850, 141850, 141850, 156850, 186580, 191092, 600140, 600273, 601313, 601785 |
| 4 | HEQCC55 | 748227 | 17 | 57-524 | 18 | Pro-35 to Trp-42, Pro-65 to Asp-72, Thr-86 to Glu-92, Pro-96 to Gly-104, Ser-138 to Gly-154. | | |
| 5 | HEMAE80 | 409495 | 20 | 12-422 | 21 | Ser-91 to Lys-98. | | |
| 5 | HEMAE80 | 1310948 | 22 | 61-471 | 23 | Ser-91 to Lys-98. | 4p16-p15 | 225500, 600593, 602363 |
| 6 | HRDFB85 | 411020 | 28 | 233-838 | 29 | Gly-147 to Met-152, Cys-177 to Lys-188. | 7q11.23 | 116860, 129900, 233700, 600079 |
| 7 | HDTAW95 | 412472 | 38 | 571-621 | 39 | | | |
| 8 | HEMCV19 | 423219 | 46 | 79-615 | 47 | Thr-19 to Ala-33, Leu-54 to Asp-82, Pro-89 to Ala-97, Pro-100 to Lys-125, Ser-127 to Phe-135, Gly-164 to Leu-169, Cys-173 to Arg-178. | | |
| 8 | HEMCV19 | 1352162 | 48 | 84-626 | 49 | Thr-19 to Ser-31, Leu-54 to Asp-82, Pro-89 to Ala-97, Pro-100 to Lys-125, Ser-127 to Phe-135. | 19q12-q13.1 | 164731, 172400, 172400, 180901, 180901, 221770, 248600, 600918, 602716 |
| 8 | HEMCV19 | 1352161 | 50 | 125-679 | 51 | Thr-19 to Ala-33, Leu-54 to Asp-82, Pro-89 to Ala-97, Pro-100 to Lys-125, Ser-127 to Phe-135, Ser-180 to Ser-185. | | |
| 9 | HETBX14 | 806447 | 61 | 207-956 | 62 | Glu-27 to Trp-35, Leu-77 to Ala-89, Pro-96 to Asn-109, Ser-149 to Arg-156, Gln-172 to Ile-182, Glu-193 to Gly-204, | 19q13.3-q13.4 | 113900, 126340, 126391, 130410, 134790, 138570, 160900, 173850, 191044, 258501, 600040, 600138, 602225, 602225 |

TABLE 1B.1-continued

| Gene No: | cDNA Clone ID | Contig ID: | SEQ ID NO: X | ORF (From-To) | AA SEQ ID NO: Y | Predicted Epitopes | Cytologic Band | OMIM Disease Reference(s) |
|---|---|---|---|---|---|---|---|---|
| | | | | | | Glu-245 to Asn-250. | | |
| 9 | HETBX14 | 422659 | 63 | 74-235 | 64 | Gly-12 to Ser-22, Pro-34 to Ser-53. | | |
| 10 | HLHSK94 | 1307727 | 72 | 112-1251 | 73 | Gly-29 to Glu-34, Arg-71 to Arg-76, Thr-176 to Cys-182, Gly-184 to Glu-199, Lys-277 to Lys-287, Ser-292 to Cys-305, Gly-318 to Tyr-341, Gln-358 to Tyr-377. | 12q14.3 | 181430, 600808, 602116 |
| 10 | HLHSK94 | 422828 | 74 | 112-1251 | 75 | Gly-29 to Glu-34, Arg-71 to Arg-76, Thr-176 to Cys-182, Gly-184 to Glu-199. | | |
| 11 | HLHFP03 | 460467 | 76 | 224-574 | 77 | Tyr-28 to Phe-34, Thr-54 to Val-60, Tyr-73 to Thr-82. | | |
| 11 | HLHFP03 | 460467 | 78 | 224-574 | 79 | Tyr-28 to Phe-34, Thr-54 to Val-60, Tyr-73 to Thr-82. | | |
| 12 | HHTLF25 | 461438 | 83 | 142-474 | 84 | Ala-28 to Ser-33, Ala-76 to Lys-111. | 19q13.1 | 164731, 172400, 172400, 180901, 180901, 221770, 248600, 600918, 602716 |
| 13 | HTADX17 | 457172 | 90 | 84-512 | 91 | Glu-15 to Arg-23, Asn-79 to Gly-84. | | |
| 13 | HTADX17 | 753289 | 92 | 92-520 | 93 | Glu-15 to Arg-23, Asn-79 to Gly-84, Ser-101 to Gly-106, Ser-111 to Asn-116. | 1q23.1 | 107300, 131210, 136132, 145001, 173610, 601652 |
| 13 | HTADX17 | 457172 | 94 | 84-512 | 95 | Glu-15 to Arg-23, Asn-79 to Gly-84. | | |
| 14 | HJACG02 | 509948 | 102 | 47-373 | 103 | Val-54 to Asp-59. | | |
| 14 | HJACG02 | 1307789 | 104 | 66-392 | 105 | Val-54 to Asp-59. | 19p13.3 | 108725, 120700, 133171, 136836, 145981, 147141, 164953, 188070, 600957, 601238, 601846, 602216, 602477 |
| 15 | HKGAJ54 | 498303 | 107 | 31-942 | 108 | Ala-55 to Thr-62, His-164 to Gly-175, Ala-197 to Glu-202. | | |
| 15 | HKGAJ54 | 1300770 | 109 | 24-1046 | 110 | Ala-55 to Thr-62, His-164 to Gly-175, Ala-197 to Thr-204, Ser-212 to Ala-220, Gln-226 to Glu-233, Pro-252 to Gly-263, Arg-318 to Glu-326, Ser-331 to Pro-340. | | |
| 16 | HE8CH92 | 609866 | 118 | 31-1167 | 119 | Ser-44 to Ser-51, Cys-53 to Cys-64, Val-76 to Lys-83, Pro-102 to Gly-108, Arg-133 to Thr-162, Thr-204 to Ala-209, Asp-235 to Glu-241, Lys-270 to Ala- | | |

TABLE 1B.1-continued

| Gene No: | cDNA Clone ID | Contig ID: | SEQ ID NO: X | ORF (From-To) | AA SEQ ID NO: Y | Predicted Epitopes | Cytologic Band | OMIM Disease Reference(s) |
|---|---|---|---|---|---|---|---|---|
| | | | | | | 282, Ala-286 to Gly-297, Ser-346 to Arg-351, Gly-368 to Gly-374. | | |
| 16 | HSVAK93 | 597462 | 116 | 21-569 | 117 | Ser-44 to Ser-51, Cys-53 to Cys-64, Val-76 to Lys-83, Pro-102 to Gly-108, Arg-133 to Thr-162, Thr-169 to Lys-183. | | |
| 16 | HSVAK93 | 1352228 | 120 | 24-1157 | 121 | Ser-44 to Ser-51, Cys-53 to Cys-64, Val-76 to Lys-83, Pro-102 to Gly-108, Arg-133 to Thr-162, Thr-204 to Ala-209, Asp-235 to Glu-241, Lys-270 to Ala-282, Ala-286 to Gly-297, Ser-346 to Arg-351, Gly-368 to Gly-374. | | |
| 17 | HSDEK49 | 625998 | 123 | 126-1043 | 124 | Val-29 to Val-37, Asp-71 to His-76, Gln-78 to Gly-84, Met-105 to His-110, Trp-117 to Gly-122, Gln-136 to Lys-141, Leu-143 to Ala-149, Thr-162 to Asp-174, Ser-181 to Lys-186, Arg-214 to Glu-220, Glu-232 to Glu-238, Cys-249 to Asp-265. | | |
| 17 | HSDEK49 | 1352253 | 125 | 60-1256 | 126 | Val-29 to Val-37, Asp-71 to His-76, Gln-78 to Gly-84, Met-105 to His-110, Trp-117 to Asn-123, Lys-179 to Pro-187, Gly-218 to Asp-224, Leu-237 to Ala-243, Thr-256 to Asp-268, Ser-275 to Lys-280, Arg-308 to Glu-314, Glu-326 to Glu-332, Cys-343 to Asp-359. | Xq12-q13.3 | 300011, 300011, 300011, 300127, 305450, 309605, 313700, 313700, 313700, 313700, 313700, 314580 |
| 18 | HWBAO62 | 838164 | 127 | 52-687 | 128 | Ile-40 to Glu-45, Cys-63 to Val-69, Glu-83 to Asn-94, Pro-107 to Cys-115, Phe-137 to Ser-143, Ser-159 to Thr-167, Glu-200 to Tyr-210. | | |
| 18 | HWBAO62 | 625914 | 129 | 81-386 | 130 | Ile-40 to Glu-45, Cys-63 to Val-69, Glu-83 to Phe-95. | | |
| 19 | HWHGU54 | 695695 | 131 | 145-1389 | 132 | Phe-25 to Tyr-30, Gln-37 to | | |

TABLE 1B.1-continued

| Gene No: | cDNA Clone ID | Contig ID: | SEQ ID NO: X | ORF (From-To) | AA SEQ ID NO: Y | Predicted Epitopes | Cytologic Band | OMIM Disease Reference(s) |
|---|---|---|---|---|---|---|---|---|
| | | | | | | Arg-42, Lys-106 to Leu-112, Leu-123 to Leu-130, Gln-142 to Phe-150, Gln-183 to Lys-188, Asp-219 to Glu-226, Lys-359 to Glu-366. | | |
| 20 | HCEJQ69 | 1243825 | 134 | 39-1457 | 135 | Thr-41 to Gly-47, Pro-170 to Asp-176, Arg-257 to Trp-262, Gln-276 to Ser-283, Phe-278 to Val-285, Arg-323 to Gly-331, Glu-348 to Ser-354, Arg-362 to Gly-385, Pro-364 to Arg-377, Arg-407 to Leu-431, Pro-409 to Ser-427, Gly-438 to Gly-448, Gly-440 to Ala-449. | | 104170, 104170, 104170, 115470, 142360, 188400, 188400, 217095, 600850, 601607 |
| 20 | HCEJQ69 | 1243825 | 134 | 39-1457 | 135 | Thr-41 to Gly-47, Pro-170 to Asp-176, Leu-257 to Trp-262, Gln-276 to Ser-283, Arg-323 to Leu-330, Pro-364 to Arg-377, Arg-407 to Leu-431, Gly-438 to Gly-448. | 22q11 | 104170, 104170, 104170, 115470, 142360, 188400, 188400, 217095, 600850, 601607 |
| 20 | HCEJQ69 | 872582 | 136 | 39-1688 | 137 | Thr-41 to Gly-47, Pro-170 to Asp-176, Arg-257 to Trp-262, Gln-276 to Ser-283, Phe-278 to Val-285, Arg-323 to Gly-331, Glu-348 to Ser-354, Arg-362 to Gly-385, Pro-364 to Arg-377, Arg-407 to Leu-431, Pro-409 to Ser-427, Gly-438 to Gly-448, Gly-440 to Ala-449, Pro-500 to Ser-514, Pro-521 to His-528. | | |
| 20 | HCEJQ69 | 872582 | 136 | 39-1688 | 137 | Thr-41 to Gly-47, Pro-170 to Asp-176, Leu-257 to Trp-262, Gln-276 to Ser-283, Arg-323 to Leu-330, Pro-364 to Phe-374, Pro-401 to Ser-409, Arg-415 to Arg-427, Ala-474 to Gln-484, Pro-500 to Ser-514, Pro-521 to His-528. | | |
| 20 | HCEJQ69 | 609999 | 138 | 39-1178 | 139 | Thr-41 to Gly-47, Pro-170 to Asp-176, Arg- | | |

TABLE 1B.1-continued

| Gene No: | cDNA Clone ID | Contig ID: | SEQ ID NO: X | ORF (From-To) | AA SEQ ID NO: Y | Predicted Epitopes | Cytologic Band | OMIM Disease Reference(s) |
|---|---|---|---|---|---|---|---|---|
| | | | | | | 257 to Trp-262, Gln-276 to Ser-283, Phe-278 to Val-285, Arg-323 to Gly-331, Glu-348 to Ser-354. | | |
| 20 | HCEJQ69 | 609999 | 138 | 39-1178 | 139 | Thr-41 to Gly-47, Pro-170 to Asp-176, Leu-257 to Trp-262, Gln-276 to Ser-283, Arg-323 to Leu-330, Pro-362 to Val-374. | | |
| 21 | HT5GJ57 | 740767 | 159 | 122-694 | 160 | Ser-29 to Thr-57, Pro-74 to Lys-79, Pro-85 to Glu-107, Tyr-118 to Tyr-136, Gln-144 to Gln-152, Ala-182 to Glu-188. | 7q11.23 | 116860, 129900, 233700, 600079 |
| 21 | HT5GJ57 | 1299921 | 161 | 105-836 | 162 | Ser-29 to Thr-57, Pro-74 to Lys-79, Pro-85 to Glu-107, Tyr-118 to Tyr-136, Gln-144 to Gln-152, Ala-182 to Asn-195, Arg-203 to Val-208, Leu-212 to Ser-217, Gly-222 to Val-234. | 7q11.23 | 116860, 129900, 233700, 600079 |
| 22 | HPIBX03 | 743314 | 169 | 81-2207 | 170 | | 3p24.3-p22.1 | 154705, 182280, 190160, 227646, 261510, 600163, 601154 |
| 23 | HDPBO81 | 892018 | 174 | 265-1308 | 175 | Asp-53 to Tyr-61, Pro-105 to Ile-128, Arg-133 to Leu-140, Gln-182 to Ala-188, Pro-205 to Asn-218, Gly-259 to Ala-264, Asn-290 to Ser-302, Glu-307 to Tyr-314, Tyr-317 to Lys-332. | | |
| 23 | HDPBO81 | 790188 | 176 | 255-1301 | 177 | Asp-53 to Tyr-61, Pro-105 to Ile-128, Arg-133 to Leu-140, Gln-182 to Ala-188, Pro-205 to Asn-218, Gly-259 to Ser-264. | | |
| 24 | HWBFY57 | 837478 | 179 | 113-985 | 180 | Ser-69 to Arg-79, Ile-82 to Arg-89, Pro-129 to Ser-137, Leu-146 to Lys-151. | | |
| 25 | HYABV21 | 1281466 | 182 | 55-960 | 183 | | | |
| 25 | HYABV21 | 1213593 | 184 | 63-728 | 185 | | | |
| 26 | HOHBY69 | 827480 | 186 | 82-3648 | 187 | Phe-23 to Arg-31, Leu-62 to Asp-72, Val-96 to Asp-101, Thr-111 to Asn-116, Glu-128 to Thr-135, Val-142 to Ser-149, Asn-217 to Val-222, Glu-233 to Arg-241, Gly- | 15q22.3-q23 | 118485, 151670, 231680, 272800, 272800, 272800, 276700, 600374, 601780 |

TABLE 1B.1-continued

| Gene No: | cDNA Clone ID | Contig ID: | SEQ ID NO: X | ORF (From-To) | AA SEQ ID NO: Y | Predicted Epitopes | Cytologic Band | OMIM Disease Reference(s) |
|---|---|---|---|---|---|---|---|---|
| | | | | | | 272 to Leu-280, Gln-286 to Thr-293, Tyr-303 to Ile-308, Gly-354 to Thr-360, Glu-408 to Lys-419, Glu-508 to Lys-514, Arg-521 to Val-526, Gly-529 to Phe-542, Asp-551 to Tyr-557, Thr-587 to Thr-593, His-656 to Asp-665, Met-697 to Arg-705, Asp-709 to Thr-716, Glu-755 to Gly-760, Asn-779 to His-786, Leu-810 to Asp-816, Leu-844 to Ala-851, Gln-871 to Gly-877, Glu-884 to Gln-889, Ser-931 to Asn-943, Ser-974 to Ile-982, Gly-1039 to Gln-1058, Arg-1121 to Arg-1127, Ser-1134 to Trp-1139, Ser-1172 to Pro-1183. | | |
| 26 | HOHBY69 | 815681 | 188 | 84-3185 | 189 | Phe-23 to Arg-31, Leu-62 to Asp-72, Val-96 to Asp-101, Thr-111 to Asn-116, Glu-128 to Thr-135, Val-142 to Ser-149, Asn-217 to Val-222, Glu-233 to Arg-241, Gly-272 to Leu-280, Gln-286 to Thr-293, Tyr-303 to Ile-308, Gly-354 to Thr-360, Glu-408 to Lys-419, Glu-508 to Lys-514, Arg-521 to Val-526, Gly-529 to Phe-542, Asp-551 to Tyr-557, Thr-587 to Thr-593, His-656 to Asp-665, Met-697 to Arg-705, Asp-709 to Thr-716, Glu-755 to Gly-760, Asn-779 to His-786, Leu-810 to Asp-816, Leu-844 to Ala-851, Gln-871 to Gly-877, Glu-884 to Gln-889, Ser-931 to Asn-943, Ser-974 to Ile-982. | | |
| 27 | HDHMA45 | 902513 | 202 | 199-1440 | 203 | Ala-145 to Ser-154, Ala-258 to Tyr-263, Ala- | 11q | |

TABLE 1B.1-continued

| Gene No: | cDNA Clone ID | Contig ID: | SEQ ID NO: X | ORF (From-To) | AA SEQ ID NO: Y | Predicted Epitopes | Cytologic Band | OMIM Disease Reference(s) |
|---|---|---|---|---|---|---|---|---|
| | | | | | | 287 to Arg-297, Thr-306 to Met-316. | | |
| 27 | HDHMA45 | 812764 | 204 | 204-1445 | 205 | Ala-145 to Ser-154, Ala-258 to Tyr-263, Ala-287 to Arg-297, Thr-306 to Met-316. | | |
| 28 | HMADJ14 | 1099342 | 206 | 278-1333 | 207 | Asp-229 to Gln-236, Asn-244 to Lys-250, Trp-258 to Asn-266. | 8q22 | 216550, 259730 |
| 28 | HMADJ14 | 889659 | 208 | 264-1037 | 209 | Asp-229 to Gln-236, Asn-244 to Phe-251. | | |
| 28 | HMADJ14 | 843725 | 212 | 125-898 | 213 | Asp-229 to Gln-236, Asn-244 to Phe-251. | 8q22 | 216550, 259730 |
| 28 | HMADJ14 | 795479 | 214 | 264-1139 | 215 | Asp-229 to Cys-239, Asn-244 to Glu-253, Thr-271 to Ser-278. | | |
| 28 | HMADJ14 | 426068 | 216 | 47-772 | 217 | | | |
| 30 | HEMFA84 | 608198 | 222 | 42-815 | 223 | Leu-23 to Asp-34, Cys-97 to Pro-106, Ser-202 to Gly-208, Pro-251 to Gly-257. | 17p13.3 | 113721, 247200, 600059, 601545 |
| 31 | HDPPA04 | 904765 | 224 | 271-1122 | 225 | Lys-61 to Arg-72, Arg-95 to Tyr-100, Ala-121 to Ile-126, Asn-163 to Gly-172, Lys-183 to Asn-189, Ser-211 to His-218, Leu-251 to Val-269. | | |
| 31 | HDPPA04 | 905419 | 226 | 1003-1074 | 227 | Ser-16 to Lys-23. | | |
| 31 | HDPPA04 | 905418 | 228 | 261-542 | 229 | Lys-61 to Arg-72. | | |
| 32 | HE2OA95 | 637595 | 230 | 1224-1331 | 231 | | 2q32.3 | 600258, 602087 |
| 33 | HKABZ65 | 862030 | 232 | 77-808 | 233 | Ser-25 to Ala-31, Gln-146 to Ser-151, His-231 to Asn-236. | | |
| 33 | HKABZ65 | 665424 | 234 | 69-800 | 235 | Ser-25 to Ala-31, Gln-146 to Ser-151, His-231 to Asn-236. | | |

TABLE 1B.2

| Gene No: | cDNA Clone ID | Contig ID: | SEQ ID NO: X | Tissue Distribution Library Code: Count (see Table 4 for Library Codes) |
|---|---|---|---|---|
| 3 | HTEEB42 | 206980 | 9 | AR174: 12, AR191: 12, AR190: 11, AR244: 11, AR181: 11, AR291: 10, AR186: 10, AR180: 10, AR175: 10, AR192: 10, AR1899, AR1769, AR2409, AR2699, AR2419, AR1789, AR2709, AR1778, AR2668, AR2688, AR1838, AR2738, AR2748, AR1658, AR2477, AR1647, AR1987, AR1847, AR1667, AR1627, AR2027, AR1617, AR1637, AR2467, AR2456, AR1976, AR2896, AR1736, AR2016, AR2676, AR1826, AR2716, AR0526, AR2066, AR3096, AR1856, AR1886, AR2756, AR2636, AR2515, AR2365, AR2845, AR1945, AR2955, AR2555, AR2355, AR2775, AR2995, AR1795, AR0555, AR2905, AR1045, AR0335, AR1935, AR2284, AR2304, AR2044, AR1964, AR1704, AR2854, AR2564, AR1724, AR2724, AR2574, AR2624, AR2054, AR2334, AR3084, AR2614, |

TABLE 1B.2-continued

| Gene No: | cDNA Clone ID | Contig ID: | SEQ ID NO: X | Tissue Distribution Library Code: Count (see Table 4 for Library Codes) |
|---|---|---|---|---|
| | | | | AR1954, AR2524, AR3004, AR2234, AR0894, AR2874, AR2384, AR2434, AR2144, AR2964, AR2374, AR2654, AR2504, AR2394, AR2884, AR2984, AR2243, AR2943, AR2293, AR2483, AR3163, AR2073, AR2863, AR3123, AR2973, AR2643, AR1993, AR0613, AR2933, AR0533, AR2273, AR0603, AR3113, AR2113, AR2493, AR2253, AR2923, AR2193, AR2583, AR0393, AR2153, AR3133, AR2823, AR2263, AR2603, AR2312, AR2422, AR2032, AR1712, AR1682, AR2102, AR2002, AR2592, AR2342, AR0962, AR2322, AR1692, AR2222, AR2542, AR2182, AR2212, AR2532, AR2832, AR2131, AR2161, AR2171, AR3101 L0794: 4, H0624: 2, H0038: 2, L0375: 2, S0330: 2, L0750: 2, L0779: 2, H0031: 1, H0644: 1, H0124: 1, H0591: 1, H0616: 1, H0264: 1, H0623: 1, L0770: 1, L0637: 1, L0805: 1, L0663: 1, L0749: 1, L0777: 1, L0780: 1 and L0599: 1. |
| 4 | HEMCM42 | 407085 | 11 | |
| 4 | HEQCC55 | 884824 | 13 | |
| 4 | HEQCC55 | 1352368 | 15 | AR216: 11, AR217: 10, AR2149, AR2079, AR2638, AR1958, AR1658, AR2538, AR2248, AR2428, AR0538, AR1648, AR1638, AR2468, AR1618, AR2228, AR2458, AR1668, AR1708, AR1628, AR3087, AR1977, AR2127, AR3097, AR2237, AR3127, AR1987, AR3116, AR2506, AR2546, AR2056, AR2436, AR2136, AR2746, AR1686, AR2646, AR1935, AR2965, AR2015, AR2725, AR2385, AR0335, AR2755, AR1755, AR2824, AR3134, AR2214, AR2914, AR2834, AR2254, AR1744, AR2354, AR1044, AR2614, AR1714, AR2774, AR2974, AR2884, AR1774, AR3004, AR1834, AR2954, AR1694, AR3164, AR1924, AR2704, AR1814, AR0894, AR2664, AR2893, AR2693, AR1783, AR2263, AR1733, AR1723, AR2393, AR2683, AR2993, AR2903, AR2933, AR1893, AR1963, AR1853, AR2313, AR2573, AR2403, AR2853, AR2473, AR1763, AR0393, AR2103, AR2713, AR2553, AR1913, AR2673, AR2043, AR1823, AR0963, AR2623, AR2003, AR1793, AR2373, AR2273, AR1993, AR2863, AR0603, AR2343, AR2333, AR2323, AR0612, AR1902, AR2942, AR2872, AR2582, AR1882, AR2292, AR0552, AR2302, AR2152, AR2282, AR2032, AR2362, AR2112, AR2192, AR2181, AR2561 L0803: 5, L0755: 5, L0666: 4, S0418: 3, H0059: 3, H0494: 3, S0420: 2, H0086: 2, H0551: 2, H0413: 2, L0763: 2, L3904: 2, L0646: 2, L0800: 2, L0775: 2, L0659: 2, L0809: 2, H0144: 2, H0435: 2, H0670: 2, L0731: 2, S0342: 1, H0294: 1, S0180: 1, H0734: 1, S0046: 1, S0278: 1, H0437: 1, H0392: 1, H0544: 1, H0545: 1, L0471: 1, H0012: 1, H0375: 1, H0286: 1, S0250: 1, H0039: 1, H0553: 1, H0628: 1, H0646: 1, L0769: 1, L5565: 1, L0761: 1, L0764: 1, L0773: 1, L0662: 1, L0649: 1, L0804: 1, L0774: 1, L0806: 1, L0653: 1, L0657: 1, L0512: 1, L0789: 1, L0663: 1, S0406: 1, L0743: 1, L0754: 1, L0750: 1, L0780: 1, L0581: 1, L0603: 1 and H0665: 1. |
| 4 | HEMCM42 | 1352150 | 15 | AR205: 54, AR202: 41, AR206: 35, AR204: 29, AR244: 19, AR192: 15, AR194: 11, AR296: 10, AR198: 10, AR274: 10, AR2319, AR2419, AR2468, AR1867, AR0606, AR1046, AR1826, AR2346, AR2896, AR2515, AR2435, AR0525, AR2824, AR0614, AR2194, AR2664, AR0534, AR0554, AR2704, AR2923, AR2683, AR0393, AR2983, AR2933, AR2903, AR2693, AR3163, AR2833, AR1833, AR0333, AR2372, AR0892, AR2482, AR1772, AR2292, AR2182, AR2402, AR3102, AR3122, AR3002, AR1752, AR2772, AR2672, AR3131, AR1851, AR2561, AR2991, AR0961 H0494: 9, L0803: 5, L0755: 5, S0418: 4, H0551: 4, L3904: 4, L0666: 4, L2260: 4, H0435: 4, H0734: 3, H0510: 3, H0059: 3, S0436: 3, S0420: 2, H0545: 2, H0086: 2, H0628: 2, H0413: 2, L0763: 2, L0646: 2, L0800: 2, L0775: 2, L0659: 2, L0809: 2, L0663: 2, H0144: 2, H0670: 2, S0380: 2, S0406: 2, L0731: 2, L0581: 2, S0342: 1, H0294: 1, S0180: 1, S0212: 1, H0484: 1, S0408: 1, S0046: 1, H0393: 1, S0278: 1, H0437: 1, H0392: 1, H0587: 1, H0599: 1, H0748: 1, H0544: 1, L0471: 1, H0012: 1, H0375: 1, H0286: 1, S0250: 1, H0039: 1, H0553: 1, H0646: 1, H0652: 1, S0144: 1, S0422: 1, L0769: 1, L5565: 1, L0761: 1, L0764: 1, L0773: 1, L0662: 1, L0649: 1, L0804: 1, L0774: 1, L0806: 1, L0653: 1, L0657: 1, L0512: 1, L0789: 1, H0519: 1, |

TABLE 1B.2-continued

| Gene No: | cDNA Clone ID | Contig ID: | SEQ ID NO: X | Tissue Distribution Library Code: Count (see Table 4 for Library Codes) |
|---|---|---|---|---|
| | | | | H0593: 1, S0126: 1, H0684: 1, H0672: 1, H0555: 1, L0743: 1, L0754: 1, L0750: 1, L0780: 1, L0603: 1 and H0665: 1. |
| 4 | HEQCC55 | 748227 | 17 | |
| 5 | HEMAE80 | 409495 | 20 | |
| 5 | HEMAE80 | 1310948 | 22 | AR055: 113, AR060: 64, AR185: 56, AR283: 50, AR299: 49, AR300: 47, AR240: 43, AR277: 42, AR282: 42, AR104: 41, AR039: 41, AR089: 36, AR316: 33, AR218: 31, AR219: 31, AR096: 28, AR313: 16 S0126: 7, L0748: 6, S0338: 3, L0759: 3, S0318: 2, S0046: 1, H0251: 1, S0334: 1, S0336: 1, S0316: 1, S0312: 1, S0314: 1, H0056: 1, L0769: 1, L0659: 1, L0747: 1, L0749: 1, L0750: 1, L0777: 1, L0780: 1, S0194: 1 and S0276: 1. |
| 6 | HRDFB85 | 411020 | 28 | AR205: 15, AR1949, AR2448, AR2467, AR2737, AR2637, AR2046, AR2705, AR2435, AR2065, AR3105, AR2745, AR1984, AR2414, AR1864, AR1824, AR0394, AR3094, AR3123, AR2823, AR2473, AR2533, AR2403, AR0893, AR2713, AR2893, AR0523, AR2693, AR2773, AR0603, AR2513, AR2653, AR1833, AR3163, AR1923, AR0532, AR2982, AR2672, AR2842, AR2992, AR0612, AR1842, AR1752, AR2132, AR2342, AR2682, AR0552, AR2952, AR2752, AR2662, AR2272, AR2492, AR2932, AR3002, AR0332, AR2912, AR2942, AR2902, AR1852, AR2312, AR2852, AR3132, AR0962, AR2962, AR2382, AR2261, AR2371, AR2331, AR2181, AR2291, AR2811, AR2861, AR1041, AR2831, AR2921, AR2591, AR2561 S0436: 29, S0406: 23, S0440: 20, S0442: 16, S0358: 15, H0622: 15, S0354: 14, S0408: 12, S0444: 11, H0435: 11, S0360: 10, S0356: 9, H0039: 9, L0666: 9, L0751: 9, H0553: 8, H0506: 8, H0689: 7, L0748: 7, H0661: 6, L0659: 6, L0809: 6, L0665: 6, S0376: 5, L3818: 5, L0743: 5, H0484: 4, H0483: 4, H0059: 4, L0764: 4, L0771: 4, L0662: 4, S0330: 4, H0696: 4, H0615: 3, H0688: 3, H0040: 3, L0763: 3, L0364: 3, L0774: 3, L0663: 3, H0683: 3, H0670: 3, H0672: 3, L0750: 3, L0731: 3, S0434: 3, L0601: 3, H0663: 2, H0549: 2, H0046: 2, H0014: 2, H0124: 2, H0494: 2, S0450: 2, L0374: 2, L0765: 2, L0804: 2, L0378: 2, L0805: 2, L0653: 2, L0529: 2, H0593: 2, H0658: 2, S0152: 2, L0439: 2, L0779: 2, H0294: 1, S0430: 1, H0675: 1, H0676: 1, H0749: 1, H0370: 1, H0587: 1, H0642: 1, T0109: 1, H0204: 1, L0040: 1, L0738: 1, H0620: 1, H0024: 1, H0356: 1, H0375: 1, L0194: 1, T0023: 1, L0483: 1, H0033: 1, H0424: 1, H0644: 1, H0264: 1, H0488: 1, H0413: 1, H0334: 1, S0352: 1, S0306: 1, H0647: 1, H0646: 1, H0652: 1, L0373: 1, L0646: 1, L0648: 1, L0794: 1, L0803: 1, L0375: 1, L0376: 1, L0806: 1, L0658: 1, L0382: 1, L0528: 1, L5623: 1, L0664: 1, S0374: 1, H0690: 1, H0682: 1, H0648: 1, S0328: 1, H0478: 1, S0432: 1, L0744: 1, L0747: 1, L0749: 1, L0755: 1, L0759: 1, H0707: 1, L0596: 1, H0543: 1, S0462: 1 and H0352: 1. |
| 7 | HDTAW95 | 412472 | 38 | AR219: 109, AR218: 78, AR282: 11, AR3164, AR2993, AR3132, AR3002, AR2402, AR0391, AR0551 S0360: 9, L0794: 8, L0659: 6, S0436: 6, H0622: 5, S0126: 4, H0170: 3, H0587: 3, S0422: 3, L0800: 3, L0649: 3, S0390: 3, S0028: 3, L0777: 3, L0757: 3, H0662: 2, H0586: 2, H0013: 2, H0150: 2, H0551: 2, L0770: 2, L0761: 2, L0773: 2, H0682: 2, H0648: 2, S0406: 2, L0743: 2, L0751: 2, L0779: 2, S0026: 2, S0194: 2, H0506: 2, H0624: 1, S0212: 1, S0356: 1, S0354: 1, S0376: 1, H0643: 1, H0486: 1, H0427: 1, H0156: 1, L0021: 1, L0105: 1, H0031: 1, H0628: 1, H0316: 1, H0090: 1, H0412: 1, S0450: 1, S0440: 1, H0647: 1, L0763: 1, L0372: 1, L0646: 1, L0771: 1, L0648: 1, L0767: 1, L0768: 1, L0805: 1, L0653: 1, L0606: 1, L0789: 1, L4501: 1, H0144: 1, H0762: 1, H0547: 1, H0690: 1, H0684: 1, H0435: 1, S0152: 1, S0332: 1, H0626: 1, S0037: 1, S3014: 1, L0747: 1, L0480: 1, S0192: 1 and S0196: 1. |
| 8 | HEMCV19 | 423219 | 46 | |
| 8 | HEMCV19 | 1352162 | 48 | AR277: 50, AR283: 34, AR219: 33, AR096: 32, AR240: 32, AR218: 31, AR316: 30, AR089: 23, AR282: 23, AR039: 23, AR104: 23, AR313: 23, AR299: 21, AR300: 20, AR185: 20, AR055: 17, AR060: 17 H0617: 7, S0114: 5, H0486: 5, H0069: 5, |

TABLE 1B.2-continued

| Gene No: | cDNA Clone ID | Contig ID: | SEQ ID NO: X | Tissue Distribution Library Code: Count (see Table 4 for Library Codes) |
|---|---|---|---|---|
| | | | | S0344: 5, L0794: 5, H0436: 5, L0748: 5, H0341: 4, H0255: 4, L0744: 4, S0436: 4, H0295: 3, H0294: 3, T0049: 3, H0661: 3, S0356: 3, S0476: 3, H0581: 3, H0271: 3, H0038: 3, H0087: 3, H0529: 3, L0364: 3, L0766: 3, S0126: 3, L0747: 3, L0749: 3, H0423: 3, H0740: 2, H0657: 2, S0376: 2, H0497: 2, H0635: 2, H0616: 2, S0440: 2, S0144: 2, S0142: 2, L0771: 2, L0378: 2, L0806: 2, L0518: 2, H0658: 2, S0044: 2, S3014: 2, S0027: 2, L0754: 2, L0777: 2, L0731: 2, H0445: 2, L0588: 2, L0599: 2, S0424: 2, L2852: 2, H0556: 1, T0002: 1, S0040: 1, H0717: 1, L2865: 1, H0656: 1, L2919: 1, H0381: 1, H0402: 1, H0305: 1, S0360: 1, H0580: 1, H0722: 1, H0728: 1, S0046: 1, H0747: 1, S0278: 1, H0549: 1, H0586: 1, H0333: 1, T0060: 1, L0021: 1, H0575: 1, T0048: 1, H0318: 1, H0421: 1, H0263: 1, H0597: 1, H0530: 1, H0545: 1, H0041: 1, S0388: 1, H0266: 1, S0334: 1, H0688: 1, L0483: 1, H0424: 1, H0644: 1, H0628: 1, H0182: 1, H0316: 1, H0090: 1, H0591: 1, H0063: 1, H0551: 1, H0264: 1, H0412: 1, H0100: 1, H0280: 1, S0426: 1, H0743: 1, L0369: 1, L0520: 1, L4497: 1, L0770: 1, L0769: 1, L3904: 1, L0761: 1, L0772: 1, L0800: 1, L0662: 1, L5569: 1, L0381: 1, L0775: 1, L0805: 1, L0654: 1, L0776: 1, L0655: 1, L0657: 1, L0656: 1, L0382: 1, L0809: 1, L0543: 1, L0791: 1, L0666: 1, L0664: 1, H0697: 1, H0699: 1, H0689: 1, H0690: 1, H0660: 1, H0518: 1, H0521: 1, H0696: 1, S0406: 1, H0576: 1, S3012: 1, L0743: 1, L0780: 1, L0757: 1, L0759: 1, S0031: 1, L0593: 1, L0595: 1, H0542: 1, H0543: 1, H0422: 1 and H0506: 1. |
| 8 | HEMCV19 | 1352161 | 50 | |
| 9 | HETBX14 | 806447 | 61 | AR277: 75, AR269: 27, AR163: 22, AR165: 22, AR162: 21, AR161: 21, AR164: 21, AR089: 21, AR282: 21, AR166: 20, AR173: 17, AR243: 16, AR183: 16, AR188: 16, AR182: 15, AR268: 14, AR060: 14, AR196: 14, AR290: 14, AR238: 13, AR270: 12, AR240: 12, AR246: 12, AR291: 12, AR193: 11, AR300: 11, AR176: 11, AR245: 11, AR175: 11, AR180: 11, AR267: 10, AR191: 10, AR205: 10, AR316: 10, AR254: 10, AR250: 10, AR242: 10, AR255: 10, AR2339, AR2479, AR0969, AR2979, AR2379, AR1819, AR0398, AR1988, AR2318, AR2968, AR2108, AR1978, AR1898, AR2858, AR2758, AR2138, AR2347, AR0617, AR2397, AR1747, AR2667, AR2837, AR2007, AR3137, AR2017, AR1797, AR1777, AR1787, AR2327, AR2727, AR2717, AR2957, AR3087, AR2197, AR2877, AR2537, AR3127, AR2267, AR2276, AR2366, AR2886, AR2036, AR2996, AR2286, AR2616, AR1926, AR1856, AR2746, AR2296, AR1996, AR0536, AR1906, AR1956, AR2936, AR2606, AR2116, AR2576, AR0335, AR3115, AR2125, AR2165, AR2645, AR2255, AR3095, AR2155, AR1695, AR2895, AR2865, AR2185, AR1685, AR2235, AR2945, AR2175, AR2585, AR2044, AR2354, AR2244, AR2524, AR1714, AR2624, AR2304, AR0554, AR1704, AR2143, AR1043, AR1723, AR2633, AR2563, AR2213, AR2072, AR2222 L0751: 6, L0809: 5, S0328: 5, H0046: 4, L0758: 4, L0764: 3, L0665: 2, L0747: 2, H0592: 1, H0486: 1, H0263: 1, H0598: 1, H0063: 1, H0646: 1, L0662: 1, L0657: 1, L0543: 1, L5622: 1, L0793: 1, L0666: 1, L2654: 1, H0658: 1, S0330: 1 and S0044: 1. |
| 9 | HETBX14 | 422659 | 63 | |
| 10 | HLHSK94 | 1307727 | 72 | AR283: 613, AR104: 327, AR219: 244, AR218: 219, AR055: 199, AR316: 176, AR313: 160, AR089: 107, AR060: 106, AR039: 106, AR096: 99, AR299: 86, AR185: 65, AR240: 56, AR282: 51, AR300: 46, AR277: 26, AR2524, AR2463, AR2233, AR2353, AR2533, AR2663, AR1703, AR1693, AR2302, AR2432, AR2622, AR3122, AR2142, AR3092, AR2612, AR1972, AR2742, AR1932, AR2552, AR0532, AR2972, AR2252, AR1682, AR2722, AR1811, AR2171, AR2871, AR2571, AR2051, AR2911, AR0331, AR1911, AR1901, AR2361, AR1751 H0046: 44, H0135: 10, H0539: 10, L0455: 7, S0010: 3, L0456: 3, L0750: 3, L0663: 2, L0746: 2, L0747: 2, L0779: 2, L0777: 2, H0624: 1, S0116: 1, H0208: 1, L0717: 1, H0549: 1, H0333: 1, H0013: 1, |

TABLE 1B.2-continued

| Gene No: | cDNA Clone ID | Contig ID: | SEQ ID NO: X | Tissue Distribution Library Code: Count (see Table 4 for Library Codes) |
|---|---|---|---|---|
| | | | | L0157: 1, T0006: 1, H0652: 1, L0666: 1, H0144: 1, L3811: 1, S0328: 1, H0696: 1 and L0439: 1. |
| 10 | HLHSK94 | 422828 | 74 | |
| 11 | HLHFP03 | 460467 | 76 | AR194: 6, AR186: 6, AR169: 6, AR170: 5, AR202: 5, AR060: 5, AR206: 5, AR184: 5, AR176: 5, AR273: 4, AR249: 4, AR248: 4, AR223: 4, AR161: 4, AR162: 4, AR251: 4, AR163: 4, AR061: 4, AR244: 4, AR052: 4, AR055: 4, AR310: 4, AR282: 4, AR053: 4, AR267: 4, AR253: 3, AR235: 3, AR183: 3, AR269: 3, AR182: 3, AR312: 3, AR204: 3, AR266: 3, AR192: 3, AR246: 3, AR275: 3, AR185: 3, AR270: 3, AR283: 3, AR089: 3, AR298: 3, AR295: 3, AR039: 3, AR241: 3, AR271: 3, AR309: 3, AR181: 3, AR166: 3, AR291: 3, AR263: 3, AR257: 3, AR217: 3, AR316: 3, AR289: 3, AR299: 3, AR296: 3, AR033: 3, AR238: 3, AR292: 3, AR205: 2, AR247: 2, AR313: 2, AR104: 2, AR193: 2, AR231: 2, AR213: 2, AR268: 2, AR168: 2, AR284: 2, AR262: 2, AR277: 2, AR237: 2, AR212: 2, AR243: 2, AR274: 2, AR297: 2, AR286: 2, AR228: 2, AR240: 2, AR233: 2, AR272: 2, AR285: 2, AR300: 2, AR165: 2, AR229: 2, AR226: 2, AR096: 2, AR293: 2, AR255: 2, AR294: 2, AR191: 2, AR290: 2, AR164: 2, AR172: 2, AR264: 2, AR227: 2, AR174: 2, AR287: 2, AR198: 2, AR265: 2, AR232: 2, AR171: 2, AR216: 2, AR177: 2, AR311: 1, AR234: 1, AR175: 1, AR239: 1, AR203: 1, AR236: 1, AR230: 1, AR196: 1, AR261: 1, AR260: 1, AR259: 1, AR201: 1, AR189: 1, AR179: 1, L0742: 4 and H0024: 1. |
| 11 | HLHFP03 | 460467 | 78 | AR1946, AR1866, AR1696, AR1705, AR2025, AR0605, AR2065, AR1845, AR1765, AR2734, AR2494, AR2484, AR2234, AR1614, AR0554, AR1624, AR2514, AR1634, AR0614, AR2824, AR2444, AR0524, AR3104, AR0534, AR2674, AR2533, AR2353, AR1833, AR2693, AR1823, AR3123, AR2043, AR2663, AR1923, AR2463, AR2753, AR2703, AR1043, AR1853, AR2983, AR0893, AR2953, AR2413, AR2713, AR3093, AR1813, AR1663, AR2913, AR2633, AR2573, AR2173, AR2893, AR2963, AR0333, AR2383, AR2833, AR2773, AR2923, AR2052, AR2472, AR2992, AR1932, AR2312, AR2132, AR2682, AR1682, AR2842, AR2622, AR2372, AR2122, AR2432, AR2742, AR2972, AR3002, AR2862, AR2282, AR2402, AR2332, AR2722, AR2852, AR3162, AR1652, AR2292, AR0962, AR2262, AR2932, AR3132, AR2552, AR2942, AR1912, AR2902, AR1642, AR1722, AR2642, AR2272, AR1742, AR0392, AR2872, AR1982, AR2652, AR2322, AR1712, AR2162, AR1772, AR3111, AR2341, AR1751, AR2391, AR2031, AR2361, AR2301, AR2181, AR1961, AR2611, AR2601, AR2591, AR2011, AR1891, AR1791 L0742: 4 and H0024: 1. |
| 12 | HHTLF25 | 461438 | 83 | AR251: 168, AR248: 141, AR249: 139, AR265: 60, AR253: 50, AR263: 41, AR096: 37, AR244: 32, AR268: 26, AR264: 24, AR290: 20, AR246: 18, AR240: 17, AR177: 16, AR267: 14, AR183: 14, AR270: 13, AR229: 13, AR184: 12, AR055: 11, AR269: 10, AR274: 9, AR194: 8, AR175: 8, AR247: 7, AR202: 7, AR316: 7, AR234: 7, AR033: 6, AR180: 6, AR198: 6, AR271: 6, AR182: 6, AR238: 6, AR299: 5, AR206: 5, AR190: 5, AR205: 5, AR313: 5, AR188: 5, AR275: 5, AR272: 5, AR061: 5, AR196: 5, AR284: 5, AR241: 5, AR273: 5, AR173: 5, AR189: 5, AR203: 5, AR199: 5, AR237: 5, AR179: 4, AR200: 4, AR039: 4, AR172: 4, AR191: 4, AR298: 4, AR192: 4, AR181: 4, AR291: 4, AR282: 4, AR289: 4, AR176: 4, AR224: 4, AR292: 4, AR186: 3, AR226: 3, AR174: 3, AR300: 3, AR165: 3, AR161: 3, AR162: 3, AR266: 3, AR285: 3, AR163: 3, AR164: 3, AR231: 3, AR052: 3, AR215: 3, AR295: 3, AR212: 3, AR243: 3, AR309: 3, AR221: 3, AR166: 3, AR169: 3, AR296: 3, AR232: 2, AR053: 2, AR185: 2, AR223: 2, AR225: 2, AR089: 2, AR104: 2, AR277: 2, AR233: 2, AR213: 2, AR308: 2, AR286: 2, AR256: 2, AR257: 2, AR310: 2, AR283: 2, AR235: 2, AR217: 2, AR227: 2, AR204: 2, AR288: 2, AR195: 2, AR281: 2, AR293: 1, AR312: 1, AR214: 1, AR261: |

TABLE 1B.2-continued

| Gene No: | cDNA Clone ID | Contig ID: | SEQ ID NO: X | Tissue Distribution Library Code: Count (see Table 4 for Library Codes) |
|---|---|---|---|---|
| | | | | 1, AR294: 1, AR236: 1, AR216: 1, AR193: 1, AR259: 1, AR230: 1, S0144: 10, L0775: 10, S0278: 6, H0638: 5, H0641: 5, L0438: 5, H0580: 4, S0142: 4, H0521: 4, H0522: 4, L0747: 4, H0441: 3, S0388: 3, S0428: 3, H0402: 2, S0358: 2, S0408: 2, S0140: 2, H0392: 2, H0438: 2, H0086: 2, L0520: 2, L0763: 2, L0770: 2, L0772: 2, L0771: 2, L0774: 2, L0776: 2, L0526: 2, H0658: 2, L0743: 2, L0439: 2, L0751: 2, L0754: 2, L0756: 2, L0605: 2, S0134: 1, S0116: 1, H0662: 1, S0444: 1, S0360: 1, H0637: 1, S0045: 1, S0222: 1, S6014: 1, H0455: 1, H0592: 1, H0250: 1, H0069: 1, H0575: 1, T0082: 1, H0036: 1, H0581: 1, H0457: 1, S0050: 1, S0051: 1, H0399: 1, H0354: 1, H0594: 1, H0247: 1, H0271: 1, L0055: 1, S0036: 1, S0038: 1, S0438: 1, H0646: 1, L0769: 1, L0764: 1, L0375: 1, L0787: 1, S0053: 1, S0374: 1, H0682: 1, H0648: 1, H0710: 1, L0744: 1, L0755: 1, L0731: 1, L0758: 1, L0599: 1, L0603: 1, H0423: 1 and H0352: 1. |
| 12 | HHTLF25 | 461438 | 83 | AR251: 168, AR248: 141, AR249: 139, AR265: 60, AR253: 50, AR263: 41, AR244: 32, AR096: 32, AR268: 26, AR264: 24, AR290: 20, AR246: 18, AR240: 17, AR177: 16, AR267: 14, AR183: 14, AR270: 13, AR229: 13, AR184: 12, AR269: 10, AR2749, AR1948, AR1758, AR3167, AR2477, AR2027, AR3137, AR2347, AR0556, AR2996, AR0336, AR1806, AR1986, AR2716, AR1826, AR2386, AR2065, AR1905, AR2055, AR1885, AR2755, AR2725, AR0615, AR1965, AR2845, AR2415, AR2735, AR1735, AR1895, AR2035, AR1995, AR2375, AR1794, AR0394, AR2004, AR1724, AR1914, AR2984, AR1924, AR1814, AR2914, AR1044, AR2894, AR1764, AR2244, AR2924, AR1863, AR2823, AR2263, AR1743, AR3003, AR1653, AR1613, AR1623, AR2663, AR2853, AR1633, AR1643, AR2313, AR1853, AR0523, AR2153, AR2953, AR2123, AR2433, AR3093, AR2213, AR1663, AR1693, AR2963, AR2322, AR0532, AR2232, AR2252, AR0892, AR2772, AR2332, AR2132, AR3082, AR2862, AR2562, AR2572, AR2832, AR3102, AR2352, AR2172, AR2272, AR2042, AR2882, AR1952, AR2812, AR2931, AR3121, AR2141, AR2611, AR2941, AR2361, AR2161, AR1931, AR2591, AR2301 S0144: 10, L0775: 10, S0278: 6, H0638: 5, H0580: 5, H0641: 5, L0438: 5, H0521: 5, H0740: 4, H0392: 4, H0522: 4, L0747: 4, S0408: 3, H0749: 3, H0441: 3, H0438: 3, S0388: 3, S0428: 3, H0658: 3, H0402: 2, S0358: 2, S0444: 2, S0140: 2, H0747: 2, H0086: 2, S0142: 2, L0520: 2, L0763: 2, L0770: 2, L0772: 2, L0771: 2, L0774: 2, L0776: 2, L0526: 2, L0743: 2, L0439: 2, L0751: 2, L0754: 2, L0756: 2, L0605: 2, S0116: 1, H0662: 1, S0360: 1, L3646: 1, H0637: 1, S0045: 1, S0222: 1, S6014: 1, H0455: 1, H0592: 1, H0250: 1, H0069: 1, H0575: 1, T0082: 1, H0036: 1, H0581: 1, H0457: 1, S0050: 1, S0051: 1, H0399: 1, H0354: 1, H0594: 1, H0247: 1, H0271: 1, L0055: 1, S0036: 1, S0038: 1, S0438: 1, H0646: 1, L0769: 1, L0764: 1, L0375: 1, L0787: 1, S0053: 1, S0374: 1, H0682: 1, H0648: 1, H0710: 1, S0152: 1, H0727: 1, L0744: 1, L0755: 1, L0731: 1, L0758: 1, L0599: 1, L0603: 1, H0423: 1 and H0352: 1. |
| 13 | HTADX17 | 457172 | 90 | AR227: 8, AR293: 7, AR176: 7, AR233: 7, AR229: 7, AR232: 6, AR179: 6, AR182: 6, AR237: 6, AR296: 6, AR266: 6, AR060: 5, AR294: 5, AR287: 5, AR252: 4, AR185: 4, AR286: 4, AR239: 4, AR255: 4, AR200: 4, AR230: 4, AR271: 4, AR221: 3, AR289: 3, AR282: 3, AR297: 3, AR162: 3, AR089: 3, AR291: 3, AR290: 3, AR275: 3, AR257: 3, AR096: 3, AR316: 3, AR253: 2, AR270: 2, AR175: 2, AR242: 2, AR228: 2, AR061: 2, AR262: 2, AR269: 2, AR172: 2, AR161: 2, AR283: 2, AR168: 2, AR183: 2, AR181: 2, AR205: 2, AR300: 2, AR231: 2, AR177: 2, AR267: 2, AR104: 2, AR261: 2, AR033: 2, AR264: 2, AR225: 2, AR277: 2, AR195: 2, AR215: 2, AR214: 2, AR238: 2, AR173: 2, AR197: 2, AR201: 2, AR268: 2, AR246: 2, AR299: 2, AR188: 2, AR313: 2, AR288: 2, AR216: 2, AR285: 2, AR234: 1, AR309: 1, AR169: 1, AR240: 1, AR224: 1, AR174: 1, AR190: 1, AR165: 1, AR274: 1, AR039: 1, AR178: 1, AR217: |

TABLE 1B.2-continued

| Gene No: | cDNA Clone ID | Contig ID: | SEQ ID NO: X | Tissue Distribution Library Code: Count (see Table 4 for Library Codes) |
|---|---|---|---|---|
| | | | | 1, AR260: 1, AR196: 1, AR191: 1, AR204: 1, AR311: 1, AR055: 1, AR166: 1, AR222: 1, AR210: 1, AR171: 1, AR199: 1, AR258: 1, H0069: 5, H0634: 1 and L0772: 1. |
| 13 | HTADX17 | 753289 | 92 | AR2278, AR2937, AR1767, AR2337, AR2297, AR2326, AR1796, AR1826, AR2376, AR2966, AR2666, AR0605, AR2945, AR0555, AR2875, AR2524, AR2864, AR1854, AR2394, AR2554, AR2004, AR2304, AR2714, AR2213, AR2893, AR2823, AR2973, AR1623, AR0893, AR2913, AR2903, AR2753, AR2573, AR0963, AR2532, AR2702, AR1752, AR2422, AR2282, AR3162, AR0612, AR2622, AR2692, AR1722, AR1612, AR3002, AR1682, AR2832, AR1832, AR1812, AR2052, AR2312, AR1772, AR2672, AR2612, AR0332, AR2642, AR2252, AR1952, AR2772, AR2152, AR3132, AR2142, AR2382, AR1732, AR1972, AR0392, AR2012, AR2682, AR1042, AR2462, AR2182, AR1882, AR2882, AR2162, AR2992, AR2852, AR2341, AR3091, AR1691, AR2401, AR2241, AR1741, AR1901, AR1651, AR2741, AR1781, AR2171, AR2601, AR1961, AR1911, AR2041, AR3111, AR1661, AR2221, AR2101, AR1711, AR1991, AR2581 H0069: 5, H0634: 1 and L0772: 1. |
| 13 | HTADX17 | 457172 | 94 | |
| 14 | HJACG02 | 509948 | 102 | AR207: 37, AR195: 33, AR283: 32, AR263: 32, AR264: 29, AR223: 28, AR214: 28, AR089: 28, AR277: 27, AR222: 27, AR309: 27, AR311: 27, AR212: 26, AR316: 26, AR169: 26, AR224: 24, AR096: 24, AR055: 24, AR197: 23, AR213: 23, AR282: 22, AR104: 22, AR245: 22, AR171: 22, AR218: 22, AR162: 22, AR192: 21, AR217: 21, AR161: 21, AR193: 21, AR163: 20, AR308: 20, AR165: 20, AR168: 20, AR216: 20, AR170: 20, AR164: 20, AR235: 19, AR172: 19, AR053: 19, AR166: 19, AR060: 19, AR219: 19, AR242: 19, AR271: 19, AR299: 19, AR210: 19, AR039: 19, AR033: 19, AR240: 18, AR225: 18, AR313: 18, AR312: 18, AR201: 18, AR221: 17, AR261: 17, AR198: 17, AR246: 17, AR288: 17, AR252: 17, AR295: 17, AR176: 16, AR177: 16, AR215: 15, AR297: 15, AR253: 15, AR205: 15, AR270: 15, AR196: 15, AR185: 15, AR275: 15, AR286: 15, AR285: 14, AR260: 14, AR287: 14, AR233: 14, AR236: 14, AR183: 14, AR227: 13, AR175: 13, AR211: 13, AR300: 13, AR250: 13, AR294: 13, AR181: 13, AR274: 13, AR272: 13, AR229: 13, AR174: 12, AR256: 12, AR182: 12, AR234: 12, AR204: 12, AR269: 12, AR228: 12, AR293: 12, AR178: 12, AR226: 12, AR268: 11, AR266: 11, AR173: 11, AR262: 11, AR200: 11, AR243: 11, AR199: 11, AR258: 11, AR231: 11, AR291: 11, AR180: 11, AR289: 11, AR247: 11, AR239: 10, AR257: 10, AR267: 10, AR255: 10, AR188: 10, AR254: 10, AR203: 10, AR232: 10, AR238: 9, AR191: 9, AR189: 9, AR190: 9, AR061: 9, AR230: 9, AR296: 9, AR179: 9, AR290: 8, AR237: 7, S0442: 4, L0764: 4, S0408: 3, H0306: 2, H0263: 2, H0596: 2, L0800: 2, L0755: 2, S0116: 1, S0358: 1, H0489: 1, H0597: 1, T0041: 1 and L0772: 1. |
| 14 | HJACG02 | 1307789 | 104 | AR207: 37, AR195: 33, AR283: 32, AR263: 32, AR264: 29, AR223: 28, AR214: 28, AR089: 28, AR277: 27, AR222: 27, AR309: 27, AR311: 27, AR212: 26, AR169: 26, AR316: 25, AR224: 24, AR096: 24, AR055: 24, AR197: 23, AR213: 23, AR282: 22, AR104: 22, AR245: 22, AR171: 22, AR218: 22, AR162: 22, AR192: 21, AR217: 21, AR161: 21, AR193: 21, AR163: 20, AR308: 20, AR165: 20, AR168: 20, AR216: 20, AR170: 20, AR164: 20, AR235: 19, AR172: 19, AR053: 19, AR166: 19, AR060: 19, AR219: 19, AR242: 19, AR271: 19, AR299: 19, AR210: 19, AR039: 19, AR033: 19, AR240: 18, AR225: 18, AR313: 18, AR312: 18, AR201: 18, AR221: 17, AR261: 17, AR198: 17, AR246: 17, AR288: 17, AR252: 17, AR295: 17, AR176: 16, AR177: 16, AR215: 15, AR297: 15, AR253: 15, AR205: 15, AR270: 15, AR196: 15, AR185: 15, AR275: 15, AR286: 15, AR285: 14, AR260: 14, AR287: 14, AR233: 14, |

TABLE 1B.2-continued

| Gene No: | cDNA Clone ID | Contig ID: | SEQ ID NO: X | Tissue Distribution Library Code: Count (see Table 4 for Library Codes) |
|---|---|---|---|---|
| | | | | AR236: 14, AR183: 14, AR227: 13, AR175: 13, AR211: 13, AR300: 13, AR250: 13, AR294: 13, AR181: 13, AR274: 13, AR272: 13, AR229: 13, AR174: 12, AR256: 12, AR182: 12, AR234: 12, AR204: 12, AR269: 12, AR228: 12, AR293: 12, AR178: 12, AR226: 12, AR268: 11, AR266: 11, AR173: 11, AR262: 11, AR200: 11, AR243: 11, AR199: 11, AR258: 11, AR231: 11, AR291: 11, AR180: 11, AR289: 11, AR247: 11, AR239: 10, AR257: 10, AR267: 10, AR255: 10, AR188: 10, AR254: 10, AR203: 10, AR232: 10, AR2389, AR1919, AR1899, AR1909, AR0619, AR2309, AR2969, AR1799, AR2908, AR2377 S0442: 4, L0764: 4, S0408: 3, H0306: 2, H0263: 2, H0596: 2, L0800: 2, L0755: 2, S0116: 1, S0358: 1, H0489: 1, H0597: 1, T0041: 1 and L0772: 1. |
| 15 | HKGAJ54 | 498303 | 107 | AR218: 7, AR219: 6, AR242: 6, AR315: 6, AR225: 5, AR248: 4, AR244: 4, AR273: 4, AR263: 4, AR310: 4, AR280: 4, AR214: 4, AR282: 4, AR314: 3, AR221: 3, AR170: 3, AR311: 3, AR052: 3, AR213: 3, AR162: 3, AR217: 3, AR281: 3, AR243: 3, AR253: 2, AR270: 2, AR265: 2, AR186: 2, AR277: 2, AR055: 2, AR207: 2, AR104: 2, AR257: 2, AR316: 2, AR212: 2, AR194: 2, AR312: 2, AR206: 2, AR089: 2, AR195: 2, AR283: 2, AR171: 2, AR193: 1, AR240: 1, AR284: 1, AR199: 1, AR039: 1, AR163: 1, AR053: 1, AR183: 1, AR288: 1, AR033: 1, AR309: 1, AR060: 1, AR096: 1, AR236: 1, AR188: 1, AR266: 1, AR216: 1, AR161: 1, AR201: 1, AR205: 1, S0474: 2, S0400: 1, H0661: 1, S0045: 1, T0039: 1, S0003: 1, H0412: 1, H0056: 1, H0494: 1, H0646: 1, H0538: 1, S0422: 1, L0533: 1, H0539: 1, L0740: 1, L0777: 1, S0436: 1 and L0588: 1. |
| 15 | HKGAJ54 | 1300770 | 109 | AR2187, AR2196, AR2426, AR3156, AR2255, AR2484, AR2444, AR2734, AR2634, AR3104, AR2804, AR2144, AR2824, AR3143, AR2213, AR1703, AR3113, AR0523, AR2133, AR1623, AR2173, AR2813, AR2433, AR2532, AR2702, AR2652, AR1862, AR2772, AR0552, AR3162, AR2072, AR1042, AR2572, AR2122, AR1942, AR3122, AR2062, AR0892, AR1952, AR2832, AR1712, AR1931, AR2401, AR2841, AR1991, AR0391, AR1631, AR0531, AR1831, AR2881, AR0331, AR3091, AR0601, AR0961, AR2361, AR1881, AR2661, AR2161, AR1611, AR2011, AR2051 S0474: 2, S0400: 1, H0661: 1, S0045: 1, T0039: 1, S0003: 1, H0412: 1, H0056: 1, H0494: 1, H0646: 1, H0773: 1, H0538: 1, S0422: 1, L0533: 1, H0539: 1, L0740: 1, L0777: 1, S0436: 1 and L0588: 1. |
| 16 | HSVAK93 | 597462 | 116 | |
| 16 | HE8CH92 | 609866 | 118 | AR290: 19, AR268: 11, AR2679, AR3129, AR3098, AR2518, AR2707, AR3107, AR0537, AR2826, AR2666, AR3136, AR0526, AR2656, AR2635, AR0615, AR2695, AR2935, AR0605, AR0335, AR1825, AR2925, AR2955, AR2864, AR2484, AR0554, AR2384, AR2414, AR2534, AR2984, AR2134, AR0394, AR2474, AR2854, AR2894, AR1754, AR2914, AR2294, AR2944, AR2964, AR0893, AR2993, AR1773, AR2493, AR0963, AR2843, AR2563, AR2373, AR2333, AR3163, AR2343, AR2263, AR3003, AR1843, AR2593, AR1853, AR2313, AR2833, AR1832, AR2402, AR2322, AR2772, AR1042, AR1862, AR2192, AR2272, AR2182, AR2582, AR1792 L0769: 7, L0754: 7, H0657: 4, L0764: 4, L0751: 4, L0752: 4, S0408: 3, S0222: 3, H0327: 3, H0046: 3, H0056: 3, L0756: 3, S0282: 2, S0356: 2, S0444: 2, H0580: 2, L3653: 2, H0250: 2, H0318: 2, S0474: 2, H0622: 2, H0625: 2, L0803: 2, L0809: 2, L0666: 2, L2654: 2, H0648: 2, H0672: 2, S0380: 2, S0146: 2, L0748: 2, L0745: 2, L0747: 2, L0777: 2, L0731: 2, L0600: 2, H0556: 1, H0740: 1, S0116: 1, H0305: 1, H0125: 1, S0410: 1, H0637: 1, S0476: 1, H0393: 1, H0586: 1, H0643: 1, H0486: 1, H0013: 1, H0635: 1, H0599: 1, H0575: 1, S0346: 1, H0052: 1, H0309: 1, H0050: 1, H0024: 1, H0266: 1, H0271: 1, H0188: 1, H0286: 1, H0615: 1, H0124: 1, H0135: 1, H0634: 1, H0264: 1, H0413: 1, T0042: 1, H0396: 1, H0132: 1, H0641: 1, H0652: 1, S0422: 1, L0639: 1, L0646: 1, L0771: 1, L0773: 1, L0662: 1, L0766: 1, L0774: 1, L0776: 1, L0655: 1, L0807: 1, L0659: 1, L0367: 1, L2261: 1, L2440: 1, |

TABLE 1B.2-continued

| Gene No: | cDNA Clone ID | Contig ID: | SEQ ID NO: X | Tissue Distribution Library Code: Count (see Table 4 for Library Codes) |
|---|---|---|---|---|
| | | | | L2464: 1, H0726: 1, H0547: 1, H0670: 1, H0521: 1, H0696: 1, S0404: 1, S0406: 1, L0740: 1, L0749: 1, L0779: 1, L0755: 1, L0759: 1, H0445: 1, S0434: 1, S0026: 1, H0653: 1, H0667: 1, S0242: 1, S0412: 1, H0506: 1 and: 1. |
| 16 | HSVAK93 | 1352228 | 120 | AR205: 32, AR269: 30, AR275: 23, AR234: 22, AR281: 21, AR299: 20, AR315: 17, AR194: 17, AR231: 17, AR271: 17, AR274: 16, AR282: 16, AR177: 16, AR202: 15, AR283: 15, AR266: 15, AR246: 15, AR310: 14, AR280: 14, AR273: 14, AR265: 14, AR033: 14, AR244: 13, AR268: 13, AR206: 13, AR204: 13, AR053: 13, AR175: 13, AR289: 12, AR052: 12, AR192: 12, AR309: 12, AR314: 12, AR237: 12, AR039: 12, AR247: 12, AR198: 12, AR184: 11, AR238: 11, AR295: 11, AR284: 11, AR243: 11, AR270: 11, AR213: 11, AR241: 11, AR277: 11, AR291: 10, AR055: 10, AR312: 10, AR183: 10, AR285: 10, AR256: 10, AR290: 10, AR267: 10, AR263: 10, AR292: 10, AR2869, AR2969, AR2519, AR2989, AR1859, AR2408, AR1868, AR0618, AR3168, AR3008, AR2938, AR2278, AR2328, AR0898, AR2947, AR1827, AR3137, AR2297, AR2267, AR1047, AR2187, AR0966, AR2336, AR2196, AR2486, AR2535, AR2595, AR1795, AR2495, AR2585, AR0605 L0438: 4, L0439: 4, S0116: 3, L0749: 3, H0663: 2, H0309: 2, H0032: 2, H0616: 2, L0646: 2, L0774: 2, S0428: 2, L0748: 2, L0777: 2, H0445: 2, H0556: 1, S0134: 1, H0586: 1, H0632: 1, H0013: 1, H0427: 1, H0575: 1, H0318: 1, H0421: 1, H0050: 1, S0050: 1, H0051: 1, H0598: 1, H0413: 1, H0494: 1, H0396: 1, S0344: 1, L0769: 1, L0772: 1, L0666: 1, L0664: 1, L0665: 1, S0216: 1, H0726: 1, H0435: 1, S0378: 1, H0521: 1, S0146: 1, L0779: 1, L0755: 1 and L0731: 1. |
| 17 | HSDEK49 | 625998 | 123 | |
| 17 | HSDEK49 | 1352253 | 125 | AR290: 45, AR268: 37, AR240: 23, AR267: 22, AR269: 16, AR270: 14, AR234: 10, AR055: 10, AR238: 10, AR1849, AR2928, AR2918, AR1798, AR1838, AR2847, AR1777, AR1826, AR0606, AR2995, AR2955, AR2855, AR2445, AR2935, AR1755, AR0964, AR1853, AR2293, AR2493, AR2963, AR3163, AR2313, AR2983, AR2893, AR1043, AR2373, AR2862, AR0892, AR2262, AR2042, AR2662, AR2822, AR2942, AR2272, AR3132, AR2472, AR3002, AR2332, AR2482, AR2592, AR2752, AR2562, AR0391, AR0331, AR2771, AR2631, AR0611, AR2581, AR2321, AR2711, AR2831, AR3101 H0031: 7, L0439: 7, L0754: 7, L3388: 6, L0731: 6, S0002: 5, H0580: 4, H0575: 3, H0309: 3, L0438: 3, H0555: 3, L0758: 3, S0360: 2, L3649: 2, H0553: 2, S0344: 2, S0426: 2, L0775: 2, S0330: 2, L0747: 2, L0779: 2, S0260: 2, L0599: 2, L0603: 2, H0739: 1, H0170: 1, S0116: 1, S0354: 1, S0444: 1, L3645: 1, H0270: 1, S0280: 1, H0590: 1, H0581: 1, H0251: 1, H0014: 1, H0355: 1, H0030: 1, H0644: 1, H0674: 1, H0090: 1, H0063: 1, S0142: 1, L0770: 1, L0769: 1, L0651: 1, L0776: 1, L0659: 1, L0519: 1, L0664: 1, H0682: 1, L0749: 1, L0752: 1, S0031: 1 and H0506: 1. |
| 18 | HWBAO62 | 838164 | 127 | AR252: 43, AR264: 25, AR311: 20, AR308: 19, AR245: 16, AR254: 15, AR250: 15, AR246: 14, AR309: 13, AR195: 13, AR197: 13, AR201: 13, AR263: 13, AR212: 12, AR272: 11, AR193: 10, AR1749, AR2059, AR0539, AR2079, AR2438, AR2008, AR2258, AR1988, AR2538, AR2238, AR1888, AR2228, AR2247, AR3127, AR1897, AR1707, AR1637, AR2137, AR1927, AR2216, AR1616, AR1966, AR1626, AR1916, AR1656, AR2426, AR1646, AR1736, AR1805, AR1785, AR1695, AR2115, AR2405, AR2105, AR2745, AR1905, AR1725, AR2885, AR1665, AR2035, AR1815, AR1995, AR2165, AR2905, AR2575, AR2185, AR2615, AR1845, AR2695, AR2044, AR2974, AR1684, AR1764, AR2144, AR2304, AR1834, AR2874, AR2624, AR2354, AR2554, AR2684, AR2704, AR2674, AR2664, AR1793, AR2173, AR2193, AR1853, AR1713, AR1773, AR2963, AR1753, AR2823, AR3133, AR0393, AR0963, AR2153, AR2753, AR2363, AR1823, AR0893, AR2343, AR2473, AR3163, AR2953, AR0333, AR2313, AR2913, AR2383, AR2653, AR2392, AR2892, AR3002, AR0522, AR2772, AR2852, |

TABLE 1B.2-continued

| Gene No: | cDNA Clone ID | Contig ID: | SEQ ID NO: X | Tissue Distribution Library Code: Count (see Table 4 for Library Codes) |
|---|---|---|---|---|
| | | | | AR2712, AR2332, AR2292, AR2282, AR2582, AR2372, AR2322, AR0602, AR2932, AR2942, AR2602, AR2862, AR2992, AR2262, AR2062, AR3102, AR0612, AR2732, AR1862, AR2921, AR2561, AR1041, AR2811, AR2271, AR2831 H0580: 1 and H0427: 1. |
| 18 | HWBAO62 | 625914 | 129 | |
| 19 | HWHGU54 | 695695 | 131 | AR223: 5, AR169: 4, AR171: 4, AR221: 4, AR224: 4, AR264: 4, AR214: 4, AR261: 3, AR235: 3, AR263: 3, AR195: 3, AR225: 3, AR311: 3, AR168: 3, AR216: 3, AR222: 3, AR238: 3, AR183: 3, AR172: 3, AR297: 2, AR212: 2, AR162: 2, AR161: 2, AR251: 2, AR170: 2, AR217: 2, AR269: 2, AR207: 2, AR272: 2, AR228: 2, AR288: 2, AR308: 2, AR237: 2, AR231: 2, AR163: 2, AR266: 2, AR312: 2, AR176: 2, AR282: 2, AR165: 2, AR257: 2, AR262: 2, AR277: 2, AR200: 2, AR196: 2, AR198: 2, AR173: 2, AR254: 2, AR213: 2, AR166: 2, AR180: 2, AR226: 2, AR181: 2, AR234: 2, AR298: 2, AR189: 2, AR096: 2, AR236: 2, AR089: 2, AR271: 2, AR197: 2, AR246: 2, AR295: 2, AR193: 2, AR239: 2, AR274: 1, AR178: 1, AR061: 1, AR227: 1, AR300: 1, AR177: 1, AR039: 1, AR164: 1, AR188: 1, AR267: 1, AR247: 1, AR287: 1, AR229: 1, AR211: 1, AR243: 1, AR201: 1, AR191: 1, AR204: 1, AR190: 1, AR179: 1, AR270: 1, AR182: 1, AR055: 1, AR230: 1, AR294: 1, AR199: 1, AR285: 1, AR291: 1, AR290: 1, AR316: 1, AR286: 1, AR296: 1, AR060: 1, AR309: 1, AR210: 1, H0586: 3 and L0777: 2. |
| 19 | HWHGU54 | 695695 | 131 | AR2235, AR1694, AR1714, AR2214, AR2244, AR2644, AR2144, AR2613, AR2353, AR2633, AR1953, AR2253, AR3113, AR1683, AR2163, AR2223, AR2383, AR1833, AR1723, AR2972, AR2122, AR1622, AR1612, AR2512, AR1702, AR2172, AR2692, AR2072, AR2722, AR2282, AR2882, AR3082, AR2372, AR2312, AR1632, AR2662, AR3122, AR1762, AR2822, AR1652, AR2572, AR2622, AR2772, AR2002, AR1962, AR1982, AR1732, AR2542, AR2132, AR1662, AR1802, AR2262, AR1812, AR2342, AR2982, AR1892, AR2362, AR2712, AR1972, AR0892, AR2462, AR2952, AR1932, AR2392, AR2741, AR1781, AR0611, AR2271, AR3001, AR1771, AR1641, AR1881, AR2671, AR2471, AR0961, AR2871, AR2291, AR2111, AR2431, AR2011, AR1911, AR2041, AR1901, AR1791, AR2701, AR1821, AR2301, AR2941, AR1991, AR2851, AR2911, AR2901, AR3161, AR2861, AR2961, AR0601, AR3091, AR2101 H0586: 3 and L0777: 2. |
| 20 | HCEJQ69 | 1243825 | 134 | AR273: 54, AR251: 54, AR186: 47, AR249: 31, AR052: 30, AR292: 30, AR241: 24, AR184: 24, AR061: 23, AR259: 23, AR310: 23, AR206: 22, AR194: 22, AR298: 21, AR248: 20, AR265: 18, AR274: 18, AR244: 16, AR198: 15, AR237: 15, AR243: 15, AR202: 14, AR309: 14, AR229: 14, AR033: 14, AR227: 13, AR053: 13, AR271: 13, AR204: 13, AR096: 12, AR104: 12, AR275: 12, AR192: 12, AR185: 12, AR313: 12, AR284: 11, AR296: 11, AR293: 10, AR233: 10, AR312: 10, AR282: 10, AR294: 10, AR232: 10, AR055: 10, AR283: 9, AR263: 9, AR300: 9, AR215: 9, AR266: 9, AR183: 9, AR247: 9, AR219: 9, AR256: 9, AR231: 8, AR175: 8, AR213: 8, AR267: 8, AR177: 8, AR238: 8, AR089: 8, AR218: 8, AR289: 8, AR039: 8, AR246: 7, AR277: 7, AR253: 7, AR295: 7, AR285: 7, AR299: 7, AR205: 7, AR182: 7, AR240: 7, AR286: 7, AR221: 7, AR226: 7, AR316: 6, AR234: 6, AR291: 6, AR269: 6, AR270: 6, AR060: 6, AR170: 6, AR290: 5, AR223: 5, AR179: 5, AR268: 5, AR214: 5, AR172: 5, AR224: 5, AR258: 5, AR245: 4, AR171: 4, AR216: 4, AR168: 4, AR222: 4, AR165: 4, AR254: 4, AR164: 4, AR217: 3, AR161: 3, AR225: 3, AR197: 3, AR162: 3, AR166: 3, AR163: 3, AR308: 3, AR272: 3, AR264: 3, AR257: 3, AR169: 3, AR311: 2, AR195: 2, AR212: 2, AR199: 2, AR210: 2, AR235: 2, AR180: 2, AR242: 2, AR188: 2, AR181: 2, AR288: 2, AR262: 2, AR173: 2, AR201: 2, AR178: 2, AR207: 2, AR189: 2, AR261: 2, AR196: 2, AR203: 2, AR255: 2, AR297: 2, AR236: 2, AR176: 1, |

TABLE 1B.2-continued

| Gene No: | cDNA Clone ID | Contig ID: | SEQ ID NO: X | Tissue Distribution Library Code: Count (see Table 4 for Library Codes) |
|---|---|---|---|---|
| | | | | AR211: 1, AR193: 1, AR287: 1, AR230: 1, AR200: 1, AR191: 1, AR174: 1, AR239: 1, AR190: 1, AR228: 1, H0052: 3, L0439: 3, H0194: 1, H0546: 1, H0615: 1, H0135: 1, H0087: 1, L0759: 1, S0436: 1 and S0456: 1. |
| 20 | HCEJQ69 | 1243825 | 134 | AR273: 54, AR251: 54, AR186: 47, AR249: 31, AR052: 30, AR292: 30, AR241: 24, AR184: 24, AR061: 23, AR259: 23, AR310: 23, AR206: 22, AR194: 22, AR298: 21, AR248: 20, AR265: 18, AR274: 18, AR244: 16, AR198: 15, AR314: 15, AR237: 15, AR243: 15, AR202: 14, AR309: 14, AR229: 14, AR280: 14, AR033: 14, AR227: 13, AR053: 13, AR271: 13, AR204: 13, AR315: 13, AR104: 12, AR275: 12, AR192: 12, AR185: 12, AR313: 12, AR284: 11, AR296: 11, AR293: 10, AR233: 10, AR096: 10, AR281: 10, AR312: 10, AR282: 10, AR294: 10, AR219: 10, AR232: 10, AR0399, AR2839, AR2639, AR3009, AR2159, AR0559, AR2669, AR1839, AR2479, AR2569, AR2318, AR1758, AR2138, AR2678, AR1778, AR2388, AR2898, AR2467, AR2777, AR2537, AR0897, AR2957, AR2857, AR2997, AR2187, AR2057, AR1827, AR2407, AR2867, AR2217, AR2267, AR3166, AR2346, AR2916, AR2696, AR2706, AR0606, AR1706, AR2905, AR2235, AR1795, AR2685, AR2145, AR1725, AR2245, AR2585, AR2454, AR1714, AR2164, AR1684, AR2224, AR1654, AR2544, AR1644, AR2173, AR1613, AR2253, AR1973, AR1623, AR1663, AR1633, AR3083, AR2723, AR2643, AR2573, AR1693, AR3112, AR1952, AR2122, AR1992, AR2102, AR2352, AR1802, AR2422, AR1882, AR1812, AR2882, AR2622, AR1732, AR2012, AR1782, AR2072, AR1892, AR2612, AR1962, AR2032, AR2552, AR2972, AR2362, AR1761, AR2111, AR1931, AR2871, AR2301, AR2001, AR1911, AR1741, AR2391, AR1901, AR2281 H0052: 3, L0439: 3, H0194: 1, H0546: 1, H0615: 1, H0135: 1, H0087: 1, L3841: 1, L0759: 1, S0436: 1 and S0456: 1. |
| 20 | HCEJQ69 | 872582 | 136 | |
| 20 | HCEJQ69 | 609999 | 138 | |
| 21 | HT5GJ57 | 740767 | 159 | AR213: 5, AR264: 4, AR224: 4, AR254: 4, AR253: 4, AR207: 4, AR053: 3, AR197: 3, AR161: 3, AR162: 3, AR163: 3, AR250: 3, AR221: 3, AR171: 3, AR311: 3, AR212: 3, AR165: 3, AR215: 3, AR282: 3, AR217: 2, AR309: 2, AR263: 2, AR193: 2, AR195: 2, AR089: 2, AR168: 2, AR166: 2, AR164: 2, AR312: 2, AR308: 2, AR223: 2, AR183: 2, AR267: 2, AR169: 2, AR198: 2, AR266: 2, AR033: 2, AR216: 2, AR271: 2, AR096: 1, AR210: 1, AR192: 1, AR277: 1, AR272: 1, AR240: 1, AR286: 1, AR313: 1, AR060: 1, AR180: 1, AR204: 1, AR299: 1, AR039: 1, AR246: 1, AR104: 1, AR201: 1, AR270: 1, AR205: 1, AR055: 1, AR225: 1, AR247: 1, AR258: 1, AR182: 1, AR274: 1, AR214: 1, AR287: 1, AR243: 1, H0584: 3, H0341: 3, H0271: 3, H0318: 2, H0090: 2, H0264: 2, S0052: 2, H0656: 1, H0580: 1, S0278: 1, H0431: 1, H0013: 1, H0457: 1, H0284: 1, S0003: 1, S0144: 1, S0142: 1, S0002: 1, H0702: 1, H0522: 1 and H0445: 1. |
| 21 | HT5GJ57 | 1299921 | 161 | AR2135, AR2644, AR2244, AR2544, AR2534, AR2074, AR0533, AR1973, AR1613, AR1623, AR1633, AR2503, AR2213, AR1713, AR3113, AR2123, AR1653, AR2153, AR2172, AR3092, AR2632, AR1932, AR2822, AR1952, AR1682, AR1662, AR0892, AR1642, AR3122, AR3082, AR2232, AR1832, AR2672, AR1692, AR1982, AR2662, AR0332, AR2162, AR2712, AR2101, AR1921, AR2721, AR2401, AR2861, AR2771, AR0601, AR1801, AR2041, AR3131, AR2461, AR1041, AR2011, AR0961, AR2701, AR2051, AR2251, AR2471, AR2991, AR2581, AR1821, AR2741, AR2141, AR2871, AR2431 H0584: 3, H0341: 3, H0318: 2, H0271: 2, H0090: 2, H0264: 2, S0052: 2, H0521: 2, H0556: 1, H0740: 1, H0656: 1, H0580: 1, S0278: 1, H0431: 1, H0013: 1, H0284: 1, S0003: 1, S0144: 1, S0142: 1, S0002: 1, H0702: 1, L3832: 1, H0522: 1 and H0445: 1. |
| 22 | HPIBX03 | 743314 | 169 | AR202: 71, AR194: 67, AR244: 58, AR281: 55, AR206: 54, AR241: 40, AR310: 38, AR315: 37, AR265: 36, AR283: 35, AR280: 35, AR246: 35, AR314: 34, AR104: 29, AR284: 29, AR186: 28, |

TABLE 1B.2-continued

| Gene No: | cDNA Clone ID | Contig ID: | SEQ ID NO: X | Tissue Distribution Library Code: Count (see Table 4 for Library Codes) |
|---|---|---|---|---|
| | | | | AR273: 26, AR292: 26, AR052: 25, AR198: 25, AR205: 25, AR243: 25, AR033: 23, AR039: 23, AR263: 22, AR271: 20, AR096: 20, AR282: 20, AR298: 20, AR251: 20, AR192: 19, AR204: 19, AR289: 18, AR259: 17, AR275: 17, AR274: 17, AR277: 17, AR055: 17, AR313: 16, AR291: 16, AR266: 16, AR286: 16, AR312: 15, AR285: 15, AR299: 15, AR218: 15, AR295: 15, AR240: 15, AR316: 14, AR309: 14, AR300: 14, AR247: 14, AR219: 14, AR294: 13, AR053: 13, AR213: 13, AR089: 12, AR061: 12, AR248: 12, AR249: 12, AR232: 12, AR177: 12, AR184: 12, AR296: 11, AR293: 11, AR268: 11, AR185: 11, AR270: 11, AR182: 10, AR227: 10, AR256: 10, AR290: 10, AR183: 10, AR269: 10, AR1759, AR2269, AR2589, AR2299, AR2389, AR2678, AR0608, AR2318, AR2378, AR1707, AR2337, AR2537, AR2347, AR2236, AR2256, AR1726, AR1715, AR1685, AR1765, AR2145, AR2175, AR2165, AR2245, AR2154, AR2214, AR1794, AR1614, AR1644, AR1664, AR2574, AR2224, AR2004, AR1623, AR1633, AR1803, AR2363, AR2613, AR1733, AR2553, AR1693, AR2723, AR2643, AR1653, AR2283, AR2883, AR2303, AR2873, AR1963, AR1813, AR2623, AR2392, AR1912, AR1932, AR1882, AR1902, AR1972, AR2102, AR1782, AR1952, AR1892, AR2122, AR2012, AR1741, AR2601, AR2971, AR2031 H0031: 4, S0442: 2, S0358: 2, S0150: 2, L0768: 2, S0152: 2, S0444: 1, S0132: 1, S0476: 1, H0620: 1, H0494: 1, S0002: 1, S0426: 1, L0776: 1, S0126: 1 and L0596: 1. |
| 23 | HDPBO81 | 892018 | 174 | AR0533, AR2513, AR2623, AR2872, AR1642, AR2022, AR2522, AR1652, AR2822, AR1952, AR1682, AR1762, AR2612, AR2252, AR2572, AR2542, AR2972, AR2672, AR2942, AR2852, AR1722, AR2152, AR1622, AR2702, AR3092, AR2261, AR2141, AR2121, AR1931, AR2911, AR2131, AR1631, AR2171, AR2501, AR1751, AR0601, AR3121, AR2771, AR1611, AR1811, AR2341, AR1821, AR1961, AR1801, AR3001, AR0891, AR2211, AR2741 H0521: 6, L0804: 2, H0634: 1 and S0440: 1. |
| 23 | HDPBO81 | 790188 | 176 | |
| 24 | HWBFY57 | 837478 | 179 | AR207: 12, AR245: 10, AR197: 10, AR250: 10, AR2019, AR2429, AR1959, AR2548, AR2528, AR2488, AR1847, AR1937, AR2127, AR0967, AR2646, AR1986, AR1666, AR2536, AR1656, AR1615, AR1625, AR1645, AR3085, AR2145, AR1635, AR2245, AR3115, AR2495, AR2465, AR2434, AR1924, AR2054, AR2714, AR2224, AR0534, AR2174, AR2234, AR2404, AR2724, AR2773, AR1743, AR2363, AR2043, AR2823, AR2633, AR2163, AR2133, AR1813, AR1823, AR1703, AR3123, AR2303, AR2883, AR1683, AR2703, AR2683, AR3163, AR2973, AR1833, AR1802, AR3092, AR2692, AR0602, AR3132, AR2852, AR0892, AR2962, AR2472, AR1782, AR1772, AR2292, AR2902, AR2952, AR0332, AR3002, AR2752, AR0522, AR2912, AR2892, AR2842, AR2662, AR0392, AR2342, AR2312, AR2612, AR2862, AR2982, AR2922, AR1732, AR1882, AR2872, AR2572, AR2992, AR0552, AR2062, AR2932, AR2282, AR1792, AR2111, AR2811, AR2621, AR2331, AR1851, AR2941, AR2261, AR2831, AR2321, AR2251, AR2351, AR2671, AR2741, AR2271, AR1861, AR1941, AR1751, AR0611, AR1891, AR1991, AR1041, AR2381, AR1711, AR2101 L0794: 6, H0580: 4, H0457: 3, L0785: 1, S0360: 1, S0002: 1, L0804: 1, L0806: 1, L0805: 1 and L0789: 1. |
| 25 | HYABV21 | 1281466 | 182 | L0766: 6, L0748: 3, H0656: 2, H0264: 2, H0583: 1, H0650: 1, H0657: 1, L0655: 1, L0659: 1, L0790: 1, H0518: 1 and L0749: 1. |
| 25 | HYABV21 | 1213593 | 184 | |
| 26 | HOHBY69 | 827480 | 186 | AR2445, AR2213, AR1683, AR2843, AR2823, AR1842, AR2242, AR1952, AR3102, AR1622, AR1612, AR1632, AR2641, AR1811, AR1821, AR1861, AR1711, AR2771, AR3081, AR2831, AR2631 S0250: 5, H0545: 2, S0210: 2, S0040: 1, S0342: 1, H0661: 1, S0418: 1, S0360: 1, H0549: 1, H0251: 1, H0544: 1, S0003: 1, H0124: 1, L0564: 1, L0807: 1, L0565: 1, S0037: 1, L0744: 1, L0757: 1 and S0276: 1. |
| 26 | HOHBY69 | 815681 | 188 | |
| 27 | HDHMA45 | 902513 | 202 | AR2259, AR2778, AR2148, AR2238, AR2158, AR1657, AR1717, AR1646, AR1706, AR1686, AR1666, AR2246, |

TABLE 1B.2-continued

| Gene No: | cDNA Clone ID | Contig ID: | SEQ ID NO: X | Tissue Distribution Library Code: Count (see Table 4 for Library Codes) |
|---|---|---|---|---|
| | | | | AR2226, AR2356, AR1726, AR1625, AR2165, AR1615, AR2825, AR2175, AR2645, AR1635, AR2975, AR2215, AR2885, AR1805, AR3115, AR2074, AR2124, AR2614, AR2634, AR1784, AR2874, AR2574, AR2524, AR1833, AR1763, AR1923, AR0603, AR2913, AR3093, AR0893, AR2403, AR3083, AR2893, AR1813, AR1963, AR1733, AR2853, AR2833, AR2393, AR2623, AR2953, AR3163, AR2333, AR2963, AR2323, AR2003, AR2863, AR3123, AR1953, AR2283, AR2993, AR2133, AR2343, AR1913, AR2933, AR2383, AR2943, AR0963, AR1043, AR2473, AR2293, AR3003, AR1843, AR2663, AR2423, AR2713, AR2112, AR1692, AR2552, AR2452, AR2362, AR3132, AR2312, AR2582, AR2692, AR2012, AR2682, AR1982, AR2032, AR0392, AR2602, AR1792, AR1742, AR1902, AR2302, AR0552, AR1752, AR2902, AR2752, AR1852, AR0332, AR1772, AR1892, AR2702, AR2102, AR2052, AR2272, AR1882, AR2532, AR2432, AR2672, AR1822, AR2262, AR3102, AR2742, AR2022, AR2731, AR2721, AR1991, AR0531, AR2371, AR2541, AR2181, AR0611, AR2561, AR2651, AR2921, AR1931, AR2841 L0794: 5, L0769: 4, L0749: 3, S0110: 1, H0572: 1, H0050: 1, L0765: 1, L0756: 1, L0755: 1 and L0758: 1. |
| 27 | HDHMA45 | 812764 | 204 | |
| 28 | HMADJ14 | 1099342 | 206 | AR184: 30, AR298: 28, AR259: 25, AR292: 24, AR249: 18, AR251: 17, AR229: 14, AR314: 13, AR237: 13, AR294: 13, AR296: 12, AR293: 12, AR233: 11, AR284: 11, AR227: 11, AR315: 11, AR182: 11, AR280: 10, AR266: 10, AR0399, AR2319, AR0619, AR0339, AR2488, AR2328, AR2868, AR2678, AR2818, AR2698, AR2268, AR2567, AR2897, AR2857, AR2347, AR2907, AR2387, AR1837, AR1777, AR2957, AR1756, AR0556, AR2916, AR1866, AR1856, AR1766, AR0895, AR2705, AR2685, AR2585, AR3005, AR1615, AR1625, AR1635, AR2285, AR2355, AR2635, AR2825, AR3135, AR3104, AR1794, AR0964, AR2194, AR1814, AR2014, AR1044, AR2184, AR3164, AR1724, AR0604, AR2774, AR2614, AR2994, AR2234, AR2023, AR1683, AR2833, AR0533, AR2453, AR2363, AR1653, AR2473, AR1643, AR2173, AR2553, AR3093, AR2713, AR2303, AR1663, AR2883, AR1913, AR2623, AR2403, AR1783, AR2533, AR2573, AR2523, AR2153, AR3113, AR2393, AR1963, AR1903, AR2873, AR2643, AR1713, AR2253, AR1733, AR2723, AR2002, AR2162, AR2742, AR2422, AR2972, AR2142, AR1932, AR1882, AR2032, AR2222, AR2242, AR2432, AR2752, AR2042, AR3122, AR1892, AR1992, AR2062, AR2072, AR1952, AR2652, AR2461, AR2111, AR3081, AR1741, AR1971, AR1801, AR2601, AR0521, AR2211 S0144: 6, S0278: 5, S0344: 3, S0002: 3, H0521: 3, S0003: 2, H0575: 1, S0214: 1, H0068: 1, H0591: 1, L0806: 1, L0805: 1, L0776: 1 and L0791: 1. |
| 28 | HMADJ14 | 889659 | 208 | |
| 28 | HMADJ14 | 843725 | 210 | |
| 28 | HMADJ14 | 843725 | 212 | AR184: 30, AR298: 28, AR259: 25, AR292: 24, AR249: 18, AR251: 17, AR229: 14, AR314: 13, AR237: 13, AR294: 13, AR296: 12, AR293: 12, AR233: 11, AR284: 11, AR227: 11, AR315: 11, AR182: 11, AR280: 10, AR266: 10, AR039: 9, AR231: 9, AR061: 9, AR033: 9, AR248: 8, AR232: 8, AR286: 8, AR267: 8, AR281: 8, AR269: 8, AR226: 8, AR256: 7, AR289: 7, AR285: 7, AR234: 7, AR290: 7, AR238: 7, AR183: 7, AR177: 7, AR295: 7, AR175: 6, AR055: 6, AR291: 6, AR186: 6, AR185: 6, AR176: 6, AR089: 5, AR270: 5, AR268: 5, AR258: 5, AR300: 5, AR161: 5, AR162: 5, AR163: 5, AR228: 5, AR235: 5, AR263: 5, AR282: 5, AR313: 5, AR310: 4, AR179: 4, AR096: 4, AR219: 4, AR181: 4, AR201: 4, AR104: 4, AR218: 4, AR316: 4, AR172: 4, AR060: 4, AR277: 4, AR261: 4, AR299: 4, AR223: 4, AR202: 3, AR168: 3, AR283: 3, AR053: 3, AR245: 3, AR236: 3, AR165: 3, AR247: 3, AR164: 3, AR217: 3, AR255: 3, AR309: 3, AR271: 3, AR230: 3, AR166: 3, AR288: 3, AR191: 3, AR262: 3, AR240: 3, AR178: 3, AR253: 3, AR257: 3, AR252: 3, AR215: 3, AR311: 3, AR239: 3, AR196: 3, AR190: 3, AR287: 3, AR264: 3, AR171: 3, AR225: 3, AR173: 3, AR272: 3, AR200: 2, AR216: 2, AR274: 2, AR242: 2, AR297: 2, AR214: 2, AR193: 2, AR188: 2, AR203: 2, AR222: 2, AR224: 2, AR243: 2, AR275: 2, |

TABLE 1B.2-continued

| Gene No: | cDNA Clone ID | Contig ID: | SEQ ID NO: X | Tissue Distribution Library Code: Count (see Table 4 for Library Codes) |
|---|---|---|---|---|
| | | | | AR204: 2, AR312: 2, AR189: 2, AR199: 2, AR206: 2, AR207: 2, AR195: 2, AR265: 2, AR246: 1, AR211: 1, AR308: 1, AR174: 1, AR197: 1, AR180: 1, AR260: 1, AR052: 1, AR221: 1, S0144: 6, S0278: 5, S0344: 3, S0002: 3, H0521: 3, S0003: 2, H0575: 1, S0214: 1, H0068: 1, H0591: 1, L0806: 1, L0805: 1, L0776: 1 and L0791: 1. |
| 28 | HMADJ14 | 795479 | 214 | |
| 28 | HMADJ14 | 426068 | 216 | |
| 30 | HEMFA84 | 608198 | 222 | AR0606, AR0894, AR0554, AR2194, AR2823, AR3163, AR0963, AR1043, AR2183, AR2403, AR3132, AR2992, AR2472, AR2922, AR2832, AR0392, AR2462, AR2942, AR1852, AR3002, AR2481, AR2681, AR2771, AR3121, AR0331, AR1831, AR2631, AR2671, AR3101, AR0531, AR2381 L0747: 5, H0556: 4, L0769: 4, L0806: 3, L5622: 3, L0790: 3, L0779: 3, H0265: 2, H0013: 2, L0666: 2, L0439: 2, L0740: 2, L0749: 2, L0752: 2, L0757: 2, L0596: 2, T0049: 1, S0046: 1, S0132: 1, S0476: 1, L0717: 1, H0549: 1, H0600: 1, H0559: 1, H0046: 1, H0083: 1, H0266: 1, S0314: 1, H0622: 1, H0674: 1, H0135: 1, H0090: 1, L0564: 1, H0494: 1, S0440: 1, L0772: 1, L0800: 1, L0644: 1, L0794: 1, L0766: 1, L0776: 1, L0807: 1, L0809: 1, L0791: 1, L0665: 1, H0144: 1, H0660: 1, S0406: 1, L0780: 1, S0434: 1 and L0595: 1. |
| 31 | HDPPA04 | 904765 | 224 | AR2517, AR1806, AR2524, AR1944, AR2494, AR1974, AR1693, AR1783, AR2353, AR2413, AR1903, AR1842, AR1722, AR2902, AR2712, AR1912, AR1742, AR2252, AR1662, AR2732, AR1752, AR2682, AR2242, AR2142, AR2912, AR1642, AR2822, AR1682, AR2532, AR1652, AR2952, AR2122, AR1832, AR2461, AR2871, AR0961, AR3111, AR2721, AR1881, AR3081, AR2041, AR2771, AR3101, AR2971, AR2011, AR2191, AR1861, AR2101, AR2131, AR2301, AR1891, AR2811, AR3131, AR2571, AR2021 H0521: 4, L0731: 4, H0591: 2, H0641: 2, L0794: 2, T0049: 1, S0476: 1, H0004: 1, H0494: 1, L0791: 1, H0522: 1, L0758: 1 and S0452: 1. |
| 31 | HDPPA04 | 905419 | 226 | |
| 31 | HDPPA04 | 905418 | 228 | |
| 32 | HE2OA95 | 637595 | 230 | AR223: 26, AR089: 25, AR216: 25, AR224: 23, AR222: 22, AR214: 22, AR215: 21, AR308: 21, AR210: 21, AR272: 21, AR221: 19, AR219: 18, AR235: 18, AR211: 17, AR261: 17, AR225: 17, AR218: 17, AR309: 17, AR217: 16, AR283: 16, AR311: 16, AR172: 16, AR196: 16, AR168: 16, AR274: 15, AR169: 15, AR171: 15, AR199: 15, AR316: 15, AR104: 15, AR188: 14, AR170: 14, AR264: 13, AR096: 13, AR295: 12, AR313: 12, AR312: 11, AR285: 11, AR165: 11, AR236: 11, AR189: 11, AR055: 11, AR247: 11, AR164: 11, AR263: 11, AR299: 10, AR166: 10, AR282: 10, AR161: 10, AR162: 10, AR200: 10, AR297: 9, AR163: 9, AR293: 9, AR288: 9, AR262: 9, AR296: 9, AR240: 9, AR060: 8, AR191: 8, AR039: 8, AR291: 8, AR181: 8, AR277: 8, AR203: 8, AR177: 8, AR255: 7, AR275: 7, AR231: 7, AR185: 7, AR190: 7, AR174: 6, AR290: 6, AR287: 6, AR173: 6, AR175: 6, AR286: 6, AR300: 6, AR183: 5, AR270: 5, AR269: 5, AR267: 5, AR258: 5, AR239: 5, AR294: 5, AR179: 5, AR289: 5, AR256: 5, AR268: 5, AR257: 5, AR061: 4, AR266: 4, AR230: 4, AR178: 4, AR234: 4, AR176: 4, AR232: 4, AR238: 4, AR229: 4, AR237: 3, AR180: 3, AR260: 3, AR226: 3, AR233: 3, AR227: 3, AR182: 3, AR228: 2, AR033: 2, AR197: 2, AR195: 2, AR205: 1, AR201: 1, L0005: 4, L0439: 4, H0013: 3, H0674: 3, H0144: 3, H0170: 2, L0157: 2, L0435: 2, L0540: 2, L0438: 2, L0756: 2, L0759: 2, S0045: 1, H0599: 1, H0178: 1, H0572: 1, H0050: 1, H0024: 1, H0051: 1, S6028: 1, L0142: 1, H0673: 1, H0616: 1, H0551: 1, H0623: 1, L0809: 1, L0666: 1, H0520: 1, H0547: 1, H0519: 1, S0126: 1, H0539: 1, H0696: 1, H0694: 1, L0742: 1, L0777: 1, L0758: 1, L0592: 1 and L0595: 1. |
| 33 | HKABZ65 | 862030 | 232 | AR313: 41, AR242: 32, AR039: 28, AR165: 25, AR163: 25, AR164: 24, AR161: 24, AR162: 24, AR166: 24, AR089: 24, AR096: 23, AR173: 22, AR196: 20, AR193: 20, AR299: 20, AR300: 20, AR258: 20, AR180: 19, AR175: 19, AR178: 18, AR240: 18, AR229: 18, AR234: 18, AR185: 17, AR247: 17, AR218: 17, AR262: 17, AR179: 16, |

TABLE 1B.2-continued

| Gene No: | cDNA Clone ID | Contig ID: | SEQ ID NO: X | Tissue Distribution Library Code: Count (see Table 4 for Library Codes) |
|---|---|---|---|---|
| | | | | AR285: 16, AR183: 16, AR269: 16, AR293: 15, AR174: 15, AR199: 15, AR182: 15, AR181: 15, AR238: 14, AR191: 14, AR296: 14, AR236: 14, AR257: 14, AR316: 14, AR270: 14, AR226: 13, AR219: 13, AR297: 13, AR277: 13, AR264: 12, AR200: 12, AR312: 12, AR195: 12, AR213: 12, AR192: 12, AR203: 12, AR268: 12, AR212: 12, AR294: 12, AR286: 11, AR060: 11, AR230: 11, AR177: 11, AR189: 11, AR233: 11, AR260: 10, AR231: 10, AR198: 10, AR290: 10, AR188: 10, AR204: 10, AR0539, AR2879, AR2889, AR2559, AR2959, AR0339, AR2619, AR2829, AR1049, AR2459, AR2439, AR2359, AR2288, AR3088, AR2638, AR2758, AR2918, AR2018, AR2748, AR2377, AR1977, AR2397, AR2247, AR3117, AR1767, AR2677, AR1727, AR2567, AR2237, AR2057, AR1716, AR2276, AR1686, AR2146, AR2076, AR1696, AR2256, AR2526, AR2506, AR2716, AR2156, AR1706, AR2116, AR2216, AR3095, AR2835, AR2665, AR2545, AR2225, AR1905, AR2105, AR2165, AR2175, AR2325, AR0555, AR2894, AR2534, AR2464, AR2723, AR0612 H0494: 1 |
| 33 | HKABZ65 | 665424 | 234 | |

Table 1C summarizes additional polynucleotides encompassed by the invention (including cDNA clones related to the sequences (Clone ID:), contig sequences (contig identifier (Contig ID:) contig nucleotide sequence identifiers (SEQ ID NO:X)), and genomic sequences (SEQ ID NO:B). The first column provides a unique clone identifier, "cDNA Clone ID", for a cDNA clone related to each contig sequence. The second column provides the sequence identifier, "SEQ ID NO:X", for each contig sequence. The third column provides a unique contig identifier, "Contig ID:" for each contig sequence. The fourth column, provides a BAC identifier "BAC ID: A" for the BAC clone referenced in the corresponding row of the table. The fifth column provides the nucleotide sequence identifier, "SEQ ID NO:B" for a fragment of the BAC clone identified in column four of the corresponding row of the table. The sixth column, "Exon From-To", provides the location (i.e., nucleotide position numbers) within the polynucleotide sequence of SEQ ID NO:B which delineate certain polynucleotides of the invention that are also exemplary members of polynucleotide sequences that encode polypeptides of the invention (e.g., polypeptides containing amino acid sequences encoded by the polynucleotide sequences delineated in column six, and fragments and variants thereof). Table 1C from U.S. patent application Ser. No. 10/472,532, filed Sep. 20, 2003, is herein incorporated by reference. Table 1C in priority Application No. PCT/US02/09785, filed Mar. 19, 2002, which corresponds to Publication No. WO02/95010, published Nov. 28, 2002 (e.g., pages 228 to 235 of Publication No. WO02/95010) is incorporated by reference herein in its entirety.

TABLE 1C

| cDNA Clone ID | SEQ ID NO: X | CONTIG ID: | BAC ID: A | SEQ ID NO: B | EXON From-To |
|---|---|---|---|---|---|
| HETBX14 | 61 | 806447 | AC011473 | 247 | 1-205<br>727-1286<br>1995-2071<br>2865-3025<br>3352-3617<br>4434-4573<br>4958-5431 |
| HETBX14 | 61 | 806447 | AC011473 | 248 | 1-77<br>241-299 |

TABLE 1C-continued

| cDNA Clone ID | SEQ ID NO: X | CONTIG ID: | BAC ID: A | SEQ ID NO: B | EXON From-To |
|---|---|---|---|---|---|
| | | | | | 745-906<br>1417-1520<br>2346-2501<br>2754-2852<br>2923-3002<br>3962-4096<br>5422-5791 |
| HLHFP03 | 76 | 460467 | AC011976 | 251 | 1-467<br>1023-1116<br>2101-2317<br>2529-2630<br>2860-3097 |
| HLHFP03 | 76 | 460467 | AC011976 | 252 | 1-391 |
| HTADX17 | 90 | 457172 | AL357565 | 249 | 1-937<br>945-1293<br>2068-2336<br>2732-3109 |
| HTADX17 | 90 | 457172 | AL357565 | 250 | 1-104 |
| HJACG02 | 102 | 509948 | AC008763 | | 1-47<br>243-371<br>736-823<br>1144-1381 |
| HJACG02 | 102 | 509948 | AC008763 | | 1-32<br>407-497<br>818-1357<br>2275-2380<br>2384-2560 |
| HT5GJ57 | 159 | 740767 | AC005081 | 253 | 1-149<br>1029-1450<br>4881-5071<br>5302-5397<br>6004-6132<br>6888-6926<br>7229-7329<br>9066-9254<br>9805-9848<br>9852-10211<br>10276-10315<br>10619-10807<br>10855-11472<br>11695-11852<br>12358-12468<br>13770-13847<br>14053-14259<br>14695-14822<br>16101-16553 |

TABLE 1C-continued

| cDNA Clone ID | SEQ ID NO: X | CONTIG ID: | BAC ID: A | SEQ ID NO: B | EXON From-To |
|---|---|---|---|---|---|
| | | | | | 18233-18690 |
| | | | | | 18750-19965 |
| HT5GJ57 | 159 | 740767 | AC016675 | 254 | 1-149 |
| | | | | | 1029-1450 |
| | | | | | 1623-1790 |
| | | | | | 4908-5098 |
| | | | | | 5329-5424 |
| | | | | | 6031-6159 |
| | | | | | 6915-6953 |
| | | | | | 7256-7356 |
| | | | | | 9095-9306 |
| | | | | | 9834-9877 |
| | | | | | 9881-10239 |
| | | | | | 10304-10343 |
| | | | | | 10647-10835 |
| | | | | | 10883-11500 |
| | | | | | 11724-11881 |
| | | | | | 13799-13876 |
| | | | | | 14082-14288 |
| | | | | | 14725-14852 |
| | | | | | 16131-16583 |
| | | | | | 18262-18719 |
| | | | | | 18757-19994 |
| | | | | | 20161-20420 |
| HT5GJ57 | 159 | 740767 | AC005081 | 255 | 1-233 |
| HT5GJ57 | 159 | 740767 | AC016675 | 256 | 1-720 |
| | | | | | 2099-2265 |
| | | | | | 2776-3550 |
| | | | | | 3946-4146 |
| | | | | | 4976-5104 |
| | | | | | 5781-6171 |
| | | | | | 6476-7039 |
| | | | | | 7384-7738 |
| | | | | | 7837-8009 |
| | | | | | 8434-8593 |
| | | | | | 11644-11746 |

Tables 1D, 1E, 1E.1, and 1E.2: The polynucleotides or polypeptides, or agonists or antagonists of the present invention can be used in assays to test for one or more biological activities. If these polynucleotides and polypeptides do exhibit activity in a particular assay, it is likely that these molecules may be involved in the diseases associated with the biological activity. Thus, the polynucleotides or polypeptides, or agonists or antagonists could be used to treat the associated disease.

The present invention encompasses methods of detecting, preventing, diagnosing, prognosticating, treating, and/or ameliorating a disease or disorder. In preferred embodiments, the present invention encompasses a method of treating a disease or disorder (such as a disease listed in the "Preferred Indications" columns of Tables 1D, 1E, 1E.2, or 1F, and in particular, an immune, cardiovascular, cancer, or other proliferative disease or disorder) comprising administering to a patient in which such detection, treatment, prevention, and/or amelioration is desired a protein, nucleic acid, or antibody of the invention (or fragment or variant thereof) in an amount effective to detect, prevent, diagnose, prognosticate, treat, and/or ameliorate the disease or disorder. The first and second columns of Table 1D show the "Gene No." and "cDNA Clone ID No.", respectively, indicating certain nucleic acids and proteins (or antibodies against the same) of the invention (including polynucleotide, polypeptide, and antibody fragments or variants thereof) that may be used in preventing, treating, diagnosing, or ameliorating the disease(s) or disorder(s) indicated in the corresponding row in Column 3 of Table 1D.

In another embodiment, the present invention also encompasses methods of detecting, preventing, diagnosing, prognosticating, treating, and/or ameliorating a disease or disorder (such as a disease listed in the "Preferred Indications" columns of Tables 1D, 1E, 1E.2, or 1F, and in particular, an immune, cardiovascular, cancer, or other proliferative disease or disorder); comprising administering to a patient combinations of the proteins, nucleic acids, or antibodies of the invention (or fragments or variants thereof), sharing similar indications as shown in the corresponding rows in Column 3 of Table 1D or in the "Preferred Indications" columns of Tables 1E, 1E.2, or 1F.

The "Preferred Indications" columns of Tables 1D, 1E, 1E.2, and 1F describe diseases, disorders, and/or conditions that may be treated, prevented, diagnosed, or ameliorated by a protein, nucleic acid, or antibody of the invention (or fragment or variant thereof).

The recitation of "Cancer" in the "Preferred Indications" columns indicates that the corresponding nucleic acid and protein, or antibody against the same, of the invention (or fragment or variant thereof) may be used for example, to diagnose, treat, prevent, and/or ameliorate diseases and/or disorders relating to neoplastic diseases (e.g., leukemias, cancers, and/or as described below under "Hyperproliferative Disorders").

In specific embodiments, a protein, nucleic acid, or antibody of the invention (or fragment or variant thereof) having a "Cancer" recitation in the "Preferred Indication" column of Table 1D may be used for example, to diagnose, treat, prevent, and/or ameliorate a neoplasm located in a tissue selected from the group consisting of: colon, abdomen, bone, breast, digestive system, liver, pancreas, prostate, peritoneum, lung, blood (e.g., leukemia), endocrine glands (adrenal, parathyroid, pituitary, testicles, ovary, thymus, thyroid), uterus, eye, head and neck, nervous (central and peripheral), lymphatic system, pelvic, skin, soft tissue, spleen, thoracic, and urogenital.

In specific embodiments, a protein, nucleic acid, or antibody of the invention (or fragment or variant thereof) having a "Cancer" recitation in the "Preferred Indication" column of Table 1D, may be used for example, to diagnose, treat, prevent, and/or ameliorate a pre-neoplastic condition, selected from the group consisting of: hyperplasia (e.g., endometrial hyperplasia and/or as described in the section entitled "Hyperproliferative Disorders"), metaplasia (e.g., connective tissue metaplasia, atypical metaplasia, and/or as described in the section entitled "Hyperproliferative Disorders"), and/or dysplasia (e.g., cervical dysplasia, and bronchopulmonary dysplasia).

In another specific embodiment, a protein, nucleic acid, or antibody of the invention (or fragment or variant thereof) having a "Cancer" recitation in the "Preferred Indication" column of Table 1D, may be used for example, to diagnose, treat, prevent, and/or ameliorate a benign dysproliferative disorder selected from the group consisting of: benign tumors, fibrocystic conditions, tissue hypertrophy, and/or as described in the section entitled "Hyperproliferative Disorders".

The recitation of "Immune/Hematopoietic" in the "Preferred Indication" column indicates that the corresponding nucleic acid and protein, or antibody against the same, of the invention (or fragment or variant thereof), may be used for example, to diagnose, treat, prevent, and/or ameliorate diseases and/or disorders relating to neoplastic diseases (e.g., as described below under "Hyperproliferative Disorders"), blood disorders (e.g., as described below under "Immune Activity" "Cardiovascular Disorders" and/or "Blood-Related Disorders"), and infections (e.g., as described below under "Infectious Disease").

In specific embodiments, a protein, nucleic acid, or antibody of the invention (or fragment or variant thereof) having the "Immune/Hematopoietic" recitation in the "Preferred Indication" column of Table 1D, may be used for example, to diagnose, treat, prevent, and/or ameliorate a disease or disorder selected from the group consisting of: anemia, pancytopenia, leukopenia, thrombocytopenia, leukemias, Hodgkin's disease, non-Hodgkin's lymphoma, acute lymphocytic anemia (ALL), plasmacytomas, multiple myeloma, Burkitt's lymphoma, arthritis, asthma, AIDS, autoimmune disease, rheumatoid arthritis, granulomatous disease, immune deficiency, inflammatory bowel disease, sepsis, neutropenia, neutrophilia, psoriasis, immune reactions to transplanted organs and tissues, systemic lupus erythematosis, hemophilia, hypercoagulation, diabetes mellitus, endocarditis, meningitis, Lyme Disease, and allergies.

The recitation of "Reproductive" in the "Preferred Indication" column indicates that the corresponding nucleic acid and protein, or antibody against the same, of the invention (or fragment or variant thereof), may be used for example, to diagnose, treat, prevent, and/or ameliorate diseases and/or disorders relating to neoplastic diseases (e.g., as described below under "Hyperproliferative Disorders"), and disorders of the reproductive system (e.g., as described below under "Reproductive System Disorders").

In specific embodiments, a protein, nucleic acid, or antibody of the invention (or fragment or variant thereof) having a "Reproductive" recitation in the "Preferred Indication" column of Table 1D, may be used for example, to diagnose, treat, prevent, and/or ameliorate a disease or disorder selected from the group consisting of: cryptorchism, prostatitis, inguinal hernia, varicocele, leydig cell tumors, verrucous carcinoma, prostatitis, malacoplakia, Peyronie's disease, penile carcinoma, squamous cell hyperplasia, dysmenorrhea, ovarian adenocarcinoma, Turner's syndrome, mucopurulent cervicitis, Sertoli-leydig tumors, ovarian cancer, uterine cancer, pelvic inflammatory disease, testicular cancer, prostate cancer, Klinefelter's syndrome, Young's syndrome, premature ejaculation, diabetes mellitus, cystic fibrosis, Kartagener's syndrome, testicular atrophy, testicular feminization, anorchia, ectopic testis, epididymitis, orchitis, gonorrhea, syphilis, testicular torsion, vasitis nodosa, germ cell tumors, stromal tumors, dysmenorrhea, retroverted uterus, endometriosis, fibroids, adenomyosis, anovulatory bleeding, amenorrhea, Cushing's syndrome, hydatidiform moles, Asherman's syndrome, premature menopause, precocious puberty, uterine polyps, dysfunctional uterine bleeding, cervicitis, chronic cervicitis, mucopurulent cervicitis, cervical dysplasia, cervical polyps, Nabothian cysts, cervical erosion, cervical incompetence, cervical neoplasms, pseudohermaphroditism, and premenstrual syndrome.

The recitation of "Musculoskeletal" in the "Preferred Indication" column indicates that the corresponding nucleic acid and protein, or antibody against the same, of the invention (or fragment or variant thereof), may be used for example, to diagnose, treat, prevent, and/or ameliorate diseases and/or disorders relating to neoplastic diseases (e.g., as described below under "Hyperproliferative Disorders"), and disorders of the immune system (e.g., as described below under "Immune Activity").

In specific embodiments, a protein, nucleic acid, or antibody of the invention (or fragment or variant thereof) having a "Musculoskeletal" recitation in the "Preferred Indication" column of Table 1D, may be used for example, to diagnose, treat, prevent, and/or ameliorate a disease or disorder selected from the group consisting of: bone cancers (e.g., osteochondromas, benign chondromas, chondroblastoma, chondromyxoid fibromas, osteoid osteomas, giant cell tumors, multiple myeloma, osteosarcomas), Paget's Disease, rheumatoid arthritis, systemic lupus erythematosus, osteomyelitis, Lyme Disease, gout, bursitis, tendonitis, osteoporosis, osteoarthritis, muscular dystrophy, mitochondrial myopathy, cachexia, and multiple sclerosis.

The recitation of "Cardiovascular" in the "Preferred Indication" column indicates that the corresponding nucleic acid and protein, or antibody against the same, of the invention (or fragment or variant thereof), may be used for example, to diagnose, treat, prevent, and/or ameliorate diseases and/or disorders relating to neoplastic diseases (e.g., as described below under "Hyperproliferative Disorders"), and disorders of the cardiovascular system (e.g., as described below under "Cardiovascular Disorders").

In specific embodiments, a protein, nucleic acid, or antibody of the invention (or fragment or variant thereof) having a "Cardiovascular" recitation in the "Preferred Indication" column of Table 1D, may be used for example, to diagnose, treat, prevent, and/or ameliorate a disease or disorder selected from the group consisting of: myxomas, fibromas, rhabdomyomas, cardiovascular abnormalities (e.g., congenital heart defects, cerebral arteriovenous malformations, septal defects), heart disease (e.g., heart failure, congestive heart disease, arrhythmia, tachycardia, fibrillation, pericardial Disease, endocarditis), cardiac arrest, heart valve disease (e.g., stenosis, regurgitation, prolapse), vascular disease (e.g., hypertension, coronary artery disease, angina, aneurysm, arteriosclerosis, peripheral vascular disease), hyponatremia, hypernatremia, hypokalemia, and hyperkalemia.

The recitation of "Mixed Fetal" in the "Preferred Indication" column indicates that the corresponding nucleic acid and protein, or antibody against the same, of the invention (or fragment or variant thereof), may be used for example, to diagnose, treat, prevent, and/or ameliorate diseases and/or disorders relating to neoplastic diseases (e.g., as described below under "Hyperproliferative Disorders").

In specific embodiments, a protein, nucleic acid, or antibody of the invention (or fragment or variant thereof) having a "Mixed Fetal" recitation in the "Preferred Indication" column of Table 1D, may be used for example, to diagnose, treat, prevent, and/or ameliorate a disease or disorder selected from the group consisting of: spina bifida, hydranencephaly, neurofibromatosis, fetal alcohol syndrome, diabetes mellitus, PKU, Down's syndrome, Patau syndrome, Edwards syndrome, Turner syndrome, Apert syndrome, Carpenter syndrome, Conradi syndrome, Crouzon syndrome, cutis laxa, Cornelia de Lange syndrome, Ellis-van Creveld syndrome, Holt-Oram syndrome, Kartagener syndrome, Meckel-Gruber syndrome, Noonan syndrome, Pallister-Hall syndrome, Rubinstein-Taybi syndrome, Scimitar syndrome, Smith-Lemli-Opitz syndrome, thromocytopenia-absent radius (TAR) syndrome, Treacher Collins syndrome, Williams syndrome, Hirschsprung's disease, Meckel's diverticulum, polycystic kidney disease, Turner's syndrome, and gonadal dysgenesis, Klippel-Feil syndrome, Ostogenesis imperfecta, muscular dystrophy, Tay-Sachs disease, Wilm's tumor, neuroblastoma, and retinoblastoma.

The recitation of "Excretory" in the "Preferred Indication" column indicates that the corresponding nucleic acid and protein, or antibody against the same, of the invention (or fragment or variant thereof), may be used for example, to diagnose, treat, prevent, and/or ameliorate diseases and/or disorders relating to neoplastic diseases (e.g., as described below under "Hyperproliferative Disorders") and renal disorders (e.g., as described below under "Renal Disorders").

In specific embodiments, a protein, nucleic acid, or antibody of the invention (or fragment or variant thereof) having a "Excretory" recitation in the "Preferred Indication" column of Table 1D, may be used for example, to diagnose, treat, prevent, and/or ameliorate a disease or disorder selected from the group consisting of: bladder cancer, prostate cancer, benign prostatic hyperplasia, bladder disorders (e.g., urinary incontinence, urinary retention, urinary obstruction, urinary tract Infections, interstitial cystitis, prostatitis, neurogenic bladder, hematuria), renal disorders (e.g., hydronephrosis, proteinuria, renal failure, pyelonephritis, urolithiasis, reflux nephropathy, and unilateral obstructive uropathy).

The recitation of "Neural/Sensory" in the "Preferred Indication" column indicates that the corresponding nucleic acid and protein, or antibody against the same, of the invention (or fragment or variant thereof), may be used for example, to diagnose, treat, prevent, and/or ameliorate diseases and/or disorders relating to neoplastic diseases (e.g., as described below under "Hyperproliferative Disorders") and diseases or disorders of the nervous system (e.g., as described below under "Neural Activity and Neurological Diseases").

In specific embodiments, a protein, nucleic acid, or antibody of the invention (or fragment or variant thereof) having a "Neural/Sensory" recitation in the "Preferred Indication" column of Table 1D, may be used for example, to diagnose, treat, prevent, and/or ameliorate a disease or disorder selected from the group consisting of: brain cancer (e.g., brain stem glioma, brain tumors, central nervous system (Primary) lymphoma, central nervous system lymphoma, cerebellar astrocytoma, and cerebral astrocytoma, neurodegenerative disorders (e.g., Alzheimer's Disease, Creutzfeldt-Jakob Disease, Parkinson's Disease, and Idiopathic Presenile Dementia), encephalomyelitis, cerebral malaria, meningitis, metabolic brain diseases (e.g., phenylketonuria and pyruvate carboxylase deficiency), cerebellar ataxia, ataxia telangiectasia, and AIDS Dementia Complex, schizophrenia, attention deficit disorder, hyperactive attention deficit disorder, autism, and obsessive compulsive disorders.

The recitation of "Respiratory" in the "Preferred Indication" column indicates that the corresponding nucleic acid and protein, or antibody against the same, of the invention (or fragment or variant thereof), may be used for example, to diagnose, treat, prevent, and/or ameliorate diseases and/or disorders relating to neoplastic diseases (e.g., as described below under "Hyperproliferative Disorders") and diseases or disorders of the respiratory system (e.g., as described below under "Respiratory Disorders").

In specific embodiments, a protein, nucleic acid, or antibody of the invention (or fragment or variant thereof) having a "Respiratory" recitation in the "Preferred Indication" column of Table 1D, may be used for example, to diagnose, treat, prevent, and/or ameliorate a disease or disorder selected from the group consisting of: cancers of the respiratory system such as larynx cancer, pharynx cancer, trachea cancer, epiglottis cancer, lung cancer, squamous cell carcinomas, small cell (oat cell) carcinomas, large cell carcinomas, and adenocarcinomas. Allergic reactions, cystic fibrosis, sarcoidosis, histiocytosis X, infiltrative lung diseases (e.g., pulmonary fibrosis and lymphoid interstitial pneumonia), obstructive airway diseases (e.g., asthma, emphysema, chronic or acute bronchitis), occupational lung diseases (e.g., silicosis and asbestosis), pneumonia, and pleurisy.

The recitation of "Endocrine" in the "Preferred Indication" column indicates that the corresponding nucleic acid and protein, or antibody against the same, of the invention (or fragment or variant thereof), may be used for example, to diagnose, treat, prevent, and/or ameliorate diseases and/or disorders relating to neoplastic diseases (e.g., as described below under "Hyperproliferative Disorders") and diseases or disorders of the respiratory system (e.g., as described below under "Respiratory Disorders"), renal disorders (e.g., as described below under "Renal Disorders"), and disorders of the endocrine system (e.g., as described below under "Endocrine Disorders".

In specific embodiments, a protein, nucleic acid, or antibody of the invention (or fragment or variant thereof) having an "Endocrine" recitation in the "Preferred Indication" column of Table 1D, may be used for example, to diagnose, treat, prevent, and/or ameliorate a disease or disorder selected from the group consisting of: cancers of endocrine tissues and organs (e.g., cancers of the hypothalamus, pituitary gland, thyroid gland, parathyroid glands, pancreas, adrenal glands, ovaries, and testes), diabetes (e.g., diabetes insipidus, type I and type II diabetes mellitus), obesity, disorders related to pituitary glands (e.g., hyperpituitarism, hypopituitarism, and pituitary dwarfism), hypothyroidism, hyperthyroidism, goiter, reproductive disorders (e.g. male and female infertility), disorders related to adrenal glands (e.g., Addison's Disease, corticosteroid deficiency, and Cushing's Syndrome), kidney cancer (e.g., hypernephroma, transitional cell cancer, and Wilm's tumor), diabetic nephropathy, interstitial nephritis, polycystic kidney disease, glomerulonephritis (e.g., IgM mesangial proliferative glomerulonephritis and glomerulonephritis caused by autoimmune disorders; such as Goodpasture's syndrome), and nephrocalcinosis.

The recitation of "Digestive" in the "Preferred Indication" column indicates that the corresponding nucleic acid and protein, or antibody against the same, of the invention (or fragment or variant thereof), may be used for example, to diagnose, treat, prevent, and/or ameliorate diseases and/or disorders relating to neoplastic diseases (e.g., as described below under "Hyperproliferative Disorders") and diseases or disorders of the gastrointestinal system (e.g., as described below under "Gastrointestinal Disorders".

In specific embodiments, a protein, nucleic acid, or antibody of the invention (or fragment or variant thereof) having a "Digestive" recitation in the "Preferred Indication" column of Table 1D, may be used for example, to diagnose, treat, prevent, and/or ameliorate a disease or disorder selected from the group consisting of: ulcerative colitis, appendicitis, Crohn's disease, hepatitis, hepatic encephalopathy, portal hypertension, cholelithiasis, cancer of the digestive system (e.g., biliary tract cancer, stomach cancer, colon cancer, gastric cancer, pancreatic cancer, cancer of the bile duct, tumors of the colon (e.g., polyps or cancers), and cirrhosis), pancreatitis, ulcerative disease, pyloric stenosis, gastroenteritis, gastritis, gastric atropy, benign tumors of the duodenum, distension, irritable bowel syndrome, malabsorption, congenital disorders of the small intestine, bacterial and parasitic infection, megacolon, Hirschsprung's disease, aganglionic megacolon, acquired megacolon, colitis, anorectal disorders (e.g., anal fistulas, hemorrhoids), congenital disorders of the liver (e.g., Wilson's disease, hemochromatosis, cystic fibrosis, biliary atresia, and alpha1-antitrypsin deficiency), portal hypertension, cholelithiasis, and jaundice.

The recitation of "Connective/Epithelial" in the "Preferred Indication" column indicates that the corresponding nucleic acid and protein, or antibody against the same, of the invention (or fragment or variant thereof), may be used for example, to diagnose, treat, prevent, and/or ameliorate diseases and/or disorders relating to neoplastic diseases (e.g., as described below under "Hyperproliferative Disorders"), cellular and genetic abnormalities (e.g., as described below under "Diseases at the Cellular Level"), angiogenesis (e.g., as described below under "Anti-Angiogenesis Activity"), and or to promote or inhibit regeneration (e.g., as described below under "Regeneration"), and wound healing (e.g., as described below under "Wound Healing and Epithelial Cell Proliferation").

In specific embodiments, a protein, nucleic acid, or antibody of the invention (or fragment or variant thereof) having a "Connective/Epithelial" recitation in the "Preferred Indication" column of Table 1D, may be used for example, to diagnose, treat, prevent, and/or ameliorate a disease or disorder selected from the group consisting of: connective tissue metaplasia, mixed connective tissue disease, focal epithelial hyperplasia, epithelial metaplasia, mucoepithelial dysplasia, graft v. host disease, polymyositis, cystic hyperplasia, cerebral dysplasia, tissue hypertrophy, Alzheimer's disease, lymphoproliferative disorder, Waldenstron's macroglobulinemia, Crohn's disease, pernicious anemia, idiopathic Addison's disease, glomerulonephritis, bullous pemphigoid, Sjogren's syndrome, diabetes mellitus, cystic fibrosis, osteoblastoma, osteoclastoma, osteosarcoma, chondrosarcoma, osteoporosis, osteocarthritis, periodontal disease, wound healing, relapsing polychondritis, vasculitis, polyarteritis nodosa, Wegener's granulomatosis, cellulitis, rheumatoid arthritis, psoriatic arthritis, discoid lupus erythematosus, systemic lupus erythematosus, scleroderma, CREST syndrome, Sjogren's syndrome, polymyositis, dermatomyositis, mixed connective tissue disease, relapsing polychondritis, vasculitis, Henoch-Schonlein syndrome, erythema nodosum, polyarteritis nodosa, temporal (giant cell) arteritis, Takayasu's arteritis, Wegener's granulomatosis, Reiter's syndrome, Behcet's syndrome, ankylosing spondylitis, cellulitis, keloids, Ehler Danlos syndrome, Marfan syndrome, pseudoxantoma elasticum, osteogenese imperfecta, chondrodysplasias, epidermolysis bullosa, Alport syndrome, and cutis laxa.

TABLE 1D

| Gene No. | cDNA Clone ID | Preferred Indications |
|---|---|---|
| 3 | HTEEB42 | Cancer |
| 4 | HEMCM42 | Cancer |
| 4 | HEQCC55 | Cancer |
| 5 | HEMAE80 | Cardiovascular, Musculoskeletal, Reproductive |
| 6 | HRDFB85 | Cancer |
| 7 | HDTAW95 | Cancer |
| 8 | HEMCV19 | Cancer |
| 9 | HETBX14 | Cancer |
| 10 | HLHSK94 | Cancer |
| 11 | HLHFP03 | Respiratory |
| 11 | HLHFP03 | Respiratory |
| 12 | HHTLF25 | Cancer |
| 13 | HTADX17 | Immune/Hematopoetic, Reproductive |
| 13 | HTADX17 | Immune/Hematopoetic, Reproductive |
| 14 | HJACG02 | Digestive, Immune/Hematopoetic |
| 15 | HKGAJ54 | Cancer |

TABLE 1D-continued

| Gene No. | cDNA Clone ID | Preferred Indications |
|---|---|---|
| 16 | HE8CH92 | Cancer |
| 16 | HSVAK93 | Cancer |
| 17 | HSDEK49 | Cancer |
| 18 | HWBAO62 | Connective/Epithelial, Immune/Hematopoetic |
| 19 | HWHGU54 | Connective/Epithelial |
| 20 | HCEJQ69 | Cancer |
| 21 | HT5GJ57 | Cancer |
| 21 | HT5GJ57 | Cancer |
| 22 | HPIBX03 | Cancer |
| 23 | HDPBO81 | Digestive, Immune/Hematopoetic, Reproductive |
| 24 | HWBFY57 | Digestive, Immune/Hematopoetic |
| 25 | HYABV21 | Immune/Hematopoietic |
| 26 | HOHBY69 | Cancer |
| 27 | HDHMA45 | Cardiovascular, Neural/Sensory |
| 28 | HMADJ14 | Connective/Epithelial, Immune/Hematopoetic, Musculoskeletal |
| 28 | HMADJ14 | Connective/Epithelial, Immune/Hematopoietic, Musculoskeletal |
| 30 | HEMFA84 | Cancer |
| 31 | HDPPA04 | Cardiovascular, Connective/Epithelial, Immune/Hematopoetic |
| 32 | HE2OA95 | Cancer |
| 33 | HKABZ65 | Connective/Epithelial |

Table 1E provides information related to biological activities and preferred indications for polynucleotides and polypeptides of the invention (including antibodies, agonists, and/or antagonists thereof). Table 1E also provides information related to assays which may be used to test polynucleotides and polypeptides of the invention (including antibodies, agonists, and/or antagonists thereof) for the corresponding biological activities. The first column ("Gene No.") provides the gene number in the application for each clone identifier. The second column ("cDNA Clone ID") provides the unique clone identifier for each clone as previously described and indicated in Tables 1A, 1B.1, 1B.2, 1C, and 1D. The third column ("AA SEQ ID NO:Y") indicates the Sequence Listing SEQ ID Number for polypeptide sequences encoded by the corresponding cDNA clones (also as indicated in Tables 1A and 1B.1). The fourth column ("Biological Activity") indicates a biological activity corresponding to the indicated polypeptides (or polynucleotides encoding said polypeptides). The fifth column ("Exemplary Activity Assay") further describes the corresponding biological activity and also provides information pertaining to the various types of assays which may be performed to test, demonstrate, or quantify the corresponding biological activity. The sixth column ("Preferred Indications") describes particular embodiments of the invention as well as indications (e.g. pathologies, diseases, disorders, abnormalities, etc.) for which polynucleotides and polypeptides of the invention (including antibodies, agonists, and/or antagonists thereof) may be used in detecting, diagnosing, preventing, and/or treating.

TABLE 1E

| Gene No. | cDNA Clone ID | AA SEQ ID NO: Y | Biological Activity | Exemplary Activity Assay | Preferred Indication |
|---|---|---|---|---|---|
| 3 | HTEEB42 | 10 | Regulation of transcription of Malic Enzyme in hepatocytes | Assays for the regulation of transcription of Malic Enzyme are well-known in the art and may be used or routinely modified to assess the ability of polypeptides of the invention (including antibodies and | A highly preferred indication is 'diabetes mellitus. An additional highly preferred indication is a complication associated with diabetes (e.g., diabetic retinopathy, diabetic nephropathy, kidney disease (e.g., renal failure, nephropathy and/or other diseases and disorders as |

TABLE 1E-continued

| Gene No. | cDNA Clone ID | AA SEQ ID NO: Y | Biological Activity | Exemplary Activity Assay | Preferred Indication |
|---|---|---|---|---|---|
| | | | | agonists or antagonists of the invention) to regulate transcription of Malic Enzyme, a key enzyme in lipogenesis. Malic enzyme is involved in lipogenesisand its expression is stimulted by insulin. ME promoter contains two direct repeat (DR1)-like elements MEp and MEd identified as putative PPAR response elements. ME promoter may also responds to AP1 and other transcription factors. Exemplary assays that may be used or routinely modified to test for regulation of transcription of Malic Enzyme (in hepatocytes) by polypeptides of the invention (including antibodies and agonists or antagonists of the invention) include assays disclosed in: Streeper, R. S., et al., Mol Endocrinol, 12(11): 1778-91 (1998); Garcia-Jimenez, C., et al., Mol Endocrinol, 8(10): 1361-9 (1994); Barroso, I., et al., J Biol Chem, 274(25): 17997-8004 (1999); Ijpenberg, A., et al., J Biol Chem, 272(32): 20108-20117 (1997); Berger, et al., Gene 66: 1-10 (1988); and, Cullen, B., et al., Methods in Enzymol. 216: 362-368 (1992), the contents of each of which is herein incorporated by reference in its entirety. Hepatocytes that may be used according to these assays are publicly available (e.g., through the ATCC ™) and/or may be routinely generated. Exemplary hepatocytes that may be used according to these assays includes the mouse 3T3-L1 cell line. 3T3-L1 is a mouse preadipocyte cell line (adherent). It is a continuous substrain of 3T3 fibroblasts developed through clonal isolation. Cells undergo a pre-adipocyte to adipose-like conversion under appropriate differentiation culture conditions. | described in the "Renal Disorders" section below), diabetic neuropathy, nerve disease and nerve damage (e.g., due to diabetic neuropathy), blood vessel blockage, heart disease, stroke, impotence (e.g., due to diabetic neuropathy or blood vessel blockage), seizures, mental confusion, drowsiness, nonketotic hyperglycemic-hyperosmolar coma, cardiovascular disease (e.g., heart disease, atherosclerosis, microvascular disease, hypertension, stroke, and other diseases and disorders as described in the "Cardiovascular Disorders" section below), dyslipidemia, endocrine disorders (as described in the "Endocrine Disorders" section below), neuropathy, vision impairment (e.g., diabetic retinopathy and blindness), ulcers and impaired wound healing, and infection (e.g., infectious diseases and disorders as described in the "Infectious Diseases" section below, especially of the urinary tract and skin), carpal tunnel syndrome and Dupuytren's contracture). An additional highly preferred indication is obesity and/or complications associated with obesity. Additional highly preferred indications include weight loss or alternatively, weight gain. Aditional highly preferred indications are complications associated with insulin resistance. |
| 4 | HEQCC55 | 16 | Production of MCP-1 | MCP-1 FMAT. Assays for immunomodulatory proteins that are produced by a large variety of cells and act to induce chemotaxis and activation of monocytes and T cells are well known in the art and may be used or routinely modified to assess the ability of polypeptides of the invention (including antibodies and agonists or antagonists of the invention) to mediate immunomodulation, induce chemotaxis, and modulate immune cell activation. Exemplary assays that test for immunomodulatory proteins | A highly preferred embodiment of the invention includes a method for stimulating (e.g., increasing) MCP-1 production. An alternative highly preferred embodiment of the invention includes a method for inhibiting (e.g., reducing) MCP-1 production. A highly preferred indication is infection (e.g., an infectious disease as described below under "Infectious Disease"). Additional highly preferred indications include inflammation and inflammatory disorders. Preferred indications include blood disorders (e.g., as described below under "Immune Activity", "Blood-Related Disorders", and/or "Cardiovascular Disorders"). Highly preferred indications include autoimmune diseases (e.g., rheumatoid arthritis, |

TABLE 1E-continued

| Gene No. | cDNA Clone ID | AA SEQ ID NO: Y | Biological Activity | Exemplary Activity Assay | Preferred Indication |
|---|---|---|---|---|---|
| | | | | evaluate the production of cell surface markers, such as monocyte chemoattractant protein (MCP), and the activation of monocytes and T cells. Such assays that may be used or routinely modified to test immunomodulatory and differentiation activity of polypeptides of the invention (including antibodies and agonists or antagonists of the invention) include assays disclosed in Miraglia et al., J Biomolecular Screening 4: 193-204 (1999); Rowland et al., "Lymphocytes: a practical approach" Chapter 6: 138-160 (2000); Satthaporn and Eremin, J R Coll Surg Ednb 45(1): 9-19 (2001); and Verhasselt et al., J Immunol 158: 2919-2925 (1997), the contents of each of which are herein incorporated by reference in its entirety. Human dendritic cells that may be used according to these assays may be isolated using techniques disclosed herein or otherwise known in the art. Human dendritic cells are antigen presenting cells in suspension culture, which, when activated by antigen and/or cytokines, initiate and upregulate T cell proliferation and functional activities. | systemic lupus erythematosis, multiple sclerosis and/or as described below) and immunodeficiencies (e.g., as described below). Preferred indications also include anemia, pancytopenia, leukopenia, thrombocytopenia, Hodgkin's disease, acute lymphocytic anemia (ALL), plasmacytomas, multiple myeloma, Burkitt's lymphoma, arthritis, AIDS, granulomatous disease, inflammatory bowel disease, sepsis, neutropenia, neutrophilia, psoriasis, suppression of immune reactions to transplanted organs and tissues, hemophilia, hypercoagulation, diabetes mellitus, endocarditis, meningitis (bacterial and viral), Lyme Disease, asthma, and allergy Preferred indications also include neoplastic diseases (e.g., leukemia, lymphoma, and/or as described below under "Hyperproliferative Disorders"). Highly preferred indications include neoplasms and cancers, such as, leukemia, lymphoma, prostate, breast, lung, colon, pancreatic, esophageal, stomach, brain, liver, and urinary cancer. Other preferred indications include benign dysproliferative disorders and pre-neoplastic conditions, such as, for example, hyperplasia, metaplasia, and/or dysplasia. |
| 4 | HEQCC55 | 16 | Production of IL-13 and activation of T-cells. | Assays for production of IL-13 and activation of T-cells are well known in the art and may be used or routinely modified to assess the ability of polypeptides of the invention (including antibodies and agonists or antagonists of the invention) to stimulate or inhibit production of IL-13 and/or activation of T-cells. Exemplary assays for IL-13 production that may be used or routinely modified to test activity of polypeptides and antibodies of the invention (including agonists or antagonists of the invention) include, for example, assays such as disclosed and/or cited in: Grunig, G, et al., "Requirement for IL-13 independently of IL-4 in Experimental asthma" Science; 282: 2261-2263 (1998), and Wills-Karp M, et al., "Interleukin-13: central mediator of allergic asthma" Science; 282: 2258-2261 (1998); the contents of each of which are herein incorporated by reference in their entirety. Exemplary cells that may be used according to these assays include Th2 cells. IL13, a Th2 type cytokine, is a potent stimulus for mucus production, airway hyper-responsiveness | Highly preferred indications include allergy and asthma. Additional highly preferred indications include immune and hematopoietic disorders (e.g., as described below under "Immune Activity", and "Blood-Related Disorders"), autoimmune diseases (e.g., rheumatoid arthritis, systemic lupus erythematosis, Crohn''s disease, multiple sclerosis and/or as described below), immunodeficiencies (e.g., as described below), boosting a T cell-mediated immune response, and suppressing a T cell-mediated immune response. |

TABLE 1E-continued

| Gene No. | cDNA Clone ID | AA SEQ ID NO: Y | Biological Activity | Exemplary Activity Assay | Preferred Indication |
|---|---|---|---|---|---|
| | | | | and allergic asthma. Th2 cells are a class of T cells that secrete IL4, IL10, IL13, IL5 and IL6. Factors that induce differentiation and activation of Th2 cells play a major role in the initiation and pathogenesis of allergy and asthma. Primary T helper 2 cells are generated in in vitro culture under Th2 polarizing conditions using peripheral blood lymphocytes isolated from cord blood. | |
| 11 | HLHFP03 | 77 | Activation of T-Cell p38 or JNK Signaling Pathway. | Kinase assay. JNK and p38 kinase assays for signal transduction that regulate cell proliferation, activation, or apoptosis are well known in the art and may be used or routinely modified to assess the ability of polypeptides of the invention (including antibodies and agonists or antagonists of the invention) to promote or inhibit immune cell (e.g. T-cell) proliferation, activation, and apoptosis. Exemplary assays for JNK and p38 kinase activity that may be used or routinely modified to test JNK and p38 kinase-induced activity of polypeptides of the invention (including antibodies and agonists or antagonists of the invention) include the assays disclosed in Forrer et al., Biol Chem 379(8-9): 1101-1110 (1998); Gupta et al., Exp Cell Res 247(2): 495-504 (1999); Kyriakis J M, Biochem Soc Symp 64: 29-48 (1999); Chang and Karin, Nature 410(6824): 37-40 (2001); and Cobb M H, Prog Biophys Mol Biol 71(3-4): 479-500 (1999); the contents of each of which are herein incorporated by reference in its entirety. T cells that may be used according to these assays are publicly available (e.g., through the ATCC ™). Exemplary mouse T cells that may be used according to these assays include the CTLL cell line, which is an IL-2 dependent suspension-culture cell line with cytotoxic activity. | Preferred indications include neoplastic diseases (e.g., as described below under "Hyperproliferative Disorders"), blood disorders (e.g., as described below under "Immune Activity", "Cardiovascular Disorders", and/or "Blood-Related Disorders"), and infection (e.g., an infectious disease as described below under "Infectious Disease"). Highly preferred indications include autoimmune diseases (e.g., rheumatoid arthritis, systemic lupus erythematosis, multiple sclerosis and/or as described below) and immunodeficiencies (e.g., as described below). Additional highly preferred indications include inflammation and inflammatory disorders. Highly preferred indications also include neoplastic diseases (e.g., leukemia, lymphoma, and/or as described below under "Hyperproliferative Disorders"). Highly preferred indications include neoplasms and cancers, such as, leukemia, lymphoma, prostate, breast, lung, colon, pancreatic, esophageal, stomach, brain, liver, and urinary cancer. Other preferred indications include benign dysproliferative disorders and pre-neoplastic conditions, such as, for example, hyperplasia, metaplasia, and/or dysplasia. Preferred indications include arthritis, asthma, AIDS, allergy, anemia, pancytopenia, leukopenia, thrombocytopenia, Hodgkin''s disease, acute lymphocytic anemia (ALL), plasmacytomas, multiple myeloma, Burkitt''s lymphoma, granulomatous disease, inflammatory bowel disease, sepsis, psoriasis, suppression of immune reactions to transplanted organs and tissues, endocarditis, meningitis, and Lyme Disease. |
| 11 | HLHFP03 | 79 | Activation of T-Cell p38 or JNK Signaling Pathway. | Kinase assay. JNK and p38 kinase assays for signal transduction that regulate cell proliferation, activation, or apoptosis are well known in the art and may be used or routinely modified to assess the ability of polypeptides of the invention (including antibodies and agonists or antagonists of the invention) to promote or inhibit immune cell (e.g. T-cell) proliferation, activation, and apoptosis. Exemplary assays for JNK and p38 kinase activity that may be used or routinely modified to test JNK and p38 | Preferred indications include neoplastic diseases (e.g., as described below under "Hyperproliferative Disorders"), blood disorders (e.g., as described below under "Immune Activity", "Cardiovascular Disorders", and/or "Blood-Related Disorders"), and infection (e.g., an infectious disease as described below under "Infectious Disease"). Highly preferred indications include autoimmune diseases (e.g., rheumatoid arthritis, systemic lupus erythematosis, multiple sclerosis and/or as described below) and immunodeficiencies (e.g., as described below). Additional highly preferred indications include inflammation and inflammatory disorders. Highly preferred indications also include |

TABLE 1E-continued

| Gene No. | cDNA Clone ID | AA SEQ ID NO: Y | Biological Activity | Exemplary Activity Assay | Preferred Indication |
|---|---|---|---|---|---|
| | | | | kinase-induced activity of polypeptides of the invention (including antibodies and agonists or antagonists of the invention) include the assays disclosed in Forrer et al., Biol Chem 379(8-9): 1101-1110 (1998); Gupta et al., Exp Cell Res 247(2): 495-504 (1999); Kyriakis J M, Biochem Soc Symp 64: 29-48 (1999); Chang and Karin, Nature 410(6824): 37-40 (2001); and Cobb M H, Prog Biophys Mol Biol 71(3-4): 479-500 (1999); the contents of each of which are herein incorporated by reference in its entirety. T cells that may be used according to these assays are publicly available (e.g., through the ATCC ™). Exemplary mouse T cells that may be used according to these assays include the CTLL cell line, which is an IL-2 dependent suspension-culture cell line with cytotoxic activity. | neoplastic diseases (e.g., leukemia, lymphoma, and/or as described below under "Hyperproliferative Disorders"). Highly preferred indications include neoplasms and cancers, such as, leukemia, lymphoma, prostate, breast, lung, colon, pancreatic, esophageal, stomach, brain, liver, and urinary cancer. Other preferred indications include benign dysproliferative disorders and pre-neoplastic conditions, such as, for example, hyperplasia, metaplasia, and/or dysplasia. Preferred indications include arthritis, asthma, AIDS, allergy, anemia, pancytopenia, leukopenia, thrombocytopenia, Hodgkin"s disease, acute lymphocytic anemia (ALL), plasmacytomas, multiple myeloma, Burkitt"s lymphoma, granulomatous disease, inflammatory bowel disease, sepsis, psoriasis, suppression of immune reactions to transplanted organs and tissues, endocarditis, meningitis, and Lyme Disease. |
| 11 | HLHFP03 | 79 | SEAP in HIB/CRE | | |
| 11 | HLHFP03 | 79 | VEGF in HT1080 | | |
| 11 | HLHFP03 | 79 | Production of VCAM in endothelial cells (such as human umbilical vein endothelial cells (HUVEC)) | Assays for measuring expression of VCAM are well-known in the art and may be used or routinely modified to assess the ability of polypeptides of the invention (including antibodies and agonists or antagonists of the invention) to regulate VCAM expression. For example, FMAT may be used to meaure the upregulation of cell surface VCAM-1 expresssion in endothelial cells. Endothelial cells are cells that line blood vessels, and are involved in functions that include, but are not limited to, angiogenesis, vascular permeability, vascular tone, and immune cell extravasation. Exemplary endothelial cells that may be used according to these assays include human umbilical vein endothelial cells (HUVEC), which are available from commercial sources. The expression of VCAM (CD106), a membrane-associated protein, can be upregulated by cytokines or other factors, and contributes to the extravasation of lymphocytes, leucocytes and other immune cells from blood vessels; thus VCAM expression plays a role in promoting immune and inflammatory responses. | Highly preferred indications include inflammation (acute and chronic), restnosis, atherosclerosis, asthma and allergy. Highly preferred indications include inflammation and inflammatory disorders, immunological disorders, neoplastic disorders (e.g. cancer/tumorigenesis), and cardiovascular disorders (such as described below under "Immune Activity", "Blood-Related Disorders", "Hyperproliferative Disorders" and/or "Cardiovascular Disorders"). Highly preferred indications include neoplasms and cancers such as, for example, leukemia, lymphoma, melanoma, renal cell carcinoma, and prostate, breast, lung, colon, pancreatic, esophageal, stomach, brain, liver and urinary cancer. Other preferred indications include benign dysproliferative disorders and pre-neoplastic conditions, such as, for example, hyperplasia, metaplasia, and/or dysplasia. |
| 11 | HLHFP03 | 79 | SEAP in OE-21 | | |
| 12 | HHTLF25 | 84 | Production of IL-10 and downregulation | IL-10 FMAT. Assays for immunomodulatory proteins produced by activated T cells, | A highly preferred embodiment of the invention includes a method for stimulating the production of IL-10. An alternative |

TABLE 1E-continued

| Gene No. | cDNA Clone ID | AA SEQ ID NO: Y | Biological Activity | Exemplary Activity Assay | Preferred Indication |
|---|---|---|---|---|---|
| | | | of immune responses | B cells, and monocytes that exhibit anti-inflammatory activity and downregulate monocyte/macrophage function and expression of cytokines are well known in the art and may be used or routinely modified to assess the ability of the polypeptides of the invention (including antibodies and agonists or antagonists of the invention) to mediate immunomodulation, regulate inflammatory activities, and modulate immune cell function and cytokine production. Exemplary assays that test for immunomodulatory proteins evaluate the production of cytokines, such as IL-10, and the downmodulation of immune responses. Such assays that may be used or routinely modified to test immunomodulatory activity of polypeptides of the invention (including antibodies and agonists or antagonists of the invention) include the assays disclosed in Miraglia et al., J Biomolecular Screening 4: 193-204 (1999); Rowland et al., "Lymphocytes: a practical approach" Chapter 6: 138-160 (2000); and Koning et al., Cytokine 9(6): 427-436 (1997), the contents of each of which are herein incorporated by reference in its entirety. Human T cells that may be used according to these assays may be isolated using techniques disclosed herein or otherwise known in the art. Human T cells are primary human lymphocytes that mature in the thymus and express a T cell receptor and CD3, CD4, or CD8. These cells mediate humoral or cell-mediated immunity and may be preactivated to enhance responsiveness to immunomodulatory factors. | preferred embodiment of the invention includes a method for inhibiting the production of IL-10. Highly preferred indications include inflammation and inflammatory disorders (e.g. inflammatory bowel disease). An additional highly preferred indication includes inflammatory bowel disease. Additional highly preferred indications include blood disorders (e.g., as described below under "Immune Activity" (e.g. autoimmune disorders), "Blood-Related Disorders", and/or "Cardiovascular Disorders"). Highly preferred indications include autoimmune diseases (e.g., rheumatoid arthritis, systemic lupus erythematosis, multiple sclerosis and/or as described below) and immunodeficiencies (e.g., as described below). Preferred indications include neoplastic diseases (e.g., leukemia, lymphoma, melanoma, and/or as described below under "Hyperproliferative Disorders"). Preferred indications include neoplasms and cancers, such as, for example, leukemia, lymphoma, melanoma, and prostate, breast, lung, colon, pancreatic, esophageal, stomach, brain, liver and urinary cancer. Other preferred indications include benign dysproliferative disorders and pre-neoplastic conditions, such as, for example, hyperplasia, metaplasia, and/or dysplasia. Preferred indications include anemia, pancytopenia, leukopenia, thrombocytopenia, Hodgkin's disease, acute lymphocytic anemia (ALL), plasmacytomas, multiple myeloma, Burkitt's lymphoma, Crohn"s disease, arthritis, AIDS, granulomatous disease, sepsis, neutropenia, neutrophilia, psoriasis, suppression of immune reactions to transplanted organs and tissues, hemophilia, hypercoagulation, diabetes mellitus, endocarditis, meningitis, Lyme Disease, asthma and allergy. An additional preferred indication is infection (e.g., as described below under "Infectious Disease"). |
| 13 | HTADX17 | 91 | Activation of transcription through NFAT response in immune cells (such as T-cells). | Assays for the activation of transcription through the Nuclear Factor of Activated T cells (NFAT) response element are well-known in the art and may be used or routinely modified to assess the ability of polypeptides of the invention (including antibodies and agonists or antagonists of the invention) to regulate NFAT transcription factors and modulate expression of genes involved in immunomodulatory functions. Exemplary assays for transcription through the NFAT response element that may be used or routinely modified to test NFAT-response element activity of polypeptides of the invention | Highly preferred indications include blood disorders (e.g., as described below under "Immune Activity", "Blood-Related Disorders", and/or ""Cardiovascular Disorders""). Highly preferred indications include autoimmune diseases (e.g., rheumatoid arthritis, systemic lupus erythematosis, multiple sclerosis and/or as described below), immunodeficiencies (e.g., as described below), boosting a T cell-mediated immune response, and suppressing a T cell-mediated immune response. Additional highly preferred indications include inflammation and inflammatory disorders. An additional highly preferred indication is infection (e.g., an infectious disease as described below under "Infectious Disease"). Preferred indications include neoplastic diseases (e.g., leukemia, lymphoma, and/or as described below under |

TABLE 1E-continued

| Gene No. | cDNA Clone ID | AA SEQ ID NO: Y | Biological Activity | Exemplary Activity Assay | Preferred Indication |
|---|---|---|---|---|---|
| | | | | (including antibodies and agonists or antagonists of the invention) include assays disclosed in Berger et al., Gene 66: 1-10 (1998); Cullen and Malm, Methods in Enzymol 216: 362-368 (1992); Henthorn et al., Proc Natl Acad Sci USA 85: 6342-6346 (1988); Serfling et al., Biochim Biophys Acta 1498(1): 1-18 (2000); De Boer et al., Int J Biochem Cell Biol 31(10): 1221-1236 (1999); Fraser et al., Eur J Immunol 29(3): 838-844 (1999); and Yeseen et al., J Biol Chem 268(19): 14285-14293 (1993), the contents of each of which are herein incorporated by reference in its entirety. T cells that may be used according to these assays are publicly available (e.g., through the ATCC ™). Exemplary human T cells that may be used according to these assays include the JURKAT cell line, which is a suspension culture of leukemia cells that produce IL-2 when stimulated. | "Hyperproliferative Disorders"). Preferred indications include neoplasms and cancers, such as, for example, leukemia, lymphoma, and prostate, breast, lung, colon, pancreatic, esophageal, stomach, brain, liver and urinary cancer. Other preferred indications include benign dysproliferative disorders and pre-neoplastic conditions, such as, for example, hyperplasia, metaplasia, and/or dysplasia. Preferred indications also include anemia, pancytopenia, leukopenia, thrombocytopenia, Hodgkin's disease, acute lymphocytic anemia (ALL), plasmacytomas, multiple myeloma, Burkitt's lymphoma, arthritis, AIDS, granulomatous disease, inflammatory bowel disease, sepsis, neutropenia, neutrophilia, psoriasis, suppression of immune reactions to transplanted organs and tissues, hemophilia, hypercoagulation, diabetes mellitus, endocarditis, meningitis, Lyme Disease, asthma and allergy. |
| 13 | HTADX17 | 91 | Activation of transcription through GAS response element in immune cells (such as T-cells). | Assays for the activation of transcription through the Gamma Interferon Activation Site (GAS) response element are well-known in the art and may be used or routinely modified to assess the ability of polypeptides of the invention (including antibodies and agonists or antagonists of the invention) to regulate STAT transcription factors and modulate gene expression involved in a wide variety of cell functions. Exemplary assays for transcription through the GAS response element that may be used or routinely modified to test GAS-response element activity of polypeptides of the invention (including antibodies and agonists or antagonists of the invention) include assays disclosed in Berger et al., Gene 66: 1-10 (1998); Cullen and Malm, Methods in Enzymol 216: 362-368 (1992); Henthorn et al., Proc Natl Acad Sci USA 85: 6342-6346 (1988); Matikainen et al., Blood 93(6): 1980-1991 (1999); and Henttinen et al., J Immunol 155(10): 4582-4587 (1995), the contents of each of which are herein incorporated by reference in its entirety. Exemplary human T cells, such as the MOLT4 cell line, that may be used according to these assays are publicly available (e.g., through the ATCC ™). | Highly preferred indications include neoplastic diseases (e.g., leukemia, lymphoma, and/or as described below under "Hyperproliferative Disorders"). Highly preferred indications include neoplasms and cancers, such as, for example, leukemia, lymphoma (e.g., T cell lymphoma, Burkitt's lymphoma, non-Hodgkins lymphoma, Hodgkin's disease), melanoma, and prostate, breast, lung, colon, pancreatic, esophageal, stomach, brain, liver and urinary cancer. Other preferred indications include benign dysproliferative disorders and pre-neoplastic conditions, such as, for example, hyperplasia, metaplasia, and/or dysplasia. Preferred indications include autoimmune diseases (e.g., rheumatoid arthritis, systemic lupus erythematosis, multiple sclerosis and/or as described below), immunodeficiencies (e.g., as described below), boosting a T cell-mediated immune response, and suppressing a T cell-mediated immune response. Additional preferred indications include inflammation and inflammatory disorders. Highly preferred indications include blood disorders (e.g., as described below under "Immune Activity", "Blood-Related Disorders", and/or ""Cardiovascular Disorders""), and infection (e.g., viral infections, tuberculosis, infections associated with chronic granulomatosus disease and malignant osteoporosis, and/or an infectious disease as described below under "Infectious Disease"). An additional preferred indication is idiopathic pulmonary fibrosis. Preferred indications include anemia, pancytopenia, leukopenia, thrombocytopenia, acute lymphocytic anemia (ALL), plasmacytomas, multiple myeloma, arthritis, AIDS, granulomatous disease, inflammatory bowel disease, sepsis, neutropenia, neutrophilia, psoriasis, suppression of immune reactions to |

TABLE 1E-continued

| Gene No. | cDNA Clone ID | AA SEQ ID NO: Y | Biological Activity | Exemplary Activity Assay | Preferred Indication |
|---|---|---|---|---|---|
| | | | | | transplanted organs and tissues, hemophilia, hypercoagulation, diabetes mellitus, endocarditis, meningitis, Lyme Disease, and asthma and allergy. |
| 13 | HTADX17 | 91 | Activation of transcription through NFKB response element in immune cells (such as T-cells). | Assays for the activation of transcription through the NFKB response element are well-known in the art and may be used or routinely modified to assess the ability of polypeptides of the invention (including antibodies and agonists or antagonists of the invention) to regulate NFKB transcription factors and modulate expression of immunomodulatory genes. Exemplary assays for transcription through the NFKB response element that may be used or rountinely modified to test NFKB-response element activity of polypeptides of the invention (including antibodies and agonists or antagonists of the invention) include assays disclosed in Berger et al., Gene 66: 1-10 (1998); Cullen and Malm, Methods in Enzymol 216: 362-368 (1992); Henthorn et al., Proc Natl Acad Sci USA 85: 6342-6346 (1988); Black et al., Virus Gnes 15(2): 105-117 (1997); and Fraser et al., 29(3): 838-844 (1999), the contents of each of which are herein incorporated by reference in its entirety. Exemplary human T cells, such as the MOLT4, that may be used according to these assays are publicly available (e.g., through the ATCC ™). | Highly preferred indications include inflammation and inflammatory disorders. Highly preferred indications include blood disorders (e.g., as described below under "Immune Activity", "Blood-Related Disorders", and/or ""Cardiovascular Disorders""). Highly preferred indications include autoimmune diseases (e.g., rheumatoid arthritis, systemic lupus erythematosis, multiple sclerosis and/or as described below), and immunodeficiencies (e.g., as described below). An additional highly preferred indication is infection (e.g., AIDS, and/or an infectious disease as described below under "Infectious Disease"). Highly preferred indications include neoplastic diseases (e.g., melanoma, leukemia, lymphoma, and/or as described below under "Hyperproliferative Disorders"). Highly preferred indications include neoplasms and cancers, such as, for example, melanoma, renal cell carcinoma, leukemia, lymphoma, and prostate, breast, lung, colon, pancreatic, esophageal, stomach, brain, liver and urinary cancer. Other preferred indications include benign dysproliferative disorders and pre-neoplastic conditions, such as, for example, hyperplasia, metaplasia, and/or dysplasia. Preferred indications also include anemia, pancytopenia, leukopenia, thrombocytopenia, Hodgkin's disease, acute lymphocytic anemia (ALL), plasmacytomas, multiple myeloma, Burkitt's lymphoma, arthritis, AIDS, granulomatous disease, inflammatory bowel disease, sepsis, neutropenia, neutrophilia, psoriasis, hemophilia, hypercoagulation, diabetes mellitus, endocarditis, meningitis, Lyme Disease, suppression of immune reactions to transplanted organs, asthma and allergy. |
| 13 | HTADX17 | 93 | Activation of transcription through NFAT response in immune cells (such as T-cells). | Assays for the activation of transcription through the Nuclear Factor of Activated T cells (NFAT) response element are well-known in the art and may be used or routinely modified to assess the ability of polypeptides of the invention (including antibodies and agonists or antagonists of the invention) to regulate NFAT transcription factors and modulate expression of genes involved in immunomodulatory functions. Exemplary assays for transcription through the NFAT response element that may be used or routinely modified to test NFAT-response element activity of polypeptides of the invention (including antibodies and agonists or antagonists of the invention) include assays disclosed in Berger et al., Gene 66: 1-10 (1998); Cullen and Malm, Methods in Enzymol 216: 362-368 (1992); Henthorn | Highly preferred indications include blood disorders (e.g., as described below under "Immune Activity", "Blood-Related Disorders", and/or "Cardiovascular Disorders"). Highly preferred indications include autoimmune diseases (e.g., rheumatoid arthritis, systemic lupus erythematosis, multiple sclerosis and/or as described below), immunodeficiencies (e.g., as described below), boosting a T cell-mediated immune response, and suppressing a T cell-mediated immune response. Additional highly preferred indications include inflammation and inflammatory disorders. An additional highly preferred indication is infection (e.g., an infectious disease as described below under "Infectious Disease"). Preferred indications include neoplastic diseases (e.g., leukemia, lymphoma, and/or as described below under "Hyperproliferative Disorders"). Preferred indications include neoplasms and cancers, such as, for example, leukemia, lymphoma, and prostate, breast, lung, colon, pancreatic, esophageal, stomach, brain, liver and urinary cancer. Other preferred indications include benign dysproliferative |

TABLE 1E-continued

| Gene No. | cDNA Clone ID | AA SEQ ID NO: Y | Biological Activity | Exemplary Activity Assay | Preferred Indication |
|---|---|---|---|---|---|
| | | | | et al., Proc Natl Acad Sci USA 85: 6342-6346 (1988); Serfling et al., Biochim Biophys Acta 1498(1): 1-18 (2000); De Boer et al., Int J Biochem Cell Biol 31(10): 1221-1236 (1999); Fraser et al., Eur J Immunol 29(3): 838-844 (1999); and Yeseen et al., J Biol Chem 268(19): 14285-14293 (1993), the contents of each of which are herein incorporated by reference in its entirety. T cells that may be used according to these assays are publicly available (e.g., through the ATCC ™). Exemplary human T cells that may be used according to these assays include the JURKAT cell line, which is a suspension culture of leukemia cells that produce IL-2 when stimulated. | disorders and pre-neoplastic conditions, such as, for example, hyperplasia, metaplasia, and/or dysplasia. Preferred indications also include anemia, pancytopenia, leukopenia, thrombocytopenia, Hodgkin's disease, acute lymphocytic anemia (ALL), plasmacytomas, multiple myeloma, Burkitt's lymphoma, arthritis, AIDS, granulomatous disease, inflammatory bowel disease, sepsis, neutropenia, neutrophilia, psoriasis, suppression of immune reactions to transplanted organs and tissues, hemophilia, hypercoagulation, diabetes mellitus, endocarditis, meningitis, Lyme Disease, asthma and allergy. |
| 13 | HTADX17 | 93 | Activation of transcription through GAS response element in immune cells (such as T-cells). | Assays for the activation of transcription through the Gamma Interferon Activation Site (GAS) response element are well-known in the art and may be used or routinely modified to assess the ability of polypeptides of the invention (including antibodies and agonists or antagonists of the invention) to regulate STAT transcription factors and modulate gene expression involved in a wide variety of cell functions. Exemplary assays for transcription through the GAS response element that may be used or routinely modified to test GAS-response element activity of polypeptides of the invention (including antibodies and agonists or antagonists of the invention) include assays disclosed in Berger et al., Gene 66: 1-10 (1998); Cullen and Malm, Methods in Enzymol 216: 362-368 (1992); Henthorn et al., Proc Natl Acad Sci USA 85: 6342-6346 (1988); Matikainen et al., Blood 93(6): 1980-1991 (1999); and Henttinen et al., J Immunol 155(10): 4582-4587 (1995), the contents of each of which are herein incorporated by reference in its entirety. Exemplary human T cells, such as the MOLT4 cell line, that may be used according to these assays are publicly available (e.g., through the ATCC ™). | Highly preferred indications include neoplastic diseases (e.g., leukemia, lymphoma, and/or as described below under "Hyperproliferative Disorders"). Highly preferred indications include neoplasms and cancers, such as, for example, leukemia, lymphoma (e.g., T cell lymphoma, Burkitt's lymphoma, non-Hodgkins lymphoma, Hodgkin''s disease), melanoma, and prostate, breast, lung, colon, pancreatic, esophageal, stomach, brain, liver and urinary cancer. Other preferred indications include benign dysproliferative disorders and pre-neoplastic conditions, such as, for example, hyperplasia, metaplasia, and/or dysplasia. Preferred indications include autoimmune diseases (e.g., rheumatoid arthritis, systemic lupus erythematosis, multiple sclerosis and/or as described below), immunodeficiencies (e.g., as described below), boosting a T cell-mediated immune response, and suppressing a T cell-mediated immune response. Additional preferred indications include inflammation and inflammatory disorders. Highly preferred indications include blood disorders (e.g., as described below under "Immune Activity", "Blood-Related Disorders", and/or "Cardiovascular Disorders"), and infection (e.g., viral infections, tuberculosis, infections associated with chronic granulomatosus disease and malignant osteoporosis, and/or an infectious disease as described below under "Infectious Disease"). An additional preferred indication is idiopathic pulmonary fibrosis. Preferred indications include anemia, pancytopenia, leukopenia, thrombocytopenia, acute lymphocytic anemia (ALL), plasmacytomas, multiple myeloma, arthritis, AIDS, granulomatous disease, inflammatory bowel disease, sepsis, neutropenia, neutrophilia, psoriasis, suppression of immune reactions to transplanted organs and tissues, hemophilia, hypercoagulation, diabetes mellitus, endocarditis, meningitis, Lyme Disease, and asthma and allergy. |
| 13 | HTADX17 | 93 | Activation of transcription | Assays for the activation of transcription through the NFKB | Highly preferred indications include inflammation and inflammatory disorders. |

TABLE 1E-continued

| Gene No. | cDNA Clone ID | AA SEQ ID NO: Y | Biological Activity | Exemplary Activity Assay | Preferred Indication |
|---|---|---|---|---|---|
| | | | through NFKB response element in immune cells (such as T-cells). | response element are well-known in the art and may be used or routinely modified to assess the ability of polypeptides of the invention (including antibodies and agonists or antagonists of the invention) to regulate NFKB transcription factors and modulate expression of immunomodulatory genes. Exemplary assays for transcription through the NFKB response element that may be used or rountinely modified to test NFKB-response element activity of polypeptides of the invention (including antibodies and agonists or antagonists of the invention) include assays disclosed in Berger et al., Gene 66: 1-10 (1998); Cullen and Malm, Methods in Enzymol 216: 362-368 (1992); Henthorn et al., Proc Natl Acad Sci USA 85: 6342-6346 (1988); Black et al., Virus Gnes 15(2): 105-117 (1997); and Fraser et al., 29(3): 838-844 (1999), the contents of each of which are herein incorporated by reference in its entirety. Exemplary human T cells, such as the MOLT4, that may be used according to these assays are publicly available (e.g., through the ATCC ™). | Highly preferred indications include blood disorders (e.g., as described below under "Immune Activity", "Blood-Related Disorders", and/or "Cardiovascular Disorders"). Highly preferred indications include autoimmune diseases (e.g., rheumatoid arthritis, systemic lupus erythematosis, multiple sclerosis and/or as described below), and immunodeficiencies (e.g., as described below). An additional highly preferred indication is infection (e.g., AIDS, and/or an infectious disease as described below under "Infectious Disease"). Highly preferred indications include neoplastic diseases (e.g., melanoma, leukemia, lymphoma, and/or as described below under "Hyperproliferative Disorders"). Highly preferred indications include neoplasms and cancers, such as, for example, melanoma, renal cell carcinoma, leukemia, lymphoma, and prostate, breast, lung, colon, pancreatic, esophageal, stomach, brain, liver and urinary cancer. Other preferred indications include benign dysproliferative disorders and pre-neoplastic conditions, such as, for example, hyperplasia, metaplasia, and/or dysplasia. Preferred indications also include anemia, pancytopenia, leukopenia, thrombocytopenia, Hodgkin's disease, acute lymphocytic anemia (ALL), plasmacytomas, multiple myeloma, Burkitt's lymphoma, arthritis, AIDS, granulomatous disease, inflammatory bowel disease, sepsis, neutropenia, neutrophilia, psoriasis, hemophilia, hypercoagulation, diabetes mellitus, endocarditis, meningitis, Lyme Disease, suppression of immune reactions to transplanted organs, asthma and allergy. |
| 13 | HTADX17 | 93 | IL-8 in Normal Human Bronchial Epitheliae | | |
| 14 | HJACG02 | 105 | MIP-1a in HMC | | |
| 14 | HJACG02 | 105 | Proliferation of pre-adipose cells (such as 3T3-L1 cells) | Assays for the regulation (i.e. increases or decreases) of viability and proliferation of cells in vitro are well-known in the art and may be used or routinely modified to assess the ability of polypeptides of the invention (including antibodies and agonists or antagonists of the invention) to regulate viability and proliferation of pre-adipose cells and cell lines. For example, the CellTiter-Gloô Luminescent Cell Viability Assay (PROMEGA ™ Corp., Madison, WI, USA) can be used to measure the number of viable cells in culture based on quantitation of the ATP present which signals the presence of metabolically active cells. 3T3-L1 is a mouse preadipocyte cell line. It is a continuous substrain of 3T3 fibroblast cells developed through clonal isolation. Cells were differentiated to an adipose-like state before being | |

TABLE 1E-continued

| Gene No. | cDNA Clone ID | AA SEQ ID NO: Y | Biological Activity | Exemplary Activity Assay | Preferred Indication |
|---|---|---|---|---|---|
| | | | | used in the screen. See Green H and Meuth M., Cell 3: 127-133 (1974), which is herein incorporated by reference in its entirety. | |
| 14 | HJACG02 | 105 | MCP-1 in HUVEC | | |
| 14 | HJACG02 | 105 | Activation or inhibition of transcription through NFKB response element in immune cells (such as basophils). | This reporter assay measures activation or inhibition of the NFkB signaling pathway in Ku812 human basophil cell line. Assays for the activation or inhibition of transcription through the NFKB response element are well-known in the art and may be used or routinely modified to assess the ability of polypeptides of the invention (including antibodies and agonists or antagonists of the invention) to regulate NFKB transcription factors and modulate expression of immunomodulatory genes. NFkB is important in the pathogenesis of asthma. Exemplary assays for transcription through the NFKB response element that may be used or rountinely modified to test NFKB-response element activity of polypeptides of the invention (including antibodies and agonists or antagonists of the invention) include assays disclosed in Berger et al., Gene 66: 1-10 (1998); Cullen and Malm, Methods in Enzymol 216: 362-368 (1992); Henthorn et al., Proc Natl Acad Sci USA 85: 6342-6346 (1988); Marone et al, Int Arch Allergy Immunol 114(3): 207-17 (1997), the contents of each of which are herein incorporated by reference in its entirety. Cells were pretreated with SID supernatants or controls for 15-18 hours, and then 10 ng/mL of TNF was added to stimulate the NFkB reporter. SEAP activity was measured after 48 hours. Basophils that may be used according to these assays are publicly available (e.g., through the ATCC ™). Exemplary human basophil cell lines that may be used according to these assays include Ku812, originally established from a patient with chronic myelogenous leukemia. It is an immature prebasophilic cell line that can be induced to differentiate into mature basophils. See, Kishi et al., Leuk Res. 9: 381-390 (1985); Blom et al., Eur J Immunol. 22: 2025-32 (1992), where the contents of each are herein incorporated by reference in its entirety. | |
| 16 | HSVAK93 | 121 | Production of VCAM in endothelial | Assays for measuring expression of VCAM are well-known in the art and may be | Highly preferred indications include inflammation (acute and chronic), restnosis, atherosclerosis, asthma and |

TABLE 1E-continued

| Gene No. | cDNA Clone ID | AA SEQ ID NO: Y | Biological Activity | Exemplary Activity Assay | Preferred Indication |
|---|---|---|---|---|---|
| | | | cells (such as human umbilical vein endothelial cells (HUVEC)) | used or routinely modified to assess the ability of polypeptides of the invention (including antibodies and agonists or antagonists of the invention) to regulate VCAM expression. For example, FMAT may be used to meaure the upregulation of cell surface VCAM-1 expresssion in endothelial cells. Endothelial cells are cells that line blood vessels, and are involved in functions that include, but are not limited to, angiogenesis, vascular permeability, vascular tone, and immune cell extravasation. Exemplary endothelial cells that may be used according to these assays include human umbilical vein endothelial cells (HUVEC), which are available from commercial sources. The expression of VCAM (CD106), a membrane-associated protein, can be upregulated by cytokines or other factors, and contributes to the extravasation of lymphocytes, leucocytes and other immune cells from blood vessels; thus VCAM expression plays a role in promoting immune and inflammatory responses. | allergy. Highly preferred indications include inflammation and inflammatory disorders, immunological disorders, neoplastic disorders (e.g. cancer/tumorigenesis), and cardiovascular disorders (such as described below under "Immune Activity", "Blood-Related Disorders", "Hyperproliferative Disorders" and/or "Cardiovascular Disorders"). Highly preferred indications include neoplasms and cancers such as, for example, leukemia, lymphoma, melanoma, renal cell carcinoma, and prostate, breast, lung, colon, pancreatic, esophageal, stomach, brain, liver and urinary cancer. Other preferred indications include benign dysproliferative disorders and pre-neoplastic conditions, such as, for example, hyperplasia, metaplasia, and/or dysplasia. |
| 17 | HSDEK49 | 126 | Activation of transcription through serum response element in immune cells (such as T-cells). | Assays for the activation of transcription through the Serum Response Element (SRE) are well-known in the art and may be used or routinely modified to assess the ability of polypeptides of the invention (including antibodies and agonists or antagonists of the invention) to regulate the serum response factors and modulate the expression of genes involved in growth. Exemplary assays for transcription through the SRE that may be used or routinely modified to test SRE activity of the polypeptides of the invention (including antibodies and agonists or antagonists of the invention) include assays disclosed in Berger et al., Gene 66: 1-10 (1998); Cullen and Malm, Methods in Enzymol 216: 362-368 (1992); Henthorn et al., Proc Natl Acad Sci USA 85: 6342-6346 (1988); and Black et al., Virus Genes 12(2): 105-117 (1997), the content of each of which are herein incorporated by reference in its entirety. T cells that may be used according to these assays are publicly available (e.g., through the ATCC ™™). Exemplary mouse T cells that may be used according to these assays include the CTLL cell line, which is an IL-2 dependent | A preferred embodiment of the invention includes a method for inhibiting (e.g., reducing) TNF alpha production. An alternative preferred embodiment of the invention includes a method for stimulating (e.g., increasing) TNF alpha production. Preferred indications include blood disorders (e.g., as described below under "Immune Activity", "Blood-Related Disorders", and/or "Cardiovascular Disorders"), Highly preferred indications include autoimmune diseases (e.g., rheumatoid arthritis, systemic lupus erythematosis, Crohn"s disease, multiple sclerosis and/or as described below), immunodeficiencies (e.g., as described below), boosting a T cell-mediated immune response, and suppressing a T cell-mediated immune response. Additional highly preferred indications include inflammation and inflammatory disorders, and treating joint damage in patients with rheumatoid arthritis. An additional highly preferred indication is sepsis. Highly preferred indications include neoplastic diseases (e.g., leukemia, lymphoma, and/or as described below under "Hyperproliferative Disorders"). Additionally, highly preferred indications include neoplasms and cancers, such as, for example, leukemia, lymphoma, melanoma, glioma (e.g., malignant glioma), solid tumors, and prostate, breast, lung, colon, pancreatic, esophageal, stomach, brain, liver and urinary cancer. Other preferred indications include benign dysproliferative disorders and pre-neoplastic conditions, such as, for example, hyperplasia, metaplasia, and/or dysplasia. Preferred indications include anemia, pancytopenia, |

TABLE 1E-continued

| Gene No. | cDNA Clone ID | AA SEQ ID NO: Y | Biological Activity | Exemplary Activity Assay | Preferred Indication |
|---|---|---|---|---|---|
| | | | | suspension culture of T cells with cytotoxic activity. | leukopenia, thrombocytopenia, Hodgkin's disease, acute lymphocytic anemia (ALL), plasmacytomas, multiple myeloma, Burkitt's lymphoma, arthritis, AIDS, granulomatous disease, inflammatory bowel disease, neutropenia, neutrophilia, psoriasis, suppression of immune reactions to transplanted organs and tissues, hemophilia, hypercoagulation, diabetes mellitus, endocarditis, meningitis, Lyme Disease, cardiac reperfusion injury, and asthma and allergy. An additional preferred indication is infection (e.g., an infectious disease as described below under "Infectious Disease"). |
| 17 | HSDEK49 | 126 | Regulation of transcription of Malic Enzyme in adipocytes | Assays for the regulation of transcription of Malic Enzyme are well-known in the art and may be used or routinely modified to assess the ability of polypeptides of the invention (including antibodies and agonists or antagonists of the invention) to regulate transcription of Malic Enzyme, a key enzyme in lipogenesis. Malic enzyme is involved in lipogenesisand its expression is stimulted by insulin. ME promoter contains two direct repeat (DR1)-like elements MEp and MEd identified as putative PPAR response elements. ME promoter may also responds to AP1 and other transcription factors. Exemplary assays that may be used or routinely modified to test for regulation of transcription of Malic Enzyme (in adipoocytes) by polypeptides of the invention (including antibodies and agonists or antagonists of the invention) include assays disclosed in: Streeper, R. S., et al., Mol Endocrinol, 12(11): 1778-91 (1998); Garcia-Jimenez, C., et al., Mol Endocrinol, 8(10): 1361-9 (1994); Barroso, I., et al., J Biol Chem, 274(25): 17997-8004 (1999); Ijpenberg, A., et al., J Biol Chem, 272(32): 20108-20117 (1997); Berger, et al., Gene 66: 1-10 (1988); and, Cullen, B., et al., Methods in Enzymol. 216: 362-368 (1992), the contents of each of which is herein incorporated by reference in its entirety. Hepatocytes that may be used according to these assays are publicly available (e.g., through the ATCC ™™) and/or may be routinely generated. Exemplary hepatocytes that may be used according to these assays includes the H4IIE rat liver hepatoma cell line. | A highly preferred indication is diabetes mellitus. An additional highly preferred indication is a complication associated with diabetes (e.g., diabetic retinopathy, diabetic nephropathy, kidney disease (e.g., renal failure, nephropathy and/or other diseases and disorders as described in the "Renal Disorders" section below), diabetic neuropathy, nerve disease and nerve damage (e.g., due to diabetic neuropathy), blood vessel blockage, heart disease, stroke, impotence (e.g., due to diabetic neuropathy or blood vessel blockage), seizures, mental confusion, drowsiness, nonketotic hyperglycemic-hyperosmolar coma, cardiovascular disease (e.g., heart disease, atherosclerosis, microvascular disease, hypertension, stroke, and other diseases and disorders as described in the "Cardiovascular Disorders" section below), dyslipidemia, endocrine disorders (as described in the "Endocrine Disorders" section below), neuropathy, vision impairment (e.g., diabetic retinopathy and blindness), ulcers and impaired wound healing, and infection (e.g., infectious diseases and disorders as described in the "Infectious Diseases" section below, especially of the urinary tract and skin), carpal tunnel syndrome and Dupuytren's contracture). An additional highly preferred indication is obesity and/or complications associated with obesity. Additional highly preferred indications include weight loss or alternatively, weight gain. Aditional highly preferred indications are complications associated with insulin resistance. |
| 17 | HSDEK49 | 126 | MIP-1a in HMC | | |
| 18 | HWBAO62 | 128 | Activation of transcription through CD28 | Assays for the activation of transcription through the CD28 response element are well- | A highly preferred embodiment of the invention includes a method for stimulating T cell proliferation. An alternative highly |

TABLE 1E-continued

| Gene No. | cDNA Clone ID | AA SEQ ID NO: Y | Biological Activity | Exemplary Activity Assay | Preferred Indication |
|---|---|---|---|---|---|
| | | | response element in immune cells (such as T-cells). | known in the art and may be used or routinely modified to assess the ability of polypeptides of the invention (including antibodies and agonists or antagonists of the invention) to stimulate IL-2 expression in T cells. Exemplary assays for transcription through the CD28 response element that may be used or routinely modified to test CD28-response element activity of polypeptides of the invention (including antibodies and agonists or antagonists of the invention) include assays disclosed in Berger et al., Gene 66: 1-10 (1998); Cullen and Malm, Methods in Enzymol 216: 362-368 (1992); Henthorn et al., Proc Natl Acad Sci USA 85: 6342-6346 (1988); McGuire and Iacobelli, J Immunol 159(3): 1319-1327 (1997); Parra et al., J Immunol 166(4): 2437-2443 (2001); and Butscher et al., J Biol Chem 3(1): 552-560 (1998), the contents of each of which are herein incorporated by reference in its entirety. T cells that may be used according to these assays are publicly available (e.g., through the ATCC ™). Exemplary human T cells that may be used according to these assays include the SUPT cell line, which is a suspension culture of IL-2 and IL-4 responsive T cells. | preferred embodiment of the invention includes a method for inhibiting T cell proliferation. A highly preferred embodiment of the invention includes a method for activating T cells. An alternative highly preferred embodiment of the invention includes a method for inhibiting the activation of and/or inactivating T cells. A highly preferred embodiment of the invention includes a method for stimulating (e.g., increasing) IL-2 production. An alternative highly preferred embodiment of the invention includes a method for inhibiting (e.g., reducing) IL-2 production. Additional highly preferred indications include inflammation and inflammatory disorders. Highly preferred indications include autoimmune diseases (e.g., rheumatoid arthritis, systemic lupus erythematosis, multiple sclerosis and/or as described below), immunodeficiencies (e.g., as described below), boosting a T cell-mediated immune response, and suppressing a T cell-mediated immune response. Highly preferred indications include neoplastic diseases (e.g., melanoma, renal cell carcinoma, leukemia, lymphoma, and/or as described below under "Hyperproliferative Disorders"). Highly preferred indications include neoplasms and cancers, such as, for example, melanoma (e.g., metastatic melanoma), renal cell carcinoma (e.g., metastatic renal cell carcinoma), leukemia, lymphoma (e.g,. T cell lymphoma), and prostate, breast, lung, colon, pancreatic, esophageal, stomach, brain, liver and urinary cancer. Other preferred indications include benign dysproliferative disorders and pre-neoplastic conditions, such as, for example, hyperplasia, metaplasia, and/or dysplasia. A highly preferred indication includes infection (e.g., AIDS, tuberculosis, infections associated with granulomatous disease, and osteoporosis, and/or as described below under "Infectious Disease"). A highly preferred indication is AIDS. Additional highly preferred indications include suppression of immune reactions to transplanted organs and/or tissues, uveitis, psoriasis, and tropical spastic paraparesis. Preferred indications include blood disorders (e.g., as described below under "Immune Activity", "Blood-Related Disorders", and/or "Cardiovascular Disorders"). Preferred indications also include anemia, pancytopenia, leukopenia, thrombocytopenia, Hodgkin's disease, acute lymphocytic anemia (ALL), plasmacytomas, multiple myeloma, Burkitt's lymphoma, arthritis, granulomatous disease, inflammatory bowel disease, sepsis, neutropenia, neutrophilia, hemophilia, hypercoagulation, diabetes mellitus, endocarditis, meningitis, Lyme Disease, asthma and allergy. |
| 18 | HWBAO62 | 128 | Caspase (+paclitaxel) in SW480 | | |
| 19 | HWHGU54 | 132 | Activation of transcription through cAMP response | Assays for the activation of transcription through the cAMP response element are well-known in the art and may be | Preferred indications include blood disorders (e.g., as described below under "Immune Activity", "Blood-Related Disorders", and/or "Cardiovascular |

TABLE 1E-continued

| Gene No. | cDNA Clone ID | AA SEQ ID NO: Y | Biological Activity | Exemplary Activity Assay | Preferred Indication |
|---|---|---|---|---|---|
| | | | element in immune cells (such as T-cells). | used or routinely modified to assess the ability of polypeptides of the invention (including antibodies and agonists or antagonists of the invention) to increase cAMP and regulate CREB transcription factors, and modulate expression of genes involved in a wide variety of cell functions. Exemplary assays for transcription through the cAMP response element that may be used or routinely modified to test cAMP-response element activity of polypeptides of the invention (including antibodies and agonists or antagonists of the invention) include assays disclosed in Berger et al., Gene 66: 1-10 (1998); Cullen and Malm, Methods in Enzymol 216: 362-368 (1992); Henthorn et al., Proc Natl Acad Sci USA 85: 6342-6346 (1988); Black et al., Virus Genes 15(2): 105-117 (1997); and Belkowski et al., J Immunol 161(2): 659-665 (1998), the contents of each of which are herein incorporated by reference in its entirety. T cells that may be used according to these assays are publicly available (e.g., through the ATCC ™). Exemplary mouse T cells that may be used according to these assays include the CTLL cell line, which is a suspension culture of IL-2 dependent cytotoxic T cells. | Disorders"), and infection (e.g., an infectious disease as described below under "Infectious Disease"). Preferred indications include autoimmune diseases (e.g., rheumatoid arthritis, systemic lupus erythematosis, multiple sclerosis and/or as described below), immunodeficiencies (e.g., as described below), boosting a T cell-mediated immune response, and suppressing a T cell-mediated immune response. Additional preferred indications include inflammation and inflammatory disorders. Highly preferred indications include neoplastic diseases (e.g., leukemia, lymphoma, and/or as described below under "Hyperproliferative Disorders"). Highly preferred indications include neoplasms and cancers, such as, for example, leukemia, lymphoma (e.g., T cell lymphoma, Burkitt's lymphoma, non-Hodgkins lymphoma, Hodgkin"s disease), melanoma, and prostate, breast, lung, colon, pancreatic, esophageal, stomach, brain, liver and urinary cancer. Other preferred indications include benign dysproliferative disorders and pre-neoplastic conditions, such as, for example, hyperplasia, metaplasia, and/or dysplasia. Preferred indications include anemia, pancytopenia, leukopenia, thrombocytopenia, acute lymphocytic anemia (ALL), plasmacytomas, multiple myeloma, arthritis, AIDS, granulomatous disease, inflammatory bowel disease, sepsis, neutropenia, neutrophilia, psoriasis, suppression of immune reactions to transplanted organs and tissues, hemophilia, hypercoagulation, diabetes mellitus, endocarditis, meningitis, Lyme Disease, and asthma and allergy. |
| 19 | HWHGU54 | 132 | Production of IL-8 by by endothelial cells (such as Human Umbilical Cord Endothelial Cells). | Assays measuring production of IL-8 are well known in the art and may be used or routinely modified to assess the ability of polypeptides of the invention (including antibodies and agonists or antagonists of the invention) to regulate production and/or secretion of IL-8. For example, FMAT may be used or routinely modified to assess the ability of polypeptides of the invention (including antibodies and agonists or antagonists of the invention) to regulate production and/or secretion of IL-8 from endothelial cells (such as human umbilical vein endothelial cells (HUVEC)). HUVECs are endothelial cells which line venous blood vessels, and are involved in functions that include, but are not limited to, angiogenesis, vascular permeability, vascular tone, and immune cell extravasation. Endothelial cells play a pivotal role in the initiation and perpetuation of inflammation and secretion of IL-8 may play an important role in recruitment and activation of | Highly preferred indications include immunological and inflammatory disorders (e.g., such as allergy, asthma, leukemia, etc. and as described below under "Immune Activity", and "Blood-Related Disorders"). Highly preferred indications also includie autoimmune disorders (e.g., rheumatoid arthritis, systemic lupus erythematosis, Crohn"s disease, multiple sclerosis and/or as described below), neoplastic disorders (e.g., organ cancers such as lung, liver, colon cancer, and/or as described below under "Hyperproliferative Disorders"), and cardiovascular disorders (e.g. such as described below under "Cardiovascular Disorders"). Preferred indications include thrombosis, bacteremia and sepsis syndrome and consequent complications (such as acute respiratory distress syndrome and systemic ischemia-reperfusion resulting from septic shock), restnosis and atherosclerosis. |

TABLE 1E-continued

| Gene No. | cDNA Clone ID | AA SEQ ID NO: Y | Biological Activity | Exemplary Activity Assay | Preferred Indication |
|---|---|---|---|---|---|
| | | | | immune cells such as neutrophils, macrophages, and lymphocytes. | |
| 19 | HWHGU54 | 132 | SEAP in HIB/CRE | | |
| 19 | HWHGU54 | 132 | Proliferation of pre-adipose cells (such as 3T3-L1 cells) | Assays for the regulation (i.e. increases or decreases) of viability and proliferation of cells in vitro are well-known in the art and may be used or routinely modified to assess the ability of polypeptides of the invention (including antibodies and agonists or antagonists of the invention) to regulate viability and proliferation of pre-adipose cells and cell lines. For example, the CellTiter-Gloô Luminescent Cell Viability Assay (PROMEGA ™ Corp., Madison, WI, USA) can be used to measure the number of viable cells in culture based on quantitation of the ATP present which signals the presence of metabolically active cells. 3T3-L1 is a mouse preadipocyte cell line. It is a continuous substrain of 3T3 fibroblast cells developed through clonal isolation. Cells were differentiated to an adipose-like state before being used in the screen. See Green H and Meuth M., Cell 3: 127-133 (1974), which is herein incorporated by reference in its entirety. | |
| 19 | HWHGU54 | 132 | MCP-1 in HUVEC | | |
| 21 | HT5GJ57 | 162 | Activation of transcription through AP1 response element in immune cells (such as T-cells). | Assays for the activation of transcription through the AP1 response element are known in the art and may be used or routinely modified to assess the ability of polypeptides of the invention (including antibodies and agonists or antagonists of the invention) to modulate growth and other cell functions. Exemplary assays for transcription through the AP1 response element that may be used or routinely modified to test AP1-response element activity of polypeptides of the invention (including antibodies and agonists or antagonists of the invention) include assays disclosed in Berger et al., Gene 66: 1-10 (1988); Cullen and Malm, Methods in Enzymol 216: 362-368 (1992); Henthorn et al., Proc Natl Acad Sci USA 85: 6342-6346 (1988); Rellahan et al., J Biol Chem 272(49): 30806-30811 (1997); Chang et al., Mol Cell Biol 18(9): 4986-4993 (1998); and Fraser et al., Eur J Immunol 29(3): 838-844 (1999), the contents of each of which are herein incorporated by reference in its entirety. T cells that may be used according to | Preferred indications include neoplastic diseases (e.g., as described below under "Hyperproliferative Disorders"), blood disorders (e.g., as described below under "Immune Activity", "Cardiovascular Disorders", and/or "Blood-Related Disorders"), and infection (e.g., an infectious disease as described below under "Infectious Disease"). Highly preferred indications include autoimmune diseases (e.g., rheumatoid arthritis, systemic lupus erythematosis, multiple sclerosis and/or as described below) and immunodeficiencies (e.g., as described below). Additional highly preferred indications include inflammation and inflammatory disorders. Highly preferred indications also include neoplastic diseases (e.g., leukemia, lymphoma, and/or as described below under "Hyperproliferative Disorders"). Highly preferred indications include neoplasms and cancers, such as, leukemia, lymphoma, prostate, breast, lung, colon, pancreatic, esophageal, stomach, brain, liver, and urinary cancer. Other preferred indications include benign dysproliferative disorders and pre-neoplastic conditions, such as, for example, hyperplasia, metaplasia, and/or dysplasia. Preferred indications include arthritis, asthma, AIDS, allergy, anemia, pancytopenia, leukopenia, thrombocytopenia, Hodgkin's disease, acute lymphocytic anemia (ALL), plasmacytomas, multiple myeloma, Burkitt's lymphoma, granulomatous |

TABLE 1E-continued

| Gene No. | cDNA Clone ID | AA SEQ ID NO: Y | Biological Activity | Exemplary Activity Assay | Preferred Indication |
|---|---|---|---|---|---|
| | | | | these assays are publicly available (e.g., through the ATCC ™). Exemplary mouse T cells that may be used according to these assays include the CTLL cell line, which is an IL-2 dependent suspension-culture cell line with cytotoxic activity. | disease, inflammatory bowel disease, sepsis, psoriasis, suppression of immune reactions to transplanted organs and tissues, endocarditis, meningitis, and Lyme Disease. |
| 21 | HT5GJ57 | 162 | Production of MCP-1 | MCP-1 FMAT. Assays for immunomodulatory proteins that are produced by a large variety of cells and act to induce chemotaxis and activation of monocytes and T cells are well known in the art and may be used or routinely modified to assess the ability of polypeptides of the invention (including antibodies and agonists or antagonists of the invention) to mediate immunomodulation, induce chemotaxis, and modulate immune cell activation. Exemplary assays that test for immunomodulatory proteins evaluate the production of cell surface markers, such as monocyte chemoattractant protein (MCP), and the activation of monocytes and T cells. Such assays that may be used or routinely modified to test immunomodulatory and differentiation activity of polypeptides of the invention (including antibodies and agonists or antagonists of the invention) include assays disclosed in Miraglia et al., J Biomolecular Screening 4: 193-204 (1999); Rowland et al., “Lymphocytes: a practical approach” Chapter 6: 138-160 (2000); Satthaporn and Eremin, J R Coll Surg Ednb 45(1): 9-19 (2001); and Verhasselt et al., J Immunol 158: 2919-2925 (1997), the contents of each of which are herein incorporated by reference in its entirety. Human dendritic cells that may be used according to these assays may be isolated using techniques disclosed herein or otherwise known in the art. Human dendritic cells are antigen presenting cells in suspension culture, which, when activated by antigen and/or cytokines, initiate and upregulate T cell proliferation and functional activities. | A highly preferred embodiment of the invention includes a method for stimulating (e.g., increasing) MCP-1 production. An alternative highly preferred embodiment of the invention includes a method for inhibiting (e.g., reducing) MCP-1 production. A highly preferred indication is infection (e.g., an infectious disease as described below under “Infectious Disease”). Additional highly preferred indications include inflammation and inflammatory disorders. Preferred indications include blood disorders (e.g., as described below under “Immune Activity”, “Blood-Related Disorders”, and/or “Cardiovascular Disorders”). Highly preferred indications include autoimmune diseases (e.g., rheumatoid arthritis, systemic lupus erythematosis, multiple sclerosis and/or as described below) and immunodeficiencies (e.g., as described below). Preferred indications also include anemia, pancytopenia, leukopenia, thrombocytopenia, Hodgkin’s disease, acute lymphocytic anemia (ALL), plasmacytomas, multiple myeloma, Burkitt’s lymphoma, arthritis, AIDS, granulomatous disease, inflammatory bowel disease, sepsis, neutropenia, neutrophilia, psoriasis, suppression of immune reactions to transplanted organs and tissues, hemophilia, hypercoagulation, diabetes mellitus, endocarditis, meningitis (bacterial and viral), Lyme Disease, asthma, and allergy Preferred indications also include neoplastic diseases (e.g., leukemia, lymphoma, and/or as described below under “Hyperproliferative Disorders”). Highly preferred indications include neoplasms and cancers, such as, leukemia, lymphoma, prostate, breast, lung, colon, pancreatic, esophageal, stomach, brain, liver, and urinary cancer. Other preferred indications include benign dysproliferative disorders and pre-neoplastic conditions, such as, for example, hyperplasia, metaplasia, and/or dysplasia. |
| 21 | HT5GJ57 | 162 | Inhibition of squalene synthetase gene transcription. | Reporter Assay: construct contains regulatory and coding sequence of squalene synthetase, the first specific enzyme in the cholesterol biosynthetic pathway. See Jiang, et al., J. Biol. Chem. 268: 12818-128241(993), the contents of which are herein incorporated by reference in its entirety. Cells were treated | |

TABLE 1E-continued

| Gene No. | cDNA Clone ID | AA SEQ ID NO: Y | Biological Activity | Exemplary Activity Assay | Preferred Indication |
|---|---|---|---|---|---|
| | | | | with SID supernatants, and SEAP activity was measured after 72 hours. HepG2 is a human hepatocellular carcinoma cell line (ATCC ™ HB-8065). See Knowles et al., Science. 209: 497-9 (1980), the contents of which are herein incorporated by reference in its entirety. | |
| 21 | HT5GJ57 | 162 | IgG in Human B cells SAC | | |
| 21 | HT5GJ57 | 162 | IL-10 in Human T-cell 2B9 | | |
| 21 | HT5GJ57 | 162 | TNFa in Human T-cell 2B9 | | |
| 21 | HT5GJ57 | 162 | Caspase (+paclitaxel) in SW480 | | |
| 27 | HDHMA45 | 203 | Production of IL-10 and activation of T-cells. | Assays for production of IL-10 and activation of T-cells are well known in the art and may be used or routinely modified to assess the ability of polypeptides of the invention (including antibodies and agonists or antagonists of the invention) to stimulate or inhibit production of IL-10 and/or activation of T-cells. Exemplary assays that may be used or routinely modified to assess the ability of polypeptides and antibodies of the invention (including agonists or antagonists of the invention) to modulate IL-10 production and/or T-cell proliferation include, for example, assays such as disclosed and/or cited in: Robinson, D S, et al., "Th-2 cytokines in allergic disease" Br Med Bull; 56 (4): 956-968 (2000), and Cohn, et al., "T-helper type 2 cell-directed therapy for asthma" Pharmacology & Therapeutics; 88: 187-196 (2000); the contents of each of which are herein incorporated by reference in their entirety. Exemplary cells that may be used according to these assays include Th2 cells. IL10 secreted from Th2 cells may be measured as a marker of Th2 cell activation. Th2 cells are a class of T cells that secrete IL4, IL10, IL13, IL5 and IL6. Factors that induce differentiation and activation of Th2 cells play a major role in the initiation and pathogenesis of allergy and asthma. Primary T helper 2 cells are generated via in vitro culture under Th2 polarizing conditions using peripheral blood lymphocytes isolated from cord blood. | Highly preferred indications include allergy and asthma. Additional highly preferred indications include immune and hematopoietic disorders (e.g., as described below under "Immune Activity", and "Blood-Related Disorders"), autoimmune diseases (e.g., rheumatoid arthritis, systemic lupus erythematosis, Crohn''s disease, multiple sclerosis and/or as described below), immunodeficiencies (e.g., as described below), boosting a T cell-mediated immune response, and suppressing a T cell-mediated immune response. |
| 31 | HDPPA04 | 225 | Production of MIP1alpha | MIP-1alpha FMAT. Assays for immunomodulatory proteins produced by activated dendritic | A highly preferred embodiment of the invention includes a method for stimulating MIP1a production. An alternative highly |

TABLE 1E-continued

| Gene No. | cDNA Clone ID | AA SEQ ID NO: Y | Biological Activity | Exemplary Activity Assay | Preferred Indication |
|---|---|---|---|---|---|
| | | | | cells that upregulate monocyte/macrophage and T cell chemotaxis are well known in the art and may be used or routinely modified to assess the ability of polypeptides of the invention (including antibodies and agonists or antagonists of the invention) to mediate immunomodulation, modulate chemotaxis, and modulate T cell differentiation. Exemplary assays that test for immunomodulatory proteins evaluate the production of chemokines, such as macrophage inflammatory protein 1 alpha (MIP-1a), and the activation of monocytes/macrophages and T cells. Such assays that may be used or routinely modified to test immunomodulatory and chemotaxis activity of polypeptides of the invention (including antibodies and agonists or antagonists of the invention) include assays disclosed in Miraglia et al., J Biomolecular Screening 4: 193-204 (1999); Rowland et al., "Lymphocytes: a practical approach" Chapter 6: 138-160 (2000); Satthaporn and Eremin, J R Coll Surg Ednb 45(1): 9-19 (2001); Drakes et al., Transp Immunol 8(1): 17-29 (2000); Verhasselt et al., J Immunol 158: 2919-2925 (1997); and Nardelli et al., J Leukoc Biol 65: 822-828 (1999), the contents of each of which are herein incorporated by reference in its entirety. Human dendritic cells that may be used according to these assays may be isolated using techniques disclosed herein or otherwise known in the art. Human dendritic cells are antigen presenting cells in suspension culture, which, when activated by antigen and/or cytokines, initiate and upregulate T cell proliferation and functional activities. | preferred embodiment of the invention includes a method for inhibiting (e.g., reducing) MIP1a production. A highly preferred indication is infection (e.g., an infectious disease as described below under "Infectious Disease"). Preferred indications include blood disorders (e.g., as described below under "Immune Activity", "Blood-Related Disorders", and/or "Cardiovascular Disorders"). Highly preferred indications include autoimmune diseases (e.g., rheumatoid arthritis, systemic lupus erythematosis, multiple sclerosis and/or as described below) and immunodeficiencies (e.g., as described below). Additional highly preferred indications include inflammation and inflammatory disorders. Preferred indications also include anemia, pancytopenia, leukopenia, thrombocytopenia, Hodgkin's disease, acute lymphocytic anemia (ALL), plasmacytomas, multiple myeloma, Burkitt's lymphoma, arthritis, AIDS, granulomatous disease, inflammatory bowel disease, sepsis, neutropenia, neutrophilia, psoriasis, suppression of immune reactions to transplanted organs and tissues, hemophilia, hypercoagulation, diabetes mellitus, endocarditis, meningitis, Lyme Disease, asthma, and allergy. Preferred indications also include neoplastic diseases (e.g., leukemia, lymphoma, and/or as described below under "Hyperproliferative Disorders"). Highly preferred indications include neoplasms and cancers, such as, leukemia, lymphoma, prostate, breast, lung, colon, pancreatic, esophageal, stomach, brain, liver, and urinary cancer. Other preferred indications include benign dysproliferative disorders and pre-neoplastic conditions, such as, for example, hyperplasia, metaplasia, and/or dysplasia. |
| 33 | HKABZ65 | 233 | Production of IL-6 | IL-6 FMAT. IL-6 is produced by T cells and has strong effects on B cells. IL-6 participates in IL-4 induced IgE production and increases IgA production (IgA plays a role in mucosal immunity). IL-6 induces cytotoxic T cells. Deregulated expression of IL-6 has been linked to autoimmune disease, plasmacytomas, myelomas, and chronic hyperproliferative diseases. Assays for immunomodulatory and differentiation factor proteins produced by a large variety of cells where the expression level is strongly regulated by cytokines, growth factors, and hormones are well known in the | A highly preferred embodiment of the invention includes a method for stimulating (e.g., increasing) IL-6 production. An alternative highly preferred embodiment of the invention includes a method for inhibiting (e.g., reducing) IL-6 production. A highly preferrred indication is the stimulation or enhancement of mucosal immunity. Highly preferred indications include blood disorders (e.g., as described below under "Immune Activity", "Blood-Related Disorders", and/or "Cardiovascular Disorders"), and infection (e.g., as described below under "Infectious Disease"). Highly preferred indications include autoimmune diseases (e.g., rheumatoid arthritis, systemic lupus erythematosis, multiple sclerosis and/or as described below) and immunodeficiencies (e.g., as described below). Highly |

TABLE 1E-continued

| Gene No. | cDNA Clone ID | AA SEQ ID NO: Y | Biological Activity | Exemplary Activity Assay | Preferred Indication |
|---|---|---|---|---|---|
| | | | | art and may be used or routinely modified to assess the ability of polypeptides of the invention (including antibodies and agonists or antagonists of the invention) to mediate immunomodulation and differentiation and modulate T cell proliferation and function. Exemplary assays that test for immunomodulatory proteins evaluate the production of cytokines, such as IL-6, and the stimulation and upregulation of T cell proliferation and functional activities. Such assays that may be used or routinely modified to test immunomodulatory and differentiation activity of polypeptides of the invention (including antibodies and agonists or antagonists of the invention) include assays disclosed in Miraglia et al., J Biomolecular Screening 4: 193-204 (1999); Rowland et al., "Lymphocytes: a practical approach" Chapter 6: 138-160 (2000); and Verhasselt et al., J Immunol 158: 2919-2925 (1997), the contents of each of which are herein incorporated by reference in its entirety. Human dendritic cells that may be used according to these assays may be isolated using techniques disclosed herein or otherwise known in the art. Human dendritic cells are antigen presenting cells in suspension culture, which, when activated by antigen and/or cytokines, initiate and upregulate T cell proliferation and functional activities. | preferred indications also include boosting a B cell-mediated immune response and alternatively suppressing a B cell-mediated immune response. Highly preferred indications include inflammation and inflammatory disorders. Additional highly preferred indications include asthma and allergy. Highly preferred indications include neoplastic diseases (e.g., myeloma, plasmacytoma, leukemia, lymphoma, melanoma, and/or as described below under "Hyperproliferative Disorders"). Highly preferred indications include neoplasms and cancers, such as, myeloma, plasmacytoma, leukemia, lymphoma, melanoma, and prostate, breast, lung, colon, pancreatic, esophageal, stomach, brain, liver and urinary cancer. Other preferred indications include benign dysproliferative disorders and pre-neoplastic conditions, such as, for example, hyperplasia, metaplasia, and/or dysplasia. Preferred indications include anemia, pancytopenia, leukopenia, thrombocytopenia, Hodgkin's disease, acute lymphocytic anemia (ALL), multiple myeloma, Burkitt's lymphoma, arthritis, AIDS, granulomatous disease, inflammatory bowel disease, sepsis, neutropenia, neutrophilia, psoriasis, suppression of immune reactions to transplanted organs and tissues, hemophilia, hypercoagulation, diabetes mellitus, endocarditis, meningitis, and Lyme Disease. An additonal preferred indication is infection (e.g., an infectious disease as described below under "Infectious Disease"). |
| 33 | HKABZ65 | 233 | Activation of Endothelial Cell p38 or JNK Signaling Pathway. | Kinase assay. JNK and p38 kinase assays for signal transduction that regulate cell proliferation, activation, or apoptosis are well known in the art and may be used or routinely modified to assess the ability of polypeptides of the invention (including antibodies and agonists or antagonists of the invention) to promote or inhibit cell proliferation, activation, and apoptosis. Exemplary assays for JNK and p38 kinase activity that may be used or routinely modified to test JNK and p38 kinase-induced activity of polypeptides of the invention (including antibodies and agonists or antagonists of the invention) include the assays disclosed in Forrer et al., Biol Chem 379(8-9): 1101-1110 (1998); Gupta et al., Exp Cell Res 247(2): 495-504 (1999); Kyriakis J M, Biochem Soc Symp 64: 29-48 (1999); Chang and Karin, Nature 410(6824): 37-40 | A highly preferred embodiment of the invention includes a method for stimulating endothelial cell growth. An alternative highly preferred embodiment of the invention includes a method for inhibiting endothelial cell growth. A highly preferred embodiment of the invention includes a method for stimulating endothelial cell proliferation. An alternative highly preferred embodiment of the invention includes a method for inhibiting endothelial cell proliferation. A highly preferred embodiment of the invention includes a method for stimulating apoptosis of endothelial cells. An alternative highly preferred embodiment of the invention includes a method for inhibiting (e.g., decreasing) apoptosis of endothelial cells. A highly preferred embodiment of the invention includes a method for stimulating (e.g., increasing) endothelial cell activation. An alternative highly preferred embodiment of the invention includes a method for inhibiting (e.g., decreasing) the activation of and/or inactivating endothelial cells. A highly preferred embodiment of the invention includes a method for stimulating angiogenisis. An alternative highly |

TABLE 1E-continued

| Gene No. | cDNA Clone ID | AA SEQ ID NO: Y | Biological Activity | Exemplary Activity Assay | Preferred Indication |
|---|---|---|---|---|---|
| | | | | (2001); and Cobb M H, Prog Biophys Mol Biol 71(3-4): 479-500 (1999); the contents of each of which are herein incorporated by reference in its entirety. Endothelial cells that may be used according to these assays are publicly available (e.g., through the ATCC ™). Exemplary endothelial cells that may be used according to these assays include human umbilical vein endothelial cells (HUVEC), which are endothelial cells which line venous blood vessels, and are involved in functions that include, but are not limited to, angiogenesis, vascular permeability, vascular tone, and immune cell extravasation. | preferred embodiment of the invention includes a method for inhibiting angiogenesis. A highly preferred embodiment of the invention includes a method for reducing cardiac hypertrophy. An alternative highly preferred embodiment of the invention includes a method for inducing cardiac hypertrophy. Highly preferred indications include neoplastic diseases (e.g., as described below under “Hyperproliferative Disorders”), and disorders of the cardiovascular system (e.g., heart disease, congestive heart failure, hypertension, aortic stenosis, cardiomyopathy, valvular regurgitation, left ventricular dysfunction, atherosclerosis and atherosclerotic vascular disease, diabetic nephropathy, intracardiac shunt, cardiac hypertrophy, myocardial infarction, chronic hemodynamic overload, and/or as described below under “Cardiovascular Disorders”). Highly preferred indications include cardiovascular, endothelial and/or angiogenic disorders (e.g., systemic disorders that affect vessels such as diabetes mellitus, as well as diseases of the vessels themselves, such as of the arteries, capillaries, veins and/or lymphatics). Highly preferred are indications that stimulate angiogenesis and/or cardiovascularization. Highly preferred are indications that inhibit angiogenesis and/or cardiovascularization. Highly preferred indications include antiangiogenic activity to treat solid tumors, leukemias, and Kaposi’’s sarcoma, and retinal disorders. Highly preferred indications include neoplasms and cancer, such as, Kaposi’’s sarcoma, hemangioma (capillary and cavernous), glomus tumors, telangiectasia, bacillary angiomatosis, hemangioendothelioma, angiosarcoma, haemangiopericytoma, lymphangioma, lymphangiosarcoma. Highly preferred indications also include cancers such as, prostate, breast, lung, colon, pancreatic, esophageal, stomach, brain, liver, and urinary cancer. Preferred indications include benign dysproliferative disorders and pre-neoplastic conditions, such as, for example, hyperplasia, metaplasia, and/or dysplasia. Highly preferred indications also include arterial disease, such as, atherosclerosis, hypertension, coronary artery disease, inflammatory vasculitides, Reynaud’’s disease and Reynaud’’s phenomenom, aneurysms, restenosis; venous and lymphatic disorders such as thrombophlebitis, lymphangitis, and lymphedema; and other vascular disorders such as peripheral vascular disease, and cancer. Highly preferred indications also include trauma such as wounds, burns, and injured tissue (e.g., vascular injury such as, injury resulting from balloon angioplasty, and atheroschlerotic lesions), implant fixation, scarring, ischemia reperfusion injury, rheumatoid arthritis, cerebrovascular disease, renal diseases such as acute renal failure, and osteoporosis. Additional highly preferred indications include stroke, graft rejection, diabetic or other retinopathies, thrombotic and coagulative disorders, vascularitis, lymph |

TABLE 1E-continued

| Gene No. | cDNA Clone ID | AA SEQ ID NO: Y | Biological Activity | Exemplary Activity Assay | Preferred Indication |
|---|---|---|---|---|---|
| | | | | | angiogenesis, sexual disorders, age-related macular degeneration, and treatment/prevention of endometriosis and related conditions. Additional highly preferred indications include fibromas, heart disease, cardiac arrest, heart valve disease, and vascular disease. Preferred indications include blood disorders (e.g., as described below under "Immune Activity", "Blood-Related Disorders", and/or "Cardiovascular Disorders"). Preferred indications include autoimmune diseases (e.g., rheumatoid arthritis, systemic lupus erythematosis, multiple sclerosis and/or as described below) and immunodeficiencies (e.g., as described below). Additional preferred indications include inflammation and inflammatory disorders (such as acute and chronic inflammatory diseases, e.g., inflammatory bowel disease and Crohn's disease), and pain management. |
| 33 | HKABZ65 | 233 | Regulation of apoptosis in pancreatic beta cells. | Caspase Apoptosis. Assays for caspase apoptosis are well known in the art and may be used or routinely modified to assess the ability of polypeptides of the invention (including antibodies and agonists or antagonists of the invention) to promote caspase protease-mediated apoptosis. Apoptosis in pancreatic beta is associated with induction and progression of diabetes. Exemplary assays for caspase apoptosis that may be used or routinely modified to test capase apoptosis activity of polypeptides of the invention (including antibodies and agonists or antagonists of the invention) include the assays disclosed in: Loweth, A C, et al., FEBS Lett, 400(3): 285-8 (1997); Saini, K S, et al., Biochem Mol Biol Int, 39(6): 1229-36 (1996); Krautheim, A., et al., Br J Pharmacol, 129(4): 687-94 (2000); Chandra J, et al., Diabetes, 50 Suppl 1: S44-7 (2001); Suk K, et al., J Immunol, 166(7): 4481-9 (2001); Tejedo J, et al., FEBS Lett, 459(2): 238-43 (1999); Zhang, S., et al., FEBS Lett, 455(3): 315-20 (1999); Lee et al., FEBS Lett 485(2-3): 122-126 (2000); Nor et al., J Vasc Res 37(3): 209-218 (2000); and Karsan and Harlan, J Atheroscler Thromb 3(2): 75-80 (1996); the contents of each of which are herein incorporated by reference in its entirety. Pancreatic cells that may be used according to these assays are publicly available (e.g., through the ATCC ™) and/or may be routinely generated. Exemplary pancreatic cells that may be used according to these assays include RIN-m. RIN-m is a rat adherent pancreatic beta cell | A highly preferred indication is diabetes mellitus. An additional highly preferred indication is a complication associated with diabetes (e.g., diabetic retinopathy, diabetic nephropathy, kidney disease (e.g., renal failure, nephropathy and/or other diseases and disorders as described in the "Renal Disorders" section below), diabetic neuropathy, nerve disease and nerve damage (e.g., due to diabetic neuropathy), blood vessel blockage, heart disease, stroke, impotence (e.g., due to diabetic neuropathy or blood vessel blockage), seizures, mental confusion, drowsiness, nonketotic hyperglycemic-hyperosmolar coma, cardiovascular disease (e.g., heart disease, atherosclerosis, microvascular disease, hypertension, stroke, and other diseases and disorders as described in the "Cardiovascular Disorders" section below), dyslipidemia, endocrine disorders (as described in the "Endocrine Disorders" section below), neuropathy, vision impairment (e.g., diabetic retinopathy and blindness), ulcers and impaired wound healing, and infection (e.g., infectious diseases and disorders as described in the "Infectious Diseases" section below, especially of the urinary tract and skin), carpal tunnel syndrome and Dupuytren's contracture). An additional highly preferred indication is obesity and/or complications associated with obesity. Additional highly preferred indications include weight loss or alternatively, weight gain. Aditional highly preferred indications are complications associated with insulin resistance. |

TABLE 1E-continued

| Gene No. | cDNA Clone ID | AA SEQ ID NO: Y | Biological Activity | Exemplary Activity Assay | Preferred Indication |
|---|---|---|---|---|---|
| | | | | insulinoma cell line derived from a radiation induced transplantable rat islet cell tumor. The cells produce and secrete islet polypeptide hormones, and produce insulin, somatostatin, and possibly glucagon. ATTC: #CRL-2057 Chick et al. Proc. Natl. Acad. Sci. 1977 74: 628; AF et al. Proc. Natl. Acad. Sci. 1980 77: 3519. | |

Tables 1E.1 and 1E.2 provide information related to biological activities for polynucleotides and polypeptides of the invention (including antibodies, agonists, and/or antagonists thereof). Tables 1E.2 also provide information related to assays which may be used to test polynucleotides and polypeptides of the invention (including antibodies, agonists, and/or antagonists thereof) for the corresponding biological activities. The first column of Table 1E.1 ("Gene No.") provides the gene number in the application for each clone identifier. The second column of Table 1E.1 ("cDNA Clone ID:") provides the unique clone identifier for each clone as previously described and indicated in Table 1A through Table 1D. The third column of Table 1E.1 ("AA SEQ ID NO:Y") indicates the Sequence Listing SEQ ID Number for polypeptide sequences encoded by the corresponding cDNA clones (also as indicated in Tables 1A and 1B.1). The fourth column of Table 1E.1 ("Biological Activity") indicates a biological activity corresponding to the indicated polypeptides (or polynucleotides encoding said polypeptides).

In Table 1E.2, each of the biological activities of Table 1E.1 are listed by "Biological Activity Number" and the corresponding "Biological Activity" and are followed by an "Exemplary Activity Assay" column and a "Preferred Indication" column; however, for some biological activities no "Exemplary Activity Assay" or "Preferred Indication" is given. The "Exemplary Activity Assay" column describes the biological activity listed in the column that precedes it and also provides information pertaining to the various types of assays which may be performed to test, demonstrate, or quantify the corresponding biological activity. The "Preferred Indication" column also refers to the biological activity listed in the preceding column and describes disease(s) or disorder(s) that may be detected, diagnosed, prevented, treated, or ameliorated by the nucleic acids and proteins (or antibodies against the same) of the invention (including polynucleotide, polypeptide, and antibody fragments or variants thereof).

Tables 1E, 1E.1, and 1E.2 describe the use of, inter alia, FMAT technology for testing or demonstrating various biological activities. Fluorometric microvolume assay technology (FMAT) is a fluorescence-based system which provides a means to perform nonradioactive cell- and bead-based assays to detect activation of cell signal transduction pathways. This technology was designed specifically for ligand binding and immunological assays. Using this technology, fluorescent cells or beads at the bottom of the well are detected as localized areas of concentrated fluorescence using a data processing system. Unbound fluorophore comprising the background signal is ignored, allowing for a wide variety of homogeneous assays. FMAT technology may be used for peptide ligand binding assays, immunofluorescence, apoptosis, cytotoxicity, and bead-based immunocapture assays. See, Miraglia S et. al., "Homogeneous cell and bead based assays for high throughput screening using fluorometric microvolume assay technology," Journal of Biomolecular Screening; 4:193-204 (1999). In particular, FMAT technology may be used to test, confirm, and/or identify the ability of polypeptides (including polypeptide fragments and variants) to activate signal transduction pathways. For example, FMAT technology may be used to test, confirm, and/or identify the ability of polypeptides to upregulate production of immunomodulatory proteins (such as, for example, interleukins, GM-CSF, Rantes, and Tumor Necrosis factors, as well as other cellular regulators (e.g. insulin)).

Tables 1E, 1E.1, and 1E.2 also describe the use of kinase assays for testing, demonstrating, or quantifying biological activity. In this regard, the phosphorylation and de-phosphorylation of specific amino acid residues (e.g. Tyrosine, Serine, Threonine) on cell-signal transduction proteins provides a fast, reversible means for activation and de-activation of cellular signal transduction pathways. Moreover, cell signal transduction via phosphorylation/de-phosphorylation is crucial to the regulation of a wide variety of cellular processes (e.g. proliferation, differentiation, migration, apoptosis, etc.). Accordingly, kinase assays provide a powerful tool useful for testing, confirming, and/or identifying polypeptides (including polypeptide fragments and variants) that mediate cell signal transduction events via protein phosphorylation. See e.g., Forrer, P., Tamaskovic R., and Jaussi, R. "Enzyme-Linked Immunosorbent Assay for Measurement of JNK, ERK, and p38 Kinase Activities" Biol. Chem. 379(8-9): 1101-1110 (1998). Table 1D from U.S. patent application Ser. No. 10/472,532, filed Sep. 20, 2003, is herein incorporated by reference. Table 1D in priority Application No. PCT/US02/09785, filed Mar. 19, 2002, which corresponds to Publication No. WO02/95010, published Nov. 28, 2002 (e.g., pages 238 to 582 of Publication No. WO02/95010) is incorporated by reference herein in its entirety.

TABLE 1E.1

| Gene No. | cDNA Clone ID | AA SEQ ID NO: Y | Biological Activity |
|---|---|---|---|
| 3 | HTEEB42 | 10 | Biological Activity #119: Regulation of transcription of Malic Enzyme in hepatocytes |

TABLE 1E.1-continued

| Gene No. | cDNA Clone ID | AA SEQ ID NO: Y | Biological Activity |
|---|---|---|---|
| 4 | HEQCC55 | 16 | Biological Activity #94: Production of IL-13 and activation of T-cells. |
| 4 | HEQCC55 | 16 | Biological Activity #103: Production of MCP-1 |
| 11 | HLHFP03 | 79 | Biological Activity #12: Activation of T-Cell p38 or JNK Signaling Pathway. |
| 11 | HLHFP03 | 79 | Biological Activity #12: Activation of T-Cell p38 or JNK Signaling Pathway. |
| 11 | HLHFP03 | 79 | Biological Activity #110: Production of VCAM in endothelial cells (such as human umbilical vein endothelial cells (HUVEC)) |
| 12 | HHTLF25 | 84 | Biological Activity #92: Production of IL-10 and downregulation of immune responses |
| 13 | HTADX17 | 93 | Biological Activity #21: Activation of transcription through GAS response element in immune cells (such as T-cells). |
| 13 | HTADX17 | 93 | Biological Activity #27: Activation of transcription through NFAT response in immune cells (such as T-cells). |
| 13 | HTADX17 | 93 | Biological Activity #35: Activation of transcription through NFKB response element in immune cells (such as T-cells). |
| 14 | HJACG02 | 105 | Biological Activity #112: Proliferation of pre-adipose cells (such as 3T3-L1 cells) |
| 14 | HJACG02 | 105 | Biological Activity #48: Activation or inhibition of transcription through NFKB response element in immune cells (such as basophils). |
| 17 | HSDEK49 | 126 | Biological Activity #41: Activation of transcription through serum response element in immune cells (such as T-cells). |
| 17 | HSDEK49 | 126 | Biological Activity #118: Regulation of transcription of Malic Enzyme in adipocytes |
| 17 | HSDEK49 | 126 | Biological Activity #41: Activation of transcription through serum response element in immune cells (such as T-cells). |
| 17 | HSDEK49 | 126 | Biological Activity #118: Regulation of transcription of Malic Enzyme in adipocytes |
| 17 | HSDEK49 | 126 | Biological Activity #84: MIP-1a in HMC |
| 18 | HWBAO62 | 128 | Biological Activity #17: Activation of transcription through CD28 response element in immune cells (such as T-cells). |
| 19 | HWHGU54 | 132 | Biological Activity #16: Activation of transcription through cAMP response element in immune cells (such as T-cells). |
| 19 | HWHGU54 | 132 | Biological Activity #100: Production of IL-8 by endothelial cells (such as Human Umbilical Cord Endothelial Cells). |
| 21 | HT5GJ57 | 160 | Biological Activity #103: Production of MCP-1 |
| 21 | HT5GJ57 | 160 | Biological Activity #14: Activation of transcription through AP1 response element in immune cells (such as T-cells). |
| 21 | HT5GJ57 | 162 | Biological Activity #14: Activation of transcription through AP1 response element in immune cells (such as T-cells). |
| 21 | HT5GJ57 | 162 | Biological Activity #103: Production of MCP-1 |
| 27 | HDHMA45 | 203 | Biological Activity #91: Production of IL-10 and activation of T-cells. |
| 31 | HDPPA04 | 225 | Biological Activity #104: Production of MIP1alpha |
| 33 | HKABZ65 | 233 | Biological Activity #5: Activation of Endothelial Cell p38 or JNK Signaling Pathway. |
| 33 | HKABZ65 | 233 | Biological Activity #98: Production of IL-6 |
| 33 | HKABZ65 | 233 | Biological Activity #115: Regulation of apoptosis in pancreatic beta cells. |
| 33 | HKABZ65 | 233 | Biological Activity #98: Production of IL-6 |
| 33 | HKABZ65 | 233 | Biological Activity #5: Activation of Endothelial Cell p38 or JNK Signaling Pathway. |
| 33 | HKABZ65 | 233 | Biological Activity #115: Regulation of apoptosis in pancreatic beta cells. |

TABLE 1E.2

| Biological Activity No. | Biological Activity | Exemplary Activity Assay | Preferred Indication |
|---|---|---|---|
| 1 | Activation of Adipocyte ERK Signaling Pathway | Kinase assay. Kinase assays, for example an Elk-1 kinase assay, for ERK signal transduction that regulate cell proliferation or differentiation are well known in the art and may be used or routinely modified to assess the ability of polypeptides of the invention (including antibodies and agonists or antagonists of the invention) to promote or inhibit cell proliferation, activation, and differentiation. Exemplary assays for ERK kinase activity that may be used or routinely modified to test ERK kinase-induced activity of polypeptides of the invention (including antibodies and agonists or antagonists of the invention) include the assays disclosed in Forrer et al., Biol Chem 379(8-9): 1101-1110 (1998); Le Marchand-Brustel Y, Exp Clin Endocrinol Diabetes 107(2): 126-132 (1999); Kyriakis J M, Biochem Soc Symp 64: 29-48 (1999); Chang and Karin, Nature 410(6824): 37-40 (2001); and Cobb M H, Prog Biophys Mol Biol 71(3-4): 479-500 (1999); the contents of each of which are herein incorporated by reference in its entirety. Mouse adipocyte cells that may be used according to these assays are publicly available (e.g., through | A highly preferred embodiment of the invention includes a method for stimulating adipocyte proliferation. An alternative highly preferred embodiment of the invention includes a method for inhibiting adipocyte proliferation. A highly preferred embodiment of the invention includes a method for stimulating adipocyte differentiation. An alternative highly preferred embodiment of the invention includes a method for inhibiting adipocyte differentiation. A highly preferred embodiment of the invention includes a method for stimulating (e.g., increasing) adipocyte activation. An alternative highly preferred embodiment of the invention includes a method for inhibiting the activation of (e.g., decreasing) and/or inactivating adipocytes. Highly preferred indications include endocrine disorders (e.g., as described below under "Endocrine Disorders"). Highly preferred indications also include neoplastic diseases (e.g., lipomas, liposarcomas, and/or as described below under "Hyperproliferative Disorders"). Preferred indications include blood disorders (e.g., hypertension, congestive heart failure, blood vessel blockage, heart disease, stroke, impotence and/or as described below under |

TABLE 1E.2-continued

| Biological Activity No. | Biological Activity | Exemplary Activity Assay | Preferred Indication |
|---|---|---|---|
| | | the ATCC ™). Exemplary mouse adipocyte cells that may be used according to these assays include 3T3-L1 cells. 3T3-L1 is an adherent mouse preadipocyte cell line that is a continuous substrain of 3T3 fibroblast cells developed through clonal isolation and undergo a pre-adipocyte to adipose-like conversion under appropriate differentiation conditions known in the art. | "Immune Activity", "Cardiovascular Disorders", and/or "Blood-Related Disorders"), immune disorders (e.g., as described below under "Immune Activity"), neural disorders (e.g., as described below under "Neural Activity and Neurological Diseases"), and infection (e.g., as described below under "Infectious Disease"). A highly preferred indication is diabetes mellitus. An additional highly preferred indication is a complication associated with diabetes (e.g., diabetic retinopathy, diabetic nephropathy, kidney disease (e.g., renal failure, nephropathy and/or other diseases and disorders as described in the "Renal Disorders" section below), diabetic neuropathy, nerve disease and nerve damage (e.g., due to diabetic neuropathy), blood vessel blockage, heart disease, stroke, impotence (e.g., due to diabetic neuropathy or blood vessel blockage), seizures, mental confusion, drowsiness, nonketotic hyperglycemic-hyperosmolar coma, cardiovascular disease (e.g., heart disease, atherosclerosis, microvascular disease, hypertension, stroke, and other diseases and disorders as described in the "Cardiovascular Disorders" section below), dyslipidemia, endocrine disorders (as described in the "Endocrine Disorders" section below), neuropathy, vision impairment (e.g., diabetic retinopathy and blindness), ulcers and impaired wound healing, infection (e.g., infectious diseases and disorders as described in the "Infectious Diseases" section below (particularly of the urinary tract and skin). An additional highly preferred indication is obesity and/or complications associated with obesity. Additional highly preferred indications include weight loss or alternatively, weight gain. Additional highly preferred indications are complications associated with insulin resistance. Additional highly preferred indications are disorders of the musculoskeletal systems including myopathies, muscular dystrophy, and/or as described herein. Additional highly preferred indications include, hypertension, coronary artery disease, dyslipidemia, gallstones, osteoarthritis, degenerative arthritis, eating disorders, fibrosis, cachexia, and kidney diseases or disorders. Preferred indications include neoplasms and cancer, such as, lymphoma, leukemia and breast, colon, and kidney cancer. Additional preferred indications include melanoma, prostate, lung, pancreatic, esophageal, stomach, brain, liver, and urinary cancer. Highly preferred indications include lipomas and liposarcomas. Other preferred indications include benign dysproliferative disorders and pre-neoplastic conditions, such as, for example, hyperplasia, metaplasia, and/or dysplasia. |
| 2 | Activation of Adipocyte PI3 Kinase Signaling Pathway | Kinase assay. Kinase assays, for example an GSK-3 assays, for PI3 kinase signal transduction that regulate glucose metabolism and cell survival are well-known in the art and may be used or routinely modified to assess the ability of polypeptides of the invention (including antibodies and agonists or antagonists of the invention) to promote or inhibit glucose metabolism and cell survival. Exemplary assays for PI3 kinase activity that may be used or routinely modified to test PI3 kinase-induced activity of polypeptides of the invention (including antibodies and agonists or antagonists of the invention) | |

TABLE 1E.2-continued

| Biological Activity No. | Biological Activity | Exemplary Activity Assay | Preferred Indication |
|---|---|---|---|
| | | include assays disclosed in Forrer et al., Biol Chem 379(8-9): 1101-1110 (1998); Nikoulina et al., Diabetes 49(2): 263-271 (2000); and Schreyer et al., Diabetes 48(8): 1662-1666 (1999), the contents of each of which are herein incorporated by reference in its entirety. Mouse adipocyte cells that may be used according to these assays are publicly available (e.g., through the ATCC ™). Exemplary mouse adipocyte cells that may be used according to these assays include 3T3-L1 cells. 3T3-L1 is an adherent mouse preadipocyte cell line that is a continuous substrain of 3T3 fibroblast cells developed through clonal isolation and undergo a pre-adipocyte to adipose-like conversion under appropriate differentiation conditions known in the art. | |
| 3 | Activation of Endothelial Cell ERK Signaling Pathway. | Kinase assay. Kinase assays, for example an Elk-1 kinase assay, for ERK signal transduction that regulate cell proliferation or differentiation are well known in the art and may be used or routinely modified to assess the ability of polypeptides of the invention (including antibodies and agonists or antagonists of the invention) to promote or inhibit cell proliferation, activation, and differentiation. Exemplary assays for ERK kinase activity that may be used or routinely modified to test ERK kinase-induced activity of polypeptides of the invention (including antibodies and agonists or antagonists of the invention) include the assays disclosed in Forrer et al., Biol Chem 379(8-9): 1101-1110 (1998); Berra et al., Biochem Pharmacol 60(8): 1171-1178 (2000); Gupta et al., Exp Cell Res 247(2): 495-504 (1999); Chang and Karin, Nature 410(6824): 37-40 (2001); and Cobb MH, Prog Biophys Mol Biol 71(3-4): 479-500 (1999); the contents of each of which are herein incorporated by reference in its entirety. Endothelial cells that may be used according to these assays are publicly available (e.g., through the ATCC ™). Exemplary endothelial cells that may be used according to these assays include human umbilical vein endothelial cells (HUVEC), which are endothelial cells which line venous blood vessels, and are involved in functions that include, but are not limited to, angiogenesis, vascular permeability, vascular tone, and immune cell extravasation. | A highly preferred embodiment of the invention includes a method for stimulating endothelial cell growth. An alternative highly preferred embodiment of the invention includes a method for inhibiting endothelial cell growth. A highly preferred embodiment of the invention includes a method for stimulating endothelial cell proliferation. An alternative highly preferred embodiment of the invention includes a method for inhibiting endothelial cell proliferation. A highly preferred embodiment of the invention includes a method for stimulating apoptosis of endothelial cells. An alternative highly preferred embodiment of the invention includes a method for inhibiting (e.g., decreasing) apoptosis of endothelial cells. A highly preferred embodiment of the invention includes a method for stimulating (e.g., increasing) endothelial cell activation. An alternative highly preferred embodiment of the invention includes a method for inhibiting the activation of (e.g., decreasing) and/or inactivating endothelial cells. A highly preferred embodiment of the invention includes a method for stimulating endothelial cell differentiation. An alternative highly preferred embodiment of the invention includes a method for inhibiting endothelial cell differentiation. A highly preferred embodiment of the invention includes a method for stimulating angiogenisis. An alternative highly preferred embodiment of the invention includes a method for inhibiting angiogenesis. A highly preferred embodiment of the invention includes a method for reducing cardiac hypertrophy. An alternative highly preferred embodiment of the invention includes a method for inducing cardiac hypertrophy. Highly preferred indications include neoplastic diseases (e.g., as described below under "Hyperproliferative Disorders"), and disorders of the cardiovascular system (e.g., heart disease, congestive heart failure, hypertension, aortic stenosis, cardiomyopathy, valvular regurgitation, left ventricular dysfunction, atherosclerosis and atherosclerotic vascular disease, diabetic nephropathy, intracardiac shunt, cardiac hypertrophy, myocardial infarction, chronic hemodynamic overload, and/or as described below under "Cardiovascular Disorders"). Highly preferred indications include cardiovascular, endothelial and/or angiogenic disorders (e.g., systemic disorders that affect vessels such as diabetes mellitus, as well as diseases of the vessels themselves, such as of the arteries, capillaries, veins and/or lymphatics). Highly preferred are indications that stimulate angiogenesis and/or |

TABLE 1E.2-continued

| Biological Activity No. | Biological Activity | Exemplary Activity Assay | Preferred Indication |
|---|---|---|---|
| | | | cardiovascularization. Highly preferred are indications that inhibit angiogenesis and/or cardiovascularization. Highly preferred indications include antiangiogenic activity to treat solid tumors, leukemias, and Kaposi's sarcoma, and retinal disorders. Highly preferred indications include neoplasms and cancer, such as, Kaposi's sarcoma, hemangioma (capillary and cavernous), glomus tumors, telangiectasia, bacillary angiomatosis, hemangioendothelioma, angiosarcoma, haemangiopericytoma, lymphangioma, lymphangiosarcoma. Highly preferred indications also include cancers such as, prostate, breast, lung, colon, pancreatic, esophageal, stomach, brain, liver, and urinary cancer. Preferred indications include benign dysproliferative disorders and pre-neoplastic conditions, such as, for example, hyperplasia, metaplasia, and/or dysplasia. Highly preferred indications also include arterial disease, such as, atherosclerosis, hypertension, coronary artery disease, inflammatory vasculitides, Reynaud's disease and Reynaud's phenomenom, aneurysms, restenosis; venous and lymphatic disorders such as thrombophlebitis, lymphangitis, and lymphedema; and other vascular disorders such as peripheral vascular disease, and cancer. Highly preferred indications also include trauma such as wounds, burns, and injured tissue (e.g., vascular injury such as, injury resulting from balloon angioplasty, and atheroschlerotic lesions), implant fixation, scarring, ischemia reperfusion injury, rheumatoid arthritis, cerebrovascular disease, renal diseases such as acute renal failure, and osteoporosis. Additional highly preferred indications include stroke, graft rejection, diabetic or other retinopathies, thrombotic and coagulative disorders, vascularitis, lymph angiogenesis, sexual disorders, age-related macular degeneration, and treatment/ prevention of endometriosis and related conditions. Additional highly preferred indications include fibromas, heart disease, cardiac arrest, heart valve disease, and vascular disease. Preferred indications include blood disorders (e.g., as described below under "Immune Activity", "Blood-Related Disorders", and/or ""Cardiovascular Disorders""). Preferred indications include autoimmune diseases (e.g., rheumatoid arthritis, systemic lupus erythematosis, multiple sclerosis and/or as described below) and immunodeficiencies (e.g., as described below). Additional preferred indications include inflammation and inflammatory disorders (such as acute and chronic inflammatory diseases, e.g., inflammatory bowel disease and Crohn's disease), and pain management. |
| 4 | Activation of Endothelial Cell JNK Signaling Pathway. | Kinase assay. JNK kinase assays for signal transduction that regulate cell proliferation, activation, or apoptosis are well known in the art and may be used or routinely modified to assess the ability of polypeptides of the invention (including antibodies and agonists or antagonists of the invention) to promote or inhibit cell proliferation, activation, and apoptosis. Exemplary assays for JNK kinase activity that may be used or routinely modified to test JNK kinase-induced activity of polypeptides of the invention (including antibodies and agonists or antagonists of the invention) include the assays disclosed in Forrer et al., Biol Chem 379(8-9): 1101-1110 | A highly preferred embodiment of the invention includes a method for stimulating endothelial cell growth. An alternative highly preferred embodiment of the invention includes a method for inhibiting endothelial cell growth. A highly preferred embodiment of the invention includes a method for stimulating endothelial cell proliferation. An alternative highly preferred embodiment of the invention includes a method for inhibiting endothelial cell proliferation. A highly preferred embodiment of the invention includes a method for stimulating apoptosis of endothelial cells. An alternative highly preferred embodiment of the invention includes a method for inhibiting apoptosis of endothelial cells. A highly |

TABLE 1E.2-continued

| Biological Activity No. | Biological Activity | Exemplary Activity Assay | Preferred Indication |
|---|---|---|---|
| | | (1998); Gupta et al., Exp Cell Res 247(2): 495-504 (1999); Kyriakis J M, Biochem Soc Symp 64: 29-48 (1999); Chang and Karin, Nature 410(6824): 37-40 (2001); and Cobb M H, Prog Biophys Mol Biol 71(3-4): 479-500 (1999); the contents of each of which are herein incorporated by reference in its entirety. Endothelial cells that may be used according to these assays are publicly available (e.g., through the ATCC ™). Exemplary endothelial cells that may be used according to these assays include human umbilical vein endothelial cells (HUVEC), which are endothelial cells which line venous blood vessels, and are involved in functions that include, but are not limited to, angiogenesis, vascular permeability, vascular tone, and immune cell extravasation. | preferred embodiment of the invention includes a method for stimulating endothelial cell activation. An alternative highly preferred embodiment of the invention includes a method for inhibiting the activation of and/or inactivating endothelial cells. A highly preferred embodiment of the invention includes a method for stimulating angiogenisis. An alternative highly preferred embodiment of the invention includes a method for inhibiting angiogenesis. A highly preferred embodiment of the invention includes a method for reducing cardiac hypertrophy. An alternative highly preferred embodiment of the invention include a method for inducing cardiac hypertrophy. Highly preferred indications include neoplastic diseases (e.g., as described below under "Hyperproliferative Disorders"), and disorders of the cardiovascular system (e.g., heart disease, congestive heart failure, hypertension, aortic stenosis, cardiomyopathy, valvular regurgitation, left ventricular dysfunction, atherosclerosis and atherosclerotic vascular disease, diabetic nephropathy, intracardiac shunt, cardiac hypertrophy, myocardial infarction, chronic hemodynamic overload, and/or as described below under "Cardiovascular Disorders"). Highly preferred indications include cardiovascular, endothelial and/or angiogenic disorders (e.g., systemic disorders that affect vessels such as diabetes mellitus, as well as diseases of the vessels themselves, such as of the arteries, capillaries, veins and/or lymphatics). Highly preferred are indications that stimulate angiogenesis and/or cardiovascularization. Highly preferred are indications that inhibit angiogenesis and/or cardiovascularization. Highly preferred indications include antiangiogenic activity to treat solid tumors, leukemias, and Kaposi"s sarcoma, and retinal disorders. Highly preferred indications include neoplasms and cancer, such as, Kaposi"s sarcoma, hemangioma (capillary and cavernous), glomus tumors, telangiectasia, bacillary angiomatosis, hemangioendothelioma, angiosarcoma, haemangiopericytoma, lymphangioma, lymphangiosarcoma. Highly preferred indications also include cancers such as, prostate, breast, lung, colon, pancreatic, esophageal, stomach, brain, liver, and urinary cancer. Preferred indications include benign dysproliferative disorders and pre-neoplastic conditions, such as, for example, hyperplasia, metaplasia, and/or dysplasia. Highly preferred indications also include arterial disease, such as, atherosclerosis, hypertension, coronary artery disease, inflammatory vasculitides, Reynaud"s disease and Reynaud"s phenomenom, aneurysms, restenosis; venous and lymphatic disorders such as thrombophlebitis, lymphangitis, and lymphedema; and other vascular disorders such as peripheral vascular disease, and cancer. Highly preferred indications also include trauma such as wounds, burns, and injured tissue (e.g., vascular injury such as, injury resulting from balloon angioplasty, and atheroschlerotic lesions), implant fixation, scarring, ischemia reperfusion injury, rheumatoid arthritis, cerebrovascular disease, renal diseases such as acute renal failure, and osteoporosis. Additional highly preferred indications include stroke, graft rejection, diabetic or other retinopathies, thrombotic and coagulative disorders, vascularitis, lymph angiogenesis, sexual disorders, age-related |

TABLE 1E.2-continued

| Biological Activity No. | Biological Activity | Exemplary Activity Assay | Preferred Indication |
|---|---|---|---|
| | | | macular degeneration, and treatment/ prevention of endometriosis and related conditions. Additional highly preferred indications include fibromas, heart disease, cardiac arrest, heart valve disease, and vascular disease. Preferred indications include blood disorders (e.g., as described below under "Immune Activity", "Blood-Related Disorders", and/or "Cardiovascular Disorders"). Preferred indications include autoimmune diseases (e.g., rheumatoid arthritis, systemic lupus erythematosis, multiple sclerosis and/or as described below) and immunodeficiencies (e.g., as described below). Additional preferred indications include inflammation and inflammatory disorders (such as acute and chronic inflammatory diseases, e.g., inflammatory bowel disease and Crohn's disease), and pain management. |
| 5 | Activation of Endothelial Cell p38 or JNK Signaling Pathway. | Kinase assay. JNK and p38 kinase assays for signal transduction that regulate cell proliferation, activation, or apoptosis are well known in the art and may be used or routinely modified to assess the ability of polypeptides of the invention (including antibodies and agonists or antagonists of the invention) to promote or inhibit cell proliferation, activation, and apoptosis. Exemplary assays for JNK and p38 kinase activity that may be used or routinely modified to test JNK and p38 kinase-induced activity of polypeptides of the invention (including antibodies and agonists or antagonists of the invention) include the assays disclosed in Forrer et al., Biol Chem 379(8-9): 1101-1110 (1998); Gupta et al., Exp Cell Res 247(2): 495-504 (1999); Kyriakis J M, Biochem Soc Symp 64: 29-48 (1999); Chang and Karin, Nature 410(6824): 37-40 (2001); and Cobb M H, Prog Biophys Mol Biol 71(3-4): 479-500 (1999); the contents of each of which are herein incorporated by reference in its entirety. Endothelial cells that may be used according to these assays are publicly available (e.g., through the ATCC ™™). Exemplary endothelial cells that may be used according to these assays include human umbilical vein endothelial cells (HUVEC), which are endothelial cells which line venous blood vessels, and are involved in functions that include, but are not limited to, angiogenesis, vascular permeability, vascular tone, and immune cell extravasation. | A highly preferred embodiment of the invention includes a method for stimulating endothelial cell growth. An alternative highly preferred embodiment of the invention includes a method for inhibiting endothelial cell growth. A highly preferred embodiment of the invention includes a method for stimulating endothelial cell proliferation. An alternative highly preferred embodiment of the invention includes a method for inhibiting endothelial cell proliferation. A highly preferred embodiment of the invention includes a method for stimulating apoptosis of endothelial cells. An alternative highly preferred embodiment of the invention includes a method for inhibiting (e.g., decreasing) apoptosis of endothelial cells. A highly preferred embodiment of the invention includes a method for stimulating (e.g., increasing) endothelial cell activation. An alternative highly preferred embodiment of the invention includes a method for inhibiting (e.g., decreasing) the activation of and/or inactivating endothelial cells. A highly preferred embodiment of the invention includes a method for stimulating angiogenisis. An alternative highly preferred embodiment of the invention includes a method for inhibiting angiogenesis. A highly preferred embodiment of the invention includes a method for reducing cardiac hypertrophy. An alternative highly preferred embodiment of the invention includes a method for inducing cardiac hypertrophy. Highly preferred indications include neoplastic diseases (e.g., as described below under "Hyperproliferative Disorders"), and disorders of the cardiovascular system (e.g., heart disease, congestive heart failure, hypertension, aortic stenosis, cardiomyopathy, valvular regurgitation, left ventricular dysfunction, atherosclerosis and atherosclerotic vascular disease, diabetic nephropathy, intracardiac shunt, cardiac hypertrophy, myocardial infarction, chronic hemodynamic overload, and/or as described below under "Cardiovascular Disorders"). Highly preferred indications include cardiovascular, endothelial and/or angiogenic disorders (e.g., systemic disorders that affect vessels such as diabetes mellitus, as well as diseases of the vessels themselves, such as of the arteries, capillaries, veins and/or lymphatics). Highly preferred are indications that stimulate angiogenesis and/or cardiovascularization. Highly preferred are indications that inhibit angiogenesis and/or cardiovascularization. Highly preferred indications include antiangiogenic activity to treat solid tumors, leukemias, and Kaposi's |

TABLE 1E.2-continued

| Biological Activity No. | Biological Activity | Exemplary Activity Assay | Preferred Indication |
|---|---|---|---|
| | | | sarcoma, and retinal disorders. Highly preferred indications include neoplasms and cancer, such as, Kaposi's sarcoma, hemangioma (capillary and cavernous), glomus tumors, telangiectasia, bacillary angiomatosis, hemangioendothelioma, angiosarcoma, haemangiopericytoma, lymphangioma, lymphangiosarcoma. Highly preferred indications also include cancers such as, prostate, breast, lung, colon, pancreatic, esophageal, stomach, brain, liver, and urinary cancer. Preferred indications include benign dysproliferative disorders and pre-neoplastic conditions, such as, for example, hyperplasia, metaplasia, and/or dysplasia. Highly preferred indications also include arterial disease, such as, atherosclerosis, hypertension, coronary artery disease, inflammatory vasculitides, Reynaud's disease and Reynaud's phenomenom, aneurysms, restenosis; venous and lymphatic disorders such as thrombophlebitis, lymphangitis, and lymphedema; and other vascular disorders such as peripheral vascular disease, and cancer. Highly preferred indications also include trauma such as wounds, burns, and injured tissue (e.g., vascular injury such as, injury resulting from balloon angioplasty, and atheroschlerotic lesions), implant fixation, scarring, ischemia reperfusion injury, rheumatoid arthritis, cerebrovascular disease, renal diseases such as acute renal failure, and osteoporosis. Additional highly preferred indications include stroke, graft rejection, diabetic or other retinopathies, thrombotic and coagulative disorders, vascularitis, lymph angiogenesis, sexual disorders, age-related macular degeneration, and treatment/prevention of endometriosis and related conditions. Additional highly preferred indications include fibromas, heart disease, cardiac arrest, heart valve disease, and vascular disease. Preferred indications include blood disorders (e.g., as described below under "Immune Activity", "Blood-Related Disorders", and/or ""Cardiovascular Disorders""). Preferred indications include autoimmune diseases (e.g., rheumatoid arthritis, systemic lupus erythematosis, multiple sclerosis and/or as described below) and immunodeficiencies (e.g., as described below). Additional preferred indications include inflammation and inflammatory disorders (such as acute and chronic inflammatory diseases, e.g., inflammatory bowel disease and Crohn's disease), and pain management. |
| 6 | Activation of Hepatocyte ERK Signaling Pathway | Kinase assay. Kinase assays, for example an Elk-1 kinase assay, for ERK signal transduction that regulate cell proliferation or differentiation are well known in the art and may be used or routinely modified to assess the ability of polypeptides of the invention (including antibodies and agonists or antagonists of the invention) to promote or inhibit cell proliferation, activation, and differentiation. Exemplary assays for ERK kinase activity that may be used or routinely modified to test ERK kinase-induced activity of polypeptides of the invention (including antibodies and agonists or antagonists of the invention) include the assays disclosed in Forrer et al., Biol Chem 379(8-9): 1101-1110 (1998); Kyriakis J M, Biochem Soc Symp 64: 29-48 (1999); Chang and Karin, Nature 410(6824): 37-40 (2001); and Cobb M H, Prog Biophys Mol Biol 71(3-4): 479-500 (1999); the contents | A highly preferred embodiment of the invention includes a method for stimulating hepatocyte cell proliferation. An alternative highly preferred embodiment of the invention includes a method for inhibiting hepatocyte cell proliferation. A highly preferred embodiment of the invention includes a method for stimulating hepatocyte cell differentiation. An alternative highly preferred embodiment of the invention includes a method for inhibiting hepatocyte cell differentiation. A highly preferred embodiment of the invention includes a method for activating hepatocyte cells. An alternative highly preferred embodiment of the invention includes a method for inhibiting the activation of and/or inactivating hepatocyte cells. Highly preferred indications include disorders of the liver and/or endocrine disorders (e.g., as described below under "Endocrine Disorders"). Preferred indications include neoplastic diseases (e.g., as described below |

TABLE 1E.2-continued

| Biological Activity No. | Biological Activity | Exemplary Activity Assay | Preferred Indication |
|---|---|---|---|
| | | of each of which are herein incorporated by reference in its entirety. Rat liver hepatoma cells that may be used according to these assays are publicly available (e.g., through the ATCC ™). Exemplary rat liver hepatoma cells that may be used according to these assays include H4lle cells, which are known to respond to glucocorticoids, insulin, or cAMP derivatives. | under “Hyperproliferative Disorders”), blood disorders (e.g., as described below under “Immune Activity”, “Cardiovascular Disorders”, and/or “Blood-Related Disorders”), immune disorders (e.g., as described below under “Immune Activity”), neural disorders (e.g., as described below under “Neural Activity and Neurological Diseases”), and infection (e.g., as described below under “Infectious Disease”). A highly preferred indication is diabetes mellitus. An additional highly preferred indication is a complication associated with diabetes (e.g., diabetic retinopathy, diabetic nephropathy, kidney disease (e.g., renal failure, nephropathy and/or other diseases and disorders as described in the “Renal Disorders” section below), diabetic neuropathy, nerve disease and nerve damage (e.g., due to diabetic neuropathy), blood vessel blockage, heart disease, stroke, impotence (e.g., due to diabetic neuropathy or blood vessel blockage), seizures, mental confusion, drowsiness, nonketotic hyperglycemic-hyperosmolar coma, cardiovascular disease (e.g., heart disease, atherosclerosis, microvascular disease, hypertension, stroke, and other diseases and disorders as described in the “Cardiovascular Disorders” section below), dyslipidemia, endocrine disorders (as described in the “Endocrine Disorders” section below), neuropathy, vision impairment (e.g., diabetic retinopathy and blindness), ulcers and impaired wound healing, infection (e.g., infectious diseases and disorders as described in the “Infectious Diseases” section below, especially of the urinary tract and skin), carpal tunnel syndrome and Dupuytren’s contracture). An additional highly preferred indication is obesity and/or complications associated with obesity. Additional highly preferred indications include weight loss or alternatively, weight gain. Additional highly preferred indications are complications associated with insulin resistance. Additonal highly preferred indications are disorders of the musculoskeletal systems including myopathies, muscular dystrophy, and/or as described herein. Additional highly preferred indications include, hepatitis, jaundice, gallstones, cirrhosis of the liver, degenerative or necrotic liver disease, alcoholic liver diseases, fibrosis, liver regeneration, metabolic disease, dyslipidemia and chlolesterol metabolism. Additional highly preferred indications include neoplasms and cancers, such as, hepatocarcinomas, other liver cancers, and colon and pancreatic cancer. Preferred indications also include prostate, breast, lung, esophageal, stomach, brain, and urinary cancer. Other preferred indications include benign dysproliferative disorders and pre-neoplastic conditions, such as, for example, hyperplasia, metaplasia, and/or dysplasia. |
| 7 | Activation of JNK Signaling Pathway in immune cells (such as eosinophils). | Kinase assay. JNK kinase assays for signal transduction that regulate cell proliferation, activation, or apoptosis are well known in the art and may be used or routinely modified to assess the ability of polypeptides of the invention (including antibodies and agonists or antagonists of the invention) to promote or inhibit cell proliferation, activation, and apoptosis. Exemplary assays for JNK kinase activity that may be used or routinely modified to test JNK kinase-induced activity of | Highly preferred indications include asthma, allergy, hypersensitivity reactions, inflammation, and inflammatory disorders. Additional highly preferred indications include immune and hematopoietic disorders (e.g., as described below under “Immune Activity”, and “Blood-Related Disorders”), autoimmune diseases (e.g., rheumatoid arthritis, systemic lupus erythematosis, Crohn’’s disease, multiple sclerosis and/or as described below), immunodeficiencies (e.g., as described below). Highly preferred indications also include |

TABLE 1E.2-continued

| Biological Activity No. | Biological Activity | Exemplary Activity Assay | Preferred Indication |
|---|---|---|---|
| | | polypeptides of the invention (including antibodies and agonists or antagonists of the invention) include the assays disclosed in Forrer et al., Biol Chem 379(8-9): 1101-1110 (1998); Gupta et al., Exp Cell Res 247(2): 495-504 (1999); Kyriakis J M, Biochem Soc Symp 64: 29-48 (1999); Chang and Karin, Nature 410(6824): 37-40 (2001); and Cobb M H, Prog Biophys Mol Biol 71(3-4): 479-500 (1999); the contents of each of which are herein incorporated by reference in its entirety. Exemplary cells that may be used according to these assays include eosinophils. Eosinophils are important in the late stage of allergic reactions; they are recruited to tissues and mediate the inflammatory response of late stage allergic reaction. Moreover, exemplary assays that may be used or routinely modified to assess the ability of polypeptides of the invention (including antibodies and agonists or antagonists of the invention) to modulate signal transduction, cell proliferation, activation, or apoptosis in eosinophils include assays disclosed and/or cited in: Zhang J P, et al., "Role of caspases in dexamethasone-induced apoptosis and activation of c-Jun NH2-terminal kinase and p38 mitogen-activated protein kinase in human eosinophils" Clin Exp Immunol; October; 122(1): 20-7 (2000); Hebestreit H, et al., "Disruption of fas receptor signaling by nitric oxide in eosinophils" J Exp Med; February 2; 187(3): 415-25 (1998); J Allergy Clin Immunol 1999 September; 104(3 Pt 1): 565-74; and, Sousa A R, et al., "In vivo resistance to corticosteroids in bronchial asthma is associated with enhanced phosyphorylation of JUN N-terminal kinase and failure of prednisolone to inhibit JUN N-terminal kinase phosphorylation" J Allergy Clin Immunol; September; 104(3 Pt 1): 565-74 (1999); the contents of each of which are herein incorporated by reference in its entirety. | boosting or inhibiting immune cell proliferation. Preferred indications include neoplastic diseases (e.g., leukemia, lymphoma, and/or as described below under "Hyperproliferative Disorders"). Highly preferred indications include boosting an eosinophil-mediated immune response, and suppressing an eosinophil-mediated immune response. |
| 8 | Activation of Natural Killer Cell ERK Signaling Pathway. | Kinase assay. Kinase assays, for example an Elk-1 kinase assay, for ERK signal transduction that regulate cell proliferation or differentiation are well known in the art and may be used or routinely modified to assess the ability of polypeptides of the invention (including antibodies and agonists or antagonists of the invention) to promote or inhibit cell proliferation, activation, and differentiation. Exemplary assays for ERK kinase activity that may be used or routinely modified to test ERK kinase-induced activity of polypeptides of the invention (including antibodies and agonists or antagonists of the invention) include the assays disclosed in Forrer et al., Biol Chem 379(8-9): 1101-1110 (1998); Kyriakis J M, Biochem Soc Symp 64: 29-48 (1999); Chang and Karin, Nature 410(6824): 37-40 (2001); and Cobb M H, Prog Biophys Mol Biol 71(3-4): 479-500 (1999); the contents of each of which are herein incorporated by reference in its entirety. Natural killer cells that may be used according to these assays are publicly available (e.g., through the ATCC ™). Exemplary natural killer cells that may be used according to these assays include the human natural killer cell lines (for example, NK-YT cells which have cytolytic and cytotoxic activity) or primary NK cells. | A highly preferred embodiment of the invention includes a method for stimulating natural killer cell proliferation. An alternative highly preferred embodiment of the invention includes a method for inhibiting natural killer cell proliferation. A highly preferred embodiment of the invention includes a method for stimulating natural killer cell differentiation. An alternative highly preferred embodiment of the invention includes a method for inhibiting natural killer cell differentiation. Highly preferred indications include neoplastic diseases (e.g., as described below under "Hyperproliferative Disorders"), blood disorders (e.g., as described below under "Immune Activity", "Cardiovascular Disorders", and/or "Blood-Related Disorders"), immune disorders (e.g., as described below under "Immune Activity") and infections (e.g., as described below under "Infectious Disease"). Preferred indications include blood disorders (e.g., as described below under "Immune Activity", "Blood-Related Disorders", and/or "Cardiovascular Disorders"). Highly preferred indications include autoimmune diseases (e.g., rheumatoid arthritis, systemic lupus erythematosis, multiple sclerosis and/or as described below) and immunodeficiencies (e.g., as described below). Additional highly preferred indications include inflammation and inflammatory disorders. Highly preferred indications also include cancers such as, kidney, |

TABLE 1E.2-continued

| Biological Activity No. | Biological Activity | Exemplary Activity Assay | Preferred Indication |
|---|---|---|---|
| | | | melanoma, prostate, breast, lung, colon, pancreatic, esophageal, stomach, brain, liver, urinary cancer, lymphoma and leukemias. Other preferred indications include benign dysproliferative disorders and pre-neoplastic conditions, such as, for example, hyperplasia, metaplasia, and/or dysplasia. Other highly preferred indications include, pancytopenia, leukopenia, leukemias, Hodgkin's disease, acute lymphocytic anemia (ALL), arthritis, asthma, AIDS, granulomatous disease, inflammatory bowel disease, sepsis, psoriasis, immune reactions to transplanted organs and tissues, endocarditis, meningitis, Lyme Disease, and allergies. |
| 9 | Activation of Skeletal Mucle Cell PI3 Kinase Signalling Pathway | Kinase assay. Kinase assays, for example an GSK-3 kinase assay, for PI3 kinase signal transduction that regulate glucose metabolism and cell survivial are well-known in the art and may be used or routinely modified to assess the ability of polypeptides of the invention (including antibodies and agonists or antagonists of the invention) to promote or inhibit glucose metabolism and cell survival. Exemplary assays for PI3 kinase activity that may be used or routinely modified to test PI3 kinase-induced activity of polypeptides of the invention (including antibodies and agonists or antagonists of the invention) include assays disclosed in Forrer et al., Biol Chem 379(8-9): 1101-1110 (1998); Nikoulina et al., Diabetes 49(2): 263-271 (2000); and Schreyer et al., Diabetes 48(8): 1662-1666 (1999), the contents of each of which are herein incorporated by reference in its entirety. Rat myoblast cells that may be used according to these assays are publicly available (e.g., through the ATCC ™). Exemplary rat myoblast cells that may be used according to these assays include L6 cells. L6 is an adherent rat myoblast cell line, isolated from primary cultures of rat thigh muscle, that fuses to form multinucleated myotubes and striated fibers after culture in differentiation media. | A highly preferred embodiment of the invention includes a method for increasing muscle cell survival An alternative highly preferred embodiment of the invention includes a method for decreasing muscle cell survival. A preferred embodiment of the invention includes a method for stimulating muscle cell proliferation. In a specific embodiment, skeletal muscle cell proliferation is stimulated. An alternative highly preferred embodiment of the invention includes a method for inhibiting muscle cell proliferation. In a specific embodiment, skeletal muscle cell proliferation is inhibited. A preferred embodiment of the invention includes a method for stimulating muscle cell differentiation. In a specific embodiment, skeletal muscle cell differentiation is stimulated. An alternative highly preferred embodiment of the invention includes a method for inhibiting muscle cell differentiation. In a specific embodiment, skeletal muscle cell differentiation is inhibited. Highly preferred indications include disorders of the musculoskeletal system. Preferred indications include neoplastic diseases (e.g., as described below under "Hyperproliferative Disorders"), endocrine disorders (e.g., as described below under ""Endocrine Disorders""), neural disorders (e.g., as described below under ""Neural Activity and Neurological Diseases""), blood disorders (e.g., as described below under "Immune Activity", "Cardiovascular Disorders", and/or "Blood-Related Disorders"), immune disorders (e.g., as described below under ""Immune Activity""), and infection (e.g., as described below under "Infectious Disease"). A highly preferred indication is diabetes mellitus. An additional highly preferred indication is a complication associated with diabetes (e.g., diabetic retinopathy, diabetic nephropathy, kidney disease (e.g., renal failure, nephropathy and/or other diseases and disorders as described in the ""Renal Disorders"" section below), diabetic neuropathy, nerve disease and nerve damage (e.g, due to diabetic neuropathy), blood vessel blockage, heart disease, stroke, impotence (e.g., due to diabetic neuropathy or blood vessel blockage), seizures, mental confusion, drowsiness, nonketotic hyperglycemic-hyperosmolar coma, cardiovascular disease (e.g., heart disease, atherosclerosis, microvascular disease, hypertension, stroke, and other diseases and disorders as described in the ""Cardiovascular Disorders"" section below), dyslipidemia, endocrine disorders (as described in the ""Endocrine Disorders"" section below), neuropathy, vision impairment (e.g., diabetic retinopathy and blindness), ulcers and impaired wound healing, infections (e.g., infectious |

TABLE 1E.2-continued

| Biological Activity No. | Biological Activity | Exemplary Activity Assay | Preferred Indication |
|---|---|---|---|
| | | | diseases and disorders as described in the ""Infectious Diseases"" section below, especially of the urinary tract and skin), carpal tunnel syndrome and Dupuytren's contracture). An additional highly preferred indication is obesity and/or complications associated with obesity. Additional highly preferred indications include weight loss or alternatively, weight gain. Additional highly preferred indications are complications associated with insulin resistance. Additonal highly preferred indications are disorders of the musculoskeletal system including myopathies, muscular dystrophy, and/or as described herein. Additional highly preferred indications include: myopathy, atrophy, congestive heart failure, cachexia, myxomas, fibromas, congenital cardiovascular abnormalities, heart disease, cardiac arrest, heart valve disease, and vascular disease. Highly preferred indications include neoplasms and cancer, such as, rhabdomyoma, rhabdosarcoma, stomach, esophageal, prostate, and urinary cancer. Preferred indications also include breast, lung, colon, pancreatic, brain, and liver cancer. Other preferred indications include benign dysproliferative disorders and pre-neoplastic conditions, such as, hyperplasia, metaplasia, and/or dysplasia. |
| 10 | Activation of Skeletal Muscle Cell ERK Signaling Pathway | Kinase assay. Kinase assays, for example Elk-1 kinase assays, for ERK signal transduction that regulate cell proliferation or differentiation are well known in the art and may be used or routinely modified to assess the ability of polypeptides of the invention (including antibodies and agonists or antagonists of the invention) to promote or inhibit cell proliferation, activation, and differentiation. Exemplary assays for ERK kinase activity that may be used or routinely modified to test ERK kinase-induced activity of polypeptides of the invention (including antibodies and agonists or antagonists of the invention) include the assays disclosed in Forrer et al., Biol Chem 379(8-9): 1101-1110 (1998); Le Marchand-Brustel Y, Exp Clin Endocrinol Diabetes 107(2): 126-132 (1999); Kyriakis J M, Biochem Soc Symp 64: 29-48 (1999); Chang and Karin, Nature 410(6824): 37-40 (2001); and Cobb M H, Prog Biophys Mol Biol 71(3-4): 479-500 (1999); the contents of each of which are herein incorporated by reference in its entirety. Rat myoblast cells that may be used according to these assays are publicly available (e.g., through the ATCC ™). Exemplary rat myoblast cells that may be used according to these assays include L6 cells. L6 is an adherent rat myoblast cell line, isolated from primary cultures of rat thigh muscle, that fuses to form multinucleated myotubes and striated fibers after culture in differentiation media. | |
| 11 | Activation of Skeletal Muscle Cell PI3 Kinase Signaling Pathway | Kinase assay. Kinase assays, for example an GSK-3 kinase assay, for PI3 kinase signal transduction that regulate glucose metabolism and cell survival are well-known in the art and may be used or routinely modified to assess the ability of polypeptides of the invention (including antibodies and agonists or antagonists of the invention) to promote or inhibit glucose metabolism and cell survival. Exemplary assays for PI3 kinase activity that may be used or routinely modified to test PI3 kinase-induced activity of polypeptides of | |

TABLE 1E.2-continued

| Biological Activity No. | Biological Activity | Exemplary Activity Assay | Preferred Indication |
|---|---|---|---|
| | | the invention (including antibodies and agonists or antagonists of the invention) include assays disclosed in Forrer et al., Biol Chem 379(8-9): 1101-1110 (1998); Nikoulina et al., Diabetes 49(2): 263-271 (2000); and Schreyer et al., Diabetes 48(8): 1662-1666 (1999), the contents of each of which are herein incorporated by reference in its entirety. Rat myoblast cells that may be used according to these assays are publicly available (e.g., through the ATCC ™). Exemplary rat myoblast cells that may be used according to these assays include L6 cells. L6 is an adherent rat myoblast cell line, isolated from primary cultures of rat thigh muscle, that fuses to form multinucleated myotubes and striated fibers after culture in differentiation media. | |
| 12 | Activation of T-Cell p38 or JNK Signaling Pathway. | Kinase assay. JNK and p38 kinase assays for signal transduction that regulate cell proliferation, activation, or apoptosis are well known in the art and may be used or routinely modified to assess the ability of polypeptides of the invention (including antibodies and agonists or antagonists of the invention) to promote or inhibit immune cell (e.g. T-cell) proliferation, activation, and apoptosis. Exemplary assays for JNK and p38 kinase activity that may be used or routinely modified to test JNK and p38 kinase-induced activity of polypeptides of the invention (including antibodies and agonists or antagonists of the invention) include the assays disclosed in Forrer et al., Biol Chem 379(8-9): 1101-1110 (1998); Gupta et al., Exp Cell Res 247(2): 495-504 (1999); Kyriakis J M, Biochem Soc Symp 64: 29-48 (1999); Chang and Karin, Nature 410(6824): 37-40 (2001); and Cobb M H, Prog Biophys Mol Biol 71(3-4): 479-500 (1999); the contents of each of which are herein incorporated by reference in its entirety. T cells that may be used according to these assays are publicly available (e.g., through the ATCC ™). Exemplary mouse T cells that may be used according to these assays include the CTLL cell line, which is an IL-2 dependent suspension-culture cell line with cytotoxic activity. | Preferred indications include neoplastic diseases (e.g., as described below under "Hyperproliferative Disorders"), blood disorders (e.g., as described below under "Immune Activity", "Cardiovascular Disorders", and/or "Blood-Related Disorders"), and infection (e.g., an infectious disease as described below under "Infectious Disease"). Highly preferred indications include autoimmune diseases (e.g., rheumatoid arthritis, systemic lupus erythematosis, multiple sclerosis and/or as described below) and immunodeficiencies (e.g., as described below). Additional highly preferred indications include inflammation and inflammatory disorders. Highly preferred indications also include neoplastic diseases (e.g., leukemia, lymphoma, and/or as described below under "Hyperproliferative Disorders"). Highly preferred indications include neoplasms and cancers, such as, leukemia, lymphoma, prostate, breast, lung, colon, pancreatic, esophageal, stomach, brain, liver, and urinary cancer. Other preferred indications include benign dysproliferative disorders and pre-neoplastic conditions, such as, for example, hyperplasia, metaplasia, and/or dysplasia. Preferred indications include arthritis, asthma, AIDS, allergy, anemia, pancytopenia, leukopenia, thrombocytopenia, Hodgkin"s disease, acute lymphocytic anemia (ALL), plasmacytomas, multiple myeloma, Burkitt"s lymphoma, granulomatous disease, inflammatory bowel disease, sepsis, psoriasis, suppression of immune reactions to transplanted organs and tissues, endocarditis, meningitis, and Lyme Disease. |
| 13 | Activation of Transcription | Assays for activation of transcription are well-known in the art and may be used and routinely modified to assess ability of polypeptides of the invention to inhibit or activate transcription. An example of such an assay follows: Cells were pretreated with SID supernatants or controls for 15-18 hours. SEAP activity was measured after 48 hours. LS174T is an epithelial colon adenocarcinoma cell line. Its tumourigenicity in nude mice make cell line LS174T a model for studies on the mechanism of synthesis and secretion of specific tumoral markers in colon cancer. See, Patan et al., Circ Res, 89(8): 732-39 (2001), the contents of which are herein incorporated by reference in its entirety. | |
| 14 | Activation of transcription through AP1 response element in immune | Assays for the activation of transcription through the AP1 response element are known in the art and may be used or routinely modified to assess the ability of | Preferred indications include neoplastic diseases (e.g., as described below under "Hyperproliferative Disorders"), blood disorders (e.g., as described below under |

TABLE 1E.2-continued

| Biological Activity No. | Biological Activity | Exemplary Activity Assay | Preferred Indication |
|---|---|---|---|
| | cells (such as T-cells). | polypeptides of the invention (including antibodies and agonists or antagonists of the invention) to modulate growth and other cell functions. Exemplary assays for transcription through the AP1 response element that may be used or routinely modified to test AP1-response element activity of polypeptides of the invention (including antibodies and agonists or antagonists of the invention) include assays disclosed in Berger et al., Gene 66: 1-10 (1988); Cullen and Malm, Methods in Enzymol 216: 362-368 (1992); Henthorn et al., Proc Natl Acad Sci USA 85: 6342-6346 (1988); Rellahan et al., J Biol Chem 272(49): 30806-30811 (1997); Chang et al., Mol Cell Biol 18(9): 4986-4993 (1998); and Fraser et al., Eur J Immunol 29(3): 838-844 (1999), the contents of each of which are herein incorporated by reference in its entirety. T cells that may be used according to these assays are publicly available (e.g., through the ATCC ™). Exemplary mouse T cells that may be used according to these assays include the CTLL cell line, which is an IL-2 dependent suspension-culture cell line with cytotoxic activity. Additional exemplary mouse T cells that may be used according to these assays include the HT2 cell line, which is an IL-2 dependent suspension culture cell line that also responds to IL-4. Exemplary human T cells that may be used according to these assays include the SUPT cell line, which is an IL-2 and IL-4 responsive suspension-culture cell line. | "Immune Activity", "Cardiovascular Disorders", and/or "Blood-Related Disorders"), and infection (e.g., an infectious disease as described below under "Infectious Disease"). Highly preferred indications include autoimmune diseases (e.g., rheumatoid arthritis, systemic lupus erythematosis, multiple sclerosis and/or as described below) and immunodeficiencies (e.g., as described below). Additional highly preferred indications include inflammation and inflammatory disorders. Highly preferred indications also include neoplastic diseases (e.g., leukemia, lymphoma, and/or as described below under "Hyperproliferative Disorders"). Highly preferred indications include neoplasms and cancers, such as, leukemia, lymphoma, prostate, breast, lung, colon, pancreatic, esophageal, stomach, brain, liver, and urinary cancer. Other preferred indications include benign dysproliferative disorders and pre-neoplastic conditions, such as, for example, hyperplasia, metaplasia, and/or dysplasia. Preferred indications include arthritis, asthma, AIDS, allergy, anemia, pancytopenia, leukopenia, thrombocytopenia, Hodgkin's disease, acute lymphocytic anemia (ALL), plasmacytomas, multiple myeloma, Burkitt's lymphoma, granulomatous disease, inflammatory bowel disease, sepsis, psoriasis, suppression of immune reactions to transplanted organs and tissues, endocarditis, meningitis, and Lyme Disease. |
| 15 | Activation of transcription through cAMP response element (CRE) in pre-adipocytes. | Assays for the activation of transcription through the cAMP response element are well-known in the art and may be used or routinely modified to assess the ability of polypeptides of the invention (including antibodies and agonists or antagonists of the invention) to increase cAMP, regulate CREB transcription factors, and modulate expression of genes involved in a wide variety of cell functions. For example, a 3T3-L1/CRE reporter assay may be used to identify factors that activate the cAMP signaling pathway. CREB plays a major role in adipogenesis, and is involved in differentiation into adipocytes. CRE contains the binding sequence for the transcription factor CREB (CRE binding protein). Exemplary assays for transcription through the cAMP response element that may be used or routinely modified to test cAMP-response element activity of polypeptides of the invention (including antibodies and agonists or antagonists of the invention) include assays disclosed in Berger et al., Gene 66: 1-10 (1998); Cullen and Malm, Methods in Enzymol 216: 362-368 (1992); Henthorn et al., Proc Natl Acad Sci USA 85: 6342-6346 (1988); Reusch et al., Mol Cell Biol 20(3): 1008-1020 (2000); and Klemm et al., J Biol Chem 273: 917-923 (1998), the contents of each of which are herein incorporated by reference in its entirety. Pre-adipocytes that may be used according to these assays are publicly available (e.g., through the ATCC ™) and/or may be routinely generated. Exemplary mouse adipocyte cells that may be used according to these assays include 3T3-L1 cells. 3T3-L1 is an adherent mouse preadipocyte cell line that is a continuous | A highly preferred indication is obesity and/or complications associated with obesity. Additional highly preferred indications include weight loss or alternatively, weight gain. An additional highly preferred indication is diabetes mellitus. An additional highly preferred indication is a complication associated with diabetes (e.g., diabetic retinopathy, diabetic nephropathy, kidney disease (e.g., renal failure, nephropathy and/or other diseases and disorders as described in the "Renal Disorders" section below), diabetic neuropathy, nerve disease and nerve damage (e.g., due to diabetic neuropathy), blood vessel blockage, heart disease, stroke, impotence (e.g., due to diabetic neuropathy or blood vessel blockage), seizures, mental confusion, drowsiness, nonketotic hyperglycemic-hyperosmolar coma, cardiovascular disease (e.g., heart disease, atherosclerosis, microvascular disease, hypertension, stroke, and other diseases and disorders as described in the "Cardiovascular Disorders" section below), dyslipidemia, endocrine disorders (as described in the "Endocrine Disorders" section below), neuropathy, vision impairment (e.g., diabetic retinopathy and blindness), ulcers and impaired wound healing, and infection (e.g., infectious diseases and disorders as described in the "Infectious Diseases" section below, especially of the urinary tract and skin), carpal tunnel syndrome and Dupuytren's contracture). Additional highly preferred indications are complications associated with insulin resistance. |

TABLE 1E.2-continued

| Biological Activity No. | Biological Activity | Exemplary Activity Assay | Preferred Indication |
|---|---|---|---|
| | | substrain of 3T3 fibroblast cells developed through clonal isolation and undergo a pre-adipocyte to adipose-like conversion under appropriate differentiation conditions known in the art. | |
| 16 | Activation of transcription through cAMP response element in immune cells (such as T-cells). | Assays for the activation of transcription through the cAMP response element are well-known in the art and may be used or routinely modified to assess the ability of polypeptides of the invention (including antibodies and agonists or antagonists of the invention) to increase cAMP, bind to CREB transcription factor, and modulate expression of genes involved in a wide variety of cell functions. Exemplary assays for transcription through the cAMP response element that may be used or routinely modified to test cAMP-response element activity of polypeptides of the invention (including antibodies and agonists or antagonists of the invention) include assays disclosed in Berger et al., Gene 66: 1-10 (1998); Cullen and Malm, Methods in Enzymol 216: 362-368 (1992); Henthorn et al., Proc Natl Acad Sci USA 85: 6342-6346 (1988); Black et al., Virus Genes 15(2): 105-117 (1997); and Belkowski et al., J Immunol 161(2): 659-665 (1998), the contents of each of which are herein incorporated by reference in its entirety. T cells that may be used according to these assays are publicly available (e.g., through the ATCC ™). Exemplary human T cells that may be used according to these assays include the JURKAT cell line, which is a suspension culture of leukemia cells that produce IL-2 when stimulated. Exemplary mouse T cells that may be used according to these assays include the CTLL cell line, which is a suspension culture of IL-2 dependent cytotoxic T cells. Aditional exemplary mouse T cells that may be used according to these assays include the HT2 cell line, which is a suspension culture of IL-2 dependent T cells that also respond to IL-4. | Preferred indications include blood disorders (e.g., as described below under "Immune Activity", "Blood-Related Disorders", and/or "Cardiovascular Disorders"), and infection (e.g., an infectious disease as described below under "Infectious Disease"). Preferred indications include autoimmune diseases (e.g., rheumatoid arthritis, systemic lupus erythematosis, multiple sclerosis and/or as described below), immunodeficiencies (e.g., as described below), boosting a T cell-mediated immune response, and suppressing a T cell-mediated immune response. Additional preferred indications include inflammation and inflammatory disorders. Highly preferred indications include neoplastic diseases (e.g., leukemia, lymphoma, and/or as described below under "Hyperproliferative Disorders"). Highly preferred indications include neoplasms and cancers, such as, leukemia, lymphoma (e.g., T cell lymphoma, Burkitt's lymphoma, non-Hodgkins lymphoma, Hodgkin"s disease), melanoma, and prostate, breast, lung, colon, pancreatic, esophageal, stomach, brain, liver and urinary cancer. Other preferred indications include benign dysproliferative disorders and pre-neoplastic conditions, such as, for example, hyperplasia, metaplasia, and/or dysplasia. Preferred indications include anemia, pancytopenia, leukopenia, thrombocytopenia, acute lymphocytic anemia (ALL), plasmacytomas, multiple myeloma, arthritis, AIDS, granulomatous disease, inflammatory bowel disease, sepsis, neutropenia, neutrophilia, psoriasis, suppression of immune reactions to transplanted organs and tissues, hemophilia, hypercoagulation, diabetes mellitus, endocarditis, meningitis, Lyme Disease, and asthma and allergy. |
| 17 | Activation of transcription through CD28 response element in immune cells (such as T-cells). | Assays for the activation of transcription through the CD28 response element are well-known in the art and may be used or routinely modified to assess the ability of polypeptides of the invention (including antibodies and agonists or antagonists of the invention) to stimulate IL-2 expression in T cells. Exemplary assays for transcription through the CD28 response element that may be used or routinely modified to test CD28-response element activity of polypeptides of the invention (including antibodies and agonists or antagonists of the invention) include assays disclosed in Berger et al., Gene 66: 1-10 (1998); Cullen and Malm, Methods in Enzymol 216: 362-368 (1992); Henthorn et al., Proc Natl Acad Sci USA 85: 6342-6346 (1988); McGuire and Iacobelli, J Immunol 159(3): 1319-1327 (1997); Parra et al., J Immunol 166(4): 2437-2443 (2001); and Butscher et al., J Biol Chem 3(1): 552-560 (1998), the contents of each of which are herein incorporated by reference in its entirety. T cells that may be used according to these assays are publicly available (e.g., through the ATCC ™). Exemplary human T cells that may be used according to these assays include the SUPT cell line, which is a suspension culture of IL-2 and IL-4 responsive T cells. Additional | A highly preferred embodiment of the invention includes a method for stimulating T cell proliferation. An alternative highly preferred embodiment of the invention includes a method for inhibiting T cell proliferation. A highly preferred embodiment of the invention includes a method for activating T cells. An alternative highly preferred embodiment of the invention includes a method for inhibiting the activation of and/or inactivating T cells. A highly preferred embodiment of the invention includes a method for stimulating (e.g., increasing) IL-2 production. An alternative highly preferred embodiment of the invention includes a method for inhibiting (e.g., reducing) IL-2 production. Additional highly preferred indications include inflammation and inflammatory disorders. Highly preferred indications include autoimmune diseases (e.g., rheumatoid arthritis, systemic lupus erythematosis, multiple sclerosis and/or as described below), immunodeficiencies (e.g., as described below), boosting a T cell-mediated immune response, and suppressing a T cell-mediated immune response. Highly preferred indications include neoplastic diseases (e.g., melanoma, renal cell carcinoma, leukemia, lymphoma, and/or as described below under "Hyperproliferative Disorders"). Highly preferred indications include neoplasms and |

TABLE 1E.2-continued

| Biological Activity No. | Biological Activity | Exemplary Activity Assay | Preferred Indication |
|---|---|---|---|
| | | exemplary human T cells that may be used according to these assays include the JURKAT cell line, which is a suspension culture of leukemia cells that produce IL-2 when stimulated. | cancers, such as, for example, melanoma (e.g., metastatic melanoma), renal cell carcinoma (e.g., metastatic renal cell carcinoma), leukemia, lymphoma (e.g,. T cell lymphoma), and prostate, breast, lung, colon, pancreatic, esophageal, stomach, brain, liver and urinary cancer. Other preferred indications include benign dysproliferative disorders and pre-neoplastic conditions, such as, for example, hyperplasia, metaplasia, and/or dysplasia. A highly preferred indication includes infection (e.g., AIDS, tuberculosis, infections associated with granulomatous disease, and osteoporosis, and/or as described below under “Infectious Disease”). A highly preferred indication is AIDS. Additional highly preferred indications include suppression of immune reactions to transplanted organs and/or tissues, uveitis, psoriasis, and tropical spastic paraparesis. Preferred indications include blood disorders (e.g., as described below under “Immune Activity”, “Blood-Related Disorders”, and/or “Cardiovascular Disorders”). Preferred indications also include anemia, pancytopenia, leukopenia, thrombocytopenia, Hodgkin’s disease, acute lymphocytic anemia (ALL), plasmacytomas, multiple myeloma, Burkitt’s lymphoma, arthritis, granulomatous disease, inflammatory bowel disease, sepsis, neutropenia, neutrophilia, hemophilia, hypercoagulation, diabetes mellitus, endocarditis, meningitis, Lyme Disease, asthma and allergy. |
| 18 | Activation of transcription through GAS response element in epithelial cells (such as HELA cells). | Assays for the activation of transcription through the Gamma Interferon Activation Site (GAS) response element are well-known in the art and may be used or routinely modified to assess the ability of polypeptides of the invention (including antibodies and agonists or antagonists of the invention) to regulate STAT transcription factors and modulate gene expression involved in a wide variety of cell functions. Exemplary assays for transcription through the GAS response element that may be used or routinely modified to test GAS-response element activity of polypeptides of the invention (including antibodies and agonists or antagonists of the invention) include assays disclosed in: You M, et al, J Biol Chem, 272(37): 23376-23381(1997); Min W, et al., Circ Res, 83(8): 815-823 (1998); Berger et al., Gene 66: 1-10 (1998); Cullen and Malm, Methods in Enzymol 216: 362-368 (1992); Henthorn et al., Proc Natl Acad Sci USA 85: 6342-6346 (1988); Matikainen et al., Blood 93(6): 1980-1991 (1999); and Henttinen et al., J Immunol 155(10): 4582-4587 (1995), the contents of each of which are herein incorporated by reference in its entirety. Epithelial cells that may be used according to these assays are publicly available (e.g., through the ATCC ™). Exemplary epithelial cells that may be used according to these assays include the HELA cell line. | A highly preferred embodiment of the invention includes a method for stimulating endothelial cell growth. An alternative highly preferred embodiment of the invention includes a method for inhibiting endothelial cell growth. A highly preferred embodiment of the invention includes a method for stimulating endothelial cell proliferation. An alternative highly preferred embodiment of the invention includes a method for inhibiting endothelial cell proliferation. A highly preferred embodiment of the invention includes a method for stimulating apoptosis of endothelial cells. An alternative highly preferred embodiment of the invention includes a method for inhibiting (e.g., decreasing) apoptosis of endothelial cells. A highly preferred embodiment of the invention includes a method for stimulating (e.g., increasing) endothelial cell activation. An alternative highly preferred embodiment of the invention includes a method for inhibiting (e.g., decreasing) the activation of and/or inactivating endothelial cells. A highly preferred embodiment of the invention includes a method for stimulating angiogenisis. An alternative highly preferred embodiment of the invention includes a method for inhibiting angiogenesis. A highly preferred embodiment of the invention includes a method for reducing cardiac hypertrophy. An alternative highly preferred embodiment of the invention includes a method for inducing cardiac hypertrophy. Preferred embodiments of the invention include using polypeptides of the invention (or antibodies, agonists, or antagonists thereof) in detection, diagnosis, prevention, and/or treatment of Cancer, Wound Healing, and Inflamation. Highly preferred indications include neoplastic diseases (e.g., as described below under “Hyperproliferative Disorders”), and disorders of the cardiovascular system (e.g., heart disease, congestive heart failure, hypertension, aortic stenosis, cardiomyopathy, valvular |

TABLE 1E.2-continued

| Biological Activity No. | Biological Activity | Exemplary Activity Assay | Preferred Indication |
|---|---|---|---|
| | | | regurgitation, left ventricular dysfunction, atherosclerosis and atherosclerotic vascular disease, diabetic nephropathy, intracardiac shunt, cardiac hypertrophy, myocardial infarction, chronic hemodynamic overload, and/or as described below under "Cardiovascular Disorders"). Highly preferred indications include cardiovascular, endothelial and/or angiogenic disorders (e.g., systemic disorders that affect vessels such as diabetes mellitus, as well as diseases of the vessels themselves, such as of the arteries, capillaries, veins and/or lymphatics). Highly preferred are indications that stimulate angiogenesis and/or cardiovascularization. Highly preferred are indications that inhibit angiogenesis and/or cardiovascularization. Highly preferred indications include antiangiogenic activity to treat solid tumors, leukemias, and Kaposi's sarcoma, and retinal disorders. Highly preferred indications include neoplasms and cancers, such as, Kaposi's sarcoma, hemangioma (capillary and cavernous), glomus tumors, telangiectasia, bacillary angiomatosis, hemangioendothelioma, angiosarcoma, haemangiopericytoma, lymphangioma, lymphangiosarcoma. Highly preferred indications also include cancers such as, melanoma and prostate, breast, lung, colon, pancreatic, esophageal, stomach, brain, liver, and urinary cancer. Other preferred indications include benign dysproliferative disorders and pre-neoplastic conditions, such as, for example, hyperplasia, metaplasia, and/or dysplasia. Highly preferred indications also include arterial disease, such as, atherosclerosis, hypertension, coronary artery disease, inflammatory vasculitides, Reynaud's disease and Reynaud's phenomenom, aneurysms, restenosis; venous and lymphatic disorders such as thrombophlebitis, lymphangitis, and lymphedema; and other vascular disorders such as peripheral vascular disease, and cancer. Highly preferred indications also include trauma such as wounds, burns, and injured tissue (e.g., vascular injury such as, injury resulting from balloon angioplasty, and atheroschlerotic lesions), implant fixation, scarring, ischemia reperfusion injury, rheumatoid arthritis, cerebrovascular disease, renal diseases such as acute renal failure, and osteoporosis. Additional highly preferred indications include stroke, graft rejection, diabetic or other retinopathies, thrombotic and coagulative disorders, vascularitis, lymph angiogenesis, sexual disorders, age-related macular degeneration, and treatment/ prevention of endometriosis and related conditions. Additional highly preferred indications include fibromas, heart disease, cardiac arrest, heart valve disease, and vascular disease. Preferred indications include blood disorders (e.g., as described below under "Immune Activity", "Blood-Related Disorders", and/or ""Cardiovascular Disorders""). Preferred indications include autoimmune diseases (e.g., rheumatoid arthritis, systemic lupus erythematosis, multiple sclerosis and/or as described below) and immunodeficiencies (e.g., as described below). Additional preferred indications include inflammation and inflammatory disorders (such as acute and chronic inflammatory diseases, e.g., inflammatory bowel disease and Crohn's disease), and pain management. |
| 19 | Activation of transcription through | Assays for the activation of transcription through the Gamma Interferon Activation | Highly preferred indications include asthma, allergy, hypersensitivity reactions, |

TABLE 1E.2-continued

| Biological Activity No. | Biological Activity | Exemplary Activity Assay | Preferred Indication |
|---|---|---|---|
| | GAS response element in immune cells (such as eosinophils). | Site (GAS) response element are well-known in the art and may be used or routinely modified to assess the ability of polypeptides of the invention (including antibodies and agonists or antagonists of the invention) to modulate gene expression (commonly via STAT transcription factors) involved in a wide variety of cell functions. Exemplary assays for transcription through the GAS response element that may be used or routinely modified to test GAS-response element activity of polypeptides of the invention (including antibodies and agonists or antagonists of the invention) include assays disclosed in Berger et al., Gene 66: 1-10 (1998); Cullen and Malm, Methods in Enzymol 216: 362-368 (1992); Henthorn et al., Proc Natl Acad Sci USA 85: 6342-6346 (1988); Matikainen et al., Blood 93(6): 1980-1991 (1999); and Henttinen et al., J Immunol 155(10): 4582-4587 (1995); the contents of each of which are herein incorporated by reference in its entirety. Moreover, exemplary assays that may be used or routinely modified to assess the ability of polypeptides of the invention (including antibodies and agonists or antagonists of the invention) to activate or inhibit activation of immune cells include assays disclosed and/or cited in: Mayumi M., "EoL-1, a human eosinophilic cell line" Leuk Lymphoma; June; 7(3): 243-50 (1992); Bhattacharya S, "Granulocyte macrophage colony-stimulating factor and interleukin-5 activate STAT5 and induce CIS1 mRNA in human peripheral blood eosinophils" Am J Respir Cell Mol Biol; March; 24(3): 312-6 (2001); and, Du J, et al., "Engagement of the CrkL adapter in interleukin-5 signaling in eosinophils" J Biol Chem; October 20; 275(42): 33167-75 (2000); the contents of each of which are herein incorporated by reference in its entirety. Exemplary cells that may be used according to these assays include eosinophils. Eosinophils are a type of immune cell important in the late stage of allergic reactions; they are recruited to tissues and mediate the inflammatory response of late stage allergic reaction. Increases in GAS mediated transcription in eosinophils is typically a result of STAT activation, normally a direct consequence of interleukin or other cytokine receptor stimulation (e.g. IL3, IL5 or GMCSF). | inflammation, and inflammatory disorders. Additional highly preferred indications include immune and hematopoietic disorders (e.g., as described below under "Immune Activity", and "Blood-Related Disorders"), autoimmune diseases (e.g., rheumatoid arthritis, systemic lupus erythematosis, Crohn''s disease, multiple sclerosis and/or as described below), immunodeficiencies (e.g., as described below), boosting an eosinophil-mediated immune response and, alternatively, suppressing an eosinophil-mediated immune response. |
| 20 | Activation of transcription through GAS response element in immune cells (such as monocytes). | Assays for the activation of transcription through the Gamma Interferon Activation Site (GAS) response element are well-known in the art and may be used or routinely modified to assess the ability of polypeptides of the invention (including antibodies and agonists or antagonists of the invention) to regulate STAT transcription factors and modulate gene expression involved in a wide variety of cell functions. Exemplary assays for transcription through the GAS response element that may be used or routinely modified to test GAS-response element activity of polypeptides of the invention (including antibodies and agonists or antagonists of the invention) include assays disclosed in: Gustafson K S, et al., J Biol Chem, 271(33): 20035-20046 (1996); Eilers A, et al., Immunobiology, 193(2-4): 328-333 (1995); Berger et al., Gene 66: 1-10 (1998); Cullen and Malm, Methods in Enzymol 216: 362-368 (1992); Henthorn et | Preferred embodiments of the invention include using polypeptides of the invention (or antibodies, agonists, or antagonists thereof) in detection, diagnosis, prevention, and/or treatment of Inflammation, Infection, Cancer, Hypersensitivity, and Atherosclerosis. |

TABLE 1E.2-continued

| Biological Activity No. | Biological Activity | Exemplary Activity Assay | Preferred Indication |
|---|---|---|---|
| | | al., Proc Natl Acad Sci USA 85: 6342-6346 (1988); Matikainen et al., Blood 93(6): 1980-1991 (1999); and Henttinen et al., J Immunol 155(10): 4582-4587 (1995), the contents of each of which are herein incoporated by reference in its entirety. Exemplary immune cells that may be used according to these assays are publicly available (e.g., through the ATCC ™). Exemplary immune cells that may be used according to these assays include the U937 cell line, which is a monocytic cell line. | |
| 21 | Activation of transcription through GAS response element in immune cells (such as T-cells). | Assays for the activation of transcription through the Gamma Interferon Activation Site (GAS) response element are well-known in the art and may be used or routinely modified to assess the ability of polypeptides of the invention (including antibodies and agonists or antagonists of the invention) to regulate STAT transcription factors and modulate gene expression involved in a wide variety of cell functions. Exemplary assays for transcription through the GAS response element that may be used or routinely modified to test GAS-response element activity of polypeptides of the invention (including antibodies and agonists or antagonists of the invention) include assays disclosed in Berger et al., Gene 66: 1-10 (1998); Cullen and Malm, Methods in Enzymol 216: 362-368 (1992); Henthorn et al., Proc Natl Acad Sci USA 85: 6342-6346 (1988); Matikainen et al., Blood 93(6): 1980-1991 (1999); and Henttinen et al., J Immunol 155(10): 4582-4587 (1995), the contents of each of which are herein incorporated by reference in its entirety. Exemplary mouse T cells that may be used according to these assays are publicly available (e.g., through the ATCC ™). Exemplary human T cells, such as the MOLT4 cell line, that may be used according to these assays are publicly available (e.g., through the ATCC ™). Additional exemplary human T cells, such as the SUPT cell line, that may be used according to these assays are publicly available (e.g., through the ATCC ™). Additional exemplary T cells that may be used according to these assays include the CTLL cell line, which is a suspension culture of IL-2 dependent cytotoxic T cells. | Highly preferred indications include neoplastic diseases (e.g., leukemia, lymphoma, and/or as described below under "Hyperproliferative Disorders"). Highly preferred indications include neoplasms and cancers, such as, for example, leukemia, lymphoma (e.g., T cell lymphoma, Burkitt's lymphoma, non-Hodgkins lymphoma, Hodgkin's disease), melanoma, and prostate, breast, lung, colon, pancreatic, esophageal, stomach, brain, liver and urinary cancer. Other preferred indications include benign dysproliferative disorders and pre-neoplastic conditions, such as, for example, hyperplasia, metaplasia, and/or dysplasia. Preferred indications include autoimmune diseases (e.g., rheumatoid arthritis, systemic lupus erythematosis, multiple sclerosis and/or as described below), immunodeficiencies (e.g., as described below), boosting a T cell-mediated immune response, and suppressing a T cell-mediated immune response. Additional preferred indications include inflammation and inflammatory disorders. Highly preferred indications include blood disorders (e.g., as described below under "Immune Activity", "Blood-Related Disorders", and/or ""Cardiovascular Disorders""), and infection (e.g., viral infections, tuberculosis, infections associated with chronic granulomatosus disease and malignant osteoporosis, and/or an infectious disease as described below under "Infectious Disease"). An additional preferred indication is idiopathic pulmonary fibrosis. Preferred indications include anemia, pancytopenia, leukopenia, thrombocytopenia, acute lymphocytic anemia (ALL), plasmacytomas, multiple myeloma, arthritis, AIDS, granulomatous disease, inflammatory bowel disease, sepsis, neutropenia, neutrophilia, psoriasis, suppression of immune reactions to transplanted organs and tissues, hemophilia, hypercoagulation, diabetes mellitus, endocarditis, meningitis, Lyme Disease, and asthma and allergy. |
| 22 | Activation of transcription through GATA-3 response element in immune cells (such as mast cells). | This reporter assay measures activation of the GATA-3 signaling pathway in HMC-1 human mast cell line. Activation of GATA-3 in mast cells has been linked to cytokine and chemokine production. Assays for the activation of transcription through the GATA3 response element are well-known in the art and may be used or routinely modified to assess the ability of polypeptides of the invention (including antibodies and agonists or antagonists of the invention) to regulate GATA3 transcription factors and modulate expression of mast cell genes important for immune response development. Exemplary assays for transcription through the GATA3 response element that may be used or routinely modified to test GATA3-response element activity of polypeptides of the invention (including antibodies and agonists or | Highly preferred indications include allergy, asthma, and rhinitis. Additional preferred indications include infection (e.g., an infectious disease as described below under "Infectious Disease"), and inflammation and inflammatory disorders. Preferred indications also include blood disorders (e.g., as described below under "Immune Activity", "Blood-Related Disorders", and/or "Cardiovascular Disorders"). Preferred indications include autoimmune diseases (e.g., rheumatoid arthritis, systemic lupus erythematosis, multiple sclerosis and/or as described below) and immunodeficiencies (e.g., as described below). Preferred indications include neoplastic diseases (e.g., leukemia, lymphoma, melanoma, prostate, breast, lung, colon, pancreatic, esophageal, stomach, brain, liver, and urinary tract cancers and/or as described below under "Hyperproliferative Disorders"). Other preferred indications |

TABLE 1E.2-continued

| Biological Activity No. | Biological Activity | Exemplary Activity Assay | Preferred Indication |
|---|---|---|---|
| | | antagonists of the invention) include assays disclosed in Berger et al., Gene 66: 1-10 (1998); Cullen and Malm, Methods in Enzymol 216: 362-368 (1992); Henthorn et al., Proc Natl Acad Sci USA 85: 6342-6346 (1988); Flavell et al., Cold Spring Harb Symp Quant Biol 64: 563-571 (1999); Rodriguez-Palmero et al., Eur J Immunol 29(12): 3914-3924 (1999); Zheng and Flavell, Cell 89(4): 587-596 (1997); and Henderson et al., Mol Cell Biol 14(6): 4286-4294 (1994), the contents of each of which are herein incorporated by reference in its entirety. Mast cells that may be used according to these assays are publicly available (e.g., through the ATCC ™). Exemplary human mast cells that may be used according to these assays include the HMC-1 cell line, which is an immature human mast cell line established from the peripheral blood of a patient with mast cell leukemia, and exhibits many characteristics of immature mast cells. | include benign dysproliferative disorders and pre-neoplastic conditions, such as, for example, hyperplasia, metaplasia, and/or dysplasia. Preferred indications include anemia, pancytopenia, leukopenia, thrombocytopenia, leukemias, Hodgkin's disease, acute lymphocytic anemia (ALL), plasmacytomas, multiple myeloma, Burkitt's lymphoma, arthritis, AIDS, granulomatous disease, inflammatory bowel disease, sepsis, neutropenia, neutrophilia, psoriasis, suppression of immune reactions to transplanted organs and tissues, hemophilia, hypercoagulation, diabetes mellitus, endocarditis, meningitis, and Lyme Disease. |
| 23 | Activation of transcription through GATA-3 response element in immune cells (such as T-cells). | Assays for the activation of transcription through the GATA3 response element are well-known in the art and may be used or routinely modified to assess the ability of polypeptides of the invention (including antibodies and agonists or antagonists of the invention) to regulate GATA3 transcription factors and modulate expression of genes important for Th2 immune response development. Exemplary assays for transcription through the GATA3 response element that may be used or routinely modified to test GATA3-response element activity of polypeptides of the invention (including antibodies and agonists or antagonists of the invention) include assays disclosed in Berger et al., Gene 66: 1-10 (1998); Cullen and Malm, Methods in Enzymol 216: 362-368 (1992); Henthorn et al., Proc Natl Acad Sci USA 85: 6342-6346 (1988); Flavell et al., Cold Spring Harb Symp Quant Biol 64: 563-571 (1999); Rodriguez-Palmero et al., Eur J Immunol 29(12): 3914-3924 (1999); Zheng and Flavell, Cell 89(4): 587-596 (1997); and Henderson et al., Mol Cell Biol 14(6): 4286-4294 (1994), the contents of each of which are herein incorporated by reference in its entirety. T cells that may be used according to these assays are publicly available (e.g., through the ATCC ™). Exemplary mouse T cells that may be used according to these assays include the HT2 cell line, which is a suspension culture of IL-2 dependent T cells that also respond to IL-4. | |
| 24 | Activation of transcription through NFAT response element in immune cells (such as mast cells). | This reporter assay measures activation of the NFAT signaling pathway in HMC-1 human mast cell line. Activation of NFAT in mast cells has been linked to cytokine and chemokine production. Assays for the activation of transcription through the Nuclear Factor of Activated T cells (NFAT) response element are well-known in the art and may be used or routinely modified to assess the ability of polypeptides of the invention (including antibodies and agonists or antagonists of the invention) to regulate NFAT transcription factors and modulate expression of genes involved in immunomodulatory functions. Exemplary assays for transcription through the NFAT response element that may be used or routinely modified to test NFAT-response | Highly preferred indications include allergy, asthma, and rhinitis. Additional preferred indications include infection (e.g., an infectious disease as described below under "Infectious Disease"), and inflammation and inflammatory disorders. Preferred indications also include blood disorders (e.g., as described below under "Immune Activity", "Blood-Related Disorders", and/or "Cardiovascular Disorders"). Preferred indications include autoimmune diseases (e.g., rheumatoid arthritis, systemic lupus erythematosis, multiple sclerosis and/or as described below) and immunodeficiencies (e.g., as described below). Preferred indications include neoplastic diseases (e.g., leukemia, lymphoma, melanoma, prostate, breast, lung, colon, pancreatic, esophageal, stomach, brain, liver, and urinary tract cancers and/or as |

TABLE 1E.2-continued

| Biological Activity No. | Biological Activity | Exemplary Activity Assay | Preferred Indication |
|---|---|---|---|
| | | element activity of polypeptides of the invention (including antibodies and agonists or antagonists of the invention) include assays disclosed in Berger et al., Gene 66: 1-10 (1998); Cullen and Malm, Methods in Enzymol 216: 362-368 (1992); Henthorn et al., Proc Natl Acad Sci USA 85: 6342-6346 (1988); De Boer et al., Int J Biochem Cell Biol 31(10): 1221-1236 (1999); Ali et al., J Immunol 165(12): 7215-7223 (2000); Hutchinson and McCloskey, J Biol Chem 270(27): 16333-16338 (1995), and Turner et al., J Exp Med 188: 527-537 (1998), the contents of each of which are herein incorporated by reference in its entirety. Mast cells that may be used according to these assays are publicly available (e.g., through the ATCC ™). Exemplary human mast cells that may be used according to these assays include the HMC-1 cell line, which is an immature human mast cell line established from the peripheral blood of a patient with mast cell leukemia, and exhibits many characteristics of immature mast cells. | described below under "Hyperproliferative Disorders"). Other preferred indications include benign dysproliferative disorders and pre-neoplastic conditions, such as, for example, hyperplasia, metaplasia, and/or dysplasia. Preferred indications include anemia, pancytopenia, leukopenia, thrombocytopenia, leukemias, Hodgkin's disease, acute lymphocytic anemia (ALL), plasmacytomas, multiple myeloma, Burkitt's lymphoma, arthritis, AIDS, granulomatous disease, inflammatory bowel disease, sepsis, neutropenia, neutrophilia, psoriasis, suppression of immune reactions to transplanted organs and tissues, hemophilia, hypercoagulation, diabetes mellitus, endocarditis, meningitis, and Lyme Disease. |
| 25 | Activation of transcription through NFAT response element in immune cells (such as natural killer cells). | Assays for the activation of transcription through the Nuclear Factor of Activated T cells (NFAT) response element are well-known in the art and may be used or routinely modified to assess the ability of polypeptides of the invention (including antibodies and agonists or antagonists of the invention) to regulate NFAT transcription factors and modulate expression of genes involved in immunomodulatory functions. Exemplary assays for transcription through the NFAT response element that may be used or routinely modified to test NFAT-response element activity of polypeptides of the invention (including antibodies and agonists or antagonists of the invention) include assays disclosed in Berger et al., Gene 66: 1-10 (1998); Cullen and Malm, Methods in Enzymol 216: 362-368 (1992); Henthorn et al., Proc Natl Acad Sci USA 85: 6342-6346 (1988); Aramburu et al., J Exp Med 182(3): 801-810 (1995); De Boer et al., Int J Biochem Cell Biol 31(10): 1221-1236 (1999); Fraser et al., Eur J Immunol 29(3): 838-844 (1999); and Yeseen et al., J Biol Chem 268(19): 14285-14293 (1993), the contents of each of which are herein incorporated by reference in its entirety. NK cells that may be used according to these assays are publicly available (e.g., through the ATCC ™). Exemplary human NK cells that may be used according to these assays include the NK-YT cell line, which is a human natural killer cell line with cytolytic and cytotoxic activity. | Highly preferred indications include blood disorders (e.g., as described below under "Immune Activity", "Blood-Related Disorders", and/or "Cardiovascular Disorders"). Highly preferred indications include autoimmune diseases (e.g., rheumatoid arthritis, systemic lupus erythematosis, multiple sclerosis and/or as described below), immunodeficiencies (e.g., as described below), boosting a T cell-mediated immune response, and suppressing a T cell-mediated immune response. Additional highly preferred indications include inflammation and inflammatory disorders. An additional highly preferred indication is infection (e.g., an infectious disease as described below under "Infectious Disease"). Preferred indications include neoplastic diseases (e.g., leukemia, lymphoma, and/or as described below under "Hyperproliferative Disorders"). Preferred indications include neoplasms and cancers, such as, for example, leukemia, lymphoma, and prostate, breast, lung, colon, pancreatic, esophageal, stomach, brain, liver and urinary cancer. Other preferred indications include benign dysproliferative disorders and pre-neoplastic conditions, such as, for example, hyperplasia, metaplasia, and/or dysplasia. Preferred indications also include anemia, pancytopenia, leukopenia, thrombocytopenia, Hodgkin's disease, acute lymphocytic anemia (ALL), plasmacytomas, multiple myeloma, Burkitt's lymphoma, arthritis, AIDS, granulomatous disease, inflammatory bowel disease, sepsis, neutropenia, neutrophilia, psoriasis, suppression of immune reactions to transplanted organs and tissues, hemophilia, hypercoagulation, diabetes mellitus, endocarditis, meningitis, Lyme Disease, asthma and allergy. |
| 26 | Activation of transcription through NFAT response element in immune cells (such as T-cells). | Assays for the activation of transcription through the Nuclear Factor of Activated T cells (NFAT) response element are well-known in the art and may be used or routinely modified to assess the ability of polypeptides of the invention (including antibodies and agonists or antagonists of the invention) to regulate NFAT transcription factors and modulate expression of genes involved in immunomodulatory functions. Exemplary assays for transcription through | Highly preferred indications include blood disorders (e.g., as described below under "Immune Activity", "Blood-Related Disorders", and/or "Cardiovascular Disorders"). Highly preferred indications include autoimmune diseases (e.g., rheumatoid arthritis, systemic lupus erythematosis, multiple sclerosis and/or as described below), immunodeficiencies (e.g., as described below), boosting a T cell-mediated immune response, and suppressing a T cell-mediated immune |

TABLE 1E.2-continued

| Biological Activity No. | Biological Activity | Exemplary Activity Assay | Preferred Indication |
|---|---|---|---|
| | | the NFAT response element that may be used or routinely modified to test NFAT-response element activity of polypeptides of the invention (including antibodies and agonists or antagonists of the invention) include assays disclosed in Berger et al., Gene 66: 1-10 (1998); Cullen and Malm, Methods in Enzymol 216: 362-368 (1992); Henthorn et al., Proc Natl Acad Sci USA 85: 6342-6346 (1988); Serfling et al., Biochim Biophys Acta 1498(1): 1-18 (2000); De Boer et al., Int J Biochem Cell Biol 31(10): 1221-1236 (1999); Fraser et al., Eur J Immunol 29(3): 838-844 (1999); and Yeseen et al., J Biol Chem 268(19): 14285-14293 (1993), the contents of each of which are herein incorporated by reference in its entirety. T cells that may be used according to these assays are publicly available (e.g., through the ATCC ™). Exemplary human T cells that may be used according to these assays include the SUPT cell line, which is a suspension culture of IL-2 and IL-4 responsive T cells. | response. Additional highly preferred indications include inflammation and inflammatory disorders. An additional highly preferred indication is infection (e.g., an infectious disease as described below under “Infectious Disease”). Preferred indications include neoplastic diseases (e.g., leukemia, lymphoma, and/or as described below under “Hyperproliferative Disorders”). Preferred indications include neoplasms and cancers, such as, for example, leukemia, lymphoma, and prostate, breast, lung, colon, pancreatic, esophageal, stomach, brain, liver and urinary cancer. Other preferred indications include benign dysproliferative disorders and pre-neoplastic conditions, such as, for example, hyperplasia, metaplasia, and/or dysplasia. Preferred indications also include anemia, pancytopenia, leukopenia, thrombocytopenia, Hodgkin’s disease, acute lymphocytic anemia (ALL), plasmacytomas, multiple myeloma, Burkitt’s lymphoma, arthritis, AIDS, granulomatous disease, inflammatory bowel disease, sepsis, neutropenia, neutrophilia, psoriasis, suppression of immune reactions to transplanted organs and tissues, hemophilia, hypercoagulation, diabetes mellitus, endocarditis, meningitis, Lyme Disease, asthma and allergy. |
| 27 | Activation of transcription through NFAT response in immune cells (such as T-cells). | Assays for the activation of transcription through the Nuclear Factor of Activated T cells (NFAT) response element are well-known in the art and may be used or routinely modified to assess the ability of polypeptides of the invention (including antibodies and agonists or antagonists of the invention) to regulate NFAT transcription factors and modulate expression of genes involved in immunomodulatory functions. Exemplary assays for transcription through the NFAT response element that may be used or routinely modified to test NFAT-response element activity of polypeptides of the invention (including antibodies and agonists or antagonists of the invention) include assays disclosed in Berger et al., Gene 66: 1-10 (1998); Cullen and Malm, Methods in Enzymol 216: 362-368 (1992); Henthorn et al., Proc Natl Acad Sci USA 85: 6342-6346 (1988); Serfling et al., Biochim Biophys Acta 1498(1): 1-18 (2000); De Boer et al., Int J Biochem Cell Biol 31(10): 1221-1236 (1999); Fraser et al., Eur J Immunol 29(3): 838-844 (1999); and Yeseen et al., J Biol Chem 268(19): 14285-14293 (1993), the contents of each of which are herein incorporated by reference in its entirety. T cells that may be used according to these assays are publicly available (e.g., through the ATCC ™). Exemplary human T cells that may be used according to these assays include the JURKAT cell line, which is a suspension culture of leukemia cells that produce IL-2 when stimulated. | Highly preferred indications include blood disorders (e.g., as described below under “Immune Activity”, “Blood-Related Disorders”, and/or “Cardiovascular Disorders”). Highly preferred indications include autoimmune diseases (e.g., rheumatoid arthritis, systemic lupus erythematosis, multiple sclerosis and/or as described below), immunodeficiencies (e.g., as described below), boosting a T cell-mediated immune response, and suppressing a T cell-mediated immune response. Additional highly preferred indications include inflammation and inflammatory disorders. An additional highly preferred indication is infection (e.g., an infectious disease as described below under “Infectious Disease”). Preferred indications include neoplastic diseases (e.g., leukemia, lymphoma, and/or as described below under “Hyperproliferative Disorders”). Preferred indications include neoplasms and cancers, such as, for example, leukemia, lymphoma, and prostate, breast, lung, colon, pancreatic, esophageal, stomach, brain, liver and urinary cancer. Other preferred indications include benign dysproliferative disorders and pre-neoplastic conditions, such as, for example, hyperplasia, metaplasia, and/or dysplasia. Preferred indications also include anemia, pancytopenia, leukopenia, thrombocytopenia, Hodgkin’s disease, acute lymphocytic anemia (ALL), plasmacytomas, multiple myeloma, Burkitt’s lymphoma, arthritis, AIDS, granulomatous disease, inflammatory bowel disease, sepsis, neutropenia, neutrophilia, psoriasis, suppression of immune reactions to transplanted organs and tissues, hemophilia, hypercoagulation, diabetes mellitus, endocarditis, meningitis, Lyme Disease, asthma and allergy. |
| 28 | Activation of transcription through NFKB response element in epithelial cells (such as HELA cells). | Assays for the activation of transcription through the NFKB response element are well-known in the art and may be used or routinely modified to assess the ability of polypeptides of the invention (including antibodies and agonists or antagonists of the invention) to regulate NFKB transcription | Preferred embodiments of the invention include using polypeptides of the invention (or antibodies, agonists, or antagonists thereof) in detection, diagnosis, prevention, and/or treatment of Cancer, Wound Healing, and Inflamation. Highly preferred indications include neoplastic diseases (e.g., as described |

TABLE 1E.2-continued

| Biological Activity No. | Biological Activity | Exemplary Activity Assay | Preferred Indication |
|---|---|---|---|
| | | factors and modulate expression of epithhelial genes. Exemplary assays for transcription through the NFKB response element that may be used or routinely modified to test NFKB-response element activity of polypeptides of the invention (including antibodies and agonists or antagonists of the invention) include assays disclosed in: Kaltschmidt B, et al., Oncogene, 18(21): 3213-3225 (1999); Beetz A, et al., Int J Radiat Biol, 76(11): 1443-1453 (2000); Berger et al., Gene 66: 1-10 (1998); Cullen and Malm, Methods in Enzymol 216: 362-368 (1992); Henthorn et al., Proc Natl Acad Sci USA 85: 6342-6346 (1988); Valle Blazquez et al, Immunology 90(3): 455-460 (1997); Aramburau et al., J Exp Med 82(3): 801-810 (1995); and Fraser et al., 29(3): 838-844 (1999), the contents of each of which are herein incorporated by reference in its entirety. Epithelial cells that may be used according to these assays are publicly available (e.g., through the ATCC ™). Exemplary epithelial cells that may be used according to these assays include the HELA cell line. | below under "Hyperproliferative Disorders"). Highly preferred indications include neoplasms and cancers, such as, for example, melanoma, and prostate, breast, lung, colon, pancreatic, esophageal, stomach, brain, liver and urinary cancer. Other preferred indications include benign dysproliferative disorders and pre-neoplastic conditions, such as, for example, hyperplasia, metaplasia, and/or dysplasia. Preferred indications include include inflammation and inflammatory disorders. |
| 29 | Activation of transcription through NFKB response element in immune cells (such as B-cells). | Assays for the activation of transcription through the NFKB response element are well-known in the art and may be used or routinely modified to assess the ability of polypeptides of the invention (including antibodies and agonists or antagonists of the invention) to regulate NFKB transcription factors and modulate expression of immunomodulatory genes. Exemplary assays for transcription through the NFKB response element that may be used or routinely modified to test NFKB-response element activity of polypeptides of the invention (including antibodies and agonists or antagonists of the invention) include assays disclosed in: Gri G, et al., Biol Chem, 273(11): 6431-6438 (1998); Pyatt D W, et al., Cell Biol Toxicol 2000; 16(1): 41-51 (2000); Berger et al., Gene 66: 1-10 (1998); Cullen and Malm, Methods in Enzymol 216: 362-368 (1992); Henthorn et al., Proc Natl Acad Sci USA 85: 6342-6346 (1988); Valle Blazquez et al, Immunology 90(3): 455-460 (1997); Aramburau et al., J Exp Med 82(3): 801-810 (1995); and Fraser et al., 29(3): 838-844 (1999), the contents of each of which are herein incorporated by reference in its entirety. Immune cells that may be used according to these assays are publicly available (e.g., through the ATCC ™). Exemplary immune cells that may be used according to these assays include the Reh B-cell line. | |
| 30 | Activation of transcription through NFKB response element in immune cells (such as B-cells). | Assays for the activation of transcription through the NFKB response element are well-known in the art and may be used or routinely modified to assess the ability of polypeptides of the invention (including antibodies and agonists or antagonists of the invention) to regulate NFKB transcription factors and modulate expression of immunomodulatory genes. Exemplary assays for transcription through the NFKB response element that may be used or rountinely modified to test NFKB-response element activity of polypeptides of the invention (including antibodies and agonists or antagonists of the invention) include assays disclosed in: Gri G, et al., Biol | Preferred embodiments of the invention include using polypeptides of the invention (or antibodies, agonists, or antagonists thereof) in detection, diagnosis, prevention, and/or treatment of Cancer, Autoimmunity, Allergy and Asthma |

TABLE 1E.2-continued

| Biological Activity No. | Biological Activity | Exemplary Activity Assay | Preferred Indication |
|---|---|---|---|
| | | Chem, 273(11): 6431-6438 (1998); Pyatt D W, et al., Cell Biol Toxicol 2000; 16(1): 41-51 (2000); Berger et al., Gene 66: 1-10 (1998); Cullen and Malm, Methods in Enzymol 216: 362-368 (1992); Henthorn et al., Proc Natl Acad Sci USA 85: 6342-6346 (1988); Valle Blazquez et al, Immunology 90(3): 455-460 (1997); Aramburau et al., J Exp Med 82(3): 801-810 (1995); and Fraser et al., 29(3): 838-844 (1999), the contents of each of which are herein incorporated by reference in its entirety. Immune cells that may be used according to these assays are publicly available (e.g., through the ATCC ™). Exemplary immune cells that may be used according to these assays include the Reh B-cell line. | |
| 31 | Activation of transcription through NFKB response element in immune cells (such as basophils). | This reporter assay measures activation of the NFkB signaling pathway in Ku812 human basophil cell line. Assays for the activation of transcription through the NFKB response element are well-known in the art and may be used or routinely modified to assess the ability of polypeptides of the invention (including antibodies and agonists or antagonists of the invention) to regulate NFKB transcription factors and modulate expression of immunomodulatory genes. Exemplary assays for transcription through the NFKB response element that may be used or rountinely modified to test NFKB-response element activity of polypeptides of the invention (including antibodies and agonists or antagonists of the invention) include assays disclosed in Berger et al., Gene 66: 1-10 (1998); Cullen and Malm, Methods in Enzymol 216: 362-368 (1992); Henthorn et al., Proc Natl Acad Sci USA 85: 6342-6346 (1988); Marone et al, Int Arch Allergy Immunol 114(3): 207-17 (1997), the contents of each of which are herein incorporated by reference in its entirety. Basophils that may be used according to these assays are publicly available (e.g., through the ATCC ™). Exemplary human basophil cell lines that may be used according to these assays include Ku812, originally established from a patient with chronic myelogenous leukemia. It is an immature prebasophilic cell line that can be induced to differentiate into mature basophils. | Highly preferred indication includes allergy, asthma, and rhinitis. Additional highly preferred indications include infection (e.g., an infectious disease as described below under “Infectious Disease”), and inflammation and inflammatory disorders. Preferred indications include immunological and hempatopoietic disorders (e.g., as described below under “Immune Activity”, and “Blood-Related Disorders”). Preferred indications also include autoimmune diseases (e.g., rheumatoid arthritis, systemic lupus erythematosis, multiple sclerosis and/or as described below) and immunodeficiencies (e.g., as described below). Preferred indications also include neoplastic diseases (e.g., leukemia, lymphoma, melanoma, and/or as described below under “Hyperproliferative Disorders”). Preferred indications include neoplasms and cancer, such as, for example, leukemia, lymphoma, melanoma, and prostate, breast, lung, colon, pancreatic, esophageal, stomach, brain, liver, urinary tract cancers and as described below under “Hyperproliferative Disorders”. |
| 32 | Activation of transcription through NFKB response element in immune cells (such as EOL1 cells). | Assays for the activation of transcription through the NFKB response element are well-known in the art and may be used or routinely modified to assess the ability of polypeptides of the invention (including antibodies and agonists or antagonists of the invention) to regulate NFKB transcription factors and modulate expression of immunomodulatory genes. Exemplary assays for transcription through the NFKB response element that may be used or rountinely modified to test NFKB-response element activity of polypeptides of the invention (including antibodies and agonists or antagonists of the invention) include assays disclosed in Berger et al., Gene 66: 1-10 (1998); Cullen and Malm, Methods in Enzymol 216: 362-368 (1992); Henthorn et al., Proc Natl Acad Sci USA 85: 6342-6346 (1988); Valle Blazquez et al, Immunology 90(3): 455-460 (1997); Aramburau et al., J Exp Med 82(3): 801-810 (1995); and Fraser | Highly preferred indications include asthma, allergy, hypersensitivity reactions, and inflammation. Preferred indications include infection (e.g., an infectious disease as described below under “Infectious Disease”), immunological disorders, inflammation and inflammatory disorders (e.g., as described below under “Immune Activity”, and “Blood-Related Disorders”). Preferred indications include autoimmune diseases (e.g., rheumatoid arthritis, systemic lupus erythematosis, multiple sclerosis and/or as described below) and immunodeficiencies (e.g., as described below). |

TABLE 1E.2-continued

| Biological Activity No. | Biological Activity | Exemplary Activity Assay | Preferred Indication |
|---|---|---|---|
| | | et al., 29(3): 838-844 (1999), the contents of each of which are herein incorporated by reference in its entirety. For example, a reporter assay (which measures increases in transcription inducible from a NFkB responsive element in EOL-1 cells) may link the NFKB element to a repeorter gene and binds to the NFKB transcription factor, which is upregulated by cytokines and other factors. Exemplary immune cells that may be used according to these assays include eosinophils such as the human EOL-1 cell line of eosinophils. Eosinophils are a type of immune cell important in the allergic responses; they are recruited to tissues and mediate the inflammtory response of late stage allergic reaction. Eol-1 is a human eosinophil cell line. | |
| 33 | Activation of transcription through NFKB response element in immune cells (such as mast cells). | This reporter assay measures activation of the NFkB signaling pathway in HMC-1 human mast cell line. Activation of NFkB in mast cells has been linked to production of certain cytokines, such as IL-6 and IL-9. Assays for the activation of transcription through the NFKB response element are well-known in the art and may be used or routinely modified to assess the ability of polypeptides of the invention (including antibodies and agonists or antagonists of the invention) to regulate NFKB transcription factors and modulate expression of immunomodulatory genes. Exemplary assays for transcription through the NFKB response element that may be used or rountinely modified to test NFKB-response element activity of polypeptides of the invention (including antibodies and agonists or antagonists of the invention) include assays disclosed in Berger et al., Gene 66: 1-10 (1998); Cullen and Malm, Methods in Enzymol 216: 362-368 (1992); Henthorn et al., Proc Natl Acad Sci USA 85: 6342-6346 (1988); Stassen et al, J Immunol 166(7): 4391-8 (2001); and Marquardt and Walker, J Allergy Clin Immunol 105(3): 500-5 (2000), the contents of each of which are herein incorporated by reference in its entirety. Mast cells that may be used according to these assays are publicly available (e.g., through the ATCC ™). Exemplary human mast cells that may be used according to these assays include the HMC-1 cell line, which is an immature human mast cell line established from the peripheral blood of a patient with mast cell leukemia, and exhibits many characteristics of immature mast cells. | Highly preferred indication includes allergy, asthma, and rhinitis. Additional highly preferred indications include infection (e.g., an infectious disease as described below under “Infectious Disease”), and inflammation and inflammatory disorders. Preferred indications include immunological and hempatopoietic disorders (e.g., as described below under “Immune Activity”, and “Blood-Related Disorders”). Preferred indications also include autoimmune diseases (e.g., rheumatoid arthritis, systemic lupus erythematosis, multiple sclerosis and/or as described below) and immunodeficiencies (e.g., as described below). Preferred indications also include neoplastic diseases (e.g., leukemia, lymphoma, melanoma, and/or as described below under “Hyperproliferative Disorders”). Preferred indications include neoplasms and cancer, such as, for example, leukemia, lymphoma, melanoma, and prostate, breast, lung, colon, pancreatic, esophageal, stomach, brain, liver, urinary tract cancers and as described below under “Hyperproliferative Disorders”. |
| 34 | Activation of transcription through NFKB response element in immune cells (such as natural killer cells). | Assays for the activation of transcription through the NFKB response element are well-known in the art and may be used or routinely modified to assess the ability of polypeptides of the invention (including antibodies and agonists or antagonists of the invention) to regulate NFKB transcription factors and modulate expression of immunomodulatory genes. Exemplary assays for transcription through the NFKB response element that may be used or rountinely modified to test NFKB-response element activity of polypeptides of the invention (including antibodies and agonists or antagonists of the invention) include assays disclosed in Berger et al., Gene 66: 1-10 (1998); Cullen and Malm, Methods in Enzymol 216: 362-368 (1992); Henthorn et al., Proc Natl Acad Sci USA 85: 6342-6346 | Highly preferred indications include inflammation and inflammatory disorders. Highly preferred indications include blood disorders (e.g., as described below under “Immune Activity”, “Blood-Related Disorders”, and/or “Cardiovascular Disorders”). Highly preferred indications include autoimmune diseases (e.g., rheumatoid arthritis, systemic lupus erythematosis, multiple sclerosis and/or as described below), and immunodeficiencies (e.g., as described below). An additional highly preferred indication is infection (e.g., AIDS, and/or an infectious disease as described below under “Infectious Disease”). Highly preferred indications include neoplastic diseases (e.g., melanoma, leukemia, lymphoma, and/or as described below under “Hyperproliferative Disorders”). Highly preferred indications include neoplasms |

TABLE 1E.2-continued

| Biological Activity No. | Biological Activity | Exemplary Activity Assay | Preferred Indication |
|---|---|---|---|
| | | (1988); Valle Blazquez et al, Immunology 90(3): 455-460 (1997); Aramburau et al., J Exp Med 82(3): 801-810 (1995); and Fraser et al., 29(3): 838-844 (1999), the contents of each of which are herein incorporated by reference in its entirety. NK cells that may be used according to these assays are publicly available (e.g., through the ATCC ™). Exemplary NK cells that may be used according to these assays include the NK-YT cell line, which is a human natural killer cell line with cytolytic and cytotoxic activity. | and cancers, such as, for example, melanoma, renal cell carcinoma, leukemia, lymphoma, and prostate, breast, lung, colon, pancreatic, esophageal, stomach, brain, liver and urinary cancer. Other preferred indications include benign dysproliferative disorders and pre-neoplastic conditions, such as, for example, hyperplasia, metaplasia, and/or dysplasia. Preferred indications also include anemia, pancytopenia, leukopenia, thrombocytopenia, Hodgkin's disease, acute lymphocytic anemia (ALL), plasmacytomas, multiple myeloma, Burkitt's lymphoma, arthritis, AIDS, granulomatous disease, inflammatory bowel disease, sepsis, neutropenia, neutrophilia, psoriasis, hemophilia, hypercoagulation, diabetes mellitus, endocarditis, meningitis, Lyme Disease, suppression of immune reactions to transplanted organs, asthma and allergy. |
| 35 | Activation of transcription through NFKB response element in immune cells (such as T-cells). | Assays for the activation of transcription through the NFKB response element are well-known in the art and may be used or routinely modified to assess the ability of polypeptides of the invention (including antibodies and agonists or antagonists of the invention) to regulate NFKB transcription factors and modulate expression of immunomodulatory genes. Exemplary assays for transcription through the NFKB response element that may be used or rountinely modified to test NFKB-response element activity of polypeptides of the invention (including antibodies and agonists or antagonists of the invention) include assays disclosed in Berger et al., Gene 66: 1-10 (1998); Cullen and Malm, Methods in Enzymol 216: 362-368 (1992); Henthorn et al., Proc Natl Acad Sci USA 85: 6342-6346 (1988); Black et al., Virus Gnes 15(2): 105-117 (1997); and Fraser et al., 29(3): 838-844 (1999), the contents of each of which are herein incorporated by reference in its entirety. T cells that may be used according to these assays are publicly available (e.g., through the ATCC ™). Exemplary human T cells that may be used according to these assays include the SUPT cell line, which is a suspension culture of IL-2 and IL-4 responsive T cells. Additional exemplary human T cells, such as the MOLT4, that may be used according to these assays are publicly available (e.g., through the ATCC ™). | Highly preferred indications include inflammation and inflammatory disorders. Highly preferred indications include blood disorders (e.g., as described below under "Immune Activity", "Blood-Related Disorders", and/or "Cardiovascular Disorders"). Highly preferred indications include autoimmune diseases (e.g., rheumatoid arthritis, systemic lupus erythematosis, multiple sclerosis and/or as described below), and immunodeficiencies (e.g., as described below). An additional highly preferred indication is infection (e.g., AIDS, and/or an infectious disease as described below under "Infectious Disease"). Highly preferred indications include neoplastic diseases (e.g., melanoma, leukemia, lymphoma, and/or as described below under "Hyperproliferative Disorders"). Highly preferred indications include neoplasms and cancers, such as, for example, melanoma, renal cell carcinoma, leukemia, lymphoma, and prostate, breast, lung, colon, pancreatic, esophageal, stomach, brain, liver and urinary cancer. Other preferred indications include benign dysproliferative disorders and pre-neoplastic conditions, such as, for example, hyperplasia, metaplasia, and/or dysplasia. Preferred indications also include anemia, pancytopenia, leukopenia, thrombocytopenia, Hodgkin's disease, acute lymphocytic anemia (ALL), plasmacytomas, multiple myeloma, Burkitt's lymphoma, arthritis, AIDS, granulomatous disease, inflammatory bowel disease, sepsis, neutropenia, neutrophilia, psoriasis, hemophilia, hypercoagulation, diabetes mellitus, endocarditis, meningitis, Lyme Disease, suppression of immune reactions to transplanted organs, asthma and allergy. |
| 36 | Activation of transcription through NFKB response element in immune cells (such as the Jurkat human T cell line). | Assays for the activation of transcription through the NFKB response element are well-known in the art and may be used or routinely modified to assess the ability of polypeptides of the invention (including antibodies and agonists or antagonists of the invention) to regulate NFKB transcription factors and modulate expression of immunomodulatory genes. Exemplary assays for transcription through the NFKB response element that may be used or rountinely modified to test NFKB-response element activity of polypeptides of the invention (including antibodies and agonists or antagonists of the invention) include assays disclosed in Berger et al., Gene 66: 1-10 (1998); Cullen and Malm, Methods in | Highly preferred indications include inflammation and inflammatory disorders. Highly preferred indications include immunological and hematopoietic disorders (e.g., as described below under "Immune Activity", "Blood-Related Disorders", and/or "Cardiovascular Disorders"). Highly preferred indications include autoimmune diseases (e.g., rheumatoid arthritis, systemic lupus erythematosis, multiple sclerosis and/or as described below), and immunodeficiencies (e.g., as described below). An additional highly preferred indication is infection (e.g., AIDS, and/or an infectious disease as described below under "Infectious Disease"). Highly preferred indications include neoplastic diseases (e.g., melanoma, leukemia, lymphoma, and/or as |

TABLE 1E.2-continued

| Biological Activity No. | Biological Activity | Exemplary Activity Assay | Preferred Indication |
|---|---|---|---|
| | | Enzymol 216: 362-368 (1992); Henthorn et al., Proc Natl Acad Sci USA 85: 6342-6346 (1988); Valle Blazquez et al, Immunology 90(3): 455-460 (1997); Aramburau et al., J Exp Med 82(3): 801-810 (1995); and Fraser et al., 29(3): 838-844 (1999), the contents of each of which are herein incorporated by reference in its entirety. T cells that may be used according to these assays are publicly available (e.g., through the ATCC ™). T cells that may be used according to these assays are publicly available (e.g., through the ATCC ™). Exemplary human T cells that may be used according to these assays include the JURKAT cell line, which is a suspension culture of leukemia cells that produce IL-2 when stimulated. | described below under “Hyperproliferative Disorders”). Highly preferred indications include neoplasms and cancers, such as, melanoma, renal cell carcinoma, leukemia, lymphoma, and prostate, breast, lung, colon, pancreatic, esophageal, stomach, brain, liver and urinary cancer. Other preferred indications include benign dysproliferative disorders and pre-neoplastic conditions, such as, for example, hyperplasia, metaplasia, and/or dysplasia. Preferred indications also include anemia, pancytopenia, leukopenia, thrombocytopenia, Hodgkin’s disease, acute lymphocytic anemia (ALL), plasmacytomas, multiple myeloma, Burkitt’s lymphoma, arthritis, AIDS, granulomatous disease, inflammatory bowel disease, sepsis, neutropenia, neutrophilia, psoriasis, hemophilia, hypercoagulation, diabetes mellitus, endocarditis, meningitis, Lyme Disease, suppression of immune reactions to transplanted organs, asthma and allergy. |
| 37 | Activation of transcription through NFKB response element in immune cells (such as the U937 human monocyte cell line). | This assay uses a NFKB response element (which will bind NFKB transcription factors) linked to a reporter gene to measure NFKB mediated transcription in the human monocyte cell line U937. NFKB is upregulated by cytokines and other factors and NFKB element activation leads to expression of immunomodulatory genes. Activation of NFKB in monocytes can play a role in immune responses. Exemplary assays for transcription through the NFKB response element that may be used or rountinely modified to test NFKB-response element activity of polypeptides of the invention (including antibodies and agonists or antagonists of the invention) include assays disclosed in Berger et al., Gene 66: 1-10 (1998); Cullen and Malm, Methods in Enzymol 216: 362-368 (1992); Henthorn et al., Proc Natl Acad Sci USA 85: 6342-6346 (1988); Valle Blazquez et al, Immunology 90(3): 455-460 (1997); Aramburau et al., J Exp Med 82(3): 801-810 (1995); and Fraser et al., 29(3): 838-844 (1999), the contents of each of which are herein incorporated by reference in its entirety. Monocytic cells that may be used according to these assays are publicly available (e.g., through the ATCC ™). Exemplary human monocyte cells that may be used according to these assays include the U937 cell line, which is cell line derived by Sundstrom and Nilsson in 1974 from malignant cells obtained from the pleural effusion of a patient with histiocytic lymphoma. | Highly preferred indications include inflammation and inflammatory disorders. Highly preferred indications include immunological and hematopoietic disorders (e.g., as described below under “Immune Activity”, “Blood-Related Disorders”, and/or “Cardiovascular Disorders”). Highly preferred indications include autoimmune diseases (e.g., rheumatoid arthritis, systemic lupus erythematosis, multiple sclerosis and/or as described below), and immunodeficiencies (e.g., as described below). An additional highly preferred indication is infection (e.g., AIDS, and/or an infectious disease as described below under “Infectious Disease”). Highly preferred indications include neoplastic diseases (e.g., melanoma, leukemia, lymphoma, and/or as described below under “Hyperproliferative Disorders”). Highly preferred indications include neoplasms and cancers, such as, melanoma, renal cell carcinoma, leukemia, lymphoma, and prostate, breast, lung, colon, pancreatic, esophageal, stomach, brain, liver and urinary cancer. Other preferred indications include benign dysproliferative disorders and pre-neoplastic conditions, such as, for example, hyperplasia, metaplasia, and/or dysplasia. Preferred indications also include anemia, pancytopenia, leukopenia, thrombocytopenia, Hodgkin’s disease, acute lymphocytic anemia (ALL), plasmacytomas, multiple myeloma, Burkitt’s lymphoma, arthritis, AIDS, granulomatous disease, inflammatory bowel disease, sepsis, neutropenia, neutrophilia, psoriasis, hemophilia, hypercoagulation, diabetes mellitus, endocarditis, meningitis, Lyme Disease, suppression of immune reactions to transplanted organs, asthma and allergy. |
| 38 | Activation of transcription through NFKB response element in neuronal cells (such as SKNMC cells). | Assays for the activation of transcription through the NFKB response element are well-known in the art and may be used or routinely modified to assess the ability of polypeptides of the invention (including antibodies and agonists or antagonists of the invention) to regulate NFKB transcription factors and modulate expression of neuronal genes. Exemplary assays for transcription through the NFKB response element that may be used or routinely modified to test NFKB-response element activity of polypeptides of the invention (including antibodies and agonists or antagonists of the invention) include assays disclosed in: Gill J S, | |

TABLE 1E.2-continued

| Biological Activity No. | Biological Activity | Exemplary Activity Assay | Preferred Indication |
|---|---|---|---|
| | | et al., Neurobiol Dis, 7(4): 448-461 (2000); Tamatani M, et al., J Biol Chem, 274(13): 8531-8538 (1999); Berger et al., Gene 66: 1-10 (1998); Cullen and Malm, Methods in Enzymol 216: 362-368 (1992); Henthorn et al., Proc Natl Acad Sci USA 85: 6342-6346 (1988); Valle Blazquez et al, Immunology 90(3): 455-460 (1997); Aramburau et al., J Exp Med 82(3): 801-810 (1995); and Fraser et al., 29(3): 838-844 (1999), the contents of each of which are herein incorporated by reference in its entirety. Neuronal cells that may be used according to these assays are publicly available (e.g., through the ATCC ™). Exemplary neuronal cells that may be used according to these assays include the SKNMC neuronal cell line. | |
| 39 | Activation of transcription through NFKB response element in neuronal cells (such as SKNMC cells). | Assays for the activation of transcription through the NFKB response element are well-known in the art and may be used or routinely modified to assess the ability of polypeptides of the invention (including antibodies and agonists or antagonists of the invention) to regulate NFKB transcription factors and modulate expression of neuronal genes. Exemplary assays for transcription through the NFKB response element that may be used or routinely modified to test NFKB-response element activity of polypeptides of the invention (including antibodies and agonists or antagonists of the invention) include assays disclosed in: Gill J S, et al., Neurobiol Dis, 7(4): 448-461 (2000); Tamatani M, et al., J Biol Chem, 274(13): 8531-8538 (1999); Berger et al., Gene 66: 1-10 (1998); Cullen and Malm, Methods in Enzymol 216: 362-368 (1992); Henthorn et al., Proc Natl Acad Sci USA 85: 6342-6346 (1988); Valle Blazquez et al, Immunology 90(3): 455-460 (1997); Aramburau et al., J Exp Med 82(3): 801-810 (1995); and Fraser et al., 29(3): 838-844 (1999), the contents of each of which are herein incorporated by reference in its entirety. Neuronal cells that may be used according to these assays are publicly available (e.g., through the ATCC ™). Exemplary neuronal cells that may be used according to these assays include the SKNMC neuronal cell line. | Preferred embodiments of the invention include using polypeptides of the invention (or antibodies, agonists, or antagonists thereof) in detection, diagnosis, prevention, and/or treatment of Neurological Diseases and Disorders (e.g. Alzheimer"s Disease, Parkinson"s Disease, Brain Cancer, Seizures). |
| 40 | Activation of transcription through serum response element in immune cells (such as natural killer cells). | Assays for the activation of transcription through the Serum Response Element (SRE) are well-known in the art and may be used or routinely modified to assess the ability of polypeptides of the invention (including antibodies and agonists or antagonists of the invention) to regulate serum response factors and modulate the expression of genes involved in growth and upregulate the function of growth-related genes in many cell types. Exemplary assays for transcription through the SRE that may be used or routinely modified to test SRE activity of the polypeptides of the invention (including antibodies and agonists or antagonists of the invention) include assays disclosed in Berger et al., Gene 66: 1-10 (1998); Cullen and Malm, Methods in Enzymol 216: 362-368 (1992); Henthorn et al., Proc Natl Acad Sci USA 85: 6342-6346 (1988); Benson et al., J Immunol 153(9): 3862-3873 (1994); and Black et al., Virus Genes 12(2): 105-117 (1997), the content of each of which are herein incorporated by reference in its entirety. T | A preferred embodiment of the invention includes a method for inhibiting (e.g., reducing) TNF alpha production. An alternative highly preferred embodiment of the invention includes a method for stimulating (e.g., increasing) TNF alpha production. Preferred indications include blood disorders (e.g., as described below under "Immune Activity", "Blood-Related Disorders", and/or "Cardiovascular Disorders"), Highly preferred indications include autoimmune diseases (e.g., rheumatoid arthritis, systemic lupus erythematosis, Crohn"s disease, multiple sclerosis and/or as described below), immunodeficiencies (e.g., as described below), boosting a T cell-mediated immune response, and suppressing a T cell-mediated immune response. Additional highly preferred indications include inflammation and inflammatory disorders, and treating joint damage in patients with rheumatoid arthritis. An additional highly preferred indication is sepsis. Highly preferred indications include neoplastic diseases (e.g., leukemia, lymphoma, and/or as described below under "Hyperproliferative Disorders"). Additionally, |

TABLE 1E.2-continued

| Biological Activity No. | Biological Activity | Exemplary Activity Assay | Preferred Indication |
|---|---|---|---|
| | | cells that may be used according to these assays are publicly available (e.g., through the ATCC ™). Exemplary T cells that may be used according to these assays include the NK-YT cell line, which is a human natural killer cell line with cytolytic and cytotoxic activity. | highly preferred indications include neoplasms and cancers, such as, for example, leukemia, lymphoma, melanoma, glioma (e.g., malignant glioma), solid tumors, and prostate, breast, lung, colon, pancreatic, esophageal, stomach, brain, liver and urinary cancer. Other preferred indications include benign dysproliferative disorders and pre-neoplastic conditions, such as, for example, hyperplasia, metaplasia, and/or dysplasia. Preferred indications include anemia, pancytopenia, leukopenia, thrombocytopenia, Hodgkin's disease, acute lymphocytic anemia (ALL), plasmacytomas, multiple myeloma, Burkitt's lymphoma, arthritis, AIDS, granulomatous disease, inflammatory bowel disease, neutropenia, neutrophilia, psoriasis, suppression of immune reactions to transplanted organs and tissues, hemophilia, hypercoagulation, diabetes mellitus, endocarditis, meningitis, Lyme Disease, cardiac reperfusion injury, and asthma and allergy. An additional preferred indication is infection (e.g., an infectious disease as described below under "Infectious Disease"). |
| 41 | Activation of transcription through serum response element in immune cells (such as T-cells). | Assays for the activation of transcription through the Serum Response Element (SRE) are well-known in the art and may be used or routinely modified to assess the ability of polypeptides of the invention (including antibodies and agonists or antagonists of the invention) to regulate the serum response factors and modulate the expression of genes involved in growth. Exemplary assays for transcription through the SRE that may be used or routinely modified to test SRE activity of the polypeptides of the invention (including antibodies and agonists or antagonists of the invention) include assays disclosed in Berger et al., Gene 66: 1-10 (1998); Cullen and Malm, Methods in Enzymol 216: 362-368 (1992); Henthorn et al., Proc Natl Acad Sci USA 85: 6342-6346 (1988); and Black et al., Virus Genes 12(2): 105-117 (1997), the content of each of which are herein incorporated by reference in its entirety. T cells that may be used according to these assays are publicly available (e.g., through the ATCC ™). Exemplary mouse T cells that may be used according to these assays include the CTLL cell line, which is an IL-2 dependent suspension culture of T cells with cytotoxic activity. Exemplary human T cells, such as the MOLT4, that may be used according to these assays are publicly available (e.g., through the ATCC ™). Additional exemplary human T cells that may be used according to these assays include the JURKAT cell line, which is a suspension culture of leukemia cells that produce IL-2 when stimulated. | A preferred embodiment of the invention includes a method for inhibiting (e.g., reducing) TNF alpha production. An alternative preferred embodiment of the invention includes a method for stimulating (e.g., increasing) TNF alpha production. Preferred indications include blood disorders (e.g., as described below under "Immune Activity", "Blood-Related Disorders", and/or ""Cardiovascular Disorders""), Highly preferred indications include autoimmune diseases (e.g., rheumatoid arthritis, systemic lupus erythematosis, Crohn's disease, multiple sclerosis and/or as described below), immunodeficiencies (e.g., as described below), boosting a T cell-mediated immune response, and suppressing a T cell-mediated immune response. Additional highly preferred indications include inflammation and inflammatory disorders, and treating joint damage in patients with rheumatoid arthritis. An additional highly preferred indication is sepsis. Highly preferred indications include neoplastic diseases (e.g., leukemia, lymphoma, and/or as described below under "Hyperproliferative Disorders"). Additionally, highly preferred indications include neoplasms and cancers, such as, for example, leukemia, lymphoma, melanoma, glioma (e.g., malignant glioma), solid tumors, and prostate, breast, lung, colon, pancreatic, esophageal, stomach, brain, liver and urinary cancer. Other preferred indications include benign dysproliferative disorders and pre-neoplastic conditions, such as, for example, hyperplasia, metaplasia, and/or dysplasia. Preferred indications include anemia, pancytopenia, leukopenia, thrombocytopenia, Hodgkin's disease, acute lymphocytic anemia (ALL), plasmacytomas, multiple myeloma, Burkitt's lymphoma, arthritis, AIDS, granulomatous disease, inflammatory bowel disease, neutropenia, neutrophilia, psoriasis, suppression of immune reactions to transplanted organs and tissues, hemophilia, hypercoagulation, diabetes mellitus, endocarditis, meningitis, Lyme Disease, cardiac reperfusion injury, and asthma and allergy. An additional preferred indication is infection (e.g., an infectious disease as described below under "Infectious Disease"). |
| 42 | Activation of transcription through | Assays for the activation of transcription through the Serum Response Element | A highly preferred indication is obesity and/or complications associated with obesity. |

TABLE 1E.2-continued

| Biological Activity No. | Biological Activity | Exemplary Activity Assay | Preferred Indication |
|---|---|---|---|
| | serum response element in pre-adipocytes. | (SRE) are well-known in the art and may be used or routinely modified to assess the ability of polypeptides of the invention (including antibodies and agonists or antagonists of the invention) to regulate the serum response factors and modulate the expression of genes involved in growth. Exemplary assays for transcription through the SRE that may be used or routinely modified to test SRE activity of the polypeptides of the invention (including antibodies and agonists or antagonists of the invention) include assays disclosed in Berger et al., Gene 66: 1-10 (1998); Cullen and Malm, Methods in Enzymol 216: 362-368 (1992); Henthorn et al., Proc Natl Acad Sci USA 85: 6342-6346 (1988); and Black et al., Virus Genes 12(2): 105-117 (1997), the content of each of which are herein incorporated by reference in its entirety. Pre-adipocytes that may be used according to these assays are publicly available (e.g., through the ATCC ™) and/or may be routinely generated. Exemplary mouse adipocyte cells that may be used according to these assays include 3T3-L1 cells. 3T3-L1 is an adherent mouse preadipocyte cell line that is a continuous substrain of 3T3 fibroblast cells developed through clonal isolation and undergo a pre-adipocyte to adipose-like conversion under appropriate differentiation conditions known in the art. | Additional highly preferred indications include weight loss or alternatively, weight gain. An additional highly preferred indication is diabetes mellitus. An additional highly preferred indication is a complication associated with diabetes (e.g., diabetic retinopathy, diabetic nephropathy, kidney disease (e.g., renal failure, nephropathy and/or other diseases and disorders as described in the "Renal Disorders" section below), diabetic neuropathy, nerve disease and nerve damage (e.g., due to diabetic neuropathy), blood vessel blockage, heart disease, stroke, impotence (e.g., due to diabetic neuropathy or blood vessel blockage), seizures, mental confusion, drowsiness, nonketotic hyperglycemic-hyperosmolar coma, cardiovascular disease (e.g., heart disease, atherosclerosis, microvascular disease, hypertension, stroke, and other diseases and disorders as described in the "Cardiovascular Disorders" section below), dyslipidemia, endocrine disorders (as described in the "Endocrine Disorders" section below), neuropathy, vision impairment (e.g., diabetic retinopathy and blindness), ulcers and impaired wound healing, and infection (e.g., infectious diseases and disorders as described in the "Infectious Diseases" section below). Additional highly preferred indications are complications associated with insulin resistance. |
| 43 | Activation of transcription through STAT6 response element in immune cells (such as mast cells). | Assays for the activation of transcription through the Signal Transducers and Activators of Transcription (STAT6) response element in immune cells (such as in the human HMC-1 mast cell line) are well-known in the art and may be used or routinely modified to assess the ability of polypeptides of the invention (including antibodies and agonists or antagonists of the invention) to regulate STAT6 transcription factors and modulate the expression of multiple genes. Exemplary assays for transcription through the STAT6 response element that may be used or routinely modified to test STAT6 response element activity of the polypeptides of the invention (including antibodies and agonists or antagonists of the invention) include assays disclosed in Berger et al., Gene 66: 1-10 (1998); Cullen and Malm, Methods in Enzymol 216: 362-368 (1992); Henthorn et al., Proc Natl Acad Sci USA 85: 6342-6346 (1988); Sherman, Immunol Rev 179: 48-56 (2001); Malaviya and Uckun, J Immunol 168: 421-426 (2002); Masuda et al., J Biol Chem 275(38): 29331-29337 (2000); and Masuda et al., J Biol Chem 276: 26107-26113 (2001), the contents of each of which are herein incorporated by reference in its entirety. Mast cells that may be used according to these assays are publicly available (e.g., through the ATCC ™). Exemplary human mast cells that may be used according to these assays include the HMC-1 cell line, which is an immature human mast cell line established from the peripheral blood of a patient with mast cell leukemia, and exhibits many characteristics of immature mast cells. | Highly preferred indications include allergy, asthma, and rhinitis. Additional highly preferred indications include infection (e.g., an infectious disease as described below under "Infectious Disease"), and inflammation and inflammatory disorders. Preferred indications also include hematopoietic and immunological disorders (e.g., as described below under "Immune Activity", "Blood-Related Disorders", and/or "Cardiovascular Disorders"), autoimmune diseases (e.g., rheumatoid arthritis, systemic lupus erythematosis, multiple sclerosis and/or as described below), and immunodeficiencies (e.g., as described below). Preferred indications include neoplastic diseases (e.g., leukemia, lymphoma, melanoma, and/or as described below under "Hyperproliferative Disorders"). Preferred indications include neoplasms and cancer, such as, for example, leukemia, lymphoma, melanoma, and prostate, breast, lung, colon, pancreatic, esophageal, stomach, brain, liver and urinary cancer. Other preferred indications include benign dysproliferative disorders and pre-neoplastic conditions, such as, for example, hyperplasia, metaplasia, and/or dysplasia. Preferred indications include hematopoietic and immunological disorders such as arthritis, AIDS, granulomatous disease, inflammatory bowel disease, sepsis, neutropenia, neutrophilia, psoriasis, suppression of immune reactions to transplanted organs and tissues, hemophilia, hypercoagulation, diabetes mellitus, endocarditis, meningitis, and Lyme Disease. |
| 44 | Activation of transcription through STAT6 response element in immune cells (such as natural | Assays for the activation of transcription through the Signal Transducers and Activators of Transcription (STAT6) response element are well-known in the art and may be used or routinely modified to | |

TABLE 1E.2-continued

| Biological Activity No. | Biological Activity | Exemplary Activity Assay | Preferred Indication |
|---|---|---|---|
| | killer cells). | assess the ability of polypeptides of the invention (including antibodies and agonists or antagonists of the invention) to regulate STAT6 transcription factors and modulate the expression of multiple genes. Exemplary assays for transcription through the STAT6 response element that may be used or routinely modified to test STAT6 response element activity of the polypeptides of the invention (including antibodies and agonists or antagonists of the invention) include assays disclosed in Berger et al., Gene 66: 1-10 (1998); Cullen and Malm, Methods in Enzymol 216: 362-368 (1992); Henthorn et al., Proc Natl Acad Sci USA 85: 6342-6346 (1988); Georas et al., Blood 92(12): 4529-4538 (1998); Moffatt et al., Transplantation 69(7): 1521-1523 (2000); Curiel et al., Eur J Immunol 27(8): 1982-1987 (1997); and Masuda et al., J Biol Chem 275(38): 29331-29337 (2000), the contents of each of which are herein incorporated by reference in its entirety. T cells that may be used according to these assays are publicly available (e.g., through the ATCC ™). Exemplary rat natural killer cells that may be used according to these assays are publicly available (e.g., through the ATCC ™). | |
| 45 | Activation of transcription through STAT6 response element in immune cells (such as T-cells). | Assays for the activation of transcription through the Signal Transducers and Activators of Transcription (STAT6) response element are well-known in the art and may be used or routinely modified to assess the ability of polypeptides of the invention (including antibodies and agonists or antagonists of the invention) to regulate STAT6 transcription factors and modulate the expression of multiple genes. Exemplary assays for transcription through the STAT6 response element that may be used or routinely modified to test STAT6 response element activity of the polypeptides of the invention (including antibodies and agonists or antagonists of the invention) include assays disclosed in Berger et al., Gene 66: 1-10 (1998); Cullen and Malm, Methods in Enzymol 216: 362-368 (1992); Henthorn et al., Proc Natl Acad Sci USA 85: 6342-6346 (1988); Georas et al., Blood 92(12): 4529-4538 (1998); Moffatt et al., Transplantation 69(7): 1521-1523 (2000); Curiel et al., Eur J Immunol 27(8): 1982-1987 (1997); and Masuda et al., J Biol Chem 275(38): 29331-29337 (2000), the contents of each of which are herein incorporated by reference in its entirety. T cells that may be used according to these assays are publicly available (e.g., through the ATCC ™). Exemplary T cells that may be used according to these assays include the SUPT cell line, which is a suspension culture of IL-2 and IL-4 responsive T cells. | A highly preferred indication is allergy. Another highly preferred indication is asthma. Additional highly preferred indications include inflammation and inflammatory disorders. Preferred indications include blood disorders (e.g., as described below under "Immune Activity", "Blood-Related Disorders", and/or "Cardiovascular Disorders"). Preferred indications include autoimmune diseases (e.g., rheumatoid arthritis, systemic lupus erythematosis, multiple sclerosis and/or as described below) and immunodeficiencies (e.g., as described below). Preferred indications include neoplastic diseases (e.g., leukemia, lymphoma, melanoma, and/or as described below under "Hyperproliferative Disorders"). Preferred indications include neoplasms and cancers, such as, leukemia, lymphoma, melanoma, and prostate, breast, lung, colon, pancreatic, esophageal, stomach, brain, liver and urinary cancer. Other preferred indications include benign dysproliferative disorders and pre-neoplastic conditions, such as, for example, hyperplasia, metaplasia, and/or dysplasia. Preferred indications include anemia, pancytopenia, leukopenia, thrombocytopenia, Hodgkin's disease, acute lymphocytic anemia (ALL), plasmacytomas, multiple myeloma, Burkitt's lymphoma, arthritis, AIDS, granulomatous disease, inflammatory bowel disease, sepsis, neutropenia, neutrophilia, psoriasis, suppression of immune reactions to transplanted organs and tissues, hemophilia, hypercoagulation, diabetes mellitus, endocarditis, meningitis, and Lyme Disease. An additional preferred indication is infection (e.g., an infectious disease as described below under "Infectious Disease"). |
| 46 | Activation of transcription through the EGR (Early Growth Response) element in immune cells (such as B-cells). | Assays for the activation of transcription through the EGR response element are well-known in the art and may be used or routinely modified to assess the ability of polypeptides of the invention (including antibodies and agonists or antagonists of the invention) to regulate EGR transcription factors and modulate expression of | |

TABLE 1E.2-continued

| Biological Activity No. | Biological Activity | Exemplary Activity Assay | Preferred Indication |
|---|---|---|---|
| | | immunomodulatory genes. Exemplary assays for transcription through the EGR response element that may be used or routinely modified to test EGR response element activity of polypeptides of the invention (including antibodies and agonists or antagonists of the invention) include assays disclosed in: Richards J D, et al., J Immunol, 166(6): 3855-3864 (2001); Dinkel, A, et al., J Exp Med, 188(12): 2215-2224 (1998); and, Newton, J S, et al., Eur J Immunol 1996 April; 26(4): 811-816 (1996), the contents of each of which are herein incorporated by reference in its entirety. Immune cells that may be used according to these assays are publicly available (e.g., through the ATCC ™). Exemplary epithelial cells that may be used according to these assays include the Raji cell line. | |
| 47 | Activation of transcription through the EGR (Early Growth Response) element in immune cells (such as B-cells). | Assays for the activation of transcription through the EGR response element are well-known in the art and may be used or routinely modified to assess the ability of polypeptides of the invention (including antibodies and agonists or antagonists of the invention) to regulate EGR transcription factors and modulate expression of immunomodulatory genes. Exemplary assays for transcription through the EGR response element that may be used or routinely modified to test EGR response element activity of polypeptides of the invention (including antibodies and agonists or antagonists of the invention) include assays disclosed in: Richards J D, et al., J Immunol, 166(6): 3855-3864 (2001); Dinkel, A, et al., J Exp Med, 188(12): 2215-2224 (1998); and, Newton, J S, et al., Eur J Immunol 1996 April; 26(4): 811-816 (1996), the contents of each of which are herein incorporated by reference in its entirety. Immune cells that may be used according to these assays are publicly available (e.g., through the ATCC ™). Exemplary epithelial cells that may be used according to these assays include the Raji cell line. | Preferred embodiments of the invention include using polypeptides of the invention (or antibodies, agonists, or antagonists thereof) in detection, diagnosis, prevention, and/or treatment of Cancer, Autoimmunity, Allergy and Asthma. |
| 48 | Activation or inhibition of transcription through NFKB response element in immune cells (such as basophils). | This reporter assay measures activation or inhibition of the NFkB signaling pathway in Ku812 human basophil cell line. Assays for the activation or inhibition of transcription through the NFKB response element are well-known in the art and may be used or routinely modified to assess the ability of polypeptides of the invention (including antibodies and agonists or antagonists of the invention) to regulate NFKB transcription factors and modulate expression of immunomodulatory genes. NFkB is important in the pathogenesis of asthma. Exemplary assays for transcription through the NFKB response element that may be used or rountinely modified to test NFKB-response element activity of polypeptides of the invention (including antibodies and agonists or antagonists of the invention) include assays disclosed in Berger et al., Gene 66: 1-10 (1998); Cullen and Malm, Methods in Enzymol 216: 362-368 (1992); Henthorn et al., Proc Natl Acad Sci USA 85: 6342-6346 (1988); Marone et al, Int Arch Allergy Immunol 114(3): 207-17 (1997), the contents of each of which are herein incorporated by reference in its entirety. Cells were pretreated with SID supernatants or controls for 15-18 hours, and then 10 ng/mL of TNF was added to | |

TABLE 1E.2-continued

| Biological Activity No. | Biological Activity | Exemplary Activity Assay | Preferred Indication |
|---|---|---|---|
| | | stimulate the NFkB reporter. SEAP activity was measured after 48 hours. Basophils that may be used according to these assays are publicly available (e.g., through the ATCC ™). Exemplary human basophil cell lines that may be used according to these assays include Ku812, originally established from a patient with chronic myelogenous leukemia. It is an immature prebasophilic cell line that can be induced to differentiate into mature basophils. See, Kishi et al., Leuk Res. 9: 381-390 (1985); Blom et al., Eur J Immunol. 22: 2025-32 (1992), where the contents of each are herein incorporated by reference in its entirety. | |
| 49 | ATF-2 in CTLL-2 | final_assay_desc | final_assay_embodiment |
| 50 | Bone marrow cell proliferation (fibronectin enhanced) | Assay for measuring regulation of proliferation of mouse bone marrow cells (in the presence or absence of exogenous Stem Cell Factor (SCF)) on a fibronectin extracellular matrix. Mouse bone marrow cells are plated onto 96-well fibronectin fragment coated plates in 0.2 ml of serum-free medium. Secreted protein factors (test factors) are tested with appropriate negative controls in the presence and absence of SCF (5.0 ng/ml), where secreted test factor supernates represent 10% of the total assay volume. The cells are grown for 7 days. The number of proliferating cells within the wells is quantitated by measuring thymidine incorporation into cellular DNA. This and similar assays may be used or routinely modified to assess the ability of polypeptides of the invention (including antibodies and agonists or antagonists of the invention) to regulate proliferation of bone marrow cells. Interactions between adhesion receptors on progenitor cells and their extracellular matrix ligands are essential for the control of hematopoiesis in bone marrow stroma. These interactions may help retain CD34+ hematopoietic progenitor cells within the an appropriate bone marrow environment, and adhesive interactions can also provide important costimulatory signals. As the ability of stem cells to undergo self-renewal in vitro is dependent upon their interaction with the stromal cells and the extracellular matrix (ECM), this assay identify factors which integrate with the ECM environment and are important for stimulating stem cell self-renewal. | |
| 51 | Calcium flux in chondrocytes | Assays for measuring calcium flux are well-known in the art and may be used or routinely modified to assess the ability of polypeptides of the invention (including antibodies and agonists or antagonists of the invention) to mobilize calcium. Cells normally have very low concentrations of cytosolic calcium compared to much higher extracellular calcium. Extracellular factors can cause an influx of calcium, leading to activation of calcium responsive signaling pathways and alterations in cell functions. Exemplary assays that may be used or routinely modified to measure calcium flux in chondrocytes include assays disclosed in: Asada S, et al., Inflamm Res, 50(1): 19-23 (2001); Schwartz Z, et al., J Bone Miner Res, 6(7): 709-718 (1991); Iannotti J P, et al., J Bone Joint Surg Am, 67(1): 113-120 (1985); Sullivan E., et al., Methods Mol Biol 1999; 114: 125-133 (1999), the contents of each of which is herein | Preferred embodiments of the invention include using polypeptides of the invention (or antibodies, agonists, or antagonists thereof) in detection, diagnosis, prevention, and/or treatment of Bone and Cartilage Diseases, including but not limited to Arthritis, Cartilige repair, Bone Repair, Osteoporosis, and related tumors including chondrosarcomas, chondroblastomas, and chondromas. |

TABLE 1E.2-continued

| Biological Activity No. | Biological Activity | Exemplary Activity Assay | Preferred Indication |
|---|---|---|---|
| | | incorporated by reference in its entirety. Cells that may be used according to these assays are publicly available (e.g., through the ATCC ™) and/or may be routinely generated. Exemplary cells that may be used according to these assays include bovine chondrocytes. | |
| 52 | Calcium flux in immune cells (such as monocytes) | Assays for measuring calcium flux are well-known in the art and may be used or routinely modified to assess the ability of polypeptides of the invention (including antibodies and agonists or antagonists of the invention) to mobilize calcium. Cells normally have very low concentrations of cytosolic calcium compared to much higher extracellular calcium. Extracellular factors can cause an influx of calcium, leading to activation of calcium responsive signaling pathways and alterations in cell functions. Exemplary assays that may be used or routinely modified to measure calcium flux in immune cells (such as monocytes) include assays disclosed in: Chan, C C, et al., J Pharmacol Exp Ther, 269(3): 891-896 (1994); Andersson, K, et al., Cytokine, 12(12): 1784-1787 (2000); Scully, S P, et al., J Clin Invest, 74(2) 589-599 (1984); and, Sullivan, E, et al., Methods Mol Biol, 114: 125-133 (1999), the contents of each of which is herein incorporated by reference in its entirety. Cells that may be used according to these assays are publicly available (e.g., through the ATCC ™) and/or may be routinely generated. Exemplary cells that may be used according to these assays include the THP-1 monocyte cell line. | Preferred embodiments of the invention include using polypeptides of the invention (or antibodies, agonists, or antagonists thereof) in detection, diagnosis, prevention, and/or treatment of Infection, Inflammation, Atherosclerosis, Hypersensitivity, and Leukemias |
| 53 | Caspase (+camptothecin) in SW480 | | |
| 54 | Caspase (+paclitaxel) in SW480 | | |
| 55 | CD152 in Human T cells | | |
| 56 | CD69 in Human T cells | | |
| 57 | CXCR4 in HT1080 | | |
| 58 | CXCR4 in SW480 | | |
| 59 | Endothelial Cell Apoptosis | Caspase Apoptosis. Assays for caspase apoptosis are well known in the art and may be used or routinely modified to assess the ability of polypeptides of the invention (including antibodies and agonists or antagonists of the invention) to promote caspase protease-mediated apoptosis. Induction of apoptosis in endothelial cells supporting the vasculature of tumors is associated with tumor regression due to loss of tumor blood supply. Exemplary assays for caspase apoptosis that may be used or routinely modified to test capase apoptosis activity of polypeptides of the invention (including antibodies and agonists or antagonists of the invention) include the assays disclosed in Lee et al., FEBS Lett 485(2-3): 122-126 (2000); Nor et al., J Vasc Res 37(3): 209-218 (2000); and Karsan and Harlan, J Atheroscler Thromb 3(2): 75-80 (1996); the contents of each of which are herein incorporated by reference in its entirety. Endothelial cells that may be used according to these assays are publicly available (e.g., through commercial sources). Exemplary endothelial cells that may be used according to these assays include bovine aortic endothelial cells | A highly preferred embodiment of the invention includes a method for stimulating endothelial cell growth. An alternative highly preferred embodiment of the invention includes a method for inhibiting endothelial cell growth. A highly preferred embodiment of the invention includes a method for stimulating endothelial cell proliferation. An alternative highly preferred embodiment of the invention includes a method for inhibiting endothelial cell proliferation. A highly preferred embodiment of the invention includes a method for stimulating apoptosis of endothelial cells. An alternative highly preferred embodiment of the invention includes a method for inhibiting (e.g., decreasing) apoptosis of endothelial cells. A highly preferred embodiment of the invention includes a method for stimulating angiogenisis. An alternative highly preferred embodiment of the invention includes a method for inhibiting angiogenesis. A highly preferred embodiment of the invention includes a method for reducing cardiac hypertrophy. An alternative highly preferred embodiment of the invention includes a method for inducing cardiac hypertrophy. Highly preferred indications include neoplastic diseases (e.g., as described below under "Hyperproliferative |

TABLE 1E.2-continued

| Biological Activity No. | Biological Activity | Exemplary Activity Assay | Preferred Indication |
|---|---|---|---|
| | | (bAEC), which are an example of endothelial cells which line blood vessels and are involved in functions that include, but are not limited to, angiogenesis, vascular permeability, vascular tone, and immune cell extravasation. | Disorders"), and disorders of the cardiovascular system (e.g., heart disease, congestive heart failure, hypertension, aortic stenosis, cardiomyopathy, valvular regurgitation, left ventricular dysfunction, atherosclerosis and atherosclerotic vascular disease, diabetic nephropathy, intracardiac shunt, cardiac hypertrophy, myocardial infarction, chronic hemodynamic overload, and/or as described below under "Cardiovascular Disorders"). Highly preferred indications include cardiovascular, endothelial and/or angiogenic disorders (e.g., systemic disorders that affect vessels such as diabetes mellitus, as well as diseases of the vessels themselves, such as of the arteries, capillaries, veins and/or lymphatics). Highly preferred are indications that stimulate angiogenesis and/or cardiovascularization. Highly preferred are indications that inhibit angiogenesis and/or cardiovascularization. Highly preferred indications include antiangiogenic activity to treat solid tumors, leukemias, and Kaposi''s sarcoma, and retinal disorders. Highly preferred indications include neoplasms and cancer, such as, Kaposi''s sarcoma, hemangioma (capillary and cavernous), glomus tumors, telangiectasia, bacillary angiomatosis, hemangioendothelioma, angiosarcoma, haemangiopericytoma, lymphangioma, lymphangiosarcoma. Highly preferred indications also include cancers such as, prostate, breast, lung, colon, pancreatic, esophageal, stomach, brain, liver, and urinary cancer. Preferred indications include benign dysproliferative disorders and pre-neoplastic conditions, such as, for example, hyperplasia, metaplasia, and/or dysplasia. Highly preferred indications also include arterial disease, such as, atherosclerosis, hypertension, coronary artery disease, inflammatory vasculitides, Reynaud''s disease and Reynaud''s phenomenom, aneurysms, restenosis; venous and lymphatic disorders such as thrombophlebitis, lymphangitis, and lymphedema; and other vascular disorders such as peripheral vascular disease, and cancer. Highly preferred indications also include trauma such as wounds, burns, and injured tissue (e.g., vascular injury such as, injury resulting from balloon angioplasty, and atheroschlerotic lesions), implant fixation, scarring, ischemia reperfusion injury, rheumatoid arthritis, cerebrovascular disease, renal diseases such as acute renal failure, and osteoporosis. Additional highly preferred indications include stroke, graft rejection, diabetic or other retinopathies, thrombotic and coagulative disorders, vascularitis, lymph angiogenesis, sexual disorders, age-related macular degeneration, and treatment/ prevention of endometriosis and related conditions. Additional highly preferred indications include fibromas, heart disease, cardiac arrest, heart valve disease, and vascular disease. Preferred indications include blood disorders (e.g., as described below under "Immune Activity", "Blood-Related Disorders", and/or "Cardiovascular Disorders"). Preferred indications include autoimmune diseases (e.g., rheumatoid arthritis, systemic lupus erythematosis, multiple sclerosis and/or as described below) and immunodeficiencies (e.g., as described below). Additional preferred indications include inflammation and inflammatory disorders (such as acute and chronic inflammatory diseases, e.g., |

TABLE 1E.2-continued

| Biological Activity No. | Biological Activity | Exemplary Activity Assay | Preferred Indication |
|---|---|---|---|
| | | | inflammatory bowel disease and Crohn's disease), and pain management. |
| 60 | Glucose Production in H4IIE | | |
| 61 | Hexosaminidase in RBL-2H3 | | |
| 62 | HLA-DR in Human T cells | | |
| 63 | ICAM in Normal Human Bronchial Epitheliae | | |
| 64 | ICAM in OE19 | | |
| 65 | IFNg in Human T-cell 293T | | |
| 66 | IFNg in Human T-cell 2B9 | | |
| 67 | IgG in Human B cells | | |
| 68 | IgG in Human B cells SAC | | |
| 69 | IL-10 in Human T-cell 293T | | |
| 70 | IL-10 in Human T-cell 2B9 | | |
| 71 | IL-13 in HMC | | |
| 72 | IL-13 in Human T cells | | |
| 73 | IL-2 in Human T cells | | |
| 74 | IL-2 in Human T-cell 293T | | |
| 75 | IL-4 in HMC | | |
| 76 | IL-6 in HUVEC | | |
| 77 | IL-8 in Normal Human Bronchial Epitheliae | | |
| 78 | IL-8 in SW480 | | |
| 79 | Inhibition of adipocyte ERK signaling pathway. | Kinase assay: measures the phosphorylation of Elk-1, an indication of activation of extracellular signal regulated kinase (ERK). ERK pathway regulates cell growth, proliferation and differentiation. Cells were pretreated with SID supernatants for 15-18 hours, and then 100 nM of insulin was added to stimulate ERK kinase. Phosphorylation of Elk-1 was measured after a 20 minute incubation. Pre-adipocytes that may be used according to these assays are publicly available (e.g., through the ATCC ™) and/or may be routinely generated. Exemplary mouse adipocyte cells that may be used according to these assays include 3T3-L1 cells. 3T3-L1 is an adherent mouse preadipocyte cell line that is a continuous substrain of 3T3 fibroblast cells developed through clonal isolation and undergo a pre-adipocyte to adipose-like conversion under appropriate differentiation conditions known in the art. Cells were differentiated to an adipose-like state before being used in the screen. See Green et al., Cell 3: 127-133 (1974), the contents of which are herein incorporated by reference in its entirety. | |
| 80 | Inhibition of squalene synthetase gene transcription. | Reporter Assay: construct contains regulatory and coding sequence of squalene synthetase, the first specific enzyme in the cholesterol biosynthetic pathway. See Jiang, et al., J. Biol. Chem. 268: 12818-128241 (993), the contents of which are herein incorporated by reference in its entirety. Cells were treated with SID supernatants, and SEAP activity was measured after 72 hours. HepG2 is a human hepatocellular carcinoma cell line (ATCC ™ HB-8065). See Knowles et al., Science. 209: 497-9 (1980), the contents of | |

TABLE 1E.2-continued

| Biological Activity No. | Biological Activity | Exemplary Activity Assay | Preferred Indication |
|---|---|---|---|
| | | which are herein incorporated by reference in its entirety. | |
| 81 | Insulin Secretion | Assays for measuring secretion of insulin are well-known in the art and may be used or routinely modified to assess the ability of polypeptides of the invention (including antibodies and agonists or antagonists of the invention) to stimulate insulin secretion. For example, insulin secretion is measured by FMAT using anti-rat insulin antibodies. Insulin secretion from pancreatic beta cells is upregulated by glucose and also by certain proteins/peptides, and disregulation is a key component in diabetes. Exemplary assays that may be used or routinely modified to test for stimulation of insulin secretion (from pancreatic cells) by polypeptides of the invention (including antibodies and agonists or antagonists of the invention) include assays disclosed in: Shimizu, H., et al., Endocr J, 47(3): 261-9 (2000); Salapatek, A. M., et al., Mol Endocrinol, 13(8): 1305-17 (1999); Filipsson, K., et al., Ann N Y Acad Sci, 865: 441-4 (1998); Olson, L. K., et al., J Biol Chem, 271(28): 16544-52 (1996); and, Miraglia S et. al., Journal of Biomolecular Screening, 4: 193-204 (1999), the contents of each of which is herein incorporated by reference in its entirety. Pancreatic cells that may be used according to these assays are publicly available (e.g., through the ATCC ™) and/or may be routinely generated. Exemplary pancreatic cells that may be used according to these assays include HITT15 Cells. HITT15 are an adherent epithelial cell line established from Syrian hamster islet cells transformed with SV40. These cells express glucagon, somatostatin, and glucocorticoid receptors. The cells secrete insulin, which is stimulated by glucose and glucagon and suppressed by somatostatin or glucocorticoids. ATTC# CRL-1777 Refs: Lord and Ashcroft. Biochem. J. 219: 547-551; Santerre et al. Proc. Natl. Acad. Sci. USA 78: 4339-4343, 1981. | A highly preferred indication is diabetes mellitus. An additional highly preferred indication is a complication associated with diabetes (e.g., diabetic retinopathy, diabetic nephropathy, kidney disease (e.g., renal failure, nephropathy and/or other diseases and disorders as described in the "Renal Disorders" section below), diabetic neuropathy, nerve disease and nerve damage (e.g., due to diabetic neuropathy), blood vessel blockage, heart disease, stroke, impotence (e.g., due to diabetic neuropathy or blood vessel blockage), seizures, mental confusion, drowsiness, nonketotic hyperglycemic-hyperosmolar coma, cardiovascular disease (e.g., heart disease, atherosclerosis, microvascular disease, hypertension, stroke, and other diseases and disorders as described in the "Cardiovascular Disorders" section below), dyslipidemia, endocrine disorders (as described in the "Endocrine Disorders" section below), neuropathy, vision impairment (e.g., diabetic retinopathy and blindness), ulcers and impaired wound healing, and infection (e.g., infectious diseases and disorders as described in the "Infectious Diseases" section below, especially of the urinary tract and skin), carpal tunnel syndrome and Dupuytren's contracture). An additional highly preferred indication is obesity and/or complications associated with obesity. Additional highly preferred indications include weight loss or alternatively, weight gain. Additional highly preferred indications are complications associated with insulin resistance. |
| 82 | MCP-1 in Eol-1 | | |
| 83 | MCP-1 in HUVEC | | |
| 84 | MIP-1a in HMC | | |
| 85 | Myoblast cell proliferation | Assays for muscle cell proliferation are well known in the art and may be used or routinely modified to assess the ability of polypeptides of the invention (including antibodies and agonists or antagonists of the invention) to stimulate or inhibit myoblast cell proliferation. Exemplary assays for myoblast cell proliferation that may be used or routinely modified to test activity of polypeptides and antibodies of the invention (including agonists or antagonists of the invention) include, for example, assays disclosed in: Soeta, C., et al. "Possible role for the c-ski gene in the proliferation of myogenic cells in regenerating skeletal muscles of rats" Dev Growth Differ April; 43(2): 155-64 (2001); Ewton D Z, et al., "IGF binding proteins-4, -5 and -6 may play specialized roles during L6 myoblast proliferation and differentiation" J Endocrinol March; 144(3): 539-53 (1995); and, Pampusch M S, et al., "Effect of transforming growth factor beta on proliferation of L6 and embryonic porcine myogenic cells" J Cell Physiol June; 143(3): 524-8 (1990); the contents of each of which are herein | Highly preferred indications include diabetes, myopathy, muscle cell atrophy, cancers of muscle (such as, rhabdomyoma, and rhabdosarcoma), cardiovascular disorders (such as congestive heart failure, cachexia, myxomas, fibromas, congenital cardiovascular abnormalities, heart disease, cardiac arrest, heart valve disease, vascular disease, and also as described below under "Cardiovascular Disorders"), stimulating myoblast proliferation, and inhibiting myoblast proliferation. |

TABLE 1E.2-continued

| Biological Activity No. | Biological Activity | Exemplary Activity Assay | Preferred Indication |
|---|---|---|---|
| | | incorporated by reference in their entirety. Exemplary myoblast cells that may be used according to these assays include the rat myoblast L6 cell line. Rat myoblast L6 cells are an adherent rat myoblast cell line, isolated from primary cultures of rat thigh muscle, that fuse to form multinucleated myotubes and striated fibers after culture in differentiation media. | |
| 86 | Production of GM-CSF | GM-CSF FMAT. GM-CSF is expressed by activated T cells, macrophages, endothelial cells, and fibroblasts. GM-CSF regulates differentiation and proliferation of granulocytes-macrophage progenitors and enhances antimicrobial activity in neutrophils, monocytes and macrophage. Additionally, GM-CSF plays an important role in the differentiation of dendritic cells and monocytes, and increases antigen presentation. GM-CSF is considered to be a proinflammatory cytokine. Assays for immunomodulatory proteins that promote the production of GM-CSF are well known in the art and may be used or routinely modified to assess the ability of polypeptides of the invention (including antibodies and agonists or antagonists of the invention) to mediate immunomodulation and modulate the growth and differentiation of leukocytes. Exemplary assays that test for immunomodulatory proteins evaluate the production of cytokines, such as GM-CSF, and the activation of T cells. Such assays that may be used or routinely modified to test immunomodulatory activity of polypeptides of the invention (including antibodies and agonists or antagonists of the invention) include the assays disclosed in Miraglia et al., J Biomolecular Screening 4: 193-204 (1999); Rowland et al., “Lymphocytes: a practical approach” Chapter 6: 138-160 (2000); and Ye et al., J Leukoc Biol (58(2): 225-233, the contents of each of which are herein incorporated by reference in its entirety. Natural killer cells that may be used according to these assays are publicly available (e.g., through the ATCC ™) or may be isolated using techniques disclosed herein or otherwise known in the art. Natural killer (NK) cells are large granular lymphocytes that have cytotoxic activity but do bind antigen. NK cells show antibody-independent killing of tumor cells and also recognize antibody bound on target cells, via NK Fc receptors, leading to cell-mediated cytotoxicity. | A highly preferred embodiment of the invention includes a method for stimulating the production of GM-CSF. An alternative highly preferred embodiment of the invention includes a method for inhibiting the production of GM-CSF. Highly preferred indications include inflammation and inflammatory disorders. An additional highly preferred indication is infection (e.g., as described below under “Infectious Disease”. Highly preferred indications include blood disorders (e.g., neutropenia (and the prevention of neutropenia (e.g., in HIV infected patients), and/or as described below under “Immune Activity”, “Blood-Related Disorders”, and/or “Cardiovascular Disorders”). Highly preferred indications also include autoimmune diseases (e.g., rheumatoid arthritis, systemic lupus erythematosis, multiple sclerosis and/or as described below) and immunodeficiencies (e.g., as described below). Additional highly preferred indications include asthma. Highly preferred indications include neoplastic diseases (e.g., leukemia (e.g., acute lymphoblastic leukemia, and acute myelogenous leukemia), lymphoma (e.g., non-Hodgkin’’s lymphoma and Hodgkin’’s disease), and/or as described below under “Hyperproliferative Disorders”). Highly preferred indications include neoplasms and cancers, such as, leukemia, lymphoma, melanoma, and prostate, breast, lung, colon, pancreatic, esophageal, stomach, brain, liver and urinary cancer. Other preferred indications include benign dysproliferative disorders and pre-neoplastic conditions, such as, for example, hyperplasia, metaplasia, and/or dysplasia. Highly preferred indications include: suppression of immune reactions to transplanted organs and tissues (e.g., bone marrow transplant); accelerating myeloid recovery; and mobilizing hematopoietic progenitor cells. Preferred indications include boosting a T cell-mediated immune response, and alternatively, suppressing a T cell-mediated immune response. Preferred indications include anemia, pancytopenia, leukopenia, thrombocytopenia, acute lymphocytic anemia (ALL), plasmacytomas, multiple myeloma, Burkitt’s lymphoma, arthritis, AIDS, granulomatous disease, inflammatory bowel disease, sepsis, neutrophilia, psoriasis, hemophilia, hypercoagulation, diabetes mellitus, endocarditis, meningitis, Lyme Disease, and allergy. |
| 87 | Production of ICAM in endothelial cells (such as human umbilical vein endothelial cells (HUVEC)) | Endothelial cells, which are cells that line blood vessels, and are involved in functions that include, but are not limited to, angiogenesis, vascular permeability, vascular tone, and immune cell extravasation. Exemplary endothelial cells that may be used in ICAM production assays include human umbilical vein endothelial cells (HUVEC), and are available from commercial sources. The expression of ICAM (CD54), a intergral membrane protein, can be upregulated by cytokines or other factors, and ICAM | Highly preferred indications include inflammation (acute and chronic), restnosis, atherosclerosis, asthma and allergy. Highly preferred indications include inflammation and inflammatory disorders, immunological disorders, neoplastic disorders (e.g. cancer/tumorigenesis), and cardiovascular disorders (such as described below under “Immune Activity”, “Blood-Related Disorders”, “Hyperproliferative Disorders” and/or “Cardiovascular Disorders”). Highly preferred indications include neoplasms and cancers such as, for example, leukemia, |

TABLE 1E.2-continued

| Biological Activity No. | Biological Activity | Exemplary Activity Assay | Preferred Indication |
|---|---|---|---|
| | | expression is important in mediating immune and endothelial cell interactions leading to immune and inflammatory responses. Assays for measuring expression of ICAM-1 are well-known in the art and may be used or routinely modified to assess the ability of polypeptides of the invention (including antibodies and agonists or antagonists of the invention) to regulate ICAM-1 expression. Exemplary assays that may be used or routinely modified to measure ICAM-1 expression include assays disclosed in: Rolfe B E, et al., Atherosclerosis, 149(1): 99-110 (2000); Panettieri R A Jr, et al., J Immunol, 154(5): 2358-2365 (1995); and, Grunstein M M, et al., Am J Physiol Lung Cell Mol Physiol, 278(6): L1154-L1163 (2000), the contents of each of which is herein incorporated by reference in its entirety. | lymphoma, melanoma, renal cell carcinoma, and prostate, breast, lung, colon, pancreatic, esophageal, stomach, brain, liver and urinary cancer. Other preferred indications include benign dysproliferative disorders and pre-neoplastic conditions, such as, for example, hyperplasia, metaplasia, and/or dysplasia. |
| 88 | Production of ICAM-1 | Assays for measuring expression of ICAM-1 are well-known in the art and may be used or routinely modified to assess the ability of polypeptides of the invention (including antibodies and agonists or antagonists of the invention) to regulate ICAM-1 expression. Exemplary assays that may be used or routinely modified to measure ICAM-1 expression include assays disclosed in: Rolfe B E, et al., Atherosclerosis, 149(1): 99-110 (2000); Panettieri R A Jr, et al., J Immunol, 154(5): 2358-2365 (1995); and, Grunstein M M, et al., Am J Physiol Lung Cell Mol Physiol, 278(6): L1154-L1163 (2000), the contents of each of which is herein incorporated by reference in its entirety. Cells that may be used according to these assays are publicly available (e.g., through the ATCC ™) and/or may be routinely generated. Exemplary cells that may be used according to these assays include Aortic Smooth Muscle Cells (AOSMC); such as bovine AOSMC. Exemplary cells that may be used according to these assays include microvascular endothelial cells (MVEC). | Preferred embodiments of the invention include using polypeptides of the invention (or antibodies, agonists, or antagonists thereof) in detection, diagnosis, prevention, and/or treatment of Vascular Disease, Atherosclerosis, Restenosis, Stroke, and Asthma. |
| 89 | Production of IFNgamma using a T cells | IFNgamma FMAT. IFNg plays a central role in the immune system and is considered to be a proinflammatory cytokine. IFNg promotes TH1 and inhibits TH2 differentiation; promotes IgG2a and inhibits IgE secretion; induces macrophage activation; and increases MHC expression. Assays for immunomodulatory proteins produced by T cells and NK cells that regulate a variety of inflammatory activities and inhibit TH2 helper cell functions are well known in the art and may be used or routinely modified to assess the ability of polypeptides of the invention (including antibodies and agonists or antagonists of the invention) to mediate immunomodulation, regulate inflammatory activities, modulate TH2 helper cell function, and/or mediate humoral or cell-mediated immunity. Exemplary assays that test for immunomodulatory proteins evaluate the production of cytokines, such as Interferon gamma (IFNg), and the activation of T cells. Such assays that may be used or routinely modified to test immunomodulatory activity of polypeptides of the invention (including antibodies and agonists or antagonists of the invention) include the assays disclosed in Miraglia et al., J Biomolecular Screening 4: 193-204 | A highly preferred embodiment of the invention includes a method for stimulating the production of IFNg. An alternative highly preferred embodiment of the invention includes a method for inhibiting the production of IFNg. Highly preferred indications include blood disorders (e.g., as described below under "Immune Activity", "Blood-Related Disorders", and/or ""Cardiovascular Disorders""), and infection (e.g., viral infections, tuberculosis, infections associated with chronic granulomatosus disease and malignant osteoporosis, and/or as described below under "Infectious Disease"). Highly preferred indications include autoimmune disease (e.g., rheumatoid arthritis, systemic lupus erythematosis, multiple sclerosis and/or as described below), immunodeficiency (e.g., as described below), boosting a T cell-mediated immune response, and suppressing a T cell-mediated immune response. Additional highly preferred indications include inflammation and inflammatory disorders. Additional preferred indications include idiopathic pulmonary fibrosis. Highly preferred indications include neoplastic diseases (e.g., leukemia, lymphoma, melanoma, and/or as described below under "Hyperproliferative Disorders"). Highly preferred indications include neoplasms and cancers, such as, for example, leukemia, |

TABLE 1E.2-continued

| Biological Activity No. | Biological Activity | Exemplary Activity Assay | Preferred Indication |
|---|---|---|---|
| | | (1999); Rowland et al., ""Lymphocytes: a practical approach"" Chapter 6: 138-160 (2000); Gonzalez et al., J Clin Lab Anal 8(5): 225-233 (1995); Billiau et al., Ann NY Acad Sci 856: 22-32 (1998); Boehm et al., Annu Rev Immunol 15: 749-795 (1997), and Rheumatology (Oxford) 38(3): 214-20 (1999), the contents of each of which are herein incorporated by reference in its entirety. Human T cells that may be used according to these assays may be isolated using techniques disclosed herein or otherwise known in the art. Human T cells are primary human lymphocytes that mature in the thymus and express a T Cell receptor and CD3, CD4, or CD8. These cells mediate humoral or cell-mediated immunity and may be preactivated to enhance responsiveness to immunomodulatory factors. | lymphoma, melanoma, and prostate, breast, lung, colon, pancreatic, esophageal, stomach, brain, liver and urinary cancer. Other preferred indications include benign dysproliferative disorders and pre-neoplastic conditions, such as, for example, hyperplasia, metaplasia, and/or dysplasia. Preferred indications include anemia, pancytopenia, leukopenia, thrombocytopenia, Hodgkin's disease, acute lymphocytic anemia (ALL), plasmacytomas, multiple myeloma, Burkitt's lymphoma, arthritis, AIDS, granulomatous disease, inflammatory bowel disease, sepsis, neutropenia, neutrophilia, psoriasis, suppression of immune reactions to transplanted organs and tissues, hemophilia, hypercoagulation, diabetes mellitus, endocarditis, meningitis, Lyme Disease, asthma and allergy. |
| 90 | Production of IFNgamma using Natural Killer cells | IFNgamma FMAT. IFNg plays a central role in the immune system and is considered to be a proinflammatory cytokine. IFNg promotes TH1 and inhibits TH2; promotes IgG2a and inhibits IgE; induces macrophage activation; and increases MHC expression. Assays for immunomodulatory proteins produced by T cells and NK cells that regulate a variety of inflammatory activities and inhibit TH2 helper cell functions are well known in the art and may be used or routinely modified to assess the ability of polypeptides of the invention (including antibodies and agonists or antagonists of the invention) to mediate immunomodulation, regulate inflammatory activities, modulate TH2 helper cell function, and/or mediate humoral or cell-mediated immunity. Exemplary assays that test for immunomodulatory proteins evaluate the production of cytokines, such as Interferon gamma (IFNg), and the activation of T cells. Such assays that may be used or routinely modified to test immunomodulatory activity of polypeptides of the invention (including antibodies and agonists or antagonists of the invention) include the assays disclosed in Miraglia et al., J Biomolecular Screening 4: 193-204 (1999); Rowland et al., "Lymphocytes: a practical approach" Chapter 6: 138-160 (2000); Gonzalez et al., J Clin Lab Anal 8(5): 225-233 (1995); Billiau et al., Ann NY Acad Sci 856: 22-32 (1998); Boehm et al., Annu Rev Immunol 15: 749-795 (1997), and Rheumatology (Oxford) 38(3): 214-20 (1999), the contents of each of which are herein incorporated by reference in its entirety. Natural Killer (NK) cells that may be used according to these assays are publicly available (e.g., through the ATCC ™) or may be isolated using techniques disclosed herein or otherwise known in the art. Natural killer (NK) cells are large granular lymphocytes that have cytotoxic activity but do bind antigen. NK cells show antibody-independent killing of tumor cells and also recognize antibody bound on target cells, via NK Fc receptors, leading to cell-mediated cytotoxicity. | |
| 91 | Production of IL-10 and activation of T-cells. | Assays for production of IL-10 and activation of T-cells are well known in the art and may be used or routinely modified to assess the ability of polypeptides of the invention (including antibodies and agonists or antagonists of the invention) to stimulate | Highly preferred indications include allergy and asthma. Additional highly preferred indications include immune and hematopoietic disorders (e.g., as described below under "Immune Activity", and "Blood-Related Disorders"), autoimmune diseases (e.g., rheumatoid arthritis, |

TABLE 1E.2-continued

| Biological Activity No. | Biological Activity | Exemplary Activity Assay | Preferred Indication |
|---|---|---|---|
| | | or inhibit production of IL-10 and/or activation of T-cells. Exemplary assays that may be used or routinely modified to assess the ability of polypeptides and antibodies of the invention (including agonists or antagonists of the invention) to modulate IL-10 production and/or T-cell proliferation include, for example, assays such as disclosed and/or cited in: Robinson, D S, et al., "Th-2 cytokines in allergic disease" Br Med Bull; 56 (4): 956-968 (2000), and Cohn, et al., "T-helper type 2 cell-directed therapy for asthma" Pharmacology & Therapeutics; 88: 187-196 (2000); the contents of each of which are herein incorporated by reference in their entirety. Exemplary cells that may be used according to these assays include Th2 cells. IL10 secreted from Th2 cells may be measured as a marker of Th2 cell activation. Th2 cells are a class of T cells that secrete IL4, IL10, IL13, IL5 and IL6. Factors that induce differentiation and activation of Th2 cells play a major role in the initiation and pathogenesis of allergy and asthma. Primary T helper 2 cells are generated via in vitro culture under Th2 polarizing conditions using peripheral blood lymphocytes isolated from cord blood. | systemic lupus erythematosis, Crohn"s disease, multiple sclerosis and/or as described below), immunodeficiencies (e.g., as described below), boosting a T cell-mediated immune response, and suppressing a T cell-mediated immune response. |
| 92 | Production of IL-10 and downregulation of immune responses | IL-10 FMAT. Assays for immunomodulatory proteins produced by activated T cells, B cells, and monocytes that exhibit anti-inflammatory activity and downregulate monocyte/macrophage function and expression of cytokines are well known in the art and may be used or routinely modified to assess the ability of the polypeptides of the invention (including antibodies and agonists or antagonists of the invention) to mediate immunomodulation, regulate inflammatory activities, and modulate immune cell function and cytokine production. Exemplary assays that test for immunomodulatory proteins evaluate the production of cytokines, such as IL-10, and the downmodulation of immune responses. Such assays that may be used or routinely modified to test immunomodulatory activity of polypeptides of the invention (including antibodies and agonists or antagonists of the invention) include the assays disclosed in Miraglia et al., J Biomolecular Screening 4: 193-204 (1999); Rowland et al., "Lymphocytes: a practical approach" Chapter 6: 138-160 (2000); and Koning et al., Cytokine 9(6): 427-436 (1997), the contents of each of which are herein incorporated by reference in its entirety. Human T cells that may be used according to these assays may be isolated using techniques disclosed herein or otherwise known in the art. Human T cells are primary human lymphocytes that mature in the thymus and express a T cell receptor and CD3, CD4, or CD8. These cells mediate humoral or cell-mediated immunity and may be preactivated to enhance responsiveness to immunomodulatory factors. | |
| 93 | Production of IL-13 | IL-13 FMAT. IL-13 enhances IgM, IgG, and IgE production and induces FcER1. IL-13 has anti-inflammatory activity on monocytes and macrophages. Assays for immunomodulatory proteins produced by T cells that inhibit activation and release of cytokines by macrophages are well known | |

TABLE 1E.2-continued

| Biological Activity No. | Biological Activity | Exemplary Activity Assay | Preferred Indication |
|---|---|---|---|
| | | in the art and may be used or routinely modified to assess the ability of polypeptides of the invention (including antibodies and agonists or antagonists of the invention) to mediate immunomodulation, regulate cytokine release, stimulate immune cells through the binding of IL-13 and IL-4 receptors, and/or mediate humoral or cell-mediated immunity. Exemplary assays that test for immunomodulatory proteins evaluate the production of cytokines, such as IL-13, the inhibition of cytokines released by macrophages. Such assays that may be used or routinely modified to test immunomodulatory activity of polypeptides of the invention (including antibodies and agonists or antagonists of the invention) include the assays disclosed in Miraglia et al., J Biomolecular Screening 4: 193-204 (1999); Rowland et al., "Lymphocytes: a practical approach" Chapter 6: 138-160 (2000); and Ohshima et al., Blood 92(9): 3338-3345 (1998), the contents of each of which are herein incorporated by reference in its entirety. Human T cells that may be used according to these assays may be isolated using techniques disclosed herein or otherwise known in the art. Human T cells are primary human lymphocytes that mature in the thymus and express a T cell receptor and CD3, CD4, or CD8. These cells mediate humoral or cell-mediated immunity and may be preactivated to enhance responsiveness to immunomodulatory factors. | |
| 94 | Production of IL-13 and activation of T-cells. | Assays for production of IL-13 and activation of T-cells are well known in the art and may be used or routinely modified to assess the ability of polypeptides of the invention (including antibodies and agonists or antagonists of the invention) to stimulate or inhibit production of IL-13 and/or activation of T-cells. Exemplary assays for IL-13 production that may be used or routinely modified to test activity of polypeptides and antibodies of the invention (including agonists or antagonists of the invention) include, for example, assays such as disclosed and/or cited in: Grunig, G, et al., "Requirement for IL-13 independently of IL-4 in Experimental asthma" Science; 282: 2261-2263 (1998), and Wills-Karp M, et al., "Interleukin-13: central mediator of allergic asthma" Science; 282: 2258-2261 (1998); the contents of each of which are herein incorporated by reference in their entirety. Exemplary cells that may be used according to these assays include Th2 cells. IL13, a Th2 type cytokine, is a potent stimulus for mucus production, airway hyper-responsiveness and allergic asthma. Th2 cells are a class of T cells that secrete IL4, IL10, IL13, IL5 and IL6. Factors that induce differentiation and activation of Th2 cells play a major role in the initiation and pathogenesis of allergy and asthma. Primary T helper 2 cells are generated in in vitro culture under Th2 polarizing conditions using peripheral blood lymphocytes isolated from cord blood. | |
| 95 | Production of IL-2 and activation of T cells | IL-2 FMAT. IL-2 is the principal T cell factor that allows T cell expansion and differentiation into effector cells. Assays for immunomodulatory proteins secreted by TH1 cells that promote T cell and NK cell growth and differentiation are well known | |

TABLE 1E.2-continued

| Biological Activity No. | Biological Activity | Exemplary Activity Assay | Preferred Indication |
|---|---|---|---|
| | | in the art and may be used or routinely modified to assess the ability of polypeptides of the invention (including antibodies and agonists or antagonists of the invention) to mediate immunomodulation, promote immune cell growth and differentiation, and/or mediate humoral or cell-mediated immunity. Exemplary assays that test for immunomodulatory proteins evaluate the production of cytokines, such as IL-2, and the activation of T cells. Such assays that may be used or routinely modified to test immunomodulatory activity of polypeptides of the invention (including antibodies and agonists or antagonists of the invention) include the assays disclosed in Miraglia et al., J Biomolecular Screening 4: 193-204 (1999); Rowland et al., “Lymphocytes: a practical approach” Chapter 6: 138-160 (2000); Laduda et al., Immunology 94(4): 496-502 (1998); and Powell et al., Immunol Rev 165: 287-300 (1998), the contents of each of which are herein incorporated by reference in its entirety. Human T cells that may be used according to these assays may be isolated using techniques disclosed herein or otherwise known in the art. Human T cells are primary human lymphocytes that mature in the thymus and express a T cell receptor and CD3, CD4, or CD8. These cells mediate humoral or cell-mediated immunity and may be preactivated to enhance responsiveness to immunomodulatory factors. | |
| 96 | Production of IL-4 | IL-4 FMAT. Assays for immunomodulatory proteins secreted by TH2 cells that stimulate B cells, T cells, macrophages and mast cells and promote polarization of CD4+ cells into TH2 cells are well known in the art and may be used or routinely modified to assess the ability of polypeptides of the invention (including antibodies and agonists or antagonists of the invention) to mediate immunomodulation, stimulate immune cells, modulate immune cell polarization, and/or mediate humoral or cell-mediated immunity. Exemplary assays that test for immunomodulatory proteins evaluate the production of cytokines, such as IL-4, and the stimulation of immune cells, such as B cells, T cells, macrophages and mast cells. Such assays that may be used or routinely modified to test immunomodulatory activity of polypeptides of the invention (including antibodies and agonists or antagonists of the invention) include the assays disclosed in Miraglia et al., J Biomolecular Screening 4: 193-204 (1999); Rowland et al., “Lymphocytes: a practical approach” Chapter 6: 138-160 (2000); Gonzalez et al., J Clin Lab Anal 8(5): 277-283 (1194); Yssel et al., Res Immunol 144(8): 610-616 (1993); Bagley et al., Nat Immunol 1(3): 257-261 (2000); and van der Graaff et al., Rheumatology (Oxford) 38(3): 214-220 (1999), the contents of each of which are herein incorporated by reference in its entirety. Human T cells that may be used according to these assays may be isolated using techniques disclosed herein or otherwise known in the art. Human T cells are primary human lymphocytes that mature in the thymus and express a T cell receptor and CD3, CD4, or CD8. These cells mediate humoral or cell- | A highly preferred embodiment of the invention includes a method for stimulating (e.g., increasing) IL-4 production. An alternative highly preferred embodiment of the invention includes a method for inhibiting (e.g., reducing) IL-4 production. A highly preferred indication includes asthma. A highly preferred indication includes allergy. A highly preferred indication includes rhinitis. Additional highly preferred indications include inflammation and inflammatory disorders. Highly preferred indications include neoplastic diseases (e.g., leukemia, lymphoma, melanoma, and/or as described below under “Hyperproliferative Disorders”). Preferred indications include neoplasms and cancers, such as, for example, leukemia, lymphoma, melanoma, and prostate, breast, lung, colon, pancreatic, esophageal, stomach, brain, liver and urinary cancer. Other preferred indications include benign dysproliferative disorders and pre-neoplastic conditions, such as, for example, hyperplasia, metaplasia, and/or dysplasia. Preferred indications include blood disorders (e.g., as described below under “Immune Activity”, “Blood-Related Disorders”, and/or “Cardiovascular Disorders”). Preferred indications include autoimmune diseases (e.g., rheumatoid arthritis, systemic lupus erythematosis, multiple sclerosis and/or as described below) and immunodeficiencies (e.g., as described below). Preferred indications include anemia, pancytopenia, leukopenia, thrombocytopenia, Hodgkin’s disease, acute lymphocytic anemia (ALL), plasmacytomas, multiple myeloma, Burkitt’s lymphoma, arthritis, AIDS, granulomatous disease, inflammatory bowel disease, sepsis, neutropenia, neutrophilia, psoriasis, suppression of immune reactions to transplanted organs and tissues, hemophilia, hypercoagulation, diabetes |

TABLE 1E.2-continued

| Biological Activity No. | Biological Activity | Exemplary Activity Assay | Preferred Indication |
|---|---|---|---|
| | | mediated immunity and may be preactivated to enhance responsiveness to immunomodulatory factors. | mellitus, endocarditis, meningitis, and Lyme Disease. An additonal preferred indication is infection (e.g., an infectious disease as described below under "Infectious Disease"). |
| 97 | Production of IL-5 | IL-5 FMAT. Assays for immunomodulatory proteins secreted by TH2 cells, mast cells, basophils, and eosinophils that stimulate eosinophil function and B cell Ig production and promote polarization of CD4+ cells into TH2 cells are well known in the art and may be used or routinely modified to assess the ability of polypeptides of the invention (including antibodies and agonists or antagonists of the invention) to mediate immunomodulation, stimulate immune cell function, modulate B cell Ig production, modulate immune cell polarization, and/or mediate humoral or cell-mediated immunity. Exemplary assays that test for immunomodulatory proteins evaluate the production of cytokines, such as IL-5, and the stimulation of eosinophil function and B cell Ig production. Such assays that may be used or routinely modified to test immunomodulatory activity of polypeptides of the invention (including antibodies and agonists or antagonists of the invention) include the assays disclosed in Miraglia et al., J Biomolecular Screening 4: 193-204 (1999); Rowland et al., ""Lymphocytes: a practical approach"" Chapter 6: 138-160 (2000); Ohshima et al., Blood 92(9): 3338-3345 (1998); Jung et al., Eur J Immunol 25(8): 2413-2416 (1995); Mori et al., J Allergy Clin Immunol 106(1 Pt 2): 558-564 (2000); and Koning et al., Cytokine 9(6): 427-436 (1997), the contents of each of which are herein incorporated by reference in its entirety. Human T cells that may be used according to these assays may be isolated using techniques disclosed herein or otherwise known in the art. Human T cells are primary human lymphocytes that mature in the thymus and express a T cell receptor and CD3, CD4, or CD8. These cells mediate humoral or cell-mediated immunity and may be preactivated to enhance responsiveness to immunomodulatory factors. | A highly preferred embodiment of the invention includes a method for inhibiting (e.g., reducing) IL-5 production. An alternative highly preferred embodiment of the invention includes a method for stimulating (e.g., increasing) IL-5 production. A highly preferred embodiment of the invention includes a method for stimulating (e.g., increasing) immunoglobulin production. An alternative highly preferred embodiment of the invention includes a method for inhibiting (e.g., decreasing) immunoglobulin production. A highly preferred indication includes allergy. A highly preferred indication includes asthma. A highly preferred indication includes rhinitis. An additional highly preferred indication is infection (e.g., an infectious disease as described below under ""Infectious Disease""), and inflammation and inflammatory disorders. Preferred indications include blood disorders (e.g., as described below under "Immune Activity", "Blood-Related Disorders", and/or ""Cardiovascular Disorders""). Preferred indications include autoimmune diseases (e.g., rheumatoid arthritis, systemic lupus erythematosis, multiple sclerosis and/or as described below) and immunodeficiencies (e.g., as described below). Preferred indications include neoplastic diseases (e.g., leukemia, lymphoma, melanoma, and/or as described below under "Hyperproliferative Disorders"). Preferred indications include neoplasms and cancers, such as, leukemia, lymphoma, melanoma, and prostate, breast, lung, colon, pancreatic, esophageal, stomach, brain, liver and urinary cancer. Other preferred indications include benign dysproliferative disorders and pre-neoplastic conditions, such as, for example, hyperplasia, metaplasia, and/or dysplasia. Preferred indications include anemia, pancytopenia, leukopenia, thrombocytopenia, leukemias, Hodgkin's disease, acute lymphocytic anemia (ALL), plasmacytomas, multiple myeloma, Burkitt's lymphoma, arthritis, AIDS, granulomatous disease, inflammatory bowel disease, sepsis, neutropenia, neutrophilia, psoriasis, immune reactions to transplanted organs and tissues, hemophilia, hypercoagulation, diabetes mellitus, endocarditis, meningitis, and Lyme Disease. |
| 98 | Production of IL-6 | IL-6 FMAT. IL-6 is produced by T cells and has strong effects on B cells. IL-6 participates in IL-4 induced IgE production and increases IgA production (IgA plays a role in mucosal immunity). IL-6 induces cytotoxic T cells. Deregulated expression of IL-6 has been linked to autoimmune disease, plasmacytomas, myelomas, and chronic hyperproliferative diseases. Assays for immunomodulatory and differentiation factor proteins produced by a large variety of cells where the expression level is strongly regulated by cytokines, growth factors, and hormones are well known in the art and may be used or routinely modified to assess the ability of polypeptides of the invention (including antibodies and agonists or antagonists of the invention) to mediate immunomodulation and differentiation and modulate T cell proliferation and function. Exemplary assays that test for | A highly preferred embodiment of the invention includes a method for stimulating (e.g., increasing) IL-6 production. An alternative highly preferred embodiment of the invention includes a method for inhibiting (e.g., reducing) IL-6 production. A highly preferrred indication is the stimulation or enhancement of mucosal immunity. Highly preferred indications include blood disorders (e.g., as described below under "Immune Activity", "Blood-Related Disorders", and/or ""Cardiovascular Disorders""), and infection (e.g., as described below under "Infectious Disease"). Highly preferred indications include autoimmune diseases (e.g., rheumatoid arthritis, systemic lupus erythematosis, multiple sclerosis and/or as described below) and immunodeficiencies (e.g., as described below). Highly preferred indications also include boosting a B cell-mediated immune response and alternatively suppressing a B cell-mediated immune |

TABLE 1E.2-continued

| Biological Activity No. | Biological Activity | Exemplary Activity Assay | Preferred Indication |
|---|---|---|---|
| | | immunomodulatory proteins evaluate the production of cytokines, such as IL-6, and the stimulation and upregulation of T cell proliferation and functional activities. Such assays that may be used or routinely modified to test immunomodulatory and differentiation activity of polypeptides of the invention (including antibodies and agonists or antagonists of the invention) include assays disclosed in Miraglia et al., J Biomolecular Screening 4: 193-204(1999); Rowland et al., ""Lymphocytes: a practical approach"" Chapter 6: 138-160 (2000); and Verhasselt et al., J Immunol 158: 2919-2925 (1997), the contents of each of which are herein incorporated by reference in its entirety. Human dendritic cells that may be used according to these assays may be isolated using techniques disclosed herein or otherwise known in the art. Human dendritic cells are antigen presenting cells in suspension culture, which, when activated by antigen and/or cytokines, initiate and upregulate T cell proliferation and functional activities. | response. Highly preferred indications include inflammation and inflammatory disorders. Additional highly preferred indications include asthma and allergy. Highly preferred indications include neoplastic diseases (e.g., myeloma, plasmacytoma, leukemia, lymphoma, melanoma, and/or as described below under "Hyperproliferative Disorders"). Highly preferred indications include neoplasms and cancers, such as, myeloma, plasmacytoma, leukemia, lymphoma, melanoma, and prostate, breast, lung, colon, pancreatic, esophageal, stomach, brain, liver and urinary cancer. Other preferred indications include benign dysproliferative disorders and pre-neoplastic conditions, such as, for example, hyperplasia, metaplasia, and/or dysplasia. Preferred indications include anemia, pancytopenia, leukopenia, thrombocytopenia, Hodgkin's disease, acute lymphocytic anemia (ALL), multiple myeloma, Burkitt's lymphoma, arthritis, AIDS, granulomatous disease, inflammatory bowel disease, sepsis, neutropenia, neutrophilia, psoriasis, suppression of immune reactions to transplanted organs and tissues, hemophilia, hypercoagulation, diabetes mellitus, endocarditis, meningitis, and Lyme Disease. An additonal preferred indication is infection (e.g., an infectious disease as described below under ""Infectious Disease""). |
| 99 | Production of IL-8 by by endothelial cells (such as Human Umbilical Cord Endothelial Cells). | Assays measuring production of IL-8 are well known in the art and may be used or routinely modified to assess the ability of polypeptides of the invention (including antibodies and agonists or antagonists of the invention) to regulate production and/or secretion of IL-8. For example, FMAT may be used or routinely modified to assess the ability of polypeptides of the invention (including antibodies and agonists or antagonists of the invention) to regulate production and/or secretion of IL-8 from endothelial cells (such as human umbilical vein endothelial cells (HUVEC)). HUVECs are endothelial cells which line venous blood vessels, and are involved in functions that include, but are not limited to, angiogenesis, vascular permeability, vascular tone, and immune cell extravasation. Endothelial cells play a pivotal role in the initiation and perpetuation of inflammation and secretion of IL-8 may play an important role in recruitment and activation of immune cells such as neutrophils, macrophages, and lymphocytes. | Highly preferred indications include immunological and inflammatory disorders (e.g., such as allergy, asthma, leukemia, etc. and as described below under "Immune Activity", and "Blood-Related Disorders"). Highly preferred indications also includie autoimmune disorders (e.g., rheumatoid arthritis, systemic lupus erythematosis, Crohn''s disease, multiple sclerosis and/or as described below), neoplastic disorders (e.g., organ cancers such as lung, liver, colon cancer, and/or as described below under "Hyperproliferative Disorders"), and cardiovascular disorders (e.g. such as described below under "Cardiovascular Disorders"). Preferred indications include thrombosis, bacteremia and sepsis syndrome and consequent complications (such as acute respiratory distress syndrome and systemic ischemia-reperfusion resulting from septic shock), restnosis and atherosclerosis. |
| 100 | Production of IL-8 by endothelial cells (such as Human Umbilical Cord Endothelial Cells). | Assays measuring production of IL-8 are well known in the art and may be used or routinely modified to assess the ability of polypeptides of the invention (including antibodies and agonists or antagonists of the invention) to regulate production and/or secretion of IL-8. For example, FMAT may be used or routinely modified to assess the ability of polypeptides of the invention (including antibodies and agonists or antagonists of the invention) to regulate production and/or secretion of IL-8 from endothelial cells (such as human umbilical vein endothelial cells (HUVEC)). HUVECs are endothelial cells which line venous blood vessels, and are involved in functions that include, but are not limited to, angiogenesis, vascular permeability, vascular tone, and immune cell extravasation. Endothelial cells play a | |

TABLE 1E.2-continued

| Biological Activity No. | Biological Activity | Exemplary Activity Assay | Preferred Indication |
|---|---|---|---|
| | | pivotal role in the initiation and perpetuation of inflammation and secretion of IL-8 may play an important role in recruitment and activation of immune cells such as neutrophils, macrophages, and lymphocytes. | |
| 101 | Production of IL-8 by immune cells (such as the human EOL-1 eosinophil cells) | Assay that measures the production of the chemokine interleukin-8 (IL-8) from immune cells (such as the EOL-1 human eosinophil cell line) are well known in the art (for example, measurement of IL-8 production by FMAT) and may be used or routinely modified to assess the ability of polypeptides of the invention (including antibodies and agonists or antagonists of the invention) to promote or inhibit. Eosinophils are a type of immune cell important in allergic responses; they are recruited to tissues and mediate the inflammatory response of late stage allergic reaction. IL8 is a strong immunomodulator and may have a potential proinflammatory role in immunological diseases and disorders (such as allergy and asthma). | |
| 102 | Production of IL6 by primary human aortic smooth muscle or normal human dermal fibroblast cells (without or with costimulation with TNFalpha). | Assay to measure regulation of production of Interleukin-6 (IL-6) by either human aortic smooth muscle cells or normal human dermal fibroblasts minus or plus costimulation with TNFalpha (TNFa). Human aortic smooth muscle cells or normal human dermal fibroblasts may be obtained from commercial sources; these cells are important structural and functional components of blood vessels and connective tissue, respectively. Interleukin-6 (IL-6) is a key molecule in chronic inflammation and has been implicated in the progression of arteriosclerosis, stroke, arthritis and other vascular and inflammatory diseases. Deregulated expression of IL-6 has been linked to autoimmune disease, plasmacytomas, myelomas, and chronic hyperproliferative diseases. Assays for immunomodulatory and differentiation factor proteins produced by a large variety of cells where the expression level is strongly regulated by cytokines, growth factors, and hormones are well known in the art and may be used or routinely modified to assess the ability of polypeptides of the invention (including antibodies and agonists or antagonists of the invention) to mediate immunomodulation and production of IL-6. | |
| 103 | Production of MCP-1 | MCP-1 FMAT. Assays for immunomodulatory proteins that are produced by a large variety of cells and act to induce chemotaxis and activation of monocytes and T cells are well known in the art and may be used or routinely modified to assess the ability of polypeptides of the invention (including antibodies and agonists or antagonists of the invention) to mediate immunomodulation, induce chemotaxis, and modulate immune cell activation. Exemplary assays that test for immunomodulatory proteins evaluate the production of cell surface markers, such as monocyte chemoattractant protein (MCP), and the activation of monocytes and T cells. Such assays that may be used or routinely modified to test immunomodulatory and differentiation activity of polypeptides of the invention (including antibodies and agonists or antagonists of the invention) include assays disclosed in Miraglia et al., J Biomolecular | A highly preferred embodiment of the invention includes a method for stimulating (e.g., increasing) MCP-1 production. An alternative highly preferred embodiment of the invention includes a method for inhibiting (e.g., reducing) MCP-1 production. A highly preferred indication is infection (e.g., an infectious disease as described below under "Infectious Disease"). Additional highly preferred indications include inflammation and inflammatory disorders. Preferred indications include blood disorders (e.g., as described below under "Immune Activity", "Blood-Related Disorders", and/or ""Cardiovascular Disorders""). Highly preferred indications include autoimmune diseases (e.g., rheumatoid arthritis, systemic lupus erythematosis, multiple sclerosis and/or as described below) and immunodeficiencies (e.g., as described below). Preferred indications also include anemia, pancytopenia, leukopenia, thrombocytopenia, Hodgkin's disease, acute lymphocytic anemia (ALL), plasmacytomas, |

TABLE 1E.2-continued

| Biological Activity No. | Biological Activity | Exemplary Activity Assay | Preferred Indication |
|---|---|---|---|
| | | Screening 4: 193-204(1999); Rowland et al., ""Lymphocytes: a practical approach"" Chapter 6: 138-160 (2000); Satthaporn and Eremin, J R Coll Surg Ednb 45(1): 9-19 (2001); and Verhasselt et al., J Immunol 158: 2919-2925 (1997), the contents of each of which are herein incorporated by reference in its entirety. Human dendritic cells that may be used according to these assays may be isolated using techniques disclosed herein or otherwise known in the art. Human dendritic cells are antigen presenting cells in suspension culture, which, when activated by antigen and/or cytokines, initiate and upregulate T cell proliferation and functional activities. | multiple myeloma, Burkitt's lymphoma, arthritis, AIDS, granulomatous disease, inflammatory bowel disease, sepsis, neutropenia, neutrophilia, psoriasis, suppression of immune reactions to transplanted organs and tissues, hemophilia, hypercoagulation, diabetes mellitus, endocarditis, meningitis (bacterial and viral), Lyme Disease, asthma, and allergy Preferred indications also include neoplastic diseases (e.g., leukemia, lymphoma, and/or as described below under "Hyperproliferative Disorders"). Highly preferred indications include neoplasms and cancers, such as, leukemia, lymphoma, prostate, breast, lung, colon, pancreatic, esophageal, stomach, brain, liver, and urinary cancer. Other preferred indications include benign dysproliferative disorders and pre-neoplastic conditions, such as, for example, hyperplasia, metaplasia, and/or dysplasia. |
| 104 | Production of MIP1alpha | MIP-1alpha FMAT. Assays for immunomodulatory proteins produced by activated dendritic cells that upregulate monocyte/macrophage and T cell chemotaxis are well known in the art and may be used or routinely modified to assess the ability of polypeptides of the invention (including antibodies and agonists or antagonists of the invention) to mediate immunomodulation, modulate chemotaxis, and modulate T cell differentiation. Exemplary assays that test for immunomodulatory proteins evaluate the production of chemokines, such as macrophage inflammatory protein 1 alpha (MIP-1a), and the activation of monocytes/macrophages and T cells. Such assays that may be used or routinely modified to test immunomodulatory and chemotaxis activity of polypeptides of the invention (including antibodies and agonists or antagonists of the invention) include assays disclosed in Miraglia et al., J Biomolecular Screening 4: 193-204(1999); Rowland et al., ""Lymphocytes: a practical approach"" Chapter 6: 138-160 (2000); Satthaporn and Eremin, J R Coll Surg Ednb 45(1): 9-19 (2001); Drakes et al., Transp Immunol 8(1): 17-29 (2000); Verhasselt et al., J Immunol 158: 2919-2925 (1997); and Nardelli et al., J Leukoc Biol 65: 822-828 (1999), the contents of each of which are herein incorporated by reference in its entirety. Human dendritic cells that may be used according to these assays may be isolated using techniques disclosed herein or otherwise known in the art. Human dendritic cells are antigen presenting cells in suspension culture, which, when activated by antigen and/or cytokines, initiate and upregulate T cell proliferation and functional activities. | A highly preferred embodiment of the invention includes a method for stimulating MIP1a production. An alternative highly preferred embodiment of the invention includes a method for inhibiting (e.g., reducing) MIP1a production. A highly preferred indication is infection (e.g., an infectious disease as described below under "Infectious Disease"). Preferred indications include blood disorders (e.g., as described below under "Immune Activity", "Blood-Related Disorders", and/or ""Cardiovascular Disorders""). Highly preferred indications include autoimmune diseases (e.g., rheumatoid arthritis, systemic lupus erythematosis, multiple sclerosis and/or as described below) and immunodeficiencies (e.g., as described below). Additional highly preferred indications include inflammation and inflammatory disorders. Preferred indications also include anemia, pancytopenia, leukopenia, thrombocytopenia, Hodgkin's disease, acute lymphocytic anemia (ALL), plasmacytomas, multiple myeloma, Burkitt's lymphoma, arthritis, AIDS, granulomatous disease, inflammatory bowel disease, sepsis, neutropenia, neutrophilia, psoriasis, suppression of immune reactions to transplanted organs and tissues, hemophilia, hypercoagulation, diabetes mellitus, endocarditis, meningitis, Lyme Disease, asthma, and allergy. Preferred indications also include neoplastic diseases (e.g., leukemia, lymphoma, and/or as described below under "Hyperproliferative Disorders"). Highly preferred indications include neoplasms and cancers, such as, leukemia, lymphoma, prostate, breast, lung, colon, pancreatic, esophageal, stomach, brain, liver, and urinary cancer. Other preferred indications include benign dysproliferative disorders and pre-neoplastic conditions, such as, for example, hyperplasia, metaplasia, and/or dysplasia. |
| 105 | Production of RANTES | RANTES FMAT. Assays for immunomodulatory proteins that induce chemotaxis of T cells, monocytes, and eosinophils are well known in the art and may be used or routinely modified to assess the ability of polypeptides of the invention (including antibodies and agonists or antagonists of the invention) to mediate immunomodulation, induce chemotaxis, and/or mediate humoral or cell-mediated immunity. Exemplary assays that test for immunomodulatory proteins evaluate the production of cytokines, such as RANTES, and the induction of chemotactic responses | |

TABLE 1E.2-continued

| Biological Activity No. | Biological Activity | Exemplary Activity Assay | Preferred Indication |
|---|---|---|---|
| | | in immune cells. Such assays that may be used or routinely modified to test immunomodulatory activity of polypeptides of the invention (including antibodies and agonists or antagonists of the invention) include the assays disclosed in Miraglia et al., J Biomolecular Screening 4: 193-204 (1999); Rowland et al., "Lymphocytes: a practical approach" Chapter 6: 138-160 (2000): Cocchi et al., Science 270(5243): 1811-1815 (1995); and Robinson et al., Clin Exp Immunol 101(3): 398-407 (1995), the contents of each of which are herein incorporated by reference in its entirety. Human immune cells that may be used according to these assays may be isolated using techniques disclosed herein or otherwise known in the art. | |
| 106 | Production of RANTES in bronchial epithelium cells | RANTES FMAT. Assays for immunomodulatory proteins that induce chemotaxis of T cells, monocytes, and eosinophils are well known in the art and may be used or routinely modified to assess the ability of polypeptides of the invention (including antibodies and agonists or antagonists of the invention) to mediate immunomodulation, induce chemotaxis, and/or mediate humoral or cell-mediated immunity. Exemplary assays that test for immunomodulatory proteins evaluate the production of cytokines, such as RANTES, and the induction of chemotactic responses in immune cells. Such assays that may be used or routinely modified to test immunomodulatory activity of polypeptides of the invention (including antibodies and agonists or antagonists of the invention) include the assays disclosed in Miraglia et al., J Biomolecular Screening 4: 193-204 (1999); Rowland et al., "Lymphocytes: a practical approach" Chapter 6: 138-160 (2000): Cocchi et al., Science 270(5243): 1811-1815 (1995); and Robinson et al., Clin Exp Immunol 101(3): 398-407 (1995), the contents of each of which are herein incorporated by reference in its entirety. Epithelial cells were isolated from bronchia/trachea immediately postmortem from humans who were free of known respiratory diseases. See Wu et al., Am Rev Respir Dis. 132(2): 311-20 (1985), the contents of which are herein incorporated by reference in its entirety. | |
| 107 | Production of RANTES in endothelial cells (such as human umbilical vein endothelial cells (HUVEC)) | RANTES FMAT. Assays for immunomodulatory proteins that induce chemotaxis of T cells, monocytes, and eosinophils are well known in the art and may be used or routinely modified to assess the ability of polypeptides of the invention (including antibodies and agonists or antagonists of the invention) to mediate immunomodulation, induce chemotaxis, and/or mediate humoral or cell-mediated immunity. Exemplary assays that test for immunomodulatory proteins evaluate the production of cytokines, such as RANTES, and the induction of chemotactic responses in immune cells. Such assays that may be used or routinely modified to test immunomodulatory activity of polypeptides of the invention (including antibodies and agonists or antagonists of the invention) include the assays disclosed in Miraglia et al., J Biomolecular Screening 4: 193-204 (1999); Rowland et al., "Lymphocytes: a practical approach" Chapter 6: 138-160 | |

TABLE 1E.2-continued

| Biological Activity No. | Biological Activity | Exemplary Activity Assay | Preferred Indication |
|---|---|---|---|
| | | (2000): Cocchi et al., Science 270(5243): 1811-1815 (1995); and Robinson et al., Clin Exp Immunol 101(3): 398-407 (1995), the contents of each of which are herein incorporated by reference in its entirety. Endothelial cells that may be used according to these assays are publicly available (e.g., through the ATCC ™). Exemplary endothelial cells that may be used according to these assays include human umbilical vein endothelial cells (HUVEC), which are endothelial cells which line venous blood vessels, and are involved in functions that include, but are not limited to, angiogenesis, vascular permeability, vascular tone, and immune cell extravasation. | |
| 108 | Production of TNF alpha by dendritic cells | TNFa FMAT. Assays for immunomodulatory proteins produced by activated macrophages, T cells, fibroblasts, smooth muscle, and other cell types that exert a wide variety of inflammatory and cytotoxic effects on a variety of cells are well known in the art and may be used or routinely modified to assess the ability of polypeptides of the invention (including antibodies and agonists or antagonists of the invention) to mediate immunomodulation, modulate inflammation and cytotoxicity. Exemplary assays that test for immunomodulatory proteins evaluate the production of cytokines such as tumor necrosis factor alpha (TNFa), and the induction or inhibition of an inflammatory or cytotoxic response. Such assays that may be used or routinely modified to test immunomodulatory activity of polypeptides of the invention (including antibodies and agonists or antagonists of the invention) include assays disclosed in Miraglia et al., J Biomolecular Screening 4: 193-204(1999); Rowland et al., ""Lymphocytes: a practical approach"" Chapter 6: 138-160 (2000); Verhasselt et al., Eur J Immunol 28(11): 3886-3890 (1198); Dahlen et al., J Immunol 160(7): 3585-3593 (1998); Verhasselt et al., J Immunol 158: 2919-2925 (1997); and Nardelli et al., J Leukoc Biol 65: 822-828 (1999), the contents of each of which are herein incorporated by reference in its entirety. Human dendritic cells that may be used according to these assays may be isolated using techniques disclosed herein or otherwise known in the art. Human dendritic cells are antigen presenting cells in suspension culture, which, when activated by antigen and/or cytokines, initiate and upregulate T cell proliferation and functional activities. | A highly preferred embodiment of the invention includes a method for inhibiting (e.g., decreasing) TNF alpha production. An alternative highly preferred embodiment of the invention includes a method for stimulating (e.g., increasing) TNF alpha production. Highly preferred indications include blood disorders (e.g., as described below under "Immune Activity", "Blood-Related Disorders", and/or ""Cardiovascular Disorders""), Highly preferred indications include autoimmune diseases (e.g., rheumatoid arthritis, systemic lupus erythematosis, Crohn's disease, multiple sclerosis and/or as described below), immunodeficiencies (e.g., as described below), boosting a T cell-mediated immune response, and suppressing a T cell-mediated immune response. Additional highly preferred indications include inflammation and inflammatory disorders, and treating joint damage in patients with rheumatoid arthritis. An additional highly preferred indication is sepsis. Highly preferred indications include neoplastic diseases (e.g., leukemia, lymphoma, and/or as described below under "Hyperproliferative Disorders"). Additionally, highly preferred indications include neoplasms and cancers, such as, leukemia, lymphoma, melanoma, glioma (e.g., malignant glioma), solid tumors, and prostate, breast, lung, colon, pancreatic, esophageal, stomach, brain, liver and urinary cancer. Other preferred indications include benign dysproliferative disorders and pre-neoplastic conditions, such as, for example, hyperplasia, metaplasia, and/or dysplasia. Preferred indications include anemia, pancytopenia, leukopenia, thrombocytopenia, Hodgkin's disease, acute lymphocytic anemia (ALL), plasmacytomas, multiple myeloma, Burkitt's lymphoma, arthritis, AIDS, granulomatous disease, inflammatory bowel disease, neutropenia, neutrophilia, psoriasis, suppression of immune reactions to transplanted organs and tissues, hemophilia, hypercoagulation, diabetes mellitus, endocarditis, meningitis, Lyme Disease, cardiac reperfusion injury, and asthma and allergy. An additional preferred indication is infection (e.g., an infectious disease as described below under "Infectious Disease"). |
| 109 | Production of TNF alpha by T cells | TNFa FMAT. Assays for immunomodulatory proteins produced by activated macrophages, T cells, fibroblasts, smooth muscle, and other cell types that exert a wide variety of inflammatory and cytotoxic effects on a variety of cells are well known in the art and may be used or routinely modified to assess the ability of polypeptides of the invention (including | |

TABLE 1E.2-continued

| Biological Activity No. | Biological Activity | Exemplary Activity Assay | Preferred Indication |
|---|---|---|---|
| | | antibodies and agonists or antagonists of the invention) to mediate immunomodulation, modulate inflammation and cytotoxicity, and mediate humoral and/or cell-mediated immunity. Exemplary assays that test for immunomodulatory proteins evaluate the production of cytokines such as tumor necrosis factor alpha (TNFa), and the induction or inhibition of an inflammatory or cytotoxic response. Such assays that may be used or routinely modified to test immunomodulatory activity of polypeptides of the invention (including antibodies and agonists or antagonists of the invention) include assays disclosed in Miraglia et al., J Biomolecular Screening 4: 193-204 (1999); Rowland et al., "Lymphocytes: a practical approach" Chapter 6: 138-160 (2000); Verhasselt et al., Eur J Immunol 28(11): 3886-3890 (1198); Dahlen et al., J Immunol 160(7): 3585-3593 (1998); Verhasselt et al., J Immunol 158: 2919-2925 (1997); and Nardelli et al., J Leukoc Biol 65: 822-828 (1999), the contents of each of which are herein incorporated by reference in its entirety. Human T cells that may be used according to these assays may be isolated using techniques disclosed herein or otherwise known in the art. Human T cells are primary human lymphocytes that mature in the thymus and express a T cell receptor and CD3, CD4, or CD8. These cells mediate humoral or cell-mediated immunity and may be preactivated to enhance responsiveness to immunomodulatory factors. | |
| 110 | Production of VCAM in endothelial cells (such as human umbilical vein endothelial cells (HUVEC)) | Assays for measuring expression of VCAM are well-known in the art and may be used or routinely modified to assess the ability of polypeptides of the invention (including antibodies and agonists or antagonists of the invention) to regulate VCAM expression. For example, FMAT may be used to meaure the upregulation of cell surface VCAM-1 expresssion in endothelial cells. Endothelial cells are cells that line blood vessels, and are involved in functions that include, but are not limited to, angiogenesis, vascular permeability, vascular tone, and immune cell extravasation. Exemplary endothelial cells that may be used according to these assays include human umbilical vein endothelial cells (HUVEC), which are available from commercial sources. The expression of VCAM (CD106), a membrane-associated protein, can be upregulated by cytokines or other factors, and contributes to the extravasation of lymphocytes, leucocytes and other immune cells from blood vessels; thus VCAM expression plays a role in promoting immune and inflammatory responses. | Highly preferred indications include inflammation (acute and chronic), restnosis, atherosclerosis, asthma and allergy. Highly preferred indications include inflammation and inflammatory disorders, immunological disorders, neoplastic disorders (e.g. cancer/tumorigenesis), and cardiovascular disorders (such as described below under "Immune Activity", "Blood-Related Disorders", "Hyperproliferative Disorders" and/or "Cardiovascular Disorders"). Highly preferred indications include neoplasms and cancers such as, for example, leukemia, lymphoma, melanoma, renal cell carcinoma, and prostate, breast, lung, colon, pancreatic, esophageal, stomach, brain, liver and urinary cancer. Other preferred indications include benign dysproliferative disorders and pre-neoplastic conditions, such as, for example, hyperplasia, metaplasia, and/or dysplasia. |
| 111 | Proliferation of immune cells (such as the HMC-1 human mast cell line) | Assays for the regulation (i.e. increases or decreases) of viability and proliferation of cells in vitro are well-known in the art and may be used or routinely modified to assess the ability of polypeptides of the invention (including antibodies and agonists or antagonists of the invention) to regulate viability and proliferation of eosinophil cells and cell lines. For example, the CellTiter-Gloô Luminescent Cell Viability Assay (Promega Corp., Madison, WI, USA) can be used to measure the number of viable cells in culture based on quantitation of the ATP present which signals the | Highly preferred indications include asthma, allergy, mastocytosis (a rare, heterogeneous disorder characterized by excessive accumulation of mast cells, and their proliferation and action in the skin, central nervous system, and other organs). Preferred indications also include hematopoietic and immunological disorders (e.g., as described below under "Immune Activity", and "Blood-Related Disorders"), infection (e.g., as described below under "Infectious Disease"), autoimmune diseases (e.g., rheumatoid arthritis, systemic lupus erythematosis, multiple sclerosis and/or as described below), and |

TABLE 1E.2-continued

| Biological Activity No. | Biological Activity | Exemplary Activity Assay | Preferred Indication |
|---|---|---|---|
| | | presence of metabolically active cells. Mast cells are found in connective and mucosal tissues throughout the body. Mast cell activation (via immunoglobulin E-antigen, promoted by T helper cell type 2 cytokines) is an important component of allergic disease. Dysregulation of mast cell apoptosis may play a role in allergic disease and mast cell tumor survival. Mast cell lines that may be used according to these assays are publicly available and/or may be routinely generated. Exemplary mast cells that may be used according to these assays include HMC-1, which is an immature human mast cell line established from the peripheral blood of a patient with mast cell leukemia, and exhibits many characteristics of immature mast cells. | immunodeficiencies (e.g., as described below). |
| 112 | Proliferation of pre-adipose cells (such as 3T3-L1 cells) | Assays for the regulation (i.e. increases or decreases) of viability and proliferation of cells in vitro are well-known in the art and may be used or routinely modified to assess the ability of polypeptides of the invention (including antibodies and agonists or antagonists of the invention) to regulate viability and proliferation of pre-adipose cells and cell lines. For example, the CellTiter-Gloô Luminescent Cell Viability Assay (Promega Corp., Madison, WI, USA) can be used to measure the number of viable cells in culture based on quantitation of the ATP present which signals the presence of metabolically active cells. 3T3-L1 is a mouse preadipocyte cell line. It is a continuous substrain of 3T3 fibroblast cells developed through clonal isolation. Cells were differentiated to an adipose-like state before being used in the screen. See Green H and Meuth M., Cell 3: 127-133 (1974), which is herein incorporated by reference in its entirety. | |
| 113 | Protection from Endothelial Cell Apoptosis. | Caspase Apoptosis Rescue. Assays for caspase apoptosis rescue are well known in the art and may be used or routinely modified to assess the ability of the polypeptides of the invention (including antibodies and agonists or antagonists of the invention) to inhibit caspase protease-mediated apoptosis. Exemplary assays for caspase apoptosis that may be used or routinely modified to test caspase apoptosis rescue of polypeptides of the invention (including antibodies and agonists or antagonists of the invention) include the assays disclosed in Romeo et al., Cardiovasc Res 45(3): 788-794 (2000); Messmer et al., Br J Pharmacol 127(7): 1633-1640 (1999); and J Atheroscler Thromb 3(2): 75-80 (1996); the contents of each of which are herein incorporated by reference in its entirety. Endothelial cells that may be used according to these assays are publicly available (e.g., through commercial sources). Exemplary endothelial cells that may be used according to these assays include bovine aortic endothelial cells (bAEC), which are an example of endothelial cells which line blood vessels and are involved in functions that include, but are not limited to, angiogenesis, vascular permeability, vascular tone, and immune cell extravasation. | A highly preferred embodiment of the invention includes a method for stimulating endothelial cell growth. An alternative highly preferred embodiment of the invention includes a method for inhibiting endothelial cell growth. A highly preferred embodiment of the invention includes a method for stimulating endothelial cell proliferation. An alternative highly preferred embodiment of the invention includes a method for inhibiting endothelial cell proliferation. A highly preferred embodiment of the invention includes a method for stimulating endothelial cell growth. An alternative highly preferred embodiment of the invention includes a method for inhibiting endothelial cell growth. A highly preferred embodiment of the invention includes a method for stimulating apoptosis of endothelial cells. An alternative highly preferred embodiment of the invention includes a method for inhibiting (e.g., decreasing) apoptosis of endothelial cells. A highly preferred embodiment of the invention includes a method for stimulating angiogenisis. An alternative highly preferred embodiment of the invention includes a method for inhibiting angiogenesis. A highly preferred embodiment of the invention includes a method for reducing cardiac hypertrophy. An alternative highly preferred embodiment of the invention includes a method for inducing cardiac hypertrophy. Highly preferred indications include neoplastic diseases (e.g., as described below under "Hyperproliferative Disorders"), and disorders of the cardiovascular system (e.g., heart disease, congestive heart |

TABLE 1E.2-continued

| Biological Activity No. | Biological Activity | Exemplary Activity Assay | Preferred Indication |
|---|---|---|---|
| | | | failure, hypertension, aortic stenosis, cardiomyopathy, valvular regurgitation, left ventricular dysfunction, atherosclerosis and atherosclerotic vascular disease, diabetic nephropathy, intracardiac shunt, cardiac hypertrophy, myocardial infarction, chronic hemodynamic overload, and/or as described below under "Cardiovascular Disorders"). Highly preferred indications include cardiovascular, endothelial and/or angiogenic disorders (e.g., systemic disorders that affect vessels such as diabetes mellitus, as well as diseases of the vessels themselves, such as of the arteries, capillaries, veins and/or lymphatics). Highly preferred are indications that stimulate angiogenesis and/or cardiovascularization. Highly preferred are indications that inhibit angiogenesis and/or cardiovascularization. Highly preferred indications include antiangiogenic activity to treat solid tumors, leukemias, and Kaposi''s sarcoma, and retinal disorders. Highly preferred indications include neoplasms and cancer, such as, Kaposi''s sarcoma, hemangioma (capillary and cavernous), glomus tumors, telangiectasia, bacillary angiomatosis, hemangioendothelioma, angiosarcoma, haemangiopericytoma, lymphangioma, lymphangiosarcoma. Highly preferred indications also include cancers such as, prostate, breast, lung, colon, pancreatic, esophageal, stomach, brain, liver, and urinary cancer. Preferred indications include benign dysproliferative disorders and pre-neoplastic conditions, such as, for example, hyperplasia, metaplasia, and/or dysplasia. Highly preferred indications also include arterial disease, such as, atherosclerosis, hypertension, coronary artery disease, inflammatory vasculitides, Reynaud''s disease and Reynaud''s phenomenom, aneurysms, restenosis; venous and lymphatic disorders such as thrombophlebitis, lymphangitis, and lymphedema; and other vascular disorders such as peripheral vascular disease, and cancer. Highly preferred indications also include trauma such as wounds, burns, and injured tissue (e.g., vascular injury such as, injury resulting from balloon angioplasty, and atheroschlerotic lesions), implant fixation, scarring, ischemia reperfusion injury, rheumatoid arthritis, cerebrovascular disease, renal diseases such as acute renal failure, and osteoporosis. Additional highly preferred indications include stroke, graft rejection, diabetic or other retinopathies, thrombotic and coagulative disorders, vascularitis, lymph angiogenesis, sexual disorders, age-related macular degeneration, and treatment/prevention of endometriosis and related conditions. Additional highly preferred indications include fibromas, heart disease, cardiac arrest, heart valve disease, and vascular disease. Preferred indications include blood disorders (e.g., as described below under "Immune Activity", "Blood-Related Disorders", and/or "Cardiovascular Disorders"). Preferred indications include autoimmune diseases (e.g., rheumatoid arthritis, systemic lupus erythematosis, multiple sclerosis and/or as described below) and immunodeficiencies (e.g., as described below). Additional preferred indications include inflammation and inflammatory disorders (such as acute and chronic inflammatory diseases, e.g., inflammatory bowel disease and Crohn's disease), and pain management. |

TABLE 1E.2-continued

| Biological Activity No. | Biological Activity | Exemplary Activity Assay | Preferred Indication |
|---|---|---|---|
| 114 | Regulation (inhibition or activation) of immune cell proliferation. | The mixed lymphocyte reaction assay (MLR) (see e.g., Example: "Detection of Inhibition of a Mixed Lymphocyte Reaction" below) is a complex in vitro assay of T-cell responsiveness and immune cell activation. This assay is useful, for example, as an in vitro model of allograft rejection and graft versus host disease. In this assays PBMCs from human donors are mixed, cultured, and monitored for thymidine incorporation (a measure of cell proliferation) to identify polypeptides of the invention (including antibodies and agonists or antagonists of the invention) that may activate or inhibit immune responses. | |
| 115 | Regulation of apoptosis in pancreatic beta cells. | Caspase Apoptosis. Assays for caspase apoptosis are well known in the art and may be used or routinely modified to assess the ability of polypeptides of the invention (including antibodies and agonists or antagonists of the invention) to promote caspase protease-mediated apoptosis. Apoptosis in pancreatic beta is associated with induction and progression of diabetes. Exemplary assays for caspase apoptosis that may be used or routinely modified to test capase apoptosis activity of polypeptides of the invention (including antibodies and agonists or antagonists of the invention) include the assays disclosed in: Loweth, A C, et al., FEBS Lett, 400(3): 285-8 (1997); Saini, K S, et al., Biochem Mol Biol Int, 39(6): 1229-36 (1996); Krautheim, A., et al., Br J Pharmacol, 129(4): 687-94 (2000); Chandra J, et al., Diabetes, 50 Suppl 1: S44-7 (2001); Suk K, et al., J Immunol, 166(7): 4481-9 (2001); Tejedo J, et al., FEBS Lett, 459(2): 238-43 (1999); Zhang, S., et al., FEBS Lett, 455(3): 315-20 (1999); Lee et al., FEBS Lett 485(2-3): 122-126 (2000); Nor et al., J Vasc Res 37(3): 209-218 (2000); and Karsan and Harlan, J Atheroscler Thromb 3(2): 75-80 (1996); the contents of each of which are herein incorporated by reference in its entirety. Pancreatic cells that may be used according to these assays are publicly available (e.g., through the ATCC ™) and/or may be routinely generated. Exemplary pancreatic cells that may be used according to these assays include RIN-m. RIN-m is a rat adherent pancreatic beta cell insulinoma cell line derived from a radiation induced transplantable rat islet cell tumor. The cells produce and secrete islet polypeptide hormones, and produce insulin, somatostatin, and possibly glucagon. ATTC: #CRL-2057 Chick et al. Proc. Natl. Acad. Sci. 1977 74: 628; AF et al. Proc. Natl. Acad. Sci. 1980 77: 3519. | A highly preferred indication is diabetes mellitus. An additional highly preferred indication is a complication associated with diabetes (e.g., diabetic retinopathy, diabetic nephropathy, kidney disease (e.g., renal failure, nephropathy and/or other diseases and disorders as described in the ""Renal Disorders"" section below), diabetic neuropathy, nerve disease and nerve damage (e.g., due to diabetic neuropathy), blood vessel blockage, heart disease, stroke, impotence (e.g., due to diabetic neuropathy or blood vessel blockage), seizures, mental confusion, drowsiness, nonketotic hyperglycemic-hyperosmolar coma, cardiovascular disease (e.g., heart disease, atherosclerosis, microvascular disease, hypertension, stroke, and other diseases and disorders as described in the ""Cardiovascular Disorders"" section below), dyslipidemia, endocrine disorders (as described in the ""Endocrine Disorders"" section below), neuropathy, vision impairment (e.g., diabetic retinopathy and blindness), ulcers and impaired wound healing, and infection (e.g., infectious diseases and disorders as described in the ""Infectious Diseases"" section below, especially of the urinary tract and skin), carpal tunnel syndrome and Dupuytren's contracture). An additional highly preferred indication is obesity and/or complications associated with obesity. Additional highly preferred indications include weight loss or alternatively, weight gain. Aditional highly preferred indications are complications associated with insulin resistance. |
| 116 | Regulation of apoptosis of immune cells (such as mast cells). | Caspase Apoptosis. Assays for caspase apoptosis are well known in the art and may be used or routinely modified to assess the ability of polypeptides of the invention (including antibodies and agonists or antagonists of the invention) to regulate caspase protease-mediated apoptosis in immune cells (such as, for example, in mast cells). Mast cells are found in connective and mucosal tissues throughout the body, and their activation via immunoglobulin E-antigen, promoted by T helper cell type 2 cytokines, is an important component of allergic disease. Dysregulation of mast cell apoptosis may play a role in allergic disease and mast cell tumor survival. Exemplary | Preferred embodiments of the invention include using polypeptides of the invention (or antibodies, agonists, or antagonists thereof) in detection, diagnosis, prevention, and/or treatment of asthma, allergy, hypersensitivity and inflammation. |

TABLE 1E.2-continued

| Biological Activity No. | Biological Activity | Exemplary Activity Assay | Preferred Indication |
|---|---|---|---|
| | | assays for caspase apoptosis that may be used or routinely modified to test capase apoptosis activity induced by polypeptides of the invention (including antibodies and agonists or antagonists of the invention) include the assays disclosed in: Masuda A, et al., J Biol Chem, 276(28): 26107-26113 (2001); Yeatman C F 2nd, et al., J Exp Med, 192(8): 1093-1103 (2000); Lee et al., FEBS Lett 485(2-3): 122-126 (2000); Nor et al., J Vasc Res 37(3): 209-218 (2000); and Karsan and Harlan, J Atheroscler Thromb 3(2): 75-80 (1996); the contents of each of which are herein incorporated by reference in its entirety. Immune cells that may be used according to these assays are publicly available (e.g., through commercial sources). Exemplary immune cells that may be used according to these assays include mast cells such as the HMC human mast cell line. | |
| 117 | Regulation of proliferation and/or differentiation in immune cells (such as mast cells). | Kinase assays, for example an Elk-1 kinase assay for ERK signal transduction that regulates cell proliferation or differentiation, are well known in the art and may be used or routinely modified to assess the ability of polypeptides of the invention (including antibodies and agonists or antagonists of the invention) to promote or inhibit cell proliferation, activation, and differentiation. Exemplary assays for ERK kinase activity that may be used or routinely modified to test ERK kinase-induced activity of polypeptides of the invention (including antibodies and agonists or antagonists of the invention) include the assays disclosed in: Ali H, et al., J Immunol, 165(12): 7215-7223 (2000); Tam S Y, et al., Blood, 90(5): 1807-1820 (1997); Forrer et al., Biol Chem 379(8-9): 1101-1110 (1998); Berra et al., Biochem Pharmacol 60(8): 1171-1178 (2000); Gupta et al., Exp Cell Res 247(2): 495-504 (1999); Chang and Karin, Nature 410(6824): 37-40 (2001); and Cobb M H, Prog Biophys Mol Biol 71(3-4): 479-500 (1999); the contents of each of which are herein incorporated by reference in its entirety. Exemplary immune cells that may be used according to these assays include human mast cells such as the HMC-1 cell line. | Preferred embodiments of the invention include using polypeptides of the invention (or antibodies, agonists, or antagonists thereof) in detection, diagnosis, prevention, and/or treatment of asthma, allergy, hypersensitivity and inflammation. |
| 118 | Regulation of transcription of Malic Enzyme in adipocytes | Assays for the regulation of transcription of Malic Enzyme are well-known in the art and may be used or routinely modified to assess the ability of polypeptides of the invention (including antibodies and agonists or antagonists of the invention) to regulate transcription of Malic Enzyme, a key enzyme in lipogenesis. Malic enzyme is involved in lipogenesis and its expression is stimulted by insulin. ME promoter contains two direct repeat (DR1)-like elements MEp and MEd identified as putative PPAR response elements. ME promoter may also responds to AP1 and other transcription factors. Exemplary assays that may be used or routinely modified to test for regulation of transcription of Malic Enzyme (in adipoocytes) by polypeptides of the invention (including antibodies and agonists or antagonists of the invention) include assays disclosed in: Streeper, R. S., et al., Mol Endocrinol, 12(11): 1778-91 (1998); Garcia-Jimenez, C., et al., Mol Endocrinol, 8(10): 1361-9 (1994); Barroso, I., et al., J Biol Chem, 274(25): 17997-8004 (1999); | A highly preferred indication is diabetes mellitus. An additional highly preferred indication is a complication associated with diabetes (e.g., diabetic retinopathy, diabetic nephropathy, kidney disease (e.g., renal failure, nephropathy and/or other diseases and disorders as described in the “Renal Disorders” section below), diabetic neuropathy, nerve disease and nerve damage (e.g., due to diabetic neuropathy), blood vessel blockage, heart disease, stroke, impotence (e.g., due to diabetic neuropathy or blood vessel blockage), seizures, mental confusion, drowsiness, nonketotic hyperglycemic-hyperosmolar coma, cardiovascular disease (e.g., heart disease, atherosclerosis, microvascular disease, hypertension, stroke, and other diseases and disorders as described in the “Cardiovascular Disorders” section below), dyslipidemia, endocrine disorders (as described in the “Endocrine Disorders” section below), neuropathy, vision impairment (e.g., diabetic retinopathy and blindness), ulcers and impaired wound healing, and infection (e.g., infectious diseases and disorders as described in the |

TABLE 1E.2-continued

| Biological Activity No. | Biological Activity | Exemplary Activity Assay | Preferred Indication |
|---|---|---|---|
| | | Ijpenberg, A., et al., J Biol Chem, 272(32): 20108-20117 (1997); Berger, et al., Gene 66: 1-10 (1988); and, Cullen, B., et al., Methods in Enzymol. 216: 362-368 (1992), the contents of each of which is herein incorporated by reference in its entirety. Hepatocytes that may be used according to these assays are publicly available (e.g., through the ATCC ™) and/or may be routinely generated. Exemplary hepatocytes that may be used according to these assays includes the H4IIE rat liver hepatoma cell line. | "Infectious Diseases" section below, especially of the urinary tract and skin), carpal tunnel syndrome and Dupuytren's contracture). An additional highly preferred indication is obesity and/or complications associated with obesity. Additional highly preferred indications include weight loss or alternatively, weight gain. Aditional highly preferred indications are complications associated with insulin resistance. |
| 119 | Regulation of transcription of Malic Enzyme in hepatocytes | Assays for the regulation of transcription of Malic Enzyme are well-known in the art and may be used or routinely modified to assess the ability of polypeptides of the invention (including antibodies and agonists or antagonists of the invention) to regulate transcription of Malic Enzyme, a key enzyme in lipogenesis. Malic enzyme is involved in lipogenesis and its expression is stimulted by insulin. ME promoter contains two direct repeat (DR1)-like elements MEp and MEd identified as putative PPAR response elements. ME promoter may also responds to AP1 and other transcription factors. Exemplary assays that may be used or routinely modified to test for regulation of transcription of Malic Enzyme (in hepatocytes) by polypeptides of the invention (including antibodies and agonists or antagonists of the invention) include assays disclosed in: Streeper, R. S., et al., Mol Endocrinol, 12(11): 1778-91 (1998); Garcia-Jimenez, C., et al., Mol Endocrinol, 8(10): 1361-9 (1994); Barroso, I., et al., J Biol Chem, 274(25): 17997-8004 (1999); Ijpenberg, A., et al., J Biol Chem, 272(32): 20108-20117 (1997); Berger, et al., Gene 66: 1-10 (1988); and, Cullen, B., et al., Methods in Enzymol. 216: 362-368 (1992), the contents of each of which is herein incorporated by reference in its entirety. Hepatocytes that may be used according to these assays are publicly available (e.g., through the ATCC ™) and/or may be routinely generated. Exemplary hepatocytes that may be used according to these assays includes the mouse 3T3-L1 cell line. 3T3-L1 is a mouse preadipocyte cell line (adherent). It is a continuous substrain of 3T3 fibroblasts developed through clonal isolation. Cells undergo a pre-adipocyte to adipose-like conversion under appropriate differentiation culture conditions. | A highly preferred indication is diabetes mellitus. An additional highly preferred indication is a complication associated with diabetes (e.g., diabetic retinopathy, diabetic nephropathy, kidney disease (e.g., renal failure, nephropathy and/or other diseases and disorders as described in the ""Renal Disorders"" section below), diabetic neuropathy, nerve disease and nerve damage (e.g., due to diabetic neuropathy), blood vessel blockage, heart disease, stroke, impotence (e.g., due to diabetic neuropathy or blood vessel blockage), seizures, mental confusion, drowsiness, nonketotic hyperglycemic-hyperosmolar coma, cardiovascular disease (e.g., heart disease, atherosclerosis, microvascular disease, hypertension, stroke, and other diseases and disorders as described in the ""Cardiovascular Disorders"" section below), dyslipidemia, endocrine disorders (as described in the ""Endocrine Disorders"" section below), neuropathy, vision impairment (e.g., diabetic retinopathy and blindness), ulcers and impaired wound healing, and infection (e.g., infectious diseases and disorders as described in the ""Infectious Diseases"" section below, especially of the urinary tract and skin), carpal tunnel syndrome and Dupuytren's contracture). An additional highly preferred indication is obesity and/or complications associated with obesity. Additional highly preferred indications include weight loss or alternatively, weight gain. Aditional highly preferred indications are complications associated with insulin resistance. |
| 120 | Regulation of transcription through the FAS promoter element in hepatocytes | Assays for the regulation of transcription through the FAS promoter element are well-known in the art and may be used or routinely modified to assess the ability of polypeptides of the invention (including antibodies and agonists or antagonists of the invention) to activate the FAS promoter element in a reporter construct and to regulate transcription of FAS, a key enzyme for lipogenesis. FAS promoter is regulated by many transcription factors including SREBP. Insulin increases FAS gene transcription in livers of diabetic mice. This stimulation of transcription is also somewhat glucose dependent. Exemplary assays that may be used or routinely modified to test for FAS promoter element activity (in hepatocytes) by polypeptides of the invention (including antibodies and agonists or antagonists of the invention) | A highly preferred indication is diabetes mellitus. An additional highly preferred indication is a complication associated with diabetes (e.g., diabetic retinopathy, diabetic nephropathy, kidney disease (e.g., renal failure, nephropathy and/or other diseases and disorders as described in the "Renal Disorders" section below), diabetic neuropathy, nerve disease and nerve damage (e.g., due to diabetic neuropathy), blood vessel blockage, heart disease, stroke, impotence (e.g., due to diabetic neuropathy or blood vessel blockage), seizures, mental confusion, drowsiness, nonketotic hyperglycemic-hyperosmolar coma, cardiovascular disease (e.g., heart disease, atherosclerosis, microvascular disease, hypertension, stroke, and other diseases and disorders as described in the "Cardiovascular Disorders" section below), dyslipidemia, endocrine disorders (as described in the |

TABLE 1E.2-continued

| Biological Activity No. | Biological Activity | Exemplary Activity Assay | Preferred Indication |
|---|---|---|---|
| | | include assays disclosed in Xiong, S., et al., Proc Natl Acad Sci U.S.A., 97(8): 3948-53 (2000); Roder, K., et al., Eur J Biochem, 260(3): 743-51 (1999); Oskouian B, et al., Biochem J, 317 (Pt 1): 257-65 (1996); Berger, et al., Gene 66: 1-10 (1988); and, Cullen, B., et al., Methods in Enzymol. 216: 362-368 (1992), the contents of each of which is herein incorporated by reference in its entirety. Hepatocytes that may be used according to these assays, such as H4IIE cells, are publicly available (e.g., through the ATCC ™) and/or may be routinely generated. Exemplary hepatocytes that may be used according to these assays include rat liver hepatoma cell line(s) inducible with glucocorticoids, insulin, or cAMP derivatives. | "Endocrine Disorders" section below), neuropathy, vision impairment (e.g., diabetic retinopathy and blindness), ulcers and impaired wound healing, and infection (e.g., infectious diseases and disorders as described in the "Infectious Diseases" section below, especially of the urinary tract and skin), carpal tunnel syndrome and Dupuytren's contracture).<br>An additional highly preferred indication is obesity and/or complications associated with obesity. Additional highly preferred indications include weight loss or alternatively, weight gain. Additional highly preferred indications are complications associated with insulin resistance. |
| 121 | Regulation of transcription through the PEPCK promoter in hepatocytes | Assays for the regulation of transcription through the PEPCK promoter are well-known in the art and may be used or routinely modified to assess the ability of polypeptides of the invention (including antibodies and agonists or antagonists of the invention) to activate the PEPCK promoter in a reporter construct and regulate liver gluconeogenesis. Exemplary assays for regulation of transcription through the PEPCK promoter that may be used or routinely modified to test for PEPCK promoter activity (in hepatocytes) of polypeptides of the invention (including antibodies and agonists or antagonists of the invention) include assays disclosed in Berger et al., Gene 66: 1-10 (1998); Cullen and Malm, Methods in Enzymol 216: 362-368 (1992); Henthorn et al., Proc Natl Acad Sci USA 85: 6342-6346 (1988); Lochhead et al., Diabetes 49(6): 896-903 (2000); and Yeagley et al., J Biol Chem 275(23): 17814-17820 (2000), the contents of each of which is herein incorporated by reference in its entirety. Hepatocyte cells that may be used according to these assays are publicly available (e.g., through the ATCC ™) and/or may be routinely generated. Exemplary liver hepatoma cells that may be used according to these assays include H4lle cells, which contain a tyrosine amino transferase that is inducible with glucocorticoids, insulin, or cAMP derivatives. | A highly preferred indication is diabetes mellitus. An additional highly preferred indication is a complication associated with diabetes (e.g., diabetic retinopathy, diabetic nephropathy, kidney disease (e.g., renal failure, nephropathy and/or other diseases and disorders as described in the "Renal Disorders" section below), diabetic neuropathy, nerve disease and nerve damage (e.g., due to diabetic neuropathy), blood vessel blockage, heart disease, stroke, impotence (e.g., due to diabetic neuropathy or blood vessel blockage), seizures, mental confusion, drowsiness, nonketotic hyperglycemic-hyperosmolar coma, cardiovascular disease (e.g., heart disease, atherosclerosis, microvascular disease, hypertension, stroke, and other diseases and disorders as described in the "Cardiovascular Disorders" section below), dyslipidemia, endocrine disorders (as described in the "Endocrine Disorders" section below), neuropathy, vision impairment (e.g., diabetic retinopathy and blindness), ulcers and impaired wound healing, infection (e.g., an infectious diseases or disorders as described in the "Infectious Diseases" section below, especially of the urinary tract and skin), carpal tunnel syndrome and Dupuytren's contracture).<br>An additional highly preferred indication is obesity and/or complications associated with obesity. Additional highly preferred indications include weight loss or alternatively, weight gain. Additional highly preferred indications are complications associated with insulin resistance. Additional highly preferred indications are disorders of the musculoskeletal systems including myopathies, muscular dystrophy, and/or as described herein.<br>Additional highly preferred indications include glycogen storage disease (e.g., glycogenoses), hepatitis, gallstones, cirrhosis of the liver, degenerative or necrotic liver disease, alcoholic liver diseases, fibrosis, liver regeneration, metabolic disease, dyslipidemia and cholesterol metabolism, and hepatocarcinomas.<br>Highly preferred indications include blood disorders (e.g., as described below under "Immune Activity", "Cardiovascular Disorders", and/or "Blood-Related Disorders"), immune disorders (e.g., as described below under "Immune Activity"), infection (e.g., an infectious disease and/or disorder as described below under "Infectious Disease"), endocrine disorders (e.g., as described below under "Endocrine Disorders"), and neural disorders (e.g., as described below under "Neural Activity and Neurological Diseases").<br>Additional preferred indications include |

TABLE 1E.2-continued

| Biological Activity No. | Biological Activity | Exemplary Activity Assay | Preferred Indication |
|---|---|---|---|
| | | | neoplastic diseases (e.g., as described below under "Hyperproliferative Disorders"). Preferred indications include neoplasms and cancers, such as, leukemia, lymphoma, prostate, breast, lung, colon, pancreatic, esophageal, stomach, brain, and urinary cancer. A highly preferred indication is liver cancer. Other preferred indications include benign dysproliferative disorders and pre-neoplastic conditions, such as, for example, hyperplasia, metaplasia, and/or dysplasia. |
| 122 | Regulation of transcription via DMEF1 response element in adipocytes and pre-adipocytes | Assays for the regulation of transcription through the DMEF1 response element are well-known in the art and may be used or routinely modified to assess the ability of polypeptides of the invention (including antibodies and agonists or antagonists of the invention) to activate the DMEF1 response element in a reporter construct (such as that containing the GLUT4 promoter) and to regulate insulin production. The DMEF1 response element is present in the GLUT4 promoter and binds to MEF2 transcription factor and another transcription factor that is required for insulin regulation of Glut4 expression in skeletal muscle. GLUT4 is the primary insulin-responsive glucose transporter in fat and muscle tissue. Exemplary assays that may be used or routinely modified to test for DMEF1 response element activity (in adipocytes and pre-adipocytes) by polypeptides of the invention (including antibodies and agonists or antagonists of the invention) include assays disclosed in Thai, M. V., et al., J Biol Chem, 273(23): 14285-92 (1998); Mora, S., et al., J Biol Chem, 275(21): 16323-8 (2000); Liu, M. L., et al., J Biol Chem, 269(45): 28514-21 (1994); "Identification of a 30-base pair regulatory element and novel DNA binding protein that regulates the human GLUT4 promoter in transgenic mice", J Biol Chem. 2000 August 4; 275(31): 23666-73; Berger, et al., Gene 66: 1-10 (1988); and, Cullen, B., et al., Methods in Enzymol. 216: 362-368 (1992), the contents of each of which is herein incorporated by reference in its entirety. Adipocytes and pre-adipocytes that may be used according to these assays are publicly available (e.g., through the ATCC ™) and/or may be routinely generated. Exemplary cells that may be used according to these assays include the mouse 3T3-L1 cell line which is an adherent mouse preadipocyte cell line. Mouse 3T3-L1 cells are a continuous substrain of 3T3 fibroblasts developed through clonal isolation. These cells undergo a pre-adipocyte to adipose-like conversion under appropriate differentiation culture conditions. | A highly preferred indication is diabetes mellitus. Additional highly preferred indications include complications associated with diabetes (e.g., diabetic retinopathy, diabetic nephropathy, kidney disease (e.g., renal failure, nephropathy and/or other diseases and disorders as described in the "Renal Disorders" section below), diabetic neuropathy, nerve disease and nerve damage (e.g., due to diabetic neuropathy), blood vessel blockage, heart disease, stroke, impotence (e.g., due to diabetic neuropathy or blood vessel blockage), seizures, mental confusion, drowsiness, nonketotic hyperglycemic-hyperosmolar coma, cardiovascular disease (e.g., heart disease, atherosclerosis, microvascular disease, hypertension, stroke, and other diseases and disorders as described in the "Cardiovascular Disorders" section below), dyslipidemia, endocrine disorders (as described in the "Endocrine Disorders" section below), neuropathy, vision impairment (e.g., diabetic retinopathy and blindness), ulcers and impaired wound healing, and infection (e.g., infectious diseases and disorders as described in the "Infectious Diseases" section below, especially of the urinary tract and skin). An additional highly preferred indication is obesity and/or complications associated with obesity. Additional highly preferred indications include weight loss or alternatively, weight gain. Additional highly preferred indications are complications associated with insulin resistance. |
| 123 | Regulation of viability and proliferation of pancreatic beta cells. | Assays for the regulation of viability and proliferation of cells in vitro are well-known in the art and may be used or routinely modified to assess the ability of polypeptides of the invention (including antibodies and agonists or antagonists of the invention) to regulate viability and proliferation of pancreatic beta cells. For example, the Cell Titer-Glo luminescent cell viability assay measures the number of viable cells in culture based on quantitation of the ATP present which signals the presence of metabolically active cells. Exemplary assays that may be used or routinely modified to test regulation of | A highly preferred indication is diabetes mellitus. An additional highly preferred indication is a complication associated with diabetes (e.g., diabetic retinopathy, diabetic nephropathy, kidney disease (e.g., renal failure, nephropathy and/or other diseases and disorders as described in the ""Renal Disorders"" section below), diabetic neuropathy, nerve disease and nerve damage (e.g., due to diabetic neuropathy), blood vessel blockage, heart disease, stroke, impotence (e.g., due to diabetic neuropathy or blood vessel blockage), seizures, mental confusion, drowsiness, nonketotic hyperglycemic-hyperosmolar coma, cardiovascular disease (e.g., heart disease, |

TABLE 1E.2-continued

| Biological Activity No. | Biological Activity | Exemplary Activity Assay | Preferred Indication |
|---|---|---|---|
| | | viability and proliferation of pancreatic beta cells by polypeptides of the invention (including antibodies and agonists or antagonists of the invention) include assays disclosed in: Friedrichsen B N, et al., Mol Endocrinol, 15(1): 136-48 (2001); Huotari M A, et al., Endocrinology, 139(4): 1494-9 (1998); Hugl S R, et al., J Biol Chem 1998 July10; 273(28): 17771-9 (1998), the contents of each of which is herein incorporated by reference in its entirety. Pancreatic cells that may be used according to these assays are publicly available (e.g., through the ATCC ™) and/or may be routinely generated. Exemplary pancreatic cells that may be used according to these assays include rat INS-1 cells. INS-1 cells are a semi-adherent cell line established from cells isolated from an X-ray induced rat transplantable insulinoma. These cells retain characteristics typical of native pancreatic beta cells including glucose inducible insulin secretion. References: Asfari et al. Endocrinology 1992 130: 167. Additional exemplary pancreatic cells that may be used according to these assays include HITT15 Cells. HITT15 are an adherent epithelial cell line established from Syrian hamster islet cells transformed with SV40. These cells express glucagon, somatostatin, and glucocorticoid receptors. The cells secrete insulin, which is stimulated by glucose and glucagon and suppressed by somatostatin or glucocorticoids. ATTC# CRL-1777 Refs: Lord and Ashcroft. Biochem. J. 219: 547-551; Santerre et al. Proc. Natl. Acad. Sci. USA 78: 4339-4343, 1981. | atherosclerosis, microvascular disease, hypertension, stroke, and other diseases and disorders as described in the ""Cardiovascular Disorders"" section below), dyslipidemia, endocrine disorders (as described in the ""Endocrine Disorders"" section below), neuropathy, vision impairment (e.g., diabetic retinopathy and blindness), ulcers and impaired wound healing, and infection (e.g., infectious diseases and disorders as described in the ""Infectious Diseases"" section below, especially of the urinary tract and skin), carpal tunnel syndrome and Dupuytren's contracture). An additional highly preferred indication is obesity and/or complications associated with obesity. Additional highly preferred indications include weight loss or alternatively, weight gain. Additional highly preferred indications are complications associated with insulin resistance. |
| 124 | Regulation of viability or proliferation of immune cells (such as human eosinophil EOL-1 cells). | Assays for the regulation (i.e. increases or decreases) of viability and proliferation of cells in vitro are well-known in the art and may be used or routinely modified to assess the ability of polypeptides of the invention (including antibodies and agonists or antagonists of the invention) to regulate viability and proliferation of eosinophil cells and cell lines. For example, the CellTiter-Gloô Luminescent Cell Viability Assay (Promega Corp., Madison, WI, USA) can be used to measure the number of viable cells in culture based on quantitation of the ATP present which signals the presence of metabolically active cells. Eosinophils are a type of immune cell important in allergic responses; they are recruited to tissues and mediate the inflammtory response of late stage allergic reaction. Eosinophil cell lines that may be used according to these assays are publicly available and/or may be routinely generated. Exemplary eosinophil cells that may be used according to these assays include EOL-1 Cells. | Highly preferred indications include eosinophilia, asthma, allergy, hypersensitivity reactions, inflammation, and inflammatory disorders. Additional highly preferred indications include immune and hematopoietic disorders (e.g., as described below under "Immune Activity", and "Blood-Related Disorders"), autoimmune diseases (e.g., rheumatoid arthritis, systemic lupus erythematosis, Crohn"s disease, multiple sclerosis and/or as described below), immunodeficiencies (e.g., as described below). Highly preferred indications also include boosting or inhibiting immune cell proliferation. Preferred indications include neoplastic diseases (e.g., leukemia, lymphoma, and/or as described below under "Hyperproliferative Disorders"). Highly preferred indications include boosting an eosinophil-mediated immune response, and suppressing an eosinophil-mediated immune response. |
| 125 | SEAP in 293/ISRE | | |
| 126 | SEAP in Alk Phos C2C12 | | |
| 127 | SEAP in ATP-3T3-L1 | | |
| 128 | SEAP in HepG2/Squale-synthetase(stimulation) | | |
| 129 | SEAP in HIB/CRE | | |
| 130 | SEAP in Jurkat-AP1 | | |
| 131 | SEAP in Jurkat/IL4 promoter | | |
| 132 | SEAP in Jurkat/IL4 | | |

TABLE 1E.2-continued

| Biological Activity No. | Biological Activity | Exemplary Activity Assay | Preferred Indication |
|---|---|---|---|
| | promoter (antiCD3 co-stim) | | |
| 133 | SEAP in Ku812/NFkB (TNF synergy) | | |
| 134 | SEAP in Molt4/SRE | | |
| 135 | SEAP in NK16/STAT6 | | |
| 136 | SEAP in OE-21 | | |
| 137 | SEAP in OE-33 | | |
| 138 | SEAP in SW480 | | |
| 139 | SEAP in UMR-106 | | |
| 140 | Stimulation of Calcium Flux in pancreatic beta cells. | Assays for measuring calcium flux are well-known in the art and may be used or routinely modified to assess the ability of polypeptides of the invention (including antibodies and agonists or antagonists of the invention) to mobilize calcium. For example, the FLPR assay may be used to measure influx of calcium. Cells normally have very low concentrations of cytosolic calcium compared to much higher extracellular calcium. Extracellular factors can cause an influx of calcium, leading to activation of calcium responsive signaling pathways and alterations in cell functions. Exemplary assays that may be used or routinely modified to measure calcium flux by polypeptides of the invention (including antibodies and agonists or antagonists of the invention) include assays disclosed in: Satin L S, et al., Endocrinology, 136(10): 4589-601 (1995); Mogami H, et al., Endocrinology, 136(7): 2960-6 (1995); Richardson S B, et al., Biochem J, 288 (Pt 3): 847-51 (1992); and, Meats, J E, et al., Cell Calcium 1989 November-December; 10(8): 535-41 (1989), contents the of each of which is herein incorporated by reference in its entirety. Pancreatic cells that may be used according to these assays are publicly available (e.g., through the ATCC ™) and/or may be routinely generated. Exemplary pancreatic cells that may be used according to these assays include HITT15 Cells. HITT15 are an adherent epithelial cell line established from Syrian hamster islet cells transformed with SV40. These cells express glucagon, somatostatin, and glucocorticoid receptors. The cells secrete insulin, which is stimulated by glucose and glucagon and suppressed by somatostatin or glucocorticoids. ATTC# CRL-1777 Refs: Lord and Ashcroft. Biochem. J. 219: 547-551; Santerre et al. Proc. Natl. Acad. Sci. USA 78: 4339-4343, 1981. | A highly preferred indication is diabetes mellitus. An additional highly preferred indication is a complication associated with diabetes (e.g., diabetic retinopathy, diabetic nephropathy, kidney disease (e.g., renal failure, nephropathy and/or other diseases and disorders as described in the "Renal Disorders" section below), diabetic neuropathy, nerve disease and nerve damage (e.g., due to diabetic neuropathy), blood vessel blockage, heart disease, stroke, impotence (e.g., due to diabetic neuropathy or blood vessel blockage), seizures, mental confusion, drowsiness, nonketotic hyperglycemic-hyperosmolar coma, cardiovascular disease (e.g., heart disease, atherosclerosis, microvascular disease, hypertension, stroke, and other diseases and disorders as described in the "Cardiovascular Disorders" section below), dyslipidemia, endocrine disorders (as described in the "Endocrine Disorders" section below), neuropathy, vision impairment (e.g., diabetic retinopathy and blindness), ulcers and impaired wound healing, and infection (e.g., infectious diseases and disorders as described in the "Infectious Diseases" section below, especially of the urinary tract and skin), carpal tunnel syndrome and Dupuytren's contracture).<br>An additional highly preferred indication is obesity and/or complications associated with obesity. Additional highly preferred indications include weight loss or alternatively, weight gain. Aditional highly preferred indications are complications associated with insulin resistance. |
| 141 | Stimulation of insulin secretion from pancreatic beta cells. | Assays for measuring secretion of insulin are well-known in the art and may be used or routinely modified to assess the ability of polypeptides of the invention (including antibodies and agonists or antagonists of the invention) to stimulate insulin secretion. For example, insulin secretion is measured by FMAT using anti-rat insulin antibodies. Insulin secretion from pancreatic beta cells is upregulated by glucose and also by certain proteins/peptides, and disregulation is a key component in diabetes. Exemplary assays that may be used or routinely modified to test for stimulation of insulin secretion (from pancreatic cells) by polypeptides of the invention (including antibodies and agonists or antagonists of the invention) include assays disclosed in: Ahren, B., et al., Am J Physiol, 277(4 Pt 2): R959-66 (1999); Li, M., et al., | A highly preferred indication is diabetes mellitus. An additional highly preferred indication is a complication associated with diabetes (e.g., diabetic retinopathy, diabetic nephropathy, kidney disease (e.g., renal failure, nephropathy and/or other diseases and disorders as described in the ""Renal Disorders"" section below), diabetic neuropathy, nerve disease and nerve damage (e.g., due to diabetic neuropathy), blood vessel blockage, heart disease, stroke, impotence (e.g., due to diabetic neuropathy or blood vessel blockage), seizures, mental confusion, drowsiness, nonketotic hyperglycemic-hyperosmolar coma, cardiovascular disease (e.g., heart disease, atherosclerosis, microvascular disease, hypertension, stroke, and other diseases and disorders as described in the ""Cardiovascular Disorders"" section below), dyslipidemia, endocrine disorders (as described in the |

TABLE 1E.2-continued

| Biological Activity No. | Biological Activity | Exemplary Activity Assay | Preferred Indication |
|---|---|---|---|
| | | Endocrinology, 138(9): 3735-40 (1997); Kim, K. H., et al., FEBS Lett, 377(2): 237-9 (1995); and, Miraglia S et. al., Journal of Biomolecular Screening, 4: 193-204 (1999), the contents of each of which is herein incorporated by reference in its entirety. Pancreatic cells that may be used according to these assays are publicly available (e.g., through the ATCC ™) and/or may be routinely generated. Exemplary pancreatic cells that may be used according to these assays include rat INS-1 cells. INS-1 cells are a semi-adherent cell line established from cells isolated from an X-ray induced rat transplantable insulinoma. These cells retain characteristics typical of native pancreatic beta cells including glucose inducible insulin secretion. References: Asfari et al. Endocrinology 1992 130: 167. | ""Endocrine Disorders"" section below), neuropathy, vision impairment (e.g., diabetic retinopathy and blindness), ulcers and impaired wound healing, and infection (e.g., infectious diseases and disorders as described in the ""Infectious Diseases"" section below, especially of the urinary tract and skin), carpal tunnel syndrome and Dupuytren's contracture). An additional highly preferred indication is obesity and/or complications associated with obesity. Additional highly preferred indications include weight loss or alternatively, weight gain. Aditional highly preferred indications are complications associated with insulin resistance. |
| 142 | TNFa in Human T-cell 293T | | |
| 143 | TNFa in Human T-cell 2B9 | | |
| 144 | Upregulation of CD152 and activation of T cells | CD152 FMAT. CD152 (a.k.a. CTLA-4) expression is restricted to activated T cells. CD152 is a negative regulator of T cell proliferation. Reduced CD152 expression has been linked to hyperproliferative and autoimmune diseases. Overexpression of CD152 may lead to impaired immunoresponses. Assays for immunomodulatory proteins important in the maintenance of T cell homeostasis and expressed almost exclusively on CD4+ and CD8+ T cells are well known in the art and may be used or routinely modified to assess the ability of polypeptides of the invention (including antibodies and agonists or antagonists of the invention) to modulate the activation of T cells, maintain T cell homeostasis, and/or mediate humoral or cell-mediated immunity. Exemplary assays that test for immunomodulatory proteins evaluate the upregulation of cell surface markers, such as CD152, and the activation of T cells. Such assays that may be used or routinely modified to test immunomodulatory activity of polypeptides of the invention (including antibodies and agonists or antagonists of the invention) include, for example, the assays disclosed in Miraglia et al., J Biomolecular Screening 4: 193-204 (1999); Rowland et al., ""Lymphocytes: a practical approach"" Chapter 6: 138-160 (2000); McCoy et al., Immunol Cell Biol 77(1): 1-10 (1999); Oostervegal et al., Curr Opin Immunol 11(3): 294-300 (1999); and Saito T, Curr Opin Immunol 10(3): 313-321 (1998), the contents of each of which are herein incorporated by reference in its entirety. Human T cells that may be used according to these assays may be isolated using techniques disclosed herein or otherwise known in the art. Human T cells are primary human lymphocytes that mature in the thymus and express a T Cell receptor and CD3, CD4, or CD8. These cells mediate humoral or cell-mediated immunity and may be preactivated to enhance responsiveness to immunomodulatory factors. | A highly preferred embodiment of the invention includes a method for activating T cells. An alternative highly preferred embodiment of the invention includes a method for inhibiting the activation of and/or inactivating T cells. A highly preferred embodiment of the invention includes a method for inhibiting T cell proliferation. An alternative highly preferred embodiment of the invention includes a method for stimulating T cell proliferation. Highly preferred indications include blood disorders (e.g., as described below under "Immune Activity", "Blood-Related Disorders", and/or ""Cardiovascular Disorders""), Highly preferred indications include autoimmune diseases (e.g., rheumatoid arthritis, systemic lupus erythematosis, multiple sclerosis and/or as described below), immunodeficiencies (e.g., as described below), boosting a T cell-mediated immune response, and suppressing a T cell-mediated immune response. Highly preferred indications include neoplastic diseases (e.g., leukemia, lymphoma, and/or as described below under "Hyperproliferative Disorders"). Additionally, highly preferred indications include neoplasms and cancers, such as, for example, leukemia, lymphoma, melanoma, and prostate, breast, lung, colon, pancreatic, esophageal, stomach, brain, liver and urinary cancer. Other preferred indications include benign dysproliferative disorders and pre-neoplastic conditions, such as, for example, hyperplasia, metaplasia, and/or dysplasia. Preferred indications include anemia, pancytopenia, leukopenia, thrombocytopenia, Hodgkin's disease, acute lymphocytic anemia (ALL), plasmacytomas, multiple myeloma, Burkitt's lymphoma, arthritis, AIDS, granulomatous disease, inflammatory bowel disease, sepsis, neutropenia, neutrophilia, psoriasis, immune reactions to transplanted organs and tissues, hemophilia, hypercoagulation, diabetes mellitus, endocarditis, meningitis, Lyme Disease, inflammation and inflammatory disorders, and asthma and allergy. An additional preferred indication is infection (e.g., as described below under "Infectious Disease"). |
| 145 | Upregulation of CD154 and activation of T cells | CD154 FMAT. CD154 (a.k.a., CD40L) expression is induced following activation of T cells. Interaction between CD154 and CD40 on B cells is required for correct | |

TABLE 1E.2-continued

| Biological Activity No. | Biological Activity | Exemplary Activity Assay | Preferred Indication |
|---|---|---|---|
| | | antibody class switching and germinal center formation. Mutations in CD154 are linked to immunodeficiencies and increased susceptibility to infections. Assays for immunomodulatory proteins important for antibody class switching and TH1 function and expressed on activated T helper lymphocytes are well known in the art and may be used or routinely modified to assess the ability of polypeptides of the invention (including antibodies and agonists or antagonists of the invention) to modulate the activation of T cells, modulate antibody class switching, mediate TH1 function, and/or mediate humoral or cell-mediated immunity. Exemplary assays that test for immunomodulatory proteins evaluate the upregulation of cell surface markers, such as CD154, and the activation of T cells. Such assays that may be used or routinely modified to test immunomodulatory activity of polypeptides of the invention (including antibodies and agonists or antagonists of the invention) include, for example, the assays disclosed in Miraglia et al., J Biomolecular Screening 4: 193-204 (1999); Rowland et al., "Lymphocytes: a practical approach" Chapter 6: 138-160 (2000); Mackey et al., J Leukoc Biol 63(4): 418: 428 (1998); and Skov et al., 164(7): 3500-3505 (2000), the contents of each of which are herein incorporated by reference in its entirety. Human T cells that may be used according to these assays may be isolated using techniques disclosed herein or otherwise known in the art. Human T cells are primary human lymphocytes that mature in the thymus and express a T Cell receptor and CD3, CD4, or CD8. These cells mediate humoral or cell-mediated immunity and may be preactivated to enhance responsiveness to immunomodulatory factors. | |
| 146 | Upregulation of CD69 and activation of T cells | CD69 FMAT. CD69 is an activation marker that is expressed on activated T cells, B cells, and NK cells. CD69 is not expressed on resting T cells, B cells, or NK cells. CD69 has been found to be associated with inflammation. Assays for immunomodulatory proteins expressed in T cells, B cells, and leukocytes are well known in the art and may be used or routinely modified to assess the ability of polypeptides of the invention (including antibodies and agonists or antagonists of the invention) to modulate the activation of T cells, and/or mediate humoral or cell-mediated immunity. Exemplary assays that test for immunomodulatory proteins evaluate the upregulation of cell surface markers, such as CD69, and the activation of T cells. Such assays that may be used or routinely modified to test immunomodulatory activity of polypeptides of the invention (including antibodies and agonists or antagonists of the invention) include, for example, the assays disclosed in Miraglia et al., J Biomolecular Screening 4: 193-204 (1999); Rowland et al., ""Lymphocytes: a practical approach"" Chapter 6: 138-160 (2000); Ferenczi et al., J Autoimmun 14(1): 63-78 (200); Werfel et al., Allergy 52(4): 465-469 (1997); Taylor-Fishwick and Siegel, Eur J Immunol 25(12): 3215-3221 (1995); and Afetra et al., Ann Rheum Dis 52(6): 457-460 (1993), the | A highly preferred embodiment of the invention includes a method for activating T cells. An alternative highly preferred embodiment of the invention includes a method for inhibiting the activation of and/or inactivating T cells. A highly preferred embodiment of the invention includes a method for activation B cells. An alternative highly preferred embodiment of the invention includes a method for inhibiting the activation of and/or inactivating B cells. A highly preferred embodiment of the invention includes a method for activating NK cells. An alternative highly preferred embodiment of the invention includes a method for inhibiting activation of and/or inactivation NK cells. Highly preferred indications include inflammation and inflammatory disorders (e.g., as described below under "Immune Activity"). Preferred indications include blood disorders (e.g., as described below under "Immune Activity", "Blood-Related Disorders", and/or ""Cardiovascular Disorders""). Highly preferred indications include autoimmune diseases (e.g., rheumatoid arthritis, systemic lupus erythematosis, multiple sclerosis and/or as described below), immunodeficiencies (e.g., as described below), boosting a T cell-mediated immune response and alternatively suppressing a T cell-mediated immune response, and boosting a B cell-mediated immune response and alternatively suppressing a B cell-mediated immune response. An additional highly preferred indication includes infection (e.g., as |

TABLE 1E.2-continued

| Biological Activity No. | Biological Activity | Exemplary Activity Assay | Preferred Indication |
|---|---|---|---|
| | | contents of each of which are herein incorporated by reference in its entirety. Human T cells that may be used according to these assays may be isolated using techniques disclosed herein or otherwise known in the art. Human T cells are primary human lymphocytes that mature in the thymus and express a T Cell receptor and CD3, CD4, or CD8. These cells mediate humoral or cell-mediated immunity and may be preactivated to enhance responsiveness to immunomodulatory factors. | described below under "Infectious Disease"). Preferred indications also include anemia, pancytopenia, leukopenia, thrombocytopenia, Hodgkin's disease, acute lymphocytic anemia (ALL), plasmacytomas, multiple myeloma, Burkitt's lymphoma, arthritis, AIDS, granulomatous disease, inflammatory bowel disease, sepsis, neutropenia, neutrophilia, psoriasis, suppression of immune reactions to transplanted organs and tissues, hemophilia, hypercoagulation, diabetes mellitus, endocarditis, meningitis, Lyme Disease, inflammation and inflammatory disorders, asthma, and allergies. Preferred indications also include neoplastic diseases (e.g., leukemia, lymphoma, and/or as described below under "Hyperproliferative Disorders"). Preferred indications include neoplasms, such as, for example, leukemia, lymphoma, and prostate, breast, lung, colon, pancreatic, esophageal, stomach, brain, liver and urinary cancer. Other preferred indications include benign dysproliferative disorders and pre-neoplastic conditions, such as, for example, hyperplasia, metaplasia, and/or dysplasia. |
| 147 | Upregulation of CD71 and activation of T cells | CD71 FMAT. CD71 is the transferrin receptor. Transferrin is a major iron carrying protein that is essential for cell proliferation. CD71 is expressed predominantly on cells that are actively proliferating. Assays for immunomodulatory proteins expressed on activated T cells, B cells, and most proliferating cells are well known in the art and may be used or routinely modified to assess the ability of polypeptides of the invention (including antibodies and agonists or antagonists of the invention) to modulate the activation of T cells, and/or mediate humoral or cell-mediated immunity. Exemplary assays that test for immunomodulatory proteins evaluate the upregulation of cell surface markers, such as CD71, and the activation of T cells. Such assays that may be used or routinely modified to test immunomodulatory activity of polypeptides of the invention (including antibodies and agonists or antagonists of the invention) include, for example, the assays disclosed in Miraglia et al., J Biomolecular Screening 4: 193-204 (1999); Rowland et al., "Lymphocytes: a practical approach" Chapter 6: 138-160 (2000); and Afetra et al., Ann Rheum Dis 52(6): 457-460 (1993), the contents of each of which are herein incorporated by reference in its entirety. Human T cells that may be used according to these assays may be isolated using techniques disclosed herein or otherwise known in the art. Human T cells are primary human lymphocytes that mature in the thymus and express a T Cell receptor and CD3, CD4, or CD8. These cells mediate humoral or cell-mediated immunity and may be preactivated to enhance responsiveness to immunomodulatory factors. | |
| 148 | Upregulation of HLA-DR and activation of T cells | HLA-DR FMAT. MHC class II is essential for correct presentation of antigen to CD4+ T cells. Deregulation of MHC class II has been associated with autoimmune diseases (e.g., diabetes, rheumatoid arthritis, systemic lupus erythematosis, and multiple sclerosis). Assays for immunomodulatory proteins expressed on MHC class II expressing T cells and antigen presenting | |

TABLE 1E.2-continued

| Biological Activity No. | Biological Activity | Exemplary Activity Assay | Preferred Indication |
|---|---|---|---|
| | | cells are well known in the art and may be used or routinely modified to assess the ability of polypeptides of the invention (including antibodies and agonists or antagonists of the invention) to modulate the activation of T cells, and/or mediate humoral or cell-mediated immunity. Exemplary assays that test for immunomodulatory proteins evaluate the upregulation of MHC class II products, such as HLA-DR antigens, and the activation of T cells. Such assays that may be used or routinely modified to test immunomodulatory activity of polypeptides of the invention (including antibodies and agonists or antagonists of the invention) include, for example, the assays disclosed in Miraglia et al., J Biomolecular Screening 4: 193-204 (1999); Rowland et al., "Lymphocytes: a practical approach" Chapter 6: 138-160 (2000); Lamour et al., Clin Exp Immunol 89(2): 217-222 (1992); Hurme and Sihvola, Immunol Lett 20(3): 217-222 (1989); Gansbacher and Zier, Cell Immunol 117(1): 22-34 (1988); and Itoh et al., J Histochem Cytochem 40(11): 1675-1683, the contents of each of which are herein incorporated by reference in its entirety. Human T cells that may be used according to these assays may be isolated using techniques disclosed herein or otherwise known in the art. Human T cells are primary human lymphocytes that mature in the thymus and express a T Cell receptor and CD3, CD4, or CD8. These cells mediate humoral or cell-mediated immunity and may be preactivated to enhance responsiveness to immunomodulatory factors. | |
| 149 | VEGF in SW480 | | |

Table 1F: Polynucleotides encoding polypeptides of the present invention can be used in assays to test for one or more biological activities. One such biological activity which may be tested includes the ability of polynucleotides and polypeptides of the invention to stimulate up-regulation or down-regulation of expression of particular genes and proteins. Hence, if polynucleotides and polypeptides of the present invention exhibit activity in altering particular gene and protein expression patterns, it is likely that these polynucleotides and polypeptides of the present invention may be involved in, or capable of effecting changes in, diseases associated with the altered gene and protein expression profiles. Hence, polynucleotides, polypeptides, or antibodies of the present invention could be used to treat said associated diseases.

TaqMan® assays may be performed to assess the ability of polynucleotides (and polypeptides they encode) to alter the expression pattern of particular "target" genes. TaqMan® reactions are performed to evaluate the ability of a test agent to induce or repress expression of specific genes in different cell types. TaqMan® gene expression quantification assays ("TaqMan® assays") are well known to, and routinely performed by, those of ordinary skill in the art. TaqMan® assays are performed in a two step reverse transcription/polymerase chain reaction (RT-PCR). In the first (RT) step, cDNA is reverse transcribed from total RNA samples using random hexamer primers. In the second (PCR) step, PCR products are synthesized from the cDNA using gene specific primers.

To quantify gene expression the TaqMan® PCR reaction exploits the 5' nuclease activity of AmpliTaq Gold® DNA Polymerase to cleave a TaqMan® probe (distinct from the primers) during PCR. The TaqMan® probe contains a reporter dye at the 5'-end of the probe and a quencher dye at the 3' end of the probe. When the probe is intact, the proximity of the reporter dye to the quencher dye results in suppression of the reporter fluorescence. During PCR, if the target of interest is present, the probe specifically anneals between the forward and reverse primer sites. AmpliTaq Gold® DNA Polymerase then cleaves the probe between the reporter and quencher when the probe hybridizes to the target, resulting in increased fluorescence of the reporter (see FIG. 2). Accumulation of PCR products is detected directly by monitoring the increase in fluorescence of the reporter dye.

After the probe fragments are displaced from the target, polymerization of the strand continues. The 3'-end of the probe is blocked to prevent extension of the probe during PCR. This process occurs in every cycle and does not interfere with the exponential accumulation of product. The increase in fluorescence signal is detected only if the target sequence is complementary to the probe and is amplified during PCR. Because of these requirements, any nonspecific amplification is not detected.

For test sample preparation, vector controls or constructs containing the coding sequence for the gene of interest are transfected into cells, such as for example 293T cells, and supernatants collected after 48 hours. For cell treatment and RNA isolation, multiple primary human cells or human cell lines are used; such cells may include but are not limited to, Normal Human Dermal Fibroblasts, Aortic Smooth Muscle, Human Umbilical Vein Endothelial Cells, HepG2, Daudi, Jurkat, U937, Caco, and THP-1 cell lines. Cells are plated in growth media and growth is arrested by culturing without media change for 3 days, or by switching cells to low serum media and incubating overnight. Cells are treated for 1, 6, or 24 hours with either vector control supernatant or sample supernatant (or purified/partially purified protein preparations in buffer). Total RNA is isolated; for example, by using TRIZOL™ extraction or by using the Ambion RNAqueous™-4PCR RNA isolation system. Expression levels of multiple genes are analyzed using TaqMan®, and expression in the test sample is compared to control vector samples to identify genes induced or repressed. Each of the above described techniques are well known to, and routinely performed by, those of ordinary skill in the art.

Table 1F indicates particular disease classes and preferred indications for which polynucleotides, polypeptides, or antibodies of the present invention may be used in detecting, diagnosing, preventing, treating and/or ameliorating said diseases and disorders based on "target" gene expression patterns which may be up- or down-regulated by polynucleotides (and the encoded polypeptides) corresponding to each indicated cDNA Clone ID (shown in Table 1F, Column 2).

Thus, in preferred embodiments, the present invention encompasses a method of detecting, diagnosing, preventing, treating, and/or ameliorating a disease or disorder listed in the "Disease Class" and/or "Preferred Indication" columns of Table 1F; comprising administering to a patient in which such detection, diagnosis, prevention, or treatment is desired a protein, nucleic acid, or antibody of the invention (or fragment or variant thereof) in an amount effective to detect, diagnose, prevent, treat, or ameliorate the disease or disorder. The first and second columns of Table 1F shows the "Gene No." and "cDNA Clone ID No.", respectively, indicating certain nucleic acids and proteins (or antibodies against the same) of the invention (including polynucleotide, polypeptide, and antibody fragments or variants thereof) that may be used in detecting, diagnosing, preventing, treating, or ameliorating the disease(s) or disorder(s) indicated in the corresponding row in the "Disease Class" or "Preferred Indication" Columns of Table 1F.

In another embodiment, the present invention also encompasses methods of detecting, diagnosing, preventing, treating, or ameliorating a disease or disorder listed in the "Disease Class" or "Preferred Indication" Columns of Table 1F; comprising administering to a patient combinations of the proteins, nucleic acids, or antibodies of the invention (or fragments or variants thereof), sharing similar indications as shown in the corresponding rows in the "Disease Class" or "Preferred Indication" Columns of Table 1F.

The "Disease Class" Column of Table 1F provides a categorized descriptive heading for diseases, disorders, and/or conditions (more fully described below) that may be detected, diagnosed, prevented, treated, or ameliorated by a protein, nucleic acid, or antibody of the invention (or fragment or variant thereof).

The "Preferred Indication" Column of Table 1F describes diseases, disorders, and/or conditions that may be detected, diagnosed, prevented, treated, or ameliorated by a protein, nucleic acid, or antibody of the invention (or fragment or variant thereof).

The "Cell Line" and "Exemplary Targets" Columns of Table 1F indicate particular cell lines and target genes, respectively, which may show altered gene expression patterns (i.e., up- or down-regulation of the indicated target gene) in TaqMan® assays, performed as described above, utilizing polynucleotides of the cDNA Clone ID shown in the corresponding row. Alteration of expression patterns of the indicated "Exemplary Target" genes is correlated with a particular "Disease Class" and/or "Preferred Indication" as shown in the corresponding row under the respective column headings.

The "Exemplary Accessions" Column indicates GenBank Accessions (available online through the National Center for Biotechnology Information (NCBI) at the world wide web at ncbi.nlm.nih.gov/) which correspond to the "Exemplary Targets" shown in the adjacent row.

The recitation of "Cancer" in the "Disease Class" Column indicates that the corresponding nucleic acid and protein, or antibody against the same, of the invention (or fragment or variant thereof) may be used for example, to detect, diagnose, prevent, treat, and/or ameliorate neoplastic diseases and/or disorders (e.g., leukemias, cancers, etc., as described below under "Hyperproliferative Disorders").

The recitation of "Immune" in the "Disease Class" column indicates that the corresponding nucleic acid and protein, or antibody against the same, of the invention (or fragment or variant thereof), may be used for example, to detect, diagnose, prevent, treat, and/or ameliorate diseases and/or disorders relating to neoplastic diseases (e.g., as described below under "Hyperproliferative Disorders"), blood disorders (e.g., as described below under "Immune Activity" "Cardiovascular Disorders" and/or "Blood-Related Disorders"), and infections (e.g., as described below under "Infectious Disease").

The recitation of "Angiogenesis" in the "Disease Class" column indicates that the corresponding nucleic acid and protein, or antibody against the same, of the invention (or fragment or variant thereof), may be used for example, to detect, diagnose, treat, prevent, and/or ameliorate diseases and/or disorders relating to neoplastic diseases (e.g., as described below under "Hyperproliferative Disorders"), diseases and/or disorders of the cardiovascular system (e.g., as described below under "Cardiovascular Disorders"), diseases and/or disorders involving cellular and genetic abnormalities (e.g., as described below under "Diseases at the Cellular Level"), diseases and/or disorders involving angiogenesis (e.g., as described below under "Anti-Angiogenesis Activity"), to promote or inhibit cell or tissue regeneration (e.g., as described below under "Regeneration"), or to promote wound healing (e.g., as described below under "Wound Healing and Epithelial Cell Proliferation"). Highly preferred indications include diagnosis, prevention, treatment, and/or amelioration of diseases and disorders involving angiogenesis, wound healing, neoplasia (particularly including, but not limited to, tumor metastases), and cardiovascular diseases and disorders; as described herein under the headings "Hyperproliferative Disorders," "Regeneration," "Anti-Angiogenesis Activity," "Diseases at the Cellular Level," and "Wound Healing and Epithelial Cell Proliferation."

The recitation of "Diabetes" in the "Disease Class" column indicates that the corresponding nucleic acid and protein, or antibody against the same, of the invention (or fragment or variant thereof), may be used for example, to detect, diagnose, treat, prevent, and/or ameliorate diabetes (including diabetes mellitus types I and II), as well as diseases and/or disorders associated with, or consequential to, diabetes (e.g. as described below under "Endocrine Disorders," "Renal Disorders," and "Gastrointestinal Disorders").

TABLE 1F

| Gene No. | cDNA Clone ID | Disease Class | Preferred Indications | Cell Line | Exemplary Targets | Exemplary Accessions |
|---|---|---|---|---|---|---|
| 14 | HJACG02 | Angiogenesis | Highly preferred indications include diagnosis, prevention, treatment, and/or amelioration of diseases and disorders involving angiogenesis, wound healing, neoplasia (particularly including, but not limited to, tumor metastases), and cardiovascular diseases and disorders; as described herein under the headings "Hyperproliferative Disorders," "Regeneration," "Anti-Angiogenesis Activity," "Diseases at the Cellular Level," and "Wound Healing and Epithelial Cell Proliferation." | Adipocytes-Mar. 12, 2001 | ICAM<br>PAI<br>Vegf1 | gb\|X06990\|HSICAM1<br>gb\|X12701\|HSENDPAI<br>gb\|AF024710\|AF024710 |
| 14 | HJACG02 | Angiogenesis | Highly preferred indications include diagnosis, prevention, treatment, and/or amelioration of diseases and disorders involving angiogenesis, wound healing, neoplasia (particularly including, but not limited to, tumor metastases), and cardiovascular diseases and disorders; as described herein under the headings "Hyperproliferative Disorders," "Regeneration," "Anti-Angiogenesis Activity," "Diseases at the Cellular Level," and "Wound Healing and Epithelial Cell Proliferation."(AOSMC cells are aortic smooth muscle cells). | AOSMC | VCAM | gb\|A30922\|A30922 |
| 14 | HJACG02 | Angiogenesis | Highly preferred indications include diagnosis, prevention, treatment, and/or amelioration of diseases and disorders involving angiogenesis, wound healing, neoplasia (particularly including, but not limited to, tumor metastases), and cardiovascular diseases and disorders; as described herein under the headings "Hyperproliferative Disorders," "Regeneration," "Anti-Angiogenesis Activity," "Diseases at the Cellular Level," and "Wound Healing and Epithelial Cell Proliferation."(The Daudi cell line is a human B lymphoblast cell line available through the ATCC ™ as cell line number CCL-213). | Daudi | ICAM<br>VCAM | gb\|X06990\|HSICAM1<br>gb\|A30922\|A30922 |

TABLE 1F-continued

| Gene No. | cDNA Clone ID | Disease Class | Preferred Indications | Cell Line | Exemplary Targets | Exemplary Accessions |
|---|---|---|---|---|---|---|
| 14 | HJACG02 | Angiogenesis | Highly preferred indications include diagnosis, prevention, treatment, and/or amelioration of diseases and disorders involving angiogenesis, wound healing, neoplasia (particularly including, but not limited to, tumor metastases), and cardiovascular diseases and disorders; as described herein under the headings “Hyperproliferative Disorders,” “Regeneration,” “Anti-Angiogenesis Activity,” “Diseases at the Cellular Level,” and “Wound Healing and Epithelial Cell Proliferation.”(HUVEC cells are human umbilical vein endothelial cells). | HUVEC | ICAM<br>TSP-1<br>Vegf1 | gb\|X06990\|HSICAM1<br>gb\|X04665\|HSTHROMR<br>gb\|AF024710\|AF024710 |
| 14 | HJACG02 | Cancer | Highly preferred indications include neoplastic diseases (e.g. cancer) such as described herein under the heading “Hyperproliferative Disordersî (particularly including, but not limited to, cancer involving adipocytes). Highly preferred embodiments of the invention include methods of preventing, detecting, diagnosing, treating and/or ameliorating cancer and hyperproliferative disorders. (Primary adipocytes) | Adipocytes-Mar. 12, 2001 | Egr1 | |
| 14 | HJACG02 | Cancer | Highly preferred indications include neoplastic diseases (e.g. cancer) such as described herein under the heading “Hyperproliferative Disordersî (particularly including, but not limited to, cancers of muscle tissues and the cardiovascular system (e.g. heart, lungs, circulatory system)). Highly preferred embodiments of the invention include methods of preventing, detecting, diagnosing, treating and/or ameliorating cancer and hyperproliferative disorders. (AOSMC cells are aortic smooth muscle cells). | AOSMC | M1 RIBO R | gb\|X59543\|HSRIREM1 |
| 14 | HJACG02 | Cancer | Highly preferred indications include neoplastic diseases (e.g. cancer) such as described herein under the heading “Hyperproliferative Disordersî (particularly including, but not limited | Daudi | Cyclin A1 | gb\|U97680\|HSU97680 |

TABLE 1F-continued

| Gene No. | cDNA Clone ID | Disease Class | Preferred Indications | Cell Line | Exemplary Targets | Exemplary Accessions |
|---|---|---|---|---|---|---|
| | | | to, cancers of immune cells, such as B-cells). Highly preferred embodiments of the invention include methods of preventing, detecting, diagnosing, treating and/or ameliorating cancer and hyperproliferative disorders involving immune cells (such as B-cells). (The Daudi cell line is a human B lymphoblast cell line available through the ATCC ™ as cell line number CCL-213). | | | |
| 14 | HJACG02 | Cancer | Highly preferred indications include neoplastic diseases (e.g. cancer) such as described herein under the heading "Hyperproliferative Disordersî (particularly including, but not limited to, cancers of epithelial cells or cancers involving the renal system). Highly preferred embodiments of the invention include methods of preventing, detecting, diagnosing, treating and/or ameliorating cancer and hyperproliferative disorders involving epithelial cells or the renal system. (The 293 cell line human embryonal kidney epithelial cell line available through the ATCC ™ as cell line number CRL-1573). | HEK293 | E-cadherin | gb\|Z35408\|HSECAD9 |
| 14 | HJACG02 | Cancer | Highly preferred indications include neoplastic diseases (e.g. cancer) such as described herein under the heading "Hyperproliferative Disordersî (particularly including, but not limited to, cancers of immune cells, such as T-cells). Highly preferred embodiments of the invention include methods of preventing, detecting, diagnosing, treating and/or ameliorating cancer and hyperproliferative disorders involving immune cells (such as T-cells). (The Jurkat cell line is a human T lymphocyte cell line available through the ATCC ™ as cell line number TIB-152). | Jurkat | Cyclin A1 | gb\|U97680\|HSU97680 |
| 14 | HJACG02 | Cancer | Highly preferred indications include neoplastic diseases (e.g. cancer) such as described herein under the heading "Hyperproliferative Disordersî (particularly including, but not limited | Liver | Cyclin D2 | gb\|X68452\|HSCYCD2 |

TABLE 1F-continued

| Gene No. | cDNA Clone ID | Disease Class | Preferred Indications | Cell Line | Exemplary Targets | Exemplary Accessions |
|---|---|---|---|---|---|---|
| | | | to, cancers involving cells of the hepatic system). Highly preferred embodiments of the invention include methods of preventing, detecting, diagnosing, treating and/or ameliorating cancer and hyperproliferative disorders involving cells of the hepatic system. | | | |
| 14 | HJACG02 | Cancer | Highly preferred indications include neoplastic diseases (e.g. cancer) such as described herein under the heading "Hyperproliferative Disordersî (particularly including, but not limited to cancers involving cells of the skin). Highly preferred embodiments of the invention include methods of preventing, detecting, diagnosing, treating and/or ameliorating cancer and hyperproliferative disorders involving skin cells. (NHDF cells are normal human dermal fibroblasts). | NHDF | Cyclin A1 | gb\|U97680\|HSU97680 |
| 14 | HJACG02 | Diabetes | A highly preferred indication is diabetes. Additional highly preferred indications include complications associated with diabetes (e.g., diabetic retinopathy, diabetic nephropathy, kidney disease (e.g., renal failure, nephropathy and/or other diseases and disorders as described in the "Renal Disorders" section below), diabetic neuropathy, nerve disease and nerve damage (e.g., due to diabetic neuropathy), blood vessel blockage, heart disease, stroke, impotence (e.g., due to diabetic neuropathy or blood vessel blockage), seizures, mental confusion, drowsiness, nonketotic hyperglycemic-hyperosmolar coma, cardiovascular disease (e.g., heart disease, atherosclerosis, microvascular disease, hypertension, stroke, and other diseases and disorders as described in the "Cardiovascular Disorders" section below), dyslipidemia, endocrine disorders (as described in the "Endocrine Disorders" section below), neuropathy, vision impairment (e.g., diabetic | Adipocytes (4D)- Sep. 1, 2001 | CAP<br>PEPCK1 | gb\|AF136380\|AF136380<br>gb\|L05144\|HUMPHOCAR |

TABLE 1F-continued

| Gene No. | cDNA Clone ID | Disease Class | Preferred Indications | Cell Line | Exemplary Targets | Exemplary Accessions |
|---|---|---|---|---|---|---|
| | | | retinopathy and blindness), ulcers and impaired wound healing, and infection (e.g., infectious diseases and disorders as described in the "Infectious Diseases" section below, especially of the urinary tract and skin). Highly preferred indications also include obesity, weight gain, and weight loss, as well as complications associated with obesity, weight gain, and weight loss. Preferred embodiments of the invention include methods of preventing, detecting, diagnosing, treating and/or ameliorating the above mentioned conditions, disorders, and diseases. | | | |
| 14 | HJACG02 | Diabetes | A highly preferred indication is diabetes. Additional highly preferred indications include complications associated with diabetes (e.g., diabetic retinopathy, diabetic nephropathy, kidney disease (e.g., renal failure, nephropathy and/or other diseases and disorders as described in the "Renal Disorders" section below), diabetic neuropathy, nerve disease and nerve damage (e.g., due to diabetic neuropathy), blood vessel blockage, heart disease, stroke, impotence (e.g., due to diabetic neuropathy or blood vessel blockage), seizures, mental confusion, drowsiness, nonketotic hyperglycemic-hyperosmolar coma, cardiovascular disease (e.g., heart disease, atherosclerosis, microvascular disease, hypertension, stroke, and other diseases and disorders as described in the "Cardiovascular Disorders" section below), dyslipidemia, endocrine disorders (as described in the "Endocrine Disorders" section below), neuropathy, vision impairment (e.g., diabetic retinopathy and blindness), ulcers and impaired wound healing, and infection (e.g., infectious diseases and disorders as described in the "Infectious Diseases" section below, especially of the urinary tract and | Adipocytes-Mar. 12, 2001 | CAP Hexokinase II | gb\|AF136380\|AF136380 gb\|Z46354\|HSHKEX1 |

TABLE 1F-continued

| Gene No. | cDNA Clone ID | Disease Class | Preferred Indications | Cell Line | Exemplary Targets | Exemplary Accessions |
|---|---|---|---|---|---|---|
| | | | skin). Highly preferred indications also include obesity, weight gain, and weight loss, as well as complications associated with obesity, weight gain, and weight loss. Preferred embodiments of the invention include methods of preventing, detecting, diagnosing, treating and/or ameliorating the above mentioned conditions, disorders, and diseases. | | | |
| 14 | HJACG02 | Diabetes | A highly preferred indication is diabetes. Additional highly preferred indications include complications associated with diabetes (e.g., diabetic retinopathy, diabetic nephropathy, kidney disease (e.g., renal failure, nephropathy and/or other diseases and disorders as described in the "Renal Disorders" section below), diabetic neuropathy, nerve disease and nerve damage (e.g., due to diabetic neuropathy), blood vessel blockage, heart disease, stroke, impotence (e.g., due to diabetic neuropathy or blood vessel blockage), seizures, mental confusion, drowsiness, nonketotic hyperglycemic-hyperosmolar coma, cardiovascular disease (e.g., heart disease, atherosclerosis, microvascular disease, hypertension, stroke, and other diseases and disorders as described in the "Cardiovascular Disorders" section below), dyslipidemia, endocrine disorders (as described in the "Endocrine Disorders" section below), neuropathy, vision impairment (e.g., diabetic retinopathy and blindness), ulcers and impaired wound healing, and infection (e.g., infectious diseases and disorders as described in the "Infectious Diseases" section below, especially of the urinary tract and skin). Highly preferred indications also include obesity, weight gain, and weight loss, as well as complications associated with obesity, weight gain, and weight loss. Preferred embodiments of the invention include | AOSMC | IRS1 PPARg | gb\|X90563\|HSPPARGAM |

TABLE 1F-continued

| Gene No. | cDNA Clone ID | Disease Class | Preferred Indications | Cell Line | Exemplary Targets | Exemplary Accessions |
|---|---|---|---|---|---|---|
| | | | methods of preventing, detecting, diagnosing, treating and/or ameliorating the above mentioned conditions, disorders, and diseases. (AOSMC cells are human aortic smooth muscle cells). | | | |
| 14 | HJACG02 | Diabetes | A highly preferred indication is diabetes. Additional highly preferred indications include complications associated with diabetes (e.g., diabetic retinopathy, diabetic nephropathy, kidney disease (e.g., renal failure, nephropathy and/or other diseases and disorders as described in the "Renal Disorders" section below), diabetic neuropathy, nerve disease and nerve damage (e.g., due to diabetic neuropathy), blood vessel blockage, heart disease, stroke, impotence (e.g., due to diabetic neuropathy or blood vessel blockage), seizures, mental confusion, drowsiness, nonketotic hyperglycemic-hyperosmolar coma, cardiovascular disease (e.g., heart disease, atherosclerosis, microvascular disease, hypertension, stroke, and other diseases and disorders as described in the "Cardiovascular Disorders" section below), dyslipidemia, endocrine disorders (as described in the "Endocrine Disorders" section below), neuropathy, vision impairment (e.g., diabetic retinopathy and blindness), ulcers and impaired wound healing, and infection (e.g., infectious diseases and disorders as described in the "Infectious Diseases" section below, especially of the urinary tract and skin). Highly preferred indications also include obesity, weight gain, and weight loss, as well as complications associated with obesity, weight gain, and weight loss. Preferred embodiments of the invention include methods of preventing, detecting, diagnosing, treating and/or ameliorating the above mentioned conditions, disorders, and diseases. | Liver | Glucose6 phosphatase | gb\|U91844\|CFU91844 |

TABLE 1F-continued

| Gene No. | cDNA Clone ID | Disease Class | Preferred Indications | Cell Line | Exemplary Targets | Exemplary Accessions |
|---|---|---|---|---|---|---|
| 14 | HJACG02 | Immune | Highly preferred indications include immunological disorders such as described herein under the heading "Immune Activity" and/or "Blood-Related Disorders" (particularly including, but not limited to, immune disorders involving adipocytes). Highly preferred embodiments of the invention include methods of preventing, detecting, diagnosing, treating and/or ameliorating disorders of the immune system (particularly including, but not limited to, immune disorders involving adipocytes). | Adipocytes-Mar. 12, 2001 | ICAM<br>Il6<br>Rag1 | gb\|X06990\|HSICAM1<br>gb\|X04403\|HS26KDAR<br>gb\|M29474\|HUMRAG1 |
| 14 | HJACG02 | Immune | Highly preferred indications include immunological disorders such as described herein under the heading "Immune Activity" and/or "Blood-Related Disorders" (particularly including, but not limited to, immune disorders involving muscle tissues and the cardiovascular system (e.g. heart, lungs, circulatory system)). Highly preferred embodiments of the invention include methods of preventing, detecting, diagnosing, treating and/or ameliorating disorders of the immune system (particularly including, but not limited to, immune disorders involving muscle tissue or the cardiovascular system). (AOSMC cells are human aortic smooth muscle cells). | AOSMC | CD30<br>CD40<br>IL1B<br>IL5<br>TNF<br>VCAM | gb\|AJ300189\|HSA30018<br>gb\|X02532\|HSIL1BR<br>gb\|X12705\|HSBCDFIA<br>gb\|AJ270944\|HSA27094<br>gb\|A30922\|A30922 |
| 14 | HJACG02 | Immune | Highly preferred indications include immunological disorders such as described herein under the heading "Immune Activity" and/or "Blood-Related Disorders" (particularly including, but not limited to, immune disorders involving the cells of the gastrointestinal tract). Highly preferred embodiments of the invention include methods of preventing, detecting, diagnosing, treating and/or ameliorating disorders of the immune system (particularly including, but not limited to, immune disorders involving cells of the | Caco-2 | Rag1 | gb\|M29474\|HUMRAG1 |

TABLE 1F-continued

| Gene No. | cDNA Clone ID | Disease Class | Preferred Indications | Cell Line | Exemplary Targets | Exemplary Accessions |
|---|---|---|---|---|---|---|
| | | | gastrointestinal tract). (The Caco-2 cell line is a human colorectal adenocarcinoma cell line available through the ATCC ™ as cell line number HTB-37). | | | |
| 14 | HJACG02 | Immune | Highly preferred indications include immunological disorders such as described herein under the heading “Immune Activity” and/or “Blood-Related Disorders” (particularly including, but not limited to, immune disorders involving the B-cells). Highly preferred embodiments of the invention include methods of preventing, detecting, diagnosing, treating and/or ameliorating disorders of the immune system (particularly including, but not limited to, immune disorders involving B-cells). (The Daudi cell line is a human B lymphoblast cell line available through the ATCC ™ as cell line number CCL-213). | Daudi | ICAM<br>Rag1<br>VCAM | gb\|X06990\|HSICAM1<br>gb\|M29474\|HUMRAG1<br>gb\|A30922\|A30922 |
| 14 | HJACG02 | Immune | Highly preferred indications include immunological disorders such as described herein under the heading “Immune Activity” and/or “Blood-Related Disorders” (particularly including, but not limited to, immune disorders involving epithelial cells or the renal system). Highly preferred embodiments of the invention include methods of preventing, detecting, diagnosing, treating and/or ameliorating disorders of the immune system (particularly including, but not limited to, immune disorders involving epithelial cells or the renal system). (The 293 cell line is a human embryonal kidney epithelial cell line available through the ATCC ™ as cell line number CRL-1573). | HEK293 | c-maf | gb\|AF055377\|AF055377 |
| 14 | HJACG02 | Immune | Highly preferred indications include immunological disorders such as described herein under the heading “Immune Activity” and/or “Blood-Related Disorders” (particularly including, but not limited to, immune disorders involving endothelial | HUVEC | ICAM | gb\|X06990\|HSICAM1 |

TABLE 1F-continued

| Gene No. | cDNA Clone ID | Disease Class | Preferred Indications | Cell Line | Exemplary Targets | Exemplary Accessions |
|---|---|---|---|---|---|---|
| | | | cells). Highly preferred embodiments of the invention include methods of preventing, detecting, diagnosing, treating and/or ameliorating disorders of the immune system (particularly including, but not limited to, immune disorders involving endothelial cells). (HUVEC cells are human umbilical vein endothelial cells). | | | |
| 14 | HJACG02 | Immune | Highly preferred indications include immunological disorders such as described herein under the heading “Immune Activity” and/or “Blood-Related Disorders” (particularly including, but not limited to, immune disorders involving T-cells). Highly preferred embodiments of the invention include methods of preventing, detecting, diagnosing, treating and/or ameliorating disorders of the immune system (particularly including, but not limited to, immune disorders involving T-cells). (The Jurkat cell line is a human T lymphocyte cell line available through the ATCC ™ as cell line number TIB-152). | Jurkat | Rag2<br>TNF | gb\|AY011962\|AY011962<br>gb\|AJ270944\|HSA27094 |
| 14 | HJACG02 | Immune | Highly preferred indications include immunological disorders such as described herein under the heading “Immune Activity” and/or “Blood-Related Disorders” (particularly including, but not limited to, immune disorders involving the skin). Highly preferred embodiments of the invention include methods of preventing, detecting, diagnosing, treating and/or ameliorating disorders of the immune system (particularly including, but not limited to, immune disorders involving the skin). (NHDF cells are normal human dermal fibroblasts). | NHDF | Rag1 | gb\|M29474\|HUMRAG1 |
| 14 | HJACG02 | Immune | Highly preferred indications include immunological disorders such as described herein under the heading “Immune Activity” and/or “Blood-Related Disorders” (particularly | U937 | GATA1<br>IL5<br>TNF | gb\|X17254\|HSERYF1<br>gb\|X12705\|HSBCDFIA<br>gb\|AJ270944\|HSA27094 |

TABLE 1F-continued

| Gene No. | cDNA Clone ID | Disease Class | Preferred Indications | Cell Line | Exemplary Targets | Exemplary Accessions |
|---|---|---|---|---|---|---|
| | | | including, but not limited to, immune disorders involving monocytes). Highly preferred embodiments of the invention include methods of preventing, detecting, diagnosing, treating and/or ameliorating disorders of the immune system (particularly including, but not limited to, immune disorders involving monocytes). (The U937 cell line is a human monocyte cell line available through the ATCC ™ as cell line number CRL-1593.2). | | | |
| 14 | HJACG02 | Immune | Highly preferred indications include immunological disorders such as described herein under the heading “Immune Activity” and/or “Blood-Related Disorders” (particularly including, but not limited to, immune disorders involving adipocytes). Highly preferred embodiments of the invention include methods of preventing, detecting, diagnosing, treating and/or ameliorating disorders of the immune system (particularly including, but not limited to, immune disorders involving adipocytes). | Adipocytes-Mar. 12, 2001 | ICAM<br>Il6<br>Rag1 | gb\|X06990\|HSICAM1<br>gb\|X04403\|HS26KDAR<br>gb\|M29474\|HUMRAG1 |
| 14 | HJACG02 | Immune | Highly preferred indications include immunological disorders such as described herein under the heading “Immune Activity” and/or “Blood-Related Disorders” (particularly including, but not limited to, immune disorders involving muscle tissues and the cardiovascular system (e.g. heart, lungs, circulatory system)). Highly preferred embodiments of the invention include methods of preventing, detecting, diagnosing, treating and/or ameliorating disorders of the immune system (particularly including, but not limited to, immune disorders involving muscle tissue or the cardiovascular system). (AOSMC cells are human aortic smooth muscle cells). | AOSMC | CD30<br>CD40<br>IL1B<br>IL5<br>TNF<br>VCAM | <br>gb\|AJ300189\|HSA30018<br>gb\|X02532\|HSIL1BR<br>gb\|X12705\|HSBCDFIA<br>gb\|AJ270944\|HSA27094<br>gb\|A30922\|A30922 |
| 14 | HJACG02 | Immune | Highly preferred indications include immunological disorders such as described herein | Caco-2 | Rag1 | gb\|M29474\|HUMRAG1 |

TABLE 1F-continued

| Gene No. | cDNA Clone ID | Disease Class | Preferred Indications | Cell Line | Exemplary Targets | Exemplary Accessions |
|---|---|---|---|---|---|---|
| | | | under the heading "Immune Activity" and/or "Blood-Related Disorders" (particularly including, but not limited to, immune disorders involving the cells of the gastrointestinal tract). Highly preferred embodiments of the invention include methods of preventing, detecting, diagnosing, treating and/or ameliorating disorders of the immune system (particularly including, but not limited to, immune disorders involving cells of the gastrointestinal tract). (The Caco-2 cell line is a human colorectal adenocarcinoma cell line available through the ATCC ™ as cell line number HTB-37). | | | |

Table 2 further characterizes certain encoded polypeptides of the invention, by providing the results of comparisons to protein and protein family databases. The first column provides a unique clone identifier, "Clone ID NO:", corresponding to a cDNA clone disclosed in Tables 1A, 1B.1, and/or 1B.2. The second column provides the unique contig identifier, "Contig ID:" which allows correlation with the information in Tables 1B.1 and 1B.2. The third column provides the sequence identifier, "SEQ ID NO:", for the contig polynucleotide sequences. The fourth column provides the analysis method by which the homology/identity disclosed in the Table was determined. The fifth column provides a description of the PFAM/NR hit identified by each analysis. Column six provides the accession number of the PFAM/NR hit disclosed in the fifth column. Column seven, score/percent identity, provides a quality score or the percent identity, of the hit disclosed in column five. Comparisons were made between polypeptides encoded by polynucleotides of the invention and a non-redundant protein database (herein referred to as "NR"), or a database of protein families (herein referred to as "PFAM"), as described below.

The NR database, which comprises the NBRF PIR database, the NCBI GenPept database, and the SIB SwissProt and TrEMBL databases, was made non-redundant using the computer program nrdb2 (Warren Gish, Washington University in Saint Louis). Each of the polynucleotides shown in Tables 1B.1 and 1B.2, column 3 (e.g., SEQ ID NO:X or the 'Query' sequence) was used to search against the NR database. The computer program BLASTX was used to compare a 6-frame translation of the Query sequence to the NR database (for information about the BLASTX algorithm please see Altshul et al., J. Mol. Biol. 215:403-410 (1990), and Gish and States, Nat. Genet. 3:266-272 (1993). A description of the sequence that is most similar to the Query sequence (the highest scoring 'Subject') is shown in column five of Table 2 and the database accession number for that sequence is provided in column six. The highest scoring 'Subject' is reported in Table 2 if (a) the estimated probability that the match occurred by chance alone is less than 1.0e-07, and (b) the match was not to a known repetitive element. BLASTX returns alignments of short polypeptide segments of the Query and Subject sequences which share a high degree of similarity; these segments are known as High-Scoring Segment Pairs or HSPs. Table 2 reports the degree of similarity between the Query and the Subject for each HSP as a percent identity in Column 7. The percent identity is determined by dividing the number of exact matches between the two aligned sequences in the HSP, dividing by the number of Query amino acids in the HSP and multiplying by 100. The polynucleotides of SEQ ID NO:X which encode the polypeptide sequence that generates an HSP are delineated by columns 8 and 9 of Table 2.

The PFAM database, PFAM version 2.1, (Sonnhammer, Nucl. Acids Res., 26:320-322, 1998)) consists of a series of multiple sequence alignments; one alignment for each protein family. Each multiple sequence alignment is converted into a probability model called a Hidden Markov Model, or HMM, that represents the position-specific variation among the sequences that make up the multiple sequence alignment (see, e.g., Durbin, et al., *Biological sequence analysis: probabilistic models of proteins and nucleic acids*, Cambridge University Press, 1998 for the theory of HMMs). The program HMMER version 1.8 (Sean Eddy, Washington University in Saint Louis) was used to compare the predicted protein sequence for each Query sequence (SEQ ID NO:Y in Table 1B.1) to each of the HMMs derived from PFAM version 2.1. A HMM derived from PFAM version 2.1 was said to be a significant match to a polypeptide of the invention if the score returned by HMMER 1.8 was greater than 0.8 times the HMMER 1.8 score obtained with the most distantly related known member of that protein family. The description of the PFAM family which shares a significant match with a polypeptide of the invention is listed in column 5 of Table 2, and the database accession number of the PFAM hit is provided in column 6. Column 7 provides the score returned by HMMER version 1.8 for the alignment. Columns 8 and 9 delineate the polynucleotides of SEQ ID NO:X which encode the polypeptide sequence which show a significant match to a PFAM protein family.

As mentioned, columns 8 and 9 in Table 2, "NT From" and "NT To", delineate the polynucleotides of "SEQ ID NO:X" that encode a polypeptide having a significant match to the PFAM/NR database as disclosed in the fifth column. In one embodiment, the invention provides a protein comprising, or alternatively consisting of, a polypeptide encoded by the polynucleotides of SEQ ID NO:X delineated in columns 8 and 9 of Table 2. Also provided are polynucleotides encoding such proteins, and the complementary strand thereto.

The nucleotide sequence SEQ ID NO:X and the translated SEQ ID NO:Y are sufficiently accurate and otherwise suitable for a variety of uses well known in the art and described further below. For instance, the nucleotide sequences of SEQ ID NO:X are useful for designing nucleic acid hybridization probes that will detect nucleic acid sequences contained in SEQ ID NO:X or the cDNA contained in ATCC™ Deposit No:Z. These probes will also hybridize to nucleic acid molecules in biological samples, thereby enabling immediate applications in chromosome mapping, linkage analysis, tissue identification and/or typing, and a variety of forensic and diagnostic methods of the invention. Similarly, polypeptides identified from SEQ ID NO:Y may be used to generate antibodies which bind specifically to these polypeptides, or fragments thereof, and/or to the polypeptides encoded by the cDNA clones identified in, for example, Table 1A and/or 1B.

Nevertheless, DNA sequences generated by sequencing reactions can contain sequencing errors. The errors exist as misidentified nucleotides, or as insertions or deletions of nucleotides in the generated DNA sequence. The erroneously inserted or deleted nucleotides cause frame shifts in the reading frames of the predicted amino acid sequence. In these cases, the predicted amino acid sequence diverges from the actual amino acid sequence, even though the generated DNA sequence may be greater than 99.9% identical to the actual DNA sequence (for example, one base insertion or deletion in an open reading frame of over 1000 bases).

Accordingly, for those applications requiring precision in the nucleotide sequence or the amino acid sequence, the present invention provides not only the generated nucleotide sequence identified as SEQ ID NO:X, and a predicted translated amino acid sequence identified as SEQ ID NO:Y, but also a sample of plasmid DNA containing cDNA ATCC™ Deposit No:Z (e.g., as set forth in columns 2 and 3 of Table 1A and/or as set forth, for example, in Tables 6 and 7). The nucleotide sequence of each deposited clone can readily be determined by sequencing the deposited clone in accordance with known methods. Further, techniques known in the art can be used to verify the nucleotide sequences of SEQ ID NO:X. The predicted amino acid sequence can then be verified from such deposits. Moreover, the amino acid sequence of the protein encoded by a particular clone can also be directly determined by peptide sequencing or by expressing the protein in a suitable host cell containing the deposited human cDNA, collecting the protein, and determining its sequence.

TABLE 2

| cDNA Clone ID | Contig ID: | SEQ ID NO: X | Analysis Method | PFam/NR Description | PFam/NR Accession Number | Score/ Percent Identity | NT From | NT To |
|---|---|---|---|---|---|---|---|---|
| HTEEB42 | 206980 | 9 | HMMER 2.1.1 | PFAM: Immunoglobulin domain | PF00047 | 48.5 | 500 | 706 |
| HTEEB42 | 206980 | 9 | WUblastx.64 | (AAG49022) Junctional adhesion molecule 2. | AAG49022 | 94% | 110 | 952 |
| HTEEB42 | 206980 | 9 | WUblastx.64 | (AAG49022) Junctional adhesion molecule 2. | AAG49022 | 99% | 59 | 952 |
| HEMCM42 | 407085 | 11 | WUblastx.64 | (Q9QZW3) TYPE I TRANSMEMBRANE PROTEIN FN14. | Q9QZW3 | 91%<br>88% | 372<br>133 | 443<br>360 |
| HEQCC55 | 884824 | 13 | WUblastx.64 | (Q9NP84) TYPE I TRANSMENMBRANE PROTEIN PRECURSOR (TYPE I TRANSMEMBRAN | Q9NP84 | 64% | 62 | 397 |
| HEMAE80 | 409495 | 20 | WUblastx.64 | (Q9NRR1) CYTOKINE-LIKE PROTEIN C17. | Q9NRR1 | 100% | 12 | 419 |
| HEMAE80 | 1310948 | 22 | WUblastx.64 | (Q9NRR1) CYTOKINE-LIKE PROTEIN C17. | Q9NRR1 | 100% | 136 | 468 |
| HRDFB85 | 411020 | 28 | HMMER 2.1.1 | PFAM: PMP-22/EMP/MP20/Claudin family | PF00822 | 150.2 | 282 | −233 |
| HRDFB85 | 411020 | 28 | WUblastx.64 | (AAH00671) Claudin 4. | AAH00671 | 100% | 209 | 835 |
| HDTAW95 | 412472 | 38 | WUblastx.64 | (Q96CG8) Similar to RIKEN cDNA 1110014B07 gene. | Q96CG8 | 100%<br>97% | 130<br>230 | 249<br>856 |
| HEMCV19 | 423219 | 46 | HMMER 2.1.1 | PFAM: ATP1G1/PLM/MAT8 family | PF02038 | 70.5 | 475 | 609 |
| HEMCV19 | 423219 | 46 | WUblastx.64 | (Q96DB9) FXYD domain-containing ion transport regulator 5 p | FXY5_HUMAN | 88% | 79 | 612 |
| HETBX14 | 806447 | 61 | HMMER 2.1.1 | PFAM: Trypsin | PF00089 | 281.2 | 270 | 935 |
| HETBX14 | 806447 | 61 | WUblastx.64 | (Q9NS65) PROSTATE-TYPE HIPPOSTASIN. | Q9NS65 | 94% | 111 | 956 |
| HETBX14 | 422659 | 63 | WUblastx.64 | (Q9NS65) PROSTATE-TYPE HIPPOSTASIN. | Q9NS65 | 89% | 4 | 810 |
| HLHSK94 | 1307727 | 72 | WUblastx.64 | (AAH18037) Wnt inhibitory factor-1. | AAH18037 | 90% | 112 | 1248 |
| HLHSK94 | 422828 | 74 | HMMER 2.1.1 | PFAM: EGF-like domain | PF00008 | 43.9 | −527 | −610 |
| HLHSK94 | 422828 | 74 | WUblastx.64 | (AAH18037) Wnt inhibitory factor-1. | AAH18037 | 99% | 112 | 1248 |
| HLHFP03 | 460467 | 76 | blastx.2 | (AX058598) unnamed protein product [*Homo sapiens*] | emb\|CAC22514.1\| | 95% | 390 | 43 |
| HLHFP03 | 460467 | 78 | WUblastx.64 | (Q9WVC2) LY-6/NEUROTOXIN HOMOLOG (ADULT MALE HIPPOCAMPUS CDNA, RIKEN | Q9WVC2 | 81% | 224 | 571 |
| HHTLF25 | 461438 | 83 | WUblastx.64 | (Q9UMT3) KILLER ACTIVATING RECEPTOR ASSOCIATED PROTEIN, ISOFORM B. | Q9UMT3 | 91% | 142 | 474 |

TABLE 2-continued

| cDNA Clone ID | Contig ID: | SEQ ID NO: X | Analysis Method | PFam/NR Description | PFam/NR Accession Number | Score/ Percent Identity | NT From | NT To |
|---|---|---|---|---|---|---|---|---|
| HHTLF25 | 461438 | 83 | blastx.2 | KILLER ACTIVATING RECEPTOR ASSOCIATED PROTEIN, ISOFORM B. | sp\|Q9UMT3\|Q9UMT3 | 99% | 142 | 474 |
| HTADX17 | 457172 | 90 | WUblastx.64 | (AK009505) putative [*Mus musculus*] | dbj\|BAB26328.1\| | 67% | 548 | 778 |
| | | | | | | 53% | 490 | 585 |
| | | | | | | 58% | 165 | 488 |
| HTADX17 | 753289 | 92 | WUblastx.64 | (Q96A28) CD84-H1 (CD2 FAMILY 10). | Q96A28 | 93% | 92 | 412 |
| | | | | | | 79% | 408 | 959 |
| HTADX17 | 753289 | 92 | WUblastx.64 | (Q96A28) CD84-H1 (CD2 FAMILY 10). | Q96A28 | 100% | 92 | 412 |
| | | | | | | 99% | 408 | 959 |
| HTADX17 | 457172 | 94 | WUblastx.64 | (Q96A28) CD84-H1 (CD2 FAMILY 10). | Q96A28 | 78% | 490 | 585 |
| | | | | | | 97% | 548 | 952 |
| | | | | | | 99% | 84 | 488 |
| HJACG02 | 509948 | 102 | WUblastx.64 | (Q9HD89) CYSTEINE-RICH SECRETED PROTEIN (C/EBP-EPSILON REGULATED MYEL | Q9HD89 | 100% | 47 | 370 |
| HJACG02 | 509948 | 102 | WUblastx.64 | (Q9HD89) CYSTEINE-RICH SECRETED PROTEIN (C/EBP-EPSILON REGULATED MYEL | Q9HD89 | 100% | 92 | 370 |
| HJACG02 | 1307789 | 104 | WUblastx.64 | (Q9HD89) CYSTEINE-RICH SECRETED PROTEIN (C/EBP-EPSILON REGULATED MYEL | Q9HD89 | 100% | 111 | 389 |
| HJACG02 | 1307789 | 104 | WUblastx.64 | (Q9HD89) CYSTEINE-RICH SECRETED PROTEIN (C/EBP-EPSILON REGULATED MYEL | Q9HD89 | 100% | 66 | 389 |
| HKGAJ54 | 498303 | 107 | HMMER 2.1.1 | PFAM: Immunoglobulin domain | PF00047 | 52.8 | 481 | 657 |
| HKGAJ54 | 498303 | 107 | WUblastx.64 | (AAL31867) Magic roundabout. | AAL31867 | 96% | 846 | 929 |
| | | | | | | 98% | 31 | 849 |
| HKGAJ54 | 498303 | 107 | WUblastx.64 | (BAB55411) CDNA FLJ14946 fis, clone PLACE2000034, w | BAB55411 | 96% | 846 | 929 |
| | | | | | | 90% | 109 | 849 |
| HKGAJ54 | 1300770 | 109 | WUblastx.64 | (BAB55411) CDNA FLJ14946 fis, clone PLACE2000034, w | BAB55411 | 91% | 102 | 923 |
| HSVAK93 | 597462 | 116 | HMMER 2.1.1 | PFAM: Immunoglobulin domain | PF00047 | 23.6 | 117 | 362 |
| HSVAK93 | 597462 | 116 | WUblastx.64 | (AAH08988) Unknown (protein for MGC: 17333). | AAH08988 | 100% | 21 | 530 |
| HE8CH92 | 609866 | 118 | HMMER 2.1.1 | PFAM: Immunoglobulin domain | PF00047 | 23.6 | 127 | 372 |
| HE8CH92 | 609866 | 118 | WUblastx.64 | (AAH08988) Unknown (protein for MGC: 17333). | AAH08988 | 100% | 31 | 1164 |
| HSDEK49 | 625998 | 123 | HMMER 2.1.1 | PFAM: Immunoglobulin domain | PF00047 | 18.7 | 225 | 470 |
| HSDEK49 | 625998 | 123 | WUblastx.64 | (Q9Y279) Z39IG PROTEIN PRECURSOR. | Q9Y279 | 88% | 444 | 1040 |
| | | | | | | 99% | 126 | 542 |
| HSDEK49 | 1352253 | 125 | WUblastx.64 | (Q9Y279) Z39IG PROTEIN PRECURSOR. | Q9Y279 | 100% | 60 | 1256 |
| HWBAO62 | 838164 | 127 | HMMER 2.1.1 | PFAM: Immunoglobulin domain | PF00047 | 27.9 | 202 | 402 |
| HWBAO62 | 838164 | 127 | WUblastx.64 | (Q14288) HYPOTHETICAL PROTEIN (FRAGMENT). | Q14288 | 45% | 1331 | 1618 |
| | | | | | | 66% | 1158 | 1334 |
| | | | | | | 62% | 1847 | 1894 |
| | | | | | | 55% | 1594 | 1839 |
| HWBAO62 | 625914 | 129 | WUblastx.64 | (Q14288) HYPOTHETICAL PROTEIN (FRAGMENT). | Q14288 | 43% | 1358 | 1645 |
| | | | | | | 62% | 1874 | 1921 |
| | | | | | | 66% | 1185 | 1361 |
| | | | | | | 55% | 1621 | 1866 |
| HWHGU54 | 695695 | 131 | HMMER 2.1.1 | PFAM: Serpins (serine protease inhibitors) | PF00079 | 501.1 | 277 | 1377 |
| HWHGU54 | 695695 | 131 | WUblastx.64 | (Q9CQ32) 4632419J12RIK PROTEIN. | Q9CQ32 | 61% | 145 | 1383 |
| HWHGU54 | 695695 | 131 | WUblastx.64 | (AAL99574) OL-64 protein. | AAL99574 | 62% | 145 | 1377 |
| HWHGU54 | 695695 | 131 | WUblastx.64 | (Q9CQ32) 4632419J12RIK PROTEIN. | Q9CQ32 | 59% | 145 | 1383 |
| HCEJQ69 | 1243825 | 134 | HMMER 2.1.1 | PFAM: Leucine Rich Repeat | PF00560 | 116.2 | 573 | 644 |
| HCEJQ69 | 1243825 | 134 | WUblastx.64 | (Q9BZR6) NOGO RECEPTOR. | Q9BZR6 | 87% | 39 | 1457 |
| HCEJQ69 | 1243825 | 134 | WUblastx.64 | (AF283463) Nogo receptor [*Homo sapiens*] | gb\|AAG53612.1\|AF283463_1 | 87% | 39 | 1457 |
| HCEJQ69 | 872582 | 136 | HMMER 2.1.1 | PFAM: Leucine Rich Repeat | PF00560 | 116.2 | 573 | 644 |
| HCEJQ69 | 872582 | 136 | WUblastx.64 | (Q9BZR6) NOGO RECEPTOR. | Q9BZR6 | 90% | 39 | 1361 |
| HCEJQ69 | 609999 | 138 | HMMER 2.1.1 | PFAM: Leucine Rich Repeat | PF00560 | 114.5 | 573 | 644 |
| HCEJQ69 | 609999 | 138 | WUblastx.64 | (Q9BZR6) NOGO RECEPTOR. | Q9BZR6 | 59% | 1100 | 1462 |
| | | | | | | 85% | 39 | 1460 |
| HCEJQ69 | 609999 | 138 | WUblastx.64 | (Q9BZR6) NOGO RECEPTOR. | Q9BZR6 | 85% | 39 | 1364 |
| | | | | | | 45% | 1100 | 1462 |
| HT5GJ57 | 740767 | 159 | WUblastx.64 | (Q9NZY9) HSPC046. | Q9NZY9 | 90% | 754 | 1002 |
| | | | | | | 70% | 122 | 799 |
| HT5GJ57 | 740767 | 159 | WUblastx.64 | (Q9GZY6) CDNA FLJ11237 FIS, CLONE PLACE1008531 (WBSCR5) (WBSCR15 PROT | Q9GZY6 | 84% | 122 | 856 |
| HT5GJ57 | 740767 | 159 | WUblastx.64 | (AX083396) unnamed protein product [*Homo sapiens*] | emb\|CAC33299.1\| | 84% | 122 | 856 |

TABLE 2-continued

| cDNA Clone ID | Contig ID: | SEQ ID NO: X | Analysis Method | PFam/NR Description | PFam/NR Accession Number | Score/ Percent Identity | NT From | NT To |
|---|---|---|---|---|---|---|---|---|
| HT5GJ57 | 1299921 | 161 | WUblastx.64 | (Q9GZY6) CDNA FLJ11237 FIS, CLONE PLACE1008531 (WBSCR5) (WBSCR15 PROT | Q9GZY6 | 89% | 105 | 833 |
| HPIBX03 | 743314 | 169 | WUblastx.64 | (Q9H5V8) CDNA: FLJ22969 FIS, CLONE KAT10759. | Q9H5V8 | 98% | 81 | 2207 |
| HDPBO81 | 892018 | 174 | WUblastx.64 | (Q9ES58) OX2 RECEPTOR PRECURSOR. | Q9ES58 | 57%<br>38% | 400<br>265 | 1323<br>381 |
| HWBFY57 | 837478 | 179 | HMMER 2.1.1 | PFAM: Immunoglobulin domain | PF00047 | 19.2 | 209 | 442 |
| HWBFY57 | 837478 | 179 | WUblastx.64 | (AAH19814) Hypothetical 25.0 kDa protein. | AAH19814 | 54% | 134 | 535 |
| HYABV21 | 1281466 | 182 | HMMER 2.1.1 | PFAM: Immunoglobulin domain | PF00047 | 46 | 166 | 342 |
| HYABV21 | 1281466 | 182 | blastx.2 | MMAN-g protein precursor. | sp\|BAB18569\|BAB18569 | 54% | 109 | 672 |
| HYABV21 | 1213593 | 184 | HMMER 2.1.1 | PFAM: Immunoglobulin domain | PF00047 | 46 | 174 | 350 |
| HYABV21 | 1213593 | 184 | blastx.2 | MMAN-g protein precursor. | sp\|BAB18569\|BAB18569 | 49% | 117 | 686 |
| HOHBY69 | 827480 | 186 | HMMER 2.1.1 | PFAM: FG-GAP repeat | PF01839 | 223 | 1696 | 1875 |
| HOHBY69 | 827480 | 186 | WUblastx.64 | (Q9UKX5) INTEGRIN ALPHA-11 PRECURSOR. | ITAH_HUMAN | 98% | 82 | 3648 |
| HOHBY69 | 815681 | 188 | HMMER 2.1.1 | PFAM: FG-GAP repeat | PF01839 | 223 | 1698 | 1877 |
| HOHBY69 | 815681 | 188 | blastx.2 | (AF109681) integrin alpha-11 subunit precursor [*Homo sapiens*] | gb\|AAF01258.1\|AF109681_1 | 99%<br>99% | 84<br>3172 | 3170<br>3648 |
| HDHMA45 | 902513 | 202 | WUblastx.64 | (Q9H3S3) TRANSMEMBRANE PROTEASE, SERINE 5 (EC 3.4.21.—) (SP | TMS5_HUMAN | 91% | 175 | 1428 |
| HDHMA45 | 812764 | 204 | HMMER 2.1.1 | PFAM: Trypsin | PF00089 | 296.3 | 723 | 1415 |
| HDHMA45 | 812764 | 204 | WUblastx.64 | (Q9H3S3) TRANSMEMBRANE PROTEASE, SERINE 5 (EC 3.4.21.—) (SP | TMS5_HUMAN | 99% | 180 | 1442 |
| HMADJ14 | 1099342 | 206 | WUblastx.64 | (Q9H295) DC-SPECIFIC TRANSMEMBRANE PROTEIN. | Q9H295 | 99% | 200 | 1306 |
| HMADJ14 | 889659 | 208 | blastx.2 | (AF305068) DC-specific transmembrane protein [*Homo sapiens*] | gb\|AAG39167.1\|AF305068_1 | 90%<br>96% | 186<br>1010 | 1019<br>1084 |
| HMADJ14 | 843725 | 210 | WUblastx.64 | (Q9H295) DC-SPECIFIC TRANSMEMBRANE PROTEIN. | Q9H295 | 96%<br>90% | 871<br>47 | 945<br>880 |
| HMADJ14 | 843725 | 212 | WUblastx.64 | (Q9H295) DC-SPECIFIC TRANSMEMBRANE PROTEIN. | Q9H295 | 96%<br>90% | 871<br>47 | 945<br>880 |
| HMADJ14 | 795479 | 214 | WUblastx.64 | (Q9H295) DC-SPECIFIC TRANSMEMBRANE PROTEIN. | Q9H295 | 100%<br>93% | 1010<br>186 | 1393<br>1067 |
| HMADJ14 | 426068 | 216 | blastx.2 | (AF305068) DC-specific transmembrane protein [*Homo sapiens*] | gb\|AAG39167.1\|AF305068_1 | 91%<br>78%<br>96% | 47<br>675<br>872 | 685<br>881<br>946 |
| HEMFA84 | 608198 | 222 | WUblastx.64 | (Q9H6H3) CDNA: FLJ22282 FIS, CLONE HRC03861. | Q9H6H3 | 100% | 42 | 812 |
| HDPPA04 | 904765 | 224 | HMMER 2.1.1 | PFAM: Immunoglobulin domain | PF00047 | 19.1 | 373 | 582 |
| HDPPA04 | 904765 | 224 | WUblastx.64 | (Q9BQ51) BUTYROPHILIN PRECURSOR B7-DC (PD-1-LIGAND 2 PROTEIN). | Q9BQ51 | 92% | 271 | 1089 |
| HE2OA95 | 637595 | 230 | WUblastx.64 | (Q9UIK5) TMEFF2 PROTEIN PRECURSOR (TRANSMEMBRANE PROTEIN TENB2) (TPEF | Q9UIK5 | 99% | 1647 | 1231 |
| HKABZ65 | 862030 | 232 | WUblastx.64 | (Q96LB9) Peptidoglycan recognition protein-I-alpha precursor. | Q96LB9 | 90%<br>39% | 77<br>137 | 802<br>541 |
| HKABZ65 | 862030 | 232 | WUblastx.64 | (Q96LB9) Peptidoglycan recognition protein-I-alpha precursor. | Q96LB9 | 99%<br>45% | 77<br>137 | 802<br>541 |
| HKABZ65 | 665424 | 234 | WUblastx.64 | (Q96LB9) Peptidoglycan recognition protein-I-alpha precursor. | Q96LB9 | 99%<br>45% | 69<br>129 | 794<br>533 |

RACE Protocol for Recovery of Full-Length Genes

Partial cDNA clones can be made full-length by utilizing the rapid amplification of cDNA ends (RACE) procedure described in Frohman, M. A., et al., Proc. Nat'l. Acad. Sci. USA, 85:8998-9002 (1988). A cDNA clone missing either the 5' or 3' end can be reconstructed to include the absent base pairs extending to the translational start or stop codon, respectively. In some cases, cDNAs are missing the start codon of translation, therefor. The following briefly describes a modification of this original 5' RACE procedure. Poly A+ or total RNA is reverse transcribed with Superscript II (Gibco/BRL) and an antisense or complementary primer specific to the cDNA sequence. The primer is removed from the reaction with a Microcon Concentrator (Amicon). The first-strand cDNA is then tailed with dATP and terminal deoxynucleotide transferase (Gibco/BRL). Thus, an anchor sequence is produced which is needed for PCR amplification. The second strand is synthesized from the dA-tail in PCR buffer, Taq DNA polymerase (Perkin-Elmer Cetus), an oligo-dT primer containing three adjacent restriction sites (XhoI, SalI and ClaI) at the 5' end and a primer containing just these restriction sites. This double-stranded cDNA is PCR amplified for 40 cycles with the same primers as well as a nested cDNA-specific antisense primer. The PCR products are size-separated on an ethidium bromide-agarose gel and the region of gel containing cDNA products the predicted size of missing protein-coding DNA is removed. cDNA is purified from the agarose with the Magic PCR Prep kit (PROMEGA™), restriction digested with XhoI or SalI, and ligated to a plasmid such as pBLUESCRIPT™ SKII (STRATAGENE™) at XhoI and EcoRV sites. This DNA is transformed into bacteria and the plasmid clones sequenced to identify the correct protein-coding inserts. Correct 5' ends are confirmed by comparing this sequence with the putatively identified homologue and overlap with the partial cDNA clone. Similar methods known in the art and/or commercial kits are used to amplify and recover 3' ends.

Several quality-controlled kits are commercially available for purchase. Similar reagents and methods to those above are supplied in kit form from Gibco/BRL for both 5' and 3' RACE for recovery of full length genes. A second kit is available from CLONTECH™ which is a modification of a related technique, SLIC (single-stranded ligation to single-stranded cDNA), developed by Dumas et al., Nucleic Acids Res., 19:5227-32 (1991). The major differences in procedure are that the RNA is alkaline hydrolyzed after reverse transcription and RNA ligase is used to join a restriction site-containing anchor primer to the first-strand cDNA. This obviates the necessity for the dA-tailing reaction which results in a polyT stretch that is difficult to sequence past.

An alternative to generating 5' or 3' cDNA from RNA is to use cDNA library double-stranded DNA. An asymmetric PCR-amplified antisense cDNA strand is synthesized with an antisense cDNA-specific primer and a plasmid-anchored primer. These primers are removed and a symmetric PCR reaction is performed with a nested cDNA-specific antisense primer and the plasmid-anchored primer.

RNA Ligase Protocol for Generating the 5' or 3' End Sequences to Obtain Full Length Genes Once a gene of interest is identified, several methods are available for the identification of the 5' or 3' portions of the gene which may not be present in the original cDNA plasmid. These methods include, but are not limited to, filter probing, clone enrichment using specific probes and protocols similar and identical to 5' and 3' RACE. While the full length gene may be present in the library and can be identified by probing, a useful method for generating the 5' or 3' end is to use the existing sequence information from the original cDNA to generate the missing information. A method similar to 5' RACE is available for generating the missing 5' end of a desired full-length gene. (This method was published by Fromont-Racine et al., Nucleic Acids Res., 21(7):1683-1684 (1993)). Briefly, a specific RNA oligonucleotide is ligated to the 5' ends of a population of RNA presumably containing full-length gene RNA transcript and a primer set containing a primer specific to the ligated RNA oligonucleotide and a primer specific to a known sequence of the gene of interest, is used to PCR amplify the 5' portion of the desired full length gene which may then be sequenced and used to generate the full length gene. This method starts with total RNA isolated from the desired source, poly A RNA may be used but is not a prerequisite for this procedure. The RNA preparation may then be treated with phosphatase if necessary to eliminate 5' phosphate groups on degraded or damaged RNA which may interfere with the later RNA ligase step. The phosphatase if used is then inactivated and the RNA is treated with tobacco acid pyrophosphatase in order to remove the cap structure present at the 5' ends of messenger RNAs. This reaction leaves a 5' phosphate group at the 5' end of the cap cleaved RNA which can then be ligated to an RNA oligonucleotide using T4 RNA ligase. This modified RNA preparation can then be used as a template for first strand cDNA synthesis using a gene specific oligonucleotide. The first strand synthesis reaction can then be used as a template for PCR amplification of the desired 5' end using a primer specific to the ligated RNA oligonucleotide and a primer specific to the known sequence of the gene of interest. The resultant product is then sequenced and analyzed to confirm that the 5' end sequence belongs to the relevant gene.

The present invention also relates to vectors or plasmids which include such DNA sequences, as well as the use of the DNA sequences. The material deposited with the ATCC™ (e.g., as described in columns 2 and 3 of Table 1A, and/or as set forth in Table 6 or 7) is a mixture of cDNA clones derived from a variety of human tissue and cloned in either a plasmid vector or a phage vector, as described, for example, in Tables 1A and 7. These deposits are referred to as "the deposits" herein. The tissues from which some of the clones were derived are listed in Table 7, and the vector in which the corresponding cDNA is contained is also indicated in Table 7. The deposited material includes cDNA clones corresponding to SEQ ID NO:X described, for example, in Table 1A (ATCC™ Deposit No:Z). A clone which is isolatable from the ATCC™ Deposits by use of a sequence listed as SEQ ID NO:X, may include the entire coding region of a human gene or in other cases such clone may include a substantial portion of the coding region of a human gene. Furthermore, although the sequence listing may in some instances list only a portion of the DNA sequence in a clone included in the ATCC™ Deposits, it is well within the ability of one skilled in the art to sequence the DNA included in a clone contained in the ATCC™ Deposits by use of a sequence (or portion thereof) described in, for example Tables 1A, 1B.1, 1B.2, or 2, by procedures hereinafter further described, and others apparent to those skilled in the art.

Also provided in Tables 1A and 7 is the name of the vector which contains the cDNA clone. Each vector is routinely used in the art. The following additional information is provided for convenience.

Vectors Lambda Zap (U.S. Pat. Nos. 5,128,256 and 5,286,636), Uni-Zap XR (U.S. Pat. Nos. 5,128,256 and 5,286,636), Zap Express (U.S. Pat. Nos. 5,128,256 and 5,286,636), pBLUESCRIPT™ (pBS) (Short, J. M. et al., *Nucleic Acids Res.* 16:7583-7600 (1988); Alting-Mees, M. A. and Short, J. M., *Nucleic Acids Res.* 17:9494 (1989)) and pBK (Alting-Mees, M. A. et al., *Strategies* 5:58-61 (1992)) are commercially available from STRATAGENE™ Cloning Systems, Inc., 11011 N. Torrey Pines Road, La Jolla, Calif., 92037. pBS contains an ampicillin resistance gene and pBK contains a neomycin resistance gene. Phagemid pBS may be excised from the Lambda Zap and Uni-Zap XR vectors, and phagemid pBK may be excised from the Zap Express vector. Both phagemids may be transformed into *E. coli* strain XL-1 Blue, also available from STRATAGENE™.

Vectors pSport1, pCMVSport 1.0, pCMVSport 2.0 and pCMVSport 3.0, were obtained from LIFE TECHNOLOGIES™, Inc., P.O. Box 6009, Gaithersburg, Md. 20897. All Sport vectors contain an ampicillin resistance gene and may be transformed into *E. coli* strain DH10B, also available from LIFE TECHNOLOGIES™. See, for instance, Gruber, C. E., et al., *Focus* 15:59-(1993). Vector lafmid BA (Bento Soares, Columbia University, New York, N.Y.) contains an ampicillin resistance gene and can be transformed into *E. coli* strain XL-1 Blue. Vector pCR®2.1, which is available from Invitrogen, 1600 Faraday Avenue, Carlsbad, Calif. 92008, contains an ampicillin resistance gene and may be transformed into *E. coli* strain DH10B, available from LIFE TECHNOLOGIES™. See, for instance, Clark, J. M., *Nuc. Acids Res.* 16:9677-9686 (1988) and Mead, D. et al., *Bio/Technology* 9: (1991).

The present invention also relates to the genes corresponding to SEQ ID NO:X, SEQ ID NO:Y, and/or the deposited clone (ATCC™ Deposit No:Z). The corresponding gene can be isolated in accordance with known methods using the sequence information disclosed herein. Such methods include preparing probes or primers from the disclosed sequence and identifying or amplifying the corresponding gene from appropriate sources of genomic material.

Also provided in the present invention are allelic variants, orthologs, and/or species homologs. Procedures known in the art can be used to obtain full-length genes, allelic variants, splice variants, full-length coding portions, orthologs, and/or species homologs of genes corresponding to SEQ ID NO:X or the complement thereof, polypeptides encoded by genes corresponding to SEQ ID NO:X or the complement thereof, and/or the cDNA contained in ATCC™ Deposit No:Z, using information from the sequences disclosed herein or the clones deposited with the ATCC™. For example, allelic variants and/or species homologs may be isolated and identified by making suitable probes or primers from the sequences provided herein and screening a suitable nucleic acid source for allelic variants and/or the desired homologue.

The polypeptides of the invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

The polypeptides may be in the form of the secreted protein, including the mature form, or may be a part of a larger protein, such as a fusion protein (see below). It is often advantageous to include an additional amino acid sequence which contains secretory or leader sequences, pro-sequences, sequences which aid in purification, such as multiple histidine residues, or an additional sequence for stability during recombinant production.

The polypeptides of the present invention are preferably provided in an isolated form, and preferably are substantially purified. A recombinantly produced version of a polypeptide, including the secreted polypeptide, can be substantially purified using techniques described herein or otherwise known in the art, such as, for example, by the one-step method described in Smith and Johnson, Gene 67:31-40 (1988). Polypeptides of the invention also can be purified from natural, synthetic or recombinant sources using techniques described herein or otherwise known in the art, such as, for example, antibodies of the invention raised against the polypeptides of the present invention in methods which are well known in the art.

The present invention provides a polynucleotide comprising, or alternatively consisting of, the nucleic acid sequence of SEQ ID NO:X, and/or the cDNA sequence contained in ATCC™ Deposit No:Z. The present invention also provides a polypeptide comprising, or alternatively, consisting of, the polypeptide sequence of SEQ ID NO:Y, a polypeptide encoded by SEQ ID NO:X or a complement thereof, a polypeptide encoded by the cDNA contained in ATCC™ Deposit No:Z, and/or the polypeptide sequence encoded by a nucleotide sequence in SEQ ID NO:B as defined in column 6 of Table 1C. Polynucleotides encoding a polypeptide comprising, or alternatively consisting of the polypeptide sequence of SEQ ID NO:Y, a polypeptide encoded by SEQ ID NO:X, a polypeptide encoded by the cDNA contained in ATCC™ Deposit No:Z, and/or a polypeptide sequence encoded by a nucleotide sequence in SEQ ID NO:B as defined in column 6 of Table 1C are also encompassed by the invention. The present invention further encompasses a polynucleotide comprising, or alternatively consisting of, the complement of the nucleic acid sequence of SEQ ID NO:X, a nucleic acid sequence encoding a polypeptide encoded by the complement of the nucleic acid sequence of SEQ ID NO:X, and/or the cDNA contained in ATCC™ Deposit No:Z.

Moreover, representative examples of polynucleotides of the invention comprise, or alternatively consist of, one, two, three, four, five, six, seven, eight, nine, ten, or more of the sequences delineated in column 6 of Table 1C, or any combination thereof. Additional, representative examples of polynucleotides of the invention comprise, or alternatively consist of, one, two, three, four, five, six, seven, eight, nine, ten, or more of the complementary strand(s) of the sequences delineated in column 6 of Table 1C, or any combination thereof. In further embodiments, the above-described polynucleotides of the invention comprise, or alternatively consist of, sequences delineated in column 6 of Table 1C, and have a nucleic acid sequence which is different from that of the BAC fragment having the sequence disclosed in SEQ ID NO:B (see Table 1C, column 5). In additional embodiments, the above-described polynucleotides of the invention comprise, or alternatively consist of, sequences delineated in Table 1C, column 6, and have a nucleic acid sequence which is different from that published for the BAC clone identified as BAC ID NO:A (see Table 1C, column 4). In additional embodiments, the above-described polynucleotides of the invention comprise, or alternatively consist of, sequences delineated in Table 1C, column 6, and have a nucleic acid sequence which is different from that contained in the BAC clone identified as BAC ID NO:A (see Table 1C, column 4). Polypeptides encoded by these polynucleotides, other polynucleotides that encode these polypeptides, and antibodies that bind these polypeptides are also encompassed by the invention. Additionally, fragments and variants of the above-described polynucleotides and polypeptides are also encompassed by the invention.

Further, representative examples of polynucleotides of the invention comprise, or alternatively consist of, one, two, three, four, five, six, seven, eight, nine, ten, or more of the sequences delineated in column 6 of Table 1C which correspond to the same Clone ID (see Table 1C, column 1), or any combination thereof. Additional, representative examples of polynucleotides of the invention comprise, or alternatively consist of, one, two, three, four, five, six, seven, eight, nine, ten, or more of the complementary strand(s) of the sequences delineated in column 6 of Table 1C which correspond to the same Clone ID (see Table 1C, column 1), or any combination thereof. In further embodiments, the above-described polynucleotides of the invention comprise, or alternatively consist of, sequences delineated in column 6 of Table 1C which correspond to the same Clone ID (see Table 1C, column 1) and have a nucleic acid sequence which is different from that of the BAC fragment having the sequence disclosed in SEQ ID NO:B (see Table 1C, column 5). In additional embodiments, the above-described polynucleotides of the invention comprise, or alternatively consist of, sequences delineated in column 6 of Table 1C which correspond to the same Clone ID (see Table 1C, column 1) and have a nucleic acid sequence which is different from that published for the BAC clone identified as BAC ID NO:A (see Table 1C, column 4). In additional embodiments, the above-described polynucleotides of the invention comprise, or alternatively consist of, sequences delineated in column 6 of Table 1C which correspond to the same Clone ID (see Table 1C, column 1) and have a nucleic acid sequence which is different from that contained in the BAC clone identified as BAC ID NO:A (see Table 1C, column 4). Polypeptides encoded by these polynucleotides, other polynucleotides that encode these polypeptides, and antibodies that bind these polypeptides are also encompassed by the invention. Additionally, fragments and variants of the above-described polynucleotides and polypeptides are also encompassed by the invention.

Further, representative examples of polynucleotides of the invention comprise, or alternatively consist of, one, two, three, four, five, six, seven, eight, nine, ten, or more of the sequences delineated in column 6 of Table 1C which correspond to the same contig sequence identifier SEQ ID NO:X (see Table 1C, column 2), or any combination thereof. Additional, representative examples of polynucleotides of the invention comprise, or alternatively consist of, one, two, three, four, five, six, seven, eight, nine, ten, or more of the complementary strand(s) of the sequences delineated in column 6 of Table 1C which correspond to the same contig sequence identifier SEQ ID NO:X (see Table 1C, column 2), or any combination thereof. In further embodiments, the above-described polynucleotides of the invention comprise, or alternatively consist of, sequences delineated in column 6 of Table 1C which correspond to the same contig sequence identifier SEQ ID NO:X (see Table 1C, column 2) and have a nucleic acid sequence which is different from that of the BAC fragment having the sequence disclosed in SEQ ID NO:B (see Table 1C, column 5). In additional embodiments, the above-described polynucleotides of the invention comprise, or alternatively consist of, sequences delineated in column 6 of Table 1C which correspond to the same contig sequence identifier SEQ ID NO:X (see Table 1C, column 2) and have a nucleic acid sequence which is different from that published for the BAC clone identified as BAC ID NO:A (see Table 1C, column 4). In additional embodiments, the above-described polynucleotides of the invention comprise, or alternatively consist of, sequences delineated in column 6 of Table 1C which correspond to the same contig sequence identifier SEQ ID NO:X (see Table 1C, column 2) and have a nucleic acid sequence which is different from that contained in the BAC clone identified as BAC ID NO:A (See Table 1C, column 4). Polypeptides encoded by these polynucleotides, other polynucleotides that encode these polypeptides, and antibodies that bind these polypeptides are also encompassed by the invention. Additionally, fragments and variants of the above-described polynucleotides and polypeptides are also encompassed by the invention.

Moreover, representative examples of polynucleotides of the invention comprise, or alternatively consist of, one, two, three, four, five, six, seven, eight, nine, ten, or more of the sequences delineated in the same row of Table 1C column 6, or any combination thereof. Additional, representative examples of polynucleotides of the invention comprise, or alternatively consist of, one, two, three, four, five, six, seven, eight, nine, ten, or more of the complementary strand(s) of the sequences delineated in the same row of Table 1C column 6, or any combination thereof. In preferred embodiments, the polynucleotides of the invention comprise, or alternatively consist of, one, two, three, four, five, six, seven, eight, nine, ten, or more of the complementary strand(s) of the sequences delineated in the same row of Table 1C column 6, wherein sequentially delineated sequences in the table (i.e. corresponding to those exons located closest to each other) are directly contiguous in a 5' to 3' orientation. In further embodiments, above-described polynucleotides of the invention comprise, or alternatively consist of, sequences delineated in the same row of Table 1C, column 6, and have a nucleic acid sequence which is different from that of the BAC fragment having the sequence disclosed in SEQ ID NO:B (see Table 1C, column 5). In additional embodiments, the above-described polynucleotides of the invention comprise, or alternatively consist of, sequences delineated in the same row of Table 1C, column 6, and have a nucleic acid sequence which is different from that published for the BAC clone identified as BAC ID NO:A (see Table 1C, column 4). In additional embodiments, the above-described polynucleotides of the invention comprise, or alternatively consist of, sequences delineated in the same row of Table 1C, column 6, and have a nucleic acid sequence which is different from that contained in the BAC clone identified as BAC ID NO:A (see Table 1C, column 4). Polypeptides encoded by these polynucleotides, other polynucleotides that encode these polypeptides, and antibodies that bind these polypeptides are also encompassed by the invention.

In additional specific embodiments, polynucleotides of the invention comprise, or alternatively consist of, one, two, three, four, five, six, seven, eight, nine, ten, or more of the sequences delineated in column 6 of Table 1C, and the polynucleotide sequence of SEQ ID NO:X (e.g., as defined in Table 1C, column 2) or fragments or variants thereof. Polypeptides encoded by these polynucleotides, other polynucleotides that encode these polypeptides, and antibodies that bind these polypeptides are also encompassed by the invention.

In additional specific embodiments, polynucleotides of the invention comprise, or alternatively consist of, one, two, three, four, five, six, seven, eight, nine, ten, or more of the sequences delineated in column 6 of Table 1C which correspond to the same Clone ID (see Table 1C, column 1), and the polynucleotide sequence of SEQ ID NO:X (e.g., as defined in Table 1A, 1B.1, 1B.2, or 1C) or fragments or variants thereof. In preferred embodiments, the delineated sequence(s) and polynucleotide sequence of SEQ ID NO:X correspond to the same Clone ID. Polypeptides encoded by these polynucleotides, other polynucleotides that encode these polypeptides, and antibodies that bind these polypeptides are also encompassed by the invention.

In further specific embodiments, polynucleotides of the invention comprise, or alternatively consist of, one, two, three, four, five, six, seven, eight, nine, ten, or more of the sequences delineated in the same row of column 6 of Table 1C, and the polynucleotide sequence of SEQ ID NO:X (e.g., as defined in Table 1A, 1B.1, 1B.2, or 1C) or fragments or variants thereof. In preferred embodiments, the delineated sequence(s) and polynucleotide sequence of SEQ ID NO:X correspond to the same row of column 6 of Table 1C. Polypeptides encoded by these polynucleotides, other polynucleotides that encode these polypeptides, and antibodies that bind these polypeptides are also encompassed by the invention.

In additional specific embodiments, polynucleotides of the invention comprise, or alternatively consist of a polynucleotide sequence in which the 3' 10 polynucleotides of one of the sequences delineated in column 6 of Table 1C and the 5' 10 polynucleotides of the sequence of SEQ ID NO:X are directly contiguous. Nucleic acids which hybridize to the complement of these 20 contiguous polynucleotides under stringent hybridization conditions or alternatively, under lower stringency conditions, are also encompassed by the invention. Polypeptides encoded by these polynucleotides and/or nucleic acids, other polynucleotides and/or nucleic acids that encode these polypeptides, and antibodies that bind these polypeptides are also encompassed by the invention. Additionally, fragments and variants of the above-described polynucleotides, nucleic acids, and polypeptides are also encompassed by the invention.

In additional specific embodiments, polynucleotides of the invention comprise, or alternatively consist of, a polynucleotide sequence in which the 3' 10 polynucleotides of one of the sequences delineated in column 6 of Table 1C and the 5' 10 polynucleotides of a fragment or variant of the sequence of SEQ ID NO:X are directly contiguous Nucleic acids which hybridize to the complement of these 20 contiguous polynucleotides under stringent hybridization conditions or alternatively, under lower stringency conditions, are also encompassed by the invention. Polypeptides encoded by these polynucleotides and/or nucleic acids, other polynucleotides and/or nucleic acids encoding these polypeptides, and antibodies that bind these polypeptides are also encompassed by the invention. Additionally, fragments and variants of the above-described polynucleotides, nucleic acids, and polypeptides are also encompassed by the invention.

In specific embodiments, polynucleotides of the invention comprise, or alternatively consist of, a polynucleotide sequence in which the 3' 10 polynucleotides of the sequence of SEQ ID NO:X and the 5' 10 polynucleotides of the sequence of one of the sequences delineated in column 6 of Table 1C are directly contiguous. Nucleic acids which hybridize to the complement of these 20 contiguous polynucleotides under stringent hybridization conditions or alternatively, under lower stringency conditions, are also encompassed by the invention. Polypeptides encoded by these polynucleotides and/or nucleic acids, other polynucleotides and/or nucleic acids encoding these polypeptides, and antibodies that bind these polypeptides are also encompassed by the invention. Additionally, fragments and variants of the above-described polynucleotides, nucleic acids, and polypeptides are also encompassed by the invention.

In specific embodiments, polynucleotides of the invention comprise, or alternatively consist of, a polynucleotide sequence in which the 3' 10 polynucleotides of a fragment or variant of the sequence of SEQ ID NO:X and the 5' 10 polynucleotides of the sequence of one of the sequences delineated in column 6 of Table 1C are directly contiguous. Nucleic acids which hybridize to the complement of these 20 contiguous polynucleotides under stringent hybridization conditions or alternatively, under lower stringency conditions, are also encompassed by the invention. Polypeptides encoded by these polynucleotides and/or nucleic acids, other polynucleotides and/or nucleic acids encoding these polypeptides, and antibodies that bind these polypeptides are also encompassed by the invention. Additionally, fragments and variants of the above-described polynucleotides, nucleic acids, and polypeptides, are also encompassed by the invention.

In further specific embodiments, polynucleotides of the invention comprise, or alternatively consist of, a polynucleotide sequence in which the 3' 10 polynucleotides of one of the sequences delineated in column 6 of Table 1C and the 5' 10 polynucleotides of another sequence in column 6 are directly contiguous. Nucleic acids which hybridize to the complement of these 20 contiguous polynucleotides under stringent hybridization conditions or alternatively, under lower stringency conditions, are also encompassed by the invention. Polypeptides encoded by these polynucleotides and/or nucleic acids, other polynucleotides and/or nucleic acids encoding these polypeptides, and antibodies that bind these polypeptides are also encompassed by the invention. Additionally, fragments and variants of the above-described polynucleotides, nucleic acids, and polypeptides are also encompassed by the invention.

In specific embodiments, polynucleotides of the invention comprise, or alternatively consist of, a polynucleotide sequence in which the 3' 10 polynucleotides of one of the sequences delineated in column 6 of Table 1C and the 5' 10 polynucleotides of another sequence in column 6 corresponding to the same Clone ID (see Table 1C, column 1) are directly contiguous. Nucleic acids which hybridize to the complement of these 20 lower stringency conditions, are also encompassed by the invention. Polypeptides encoded by these polynucleotides and/or nucleic acids, other polynucleotides and/or nucleic acids encoding these polypeptides, and antibodies that bind these polypeptides are also encompassed by the invention. Additionally, fragments and variants of the above-described polynucleotides, nucleic acids, and polypeptides are also encompassed by the invention.

In specific embodiments, polynucleotides of the invention comprise, or alternatively consist of, a polynucleotide sequence in which the 3' 10 polynucleotides of one sequence in column 6 corresponding to the same contig sequence identifier SEQ ID NO:X (see Table 1C, column 2) are directly contiguous. Nucleic acids which hybridize to the complement of these 20 contiguous polynucleotides under stringent hybridization conditions or alternatively, under lower stringency conditions, are also encompassed by the invention. Polypeptides encoded by these polynucleotides and/or nucleic acids, other polynucleotides and/or nucleic acids encoding these polypeptides, and antibodies that bind these polypeptides are also encompassed by the invention. Additionally, fragments and variants of the above-described polynucleotides, nucleic acids, and polypeptides are also encompassed by the invention.

In specific embodiments, polynucleotides of the invention comprise, or alternatively consist of a polynucleotide sequence in which the 3' 10 polynucleotides of one of the sequences delineated in column 6 of Table 1C and the 5' 10 polynucleotides of another sequence in column 6 corresponding to the same row are directly contiguous. In preferred embodiments, the 3' 10 polynucleotides of one of the sequences delineated in column 6 of Table 1C is directly contiguous with the 5' 10 polynucleotides of the next sequential exon delineated in Table 1C, column 6. Nucleic acids which hybridize to the complement of these 20 contiguous polynucleotides under stringent hybridization conditions or alternatively, under lower stringency conditions, are also encompassed by the invention. Polypeptides encoded by these polynucleotides and/or nucleic acids, other polynucleotides and/or nucleic acids encoding these polypeptides, and antibodies that bind these polypeptides are also encompassed by the invention. Additionally, fragments and variants of the above-described polynucleotides, nucleic acids, and polypeptides are also encompassed by the invention.

Table 3

Many polynucleotide sequences, such as EST sequences, are publicly available and accessible through sequence databases and may have been publicly available prior to conception of the present invention. Preferably, such related polynucleotides are specifically excluded from the scope of the present invention. Accordingly, for each contig sequence (SEQ ID NO:X) listed in the fifth column of Table 1A and/or in fourth column of Tables 1B.1 or 1B.2, preferably excluded are one or more polynucleotides comprising a nucleotide sequence described by the general formula of a–b, where a is any integer between 1 and the final nucleotide minus 15 of SEQ ID NO:X, b is an integer of 15 to the final nucleotide of SEQ ID NO:X, where both a and b correspond to the positions of nucleotide residues shown in SEQ ID NO:X, and where b is greater than or equal to a+14. More specifically, preferably excluded are one or more polynucleotides comprising a nucleotide sequence described by the general formula of a–b, where a and b are integers as defined in columns 4 and 5, respectively, of Table 3. In specific embodiments, the polynucleotides of the invention do not consist of at least one, two, three, four, five, ten, or more of the specific polynucleotide sequences referenced by the Genbank Accession No. as disclosed in column 6 of Table 3 (including for example, published sequence in connection with a particular BAC clone). In further embodiments, preferably excluded from the invention are the specific polynucleotide sequence(s) contained in the clones corresponding to at least one, two, three, four, five, ten, or more of the available material having the accession numbers identified in the sixth column of this Table (including for example, the actual sequence contained in an identified BAC clone). In no way is this listing meant to encompass all of the sequences which may be excluded by the general formula, it is just a representative example. All references available through these accessions are hereby incorporated by reference in their entirety. Table 3, from U.S. patent application Ser. No. 10/472,532, filed Sep. 20, 2003, is herein incorporated by reference. Table 3 in priority Application No. PCT/US02/09785, filed Mar. 19, 2002, which corresponds to Publication No. WO02/95010, published Nov. 28, 2002 (e.g., pages 643 to 798 of Publication No. WO02/95010) is incorporated by reference herein in its entirety.

TABLE 3

| cDNA Clone ID | SEQ ID NO: X | Contig ID: | EST Disclaimer Range of a | EST Disclaimer Range of b | Accession Numbers |
|---|---|---|---|---|---|
| HNFIP24 | 1 | 351534 | | | H04128, AA099288, AA101983 |
| HETBY74 | 7 | 361396 | | | R23770, R26913, R32172, R32216, R38317, R39395, R63720, R63767, R70906, R70940, R70993, R77169, R82584, R82585, H01942, H04495, H21696, H21906, H97740, H99748, N62092, N95055, W38893, W93362, W93394, W93606, AA016203, AA016243, AA076610, AA079633, AA079807, AA086218, AA158761, AA159815, AA159816, AA159710, AA159711, AA159565, AA160381, AA186897, AA188520 |
| HTEEB42 | 9 | 206980 | 1-1008 | 15-1022 | AL522795, AA725566, AI421450, AL522796, AI199779, AA406389, AA912674, AW022835, AI952846, AI123727, BE218057, AW022646, N90730, BF846982, BF845761, AI652914, BF056970, AW020783, AI312805, AW393829, AI017553, AW393887, AW474261, AW264246, BF848293, AI366088, AI418268, T89217, AI052637, AW082343, BF221504, AW593293, AA865038, AI201753, BF091146, AI140139, AA987434, AA410345, BF846977, BF846980, AW900593, BF932982, BF932991, AW865421, AW136481, AI650503, AI432092, T89127, AA974715, AW261924, BE938414, AF255910.1, AY016009.1, AP001694.1, AP000087.1, AP000225.1, AP000226.1, AP000086.1, AP000223.1. |
| HTEEB42 | 9 | 206980 | 1-1008 | 15-1022 | AL522795, AA725566, AI421450, AL522796, AI199779, AA406389, AA912674, AW022835, AI952846, AI123727, BE218057, AW022646, N90730, BF846982, BF845761, AI652914, BF056970, AW020783, AI312805, AW393829, AI017553, AW393887, AW474261, AW264246, BF848293, AI366088, AI418268, T89217, AI052637, AW082343, BF221504, AW593293, AA865038, AI201753, BF091146, AI140139, AA987434, AA410345, BF846977, BF846980, AW900593, BF932982, BF932991, AW865421, AW136481, AI650503, AI432092, T89127, AA974715, AW261924, BE938414, AF255910, AP001694, AP000087, AF255911, AX036060, AP000225, AP000226, AP000086, and AP000223. |
| HEQCC55 | 15 | 1352368 | 1-986 | 15-1000 | BF344112, BE275042, BE275057, BE563860, BE876310, BE880309, BE910481, BE733268, BF526321, BG169508, BE876530, BE878582, BE384718, BE562629, BG170369, BG170840, BE304867, AI492143, |

TABLE 3-continued

| cDNA Clone ID | SEQ ID NO: X | Contig ID: | EST Disclaimer Range of a | Range of b | Accession Numbers |
|---|---|---|---|---|---|
| | | | | | AI768116, BE876850, BG164974, BF338794, BE274902, AA149044, AW204761, AI768403, AI221536, BE395085, BG032898, AW172990, BG248912, AW051452, AW262030, BF114971, AI800959, AW338518, AI827127, AI568941, AI761510, F25336, AI313436, AI086734, N41733, AA994944, AW938942, BF063028, AW628237, AI219327, AW859588, AI718198, BF108787, AI004154, AI864228, BF197631, AI767239, AW001699, AI796303, T56712, AA576558, AI911799, AW149867, AI470703, AA149043, BG236779, AI470484, N83862, BG249788, AA631934, AI270718, AA610401, AI813825, AI401800, AI358289, AI799902, H95227, AW166567, AI264959, AI611273, R48167, BE730123, AI867518, AW815436, AW815444, BF338447, AW391445, AW815697, AI167239, AA970894, AW815514, T74424, BE076102, AW815626, BE076131, BG168390, BG169301, AI910684, AI189491, BE075966, AW843216, AA386018, BE076032, AA873480, R33355, T74049, BF338531, BF734770, AI919408, AI858303, AI701259, D29265, BF331419, BF982285, BE042437, AA996249, BG002211, AW374913, BC002718.1, AF191148.1, AB035480.1, AC004643.1, AB035481.1. |
| HEMCM42 | 15 | 1352150 | 1-986 | 15-1000 | BF344112, BE275042, BE275057, BE563860, BE876310, BE880309, BE910481, BE733268, BF526321, BG169508, BE876530, BE878582, BE384718, BE562629, BG170369, BG170840, BE304867, AI492143, AI768116, BE876850, BG164974, BF338794, BE274902, AA149044, AW204761, AI768403, AI221536, BE395085, BG032898, AW172990, BG248912, AW051452, AW262030, BF114971, AI800959, AW338518, AI827127, AI568941, AI761510, F25336, AI313436, AI086734, N41733, AA994944, AW938942, BF063028, AW628237, AI219327, AW859588, AI718198, BF108787, AI004154, AI864228, BF197631, AI767239, AW001699, AI796303, T56712, AA576558, AI911799, AW149867, AI470703, AA149043, BG236779, AI470484, N83862, BG249788, AA631934, AI270718, AA610401, AI813825, AI401800, AI358289, AI799902, H95227, AW166567, AI264959, AI611273, R48167, BE730123, AI867518, AW815436, AW815444, BF338447, AW391445, AW815697, AI167239, AA970894, AW815514, T74424, BE076102, AW815626, BE076131, BG168390, BG169301, AI910684, AI189491, BE075966, AW843216, AA386018, BE076032, AA873480, R33355, T74049, BF338531, BF734770, AI919408, AI858303, AI701259, D29265, BF331419, |

TABLE 3-continued

| cDNA Clone ID | SEQ ID NO: X | Contig ID: | EST Disclaimer Range of a | Range of b | Accession Numbers |
|---|---|---|---|---|---|
| | | | | | BF982285, BE042437, AA996249, BG002211, AW374913, BC002718.1, AF191148.1, AB035480.1, AC004643.1, AB035481.1. |
| HEMAE80 | 20 | 409495 | | | T71556, T90634, T82005, T83161, H57113, H61567, AA233071 |
| HEMAE80 | 22 | 1310948 | 1-1078 | 15-1092 | AI742654, AA461037, BF949730, AA460463, AI571360, AA701618, AI127309, AI633508, AA233071, AA448648, AA448744, AA897786, BF477408, AI206655, T82005, AI589742, T71556, T83161, T90634, H61567, H57113, H60996, AV707024, AV725948, AV701724, AV727990, AV706677, AV702026, AV729131, AV703989, AW949478, AV728436, AV727314, AV727935, AW949477, AV728518, AV728523, AV725134, AV656283, AV696791, AV698429, AV684604, AV692972, AV685688, AV689800, AV693005, AV656478, AV702516, AW964421, AV702266, AV709660, AV687909, AV656903, AV661704, AV697196, AV655280, AV659322, AV709314, AV708381, AV660728, AV691080, AV703169, AV659536, AV706721, AV729220, AV687035, AV655096, AV706223, AV726816, AV695545, AV708025, AV707933, AV708980, AV692691, AV701914, AV708992, AV726103, AV727029, AV728733, AV727100, AV705280, AV686064, AW960720, AV686060, AV703515, AV703472, AW955900, AW951263, AW967047, AV704553, AV704785, AW953797, AV692600, AV651955, AV725208, AW952751, AV727238, AV709880, AV696866, AV725920, AV693523, AV706342, AV725826, AW949353, AV654908, AV728546, AV692345, AV726584, AV698290, AV698609, AV725582, AV649758, AV708438, AV696106, AV689111, AV728157, AV708893, AV704217, AV702280, AV725031, AW951280, AV696931, AV726624, AV709604, AV652001, AV701946, AV704955, AV702117, AW954248, AV701707, AV707753, AV704269, AV702832, AV701560, AV705693, AV708704, AV726738, AV703495, AW964095, AV702772, AV726156, AV697288, AV652290, AV648263, AV647789, AV727787, AV660608, AV698545, AW955053, AV725497, AW952410, AV699089, AW950443, AV654035, AV706854, AV728997, AV656256, AW960601, AW956199, AW952403, AV704234, AV729378, AW952183, AV705159, AW959806, AV709407, AV703494, AV725633, AW956075, AV645936, AV709587, AW955723, AV658084, AW962384, AV650315, AV659389, AV697880, |

TABLE 3-continued

| cDNA Clone ID | SEQ ID NO: X | Contig ID: | EST Disclaimer Range of a | Range of b | Accession Numbers |
|---|---|---|---|---|---|
| | | | | | AV727613, AV726010, AV660258, AV708109, AW956474, AV659294, AV703146, AV725745, AV728148, AW951239, AW020543, AV726590, AV653353, AV654070, AW951281, AV706219, AV702385, AV658275, AW949802, AV702790, AV703669, AV707979, AV726194, AV727003, AV709580, AV702372, AV708786, AV659547, AW957517, AW959543, AV727526, AV705416, AV651920, AV725618, AW954439, AV707541, AV725577, AV725033, AV728924, AF193766.1, AF274956.1, Z59544.1, Y08991.1, AF217994.1. |
| HRDFB85 | 28 | 411020 | 1-1691 | 15-1705 | AL526995, AU133713, AU122264, AU133716, AU133898, AU133901, AU121966, AU141449, BE792903, BE786350, AU133817, AU136746, AU133887, AU121817, BG254161, AU133655, AU133578, AU121969, AU133752, BE907881, BG260814, AU133916, AU136516, BG179180, AU134354, BF038418, BF036516, BF037422, AU138430, BE734836, BE873066, AU133630, BE875603, AW844114, AU122380, AU134380, BE616872, BE871117, BE880804, BE871864, AU134369, BE902820, BG256045, BE536853, AU133618, BE304643, BE787818, AU147972, AU138507, AA700004, AI927220, AW170580, W74492, BF446247, BE812430, AU147690, BE870378, AI991311, AW935041, AA523290, AI859845, BF681403, AU136509, AI081052, AU155374, AA535079, AU159009, AI400364, AU147886, AI335984, AU155390, BG254485, AW193221, AW874638, AU155077, BE564185, AW170345, AA622540, AU155064, AI273767, AA522795, AW474974, AW770097, BF445088, AW168283, AI188508, AI559433, AI420481, AI246782, AU157642, BF182989, BF825787, AW815382, BF110949, AW662920, AI928146, AA157892, BG000738, AU133955, AA314960, AW815398, AI281336, AU155007, BE740807, AU155054, BF447199, AU154870, AA838633, AA844471, AW589514, AI401064, AW844815, AW815552, AI949231, AU154943, AI911649, AI268908, AI874198, AI186144, AI819846, BF742353, AW193220, AI863584, AL036495, BE930559, AA149417, AW168206, AA565989, W79089, BE819070, AA506616, AI564546, BF987328, BF435486, BE903940, AA434123, AA149738, W02467, AW194453, AA948146, AU155067, AL526954, C06165, AI276313, BG002911, AI963847, BG254948, AI874344, BF476318, BF987337, AI660464, AI567796, BE745379, BE673504, BF446395, AW167101, BF990584, AA434059, AI739607, AI560666, AI280032, AI961910, R48300, |

TABLE 3-continued

| cDNA Clone ID | SEQ ID NO: X | Contig ID: | EST Disclaimer Range of a | EST Disclaimer Range of b | Accession Numbers |
|---|---|---|---|---|---|
| | | | | | AW009339, BE840036, AA551656, BE840048, AW167849, AW513272, BF001751, AI346572, AI923100, AI005290, AI091394, H93341, AI588982, AI819915, AI950029, AI991855, AI347074, AI347076, AI660868, AA295491, BE930558, AW874110, AI682624, AI348165, AI949885, BF001991, AW374558, AW516096, AI347071, AU154878, AW014104, AI343369, AI860565, AW167111, AI222884, AI861959, AW194388, BE840202, BF109128, AI283186, AI347501, AI305833, AI031766, AI346386, AI346944, AW189088, AI032425, H27323, AI283162, BE048493, BF569270, AI347072, AW510456, BE840244, BF001523, BF111772, AI214245, AI346606, AI743195, BE840045, AW015201, AI347060, AI346569, AW572261, AW275383, AI281140, AI346475, AI743978, AI274133, AI738882, AI347930, AI273374, AI738627, AI991114, AI097004, AI144005, U46417, AI304544, AA157596, AI281141, AA569935, AI274318, AI285074, AI346274, AI336454, AI346908, AI339875, AK026651, AB000712, D88492, AX014904, AB000714, AF007189, AF095905, AJ011656, M74067, AJ130941, AC004643, AJ249735, R12121, T96099, R05961, R05962, R36883, R48403, R50075, R50076, H13937, H27324, H27350, H44304, H93844, N72688, W21446, AA149303, AA149402. |
| HDTAW95 | 38 | 412472 | 1-1274 | 15-1288 | AL532456, BE896915, BE387335, AW071610, AA584310, AI762109, BF691507, AW994682, AI085616, BE550475, AI422726, AW316980, AI809642, AI743774, BF000103, AA482398, BE551643, AI359844, BE550264, AI379443, AA406425, AA482544, AW518948, BE221566, AW276370, AI656907, AA410434, AI380885, AW236626, BE169370, AI963298, AA857920, AW519014, AI352209, AV649395, AI469175, AI920963, AI631574, AI700002, AI750892, AI218433, AA335862, C01758, AI760411, BF432104, AA335551, AW594188, AW084890, AA723450, AI653051, AA738416, AI074769, AI081084, AA974239, AA969841, AW137377, AI239604, AI391517, AW594685, AW518917, BF000821, AI370649, AW662493, R46762, BE843536, AA507081, BF507778, AW630561, AI750893, AW837990, R46857, AW608087, AW838003, AI074870, AI369474, BE504418, D62262, BE698661, F13673, AW627356, D79314, AI418593, AI337269, AW627526, AA588673, BF573143. |
| HEMCV19 | 46 | 423219 | | | R39576, R39644, R55519, R55520, H25585, H25630, H42497, H43485, R95168, H73675, H73419, H80718, H80719, W95391, W95348, AA034079, AA044081, AA187305, AA187096 |

TABLE 3-continued

| cDNA Clone ID | SEQ ID NO: X | Contig ID: | EST Disclaimer Range of a | Range of b | Accession Numbers |
|---|---|---|---|---|---|
| HEMCV19 | 48 | 1352162 | 1-722 | 15-736 | BE614883, BE873075, BG025158, BE253565, BE875979, BE395207, AW954217, BE734057, BE789549, BF529722, BE614806, BE738333, BE785505, AA044211, BF340317, AW238972, AW406916, R95168, BF737302, BF812968, BF738993, AA075901, BF792671, BG012029, AW796084, H25630, BE876237, BE183450, BF901660, BE810793, H43485, AA296837, H80718, AA287470, AA298795, AA296826, AA296696, AI342703, AA296869, AA218811, AW802996, AA034079, BE737872, H73675, R55519, W95348, BF331433, AV743953, BF082160, BF868942, BF809994, BE775061, C00212, AL532494, BF997411, R39644, BE828356, BF804848, AA806231, AL532493, BF799156, BF895320, AA187096, AA297863, BF245896, BF905334, N86960, T10507, BE904822, BF931829, BF829581, BE140100, AI819836, BE396147, BF747982, BF056207, BF763569, BF807379, AA465105, BF811185, BF446055, AA583464, AA485829, AI582284, AA983595, BF771777, BF750444, AA523623, BF771828, AI952620, AA044081, BF736987, AI346295, BF978464, BF248485, AA912088, AW512207, AI028038, AI066489, AI424071, AI521467, AA699982, AI358167, AA722634, H42497, AC002390.1, AF177940. 1. |
| HETBX14 | 61 | 806447 | 1-1278 | 15-1292 | BE867930, BE219655, BF476474, AW511566, AI521607, AI217150, AI183346, AI283289, AW000834, AA436049, AA435952, AA532717, AA403004, BE673570, AI624187, BE898804, W60282, AI913780, W60374, AA402971, AA477283, BF679282, AA412318, AA477282, AW969530, BE150851, AA482081, BF222155, AA402028, BE646241, BF677072, AA514646, BE150769, AA503821, AI611257, AI659265, BE828491, BF515767, AW578446, AW166796, AI874153, BF573830, AW874467, AB041036, AB012917, AX016289, AX016287, AB013730, AC011473, AF164623, AF243527, AR060847, AB016226, AF135025, AC011473, AC011473. |
| HETBX14 | 65 | 422659 | | | W60282 |
| HLHSK94 | 70 | 422828 | | | R55809, H83295, N92239, W37154, W38638, N90902, AA017680, AA040604, AA040705 |
| HLHSK94 | 72 | 1307727 | 1-1775 | 15-1789 | AW956492, BF352284, BE709448, W29010, AV751953, AI829559, BE179448, AI571060, AI083491, AA905071, AW118125, AI049799, W22553, N90902, W27632, AI273588, AI890622, W27896, AW195777, W22119, BF844755, AA040604, W23268, AW269932, W38638, W37154, AA904910, W27944, R55894, W27681, AW607334, AA337059, AW367713, AW607165, BF351195, AW966017, AA298658, R55809, C02576, BE163743, AI376671, AA364393, AV746728, |

TABLE 3-continued

| cDNA Clone ID | SEQ ID NO: X | Contig ID: | EST Disclaimer Range of a | Range of b | Accession Numbers |
|---|---|---|---|---|---|
| | | | | | AI393483, W23093, BE708746, W28670, W27851, BF844715, H83295, BF437730, N92239, AI194027, W27371, D81988, BE163611, BE163731, C14616, C14877, AA040705, AA897696, AV747434, BF850779, AA017680, H83294, AW974810, AF122922. 1. |
| HLHFP03 | 76 | 460467 | 1-599 | 15-613 | H46196, AI421986, H19572, H46195, BF947135, H19490, BF738481, BF994257, BF127477, AW139949, BF947011, AF141377, AF169202, AC011976, and AC011976. |
| HLHFP03 | 78 | 460467 | 1-599 | 15-613 | H46196, AI421986, H19572, H46195, BF947135, H19490, BF738481, BF994257, BF127477, AW139949, BF947011, AF321824. 1. |
| HHTLF25 | 83 | 461438 | 1-683 | 15-697 | AA481924, BF343628, AI276798, BE858514, BF915546, BG058647, BF917552, AI299346, N41026, BF914451, AA989053, W60864, BF915075, AI423526, BF106006, AI289858, AA746220, BF915128, AI306602, AW015647, AA633118, AI207255, BF913974, AI301688, W92376, AI139176, AA971275, AA480109, H12338, BF912934, AA865668, BF901361, F30553, AW975896, AA991168, AI302882, BF915115, AA729941, AA627378, AA865651, AW607348, H39980, AA729534, T55959, T57206, AW607175, W60940, BE155729, AI880682, AW383808, BG058709, AW383055, AW383057, BE154544, AW383016, AW383047, AW383871, AW383051, BF901355, AW383000, AI919456, BE154555, AW383784, BF914191, F32872, AI017727, AA974881, BE154538, AW383009, BF092099, AI243983, AA991170, R49835, R49793, AA318120, BF893642, W74783, AW382999, AV712713, AW579628, AW382994, H12392, AW372144, AW372157, AW383836, T52100, AW372154, AW383822, AW383837, AW579627, AW383817, AW372166, BF881098, AW382997, D20493, AW372161, AW383865, AA918360, N47127, AW579992, AA937670, AW579601, AW579998, AU076484, AI245273, BF831159, AA664094, AA878598, AA865673, AI807718, AA937805, BF350664, AI525220, AD000833.1, AF019563.1, AF019562.1, AJ010098.1, AD000864.1, X78928.1, AF072845. 1. |
| HHTLF25 | 83 | 461438 | 1-683 | 15-697 | AA481924, BF343628, AI276798, BE858514, BF915546, BG058647, BF917552, AI299346, N41026, BF914451, AA989053, W60864, BF915075, AI423526, BF106006, AI289858, AA746220, BF915128, AI306602, AW015647, AA633118, AI207255, BF913974, AI301688, W92376, AI139176, AA971275, AA480109, H12338, BF912934, AA865668, BF901361, F30553, |

TABLE 3-continued

| cDNA Clone ID | SEQ ID NO: X | Contig ID: | Range of a | Range of b | EST Disclaimer Accession Numbers |
|---|---|---|---|---|---|
| | | | | | AW975896, AA991168, AI302882, BF915115, AA729941, AA627378, AA865651, AW607348, H39980, AA729534, T55959, T57206, AW607175, W60940, BE155729, AI880682, AW383808, BG058709, AW383055, AW383057, BE154544, AW383016, AW383047, AW383871, AW383051, BF901355, AW383000, AI919456, BE154555, AW383784, BF914191, F32872, AI017727, AA974881, BE154538, AW383009, BF092099, AI243983, AA991170, R49835, R49793, AA318120, BF893642, W74783, AW382999, AV712713, AW579628, AW382994, H12392, AW372144, AW372157, AW383836, T52100, AW372154, AW383822, AW383837, AW579627, AW383817, AW372166, BF881098, AW382997, D20493, AW372161, AW383865, AA918360, N47127, AW579992, AA937670, AW579601, AW579998, AU076484, AI245273, BF831159, AA664094, AA878598, AA865673, AI807718, AA937805, BF350664, AI525220, AD000833, AF019563, AF019562, AJ010098, A83704, AF152021, AF247680, AD000864, AF285446, 125670, X78928, and AF072845. |
| HTADX17 | 90 | 457172 | 1-1126 | 15-1140 | AA446344, AA612751, AA298785, AA298780, AA298784, AA446524, AA298781, AA381170, AL357565, and AL357565. |
| HTADX17 | 92 | 753289 | 1-1133 | 15-1147 | AA446344, AA612751, AA298785, AA298780, AA298784, AA446524, AA298781, AA381170. |
| HJACG02 | 104 | 1307789 | 1-561 | 15-575 | AA311223, BF002026, N41594, N30820, BF982046, AI829327, BE047833, AI457369, AW071417, BF968205, AI340627, R36271, AL036980, BF061283, BG168549, AW022682, BG034550, AV682418, AL047042, BF343172, BG113299, AW020693, BF751308, AI452560, AI690748, AI349645, AW946806, AI340511, BF924882, AW074869, AW196299, AL038445, BE781369, AW302992, BG110684, BE887488, AL514193, AI310575, BG164558, AI340533, AI349957, AI433384, BF680133, AV715560, AI309401, AI345005, BG163618, AI343112, AV743962, AI826225, AI811785, AI494201, AW054931, AW268302, AW301300, AI349598, BF672397, AW072719, AW075207, BF526020, AV741327, AI345735, BG036846, AI697243, BE536058, AW193134, AI889147, BF904189, BE910373, AI500077, AA225339, BE138712, AI307210, BG033723, AI589267, AI269862, BE885353, AI313320, BG058150, BE886728, AW827106, BF527014, AI313352, BG110517, AL039086, AW079336, AI251434, AI274728, BF868928, AI524780, AI589947, AV682724, AI439717, AI312146, AI312339, AI814087, AI345745, AL036925, |

TABLE 3-continued

| cDNA Clone ID | SEQ ID NO: X | Contig ID: | EST Disclaimer Range of a | EST Disclaimer Range of b | Accession Numbers |
|---|---|---|---|---|---|
| | | | | | AI345258, AI932638, AI470651, AL036857, AW050578, AW196105, AV682227, AI306705, AW269097, AI620639, AI611348, AW090393, AL042628, AW152469, AA833760, BG256090, AI866798, AW074993, AI567351, AI431424, AI349614, AI311604, AW105601, BE966990, AL044207, AW167918, AI611738, AW169604, AW268253, AI862144, AI567612, BE886827, BF793308, AI890806, AI349256, AL036664, AI554821, AI312152, AI955906, AI336495, BF970768, BF885000, AW075084, AL120854, BE895585, AI950664, BE897632, BE964078, BF872670, AW022699, AI349937, AL036923, AW089572, AI334884, AI307543, AW151138, AW071412, BF885081, AI307708, AI312325, AI500659, AI868204, AI340659, BF816037, AI280655, AI612885, BF092710, AW302965, BF339322, AI334930, AI309443, AV699211, AV734185, AI307520, AI445237, AV724373, AI590423, AV756798, AI345739, AI889168, AI440263, AW117743, AI312143, AW673635, AW806761, AI343037, AV708834, AI434256, AI312428, W33163, BG109270, BE966829, AI349955, AW075093, AI371228, BE548914, AW827206, AI348897, AA427700, AI306613, AI312357, AI335426, AI348777, AI308032, AI569583, AI687127, BG249582, AI783997, BG030364, BG104820, AW161579, AI627988, AI344785, BG113662, BE971716, BF970449, AL079963, AL036718, BE047852, BE785868, AI207454, AI382670, AW020095, AI874166, AL036901, BE047952, AI670009, BG180996, BF970990, BF526262, BG027280, AL036274, BF061286, AI497733, AL041150, AI288285, AI890507, BG026428, AW827115, AW268964, AI343091, AI318280, AI567582, BG165051, AI554245, BE963035, BE138658, BG260037, AI310582, BG032208, BF344691, BE885490, AF352730.1, AF205952.1, AF323081.1, AK024538.1, X53587.1, AL512765.1, AL050393.1, AK025254.1, AF090901.1, AK026542.1, AL136787.1, AK026597.1, BC006525.1, AF218031.1, BC001963.1, BC007326.1, AB055366.1, AK027213.1, AL389939.1, AK026528.1, AK026855.1, AL122110.1, BC008780.1, AF090943.1, AL133098.1, AL136799.1, BC008070.1, BC003687.1, AK024524.1, AF091084.1, AL049466.1, AK025967.1, AK026480.1, BC002839.1, BC006807.1, AL136789.1, AL157482.1, AL117394.1, AK025391.1, AL137560.1, AY034001.1, AK025349.1, AF125948.1, AL359615.1, AJ242859.1, AK025906.1, |

TABLE 3-continued

| cDNA Clone ID | SEQ ID NO: X | Contig ID: | EST Disclaimer Range of a | Range of b | Accession Numbers |
|---|---|---|---|---|---|
| | | | | | AL136915.1, AL110221.1, AL050092.1, AL512718.1, AB056427.1, AK027146.1, AB060825.1, AL133075.1, AK025484.1, AK000391.1, AF056191.1, AB051158.1, AK026583.1, AB060908.1, AL133557.1, AL117457.1, AL110225.1, AK026526.1, AL080159.1, AL137550.1, AK026629.1, AL133640.1, AB063046.1, AF217987.1, AK026452.1, U42766.1, AL133606.1, AK026534.1, AL133067.1, AK024588.1, AB047615.1, AB048954.1, AK027182.1, AL049464.1, AL133113.1, AL133560.1, AL137521.1, BC008983.1, AB060912.1, AF097996.1, AK026353.1, BC008899.1, BC001967.1, AK026959.1, AL137459.1, AB060839.1, BC003548.1, AF090900.1, AL050116.1, AB052200.1, AL133016.1, AL359620.1, AB060214.1, AF057300.1, AF057299.1, X72889.1, AK000618.1, BC002643.1, BC008417.1, AK026164.1, AK026506.1, AK026741.1, AL359618.1, AL442082.1, BC007199.1, AK025465.1, U91329.1, L19437.2, AL049314.1, AB056421.1, BC004958.1, AK027164.1, AB056809.1, AL162062.1, AL050149.1, AL389982.1, AL137463.1, AL122123.1, AF230496.1, AL162002.1, AB048964.1, AL133080.1, AL390154.1, BC006164.1, AK000137.1, AK026762.1, AL117460.1, AK026630.1, AL512689.1, AL512719.1, AL050108.1, AK026593.1, AB063100.1, S61953.1, AL049300.1, AL049452.1, BC005151.1, AK000647.1, BC001045.1, AB063079.1, BC002733.1, AL136893.1, BC002342.1, AK025383.1, BC004556.1, BC009284.1, AL080086.1, BC005678.1, AF078844.1, AF026816.2, AL136928.1, AL512750.1, BC003627.1, Y16645.1, AB062942.1, AF051325.1, AL512754.1, BC006103.1, U58996.2, AB060863.1, AL136844.1, AK000212.1, AL080074.1, AL359601.1, AF262032.1, AK026600.1, AL136864.1, U80742.1, AL136845.1, AL122093.1, BC008893.1, AL136892.1, BC006201.1, AL117435.1, BC008365.1, AL110280.1, AF061943.1, AL136749.1, AK027868.1, AB019565.1, AF162270.1, BC008382.1, AL133104.1, AF003737.1, AF353396.1, AL137557.1, AK000445.1, BC008284.1, AK000432.1, AF218014.1, AL136786.1, |

TABLE 3-continued

| cDNA Clone ID | SEQ ID NO: X | Contig ID: | EST Disclaimer Range of a | Range of b | Accession Numbers |
|---|---|---|---|---|---|
| | | | | | AB050510.1, AK024601.1, AL117583.1, AL137648.1, AB060929.1, AK025491.1, AL117585.1, AL122098.1, AK025573.1, AF219137.1, AF090903.1, AF125949.1, AF260566.1, AL050146.1, AF111847.1, AL442072.1, AB062978.1, AJ006417.1, AL122121.1, AJ012755.1, AL136784.1, AF104032.1, BC008488.1, AL080060.1, AB055315.1, AL137478.1, AB047887.1, AF132676.1, AF061836.1, AF183393.1, AK027204.1, AL080127.1, AK026647.1, AK027116.1, AL096744.1, AB055361.1, AL353940.1, BC008387.1, AL137556.1, X82434.1, AF090934.1, AL122049.1, AL162008.1, AB063070.1, AL122050.1, AL162003.1, AL137271.1, BC005168.1, AB048974.1, AK025798.1, AB055368.1, S78214.1, AK000486.1. |
| HKGAJ54 | 107 | 498303 | 1-1332 | 15-1346 | H97115, AA130346, and AA193462. |
| HKGAJ54 | 109 | 1300770 | 1-1318 | 15-1332 | AA757140, BE301253, AL528730, AI761849, AL520073, BG150431, AI288886, BE301262, AW380873, BE018216, AA227523, AA227644, AI224842, AI417635, AI094181, H97115, AA193462, AW371297, AL039859, AA262346, AW957515, AA577940, AI435978, AA373648, AW381560, AW380920, H96998, AI240420, AA130346, W88873, W90542, AA001144, AW381554, AF074684, AA253322, BF083570, AA193344, AL520074, BE173261, AA368803, AI718525, AA831401, AA741509, AI741117, AK027852.1, BC008993.1. |
| HE8CH92 | 118 | 609866 | 1-1268 | 15-1282 | BF338867, AI862534, AA861640, AI149724, AA400490, AA759080, AA400536, AI218853, H52956, BE550640, AI476417, AW274868, BE552351, H53024, AA843555, H53025, AA936598, AW516351, T81709, AL079515, AW292593, AI280269, AA629002, AL079514. |
| HSVAK93 | 120 | 1352228 | 1-1226 | 15-1240 | BF338867, AI862534, AI149724, AA400536, AA400490, AA861640, AA759080, H52956, AI218853, H53024, BE550640, AW274868, BE552351, AI476417, H53025, AA843555, AA936598, AW516351, T81709, AL079515, AW292593, AL079514, AI280269, AA629002, BC008988.1, AC008491.6, AC010315.6. |
| HSDEK49 | 125 | 1352253 | 1-1768 | 15-1782 | AL513706, AL513705, AV700980, BF343961, AV710516, AV716397, AV715849, BF351156, AV717025, AW071975, AI922669, AI129815, BF106386, AA702864, W32947, AV690218, AV685715, AV693576, AV686846, AV695322, AV697709, BF924861, AI168499, AI343825, AA627735, AI554367, AI335089, AV697729, AI290781, AA875852, AA442570, AV686969, AV698914, AA486920, AI357884, AI088635, |

TABLE 3-continued

| cDNA Clone ID | SEQ ID NO: X | Contig ID: | EST Disclaimer Range of a | EST Disclaimer Range of b | Accession Numbers |
|---|---|---|---|---|---|
| | | | | | W79882, R39812, AV683817, BF932594, W17367, N78991, AA972857, R62969, R59135, AW961380, R56601, BE857524, R66262, W74268, AA436814, AA813538, H05057, AA133776, Z43556, R14044, R81029, T48889, AA228697, R56602, AA142932, R63023, Z39624, F02373, AA993978, R66723, R67603, R59136, R80928, AA133775, AW874480, T48888, AA228698, AA368546, BF525711, AA115592, AA328299, AA486747, BG001652, AJ132502.1, AL034397.1. |
| HWBAO62 | 127 | 838164 | 1-1889 | 15-1903 | AI683471, AI792952. |
| HWHGU54 | 131 | 695695 | 1-1431 | 15-1445 | AA458648, BE140448, AA455546, AL132708.3, AL132990.3. |
| HWHGU54 | 131 | 695695 | 1-1431 | 15-1445 | AA458648, BE140448, AA455546, AL132708, and AL132990. |
| HCEJQ69 | 134 | 1243825 | 1-1763 | 15-1777 | BE889609, BF183110, BG248693, AI621234, AA452195, AI821464, AI821685, AI820935, AI745288, AI655244, AA436362, BF432211, AW770404, BF196926, AA427404, H08678, AA410412, H61387, AI432244, AA428418, H08677, AA410413, AA410253, H14737, BF351660, BG170733, H62405, AI968569, AW002476, AW166810, BE350305, BF530203, H09849, AW748526, AF283463.1, AC058790.14, AC007663.29, AC006549.28, AB045987.1. |
| HCEJQ69 | 134 | 1243825 | 1-1763 | 15-1777 | BE889609, BF183110, BG248693, AI621234, AA452195, AI821464, AI821685, AI820935, AI745288, AI655244, AA436362, BF432211, AW770404, BF196926, AA427404, H08678, AA410412, H61387, AI432244, AA428418, H08677, AA410413, AA410253, H14737, BF351660, BG170733, H62405, AI968569, AW002476, AW166810, BE350305, BF530203, H09849, AW748526, AX047642, AC058790, AC007663, AC006549, and AB045987. |
| HT5GJ57 | 159 | 740767 | 1-1783 | 15-1797 | AW574516, BG259057, BF975647, AW575080, BF795582, BE559713, BE396519, AI521311, BE397179, AW237047, AI446257, BF238156, BF663664, AI862389, AI573063, BE513368, AW296989, AU157608, BF128855, AA811488, AA827120, AW338778, AI439638, BE560794, AI250231, BG120258, AI312540, AA633095, AV742373, AI343438, AA604586, BE269253, AI669176, AI149413, AA723128, AW403042, AA722908, W57991, AI826124, BE246032, AU138425, BE513265, AI865336, AI219708, AI589599, AW732709, H23560, AA765412, AI589912, BE560732, T61448, AW444827, AA594614, AA648496, AA361096, N34423, W58075, AV742389, N48728, AA975334, AA731435, AA166766, BE247378, AA810638, AW298682, AI919140, AW402333, AI341517, BE245894, AV743440, AI962720, BF062274, T30849, AI982795, AW405561, T25945, AA810222, AA807717, Z39117, AV756294, |

TABLE 3-continued

| cDNA Clone ID | SEQ ID NO: X | Contig ID: | EST Disclaimer Range of a | Range of b | Accession Numbers |
|---|---|---|---|---|---|
| | | | | | AV724221, BG120887, AA593214, N48658, AW083122, AA639378, H23535, AI492348, AI656821, AF045555, AK002099, AF257135, AF161531, AC005081, AF086239, AC016675, AC016675, AC005081, and AC005081. |
| HT5GJ57 | 161 | 1299921 | 1-1759 | 15-1773 | BF975647, AW574516, BG259057, BE397179, BE396519, AW575080, BF795582, BF663664, AI521311, AW237047, AI446257, AI862389, BE559713, BF128855, AI573063, BF238156, AW296989, AU157608, AA811488, AA827120, AW338778, AI439638, AI250231, AI312540, AA633095, AV742373, AI343438, BE513368, AA604586, AI669176, AI149413, AW732709, AA723128, AW403042, BE269253, BE560794, AA722908, W57991, AI826124, BE246032, BG120258, AU138425, BE513265, AI865336, AI219708, AI589599, H23560, AA765412, AI589912, T61448, BE247378, BE560732, AW444827, AA594614, AA361096, AA648496, N34423, AV743440, W58075, N48728, AV742389, AA975334, AA731435, AA166766, AA810638, AW298682, AI919140, AI341517, BE245894, AI962720, BF062274, T30849, AW402333, AI982795, T25945, AA810222, AA807717, Z39117, AV756294, N48658, AW405561, AV724221, BG120887, AA593214, AW083122, AA639378, AI492348, H23535, AI656821, AF252613.1, BC009204.1, BC001609.1, AF252611.1, AF252614.1, AK002099.1, AF257135.1, AF252612.1, AF045555.1, BC006080.1, AC005081.3, AF086239.1. |
| HPIBX03 | 169 | 743314 | 1-2195 | 15-2209 | BG163962, AU140819, BF336602, BG168220, AU147884, AW996615, BF760456, AA922764, AA770561, AA976914, AA045899, BF063943, BF851894, BF815498, AA045900, BF764764, AW769303, AW996391, AW812414, AA132854, AB033417, AA132760, AK026622, AK023834, AK026187, AC010170. |
| HDPBO81 | 174 | 892018 | 1-3784 | 15-3798 | AI393580, BE041810, AI867153, AI307279, BE568549, AX047952, AX047936, AX047940. |
| HWBFY57 | 179 | 837478 | 1-1782 | 15-1796 | AW003259, BE673705, AW236996, AW590159, BF478096, BE218330, AI802017, AI707979, AW590572, AI970192, BF062678, AW615365, AA984871, AI796486, AI365178, AW138945, AI310573, C01628, AA324946. |
| HYABV21 | 182 | 1281466 | 1-2724 | 15-2738 | AW969109, AA278948, AA677057, AA813919, AW976932, AI572979, AW294948, AW503289, AW198126, AI419925, AA810016, AA278822, AA809271, T89787, AA505047, AA804243, R09908, AW500471, R12559, AA281955, AW383680, AA767265, AW503702, AW504600, T89422, H50970, AL356276, AC024085, U85195, |

TABLE 3-continued

| cDNA Clone ID | SEQ ID NO: X | Contig ID: | EST Disclaimer Range of a | Range of b | Accession Numbers |
|---|---|---|---|---|---|
| | | | | | AE000658, AC009248, and AC004671. |
| HOHBY69 | 186 | 827480 | 1-4981 | 15-4995 | BF965934, BF358074, AW753022, BG258877, AI621089, AW851445, AI751442, AW069755, W45174, H15811, AW339880, AI752628, AI751441, AW068275, BF509527, AW604115, BF056654, H16112, AI825217, W45078, BF749563, BF770980, BF770976, U53091, AA852615, AI738528, BF770978, BF928722, BF770979, AI750918, BF365293, AW888738, AA665807, BF328395, BG013602, AA852614, BF770969, AI752385, AI752488, BF770975, BF770962, AA316377, BF770974, AI752355, BF769640, BF758396, BF758424, BF830392, AI750919, AV699874, AV700783, AW166270, AF109681, AF137378, AL359064, Z50167, Z50157. |
| HDHMA45 | 202 | 902513 | 1-2170 | 15-2184 | AL538140, AI653241, AI826089, AI967938, AW003801, BE222599, AI056603, AI085672, AI201055, AI367072, AI052212, AI631456, AI278127, BF515139, AI597622, AI825589, BF961191, N47437, AA506257, AI197773, AI040587, BF934870, BF934966, AB028140.1, AP002436.3. |
| HMADJ14 | 206 | 1099342 | 1-1350 | 15-1364 | AI268407, AW450309, AI831182, AW295136, AF305068. |
| HMADJ14 | 212 | 843725 | 1-1430 | 15-1444 | AI268407, BE162690, AI831182, AW450309, AW295136, AA380009, AF305068. |
| HEAAL31 | 218 | 639007 | | | AA151656, AA151652, AA151733, AA151736 |
| HEAAL31 | 220 | 361221 | | | T56046, T56062, T56080, T56096, T90475, T90482, T90571, T90577, T74331, T89037, R10054, R11653, R54570, H22902, H24285, H24287, H50611, H50610, H67882, H67927, N27199, N36263, N39942, N40544, N44078, N46591, N58937, N73790, N94307, N95519, N99415, W02128, W19438, W32393, W57988, W58072, W73132, W90660, N90316, AA009898, AA022614, AA022615, AA025590, AA081613, AA084503, AA085189 |
| HEMFA84 | 222 | 608198 | 1-971 | 15-985 | BE743873, BE382707, BF316838, BE262654, AI344021, AW451305, AW291138, AW301011, BE784787, BG026465, AW957567, BG253034, AI807860, AI970736, N99472, AA378218, H23090, W31086, BE185755, AK025935, AF258545. |
| HDPPA04 | 224 | 904765 | 1-2392 | 15-2406 | AU135908, AI990290, AW961323, AI798762, AA044757, AW105205, AW197379, AU156359, AA039608, AA247117, AW889458, AA303575, AA036918, AA247128, AI214428, AW449368, AA044631, AI762460, AL162253.17, AK001872.1, AF344424.1, AF329193.1. |
| HE2OA95 | 230 | 637595 | 1-1657 | 15-1671 | AI620217, AL528146, AI056665, AW964795, AI744518, AI038199, AA236476, AA747220, AI368718, AI888960, N47941, AA234584, H19150, AI360711, BF445507, BF475619, AI682413, AI468582, H05762, AA297549, R52959, N46864, T27100, AA736703, |

TABLE 3-continued

| cDNA Clone ID | SEQ ID NO: X | Contig ID: | EST Disclaimer Range of a | Range of b | Accession Numbers |
|---|---|---|---|---|---|
| | | | | | AA579494, H18483, BE855666, Z40989, AI474169, R41378, AW973144, BF982162, N49148, AL157430, AF179274, AR052523, AB041565, AB017270, AR052522, AB004064. |
| HKABZ65 | 232 | 862030 | 1-1175 | 15-1189 | AA715814, AA503019, AV762033, BE155099, AV734997, BF917346, AW338860, AC011666.28, AF242518.1, AF109907.1, AC004867.5, AC020917.4, AC004166.12, AL356915.19, AC005071.2, AC004878.2, AC005052.2, AC005081.3, AC002549.1, AL590763.1, AC020663.1, AC006064.9, AC008745.6, AC004858.2, AC022405.5, AC007666.12, AC008750.7, AL451144.5, AP001716.1, AC009131.6, AC004656.1, AL109825.23, AL355312.24, AL035086.12, AC010605.4, AC004067.1, AC004477.1, AC008736.6, AL109915.10, AC006023.2, AL033529.25, AC007637.9, AL139317.5, AL031311.1, AL049776.3, AC004971.3, AC009220.10, AL080243.21, AC005015.2, AC004686.1, AL022318.2, AC002310.1, AC009123.6, Z93015.9, AC021999.4, AL355353.23, AL050318.13, AL161756.6, AC011464.5, AL132712.4, AL359513.12, AC007546.5, AP001695.1, AL035683.9, AC018711.4, D87675.1, AL133444.4, AL139100.9, AF030453.1, AC006077.1, AC008895.7, AP001713.1, Z84487.2, AL357153.4, AL163636.6, AL359382.23, AC004770.1, AP001972.4, AC004675.1, AL355392.7, AC020906.6, AL138784.30, AC020754.4, AL162426.20, AC002288.1, AC009068.10, AC008101.15, AC008623.4, AC008891.7, Z98884.11, AL136137.15, AC011247.10, AL133163.2, AP001727.1, AC005098.2, AC004659.1, AC005670.1, AL139022.4, AC009812.17, AF088219.1, AL035404.20, AL139801.17, AF228703.1, AC002492.1, AC006084.1, AL353594.13, AC005077.5, AL160271.19, AP001724.1, AC008537.5, AC024561.4, AL139353.3, AC004491.1, AC008626.5, AL391987.15, AC010530.7, AP003352.2, AC009267.15, AL122013.5, AP000008.1, AC087071.2, AC009314.4, AC020913.6, AL078463.11, AL096700.14, AC002369.1, AC010102.3, AP003357.2, AL031123.14, Z95331.2, AL513008.14, AL118501.22, AP001435.2, AC005200.1, AJ400877.1, AC011469.6, AC016772.8, AC005089.2, AC005088.2, AF312912.1, |

TABLE 3-continued

| cDNA Clone ID | SEQ ID NO: X | Contig ID: | EST Disclaimer Range of a | Range of b | Accession Numbers |
|---|---|---|---|---|---|
| | | | | | AL022316.2, AL080317.11, AP001693.1, AP000553.1, AL390294.19, AC006345.4, AC091394.2, AL359813.23, AC007283.3, AL353807.18, AL109921.21, AC074121.16, Z98742.5, AC007383.4, AF243527.1, AC027130.5, AC010504.7, AL035462.21, AC010650.8, AC005180.2, AF334404.1, AL139187.19, AC005037.2, AL021391.2. |

Table 4

Table 4 provides a key to the tissue/cell source identifier code disclosed in Table 1B.2, column 5. Column 1 of Table 4 provides the tissue/cell source identifier code disclosed in Table 1B.2, column 5. Columns 2-5 provide a description of the tissue or cell source. Note that "Description" and "Tissue" sources (i.e. columns 2 and 3) having the prefix "a_" indicates organs, tissues, or cells derived from "adult" sources. Codes corresponding to diseased tissues are indicated in column 6 with the word "disease." The use of the word "disease" in column 6 is non-limiting. The tissue or cell source may be specific (e.g. a neoplasm), or may be disease-associated (e.g., a tissue sample from a normal portion of a diseased organ). Furthermore, tissues and/or cells lacking the "disease" designation may still be derived from sources directly or indirectly involved in a disease state or disorder, and therefore may have a further utility in that disease state or disorder. In numerous cases where the tissue/cell source is a library, column 7 identifies the vector used to generate the library.

TABLE 4

| Code | Description | Tissue | Organ | Cell Line | Disease | Vector |
|---|---|---|---|---|---|---|
| AR022 | a_Heart | a_Heart | | | | |
| AR023 | a_Liver | a_Liver | | | | |
| AR024 | a_mammary gland | a_mammary gland | | | | |
| AR025 | a_Prostate | a_Prostate | | | | |
| AR026 | a_small intestine | a_small intestine | | | | |
| AR027 | a_Stomach | a_Stomach | | | | |
| AR028 | Blood B cells | Blood B cells | | | | |
| AR029 | Blood B cells activated | Blood B cells activated | | | | |
| AR030 | Blood B cells resting | Blood B cells resting | | | | |
| AR031 | Blood T cells activated | Blood T cells activated | | | | |
| AR032 | Blood T cells resting | Blood T cells resting | | | | |
| AR033 | brain | brain | | | | |
| AR034 | breast | breast | | | | |
| AR035 | breast cancer | breast cancer | | | | |
| AR036 | Cell Line CAOV3 | Cell Line CAOV3 | | | | |
| AR037 | cell line PA-1 | cell line PA-1 | | | | |
| AR038 | cell line transformed | cell line transformed | | | | |
| AR039 | colon | colon | | | | |
| AR040 | colon (9808co65R) | colon (9808co65R) | | | | |
| AR041 | colon (9809co15) | colon (9809co15) | | | | |
| AR042 | colon cancer | colon cancer | | | | |
| AR043 | colon cancer (9808co64R) | colon cancer (9808co64R) | | | | |
| AR044 | colon cancer 9809co14 | colon cancer 9809co14 | | | | |
| AR045 | corn clone 5 | corn clone 5 | | | | |
| AR046 | corn clone 6 | corn clone 6 | | | | |
| AR047 | corn clone2 | corn clone2 | | | | |
| AR048 | corn clone3 | corn clone3 | | | | |
| AR049 | Corn Clone4 | Corn Clone4 | | | | |
| AR050 | Donor II B Cells 24 hrs | Donor II B Cells 24 hrs | | | | |
| AR051 | Donor II B Cells 72 hrs | Donor II B Cells 72 hrs | | | | |
| AR052 | Donor II B-Cells 24 hrs. | Donor II B-Cells 24 hrs. | | | | |
| AR053 | Donor II B-Cells 72 hrs | Donor II B-Cells 72 hrs | | | | |
| AR054 | Donor II Resting B Cells | Donor II Resting B Cells | | | | |
| AR055 | Heart | Heart | | | | |
| AR056 | Human Lung (CLONTECH ™) | Human Lung (CLONTECH ™) | | | | |
| AR057 | Human Mammary (CLONTECH ™) | Human Mammary (CLONTECH ™) | | | | |
| AR058 | Human Thymus (CLONTECH ™) | Human Thymus (CLONTECH ™) | | | | |
| AR059 | Jurkat (unstimulated) | Jurkat (unstimulated) | | | | |
| AR060 | Kidney | Kidney | | | | |
| AR061 | Liver | Liver | | | | |

TABLE 4-continued

| Code | Description | Tissue | Organ | Cell Line | Disease | Vector |
|---|---|---|---|---|---|---|
| AR062 | Liver (CLONTECH ™) | Liver (CLONTECH ™) | | | | |
| AR063 | Lymphocytes chronic lymphocytic leukaemia | Lymphocytes chronic lymphocytic leukaemia | | | | |
| AR064 | Lymphocytes diffuse large B cell lymphoma | Lymphocytes diffuse large B cell lymphoma | | | | |
| AR065 | Lymphocytes follicular lymphoma | Lymphocytes follicular lymphoma | | | | |
| AR066 | normal breast | normal breast | | | | |
| AR067 | Normal Ovarian (4004901) | Normal Ovarian (4004901) | | | | |
| AR068 | Normal Ovary 9508G045 | Normal Ovary 9508G045 | | | | |
| AR069 | Normal Ovary 9701G208 | Normal Ovary 9701G208 | | | | |
| AR070 | Normal Ovary 9806G005 | Normal Ovary 9806G005 | | | | |
| AR071 | Ovarian Cancer | Ovarian Cancer | | | | |
| AR072 | Ovarian Cancer (9702G001) | Ovarian Cancer (9702G001) | | | | |
| AR073 | Ovarian Cancer (9707G029) | Ovarian Cancer (9707G029) | | | | |
| AR074 | Ovarian Cancer (9804G011) | Ovarian Cancer (9804G011) | | | | |
| AR075 | Ovarian Cancer (9806G019) | Ovarian Cancer (9806G019) | | | | |
| AR076 | Ovarian Cancer (9807G017) | Ovarian Cancer (9807G017) | | | | |
| AR077 | Ovarian Cancer (9809G001) | Ovarian Cancer (9809G001) | | | | |
| AR078 | ovarian cancer 15799 | ovarian cancer 15799 | | | | |
| AR079 | Ovarian Cancer 17717AID | Ovarian Cancer 17717AID | | | | |
| AR080 | Ovarian Cancer 4004664B1 | Ovarian Cancer 4004664B1 | | | | |
| AR081 | Ovarian Cancer 4005315A1 | Ovarian Cancer 4005315A1 | | | | |
| AR082 | ovarian cancer 94127303 | ovarian cancer 94127303 | | | | |
| AR083 | Ovarian Cancer 96069304 | Ovarian Cancer 96069304 | | | | |
| AR084 | Ovarian Cancer 9707G029 | Ovarian Cancer 9707G029 | | | | |
| AR085 | Ovarian Cancer 9807G045 | Ovarian Cancer 9807G045 | | | | |
| AR086 | ovarian cancer 9809G001 | ovarian cancer 9809G001 | | | | |
| AR087 | Ovarian Cancer 9905C032RC | Ovarian Cancer 9905C032RC | | | | |
| AR088 | Ovarian cancer 9907 C00 3rd | Ovarian cancer 9907 C00 3rd | | | | |
| AR089 | Prostate | Prostate | | | | |
| AR090 | Prostate (CLONTECH ™) | Prostate (CLONTECH ™) | | | | |
| AR091 | prostate cancer | prostate cancer | | | | |
| AR092 | prostate cancer #15176 | prostate cancer #15176 | | | | |
| AR093 | prostate cancer #15509 | prostate cancer #15509 | | | | |
| AR094 | prostate cancer #15673 | prostate cancer #15673 | | | | |
| AR095 | Small Intestine (CLONTECH ™) | Small Intestine (CLONTECH ™) | | | | |
| AR096 | Spleen | Spleen | | | | |
| AR097 | Thymus T cells activated | Thymus T cells activated | | | | |
| AR098 | Thymus T cells resting | Thymus T cells resting | | | | |
| AR099 | Tonsil | Tonsil | | | | |
| AR100 | Tonsil geminal center centroblast | Tonsil geminal center centroblast | | | | |
| AR101 | Tonsil germinal center B cell | Tonsil germinal center B cell | | | | |
| AR102 | Tonsil lymph node | Tonsil lymph node | | | | |
| AR103 | Tonsil memory B cell | Tonsil memory B cell | | | | |
| AR104 | Whole Brain | Whole Brain | | | | |
| AR105 | Xenograft ES-2 | Xenograft ES-2 | | | | |
| AR106 | Xenograft SW626 | Xenograft SW626 | | | | |
| AR119 | 001: IL-2 | 001: IL-2 | | | | |
| AR120 | 001: IL-2.1 | 001: IL-2.1 | | | | |
| AR121 | 001: IL-2_b | 001: IL-2_b | | | | |
| AR124 | 002: Monocytes untreated (1 hr) | 002: Monocytes untreated (1 hr) | | | | |
| AR125 | 002: Monocytes untreated (5 hrs) | 002: Monocytes untreated (5 hrs) | | | | |
| AR126 | 002: Control.1C | 002: Control.1C | | | | |
| AR127 | 002: IL2.1C | 002: IL2.1C | | | | |
| AR130 | 003: Placebo-treated Rat Lacrimal Gland | 003: Placebo-treated Rat Lacrimal Gland | | | | |
| AR131 | 003: Placebo-treated Rat Submandibular Gland | 003: Placebo-treated Rat Submandibular Gland | | | | |
| AR135 | 004: Monocytes untreated (5 hrs) | 004: Monocytes untreated (5 hrs) | | | | |
| AR136 | 004: Monocytes untreated 1 hr | 004: Monocytes untreated 1 hr | | | | |
| AR139 | 005: Placebo (48 hrs) | 005: Placebo (48 hrs) | | | | |
| AR140 | 006: pC4 (24 hrs) | 006: pC4 (24 hrs) | | | | |

TABLE 4-continued

| Code | Description | Tissue | Organ | Cell Line | Disease | Vector |
|---|---|---|---|---|---|---|
| AR141 | 006: pC4 (48 hrs) | 006: pC4 (48 hrs) | | | | |
| AR152 | 007: PHA(1 hr) | 007: PHA(1 hr) | | | | |
| AR153 | 007: PHA(6 HRS) | 007: PHA(6 HRS) | | | | |
| AR154 | 007: PMA(6 hrs) | 007: PMA(6 hrs) | | | | |
| AR155 | 008: 1449_#2 | 008: 1449_#2 | | | | |
| AR161 | 01: A - max 24 | 01: A - max 24 | | | | |
| AR162 | 01: A - max 26 | 01: A - max 26 | | | | |
| AR163 | 01: A - max 30 | 01: A - max 30 | | | | |
| AR164 | 01: B - max 24 | 01: B - max 24 | | | | |
| AR165 | 01: B - max 26 | 01: B - max 26 | | | | |
| AR166 | 01: B - max 30 | 01: B - max 30 | | | | |
| AR167 | 1449 Sample | 1449 Sample | | | | |
| AR168 | 3T3P10 1.0 uM insulin | 3T3P10 1.0 uM insulin | | | | |
| AR169 | 3T3P10 10 nM Insulin | 3T3P10 10 nM Insulin | | | | |
| AR170 | 3T3P10 10 uM insulin | 3T3P10 10 uM insulin | | | | |
| AR171 | 3T3P10 No Insulin | 3T3P10 No Insulin | | | | |
| AR172 | 3T3P4 | 3T3P4 | | | | |
| AR173 | Adipose (41892) | Adipose (41892) | | | | |
| AR174 | Adipose Diabetic (41611) | Adipose Diabetic (41611) | | | | |
| AR175 | Adipose Diabetic (41661) | Adipose Diabetic (41661) | | | | |
| AR176 | Adipose Diabetic (41689) | Adipose Diabetic (41689) | | | | |
| AR177 | Adipose Diabetic (41706) | Adipose Diabetic (41706) | | | | |
| AR178 | Adipose Diabetic (42352) | Adipose Diabetic (42352) | | | | |
| AR179 | Adipose Diabetic (42366) | Adipose Diabetic (42366) | | | | |
| AR180 | Adipose Diabetic (42452) | Adipose Diabetic (42452) | | | | |
| AR181 | Adipose Diabetic (42491) | Adipose Diabetic (42491) | | | | |
| AR182 | Adipose Normal (41843) | Adipose Normal (41843) | | | | |
| AR183 | Adipose Normal (41893) | Adipose Normal (41893) | | | | |
| AR184 | Adipose Normal (42452) | Adipose Normal (42452) | | | | |
| AR185 | Adrenal Gland | Adrenal Gland | | | | |
| AR186 | Adrenal Gland + Whole Brain | Adrenal Gland + Whole Brain | | | | |
| AR187 | B7(1 hr) + (inverted) | B7(1 hr) + (inverted) | | | | |
| AR188 | Breast (18275A2B) | Breast (18275A2B) | | | | |
| AR189 | Breast (4004199) | Breast (4004199) | | | | |
| AR190 | Breast (4004399) | Breast (4004399) | | | | |
| AR191 | Breast (4004943B7) | Breast (4004943B7) | | | | |
| AR192 | Breast (4005570B1) | Breast (4005570B1) | | | | |
| AR193 | Breast Cancer (4004127A30) | Breast Cancer (4004127A30) | | | | |
| AR194 | Breast Cancer (400443A21) | Breast Cancer (400443A21) | | | | |
| AR195 | Breast Cancer (4004643A2) | Breast Cancer (4004643A2) | | | | |
| AR196 | Breast Cancer (4004710A7) | Breast Cancer (4004710A7) | | | | |
| AR197 | Breast Cancer (4004943A21) | Breast Cancer (4004943A21) | | | | |
| AR198 | Breast Cancer (400553A2) | Breast Cancer (400553A2) | | | | |
| AR199 | Breast Cancer (9805C046R) | Breast Cancer (9805C046R) | | | | |
| AR200 | Breast Cancer (9806C012R) | Breast Cancer (9806C012R) | | | | |
| AR201 | Breast Cancer (ODQ 45913) | Breast Cancer (ODQ 45913) | | | | |
| AR202 | Breast Cancer (ODQ45913) | Breast Cancer (ODQ45913) | | | | |
| AR203 | Breast Cancer (ODQ4591B) | Breast Cancer (ODQ4591B) | | | | |
| AR204 | Colon Cancer (15663) | Colon Cancer (15663) | | | | |
| AR205 | Colon Cancer (4005144A4) | Colon Cancer (4005144A4) | | | | |
| AR206 | Colon Cancer (4005413A4) | Colon Cancer (4005413A4) | | | | |
| AR207 | Colon Cancer (4005570B1) | Colon Cancer (4005570B1) | | | | |
| AR208 | Control RNA #1 | Control RNA #1 | | | | |
| AR209 | Control RNA #2 | Control RNA #2 | | | | |
| AR210 | Cultured Preadipocyte (blue) | Cultured Preadipocyte (blue) | | | | |
| AR211 | Cultured Preadipocyte (Red) | Cultured Preadipocyte (Red) | | | | |
| AR212 | Donor II B-Cells 24 hrs | Donor II B-Cells 24 hrs | | | | |
| AR213 | Donor II Resting B-Cells | Donor II Resting B-Cells | | | | |
| AR214 | H114EP12 10 nM Insulin | H114EP12 10 nM Insulin | | | | |
| AR215 | H114EP12 (10 nM insulin) | H114EP12 (10 nM insulin) | | | | |
| AR216 | H114EP12 (2.6 ug/ul) | H114EP12 (2.6 ug/ul) | | | | |
| AR217 | H114EP12 (3.6 ug/ul) | H114EP12 (3.6 ug/ul) | | | | |
| AR218 | HUVEC #1 | HUVEC #1 | | | | |
| AR219 | HUVEC #2 | HUVEC #2 | | | | |
| AR221 | L6 undiff. | L6 undiff. | | | | |
| AR222 | L6 Undifferentiated | L6 Undifferentiated | | | | |
| AR223 | L6P8 + 10 nM Insulin | L6P8 + 10 nM Insulin | | | | |
| AR224 | L6P8 + HS | L6P8 + HS | | | | |
| AR225 | L6P8 10 nM Insulin | L6P8 10 nM Insulin | | | | |

TABLE 4-continued

| Code | Description | Tissue | Organ | Cell Line | Disease | Vector |
|---|---|---|---|---|---|---|
| AR226 | Liver (00-06-A007B) | Liver (00-06-A007B) | | | | |
| AR227 | Liver (96-02-A075) | Liver (96-02-A075) | | | | |
| AR228 | Liver (96-03-A144) | Liver (96-03-A144) | | | | |
| AR229 | Liver (96-04-A138) | Liver (96-04-A138) | | | | |
| AR230 | Liver (97-10-A074B) | Liver (97-10-A074B) | | | | |
| AR231 | Liver (98-09-A242A) | Liver (98-09-A242A) | | | | |
| AR232 | Liver Diabetic (1042) | Liver Diabetic (1042) | | | | |
| AR233 | Liver Diabetic (41616) | Liver Diabetic (41616) | | | | |
| AR234 | Liver Diabetic (41955) | Liver Diabetic (41955) | | | | |
| AR235 | Liver Diabetic (42352R) | Liver Diabetic (42352R) | | | | |
| AR236 | Liver Diabetic (42366) | Liver Diabetic (42366) | | | | |
| AR237 | Liver Diabetic (42483) | Liver Diabetic (42483) | | | | |
| AR238 | Liver Diabetic (42491) | Liver Diabetic (42491) | | | | |
| AR239 | Liver Diabetic (99-09-A281A) | Liver Diabetic (99-09-A281A) | | | | |
| AR240 | Lung | Lung | | | | |
| AR241 | Lung (27270) | Lung (27270) | | | | |
| AR242 | Lung (2727Q) | Lung (2727Q) | | | | |
| AR243 | Lung Cancer (4005116A1) | Lung Cancer (4005116A1) | | | | |
| AR244 | Lung Cancer (4005121A5) | Lung Cancer (4005121A5) | | | | |
| AR245 | Lung Cancer (4005121A5)) | Lung Cancer (4005121A5)) | | | | |
| AR246 | Lung Cancer (4005340A4) | Lung Cancer (4005340A4) | | | | |
| AR247 | Mammary Gland | Mammary Gland | | | | |
| AR248 | Monocyte (CT) | Monocyte (CT) | | | | |
| AR249 | Monocyte (OCT) | Monocyte (OCT) | | | | |
| AR250 | Monocytes (CT) | Monocytes (CT) | | | | |
| AR251 | Monocytes (INFG 18 hr) | Monocytes (INFG 18 hr) | | | | |
| AR252 | Monocytes (INFG 18 hr) | Monocytes (INFG 18 hr) | | | | |
| AR253 | Monocytes (INFG 8-11) | Monocytes (INFG 8-11) | | | | |
| AR254 | Monocytes (O CT) | Monocytes (O CT) | | | | |
| AR255 | Muscle (91-01-A105) | Muscle (91-01-A105) | | | | |
| AR256 | Muscle (92-04-A059) | Muscle (92-04-A059) | | | | |
| AR257 | Muscle (97-11-A056d) | Muscle (97-11-A056d) | | | | |
| AR258 | Muscle (99-06-A210A) | Muscle (99-06-A210A) | | | | |
| AR259 | Muscle (99-07-A203B) | Muscle (99-07-A203B) | | | | |
| AR260 | Muscle (99-7-A203B) | Muscle (99-7-A203B) | | | | |
| AR261 | Muscle Diabetic (42352R) | Muscle Diabetic (42352R) | | | | |
| AR262 | Muscle Diabetic (42366) | Muscle Diabetic (42366) | | | | |
| AR263 | NK-19 Control | NK-19 Control | | | | |
| AR264 | NK-19 IL Treated 72 hrs | NK-19 IL Treated 72 hrs | | | | |
| AR265 | NK-19 UK Treated 72 hrs. | NK-19 UK Treated 72 hrs. | | | | |
| AR266 | Omentum Normal (94-08-B009) | Omentum Normal (94-08-B009) | | | | |
| AR267 | Omentum Normal (97-01-A039A) | Omentum Normal (97-01-A039A) | | | | |
| AR268 | Omentum Normal (97-04-A114C) | Omentum Normal (97-04-A114C) | | | | |
| AR269 | Omentum Normal (97-06-A117C) | Omentum Normal (97-06-A117C) | | | | |
| AR270 | Omentum Normal (97-09-B004C) | Omentum Normal (97-09-B004C) | | | | |
| AR271 | Ovarian Cancer (17717AID) | Ovarian Cancer (17717AID) | | | | |
| AR272 | Ovarian Cancer (9905C023RC) | Ovarian Cancer (9905C023RC) | | | | |
| AR273 | Ovarian Cancer (9905C032RC) | Ovarian Cancer (9905C032RC) | | | | |
| AR274 | Ovary (9508G045) | Ovary (9508G045) | | | | |
| AR275 | Ovary (9701G208) | Ovary (9701G208) | | | | |
| AR276 | Ovary 9806G005 | Ovary 9806G005 | | | | |
| AR277 | Pancreas | Pancreas | | | | |
| AR278 | Placebo | Placebo | | | | |
| AR279 | rIL2 Control | rIL2 Control | | | | |
| AR280 | RSS288L | RSS288L | | | | |
| AR281 | RSS288LC | RSS288LC | | | | |
| AR282 | Salivary Gland | Salivary Gland | | | | |
| AR283 | Skeletal Muscle | Skeletal Muscle | | | | |
| AR284 | Skeletal Muscle (91-01-A105) | Skeletal Muscle (91-01-A105) | | | | |
| AR285 | Skeletal Muscle (42180) | Skeletal Muscle (42180) | | | | |
| AR286 | Skeletal Muscle (42386) | Skeletal Muscle (42386) | | | | |
| AR287 | Skeletal Muscle (42461) | Skeletal Muscle (42461) | | | | |
| AR288 | Skeletal Muscle (91-01-A105) | Skeletal Muscle (91-01-A105) | | | | |
| AR289 | Skeletal Muscle (92-04-A059) | Skeletal Muscle (92-04-A059) | | | | |
| AR290 | Skeletal Muscle (96-08-A171) | Skeletal Muscle (96-08-A171) | | | | |

TABLE 4-continued

| Code | Description | Tissue | Organ | Cell Line | Disease | Vector |
|---|---|---|---|---|---|---|
| AR291 | Skeletal Muscle (97-07-A190A) | Skeletal Muscle (97-07-A190A) | | | | |
| AR292 | Skeletal Muscle Diabetic (42352) | Skeletal Muscle Diabetic (42352) | | | | |
| AR293 | Skeletal Muscle Diabetic (42366) | Skeletal Muscle Diabetic (42366) | | | | |
| AR294 | Skeletal Muscle Diabetic (42395) | Skeletal Muscle Diabetic (42395) | | | | |
| AR295 | Skeletal Muscle Diabetic (42483) | Skeletal Muscle Diabetic (42483) | | | | |
| AR296 | Skeletal Muscle Diabetic (42491) | Skeletal Muscle Diabetic (42491) | | | | |
| AR297 | Skeletal Muscle Diabetic 42352 | Skeletal Muscle Diabetic 42352 | | | | |
| AR298 | Skeletal Musle (42461) | Skeletal Musle (42461) | | | | |
| AR299 | Small Intestine | Small Intestine | | | | |
| AR300 | Stomach | Stomach | | | | |
| AR301 | T-Cell + HDPBQ71.fc 1449 16 hrs | T-Cell + HDPBQ71.fc 1449 16 hrs | | | | |
| AR302 | T-Cell + HDPBQ71.fc 1449 6 hrs | T-Cell + HDPBQ71.fc 1449 6 hrs | | | | |
| AR303 | T-Cell + IL2 16 hrs | T-Cell + IL2 16 hrs | | | | |
| AR304 | T-Cell + IL2 6 hrs | T-Cell + IL2 6 hrs | | | | |
| AR306 | T-Cell Untreated 16 hrs | T-Cell Untreated 16 hrs | | | | |
| AR307 | T-Cell Untreated 6 hrs | T-Cell Untreated 6 hrs | | | | |
| AR308 | T-Cells 24 hours | T-Cells 24 hours | | | | |
| AR309 | T-Cells 24 hrs | T-Cells 24 hrs | | | | |
| AR310 | T-Cells 24 hrs. | T-Cells 24 hrs. | | | | |
| AR311 | T-Cells 24 hrs | T-Cells 24 hrs | | | | |
| AR312 | T-Cells 4 days | T-Cells 4 days | | | | |
| AR313 | Thymus | Thymus | | | | |
| AR314 | TRE | TRE | | | | |
| AR315 | TREC | TREC | | | | |
| AR316 | Virtual Mixture | Virtual Mixture | | | | |
| AR317 | B lymphocyte, | B lymphocyte, | | | | |
| AR318 | (non-T; non-B) | (non-T; non-B) | | | | |
| AR326 | 001-293 RNA (Vector Control) | 001-293 RNA (Vector Control) | | | | |
| AR327 | 001: Control | 001: Control | | | | |
| AR328 | 001: Control.1 | 001: Control.1 | | | | |
| AR355 | Acute Lymphocyte Leukemia | Acute Lymphocyte Leukemia | | | | |
| AR356 | AML Patient #11 | AML Patient #11 | | | | |
| AR357 | AML Patient #2 | AML Patient #2 | | | | |
| AR358 | AML Patient #2 SGAH | AML Patient #2 SGAH | | | | |
| AR359 | AML Patient#2 | AML Patient#2 | | | | |
| AR360 | Aorta | Aorta | | | | |
| AR361 | B Cell | B Cell | | | | |
| AR362 | B lymphoblast | B lymphoblast | | | | |
| AR363 | B lymphocyte | B lymphocyte | | | | |
| AR364 | B lymphocytes | B lymphocytes | | | | |
| AR365 | B-cell | B-cell | | | | |
| AR366 | B-Cells | B-Cells | | | | |
| AR367 | B-Lymphoblast | B-Lymphoblast | | | | |
| AR368 | B-Lymphocytes | B-Lymphocytes | | | | |
| AR369 | Bladder | Bladder | | | | |
| AR370 | Bone Marrow | Bone Marrow | | | | |
| AR371 | Bronchial Epithelial Cell | Bronchial Epithelial Cell | | | | |
| AR372 | Bronchial Epithelial Cells | Bronchial Epithelial Cells | | | | |
| AR373 | Caco-2A | Caco-2A | | | | |
| AR374 | Caco-2B | Caco-2B | | | | |
| AR375 | Caco-2C | Caco-2C | | | | |
| AR376 | Cardiac #1 | Cardiac #1 | | | | |
| AR377 | Cardiac #2 | Cardiac #2 | | | | |
| AR378 | Chest Muscle | Chest Muscle | | | | |
| AR381 | Dendritic Cell | Dendritic Cell | | | | |
| AR382 | Dendritic cells | Dendritic cells | | | | |
| AR383 | *E. coli* | *E. coli* | | | | |
| AR384 | Epithelial Cells | Epithelial Cells | | | | |
| AR385 | Esophagus | Esophagus | | | | |
| AR386 | FPPS | FPPS | | | | |
| AR387 | FPPSC | FPPSC | | | | |
| AR388 | HepG2 Cell Line | HepG2 Cell Line | | | | |
| AR389 | HepG2 Cell line Buffer 1 hr. | HepG2 Cell line Buffer 1 hr. | | | | |
| AR390 | HepG2 Cell line Buffer 06 hr | HepG2 Cell line Buffer 06 hr | | | | |
| AR391 | HepG2 Cell line Buffer 24 hr. | HepG2 Cell line Buffer 24 hr. | | | | |
| AR392 | HepG2 Cell line Insulin 01 hr. | HepG2 Cell line Insulin 01 hr. | | | | |
| AR393 | HepG2 Cell line Insulin 06 hr. | HepG2 Cell line Insulin 06 hr. | | | | |

TABLE 4-continued

| Code | Description | Tissue | Organ | Cell Line | Disease | Vector |
|---|---|---|---|---|---|---|
| AR394 | HepG2 Cell line Insulin 24 hr. | HepG2 Cell line Insulin 24 hr. | | | | |
| AR398 | HMC-1 | HMC-1 | | | | |
| AR399 | HMCS | HMCS | | | | |
| AR400 | HMSC | HMSC | | | | |
| AR401 | HUVEC #3 | HUVEC #3 | | | | |
| AR402 | HUVEC #4 | HUVEC #4 | | | | |
| AR404 | KIDNEY NORMAL | KIDNEY NORMAL | | | | |
| AR405 | KIDNEY TUMOR | KIDNEY TUMOR | | | | |
| AR406 | KIDNEY TUMOR | | | | | |
| AR407 | Lymph Node | Lymph Node | | | | |
| AR408 | Macrophage | Macrophage | | | | |
| AR409 | Megakarioblast | Megakarioblast | | | | |
| AR410 | Monocyte | Monocyte | | | | |
| AR411 | Monocytes | Monocytes | | | | |
| AR412 | Myocardium | Myocardium | | | | |
| AR413 | Myocardium #3 | Myocardium #3 | | | | |
| AR414 | Myocardium #4 | Myocardium #4 | | | | |
| AR415 | Myocardium #5 | Myocardium #5 | | | | |
| AR416 | NK | NK | | | | |
| AR417 | NK cell | NK cell | | | | |
| AR418 | NK cells | NK cells | | | | |
| AR419 | NKYa | NKYa | | | | |
| AR420 | NKYa019 | NKYa019 | | | | |
| AR421 | Ovary | Ovary | | | | |
| AR422 | Patient #11 | Patient #11 | | | | |
| AR423 | Peripheral blood | Peripheral blood | | | | |
| AR424 | Primary Adipocytes | Primary Adipocytes | | | | |
| AR425 | Promyeloblast | Promyeloblast | | | | |
| AR427 | RSSWT | RSSWT | | | | |
| AR428 | RSSWTC | RSSWTC | | | | |
| AR429 | SW 480(G1) | SW 480(G1) | | | | |
| AR430 | SW 480(G2) | SW 480(G2) | | | | |
| AR431 | SW 480(G3) | SW 480(G3) | | | | |
| AR432 | SW 480(G4) | SW 480(G4) | | | | |
| AR433 | SW 480(G5) | SW 480(G5) | | | | |
| AR434 | T Lymphoblast | T Lymphoblast | | | | |
| AR435 | T Lymphocyte | T Lymphocyte | | | | |
| AR436 | T-Cell | T-Cell | | | | |
| AR438 | T-Cell, | T-Cell, | | | | |
| AR439 | T-Cells | T-Cells | | | | |
| AR440 | T-lymphoblast | T-lymphoblast | | | | |
| AR441 | Th 1 | Th 1 | | | | |
| AR442 | Th 2 | Th 2 | | | | |
| AR443 | Th1 | Th1 | | | | |
| AR444 | Th2 | Th2 | | | | |
| H0002 | Human Adult Heart | Human Adult Heart | Heart | | | UNI-ZAP ™ XR |
| H0003 | Human Adult Liver | Human Adult Liver | Liver | | | UNI-ZAP ™ XR |
| H0004 | Human Adult Spleen | Human Adult Spleen | Spleen | | | UNI-ZAP ™ XR |
| H0006 | Human Frontal Lobe of Brain | | | | | UNI-ZAP ™ XR |
| H0007 | Human Cerebellum | Human Cerebellum | Brain | | | UNI-ZAP ™ XR |
| H0008 | Whole 6 Week Old Embryo | | | | | UNI-ZAP ™ XR |
| H0009 | Human Fetal Brain | | | | | UNI-ZAP ™ XR |
| H0009 | Human Fetal Brain | Human Fetal Brain | Brain | | | UNI-ZAP ™ XR |
| H0010 | Human Fetal Hepatic | Human Fetal Liver | Liver | | | UNI-ZAP ™ XR |
| H0011 | Human Fetal Kidney | Human Fetal Kidney | Kidney | | | UNI-ZAP ™ XR |
| H0012 | Human Fetal Kidney | Human Fetal Kidney | Kidney | | | UNI-ZAP ™ XR |
| H0013 | Human 8 Week Whole Embryo | Human 8 Week Old Embryo | Embryo | | | UNI-ZAP ™ XR |
| H0014 | Human Gall Bladder | Human Gall Bladder | Gall Bladder | | | UNI-ZAP ™ XR |
| H0015 | Human Gall Bladder, fraction II | Human Gall Bladder | Gall Bladder | | | UNI-ZAP ™ XR |
| H0016 | Human Greater Omentum | Human Greater Omentum | peritoneum | | | UNI-ZAP ™ XR |
| H0017 | Human Greater Omentum | Human Greater Omentum | peritoneum | | | UNI-ZAP ™ XR |

TABLE 4-continued

| Code | Description | Tissue | Organ | Cell Line | Disease | Vector |
|---|---|---|---|---|---|---|
| H0018 | Human Greater Omentum, fII remake | Human Greater Omentum | peritoneum | | | UNI-ZAP ™ XR |
| H0019 | Human Fetal Heart | Human Fetal Heart | Heart | | | pBLUESCRIPT ™ |
| H0020 | Human Hippocampus | Human Hippocampus | Brain | | | UNI-ZAP ™ XR |
| H0021 | Human Infant Adrenal Gland | Human Infant Adrenal Gland | Adrenal gland | | | UNI-ZAP ™ XR |
| H0022 | Jurkat Cells | Jurkat T-Cell Line | | | | LAMBDA ZAP ™ II |
| H0023 | Human Fetal Lung | | | | | UNI-ZAP ™ XR |
| H0024 | Human Fetal Lung III | Human Fetal Lung | Lung | | | UNI-ZAP ™ XR |
| H0025 | Human Adult Lymph Node | Human Adult Lymph Node | Lymph Node | | | LAMBDA ZAP ™ II |
| H0026 | Namalwa Cells | Namalwa B-Cell Line, EBV immortalized | | | | LAMBDA ZAP ™ II |
| H0028 | Human Old Ovary | Human Old Ovary | Ovary | | | pBLUESCRIPT ™ |
| H0029 | Human Pancreas | Human Pancreas | Pancreas | | | UNI-ZAP ™ XR |
| H0030 | Human Placenta | | | | | UNI-ZAP ™ XR |
| H0031 | Human Placenta | Human Placenta | Placenta | | | UNI-ZAP ™ XR |
| H0032 | Human Prostate | Human Prostate | Prostate | | | UNI-ZAP ™ XR |
| H0033 | Human Pituitary | Human Pituitary | | | | UNI-ZAP ™ XR |
| H0034 | Human Parathyroid Tumor | Human Parathyroid Tumor | Parathyroid | | disease | UNI-ZAP ™ XR |
| H0035 | Human Salivary Gland | Human Salivary Gland | Salivary gland | | | UNI-ZAP ™ XR |
| H0036 | Human Adult Small Intestine | Human Adult Small Intestine | Small Int. | | | UNI-ZAP ™ XR |
| H0037 | Human Adult Small Intestine | Human Adult Small Intestine | Small Int. | | | pBLUESCRIPT ™ |
| H0038 | Human Testes | Human Testes | Testis | | | UNI-ZAP ™ XR |
| H0039 | Human Pancreas Tumor | Human Pancreas Tumor | Pancreas | | disease | UNI-ZAP ™ XR |
| H0040 | Human Testes Tumor | Human Testes Tumor | Testis | | disease | UNI-ZAP ™ XR |
| H0041 | Human Fetal Bone | Human Fetal Bone | Bone | | | UNI-ZAP ™ XR |
| H0042 | Human Adult Pulmonary | Human Adult Pulmonary | Lung | | | UNI-ZAP ™ XR |
| H0044 | Human Cornea | Human Cornea | eye | | | UNI-ZAP ™ XR |
| H0045 | Human Esophagus, Cancer | Human Esophagus, cancer | Esophagus | | disease | UNI-ZAP ™ XR |
| H0046 | Human Endometrial Tumor | Human Endometrial Tumor | Uterus | | disease | UNI-ZAP ™ XR |
| H0047 | Human Fetal Liver | Human Fetal Liver | Liver | | | UNI-ZAP ™ XR |
| H0048 | Human Pineal Gland | Human Pineal Gland | | | | UNI-ZAP ™ XR |
| H0049 | Human Fetal Kidney | Human Fetal Kidney | Kidney | | | UNI-ZAP ™ XR |
| H0050 | Human Fetal Heart | Human Fetal Heart | Heart | | | UNI-ZAP ™ XR |
| H0051 | Human Hippocampus | Human Hippocampus | Brain | | | UNI-ZAP ™ XR |
| H0052 | Human Cerebellum | Human Cerebellum | Brain | | | UNI-ZAP ™ XR |
| H0053 | Human Adult Kidney | Human Adult Kidney | Kidney | | | UNI-ZAP ™ XR |
| H0056 | Human Umbilical Vein, Endo. remake | Human Umbilical Vein Endothelial Cells | Umbilical vein | | | UNI-ZAP ™ XR |
| H0057 | Human Fetal Spleen | | | | | UNI-ZAP ™ XR |
| H0058 | Human Thymus Tumor | Human Thymus Tumor | Thymus | | disease | LAMBDA ZAP ™ II |
| H0059 | Human Uterine Cancer | Human Uterine Cancer | Uterus | | disease | LAMBDA ZAP ™ II |
| H0060 | Human Macrophage | Human Macrophage | Blood | Cell Line | | pBLUESCRIPT ™ |
| H0061 | Human Macrophage | Human Macrophage | Blood | Cell Line | | pBLUESCRIPT ™ |
| H0062 | Human Thymus | Human Thymus | Thymus | | | UNI-ZAP ™ XR |

TABLE 4-continued

| Code | Description | Tissue | Organ | Cell Line | Disease | Vector |
|---|---|---|---|---|---|---|
| H0063 | Human Thymus | Human Thymus | Thymus | | | UNI-ZAP ™ XR |
| H0064 | Human Right Hemisphere of Brain | Human Brain, right hemisphere | Brain | | | UNI-ZAP ™ XR |
| H0065 | Human Esophagus, Normal | Human Esophagus, normal | Esophagus | | | UNI-ZAP ™ XR |
| H0067 | Human left hemisphere, adult | Human Left Hemisphere, Adult | Brain | | | LAMBDA ZAP ™ II |
| H0068 | Human Skin Tumor | Human Skin Tumor | Skin | | disease | UNI-ZAP ™ XR |
| H0069 | Human Activated T-Cells | Activated T-Cells | Blood | Cell Line | | UNI-ZAP ™ XR |
| H0070 | Human Pancreas | Human Pancreas | Pancreas | | | UNI-ZAP ™ XR |
| H0071 | Human Infant Adrenal Gland | Human Infant Adrenal Gland | Adrenal gland | | | UNI-ZAP ™ XR |
| H0073 | Human Leiomyeloid Carcinoma | Human Leiomyeloid Carcinoma | Muscle | | disease | UNI-ZAP ™ XR |
| H0074 | Human Platelets | Human Platelets | Blood | Cell Line | | UNI-ZAP ™ XR |
| H0075 | Human Activated T-Cells (II) | Activated T-Cells | Blood | Cell Line | | UNI-ZAP ™ XR |
| H0076 | Human Membrane Bound Polysomes | Human Membrane Bound Polysomes | Blood | Cell Line | | UNI-ZAP ™ XR |
| H0077 | Human Thymus Tumor | Human Thymus Tumor | Thymus | | disease | LAMBDA ZAP ™ II |
| H0078 | Human Lung Cancer | Human Lung Cancer | Lung | | disease | LAMBDA ZAP ™ II |
| H0079 | Human Whole 7 Week Old Embryo (II) | Human Whole 7 Week Old Embryo | Embryo | | | UNI-ZAP ™ XR |
| H0080 | Human Whole 6 Week Old Embryo (II) | Human Whole Six Week Old Embryo | Embryo | | | LAMBDA ZAP ™ II |
| H0081 | Human Fetal Epithelium (Skin) | Human Fetal Skin | Skin | | | UNI-ZAP ™ XR |
| H0082 | Human Fetal Muscle | Human Fetal Muscle | Sk Muscle | | | UNI-ZAP ™ XR |
| H0083 | HUMAN JURKAT MEMBRANE BOUND POLYSOMES | Jurkat Cells | | | | UNI-ZAP ™ XR |
| H0085 | Human Colon | Human Colon | | | | LAMBDA ZAP ™ II |
| H0086 | Human epithelioid sarcoma | Epithelioid Sarcoma, muscle | Sk Muscle | | disease | UNI-ZAP ™ XR |
| H0087 | Human Thymus | Human Thymus | | | | pBLUESCRIPT ™ |
| H0090 | Human T-Cell Lymphoma | T-Cell Lymphoma | T-Cell | | disease | UNI-ZAP ™ XR |
| H0092 | Human Pancreas Tumor | Human Pancreas Tumor | Pancreas | | disease | UNI-ZAP ™ XR |
| H0093 | Human Greater Omentum Tumor | Human Greater Omentum | peritoneum | | disease | UNI-ZAP ™ XR |
| H0095 | Human Greater Omentum, RNA Remake | Human Greater Omentum | peritoneum | | | UNI-ZAP ™ XR |
| H0096 | Human Parotid Cancer | Human Parotid Cancer | Parotid | | disease | LAMBDA ZAP ™ II |
| H0097 | Human Adult Heart, subtracted | Human Adult Heart | Heart | | | pBLUESCRIPT ™ |
| H0098 | Human Adult Liver, subtracted | Human Adult Liver | Liver | | | UNI-ZAP ™ XR |
| H0099 | Human Lung Cancer, subtracted | Human Lung Cancer | Lung | | | pBLUESCRIPT ™ |
| H0100 | Human Whole Six Week Old Embryo | Human Whole Six Week Old Embryo | Embryo | | | UNI-ZAP ™ XR |
| H0101 | Human 7 Weeks Old Embryo, subtracted | Human Whole 7 Week Old Embryo | Embryo | | | LAMBDA ZAP ™ II |
| H0102 | Human Whole 6 Week Old Embryo (II), subt | Human Whole Six Week Old Embryo | Embryo | | | pBLUESCRIPT ™ |
| H0103 | Human Fetal Brain, subtracted | Human Fetal Brain | Brain | | | UNI-ZAP ™ XR |
| H0105 | Human Fetal Heart, subtracted | Human Fetal Heart | Heart | | | pBLUESCRIPT ™ |
| H0106 | Human Right Hemisphere of Brain, subtrac | Human Brain, right hemisphere | Brain | | | UNI-ZAP ™ XR |
| H0107 | Human Infant Adrenal Gland, subtracted | Human Infant Adrenal Gland | Adrenal gland | | | pBLUESCRIPT ™ |
| H0108 | Human Adult Lymph Node, subtracted | Human Adult Lymph Node | Lymph Node | | | UNI-ZAP ™ XR |
| H0109 | Human Macrophage, subtracted | Macrophage | Blood | Cell Line | | pBLUESCRIPT ™ |
| H0110 | Human Old Ovary, subtracted | Human Old Ovary | Ovary | | | pBLUESCRIPT ™ |
| H0111 | Human Placenta, subtracted | Human Placenta | Placenta | | | pBLUESCRIPT ™ |
| H0112 | Human Parathyroid Tumor, subtracted | Human Parathyroid Tumor | Parathyroid | | | pBLUESCRIPT ™ |

TABLE 4-continued

| Code | Description | Tissue | Organ | Cell Line | Disease | Vector |
|---|---|---|---|---|---|---|
| H0113 | Human skin Tumor, subtracted | Human Skin Tumor | Skin | | | UNI-ZAP ™ XR |
| H0116 | Human Thymus Tumor, subtracted | Human Thymus Tumor | Thymus | | | pBLUESCRIPT ™ |
| H0117 | Human Uterine Cancer, subtracted | Human Uterine Cancer | Uterus | | | pBLUESCRIPT ™ |
| H0118 | Human Adult Kidney | Human Adult Kidney | Kidney | | | UNI-ZAP ™ XR |
| H0119 | Human Pediatric Kidney | Human Pediatric Kidney | Kidney | | | UNI-ZAP ™ XR |
| H0120 | Human Adult Spleen, subtracted | Human Adult Spleen | Spleen | | | UNI-ZAP ™ XR |
| H0121 | Human Cornea, subtracted | Human Cornea | eye | | | UNI-ZAP ™ XR |
| H0122 | Human Adult Skeletal Muscle | Human Skeletal Muscle | Sk Muscle | | | UNI-ZAP ™ XR |
| H0123 | Human Fetal Dura Mater | Human Fetal Dura Mater | Brain | | | UNI-ZAP ™ XR |
| H0124 | Human Rhabdomyosarcoma | Human Rhabdomyosarcoma | Sk Muscle | | disease | UNI-ZAP ™ XR |
| H0125 | Cem cells cyclohexamide treated | Cyclohexamide Treated Cem, Jurkat, Raji, and Supt | Blood | Cell Line | | UNI-ZAP ™ XR |
| H0128 | Jurkat cells, thiouridine activated | Jurkat Cells | | | | UNI-ZAP ™ XR |
| H0129 | Jurkat cells, thiouridine activated, fract II | Jurkat Cells | | | | UNI-ZAP ™ XR |
| H0130 | LNCAP untreated | LNCAP Cell Line | Prostate | Cell Line | | UNI-ZAP ™ XR |
| H0131 | LNCAP + o.3 nM R1881 | LNCAP Cell Line | Prostate | Cell Line | | UNI-ZAP ™ XR |
| H0132 | LNCAP + 30 nM R1881 | LNCAP Cell Line | Prostate | Cell Line | | UNI-ZAP ™ XR |
| H0134 | Raji Cells, cyclohexamide treated | Cyclohexamide Treated Cem, Jurkat, Raji, and Supt | Blood | Cell Line | | UNI-ZAP ™ XR |
| H0135 | Human Synovial Sarcoma | Human Synovial Sarcoma | Synovium | | | UNI-ZAP ™ XR |
| H0136 | Supt Cells, cyclohexamide treated | Cyclohexamide Treated Cem, Jurkat, Raji, and Supt | Blood | Cell Line | | UNI-ZAP ™ XR |
| H0138 | Activated T-Cells, 0 hrs. | Activated T-Cells | Blood | Cell Line | | UNI-ZAP ™ XR |
| H0139 | Activated T-Cells, 4 hrs. | Activated T-Cells | Blood | Cell Line | | UNI-ZAP ™ XR |
| H0140 | Activated T-Cells, 8 hrs. | Activated T-Cells | Blood | Cell Line | | UNI-ZAP ™ XR |
| H0141 | Activated T-Cells, 12 hrs. | Activated T-Cells | Blood | Cell Line | | UNI-ZAP ™ XR |
| H0142 | MCF7 Cell Line | MCF7 Cell line | Breast | Cell Line | | UNI-ZAP ™ XR |
| H0144 | Nine Week Old Early Stage Human | 9 Wk Old Early Stage Human | Embryo | | | UNI-ZAP ™ XR |
| H0147 | Human Adult Liver | Human Adult Liver | Liver | | | UNI-ZAP ™ XR |
| H0149 | 7 Week Old Early Stage Human, subtracted | Human Whole 7 Week Old Embryo | Embryo | | | UNI-ZAP ™ XR |
| H0150 | Human Epididymus | Epididymis | Testis | | | UNI-ZAP ™ XR |
| H0151 | Early Stage Human Liver | Human Fetal Liver | Liver | | | UNI-ZAP ™ XR |
| H0152 | Early Stage Human Liver, fract (II) | Human Fetal Liver | Liver | | | UNI-ZAP ™ XR |
| H0154 | Human Fibrosarcoma | Human Skin Fibrosarcoma | Skin | | disease | UNI-ZAP ™ XR |
| H0155 | Human Thymus, subtracted | Human Thymus Tumor | Thymus | | | pBLUESCRIPT ™ |
| H0156 | Human Adrenal Gland Tumor | Human Adrenal Gland Tumor | Adrenal Gland | | disease | UNI-ZAP ™ XR |
| H0157 | Activated T-Cells, 0 hrs, ligation 2 | Activated T-Cells | Blood | Cell Line | | UNI-ZAP ™ XR |
| H0158 | Activated T-Cells, 4 hrs., ligation 2 | Activated T-Cells | Blood | Cell Line | | UNI-ZAP ™ XR |
| H0159 | Activated T-Cells, 8 hrs., ligation 2 | Activated T-Cells | Blood | Cell Line | | UNI-ZAP ™ XR |
| H0160 | Activated T-Cells, 12 hrs., ligation 2 | Activated T-Cells | Blood | Cell Line | | UNI-ZAP ™ XR |
| H0161 | Activated T-Cells, 24 hrs., ligation 2 | Activated T-Cells | Blood | Cell Line | | UNI-ZAP ™ XR |
| H0163 | Human Synovium | Human Synovium | Synovium | | | UNI-ZAP ™ XR |

TABLE 4-continued

| Code | Description | Tissue | Organ | Cell Line | Disease | Vector |
|---|---|---|---|---|---|---|
| H0164 | Human Trachea Tumor | Human Trachea Tumor | Trachea | | disease | UNI-ZAP ™ XR |
| H0165 | Human Prostate Cancer, Stage B2 | Human Prostate Cancer, stage B2 | Prostate | | disease | UNI-ZAP ™ XR |
| H0166 | Human Prostate Cancer, Stage B2 fraction | Human Prostate Cancer, stage B2 | Prostate | | disease | UNI-ZAP ™ XR |
| H0167 | Activated T-Cells, 24 hrs. | Activated T-Cells | Blood | Cell Line | | UNI-ZAP ™ XR |
| H0168 | Human Prostate Cancer, Stage C | Human Prostate Cancer, stage C | Prostate | | disease | UNI-ZAP ™ XR |
| H0169 | Human Prostate Cancer, Stage C fraction | Human Prostate Cancer, stage C | Prostate | | disease | UNI-ZAP ™ XR |
| H0170 | 12 Week Old Early Stage Human | Twelve Week Old Early Stage Human | Embryo | | | UNI-ZAP ™ XR |
| H0171 | 12 Week Old Early Stage Human, II | Twelve Week Old Early Stage Human | Embryo | | | UNI-ZAP ™ XR |
| H0172 | Human Fetal Brain, random primed | Human Fetal Brain | Brain | | | LAMBDA ZAP ™ II |
| H0173 | Human Cardiomyopathy, RNA remake | Human Cardiomyopathy | Heart | | disease | UNI-ZAP ™ XR |
| H0175 | H. Adult Spleen, ziplox | | | | | pSport1 |
| H0176 | CAMA1Ee Cell Line | CAMA1Ee Cell Line | Breast | Cell Line | | UNI-ZAP ™ XR |
| H0177 | CAMA1Ee Cell Line | CAMA1Ee Cell Line | Breast | Cell Line | | UNI-ZAP ™ XR |
| H0178 | Human Fetal Brain | Human Fetal Brain | Brain | | | UNI-ZAP ™ XR |
| H0179 | Human Neutrophil | Human Neutrophil | Blood | Cell Line | | UNI-ZAP ™ XR |
| H0180 | Human Primary Breast Cancer | Human Primary Breast Cancer | Breast | | disease | UNI-ZAP ™ XR |
| H0181 | Human Primary Breast Cancer | Human Primary Breast Cancer | Breast | | disease | UNI-ZAP ™ XR |
| H0182 | Human Primary Breast Cancer | Human Primary Breast Cancer | Breast | | disease | UNI-ZAP ™ XR |
| H0183 | Human Colon Cancer | Human Colon Cancer | Colon | | disease | UNI-ZAP ™ XR |
| H0184 | Human Colon Cancer, metasticized to live | Human Colon Cancer, metasticized to liver | Liver | | disease | LAMBDA ZAP ™ II |
| H0185 | Activated T-Cell labeled with 4-thioluri | T-Cells | Blood | Cell Line | | LAMBDA ZAP ™ II |
| H0186 | Activated T-Cell | T-Cells | Blood | Cell Line | | LAMBDA ZAP ™ II |
| H0187 | Resting T-Cell | T-Cells | Blood | Cell Line | | LAMBDA ZAP ™ II |
| H0188 | Human Normal Breast | Human Normal Breast | Breast | | | UNI-ZAP ™ XR |
| H0189 | Human Resting Macrophage | Human Macrophage/Monocytes | Blood | Cell Line | | UNI-ZAP ™ XR |
| H0190 | Human Activated Macrophage (LPS) | Human Macrophage/Monocytes | Blood | Cell Line | | UNI-ZAP ™ XR |
| H0191 | Human Activated Macrophage (LPS), thiour | Human Macrophage/Monocytes | Blood | Cell Line | | UNI-ZAP ™ XR |
| H0192 | Cem Cells, cyclohexamide treated, subtra | Cyclohexamide Treated Cem, Jurkat, Raji, and Supt | Blood | Cell Line | | UNI-ZAP ™ XR |
| H0193 | Cem Cells, cyclohexamide treated, differ | Cyclohexamide Treated Cem, Jurkat, Raji, and Supt | Blood | Cell Line | | UNI-ZAP ™ XR |
| H0194 | Human Cerebellum, subtracted | Human Cerebellum | Brain | | | pBLUESCRIPT ™ |
| H0196 | Human Cardiomyopathy, subtracted | Human Cardiomyopathy | Heart | | | UNI-ZAP ™ XR |
| H0197 | Human Fetal Liver, subtracted | Human Fetal Liver | Liver | | | UNI-ZAP ™ XR |
| H0198 | Human Fetal Liver, subtracted, pos. clon | Human Fetal Liver | Liver | | | UNI-ZAP ™ XR |
| H0199 | Human Fetal Liver, subtracted, neg clone | Human Fetal Liver | Liver | | | UNI-ZAP ™ XR |
| H0200 | Human Greater Omentum, fract II remake, | Human Greater Omentum | peritoneum | | | UNI-ZAP ™ XR |
| H0201 | Human Hippocampus, subtracted | Human Hippocampus | Brain | | | pBLUESCRIPT ™ |
| H0202 | Jurkat Cells, cyclohexamide treated, subtraction | Cyclohexamide Treated Cem, Jurkat, Raji, and Supt | Blood | Cell Line | | UNI-ZAP ™ XR |
| H0203 | Jurkat Cells, cyclohexamide treated, dif | Cyclohexamide Treated Cem, Jurkat, Raji, and Supt | Blood | Cell Line | | UNI-ZAP ™ XR |
| H0204 | Human Colon Cancer, subtracted | Human Colon Cancer | Colon | | | pBLUESCRIPT ™ |
| H0205 | Human Colon Cancer, differential | Human Colon Cancer | Colon | | | pBLUESCRIPT ™ |
| H0207 | LNCAP, differential expression | LNCAP Cell Line | Prostate | Cell Line | | pBLUESCRIPT ™ |
| H0208 | Early Stage Human Lung, subtracted | Human Fetal Lung | Lung | | | pBLUESCRIPT ™ |

TABLE 4-continued

| Code | Description | Tissue | Organ | Cell Line | Disease | Vector |
|---|---|---|---|---|---|---|
| H0209 | Human Cerebellum, differentially expressed | Human Cerebellum | Brain | | | UNI-ZAP ™ XR |
| H0211 | Human Prostate, differential expression | Human Prostate | Prostate | | | pBLUESCRIPT ™ |
| H0212 | Human Prostate, subtracted | Human Prostate | Prostate | | | pBLUESCRIPT ™ |
| H0213 | Human Pituitary, subtracted | Human Pituitary | | | | UNI-ZAP ™ XR |
| H0214 | Raji cells, cyclohexamide treated, subtracted | Cyclohexamide Treated Cem, Jurkat, Raji, and Supt | Blood | Cell Line | | pBLUESCRIPT ™ |
| H0215 | Raji cells, cyclohexamide treated, differentially expressed | Cyclohexamide Treated Cem, Jurkat, Raji, and Supt | Blood | Cell Line | | pBLUESCRIPT ™ |
| H0216 | Supt cells, cyclohexamide treated, subtracted | Cyclohexamide Treated Cem, Jurkat, Raji, and Supt | Blood | Cell Line | | pBLUESCRIPT ™ |
| H0217 | Supt cells, cyclohexamide treated, differentially expressed | Cyclohexamide Treated Cem, Jurkat, Raji, and Supt | Blood | Cell Line | | pBLUESCRIPT ™ |
| H0218 | Activated T-Cells, 0 hrs, subtracted | Activated T-Cells | Blood | Cell Line | | UNI-ZAP ™ XR |
| H0219 | Activated T-Cells, 0 hrs, differentially expressed | Activated T-Cells | Blood | Cell Line | | UNI-ZAP ™ XR |
| H0220 | Activated T-Cells, 4 hrs, subtracted | Activated T-Cells | Blood | Cell Line | | UNI-ZAP ™ XR |
| H0221 | Activated T-Cells, 4 hrs, differentially expressed | Activated T-Cells | Blood | Cell Line | | UNI-ZAP ™ XR |
| H0222 | Activated T-Cells, 8 hrs, subtracted | Activated T-Cells | Blood | Cell Line | | UNI-ZAP ™ XR |
| H0223 | Activated T-Cells, 8 hrs, differentially expressed | Activated T-Cells | Blood | Cell Line | | UNI-ZAP ™ XR |
| H0224 | Activated T-Cells, 12 hrs, subtracted | Activated T-Cells | Blood | Cell Line | | UNI-ZAP ™ XR |
| H0225 | Activated T-Cells, 12 hrs, differentially expressed | Activated T-Cells | Blood | Cell Line | | UNI-ZAP ™ XR |
| H0228 | C7MCF7 cell line, estrogen treated | C7MCF7 Cell Line, estrogen treated | Breast | Cell Line | | UNI-ZAP ™ XR |
| H0229 | Early Stage Human Brain, random primed | Early Stage Human Brain | Brain | | | LAMBDA ZAP ™ II |
| H0230 | Human Cardiomyopathy, diff exp | Human Cardiomyopathy | Heart | | disease | UNI-ZAP ™ XR |
| H0231 | Human Colon, subtraction | Human Colon | | | | pBLUESCRIPT ™ |
| H0232 | Human Colon, differential expression | Human Colon | | | | pBLUESCRIPT ™ |
| H0233 | Human Fetal Heart, Differential (Adult-Specific) | Human Fetal Heart | Heart | | | pBLUESCRIPT ™ |
| H0234 | human colon cancer, metastatic to liver, differentially expressed | Human Colon Cancer, metasticized to liver | Liver | | | pBLUESCRIPT ™ |
| H0235 | Human colon cancer, metaticized to liver, subtraction | Human Colon Cancer, metasticized to liver | Liver | | | pBLUESCRIPT ™ |
| H0238 | Human Myometrium Leiomyoma | Human Myometrium Leiomyoma | Uterus | | disease | UNI-ZAP ™ XR |
| H0239 | Human Kidney Tumor | Human Kidney Tumor | Kidney | | disease | UNI-ZAP ™ XR |
| H0240 | C7MCF7 cell line, estrogen treated, Differential | C7MCF7 Cell Line, estrogen treated | Breast | Cell Line | | UNI-ZAP ™ XR |
| H0241 | C7MCF7 cell line, estrogen treated, subtraction | C7MCF7 Cell Line, estrogen treated | Breast | Cell Line | | UNI-ZAP ™ XR |
| H0242 | Human Fetal Heart, Differential (Fetal-Specific) | Human Fetal Heart | Heart | | | pBLUESCRIPT ™ |
| H0244 | Human 8 Week Whole Embryo, subtracted | Human 8 Week Old Embryo | Embryo | | | UNI-ZAP ™ XR |
| H0246 | Human Fetal Liver-Enzyme subtraction | Human Fetal Liver | Liver | | | UNI-ZAP ™ XR |
| H0247 | Human Membrane Bound Polysomes-Enzyme Subtraction | Human Membrane Bound Polysomes | Blood | Cell Line | | UNI-ZAP ™ XR |
| H0249 | HE7, subtracted by hybridization with E7 cDNA | Human Whole 7 Week Old Embryo | Embryo | | | UNI-ZAP ™ XR |
| H0250 | Human Activated Monocytes | Human Monocytes | | | | UNI-ZAP ™ XR |
| H0251 | Human Chondrosarcoma | Human Chondrosarcoma | Cartilage | | disease | UNI-ZAP ™ XR |
| H0252 | Human Osteosarcoma | Human Osteosarcoma | Bone | | disease | UNI-ZAP ™ XR |
| H0253 | Human adult testis, large inserts | Human Adult Testis | Testis | | | UNI-ZAP ™ XR |
| H0254 | Breast Lymph node cDNA library | Breast Lymph Node | Lymph Node | | | UNI-ZAP ™ XR |
| H0255 | breast lymph node CDNA library | Breast Lymph Node | Lymph Node | | | LAMBDA ZAP ™ II |
| H0256 | HL-60, unstimulated | Human HL-60 Cells, unstimulated | Blood | Cell Line | | UNI-ZAP ™ XR |

TABLE 4-continued

| Code | Description | Tissue | Organ | Cell Line | Disease | Vector |
|---|---|---|---|---|---|---|
| H0257 | HL-60, PMA 4H | HL-60 Cells, PMA stimulated 4H | Blood | Cell Line | | UNI-ZAP ™ XR |
| H0261 | H. cerebellum, Enzyme subtracted | Human Cerebellum | Brain | | | UNI-ZAP ™ XR |
| H0263 | human colon cancer | Human Colon Cancer | Colon | | disease | LAMBDA ZAP ™ II |
| H0264 | human tonsils | Human Tonsil | Tonsil | | | UNI-ZAP ™ XR |
| H0265 | Activated T-Cell (12 hs)/Thiouridine labelledEco | T-Cells | Blood | Cell Line | | UNI-ZAP ™ XR |
| H0266 | Human Microvascular Endothelial Cells, fract. A | HMEC | Vein | Cell Line | | LAMBDA ZAP ™ II |
| H0267 | Human Microvascular Endothelial Cells, fract. B | HMEC | Vein | Cell Line | | LAMBDA ZAP ™ II |
| H0268 | Human Umbilical Vein Endothelial Cells, fract. A | HUVE Cells | Umbilical vein | Cell Line | | LAMBDA ZAP ™ II |
| H0269 | Human Umbilical Vein Endothelial Cells, fract. B | HUVE Cells | Umbilical vein | Cell Line | | LAMBDA ZAP ™ II |
| H0270 | HPAS (human pancreas, subtracted) | Human Pancreas | Pancreas | | | UNI-ZAP ™ XR |
| H0271 | Human Neutrophil, Activated | Human Neutrophil-Activated | Blood | Cell Line | | UNI-ZAP ™ XR |
| H0272 | HUMAN TONSILS, FRACTION 2 | Human Tonsil | Tonsil | | | UNI-ZAP ™ XR |
| H0274 | Human Adult Spleen, fractionII | Human Adult Spleen | Spleen | | | UNI-ZAP ™ XR |
| H0275 | Human Infant Adrenal Gland, Subtracted | Human Infant Adrenal Gland | Adrenal gland | | | pBLUESCRIPT ™ |
| H0279 | K562 cells | K562 Cell line | cell line | Cell Line | | ZAP EXPRESS ™ |
| H0280 | K562 + PMA (36 hrs) | K562 Cell line | cell line | Cell Line | | ZAP EXPRESS ™ |
| H0281 | Lymph node, abnorm. cell line (ATCC ™ #7225) | Lymph Node, abnormal cell line | Lymph Node | Cell Line | | ZAP EXPRESS ™ |
| H0282 | HBGB''s differential consolidation | Human Primary Breast Cancer | Breast | | | UNI-ZAP ™ XR |
| H0284 | Human OB MG63 control fraction I | Human Osteoblastoma MG63 cell line | Bone | Cell Line | | UNI-ZAP ™ XR |
| H0286 | Human OB MG63 treated (10 nM E2) fraction I | Human Osteoblastoma MG63 cell line | Bone | Cell Line | | UNI-ZAP ™ XR |
| H0288 | Human OB HOS control fraction I | Human Osteoblastoma HOS cell line | Bone | Cell Line | | UNI-ZAP ™ XR |
| H0290 | Human OB HOS treated (1 nM E2) fraction I | Human Osteoblastoma HOS cell line | Bone | Cell Line | | UNI-ZAP ™ XR |
| H0292 | Human OB HOS treated (10 nM E2) fraction I | Human Osteoblastoma HOS cell line | Bone | Cell Line | | UNI-ZAP ™ XR |
| H0293 | WI 38 cells | | | | | UNI-ZAP ™ XR |
| H0294 | Amniotic Cells - TNF induced | Amniotic Cells - TNF induced | Placenta | Cell Line | | UNI-ZAP ™ XR |
| H0295 | Amniotic Cells - Primary Culture | Amniotic Cells - Primary Culture | Placenta | Cell Line | | UNI-ZAP ™ XR |
| H0298 | HCBB''s differential consolidation | CAMA1Ee Cell Line | Breast | Cell Line | | UNI-ZAP ™ XR |
| H0299 | HCBA''s differential consolidation | CAMA1Ee Cell Line | Breast | Cell Line | | UNI-ZAP ™ XR |
| H0300 | CD34 positive cells (Cord Blood) | CD34 Positive Cells | Cord Blood | | | ZAP EXPRESS ™ |
| H0305 | CD34 positive cells (Cord Blood) | CD34 Positive Cells | Cord Blood | | | ZAP EXPRESS ™ |
| H0306 | CD34 depleted Buffy Coat (Cord Blood) | CD34 Depleted Buffy Coat (Cord Blood) | Cord Blood | | | ZAP EXPRESS ™ |
| H0309 | Human Chronic Synovitis | Synovium, Chronic Synovitis/Osteoarthritis | Synovium | | disease | UNI-ZAP ™ XR |
| H0310 | human caudate nucleus | Brain | Brain | | | UNI-ZAP ™ XR |
| H0313 | human pleural cancer | pleural cancer | | | disease | pBLUESCRIPT ™ |
| H0316 | HUMAN STOMACH | Human Stomach | Stomach | | | UNI-ZAP ™ XR |
| H0318 | HUMAN B CELL LYMPHOMA | Human B Cell Lymphoma | Lymph Node | | disease | UNI-ZAP ™ XR |
| H0320 | Human frontal cortex | Human Frontal Cortex | Brain | | | UNI-ZAP ™ XR |
| H0321 | HUMAN SCHWANOMA | Schwanoma | Nerve | | disease | UNI-ZAP ™ XR |
| H0327 | human corpus colosum | Human Corpus Callosum | Brain | | | UNI-ZAP ™ XR |

TABLE 4-continued

| Code | Description | Tissue | Organ | Cell Line | Disease | Vector |
|---|---|---|---|---|---|---|
| H0328 | human ovarian cancer | Ovarian Cancer | Ovary | | disease | UNI-ZAP ™ XR |
| H0329 | Dermatofibrosarcoma Protuberance | Dermatofibrosarcoma Protuberans | Skin | | disease | UNI-ZAP ™ XR |
| H0330 | HCBB''s Subtractive (-mito genes) | CAMA1Ee Cell Line | Breast | Cell Line | | UNI-ZAP ™ XR |
| H0331 | Hepatocellular Tumor | Hepatocellular Tumor | Liver | | disease | LAMBDA ZAP ™ II |
| H0333 | Hemangiopericytoma | Hemangiopericytoma | Blood vessel | | disease | LAMBDA ZAP ™ II |
| H0334 | Kidney cancer | Kidney Cancer | Kidney | | disease | UNI-ZAP ™ XR |
| H0339 | Duodenum | Duodenum | | | | UNI-ZAP ™ XR |
| H0340 | Corpus Callosum | Corpus Collosum-93052 | | | | UNI-ZAP ™ XR |
| H0341 | Bone Marrow Cell Line (RS4; 11) | Bone Marrow Cell Line RS4; 11 | Bone Marrow | Cell Line | | UNI-ZAP ™ XR |
| H0342 | Lingual Gyrus | Lingual Gyrus | Brain | | | UNI-ZAP ™ XR |
| H0343 | stomach cancer (human) | Stomach Cancer - 5383A (human) | | | disease | UNI-ZAP ™ XR |
| H0344 | Adipose tissue (human) | Adipose - 6825A (human) | | | | UNI-ZAP ™ XR |
| H0345 | SKIN | Skin - 4000868H | Skin | | | UNI-ZAP ™ XR |
| H0346 | Brain-medulloblastoma | Brain (Medulloblastoma)-9405C006R | Brain | | disease | UNI-ZAP ™ XR |
| H0349 | human adult liver cDNA library | Human Adult Liver | Liver | | | pCMVSport 1 |
| H0350 | Human Fetal Liver, mixed 10 & 14 week | Human Fetal Liver, mixed 10&14 Week | Liver | | | UNI-ZAP ™ XR |
| H0351 | Glioblastoma | Glioblastoma | Brain | | disease | UNI-ZAP ™ XR |
| H0352 | wilm''s tumor | Wilm''s Tumor | | | disease | UNI-ZAP ™ XR |
| H0354 | Human Leukocytes | Human Leukocytes | Blood | Cell Line | | pCMVSport 1 |
| H0355 | Human Liver | Human Liver, normal Adult | | | | pCMVSport 1 |
| H0356 | Human Kidney | Human Kidney | Kidney | | | pCMVSport 1 |
| H0357 | H. Normalized Fetal Liver, II | Human Fetal Liver | Liver | | | UNI-ZAP ™ XR |
| H0359 | KMH2 cell line | KMH2 | | | | ZAP EXPRESS ™ |
| H0360 | Hemangiopericytoma | Hemangiopericytoma | | | disease | |
| H0361 | Human rejected kidney | Human Rejected Kidney | | | disease | pBLUESCRIPT ™ |
| H0362 | HeLa cell line | HELA CELL LINE | | | | pSport1 |
| H0363 | Human Brain Medulla, subtracted | Human Brain Medulla | | | | pBLUESCRIPT ™ |
| H0364 | Human Osteoclastoma, excised | Human Osteoclastoma | | | disease | pBLUESCRIPT ™ |
| H0365 | Osteoclastoma-normalized B | Human Osteoclastoma | | | disease | UNI-ZAP ™ XR |
| H0366 | L428 cell line | L428 | | | | ZAP EXPRESS ™ |
| H0369 | H. Atrophic Endometrium | Atrophic Endometrium and myometrium | | | | UNI-ZAP ™ XR |
| H0370 | H. Lymph node breast Cancer | Lymph node with Met. Breast Cancer | | | disease | UNI-ZAP ™ XR |
| H0371 | Eosinophils-Hypereosinophilia patient | Eosinophils-Hypereosinophilia patient | | | disease | UNI-ZAP ™ XR |
| H0372 | Human Testes | Human Testes | Testis | | | pCMVSport 1 |
| H0373 | Human Heart | Human Adult Heart | Heart | | | pCMVSport 1 |
| H0374 | Human Brain | Human Brain | | | | pCMVSport 1 |
| H0375 | Human Lung | Human Lung | | | | pCMVSport 1 |
| H0376 | Human Spleen | Human Adult Spleen | Spleen | | | pCMVSport 1 |
| H0379 | Human Tongue, frac 1 | Human Tongue | | | | pSport1 |
| H0380 | Human Tongue, frac 2 | Human Tongue | | | | pSport1 |
| H0381 | Bone Cancer | Bone Cancer | | | disease | UNI-ZAP ™ XR |
| H0383 | Human Prostate BPH, re-excision | Human Prostate BPH | | | | UNI-ZAP ™ XR |
| H0384 | Brain, Kozak | Human Brain | | | | pCMVSport 1 |
| H0385 | H. Leukocytes, Kozak | Human Leukocytes | Blood | Cell Line | | pCMVSport 1 |
| H0386 | Leukocyte and Lung; 4 screens | Human Leukocytes | Blood | Cell Line | | pCMVSport 1 |
| H0388 | Human Rejected Kidney, 704 re-excision | Human Rejected Kidney | | | disease | pBLUESCRIPT ™ |
| H0389 | H. Brain, X-Chromosome hybridization | Human Brain | | | | pCMVSport 1 |
| H0390 | Human Amygdala Depression, re-excision | Human Amygdala Depression | | | disease | pBLUESCRIPT ™ |
| H0391 | H. Meniingima, M6 | Human Meningima | brain | | | pSport1 |

TABLE 4-continued

| Code | Description | Tissue | Organ | Cell Line | Disease | Vector |
|---|---|---|---|---|---|---|
| H0392 | H. Meningima, M1 | Human Meningima | brain | | | pSport1 |
| H0393 | Fetal Liver, subtraction II | Human Fetal Liver | Liver | | | pBLUESCRIPT ™ |
| H0394 | A-14 cell line | Redd-Sternberg cell | | | | ZAP EXPRESS ™ |
| H0395 | A1-CELL LINE | Redd-Sternberg cell | | | | ZAP EXPRESS ™ |
| H0396 | L1 Cell line | Redd-Sternberg cell | | | | ZAP EXPRESS ™ |
| H0398 | Human Newborn Bladder | Human Newborn Bladder | | | | pBLUESCRIPT ™ |
| H0399 | Human Kidney Cortex, re-rescue | Human Kidney Cortex | | | | LAMBDA ZAP ™ II |
| H0400 | Human Striatum Depression, re-rescue | Human Brain, Striatum Depression | Brain | | | LAMBDA ZAP ™ II |
| H0401 | Human Pituitary, subtracted V | Human Pituitary | | | | pBLUESCRIPT ™ |
| H0402 | CD34 depleted Buffy Coat (Cord Blood), re-excision | CD34 Depleted Buffy Coat (Cord Blood) | Cord Blood | | | ZAP EXPRESS ™ |
| H0403 | H. Umbilical Vein Endothelial Cells, IL4 induced | HUVE Cells | Umbilical vein | Cell Line | | UNI-ZAP ™ XR |
| H0404 | H. Umbilical Vein endothelial cells, uninduced | HUVE Cells | Umbilical vein | Cell Line | | UNI-ZAP ™ XR |
| H0405 | Human Pituitary, subtracted VI | Human Pituitary | | | | pBLUESCRIPT ™ |
| H0406 | H Amygdala Depression, subtracted | Human Amygdala Depression | | | | UNI-ZAP ™ XR |
| H0408 | Human kidney Cortex, subtracted | Human Kidney Cortex | | | | pBLUESCRIPT ™ |
| H0409 | H. Striatum Depression, subtracted | Human Brain, Striatum Depression | Brain | | | pBLUESCRIPT ™ |
| H0410 | H. Male bladder, adult | H Male Bladder, Adult | Bladder | | | pSport1 |
| H0411 | H Female Bladder, Adult | Human Female Adult Bladder | Bladder | | | pSport1 |
| H0412 | Human umbilical vein endothelial cells, IL-4 induced | HUVE Cells | Umbilical vein | Cell Line | | pSport1 |
| H0413 | Human Umbilical Vein Endothelial Cells, uninduced | HUVE Cells | Umbilical vein | Cell Line | | pSport1 |
| H0414 | Ovarian Tumor I, OV5232 | Ovarian Tumor, OV5232 | Ovary | | disease | pSport1 |
| H0415 | H. Ovarian Tumor, II, OV5232 | Ovarian Tumor, OV5232 | Ovary | | disease | pCMVSport 2.0 |
| H0416 | Human Neutrophils, Activated, re-excision | Human Neutrophil - Activated | Blood | Cell Line | | pBLUESCRIPT ™ |
| H0417 | Human Pituitary, subtracted VIII | Human Pituitary | | | | pBLUESCRIPT ™ |
| H0418 | Human Pituitary, subtracted VII | Human Pituitary | | | | pBLUESCRIPT ™ |
| H0419 | Bone Cancer, re-excision | Bone Cancer | | | | UNI-ZAP ™ XR |
| H0421 | Human Bone Marrow, re-excision | Bone Marrow | | | | pBLUESCRIPT ™ |
| H0422 | T-Cell PHA 16 hrs | T-Cells | Blood | Cell Line | | pSport1 |
| H0423 | T-Cell PHA 24 hrs | T-Cells | Blood | Cell Line | | pSport1 |
| H0424 | Human Pituitary, subt IX | Human Pituitary | | | | pBLUESCRIPT ™ |
| H0427 | Human Adipose | Human Adipose, left hiplipoma | | | | pSport1 |
| H0428 | Human Ovary | Human Ovary Tumor | Ovary | | | pSport1 |
| H0429 | K562 + PMA (36 hrs), re-excision | K562 Cell line | cell line | Cell Line | | ZAP EXPRESS ™ |
| H0431 | H. Kidney Medulla, re-excision | Kidney medulla | Kidney | | | pBLUESCRIPT ™ |
| H0432 | H. Kidney Pyramid | Kidney pyramids | Kidney | | | pBLUESCRIPT ™ |
| H0433 | Human Umbilical Vein Endothelial cells, frac B, re-excision | HUVE Cells | Umbilical vein | Cell Line | | pBLUESCRIPT ™ |
| H0434 | Human Brain, striatum, re-excision | Human Brain, Striatum | | | | pBLUESCRIPT ™ |
| H0435 | Ovarian Tumor Oct. 3, 1995 | Ovarian Tumor, OV350721 | Ovary | | | pCMVSport 2.0 |
| H0436 | Resting T-Cell Library, II | T-Cells | Blood | Cell Line | | pSport1 |
| H0437 | H Umbilical Vein Endothelial Cells, frac A, re-excision | HUVE Cells | Umbilical vein | Cell Line | | LAMBDA ZAP ™ II |
| H0438 | H. Whole Brain #2, re-excision | Human Whole Brain #2 | | | | ZAP EXPRESS ™ |
| H0439 | Human Eosinophils | Eosinophils | | | | pBLUESCRIPT ™ |
| H0440 | FGF enriched mixed library | Mixed libraries | | | | pCMVSport 1 |
| H0441 | H. Kidney Cortex, subtracted | Kidney cortex | Kidney | | | pBLUESCRIPT ™ |
| H0442 | H. Striatum Depression, subt II | Human Brain, Striatum Depression | Brain | | | pBLUESCRIPT ™ |
| H0443 | H. Adipose, subtracted | Human Adipose, left hiplipoma | | | | pSport1 |
| H0444 | Spleen metastic melanoma | Spleen, Metastic malignant melanoma | Spleen | | disease | pSport1 |
| H0445 | Spleen, Chronic lymphocytic leukemia | Human Spleen, CLL | Spleen | | disease | pSport1 |
| H0447 | Salivary gland, re-excision | Human Salivary Gland | Salivary gland | | | UNI-ZAP ™ XR |
| H0448 | Salivary gland, subtracted | Human Salivary Gland | Salivary gland | | | LAMBDA ZAP ™ II |

TABLE 4-continued

| Code | Description | Tissue | Organ | Cell Line | Disease | Vector |
|---|---|---|---|---|---|---|
| H0449 | CD34+ cell, I | CD34 positive cells | | | | pSport1 |
| H0450 | CD34+ cells, II | CD34 positive cells | | | | pCMVSport 2.0 |
| H0453 | H. Kidney Pyramid, subtracted | Kidney pyramids | Kidney | | | pBLUESCRIPT ™ |
| H0455 | H. Striatum Depression, subt | Human Brain, Striatum Depression | Brain | | | pBLUESCRIPT ™ |
| H0456 | H Kidney Cortex, subtracted III | Human Kidney Cortex | | | | pBLUESCRIPT ™ |
| H0457 | Human Eosinophils | Human Eosinophils | | | | pSport1 |
| H0458 | CD34+ cell, I, frac II | CD34 positive cells | | | | pSport1 |
| H0459 | CD34+ cells, II, FRACTION 2 | CD34 positive cells | | | | pCMVSport 2.0 |
| H0461 | H. Kidney Medulla, subtracted | Kidney medulla | Kidney | | | pBLUESCRIPT ™ |
| H0462 | H. Amygdala Depression, subtracted | | Brain | | | pBLUESCRIPT ™ |
| H0477 | Human Tonsil, Lib 3 | Human Tonsil | Tonsil | | | pSport1 |
| H0478 | Salivary Gland, Lib 2 | Human Salivary Gland | Salivary gland | | | pSport1 |
| H0479 | Salivary Gland, Lib 3 | Human Salivary Gland | Salivary gland | | | pSport1 |
| H0480 | L8 cell line | L8 cell line | | | | ZAP EXPRESS ™ |
| H0483 | Breast Cancer cell line, MDA 36 | Breast Cancer Cell line, MDA 36 | | | | pSport1 |
| H0484 | Breast Cancer Cell line, angiogenic | Breast Cancer Cell line, Angiogenic, 36T3 | | | | pSport1 |
| H0485 | Hodgkin''s Lymphoma I | Hodgkin''s Lymphoma I | | | disease | pCMVSport 2.0 |
| H0486 | Hodgkin''s Lymphoma II | Hodgkin''s Lymphoma II | | | disease | pCMVSport 2.0 |
| H0487 | Human Tonsils, lib I | Human Tonsils | | | | pCMVSport 2.0 |
| H0488 | Human Tonsils, Lib 2 | Human Tonsils | | | | pCMVSport 2.0 |
| H0489 | Crohn''s Disease | Ileum | Intestine | | disease | pSport1 |
| H0490 | H1-60, untreated, subtracted | Human HL-60 Cells, unstimulated | Blood | Cell Line | | UNI-ZAP ™ XR |
| H0491 | HL-60, PMA 4 H, subtracted | HL-60 Cells, PMA stimulated 4 H | Blood | Cell Line | | UNI-ZAP ™ XR |
| H0492 | HL-60, RA 4 h, Subtracted | HL-60 Cells, RA stimulated for 4 H | Blood | Cell Line | | UNI-ZAP ™ XR |
| H0493 | HL-60, PMA 1 d, subtracted | HL-60 Cells, PMA stimulated for 1 day | Blood | Cell Line | | UNI-ZAP ™ XR |
| H0494 | Keratinocyte | Keratinocyte | | | | pCMVSport 2.0 |
| H0497 | HEL cell line | HEL cell line | | HEL 92.1.7 | | pSport1 |
| H0505 | Human Astrocyte | Human Astrocyte | | | | pSport1 |
| H0506 | Ulcerative Colitis | Colon | Colon | | | pSport1 |
| H0509 | Liver, Hepatoma | Human Liver, Hepatoma, patient 8 | Liver | | disease | pCMVSport 3.0 |
| H0510 | Human Liver, normal | Human Liver, normal, Patient # 8 | Liver | | | pCMVSport 3.0 |
| H0512 | Keratinocyte, lib 3 | Keratinocyte | | | | pCMVSport 2.0 |
| H0517 | Nasal polyps | Nasal polyps | | | | pCMVSport 2.0 |
| H0518 | pBMC stimulated w/poly I/C | pBMC stimulated with poly I/C | | | | pCMVSport 3.0 |
| H0519 | NTERA2, control | NTERA2, Teratocarcinoma cell line | | | | pCMVSport 3.0 |
| H0520 | NTERA2 + retinoic acid, 14 days | NTERA2, Teratocarcinoma cell line | | | | pSport1 |
| H0521 | Primary Dendritic Cells, lib 1 | Primary Dendritic cells | | | | pCMVSport 3.0 |
| H0522 | Primary Dendritic cells, frac 2 | Primary Dendritic cells | | | | pCMVSport 3.0 |
| H0523 | Primary Dendritic cells, CapFinder2, frac 1 | Primary Dendritic cells | | | | pSport1 |
| H0524 | Primary Dendritic Cells, CapFinder, frac 2 | Primary Dendritic cells | | | | pSport1 |
| H0525 | PCR, pBMC I/C treated | pBMC stimulated with poly I/C | | | | pCR II [Invitrogen] |
| H0528 | Poly[I]/Poly[C] Normal Lung Fibroblasts | Poly[I]/Poly[C] Normal Lung Fibroblasts | | | | pCMVSport 3.0 |
| H0529 | Myoloid Progenitor Cell Line | TF-1 Cell Line; Myoloid progenitor cell line | | | | pCMVSport 3.0 |
| H0530 | Human Dermal Endothelial Cells, untreated | Human Dermal Endothelial Cells; untreated | | | | pSport1 |
| H0533 | Human Stromal endometrial fibroblasts, treated w/estradiol | Human Stromal endometrial fibroblasts, treated wit | | | | pSport1 |
| H0535 | Human ovary tumor cell OV350721 | Ovarian Tumor, OV350721 | Ovary | | disease | pSport1 |
| H0537 | H. Primary Dendritic Cells, lib 3 | Primary Dendritic cells | | | | pCMVSport 2.0 |
| H0538 | Merkel Cells | Merkel cells | Lymph node | | | pSport1 |
| H0539 | Pancreas Islet Cell Tumor | Pancreas Islet Cell Tumour | Pancreas | | disease | pSport1 |
| H0540 | Skin, burned | Skin, leg burned | Skin | | | pSport1 |
| H0542 | T Cell helper I | Helper T cell | | | | pCMVSport 3.0 |
| H0543 | T cell helper II | Helper T cell | | | | pCMVSport 3.0 |

TABLE 4-continued

| Code | Description | Tissue | Organ | Cell Line | Disease | Vector |
|---|---|---|---|---|---|---|
| H0544 | Human endometrial stromal cells | Human endometrial stromal cells | | | | pCMVSport 3.0 |
| H0545 | Human endometrial stromal cells-treated with progesterone | Human endometrial stromal cells-treated with proge | | | | pCMVSport 3.0 |
| H0546 | Human endometrial stromal cells-treated with estradiol | Human endometrial stromal cells-treated with estra | | | | pCMVSport 3.0 |
| H0547 | NTERA2 teratocarcinoma cell line + retinoic acid (14 days) | NTERA2, Teratocarcinoma cell line | | | | pSport1 |
| H0548 | Human Skin Fibroblasts, normal | Human Skin Fibroblasts | | | | pBLUESCRIPT ™ |
| H0549 | H. Epididiymus, caput & corpus | Human Epididiymus, caput and corpus | | | | UNI-ZAP ™ XR |
| H0550 | H. Epididiymus, cauda | Human Epididiymus, cauda | | | | UNI-ZAP ™ XR |
| H0551 | Human Thymus Stromal Cells | Human Thymus Stromal Cells | | | | pCMVSport 3.0 |
| H0552 | Signal trap, Femur Bone Marrow, pooled | Femur Bone marrow, pooled from 8 male/female | | | | Other |
| H0553 | Human Placenta | Human Placenta | | | | pCMVSport 3.0 |
| H0555 | Rejected Kidney, lib 4 | Human Rejected Kidney | Kidney | | disease | pCMVSport 3.0 |
| H0556 | Activated T-cell(12 h)/Thiouridine-re-excision | T-Cells | Blood | Cell Line | | UNI-ZAP ™ XR |
| H0559 | HL-60, PMA 4 H, re-excision | HL-60 Cells, PMA stimulated 4 H | Blood | Cell Line | | UNI-ZAP ™ XR |
| H0560 | KMH2 | KMH2 | | | | pCMVSport 3.0 |
| H0561 | L428 | L428 | | | | pCMVSport 3.0 |
| H0562 | Human Fetal Brain, normalized c5-11-26 | Human Fetal Brain | | | | pCMVSport 2.0 |
| H0563 | Human Fetal Brain, normalized 50021F | Human Fetal Brain | | | | pCMVSport 2.0 |
| H0564 | Human Fetal Brain, normalized C5001F | Human Fetal Brain | | | | pCMVSport 2.0 |
| H0565 | Human Fetal Brain, normalized 100024F | Human Fetal Brain | | | | pCMVSport 2.0 |
| H0566 | Human Fetal Brain, normalized c50F | Human Fetal Brain | | | | pCMVSport 2.0 |
| H0567 | Human Fetal Brain, normalized A5002F | Human Fetal Brain | | | | pCMVSport 2.0 |
| H0569 | Human Fetal Brain, normalized CO | Human Fetal Brain | | | | pCMVSport 2.0 |
| H0570 | Human Fetal Brain, normalized C500H | Human Fetal Brain | | | | pCMVSport 2.0 |
| H0571 | Human Fetal Brain, normalized C500HE | Human Fetal Brain | | | | pCMVSport 2.0 |
| H0572 | Human Fetal Brain, normalized AC5002 | Human Fetal Brain | | | | pCMVSport 2.0 |
| H0574 | Hepatocellular Tumor; re-excision | Hepatocellular Tumor | Liver | | disease | LAMBDA ZAP ™ II |
| H0575 | Human Adult Pulmonary; re-excision | Human Adult Pulmonary | Lung | | | UNI-ZAP ™ XR |
| H0576 | Resting T-Cell; re-excision | T-Cells | Blood | Cell Line | | LAMBDA ZAP ™ II |
| H0578 | Human Fetal Thymus | Fetal Thymus | Thymus | | | pSport1 |
| H0579 | Pericardium | Pericardium | Heart | | | pSport1 |
| H0580 | Dendritic cells, pooled | Pooled dendritic cells | | | | pCMVSport 3.0 |
| H0581 | Human Bone Marrow, treated | Human Bone Marrow | Bone Marrow | | | pCMVSport 3.0 |
| H0583 | B Cell lymphoma | B Cell Lymphoma | B Cell | | disease | pCMVSport 3.0 |
| H0584 | Activated T-cells, 24 hrs, re-excision | Activated T-Cells | Blood | Cell Line | | UNI-ZAP ™ XR |
| H0585 | Activated T-Cells, 12 hrs, re-excision | Activated T-Cells | Blood | Cell Line | | UNI-ZAP ™ XR |
| H0586 | Healing groin wound, 6.5 hours post incision | healing groin wound, 6.5 hours post incision-2/ | groin | | disease | pCMVSport 3.0 |
| H0587 | Healing groin wound; 7.5 hours post incision | Groin-Feb. 19, 1997 | groin | | disease | pCMVSport 3.0 |
| H0589 | CD34 positive cells (cord blood), re-ex | CD34 Positive Cells | Cord Blood | | | ZAP EXPRESS ™ |
| H0590 | Human adult small intestine, re-excision | Human Adult Small Intestine | Small Int. | | | UNI-ZAP ™ XR |
| H0591 | Human T-cell lymphoma; re-excision | T-Cell Lymphoma | T-Cell | | disease | UNI-ZAP ™ XR |
| H0592 | Healing groin wound - zero hr post-incision (control) | HGS wound healing project; abdomen | | | disease | pCMVSport 3.0 |
| H0593 | Olfactory epithelium; nasalcavity | Olfactory epithelium from roof of left nasal cacit | | | | pCMVSport 3.0 |
| H0594 | Human Lung Cancer; re-excision | Human Lung Cancer | Lung | | disease | LAMBDA ZAP ™ II |

TABLE 4-continued

| Code | Description | Tissue | Organ | Cell Line | Disease | Vector |
|---|---|---|---|---|---|---|
| H0595 | Stomach cancer (human); re-excision | Stomach Cancer-5383A (human) | | | disease | UNI-ZAP ™ XR |
| H0596 | Human Colon Cancer; re-excision | Human Colon Cancer | Colon | | | LAMBDA ZAP ™ II |
| H0597 | Human Colon; re-excision | Human Colon | | | | LAMBDA ZAP ™ II |
| H0598 | Human Stomach; re-excision | Human Stomach | Stomach | | | UNI-ZAP ™ XR |
| H0599 | Human Adult Heart; re-excision | Human Adult Heart | Heart | | | UNI-ZAP ™ XR |
| H0600 | Healing Abdomen wound; 70&90 min post incision | Abdomen | | | disease | pCMVSport 3.0 |
| H0601 | Healing Abdomen Wound; 15 days post incision | Abdomen | | | disease | pCMVSport 3.0 |
| H0602 | Healing Abdomen Wound; 21&29 days post incision | Abdomen | | | disease | pCMVSport 3.0 |
| H0604 | Human Pituitary, re-excision | Human Pituitary | | | | pBLUESCRIPT ™ |
| H0606 | Human Primary Breast Cancer; re-excision | Human Primary Breast Cancer | Breast | | disease | UNI-ZAP ™ XR |
| H0607 | H. Leukocytes, normalized cot 50A3 | H. Leukocytes | | | | pCMVSport 1 |
| H0608 | H. Leukocytes, control | H. Leukocytes | | | | pCMVSport 1 |
| H0609 | H. Leukocytes, normalized cot >500A | H. Leukocytes | | | | pCMVSport 1 |
| H0610 | H. Leukocytes, normalized cot 5A | H. Leukocytes | | | | pCMVSport 1 |
| H0611 | H. Leukocytes, normalized cot 500 B | H. Leukocytes | | | | pCMVSport 1 |
| H0612 | H. Leukocytes, normalized cot 50 B | H. Leukocytes | | | | pCMVSport 1 |
| H0613 | H. Leukocytes, normalized cot 5B | H. Leukocytes | | | | pCMVSport 1 |
| H0614 | H. Leukocytes, normalized cot 500 A | H. Leukocytes | | | | pCMVSport 1 |
| H0615 | Human Ovarian Cancer Reexcision | Ovarian Cancer | Ovary | | disease | UNI-ZAP ™ XR |
| H0616 | Human Testes, Reexcision | Human Testes | Testis | | | UNI-ZAP ™ XR |
| H0617 | Human Primary Breast Cancer Reexcision | Human Primary Breast Cancer | Breast | | disease | UNI-ZAP ™ XR |
| H0618 | Human Adult Testes, Large Inserts, Reexcision | Human Adult Testis | Testis | | | UNI-ZAP ™ XR |
| H0619 | Fetal Heart | Human Fetal Heart | Heart | | | UNI-ZAP ™ XR |
| H0620 | Human Fetal Kidney; Reexcision | Human Fetal Kidney | Kidney | | | UNI-ZAP ™ XR |
| H0622 | Human Pancreas Tumor; Reexcision | Human Pancreas Tumor | Pancreas | | disease | UNI-ZAP ™ XR |
| H0623 | Human Umbilical Vein; Reexcision | Human Umbilical Vein Endothelial Cells | Umbilical vein | | | UNI-ZAP ™ XR |
| H0624 | 12 Week Early Stage Human II; Reexcision | Twelve Week Old Early Stage Human | Embryo | | | UNI-ZAP ™ XR |
| H0625 | Ku 812F Basophils Line | Ku 812F Basophils | | | | pSport1 |
| H0626 | Saos2 Cells; Untreated | Saos2 Cell Line; Untreated | | | | pSport1 |
| H0627 | Saos2 Cells; Vitamin D3 Treated | Saos2 Cell Line; Vitamin D3 Treated | | | | pSport1 |
| H0628 | Human Pre-Differentiated Adipocytes | Human Pre-Differentiated Adipocytes | | | | UNI-ZAP ™ XR |
| H0629 | Human Leukocyte, control #2 | Human Normalized leukocyte | | | | pCMVSport 1 |
| H0630 | Human Leukocytes, normalized control #4 | Human Normalized leukocyte | | | | pCMVSport 1 |
| H0631 | Saos2, Dexamethosome Treated | Saos2 Cell Line; Dexamethosome Treated | | | | pSport1 |
| H0632 | Hepatocellular Tumor; re-excision | Hepatocellular Tumor | Liver | | | LAMBDA ZAP ™ II |
| H0633 | Lung Carcinoma A549 TNFalpha activated | TNFalpha activated A549-Lung Carcinoma | | | disease | pSport1 |
| H0634 | Human Testes Tumor, re-excision | Human Testes Tumor | Testis | | disease | UNI-ZAP ™ XR |
| H0635 | Human Activated T-Cells, re-excision | Activated T-Cells | Blood | Cell Line | | UNI-ZAP ™ XR |
| H0637 | Dendritic Cells From CD34 Cells | Dentritic cells from CD34 cells | | | | pSport1 |
| H0638 | CD40 activated monocyte dendridic cells | CD40 activated monocyte dendridic cells | | | | pSport1 |
| H0639 | Ficolled Human Stromal Cells, 5Fu treated | Ficolled Human Stromal Cells, 5Fu treated | | | | Other |

TABLE 4-continued

| Code | Description | Tissue | Organ | Cell Line | Disease | Vector |
|---|---|---|---|---|---|---|
| H0640 | FICOLL ™ed Human Stromal Cells, Untreated | FICOLL ™ed Human Stromal Cells, Untreated | | | | Other |
| H0641 | LPS activated derived dendritic cells | LPS activated monocyte derived dendritic cells | | | | pSport1 |
| H0642 | Hep G2 Cells, lambda library | Hep G2 Cells | | | | Other |
| H0643 | Hep G2 Cells, PCR library | Hep G2 Cells | | | | Other |
| H0644 | Human Placenta (re-excision) | Human Placenta | Placenta | | | UNI-ZAP ™ XR |
| H0645 | Fetal Heart, re-excision | Human Fetal Heart | Heart | | | UNI-ZAP ™ XR |
| H0646 | Lung, Cancer (4005313 A3): Invasive Poorly Differentiated Lung Adenocarcinoma, | Metastatic squamous cell lung carcinoma, poorly di | | | | pSport1 |
| H0647 | Lung, Cancer (4005163 B7): Invasive, Poorly Diff. Adenocarcinoma, Metastatic | Invasive poorly differentiated lung adenocarcinoma | | | disease | pSport1 |
| H0648 | Ovary, Cancer: (4004562 B6) Papillary Serous Cystic Neoplasm, Low Malignant Pot | Papillary Cstic neoplasm of low malignant potentia | | | disease | pSport1 |
| H0649 | Lung, Normal: (4005313 B1) | Normal Lung | | | | pSport1 |
| H0650 | B-Cells | B-Cells | | | | pCMVSport 3.0 |
| H0651 | Ovary, Normal: (9805C040R) | Normal Ovary | | | | pSport1 |
| H0652 | Lung, Normal: (4005313 B1) | Normal Lung | | | | pSport1 |
| H0653 | Stromal Cells | Stromal Cells | | | | pSport1 |
| H0654 | Lung, Cancer: (4005313 A3) Invasive Poorly-differentiated Metastatic lung adenoc | Metastatic Squamous cell lung Carcinoma poorly dif | | | | Other |
| H0656 | B-cells (unstimulated) | B-cells (unstimulated) | | | | pSport1 |
| H0657 | B-cells (stimulated) | B-cells (stimulated) | | | | pSport1 |
| H0658 | Ovary, Cancer (9809C332): Poorly differentiated adenocarcinoma | 9809C332-Poorly differentiate | Ovary & Fallopian Tubes | | disease | pSport1 |
| H0659 | Ovary, Cancer (15395A1F): Grade II Papillary Carcinoma | Grade II Papillary Carcinoma, Ovary | Ovary | | disease | pSport1 |
| H0660 | Ovary, Cancer: (15799A1F) Poorly differentiated carcinoma | Poorly differentiated carcinoma, ovary | | | disease | pSport1 |
| H0661 | Breast, Cancer: (4004943 A5) | Breast cancer | | | disease | pSport1 |
| H0662 | Breast, Normal: (4005522B2) | Normal Breast-#4005522(B2) | Breast | | | pSport1 |
| H0663 | Breast, Cancer: (4005522 A2) | Breast Cancer-#4005522(A2) | Breast | | disease | pSport1 |
| H0664 | Breast, Cancer: (9806C012R) | Breast Cancer | Breast | | disease | pSport1 |
| H0665 | Stromal cells 3.88 | Stromal cells 3.88 | | | | pSport1 |
| H0666 | Ovary, Cancer: (4004332 A2) | Ovarian Cancer, Sample #4004332A2 | | | disease | pSport1 |
| H0667 | Stromal cells(HBM3.18) | Stromal cell(HBM 3.18) | | | | pSport1 |
| H0668 | stromal cell clone 2.5 | stromal cell clone 2.5 | | | | pSport1 |
| H0669 | Breast, Cancer: (4005385 A2) | Breast Cancer (4005385A2) | Breast | | | pSport1 |
| H0670 | Ovary, Cancer(4004650 A3): Well-Differentiated Micropapillary Serous Carcinoma | Ovarian Cancer-4004650A3 | | | | pSport1 |
| H0671 | Breast, Cancer: (9802C02OE) | Breast Cancer-Sample # 9802C02OE | | | | pSport1 |
| H0672 | Ovary, Cancer: (4004576 A8) | Ovarian Cancer(4004576A8) | Ovary | | | pSport1 |
| H0673 | Human Prostate Cancer, Stage B2; re-excision | Human Prostate Cancer, stage B2 | Prostate | | | UNI-ZAP ™ XR |
| H0674 | Human Prostate Cancer, Stage C; re-excission | Human Prostate Cancer, stage C | Prostate | | | UNI-ZAP ™ XR |
| H0675 | Colon, Cancer: (9808C064R) | Colon Cancer 9808C064R | | | | pCMVSport 3.0 |
| H0676 | Colon, Cancer: (9808C064R)-total RNA | Colon Cancer 9808C064R | | | | pCMVSport 3.0 |
| H0677 | TNFR degenerate oligo | B-Cells | | | | pCR II [Invitrogen] |
| H0678 | screened clones from placental library | Placenta | Placenta | | | Other |
| H0679 | screened clones from Tonsil library | Human Tonsils | | | | Other |
| H0682 | Serous Papillary Adenocarcinoma | serous papillary adenocarcinoma (9606G304SPA3B) | | | | pCMVSport 3.0 |
| H0683 | Ovarian Serous Papillary Adenocarcinoma | Serous papillary adenocarcinoma, stage 3C (9804G01 | | | | pCMVSport 3.0 |
| H0684 | Serous Papillary Adenocarcinoma | Ovarian Cancer-9810G606 | Ovaries | | | pCMVSport 3.0 |
| H0685 | Adenocarcinoma of Ovary, Human Cell Line, # OVCAR-3 | Adenocarcinoma of Ovary, Human Cell Line, # OVCAR- | | | | pCMVSport 3.0 |

TABLE 4-continued

| Code | Description | Tissue | Organ | Cell Line | Disease | Vector |
|---|---|---|---|---|---|---|
| H0686 | Adenocarcinoma of Ovary, Human Cell Line | Adenocarcinoma of Ovary, Human Cell Line, # SW-626 | | | | pCMVSport 3.0 |
| H0687 | Human normal ovary(#9610G215) | Human normal ovary(#9610G215) | Ovary | | | pCMVSport 3.0 |
| H0688 | Human Ovarian Cancer(#9807G017) | Human Ovarian cancer(#9807G017), mRNA from Maura Ru | | | | pCMVSport 3.0 |
| H0689 | Ovarian Cancer | Ovarian Cancer, #9806G019 | | | | pCMVSport 3.0 |
| H0690 | Ovarian Cancer, # 9702G001 | Ovarian Cancer, #9702G001 | | | | pCMVSport 3.0 |
| H0691 | Normal Ovary, #9710G208 | normal ovary, #9710G208 | | | | pCMVSport 3.0 |
| H0692 | BLyS Receptor from Expression Cloning | B Cell Lymphoma | B Cell | | | pCMVSport 3.0 |
| H0693 | Normal Prostate #ODQ3958EN | Normal Prostate Tissue # ODQ3958EN | | | | pCMVSport 3.0 |
| H0694 | Prostate gland adenocarcinoma | Prostate gland, adenocarcinoma, mod/diff, gleason | prostate gland | | | pCMVSport 3.0 |
| H0695 | mononucleocytes from patient | mononucleocytes from patient at Shady Grove Hospit | | | | pCMVSport 3.0 |
| L0002 | Atrium cDNA library Human heart | | | | | |
| L0004 | CLONTECH ™ HL 1065a | | | | | |
| L0005 | CLONTECH ™ human aorta polyA+ mRNA (#6572) | | | | | |
| L0009 | EST from 8p21.3-p22 | | | | | |
| L0012 | HDMEC cDNA library | | | | | |
| L0015 | Human | | | | | |
| L0017 | Human (J. Swensen) | | | | | |
| L0018 | Human (M. Lovett) | | | | | |
| L0021 | Human adult (K. Okubo) | | | | | |
| L0022 | Human adult lung 3" directed MboI cDNA | | | | | |
| L0023 | human adult testis | | | | | |
| L0024 | Human brain A RSanders | | | | | |
| L0025 | Human brain striatum | | | | | |
| L0032 | Human chromosome 12p cDNAs | | | | | |
| L0033 | Human chromosome 13q14 cDNA | | | | | |
| L0034 | Human chromosome 14 | | | | | |
| L0038 | Human chromosome 6 | | | | | |
| L0040 | Human colon mucosa | | | | | |
| L0041 | Human epidermal keratinocyte | | | | | |
| L0045 | Human keratinocyte differential display (B. Lin) | | | | | |
| L0051 | Human mRNA (Tripodis and Ragoussis) | | | | | |
| L0052 | Human normalized K562-cDNA | | | | | |
| L0053 | Human pancreatic tumor | | | | | |
| L0055 | Human promyelocyte | | | | | |
| L0060 | Human thymus NSTH II | | | | | |
| L0065 | Liver HepG2 cell line. | | | | | |
| L0070 | Selected chromosome 21 cDNA library | | | | | |
| L0096 | Subtracted human retina | | | | | |
| L0097 | Subtracted human retinal pigment epithelium (RPE) | | | | | |
| L0103 | DKFZphamy1 | amygdala | | | | |
| L0105 | Human aorta polyA+ (TFujiwara) | aorta | | | | |
| L0109 | Human brain cDNA | brain | | | | |
| L0114 | Human fetal brain (R. L. Margolis) | brain | | | | |
| L0117 | Human fetal brain cDNA (T. M. Gress) | brain | | | | |
| L0118 | Human fetal brain S. Meier-Ewert | brain | | | | |
| L0121 | Stratagene catalog #936206 | brain | | | | |
| L0126 | Human fibroblast cDNA | fibroblast | | | | |
| L0130 | Human hippocampus, Stratagene catalog #936205 | hippocampus | | | | |
| L0136 | Human neuroepithelium (N. Jiang) | neuroepithelium | | | | |
| L0138 | Human normal gingiva | normal gingiva | | | | |
| L0140 | Human pancreatic cancer (C Wallrapp) | pancreatic cancer | | | | |
| L0141 | Human pancreatic islet cell | pancreatic islet | | | | |

TABLE 4-continued

| Code | Description | Tissue | Organ | Cell Line | Disease | Vector |
|---|---|---|---|---|---|---|
| L0142 | Human placenta cDNA (T Fujiwara) | placenta | | | | |
| L0143 | Human placenta polyA+ (T Fujiwara) | placenta | | | | |
| L0145 | Human retina (D. Swanson) | retina | | | | |
| L0146 | Human fovea cDNA | retinal fovea | | | | |
| L0149 | DKFZphsnu1 | subthalamic nucleus | | | | |
| L0151 | Human testis (C. De Smet) | testis | | | | |
| L0157 | Human fetal brain (T Fujiwara) | | brain | | | |
| L0158 | Human fetal brain Q Boqin | | brain | | | |
| L0162 | Human brain frontal cortex | frontal cortex | brain | | | |
| L0163 | Human heart cDNA (Y Nakamura) | | heart | | | |
| L0171 | Human lung adenocarcinoma A549 | lung adenocarcinoma | | A549 | | |
| L0175 | Human retina cell line ARPE-19 | retina | | ARPE-19 | | |
| L0177 | Human newborn melanocytes (T. Vogt) | | | Clonetics Corp. (San Diego, CA) strain #68 and 2486 | | |
| L0182 | Human HeLa (Y. Wang) | | | HeLa | | |
| L0183 | Human HeLa cells (M. Lovett) | | | HeLa | | |
| L0185 | Human immortalized fibroblasts (H. L. Ozer) | | | HS74 and its SV40-transformed sublines | | |
| L0186 | Human salivary gland cell line HSG | salivary gland | | HSG | | |
| L0187 | Human fibrosarcoma cell line HT1080 | fibrosarcoma | | HT1080 | | |
| L0194 | Human pancreatic cancer cell line Patu 8988t | pancreatic cancer | | Patu 8988t | | |
| L0295 | Human liver EST (Y. L. Yu) | | liver | | | |
| L0307 | Human C3-A11N | | | C3-A11N; clonally related variant of OCI LY8-C3P | | |
| L0309 | Human E8CASS | breast adenocarcinoma | | E8CASS; variant of MCF7 | | |
| L0351 | Infant brain, Bento Soares | | | | | BA, M13-derived |
| L0352 | Normalized infant brain, Bento Soares | | | | | BA, M13-derived |
| L0353 | 21q Placenta, F. Tassone and K. Gardiner | | | | | pBLUESCRIPT ™ |
| L0354 | JG, Human foetal Kidney tissue | | | | | pBLUESCRIPT ™ |
| L0355 | P, Human foetal Brain Whole tissue | | | | | pBLUESCRIPT ™ |
| L0356 | S, Human foetal Adrenals tissue | | | | | pBLUESCRIPT ™ |
| L0357 | V, Human Placenta tissue | | | | | Bluescript KS II+ |
| L0361 | STRATAGENE ™ ovary (#937217) | | ovary | | | pBLUESCRIPT ™ SK |
| L0362 | STRATAGENE ™ ovarian cancer (#937219) | | | | | pBLUESCRIPT ™ SK− |
| L0363 | NCI_CGAP_GC2 | germ cell tumor | | | | pBLUESCRIPT ™ SK− |
| L0364 | NCI_CGAP_GC5 | germ cell tumor | | | | pBLUESCRIPT ™ SK− |
| L0365 | NCI_CGAP_Phe1 | pheochromocytoma | | | | pBLUESCRIPT ™ SK− |
| L0366 | STRATAGENE ™ schizo brain S11 | schizophrenic brain S-11 frontal lobe | | | | pBLUESCRIPT ™ SK− |
| L0367 | NCI_CGAP_Sch1 | Schwannoma tumor | | | | pBLUESCRIPT ™ SK− |
| L0368 | NCI_CGAP_SS1 | synovial sarcoma | | | | pBLUESCRIPT ™ SK− |
| L0369 | NCI_CGAP_AA1 | adrenal adenoma | adrenal gland | | | pBLUESCRIPT ™ SK− |
| L0370 | Johnston frontal cortex | pooled frontal lobe | brain | | | pBLUESCRIPT ™ SK− |
| L0371 | NCI_CGAP_Br3 | breast tumor | breast | | | pBLUESCRIPT ™ SK− |
| L0372 | NCI_CGAP_Co12 | colon tumor | colon | | | pBLUESCRIPT ™ SK− |

TABLE 4-continued

| Code | Description | Tissue | Organ | Cell Line | Disease | Vector |
|---|---|---|---|---|---|---|
| L0373 | NCI_CGAP_Co11 | tumor | colon | | | pBLUESCRIPT ™ SK− |
| L0374 | NCI_CGAP_Co2 | tumor | colon | | | pBLUESCRIPT ™ SK− |
| L0375 | NCI_CGAP_Kid6 | kidney tumor | kidney | | | pBLUESCRIPT ™ SK− |
| L0376 | NCI_CGAP_Lar1 | larynx | larynx | | | pBLUESCRIPT ™ SK− |
| L0377 | NCI_CGAP_HN2 | squamous cell carcinoma from vocal cord | larynx | | | pBLUESCRIPT ™ SK− |
| L0378 | NCI_CGAP_Lu1 | lung tumor | lung | | | pBLUESCRIPT ™ SK− |
| L0379 | NCI_CGAP_Lym3 | lymphoma | lymph node | | | pBLUESCRIPT ™ SK− |
| L0380 | NCI_CGAP_HN1 | squamous cell carcinoma | lymph node | | | pBLUESCRIPT ™ SK− |
| L0381 | NCI_CGAP_HN4 | squamous cell carcinoma | pharynx | | | pBLUESCRIPT ™ SK− |
| L0382 | NCI_CGAP_Pr25 | epithelium (cell line) | prostate | | | pBLUESCRIPT ™ SK− |
| L0383 | NCI_CGAP_Pr24 | invasive tumor (cell line) | prostate | | | pBLUESCRIPT ™ SK− |
| L0384 | NCI_CGAP_Pr23 | prostate tumor | prostate | | | pBLUESCRIPT ™ SK− |
| L0385 | NCI_CGAP_Gas1 | gastric tumor | stomach | | | pBLUESCRIPT ™ SK− |
| L0386 | NCI_CGAP_HN3 | squamous cell carcinoma from base of tongue | tongue | | | pBLUESCRIPT ™ SK− |
| L0387 | NCI_CGAP_GCB0 | germinal center B-cells | tonsil | | | pBLUESCRIPT ™ SK− |
| L0388 | NCI_CGAP_HN6 | normal gingiva (cell line from immortalized kerati | | | | pBLUESCRIPT ™ SK− |
| L0389 | NCI_CGAP_HN5 | normal gingiva (cell line from primary keratinocyt | | | | pBLUESCRIPT ™ SK− |
| L0393 | B, Human Liver tissue | | | | | gt11 |
| L0394 | H, Human adult Brain Cortex tissue | | | | | gt11 |
| L0404 | b4HB3MA Cot109 + 103 + 85-Bio | | | | | Lafmid A |
| L0405 | b4HB3MA Cot109 + 103-Bio | | | | | Lafmid A |
| L0411 | 1-NIB | | | | | Lafmid BA |
| L0414 | b4HB3MA | | | | | Lafmid BA |
| L0415 | b4HB3MA Cot8-HAP-Ft | | | | | Lafmid BA |
| L0416 | b4HB3MA-Cot0.38-HAP-B | | | | | Lafmid BA |
| L0417 | b4HB3MA-Cot0.38-HAP-Ft-6 | | | | | Lafmid BA |
| L0418 | b4HB3MA-Cot109 + 10-Bio | | | | | Lafmid BA |
| L0419 | b4HB3MA-Cot109 + 103 + 85-Bio | | | | | Lafmid BA |
| L0422 | b4HB3MA-Cot12-HAP-B | | | | | Lafmid BA |
| L0424 | b4HB3MA-Cot14.5 | | | | | Lafmid BA |
| L0425 | b4HB3MA-Cot18-Bio | | | | | Lafmid BA |
| L0426 | b4HB3MA-Cot51.5-HAP-Ft | | | | | Lafmid BA |
| L0427 | b4HB3MA-FT20%-Biotin | | | | | Lafmid BA |
| L0428 | Cot1374Ft-4HB3MA | | | | | Lafmid BA |
| L0430 | Cot250Ft-b4HB3MA | | | | | Lafmid BA |
| L0433 | HWM42YA | | | | | Lafmid BA |
| L0434 | Infant brain library of Dr. M. Soares | | | | | Lafmid BA |
| L0435 | Infant brain, LLNL array of Dr. M. Soares 1NIB | | | | | Lafmid BA |
| L0437 | N-b4HB3MA-Cot109 | | | | | Lafmid BA |
| L0438 | normalized infant brain cDNA | total brain | brain | | | Lafmid BA |
| L0439 | Soares infant brain 1NIB | | whole brain | | | Lafmid BA |
| L0441 | 2HB3MK | | | | | Lafmid BK |
| L0442 | 4HB3MK | | | | | Lafmid BK |
| L0443 | b4HB3MK | | | | | Lafmid BK |
| L0446 | N4HB3MK | | | | | Lafmid BK |
| L0447 | NHB3MK | | | | | Lafmid BK |
| L0448 | 3HFLSK20 | | | | | Lafmid K |
| L0451 | N3HFLSK20 | | | | | Lafmid K |
| L0453 | BATM1 | | | | | lambda gt10 |
| L0454 | CLONTECH ™ adult human fat cell library HL1108A | | | | | lambda gt10 |
| L0455 | Human retina cDNA randomly primed sublibrary | retina | eye | | | lambda gt10 |
| L0456 | Human retina cDNA Tsp509I-cleaved sublibrary | retina | eye | | | lambda gt10 |
| L0457 | multi-tissue normalized short-fragment | multi-tissue | pooled | | | lambda gt10 |
| L0459 | Adult heart, CLONTECH ™ | | | | | Lambda gt11 |
| L0460 | Adult heart, Lambda gt11 | | | | | Lambda gt11 |

TABLE 4-continued

| Code | Description | Tissue | Organ | Cell Line | Disease | Vector |
|---|---|---|---|---|---|---|
| L0462 | WATM1 | | | | | lambda gt11 |
| L0463 | fetal brain cDNA | brain | brain | | | lambda gt11 |
| L0465 | TEST1, Human adult Testis tissue | | | | | lambda nm1149 |
| L0467 | Fetal heart, Lambda ZAP Express | | | | | Lambda ZAP |
| L0468 | HE6W | | | | | lambda zap |
| L0469 | T, Human adult Rhabdomyosarcoma cell-line | | | | | Lambda Zap |
| L0470 | BL29 Burkitt"s lymphoma, Pascalis Sideras | | | | | LAMBDA ZAP ™ II |
| L0471 | Human fetal heart, LAMBDA ZAP ™ Express | | | | | LAMBDA ZAP ™ Express (STRATAGENE ™) |
| L0475 | KG1-a Lambda Zap Express cDNA library | | | KG1-a | | Lambda Zap Express (STRATAGENE ™) |
| L0476 | Fetal brain, STRATAGENE ™ | | | | | LAMBDA ZAP ™ II |
| L0477 | HPLA CCLee | placenta | | | | LAMBDA ZAP ™ II |
| L0480 | STRATAGENE ™ cat#937212 (1992) | | | | | Lambda ZAP, pBLUESCRIPT ™ SK− |
| L0481 | CD34 + DIRECTIONAL | | | | | LAMBDA ZAP ™ II |
| L0482 | HT29M6 | | | | | LAMBDA ZAP ™ II |
| L0483 | Human pancreatic islet | | | | | LAMBDA ZAP ™ II |
| L0485 | STRATAGENE ™ Human skeletal muscle cDNA library, cat. #936215. | skeletal muscle | leg muscle | | | LAMBDA ZAP ™ II |
| L0486 | Human promyelocytic HL60 cell line (S. Herblot) | | | promyelocytic HL60 cell line | | LAMBDA ZAP ™ II |
| L0487 | Human peripheral blood (Steve Elledge) | whole peripheral blood | | | | Lambda-Yes |
| L0492 | Human Genomic | | | | | pAMP |
| L0493 | NCI_CGAP_Ov26 | papillary serous carcinoma | ovary | | | pAMP1 |
| L0497 | NCI_CGAP_HSC4 | CD34+, CD38− from normal bone marrow donor | bone marrow | | | pAMP1 |
| L0498 | NCI_CGAP_HSC3 | CD34+, T negative, patient with chronic myelogenou | bone marrow | | | pAMP1 |
| L0499 | NCI_CGAP_HSC2 | stem cell 34+/38+ | bone marrow | | | pAMP1 |
| L0500 | NCI_CGAP_Brn20 | oligodendroglioma | brain | | | pAMP1 |
| L0501 | NCI_CGAP_Brn21 | oligodendroglioma | brain | | | pAMP1 |
| L0502 | NCI_CGAP_Br15 | adenocarcinoma | breast | | | pAMP1 |
| L0503 | NCI_CGAP_Br17 | adenocarcinoma | breast | | | pAMP1 |
| L0504 | NCI_CGAP_Br13 | breast carcinoma in situ | breast | | | pAMP1 |
| L0505 | NCI_CGAP_Br12 | invasive carcinoma | breast | | | pAMP1 |
| L0506 | NCI_CGAP_Br16 | lobullar carcinoma in situ | breast | | | pAMP1 |
| L0507 | NCI_CGAP_Br14 | normal epithelium | breast | | | pAMP1 |
| L0508 | NCI_CGAP_Lu25 | bronchioalveolar carcinoma | lung | | | pAMP1 |
| L0509 | NCI_CGAP_Lu26 | invasive adenocarcinoma | lung | | | pAMP1 |
| L0510 | NCI_CGAP_Ov33 | borderline ovarian carcinoma | ovary | | | pAMP1 |
| L0511 | NCI_CGAP_Ov34 | borderline ovarian carcinoma | ovary | | | pAMP1 |
| L0512 | NCI_CGAP_Ov36 | borderline ovarian carcinoma | ovary | | | pAMP1 |
| L0513 | NCI_CGAP_Ov37 | early stage papillary serous carcinoma | ovary | | | pAMP1 |
| L0514 | NCI_CGAP_Ov31 | papillary serous carcinoma | ovary | | | pAMP1 |
| L0515 | NCI_CGAP_Ov32 | papillary serous carcinoma | ovary | | | pAMP1 |
| L0516 | Chromosome 19p12-p13.1 exon | | | | | pAMP10 |
| L0517 | NCI_CGAP_Pr1 | | | | | pAMP10 |
| L0518 | NCI_CGAP_Pr2 | | | | | pAMP10 |
| L0519 | NCI_CGAP_Pr3 | | | | | pAMP10 |
| L0520 | NCI_CGAP_Alv1 | alveolar rhabdomyosarcoma | | | | pAMP10 |
| L0521 | NCI_CGAP_Ew1 | Ewing"s sarcoma | | | | pAMP10 |
| L0522 | NCI_CGAP_Kid1 | kidney | | | | pAMP10 |
| L0523 | NCI_CGAP_Lip2 | liposarcoma | | | | pAMP10 |
| L0524 | NCI_CGAP_Li1 | liver | | | | pAMP10 |
| L0525 | NCI_CGAP_Li2 | liver | | | | pAMP10 |
| L0526 | NCI_CGAP_Pr12 | metastatic prostate bone lesion | | | | pAMP10 |
| L0527 | NCI_CGAP_Ov2 | ovary | | | | pAMP10 |
| L0528 | NCI_CGAP_Pr5 | prostate | | | | pAMP10 |

TABLE 4-continued

| Code | Description | Tissue | Organ | Cell Line | Disease | Vector |
|---|---|---|---|---|---|---|
| L0529 | NCI_CGAP_Pr6 | prostate | | | | pAMP10 |
| L0530 | NCI_CGAP_Pr8 | prostate | | | | pAMP10 |
| L0531 | NCI_CGAP_Pr20 | prostate metastasis, liver | | | | pAMP10 |
| L0532 | NCI_CGAP_Thy1 | thyroid | | | | pAMP10 |
| L0533 | NCI_CGAP_HSC1 | stem cells | bone marrow | | | pAMP10 |
| L0534 | Chromosome 7 Fetal Brain cDNA Library | brain | brain | | | pAMP10 |
| L0535 | NCI_CGAP_Br5 | infiltrating ductal carcinoma | breast | | | pAMP10 |
| L0536 | NCI_CGAP_Br4 | normal ductal tissue | breast | | | pAMP10 |
| L0537 | NCI_CGAP_Ov6 | normal cortical stroma | ovary | | | pAMP10 |
| L0538 | NCI_CGAP_Ov5 | normal surface epithelium | ovary | | | pAMP10 |
| L0539 | Chromosome 7 Placental cDNA Library | | placenta | | | pAMP10 |
| L0540 | NCI_CGAP_Pr10 | invasive prostate tumor | prostate | | | pAMP10 |
| L0541 | NCI_CGAP_Pr7 | low-grade prostatic neoplasia | prostate | | | pAMP10 |
| L0542 | NCI_CGAP_Pr11 | normal prostatic epithelial cells | prostate | | | pAMP10 |
| L0543 | NCI_CGAP_Pr9 | normal prostatic epithelial cells | prostate | | | pAMP10 |
| L0544 | NCI_CGAP_Pr4 | prostatic intraepithelial neoplasia - high grade | prostate | | | pAMP10 |
| L0545 | NCI_CGAP_Pr4.1 | prostatic intraepithelial neoplasia - high grade | prostate | | | pAMP10 |
| L0546 | NCI_CGAP_Pr18 | stroma | prostate | | | pAMP10 |
| L0547 | NCI_CGAP_Pr16 | tumor | prostate | | | pAMP10 |
| L0548 | Chromosome 7 Thymus cDNA Library | thymus | thymus | | | pAMP10 |
| L0549 | NCI_CGAP_HN10 | carcinoma in situ from retromolar trigone | | | | pAMP10 |
| L0550 | NCI_CGAP_HN9 | normal squamous epithelium from retromolar trigone | | | | pAMP10 |
| L0551 | NCI_CGAP_HN7 | normal squamous epithelium, floor of mouth | | | | pAMP10 |
| L0552 | NCI_CGAP_HN8 | well-differentiated invasive carcinoma, floor of m | | | | pAMP10 |
| L0553 | NCI_CGAP_Co22 | colonic adenocarcinoma | colon | | | pAMP10 |
| L0554 | NCI_CGAP_Li8 | | liver | | | pAMP10 |
| L0555 | NCI_CGAP_Lu34 | large cell carcinoma | lung | | | pAMP10 |
| L0556 | NCI_CGAP_Lu34.1 | large cell carcinoma | lung | | | pAMP10 |
| L0557 | NCI_CGAP_Lu21 | small cell carcinoma | lung | | | pAMP10 |
| L0558 | NCI_CGAP_Ov40 | endometrioid ovarian metastasis | ovary | | | pAMP10 |
| L0559 | NCI_CGAP_Ov39 | papillary serous ovarian metastasis | ovary | | | pAMP10 |
| L0560 | NCI_CGAP_HN12 | moderate to poorly differentiated invasive carcino | tongue | | | pAMP10 |
| L0561 | NCI_CGAP_HN11 | normal squamous epithelium | tongue | | | pAMP10 |
| L0562 | Chromosome 7 HeLa cDNA Library | | | HeLa cell line; ATCC ™ | | pAMP10 |
| L0563 | Human Bone Marrow Stromal Fibroblast | bone marrow | | | | pBLUESCRIPT ™ |
| L0564 | Jia bone marrow stroma | bone marrow stroma | | | | pBLUESCRIPT ™ |
| L0565 | Normal Human Trabecular Bone Cells | Bone | Hip | | | pBLUESCRIPT ™ |
| L0579 | Human fetal brain QBoqin2 | cerebrum and cerebellum | | | | pBLUESCRIPT ™ SK |
| L0581 | STRATAGENE ™ liver (#937224) | | liver | | | pBLUESCRIPT ™ SK |
| L0583 | STRATAGENE ™ cDNA library Human fibroblast, cat#937212 | | | | | pBLUESCRIPT ™ SK |
| L0584 | STRATAGENE ™ cDNA library Human heart, cat#936208 | | | | | pBLUESCRIPT ™ SK |
| L0586 | HTCDL1 | | | | | pBLUESCRIPT ™ SK− |
| L0587 | STRATAGENE ™ colon HT29 (#937221) | | | | | pBLUESCRIPT ™ SK− |
| L0588 | STRATAGENE ™ endothelial cell 937223 | | | | | pBLUESCRIPT ™ SK− |
| L0589 | STRATAGENE ™ fetal retina 937202 | | | | | pBLUESCRIPT ™ SK− |
| L0590 | STRATAGENE ™ fibroblast (#937212) | | | | | pBLUESCRIPT ™ SK− |

TABLE 4-continued

| Code | Description | Tissue | Organ | Cell Line | Disease | Vector |
|---|---|---|---|---|---|---|
| L0591 | STRATAGENE ™ HeLa cell s3 937216 | | | | | pBLUESCRIPT ™ SK− |
| L0592 | STRATAGENE ™ hNT neuron (#937233) | | | | | pBLUESCRIPT ™ SK− |
| L0593 | STRATAGENE ™ neuroepithelium (#937231) | | | | | pBLUESCRIPT ™ SK− |
| L0594 | STRATAGENE ™ neuroepithelium NT2RAMI 937234 | | | | | pBLUESCRIPT ™ SK− |
| L0595 | STRATAGENE ™ NT2 neuronal precursor 937230 | neuroepithelial cells | brain | | | pBLUESCRIPT ™ SK− |
| L0596 | STRATAGENE ™ colon (#937204) | | colon | | | pBLUESCRIPT ™ SK− |
| L0597 | STRATAGENE ™ corneal stroma (#937222) | | cornea | | | pBLUESCRIPT ™ SK− |
| L0598 | Morton Fetal Cochlea | cochlea | ear | | | pBLUESCRIPT ™ SK− |
| L0599 | STRATAGENE ™ lung (#937210) | | lung | | | pBLUESCRIPT ™ SK− |
| L0600 | Weizmann Olfactory Epithelium | olfactory epithelium | nose | | | pBLUESCRIPT ™ SK− |
| L0601 | STRATAGENE ™ pancreas (#937208) | | pancreas | | | pBLUESCRIPT ™ SK− |
| L0602 | Pancreatic Islet | pancreatic islet | pancreas | | | pBLUESCRIPT ™ SK− |
| L0603 | STRATAGENE ™ placenta (#937225) | | placenta | | | pBLUESCRIPT ™ SK− |
| L0604 | STRATAGENE ™ muscle 937209 | muscle | skeletal muscle | | | pBLUESCRIPT ™ SK− |
| L0605 | STRATAGENE ™ fetal spleen (#937205) | fetal spleen | spleen | | | pBLUESCRIPT ™ SK− |
| L0606 | NCI_CGAP_Lym5 | follicular lymphoma | lymph node | | | pBLUESCRIPT ™ SK− |
| L0607 | NCI_CGAP_Lym6 | mantle cell lymphoma | lymph node | | | pBLUESCRIPT ™ SK− |
| L0608 | STRATAGENE ™ lung carcinoma 937218 | lung carcinoma | lung | NCI-H69 | | pBLUESCRIPT ™ SK− |
| L0609 | Schiller astrocytoma | astrocytoma | brain | | | pBLUESCRIPT ™ SK− (STRATAGENE ™) |
| L0610 | Schiller glioblastoma multiforme | glioblastoma multiforme | brain | | | pBLUESCRIPT ™ SK− (STRATAGENE ™) |
| L0611 | Schiller meningioma | meningioma | brain | | | pBLUESCRIPT ™ SK− (STRATAGENE ™) |
| L0612 | Schiller oligodendroglioma | oligodendroglioma | brain | | | pBLUESCRIPT ™ SK− (STRATAGENE ™) |
| L0615 | 22 week old human fetal liver cDNA library | | | | | pBLUESCRIPT ™ II SK− |
| L0616 | Chromosome 21 exon | | | | | pBLUESCRIPT ™ IIKS+ |
| L0617 | Chromosome 22 exon | | | | | pBLUESCRIPT ™ IIKS+ |
| L0618 | Chromosome 9 exon | | | | | pBLUESCRIPT ™ IIKS+ |
| L0619 | Chromosome 9 exon II | | | | | pBLUESCRIPT ™ IIKS+ |
| L0622 | HM1 | | | | | pcDNAII (Invitrogen) |
| L0623 | HM3 | pectoral muscle (after mastectomy) | | | | pcDNAII (Invitrogen) |
| L0625 | NCI_CGAP_AR1 | bulk alveolar tumor | | | | pCMV-SPORT2 |
| L0626 | NCI_CGAP_GC1 | bulk germ cell seminoma | | | | pCMV-SPORT2 |
| L0627 | NCI_CGAP_Co1 | bulk tumor | colon | | | pCMV-SPORT2 |
| L0628 | NCI_CGAP_Ov1 | ovary bulk tumor | ovary | | | pCMV-SPORT2 |
| L0629 | NCI_CGAP_Mel3 | metastatic melanoma to bowel | bowel (skin primary) | | | pCMV-SPORT4 |
| L0630 | NCI_CGAP_CNS1 | substantia nigra | brain | | | pCMV-SPORT4 |
| L0631 | NCI_CGAP_Br7 | | breast | | | pCMV-SPORT4 |

TABLE 4-continued

| Code | Description | Tissue | Organ | Cell Line | Disease | Vector |
|---|---|---|---|---|---|---|
| L0632 | NCI_CGAP_Li5 | hepatic adenoma | liver | | | pCMV-SPORT4 |
| L0633 | NCI_CGAP_Lu6 | small cell carcinoma | lung | | | pCMV-SPORT4 |
| L0634 | NCI_CGAP_Ov8 | serous adenocarcinoma | ovary | | | pCMV-SPORT4 |
| L0635 | NCI_CGAP_PNS1 | dorsal root ganglion | peripheral nervous system | | | pCMV-SPORT4 |
| L0636 | NCI_CGAP_Pit1 | four pooled pituitary adenomas | brain | | | pCMV-SPORT6 (LIFE TECHNOLOGIES ™) |
| L0637 | NCI_CGAP_Brn53 | three pooled meningiomas | brain | | | pCMV-SPORT6 (LIFE TECHNOLOGIES ™) |
| L0638 | NCI_CGAP_Brn35 | tumor, 5 pooled (see description) | brain | | | pCMV-SPORT6 (LIFE TECHNOLOGIES ™) |
| L0639 | NCI_CGAP_Brn52 | tumor, 5 pooled (see description) | brain | | | pCMV-SPORT6 (LIFE TECHNOLOGIES ™) |
| L0640 | NCI_CGAP_Br18 | four pooled high-grade tumors, including two prima | breast | | | pCMV-SPORT6 (LIFE TECHNOLOGIES ™) |
| L0641 | NCI_CGAP_Co17 | juvenile granulosa tumor | colon | | | pCMV-SPORT6 (LIFE TECHNOLOGIES ™) |
| L0642 | NCI_CGAP_Co18 | moderately differentiated adenocarcinoma | colon | | | pCMV-SPORT6 (LIFE TECHNOLOGIES ™) |
| L0643 | NCI_CGAP_Co19 | moderately differentiated adenocarcinoma | colon | | | pCMV-SPORT6 (LIFE TECHNOLOGIES ™) |
| L0644 | NCI_CGAP_Co20 | moderately differentiated adenocarcinoma | colon | | | pCMV-SPORT6 (LIFE TECHNOLOGIES ™) |
| L0645 | NCI_CGAP_Co21 | moderately differentiated adenocarcinoma | colon | | | pCMV-SPORT6 (LIFE TECHNOLOGIES ™) |
| L0646 | NCI_CGAP_Co14 | moderately-differentiated adenocarcinoma | colon | | | pCMV-SPORT6 (LIFE TECHNOLOGIES ™) |
| L0647 | NCI_CGAP_Sar4 | five pooled sarcomas, including myxoid liposarcoma | connective tissue | | | pCMV-SPORT6 (LIFE TECHNOLOGIES ™) |
| L0648 | NCI_CGAP_Eso2 | squamous cell carcinoma | esophagus | | | pCMV-SPORT6 (LIFE TECHNOLOGIES ™) |
| L0649 | NCI_CGAP_GU1 | 2 pooled high-grade transitional cell tumors | genitourinary tract | | | pCMV-SPORT6 (LIFE TECHNOLOGIES ™) |
| L0650 | NCI_CGAP_Kid13 | 2 pooled Wilms'' tumors, one primary and one metast | kidney | | | pCMV-SPORT6 (LIFE TECHNOLOGIES ™) |
| L0651 | NCI_CGAP_Kid8 | renal cell tumor | kidney | | | pCMV-SPORT6 (LIFE TECHNOLOGIES ™) |
| L0652 | NCI_CGAP_Lu27 | four pooled poorly-differentiated adenocarcinomas | lung | | | pCMV-SPORT6 (LIFE TECHNOLOGIES ™) |
| L0653 | NCI_CGAP_Lu28 | two pooled squamous cell carcinomas | lung | | | pCMV-SPORT6 (LIFE TECHNOLOGIES ™) |
| L0654 | NCI_CGAP_Lu31 | | lung, cell line | | | pCMV-SPORT6 (LIFE TECHNOLOGIES ™) |
| L0655 | NCI_CGAP_Lym12 | lymphoma, follicular mixed small and large cell | lymph node | | | pCMV-SPORT6 (LIFE TECHNOLOGIES ™) |
| L0656 | NCI_CGAP_Ov38 | normal epithelium | ovary | | | pCMV-SPORT6 (LIFE TECHNOLOGIES ™) |
| L0657 | NCI_CGAP_Ov23 | tumor, 5 pooled (see description) | ovary | | | pCMV-SPORT6 (LIFE TECHNOLOGIES ™) |
| L0658 | NCI_CGAP_Ov35 | tumor, 5 pooled (see description) | ovary | | | pCMV-SPORT6 (LIFE TECHNOLOGIES ™) |

TABLE 4-continued

| Code | Description | Tissue | Organ | Cell Line | Disease | Vector |
|---|---|---|---|---|---|---|
| L0659 | NCI_CGAP_Pan1 | adenocarcinoma | pancreas | | | pCMV-SPORT6 (LIFE TECHNOLOGIES ™) |
| L0661 | NCI_CGAP_Mel15 | malignant melanoma, metastatic to lymph node | skin | | | pCMV-SPORT6 (LIFE TECHNOLOGIES ™) |
| L0662 | NCI_CGAP_Gas4 | poorly differentiated adenocarcinoma with signet r | stomach | | | pCMV-SPORT6 (LIFE TECHNOLOGIES ™) |
| L0663 | NCI_CGAP_Ut2 | moderately-differentiated endometrial adenocarcino | uterus | | | pCMV-SPORT6 (LIFE TECHNOLOGIES ™) |
| L0664 | NCI_CGAP_Ut3 | poorly-differentiated endometrial adenocarcinoma, | uterus | | | pCMV-SPORT6 (LIFE TECHNOLOGIES ™) |
| L0665 | NCI_CGAP_Ut4 | serous papillary carcinoma, high grade, 2 pooled t | uterus | | | pCMV-SPORT6 (LIFE TECHNOLOGIES ™) |
| L0666 | NCI_CGAP_Ut1 | well-differentiated endometrial adenocarcinoma, 7 | uterus | | | pCMV-SPORT6 (LIFE TECHNOLOGIES ™) |
| L0667 | NCI_CGAP_CML1 | myeloid cells, 18 pooled CML cases, BCR/ABL rearra | whole blood | | | pCMV-SPORT6 (LIFE TECHNOLOGIES ™) |
| L0669 | Human MCF7 cDNA subtracted with MDA-MB-231 cDNA | breast adenocarcinoma | breast | MCF7 | | pCR II [Invitrogen] |
| L0681 | Stanley Frontal SN individual | frontal lobe (see description) | brain | | | pCR2.1 (Invitrogen) |
| L0682 | Stanley Frontal NB pool 2 | frontal lobe (see description) | brain | | | pCR2.1-TOPO (Invitrogen) |
| L0683 | Stanley Frontal NS pool 2 | frontal lobe (see description) | brain | | | pCR2.1-TOPO (Invitrogen) |
| L0684 | Stanley Frontal SB pool 1 | frontal lobe (see description) | brain | | | pCR2.1-TOPO (Invitrogen) |
| L0685 | Stanley Frontal SN pool 1 | frontal lobe (see description) | brain | | | pCR2.1-TOPO (Invitrogen) |
| L0686 | Stanley Frontal SN pool 2 | frontal lobe (see description) | brain | | | pCR2.1-TOPO (Invitrogen) |
| L0687 | Stanley Hippocampus NB pool 1 | hippocampus (see description) | brain | | | pCR2.1-TOPO (Invitrogen) |
| L0688 | Stanley Hippocampus SB pool 1 | hippocampus (see description) | brain | | | pCR2.1-TOPO (Invitrogen) |
| L0689 | Stanley Hippocampus SN pool 1 | hippocampus (see description) | brain | | | pCR2.1-TOPO (Invitrogen) |
| L0690 | Testis, Subtracted | | | | | pCR II [Invitrogen] |
| L0695 | Human Glialblastoma Cell | | Brain | BT-325 | | pCR II [Invitrogen] |
| L0697 | Testis 1 | | | | | PGEM 5zf(+) |
| L0698 | Testis 2 | | | | | PGEM 5zf(+) |
| L0700 | Outward Alu-primed hncDNA library | | | | | pGEM-3Z |
| L0708 | NIH_MGC_17 | rhabdomyosarcoma | muscle | | | pOTB7 |
| L0709 | NIH_MGC_21 | choriocarcinoma | placenta | | | pOTB7 |
| L0710 | NIH_MGC_7 | small cell carcinoma | lung | MGC3 | | pOTB7 |
| L0716 | PMA-induced HL60 cell subtraction library | | | PMA-induced HL60 human leukemic cell line | | pSport1 |
| L0717 | Gessler Wilms tumor | | | | | pSport1 |
| L0718 | Testis 5 | | | | | pSport1 |
| L0719 | human embryo cDNA library | Whole embryo | | | | pSport1 |
| L0720 | PN001-Normal Human Prostate | | prostate | | | pSport1 |
| L0731 | Soares_pregnant_uterus_NbHPU | | uterus | | | pT7T3-Pac |
| L0738 | Human colorectal cancer | | | | | pT7T3D |
| L0740 | Soares melanocyte 2NbHM | melanocyte | | | | pT7T3D (PHARMACIA ™) with a modified polylinker |
| L0741 | Soares adult brain N2b4HB55Y | | brain | | | pT7T3D (PHARMACIA ™) with a modified polylinker |
| L0742 | Soares adult brain N2b5HB55Y | | brain | | | pT7T3D (PHARMACIA ™) with a |

TABLE 4-continued

| Code | Description | Tissue | Organ | Cell Line | Disease | Vector |
|---|---|---|---|---|---|---|
| | | | | | | modified polylinker |
| L0743 | Soares breast 2NbHBst | | breast | | | pT7T3D (PHARMACIA ™) with a modified polylinker |
| L0744 | Soares breast 3NbHBst | | breast | | | pT7T3D (PHARMACIA ™) with a modified polylinker |
| L0745 | Soares retina N2b4HR | retina | eye | | | pT7T3D (PHARMACIA ™) with a modified polylinker |
| L0746 | Soares retina N2b5HR | retina | eye | | | pT7T3D (PHARMACIA ™) with a modified polylinker |
| L0747 | Soares_fetal_heart_NbHH19W | | heart | | | pT7T3D (PHARMACIA ™) with a modified polylinker |
| L0748 | Soares fetal liver spleen 1NFLS | | Liver and Spleen | | | pT7T3D (PHARMACIA ™) with a modified polylinker |
| L0749 | Soares_fetal_liver_ spleen_1NFLS_S1 | | Liver and Spleen | | | pT7T3D (PHARMACIA ™) with a modified polylinker |
| L0750 | Soares_fetal_lung_NbHL19W | | lung | | | pT7T3D (PHARMACIA ™) with a modified polylinker |
| L0751 | Soares ovary tumor NbHOT | ovarian tumor | ovary | | | pT7T3D (PHARMACIA ™) with a modified polylinker |
| L0752 | Soares_parathyroid_tumor_NbHPA | parathyroid tumor | parathyroid gland | | | pT7T3D (PHARMACIA ™) with a modified polylinker |
| L0753 | Soares_pineal_gland_N3HPG | | pineal gland | | | pT7T3D (PHARMACIA ™) with a modified polylinker |
| L0754 | Soares placenta Nb2HP | | placenta | | | pT7T3D (PHARMACIA ™) with a modified polylinker |
| L0755 | Soares_placenta_8to9weeks_ 2NbHP8to9W | | placenta | | | pT7T3D (PHARMACIA ™) with a modified polylinker |
| L0756 | Soares_multiple_sclerosis_ 2NbHMSP | multiple sclerosis lesions | | | | pT7T3D (PHARMACIA ™) with a modified polylinker V_TYPE |
| L0757 | Soares_senescent_fibroblasts_Nb HSF | senescent fibroblast | | | | pT7T3D (PHARMACIA ™) with a modified |

TABLE 4-continued

| Code | Description | Tissue | Organ | Cell Line | Disease | Vector |
|---|---|---|---|---|---|---|
| | | | | | | polylinker V_TYPE |
| L0758 | Soares_testis_NHT | | | | | pT7T3D-Pac (PHARMACIA ™) with a modified polylinker |
| L0759 | Soares_total_fetus_Nb2HF8_9w | | | | | pT7T3D-Pac (PHARMACIA ™) with a modified polylinker |
| L0760 | Barstead aorta HPLRB3 | aorta | | | | pT7T3D-Pac (PHARMACIA ™) with a modified polylinker |
| L0761 | NCI_CGAP_CLL1 | B-cell, chronic lymphotic leukemia | | | | pT7T3D-Pac (PHARMACIA ™) with a modified polylinker |
| L0762 | NCI_CGAP_Br1.1 | breast | | | | pT7T3D-Pac (PHARMACIA ™) with a modified polylinker |
| L0763 | NCI_CGAP_Br2 | breast | | | | pT7T3D-Pac (PHARMACIA ™) with a modified polylinker |
| L0764 | NCI_CGAP_Co3 | colon | | | | pT7T3D-Pac (PHARMACIA ™) with a modified polylinker |
| L0765 | NCI_CGAP_Co4 | colon | | | | pT7T3D-Pac (PHARMACIA ™) with a modified polylinker |
| L0766 | NCI_CGAP_GCB1 | germinal center B cell | | | | pT7T3D-Pac (PHARMACIA ™) with a modified polylinker |
| L0767 | NCI_CGAP_GC3 | pooled germ cell tumors | | | | pT7T3D-Pac (PHARMACIA ™) with a modified polylinker |
| L0768 | NCI_CGAP_GC4 | pooled germ cell tumors | | | | pT7T3D-Pac (PHARMACIA ™) with a modified polylinker |
| L0769 | NCI_CGAP_Brn25 | anaplastic oligodendroglioma | brain | | | pT7T3D-Pac (PHARMACIA ™) with a modified polylinker |
| L0770 | NCI_CGAP_Brn23 | glioblastoma (pooled) | brain | | | pT7T3D-Pac (PHARMACIA ™) with a modified polylinker |
| L0771 | NCI_CGAP_Co8 | adenocarcinoma | colon | | | pT7T3D-Pac (PHARMACIA ™) with a modified polylinker |
| L0772 | NCI_CGAP_Co10 | colon tumor RER+ | colon | | | pT7T3D-Pac (PHARMACIA ™) with a modified polylinker |

TABLE 4-continued

| Code | Description | Tissue | Organ | Cell Line | Disease | Vector |
|---|---|---|---|---|---|---|
| L0773 | NCI_CGAP_Co9 | colon tumor RER+ | colon | | | pT7T3D-Pac (PHARMACIA ™) with a modified polylinker |
| L0774 | NCI_CGAP_Kid3 | | kidney | | | pT7T3D-Pac (PHARMACIA ™) with a modified polylinker |
| L0775 | NCI_CGAP_Kid5 | 2 pooled tumors (clear cell type) | kidney | | | pT7T3D-Pac (PHARMACIA ™) with a modified polylinker |
| L0776 | NCI_CGAP_Lu5 | carcinoid | lung | | | pT7T3D-Pac (PHARMACIA ™) with a modified polylinker |
| L0777 | Soares_NhHMPu_S1 | Pooled human melanocyte, fetal heart, and pregnant | mixed (see below) | | | pT7T3D-Pac (PHARMACIA ™) with a modified polylinker |
| L0778 | Barstead pancreas HPLRB1 | | pancreas | | | pT7T3D-Pac (PHARMACIA ™) with a modified polylinker |
| L0779 | Soares_NFL_T_GBC_S1 | | pooled | | | pT7T3D-Pac (PHARMACIA ™) with a modified polylinker |
| L0780 | Soares_NSF_F8_ 9W_OT_PA_P_S1 | | pooled | | | pT7T3D-Pac (PHARMACIA ™) with a modified polylinker |
| L0782 | NCI_CGAP_Pr21 | normal prostate | prostate | | | pT7T3D-Pac (PHARMACIA ™) with a modified polylinker |
| L0783 | NCI_CGAP_Pr22 | normal prostate | prostate | | | pT7T3D-Pac (PHARMACIA ™) with a modified polylinker |
| L0784 | NCI_CGAP_Lei2 | leiomyosarcoma | soft tissue | | | pT7T3D-Pac (PHARMACIA ™) with a modified polylinker |
| L0785 | Barstead spleen HPLRB2 | | spleen | | | pT7T3D-Pac (PHARMACIA ™) with a modified polylinker |
| L0786 | Soares_NbHFB | | whole brain | | | pT7T3D-Pac (PHARMACIA ™) with a modified polylinker |
| L0787 | NCI_CGAP_Sub1 | | | | | pT7T3D-Pac (PHARMACIA ™) with a modified polylinker |
| L0788 | NCI_CGAP_Sub2 | | | | | pT7T3D-Pac (PHARMACIA ™) with a modified polylinker |
| L0789 | NCI_CGAP_Sub3 | | | | | pT7T3D-Pac (PHARMACIA ™) with a |

TABLE 4-continued

| Code | Description | Tissue | Organ | Cell Line | Disease | Vector |
|---|---|---|---|---|---|---|
| | | | | | | modified polylinker |
| L0790 | NCI_CGAP_Sub4 | | | | | pT7T3D-Pac (PHARMACIA ™) with a modified polylinker |
| L0791 | NCI_CGAP_Sub5 | | | | | pT7T3D-Pac (PHARMACIA ™) with a modified polylinker |
| L0792 | NCI_CGAP_Sub6 | | | | | pT7T3D-Pac (PHARMACIA ™) with a modified polylinker |
| L0793 | NCI_CGAP_Sub7 | | | | | pT7T3D-Pac (PHARMACIA ™) with a modified polylinker |
| L0794 | NCI_CGAP_GC6 | pooled germ cell tumors | | | | pT7T3D-Pac (PHARMACIA ™) with a modified polylinker |
| L0796 | NCI_CGAP_Brn50 | medulloblastoma | brain | | | pT7T3D-Pac (PHARMACIA ™) with a modified polylinker |
| L0800 | NCI_CGAP_Co16 | colon tumor, RER+ | colon | | | pT7T3D-Pac (PHARMACIA ™) with a modified polylinker |
| L0803 | NCI_CGAP_Kid11 | | kidney | | | pT7T3D-Pac (PHARMACIA ™) with a modified polylinker |
| L0804 | NCI_CGAP_Kid12 | 2 pooled tumors (clear cell type) | kidney | | | pT7T3D-Pac (PHARMACIA ™) with a modified polylinker |
| L0805 | NCI_CGAP_Lu24 | carcinoid | lung | | | pT7T3D-Pac (PHARMACIA ™) with a modified polylinker |
| L0806 | NCI_CGAP_Lu19 | squamous cell carcinoma, poorly differentiated (4 | lung | | | pT7T3D-Pac (PHARMACIA ™) with a modified polylinker |
| L0807 | NCI_CGAP_Ov18 | fibrotheoma | ovary | | | pT7T3D-Pac (PHARMACIA ™) with a modified polylinker |
| L0808 | Barstead prostate BPH HPLRB41 | | prostate | | | pT7T3D-Pac (PHARMACIA ™) with a modified polylinker |
| L0809 | NCI_CGAP_Pr28 | | prostate | | | pT7T3D-Pac (PHARMACIA ™) with a modified polylinker |
| L0811 | BATM2 | | | | | PTZ18 |
| L0879 | BT0254 | | breast | | | puc18 |
| L0930 | BT0314 | | breast | | | puc18 |
| L0946 | BT0333 | | breast | | | puc18 |
| L0988 | BT0387 | | breast | | | puc18 |
| L1057 | BT0559 | | breast | | | puc18 |

TABLE 4-continued

| Code | Description | Tissue | Organ | Cell Line | Disease | Vector |
|---|---|---|---|---|---|---|
| L1278 | BN0005 | | breast_normal | | | puc18 |
| L1430 | CT0225 | | colon | | | puc18 |
| L1441 | CT0249 | | colon | | | puc18 |
| L1446 | CT0254 | | colon | | | puc18 |
| L1477 | CT0297 | | colon | | | puc18 |
| L1499 | CT0322 | | colon | | | puc18 |
| L1548 | CN0007 | | colon_normal | | | puc18 |
| L1561 | CN0026 | | colon_normal | | | puc18 |
| L1562 | CN0027 | | colon_normal | | | puc18 |
| L1607 | DT0041 | | denis_drash | | | puc18 |
| L1651 | HT0059 | | head_neck | | | puc18 |
| L1727 | HT0158 | | head_neck | | | puc18 |
| L1788 | HT0229 | | head_neck | | | puc18 |
| L1819 | HT0268 | | head_neck | | | puc18 |
| L1872 | HT0335 | | head_neck | | | puc18 |
| L1877 | HT0340 | | head_neck | | | puc18 |
| L1878 | HT0342 | | head_neck | | | puc18 |
| L1886 | HT0350 | | head_neck | | | puc18 |
| L1894 | HT0366 | | head_neck | | | puc18 |
| L1942 | HT0452 | | head_neck | | | puc18 |
| L1948 | HT0470 | | head_neck | | | puc18 |
| L2094 | ST0125 | | stomach | | | puc18 |
| L2138 | ST0186 | | stomach | | | puc18 |
| L2174 | ST0240 | | stomach | | | puc18 |
| L2197 | ST0278 | | stomach | | | puc18 |
| L2210 | ST0293 | | stomach | | | puc18 |
| L2242 | subtracted 3" EST library | | pancreas | AsPC-1(ATCC ™:CRL-1682) | | pUC18 |
| L2245 | NEM subtracted human fetal kidney cDNA | | | | | pUEX1 |
| L2250 | Human cerebral cortex | cerebral cortex | | | | |
| L2251 | Human fetal lung | Fetal lung | | | | |
| L2252 | Human placenta | placenta | | | | |
| L2255 | GLC | corresponding non cancerous liver tissue | | | | pBLUESCRIPT ™ SK− |
| L2257 | NIH_MGC_65 | adenocarcinoma | colon | | | pCMV-SPORT6 (LIFE TECHNOLOGIES ™) |
| L2258 | NIH_MGC_67 | retinoblastoma | eye | | | pCMV-SPORT6 (LIFE TECHNOLOGIES ™) |
| L2259 | NIH_MGC_68 | large cell carcinoma | lung | | | pCMV-SPORT6 (LIFE TECHNOLOGIES ™) |
| L2260 | NIH_MGC_69 | large cell carcinoma, undifferentiated | lung | | | pCMV-SPORT6 (LIFE TECHNOLOGIES ™) |
| L2261 | NIH_MGC_70 | epithelioid carcinoma | pancreas | | | pCMV-SPORT6 (LIFE TECHNOLOGIES ™) |
| L2262 | NIH_MGC_72 | melanotic melanoma | skin | | | pCMV-SPORT6 (LIFE TECHNOLOGIES ™) |
| L2263 | NIH_MGC_66 | adenocarcinoma | ovary | | | pCMV-SPORT6 (LIFE TECHNOLOGIES ™) |
| L2264 | NIH_MGC_71 | leiomyosarcoma | uterus | | | pCMV-SPORT6 (LIFE TECHNOLOGIES ™) |
| L2265 | NIH_MGC_39 | adenocarcinoma | pancreas | | | pOTB7 |
| L2269 | NCI_CGAP_Thy11 | follicular carcinoma | thyroid | | | pAMP10 |
| L2270 | Lupski_dorsal_root_ganglion | dorsal root ganglia | | | | pCMV-SPORT6 (LIFE TECHNOLOGIES ™) |
| L2277 | BT0626 | | breast | | | puc18 |
| L2279 | BT0659 | | breast | | | puc18 |
| L2281 | BT0701 | | breast | | | puc18 |
| L2283 | BT0705 | | breast | | | puc18 |
| L2285 | BT0723 | | breast | | | puc18 |
| L2289 | BT0757 | | breast | | | puc18 |
| L2291 | BT0760 | | breast | | | puc18 |
| L2293 | BT0762 | | breast | | | puc18 |
| L2294 | BT0763 | | breast | | | puc18 |
| L2300 | BT0789 | | breast | | | puc18 |
| L2301 | BT0792 | | breast | | | puc18 |
| L2308 | CT0383 | | colon | | | puc18 |
| L2317 | CT0400 | | colon | | | puc18 |

TABLE 4-continued

| Code | Description | Tissue | Organ | Cell Line | Disease | Vector |
|---|---|---|---|---|---|---|
| L2323 | CT0406 | | colon | | | puc18 |
| L2328 | CT0412 | | colon | | | puc18 |
| L2332 | CT0416 | | colon | | | puc18 |
| L2333 | CT0417 | | colon | | | puc18 |
| L2336 | CT0428 | | colon | | | puc18 |
| L2338 | CT0432 | | colon | | | puc18 |
| L2339 | CT0434 | | colon | | | puc18 |
| L2346 | CT0483 | | colon | | | puc18 |
| L2348 | CT0491 | | colon | | | puc18 |
| L2352 | UT0001 | | uterus_tumor | | | puc18 |
| L2353 | UT0003 | | uterus_tumor | | | puc18 |
| L2354 | UT0005 | | uterus_tumor | | | puc18 |
| L2357 | UT0021 | | uterus_tumor | | | puc18 |
| L2359 | UT0023 | | uterus_tumor | | | puc18 |
| L2361 | UT0028 | | uterus_tumor | | | puc18 |
| L2364 | UT0033 | | uterus_tumor | | | puc18 |
| L2367 | UT0039 | | uterus_tumor | | | puc18 |
| L2368 | UT0041 | | uterus_tumor | | | puc18 |
| L2372 | NN0034 | | nervous_normal | | | puc18 |
| L2377 | NN0054 | | nervous_normal | | | puc18 |
| L2380 | NN0068 | | nervous_normal | | | puc18 |
| L2381 | NN0070 | | nervous_normal | | | puc18 |
| L2382 | NN0073 | | nervous_normal | | | puc18 |
| L2389 | NN0087 | | nervous_normal | | | puc18 |
| L2400 | NN0116 | | nervous_normal | | | puc18 |
| L2402 | NN0118 | | nervous_normal | | | puc18 |
| L2412 | NN0136 | | nervous_normal | | | puc18 |
| L2413 | NN0141 | | nervous_normal | | | puc18 |
| L2439 | NN1022 | | nervous_normal | | | puc18 |
| L2440 | NN1023 | | nervous_normal | | | puc18 |
| L2449 | NN1063 | | nervous_normal | | | puc18 |
| L2450 | NN1065 | | nervous_normal | | | puc18 |
| L2462 | NN1089 | | nervous_normal | | | puc18 |
| L2464 | NN1104 | | nervous_normal | | | puc18 |
| L2466 | NN1111 | | nervous_normal | | | puc18 |
| L2467 | NN1112 | | nervous_normal | | | puc18 |
| L2471 | NN1123 | | nervous_normal | | | puc18 |
| L2472 | NN1124 | | nervous_normal | | | puc18 |
| L2477 | HT0408 | | head_neck | | | puc18 |
| L2478 | HT0445 | | head_neck | | | puc18 |
| L2482 | HT0497 | | head_neck | | | puc18 |
| L2486 | HT0527 | | head_neck | | | puc18 |
| L2487 | HT0542 | | head_neck | | | puc18 |
| L2490 | HT0545 | | head_neck | | | puc18 |
| L2491 | HT0559 | | head_neck | | | puc18 |
| L2493 | HT0576 | | head_neck | | | puc18 |
| L2494 | HT0577 | | head_neck | | | puc18 |
| L2495 | HT0594 | | head_neck | | | puc18 |
| L2497 | HT0618 | | head_neck | | | puc18 |
| L2498 | HT0619 | | head_neck | | | puc18 |
| L2499 | HT0622 | | head_neck | | | puc18 |
| L2500 | HT0623 | | head_neck | | | puc18 |
| L2504 | HT0636 | | head_neck | | | puc18 |
| L2506 | HT0638 | | head_neck | | | puc18 |
| L2513 | HT0678 | | head_neck | | | puc18 |
| L2518 | HT0697 | | head_neck | | | puc18 |
| L2519 | HT0698 | | head_neck | | | puc18 |
| L2521 | HT0702 | | head_neck | | | puc18 |
| L2522 | HT0704 | | head_neck | | | puc18 |
| L2525 | HT0710 | | head_neck | | | puc18 |
| L2528 | HT0713 | | head_neck | | | puc18 |
| L2535 | HT0723 | | head_neck | | | puc18 |
| L2539 | HT0727 | | head_neck | | | puc18 |
| L2540 | HT0728 | | head_neck | | | puc18 |
| L2543 | HT0734 | | head_neck | | | puc18 |
| L2545 | HT0736 | | head_neck | | | puc18 |
| L2550 | HT0743 | | head_neck | | | puc18 |
| L2551 | HT0744 | | head_neck | | | puc18 |
| L2552 | HT0745 | | head_neck | | | puc18 |
| L2558 | HT0756 | | head_neck | | | puc18 |
| L2560 | HT0758 | | head_neck | | | puc18 |
| L2562 | HT0760 | | head_neck | | | puc18 |
| L2565 | HT0764 | | head_neck | | | puc18 |
| L2570 | HT0771 | | head_neck | | | puc18 |
| L2571 | HT0773 | | head_neck | | | puc18 |
| L2578 | HT0785 | | head_neck | | | puc18 |
| L2581 | HT0790 | | head_neck | | | puc18 |
| L2587 | HT0797 | | head_neck | | | puc18 |

TABLE 4-continued

| Code | Description | Tissue | Organ | Cell Line | Disease | Vector |
|---|---|---|---|---|---|---|
| L2596 | HT0807 | | head_neck | | | puc18 |
| L2598 | HT0809 | | head_neck | | | puc18 |
| L2599 | HT0810 | | head_neck | | | puc18 |
| L2610 | HT0837 | | head_neck | | | puc18 |
| L2615 | HT0843 | | head_neck | | | puc18 |
| L2618 | HT0847 | | head_neck | | | puc18 |
| L2630 | HT0865 | | head_neck | | | puc18 |
| L2634 | HT0872 | | head_neck | | | puc18 |
| L2635 | HT0875 | | head_neck | | | puc18 |
| L2637 | HT0877 | | head_neck | | | puc18 |
| L2638 | HT0878 | | head_neck | | | puc18 |
| L2640 | HT0881 | | head_neck | | | puc18 |
| L2644 | HT0886 | | head_neck | | | puc18 |
| L2647 | HT0894 | | head_neck | | | puc18 |
| L2649 | HT0905 | | head_neck | | | puc18 |
| L2650 | HT0934 | | head_neck | | | puc18 |
| L2651 | NIH_MGC_20 | melanotic melanoma | skin | | | pOTB7 |
| L2652 | NIH_MGC_57 | glioblastoma | brain | | | pDNR-LIB (CLONTECH ™) |
| L2653 | NIH_MGC_58 | hypernephroma | kidney | | | pDNR-LIB (CLONTECH ™) |
| L2654 | NIH_MGC_9 | adenocarcinoma cell line | ovary | | | pOTB7 |
| L2655 | NIH_MGC_55 | from acute myelogenous leukemia | bone marrow | | | pDNR-LIB (CLONTECH ™) |
| L2657 | NIH_MGC_54 | from chronic myelogenous leukemia | bone marrow | | | pDNR-LIB (CLONTECH ™) |
| L2667 | NT0013 | | nervous_tumor | | | puc18 |
| L2668 | NT0018 | | nervous_tumor | | | puc18 |
| L2669 | NT0022 | | nervous_tumor | | | puc18 |
| L2670 | NT0023 | | nervous_tumor | | | puc18 |
| L2671 | NT0024 | | nervous_tumor | | | puc18 |
| L2673 | NT0028 | | nervous_tumor | | | puc18 |
| L2674 | NT0029 | | nervous_tumor | | | puc18 |
| L2675 | NT0033 | | nervous_tumor | | | puc18 |
| L2677 | NT0039 | | nervous_tumor | | | puc18 |
| L2681 | NT0048 | | nervous_tumor | | | puc18 |
| L2683 | NT0053 | | nervous_tumor | | | puc18 |
| L2686 | NT0058 | | nervous_tumor | | | puc18 |
| L2689 | NT0073 | | nervous_tumor | | | puc18 |
| L2696 | NT0084 | | nervous_tumor | | | puc18 |
| L2702 | NT0098 | | nervous_tumor | | | puc18 |
| L2705 | NT0101 | | nervous_tumor | | | puc18 |
| L2706 | NT0102 | | nervous_tumor | | | puc18 |
| L2708 | NT0104 | | nervous_tumor | | | puc18 |
| L2709 | NT0105 | | nervous_tumor | | | puc18 |
| L2716 | NT0117 | | nervous_tumor | | | puc18 |
| L2730 | GN0021 | | placenta_normal | | | puc18 |
| L2731 | GN0023 | | placenta_normal | | | puc18 |
| L2733 | GN0037 | | placenta_normal | | | puc18 |
| L2737 | GN0047 | | placenta_normal | | | puc18 |
| L2738 | GN0049 | | placenta_normal | | | puc18 |
| L2744 | FT0004 | | prostate_tumor | | | puc18 |
| L2754 | FT0022 | | prostate_tumor | | | puc18 |
| L2755 | FT0023 | | prostate_tumor | | | puc18 |
| L2756 | FT0024 | | prostate_tumor | | | puc18 |
| L2757 | FT0025 | | prostate_tumor | | | puc18 |
| L2758 | FT0027 | | prostate_tumor | | | puc18 |
| L2759 | FT0028 | | prostate_tumor | | | puc18 |
| L2763 | FT0039 | | prostate_tumor | | | puc18 |
| L2766 | FT0042 | | prostate_tumor | | | puc18 |
| L2767 | FT0044 | | prostate_tumor | | | puc18 |
| L2771 | FT0050 | | prostate_tumor | | | puc18 |
| L2777 | FT0056 | | prostate_tumor | | | puc18 |
| L2779 | FT0058 | | prostate_tumor | | | puc18 |
| L2788 | FT0071 | | prostate_tumor | | | puc18 |
| L2791 | FT0077 | | prostate_tumor | | | puc18 |
| L2793 | FT0080 | | prostate_tumor | | | puc18 |
| L2799 | FT0096 | | prostate_tumor | | | puc18 |
| L2800 | FT0097 | | prostate_tumor | | | puc18 |
| L2804 | FT0103 | | prostate_tumor | | | puc18 |
| L2809 | FT0117 | | prostate_tumor | | | puc18 |
| L2810 | FT0119 | | prostate_tumor | | | puc18 |
| L2811 | FT0122 | | prostate_tumor | | | puc18 |
| L2812 | FT0123 | | prostate_tumor | | | puc18 |
| L2814 | FT0128 | | prostate_tumor | | | puc18 |
| L2815 | FT0129 | | prostate_tumor | | | puc18 |
| L2817 | FT0131 | | prostate_tumor | | | puc18 |
| L2819 | FT0134 | | prostate_tumor | | | puc18 |

TABLE 4-continued

| Code | Description | Tissue | Organ | Cell Line | Disease | Vector |
|---|---|---|---|---|---|---|
| L2831 | FT0162 | | prostate_tumor | | | puc18 |
| L2833 | FT0164 | | prostate_tumor | | | puc18 |
| L2836 | FT0169 | | prostate_tumor | | | puc18 |
| L2842 | UM0009 | | uterus | | | puc18 |
| L2843 | UM0017 | | uterus | | | puc18 |
| L2844 | UM0018 | | uterus | | | puc18 |
| L2845 | UM0021 | | uterus | | | puc18 |
| L2846 | UM0022 | | uterus | | | puc18 |
| L2848 | UM0053 | | uterus | | | puc18 |
| L2852 | UM0077 | | uterus | | | puc18 |
| L2854 | UM0091 | | uterus | | | puc18 |
| L2865 | AN0004 | | amnion_normal | | | puc18 |
| L2869 | AN0012 | | amnion_normal | | | puc18 |
| L2870 | AN0013 | | amnion_normal | | | puc18 |
| L2877 | AN0027 | | amnion_normal | | | puc18 |
| L2878 | AN0029 | | amnion_normal | | | puc18 |
| L2879 | AN0032 | | amnion_normal | | | puc18 |
| L2884 | AN0041 | | amnion_normal | | | puc18 |
| L2888 | AN0056 | | amnion_normal | | | puc18 |
| L2893 | AN0062 | | amnion_normal | | | puc18 |
| L2899 | AN0094 | | amnion_normal | | | puc18 |
| L2902 | BN0036 | | breast_normal | | | puc18 |
| L2903 | BN0039 | | breast_normal | | | puc18 |
| L2904 | BN0042 | | breast_normal | | | puc18 |
| L2905 | BN0046 | | breast_normal | | | puc18 |
| L2906 | BN0047 | | breast_normal | | | puc18 |
| L2909 | BN0067 | | breast_normal | | | puc18 |
| L2910 | BN0070 | | breast_normal | | | puc18 |
| L2914 | BN0090 | | breast_normal | | | puc18 |
| L2915 | BN0098 | | breast_normal | | | puc18 |
| L2918 | BN0114 | | breast_normal | | | puc18 |
| L2919 | BN0115 | | breast_normal | | | puc18 |
| L2924 | BN0138 | | breast_normal | | | puc18 |
| L2938 | BN0174 | | breast_normal | | | puc18 |
| L2962 | BN0221 | | breast_normal | | | puc18 |
| L2978 | BN0247 | | breast_normal | | | puc18 |
| L2985 | BN0257 | | breast_normal | | | puc18 |
| L2987 | BN0259 | | breast_normal | | | puc18 |
| L2991 | BN0264 | | breast_normal | | | puc18 |
| L2999 | BN0273 | | breast_normal | | | puc18 |
| L3001 | BN0275 | | breast_normal | | | puc18 |
| L3002 | BN0276 | | breast_normal | | | puc18 |
| L3010 | BN0294 | | breast_normal | | | puc18 |
| L3011 | BN0295 | | breast_normal | | | puc18 |
| L3012 | BN0296 | | breast_normal | | | puc18 |
| L3019 | BN0303 | | breast_normal | | | puc18 |
| L3020 | BN0304 | | breast_normal | | | puc18 |
| L3041 | BN0332 | | breast_normal | | | puc18 |
| L3058 | EN0004 | | lung_normal | | | puc18 |
| L3066 | EN0018 | | lung_normal | | | puc18 |
| L3071 | EN0026 | | lung_normal | | | puc18 |
| L3078 | EN0042 | | lung_normal | | | puc18 |
| L3080 | ET0001 | | lung_tumor | | | puc18 |
| L3081 | ET0005 | | lung_tumor | | | puc18 |
| L3089 | ET0018 | | lung_tumor | | | puc18 |
| L3092 | ET0023 | | lung_tumor | | | puc18 |
| L3093 | ET0024 | | lung_tumor | | | puc18 |
| L3095 | ET0027 | | lung_tumor | | | puc18 |
| L3104 | ET0041 | | lung_tumor | | | puc18 |
| L3109 | ET0046 | | lung_tumor | | | puc18 |
| L3111 | ET0058 | | lung_tumor | | | puc18 |
| L3117 | ET0068 | | lung_tumor | | | puc18 |
| L3118 | ET0070 | | lung_tumor | | | puc18 |
| L3119 | ET0072 | | lung_tumor | | | puc18 |
| L3127 | ET0084 | | lung_tumor | | | puc18 |
| L3128 | MT0016 | | marrow | | | puc18 |
| L3132 | MT0022 | | marrow | | | puc18 |
| L3134 | MT0024 | | marrow | | | puc18 |
| L3140 | MT0031 | | marrow | | | puc18 |
| L3144 | MT0035 | | marrow | | | puc18 |
| L3153 | MT0049 | | marrow | | | puc18 |
| L3154 | MT0050 | | marrow | | | puc18 |
| L3158 | MT0057 | | marrow | | | puc18 |
| L3160 | MT0059 | | marrow | | | puc18 |
| L3180 | MT0101 | | marrow | | | puc18 |
| L3181 | MT0107 | | marrow | | | puc18 |
| L3182 | MT0108 | | marrow | | | puc18 |
| L3184 | MT0111 | | marrow | | | puc18 |

TABLE 4-continued

| Code | Description | Tissue | Organ | Cell Line | Disease | Vector |
|---|---|---|---|---|---|---|
| L3186 | MT0113 | | marrow | | | puc18 |
| L3199 | OT0019 | | ovary | | | puc18 |
| L3204 | OT0034 | | ovary | | | puc18 |
| L3207 | OT0063 | | ovary | | | puc18 |
| L3210 | OT0067 | | ovary | | | puc18 |
| L3211 | OT0072 | | ovary | | | puc18 |
| L3212 | OT0076 | | ovary | | | puc18 |
| L3213 | OT0078 | | ovary | | | puc18 |
| L3215 | OT0083 | | ovary | | | puc18 |
| L3216 | OT0086 | | ovary | | | puc18 |
| L3217 | OT0091 | | ovary | | | puc18 |
| L3226 | FN0019 | | prostate_normal | | | puc18 |
| L3250 | FN0058 | | prostate_normal | | | puc18 |
| L3255 | FN0064 | | prostate_normal | | | puc18 |
| L3262 | FN0073 | | prostate_normal | | | puc18 |
| L3264 | FN0080 | | prostate_normal | | | puc18 |
| L3271 | FN0094 | | prostate_normal | | | puc18 |
| L3274 | FN0098 | | prostate_normal | | | puc18 |
| L3278 | FN0104 | | prostate_normal | | | puc18 |
| L3280 | FN0106 | | prostate_normal | | | puc18 |
| L3281 | FN0107 | | prostate_normal | | | puc18 |
| L3295 | FN0138 | | prostate_normal | | | puc18 |
| L3297 | FN0140 | | prostate_normal | | | puc18 |
| L3300 | FN0143 | | prostate_normal | | | puc18 |
| L3311 | FN0180 | | prostate_normal | | | puc18 |
| L3312 | FN0181 | | prostate_normal | | | puc18 |
| L3316 | FN0188 | | prostate_normal | | | puc18 |
| L3327 | SN0024 | | stomach_normal | | | puc18 |
| L3330 | SN0041 | | stomach_normal | | | puc18 |
| L3336 | SN0066 | | stomach_normal | | | puc18 |
| L3352 | TN0027 | | testis_normal | | | puc18 |
| L3355 | TN0032 | | testis_normal | | | puc18 |
| L3357 | TN0034 | | testis_normal | | | puc18 |
| L3358 | TN0035 | | testis_normal | | | puc18 |
| L3359 | TN0036 | | testis_normal | | | puc18 |
| L3369 | TN0065 | | testis_normal | | | puc18 |
| L3372 | TN0068 | | testis_normal | | | puc18 |
| L3374 | TN0070 | | testis_normal | | | puc18 |
| L3377 | TN0079 | | testis_normal | | | puc18 |
| L3378 | TN0080 | | testis_normal | | | puc18 |
| L3385 | *Homo sapiens* HeLa | | | HeLa | | |
| L3387 | GKB | hepatocellular carcinoma | | | | pBLUESCRIPT ™ SK− |
| L3388 | GKC | hepatocellular carcinoma | | | | pBLUESCRIPT ™ SK− |
| L3389 | GKD | hepatocellular carcinoma | | | | pBLUESCRIPT ™ SK− |
| L3391 | NIH_MGC_53 | carcinoma, cell line | bladder | | | pDNR-LIB (CLONTECH ™) |
| L3401 | AN0085 | | amnion_normal | | | puc18 |
| L3402 | AN0086 | | amnion_normal | | | puc18 |
| L3403 | AN0087 | | amnion_normal | | | puc18 |
| L3404 | AN0089 | | amnion_normal | | | puc18 |
| L3421 | BT0634 | | breast | | | puc18 |
| L3431 | CT0451 | | colon | | | puc18 |
| L3432 | CT0461 | | colon | | | puc18 |
| L3435 | CT0465 | | colon | | | puc18 |
| L3443 | CT0482 | | colon | | | puc18 |
| L3445 | CT0497 | | colon | | | puc18 |
| L3450 | CT0508 | | colon | | | puc18 |
| L3459 | FT0175 | | prostate_tumor | | | puc18 |
| L3463 | GN0016 | | placenta_normal | | | puc18 |
| L3464 | GN0018 | | placenta_normal | | | puc18 |
| L3466 | GN0020 | | placenta_normal | | | puc18 |
| L3476 | GN0051 | | placenta_normal | | | puc18 |
| L3480 | GN0057 | | placenta_normal | | | puc18 |
| L3484 | GN0067 | | placenta_normal | | | puc18 |
| L3485 | GN0070 | | placenta_normal | | | puc18 |
| L3490 | GN0075 | | placenta_normal | | | puc18 |
| L3491 | GN0076 | | placenta_normal | | | puc18 |
| L3494 | HT0539 | | head_neck | | | puc18 |
| L3495 | HT0570 | | head_neck | | | puc18 |
| L3496 | HT0572 | | head_neck | | | puc18 |
| L3497 | HT0600 | | head_neck | | | puc18 |
| L3499 | HT0617 | | head_neck | | | puc18 |
| L3503 | HT0870 | | head_neck | | | puc18 |
| L3504 | HT0873 | | head_neck | | | puc18 |
| L3506 | HT0879 | | head_neck | | | puc18 |

TABLE 4-continued

| Code | Description | Tissue | Organ | Cell Line | Disease | Vector |
|---|---|---|---|---|---|---|
| L3511 | HT0900 | | head_neck | | | puc18 |
| L3516 | HT0913 | | head_neck | | | puc18 |
| L3518 | HT0915 | | head_neck | | | puc18 |
| L3520 | HT0918 | | head_neck | | | puc18 |
| L3521 | HT0919 | | head_neck | | | puc18 |
| L3526 | HT0931 | | head_neck | | | puc18 |
| L3530 | HT0939 | | head_neck | | | puc18 |
| L3540 | MT0126 | | marrow | | | puc18 |
| L3546 | NN0044 | | nervous_normal | | | puc18 |
| L3554 | OT0035 | | ovary | | | puc18 |
| L3560 | TN0023 | | testis_normal | | | puc18 |
| L3561 | TN0025 | | testis_normal | | | puc18 |
| L3562 | TN0030 | | testis_normal | | | puc18 |
| L3563 | TN0037 | | testis_normal | | | puc18 |
| L3565 | TN0045 | | testis_normal | | | puc18 |
| L3566 | TN0046 | | testis_normal | | | puc18 |
| L3576 | TN0086 | | testis_normal | | | puc18 |
| L3585 | TN0119 | | testis_normal | | | puc18 |
| L3586 | TN0120 | | testis_normal | | | puc18 |
| L3592 | TN0129 | | testis_normal | | | puc18 |
| L3603 | UM0093 | | uterus | | | puc18 |
| L3605 | UM0104 | | uterus | | | puc18 |
| L3609 | UT0007 | | uterus_tumor | | | puc18 |
| L3612 | UT0011 | | uterus_tumor | | | puc18 |
| L3618 | UT0050 | | uterus_tumor | | | puc18 |
| L3625 | UT0063 | | uterus_tumor | | | puc18 |
| L3630 | UT0071 | | uterus_tumor | | | puc18 |
| L3631 | UT0072 | | uterus_tumor | | | puc18 |
| L3632 | UT0074 | | uterus_tumor | | | puc18 |
| L3634 | NIH_MGC_56 | primitive neuroectoderm | brain | | | pDNR-LIB (CLONTECH ™) |
| L3635 | NIH_MGC_62 | melanotic melanoma, high MDR | skin | | | pDNR-LIB (CLONTECH ™) |
| L3636 | NIH_MGC_73 | | brain | | | pDNR-LIB (CLONTECH ™) |
| L3637 | NIH_MGC_74 | | heart | | | pDNR-LIB (CLONTECH ™) |
| L3638 | NIH_MGC_78 | | pancreas | | | pDNR-LIB (CLONTECH ™) |
| L3641 | NIH_MGC_83 | | prostate | | | pDNR-LIB (CLONTECH ™) |
| L3642 | ADA | Adrenal gland | | | | pBLUESCRIPT ™ SK− |
| L3643 | ADB | Adrenal gland | | | | pBLUESCRIPT ™ SK− |
| L3644 | ADC | Adrenal gland | | | | pBLUESCRIPT ™ SK− |
| L3645 | Cu | adrenal cortico adenoma for Cushing''s syndrome | | | | pBLUESCRIPT ™ SK− |
| L3646 | DCA | | | | | pTriplEx2 |
| L3647 | Human HO-1 melanoma cells | | | | | |
| L3649 | DCB | | | | | pTriplEx2 |
| L3651 | FHTA | hypothalamus | | | | pTriplEx2 |
| L3652 | FHTB | hypothalamus | | | | pTriplEx2 |
| L3653 | HTB | Hypothalamus | | | | pBLUESCRIPT ™ SK− |
| L3655 | HTC | Hypothalamus | | | | pBLUESCRIPT ™ SK− |
| L3656 | HTE | Hypothalamus | | | | pBLUESCRIPT ™ SK− |
| L3657 | HTF | Hypothalamus | | | | pBLUESCRIPT ™ SK− |
| L3658 | cdA | pheochromocytoma | | | | pTriplEx2 |
| L3659 | CB | cord blood | | | | pBLUESCRIPT ™ |
| L3660 | NP1 | pituitary | | | | pBLUESCRIPT ™ SK− |
| L3661 | NPA | pituitary | | | | pBLUESCRIPT ™ SK− |
| L3663 | NIH_MGC_60 | adenocarcinoma | prostate | | | pDNR-LIB (CLONTECH ™) |
| L3664 | NIH_MGC_61 | embryonal carcinoma | testis | | | pDNR-LIB (CLONTECH ™) |
| L3665 | NIH_MGC_75 | | kidney | | | pDNR-LIB (CLONTECH ™) |
| L3666 | NIH_MGC_77 | | lung | | | pDNR-LIB (CLONTECH ™) |
| L3667 | NIH_MGC_79 | | placenta | | | pDNR-LIB (CLONTECH ™) |

TABLE 4-continued

| Code | Description | Tissue | Organ | Cell Line | Disease | Vector |
|---|---|---|---|---|---|---|
| L3668 | AN0063 | | amnion_normal | | | puc18 |
| L3672 | AN0083 | | amnion_normal | | | puc18 |
| L3673 | AN0084 | | amnion_normal | | | puc18 |
| L3684 | BT0812 | | breast | | | puc18 |
| L3693 | CI0018 | | colon_ins | | | puc18 |
| L3697 | CS0012 | | colon_est | | | puc18 |
| L3699 | CT0437 | | colon | | | puc18 |
| L3705 | CT0486 | | colon | | | puc18 |
| L3709 | CT0515 | | colon | | | puc18 |
| L3713 | CT0524 | | colon | | | puc18 |
| L3718 | CT0532 | | colon | | | puc18 |
| L3722 | GN0030 | | placenta_normal | | | puc18 |
| L3724 | GN0034 | | placenta_normal | | | puc18 |
| L3726 | GN0038 | | placenta_normal | | | puc18 |
| L3728 | GN0077 | | placenta_normal | | | puc18 |
| L3729 | GN0079 | | placenta_normal | | | puc18 |
| L3738 | GN0092 | | placenta_normal | | | puc18 |
| L3739 | HT0540 | | head_neck | | | puc18 |
| L3744 | HT0916 | | head_neck | | | puc18 |
| L3750 | HT0945 | | head_neck | | | puc18 |
| L3752 | HT0947 | | head_neck | | | puc18 |
| L3761 | NN1141 | | nervous_normal | | | puc18 |
| L3763 | SN0036 | | stomach_normal | | | puc18 |
| L3768 | TN0073 | | testis_normal | | | puc18 |
| L3778 | TN0112 | | testis_normal | | | puc18 |
| L3783 | TN0136 | | testis_normal | | | puc18 |
| L3790 | TN0150 | | testis_normal | | | puc18 |
| L3796 | UT0042 | | uterus_tumor | | | puc18 |
| L3802 | UT0052 | | uterus_tumor | | | puc18 |
| L3804 | UT0073 | | uterus_tumor | | | puc18 |
| L3805 | UT0075 | | uterus_tumor | | | puc18 |
| L3807 | UT0077 | | uterus_tumor | | | puc18 |
| L3808 | UT0078 | | uterus_tumor | | | puc18 |
| L3811 | NPC | pituitary | | | | pBLUESCRIPT ™ SK− |
| L3812 | NPD | pituitary | | | | pBLUESCRIPT ™ SK− |
| L3813 | TP | pituitary tumor | | | | pTriplEx2 |
| L3814 | BM | Bone marrow | | | | pTriplEx2 |
| L3815 | MDS | Bone marrow | | | | pTriplEx2 |
| L3816 | HEMBA1 | whole embryo, mainly head | | | | pME18SFL3 |
| L3817 | HEMBB1 | whole embryo, mainly body | | | | pME18SFL3 |
| L3818 | MAMMA1 | mammary gland | | | | pME18SFL3 |
| L3819 | NIH_MGC_76 | | liver | | | pDNR-LIB (CLONTECH ™) |
| L3820 | NIH_MGC_46 | leiomyosarcoma cell line | uterus | | | pOTB7 |
| L3821 | NIH_MGC_48 | primary B-cells from tonsils (cell line) | B-cells | | | pOTB7 |
| L3822 | NIH_MGC_59 | mucoepidermoid carcinoma | lung | | | pDNR-LIB (CLONTECH ™) |
| L3823 | NT2RM1 | | | NT2 | | pUC19FL3 |
| L3824 | NT2RM2 | | | NT2 | | pME18SFL3 |
| L3825 | NT2RM4 | | | NT2 | | pME18SFL3 |
| L3826 | NT2RP1 | | | NT2 | | pUC19FL3 |
| L3827 | NT2RP2 | | | NT2 | | pME18SFL3 |
| L3828 | NT2RP3 | | | NT2 | | pME18SFL3 |
| L3829 | NT2RP4 | | | NT2 | | pME18SFL3 |
| L3831 | OVARC1 | ovary, tumor tissue | | | | pME18SFL3 |
| L3832 | PLACE1 | placenta | | | | pME18SFL3 |
| L3833 | PLACE2 | placenta | | | | pME18SFL3 |
| L3834 | PLACE3 | placenta | | | | pME18SFL3 |
| L3835 | PLACE4 | placenta | | | | pME18SFL3 |
| L3836 | SKNMC1 | | | SK-N-MC | | pME18SFL3 |
| L3837 | THYRO1 | thyroid gland | | | | pME18SFL3 |
| L3839 | Y79AA1 | | | Y79 | | pME18SFL3 |
| L3841 | NIH_MGC_18 | large cell carcinoma | lung | | | pOTB7 |
| L3854 | BT0817 | | breast | | | puc18 |
| L3871 | NIH_MGC_19 | neuroblastoma | brain | | | pOTB7 |
| L3872 | NCI_CGAP_Skn1 | | skin, normal, 4 pooled sa | | | pCMV-SPORT6 (LIFE TECHNOLOGIES ™) |
| L3873 | Human esophageal carcinoma mRNA | esophageal squamous cell carcinoma | | | | pGEM-T (Promega) |
| L3904 | NCI_CGAP_Brn64 | glioblastoma with EGFR amplification | brain | | | pCMV-SPORT6 (LIFE TECHNOLOGIES ™) |

TABLE 4-continued

| Code | Description | Tissue | Organ | Cell Line | Disease | Vector |
|---|---|---|---|---|---|---|
| L3905 | NCI_CGAP_Brn67 | anaplastic oligodendroglioma with 1p/19q loss | brain | | | pCMV-SPORT6 (LIFE TECHNOLOGIES ™) |
| L4497 | NCI_CGAP_Br22 | invasive ductal carcinoma, 3 pooled samples | breast | | | pCMV-SPORT6 (LIFE TECHNOLOGIES ™) |
| L4500 | NCI_CGAP_HN16 | moderate to poorly differentiated invasive carcino | mouth | | | pAMP10 |
| L4501 | NCI_CGAP_Sub8 | | | | | pT7T3D-Pac (PHARMACIA ™) with a modified polylinker |
| L4507 | NCI_CGAP_Thy6 | normal epithelium | thyroid | | | pAMP10 |
| L4508 | NCI_CGAP_Thy8 | normal epithelium | thyroid | | | pAMP10 |
| L4535 | NCI_CGAP_Thy4 | normal epithelium | thyroid | | | pAMP10 |
| L4537 | NCI_CGAP_Thy7 | follicular adenoma (benign lesion) | thyroid | | | pAMP10 |
| L4556 | NCI_CGAP_HN13 | squamous cell carcinoma | tongue | | | pCMV-SPORT6 (LIFE TECHNOLOGIES ™) |
| L4557 | NCI_CGAP_Adr1 | neuroblastoma | adrenal gland | | | pCMV-SPORT6 (LIFE TECHNOLOGIES ™) |
| L4558 | NCI_CGAP_Pan3 | | pancreas | | | pCMV-SPORT6 (LIFE TECHNOLOGIES ™) |
| L4559 | NCI_CGAP_Thy3 | follicular carcinoma | thyroid | | | pCMV-SPORT6 (LIFE TECHNOLOGIES ™) |
| L4560 | NCI_CGAP_Ut7 | tumor | uterus | | | pCMV-SPORT6 (LIFE TECHNOLOGIES ™) |
| L4669 | NCI_CGAP_Ov41 | serous papillary tumor | ovary | | | pCMV-SPORT6 (LIFE TECHNOLOGIES ™) |
| L4747 | NCI_CGAP_Brn41 | oligodendroglioma | brain | | | pT7T3D-Pac (PHARMACIA ™) with a modified polylinker |
| L4753 | NCI_CGAP_HN15 | leukoplakia of the buccal mucosa | mouth | | | pAMP10 |
| L4775 | NCI_CGAP_Thy12 | papillary carcinoma | thyroid | | | pAMP10 |
| L5286 | NCI_CGAP_Thy10 | medullary carcinoma | thyroid | | | pAMP10 |
| L5564 | NCI_CGAP_HN20 | | normal head/neck tissue | | | pAMP1 |
| L5565 | NCI_CGAP_Brn66 | glioblastoma with probably TP53 mutation and witho | brain | | | pCMV-SPORT6 (LIFE TECHNOLOGIES ™) |
| L5566 | NCI_CGAP_Brn70 | anaplastic oligodendroglioma | brain | | | pCMV-SPORT6.ccdb |
| L5568 | NCI_CGAP_HN21 | nasopharyngeal carcinoma | head/neck | | | pAMP1 |
| L5569 | NCI_CGAP_HN17 | normal epithelium | nasopharynx | | | pAMP10 |
| L5570 | NCI_CGAP_Co28 | normal colonic mucosa | colon | | | pAMP1 |
| L5572 | NCI_CGAP_Co27 | adenocarcinoma (mucinous component) | colon | | | pAMP1 |
| L5574 | NCI_CGAP_HN19 | normal epithelium | nasopharynx | | | pAMP10 |
| L5575 | NCI_CGAP_Brn65 | glioblastoma without EGFR amplification | brain | | | pCMV-SPORT6 (LIFE TECHNOLOGIES ™) |
| L5622 | NCI_CGAP_Skn3 | | skin | | | pCMV-SPORT6 (LIFE TECHNOLOGIES ™) |
| L5623 | NCI_CGAP_Skn4 | squamous cell carcinoma | skin | | | pCMV-SPORT6 (LIFE TECHNOLOGIES ™) |
| N0003 | Human Fetal Brain | Human Fetal Brain | | | | |
| N0004 | Human Hippocampus | Human Hippocampus | | | | |
| N0006 | Human Fetal Brain | Human Fetal Brain | | | | |
| N0007 | Human Hippocampus | Human Hippocampus | | | | |
| N0009 | Human Hippocampus, prescreened | Human Hippocampus | | | | |
| N0011 | Human Brain | Human Brain | | | | |
| S0001 | Brain frontal cortex | Brain frontal cortex | Brain | | | LAMBDA ZAP ™ II |

TABLE 4-continued

| Code | Description | Tissue | Organ | Cell Line | Disease | Vector |
|---|---|---|---|---|---|---|
| S0002 | Monocyte activated | Monocyte-activated | blood | Cell Line | | UNI-ZAP ™ XR |
| S0003 | Human Osteoclastoma | Osteoclastoma | bone | | disease | UNI-ZAP ™ XR |
| S0004 | Prostate | Prostate BPH | Prostate | | | LAMBDA ZAP ™ II |
| S0005 | Heart | Heart-left ventricle | Heart | | | pCDNA |
| S0006 | Neuroblastoma | Human Neural Blastoma | | | disease | pCDNA |
| S0007 | Early Stage Human Brain | Human Fetal Brain | | | | UNI-ZAP ™ XR |
| S0008 | Osteoclastoma | Osteoclastoma | bone | | disease | UNI-ZAP ™ XR |
| S0010 | Human Amygdala | Amygdala | | | | UNI-ZAP ™ XR |
| S0011 | STROMAL-OSTEOCLASTOMA | Osteoclastoma | bone | | disease | UNI-ZAP ™ XR |
| S0013 | Prostate | Prostate | prostate | | | UNI-ZAP ™ XR |
| S0014 | Kidney Cortex | Kidney cortex | Kidney | | | UNI-ZAP ™ XR |
| S0015 | Kidney medulla | Kidney medulla | Kidney | | | UNI-ZAP ™ XR |
| S0016 | Kidney Pyramids | Kidney pyramids | Kidney | | | UNI-ZAP ™ XR |
| S0020 | Seven Trans Membrane Receptor Family | 7TMD1 | | | | |
| S0021 | Whole brain | Whole brain | Brain | | | ZAP EXPRESS ™ |
| S0022 | Human Osteoclastoma Stromal Cells - unamplified | Osteoclastoma Stromal Cells | | | | UNI-ZAP ™ XR |
| S0023 | Human Kidney Cortex - unamplified | Human Kidney Cortex | | | | |
| S0024 | Human Kidney Medulla - unamplified | Human Kidney Medulla | | | | |
| S0025 | Human Kidney Pyramids - unamplified | Human Kidney Pyramids | | | | |
| S0026 | Stromal cell TF274 | stromal cell | Bone marrow | Cell Line | | UNI-ZAP ™ XR |
| S0027 | Smooth muscle, serum treated | Smooth muscle | Pulmanary artery | Cell Line | | UNI-ZAP ™ XR |
| S0028 | Smooth muscle, control | Smooth muscle | Pulmanary artery | Cell Line | | UNI-ZAP ™ XR |
| S0029 | brain stem | Brain stem | brain | | | UNI-ZAP ™ XR |
| S0030 | Brain pons | Brain Pons | Brain | | | UNI-ZAP ™ XR |
| S0031 | Spinal cord | Spinal cord | spinal cord | | | UNI-ZAP ™ XR |
| S0032 | Smooth muscle-ILb induced | Smooth muscle | Pulmanary artery | Cell Line | | UNI-ZAP ™ XR |
| S0035 | Brain medulla oblongata | Brain medulla oblongata | Brain | | | UNI-ZAP ™ XR |
| S0036 | Human Substantia Nigra | Human Substantia Nigra | | | | UNI-ZAP ™ XR |
| S0037 | Smooth muscle, IL1b induced | Smooth muscle | Pulmanary artery | Cell Line | | UNI-ZAP ™ XR |
| S0038 | Human Whole Brain #2 - Oligo dT >1.5 Kb | Human Whole Brain #2 | | | | ZAP EXPRESS ™ |
| S0039 | Hypothalamus | Hypothalamus | Brain | | | UNI-ZAP ™ XR |
| S0040 | Adipocytes | Human Adipocytes from Osteoclastoma | | | | UNI-ZAP ™ XR |
| S0041 | Thalamus | Human Thalamus | | | | UNI-ZAP ™ XR |
| S0042 | Testes | Human Testes | | | | ZAP EXPRESS ™ |
| S0044 | Prostate BPH | prostate BPH | Prostate | | disease | UNI-ZAP ™ XR |
| S0045 | Endothelial cells-control | Endothelial cell | endothelial cell-lung | Cell Line | | UNI-ZAP ™ XR |
| S0046 | Endothelial-induced | Endothelial cell | endothelial cell-lung | Cell Line | | UNI-ZAP ™ XR |
| S0048 | Human Hypothalamus, Alzheimer''s | Human Hypothalamus, Alzheimer''s | | | disease | UNI-ZAP ™ XR |
| S0049 | Human Brain, Striatum | Human Brain, Striatum | | | | UNI-ZAP ™ XR |
| S0050 | Human Frontal Cortex, Schizophrenia | Human Frontal Cortex, Schizophrenia | | | disease | UNI-ZAP ™ XR |

TABLE 4-continued

| Code | Description | Tissue | Organ | Cell Line | Disease | Vector |
|---|---|---|---|---|---|---|
| S0051 | Human Hypothalmus, Schizophrenia | Human Hypothalamus, Schizophrenia | | | disease | UNI-ZAP ™ XR |
| S0052 | neutrophils control | human neutrophils | blood | Cell Line | | UNI-ZAP ™ XR |
| S0053 | Neutrophils IL-1 and LPS induced | human neutrophil induced | blood | Cell Line | | UNI-ZAP ™ XR |
| S0106 | STRIATUM DEPRESSION | | BRAIN | | disease | UNI-ZAP ™ XR |
| S0110 | Brain Amygdala Depression | | Brain | | disease | UNI-ZAP ™ XR |
| S0112 | Hypothalamus | | Brain | | | UNI-ZAP ™ XR |
| S0114 | Anergic T-cell | Anergic T-cell | | Cell Line | | UNI-ZAP ™ XR |
| S0116 | Bone marrow | Bone marrow | Bone marrow | | | UNI-ZAP ™ XR |
| S0118 | Smooth muscle control 2 | Smooth muscle | Pulmanary artery | Cell Line | | UNI-ZAP ™ XR |
| S0122 | Osteoclastoma-normalized A | Osteoclastoma | bone | | disease | pBLUESCRIPT ™ |
| S0124 | Smooth muscle-edited A | Smooth muscle | Pulmanary artery | Cell Line | | UNI-ZAP ™ XR |
| S0126 | Osteoblasts | Osteoblasts | Knee | Cell Line | | UNI-ZAP ™ XR |
| S0132 | Epithelial-TNFa and INF induced | Airway Epithelial | | | | UNI-ZAP ™ XR |
| S0134 | Apoptotic T-cell | apoptotic cells | | Cell Line | | UNI-ZAP ™ XR |
| S0136 | PERM TF274 | stromal cell | Bone marrow | Cell Line | | LAMBDA ZAP ™ II |
| S0140 | eosinophil-IL5 induced | eosinophil | lung | Cell Line | | UNI-ZAP ™ XR |
| S0142 | Macrophage-oxLDL | macrophage-oxidized LDL treated | blood | Cell Line | | UNI-ZAP ™ XR |
| S0144 | Macrophage (GM-CSF treated) | Macrophage (GM-CSF treated) | | | | UNI-ZAP ™ XR |
| S0146 | prostate-edited | prostate BPH | Prostate | | | UNI-ZAP ™ XR |
| S0148 | Normal Prostate | Prostate | prostate | | | UNI-ZAP ™ XR |
| S0150 | LNCAP prostate cell line | LNCAP Cell Line | Prostate | Cell Line | | UNI-ZAP ™ XR |
| S0152 | PC3 Prostate cell line | PC3 prostate cell line | | | | UNI-ZAP ™ XR |
| S0168 | Prostate/LNCAP, subtraction I | PC3 prostate cell line | | | | pBLUESCRIPT ™ |
| S0174 | Prostate-BPH subtracted II | Human Prostate BPH | | | | pBLUESCRIPT ™ |
| S0176 | Prostate, normal, subtraction I | Prostate | prostate | | | UNI-ZAP ™ XR |
| S0180 | Bone Marrow Stroma, TNF&LPS ind | Bone Marrow Stroma, TNF & LPS induced | | | disease | UNI-ZAP ™ XR |
| S0182 | Human B Cell 8866 | Human B-Cell 8866 | | | | UNI-ZAP ™ XR |
| S0184 | 7TM Receptor enriched, lib II | PBLS, 7TM receptor enriched | | | | Other |
| S0188 | Prostate, BPH, Lib 2 | Human Prostate BPH | | | disease | pSport1 |
| S0190 | Prostate BPH, Lib 2, subtracted | Human Prostate BPH | | | | pSport1 |
| S0192 | Synovial Fibroblasts (control) | Synovial Fibroblasts | | | | pSport1 |
| S0194 | Synovial hypoxia | Synovial Fibroblasts | | | | pSport1 |
| S0196 | Synovial IL-1/TNF stimulated | Synovial Fibroblasts | | | | pSport1 |
| S0198 | 7TM-pbfd | PBLS, 7TM receptor enriched | | | | pCR II [Invitrogen] |
| S0202 | 7TM-pbdd | PBLS, 7TM receptor enriched | | | | pCR II [Invitrogen] |
| S0206 | Smooth Muscle-HASTE normalized | Smooth muscle | Pulmanary artery | Cell Line | | pBLUESCRIPT ™ |
| S0208 | Messangial cell, frac 1 | Messangial cell | | | | pSport1 |
| S0210 | Messangial cell, frac 2 | Messangial cell | | | | pSport1 |
| S0212 | Bone Marrow Stromal Cell, untreated | Bone Marrow Stromal Cell, untreated | | | | pSport1 |
| S0214 | Human Osteoclastoma, re-excision | Osteoclastoma | bone | | disease | UNI-ZAP ™ XR |
| S0216 | Neutrophils IL-1 and LPS induced | human neutrophil induced | blood | Cell Line | | UNI-ZAP ™ XR |
| S0218 | Apoptotic T-cell, re-excision | apoptotic cells | | Cell Line | | UNI-ZAP ™ XR |
| S0220 | H. hypothalamus, frac A; re-excision | Hypothalamus | Brain | | | ZAP EXPRESS ™ |
| S0222 | H. Frontal cortex, epileptic; re-excision | H. Brain, Frontal Cortex, Epileptic | Brain | | disease | UNI-ZAP ™ XR |

TABLE 4-continued

| Code | Description | Tissue | Organ | Cell Line | Disease | Vector |
|---|---|---|---|---|---|---|
| S0228 | PSMIX | PBLS, 7TM receptor enriched | | | | pCR II [Invitrogen] |
| S0242 | Synovial Fibroblasts (Il1/TNF), subt | Synovial Fibroblasts | | | | pSport1 |
| S0250 | Human Osteoblasts II | Human Osteoblasts | Femur | | disease | pCMVSport 2.0 |
| S0252 | 7TM-PIMIX | PBLS, 7TM receptor enriched | | | | pCR II [Invitrogen] |
| S0256 | 7TM-PHMIX | PBLS, 7TM receptor enriched | | | | pCR II [Invitrogen] |
| S0260 | Spinal Cord, re-excision | Spinal cord | spinal cord | | | UNI-ZAP ™ XR |
| S0262 | PYCS | Human Antrum (PY_CS) | | | | pCR II [Invitrogen] |
| S0264 | PPMIX | PPMIX (Human Pituitary) | Pituitary | | | pCR II [Invitrogen] |
| S0266 | PLMIX | PLMIX (Human Lung) | Lung | | | pCR II [Invitrogen] |
| S0268 | PRMIX | PRMIX (Human Prostate) | prostate | | | pCR II [Invitrogen] |
| S0270 | PTMIX | PTMIX (Human Thymus) | Thymus | | | pCR II [Invitrogen] |
| S0274 | PCMIX | PCMIX (Human Cerebellum) | Brain | | | pCR II [Invitrogen] |
| S0276 | Synovial hypoxia-RSF subtracted | Synovial fobroblasts (rheumatoid) | Synovial tissue | | | pSport1 |
| S0278 | H Macrophage (GM-CSF treated), re-excision | Macrophage (GM-CSF treated) | | | | UNI-ZAP ™ XR |
| S0280 | Human Adipose Tissue, re-excision | Human Adipose Tissue | | | | UNI-ZAP ™ XR |
| S0282 | Brain Frontal Cortex, re-excision | Brain frontal cortex | Brain | | | LAMBDA ZAP ™ II |
| S0284 | 7TMCTT (Testis) | 7TMCTP (Placenta) | Testis | | | pCR II [Invitrogen] |
| S0290 | H7TMCTB (Brain) | 7TMCTB (Brain) | Kidney | | | pCR II [Invitrogen] |
| S0292 | Osteoarthritis (OA-4) | Human Osteoarthritic Cartilage | Bone | | disease | pSport1 |
| S0294 | Larynx tumor | Larynx tumor | Larynx, vocal cord | | disease | pSport1 |
| S0296 | Normal lung | Normal lung | Lung | | | pSport1 |
| S0298 | Bone marrow stroma, treated | Bone marrow stroma, treatedSB | Bone marrow | | | pSport1 |
| S0300 | Frontal lobe, dementia; re-excision | Frontal Lobe dementia/Alzheimer"s | Brain | | | UNI-ZAP ™ XR |
| S0306 | Larynx normal #10 261-273 | Larynx normal | | | | pSport1 |
| S0308 | Spleen/normal | Spleen normal | | | | pSport1 |
| S0310 | Normal trachea | Normal trachea | | | | pSport1 |
| S0312 | Human osteoarthritic; fraction II | Human osteoarthritic cartilage | | | disease | pSport1 |
| S0314 | Human osteoarthritis; fraction I | Human osteoarthritic cartilage | | | disease | pSport1 |
| S0316 | Human Normal Cartilage, Fraction I | Human Normal Cartilage | | | | pSport1 |
| S0318 | Human Normal Cartilage Fraction II | Human Normal Cartilage | | | | pSport1 |
| S0320 | Human Larynx | Larynx | Epiglottis | | | pSport1 |
| S0322 | Siebben Polyposis | Siebben Polyposis | | | | pSport1 |
| S0324 | Human Brain | Brain | Cerebellum | | | pSport1 |
| S0326 | Mammary Gland | Mammary Gland | Whole mammary gland | | | pSport1 |
| S0328 | Palate carcinoma | Palate carcinoma | Uvula | | disease | pSport1 |
| S0330 | Palate normal | Palate normal | Uvula | | | pSport1 |
| S0332 | Pharynx carcinoma | Pharynx carcinoma | Hypopharynx | | | pSport1 |
| S0334 | Human Normal Cartilage Fraction III | Human Normal Cartilage | | | | pSport1 |
| S0336 | Human Normal Cartilage Fraction IV | Human Normal Cartilage | | | | pSport1 |
| S0338 | Human Osteoarthritic Cartilage Fraction III | Human osteoarthritic cartilage | | | disease | pSport1 |
| S0340 | Human Osteoarthritic Cartilage Fraction IV | Human osteoarthritic cartilage | | | disease | pSport1 |
| S0342 | Adipocytes; re-excision | Human Adipocytes from Osteoclastoma | | | | UNI-ZAP ™ XR |
| S0344 | Macrophage-oxLDL; re-excision | macrophage-oxidized LDL treated | blood | Cell Line | | UNI-ZAP ™ XR |
| S0346 | Human Amygdala; re-excision | Amygdala | | | | UNI-ZAP ™ XR |

TABLE 4-continued

| Code | Description | Tissue | Organ | Cell Line | Disease | Vector |
|---|---|---|---|---|---|---|
| S0348 | Cheek Carcinoma | Cheek Carcinoma | | | disease | pSport1 |
| S0350 | Pharynx Carcinoma | Pharynx carcinoma | Hypopharynx | | disease | pSport1 |
| S0352 | Larynx Carcinoma | Larynx carcinoma | | | disease | pSport1 |
| S0354 | Colon Normal II | Colon Normal | Colon | | | pSport1 |
| S0356 | Colon Carcinoma | Colon Carcinoma | Colon | | disease | pSport1 |
| S0358 | Colon Normal III | Colon Normal | Colon | | | pSport1 |
| S0360 | Colon Tumor II | Colon Tumor | Colon | | disease | pSport1 |
| S0362 | Human Gastrocnemius | Gastrocnemius muscle | | | | pSport1 |
| S0364 | Human Quadriceps | Quadriceps muscle | | | | pSport1 |
| S0366 | Human Soleus | Soleus Muscle | | | | pSport1 |
| S0368 | Human Pancreatic Langerhans | Islets of Langerhans | | | | pSport1 |
| S0370 | Larynx carcinoma II | Larynx carcinoma | | | disease | pSport1 |
| S0372 | Larynx carcinoma III | Larynx carcinoma | | | disease | pSport1 |
| S0374 | Normal colon | Normal colon | | | | pSport1 |
| S0376 | Colon Tumor | Colon Tumor | | | disease | pSport1 |
| S0378 | Pancreas normal PCA4 No | Pancreas Normal PCA4 No | | | | pSport1 |
| S0380 | Pancreas Tumor PCA4 Tu | Pancreas Tumor PCA4 Tu | | | disease | pSport1 |
| S0382 | Larynx carcinoma IV | Larynx carcinoma | | | disease | pSport1 |
| S0384 | Tongue carcinoma | Tongue carcinoma | | | disease | pSport1 |
| S0386 | Human Whole Brain, re-excision | Whole brain | Brain | | | ZAP EXPRESS ™ |
| S0388 | Human Hypothalamus, schizophrenia, re-excision | Human Hypothalamus, Schizophrenia | | | disease | UNI-ZAP ™ XR |
| S0390 | Smooth muscle, control; re-excision | Smooth muscle | Pulmanary artery | Cell Line | | UNI-ZAP ™ XR |
| S0392 | Salivary Gland | Salivary gland; normal | | | | pSport1 |
| S0394 | Stomach; normal | Stomach; normal | | | | pSport1 |
| S0396 | Uterus; normal | Uterus; normal | | | | pSport1 |
| S0398 | Testis; normal | Testis; normal | | | | pSport1 |
| S0400 | Brain; normal | Brain; normal | | | | pSport1 |
| S0402 | Adrenal Gland, normal | Adrenal gland; normal | | | | pSport1 |
| S0404 | Rectum normal | Rectum, normal | | | | pSport1 |
| S0406 | Rectum tumour | Rectum tumour | | | | pSport1 |
| S0408 | Colon, normal | Colon, normal | | | | pSport1 |
| S0410 | Colon, tumour | Colon, tumour | | | | pSport1 |
| S0412 | Temporal cortex-Alzheizmer; subtracted | Temporal cortex, alzheimer | | | disease | Other |
| S0414 | Hippocampus, Alzheimer Subtracted | Hippocampus, Alzheimer Subtracted | | | | Other |
| S0418 | CHME Cell Line; treated 5 hrs | CHME Cell Line; treated | | | | pCMVSport 3.0 |
| S0420 | CHME Cell Line, untreated | CHME Cell line, untreatetd | | | | pSport1 |
| S0422 | Mo7e Cell Line GM-CSF treated (1 ng/ml) | Mo7e Cell Line GM-CSF treated (1 ng/ml) | | | | pCMVSport 3.0 |
| S0424 | TF-1 Cell Line GM-CSF Treated | TF-1 Cell Line GM-CSF Treated | | | | pSport1 |
| S0426 | Monocyte activated; re-excision | Monocyte-activated | blood | Cell Line | | UNI-ZAP ™ XR |
| S0428 | Neutrophils control; re-excision | human neutrophils | blood | Cell Line | | UNI-ZAP ™ XR |
| S0430 | Aryepiglottis Normal | Aryepiglottis Normal | | | | pSport1 |
| S0432 | Sinus piniformis Tumour | Sinus piniformis Tumour | | | | pSport1 |
| S0434 | Stomach Normal | Stomach Normal | | | disease | pSport1 |
| S0436 | Stomach Tumour | Stomach Tumour | | | disease | pSport1 |
| S0438 | Liver Normal Met5No | Liver Normal Met5No | | | | pSport1 |
| S0440 | Liver Tumour Met 5 Tu | Liver Tumour | | | | pSport1 |
| S0442 | Colon Normal | Colon Normal | | | | pSport1 |
| S0444 | Colon Tumor | Colon Tumour | | | disease | pSport1 |
| S0446 | Tongue Tumour | Tongue Tumour | | | | pSport1 |
| S0448 | Larynx Normal | Larynx Normal | | | | pSport1 |
| S0450 | Larynx Tumour | Larynx Tumour | | | | pSport1 |
| S0452 | Thymus | Thymus | | | | pSport1 |
| S0454 | Placenta | Placenta | Placenta | | | pSport1 |
| S0456 | Tongue Normal | Tongue Normal | | | | pSport1 |
| S0458 | Thyroid Normal (SDCA2 No) | Thyroid normal | | | | pSport1 |
| S0460 | Thyroid Tumour | Thyroid Tumour | | | | pSport1 |
| S0462 | Thyroid Thyroiditis | Thyroid Thyroiditis | | | | pSport1 |
| S0464 | Larynx Normal | Larynx Normal | | | | pSport1 |
| S0466 | Larynx Tumor | Larynx Tumor | | | disease | pSport1 |
| S0468 | Ea.hy.926 cell line | Ea.hy.926 cell line | | | | pSport1 |
| S0470 | Adenocarcinoma | PYFD | | | disease | pSport1 |
| S0472 | Lung Mesothelium | PYBT | | | | pSport1 |
| S0474 | Human blood platelets | Platelets | Blood platelets | | | Other |
| S0665 | Human Amygdala; re-excission | Amygdala | | | | UNI-ZAP ™ XR |
| S3012 | Smooth Muscle Serum Treated, Norm | Smooth muscle | Pulmanary artery | Cell Line | | pBLUESCRIPT ™ |

TABLE 4-continued

| Code | Description | Tissue | Organ | Cell Line | Disease | Vector |
|---|---|---|---|---|---|---|
| S3014 | Smooth muscle, serum induced, re-exc | Smooth muscle | Pulmanary artery | Cell Line | | pBLUESCRIPT ™ |
| S3018 | TH1 cells | TH1 cells | | | | UNI-ZAP ™ XR |
| S6014 | H. hypothalamus, frac A | Hypothalamus | Brain | | | ZAP EXPRESS ™ |
| S6016 | H. Frontal Cortex, Epileptic | H. Brain, Frontal Cortex, Epileptic | Brain | | disease | UNI-ZAP ™ XR |
| S6022 | H. Adipose Tissue | Human Adipose Tissue | | | | UNI-ZAP ™ XR |
| S6024 | Alzheimers, spongy change | Alzheimer”s/Spongy change | Brain | | disease | UNI-ZAP ™ XR |
| S6026 | Frontal Lobe, Dementia | Frontal Lobe dementia/Alzheimer”s | Brain | | | UNI-ZAP ™ XR |
| S6028 | Human Manic Depression Tissue | Human Manic depression tissue | Brain | | disease | UNI-ZAP ™ XR |
| T0001 | Human Brown Fat | Brown Fat | | | | pBLUESCRIPT ™ SK− |
| T0002 | Activated T-cells | Activated T-Cell, PBL fraction | Blood | Cell Line | | pBLUESCRIPT ™ SK− |
| T0003 | Human Fetal Lung | Human Fetal Lung | | | | pBLUESCRIPT ™ SK− |
| T0004 | Human White Fat | Human White Fat | | | | pBLUESCRIPT ™ SK− |
| T0006 | Human Pineal Gland | Human Pinneal Gland | | | | pBLUESCRIPT ™ SK− |
| T0007 | Colon Epithelium | Colon Epithelium | | | | pBLUESCRIPT ™ SK− |
| T0008 | Colorectal Tumor | Colorectal Tumor | | | disease | pBLUESCRIPT ™ SK− |
| T0010 | Human Infant Brain | Human Infant Brain | | | | Other |
| T0023 | Human Pancreatic Carcinoma | Human Pancreatic Carcinoma | | | disease | pBLUESCRIPT ™ SK− |
| T0039 | HSA 172 Cells | Human HSA172 cell line | | | | pBLUESCRIPT ™ SK− |
| T0040 | HSC172 cells | SA172 Cells | | | | pBLUESCRIPT ™ SK− |
| T0041 | Jurkat T-cell G1 phase | Jurkat T-cell | | | | pBLUESCRIPT ™ SK− |
| T0042 | Jurkat T-Cell, S phase | Jurkat T-Cell Line | | | | pBLUESCRIPT ™ SK− |
| T0047 | T lymphocytes >70 | T lymphocytes >70 | | | | pBLUESCRIPT ™ SK− |
| T0048 | Human Aortic Endothelium | Human Aortic Endothilium | | | | pBLUESCRIPT ™ SK− |
| T0049 | Aorta endothelial cells + TNF-a | Aorta endothelial cells | | | | pBLUESCRIPT ™ SK− |
| T0060 | Human White Adipose | Human White Fat | | | | pBLUESCRIPT ™ SK− |
| T0067 | Human Thyroid | Human Thyroid | | | | pBLUESCRIPT ™ SK− |
| T0067 | Human Thyroid | Human Thyroid | | | | PPBLUESCRIPT ™ SK− |
| T0068 | Normal Ovary, Premenopausal | Normal Ovary, Premenopausal | | | | pBLUESCRIPT ™ SK− |
| T0069 | Human Uterus, normal | Human Uterus, normal | | | | pBLUESCRIPT ™ SK− |
| T0070 | Human Adrenal Gland | Human Adrenal Gland | | | | pBLUESCRIPT ™ SK− |
| T0071 | Human Bone Marrow | Human Bone Marrow | | | | pBLUESCRIPT ™ SK− |
| T0074 | Human Adult Retina | Human Adult Retina | | | | pBluescriptISK− |
| T0078 | Human Liver, normal adult | Human Liver, normal Adult | | | | pBLUESCRIPT ™ SK− |
| T0079 | Human Kidney, normal Adult | Human Kidney, normal Adult | | | | pBLUESCRIPT ™ SK− |
| T0082 | Human Adult Retina | Human Adult Retina | | | | pBLUESCRIPT ™ SK− |
| T0082 | Human Adult Retina | Human Adult Retina | | | | PPBLUESCRIPT ™ SK− |
| T0086 | Human Pancreatic Carcinoma - Screened | Human Pancreatic Carcinoma | | | disease | pBLUESCRIPT ™ SK− |
| T0087 | Alzheimer”s, exon trap, 712P | | | | disease | pAMP |
| T0090 | Liver, normal | | | | | pBLUESCRIPT ™ SK− |
| T0091 | Liver, hepatocellular carcinoma | | | | | pBLUESCRIPT ™ SK− |

TABLE 4-continued

| Code | Description | Tissue | Organ | Cell Line | Disease | Vector |
|---|---|---|---|---|---|---|
| T0103 | Human colon carcinoma (HCC) cell line | | | | | pBLUESCRIPT ™ SK− |
| T0104 | HCC cell line metastisis to liver | | | | | pBLUESCRIPT ™ SK− |
| T0109 | Human (HCC) cell line liver (mouse) metastasis, remake | | | | | pBLUESCRIPT ™ SK− |
| T0110 | Human colon carcinoma (HCC) cell line, remake | | | | | pBLUESCRIPT ™ SK− |
| T0112 | Human (Caco-2) cell line, adenocarcinoma, colon | | | | | pBLUESCRIPT ™ SK− |
| T0114 | Human (Caco-2) cell line, adenocarcinoma, colon, remake | | | | | pBLUESCRIPT ™ SK− |
| T0115 | Human Colon Carcinoma (HCC) cell line | | | | | pBLUESCRIPT ™ SK− |

Table 5

Table 5 provides a key to the OMIM reference identification numbers disclosed in Table 1B.1, column 9. OMIM reference identification numbers (Column 1) were derived from Online Mendelian Inheritance in Man (Online Mendelian Inheritance in Man, OMIM. McKusick-Nathans Institute for Genetic Medicine, Johns Hopkins University (Baltimore, Md.) and National Center for Biotechnology Information, National Library of Medicine, (Bethesda, Md.) 2000 (world wide web at ncbi.nlm.nih.gov/omim/). Column 2 provides diseases associated with the cytologic band disclosed in Table 1B.1, column 8, as determined using the Morbid Map database.

TABLE 5

| OMIM Reference | Description |
|---|---|
| 100678 | ACAT2 deficiency |
| 100690 | Myasthenic syndrome, slow-channel congenital, 601462 |
| 100710 | Myasthenic syndrome, slow-channel congenital, 601462 |
| 100730 | Myasthenia gravis, neonatal transient |
| 101000 | Meningioma, NF2-related, sporadic Schwannoma, sporadic |
| 102200 | Somatotrophinoma |
| 102480 | Male infertility due to acrosin deficiency |
| 102540 | Cardiomyopathy, idiopathic dilated |
| 102578 | Leukemia, acute promyelocytic, PML/RARA type |
| 102700 | Severe combined immunodeficiency due to ADA deficiency |
| 102770 | Myoadenylate deaminase deficiency |
| 102772 | [AMP deaminase deficiency, erythrocytic] |
| 103000 | Hemolytic anemia due to adenylate kinase deficiency |
| 103050 | Autism, succinylpurinemic |
| 103581 | Albright hereditary osteodystrophy-2 |
| 103600 | [Dysalbuminemic hyperthyroxinemia] |
| 103720 | Alcoholism, susceptibility to |
| 103850 | Aldolase A deficiency |
| 103950 | Emphysema due to alpha-2-macroglobulin deficiency |
| 104150 | [AFP deficiency, congenital] |
| 104170 | NAGA deficiency, mild |
| 104311 | Alzheimer disease-3 |
| 104500 | Amelogenesis imperfecta-2, hypoplastic local type |
| 104770 | Amyloidosis, secondary, susceptibility to |
| 105580 | Anal canal carcinoma |
| 105600 | Dyserythropoietic anemia, congenital, type III |
| 106100 | Angioedema, hereditary |
| 106150 | Hypertension, essential, susceptibility to |
| 106165 | Hypertension, essential, 145500 |
| 106180 | Myocardial infarction, susceptibility to |
| 106210 | Peters anomaly |
| 106300 | Ankylosing spondylitis |
| 107250 | Anterior segment mesenchymal dysgenesis |
| 107271 | CD59 deficiency |
| 107300 | Antithrombin III deficiency |
| 107470 | Atypical mycobacterial infection, familial disseminated, 209950 |
| 107670 | Apolipoprotein A-II deficiency |

TABLE 5-continued

| OMIM Reference | Description |
|---|---|
| 107680 | ApoA-I and apoC-III deficiency, combined |
| 107720 | Hypertriglyceridemia |
| 107741 | Hyperlipoproteinemia, type III |
| 107776 | Colton blood group, 110450 |
| 107777 | Diabetes insipidus, nephrogenic, autosomal recessive, 222000 |
| 107910 | Virilization, maternal and fetal, from placental aromatase deficiency |
| 107970 | Arrhythmogenic right ventricular dysplasia-1 |
| 108120 | Distal arthrogryposis-1 |
| 108725 | Atherosclerosis, susceptibility to |
| 108730 | Brody myopathy, 601003 |
| 108800 | Atrial septal defect, secundum type |
| 108962 | Hypertension, salt-resistant |
| 108985 | Atrophia areata |
| 109150 | Machado-Joseph disease |
| 109270 | Renal tubular acidosis, distal, 179800 |
| 109400 | Basal cell nevus syndrome |
| 109560 | Leukemia/lymphoma, B-cell, 3 |
| 109565 | Lymphoma, B-cell |
| 109690 | Asthma, nocturnal, susceptibility to |
| 109700 | Hemodialysis-related amyloidosis |
| 110100 | Blepharophimosis, epicanthus inversus, and ptosis, type 1 |
| 110700 | Vivax malaria, susceptibility to |
| 112250 | Bone dysplasia with medullary fibrosarcoma |
| 112261 | Fibrodysplasia ossificans progressiva |
| 112262 | Fibrodysplasia ossificans progressiva, 135100 |
| 112410 | Hypertension with brachydactyly |
| 113100 | Brachydactyly, type C |
| 113520 | Hyperleucinemia-isoleucinemia or hypervalinemia |
| 113721 | Breast cancer |
| 113811 | Epidermolysis bullosa, generalized atrophic benign, 226650 |
| 113900 | Heart block, progressive familial, type I |
| 114130 | Osteoporosis |
| 114208 | Malignant hyperthermia susceptibility 5, 601887 |
| 114240 | Muscular dystrophy, limb-girdle, type 2A, 253600 |
| 114290 | Campomelic dysplasia with autosomal sex reversal |
| 114350 | Leukemia, acute myeloid |
| 114400 | Lynch cancer family syndrome II |
| 114550 | Hepatocellular carcinoma |
| 114835 | Monocyte carboxyesterase deficiency |
| 115200 | Cardiomyopathy, dilated, 1A |
| 115470 | Cat eye syndrome |
| 115500 | Acatalasemia |
| 115650 | Cataract, anterior polar-1 |
| 115660 | Cataract, cerulean, type 1 |
| 115665 | Cataract, congenital, Volkmann type |
| 116600 | Cataract, posterior polar |
| 116800 | Cataract, Marner type |
| 116806 | Colorectal cancer |
| 116860 | Cavernous angiomatous malformations |
| 117700 | [Hypoceruloplasminemia, hereditary] |
| 118210 | Charcot-Marie-Tooth neuropathy-2A |
| 118425 | Myotonia congenita, dominant, 160800 |
| 118470 | [CETP deficiency] |

TABLE 5-continued

| OMIM Reference | Description |
|---|---|
| 118485 | Polycystic ovary syndrome with hyperandrogenemia |
| 118504 | Epilepsy, benign neonatal, type 1, 121200 |
| 118511 | Schizophrenia, neurophysiologic defect in |
| 118800 | Choreoathetosis, familial paroxysmal |
| 119300 | van der Woude syndrome |
| 119530 | Orofacial cleft-1 |
| 120070 | Alport syndrome, autosomal recessive, 203780 |
| 120110 | Metaphyseal chondrodysplasia, Schmid type |
| 120120 | Epidermolysis bullosa dystrophica, dominant, 131750 |
| 120131 | Alport syndrome, autosomal recessive, 203780 |
| 120140 | Osteoarthrosis, precocious |
| 120150 | Osteogenesis imperfecta, 4 clinical forms, 166200, 166210, 259420, 166220 |
| 120160 | Osteogenesis imperfecta, 4 clinical forms, 166200, 166210, 259420, 166220 |
| 120180 | Ehlers-Danlos syndrome, type III |
| 120190 | Ehlers-Danlos syndrome, type I, 130000 |
| 120215 | Ehlers-Danlos syndrome, type I, 130000 |
| 120220 | Bethlem myopathy, 158810 |
| 120240 | Bethlem myopathy, 158810 |
| 120260 | Epiphyseal dysplasia, multiple, type 2, 600204 |
| 120280 | Stickler syndrome, type III |
| 120290 | OSMED syndrome, 215150 |
| 120435 | Muir-Torre syndrome, 158320 |
| 120436 | Muir-Torre family cancer syndrome, 158320 |
| 120550 | C1q deficiency, type A |
| 120570 | C1q deficiency, type B |
| 120575 | C1q deficiency, type C |
| 120580 | C1r/C1s deficiency, combined |
| 120620 | SLE susceptibility |
| 120700 | C3 deficiency |
| 120810 | C4 deficiency |
| 120820 | C4 deficiency |
| 120900 | C5 deficiency |
| 120920 | Measles, susceptibility to |
| 120940 | C9 deficiency |
| 120950 | C8 deficiency, type I |
| 120960 | C8 deficiency, type II |
| 121011 | Deafness, autosomal dominant 3, 601544 |
| 121014 | Heterotaxia, visceroatrial, autosomal recessive |
| 121050 | Contractural arachnodactyly, congenital |
| 121300 | Coproporphyria |
| 121360 | Myeloid leukemia, acute, M4Eo subtype |
| 121800 | Corneal dystrophy, crystalline, Schnyder |
| 122720 | Nicotine addiction, protection from |
| 123000 | Craniometaphyseal dysplasia |
| 123100 | Craniosynostosis, type 1 |
| 123101 | Craniosynostosis, type 2 |
| 123270 | [Creatine kinase, brain type, ectopic expression of] |
| 123580 | Cataract, congenital, autosomal dominant |
| 123620 | Cataract, cerulean, type 2, 601547 |
| 123660 | Cataract, Coppock-like |
| 123829 | Melanoma |
| 123940 | White sponge nevus, 193900 |
| 124020 | Mephenytoin poor metabolizer |
| 124030 | Parkinsonism, susceptibility to |
| 124200 | Darier disease (keratosis follicularis) |
| 125264 | Leukemia, acute nonlymphocytic |
| 125270 | Porphyria, acute hepatic |
| 125370 | Dentatorubro-pallidoluysian atrophy |
| 125490 | Dentinogenesis imperfecta-1 |
| 125660 | Myopathy, desminopathic |
| 125852 | Insulin-dependent diabetes mellitus-2 |
| 126060 | Anemia, megaloblastic, due to DHFR deficiency |
| 126090 | Hyperphenylalaninemia due to pterin-4a-carbinolamine dehydratase deficiency, 264070 |
| 126337 | Myxoid liposarcoma |
| 126340 | Xeroderma pigmentosum, group D, 278730 |
| 126391 | DNA ligase I deficiency |
| 126451 | Schizophrenia, susceptibility to |
| 126452 | Autonomic nervous system dysfunction |
| 126600 | Doyne honeycomb retinal dystrophy |
| 126650 | Chloride diarrhea, congenital, Finnish type, 214700 |
| 128100 | Dystonia-1, torsion |
| 129010 | Neuropathy, congenital hypomyelinating, 1 |
| 129490 | Ectodermal dysplasia-3, anhidrotic |
| 129500 | Ectodermal dysplasia, hidrotic |

TABLE 5-continued

| OMIM Reference | Description |
|---|---|
| 129900 | EEC syndrome-1 |
| 130410 | Glutaricaciduria, type IIB |
| 130500 | Elliptocytosis-1 |
| 130650 | Beckwith-Wiedemann syndrome |
| 131100 | Multiple endocrine neoplasia I |
| 131195 | Hereditary hemorrhagic telangiectasia-1, 187300 |
| 131210 | Atherosclerosis, susceptibility to |
| 131242 | Shah-Waardenburg syndrome, 277580 |
| 131244 | Hirschsprung disease-2, 600155 |
| 131400 | Eosinophilia, familial |
| 131440 | Eosinophilic myeloproliferative disorder |
| 131950 | Epidermolysis bullosa, Ogna type |
| 132700 | Cylindromatosis |
| 132800 | Basal cell carcinoma |
| 132810 | Diphenylhydantoin toxicity |
| 133170 | Erythremia |
| 133171 | [Erythrocytosis, familial], 133100 |
| 133200 | Erythrokeratodermia variabilis |
| 133430 | Breast cancer |
| 133450 | Neuroepithelioma |
| 133510 | Trichothiodystrophy |
| 133530 | Xeroderma pigmentosum, group G, 278780 |
| 133550 | Dicarboxylicaminoaciduria, 222730 |
| 133700 | Chondrosarcoma, 215300 |
| 133701 | Exostoses, multiple, type 2 |
| 133780 | Vitreoretinopathy, exudative, familial |
| 134370 | Membroproliferative glomerulonephritis |
| 134570 | Factor XIIIA deficiency |
| 134580 | Factor XIIIB deficiency |
| 134637 | Autoimmune lymphoproliferative syndrome |
| 134638 | Systemic lupus erythematosus, susceptibility, 152700 |
| 134790 | Hyperferritinemia-cataract syndrome, 600886 |
| 134797 | Shprintzen-Goldberg syndrome, 182212 |
| 134820 | Dysfibrinogenemia, alpha type, causing bleeding diathesis |
| 134830 | Dysfibrinogenemia, beta type |
| 134850 | Dysfibrinogenemia, gamma type |
| 134934 | Thanatophoric dysplasia, types I and II, 187600 |
| 135300 | Fibromatosis, gingival |
| 135600 | Ehlers-Danlos syndrome, type X |
| 135700 | Fibrosis of extraocular muscles, congenital, 1 |
| 135940 | Ichthyosis vulgaris, 146700 |
| 136132 | [Fish-odor syndrome], 602079 |
| 136350 | Pfeiffer syndrome, 101600 |
| 136435 | Ovarian dysgenesis, hypergonadotropic, with normal karyotype, 233300 |
| 136530 | Male infertility, familial |
| 136550 | Macular dystrophy, North Carolina type |
| 136836 | Fucosyltransferase-6 deficiency |
| 137350 | Amyloidosis, Finnish type, 105120 |
| 137600 | Iridogoniodysgenesis syndrome |
| 138030 | [Hyperproglucagonemia] |
| 138033 | Diabetes mellitus, type II |
| 138040 | Cortisol resistance |
| 138079 | Hyperinsulinism, familial, 602485 |
| 138130 | Hyperinsulinism-hyperammonemia syndrome |
| 138140 | Glucose transport defect, blood-brain barrier |
| 138160 | Diabetes mellitus, noninsulin-dependent |
| 138190 | Diabetes mellitus, noninsulin-dependent |
| 138250 | P5CS deficiency |
| 138300 | Hemolytic anemia due to glutathione reductase deficiency |
| 138320 | Hemolytic anemia due to glutathione peroxidase deficiency |
| 138491 | Startle disease, autosomal recessive |
| 138570 | Non-insulin dependent diabetes mellitus, susceptibility to |
| 138571 | Glycogen synthase, liver, deficiency of, 240600 |
| 138700 | [Apolipoprotein H deficiency] |
| 138720 | Bernard-Soulier syndrome, type B |
| 138760 | [Glyoxalase II deficiency] |
| 138971 | Kostmann neutropenia, 202700 |
| 138981 | Pulmonary alveolar proteinosis, 265120 |
| 139130 | Hypertension, essential, susceptibility to, 145500 |
| 139150 | Basal cell carcinoma |
| 139190 | Gigantism due to GHRF hypersecretion |
| 139191 | Growth hormone deficient dwarfism |
| 139250 | Isolated growth hormone deficiency, Illig type with absent GH and Kowarski type with bioinactive GH |
| 139320 | Pituitary ACTH secreting adenoma |
| 139330 | Night blindness, congenital stationary |

TABLE 5-continued

| OMIM Reference | Description |
|---|---|
| 139350 | Epidermolytic hyperkeratosis, 113800 |
| 139360 | Pituitary ACTH-secreting adenoma |
| 140100 | [Anhaptoglobinemia] |
| 141750 | Alpha-thalassemia/mental retardation syndrome, type 1 |
| 141800 | Methemoglobinemias, alpha- |
| 141850 | Thalassemia, alpha- |
| 141900 | Methemoglobinemias, beta- |
| 142000 | Thalassemia due to Hb Lepore |
| 142200 | HPFH, nondeletion type A |
| 142250 | HPFH, nondeletion type G |
| 142270 | Hereditary persistence of fetal hemoglobin |
| 142335 | Hereditary persistence of fetal hemoglobin, heterocellular, Indian type |
| 142360 | Thrombophilia due to heparin cofactor II deficiency |
| 142380 | Hepatocellular carcinoma |
| 142470 | [Hereditary persistence of fetal hemoglobin, heterocellular] |
| 142600 | Hemolytic anemia due to hexokinase deficiency |
| 142640 | Thrombophilia due to elevated HRG |
| 142680 | Periodic fever, familial |
| 142857 | Pemphigoid, susceptibility to |
| 142858 | Beryllium disease, chronic, susceptibility to |
| 142946 | Holoprosencephaly-4 |
| 142959 | Hand-foot-uterus syndrome, 140000 |
| 142989 | Synpolydactyly, type II, 186000 |
| 143100 | Huntington disease |
| 143200 | Wagner syndrome |
| 143890 | Hypercholesterolemia, familial |
| 144120 | Hyperimmunoglobulin G1 syndrome |
| 144200 | Epidermolytic palmoplantar keratoderma |
| 145001 | Hyperparathyroidism-jaw tumor syndrome |
| 145260 | Pseudohypoaldosteronism, type II |
| 145410 | Opitz G syndrome, type II |
| 145505 | Hypertension, essential |
| 145981 | Hypocalciuric hypercalcemia, type II |
| 146150 | Hypomelanosis of Ito |
| 146200 | Hypoparathyroidism, familial |
| 146740 | Neutropenia, alloimmune neonatal |
| 146760 | [IgG receptor I, phagocytic, familial deficiency of] |
| 146790 | Lupus nephritis, susceptibility to |
| 147020 | Agammaglobulinemia, 601495 |
| 147050 | Atopy |
| 147061 | Allergy and asthma susceptibility |
| 147110 | IgG2 deficiency, selective |
| 147141 | Leukemia, acute lymphoblastic |
| 147200 | [Kappa light chain deficiency] |
| 147280 | Hepatocellular carcinoma |
| 147440 | Growth retardation with deafness and mental retardation |
| 147450 | Amytrophic lateral sclerosis, due to SOD1 deficiency, 105400 |
| 147545 | Diabetes mellitus, noninsulin-dependent |
| 147570 | Interferon, immune, deficiency |
| 147575 | Myelodysplastic syndrome, preleukemic |
| 147660 | Interferon, alpha, deficiency |
| 147670 | Rabson-Mendenhall syndrome |
| 147680 | Severe combined immunodeficiency due to IL2 deficiency |
| 147730 | Interleukin-2 receptor, alpha chain, deficiency of |
| 147781 | Atopy, susceptibility to |
| 147790 | Leukemia, acute lymphocytic, with 4/11 translocation |
| 147791 | Jacobsen syndrome |
| 148040 | Epidermolysis bullosa simplex, Koebner, Dowling-Meara, and Weber-Cockayne types, 131900, 131760, 131800 |
| 148041 | Pachyonychia congenita, Jadassohn-Lewandowsky type, 167200 |
| 148043 | Meesmann corneal dystrophy, 122100 |
| 148065 | White sponge nevus, 193900 |
| 148066 | Epidermolysis bullosa simplex, Koebner, Dowling-Meara, and Weber-Cockayne types, 131900, 131760, 131800 |
| 148067 | Nonepidermolytic palmoplantar keratoderma, 600962 |
| 148069 | Pachyonychia congenita, Jackson-Lawler type, 167210 |
| 148070 | Liver disease, susceptibility to, from hepatotoxins or viruses |
| 148080 | Epidermolytic hyperkeratosis, 113800 |
| 148370 | Keratolytic winter erythema |
| 148500 | Tylosis with esophageal cancer |
| 148900 | Klippel-Feil syndrome with laryngeal malformation |
| 150000 | Exertional myoglobinuria due to deficiency of LDH-A |
| 150100 | Lactate dehydrogenase-B deficiency |
| 150200 | [Placental lactogen deficiency] |

TABLE 5-continued

| OMIM Reference | Description |
|---|---|
| 150210 | Lactoferrin-deficient neutrophils, 245480 |
| 150230 | Langer-Giedion syndrome |
| 150240 | Cutis laxa, marfanoid neonatal type |
| 150250 | Larsen syndrome, autosomal dominant |
| 150270 | Laryngeal adductor paralysis |
| 150292 | Epidermolysis bullosa, Herlitz junctional type, 226700 |
| 150310 | Epidermolysis bullosa, Herlitz junctional type, 226700 |
| 151385 | Leukemia, acute myeloid |
| 151390 | Leukemia, acute T-cell |
| 151400 | Leukemia/lymphoma, B-cell, 1 |
| 151410 | Leukemia, chronic myeloid |
| 151440 | Leukemia, T-cell acute lymphoblastoid |
| 151670 | Hepatic lipase deficiency |
| 152200 | Coronary artery disease, susceptibility to |
| 152427 | Long QT syndrome-2 |
| 152445 | Vohwinkel syndrome, 124500 |
| 152760 | Hypogonadotropic hypogonadism due to GNRH deficiency, 227200 |
| 152780 | Hypogonadism, hypergonadotropic |
| 152790 | Precocious puberty, male, 176410 |
| 153454 | Ehlers-Danlos syndrome, type VI, 225400 |
| 153455 | Cutis laxa, recessive, type I, 219100 |
| 153700 | Macular dystrophy, vitelliform type |
| 153840 | Macular dystrophy, atypical vitelliform |
| 153880 | Macular dystrophy, dominant cystoid |
| 153900 | Stargardt disease-2 |
| 154275 | Malignant hyperthermia susceptibility 2 |
| 154276 | Malignant hyperthermia susceptibility 3 |
| 154400 | Acrofacial dysostosis, Nager type |
| 154500 | Treacher Collins mandibulofacial dysostosis |
| 154545 | Chronic infections, due to opsonin defect |
| 154550 | Carbohydrate-deficient glycoprotein syndrome, type Ib, 602579 |
| 154705 | Marfan syndrome, type II |
| 155555 | [Red hair/fair skin] |
| 155600 | Malignant melanoma, cutaneous |
| 156225 | Muscular dystrophy, congenital merosin-deficient |
| 156232 | Mesomelic dysplasia, Kantaputra type |
| 156570 | Methylcobalamin deficiency, cbl G type |
| 156600 | Microcoria, congenital |
| 156845 | Tietz syndrome, 103500 |
| 156850 | Cataract, congenital, with microphthalmia |
| 157140 | Dementia, frontotemporal, with parkinsonism, 601630 |
| 157147 | Abetalipoproteinemia, 200100 |
| 157170 | Holoprosencephaly-2 |
| 157640 | PEO with mitochondrial DNA deletions, type 1 |
| 157655 | Lactic acidosis due to defect in iron-sulfur cluster of complex I |
| 157900 | Moebius syndrome |
| 158590 | Spinal muscular atrophy-4 |
| 159000 | Muscular dystrophy, limb-girdle, type 1A |
| 159001 | Muscular dystrophy, limb-girdle, type 1B |
| 159440 | Charcot-Marie-Tooth neuropathy-1B, 118200 |
| 159555 | Leukemia, myeloid/lymphoid or mixed-lineage |
| 159595 | Leukemia, transient, of Down syndrome |
| 160760 | Cardiomyopathy, familial hypertrophic, 1, 192600 |
| 160777 | Griscelli disease, 214450 |
| 160781 | Cardiomyopathy, hypertrophic, mid-left ventricular chamber type |
| 160900 | Myotonic dystrophy |
| 160980 | Carney myxoma-endocrine complex |
| 161015 | Mitochondrial complex I deficiency, 252010 |
| 162100 | Neuralgic amyotrophy with predilection for brachial plexus |
| 162150 | Obestiy with impaired prohormone processing, 600955 |
| 162200 | Neurofibromatosis, type 1 |
| 162400 | Neuropathy, hereditary sensory and autonomic, type 1 |
| 163729 | Hypertension, pregnancy-induced |
| 163890 | Parkinson disease, type 1, 601508 |
| 163950 | Noonan syndrome-1 |
| 164009 | Leukemia, acute promyelocytic, NUMA/RARA type |
| 164040 | Leukemia, acute promyelocytic, NPM/RARA type |
| 164160 | Obesity, severe, due to leptin deficiency |
| 164200 | Oculodentodigital dysplasia |
| 164500 | Spinocerebellar ataxia-7 |
| 164731 | Ovarian carcinoma, 167000 |
| 164759 | Ovarian carcinoma |
| 164761 | Medullary thyroid carcinoma, 155240 |

TABLE 5-continued

| OMIM Reference | Description |
|---|---|
| 164770 | Myeloid malignancy, predisposition to |
| 164790 | Colorectal cancer |
| 164860 | Renal cell carcinoma, papillary, familial and sporadic |
| 164920 | Piebaldism |
| 164953 | Liposarcoma |
| 165240 | Pallister-Hall syndrome, 146510 |
| 165320 | Hepatocellular carcinoma |
| 165500 | Optic atrophy 1 |
| 166600 | Osteopetrosis, AD, type II |
| 166800 | Otosclerosis |
| 167000 | Ovarian cancer, serous |
| 167250 | Paget disease of bone |
| 167409 | Optic nerve coloboma with renal disease, 120330 |
| 167410 | Rhabdomyosarcoma, alveolar, 268220 |
| 167415 | Hypothyroidism, congenital, due to thyroid dysgenesis or hypoplasia |
| 168000 | Paraganglioma, familial nonchromaffin, 1 |
| 168360 | Paraneoplastic sensory neuropathy |
| 168450 | Hypoparathyroidism, autosomal dominant |
| 168461 | Multiple myeloma, 254250 |
| 168468 | Metaphyseal chondrodysplasia, Murk Jansen type, 156400 |
| 168470 | Humoral hypercalcemia of malignancy |
| 168500 | Parietal foramina |
| 169600 | Hailey-Hailey disease |
| 170261 | Bare lymphocyte syndrome, type I, due to TAP2 deficiency |
| 170500 | Myotonia congenita, atypical acetazolamide-responsive |
| 170650 | Periodontitis, juvenile |
| 170995 | Zellweger syndrome-2 |
| 171050 | Colchicine resistance |
| 171060 | Cholestasis, progressive familial intrahepatic, type III, 602347 |
| 171190 | Hypertension, essential, 145500 |
| 171650 | Lysosomal acid phosphatase deficiency |
| 171760 | Hypophosphatasia, adult, 146300 |
| 171860 | Hemolytic anemia due to phosphofructokinase deficiency |
| 172400 | Hemolytic anemia due to glucosephosphate isomerase deficiency |
| 172411 | Colorectal cancer, resistance to |
| 172430 | Enolase deficiency |
| 172471 | Glycogenosis, hepatic, autosomal |
| 172490 | Phosphorylase kinase deficiency of liver and muscle, 261750 |
| 173110 | Pituitary hormone deficiency, combined |
| 173350 | Plasminogen Tochigi disease |
| 173360 | Thrombophilia due to excessive plasminogen activator inhibitor |
| 173370 | Plasminogen activator deficiency |
| 173470 | Glanzmann thrombasthenia, type B |
| 173610 | Platelet alpha/delta storage pool deficiency |
| 173850 | Polio, susceptibility to |
| 173870 | Xeroderma pigmentosum |
| 173910 | Polycystic kidney disease, adult, type II |
| 174000 | Medullary cystic kidney disease, AD |
| 174810 | Osteolysis, familial expansile |
| 174900 | Polyposis, juvenile intestinal |
| 175100 | Turcot syndrome, 276300 |
| 176000 | Porphyria, acute intermittent |
| 176100 | Porphyria cutanea tarda |
| 176260 | Episodic ataxia/myokymia syndrome, 160120 |
| 176261 | Jervell and Lange-Nielsen syndrome, 220400 |
| 176270 | Prader-Willi syndrome |
| 176300 | [Dystransthyretinemic hyperthyroxinemia] |
| 176310 | Leukemia, acute pre-B-cell |
| 176450 | Sacral agenesis-1 |
| 176640 | Creutzfeldt-Jakob disease, 123400 |
| 176730 | Diabetes mellitus, rare form |
| 176801 | Metachromatic leukodystrophy due to deficiency of SAP-1 |
| 176830 | Obesity, adrenal insufficiency, and red hair |
| 176860 | Purpura fulminans, neonatal |
| 176880 | Protein S deficiency |
| 176930 | Dysprothrombinemia |
| 176943 | Apert syndrome, 101200 |
| 176947 | Selective T-cell defect |
| 176960 | Pituitary tumor, invasive |
| 177070 | Spherocytosis, hereditary, Japanese type |
| 177400 | Apnea, postanesthetic |
| 177900 | Psoriasis susceptibility-1 |
| 178300 | Ptosis, hereditary congenital, 1 |

TABLE 5-continued

| OMIM Reference | Description |
|---|---|
| 178600 | Pulmonary hypertension, familial primary |
| 178640 | Pulmonary alveolar proteinosis, congenital, 265120 |
| 179095 | Male infertility |
| 179450 | Ragweed sensitivity |
| 179605 | Retinitis pigmentosa, digenic |
| 179615 | Reticulosis, familial histiocytic, 267700 |
| 179616 | Severe combined immunodeficiency, B cell-negative, 601457 |
| 179755 | Renal cell carcinoma, papillary, 1 |
| 179820 | [Hyperproreninemia] |
| 180020 | Retinal cone dystrophy-1 |
| 180069 | Retinal dystrophy, autosomal recessive, childhood-onset |
| 180071 | Retinitis pigmentosa, autosomal recessive |
| 180072 | Night blindness, congenital stationary, type 3, 163500 |
| 180090 | Retinitis pigmentosa, autosomal recessive |
| 180100 | Retinitis pigmentosa-1 |
| 180104 | Retinitis pigmentosa-9 |
| 180105 | Retinitis pigmentosa-10 |
| 180200 | Osteosarcoma, 259500 |
| 180240 | Leukemia, acute promyelocytic |
| 180250 | Retinol binding protein, deficiency of |
| 180297 | Anemia, hemolytic, Rh-null, suppressor type, 268150 |
| 180380 | Night blindness, congenital stationery, rhodopsin-related |
| 180381 | Oguchi disease-2, 258100 |
| 180385 | Leukemia, acute T-cell |
| 180721 | Retinitis pigmentosa, digenic |
| 180840 | Susceptibility to IDDM |
| 180860 | Russell-Silver syndrome |
| 180901 | Malignant hyperthermia susceptibility 1, 145600 |
| 181030 | Salivary gland pleomorphic adenoma |
| 181031 | Oguchi disease-1, 258100 |
| 181405 | Scapuloperoneal spinal muscular atrophy, New England type |
| 181430 | Scapuloperoneal syndrome, myopathic type |
| 181460 | Schistosoma mansoni, susceptibility/resistance to |
| 181510 | Schizophrenia |
| 181600 | Sclerotylosis |
| 182138 | Anxiety-related personality traits |
| 182279 | Prader-Willi syndrome |
| 182280 | Small-cell cancer of lung |
| 182290 | Smith-Magenis syndrome |
| 182380 | Glucose/galactose malabsorption |
| 182381 | Renal glucosuria, 253100 |
| 182452 | Lung cancer, small cell |
| 182500 | Cataract, congenital |
| 182600 | Spastic paraplegia-3A |
| 182601 | Spastic paraplegia-4 |
| 182860 | Pyropoikilocytosis |
| 182870 | Spherocytosis-1 |
| 182900 | Spherocytosis-2 |
| 183600 | Split hand/foot malformation, type 1 |
| 185000 | Stomatocytosis I |
| 185430 | Atherosclerosis, susceptibility to |
| 185470 | Myopathy due to succinate dehydrogenase deficiency |
| 185800 | Symphalangism, proximal |
| 186580 | Arthrocutaneouveal granulomatosis |
| 186740 | Immunodeficiency due to defect in CD3-gamma |
| 186770 | Leukemia, T-cell acute lymphocytic |
| 186780 | CD3, zeta chain, deficiency |
| 186830 | Immunodeficiency, T-cell receptor/CD3 complex |
| 186855 | Leukemia-2, T-cell acute lymphoblastic |
| 186860 | Leukemia/lymphoma, T-cell |
| 186880 | Leukemia/lymphoma, T-cell |
| 186921 | Leukemia, T-cell acute lymphoblastic |
| 186940 | [CD4(+) lymphocyte deficiency] |
| 187040 | Leukemia-1, T-cell acute lymphoblastic |
| 187680 | 6-mercaptopurine sensitivity |
| 188025 | Thrombocytopenia, Paris-Trousseau type |
| 188070 | Bleeding disorder due to defective thromboxane A2 receptor |
| 188400 | Velocardiofacial syndrome, 192430 |
| 188450 | Goiter, adolescent multinodular |
| 188540 | Hypothyroidism, nongoitrous |
| 188550 | Thyroid papillary carcinoma |
| 188826 | Sorsby fundus dystrophy, 136900 |
| 189800 | Preeclampsia/eclampsia |
| 189980 | Leukemia, chronic myeloid |
| 190000 | Atransferrinemia |
| 190020 | Bladder cancer, 109800 |

TABLE 5-continued

| OMIM Reference | Description |
|---|---|
| 190040 | Meningioma, SIS-related |
| 190070 | Colorectal adenoma |
| 190100 | Geniospasm |
| 190160 | Thyroid hormone resistance, 274300, 188570 |
| 190182 | Colon cancer |
| 190195 | Ichthyosiform erythroderma, congenital, 242100 |
| 190198 | Leukemia, T-cell acute lymphoblastic |
| 190300 | Tremor, familial essential, 1 |
| 190450 | Hemolytic anemia due to triosephosphate isomerase deficiency |
| 190605 | Triphalangeal thumb-polysyndactyly syndrome |
| 190685 | Down syndrome |
| 190900 | Colorblindness, tritan |
| 191010 | Cardiomyopathy, familial hypertrophic, 3, 115196 |
| 191030 | Nemaline myopathy-1, 161800 |
| 191044 | Cardiomyopathy, familial hypertrophic |
| 191045 | Cardiomyopathy, familial hypertrophic, 2, 115195 |
| 191092 | Tuberous sclerosis-2 |
| 191100 | Tuberous sclerosis-1 |
| 191170 | Colorectal cancer, 114500 |
| 191181 | Cervical carcinoma |
| 191290 | Segawa syndrome, recessive |
| 191315 | Insensitivity to pain, congenital, with anhidrosis, 256800 |
| 191540 | [Urate oxidase deficiency] |
| 192090 | Ovarian carcinoma |
| 192340 | Diabetes insipidus, neurohypophyseal, 125700 |
| 192500 | Jervell and Lange-Nielsen syndrome, 220400 |
| 192974 | Neonatal alloimmune thrombocytopenia |
| 193100 | Hypophosphatemic rickets, autosomal dominant |
| 193235 | Vitreoretinopathy, neovascular inflammatory |
| 193300 | Renal cell carcinoma |
| 193400 | von Willebrand disease |
| 193500 | Rhabdomyosarcoma, alveolar, 268220 |
| 194070 | Wilms tumor, type 1 |
| 194071 | Wilms tumor, type 2 |
| 194190 | Wolf-Hirschhorn syndrome |
| 200150 | Choreoacanthocytosis |
| 200990 | Acrocallosal syndrome |
| 201450 | Acyl-CoA dehydrogenase, medium chain, deficiency of |
| 201460 | Acyl-CoA dehydrogenase, long chain, deficiency of |
| 201470 | Acyl-CoA dehydrogenase, short-chain, deficiency of |
| 201475 | VLCAD deficiency |
| 201810 | 3-beta-hydroxysteroid dehydrogenase, type II, deficiency |
| 201910 | Adrenal hyperplasia, congenital, due to 21-hydroxylase deficiency |
| 202110 | Adrenal hyperplasia, congenital, due to 17-alpha-hydroxylase deficiency |
| 203100 | Waardenburg syndrome/ocular albinism, digenic, 103470 |
| 203200 | Albinism, ocular, autosomal recessive |
| 203300 | Hermansky-Pudlak syndrome |
| 203310 | Ocular albinism, autosomal recessive |
| 203500 | Alkaptonuria |
| 203740 | Alpha-ketoglutarate dehydrogenase deficiency |
| 203750 | 3-ketothiolase deficiency |
| 203800 | Alstrom syndrome |
| 204500 | Ceroid-lipofuscinosis, neuronal 2, classic late infantile |
| 205100 | Amyotrophic lateral sclerosis, juvenile |
| 205900 | Anemia, Diamond-Blackfan |
| 207750 | Hyperlipoproteinemia, type Ib |
| 207800 | Argininemia |
| 208100 | Arthrogryposis multiplex congenita, neurogenic |
| 208250 | Jacobs syndrome |
| 208400 | Aspartylglucosaminuria |
| 208900 | Ataxia-telangiectasia |
| 209900 | Bardet-Biedl syndrome 2 |
| 209901 | Bardet-Biedl syndrome 1 |
| 210900 | Bloom syndrome |
| 211420 | Breast cancer, ductal |
| 212138 | Carnitine-acylcarnitine translocase deficiency |
| 214300 | Klippel-Feil syndrome |
| 214400 | Charcot-Marie-Tooth neuropathy-4A |
| 214500 | Chediak-Higashi syndrome |
| 215700 | Citrullinemia |
| 216550 | Cohen syndrome |
| 216900 | Achromatopsia |
| 216950 | C1r/C1s deficiency, combined |
| 217000 | C2 deficiency |

TABLE 5-continued

| OMIM Reference | Description |
|---|---|
| 217030 | C3b inactivator deficiency |
| 217050 | C6 deficiency |
| 217070 | C7 deficiency |
| 217095 | Conotruncal cardiac anomalies |
| 217300 | Cornea plana congenita, recessive |
| 217800 | Macular corneal dystrophy |
| 218000 | Andermann syndrome |
| 218030 | Apparent mineralocorticoid excess, hypertension due to |
| 219800 | Cystinosis, nephropathic |
| 221770 | Polycystic lipomembranous osteodysplasia with sclerosing leukencephalopathy |
| 221820 | Gliosis, familial progressive subcortical |
| 222100 | Diabetes mellitus, insulin-dependent-1 |
| 222600 | Atelosteogenesis II, 256050 |
| 222700 | Lysinuric protein intolerance |
| 222745 | DECR deficiency |
| 222800 | Hemolytic anemia due to bisphosphoglycerate mutase deficiency |
| 222900 | Sucrose intolerance |
| 223000 | Lactase deficiency, adult, 223100 |
| 223360 | Dopamine-beta-hydroxylase deficiency |
| 223900 | Dysautonomia, familial |
| 224100 | Congenital dyserythropoietic anemia II |
| 224120 | Dyserythropoietic anemia, contenital, type I |
| 225500 | Ellis-van Creveld syndrome |
| 226450 | Epidermolysis bullosa inversa, junctional |
| 227220 | [Eye color, brown] |
| 227400 | Thromboembolism susceptibility due to factor V Leiden |
| 227500 | Factor VII deficiency |
| 227600 | Factor X deficiency |
| 227645 | Fanconi anemia, type C |
| 227646 | Fanconi anemia, type D |
| 227650 | Fanconi anemia, type A |
| 228960 | [Kininogen deficiency] |
| 229300 | Friedreich ataxia |
| 229600 | Fructose intolerance |
| 229700 | Fructose-bisphosphatase deficiency |
| 229800 | [Fructosuria] |
| 230000 | Fucosidosis |
| 230200 | Galactokinase deficiency with cataracts |
| 230350 | Galactose epimerase deficiency |
| 230400 | Galactosemia |
| 230450 | Hemolytic anemia due to gamma-glutamylcysteine synthetase deficiency |
| 230800 | Gaucher disease |
| 231550 | Achalasia-addisonianism-alacrimia syndrome |
| 231670 | Glutaricaciduria, type I |
| 231675 | Glutaricaciduria, type IIC |
| 231680 | Glutaricaciduria, type IIA |
| 231950 | Glutathioninuria |
| 232000 | Propionicacidemia, type I or pccA type |
| 232050 | Propionicacidemia, type II or pccB type |
| 232300 | Glycogen storage disease II |
| 232400 | Glycogen storage disease IIIa |
| 232500 | Glycogen storage disease IV |
| 232600 | McArdle disease |
| 232700 | Glycogen storage disease VI |
| 232800 | Glycogen storage disease VII |
| 233100 | [Renal glucosuria] |
| 233700 | Chronic granulomatous disease due to deficiency of NCF-1 |
| 233710 | Chronic granulomatous disease due to deficiency of NCF-2 |
| 234000 | Factor XII deficiency |
| 234200 | Neurodegeneration with brain iron accumulation |
| 235200 | Hemochromatosis |
| 235800 | [Histidinemia] |
| 236100 | Holoprosencephaly-1 |
| 236200 | Homocystinuria, B6-responsive and nonresponsive types |
| 236250 | Homocystinuria due to MTHFR deficiency |
| 236700 | McKusick-Kaufman syndrome |
| 236730 | Urofacial syndrome |
| 237300 | Carbamoylphosphate synthetase I deficiency |
| 238300 | Hyperglycinemia, nonketotic, type I |
| 238310 | Hyperglycinemia, nonketotic, type II |
| 238600 | Chylomicronemia syndrome, familial |
| 238970 | HHH syndrome |
| 239100 | Van Buchem disease |
| 239500 | Hyperprolinemia, type I |

TABLE 5-continued

| OMIM Reference | Description |
|---|---|
| 240300 | Autoimmune polyglandular disease, type I |
| 240400 | Scurvy |
| 243500 | Isovalericacidemia |
| 245000 | Papillon-Lefevre syndrome |
| 245050 | Ketoacidosis due to SCOT deficiency |
| 245200 | Krabbe disease |
| 245349 | Lacticacidemia due to PDX1 deficiency |
| 245900 | Norum disease |
| 246450 | HMG-CoA lyase deficiency |
| 246530 | Leukotriene C4 synthase deficiency |
| 246600 | Pancreatic lipase deficiency |
| 246900 | Lipoamide dehydrogenase deficiency |
| 247200 | Miller-Dieker lissencephaly syndrome |
| 247640 | Leukemia, acute lymphoblastic |
| 248510 | Mannosidosis, beta- |
| 248600 | Maple syrup urine disease, type Ia |
| 248610 | Maple syrup urine disease, type II |
| 248611 | Maple syrup urine disease, type Ib |
| 249000 | Meckel syndrome |
| 249100 | Familial Mediterranean fever |
| 249270 | Thiamine-responsive megaloblastic anemia |
| 250100 | Metachromatic leukodystrophy |
| 250250 | Cartilage-hair hypoplasia |
| 250790 | Methemoglobinemia due to cytochrome b5 deficiency |
| 250800 | Methemoglobinemia, type I |
| 250850 | Hypermethioninemia, persistent, autosomal dominant, due to methionine adenosyltransferase I/III deficiency |
| 251000 | Methylmalonicaciduria, mutase deficiency type |
| 251170 | Mevalonicaciduria |
| 251600 | Microphthalmia, autosomal recessive |
| 252500 | Mucolipidosis II |
| 252800 | Mucopolysaccharidosis Ih |
| 252900 | Sanfilippo syndrome, type A |
| 252940 | Sanfilippo syndrome, type D |
| 253000 | Mucopolysaccharidosis IV A |
| 253200 | Maroteaux-Lamy syndrome, several forms |
| 253250 | Mulibrey nanism |
| 253270 | Multiple carboxylase deficiency, biotin-responsive |
| 253601 | Miyoshi myopathy, 254130 |
| 253700 | Muscular dystrophy, limb-girdle, type 2C |
| 253800 | Walker-Warburg syndrome, 236670 |
| 254210 | Myasthenia gravis, familial infantile |
| 254770 | Epilepsy, juvenile myoclonic |
| 254780 | Myoclonus epilepsy, Lafora type |
| 255800 | Schwartz-Jampel syndrome |
| 256030 | Nemaline myopathy-2 |
| 256100 | Nephronophthisis, juvenile |
| 256540 | Galactosialidosis |
| 256550 | Sialidosis, type I |
| 256700 | Neuroblastoma |
| 256731 | Ceroid-lipofuscinosis, neuronal-5, variant late infantile |
| 256850 | Giant axonal neuropathy-1 |
| 257200 | Niemann-Pick disease, type A |
| 257220 | Niemann-Pick disease, type C |
| 258501 | 3-methylglutaconicaciduria, type III |
| 258870 | Gyrate atrophy of choroid and retina with ornithinemia, B6 responsive or unresponsive |
| 258900 | Oroticaciduria |
| 259700 | Osteopetrosis, recessive |
| 259730 | Renal tubular acidosis-osteopetrosis syndrome |
| 259770 | Osteoporosis-pseudoglioma syndrome |
| 259900 | Hyperoxaluria, primary, type 1 |
| 261510 | Pseudo-Zellweger syndrome |
| 261515 | Peroxisomal bifunctional enzyme deficiency |
| 261600 | Phenylketonuria |
| 261640 | Phenylketonuria due to PTS deficiency |
| 261670 | Myopathy due to phosphoglycerate mutase deficiency |
| 262000 | Bjornstad syndrome |
| 263200 | Polycystic kidney disease, autosomal recessive |
| 263700 | Porphyria, congenital erythropoietic |
| 264300 | Pseudohermaphroditism, male, with gynecomastia |
| 264470 | Adrenoleukodystrophy, pseudoneonatal |
| 264700 | Pseudo-vitamin D dependency rickets 1 |
| 266100 | Pyridoxine dependency with seizures |
| 266150 | Pyruvate carboxylase deficiency |
| 266200 | Anemia, hemolytic, due to PK deficiency |
| 266300 | [Hair color, red] |

TABLE 5-continued

| OMIM Reference | Description |
|---|---|
| 266600 | Inflammatory bowel disease-1 |
| 267750 | Knobloch syndrome |
| 268800 | Sandhoff disease, infantile, juvenile, and adult forms |
| 268900 | [Sarcosinemia] |
| 269920 | Salla disease |
| 270100 | Situs inversus viscerum |
| 270200 | Sjogren-Larsson syndrome |
| 270800 | Spastic paraplegia-5A |
| 271245 | Spinocerebellar ataxia-8, infantile, with sensory neuropathy |
| 271900 | Canavan disease |
| 272750 | GM2-gangliosidosis, AB variant |
| 272800 | Tay-Sachs disease |
| 273300 | Male germ cell tumor |
| 273800 | Thrombocytopenia, neonatal alloimmune |
| 274180 | Thromboxane synthase deficiency |
| 274270 | Thymine-uraciluria |
| 274600 | Pendred syndrome |
| 275200 | Thyroid adenoma, hyperfunctioning |
| 275350 | Transcobalamin II deficiency |
| 276000 | Pancreatitis, hereditary, 167800 |
| 276600 | Tyrosinemia, type II |
| 276700 | Tyrosinemia, type I |
| 276710 | Tyrosinemia, type III |
| 276900 | Usher syndrome, type 1A |
| 276901 | Usher syndrome, type 2 |
| 276902 | Usher syndrome, type 3 |
| 276903 | Usher syndrome, type 1B |
| 276904 | Usher syndrome, type 1C |
| 277700 | Werner syndrome |
| 277730 | Wernicke-Korsakoff syndrome, susceptibility to |
| 277900 | Wilson disease |
| 278000 | Wolman disease |
| 278250 | Wrinkly skin syndrome |
| 278300 | Xanthinuria, type I |
| 278700 | Xeroderma pigmentosum, group A |
| 278760 | Xeroderma pigmentosum, group F |
| 300000 | Opitz G syndrome, type I |
| 300008 | Nephrolithiasis, type I, 310468 |
| 300011 | Menkes disease, 309400 |
| 300031 | Mental retardation, X-linked, FRAXF type |
| 300032 | Alpha-thalassemia/mental retardation syndrome, type 2, 301040 |
| 300037 | Simpson dysmorphia syndrome, 312870 |
| 300039 | Deafness, X-linked 3, conductive, with stapes fixation, 304400 |
| 300044 | Wernicke-Korsakoff syndrome, susceptibility to |
| 300046 | Mental retardation, X-linked 23, nonspecific |
| 300047 | Mental retardation, X-linked 20 |
| 300048 | Intestinal pseudoobstruction, neuronal, X-linked |
| 300049 | Nodular heterotopia, bilateral periventricular |
| 300055 | Mental retardation with psychosis, pyramidal signs, and macroorchidism |
| 300062 | Mental retardation, X-linked 14 |
| 300066 | Deafness, X-linked 6, sensorineural |
| 300067 | Subcortical laminar heterotopia, X-linked dominant |
| 300071 | Night blindness, congenital stationary, type 2 |
| 300075 | Coffin-Lowry syndrome, 303600 |
| 300076 | Wood neuroimmunologic syndrome |
| 300077 | Mental retardation, X-linked 29 |
| 300088 | Epilepsy, female restricted, with mental retardation |
| 300100 | Adrenoleukodystrophy |
| 300104 | Mental retardation, X-linked nonspecific, 309541 |
| 300110 | Night blindness, congenital stationary, X-linked incomplete, 300071 |
| 300121 | Subcortical laminal heteropia, X-linked, 300067 |
| 300123 | Mental retardation with isolated growth hormone deficiency |
| 300126 | Dyskeratosis congenita-1, 305000 |
| 300127 | Mental retardation, X-linked, 60 |
| 300136 | Diabetes mellitus, insulin-dependent, X-linked, susceptibility to |
| 300300 | XLA and isolated growth hormone deficiency, 307200 |
| 300310 | Agammaglobulinemia, type 2, X-linked |
| 300500 | Ocular albinism, Nettleship-Falls type |
| 300600 | Ocular albinism, Forsius-Eriksson type |
| 300650 | Ocular albinism with sensorineural deafness |
| 301000 | Thrombocytopenia, X-linked, 313900 |
| 301200 | Amelogenesis imperfecta |

TABLE 5-continued

| OMIM Reference | Description |
|---|---|
| 301201 | Amelogenesis imperfecta-3, hypoplastic type |
| 301220 | Partington syndrome II |
| 301300 | Anemia, sideroblastic/hypochromic |
| 301310 | Anemia, sideroblastic, with spinocerebellar ataxia |
| 301500 | Fabry disease |
| 301590 | Anophthalmos-1 |
| 301830 | Arthrogryposis, X-linked (spinal muscular atrophy, infantile, X-linked) |
| 301835 | Arts syndrome |
| 301845 | Bazex syndrome |
| 301900 | Borjeson-Forssman-Lehmann syndrome |
| 302060 | Noncompaction of left ventricular myocardium, isolated |
| 302350 | Nance-Horan syndrome |
| 302801 | Charcot-Marie-Tooth neuropathy, X-linked-2, recessive |
| 302950 | Chondrodysplasia punctata, X-linked recessive, 302940 |
| 302960 | Chondrodysplasia punctata, X-linked dominant |
| 303400 | Cleft palate, X-linked |
| 303630 | Alport syndrome, 301050 |
| 303631 | Leiomyomatosis, diffuse, with Alport syndrome |
| 303700 | Colorblindness, blue monochromatic |
| 303800 | Colorblindness, deutan |
| 303900 | Colorblindness, protan |
| 304020 | Cone dystrophy, progressive X-linked, 1 |
| 304040 | Charcot-Marie-Tooth neuropathy, X-linked-1, dominant, 302800 |
| 304050 | Aicardi syndrome |
| 304110 | Craniofrontonasal dysplasia |
| 304340 | Mental retardation, X-linked, syndromic-5, with Dandy-Walker malformation, basal ganglia disease, and seizures |
| 304500 | Deafness, X-linked 2, perceptive congenital |
| 304700 | Mohr-Tranebjaerg syndrome |
| 304800 | Diabetes insipidus, nephrogenic |
| 305100 | Anhidrotic ectodermal dysplasia |
| 305400 | Aarskog-Scott syndrome |
| 305435 | Heterocellular hereditary persistence of fetal hemoglobin, Swiss type |
| 305450 | FG syndrome |
| 305900 | Favism |
| 306000 | Glycogenosis, X-linked hepatic, type I |
| 306100 | Gonadal dysgenesis, XY female type |
| 306400 | Chronic granulomatous disease, X-linked |
| 306700 | Hemophilia A |
| 306900 | Hemophilia B |
| 306995 | [Homosexuality, male] |
| 307150 | Hypertrichosis, congenital generalized |
| 307700 | Hypoparathyroidism, X-linked |
| 307800 | Hypophosphatemia, hereditary |
| 308000 | HPRT-related gout |
| 308230 | Immunodeficiency, X-linked, with hyper-IgM |
| 308240 | Lymphoproliferative syndrome, X-linked |
| 308300 | Incontinentia pigmenti, sporadic type |
| 308310 | Incontinentia pigmenti, familial |
| 308380 | Severe combined immunodeficiency, X-linked, 300400 |
| 308700 | Kallmann syndrome |
| 308800 | Keratosis follicularis spinulosa decalvans |
| 308840 | Spastic paraplegia, 312900 |
| 309000 | Lowe syndrome |
| 309200 | Manic-depressive illness, X-linked |
| 309300 | Megalocornea, X-linked |
| 309470 | Mental retardation, X-linked, syndromic-3, with spastic diplegia |
| 309500 | Renpenning syndrome-1 |
| 309510 | Mental retardation, X-linked, syndromic-1, with dystonic movements, ataxia, and seizures |
| 309530 | Mental retardation, X-linked 1, non-dysmorphic |
| 309545 | Mental retardation, X-linked nonspecific, with aphasia |
| 309548 | Mental retardation, X-linked, FRAXE type |
| 309555 | Gustavson syndrome |
| 309585 | Mental retardation, X-linked, syndromic-6, with gynecomastia and obesity |
| 309600 | Allan-Herndon syndrome |
| 309605 | Mental retardation, X-linked, syndromic-4, with congenital contractures and low fingertip arches |
| 309610 | Mental retardation, X-linked, syndromic-2, with dysmorphism and cerebral atrophy |
| 309620 | Mental retardation-skeletal dysplasia |
| 309850 | Brunner syndrome |
| 309900 | Mucopolysaccharidosis II |
| 310300 | Emery-Dreifuss muscular dystrophy |
| 310400 | Myotubular myopathy, X-linked |
| 310460 | Myopia-1 |
| 310490 | Cowchock syndrome |
| 310500 | Night blindness, congenital stationary, type 1 |
| 311050 | Optic atrophy, X-linked |
| 311200 | Oral-facial-digital syndrome 1 |
| 311250 | Ornithine transcarbamylase deficiency |
| 311300 | Otopalatodigital syndrome, type I |
| 311360 | Ovarian failure, premature |
| 311510 | Waisman parkinsonism-mental retardation syndrome |
| 311800 | Myoglobinuria/hemolysis due to PGK deficiency |
| 311850 | Phosphoribosyl pyrophosphate synthetase-related gout |
| 311870 | Muscle glycogenosis |
| 312000 | Panhypopituitarism, X-linked |
| 312040 | N syndrome, 310465 |
| 312060 | Properdin deficiency, X-linked |
| 312080 | Pelizaeus-Merzbacher disease |
| 312170 | Pyruvate dehydrogenase deficiency |
| 312600 | Retinitis pigmentosa-2 |
| 312610 | Retinitis pigmentosa-3 |
| 312700 | Retinoschisis |
| 312760 | Turner syndrome |
| 313350 | Split hand/foot malformation, type 2 |
| 313400 | Spondyloepiphyseal dysplasia tarda |
| 313700 | Perineal hypospadias |
| 313850 | Thoracoabdominal syndrome |
| 314200 | [Euthyroidal hyper- and hypothyroxinemia] |
| 314250 | Dystonia-3, torsion, with parkinsonism, Filipino type |
| 314300 | Goeminne TKCR syndrome |
| 314400 | Cardiac valvular dysplasia-1 |
| 314580 | Wieacker-Wolff syndrome |
| 314850 | McLeod phenotype |
| 600020 | Prostate cancer, 176807 |
| 600035 | Schizencephaly |
| 600040 | Colorectal cancer |
| 600044 | Thrombocythemia, essential, 187950 |
| 600045 | Xeroderma pigmentosum, group E, subtype 2 |
| 600048 | Breast cancer-3 |
| 600059 | Retinitis pigmentosa-13 |
| 600065 | Leukocyte adhesion deficiency, 116920 |
| 600079 | Colon cancer |
| 600095 | Split hand/foot malformation, type 3 |
| 600101 | Deafness, autosomal dominant 2 |
| 600105 | Retinitis pigmentosa-12, autosomal recessive |
| 600119 | Muscular dystrophy, Duchenne-like, type 2 |
| 600138 | Retinitis pigmentosa-11 |
| 600140 | Rubenstein-Taybi syndrome, 180849 |
| 600143 | Epilepsy, progressive, with mental retardation |
| 600151 | Bardet-Biedl syndrome 3 |
| 600160 | Melanoma, 155601 |
| 600163 | Long QT syndrome-3 |
| 600173 | SCID, autosomal recessive, T-negative/B-positive type |
| 600175 | Spinal muscular atrophy, congenital nonprogressive, of lower limbs |
| 600179 | Leber congenital amaurosis, type I, 204000 |
| 600184 | Carnitine acetyltransferase deficiency |
| 600185 | Pancreatic cancer |
| 600194 | Ichthyosis bullosa of Siemens, 146800 |
| 600202 | Dyslexia, specific, 2 |
| 600211 | Cleidocranial dysplasia, 119600 |
| 600221 | Venous malformations, multiple cutaneous and mucosal, 600195 |
| 600223 | Spinocerebellar ataxia-4 |
| 600225 | Phenylketonuria, atypical, due to GCH1 deficiency, 233910 |
| 600228 | Pseudohypoaldosteronism, type I, 264350 |
| 600231 | Palmoplantar keratoderma, Bothnia type |
| 600234 | HMG-CoA synthease-2 deficiency |
| 600243 | Temperature-sensitive apoptosis |
| 600258 | Colorectal cancer, hereditary nonpolyposis, type 3 |
| 600259 | Turcot syndrome with glioblastoma, 276300 |
| 600261 | Ehlers-Danlos-like syndrome |
| 600266 | Resistance/susceptibility to TB, etc. |
| 600273 | Polycystic kidney disease, infantile severe, with tuberous sclerosis |

TABLE 5-continued

| OMIM Reference | Description |
|---|---|
| 600276 | Cerebral arteriopathy with subcortical infarcts and leukoencephalopathy, 125310 |
| 600281 | Non-insulin-dependent diabetes mellitus, 125853 |
| 600309 | Atrioventricular canal defect-1 |
| 600310 | Pseudoachondroplasia, 177170 |
| 600318 | Diabetes mellitus, insulin-dependent, 3 |
| 600319 | Diabetes mellitus, insulin-dependent, 4 |
| 600320 | Insulin-dependent diabetes mellitus-5 |
| 600321 | Diabetes mellitus, insulin-dependent, 7 |
| 600332 | Rippling muscle disease-1 |
| 600354 | Spinal muscular atrophy-1, 253300 |
| 600359 | Bartter syndrome, type 2 |
| 600363 | Spastic paraplegia-6 |
| 600364 | Cone dystrophy-3, 602093 |
| 600374 | Bardet-Biedl syndrome 4 |
| 600414 | Adrenoleukodystrophy, neonatal, 202370 |
| 600415 | Ataxia with isolated vitamin E deficiency, 277460 |
| 600429 | [Ii blood group, 110800] |
| 600509 | Persistent hyperinsulinemic hypoglycemia of infancy, 256450 |
| 600510 | Pigment dispersion syndrome |
| 600511 | Schizophrenia-3 |
| 600512 | Epilepsy, partial |
| 600525 | Trichodontoosseous syndrome, 190320 |
| 600528 | CPT deficiency, hepatic, type I, 255120 |
| 600536 | Myopathy, congenital |
| 600542 | Chondrosarcoma, extraskeletal myxoid |
| 600584 | Atrial septal defect with atrioventricular conduction defects, 108900 |
| 600593 | Craniosynostosis, Adelaide type |
| 600617 | Lipoid adrenal hyperplasia, 201710 |
| 600618 | Leukemia, acute lymphoblastic |
| 600623 | Prostate cancer, 176807 |
| 600624 | Cone-rod retinal dystrophy-1 |
| 600631 | Enuresis, nocturnal, 1 |
| 600650 | Myopathy due to CPT II deficiency, 255110 |
| 600652 | Deafness, autosomal dominant 4 |
| 600669 | Epilepsy, generalized, idiopathic |
| 600678 | Cancer susceptibility |
| 600698 | Salivary adenoma |
| 600700 | Lipoma |
| 600701 | Lipoma |
| 600722 | Ceroid lipofuscinosis, neuronal, variant juvenile type, with granular osmiophilic deposits |
| 600725 | Holoprosencephaly-3, 142945 |
| 600757 | Orofacial cleft-3 |
| 600759 | Alzheimer disease-4 |
| 600760 | Pseudohypoaldosteronism, type I, 264350 |
| 600761 | Pseudohypoaldosteronism, type I, 264350 |
| 600792 | Deafness, autosomal recessive 5 |
| 600795 | Dementia, familial, nonspecific |
| 600807 | Bronchial asthma |
| 600808 | Enuresis, nocturnal, 2 |
| 600811 | Xeroderma pigmentosum, group E, DDB-negative subtype, 278740 |
| 600835 | AIDS, resistance to |
| 600837 | Hirschsprung disease, 142623 |
| 600839 | Bartter syndrome, 241200 |
| 600850 | Schizophrenia disorder-4 |
| 600852 | Retinitis pigmentosa-17 |
| 600856 | Beckwith-Wiedemann syndrome, 130650 |
| 600881 | Cataract, congenital, zonular, with sutural opacities |
| 600882 | Charcot-Marie-Tooth neuropathy-2B |
| 600883 | Diabetes mellitus, insulin-dependent, 8 |
| 600884 | Cardiomyopathy, familial dilated 1B |
| 600887 | Endometrial carcinoma |
| 600897 | Cataract, zonular pulverulent-1, 116200 |
| 600900 | Muscular dystrophy, limb-girdle, type 2E |
| 600918 | Cystinuria, type III |
| 600919 | Long QT syndrome-4 with sinus bradycardia |
| 600923 | Porphyria variegata, 176200 |
| 600937 | Persistent hyperinsulinemic hypoglycemia of infancy, 256450 |
| 600946 | Short stature, autosomal dominant, with normal serum growth hormone binding protein |
| 600956 | Persistent Mullerian duct syndrome, type II, 261550 |
| 600957 | Persistent Mullerian duct syndrome, type I, 261550 |
| 600958 | Cardiomyopathy, familial hypertrophic, 4, 115197 |
| 600965 | Deafness, autosomal dominant 6 |
| 600968 | Gitelman syndrome, 263800 |
| 600971 | Deafness, autosomal recessive 6 |
| 600974 | Deafness, autosomal recessive 7 |
| 600975 | Glaucoma 3, primary infantile, B |
| 600977 | Cone dystrophy, progressive |
| 600983 | Pseudohypoaldosteronism type I, autosomal dominant, 177735 |
| 600993 | Pancreatic cancer |
| 600994 | Deafness, autosomal dominant 5 |
| 600995 | Nephrotic syndrome, idiopathic, steroid-resistant |
| 600996 | Arrhythmogenic right ventricular dysplasia-2 |
| 600998 | Bleeding diathesis due to GNAQ deficiency |
| 601002 | 5-oxoprolinuria, 266130 |
| 601011 | Spinocerebellar ataxia-6, 183086 |
| 601071 | Deafness, autosomal recessive 9 |
| 601072 | Deafness, autosomal recessive 8 |
| 601090 | Iridogoniodysgenesis, 601631 |
| 601097 | Neuropathy, recurrent, with pressure palsies, 162500 |
| 601105 | Pycnodysostosis, 265800 |
| 601107 | Dubin-Johnson syndrome, 237500 |
| 601130 | Tolbutamide poor metabolizer |
| 601145 | Epilepsy, progressive myoclonic 1, 254800 |
| 601146 | Brachydactyly, type C, 113100 |
| 601154 | Cardiomyopathy, dilated, 1E |
| 601199 | Neonatal hyperparathyroidism, 239200 |
| 601202 | Cataract, anterior polar-2 |
| 601208 | Insulin-dependent diabetes mellitus-11 |
| 601226 | Progressive external ophthalmoplegia, type 2 |
| 601238 | Cerebellar ataxia, Cayman type |
| 601267 | HIV infection, susceptibility/resistence to |
| 601277 | Ichthyosis, lamellar, type 2 |
| 601282 | Muscular dystrophy with epidermolysis bullosa simplex, 226670 |
| 601284 | Hereditary hemorrhagic telangiectasia-2, 600376 |
| 601295 | Bile acid malabsorption, primary |
| 601309 | Basal cell carcinoma, sporadic |
| 601313 | Polycystic kidney disease, adult type I, 173900 |
| 601316 | Deafness, autosomal dominant 10 |
| 601318 | Diabetes mellitus, insulin-dependent, 13 |
| 601362 | DiGeorge syndrome/velocardiofacial syndrome complex-2 |
| 601363 | Wilms tumor, type 4 |
| 601369 | Deafness, autosomal dominant 9 |
| 601373 | HIV infection, susceptibility/resistance to |
| 601382 | Charcot-Marie-Tooth neuropathy-4B |
| 601385 | Prostate cancer |
| 601386 | Deafness, autosomal recessive 12 |
| 601387 | Breast cancer |
| 601399 | Platelet disorder, familial, with associated myeloid malignancy |
| 601402 | Leukemia, myeloid, acute |
| 601406 | B-cell non-Hodgkin lymphoma, high-grade |
| 601410 | Diabetes mellitus, transient neonatal |
| 601411 | Muscular dystrophy, limb-girdle, type 2F, 601287 |
| 601412 | Deafness, autosomal dominant 7 |
| 601414 | Retinitis pigmentosa-18 |
| 601455 | Hereditary motor and sensory neuropathy, Lom type |
| 601458 | Inflammatory bowel disease-2 |
| 601471 | Moebius syndrome-2 |
| 601472 | Charcot-Marie-Tooth neuropathy-2D |
| 601493 | Cardiomyopathy, dilated 1C |
| 601494 | Cardiomyopathy, familial, dilated-2 |
| 601498 | Peroxisomal biogenesis disorder, complementation group 4 |
| 601517 | Spinocerebellar ataxia-2, 183090 |
| 601518 | Prostate cancer, hereditary, 1, 176807 |
| 601542 | Rieger syndrome, type 1, 180500 |
| 601545 | Lissencephaly-1 |
| 601556 | Spinocerebellar ataxia-1, 164400 |
| 601567 | Combined factor V and VIII deficiency, 227300 |
| 601596 | Charcot-Marie-Tooth neuropathy, demyelinating |
| 601604 | Mycobacterial and salmonella infections, susceptibility to |
| 601606 | Trichoepithelioma, multiple familial |
| 601607 | Rhabdoid tumors |
| 601620 | Holt-Oram syndrome, 142900 |
| 601621 | Ulnar-mammary syndrome, 181450 |
| 601622 | Saethre-Chotzen syndrome, 101400 |

TABLE 5-continued

| OMIM Reference | Description |
|---|---|
| 601623 | Angelman syndrome |
| 601649 | Blepharophimosis, epicanthus inversus, and ptosis, type 2 |
| 601650 | Paraganglioma, familial nonchromaffin, 2 |
| 601652 | Glaucoma 1A, primary open angle, juvenile-onset, 137750 |
| 601653 | Branchiootic syndrome |
| 601666 | Insulin-dependent diabetes mellitus-15 |
| 601669 | Hirschsprung disease, one form |
| 601676 | Acute insulin response |
| 601680 | Distal arthrogryposis, type 2B |
| 601682 | Glaucoma 1C, primary open angle |
| 601687 | Meesmann corneal dystrophy, 122100 |
| 601690 | Platelet-activating factor acetylhydrolase deficiency |
| 601691 | Retinitis pigmentosa-19, 601718 |
| 601692 | Reis-Bucklers corneal dystrophy |
| 601718 | Retinitis pigmentosa-19 |
| 601728 | Bannayan-Zonana syndrome, 153480 |
| 601744 | Systemic lupus erythematosus, susceptibility to, 1 |
| 601757 | Rhizomelic chondrodysplasia punctata, type 1, 215100 |
| 601768 | Leukemia, acute myeloid |
| 601769 | Osteoporosis, involutional |
| 601771 | Glaucoma 3A, primary infantile, 231300 |
| 601777 | Cone dystrophy, progressive |
| 601780 | Ceroid-lipofuscinosis, neuronal-6, variant late infantile |
| 601785 | Carbohydrate-deficient glycoprotein syndrome, type I, 212065 |
| 601800 | [Hair color, brown] |
| 601843 | Hypothyroidism, congenital, 274400 |
| 601844 | Pseudohypoaldosteronism type II |
| 601846 | Muscular dystrophy with rimmed vacuoles |
| 601847 | Progressive intrahepatic cholestasis-2 |
| 601850 | Retinitis pigmentosa-deafness syndrome |
| 601863 | Bare lymphocyte syndrome, complementation group C |
| 601868 | Deafness, autosomal dominant 13 |
| 601884 | [High bone mass] |
| 601885 | Cataract, zonular pulverulent-2 |
| 601889 | Lymphoma, diffuse large cell |
| 601916 | Pancreatic cancer |
| 601920 | Alagille syndrome, 118450 |
| 601928 | Monilethrix, 158000 |
| 601941 | Insulin-dependent diabetes mellitus-6 |
| 601954 | Muscular dystrophy, limb-girdle, type 2G |
| 601969 | Medulloblastoma, 155255 |
| 601975 | Ectodermal dysplasia/skin fragility syndrome |
| 601990 | Neuroblastoma |
| 602014 | Hypomagnesemia with secondary hypocalcemia |
| 602023 | Bartter syndrome, type 3 |
| 602025 | Obesity/hyperinsulinism, susceptibility to |
| 602028 | Multiple myeloma |
| 602066 | Convulsions, infantile and paroxysmal choreoathetosis |
| 602067 | Cardiomyopathy, dilated, 1F |
| 602078 | Fibrosis of extraocular muscles, congenital, 2 |
| 602080 | Paget disease of bone-2 |
| 602081 | Speech-language disorder-1 |
| 602082 | Corneal dystrophy, Thiel-Behnke type |
| 602084 | Endometrial carcinoma |
| 602085 | Postaxial polydactyly, type A2 |
| 602086 | Arrhythmogenic right ventricular dysplasia-3 |
| 602087 | Arrhythmogenic right ventricular dysplasia-4 |
| 602088 | Nephronophthisis, infantile |
| 602089 | Hemangioma, capillary, hereditary |
| 602091 | Marfan syndrome, atypical |
| 602092 | Deafness, autosomal recessive 18 |
| 602094 | Lipodystrophy, familial partial |
| 602096 | Alzheimer disease-5 |
| 602099 | Amytrophic lateral sclerosis-5 |
| 602116 | Glioma |
| 602117 | Prader-Willi syndrome |
| 602121 | Deafness, autosomal dominant nonsyndromic sensorineural, 1, 124900 |
| 602134 | Tremor, familial essential, 2 |
| 602136 | Refsum disease, infantile, 266510 |
| 602153 | Monilethrix, 158000 |
| 602216 | Peutz-Jeghers syndrome, 175200 |
| 602221 | Stem-cell leukemia/lymphoma syndrome |
| 602225 | Cone-rod retinal dystrophy-2, 120970 |
| 602229 | Waardenburg-Shah syndrome, 277580 |
| 602232 | Epilepsy, benign neonatal, type 2, 121201 |
| 602235 | Epilepsy, benign, neonatal, type 1, 121200 |
| 602279 | Oculopharyngeal muscular dystorphy, 164300 |
| 602280 | Retinitis pigmentosa-14, 600132 |
| 602363 | Ellis-van Creveld-like syndrome |
| 602397 | Cholestasis, benign recurrent intrahepatic, 243300 |
| 602403 | Alzheimer disease, susceptibility to |
| 602404 | Parkinson disease, type 3 |
| 602421 | Sweat chloride elevation without CF |
| 602447 | Coronary artery disease, susceptibility to |
| 602460 | Deafness, autosomal dominant 15, 602459 |
| 602475 | Ossification of posterior longitudinal ligament of spine |
| 602476 | Febrile convulsions, familial, 1 |
| 602477 | Febrile convulsions, familial, 2 |
| 602491 | Hyperlipidemia, familial combined, 1 |
| 602522 | Bartter syndrome, infantile, with sensorineural deafness |
| 602544 | Parkinson disease, juvenile, type 2, 600116 |
| 602568 | Homocystinuria-megaloblastic anemia, cbl E type, 236270 |
| 602574 | Deafness, autosomal dominant 12, 601842 |
| 602575 | Nail-patella syndrome with open-angle glaucoma, 137750 |
| 602616 | Carbohydrate-deficient glycoprotein syndrome, type II, 212066 |
| 602629 | Dystonia-6, torsion |
| 602631 | Rhabdomyosarcoma, 268210 |
| 602666 | Deafness, autosomal recessive 3, 600316 |
| 602669 | Anterior segment mesenchymal dysgenesis and cataract, 107250 |
| 602685 | Mental retardation, severe, with spasticity and tapetoretinal degeneration |
| 602716 | Nephrosis-1, congenital, Finnish type, 256300 |
| 602759 | Prostate cancer, hereditary, 2, 176807 |
| 602771 | Muscular dystrophy, congenital, with early spine rigidity |
| 602772 | Retinitis pitmentosa-24 |
| 602782 | Faisalabad histiocytosis |
| 602783 | Spastic paraplegia-7 |

Mature Polypeptides

The present invention also encompasses mature forms of a polypeptide having the amino acid sequence of SEQ ID NO:Y and/or the amino acid sequence encoded by the cDNA in a deposited clone. Polynucleotides encoding the mature forms (such as, for example, the polynucleotide sequence in SEQ ID NO:X and/or the polynucleotide sequence contained in the cDNA of a deposited clone) are also encompassed by the invention. Moreover, fragments or variants of these polypeptides (such as, fragments as described herein, polypeptides at least 80%, 85%, 90%, 95%, 96%, 97%, 98%, 99%, or 100% identical to these polypeptides, or polypeptides encoded by a polynucleotide that hybridizes under stringent conditions to the complementary strand of the polynucleotide encoding these polypeptides) are also encompassed by the invention. In preferred embodiments, these fragments or variants retain one or more functional activities of the full-length or mature form of the polypeptide (e.g., biological activity (such as, for example, activity useful in detecting, preventing, diagnosing, prognosticating, treating, and/or ameliorating disorders such as immune, cardiovascular, cancer, and other proliferative disorders), antigenicity (ability to bind, or compete with a polypeptide of the invention for binding, to an anti-polypeptide of the invention antibody), immunogenicity (ability to generate antibody which binds to a specific polypeptide of the invention), ability to form multimers with polypeptides of the invention, and ability to bind to a receptor or ligand for a polypeptide of the invention). Antibodies that bind the polypeptides of the invention, and polynucleotides encoding these polypeptides are also encompassed by the invention.

According to the signal hypothesis, proteins secreted by mammalian cells have a signal or secretary leader sequence that is cleaved from the mature protein once export of the growing protein chain across the rough endoplasmic reticulum has been initiated. Most mammalian cells and even insect cells cleave secreted proteins with the same specificity. However, in some cases, cleavage of a secreted protein is not entirely uniform, which results in two or more mature species of the protein. Further, it has long been known that cleavage specificity of a secreted protein is ultimately determined by the primary structure of the complete protein, that is, it is inherent in the amino acid sequence of the polypeptide.

Methods for predicting whether a protein has a signal sequence, as well as the cleavage point for that sequence, are available. For instance, the method of McGeoch, Virus Res. 3:271-286 (1985), uses the information from a short N-terminal charged region and a subsequent uncharged region of the complete (uncleaved) protein. The method of von Heinje, Nucleic Acids Res. 14:4683-4690 (1986) uses the information from the residues surrounding the cleavage site, typically residues −13 to +2, where +1 indicates the amino terminus of the secreted protein. The accuracy of predicting the cleavage points of known mammalian secretory proteins for each of these methods is in the range of 75-80%. (von Heinje, supra.) However, the two methods do not always produce the same predicted cleavage point(s) for a given protein.

In the present case, the deduced amino acid sequence of the secreted polypeptide was analyzed by a computer program called SignalP (Henrik Nielsen et al., Protein Engineering 10:1-6 (1997)), which predicts the cellular location of a protein based on the amino acid sequence. As part of this computational prediction of localization, the methods of McGeoch and von Heinje are incorporated. The analysis of the amino acid sequences of the secreted proteins described herein by this program provided the results shown in Table 1A.

In specific embodiments, polypeptides of the invention comprise, or alternatively consist of, the predicted mature form of the polypeptide as delineated in columns 14 and 15 of Table 1A. Moreover, fragments or variants of these polypeptides (such as, fragments as described herein, polypeptides at least 80%, 85%, 90%, 95%, 96%, 97%, 98%, 99%, or 100% identical to these polypeptides, or polypeptides encoded by a polynucleotide that hybridizes under stringent conditions to the complementary strand of the polynucleotide encoding these polypeptides) are also encompassed by the invention. In preferred embodiments, these fragments or variants retain one or more functional activities of the full-length or mature form of the polypeptide (e.g., biological activity (such as, for example, activity useful in detecting, preventing, diagnosing, prognosticating, treating, and/or ameliorating disorders such as immune, cardiovascular, cancer, and other proliferative disorders), antigenicity (ability to bind, or compete with a polypeptide of the invention for binding, to an anti-polypeptide of the invention antibody), immunogenicity (ability to generate antibody which binds to a specific polypeptide of the invention), ability to form multimers with polypeptides of the invention, and ability to bind to a receptor or ligand for a polypeptide of the invention). Antibodies that bind the polypeptides of the invention, and polynucleotides encoding these polypeptides are also encompassed by the invention.

Polynucleotides encoding proteins comprising, or consisting of, the predicted mature form of polypeptides of the invention (e.g., polynucleotides having the sequence of SEQ ID NO:X (Table 1A, column 5), the sequence delineated in columns 7 and 8 of Table 1A, and a sequence encoding the mature polypeptide delineated in columns 14 and 15 of Table 1A (e.g., the sequence of SEQ ID NO:X encoding the mature polypeptide delineated in columns 14 and 15 of Table 1A) are also encompassed by the invention, as are fragments or variants of these polynucleotides (such as, fragments as described herein, polynucleotides at least 80%, 85%, 90%, 95%, 96%, 97%, 98%, 99%, or 100% identical to these polynucleotides, and nucleic acids which hybridizes under stringent conditions to the complementary strand of the polynucleotide).

As one of ordinary skill would appreciate, however, cleavage sites sometimes vary from organism to organism and cannot be predicted with absolute certainty. Accordingly, the present invention provides secreted polypeptides having a sequence shown in SEQ ID NO:Y which have an N-terminus beginning within 15 residues of the predicted cleavage point (i.e., having 1, 2, 3, 4, 5, 6, 7, 8, 9, 10, 11, 12, 13, 14, or 15 more or less contiguous residues of SEQ ID NO:Y at the N-terminus when compared to the predicted mature form of the polypeptide (e.g., the mature polypeptide delineated in columns 14 and 15 of Table 1A). Similarly, it is also recognized that in some cases, cleavage of the signal sequence from a secreted protein is not entirely uniform, resulting in more than one secreted species. These polypeptides, and the polynucleotides encoding such polypeptides, are contemplated by the present invention.

Moreover, the signal sequence identified by the above analysis may not necessarily predict the naturally occurring signal sequence. For example, the naturally occurring signal sequence may be further upstream from the predicted signal sequence. However, it is likely that the predicted signal sequence will be capable of directing the secreted protein to the ER. Nonetheless, the present invention provides the mature protein produced by expression of the polynucleotide sequence of SEQ ID NO:X and/or the polynucleotide sequence contained in the cDNA of a deposited clone, in a mammalian cell (e.g., COS cells, as described below). These polypeptides, and the polynucleotides encoding such polypeptides, are contemplated by the present invention.

Polynucleotide and Polypeptide Variants

The present invention is also directed to variants of the polynucleotide sequence disclosed in SEQ ID NO:X or the complementary strand thereto, nucleotide sequences encoding the polypeptide of SEQ ID NO:Y, the nucleotide sequence of SEQ ID NO:X that encodes the polypeptide sequence as defined in columns 11, 12, 13, 14, and/or 15 of Table 1A, nucleotide sequences encoding the polypeptide sequence as defined in columns 11, 12, 13, 14, and/or 15 of Table 1A, the nucleotide sequence of SEQ ID NO:X encoding the polypeptide sequence as defined in Table 1B.1 (such as the sequence defined in column 5 of Table 1B.1), nucleotide sequences encoding the polypeptide as defined in Table 1B.1 (such as the sequence defined in columns 6 and 7 of Table 1B.1), the nucleotide sequence as defined in columns 8 and 9 of Table 2, nucleotide sequences encoding the polypeptide encoded by the nucleotide sequence as defined in columns 8 and 9 of Table 2, the nucleotide sequence as defined in column 6 of Table 1C, nucleotide sequences encoding the polypeptide encoded by the nucleotide sequence as defined in column 6 of Table 1C, the cDNA sequence contained in ATCC™ Deposit No:Z, nucleotide sequences encoding the polypeptide encoded by the cDNA sequence contained in ATCC™ Deposit No:Z, and/or nucleotide sequences encoding a mature (secreted) polypeptide encoded by the cDNA sequence contained in ATCC™ Deposit No:Z.

The present invention also encompasses variants of the polypeptide sequence disclosed in SEQ ID NO:Y, the polypeptide as defined in columns 11, 12, 13, 14, and/or 15 of Table 1A, the polypeptide sequence as defined in Table 1B.1 (such as the sequence defined in columns 6 and 7 of Table 1B.1), a polypeptide sequence encoded by the polynucleotide sequence in SEQ ID NO:X, a polypeptide sequence encoded by the nucleotide sequence as defined in columns 8 and 9 of Table 2, a polypeptide sequence encoded by the nucleotide sequence as defined in column 6 of Table 1C, a polypeptide sequence encoded by the complement of the polynucleotide sequence in SEQ ID NO:X, the polypeptide sequence encoded by the cDNA sequence contained in ATCC™ Deposit No:Z and/or a mature (secreted) polypeptide encoded by the cDNA sequence contained in ATCC™ Deposit No:Z.

"Variant" refers to a polynucleotide or polypeptide differing from the polynucleotide or polypeptide of the present invention, but retaining essential properties thereof. Generally, variants are overall closely similar, and, in many regions, identical to the polynucleotide or polypeptide of the present invention.

Thus, one aspect of the invention provides an isolated nucleic acid molecule comprising, or alternatively consisting of, a polynucleotide having a nucleotide sequence selected from the group consisting of: (a) a nucleotide sequence described in SEQ ID NO:X or contained in the cDNA sequence of ATCC™ Deposit No:Z; (b) a nucleotide sequence in SEQ ID NO:X or the cDNA in ATCC™ Deposit No:Z which encodes the complete amino acid sequence of SEQ ID NO:Y or the complete amino acid sequence encoded by the cDNA in ATCC™ Deposit No:Z; (c) a nucleotide sequence in SEQ ID NO:X or the cDNA in ATCC™ Deposit No:Z which encodes a mature polypeptide (i.e., a secreted polypeptide (e.g., as delineated in columns 14 and 15 of Table 1A)); (d) a nucleotide sequence in SEQ ID NO:X or the cDNA sequence of ATCC™ Deposit No:Z, which encodes a biologically active fragment of a polypeptide; (e) a nucleotide sequence in SEQ ID NO:X or the cDNA sequence of ATCC™ Deposit No:Z, which encodes an antigenic fragment of a polypeptide; (f) a nucleotide sequence encoding a polypeptide comprising the complete amino acid sequence of SEQ ID NO:Y or the complete amino acid sequence encoded by the cDNA in ATCC™ Deposit No:Z; (g) a nucleotide sequence encoding a mature polypeptide of the amino acid sequence of SEQ ID NO:Y (i.e., a secreted polypeptide (e.g., as delineated in columns 14 and 15 of Table 1A)) or a mature polypeptide of the amino acid sequence encoded by the cDNA in ATCC™ Deposit No:Z; (h) a nucleotide sequence encoding a biologically active fragment of a polypeptide having the complete amino acid sequence of SEQ ID NO:Y or the complete amino acid sequence encoded by the cDNA in ATCC™ Deposit No:Z; (i) a nucleotide sequence encoding an antigenic fragment of a polypeptide having the complete amino acid sequence of SEQ ID NO:Y or the complete amino acid sequence encoded by the cDNA in ATCC™ Deposit No:Z; and (j) a nucleotide sequence complementary to any of the nucleotide sequences in (a), (b), (c), (d), (e), (f), (g), (h), or (i) above.

The present invention is also directed to nucleic acid molecules which comprise, or alternatively consist of, a nucleotide sequence which is at least 80%, 85%, 90%, 95%, 96%, 97%, 98%, 99% or 100%, identical to, for example, any of the nucleotide sequences in (a), (b), (c), (d), (e), (f), (g), (h), (i), or (j) above, the nucleotide coding sequence in SEQ ID NO:X or the complementary strand thereto, the nucleotide coding sequence of the cDNA contained in ATCC™ Deposit No:Z or the complementary strand thereto, a nucleotide sequence encoding the polypeptide of SEQ ID NO:Y, a nucleotide sequence encoding a polypeptide sequence encoded by the nucleotide sequence in SEQ ID NO:X, a polypeptide sequence encoded by the complement of the polynucleotide sequence in SEQ ID NO:X, a nucleotide sequence encoding the polypeptide encoded by the cDNA contained in ATCC™ Deposit No:Z, the nucleotide coding sequence in SEQ ID NO:X as defined in columns 8 and 9 of Table 2 or the complementary strand thereto, a nucleotide sequence encoding the polypeptide encoded by the nucleotide sequence in SEQ ID NO:X as defined in columns 8 and 9 of Table 2 or the complementary strand thereto, the nucleotide coding sequence in SEQ ID NO:B as defined in column 6 of Table 1C or the complementary strand thereto, a nucleotide sequence encoding the polypeptide encoded by the nucleotide sequence in SEQ ID NO:B as defined in column 6 of Table 1C or the complementary strand thereto, the nucleotide sequence in SEQ ID NO:X encoding the polypeptide sequence as defined in Table 1B.1 (such as the sequence defined in columns 6 and 7 of Table 1B.1) or the complementary strand thereto, nucleotide sequences encoding the polypeptide as defined in Table 1B.1 (such as the sequence defined in columns 6 and 7 of Table 1B.1) or the complementary strand thereto, and/or polynucleotide fragments of any of these nucleic acid molecules (e.g., those fragments described herein). Polynucleotides which hybridize to the complement of these nucleic acid molecules under stringent hybridization conditions or alternatively, under lower stringency conditions, are also encompassed by the invention, as are polypeptides encoded by these polynucleotides and nucleic acids.

In a preferred embodiment, the invention encompasses nucleic acid molecules which comprise, or alternatively, consist of a polynucleotide which hybridizes under stringent hybridization conditions, or alternatively, under lower stringency conditions, to a polynucleotide in (a), (b), (c), (d), (e), (f), (g), (h), or (i), above, as are polypeptides encoded by these polynucleotides. In another preferred embodiment, polynucleotides which hybridize to the complement of these nucleic acid molecules under stringent hybridization conditions, or alternatively, under lower stringency conditions, are also encompassed by the invention, as are polypeptides encoded by these polynucleotides.

In another embodiment, the invention provides a purified protein comprising, or alternatively consisting of, a polypeptide having an amino acid sequence selected from the group consisting of: (a) the complete amino acid sequence of SEQ ID NO:Y or the complete amino acid sequence encoded by the cDNA in ATCC™ Deposit No:Z; (b) the amino acid sequence of a mature (secreted) form of a polypeptide having the amino acid sequence of SEQ ID NO:Y (e.g., as delineated in columns 14 and 15 of Table 1A) or a mature form of the amino acid sequence encoded by the cDNA in ATCC™ Deposit No:Z mature; (c) the amino acid sequence of a biologically active fragment of a polypeptide having the complete amino acid sequence of SEQ ID NO:Y or the complete amino acid sequence encoded by the cDNA in ATCC™ Deposit No:Z; and (d) the amino acid sequence of an antigenic fragment of a polypeptide having the complete amino acid sequence of SEQ ID NO:Y or the complete amino acid sequence encoded by the cDNA in ATCC™ Deposit No:Z.

The present invention is also directed to proteins which comprise, or alternatively consist of, an amino acid sequence which is at least 80%, 85%, 90%, 95%, 96%, 97%, 98%, 99% or 100%, identical to, for example, any of the amino acid sequences in (a), (b), (c), or (d), above, the amino acid sequence shown in SEQ ID NO:Y, the amino acid sequence encoded by the cDNA contained in ATCC™ Deposit No:Z, the amino acid sequence of the polypeptide encoded by the nucleotide sequence in SEQ ID NO:X as defined in columns 8 and 9 of Table 2, the amino acid sequence of the polypeptide encoded by the nucleotide sequence in SEQ ID NO:B as defined in column 6 of Table 1C, the amino acid sequence as defined in Table 1B.1 (such as the sequence defined in columns 6 and 7 of Table 1B.1), an amino acid sequence encoded by the nucleotide sequence in SEQ ID NO:X, and an amino acid sequence encoded by the complement of the polynucleotide sequence in SEQ ID NO:X. Fragments of these polypeptides are also provided (e.g., those fragments described herein). Further proteins encoded by polynucleotides which hybridize to the complement of the nucleic acid molecules encoding these amino acid sequences under stringent hybridization conditions or alternatively, under lower stringency conditions, are also encompassed by the invention, as are the polynucleotides encoding these proteins.

By a nucleic acid having a nucleotide sequence at least, for example, 95% "identical" to a reference nucleotide sequence of the present invention, it is intended that the nucleotide sequence of the nucleic acid is identical to the reference sequence except that the nucleotide sequence may include up to five point mutations per each 100 nucleotides of the reference nucleotide sequence encoding the polypeptide. In other words, to obtain a nucleic acid having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. The query sequence may be an entire sequence referred to in Tables 1B.1 or 2 as the ORF (open reading frame), or any fragment specified as described herein.

As a practical matter, whether any particular nucleic acid molecule or polypeptide is at least 80%, 85%, 90%, 95%, 96%, 97%, 98% or 99% identical to a nucleotide sequence of the present invention can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al. (Comp. App. Biosci. 6:237-245 (1990)). In a sequence alignment the query and subject sequences are both DNA sequences. An RNA sequence can be compared by converting U's to T's. The result of said global sequence alignment is expressed as percent identity. Preferred parameters used in a FASTDB alignment of DNA sequences to calculate percent identity are: Matrix=Unitary, k-tuple=4, Mismatch Penalty=1, Joining Penalty=30, Randomization Group Length=0, Cutoff Score=1, Gap Penalty=5, Gap Size Penalty 0.05, Window Size=500 or the length of the subject nucleotide sequence, whichever is shorter.

If the subject sequence is shorter than the query sequence because of 5' or 3' deletions, not because of internal deletions, a manual correction must be made to the results. This is because the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of the present invention. Only bases outside the 5' and 3' bases of the subject sequence, as displayed by the FASTDB alignment, which are not matched/aligned with the query sequence, are calculated for the purposes of manually adjusting the percent identity score.

For example, a 90 base subject sequence is aligned to a 100 base query sequence to determine percent identity. The deletions occur at the 5' end of the subject sequence and therefore, the FASTDB alignment does not show a matched/alignment of the first 10 bases at 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are to be made for the purposes of the present invention.

By a polypeptide having an amino acid sequence at least, for example, 95% "identical" to a query amino acid sequence of the present invention, it is intended that the amino acid sequence of the subject polypeptide is identical to the query sequence except that the subject polypeptide sequence may include up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence may be inserted, deleted, (indels) or substituted with another amino acid. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 80%, 85%, 90%, 95%, 96%, 97%, 98% or 99% identical to, for instance, the amino acid sequence of a polypeptide referred to in Table 1A (e.g., the amino acid sequence delineated in columns 14 and 15) or a fragment thereof, Table 1B.1 (e.g., the amino acid sequence identified in column 6) or a fragment thereof, Table 2 (e.g., the amino acid sequence of the polypeptide encoded by the polynucleotide sequence defined in columns 8 and 9 of Table 2) or a fragment thereof, the amino acid sequence of the polypeptide encoded by the polynucleotide sequence in SEQ ID NO:B as defined in column 6 of Table 1C or a fragment thereof, the amino acid sequence of the polypeptide encoded by the nucleotide sequence in SEQ ID NO:X or a fragment thereof, or the amino acid sequence of the polypeptide encoded by cDNA contained in ATCC™ Deposit No:Z, or a fragment thereof, the amino acid sequence of a mature (secreted) polypeptide encoded by cDNA contained in ATCC™ Deposit No:Z, or a fragment thereof, can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al. (Comp. App. Biosci. 6:237-245 (1990)). In a sequence alignment the query and subject sequences are either both nucleotide sequences or both amino acid sequences. The result of said global sequence alignment is expressed as percent identity. Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter.

If the subject sequence is shorter than the query sequence due to N- or C-terminal deletions, not because of internal deletions, a manual correction must be made to the results. This is because the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. Whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present invention. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence.

For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected for. No other manual corrections are to made for the purposes of the present invention.

The polynucleotide variants of the invention may contain alterations in the coding regions, non-coding regions, or both. Especially preferred are polynucleotide variants containing alterations which produce silent substitutions, additions, or deletions, but do not alter the properties or activities of the encoded polypeptide. Nucleotide variants produced by silent substitutions due to the degeneracy of the genetic code are preferred. Moreover, polypeptide variants in which less than 50, less than 40, less than 30, less than 20, less than 10, or 5-50, 5-25, 5-10, 1-5, or 1-2 amino acids are substituted, deleted, or added in any combination are also preferred. Polynucleotide variants can be produced for a variety of reasons, e.g., to optimize codon expression for a particular host (change codons in the human mRNA to those preferred by a bacterial host such as *E. coli*).

Naturally occurring variants are called "allelic variants," and refer to one of several alternate forms of a gene occupying a given locus on a chromosome of an organism. (Genes II, Lewin, B., ed., John Wiley & Sons, New York (1985)). These allelic variants can vary at either the polynucleotide and/or polypeptide level and are included in the present invention. Alternatively, non-naturally occurring variants may be produced by mutagenesis techniques or by direct synthesis.

Using known methods of protein engineering and recombinant DNA technology, variants may be generated to improve or alter the characteristics of the polypeptides of the present invention. For instance, one or more amino acids can be deleted from the N-terminus or C-terminus of the polypeptide of the present invention without substantial loss of biological function. As an example, Ron et al. (J. Biol. Chem. 268: 2984-2988 (1993)) reported variant KGF proteins having heparin binding activity even after deleting 3, 8, or 27 amino-terminal amino acid residues. Similarly, Interferon gamma exhibited up to ten times higher activity after deleting 8-10 amino acid residues from the carboxy terminus of this protein. (Dobeli et al., J. Biotechnology 7:199-216 (1988).)

Moreover, ample evidence demonstrates that variants often retain a biological activity similar to that of the naturally occurring protein. For example, Gayle and coworkers (J. Biol. Chem. 268:22105-22111 (1993)) conducted extensive mutational analysis of human cytokine IL-1a. They used random mutagenesis to generate over 3,500 individual IL-1a mutants that averaged 2.5 amino acid changes per variant over the entire length of the molecule. Multiple mutations were examined at every possible amino acid position. The investigators found that "[m]ost of the molecule could be altered with little effect on either [binding or biological activity]." In fact, only 23 unique amino acid sequences, out of more than 3,500 nucleotide sequences examined, produced a protein that significantly differed in activity from wild-type.

Furthermore, even if deleting one or more amino acids from the N-terminus or C-terminus of a polypeptide results in modification or loss of one or more biological functions, other biological activities may still be retained. For example, the ability of a deletion variant to induce and/or to bind antibodies which recognize the secreted form will likely be retained when less than the majority of the residues of the secreted form are removed from the N-terminus or C-terminus. Whether a particular polypeptide lacking N- or C-terminal residues of a protein retains such immunogenic activities can readily be determined by routine methods described herein and otherwise known in the art.

Thus, the invention further includes polypeptide variants which show a biological or functional activity of the polypeptides of the invention (such as, for example, activity useful in detecting, preventing, diagnosing, prognosticating, treating, and/or ameliorating disorders such as immune or cardiovascular disorders). Such variants include deletions, insertions, inversions, repeats, and substitutions selected according to general rules known in the art so as have little effect on activity.

The present application is directed to nucleic acid molecules at least 80%, 85%, 90%, 95%, 96%, 97%, 98%, 99% or 100% identical to the nucleic acid sequences disclosed herein, (e.g., encoding a polypeptide having the amino acid sequence of an N and/or C terminal deletion), irrespective of whether they encode a polypeptide having functional activity. This is because even where a particular nucleic acid molecule does not encode a polypeptide having functional activity, one of skill in the art would still know how to use the nucleic acid molecule, for instance, as a hybridization probe or a polymerase chain reaction (PCR) primer. Uses of the nucleic acid molecules of the present invention that do not encode a polypeptide having functional activity include, inter alia, (1) isolating a gene or allelic or splice variants thereof in a cDNA library; (2) in situ hybridization (e.g., "FISH") to metaphase chromosomal spreads to provide precise chromosomal location of the gene, as described in Verma et al., Human Chromosomes: A Manual of Basic Techniques, Pergamon Press, New York (1988); (3) Northern Blot analysis for detecting mRNA expression in specific tissues (e.g., normal or diseased tissues); and (4) in situ hybridization (e.g., histochemistry) for detecting mRNA expression in specific tissues (e.g., normal or diseased tissues).

Preferred, however, are nucleic acid molecules having sequences at least 80%, 85%, 90%, 95%, 96%, 97%, 98%, 99% or 100% identical to the nucleic acid sequences disclosed herein, which do, in fact, encode a polypeptide having functional activity. By a polypeptide having "functional activity" is meant, a polypeptide capable of displaying one or more known functional activities associated with a full-length (complete) protein and/or a mature (secreted) protein of the invention. Such functional activities include, but are not limited to, biological activity (such as, for example, activity useful in detecting, preventing, diagnosing, prognosticating, treating, and/or ameliorating diseases and disorders such as immune, cardiovascular, cancer, and other proliferative diseases and disorders), antigenicity (ability to bind, or compete with a polypeptide of the invention for binding, to an anti-polypeptide of the invention antibody), immunogenicity (ability to generate antibody which binds to a specific polypeptide of the invention), ability to form multimers with polypeptides of the invention, and ability to bind to a receptor or ligand for a polypeptide of the invention.

The functional activity of the polypeptides, and fragments, variants, derivatives, and analogs of the invention, can be assayed by various methods.

For example, in one embodiment where one is assaying for the ability to bind or compete with a full-length polypeptide of the present invention for binding to an anti-polypeptide antibody, various immunoassays known in the art can be used, including but not limited to, competitive and non-competitive assay systems using techniques such as radioimmunoassays, ELISA (enzyme linked immunosorbent assay), "sandwich" immunoassays, immunoradiometric assays, gel diffusion precipitation reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention.

In another embodiment, where a ligand is identified, or the ability of a polypeptide fragment, variant or derivative of the invention to multimerize is being evaluated, binding can be assayed, e.g., by means well-known in the art, such as, for example, reducing and non-reducing gel chromatography, protein affinity chromatography, and affinity blotting. See generally, Phizicky et al., Microbiol. Rev. 59:94-123 (1995).

In another embodiment, the ability of physiological correlates of a polypeptide of the present invention to bind to a substrate(s) of the polypeptide of the invention can be routinely assayed using techniques known in the art.

In addition, assays described herein (see Examples) and otherwise known in the art may routinely be applied to measure the ability of polypeptides of the present invention and fragments, variants, derivatives, and analogs thereof to elicit polypeptide related biological activity (either in vitro or in vivo). Other methods will be known to the skilled artisan and are within the scope of the invention.

Of course, due to the degeneracy of the genetic code, one of ordinary skill in the art will immediately recognize that a large number of the nucleic acid molecules having a sequence at least 80%, 85%, 90%, 95%, 96%, 97%, 98%, 99%, or 100% identical to, for example, the nucleic acid sequence of the cDNA contained in ATCC™ Deposit No:Z, the nucleic acid sequence referred to in Tables 1B.1 and 1B.2 (SEQ ID NO:X), the nucleic acid sequence disclosed in Table 1A (e.g., the nucleic acid sequence delineated in columns 7 and 8), the nucleic acid sequence disclosed in Table 2 (e.g., the nucleic acid sequence delineated in columns 8 and 9) or fragments thereof, will encode polypeptides "having functional activity." In fact, since degenerate variants of any of these nucleotide sequences all encode the same polypeptide, in many instances, this will be clear to the skilled artisan even without performing the above described comparison assay. It will be further recognized in the art that, for such nucleic acid molecules that are not degenerate variants, a reasonable number will also encode a polypeptide having functional activity. This is because the skilled artisan is fully aware of amino acid substitutions that are either less likely or not likely to significantly effect protein function (e.g., replacing one aliphatic amino acid with a second aliphatic amino acid), as further described below.

For example, guidance concerning how to make phenotypically silent amino acid substitutions is provided in Bowie et al., "Deciphering the Message in Protein Sequences: Tolerance to Amino Acid Substitutions," Science 247:1306-1310 (1990), wherein the authors indicate that there are two main strategies for studying the tolerance of an amino acid sequence to change.

The first strategy exploits the tolerance of amino acid substitutions by natural selection during the process of evolution. By comparing amino acid sequences in different species, conserved amino acids can be identified. These conserved amino acids are likely important for protein function. In contrast, the amino acid positions where substitutions have been tolerated by natural selection indicates that these positions are not critical for protein function. Thus, positions tolerating amino acid substitution could be modified while still maintaining biological activity of the protein.

The second strategy uses genetic engineering to introduce amino acid changes at specific positions of a cloned gene to identify regions critical for protein function. For example, site directed mutagenesis or alanine-scanning mutagenesis (introduction of single alanine mutations at every residue in the molecule) can be used. See Cunningham and Wells, Science 244:1081-1085 (1989). The resulting mutant molecules can then be tested for biological activity.

As the authors state, these two strategies have revealed that proteins are surprisingly tolerant of amino acid substitutions. The authors further indicate which amino acid changes are likely to be permissive at certain amino acid positions in the protein. For example, most buried (within the tertiary structure of the protein) amino acid residues require nonpolar side chains, whereas few features of surface side chains are generally conserved. Moreover, tolerated conservative amino acid substitutions involve replacement of the aliphatic or hydrophobic amino acids Ala, Val, Leu and Ile; replacement of the hydroxyl residues Ser and Thr; replacement of the acidic residues Asp and Glu; replacement of the amide residues Asn and Gln, replacement of the basic residues Lys, Arg, and His; replacement of the aromatic residues Phe, Tyr, and Trp, and replacement of the small-sized amino acids Ala, Ser, Thr, Met, and Gly.

Besides conservative amino acid substitution, variants of the present invention include (i) substitutions with one or more of the non-conserved amino acid residues, where the substituted amino acid residues may or may not be one encoded by the genetic code, or (ii) substitutions with one or more of the amino acid residues having a substituent group, or (iii) fusion of the mature polypeptide with another compound, such as a compound to increase the stability and/or solubility of the polypeptide (for example, polyethylene glycol), (iv) fusion of the polypeptide with additional amino acids, such as, for example, an IgG Fc fusion region peptide, serum albumin (preferably human serum albumin) or a fragment thereof, or leader or secretory sequence, or a sequence facilitating purification, or (v) fusion of the polypeptide with another compound, such as albumin (including but not limited to recombinant albumin (see, e.g., U.S. Pat. No. 5,876, 969, issued Mar. 2, 1999, EP Patent 0 413 622, and U.S. Pat. No. 5,766,883, issued Jun. 16, 1998, herein incorporated by reference in their entirety)). Such variant polypeptides are deemed to be within the scope of those skilled in the art from the teachings herein.

For example, polypeptide variants containing amino acid substitutions of charged amino acids with other charged or neutral amino acids may produce proteins with improved characteristics, such as less aggregation. Aggregation of pharmaceutical formulations both reduces activity and increases clearance due to the aggregate's immunogenic activity. See Pinckard et al., Clin. Exp. Immunol. 2:331-340 (1967); Robbins et al., Diabetes 36: 838-845 (1987); Cleland et al., Crit. Rev. Therapeutic Drug Carrier Systems 10:307-377 (1993).

A further embodiment of the invention relates to polypeptides which comprise the amino acid sequence of a polypeptide having an amino acid sequence which contains at least one amino acid substitution, but not more than 50 amino acid substitutions, even more preferably, not more than 40 amino acid substitutions, still more preferably, not more than 30 amino acid substitutions, and still even more preferably, not more than 20 amino acid substitutions from a polypeptide sequence disclosed herein. Of course it is highly preferable for a polypeptide to have an amino acid sequence which, for example, comprises the amino acid sequence of a polypeptide of SEQ ID NO:Y, the amino acid sequence of the mature (e.g., secreted) polypeptide of SEQ ID NO:Y, an amino acid sequence encoded by SEQ ID NO:X, an amino acid sequence encoded by the portion of SEQ ID NO:X as defined in columns 8 and 9 of Table 2, an amino acid sequence encoded by the complement of SEQ ID NO:X, an amino acid sequence encoded by cDNA contained in ATCC™ Deposit No:Z, and/or the amino acid sequence of a mature (secreted) polypeptide encoded by cDNA contained in ATCC™ Deposit No:Z, or a fragment thereof, which contains, in order of ever-increasing preference, at least one, but not more than 10, 9, 8, 7, 6, 5, 4, 3, 2 or 1 amino acid substitutions.

In specific embodiments, the polypeptides of the invention comprise, or alternatively, consist of, fragments or variants of a reference amino acid sequence selected from: (a) the amino acid sequence of SEQ ID NO:Y or fragments thereof (e.g., the mature form and/or other fragments described herein); (b) the amino acid sequence encoded by SEQ ID NO:X or fragments thereof; (c) the amino acid sequence encoded by the complement of SEQ ID NO:X or fragments thereof; (d) the amino acid sequence encoded by the portion of SEQ ID NO:X as defined in columns 8 and 9 of Table 2 or fragments thereof; and (e) the amino acid sequence encoded by cDNA contained in ATCC™ Deposit No:Z or fragments thereof; wherein the fragments or variants have 1-5, 5-10, 5-25, 5-50, 10-50 or 50-150, amino acid residue additions, substitutions, and/or deletions when compared to the reference amino acid sequence. In preferred embodiments, the amino acid substitutions are conservative. Polynucleotides encoding these polypeptides are also encompassed by the invention.

Polynucleotide and Polypeptide Fragments

The present invention is also directed to polynucleotide fragments of the polynucleotides (nucleic acids) of the invention. In the present invention, a "polynucleotide fragment" refers to a polynucleotide having a nucleic acid sequence which, for example: is a portion of the cDNA contained in ATCC™ Deposit No:Z or the complementary strand thereto; is a portion of the polynucleotide sequence encoding the polypeptide encoded by the cDNA contained in ATCC™ Deposit No:Z or the complementary strand thereto; is a portion of the polynucleotide sequence encoding the mature (secreted) polypeptide encoded by the cDNA contained in ATCC™ Deposit No:Z or the complementary strand thereto; is a portion of a polynucleotide sequence encoding the mature amino acid sequence as defined in columns 14 and 15 of Table 1A or the complementary strand thereto; is a portion of a polynucleotide sequence encoding the amino acid sequence encoded by the region of SEQ ID NO:X as defined in columns 8 and 9 of Table 2 or the complementary strand thereto; is a portion of the polynucleotide sequence of SEQ ID NO:X as defined in columns 8 and 9 of Table 2 or the complementary strand thereto; is a portion of the polynucleotide sequence in SEQ ID NO:X or the complementary strand thereto; is a polynucleotide sequence encoding a portion of the polypeptide of SEQ ID NO:Y; is a polynucleotide sequence encoding a portion of a polypeptide encoded by SEQ ID NO:X; is a polynucleotide sequence encoding a portion of a polypeptide encoded by the complement of the polynucleotide sequence in SEQ ID NO:X; is a portion of a polynucleotide sequence encoding the amino acid sequence encoded by the region of SEQ ID NO:B as defined in column 6 of Table 1C or the complementary strand thereto; or is a portion of the polynucleotide sequence of SEQ ID NO:B as defined in column 6 of Table 1C or the complementary strand thereto.

The polynucleotide fragments of the invention are preferably at least about 15 nt, and more preferably at least about 20 nt, still more preferably at least about 30 nt, and even more preferably, at least about 40 nt, at least about 50 nt, at least about 75 nt, or at least about 150 nt in length. A fragment "at least 20 nt in length," for example, is intended to include 20 or more contiguous bases from the cDNA sequence contained in ATCC™ Deposit No:Z, or the nucleotide sequence shown in SEQ ID NO:X or the complementary stand thereto. In this context "about" includes the particularly recited value or a value larger or smaller by several (5, 4, 3, 2, or 1) nucleotides, at either terminus or at both termini. These nucleotide fragments have uses that include, but are not limited to, as diagnostic probes and primers as discussed herein. Of course, larger fragments (e.g., at least 160, 170, 180, 190, 200, 250, 500, 600, 1000, or 2000 nucleotides in length) are also encompassed by the invention.

Moreover, representative examples of polynucleotide fragments of the invention comprise, or alternatively consist of, a sequence from about nucleotide number 1-50, 51-100, 101-

150, 151-200, 201-250, 251-300, 301-350, 351-400, 401-450, 451-500, 501-550, 551-600, 601-650, 651-700, 701-750, 751-800, 801-850, 851-900, 901-950, 951-1000, 1001-1050, 1051-1100, 1101-1150, 1151-1200, 1201-1250, 1251-1300, 1301-1350, 1351-1400, 1401-1450, 1451-1500, 1501-1550, 1551-1600, 1601-1650, 1651-1700, 1701-1750, 1751-1800, 1801-1850, 1851-1900, 1901-1950, 1951-2000, 2001-2050, 2051-2100, 2101-2150, 2151-2200, 2201-2250, 2251-2300, 2301-2350, 2351-2400, 2401-2450, 2451-2500, 2501-2550, 2551-2600, 2601-2650, 2651-2700, 2701-2750, 2751-2800, 2801-2850, 2851-2900, 2901-2950, 2951-3000, 3001-3050, 3051-3100, 3101-3150, 3151-3200, 3201-3250, 3251-3300, 3301-3350, 3351-3400, 3401-3450, 3451-3500, 3501-3550, 3551-3600, 3601-3650, 3651-3700, 3701-3750, 3751-3800, 3801-3850, 3851-3900, 3901-3950, 3951-4000, 4001-4050, 4051-4100, 4101-4150, 4151-4200, 4201-4250, 4251-4300, 4301-4350, 4351-4400, 4401-4450, 4451-4500, 4501-4550, 4551-4600, 4601-4650, 4651-4700, 4701-4750, 4751-4800, 4801-4850, 4851-4900, 4901-4950, 4951-5000, 5001-5050, 5051-5100, 5101-5150, 5151-5200, 5201-5250, 5251-5300, 5301-5350, 5351-5400, 5401-5450, 5451-5500, 5501-5550, 5551-5600, 5601-5650, 5651-5700, 5701-5750, 5751-5800, 5801-5850, 5851-5900, 5901-5950, 5951-6000, 6001-6050, 6051-6100, 6101-6150, 6151-6200, 6201-6250, 6251-6300, 6301-6350, 6351-6400, 6401-6450, 6451-6500, 6501-6550, 6551-6600, 6601-6650, 6651-6700, 6701-6750, 6751-6800, 6801-6850, 6851-6900, 6901-6950, 6951-7000, 7001-7050, 7051-7100, 7101-7150, 7151-7200, 7201-7250, 7251-7300 or 7301 to the end of SEQ ID NO:X, or the complementary strand thereto. In this context "about" includes the particularly recited range or a range larger or smaller by several (5, 4, 3, 2, or 1) nucleotides, at either terminus or at both termini. Preferably, these fragments encode a polypeptide which has a functional activity (e.g., biological activity; such as, for example, activity useful in detecting, preventing, diagnosing, prognosticating, treating, and/or ameliorating diseases and disorders such as immune, cardiovascular, cancer, and other proliferative diseases and disorders). More preferably, these polynucleotides can be used as probes or primers as discussed herein. Polynucleotides which hybridize to one or more of these polynucleotides under stringent hybridization conditions or alternatively, under lower stringency conditions are also encompassed by the invention, as are polypeptides encoded by these polynucleotides.

Further representative examples of polynucleotide fragments of the invention comprise, or alternatively consist of, a sequence from about nucleotide number 1-50, 51-100, 101-150, 151-200, 201-250, 251-300, 301-350, 351-400, 401-450, 451-500, 501-550, 551-600, 601-650, 651-700, 701-750, 751-800, 801-850, 851-900, 901-950, 951-1000, 1001-1050, 1051-1100, 1101-1150, 1151-1200, 1201-1250, 1251-1300, 1301-1350, 1351-1400, 1401-1450, 1451-1500, 1501-1550, 1551-1600, 1601-1650, 1651-1700, 1701-1750, 1751-1800, 1801-1850, 1851-1900, 1901-1950, 1951-2000, 2001-2050, 2051-2100, 2101-2150, 2151-2200, 2201-2250, 2251-2300, 2301-2350, 2351-2400, 2401-2450, 2451-2500, 2501-2550, 2551-2600, 2601-2650, 2651-2700, 2701-2750, 2751-2800, 2801-2850, 2851-2900, 2901-2950, 2951-3000, 3001-3050, 3051-3100, 3101-3150, 3151-3200, 3201-3250, 3251-3300, 3301-3350, 3351-3400, 3401-3450, 3451-3500, 3501-3550, 3551-3600, 3601-3650, 3651-3700, 3701-3750, 3751-3800, 3801-3850, 3851-3900, 3901-3950, 3951-4000, 4001-4050, 4051-4100, 4101-4150, 4151-4200, 4201-4250, 4251-4300, 4301-4350, 4351-4400, 4401-4450, 4451-4500, 4501-4550, 4551-4600, 4601-4650, 4651-4700, 4701-4750, 4751-4800, 4801-4850, 4851-4900, 4901-4950, 4951-5000, 5001-5050, 5051-5100, 5101-5150, 5151-5200, 5201-5250, 5251-5300, 5301-5350, 5351-5400, 5401-5450, 5451-5500, 5501-5550, 5551-5600, 5601-5650, 5651-5700, 5701-5750, 5751-5800, 5801-5850, 5851-5900, 5901-5950, 5951-6000, 6001-6050, 6051-6100, 6101-6150, 6151-6200, 6201-6250, 6251-6300, 6301-6350, 6351-6400, 6401-6450, 6451-6500, 6501-6550, 6551-6600, 6601-6650, 6651-6700, 6701-6750, 6751-6800, 6801-6850, 6851-6900, 6901-6950, 6951-7000, 7001-7050, 7051-7100, 7101-7150, 7151-7200, 7201-7250, 7251-7300 or 7301 to the end of the cDNA sequence contained in ATCC™ Deposit No:Z, or the complementary strand thereto. In this context "about" includes the particularly recited range or a range larger or smaller by several (5, 4, 3, 2, or 1) nucleotides, at either terminus or at both termini. Preferably, these fragments encode a polypeptide which has a functional activity (e.g., biological activity). More preferably, these polynucleotides can be used as probes or primers as discussed herein. Polynucleotides which hybridize to one or more of these polynucleotides under stringent hybridization conditions or alternatively, under lower stringency conditions are also encompassed by the invention, as are polypeptides encoded by these polynucleotides.

Moreover, representative examples of polynucleotide fragments of the invention comprise, or alternatively consist of, a nucleic acid sequence comprising one, two, three, four, five, six, seven, eight, nine, ten, or more of the above described polynucleotide fragments of the invention in combination with a polynucleotide sequence delineated in Table 1C, column 6. Additional, representative examples of polynucleotide fragments of the invention comprise, or alternatively consist of, a nucleic acid sequence comprising one, two, three, four, five, six, seven, eight, nine, ten, or more of the above described polynucleotide fragments of the invention in combination with a polynucleotide sequence that is the complementary strand of a sequence delineated in column 6 of Table 1C. In further embodiments, the above-described polynucleotide fragments of the invention comprise, or alternatively consist of, sequences delineated in Table 1C, column 6, and have a nucleic acid sequence which is different from that of the BAC fragment having the sequence disclosed in SEQ ID NO:B (see Table 1C, column 5). In additional embodiments, the above-described polynucleotide fragments of the invention comprise, or alternatively consist of, sequences delineated in Table 1C, column 6, and have a nucleic acid sequence which is different from that published for the BAC clone identified as BAC ID NO:A (see Table 1C, column 4). In additional embodiments, the above-described polynucleotides of the invention comprise, or alternatively consist of, sequences delineated Table 1C, column 6, and have a nucleic acid sequence which is different from that contained in the BAC clone identified as BAC ID NO:A (see Table 1C, column 4). Polypeptides encoded by these polynucleotides, other polynucleotides that encode these polypeptides, and antibodies that bind these polypeptides are also encompassed by the invention. Additionally, fragments and variants of the above-described polynucleotides and polypeptides are also encompassed by the invention.

In additional specific embodiments, polynucleotides of the invention comprise, or alternatively consist of, one, two, three, four, five, six, seven, eight, nine, ten, or more fragments of the sequences delineated in column 6 of Table 1C, and the polynucleotide sequence of SEQ ID NO:X (e.g., as defined in Table 1C, column 2) or fragments or variants thereof. Polypeptides encoded by these polynucleotides, other polynucleotides that encode these polypeptides, and antibodies that bind these polypeptides are also encompassed by the invention.

In additional specific embodiments, polynucleotides of the invention comprise, or alternatively consist of, one, two, three, four, five, six, seven, eight, nine, ten, or more fragments of the sequences delineated in column 6 of Table 1C which correspond to the same ATCC™ Deposit No:Z (see Table 1C, column 1), and the polynucleotide sequence of SEQ ID NO:X (e.g., as defined in Table 1A, 1B, or 1C) or fragments or variants thereof. Polypeptides encoded by these polynucleotides, other polynucleotides that encode these polypeptides, and antibodies that bind these polypeptides are also encompassed by the invention.

In further specific embodiments, polynucleotides of the invention comprise, or alternatively consist of, one, two, three, four, five, six, seven, eight, nine, ten, or more fragments of the sequences delineated in the same row of column 6 of Table 1C, and the polynucleotide sequence of SEQ ID NO:X (e.g., as defined in Table 1A, 1B, or 1C) or fragments or variants thereof. Polypeptides encoded by these polynucleotides, other polynucleotides that encode these polypeptides, and antibodies that bind these polypeptides are also encompassed by the invention.

In additional specific embodiments, polynucleotides of the invention comprise, or alternatively consist of a polynucleotide sequence in which the 3' 10 polynucleotides of one of the sequences delineated in column 6 of Table 1C and the 5' 10 polynucleotides of the sequence of SEQ ID NO:X are directly contiguous. Nucleic acids which hybridize to the complement of these 20 contiguous polynucleotides under stringent hybridization conditions or alternatively, under lower stringency conditions, are also encompassed by the invention. Polypeptides encoded by these polynucleotides and/or nucleic acids, other polynucleotides and/or nucleic acids that encode these polypeptides, and antibodies that bind these polypeptides are also encompassed by the invention. Additionally, fragments and variants of the above-described polynucleotides, nucleic acids, and polypeptides are also encompassed by the invention.

In additional specific embodiments, polynucleotides of the invention comprise, or alternatively consist of a polynucleotide sequence in which the 3' 10 polynucleotides of one of the sequences delineated in column 6 of Table 1C and the 5' 10 polynucleotides of a fragment or variant of the sequence of SEQ ID NO:X (e.g., as described herein) are directly contiguous Nucleic acids which hybridize to the complement of these 20 contiguous polynucleotides under stringent hybridization conditions or alternatively, under lower stringency conditions, are also encompassed by the invention. Polypeptides encoded by these polynucleotides and/or nucleic acids, other polynucleotides and/or nucleic acids encoding these polypeptides, and antibodies that bind these polypeptides are also encompassed by the invention. Additionally, fragments and variants of the above-described polynucleotides, nucleic acids, and polypeptides are also encompassed by the invention.

In further specific embodiments, polynucleotides of the invention comprise, or alternatively consist of a polynucleotide sequence in which the 3' 10 polynucleotides of a fragment or variant of the sequence of SEQ ID NO:X and the 5' 10 polynucleotides of the sequence of one of the sequences delineated in column 6 of Table 1C are directly contiguous. Nucleic acids which hybridize to the complement of these 20 contiguous polynucleotides under stringent hybridization conditions or alternatively, under lower stringency conditions, are also encompassed by the invention. Polypeptides encoded by these polynucleotides and/or nucleic acids, other polynucleotides and/or nucleic acids encoding these polypeptides, and antibodies that bind these polypeptides are also encompassed by the invention. Additionally, fragments and variants of the above-described polynucleotides, nucleic acids, and polypeptides are also encompassed by the invention.

In specific embodiments, polynucleotides of the invention comprise, or alternatively consist of a polynucleotide sequence in which the 3' 10 polynucleotides of one of the sequences delineated in column 6 of Table 1C and the 5' 10 polynucleotides of another sequence in column 6 are directly contiguous. In preferred embodiments, the 3' 10 polynucleotides of one of the sequences delineated in column 6 of Table 1C is directly contiguous with the 5' 10 polynucleotides of the next sequential exon delineated in Table 1C, column 6. Nucleic acids which hybridize to the complement of these 20 contiguous polynucleotides under stringent hybridization conditions or alternatively, under lower stringency conditions, are also encompassed by the invention. Polypeptides encoded by these polynucleotides and/or nucleic acids, other polynucleotides and/or nucleic acids encoding these polypeptides, and antibodies that bind these polypeptides are also encompassed by the invention. Additionally, fragments and variants of the above-described polynucleotides, nucleic acids, and polypeptides are also encompassed by the invention.

In the present invention, a "polypeptide fragment" refers to an amino acid sequence which is a portion of the amino acid sequence contained in SEQ ID NO:Y, is a portion of the mature form of SEQ ID NO:Y as defined in columns 14 and 15 of Table 1A, a portion of an amino acid sequence encoded by the portion of SEQ ID NO:X as defined in columns 8 and 9 of Table 2, is a portion of an amino acid sequence encoded by the polynucleotide sequence of SEQ ID NO:X, is a portion of an amino acid sequence encoded by the complement of the polynucleotide sequence in SEQ ID NO:X, is a portion of the amino acid sequence of a mature (secreted) polypeptide encoded by the cDNA contained in ATCC™ Deposit No:Z, and/or is a portion of an amino acid sequence encoded by the cDNA contained in ATCC™ Deposit No:Z. Protein (polypeptide) fragments may be "free-standing," or comprised within a larger polypeptide of which the fragment forms a part or region, most preferably as a single continuous region. Representative examples of polypeptide fragments of the invention, include, for example, fragments comprising, or alternatively consisting of, from about amino acid number 1-20, 21-40, 41-60, 61-80, 81-100, 101-120, 121-140, 141-160, 161-180, 181-200, 201-220, 221-240, 241-260, 261-280, 281-300, 301-320, 321-340, 341-360, 361-380, 381-400, 401-420, 421-440, 441-460, 461-480, 481-500, 501-520, 521-540, 541-560, 561-580, 581-600, 601-620, 621-640, 641-660, 661-680, 681-700, 701-720, 721-740, 741-760, 761-780, 781-800, 801-820, 821-840, 841-860, 861-880, 881-900, 901-920, 921-940, 941-960, 961-980, 981-1000, 1001-1020, 1021-1040, 1041-1060, 1061-1080, 1081-1100, 1101-1120, 1121-1140, 1141-1160, 1161-1180, 1181-1200, 1201-1220, 1221-1240, 1241-1260, 1261-1280, 1281-1300, 1301-1320, 1321-1340, 1341-1360, 1361-1380, 1381-1400, 1401-1420, 1421-1440, or 1441 to the end of the coding region of cDNA and SEQ ID NO:Y. In a preferred embodiment, polypeptide fragments of the invention include, for example, fragments comprising, or alternatively consisting of, from about amino acid number 1-20, 21-40, 41-60, 61-80, 81-100, 101-120, 121-140, 141-160, 161-180, 181-200, 201-220, 221-240, 241-260, 261-280, 281-300, 301-320, 321-340, 341-360, 361-380, 381-400, 401-420, 421-440, 441-460, 461-480, 481-500, 501-520, 521-540, 541-560, 561-580, 581-600, 601-620, 621-640, 641-660, 661-680, 681-700, 701-720, 721-740, 741-760, 761-780, 781-800, 801-

820, 821-840, 841-860, 861-880, 881-900, 901-920, 921-940, 941-960, 961-980, 981-1000, 1001-1020, 1021-1040, 1041-1060, 1061-1080, 1081-1100, 1101-1120, 1121-1140, 1141-1160, 1161-1180, 1181-1200, 1201-1220, 1221-1240, 1241-1260, 1261-1280, 1281-1300, 1301-1320, 1321-1340, 1341-1360, 1361-1380, 1381-1400, 1401-1420, 1421-1440, or 1441 to the end of the coding region of SEQ ID NO:Y. Moreover, polypeptide fragments of the invention may be at least about 10, 15, 20, 25, 30, 35, 40, 45, 50, 55, 60, 65, 70, 75, 80, 85, 90, 100, 110, 120, 130, 140, or 150 amino acids in length. In this context "about" includes the particularly recited ranges or values, or ranges or values larger or smaller by several (5, 4, 3, 2, or 1) amino acids, at either extreme or at both extremes. Polynucleotides encoding these polypeptide fragments are also encompassed by the invention.

Even if deletion of one or more amino acids from the N-terminus of a protein results in modification of loss of one or more biological functions of the protein, other functional activities (e.g., biological activities; such as, for example, activity useful in detecting, preventing, diagnosing, prognosticating, treating, and/or ameliorating diseases and disorders such as immune, cardiovascular, cancer, and other proliferative diseases and disorders; ability to multimerize; ability to bind a ligand; antigenic ability useful for production of polypeptide specific antibodies) may still be retained. For example, the ability of shortened muteins to induce and/or bind to antibodies which recognize the complete or mature forms of the polypeptides generally will be retained when less than the majority of the residues of the complete or mature polypeptide are removed from the N-terminus. Whether a particular polypeptide lacking N-terminal residues of a complete polypeptide retains such immunologic activities can readily be determined by routine methods described herein and otherwise known in the art. It is not unlikely that a mutein with a large number of deleted N-terminal amino acid residues may retain some biological or immunogenic activities. In fact, peptides composed of as few as six amino acid residues may often evoke an immune response.

Accordingly, polypeptide fragments include the secreted protein as well as the mature form. Further preferred polypeptide fragments include the secreted protein or the mature form having a continuous series of deleted residues from the amino or the carboxy terminus, or both. For example, any number of amino acids, ranging from 1-60, can be deleted from the amino terminus of either the secreted polypeptide or the mature form. Similarly, any number of amino acids, ranging from 1-30, can be deleted from the carboxy terminus of the secreted protein or mature form. Furthermore, any combination of the above amino and carboxy terminus deletions are preferred. Similarly, polynucleotides encoding these polypeptide fragments are also preferred.

The present invention further provides polypeptides having one or more residues deleted from the amino terminus of the amino acid sequence of a polypeptide disclosed herein (e.g., a polypeptide of SEQ ID NO:Y, a polypeptide as defined in columns 14 and 15 of Table 1A, a polypeptide encoded by the polynucleotide sequence contained in SEQ ID NO:X or the complement thereof, a polypeptide encoded by the portion of SEQ ID NO:X as defined in columns 8 and 9 of Table 2, a polypeptide encoded by the portion of SEQ ID NO:B as defined in column 6 of Table 1C, a polypeptide encoded by the cDNA contained in ATCC™ Deposit No:Z, and/or a mature polypeptide encoded by the cDNA contained in ATCC™ Deposit No:Z). In particular, N-terminal deletions may be described by the general formula m−q, where q is a whole integer representing the total number of amino acid residues in a polypeptide of the invention (e.g., the polypeptide disclosed in SEQ ID NO:Y, the mature (secreted) portion of SEQ ID NO:Y as defined in columns 14 and 15 of Table 1A, or the polypeptide encoded by the portion of SEQ ID NO:X as defined in columns 8 and 9 of Table 2), and m is defined as any integer ranging from 2 to q−6. Polynucleotides encoding these polypeptides are also encompassed by the invention.

The present invention further provides polypeptides having one or more residues from the carboxy terminus of the amino acid sequence of a polypeptide disclosed herein (e.g., a polypeptide of SEQ ID NO:Y, the mature (secreted) portion of SEQ ID NO:Y as defined in columns 14 and 15 of Table 1A, a polypeptide encoded by the polynucleotide sequence contained in SEQ ID NO:X, a polypeptide encoded by the portion of SEQ ID NO:X as defined in columns 8 and 9 of Table 2, a polypeptide encoded by the portion of SEQ ID NO:B as defined in column 6 of Table 1C, a polypeptide encoded by the cDNA contained in ATCC™ Deposit No:Z, and/or a mature polypeptide encoded by the cDNA contained in ATCC™ Deposit No:Z). In particular, C-terminal deletions may be described by the general formula 1−n, where n is any whole integer ranging from 6 to q−1, and where n corresponds to the position of amino acid residue in a polypeptide of the invention. Polynucleotides encoding these polypeptides are also encompassed by the invention.

In addition, any of the above described N- or C-terminal deletions can be combined to produce a N- and C-terminal deleted polypeptide. The invention also provides polypeptides having one or more amino acids deleted from both the amino and the carboxyl termini, which may be described generally as having residues m-n of a polypeptide encoded by SEQ ID NO:X (e.g., including, but not limited to, the preferred polypeptide disclosed as SEQ ID NO:Y, the mature (secreted) portion of SEQ ID NO:Y as defined in columns 14 and 15 of Table 1A, and the polypeptide encoded by the portion of SEQ ID NO:X as defined in columns 8 and 9 of Table 2), the cDNA contained in ATCC™ Deposit No:Z, and/or the complement thereof, where n and m are integers as described above. Polynucleotides encoding these polypeptides are also encompassed by the invention.

Also as mentioned above, even if deletion of one or more amino acids from the C-terminus of a protein results in modification of loss of one or more biological functions of the protein, other functional activities (e.g., biological activities such as, for example, activity useful in detecting, preventing, diagnosing, prognosticating, treating, and/or ameliorating diseases and disorders such as immune, cardiovascular, cancer, and other proliferative diseases and disorders; ability to multimerize; ability to bind a ligand; antigenic ability useful for production of polypeptide specific antibodies) may still be retained. For example the ability of the shortened mutein to induce and/or bind to antibodies which recognize the complete or mature forms of the polypeptide generally will be retained when less than the majority of the residues of the complete or mature polypeptide are removed from the C-terminus. Whether a particular polypeptide lacking C-terminal residues of a complete polypeptide retains such immunologic activities can readily be determined by routine methods described herein and otherwise known in the art. It is not unlikely that a mutein with a large number of deleted C-terminal amino acid residues may retain some biological or immunogenic activities. In fact, peptides composed of as few as six amino acid residues may often evoke an immune response.

The present application is also directed to proteins containing polypeptides at least 80%, 85%, 90%, 95%, 96%, 97%, 98% or 99% identical to a polypeptide sequence set forth herein. In preferred embodiments, the application is directed to proteins containing polypeptides at least 80%, 85%, 90%, 95%, 96%, 97%, 98% or 99% identical to polypeptides having the amino acid sequence of the specific N- and C-terminal deletions. Polynucleotides encoding these polypeptides are also encompassed by the invention.

Any polypeptide sequence encoded by, for example, the polynucleotide sequences set forth as SEQ ID NO:X or the complement thereof, (presented, for example, in Tables 1A and 2), the cDNA contained in ATCC™ Deposit No:Z, or the polynucleotide sequence as defined in column 6 of Table 1C, may be analyzed to determine certain preferred regions of the polypeptide. For example, the amino acid sequence of a polypeptide encoded by a polynucleotide sequence of SEQ ID NO:X (e.g., the polypeptide of SEQ ID NO:Y and the polypeptide encoded by the portion of SEQ ID NO:X as defined in columns 8 and 9 of Table 2) or the cDNA contained in ATCC™ Deposit No:Z may be analyzed using the default parameters of the DNASTAR computer algorithm (DNASTAR, Inc., 1228 S. Park St., Madison, Wis. 53715 USA, world wide web at dnastar.com/).

Also preferred are polypeptide and polynucleotide fragments characterized by structural or functional domains, such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions. Polypeptide regions that may be routinely obtained using the DNASTAR computer algorithm include, but are not limited to, Garnier-Robson alpha-regions, beta-regions, turn-regions, and coil-regions; Chou-Fasman alpha-regions, beta-regions, and turn-regions; Kyte-Doolittle hydrophilic regions and hydrophobic regions; Eisenberg alpha- and beta-amphipathic regions; Karplus-Schulz flexible regions; Emini surface-forming regions; and Jameson-Wolf regions of high antigenic index. Among highly preferred polynucleotides of the invention in this regard are those that encode polypeptides comprising regions that combine several structural features, such as several (e.g., 1, 2, 3 or 4) of the features set out above. Polypeptide fragments of SEQ ID NO:Y falling within conserved domains are specifically contemplated by the present invention. Moreover, polynucleotides encoding these domains are also contemplated.

Additionally, Kyte-Doolittle hydrophilic regions and hydrophobic regions, Emini surface-forming regions, and Jameson-Wolf regions of high antigenic index (i.e., containing four or more contiguous amino acids having an antigenic index of greater than or equal to 1.5, as identified using the default parameters of the Jameson-Wolf program) can routinely be used to determine polypeptide regions that exhibit a high degree of potential for antigenicity. Regions of high antigenicity are determined from data by DNASTAR analysis by choosing values which represent regions of the polypeptide which are likely to be exposed on the surface of the polypeptide in an environment in which antigen recognition may occur in the process of initiation of an immune response.

Preferred polypeptide fragments of the invention are fragments comprising, or alternatively, consisting of, an amino acid sequence that displays a functional activity (e.g. biological activity such as, for example, activity useful in detecting, preventing, diagnosing, prognosticating, treating, and/or ameliorating diseases and disorders such as immune, cardiovascular, cancer, and other proliferative diseases and disorders; ability to multimerize; ability to bind a ligand; antigenic ability useful for production of polypeptide specific antibodies) of the polypeptide sequence of which the amino acid sequence is a fragment. By a polypeptide displaying a "functional activity" is meant a polypeptide capable of one or more known functional activities associated with a full-length protein, such as, for example, biological activity, antigenicity, immunogenicity, and/or multimerization, as described herein.

Other preferred polypeptide fragments are biologically active fragments. Biologically active fragments are those exhibiting activity similar, but not necessarily identical, to an activity of the polypeptide of the present invention. The biological activity of the fragments may include an improved desired activity, or a decreased undesirable activity. Polynucleotides encoding these polypeptide fragments are also encompassed by the invention.

Preferably, the polynucleotide fragments of the invention encode a polypeptide which demonstrates a functional activity. By a polypeptide demonstrating a "functional activity" is meant, a polypeptide capable of displaying one or more known functional activities associated with a full-length (complete) polypeptide of invention protein. Such functional activities include, but are not limited to, biological activity, antigenicity [ability to bind (or compete with a polypeptide of the invention for binding) to an antibody to the polypeptide of the invention], immunogenicity (ability to generate antibody which binds to a polypeptide of the invention), ability to form multimers with polypeptides of the invention, and ability to bind to a receptor or ligand for a polypeptide of the invention.

The functional activity of polypeptides of the invention, and fragments, variants derivatives, and analogs thereof, can be assayed by various methods.

In preferred embodiments, polypeptides of the invention comprise, or alternatively consist of, one, two, three, four, five or more of the antigenic fragments of the polypeptide of SEQ ID NO:Y, or portions thereof. Polynucleotides encoding these polypeptides are also encompassed by the invention.

Epitopes and Antibodies

The present invention encompasses polypeptides comprising, or alternatively consisting of, an epitope of: the polypeptide sequence shown in SEQ ID NO:Y; a polypeptide sequence encoded by SEQ ID NO:X or the complementary strand thereto; the polypeptide sequence encoded by the portion of SEQ ID NO:X as defined in columns 8 and 9 of Table 2; the polypeptide sequence encoded by the portion of SEQ ID NO:B as defined in column 6 of Table 1C or the complement thereto; the polypeptide sequence encoded by the cDNA contained in ATCC™ Deposit No:Z; or the polypeptide sequence encoded by a polynucleotide that hybridizes to the sequence of SEQ ID NO:X, the complement of the sequence of SEQ ID NO:X, the complement of a portion of SEQ ID NO:X as defined in columns 8 and 9 of Table 2, or the cDNA sequence contained in ATCC™ Deposit No:Z under stringent hybridization conditions or alternatively, under lower stringency hybridization as defined supra. The present invention further encompasses polynucleotide sequences encoding an epitope of a polypeptide sequence of the invention (such as, for example, the sequence disclosed in SEQ ID NO:X, or a fragment thereof), polynucleotide sequences of the complementary strand of a polynucleotide sequence encoding an epitope of the invention, and polynucleotide sequences which hybridize to the complementary strand under stringent hybridization conditions or alternatively, under lower stringency hybridization conditions defined supra.

The term "epitopes," as used herein, refers to portions of a polypeptide having antigenic or immunogenic activity in an animal, preferably a mammal, and most preferably in a human. In a preferred embodiment, the present invention encompasses a polypeptide comprising an epitope, as well as the polynucleotide encoding this polypeptide. An "immunogenic epitope," as used herein, is defined as a portion of a protein that elicits an antibody response in an animal, as determined by any method known in the art, for example, by the methods for generating antibodies described infra. (See, for example, Geysen et al., Proc. Natl. Acad. Sci. USA 81:3998-4002 (1983)). The term "antigenic epitope," as used herein, is defined as a portion of a protein to which an antibody can immunospecifically bind its antigen as determined by any method well known in the art, for example, by the immunoassays described herein. Immunospecific binding excludes non-specific binding but does not necessarily exclude cross-reactivity with other antigens. Antigenic epitopes need not necessarily be immunogenic.

Fragments which function as epitopes may be produced by any conventional means. (See, e.g., Houghten, R. A., Proc. Natl. Acad. Sci. USA 82:5131-5135 (1985) further described in U.S. Pat. No. 4,631,211.)

In the present invention, antigenic epitopes preferably contain a sequence of at least 4, at least 5, at least 6, at least 7, more preferably at least 8, at least 9, at least 10, at least 11, at least 12, at least 13, at least 14, at least 15, at least 20, at least 25, at least 30, at least 40, at least 50, and, most preferably, between about 15 to about 30 amino acids. Preferred polypeptides comprising immunogenic or antigenic epitopes are at least 10, 15, 20, 25, 30, 35, 40, 45, 50, 55, 60, 65, 70, 75, 80, 85, 90, 95, or 100 amino acid residues in length. Additional non-exclusive preferred antigenic epitopes include the antigenic epitopes disclosed herein, as well as portions thereof. Antigenic epitopes are useful, for example, to raise antibodies, including monoclonal antibodies, that specifically bind the epitope. Preferred antigenic epitopes include the antigenic epitopes disclosed herein, as well as any combination of two, three, four, five or more of these antigenic epitopes. Antigenic epitopes can be used as the target molecules in immunoassays. (See, for instance, Wilson et al., Cell 37:767-778 (1984); Sutcliffe et al., Science 219:660-666 (1983)).

Non-limiting examples of epitopes of polypeptides that can be used to generate antibodies of the invention include a polypeptide comprising, or alternatively consisting of, at least one, two, three, four, five, six or more of the portion(s) of SEQ ID NO:Y specified in Table 1B.1 (such as the sequence specified in column 6 of Table 1B.1). These polypeptide fragments have been determined to bear antigenic epitopes of the proteins of the invention by the analysis of the Jameson-Wolf antigenic index that is included in the DNAStar suite of computer programs. By "comprise" it is intended that a polypeptide contains at least one, two, three, four, five, six or more of the portion(s) of SEQ ID NO:Y shown in Table 1B.1 (such as the sequence specified in column 6 of Table 1B.1), but it may contain additional flanking residues on either the amino or carboxyl termini of the recited portion. Such additional flanking sequences are preferably sequences naturally found adjacent to the portion; i.e., contiguous sequence shown in SEQ ID NO:Y. The flanking sequence may, however, be sequences from a heterologous polypeptide, such as from another protein described herein or from a heterologous polypeptide not described herein. In particular embodiments, epitope portions of a polypeptide of the invention comprise one, two, three, or more of the portions of SEQ ID NO:Y shown in Table 1B.1 (such as the sequence specified in column 6 of Table 1B.1).

Similarly, immunogenic epitopes can be used, for example, to induce antibodies according to methods well known in the art. See, for instance, Sutcliffe et al., supra; Wilson et al., supra; Chow et al., Proc. Natl. Acad. Sci. USA 82:910-914; and Bittle et al., J. Gen. Virol. 66:2347-2354 (1985). Preferred immunogenic epitopes include the immunogenic epitopes disclosed herein, as well as any combination of two, three, four, five or more of these immunogenic epitopes. The polypeptides comprising one or more immunogenic epitopes may be presented for eliciting an antibody response together with a carrier protein, such as an albumin, to an animal system (such as rabbit or mouse), or, if the polypeptide is of sufficient length (at least about 25 amino acids), the polypeptide may be presented without a carrier. However, immunogenic epitopes comprising as few as 8 to 10 amino acids have been shown to be sufficient to raise antibodies capable of binding to, at the very least, linear epitopes in a denatured polypeptide (e.g., in Western blotting).

As used herein, the term "antibody" (Ab) or "monoclonal antibody" (Mab) is meant to include intact molecules as well as antibody fragments (such as, for example, Fab and F(ab')2 fragments) which are capable of specifically binding to protein. Fab and F(ab')2 fragments lack the Fc fragment of intact antibody, clear more rapidly from the circulation, and may have less non-specific tissue binding than an intact antibody. (Wahl et al., J. Nucl. Med. 24:316-325 (1983).) Thus, these fragments are preferred, as well as the products of a FAB or other immunoglobulin expression library. Moreover, antibodies of the present invention include chimeric, single chain, and humanized antibodies.

Epitope-bearing polypeptides of the present invention may be used to induce antibodies according to methods well known in the art including, but not limited to, in vivo immunization, in vitro immunization, and phage display methods. See, e.g., Sutcliffe et al., supra; Wilson et al., supra, and Bittle et al., J. Gen. Virol., 66:2347-2354 (1985). If in vivo immunization is used, animals may be immunized with free peptide; however, anti-peptide antibody titer may be boosted by coupling the peptide to a macromolecular carrier, such as keyhole limpet hemacyanin (KLH) or tetanus toxoid. For instance, peptides containing cysteine residues may be coupled to a carrier using a linker such as maleimidobenzoyl-N-hydroxysuccinimide ester (MBS), while other peptides may be coupled to carriers using a more general linking agent such as glutaraldehyde. Animals such as rabbits, rats and mice are immunized with either free or carrier-coupled peptides, for instance, by intraperitoneal and/or intradermal injection of emulsions containing about 100 μg of peptide or carrier protein and Freund's adjuvant or any other adjuvant known for stimulating an immune response. Several booster injections may be needed, for instance, at intervals of about two weeks, to provide a useful titer of anti-peptide antibody which can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

As one of skill in the art will appreciate, and as discussed above, the polypeptides of the present invention (e.g., those comprising an immunogenic or antigenic epitope) can be fused to heterologous polypeptide sequences. For example, polypeptides of the present invention (including fragments or variants thereof), may be fused with the constant domain of immunoglobulins (IgA, IgE, IgG, IgM), or portions thereof (CH1, CH2, CH3, or any combination thereof and portions thereof, resulting in chimeric polypeptides. By way of another non-limiting example, polypeptides and/or antibodies of the present invention (including fragments or variants thereof) may be fused with albumin (including but not limited to recombinant human serum albumin or fragments or variants thereof (see, e.g., U.S. Pat. No. 5,876,969, issued Mar. 2, 1999, EP Patent 0 413 622, and U.S. Pat. No. 5,766,883, issued Jun. 16, 1998, herein incorporated by reference in their entirety)). In a preferred embodiment, polypeptides and/or antibodies of the present invention (including fragments or variants thereof) are fused with the mature form of human serum albumin (i.e., amino acids 1-585 of human serum albumin as shown in FIGS. 1 and 2 of EP Patent 0 322 094) which is herein incorporated by reference in its entirety. In another preferred embodiment, polypeptides and/or antibodies of the present invention (including fragments or variants thereof) are fused with polypeptide fragments comprising, or alternatively consisting of, amino acid residues 1-x of human serum albumin, where x is an integer from 1 to 585 and the albumin fragment has human serum albumin activity. In another preferred embodiment, polypeptides and/or antibodies of the present invention (including fragments or variants thereof) are fused with polypeptide fragments comprising, or alternatively consisting of, amino acid residues 1–z of human serum albumin, where z is an integer from 369 to 419, as described in U.S. Pat. No. 5,766,883 herein incorporated by reference in its entirety. Polypeptides and/or antibodies of the present invention (including fragments or variants thereof) may be fused to either the N- or C-terminal end of the heterologous protein (e.g., immunoglobulin Fc polypeptide or human serum albumin polypeptide). Polynucleotides encoding fusion proteins of the invention are also encompassed by the invention.

Such fusion proteins as those described above may facilitate purification and may increase half-life in vivo. This has been shown for chimeric proteins consisting of the first two domains of the human CD4-polypeptide and various domains of the constant regions of the heavy or light chains of mammalian immunoglobulins. See, e.g., EP 394,827; Traunecker et al., Nature, 331:84-86 (1988). Enhanced delivery of an antigen across the epithelial barrier to the immune system has been demonstrated for antigens (e.g., insulin) conjugated to an FcRn binding partner such as IgG or Fc fragments (see, e.g., PCT Publications WO 96/22024 and WO 99/04813). IgG fusion proteins that have a disulfide-linked dimeric structure due to the IgG portion disulfide bonds have also been found to be more efficient in binding and neutralizing other molecules than monomeric polypeptides or fragments thereof alone. See, e.g., Fountoulakis et al., J. Biochem., 270:3958-3964 (1995). Nucleic acids encoding the above epitopes can also be recombined with a gene of interest as an epitope tag (e.g., the hemagglutinin (HA) tag or flag tag) to aid in detection and purification of the expressed polypeptide. For example, a system described by Janknecht et al. allows for the ready purification of non-denatured fusion proteins expressed in human cell lines (Janknecht et al., 1991, Proc. Natl. Acad. Sci. USA 88:8972-897). In this system, the gene of interest is subcloned into a vaccinia recombination plasmid such that the open reading frame of the gene is translationally fused to an amino-terminal tag consisting of six histidine residues. The tag serves as a matrix binding domain for the fusion protein. Extracts from cells infected with the recombinant vaccinia virus are loaded onto Ni2+ nitriloacetic acid-agarose column and histidine-tagged proteins can be selectively eluted with imidazole-containing buffers.

Fusion Proteins

Any polypeptide of the present invention can be used to generate fusion proteins. For example, the polypeptide of the present invention, when fused to a second protein, can be used as an antigenic tag. Antibodies raised against the polypeptide of the present invention can be used to indirectly detect the second protein by binding to the polypeptide. Moreover, because secreted proteins target cellular locations based on trafficking signals, polypeptides of the present invention which are shown to be secreted can be used as targeting molecules once fused to other proteins.

Examples of domains that can be fused to polypeptides of the present invention include not only heterologous signal sequences, but also other heterologous functional regions. The fusion does not necessarily need to be direct, but may occur through linker sequences.

In certain preferred embodiments, proteins of the invention are fusion proteins comprising an amino acid sequence that is an N and/or C-terminal deletion of a polypeptide of the invention. In preferred embodiments, the invention is directed to a fusion protein comprising an amino acid sequence that is at least 90%, 95%, 96%, 97%, 98% or 99% identical to a polypeptide sequence of the invention. Polynucleotides encoding these proteins are also encompassed by the invention.

Moreover, fusion proteins may also be engineered to improve characteristics of the polypeptide of the present invention. For instance, a region of additional amino acids, particularly charged amino acids, may be added to the N-terminus of the polypeptide to improve stability and persistence during purification from the host cell or subsequent handling and storage. Also, peptide moieties may be added to the polypeptide to facilitate purification. Such regions may be removed prior to final preparation of the polypeptide. The addition of peptide moieties to facilitate handling of polypeptides are familiar and routine techniques in the art.

As one of skill in the art will appreciate that, as discussed above, polypeptides of the present invention, and epitope-bearing fragments thereof, can be combined with heterologous polypeptide sequences. For example, the polypeptides of the present invention may be fused with heterologous polypeptide sequences, for example, the polypeptides of the present invention may be fused with the constant domain of immunoglobulins (IgA, IgE, IgG, IgM) or portions thereof (CH1, CH2, CH3, and any combination thereof, including both entire domains and portions thereof), or albumin (including, but not limited to, native or recombinant human albumin or fragments or variants thereof (see, e.g., U.S. Pat. No. 5,876,969, issued Mar. 2, 1999, EP Patent 0 413 622, and U.S. Pat. No. 5,766,883, issued Jun. 16, 1998, herein incorporated by reference in their entirety)), resulting in chimeric polypeptides. These fusion proteins facilitate purification and show an increased half-life in vivo. One reported example describes chimeric proteins consisting of the first two domains of the human CD4-polypeptide and various domains of the constant regions of the heavy or light chains of mammalian immunoglobulins. (EP A 394,827; Traunecker et al., Nature 331:84-86 (1988).) Fusion proteins having disulfide-linked dimeric structures (due to the IgG) can also be more efficient in binding and neutralizing other molecules, than the monomeric secreted protein or protein fragment alone. (Fountoulakis et al., J. Biochem. 270:3958-3964 (1995).) For example, EP-A-0 464 533 (Canadian counterpart 2045869) discloses fusion proteins comprising various portions of constant region of immunoglobulin molecules together with another human protein or part thereof. In many cases, the Fc part in a fusion protein is beneficial in therapy and diagnosis, and thus can result in, for example, improved pharmacokinetic properties (EP-A 0232 262). Alternatively, deleting the Fc part after the fusion protein has been expressed, detected, and purified, would be desired. For example, the Fc portion may hinder therapy and diagnosis if the fusion protein is used as an antigen for immunizations. In drug discovery, for example, human proteins, such as hIL-5, have been fused with Fc portions for the purpose of high-throughput screening assays to identify antagonists of hIL-5 See, D. Bennett et al., J. Molecular Recognition 8:52-58 (1995); K. Johanson et al., J. Biol. Chem. 270:9459-9471 (1995). Polynucleotides comprising or alternatively consisting of nucleic acids which encode these fusion proteins are also encompassed by the invention.

Moreover, the polypeptides of the present invention can be fused to marker sequences, such as a polypeptide which facilitates purification of the fused polypeptide. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821-824 (1989), for instance, hexa-histidine provides for convenient purification of the fusion protein. Another peptide tag useful for purification, the "HA" tag, corresponds to an epitope derived from the influenza hemagglutinin protein (Wilson et al., Cell 37:767 (1984)).

Additional fusion proteins of the invention may be generated through the techniques of gene-shuffling, motif-shuffling, exon-shuffling, and/or codon-shuffling (collectively referred to as "DNA shuffling"). DNA shuffling may be employed to modulate the activities of polypeptides of the invention, such methods can be used to generate polypeptides with altered activity, as well as agonists and antagonists of the polypeptides. See, generally, U.S. Pat. Nos. 5,605,793; 5,811,238; 5,830,721; 5,834,252; and 5,837,458, and Patten et al., Curr. Opinion Biotechnol. 8:724-33 (1997); Harayama, Trends Biotechnol. 16(2):76-82 (1998); Hansson, et al., J. Mol. Biol. 287:265-76 (1999); and Lorenzo and Blasco, Biotechniques 24(2):308-13 (1998) (each of these patents and publications are hereby incorporated by reference in its entirety). In one embodiment, alteration of polynucleotides corresponding to SEQ ID NO:X and the polypeptides encoded by these polynucleotides may be achieved by DNA shuffling. DNA shuffling involves the assembly of two or more DNA segments by homologous or site-specific recombination to generate variation in the polynucleotide sequence. In another embodiment, polynucleotides of the invention, or the encoded polypeptides, may be altered by being subjected to random mutagenesis by error-prone PCR, random nucleotide insertion or other methods prior to recombination. In another embodiment, one or more components, motifs, sections, parts, domains, fragments, etc., of a polynucleotide encoding a polypeptide of the invention may be recombined with one or more components, motifs, sections, parts, domains, fragments, etc. of one or more heterologous molecules.

Thus, any of these above fusions can be engineered using the polynucleotides or the polypeptides of the present invention.

Recombinant and Synthetic Production of Polypeptides of the Invention

The present invention also relates to vectors containing the polynucleotide of the present invention, host cells, and the production of polypeptides by synthetic and recombinant techniques. The vector may be, for example, a phage, plasmid, viral, or retroviral vector. Retroviral vectors may be replication competent or replication defective. In the latter case, viral propagation generally will occur only in complementing host cells.

The polynucleotides of the invention may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

The polynucleotide insert should be operatively linked to an appropriate promoter, such as the phage lambda PL promoter, the *E. coli* lac, trp, phoA and tac promoters, the SV40 early and late promoters and promoters of retroviral LTRs, to name a few. Other suitable promoters will be known to the skilled artisan. The expression constructs will further contain sites for transcription initiation, termination, and, in the transcribed region, a ribosome binding site for translation. The coding portion of the transcripts expressed by the constructs will preferably include a translation initiating codon at the beginning and a termination codon (UAA, UGA or UAG) appropriately positioned at the end of the polypeptide to be translated.

As indicated, the expression vectors will preferably include at least one selectable marker. Such markers include dihydrofolate reductase, G418, glutamine synthase, or neomycin resistance for eukaryotic cell culture, and tetracycline, kanamycin or ampicillin resistance genes for culturing in *E. coli* and other bacteria. Representative examples of appropriate hosts include, but are not limited to, bacterial cells, such as *E. coli, Streptomyces* and *Salmonella typhimurium* cells; fungal cells, such as yeast cells (e.g., *Saccharomyces cerevisiae* or *Pichia pastoris* (ATCC™ Accession No. 201178)); insect cells such as *Drosophila* S2 and *Spodoptera* Sf9 cells; animal cells such as CHO, COS, 293, and Bowes melanoma cells; and plant cells. Appropriate culture mediums and conditions for the above-described host cells are known in the art.

Among vectors preferred for use in bacteria include pQE70, pQE60 and pQE-9, available from QIAGEN, Inc.; pBLUESCRIPT™ vectors, Phagescript vectors, pNH8A, pNH16a, pNH18A, pNH46A, available from STRATAGENE™ Cloning Systems, Inc.; and ptrc99a, pKK223-3, pKK233-3, pDR540, pRIT5 available from PHARMACIA™ Biotech, Inc. Among preferred eukaryotic vectors are pWLNEO, pSV2CAT, pOG44, pXT1 and pSG available from STRATAGENE™; and pSVK3, pBPV, pMSG and pSVL available from PHARMACIA™. Preferred expression vectors for use in yeast systems include, but are not limited to pYES2, pYD1, pTEF1/Zeo, pYES2/GS, pPICZ, pGAPZ, pGAPZalph, pPIC9, pPIC3.5, pHIL-D2, pHIL-S1, pPIC3.5K, pPIC9K, and PAO815 (all available from Invitrogen, Carlbad, Calif.). Other suitable vectors will be readily apparent to the skilled artisan.

Vectors which use glutamine synthase (GS) or DHFR as the selectable markers can be amplified in the presence of the drugs methionine sulphoximine or methotrexate, respectively. An advantage of glutamine synthase based vectors is the availability of cell lines (e.g., the murine myeloma cell line, NS0) which are glutamine synthase negative. Glutamine synthase expression systems can also function in glutamine synthase expressing cells (e.g., Chinese Hamster Ovary (CHO) cells) by providing additional inhibitor to prevent the functioning of the endogenous gene. A glutamine synthase expression system and components thereof are detailed in PCT publications: WO87/04462; WO86/05807; WO89/01036; WO89/10404; and WO91/06657, which are hereby incorporated in their entireties by reference herein. Additionally, glutamine synthase expression vectors can be obtained from Lonza Biologics, Inc. (Portsmouth, N.H.). Expression and production of monoclonal antibodies using a GS expression system in murine myeloma cells is described in Bebbington et al., *Bio/technology* 10:169 (1992) and in Biblia and Robinson *Biotechnol. Prog.* 11:1 (1995) which are herein incorporated by reference.

The present invention also relates to host cells containing the above-described vector constructs described herein, and additionally encompasses host cells containing nucleotide sequences of the invention that are operably associated with one or more heterologous control regions (e.g., promoter and/or enhancer) using techniques known of in the art. The host cell can be a higher eukaryotic cell, such as a mammalian cell (e.g., a human derived cell), or a lower eukaryotic cell, such as a yeast cell, or the host cell can be a prokaryotic cell, such as a bacterial cell. A host strain may be chosen which modulates the expression of the inserted gene sequences, or modifies and processes the gene product in the specific fashion desired. Expression from certain promoters can be elevated in the presence of certain inducers; thus expression of the genetically engineered polypeptide may be controlled. Furthermore, different host cells have characteristics and specific mechanisms for the translational and post-translational processing and modification (e.g., phosphorylation, cleavage) of proteins. Appropriate cell lines can be chosen to ensure the desired modifications and processing of the foreign protein expressed.

Introduction of the nucleic acids and nucleic acid constructs of the invention into the host cell can be effected by calcium phosphate transfection, DEAE-dextran mediated transfection, cationic lipid-mediated transfection, electroporation, transduction, infection, or other methods. Such methods are described in many standard laboratory manuals, such as Davis et al., Basic Methods In Molecular Biology (1986). It is specifically contemplated that the polypeptides of the present invention may in fact be expressed by a host cell lacking a recombinant vector.

In addition to encompassing host cells containing the vector constructs discussed herein, the invention also encompasses primary, secondary, and immortalized host cells of vertebrate origin, particularly mammalian origin, that have been engineered to delete or replace endogenous genetic material (e.g., the coding sequence), and/or to include genetic material (e.g., heterologous polynucleotide sequences) that is operably associated with polynucleotides of the invention, and which activates, alters, and/or amplifies endogenous polynucleotides. For example, techniques known in the art may be used to operably associate heterologous control regions (e.g., promoter and/or enhancer) and endogenous polynucleotide sequences via homologous recombination (see, e.g., U.S. Pat. No. 5,641,670, issued Jun. 24, 1997; U.S. Pat. No. 5,733,761, issued Mar. 31, 1998; International Publication Number WO 96/29411; International Publication Number WO 94/12650; Koller et al., *Proc. Natl. Acad. Sci. USA* 86:8932-8935 (1989); and Zijlstra et al., *Nature* 342: 435-438 (1989), the disclosures of each of which are incorporated by reference in their entireties).

Polypeptides of the invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification.

Polypeptides of the present invention can also be recovered from: products purified from natural sources, including bodily fluids, tissues and cells, whether directly isolated or cultured; products of chemical synthetic procedures; and products produced by recombinant techniques from a prokaryotic or eukaryotic host, including, for example, bacterial, yeast, higher plant, insect, and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes. Thus, it is well known in the art that the N-terminal methionine encoded by the translation initiation codon generally is removed with high efficiency from any protein after translation in all eukaryotic cells. While the N-terminal methionine on most proteins also is efficiently removed in most prokaryotes, for some proteins, this prokaryotic removal process is inefficient, depending on the nature of the amino acid to which the N-terminal methionine is covalently linked.

In one embodiment, the yeast *Pichia pastoris* is used to express polypeptides of the invention in a eukaryotic system. *Pichia pastoris* is a methylotrophic yeast which can metabolize methanol as its sole carbon source. A main step in the methanol metabolization pathway is the oxidation of methanol to formaldehyde using $O_2$. This reaction is catalyzed by the enzyme alcohol oxidase. In order to metabolize methanol as its sole carbon source, *Pichia pastoris* must generate high levels of alcohol oxidase due, in part, to the relatively low affinity of alcohol oxidase for $O_2$. Consequently, in a growth medium depending on methanol as a main carbon source, the promoter region of one of the two alcohol oxidase genes (AOX1) is highly active. In the presence of methanol, alcohol oxidase produced from the AOX1 gene comprises up to approximately 30% of the total soluble protein in *Pichia pastoris*. See Ellis, S. B., et al., *Mol. Cell. Biol.* 5:1111-21 (1985); Koutz, P. J, et al., *Yeast* 5:167-77 (1989); Tschopp, J. F., et al., *Nucl. Acids Res.* 15:3859-76 (1987). Thus, a heterologous coding sequence, such as, for example, a polynucleotide of the present invention, under the transcriptional regulation of all or part of the AOX1 regulatory sequence is expressed at exceptionally high levels in *Pichia* yeast grown in the presence of methanol.

In one example, the plasmid vector pPIC9K is used to express DNA encoding a polypeptide of the invention, as set forth herein, in a *Pichea* yeast system essentially as described in "*Pichia* Protocols: Methods in Molecular Biology," D. R. Higgins and J. Cregg, eds. The Humana Press, Totowa, N.J., 1998. This expression vector allows expression and secretion of a polypeptide of the invention by virtue of the strong AOX1 promoter linked to the *Pichia pastoris* alkaline phosphatase (PHO) secretory signal peptide (i.e., leader) located upstream of a multiple cloning site.

Many other yeast vectors could be used in place of pPIC9K, such as, pYES2, pYD1, pTEF1/Zeo, pYES2/GS, pPICZ, pGAPZ, pGAPZalpha, pPIC9, pPIC3.5, pHIL-D2, pHIL-S1, pPIC3.5K, and PAO815, as one skilled in the art would readily appreciate, as long as the proposed expression construct provides appropriately located signals for transcription, translation, secretion (if desired), and the like, including an in-frame AUG as required.

In another embodiment, high-level expression of a heterologous coding sequence, such as, for example, a polynucleotide of the present invention, may be achieved by cloning the heterologous polynucleotide of the invention into an expression vector such as, for example, pGAPZ or pGAPZalpha, and growing the yeast culture in the absence of methanol.

In addition to encompassing host cells containing the vector constructs discussed herein, the invention also encompasses primary, secondary, and immortalized host cells of vertebrate origin, particularly mammalian origin, that have been engineered to delete or replace endogenous genetic material (e.g., coding sequence), and/or to include genetic material (e.g., heterologous polynucleotide sequences) that is operably associated with polynucleotides of the invention, and which activates, alters, and/or amplifies endogenous polynucleotides. For example, techniques known in the art may be used to operably associate heterologous control regions (e.g., promoter and/or enhancer) and endogenous polynucleotide sequences via homologous recombination (see, e.g., U.S. Pat. No. 5,641,670, issued Jun. 24, 1997; International Publication No. WO 96/29411, published Sep. 26, 1996; International Publication No. WO 94/12650, published Aug. 4, 1994; Koller et al., Proc. Natl. Acad. Sci. USA 86:8932-8935 (1989); and Zijlstra et al., Nature 342:435-438 (1989), the disclosures of each of which are incorporated by reference in their entireties).

In addition, polypeptides of the invention can be chemically synthesized using techniques known in the art (e.g., see Creighton, 1983, Proteins: Structures and Molecular Principles, W.H. Freeman & Co., N.Y., and Hunkapiller et al., *Nature,* 310:105-111 (1984)). For example, a polypeptide corresponding to a fragment of a polypeptide can be synthesized by use of a peptide synthesizer. Furthermore, if desired, nonclassical amino acids or chemical amino acid analogs can be introduced as a substitution or addition into the polypeptide sequence. Non-classical amino acids include, but are not limited to, to the D-isomers of the common amino acids, 2,4-diaminobutyric acid, a-amino isobutyric acid, 4-aminobutyric acid, Abu, 2-amino butyric acid, g-Abu, e-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, b-alanine, fluoro-amino acids, designer amino acids such as b-methyl amino acids, Ca-methyl amino acids, Na-methyl amino acids, and amino acid analogs in general. Furthermore, the amino acid can be D (dextrorotary) or L (levorotary).

The invention encompasses polypeptides of the present invention which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited, to specific chemical cleavage by cyanogen bromide, trypsin, chymotrypsin, papain, V8 protease, $NaBH_4$; acetylation, formylation, oxidation, reduction; metabolic synthesis in the presence of tunicamycin; etc.

Additional post-translational modifications encompassed by the invention include, for example, e.g., N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue as a result of procaryotic host cell expression. The polypeptides may also be modified with a detectable label, such as an enzymatic, fluorescent, isotopic or affinity label to allow for detection and isolation of the protein.

Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include iodine ($^{121}I$, $^{123}I$, $^{125}I$, $^{131}I$), carbon ($^{14}C$), sulfur ($^{35}S$), tritium ($^{3}H$), indium ($^{111}In$, $^{112}In$, $^{113m}In$, $^{115m}In$), technetium ($^{99}Tc$, $^{99m}Tc$), thallium ($^{201}Ti$), gallium ($^{68}Ga$, $^{67}Ga$), palladium ($^{103}Pd$) molybdenum ($^{99}Mo$), xenon ($^{133}Xe$), fluorine ($^{18}F$), $^{153}Sm$, $^{177}Lu$, $^{159}Gd$, $^{149}Pm$, $^{140}La$, $^{175}Yb$, $^{166}Ho$, $^{90}Y$, $^{47}Sc$, $^{186}Re$, $^{188}Re$, $^{142}Pr$, $^{105}Rh$ and $^{97}Ru$.

In specific embodiments, a polypeptide of the present invention or fragment or variant thereof is attached to macrocyclic chelators that associate with radiometal ions, including but not limited to, $^{177}Lu$, $^{90}Y$, $^{166}Ho$, and $^{153}Sm$, to polypeptides. In a preferred embodiment the radiometal ion associated with the macrocyclic chelators is $^{111}In$. In another preferred embodiment, the radiometal ion associated with the macrocyclic chelator is $^{90}Y$. In specific embodiments, the macrocyclic chelator is 1,4,7,10-tetraazacyclododecane-N,N',N",N"'-tetraacetic acid (DOTA). In other specific embodiments, DOTA is attached to an antibody of the invention or fragment thereof via a linker molecule. Examples of linker molecules useful for conjugating DOTA to a polypeptide are commonly known in the art—see, for example, DeNardo et al., Clin Cancer Res. 4(10):2483-90 (1998); Peterson et al., Bioconjug. Chem. 10(4):553-7 (1999); and Zimmerman et al, Nucl. Med. Biol. 26(8):943-50 (1999); which are hereby incorporated by reference in their entirety.

As mentioned, the proteins of the invention may be modified by either natural processes, such as posttranslational processing, or by chemical modification techniques which are well known in the art. It will be appreciated that the same type of modification may be present in the same or varying degrees at several sites in a given polypeptide. Polypeptides of the invention may be branched, for example, as a result of ubiquitination, and they may be cyclic, with or without branching. Cyclic, branched, and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, PROTEINS—STRUCTURE AND MOLECULAR PROPERTIES, 2nd Ed., T. E. Creighton, W. H. Freeman and Company, New York (1993); POSTTRANSLATIONAL COVALENT MODIFICATION OF PROTEINS, B. C. Johnson, Ed., Academic Press, New York, pgs. 1-12 (1983); Seifter et al., Meth. Enzymol. 182: 626-646 (1990); Rattan et al., Ann. N.Y. Acad. Sci. 663:48-62 (1992)).

Also provided by the invention are chemically modified derivatives of the polypeptides of the invention which may provide additional advantages such as increased solubility, stability and circulating time of the polypeptide, or decreased immunogenicity (see U.S. Pat. No. 4,179,337). The chemical moieties for derivitization may be selected from water soluble polymers such as polyethylene glycol, ethylene glycol/propylene glycol copolymers, carboxymethylcellulose, dextran, polyvinyl alcohol and the like. The polypeptides may be modified at random positions within the molecule, or at predetermined positions within the molecule and may include one, two, three or more attached chemical moieties.

The polymer may be of any molecular weight, and may be branched or unbranched. For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog). For example, the polyethylene glycol may have an average molecular weight of about 200, 500, 1000, 1500, 2000, 2500, 3000, 3500, 4000, 4500, 5000, 5500, 6000, 6500, 7000, 7500, 8000, 8500, 9000, 9500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, 20,000, 25,000, 30,000, 35,000, 40,000, 45,000, 50,000, 55,000, 60,000, 65,000, 70,000, 75,000, 80,000, 85,000, 90,000, 95,000, or 100,000 kDa.

As noted above, the polyethylene glycol may have a branched structure. Branched polyethylene glycols are described, for example, in U.S. Pat. No. 5,643,575; Morpurgo et al., *Appl. Biochem. Biotechnol.* 56:59-72 (1996); Vorobjev et al., *Nucleosides Nucleotides* 18:2745-2750 (1999); and Caliceti et al., *Bioconjug. Chem.* 10:638-646 (1999), the disclosures of each of which are incorporated herein by reference.

The polyethylene glycol molecules (or other chemical moieties) should be attached to the protein with consideration of effects on functional or antigenic domains of the protein. There are a number of attachment methods available to those skilled in the art, such as, for example, the method disclosed in EP 0 401 384 (coupling PEG to G-CSF), herein incorporated by reference; see also Malik et al., Exp. Hematol. 20:1028-1035 (1992), reporting pegylation of GM-CSF using tresyl chloride. For example, polyethylene glycol may be covalently bound through amino acid residues via a reactive group, such as a free amino or carboxyl group. Reactive groups are those to which an activated polyethylene glycol molecule may be bound. The amino acid residues having a free amino group may include lysine residues and the N-terminal amino acid residues; those having a free carboxyl group may include aspartic acid residues glutamic acid residues and the C-terminal amino acid residue. Sulfhydryl groups may also be used as a reactive group for attaching the polyethylene glycol molecules. Preferred for therapeutic purposes is attachment at an amino group, such as attachment at the N-terminus or lysine group.

As suggested above, polyethylene glycol may be attached to proteins via linkage to any of a number of amino acid residues. For example, polyethylene glycol can be linked to proteins via covalent bonds to lysine, histidine, aspartic acid, glutamic acid, or cysteine residues. One or more reaction chemistries may be employed to attach polyethylene glycol to specific amino acid residues (e.g., lysine, histidine, aspartic acid, glutamic acid, or cysteine) of the protein or to more than one type of amino acid residue (e.g., lysine, histidine, aspartic acid, glutamic acid, cysteine and combinations thereof) of the protein.

One may specifically desire proteins chemically modified at the N-terminus. Using polyethylene glycol as an illustration of the present composition, one may select from a variety of polyethylene glycol molecules (by molecular weight, branching, etc.), the proportion of polyethylene glycol molecules to protein (polypeptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective proteins chemically modified at the N-terminus modification may be accomplished by reductive alkylation that exploits differential reactivity of different types of primary amino groups (lysine versus the N-terminal) available for derivatization in a particular protein. Under the appropriate reaction conditions, substantially selective derivatization of the protein at the N-terminus with a carbonyl group containing polymer is achieved.

As indicated above, pegylation of the proteins of the invention may be accomplished by any number of means. For example, polyethylene glycol may be attached to the protein either directly or by an intervening linker. Linkerless systems for attaching polyethylene glycol to proteins are described in Delgado et al., Crit. Rev. Thera. Drug Carrier Sys. 9:249-304 (1992); Francis et al., Intern. J. of Hematol. 68:1-18 (1998); U.S. Pat. No. 4,002,531; U.S. Pat. No. 5,349,052; WO 95/06058; and WO 98/32466, the disclosures of each of which are incorporated herein by reference.

One system for attaching polyethylene glycol directly to amino acid residues of proteins without an intervening linker employs tresylated MPEG, which is produced by the modification of monomethoxy polyethylene glycol (MPEG) using tresylchloride ($ClSO_2CH_2CF_3$). Upon reaction of protein with tresylated MPEG, polyethylene glycol is directly attached to amine groups of the protein. Thus, the invention includes protein-polyethylene glycol conjugates produced by reacting proteins of the invention with a polyethylene glycol molecule having a 2,2,2-trifluoroethane sulphonyl group.

Polyethylene glycol can also be attached to proteins using a number of different intervening linkers. For example, U.S. Pat. No. 5,612,460, the entire disclosure of which is incorporated herein by reference, discloses urethane linkers for connecting polyethylene glycol to proteins. Protein-polyethylene glycol conjugates wherein the polyethylene glycol is attached to the protein by a linker can also be produced by reaction of proteins with compounds such as MPEG-succinimidylsuccinate, MPEG activated with 1,1'-carbonyldiimidazole, MPEG-2,4,5-trichlorophenylcarbonate, MPEG-p-nitrophenolcarbonate, and various MPEG-succinate derivatives. A number of additional polyethylene glycol derivatives and reaction chemistries for attaching polyethylene glycol to proteins are described in International Publication No. WO 98/32466, the entire disclosure of which is incorporated herein by reference. Pegylated protein products produced using the reaction chemistries set out herein are included within the scope of the invention.

The number of polyethylene glycol moieties attached to each protein of the invention (i.e., the degree of substitution) may also vary. For example, the pegylated proteins of the invention may be linked, on average, to 1, 2, 3, 4, 5, 6, 7, 8, 9, 10, 12, 15, 17, 20, or more polyethylene glycol molecules. Similarly, the average degree of substitution within ranges such as 1-3, 2-4, 3-5, 4-6, 5-7, 6-8, 7-9, 8-10, 9-11, 10-12, 11-13, 12-14, 13-15, 14-16, 15-17, 16-18, 17-19, or 18-20 polyethylene glycol moieties per protein molecule. Methods for determining the degree of substitution are discussed, for example, in Delgado et al., Crit. Rev. Thera. Drug Carrier Sys. 9:249-304 (1992).

The polypeptides of the invention can be recovered and purified from chemical synthesis and recombinant cell cultures by standard methods which include, but are not limited to, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Well known techniques for refolding protein may be employed to regenerate active conformation when the polypeptide is denatured during isolation and/or purification.

The polypeptides of the invention may be in monomers or multimers (i.e., dimers, trimers, tetramers and higher multimers). Accordingly, the present invention relates to monomers and multimers of the polypeptides of the invention, their preparation, and compositions (preferably, Therapeutics) containing them. In specific embodiments, the polypeptides of the invention are monomers, dimers, trimers or tetramers. In additional embodiments, the multimers of the invention are at least dimers, at least trimers, or at least tetramers.

Multimers encompassed by the invention may be homomers or heteromers. As used herein, the term homomer refers to a multimer containing only polypeptides corresponding to a protein of the invention (e.g., the amino acid sequence of SEQ ID NO:Y, an amino acid sequence encoded by SEQ ID NO:X or the complement of SEQ ID NO:X, the amino acid sequence encoded by the portion of SEQ ID NO:X as defined in columns 8 and 9 of Table 2, and/or an amino acid sequence encoded by cDNA contained in ATCC™ Deposit No:Z (including fragments, variants, splice variants, and fusion proteins, corresponding to these as described herein)). These homomers may contain polypeptides having identical or different amino acid sequences. In a specific embodiment, a homomer of the invention is a multimer containing only polypeptides having an identical amino acid sequence. In another specific embodiment, a homomer of the invention is a multimer containing polypeptides having different amino acid sequences. In specific embodiments, the multimer of the invention is a homodimer (e.g., containing two polypeptides having identical or different amino acid sequences) or a homotrimer (e.g., containing three polypeptides having identical and/or different amino acid sequences). In additional embodiments, the homomeric multimer of the invention is at least a homodimer, at least a homotrimer, or at least a homotetramer.

As used herein, the term heteromer refers to a multimer containing one or more heterologous polypeptides (i.e., polypeptides of different proteins) in addition to the polypeptides of the invention. In a specific embodiment, the multimer of the invention is a heterodimer, a heterotrimer, or a heterotetramer. In additional embodiments, the heteromeric multimer of the invention is at least a heterodimer, at least a heterotrimer, or at least a heterotetramer.

Multimers of the invention may be the result of hydrophobic, hydrophilic, ionic and/or covalent associations and/or may be indirectly linked by, for example, liposome formation. Thus, in one embodiment, multimers of the invention, such as, for example, homodimers or homotrimers, are formed when polypeptides of the invention contact one another in solution. In another embodiment, heteromultimers of the invention, such as, for example, heterotrimers or heterotetramers, are formed when polypeptides of the invention contact antibodies to the polypeptides of the invention (including antibodies to the heterologous polypeptide sequence in a fusion protein of the invention) in solution. In other embodiments, multimers of the invention are formed by covalent associations with and/or between the polypeptides of the invention. Such covalent associations may involve one or more amino acid residues contained in the polypeptide sequence (e.g., that recited in SEQ ID NO:Y, encoded by the portion of SEQ ID NO:X as defined in columns 8 and 9 of Table 2, and/or encoded by the cDNA contained in ATCC™ Deposit No:Z). In one instance, the covalent associations are cross-linking between cysteine residues located within the polypeptide sequences which interact in the native (i.e., naturally occurring) polypeptide. In another instance, the covalent associations are the consequence of chemical or recombinant manipulation. Alternatively, such covalent associations may involve one or more amino acid residues contained in the heterologous polypeptide sequence in a fusion protein. In one example, covalent associations are between the heterologous sequence contained in a fusion protein of the invention (see, e.g., U.S. Pat. No. 5,478,925). In a specific example, the covalent associations are between the heterologous sequence contained in a Fc fusion protein of the invention (as described herein). In another specific example, covalent associations of fusion proteins of the invention are between heterologous polypeptide sequence from another protein that is capable of forming covalently associated multimers, such as for example, osteoprotegerin (see, e.g., International Publication NO: WO 98/49305, the contents of which are herein incorporated by reference in its entirety). In another embodiment, two or more polypeptides of the invention are joined through peptide linkers. Examples include those peptide linkers described in U.S. Pat. No. 5,073,627 (hereby incorporated by reference). Proteins comprising multiple polypeptides of the invention separated by peptide linkers may be produced using conventional recombinant DNA technology.

Another method for preparing multimer polypeptides of the invention involves use of polypeptides of the invention fused to a leucine zipper or isoleucine zipper polypeptide sequence. Leucine zipper and isoleucine zipper domains are polypeptides that promote multimerization of the proteins in which they are found. Leucine zippers were originally identified in several DNA-binding proteins (Landschulz et al., Science 240:1759, (1988)), and have since been found in a variety of different proteins. Among the known leucine zippers are naturally occurring peptides and derivatives thereof that dimerize or trimerize. Examples of leucine zipper domains suitable for producing soluble multimeric proteins of the invention are those described in PCT application WO 94/10308, hereby incorporated by reference. Recombinant fusion proteins comprising a polypeptide of the invention fused to a polypeptide sequence that dimerizes or trimerizes in solution are expressed in suitable host cells, and the resulting soluble multimeric fusion protein is recovered from the culture supernatant using techniques known in the art.

Trimeric polypeptides of the invention may offer the advantage of enhanced biological activity. Preferred leucine zipper moieties and isoleucine moieties are those that preferentially form trimers. One example is a leucine zipper derived from lung surfactant protein D (SPD), as described in Hoppe et al. (FEBS Letters 344:191, (1994)) and in U.S. patent application Ser. No. 08/446,922, hereby incorporated by reference. Other peptides derived from naturally occurring trimeric proteins may be employed in preparing trimeric polypeptides of the invention.

In another example, proteins of the invention are associated by interactions between Flag® polypeptide sequence contained in fusion proteins of the invention containing Flag® polypeptide sequence. In a further embodiment, proteins of the invention are associated by interactions between heterologous polypeptide sequence contained in Flag® fusion proteins of the invention and anti-Flag® antibody.

The multimers of the invention may be generated using chemical techniques known in the art. For example, polypeptides desired to be contained in the multimers of the invention may be chemically cross-linked using linker molecules and linker molecule length optimization techniques known in the art (see, e.g., U.S. Pat. No. 5,478,925, which is herein incorporated by reference in its entirety). Additionally, multimers of the invention may be generated using techniques known in the art to form one or more inter-molecule cross-links between the cysteine residues located within the sequence of the polypeptides desired to be contained in the multimer (see, e.g., U.S. Pat. No. 5,478,925, which is herein incorporated by reference in its entirety). Further, polypeptides of the invention may be routinely modified by the addition of cysteine or biotin to the C-terminus or N-terminus of the polypeptide and techniques known in the art may be applied to generate multimers containing one or more of these modified polypeptides (see, e.g., U.S. Pat. No. 5,478,925, which is herein incorporated by reference in its entirety). Additionally, techniques known in the art may be applied to generate liposomes containing the polypeptide components desired to be contained in the multimer of the invention (see, e.g., U.S. Pat. No. 5,478,925, which is herein incorporated by reference in its entirety).

Alternatively, multimers of the invention may be generated using genetic engineering techniques known in the art. In one embodiment, polypeptides contained in multimers of the invention are produced recombinantly using fusion protein technology described herein or otherwise known in the art (see, e.g., U.S. Pat. No. 5,478,925, which is herein incorporated by reference in its entirety). In a specific embodiment, polynucleotides coding for a homodimer of the invention are generated by ligating a polynucleotide sequence encoding a polypeptide of the invention to a sequence encoding a linker polypeptide and then further to a synthetic polynucleotide encoding the translated product of the polypeptide in the reverse orientation from the original C-terminus to the N-terminus (lacking the leader sequence) (see, e.g., U.S. Pat. No. 5,478,925, which is herein incorporated by reference in its entirety). In another embodiment, recombinant techniques described herein or otherwise known in the art are applied to generate recombinant polypeptides of the invention which contain a transmembrane domain (or hydrophobic or signal peptide) and which can be incorporated by membrane reconstitution techniques into liposomes (see, e.g., U.S. Pat. No. 5,478,925, which is herein incorporated by reference in its entirety).

Antibodies

Further polypeptides of the invention relate to antibodies and T-cell antigen receptors (TCR) which immunospecifically bind a polypeptide, polypeptide fragment, or variant of the invention (e.g., a polypeptide or fragment or variant of the amino acid sequence of SEQ ID NO:Y or a polypeptide encoded by the cDNA contained in ATCC™ Deposit No:Z, and/or an epitope, of the present invention) as determined by immunoassays well known in the art for assaying specific antibody-antigen binding. Antibodies of the invention include, but are not limited to, polyclonal, monoclonal, multispecific, human, humanized or chimeric antibodies, single chain antibodies, Fab fragments, F(ab') fragments, fragments produced by a Fab expression library, anti-idiotypic (anti-Id) antibodies (including, e.g., anti-Id antibodies to antibodies of the invention), intracellularly-made antibodies (i.e., intrabodies), and epitope-binding fragments of any of the above. The term "antibody," as used herein, refers to immunoglobulin molecules and immunologically active portions of immunoglobulin molecules, i.e., molecules that contain an antigen binding site that immunospecifically binds an antigen. The immunoglobulin molecules of the invention can be of any type (e.g., IgG, IgE, IgM, IgD, IgA and IgY), class (e.g., IgG1, IgG2, IgG3, IgG4, IgA1 and IgA2) or subclass of immunoglobulin molecule. In preferred embodiments, the immunoglobulin molecules of the invention are IgG1. In other preferred embodiments, the immunoglobulin molecules of the invention are IgG4.

Most preferably the antibodies are human antigen-binding antibody fragments of the present invention and include, but are not limited to, Fab, Fab' and F(ab')2, Fd, single-chain Fvs (scFv), single-chain antibodies, disulfide-linked Fvs (sdFv) and fragments comprising either a VL or VH domain. Antigen-binding antibody fragments, including single-chain antibodies, may comprise the variable region(s) alone or in combination with the entirety or a portion of the following: hinge region, CH1, CH2, and CH3 domains. Also included in the invention are antigen-binding fragments also comprising any combination of variable region(s) with a hinge region, CH1, CH2, and CH3 domains. The antibodies of the invention may be from any animal origin including birds and mammals. Preferably, the antibodies are human, murine (e.g., mouse and rat), donkey, ship rabbit, goat, guinea pig, camel, horse, or chicken. As used herein, "human" antibodies include antibodies having the amino acid sequence of a human immunoglobulin and include antibodies isolated from human immunoglobulin libraries or from animals transgenic for one or more human immunoglobulin and that do not express endogenous immunoglobulins, as described infra and, for example in, U.S. Pat. No. 5,939,598 by Kucherlapati et al.

The antibodies of the present invention may be monospecific, bispecific, trispecific or of greater multispecificity. Multispecific antibodies may be specific for different epitopes of a polypeptide of the present invention or may be specific for both a polypeptide of the present invention as well as for a heterologous epitope, such as a heterologous polypeptide or solid support material. See, e.g., PCT publications WO 93/17715; WO 92/08802; WO 91/00360; WO 92/05793; Tutt, et al., J. Immunol. 147:60-69 (1991); U.S. Pat. Nos. 4,474,893; 4,714,681; 4,925,648; 5,573,920; 5,601,819; Kostelny et al., J. Immunol. 148:1547-1553 (1992).

Antibodies of the present invention may be described or specified in terms of the epitope(s) or portion(s) of a polypeptide of the present invention which they recognize or specifically bind. The epitope(s) or polypeptide portion(s) may be specified as described herein, e.g., by N-terminal and C-terminal positions, or by size in contiguous amino acid residues, or listed in the Tables and Figures. Preferred epitopes of the invention include the predicted epitopes shown in Table 1B.1 (such as epitopes shown in column 7 of Table 1B.1), as well as polynucleotides that encode these epitopes. Antibodies which specifically bind any epitope or polypeptide of the present invention may also be excluded. Therefore, the present invention includes antibodies that specifically bind polypeptides of the present invention, and allows for the exclusion of the same.

Antibodies of the present invention may also be described or specified in terms of their cross-reactivity. Antibodies that do not bind any other analog, ortholog, or homolog of a polypeptide of the present invention are included. Antibodies that bind polypeptides with at least 95%, at least 90%, at least 85%, at least 80%, at least 75%, at least 70%, at least 65%, at least 60%, at least 55%, and at least 50% identity (as calculated using methods known in the art and described herein) to a polypeptide of the present invention are also included in the present invention. In specific embodiments, antibodies of the present invention cross-react with murine, rat and/or rabbit homologs of human proteins and the corresponding epitopes thereof. Antibodies that do not bind polypeptides with less than 95%, less than 90%, less than 85%, less than 80%, less than 75%, less than 70%, less than 65%, less than 60%, less than 55%, and less than 50% identity (as calculated using methods known in the art and described herein) to a polypeptide of the present invention are also included in the present invention. In a specific embodiment, the above-described cross-reactivity is with respect to any single specific antigenic or immunogenic polypeptide, or combination(s) of 2, 3, 4, 5, or more of the specific antigenic and/or immunogenic polypeptides disclosed herein. Further included in the present invention are antibodies which bind polypeptides encoded by polynucleotides which hybridize to a polynucleotide of the present invention under stringent hybridization conditions (as described herein). Antibodies of the present invention may also be described or specified in terms of their binding affinity to a polypeptide of the invention. Preferred binding affinities include those with a dissociation constant or Kd less than $5\times10^{-2}$ M, $10^{-2}$ M, $5\times10^{-3}$ M, $10^{-3}$ M, $5\times10^{-4}$ M, $10^{-4}$ M, $5\times10^{-5}$ M, $10^{-5}$ M, $5\times10^{-6}$ M, $10^{-6}$M, $5\times10^{-7}$ M, $10^{7}$ M, $5\times10^{-8}$ M, $10^{-8}$ M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, $10^{-13}$ M, $5\times10^{-14}$ M, $10^{-14}$ M, $5\times10^{-15}$ M, or $10^{-15}$ M.

The invention also provides antibodies that competitively inhibit binding of an antibody to an epitope of the invention as determined by any method known in the art for determining competitive binding, for example, the immunoassays described herein. In preferred embodiments, the antibody competitively inhibits binding to the epitope by at least 95%, at least 90%, at least 85%, at least 80%, at least 75%, at least 70%, at least 60%, or at least 50%.

Antibodies of the present invention may act as agonists or antagonists of the polypeptides of the present invention. For example, the present invention includes antibodies which disrupt the receptor/ligand interactions with the polypeptides of the invention either partially or fully. Preferably, antibodies of the present invention bind an antigenic epitope disclosed herein, or a portion thereof. The invention features both receptor-specific antibodies and ligand-specific antibodies. The invention also features receptor-specific antibodies which do not prevent ligand binding but prevent receptor activation. Receptor activation (i.e., signaling) may be determined by techniques described herein or otherwise known in the art. For example, receptor activation can be determined by detecting the phosphorylation (e.g., tyrosine or serine/threonine) of the receptor or its substrate by immunoprecipitation followed by western blot analysis (for example, as described supra). In specific embodiments, antibodies are provided that inhibit ligand activity or receptor activity by at least 95%, at least 90%, at least 85%, at least 80%, at least 75%, at least 70%, at least 60%, or at least 50% of the activity in absence of the antibody.

The invention also features receptor-specific antibodies which both prevent ligand binding and receptor activation as well as antibodies that recognize the receptor-ligand complex, and, preferably, do not specifically recognize the unbound receptor or the unbound ligand. Likewise, included in the invention are neutralizing antibodies which bind the ligand and prevent binding of the ligand to the receptor, as well as antibodies which bind the ligand, thereby preventing receptor activation, but do not prevent the ligand from binding the receptor. Further included in the invention are antibodies which activate the receptor. These antibodies may act as receptor agonists, i.e., potentiate or activate either all or a subset of the biological activities of the ligand-mediated receptor activation, for example, by inducing dimerization of the receptor. The antibodies may be specified as agonists, antagonists or inverse agonists for biological activities comprising the specific biological activities of the peptides of the invention disclosed herein. The above antibody agonists can be made using methods known in the art. See, e.g., PCT publication WO 96/40281; U.S. Pat. No. 5,811,097; Deng et al., Blood 92(6):1981-1988 (1998); Chen et al., Cancer Res. 58(16):3668-3678 (1998); Harrop et al., J. Immunol. 161(4): 1786-1794 (1998); Zhu et al., Cancer Res. 58(15):3209-3214 (1998); Yoon et al., J. Immunol. 160(7):3170-3179 (1998); Prat et al., J. Cell. Sci. 111(Pt2):237-247 (1998); Pitard et al., J. Immunol. Methods 205(2):177-190 (1997); Liautard et al., Cytokine 9(4):233-241 (1997); Carlson et al., J. Biol. Chem. 272(17):11295-11301 (1997); Taryman et al., Neuron 14(4): 755-762 (1995); Muller et al., Structure 6(9):1153-1167 (1998); Bartunek et al., Cytokine 8(1):14-20 (1996) (which are all incorporated by reference herein in their entireties).

Antibodies of the present invention may be used, for example, to purify, detect, and target the polypeptides of the present invention, including both in vitro and in vivo diagnostic and therapeutic methods. For example, the antibodies have utility in immunoassays for qualitatively and quantitatively measuring levels of the polypeptides of the present invention in biological samples. See, e.g., Harlow et al., Antibodies: A Laboratory Manual, (Cold Spring Harbor Laboratory Press, 2nd ed. 1988); incorporated by reference herein in its entirety.

As discussed in more detail below, the antibodies of the present invention may be used either alone or in combination with other compositions. The antibodies may further be recombinantly fused to a heterologous polypeptide at the N- or C-terminus or chemically conjugated (including covalent and non-covalent conjugations) to polypeptides or other compositions. For example, antibodies of the present invention may be recombinantly fused or conjugated to molecules useful as labels in detection assays and effector molecules such as heterologous polypeptides, drugs, radionuclides, or toxins. See, e.g., PCT publications WO 92/08495; WO 91/14438; WO 89/12624; U.S. Pat. No. 5,314,995; and EP 396,387; the disclosures of which are incorporated herein by reference in their entireties.

The antibodies of the invention include derivatives that are modified, i.e, by the covalent attachment of any type of molecule to the antibody such that covalent attachment does not prevent the antibody from generating an anti-idiotypic response. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

The antibodies of the present invention may be generated by any suitable method known in the art. Polyclonal antibodies to an antigen-of-interest can be produced by various procedures well known in the art. For example, a polypeptide of the invention can be administered to various host animals including, but not limited to, rabbits, mice, rats, etc. to induce the production of sera containing polyclonal antibodies specific for the antigen. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum*. Such adjuvants are also well known in the art.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling, et al., in: Monoclonal Antibodies and T-Cell Hybridomas 563-681 (Elsevier, N.Y., 1981) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art and are discussed in detail in the Examples. In a non-limiting example, mice can be immunized with a polypeptide of the invention or a cell expressing such peptide. Once an immune response is detected, e.g., antibodies specific for the antigen are detected in the mouse serum, the mouse spleen is harvested and splenocytes isolated. The splenocytes are then fused by well known techniques to any suitable myeloma cells, for example cells from cell line SP20 available from the ATCC™. Hybridomas are selected and cloned by limited dilution. The hybridoma clones are then assayed by methods known in the art for cells that secrete antibodies capable of binding a polypeptide of the invention. Ascites fluid, which generally contains high levels of antibodies, can be generated by immunizing mice with positive hybridoma clones.

Accordingly, the present invention provides methods of generating monoclonal antibodies as well as antibodies produced by the method comprising culturing a hybridoma cell secreting an antibody of the invention wherein, preferably, the hybridoma is generated by fusing splenocytes isolated from a mouse immunized with an antigen of the invention with myeloma cells and then screening the hybridomas resulting from the fusion for hybridoma clones that secrete an antibody able to bind a polypeptide of the invention.

Another well known method for producing both polyclonal and monoclonal human B cell lines is transformation using Epstein Barr Virus (EBV). Protocols for generating EBV-transformed B cell lines are commonly known in the art, such as, for example, the protocol outlined in Chapter 7.22 of Current Protocols in Immunology, Coligan et al., Eds., 1994, John Wiley & Sons, NY, which is hereby incorporated in its entirety by reference. The source of B cells for transformation is commonly human peripheral blood, but B cells for transformation may also be derived from other sources including, but not limited to, lymph nodes, tonsil, spleen, tumor tissue, and infected tissues. Tissues are generally made into single cell suspensions prior to EBV transformation. Additionally, steps may be taken to either physically remove or inactivate T cells (e.g., by treatment with cyclosporin A) in B cell-containing samples, because T cells from individuals seropositive for anti-EBV antibodies can suppress B cell immortalization by EBV.

In general, the sample containing human B cells is innoculated with EBV, and cultured for 3-4 weeks. A typical source of EBV is the culture supernatant of the B95-8 cell line (ATCC™ #VR-1492). Physical signs of EBV transformation can generally be seen towards the end of the 3-4 week culture period. By phase-contrast microscopy, transformed cells may appear large, clear, hairy and tend to aggregate in tight clusters of cells. Initially, EBV lines are generally polyclonal. However, over prolonged periods of cell cultures, EBV lines may become monoclonal or polyclonal as a result of the selective outgrowth of particular B cell clones. Alternatively, polyclonal EBV transformed lines may be subcloned (e.g., by limiting dilution culture) or fused with a suitable fusion partner and plated at limiting dilution to obtain monoclonal B cell lines. Suitable fusion partners for EBV transformed cell lines include mouse myeloma cell lines (e.g., SP2/0, X63-Ag8.653), heteromyeloma cell lines (human×mouse; e.g, SPAM-8, SBC-H20, and CB-F7), and human cell lines (e.g., GM 1500, SKO-007, RPMI 8226, and KR-4). Thus, the present invention also provides a method of generating polyclonal or monoclonal human antibodies against polypeptides of the invention or fragments thereof, comprising EBV-transformation of human B cells.

Antibody fragments which recognize specific epitopes may be generated by known techniques. For example, Fab and F(ab')2 fragments of the invention may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CH1 domain of the heavy chain.

For example, the antibodies of the present invention can also be generated using various phage display methods known in the art. In phage display methods, functional antibody domains are displayed on the surface of phage particles which carry the polynucleotide sequences encoding them. In a particular embodiment, such phage can be utilized to display antigen binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Examples of phage display methods that can be used to make the antibodies of the present invention include those disclosed in Brinkman et al., J. Immunol. Methods 182:41-50 (1995); Ames et al., J. Immunol. Methods 184:177-186 (1995); Kettleborough et al., Eur. J. Immunol. 24:952-958 (1994); Persic et al., Gene 187 9-18 (1997); Burton et al., Advances in Immunology 57:191-280 (1994); PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described in detail below. For example, techniques to recombinantly produce Fab, Fab' and F(ab')2 fragments can also be employed using methods known in the art such as those disclosed in PCT publication WO 92/22324; Mullinax et al., BioTechniques 12(6):864-869 (1992); and Sawai et al., AJRI 34:26-34 (1995); and Better et al., Science 240:1041-1043 (1988) (said references incorporated by reference in their entireties).

Examples of techniques which can be used to produce single-chain Fvs and antibodies include those described in U.S. Pat. Nos. 4,946,778 and 5,258,498; Huston et al., Methods in Enzymology 203:46-88 (1991); Shu et al., PNAS 90:7995-7999 (1993); and Skerra et al., Science 240:1038-1040 (1988). For some uses, including in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See e.g., Morrison, Science 229:1202 (1985); Oi et al., BioTechniques 4:214 (1986); Gillies et al., (1989) J. Immunol. Methods 125:191-202; U.S. Pat. Nos. 5,807,715; 4,816,567; and 4,816397, which are incorporated herein by reference in their entirety. Humanized antibodies are antibody molecules from non-human species antibody that binds the desired antigen having one or more complementarity determining regions (CDRs) from the non-human species and a framework region from a human immunoglobulin molecule. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., Nature 332:323 (1988), which are incorporated herein by reference in their entireties.) Antibodies can be humanized using a variety of techniques known in the art including, for example, CDR-grafting (EP 239,400; PCT publication WO 91/09967; U.S. Pat. Nos. 5,225,539; 5,530,101; and 5,585,089), veneering or resurfacing (EP 592,106; EP 519,596; Padlan, Molecular Immunology 28(4/5):489-498 (1991); Studnicka et al., Protein Engineering 7(6):805-814 (1994); Roguska. et al., PNAS 91:969-973 (1994)), and chain shuffling (U.S. Pat. No. 5,565,332).

Completely human antibodies are particularly desirable for therapeutic treatment of human patients. Human antibodies can be made by a variety of methods known in the art including phage display methods described above using antibody libraries derived from human immunoglobulin sequences. See also, U.S. Pat. Nos. 4,444,887 and 4,716,111; and PCT publications WO 98/46645, WO 98/50433, WO 98/24893, WO 98/16654, WO 96/34096, WO 96/33735, and WO 91/10741; each of which is incorporated herein by reference in its entirety.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar, Int. Rev. Immunol. 13:65-93 (1995). For a detailed discussion of this technology for producing human antibodies and human monoclonal antibodies and protocols for producing such antibodies, see, e.g., PCT publications WO 98/24893; WO 92/01047; WO 96/34096; WO 96/33735; European Patent No. 0 598 877; U.S. Pat. Nos. 5,413,923; 5,625,126; 5,633,425; 5,569,825; 5,661,016; 5,545,806; 5,814,318; 5,885,793; 5,916,771; 5,939,598; 6,075,181; and 6,114,598, which are incorporated by reference herein in their entirety. In addition, companies such as ABGENIX™, Inc. (Freemont, Calif.) and Genpharm (San Jose, Calif.) can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al., Bio/technology 12:899-903 (1988)).

Further, antibodies to the polypeptides of the invention can, in turn, be utilized to generate anti-idiotype antibodies that "mimic" polypeptides of the invention using techniques well known to those skilled in the art. (See, e.g., Greenspan & Bona, FASEB J. 7(5):437-444; (1989) and Nissinoff, J. Immunol. 147(8):2429-2438 (1991)). For example, antibodies which bind to and competitively inhibit polypeptide multimerization and/or binding of a polypeptide of the invention to a ligand can be used to generate anti-idiotypes that "mimic" the polypeptide multimerization and/or binding domain and, as a consequence, bind to and neutralize polypeptide and/or its ligand. Such neutralizing anti-idiotypes or Fab fragments of such anti-idiotypes can be used in therapeutic regimens to neutralize polypeptide ligand(s)/receptor(s). For example, such anti-idiotypic antibodies can be used to bind a polypeptide of the invention and/or to bind its ligand(s)/receptor(s), and thereby block its biological activity. Alternatively, antibodies which bind to and enhance polypeptide multimerization and/or binding, and/or receptor/ligand multimerization, binding and/or signaling can be used to generate anti-idiotypes that function as agonists of a polypeptide of the invention and/or its ligand/receptor. Such agonistic anti-idiotypes or Fab fragments of such anti-idiotypes can be used in therapeutic regimens as agonists of the polypeptides of the invention or its ligand(s)/receptor(s). For example, such anti-idiotypic antibodies can be used to bind a polypeptide of the invention and/or to bind its ligand(s)/receptor(s), and thereby promote or enhance its biological activity.

Intrabodies of the invention can be produced using methods known in the art, such as those disclosed and reviewed in Chen et al., Hum. Gene Ther. 5:595-601 (1994); Marasco, W. A., Gene Ther. 4:11-15 (1997); Rondon and Marasco, Annu. Rev. Microbiol. 51:257-283 (1997); Proba et al., J. Mol. Biol. 275:245-253 (1998); Cohen et al., Oncogene 17:2445-2456 (1998); Ohage and Steipe, J. Mol. Biol. 291:1119-1128 (1999); Ohage et al., J. Mol. Biol. 291:1129-1134 (1999); Wirtz and Steipe, Protein Sci. 8:2245-2250 (1999); Zhu et al., J. Immunol. Methods 231:207-222 (1999); and references cited therein.

Polynucleotides Encoding Antibodies

The invention further provides polynucleotides comprising a nucleotide sequence encoding an antibody of the invention and fragments thereof. The invention also encompasses polynucleotides that hybridize under stringent or alternatively, under lower stringency hybridization conditions, e.g., as defined supra, to polynucleotides that encode an antibody, preferably, that specifically binds to a polypeptide of the invention, preferably, an antibody that binds to a polypeptide having the amino acid sequence of SEQ ID NO:Y, to a polypeptide encoded by a portion of SEQ ID NO:X as defined in columns 8 and 9 of Table 2, and/or to a polypeptide encoded by the cDNA contained in ATCC™ Deposit No:Z.

The polynucleotides may be obtained, and the nucleotide sequence of the polynucleotides determined, by any method known in the art. For example, if the nucleotide sequence of the antibody is known, a polynucleotide encoding the antibody may be assembled from chemically synthesized oligonucleotides (e.g., as described in Kutmeier et al., BioTechniques 17:242 (1994)), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody may be generated from nucleic acid from a suitable source. If a clone containing a nucleic acid encoding a particular antibody is not available, but the sequence of the antibody molecule is known, a nucleic acid encoding the immunoglobulin may be chemically synthesized or obtained from a suitable source (e.g., an antibody cDNA library, or a cDNA library generated from, or nucleic acid, preferably poly A+ RNA, isolated from, any tissue or cells expressing the antibody, such as hybridoma cells selected to express an antibody of the invention) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence and corresponding amino acid sequence of the antibody is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook et al., 1990, Molecular Cloning, A Laboratory Manual, 2d Ed., Cold Spring Harbor Laboratory, Cold Spring Harbor, N.Y. and Ausubel et al., eds., 1998, Current Protocols in Molecular Biology, John Wiley & Sons, NY, which are both incorporated by reference herein in their entireties), to generate antibodies having a different amino acid sequence, for example to create amino acid substitutions, deletions, and/or insertions.

In a specific embodiment, the amino acid sequence of the heavy and/or light chain variable domains may be inspected to identify the sequences of the complementarity determining regions (CDRs) by methods that are well know in the art, e.g., by comparison to known amino acid sequences of other heavy and light chain variable regions to determine the regions of sequence hypervariability. Using routine recombinant DNA techniques, one or more of the CDRs may be inserted within framework regions, e.g., into human framework regions to humanize a non-human antibody, as described supra. The framework regions may be naturally occurring or consensus framework regions, and preferably human framework regions (see, e.g., Chothia et al., J. Mol. Biol. 278: 457-479 (1998) for a listing of human framework regions). Preferably, the polynucleotide generated by the combination of the framework regions and CDRs encodes an antibody that specifically binds a polypeptide of the invention. Preferably, as discussed supra, one or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present invention and within the skill of the art.

In addition, techniques developed for the production of "chimeric antibodies" (Morrison et al., Proc. Natl. Acad. Sci. 81:851-855 (1984); Neuberger et al., Nature 312:604-608 (1984); Takeda et al., Nature 314:452-454 (1985)) by splicing genes from a mouse antibody molecule of appropriate antigen specificity together with genes from a human antibody molecule of appropriate biological activity can be used. As described supra, a chimeric antibody is a molecule in which different portions are derived from different animal species, such as those having a variable region derived from a murine mAb and a human immunoglobulin constant region, e.g., humanized antibodies.

Alternatively, techniques described for the production of single chain antibodies (U.S. Pat. No. 4,946,778; Bird, Science 242:423-42 (1988); Huston et al., Proc. Natl. Acad. Sci. USA 85:5879-5883 (1988); and Ward et al., Nature 334:544-54 (1989)) can be adapted to produce single chain antibodies. Single chain antibodies are formed by linking the heavy and light chain fragments of the Fv region via an amino acid bridge, resulting in a single chain polypeptide. Techniques for the assembly of functional Fv fragments in *E. coli* may also be used (Skerra et al., Science 242:1038-1041 (1988)).

Methods of Producing Antibodies

The antibodies of the invention can be produced by any method known in the art for the synthesis of antibodies, in particular, by chemical synthesis or preferably, by recombinant expression techniques. Methods of producing antibodies include, but are not limited to, hybridoma technology, EBV transformation, and other methods discussed herein as well as through the use recombinant DNA technology, as discussed below.

Recombinant expression of an antibody of the invention, or fragment, derivative or analog thereof, (e.g., a heavy or light chain of an antibody of the invention or a single chain antibody of the invention), requires construction of an expression vector containing a polynucleotide that encodes the antibody. Once a polynucleotide encoding an antibody molecule or a heavy or light chain of an antibody, or portion thereof (preferably containing the heavy or light chain variable domain), of the invention has been obtained, the vector for the production of the antibody molecule may be produced by recombinant DNA technology using techniques well known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, or a heavy or light chain thereof, or a heavy or light chain variable domain, operably linked to a promoter. Such vectors may include the nucleotide sequence encoding the constant region of the antibody molecule (see, e.g., PCT Publication WO 86/05807; PCT Publication WO 89/01036; and U.S. Pat. No. 5,122,464) and the variable domain of the antibody may be cloned into such a vector for expression of the entire heavy or light chain.

The expression vector is transferred to a host cell by conventional techniques and the transfected cells are then cultured by conventional techniques to produce an antibody of the invention. Thus, the invention includes host cells containing a polynucleotide encoding an antibody of the invention, or a heavy or light chain thereof, or a single chain antibody of the invention, operably linked to a heterologous promoter. In preferred embodiments for the expression of double-chained antibodies, vectors encoding both the heavy and light chains may be co-expressed in the host cell for expression of the entire immunoglobulin molecule, as detailed below.

A variety of host-expression vector systems may be utilized to express the antibody molecules of the invention. Such host-expression systems represent vehicles by which the coding sequences of interest may be produced and subsequently purified, but also represent cells which may, when transformed or transfected with the appropriate nucleotide coding sequences, express an antibody molecule of the invention in situ. These include but are not limited to microorganisms such as bacteria (e.g., *E. coli, B. subtilis*) transformed with recombinant bacteriophage DNA, plasmid DNA or cosmid DNA expression vectors containing antibody coding sequences; yeast (e.g., *Saccharomyces, Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli*, and more preferably, eukaryotic cells, especially for the expression of whole recombinant antibody molecule, are used for the expression of a recombinant antibody molecule. For example, mammalian cells, such as Chinese hamster ovary cells (CHO), in conjunction with a vector such as the major intermediate early gene promoter element from human cytomegalovirus is an effective expression system for antibodies (Foecking et al., Gene 45:101 (1986); Cockett et al., Bio/Technology 8:2 (1990)).

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited, to the *E. coli* expression vector pUR278 (Ruther et al., EMBO J. 2:1791 (1983)), in which the antibody coding sequence may be ligated individually into the vector in frame with the lac Z coding region so that a fusion protein is produced; pIN vectors (Inouye & Inouye, Nucleic Acids Res. 13:3101-3109 (1985); Van Heeke & Schuster, J. Biol. Chem. 24:5503-5509 (1989)); and the like. pGEX vectors may also be used to express foreign polypeptides as fusion proteins with glutathione S-transferase (GST). In general, such fusion proteins are soluble and can easily be purified from lysed cells by adsorption and binding to matrix glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts. (e.g., see Logan & Shenk, Proc. Natl. Acad. Sci. USA 81:355-359 (1984)). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., Methods in Enzymol. 153:51-544 (1987)).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, 293, 3T3, WI38, and in particular, breast cancer cell lines such as, for example, BT483, Hs578T, HTB2, BT20 and T47D, and normal mammary gland cell line such as, for example, CRL7030 and Hs578Bst.

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci that in turn can be cloned and expanded into cell lines. This method may advantageously be used to engineer cell lines which express the antibody molecule. Such engineered cell lines may be particularly useful in screening and evaluation of compounds that interact directly or indirectly with the antibody molecule.

A number of selection systems may be used, including but not limited to the herpes simplex virus thymidine kinase (Wigler et al., Cell 11:223 (1977)), hypoxanthine-guanine phosphoribosyltransferase (Szybalska & Szybalski, Proc. Natl. Acad. Sci. USA 48:202 (1992)), and adenine phosphoribosyltransferase (Lowy et al., Cell 22:817 (1980)) genes can be employed in tk-, hgprt- or aprt-cells, respectively. Also, antimetabolite resistance can be used as the basis of selection for the following genes: dhfr, which confers resistance to methotrexate (Wigler et al., Natl. Acad. Sci. USA 77:357 (1980); O'Hare et al., Proc. Natl. Acad. Sci. USA 78:1527 (1981)); gpt, which confers resistance to mycophenolic acid (Mulligan & Berg, Proc. Natl. Acad. Sci. USA 78:2072 (1981)); neo, which confers resistance to the aminoglycoside G-418 Clinical Pharmacy 12:488-505; Wu and Wu, Biotherapy 3:87-95 (1991); Tolstoshev, Ann. Rev. Pharmacol. Toxicol. 32:573-596 (1993); Mulligan, Science 260:926-932 (1993); and Morgan and Anderson, Ann. Rev. Biochem. 62:191-217 (1993); May, 1993, TIB TECH 11(5):155-215 (1993)); and hygro, which confers resistance to hygromycin (Santerre et al., Gene 30:147 (1984)). Methods commonly known in the art of recombinant DNA technology may be routinely applied to select the desired recombinant clone, and such methods are described, for example, in Ausubel et al. (eds.), Current Protocols in Molecular Biology, John Wiley & Sons, NY (1993); Kriegler, Gene Transfer and Expression, A Laboratory Manual, Stockton Press, NY (1990); and in Chapters 12 and 13, Dracopoli et al. (eds), Current Protocols in Human Genetics, John Wiley & Sons, NY (1994); Colberre-Garapin et al., J. Mol. Biol. 150:1 (1981), which are incorporated by reference herein in their entireties.

The expression levels of an antibody molecule can be increased by vector amplification (for a review, see Bebbington and Hentschel, The use of vectors based on gene amplification for the expression of cloned genes in mammalian cells in DNA cloning, Vol. 3. (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., Mol. Cell. Biol. 3:257 (1983)).

Vectors which use glutamine synthase (GS) or DHFR as the selectable markers can be amplified in the presence of the drugs methionine sulphoximine or methotrexate, respectively. An advantage of glutamine synthase based vectors are the availability of cell lines (e.g., the murine myeloma cell line, NS0) which are glutamine synthase negative. Glutamine synthase expression systems can also function in glutamine synthase expressing cells (e.g. Chinese Hamster Ovary (CHO) cells) by providing additional inhibitor to prevent the functioning of the endogenous gene. A glutamine synthase expression system and components thereof are detailed in PCT publications: WO87/04462; WO86/05807; WO89/01036; WO89/10404; and WO91/06657 which are incorporated in their entireties by reference herein. Additionally, glutamine synthase expression vectors that may be used according to the present invention are commercially available from suppliers, including, for example Lonza Biologics, Inc. (Portsmouth, N.H.). Expression and production of monoclonal antibodies using a GS expression system in murine myeloma cells is described in Bebbington et al., *Bio/technology* 10:169 (1992) and in Biblia and Robinson *Biotechnol. Prog.* 11:1 (1995) which are incorporated in their entireties by reference herein.

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes, and is capable of expressing, both heavy and light chain polypeptides. In such situations, the light chain should be placed before the heavy chain to avoid an excess of toxic free heavy chain (Proudfoot, Nature 322:52 (1986); Kohler, Proc. Natl. Acad. Sci. USA 77:2197 (1980)). The coding sequences for the heavy and light chains may comprise cDNA or genomic DNA.

Once an antibody molecule of the invention has been produced by an animal, chemically synthesized, or recombinantly expressed, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. In addition, the antibodies of the present invention or fragments thereof can be fused to heterologous polypeptide sequences described herein or otherwise known in the art, to facilitate purification.

The present invention encompasses antibodies recombinantly fused or chemically conjugated (including both covalently and non-covalently conjugations) to a polypeptide (or portion thereof, preferably at least 10, 20, 30, 40, 50, 60, 70, 80, 90 or 100 amino acids of the polypeptide) of the present invention to generate fusion proteins. The fusion does not necessarily need to be direct, but may occur through linker sequences. The antibodies may be specific for antigens other than polypeptides (or portion thereof, preferably at least 10, 20, 30, 40, 50, 60, 70, 80, 90 or 100 amino acids of the polypeptide) of the present invention. For example, antibodies may be used to target the polypeptides of the present invention to particular cell types, either in vitro or in vivo, by fusing or conjugating the polypeptides of the present invention to antibodies specific for particular cell surface receptors.

Antibodies fused or conjugated to the polypeptides of the present invention may also be used in in vitro immunoassays and purification methods using methods known in the art. See e.g., Harbor et al., supra, and PCT publication WO 93/21232; EP 439,095; Naramura et al., Immunol. Lett. 39:91-99 (1994); U.S. Pat. No. 5,474,981; Gillies et al., PNAS 89:1428-1432 (1992); Fell et al., J. Immunol. 146:2446-2452 (1991), which are incorporated by reference in their entireties.

The present invention further includes compositions comprising the polypeptides of the present invention fused or conjugated to antibody domains other than the variable regions. For example, the polypeptides of the present invention may be fused or conjugated to an antibody Fc region, or portion thereof. The antibody portion fused to a polypeptide of the present invention may comprise the constant region, hinge region, CH1 domain, CH2 domain, and CH3 domain or any combination of whole domains or portions thereof. The polypeptides may also be fused or conjugated to the above antibody portions to form multimers. For example, Fc portions fused to the polypeptides of the present invention can form dimers through disulfide bonding between the Fc portions. Higher multimeric forms can be made by fusing the polypeptides to portions of IgA and IgM. Methods for fusing or conjugating the polypeptides of the present invention to antibody portions are known in the art. See, e.g., U.S. Pat. Nos. 5,336,603; 5,622,929; 5,359,046; 5,349,053; 5,447,851; 5,112,946; EP 307,434; EP 367,166; PCT publications WO 96/04388; WO 91/06570; Ashkenazi et al., Proc. Natl. Acad. Sci. USA 88:10535-10539 (1991); Zheng et al., J. Immunol. 154:5590-5600 (1995); and Vil et al., Proc. Natl. Acad. Sci. USA 89:11337-11341 (1992) (said references incorporated by reference in their entireties).

As discussed, supra, the polypeptides corresponding to a polypeptide, polypeptide fragment, or a variant of SEQ ID NO:Y may be fused or conjugated to the above antibody portions to increase the in vivo half life of the polypeptides or for use in immunoassays using methods known in the art. Further, the polypeptides corresponding to SEQ ID NO:Y may be fused or conjugated to the above antibody portions to facilitate purification. One reported example describes chimeric proteins consisting of the first two domains of the human CD4-polypeptide and various domains of the constant regions of the heavy or light chains of mammalian immunoglobulins. See EP 394,827; and Traunecker et al., Nature 331:84-86 (1988). The polypeptides of the present invention fused or conjugated to an antibody having disulfide-linked dimeric structures (due to the IgG) may also be more efficient in binding and neutralizing other molecules, than the monomeric secreted protein or protein fragment alone. See, for example, Fountoulakis et al., J. Biochem. 270:3958-3964 (1995). In many cases, the Fc part in a fusion protein is beneficial in therapy and diagnosis, and thus can result in, for example, improved pharmacokinetic properties. See, for example, EP A 232,262. Alternatively, deleting the Fc part after the fusion protein has been expressed, detected, and purified, would be desired. For example, the Fc portion may hinder therapy and diagnosis if the fusion protein is used as an antigen for immunizations. In drug discovery, for example, human proteins, such as hIL-5, have been fused with Fc portions for the purpose of high-throughput screening assays to identify antagonists of hIL-5. (See, Bennett et al., J. Molecular Recognition 8:52-58 (1995); Johanson et al., J. Biol. Chem. 270:9459-9471 (1995)).

Moreover, the antibodies or fragments thereof of the present invention can be fused to marker sequences, such as a peptide to facilitate purification. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821-824 (1989), for instance, hexa-histidine provides for convenient purification of the fusion protein. Other peptide tags useful for purification include, but are not limited to, the "HA" tag, which corresponds to an epitope derived from the influenza hemagglutinin protein (Wilson et al., Cell 37:767 (1984)) and the "flag" tag.

The present invention further encompasses antibodies or fragments thereof conjugated to a diagnostic or therapeutic agent. The antibodies can be used diagnostically to, for example, monitor the development or progression of a tumor as part of a clinical testing procedure to, e.g., determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. The detectable substance may be coupled or conjugated either directly to the antibody (or fragment thereof) or indirectly, through an intermediate (such as, for example, a linker known in the art) using techniques known in the art. See, for example, U.S. Pat. No. 4,741,900 for metal ions which can be conjugated to antibodies for use as diagnostics according to the present invention. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include 125I, 131I, 111In or 99Tc.

Further, an antibody or fragment thereof may be conjugated to a therapeutic moiety such as a cytotoxin, e.g., a cytostatic or cytocidal agent, a therapeutic agent or a radioactive metal ion, e.g., alpha-emitters such as, for example, 213Bi. A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thiotepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the therapeutic agent or drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, a-interferon, β-interferon, nerve growth factor, platelet derived growth factor, tissue plasminogen activator, an apoptotic agent, e.g., TNF-alpha, TNF-beta, AIM I (See, International Publication No. WO 97/33899), AIM II (See, International Publication No. WO 97/34911), Fas Ligand (Takahashi et al., *Int. Immunol.,* 6:1567-1574 (1994)), VEGI (See, International Publication No. WO 99/23105), a thrombotic agent or an anti-angiogenic agent, e.g., angiostatin or endostatin; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Techniques for conjugating such therapeutic moiety to antibodies are well known. See, for example, Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev. 62:119-58 (1982).

Alternatively, an antibody can be conjugated to a second antibody to form an antibody heteroconjugate as described by Segal in U.S. Pat. No. 4,676,980, which is incorporated herein by reference in its entirety.

An antibody, with or without a therapeutic moiety conjugated to it, administered alone or in combination with cytotoxic factor(s) and/or cytokine(s) can be used as a therapeutic.

Immunophenotyping

The antibodies of the invention may be utilized for immunophenotyping of cell lines and biological samples. Translation products of the gene of the present invention may be useful as cell-specific markers, or more specifically as cellular markers that are differentially expressed at various stages of differentiation and/or maturation of particular cell types. Monoclonal antibodies directed against a specific epitope, or combination of epitopes, will allow for the screening of cellular populations expressing the marker. Various techniques can be utilized using monoclonal antibodies to screen for cellular populations expressing the marker(s), and include magnetic separation using antibody-coated magnetic beads, "panning" with antibody attached to a solid matrix (i.e., plate), and flow cytometry (See, e.g., U.S. Pat. No. 5,985,660; and Morrison et al., *Cell,* 96:737-49 (1999)).

These techniques allow for the screening of particular populations of cells, such as might be found with hematological malignancies (i.e. minimal residual disease (MRD) in acute leukemic patients) and "non-self" cells in transplantations to prevent Graft-versus-Host Disease (GVHD). Alternatively, these techniques allow for the screening of hematopoietic stem and progenitor cells capable of undergoing proliferation and/or differentiation, as might be found in human umbilical cord blood.

Assays for Antibody Binding

The antibodies of the invention may be assayed for immunospecific binding by any method known in the art. The immunoassays which can be used include but are not limited to competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, and protein A immunoassays, to name but a few. Such assays are routine and well known in the art (see, e.g., Ausubel et al, eds, 1994, Current Protocols in Molecular Biology, Vol. 1, John Wiley & Sons, Inc., New York, which is incorporated by reference herein in its entirety). Exemplary immunoassays are described briefly below (but are not intended by way of limitation).

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody of interest to the cell lysate, incubating for a period of time (e.g., 1-4 hours) at 4° C., adding protein A and/or protein G sepharose beads to the cell lysate, incubating for about an hour or more at 4° C., washing the beads in lysis buffer and resuspending the beads in SDS/sample buffer. The ability of the antibody of interest to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel et al., eds., (1994), Current Protocols in Molecular Biology, Vol. 1, John Wiley & Sons, Inc., New York, section 10.16.1.

Western blot analysis generally comprises preparing protein samples, electrophoresis of the protein samples in a polyacrylamide gel (e.g., 8%-20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody of interest) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., 32P or 125I) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Ausubel et al, eds, (1994), Current Protocols in Molecular Biology, Vol. 1, John Wiley & Sons, Inc., New York, section 10.8.1.

ELISAs comprise preparing antigen, coating the well of a 96 well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art. For further discussion regarding ELISAs see, e.g., Ausubel et al, eds, (1994), Current Protocols in Molecular Biology, Vol. 1, John Wiley & Sons, Inc., New York, section 11.2.1.

The binding affinity of an antibody to an antigen and the off-rate of an antibody-antigen interaction can be determined by competitive binding assays. One example of a competitive binding assay is a radioimmunoassay comprising the incubation of labeled antigen (e.g., 3H or 125I) with the antibody of interest in the presence of increasing amounts of unlabeled antigen, and the detection of the antibody bound to the labeled antigen. The affinity of the antibody of interest for a particular antigen and the binding off-rates can be determined from the data by scatchard plot analysis. Competition with a second antibody can also be determined using radioimmunoassays. In this case, the antigen is incubated with antibody of interest conjugated to a labeled compound (e.g., 3H or 125I) in the presence of increasing amounts of an unlabeled second antibody.

Antibodies of the invention may be characterized using immunocytochemistry methods on cells (e.g., mammalian cells, such as CHO cells) transfected with a vector enabling the expression of an antigen or with vector alone using techniques commonly known in the art. Antibodies that bind antigen transfected cells, but not vector-only transfected cells, are antigen specific.

Therapeutic Uses

Table 1D: In preferred embodiments, the present invention encompasses a method of treating a disease or disorder listed in the "Preferred Indications" column of Table 1D; comprising administering to a patient in which such treatment, prevention, or amelioration is desired a protein, nucleic acid, or antibody of the invention (or fragment or variant thereof) represented by Table 1A and Table 1D (in the same row as the disease or disorder to be treated is listed in the "Preferred Indications" column of Table 1D) in an amount effective to treat, prevent, or ameliorate the disease or disorder.

As indicated in Table 1D, the polynucleotides, polypeptides, agonists, or antagonists of the present invention (including antibodies) can be used in assays to test for one or more biological activities. If these polynucleotides and polypeptides do exhibit activity in a particular assay, it is likely that these molecules may be involved in the diseases associated with the biological activity. Thus, the polynucleotides or polypeptides, or agonists or antagonists thereof (including antibodies) could be used to treat the associated disease.

The present invention encompasses methods of preventing, treating, diagnosing, or ameliorating a disease or disorder. In preferred embodiments, the present invention encompasses a method of treating a disease or disorder listed in the "Preferred Indications" column of Table 1D; comprising administering to a patient in which such treatment, prevention, or amelioration is desired a protein, nucleic acid, or antibody of the invention (or fragment or variant thereof) in an amount effective to treat, prevent, diagnose, or ameliorate the disease or disorder. The first and second columns of Table 1D show the "Gene No." and "cDNA Clone ID No.", respectively, indicating certain nucleic acids and proteins (or antibodies against the same) of the invention (including polynucleotide, polypeptide, and antibody fragments or variants thereof) that may be used in preventing, treating, diagnosing, or ameliorating the disease(s) or disorder(s) indicated in the corresponding row in Column 3 of Table 1D.

In another embodiment, the present invention also encompasses methods of preventing, treating, diagnosing, or ameliorating a disease or disorder listed in the "Preferred Indications" column of Table 1D; comprising administering to a patient combinations of the proteins, nucleic acids, or antibodies of the invention (or fragments or variants thereof), sharing similar indications as shown in the corresponding rows in Column 3 of Table 1D.

The "Preferred Indication" column describes diseases, disorders, and/or conditions that may be treated, prevented, diagnosed, or ameliorated by a protein, nucleic acid, or antibody of the invention (or fragment or variant thereof).

The recitation of "Cancer" in the "Preferred Indication" column indicates that the corresponding nucleic acid and protein, or antibody against the same, of the invention (or fragment or variant thereof) may be used for example, to diagnose, treat, prevent, and/or ameliorate diseases and/or disorders relating to neoplastic diseases (e.g., leukemias, cancers, and/or as described below under "Hyperproliferative Disorders").

In specific embodiments, a protein, nucleic acid, or antibody of the invention (or fragment or variant thereof) having a "Cancer" recitation in the "Preferred Indication" column of Table 1D may be used for example, to diagnose, treat, prevent, and/or ameliorate a neoplasm located in a tissue selected from the group consisting of: colon, abdomen, bone, breast, digestive system, liver, pancreas, prostate, peritoneum, lung, blood (e.g., leukemia), endocrine glands (adrenal, parathyroid, pituitary, testicles, ovary, thymus, thyroid), uterus, eye, head and neck, nervous (central and peripheral), lymphatic system, pelvic, skin, soft tissue, spleen, thoracic, and urogenital.

In specific embodiments, a protein, nucleic acid, or antibody of the invention (or fragment or variant thereof) having a "Cancer" recitation in the "Preferred Indication" column of Table 1D, may be used for example, to diagnose, treat, prevent, and/or ameliorate a pre-neoplastic condition, selected from the group consisting of: hyperplasia (e.g., endometrial hyperplasia and/or as described in the section entitled "Hyperproliferative Disorders"), metaplasia (e.g., connective tissue metaplasia, atypical metaplasia, and/or as described in the section entitled "Hyperproliferative Disorders"), and/or dysplasia (e.g., cervical dysplasia, and bronchopulmonary dysplasia).

In another specific embodiment, a protein, nucleic acid, or antibody of the invention (or fragment or variant thereof) having a "Cancer" recitation in the "Preferred Indication" column of Table 1D, may be used for example, to diagnose, treat, prevent, and/or ameliorate a benign dysproliferative disorder selected from the group consisting of: benign tumors, fibrocystic conditions, tissue hypertrophy, and/or as described in the section entitled "Hyperproliferative Disorders".

The recitation of "Immune/Hematopoietic" in the "Preferred Indication" column indicates that the corresponding nucleic acid and protein, or antibody against the same, of the invention (or fragment or variant thereof), may be used for example, to diagnose, treat, prevent, and/or ameliorate diseases and/or disorders relating to neoplastic diseases (e.g., as described below under "Hyperproliferative Disorders"), blood disorders (e.g., as described below under "Immune Activity" "Cardiovascular Disorders" and/or "Blood-Related Disorders"), and infections (e.g., as described below under "Infectious Disease").

In specific embodiments, a protein, nucleic acid, or antibody of the invention (or fragment or variant thereof) having the "Immune/Hematopoietic" recitation in the "Preferred Indication" column of Table 1D, may be used for example, to diagnose, treat, prevent, and/or ameliorate a disease or disorder selected from the group consisting of: anemia, pancytopenia, leukopenia, thrombocytopenia, leukemias, Hodgkin's disease, non-Hodgkin's lymphoma, acute lymphocytic anemia (ALL), plasmacytomas, multiple myeloma, Burkitt's lymphoma, arthritis, asthma, AIDS, autoimmune disease, rheumatoid arthritis, granulomatous disease, immune deficiency, inflammatory bowel disease, sepsis, neutropenia, neutrophilia, psoriasis, immune reactions to transplanted organs and tissues, systemic lupus erythematosis, hemophilia, hypercoagulation, diabetes mellitus, endocarditis, meningitis, Lyme Disease, and allergies.

The recitation of "Reproductive" in the "Preferred Indication" column indicates that the corresponding nucleic acid and protein, or antibody against the same, of the invention (or fragment or variant thereof), may be used for example, to diagnose, treat, prevent, and/or ameliorate diseases and/or disorders relating to neoplastic diseases (e.g., as described below under "Hyperproliferative Disorders"), and disorders of the reproductive system (e.g., as described below under "Reproductive System Disorders").

In specific embodiments, a protein, nucleic acid, or antibody of the invention (or fragment or variant thereof) having a "Reproductive" recitation in the "Preferred Indication" column of Table 1D, may be used for example, to diagnose, treat, prevent, and/or ameliorate a disease or disorder selected from the group consisting of: cryptorchism, prostatitis, inguinal hernia, varicocele, leydig cell tumors, verrucous carcinoma, prostatitis, malacoplakia, Peyronie's disease, penile carcinoma, squamous cell hyperplasia, dysmenorrhea, ovarian adenocarcinoma, Turner's syndrome, mucopurulent cervicitis, Sertoli-leydig tumors, ovarian cancer, uterine cancer, pelvic inflammatory disease, testicular cancer, prostate cancer, Klinefelter's syndrome, Young's syndrome, premature ejaculation, diabetes mellitus, cystic fibrosis, Kartagener's syndrome, testicular atrophy, testicular feminization, anorchia, ectopic testis, epididymitis, orchitis, gonorrhea, syphilis, testicular torsion, vasitis nodosa, germ cell tumors, stromal tumors, dysmenorrhea, retroverted uterus, endometriosis, fibroids, adenomyosis, anovulatory bleeding, amenorrhea, Cushing's syndrome, hydatidiform moles, Asherman's syndrome, premature menopause, precocious puberty, uterine polyps, dysfunctional uterine bleeding, cervicitis, chronic cervicitis, mucopurulent cervicitis, cervical dysplasia, cervical polyps, Nabothian cysts, cervical erosion, cervical incompetence, cervical neoplasms, pseudohermaphroditism, and premenstrual syndrome.

The recitation of "Musculoskeletal" in the "Preferred Indication" column indicates that the corresponding nucleic acid and protein, or antibody against the same, of the invention (or fragment or variant thereof), may be used for example, to diagnose, treat, prevent, and/or ameliorate diseases and/or disorders relating to neoplastic diseases (e.g., as described below under "Hyperproliferative Disorders"), and disorders of the immune system (e.g., as described below under "Immune Activity").

In specific embodiments, a protein, nucleic acid, or antibody of the invention (or fragment or variant thereof) having a "Musculoskeletal" recitation in the "Preferred Indication" column of Table 1D, may be used for example, to diagnose, treat, prevent, and/or ameliorate a disease or disorder selected from the group consisting of: bone cancers (e.g., osteochondromas, benign chondromas, chondroblastoma, chondromyxoid fibromas, osteoid osteomas, giant cell tumors, multiple myeloma, osteosarcomas), Paget's Disease, rheumatoid arthritis, systemic lupus erythematosus, osteomyelitis, Lyme Disease, gout, bursitis, tendonitis, osteoporosis, osteoarthritis, muscular dystrophy, mitochondrial myopathy, cachexia, and multiple sclerosis.

The recitation of "Cardiovascular" in the "Preferred Indication" column indicates that the corresponding nucleic acid and protein, or antibody against the same, of the invention (or fragment or variant thereof), may be used for example, to diagnose, treat, prevent, and/or ameliorate diseases and/or disorders relating to neoplastic diseases (e.g., as described below under "Hyperproliferative Disorders"), and disorders of the cardiovascular system (e.g., as described below under "Cardiovascular Disorders").

In specific embodiments, a protein, nucleic acid, or antibody of the invention (or fragment or variant thereof) having a "Cardiovascular" recitation in the "Preferred Indication" column of Table 1D, may be used for example, to diagnose, treat, prevent, and/or ameliorate a disease or disorder selected from the group consisting of: myxomas, fibromas, rhabdomyomas, cardiovascular abnormalities (e.g., congenital heart defects, cerebral arteriovenous malformations, septal defects), heart disease (e.g., heart failure, congestive heart disease, arrhythmia, tachycardia, fibrillation, pericardial Disease, endocarditis), cardiac arrest, heart valve disease (e.g., stenosis, regurgitation, prolapse), vascular disease (e.g., hypertension, coronary artery disease, angina, aneurysm, arteriosclerosis, peripheral vascular disease), hyponatremia, hypernatremia, hypokalemia, and hyperkalemia.

The recitation of "Mixed Fetal" in the "Preferred Indication" column indicates that the corresponding nucleic acid and protein, or antibody against the same, of the invention (or fragment or variant thereof), may be used for example, to diagnose, treat, prevent, and/or ameliorate diseases and/or disorders relating to neoplastic diseases (e.g., as described below under "Hyperproliferative Disorders").

In specific embodiments, a protein, nucleic acid, or antibody of the invention (or fragment or variant thereof) having a "Mixed Fetal" recitation in the "Preferred Indication" column of Table 1D, may be used for example, to diagnose, treat, prevent, and/or ameliorate a disease or disorder selected from the group consisting of: spina bifida, hydranencephaly, neurofibromatosis, fetal alcohol syndrome, diabetes mellitus, PKU, Down's syndrome, Patau syndrome, Edwards syndrome, Turner syndrome, Apert syndrome, Carpenter syndrome, Conradi syndrome, Crouzon syndrome, cutis laxa, Cornelia de Lange syndrome, Ellis-van Creveld syndrome, Holt-Oram syndrome, Kartagener syndrome, Meckel-Gruber syndrome, Noonan syndrome, Pallister-Hall syndrome, Rubinstein-Taybi syndrome, Scimitar syndrome, Smith-Lemli-Opitz syndrome, thromocytopenia-absent radius (TAR) syndrome, Treacher Collins syndrome, Williams syndrome, Hirschsprung's disease, Meckel's diverticulum, polycystic kidney disease, Turner's syndrome, and gonadal dysgenesis, Klippel-Feil syndrome, Ostogenesis imperfecta, muscular dystrophy, Tay-Sachs disease, Wilm's tumor, neuroblastoma, and retinoblastoma.

The recitation of "Excretory" in the "Preferred Indication" column indicates that the corresponding nucleic acid and protein, or antibody against the same, of the invention (or fragment or variant thereof), may be used for example, to diagnose, treat, prevent, and/or ameliorate diseases and/or disorders relating to neoplastic diseases (e.g., as described below under "Hyperproliferative Disorders") and renal disorders (e.g., as described below under "Renal Disorders").

In specific embodiments, a protein, nucleic acid, or antibody of the invention (or fragment or variant thereof) having a "Excretory" recitation in the "Preferred Indication" column of Table 1D, may be used for example, to diagnose, treat, prevent, and/or ameliorate a disease or disorder selected from the group consisting of: bladder cancer, prostate cancer, benign prostatic hyperplasia, bladder disorders (e.g., urinary incontinence, urinary retention, urinary obstruction, urinary tract Infections, interstitial cystitis, prostatitis, neurogenic bladder, hematuria), renal disorders (e.g., hydronephrosis, proteinuria, renal failure, pyelonephritis, urolithiasis, reflux nephropathy, and unilateral obstructive uropathy).

The recitation of "Neural/Sensory" in the "Preferred Indication" column indicates that the corresponding nucleic acid and protein, or antibody against the same, of the invention (or fragment or variant thereof), may be used for example, to diagnose, treat, prevent, and/or ameliorate diseases and/or disorders relating to neoplastic diseases (e.g., as described below under "Hyperproliferative Disorders") and diseases or disorders of the nervous system (e.g., as described below under "Neural Activity and Neurological Diseases").

In specific embodiments, a protein, nucleic acid, or antibody of the invention (or fragment or variant thereof) having a "Neural/Sensory" recitation in the "Preferred Indication" column of Table 1D, may be used for example, to diagnose, treat, prevent, and/or ameliorate a disease or disorder selected from the group consisting of: brain cancer (e.g., brain stem glioma, brain tumors, central nervous system (Primary) lymphoma, central nervous system lymphoma, cerebellar astrocytoma, and cerebral astrocytoma, neurodegenerative disorders (e.g., Alzheimer's Disease, Creutzfeldt-Jakob Disease, Parkinson's Disease, and Idiopathic Presenile Dementia), encephalomyelitis, cerebral malaria, meningitis, metabolic brain diseases (e.g., phenylketonuria and pyruvate carboxylase deficiency), cerebellar ataxia, ataxia telangiectasia, and AIDS Dementia Complex, schizophrenia, attention deficit disorder, hyperactive attention deficit disorder, autism, and obsessive compulsive disorders.

The recitation of "Respiratory" in the "Preferred Indication" column indicates that the corresponding nucleic acid and protein, or antibody against the same, of the invention (or fragment or variant thereof), may be used for example, to diagnose, treat, prevent, and/or ameliorate diseases and/or disorders relating to neoplastic diseases (e.g., as described below under "Hyperproliferative Disorders") and diseases or disorders of the respiratory system (e.g., as described below under "Respiratory Disorders").

In specific embodiments, a protein, nucleic acid, or antibody of the invention (or fragment or variant thereof) having a "Respiratory" recitation in the "Preferred Indication" column of Table 1D, may be used for example, to diagnose, treat, prevent, and/or ameliorate a disease or disorder selected from the group consisting of: cancers of the respiratory system such as larynx cancer, pharynx cancer, trachea cancer, epiglottis cancer, lung cancer, squamous cell carcinomas, small cell (oat cell) carcinomas, large cell carcinomas, and adenocarcinomas. Allergic reactions, cystic fibrosis, sarcoidosis, histiocytosis X, infiltrative lung diseases (e.g., pulmonary fibrosis and lymphoid interstitial pneumonia), obstructive airway diseases (e.g., asthma, emphysema, chronic or acute bronchitis), occupational lung diseases (e.g., silicosis and asbestosis), pneumonia, and pleurisy.

The recitation of "Endocrine" in the "Preferred Indication" column indicates that the corresponding nucleic acid and protein, or antibody against the same, of the invention (or fragment or variant thereof), may be used for example, to diagnose, treat, prevent, and/or ameliorate diseases and/or disorders relating to neoplastic diseases (e.g., as described below under "Hyperproliferative Disorders") and diseases or disorders of the respiratory system (e.g., as described below under "Respiratory Disorders"), renal disorders (e.g., as described below under "Renal Disorders"), and disorders of the endocrine system (e.g., as described below under "Endocrine Disorders".

In specific embodiments, a protein, nucleic acid, or antibody of the invention (or fragment or variant thereof) having an "Endocrine" recitation in the "Preferred Indication" column of Table 1D, may be used for example, to diagnose, treat, prevent, and/or ameliorate a disease or disorder selected from the group consisting of: cancers of endocrine tissues and organs (e.g., cancers of the hypothalamus, pituitary gland, thyroid gland, parathyroid glands, pancreas, adrenal glands, ovaries, and testes), diabetes (e.g., diabetes insipidus, type I and type II diabetes mellitus), obesity, disorders related to pituitary glands (e.g., hyperpituitarism, hypopituitarism, and pituitary dwarfism), hypothyroidism, hyperthyroidism, goiter, reproductive disorders (e.g. male and female infertility), disorders related to adrenal glands (e.g., Addison's Disease, corticosteroid deficiency, and Cushing's Syndrome), kidney cancer (e.g., hypernephroma, transitional cell cancer, and Wilm's tumor), diabetic nephropathy, interstitial nephritis, polycystic kidney disease, glomerulonephritis (e.g., IgM mesangial proliferative glomerulonephritis and glomerulonephritis caused by autoimmune disorders; such as Goodpasture's syndrome), and nephrocalcinosis.

The recitation of "Digestive" in the "Preferred Indication" column indicates that the corresponding nucleic acid and protein, or antibody against the same, of the invention (or fragment or variant thereof), may be used for example, to diagnose, treat, prevent, and/or ameliorate diseases and/or disorders relating to neoplastic diseases (e.g., as described below under "Hyperproliferative Disorders") and diseases or disorders of the gastrointestinal system (e.g., as described below under "Gastrointestinal Disorders".

In specific embodiments, a protein, nucleic acid, or antibody of the invention (or fragment or variant thereof) having a "Digestive" recitation in the "Preferred Indication" column of Table 1D, may be used for example, to diagnose, treat, prevent, and/or ameliorate a disease or disorder selected from the group consisting of: ulcerative colitis, appendicitis, Crohn's disease, hepatitis, hepatic encephalopathy, portal hypertension, cholelithiasis, cancer of the digestive system (e.g., biliary tract cancer, stomach cancer, colon cancer, gastric cancer, pancreatic cancer, cancer of the bile duct, tumors of the colon (e.g., polyps or cancers), and cirrhosis), pancreatitis, ulcerative disease, pyloric stenosis, gastroenteritis, gastritis, gastric atropy, benign tumors of the duodenum, distension, irritable bowel syndrome, malabsorption, congenital disorders of the small intestine, bacterial and parasitic infection, megacolon, Hirschsprung's disease, aganglionic megacolon, acquired megacolon, colitis, anorectal disorders (e.g., anal fistulas, hemorrhoids), congenital disorders of the liver (e.g., Wilson's disease, hemochromatosis, cystic fibrosis, biliary atresia, and alpha1-antitrypsin deficiency), portal hypertension, cholelithiasis, and jaundice.

The recitation of "Connective/Epithelial" in the "Preferred Indication" column indicates that the corresponding nucleic acid and protein, or antibody against the same, of the invention (or fragment or variant thereof), may be used for example, to diagnose, treat, prevent, and/or ameliorate diseases and/or disorders relating to neoplastic diseases (e.g., as described below under "Hyperproliferative Disorders"), cellular and genetic abnormalities (e.g., as described below under "Diseases at the Cellular Level"), angiogenesis (e.g., as described below under "Anti-Angiogenesis Activity"), and or to promote or inhibit regeneration (e.g., as described below under "Regeneration"), and wound healing (e.g., as described below under "Wound Healing and Epithelial Cell Proliferation").

In specific embodiments, a protein, nucleic acid, or antibody of the invention (or fragment or variant thereof) having a "Connective/Epithelial" recitation in the "Preferred Indication" column of Table 1D, may be used for example, to diagnose, treat, prevent, and/or ameliorate a disease or disorder selected from the group consisting of: connective tissue metaplasia, mixed connective tissue disease, focal epithelial hyperplasia, epithelial metaplasia, mucoepithelial dysplasia, graft v. host disease, polymyositis, cystic hyperplasia, cerebral dysplasia, tissue hypertrophy, Alzheimer's disease, lymphoproliferative disorder, Waldenstron's macroglobulinemia, Crohn's disease, pernicious anemia, idiopathic Addison's disease, glomerulonephritis, bullous pemphigoid, Sjogren's syndrome, diabetes mellitus, cystic fibrosis, osteoblastoma, osteoclastoma, osteosarcoma, chondrosarcoma, osteoporosis, osteocarthritis, periodontal disease, wound healing, relapsing polychondritis, vasculitis, polyarteritis nodosa, Wegener's granulomatosis, cellulitis, rheumatoid arthritis, psoriatic arthritis, discoid lupus erythematosus, systemic lupus erythematosus, scleroderma, CREST syndrome, Sjogren's syndrome, polymyositis, dermatomyositis, mixed connective tissue disease, relapsing polychondritis, vasculitis, Henoch-Schonlein syndrome, erythema nodosum, polyarteritis nodosa, temporal (giant cell) arteritis, Takayasu's arteritis, Wegener's granulomatosis, Reiter's syndrome, Behcet's syndrome, ankylosing spondylitis, cellulitis, keloids, Ehler Danlos syndrome, Marfan syndrome, pseudoxantoma elasticum, osteogenese imperfecta, chondrodysplasias, epidermolysis bullosa, Alport syndrome, and cutis laxa.

Table 1E also provides information regarding biological activities and preferred therapeutic uses (i.e. see, "Preferred Indications" column) for polynucleotides and polypeptides of the invention (including antibodies, agonists, and/or antagonists thereof). Table 1E also provides information regarding assays which may be used to test polynucleotides and polypeptides of the invention (including antibodies, agonists, and/or antagonists thereof) for the corresponding biological activities. The first column ("Gene No.") provides the gene number in the application for each clone identifier. The second column ("cDNA ATCC™ Deposit No:Z") provides the unique clone identifier for each clone as previously described and indicated in Tables 1A, 1B.1, 1B.2, 1C, and 1D. The third column ("AA SEQ ID NO:Y") indicates the Sequence Listing SEQ ID Number for polypeptide sequences encoded by the corresponding cDNA clones (also as indicated in Tables 1A and 1B.1). The fourth column ("Biological Activity") indicates a biological activity corresponding to the indicated polypeptides (or polynucleotides encoding said polypeptides). The fifth column ("Exemplary Activity Assay") further describes the corresponding biological activity and also provides information pertaining to the various types of assays which may be performed to test, demonstrate, or quantify the corresponding biological activity. The sixth column ("Preferred Indications") describes particular embodiments of the invention as well as indications (e.g. pathologies, diseases, disorders, abnormalities, etc.) for which polynucleotides and polypeptides of the invention (including antibodies, agonists, and/or antagonists thereof) may be used in detecting, diagnosing, preventing, and/or treating.

Tables 1E.1 and 1E.2 also provide information regarding biological activities and preferred therapeutic uses (i.e. see, "Preferred Indications" column) for polynucleotides and polypeptides of the invention (including antibodies, agonists, and/or antagonists thereof). Tables 1E.2 also provide information regarding assays which may be used to test polynucleotides and polypeptides of the invention (including antibodies, agonists, and/or antagonists thereof) for the corresponding biological activities. The first column of Table 1E.1 ("Gene No.") provides the gene number in the application for each clone identifier. The second column of Table 1E.1 ("cDNA Clone ID") provides the unique clone identifier for each clone as previously described and indicated in Tables 1A, 1B.1, 1B.2, and 1C. The third column of Table 1E.1 ("AA SEQ ID NO:Y") indicates the Sequence Listing SEQ ID Number for polypeptide sequences encoded by the corresponding cDNA clones (also as indicated in Tables 1A, 1B.1, 1B.2, and 2). The fourth column ("Biological Activity") indicates a biological activity corresponding to the indicated polypeptides (or polynucleotides encoding said polypeptides).

In Table 1E.2, each of the biological activities of Table 1E.1 are listed by "Biological Activity Number" and the corresponding "Biological Activity" and are followed by an "Exemplary Activity Assay" column and a "Preferred Indication" column; however, for some biological activities no "Exemplary Activity Assay" or "Preferred Indication" is given. The "Exemplary Activity Assay" column describes the biological activity listed in the column that precedes it and also provides information pertaining to the various types of assays which may be performed to test, demonstrate, or quantify the corresponding biological activity. The "Preferred Indication" column also refers to the biological activity listed in the preceding column and describes disease(s) or disorder(s) that may be detected, diagnosed, prevented, treated, or ameliorated by the nucleic acids and proteins (or antibodies against the same) of the invention (including polynucleotide, polypeptide, and antibody fragments or variants thereof).

The present invention is further directed to antibody-based therapies which involve administering antibodies of the invention to an animal, preferably a mammal, and most preferably a human, patient for treating one or more of the disclosed diseases, disorders, or conditions. Therapeutic compounds of the invention include, but are not limited to, antibodies of the invention (including fragments, analogs and derivatives thereof as described herein) and nucleic acids encoding antibodies of the invention (including fragments, analogs and derivatives thereof and anti-idiotypic antibodies as described herein). The antibodies of the invention can be used to detect, prevent, diagnose, prognosticate, treat, inhibit and/or ameliorate diseases, disorders or conditions associated with aberrant expression and/or activity of a polypeptide of the invention, including, but not limited to, any one or more of the diseases, disorders, or conditions described herein, such as immune, cardiovascular, cancer, and other proliferative diseases and disorders. The treatment and/or prevention of diseases, disorders, or conditions associated with aberrant expression and/or activity of a polypeptide of the invention includes, but is not limited to, alleviating symptoms associated with those diseases, disorders or conditions, such as immune, cardiovascular, cancer, and other proliferative diseases and disorders. Antibodies of the invention may be provided in pharmaceutically acceptable compositions as known in the art or as described herein.

In a specific and preferred embodiment, the present invention is directed to antibody-based therapies which involve administering antibodies of the invention to an animal, preferably a mammal, and most preferably a human, patient for treating one or more diseases, disorders, or conditions, including but not limited to: neural disorders, immune system disorders, muscular disorders, reproductive disorders, gastrointestinal disorders, pulmonary disorders, cardiovascular disorders, renal disorders, proliferative disorders, and/or cancerous diseases and conditions, and/or as described elsewhere herein. Therapeutic compounds of the invention include, but are not limited to, antibodies of the invention (e.g., antibodies directed to the full length protein expressed on the cell surface of a mammalian cell; antibodies directed to an epitope of a polypeptide of the invention (such as, for example, a predicted linear epitope shown in Table 1B.1 (such as an epitope shown in column 7 of Table 1B.1); or a conformational epitope, including fragments, analogs and derivatives thereof as described herein) and nucleic acids encoding antibodies of the invention (including fragments, analogs and derivatives thereof and anti-idiotypic antibodies as described herein). The antibodies of the invention can be used to detect, diagnose, inhibit, prevent, treat, prognosticate, and/or ameliorate diseases, disorders or conditions associated with aberrant expression and/or activity of a polypeptide of the invention, including, but not limited to, any one or more of the diseases, disorders, or conditions described herein (such as immune, cardiovascular, cancer, and other proliferative diseases and disorders). The treatment and/or prevention of diseases, disorders, or conditions (such as immune, cardiovascular, cancer, and other proliferative diseases and disorders) associated with aberrant expression and/or activity of a polypeptide of the invention includes, but is not limited to, alleviating symptoms associated with those diseases, disorders or conditions. Antibodies of the invention may be provided in pharmaceutically acceptable compositions as known in the art or as described herein.

A summary of the ways in which the antibodies of the present invention may be used therapeutically includes binding polynucleotides or polypeptides of the present invention locally or systemically in the body or by direct cytotoxicity of the antibody, e.g. as mediated by complement (CDC) or by effector cells (ADCC). Some of these approaches are described in more detail below. Armed with the teachings provided herein, one of ordinary skill in the art will know how to use the antibodies of the present invention for diagnostic, monitoring or therapeutic purposes without undue experimentation.

The antibodies of this invention may be advantageously utilized in combination with other monoclonal or chimeric antibodies, or with lymphokines or hematopoietic growth factors (such as, e.g., IL-2, IL-3 and IL-7), for example, which serve to increase the number or activity of effector cells which interact with the antibodies.

The antibodies of the invention may be administered alone or in combination with other types of treatments (e.g., radiation therapy, chemotherapy, hormonal therapy, immunotherapy and anti-tumor agents). Generally, administration of products of a species origin or species reactivity (in the case of antibodies) that is the same species as that of the patient is preferred. Thus, in a preferred embodiment, human antibodies, fragments derivatives, analogs, or nucleic acids, are administered to a human patient for therapy or prophylaxis.

It is preferred to use high affinity and/or potent in vivo inhibiting and/or neutralizing antibodies against polypeptides or polynucleotides of the present invention, fragments or regions thereof, for both immunoassays directed to and therapy of diseases and disorders (such as immune, cardiovascular, cancer, and other proliferative diseases and disorders) related to polynucleotides or polypeptides, including fragments thereof, of the present invention. Such antibodies, fragments, or regions, will preferably have an affinity for polynucleotides or polypeptides of the invention, including fragments thereof. Preferred binding affinities include those with a dissociation constant or Kd less than $5\times10^{-2}$ M, $10^{-2}$ M, $5\times10^{-3}$ M, $10^{-3}$ M, $5\times10^{-4}$ M, $10^{-4}$ M, $5\times10^{-5}$ M, $10^{-5}$ M, $5\times10^{-6}$ M, $10^{-6}$ M, $5\times10^{-7}$ M, $10^{-7}$ M, $5\times10^{-8}$ M, $10^{-8}$M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, $10^{-13}$ M, $5\times10^{-14}$ M, $10^{-14}$ M, $5\times10^{-15}$ M, and $10^{-15}$ M.

Gene Therapy

In a specific embodiment, nucleic acids comprising sequences encoding antibodies or functional derivatives thereof, are administered to treat, inhibit or prevent a disease or disorder (such an immune, cardiovascular, cancer, and other proliferative disease or disorder) associated with aberrant expression and/or activity of a polypeptide of the invention, by way of gene therapy. Gene therapy refers to therapy performed by the administration to a subject of an expressed or expressible nucleic acid. In this embodiment of the invention, the nucleic acids produce their encoded protein that mediates a therapeutic effect.

Any of the methods for gene therapy available in the art can be used according to the present invention. Exemplary methods are described below.

For general reviews of the methods of gene therapy, see Goldspiel et al., Clinical Pharmacy 12:488-505 (1993); Wu and Wu, Biotherapy 3:87-95 (1991); Tolstoshev, Ann. Rev. Pharmacol. Toxicol. 32:573-596 (1993); Mulligan, Science 260:926-932 (1993); and Morgan and Anderson, Ann. Rev. Biochem. 62:191-217 (1993); May, TIBTECH 11(5):155-215 (1993). Methods commonly known in the art of recombinant DNA technology which can be used are described in Ausubel et al. (eds.), Current Protocols in Molecular Biology, John Wiley & Sons, NY (1993); and Kriegler, Gene Transfer and Expression, A Laboratory Manual, Stockton Press, NY (1990).

In a preferred embodiment, the compound comprises nucleic acid sequences encoding an antibody, said nucleic acid sequences being part of expression vectors that express the antibody or fragments or chimeric proteins or heavy or light chains thereof in a suitable host. In particular, such nucleic acid sequences have promoters operably linked to the antibody coding region, said promoter being inducible or constitutive, and, optionally, tissue-specific. In another particular embodiment, nucleic acid molecules are used in which the antibody coding sequences and any other desired sequences are flanked by regions that promote homologous recombination at a desired site in the genome, thus providing for intrachromosomal expression of the antibody encoding nucleic acids (Koller and Smithies, Proc. Natl. Acad. Sci. USA 86:8932-8935 (1989); Zijlstra et al., Nature 342:435-438 (1989). In specific embodiments, the expressed antibody molecule is a single chain antibody; alternatively, the nucleic acid sequences include sequences encoding both the heavy and light chains, or fragments thereof, of the antibody.

Delivery of the nucleic acids into a patient may be either direct, in which case the patient is directly exposed to the nucleic acid or nucleic acid-carrying vectors, or indirect, in which case, cells are first transformed with the nucleic acids in vitro, then transplanted into the patient. These two approaches are known, respectively, as in vivo or ex vivo gene therapy.

In a specific embodiment, the nucleic acid sequences are directly administered in vivo, where it is expressed to produce the encoded product. This can be accomplished by any of numerous methods known in the art, e.g., by constructing them as part of an appropriate nucleic acid expression vector and administering it so that they become intracellular, e.g., by infection using defective or attenuated retrovirals or other viral vectors (see U.S. Pat. No. 4,980,286), or by direct injection of naked DNA, or by use of microparticle bombardment (e.g., a gene gun; BIOLISTIC™, DUPONT™), or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, J. Biol. Chem. 262:4429-4432 (1987)) (which can be used to target cell types specifically expressing the receptors), etc. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180; WO 92/22635; WO92/20316; WO93/14188, WO 93/20221). Alternatively, the nucleic acid can be introduced intracellularly and incorporated within host cell DNA for expression, by homologous recombination (Koller and Smithies, Proc. Natl. Acad. Sci. USA 86:8932-8935 (1989); Zijlstra et al., Nature 342:435-438 (1989)).

In a specific embodiment, viral vectors which contain nucleic acid sequences encoding an antibody of the invention are used. For example, a retroviral vector can be used (see Miller et al., Meth. Enzymol. 217:581-599 (1993)). These retroviral vectors contain the components necessary for the correct packaging of the viral genome and integration into the host cell DNA. The nucleic acid sequences encoding the antibody to be used in gene therapy are cloned into one or more vectors, which facilitates delivery of the gene into a patient. More detail about retroviral vectors can be found in Boesen et al., Biotherapy 6:291-302 (1994), which describes the use of a retroviral vector to deliver the mdr1 gene to hematopoietic stem cells in order to make the stem cells more resistant to chemotherapy. Other references illustrating the use of retroviral vectors in gene therapy are: Clowes et al., J. Clin. Invest. 93:644-651 (1994); Kiem et al., Blood 83:1467-1473 (1994); Salmons and Gunzberg, Human Gene Therapy 4:129-141 (1993); and Grossman and Wilson, Curr. Opin. in Genetics and Devel. 3:110-114 (1993).

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, Current Opinion in Genetics and Development 3:499-503 (1993) present a review of adenovirus-based gene therapy. Bout et al., Human Gene Therapy 5:3-10 (1994) demonstrated the use of adenovirus vectors to transfer genes to the respiratory epithelia of rhesus monkeys. Other instances of the use of adenoviruses in gene therapy can be found in Rosenfeld et al., Science 252:431-434 (1991); Rosenfeld et al., Cell 68:143-155 (1992); Mastrangeli et al., J. Clin. Invest. 91:225-234 (1993); PCT Publication WO94/12649; and Wang, et al., Gene Therapy 2:775-783 (1995). In a preferred embodiment, adenovirus vectors are used.

Adeno-associated virus (AAV) has also been proposed for use in gene therapy (Walsh et al., Proc. Soc. Exp. Biol. Med. 204:289-300 (1993); U.S. Pat. No. 5,436,146).

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see, e.g., Loeffler and Behr, Meth. Enzymol. 217:599-618 (1993); Cohen et al., Meth. Enzymol. 217:618-644 (1993); Cline, Pharmac. Ther. 29:69-92m (1985) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. Recombinant blood cells (e.g., hematopoietic stem or progenitor cells) are preferably administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as T lymphocytes, B lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

In a preferred embodiment, the cell used for gene therapy is autologous to the patient.

In an embodiment in which recombinant cells are used in gene therapy, nucleic acid sequences encoding an antibody are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention (see e.g. PCT Publication WO 94/08598; Stemple and Anderson, Cell 71:973-985 (1992); Rheinwald, Meth. Cell Bio. 21A:229 (1980); and Pittelkow and Scott, Mayo Clinic Proc. 61:771 (1986)).

In a specific embodiment, the nucleic acid to be introduced for purposes of gene therapy comprises an inducible promoter operably linked to the coding region, such that expression of the nucleic acid is controllable by the presence or absence of an appropriate inducer of transcription.

Demonstration of Therapeutic or Prophylactic Activity

The compounds or pharmaceutical compositions of the invention are preferably tested in vitro, and then in vivo for the desired therapeutic or prophylactic activity, prior to use in humans. For example, in vitro assays to demonstrate the therapeutic or prophylactic utility of a compound or pharmaceutical composition include, the effect of a compound on a cell line or a patient tissue sample. The effect of the compound or composition on the cell line and/or tissue sample can be determined utilizing techniques known to those of skill in the art including, but not limited to, rosette formation assays and cell lysis assays. In accordance with the invention, in vitro assays which can be used to determine whether administration of a specific compound is indicated, include in vitro cell culture assays in which a patient tissue sample is grown in culture, and exposed to or otherwise administered a compound, and the effect of such compound upon the tissue sample is observed.

Therapeutic/Prophylactic Administration and Composition

The invention provides methods of treatment, inhibition and prophylaxis by administration to a subject of an effective amount of a compound or pharmaceutical composition of the invention, preferably a polypeptide or antibody of the invention. In a preferred embodiment, the compound is substantially purified (e.g., substantially free from substances that limit its effect or produce undesired side-effects). The subject is preferably an animal, including but not limited to animals such as cows, pigs, horses, chickens, cats, dogs, etc., and is preferably a mammal, and most preferably human.

Formulations and methods of administration that can be employed when the compound comprises a nucleic acid or an immunoglobulin are described above; additional appropriate formulations and routes of administration can be selected from among those described herein below.

Various delivery systems are known and can be used to administer a compound of the invention, e.g., encapsulation in liposomes, microparticles, microcapsules, recombinant cells capable of expressing the compound, receptor-mediated endocytosis (see, e.g., Wu and Wu, J. Biol. Chem. 262:4429-4432 (1987)), construction of a nucleic acid as part of a retroviral or other vector, etc. Methods of introduction include but are not limited to intradermal, intramuscular, intraperitoneal, intravenous, subcutaneous, intranasal, epidural, and oral routes. The compounds or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compounds or compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compounds or compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as silastic membranes, or fibers. Preferably, when administering a protein, including an antibody, of the invention, care must be taken to use materials to which the protein does not absorb.

In another embodiment, the compound or composition can be delivered in a vesicle, in particular a liposome (see Langer, Science 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.)

In yet another embodiment, the compound or composition can be delivered in a controlled release system. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J., Macromol. Sci. Rev. Macromol. Chem. 23:61 (1983); see also Levy et al., Science 228:190 (1985); During et al., Ann. Neurol. 25:351 (1989); Howard et al., J. Neurosurg. 71:105 (1989)). In yet another embodiment, a controlled release system can be placed in proximity of the therapeutic target, e.g., the brain, thus requiring only a fraction of the systemic dose (see, e.g., Goodson, in Medical Applications of Controlled Release, supra, vol. 2, pp. 115-138 (1984)).

Other controlled release systems are discussed in the review by Langer (Science 249:1527-1533 (1990)).

In a specific embodiment where the compound of the invention is a nucleic acid encoding a protein, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; BIOLISTIC™, DUPONT™), or coating with lipids or cell-surface receptors or transfecting agents, or by administering it in linkage to a homeobox-like peptide which is known to enter the nucleus (see e.g., Joliot et al., Proc. Natl. Acad. Sci. USA 88:1864-1868 (1991)), etc. Alternatively, a nucleic acid can be introduced intracellularly and incorporated within host cell DNA for expression, by homologous recombination.

The present invention also provides pharmaceutical compositions. Such compositions comprise a therapeutically effective amount of a compound, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compounds of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The amount of the compound of the invention which will be effective in the treatment, inhibition and prevention of a disease or disorder associated with aberrant expression and/or activity of a polypeptide of the invention can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems.

For antibodies, the dosage administered to a patient is typically 0.1 mg/kg to 100 mg/kg of the patient's body weight. Preferably, the dosage administered to a patient is between 0.1 mg/kg and 20 mg/kg of the patient's body weight, more preferably 1 mg/kg to 10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies of the invention may be reduced by enhancing uptake and tissue penetration (e.g., into the brain) of the antibodies by modifications such as, for example, lipidation.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

Diagnosis and Imaging

Labeled antibodies, and derivatives and analogs thereof, which specifically bind to a polypeptide of interest can be used for diagnostic purposes to detect, diagnose, prognosticate, or monitor diseases, disorders, and/or conditions (such as immune, cardiovascular, cancer, and other proliferative diseases, disorders, and conditions) associated with the aberrant expression and/or activity of a polypeptide of the invention. The invention provides for the detection of aberrant expression of a polypeptide of interest, comprising (a) assaying the expression of the polypeptide of interest in cells or body fluid of an individual using one or more antibodies specific to the polypeptide interest and (b) comparing the level of gene expression with a standard gene expression level, whereby an increase or decrease in the assayed polypeptide gene expression level compared to the standard expression level is indicative of aberrant expression.

The invention provides a diagnostic assay for diagnosing a disease or disorder (such an immune, cardiovascular, cancer, or other proliferative disease or disorders), comprising (a) assaying the expression of the polypeptide of interest in cells or body fluid of an individual using one or more antibodies specific to the polypeptide interest and (b) comparing the level of gene expression with a standard gene expression level, whereby an increase or decrease in the assayed polypeptide gene expression level compared to the standard expression level is indicative of a particular disease or disorder. With respect to cancer and other hyperproliferative diseases and disorders (such as immunogenic cancer or cancer of the cardiovascular system), the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer or other hyperproliferative disease (such as immunogenic cancer or cancer of the cardiovascular system).

Antibodies of the invention can be used to assay protein levels in a biological sample using classical immunohistological methods known to those of skill in the art (e.g., see Jalkanen et al., J. Cell. Biol. 101:976-985 (1985); Jalkanen et al., J. Cell. Biol. 105:3087-3096 (1987)). Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase; radioisotopes, such as iodine (125I, 121I), carbon (14C), sulfur (35S), tritium (3H), indium (112In), and technetium (99Tc); luminescent labels, such as luminol; and fluorescent labels, such as fluorescein and rhodamine, and biotin.

One facet of the invention is the detection and diagnosis of a disease or disorder associated with aberrant expression of a polypeptide of interest in an animal, preferably a mammal and most preferably a human. In one embodiment, diagnosis comprises: a) administering (for example, parenterally, subcutaneously, or intraperitoneally) to a subject an effective amount of a labeled molecule which specifically binds to the polypeptide of interest; b) waiting for a time interval following the administering for permitting the labeled molecule to preferentially concentrate at sites in the subject where the polypeptide is expressed (and for unbound labeled molecule to be cleared to background level); c) determining background level; and d) detecting the labeled molecule in the subject, such that detection of labeled molecule above the background level indicates that the subject has a particular disease or disorder associated with aberrant expression of the polypeptide of interest. Background level can be determined by various methods including, comparing the amount of labeled molecule detected to a standard value previously determined for a particular system.

It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of 99mTc. The labeled antibody or antibody fragment will then preferentially accumulate at the location of cells which contain the specific protein. In vivo tumor imaging is described in S. W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982)).

Depending on several variables, including the type of label used and the mode of administration, the time interval following the administration for permitting the labeled molecule to preferentially concentrate at sites in the subject and for unbound labeled molecule to be cleared to background level is 6 to 48 hours or 6 to 24 hours or 6 to 12 hours. In another embodiment the time interval following administration is 5 to 20 days or 5 to 10 days.

In an embodiment, monitoring of the disease or disorder is carried out by repeating the method for diagnosing the disease or disease, for example, one month after initial diagnosis, six months after initial diagnosis, one year after initial diagnosis, etc.

Presence of the labeled molecule can be detected in the patient using methods known in the art for in vivo scanning. These methods depend upon the type of label used. Skilled artisans will be able to determine the appropriate method for detecting a particular label. Methods and devices that may be used in the diagnostic methods of the invention include, but are not limited to, computed tomography (CT), whole body scan such as position emission tomography (PET), magnetic resonance imaging (MRI), and sonography.

In a specific embodiment, the molecule is labeled with a radioisotope and is detected in the patient using a radiation responsive surgical instrument (Thurston et al., U.S. Pat. No. 5,441,050). In another embodiment, the molecule is labeled with a fluorescent compound and is detected in the patient using a fluorescence responsive scanning instrument. In another embodiment, the molecule is labeled with a positron emitting metal and is detected in the patent using positron emission-tomography. In yet another embodiment, the molecule is labeled with a paramagnetic label and is detected in a patient using magnetic resonance imaging (MRI).

Kits

The present invention provides kits that can be used in the above methods. In one embodiment, a kit comprises an antibody of the invention, preferably a purified antibody, in one or more containers. In a specific embodiment, the kits of the present invention contain a substantially isolated polypeptide comprising an epitope that is specifically immunoreactive with an antibody included in the kit. Preferably, the kits of the present invention further comprise a control antibody that does not react with the polypeptide of interest. In another specific embodiment, the kits of the present invention contain a means for detecting the binding of an antibody to a polypeptide of interest (e.g., the antibody may be conjugated to a detectable substrate such as a fluorescent compound, an enzymatic substrate, a radioactive compound or a luminescent compound, or a second antibody which recognizes the first antibody may be conjugated to a detectable substrate).

In another specific embodiment of the present invention, the kit is a diagnostic kit for use in screening serum containing antibodies specific against proliferative and/or cancerous polynucleotides and polypeptides. Such a kit may include a control antibody that does not react with the polypeptide of interest. Such a kit may include a substantially isolated polypeptide antigen comprising an epitope that is specifically immunoreactive with at least one anti-polypeptide antigen antibody. Further, such a kit includes means for detecting the binding of said antibody to the antigen (e.g., the antibody may be conjugated to a fluorescent compound such as fluorescein or rhodamine which can be detected by flow cytometry). In specific embodiments, the kit may include a recombinantly produced or chemically synthesized polypeptide antigen. The polypeptide antigen of the kit may also be attached to a solid support.

In a more specific embodiment the detecting means of the above-described kit includes a solid support to which said polypeptide antigen is attached. Such a kit may also include a non-attached reporter-labeled anti-human antibody. In this embodiment, binding of the antibody to the polypeptide antigen can be detected by binding of the said reporter-labeled antibody.

In an additional embodiment, the invention includes a diagnostic kit for use in screening serum containing antigens of the polypeptide of the invention. The diagnostic kit includes a substantially isolated antibody specifically immunoreactive with polypeptide or polynucleotide antigens, and means for detecting the binding of the polynucleotide or polypeptide antigen to the antibody. In one embodiment, the antibody is attached to a solid support. In a specific embodiment, the antibody may be a monoclonal antibody. The detecting means of the kit may include a second, labeled monoclonal antibody. Alternatively, or in addition, the detecting means may include a labeled, competing antigen.

In one diagnostic configuration, test serum is reacted with a solid phase reagent having a surface-bound antigen obtained by the methods of the present invention. After binding with specific antigen antibody to the reagent and removing unbound serum components by washing, the reagent is reacted with reporter-labeled anti-human antibody to bind reporter to the reagent in proportion to the amount of bound anti-antigen antibody on the solid support. The reagent is again washed to remove unbound labeled antibody, and the amount of reporter associated with the reagent is determined. Typically, the reporter is an enzyme which is detected by incubating the solid phase in the presence of a suitable fluorometric, luminescent or colorimetric substrate (SIGMA™, St. Louis, Mo.).

The solid surface reagent in the above assay is prepared by known techniques for attaching protein material to solid support material, such as polymeric beads, dip sticks, 96-well plate or filter material. These attachment methods generally include non-specific adsorption of the protein to the support or covalent attachment of the protein, typically through a free amine group, to a chemically reactive group on the solid support, such as an activated carboxyl, hydroxyl, or aldehyde group. Alternatively, streptavidin coated plates can be used in conjunction with biotinylated antigen(s).

Thus, the invention provides an assay system or kit for carrying out this diagnostic method. The kit generally includes a support with surface-bound recombinant antigens, and a reporter-labeled anti-human antibody for detecting surface-bound anti-antigen antibody.

Uses of the Polynucleotides

Each of the polynucleotides identified herein can be used in numerous ways as reagents. The following description should be considered exemplary and utilizes known techniques.

The polynucleotides of the present invention are useful for chromosome identification. There exists an ongoing need to identify new chromosome markers, since few chromosome marking reagents, based on actual sequence data (repeat polymorphisms), are presently available. Each sequence is specifically targeted to and can hybridize with a particular location on an individual human chromosome, thus each polynucleotide of the present invention can routinely be used as a chromosome marker using techniques known in the art. Table 1B.1, column 8 provides the chromosome location of some of the polynucleotides of the invention.

Briefly, sequences can be mapped to chromosomes by preparing PCR primers (preferably at least 15 bp (e.g., 15-25 bp) from the sequences shown in SEQ ID NO:X. Primers can optionally be selected using computer analysis so that primers do not span more than one predicted exon in the genomic DNA. These primers are then used for PCR screening of somatic cell hybrids containing individual human chromosomes. Only those hybrids containing the human gene corresponding to SEQ ID NO:X will yield an amplified fragment.

Similarly, somatic hybrids provide a rapid method of PCR mapping the polynucleotides to particular chromosomes. Three or more clones can be assigned per day using a single thermal cycler. Moreover, sublocalization of the polynucleotides can be achieved with panels of specific chromosome fragments. Other gene mapping strategies that can be used include in situ hybridization, prescreening with labeled flow-sorted chromosomes, preselection by hybridization to construct chromosome specific-cDNA libraries, and computer mapping techniques (See, e.g., Shuler, Trends Biotechnol 16:456-459 (1998) which is hereby incorporated by reference in its entirety).

Precise chromosomal location of the polynucleotides can also be achieved using fluorescence in situ hybridization (FISH) of a metaphase chromosomal spread. This technique uses polynucleotides as short as 500 or 600 bases; however, polynucleotides 2,000-4,000 bp are preferred. For a review of this technique, see Verma et al., "Human Chromosomes: a Manual of Basic Techniques," Pergamon Press, New York (1988).

For chromosome mapping, the polynucleotides can be used individually (to mark a single chromosome or a single site on that chromosome) or in panels (for marking multiple sites and/or multiple chromosomes). Preferred polynucleotides correspond to the noncoding regions of the cDNAs because the coding sequences are more likely conserved within gene families, thus increasing the chance of cross hybridization during chromosomal mapping.

Thus, the present invention also provides a method for chromosomal localization which involves (a) preparing PCR primers from the polynucleotide sequences in Table 1B.1 and/or 2 and SEQ ID NO:X and (b) screening somatic cell hybrids containing individual chromosomes.

The polynucleotides of the present invention would likewise be useful for radiation hybrid mapping, HAPPY mapping, and long range restriction mapping. For a review of these techniques and others known in the art, see, e.g. Dear, "Genome Mapping: A Practical Approach," IRL Press at Oxford University Press, London (1997); Aydin, J. Mol. Med. 77:691-694 (1999); Hacia et al., Mol. Psychiatry. 3:483-492 (1998); Herrick et al., Chromosome Res. 7:409-423 (1999); Hamilton et al., Methods Cell Biol. 62:265-280 (2000); and/or Ott, J. Hered. 90:68-70 (1999) each of which is hereby incorporated by reference in its entirety.

Once a polynucleotide has been mapped to a precise chromosomal location, the physical position of the polynucleotide can be used in linkage analysis. Linkage analysis establishes coinheritance between a chromosomal location and presentation of a particular disease. (Disease mapping data are found, for example, in V. McKusick, Mendelian Inheritance in Man (available on line through Johns Hopkins University Welch Medical Library)). Table 1B.1 (such as column 9 of Table 1B.1) provides an OMIM reference identification number of diseases associated with the cytologic band disclosed in Table 1B.1 (such as column 8 of Table 1B.1), as determined using techniques described herein and by reference to Table 5. Assuming 1 megabase mapping resolution and one gene per 20 kb, a cDNA precisely localized to a chromosomal region associated with the disease could be one of 50-500 potential causative genes.

Thus, once coinheritance is established, differences in a polynucleotide of the invention and the corresponding gene between affected and unaffected individuals can be examined. First, visible structural alterations in the chromosomes, such as deletions or translocations, are examined in chromosome spreads or by PCR. If no structural alterations exist, the presence of point mutations are ascertained. Mutations observed in some or all affected individuals, but not in normal individuals, indicates that the mutation may cause the disease. However, complete sequencing of the polypeptide and the corresponding gene from several normal individuals is required to distinguish the mutation from a polymorphism. If a new polymorphism is identified, this polymorphic polypeptide can be used for further linkage analysis.

Furthermore, increased or decreased expression of the gene in affected individuals as compared to unaffected individuals can be assessed using the polynucleotides of the invention. Any of these alterations (altered expression, chromosomal rearrangement, or mutation) can be used as a diagnostic or prognostic marker. Diagnostic and prognostic methods, kits and reagents encompassed by the present invention are briefly described below and more thoroughly elsewhere herein (see e.g., the sections labeled "Antibodies", "Diagnostic Assays", and "Methods for Detecting Diseases").

Thus, the invention also provides a diagnostic method useful during diagnosis of a disorder, involving measuring the expression level of polynucleotides of the present invention in cells or body fluid from an individual and comparing the measured gene expression level with a standard level of polynucleotide expression level, whereby an increase or decrease in the gene expression level compared to the standard is indicative of a disorder. Additional non-limiting examples of diagnostic methods encompassed by the present invention are more thoroughly described elsewhere herein (see, e.g., Example 12).

In still another embodiment, the invention includes a kit for analyzing samples for the presence of proliferative and/or cancerous polynucleotides derived from a test subject. In a general embodiment, the kit includes at least one polynucleotide probe containing a nucleotide sequence that will specifically hybridize with a polynucleotide of the invention and a suitable container. In a specific embodiment, the kit includes two polynucleotide probes defining an internal region of the polynucleotide of the invention, where each probe has one strand containing a 31'mer-end internal to the region. In a further embodiment, the probes may be useful as primers for polymerase chain reaction amplification.

Where a diagnosis of a related disorder, including, for example, diagnosis of a tumor, has already been made according to conventional methods, the present invention is useful as a prognostic indicator, whereby patients exhibiting enhanced or depressed polynucleotide of the invention expression will experience a worse clinical outcome relative to patients expressing the gene at a level nearer the standard level.

By "measuring the expression level of polynucleotides of the invention" is intended qualitatively or quantitatively measuring or estimating the level of the polypeptide of the invention or the level of the mRNA encoding the polypeptide of the invention in a first biological sample either directly (e.g., by determining or estimating absolute protein level or mRNA level) or relatively (e.g., by comparing to the polypeptide level or mRNA level in a second biological sample). Preferably, the polypeptide level or mRNA level in the first biological sample is measured or estimated and compared to a standard polypeptide level or mRNA level, the standard being taken from a second biological sample obtained from an individual not having the related disorder or being determined by averaging levels from a population of individuals not having a related disorder. As will be appreciated in the art, once a standard polypeptide level or mRNA level is known, it can be used repeatedly as a standard for comparison.

By "biological sample" is intended any biological sample obtained from an individual, body fluid, cell line, tissue culture, or other source that contains polypeptide of the present invention or the corresponding mRNA. As indicated, biological samples include body fluids (such as semen, lymph, vaginal pool, sera, plasma, urine, synovial fluid and spinal fluid) which contain the polypeptide of the present invention, and tissue sources found to express the polypeptide of the present invention. Methods for obtaining tissue biopsies and body fluids from mammals are well known in the art. Where the biological sample is to include mRNA, a tissue biopsy is the preferred source.

The method(s) provided above may preferably be applied in a diagnostic method and/or kits in which polynucleotides and/or polypeptides of the invention are attached to a solid support. In one exemplary method, the support may be a "gene chip" or a "biological chip" as described in U.S. Pat. Nos. 5,837,832, 5,874,219, and 5,856,174. Further, such a gene chip with polynucleotides of the invention attached may be used to identify polymorphisms between the isolated polynucleotide sequences of the invention, with polynucleotides isolated from a test subject. The knowledge of such polymorphisms (i.e. their location, as well as, their existence) would be beneficial in identifying disease loci for many disorders, such as for example, in neural disorders, immune system disorders, muscular disorders, reproductive disorders, gastrointestinal disorders, pulmonary disorders, digestive disorders, metabolic disorders, cardiovascular disorders, renal disorders, proliferative disorders, and/or cancerous diseases and conditions. Such a method is described in U.S. Pat. Nos. 5,858,659 and 5,856,104. The US patents referenced supra are hereby incorporated by reference in their entirety herein.

The present invention encompasses polynucleotides of the present invention that are chemically synthesized, or reproduced as peptide nucleic acids (PNA), or according to other methods known in the art. The use of PNAs would serve as the preferred form if the polynucleotides of the invention are incorporated onto a solid support, or gene chip. For the purposes of the present invention, a peptide nucleic acid (PNA) is a polyamide type of DNA analog and the monomeric units for adenine, guanine, thymine and cytosine are available commercially (Perceptive Biosystems). Certain components of DNA, such as phosphorus, phosphorus oxides, or deoxyribose derivatives, are not present in PNAs. As disclosed by Nielsen et al., Science 254, 1497 (1991); and Egholm et al., Nature 365, 666 (1993), PNAs bind specifically and tightly to complementary DNA strands and are not degraded by nucleases. In fact, PNA binds more strongly to DNA than DNA itself does. This is probably because there is no electrostatic repulsion between the two strands, and also the polyamide backbone is more flexible. Because of this, PNA/DNA duplexes bind under a wider range of stringency conditions than DNA/DNA duplexes, making it easier to perform multiplex hybridization. Smaller probes can be used than with DNA due to the strong binding. In addition, it is more likely that single base mismatches can be determined with PNA/DNA hybridization because a single mismatch in a PNA/DNA 15-mer lowers the melting point ($T_m$) by 8°-20° C., vs. 4°-16° C. for the DNA/DNA 15-mer duplex. Also, the absence of charge groups in PNA means that hybridization can be done at low ionic strengths and reduce possible interference by salt during the analysis.

The compounds of the present invention have uses which include, but are not limited to, detecting cancer in mammals. In particular the invention is useful during diagnosis of pathological cell proliferative neoplasias which include, but are not limited to: acute myelogenous leukemias including acute monocytic leukemia, acute myeloblastic leukemia, acute promyelocytic leukemia, acute myelomonocytic leukemia, acute erythroleukemia, acute megakaryocytic leukemia, and acute undifferentiated leukemia, etc.; and chronic myelogenous leukemias including chronic myelomonocytic leukemia, chronic granulocytic leukemia, etc. Preferred mammals include monkeys, apes, cats, dogs, cows, pigs, horses, rabbits and humans. Particularly preferred are humans.

Pathological cell proliferative disorders are often associated with inappropriate activation of proto-oncogenes. (Gelmann, E. P. et al., "The Etiology of Acute Leukemia: Molecular Genetics and Viral Oncology," in Neoplastic Diseases of the Blood, Vol 1., Wiernik, P. H. et al. eds., 161-182 (1985)). Neoplasias are now believed to result from the qualitative alteration of a normal cellular gene product, or from the quantitative modification of gene expression by insertion into the chromosome of a viral sequence, by chromosomal translocation of a gene to a more actively transcribed region, or by some other mechanism. (Gelmann et al., supra) It is likely that mutated or altered expression of specific genes is involved in the pathogenesis of some leukemias, among other tissues and cell types. (Gelmann et al., supra) Indeed, the human counterparts of the oncogenes involved in some animal neoplasias have been amplified or translocated in some cases of human leukemia and carcinoma. (Gelmann et al., supra)

For example, c-myc expression is highly amplified in the non-lymphocytic leukemia cell line HL-60. When HL-60 cells are chemically induced to stop proliferation, the level of c-myc is found to be downregulated. (International Publication Number WO 91/15580). However, it has been shown that exposure of HL-60 cells to a DNA construct that is complementary to the 5' end of c-myc or c-myb blocks translation of the corresponding mRNAs which downregulates expression of the c-myc or c-myb proteins and causes arrest of cell proliferation and differentiation of the treated cells. (International Publication Number WO 91/15580; Wickstrom et al., Proc. Natl. Acad. Sci. 85:1028 (1988); Anfossi et al., Proc. Natl. Acad. Sci. 86:3379 (1989)). However, the skilled artisan would appreciate the present invention's usefulness is not be limited to treatment, prevention, and/or prognosis of proliferative disorders of cells and tissues of hematopoietic origin, in light of the numerous cells and cell types of varying origins which are known to exhibit proliferative phenotypes.

In addition to the foregoing, a polynucleotide of the present invention can be used to control gene expression through triple helix formation or through antisense DNA or RNA. Antisense techniques are discussed, for example, in Okano, J. Neurochem. 56: 560 (1991); "Oligodeoxynucleotides as Antisense Inhibitors of Gene Expression, CRC Press, Boca Raton, Fla. (1988). Triple helix formation is discussed in, for instance Lee et al., Nucleic Acids Research 6: 3073 (1979); Cooney et al., Science 241: 456 (1988); and Dervan et al., Science 251: 1360 (1991). Both methods rely on binding of the polynucleotide to a complementary DNA or RNA. For these techniques, preferred polynucleotides are usually oligonucleotides 20 to 40 bases in length and complementary to either the region of the gene involved in transcription (triple helix—see Lee et al., Nucl. Acids Res. 6:3073 (1979); Cooney et al., Science 241:456 (1988); and Dervan et al., Science 251:1360 (1991)) or to the mRNA itself (antisense—Okano, J. Neurochem. 56:560 (1991); Oligodeoxy-nucleotides as Antisense Inhibitors of Gene Expression, CRC Press, Boca Raton, Fla. (1988)). Triple helix formation optimally results in a shut-off of RNA transcription from DNA, while antisense RNA hybridization blocks translation of an mRNA molecule into polypeptide. The oligonucleotide described above can also be delivered to cells such that the antisense RNA or DNA may be expressed in vivo to inhibit production of polypeptide of the present invention antigens. Both techniques are effective in model systems, and the information disclosed herein can be used to design antisense or triple helix polynucleotides in an effort to treat disease, and in particular, for the treatment of proliferative diseases and/or conditions. Non-limiting antisense and triple helix methods encompassed by the present invention are more thoroughly described elsewhere herein (see, e.g., the section labeled "Antisense and Ribozyme (Antagonists)").

Polynucleotides of the present invention are also useful in gene therapy. One goal of gene therapy is to insert a normal gene into an organism having a defective gene, in an effort to correct the genetic defect. The polynucleotides disclosed in the present invention offer a means of targeting such genetic defects in a highly accurate manner. Another goal is to insert a new gene that was not present in the host genome, thereby producing a new trait in the host cell. Additional non-limiting examples of gene therapy methods encompassed by the present invention are more thoroughly described elsewhere herein (see, e.g., the sections labeled "Gene Therapy Methods", and Examples 16, 17 and 18).

The polynucleotides are also useful for identifying individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identifying personnel. This method does not suffer from the current limitations of "Dog Tags" which can be lost, switched, or stolen, making positive identification difficult. The polynucleotides of the present invention can be used as additional DNA markers for RFLP.

The polynucleotides of the present invention can also be used as an alternative to RFLP, by determining the actual base-by-base DNA sequence of selected portions of an individual's genome. These sequences can be used to prepare PCR primers for amplifying and isolating such selected DNA, which can then be sequenced. Using this technique, individuals can be identified because each individual will have a unique set of DNA sequences. Once an unique ID database is established for an individual, positive identification of that individual, living or dead, can be made from extremely small tissue samples.

Forensic biology also benefits from using DNA-based identification techniques as disclosed herein. DNA sequences taken from very small biological samples such as tissues, e.g., hair or skin, or body fluids, e.g., blood, saliva, semen, synovial fluid, amniotic fluid, breast milk, lymph, pulmonary sputum or surfactant, urine, fecal matter, etc., can be amplified using PCR. In one prior art technique, gene sequences amplified from polymorphic loci, such as DQa class II HLA gene, are used in forensic biology to identify individuals. (Erlich, H., PCR Technology, Freeman and Co. (1992)). Once these specific polymorphic loci are amplified, they are digested with one or more restriction enzymes, yielding an identifying set of bands on a Southern blot probed with DNA corresponding to the DQa class II HLA gene. Similarly, polynucleotides of the present invention can be used as polymorphic markers for forensic purposes.

There is also a need for reagents capable of identifying the source of a particular tissue. Such need arises, for example, in forensics when presented with tissue of unknown origin. Appropriate reagents can comprise, for example, DNA probes or primers prepared from the sequences of the present invention, specific to tissues, including but not limited to those shown in Table 1B.2. Panels of such reagents can identify tissue by species and/or by organ type. In a similar fashion, these reagents can be used to screen tissue cultures for contamination. Additional non-limiting examples of such uses are further described herein.

The polynucleotides of the present invention are also useful as hybridization probes for differential identification of the tissue(s) or cell type(s) present in a biological sample. Similarly, polypeptides and antibodies directed to polypeptides of the present invention are useful to provide immunological probes for differential identification of the tissue(s) (e.g., immunohistochemistry assays) or cell type(s) (e.g., immunocytochemistry assays). In addition, for a number of disorders of the above tissues or cells, significantly higher or lower levels of gene expression of the polynucleotides/polypeptides of the present invention may be detected in certain tissues (e.g., tissues expressing polypeptides and/or polynucleotides of the present invention, for example, those disclosed in Table 1B.2 (such as in column 5 of Table 1B.2), and/or cancerous and/or wounded tissues) or bodily fluids (e.g., semen, lymph, vaginal pool, serum, plasma, urine, synovial fluid or spinal fluid) taken from an individual having such a disorder, relative to a "standard" gene expression level, i.e., the expression level in healthy tissue from an individual not having the disorder.

Thus, the invention provides a diagnostic method of a disorder, which involves: (a) assaying gene expression level in cells or body fluid of an individual; (b) comparing the gene expression level with a standard gene expression level, whereby an increase or decrease in the assayed gene expression level compared to the standard expression level is indicative of a disorder.

In the very least, the polynucleotides of the present invention can be used as molecular weight markers on Southern gels, as diagnostic probes for the presence of a specific mRNA in a particular cell type, as a probe to "subtract-out" known sequences in the process of discovering novel polynucleotides, for selecting and making oligomers for attachment to a "gene chip" or other support, to raise anti-DNA antibodies using DNA immunization techniques, and as an antigen to elicit an immune response.

Uses of the Polypeptides

Each of the polypeptides identified herein can be used in numerous ways. The following description should be considered exemplary and utilizes known techniques.

Polypeptides and antibodies directed to polypeptides of the invention are useful to provide immunological probes for differential identification of the tissue(s) (e.g., immunohistochemistry assays such as, for example, ABC immunoperoxidase (Hsu et al., J. Histochem. Cytochem. 29:577-580 (1981)) or cell type(s) (e.g., immunocytochemistry assays).

Antibodies can be used to assay levels of polypeptides encoded by polynucleotides of the invention in a biological sample using classical immunohistological methods known to those of skill in the art (e.g., see Jalkanen, et al., J. Cell. Biol. 101:976-985 (1985); Jalkanen, et al., J. Cell. Biol. 105: 3087-3096 (1987)). Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase; radioisotopes, such as iodine ($^{131}$I, $^{125}$I, $^{123}$I, $^{121}$I), carbon ($^{14}$C), sulfur ($^{35}$S), tritium ($^{3}$H), indium ($^{115m}$In, $^{113m}$In, $^{112}$In, $^{111}$In), and technetium ($^{99}$Tc, $^{99m}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru; luminescent labels, such as luminol; and fluorescent labels, such as fluorescein and rhodamine, and biotin.

In addition to assaying levels of polypeptide of the present invention in a biological sample, proteins can also be detected in vivo by imaging. Antibody labels or markers for in vivo imaging of protein include those detectable by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which may be incorporated into the antibody by labeling of nutrients for the relevant hybridoma.

A protein-specific antibody or antibody fragment which has been labeled with an appropriate detectable imaging moiety, such as a radioisotope (for example, $^{131}$I, $^{112}$In, $^{99m}$Tc, ($^{131}$I, $^{125}$I, $^{123}$I, $^{121}$I), carbon ($^{14}$C), sulfur ($^{35}$S), tritium ($^{3}$H), indium ($^{115m}$In, $^{113m}$In, $^{112}$In, $^{111}$In), and technetium ($^{99}$Tc, $^{99m}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F, $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru), a radio-opaque substance, or a material detectable by nuclear magnetic resonance, is introduced (for example, parenterally, subcutaneously or intraperitoneally) into the mammal to be examined for immune system disorder. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99m}$Tc. The labeled antibody or antibody fragment will then preferentially accumulate at the location of cells which express the polypeptide encoded by a polynucleotide of the invention. In vivo tumor imaging is described in S. W. Burchiel et al., "Immunopharmacokinetics of Radiolabeled Antibodies and Their Fragments" (Chapter 13 in *Tumor Imaging: The Radiochemical Detection of Cancer*, S. W. Burchiel and B. A. Rhodes, eds., Masson Publishing Inc. (1982)).

In one embodiment, the invention provides a method for the specific delivery of compositions of the invention to cells by administering polypeptides of the invention (e.g., polypeptides encoded by polynucleotides of the invention and/or antibodies) that are associated with heterologous polypeptides or nucleic acids. In one example, the invention provides a method for delivering a therapeutic protein into the targeted cell. In another example, the invention provides a method for delivering a single stranded nucleic acid (e.g., antisense or ribozymes) or double stranded nucleic acid (e.g., DNA that can integrate into the cell's genome or replicate episomally and that can be transcribed) into the targeted cell.

In another embodiment, the invention provides a method for the specific destruction of cells (e.g., the destruction of tumor cells) by administering polypeptides of the invention in association with toxins or cytotoxic prodrugs.

By "toxin" is meant one or more compounds that bind and activate endogenous cytotoxic effector systems, radioisotopes, holotoxins, modified toxins, catalytic subunits of toxins, or any molecules or enzymes not normally present in or on the surface of a cell that under defined conditions cause the cell's death. Toxins that may be used according to the methods of the invention include, but are not limited to, radioisotopes known in the art, compounds such as, for example, antibodies (or complement fixing containing portions thereof) that bind an inherent or induced endogenous cytotoxic effector system, thymidine kinase, endonuclease, RNAse, alpha toxin, ricin, abrin, *Pseudomonas* exotoxin A, diphtheria toxin, saporin, momordin, gelonin, pokeweed antiviral protein, alpha-sarcin and cholera toxin. "Toxin" also includes a cytostatic or cytocidal agent, a therapeutic agent or a radioactive metal ion, e.g., alpha-emitters such as, for example, $^{213}$Bi, or other radioisotopes such as for example $^{103}$Pd, $^{133}$Xe, $^{131}$I, $^{68}$Ge, $^{57}$Co, $^{65}$Zn, $^{85}$Sr, $^{32}$P, $^{35}$S, $^{90}$Y, $^{153}$Sm, $^{153}$Gd, $^{169}$Yb, $^{51}$Cr, $^{54}$Mn, $^{75}$Se, $^{113}$Sn, $^{90}$Yttrium, $^{117}$Tin, $^{186}$Rhenium, $^{166}$Holmium, and $^{188}$Rhenium; luminescent labels, such as luminol; and fluorescent labels, such as fluorescein and rhodamine, and biotin. In a specific embodiment, the invention provides a method for the specific destruction of cells (e.g., the destruction of tumor cells) by administering polypeptides of the invention or antibodies of the invention in association with the radioisotope $^{90}$Y. In another specific embodiment, the invention provides a method for the specific destruction of cells (e.g., the destruction of tumor cells) by administering polypeptides of the invention or antibodies of the invention in association with the radioisotope $^{111}$In. In a further specific embodiment, the invention provides a method for the specific destruction of cells (e.g., the destruction of tumor cells) by administering polypeptides of the invention or antibodies of the invention in association with the radioisotope $^{131}$I.

Techniques known in the art may be applied to label polypeptides of the invention (including antibodies). Such techniques include, but are not limited to, the use of bifunctional conjugating agents (see e.g., U.S. Pat. Nos. 5,756,065;

5,714,631; 5,696,239; 5,652,361; 5,505,931; 5,489,425; 5,435,990; 5,428,139; 5,342,604; 5,274,119; 4,994,560; and 5,808,003; the contents of each of which are hereby incorporated by reference in its entirety).

Thus, the invention provides a diagnostic method of a disorder, which involves (a) assaying the expression level of a polypeptide of the present invention in cells or body fluid of an individual; and (b) comparing the assayed polypeptide expression level with a standard polypeptide expression level, whereby an increase or decrease in the assayed polypeptide expression level compared to the standard expression level is indicative of a disorder. With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Moreover, polypeptides of the present invention can be used to treat or prevent diseases or conditions such as, for example, neural disorders, immune system disorders, muscular disorders, reproductive disorders, gastrointestinal disorders, pulmonary disorders, cardiovascular disorders, renal disorders, proliferative disorders, and/or cancerous diseases and conditions. For example, patients can be administered a polypeptide of the present invention in an effort to replace absent or decreased levels of the polypeptide (e.g., insulin), to supplement absent or decreased levels of a different polypeptide (e.g., hemoglobin S for hemoglobin B, SOD, catalase, DNA repair proteins), to inhibit the activity of a polypeptide (e.g., an oncogene or tumor suppressor), to activate the activity of a polypeptide (e.g., by binding to a receptor), to reduce the activity of a membrane bound receptor by competing with it for free ligand (e.g., soluble TNF receptors used in reducing inflammation), or to bring about a desired response (e.g., blood vessel growth inhibition, enhancement of the immune response to proliferative cells or tissues).

Similarly, antibodies directed to a polypeptide of the present invention can also be used to treat disease (as described supra, and elsewhere herein). For example, administration of an antibody directed to a polypeptide of the present invention can bind, and/or neutralize the polypeptide, and/or reduce overproduction of the polypeptide. Similarly, administration of an antibody can activate the polypeptide, such as by binding to a polypeptide bound to a membrane (receptor).

At the very least, the polypeptides of the present invention can be used as molecular weight markers on SDS-PAGE gels or on molecular sieve gel filtration columns using methods well known to those of skill in the art. Polypeptides can also be used to raise antibodies, which in turn are used to measure protein expression from a recombinant cell, as a way of assessing transformation of the host cell. Moreover, the polypeptides of the present invention can be used to test the biological activities described herein.

Diagnostic Assays

The compounds of the present invention are useful for diagnosis, treatment, prevention and/or prognosis of various disorders in mammals, preferably humans. Such disorders include, but are not limited to, those described in the legends for Tables 1D, 1E.1, and 1F, and as indicated in the "Preferred Indications" columns in Table 1D, 1E.1, and 1F; and, also as described herein under the section heading "Biological Activities." Such disorders also include, but are not limited to, those related to biological activities described in Tables 1E, 1E.1, and 1E.2.

For a number of disorders, substantially altered (increased or decreased) levels of gene expression can be detected in tissues, cells or bodily fluids (e.g., sera, plasma, urine, semen, synovial fluid or spinal fluid) taken from an individual having such a disorder, relative to a "standard" gene expression level, that is, the expression level in tissues or bodily fluids from an individual not having the disorder. Thus, the invention provides a diagnostic method useful during diagnosis of a disorder, which involves measuring the expression level of the gene encoding the polypeptide in tissues, cells or body fluid from an individual and comparing the measured gene expression level with a standard gene expression level, whereby an increase or decrease in the gene expression level(s) compared to the standard is indicative of a disorder. These diagnostic assays may be performed in vivo or in vitro, such as, for example, on blood samples, biopsy tissue or autopsy tissue.

The present invention is also useful as a prognostic indicator, whereby patients exhibiting enhanced or depressed gene expression will experience a worse clinical outcome relative to patients expressing the gene at a level nearer the standard level.

In certain embodiments, a polypeptide of the invention, or polynucleotides, antibodies, agonists, or antagonists corresponding to that polypeptide, may be used to diagnose and/or prognosticate diseases and/or disorders associated with the tissue(s) in which the polypeptide of the invention is expressed, including one, two, three, four, five, or more tissues disclosed in Table 1B.2 (such as column 5) (Tissue Distribution Library Code).

By "assaying the expression level of the gene encoding the polypeptide" is intended qualitatively or quantitatively measuring or estimating the level of the polypeptide of the invention or the level of the mRNA encoding the polypeptide of the invention in a first biological sample either directly (e.g., by determining or estimating absolute protein level or mRNA level) or relatively (e.g., by comparing to the polypeptide level or mRNA level in a second biological sample). Preferably, the polypeptide expression level or mRNA level in the first biological sample is measured or estimated and compared to a standard polypeptide level or mRNA level, the standard being taken from a second biological sample obtained from an individual not having the disorder or being determined by averaging levels from a population of individuals not having the disorder. As will be appreciated in the art, once a standard polypeptide level or mRNA level is known, it can be used repeatedly as a standard for comparison.

By "biological sample" is intended any biological sample obtained from an individual, cell line, tissue culture, or other source containing polypeptides of the invention (including portions thereof) or mRNA. As indicated, biological samples include body fluids (such as sera, plasma, urine, synovial fluid and spinal fluid) and tissue sources found to express the full length or fragments thereof of a polypeptide or mRNA. Methods for obtaining tissue biopsies and body fluids from mammals are well known in the art. Where the biological sample is to include mRNA, a tissue biopsy is the preferred source.

Total cellular RNA can be isolated from a biological sample using any suitable technique such as the single-step guanidinium-thiocyanate-phenol-chloroform method described in Chomczynski and Sacchi, Anal. Biochem. 162: 156-159 (1987). Levels of mRNA encoding the polypeptides of the invention are then assayed using any appropriate method. These include Northern blot analysis, S1 nuclease mapping, the polymerase chain reaction (PCR), reverse transcription in combination with the polymerase chain reaction (RT-PCR), and reverse transcription in combination with the ligase chain reaction (RT-LCR).

The present invention also relates to diagnostic assays such as quantitative and diagnostic assays for detecting levels of polypeptides of the invention, in a biological sample (e.g., cells and tissues), including determination of normal and abnormal levels of polypeptides. Thus, for instance, a diagnostic assay in accordance with the invention for detecting over-expression of polypeptides of the invention compared to normal control tissue samples may be used to detect the presence of tumors. Assay techniques that can be used to determine levels of a polypeptide, such as a polypeptide of the present invention in a sample derived from a host are well-known to those of skill in the art. Such assay methods include radioimmunoassays, competitive-binding assays, Western Blot analysis and ELISA assays. Assaying polypeptide levels in a biological sample can occur using any art-known method.

Assaying polypeptide levels in a biological sample can occur using antibody-based techniques. For example, polypeptide expression in tissues can be studied with classical immunohistological methods (Jalkanen et al., J. Cell. Biol. 101:976-985 (1985); Jalkanen, M., et al., J. Cell. Biol. 105:3087-3096 (1987)). Other antibody-based methods useful for detecting polypeptide gene expression include immunoassays, such as the enzyme linked immunosorbent assay (ELISA) and the radioimmunoassay (RIA). Suitable antibody assay labels are known in the art and include enzyme labels, such as, glucose oxidase, and radioisotopes, such as iodine ($^{125}I$, $^{121}I$), carbon ($^{14}C$), sulfur ($^{35}S$), tritium ($^{3}H$), indium ($^{112}In$), and technetium ($^{99m}Tc$), and fluorescent labels, such as fluorescein and rhodamine, and biotin.

The tissue or cell type to be analyzed will generally include those which are known, or suspected, to express the gene of interest (such as, for example, cancer). The protein isolation methods employed herein may, for example, be such as those described in Harlow and Lane (Harlow, E. and Lane, D., 1988, "Antibodies: A Laboratory Manual", Cold Spring Harbor Laboratory Press, Cold Spring Harbor, N.Y.), which is incorporated herein by reference in its entirety. The isolated cells can be derived from cell culture or from a patient. The analysis of cells taken from culture may be a necessary step in the assessment of cells that could be used as part of a cell-based gene therapy technique or, alternatively, to test the effect of compounds on the expression of the gene.

For example, antibodies, or fragments of antibodies, such as those described herein, may be used to quantitatively or qualitatively detect the presence of gene products or conserved variants or peptide fragments thereof. This can be accomplished, for example, by immunofluorescence techniques employing a fluorescently labeled antibody coupled with light microscopic, flow cytometric, or fluorimetric detection.

In a preferred embodiment, antibodies, or fragments of antibodies directed to any one or all of the predicted epitope domains of the polypeptides of the invention (shown in Table 1B.1 such as column 7 of Table 1B.1) may be used to quantitatively or qualitatively detect the presence of gene products or conserved variants or peptide fragments thereof. This can be accomplished, for example, by immunofluorescence techniques employing a fluorescently labeled antibody coupled with light microscopic, flow cytometric, or fluorimetric detection.

In an additional preferred embodiment, antibodies, or fragments of antibodies directed to a conformational epitope of a polypeptide of the invention may be used to quantitatively or qualitatively detect the presence of gene products or conserved variants or peptide fragments thereof. This can be accomplished, for example, by immunofluorescence techniques employing a fluorescently labeled antibody coupled with light microscopic, flow cytometric, or fluorimetric detection.

The antibodies (or fragments thereof), and/or polypeptides of the present invention may, additionally, be employed histologically, as in immunofluorescence, immunoelectron microscopy or non-immunological assays, for in situ detection of gene products or conserved variants or peptide fragments thereof. In situ detection may be accomplished by removing a histological specimen from a patient, and applying thereto a labeled antibody or polypeptide of the present invention. The antibody (or fragment thereof) or polypeptide is preferably applied by overlaying the labeled antibody (or fragment) onto a biological sample. Through the use of such a procedure, it is possible to determine not only the presence of the gene product, or conserved variants or peptide fragments, or polypeptide binding, but also its distribution in the examined tissue. Using the present invention, those of ordinary skill will readily perceive that any of a wide variety of histological methods (such as staining procedures) can be modified in order to achieve such in situ detection.

Immunoassays and non-immunoassays for gene products or conserved variants or peptide fragments thereof will typically comprise incubating a sample, such as a biological fluid, a tissue extract, freshly harvested cells, or lysates of cells which have been incubated in cell culture, in the presence of a detectably labeled antibody capable of binding gene products or conserved variants or peptide fragments thereof, and detecting the bound antibody by any of a number of techniques well-known in the art.

The biological sample may be brought in contact with and immobilized onto a solid phase support or carrier such as nitrocellulose, or other solid support that is capable of immobilizing cells, cell particles or soluble proteins. The support may then be washed with suitable buffers followed by treatment with the detectably labeled antibody or detectable polypeptide of the invention. The solid phase support may then be washed with the buffer a second time to remove unbound antibody or polypeptide. Optionally the antibody is subsequently labeled. The amount of bound label on solid support may then be detected by conventional means.

By "solid phase support or carrier" is intended any support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

The binding activity of a given lot of antibody or antigen polypeptide may be determined according to well known methods. Those skilled in the art will be able to determine operative and optimal assay conditions for each determination by employing routine experimentation.

In addition to assaying polypeptide levels or polynucleotide levels in a biological sample obtained from an individual, polypeptide or polynucleotide can also be detected in vivo by imaging. For example, in one embodiment of the invention, polypeptides and/or antibodies of the invention are used to image diseased cells, such as neoplasms. In another embodiment, polynucleotides of the invention (e.g., polynucleotides complementary to all or a portion of an mRNA) and/or antibodies (e.g., antibodies directed to any one or a combination of the epitopes of a polypeptide of the invention, antibodies directed to a conformational epitope of a polypeptide of the invention, or antibodies directed to the full length polypeptide expressed on the cell surface of a mammalian cell) are used to image diseased or neoplastic cells.

Antibody labels or markers for in vivo imaging of polypeptides of the invention include those detectable by X-radiography, NMR, MRI, CAT-scans or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which may be incorporated into the antibody by labeling of nutrients for the relevant hybridoma. Where in vivo imaging is used to detect enhanced levels of polypeptides for diagnosis in humans, it may be preferable to use human antibodies or "humanized" chimeric monoclonal antibodies. Such antibodies can be produced using techniques described herein or otherwise known in the art. For example methods for producing chimeric antibodies are known in the art. See, for review, Morrison, *Science* 229:1202 (1985); Oi et al., *BioTechniques* 4:214 (1986); Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., *Nature* 312:643 (1984); Neuberger et al., *Nature* 314:268 (1985).

Additionally, any polypeptides of the invention whose presence can be detected, can be administered. For example, polypeptides of the invention labeled with a radio-opaque or other appropriate compound can be administered and visualized in vivo, as discussed, above for labeled antibodies. Further, such polypeptides can be utilized for in vitro diagnostic procedures.

A polypeptide-specific antibody or antibody fragment that has been labeled with an appropriate detectable imaging moiety, such as a radioisotope (for example, $^{131}I$, $^{112}In$, $^{99m}Tc$), a radio-opaque substance, or a material detectable by nuclear magnetic resonance, is introduced (for example, parenterally, subcutaneously or intraperitoneally) into the mammal to be examined for a disorder. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99m}Tc$. The labeled antibody or antibody fragment will then preferentially accumulate at the location of cells which contain the antigenic protein. In vivo tumor imaging is described in S. W. Burchiel et al., "Immunopharmacokinetics of Radiolabeled Antibodies and Their Fragments" (Chapter 13 in *Tumor Imaging: The Radiochemical Detection of Cancer*, S. W. Burchiel and B. A. Rhodes, eds., Masson Publishing Inc. (1982)).

With respect to antibodies, one of the ways in which an antibody of the present invention can be detectably labeled is by linking the same to a reporter enzyme and using the linked product in an enzyme immunoassay (EIA) (Voller, A., "The Enzyme Linked Immunosorbent Assay (ELISA)", 1978, Diagnostic Horizons 2:1-7, Microbiological Associates Quarterly Publication, Walkersville, Md.); Voller et al., *J. Clin. Pathol.* 31:507-520 (1978); Butler, J. E., *Meth. Enzymol.* 73:482-523 (1981); Maggio, E. (ed.), 1980, Enzyme Immunoassay, CRC Press, Boca Raton, Fla.; Ishikawa, E. et al., (eds.), 1981, Enzyme Immunoassay, Kgaku Shoin, Tokyo). The reporter enzyme which is bound to the antibody will react with an appropriate substrate, preferably a chromogenic substrate, in such a manner as to produce a chemical moiety which can be detected, for example, by spectrophotometric, fluorimetric or by visual means. Reporter enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. Additionally, the detection can be accomplished by colorimetric methods which employ a chromogenic substrate for the reporter enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the antibodies or antibody fragments, it is possible to detect polypeptides through the use of a radioimmunoassay (RIA) (see, for example, Weintraub, B., Principles of Radioimmunoassays, Seventh Training Course on Radioligand Assay Techniques, The Endocrine Society, March, 1986, which is incorporated by reference herein). The radioactive isotope can be detected by means including, but not limited to, a gamma counter, a scintillation counter, or autoradiography.

It is also possible to label the antibody with a fluorescent compound. When the fluorescently labeled antibody is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin, ophthaldehyde and fluorescamine.

The antibody can also be detectably labeled using fluorescence emitting metals such as $^{152}Eu$, or others of the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in, which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

Methods for Detecting Diseases

In general, a disease may be detected in a patient based on the presence of one or more proteins of the invention and/or polynucleotides encoding such proteins in a biological sample (for example, blood, sera, urine, and/or tumor biopsies) obtained from the patient. In other words, such proteins may be used as markers to indicate the presence or absence of a disease or disorder, including cancer and/or as described elsewhere herein. In addition, such proteins may be useful for the detection of other diseases and cancers. The binding agents provided herein generally permit detection of the level of antigen that binds to the agent in the biological sample. Polynucleotide primers and probes may be used to detect the level of mRNA encoding polypeptides of the invention, which is also indicative of the presence or absence of a disease or disorder, including cancer. In general, polypeptides of the invention should be present at a level that is at least three fold higher in diseased tissue than in normal tissue.

There are a variety of assay formats known to those of ordinary skill in the art for using a binding agent to detect polypeptide markers in a sample. See, e.g., Harlow and Lane, supra. In general, the presence or absence of a disease in a patient may be determined by (a) contacting a biological sample obtained from a patient with a binding agent; (b) detecting in the sample a level of polypeptide that binds to the binding agent; and (c) comparing the level of polypeptide with a predetermined cut-off value.

In a preferred embodiment, the assay involves the use of a binding agent(s) immobilized on a solid support to bind to and remove the polypeptide of the invention from the remainder of the sample. The bound polypeptide may then be detected using a detection reagent that contains a reporter group and specifically binds to the binding agent/polypeptide complex. Such detection reagents may comprise, for example, a binding agent that specifically binds to the polypeptide or an antibody or other agent that specifically binds to the binding agent, such as an anti-immunoglobulin, protein G, protein A or a lectin. Alternatively, a competitive assay may be utilized, in which a polypeptide is labeled with a reporter group and allowed to bind to the immobilized binding agent after incubation of the binding agent with the sample. The extent to which components of the sample inhibit the binding of the labeled polypeptide to the binding agent is indicative of the reactivity of the sample with the immobilized binding agent. Suitable polypeptides for use within such assays include polypeptides of the invention and portions thereof, or antibodies, to which the binding agent binds, as described above.

The solid support may be any material known to those of skill in the art to which polypeptides of the invention may be attached. For example, the solid support may be a test well in a microtiter plate or a nitrocellulose or other suitable membrane. Alternatively, the support may be a bead or disc, such as glass fiberglass, latex or a plastic material such as polystyrene or polyvinylchloride. The support may also be a magnetic particle or a fiber optic sensor, such as those disclosed, for example, in U.S. Pat. No. 5,359,681. The binding agent may be immobilized on the solid support using a variety of techniques known to those of skill in the art, which are amply described in the patent and scientific literature. In the context of the present invention, the term "immobilization" refers to both noncovalent association, such as adsorption, and covalent attachment (which may be a direct linkage between the agent and functional groups on the support or may be a linkage by way of a cross-linking agent). Immobilization by adsorption to a well in a microtiter plate or to a membrane is preferred. In such cases, adsorption may be achieved by contacting the binding agent, in a suitable buffer, with the solid support for the suitable amount of time. The contact time varies with temperature, but is typically between about 1 hour and about 1 day. In general, contacting a well of plastic microtiter plate (such as polystyrene or polyvinylchloride) with an amount of binding agent ranging from about 10 ng to about 10 μg, and preferably about 100 ng to about 1 μg, is sufficient to immobilize an adequate amount of binding agent.

Covalent attachment of binding agent to a solid support may generally be achieved by first reacting the support with a bifunctional reagent that will react with both the support and a functional group, such as a hydroxyl or amino group, on the binding agent. For example, the binding agent may be covalently attached to supports having an appropriate polymer coating using benzoquinone or by condensation of an aldehyde group on the support with an amine and an active hydrogen on the binding partner (see, e.g., Pierce Immunotechnology Catalog and Handbook, 1991, at A12-A13).

Gene Therapy Methods

Also encompassed by the invention are gene therapy methods for treating or preventing disorders, diseases and conditions. The gene therapy methods relate to the introduction of nucleic acid (DNA, RNA and antisense DNA or RNA) sequences into an animal to achieve expression of the polypeptide of the present invention. This method requires a polynucleotide which codes for a polypeptide of the present invention operatively linked to a promoter and any other genetic elements necessary for the expression of the polypeptide by the target tissue. Such gene therapy and delivery techniques are known in the art, see, for example, WO90/11092, which is herein incorporated by reference.

Thus, for example, cells from a patient may be engineered with a polynucleotide (DNA or RNA) comprising a promoter operably linked to a polynucleotide of the present invention ex vivo, with the engineered cells then being provided to a patient to be treated with the polypeptide of the present invention. Such methods are well-known in the art. For example, see Belldegrun, A., et al., J. Natl. Cancer Inst. 85: 207-216 (1993); Ferrantini, M. et al., Cancer Research 53: 1107-1112 (1993); Ferrantini, M. et al., J. Immunology 153: 4604-4615 (1994); Kaido, T., et al., Int. J. Cancer 60: 221-229 (1995); Ogura, H., et al., Cancer Research 50: 5102-5106 (1990); Santodonato, L., et al., Human Gene Therapy 7:1-10 (1996); Santodonato, L., et al., Gene Therapy 4:1246-1255 (1997); and Zhang, J.-F. et al., Cancer Gene Therapy 3: 31-38 (1996)), which are herein incorporated by reference. In one embodiment, the cells which are engineered are arterial cells. The arterial cells may be reintroduced into the patient through direct injection to the artery, the tissues surrounding the artery, or through catheter injection.

As discussed in more detail below, the polynucleotide constructs can be delivered by any method that delivers injectable materials to the cells of an animal, such as, injection into the interstitial space of tissues (heart, muscle, skin, lung, liver, and the like). The polynucleotide constructs may be delivered in a pharmaceutically acceptable liquid or aqueous carrier.

In one embodiment, the polynucleotide of the present invention is delivered as a naked polynucleotide. The term "naked" polynucleotide, DNA or RNA refers to sequences that are free from any delivery vehicle that acts to assist, promote or facilitate entry into the cell, including viral sequences, viral particles, liposome formulations, LIPOFECTIN™ or precipitating agents and the like. However, the polynucleotide of the present invention can also be delivered in liposome formulations and LIPOFECTIN™ formulations and the like can be prepared by methods well known to those skilled in the art. Such methods are described, for example, in U.S. Pat. Nos. 5,593,972, 5,589,466, and 5,580,859, which are herein incorporated by reference.

The polynucleotide vector constructs used in the gene therapy method are preferably constructs that will not integrate into the host genome nor will they contain sequences that allow for replication. Appropriate vectors include pWL-NEO, pSV2CAT, pOG44, pXT1 and pSG available from STRATAGENE™; pSVK3, pBPV, pMSG and pSVL available from PHARMACIA™; and pEF1/V5, pcDNA3.1, and pRc/CMV2 available from Invitrogen. Other suitable vectors will be readily apparent to the skilled artisan.

Any strong promoter known to those skilled in the art can be used for driving the expression of the polynucleotide sequence. Suitable promoters include adenoviral promoters, such as the adenoviral major late promoter; or heterologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs; the b-actin promoter; and human growth hormone promoters. The promoter also may be the native promoter for the polynucleotide of the present invention.

Unlike other gene therapy techniques, one major advantage of introducing naked nucleic acid sequences into target cells is the transitory nature of the polynucleotide synthesis in the cells. Studies have shown that non-replicating DNA sequences can be introduced into cells to provide production of the desired polypeptide for periods of up to six months.

The polynucleotide construct can be delivered to the interstitial space of tissues within the an animal, including of muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, and connective tissue. Interstitial space of the tissues comprises the intercellular, fluid, mucopolysaccharide matrix among the reticular fibers of organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation and the lymph fluid of the lymphatic channels. Delivery to the interstitial space of muscle tissue is preferred for the reasons discussed below. They may be conveniently delivered by injection into the tissues comprising these cells. They are preferably delivered to and expressed in persistent, non-dividing cells which are differentiated, although delivery and expression may be achieved in non-differentiated or less completely differentiated cells, such as, for example, stem cells of blood or skin fibroblasts. In vivo muscle cells are particularly competent in their ability to take up and express polynucleotides.

For the naked nucleic acid sequence injection, an effective dosage amount of DNA or RNA will be in the range of from about 0.05 mg/kg body weight to about 50 mg/kg body weight. Preferably the dosage will be from about 0.005 mg/kg to about 20 mg/kg and more preferably from about 0.05 mg/kg to about 5 mg/kg. Of course, as the artisan of ordinary skill will appreciate, this dosage will vary according to the tissue site of injection. The appropriate and effective dosage of nucleic acid sequence can readily be determined by those of ordinary skill in the art and may depend on the condition being treated and the route of administration.

The preferred route of administration is by the parenteral route of injection into the interstitial space of tissues. However, other parenteral routes may also be used, such as, inhalation of an aerosol formulation particularly for delivery to lungs or bronchial tissues, throat or mucous membranes of the nose. In addition, naked DNA constructs can be delivered to arteries during angioplasty by the catheter used in the procedure.

The naked polynucleotides are delivered by any method known in the art, including, but not limited to, direct needle injection at the delivery site, intravenous injection, topical administration, catheter infusion, and so-called "gene guns". These delivery methods are known in the art.

The constructs may also be delivered with delivery vehicles such as viral sequences, viral particles, liposome formulations, LIPOFECTIN™, precipitating agents, etc. Such methods of delivery are known in the art.

In certain embodiments, the polynucleotide constructs are complexed in a liposome preparation. Liposomal preparations for use in the instant invention include cationic (positively charged), anionic (negatively charged) and neutral preparations. However, cationic liposomes are particularly preferred because a tight charge complex can be formed between the cationic liposome and the polyanionic nucleic acid. Cationic liposomes have been shown to mediate intracellular delivery of plasmid DNA (Felgner et al., Proc. Natl. Acad. Sci. USA (1987) 84:7413-7416, which is herein incorporated by reference); mRNA (Malone et al., Proc. Natl. Acad. Sci. USA (1989) 86:6077-6081, which is herein incorporated by reference); and purified transcription factors (Debs et al., J. Biol. Chem. (1990) 265:10189-10192, which is herein incorporated by reference), in functional form.

Cationic liposomes are readily available. For example, N[1-2,3-dioleyloxy)propyl]-N,N,N-triethylammonium (DOTMA) liposomes are particularly useful and are available under the trademark LIPOFECTIN™, from GIBCO BRL, Grand Island, N.Y. (See, also, Felgner et al., Proc. Natl. Acad. Sci. USA (1987) 84:7413-7416, which is herein incorporated by reference). Other commercially available liposomes include transfectace (DDAB/DOPE) and DOTAP/DOPE (BOEHRINGER™).

Other cationic liposomes can be prepared from readily available materials using techniques well known in the art. See, e.g. PCT Publication No. WO 90/11092 (which is herein incorporated by reference) for a description of the synthesis of DOTAP (1,2-bis(oleoyloxy)-3-(trimethylammonio)propane) liposomes. Preparation of DOTMA liposomes is explained in the literature, see, e.g., P. Felgner et al., Proc. Natl. Acad. Sci. USA 84:7413-7417, which is herein incorporated by reference. Similar methods can be used to prepare liposomes from other cationic lipid materials.

Similarly, anionic and neutral liposomes are readily available, such as from Avanti Polar Lipids (Birmingham, Ala.), or can be easily prepared using readily available materials. Such materials include phosphatidyl, choline, cholesterol, phosphatidyl ethanolamine, dioleoylphosphatidyl choline (DOPC), dioleoylphosphatidyl glycerol (DOPG), dioleoylphosphatidyl ethanolamine (DOPE), among others. These materials can also be mixed with the DOTMA and DOTAP starting materials in appropriate ratios. Methods for making liposomes using these materials are well known in the art.

For example, commercially dioleoylphosphatidyl choline (DOPC), dioleoylphosphatidyl glycerol (DOPG), and dioleoylphosphatidyl ethanolamine (DOPE) can be used in various combinations to make conventional liposomes, with or without the addition of cholesterol. Thus, for example, DOPG/DOPC vesicles can be prepared by drying 50 mg each of DOPG and DOPC under a stream of nitrogen gas into a sonication vial. The sample is placed under a vacuum pump overnight and is hydrated the following day with deionized water. The sample is then sonicated for 2 hours in a capped vial, using a Heat Systems model 350 sonicator equipped with an inverted cup (bath type) probe at the maximum setting while the bath is circulated at 15EC. Alternatively, negatively charged vesicles can be prepared without sonication to produce multilamellar vesicles or by extrusion through nucleopore membranes to produce unilamellar vesicles of discrete size. Other methods are known and available to those of skill in the art.

The liposomes can comprise multilamellar vesicles (MLVs), small unilamellar vesicles (SUVs), or large unilamellar vesicles (LUVs), with SUVs being preferred. The various liposome-nucleic acid complexes are prepared using methods well known in the art. See, e.g., Straubinger et al., Methods of Immunology (1983), 101:512-527, which is herein incorporated by reference. For example, MLVs containing nucleic acid can be prepared by depositing a thin film of phospholipid on the walls of a glass tube and subsequently hydrating with a solution of the material to be encapsulated. SUVs are prepared by extended sonication of MLVs to produce a homogeneous population of unilamellar liposomes. The material to be entrapped is added to a suspension of preformed MLVs and then sonicated. When using liposomes containing cationic lipids, the dried lipid film is resuspended in an appropriate solution such as sterile water or an isotonic buffer solution such as 10 mM Tris/NaCl, sonicated, and then the preformed liposomes are mixed directly with the DNA. The liposome and DNA form a very stable complex due to binding of the positively charged liposomes to the cationic DNA. SUVs find use with small nucleic acid fragments. LUVs are prepared by a number of methods, well known in the art. Commonly used methods include $Ca^{2+}$-EDTA chelation (Papahadjopoulos et al., Biochim. Biophys. Acta (1975) 394:483; Wilson et al., Cell 17:77 (1979)); ether injection (Deamer, D. and Bangham, A., Biochim. Biophys. Acta 443: 629 (1976); Ostro et al., Biochem. Biophys. Res. Commun. 76:836 (1977); Fraley et al., Proc. Natl. Acad. Sci. USA 76:3348 (1979)); detergent dialysis (Enoch, H. and Strittmatter, P., Proc. Natl. Acad. Sci. USA 76:145 (1979)); and reverse-phase evaporation (REV) (Fraley et al., J. Biol. Chem. 255:10431 (1980); Szoka, F. and Papahadjopoulos, D., Proc. Natl. Acad. Sci. USA 75:145 (1978); Schaefer-Ridder et al., Science 215:166 (1982)), which are herein incorporated by reference.

Generally, the ratio of DNA to liposomes will be from about 10:1 to about 1:10. Preferably, the ration will be from about 5:1 to about 1:5. More preferably, the ration will be about 3:1 to about 1:3. Still more preferably, the ratio will be about 1:1.

U.S. Pat. No. 5,676,954 (which is herein incorporated by reference) reports on the injection of genetic material, complexed with cationic liposomes carriers, into mice. U.S. Pat. Nos. 4,897,355, 4,946,787, 5,049,386, 5,459,127, 5,589,466, 5,693,622, 5,580,859, 5,703,055, and international publication no. WO 94/9469 (which are herein incorporated by reference) provide cationic lipids for use in transfecting DNA into cells and mammals. U.S. Pat. Nos. 5,589,466, 5,693,622, 5,580,859, 5,703,055, and international publication no. WO 94/9469 provide methods for delivering DNA-cationic lipid complexes to mammals.

In certain embodiments, cells are engineered, ex vivo or in vivo, using a retroviral particle containing RNA which comprises a sequence encoding a polypeptide of the present invention. Retroviruses from which the retroviral plasmid vectors may be derived include, but are not limited to, Moloney Murine Leukemia Virus, spleen necrosis virus, Rous sarcoma Virus, Harvey Sarcoma Virus, avian leukosis virus, gibbon ape leukemia virus, human immunodeficiency virus, Myeloproliferative Sarcoma Virus, and mammary tumor virus.

The retroviral plasmid vector is employed to transduce packaging cell lines to form producer cell lines. Examples of packaging cells which may be transfected include, but are not limited to, the PE501, PA317, R-2, R-AM, PA12, T19-14X, VT-19-17-H2, RCRE, RCRIP, GP+E-86, GP+envAm12, and DAN cell lines as described in Miller, Human Gene Therapy 1:5-14 (1990), which is incorporated herein by reference in its entirety. The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line generates infectious retroviral vector particles which include polynucleotide encoding a polypeptide of the present invention. Such retroviral vector particles then may be employed, to transduce eukaryotic cells, either in vitro or in vivo. The transduced eukaryotic cells will express a polypeptide of the present invention.

In certain other embodiments, cells are engineered, ex vivo or in vivo, with polynucleotide contained in an adenovirus vector. Adenovirus can be manipulated such that it encodes and expresses a polypeptide of the present invention, and at the same time is inactivated in terms of its ability to replicate in a normal lytic viral life cycle. Adenovirus expression is achieved without integration of the viral DNA into the host cell chromosome, thereby alleviating concerns about insertional mutagenesis. Furthermore, adenoviruses have been used as live enteric vaccines for many years with an excellent safety profile (Schwartz et al. Am. Rev. Respir. Dis. 109:233-238 (1974)). Finally, adenovirus mediated gene transfer has been demonstrated in a number of instances including transfer of alpha-1-antitrypsin and CFTR to the lungs of cotton rats (Rosenfeld, M. A. et al. (1991) Science 252:431-434; Rosenfeld et al., (1992) Cell 68:143-155). Furthermore, extensive studies to attempt to establish adenovirus as a causative agent in human cancer were uniformly negative (Green, M. et al. (1979) Proc. Natl. Acad. Sci. USA 76:6606).

Suitable adenoviral vectors useful in the present invention are described, for example, in Kozarsky and Wilson, Curr. Opin. Genet. Devel. 3:499-503 (1993); Rosenfeld et al., Cell 68:143-155 (1992); Engelhardt et al., Human Genet. Ther. 4:759-769 (1993); Yang et al., Nature Genet. 7:362-369 (1994); Wilson et al., Nature 365:691-692 (1993); and U.S. Pat. No. 5,652,224, which are herein incorporated by reference. For example, the adenovirus vector Ad2 is useful and can be grown in human 293 cells. These cells contain the E1 region of adenovirus and constitutively express E1a and E1b, which complement the defective adenoviruses by providing the products of the genes deleted from the vector. In addition to Ad2, other varieties of adenovirus (e.g., Ad3, Ad5, and Ad7) are also useful in the present invention.

Preferably, the adenoviruses used in the present invention are replication deficient. Replication deficient adenoviruses require the aid of a helper virus and/or packaging cell line to form infectious particles. The resulting virus is capable of infecting cells and can express a polynucleotide of interest that is operably linked to a promoter, but cannot replicate in most cells. Replication deficient adenoviruses may be deleted in one or more of all or a portion of the following genes: E1a, E1b, E3, E4, E2a, or L1 through L5.

In certain other embodiments, the cells are engineered, ex vivo or in vivo, using an adeno-associated virus (AAV). AAVs are naturally occurring defective viruses that require helper viruses to produce infectious particles (Muzyczka, N., Curr. Topics in Microbiol. Immunol. 158:97 (1992)). It is also one of the few viruses that may integrate its DNA into non-dividing cells. Vectors containing as little as 300 base pairs of AAV can be packaged and can integrate, but space for exogenous DNA is limited to about 4.5 kb. Methods for producing and using such AAVs are known in the art. See, for example, U.S. Pat. Nos. 5,139,941, 5,173,414, 5,354,678, 5,436,146, 5,474,935, 5,478,745, and 5,589,377.

For example, an appropriate AAV vector for use in the present invention will include all the sequences necessary for DNA replication, encapsidation, and host-cell integration. The polynucleotide construct is inserted into the AAV vector using standard cloning methods, such as those found in Sambrook et al., Molecular Cloning: A Laboratory Manual, Cold Spring Harbor Press (1989). The recombinant AAV vector is then transfected into packaging cells which are infected with a helper virus, using any standard technique, including lipofection, electroporation, calcium phosphate precipitation, etc. Appropriate helper viruses include adenoviruses, cytomegaloviruses, vaccinia viruses, or herpes viruses. Once the packaging cells are transfected and infected, they will produce infectious AAV viral particles which contain the polynucleotide construct. These viral particles are then used to transduce eukaryotic cells, either ex vivo or in vivo. The transduced cells will contain the polynucleotide construct integrated into its genome, and will express a polypeptide of the invention.

Another method of gene therapy involves operably associating heterologous control regions and endogenous polynucleotide sequences (e.g. encoding a polypeptide of the present invention) via homologous recombination (see, e.g., U.S. Pat. No. 5,641,670, issued Jun. 24, 1997; International Publication No. WO 96/29411, published Sep. 26, 1996; International Publication No. WO 94/12650, published Aug. 4, 1994; Koller et al., Proc. Natl. Acad. Sci. USA 86:8932-8935 (1989); and Zijlstra et al., Nature 342:435-438 (1989), which are herein incorporated by reference. This method involves the activation of a gene which is present in the target cells, but which is not normally expressed in the cells, or is expressed at a lower level than desired.

Polynucleotide constructs are made, using standard techniques known in the art, which contain the promoter with targeting sequences flanking the promoter. Suitable promoters are described herein. The targeting sequence is sufficiently complementary to an endogenous sequence to permit homologous recombination of the promoter-targeting sequence with the endogenous sequence. The targeting sequence will be sufficiently near the 5' end of the desired endogenous polynucleotide sequence so the promoter will be operably linked to the endogenous sequence upon homologous recombination.

The promoter and the targeting sequences can be amplified using PCR. Preferably, the amplified promoter contains distinct restriction enzyme sites on the 5' and 3' ends. Preferably, the 3' end of the first targeting sequence contains the same restriction enzyme site as the 5' end of the amplified promoter and the 5' end of the second targeting sequence contains the same restriction site as the 3' end of the amplified promoter. The amplified promoter and targeting sequences are digested and ligated together.

The promoter-targeting sequence construct is delivered to the cells, either as naked polynucleotide, or in conjunction with transfection-facilitating agents, such as liposomes, viral sequences, viral particles, whole viruses, lipofection, precipitating agents, etc., described in more detail above. The P promoter-targeting sequence can be delivered by any method, included direct needle injection, intravenous injection, topical administration, catheter infusion, particle accelerators, etc. The methods are described in more detail below.

The promoter-targeting sequence construct is taken up by cells. Homologous recombination between the construct and the endogenous sequence takes place, such that an endogenous sequence is placed under the control of the promoter. The promoter then drives the expression of the endogenous sequence.

The polynucleotide encoding a polypeptide of the present invention may contain a secretory signal sequence that facilitates secretion of the protein. Typically, the signal sequence is positioned in the coding region of the polynucleotide to be expressed towards or at the 5' end of the coding region. The signal sequence may be homologous or heterologous to the polynucleotide of interest and may be homologous or heterologous to the cells to be transfected. Additionally, the signal sequence may be chemically synthesized using methods known in the art.

Any mode of administration of any of the above-described polynucleotides constructs can be used so long as the mode results in the expression of one or more molecules in an amount sufficient to provide a therapeutic effect. This includes direct needle injection, systemic injection, catheter infusion, BIOLISTIC™ injectors, particle accelerators (i.e., “gene guns”), gelfoam sponge depots, other commercially available depot materials, osmotic pumps (e.g., Alza minipumps), oral or suppositorial solid (tablet or pill) pharmaceutical formulations, and decanting or topical applications during surgery. For example, direct injection of naked calcium phosphate-precipitated plasmid into rat liver and rat spleen or a protein-coated plasmid into the portal vein has resulted in gene expression of the foreign gene in the rat livers (Kaneda et al., Science 243:375 (1989)).

A preferred method of local administration is by direct injection. Preferably, a recombinant molecule of the present invention complexed with a delivery vehicle is administered by direct injection into or locally within the area of arteries. Administration of a composition locally within the area of arteries refers to injecting the composition centimeters and preferably, millimeters within arteries.

Another method of local administration is to contact a polynucleotide construct of the present invention in or around a surgical wound. For example, a patient can undergo surgery and the polynucleotide construct can be coated on the surface of tissue inside the wound or the construct can be injected into areas of tissue inside the wound.

Therapeutic compositions useful in systemic administration include recombinant molecules of the present invention complexed to a targeted delivery vehicle of the present invention. Suitable delivery vehicles for use with systemic administration comprise liposomes comprising ligands for targeting the vehicle to a particular site. In specific embodiments, suitable delivery vehicles for use with systemic administration comprise liposomes comprising polypeptides of the invention for targeting the vehicle to a particular site.

Preferred methods of systemic administration, include intravenous injection, aerosol, oral and percutaneous (topical) delivery. Intravenous injections can be performed using methods standard in the art. Aerosol delivery can also be performed using methods standard in the art (see, for example, Stribling et al., Proc. Natl. Acad. Sci. USA 189: 11277-11281, 1992, which is incorporated herein by reference). Oral delivery can be performed by complexing a polynucleotide construct of the present invention to a carrier capable of withstanding degradation by digestive enzymes in the gut of an animal. Examples of such carriers, include plastic capsules or tablets, such as those known in the art. Topical delivery can be performed by mixing a polynucleotide construct of the present invention with a lipophilic reagent (e.g., DMSO) that is capable of passing into the skin.

Determining an effective amount of substance to be delivered can depend upon a number of factors including, for example, the chemical structure and biological activity of the substance, the age and weight of the animal, the precise condition requiring treatment and its severity, and the route of administration. The frequency of treatments depends upon a number of factors, such as the amount of polynucleotide constructs administered per dose, as well as the health and history of the subject. The precise amount, number of doses, and timing of doses will be determined by the attending physician or veterinarian.

Therapeutic compositions of the present invention can be administered to any animal, preferably to mammals and birds. Preferred mammals include humans, dogs, cats, mice, rats, rabbits, sheep, cattle, horses and pigs, with humans being particularly preferred.

Biological Activities

Polynucleotides or polypeptides, or agonists or antagonists of the present invention, can be used in assays to test for one or more biological activities. If these polynucleotides or polypeptides, or agonists or antagonists of the present invention, do exhibit activity in a particular assay, it is likely that these molecules may be involved in the diseases associated with the biological activity. Thus, the polynucleotides and polypeptides, and agonists or antagonists could be used to treat the associated disease.

Members of the secreted family of proteins are believed to be involved in biological activities associated with, for example, cellular signaling. Accordingly, compositions of the invention (including polynucleotides, polypeptides and antibodies of the invention, and fragments and variants thereof) may be used in diagnosis, prognosis, prevention and/or treatment of diseases and/or disorders associated with aberrant activity of secreted polypeptides.

In preferred embodiments, compositions of the invention (including polynucleotides, polypeptides and antibodies of the invention, and fragments and variants thereof) may be used in the diagnosis, prognosis, prevention, treatment, and/or amelioration of diseases and/or disorders relating to the endocrine system, the nervous system (See, for example, "Neurological Disorders" section below), the immune system (See, for example, "Immune Activity" section below), the gastrointestinal system (e.g., Crohn's disease, pancreatitis, gallstones, antibiotic-associated colitis, duodenitis, gastrointestinal neoplasms, and as described in the "Gastrointestinal Disorders" section below), or the cardiovascular system (e.g., atherosclerosis, stroke, myocardial infarction, hypertension, and as described in the "Cardiovascular Disorders" section below). In preferred embodiments, compositions of the invention (including polynucleotides, polypeptides and antibodies of the invention, and fragments and variants thereof) may be used in the diagnosis, prognosis, prevention, treatment, and/or amelioration of cancer and other hyperproliferative diseases and/or disorders (e.g., as described in the "Hyperproliferative Disorders").

In certain embodiments, a polypeptide of the invention, or polynucleotides, antibodies, agonists, or antagonists corresponding to that polypeptide, may be used to diagnose and/or prognosticate diseases and/or disorders associated with the tissue(s) in which the polypeptide of the invention is expressed including one, two, three, four, five, or more tissues disclosed in Table 1B.2 (such as column 5) (Tissue Distribution Library Code).

Thus, polynucleotides, translation products and antibodies of the invention are useful in the diagnosis, detection, prevention, prognostication, and/or treatment of diseases and/or disorders associated with activities that include, but are not limited to, prohormone activation, neurotransmitter activity, cellular signaling, cellular proliferation, cellular differentiation, and cell migration.

More generally, polynucleotides, translation products and antibodies corresponding to this gene may be useful for the diagnosis, prognosis, prevention, treatment and/or amelioration of diseases and/or disorders associated with the following system or systems.

Immune Activity

Polynucleotides, polypeptides, antibodies, and/or agonists or antagonists of the present invention may be useful in preventing, diagnosing, prognosticating, treating, and/or ameliorating diseases, disorders, and/or conditions of the immune system, by, for example, activating or inhibiting the proliferation, differentiation, or mobilization (chemotaxis) of immune cells. Immune cells develop through a process called hematopoiesis, producing myeloid (platelets, red blood cells, neutrophils, and macrophages) and lymphoid (B and T lymphocytes) cells from pluripotent stem cells. The etiology of these immune diseases, disorders, and/or conditions may be genetic, somatic, such as cancer and some autoimmune diseases, acquired (e.g., by chemotherapy or toxins), or infectious. Moreover, polynucleotides, polypeptides, antibodies, and/or agonists or antagonists of the present invention can be used as a marker or detector of a particular immune system disease or disorder.

In another embodiment, a polypeptide of the invention, or polynucleotides, antibodies, agonists, or antagonists corresponding to that polypeptide, may be used to treat diseases and disorders of the immune system and/or to inhibit or enhance an immune response generated by cells associated with the tissue(s) in which the polypeptide of the invention is expressed, including one, two, three, four, five, or more tissues disclosed in Table 1B.2, column 5 (Tissue Distribution Library Code).

Polynucleotides, polypeptides, antibodies, and/or agonists or antagonists of the present invention may be useful in treating or detecting deficiencies or disorders of hematopoietic cells. Polynucleotides or polypeptides, or agonists or antagonists of the present invention could be used to increase differentiation and proliferation of hematopoietic cells, including the pluripotent stem cells, in an effort to treat and/or prevent those diseases, disorders, and/or conditions associated with a decrease in certain (or many) types hematopoietic cells.

Polynucleotides, polypeptides, antibodies, and/or agonists or antagonists of the present invention may be useful in preventing, diagnosing, prognosticating, treating and/or ameliorating immunodeficiencies, including both congenital and acquired immunodeficiencies. Examples of immunologic deficiency syndromes include, but are not limited to: blood protein disorders, ataxia telangiectasia, Digeorge Syndrome, severe combined immunodeficiency (SCIDs), Wiskott-Aldrich Disorder, anemia, thrombocytopenia, or hemoglobinuria. Examples of B cell immunodeficiencies in which immunoglobulin levels B cell function and/or B cell numbers are decreased include: X-linked agammaglobulinemia (Bruton's disease), X-linked infantile agammaglobulinemia, X-linked immunodeficiency with hyper IgM, non X-linked immunodeficiency with hyper IgM, X-linked lymphoproliferative syndrome (XLP), agammaglobulinemia including congenital and acquired agammaglobulinemia, adult onset agammaglobulinemia, late-onset agammaglobulinemia, dysgammaglobulinemia, hypogammaglobulinemia, unspecified hypogammaglobulinemia, recessive agammaglobulinemia (Swiss type), Selective IgM deficiency, selective IgA deficiency, selective IgG subclass deficiencies, IgG subclass deficiency (with or without IgA deficiency), Ig deficiency with increased IgM, IgG and IgA deficiency with increased IgM, antibody deficiency with normal or elevated Igs, Ig heavy chain deletions, kappa chain deficiency, B cell lymphoproliferative disorder (BLPD), common variable immunodeficiency (CVID), common variable immunodeficiency (CVI) (acquired), and transient hypogammaglobulinemia of infancy.

In specific embodiments, ataxia-telangiectasia or conditions associated with ataxia-telangiectasia are detected, prevented, diagnosed, prognosticated, treated, and/or ameliorated using the polypeptides or polynucleotides of the invention, and/or agonists or antagonists thereof.

Examples of congenital immunodeficiencies in which T cell and/or B cell function and/or number is decreased include, but are not limited to: DiGeorge anomaly, severe combined immunodeficiencies (SCID) (including, but not limited to, X-linked SCID, autosomal recessive SCID, adenosine deaminase deficiency, purine nucleoside phosphorylase (PNP) deficiency, Class II MHC deficiency (Bare lymphocyte syndrome), Wiskott-Aldrich syndrome, and ataxia telangiectasia), thymic hypoplasia, third and fourth pharyngeal pouch syndrome, 22q11.2 deletion, chronic mucocutaneous candidiasis, natural killer cell deficiency (NK), idiopathic CD4+ T-lymphocytopenia, immunodeficiency with predominant T cell defect (unspecified), and unspecified immunodeficiency of cell mediated immunity.

In specific embodiments, DiGeorge anomaly or conditions associated with DiGeorge anomaly are prevented, detected, diagnosed, prognosticated, treated and/or ameliorated using polypeptides or polynucleotides of the invention, or antagonists or agonists thereof.

Other immunodeficiencies that may be prevented, detected, diagnosed, prognosticated, treated and/or ameliorated using polypeptides or polynucleotides of the invention, and/or agonists or antagonists thereof, include, but are not limited to, chronic granulomatous disease, Chédiak-Higashi syndrome, myeloperoxidase deficiency, leukocyte glucose-6-phosphate dehydrogenase deficiency, X-linked lymphoproliferative syndrome (XLP), leukocyte adhesion deficiency, complement component deficiencies (including C1, C2, C3, C4, C5, C6, C7, C8 and/or C9 deficiencies), reticular dysgenesis, thymic alymphoplasia-aplasia, immunodeficiency with thymoma, severe congenital leukopenia, dysplasia with immunodeficiency, neonatal neutropenia, short limbed dwarfism, and Nezelof syndrome-combined immunodeficiency with Igs.

In a preferred embodiment, the immunodeficiencies and/or conditions associated with the immunodeficiencies recited above are prevented, detected, diagnosed, prognosticated, treated and/or ameliorated using polynucleotides, polypeptides, antibodies, and/or agonists or antagonists of the present invention.

In a preferred embodiment polynucleotides, polypeptides, antibodies, and/or agonists or antagonists of the present invention could be used as an agent to boost immunoresponsiveness among immunodeficient individuals. In specific embodiments, polynucleotides, polypeptides, antibodies, and/or agonists or antagonists of the present invention could be used as an agent to boost immunoresponsiveness among B cell and/or T cell immunodeficient individuals.

The polynucleotides, polypeptides, antibodies, and/or agonists or antagonists of the present invention may be useful in preventing, detecting, diagnosing, prognosticating, treating and/or ameliorating autoimmune disorders. Many autoimmune disorders result from inappropriate recognition of self as foreign material by immune cells. This inappropriate recognition results in an immune response leading to the destruction of the host tissue. Therefore, the administration of polynucleotides and polypeptides of the invention that can inhibit an immune response, particularly the proliferation, differentiation, or chemotaxis of T-cells, may be an effective therapy in preventing autoimmune disorders.

Autoimmune diseases or disorders that may be prevented, detected, diagnosed, prognosticated, treated, and/or ameliorated by polynucleotides, polypeptides, antibodies, and/or agonists or antagonists of the present invention include, but are not limited to, one or more of the following: systemic lupus erythematosus, rheumatoid arthritis, ankylosing spondylitis, multiple sclerosis, autoimmune thyroiditis, hypothyroidism, Hashimoto's thyroiditis, autoimmune hemolytic anemia, hemolytic anemia, thrombocytopenia, autoimmune thrombocytopenia purpura, autoimmune neonatal thrombocytopenia, idiopathic thrombocytopenia purpura, purpura (e.g., Henloch-Scoenlein purpura), autoimmunocytopenia, Goodpasture's syndrome, Pemphigus vulgaris, myasthenia gravis, Grave's disease (hyperthyroidism), inflammatory myopathies, insulin resistance, and insulin-resistant diabetes mellitus.

Additional disorders that are likely to have an autoimmune component that may be prevented, detected, diagnosed, prognosticated, treated and/or ameliorated with the compositions of the invention include, but are not limited to, type II collagen-induced arthritis, Addison's Disease, hemolytic anemia, antiphospholipid syndrome, rheumatoid arthritis, dermatitis, allergic encephalomyelitis, glomerulonephritis, Goodpasture's Syndrome, Grave's Disease, multiple sclerosis, myasthenia gravis, neuritis, ophthalmia, bullous pemphigoid, pemphigus, polyendocrinopathies, purpura, myocarditis, relapsing polychondritis, rheumatic heart disease, neuritis, uveitis ophthalmia, polyendocrinopathies, Reiter's Disease, Stiff-Man Syndrome, Autoimmune Thyroiditis, Systemic Lupus Erythematosus (SLE), autoimmune pulmonary inflammation, autism, Guillain-Barre Syndrome, insulin dependent diabetes mellitus, and autoimmune inflammatory eye disorders.

Additional disorders that are likely to have an autoimmune component that may be prevented, detected, diagnosed, prognosticated, treated and/or ameliorated with the compositions of the invention include, but are not limited to, scleroderma with anti-collagen antibodies (often characterized, e.g., by nucleolar and other nuclear antibodies), mixed connective tissue disease (often characterized, e.g., by antibodies to extractable nuclear antigens (e.g., ribonucleoprotein)), polymyositis (often characterized, e.g., by nonhistone ANA), pernicious anemia (often characterized, e.g., by antiparietal cell, microsomes, and intrinsic factor antibodies), idiopathic Addison's disease (often characterized, e.g., by humoral and cell-mediated adrenal cytotoxicity, infertility (often characterized, e.g., by antispermatozoal antibodies), glomerulonephritis (often characterized, e.g., by glomerular basement membrane antibodies or immune complexes), bullous pemphigoid (often characterized, e.g., by IgG and complement in basement membrane), Sjogren's syndrome (often characterized, e.g., by multiple tissue antibodies, and/or a specific nonhistone ANA (SS-B)), diabetes mellitus (often characterized, e.g., by cell-mediated and humoral islet cell antibodies), and adrenergic drug resistance (including adrenergic drug resistance with asthma or cystic fibrosis) (often characterized, e.g., by beta-adrenergic receptor antibodies).

Additional disorders that may have an autoimmune component that may be prevented, detected, diagnosed, prognosticated, treated and/or ameliorated with the compositions of the invention include, but are not limited to, chronic active hepatitis (often characterized, e.g., by smooth muscle antibodies), primary biliary cirrhosis (often characterized, e.g., by mitochondria antibodies), other endocrine gland failure (often characterized, e.g., by specific tissue antibodies in some cases), vitiligo (often characterized, e.g., by melanocyte antibodies), vasculitis (often characterized, e.g., by Ig and complement in vessel walls and/or low serum complement), post-MI (often characterized, e.g., by myocardial antibodies), cardiotomy syndrome (often characterized, e.g., by myocardial antibodies), urticaria (often characterized, e.g., by IgG and IgM antibodies to IgE), atopic dermatitis (often characterized, e.g., by IgG and IgM antibodies to IgE), asthma (often characterized, e.g., by IgG and IgM antibodies to IgE), and many other inflammatory, granulomatous, degenerative, and atrophic disorders.

In a preferred embodiment, the autoimmune diseases and disorders and/or conditions associated with the diseases and disorders recited above are prevented, detected, diagnosed, prognosticated, treated and/or ameliorated using for example, antagonists or agonists, polypeptides or polynucleotides, or antibodies of the present invention. In a specific preferred embodiment, rheumatoid arthritis is prevented, detected, diagnosed, prognosticated, treated and/or ameliorated using polynucleotides, polypeptides, antibodies, and/or agonists or antagonists of the present invention.

In another specific preferred embodiment, systemic lupus erythematosus is prevented, detected, diagnosed, prognosticated, treated and/or ameliorated using polynucleotides, polypeptides, antibodies, and/or agonists or antagonists of the present invention. In another specific preferred embodiment, idiopathic thrombocytopenia purpura is prevented, detected, diagnosed, prognosticated, treated and/or ameliorated using polynucleotides, polypeptides, antibodies, and/or agonists or antagonists of the present invention.

In another specific preferred embodiment IgA nephropathy is prevented, detected, diagnosed, prognosticated, treated and/or ameliorated using polynucleotides, polypeptides, antibodies, and/or agonists or antagonists of the present invention.

In a preferred embodiment, the autoimmune diseases and disorders and/or conditions associated with the diseases and disorders recited above are prevented, detected, diagnosed, prognosticated, treated and/or ameliorated using polynucleotides, polypeptides, antibodies, and/or agonists or antagonists of the present invention In preferred embodiments, polypeptides, antibodies, polynucleotides and/or agonists or antagonists of the present invention are used as a immunosuppressive agent(s).

Polynucleotides, polypeptides, antibodies, and/or agonists or antagonists of the present invention may be useful in detecting, preventing, diagnosing, prognosticating, treating, and/or ameliorating diseases, disorders, and/or conditions of hematopoietic cells. Polynucleotides, polypeptides, antibodies, and/or agonists or antagonists of the present invention could be used to increase differentiation and proliferation of hematopoietic cells, including the pluripotent stem cells, in an effort to treat or prevent those diseases, disorders, and/or conditions associated with a decrease in certain (or many) types hematopoietic cells, including but not limited to, leukopenia, neutropenia, anemia, and thrombocytopenia. Alternatively, Polynucleotides, polypeptides, antibodies, and/or agonists or antagonists of the present invention could be used to increase differentiation and proliferation of hematopoietic cells, including the pluripotent stem cells, in an effort to treat or prevent those diseases, disorders, and/or conditions associated with an increase in certain (or many) types of hematopoietic cells, including but not limited to, histiocytosis.

Allergic reactions and conditions, such as asthma (particularly allergic asthma) or other respiratory problems, may also be detected, prevented, diagnosed, prognosticated, treated, and/or ameliorated using polypeptides, antibodies, or polynucleotides of the invention, and/or agonists or antagonists thereof. Moreover, these molecules can be used to treat, prevent, prognose, and/or diagnose anaphylaxis, hypersensitivity to an antigenic molecule, or blood group incompatibility.

Additionally, polypeptides or polynucleotides of the invention, and/or agonists or antagonists thereof, may be used to detect, prevent, diagnose, prognosticate, treat, and/or ameliorate IgE-mediated allergic reactions. Such allergic reactions include, but are not limited to, asthma, rhinitis, and eczema. In specific embodiments, polynucleotides, polypeptides, antibodies, and/or agonists or antagonists of the present invention may be used to modulate IgE concentrations in vitro or in vivo.

Moreover, polynucleotides, polypeptides, antibodies, and/or agonists or antagonists of the present invention have uses in the detection, prevention, diagnosis, prognostication, treatment, and/or amelioration of inflammatory conditions. For example, since polypeptides, antibodies, or polynucleotides of the invention, and/or agonists or antagonists of the invention may inhibit the activation, proliferation and/or differentiation of cells involved in an inflammatory response, these molecules can be used to prevent and/or treat chronic and acute inflammatory conditions. Such inflammatory conditions include, but are not limited to, for example, inflammation associated with infection (e.g., septic shock, sepsis, or systemic inflammatory response syndrome), ischemia-reperfusion injury, endotoxin lethality, complement-mediated hyperacute rejection, nephritis, cytokine or chemokine induced lung injury, inflammatory bowel disease, Crohn's disease, over production of cytokines (e.g., TNF or IL-1.), respiratory disorders (e.g., asthma and allergy); gastrointestinal disorders (e.g., inflammatory bowel disease); cancers (e.g., gastric, ovarian, lung, bladder, liver, and breast); CNS disorders (e.g., multiple sclerosis; blood brain permeability, ischemic brain injury and/or stroke, traumatic brain injury, neurodegenerative disorders (e.g., Parkinson's disease and Alzheimer's disease); AIDS-related dementia; and prion disease); cardiovascular disorders (e.g., atherosclerosis, myocarditis, cardiovascular disease, and cardiopulmonary bypass complications); as well as many additional diseases, conditions, and disorders that are characterized by inflammation (e.g., hepatitis, rheumatoid arthritis, gout, trauma, septic shock, pancreatitis, sarcoidosis, dermatitis, renal ischemia-reperfusion injury, Grave's disease, systemic lupus erythematosus, diabetes mellitus, and allogenic transplant rejection).

Because inflammation is a fundamental defense mechanism, inflammatory disorders can effect virtually any tissue of the body. Accordingly, polynucleotides, polypeptides, and antibodies of the invention, as well as agonists or antagonists thereof, have uses in the treatment of tissue-specific inflammatory disorders, including, but not limited to, adrenalitis, alveolitis, angiocholecystitis, appendicitis, balanitis, blepharitis, bronchitis, bursitis, carditis, cellulitis, cervicitis, cholecystitis, chorditis, cochlitis, colitis, conjunctivitis, cystitis, dermatitis, diverticulitis, encephalitis, endocarditis, esophagitis, eustachitis, fibrositis, folliculitis, gastritis, gastroenteritis, gingivitis, glossitis, hepatosplenitis, keratitis, labyrinthitis, laryngitis, lymphangitis, mastitis, media otitis, meningitis, metritis, mucitis, myocarditis, myosititis, myringitis, nephritis, neuritis, orchitis, osteochondritis, otitis, pericarditis, peritendonitis, peritonitis, pharyngitis, phlebitis, poliomyelitis, prostatitis, pulpitis, retinitis, rhinitis, salpingitis, scleritis, sclerochoroiditis, scrotitis, sinusitis, spondylitis, steatitis, stomatitis, synovitis, syringitis, tendonitis, tonsillitis, urethritis, and vaginitis.

In specific embodiments, polypeptides, antibodies, or polynucleotides of the invention, and/or agonists or antagonists thereof, are useful to detect, prevent, diagnose, prognosticate, treat, and/or ameliorate organ transplant rejections and graft-versus-host disease (GVHD). Organ rejection occurs by host immune cell destruction of the transplanted tissue through an immune response. Similarly, an immune response is also involved in GVHD, but, in this case, the foreign transplanted immune cells destroy the host tissues. Polypeptides, antibodies, or polynucleotides of the invention, and/or agonists or antagonists thereof, that inhibit an immune response, particularly the activation, proliferation, differentiation, or chemotaxis of T-cells, may be an effective therapy in preventing organ rejection or GVHD. In specific embodiments, polypeptides, antibodies, or polynucleotides of the invention, and/or agonists or antagonists thereof, that inhibit an immune response, particularly the activation, proliferation, differentiation, or chemotaxis of T-cells, may be an effective therapy in preventing experimental allergic and hyperacute xenograft rejection.

In specific embodiments, polypeptides, antibodies, or polynucleotides of the invention, and/or agonists or antagonists thereof, are useful to diagnose, prognose, prevent, and/or treat, autoimmune and inflammatory diseases (e.g., immune complex-induced vasculitis, glomerulonephritis, hemolytic anemia, myasthenia gravis, type II collagen-induced arthritis, experimental allergic and hyperacute xenograft rejection, rheumatoid arthritis, and systemic lupus erythematosus (SLE).

Similarly, a polynucleotides or polypeptides, or agonists or antagonists of the present invention may also be used to modulate and/or diagnose inflammation. For example, the polypeptide or polynucleotide or agonists or antagonist may inhibit the proliferation and differentiation of cells involved in an inflammatory response. These molecules can be used to treat, prevent, diagnose and/or prognose inflammatory conditions, both chronic and acute conditions, including, but not limited to, chronic prostatitis, granulomatous prostatitis and malacoplakia, inflammation associated with infection (e.g., septic shock, sepsis, or systemic inflammatory response syndrome (SIRS)), ischemia-reperfusion injury, endotoxin lethality, arthritis, complement-mediated hyperacute rejection, nephritis, cytokine or chemokine induced lung injury, inflammatory bowel disease, Crohn's disease, or resulting from over production of cytokines (e.g., TNF or IL-1.)

In other embodiments, polypeptides, antibodies, or polynucleotides of the invention, and/or agonists or antagonists thereof, are useful to detect, prevent, diagnose, prognosticate, treat, and/or ameliorate immune complex diseases, including, but not limited to, serum sickness, post streptococcal glomerulonephritis, polyarteritis nodosa, and immune complex-induced vasculitis.

Polypeptides, antibodies, polynucleotides and/or agonists or antagonists of the invention can be used to treat, detect, and/or prevent infectious agents. For example, by increasing the immune response, particularly increasing the proliferation activation and/or differentiation of B and/or T cells, infectious diseases may be treated, detected, and/or prevented. The immune response may be increased by either enhancing an existing immune response, or by initiating a new immune response. Alternatively, polynucleotides, polypeptides, antibodies, and/or agonists or antagonists of the present invention may also directly inhibit the infectious agent (refer to section of application listing infectious agents, etc), without necessarily eliciting an immune response.

In another embodiment, polypeptides, antibodies, polynucleotides and/or agonists or antagonists of the present invention are used as a vaccine adjuvant that enhances immune responsiveness to an antigen. In a specific embodiment, polypeptides, antibodies, polynucleotides and/or agonists or antagonists of the present invention are used as an adjuvant to enhance tumor-specific immune responses.

In another specific embodiment, polypeptides, antibodies, polynucleotides and/or agonists or antagonists of the present invention are used as an adjuvant to enhance anti-viral immune responses. Anti-viral immune responses that may be enhanced using the compositions of the invention as an adjuvant, include virus and virus associated diseases or symptoms described herein or otherwise known in the art. In specific embodiments, the compositions of the invention are used as an adjuvant to enhance an immune response to a virus, disease, or symptom selected from the group consisting of: AIDS, meningitis, Dengue, EBV, and hepatitis (e.g., hepatitis B). In another specific embodiment, the compositions of the invention are used as an adjuvant to enhance an immune response to a virus, disease, or symptom selected from the group consisting of: HIV/AIDS, respiratory syncytial virus, Dengue, rotavirus, Japanese B encephalitis, influenza A and B, parainfluenza, measles, cytomegalovirus, rabies, Junin, Chikungunya, Rift Valley Fever, herpes simplex, and yellow fever.

In another specific embodiment, polypeptides, antibodies, polynucleotides and/or agonists or antagonists of the present invention are used as an adjuvant to enhance anti-bacterial or anti-fungal immune responses. Anti-bacterial or anti-fungal immune responses that may be enhanced using the compositions of the invention as an adjuvant, include bacteria or fungus and bacteria or fungus associated diseases or symptoms described herein or otherwise known in the art. In specific embodiments, the compositions of the invention are used as an adjuvant to enhance an immune response to a bacteria or fungus, disease, or symptom selected from the group consisting of: tetanus, Diphtheria, botulism, and meningitis type B.

In another specific embodiment, the compositions of the invention are used as an adjuvant to enhance an immune response to a bacteria or fungus, disease, or symptom selected from the group consisting of: *Vibrio cholerae, Mycobacterium leprae, Salmonella typhi, Salmonella paratyphi, Meisseria meningitidis, Streptococcus pneumoniae*, Group B *streptococcus, Shigella* spp., Enterotoxigenic *Escherichia coli*, Enterohemorrhagic *E. coli, Plasmodium* (malaria), and *Borrelia burgdorferi.*

In another specific embodiment, polypeptides, antibodies, polynucleotides and/or agonists or antagonists of the present invention are used as an adjuvant to enhance anti-parasitic immune responses. Anti-parasitic immune responses that may be enhanced using the compositions of the invention as an adjuvant, include parasite and parasite associated diseases or symptoms described herein or otherwise known in the art. In specific embodiments, the compositions of the invention are used as an adjuvant to enhance an immune response to a parasite. In another specific embodiment, the compositions of the invention are used as an adjuvant to enhance an immune response to *Plasmodium* (malaria) or *Leishmania.*

In another specific embodiment, polypeptides, antibodies, polynucleotides and/or agonists or antagonists of the present invention may also be employed to treat infectious diseases including silicosis, sarcoidosis, and idiopathic pulmonary fibrosis; for example, by preventing the recruitment and activation of mononuclear phagocytes.

In another specific embodiment, polypeptides, antibodies, polynucleotides and/or agonists or antagonists of the present invention are used as an antigen for the generation of antibodies to inhibit or enhance immune mediated responses against polypeptides of the invention.

In one embodiment, polypeptides, antibodies, polynucleotides and/or agonists or antagonists of the present invention are administered to an animal (e.g., mouse, rat, rabbit, hamster, guinea pig, pigs, micro-pig, chicken, camel, goat, horse, cow, sheep, dog, cat, non-human primate, and human, most preferably human) to boost the immune system to produce increased quantities of one or more antibodies (e.g., IgG, IgA, IgM, and IgE), to induce higher affinity antibody production and immunoglobulin class switching (e.g., IgG, IgA, IgM, and IgE), and/or to increase an immune response.

In another specific embodiment, polypeptides, antibodies, polynucleotides and/or agonists or antagonists of the present invention are used as a stimulator of B cell responsiveness to pathogens.

In another specific embodiment, polypeptides, antibodies, polynucleotides and/or agonists or antagonists of the present invention are used as an activator of T cells.

In another specific embodiment, polypeptides, antibodies, polynucleotides and/or agonists or antagonists of the present invention are used as an agent that elevates the immune status of an individual prior to their receipt of immunosuppressive therapies.

In another specific embodiment, polypeptides, antibodies, polynucleotides and/or agonists or antagonists of the present invention are used as an agent to induce higher affinity antibodies.

In another specific embodiment, polypeptides, antibodies, polynucleotides and/or agonists or antagonists of the present invention are used as an agent to increase serum immunoglobulin concentrations.

In another specific embodiment, polypeptides, antibodies, polynucleotides and/or agonists or antagonists of the present invention are used as an agent to accelerate recovery of immunocompromised individuals.

In another specific embodiment, polypeptides, antibodies, polynucleotides and/or agonists or antagonists of the present invention are used as an agent to boost immunoresponsiveness among aged populations and/or neonates.

In another specific embodiment, polypeptides, antibodies, polynucleotides and/or agonists or antagonists of the present invention are used as an immune system enhancer prior to, during, or after bone marrow transplant and/or other transplants (e.g., allogeneic or xenogeneic organ transplantation). With respect to transplantation, compositions of the invention may be administered prior to, concomitant with, and/or after transplantation. In a specific embodiment, compositions of the invention are administered after transplantation, prior to the beginning of recovery of T-cell populations. In another specific embodiment, compositions of the invention are first administered after transplantation after the beginning of recovery of T cell populations, but prior to full recovery of B cell populations.

In another specific embodiment, polypeptides, antibodies, polynucleotides and/or agonists or antagonists of the present invention are used as an agent to boost immunoresponsiveness among individuals having an acquired loss of B cell function. Conditions resulting in an acquired loss of B cell function that may be ameliorated or treated by administering the polypeptides, antibodies, polynucleotides and/or agonists or antagonists thereof, include, but are not limited to, HIV Infection, AIDS, bone marrow transplant, and B cell chronic lymphocytic leukemia (CLL).

In another specific embodiment, polypeptides, antibodies, polynucleotides and/or agonists or antagonists of the present invention are used as an agent to boost immunoresponsiveness among individuals having a temporary immune deficiency. Conditions resulting in a temporary immune deficiency that may be ameliorated or treated by administering the polypeptides, antibodies, polynucleotides and/or agonists or antagonists thereof, include, but are not limited to, recovery from viral infections (e.g., influenza), conditions associated with malnutrition, recovery from infectious mononucleosis, or conditions associated with stress, recovery from measles, recovery from blood transfusion, and recovery from surgery.

In another specific embodiment, polypeptides, antibodies, polynucleotides and/or agonists or antagonists of the present invention are used as a regulator of antigen presentation by monocytes, dendritic cells, and/or B-cells. In one embodiment, polynucleotides, polypeptides, antibodies, and/or agonists or antagonists of the present invention enhance antigen presentation or antagonizes antigen presentation in vitro or in vivo. Moreover, in related embodiments, said enhancement or antagonism of antigen presentation may be useful as an anti-tumor treatment or to modulate the immune system.

In another specific embodiment, polypeptides, antibodies, polynucleotides and/or agonists or antagonists of the present invention are used as an agent to direct an individual's immune system towards development of a humoral response (i.e. TH2) as opposed to a TH1 cellular response.

In another specific embodiment, polypeptides, antibodies, polynucleotides and/or agonists or antagonists of the present invention are used as a means to induce tumor proliferation and thus make it more susceptible to anti-neoplastic agents. For example, multiple myeloma is a slowly dividing disease and is thus refractory to virtually all anti-neoplastic regimens. If these cells were forced to proliferate more rapidly their susceptibility profile would likely change.

In another specific embodiment, polypeptides, antibodies, polynucleotides and/or agonists or antagonists of the present invention are used as a stimulator of B cell production in pathologies such as AIDS, chronic lymphocyte disorder and/or Common Variable Immunodeficiency.

In another specific embodiment, polypeptides, antibodies, polynucleotides and/or agonists or antagonists of the present invention are used as a therapy for generation and/or regeneration of lymphoid tissues following surgery, trauma or genetic defect. In another specific embodiment, polypeptides, antibodies, polynucleotides and/or agonists or antagonists of the present invention are used in the pretreatment of bone marrow samples prior to transplant.

In another specific embodiment, polypeptides, antibodies, polynucleotides and/or agonists or antagonists of the present invention are used as a gene-based therapy for genetically inherited disorders resulting in immuno-incompetence/immunodeficiency such as observed among SCID patients.

In another specific embodiment, polypeptides, antibodies, polynucleotides and/or agonists or antagonists of the present invention are used as a means of activating monocytes/macrophages to defend against parasitic diseases that effect monocytes such as *Leishmania*.

In another specific embodiment, polypeptides, antibodies, polynucleotides and/or agonists or antagonists of the present invention are used as a means of regulating secreted cytokines that are elicited by polypeptides of the invention.

In another embodiment, polypeptides, antibodies, polynucleotides and/or agonists or antagonists of the present invention are used in one or more of the applications described herein, as they may apply to veterinary medicine.

In another specific embodiment, polypeptides, antibodies, polynucleotides and/or agonists or antagonists of the present invention are used as a means of blocking various aspects of immune responses to foreign agents or self. Examples of diseases or conditions in which blocking of certain aspects of immune responses may be desired include autoimmune disorders such as lupus, and arthritis, as well as immunoresponsiveness to skin allergies, inflammation, bowel disease, injury and diseases/disorders associated with pathogens.

In another specific embodiment, polypeptides, antibodies, polynucleotides and/or agonists or antagonists of the present invention are used as a therapy for preventing the B cell proliferation and Ig secretion associated with autoimmune diseases such as idiopathic thrombocytopenic purpura, systemic lupus erythematosus and multiple sclerosis.

In another specific embodiment, polypeptides, antibodies, polynucleotides and/or agonists or antagonists of the present invention are used as a inhibitor of B and/or T cell migration in endothelial cells. This activity disrupts tissue architecture or cognate responses and is useful, for example in disrupting immune responses, and blocking sepsis.

In another specific embodiment, polypeptides, antibodies, polynucleotides and/or agonists or antagonists of the present invention are used as a therapy for chronic hypergammaglobulinemia evident in such diseases as monoclonal gammopathy of undetermined significance (MGUS), Waldenstrom's disease, related idiopathic monoclonal gammopathies, and plasmacytomas.

In another specific embodiment, polypeptides, antibodies, polynucleotides and/or agonists or antagonists of the present invention may be employed for instance to inhibit polypeptide chemotaxis and activation of macrophages and their precursors, and of neutrophils, basophils, B lymphocytes and some T-cell subsets, e.g., activated and CD8 cytotoxic T cells and natural killer cells, in certain autoimmune and chronic inflammatory and infective diseases. Examples of autoimmune diseases are described herein and include multiple sclerosis, and insulin-dependent diabetes.

The polypeptides, antibodies, polynucleotides and/or agonists or antagonists of the present invention may also be employed to treat idiopathic hyper-eosinophilic syndrome by, for example, preventing eosinophil production and migration.

In another specific embodiment, polypeptides, antibodies, polynucleotides and/or agonists or antagonists of the present invention are used to enhance or inhibit complement mediated cell lysis.

In another specific embodiment, polypeptides, antibodies, polynucleotides and/or agonists or antagonists of the present invention are used to enhance or inhibit antibody dependent cellular cytotoxicity.

In another specific embodiment, polypeptides, antibodies, polynucleotides and/or agonists or antagonists of the present invention may also be employed for treating atherosclerosis, for example, by preventing monocyte infiltration in the artery wall.

In another specific embodiment, polypeptides, antibodies, polynucleotides and/or agonists or antagonists of the present invention may be employed to treat adult respiratory distress syndrome (ARDS).

In another specific embodiment, polypeptides, antibodies, polynucleotides and/or agonists or antagonists of the present invention may be useful for stimulating wound and tissue repair, stimulating angiogenesis, and/or stimulating the repair of vascular or lymphatic diseases or disorders. Additionally, agonists and antagonists of the invention may be used to stimulate the regeneration of mucosal surfaces.

In a specific embodiment, polynucleotides or polypeptides, and/or agonists thereof are used to detect, prevent, diagnose, prognosticate, treat, and/or ameliorate a disorder characterized by primary or acquired immunodeficiency, deficient serum immunoglobulin production, recurrent infections, and/or immune system dysfunction. Moreover, polynucleotides or polypeptides, and/or agonists thereof may be used to treat or prevent infections of the joints, bones, skin, and/or parotid glands, blood-borne infections (e.g., sepsis, meningitis, septic arthritis, and/or osteomyelitis), autoimmune diseases (e.g., those disclosed herein), inflammatory disorders, and malignancies, and/or any disease or disorder or condition associated with these infections, diseases, disorders and/or malignancies) including, but not limited to, CVID, other primary immune deficiencies, HIV disease, CLL, recurrent bronchitis, sinusitis, otitis media, conjunctivitis, pneumonia, hepatitis, meningitis, herpes zoster (e.g., severe herpes zoster), and/or *pneumocystis carnii*. Other diseases and disorders that may be detected, prevented, diagnosed, prognosticated, treated, and/or ameliorated with polynucleotides or polypeptides, and/or agonists of the present invention include, but are not limited to, HIV infection, HTLV-BLV infection, lymphopenia, phagocyte bactericidal dysfunction anemia, thrombocytopenia, and hemoglobinuria.

In another embodiment, polynucleotides, polypeptides, antibodies, and/or agonists or antagonists of the present invention are used to treat, and/or diagnose an individual having common variable immunodeficiency disease ("CVID"; also known as "acquired agammaglobulinemia" and "acquired hypogammaglobulinemia") or a subset of this disease.

In a specific embodiment, polynucleotides, polypeptides, antibodies, and/or agonists or antagonists of the present invention may be used to detect, prevent, diagnose, prognosticate, treat, and/or ameliorate cancers or neoplasms including immune cell or immune tissue-related cancers or neoplasms. Examples of cancers or neoplasms that may be detected, prevented, diagnosed, prognosticated, treated, and/or ameliorated by polynucleotides, polypeptides, antibodies, and/or agonists or antagonists of the present invention include, but are not limited to, acute myelogenous leukemia, chronic myelogenous leukemia, Hodgkin's disease, non-Hodgkin's lymphoma, acute lymphocytic anemia (ALL) Chronic lymphocyte leukemia, plasmacytomas, multiple myeloma, Burkitt's lymphoma, EBV-transformed diseases, and/or diseases and disorders described in the section entitled "Hyperproliferative Disorders" elsewhere herein.

In another specific embodiment, polypeptides, antibodies, polynucleotides and/or agonists or antagonists of the present invention are used as a means of activating T cells.

In another specific embodiment, polypeptides, antibodies, polynucleotides and/or agonists or antagonists of the present invention are used as an inhibitor of graft versus host disease or transplant rejection.

In another specific embodiment, polypeptides, antibodies, polynucleotides and/or agonists or antagonists of the present invention are used as a therapy for B cell and/or T cell malignancies such as ALL, Hodgkins disease, non-Hodgkins lymphoma, Chronic lymphocyte leukemia, plasmacytomas, multiple myeloma, Burkitt's lymphoma, and EBV-transformed diseases.

In another embodiment, administration of polypeptides, antibodies, polynucleotides and/or agonists or antagonists of the invention, may be used to treat or prevent IgE-mediated allergic reactions including, but not limited to, asthma, rhinitis, and eczema.

In another specific embodiment, polypeptides, antibodies, polynucleotides and/or agonists or antagonists of the present invention are used as a therapy for decreasing cellular proliferation of Large B-cell Lymphomas.

In another specific embodiment, polypeptides, antibodies, polynucleotides and/or agonists or antagonists of the present invention are used as a means of decreasing the involvement of B cells and Ig associated with Chronic Myelogenous Leukemia.

In specific embodiments, the compositions of the invention are used as an agent to boost immunoresponsiveness among B cell immunodeficient individuals, such as, for example, an individual who has undergone a partial or complete splenectomy.

Antagonists of the invention include, for example, binding and/or inhibitory antibodies, antisense nucleic acids, ribozymes or soluble forms of the polypeptides of the present invention (e.g., Fc fusion protein; see, e.g., Example 9). Agonists of the invention include, for example, binding or stimulatory antibodies, and soluble forms of the polypeptides (e.g., Fc fusion proteins; see, e.g., Example 9). polypeptides, antibodies, polynucleotides and/or agonists or antagonists of the present invention may be employed in a composition with a pharmaceutically acceptable carrier, e.g., as described herein.

In another embodiment, polypeptides, antibodies, polynucleotides and/or agonists or antagonists of the present invention are administered to an animal (including, but not limited to, those listed above, and also including transgenic animals) incapable of producing functional endogenous antibody molecules or having an otherwise compromised endogenous immune system, but which is capable of producing human immunoglobulin molecules by means of a reconstituted or partially reconstituted immune system from another animal (see, e.g., published PCT Application Nos. WO98/24893, WO/9634096, WO/9633735, and WO/9110741). Administration of polypeptides, antibodies, polynucleotides and/or agonists or antagonists of the present invention to such animals is useful for the generation of monoclonal antibodies against the polypeptides, antibodies, polynucleotides and/or agonists or antagonists of the present invention.

Blood-Related Disorders

The polynucleotides, polypeptides, antibodies, and/or agonists or antagonists of the present invention may be used to modulate hemostatic (the stopping of bleeding) or thrombolytic (clot dissolving) activity. For example, by increasing hemostatic or thrombolytic activity, polynucleotides or polypeptides, and/or agonists or antagonists of the present invention could be used to treat or prevent blood coagulation diseases, disorders, and/or conditions (e.g., afibrinogenemia, factor deficiencies, hemophilia), blood platelet diseases, disorders, and/or conditions (e.g., thrombocytopenia), or wounds resulting from trauma, surgery, or other causes. Alternatively, polynucleotides, polypeptides, antibodies, and/or agonists or antagonists of the present invention that can decrease hemostatic or thrombolytic activity could be used to inhibit or dissolve clotting. These molecules could be important in the treatment or prevention of heart attacks (infarction), strokes, or scarring.

In specific embodiments, the polynucleotides, polypeptides, antibodies, and/or agonists or antagonists of the present invention may be used to detect, prevent, diagnose, prognosticate, treat, and/or ameliorate thrombosis, arterial thrombosis, venous thrombosis, thromboembolism, pulmonary embolism, atherosclerosis, myocardial infarction, transient ischemic attack, unstable angina. In specific embodiments, the polynucleotides, polypeptides, antibodies, and/or agonists or antagonists of the present invention may be used for the prevention of occlusion of saphenous grafts, for reducing the risk of periprocedural thrombosis as might accompany angioplasty procedures, for reducing the risk of stroke in patients with atrial fibrillation including nonrheumatic atrial fibrillation, for reducing the risk of embolism associated with mechanical heart valves and or mitral valves disease. Other uses for the polynucleotides, polypeptides, antibodies, and/or agonists or antagonists of the present invention, include, but are not limited to, the prevention of occlusions in extracorporeal devices (e.g., intravascular cannulas, vascular access shunts in hemodialysis patients, hemodialysis machines, and cardiopulmonary bypass machines).

In another embodiment, a polypeptide of the invention, or polynucleotides, antibodies, agonists, or antagonists corresponding to that polypeptide, may be used to detect, prevent, diagnose, prognosticate, treat, and/or ameliorate diseases and disorders of the blood and/or blood forming organs associated with the tissue(s) in which the polypeptide of the invention is expressed, including one, two, three, four, five, or more tissues disclosed in Table 1B.2, column 5 (Tissue Distribution Library Code).

The polynucleotides, polypeptides, antibodies, and/or agonists or antagonists of the present invention may be used to modulate hematopoietic activity (the formation of blood cells). For example, the polynucleotides, polypeptides, antibodies, and/or agonists or antagonists of the present invention may be used to increase the quantity of all or subsets of blood cells, such as, for example, erythrocytes, lymphocytes (B or T cells), myeloid cells (e.g., basophils, eosinophils, neutrophils, mast cells, macrophages) and platelets. The ability to decrease the quantity of blood cells or subsets of blood cells may be useful in the detection, prevention, diagnosis, prognostication, treatment, and/or amelioration of anemias and leukopenias described below. Alternatively, the polynucleotides, polypeptides, antibodies, and/or agonists or antagonists of the present invention may be used to decrease the quantity of all or subsets of blood cells, such as, for example, erythrocytes, lymphocytes (B or T cells), myeloid cells (e.g., basophils, eosinophils, neutrophils, mast cells, macrophages) and platelets. The ability to decrease the quantity of blood cells or subsets of blood cells may be useful in the detection, prevention, diagnosis, prognostication, treatment, and/or amelioration of leukocytoses, such as, for example eosinophilia.

The polynucleotides, polypeptides, antibodies, and/or agonists or antagonists of the present invention may be used to detect, prevent, diagnose, prognosticate, treat, and/or ameliorate blood dyscrasia.

Anemias are conditions in which the number of red blood cells or amount of hemoglobin (the protein that carries oxygen) in them is below normal. Anemia may be caused by excessive bleeding, decreased red blood cell production, or increased red blood cell destruction (hemolysis). The polynucleotides, polypeptides, antibodies, and/or agonists or antagonists of the present invention may be useful in detecting, preventing, diagnosing, prognosticating, treating, and/or ameliorating anemias. Anemias that may be treated detect, prevented, diagnosed, prognosticated, treated, and/or ameliorated by the polynucleotides, polypeptides, antibodies, and/or agonists or antagonists of the present invention include iron deficiency anemia, hypochromic anemia, microcytic anemia, chlorosis, hereditary sideroblastic anemia, idiopathic acquired sideroblastic anemia, red cell aplasia, megaloblastic anemia (e.g., pernicious anemia, (vitamin B12 deficiency) and folic acid deficiency anemia), aplastic anemia, hemolytic anemias (e.g., autoimmune helolytic anemia, microangiopathic hemolytic anemia, and paroxysmal nocturnal hemoglobinuria). The polynucleotides, polypeptides, antibodies, and/or agonists or antagonists of the present invention may be useful in detecting, preventing, diagnosing, prognosticating, treating, and/or ameliorating anemias associated with diseases including but not limited to, anemias associated with systemic lupus erythematosus, cancers, lymphomas, chronic renal disease, and enlarged spleens. The polynucleotides, polypeptides, antibodies, and/or agonists or antagonists of the present invention may be useful in detecting, preventing, diagnosing, prognosticating, treating, and/or ameliorating anemias arising from drug treatments such as anemias associated with methyldopa, dapsone, and/or sulfadrugs. Additionally, the polynucleotides, polypeptides, antibodies, and/or agonists or antagonists of the present invention may be useful in detecting, preventing, diagnosing, prognosticating, treating, and/or ameliorating anemias associated with abnormal red blood cell architecture including but not limited to, hereditary spherocytosis, hereditary elliptocytosis, glucose-6-phosphate dehydrogenase deficiency, and sickle cell anemia.

The polynucleotides, polypeptides, antibodies, and/or agonists or antagonists of the present invention may be useful in detecting, preventing, diagnosing, prognosticating, treating, and/or ameliorating hemoglobin abnormalities, (e.g., those associated with sickle cell anemia, hemoglobin C disease, hemoglobin S—C disease, and hemoglobin E disease). Additionally, the polynucleotides, polypeptides, antibodies, and/or agonists or antagonists of the present invention may be useful in detecting, preventing, diagnosing, prognosticating, treating, and/or ameliorating thalassemias, including, but not limited to major and minor forms of alpha-thalassemia and beta-thalassemia.

In another embodiment, the polynucleotides, polypeptides, antibodies, and/or agonists or antagonists of the present invention may be useful in detecting, preventing, diagnosing, prognosticating, treating, and/or ameliorating bleeding disorders including, but not limited to, thrombocytopenia (e.g., idiopathic thrombocytopenic purpura, and thrombotic thrombocytopenic purpura), Von Willebrand's disease, hereditary platelet disorders (e.g., storage pool disease such as Chediak-Higashi and Hermansky-Pudlak syndromes, thromboxane A2 dysfunction, thromboasthenia, and Bernard-Soulier syndrome), hemolytic-uremic syndrome, hemophelias such as hemophelia A or Factor VII deficiency and Christmas disease or Factor IX deficiency, Hereditary Hemorhhagic Telangiectsia, also known as Rendu-Osler-Weber syndrome, allergic purpura (Henoch Schonlein purpura) and disseminated intravascular coagulation.

The effect of the polynucleotides, polypeptides, antibodies, and/or agonists or antagonists of the present invention on the clotting time of blood may be monitored using any of the clotting tests known in the art including, but not limited to, whole blood partial thromboplastin time (PTT), the activated partial thromboplastin time (aPTT), the activated clotting time (ACT), the recalcified activated clotting time, or the Lee-White Clotting time.

Several diseases and a variety of drugs can cause platelet dysfunction. Thus, in a specific embodiment, the polynucleotides, polypeptides, antibodies, and/or agonists or antagonists of the present invention may be useful in detecting, preventing, diagnosing, prognosticating, treating, and/or ameliorating acquired platelet dysfunction such as platelet dysfunction accompanying kidney failure, leukemia, multiple myeloma, cirrhosis of the liver, and systemic lupus erythematosus as well as platelet dysfunction associated with drug treatments, including treatment with aspirin, ticlopidine, nonsteroidal anti-inflammatory drugs (used for arthritis, pain, and sprains), and penicillin in high doses.

In another embodiment, the polynucleotides, polypeptides, antibodies, and/or agonists or antagonists of the present invention may be useful in detecting, preventing, diagnosing, prognosticating, treating, and/or ameliorating diseases and disorders characterized by or associated with increased or decreased numbers of white blood cells. Leukopenia occurs when the number of white blood cells decreases below normal. Leukopenias include, but are not limited to, neutropenia and lymphocytopenia. An increase in the number of white blood cells compared to normal is known as leukocytosis. The body generates increased numbers of white blood cells during infection. Thus, leukocytosis may simply be a normal physiological parameter that reflects infection. Alternatively, leukocytosis may be an indicator of injury or other disease such as cancer. Leokocytoses, include but are not limited to, eosinophilia, and accumulations of macrophages. In specific embodiments, the polynucleotides, polypeptides, antibodies, and/or agonists or antagonists of the present invention may be useful in detecting, preventing, diagnosing, prognosticating, treating, and/or ameliorating leukopenia. In other specific embodiments, the polynucleotides, polypeptides, antibodies, and/or agonists or antagonists of the present invention may be useful in detecting, preventing, diagnosing, prognosticating, treating, and/or ameliorating leukocytosis.

Leukopenia may be a generalized decreased in all types of white blood cells, or may be a specific depletion of particular types of white blood cells. Thus, in specific embodiments, the polynucleotides, polypeptides, antibodies, and/or agonists or antagonists of the present invention may be useful in detecting, preventing, diagnosing, prognosticating, treating, and/or ameliorating decreases in neutrophil numbers, known as neutropenia. Neutropenias that may be detected, prevented, diagnosed, prognosticated, treated, and/or ameliorated by the polynucleotides, polypeptides, antibodies, and/or agonists or antagonists of the present invention include, but are not limited to, infantile genetic agranulocytosis, familial neutropenia, cyclic neutropenia, neutropenias resulting from or associated with dietary deficiencies (e.g., vitamin B 12 deficiency or folic acid deficiency), neutropenias resulting from or associated with drug treatments (e.g., antibiotic regimens such as penicillin treatment, sulfonamide treatment, anticoagulant treatment, anticonvulsant drugs, anti-thyroid drugs, and cancer chemotherapy), and neutropenias resulting from increased neutrophil destruction that may occur in association with some bacterial or viral infections, allergic disorders, autoimmune diseases, conditions in which an individual has an enlarged spleen (e.g., Felty syndrome, malaria and sarcoidosis), and some drug treatment regimens.

The polynucleotides, polypeptides, antibodies, and/or agonists or antagonists of the present invention may be useful in detecting, preventing, diagnosing, prognosticating, treating, and/or ameliorating lymphocytopenias (decreased numbers of B and/or T lymphocytes), including, but not limited lymphocytopenias resulting from or associated with stress, drug treatments (e.g., drug treatment with corticosteroids, cancer chemotherapies, and/or radiation therapies), AIDS infection and/or other diseases such as, for example, cancer, rheumatoid arthritis, systemic lupus erythematosus, chronic infections, some viral infections and/or hereditary disorders (e.g., DiGeorge syndrome, Wiskott-Aldrich Syndrome, severe combined immunodeficiency, ataxia telangiectsia).

The polynucleotides, polypeptides, antibodies, and/or agonists or antagonists of the present invention may be useful in detecting, preventing, diagnosing, prognosticating, treating, and/or ameliorating diseases and disorders associated with macrophage numbers and/or macrophage function including, but not limited to, Gaucher's disease, Niemann-Pick disease, Letterer-Siwe disease and Hand-Schuller-Christian disease.

In another embodiment, the polynucleotides, polypeptides, antibodies, and/or agonists or antagonists of the present invention may be useful in detecting, preventing, diagnosing, prognosticating, treating, and/or ameliorating diseases and disorders associated with eosinophil numbers and/or eosinophil function including, but not limited to, idiopathic hypereosinophilic syndrome, eosinophilia-myalgia syndrome, and Hand-Schuller-Christian disease.

In yet another embodiment, the polynucleotides, polypeptides, antibodies, and/or agonists or antagonists of the present invention may be useful in detecting, preventing, diagnosing, prognosticating, treating, and/or ameliorating leukemias and lymphomas including, but not limited to, acute lymphocytic (lymphpblastic) leukemia (ALL), acute myeloid (myelocytic, myelogenous, myeloblastic, or myelomonocytic) leukemia, chronic lymphocytic leukemia (e.g., B cell leukemias, T cell leukemias, Sezary syndrome, and Hairy cell leukemia), chronic myelocytic (myeloid, myelogenous, or granulocytic) leukemia, Hodgkin's lymphoma, non-hodgkin's lymphoma, Burkitt's lymphoma, and mycosis fungoides.

In other embodiments, the polynucleotides, polypeptides, antibodies, and/or agonists or antagonists of the present invention may be useful in detecting, preventing, diagnosing, prognosticating, treating, and/or ameliorating diseases and disorders of plasma cells including, but not limited to, plasma cell dyscrasias, monoclonal gammaopathies, monoclonal gammopathies of undetermined significance, multiple myeloma, macroglobulinemia, Waldenstrom's macroglobulinemia, cryoglobulinemia, and Raynaud's phenomenon.

In other embodiments, the polynucleotides, polypeptides, antibodies, and/or agonists or antagonists of the present invention may be useful in detecting, preventing, diagnosing, prognosticating, treating, and/or ameliorating myeloproliferative disorders, including but not limited to, polycythemia vera, relative polycythemia, secondary polycythemia, myelofibrosis, acute myelofibrosis, agnogenic myeloid metaplasia, thrombocythemia, (including both primary and secondary thrombocythemia) and chronic myelocytic leukemia.

In other embodiments, the polynucleotides, polypeptides, antibodies, and/or agonists or antagonists of the present invention may be useful as a treatment prior to surgery, to increase blood cell production.

In other embodiments, the polynucleotides, polypeptides, antibodies, and/or agonists or antagonists of the present invention may be useful as an agent to enhance the migration, phagocytosis, superoxide production, antibody dependent cellular cytotoxicity of neutrophils, eosionophils and macrophages.

In other embodiments, the polynucleotides, polypeptides, antibodies, and/or agonists or antagonists of the present invention may be useful as an agent to increase the number of stem cells in circulation prior to stem cells pheresis. In another specific embodiment, the polynucleotides, polypeptides, antibodies, and/or agonists or antagonists of the present invention may be useful as an agent to increase the number of stem cells in circulation prior to platelet pheresis.

In other embodiments, the polynucleotides, polypeptides, antibodies, and/or agonists or antagonists of the present invention may be useful as an agent to increase cytokine production.

In other embodiments, the polynucleotides, polypeptides, antibodies, and/or agonists or antagonists of the present invention may be useful in detecting, preventing, diagnosing, prognosticating, treating, and/or ameliorating primary hematopoietic disorders.

Hyperproliferative Disorders

In certain embodiments, polynucleotides or polypeptides, or agonists or antagonists of the present invention can be used to treat or detect hyperproliferative disorders, including neoplasms. Polynucleotides or polypeptides, or agonists or antagonists of the present invention may inhibit the proliferation of the disorder through direct or indirect interactions. Alternatively, Polynucleotides or polypeptides, or agonists or antagonists of the present invention may proliferate other cells which can inhibit the hyperproliferative disorder.

For example, by increasing an immune response, particularly increasing antigenic qualities of the hyperproliferative disorder or by proliferating, differentiating, or mobilizing T-cells, hyperproliferative disorders can be treated. This immune response may be increased by either enhancing an existing immune response, or by initiating a new immune response. Alternatively, decreasing an immune response may also be a method of treating hyperproliferative disorders, such as a chemotherapeutic agent.

Examples of hyperproliferative disorders that can be treated or detected by polynucleotides or polypeptides, or agonists or antagonists of the present invention include, but are not limited to neoplasms located in the: colon, abdomen, bone, breast, digestive system, liver, pancreas, peritoneum, endocrine glands (adrenal, parathyroid, pituitary, testicles, ovary, thymus, thyroid), eye, head and neck, nervous (central and peripheral), lymphatic system, pelvis, skin, soft tissue, spleen, thorax, and urogenital tract.

Similarly, other hyperproliferative disorders can also be treated or detected by polynucleotides or polypeptides, or agonists or antagonists of the present invention. Examples of such hyperproliferative disorders include, but are not limited to: Acute Childhood Lymphoblastic Leukemia, Acute Lymphoblastic Leukemia, Acute Lymphocytic Leukemia, Acute Myeloid Leukemia, Adrenocortical Carcinoma, Adult (Primary) Hepatocellular Cancer, Adult (Primary) Liver Cancer, Adult Acute Lymphocytic Leukemia, Adult Acute Myeloid Leukemia, Adult Hodgkin's Disease, Adult Hodgkin's Lymphoma, Adult Lymphocytic Leukemia, Adult Non-Hodgkin's Lymphoma, Adult Primary Liver Cancer, Adult Soft Tissue Sarcoma, AIDS-Related Lymphoma, AIDS-Related Malignancies, Anal Cancer, Astrocytoma, Bile Duct Cancer, Bladder Cancer, Bone Cancer, Brain Stem Glioma, Brain Tumors, Breast Cancer, Cancer of the Renal Pelvis and Ureter, Central Nervous System (Primary) Lymphoma, Central Nervous System Lymphoma, Cerebellar Astrocytoma, Cerebral Astrocytoma, Cervical Cancer, Childhood (Primary) Hepatocellular Cancer, Childhood (Primary) Liver Cancer, Childhood Acute Lymphoblastic Leukemia, Childhood Acute Myeloid Leukemia, Childhood Brain Stem Glioma, Childhood Cerebellar Astrocytoma, Childhood Cerebral Astrocytoma, Childhood Extracranial Germ Cell Tumors, Childhood Hodgkin's Disease, Childhood Hodgkin's Lymphoma, Childhood Hypothalamic and Visual Pathway Glioma, Childhood Lymphoblastic Leukemia, Childhood Medulloblastoma, Childhood Non-Hodgkin's Lymphoma, Childhood Pineal and Supratentorial Primitive Neuroectodermal Tumors, Childhood Primary Liver Cancer, Childhood Rhabdomyosarcoma, Childhood Soft Tissue Sarcoma, Childhood Visual Pathway and Hypothalamic Glioma, Chronic Lymphocytic Leukemia, Chronic Myelogenous Leukemia, Colon Cancer, Cutaneous T-Cell Lymphoma, Endocrine Pancreas Islet Cell Carcinoma, Endometrial Cancer, Ependymoma, Epithelial Cancer, Esophageal Cancer, Ewing's Sarcoma and Related Tumors, Exocrine Pancreatic Cancer, Extracranial Germ Cell Tumor, Extragonadal Germ Cell Tumor, Extrahepatic Bile Duct Cancer, Eye Cancer, Female Breast Cancer, Gaucher's Disease, Gallbladder Cancer, Gastric Cancer, Gastrointestinal Carcinoid Tumor, Gastrointestinal Tumors, Germ Cell Tumors, Gestational Trophoblastic Tumor, Hairy Cell Leukemia, Head and Neck Cancer, Hepatocellular Cancer, Hodgkin's Disease, Hodgkin's Lymphoma, Hypergammaglobulinemia, Hypopharyngeal Cancer, Intestinal Cancers, Intraocular Melanoma, Islet Cell Carcinoma, Islet Cell Pancreatic Cancer, Kaposi's Sarcoma, Kidney Cancer, Laryngeal Cancer, Lip and Oral Cavity Cancer, Liver Cancer, Lung Cancer, Lymphoproliferative Disorders, Macroglobulinemia, Male Breast Cancer, Malignant Mesothelioma, Malignant Thymoma, Medulloblastoma, Melanoma, Mesothelioma, Metastatic Occult Primary Squamous Neck Cancer, Metastatic Primary Squamous Neck Cancer, Metastatic Squamous Neck Cancer, Multiple Myeloma, Multiple Myeloma/Plasma Cell Neoplasm, Myelodysplastic Syndrome, Myelogenous Leukemia, Myeloid Leukemia, Myeloproliferative Disorders, Nasal Cavity and Paranasal Sinus Cancer, Nasopharyngeal Cancer, Neuroblastoma, Non-Hodgkin's Lymphoma During Pregnancy, Nonmelanoma Skin Cancer, Non-Small Cell Lung Cancer, Occult Primary Metastatic Squamous Neck Cancer, Oropharyngeal Cancer, Osteo-/Malignant Fibrous Sarcoma, Osteosarcoma/Malignant Fibrous Histiocytoma, Osteosarcoma/Malignant Fibrous Histiocytoma of Bone, Ovarian Epithelial Cancer, Ovarian Germ Cell Tumor, Ovarian Low Malignant Potential Tumor, Pancreatic Cancer, Paraproteinemias, Purpura, Parathyroid Cancer, Penile Cancer, Pheochromocytoma, Pituitary Tumor, Plasma Cell Neoplasm/Multiple Myeloma, Primary Central Nervous System Lymphoma, Primary Liver Cancer, Prostate Cancer, Rectal Cancer, Renal Cell Cancer, Renal Pelvis and Ureter Cancer, Retinoblastoma, Rhabdomyosarcoma, Salivary Gland Cancer, Sarcoidosis Sarcomas, Sezary Syndrome, Skin Cancer, Small Cell Lung Cancer, Small Intestine Cancer, Soft Tissue Sarcoma, Squamous Neck Cancer, Stomach Cancer, Supratentorial Primitive Neuroectodermal and Pineal Tumors, T-Cell Lymphoma, Testicular Cancer, Thymoma, Thyroid Cancer, Transitional Cell Cancer of the Renal Pelvis and Ureter, Transitional Renal Pelvis and Ureter Cancer, Trophoblastic Tumors, Ureter and Renal Pelvis Cell Cancer, Urethral Cancer, Uterine Cancer, Uterine Sarcoma, Vaginal Cancer, Visual Pathway and Hypothalamic Glioma, Vulvar Cancer, Waldenstrom's Macroglobulinemia, Wilms' Tumor, and any other hyperproliferative disease, besides neoplasia, located in an organ system listed above.

In another preferred embodiment, polynucleotides or polypeptides, or agonists or antagonists of the present invention are used to detect, prevent, diagnose, prognosticate, treat, and/or ameliorate premalignant conditions and to prevent progression to a neoplastic or malignant state, including but not limited to those disorders described above. Such uses are indicated in conditions known or suspected of preceding progression to neoplasia or cancer, in particular, where non-neoplastic cell growth consisting of hyperplasia, metaplasia, or most particularly, dysplasia has occurred (for review of such abnormal growth conditions, see Robbins and Angell, 1976, Basic Pathology, 2d Ed., W. B. Saunders Co., Philadelphia, pp. 68-79.)

Hyperplasia is a form of controlled cell proliferation, involving an increase in cell number in a tissue or organ, without significant alteration in structure or function. Hyperplastic disorders which can be detected, prevented, diagnosed, prognosticated, treated, and/or ameliorated with compositions of the invention (including polynucleotides, polypeptides, agonists or antagonists) include, but are not limited to, angiofollicular mediastinal lymph node hyperplasia, angiolymphoid hyperplasia with eosinophilia, atypical melanocytic hyperplasia, basal cell hyperplasia, benign giant lymph node hyperplasia, cementum hyperplasia, congenital adrenal hyperplasia, congenital sebaceous hyperplasia, cystic hyperplasia, cystic hyperplasia of the breast, denture hyperplasia, ductal hyperplasia, endometrial hyperplasia, fibromuscular hyperplasia, focal epithelial hyperplasia, gingival hyperplasia, inflammatory fibrous hyperplasia, inflammatory papillary hyperplasia, intravascular papillary endothelial hyperplasia, nodular hyperplasia of prostate, nodular regenerative hyperplasia, pseudoepitheliomatous hyperplasia, senile sebaceous hyperplasia, and verrucous hyperplasia.

Metaplasia is a form of controlled cell growth in which one type of adult or fully differentiated cell substitutes for another type of adult cell. Metaplastic disorders which can be detected, prevented, diagnosed, prognosticated, treated, and/or ameliorated with compositions of the invention (including polynucleotides, polypeptides, agonists or antagonists) include, but are not limited to, agnogenic myeloid metaplasia, apocrine metaplasia, atypical metaplasia, autoparenchymatous metaplasia, connective tissue metaplasia, epithelial metaplasia, intestinal metaplasia, metaplastic anemia, metaplastic ossification, metaplastic polyps, myeloid metaplasia, primary myeloid metaplasia, secondary myeloid metaplasia, squamous metaplasia, squamous metaplasia of amnion, and symptomatic myeloid metaplasia.

Dysplasia is frequently a forerunner of cancer, and is found mainly in the epithelia; it is the most disorderly form of non-neoplastic cell growth, involving a loss in individual cell uniformity and in the architectural orientation of cells. Dysplastic cells often have abnormally large, deeply stained nuclei, and exhibit pleomorphism. Dysplasia characteristically occurs where there exists chronic irritation or inflammation. Dysplastic disorders which can be detected, prevented, diagnosed, prognosticated, treated, and/or ameliorated with compositions of the invention (including polynucleotides, polypeptides, agonists or antagonists) include, but are not limited to, anhidrotic ectodermal dysplasia, anterofacial dysplasia, asphyxiating thoracic dysplasia, atriodigital dysplasia, bronchopulmonary dysplasia, cerebral dysplasia, cervical dysplasia, chondroectodermal dysplasia, cleidocranial dysplasia, congenital ectodermal dysplasia, craniodiaphysial dysplasia, craniocarpotarsal dysplasia, craniometaphysial dysplasia, dentin dysplasia, diaphysial dysplasia, ectodermal dysplasia, enamel dysplasia, encephalo-ophthalmic dysplasia, dysplasia epiphysialis hemimelia, dysplasia epiphysialis multiplex, dysplasia epiphysialis punctata, epithelial dysplasia, faciodigitogenital dysplasia, familial fibrous dysplasia of jaws, familial white folded dysplasia, fibromuscular dysplasia, fibrous dysplasia of bone, florid osseous dysplasia, hereditary renal-retinal dysplasia, hidrotic ectodermal dysplasia, hypohidrotic ectodermal dysplasia, lymphopenic thymic dysplasia, mammary dysplasia, mandibulofacial dysplasia, metaphysial dysplasia, Mondini dysplasia, monostotic fibrous dysplasia, mucoepithelial dysplasia, multiple epiphysial dysplasia, oculoauriculovertebral dysplasia, oculodentodigital dysplasia, oculovertebral dysplasia, odontogenic dysplasia, opthalmomandibulomelic dysplasia, periapical cemental dysplasia, polyostotic fibrous dysplasia, pseudoachondroplastic spondyloepiphysial dysplasia, retinal dysplasia, septo-optic dysplasia, spondyloepiphysial dysplasia, and ventriculoradial dysplasia.

Additional pre-neoplastic disorders which can be detected, prevented, diagnosed, prognosticated, treated, and/or ameliorated with compositions of the invention (including polynucleotides, polypeptides, agonists or antagonists) include, but are not limited to, benign dysproliferative disorders (e.g., benign tumors, fibrocystic conditions, tissue hypertrophy, intestinal polyps, colon polyps, and esophageal dysplasia), leukoplakia, keratoses, Bowen's disease, Farmer's Skin, solar cheilitis, and solar keratosis.

In another embodiment, a polypeptide of the invention, or polynucleotides, antibodies, agonists, or antagonists corresponding to that polypeptide, may be used to diagnose and/or prognosticate disorders associated with the tissue(s) in which the polypeptide of the invention is expressed, including one, two, three, four, five, or more tissues disclosed in Table 1B.2, column 5 (Tissue Distribution Library Code).

In another embodiment, polynucleotides, polypeptides, antibodies, and/or agonists or antagonists of the present invention conjugated to a toxin or a radioactive isotope, as described herein, may be used to treat cancers and neoplasms, including, but not limited to those described herein. In a further preferred embodiment, polynucleotides, polypeptides, antibodies, and/or agonists or antagonists of the present invention conjugated to a toxin or a radioactive isotope, as described herein, may be used to treat acute myelogenous leukemia.

Additionally, polynucleotides, polypeptides, and/or agonists or antagonists of the invention may affect apoptosis, and therefore, would be useful in treating a number of diseases associated with increased cell survival or the inhibition of apoptosis. For example, diseases associated with increased cell survival or the inhibition of apoptosis that could be detected, prevented, diagnosed, prognosticated, treated, and/or ameliorated by polynucleotides, polypeptides, and/or agonists or antagonists of the invention, include cancers (such as follicular lymphomas, carcinomas with p53 mutations, and hormone-dependent tumors, including, but not limited to colon cancer, cardiac tumors, pancreatic cancer, melanoma, retinoblastoma, glioblastoma, lung cancer, intestinal cancer, testicular cancer, stomach cancer, neuroblastoma, myxoma, myoma, lymphoma, endothelioma, osteoblastoma, osteoclastoma, osteosarcoma, chondrosarcoma, adenoma, breast cancer, prostate cancer, Kaposi's sarcoma and ovarian cancer); autoimmune disorders such as, multiple sclerosis, Sjogren's syndrome, Hashimoto's thyroiditis, biliary cirrhosis, Behcet's disease, Crohn's disease, polymyositis, systemic lupus erythematosus and immune-related glomerulonephritis and rheumatoid arthritis) and viral infections (such as herpes viruses, pox viruses and adenoviruses), inflammation, graft v. host disease, acute graft rejection, and chronic graft rejection.

In preferred embodiments, polynucleotides, polypeptides, and/or agonists or antagonists of the invention are used to inhibit growth, progression, and/or metastasis of cancers, in particular those listed above.

Additional diseases or conditions associated with increased cell survival that could be detected, prevented, diagnosed, prognosticated, treated, and/or ameliorated by polynucleotides, polypeptides, and/or agonists or antagonists of the invention, include, but are not limited to, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, emangioblastoma, acoustic neuroma, oligodendroglioma, menangioma, melanoma, neuroblastoma, and retinoblastoma.

Diseases associated with increased apoptosis that could be detected, prevented, diagnosed, prognosticated, treated, and/or ameliorated by polynucleotides, polypeptides, and/or agonists or antagonists of the invention, include AIDS; neurodegenerative disorders (such as Alzheimer's disease, Parkinson's disease, amyotrophic lateral sclerosis, retinitis pigmentosa, cerebellar degeneration and brain tumor or prior associated disease); autoimmune disorders (such as, multiple sclerosis, Sjogren's syndrome, Hashimoto's thyroiditis, biliary cirrhosis, Behcet's disease, Crohn's disease, polymyositis, systemic lupus erythematosus and immune-related glomerulonephritis and rheumatoid arthritis) myelodysplastic syndromes (such as aplastic anemia), graft v. host disease, ischemic injury (such as that caused by myocardial infarction, stroke and reperfusion injury), liver injury (e.g., hepatitis related liver injury, ischemia/reperfusion injury, cholestosis (bile duct injury) and liver cancer); toxin-induced liver disease (such as that caused by alcohol), septic shock, cachexia and anorexia.

Hyperproliferative diseases and/or disorders that could be detected, prevented, diagnosed, prognosticated, treated, and/or ameliorated by polynucleotides, polypeptides, and/or agonists or antagonists of the invention, include, but are not limited to, neoplasms located in the liver, abdomen, bone, breast, digestive system, pancreas, peritoneum, endocrine glands (adrenal, parathyroid, pituitary, testicles, ovary, thymus, thyroid), eye, head and neck, nervous system (central and peripheral), lymphatic system, pelvis, skin, soft tissue, spleen, thorax, and urogenital tract.

Similarly, other hyperproliferative disorders can also be detected, prevented, diagnosed, prognosticated, treated, and/or ameliorated by polynucleotides, polypeptides, and/or agonists or antagonists of the invention. Examples of such hyperproliferative disorders include, but are not limited to: hypergammaglobulinemia, lymphoproliferative disorders, paraproteinemias, purpura, sarcoidosis, Sezary Syndrome, Waldenstron's macroglobulinemia, Gaucher's Disease, histiocytosis, and any other hyperproliferative disease, besides neoplasia, located in an organ system listed above.

Another preferred embodiment utilizes polynucleotides of the present invention to inhibit aberrant cellular division, by gene therapy using the present invention, and/or protein fusions or fragments thereof.

Thus, the present invention provides a method for treating cell proliferative disorders by inserting into an abnormally proliferating cell a polynucleotide of the present invention, wherein said polynucleotide represses said expression.

Another embodiment of the present invention provides a method of treating cell-proliferative disorders in individuals comprising administration of one or more active gene copies of the present invention to an abnormally proliferating cell or cells. In a preferred embodiment, polynucleotides of the present invention is a DNA construct comprising a recombinant expression vector effective in expressing a DNA sequence encoding said polynucleotides. In another preferred embodiment of the present invention, the DNA construct encoding the polynucleotides of the present invention is inserted into cells to be treated utilizing a retrovirus, or more preferably an adenoviral vector (See G J. Nabel, et. al., PNAS 1999 96: 324-326, which is hereby incorporated by reference). In a most preferred embodiment, the viral vector is defective and will not transform non-proliferating cells, only proliferating cells. Moreover, in a preferred embodiment, the polynucleotides of the present invention inserted into proliferating cells either alone, or in combination with or fused to other polynucleotides, can then be modulated via an external stimulus (i.e. magnetic, specific small molecule, chemical, or drug administration, etc.), which acts upon the promoter upstream of said polynucleotides to induce expression of the encoded protein product. As such the beneficial therapeutic affect of the present invention may be expressly modulated (i.e. to increase, decrease, or inhibit expression of the present invention) based upon said external stimulus.

Polynucleotides of the present invention may be useful in repressing expression of oncogenic genes or antigens. By "repressing expression of the oncogenic genes" is intended the suppression of the transcription of the gene, the degradation of the gene transcript (pre-message RNA), the inhibition of splicing, the destruction of the messenger RNA, the prevention of the post-translational modifications of the protein, the destruction of the protein, or the inhibition of the normal function of the protein.

For local administration to abnormally proliferating cells, polynucleotides of the present invention may be administered by any method known to those of skill in the art including, but not limited to transfection, electroporation, microinjection of cells, or in vehicles such as liposomes, LIPOFECTIN™, or as naked polynucleotides, or any other method described throughout the specification. The polynucleotide of the present invention may be delivered by known gene delivery systems such as, but not limited to, retroviral vectors (Gilboa, J. Virology 44:845 (1982); Hocke, Nature 320:275 (1986); Wilson, et al., Proc. Natl. Acad. Sci. U.S.A. 85:3014), vaccinia virus system (Chakrabarty et al., Mol. Cell Biol. 5:3403 (1985) or other efficient DNA delivery systems (Yates et al., Nature 313:812 (1985)) known to those skilled in the art. These references are exemplary only and are hereby incorporated by reference. In order to specifically deliver or transfect cells which are abnormally proliferating and spare non-dividing cells, it is preferable to utilize a retrovirus, or adenoviral (as described in the art and elsewhere herein) delivery system known to those of skill in the art. Since host DNA replication is required for retroviral DNA to integrate and the retrovirus will be unable to self replicate due to the lack of the retrovirus genes needed for its life cycle. Utilizing such a retroviral delivery system for polynucleotides of the present invention will target said gene and constructs to abnormally proliferating cells and will spare the non-dividing normal cells.

The polynucleotides of the present invention may be delivered directly to cell proliferative disorder/disease sites in internal organs, body cavities and the like by use of imaging devices used to guide an injecting needle directly to the disease site. The polynucleotides of the present invention may also be administered to disease sites at the time of surgical intervention.

By "cell proliferative disease" is meant any human or animal disease or disorder, affecting any one or any combination of organs, cavities, or body parts, which is characterized by single or multiple local abnormal proliferations of cells, groups of cells, or tissues, whether benign or malignant.

Any amount of the polynucleotides of the present invention may be administered as long as it has a biologically inhibiting effect on the proliferation of the treated cells. Moreover, it is possible to administer more than one of the polynucleotide of the present invention simultaneously to the same site. By "biologically inhibiting" is meant partial or total growth inhibition as well as decreases in the rate of proliferation or growth of the cells. The biologically inhibitory dose may be determined by assessing the effects of the polynucleotides of the present invention on target malignant or abnormally proliferating cell growth in tissue culture, tumor growth in animals and cell cultures, or any other method known to one of ordinary skill in the art.

The present invention is further directed to antibody-based therapies which involve administering of anti-polypeptides and anti-polynucleotide antibodies to a mammalian, preferably human, patient for treating one or more of the described disorders. Methods for producing anti-polypeptides and anti-polynucleotide antibodies polyclonal and monoclonal antibodies are described in detail elsewhere herein. Such antibodies may be provided in pharmaceutically acceptable compositions as known in the art or as described herein.

A summary of the ways in which the antibodies of the present invention may be used therapeutically includes binding polynucleotides or polypeptides of the present invention locally or systemically in the body or by direct cytotoxicity of the antibody, e.g. as mediated by complement (CDC) or by effector cells (ADCC). Some of these approaches are described in more detail below. Armed with the teachings provided herein, one of ordinary skill in the art will know how to use the antibodies of the present invention for diagnosis, prognosis, monitoring, or therapeutic purposes without undue experimentation.

In particular, the antibodies, fragments and derivatives of the present invention are useful for treating a subject having or developing cell proliferative and/or differentiation disorders as described herein. Such treatment comprises administering a single or multiple doses of the antibody, or a fragment, derivative, or a conjugate thereof.

The antibodies of this invention may be advantageously utilized in combination with other monoclonal or chimeric antibodies, or with lymphokines or hematopoietic growth factors, for example, which serve to increase the number or activity of effector cells which interact with the antibodies.

It is preferred to use high affinity and/or potent in vivo inhibiting and/or neutralizing antibodies against polypeptides or polynucleotides of the present invention, fragments or regions thereof, for both immunoassays directed to and therapy of disorders related to polynucleotides or polypeptides, including fragments thereof, of the present invention. Such antibodies, fragments, or regions, will preferably have an affinity for polynucleotides or polypeptides, including fragments thereof. Preferred binding affinities include those with a dissociation constant or Kd less than $5\times10^{-6}$M, $10^{-6}$M, $5\times10^{-7}$M, $10^{-7}$M, $5\times10^{-8}$M, $10^{-8}$M, $5\times10^{-9}$M, $10^{-9}$M, $5\times10^{-10}$M, $10^{-10}$M, $5\times10^{-11}$M, $10^{-11}$M, $5\times10^{-12}$M, $10^{-12}$M, $5\times10^{-13}$M, $10^{-13}$M, $5\times10^{-14}$M, $10^{-14}$, $5\times10^{-15}$M, and $10^{-15}$M.

Moreover, polypeptides of the present invention are useful in inhibiting the angiogenesis of proliferative cells or tissues, either alone, as a protein fusion, or in combination with other polypeptides directly or indirectly, as described elsewhere herein. In a most preferred embodiment, said anti-angiogenesis effect may be achieved indirectly, for example, through the inhibition of hematopoietic, tumor-specific cells, such as tumor-associated macrophages (See Joseph I B, et al. J Natl Cancer Inst, 90(21):1648-53 (1998), which is hereby incorporated by reference). Antibodies directed to polypeptides or polynucleotides of the present invention may also result in inhibition of angiogenesis directly, or indirectly (See Witte L, et al., Cancer Metastasis Rev. 17(2):155-61 (1998), which is hereby incorporated by reference)).

Polypeptides, including protein fusions, of the present invention, or fragments thereof may be useful in inhibiting proliferative cells or tissues through the induction of apoptosis. Said polypeptides may act either directly, or indirectly to induce apoptosis of proliferative cells and tissues, for example in the activation of a death-domain receptor, such as tumor necrosis factor (TNF) receptor-1, CD95 (Fas/APO-1), TNF-receptor-related apoptosis-mediated protein (TRAMP) and TNF-related apoptosis-inducing ligand (TRAIL) receptor-1 and -2 (See Schulze-Osthoff K, et. al., Eur J Biochem 254(3):439-59 (1998), which is hereby incorporated by reference). Moreover, in another preferred embodiment of the present invention, said polypeptides may induce apoptosis through other mechanisms, such as in the activation of other proteins which will activate apoptosis, or through stimulating the expression of said proteins, either alone or in combination with small molecule drugs or adjuvants, such as apoptonin, galectins, thioredoxins, anti-inflammatory proteins (See for example, Mutat Res 400(1-2):447-55 (1998), Med. Hypotheses. 50(5):423-33 (1998), Chem Biol Interact. April 24; 111-112:23-34 (1998), J Mol Med. 76(6):402-12 (1998), Int J Tissue React; 20(1):3-15 (1998), which are all hereby incorporated by reference).

Polypeptides, including protein fusions to, or fragments thereof, of the present invention are useful in inhibiting the metastasis of proliferative cells or tissues. Inhibition may occur as a direct result of administering polypeptides, or antibodies directed to said polypeptides as described elsewhere herein, or indirectly, such as activating the expression of proteins known to inhibit metastasis, for example alpha 4 integrins, (See, e.g., Curr Top Microbiol Immunol 1998; 231: 125-41, which is hereby incorporated by reference). Such therapeutic effects of the present invention may be achieved either alone, or in combination with small molecule drugs or adjuvants.

In another embodiment, the invention provides a method of delivering compositions containing the polypeptides of the invention (e.g., compositions containing polypeptides or polypeptide antibodies associated with heterologous polypeptides, heterologous nucleic acids, toxins, or prodrugs) to targeted cells expressing the polypeptide of the present invention. Polypeptides or polypeptide antibodies of the invention may be associated with heterologous polypeptides, heterologous nucleic acids, toxins, or prodrugs via hydrophobic, hydrophilic, ionic and/or covalent interactions.

Polypeptides, protein fusions to, or fragments thereof, of the present invention are useful in enhancing the immunogenicity and/or antigenicity of proliferating cells or tissues, either directly, such as would occur if the polypeptides of the present invention 'vaccinated' the immune response to respond to proliferative antigens and immunogens, or indirectly, such as in activating the expression of proteins known to enhance the immune response (e.g. chemokines), to said antigens and immunogens.

Renal Disorders

Polynucleotides, polypeptides, antibodies, and/or agonists or antagonists of the present invention, may be used to detect, prevent, diagnose, prognosticate, treat, and/or ameliorate disorders of the renal system. Renal disorders which can be detected, prevented, diagnosed, prognosticated, treated, and/or ameliorated with compositions of the invention include, but are not limited to, kidney failure, nephritis, blood vessel disorders of kidney, metabolic and congenital kidney disorders, urinary disorders of the kidney, autoimmune disorders, sclerosis and necrosis, electrolyte imbalance, and kidney cancers.

Kidney diseases which can be detected, prevented, diagnosed, prognosticated, treated, and/or ameliorated with compositions of the invention include, but are not limited to, acute kidney failure, chronic kidney failure, atheroembolic renal failure, end-stage renal disease, inflammatory diseases of the kidney (e.g., acute glomerulonephritis, postinfectious glomerulonephritis, rapidly progressive glomerulonephritis, nephrotic syndrome, membranous glomerulonephritis, familial nephrotic syndrome, membranoproliferative glomerulonephritis I and II, mesangial proliferative glomerulonephritis, chronic glomerulonephritis, acute tubulointerstitial nephritis, chronic tubulointerstitial nephritis, acute post-streptococcal glomerulonephritis (PSGN), pyelonephritis, lupus nephritis, chronic nephritis, interstitial nephritis, and post-streptococcal glomerulonephritis), blood vessel disorders of the kidneys (e.g., kidney infarction, atheroembolic kidney disease, cortical necrosis, malignant nephrosclerosis, renal vein thrombosis, renal underperfusion, renal retinopathy, renal ischemia-reperfusion, renal artery embolism, and renal artery stenosis), and kidney disorders resulting form urinary tract disease (e.g., pyelonephritis, hydronephrosis, urolithiasis (renal lithiasis, nephrolithiasis), reflux nephropathy, urinary tract infections, urinary retention, and acute or chronic unilateral obstructive uropathy.)

In addition, compositions of the invention can be used to detect, prevent, diagnose, prognosticate, treat, and/or ameliorate metabolic and congenital disorders of the kidney (e.g., uremia, renal amyloidosis, renal osteodystrophy, renal tubular acidosis, renal glycosuria, nephrogenic diabetes insipidus, cystinuria, Fanconi's syndrome, renal fibrocystic osteosis (renal rickets), Hartnup disease, Bartter's syndrome, Liddle's syndrome, polycystic kidney disease, medullary cystic disease, medullary sponge kidney, Alport's syndrome, nail-patella syndrome, congenital nephrotic syndrome, CRUSH syndrome, horseshoe kidney, diabetic nephropathy, nephrogenic diabetes insipidus, analgesic nephropathy, kidney stones, and membranous nephropathy), and autoimmune disorders of the kidney (e.g., systemic lupus erythematosus (SLE), Goodpasture syndrome, IgA nephropathy, and IgM mesangial proliferative glomerulonephritis).

Compositions of the invention can also be used to detect, prevent, diagnose, prognosticate, treat, and/or ameliorate sclerotic or necrotic disorders of the kidney (e.g., glomerulosclerosis, diabetic nephropathy, focal segmental glomerulosclerosis (FSGS), necrotizing glomerulonephritis, and renal papillary necrosis), cancers of the kidney (e.g., nephroma, hypernephroma, nephroblastoma, renal cell cancer, transitional cell cancer, renal adenocarcinoma, squamous cell cancer, and Wilm's tumor), and electrolyte imbalances (e.g., nephrocalcinosis, pyuria, edema, hydronephritis, proteinuria, hyponatremia, hypernatremia, hypokalemia, hyperkalemia, hypocalcemia, hypercalcemia, hypophosphatemia, and hyperphosphatemia).

Polypeptides may be administered using any method known in the art, including, but not limited to, direct needle injection at the delivery site, intravenous injection, topical administration, catheter infusion, BIOLISTIC™ injectors, particle accelerators, gelfoam sponge depots, other commercially available depot materials, osmotic pumps, oral or suppositorial solid pharmaceutical formulations, decanting or topical applications during surgery, aerosol delivery. Such methods are known in the art. Polypeptides may be administered as part of a Therapeutic, described in more detail below. Methods of delivering polynucleotides are described in more detail herein.

Cardiovascular Disorders

Polynucleotides or polypeptides, or agonists or antagonists of the present invention, may be used to detect, prevent, diagnose, prognosticate, treat, and/or ameliorate cardiovascular diseases and disorders, including, but not limited to, peripheral artery disease, such as limb ischemia.

Cardiovascular disorders include, but are not limited to, cardiovascular abnormalities, such as arterio-arterial fistula, arteriovenous fistula, cerebral arteriovenous malformations, congenital heart defects, pulmonary atresia, and Scimitar Syndrome. Congenital heart defects include, but are not limited to, aortic coarctation, cor triatriatum, coronary vessel anomalies, crisscross heart, dextrocardia, patent ductus arteriosus, Ebstein's anomaly, Eisenmenger complex, hypoplastic left heart syndrome, levocardia, tetralogy of fallot, transposition of great vessels, double outlet right ventricle, tricuspid atresia, persistent truncus arteriosus, and heart septal defects, such as aortopulmonary septal defect, endocardial cushion defects, Lutembacher's Syndrome, trilogy of Fallot, ventricular heart septal defects.

Cardiovascular disorders also include, but are not limited to, heart disease, such as arrhythmias, carcinoid heart disease, high cardiac output, low cardiac output, cardiac tamponade, endocarditis (including bacterial), heart aneurysm, cardiac arrest, congestive heart failure, congestive cardiomyopathy, paroxysmal dyspnea, cardiac edema, heart hypertrophy, congestive cardiomyopathy, left ventricular hypertrophy, right ventricular hypertrophy, post-infarction heart rupture, ventricular septal rupture, heart valve diseases, myocardial diseases, myocardial ischemia, pericardial effusion, pericarditis (including constrictive and tuberculous), pneumopericardium, postpericardiotomy syndrome, pulmonary heart disease, rheumatic heart disease, ventricular dysfunction, hyperemia, cardiovascular pregnancy complications, Scimitar Syndrome, cardiovascular syphilis, and cardiovascular tuberculosis.

Arrhythmias include, but are not limited to, sinus arrhythmia, atrial fibrillation, atrial flutter, bradycardia, extrasystole, Adams-Stokes Syndrome, bundle-branch block, sinoatrial block, long QT syndrome, parasystole, Lown-Ganong-Levine Syndrome, Mahaim-type pre-excitation syndrome, Wolff-Parkinson-White syndrome, sick sinus syndrome, tachycardias, and ventricular fibrillation. Tachycardias include paroxysmal tachycardia, supraventricular tachycardia, accelerated idioventricular rhythm, atrioventricular nodal reentry tachycardia, ectopic atrial tachycardia, ectopic junctional tachycardia, sinoatrial nodal reentry tachycardia, sinus tachycardia, Torsades de Pointes, and ventricular tachycardia.

Heart valve diseases include, but are not limited to, aortic valve insufficiency, aortic valve stenosis, hear murmurs, aortic valve prolapse, mitral valve prolapse, tricuspid valve prolapse, mitral valve insufficiency, mitral valve stenosis, pulmonary atresia, pulmonary valve insufficiency, pulmonary valve stenosis, tricuspid atresia, tricuspid valve insufficiency, and tricuspid valve stenosis.

Myocardial diseases include, but are not limited to, alcoholic cardiomyopathy, congestive cardiomyopathy, hypertrophic cardiomyopathy, aortic subvalvular stenosis, pulmonary subvalvular stenosis, restrictive cardiomyopathy, Chagas cardiomyopathy, endocardial fibroelastosis, endomyocardial fibrosis, Kearns Syndrome, myocardial reperfusion injury, and myocarditis.

Myocardial ischemias include, but are not limited to, coronary disease, such as angina pectoris, coronary aneurysm, coronary arteriosclerosis, coronary thrombosis, coronary vasospasm, myocardial infarction and myocardial stunning.

Cardiovascular diseases also include vascular diseases such as aneurysms, angiodysplasia, angiomatosis, bacillary angiomatosis, Hippel-Lindau Disease, Klippel-Trenaunay-Weber Syndrome, Sturge-Weber Syndrome, angioneurotic edema, aortic diseases, Takayasu's Arteritis, aortitis, Leriche's Syndrome, arterial occlusive diseases, arteritis, enarteritis, polyarteritis nodosa, cerebrovascular disorders, diabetic angiopathies, diabetic retinopathy, embolisms, thrombosis, erythromelalgia, hemorrhoids, hepatic veno-occlusive disease, hypertension, hypotension, ischemia, peripheral vascular diseases, phlebitis, pulmonary veno-occlusive disease, Raynaud's disease, CREST syndrome, retinal vein occlusion, Scimitar syndrome, superior vena cava syndrome, telangiectasia, atacia telangiectasia, hereditary hemorrhagic telangiectasia, varicocele, varicose veins, varicose ulcer, vasculitis, and venous insufficiency.

Aneurysms include, but are not limited to, dissecting aneurysms, false aneurysms, infected aneurysms, ruptured aneurysms, aortic aneurysms, cerebral aneurysms, coronary aneurysms, heart aneurysms, and iliac aneurysms.

Arterial occlusive diseases include, but are not limited to, arteriosclerosis, intermittent claudication, carotid stenosis, fibromuscular dysplasias, mesenteric vascular occlusion, Moyamoya disease, renal artery obstruction, retinal artery occlusion, and thromboangiitis obliterans.

Cerebrovascular disorders include, but are not limited to, carotid artery diseases, cerebral amyloid angiopathy, cerebral aneurysm, cerebral anoxia, cerebral arteriosclerosis, cerebral arteriovenous malformation, cerebral artery diseases, cerebral embolism and thrombosis, carotid artery thrombosis, sinus thrombosis, Wallenberg's syndrome, cerebral hemorrhage, epidural hematoma, subdural hematoma, subaraxhnoid hemorrhage, cerebral infarction, cerebral ischemia (including transient), subclavian steal syndrome, periventricular leukomalacia, vascular headache, cluster headache, migraine, and vertebrobasilar insufficiency.

Embolisms include, but are not limited to, air embolisms, amniotic fluid embolisms, cholesterol embolisms, blue toe syndrome, fat embolisms, pulmonary embolisms, and thromoboembolisms. Thrombosis include, but are not limited to, coronary thrombosis, hepatic vein thrombosis, retinal vein occlusion, carotid artery thrombosis, sinus thrombosis, Wallenberg's syndrome, and thrombophlebitis.

Ischemic disorders include, but are not limited to, cerebral ischemia, ischemic colitis, compartment syndromes, anterior compartment syndrome, myocardial ischemia, reperfusion injuries, and peripheral limb ischemia. Vasculitis includes, but is not limited to, aortitis, arteritis, Behcet's Syndrome, Churg-Strauss Syndrome, mucocutaneous lymph node syndrome, thromboangiitis obliterans, hypersensitivity vasculitis, Schoenlein-Henoch purpura, allergic cutaneous vasculitis, and Wegener's granulomatosis.

Polynucleotides or polypeptides, or agonists or antagonists of the invention, are especially effective for the treatment of critical limb ischemia and coronary disease.

Polypeptides may be administered using any method known in the art, including, but not limited to, direct needle injection at the delivery site, intravenous injection, topical administration, catheter infusion, BIOLISTIC™ injectors, particle accelerators, gelfoam sponge depots, other commercially available depot materials, osmotic pumps, oral or suppositorial solid pharmaceutical formulations, decanting or topical applications during surgery, aerosol delivery. Such methods are known in the art. Polypeptides may be administered as part of a Therapeutic, described in more detail below. Methods of delivering polynucleotides are described in more detail herein.

Respiratory Disorders

Polynucleotides or polypeptides, or agonists or antagonists of the present invention may be used to detect, prevent, diagnose, prognosticate, treat, and/or ameliorate diseases and/or disorders of the respiratory system.

Diseases and disorders of the respiratory system include, but are not limited to, nasal vestibulitis, nonallergic rhinitis (e.g., acute rhinitis, chronic rhinitis, atrophic rhinitis, vasomotor rhinitis), nasal polyps, and sinusitis, juvenile angiofibromas, cancer of the nose and juvenile papillomas, vocal cord polyps, nodules (singer's nodules), contact ulcers, vocal cord paralysis, laryngoceles, pharyngitis (e.g., viral and bacterial), tonsillitis, tonsillar cellulitis, parapharyngeal abscess, laryngitis, laryngoceles, and throat cancers (e.g., cancer of the nasopharynx, tonsil cancer, larynx cancer), lung cancer (e.g., squamous cell carcinoma, small cell (oat cell) carcinoma, large cell carcinoma, and adenocarcinoma), allergic disorders (eosinophilic pneumonia, hypersensitivity pneumonitis (e.g., extrinsic allergic alveolitis, allergic interstitial pneumonitis, organic dust pneumoconiosis, allergic bronchopulmonary aspergillosis, asthma, Wegener's granulomatosis (granulomatous vasculitis), Goodpasture's syndrome)), pneumonia (e.g., bacterial pneumonia (e.g., *Streptococcus pneumoniae* (pneumoncoccal pneumonia), *Staphylococcus aureus* (staphylococcal pneumonia), Gram-negative bacterial pneumonia (caused by, e.g., *Klebsiella* and *Pseudomas* spp.), *Mycoplasma pneumoniae* pneumonia, *Hemophilus influenzae* pneumonia, *Legionella pneumophila* (Legionnaires' disease), and *Chlamydia psittaci* (Psittacosis)), and viral pneumonia (e.g., influenza, chickenpox (varicella).

Additional diseases and disorders of the respiratory system include, but are not limited to bronchiolitis, polio (poliomyelitis), croup, respiratory syncytial viral infection, mumps, erythema infectiosum (fifth disease), roseola infantum, progressive rubella panencephalitis, german measles, and subacute sclerosing panencephalitis), fungal pneumonia (e.g., Histoplasmosis, Coccidioidomycosis, Blastomycosis, fungal infections in people with severely suppressed immune systems (e.g., cryptococcosis, caused by *Cryptococcus neoformans*; aspergillosis, caused by *Aspergillus* spp.; candidiasis, caused by *Candida*; and mucormycosis)), *Pneumocystis carinii* (pneumocystis pneumonia), atypical pneumonias (e.g., *Mycoplasma* and *Chlamydia* spp.), opportunistic infection pneumonia, nosocomial pneumonia, chemical pneumonitis, and aspiration pneumonia, pleural disorders (e.g., pleurisy, pleural effusion, and pneumothorax (e.g., simple spontaneous pneumothorax, complicated spontaneous pneumothorax, tension pneumothorax)), obstructive airway diseases (e.g., asthma, chronic obstructive pulmonary disease (COPD), emphysema, chronic or acute bronchitis), occupational lung diseases (e.g., silicosis, black lung (coal workers' pneumoconiosis), asbestosis, berylliosis, occupational asthsma, byssinosis, and benign pneumoconiosis), Infiltrative Lung Disease (e.g., pulmonary fibrosis (e.g., fibrosing alveolitis, usual interstitial pneumonia), idiopathic pulmonary fibrosis, desquamative interstitial pneumonia, lymphoid interstitial pneumonia, histiocytosis X (e.g., Letterer-Siwe disease, Hand-Schüller-Christian disease, eosinophilic granuloma), idiopathic pulmonary hemosiderosis, sarcoidosis and pulmonary alveolar proteinosis), Acute respiratory distress syndrome (also called, e.g., adult respiratory distress syndrome), edema, pulmonary embolism, bronchitis (e.g., viral, bacterial), bronchiectasis, atelectasis, lung abscess (caused by, e.g., *Staphylococcus aureus* or *Legionella pneumophila*), and cystic fibrosis.

Anti Angiogenesis Activity

The naturally occurring balance between endogenous stimulators and inhibitors of angiogenesis is one in which inhibitory influences predominate. Rastinejad et al., *Cell* 56:345-355 (1989). In those rare instances in which neovascularization occurs under normal physiological conditions, such as wound healing, organ regeneration, embryonic development, and female reproductive processes, angiogenesis is stringently regulated and spatially and temporally delimited. Under conditions of pathological angiogenesis such as that characterizing solid tumor growth, these regulatory controls fail. Unregulated angiogenesis becomes pathologic and sustains progression of many neoplastic and non-neoplastic diseases. A number of serious diseases are dominated by abnormal neovascularization including solid tumor growth and metastases, arthritis, some types of eye disorders, and psoriasis. See, e.g., reviews by Moses et al., *Biotech.* 9:630-634 (1991); Folkman et al., *N. Engl. J. Med.,* 333:1757-1763 (1995); Auerbach et al., *J. Microvasc. Res.* 29:401-411 (1985); Folkman, Advances in Cancer Research, eds. Klein and Weinhouse, Academic Press, New York, pp. 175-203 (1985); Patz, *Am. J. Opthalmol.* 94:715-743 (1982); and Folkman et al., Science 221:719-725 (1983). In a number of pathological conditions, the process of angiogenesis contributes to the disease state. For example, significant data have accumulated which suggest that the growth of solid tumors is dependent on angiogenesis. Folkman and Klagsbrun, *Science* 235:442-447 (1987).

The present invention provides for treatment of diseases or disorders associated with neovascularization by administration of the polynucleotides and/or polypeptides of the invention, as well as agonists or antagonists of the present invention. Malignant and metastatic conditions which can be treated with the polynucleotides and polypeptides, or agonists or antagonists of the invention include, but are not limited to, malignancies, solid tumors, and cancers described herein and otherwise known in the art (for a review of such disorders, see Fishman et al., Medicine, 2d Ed., J. B. Lippincott Co., Philadelphia (1985)). Thus, the present invention provides a method of treating an angiogenesis-related disease and/or disorder, comprising administering to an individual in need thereof a therapeutically effective amount of a polynucleotide, polypeptide, antagonist and/or agonist of the invention. For example, polynucleotides, polypeptides, antagonists and/or agonists may be utilized in a variety of additional methods in order to therapeutically treat a cancer or tumor. Cancers which may be treated with polynucleotides, polypeptides, antagonists and/or agonists include, but are not limited to solid tumors, including prostate, lung, breast, ovarian, stomach, pancreas, larynx, esophagus, testes, liver, parotid, biliary tract, colon, rectum, cervix, uterus, endometrium, kidney, bladder, thyroid cancer; primary tumors and metastases; melanomas; glioblastoma; Kaposi's sarcoma; leiomyosarcoma; non-small cell lung cancer; colorectal cancer; advanced malignancies; and blood born tumors such as leukemias. For example, polynucleotides, polypeptides, antagonists and/or agonists may be delivered topically, in order to treat cancers such as skin cancer, head and neck tumors, breast tumors, and Kaposi's sarcoma.

Within yet other aspects, polynucleotides, polypeptides, antagonists and/or agonists may be utilized to treat superficial forms of bladder cancer by, for example, intravesical administration. Polynucleotides, polypeptides, antagonists and/or agonists may be delivered directly into the tumor, or near the tumor site, via injection or a catheter. Of course, as the artisan of ordinary skill will appreciate, the appropriate mode of administration will vary according to the cancer to be treated. Other modes of delivery are discussed herein.

Polynucleotides, polypeptides, antagonists and/or agonists may be useful in treating other disorders, besides cancers, which involve angiogenesis. These disorders include, but are not limited to: benign tumors, for example hemangiomas, acoustic neuromas, neurofibromas, trachomas, and pyogenic granulomas; artheroscleric plaques; ocular angiogenic diseases, for example, diabetic retinopathy, retinopathy of prematurity, macular degeneration, corneal graft rejection, neovascular glaucoma, retrolental fibroplasia, rubeosis, retinoblastoma, uvietis and Pterygia (abnormal blood vessel growth) of the eye; rheumatoid arthritis; psoriasis; delayed wound healing; endometriosis; vasculogenesis; granulations; hypertrophic scars (keloids); nonunion fractures; scleroderma; trachoma; vascular adhesions; myocardial angiogenesis; coronary collaterals; cerebral collaterals; arteriovenous malformations; ischemic limb angiogenesis; Osler-Webber Syndrome; plaque neovascularization; telangiectasia; hemophiliac joints; angiofibroma; fibromuscular dysplasia; wound granulation; Crohn's disease; and atherosclerosis.

For example, within one aspect of the present invention methods are provided for treating hypertrophic scars and keloids, comprising the step of administering a polynucleotide, polypeptide, antagonist and/or agonist of the invention to a hypertrophic scar or keloid.

Within one embodiment of the present invention polynucleotides, polypeptides, antagonists and/or agonists of the invention are directly injected into a hypertrophic scar or keloid, in order to prevent the progression of these lesions. This therapy is of particular value in the prophylactic treatment of conditions which are known to result in the development of hypertrophic scars and keloids (e.g., burns), and is preferably initiated after the proliferative phase has had time to progress (approximately 14 days after the initial injury), but before hypertrophic scar or keloid development. As noted above, the present invention also provides methods for treating neovascular diseases of the eye, including for example, corneal neovascularization, neovascular glaucoma, proliferative diabetic retinopathy, retrolental fibroplasia and macular degeneration.

Moreover, Ocular disorders associated with neovascularization which can be treated with the polynucleotides and polypeptides of the present invention (including agonists and/or antagonists) include, but are not limited to: neovascular glaucoma, diabetic retinopathy, retinoblastoma, retrolental fibroplasia, uveitis, retinopathy of prematurity macular degeneration, corneal graft neovascularization, as well as other eye inflammatory diseases, ocular tumors and diseases associated with choroidal or iris neovascularization. See, e.g., reviews by Waltman et al., *Am. J. Ophthal.* 85:704-710 (1978) and Gartner et al., *Surv. Ophthal.* 22:291-312 (1978).

Thus, within one aspect of the present invention methods are provided for treating neovascular diseases of the eye such as corneal neovascularization (including corneal graft neovascularization), comprising the step of administering to a patient a therapeutically effective amount of a compound (as described above) to the cornea, such that the formation of blood vessels is inhibited. Briefly, the cornea is a tissue that normally lacks blood vessels. In certain pathological conditions however, capillaries may extend into the cornea from the pericorneal vascular plexus of the limbus. When the cornea becomes vascularized, it also becomes clouded, resulting in a decline in the patient's visual acuity. Visual loss may become complete if the cornea completely opacitates. A wide variety of disorders can result in corneal neovascularization, including for example, corneal infections (e.g., trachoma, herpes simplex keratitis, leishmaniasis and onchocerciasis), immunological processes (e.g., graft rejection and Stevens-Johnson's syndrome), alkali burns, trauma, inflammation (of any cause), toxic and nutritional deficiency states, and as a complication of wearing contact lenses.

Particularly preferred embodiments of the invention may be prepared for topical administration in saline (combined with any of the preservatives and antimicrobial agents commonly used in ocular preparations), and administered in eyedrop form. The solution or suspension may be prepared in its pure form and administered several times daily. Alternatively, anti-angiogenic compositions, prepared as described above, may also be administered directly to the cornea. Within preferred embodiments, the anti-angiogenic composition is prepared with a mucoadhesive polymer that binds to cornea. Within further embodiments, the anti-angiogenic factors or anti-angiogenic compositions may be utilized as an adjunct to conventional steroid therapy. Topical therapy may also be useful prophylactically in corneal lesions which are known to have a high probability of inducing an angiogenic response (such as chemical burns). In these instances the treatment, likely in combination with steroids, may be instituted immediately to help prevent subsequent complications.

Within other embodiments, the compounds described above may be injected directly into the corneal stroma by an ophthalmologist under microscopic guidance. The preferred site of injection may vary with the morphology of the individual lesion, but the goal of the administration would be to place the composition at the advancing front of the vasculature (i.e., interspersed between the blood vessels and the normal cornea). In most cases this would involve perilimbic corneal injection to "protect" the cornea from the advancing blood vessels. This method may also be utilized shortly after a corneal insult in order to prophylactically prevent corneal neovascularization. In this situation the material could be injected in the perilimbic cornea interspersed between the corneal lesion and its undesired potential limbic blood supply. Such methods may also be utilized in a similar fashion to prevent capillary invasion of transplanted corneas. In a sustained-release form injections might only be required 2-3 times per year. A steroid could also be added to the injection solution to reduce inflammation resulting from the injection itself.

Within another aspect of the present invention, methods are provided for treating neovascular glaucoma, comprising the step of administering to a patient a therapeutically effective amount of a polynucleotide, polypeptide, antagonist and/or agonist to the eye, such that the formation of blood vessels is inhibited. In one embodiment, the compound may be administered topically to the eye in order to treat early forms of neovascular glaucoma. Within other embodiments, the compound may be implanted by injection into the region of the anterior chamber angle. Within other embodiments, the compound may also be placed in any location such that the compound is continuously released into the aqueous humor. Within another aspect of the present invention, methods are provided for treating proliferative diabetic retinopathy, comprising the step of administering to a patient a therapeutically effective amount of a polynucleotide, polypeptide, antagonist and/or agonist to the eyes, such that the formation of blood vessels is inhibited.

Within particularly preferred embodiments of the invention, proliferative diabetic retinopathy may be treated by injection into the aqueous humor or the vitreous, in order to increase the local concentration of the polynucleotide, polypeptide, antagonist and/or agonist in the retina. Preferably, this treatment should be initiated prior to the acquisition of severe disease requiring photocoagulation.

Within another aspect of the present invention, methods are provided for treating retrolental fibroplasia, comprising the step of administering to a patient a therapeutically effective amount of a polynucleotide, polypeptide, antagonist and/or agonist to the eye, such that the formation of blood vessels is inhibited. The compound may be administered topically, via intravitreous injection and/or via intraocular implants.

Additionally, disorders which can be treated with the polynucleotides, polypeptides, agonists and/or agonists include, but are not limited to, hemangioma, arthritis, psoriasis, angiofibroma, atherosclerotic plaques, delayed wound healing, granulations, hemophilic joints, hypertrophic scars, nonunion fractures, Osler-Weber syndrome, pyogenic granuloma, scleroderma, trachoma, and vascular adhesions.

Moreover, disorders and/or states, which can be detected, prevented, diagnosed, prognosticated, treated, and/or ameliorated with the polynucleotides, polypeptides, agonists and/or agonists of the invention include, but are not limited to, solid tumors, blood born tumors such as leukemias, tumor metastasis, Kaposi's sarcoma, benign tumors, for example hemangiomas, acoustic neuromas, neurofibromas, trachomas, and pyogenic granulomas, rheumatoid arthritis, psoriasis, ocular angiogenic diseases, for example, diabetic retinopathy, retinopathy of prematurity, macular degeneration, corneal graft rejection, neovascular glaucoma, retrolental fibroplasia, rubeosis, retinoblastoma, and uvietis, delayed wound healing, endometriosis, vasculogenesis, granulations, hypertrophic scars (keloids), nonunion fractures, scleroderma, trachoma, vascular adhesions, myocardial angiogenesis, coronary collaterals, cerebral collaterals, arteriovenous malformations, ischemic limb angiogenesis, Osler-Webber Syndrome, plaque neovascularization, telangiectasia, hemophiliac joints, angiofibroma fibromuscular dysplasia, wound granulation, Crohn's disease, atherosclerosis, birth control agent by preventing vascularization required for embryo implantation controlling menstruation, diseases that have angiogenesis as a pathologic consequence such as cat scratch disease (*Rochele minalia quintosa*), ulcers (*Helicobacter pylori*), Bartonellosis and bacillary angiomatosis.

In one aspect of the birth control method, an amount of the compound sufficient to block embryo implantation is administered before or after intercourse and fertilization have occurred, thus providing an effective method of birth control, possibly a "morning after" method. Polynucleotides, polypeptides, agonists and/or agonists may also be used in controlling menstruation or administered as either a peritoneal lavage fluid or for peritoneal implantation in the treatment of endometriosis.

Polynucleotides, polypeptides, agonists and/or agonists of the present invention may be incorporated into surgical sutures in order to prevent stitch granulomas.

Polynucleotides, polypeptides, agonists and/or agonists may be utilized in a wide variety of surgical procedures. For example, within one aspect of the present invention a compositions (in the form of, for example, a spray or film) may be utilized to coat or spray an area prior to removal of a tumor, in order to isolate normal surrounding tissues from malignant tissue, and/or to prevent the spread of disease to surrounding tissues. Within other aspects of the present invention, compositions (e.g., in the form of a spray) may be delivered via endoscopic procedures in order to coat tumors, or inhibit angiogenesis in a desired locale. Within yet other aspects of the present invention, surgical meshes which have been coated with anti-angiogenic compositions of the present invention may be utilized in any procedure wherein a surgical mesh might be utilized. For example, within one embodiment of the invention a surgical mesh laden with an anti-angiogenic composition may be utilized during abdominal cancer resection surgery (e.g., subsequent to colon resection) in order to provide support to the structure, and to release an amount of the anti-angiogenic factor.

Within further aspects of the present invention, methods are provided for treating tumor excision sites, comprising administering a polynucleotide, polypeptide, agonist and/or agonist to the resection margins of a tumor subsequent to excision, such that the local recurrence of cancer and the formation of new blood vessels at the site is inhibited. Within one embodiment of the invention, the anti-angiogenic compound is administered directly to the tumor excision site (e.g., applied by swabbing, brushing or otherwise coating the resection margins of the tumor with the anti-angiogenic compound). Alternatively, the anti-angiogenic compounds may be incorporated into known surgical pastes prior to administration. Within particularly preferred embodiments of the invention, the anti-angiogenic compounds are applied after hepatic resections for malignancy, and after neurosurgical operations.

Within one aspect of the present invention, polynucleotides, polypeptides, agonists and/or agonists may be administered to the resection margin of a wide variety of tumors, including for example, breast, colon, brain and hepatic tumors. For example, within one embodiment of the invention, anti-angiogenic compounds may be administered to the site of a neurological tumor subsequent to excision, such that the formation of new blood vessels at the site are inhibited.

The polynucleotides, polypeptides, agonists and/or agonists of the present invention may also be administered along with other anti-angiogenic factors. Representative examples of other anti-angiogenic factors include: Anti-Invasive Factor, retinoic acid and derivatives thereof, paclitaxel, Suramin, Tissue Inhibitor of Metalloproteinase-1, Tissue Inhibitor of Metalloproteinase-2, Plasminogen Activator Inhibitor-1, Plasminogen Activator Inhibitor-2, and various forms of the lighter "d group" transition metals.

Lighter "d group" transition metals include, for example, vanadium, molybdenum, tungsten, titanium, niobium, and tantalum species. Such transition metal species may form transition metal complexes. Suitable complexes of the above-mentioned transition metal species include oxo transition metal complexes.

Representative examples of vanadium complexes include oxo vanadium complexes such as vanadate and vanadyl complexes. Suitable vanadate complexes include metavanadate and orthovanadate complexes such as, for example, ammonium metavanadate, sodium metavanadate, and sodium orthovanadate. Suitable vanadyl complexes include, for example, vanadyl acetylacetonate and vanadyl sulfate including vanadyl sulfate hydrates such as vanadyl sulfate mono- and trihydrates.

Representative examples of tungsten and molybdenum complexes also include oxo complexes. Suitable oxo tungsten complexes include tungstate and tungsten oxide complexes. Suitable tungstate complexes include ammonium tungstate, calcium tungstate, sodium tungstate dihydrate, and tungstic acid. Suitable tungsten oxides include tungsten (IV) oxide and tungsten (VI) oxide. Suitable oxo molybdenum complexes include molybdate, molybdenum oxide, and molybdenyl complexes. Suitable molybdate complexes include ammonium molybdate and its hydrates, sodium molybdate and its hydrates, and potassium molybdate and its hydrates. Suitable molybdenum oxides include molybdenum (VI) oxide, molybdenum (VI) oxide, and molybdic acid. Suitable molybdenyl complexes include, for example, molybdenyl acetylacetonate. Other suitable tungsten and molybdenum complexes include hydroxo derivatives derived from, for example, glycerol, tartaric acid, and sugars.

A wide variety of other anti-angiogenic factors may also be utilized within the context of the present invention. Representative examples include platelet factor 4; protamine sulphate; sulphated chitin derivatives (prepared from queen crab shells), (Murata et al., Cancer Res. 51:22-26, 1991); Sulphated Polysaccharide Peptidoglycan Complex (SP-PG) (the function of this compound may be enhanced by the presence of steroids such as estrogen, and tamoxifen citrate); Staurosporine; modulators of matrix metabolism, including for example, proline analogs, cishydroxyproline, d,L-3,4-dehydroproline, Thiaproline, alpha,alpha-dipyridyl, aminopropionitrile fumarate; 4-propyl-5-(4-pyridinyl)-2(3H)-oxazolone; Methotrexate; Mitoxantrone; Heparin; Interferons; 2 Macroglobulin-serum; ChIMP-3 (Pavloff et al., J. Bio. Chem. 267:17321-17326, 1992); Chymostatin (Tomkinson et al., Biochem J. 286:475-480, 1992); Cyclodextrin Tetradecasulfate; Eponemycin; Camptothecin; Fumagillin (Ingber et al., Nature 348:555-557, 1990); Gold Sodium Thiomalate ("GST"; Matsubara and Ziff, J. Clin. Invest. 79:1440-1446, 1987); anticollagenase-serum; alpha2-antiplasmin (Holmes et al., J. Biol. Chem. 262(4):1659-1664, 1987); Bisantrene (National Cancer Institute); Lobenzarit disodium (N-(2)-carboxyphenyl-4-chloroanthronilic acid disodium or "CCA"; Takeuchi et al., Agents Actions 36:312-316, 1992); Thalidomide; Angiostatic steroid; AGM-1470; carboxynaminolmidazole; and metalloproteinase inhibitors such as BB94.

Diseases at the Cellular Level

Diseases associated with increased cell survival or the inhibition of apoptosis that could be detected, prevented, diagnosed, prognosticated, treated, and/or ameliorated using polynucleotides or polypeptides, as well as antagonists or agonists of the present invention, include cancers (such as follicular lymphomas, carcinomas with p53 mutations, and hormone-dependent tumors, including, but not limited to colon cancer, cardiac tumors, pancreatic cancer, melanoma, retinoblastoma, glioblastoma, lung cancer, intestinal cancer, testicular cancer, stomach cancer, neuroblastoma, myxoma, myoma, lymphoma, endothelioma, osteoblastoma, osteoclastoma, osteosarcoma, chondrosarcoma, adenoma, breast cancer, prostate cancer, Kaposi's sarcoma and ovarian cancer); autoimmune disorders (such as, multiple sclerosis, Sjogren's syndrome, Hashimoto's thyroiditis, biliary cirrhosis, Behcet's disease, Crohn's disease, polymyositis, systemic lupus erythematosus and immune-related glomerulonephritis and rheumatoid arthritis) and viral infections (such as herpes viruses, pox viruses and adenoviruses), inflammation, graft v. host disease, acute graft rejection, and chronic graft rejection.

In preferred embodiments, polynucleotides, polypeptides, and/or antagonists of the invention are used to inhibit growth, progression, and/or metasis of cancers, in particular those listed above.

Additional diseases or conditions associated with increased cell survival that could be treated or detected by polynucleotides or polypeptides, or agonists or antagonists of the present invention include, but are not limited to, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

Diseases associated with increased apoptosis that could be detected, prevented, diagnosed, prognosticated, treated, and/or ameliorated using polynucleotides or polypeptides, as well as agonists or antagonists of the present invention, include, but are not limited to, AIDS; neurodegenerative disorders (such as Alzheimer's disease, Parkinson's disease, Amyotrophic lateral sclerosis, Retinitis pigmentosa, Cerebellar degeneration and brain tumor or prior associated disease); autoimmune disorders (such as, multiple sclerosis, Sjogren's syndrome, Hashimoto's thyroiditis, biliary cirrhosis, Behcet's disease, Crohn's disease, polymyositis, systemic lupus erythematosus and immune-related glomerulonephritis and rheumatoid arthritis) myelodysplastic syndromes (such as aplastic anemia), graft v. host disease, ischemic injury (such as that caused by myocardial infarction, stroke and reperfusion injury), liver injury (e.g., hepatitis related liver injury, ischemia/reperfusion injury, cholestosis (bile duct injury) and liver cancer); toxin-induced liver disease (such as that caused by alcohol), septic shock, cachexia and anorexia.

Wound Healing and Epithelial Cell Proliferation

In accordance with yet a further aspect of the present invention, there is provided a process for utilizing polynucleotides or polypeptides, as well as agonists or antagonists of the present invention, for therapeutic purposes, for example, to stimulate epithelial cell proliferation and basal keratinocytes for the purpose of wound healing, and to stimulate hair follicle production and healing of dermal wounds. Polynucleotides or polypeptides, as well as agonists or antagonists of the present invention, may be clinically useful in stimulating wound healing including surgical wounds, excisional wounds, deep wounds involving damage of the dermis and epidermis, eye tissue wounds, dental tissue wounds, oral cavity wounds, diabetic ulcers, dermal ulcers, cubitus ulcers, arterial ulcers, venous stasis ulcers, burns resulting from heat exposure or chemicals, and other abnormal wound healing conditions such as uremia, malnutrition, vitamin deficiencies and complications associated with systemic treatment with steroids, radiation therapy and antineoplastic drugs and antimetabolites. Polynucleotides or polypeptides, as well as agonists or antagonists of the present invention, could be used to promote dermal reestablishment subsequent to dermal loss.

Polynucleotides or polypeptides, as well as agonists or antagonists of the present invention, could be used to increase the adherence of skin grafts to a wound bed and to stimulate re-epithelialization from the wound bed. The following are types of grafts that polynucleotides or polypeptides, agonists or antagonists of the present invention, could be used to increase adherence to a wound bed: autografts, artificial skin, allografts, autodermic graft, autoepdermic grafts, avacular grafts, Blair-Brown grafts, bone graft, brephoplastic grafts, cutis graft, delayed graft, dermic graft, epidermic graft, fascia graft, full thickness graft, heterologous graft, xenograft, homologous graft, hyperplastic graft, lamellar graft, mesh graft, mucosal graft, Ollier-Thiersch graft, omenpal graft, patch graft, pedicle graft, penetrating graft, split skin graft, thick split graft. Polynucleotides or polypeptides, as well as agonists or antagonists of the present invention, can be used to promote skin strength and to improve the appearance of aged skin.

It is believed that polynucleotides or polypeptides, as well as agonists or antagonists of the present invention, will also produce changes in hepatocyte proliferation, and epithelial cell proliferation in the lung, breast, pancreas, stomach, small intestine, and large intestine. Polynucleotides or polypeptides, as well as agonists or antagonists of the present invention, could promote proliferation of epithelial cells such as sebocytes, hair follicles, hepatocytes, type II pneumocytes, mucin-producing goblet cells, and other epithelial cells and their progenitors contained within the skin, lung, liver, and gastrointestinal tract. Polynucleotides or polypeptides, agonists or antagonists of the present invention, may promote proliferation of endothelial cells, keratinocytes, and basal keratinocytes.

Polynucleotides or polypeptides, as well as agonists or antagonists of the present invention, could also be used to reduce the side effects of gut toxicity that result from radiation, chemotherapy treatments or viral infections. Polynucleotides or polypeptides, as well as agonists or antagonists of the present invention, may have a cytoprotective effect on the small intestine mucosa. Polynucleotides or polypeptides, as well as agonists or antagonists of the present invention, may also stimulate healing of mucositis (mouth ulcers) that result from chemotherapy and viral infections.

Polynucleotides or polypeptides, as well as agonists or antagonists of the present invention, could further be used in full regeneration of skin in full and partial thickness skin defects, including burns, (i.e., repopulation of hair follicles, sweat glands, and sebaceous glands), treatment of other skin defects such as psoriasis. Polynucleotides or polypeptides, as well as agonists or antagonists of the present invention, could be used to treat epidermolysis bullosa, a defect in adherence of the epidermis to the underlying dermis which results in frequent, open and painful blisters by accelerating reepithelialization of these lesions. Polynucleotides or polypeptides, as well as agonists or antagonists of the present invention, could also be used to treat gastric and duodenal ulcers and help heal by scar formation of the mucosal lining and regeneration of glandular mucosa and duodenal mucosal lining more rapidly. Inflammatory bowel diseases, such as Crohn's disease and ulcerative colitis, are diseases which result in destruction of the mucosal surface of the small or large intestine, respectively. Thus, polynucleotides or polypeptides, as well as agonists or antagonists of the present invention, could be used to promote the resurfacing of the mucosal surface to aid more rapid healing and to prevent progression of inflammatory bowel disease. Treatment with polynucleotides or polypeptides, agonists or antagonists of the present invention, is expected to have a significant effect on the production of mucus throughout the gastrointestinal tract and could be used to protect the intestinal mucosa from injurious substances that are ingested or following surgery. Polynucleotides or polypeptides, as well as agonists or antagonists of the present invention, could be used to treat diseases associate with the under expression.

Moreover, polynucleotides or polypeptides, as well as agonists or antagonists of the present invention, could be used to prevent and heal damage to the lungs due to various pathological states. Polynucleotides or polypeptides, as well as agonists or antagonists of the present invention, which could stimulate proliferation and differentiation and promote the repair of alveoli and bronchiolar epithelium to prevent or treat acute or chronic lung damage. For example, emphysema, which results in the progressive loss of alveoli, and inhalation injuries, i.e., resulting from smoke inhalation and burns, that cause necrosis of the bronchiolar epithelium and alveoli could be effectively treated using polynucleotides or polypeptides, agonists or antagonists of the present invention. Also, polynucleotides or polypeptides, as well as agonists or antagonists of the present invention, could be used to stimulate the proliferation of and differentiation of type II pneumocytes, which may help treat or prevent disease such as hyaline membrane diseases, such as infant respiratory distress syndrome and bronchopulmonary dysplasia, in premature infants.

Polynucleotides or polypeptides, as well as agonists or antagonists of the present invention, could stimulate the proliferation and differentiation of hepatocytes and, thus, could be used to alleviate or treat liver diseases and pathologies such as fulminant liver failure caused by cirrhosis, liver damage caused by viral hepatitis and toxic substances (i.e., acetaminophen, carbon tetrachloride and other hepatotoxins known in the art).

In addition, polynucleotides or polypeptides, as well as agonists or antagonists of the present invention, could be used treat or prevent the onset of diabetes mellitus. In patients with newly diagnosed Types I and II diabetes, where some islet cell function remains, polynucleotides or polypeptides, as well as agonists or antagonists of the present invention, could be used to maintain the islet function so as to alleviate, delay or prevent permanent manifestation of the disease. Also, polynucleotides or polypeptides, as well as agonists or antagonists of the present invention, could be used as an auxiliary in islet cell transplantation to improve or promote islet cell function.

Neural Activity and Neurological Diseases

The polynucleotides, polypeptides and agonists or antagonists of the invention may be used for the detection, prevention, diagnosis, prognostication, treatment, and/or amelioration of diseases, disorders, damage or injury of the brain and/or nervous system. Nervous system disorders that can be treated with the compositions of the invention (e.g., polypeptides, polynucleotides, and/or agonists or antagonists), include, but are not limited to, nervous system injuries, and diseases or disorders which result in either a disconnection of axons, a diminution or degeneration of neurons, or demyelination. Nervous system lesions which may be treated in a patient (including human and non-human mammalian patients) according to the methods of the invention, include but are not limited to, the following lesions of either the central (including spinal cord, brain) or peripheral nervous systems: (1) ischemic lesions, in which a lack of oxygen in a portion of the nervous system results in neuronal injury or death, including cerebral infarction or ischemia, or spinal cord infarction or ischemia; (2) traumatic lesions, including lesions caused by physical injury or associated with surgery, for example, lesions which sever a portion of the nervous system, or compression injuries; (3) malignant lesions, in which a portion of the nervous system is destroyed or injured by malignant tissue which is either a nervous system associated malignancy or a malignancy derived from non-nervous system tissue; (4) infectious lesions, in which a portion of the nervous system is destroyed or injured as a result of infection, for example, by an abscess or associated with infection by human immunodeficiency virus, herpes zoster, or herpes simplex virus or with Lyme disease, tuberculosis, or syphilis; (5) degenerative lesions, in which a portion of the nervous system is destroyed or injured as a result of a degenerative process including but not limited to, degeneration associated with Parkinson's disease, Alzheimer's disease, Huntington's chorea, or amyotrophic lateral sclerosis (ALS); (6) lesions associated with nutritional diseases or disorders, in which a portion of the nervous system is destroyed or injured by a nutritional disorder or disorder of metabolism including, but not limited to, vitamin B12 deficiency, folic acid deficiency, Wernicke disease, tobacco-alcohol amblyopia, Marchiafava-Bignami disease (primary degeneration of the corpus callosum), and alcoholic cerebellar degeneration; (7) neurological lesions associated with systemic diseases including, but not limited to, diabetes (diabetic neuropathy, Bell's palsy), systemic lupus erythematosus, carcinoma, or sarcoidosis; (8) lesions caused by toxic substances including alcohol, lead, or particular neurotoxins; and (9) demyelinated lesions in which a portion of the nervous system is destroyed or injured by a demyelinating disease including, but not limited to, multiple sclerosis, human immunodeficiency virus-associated myelopathy, transverse myelopathy or various etiologies, progressive multifocal leukoencephalopathy, and central pontine myelinolysis.

In one embodiment, the polypeptides, polynucleotides, or agonists or antagonists of the invention are used to protect neural cells from the damaging effects of hypoxia. In a further preferred embodiment, the polypeptides, polynucleotides, or agonists or antagonists of the invention are used to protect neural cells from the damaging effects of cerebral hypoxia. According to this embodiment, the compositions of the invention are used to treat or prevent neural cell injury associated with cerebral hypoxia. In one non-exclusive aspect of this embodiment, the polypeptides, polynucleotides, or agonists or antagonists of the invention, are used to treat or prevent neural cell injury associated with cerebral ischemia. In another non-exclusive aspect of this embodiment, the polypeptides, polynucleotides, or agonists or antagonists of the invention are used to treat or prevent neural cell injury associated with cerebral infarction.

In another preferred embodiment, the polypeptides, polynucleotides, or agonists or antagonists of the invention are used to treat or prevent neural cell injury associated with a stroke. In a specific embodiment, the polypeptides, polynucleotides, or agonists or antagonists of the invention are used to treat or prevent cerebral neural cell injury associated with a stroke.

In another preferred embodiment, the polypeptides, polynucleotides, or agonists or antagonists of the invention are used to treat or prevent neural cell injury associated with a heart attack. In a specific embodiment, the polypeptides, polynucleotides, or agonists or antagonists of the invention are used to treat or prevent cerebral neural cell injury associated with a heart attack.

The compositions of the invention which are useful for treating or preventing a nervous system disorder may be selected by testing for biological activity in promoting the survival or differentiation of neurons. For example, and not by way of limitation, compositions of the invention which elicit any of the following effects may be useful according to the invention: (1) increased survival time of neurons in culture either in the presence or absence of hypoxia or hypoxic conditions; (2) increased sprouting of neurons in culture or in vivo; (3) increased production of a neuron-associated molecule in culture or in vivo, e.g., choline acetyltransferase or acetylcholinesterase with respect to motor neurons; or (4) decreased symptoms of neuron dysfunction in vivo. Such effects may be measured by any method known in the art. In preferred, non-limiting embodiments, increased survival of neurons may routinely be measured using a method set forth herein or otherwise known in the art, such as, for example, in Zhang et al., *Proc Natl Acad Sci USA* 97:3637-42 (2000) or in Arakawa et al., *J. Neurosci.,* 10:3507-15 (1990); increased sprouting of neurons may be detected by methods known in the art, such as, for example, the methods set forth in Pestronk et al., *Exp. Neurol.,* 70:65-82 (1980), or Brown et al., *Ann. Rev. Neurosci.,* 4:17-42 (1981); increased production of neuron-associated molecules may be measured by bioassay, enzymatic assay, antibody binding, Northern blot assay, etc., using techniques known in the art and depending on the molecule to be measured; and motor neuron dysfunction may be measured by assessing the physical manifestation of motor neuron disorder, e.g., weakness, motor neuron conduction velocity, or functional disability.

In specific embodiments, motor neuron disorders that may be treated according to the invention include, but are not limited to, disorders such as infarction, infection, exposure to toxin, trauma, surgical damage, degenerative disease or malignancy that may affect motor neurons as well as other components of the nervous system, as well as disorders that selectively affect neurons such as amyotrophic lateral sclerosis, and including, but not limited to, progressive spinal muscular atrophy, progressive bulbar palsy, primary lateral sclerosis, infantile and juvenile muscular atrophy, progressive bulbar paralysis of childhood (Fazio-Londe syndrome), poliomyelitis and the post polio syndrome, and Hereditary Motorsensory Neuropathy (Charcot-Marie-Tooth Disease).

Further, polypeptides or polynucleotides of the invention may play a role in neuronal survival; synapse formation; conductance; neural differentiation, etc. Thus, compositions of the invention (including polynucleotides, polypeptides, and agonists or antagonists) may be used to detect, prevent, diagnose, prognosticate, treat, and/or ameliorate diseases or disorders associated with these roles, including, but not limited to, learning and/or cognition disorders. The compositions of the invention may also be useful in the treatment or prevention of neurodegenerative disease states and/or behavioural disorders. Such neurodegenerative disease states and/or behavioral disorders include, but are not limited to, Alzheimer's Disease, Parkinson's Disease, Huntington's Disease, Tourette Syndrome, schizophrenia, mania, dementia, paranoia, obsessive compulsive disorder, panic disorder, learning disabilities, ALS, psychoses, autism, and altered behaviors, including disorders in feeding, sleep patterns, balance, and perception. In addition, compositions of the invention may also play a role in the treatment, prevention and/or detection of developmental disorders associated with the developing embryo, or sexually-linked disorders.

Additionally, polypeptides, polynucleotides and/or agonists or antagonists of the invention, may be useful in protecting neural cells from diseases, damage, disorders, or injury, associated with cerebrovascular disorders including, but not limited to, carotid artery diseases (e.g., carotid artery thrombosis, carotid stenosis, or Moyamoya Disease), cerebral amyloid angiopathy, cerebral aneurysm, cerebral anoxia, cerebral arteriosclerosis, cerebral arteriovenous malformations, cerebral artery diseases, cerebral embolism and thrombosis (e.g., carotid artery thrombosis, sinus thrombosis, or Wallenberg's Syndrome), cerebral hemorrhage (e.g., epidural or subdural hematoma, or subarachnoid hemorrhage), cerebral infarction, cerebral ischemia (e.g., transient cerebral ischemia, Subclavian Steal Syndrome, or vertebrobasilar insufficiency), vascular dementia (e.g., multi-infarct), leukomalacia, periventricular, and vascular headache (e.g., cluster headache or migraines).

In accordance with yet a further aspect of the present invention, there is provided a process for utilizing polynucleotides or polypeptides, as well as agonists or antagonists of the present invention, for therapeutic purposes, for example, to stimulate neurological cell proliferation and/or differentiation. Therefore, polynucleotides, polypeptides, agonists and/or antagonists of the invention may be used to treat and/or detect neurologic diseases. Moreover, polynucleotides or polypeptides, or agonists or antagonists of the invention, can be used as a marker or detector of a particular nervous system disease or disorder.

Examples of neurologic diseases which can be treated or detected with polynucleotides, polypeptides, agonists, and/or antagonists of the present invention include brain diseases, such as metabolic brain diseases which includes phenylketonuria such as maternal phenylketonuria, pyruvate carboxylase deficiency, pyruvate dehydrogenase complex deficiency, Wernicke's Encephalopathy, brain edema, brain neoplasms such as cerebellar neoplasms which include infratentorial neoplasms, cerebral ventricle neoplasms such as choroid plexus neoplasms, hypothalamic neoplasms, supratentorial neoplasms, canavan disease, cerebellar diseases such as cerebellar ataxia which include spinocerebellar degeneration such as ataxia telangiectasia, cerebellar dyssynergia, Friederich's Ataxia, Machado-Joseph Disease, olivopontocerebellar atrophy, cerebellar neoplasms such as infratentorial neoplasms, diffuse cerebral sclerosis such as encephalitis periaxialis, globoid cell leukodystrophy, metachromatic leukodystrophy and subacute sclerosing panencephalitis.

Additional neurologic diseases which can be treated or detected with polynucleotides, polypeptides, agonists, and/or antagonists of the present invention include cerebrovascular disorders (such as carotid artery diseases which include carotid artery thrombosis, carotid stenosis and Moyamoya Disease), cerebral amyloid angiopathy, cerebral aneurysm, cerebral anoxia, cerebral arteriosclerosis, cerebral arteriovenous malformations, cerebral artery diseases, cerebral embolism and thrombosis such as carotid artery thrombosis, sinus thrombosis and Wallenberg's Syndrome, cerebral hemorrhage such as epidural hematoma, subdural hematoma and subarachnoid hemorrhage, cerebral infarction, cerebral ischemia such as transient cerebral ischemia, Subclavian Steal Syndrome and vertebrobasilar insufficiency, vascular dementia such as multi-infarct dementia, periventricular leukomalacia, vascular headache such as cluster headache and migraine.

Additional neurologic diseases which can be treated or detected with polynucleotides, polypeptides, agonists, and/or antagonists of the present invention include dementia such as AIDS Dementia Complex, presenile dementia such as Alzheimer's Disease and Creutzfeldt-Jakob Syndrome, senile dementia such as Alzheimer's Disease and progressive supranuclear palsy, vascular dementia such as multi-infarct dementia, encephalitis which include encephalitis periaxialis, viral encephalitis such as epidemic encephalitis, Japanese Encephalitis, St. Louis Encephalitis, tick-borne encephalitis and West Nile Fever, acute disseminated encephalomyelitis, meningoencephalitis such as uveomeningoencephalitic syndrome, Postencephalitic Parkinson Disease and subacute sclerosing panencephalitis, encephalomalacia such as periventricular leukomalacia, epilepsy such as generalized epilepsy which includes infantile spasms, absence epilepsy, myoclonic epilepsy which includes MERRF Syndrome, tonic-clonic epilepsy, partial epilepsy such as complex partial epilepsy, frontal lobe epilepsy and temporal lobe epilepsy, post-traumatic epilepsy, status epilepticus such as Epilepsia Partialis Continua, and Hallervorden-Spatz Syndrome.

Additional neurologic diseases which can be treated or detected with polynucleotides, polypeptides, agonists, and/or antagonists of the present invention include hydrocephalus such as Dandy-Walker Syndrome and normal pressure hydrocephalus, hypothalamic diseases such as hypothalamic neoplasms, cerebral malaria, narcolepsy which includes cataplexy, bulbar poliomyelitis, cerebri pseudotumor, Rett Syndrome, Reye's Syndrome, thalamic diseases, cerebral toxoplasmosis, intracranial tuberculoma and Zellweger Syndrome, central nervous system infections such as AIDS Dementia Complex, Brain Abscess, subdural empyema, encephalomyelitis such as Equine Encephalomyelitis, Venezuelan Equine Encephalomyelitis, Necrotizing Hemorrhagic Encephalomyelitis, Visna, and cerebral malaria.

Additional neurologic diseases which can be treated or detected with polynucleotides, polypeptides, agonists, and/or antagonists of the present invention include meningitis such as arachnoiditis, aseptic meningtitis such as viral meningtitis which includes lymphocytic choriomeningitis, Bacterial meningtitis which includes *Haemophilus* Meningtitis, *Listeria* Meningtitis, Meningococcal Meningtitis such as Waterhouse-Friderichsen Syndrome, Pneumococcal Meningtitis and meningeal tuberculosis, fungal meningitis such as Cryptococcal Meningtitis, subdural effusion, meningoencephalitis such as uvemeningoencephalitic syndrome, myelitis such as transverse myelitis, neurosyphilis such as tabes dorsalis, poliomyelitis which includes bulbar poliomyelitis and postpoliomyelitis syndrome, prion diseases (such as Creutzfeldt-Jakob Syndrome, Bovine Spongiform Encephalopathy, Gerstmann-Straussler Syndrome, Kuru, Scrapie), and cerebral toxoplasmosis.

Additional neurologic diseases which can be treated or detected with polynucleotides, polypeptides, agonists, and/or antagonists of the present invention include central nervous system neoplasms such as brain neoplasms that include cerebellar neoplasms such as infratentorial neoplasms, cerebral ventricle neoplasms such as choroid plexus neoplasms, hypothalamic neoplasms and supratentorial neoplasms, meningeal neoplasms, spinal cord neoplasms which include epidural neoplasms, demyelinating diseases such as Canavan Diseases, diffuse cerebral sceloris which includes adrenoleukodystrophy, encephalitis periaxialis, globoid cell leukodystrophy, diffuse cerebral sclerosis such as metachromatic leukodystrophy, allergic encephalomyelitis, necrotizing hemorrhagic encephalomyelitis, progressive multifocal leukoencephalopathy, multiple sclerosis, central pontine myelinolysis, transverse myelitis, neuromyelitis optica, Scrapie, Swayback, Chronic Fatigue Syndrome, Visna, High Pressure Nervous Syndrome, Meningism, spinal cord diseases such as amyotonia congenita, amyotrophic lateral sclerosis, spinal muscular atrophy such as Werdnig-Hoffmann Disease, spinal cord compression, spinal cord neoplasms such as epidural neoplasms, syringomyelia, Tabes Dorsalis, Stiff-Man Syndrome, mental retardation such as Angelman Syndrome, Cri-du-Chat Syndrome, De Lange's Syndrome, Down Syndrome, Gangliosidoses such as gangliosidoses G(M1), Sandhoff Disease, Tay-Sachs Disease, Hartnup Disease, homocystinuria, Laurence-Moon-Biedl Syndrome, Lesch-Nyhan Syndrome, Maple Syrup Urine Disease, mucolipidosis such as fucosidosis, neuronal ceroid-lipofuscinosis, oculocerebrorenal syndrome, phenylketonuria such as maternal phenylketonuria, Prader-Willi Syndrome, Rett Syndrome, Rubinstein-Taybi Syndrome, Tuberous Sclerosis, WAGR Syndrome, nervous system abnormalities such as holoprosencephaly, neural tube defects such as anencephaly which includes hydrangencephaly, Arnold-Chairi Deformity, encephalocele, meningocele, meningomyelocele, spinal dysraphism such as spina bifida cystica and spina bifida occulta.

Additional neurologic diseases which can be treated or detected with polynucleotides, polypeptides, agonists, and/or antagonists of the present invention include hereditary motor and sensory neuropathies which include Charcot-Marie Disease, Hereditary optic atrophy, Refsum's Disease, hereditary spastic paraplegia, Werdnig-Hoffmann Disease, Hereditary Sensory and Autonomic Neuropathies such as Congenital Analgesia and Familial Dysautonomia, Neurologic manifestations (such as agnosia that include Gerstmann's Syndrome, Amnesia such as retrograde amnesia, apraxia, neurogenic bladder, cataplexy, communicative disorders such as hearing disorders that includes deafness, partial hearing loss, loudness recruitment and tinnitus, language disorders such as aphasia which include agraphia, anomia, broca aphasia, and Wernicke Aphasia, Dyslexia such as Acquired Dyslexia, language development disorders, speech disorders such as aphasia which includes anomia, broca aphasia and Wernicke Aphasia, articulation disorders, communicative disorders such as speech disorders which include dysarthria, echolalia, mutism and stuttering, voice disorders such as aphonia and hoarseness, decerebrate state, delirium, fasciculation, hallucinations, meningism, movement disorders such as angelman syndrome, ataxia, athetosis, chorea, dystonia, hypokinesia, muscle hypotonia, myoclonus, tic, torticollis and tremor, muscle hypertonia such as muscle rigidity such as stiff-man syndrome, muscle spasticity, paralysis such as facial paralysis which includes Herpes Zoster Oticus, Gastroparesis, Hemiplegia, opthalmoplegia such as diplopia, Duane's Syndrome, Horner's Syndrome, Chronic progressive external opthalmoplegia such as Kearns Syndrome, Bulbar Paralysis, Tropical Spastic Paraparesis, Paraplegia such as Brown-Sequard Syndrome, quadriplegia, respiratory paralysis and vocal cord paralysis, paresis, phantom limb, taste disorders such as ageusia and dysgeusia, vision disorders such as amblyopia, blindness, color vision defects, diplopia, hemianopsia, scotoma and subnormal vision, sleep disorders such as hypersomnia which includes Kleine-Levin Syndrome, insomnia, and somnambulism, spasm such as trismus, unconsciousness such as coma, persistent vegetative state and syncope and vertigo, neuromuscular diseases such as amyotonia congenita, amyotrophic lateral sclerosis, Lambert-Eaton Myasthenic Syndrome, motor neuron disease, muscular atrophy such as spinal muscular atrophy, Charcot-Marie Disease and Werdnig-Hoffmann Disease, Postpoliomyelitis Syndrome, Muscular Dystrophy, Myasthenia Gravis, Myotonia Atrophica, Myotonia Confenita, Nemaline Myopathy, Familial Periodic Paralysis, Multiplex Paramyloclonus, Tropical Spastic Paraparesis and Stiff-Man Syndrome, peripheral nervous system diseases such as acrodynia, amyloid neuropathies, autonomic nervous system diseases such as Adie's Syndrome, Barre-Lieou Syndrome, Familial Dysautonomia, Horner's Syndrome, Reflex Sympathetic Dystrophy and Shy-Drager Syndrome, Cranial Nerve Diseases such as Acoustic Nerve Diseases such as Acoustic Neuroma which includes Neurofibromatosis 2, Facial Nerve Diseases such as Facial Neuralgia, Melkersson-Rosenthal Syndrome, ocular motility disorders which includes amblyopia, nystagmus, oculomotor nerve paralysis, opthalmoplegia such as Duane's Syndrome, Horner's Syndrome, Chronic Progressive External Opthalmoplegia which includes Kearns Syndrome, Strabismus such as Esotropia and Exotropia, Oculomotor Nerve Paralysis, Optic Nerve Diseases such as Optic Atrophy which includes Hereditary Optic Atrophy, Optic Disk Drusen, Optic Neuritis such as Neuromyelitis Optica, Papilledema, Trigeminal Neuralgia, Vocal Cord Paralysis, Demyelinating Diseases such as Neuromyelitis Optica and Swayback, and Diabetic neuropathies such as diabetic foot.

Additional neurologic diseases which can be treated or detected with polynucleotides, polypeptides, agonists, and/or antagonists of the present invention include nerve compression syndromes such as carpal tunnel syndrome, tarsal tunnel syndrome, thoracic outlet syndrome such as cervical rib syndrome, ulnar nerve compression syndrome, neuralgia such as causalgia, cervico-brachial neuralgia, facial neuralgia and trigeminal neuralgia, neuritis such as experimental allergic neuritis, optic neuritis, polyneuritis, polyradiculoneuritis and radiculities such as polyradiculitis, hereditary motor and sensory neuropathies such as Charcot-Marie Disease, Hereditary Optic Atrophy, Refsum's Disease, Hereditary Spastic Paraplegia and Werdnig-Hoffmann Disease, Hereditary Sensory and Autonomic Neuropathies which include Congenital Analgesia and Familial Dysautonomia, POEMS Syndrome, Sciatica, Gustatory Sweating and Tetany).

Endocrine Disorders

Polynucleotides or polypeptides, or agonists or antagonists of the present invention, may be used to detect, prevent, diagnose, prognosticate, treat, and/or ameliorate disorders and/or diseases related to hormone imbalance, and/or disorders or diseases of the endocrine system.

Hormones secreted by the glands of the endocrine system control physical growth, sexual function, metabolism, and other functions. Disorders may be classified in two ways: disturbances in the production of hormones, and the inability of tissues to respond to hormones. The etiology of these hormone imbalance or endocrine system diseases, disorders or conditions may be genetic, somatic, such as cancer and some autoimmune diseases, acquired (e.g., by chemotherapy, injury or toxins), or infectious. Moreover, polynucleotides, polypeptides, antibodies, and/or agonists or antagonists of the present invention can be used as a marker or detector of a particular disease or disorder related to the endocrine system and/or hormone imbalance.

Endocrine system and/or hormone imbalance and/or diseases encompass disorders of uterine motility including, but not limited to: complications with pregnancy and labor (e.g., pre-term labor, post-term pregnancy, spontaneous abortion, and slow or stopped labor); and disorders and/or diseases of the menstrual cycle (e.g., dysmenorrhea and endometriosis).

Endocrine system and/or hormone imbalance disorders and/or diseases include disorders and/or diseases of the pancreas, such as, for example, diabetes mellitus, diabetes insipidus, congenital pancreatic agenesis, pheochromocytoma-islet cell tumor syndrome; disorders and/or diseases of the adrenal glands such as, for example, Addison's Disease, corticosteroid deficiency, virilizing disease, hirsutism, Cushing's Syndrome, hyperaldosteronism, pheochromocytoma; disorders and/or diseases of the pituitary gland, such as, for example, hyperpituitarism, hypopituitarism, pituitary dwarfism, pituitary adenoma, panhypopituitarism, acromegaly, gigantism; disorders and/or diseases of the thyroid, including but not limited to, hyperthyroidism, hypothyroidism, Plummer's disease, Graves' disease (toxic diffuse goiter), toxic nodular goiter, thyroiditis (Hashimoto's thyroiditis, subacute granulomatous thyroiditis, and silent lymphocytic thyroiditis), Pendred's syndrome, myxedema, cretinism, thyrotoxicosis, thyroid hormone coupling defect, thymic aplasia, Hurthle cell tumours of the thyroid, thyroid cancer, thyroid carcinoma, Medullary thyroid carcinoma; disorders and/or diseases of the parathyroid, such as, for example, hyperparathyroidism, hypoparathyroidism; disorders and/or diseases of the hypothalamus.

In specific embodiments, the polynucleotides and/or polypeptides corresponding to this gene and/or agonists or antagonists of those polypeptides (including antibodies) as well as fragments and variants of those polynucleotides, polypeptides, agonists and antagonists, may be used to diagnose, prognose, treat, prevent, or ameliorate diseases and disorders associated with aberrant glucose metabolism or glucose uptake into cells.

In a specific embodiment, the polynucleotides and/or polypeptides corresponding to this gene and/or agonists and/or antagonists thereof may be used to diagnose, prognose, treat, prevent, and/or ameliorate type I diabetes mellitus (insulin dependent diabetes mellitus, IDDM).

In another embodiment, the polynucleotides and/or polypeptides corresponding to this gene and/or agonists and/or antagonists thereof may be used to diagnose, prognose, treat, prevent, and/or ameliorate type II diabetes mellitus (insulin resistant diabetes mellitus).

Additionally, in other embodiments, the polynucleotides and/or polypeptides corresponding to this gene and/or antagonists thereof (especially neutralizing or antagonistic antibodies) may be used to diagnose, prognose, treat, prevent, and/or ameliorate conditions associated with (type I or type II) diabetes mellitus, including, but not limited to, diabetic ketoacidosis, diabetic coma, nonketotic hyperglycemic-hyperosmolar coma, seizures, mental confusion, drowsiness, cardiovascular disease (e.g., heart disease, atherosclerosis, microvascular disease, hypertension, stroke, and other diseases and disorders as described in the "Cardiovascular Disorders" section), dyslipidemia, kidney disease (e.g., renal failure, nephropathy other diseases and disorders as described in the "Renal Disorders" section), nerve damage, neuropathy, vision impairment (e.g., diabetic retinopathy and blindness), ulcers and impaired wound healing, infections (e.g., infectious diseases and disorders as described in the "Infectious Diseases" section, especially of the urinary tract and skin), carpal tunnel syndrome and Dupuytren's contracture.

In other embodiments, the polynucleotides and/or polypeptides corresponding to this gene and/or agonists or antagonists thereof are administered to an animal, preferably a mammal, and most preferably a human, in order to regulate the animal's weight. In specific embodiments the polynucleotides and/or polypeptides corresponding to this gene and/or agonists or antagonists thereof are administered to an animal, preferably a mammal, and most preferably a human, in order to control the animal's weight by modulating a biochemical pathway involving insulin. In still other embodiments the polynucleotides and/or polypeptides corresponding to this gene and/or agonists or antagonists thereof are administered to an animal, preferably a mammal, and most preferably a human, in order to control the animal's weight by modulating a biochemical pathway involving insulin-like growth factor.

In addition, endocrine system and/or hormone imbalance disorders and/or diseases may also include disorders and/or diseases of the testes or ovaries, including cancer. Other disorders and/or diseases of the testes or ovaries further include, for example, ovarian cancer, polycystic ovary syndrome, Klinefelter's syndrome, vanishing testes syndrome (bilateral anorchia), congenital absence of Leydig's cells, cryptorchidism, Noonan's syndrome, myotonic dystrophy, capillary haemangioma of the testis (benign), neoplasias of the testis and neo-testis.

Moreover, endocrine system and/or hormone imbalance disorders and/or diseases may also include disorders and/or diseases such as, for example, polyglandular deficiency syndromes, pheochromocytoma, neuroblastoma, multiple Endocrine neoplasia, and disorders and/or cancers of endocrine tissues.

In another embodiment, a polypeptide of the invention, or polynucleotides, antibodies, agonists, or antagonists corresponding to that polypeptide, may be used to detect, prevent, diagnose, prognosticate, treat, and/or ameliorate endocrine diseases and/or disorders associated with the tissue(s) in which the polypeptide of the invention is expressed, including one, two, three, four, five, or more tissues disclosed in Table 1B.2, column 5 (Tissue Distribution Library Code).

Reproductive System Disorders

The polynucleotides or polypeptides, or agonists or antagonists of the invention may be used for the detection, prevention, diagnosis, prognostication, treatment, and/or amelioration of diseases and/or disorders of the reproductive system. Reproductive system disorders that can be treated by the compositions of the invention, include, but are not limited to, reproductive system injuries, infections, neoplastic disorders, congenital defects, and diseases or disorders which result in infertility, complications with pregnancy, labor, or parturition, and postpartum difficulties.

Reproductive system disorders and/or diseases include diseases and/or disorders of the testes, including testicular atrophy, testicular feminization, cryptorchism (unilateral and bilateral), anorchia, ectopic testis, epididymitis and orchitis (typically resulting from infections such as, for example, gonorrhea, mumps, tuberculosis, and syphilis), testicular torsion, vasitis nodosa, germ cell tumors (e.g., seminomas, embryonal cell carcinomas, teratocarcinomas, choriocarcinomas, yolk sac tumors, and teratomas), stromal tumors (e.g., Leydig cell tumors), hydrocele, hematocele, varicocele, spermatocele, inguinal hernia, and disorders of sperm production (e.g., immotile cilia syndrome, aspermia, asthenozoospermia, azoospermia, oligospermia, and teratozoospermia).

Reproductive system disorders also include disorders of the prostate gland, such as acute non-bacterial prostatitis, chronic non-bacterial prostatitis, acute bacterial prostatitis, chronic bacterial prostatitis, prostatodystonia, prostatosis, granulomatous prostatitis, malacoplakia, benign prostatic hypertrophy or hyperplasia, and prostate neoplastic disorders, including adenocarcinomas, transitional cell carcinomas, ductal carcinomas, and squamous cell carcinomas.

Additionally, the compositions of the invention may be useful in the detection, prevention, diagnosis, prognostication, treatment, and/or amelioration of disorders or diseases of the penis and urethra, including inflammatory disorders, such as balanoposthitis, balanitis xerotica obliterans, phimosis, paraphimosis, syphilis, herpes simplex virus, gonorrhea, non-gonococcal urethritis, chlamydia, mycoplasma, trichomonas, HIV, AIDS, Reiter's syndrome, condyloma acuminatum, condyloma latum, and pearly penile papules; urethral abnormalities, such as hypospadias, epispadias, and phimosis; premalignant lesions, including Erythroplasia of Queyrat, Bowen's disease, Bowenoid paplosis, giant condyloma of Buscke-Lowenstein, and varrucous carcinoma; penile cancers, including squamous cell carcinomas, carcinoma in situ, verrucous carcinoma, and disseminated penile carcinoma; urethral neoplastic disorders, including penile urethral carcinoma, bulbomembranous urethral carcinoma, and prostatic urethral carcinoma; and erectile disorders, such as priapism, Peyronie's disease, erectile dysfunction, and impotence.

Moreover, diseases and/or disorders of the vas deferens include vasculititis and CBAVD (congenital bilateral absence of the vas deferens); additionally, the polynucleotides, polypeptides, and agonists or antagonists of the present invention may be used in the detection, prevention, diagnosis, prognostication, treatment, and/or amelioration of diseases and disorders of the seminal vesicles, including hydatid disease, congenital chloride diarrhea, and polycystic kidney disease.

Other disorders and/or diseases of the male reproductive system include, for example, Klinefelter's syndrome, Young's syndrome, premature ejaculation, diabetes mellitus, cystic fibrosis, Kartagener's syndrome, high fever, multiple sclerosis, and gynecomastia.

Further, the polynucleotides, polypeptides, and agonists or antagonists of the present invention may be used in the detection, prevention, diagnosis, prognostication, treatment, and/or amelioration of diseases and/or disorders of the vagina and vulva, including bacterial vaginosis, candida vaginitis, herpes simplex virus, chancroid, granuloma inguinale, lymphogranuloma venereum, scabies, human papillomavirus, vaginal trauma, vulvar trauma, adenosis, chlamydia vaginitis, gonorrhea, trichomonas vaginitis, condyloma acuminatum, syphilis, molluscum contagiosum, atrophic vaginitis, Paget's disease, lichen sclerosus, lichen planus, vulvodynia, toxic shock syndrome, vaginismus, vulvovaginitis, vulvar vestibulitis, and neoplastic disorders, such as squamous cell hyperplasia, clear cell carcinoma, basal cell carcinoma, melanomas, cancer of Bartholin's gland, and vulvar intraepithelial neoplasia.

Disorders and/or diseases of the uterus include dysmenorrhea, retroverted uterus, endometriosis, fibroids, adenomyosis, anovulatory bleeding, amenorrhea, Cushing's syndrome, hydatidiform moles, Asherman's syndrome, premature menopause, precocious puberty, uterine polyps, dysfunctional uterine bleeding (e.g., due to aberrant hormonal signals), and neoplastic disorders, such as adenocarcinomas, keiomyosarcomas, and sarcomas. Additionally, the polypeptides, polynucleotides, or agonists or antagonists of the invention may be useful as a marker or detector of, as well as in the detection, prevention, diagnosis, prognostication, treatment, and/or amelioration of congenital uterine abnormalities, such as bicornuate uterus, septate uterus, simple unicornuate uterus, unicornuate uterus with a noncavitary rudimentary horn, unicornuate uterus with a non-communicating cavitary rudimentary horn, unicornuate uterus with a communicating cavitary horn, arcuate uterus, uterine didelfus, and T-shaped uterus.

Ovarian diseases and/or disorders include anovulation, polycystic ovary syndrome (Stein-Leventhal syndrome), ovarian cysts, ovarian hypofunction, ovarian insensitivity to gonadotropins, ovarian overproduction of androgens, right ovarian vein syndrome, amenorrhea, hirutismo, and ovarian cancer (including, but not limited to, primary and secondary cancerous growth, Sertoli-Leydig tumors, endometrioid carcinoma of the ovary, ovarian papillary serous adenocarcinoma, ovarian mucinous adenocarcinoma, and Ovarian Krukenberg tumors).

Cervical diseases and/or disorders include cervicitis, chronic cervicitis, mucopurulent cervicitis, cervical dysplasia, cervical polyps, Nabothian cysts, cervical erosion, cervical incompetence, and cervical neoplasms (including, for example, cervical carcinoma, squamous metaplasia, squamous cell carcinoma, adenosquamous cell neoplasia, and columnar cell neoplasia).

Additionally, diseases and/or disorders of the reproductive system include disorders and/or diseases of pregnancy, including miscarriage and stillbirth, such as early abortion, late abortion, spontaneous abortion, induced abortion, therapeutic abortion, threatened abortion, missed abortion, incomplete abortion, complete abortion, habitual abortion, missed abortion, and septic abortion; ectopic pregnancy, anemia, Rh incompatibility, vaginal bleeding during pregnancy, gestational diabetes, intrauterine growth retardation, polyhydramnios, HELLP syndrome, abruptio placentae, placenta previa, hyperemesis, preeclampsia, eclampsia, herpes gestationis, and urticaria of pregnancy. Additionally, the polynucleotides, polypeptides, and agonists or antagonists of the present invention may be used in the detection, prevention, diagnosis, prognostication, treatment, and/or amelioration of diseases that can complicate pregnancy, including heart disease, heart failure, rheumatic heart disease, congenital heart disease, mitral valve prolapse, high blood pressure, anemia, kidney disease, infectious disease (e.g., rubella, cytomegalovirus, toxoplasmosis, infectious hepatitis, chlamydia, HIV, AIDS, and genital herpes), diabetes mellitus, Graves' disease, thyroiditis, hypothyroidism, Hashimoto's thyroiditis, chronic active hepatitis, cirrhosis of the liver, primary biliary cirrhosis, asthma, systemic lupus eryematosis, rheumatoid arthritis, myasthenia gravis, idiopathic thrombocytopenic purpura, appendicitis, ovarian cysts, gallbladder disorders, and obstruction of the intestine.

Complications associated with labor and parturition include premature rupture of the membranes, pre-term labor, post-term pregnancy, postmaturity, labor that progresses too slowly, fetal distress (e.g., abnormal heart rate (fetal or maternal), breathing problems, and abnormal fetal position), shoulder dystocia, prolapsed umbilical cord, amniotic fluid embolism, and aberrant uterine bleeding.

Further, diseases and/or disorders of the postdelivery period, including endometritis, myometritis, parametritis, peritonitis, pelvic thrombophlebitis, pulmonary embolism, endotoxemia, pyelonephritis, saphenous thrombophlebitis, mastitis, cystitis, postpartum hemorrhage, and inverted uterus.

Other disorders and/or diseases of the female reproductive system that may be detected, prevented, diagnosed, prognosticated, treated, and/or ameliorated by the polynucleotides, polypeptides, and agonists or antagonists of the present invention include, for example, Turner's syndrome, pseudohermaphroditism, premenstrual syndrome, pelvic inflammatory disease, pelvic congestion (vascular engorgement), frigidity, anorgasmia, dyspareunia, ruptured fallopian tube, and Mittelschmerz.

Infectious Disease

Polynucleotides or polypeptides, as well as agonists or antagonists of the present invention can be used to treat or detect infectious agents. For example, by increasing the immune response, particularly increasing the proliferation and differentiation of B and/or T cells, infectious diseases may be treated. The immune response may be increased by either enhancing an existing immune response, or by initiating a new immune response. Alternatively, polynucleotides or polypeptides, as well as agonists or antagonists of the present invention may also directly inhibit the infectious agent, without necessarily eliciting an immune response.

Viruses are one example of an infectious agent that can cause disease or symptoms that can be treated or detected by a polynucleotide or polypeptide and/or agonist or antagonist of the present invention. Examples of viruses, include, but are not limited to Examples of viruses, include, but are not limited to the following DNA and RNA viruses and viral families: Arbovirus, Adenoviridae, Arenaviridae, Arterivirus, Birnaviridae, Bunyaviridae, Caliciviridae, Circoviridae, Coronaviridae, Dengue, EBV, HIV, Flaviviridae, Hepadnaviridae (Hepatitis), Herpesviridae (such as, Cytomegalovirus, Herpes Simplex, Herpes Zoster), Mononegavirus (e.g., Paramyxoviridae, Morbillivirus, Rhabdoviridae), Orthomyxoviridae (e.g., Influenza A, Influenza B, and parainfluenza), Papiloma virus, Papovaviridae, Parvoviridae, Picornaviridae, Poxyiridae (such as Smallpox or Vaccinia), Reoviridae (e.g., Rotavirus), Retroviridae (HTLV-I, HTLV-II, Lentivirus), and Togaviridae (e.g., Rubivirus). Viruses falling within these families can cause a variety of diseases or symptoms, including, but not limited to: arthritis, bronchiolitis, respiratory syncytial virus, encephalitis, eye infections (e.g., conjunctivitis, keratitis), chronic fatigue syndrome, hepatitis (A, B, C, E, Chronic Active, Delta), Japanese B encephalitis, Junin, Chikungunya, Rift Valley fever, yellow fever, meningitis, opportunistic infections (e.g., AIDS), pneumonia, Burkitt's Lymphoma, chickenpox, hemorrhagic fever, Measles, Mumps, Parainfluenza, Rabies, the common cold, Polio, leukemia, Rubella, sexually transmitted diseases, skin diseases (e.g., Kaposi's, warts), and viremia. polynucleotides or polypeptides, or agonists or antagonists of the invention, can be used to treat or detect any of these symptoms or diseases. In specific embodiments, polynucleotides, polypeptides, or agonists or antagonists of the invention are used to treat: meningitis, Dengue, EBV, and/or hepatitis (e.g., hepatitis B). In an additional specific embodiment polynucleotides, polypeptides, or agonists or antagonists of the invention are used to treat patients nonresponsive to one or more other commercially available hepatitis vaccines. In a further specific embodiment polynucleotides, polypeptides, or agonists or antagonists of the invention are used to treat AIDS.

Similarly, bacterial and fungal agents that can cause disease or symptoms and that can be treated or detected by a polynucleotide or polypeptide and/or agonist or antagonist of the present invention include, but not limited to, the following Gram-Negative and Gram-positive bacteria, bacterial families, and fungi: *Actinomyces* (e.g., *Norcardia*), *Acinetobacter, Cryptococcus neoformans, Aspergillus*, Bacillaceae (e.g., *Bacillus anthrasis*), *Bacteroides* (e.g., *Bacteroides fragilis*), Blastomycosis, *Bordetella, Borrelia* (e.g., *Borrelia burgdorferi*), *Brucella, Candidia, Campylobacter, Chlamydia, Clostridium* (e.g., *Clostridium botulinum, Clostridium difficile, Clostridium perfringens, Clostridium tetani*), *Coccidioides, Corynebacterium* (e.g., *Corynebacterium diptheriae*), *Cryptococcus, Dermatocycoses, E. coli* (e.g., Enterotoxigenic *E. coli* and Enterohemorrhagic *E. coli*), *Enterobacter* (e.g. *Enterobacter aerogenes*), Enterobacteriaceae (*Klebsiella, Salmonella* (e.g., *Salmonella typhi, Salmonella enteritidis, Salmonella typhi*), *Serratia, Yersinia, Shigella*), *Erysipelothrix, Haemophilus* (e.g., *Haemophilus influenza* type B), *Helicobacter, Legionella* (e.g., *Legionella pneumophila*), *Leptospira, Listeria* (e.g., *Listeria monocytogenes*), *Mycoplasma, Mycobacterium* (e.g., *Mycobacterium leprae* and *Mycobacterium tuberculosis*), *Vibrio* (e.g., *Vibrio cholerae*), Neisseriaceae (e.g., *Neisseria gonorrhea, Neisseria meningitidis*), Pasteurellacea, Pasteurellacea Infections (e.g., *Actinobacillus, Heamophilus* (e.g., *Heamophilus influenza* type B), *Pasteurella*), Chlamydiaceae, Syphilis, *Proteus, Pseudomonas* (e.g., *Pseudomonas aeruginosa*), Rickettsiaceae, Spirochetes (e.g., *Treponema* spp., *Leptospira* spp., *Borrelia* spp.), *Shigella* spp., *Staphylococcus* (e.g., *Staphylococcus aureus*), *Meningiococcus, Pneumococcus* and *Streptococcus* (e.g., *Streptococcus pneumoniae* and Groups A, B, and C Streptococci), and Ureaplasmas. These bacterial, parasitic, and fungal families can cause diseases or symptoms, including, but not limited to: antibiotic-resistant infections, bacteremia, endocarditis, septicemia, eye infections (e.g., conjunctivitis), uveitis, tuberculosis, gingivitis, bacterial diarrhea, opportunistic infections (e.g., AIDS related infections), paronychia, prosthesis-related infections, dental caries, Reiter's Disease, respiratory tract infections, such as Whooping Cough or Empyema, sepsis, Lyme Disease, Cat-Scratch Disease, dysentery, paratyphoid fever, food poisoning, *Legionella* disease, chronic and acute inflammation, erythema, yeast infections, typhoid, pneumonia, gonorrhea, meningitis (e.g., mengitis types A and B), chlamydia, syphillis, diphtheria, leprosy, brucellosis, peptic ulcers, anthrax, spontaneous abortions, birth defects, pneumonia, lung infections, ear infections, deafness, blindness, lethargy, malaise, vomiting, chronic diarrhea, Crohn's disease, colitis, vaginosis, sterility, pelvic inflammatory diseases, candidiasis, paratuberculosis, tuberculosis, lupus, botulism, gangrene, tetanus, impetigo, Rheumatic Fever, Scarlet Fever, sexually transmitted diseases, skin diseases (e.g., cellulitis, dermatocycoses), toxemia, urinary tract infections, wound infections, nosocomial infections. Polynucleotides or polypeptides, agonists or antagonists of the invention, can be used to treat or detect any of these symptoms or diseases. In specific embodiments, polynucleotides, polypeptides, agonists or antagonists of the invention are used to treat: tetanus, diphtheria, botulism, and/or meningitis type B.

Moreover, parasitic agents causing disease or symptoms that can be detected, prevented, diagnosed, prognosticated, treated, and/or ameliorated by a polynucleotide or polypeptide and/or agonist or antagonist of the present invention include, but not limited to, the following families or class: Amebiasis, Babesiosis, Coccidiosis, Cryptosporidiosis, Dientamoebiasis, Dourine, Ectoparasitic, Giardias, Helminthiasis, Leishmaniasis, Schistisoma, Theileriasis, Toxoplasmosis, Trypanosomiasis, and Trichomonas and Sporozoans (e.g., *Plasmodium virax, Plasmodium falciparium, Plasmodium malariae* and *Plasmodium ovale*). These parasites can cause a variety of diseases or symptoms, including, but not limited to: Scabies, Trombiculiasis, eye infections, intestinal disease (e.g., dysentery, giardiasis), liver disease, lung disease, opportunistic infections (e.g., AIDS related), malaria, pregnancy complications, and toxoplasmosis. polynucleotides or polypeptides, or agonists or antagonists of the invention, can be used to detect, prevent, diagnose, prognosticate, treat, and/or ameliorate any of these symptoms or diseases. In specific embodiments, polynucleotides, polypeptides, or agonists or antagonists of the invention are used to detect, prevent, diagnose, treat, and/or ameliorate malaria.

Polynucleotides or polypeptides, as well as agonists or antagonists of the present invention of the present invention could either be by administering an effective amount of a polypeptide to the patient, or by removing cells from the patient, supplying the cells with a polynucleotide of the present invention, and returning the engineered cells to the patient (ex vivo therapy). Moreover, the polypeptide or polynucleotide of the present invention can be used as an antigen in a vaccine to raise an immune response against infectious disease.

Regeneration

Polynucleotides or polypeptides, as well as agonists or antagonists of the present invention can be used to differentiate, proliferate, and attract cells, leading to the regeneration of tissues. (See, Science 276:59-87 (1997)). The regeneration of tissues could be used to repair, replace, or protect tissue damaged by congenital defects, trauma (wounds, burns, incisions, or ulcers), age, disease (e.g. osteoporosis, osteocarthritis, periodontal disease, liver failure), surgery, including cosmetic plastic surgery, fibrosis, reperfusion injury, or systemic cytokine damage.

Tissues that could be regenerated using the present invention include organs (e.g., pancreas, liver, intestine, kidney, skin, endothelium), muscle (smooth, skeletal or cardiac), vasculature (including vascular and lymphatics), nervous, hematopoietic, and skeletal (bone, cartilage, tendon, and ligament) tissue. Preferably, regeneration occurs without or decreased scarring. Regeneration also may include angiogenesis.

Moreover, polynucleotides or polypeptides, as well as agonists or antagonists of the present invention, may increase regeneration of tissues difficult to heal. For example, increased tendon/ligament regeneration would quicken recovery time after damage. Polynucleotides or polypeptides, as well as agonists or antagonists of the present invention could also be used prophylactically in an effort to avoid damage. Specific diseases that could be treated include of tendinitis, carpal tunnel syndrome, and other tendon or ligament defects. A further example of tissue regeneration of non-healing wounds includes pressure ulcers, ulcers associated with vascular insufficiency, surgical, and traumatic wounds.

Similarly, nerve and brain tissue could also be regenerated by using polynucleotides or polypeptides, as well as agonists or antagonists of the present invention, to proliferate and differentiate nerve cells. Diseases that could be treated using this method include central and peripheral nervous system diseases, neuropathies, or mechanical and traumatic disorders (e.g., spinal cord disorders, head trauma, cerebrovascular disease, and stoke). Specifically, diseases associated with peripheral nerve injuries, peripheral neuropathy (e.g., resulting from chemotherapy or other medical therapies), localized neuropathies, and central nervous system diseases (e.g., Alzheimer's disease, Parkinson's disease, Huntington's disease, amyotrophic lateral sclerosis, and Shy-Drager syndrome), could all be treated using the polynucleotides or polypeptides, as well as agonists or antagonists of the present invention.

Gastrointestinal Disorders

Polynucleotides or polypeptides, or agonists or antagonists of the present invention, may be used to detect, prevent, diagnose, prognosticate, treat, and/or ameliorate gastrointestinal diseases and disorders, including inflammatory diseases and/or conditions, infections, cancers (e.g., intestinal neoplasms (carcinoid tumor of the small intestine, non-Hodgkin's lymphoma of the small intestine, small bowl lymphoma)), and ulcers, such as peptic ulcers.

Gastrointestinal disorders include dysphagia, odynophagia, inflammation of the esophagus, peptic esophagitis, gastric reflux, submucosal fibrosis and structuring, Mallory-Weiss lesions, leiomyomas, lipomas, epidermal cancers, adenocarcinomas, gastric retention disorders, gastroenteritis, gastric atrophy, gastric/stomach cancers, polyps of the stomach, autoimmune disorders such as pernicious anemia, pyloric stenosis, gastritis (bacterial, viral, eosinophilic, stress-induced, chronic erosive, atrophic, plasma cell, and Ménétrier's), and peritoneal diseases (e.g., chyloperioneum, hemoperitoneum, mesenteric cyst, mesenteric lymphadenitis, mesenteric vascular occlusion, panniculitis, neoplasms, peritonitis, pneumoperitoneum, bubphrenic abscess).

Gastrointestinal disorders also include disorders associated with the small intestine, such as malabsorption syndromes, distension, irritable bowel syndrome, sugar intolerance, celiac disease, duodenal ulcers, duodenitis, tropical sprue, Whipple's disease, intestinal lymphangiectasia, Crohn's disease, appendicitis, obstructions of the ileum, Meckel's diverticulum, multiple diverticula, failure of complete rotation of the small and large intestine, lymphoma, and bacterial and parasitic diseases (such as Traveler's diarrhea, typhoid and paratyphoid, cholera, infection by Roundworms (*Ascariasis lumbricoides*), Hookworms (*Ancylostoma duodenale*), Threadworms (*Enterobius vermicularis*), Tapeworms (*Taenia saginata, Echinococcus granulosus, Diphyllobothrium* spp., and *T. solium*).

Liver diseases and/or disorders include intrahepatic cholestasis (alagille syndrome, biliary liver cirrhosis), fatty liver (alcoholic fatty liver, reye syndrome), hepatic vein thrombosis, hepatolentricular degeneration, hepatomegaly, hepatopulmonary syndrome, hepatorenal syndrome, portal hypertension (esophageal and gastric varices), liver abscess (amebic liver abscess), liver cirrhosis (alcoholic, biliary and experimental), alcoholic liver diseases (fatty liver, hepatitis, cirrhosis), parasitic (hepatic echinococcosis, fascioliasis, amebic liver abscess), jaundice (hemolytic, hepatocellular, and cholestatic), cholestasis, portal hypertension, liver enlargement, ascites, hepatitis (alcoholic hepatitis, animal hepatitis, chronic hepatitis (autoimmune, hepatitis B, hepatitis C, hepatitis D, drug induced), toxic hepatitis, viral human hepatitis (hepatitis A, hepatitis B, hepatitis C, hepatitis D, hepatitis E), Wilson's disease, granulomatous hepatitis, secondary biliary cirrhosis, hepatic encephalopathy, portal hypertension, varices, hepatic encephalopathy, primary biliary cirrhosis, primary sclerosing cholangitis, hepatocellular adenoma, hemangiomas, bile stones, liver failure (hepatic encephalopathy, acute liver failure), and liver neoplasms (angiomyolipoma, calcified liver metastases, cystic liver metastases, epithelial tumors, fibrolamellar hepatocarcinoma, focal nodular hyperplasia, hepatic adenoma, hepatobiliary cystadenoma, hepatoblastoma, hepatocellular carcinoma, hepatoma, liver cancer, liver hemangioendothelioma, mesenchymal hamartoma, mesenchymal tumors of liver, nodular regenerative hyperplasia, benign liver tumors (Hepatic cysts [Simple cysts, Polycystic liver disease, Hepatobiliary cystadenoma, Choledochal cyst], Mesenchymal tumors [Mesenchymal hamartoma, Infantile hemangioendothelioma, Hemangioma, Peliosis hepatis, Lipomas, Inflammatory pseudotumor, Miscellaneous], Epithelial tumors [Bile duct epithelium (Bile duct hamartoma, Bile duct adenoma), Hepatocyte (Adenoma, Focal nodular hyperplasia, Nodular regenerative hyperplasia)], malignant liver tumors [hepatocellular, hepatoblastoma, hepatocellular carcinoma, cholangiocellular, cholangiocarcinoma, cystadenocarcinoma, tumors of blood vessels, angiosarcoma, Karposi's sarcoma, hemangioendothelioma, other tumors, embryonal sarcoma, fibrosarcoma, leiomyosarcoma, rhabdomyosarcoma, carcinosarcoma, teratoma, carcinoid, squamous carcinoma, primary lymphoma]), peliosis hepatis, erythrohepatic porphyria, hepatic porphyria (acute intermittent porphyria, porphyria cutanea tarda), Zellweger syndrome).

Pancreatic diseases and/or disorders include acute pancreatitis, chronic pancreatitis (acute necrotizing pancreatitis, alcoholic pancreatitis), neoplasms (adenocarcinoma of the pancreas, cystadenocarcinoma, insulinoma, gastrinoma, and glucagonoma, cystic neoplasms, islet-cell tumors, pancreoblastoma), and other pancreatic diseases (e.g., cystic fibrosis, cyst (pancreatic pseudocyst, pancreatic fistula, insufficiency)).

Gallbladder diseases include gallstones (cholelithiasis and choledocholithiasis), postcholecystectomy syndrome, diverticulosis of the gallbladder, acute cholecystitis, chronic cholecystitis, bile duct tumors, and mucocele.

Diseases and/or disorders of the large intestine include antibiotic-associated colitis, diverticulitis, ulcerative colitis, acquired megacolon, abscesses, fungal and bacterial infections, anorectal disorders (e.g., fissures, hemorrhoids), colonic diseases (colitis, colonic neoplasms [colon cancer, adenomatous colon polyps (e.g., villous adenoma), colon carcinoma, colorectal cancer], colonic diverticulitis, colonic diverticulosis, megacolon [Hirschsprung disease, toxic megacolon]; sigmoid diseases [proctocolitis, sigmoin neoplasms]), constipation, Crohn's disease, diarrhea (infantile diarrhea, dysentery), duodenal diseases (duodenal neoplasms, duodenal obstruction, duodenal ulcer, duodenitis), enteritis (enterocolitis), HIV enteropathy, ileal diseases (ileal neoplasms, ileitis), immunoproliferative small intestinal disease, inflammatory bowel disease (ulcerative colitis, Crohn's disease), intestinal atresia, parasitic diseases (anisakiasis, balantidiasis, blastocystis infections, cryptosporidiosis, dientamoebiasis, amebic dysentery, giardiasis), intestinal fistula (rectal fistula), intestinal neoplasms (cecal neoplasms, colonic neoplasms, duodenal neoplasms, ileal neoplasms, intestinal polyps, jejunal neoplasms, rectal neoplasms), intestinal obstruction (afferent loop syndrome, duodenal obstruction, impacted feces, intestinal pseudo-obstruction [cecal volvulus], intussusception), intestinal perforation, intestinal polyps (colonic polyps, gardner syndrome, peutz-jeghers syndrome), jejunal diseases (jejunal neoplasms), malabsorption syndromes (blind loop syndrome, celiac disease, lactose intolerance, short bowl syndrome, tropical sprue, whipple's disease), mesenteric vascular occlusion, pneumatosis cystoides intestinalis, protein-losing enteropathies (intestinal lymphagiectasis), rectal diseases (anus diseases, fecal incontinence, hemorrhoids, proctitis, rectal fistula, rectal prolapse, rectocele), peptic ulcer (duodenal ulcer, peptic esophagitis, hemorrhage, perforation, stomach ulcer, Zollinger-Ellison syndrome), postgastrectomy syndromes (dumping syndrome), stomach diseases (e.g., achlorhydria, duodenogastric reflux (bile reflux), gastric antral vascular ectasia, gastric fistula, gastric outlet obstruction, gastritis (atrophic or hypertrophic), gastroparesis, stomach dilatation, stomach diverticulum, stomach neoplasms (gastric cancer, gastric polyps, gastric adenocarcinoma, hyperplastic gastric polyp), stomach rupture, stomach ulcer, stomach volvulus), tuberculosis, visceroptosis, vomiting (e.g., hematemesis, hyperemesis gravidarum, postoperative nausea and vomiting) and hemorrhagic colitis.

Further diseases and/or disorders of the gastrointestinal system include biliary tract diseases, such as, gastroschisis, fistula (e.g., biliary fistula, esophageal fistula, gastric fistula, intestinal fistula, pancreatic fistula), neoplasms (e.g., biliary tract neoplasms, esophageal neoplasms, such as adenocarcinoma of the esophagus, esophageal squamous cell carcinoma, gastrointestinal neoplasms, pancreatic neoplasms, such as adenocarcinoma of the pancreas, mucinous cystic neoplasm of the pancreas, pancreatic cystic neoplasms, pancreatoblastoma, and peritoneal neoplasms), esophageal disease (e.g., bullous diseases, candidiasis, glycogenic acanthosis, ulceration, barrett esophagus varices, atresia, cyst, diverticulum (e.g., Zenker's diverticulum), fistula (e.g., tracheoesophageal fistula), motility disorders (e.g., CREST syndrome, deglutition disorders, achalasia, spasm, gastroesophageal reflux), neoplasms, perforation (e.g., Boerhaave syndrome, Mallory-Weiss syndrome), stenosis, esophagitis, diaphragmatic hernia (e.g., hiatal hernia); gastrointestinal diseases, such as, gastroenteritis (e.g., cholera morbus, norwalk virus infection), hemorrhage (e.g., hematemesis, melena, peptic ulcer hemorrhage), stomach neoplasms (gastric cancer, gastric polyps, gastric adenocarcinoma, stomach cancer)), hernia (e.g., congenital diaphragmatic hernia, femoral hernia, inguinal hernia, obturator hernia, umbilical hernia, ventral hernia), and intestinal diseases (e.g., cecal diseases (appendicitis, cecal neoplasms)).

Chemotaxis

Polynucleotides or polypeptides, as well as agonists or antagonists of the present invention may have chemotaxis activity. A chemotaxic molecule attracts or mobilizes cells (e.g., monocytes, fibroblasts, neutrophils, T-cells, mast cells, eosinophils, epithelial and/or endothelial cells) to a particular site in the body, such as inflammation, infection, or site of hyperproliferation. The mobilized cells can then fight off and/or heal the particular trauma or abnormality.

Polynucleotides or polypeptides, as well as agonists or antagonists of the present invention may increase chemotaxic activity of particular cells. These chemotactic molecules can then be used to treat inflammation, infection, hyperproliferative disorders, or any immune system disorder by increasing the number of cells targeted to a particular location in the body. For example, chemotaxic molecules can be used to treat wounds and other trauma to tissues by attracting immune cells to the injured location. Chemotactic molecules of the present invention can also attract fibroblasts, which can be used to treat wounds.

It is also contemplated that polynucleotides or polypeptides, as well as agonists or antagonists of the present invention may inhibit chemotactic activity. These molecules could also be used to treat disorders. Thus, polynucleotides or polypeptides, as well as agonists or antagonists of the present invention could be used as an inhibitor of chemotaxis.

Binding Activity

A polypeptide of the present invention may be used to screen for molecules that bind to the polypeptide or for molecules to which the polypeptide binds. The binding of the polypeptide and the molecule may activate (agonist), increase, inhibit (antagonist), or decrease activity of the polypeptide or the molecule bound. Examples of such molecules include antibodies, oligonucleotides, proteins (e.g., receptors), or small molecules.

Preferably, the molecule is closely related to the natural ligand of the polypeptide, e.g., a fragment of the ligand, or a natural substrate, a ligand, a structural or functional mimetic. (See, Coligan et al., Current Protocols in Immunology 1(2): Chapter 5 (1991)). Similarly, the molecule can be closely related to the natural receptor to which the polypeptide binds, or at least, a fragment of the receptor capable of being bound by the polypeptide (e.g., active site). In either case, the molecule can be rationally designed using known techniques.

Preferably, the screening for these molecules involves producing appropriate cells which express the polypeptide. Preferred cells include cells from mammals, yeast, *Drosophila*, or *E. coli*. Cells expressing the polypeptide (or cell membrane containing the expressed polypeptide) are then preferably contacted with a test compound potentially containing the molecule to observe binding, stimulation, or inhibition of activity of either the polypeptide or the molecule.

The assay may simply test binding of a candidate compound to the polypeptide, wherein binding is detected by a label, or in an assay involving competition with a labeled competitor. Further, the assay may test whether the candidate compound results in a signal generated by binding to the polypeptide.

Alternatively, the assay can be carried out using cell-free preparations, polypeptide/molecule affixed to a solid support, chemical libraries, or natural product mixtures. The assay may also simply comprise the steps of mixing a candidate compound with a solution containing a polypeptide, measuring polypeptide/molecule activity or binding, and comparing the polypeptide/molecule activity or binding to a standard.

Preferably, an ELISA assay can measure polypeptide level or activity in a sample (e.g., biological sample) using a monoclonal or polyclonal antibody. The antibody can measure polypeptide level or activity by either binding, directly or indirectly, to the polypeptide or by competing with the polypeptide for a substrate.

Additionally, the receptor to which the polypeptide of the present invention binds can be identified by numerous methods known to those of skill in the art, for example, ligand panning and FACS sorting (Coligan, et al., Current Protocols in Immun., 1(2), Chapter 5, (1991)). For example, expression cloning is employed wherein polyadenylated RNA is prepared from a cell responsive to the polypeptides, for example, NIH3T3 cells which are known to contain multiple receptors for the FGF family proteins, and SC-3 cells, and a cDNA library created from this RNA is divided into pools and used to transfect COS cells or other cells that are not responsive to the polypeptides. Transfected cells which are grown on glass slides are exposed to the polypeptide of the present invention, after they have been labeled. The polypeptides can be labeled by a variety of means including iodination or inclusion of a recognition site for a site-specific protein kinase.

Following fixation and incubation, the slides are subjected to auto-radiographic analysis. Positive pools are identified and sub-pools are prepared and re-transfected using an iterative sub-pooling and re-screening process, eventually yielding a single clones that encodes the putative receptor.

As an alternative approach for receptor identification, the labeled polypeptides can be photoaffinity linked with cell membrane or extract preparations that express the receptor molecule. Cross-linked material is resolved by PAGE analysis and exposed to X-ray film. The labeled complex containing the receptors of the polypeptides can be excised, resolved into peptide fragments, and subjected to protein microsequencing. The amino acid sequence obtained from microsequencing would be used to design a set of degenerate oligonucleotide probes to screen a cDNA library to identify the genes encoding the putative receptors.

Moreover, the techniques of gene-shuffling, motif-shuffling, exon-shuffling, and/or codon-shuffling (collectively referred to as "DNA shuffling") may be employed to modulate the activities of the polypeptide of the present invention thereby effectively generating agonists and antagonists of the polypeptide of the present invention. See generally, U.S. Pat. Nos. 5,605,793, 5,811,238, 5,830,721, 5,834,252, and 5,837,458, and Patten, P. A., et al., *Curr. Opinion Biotechnol.* 8:724-33 (1997); Harayama, S. *Trends Biotechnol.* 16(2):76-82 (1998); Hansson, L. O., et al., *J. Mol. Biol.* 287:265-76 (1999); and Lorenzo, M. M. and Blasco, R. *Biotechniques* 24(2):308-13 (1998); each of these patents and publications are hereby incorporated by reference). In one embodiment, alteration of polynucleotides and corresponding polypeptides may be achieved by DNA shuffling. DNA shuffling involves the assembly of two or more DNA segments into a desired molecule by homologous, or site-specific, recombination. In another embodiment, polynucleotides and corresponding polypeptides may be altered by being subjected to random mutagenesis by error-prone PCR, random nucleotide insertion or other methods prior to recombination. In another embodiment, one or more components, motifs, sections, parts, domains, fragments, etc., of the polypeptide of the present invention may be recombined with one or more components, motifs, sections, parts, domains, fragments, etc. of one or more heterologous molecules. In preferred embodiments, the heterologous molecules are family members. In further preferred embodiments, the heterologous molecule is a growth factor such as, for example, platelet-derived growth factor (PDGF), insulin-like growth factor (IGF-I), transforming growth factor (TGF)-alpha, epidermal growth factor (EGF), fibroblast growth factor (FGF), TGF-beta, bone morphogenetic protein (BMP)-2, BMP-4, BMP-5, BMP-6, BMP-7, activins A and B, decapentaplegic(dpp), 60A, OP-2, dorsalin, growth differentiation factors (GDFs), nodal, MIS, inhibin-alpha, TGF-beta1, TGF-beta2, TGF-beta3, TGF-beta5, and glial-derived neurotrophic factor (GDNF).

Other preferred fragments are biologically active fragments of the polypeptide of the present invention. Biologically active fragments are those exhibiting activity similar, but not necessarily identical, to an activity of the polypeptide of the present invention. The biological activity of the fragments may include an improved desired activity, or a decreased undesirable activity.

Additionally, this invention provides a method of screening compounds to identify those which modulate the action of the polypeptide of the present invention. An example of such an assay comprises combining a mammalian fibroblast cell, a the polypeptide of the present invention, the compound to be screened and $^3$[H] thymidine under cell culture conditions where the fibroblast cell would normally proliferate. A control assay may be performed in the absence of the compound to be screened and compared to the amount of fibroblast proliferation in the presence of the compound to determine if the compound stimulates proliferation by determining the uptake of $^3$[H] thymidine in each case. The amount of fibroblast cell proliferation is measured by liquid scintillation chromatography which measures the incorporation of $^3$[H] thymidine. Both agonist and antagonist compounds may be identified by this procedure.

In another method, a mammalian cell or membrane preparation expressing a receptor for a polypeptide of the present invention is incubated with a labeled polypeptide of the present invention in the presence of the compound. The ability of the compound to enhance or block this interaction could then be measured. Alternatively, the response of a known second messenger system following interaction of a compound to be screened and the receptor is measured and the ability of the compound to bind to the receptor and elicit a second messenger response is measured to determine if the compound is a potential agonist or antagonist. Such second messenger systems include but are not limited to, cAMP guanylate cyclase, ion channels or phosphoinositide hydrolysis.

All of these above assays can be used as diagnostic or prognostic markers. The molecules discovered using these assays can be used to treat disease or to bring about a particular result in a patient (e.g., blood vessel growth) by activating or inhibiting the polypeptide/molecule. Moreover, the assays can discover agents which may inhibit or enhance the production of the polypeptides of the invention from suitably manipulated cells or tissues.

Also, one could identify molecules that bind a polypeptide of the invention experimentally by using the beta-pleated sheet regions contained in the polypeptide sequence of the protein. Accordingly, specific embodiments of the invention are directed to polynucleotides encoding polypeptides which comprise, or alternatively consist of, the amino acid sequence of each beta pleated sheet regions in a disclosed polypeptide sequence. Additional embodiments of the invention are directed to polynucleotides encoding polypeptides which comprise, or alternatively consist of, any combination or all of contained in the polypeptide sequences of the invention. Additional preferred embodiments of the invention are directed to polypeptides which comprise, or alternatively consist of, the amino acid sequence of each of the beta pleated sheet regions in one of the polypeptide sequences of the invention. Additional embodiments of the invention are directed to polypeptides which comprise, or alternatively consist of, any combination or all of the beta pleated sheet regions in one of the polypeptide sequences of the invention.

Therefore, the invention includes a method of identifying compounds which bind to a polypeptide of the invention comprising the steps of: (a) incubating a candidate binding compound with a polypeptide of the present invention; and (b) determining if binding has occurred. Moreover, the invention includes a method of identifying agonists/antagonists comprising the steps of: (a) incubating a candidate compound with a polypeptide of the present invention, (b) assaying a biological activity, and (b) determining if a biological activity of the polypeptide has been altered.

Targeted Delivery

In another embodiment, the invention provides a method of delivering compositions to targeted cells expressing a receptor for a polypeptide of the invention, or cells expressing a cell bound form of a polypeptide of the invention.

As discussed herein, polypeptides or antibodies of the invention may be associated with heterologous polypeptides, heterologous nucleic acids, toxins, or prodrugs via hydrophobic, hydrophilic, ionic and/or covalent interactions. In one embodiment, the invention provides a method for the specific delivery of compositions of the invention to cells by administering polypeptides of the invention (including antibodies) that are associated with heterologous polypeptides or nucleic acids. In one example, the invention provides a method for delivering a therapeutic protein into the targeted cell. In another example, the invention provides a method for delivering a single stranded nucleic acid (e.g., antisense or ribozymes) or double stranded nucleic acid (e.g., DNA that can integrate into the cell's genome or replicate episomally and that can be transcribed) into the targeted cell.

In another embodiment, the invention provides a method for the specific destruction of cells (e.g., the destruction of tumor cells) by administering polypeptides of the invention (e.g., polypeptides of the invention or antibodies of the invention) in association with toxins or cytotoxic prodrugs.

By "toxin" is meant compounds that bind and activate endogenous cytotoxic effector systems, radioisotopes, holotoxins, modified toxins, catalytic subunits of toxins, or any molecules or enzymes not normally present in or on the surface of a cell that under defined conditions cause the cell's death. Toxins that may be used according to the methods of the invention include, but are not limited to, radioisotopes known in the art, compounds such as, for example, antibodies (or complement fixing containing portions thereof) that bind an inherent or induced endogenous cytotoxic effector system, thymidine kinase, endonuclease, RNAse, alpha toxin, ricin, abrin, *Pseudomonas* exotoxin A, diphtheria toxin, saporin, momordin, gelonin, pokeweed antiviral protein, alpha-sarcin and cholera toxin. By "cytotoxic prodrug" is meant a non-toxic compound that is converted by an enzyme, normally present in the cell, into a cytotoxic compound. Cytotoxic prodrugs that may be used according to the methods of the invention include, but are not limited to, glutamyl derivatives of benzoic acid mustard alkylating agent, phosphate derivatives of etoposide or mitomycin C, cytosine arabinoside, daunorubicin, and phenoxyacetamide derivatives of doxorubicin.

Drug Screening

Further contemplated is the use of the polypeptides of the present invention, or the polynucleotides encoding these polypeptides, to screen for molecules which modify the activities of the polypeptides of the present invention. Such a method would include contacting the polypeptide of the present invention with a selected compound(s) suspected of having antagonist or agonist activity, and assaying the activity of these polypeptides following binding.

This invention is particularly useful for screening therapeutic compounds by using the polypeptides of the present invention, or binding fragments thereof, in any of a variety of drug screening techniques. The polypeptide or fragment employed in such a test may be affixed to a solid support, expressed on a cell surface, free in solution, or located intracellularly. One method of drug screening utilizes eukaryotic or prokaryotic host cells which are stably transformed with recombinant nucleic acids expressing the polypeptide or fragment. Drugs are screened against such transformed cells in competitive binding assays. One may measure, for example, the formulation of complexes between the agent being tested and a polypeptide of the present invention.

Thus, the present invention provides methods of screening for drugs or any other agents which affect activities mediated by the polypeptides of the present invention. These methods comprise contacting such an agent with a polypeptide of the present invention or a fragment thereof and assaying for the presence of a complex between the agent and the polypeptide or a fragment thereof, by methods well known in the art. In such a competitive binding assay, the agents to screen are typically labeled. Following incubation, free agent is separated from that present in bound form, and the amount of free or uncomplexed label is a measure of the ability of a particular agent to bind to the polypeptides of the present invention.

Another technique for drug screening provides high throughput screening for compounds having suitable binding affinity to the polypeptides of the present invention, and is described in great detail in European Patent Application 84/03564, published on Sep. 13, 1984, which is incorporated herein by reference herein. Briefly stated, large numbers of different small peptide test compounds are synthesized on a solid substrate, such as plastic pins or some other surface. The peptide test compounds are reacted with polypeptides of the present invention and washed. Bound polypeptides are then detected by methods well known in the art. Purified polypeptides are coated directly onto plates for use in the aforementioned drug screening techniques. In addition, non-neutralizing antibodies may be used to capture the peptide and immobilize it on the solid support.

This invention also contemplates the use of competitive drug screening assays in which neutralizing antibodies capable of binding polypeptides of the present invention specifically compete with a test compound for binding to the polypeptides or fragments thereof. In this manner, the antibodies are used to detect the presence of any peptide which shares one or more antigenic epitopes with a polypeptide of the invention.

Antisense and Ribozyme (Antagonists)

In specific embodiments, antagonists according to the present invention are nucleic acids corresponding to the sequences contained in SEQ ID NO:X, or the complementary strand thereof, and/or to cDNA sequences contained in cDNA ATCC™ Deposit No:Z identified for example, in Table 1A. In one embodiment, antisense sequence is generated internally, by the organism, in another embodiment, the antisense sequence is separately administered (see, for example, O'Connor, J., Neurochem. 56:560 (1991). Oligodeoxynucleotides as Antisense Inhibitors of Gene Expression, CRC Press, Boca Raton, Fla. (1988). Antisense technology can be used to control gene expression through antisense DNA or RNA, or through triple-helix formation. Antisense techniques are discussed for example, in Okano, J., Neurochem. 56:560 (1991); Oligodeoxynucleotides as Antisense Inhibitors of Gene Expression, CRC Press, Boca Raton, Fla. (1988). Triple helix formation is discussed in, for instance, Lee et al., Nucleic Acids Research 6:3073 (1979); Cooney et al., Science 241:456 (1988); and Dervan et al., Science 251:1300 (1991). The methods are based on binding of a polynucleotide to a complementary DNA or RNA.

For example, the use of c-myc and c-myb antisense RNA constructs to inhibit the growth of the non-lymphocytic leukemia cell line HL-60 and other cell lines was previously described. (Wickstrom et al. (1988); Anfossi et al. (1989)). These experiments were performed in vitro by incubating cells with the oligoribonucleotide. A similar procedure for in vivo use is described in WO 91/15580. Briefly, a pair of oligonucleotides for a given antisense RNA is produced as follows: A sequence complimentary to the first 15 bases of the open reading frame is flanked by an EcoR1 site on the 5 end and a HindIII site on the 3 end. Next, the pair of oligonucleotides is heated at 90° C. for one minute and then annealed in 2× ligation buffer (20 mM TRIS HCl pH 7.5, mM MgCl2, 10 mM dithiothreitol (DTT) and 0.2 mM ATP) and then ligated to the EcoR1/Hind III site of the retroviral vector PMV7 (WO 91/15580).

For example, the 5' coding portion of a polynucleotide that encodes the polypeptide of the present invention may be used to design an antisense RNA oligonucleotide of from about 10 to 40 base pairs in length. A DNA oligonucleotide is designed to be complementary to a region of the gene involved in transcription thereby preventing transcription and the production of the receptor. The antisense RNA oligonucleotide hybridizes to the mRNA in vivo and blocks translation of the mRNA molecule into receptor polypeptide.

In one embodiment, the antisense nucleic acid of the invention is produced intracellularly by transcription from an exogenous sequence. For example, a vector or a portion thereof, is transcribed, producing an antisense nucleic acid (RNA) of the invention. Such a vector would contain a sequence encoding the antisense nucleic acid. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in vertebrate cells. Expression of the sequence encoding the polypeptide of the present invention or fragments thereof, can be by any promoter known in the art to act in vertebrate, preferably human cells. Such promoters can be inducible or constitutive. Such promoters include, but are not limited to, the SV40 early promoter region (Bernoist and Chambon, Nature 29:304-310 (1981), the promoter contained in the 3' long terminal repeat of Rous sarcoma virus (Yamamoto et al., Cell 22:787-797 (1980), the herpes thymidine promoter (Wagner et al., Proc. Natl. Acad. Sci. U.S.A. 78:1441-1445 (1981), the regulatory sequences of the metallothionein gene (Brinster, et al., Nature 296:39-42 (1982)), etc.

The antisense nucleic acids of the invention comprise a sequence complementary to at least a portion of an RNA transcript of a gene of the present invention. However, absolute complementarity, although preferred, is not required. A sequence "complementary to at least a portion of an RNA," referred to herein, means a sequence having sufficient complementarity to be able to hybridize with the RNA, forming a stable duplex; in the case of double stranded antisense nucleic acids, a single strand of the duplex DNA may thus be tested, or triplex formation may be assayed. The ability to hybridize will depend on both the degree of complementarity and the length of the antisense nucleic acid. Generally, the larger the hybridizing nucleic acid, the more base mismatches with a RNA it may contain and still form a stable duplex (or triplex as the case may be). One skilled in the art can ascertain a tolerable degree of mismatch by use of standard procedures to determine the melting point of the hybridized complex.

Oligonucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs have been shown to be effective at inhibiting translation of mRNAs as well. See generally, Wagner, R., 1994, Nature 372:333-335. Thus, oligonucleotides complementary to either the 5'- or 3'-non-translated, non-coding regions of polynucleotide sequences described herein could be used in an antisense approach to inhibit translation of endogenous mRNA. Oligonucleotides complementary to the 5' untranslated region of the mRNA should include the complement of the AUG start codon. Antisense oligonucleotides complementary to mRNA coding regions are less efficient inhibitors of translation but could be used in accordance with the invention. Whether designed to hybridize to the 5'-, 3'- or coding region of mRNA of the present invention, antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at least 50 nucleotides.

The polynucleotides of the invention can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger et al., 1989, Proc. Natl. Acad. Sci. U.S.A. 86:6553-6556; Lemaitre et al., 1987, Proc. Natl. Acad. Sci. 84:648-652; PCT Publication No. WO88/09810, published Dec. 15, 1988) or the blood-brain barrier (see, e.g., PCT Publication No. WO89/10134, published Apr. 25, 1988), hybridization-triggered cleavage agents. (See, e.g., Krol et al., 1988, BioTechniques 6:958-976) or intercalating agents. (See, e.g., Zon, 1988, Pharm. Res. 5:539-549). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including, but not limited to, 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3)w, and 2,6-diaminopurine.

The antisense oligonucleotide may also comprise at least one modified sugar moiety selected from the group including, but not limited to, arabinose, 2-fluoroarabinose, xylulose, and hexose.

In yet another embodiment, the antisense oligonucleotide comprises at least one modified phosphate backbone selected from the group including, but not limited to, a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an a-anomeric oligonucleotide. An a-anomeric oligonucleotide forms specific double-stranded hybrids with complementary RNA in which, contrary to the usual b-units, the strands run parallel to each other (Gautier et al., 1987, Nucl. Acids Res. 15:6625-6641). The oligonucleotide is a 2'-O-methylribonucleotide (Inoue et al., 1987, Nucl. Acids Res. 15:6131-6148), or a chimeric RNA-DNA analogue (Inoue et al., 1987, FEBS Lett. 215:327-330).

Polynucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (1988, Nucl. Acids Res. 16:3209), methylphosphonate oligonucleotides can be prepared by use of controlled pore glass polymer supports (Sarin et al., 1988, Proc. Natl. Acad. Sci. U.S.A. 85:7448-7451), etc.

While antisense nucleotides complementary to the coding region sequence could be used, those complementary to the transcribed untranslated region are most preferred.

Potential antagonists according to the invention also include catalytic RNA, or a ribozyme (See, e.g., PCT International Publication WO 90/11364, published Oct. 4, 1990; Sarver et al, Science 247:1222-1225 (1990). While ribozymes that cleave mRNA at site specific recognition sequences can be used to destroy mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, Nature 334:585-591 (1988). There are numerous potential hammerhead ribozyme cleavage sites within the nucleotide sequence of SEQ ID NO:X. Preferably, the ribozyme is engineered so that the cleavage recognition site is located near the 5' end of the mRNA; i.e., to increase efficiency and minimize the intracellular accumulation of non-functional mRNA transcripts.

As in the antisense approach, the ribozymes of the invention can be composed of modified oligonucleotides (e.g., for improved stability, targeting, etc.) and should be delivered to cells which express in vivo. DNA constructs encoding the ribozyme may be introduced into the cell in the same manner as described above for the introduction of antisense encoding DNA. A preferred method of delivery involves using a DNA construct "encoding" the ribozyme under the control of a strong constitutive promoter, such as, for example, pol III or pol II promoter, so that transfected cells will produce sufficient quantities of the ribozyme to destroy endogenous messages and inhibit translation. Since ribozymes unlike antisense molecules, are catalytic, a lower intracellular concentration is required for efficiency.

Antagonist/agonist compounds may be employed to inhibit the cell growth and proliferation effects of the polypeptides of the present invention on neoplastic cells and tissues, i.e. stimulation of angiogenesis of tumors, and, therefore, retard or prevent abnormal cellular growth and proliferation, for example, in tumor formation or growth.

The antagonist/agonist may also be employed to prevent hyper-vascular diseases, and prevent the proliferation of epithelial lens cells after extracapsular cataract surgery. Prevention of the mitogenic activity of the polypeptides of the present invention may also be desirous in cases such as restenosis after balloon angioplasty.

The antagonist/agonist may also be employed to prevent the growth of scar tissue during wound healing.

The antagonist/agonist may also be employed to treat the diseases described herein.

Thus, the invention provides a method of treating disorders or diseases, including but not limited to the disorders or diseases listed throughout this application, associated with overexpression of a polynucleotide of the present invention by administering to a patient (a) an antisense molecule directed to the polynucleotide of the present invention, and/or (b) a ribozyme directed to the polynucleotide of the present invention.

Binding Peptides and Other Molecules

The invention also encompasses screening methods for identifying polypeptides and nonpolypeptides that bind polypeptides of the invention, and the binding molecules identified thereby. These binding molecules are useful, for example, as agonists and antagonists of the polypeptides of the invention. Such agonists and antagonists can be used, in accordance with the invention, in the therapeutic embodiments described in detail, below.

This method comprises the steps of:

a. contacting polypeptides of the invention with a plurality of molecules; and b. identifying a molecule that binds the polypeptides of the invention.

The step of contacting the polypeptides of the invention with the plurality of molecules may be effected in a number of ways. For example, one may contemplate immobilizing the polypeptides on a solid support and bringing a solution of the plurality of molecules in contact with the immobilized polypeptides. Such a procedure would be akin to an affinity chromatographic process, with the affinity matrix being comprised of the immobilized polypeptides of the invention. The molecules having a selective affinity for the polypeptides can then be purified by affinity selection. The nature of the solid support, process for attachment of the polypeptides to the solid support, solvent, and conditions of the affinity isolation or selection are largely conventional and well known to those of ordinary skill in the art.

Alternatively, one may also separate a plurality of polypeptides into substantially separate fractions comprising a subset of or individual polypeptides. For instance, one can separate the plurality of polypeptides by gel electrophoresis, column chromatography, or like method known to those of ordinary skill for the separation of polypeptides. The individual polypeptides can also be produced by a transformed host cell in such a way as to be expressed on or about its outer surface (e.g., a recombinant phage). Individual isolates can then be "probed" by the polypeptides of the invention, optionally in the presence of an inducer should one be required for expression, to determine if any selective affinity interaction takes place between the polypeptides and the individual clone. Prior to contacting the polypeptides with each fraction comprising individual polypeptides, the polypeptides could first be transferred to a solid support for additional convenience. Such a solid support may simply be a piece of filter membrane, such as one made of nitrocellulose or nylon. In this manner, positive clones could be identified from a collection of transformed host cells of an expression library, which harbor a DNA construct encoding a polypeptide having a selective affinity for polypeptides of the invention. Furthermore, the amino acid sequence of the polypeptide having a selective affinity for the polypeptides of the invention can be determined directly by conventional means or the coding sequence of the DNA encoding the polypeptide can frequently be determined more conveniently. The primary sequence can then be deduced from the corresponding DNA sequence. If the amino acid sequence is to be determined from the polypeptide itself, one may use microsequencing techniques. The sequencing technique may include mass spectroscopy.

In certain situations, it may be desirable to wash away any unbound polypeptides from a mixture of the polypeptides of the invention and the plurality of polypeptides prior to attempting to determine or to detect the presence of a selective affinity interaction. Such a wash step may be particularly desirable when the polypeptides of the invention or the plurality of polypeptides are bound to a solid support.

The plurality of molecules provided according to this method may be provided by way of diversity libraries, such as random or combinatorial peptide or nonpeptide libraries which can be screened for molecules that specifically bind polypeptides of the invention. Many libraries are known in the art that can be used, e.g., chemically synthesized libraries, recombinant (e.g., phage display libraries), and in vitro translation-based libraries. Examples of chemically synthesized libraries are described in Fodor et al., 1991, Science 251:767-773; Houghten et al., 1991, Nature 354:84-86; Lam et al., 1991, Nature 354:82-84; Medynski, 1994, Bio/Technology 12:709-710; Gallop et al., 1994, J. Medicinal Chemistry 37(9):1233-1251; Ohlmeyer et al., 1993, Proc. Natl. Acad. Sci. USA 90:10922-10926; Erb et al., 1994, Proc. Natl. Acad. Sci. USA 91:11422-11426; Houghten et al., 1992, Biotechniques 13:412; Jayawickreme et al., 1994, Proc. Natl. Acad. Sci. USA 91:1614-1618; Salmon et al., 1993, Proc. Natl. Acad. Sci. USA 90:11708-11712; PCT Publication No. WO 93/20242; and Brenner and Lerner, 1992, Proc. Natl. Acad. Sci. USA 89:5381-5383.

Examples of phage display libraries are described in Scott and Smith, 1990, Science 249:386-390; Devlin et al., 1990, Science, 249:404-406; Christian, R. B., et al., 1992, J. Mol. Biol. 227:711-718); Lenstra, 1992, J. Immunol. Meth. 152: 149-157; Kay et al., 1993, Gene 128:59-65; and PCT Publication No. WO 94/18318 dated Aug. 18, 1994.

In vitro translation-based libraries include but are not limited to those described in PCT Publication No. WO 91/05058 dated Apr. 18, 1991; and Mattheakis et al., 1994, Proc. Natl. Acad. Sci. USA 91:9022-9026.

By way of examples of nonpeptide libraries, a benzodiazepine library (see e.g., Bunin et al., 1994, Proc. Natl. Acad. Sci. USA 91:4708-4712) can be adapted for use. Peptoid libraries (Simon et al., 1992, Proc. Natl. Acad. Sci. USA 89:9367-9371) can also be used. Another example of a library that can be used, in which the amide functionalities in peptides have been permethylated to generate a chemically transformed combinatorial library, is described by Ostresh et al. (1994, Proc. Natl. Acad. Sci. USA 91:11138-11142).

The variety of non-peptide libraries that are useful in the present invention is great. For example, Ecker and Crooke, 1995, Bio/Technology 13:351-360 list benzodiazepines, hydantoins, piperazinediones, biphenyls, sugar analogs, beta-mercaptoketones, arylacetic acids, acylpiperidines, benzopyrans, cubanes, xanthines, aminimides, and oxazolones as among the chemical species that form the basis of various libraries.

Non-peptide libraries can be classified broadly into two types: decorated monomers and oligomers. Decorated monomer libraries employ a relatively simple scaffold structure upon which a variety functional groups is added. Often the scaffold will be a molecule with a known useful pharmacological activity. For example, the scaffold might be the benzodiazepine structure.

Non-peptide oligomer libraries utilize a large number of monomers that are assembled together in ways that create new shapes that depend on the order of the monomers. Among the monomer units that have been used are carbamates, pyrrolidones, and morpholinos. Peptoids, peptide-like oligomers in which the side chain is attached to the alpha amino group rather than the alpha carbon, form the basis of another version of non-peptide oligomer libraries. The first non-peptide oligomer libraries utilized a single type of monomer and thus contained a repeating backbone. Recent libraries have utilized more than one monomer, giving the libraries added flexibility.

Screening the libraries can be accomplished by any of a variety of commonly known methods. See, e.g., the following references, which disclose screening of peptide libraries: Parmley and Smith, 1989, Adv. Exp. Med. Biol. 251:215-218; Scott and Smith, 1990, Science 249:386-390; Fowlkes et al., 1992; BioTechniques 13:422-427; Oldenburg et al., 1992, Proc. Natl. Acad. Sci. USA 89:5393-5397; Yu et al., 1994, Cell 76:933-945; Staudt et al., 1988, Science 241:577-580; Bock et al., 1992, Nature 355:564-566; Tuerk et al., 1992, Proc. Natl. Acad. Sci. USA 89:6988-6992; Ellington et al., 1992, Nature 355:850-852; U.S. Pat. No. 5,096,815, U.S. Pat. No. 5,223,409, and U.S. Pat. No. 5,198,346, all to Ladner et al.; Rebar and Pabo, 1993, Science 263:671-673; and CT Publication No. WO 94/18318.

In a specific embodiment, screening to identify a molecule that binds polypeptides of the invention can be carried out by contacting the library members with polypeptides of the invention immobilized on a solid phase and harvesting those library members that bind to the polypeptides of the invention. Examples of such screening methods, termed "panning" techniques are described by way of example in Parmley and Smith, 1988, Gene 73:305-318; Fowlkes et al., 1992, BioTechniques 13:422-427; PCT Publication No. WO 94/18318; and in references cited herein.

In another embodiment, the two-hybrid system for selecting interacting proteins in yeast (Fields and Song, 1989, Nature 340:245-246; Chien et al., 1991, Proc. Natl. Acad. Sci. USA 88:9578-9582) can be used to identify molecules that specifically bind to polypeptides of the invention.

Where the binding molecule is a polypeptide, the polypeptide can be conveniently selected from any peptide library, including random peptide libraries, combinatorial peptide libraries, or biased peptide libraries. The term “biased” is used herein to mean that the method of generating the library is manipulated so as to restrict one or more parameters that govern the diversity of the resulting collection of molecules, in this case peptides.

Thus, a truly random peptide library would generate a collection of peptides in which the probability of finding a particular amino acid at a given position of the peptide is the same for all 20 amino acids. A bias can be introduced into the library, however, by specifying, for example, that a lysine occur every fifth amino acid or that positions 4, 8, and 9 of a decapeptide library be fixed to include only arginine. Clearly, many types of biases can be contemplated, and the present invention is not restricted to any particular bias. Furthermore, the present invention contemplates specific types of peptide libraries, such as phage displayed peptide libraries and those that utilize a DNA construct comprising a lambda phage vector with a DNA insert.

As mentioned above, in the case of a binding molecule that is a polypeptide, the polypeptide may have about 6 to less than about 60 amino acid residues, preferably about 6 to about 10 amino acid residues, and most preferably, about 6 to about 22 amino acids. In another embodiment, a binding polypeptide has in the range of 15-100 amino acids, or 20-50 amino acids.

The selected binding polypeptide can be obtained by chemical synthesis or recombinant expression.

Other Activities

A polypeptide, polynucleotide, agonist, or antagonist of the present invention, as a result of the ability to stimulate vascular endothelial cell growth, may be employed in treatment for stimulating re-vascularization of ischemic tissues due to various disease conditions such as thrombosis, arteriosclerosis, and other cardiovascular conditions. The polypeptide, polynucleotide, agonist, or antagonist of the present invention may also be employed to stimulate angiogenesis and limb regeneration, as discussed above.

A polypeptide, polynucleotide, agonist, or antagonist of the present invention may also be employed for treating wounds due to injuries, burns, post-operative tissue repair, and ulcers since they are mitogenic to various cells of different origins, such as fibroblast cells and skeletal muscle cells, and therefore, facilitate the repair or replacement of damaged or diseased tissue.

A polypeptide, polynucleotide, agonist, or antagonist of the present invention may also be employed stimulate neuronal growth and to treat and prevent neuronal damage which occurs in certain neuronal disorders or neuro-degenerative conditions such as Alzheimer’s disease, Parkinson’s disease, and AIDS-related complex. A polypeptide, polynucleotide, agonist, or antagonist of the present invention may have the ability to stimulate chondrocyte growth, therefore, they may be employed to enhance bone and periodontal regeneration and aid in tissue transplants or bone grafts.

A polypeptide, polynucleotide, agonist, or antagonist of the present invention may be also be employed to prevent skin aging due to sunburn by stimulating keratinocyte growth.

A polypeptide, polynucleotide, agonist, or antagonist of the present invention may also be employed for preventing hair loss, since FGF family members activate hair-forming cells and promotes melanocyte growth. Along the same lines, a polypeptide, polynucleotide, agonist, or antagonist of the present invention may be employed to stimulate growth and differentiation of hematopoietic cells and bone marrow cells when used in combination with other cytokines.

A polypeptide, polynucleotide, agonist, or antagonist of the present invention may also be employed to maintain organs before transplantation or for supporting cell culture of primary tissues. A polypeptide, polynucleotide, agonist, or antagonist of the present invention may also be employed for inducing tissue of mesodermal origin to differentiate in early embryos.

A polypeptide, polynucleotide, agonist, or antagonist of the present invention may also increase or decrease the differentiation or proliferation of embryonic stem cells, besides, as discussed above, hematopoietic lineage.

A polypeptide, polynucleotide, agonist, or antagonist of the present invention may also be used to modulate mammalian characteristics, such as body height, weight, hair color, eye color, skin, percentage of adipose tissue, pigmentation, size, and shape (e.g., cosmetic surgery). Similarly, a polypeptide, polynucleotide, agonist, or antagonist of the present invention may be used to modulate mammalian metabolism affecting catabolism, anabolism, processing, utilization, and storage of energy.

Polypeptides, polynucleotides, agonists, or antagonists of the present invention may be used to treat weight disorders, including but not limited to, obesity, cachexia, wasting disease, anorexia, and bulimia.

A polypeptide, polynucleotide, agonist, or antagonist of the present invention may be used to change a mammal’s mental state or physical state by influencing biorhythms, circadian rhythms, depression (including depressive disorders), tendency for violence, tolerance for pain, reproductive capabilities (preferably by Activin or Inhibin-like activity), hormonal or endocrine levels, appetite, libido, memory, stress, or other cognitive qualities.

A polypeptide, polynucleotide, agonist, or antagonist of the present invention may also be used as a food additive or preservative, such as to increase or decrease storage capabilities, fat content, lipid, protein, carbohydrate, vitamins, minerals, cofactors or other nutritional components.

The above-recited applications have uses in a wide variety of hosts. Such hosts include, but are not limited to, human, murine, rabbit, goat, guinea pig, camel, horse, mouse, rat, hamster, pig, micro-pig, chicken, goat, cow, sheep, dog, cat, non-human primate, and human. In specific embodiments, the host is a mouse, rabbit, goat, guinea pig, chicken, rat, hamster, pig, sheep, dog or cat. In preferred embodiments, the host is a mammal. In most preferred embodiments, the host is a human.

Other Preferred Embodiments

Other preferred embodiments of the claimed invention include an isolated nucleic acid molecule comprising a nucleotide sequence which is at least 95% identical to a sequence of at least about 50 contiguous nucleotides in the nucleotide sequence of SEQ ID NO:X or the complementary strand thereto, the nucleotide sequence as defined in Table 1B.1 (such as column 5 of Table 1B.1) or columns 8 and 9 of Table 2 or the complementary strand thereto, and/or cDNA contained in ATCC™ Deposit No:Z. X can be any integer as defined in Table 1A. Also preferred is the above nucleic acid molecule wherein said sequence of contiguous nucleotides is included in the nucleotide sequence of SEQ ID NO:X in the range of positions beginning with the nucleotide at about the position of the 5' Nucleotide of the Clone Sequence and ending with the nucleotide at about the position of the 3' Nucleotide of the Clone Sequence as defined for SEQ ID NO:X in Table 1A. Further preferred is the above nucleic acid molecule wherein said sequence of contiguous nucleotides is included in the nucleotide sequence of SEQ ID NO:X in the range of positions beginning with the nucleotide at about the position of the 5' Nucleotide of the Start Codon and ending with the nucleotide at about the position of the 3' Nucleotide of the Clone Sequence as defined for SEQ ID NO:X in Table 1A. Similarly preferred is the above nucleic acid molecule wherein said sequence of contiguous nucleotides is included in the nucleotide sequence of SEQ ID NO:X in the range of positions beginning with the nucleotide at about the position of the 5' Nucleotide of the First Amino Acid of the Signal Peptide and ending with the nucleotide at about the position of the 3' Nucleotide of the Clone Sequence as defined for SEQ ID NO:X in Table 1A.

Also preferred is a nucleic acid molecule wherein said sequence of contiguous nucleotides is included in the nucleotide sequence of the portion of SEQ ID NO:X as defined in column 5, “ORF (From-To)”, in Table 1B.1.

Also preferred is a nucleic acid molecule wherein said sequence of contiguous nucleotides is included in the nucleotide sequence of the portion of SEQ ID NO:X as defined in columns 8 and 9, “NT From” and “NT To” respectively, in Table 2.

Also preferred is an isolated nucleic acid molecule comprising a nucleotide sequence which is at least 95% identical to a sequence of at least about 150 contiguous nucleotides in the nucleotide sequence of SEQ ID NO:X or the complementary strand thereto, the nucleotide sequence as defined in Table 1B.1 (such as column 5 of Table 1B.1) or columns 8 and 9 of Table 2 or the complementary strand thereto, and/or cDNA contained in ATCC™ Deposit No:Z.

Further preferred is an isolated nucleic acid molecule comprising a nucleotide sequence which is at least 95% identical to a sequence of at least about 500 contiguous nucleotides in the nucleotide sequence of SEQ ID NO:X or the complementary strand thereto, the nucleotide sequence as defined in Table 1B.1 (such as column 5 of Table 1B.1) or columns 8 and 9 of Table 2 or the complementary strand thereto, and/or cDNA contained in ATCC™ Deposit No:Z.

A further preferred embodiment is a nucleic acid molecule comprising a nucleotide sequence which is at least 95% identical to the nucleotide sequence of the portion of SEQ ID NO:X defined in column 5, “ORF (From-To)”, in Table 1B.1.

A further preferred embodiment is a nucleic acid molecule comprising a nucleotide sequence which is at least 95% identical to the nucleotide sequence of the portion of SEQ ID NO:X defined in columns 8 and 9, “NT From” and “NT To”, respectively, in Table 2.

A further preferred embodiment is an isolated nucleic acid molecule comprising a nucleotide sequence which is at least 95% identical to the complete nucleotide sequence of SEQ ID NO:X or the complementary strand thereto, the nucleotide sequence as defined in Table 1B.1 (such as column 5 of Table 1B.1) or columns 8 and 9 of Table 2 or the complementary strand thereto, and/or cDNA contained in ATCC™ Deposit No:Z.

Also preferred is an isolated nucleic acid molecule which hybridizes under stringent hybridization conditions to a nucleic acid molecule comprising a nucleotide sequence of SEQ ID NO:X or the complementary strand thereto, the nucleotide sequence as defined in Table 1B.1 (such as column 5 of Table 1B.1) or columns 8 and 9 of Table 2 or the complementary strand thereto, and/or cDNA contained in ATCC™ Deposit No:Z, wherein said nucleic acid molecule which hybridizes does not hybridize under stringent hybridization conditions to a nucleic acid molecule having a nucleotide sequence consisting of only A residues or of only T residues.

Also preferred is a composition of matter comprising a DNA molecule which comprises the cDNA contained in ATCC™ Deposit No:Z.

Also preferred is an isolated nucleic acid molecule comprising a nucleotide sequence which is at least 95% identical to a sequence of at least 50 contiguous nucleotides of the cDNA sequence contained in ATCC™ Deposit No:Z.

Also preferred is an isolated nucleic acid molecule, wherein said sequence of at least 50 contiguous nucleotides is included in the nucleotide sequence of an open reading frame sequence encoded by cDNA contained in ATCC™ Deposit No:Z.

Also preferred is an isolated nucleic acid molecule comprising a nucleotide sequence which is at least 95% identical to sequence of at least 150 contiguous nucleotides in the nucleotide sequence encoded by cDNA contained in ATCC™ Deposit No:Z.

A further preferred embodiment is an isolated nucleic acid molecule comprising a nucleotide sequence which is at least 95% identical to sequence of at least 500 contiguous nucleotides in the nucleotide sequence encoded by cDNA contained in ATCC™ Deposit No:Z.

A further preferred embodiment is an isolated nucleic acid molecule comprising a nucleotide sequence which is at least 95% identical to the complete nucleotide sequence encoded by cDNA contained in ATCC™ Deposit No:Z.

A further preferred embodiment is a method for detecting in a biological sample a nucleic acid molecule comprising a nucleotide sequence which is at least 95% identical to a sequence of at least 50 contiguous nucleotides in a sequence selected from the group consisting of: a nucleotide sequence of SEQ ID NO:X or the complementary strand thereto; the nucleotide sequence as defined in Table 1B.1 (such as column 5 of Table 1B.1) or columns 8 and 9 of Table 2 or the complementary strand thereto; and a nucleotide sequence encoded by cDNA contained in ATCC™ Deposit No:Z; which method comprises a step of comparing a nucleotide sequence of at least one nucleic acid molecule in said sample with a sequence selected from said group and determining whether the sequence of said nucleic acid molecule in said sample is at least 95% identical to said selected sequence.

Also preferred is the above method wherein said step of comparing sequences comprises determining the extent of nucleic acid hybridization between nucleic acid molecules in said sample and a nucleic acid molecule comprising said sequence selected from said group. Similarly, also preferred is the above method wherein said step of comparing sequences is performed by comparing the nucleotide sequence determined from a nucleic acid molecule in said sample with said sequence selected from said group. The nucleic acid molecules can comprise DNA molecules or RNA molecules.

A further preferred embodiment is a method for identifying the species, tissue or cell type of a biological sample which method comprises a step of detecting nucleic acid molecules in said sample, if any, comprising a nucleotide sequence that is at least 95% identical to a sequence of at least 50 contiguous nucleotides in a sequence selected from the group consisting of: a nucleotide sequence of SEQ ID NO:X or the complementary strand thereto; the nucleotide sequence as defined in Table 1B.1 (such as column 5 of Table 1B.1) or columns 8 and 9 of Table 2 or the complementary strand thereto; and a nucleotide sequence of the cDNA contained in ATCC™ Deposit No:Z.

The method for identifying the species, tissue or cell type of a biological sample can comprise a step of detecting nucleic acid molecules comprising a nucleotide sequence in a panel of at least two nucleotide sequences, wherein at least one sequence in said panel is at least 95% identical to a sequence of at least 50 contiguous nucleotides in a sequence selected from said group.

Also preferred is a method for diagnosing in a subject a pathological condition associated with abnormal structure or expression of a nucleotide sequence of SEQ ID NO:X or the complementary strand thereto; the nucleotide sequence as defined in Table 1B.1 (such as column 5 of Table 1B.1) or columns 8 and 9 of Table 2 or the complementary strand thereto; or the cDNA contained in ATCC™ Deposit No:Z which encodes a protein, wherein the method comprises a step of detecting in a biological sample obtained from said subject nucleic acid molecules, if any, comprising a nucleotide sequence that is at least 95% identical to a sequence of at least 50 contiguous nucleotides in a sequence selected from the group consisting of: a nucleotide sequence of SEQ ID NO:X or the complementary strand thereto; the nucleotide sequence as defined in Table 1B.1 (such as column 5 of Table 1B.1) or columns 8 and 9 of Table 2 or the complementary strand thereto; and a nucleotide sequence of cDNA contained in ATCC™ Deposit No:Z.

The method for diagnosing a pathological condition can comprise a step of detecting nucleic acid molecules comprising a nucleotide sequence in a panel of at least two nucleotide sequences, wherein at least one sequence in said panel is at least 95% identical to a sequence of at least 50 contiguous nucleotides in a sequence selected from said group.

Also preferred is a composition of matter comprising isolated nucleic acid molecules wherein the nucleotide sequences of said nucleic acid molecules comprise a panel of at least two nucleotide sequences, wherein at least one sequence in said panel is at least 95% identical to a sequence of at least 50 contiguous nucleotides in a sequence selected from the group consisting of: a nucleotide sequence of SEQ ID NO:X or the complementary strand thereto; the nucleotide sequence as defined in Table 1B.1 (such as column 5 of Table 1B.1) or columns 8 and 9 of Table 2 or the complementary strand thereto; and a nucleotide sequence encoded by cDNA contained in ATCC™ Deposit No:Z. The nucleic acid molecules can comprise DNA molecules or RNA molecules.

Also preferred is a composition of matter comprising isolated nucleic acid molecules wherein the nucleotide sequences of said nucleic acid molecules comprise a DNA microarray or "chip" of at least 1, 2, 3, 4, 5, 6, 7, 8, 9, 10, 15, 20, 25, 30, 40, 50, 100, 150, 200, 250, 300, 500, 1000, 2000, 3000, or 4000 nucleotide sequences, wherein at least one sequence in said DNA microarray or "chip" is at least 95% identical to a sequence of at least 50 contiguous nucleotides in a sequence selected from the group consisting of: a nucleotide sequence of SEQ ID NO:X wherein X is any integer as defined in Table 1A and/or Tables 1B.1 and 1B.2; and a nucleotide sequence encoded by a human cDNA clone identified by a cDNA "Clone ID" in Table 1A and/or Tables 1B.1 and 1B.2. Further preferred is the above isolated polypeptide, wherein said sequence of contiguous amino acids is included in the amino acid sequence of SEQ ID NO:Y in the range of positions beginning with the residue at about the position of the First Amino Acid of the Secreted Portion and ending with the residue at about the Last Amino Acid of the Open Reading Frame as set forth for SEQ ID NO:Y in Table 1A.

Also preferred is an isolated polypeptide comprising an amino acid sequence at least 90% identical to a sequence of at least about 10 contiguous amino acids in the polypeptide sequence of SEQ ID NO:Y; a polypeptide encoded by SEQ ID NO:X or the complementary strand thereto; the polypeptide encoded by the nucleotide sequence as defined in columns 8 and 9 of Table 2; and/or a polypeptide encoded by cDNA contained in ATCC™ Deposit No:Z.

Also preferred is an isolated polypeptide comprising an amino acid sequence at least 95% identical to a sequence of at least about 30 contiguous amino acids in the amino acid sequence of SEQ ID NO:Y; a polypeptide encoded by SEQ ID NO:X or the complementary strand thereto; the polypeptide encoded by the nucleotide sequence as defined in columns 8 and 9 of Table 2; and/or a polypeptide encoded by cDNA contained in ATCC™ Deposit No:Z.

Further preferred is an isolated polypeptide comprising an amino acid sequence at least 95% identical to a sequence of at least about 100 contiguous amino acids in the amino acid sequence of SEQ ID NO:Y; a polypeptide encoded by SEQ ID NO:X or the complementary strand thereto; the polypeptide encoded by the nucleotide sequence as defined in columns 8 and 9 of Table 2; and/or a polypeptide encoded by cDNA contained in ATCC™ Deposit No:Z.

Further preferred is an isolated polypeptide comprising an amino acid sequence at least 95% identical to the complete amino acid sequence of SEQ ID NO:Y; a polypeptide encoded by SEQ ID NO:X or the complementary strand thereto; the polypeptide encoded by the nucleotide sequence as defined in columns 8 and 9 of Table 2; and/or a polypeptide encoded by cDNA contained in ATCC™ Deposit No:Z.

Further preferred is an isolated polypeptide comprising an amino acid sequence at least 90% identical to a sequence of at least about 10 contiguous amino acids in the complete amino acid sequence of a polypeptide encoded by contained in ATCC™ Deposit No:Z Also preferred is a polypeptide wherein said sequence of contiguous amino acids is included in the amino acid sequence of a portion of said polypeptide encoded by cDNA contained in ATCC™ Deposit No:Z; a polypeptide encoded by SEQ ID NO:X or the complementary strand thereto; the polypeptide encoded by the nucleotide sequence as defined in columns 8 and 9 of Table 2; and/or the polypeptide sequence of SEQ ID NO:Y.

Also preferred is an isolated polypeptide comprising an amino acid sequence at least 95% identical to a sequence of at least about 30 contiguous amino acids in the amino acid sequence of a polypeptide encoded by the cDNA contained in ATCC™ Deposit No:Z.

Also preferred is an isolated polypeptide comprising an amino acid sequence at least 95% identical to a sequence of at least about 100 contiguous amino acids in the amino acid sequence of a polypeptide encoded by cDNA contained in ATCC™ Deposit No:Z.

Also preferred is an isolated polypeptide comprising an amino acid sequence at least 95% identical to the amino acid sequence of a polypeptide encoded by the cDNA contained in ATCC™ Deposit No:Z.

Further preferred is an isolated antibody which binds specifically to a polypeptide comprising an amino acid sequence that is at least 90% identical to a sequence of at least 10 contiguous amino acids in a sequence selected from the group consisting of: a polypeptide sequence of SEQ ID NO:Y; a polypeptide encoded by SEQ ID NO:X or the complementary strand thereto; the polypeptide encoded by the nucleotide sequence as defined in columns 8 and 9 of Table 2; and a polypeptide encoded by the cDNA contained in ATCC™ Deposit No:Z.

Further preferred is a method for detecting in a biological sample a polypeptide comprising an amino acid sequence which is at least 90% identical to a sequence of at least 10 contiguous amino acids in a sequence selected from the group consisting of: a polypeptide sequence of SEQ ID NO:Y; a polypeptide encoded by SEQ ID NO:X or the complementary strand thereto; the polypeptide encoded by the nucleotide sequence as defined in columns 8 and 9 of Table 2; and a polypeptide encoded by the cDNA contained in ATCC™ Deposit No:Z; which method comprises a step of comparing an amino acid sequence of at least one polypeptide molecule in said sample with a sequence selected from said group and determining whether the sequence of said polypeptide molecule in said sample is at least 90% identical to said sequence of at least 10 contiguous amino acids.

Also preferred is the above method wherein said step of comparing an amino acid sequence of at least one polypeptide molecule in said sample with a sequence selected from said group comprises determining the extent of specific binding of polypeptides in said sample to an antibody which binds specifically to a polypeptide comprising an amino acid sequence that is at least 90% identical to a sequence of at least 10 contiguous amino acids in a sequence selected from the group consisting of: a polypeptide sequence of SEQ ID NO:Y; a polypeptide encoded by SEQ ID NO:X or the complementary strand thereto; the polypeptide encoded by the nucleotide sequence as defined in columns 8 and 9 of Table 2; and a polypeptide encoded by the cDNA contained in ATCC™ Deposit No:Z.

Also preferred is the above method wherein said step of comparing sequences is performed by comparing the amino acid sequence determined from a polypeptide molecule in said sample with said sequence selected from said group.

Also preferred is a method for identifying the species, tissue or cell type of a biological sample which method comprises a step of detecting polypeptide molecules in said sample, if any, comprising an amino acid sequence that is at least 90% identical to a sequence of at least 10 contiguous amino acids in a sequence selected from the group consisting of: polypeptide sequence of SEQ ID NO:Y; a polypeptide encoded by SEQ ID NO:X or the complementary strand thereto; the polypeptide encoded by the nucleotide sequence as defined in columns 8 and 9 of Table 2; and a polypeptide encoded by the cDNA contained in ATCC™ Deposit No:Z.

Also preferred is the above method for identifying the species, tissue or cell type of a biological sample, which method comprises a step of detecting polypeptide molecules comprising an amino acid sequence in a panel of at least two amino acid sequences, wherein at least one sequence in said panel is at least 90% identical to a sequence of at least 10 contiguous amino acids in a sequence selected from the above group.

Also preferred is a method for diagnosing in a subject a pathological condition associated with abnormal structure or expression of a nucleic acid sequence identified in Tables 1A, 1B.1, 1B.2 or 2 encoding a polypeptide, which method comprises a step of detecting in a biological sample obtained from said subject polypeptide molecules comprising an amino acid sequence in a panel of at least two amino acid sequences, wherein at least one sequence in said panel is at least 90% identical to a sequence of at least 10 contiguous amino acids in a sequence selected from the group consisting of: polypeptide sequence of SEQ ID NO:Y; a polypeptide encoded by SEQ ID NO:X or the complementary strand thereto; the polypeptide encoded by the nucleotide sequence as defined in columns 8 and 9 of Table 2; and a polypeptide encoded by the cDNA contained in ATCC™ Deposit No:Z.

In any of these methods, the step of detecting said polypeptide molecules includes using an antibody.

Also preferred is an isolated nucleic acid molecule comprising a nucleotide sequence which is at least 95% identical to a nucleotide sequence encoding a polypeptide wherein said polypeptide comprises an amino acid sequence that is at least 90% identical to a sequence of at least 10 contiguous amino acids in a sequence selected from the group consisting of: polypeptide sequence of SEQ ID NO:Y; a polypeptide encoded by SEQ ID NO:X or the complementary strand thereto; the polypeptide encoded by the nucleotide sequence as defined in columns 8 and 9 of Table 2; and a polypeptide encoded by the cDNA contained in ATCC™ Deposit No:Z.

Also preferred is an isolated nucleic acid molecule, wherein said nucleotide sequence encoding a polypeptide has been optimized for expression of said polypeptide in a prokaryotic host.

Also preferred is a polypeptide molecule, wherein said polypeptide comprises an amino acid sequence selected from the group consisting of: polypeptide sequence of SEQ ID NO:Y; a polypeptide encoded by SEQ ID NO:X or the complementary strand thereto; the polypeptide encoded by the nucleotide sequence as defined in columns 8 and 9 of Table 2; and a polypeptide encoded by the cDNA contained in ATCC™ Deposit No:Z.

Further preferred is a method of making a recombinant vector comprising inserting any of the above isolated nucleic acid molecules into a vector. Also preferred is the recombinant vector produced by this method. Also preferred is a method of making a recombinant host cell comprising introducing the vector into a host cell, as well as the recombinant host cell produced by this method.

Also preferred is a method of making an isolated polypeptide comprising culturing this recombinant host cell under conditions such that said polypeptide is expressed and recovering said polypeptide. Also preferred is this method of making an isolated polypeptide, wherein said recombinant host cell is a eukaryotic cell and said polypeptide is a human protein comprising an amino acid sequence selected from the group consisting of: polypeptide sequence of SEQ ID NO:Y; an amino acid sequence of SEQ ID NO:Y beginning with the residue at the position of the First Amino Acid of the Secreted Portion of SEQ ID NO:Y wherein Y is an integer set forth in Table 1A and said position of the First Amino Acid of the Secreted Portion of SEQ ID NO:Y is defined in Table 1A; and an amino acid sequence of a secreted portion of a protein encoded by a human cDNA clone identified by a cDNA Clone Identifier in Table 1A and contained in the deposit with ATCC™ Deposit No:Z; a polypeptide encoded by SEQ ID NO:X or the complementary strand thereto; the polypeptide encoded by the nucleotide sequence as defined in columns 8 and 9 of Table 2; and a polypeptide encoded by the cDNA contained in ATCC™ Deposit No:Z. The isolated polypeptide produced by this method is also preferred.

Also preferred is a method of treatment of an individual in need of an increased level of a protein activity, which method comprises administering to such an individual a Therapeutic comprising an amount of an isolated polypeptide, polynucleotide, immunogenic fragment or analogue thereof, binding agent, antibody, or antigen binding fragment of the claimed invention effective to increase the level of said protein activity in said individual.

Also preferred is an isolated nucleic acid molecule comprising a polynucleotide having a nucleotide sequence at least 95% identical to a sequence selected from the group consisting of: (a) a polynucleotide fragment of SEQ ID NO:X or a polynucleotide fragment of the cDNA sequence included in ATCC™ Deposit No:Z, which is hybridizable to SEQ ID NO:X; (b) a polynucleotide encoding a polypeptide fragment of SEQ ID NO:Y or a polypeptide fragment encoded by the cDNA sequence included in ATCC™ Deposit No:Z, which is hybridizable to SEQ ID NO:X; (c) a polynucleotide encoding a polypeptide domain of SEQ ID NO:Y or a polypeptide domain encoded by the cDNA sequence included in ATCC™ Deposit No:Z, which is hybridizable to SEQ ID NO:X; (d) a polynucleotide encoding a polypeptide epitope of SEQ ID NO:Y or a polypeptide epitope encoded by the cDNA sequence included in ATCC™ Deposit No:Z, which is hybridizable to SEQ ID NO:X; (e) a polynucleotide encoding a polypeptide of SEQ ID NO:Y or the cDNA sequence included in ATCC™ Deposit No:Z, which is hybridizable to SEQ ID NO:X, having biological activity; (f) a polynucleotide which is a variant of SEQ ID NO:X; (g) a polynucleotide which is an allelic variant of SEQ ID NO:X; (h) a polynucleotide which encodes a species homologue of the SEQ ID NO:Y; and (i) a polynucleotide capable of hybridizing under stringent conditions to any one of the polynucleotides specified in (a)-(h), wherein said polynucleotide does not hybridize under stringent conditions to a nucleic acid molecule having a nucleotide sequence of only A residues or of only T residues.

Also preferred is the isolated nucleic acid molecule as described in preferred embodiment I, wherein the polynucleotide fragment comprises a nucleotide sequence encoding a secreted protein. The nucleotide sequence encoding a secreted protein may further comprise sequential nucleotide deletions from either the C-terminus or the N-terminus.

Also preferred is the isolated nucleic acid molecule as described in preferred embodiment I, wherein the polynucleotide fragment comprises a nucleotide sequence encoding the sequence identified as SEQ ID NO:Y or the polypeptide encoded by the cDNA sequence included in ATCC™ Deposit No:Z, which is hybridizable to SEQ ID NO:X. The nucleotide sequence encoding the sequence identified as SEQ ID NO:Y or the polypeptide encoded by the cDNA sequence included in ATCC™ Deposit No:Z may further comprise sequential nucleotide deletions from either the C-terminus or the N-terminus.

Also preferred is the isolated nucleic acid molecule as described in preferred embodiment I, wherein the polynucleotide fragment comprises the entire nucleotide sequence of SEQ ID NO:X or the cDNA sequence included in ATCC™ Deposit No:Z, which is hybridizable to SEQ ID NO:X.

Also preferred is a recombinant vector comprising the isolated nucleic acid molecule described in preferred embodiment I.

Also preferred is a recombinant host cell comprising the isolated nucleic acid molecule described in preferred embodiment I and the method of making the recombinant host cell. The recombinant host cell may further comprise vector sequences.

Also preferred is a method of diagnosing a pathological condition or a susceptibility to a pathological condition in a subject comprising determining the presence or absence of a mutation in the polynucleotide described in preferred embodiment I and diagnosing a pathological condition or a susceptibility to a pathological condition based on the presence or absence of the mutation.

An isolated polypeptide comprising an amino acid sequence at least 95% identical to a sequence selected from the group consisting of: (a) a polypeptide fragment of SEQ ID NO:Y or the encoded sequence included in ATCC™ Deposit No:Z; (b) a polypeptide fragment of SEQ ID NO:Y or the encoded sequence included in ATCC™ Deposit No:Z, having biological activity; (c) a polypeptide domain of SEQ ID NO:Y or the encoded sequence included in ATCC™ Deposit No:Z; (d) a polypeptide epitope of SEQ ID NO:Y or the encoded sequence included in ATCC™ Deposit No:Z; (e) a secreted form of SEQ ID NO:Y or the encoded sequence included in ATCC™ Deposit No:Z; (f) a full length protein of SEQ ID NO:Y or the encoded sequence included in ATCC™ Deposit No:Z; (g) a variant of SEQ ID NO:Y; (h) an allelic variant of SEQ ID NO:Y; and (i) a species homologue of SEQ ID NO:Y.

Also preferred is the isolated polypeptide as described in preferred embodiment II, wherein the secreted form or the full length protein comprises sequential amino acid deletions from either the C-terminus or the N-terminus.

Also preferred is an isolated antibody that binds specifically to the isolated polypeptide described in preferred embodiment II.

Also preferred is a recombinant host cell that expresses the isolated polypeptide described in preferred embodiment II.

Also preferred is a method of making an isolated polypeptide that comprises culturing the recombinant host cells that expresses the isolated polypeptide described in preferred embodiment II and recovering said polypeptide. Further envisioned is the polypeptide produced by this method.

Also preferred is a method of diagnosing a pathological condition or a susceptibility to a pathological condition in a subject comprising: (a) determining the presence or amount of expression of the polypeptide described in preferred embodiment II in a biological sample; and (b) diagnosing a pathological condition or a susceptibility to a pathological condition based on the presence or amount of expression of the polypeptide.

Also preferred is a method for identifying a binding partner to the polypeptide described in preferred embodiment II comprising: (a) contacting the polypeptide with a binding partner; and (b) determining whether the binding partner effects an activity of the polypeptide The gene corresponding to the cDNA sequence of SEQ ID NO:X.

A method of identifying an activity in a biological assay, wherein the method comprises: (a) expressing SEQ ID NO:X in a cell; (b) isolating the supernatent; (c) detecting an activity in a biological assay; and (d) identifying the protein in the supernatent having the activity. Preferred embodiment IV may further include the product produced by the method.

Also preferred is a method for preventing, treating, or ameliorating a medical condition comprising administering to a mammalian subject a therapeutically effective amount of the polynucleotide described in preferred embodiment I or the polypeptide described in preferred embodiment II.

Also preferred is a method of treatment of an individual in need of a decreased level of a protein activity, which method comprised administering to such an individual a Therapeutic comprising an amount of an isolated polypeptide, polynucleotide, immunogenic fragment or analogue thereof, binding agent, antibody, or antigen binding fragment of the claimed invention effective to decrease the level of said protein activity in said individual.

Also preferred is a method of treatment of an individual in need of a specific delivery of toxic compositions to diseased cells (e.g., tumors, leukemias or lymphomas), which method comprises administering to such an individual a Therapeutic comprising an amount of an isolated polypeptide of the invention, including, but not limited to a binding agent, or antibody of the claimed invention that are associated with toxin or cytotoxic prodrugs.

Having generally described the invention, the same will be more readily understood by reference to the examples disclosed herein, which are provided by way of illustration and are not intended as limiting.

In specific embodiments of the invention, for each "Contig ID" listed in the second column of Table 2, preferably excluded are one or more polynucleotides comprising, or alternatively consisting of, a nucleotide sequence referenced in the fifth column of Table 2 and described by the general formula of a–b, whereas a and b are uniquely determined for the corresponding SEQ ID NO:X referred to in column 3 of Table 2. Further specific embodiments are directed to polynucleotide sequences excluding one, two, three, four, or more of the specific polynucleotide sequences referred to in the fifth column of Table 2. In no way is this listing meant to encompass all of the sequences which may be excluded by the general formula, it is just a representative example. All references available through these accessions are hereby incorporated by reference in their entirety.

Table 6

Table 6 summarizes some of the ATCC™ Deposits, Deposit dates, and ATCC™ designation numbers of deposits made with the ATCC™ in connection with the present application. These deposits were made in addition to those described in the Table 1A.

TABLE 6

| ATCC ™ Deposits | Deposit Date | ATCC ™ Designation Number |
|---|---|---|
| LP01, LP02, LP03, LP04, LP05, LP06, LP07, LP08, LP09, LP10, LP11 | May 20, 1997 | 209059, 209060, 209061, 209062, 209063, 209064, 209065, 209066, 209067, 209068, 209069 |
| LP12 | Jan. 12, 1998 | 209579 |
| LP13 | Jan. 12, 1998 | 209578 |
| LP14 | Jul. 16, 1998 | 203067 |
| LP15 | Jul. 16, 1998 | 203068 |
| LP16 | Feb. 1, 1999 | 203609 |
| LP17 | Feb. 1, 1999 | 203610 |
| LP20 | Nov. 17, 1998 | 203485 |
| LP21 | Jun. 18, 1999 | PTA-252 |
| LP22 | Jun. 18, 1999 | PTA-253 |
| LP23 | Dec. 22, 1999 | PTA-1081 |

EXAMPLES

Example 1

Isolation of a Selected cDNA Clone from the Deposited Sample

Each ATCC™ Deposit No:Z is contained in a plasmid vector. Table 1A identifies the vectors used to construct the cDNA library from which each clone was isolated. In many cases, the vector used to construct the library is a phage vector from which a plasmid has been excised. The following correlates the related plasmid for each phage vector used in constructing the cDNA library. For example, where a particular clone is identified in Table 1A as being isolated in the vector "LAMBDA ZAP™," the corresponding deposited clone is in "pBLUESCRIPT™."

| Vector Used to Construct Library | Corresponding Deposited Plasmid |
|---|---|
| LAMBDA ZAP ™ | pBLUESCRIPT ™ (pBS) |
| UNI-ZAP ™ XR | pBLUESCRIPT ™ (pBS) |
| ZAP EXPRESS ™ | pBK |
| lafmid BA | plafmid BA |
| pSport1 | pSport1 |
| pCMVSport 2.0 | pCMVSport 2.0 |
| pCMVSport 3.0 | pCMVSport 3.0 |
| pCR ® 2.1 | pCR ® 2.1 |

Vectors LAMBDA ZAP™ (U.S. Pat. Nos. 5,128,256 and 5,286,636), UNI-ZAP™ XR (U.S. Pat. Nos. 5,128,256 and 5,286,636), ZAP EXPRESS™ (U.S. Pat. Nos. 5,128,256 and 5,286,636), pBLUESCRIPT™ (pBS) (Short, J. M. et al., Nucleic Acids Res. 16:7583-7600 (1988); Alting-Mees, M. A. and Short, J. M., Nucleic Acids Res. 17:9494 (1989)) and pBK (Alting-Mees, M. A. et al., Strategies 5:58-61 (1992)) are commercially available from STRATAGENE™ Cloning Systems, Inc., 11011 N. Torrey Pines Road, La Jolla, Calif., 92037. pBS contains an ampicillin resistance gene and pBK contains a neomycin resistance gene. Both can be transformed into *E. coli* strain XL-1 Blue, also available from STRATAGENE™. pBS comes in 4 forms SK+, SK−, KS+ and KS. The S and K refers to the orientation of the polylinker to the T7 and T3 primer sequences which flank the polylinker region ("S" is for SacI and "K" is for KpnI which are the first sites on each respective end of the linker). "+" or "−" refer to the orientation of the f1 origin of replication ("ori"), such that in one orientation, single stranded rescue initiated from the f1 on generates sense strand DNA and in the other, antisense.

Vectors pSport1, pCMVSport 2.0 and pCMVSport 3.0, were obtained from LIFE TECHNOLOGIES™, Inc., P.O. Box 6009, Gaithersburg, Md. 20897. All Sport vectors contain an ampicillin resistance gene and may be transformed into *E. coli* strain DH10B, also available from LIFE TECHNOLOGIES™. (See, for instance, Gruber, C. E., et al., Focus 15:59 (1993)). Vector lafmid BA (Bento Soares, Columbia University, NY) contains an ampicillin resistance gene and can be transformed into *E. coli* strain XL-1 Blue. Vector pCR®2.1, which is available from Invitrogen, 1600 Faraday Avenue, Carlsbad, Calif. 92008, contains an ampicillin resistance gene and may be transformed into *E. coli* strain DH10B, available from LIFE TECHNOLOGIES™. (See, for instance, Clark, J. M., Nuc. Acids Res. 16:9677-9686 (1988) and Mead, D. et al., Bio/Technology 9: (1991)). Preferably, a polynucleotide of the present invention does not comprise the phage vector sequences identified for the particular clone in Table 1A, as well as the corresponding plasmid vector sequences designated above.

The deposited material in the sample assigned the ATCC™ Deposit Number cited by reference to Tables 1A, 6, and 7 for any given cDNA clone also may contain one or more additional plasmids, each comprising a cDNA clone different from that given clone. Thus, deposits sharing the same ATCC™ Deposit Number contain at least a plasmid for each ATCC™ Deposit No:Z.

TABLE 7

| Libraries owned by Catalog | Catalog Description | Vector | ATCC ™ Deposit |
|---|---|---|---|
| HUKA HUKB HUKC HUKD HUKE HUKF HUKG | Human Uterine Cancer | Lambda ZAP II | LP01 |
| HCNA HCNB | Human Colon | Lambda Zap II | LP01 |
| HFFA | Human Fetal Brain, random primed | Lambda Zap II | LP01 |
| HTWA | Resting T-Cell | Lambda ZAP II | LP01 |
| HBQA | Early Stage Human Brain, random primed | Lambda ZAP II | LP01 |
| HLMB HLMF HLMG HLMH HLMI HLMJ HLMM HLMN | breast lymph node CDNA library | Lambda ZAP II | LP01 |
| HCQA HCQB | human colon cancer | Lamda ZAP II | LP01 |
| HMEA HMEC HMED HMEE HMEF HMEG HMEI HMEJ HMEK HMEL | Human Microvascular Endothelial Cells, fract. A | Lambda ZAP II | LP01 |
| HUSA HUSC | Human Umbilical Vein Endothelial Cells, fract. A | Lambda ZAP II | LP01 |
| HLQA HLQB | Hepatocellular Tumor | Lambda ZAP II | LP01 |
| HHGA HHGB HHGC HHGD | Hemangiopericytoma | Lambda ZAP II | LP01 |
| HSDM | Human Striatum Depression, re-rescue | Lambda ZAP II | LP01 |
| HUSH | H Umbilical Vein Endothelial Cells, frac A, re-excision | Lambda ZAP II | LP01 |
| HSGS | Salivary gland, subtracted | Lambda ZAP II | LP01 |
| HFXA HFXB HFXC HFXD HFXE HFXF HFXG HFXH | Brain frontal cortex | Lambda ZAP II | LP01 |
| HPQA HPQB HPQC | PERM TF274 | Lambda ZAP II | LP01 |
| HFXJ HFXK | Brain Frontal Cortex, re-excision | Lambda ZAP II | LP01 |
| HCWA HCWB HCWC HCWD HCWE HCWF HCWG HCWH HCWI HCWJ HCWK | CD34 positive cells (Cord Blood) | ZAP Express | LP02 |
| HCUA HCUB HCUC | CD34 depleted Buffy Coat (Cord Blood) | ZAP Express | LP02 |
| HRSM | A-14 cell line | ZAP Express | LP02 |
| HRSA | A1-CELL LINE | ZAP Express | LP02 |
| HCUD HCUE HCUF HCUG HCUH HCUI | CD34 depleted Buffy Coat (Cord Blood), re-excision | ZAP Express | LP02 |
| HBXE HBXF HBXG | H. Whole Brain #2, re-excision | ZAP Express | LP02 |
| HRLM | L8 cell line | ZAP Express | LP02 |
| HBXA HBXB HBXC HBXD | Human Whole Brain #2 - Oligo dT >1.5 Kb | ZAP Express | LP02 |
| HUDA HUDB HUDC | Testes | ZAP Express | LP02 |
| HHTM HHTN HHTO | H. hypothalamus, frac A; re-excision | ZAP Express | LP02 |
| HHTL | H. hypothalamus, frac A | ZAP Express | LP02 |
| HASA HASD | Human Adult Spleen | Uni-ZAP XR | LP03 |
| HFKC HFKD HFKE HFKF HFKG | Human Fetal Kidney | Uni-ZAP XR | LP03 |
| HE8A HE8B HE8C HE8D HE8E HE8F HE8M HE8N | Human 8 Week Whole Embryo | Uni-ZAP XR | LP03 |
| HGBA HGBD HGBE HGBF HGBG HGBH HGBI | Human Gall Bladder | Uni-ZAP XR | LP03 |
| HLHA HLHB HLHC HLHD HLHE HLHF HLHG HLHH HLHQ | Human Fetal Lung III | Uni-ZAP XR | LP03 |
| HPMA HPMB HPMC HPMD HPME HPMF HPMG HPMH | Human Placenta | Uni-ZAP XR | LP03 |
| HPRA HPRB HPRC HPRD | Human Prostate | Uni-ZAP XR | LP03 |
| HSIA HSIC HSID HSIE | Human Adult Small Intestine | Uni-ZAP XR | LP03 |
| HTEA HTEB HTEC HTED HTEE HTEF HTEG HTEH HTEI HTEJ HTEK | Human Testes | Uni-ZAP XR | LP03 |
| HTPA HTPB HTPC HTPD HTPE | Human Pancreas Tumor | Uni-ZAP XR | LP03 |
| HTTA HTTB HTTC HTTD HTTE HTTF | Human Testes Tumor | Uni-ZAP XR | LP03 |
| HAPA HAPB HAPC HAPM | Human Adult Pulmonary | Uni-ZAP XR | LP03 |
| HETA HETB HETC HETD HETE HETF HETG HETH HETI | Human Endometrial Tumor | Uni-ZAP XR | LP03 |
| HHFB HHFC HHFD HHFE HHFF HHFG HHFH HHFI | Human Fetal Heart | Uni-ZAP XR | LP03 |
| HHPB HHPC HHPD HHPE HHPF HHPG HHPH | Human Hippocampus | Uni-ZAP XR | LP03 |

TABLE 7-continued

| Libraries owned by Catalog | Catalog Description | Vector | ATCC ™ Deposit |
|---|---|---|---|
| HCE1 HCE2 HCE3 HCE4 HCE5 HCEB HCEC HCED HCEE HCEF HCEG | Human Cerebellum | Uni-ZAP XR | LP03 |
| HUVB HUVC HUVD HUVE | Human Umbilical Vein, Endo. remake | Uni-ZAP XR | LP03 |
| HSTA HSTB HSTC HSTD | Human Skin Tumor | Uni-ZAP XR | LP03 |
| HTAA HTAB HTAC HTAD HTAE | Human Activated T-Cells | Uni-ZAP XR | LP03 |
| HFEA HFEB HFEC | Human Fetal Epithelium (Skin) | Uni-ZAP XR | LP03 |
| HJPA HJPB HJPC HJPD | HUMAN JURKAT MEMBRANE BOUND POLYSOMES | Uni-ZAP XR | LP03 |
| HESA | Human epithelioid sarcoma | Uni-Zap XR | LP03 |
| HLTA HLTB HLTC HLTD HLTE HLTF | Human T-Cell Lymphoma | Uni-ZAP XR | LP03 |
| HFTA HFTB HFTC HFTD | Human Fetal Dura Mater | Uni-ZAP XR | LP03 |
| HRDA HRDB HRDC HRDD HRDE HRDF | Human Rhabdomyosarcoma | Uni-ZAP XR | LP03 |
| HCAA HCAB HCAC | Cem cells cyclohexamide treated | Uni-ZAP XR | LP03 |
| HRGA HRGB HRGC HRGD | Raji Cells, cyclohexamide treated | Uni-ZAP XR | LP03 |
| HSUA HSUB HSUC HSUM | Supt Cells, cyclohexamide treated | Uni-ZAP XR | LP03 |
| HT4A HT4C HT4D | Activated T-Cells, 12 hrs. | Uni-ZAP XR | LP03 |
| HE9A HE9B HE9C HE9D HE9E HE9F HE9G HE9H HE9M HE9N | Nine Week Old Early Stage Human | Uni-ZAP XR | LP03 |
| HATA HATB HATC HATD HATE | Human Adrenal Gland Tumor | Uni-ZAP XR | LP03 |
| HT5A | Activated T-Cells, 24 hrs. | Uni-ZAP XR | LP03 |
| HFGA HFGM | Human Fetal Brain | Uni-ZAP XR | LP03 |
| HNEA HNEB HNEC HNED HNEE | Human Neutrophil | Uni-ZAP XR | LP03 |
| HBGB HBGD | Human Primary Breast Cancer | Uni-ZAP XR | LP03 |
| HBNA HBNB | Human Normal Breast | Uni-ZAP XR | LP03 |
| HCAS | Cem Cells, cyclohexamide treated, subtra | Uni-ZAP XR | LP03 |
| HHPS | Human Hippocampus, subtracted | pBS | LP03 |
| HKCS HKCU | Human Colon Cancer, subtracted | pBS | LP03 |
| HRGS | Raji cells, cyclohexamide treated, subtracted | pBS | LP03 |
| HSUT | Supt cells, cyclohexamide treated, differentially expressed | pBS | LP03 |
| HT4S | Activated T-Cells, 12 hrs, subtracted | Uni-ZAP XR | LP03 |
| HCDA HCDB HCDC HCDD HCDE | Human Chondrosarcoma | Uni-ZAP XR | LP03 |
| HOAA HOAB HOAC | Human Osteosarcoma | Uni-ZAP XR | LP03 |
| HTLA HTLB HTLC HTLD HTLE HTLF | Human adult testis, large inserts | Uni-ZAP XR | LP03 |
| HLMA HLMC HLMD | Breast Lymph node cDNA library | Uni-ZAP XR | LP03 |
| H6EA H6EB H6EC | HL-60, PMA 4 H | Uni-ZAP XR | LP03 |
| HTXA HTXB HTXC HTXD HTXE HTXF HTXG HTXH | Activated T-Cell (12 hs)/Thiouridine labelledEco | Uni-ZAP XR | LP03 |
| HNFA HNFB HNFC HNFD HNFE HNFF HNFG HNFH HNFJ | Human Neutrophil, Activated | Uni-ZAP XR | LP03 |
| HTOB HTOC | HUMAN TONSILS, FRACTION 2 | Uni-ZAP XR | LP03 |
| HMGB | Human OB MG63 control fraction I | Uni-ZAP XR | LP03 |
| HOPB | Human OB HOS control fraction I | Uni-ZAP XR | LP03 |
| HORB | Human OB HOS treated (10 nM E2) fraction I | Uni-ZAP XR | LP03 |
| HSVA HSVB HSVC | Human Chronic Synovitis | Uni-ZAP XR | LP03 |
| HROA | HUMAN STOMACH | Uni-ZAP XR | LP03 |

TABLE 7-continued

| Libraries owned by Catalog | Catalog Description | Vector | ATCC ™ Deposit |
|---|---|---|---|
| HBJA HBJB HBJC HBJD HBJE HBJF HBJG HBJH HBJI HBJJ HBJK | HUMAN B CELL LYMPHOMA | Uni-ZAP XR | LP03 |
| HCRA HCRB HCRC | human corpus colosum | Uni-ZAP XR | LP03 |
| HODA HODB HODC HODD | human ovarian cancer | Uni-ZAP XR | LP03 |
| HDSA | Dermatofibrosarcoma Protuberance | Uni-ZAP XR | LP03 |
| HMWA HMWB HMWC HMWD HMWE HMWF HMWG HMWH HMWI HMWJ | Bone Marrow Cell Line (RS4; 11) | Uni-ZAP XR | LP03 |
| HSOA | stomach cancer (human) | Uni-ZAP XR | LP03 |
| HERA | SKIN | Uni-ZAP XR | LP03 |
| HMDA | Brain-medulloblastoma | Uni-ZAP XR | LP03 |
| HGLA HGLB HGLD | Glioblastoma | Uni-ZAP XR | LP03 |
| HEAA | H. Atrophic Endometrium | Uni-ZAP XR | LP03 |
| HBCA HBCB | H. Lymph node breast Cancer | Uni-ZAP XR | LP03 |
| HPWT | Human Prostate BPH, re-excision | Uni-ZAP XR | LP03 |
| HFVG HFVH HFVI | Fetal Liver, subtraction II | pBS | LP03 |
| HNFI | Human Neutrophils, Activated, re-excision | pBS | LP03 |
| HBMB HBMC HBMD | Human Bone Marrow, re-excision | pBS | LP03 |
| HKML HKMM HKMN | H. Kidney Medulla, re-excision | pBS | LP03 |
| HKIX HKIY | H. Kidney Cortex, subtracted | pBS | LP03 |
| HADT | H. Amygdala Depression, subtracted | pBS | LP03 |
| H6AS | Hl-60, untreated, subtracted | Uni-ZAP XR | LP03 |
| H6ES | HL-60, PMA 4 H, subtracted | Uni-ZAP XR | LP03 |
| H6BS | HL-60, RA 4 h, Subtracted | Uni-ZAP XR | LP03 |
| H6CS | HL-60, PMA 1 d, subtracted | Uni-ZAP XR | LP03 |
| HTXJ HTXK | Activated T-cell(12 h)/Thiouridine-re-excision | Uni-ZAP XR | LP03 |
| HMSA HMSB HMSC HMSD HMSE HMSF HMSG HMSH HMSI HMSJ HMSK | Monocyte activated | Uni-ZAP XR | LP03 |
| HAGA HAGB HAGC HAGD HAGE HAGF | Human Amygdala | Uni-ZAP XR | LP03 |
| HSRA HSRB HSRE | STROMAL - OSTEOCLASTOMA | Uni-ZAP XR | LP03 |
| HSRD HSRF HSRG HSRH | Human Osteoclastoma Stromal Cells - unamplified | Uni-ZAP XR | LP03 |
| HSQA HSQB HSQC HSQD HSQE HSQF HSQG | Stromal cell TF274 | Uni-ZAP XR | LP03 |
| HSKA HSKB HSKC HSKD HSKE HSKF HSKZ | Smooth muscle, serum treated | Uni-ZAP XR | LP03 |
| HSLA HSLB HSLC HSLD HSLE HSLF HSLG | Smooth muscle, control | Uni-ZAP XR | LP03 |
| HSDA HSDD HSDE HSDF HSDG HSDH | Spinal cord | Uni-ZAP XR | LP03 |
| HPWS | Prostate-BPH subtracted II | pBS | LP03 |
| HSKW HSKX HSKY | Smooth Muscle-HASTE normalized | pBS | LP03 |
| HFPB HFPC HFPD | H. Frontal cortex, epileptic; re-excision | Uni-ZAP XR | LP03 |
| HSDI HSDJ HSDK | Spinal Cord, re-excision | Uni-ZAP XR | LP03 |
| HSKN HSKO | Smooth Muscle Serum Treated, Norm | pBS | LP03 |
| HSKG HSKH HSKI | Smooth muscle, serum induced, re-exc | pBS | LP03 |
| HFCA HFCB HFCC HFCD HFCE HFCF | Human Fetal Brain | Uni-ZAP XR | LP04 |
| HPTA HPTB HPTD | Human Pituitary | Uni-ZAP XR | LP04 |
| HTHB HTHC HTHD | Human Thymus | Uni-ZAP XR | LP04 |
| HE6B HE6C HE6D HE6E HE6F HE6G HE6S | Human Whole Six Week Old Embryo | Uni-ZAP XR | LP04 |
| HSSA HSSB HSSC HSSD HSSE HSSF HSSG HSSH HSSI HSSJ HSSK | Human Synovial Sarcoma | Uni-ZAP XR | LP04 |
| HE7T | 7 Week Old Early Stage Human, subtracted | Uni-ZAP XR | LP04 |
| HEPA HEPB HEPC | Human Epididymus | Uni-ZAP XR | LP04 |
| HSNA HSNB HSNC HSNM HSNN | Human Synovium | Uni-ZAP XR | LP04 |

TABLE 7-continued

| Libraries owned by Catalog | Catalog Description | Vector | ATCC ™ Deposit |
|---|---|---|---|
| HPFB HPFC HPFD HPFE | Human Prostate Cancer, Stage C fraction | Uni-ZAP XR | LP04 |
| HE2A HE2D HE2E HE2H HE2I HE2M HE2N HE2O | 12 Week Old Early Stage Human | Uni-ZAP XR | LP04 |
| HE2B HE2C HE2F HE2G HE2P HE2Q | 12 Week Old Early Stage Human, II | Uni-ZAP XR | LP04 |
| HPTS HPTT HPTU | Human Pituitary, subtracted | Uni-ZAP XR | LP04 |
| HAUA HAUB HAUC | Amniotic Cells - TNF induced | Uni-ZAP XR | LP04 |
| HAQA HAQB HAQC HAQD | Amniotic Cells - Primary Culture | Uni-ZAP XR | LP04 |
| HWTA HWTB HWTC | wilm's tumor | Uni-ZAP XR | LP04 |
| HBSD | Bone Cancer, re-excision | Uni-ZAP XR | LP04 |
| HSGB | Salivary gland, re-excision | Uni-ZAP XR | LP04 |
| HSJA HSJB HSJC | Smooth muscle-ILb induced | Uni-ZAP XR | LP04 |
| HSXA HSKB HSXC HSXD | Human Substantia Nigra | Uni-ZAP XR | LP04 |
| HSHA HSHB HSHC | Smooth muscle, IL1b induced | Uni-ZAP XR | LP04 |
| HOUA HOUB HOUC HOUD HOUE | Adipocytes | Uni-ZAP XR | LP04 |
| HPWA HPWB HPWC HPWD HPWE | Prostate BPH | Uni-ZAP XR | LP04 |
| HELA HELB HELC HELD HELE HELF HELG HELH | Endothelial cells-control | Uni-ZAP XR | LP04 |
| HEMA HEMB HEMC HEMD HEME HEMF HEMG HEMH | Endothelial-induced | Uni-ZAP XR | LP04 |
| HBIA HBIB HBIC | Human Brain, Striatum | Uni-ZAP XR | LP04 |
| HHSA HHSB HHSC HHSD HHSE | Human Hypothalmus, Schizophrenia | Uni-ZAP XR | LP04 |
| HNGA HNGB HNGC HNGD HNGE HNGF HNGG HNGH HNGI HNGJ | neutrophils control | Uni-ZAP XR | LP04 |
| HNHA HNHB HNHC HNHD HNHE HNHF HNHG HNHH HNHI HNHJ | Neutrophils IL-1 and LPS induced | Uni-ZAP XR | LP04 |
| HSDB HSDC | STRIATUM DEPRESSION | Uni-ZAP XR | LP04 |
| HHPT | Hypothalamus | Uni-ZAP XR | LP04 |
| HSAT HSAU HSAV HSAW HSAX HSAY HSAZ | Anergic T-cell | Uni-ZAP XR | LP04 |
| HBMS HBMT HBMU HBMV HBMW HBMX | Bone marrow | Uni-ZAP XR | LP04 |
| HOEA HOEB HOEC HOED HOEE HOEF HOEJ | Osteoblasts | Uni-ZAP XR | LP04 |
| HAIA HAIB HAIC HAID HALE HALF | Epithelial-TNFa and INF induced | Uni-ZAP XR | LP04 |
| HTGA HTGB HTGC HTGD | Apoptotic T-cell | Uni-ZAP XR | LP04 |
| HMCA HMCB HMCC HMCD HMCE | Macrophage-oxLDL | Uni-ZAP XR | LP04 |
| HMAA HMAB HMAC HMAD HMAE HMAF HMAG | Macrophage (GM-CSF treated) | Uni-ZAP XR | LP04 |
| HPHA | Normal Prostate | Uni-ZAP XR | LP04 |
| HPIA HPIB HPIC | LNCAP prostate cell line | Uni-ZAP XR | LP04 |
| HPJA HPJB HPJC | PC3 Prostate cell line | Uni-ZAP XR | LP04 |
| HOSE HOSF HOSG | Human Osteoclastoma, re-excision | Uni-ZAP XR | LP04 |
| HTGE HTGF | Apoptotic T-cell, re-excision | Uni-ZAP XR | LP04 |
| HMAJ HMAK | H Macrophage (GM-CSF treated), re-excision | Uni-ZAP XR | LP04 |
| HACB HACC HACD | Human Adipose Tissue, re-excision | Uni-ZAP XR | LP04 |
| HFPA | H. Frontal Cortex, Epileptic | Uni-ZAP XR | LP04 |
| HFAA HFAB HFAC HFAD HFAE | Alzheimer's, spongy change | Uni-ZAP XR | LP04 |
| HFAM | Frontal Lobe, Dementia | Uni-ZAP XR | LP04 |
| HMIA HMIB HMIC | Human Manic Depression Tissue | Uni-ZAP XR | LP04 |
| HTSA HTSE HTSF HTSG HTSH | Human Thymus | pBS | LP05 |
| HPBA HPBB HPBC HPBD HPBE | Human Pineal Gland | pBS | LP05 |
| HSAA HSAB HSAC | HSA 172 Cells | pBS | LP05 |
| HSBA HSBB HSBC HSBM | HSC172 cells | pBS | LP05 |
| HJAA HJAB HJAC HJAD | Jurkat T-cell G1 phase | pBS | LP05 |
| HJBA HJBB HJBC HJBD | Jurkat T-Cell, S phase | pBS | LP05 |
| HAFA HAFB | Aorta endothelial cells + TNF-a | pBS | LP05 |

TABLE 7-continued

| Libraries owned by Catalog | Catalog Description | Vector | ATCC ™ Deposit |
|---|---|---|---|
| HAWA HAWB HAWC | Human White Adipose | pBS | LP05 |
| HTNA HTNB | Human Thyroid | pBS | LP05 |
| HONA | Normal Ovary, Premenopausal | pBS | LP05 |
| HARA HARB | Human Adult Retina | pBS | LP05 |
| HLJA HLJB | Human Lung | pCMVSport 1 | LP06 |
| HOFM HOFN HOFO | H. Ovarian Tumor, II, OV5232 | pCMVSport 2.0 | LP07 |
| HOGA HOGB HOGC | OV 10-3-95 | pCMVSport 2.0 | LP07 |
| HCGL | CD34+cells, II | pCMVSport 2.0 | LP07 |
| HDLA | Hodgkin's Lymphoma I | pCMVSport 2.0 | LP07 |
| HDTA HDTB HDTC HDTD HDTE | Hodgkin's Lymphoma II | pCMVSport 2.0 | LP07 |
| HKAA HKAB HKAC HKAD HKAE HKAF HKAG HKAH | Keratinocyte | pCMVSport2.0 | LP07 |
| HCIM | CAPFINDER, Crohn's Disease, lib 2 | pCMVSport 2.0 | LP07 |
| HKAL | Keratinocyte, lib 2 | pCMVSport2.0 | LP07 |
| HKAT | Keratinocyte, lib 3 | pCMVSport2.0 | LP07 |
| HNDA | Nasal polyps | pCMVSport2.0 | LP07 |
| HDRA | H. Primary Dendritic Cells, lib 3 | pCMVSport2.0 | LP07 |
| HOHA HOHB HOHC | Human Osteoblasts II | pCMVSport2.0 | LP07 |
| HLDA HLDB HLDC | Liver, Hepatoma | pCMVSport3.0 | LP08 |
| HLDN HLDO HLDP | Human Liver, normal | pCMVSport3.0 | LP08 |
| HMTA | pBMC stimulated w/ poly I/C | pCMVSport3.0 | LP08 |
| HNTA | NTERA2, control | pCMVSport3.0 | LP08 |
| HDPA HDPB HDPC HDPD HDPF HDPG HDPH HDPI HDPJ HDPK | Primary Dendritic Cells, lib 1 | pCMVSport3.0 | LP08 |
| HDPM HDPN HDPO HDPP | Primary Dendritic cells, frac 2 | pCMVSport3.0 | LP08 |
| HMUA HMUB HMUC | Myoloid Progenitor Cell Line | pCMVSport3.0 | LP08 |
| HHEA HHEB HHEC HHED | T Cell helper I | pCMVSport3.0 | LP08 |
| HHEM HHEN HHEO HHEP | T cell helper II | pCMVSport3.0 | LP08 |
| HEQA HEQB HEQC | Human endometrial stromal cells | pCMVSport3.0 | LP08 |
| HJMA HJMB | Human endometrial stromal cells-treated with progesterone | pCMVSport3.0 | LP08 |
| HSWA HSWB HSWC | Human endometrial stromal cells-treated with estradiol | pCMVSport3.0 | LP08 |
| HSYA HSYB HSYC | Human Thymus Stromal Cells | pCMVSport3.0 | LP08 |
| HLWA HLWB HLWC | Human Placenta | pCMVSport3.0 | LP08 |
| HRAA HRAB HRAC | Rejected Kidney, lib 4 | pCMVSport3.0 | LP08 |
| HMTM | PCR, pBMC I/C treated | PCRII | LP09 |
| HMJA | H. Meniingima, M6 | pSport 1 | LP10 |
| HMKA HMKB HMKC HMKD HMKE | H. Meningima, M1 | pSport 1 | LP10 |
| HUSG HUSI | Human umbilical vein endothelial cells, IL-4 induced | pSport 1 | LP10 |
| HUSX HUSY | Human Umbilical Vein Endothelial Cells, uninduced | pSport 1 | LP10 |
| HOFA | Ovarian Tumor I, OV5232 | pSport 1 | LP10 |
| HCFA HCFB HCFC HCFD | T-Cell PHA 16 hrs | pSport 1 | LP10 |
| HCFL HCFM HCFN HCFO | T-Cell PHA 24 hrs | pSport 1 | LP10 |
| HADA HADC HADD HADE HADF HADG | Human Adipose | pSport 1 | LP10 |
| HOVA HOVB HOVC | Human Ovary | pSport 1 | LP10 |
| HTWB HTWC HTWD HTWE HTWF | Resting T-Cell Library, II | pSport 1 | LP10 |
| HMMA | Spleen metastic melanoma | pSport 1 | LP10 |
| HLYA HLYB HLYC HLYD HLYE | Spleen, Chronic lymphocytic leukemia | pSport 1 | LP10 |
| HCGA | CD34+ cell, I | pSport 1 | LP10 |
| HEOM HEON | Human Eosinophils | pSport 1 | LP10 |
| HTDA | Human Tonsil, Lib 3 | pSport 1 | LP10 |
| HSPA | Salivary Gland, Lib 2 | pSport 1 | LP10 |
| HCHA HCHB HCHC | Breast Cancer cell line, MDA 36 | pSport 1 | LP10 |
| HCHM HCHN | Breast Cancer Cell line, angiogenic | pSport 1 | LP10 |
| HCIA | Crohn's Disease | pSport 1 | LP10 |
| HDAA HDAB HDAC | HEL cell line | pSport 1 | LP10 |
| HABA | Human Astrocyte | pSport 1 | LP10 |
| HUFA HUFB HUFC | Ulcerative Colitis | pSport 1 | LP10 |
| HNTM | NTERA2 + retinoic acid, 14 days | pSport 1 | LP10 |

TABLE 7-continued

| Libraries owned by Catalog | Catalog Description | Vector | ATCC ™ Deposit |
|---|---|---|---|
| HDQA | Primary Dendritic cells, CapFinder2, frac 1 | pSport 1 | LP10 |
| HDQM | Primary Dendritic Cells, CapFinder, frac 2 | pSport 1 | LP10 |
| HLDX | Human Liver, normal, CapFinder | pSport 1 | LP10 |
| HULA HULB HULC | Human Dermal Endothelial Cells, untreated | pSport1 | LP10 |
| HUMA | Human Dermal Endothelial cells, treated | pSport1 | LP10 |
| HCJA | Human Stromal Endometrial fibroblasts, untreated | pSport1 | LP10 |
| HCJM | Human Stromal endometrial fibroblasts, treated w/ estradiol | pSport1 | LP10 |
| HEDA | Human Stromal endometrial fibroblasts, treated with progesterone | pSport1 | LP10 |
| HFNA | Human ovary tumor cell OV350721 | pSport1 | LP10 |
| HKGA HKGB HKGC HKGD | Merkel Cells | pSport1 | LP10 |
| HISA HISB HISC | Pancreas Islet Cell Tumor | pSport1 | LP10 |
| HLSA | Skin, burned | pSport1 | LP10 |
| HBZA | Prostate, BPH, Lib 2 | pSport 1 | LP10 |
| HBZS | Prostate BPH, Lib 2, subtracted | pSport 1 | LP10 |
| HFIA HFIB HFIC | Synovial Fibroblasts (control) | pSport 1 | LP10 |
| HFIH HFII HFIJ | Synovial hypoxia | pSport 1 | LP10 |
| HFIT HFIU HFIV | Synovial IL-1/TNF stimulated | pSport 1 | LP10 |
| HGCA | Messangial cell, frac 1 | pSport1 | LP10 |
| HMVA HMVB HMVC | Bone Marrow Stromal Cell, untreated | pSport1 | LP10 |
| HFIX HFIY HFIZ | Synovial Fibroblasts (Il1/TNF), subt | pSport1 | LP10 |
| HFOX HFOY HFOZ | Synovial hypoxia-RSF subtracted | pSport1 | LP10 |
| HMQA HMQB HMQC HMQD | Human Activated Monocytes | Uni-ZAP XR | LP11 |
| HLIA HLIB HLIC | Human Liver | pCMVSport 1 | LP012 |
| HHBA HHBB HHBC HHBD HHBE | Human Heart | pCMVSport 1 | LP012 |
| HBBA HBBB | Human Brain | pCMVSport 1 | LP012 |
| HLJA HLJB HLJC HLJD HLJE | Human Lung | pCMVSport 1 | LP012 |
| HOGA HOGB HOGC | Ovarian Tumor | pCMVSport 2.0 | LP012 |
| HTJM | Human Tonsils, Lib 2 | pCMVSport 2.0 | LP012 |
| HAMF HAMG | KMH2 | pCMVSport 3.0 | LP012 |
| HAJA HAJB HAJC | L428 | pCMVSport 3.0 | LP012 |
| HWBA HWBB HWBC HWBD HWBE | Dendritic cells, pooled | pCMVSport 3.0 | LP012 |
| HWAA HWAB HWAC HWAD HWAE | Human Bone Marrow, treated | pCMVSport 3.0 | LP012 |
| HYAA HYAB HYAC | B Cell lymphoma | pCMVSport 3.0 | LP012 |
| HWHG HWHH HWHI | Healing groin wound, 6.5 hours post incision | pCMVSport 3.0 | LP012 |
| HWHP HWHQ HWHR | Healing groin wound; 7.5 hours post incision | pCMVSport 3.0 | LP012 |
| HARM | Healing groin wound - zero hr post-incision (control) | pCMVSport 3.0 | LP012 |
| HBIM | Olfactory epithelium; nasalcavity | pCMVSport 3.0 | LP012 |
| HWDA | Healing Abdomen wound; 70&90 min post incision | pCMVSport 3.0 | LP012 |
| HWEA | Healing Abdomen Wound; 15 days post incision | pCMVSport 3.0 | LP012 |
| HWJA | Healing Abdomen Wound; 21&29 days | pCMVSport 3.0 | LP012 |
| HNAL | Human Tongue, frac 2 | pSport1 | LP012 |
| HMJA | H. Meniingima, M6 | pSport1 | LP012 |
| HMKA HMKB HMKC HMKD HMKE | H. Meningima, M1 | pSport1 | LP012 |
| HOFA | Ovarian Tumor I, OV5232 | pSport1 | LP012 |
| HCFA HCFB HCFC HCFD | T-Cell PHA 16 hrs | pSport1 | LP012 |
| HCFL HCFM HCFN HCFO | T-Cell PHA 24 hrs | pSport1 | LP012 |
| HMMA HMMB HMMC | Spleen metastic melanoma | pSport1 | LP012 |
| HTDA | Human Tonsil, Lib 3 | pSport1 | LP012 |
| HDBA | Human Fetal Thymus | pSport1 | LP012 |

TABLE 7-continued

| Libraries owned by Catalog | Catalog Description | Vector | ATCC ™ Deposit |
|---|---|---|---|
| HDUA | Pericardium | pSport1 | LP012 |
| HBZA | Prostate, BPH, Lib 2 | pSport1 | LP012 |
| HWCA | Larynx tumor | pSport1 | LP012 |
| HWKA | Normal lung | pSport1 | LP012 |
| HSMB | Bone marrow stroma, treated | pSport1 | LP012 |
| HBHM | Normal trachea | pSport1 | LP012 |
| HLFC | Human Larynx | pSport1 | LP012 |
| HLRB | Siebben Polyposis | pSport1 | LP012 |
| HNIA | Mammary Gland | pSport1 | LP012 |
| HNJB | Palate carcinoma | pSport1 | LP012 |
| HNKA | Palate normal | pSport1 | LP012 |
| HMZA | Pharynx carcinoma | pSport1 | LP012 |
| HABG | Cheek Carcinoma | pSport1 | LP012 |
| HMZM | Pharynx Carcinoma | pSport1 | LP012 |
| HDRM | Larynx Carcinoma | pSport1 | LP012 |
| HVAA | Pancreas normal PCA4 No | pSport1 | LP012 |
| HICA | Tongue carcinoma | pSport1 | LP012 |
| HUKA HUKB HUKC HUKD HUKE | Human Uterine Cancer | Lambda ZAP II | LP013 |
| HFFA | Human Fetal Brain, random primed | Lambda ZAP II | LP013 |
| HTUA | Activated T-cell labeled with 4-thioluri | Lambda ZAP II | LP013 |
| HBQA | Early Stage Human Brain, random primed | Lambda ZAP II | LP013 |
| HMEB | Human microvascular Endothelial cells, fract. B | Lambda ZAP II | LP013 |
| HUSH | Human Umbilical Vein Endothelial cells, fract. A, re-excision | Lambda ZAP II | LP013 |
| HLQC HLQD | Hepatocellular tumor, re-excision | Lambda ZAP II | LP013 |
| HTWJ HTWK HTWL | Resting T-cell, re-excision | Lambda ZAP II | LP013 |
| HF6S | Human Whole 6 week Old Embryo (II), subt | pBLUESCRIPT ™ | LP013 |
| HHPS | Human Hippocampus, subtracted | pBLUESCRIPT ™ | LP013 |
| HL1S | LNCAP, differential expression | pBLUESCRIPT ™ | LP013 |
| HLHS HLHT | Early Stage Human Lung, Subtracted | pBLUESCRIPT ™ | LP013 |
| HSUS | Supt cells, cyclohexamide treated, subtracted | pBLUESCRIPT ™ | LP013 |
| HSUT | Supt cells, cyclohexamide treated, differentially expressed | pBLUESCRIPT ™ | LP013 |
| HSDS | H. Striatum Depression, subtracted | pBLUESCRIPT ™ | LP013 |
| HPTZ | Human Pituitary, Subtracted VII | pBLUESCRIPT ™ | LP013 |
| HSDX | H. Striatum Depression, subt II | pBLUESCRIPT ™ | LP013 |
| HSDZ | H. Striatum Depression, subt | pBLUESCRIPT ™ | LP013 |
| HPBA HPBB HPBC HPBD HPBE | Human Pineal Gland | pBLUESCRIPT ™ SK– | LP013 |
| HRTA | Colorectal Tumor | pBLUESCRIPT ™ SK– | LP013 |
| HSBA HSBB HSBC HSBM | HSC172 cells | pBLUESCRIPT ™ SK– | LP013 |
| HJAA HJAB HJAC HJAD | Jurkat T-cell G1 phase | pBLUESCRIPT ™ SK– | LP013 |
| HJBA HJBB HJBC HJBD | Jurkat T-cell, S1 phase | pBLUESCRIPT ™ SK– | LP013 |
| HTNA HTNB | Human Thyroid | pBLUESCRIPT ™ SK– | LP013 |
| HAHA HAHB | Human Adult Heart | Uni-ZAP XR | LP013 |
| HE6A | Whole 6 week Old Embryo | Uni-ZAP XR | LP013 |
| HFCA HFCB HFCC HFCD HFCE | Human Fetal Brain | Uni-ZAP XR | LP013 |
| HFKC HFKD HFKE HFKF HFKG | Human Fetal Kidney | Uni-ZAP XR | LP013 |
| HGBA HGBD HGBE HGBF HGBG | Human Gall Bladder | Uni-ZAP XR | LP013 |
| HPRA HPRB HPRC HPRD | Human Prostate | Uni-ZAP XR | LP013 |
| HTEA HTEB HTEC HTED HTEE | Human Testes | Uni-ZAP XR | LP013 |

TABLE 7-continued

| Libraries owned by Catalog | Catalog Description | Vector | ATCC ™ Deposit |
|---|---|---|---|
| HTTA HTTB HTTC HTTD HTTE | Human Testes Tumor | Uni-ZAP XR | LP013 |
| HYBA HYBB | Human Fetal Bone | Uni-ZAP XR | LP013 |
| HFLA | Human Fetal Liver | Uni-ZAP XR | LP013 |
| HHFB HHFC HHFD HHFE HHFF | Human Fetal Heart | Uni-ZAP XR | LP013 |
| HUVB HUVC HUVD HUVE | Human Umbilical Vein, End. remake | Uni-ZAP XR | LP013 |
| HTHB HTHC HTHD | Human Thymus | Uni-ZAP XR | LP013 |
| HSTA HSTB HSTC HSTD | Human Skin Tumor | Uni-ZAP XR | LP013 |
| HTAA HTAB HTAC HTAD HTAE | Human Activated T-cells | Uni-ZAP XR | LP013 |
| HFEA HFEB HFEC | Human Fetal Epithelium (skin) | Uni-ZAP XR | LP013 |
| HJPA HJPB HJPC HJPD | Human Jurkat Membrane Bound Polysomes | Uni-ZAP XR | LP013 |
| HESA | Human Epithelioid Sarcoma | Uni-ZAP XR | LP013 |
| HALS | Human Adult Liver, Subtracted | Uni-ZAP XR | LP013 |
| HFTA HFTB HFTC HFTD | Human Fetal Dura Mater | Uni-ZAP XR | LP013 |
| HCAA HCAB HCAC | Cem cells, cyclohexamide treated | Uni-ZAP XR | LP013 |
| HRGA HRGB HRGC HRGD | Raji Cells, cyclohexamide treated | Uni-ZAP XR | LP013 |
| HE9A HE9B HE9C HE9D HE9E | Nine Week Old Early Stage Human | Uni-ZAP XR | LP013 |
| HSFA | Human Fibrosarcoma | Uni-ZAP XR | LP013 |
| HATA HATB HATC HATD HATE | Human Adrenal Gland Tumor | Uni-ZAP XR | LP013 |
| HTRA | Human Trachea Tumor | Uni-ZAP XR | LP013 |
| HE2A HE2D HE2E HE2H HE2I | 12 Week Old Early Stage Human | Uni-ZAP XR | LP013 |
| HE2B HE2C HE2F HE2G HE2P | 12 Week Old Early Stage Human, II | Uni-ZAP XR | LP013 |
| HNEA HNEB HNEC HNED HNEE | Human Neutrophil | Uni-ZAP XR | LP013 |
| HBGA | Human Primary Breast Cancer | Uni-ZAP XR | LP013 |
| HPTS HPTT HPTU | Human Pituitary, subtracted | Uni-ZAP XR | LP013 |
| HMQA HMQB HMQC HMQD | Human Activated Monocytes | Uni-ZAP XR | LP013 |
| HOAA HOAB HOAC | Human Osteosarcoma | Uni-ZAP XR | LP013 |
| HTOA HTOD HTOE HTOF HTOG | human tonsils | Uni-ZAP XR | LP013 |
| HMGB | Human OB MG63 control fraction I | Uni-ZAP XR | LP013 |
| HOPB | Human OB HOS control fraction I | Uni-ZAP XR | LP013 |
| HOQB | Human OB HOS treated (1 nM E2) fraction I | Uni-ZAP XR | LP013 |
| HAUA HAUB HAUC | Amniotic Cells - TNF induced | Uni-ZAP XR | LP013 |
| HAQA HAQB HAQC HAQD | Amniotic Cells - Primary Culture | Uni-ZAP XR | LP013 |
| HROA HROC | HUMAN STOMACH | Uni-ZAP XR | LP013 |
| HBJA HBJB HBJC HBJD HBJE | HUMAN B CELL LYMPHOMA | Uni-ZAP XR | LP013 |
| HODA HODB HODC HODD | human ovarian cancer | Uni-ZAP XR | LP013 |
| HCPA | Corpus Callosum | Uni-ZAP XR | LP013 |
| HSOA | stomach cancer (human) | Uni-ZAP XR | LP013 |
| HERA | SKIN | Uni-ZAP XR | LP013 |
| HMDA | Brain-medulloblastoma | Uni-ZAP XR | LP013 |
| HGLA HGLB HGLD | Glioblastoma | Uni-ZAP XR | LP013 |
| HWTA HWTB HWTC | wilm's tumor | Uni-ZAP XR | LP013 |
| HEAA | H. Atrophic Endometrium | Uni-ZAP XR | LP013 |
| HAPN HAPO HAPP HAPQ HAPR | Human Adult Pulmonary; re-excision | Uni-ZAP XR | LP013 |
| HLTG HLTH | Human T-cell lymphoma; re-excision | Uni-ZAP XR | LP013 |
| HAHC HAHD HAHE | Human Adult Heart; re-excision | Uni-ZAP XR | LP013 |
| HAGA HAGB HAGC HAGD HAGE | Human Amygdala | Uni-ZAP XR | LP013 |
| HSJA HSJB HSJC | Smooth muscle-ILb induced | Uni-ZAP XR | LP013 |
| HSHA HSHB HSHC | Smooth muscle, IL1b induced | Uni-ZAP XR | LP013 |
| HPWA HPWB HPWC HPWD HPWE | Prostate BPH | Uni-ZAP XR | LP013 |

TABLE 7-continued

| Libraries owned by Catalog | Catalog Description | Vector | ATCC ™ Deposit |
|---|---|---|---|
| HPIA HPIB HPIC | LNCAP prostate cell line | Uni-ZAP XR | LP013 |
| HPJA HPJB HPJC | PC3 Prostate cell line | Uni-ZAP XR | LP013 |
| HBTA | Bone Marrow Stroma, TNF&LPS ind | Uni-ZAP XR | LP013 |
| HMCF HMCG HMCH HMCI HMCJ | Macrophage-oxLDL; re-excision | Uni-ZAP XR | LP013 |
| HAGG HAGH HAGI | Human Amygdala; re-excision | Uni-ZAP XR | LP013 |
| HACA | H. Adipose Tissue | Uni-ZAP XR | LP013 |
| HKFB | K562 + PMA (36 hrs), re-excision | ZAP Express | LP013 |
| HCWT HCWU HCWV | CD34 positive cells (cord blood), re-ex | ZAP Express | LP013 |
| HBWA | Whole brain | ZAP Express | LP013 |
| HBXA HBXB HBXC HBXD | Human Whole Brain #2 - Oligo dT >1.5 Kb | ZAP Express | LP013 |
| HAVM | Temporal cortex-Alzheizmer | pT-Adv | LP014 |
| HAVT | Hippocampus, Alzheimer Subtracted | pT-Adv | LP014 |
| HHAS | CHME Cell Line | Uni-ZAP XR | LP014 |
| HAJR | Larynx normal | pSport 1 | LP014 |
| HWLE HWLF HWLG HWLH | Colon Normal | pSport 1 | LP014 |
| HCRM HCRN HCRO | Colon Carcinoma | pSport 1 | LP014 |
| HWLI HWLJ HWLK | Colon Normal | pSport 1 | LP014 |
| HWLQ HWLR HWLS HWLT | Colon Tumor | pSport 1 | LP014 |
| HBFM | Gastrocnemius Muscle | pSport 1 | LP014 |
| HBOD HBOE | Quadriceps Muscle | pSport 1 | LP014 |
| HBKD HBKE | Soleus Muscle | pSport 1 | LP014 |
| HCCM | Pancreatic Langerhans | pSport 1 | LP014 |
| HWGA | Larynx carcinoma | pSport 1 | LP014 |
| HWGM HWGN | Larynx carcinoma | pSport 1 | LP014 |
| HWLA HWLB HWLC | Normal colon | pSport 1 | LP014 |
| HWLM HWLN | Colon Tumor | pSport 1 | LP014 |
| HVAM HVAN HVAO | Pancreas Tumor | pSport 1 | LP014 |
| HWGQ | Larynx carcinoma | pSport 1 | LP014 |
| HAQM HAQN | Salivary Gland | pSport 1 | LP014 |
| HASM | Stomach; normal | pSport 1 | LP014 |
| HBCM | Uterus; normal | pSport 1 | LP014 |
| HCDM | Testis; normal | pSport 1 | LP014 |
| HDJM | Brain; normal | pSport 1 | LP014 |
| HEFM | Adrenal Gland, normal | pSport 1 | LP014 |
| HBAA | Rectum normal | pSport 1 | LP014 |
| HFDM | Rectum tumour | pSport 1 | LP014 |
| HGAM | Colon, normal | pSport 1 | LP014 |
| HHMM | Colon, tumour | pSport 1 | LP014 |
| HCLB HCLC | Human Lung Cancer | Lambda Zap II | LP015 |
| HRLA | L1 Cell line | ZAP Express | LP015 |
| HHAM | Hypothalamus, Alzheimer's | pCMVSport 3.0 | LP015 |
| HKBA | Ku 812F Basophils Line | pSport 1 | LP015 |
| HS2S | Saos2, Dexamethosome Treated | pSport 1 | LP016 |
| HA5A | Lung Carcinoma A549 TNFalpha activated | pSport 1 | LP016 |
| HTFM | TF-1 Cell Line GM-CSF Treated | pSport 1 | LP016 |
| HYAS | Thyroid Tumour | pSport 1 | LP016 |
| HUTS | Larynx Normal | pSport 1 | LP016 |
| HXOA | Larynx Tumor | pSport 1 | LP016 |
| HEAH | Ea.hy.926 cell line | pSport 1 | LP016 |
| HINA | Adenocarcinoma Human | pSport 1 | LP016 |
| HRMA | Lung Mesothelium | pSport 1 | LP016 |
| HLCL | Human Pre-Differentiated Adipocytes | Uni-Zap XR | LP017 |
| HS2A | Saos2 Cells | pSport 1 | LP020 |
| HS2I | Saos2 Cells; Vitamin D3 Treated | pSport 1 | LP020 |
| HUCM | CHME Cell Line, untreated | pSport 1 | LP020 |
| HEPN | Aryepiglottis Normal | pSport 1 | LP020 |
| HPSN | Sinus Piniformis Tumour | pSport 1 | LP020 |
| HNSA | Stomach Normal | pSport 1 | LP020 |
| HNSM | Stomach Tumour | pSport 1 | LP020 |
| HNLA | Liver Normal Met5No | pSport 1 | LP020 |
| HUTA | Liver Tumour Met 5 Tu | pSport 1 | LP020 |
| HOCN | Colon Normal | pSport 1 | LP020 |
| HOCT | Colon Tumor | pSport 1 | LP020 |

TABLE 7-continued

| Libraries owned by Catalog | Catalog Description | Vector | ATCC ™ Deposit |
|---|---|---|---|
| HTNT | Tongue Tumour | pSport 1 | LP020 |
| HLXN | Larynx Normal | pSport 1 | LP020 |
| HLXT | Larynx Tumour | pSport 1 | LP020 |
| HTYN | Thymus | pSport 1 | LP020 |
| HPLN | Placenta | pSport 1 | LP020 |
| HTNG | Tongue Normal | pSport 1 | LP020 |
| HZAA | Thyroid Normal (SDCA2 No) | pSport 1 | LP020 |
| HWES | Thyroid Thyroiditis | pSport 1 | LP020 |
| HFHD | FICOLL ™ ed Human Stromal Cells, 5Fu treated | pTrip1Ex2 | LP021 |
| HFHM, HFHN | FICOLL ™ ed Human Stromal Cells, Untreated | pTrip1Ex2 | LP021 |
| HPCI | Hep G2 Cells, lambda library | lambda Zap-CMV XR | LP021 |
| HBCA, HBCB, HBCC | H. Lymph node breast Cancer | Uni-ZAP XR | LP021 |
| HCOK | Chondrocytes | pSPORT1 | LP022 |
| HDCA, HDCB, HDCC | Dendritic Cells From CD34 Cells | pSPORT1 | LP022 |
| HDMA, HDMB | CD40 activated monocyte dendritic cells | pSPORT1 | LP022 |
| HDDM, HDDN, HDDO | LPS activated derived dendritic cells | pSPORT1 | LP022 |
| HPCR | Hep G2 Cells, PCR library | lambda Zap-CMV XR | LP022 |
| HAAA, HAAB, HAAC | Lung, Cancer (4005313A3): Invasive Poorly Differentiated Lung Adenocarcinoma | pSPORT1 | LP022 |
| HIPA, HIPB, HIPC | Lung, Cancer (4005163 B7): Invasive, Poorly Diff. Adenocarcinoma, Metastatic | pSPORT1 | LP022 |
| HOOH, HOOI | Ovary, Cancer: (4004562 B6) Papillary Serous Cystic Neoplasm, Low Malignant Pot | pSPORT1 | LP022 |
| HIDA | Lung, Normal: (4005313 B1) | pSPORT1 | LP022 |
| HUJA, HUJB, HUJC, HUJD, HUJE | B-Cells | pCMVSport 3.0 | LP022 |
| HNOA, HNOB, HNOC, HNOD | Ovary, Normal: (9805C040R) | pSPORT1 | LP022 |
| HNLM | Lung, Normal: (4005313 B1) | pSPORT1 | LP022 |
| HSCL | Stromal Cells | pSPORT1 | LP022 |
| HAAX | Lung, Cancer: (4005313 A3) Invasive Poorly-differentiated Metastatic lung adenocarcinoma | pSPORT1 | LP022 |
| HUUA, HUUB, HUUC, HUUD | B-cells (unstimulated) | pTrip1Ex2 | LP022 |
| HWWA, HWWB, HWWC, HWWD, HWWE, HWWF, HWWG | B-cells (stimulated) | pSPORT1 | LP022 |
| HCCC | Colon, Cancer: (9808C064R) | pCMVSport 3.0 | LP023 |
| HPDO HPDP HPDQ HPDR HPD | Ovary, Cancer (9809C332): Poorly differentiated adenocarcinoma | pSport 1 | LP023 |
| HPCO HPCP HPCQ HPCT | Ovary, Cancer (15395A1F): Grade II Papillary Carcinoma | pSport 1 | LP023 |
| HOCM HOCO HOCP HOCQ | Ovary, Cancer: (15799A1F) Poorly differentiated carcinoma | pSport 1 | LP023 |
| HCBM HCBN HCBO | Breast, Cancer: (4004943 A5) | pSport 1 | LP023 |
| HNBT HNBU HNBV | Breast, Normal: (4005522B2) | pSport 1 | LP023 |
| HBCP HBCQ | Breast, Cancer: (4005522 A2) | pSport 1 | LP023 |
| HBCJ | Breast, Cancer: (9806C012R) | pSport 1 | LP023 |
| HSAM HSAN | Stromal cells 3.88 | pSport 1 | LP023 |
| HVCA HVCB HVCC HVCD | Ovary, Cancer: (4004332 A2) | pSport 1 | LP023 |
| HSCK HSEN HSEO | Stromal cells (HBM3.18) | pSport 1 | LP023 |
| HSCP HSCQ | stromal cell clone 2.5 | pSport 1 | LP023 |
| HUXA | Breast Cancer: (4005385 A2) | pSport 1 | LP023 |
| HCOM HCON HCOO HCOP HCOQ | Ovary, Cancer (4004650 A3): Well-Differentiated Micropapillary Serous Carcinoma | pSport 1 | LP023 |
| HBNM | Breast, Cancer: (9802C020E) | pSport 1 | LP023 |
| HVVA HVVB HVVC HVVD HVVE | Human Bone Marrow, treated | pSport 1 | LP023 |

Two nonlimiting examples are provided below for isolating a particular clone from the deposited sample of plasmid cDNAs cited for that clone in Table 1A. First, a plasmid is directly isolated by screening the clones using a polynucleotide probe corresponding to the nucleotide sequence of SEQ ID NO:X.

Particularly, a specific polynucleotide with 30-40 nucleotides is synthesized using an Applied Biosystems DNA synthesizer according to the sequence reported. The oligonucleotide is labeled, for instance, with $^{32}P$-γ-ATP using T4 polynucleotide kinase and purified according to routine methods. (E.g., Maniatis et al., Molecular Cloning: A Laboratory Manual, Cold Spring Harbor Press, Cold Spring, N.Y. (1982)). The plasmid mixture is transformed into a suitable host, as indicated above (such as XL-1 Blue (STRATAGENE™)) using techniques known to those of skill in the art, such as those provided by the vector supplier or in related publications or patents cited above. The transformants are plated on 1.5% agar plates (containing the appropriate selection agent, e.g., ampicillin) to a density of about 150 transformants (colonies) per plate. These plates are screened using Nylon membranes according to routine methods for bacterial colony screening (e.g., Sambrook et al., Molecular Cloning: A Laboratory Manual, 2nd Edit., (1989), Cold Spring Harbor Laboratory Press, pages 1.93 to 1.104), or other techniques known to those of skill in the art.

Alternatively, two primers of 17-20 nucleotides derived from both ends of the nucleotide sequence of SEQ ID NO:X are synthesized and used to amplify the desired cDNA using the deposited cDNA plasmid as a template. The polymerase chain reaction is carried out under routine conditions, for instance, in 25 μl of reaction mixture with 0.5 μg of the above cDNA template. A convenient reaction mixture is 1.5-5 mM $MgCl_2$, 0.01% (w/v) gelatin, 20 μM each of dATP, dCTP, dGTP, dTTP, 25 pmol of each primer and 0.25 Unit of Taq polymerase. Thirty five cycles of PCR (denaturation at 94° C. for 1 min; annealing at 55° C. for 1 min; elongation at 72° C. for 1 min) are performed with a Perkin-Elmer Cetus automated thermal cycler. The amplified product is analyzed by agarose gel electrophoresis and the DNA band with expected molecular weight is excised and purified. The PCR product is verified to be the selected sequence by subcloning and sequencing the DNA product.

Several methods are available for the identification of the 5' or 3' non-coding portions of a gene which may not be present in the deposited clone. These methods include but are not limited to, filter probing, clone enrichment using specific probes, and protocols similar or identical to 5' and 3' "RACE" protocols which are well known in the art. For instance, a method similar to 5' RACE is available for generating the missing 5' end of a desired full-length transcript. (Fromont-Racine et al., Nucleic Acids Res. 21(7):1683-1684 (1993)).

Briefly, a specific RNA oligonucleotide is ligated to the 5' ends of a population of RNA presumably containing full-length gene RNA transcripts. A primer set containing a primer specific to the ligated RNA oligonucleotide and a primer specific to a known sequence of the gene of interest is used to PCR amplify the 5' portion of the desired full-length gene. This amplified product may then be sequenced and used to generate the full length gene.

This above method starts with total RNA isolated from the desired source, although poly-A+ RNA can be used. The RNA preparation can then be treated with phosphatase if necessary to eliminate 5' phosphate groups on degraded or damaged RNA which may interfere with the later RNA ligase step. The phosphatase should then be inactivated and the RNA treated with tobacco acid pyrophosphatase in order to remove the cap structure present at the 5' ends of messenger RNAs. This reaction leaves a 5' phosphate group at the 5' end of the cap cleaved RNA which can then be ligated to an RNA oligonucleotide using T4 RNA ligase.

This modified RNA preparation is used as a template for first strand cDNA synthesis using a gene specific oligonucleotide. The first strand synthesis reaction is used as a template for PCR amplification of the desired 5' end using a primer specific to the ligated RNA oligonucleotide and a primer specific to the known sequence of the gene of interest. The resultant product is then sequenced and analyzed to confirm that the 5' end sequence belongs to the desired gene.

Example 2

Isolation of Genomic Clones Corresponding to a Polynucleotide

A human genomic P1 library (Genomic Systems, Inc.) is screened by PCR using primers selected for the sequence corresponding to SEQ ID NO:X according to the method described in Example 1. (See also, Sambrook.)

Example 3

Tissue Specific Expression Analysis

Tissue distribution of mRNA expression of polynucleotides of the present invention is determined using protocols for Northern blot analysis, described by, among others, Sambrook et al. For example, a cDNA probe produced by the method described in Example 1 is labeled with $P^{32}$ using the REDIPRIME™ DNA labeling system (Amersham Life Science), according to manufacturer's instructions. After labeling, the probe is purified using CHROMA SPN-100™ column (CLONTECH™ Laboratories, Inc.), according to manufacturer's protocol number PT1200-1. The purified labeled probe is then used to examine various human tissues for mRNA expression.

Multiple Tissue Northern (MTN) blots containing various human tissues (H) or human immune system tissues (IM) (CLONTECH™) are examined with the labeled probe using EXPRESSHYB™ hybridization solution (CLONTECH™) according to manufacturer's protocol number PT1190-1. Following hybridization and washing, the blots are mounted and exposed to film at −70° C. overnight, and the films developed according to standard procedures.

The Human Genome Sciences, Inc. (HGS) database is derived from sequencing tissue and/or disease specific cDNA libraries. Libraries generated from a particular tissue are selected and the specific tissue expression pattern of EST groups or assembled contigs within these libraries is determined by comparison of the expression patterns of those groups or contigs within the entire database. ESTs and assembled contigs which show tissue specific expression are selected.

The original clone from which the specific EST sequence was generated, or in the case of an assembled contig, the clone from which the 5' most EST sequence was generated, is obtained from the catalogued library of clones and the insert amplified by PCR using methods known in the art. The PCR product is denatured and then transferred in 96 or 384 well format to a nylon membrane (Schleicher and Scheull) generating an array filter of tissue specific clones. Housekeeping genes, maize genes, and known tissue specific genes are included on the filters. These targets can be used in signal normalization and to validate assay sensitivity. Additional targets are included to monitor probe length and specificity of hybridization.

Radioactively labeled hybridization probes are generated by first strand cDNA synthesis per the manufacturer's instructions (LIFE TECHNOLOGIES™) from mRNA/RNA samples prepared from the specific tissue being analyzed (e.g., prostate, prostate cancer, ovarian, ovarian cancer, etc.). The hybridization probes are purified by gel exclusion chromatography, quantitated, and hybridized with the array filters in hybridization bottles at 65° C. overnight. The filters are washed under stringent conditions and signals are captured using a Fuji phosphorimager.

Data is extracted using AIS software and following background subtraction, signal normalization is performed. This includes a normalization of filter-wide expression levels between different experimental runs. Genes that are differentially expressed in the tissue of interest are identified.

Example 4

Chromosomal Mapping of the Polynucleotides

An oligonucleotide primer set is designed according to the sequence at the 5' end of SEQ ID NO:X. This primer preferably spans about 100 nucleotides. This primer set is then used in a polymerase chain reaction under the following set of conditions: 30 seconds, 95° C.; 1 minute, 56° C.; 1 minute, 70° C. This cycle is repeated 32 times followed by one 5 minute cycle at 70° C. Human, mouse, and hamster DNA is used as template in addition to a somatic cell hybrid panel containing individual chromosomes or chromosome fragments (Bios, Inc). The reactions are analyzed on either 8% polyacrylamide gels or 3.5% agarose gels. Chromosome mapping is determined by the presence of an approximately 100 bp PCR fragment in the particular somatic cell hybrid.

Example 5

Bacterial Expression of a Polypeptide

A polynucleotide encoding a polypeptide of the present invention is amplified using PCR oligonucleotide primers corresponding to the 5' and 3' ends of the DNA sequence, as outlined in Example 1, to synthesize insertion fragments. The primers used to amplify the cDNA insert should preferably contain restriction sites, such as BamHI and XbaI, at the 5' end of the primers in order to clone the amplified product into the expression vector. For example, BamHI and XbaI correspond to the restriction enzyme sites on the bacterial expression vector pQE-9. (Qiagen, Inc., Chatsworth, Calif.). This plasmid vector encodes antibiotic resistance ($Amp^r$), a bacterial origin of replication (ori), an IPTG-regulatable promoter/operator (P/O), a ribosome binding site (RBS), a 6-histidine tag (6-His), and restriction enzyme cloning sites.

The pQE-9 vector is digested with BamHI and XbaI and the amplified fragment is ligated into the pQE-9 vector maintaining the reading frame initiated at the bacterial RBS. The ligation mixture is then used to transform the *E. coli* strain M15/rep4 (Qiagen, Inc.) which contains multiple copies of the plasmid pREP4, which expresses the lad repressor and also confers kanamycin resistance ($Kan^r$). Transformants are identified by their ability to grow on LB plates and ampicillin/kanamycin resistant colonies are selected. Plasmid DNA is isolated and confirmed by restriction analysis.

Clones containing the desired constructs are grown overnight (O/N) in liquid culture in LB media supplemented with both Amp (100 μg/ml) and Kan (25 μg/ml). The O/N culture is used to inoculate a large culture at a ratio of 1:100 to 1:250. The cells are grown to an optical density 600 ($O.D.^{600}$) of between 0.4 and 0.6. IPTG (Isopropyl-B-D-thiogalacto pyranoside) is then added to a final concentration of 1 mM. IPTG induces by inactivating the lad repressor, clearing the P/O leading to increased gene expression.

Cells are grown for an extra 3 to 4 hours. Cells are then harvested by centrifugation (20 min at 6000×g). The cell pellet is solubilized in the chaotropic agent 6 Molar Guanidine HCl by stirring for 3-4 hours at 4° C. The cell debris is removed by centrifugation, and the supernatant containing the polypeptide is loaded onto a nickel-nitrilo-tri-acetic acid ("Ni-NTA") affinity resin column (available from QIAGEN, Inc., supra). Proteins with a 6×His tag bind to the Ni-NTA resin with high affinity and can be purified in a simple one-step procedure (for details see: The QIAexpressionist (1995) QIAGEN, Inc., supra).

Briefly, the supernatant is loaded onto the column in 6 M guanidine-HCl, pH 8. The column is first washed with 10 volumes of 6 M guanidine-HCl, pH 8, then washed with 10 volumes of 6 M guanidine-HCl pH 6, and finally the polypeptide is eluted with 6 M guanidine-HCl, pH 5.

The purified protein is then renatured by dialyzing it against phosphate-buffered saline (PBS) or 50 mM Na-acetate, pH 6 buffer plus 200 mM NaCl. Alternatively, the protein can be successfully refolded while immobilized on the Ni-NTA column. The recommended conditions are as follows: renature using a linear 6M-1M urea gradient in 500 mM NaCl, 20% glycerol, 20 mM Tris/HCl pH 7.4, containing protease inhibitors. The renaturation should be performed over a period of 1.5 hours or more. After renaturation the proteins are eluted by the addition of 250 mM imidazole. Imidazole is removed by a final dialyzing step against PBS or 50 mM sodium acetate pH 6 buffer plus 200 mM NaCl. The purified protein is stored at 4° C. or frozen at −80° C.

In addition to the above expression vector, the present invention further includes an expression vector, called pHE4a (ATCC™ Accession Number 209645, deposited on Feb. 25, 1998) which contains phage operator and promoter elements operatively linked to a polynucleotide of the present invention, called pHE4a. (ATCC™ Accession Number 209645, deposited on Feb. 25, 1998.) This vector contains: 1) a neomycinphosphotransferase gene as a selection marker, 2) an *E. coli* origin of replication, 3) a T5 phage promoter sequence, 4) two lac operator sequences, 5) a Shine-Delgarno sequence, and 6) the lactose operon repressor gene (lacIq). The origin of replication (oriC) is derived from pUC19 (LTI, Gaithersburg, Md.). The promoter and operator sequences are made synthetically.

DNA can be inserted into the pHE4a by restricting the vector with NdeI and XbaI, BamHI, XhoI, or Asp718, running the restricted product on a gel, and isolating the larger fragment (the stuffer fragment should be about 310 base pairs). The DNA insert is generated according to the PCR protocol described in Example 1, using PCR primers having restriction sites for NdeI (5' primer) and XbaI, BamHI, XhoI, or Asp718 (3' primer). The PCR insert is gel purified and restricted with compatible enzymes. The insert and vector are ligated according to standard protocols.

The engineered vector could easily be substituted in the above protocol to express protein in a bacterial system.

Example 6

Purification of a Polypeptide from an Inclusion Body

The following alternative method can be used to purify a polypeptide expressed in *E. coli* when it is present in the form of inclusion bodies. Unless otherwise specified, all of the following steps are conducted at 4-10° C.

Upon completion of the production phase of the *E. coli* fermentation, the cell culture is cooled to 4-10° C. and the cells harvested by continuous centrifugation at 15,000 rpm (Heraeus Sepatech). On the basis of the expected yield of protein per unit weight of cell paste and the amount of purified protein required, an appropriate amount of cell paste, by weight, is suspended in a buffer solution containing 100 mM Tris, 50 mM EDTA, pH 7.4. The cells are dispersed to a homogeneous suspension using a high shear mixer.

The cells are then lysed by passing the solution through a microfluidizer (Microfluidics, Corp. or APV Gaulin, Inc.) twice at 4000-6000 psi. The homogenate is then mixed with NaCl solution to a final concentration of 0.5 M NaCl, followed by centrifugation at 7000×g for 15 min. The resultant pellet is washed again using 0.5M NaCl, 100 mM Tris, 50 mM EDTA, pH 7.4.

The resulting washed inclusion bodies are solubilized with 1.5 M guanidine hydrochloride (GuHCl) for 2-4 hours. After 7000×g centrifugation for 15 min., the pellet is discarded and the polypeptide containing supernatant is incubated at 4° C. overnight to allow further GuHCl extraction.

Following high speed centrifugation (30,000×g) to remove insoluble particles, the GuHCl solubilized protein is refolded by quickly mixing the GuHCl extract with 20 volumes of buffer containing 50 mM sodium, pH 4.5, 150 mM NaCl, 2 mM EDTA by vigorous stirring. The refolded diluted protein solution is kept at 4° C. without mixing for 12 hours prior to further purification steps.

To clarify the refolded polypeptide solution, a previously prepared tangential filtration unit equipped with 0.16 μm membrane filter with appropriate surface area (e.g., Filtron), equilibrated with 40 mM sodium acetate, pH 6.0 is employed. The filtered sample is loaded onto a cation exchange resin (e.g., Poros HS-50, Perseptive Biosystems). The column is washed with 40 mM sodium acetate, pH 6.0 and eluted with 250 mM, 500 mM, 1000 mM, and 1500 mM NaCl in the same buffer, in a stepwise manner. The absorbance at 280 nm of the effluent is continuously monitored. Fractions are collected and further analyzed by SDS-PAGE.

Fractions containing the polypeptide are then pooled and mixed with 4 volumes of water. The diluted sample is then loaded onto a previously prepared set of tandem columns of strong anion (Poros HQ-50, Perseptive Biosystems) and weak anion (Poros CM-20, Perseptive Biosystems) exchange resins. The columns are equilibrated with 40 mM sodium acetate, pH 6.0. Both columns are washed with 40 mM sodium acetate, pH 6.0, 200 mM NaCl. The CM-20 column is then eluted using a 10 column volume linear gradient ranging from 0.2 M NaCl, 50 mM sodium acetate, pH 6.0 to 1.0 M NaCl, 50 mM sodium acetate, pH 6.5. Fractions are collected under constant $A_{280}$ monitoring of the effluent. Fractions containing the polypeptide (determined, for instance, by 16% SDS-PAGE) are then pooled.

The resultant polypeptide should exhibit greater than 95% purity after the above refolding and purification steps. No major contaminant bands should be observed from Commassie blue stained 16% SDS-PAGE gel when 5 μg of purified protein is loaded. The purified protein can also be tested for endotoxin/LPS contamination, and typically the LPS content is less than 0.1 ng/ml according to LAL assays.

Example 7

Cloning and Expression of a Polypeptide in a Baculovirus Expression System

In this example, the plasmid shuttle vector pA2 is used to insert a polynucleotide into a baculovirus to express a polypeptide. This expression vector contains the strong polyhedrin promoter of the *Autographa californica* nuclear polyhedrosis virus (AcMNPV) followed by convenient restriction sites such as BamHI, Xba I and Asp718. The polyadenylation site of the simian virus 40 ("SV40") is used for efficient polyadenylation. For easy selection of recombinant virus, the plasmid contains the beta-galactosidase gene from *E. coli* under control of a weak *Drosophila* promoter in the same orientation, followed by the polyadenylation signal of the polyhedrin gene. The inserted genes are flanked on both sides by viral sequences for cell-mediated homologous recombination with wild-type viral DNA to generate a viable virus that express the cloned polynucleotide.

Many other baculovirus vectors can be used in place of the vector above, such as pAc373, pVL941, and pAcIM1, as one skilled in the art would readily appreciate, as long as the construct provides appropriately located signals for transcription, translation, secretion and the like, including a signal peptide and an in-frame AUG as required. Such vectors are described, for instance, in Luckow et al., Virology 170:31-39 (1989).

Specifically, the cDNA sequence contained in the deposited clone, including the AUG initiation codon, is amplified using the PCR protocol described in Example 1. If a naturally occurring signal sequence is used to produce the polypeptide of the present invention, the pA2 vector does not need a second signal peptide. Alternatively, the vector can be modified (pA2 GP) to include a baculovirus leader sequence, using the standard methods described in Summers et al., "A Manual of Methods for Baculovirus Vectors and Insect Cell Culture Procedures," Texas Agricultural Experimental Station Bulletin No. 1555 (1987).

The amplified fragment is isolated from a 1% agarose gel using a commercially available kit ("GENECLEAN™," BIO 101 Inc., La Jolla, Calif.). The fragment then is digested with appropriate restriction enzymes and again purified on a 1% agarose gel.

The plasmid is digested with the corresponding restriction enzymes and optionally, can be dephosphorylated using calf intestinal phosphatase, using routine procedures known in the art. The DNA is then isolated from a 1% agarose gel using a commercially available kit ("GENECLEAN™" BIO 101 Inc., La Jolla, Calif.).

The fragment and the dephosphorylated plasmid are ligated together with T4 DNA ligase. *E. coli* HB101 or other suitable *E. coli* hosts such as XL-1 Blue (STRATAGENE™ Cloning Systems, La Jolla, Calif.) cells are transformed with the ligation mixture and spread on culture plates. Bacteria containing the plasmid are identified by digesting DNA from individual colonies and analyzing the digestion product by gel electrophoresis. The sequence of the cloned fragment is confirmed by DNA sequencing.

Five μg of a plasmid containing the polynucleotide is co-transfected with 1.0 μg of a commercially available linearized baculovirus DNA ("BACULOGOLD™ baculovirus DNA, Pharmingen, San Diego, Calif.), using the lipofection method described by Felgner et al., Proc. Natl. Acad. Sci. USA 84:7413-7417 (1987). One μg of BACULOGOLD™ virus DNA and 5 μg of the plasmid are mixed in a sterile well of a microtiter plate containing 50 μl of serum-free Grace's medium (LIFE TECHNOLOGIES™ Inc., Gaithersburg, Md.). Afterwards, 10 μl LIPOFECTIN™ plus 90 μl Grace's medium are added, mixed and incubated for 15 minutes at room temperature. Then the transfection mixture is added drop-wise to Sf9 insect cells (ATCC™ CRL 1711) seeded in a 35 mm tissue culture plate with 1 ml Grace's medium without serum. The plate is then incubated for 5 hours at 27° C. The transfection solution is then removed from the plate and 1 ml of Grace's insect medium supplemented with 10% fetal calf serum is added. Cultivation is then continued at 27° C. for four days.

After four days the supernatant is collected and a plaque assay is performed, as described by Summers and Smith, supra. An agarose gel with "Blue Gal" (LIFE TECHNOLOGIES™ Inc., Gaithersburg) is used to allow easy identification and isolation of gal-expressing clones, which produce blue-stained plaques. (A detailed description of a "plaque assay" of this type can also be found in the user's guide for insect cell culture and baculovirology distributed by LIFE TECHNOLOGIES™ Inc., Gaithersburg, page 9-10.) After appropriate incubation, blue stained plaques are picked with the tip of a micropipettor (e.g., Eppendorf). The agar containing the recombinant viruses is then resuspended in a microcentrifuge tube containing 200 μl of Grace's medium and the suspension containing the recombinant baculovirus is used to infect Sf9 cells seeded in 35 mm dishes. Four days later the supernatants of these culture dishes are harvested and then they are stored at 4° C.

To verify the expression of the polypeptide, Sf9 cells are grown in Grace's medium supplemented with 10% heat-inactivated FBS. The cells are infected with the recombinant baculovirus containing the polynucleotide at a multiplicity of infection ("MOI") of about 2. If radiolabeled proteins are desired, 6 hours later the medium is removed and is replaced with SF900 II medium minus methionine and cysteine (available from LIFE TECHNOLOGIES™ Inc., Rockville, Md.). After 42 hours, 5 μCi of $^{35}$S-methionine and 5 μCi $^{35}$S-cysteine (available from Amersham) are added. The cells are further incubated for 16 hours and then are harvested by centrifugation. The proteins in the supernatant as well as the intracellular proteins are analyzed by SDS-PAGE followed by autoradiography (if radiolabeled).

Microsequencing of the amino acid sequence of the amino terminus of purified protein may be used to determine the amino terminal sequence of the produced protein.

Example 8

Expression of a Polypeptide in Mammalian Cells

The polypeptide of the present invention can be expressed in a mammalian cell. A typical mammalian expression vector contains a promoter element, which mediates the initiation of transcription of mRNA, a protein coding sequence, and signals required for the termination of transcription and polyadenylation of the transcript. Additional elements include enhancers, Kozak sequences and intervening sequences flanked by donor and acceptor sites for RNA splicing. Highly efficient transcription is achieved with the early and late promoters from SV40, the long terminal repeats (LTRs) from Retroviruses, e.g., RSV, HTLVI, HIVI and the early promoter of the cytomegalovirus (CMV). However, cellular elements can also be used (e.g., the human actin promoter).

Suitable expression vectors for use in practicing the present invention include, for example, vectors such as pSVL and pMSG (PHARMACIA™, Uppsala, Sweden), pRSVcat (ATCC™ 37152), pSV2dhfr (ATCC™ 37146), pBC12MI (ATCC™ 67109), pCMVSport 2.0, and pCMVSport 3.0. Mammalian host cells that could be used include, human Hela, 293, H9 and Jurkat cells, mouse NIH3T3 and C127 cells, Cos 1, Cos 7 and CV1, quail QC1-3 cells, mouse L cells and Chinese hamster ovary (CHO) cells.

Alternatively, the polypeptide can be expressed in stable cell lines containing the polynucleotide integrated into a chromosome. The co-transfection with a selectable marker such as DHFR, gpt, neomycin, or hygromycin allows the identification and isolation of the transfected cells.

The transfected gene can also be amplified to express large amounts of the encoded protein. The DHFR (dihydrofolate reductase) marker is useful in developing cell lines that carry several hundred or even several thousand copies of the gene of interest. (See, e.g., Alt, F. W., et al., J. Biol. Chem. 253:1357-1370 (1978); Hamlin, J. L. and Ma, C., Biochem. et Biophys. Acta, 1097:107-143 (1990); Page, M. J. and Sydenham, M. A., Biotechnology 9:64-68 (1991)). Another useful selection marker is the enzyme glutamine synthase (GS) (Murphy et al., Biochem J. 227:277-279 (1991); Bebbington et al., Bio/Technology 10:169-175 (1992). Using these markers, the mammalian cells are grown in selective medium and the cells with the highest resistance are selected. These cell lines contain the amplified gene(s) integrated into a chromosome. Chinese hamster ovary (CHO) and NSO cells are often used for the production of proteins.

Derivatives of the plasmid pSV2-dhfr (ATCC™ Accession No. 37146), the expression vectors pC4 (ATCC™ Accession No. 209646) and pC6 (ATCC™ Accession No. 209647) contain the strong promoter (LTR) of the Rous Sarcoma Virus (Cullen et al., Molecular and Cellular Biology, 438-447 (March, 1985)) plus a fragment of the CMV-enhancer (Boshart et al., Cell 41:521-530 (1985)). Multiple cloning sites, e.g., with the restriction enzyme cleavage sites BamHI, XbaI and Asp718, facilitate the cloning of the gene of interest. The vectors also contain the 3' intron, the polyadenylation and termination signal of the rat preproinsulin gene, and the mouse DHFR gene under control of the SV40 early promoter.

Specifically, the plasmid pC6, for example, is digested with appropriate restriction enzymes and then dephosphorylated using calf intestinal phosphates by procedures known in the art. The vector is then isolated from a 1% agarose gel.

A polynucleotide of the present invention is amplified according to the protocol outlined in Example 1. If a naturally occurring signal sequence is used to produce the polypeptide of the present invention, the vector does not need a second signal peptide. Alternatively, if a naturally occurring signal sequence is not used, the vector can be modified to include a heterologous signal sequence. (See, e.g., International Publication No. WO 96/34891.)

The amplified fragment is isolated from a 1% agarose gel using a commercially available kit ("GENECLEAN™," BIO 101 Inc., La Jolla, Calif.). The fragment then is digested with appropriate restriction enzymes and again purified on a 1% agarose gel.

The amplified fragment is then digested with the same restriction enzyme and purified on a 1% agarose gel. The isolated fragment and the dephosphorylated vector are then ligated with T4 DNA ligase. *E. coli* HB101 or XL-1 Blue cells are then transformed and bacteria are identified that contain the fragment inserted into plasmid pC6 using, for instance, restriction enzyme analysis.

Chinese hamster ovary cells lacking an active DHFR gene are used for transfection. Five μg of the expression plasmid pC6 or pC4 is cotransfected with 0.5 μg of the plasmid pSV-neo using LIPOFECTIN™ (Felgner et al., supra). The plasmid pSV2-neo contains a dominant selectable marker, the neo gene from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) in alpha minus MEM supplemented with 10, 25, or 50 ng/ml of methotrexate plus 1 mg/ml G418. After about 10-14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 μM, 2 μM, 5 μM, 10 mM, 20 mM). The same procedure is repeated until clones are obtained which grow at a concentration of 100-200 μM. Expression of the desired gene product is analyzed, for instance, by SDS-PAGE and Western blot or by reversed phase HPLC analysis.

Example 9

Protein Fusions

The polypeptides of the present invention are preferably fused to other proteins. These fusion proteins can be used for a variety of applications. For example, fusion of the present polypeptides to His-tag, HA-tag, protein A, IgG domains, and maltose binding protein facilitates purification. (See Example 5; see also EPA 394,827; Traunecker, et al., Nature 331:84-86 (1988)). Similarly, fusion to IgG-1, IgG-3, and albumin increases the halflife time in vivo. Nuclear localization signals fused to the polypeptides of the present invention can target the protein to a specific subcellular localization, while covalent heterodimer or homodimers can increase or decrease the activity of a fusion protein. Fusion proteins can also create chimeric molecules having more than one function. Finally, fusion proteins can increase solubility and/or stability of the fused protein compared to the non-fused protein. All of the types of fusion proteins described above can be made by modifying the following protocol, which outlines the fusion of a polypeptide to an IgG molecule, or the protocol described in Example 5.

Briefly, the human Fc portion of the IgG molecule can be PCR amplified, using primers that span the 5' and 3' ends of the sequence described below. These primers also should have convenient restriction enzyme sites that will facilitate cloning into an expression vector, preferably a mammalian expression vector.

For example, if pC4 (ATCC™ Accession No. 209646) is used, the human Fc portion can be ligated into the BamHI cloning site. Note that the 3' BamHI site should be destroyed. Next, the vector containing the human Fc portion is re-restricted with BamHI, linearizing the vector, and a polynucleotide of the present invention, isolated by the PCR protocol described in Example 1, is ligated into this BamHI site. Note that the polynucleotide is cloned without a stop codon, otherwise a fusion protein will not be produced.

If the naturally occurring signal sequence is used to produce the polypeptide of the present invention, pC4 does not need a second signal peptide. Alternatively, if the naturally occurring signal sequence is not used, the vector can be modified to include a heterologous signal sequence. (See, e.g., International Publication No. WO 96/34891.)

```
Human IgG Fc region:
                                        (SEQ ID NO: 236)
GGGATCCGGAGCCCAAATCTTCTGACAAAACTCACACATGCCCACCGTGC

CCAGCACCTGAATTCGAGGGTGCACCGTCAGTCTTCCTCTTCCCCCCAAA

ACCCAAGGACACCCTCATGATCTCCCGGACTCCTGAGGTCACATGCGTGG

TGGTGGACGTAAGCCACGAAGACCCTGAGGTCAAGTTCAACTGGTACGTG

GACGGCGTGGAGGTGCATAATGCCAAGACAAAGCCGCGGGAGGAGCAGTA
```

-continued

```
CAACAGCACGTACCGTGTGGTCAGCGTCCTCACCGTCCTGCACCAGGACT

GGCTGAATGGCAAGGAGTACAAGTGCAAGGTCTCCAACAAAGCCCTCCCA

ACCCCCATCGAGAAAACCATCTCCAAAGCCAAAGGGCAGCCCCGAGAACC

ACAGGTGTACACCCTGCCCCCATCCCGGGATGAGCTGACCAAGAACCAGG

TCAGCCTGACCTGCCTGGTCAAAGGCTTCTATCCAAGCGACATCGCCGTG

GAGTGGGAGAGCAATGGGCAGCCGGAGAACAACTACAAGACCACGCCTCC

CGTGCTGGACTCCGACGGCTCCTTCTTCCTCTACAGCAAGCTCACCGTGG

ACAAGAGCAGGTGGCAGCAGGGGAACGTCTTCTCATGCTCCGTGATGCAT

GAGGCTCTGCACAACCACTACACGCAGAAGAGCCTCTCCCTGTCTCCGGG

TAAATGAGTGCGACGGCCGCGACTCTAGAGGAT
```

Example 10

Production of an Antibody from a Polypeptide a) Hybridoma Technology

The antibodies of the present invention can be prepared by a variety of methods. (See, Current Protocols, Chapter 2.) As one example of such methods, cells expressing a polypeptide of the present invention are administered to an animal to induce the production of sera containing polyclonal antibodies. In a preferred method, a preparation of a polypeptide of the present invention is prepared and purified to render it substantially free of natural contaminants. Such a preparation is then introduced into an animal in order to produce polyclonal antisera of greater specific activity.

Monoclonal antibodies specific for a polypeptide of the present invention are prepared using hybridoma technology (Kohler et al., Nature 256:495 (1975); Kohler et al., Eur. J. Immunol. 6:511 (1976); Kohler et al., Eur. J. Immunol. 6:292 (1976); Hammerling et al., in: Monoclonal Antibodies and T-Cell Hybridomas, Elsevier, N.Y., pp. 563-681 (1981)). In general, an animal (preferably a mouse) is immunized with a polypeptide of the present invention or, more preferably, with a secreted polypeptide-expressing cell. Such polypeptide-expressing cells are cultured in any suitable tissue culture medium, preferably in Earle's modified Eagle's medium supplemented with 10% fetal bovine serum (inactivated at about 56° C.), and supplemented with about 10 g/l of nonessential amino acids, about 1,000 U/ml of penicillin, and about 100 μg/ml of streptomycin.

The splenocytes of such mice are extracted and fused with a suitable myeloma cell line. Any suitable myeloma cell line may be employed in accordance with the present invention; however, it is preferable to employ the parent myeloma cell line (SP2O), available from the ATCC™. After fusion, the resulting hybridoma cells are selectively maintained in HAT medium, and then cloned by limiting dilution as described by Wands et al. (Gastroenterology 80:225-232 (1981)). The hybridoma cells obtained through such a selection are then assayed to identify clones which secrete antibodies capable of binding the polypeptide of the present invention.

Alternatively, additional antibodies capable of binding to a polypeptide of the present invention can be produced in a two-step procedure using anti-idiotypic antibodies. Such a method makes use of the fact that antibodies are themselves antigens, and therefore, it is possible to obtain an antibody that binds to a second antibody. In accordance with this method, protein specific antibodies are used to immunize an animal, preferably a mouse. The splenocytes of such an animal are then used to produce hybridoma cells, and the hybridoma cells are screened to identify clones which produce an antibody whose ability to bind to the polypeptide-specific antibody can be blocked by said polypeptide. Such antibodies comprise anti-idiotypic antibodies to the polypeptide-specific antibody and are used to immunize an animal to induce formation of further polypeptide-specific antibodies.

It will be appreciated that Fab and F(ab')2 and other fragments of the antibodies of the present invention may be used according to the methods disclosed herein. Such fragments are typically produced by proteolytic cleavage, using enzymes such as papain (to produce Fab fragments) or pepsin (to produce F(ab')2 fragments). Alternatively, secreted protein-binding fragments can be produced through the application of recombinant DNA technology or through synthetic chemistry.

For in vivo use of antibodies in humans, an antibody is "humanized". Such antibodies can be produced using genetic constructs derived from hybridoma cells producing the monoclonal antibodies described above. Methods for producing chimeric and humanized antibodies are known in the art and are discussed herein. (See, for review, Morrison, Science 229:1202 (1985); Oi et al., BioTechniques 4:214 (1986); Cabilly et al., U.S. Pat. No. 4,816,567; Taniguchi et al., EP 171496; Morrison et al., EP 173494; Neuberger et al., WO 8601533; Robinson et al., International Publication No. WO 8702671; Boulianne et al., Nature 312:643 (1984); Neuberger et al., Nature 314:268 (1985)).

b) Isolation of Antibody Fragments Directed Against a Polypeptide of the Present Invention from a Library of scFvs Naturally occurring V-genes isolated from human PBLs are constructed into a library of antibody fragments which contain reactivities against a polypeptide of the present invention to which the donor may or may not have been exposed (see e.g., U.S. Pat. No. 5,885,793 incorporated herein by reference in its entirety).

Rescue of the Library. A library of scFvs is constructed from the RNA of human PBLs as described in International Publication No. WO 92/01047. To rescue phage displaying antibody fragments, approximately $10^9$ *E. coli* harboring the phagemid are used to inoculate 50 ml of 2×TY containing 1% glucose and 100 μg/ml of ampicillin (2×TY-AMP-GLU) and grown to an O.D. of 0.8 with shaking Five ml of this culture is used to inoculate 50 ml of 2×TY-AMP-GLU, 2×108 TU of delta gene 3 helper (M13 delta gene III, see International Publication No. WO 92/01047) are added and the culture incubated at 37° C. for 45 minutes without shaking and then at 37° C. for 45 minutes with shaking. The culture is centrifuged at 4000 r.p.m. for 10 min. and the pellet resuspended in 2 liters of 2×TY containing 100 μg/ml ampicillin and 50 μg/ml kanamycin and grown overnight. Phage are prepared as described in International Publication No. WO 92/01047.

M13 delta gene III is prepared as follows: M13 delta gene III helper phage does not encode gene III protein, hence the phage(mid) displaying antibody fragments have a greater avidity of binding to antigen. Infectious M13 delta gene III particles are made by growing the helper phage in cells harboring a pUC19 derivative supplying the wild type gene III protein during phage morphogenesis. The culture is incubated for 1 hour at 37° C. without shaking and then for a further hour at 37° C. with shaking Cells are spun down (IEC-Centra 8,400 r.p.m. for 10 min), resuspended in 300 ml 2×TY broth containing 100 μg ampicillin/ml and 25 μg kanamycin/ml (2×TY-AMP-KAN) and grown overnight, shaking at 37° C. Phage particles are purified and concentrated from the culture medium by two PEG-precipitations (Sambrook et al., 1990), resuspended in 2 ml PBS and passed through a 0.45 μm filter (Minisart NML; Sartorius) to give a final concentration of approximately $10^{13}$ transducing units/ml (ampicillin-resistant clones).

Panning of the Library. Immunotubes (Nunc) are coated overnight in PBS with 4 ml of either 100 μg/ml or 10 μg/ml of a polypeptide of the present invention. Tubes are blocked with 2% Marvel-PBS for 2 hours at 37° C. and then washed 3 times in PBS. Approximately $10^{13}$ TU of phage is applied to the tube and incubated for 30 minutes at room temperature tumbling on an over and under turntable and then left to stand for another 1.5 hours. Tubes are washed 10 times with PBS 0.1% Tween-20 and 10 times with PBS. Phage are eluted by adding 1 ml of 100 mM triethylamine and rotating 15 minutes on an under and over turntable after which the solution is immediately neutralized with 0.5 ml of 1.0M Tris-HCl, pH 7.4. Phage are then used to infect 10 ml of mid-log *E. coli* TG1 by incubating eluted phage with bacteria for 30 minutes at 37° C. The *E. coli* are then plated on TYE plates containing 1% glucose and 100 μg/ml ampicillin. The resulting bacterial library is then rescued with delta gene 3 helper phage as described above to prepare phage for a subsequent round of selection. This process is then repeated for a total of 4 rounds of affinity purification with tube-washing increased to 20 times with PBS, 0.1% Tween-20 and 20 times with PBS for rounds 3 and 4.

Characterization of Binders. Eluted phage from the 3rd and 4th rounds of selection are used to infect *E. coli* HB 2151 and soluble scFv is produced (Marks, et al., 1991) from single colonies for assay. ELISAs are performed with microtitre plates coated with either 10 pg/ml of the polypeptide of the present invention in 50 mM bicarbonate pH 9.6. Clones positive in ELISA are further characterized by PCR fingerprinting (see, e.g., International Publication No. WO 92/01047) and then by sequencing. These ELISA positive clones may also be further characterized by techniques known in the art, such as, for example, epitope mapping, binding affinity, receptor signal transduction, ability to block or competitively inhibit antibody/antigen binding, and competitive agonistic or antagonistic activity.

Example 11

Method of Determining Alterations in a Gene Corresponding to a Polynucleotide RNA from entire families or individual patients presenting with a phenotype of interest (such as a disease or disorder, e.g., an immune, cardiovascular, cancer, or other proliferative disease or disorder) is isolated. cDNA is then generated from these RNA samples using protocols known in the art. (See, Sambrook.) The cDNA is then used as a template for PCR, employing primers surrounding regions of interest in SEQ ID NO:X; and/or the nucleotide sequence of the cDNA contained in ATCC™ Deposit No:Z. Suggested PCR conditions consist of 35 cycles at 95° C. for 30 seconds; 60-120 seconds at 52-58° C.; and 60-120 seconds at 70° C., using buffer solutions described in Sidransky et al., Science 252:706 (1991).

PCR products are then sequenced using primers labeled at their 5' end with T4 polynucleotide kinase, employing SequiTherm Polymerase (Epicentre Technologies). The intron-exon boundaries of selected exons is also determined and genomic PCR products analyzed to confirm the results. PCR products harboring suspected mutations are then cloned and sequenced to validate the results of the direct sequencing.

PCR products are cloned into T-tailed vectors as described in Holton et al., Nucleic Acids Research, 19:1156 (1991) and sequenced with T7 polymerase (United States Biochemical). Affected individuals are identified by mutations not present in unaffected individuals.

Genomic rearrangements are also observed as a method of determining alterations in a gene corresponding to a polynucleotide. Genomic clones isolated according to Example 2 are nick-translated with digoxigenindeoxy-uridine 5'-triphosphate (BOEHRINGER™ Manheim), and FISH performed as described in Johnson et al., Methods Cell Biol. 35:73-99 (1991). Hybridization with the labeled probe is carried out using a vast excess of human cot-1 DNA for specific hybridization to the corresponding genomic locus.

Chromosomes are counterstained with 4,6-diamino-2-phenylidole and propidium iodide, producing a combination of C- and R-bands. Aligned images for precise mapping are obtained using a triple-band filter set (Chroma Technology, Brattleboro, Vt.) in combination with a cooled charge-coupled device camera (Photometrics, Tucson, Ariz.) and variable excitation wavelength filters. (Johnson et al., Genet. Anal. Tech. Appl., 8:75 (1991)). Image collection, analysis and chromosomal fractional length measurements are performed using the ISee Graphical Program System. (Inovision Corporation, Durham, N.C.) Chromosome alterations of the genomic region hybridized by the probe are identified as insertions, deletions, and translocations. These alterations are used as a diagnostic marker for an associated disease.

Example 12

Method of Detecting Abnormal Levels of a Polypeptide in a Biological Sample

A polypeptide of the present invention can be detected in a biological sample, and if an increased or decreased level of the polypeptide is detected, this polypeptide is a marker for a particular phenotype. Methods of detection are numerous, and thus, it is understood that one skilled in the art can modify the following assay to fit their particular needs.

For example, antibody-sandwich ELISAs are used to detect polypeptides in a sample, preferably a biological sample. Wells of a microtiter plate are coated with specific antibodies, at a final concentration of 0.2 to 10 μg/ml. The antibodies are either monoclonal or polyclonal and are produced by the method described in Example 10. The wells are blocked so that non-specific binding of the polypeptide to the well is reduced.

The coated wells are then incubated for >2 hours at RT with a sample containing the polypeptide. Preferably, serial dilutions of the sample should be used to validate results. The plates are then washed three times with deionized or distilled water to remove unbound polypeptide.

Next, 50 μl of specific antibody-alkaline phosphatase conjugate, at a concentration of 25-400 ng, is added and incubated for 2 hours at room temperature. The plates are again washed three times with deionized or distilled water to remove unbound conjugate.

Add 75 μl of 4-methylumbelliferyl phosphate (MUP) or p-nitrophenyl phosphate (NPP) substrate solution to each well and incubate 1 hour at room temperature. Measure the reaction by a microtiter plate reader. Prepare a standard curve, using serial dilutions of a control sample, and plot polypeptide concentration on the X-axis (log scale) and fluorescence or absorbance of the Y-axis (linear scale). Interpolate the concentration of the polypeptide in the sample using the standard curve.

Example 13

Formulation

The invention also provides methods of preventing, treating and/or ameliorating a disease or disorder (such as, for example, any one or more of the diseases or disorders disclosed herein, e.g., an immune, cardiovascular, cancer, or other proliferative disease or disorder) by administration to a subject of an effective amount of a Therapeutic. By therapeutic is meant polynucleotides or polypeptides of the invention (including fragments and variants), agonists or antagonists thereof, and/or antibodies thereto, in combination with a pharmaceutically acceptable carrier type (e.g., a sterile carrier).

The Therapeutic will be formulated and dosed in a fashion consistent with good medical practice, taking into account the clinical condition of the individual patient (especially the side effects of treatment with the Therapeutic alone), the site of delivery, the method of administration, the scheduling of administration, and other factors known to practitioners. The "effective amount" for purposes herein is thus determined by such considerations.

As a general proposition, the total pharmaceutically effective amount of the Therapeutic administered parenterally per dose will be in the range of about 1 ug/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day for the hormone. If given continuously, the Therapeutic is typically administered at a dose rate of about 1 μg/kg/hour to about 50 μg/kg/hour, either by 1-4 injections per day or by continuous subcutaneous infusions, for example, using a mini-pump. An intravenous bag solution may also be employed. The length of treatment needed to observe changes and the interval following treatment for responses to occur appears to vary depending on the desired effect.

Therapeutics can be administered orally, rectally, parenterally, intracistemally, intravaginally, intraperitoneally, topically (as by powders, ointments, gels, drops or transdermal patch), bucally, or as an oral or nasal spray. "Pharmaceutically acceptable carrier" refers to a non-toxic solid, semisolid or liquid filler, diluent, encapsulating material or formulation auxiliary of any. The term "parenteral" as used herein refers to modes of administration which include intravenous, intramuscular, intraperitoneal, intrasternal, subcutaneous and intraarticular injection and infusion.

Therapeutics of the invention are also suitably administered by sustained-release systems. Suitable examples of sustained-release Therapeutics are administered orally, rectally, parenterally, intracistemally, intravaginally, intraperitoneally, topically (as by powders, ointments, gels, drops or transdermal patch), bucally, or as an oral or nasal spray. "Pharmaceutically acceptable carrier" refers to a non-toxic solid, semisolid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

Therapeutics of the invention are also suitably administered by sustained-release systems. Suitable examples of sustained-release Therapeutics include suitable polymeric materials (such as, for example, semi-permeable polymer matrices in the form of shaped articles, e.g., films, or microcapsules), suitable hydrophobic materials (for example as an emulsion in an acceptable oil) or ion exchange resins, and sparingly soluble derivatives (such as, for example, a sparingly soluble salt).

Sustained-release matrices include polylactides (U.S. Pat. No. 3,773,919, EP 58,481), copolymers of L-glutamic acid and gamma-ethyl-L-glutamate (Sidman et al., Biopolymers 22:547-556 (1983)), poly(2-hydroxyethyl methacrylate) (Langer et al., J. Biomed. Mater. Res. 15:167-277 (1981), and Langer, Chem. Tech. 12:98-105 (1982)), ethylene vinyl acetate (Langer et al., Id.) or poly-D-(−)-3-hydroxybutyric acid (EP 133,988).

In a preferred embodiment, polypeptide, polynucleotide, and antibody compositions of the invention are formulated in a biodegradable, polymeric drug delivery system, for example as described in U.S. Pat. Nos. 4,938,763; 5,278,201; 5,278,202; 5,324,519; 5,340,849; and 5,487,897 and in International Publication Numbers WO01/35929, WO00/24374, and WO00/06117 which are hereby incorporated by reference in their entirety. In specific preferred embodiments the polypeptide, polynucleotide, and antibody compositions of the invention are formulated using the ATRIGEL® Biodegradable System of Atrix Laboratories, Inc. (Fort Collins, Colo.).

Examples of biodegradable polymers which can be used in the formulation of polypeptide, polynucleotide, and antibody compositions, include but are not limited to, polylactides, polyglycolides, polycaprolactones, polyanhydrides, polyamides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyalkylene oxalates, polyalkylene succinates, poly(malic acid), poly(amino acids), poly(methyl vinyl ether), poly(maleic anhydride), polyvinylpyrrolidone, polyethylene glycol, polyhydroxycellulose, chitin, chitosan, and copolymers, terpolymers, or combinations or mixtures of the above materials. The preferred polymers are those that have a lower degree of crystallization and are more hydrophobic. These polymers and copolymers are more soluble in the biocompatible solvents than the highly crystalline polymers such as polyglycolide and chitin which also have a high degree of hydrogen-bonding. Preferred materials with the desired solubility parameters are the polylactides, polycaprolactones, and copolymers of these with glycolide in which there are more amorphous regions to enhance solubility. In specific preferred embodiments, the biodegradable polymers which can be used in the formulation of polypeptide, polynucleotide, and antibody compositions are poly(lactide-co-glycolides). Polymer properties such as molecular weight, hydrophobicity, and lactide/glycolide ratio may be modified to obtain the desired polypeptide, polynucleotide, or antibody release profile (See, e.g., Ravivarapu et al., Journal of Pharmaceutical Sciences 89:732-741 (2000), which is hereby incorporated by reference in its entirety).

It is also preferred that the solvent for the biodegradable polymer be non-toxic, water miscible, and otherwise biocompatible. Examples of such solvents include, but are not limited to, N-methyl-2-pyrrolidone, 2-pyrrolidone, C2 to C6 alkanols, C1 to C15 alcohols, dils, triols, and tetraols such as ethanol, glycerine propylene glycol, butanol; C3 to C15 alkyl ketones such as acetone, diethyl ketone and methyl ethyl ketone; C3 to C15 esters such as methyl acetate, ethyl acetate, ethyl lactate; alkyl ketones such as methyl ethyl ketone, C1 to C15 amides such as dimethylformamide, dimethylacetamide and caprolactam; C3 to C20 ethers such as tetrahydrofuran, or solketal; tweens, triacetin, propylene carbonate, decylmethylsulfoxide, dimethyl sulfoxide, oleic acid, 1-dodecylazacycloheptan-2-one, Other preferred solvents are benzyl alcohol, benzyl benzoate, dipropylene glycol, tributyrin, ethyl oleate, glycerin, glycofural, isopropyl myristate, isopropyl palmitate, oleic acid, polyethylene glycol, propylene carbonate, and triethyl citrate. The most preferred solvents are N-methyl-2-pyrrolidone, 2-pyrrolidone, dimethyl sulfoxide, triacetin, and propylene carbonate because of the solvating ability and their compatibility.

Additionally, formulations comprising polypeptide, polynucleotide, and antibody compositions and a biodegradable polymer may also include release-rate modification agents and/or pore-forming agents. Examples of release-rate modification agents include, but are not limited to, fatty acids, triglycerides, other like hydrophobic compounds, organic solvents, plasticizing compounds and hydrophilic compounds. Suitable release rate modification agents include, for example, esters of mono-, di-, and tricarboxylic acids, such as 2-ethoxyethyl acetate, methyl acetate, ethyl acetate, diethyl phthalate, dimethyl phthalate, dibutyl phthalate, dimethyl adipate, dimethyl succinate, dimethyl oxalate, dimethyl citrate, triethyl citrate, acetyl tributyl citrate, acetyl triethyl citrate, glycerol triacetate, di(n-butyl)sebecate, and the like; polyhydroxy alcohols, such as propylene glycol, polyethylene glycol, glycerin, sorbitol, and the like; fatty acids; triesters of glycerol, such as triglycerides, epoxidized soybean oil, and other epoxidized vegetable oils; sterols, such as cholesterol; alcohols, such as C.sub.6-C.sub.12 alkanols, 2-ethoxyethanol. The release rate modification agent may be used singly or in combination with other such agents. Suitable combinations of release rate modification agents include, but are not limited to, glycerin/propylene glycol, sorbitol/glycerine, ethylene oxide/propylene oxide, butylene glycol/adipic acid, and the like. Preferred release rate modification agents include, but are not limited to, dimethyl citrate, triethyl citrate, ethyl heptanoate, glycerin, and hexanediol. Suitable pore-forming agents that may be used in the polymer composition include, but are not limited to, sugars such as sucrose and dextrose, salts such as sodium chloride and sodium carbonate, polymers such as hydroxylpropylcellulose, carboxymethylcellulose, polyethylene glycol, and polyvinylpyrrolidone. Solid crystals that will provide a defined pore size, such as salt or sugar, are preferred.

In specific preferred embodiments the polypeptide, polynucleotide, and antibody compositions of the invention are formulated using the BEMA™ BioErodible Mucoadhesive System, MCA™ MucoCutaneous Absorption System, SMP™ Solvent MicroParticle System, or BCP™ BioCompatible Polymer System of Atrix Laboratories, Inc. (Fort Collins, Colo.).

Sustained-release Therapeutics also include liposomally entrapped Therapeutics of the invention (see generally, Langer, *Science* 249:1527-1533 (1990); Treat et al., in *Liposomes in the Therapy of Infectious Disease and Cancer*, Lopez-Berestein and Fidler (eds.), Liss, New York, pp. 317-327 and 353-365 (1989)). Liposomes containing the Therapeutic are prepared by methods known per se: DE 3,218,121; Epstein et al., Proc. Natl. Acad. Sci. (USA) 82:3688-3692 (1985); Hwang et al., Proc. Natl. Acad. Sci. (USA) 77:4030-4034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324. Ordinarily, the liposomes are of the small (about 200-800 Angstroms) unilamellar type in which the lipid content is greater than about 30 mol. percent cholesterol, the selected proportion being adjusted for the optimal Therapeutic.

In yet an additional embodiment, the Therapeutics of the invention are delivered by way of a pump (see Langer, supra;

Sefton, CRC Crit. Ref. Biomed. Eng. 14:201 (1987); Buchwald et al., Surgery 88:507 (1980); Saudek et al., N. Engl. J. Med. 321:574 (1989)).

Other controlled release systems are discussed in the review by Langer (Science 249:1527-1533 (1990)).

For parenteral administration, in one embodiment, the Therapeutic is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to the Therapeutic.

Generally, the formulations are prepared by contacting the Therapeutic uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, manose, or dextrins; chelating agents such as EDTA; sugar alcohols such as mannitol or sorbitol; counterions such as sodium; and/or nonionic surfactants such as polysorbates, poloxamers, or PEG.

The Therapeutic is typically formulated in such vehicles at a concentration of about 0.1 mg/ml to 100 mg/ml, preferably 1-10 mg/ml, at a pH of about 3 to 8. It will be understood that the use of certain of the foregoing excipients, carriers, or stabilizers will result in the formation of polypeptide salts.

Any pharmaceutical used for therapeutic administration can be sterile. Sterility is readily accomplished by filtration through sterile filtration membranes (e.g., 0.2 micron membranes). Therapeutics generally are placed into a container having a sterile access port, for example, an intravenous solution bag or vial having a stopper pierceable by a hypodermic injection needle.

Therapeutics ordinarily will be stored in unit or multi-dose containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous Therapeutic solution, and the resulting mixture is lyophilized. The infusion solution is prepared by reconstituting the lyophilized Therapeutic using bacteriostatic Water-for-Injection.

The invention also provides a pharmaceutical pack or kit comprising one or more containers filled with one or more of the ingredients of the Therapeutics of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the Therapeutics may be employed in conjunction with other therapeutic compounds.

The Therapeutics of the invention may be administered alone or in combination with adjuvants. Adjuvants that may be administered with the Therapeutics of the invention include, but are not limited to, alum, alum plus deoxycholate (ImmunoAg), MTP-PE (Biocine Corp.), QS21 (GENENTECH™, Inc.), BCG (e.g., THERACYS®), MPL and nonviable preparations of *Corynebacterium parvum*. In a specific embodiment, Therapeutics of the invention are administered in combination with alum. In another specific embodiment, Therapeutics of the invention are administered in combination with QS-21. Further adjuvants that may be administered with the Therapeutics of the invention include, but are not limited to, Monophosphoryl lipid immunomodulator, AdjuVax 100a, QS-21, QS-18, CRL1005, Aluminum salts, MF-59, and Virosomal adjuvant technology. Vaccines that may be administered with the Therapeutics of the invention include, but are not limited to, vaccines directed toward protection against MMR (measles, mumps, rubella), polio, varicella, tetanus/diphtheria, hepatitis A, hepatitis B, *haemophilus influenzae* B, whooping cough, pneumonia, influenza, Lyme's Disease, rotavirus, cholera, yellow fever, Japanese encephalitis, poliomyelitis, rabies, typhoid fever, and pertussis. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

The Therapeutics of the invention may be administered alone or in combination with other therapeutic agents. Therapeutic agents that may be administered in combination with the Therapeutics of the invention, include but are not limited to, chemotherapeutic agents, antibiotics, steroidal and non-steroidal anti-inflammatories, conventional immunotherapeutic agents, cytokines, growth factors, and/or therapeutic treatments described below. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

In one embodiment, the Therapeutics of the invention are administered in combination with an anticoagulant. Anticoagulants that may be administered with the compositions of the invention include, but are not limited to, heparin, low molecular weight heparin, warfarin sodium (e.g., COUMADIN®), dicumarol, 4-hydroxycoumarin, anisindione (e.g., MIRADON™), acenocoumarol (e.g., nicoumalone, SINTHROME™), indan-1,3-dione, phenprocoumon (e.g., MARCUMAR™), ethyl biscoumacetate (e.g., TROMEXAN™), and aspirin. In a specific embodiment, compositions of the invention are administered in combination with heparin and/or warfarin. In another specific embodiment, compositions of the invention are administered in combination with warfarin. In another specific embodiment, compositions of the invention are administered in combination with warfarin and aspirin. In another specific embodiment, compositions of the invention are administered in combination with heparin. In another specific embodiment, compositions of the invention are administered in combination with heparin and aspirin.

In another embodiment, the Therapeutics of the invention are administered in combination with thrombolytic drugs. Thrombolytic drugs that may be administered with the compositions of the invention include, but are not limited to, plasminogen, lys-plasminogen, alpha2-antiplasmin, streptokinae (e.g., KABIKINASE™), antiresplace (e.g., EMINASE™), tissue plasminogen activator (t-PA, altevase, ACTIVASE™), urokinase (e.g., ABBOKINASE™), sauruplase, (Prourokinase, single chain urokinase), and aminocaproic acid (e.g., AMICAR™). In a specific embodiment, compositions of the invention are administered in combination with tissue plasminogen activator and aspirin.

In another embodiment, the Therapeutics of the invention are administered in combination with antiplatelet drugs. Antiplatelet drugs that may be administered with the compositions of the invention include, but are not limited to, aspirin, dipyridamole (e.g., PERSANTINE™), and ticlopidine (e.g., TICLID™).

In specific embodiments, the use of anti-coagulants, thrombolytic and/or antiplatelet drugs in combination with Therapeutics of the invention is contemplated for the detection, prevention, diagnosis, prognostication, treatment, and/or amelioration of thrombosis, arterial thrombosis, venous thrombosis, thromboembolism, pulmonary embolism, atherosclerosis, myocardial infarction, transient ischemic attack, unstable angina. In specific embodiments, the use of anticoagulants, thrombolytic drugs and/or antiplatelet drugs in combination with Therapeutics of the invention is contemplated for the prevention of occlusion of saphenous grafts, for reducing the risk of periprocedural thrombosis as might accompany angioplasty procedures, for reducing the risk of stroke in patients with atrial fibrillation including nonrheumatic atrial fibrillation, for reducing the risk of embolism associated with mechanical heart valves and or mitral valves disease. Other uses for the therapeutics of the invention, alone or in combination with antiplatelet, anticoagulant, and/or thrombolytic drugs, include, but are not limited to, the prevention of occlusions in extracorporeal devices (e.g., intravascular cannulas, vascular access shunts in hemodialysis patients, hemodialysis machines, and cardiopulmonary bypass machines).

Therapeutics of the invention may also be administered in combination with additional cardiovascular agents, such as, for example, beta-adrenergic blockers, calcium channel blockers, ACE inhibitors, angiotensin II blockers, alpha adrenergic blockers, hypotensive agents, antilipemic agents, and vasodilating agents.

Non-limiting examples of beta-adrenergic blockers includes TENORMIN™ (atenolol), BREVIBLOC™ (esmolol), NORMODYNE™ (labetalol), TRANDATE™, LOPRESSOR™ (metoprolol), INDERAL™ (propranolol), and BETApp96™ (sotalol). Calcium channel blockers includes, for example, NORVASC™ (amlodipine), CARDIZEM™ (diltiazem), PLENDIL™ (felodipine), DYNACRIC™ (isradipine), CARDENE™ (nicardipine), ADALAT™ (nifedipine), and CALAN™ (verapamil). ACE inhibitors includes, for example, LOTENSIN™ (benazepril), CAPOTEN™ (captopril), VASOTEC™ (enalapril), MONOPRIL™ (fosinopril), PRINIVIL™ (lisinopril), ACCUPRIL™ (quinapril), and ALTACE™ (ramipril). Non-limiting examples of angiotensin II blockers includes AVAPRO™ (irbesartan), COZAAR™ (losartan), and DIOVAN™ (valsartan). Alpha adrenergic blockers include, for example, CARDURA™ (doxazosin), MINIPRESS™ (prazosin), FLOMAX™ (tamsulosin), and terazosin. Hypotensive agents include, for example, CATAPRES™ (clonidine), APRESOLINE™ (hydralazine), ALDOMET™ (methyldopa), LONITEN™ (minoxidil), NIPRIDE™ (nitroprusside) and reserpine. Antilipemic agents include, for example, LIPITOR™ (atorvastatin), QUESTRAN™ (cholestyramine), LOLESTID™ (colestipol), TRICOR™ (fenofibrate), LOPID™ (gemfibrate), MEVACOR™ (lovstatin), PRAVACHOL™ (pravastatin), and ZOCOR™ (simvastatin). Non-limiting examples of vasodilating agents include alprostadil, amyl nitrite, PERSANTIN™ (dipyridamole), FLONAN™ (epoprostenol), ISORDIL™ (isosorbide dinitrate), IMDUR™ (isosorbide mononitrate), NIMOTOP™ (nimodipine), INOmax™ (nitric oxide gas), nitroglycerin, papaverine, and PRISCOLINE™ (tolazoline).

In certain embodiments, therapeutics of the invention are administered in combination with antiretroviral agents, nucleoside/nucleotide reverse transcriptase inhibitors (NRTIs), non-nucleoside reverse transcriptase inhibitors (NNRTIs), and/or protease inhibitors (PIs). NRTIs that may be administered in combination with the Therapeutics of the invention, include, but are not limited to, RETROVIR™ (zidovudine/AZT), VIDEX™ (didanosine/ddI), HIVID™ (zalcitabine/ddC), ZERIT™ (stavudine/d4T), EPIVIR™ (lamivudine/3TC), and COMBIVIR™ (zidovudine/lamivudine). NNRTIs that may be administered in combination with the Therapeutics of the invention, include, but are not limited to, VIRAMUNE™ (nevirapine), RESCRIPTOR™ (delavirdine), and SUSTIVA™ (efavirenz). Protease inhibitors that may be administered in combination with the Therapeutics of the invention, include, but are not limited to, CRIXIVAN™ (indinavir), NORVIR™ (ritonavir), INVIRASE™ (saquinavir), and VIRACEPT™ (nelfinavir). In a specific embodiment, antiretroviral agents, nucleoside reverse transcriptase inhibitors, non-nucleoside reverse transcriptase inhibitors, and/or protease inhibitors may be used in any combination with Therapeutics of the invention to treat AIDS and/or to prevent or treat HIV infection.

Additional NRTIs include LODENOSINE™ (F-ddA; an acid-stable adenosine NRTI; Triangle/ABBOTT™; COVIRACIL™ (emtricitabine/FTC; structurally related to lamivudine (3TC) but with 3- to 10-fold greater activity in vitro; Triangle/ABBOTT™); dOTC (BCH-10652, also structurally related to lamivudine but retains activity against a substantial proportion of lamivudine-resistant isolates; Biochem Pharma); Adefovir (refused approval for anti-HIV therapy by FDA; Gilead Sciences); PREVEON® (Adefovir Dipivoxil, the active prodrug of adefovir; its active form is PMEA-pp); TENOFOVIR™ (bis-POC PMPA, a PMPA prodrug; Gilead); DAPD/DXG (active metabolite of DAPD; Triangle/ABBOTT™); D-D4FC (related to 3TC, with activity against AZT/3TC-resistant virus); GW420867X (Glaxo Wellcome); ZIAGEN™ (abacavir/159U89; Glaxo Wellcome Inc.); CS-87 (3' azido-2',3'-dideoxyuridine; WO 99/66936); and S-acyl-2-thioethyl (SATE)-bearing prodrug forms of 13-L-FD4C and 13-L-FddC (WO 98/17281).

Additional NNRTIs include COACTINON™ (Emivirine/MKC-442, potent NNRTI of the HEPT class; Triangle/ABBOTT™); CAPRAVIRINE™ (AG-1549/S-1153, a next generation NNRTI with activity against viruses containing the K103N mutation; AGOURON™); PNU-142721 (has 20- to 50-fold greater activity than its predecessor delavirdine and is active against K103N mutants; PHARMACIA™ & Upjohn); DPC-961 and DPC-963 (second-generation derivatives of efavirenz, designed to be active against viruses with the K103N mutation; DUPONT™); GW-420867X (has 25-fold greater activity than HBY097 and is active against K103N mutants; Glaxo Wellcome); CALANOLIDE A (naturally occurring agent from the latex tree; active against viruses containing either or both the Y181C and K103N mutations); and Propolis (WO 99/49830).

Additional protease inhibitors include LOPINAVIR™ (ABT378/r; ABBOTT™ Laboratories); BMS-232632 (an azapeptide; BRISTOL-MYERS SQUIBB™); TIPRANAVIR™ (PNU-140690, a non-peptic dihydropyrone; PHARIVIACIA™ & Upjohn); PD-178390 (a nonpeptidic dihydropyrone; Parke-Davis); BMS 232632 (an azapeptide; BRISTOL-MYERS SQUIBB™); L-756,423 (an indinavir analog; Merck); DMP-450 (a cyclic urea compound; Avid & DUPONT™); AG-1776 (a peptidomimetic with in vitro activity against protease inhibitor-resistant viruses; AGOURON™); VX-175/GW-433908 (phosphate prodrug of amprenavir; Vertex & Glaxo Wellcome); CGP61755 (Ciba); and AGENERASE™ (amprenavir; Glaxo Wellcome Inc.).

Additional antiretroviral agents include fusion inhibitors/gp41 binders. Fusion inhibitors/gp41 binders include T-20 (a peptide from residues 643-678 of the HIV gp41 transmembrane protein ectodomain which binds to gp41 in its resting state and prevents transformation to the fusogenic state; Trimeris) and T-1249 (a second-generation fusion inhibitor; Trimeris).

Additional antiretroviral agents include fusion inhibitors/chemokine receptor antagonists. Fusion inhibitors/chemokine receptor antagonists include CXCR4 antagonists such as AMD 3100 (a bicyclam), SDF-1 and its analogs, and ALX40-4C (a cationic peptide), T22 (an 18 amino acid peptide; Trimeris) and the T22 analogs T134 and T140; CCR5 antagonists such as RANTES (9-68), AOP-RANTES, NNY-RANTES, and TAK-779; and CCR5/CXCR4 antagonists such as NSC 651016 (a distamycin analog). Also included are CCR2B, CCR3, and CCR6 antagonists. Chemokine receptor agonists such as RANTES, SDF-1, MIP-1α, MIP-1β, etc., may also inhibit fusion.

Additional antiretroviral agents include integrase inhibitors. Integrase inhibitors include dicaffeoylquinic (DFQA) acids; L-chicoric acid (a dicaffeoyltartaric (DCTA) acid); quinalizarin (QLC) and related anthraquinones; ZINTEVIR™ (AR 177, an oligonucleotide that probably acts at cell surface rather than being a true integrase inhibitor; Arondex); and naphthols such as those disclosed in WO 98/50347.

Additional antiretroviral agents include hydroxyurea-like compounds such as BCX-34 (a purine nucleoside phosphorylase inhibitor; Biocryst); ribonucleotide reductase inhibitors such as DIDOX™ (Molecules for Health); inosine monophosphate dehydrogenase (IMPDH) inhibitors such as VX-497 (Vertex); and mycopholic acids such as CellCept (mycophenolate mofetil; ROCHE™).

Additional antiretroviral agents include inhibitors of viral integrase, inhibitors of viral genome nuclear translocation such as arylene bis(methylketone) compounds; inhibitors of HIV entry such as AOP-RANTES, NNY-RANTES, RANTES-IgG fusion protein, soluble complexes of RANTES and glycosaminoglycans (GAG), and AMD-3100; nucleocapsid zinc finger inhibitors such as dithiane compounds; targets of HIV Tat and Rev; and pharmacoenhancers such as ABT-378.

Other antiretroviral therapies and adjunct therapies include cytokines and lymphokines such as MIP-1α, MIP-1β, SDF-1α, IL-2, PROLEUKIN™ (aldesleukin/L2-7001; CHIRON™), IL-4, IL-10, IL-12, and IL-13; interferons such as IFN-α2a; antagonists of TNFs, NFκB, GM-CSF, M-CSF, and IL-10; agents that modulate immune activation such as cyclosporin and prednisone; vaccines such as Remune™ (HIV Immunogen), APL 400-003 (Apollon), recombinant gp120 and fragments, bivalent (B/E) recombinant envelope glycoprotein, rgp120CM235, MN rgp120, SF-2 rgp120, gp120/soluble CD4 complex, Delta JR-FL protein, branched synthetic peptide derived from discontinuous gp120 C3/C4 domain, fusion-competent immunogens, and Gag, Pol, Nef, and Tat vaccines; gene-based therapies such as genetic suppressor elements (GSEs; WO 98/54366), and intrakines (genetically modified CC chemokines targeted to the ER to block surface expression of newly synthesized CCR5 (Yang et al., *PNAS* 94:11567-72 (1997); Chen et al., *Nat. Med.* 3:1110-16 (1997)); antibodies such as the anti-CXCR4 antibody 12G5, the anti-CCR5 antibodies 2D7, 5C7, PA8, PA9, PA10, PA11, PA12, and PA14, the anti-CD4 antibodies Q4120 and RPA-T4, the anti-CCR3 antibody 7B11, the anti-gp120 antibodies 17b, 48d, 447-52D, 257-D, 268-D and 50.1, anti-Tat antibodies, anti-TNF-α antibodies, and monoclonal antibody 33A; aryl hydrocarbon (AH) receptor agonists and antagonists such as TCDD, 3,3',4,4',5-pentachlorobiphenyl, 3,3',4,4'-tetrachlorobiphenyl, and α-naphthoflavone (WO 98/30213); and antioxidants such as γ-L-glutamyl-L-cysteine ethyl ester (γ-GCE; WO 99/56764).

In a further embodiment, the Therapeutics of the invention are administered in combination with an antiviral agent. Antiviral agents that may be administered with the Therapeutics of the invention include, but are not limited to, acyclovir, ribavirin, amantadine, and remantidine.

In other embodiments, Therapeutics of the invention may be administered in combination with anti-opportunistic infection agents. Anti-opportunistic agents that may be administered in combination with the Therapeutics of the invention, include, but are not limited to, TRIMETHOPRIM-SULFAMETHOXAZOLE™, DAPSONE™, PENTAMIDINE™, ATOVAQUONE™, ISONIAZID™, RIFAMPIN™, PYRAZINAMIDE™, ETHAMBUTOL™, RIFABUTIN™, CLARITHROMYCIN™, AZITHROMYCIN™, GANCICLOVIR™, FOSCARNET™, CIDOFOVIR™, FLUCONAZOLE™, ITRACONAZOLE™, KETOCONAZOLE™, ACYCLOVIR™, FAMCICOLVIR™, PYRIMETHAMINE™, LEUCOVORIN™, NEUPOGEN™ (filgrastim/G-CSF), and LEUKINE™ (sargramostim/GM-CSF). In a specific embodiment, Therapeutics of the invention are used in any combination with TRIMETHOPRIM-SULFAMETHOXAZOLE™, DAPSONE™, PENTAMIDINE™, and/or ATOVAQUONE™ to prophylactically treat or prevent an opportunistic *Pneumocystis carinii* pneumonia infection. In another specific embodiment, Therapeutics of the invention are used in any combination with ISONIAZID™, RIFAMPIN™, PYRAZINAMIDE™, and/or ETHAMBUTOL™ to prophylactically treat or prevent an opportunistic *Mycobacterium avium* complex infection. In another specific embodiment, Therapeutics of the invention are used in any combination with RIFABUTIN™, CLARITHROMYCIN™, and/or AZITHROMYCIN™ to prophylactically treat or prevent an opportunistic *Mycobacterium tuberculosis* infection. In another specific embodiment, Therapeutics of the invention are used in any combination with GANCICLOVIR™, FOSCARNET™, and/or CIDOFOVIR™ to prophylactically treat or prevent an opportunistic cytomegalovirus infection. In another specific embodiment, Therapeutics of the invention are used in any combination with FLUCONAZOLE™, ITRACONAZOLE™, and/or KETOCONAZOLE™ to prophylactically treat or prevent an opportunistic fungal infection. In another specific embodiment, Therapeutics of the invention are used in any combination with ACYCLOVIR™ and/or FAMCICOLVIR™ to prophylactically treat or prevent an opportunistic herpes simplex virus type I and/or type II infection. In another specific embodiment, Therapeutics of the invention are used in any combination with PYRIMETHAMINE™ and/or LEUCOVORIN™ to prophylactically treat or prevent an opportunistic *Toxoplasma gondii* infection. In another specific embodiment, Therapeutics of the invention are used in any combination with LEUCOVORIN™ and/or NEUPOGEN™ to prophylactically treat or prevent an opportunistic bacterial infection.

In a further embodiment, the Therapeutics of the invention are administered in combination with an antibiotic agent. Antibiotic agents that may be administered with the Therapeutics of the invention include, but are not limited to, amoxicillin, beta-lactamases, aminoglycosides, beta-lactam (glycopeptide), beta-lactamases, Clindamycin, chloramphenicol, cephalosporins, ciprofloxacin, erythromycin, fluoroquinolones, macrolides, metronidazole, penicillins, quinolones, rapamycin, rifampin, streptomycin, sulfonamide, tetracyclines, trimethoprim, trimethoprim-sulfamethoxazole, and vancomycin.

In other embodiments, the Therapeutics of the invention are administered in combination with immunostimulants. Immunostimulants that may be administered in combination with the Therapeutics of the invention include, but are not limited to, levamisole (e.g., ERGAMISOL™), isoprinosine (e.g. INOSIPLEX™), interferons (e.g. interferon alpha), and interleukins (e.g., IL-2).

In other embodiments, Therapeutics of the invention are administered in combination with immunosuppressive agents. Immunosuppressive agents that may be administered in combination with the Therapeutics of the invention include, but are not limited to, steroids, cyclosporine, cyclosporine analogs, cyclophosphamide methylprednisone, prednisone, azathioprine, FK-506, 15-deoxyspergualin, and other immunosuppressive agents that act by suppressing the function of responding T cells. Other immunosuppressive agents that may be administered in combination with the Therapeutics of the invention include, but are not limited to, prednisolone, methotrexate, thalidomide, methoxsalen, rapamycin, leflunomide, mizoribine (BREDININ™), brequinar, deoxyspergualin, and azaspirane (SKF 105685), ORTHOCLONE OKT® 3 (muromonab-CD3), SANDIMMUNE™, NEORAL™, SANGDYA™ (cyclosporine), PROGRAF® (FK506, tacrolimus), CELLCEPT® (mycophenolate motefil, of which the active metabolite is mycophenolic acid), IMURAN™ (azathioprine), glucocorticosteroids, adrenocortical steroids such as DELTASONE™ (prednisone) and HYDELTRASOL™ (prednisolone), FOLEX™ and MEXATE™ (methotrxate), OXSORALEN-ULTRA™ (methoxsalen) and RAPAMUNE™ (sirolimus). In a specific embodiment, immunosuppressants may be used to prevent rejection of organ or bone marrow transplantation.

In an additional embodiment, Therapeutics of the invention are administered alone or in combination with one or more intravenous immune globulin preparations. Intravenous immune globulin preparations that may be administered with the Therapeutics of the invention include, but not limited to, GAMMAR™, IVEEGAM™, SANDOGLOBULIN™, GAMMAGARD S/D™, ATGAM™ (antithymocyte glubulin), and GAMIMUNE™. In a specific embodiment, Therapeutics of the invention are administered in combination with intravenous immune globulin preparations in transplantation therapy (e.g., bone marrow transplant).

In certain embodiments, the Therapeutics of the invention are administered alone or in combination with an anti-inflammatory agent. Anti-inflammatory agents that may be administered with the Therapeutics of the invention include, but are not limited to, corticosteroids (e.g. betamethasone, budesonide, cortisone, dexamethasone, hydrocortisone, methylprednisolone, prednisolone, prednisone, and triamcinolone), nonsteroidal anti-inflammatory drugs (e.g., diclofenac, diflunisal, etodolac, fenoprofen, floctafenine, flurbiprofen, ibuprofen, indomethacin, ketoprofen, meclofenamate, mefenamic acid, meloxicam, nabumetone, naproxen, oxaprozin, phenylbutazone, piroxicam, sulindac, tenoxicam, tiaprofenic acid, and tolmetin.), as well as antihistamines, aminoarylcarboxylic acid derivatives, arylacetic acid derivatives, arylbutyric acid derivatives, arylcarboxylic acids, arylpropionic acid derivatives, pyrazoles, pyrazolones, salicylic acid derivatives, thiazinecarboxamides, e-acetamidocaproic acid, S-adenosylmethionine, 3-amino-4-hydroxybutyric acid, amixetrine, bendazac, benzydamine, bucolome, difenpiramide, ditazol, emorfazone, guaiazulene, nabumetone, nimesulide, orgotein, oxaceprol, paranyline, perisoxal, pifoxime, proquazone, proxazole, and tenidap.

In an additional embodiment, the compositions of the invention are administered alone or in combination with an anti-angiogenic agent. Anti-angiogenic agents that may be administered with the compositions of the invention include, but are not limited to, Angiostatin (ENTREMED™, Rockville, Md.), Troponin-1 (Boston Life Sciences, Boston, Mass.), anti-Invasive Factor, retinoic acid and derivatives thereof, paclitaxel (TAXOL™), Suramin, Tissue Inhibitor of Metalloproteinase-1, Tissue Inhibitor of Metalloproteinase-2, VEGI, Plasminogen Activator Inhibitor-1, Plasminogen Activator Inhibitor-2, and various forms of the lighter "d group" transition metals.

Lighter "d group" transition metals include, for example, vanadium, molybdenum, tungsten, titanium, niobium, and tantalum species. Such transition metal species may form transition metal complexes. Suitable complexes of the above-mentioned transition metal species include oxo transition metal complexes.

Representative examples of vanadium complexes include oxo vanadium complexes such as vanadate and vanadyl complexes. Suitable vanadate complexes include metavanadate and orthovanadate complexes such as, for example, ammonium metavanadate, sodium metavanadate, and sodium orthovanadate. Suitable vanadyl complexes include, for example, vanadyl acetylacetonate and vanadyl sulfate including vanadyl sulfate hydrates such as vanadyl sulfate mono- and trihydrates.

Representative examples of tungsten and molybdenum complexes also include oxo complexes. Suitable oxo tungsten complexes include tungstate and tungsten oxide complexes. Suitable tungstate complexes include ammonium tungstate, calcium tungstate, sodium tungstate dihydrate, and tungstic acid. Suitable tungsten oxides include tungsten (IV) oxide and tungsten (VI) oxide. Suitable oxo molybdenum complexes include molybdate, molybdenum oxide, and molybdenyl complexes. Suitable molybdate complexes include ammonium molybdate and its hydrates, sodium molybdate and its hydrates, and potassium molybdate and its hydrates. Suitable molybdenum oxides include molybdenum (VI) oxide, molybdenum (VI) oxide, and molybdic acid. Suitable molybdenyl complexes include, for example, molybdenyl acetylacetonate. Other suitable tungsten and molybdenum complexes include hydroxo derivatives derived from, for example, glycerol, tartaric acid, and sugars.

A wide variety of other anti-angiogenic factors may also be utilized within the context of the present invention. Representative examples include, but are not limited to, platelet factor 4; protamine sulphate; sulphated chitin derivatives (prepared from queen crab shells), (Murata et al., Cancer Res. 51:22-26, (1991)); Sulphated Polysaccharide Peptidoglycan Complex (SP-PG) (the function of this compound may be enhanced by the presence of steroids such as estrogen, and tamoxifen citrate); Staurosporine; modulators of matrix metabolism, including for example, proline analogs, cishydroxyproline, d,L-3,4-dehydroproline, Thiaproline, alpha,alpha-dipyridyl, aminopropionitrile fumarate; 4-propyl-5-(4-pyridinyl)-2(3H)-oxazolone; Methotrexate; Mitoxantrone; Heparin; Interferons; 2 Macroglobulin-serum; ChIMP-3 (Pavloff et al., J. Bio. Chem. 267:17321-17326, (1992)); Chymostatin (Tomkinson et al., Biochem J. 286:475-480, (1992)); Cyclodextrin Tetradecasulfate; Eponemycin; Camptothecin; Fumagillin (Ingber et al., Nature 348:555-557, (1990)); Gold Sodium Thiomalate ("GST"; Matsubara and Ziff, J. Clin. Invest. 79:1440-1446, (1987)); anticollagenase-serum; alpha2-antiplasmin (Holmes et al., J. Biol. Chem. 262 (4): 1659-1664, (1987)); Bisantrene (National Cancer Institute); Lobenzarit disodium (N-(2)-carboxyphenyl-4-chloroanthronilic acid disodium or "CCA"; (Takeuchi et al., Agents Actions 36:312-316, (1992)); and metalloproteinase inhibitors such as BB94.

Additional anti-angiogenic factors that may also be utilized within the context of the present invention include Thalidomide, (CELGENE™, Warren, N.J.); Angiostatic steroid; AGM-1470 (H. Brem and J. Folkman *J Pediatr. Surg.* 28:445-51 (1993)); an integrin alpha v beta 3 antagonist (C. Storgard et al., *J Clin. Invest.* 103:47-54 (1999)); carboxynaminolmidazole; Carboxyamidotriazole (CAI) (National Cancer Institute, Bethesda, Md.); Conbretastatin A-4 (CA4P) (OXIGENE™, Boston, Mass.); Squalamine (Magainin Pharmaceuticals, Plymouth Meeting, Pa.); TNP-470, (TAP PHARMACEUTICALS™, Deerfield, Ill.); ZD-0101 ASTRAZENECA™ (London, UK); APRA (CT2584); Benefin, Byrostatin-1 (SC339555); CGP-41251 (PKC 412); CM101; Dexrazoxane (ICRF187); DMXAA; Endostatin; Flavopridiol; Genestein; GTE; ImmTher; Iressa (ZD1839); Octreotide (Somatostatin); Panretin; Penacillamine; Photopoint; PI-88; Prinomastat (AG-3340) Purlytin; Suradista (FCE26644); Tamoxifen (NOLVADEX™); Tazarotene; Tetrathiomolybdate; XELODA™ (Capecitabine); and 5-Fluorouracil.

Anti-angiogenic agents that may be administed in combination with the compounds of the invention may work through a variety of mechanisms including, but not limited to, inhibiting proteolysis of the extracellular matrix, blocking the function of endothelial cell-extracellular matrix adhesion molecules, by antagonizing the function of angiogenesis inducers such as growth factors, and inhibiting integrin receptors expressed on proliferating endothelial cells. Examples of anti-angiogenic inhibitors that interfere with extracellular matrix proteolysis and which may be administered in combination with the compositions of the invention include, but are not limited to, AG-3340 (AGOURON™, La Jolla, Calif.), BAY-12-9566 (BAYER™, West Haven, Conn.), BMS-275291 (BRISTOL-MYERS SQUIBB™, Princeton, N.J.), CGS-27032A (NOVARTIS™, East Hanover, N.J.), Marimastat (British Biotech, Oxford, UK), and METASTAT™ (AETERNA™, St-Foy, Quebec). Examples of anti-angiogenic inhibitors that act by blocking the function of endothelial cell-extracellular matrix adhesion molecules and which may be administered in combination with the compositions of the invention include, but are not limited to, EMD-121974 (MERCK™ KcgaA Darmstadt, Germany) and VITAXIN™ (IXSYS™, La Jolla, Calif./MEDIMMUNE™, Gaithersburg, Md.). Examples of anti-angiogenic agents that act by directly antagonizing or inhibiting angiogenesis inducers and which may be administered in combination with the compositions of the invention include, but are not limited to, Angiozyme (Ribozyme, Boulder, Colo.), Anti-VEGF antibody (GENENTECH™, S. San Francisco, Calif.), PTK-787/ZK-225846 (NOVARTIS™, Basel, Switzerland), SU-101 (SUGEN™, S. San Francisco, Calif.), SU-5416 (SUGEN™/PHARMACIA™ Upjohn, Bridgewater, N.J.), and SU-6668 (SUGEN™). Other anti-angiogenic agents act to indirectly inhibit angiogenesis. Examples of indirect inhibitors of angiogenesis which may be administered in combination with the compositions of the invention include, but are not limited to, IM-862 (CYTRAN™, Kirkland, Wash.), Interferon-alpha, IL-12 (ROCHE™, Nutley, N.J.), and Pentosan polysulfate (Georgetown University, Washington, D.C.).

In particular embodiments, the use of compositions of the invention in combination with anti-angiogenic agents is contemplated for the treatment, prevention, and/or amelioration of an autoimmune disease, such as for example, an autoimmune disease described herein.

In a particular embodiment, the use of compositions of the invention in combination with anti-angiogenic agents is contemplated for the treatment, prevention, and/or amelioration of arthritis. In a more particular embodiment, the use of compositions of the invention in combination with anti-angiogenic agents is contemplated for the treatment, prevention, and/or amelioration of rheumatoid arthritis.

In another embodiment, the polynucleotides encoding a polypeptide of the present invention are administered in combination with an angiogenic protein, or polynucleotides encoding an angiogenic protein. Examples of angiogenic proteins that may be administered with the compositions of the invention include, but are not limited to, acidic and basic fibroblast growth factors, VEGF-1, VEGF-2, VEGF-3, epidermal growth factor alpha and beta, platelet-derived endothelial cell growth factor, platelet-derived growth factor, tumor necrosis factor alpha, hepatocyte growth factor, insulin-like growth factor, colony stimulating factor, macrophage colony stimulating factor, granulocyte/macrophage colony stimulating factor, and nitric oxide synthase.

In additional embodiments, compositions of the invention are administered in combination with a chemotherapeutic agent. Chemotherapeutic agents that may be administered with the Therapeutics of the invention include, but are not limited to alkylating agents such as nitrogen mustards (for example, Mechlorethamine, cyclophosphamide, Cyclophosphamide Ifosfamide, Melphalan (L-sarcolysin), and Chlorambucil), ethylenimines and methylmelamines (for example, Hexamethylmelamine and Thiotepa), alkyl sulfonates (for example, Busulfan), nitrosoureas (for example, Carmustine (BCNU), Lomustine (CCNU), Semustine (methyl-CCNU), and Streptozocin (streptozotocin)), triazenes (for example, Dacarbazine (DTIC; dimethyltriazenoimidazolecarboxamide)), folic acid analogs (for example, Methotrexate (amethopterin)), pyrimidine analogs (for example, Fluorouacil (5-fluorouracil; 5-FU), Floxuridine (fluorodeoxyuridine; FudR), and Cytarabine (cytosine arabinoside)), purine analogs and related inhibitors (for example, Mercaptopurine (6-mercaptopurine; 6-MP), Thioguanine (6-thioguanine; TG), and Pentostatin (2'-deoxycoformycin)), vinca alkaloids (for example, Vinblastine (VLB, vinblastine sulfate)) and Vincristine (vincristine sulfate)), epipodophyllotoxins (for example, Etoposide and Teniposide), antibiotics (for example, Dactinomycin (actinomycin D), Daunorubicin (daunomycin; rubidomycin), Doxorubicin, Bleomycin, Plicamycin (mithramycin), and Mitomycin (mitomycin C), enzymes (for example, L-Asparaginase), biological response modifiers (for example, Interferon-alpha and interferon-alpha-2b), platinum coordination compounds (for example, Cisplatin (cis-DDP) and Carboplatin), anthracenedione (Mitoxantrone), substituted ureas (for example, Hydroxyurea), methylhydrazine derivatives (for example, Procarbazine (N-methylhydrazine; MIH), adrenocorticosteroids (for example, Prednisone), progestins (for example, Hydroxyprogesterone caproate, Medroxyprogesterone, Medroxyprogesterone acetate, and Megestrol acetate), estrogens (for example, Diethylstilbestrol (DES), Diethylstilbestrol diphosphate, Estradiol, and Ethinyl estradiol), antiestrogens (for example, Tamoxifen), androgens (Testosterone proprionate, and Fluoxymesterone), antiandrogens (for example, Flutamide), gonadotropin-releasing hormone analogs (for example, Leuprolide), other hormones and hormone analogs (for example, methyltestosterone, estramustine, estramustine phosphate sodium, chlorotrianisene, and testolactone), and others (for example, dicarbazine, glutamic acid, and mitotane).

In one embodiment, the compositions of the invention are administered in combination with one or more of the following drugs: infliximab (also known as Remicade™ Centocor, Inc.), Trocade (ROCHE™, RO-32-3555), Leflunomide (also known as Arava™ from HOECHST MARION ROUSSEL™), Kineret™ (an IL-1 Receptor antagonist also known as Anakinra from AMGEN™, Inc.)

In a specific embodiment, compositions of the invention are administered in combination with CHOP (cyclophosphamide, doxorubicin, vincristine, and prednisone) or combination of one or more of the components of CHOP. In one embodiment, the compositions of the invention are administered in combination with anti-CD20 antibodies, human monoclonal anti-CD20 antibodies. In another embodiment, the compositions of the invention are administered in combination with anti-CD20 antibodies and CHOP, or anti-CD20 antibodies and any combination of one or more of the components of CHOP, particularly cyclophosphamide and/or prednisone. In a specific embodiment, compositions of the invention are administered in combination with Rituximab. In a further embodiment, compositions of the invention are administered with Rituximab and CHOP, or Rituximab and any combination of one or more of the components of CHOP, particularly cyclophosphamide and/or prednisone. In a specific embodiment, compositions of the invention are administered in combination with tositumomab. In a further embodiment, compositions of the invention are administered with tositumomab and CHOP, or tositumomab and any combination of one or more of the components of CHOP, particularly cyclophosphamide and/or prednisone. The anti-CD20 antibodies may optionally be associated with radioisotopes, toxins or cytotoxic prodrugs.

In another specific embodiment, the compositions of the invention are administered in combination ZEVALIN™. In a further embodiment, compositions of the invention are administered with ZEVALIN™ and CHOP, or ZEVALIN™ and any combination of one or more of the components of CHOP, particularly cyclophosphamide and/or prednisone. ZEVALIN™ may be associated with one or more radioisotopes. Particularly preferred isotopes are $^{90}$Y and $^{111}$In.

In an additional embodiment, the Therapeutics of the invention are administered in combination with cytokines. Cytokines that may be administered with the Therapeutics of the invention include, but are not limited to, IL2, IL3, IL4, IL5, IL6, IL7, IL10, IL12, IL13, IL15, anti-CD40, CD40L, IFN-gamma and TNF-alpha. In another embodiment, Therapeutics of the invention may be administered with any interleukin, including, but not limited to, IL-1alpha, IL-1beta, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, and IL-21.

In one embodiment, the Therapeutics of the invention are administered in combination with members of the TNF family. TNF, TNF-related or TNF-like molecules that may be administered with the Therapeutics of the invention include, but are not limited to, soluble forms of TNF-alpha, lymphotoxin-alpha (LT-alpha, also known as TNF-beta), LT-beta (found in complex heterotrimer LT-alpha2-beta), OPGL, FasL, CD27L, CD30L, CD40L, 4-1BBL, DcR3, OX40L, TNF-gamma (International Publication No. WO 96/14328), AIM-I (International Publication No. WO 97/33899), endokine-alpha (International Publication No. WO 98/07880), TR6 (International Publication No. WO 98/30694), OPG, and neutrokine-alpha (International Publication No. WO 98/18921, OX40, and nerve growth factor (NGF), and soluble forms of Fas, CD30, CD27, CD40 and 4-IBB, TR2 (International Publication No. WO 96/34095), DR3 (International Publication No. WO 97/33904), DR4 (International Publication No. WO 98/32856), TR5 (International Publication No. WO 98/30693), TRANK, TR9 (International Publication No. WO 98/56892), TR10 (International Publication No. WO 98/54202), 312C2 (International Publication No. WO 98/06842), and TR12, and soluble forms CD154, CD70, and CD153.

In an additional embodiment, the Therapeutics of the invention are administered in combination with angiogenic proteins. Angiogenic proteins that may be administered with the Therapeutics of the invention include, but are not limited to, Glioma Derived Growth Factor (GDGF), as disclosed in European Patent Number EP-399816; Platelet Derived Growth Factor-A (PDGF-A), as disclosed in European Patent Number EP-682110; Platelet Derived Growth Factor-B (PDGF-B), as disclosed in European Patent Number EP-282317; Placental Growth Factor (PlGF), as disclosed in International Publication Number WO 92/06194; Placental Growth Factor-2 (PlGF-2), as disclosed in Hauser et al., Growth Factors, 4:259-268 (1993); Vascular Endothelial Growth Factor (VEGF), as disclosed in International Publication Number WO 90/13649; Vascular Endothelial Growth Factor-A (VEGF-A), as disclosed in European Patent Number EP-506477; Vascular Endothelial Growth Factor-2 (VEGF-2), as disclosed in International Publication Number WO 96/39515; Vascular Endothelial Growth Factor B (VEGF-3); Vascular Endothelial Growth Factor B-186 (VEGF-B186), as disclosed in International Publication Number WO 96/26736; Vascular Endothelial Growth Factor-D (VEGF-D), as disclosed in International Publication Number WO 98/02543; Vascular Endothelial Growth Factor-D (VEGF-D), as disclosed in International Publication Number WO 98/07832; and Vascular Endothelial Growth Factor-E (VEGF-E), as disclosed in German Patent Number DE19639601. The above mentioned references are herein incorporated by reference in their entireties.

In an additional embodiment, the Therapeutics of the invention are administered in combination with Fibroblast Growth Factors. Fibroblast Growth Factors that may be administered with the Therapeutics of the invention include, but are not limited to, FGF-1, FGF-2, FGF-3, FGF-4, FGF-5, FGF-6, FGF-7, FGF-8, FGF-9, FGF-10, FGF-11, FGF-12, FGF-13, FGF-14, and FGF-15.

In an additional embodiment, the Therapeutics of the invention are administered in combination with hematopoietic growth factors. Hematopoietic growth factors that may be administered with the Therapeutics of the invention include, but are not limited to, granulocyte macrophage colony stimulating factor (GM-CSF) (sargramostim, LEUKINE™, PROKINE™), granulocyte colony stimulating factor (G-CSF) (filgrastim, NEUPOGEN™), macrophage colony stimulating factor (M-CSF, CSF-1) erythropoietin (epoetin alfa, EPOGEN™, PROCRIT™), stem cell factor (SCF, c-kit ligand, steel factor), megakaryocyte colony stimulating factor, PIXY321 (a GMCSF/IL-3 fusion protein), interleukins, especially any one or more of IL-1 through IL-12, interferon-gamma, or thrombopoietin.

In certain embodiments, Therapeutics of the present invention are administered in combination with adrenergic blockers, such as, for example, acebutolol, atenolol, betaxolol, bisoprolol, carteolol, osmolol, labetalol, metoprolol, nadolol, oxprenolol, penbutolol, pindolol, propranolol, sotalol, and timolol.

In another embodiment, the Therapeutics of the invention are administered in combination with an antiarrhythmic drug (e.g., adenosine, amiodarone, bretylium, digitalis, digoxin, digitoxin, diliazem, diisopyramide, esmolol, flecaimide, lidocaine, mexiletine, moricizine, phenyloin, procainamide, N-acetyl procainamide, propafenone, propranolol, quinidine, sotalol, tocamide, and verapamil).

In another embodiment, the Therapeutics of the invention are administered in combination with diuretic agents, such as carbonic anhydrase-inhibiting agents (e.g., acetazolamide, dichlorphenamide, and methazolamide), osmotic diuretics (e.g., glycerin, isosorbide, mannitol, and urea), diuretics that inhibit $Na^+$—$K^+$-$2Cl^-$ symport (e.g., furosemide, bumetamide, azosemide, piretanide, tripamide, ethacrynic acid, muzolimine, and torsemide), thiazide and thiazide-like diuretics (e.g., bendroflumethiazide, benzthiazide, chlorothiazide, hydrochlorothiazide, hydroflumethiazide, methylclothiazide, polythiazide, trichormethiazide, chlorthalidone, indapamide, metolazone, and quinethazone), potassium sparing diuretics (e.g., amiloride and triamterene), and mineralcorticoid receptor antagonists (e.g., spironolactone, canrenone, and potassium canrenoate).

In one embodiment, the Therapeutics of the invention are administered in combination with treatments for endocrine and/or hormone imbalance disorders. Treatments for endocrine and/or hormone imbalance disorders include, but are not limited to, $^{127}I$, radioactive isotopes of iodine such as $^{131}I$ and $^{123}I$; recombinant growth hormone, such as HUMATROPE™ (recombinant somatropin); growth hormone analogs such as PROTROPIN™ (somatrem); dopamine agonists such as PARLODEL™ (bromocriptine); somatostatin analogs such as SANDOSTATIN™ (octreotide); gonadotropin preparations such as PREGNYL™, A.P.L.™ and PROFASI™ (chorionic gonadotropin (CG)), PERGONAL™ (menotropins), and METRODIN™ (urofollitropin (uFSH)); synthetic human gonadotropin releasing hormone preparations such as FACTREL™ and LUTREPULSE™ (gonadorelin hydrochloride); synthetic gonadotropin agonists such as LUPRON™ (leuprolide acetate), SUPPRELIN™ (histrelin acetate), SYNAREL™ (nafarelin acetate), and ZOLADEX™ (goserelin acetate); synthetic preparations of thyrotropin-releasing hormone such as RELEFACT TRH™ and THYPINONE™ (protirelin); recombinant human TSH such as THYROGEN™; synthetic preparations of the sodium salts of the natural isomers of thyroid hormones such as L-$T_4$™, SYNTHROID™ and LEVOTHROID™ (levothyroxine sodium), L-$T_3$™, CYTOMEL™ and TRIOSTAT™ (liothyroine sodium), and THYROLAR™ (liotrix); antithyroid compounds such as 6-n-propylthiouracil (propylthiouracil), 1-methyl-2-mercaptoimidazole and TAPAZOLE™ (methimazole), NEO-MERCAZOLE™ (carbimazole); beta-adrenergic receptor antagonists such as propranolol and esmolol; $Ca^{2+}$ channel blockers; dexamethasone and iodinated radiological contrast agents such as TELEPAQUE™ (iopanoic acid) and ORAGRAFIN™ (sodium ipodate).

Additional treatments for endocrine and/or hormone imbalance disorders include, but are not limited to, estrogens or conjugated estrogens such as ESTRACE™ (estradiol), ESTINYL™ (ethinyl estradiol), PREMARIN™, ESTRATAB™, ORTHO-EST™, OGEN™ and estropipate (estrone), ESTROVIS™ (quinestrol), ESTRADERM™ (estradiol), DELESTROGEN™ and VALERGEN™ (estradiol valerate), DEPO-ESTRADIOL CYPIONATE™ and ESTROJECT LA™ (estradiol cypionate); antiestrogens such as NOLVADEX™ (tamoxifen), SEROPHENE™ and CLOMID™ (clomiphene); progestins such as DURALUTIN™ (hydroxyprogesterone caproate), MPA™ and DEPO-PROVERA™ (medroxyprogesterone acetate), PROVERA™ and CYCRIN™ (MPA), MEGACE™ (megestrol acetate), NORLUTIN™ (norethindrone), and NORLUTATE™ and AYGESTIN™ (norethindrone acetate); progesterone implants such as NORPLANT SYSTEM™ (subdermal implants of norgestrel); antiprogestins such as RU 486™ (mifepristone); hormonal contraceptives such as ENOVID™ (norethynodrel plus mestranol), PROGESTASERT™ (intrauterine device that releases progesterone), LOESTRIN™, BREVICON™, MODICON™, GENORA™, NELONA™, NORINYL™, OVACON-35™ and OVACON-50™ (ethinyl estradiol/norethindrone), LEVLEN™, NORDETTE™, TRI-LEVLEN™ and TRIPHASIL-21™ (ethinyl estradiol/levonorgestrel) LO/OVRAL™ and OVRAL™ (ethinyl estradiol/norgestrel), DEMULEN™ (ethinyl estradiol/ethynodiol diacetate), NORINYL™, ORTHO-NOVUM™, NORETHIN™, GENORA™, and NELOVA™ (norethindrone/mestranol), DESOGEN™ and ORTHO-CEPT™ (ethinyl estradiol/desogestrel), ORTHO-CYCLEN™ and ORTHO-TRICYCLEN™ (ethinyl estradiol/norgestimate), MICRONOR™ and NOR-QD™ (norethindrone), and OVRETTE™ (norgestrel).

Additional treatments for endocrine and/or hormone imbalance disorders include, but are not limited to, testosterone esters such as methenolone acetate and testosterone undecanoate; parenteral and oral androgens such as TESTOJECT-50™ (testosterone), TESTEX™ (testosterone propionate), DELATESTRYL™ (testosterone enanthate), DEPO-TESTOSTERONE™ (testosterone cypionate), DANOCRINE™ (danazol), HALOTESTIN™ (fluoxymesterone), ORETON METHYL™, TESTRED™ and VIRILON™ (methyltestosterone), and OXANDRIN™ (oxandrolone); testosterone transdermal systems such as TESTODERM™; androgen receptor antagonist and 5-alpha-reductase inhibitors such as ANDROCUR™ (cyproterone acetate), EULEXIN™ (flutamide), and PROSCAR™ (finasteride); adrenocorticotropic hormone preparations such as CORTROSYN™ (cosyntropin); adrenocortical steroids and their synthetic analogs such as ACLOVATE™ (alclometasone dipropionate), CYCLOCORT™ (amcinonide), BECLOVENT™ and VANCERIL™ (beclomethasone dipropionate), CELESTONE™ (betamethasone), BENISONE™ and UTICORT™ (betamethasone benzoate), DIPROSONE™ (betamethasone dipropionate), CELESTONE PHOSPHATE™ (betamethasone sodium phosphate), CELESTONE SOLUSPAN™ (betamethasone sodium phosphate and acetate), BETA-VAL™ and VALISONE™ (betamethasone valerate), TEMOVATE™ (clobetasol propionate), CLODERM™ (clocortolone pivalate), CORTEF™ and HYDROCORTONE™ (cortisol (hydrocortisone)), HYDROCORTONE ACETATE™ (cortisol (hydrocortisone) acetate), LOCOID™ (cortisol (hydrocortisone) butyrate), HYDROCORTONE PHOSPHATE™ (cortisol (hydrocortisone) sodium phosphate), A-HYDROCORT™ and SOLU CORTEF™ (cortisol (hydrocortisone) sodium succinate), WESTCORT™ (cortisol (hydrocortisone) valerate), CORTISONE ACETATE™ (cortisone acetate), DESOWEN™ and TRIDESILON™ (desonide), TOPICORT™ (desoximetasone), DECADRON™ (dexamethasone), DECADRON LA™ (dexamethasone acetate), DECADRON PHOSPHATE™ and HEXADROL PHOSPHATE™ (dexamethasone sodium phosphate), FLORONE™ and MAXIFLOR™ (diflorasone diacetate), FLORINEF ACETATE™ (fludrocortisone acetate), AEROBID™ and NASALIDE™ (flunisolide), FLUONID™ and SYNALAR™ (fluocinolone acetonide), LIDEX™ (fluocinonide), FLUOROP™ and FML™ (fluorometholone), CORDRAN™ (flurandrenolide), HALOG™ (halcinonide), HMS LIZUIFILM™ (medrysone), MEDROL™ (methylprednisolone), DEPO-MEDROL™ and MEDROL ACETATE™ (methylprednisone acetate), A-METHAPRED™ and SOLUMEDROL™ (methylprednisolone sodium succinate), ELOCON™ (mometasone furoate), HALDRONE™ (paramethasone acetate), DELTA-CORTEF™ (prednisolone), ECONOPRED™ (prednisolone acetate), HYDELTRASOL™ (prednisolone sodium phosphate), HYDELTRA-T.B.A™ (prednisolone tebutate), DELTASONE™ (prednisone), ARISTOCORT™ and KENACORT™ (triamcinolone), KENALOG™ (triamcinolone acetonide), ARISTOCORT™ and KENACORT DIACETATE™ (triamcinolone diacetate), and ARISTOSPAN™ (triamcinolone hexacetonide); inhibitors of biosynthesis and action of adrenocortical steroids such as CYTADREN™ (aminoglutethimide), NIZORAL™ (ketoconazole), MODRASTANE™ (trilostane), and METOPIRONE™ (metyrapone); bovine, porcine or human insulin or mixtures thereof; insulin analogs; recombinant human insulin such as HUMULIN™ and NOVOLIN™; oral hypoglycemic agents such as ORAMIDE™ and ORINASE™ (tolbutamide), DIABINESE™ (chlorpropamide), TOLAMIDE™ and TOLINASE™ (tolazamide), DYMELOR™ (acetohexamide), glibenclamide, MICRONASE™, DIBETA™ and GLYNASE™ (glyburide), GLUCOTROL™ (glipizide), and DIAMICRON™ (gliclazide), GLUCOPHAGE™ (metformin), PRECOSE™ (acarbose), AMARYL™ (glimepiride), and ciglitazone; thiazolidinediones (TZDs) such as rosiglitazone, AVANDIA™ (rosiglitazone maleate), ACTOS™ (piogliatazone), troglitazone, ciglitazone, pioglitazone, and alpha-glucosidase inhibitors; bovine or porcine glucagon; somatostatins such as SANDOSTATIN™ (octreotide); and diazoxides such as PROGLYCEM™ (diazoxide). In still other embodiments, Therapeutics of the invention are administered in combination with one or more of the following: a biguanide antidiabetic agent, a glitazone antidiabetic agent, and a sulfonylurea antidiabetic agent.

In one embodiment, the Therapeutics of the invention are administered in combination with treatments for uterine motility disorders. Treatments for uterine motility disorders include, but are not limited to, estrogen drugs such as conjugated estrogens (e.g., PREMARIN® and ESTRATAB®), estradiols (e.g., CLIMARA® and ALORA®), estropipate, and chlorotrianisene; progestin drugs (e.g., AMEN® (medroxyprogesterone), MICRONOR® (norethidrone acetate), PROMETRIUM® progesterone, and megestrol acetate); and estrogen/progesterone combination therapies such as, for example, conjugated estrogens/medroxyprogesterone (e.g., PREMPRO™ and PREMPHASE®) and norethindrone acetate/ethinyl estsradiol (e.g., FEMHRT™).

In an additional embodiment, the Therapeutics of the invention are administered in combination with drugs effective in treating iron deficiency and hypochromic anemias, including but not limited to, ferrous sulfate (iron sulfate, FEOSOL™), ferrous fumarate (e.g., FEOSTAT™), ferrous gluconate (e.g., FERGON™), polysaccharide-iron complex (e.g., NIFEREX™), iron dextran injection (e.g., INFED™), cupric sulfate, pyroxidine, riboflavin, Vitamin $B_{12}$, cyancobalamin injection (e.g., REDISOL™, RUBRAMIN PC™), hydroxocobalamin, folic acid (e.g., FOLVITE™), leucovorin (folinic acid, 5-CHOH4PteGlu, citrovorum factor) or WELLCOVORIN (Calcium salt of leucovorin), transferrin or ferritin.

In certain embodiments, the Therapeutics of the invention are administered in combination with agents used to treat psychiatric disorders. Psychiatric drugs that may be administered with the Therapeutics of the invention include, but are not limited to, antipsychotic agents (e.g., chlorpromazine, chlorprothixene, clozapine, fluphenazine, haloperidol, loxapine, mesoridazine, molindone, olanzapine, perphenazine, pimozide, quetiapine, risperidone, thioridazine, thiothixene, trifluoperazine, and triflupromazine), antimanic agents (e.g., carbamazepine, divalproex sodium, lithium carbonate, and lithium citrate), antidepressants (e.g., amitriptyline, amoxapine, bupropion, citalopram, clomipramine, desipramine, doxepin, fluvoxamine, fluoxetine, imipramine, isocarboxazid, maprotiline, mirtazapine, nefazodone, nortriptyline, paroxetine, phenelzine, protriptyline, sertraline, tranylcypromine, trazodone, trimipramine, and venlafaxine), antianxiety agents (e.g., alprazolam, buspirone, chlordiazepoxide, clorazepate, diazepam, halazepam, lorazepam, oxazepam, and prazepam), and stimulants (e.g., d-amphetamine, methylphenidate, and pemoline).

In other embodiments, the Therapeutics of the invention are administered in combination with agents used to treat neurological disorders. Neurological agents that may be administered with the Therapeutics of the invention include, but are not limited to, antiepileptic agents (e.g., carbamazepine, clonazepam, ethosuximide, phenobarbital, phenyloin, primidone, valproic acid, divalproex sodium, felbamate, gabapentin, lamotrigine, levetiracetam, oxcarbazepine, tiagabine, topiramate, zonisamide, diazepam, lorazepam, and clonazepam), antiparkinsonian agents (e.g., levodopa/carbidopa, selegiline, amantadine, bromocriptine, pergolide, ropinirole, pramipexole, benztropine; biperiden; ethopropazine; procyclidine; trihexyphenidyl, tolcapone), and ALS therapeutics (e.g. riluzole).

In another embodiment, Therapeutics of the invention are administered in combination with vasodilating agents and/or calcium channel blocking agents. Vasodilating agents that may be administered with the Therapeutics of the invention include, but are not limited to, Angiotensin Converting Enzyme (ACE) inhibitors (e.g., papaverine, isoxsuprine, benazepril, captopril, cilazapril, enalapril, enelaprilat, fosinopril, lisinopril, moexipril, perindopril, quinapril, ramipril, spirapril, trandolapril, and nylidrin), and nitrates (e.g., amyl nitrite, isosorbide dinitrate, isosorbide mononitrate, nitric oxide gas, and nitroglycerin). Examples of calcium channel blocking agents that may be administered in combination with the Therapeutics of the invention include, but are not limited to amlodipine, bepridil, diltiazem, felodipine, flunarizine, isradipine, nicardipine, nifedipine, nimodipine, and verapamil.

Other vasodilating agents that may be administered with the Therapeutics of the invention include, but are not limited to, epoprostenol and alprostadil.

In certain embodiments, the Therapeutics of the invention are administered in combination with treatments for cardiovascular disorders. Treatments for cardiovascular disorders that may be administered with the Therapeutic of the invention include, but are not limited to, angiotensin II blockers (e.g., irbesartan, losartan, and valsartan), alpha adrenergic blockers (e.g., doxazosin, prazosin, tamsulosin, and terazosin), hypotensive agents (e.g., clonidine, hydralazine, methyldopa, minoxidil, nitroprusside, and reserpine) and antilipemic agents (e.g., atorvastatin, cholestyramine, colestipol, fenofibrate, gemfibrate, lovstatin, pravastatin, and simvastatin).

In certain embodiments, the Therapeutics of the invention are administered in combination with treatments for gastrointestinal disorders. Treatments for gastrointestinal disorders that may be administered with the Therapeutic of the invention include, but are not limited to, $H_2$ histamine receptor antagonists (e.g., TAGAMET™ (cimetidine), ZANTAC™ (ranitidine), PEPCID™ (famotidine), and AXID™ (nizatidine)); inhibitors of $H^+$, $K^+$ ATPase (e.g., PREVACID™ (lansoprazole) and PRILOSEC™ (omeprazole)); Bismuth compounds (e.g., PEPTO-BISMOL™ (bismuth subsalicylate) and DE-NOL™ (bismuth subcitrate)); various antacids; sucralfate; prostaglandin analogs (e.g. CYTOTEC™ (misoprostol)); muscarinic cholinergic antagonists; laxatives (e.g., surfactant laxatives, stimulant laxatives, saline and osmotic laxatives); antidiarrheal agents (e.g., LOMOTIL™ (diphenoxylate), MOTOFEN™ (diphenoxin), and IMODIUM™ (loperamide hydrochloride)), synthetic analogs of somatostatin such as SANDOSTATIN™ (octreotide), antiemetic agents (e.g., ZOFRAN™ (ondansetron), KYTRIL™ (granisetron hydrochloride), tropisetron, dolasetron, metoclopramide, chlorpromazine, perphenazine, proclorperazine, promethazine, thiethylperazine, triflupromazine, domperidone, haloperidol, droperidol, trimethobenzamide, dexamethasone, methylprednisolone, dronabinol, and nabilone); D2 antagonists (e.g., metoclopramide, trimethobenzamide and chlorpromazine); bile salts; chenodeoxycholic acid; ursodeoxycholic acid; and pancreatic enzyme preparations such as pancreatin and pancrelipase.

In additional embodiments, the Therapeutics of the invention are administered in combination with other therapeutic or prophylactic regimens, such as, for example, radiation therapy.

Example 14

Method of Treating Decreased Levels of the Polypeptide

The present invention relates to a method for treating an individual in need of an increased level of a polypeptide of the invention in the body comprising administering to such an individual a composition comprising a therapeutically effective amount of polypeptides (including agonists thereto), and/or antibodies of the invention. Moreover, it will be appreciated that conditions caused by a decrease in the standard or normal expression level of a polypeptide of the present invention in an individual may be treated by administering agonists of said polypeptide. Thus, the invention also provides a method of treatment of an individual in need of an increased level of the polypeptide comprising administering to such an individual a Therapeutic comprising an amount of the agonist (including polypeptides and antibodies of the present invention) to increase the activity level of the polypeptide in such an individual.

For example, a patient with decreased levels of a polypeptide receives a daily dose 0.1-100 μg/kg of the agonist for six consecutive days. The exact details of the dosing scheme, based on administration and formulation, are provided in Example 13.

Example 15

Method of Treating Increased Levels of the Polypeptide

The present invention also relates to a method of treating an individual in need of a decreased level of a polypeptide of the invention in the body comprising administering to such an individual a composition comprising a therapeutically effective amount of an antagonist of the invention (including polypeptides and antibodies of the invention).

In one example, antisense technology is used to inhibit production of a polypeptide of the present invention. This technology is one example of a method of decreasing levels of a polypeptide, due to a variety of etiologies, such as cancer.

For example, a patient diagnosed with abnormally increased levels of a polypeptide is administered intravenously antisense polynucleotides at 0.5, 1.0, 1.5, 2.0 and 3.0 mg/kg day for 21 days. This treatment is repeated after a 7-day rest period if the treatment was well tolerated. The antisense polynucleotides of the present invention can be formulated using techniques and formulations described herein (e.g. see Example 13), or otherwise known in the art.

Example 16

Method of Treatment Using Gene Therapy—Ex Vivo

One method of gene therapy transplants fibroblasts, which are capable of expressing a polypeptide, onto a patient. Generally, fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin) is added. The flasks are then incubated at 37 degree C. for approximately one week.

At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al., DNA, 7:219-25 (1988)), flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding a polypeptide of the present invention can be amplified using PCR primers which correspond to the 5' and 3' end sequences respectively as set forth in Example 1 using primers and having appropriate restriction sites and initiation/stop codons, if necessary. Preferably, the 5' primer contains an EcoRI site and the 3' primer includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is then used to transform bacteria HB101, which are then plated onto agar containing kanamycin for the purpose of confirming that the vector has the gene of interest properly inserted.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the gene is then added to the media and the packaging cells transduced with the vector. The packaging cells now produce infectious viral particles containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his. Once the fibroblasts have been efficiently infected, the fibroblasts are analyzed to determine whether protein is produced.

The engineered fibroblasts are then transplanted onto the host, either alone or after having been grown to confluence on cytodex 3 microcarrier beads.

Example 17

Gene Therapy Using Endogenous Genes Corresponding to Polynucleotides of the Invention Another method of gene therapy according to the present invention involves operably associating the endogenous polynucleotide sequence of the invention with a promoter via homologous recombination as described, for example, in U.S. Pat. No. 5,641,670, issued Jun. 24, 1997; International Publication NO: WO 96/29411, published Sep. 26, 1996; International Publication NO: WO 94/12650, published Aug. 4, 1994; Koller et al., *Proc. Natl. Acad. Sci. USA,* 86:8932-8935 (1989); and Zijlstra et al., *Nature,* 342:435-438 (1989). This method involves the activation of a gene which is present in the target cells, but which is not expressed in the cells, or is expressed at a lower level than desired.

Polynucleotide constructs are made which contain a promoter and targeting sequences, which are homologous to the 5' non-coding sequence of endogenous polynucleotide sequence, flanking the promoter. The targeting sequence will be sufficiently near the 5' end of the polynucleotide sequence so the promoter will be operably linked to the endogenous sequence upon homologous recombination. The promoter and the targeting sequences can be amplified using PCR. Preferably, the amplified promoter contains distinct restriction enzyme sites on the 5' and 3' ends. Preferably, the 3' end of the first targeting sequence contains the same restriction enzyme site as the 5' end of the amplified promoter and the 5' end of the second targeting sequence contains the same restriction site as the 3' end of the amplified promoter.

The amplified promoter and the amplified targeting sequences are digested with the appropriate restriction enzymes and subsequently treated with calf intestinal phosphatase. The digested promoter and digested targeting sequences are added together in the presence of T4 DNA ligase. The resulting mixture is maintained under conditions appropriate for ligation of the two fragments. The construct is size fractionated on an agarose gel, then purified by phenol extraction and ethanol precipitation.

In this Example, the polynucleotide constructs are administered as naked polynucleotides via electroporation. However, the polynucleotide constructs may also be administered with transfection-facilitating agents, such as liposomes, viral sequences, viral particles, precipitating agents, etc. Such methods of delivery are known in the art.

Once the cells are transfected, homologous recombination will take place which results in the promoter being operably linked to the endogenous polynucleotide sequence. This results in the expression of polynucleotide corresponding to the polynucleotide in the cell. Expression may be detected by immunological staining, or any other method known in the art.

Fibroblasts are obtained from a subject by skin biopsy. The resulting tissue is placed in DMEM+10% fetal calf serum. Exponentially growing or early stationary phase fibroblasts are trypsinized and rinsed from the plastic surface with nutrient medium. An aliquot of the cell suspension is removed for counting, and the remaining cells are subjected to centrifugation. The supernatant is aspirated and the pellet is resuspended in 5 ml of electroporation buffer (20 mM HEPES pH 7.3, 137 mM NaCl, 5 mM KCl, 0.7 mM $Na_2HPO_4$, 6 mM dextrose). The cells are recentrifuged, the supernatant aspirated, and the cells resuspended in electroporation buffer containing 1 mg/ml acetylated bovine serum albumin. The final cell suspension contains approximately $3\times10^6$ cells/ml. Electroporation should be performed immediately following resuspension.

Plasmid DNA is prepared according to standard techniques. For example, to construct a plasmid for targeting to the locus corresponding to the polynucleotide of the invention, plasmid pUC18 (MBI Fermentas, Amherst, N.Y.) is digested with HindIII. The CMV promoter is amplified by PCR with an XbaI site on the 5' end and a BamHI site on the 3' end. Two non-coding sequences are amplified via PCR: one non-coding sequence (fragment 1) is amplified with a HindIII site at the 5' end and an Xba site at the 3' end; the other non-coding sequence (fragment 2) is amplified with a BamHI site at the 5' end and a HindIII site at the 3' end. The CMV promoter and the fragments (1 and 2) are digested with the appropriate enzymes (CMV promoter—XbaI and BamHI; fragment 1—XbaI; fragment 2—BamHI) and ligated together. The resulting ligation product is digested with HindIII, and ligated with the HindIII-digested pUC18 plasmid.

Plasmid DNA is added to a sterile cuvette with a 0.4 cm electrode gap (Bio-Rad). The final DNA concentration is generally at least 120 μg/ml. 0.5 ml of the cell suspension (containing approximately $1.5\times10^6$ cells) is then added to the cuvette, and the cell suspension and DNA solutions are gently mixed. Electroporation is performed with a Gene-Pulser apparatus (Bio-Rad). Capacitance and voltage are set at 960 μF and 250-300 V, respectively. As voltage increases, cell survival decreases, but the percentage of surviving cells that stably incorporate the introduced DNA into their genome increases dramatically. Given these parameters, a pulse time of approximately 14-20 mSec should be observed.

Electroporated cells are maintained at room temperature for approximately 5 min, and the contents of the cuvette are then gently removed with a sterile transfer pipette. The cells are added directly to 10 ml of prewarmed nutrient media (DMEM with 15% calf serum) in a 10 cm dish and incubated at 37 degree C. The following day, the media is aspirated and replaced with 10 ml of fresh media and incubated for a further 16-24 hours.

The engineered fibroblasts are then injected into the host, either alone or after having been grown to confluence on cytodex 3 microcarrier beads. The fibroblasts now produce the protein product. The fibroblasts can then be introduced into a patient as described above.

Example 18

Method of Treatment Using Gene Therapy—In Vivo

Another aspect of the present invention is using in vivo gene therapy methods to prevent, treat, and/or ameliorate diseases, disorders, and conditions (such as immune, cardiovascular, cancer, and other proliferative diseases, disorders, and conditions). The gene therapy method relates to the introduction of naked nucleic acid (DNA, RNA, and antisense DNA or RNA) sequences into an animal to increase or decrease the expression of the polypeptide. The polynucleotide of the present invention may be operatively linked to (i.e., associated with) a promoter or any other genetic elements necessary for the expression of the polypeptide by the target tissue. Such gene therapy and delivery techniques and methods are known in the art, see, for example, WO90/11092, WO98/11779; U.S. Pat. No. 5,693,622, U.S. Pat. No. 5,705,151, U.S. Pat. No. 5,580,859; Tabata et al., Cardiovasc. Res. 35(3):470-479 (1997); Chao et al., Pharmacol. Res. 35(6): 517-522 (1997); Wolff, Neuromuscul. Disord. 7(5):314-318 (1997); Schwartz et al., Gene Ther. 3(5):405-411 (1996); Tsurumi et al., Circulation 94(12):3281-3290 (1996) (incorporated herein by reference).

The polynucleotide constructs may be delivered by any method that delivers injectable materials to the cells of an animal, such as, injection into the interstitial space of tissues (heart, muscle, skin, lung, liver, intestine and the like). The polynucleotide constructs can be delivered in a pharmaceutically acceptable liquid or aqueous carrier.

The term "naked" polynucleotide, DNA or RNA, refers to sequences that are free from any delivery vehicle that acts to assist, promote, or facilitate entry into the cell, including viral sequences, viral particles, liposome formulations, LIPOFECTIN™ or precipitating agents and the like. However, the polynucleotides of the present invention may also be delivered in liposome formulations (such as those taught in Felgner P. L. et al. (1995) Ann. NY Acad. Sci. 772:126-139 and Abdallah B. et al. (1995) Biol. Cell 85(1):1-7) which can be prepared by methods well known to those skilled in the art.

The polynucleotide vector constructs used in the gene therapy method are preferably constructs that will not integrate into the host genome nor will they contain sequences that allow for replication. Any strong promoter known to those skilled in the art can be used for driving the expression of DNA. Unlike other gene therapy techniques, one major advantage of introducing naked nucleic acid sequences into target cells is the transitory nature of the polynucleotide synthesis in the cells. Studies have shown that non-replicating DNA sequences can be introduced into cells to provide production of the desired polypeptide for periods of up to six months.

The polynucleotide construct can be delivered to the interstitial space of tissues within an animal, including muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, and connective tissue. Interstitial space of the tissues comprises the intercellular fluid, mucopolysaccharide matrix among the reticular fibers of organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation and the lymph fluid of the lymphatic channels. Delivery to the interstitial space of muscle tissue is preferred for the reasons discussed below. They may be conveniently delivered by injection into the tissues comprising these cells. They are preferably delivered to and expressed in persistent, non-dividing cells which are differentiated, although delivery and expression may be achieved in non-differentiated or less completely differentiated cells, such as, for example, stem cells of blood or skin fibroblasts. In vivo muscle cells are particularly competent in their ability to take up and express polynucleotides.

For the naked polynucleotide injection, an effective dosage amount of DNA or RNA will be in the range of from about 0.05 g/kg body weight to about 50 mg/kg body weight. Preferably the dosage will be from about 0.005 mg/kg to about 20 mg/kg and more preferably from about 0.05 mg/kg to about 5 mg/kg. Of course, as the artisan of ordinary skill will appreciate, this dosage will vary according to the tissue site of injection. The appropriate and effective dosage of nucleic acid sequence can readily be determined by those of ordinary skill in the art and may depend on the condition being treated and the route of administration. The preferred route of administration is by the parenteral route of injection into the interstitial space of tissues. However, other parenteral routes may also be used, such as, inhalation of an aerosol formulation particularly for delivery to lungs or bronchial tissues, throat or mucous membranes of the nose. In addition, naked polynucleotide constructs can be delivered to arteries during angioplasty by the catheter used in the procedure.

The dose response effects of injected polynucleotide in muscle in vivo is determined as follows. Suitable template DNA for production of mRNA coding for polypeptide of the present invention is prepared in accordance with a standard recombinant DNA methodology. The template DNA, which may be either circular or linear, is either used as naked DNA or complexed with liposomes. The quadriceps muscles of mice are then injected with various amounts of the template DNA.

Five to six week old female and male Balb/C mice are anesthetized by intraperitoneal injection with 0.3 ml of 2.5% Avertin™. A 1.5 cm incision is made on the anterior thigh, and the quadriceps muscle is directly visualized. The template DNA is injected in 0.1 ml of carrier in a 1 cc syringe through a 27 gauge needle over one minute, approximately 0.5 cm from the distal insertion site of the muscle into the knee and about 0.2 cm deep. A suture is placed over the injection site for future localization, and the skin is closed with stainless steel clips.

After an appropriate incubation time (e.g., 7 days) muscle extracts are prepared by excising the entire quadriceps. Every fifth 15 μm cross-section of the individual quadriceps muscles is histochemically stained for protein expression. A time course for protein expression may be done in a similar fashion except that quadriceps from different mice are harvested at different times. Persistence of DNA in muscle following injection may be determined by Southern blot analysis after preparing total cellular DNA and HIRT supernatants from injected and control mice. The results of the above experimentation in mice can be used to extrapolate proper dosages and other treatment parameters in humans and other animals using naked DNA.

Example 19

Transgenic Animals

The polypeptides of the invention can also be expressed in transgenic animals. Animals of any species, including, but not limited to, mice, rats, rabbits, hamsters, guinea pigs, pigs, micro-pigs, goats, sheep, cows and non-human primates, e.g., baboons, monkeys, and chimpanzees may be used to generate transgenic animals. In a specific embodiment, techniques described herein or otherwise known in the art, are used to express polypeptides of the invention in humans, as part of a gene therapy protocol.

Any technique known in the art may be used to introduce the transgene (i.e., polynucleotides of the invention) into animals to produce the founder lines of transgenic animals. Such techniques include, but are not limited to, pronuclear microinjection (Paterson et al., Appl. Microbiol. Biotechnol. 40:691-698 (1994); Carver et al., Biotechnology (NY) 11:1263-1270 (1993); Wright et al., Biotechnology (NY) 9:830-834 (1991); and Hoppe et al., U.S. Pat. No. 4,873,191 (1989)); retrovirus mediated gene transfer into germ lines (Van der Putten et al., Proc. Natl. Acad. Sci., USA 82:6148-6152 (1985)), blastocysts or embryos; gene targeting in embryonic stem cells (Thompson et al., Cell 56:313-321 (1989)); electroporation of cells or embryos (Lo, 1983, Mol Cell. Biol. 3:1803-1814 (1983)); introduction of the polynucleotides of the invention using a gene gun (see, e.g., Ulmer et al., Science 259:1745 (1993); introducing nucleic acid constructs into embryonic pleuripotent stem cells and transferring the stem cells back into the blastocyst; and sperm-mediated gene transfer (Lavitrano et al., Cell 57:717-723 (1989); etc. For a review of such techniques, see Gordon, “Transgenic Animals,” Intl. Rev. Cytol. 115:171-229 (1989), which is incorporated by reference herein in its entirety.

Any technique known in the art may be used to produce transgenic clones containing polynucleotides of the invention, for example, nuclear transfer into enucleated oocytes of nuclei from cultured embryonic, fetal, or adult cells induced to quiescence (Campell et al., Nature 380:64-66 (1996); Wilmut et al., Nature 385:810-813 (1997)).

The present invention provides for transgenic animals that carry the transgene in all their cells, as well as animals which carry the transgene in some, but not all their cells, i.e., mosaic animals or chimeric. The transgene may be integrated as a single transgene or as multiple copies such as in concatamers, e.g., head-to-head tandems or head-to-tail tandems. The transgene may also be selectively introduced into and activated in a particular cell type by following, for example, the teaching of Lasko et al. (Lasko et al., Proc. Natl. Acad. Sci. USA 89:6232-6236 (1992)). The regulatory sequences required for such a cell-type specific activation will depend upon the particular cell type of interest, and will be apparent to those of skill in the art. When it is desired that the polynucleotide transgene be integrated into the chromosomal site of the endogenous gene, gene targeting is preferred. Briefly, when such a technique is to be utilized, vectors containing some nucleotide sequences homologous to the endogenous gene are designed for the purpose of integrating, via homologous recombination with chromosomal sequences, into and disrupting the function of the nucleotide sequence of the endogenous gene. The transgene may also be selectively introduced into a particular cell type, thus inactivating the endogenous gene in only that cell type, by following, for example, the teaching of Gu et al. (Gu et al., Science 265: 103-106 (1994)). The regulatory sequences required for such a cell-type specific inactivation will depend upon the particular cell type of interest, and will be apparent to those of skill in the art.

Once transgenic animals have been generated, the expression of the recombinant gene may be assayed utilizing standard techniques. Initial screening may be accomplished by Southern blot analysis or PCR techniques to analyze animal tissues to verify that integration of the transgene has taken place. The level of mRNA expression of the transgene in the tissues of the transgenic animals may also be assessed using techniques which include, but are not limited to, Northern blot analysis of tissue samples obtained from the animal, in situ hybridization analysis, and reverse transcriptase-PCR (rt-PCR). Samples of transgenic gene-expressing tissue may also be evaluated immunocytochemically or immunohistochemically using antibodies specific for the transgene product.

Once the founder animals are produced, they may be bred, inbred, outbred, or crossbred to produce colonies of the particular animal. Examples of such breeding strategies include, but are not limited to: outbreeding of founder animals with more than one integration site in order to establish separate lines; inbreeding of separate lines in order to produce compound transgenics that express the transgene at higher levels because of the effects of additive expression of each transgene; crossing of heterozygous transgenic animals to produce animals homozygous for a given integration site in order to both augment expression and eliminate the need for screening of animals by DNA analysis; crossing of separate homozygous lines to produce compound heterozygous or homozygous lines; and breeding to place the transgene on a distinct background that is appropriate for an experimental model of interest.

Transgenic animals of the invention have uses which include, but are not limited to, animal model systems useful in elaborating the biological function of polypeptides of the present invention, studying conditions and/or disorders associated with aberrant expression, and in screening for compounds effective in ameliorating such conditions and/or disorders.

Example 20

Knock-Out Animals

Endogenous gene expression can also be reduced by inactivating or “knocking out” the gene and/or its promoter using targeted homologous recombination. (e.g., see Smithies et al., Nature 317:230-234 (1985); Thomas & Capecchi, Cell 51:503-512 (1987); Thompson et al., Cell 5:313-321 (1989); each of which is incorporated by reference herein in its entirety). For example, a mutant, non-functional polynucleotide of the invention (or a completely unrelated DNA sequence) flanked by DNA homologous to the endogenous polynucleotide sequence (either the coding regions or regulatory regions of the gene) can be used, with or without a selectable marker and/or a negative selectable marker, to transfect cells that express polypeptides of the invention in vivo. In another embodiment, techniques known in the art are used to generate knockouts in cells that contain, but do not express the gene of interest. Insertion of the DNA construct, via targeted homologous recombination, results in inactivation of the targeted gene. Such approaches are particularly suited in research and agricultural fields where modifications to embryonic stem cells can be used to generate animal offspring with an inactive targeted gene (e.g., see Thomas & Capecchi 1987 and Thompson 1989, supra). However this approach can be routinely adapted for use in humans provided the recombinant DNA constructs are directly administered or targeted to the required site in vivo using appropriate viral vectors that will be apparent to those of skill in the art.

In further embodiments of the invention, cells that are genetically engineered to express the polypeptides of the invention, or alternatively, that are genetically engineered not to express the polypeptides of the invention (e.g., knockouts) are administered to a patient in vivo. Such cells may be obtained from the patient (i.e., animal, including human) or an MHC compatible donor and can include, but are not limited to fibroblasts, bone marrow cells, blood cells (e.g., lymphocytes), adipocytes, muscle cells, endothelial cells etc. The cells are genetically engineered in vitro using recombinant DNA techniques to introduce the coding sequence of polypeptides of the invention into the cells, or alternatively, to disrupt the coding sequence and/or endogenous regulatory sequence associated with the polypeptides of the invention, e.g., by transduction (using viral vectors, and preferably vectors that integrate the transgene into the cell genome) or transfection procedures, including, but not limited to, the use of plasmids, cosmids, YACs, naked DNA, electroporation, liposomes, etc. The coding sequence of the polypeptides of the invention can be placed under the control of a strong constitutive or inducible promoter or promoter/enhancer to achieve expression, and preferably secretion, of the polypeptides of the invention. The engineered cells which express and preferably secrete the polypeptides of the invention can be introduced into the patient systemically, e.g., in the circulation, or intraperitoneally.

Alternatively, the cells can be incorporated into a matrix and implanted in the body, e.g., genetically engineered fibroblasts can be implanted as part of a skin graft; genetically engineered endothelial cells can be implanted as part of a lymphatic or vascular graft. (See, for example, Anderson et al. U.S. Pat. No. 5,399,349; and Mulligan & Wilson, U.S. Pat. No. 5,460,959 each of which is incorporated by reference herein in its entirety).

When the cells to be administered are non-autologous or non-MHC compatible cells, they can be administered using well known techniques which prevent the development of a host immune response against the introduced cells. For example, the cells may be introduced in an encapsulated form that, while allowing for an exchange of components with the immediate extracellular environment, does not allow the introduced cells to be recognized by the host immune system.

Transgenic and "knock-out" animals of the invention have uses which include, but are not limited to, animal model systems useful in elaborating the biological function of polypeptides of the present invention, studying conditions and/or disorders associated with aberrant expression, and in screening for compounds effective in ameliorating such conditions and/or disorders.

Example 21

Assays Detecting Stimulation or Inhibition of B Cell Proliferation and Differentiation Generation of functional humoral immune responses requires both soluble and cognate signaling between B-lineage cells and their microenvironment. Signals may impart a positive stimulus that allows a B-lineage cell to continue its programmed development, or a negative stimulus that instructs the cell to arrest its current developmental pathway. To date, numerous stimulatory and inhibitory signals have been found to influence B cell responsiveness including IL-2, IL-4, IL-5, IL-6, IL-7, IL10, IL-13, IL-14 and IL-15. Interestingly, these signals are by themselves weak effectors but can, in combination with various co-stimulatory proteins, induce activation, proliferation, differentiation, homing, tolerance and death among B cell populations.

One of the best studied classes of B-cell co-stimulatory proteins is the TNF-superfamily. Within this family CD40, CD27, and CD30 along with their respective ligands CD154, CD70, and CD153 have been found to regulate a variety of immune responses. Assays which allow for the detection and/or observation of the proliferation and differentiation of these B-cell populations and their precursors are valuable tools in determining the effects various proteins may have on these B-cell populations in terms of proliferation and differentiation. Listed below are two assays designed to allow for the detection of the differentiation, proliferation, or inhibition of B-cell populations and their precursors.

In Vitro Assay—Agonists or antagonists of the invention can be assessed for its ability to induce activation, proliferation, differentiation or inhibition and/or death in B-cell populations and their precursors. The activity of the agonists or antagonists of the invention on purified human tonsillar B cells, measured qualitatively over the dose range from 0.1 to 10,000 ng/mL, is assessed in a standard B-lymphocyte co-stimulation assay in which purified tonsillar B cells are cultured in the presence of either formalin-fixed *Staphylococcus aureus* Cowan I (SAC) or immobilized anti-human IgM antibody as the priming agent. Second signals such as IL-2 and IL-15 synergize with SAC and IgM crosslinking to elicit B cell proliferation as measured by tritiated-thymidine incorporation. Novel synergizing agents can be readily identified using this assay. The assay involves isolating human tonsillar B cells by magnetic bead (MACS) depletion of CD3-positive cells. The resulting cell population is greater than 95% B cells as assessed by expression of CD45R(B220).

Various dilutions of each sample are placed into individual wells of a 96-well plate to which are added $10^5$ B-cells suspended in culture medium (RPMI 1640 containing 10% FBS, $5\times10^{-5}$M 2ME, 100 U/ml penicillin, 10 μg/ml streptomycin, and $10^{-5}$ dilution of SAC) in a total volume of 150 μl. Proliferation or inhibition is quantitated by a 20 h pulse (1 uCi/well) with 3H-thymidine (6.7 Ci/mM) beginning 72 h post factor addition. The positive and negative controls are IL2 and medium respectively.

In vivo Assay—BALB/c mice are injected (i.p.) twice per day with buffer only, or 2 mg/Kg of agonists or antagonists of the invention, or truncated forms thereof. Mice receive this treatment for 4 consecutive days, at which time they are sacrificed and various tissues and serum collected for analyses. Comparison of H&E sections from normal spleens and spleens treated with agonists or antagonists of the invention identify the results of the activity of the agonists or antagonists on spleen cells, such as the diffusion of peri-arterial lymphatic sheaths, and/or significant increases in the nucleated cellularity of the red pulp regions, which may indicate the activation of the differentiation and proliferation of B-cell populations. Immunohistochemical studies using a B cell marker, anti-CD45R(B220), are used to determine whether any physiological changes to splenic cells, such as splenic disorganization, are due to increased B-cell representation within loosely defined B-cell zones that infiltrate established T-cell regions.

Flow cytometric analyses of the spleens from mice treated with agonist or antagonist are used to indicate whether the agonists or antagonists specifically increases the proportion of ThB+, CD45R(B220)dull B cells over that which is observed in control mice.

Likewise, a predicted consequence of increased mature B-cell representation in vivo is a relative increase in serum Ig titers. Accordingly, serum IgM and IgA levels are compared between buffer and agonists or antagonists-treated mice.

The studies described in this example tested activity of agonists or antagonists of the invention. However, one skilled in the art could easily modify the exemplified studies to test the activity of polynucleotides or polypeptides of the invention (e.g., gene therapy).

Example 22

T Cell Proliferation Assay

Proliferation Assay for Resting PBLs

A CD3-induced proliferation assay is performed on PBMCs and is measured by the uptake of $^3$H-thymidine. The assay is performed as follows. Ninety-six well plates are coated with 100 μl/well of mAb to CD3 (HIT3a, Pharmingen) or isotype-matched control mAb (B33.1) overnight at 4° C. (1 μg/ml in 0.05M bicarbonate buffer, pH 9.5), then washed three times with PBS. PBMC are isolated by F/H gradient centrifugation from human peripheral blood and added to quadruplicate wells ($5\times10^4$/well) of mAb coated plates in RPMI containing 10% FCS and P/S in the presence of varying concentrations of agonists or antagonists of the invention (total volume 200 μl). Relevant protein buffer and medium alone are controls. After 48 hr. culture at 37° C., plates are spun for 2 min. at 1000 rpm and 100 μl of supernatant is removed and stored at −20° C. for measurement of IL-2 (or other cytokines) if effect on proliferation is observed. Wells are supplemented with 100 μl of medium containing 0.5 μCi of $^3$H-thymidine and cultured at 37° C. for 18-24 hr. Wells are harvested and incorporation of $^3$H-thymidine used as a measure of proliferation. Anti-CD3 alone is the positive control for proliferation. IL-2 (100 U/ml) is also used as a control which enhances proliferation. Control antibody which does not induce proliferation of T cells is used as the negative control for the effects of agonists or antagonists of the invention.

Alternatively, a proliferation assay on resting PBL (peripheral blood lymphocytes) is measured by the up-take of $^3$H-thymidine. The assay is performed as follows. PBMC are isolated by FICOLL™ (LSM, ICN Biotechnologies, Aurora, Ohio) gradient centrifugation from human peripheral blood, and are cultured overnight in 10% (Fetal Calf Serum, Biofluids, Rockville, Md.)/RPMI (Gibco BRL, Gaithersburg, Md.). This overnight incubation period allows the adherent cells to attach to the plastic, which results in a lower background in the assay as there are fewer cells that can act as antigen presenting cells or that might be producing growth factors. The following day the non-adherent cells are collected, washed and used in the proliferation assay. The assay is performed in a 96 well plate using $2\times10^4$ cells/well in a final volume of 200 μl. The supernatants (e.g., CHO or 293T supernatants) expressing the protein of interest are tested at a 30% final dilution, therefore 60 μl are added to 140 μl of 10% FCS/RPMI containing the cells. Control supernatants are used at the same final dilution and express the following proteins: vector (negative control), IL-2 (*), IFNγ, TNFα, IL-10 and TR2. In addition to the control supernatants, recombinant human IL-2 (R & D Systems, Minneapolis, Minn.) at a final concentration of 100 ng/ml is also used. After 24 hours of culture, each well is pulsed with 1 μCi of $^3$H-thymidine (Nen, Boston, Mass.). Cells are then harvested 20 hours following pulsing and incorporation of $^3$H-thymidine is used as a measure of proliferation. Results are expressed as an average of triplicate samples plus or minus standard error. (*) The amount of the control cytokines IL-2, IFNγ, TNFα, and IL-10 produced in each transfection varies between 300 pg to 5 ng/ml.

Costimulation Assay.

A costimulation assay on resting PBL (peripheral blood lymphocytes) is performed in the presence of immobilized antibodies to CD3 and CD28. The use of antibodies specific for the invariant regions of CD3 mimic the induction of T cell activation that would occur through stimulation of the T cell receptor by an antigen. Cross-linking of the TCR (first signal) in the absence of a costimulatory signal (second signal) causes very low induction of proliferation and will eventually result in a state of "anergy", which is characterized by the absence of growth and inability to produce cytokines. The addition of a costimulatory signal such as an antibody to CD28 mimics the action of the costimulatory molecule. B7-1 expressed on activated APCs, results in enhancement of T cell responses including cell survival and production of IL-2. Therefore this type of assay allows to detect both positive and negative effects caused by addition of supernatants expressing the proteins of interest on T cell proliferation.

The assay is performed as follows. Ninety-six well plates are coated with 100 ng/ml anti-CD3 and 5 μg/ml anti-CD28 (Pharmingen, San Diego, Calif.) in a final volume of 100 ul and incubated overnight at 4° C. Plates are washed twice with PBS before use. PBMC are isolated by FICOLL™ (LSM, ICN Biotechnologies, Aurora, Ohio) gradient centrifugation from human peripheral blood, and are cultured overnight in 10% FCS (Fetal Calf Serum, Biofluids, Rockville, Md.)/RPMI (Gibco BRL, Gaithersburg, Md.). This overnight incubation period allows the adherent cells to attach to the plastic, which results in a lower background in the assay as there are fewer cells that can act as antigen presenting cells or that might be producing growth factors. The following day the non adherent cells are collected, washed and used in the proliferation assay. The assay is performed in a 96 well plate using $2\times10^4$ cells/well in a final volume of 200 μl. The supernatants (e.g., CHO or 293T supernatants) expressing the protein of interest are tested at a 30% final dilution, therefore 60 ul are added to 140 μl of 10% FCS/RPMI containing the cells. Control supernatants are used at the same final dilution and express the following proteins: vector only (negative control), IL-2, IFNγ, TNFα, IL-10 and TR2. In addition to the control supernatants recombinant human IL-2 (R & D Systems, Minneapolis, Minn.) at a final concentration of 10 ng/ml is also used. After 24 hours of culture, each well is pulsed with 1 μCi of $^3$H-thymidine (Nen, Boston, Mass.). Cells are then harvested 20 hours following pulsing and incorporation of $^3$H-thymidine is used as a measure of proliferation. Results are expressed as an average of triplicate samples plus or minus standard error.

Costimulation Assay: IFN γ and IL-2 ELISA.

The assay is performed as follows. Twenty-four well plates are coated with either 300 ng/ml or 600 ng/ml anti-CD3 and 5 μg/ml anti-CD28 (Pharmingen, San Diego, Calif.) in a final volume of 500 ul and incubated overnight at 4° C. Plates are washed twice with PBS before use. PBMC are isolated by FICOLL™ (LSM, ICN Biotechnologies, Aurora, Ohio) gradient centrifugation from human peripheral blood, and are cultured overnight in 10% FCS (Fetal Calf Serum, Biofluids, Rockville, Md.)/RPMI (Gibco BRL, Gaithersburg, Md.). This overnight incubation period allows the adherent cells to attach to the plastic, which results in a lower background in the assay as there are fewer cells that can act as antigen presenting cells or that might be producing growth factors. The following day the non adherent cells are collected, washed and used in the costimulation assay. The assay is performed in the pre-coated twenty-four well plate using $1\times10^5$ cells/well in a final volume of 900 μl. The supernatants (293T supernatants) expressing the protein of interest are tested at a 30% final dilution, therefore 300 μl are added to 600 μl of 10% FCS/RPMI containing the cells. Control supernatants are used at the same final dilution and express the following proteins: vector only (negative control), IL-2, IFNγ, IL-12 and IL-18. In addition to the control supernatants recombinant human IL-2 (all cytokines were purchased from R & D Systems, Minneapolis, Minn.) at a final concentration of 10 ng/ml, IL-12 at a final concentration of 1 ng/ml and IL-18 at a final concentration of 50 ng/ml are also used. Controls and unknown samples are tested in duplicate. Supernatant samples (250 μl) are collected 2 days and 5 days after the beginning of the assay. ELISAs to test for IFNγ and IL-2 secretion are performed using kits purchased from R & D Systems, (Minneapolis, Minn.). Results are expressed as an average of duplicate samples plus or minus standard error.

Proliferation Assay for Preactivated-Resting T Cells.

A proliferation assay on preactivated-resting T cells is performed on cells that are previously activated with the lectin phytohemagglutinin (PHA). Lectins are polymeric plant proteins that can bind to residues on T cell surface glycoproteins including the TCR and act as polyclonal activators. PBLs treated with PHA and then cultured in the presence of low doses of IL-2 resemble effector T cells. These cells are generally more sensitive to further activation induced by growth factors such as IL-2. This is due to the expression of high affinity IL-2 receptors that allows this population to respond to amounts of IL-2 that are 100 fold lower than what would have an effect on a naïve T cell. Therefore the use of this type of cells might enable to detect the effect of very low doses of an unknown growth factor, that would not be sufficient to induce proliferation on resting (naïve) T cells.

The assay is performed as follows. PBMC are isolated by F/H gradient centrifugation from human peripheral blood, and are cultured in 10% FCS (Fetal Calf Serum, Biofluids, Rockville, Md.)/RPMI (Gibco BRL, Gaithersburg, Md.) in the presence of 2 ug/ml PHA (SIGMA™, Saint Louis, Mo.) for three days. The cells are then washed in PBS and cultured in 10% FCS/RPMI in the presence of 5 ng/ml of human recombinant IL-2 (R & D Systems, Minneapolis, Minn.) for 3 days. The cells are washed and rested in starvation medium (1% FCS/RPMI) for 16 hours prior to the beginning of the proliferation assay. An aliquot of the cells is analyzed by FACS to determine the percentage of T cells (CD3 positive cells) present; this usually ranges between 93-97% depending on the donor. The assay is performed in a 96 well plate using $2\times10^4$ cells/well in a final volume of 200 μl. The supernatants (e.g., CHO or 293T supernatants) expressing the protein of interest are tested at a 30% final dilution, therefore 60 μl are added to 140 μl of in 10% FCS/RPMI containing the cells. Control supernatants are used at the same final dilution and express the following proteins: vector (negative control), IL-2, IFNγ, TNFα, IL-10 and TR2. In addition to the control supernatants recombinant human IL-2 at a final concentration of 10 ng/ml is also used. After 24 hours of culture, each well is pulsed with 1 μCi of $^3$H-thymidine (Nen, Boston, Mass.). Cells are then harvested 20 hours following pulsing and incorporation of $^3$H-thymidine is used as a measure of proliferation. Results are expressed as an average of triplicate samples plus or minus standard error.

The studies described in this example tested activity of agonists or antagonists of the invention. However, one skilled in the art could easily modify the exemplified studies to test the activity of polynucleotides or polypeptides of the invention (e.g., gene therapy).

Example 23

Effect of Agonists or Antagonists of the Invention on the Expression of MHC Class II, Costimulatory and Adhesion Molecules and Cell Differentiation of Monocytes and Monocyte-Derived Human Dendritic Cells Dendritic cells are generated by the expansion of proliferating precursors found in the peripheral blood: adherent PBMC or elutriated monocytic fractions are cultured for 7-10 days with GM-CSF (50 ng/ml) and IL-4 (20 ng/ml). These dendritic cells have the characteristic phenotype of immature cells (expression of CD1, CD80, CD86, CD40 and MHC class II antigens). Treatment with activating factors, such as TNF-α, causes a rapid change in surface phenotype (increased expression of MHC class I and II, costimulatory and adhesion molecules, downregulation of FCγRII, upregulation of CD83). These changes correlate with increased antigen-presenting capacity and with functional maturation of the dendritic cells.

FACS analysis of surface antigens is performed as follows. Cells are treated 1-3 days with increasing concentrations of agonist or antagonist of the invention or LPS (positive control), washed with PBS containing 1% BSA and 0.02 mM sodium azide, and then incubated with 1:20 dilution of appropriate FITC- or PE-labeled monoclonal antibodies for 30 minutes at 4° C. After an additional wash, the labeled cells are analyzed by flow cytometry on a FACScan (Becton Dickinson).

Effect on the production of cytokines. Cytokines generated by dendritic cells, in particular IL-12, are important in the initiation of T-cell dependent immune responses. IL-12 strongly influences the development of Th1 helper T-cell immune response, and induces cytotoxic T and NK cell function. An ELISA is used to measure the IL-12 release as follows. Dendritic cells ($10^6$/ml) are treated with increasing concentrations of agonists or antagonists of the invention for 24 hours. LPS (100 ng/ml) is added to the cell culture as positive control. Supernatants from the cell cultures are then collected and analyzed for IL-12 content using commercial ELISA kit (e.g., R & D Systems (Minneapolis, Minn.)). The standard protocols provided with the kits are used.

Effect on the expression of MHC Class II, costimulatory and adhesion molecules. Three major families of cell surface antigens can be identified on monocytes: adhesion molecules, molecules involved in antigen presentation, and Fc receptor. Modulation of the expression of MHC class II antigens and other costimulatory molecules, such as B7 and ICAM-1, may result in changes in the antigen presenting capacity of monocytes and ability to induce T cell activation. Increased expression of Fc receptors may correlate with improved monocyte cytotoxic activity, cytokine release and phagocytosis.

FACS analysis is used to examine the surface antigens as follows. Monocytes are treated 1-5 days with increasing concentrations of agonists or antagonists of the invention or LPS (positive control), washed with PBS containing 1% BSA and 0.02 mM sodium azide, and then incubated with 1:20 dilution of appropriate FITC- or PE-labeled monoclonal antibodies for 30 minutes at 4 degrees C. After an additional wash, the labeled cells are analyzed by flow cytometry on a FACScan (Becton Dickinson).

Monocyte activation and/or increased survival. Assays for molecules that activate (or alternatively, inactivate) monocytes and/or increase monocyte survival (or alternatively, decrease monocyte survival) are known in the art and may routinely be applied to determine whether a molecule of the invention functions as an inhibitor or activator of monocytes. Agonists or antagonists of the invention can be screened using the three assays described below. For each of these assays, Peripheral blood mononuclear cells (PBMC) are purified from single donor leukopacks (American Red Cross, Baltimore, Md.) by centrifugation through a HISTOPAQUE™ gradient (SIGMA™). Monocytes are isolated from PBMC by counterflow centrifugal elutriation.

Monocyte Survival Assay. Human peripheral blood monocytes progressively lose viability when cultured in absence of serum or other stimuli. Their death results from internally regulated processes (apoptosis). Addition to the culture of activating factors, such as TNF-alpha dramatically improves cell survival and prevents DNA fragmentation. Propidium iodide (PI) staining is used to measure apoptosis as follows. Monocytes are cultured for 48 hours in polypropylene tubes in serum-free medium (positive control), in the presence of 100 ng/ml TNF-alpha (negative control), and in the presence of varying concentrations of the compound to be tested. Cells are suspended at a concentration of $2\times10^6$/ml in PBS containing PI at a final concentration of 5 μg/ml, and then incubated at room temperature for 5 minutes before FACScan analysis. PI uptake has been demonstrated to correlate with DNA fragmentation in this experimental paradigm.

Effect on cytokine release. An important function of monocytes/macrophages is their regulatory activity on other cellular populations of the immune system through the release of cytokines after stimulation. An ELISA to measure cytokine release is performed as follows. Human monocytes are incubated at a density of $5\times10^5$ cells/ml with increasing concentrations of agonists or antagonists of the invention and under the same conditions, but in the absence of agonists or antagonists. For IL-12 production, the cells are primed overnight with IFN (100 U/ml) in the presence of agonist or antagonist of the invention. LPS (10 ng/ml) is then added. Conditioned media are collected after 24 h and kept frozen until use. Measurement of TNF-alpha, IL-10, MCP-1 and IL-8 is then performed using a commercially available ELISA kit (e.g., R & D Systems (Minneapolis, Minn.)) and applying the standard protocols provided with the kit.

Oxidative burst. Purified monocytes are plated in 96-well plate at $2\text{-}1\times10^5$ cell/well. Increasing concentrations of agonists or antagonists of the invention are added to the wells in a total volume of 0.2 ml culture medium (RPMI 1640+10% FCS, glutamine and antibiotics). After 3 days incubation, the plates are centrifuged and the medium is removed from the wells. To the macrophage monolayers, 0.2 ml per well of phenol red solution (140 mM NaCl, 10 mM potassium phosphate buffer pH 7.0, 5.5 mM dextrose, 0.56 mM phenol red and 19 U/ml of HRPO) is added, together with the stimulant (200 nM PMA). The plates are incubated at 37° C. for 2 hours and the reaction is stopped by adding 20 μl 1N NaOH per well. The absorbance is read at 610 nm. To calculate the amount of $H_2O_2$ produced by the macrophages, a standard curve of a $H_2O_2$ solution of known molarity is performed for each experiment.

The studies described in this example tested activity of agonists or antagonists of the invention. However, one skilled in the art could easily modify the exemplified studies to test the activity of polynucleotides or polypeptides of the invention (e.g., gene therapy).

Example 24

Biological Effects of Agonists or Antagonists of the Invention Astrocyte and Neuronal Assays Agonists or antagonists of the invention, expressed in *Escherichia coli* and purified as described above, can be tested for activity in promoting the survival, neurite outgrowth, or phenotypic differentiation of cortical neuronal cells and for inducing the proliferation of glial fibrillary acidic protein immunopositive cells, astrocytes. The selection of cortical cells for the bioassay is based on the prevalent expression of FGF-1 and FGF-2 in cortical structures and on the previously reported enhancement of cortical neuronal survival resulting from FGF-2 treatment. A thymidine incorporation assay, for example, can be used to elucidate an agonist or antagonist of the invention's activity on these cells.

Moreover, previous reports describing the biological effects of FGF-2 (basic FGF) on cortical or hippocampal neurons in vitro have demonstrated increases in both neuron survival and neurite outgrowth (Walicke et al., "Fibroblast growth factor promotes survival of dissociated hippocampal neurons and enhances neurite extension." *Proc. Natl. Acad. Sci. USA* 83:3012-3016. (1986), assay herein incorporated by reference in its entirety). However, reports from experiments done on PC-12 cells suggest that these two responses are not necessarily synonymous and may depend on not only which FGF is being tested but also on which receptor(s) are expressed on the target cells. Using the primary cortical neuronal culture paradigm, the ability of an agonist or antagonist of the invention to induce neurite outgrowth can be compared to the response achieved with FGF-2 using, for example, a thymidine incorporation assay.

Fibroblast and Endothelial Cell Assays.

Human lung fibroblasts are obtained from Clonetics (San Diego, Calif.) and maintained in growth media from Clonetics. Dermal microvascular endothelial cells are obtained from Cell Applications (San Diego, Calif.). For proliferation assays, the human lung fibroblasts and dermal microvascular endothelial cells can be cultured at 5,000 cells/well in a 96-well plate for one day in growth medium. The cells are then incubated for one day in 0.1% BSA basal medium. After replacing the medium with fresh 0.1% BSA medium, the cells are incubated with the test proteins for 3 days. ALAMAR BLUE™ (Alamar Biosciences, Sacramento, Calif.) is added to each well to a final concentration of 10%. The cells are incubated for 4 hr. Cell viability is measured by reading in a CYTOFLUOR™ fluorescence reader. For the $PGE_2$ assays, the human lung fibroblasts are cultured at 5,000 cells/well in a 96-well plate for one day. After a medium change to 0.1% BSA basal medium, the cells are incubated with FGF-2 or agonists or antagonists of the invention with or without IL-1α for 24 hours. The supernatants are collected and assayed for $PGE_2$ by EIA kit (Cayman, Ann Arbor, Mich.). For the IL-6 assays, the human lung fibroblasts are cultured at 5,000 cells/well in a 96-well plate for one day. After a medium change to 0.1% BSA basal medium, the cells are incubated with FGF-2 or with or without agonists or antagonists of the invention IL-1α for 24 hours. The supernatants are collected and assayed for IL-6 by ELISA kit (Endogen, Cambridge, Mass.).

Human lung fibroblasts are cultured with FGF-2 or agonists or antagonists of the invention for 3 days in basal medium before the addition of ALAMAR BLUE™ to assess effects on growth of the fibroblasts. FGF-2 should show a stimulation at 10-2500 ng/ml which can be used to compare stimulation with agonists or antagonists of the invention.

Parkinson Models.

The loss of motor function in Parkinson's disease is attributed to a deficiency of striatal dopamine resulting from the degeneration of the nigrostriatal dopaminergic projection neurons. An animal model for Parkinson's that has been extensively characterized involves the systemic administration of 1-methyl-4 phenyl 1,2,3,6-tetrahydropyridine (MPTP). In the CNS, MPTP is taken-up by astrocytes and catabolized by monoamine oxidase B to 1-methyl-4-phenyl pyridine ($MPP^+$) and released. Subsequently, $MPP^+$ is actively accumulated in dopaminergic neurons by the high-affinity reuptake transporter for dopamine. $MPP^+$ is then concentrated in mitochondria by the electrochemical gradient and selectively inhibits nicotidamide adenine disphosphate: ubiquinone oxidoreductionase (complex I), thereby interfering with electron transport and eventually generating oxygen radicals.

It has been demonstrated in tissue culture paradigms that FGF-2 (basic FGF) has trophic activity towards nigral dopaminergic neurons (Ferrari et al., Dev. Biol. 1989). Recently, Dr. Unsicker's group has demonstrated that administering FGF-2 in gel foam implants in the striatum results in the near complete protection of nigral dopaminergic neurons from the toxicity associated with MPTP exposure (Otto and Unsicker, J. Neuroscience, 1990).

Based on the data with FGF-2, agonists or antagonists of the invention can be evaluated to determine whether it has an action similar to that of FGF-2 in enhancing dopaminergic neuronal survival in vitro and it can also be tested in vivo for protection of dopaminergic neurons in the striatum from the damage associated with MPTP treatment. The potential effect of an agonist or antagonist of the invention is first examined in vitro in a dopaminergic neuronal cell culture paradigm. The cultures are prepared by dissecting the midbrain floor plate from gestation day 14 Wistar rat embryos. The tissue is dissociated with trypsin and seeded at a density of 200,000 $cells/cm^2$ on polyorthinine-laminin coated glass coverslips. The cells are maintained in Dulbecco's Modified Eagle's medium and F12 medium containing hormonal supplements (N1). The cultures are fixed with paraformaldehyde after 8 days in vitro and are processed for tyrosine hydroxylase, a specific marker for dopaminergic neurons, immunohistochemical staining. Dissociated cell cultures are prepared from embryonic rats. The culture medium is changed every third day and the factors are also added at that time.

Since the dopaminergic neurons are isolated from animals at gestation day 14, a developmental time which is past the stage when the dopaminergic precursor cells are proliferating, an increase in the number of tyrosine hydroxylase immunopositive neurons would represent an increase in the number of dopaminergic neurons surviving in vitro. Therefore, if an agonist or antagonist of the invention acts to prolong the survival of dopaminergic neurons, it would suggest that the agonist or antagonist may be involved in Parkinson's Disease.

The studies described in this example tested activity of agonists or antagonists of the invention. However, one skilled in the art could easily modify the exemplified studies to test the activity of polynucleotides or polypeptides of the invention (e.g., gene therapy).

Example 25

The Effect of Agonists or Antagonists of the Invention on the Growth of Vascular Endothelial Cells On day 1, human umbilical vein endothelial cells (HUVEC) are seeded at $2\text{-}5\times10^4$ cells/35 mm dish density in M199 medium containing 4% fetal bovine serum (FBS), 16 units/ml heparin, and 50 units/ml endothelial cell growth supplements (ECGS, Biotechnique, Inc.). On day 2, the medium is replaced with M199 containing 10% FBS, 8 units/ml heparin. An agonist or antagonist of the invention, and positive controls, such as VEGF and basic FGF (bFGF) are added, at varying concentrations. On days 4 and 6, the medium is replaced. On day 8, cell number is determined with a Coulter Counter.

An increase in the number of HUVEC cells indicates that the compound of the invention may proliferate vascular endothelial cells, while a decrease in the number of HUVEC cells indicates that the compound of the invention inhibits vascular endothelial cells.

The studies described in this example tested activity of a polypeptide of the invention. However, one skilled in the art could easily modify the exemplified studies to test the activity of polynucleotides or polypeptides of the invention (e.g., gene therapy).

Example 26

Stimulatory Effect of Polypeptides of the Invention on the Proliferation of Vascular Endothelial Cells For evaluation of mitogenic activity of growth factors, the colorimetric MTS (3-(4,5-dimethylthiazol-2-yl)-5-(3-carboxymethoxyphenyl)-2-(4-sulfophenyl)2H-tetrazolium) assay with the electron coupling reagent PMS (phenazine methosulfate) was performed (CellTiter 96 AQ, PROMEGA™). Cells are seeded in a 96-well plate (5,000 cells/well) in 0.1 mL serum-supplemented medium and are allowed to attach overnight. After serum-starvation for 12 hours in 0.5% FBS, conditions (bFGF, $VEGF_{165}$ or a polypeptide of the invention in 0.5% FBS) with or without Heparin (8 U/ml) are added to wells for 48 hours. 20 mg of MTS/PMS mixture (1:0.05) are added per well and allowed to incubate for 1 hour at 37° C. before measuring the absorbance at 490 nm in an ELISA plate reader. Background absorbance from control wells (some media, no cells) is subtracted, and seven wells are performed in parallel for each condition. See, Leak et al. *In Vitro Cell. Dev. Biol.* 30A:512-518 (1994).

The studies described in this example tested activity of a polypeptide of the invention. However, one skilled in the art could easily modify the exemplified studies to test the activity of polynucleotides (e.g., gene therapy), agonists, and/or antagonists of the invention.

Example 27

Inhibition of PDGF-induced Vascular Smooth Muscle Cell Proliferation Stimulatory Effect HAoSMC proliferation can be measured, for example, by BrdUrd incorporation. Briefly, subconfluent, quiescent cells grown on the 4-chamber slides are transfected with CRP or FITC-labeled AT2-3LP. Then, the cells are pulsed with 10% calf serum and 6 mg/ml BrdUrd. After 24 h, immunocytochemistry is performed by using BrdUrd Staining Kit (Zymed Laboratories). In brief, the cells are incubated with the biotinylated mouse anti-BrdUrd antibody at 4 degrees C. for 2 h after being exposed to denaturing solution and then incubated with the streptavidin-peroxidase and diaminobenzidine. After counterstaining with hematoxylin, the cells are mounted for microscopic examination, and the BrdUrd-positive cells are counted. The BrdUrd index is calculated as a percent of the BrdUrd-positive cells to the total cell number.

In addition, the simultaneous detection of the BrdUrd staining (nucleus) and the FITC uptake (cytoplasm) is performed for individual cells by the concomitant use of bright field illumination and dark field-UV fluorescent illumination. See, Hayashida et al., J. Biol. Chem. 6:271(36):21985-21992 (1996).

The studies described in this example tested activity of a polypeptide of the invention. However, one skilled in the art could easily modify the exemplified studies to test the activity of polynucleotides (e.g., gene therapy), agonists, and/or antagonists of the invention.

Example 28

Stimulation of Endothelial Migration

This example will be used to explore the possibility that a polypeptide of the invention may stimulate lymphatic endothelial cell migration.

Endothelial cell migration assays are performed using a 48 well microchemotaxis chamber (Neuroprobe Inc., Cabin John, Md.; Falk, W., et al., J. Immunological Methods 1980; 33:239-247). Polyvinylpyrrolidone-free polycarbonate filters with a pore size of 8 μM (Nucleopore Corp. Cambridge, Mass.) are coated with 0.1% gelatin for at least 6 hours at room temperature and dried under sterile air. Test substances are diluted to appropriate concentrations in M199 supplemented with 0.25% bovine serum albumin (BSA), and 25 ul of the final dilution is placed in the lower chamber of the modified Boyden apparatus. Subconfluent, early passage (2-6) HUVEC or BMEC cultures are washed and trypsinized for the minimum time required to achieve cell detachment. After placing the filter between lower and upper chamber, $2.5\times10^5$ cells suspended in 50 ul M199 containing 1% FBS are seeded in the upper compartment. The apparatus is then incubated for 5 hours at 37° C. in a humidified chamber with 5% CO2 to allow cell migration. After the incubation period, the filter is removed and the upper side of the filter with the non-migrated cells is scraped with a rubber policeman. The filters are fixed with methanol and stained with a Giemsa solution (Diff-Quick, Baxter, McGraw Park, Ill.). Migration is quantified by counting cells of three random high-power fields (40×) in each well, and all groups are performed in quadruplicate.

The studies described in this example tested activity of a polypeptide of the invention. However, one skilled in the art could easily modify the exemplified studies to test the activity of polynucleotides (e.g., gene therapy), agonists, and/or antagonists of the invention.

Example 29

Stimulation of Nitric Oxide Production by Endothelial Cells

Nitric oxide released by the vascular endothelium is believed to be a mediator of vascular endothelium relaxation. Thus, activity of a polypeptide of the invention can be assayed by determining nitric oxide production by endothelial cells in response to the polypeptide.

Nitric oxide is measured in 96-well plates of confluent microvascular endothelial cells after 24 hours starvation and a subsequent 4 hr exposure to various levels of a positive control (such as VEGF-1) and the polypeptide of the invention. Nitric oxide in the medium is determined by use of the Griess reagent to measure total nitrite after reduction of nitric oxide-derived nitrate by nitrate reductase. The effect of the polypeptide of the invention on nitric oxide release is examined on HUVEC.

Briefly, NO release from cultured HUVEC monolayer is measured with a NO-specific polarographic electrode connected to a NO meter (Iso-NO, World Precision Instruments Inc.) (1049). Calibration of the NO elements is performed according to the following equation:

$$2KNO_2+2KI+2H_2SO_462NO+I_2+2H_2O+2K_2SO_4$$

The standard calibration curve is obtained by adding graded concentrations of $KNO_2$ (0, 5, 10, 25, 50, 100, 250, and 500 nmol/L) into the calibration solution containing $K_1$ and $H_2SO_4$. The specificity of the Iso-NO electrode to NO is previously determined by measurement of NO from authentic NO gas (1050). The culture medium is removed and HUVECs are washed twice with Dulbecco's phosphate buffered saline. The cells are then bathed in 5 ml of filtered Krebs-Henseleit solution in 6-well plates, and the cell plates are kept on a slide warmer (Lab Line Instruments Inc.) To maintain the temperature at 37° C. The NO sensor probe is inserted vertically into the wells, keeping the tip of the electrode 2 mm under the surface of the solution, before addition of the different conditions. S-nitroso acetyl penicillamin (SNAP) is used as a positive control. The amount of released NO is expressed as picomoles per $1\times10^6$ endothelial cells. All values reported are means of four to six measurements in each group (number of cell culture wells). See, Leak et al. *Biochem. and Biophys. Res. Comm.* 217:96-105 (1995).

The studies described in this example tested activity of polypeptides of the invention. However, one skilled in the art could easily modify the exemplified studies to test the activity of polynucleotides (e.g., gene therapy), agonists, and/or antagonists of the invention.

Example 30

Effect of Polypeptides of the Invention on Cord Formation in Angiogenesis

Another step in angiogenesis is cord formation, marked by differentiation of endothelial cells. This bioassay measures the ability of microvascular endothelial cells to form capillary-like structures (hollow structures) when cultured in vitro.

CADMEC (microvascular endothelial cells) are purchased from Cell Applications, Inc. as proliferating (passage 2) cells and are cultured in Cell Applications' CADMEC Growth Medium and used at passage 5. For the in vitro angiogenesis assay, the wells of a 48-well cell culture plate are coated with Cell Applications' Attachment Factor Medium (200 ml/well) for 30 min. at 37° C. CADMEC are seeded onto the coated wells at 7,500 cells/well and cultured overnight in Growth Medium. The Growth Medium is then replaced with 300 mg Cell Applications' Chord Formation Medium containing control buffer or a polypeptide of the invention (0.1 to 100 ng/ml) and the cells are cultured for an additional 48 hr. The numbers and lengths of the capillary-like chords are quantitated through use of the Boeckeler VIA-170 video image analyzer. All assays are done in triplicate.

Commercial (R&D) VEGF (50 ng/ml) is used as a positive control. b-estradiol (1 ng/ml) is used as a negative control. The appropriate buffer (without protein) is also utilized as a control.

The studies described in this example tested activity of a polypeptide of the invention. However, one skilled in the art could easily modify the exemplified studies to test the activity of polynucleotides (e.g., gene therapy), agonists, and/or antagonists of the invention.

Example 31

Angiogenic Effect on Chick Chorioallantoic Membrane

Chick chorioallantoic membrane (CAM) is a well-established system to examine angiogenesis. Blood vessel formation on CAM is easily visible and quantifiable. The ability of polypeptides of the invention to stimulate angiogenesis in CAM can be examined.

Fertilized eggs of the White Leghorn chick (*Gallus gallus*) and the Japanese quail (*Coturnix coturnix*) are incubated at 37.8° C. and 80% humidity. Differentiated CAM of 16-day-old chick and 13-day-old quail embryos is studied with the following methods.

On Day 4 of development, a window is made into the egg shell of chick eggs. The embryos are checked for normal development and the eggs sealed with cellotape. They are further incubated until Day 13. THERMANOX™ coverslips (Nunc, Naperville, Ill.) are cut into disks of about 5 mm in diameter. Sterile and salt-free growth factors are dissolved in distilled water and about 3.3 mg/5 ml are pipetted on the disks. After air-drying, the inverted disks are applied on CAM. After 3 days, the specimens are fixed in 3% glutaraldehyde and 2% formaldehyde and rinsed in 0.12 M sodium cacodylate buffer. They are photographed with a stereo microscope [Wild M8] and embedded for semi- and ultrathin sectioning as described above. Controls are performed with carrier disks alone.

The studies described in this example tested activity of a polypeptide of the invention. However, one skilled in the art could easily modify the exemplified studies to test the activity of polynucleotides (e.g., gene therapy), agonists, and/or antagonists of the invention.

Example 32

Angiogenesis Assay Using a MATRIGEL™ Implant in Mouse

In vivo angiogenesis assay of a polypeptide of the invention measures the ability of an existing capillary network to form new vessels in an implanted capsule of murine extracellular matrix material (MATRIGEL™). The protein is mixed with the liquid MATRIGEL™ at 4 degree C. and the mixture is then injected subcutaneously in mice where it solidifies. After 7 days, the solid “plug” of MATRIGEL™ is removed and examined for the presence of new blood vessels. MATRIGEL™ is purchased from Becton Dickinson Labware/Collaborative Biomedical Products.

When thawed at 4 degree C. the MATRIGEL™ material is a liquid. The MATRIGEL™ is mixed with a polypeptide of the invention at 150 ng/ml at 4 degrees C. and drawn into cold 3 ml syringes. Female C57B1/6 mice approximately 8 weeks old are injected with the mixture of MATRIGEL™ and experimental protein at 2 sites at the midventral aspect of the abdomen (0.5 ml/site). After 7 days, the mice are sacrificed by cervical dislocation, the MATRIGEL™ plugs are removed and cleaned (i.e., all clinging membranes and fibrous tissue is removed). Replicate whole plugs are fixed in neutral buffered 10% formaldehyde, embedded in paraffin and used to produce sections for histological examination after staining with Masson’s Trichrome. Cross sections from 3 different regions of each plug are processed. Selected sections are stained for the presence of vWF. The positive control for this assay is bovine basic FGF (150 ng/ml). MATRIGEL™ alone is used to determine basal levels of angiogenesis.

The studies described in this example tested activity of a polypeptide of the invention. However, one skilled in the art could easily modify the exemplified studies to test the activity of polynucleotides (e.g., gene therapy), agonists, and/or antagonists of the invention.

Example 33

Rescue of Ischemia in Rabbit Lower Limb Model

To study the in vivo effects of polynucleotides and polypeptides of the invention on ischemia, a rabbit hindlimb ischemia model is created by surgical removal of one femoral artery as described previously (Takeshita et al., *Am J. Pathol* 147:1649-1660 (1995)). The excision of the femoral artery results in retrograde propagation of thrombus and occlusion of the external iliac artery. Consequently, blood flow to the ischemic limb is dependent upon collateral vessels originating from the internal iliac artery (Takeshita et al. *Am J. Pathol* 147:1649-1660 (1995)). An interval of 10 days is allowed for post-operative recovery of rabbits and development of endogenous collateral vessels. At 10 day post-operatively (day 0), after performing a baseline angiogram, the internal iliac artery of the ischemic limb is transfected with 500 mg naked expression plasmid containing a polynucleotide of the invention by arterial gene transfer technology using a hydrogel-coated balloon catheter as described (Riessen et al. *Hum Gene Ther.* 4:749-758 (1993); Leclerc et al. *J. Clin. Invest.* 90: 936-944 (1992)). When a polypeptide of the invention is used in the treatment, a single bolus of 500 mg polypeptide of the invention or control is delivered into the internal iliac artery of the ischemic limb over a period of 1 min. through an infusion catheter. On day 30, various parameters are measured in these rabbits: (a) BP ratio—The blood pressure ratio of systolic pressure of the ischemic limb to that of normal limb; (b) Blood Flow and Flow Reserve—Resting FL: the blood flow during undilated condition and Max FL: the blood flow during fully dilated condition (also an indirect measure of the blood vessel amount) and Flow Reserve is reflected by the ratio of max FL:resting FL; (c) Angiographic Score—This is measured by the angiogram of collateral vessels. A score is determined by the percentage of circles in an overlaying grid that with crossing opacified arteries divided by the total number m the rabbit thigh; (d) Capillary density—The number of collateral capillaries determined in light microscopic sections taken from hindlimbs.

The studies described in this example tested activity of polynucleotides and polypeptides of the invention. However, one skilled in the art could easily modify the exemplified studies to test the agonists, and/or antagonists of the invention.

Example 34

Effect of Polypeptides of the Invention on Vasodilation

Since dilation of vascular endothelium is important in reducing blood pressure, the ability of polypeptides of the invention to affect the blood pressure in spontaneously hypertensive rats (SHR) is examined. Increasing doses (0, 10, 30, 100, 300, and 900 mg/kg) of the polypeptides of the invention are administered to 13-14 week old spontaneously hypertensive rats (SHR). Data are expressed as the mean+/−SEM. Statistical analysis are performed with a paired t-test and statistical significance is defined as $p<0.05$ vs. the response to buffer alone.

The studies described in this example tested activity of a polypeptide of the invention. However, one skilled in the art could easily modify the exemplified studies to test the activity of polynucleotides (e.g., gene therapy), agonists, and/or antagonists of the invention.

Example 35

Rat Ischemic Skin Flap Model

The evaluation parameters include skin blood flow, skin temperature, and factor VIII immunohistochemistry or endothelial alkaline phosphatase reaction. Expression of polypeptides of the invention, during the skin ischemia, is studied using in situ hybridization.

The study in this model is divided into three parts as follows:

Ischemic skin

Ischemic skin wounds

Normal wounds

The experimental protocol includes:

Raising a 3×4 cm, single pedicle full-thickness random skin flap (myocutaneous flap over the lower back of the animal).

An excisional wounding (4-6 mm in diameter) in the ischemic skin (skin-flap).

Topical treatment with a polypeptide of the invention of the excisional wounds (day 0, 1, 2, 3, 4 post-wounding) at the following various dosage ranges: 1 mg to 100 mg.

Harvesting the wound tissues at day 3, 5, 7, 10, 14 and 21 post-wounding for histological, immunohistochemical, and in situ studies.

The studies described in this example tested activity of a polypeptide of the invention. However, one skilled in the art could easily modify the exemplified studies to test the activity of polynucleotides (e.g., gene therapy), agonists, and/or antagonists of the invention.

Example 36

Peripheral Arterial Disease Model

Angiogenic therapy using a polypeptide of the invention is a novel therapeutic strategy to obtain restoration of blood flow around the ischemia in case of peripheral arterial diseases. The experimental protocol includes:

One side of the femoral artery is ligated to create ischemic muscle of the hindlimb, the other side of hindlimb serves as a control.

A polypeptide of the invention, in a dosage range of 20 mg-500 mg, is delivered intravenously and/or intramuscularly 3 times (perhaps more) per week for 2-3 weeks.

The ischemic muscle tissue is collected after ligation of the femoral artery at 1, 2, and 3 weeks for the analysis of expression of a polypeptide of the invention and histology. Biopsy is also performed on the other side of normal muscle of the contralateral hindlimb.

The studies described in this example tested activity of a polypeptide of the invention. However, one skilled in the art could easily modify the exemplified studies to test the activity of polynucleotides (e.g., gene therapy), agonists, and/or antagonists of the invention.

Example 37

Ischemic Myocardial Disease Model

A polypeptide of the invention is evaluated as a potent mitogen capable of stimulating the development of collateral vessels, and restructuring new vessels after coronary artery occlusion. Alteration of expression of the polypeptide is investigated in situ. The experimental protocol includes:

The heart is exposed through a left-side thoracotomy in the rat. Immediately, the left coronary artery is occluded with a thin suture (6-0) and the thorax is closed.

A polypeptide of the invention, in a dosage range of 20 mg-500 mg, is delivered intravenously and/or intramuscularly 3 times (perhaps more) per week for 2-4 weeks.

Thirty days after the surgery, the heart is removed and cross-sectioned for morphometric and in situ analyzes.

The studies described in this example tested activity of a polypeptide of the invention. However, one skilled in the art could easily modify the exemplified studies to test the activity of polynucleotides (e.g., gene therapy), agonists, and/or antagonists of the invention.

Example 38

Rat Corneal Wound Healing Model

This animal model shows the effect of an agonist or antagonist of the invention on neovascularization. The experimental protocol includes:

a) Making a 1-1.5 mm long incision from the center of cornea into the stromal layer.

b) Inserting a spatula below the lip of the incision facing the outer corner of the eye.

c) Making a pocket (its base is 1-1.5 mm form the edge of the eye).

d) Positioning a pellet, containing 50 ng-5 μg of an agonist or antagonist of the invention, within the pocket.

e) Treatment with an agonist or antagonist of the invention can also be applied topically to the corneal wounds in a dosage range of 20 mg-500 mg (daily treatment for five days).

The studies described in this example tested activity of agonists or antagonists of the invention. However, one skilled in the art could easily modify the exemplified studies to test the activity of polynucleotides or polypeptides of the invention (e.g., gene therapy).

Example 39

Diabetic Mouse and Glucocorticoid-Impaired Wound Healing Models

Diabetic db+/db+ Mouse Model.

To demonstrate that an agonist or antagonist of the invention accelerates the healing process, the genetically diabetic mouse model of wound healing is used. The full thickness wound healing model in the db+/db+ mouse is a well characterized, clinically relevant and reproducible model of impaired wound healing. Healing of the diabetic wound is dependent on formation of granulation tissue and re-epithelialization rather than contraction (Gartner, M. H. et al., *J. Surg. Res.* 52:389 (1992); Greenhalgh, D. G. et al., *Am. J. Pathol.* 136:1235 (1990)).

The diabetic animals have many of the characteristic features observed in Type II diabetes mellitus. Homozygous (db+/db+) mice are obese in comparison to their normal heterozygous (db+/+m) littermates. Mutant diabetic (db+/db+)

mice have a single autosomal recessive mutation on chromosome 4 (db+) (Coleman et al. *Proc. Natl. Acad. Sci. USA* 77:283-293 (1982)). Animals show polyphagia, polydipsia and polyuria. Mutant diabetic mice (db+/db+) have elevated blood glucose, increased or normal insulin levels, and suppressed cell-mediated immunity (Mandel et al., *J. Immunol.* 120:1375 (1978); Debray-Sachs, M. et al., *Clin. Exp. Immunol.* 51(1):1-7 (1983); Leiter et al., *Am. J. of Pathol.* 114:46-55 (1985)). Peripheral neuropathy, myocardial complications, and microvascular lesions, basement membrane thickening and glomerular filtration abnormalities have been described in these animals (Norido, F. et al., *Exp. Neurol.* 83(2):221-232 (1984); Robertson et al., *Diabetes* 29(1):60-67 (1980); Giacomelli et al., *Lab Invest.* 40(4):460-473 (1979); Coleman, D. L., *Diabetes* 31 (*Suppl*):1-6 (1982)). These homozygous diabetic mice develop hyperglycemia that is resistant to insulin analogous to human type II diabetes (Mandel et al., *J. Immunol.* 120:1375-1377 (1978)).

The characteristics observed in these animals suggests that healing in this model may be similar to the healing observed in human diabetes (Greenhalgh, et al., *Am. J. of Pathol.* 136: 1235-1246 (1990)).

Genetically diabetic female C57BL/KsJ (db+/db+) mice and their non-diabetic (db+/+m) heterozygous littermates are used in this study (Jackson Laboratories). The animals are purchased at 6 weeks of age and are 8 weeks old at the beginning of the study. Animals are individually housed and received food and water ad libitum. All manipulations are performed using aseptic techniques. The experiments are conducted according to the rules and guidelines of Human Genome Sciences, Inc. Institutional Animal Care and Use Committee and the Guidelines for the Care and Use of Laboratory Animals.

Wounding protocol is performed according to previously reported methods (Tsuboi, R. and Rifkin, D. B., *J. Exp. Med.* 172:245-251 (1990)). Briefly, on the day of wounding, animals are anesthetized with an intraperitoneal injection of Avertin™ (0.01 mg/mL), 2,2,2-tribromoethanol and 2-methyl-2-butanol dissolved in deionized water. The dorsal region of the animal is shaved and the skin washed with 70% ethanol solution and iodine. The surgical area is dried with sterile gauze prior to wounding. An 8 mm full-thickness wound is then created using a Keyes tissue punch. Immediately following wounding, the surrounding skin is gently stretched to eliminate wound expansion. The wounds are left open for the duration of the experiment. Application of the treatment is given topically for 5 consecutive days commencing on the day of wounding. Prior to treatment, wounds are gently cleansed with sterile saline and gauze sponges.

Wounds are visually examined and photographed at a fixed distance at the day of surgery and at two day intervals thereafter. Wound closure is determined by daily measurement on days 1-5 and on day 8. Wounds are measured horizontally and vertically using a calibrated Jameson caliper. Wounds are considered healed if granulation tissue is no longer visible and the wound is covered by a continuous epithelium.

An agonist or antagonist of the invention is administered using at a range different doses, from 4 mg to 500 mg per wound per day for 8 days in vehicle. Vehicle control groups received 50 mL of vehicle solution.

Animals are euthanized on day 8 with an intraperitoneal injection of sodium pentobarbital (300 mg/kg). The wounds and surrounding skin are then harvested for histology and immunohistochemistry. Tissue specimens are placed in 10% neutral buffered formalin in tissue cassettes between biopsy sponges for further processing.

Three groups of 10 animals each (5 diabetic and 5 non-diabetic controls) are evaluated: 1) Vehicle placebo control, 2) untreated group, and 3) treated group.

Wound closure is analyzed by measuring the area in the vertical and horizontal axis and obtaining the total square area of the wound. Contraction is then estimated by establishing the differences between the initial wound area (day 0) and that of post treatment (day 8). The wound area on day 1 is 64 $mm^2$, the corresponding size of the dermal punch. Calculations are made using the following formula:

[Open area on day 8]−[Open area on day 1]/[Open area on day 1]

Specimens are fixed in 10% buffered formalin and paraffin embedded blocks are sectioned perpendicular to the wound surface (5 mm) and cut using a Reichert-Jung microtome. Routine hematoxylin-eosin (H&E) staining is performed on cross-sections of bisected wounds. Histologic examination of the wounds are used to assess whether the healing process and the morphologic appearance of the repaired skin is altered by treatment with an agonist or antagonist of the invention. This assessment included verification of the presence of cell accumulation, inflammatory cells, capillaries, fibroblasts, re-epithelialization and epidermal maturity (Greenhalgh, D. G. et al., *Am. J. Pathol.* 136:1235 (1990)). A calibrated lens micrometer is used by a blinded observer.

Tissue sections are also stained immunohistochemically with a polyclonal rabbit anti-human keratin antibody using ABC Elite detection system. Human skin is used as a positive tissue control while non-immune IgG is used as a negative control. Keratinocyte growth is determined by evaluating the extent of reepithelialization of the wound using a calibrated lens micrometer.

Proliferating cell nuclear antigen/cyclin (PCNA) in skin specimens is demonstrated by using anti-PCNA antibody (1:50) with an ABC Elite detection system. Human colon cancer served as a positive tissue control and human brain tissue is used as a negative tissue control. Each specimen included a section with omission of the primary antibody and substitution with non-immune mouse IgG. Ranking of these sections is based on the extent of proliferation on a scale of 0-8, the lower side of the scale reflecting slight proliferation to the higher side reflecting intense proliferation.

Experimental data are analyzed using an unpaired t test. A p value of <0.05 is considered significant.

Steroid Impaired Rat Model

The inhibition of wound healing by steroids has been well documented in various in vitro and in vivo systems (Wahl, Glucocorticoids and Wound healing. In: Anti-Inflammatory Steroid Action: Basic and Clinical Aspects. 280-302 (1989); Wahl et al., *J. Immunol.* 115: 476-481 (1975); Werb et al., *J. Exp. Med.* 147:1684-1694 (1978)). Glucocorticoids retard wound healing by inhibiting angiogenesis, decreasing vascular permeability (Ebert et al., *An. Intern. Med.* 37:701-705 (1952)), fibroblast proliferation, and collagen synthesis (Beck et al., *Growth Factors.* 5: 295-304 (1991); Haynes et al., *J. Clin. Invest.* 61: 703-797 (1978)) and producing a transient reduction of circulating monocytes (Haynes et al., *J. Clin. Invest.* 61: 703-797 (1978); Wahl, "Glucocorticoids and wound healing", In: Antiinflammatory Steroid Action: Basic and Clinical Aspects, Academic Press, New York, pp. 280-302 (1989)). The systemic administration of steroids to impair wound healing is a well establish phenomenon in rats (Beck et al., *Growth Factors.* 5: 295-304 (1991); Haynes et al., *J. Clin. Invest.* 61: 703-797 (1978); Wahl, "Glucocorticoids and wound healing", In: Antiinflammatory Steroid Action: Basic and Clinical Aspects, Academic Press, New York, pp. 280-302 (1989); Pierce et al., *Proc. Natl. Acad. Sci. USA* 86: 2229-2233 (1989)).

To demonstrate that an agonist or antagonist of the invention can accelerate the healing process, the effects of multiple topical applications of the agonist or antagonist on full thickness excisional skin wounds in rats in which healing has been impaired by the systemic administration of methylprednisolone is assessed.

Young adult male Sprague Dawley rats weighing 250-300 g (Charles River Laboratories) are used in this example. The animals are purchased at 8 weeks of age and are 9 weeks old at the beginning of the study. The healing response of rats is impaired by the systemic administration of methylprednisolone (17 mg/kg/rat intramuscularly) at the time of wounding. Animals are individually housed and received food and water ad libitum. All manipulations are performed using aseptic techniques. This study is conducted according to the rules and guidelines of Human Genome Sciences, Inc. Institutional Animal Care and Use Committee and the Guidelines for the Care and Use of Laboratory Animals.

The wounding protocol is followed according to section A, above. On the day of wounding, animals are anesthetized with an intramuscular injection of ketamine (50 mg/kg) and xylazine (5 mg/kg). The dorsal region of the animal is shaved and the skin washed with 70% ethanol and iodine solutions. The surgical area is dried with sterile gauze prior to wounding. An 8 mm full-thickness wound is created using a Keyes tissue punch. The wounds are left open for the duration of the experiment. Applications of the testing materials are given topically once a day for 7 consecutive days commencing on the day of wounding and subsequent to methylprednisolone administration. Prior to treatment, wounds are gently cleansed with sterile saline and gauze sponges.

Wounds are visually examined and photographed at a fixed distance at the day of wounding and at the end of treatment. Wound closure is determined by daily measurement on days 1-5 and on day 8. Wounds are measured horizontally and vertically using a calibrated Jameson caliper. Wounds are considered healed if granulation tissue is no longer visible and the wound is covered by a continuous epithelium.

The agonist or antagonist of the invention is administered using at a range different doses, from 4 mg to 500 mg per wound per day for 8 days in vehicle. Vehicle control groups received 50 mL of vehicle solution.

Animals are euthanized on day 8 with an intraperitoneal injection of sodium pentobarbital (300 mg/kg). The wounds and surrounding skin are then harvested for histology. Tissue specimens are placed in 10% neutral buffered formalin in tissue cassettes between biopsy sponges for further processing.

Three groups of 10 animals each (5 with methylprednisolone and 5 without glucocorticoid) are evaluated: 1) Untreated group 2) Vehicle placebo control 3) treated groups.

Wound closure is analyzed by measuring the area in the vertical and horizontal axis and obtaining the total area of the wound. Closure is then estimated by establishing the differences between the initial wound area (day 0) and that of post treatment (day 8). The wound area on day 1 is 64 $mm^2$, the corresponding size of the dermal punch. Calculations are made using the following formula:

$$[\text{Open area on day 8}]-[\text{Open area on day 1}]/[\text{Open area on day 1}]$$

Specimens are fixed in 10% buffered formalin and paraffin embedded blocks are sectioned perpendicular to the wound surface (5 mm) and cut using an Olympus microtome. Routine hematoxylin-eosin (H&E) staining is performed on cross-sections of bisected wounds. Histologic examination of the wounds allows assessment of whether the healing process and the morphologic appearance of the repaired skin is improved by treatment with an agonist or antagonist of the invention. A calibrated lens micrometer is used by a blinded observer to determine the distance of the wound gap.

Experimental data are analyzed using an unpaired t test. A p value of $<0.05$ is considered significant.

The studies described in this example tested activity of agonists or antagonists of the invention. However, one skilled in the art could easily modify the exemplified studies to test the activity of polynucleotides or polypeptides of the invention (e.g., gene therapy).

Example 40

Lymphadema Animal Model

The purpose of this experimental approach is to create an appropriate and consistent lymphedema model for testing the therapeutic effects of an agonist or antagonist of the invention in lymphangiogenesis and re-establishment of the lymphatic circulatory system in the rat hind limb. Effectiveness is measured by swelling volume of the affected limb, quantification of the amount of lymphatic vasculature, total blood plasma protein, and histopathology. Acute lymphedema is observed for 7-10 days. Perhaps more importantly, the chronic progress of the edema is followed for up to 3-4 weeks.

Prior to beginning surgery, blood sample is drawn for protein concentration analysis. Male rats weighing approximately ~350 g are dosed with Pentobarbital. Subsequently, the right legs are shaved from knee to hip. The shaved area is swabbed with gauze soaked in 70% EtOH. Blood is drawn for serum total protein testing. Circumference and volumetric measurements are made prior to injecting dye into paws after marking 2 measurement levels (0.5 cm above heel, at mid-pt of dorsal paw). The intradermal dorsum of both right and left paws are injected with 0.05 ml of 1% Evan's Blue. Circumference and volumetric measurements are then made following injection of dye into paws.

Using the knee joint as a landmark, a mid-leg inguinal incision is made circumferentially allowing the femoral vessels to be located. Forceps and hemostats are used to dissect and separate the skin flaps. After locating the femoral vessels, the lymphatic vessel that runs along side and underneath the vessel(s) is located. The main lymphatic vessels in this area are then electrically coagulated or suture ligated.

Using a microscope, muscles in back of the leg (near the semitendinosis and adductors) are bluntly dissected. The popliteal lymph node is then located. The 2 proximal and 2 distal lymphatic vessels and distal blood supply of the popliteal node are then ligated by suturing. The popliteal lymph node, and any accompanying adipose tissue, is then removed by cutting connective tissues.

Care is taken to control any mild bleeding resulting from this procedure. After lymphatics are occluded, the skin flaps are sealed by using liquid skin (Vetbond) (AJ Buck). The separated skin edges are sealed to the underlying muscle tissue while leaving a gap of ~0.5 cm around the leg. Skin also may be anchored by suturing to underlying muscle when necessary.

To avoid infection, animals are housed individually with mesh (no bedding). Recovering animals are checked daily through the optimal edematous peak, which typically occurred by day 5-7. The plateau edematous peak are then observed. To evaluate the intensity of the lymphedema, the circumference and volumes of 2 designated places on each paw before operation and daily for 7 days are measured. The effect of plasma proteins on lymphedema is determined and whether protein analysis is a useful testing perimeter is also investigated. The weights of both control and edematous limbs are evaluated at 2 places. Analysis is performed in a blind manner.

Circumference Measurements: Under brief gas anesthetic to prevent limb movement, a cloth tape is used to measure limb circumference. Measurements are done at the ankle bone and dorsal paw by 2 different people and those 2 readings are averaged. Readings are taken from both control and edematous limbs.

Volumetric Measurements: On the day of surgery, animals are anesthetized with Pentobarbital and are tested prior to surgery. For daily volumetrics animals are under brief halothane anesthetic (rapid immobilization and quick recovery), and both legs are shaved and equally marked using waterproof marker on legs. Legs are first dipped in water, then dipped into the instrument to each marked level then measured by Buxco edema software (Chen/Victor). Data is recorded by one person, while the other is dipping the limb to marked area.

Blood-plasma protein measurements: Blood is drawn, spun, and serum separated prior to surgery and then at conclusion for total protein and $Ca2^{+}$ comparison.

Limb Weight Comparison: After drawing blood, the animal is prepared for tissue collection. The limbs are amputated using a quillitine, then both experimental and control legs are cut at the ligature and weighed. A second weighing is done as the tibio-cacaneal joint is disarticulated and the foot is weighed.

Histological Preparations: The transverse muscle located behind the knee (popliteal) area is dissected and arranged in a metal mold, filled with freezeGel, dipped into cold methylbutane, placed into labeled sample bags at −80 EC until sectioning. Upon sectioning, the muscle is observed under fluorescent microscopy for lymphatics.

The studies described in this example tested activity of agonists or antagonists of the invention. However, one skilled in the art could easily modify the exemplified studies to test the activity of polynucleotides or polypeptides of the invention (e.g., gene therapy).

Example 41

Suppression of TNF Alpha-Induced Adhesion Molecule Expression by an Agonist or Antagonist of the Invention The recruitment of lymphocytes to areas of inflammation and angiogenesis involves specific receptor-ligand interactions between cell surface adhesion molecules (CAMs) on lymphocytes and the vascular endothelium. The adhesion process, in both normal and pathological settings, follows a multi-step cascade that involves intercellular adhesion molecule-1 (ICAM-1), vascular cell adhesion molecule-1 (VCAM-1), and endothelial leukocyte adhesion molecule-1 (E-selectin) expression on endothelial cells (EC). The expression of these molecules and others on the vascular endothelium determines the efficiency with which leukocytes may adhere to the local vasculature and extravasate into the local tissue during the development of an inflammatory response. The local concentration of cytokines and growth factor participate in the modulation of the expression of these CAMs.

Tumor necrosis factor alpha (TNF-a), a potent proinflammatory cytokine, is a stimulator of all three CAMs on endothelial cells and may be involved in a wide variety of inflammatory responses, often resulting in a pathological outcome.

The potential of an agonist or antagonist of the invention to mediate a suppression of TNF-a induced CAM expression can be examined. A modified ELISA assay which uses ECs as a solid phase absorbent is employed to measure the amount of CAM expression on TNF-a treated ECs when co-stimulated with a member of the FGF family of proteins.

To perform the experiment, human umbilical vein endothelial cell (HUVEC) cultures are obtained from pooled cord harvests and maintained in growth medium (EGM-2; Clonetics, San Diego, Calif.) supplemented with 10% FCS and 1% penicillin/streptomycin in a 37 degree C. humidified incubator containing 5% $CO_2$. HUVECs are seeded in 96-well plates at concentrations of $1\times10^4$ cells/well in EGM medium at 37 degree C. for 18-24 hrs or until confluent. The monolayers are subsequently washed 3 times with a serum-free solution of RPMI-1640 supplemented with 100 U/ml penicillin and 100 mg/ml streptomycin, and treated with a given cytokine and/or growth factor(s) for 24 h at 37 degree C. Following incubation, the cells are then evaluated for CAM expression.

Human Umbilical Vein Endothelial cells (HUVECs) are grown in a standard 96 well plate to confluence. Growth medium is removed from the cells and replaced with 90 μl of 199 Medium (10% FBS). Samples for testing and positive or negative controls are added to the plate in triplicate (in 10 μl volumes). Plates are incubated at 37 degree C. for either 5 h (selectin and integrin expression) or 24 h (integrin expression only). Plates are aspirated to remove medium and 100 μl of 0.1% paraformaldehyde-PBS (with Ca++ and Mg++) is added to each well. Plates are held at 4° C. for 30 min.

Fixative is then removed from the wells and wells are washed 1× with PBS(+Ca,Mg)+0.5% BSA and drained. The wells should not be allowed to dry. 10 μl of diluted primary antibody is then added to the test and control wells. Anti-ICAM-1-Biotin, Anti-VCAM-1-Biotin and Anti-E-selectin-Biotin are used at a concentration of 10 μg/ml (1:10 dilution of 0.1 mg/ml stock antibody). Cells are incubated at 37° C. for 30 min. in a humidified environment. Wells are washed ×3 with PBS(+Ca,Mg)+0.5% BSA.

Then add 20 μl of diluted Extravidin®-Alkaline Phosphotase (1:5,000 dilution) to each well and incubated at 37° C. for 30 min. Wells are washed ×3 with PBS(+Ca,Mg)+0.5% BSA. 1 tablet of p-Nitrophenol Phosphate pNPP is dissolved in 5 ml of glycine buffer (pH 10.4). 100 μl of pNPP substrate in glycine buffer is added to each test well. Standard wells in triplicate are prepared from the working dilution of the Extravidin®-Alkaline Phosphotase in glycine buffer: 1:5,000 $(10^0)>10^{-0.5}>10^{-1}>10^{-1.5}$. 5 μl of each dilution is added to triplicate wells and the resulting AP content in each well is 5.50 ng, 1.74 ng, 0.55 ng, 0.18 ng. 100 μl of pNNP reagent must then be added to each of the standard wells. The plate must be incubated at 37° C. for 4 h. A volume of 50 μl of 3M NaOH is added to all wells. The results are quantified on a plate reader at 405 nm. The background subtraction option is used on blank wells filled with glycine buffer only. The template is set up to indicate the concentration of AP-conjugate in each standard well [5.50 ng; 1.74 ng; 0.55 ng; 0.18 ng]. Results are indicated as amount of bound AP-conjugate in each sample.

The studies described in this example tested activity of agonists or antagonists of the invention. However, one skilled in the art could easily modify the exemplified studies to test the activity of polynucleotides or polypeptides of the invention (e.g., gene therapy).

Example 42

Production of Polypeptide of the Invention for High-Throughput Screening Assays

The following protocol produces a supernatant containing polypeptide of the present invention to be tested. This supernatant can then be used in the Screening Assays described in Examples 44-53.

First, dilute Poly-D-Lysine (644 587 BOEHRINGER™ Mannheim) stock solution (1 mg/ml in PBS) 1:20 in PBS (w/o calcium or magnesium 17-516F Biowhittaker) for a working solution of 50 ug/ml. Add 200 μl of this solution to each well (24 well plates) and incubate at RT for 20 minutes. Be sure to distribute the solution over each well (note: a 12-channel pipetter may be used with tips on every other channel). Aspirate off the Poly-D-Lysine solution and rinse with 1 ml PBS (Phosphate Buffered Saline). The PBS should remain in the well until just prior to plating the cells and plates may be poly-lysine coated in advance for up to two weeks.

Plate 293T cells (do not carry cells past P+20) at $2\times10^5$ cells/well in 0.5 ml DMEM (Dulbecco's Modified Eagle Medium)(with 4.5 G/L glucose and L-glutamine (12-604F Biowhittaker))/10% heat inactivated FBS (14-503F Biowhittaker)/1× Penstrep (17-602E Biowhittaker). Let the cells grow overnight.

The next day, mix together in a sterile solution basin: 300 μl LIPOFECTAMINE™ (18324-012 Gibco/BRL) and 5 ml OPTI-MEM™ I (31985070 Gibco/BRL)/96-well plate. With a small volume multi-channel pipetter, aliquot approximately 2 μg of an expression vector containing a polynucleotide insert, produced by the methods described in Examples 8-10, into an appropriately labeled 96-well round bottom plate. With a multi-channel pipetter, add 50 μl of the LIPOFECTAMINE™/OPTI-MEM™ I mixture to each well. Pipette up and down gently to mix. Incubate at RT 15-45 minutes. After about 20 minutes, use a multi-channel pipetter to add 150 μl OPTI-MEM™ I to each well. As a control, one plate of vector DNA lacking an insert should be transfected with each set of transfections.

Preferably, the transfection should be performed by tag-teaming the following tasks. By tag-teaming, hands on time is cut in half, and the cells do not spend too much time on PBS. First, person A aspirates off the media from four 24-well plates of cells, and then person B rinses each well with 0.5-1 ml PBS. Person A then aspirates off PBS rinse, and person B, using a12-channel pipetter with tips on every other channel, adds the 200 μl of DNA/LIPOFECTAMINE™/OPTI-MEM™ I complex to the odd wells first, then to the even wells, to each row on the 24-well plates. Incubate at 37 degree C. for 6 hours.

While cells are incubating, prepare appropriate media, either 1% BSA in DMEM with 1× penstrep, or HGS CHO-5 media (116.6 mg/L of CaCl2 (anhyd); 0.00130 mg/L $CuSO_4$-$5H_2O$; 0.050 mg/L of $Fe(NO_3)_3$-$9H_2O$; 0.417 mg/L of $FeSO_4$-$7H_2O$; 311.80 mg/L of Kcl; 28.64 mg/L of $MgCl_2$; 48.84 mg/L of $MgSO_4$; 6995.50 mg/L of NaCl; 2400.0 mg/L of $NaHCO_3$; 62.50 mg/L of $NaH_2PO_4$—$H_2$0; 71.02 mg/L of $Na_2$HPO4; 0.4320 mg/L of $ZnSO_4$-$7H_2O$; 0.002 mg/L of Arachidonic Acid; 1.022 mg/L of Cholesterol; 0.070 mg/L of DL-alpha-Tocopherol-Acetate; 0.0520 mg/L of Linoleic Acid; 0.010 mg/L of Linolenic Acid; 0.010 mg/L of Myristic Acid; 0.010 mg/L of Oleic Acid; 0.010 mg/L of Palmitric Acid; 0.010 mg/L of Palmitic Acid; 100 mg/L of Pluronic F-68; 0.010 mg/L of Stearic Acid; 2.20 mg/L of Tween 80; 4551 mg/L of D-Glucose; 130.85 mg/ml of L-Alanine; 147.50 mg/ml of L-Arginine-HCL; 7.50 mg/ml of L-Asparagine-$H_2O$; 6.65 mg/ml of L-Aspartic Acid; 29.56 mg/ml of L-Cystine-2HCL-$H_2$0; 31.29 mg/ml of L-Cystine-2HCL; 7.35 mg/ml of L-Glutamic Acid; 365.0 mg/ml of L-Glutamine; 18.75 mg/ml of Glycine; 52.48 mg/ml of L-Histidine-HCL-$H_2$0; 106.97 mg/ml of L-Isoleucine; 111.45 mg/ml of L-Leucine; 163.75 mg/ml of L-Lysine HCL; 32.34 mg/ml of L-Methionine; 68.48 mg/ml of L-Phenylalanine; 40.0 mg/ml of L-Proline; 26.25 mg/ml of L-Serine; 101.05 mg/ml of L-Threonine; 19.22 mg/ml of L-Tryptophan; 91.79 mg/ml of L-Tryosine-2Na-$2H_2$0; and 99.65 mg/ml of L-Valine; 0.0035 mg/L of Biotin; 3.24 mg/L of D-Ca Pantothenate; 11.78 mg/L of Choline Chloride; 4.65 mg/L of Folic Acid; 15.60 mg/L of i-Inositol; 3.02 mg/L of Niacinamide; 3.00 mg/L of Pyridoxal HCL; 0.031 mg/L of Pyridoxine HCL; 0.319 mg/L of Riboflavin; 3.17 mg/L of Thiamine HCL; 0.365 mg/L of Thymidine; 0.680 mg/L of Vitamin $B_{12}$; 25 mM of HEPES Buffer; 2.39 mg/L of Na Hypoxanthine; 0.105 mg/L of Lipoic Acid; 0.081 mg/L of Sodium Putrescine-2HCL; 55.0 mg/L of Sodium Pyruvate; 0.0067 mg/L of Sodium Selenite; 20 μM of Ethanolamine; 0.122 mg/L of Ferric Citrate; 41.70 mg/L of Methyl-B-Cyclodextrin complexed with Linoleic Acid; 33.33 mg/L of Methyl-B-Cyclodextrin complexed with Oleic Acid; 10 mg/L of Methyl-B-Cyclodextrin complexed with Retinal Acetate. Adjust osmolarity to 327 mOsm) with 2 mm glutamine and 1× penstrep. (BSA (81-068-3 BAYER™) 100 gm dissolved in 1 L DMEM for a 10% BSA stock solution). Filter the media and collect 50 μl for endotoxin assay in 15 ml polystyrene conical.

The transfection reaction is terminated, preferably by tag-teaming, at the end of the incubation period. Person A aspirates off the transfection media, while person B adds 1.5 ml appropriate media to each well. Incubate at 37 degree C. for 45 or 72 hours depending on the media used: 1% BSA for 45 hours or CHO-5 for 72 hours.

On day four, using a 300 μl multichannel pipetter, aliquot 600 μl in one 1 ml deep well plate and the remaining supernatant into a 2 ml deep well. The supernatants from each well can then be used in the assays described in Examples 44-51.

It is specifically understood that when activity is obtained in any of the assays described below using a supernatant, the activity originates from either the polypeptide of the present invention directly (e.g., as a secreted protein) or by polypeptide of the present invention inducing expression of other proteins, which are then secreted into the supernatant. Thus, the invention further provides a method of identifying the protein in the supernatant characterized by an activity in a particular assay.

Example 43

Construction of GAS Reporter Construct

One signal transduction pathway involved in the differentiation and proliferation of cells is called the Jaks-STATs pathway. Activated proteins in the Jaks-STATs pathway bind to gamma activation site "GAS" elements or interferon-sensitive responsive element ("ISRE"), located in the promoter of many genes. The binding of a protein to these elements alter the expression of the associated gene.

GAS and ISRE elements are recognized by a class of transcription factors called Signal Transducers and Activators of Transcription, or "STATs." There are six members of the STATs family. Stat1 and Stat3 are present in many cell types, as is Stat2 (as response to IFN-alpha is widespread). Stat4 is more restricted and is not in many cell types though it has been found in T helper class I, cells after treatment with IL-12. Stat5 was originally called mammary growth factor, but has been found at higher concentrations in other cells including myeloid cells. It can be activated in tissue culture cells by many cytokines.

The STATs are activated to translocate from the cytoplasm to the nucleus upon tyrosine phosphorylation by a set of kinases known as the Janus Kinase ("Jaks") family. Jaks represent a distinct family of soluble tyrosine kinases and include Tyk2, Jak1, Jak2, and Jak3. These kinases display significant sequence similarity and are generally catalytically inactive in resting cells.

The Jaks are activated by a wide range of receptors summarized in the Table below. (Adapted from review by Schidler and Darnell, Ann. Rev. Biochem. 64:621-51 (1995)). A cytokine receptor family, capable of activating Jaks, is divided into two groups: (a) Class 1 includes receptors for IL-2, IL-3, IL-4, IL-6, IL-7, IL-9, IL-11, IL-12, IL-15, Epo, PRL, GH, G-CSF, GM-CSF, LIF, CNTF, and thrombopoietin; and (b) Class 2 includes IFN-a, IFN-g, and IL-10. The Class 1 receptors share a conserved cysteine motif (a set of four conserved cysteines and one tryptophan) and a WSXWS motif (a membrane proximal region encoding Trp-Ser-Xaa-Trp-Ser (SEQ ID NO:237)).

Thus, on binding of a ligand to a receptor, Jaks are activated, which in turn activate STATs, which then translocate and bind to GAS elements. This entire process is encompassed in the Jaks-STATs signal transduction pathway. Therefore, activation of the Jaks-STATs pathway, reflected by the binding of the GAS or the ISRE element, can be used to indicate proteins involved in the proliferation and differentiation of cells. For example, growth factors and cytokines are known to activate the Jaks-STATs pathway (See Table below). Thus, by using GAS elements linked to reporter molecules, activators of the Jaks-STATs pathway can be identified.

| | JAKs | | | | | |
|---|---|---|---|---|---|---|
| Ligand | tyk2 | Jak1 | Jak2 | Jak3 | STATS | GAS(elements) or ISRE |
| IFN family | | | | | | |
| IFN-a/B | + | + | − | − | 1, 2, 3 | ISRE |
| IFN-g | | + | + | − | 1 | GAS (IRF1 > Lys6 > IFP) |
| Il-10 | + | ? | ? | − | 1, 3 | |
| gp130 family | | | | | | |
| IL-6 (Pleiotropic) | + | + | + | ? | 1, 3 | GAS (IRF1 > Lys6 > IFP) |
| Il-11 (Pleiotropic) | ? | + | ? | ? | 1, 3 | |
| OnM (Pleiotropic) | ? | + | + | ? | 1, 3 | |
| LIF (Pleiotropic) | ? | + | + | ? | 1, 3 | |
| CNTF (Pleiotropic) | −/+ | + | + | ? | 1, 3 | |
| G-CSF (Pleiotropic) | ? | + | ? | ? | 1, 3 | |
| IL-12 (Pleiotropic) | + | − | + | + | 1, 3 | |
| g-C family | | | | | | |
| IL-2 (lymphocytes) | − | + | − | + | 1, 3, 5 | GAS |
| IL-4 (lymph/myeloid) | − | + | − | + | 6 | GAS (IRF1 = IFP >> Ly6)(IgH) |
| IL-7 (lymphocytes) | − | + | − | + | 5 | GAS |
| IL-9 (lymphocytes) | − | + | − | + | 5 | GAS |
| IL-13 (lymphocyte) | − | + | ? | ? | 6 | GAS |
| IL-15 | ? | + | ? | + | 5 | GAS |
| gp140 family | | | | | | |
| IL-3 (myeloid) | − | − | + | − | 5 | GAS (IRF1 > IFP >> Ly6) |
| IL-5 (myeloid) | − | − | + | − | 5 | GAS |
| GM-CSF (myeloid) | − | − | + | − | 5 | GAS |
| Growth hormone family | | | | | | |
| GH | ? | − | + | − | 5 | |
| PRL | ? | +/− | + | − | 1, 3, 5 | |
| EPO | ? | − | + | − | 5 | GAS(B-CAS > IRF1 = IFP >> Ly6) |
| Receptor Tyrosine Kinases | | | | | | |
| EGF | ? | + | + | − | 1, 3 | GAS (IRF1) |
| PDGF | ? | + | + | − | 1, 3 | |
| CSF-1 | ? | + | + | − | 1, 3 | GAS (not IRF1) |

To construct a synthetic GAS containing promoter element, which is used in the Biological Assays described in Examples 44-45, a PCR based strategy is employed to generate a GAS-SV40 promoter sequence. The 5' primer contains four tandem copies of the GAS binding site found in the IRF1 promoter and previously demonstrated to bind STATs upon induction with a range of cytokines (Rothman et al., Immunity 1:457-468 (1994).), although other GAS or ISRE elements can be used instead. The 5' primer also contains 18 bp of sequence complementary to the SV40 early promoter sequence and is flanked with an XhoI site. The sequence of the 5' primer is:

(SEQ ID NO: 238)

5':GCGCCTCGAGATTTCCCCGAAATCTAGATTTCCCCGAAATGATTTC

CCCGAAATGATTTCCCCGAAATATCTGCCATCTCAATTAG:3'

The downstream primer is complementary to the SV40 promoter and is flanked with a Hind III site: 5':GCGGCAAGCTTTTTGCAAAGCCTAGGC:3' (SEQ ID NO:239)

PCR amplification is performed using the SV40 promoter template present in the B-gal:promoter plasmid obtained from CLONTECH™. The resulting PCR fragment is digested with XhoI/Hind III and subcloned into BLSK2-. (STRATAGENE™.) Sequencing with forward and reverse primers confirms that the insert contains the following sequence:

(SEQ ID NO: 240)

5':CTCGAGATTTCCCCGAAATCTAGATTTCCCCGAAATGATTTCCCCG

AAATGATTTCCCCGAAATATCTGCCATCTCAATTAGTCAGCAACCATAGT

CCCGCCCCTAACTCCGCCCATCCCGCCCCTAACTCCGCCCAGTTCCGCCC

ATTCTCCGCCCCATGGCTGACTAATTTTTTTTATTTATGCAGAGGCCGAG

GCCGCCTCGGCCTCTGAGCTATTCCAGAAGTAGTGAGGAGGCTTTTTTGG

AGGCCTAGGCTTTTGCAAAAAGCTT:3'

With this GAS promoter element linked to the SV40 promoter, a GAS:SEAP2 reporter construct is next engineered. Here, the reporter molecule is a secreted alkaline phosphatase, or "SEAP." Clearly, however, any reporter molecule can be instead of SEAP, in this or in any of the other Examples. Well known reporter molecules that can be used instead of SEAP include chloramphenicol acetyltransferase (CAT), luciferase, alkaline phosphatase, B-galactosidase, green fluorescent protein (GFP), or any protein detectable by an antibody.

The above sequence confirmed synthetic GAS-SV40 promoter element is subcloned into the pSEAP-Promoter vector obtained from CLONTECH™ using HindIII and XhoI, effectively replacing the SV40 promoter with the amplified GAS: SV40 promoter element, to create the GAS-SEAP vector. However, this vector does not contain a neomycin resistance gene, and therefore, is not preferred for mammalian expression systems.

Thus, in order to generate mammalian stable cell lines expressing the GAS-SEAP reporter, the GAS-SEAP cassette is removed from the GAS-SEAP vector using SalI and NotI, and inserted into a backbone vector containing the neomycin resistance gene, such as pGFP-1 (CLONTECH™), using these restriction sites in the multiple cloning site, to create the GAS-SEAP/Neo vector. Once this vector is transfected into mammalian cells, this vector can then be used as a reporter molecule for GAS binding as described in Examples 44-45.

Other constructs can be made using the above description and replacing GAS with a different promoter sequence. For example, construction of reporter molecules containing EGR and NF-KB promoter sequences are described in Examples 46 and 47. However, many other promoters can be substituted using the protocols described in these Examples. For instance, SRE, IL-2, NFAT, or Osteocalcin promoters can be substituted, alone or in combination (e.g., GAS/NF-KB/EGR, GAS/NF-KB, Il-2/NFAT, or NF-KB/GAS). Similarly, other cell lines can be used to test reporter construct activity, such as HELA (epithelial), HUVEC (endothelial), Reh (B-cell), Saos-2 (osteoblast), HUVAC (aortic), or Cardiomyocyte.

Example 44

High-Throughput Screening Assay for T-Cell Activity

The following protocol is used to assess T-cell activity by identifying factors, and determining whether supernatant containing a polypeptide of the invention proliferates and/or differentiates T-cells. T-cell activity is assessed using the GAS/SEAP/Neo construct produced in Example 43. Thus, factors that increase SEAP activity indicate the ability to activate the Jaks-STATS signal transduction pathway. The T-cell used in this assay is Jurkat T-cells (ATCC™ Accession No. TIB-152), although Molt-3 cells (ATCC™ Accession No. CRL-1552) and Molt-4 cells (ATCC™ Accession No. CRL-1582) cells can also be used.

Jurkat T-cells are lymphoblastic CD4+ Th1 helper cells. In order to generate stable cell lines, approximately 2 million Jurkat cells are transfected with the GAS-SEAP/neo vector using DMRIE-C (LIFE TECHNOLOGIES™) (transfection procedure described below). The transfected cells are seeded to a density of approximately 20,000 cells per well and transfectants resistant to 1 mg/ml geneticin selected. Resistant colonies are expanded and then tested for their response to increasing concentrations of interferon gamma. The dose response of a selected clone is demonstrated.

Specifically, the following protocol will yield sufficient cells for 75 wells containing 200 μl of cells. Thus, it is either scaled up, or performed in multiple to generate sufficient cells for multiple 96 well plates. Jurkat cells are maintained in RPMI+10% serum with 1% Pen-Strep. Combine 2.5 mls of OPTI-MEM™ (LIFE TECHNOLOGIES™) with 10 μg of plasmid DNA in a T25 flask. Add 2.5 ml OPTI-MEM™ containing 50 μl of DMRIE-C and incubate at room temperature for 15-45 mins.

During the incubation period, count cell concentration, spin down the required number of cells ($10^7$ per transfection), and resuspend in OPTI-MEM™ to a final concentration of $10^7$ cells/ml. Then add 1 ml of $1\times10^7$ cells in OPTI-MEM™ to T25 flask and incubate at 37 degree C. for 6 hrs. After the incubation, add 10 ml of RPMI+15% serum.

The Jurkat:GAS-SEAP stable reporter lines are maintained in RPMI+10% serum, 1 mg/ml Geneticin, and 1% Pen-Strep. These cells are treated with supernatants containing polypeptide of the present invention or polypeptide of the present invention induced polypeptides as produced by the protocol described in Example 42.

On the day of treatment with the supernatant, the cells should be washed and resuspended in fresh RPMI+10% serum to a density of 500,000 cells per ml. The exact number of cells required will depend on the number of supernatants being screened. For one 96 well plate, approximately 10 million cells (for 10 plates, 100 million cells) are required.

Transfer the cells to a triangular reservoir boat, in order to dispense the cells into a 96 well dish, using a 12 channel pipette. Using a 12 channel pipette, transfer 200 μl of cells into each well (therefore adding 100,000 cells per well).

After all the plates have been seeded, 50 μl of the supernatants are transferred directly from the 96 well plate containing the supernatants into each well using a 12 channel pipette. In addition, a dose of exogenous interferon gamma (0.1, 1.0, 10 ng) is added to wells H9, H10, and H11 to serve as additional positive controls for the assay.

The 96 well dishes containing Jurkat cells treated with supernatants are placed in an incubator for 48 hrs (note: this time is variable between 48-72 hrs). 35 μl samples from each well are then transferred to an opaque 96 well plate using a 12 channel pipette. The opaque plates should be covered (using sellophene covers) and stored at −20 degree C. until SEAP assays are performed according to Example 48. The plates containing the remaining treated cells are placed at 4 degree C. and serve as a source of material for repeating the assay on a specific well if desired.

As a positive control, 100 Unit/ml interferon gamma can be used which is known to activate Jurkat T cells. Over 30 fold induction is typically observed in the positive control wells.

The above protocol may be used in the generation of both transient, as well as, stable transfected cells, which would be apparent to those of skill in the art.

Example 45

High-Throughput Screening Assay Identifying Myeloid Activity

The following protocol is used to assess myeloid activity of polypeptide of the present invention by determining whether polypeptide of the present invention proliferates and/or differentiates myeloid cells. Myeloid cell activity is assessed using the GAS/SEAP/Neo construct produced in Example 43. Thus, factors that increase SEAP activity indicate the ability to activate the Jaks-STATS signal transduction pathway. The myeloid cell used in this assay is U937, a pre-monocyte cell line, although TF-1, HL60, or KG1 can be used.

To transiently transfect U937 cells with the GAS/SEAP/Neo construct produced in Example 43, a DEAE-Dextran method (Kharbanda et. al., 1994, Cell Growth & Differentiation, 5:259-265) is used. First, harvest $2\times10^7$ U937 cells and wash with PBS. The U937 cells are usually grown in RPMI 1640 medium containing 10% heat-inactivated fetal bovine serum (FBS) supplemented with 100 units/ml penicillin and 100 mg/ml streptomycin.

Next, suspend the cells in 1 ml of 20 mM Tris-HCl (pH 7.4) buffer containing 0.5 mg/ml DEAE-Dextran, 8 μg GAS-SEAP2 plasmid DNA, 140 mM NaCl, 5 mM KCl, 375 μM $Na_2HPO_4.7H_2O$, 1 mM $MgCl_2$, and 675 μM $CaCl_2$. Incubate at 37 degrees C. for 45 min.

Wash the cells with RPMI 1640 medium containing 10% FBS and then resuspend in 10 ml complete medium and incubate at 37 degree C. for 36 hr.

The GAS-SEAP/U937 stable cells are obtained by growing the cells in 400 μg/ml G418. The G418-free medium is used for routine growth but every one to two months, the cells should be re-grown in 400 μg/ml G418 for couple of passages.

These cells are tested by harvesting $1\times10^8$ cells (this is enough for ten 96-well plates assay) and wash with PBS. Suspend the cells in 200 ml above described growth medium, with a final density of $5\times10^5$ cells/ml. Plate 200 μl cells per well in the 96-well plate (or $1\times10^5$ cells/well).

Add 50 μl of the supernatant prepared by the protocol described in Example 42. Incubate at 37 degree C. for 48 to 72 hr. As a positive control, 100 Unit/ml interferon gamma can be used which is known to activate U937 cells. Over 30 fold induction is typically observed in the positive control wells. SEAP assay the supernatant according to the protocol described in Example 48.

Example 46

High-Throughput Screening Assay Identifying Neuronal Activity

When cells undergo differentiation and proliferation, a group of genes are activated through many different signal transduction pathways. One of these genes, EGR1 (early growth response gene 1), is induced in various tissues and cell types upon activation. The promoter of EGR1 is responsible for such induction. Using the EGR1 promoter linked to reporter molecules, activation of cells can be assessed by polypeptide of the present invention.

Particularly, the following protocol is used to assess neuronal activity in PC12 cell lines. PC12 cells (rat pheochromocytoma cells) are known to proliferate and/or differentiate by activation with a number of mitogens, such as TPA (tetradecanoyl phorbol acetate), NGF (nerve growth factor), and EGF (epidermal growth factor). The EGR1 gene expression is activated during this treatment. Thus, by stably transfecting PC12 cells with a construct containing an EGR promoter linked to SEAP reporter, activation of PC12 cells by polypeptide of the present invention can be assessed.

The EGR/SEAP reporter construct can be assembled by the following protocol. The EGR-1 promoter sequence (−633 to +1) (Sakamoto K et al., Oncogene 6:867-871 (1991)) can be PCR amplified from human genomic DNA using the following primers:

```
5' GCGCTCGAGGGATGACAGCGATAGAACCCCG (SEQ ID NO: 241)
G-3'

5' GCGAAGCTTCGCGACTCCCCGGATCCGCCT  (SEQ ID NO: 242)
C-3'
```

Using the GAS:SEAP/Neo vector produced in Example 43, EGR1 amplified product can then be inserted into this vector. Linearize the GAS:SEAP/Neo vector using restriction enzymes XhoI/HindIII, removing the GAS/SV40 stuffer. Restrict the EGR1 amplified product with these same enzymes. Ligate the vector and the EGR1 promoter.

To prepare 96 well-plates for cell culture, two mls of a coating solution (1:30 dilution of collagen type I (Upstate Biotech Inc. Cat#08-115) in 30% ethanol (filter sterilized)) is added per one 10 cm plate or 50 ml per well of the 96-well plate, and allowed to air dry for 2 hr.

PC12 cells are routinely grown in RPMI-1640 medium (Bio Whittaker) containing 10% horse serum (JRH BIOSCIENCES, Cat. #12449-78P), 5% heat-inactivated fetal bovine serum (FBS) supplemented with 100 units/ml penicillin and 100 μg/ml streptomycin on a precoated 10 cm tissue culture dish. One to four split is done every three to four days. Cells are removed from the plates by scraping and resuspended with pipetting up and down for more than 15 times.

Transfect the EGR/SEAP/Neo construct into PC12 using the LIPOFECTAMINE™ protocol described in Example 42. EGR-SEAP/PC12 stable cells are obtained by growing the cells in 300 μg/ml G418. The G418-free medium is used for routine growth but every one to two months, the cells should be re-grown in 300 μg/ml G418 for couple of passages.

To assay for neuronal activity, a 10 cm plate with cells around 70 to 80% confluent is screened by removing the old medium. Wash the cells once with PBS (Phosphate buffered saline). Then starve the cells in low serum medium (RPMI-1640 containing 1% horse serum and 0.5% FBS with antibiotics) overnight.

The next morning, remove the medium and wash the cells with PBS. Scrape off the cells from the plate, suspend the cells well in 2 ml low serum medium. Count the cell number and add more low serum medium to reach final cell density as $5\times10^5$ cells/ml.

Add 200 μl of the cell suspension to each well of 96-well plate (equivalent to $1\times10^5$ cells/well). Add 50 μl supernatant produced by Example 42, 37 degree C. for 48 to 72 hr. As a positive control, a growth factor known to activate PC12 cells through EGR can be used, such as 50 ng/μl of Neuronal Growth Factor (NGF). Over fifty-fold induction of SEAP is typically seen in the positive control wells. SEAP assay the supernatant according to Example 48.

Example 47

High-Throughput Screening Assay for T-Cell Activity

NF-KB (Nuclear Factor KB) is a transcription factor activated by a wide variety of agents including the inflammatory cytokines IL-1 and TNF, CD30 and CD40, lymphotoxin-alpha and lymphotoxin-beta, by exposure to LPS or thrombin, and by expression of certain viral gene products. As a transcription factor, NF-KB regulates the expression of genes involved in immune cell activation, control of apoptosis (NF-KB appears to shield cells from apoptosis), B and T-cell development, anti-viral and antimicrobial responses, and multiple stress responses.

In non-stimulated conditions, NF-KB is retained in the cytoplasm with I-KB (Inhibitor KB). However, upon stimulation, I-KB is phosphorylated and degraded, causing NF-KB to shuttle to the nucleus, thereby activating transcription of target genes. Target genes activated by NF-KB include IL-2, IL-6, GM-CSF, ICAM-1 and class 1 MHC.

Due to its central role and ability to respond to a range of stimuli, reporter constructs utilizing the NF-KB promoter element are used to screen the supernatants produced in Example 42. Activators or inhibitors of NF-KB would be useful in detecting, preventing, diagnosing, prognosticating, treating, and/or ameliorating diseases. For example, inhibitors of NF-KB could be used to treat those diseases related to the acute or chronic activation of NF-KB, such as rheumatoid arthritis.

To construct a vector containing the NF-KB promoter element, a PCR based strategy is employed. The upstream primer contains four tandem copies of the NF-KB binding site (GGGGACTTTCCC) (SEQ ID NO:243), 18 by of sequence complementary to the 5' end of the SV40 early promoter sequence, and is flanked with an XhoI site:

(SEQ ID NO: 244)
5':GCGGCCTCGAGGGGACTTTCCCGGGGACTTTCCGGGGACTTTCCGG

GACTTTCCATCCTGCCATCTCAATTAG:3'

The downstream primer is complementary to the 3' end of the SV40 promoter and is flanked with a Hind III site:

(SEQ ID NO: 239)
5':GCGGCAAGCTTTTTGCAAAGCCTAGGC:3'

PCR amplification is performed using the SV40 promoter template present in the pB-gal:promoter plasmid obtained from CLONTECH™. The resulting PCR fragment is digested with XhoI and Hind III and subcloned into BLSK2-. (STRATAGENE™) Sequencing with the T7 and T3 primers confirms the insert contains the following sequence:

(SEQ ID NO: 245)
5':CTCGAGGGGACTTTCCCGGGGACTTTCCGGGGACTTTCCGGGACTT

TCCATCTGCCATCTCAATTAGTCAGCAACCATAGTCCCGCCCCTAACTCC

GCCCATCCCGCCCCTAACTCCGCCCAGTTCCGCCCATTCTCCGCCCCATG

GCTGACTAATTTTTTTTATTTATGCAGAGGCCGAGGCCGCCTCGGCCTCT

GAGCTATTCCAGAAGTAGTGAGGAGGCTTTTTTGGAGGCCTAGGCTTTTG

CAAAAAGCTT:3'

Next, replace the SV40 minimal promoter element present in the pSEAP2-promoter plasmid (CLONTECH™) with this NF-KB/SV40 fragment using XhoI and HindIII. However, this vector does not contain a neomycin resistance gene, and therefore, is not preferred for mammalian expression systems.

In order to generate stable mammalian cell lines, the NF-KB/SV40/SEAP cassette is removed from the above NF-KB/SEAP vector using restriction enzymes SalI and NotI, and inserted into a vector containing neomycin resistance. Particularly, the NF-KB/SV40/SEAP cassette was inserted into pGFP-1 (CLONTECH™), replacing the GFP gene, after restricting pGFP-1 with SalI and NotI.

Once NF-KB/SV40/SEAP/Neo vector is created, stable Jurkat T-cells are created and maintained according to the protocol described in Example 44. Similarly, the method for assaying supernatants with these stable Jurkat T-cells is also described in Example 44. As a positive control, exogenous TNF alpha (0.1, 1, 10 ng) is added to wells H9, H10, and H11, with a 5-10 fold activation typically observed.

Example 48

Assay for SEAP Activity

As a reporter molecule for the assays described in Examples 44-47, SEAP activity is assayed using the Tropix Phospho-light Kit (Cat. BP-400) according to the following general procedure. The Tropix Phospho-light Kit supplies the Dilution, Assay, and Reaction Buffers used below.

Prime a dispenser with the 2.5× Dilution Buffer and dispense 15 μl of 2.5× dilution buffer into Optiplates containing 35 μl of a supernatant. Seal the plates with a plastic sealer and incubate at 65 degree C. for 30 min. Separate the Optiplates to avoid uneven heating.

Cool the samples to room temperature for 15 minutes. Empty the dispenser and prime with the Assay Buffer. Add 50 ml Assay Buffer and incubate at room temperature 5 min. Empty the dispenser and prime with the Reaction Buffer (see the Table below). Add 50 μl Reaction Buffer and incubate at room temperature for 20 minutes. Since the intensity of the chemiluminescent signal is time dependent, and it takes about 10 minutes to read 5 plates on a luminometer, thus one should treat 5 plates at each time and start the second set 10 minutes later.

Read the relative light unit in the luminometer. Set H12 as blank, and print the results. An increase in chemiluminescence indicates reporter activity.

Reaction Buffer Formulation:

| # of plates | Rxn buffer diluent (ml) | CSPD (ml) |
|---|---|---|
| 10 | 60 | 3 |
| 11 | 65 | 3.25 |
| 12 | 70 | 3.5 |
| 13 | 75 | 3.75 |
| 14 | 80 | 4 |
| 15 | 85 | 4.25 |
| 16 | 90 | 4.5 |
| 17 | 95 | 4.75 |
| 18 | 100 | 5 |
| 19 | 105 | 5.25 |
| 20 | 110 | 5.5 |
| 21 | 115 | 5.75 |
| 22 | 120 | 6 |
| 23 | 125 | 6.25 |
| 24 | 130 | 6.5 |

-continued

| # of plates | Rxn buffer diluent (ml) | CSPD (ml) |
|---|---|---|
| 25 | 135 | 6.75 |
| 26 | 140 | 7 |
| 27 | 145 | 7.25 |
| 28 | 150 | 7.5 |
| 29 | 155 | 7.75 |
| 30 | 160 | 8 |
| 31 | 165 | 8.25 |
| 32 | 170 | 8.5 |
| 33 | 175 | 8.75 |
| 34 | 180 | 9 |
| 35 | 185 | 9.25 |
| 36 | 190 | 9.5 |
| 37 | 195 | 9.75 |
| 38 | 200 | 10 |
| 39 | 205 | 10.25 |
| 40 | 210 | 10.5 |
| 41 | 215 | 10.75 |
| 42 | 220 | 11 |
| 43 | 225 | 11.25 |
| 44 | 230 | 11.5 |
| 45 | 235 | 11.75 |
| 46 | 240 | 12 |
| 47 | 245 | 12.25 |
| 48 | 250 | 12.5 |
| 49 | 255 | 12.75 |
| 50 | 260 | 13 |

Example 49

High-Throughput Screening Assay Identifying Changes in Small Molecule Concentration and Membrane Permeability Binding of a ligand to a receptor is known to alter intracellular levels of small molecules, such as calcium, potassium, sodium, and pH, as well as alter membrane potential. These alterations can be measured in an assay to identify supernatants which bind to receptors of a particular cell. Although the following protocol describes an assay for calcium, this protocol can easily be modified to detect changes in potassium, sodium, pH, membrane potential, or any other small molecule which is detectable by a fluorescent probe.

The following assay uses Fluorometric Imaging Plate Reader ("FLIPR") to measure changes in fluorescent molecules (Molecular Probes) that bind small molecules. Clearly, any fluorescent molecule detecting a small molecule can be used instead of the calcium fluorescent molecule, fluo-4 (Molecular Probes, Inc.; catalog no. F-14202), used here.

For adherent cells, seed the cells at 10,000-20,000 cells/well in a Co-star black 96-well plate with clear bottom. The plate is incubated in a $CO_2$ incubator for 20 hours. The adherent cells are washed two times in Biotek washer with 200 µl of HBSS (Hank's Balanced Salt Solution) leaving 100 µl of buffer after the final wash.

A stock solution of 1 mg/ml fluo-4 is made in 10% pluronic acid DMSO. To load the cells with fluo-4, 50 µl of 12 µg/ml fluo-4 is added to each well. The plate is incubated at 37 degrees C. in a $CO_2$ incubator for 60 min. The plate is washed four times in the Biotek washer with HBSS leaving 100 µl of buffer.

For non-adherent cells, the cells are spun down from culture media. Cells are re-suspended to $2\text{-}5\times10^6$ cells/ml with HBSS in a 50-ml conical tube. 4 µl of 1 mg/ml fluo-4 solution in 10% pluronic acid DMSO is added to each ml of cell suspension. The tube is then placed in a 37 degrees C. water bath for 30-60 min. The cells are washed twice with HBSS, resuspended to $1\times10^6$ cells/ml, and dispensed into a microplate, 100 µl/well. The plate is centrifuged at 1000 rpm for 5 min. The plate is then washed once in Denley Cell Wash with 200 µl, followed by an aspiration step to 100 µl final volume.

For a non-cell based assay, each well contains a fluorescent molecule, such as fluo-4. The supernatant is added to the well, and a change in fluorescence is detected.

To measure the fluorescence of intracellular calcium, the FLIPR is set for the following parameters: (1) System gain is 300-800 mW; (2) Exposure time is 0.4 second; (3) Camera F/stop is F/2; (4) Excitation is 488 nm; (5) Emission is 530 nm; and (6) Sample addition is 50 µl. Increased emission at 530 nm indicates an extracellular signaling event caused by the a molecule, either polypeptide of the present invention or a molecule induced by polypeptide of the present invention, which has resulted in an increase in the intracellular $Ca^{++}$ concentration.

Example 50

High-Throughput Screening Assay Identifying Tyrosine Kinase Activity

The Protein Tyrosine Kinases (PTK) represent a diverse group of transmembrane and cytoplasmic kinases. Within the Receptor Protein Tyrosine Kinase RPTK) group are receptors for a range of mitogenic and metabolic growth factors including the PDGF, FGF, EGF, NGF, HGF and Insulin receptor subfamilies. In addition there are a large family of RPTKs for which the corresponding ligand is unknown. Ligands for RPTKs include mainly secreted small proteins, but also membrane-bound and extracellular matrix proteins.

Activation of RPTK by ligands involves ligand-mediated receptor dimerization, resulting in transphosphorylation of the receptor subunits and activation of the cytoplasmic tyrosine kinases. The cytoplasmic tyrosine kinases include receptor associated tyrosine kinases of the src-family (e.g., src, yes, lck, lyn, fyn) and non-receptor linked and cytosolic protein tyrosine kinases, such as the Jak family, members of which mediate signal transduction triggered by the cytokine superfamily of receptors (e.g., the Interleukins, Interferons, GM-CSF, and Leptin).

Because of the wide range of known factors capable of stimulating tyrosine kinase activity, identifying whether polypeptide of the present invention or a molecule induced by polypeptide of the present invention is capable of activating tyrosine kinase signal transduction pathways is of interest. Therefore, the following protocol is designed to identify such molecules capable of activating the tyrosine kinase signal transduction pathways.

Seed target cells (e.g., primary keratinocytes) at a density of approximately 25,000 cells per well in a 96 well LOPRODYNE™ Silent Screen Plates purchased from Nalge Nunc (Naperville, Ill.). The plates are sterilized with two 30 minute rinses with 100% ethanol, rinsed with water and dried overnight. Some plates are coated for 2 hr with 100 ml of cell culture grade type I collagen (50 mg/ml), gelatin (2%) or polylysine (50 mg/ml), all of which can be purchased from SIGMA™ Chemicals (St. Louis, Mo.) or 10% MATRIGEL™ purchased from Becton Dickinson (Bedford, Mass.), or calf serum, rinsed with PBS and stored at 4 degree C. Cell growth on these plates is assayed by seeding 5,000 cells/well in growth medium and indirect quantitation of cell number through use of ALAMAR BLUE™ as described by the manufacturer Alamar Biosciences, Inc. (Sacramento, Calif.) after 48 hr. Falcon plate covers #3071 from Becton Dickinson (Bedford, Mass.) are used to cover the LOPRODYNE™

Silent Screen Plates. Falcon Microtest III cell culture plates can also be used in some proliferation experiments.

To prepare extracts, A431 cells are seeded onto the nylon membranes of LOPRODYNE™ plates (20,000/200 ml/well) and cultured overnight in complete medium. Cells are quiesced by incubation in serum-free basal medium for 24 hr. After 5-20 minutes treatment with EGF (60 ng/ml) or 50 μl of the supernatant produced in Example 42, the medium was removed and 100 ml of extraction buffer ((20 mM HEPES pH 7.5, 0.15 M NaCl, 1% Triton X-100, 0.1% SDS, 2 αmM Na3VO4, 2 mM Na4P2O7 and a cocktail of protease inhibitors (#1836170) obtained from Boeheringer Mannheim (Indianapolis, Ind.)) is added to each well and the plate is shaken on a rotating shaker for 5 minutes at 4° C. The plate is then placed in a vacuum transfer manifold and the extract filtered through the 0.45 mm membrane bottoms of each well using house vacuum. Extracts are collected in a 96-well catch/assay plate in the bottom of the vacuum manifold and immediately placed on ice. To obtain extracts clarified by centrifugation, the content of each well, after detergent solubilization for 5 minutes, is removed and centrifuged for 15 minutes at 4 degree C. at 16,000×g.

Test the filtered extracts for levels of tyrosine kinase activity. Although many methods of detecting tyrosine kinase activity are known, one method is described here.

Generally, the tyrosine kinase activity of a supernatant is evaluated by determining its ability to phosphorylate a tyrosine residue on a specific substrate (a biotinylated peptide). Biotinylated peptides that can be used for this purpose include PSK1 (corresponding to amino acids 6-20 of the cell division kinase cdc2-p34) and PSK2 (corresponding to amino acids 1-17 of gastrin). Both peptides are substrates for a range of tyrosine kinases and are available from BOEHRINGER™ Mannheim.

The tyrosine kinase reaction is set up by adding the following components in order. First, add 10 μl of 5 uM Biotinylated Peptide, then 10 μl ATP/$Mg_{2+}$ (5 mM ATP/50 mM $MgCl_2$), then 10 μl of 5× Assay Buffer (40 mM imidazole hydrochloride, pH7.3, 40 mM beta-glycerophosphate, 1 mM EGTA, 100 mM $MgCl_2$, 5 mM $MnCl_2$ 0.5 mg/ml BSA), then 5 μl of Sodium Vanadate (1 mM), and then 5 μl of water. Mix the components gently and preincubate the reaction mix at 30 degree C. for 2 min. Initial the reaction by adding 10 μl of the control enzyme or the filtered supernatant.

The tyrosine kinase assay reaction is then terminated by adding 10 μl of 120 mm EDTA and place the reactions on ice.

Tyrosine kinase activity is determined by transferring 50 μl aliquot of reaction mixture to a microtiter plate (MTP) module and incubating at 37 degree C. for 20 min. This allows the streptavidin coated 96 well plate to associate with the biotinylated peptide. Wash the MTP module with 300 ul/well of PBS four times. Next add 75 μl of anti-phosphotyrosine antibody conjugated to horse radish peroxidase (anti-P-Tyr-POD (0.5 u/ml)) to each well and incubate at 37 degree C. for one hour. Wash the well as above.

Next add 100 μl of peroxidase substrate solution (BOEHRINGER™ Mannheim) and incubate at room temperature for at least 5 mins (up to 30 min). Measure the absorbance of the sample at 405 nm by using ELISA reader. The level of bound peroxidase activity is quantitated using an ELISA reader and reflects the level of tyrosine kinase activity.

Example 51

High-Throughput Screening Assay Identifying Phosphorylation Activity

As a potential alternative and/or complement to the assay of protein tyrosine kinase activity described in Example 50, an assay which detects activation (phosphorylation) of major intracellular signal transduction intermediates can also be used. For example, as described below one particular assay can detect tyrosine phosphorylation of the Erk-1 and Erk-2 kinases. However, phosphorylation of other molecules, such as Raf, JNK, p38 MAP, Map kinase kinase (MEK), MEK kinase, Src, Muscle specific kinase (MuSK), IRAK, Tec, and Janus, as well as any other phosphoserine, phosphotyrosine, or phosphothreonine molecule, can be detected by substituting these molecules for Erk-1 or Erk-2 in the following assay.

Specifically, assay plates are made by coating the wells of a 96-well ELISA plate with 0.1 ml of protein G (1 ug/ml) for 2 hr at room temp, (RT). The plates are then rinsed with PBS and blocked with 3% BSA/PBS for 1 hr at RT. The protein G plates are then treated with 2 commercial monoclonal antibodies (100 ng/well) against Erk-1 and Erk-2 (1 hr at RT) (Santa Cruz Biotechnology). (To detect other molecules, this step can easily be modified by substituting a monoclonal antibody detecting any of the above described molecules.) After 3-5 rinses with PBS, the plates are stored at 4 degree C. until use.

A431 cells are seeded at 20,000/well in a 96-well LOPRODYNE™ filterplate and cultured overnight in growth medium. The cells are then starved for 48 hr in basal medium (DMEM) and then treated with EGF (6 ng/well) or 50 μl of the supernatants obtained in Example 42 for 5-20 minutes. The cells are then solubilized and extracts filtered directly into the assay plate.

After incubation with the extract for 1 hr at RT, the wells are again rinsed. As a positive control, a commercial preparation of MAP kinase (10 ng/well) is used in place of A431 extract. Plates are then treated with a commercial polyclonal (rabbit) antibody (1 ug/ml) which specifically recognizes the phosphorylated epitope of the Erk-1 and Erk-2 kinases (1 hr at RT). This antibody is biotinylated by standard procedures. The bound polyclonal antibody is then quantitated by successive incubations with Europium-streptavidin and Europium fluorescence enhancing reagent in the Wallac DELFIA instrument (time-resolved fluorescence). An increased fluorescent signal over background indicates a phosphorylation by polypeptide of the present invention or a molecule induced by polypeptide of the present invention.

Example 52

Assay for the Stimulation of Bone Marrow CD34+ Cell Proliferation

This assay is based on the ability of human CD34+ to proliferate in the presence of hematopoietic growth factors and evaluates the ability of isolated polypeptides expressed in mammalian cells to stimulate proliferation of CD34+ cells.

It has been previously shown that most mature precursors will respond to only a single signal. More immature precursors require at least two signals to respond. Therefore, to test the effect of polypeptides on hematopoietic activity of a wide range of progenitor cells, the assay contains a given polypeptide in the presence or absence of other hematopoietic growth factors. Isolated cells are cultured for 5 days in the presence of Stem Cell Factor (SCF) in combination with tested sample. SCF alone has a very limited effect on the proliferation of bone marrow (BM) cells, acting in such conditions only as a "survival" factor. However, combined with any factor exhibiting stimulatory effect on these cells (e.g., IL-3), SCF will cause a synergistic effect. Therefore, if the tested polypeptide has a stimulatory effect on hematopoietic progenitors, such activity can be easily detected. Since normal BM cells have a low level of cycling cells, it is likely that any inhibitory effect of a given polypeptide, or agonists or antagonists thereof, might not be detected. Accordingly, assays for an inhibitory effect on progenitors is preferably tested in cells that are first subjected to in vitro stimulation with SCF+IL+3, and then contacted with the compound that is being evaluated for inhibition of such induced proliferation.

Briefly, CD34+ cells are isolated using methods known in the art. The cells are thawed and resuspended in medium (QBSF 60 serum-free medium with 1% L-glutamine (500 ml) Quality Biological, Inc., Gaithersburg, Md. Cat#160-204-101). After several gentle centrifugation steps at 200×g, cells are allowed to rest for one hour. The cell count is adjusted to $2.5\times10^5$ cells/ml. During this time, 100 μl of sterile water is added to the peripheral wells of a 96-well plate. The cytokines that can be tested with a given polypeptide in this assay is rhSCF (R&D Systems, Minneapolis, Minn., Cat#255-SC) at 50 ng/ml alone and in combination with rhSCF and rhIL-3 (R&D Systems, Minneapolis, Minn., Cat#203-ML) at 30 ng/ml. After one hour, 10 μl of prepared cytokines, 50 μl of the supernatants prepared in Example 42 (supernatants at 1:2 dilution=50 μl) and 20 μl of diluted cells are added to the media which is already present in the wells to allow for a final total volume of 100 μl. The plates are then placed in a 37° C./5% $CO_2$ incubator for five days.

Eighteen hours before the assay is harvested, 0.5 μCi/well of [3H] Thymidine is added in a 10 μl volume to each well to determine the proliferation rate. The experiment is terminated by harvesting the cells from each 96-well plate to a filtermat using the Tomtec Harvester 96. After harvesting, the filtermats are dried, trimmed and placed into OMNIFILTER™ assemblies consisting of one OMNIFILTER™ plate and one OMNIFILTER™ Tray. 60 μl MICROSCINT™ is added to each well and the plate sealed with TopSeal-A press-on sealing film. A bar code 15 sticker is affixed to the first plate for counting. The sealed plates are then loaded and the level of radioactivity determined via the Packard Top Count and the printed data collected for analysis. The level of radioactivity reflects the amount of cell proliferation.

The studies described in this example test the activity of a given polypeptide to stimulate bone marrow CD34+ cell proliferation. One skilled in the art could easily modify the exemplified studies to test the activity of polynucleotides (e.g., gene therapy), antibodies, agonists, and/or antagonists and fragments and variants thereof. As a nonlimiting example, potential antagonists tested in this assay would be expected to inhibit cell proliferation in the presence of cytokines and/or to increase the inhibition of cell proliferation in the presence of cytokines and a given polypeptide. In contrast, potential agonists tested in this assay would be expected to enhance cell proliferation and/or to decrease the inhibition of cell proliferation in the presence of cytokines and a given polypeptide.

The ability of a gene to stimulate the proliferation of bone marrow CD34+ cells indicates that polynucleotides and polypeptides corresponding to the gene are useful for the detection, prevention, diagnosis, prognostication, treatment, and/or amelioration of disorders affecting the immune system and hematopoiesis. Representative uses are described in the "Immune Activity" and "Infectious Disease" sections above, and elsewhere herein.

Example 53

Assay for Extracellular Matrix Enhanced Cell Response (EMECR)

The objective of the Extracellular Matrix Enhanced Cell Response (EMECR) assay is to identify gene products (e.g., isolated polypeptides) that act on the hematopoietic stem cells in the context of the extracellular matrix (ECM) induced signal.

Cells respond to the regulatory factors in the context of signal(s) received from the surrounding microenvironment. For example, fibroblasts, and endothelial and epithelial stem cells fail to replicate in the absence of signals from the ECM. Hematopoietic stem cells can undergo self-renewal in the bone marrow, but not in in vitro suspension culture. The ability of stem cells to undergo self-renewal in vitro is dependent upon their interaction with the stromal cells and the ECM protein fibronectin (fn). Adhesion of cells to fn is mediated by the $\alpha_5.\beta_1$ and $\alpha_4.\beta_1$ integrin receptors, which are expressed by human and mouse hematopoietic stem cells. The factor(s) which integrate with the ECM environment and are responsible for stimulating stem cell self-renewal have not yet been identified. Discovery of such factors should be of great interest in gene therapy and bone marrow transplant applications Briefly, polystyrene, non tissue culture treated, 96-well plates are coated with fn fragment at a coating concentration of 0.2 μg/cm$^2$. Mouse bone marrow cells are plated (1,000 cells/well) in 0.2 ml of serum-free medium. Cells cultured in the presence of IL-3 (5 ng/ml)+SCF (50 ng/ml) would serve as the positive control, conditions under which little self-renewal but pronounced differentiation of the stem cells is to be expected. Gene products of the invention (e.g., including, but not limited to, polynucleotides and polypeptides of the present invention, and supernatants produced in Example 42), are tested with appropriate negative controls in the presence and absence of SCF (5.0 ng/ml), where test factor supernatants represent 10% of the total assay volume. The plated cells are then allowed to grow by incubating in a low oxygen environment (5% $CO_2$, 7% $O_2$, and 88% $N_2$) tissue culture incubator for 7 days. The number of proliferating cells within the wells is then quantitated by measuring thymidine incorporation into cellular DNA. Verification of the positive hits in the assay will require phenotypic characterization of the cells, which can be accomplished by scaling up of the culture system and using appropriate antibody reagents against cell surface antigens and FACScan.

One skilled in the art could easily modify the exemplified studies to test the activity of polynucleotides (e.g., gene therapy), antibodies, agonists, and/or antagonists and fragments and variants thereof.

If a particular polypeptide of the present invention is found to be a stimulator of hematopoietic progenitors, polynucleotides and polypeptides corresponding to the gene encoding said polypeptide may be useful for the detection, prevention, diagnosis, prognostication, treatment, and/or amelioration of disorders affecting the immune system and hematopoiesis. Representative uses are described in the "Immune Activity" and "Infectious Disease" sections above, and elsewhere herein. The gene product may also be useful in the expansion of stem cells and committed progenitors of various blood lineages, and in the differentiation and/or proliferation of various cell types.

Additionally, the polynucleotides and/or polypeptides of the gene of interest and/or agonists and/or antagonists thereof, may also be employed to inhibit the proliferation and differentiation of hematopoietic cells and therefore may be employed to protect bone marrow stem cells from chemotherapeutic agents during chemotherapy. This antiproliferative effect may allow administration of higher doses of chemotherapeutic agents and, therefore, more effective chemotherapeutic treatment.

Moreover, polynucleotides and polypeptides corresponding to the gene of interest may also be useful for the detection, prevention, diagnosis, prognostication, treatment, and/or amelioration of hematopoietic related disorders such as, for example, anemia, pancytopenia, leukopenia, thrombocytopenia or leukemia since stromal cells are important in the production of cells of hematopoietic lineages. The uses include bone marrow cell ex-vivo culture, bone marrow transplantation, bone marrow reconstitution, radiotherapy or chemotherapy of neoplasia.

Example 54

Human Dermal Fibroblast and Aortic Smooth Muscle Cell Proliferation

The polypeptide of interest is added to cultures of normal human dermal fibroblasts (NHDF) and human aortic smooth muscle cells (AoSMC) and two co-assays are performed with each sample. The first assay examines the effect of the polypeptide of interest on the proliferation of normal human dermal fibroblasts (NHDF) or aortic smooth muscle cells (AoSMC). Aberrant growth of fibroblasts or smooth muscle cells is a part of several pathological processes, including fibrosis, and restenosis. The second assay examines IL6 production by both NHDF and SMC. IL6 production is an indication of functional activation. Activated cells will have increased production of a number of cytokines and other factors, which can result in a proinflammatory or immunomodulatory outcome. Assays are run with and without co-TNFa stimulation, in order to check for costimulatory or inhibitory activity.

Briefly, on day 1, 96-well black plates are set up with 1000 cells/well (NHDF) or 2000 cells/well (AoSMC) in 100 μl culture media. NHDF culture media contains: Clonetics FB basal media, 1 mg/ml hFGF, 5 mg/ml insulin, 50 mg/ml gentamycin, 2% FBS, while AoSMC culture media contains Clonetics SM basal media, 0.5 μg/ml hEGF, 5 mg/ml insulin, 1 μg/ml hFGF, 50 mg/ml gentamycin, 50 μg/ml Amphotericin B, 5% FBS. After incubation at 37° C. for at least 4-5 hours culture media is aspirated and replaced with growth arrest media. Growth arrest media for NHDF contains fibroblast basal media, 50 mg/ml gentamycin, 2% FBS, while growth arrest media for AoSMC contains SM basal media, 50 mg/ml gentamycin, 50 μg/ml Amphotericin B, 0.4% FBS. Incubate at 37° C. until day 2.

On day 2, serial dilutions and templates of the polypeptide of interest are designed such that they always include media controls and known-protein controls. For both stimulation and inhibition experiments, proteins are diluted in growth arrest media. For inhibition experiments, TNFa is added to a final concentration of 2 ng/ml (NHDF) or 5 ng/ml (AoSMC). Add ⅓ vol media containing controls or polypeptides of the present invention and incubate at 37° C./5% $CO_2$ until day 5.

Transfer 60 μl from each well to another labeled 96-well plate, cover with a plate-sealer, and store at 4° C. until Day 6 (for IL6 ELISA). To the remaining 100 μl in the cell culture plate, aseptically add ALAMAR BLUE™ in an amount equal to 10% of the culture volume (10 μl). Return plates to incubator for 3 to 4 hours. Then measure fluorescence with excitation at 530 nm and emission at 590 nm using the CYTOFLUOR™. This yields the growth stimulation/inhibition data.

On day 5, the IL6 ELISA is performed by coating a 96 well plate with 50-100 μl/well of Anti-Human IL6 Monoclonal antibody diluted in PBS, pH 7.4, incubate ON at room temperature.

On day 6, empty the plates into the sink and blot on paper towels. Prepare Assay Buffer containing PBS with 4% BSA. Block the plates with 200 μl/well of Pierce Super Block blocking buffer in PBS for 1-2 hr and then wash plates with wash buffer (PBS, 0.05% Tween-20). Blot plates on paper towels. Then add 50 μl/well of diluted Anti-Human IL-6 Monoclonal, Biotin-labeled antibody at 0.50 mg/ml. Make dilutions of IL-6 stock in media (30, 10, 3, 1, 0.3, 0 ng/ml). Add duplicate samples to top row of plate. Cover the plates and incubate for 2 hours at RT on shaker.

Plates are washed with wash buffer and blotted on paper towels. Dilute EU-labeled Streptavidin 1:1000 in Assay buffer, and add 100 μl/well. Cover the plate and incubate 1 h at RT. Plates are again washed with wash buffer and blotted on paper towels.

Add 100 μl/well of Enhancement Solution. Shake for 5 minutes. Read the plate on the Wallac DELFIA Fluorometer. Readings from triplicate samples in each assay were tabulated and averaged.

A positive result in this assay suggests AoSMC cell proliferation and that the polypeptide of the present invention may be involved in dermal fibroblast proliferation and/or smooth muscle cell proliferation. A positive result also suggests many potential uses of polypeptides, polynucleotides, agonists and/or antagonists of the polynucleotide/polypeptide of the present invention which gives a positive result. For example, inflammation and immune responses, wound healing, and angiogenesis, as detailed throughout this specification. Particularly, polypeptides of the present invention and polynucleotides of the present invention may be used in wound healing and dermal regeneration, as well as the promotion of vasculogenesis, both of the blood vessels and lymphatics. The growth of vessels can be used in the treatment of, for example, cardiovascular diseases. Additionally, antagonists of polypeptides and polynucleotides of the invention may be useful in treating diseases, disorders, and/or conditions which involve angiogenesis by acting as an anti-vascular agent (e.g., anti-angiogenesis). These diseases, disorders, and/or conditions are known in the art and/or are described herein, such as, for example, malignancies, solid tumors, benign tumors, for example hemangiomas, acoustic neuromas, neurofibromas, trachomas, and pyogenic granulomas; artheroscleric plaques; ocular angiogenic diseases, for example, diabetic retinopathy, retinopathy of prematurity, macular degeneration, corneal graft rejection, neovascular glaucoma, retrolental fibroplasia, rubeosis, retinoblastoma, uvietis and Pterygia (abnormal blood vessel growth) of the eye; rheumatoid arthritis; psoriasis; delayed wound healing; endometriosis; vasculogenesis; granulations; hypertrophic scars (keloids); nonunion fractures; scleroderma; trachoma; vascular adhesions; myocardial angiogenesis; coronary collaterals; cerebral collaterals; arteriovenous malformations; ischemic limb angiogenesis; Osler-Webber Syndrome; plaque neovascularization; telangiectasia; hemophiliac joints; angiofibroma; fibromuscular dysplasia; wound granulation; Crohn's disease; and atherosclerosis. Moreover, antagonists of polypeptides and polynucleotides of the invention may be useful in treating anti-hyperproliferative diseases and/or anti-inflammatory known in the art and/or described herein.

One skilled in the art could easily modify the exemplified studies to test the activity of polynucleotides (e.g., gene therapy), antibodies, agonists, and/or antagonists and fragments and variants thereof.

Example 55

Cellular Adhesion Molecule (CAM) Expression on Endothelial Cells

The recruitment of lymphocytes to areas of inflammation and angiogenesis involves specific receptor-ligand interactions between cell surface adhesion molecules (CAMs) on lymphocytes and the vascular endothelium. The adhesion process, in both normal and pathological settings, follows a multi-step cascade that involves intercellular adhesion molecule-1 (ICAM-1), vascular cell adhesion molecule-1 (VCAM-1), and endothelial leukocyte adhesion molecule-1 (E-selectin) expression on endothelial cells (EC). The expression of these molecules and others on the vascular endothelium determines the efficiency with which leukocytes may adhere to the local vasculature and extravasate into the local tissue during the development of an inflammatory response. The local concentration of cytokines and growth factor participate in the modulation of the expression of these CAMs.

Briefly, endothelial cells (e.g., Human Umbilical Vein Endothelial cells (HUVECs)) are grown in a standard 96 well plate to confluence, growth medium is removed from the cells and replaced with 100 μl of 199 Medium (10% fetal bovine serum (FBS)). Samples for testing and positive or negative controls are added to the plate in triplicate (in 10 μl volumes). Plates are then incubated at 37° C. for either 5 h (selectin and integrin expression) or 24 h (integrin expression only). Plates are aspirated to remove medium and 100 μl of 0.1% paraformaldehyde-PBS (with Ca++ and Mg++) is added to each well. Plates are held at 4° C. for 30 min. Fixative is removed from the wells and wells are washed 1× with PBS(+Ca,Mg)+0.5% BSA and drained. 10 μl of diluted primary antibody is added to the test and control wells. Anti-ICAM-1-Biotin, Anti-VCAM-1-Biotin and Anti-E-selectin-Biotin are used at a concentration of 10 μg/ml (1:10 dilution of 0.1 mg/ml stock antibody). Cells are incubated at 37° C. for 30 min. in a humidified environment. Wells are washed three times with PBS (+Ca,Mg)+0.5% BSA. 20 μl of diluted Extravidin®-Alkaline Phosphatase (1:5,000 dilution, referred to herein as the working dilution) are added to each well and incubated at 37° C. for 30 min. Wells are washed three times with PBS (+Ca, Mg)+0.5% BSA. Dissolve 1 tablet of p-Nitrophenol Phosphate pNPP per 5 ml of glycine buffer (pH 10.4). 100 μl of pNPP substrate in glycine buffer is added to each test well. Standard wells in triplicate are prepared from the working dilution of the ExtrAvidin®-Alkaline Phosphotase in glycine buffer: 1:5,000 ($10^0$)>$10^{-0.5}$>$10^{-1}$>$10^{-1.5}$. 5 μl of each dilution is added to triplicate wells and the resulting AP content in each well is 5.50 ng, 1.74 ng, 0.55 ng, 0.18 ng. 100 μl of pNNP reagent is then added to each of the standard wells. The plate is incubated at 37° C. for 4 h. A volume of 50 μl of 3M NaOH is added to all wells. The plate is read on a plate reader at 405 nm using the background subtraction option on blank wells filled with glycine buffer only. Additionally, the template is set up to indicate the concentration of AP-conjugate in each standard well [5.50 ng; 1.74 ng; 0.55 ng; 0.18 ng]. Results are indicated as amount of bound AP-conjugate in each sample.

Example 56

ALAMAR BLUE™ Endothelial Cells Proliferation Assay

This assay may be used to quantitatively determine protein mediated inhibition of bFGF-induced proliferation of Bovine Lymphatic Endothelial Cells (LECs), Bovine Aortic Endothelial Cells (BAECs) or Human Microvascular Uterine Myometrial Cells (UTMECs). This assay incorporates a fluorometric growth indicator based on detection of metabolic activity. A standard ALAMAR BLUE™ Proliferation Assay is prepared in EGM-2MV with 10 ng/ml of bFGF added as a source of endothelial cell stimulation. This assay may be used with a variety of endothelial cells with slight changes in growth medium and cell concentration. Dilutions of the protein batches to be tested are diluted as appropriate. Serum-free medium (GIBCO SFM) without bFGF is used as a non-stimulated control and Angiostatin or TSP-1 are included as a known inhibitory controls.

Briefly, LEC, BAECs or UTMECs are seeded in growth media at a density of 5000 to 2000 cells/well in a 96 well plate and placed at 37° C. overnight. After the overnight incubation of the cells, the growth media is removed and replaced with GIBCO EC-SFM. The cells are treated with the appropriate dilutions of the protein of interest or control protein sample(s) (prepared in SFM) in triplicate wells with additional bFGF to a concentration of 10 ng/ml. Once the cells have been treated with the samples, the plate(s) is/are placed back in the 37° C. incubator for three days. After three days 10 ml of stock ALAMAR BLUE™ (Biosource Cat# DAL1100) is added to each well and the plate(s) is/are placed back in the 37° C. incubator for four hours. The plate(s) are then read at 530 nm excitation and 590 nm emission using the CYTOFLUOR™ fluorescence reader. Direct output is recorded in relative fluorescence units.

ALAMAR BLUE™ is an oxidation-reduction indicator that both fluoresces and changes color in response to chemical reduction of growth medium resulting from cell growth. As cells grow in culture, innate metabolic activity results in a chemical reduction of the immediate surrounding environment. Reduction related to growth causes the indicator to change from oxidized (non-fluorescent blue) form to reduced (fluorescent red) form (i.e., stimulated proliferation will produce a stronger signal and inhibited proliferation will produce a weaker signal and the total signal is proportional to the total number of cells as well as their metabolic activity). The background level of activity is observed with the starvation medium alone. This is compared to the output observed from the positive control samples (bFGF in growth medium) and protein dilutions.

Example 57

Detection of Inhibition of a Mixed Lymphocyte Reaction

This assay can be used to detect and evaluate inhibition of a Mixed Lymphocyte Reaction (MLR) by gene products (e.g., isolated polypeptides). Inhibition of a MLR may be due to a direct effect on cell proliferation and viability, modulation of costimulatory molecules on interacting cells, modulation of adhesiveness between lymphocytes and accessory cells, or modulation of cytokine production by accessory cells. Multiple cells may be targeted by these polypeptides since the peripheral blood mononuclear fraction used in this assay includes T, B and natural killer lymphocytes, as well as monocytes and dendritic cells.

Polypeptides of interest found to inhibit the MLR may find application in diseases associated with lymphocyte and monocyte activation or proliferation. These include, but are not limited to, diseases such as asthma, arthritis, diabetes, inflammatory skin conditions, psoriasis, eczema, systemic lupus erythematosus, multiple sclerosis, glomerulonephritis, inflammatory bowel disease, crohn's disease, ulcerative colitis, arteriosclerosis, cirrhosis, graft vs. host disease, host vs. graft disease, hepatitis, leukemia and lymphoma.

Briefly, PBMCs from human donors are purified by density gradient centrifugation using Lymphocyte Separation Medium (LSM®, density 1.0770 g/ml, Organon Teknika Corporation, West Chester, Pa.). PBMCs from two donors are adjusted to $2\times10^6$ cells/ml in RPMI-1640 (LIFE TECH- NOLOGIES™, Grand Island, N.Y.) supplemented with 10% FCS and 2 mM glutamine. PBMCs from a third donor are adjusted to $2\times10^5$ cells/ml. Fifty microliters of PBMCs from each donor is added to wells of a 96-well round bottom microtiter plate. Dilutions of test materials (50 μl) are added in triplicate to microtiter wells. Test samples (of the protein of interest) are added for final dilution of 1:4; rhuIL-2 (R&D Systems, Minneapolis, Minn., catalog number 202-IL) is added to a final concentration of 1 μg/ml; anti-CD4 mAb (R&D Systems, clone 34930.11, catalog number MAB379) is added to a final concentration of 10 μg/ml. Cells are cultured for 7-8 days at 37° C. in 5% $CO_2$, and 1 μC of [$^3$H] thymidine is added to wells for the last 16 hrs of culture. Cells are harvested and thymidine incorporation determined using a Packard TopCount. Data is expressed as the mean and standard deviation of triplicate determinations.

Samples of the protein of interest are screened in separate experiments and compared to the negative control treatment, anti-CD4 mAb, which inhibits proliferation of lymphocytes and the positive control treatment, IL-2 (either as recombinant material or supernatant), which enhances proliferation of lymphocytes.

One skilled in the art could easily modify the exemplified studies to test the activity of polynucleotides (e.g., gene therapy), antibodies, agonists, and/or antagonists and fragments and variants thereof.

Example 58

Assays for Protease Activity

The following assay may be used to assess protease activity of the polypeptides of the invention.

Gelatin and casein zymography are performed essentially as described (Heusen et al., *Anal. Biochem.,* 102:196-202 (1980); Wilson et al., *Journal of Urology,* 149:653-658 (1993)). Samples are run on 10% polyacrylamide/0.1% SDS gels containing 1% gelatin orcasein, soaked in 2.5% triton at room temperature for 1 hour, and in 0.1M glycine, pH 8.3 at 37° C. 5 to 16 hours. After staining in amido black areas of proteolysis appear as clear areas against the blue-black background. Trypsin (SIGMA™ T8642) is used as a positive control.

Protease activity is also determined by monitoring the cleavage of n-a-benzoyl-L-arginine ethyl ester (BAEE) (SIGMA™ B-4500). Reactions are set up in (25 mM$NaPO_4$, 1 mM EDTA, and 1 mM BAEE), pH 7.5. Samples are added and the change in absorbance at 260 nm is monitored on the Beckman DU-6 spectrophotometer in the time-drive mode. Trypsin is used as a positive control.

Additional assays based upon the release of acid-soluble peptides from casein or hemoglobin measured as absorbance at 280 nm or colorimetrically using the Folin method are performed as described in Bergmeyer, et al., *Methods of Enzymatic Analysis,* 5 (1984). Other assays involve the solubilization of chromogenic substrates (Ward, *Applied Science,* 251-317 (1983)).

Example 59

Identifying Serine Protease Substrate Specificity

Methods known in the art or described herein may be used to determine the substrate specificity of the polypeptides of the present invention having serine protease activity. A preferred method of determining substrate specificity is by the use of positional scanning synthetic combinatorial libraries as described in GB 2 324 529 (incorporated herein in its entirety).

Example 60

Ligand Binding Assays

The following assay may be used to assess ligand binding activity of the polypeptides of the invention.

Ligand binding assays provide a direct method for ascertaining receptor pharmacology and are adaptable to a high throughput format. The purified ligand for a polypeptide is radiolabeled to high specific activity (50-2000 Ci/mmol) for binding studies. A determination is then made that the process of radiolabeling does not diminish the activity of the ligand towards its polypeptide. Assay conditions for buffers, ions, pH and other modulators such as nucleotides are optimized to establish a workable signal to noise ratio for both membrane and whole cell polypeptide sources. For these assays, specific polypeptide binding is defined as total associated radioactivity minus the radioactivity measured in the presence of an excess of unlabeled competing ligand. Where possible, more than one competing ligand is used to define residual nonspecific binding.

Example 61

Functional Assay in *Xenopus* Oocytes

Capped RNA transcripts from linearized plasmid templates encoding the polypeptides of the invention are synthesized in vitro with RNA polymerases in accordance with standard procedures. In vitro transcripts are suspended in water at a final concentration of 0.2 mg/ml. Ovarian lobes are removed from adult female toads, Stage V defolliculated oocytes are obtained, and RNA transcripts (10 ng/oocyte) are injected in a 50 nl bolus using a microinjection apparatus. Two electrode voltage clamps are used to measure the currents from individual *Xenopus* oocytes in response polypeptides and polypeptide agonist exposure. Recordings are made in Ca2+ free Barth's medium at room temperature. The *Xenopus* system can be used to screen known ligands and tissue/cell extracts for activating ligands.

Example 62

Microphysiometric Assays

Activation of a wide variety of secondary messenger systems results in extrusion of small amounts of acid from a cell. The acid formed is largely as a result of the increased metabolic activity required to fuel the intracellular signaling process. The pH changes in the media surrounding the cell are very small but are detectable by the CYTOSENSOR microphysiometer (Molecular Devices Ltd., Menlo Park, Calif.). The CYTOSENSOR is thus capable of detecting the activation of polypeptide that is coupled to an energy utilizing intracellular signaling pathway.

Example 63

Extract/Cell Supernatant Screening

A large number of mammalian receptors exist for which there remains, as yet, no cognate activating ligand (agonist). Thus, active ligands for these receptors may not be included within the ligands banks as identified to date. Accordingly, the polypeptides of the invention can also be functionally screened (using calcium, cAMP, microphysiometer, oocyte electrophysiology, etc., functional screens) against tissue extracts to identify its natural ligands. Extracts that produce positive functional responses can be sequentially subfractionated until an activating ligand is isolated and identified.

Example 64

Calcium and cAMP Functional Assays

Seven transmembrane receptors which are expressed in HEK 293 cells have been shown to be coupled functionally to activation of PLC and calcium mobilization and/or cAMP stimulation or inhibition. Basal calcium levels in the HEK 293 cells in receptor-transfected or vector control cells were observed to be in the normal, 100 nM to 200 nM, range. HEK 293 cells expressing recombinant receptors are loaded with fura 2 and in a single day >150 selected ligands or tissue/cell extracts are evaluated for agonist induced calcium mobilization. Similarly, HEK 293 cells expressing recombinant receptors are evaluated for the stimulation or inhibition of cAMP production using standard cAMP quantitation assays. Agonists presenting a calcium transient or cAMP fluctuation are tested in vector control cells to determine if the response is unique to the transfected cells expressing receptor.

Example 65

ATP-Binding Assay

The following assay may be used to assess ATP-binding activity of polypeptides of the invention.

ATP-binding activity of the polypeptides of the invention may be detected using the ATP-binding assay described in U.S. Pat. No. 5,858,719, which is herein incorporated by reference in its entirety. Briefly, ATP-binding to polypeptides of the invention is measured via photoaffinity labeling with 8-azido-ATP in a competition assay. Reaction mixtures containing 1 mg/ml of the ABC transport protein of the present invention are incubated with varying concentrations of ATP, or the non-hydrolyzable ATP analog adenyl-5'-imidodiphosphate for 10 minutes at 4° C. A mixture of 8-azido-ATP (SIGMA™ Chem. Corp., St. Louis, Mo.) plus 8-azido-ATP ($^{32}$P-ATP) (5 mCi/μmol, ICN, Irvine Calif.) is added to a final concentration of 100 μM and 0.5 ml aliquots are placed in the wells of a porcelain spot plate on ice. The plate is irradiated using a short wave 254 nm UV lamp at a distance of 2.5 cm from the plate for two one-minute intervals with a one-minute cooling interval in between. The reaction is stopped by addition of dithiothreitol to a final concentration of 2 mM. The incubations are subjected to SDS-PAGE electrophoresis, dried, and autoradiographed. Protein bands corresponding to the particular polypeptides of the invention are excised, and the radioactivity quantified. A decrease in radioactivity with increasing ATP or adenyl-5'-imidodiphosphate provides a measure of ATP affinity to the polypeptides.

Example 66

Small Molecule Screening

This invention is particularly useful for screening therapeutic compounds by using the polypeptides of the invention, or binding fragments thereof, in any of a variety of drug screening techniques. The polypeptide or fragment employed in such a test may be affixed to a solid support, expressed on a cell surface, free in solution, or located intracellularly. One method of drug screening utilizes eukaryotic or prokaryotic host cells which are stably transformed with recombinant nucleic acids expressing the polypeptide or fragment. Drugs are screened against such transformed cells in competitive binding assays. One may measure, for example, the formulation of complexes between the agent being tested and polypeptide of the invention.

Thus, the present invention provides methods of screening for drugs or any other agents which affect activities mediated by the polypeptides of the invention. These methods comprise contacting such an agent with a polypeptide of the invention or fragment thereof and assaying for the presence of a complex between the agent and the polypeptide or fragment thereof, by methods well known in the art. In such a competitive binding assay, the agents to screen are typically labeled. Following incubation, free agent is separated from that present in bound form, and the amount of free or uncomplexed label is a measure of the ability of a particular agent to bind to the polypeptides of the invention.

Another technique for drug screening provides high throughput screening for compounds having suitable binding affinity to the polypeptides of the invention, and is described in great detail in European Patent Application 84/03564, published on Sep. 13, 1984, which is herein incorporated by reference in its entirety. Briefly stated, large numbers of different small molecule test compounds are synthesized on a solid substrate, such as plastic pins or some other surface. The test compounds are reacted with polypeptides of the invention and washed. Bound polypeptides are then detected by methods well known in the art. Purified polypeptides are coated directly onto plates for use in the aforementioned drug screening techniques. In addition, non-neutralizing antibodies may be used to capture the peptide and immobilize it on the solid support.

This invention also contemplates the use of competitive drug screening assays in which neutralizing antibodies capable of binding polypeptides of the invention specifically compete with a test compound for binding to the polypeptides or fragments thereof. In this manner, the antibodies are used to detect the presence of any peptide that shares one or more antigenic epitopes with a polypeptide of the invention.

Example 67

Phosphorylation Assay

In order to assay for phosphorylation activity of the polypeptides of the invention, a phosphorylation assay as described in U.S. Pat. No. 5,958,405 (which is herein incorporated by reference) is utilized. Briefly, phosphorylation activity may be measured by phosphorylation of a protein substrate using gamma-labeled $^{32}$P-ATP and quantitation of the incorporated radioactivity using a gamma radioisotope counter. The polypeptides of the invention are incubated with the protein substrate, $^{32}$P-ATP, and a kinase buffer. The $^{32}$P incorporated into the substrate is then separated from free $^{32}$P-ATP by electrophoresis, and the incorporated $^{32}$P is counted and compared to a negative control. Radioactivity counts above the negative control are indicative of phosphorylation activity of the polypeptides of the invention.

Example 68

Detection of Phosphorylation Activity (Activation) of the Polypeptides of the Invention in the Presence of Polypeptide Ligands Methods known in the art or described herein may be used to determine the phosphorylation activity of the polypeptides of the invention. A preferred method of determining phosphorylation activity is by the use of the tyrosine phosphorylation assay as described in U.S. Pat. No. 5,817,471 (incorporated herein by reference).

Example 69

Identification of Signal Transduction Proteins that Interact with Polypeptides of the Present Invention The purified polypeptides of the invention are research tools for the identification, characterization and purification of additional signal transduction pathway proteins or receptor proteins. Briefly, labeled polypeptides of the invention are useful as reagents for the purification of molecules with which it interacts. In one embodiment of affinity purification, polypeptides of the invention are covalently coupled to a chromatography column. Cell-free extract derived from putative target cells, such as carcinoma tissues, is passed over the column, and molecules with appropriate affinity bind to the polypeptides of the invention. The protein complex is recovered from the column, dissociated, and the recovered molecule subjected to N-terminal protein sequencing. This amino acid sequence is then used to identify the captured molecule or to design degenerate oligonucleotide probes for cloning the relevant gene from an appropriate cDNA library.

Example 70

IL-6 Bioassay

To test the proliferative effects of the polypeptides of the invention, the IL-6 Bioassay as described by Marz et al. is utilized (*Proc. Natl. Acad. Sci., U.S.A.,* 95:3251-56 (1998), which is herein incorporated by reference). Briefly, IL-6 dependent B9 murine cells are washed three times in IL-6 free medium and plated at a concentration of 5,000 cells per well in 50 μl, and 50 μl of the IL-6-like polypeptide is added. After 68 hrs. at 37° C., the number of viable cells is measured by adding the tetrazolium salt thiazolyl blue (MTT) and incubating for a further 4 hrs. at 37° C. B9 cells are lysed by SDS and optical density is measured at 570 nm. Controls containing IL-6 (positive) and no cytokine (negative) are utilized. Enhanced proliferation in the test sample(s) relative to the negative control is indicative of proliferative effects mediated by polypeptides of the invention.

Example 71

Support of Chicken Embryo Neuron Survival

To test whether sympathetic neuronal cell viability is supported by polypeptides of the invention, the chicken embryo neuronal survival assay of Senaldi et al is utilized (*Proc. Natl. Acad. Sci., U.S.A.,* 96:11458-63 (1998), which is herein incorporated by reference). Briefly, motor and sympathetic neurons are isolated from chicken embryos, resuspended in L15 medium (with 10% FCS, glucose, sodium selenite, progesterone, conalbumin, putrescine, and insulin; LIFE TECHNOLOGIES™, Rockville, Md.) and Dulbecco's modified Eagles medium [with 10% FCS, glutamine, penicillin, and 25 mM Hepes buffer (pH 7.2); LIFE TECHNOLOGIES™, Rockville, Md.], respectively, and incubated at 37° C. in 5% $CO_2$ in the presence of different concentrations of the purified IL-6-like polypeptide, as well as a negative control lacking any cytokine. After 3 days, neuron survival is determined by evaluation of cellular morphology, and through the use of the colorimetric assay of Mosmann (Mosmann, T., *J. Immunol. Methods,* 65:55-63 (1983)). Enhanced neuronal cell viability as compared to the controls lacking cytokine is indicative of the ability of the inventive purified IL-6-like polypeptide(s) to enhance the survival of neuronal cells.

Example 72

Assay for Phosphatase Activity

The following assay may be used to assess serine/threonine phosphatase (PTPase) activity of the polypeptides of the invention.

In order to assay for serine/threonine phosphatase (PTPase) activity, assays can be utilized which are widely known to those skilled in the art. For example, the serine/threonine phosphatase (PSPase) activity is measured using a PSPase assay kit from New England Biolabs, Inc. Myelin basic protein (MyBP), a substrate for PSPase, is phosphorylated on serine and threonine residues with cAMP-dependent Protein Kinase in the presence of [$^{32}$P]ATP. Protein serine/threonine phosphatase activity is then determined by measuring the release of inorganic phosphate from 32P-labeled MyBP.

Example 73

Interaction of Serine/Threonine Phosphatases with Other Proteins

The polypeptides of the invention with serine/threonine phosphatase activity as determined in Example 72 are research tools for the identification, characterization and purification of additional interacting proteins or receptor proteins, or other signal transduction pathway proteins. Briefly, labeled polypeptide(s) of the invention is useful as a reagent for the purification of molecules with which it interacts. In one embodiment of affinity purification, polypeptide of the invention is covalently coupled to a chromatography column. Cell-free extract derived from putative target cells, such as neural or liver cells, is passed over the column, and molecules with appropriate affinity bind to the polypeptides of the invention. The polypeptides of the invention—complex is recovered from the column, dissociated, and the recovered molecule subjected to N-terminal protein sequencing. This amino acid sequence is then used to identify the captured molecule or to design degenerate oligonucleotide probes for cloning the relevant gene from an appropriate cDNA library.

Example 74

Assaying for Heparanase Activity

In order to assay for heparanase activity of the polypeptides of the invention, the heparanase assay described by Vlodaysky et al is utilized (Vlodaysky, I., et al., Nat. Med., 5:793-802 (1999)). Briefly, cell lysates, conditioned media or intact cells ($1\times10^6$ cells per 35-mm dish) are incubated for 18 hrs at 37° C., pH 6.2-6.6, with $^{35}$S-labeled ECM or soluble ECM derived peak I proteoglycans. The incubation medium is centrifuged and the supernatant is analyzed by gel filtration on a Sepharose CL-6B column (0.9×30 cm). Fractions are eluted with PBS and their radioactivity is measured. Degradation fragments of heparan sulfate side chains are eluted from Sepharose 6B at $0.5<K_{av}<0.8$ (peak II). Each experiment is done at least three times. Degradation fragments corresponding to "peak II," as described by Vlodaysky et al., is indicative of the activity of the polypeptides of the invention in cleaving heparan sulfate.

Example 75

Immobilization of Biomolecules

This example provides a method for the stabilization of polypeptides of the invention in non-host cell lipid bilayer constructs (see, e.g., Bieri et al., Nature Biotech 17:1105-1108 (1999), hereby incorporated by reference in its entirety herein) that can be adapted for the study of polypeptides of the invention in the various functional assays described above. Briefly, carbohydrate-specific chemistry for biotinylation is used to confine a biotin tag to the extracellular domain of the polypeptides of the invention, thus allowing uniform orientation upon immobilization. A 50 uM solution of polypeptides of the invention in washed membranes is incubated with 20 mM NaIO4 and 1.5 mg/ml (4 mM) BACH or 2 mg/ml (7.5 mM) biotin-hydrazide for 1 hr at room temperature (reaction volume, 150 ul). Then the sample is dialyzed (Pierce Slidealizer Cassett, 10 kDa cutoff; Pierce Chemical Co., Rockford Ill.) at 4° C. first for 5 h, exchanging the buffer after each hour, and finally for 12 h against 500 ml buffer R (0.15 M NaCl, 1 mM $MgCl_2$, 10 mM sodium phosphate, pH7). Just before addition into a cuvette, the sample is diluted 1:5 in buffer ROG50 (Buffer R supplemented with 50 mM octylglucoside).

Example 76

TAQMAN®

Quantitative PCR (QPCR). Total RNA from cells in culture are extracted by TRIZOL™ separation as recommended by the supplier (LifeTechnologies). (Total RNA is treated with DNase I (LIFE TECHNOLOGIES™) to remove any contaminating genomic DNA before reverse transcription.) Total RNA (50 ng) is used in a one-step, 50 ul, RT-QPCR, consisting of TaqMan® Buffer A (Perkin-Elmer; 50 mM KCl/10 mM Tris, pH 8.3), 5.5 mM $MgCl_2$, 240 μM each dNTP, 0.4 units RNase inhibitor (PROMEGA™), 8% glycerol, 0.012% Tween-20, 0.05% gelatin, 0.3 μM primers, 0.1 μM probe, 0.025 units Amplitaq Gold® (Perkin-Elmer) and 2.5 units Superscript II reverse transcriptase (LIFE TECHNOLOGIES™). As a control for genomic contamination, parallel reactions are setup without reverse transcriptase. The relative abundance of (unknown) and 18S RNAs are assessed by using the Applied Biosystems Prism 7700 Sequence Detection System (Livak, K. J., Flood, S. J., Marmaro, J., Giusti, W. & Deetz, K. (1995) PCR Methods Appl. 4, 357-362). Reactions are carried out at 48° C. for 30 min, 95° C. for 10 min, followed by 40 cycles of 95° C. for 15 s, 60° C. for 1 min. Reactions are performed in triplicate.

Primers (f & r) and FRET probes sets are designed using Primer Express Software (Perkin-Elmer). Probes are labeled at the 5'-end with the reporter dye 6-FAM and on the 3'-end with the quencher dye TAMRA (Biosource International, Camarillo, Calif. or Perkin-Elmer).

Example 77

Assays for Metalloproteinase Activity

Metalloproteinases (EC 3.4.24.-) are peptide hydrolases which use metal ions, such as $Zn^{2+}$, as the catalytic mechanism. Metalloproteinase activity of polypeptides of the present invention can be assayed according to the following methods.

Proteolysis of Alpha-2-Macroglobulin

To confirm protease activity, purified polypeptides of the invention are mixed with the substrate alpha-2-macroglobulin (0.2 unit/ml; BOEHRINGER™ Mannheim, Germany) in 1× assay buffer (50 mM HEPES, pH 7.5, 0.2 M NaCl, 10 mM $CaCl_2$, 25 μM $ZnCl_2$ and 0.05% Brij-35) and incubated at 37° C. for 1-5 days. Trypsin is used as positive control. Negative controls contain only alpha-2-macroglobulin in assay buffer. The samples are collected and boiled in SDS-PAGE sample buffer containing 5% 2-mercaptoethanol for 5-min, then loaded onto 8% SDS-polyacrylamide gel. After electrophoresis the proteins are visualized by silver staining Proteolysis is evident by the appearance of lower molecular weight bands as compared to the negative control.

Inhibition of Alpha-2-Macroglobulin Proteolysis by Inhibitors of Metalloproteinases Known metalloproteinase inhibitors (metal chelators (EDTA, EGTA, AND $HgCl_2$), peptide metalloproteinase inhibitors (TIMP-1 and TIMP-2), and commercial small molecule MMP inhibitors) are used to characterize the proteolytic activity of polypeptides of the invention. The three synthetic MMP inhibitors used are: MMP inhibitor I, [$IC_{50}$=1.0 μM against MMP-1 and MMP-8; $IC_{50}$=30 μM against MMP-9; $IC_{50}$=150 μM against MMP-3]; MMP-3 (stromelysin-1) inhibitor I [$IC_{50}$=5 μM against MMP-3], and MMP-3 inhibitor II [$K_i$=130 nM against MMP-3]; inhibitors available through Calbiochem, catalog #444250, 444218, and 444225, respectively). Briefly, different concentrations of the small molecule MMP inhibitors are mixed with purified polypeptides of the invention (50 μg/ml) in 22.9 μl of 1×HEPES buffer (50 mM HEPES, pH 7.5, 0.2 M NaCl, 10 mM $CaCl_2$, 25 μM $ZnCl_2$ and 0.05% Brij-35) and incubated at room temperature (24° C.) for 2-hr, then 7.1 μl of substrate alpha-2-macroglobulin (0.2 unit/ml) is added and incubated at 37° C. for 20-hr. The reactions are stopped by adding 4× sample buffer and boiled immediately for 5 minutes. After SDS-PAGE, the protein bands are visualized by silver stain.

Synthetic Fluorogenic Peptide Substrates Cleavage Assay

The substrate specificity for polypeptides of the invention with demonstrated metalloproteinase activity can be determined using synthetic fluorogenic peptide substrates (purchased from BACHEM Bioscience Inc). Test substrates include, M-1985, M-2225, M-2105, M-2110, and M-2255. The first four are MMP substrates and the last one is a substrate of tumor necrosis factor-α (TNF-α) converting enzyme (TACE). All the substrates are prepared in 1:1 dimethyl sulfoxide (DMSO) and water. The stock solutions are 50-500 μM. Fluorescent assays are performed by using a Perkin Elmer LS 50B luminescence spectrometer equipped with a constant temperature water bath. The excitation λ is 328 nm and the emission λ is 393 nm. Briefly, the assay is carried out by incubating 176 μl 1×HEPES buffer (0.2 M NaCl, 10 mM $CaCl_2$, 0.05% Brij-35 and 50 mM HEPES, pH 7.5) with 4 μl of substrate solution (50 μM) at 25° C. for 15 minutes, and then adding 20 μl of a purified polypeptide of the invention into the assay cuvett. The final concentration of substrate is 1 μM. Initial hydrolysis rates are monitored for 30-min.

Example 78

Characterization of the cDNA Contained in a Deposited Plasmid

The size of the cDNA insert contained in a deposited plasmid may be routinely determined using techniques known in the art, such as PCR amplification using synthetic primers hybridizable to the 3' and 5' ends of the cDNA sequence. For example, two primers of 17-30 nucleotides derived from each end of the cDNA (i.e., hybridizable to the absolute 5' nucleotide or the 3' nucleotide end of the sequence of SEQ ID NO:X, respectively) are synthesized and used to amplify the cDNA using the deposited cDNA plasmid as a template. The polymerase chain reaction is carried out under routine conditions, for instance, in 25 μl of reaction mixture with 0.5 μg of the above cDNA template. A convenient reaction mixture is 1.5-5 mM $MgCl_2$, 0.01% (w/v) gelatin, 20 μM each of dATP, dCTP, dGTP, dTTP, 25 pmol of each primer and 0.25 Unit of Taq polymerase. Thirty five cycles of PCR (denaturation at 94 degree C. for 1 min; annealing at 55 degree C. for 1 min; elongation at 72 degree C. for 1 min) are performed with a Perkin-Elmer Cetus automated thermal cycler. The amplified product is analyzed by agarose gel electrophoresis. The PCR product is verified to be the selected sequence by subcloning and sequencing the DNA product. It will be clear that the invention may be practiced otherwise than as particularly described in the foregoing description and examples. Numerous modifications and variations of the present invention are possible in light of the above teachings and, therefore, are within the scope of the appended claims.

Example 79

Cloning, Sequence Analysis and Chromosomal Localization of the Novel Human Integrin Alpha 11 Subunit The integrins are a large family of cell adhesion molecules consisting of noncovalently associated αβ heterodimers. We have cloned and sequenced a novel human integrin α-subunit cDNA, designated α11. The α11 cDNA encodes a protein with a 22 amino acid signal peptide, a large 1120 residue extracellular domain that contains an I-domain of 207 residues and is linked by a transmembrane domain to a short cytoplasmic domain of 24 amino acids. The deduced α11 protein shows the typical structural features of integrin α-subunits and is similar to a distinct group of α-subunits from collagen-binding integrins. However, it differs from most integrin α-chains by an incompletely preserved cytoplasmic GFFKR motif. The human ITGA11 gene was located to bands q22.3-23 on chromosome 15, and its transcripts were found predominantly in bone, cartilage as well as in cardiac and skeletal muscle. Expression of the 5.5 kilobase α11 mRNA was also detectable in ovary and small intestine.

Introduction

All vertebrate cells express members of the integrin family of cell adhesion molecules, which mediate cellular adhesion to other cells and extracellular subtratum, cell migration and participate in important physiologic processes from signal transduction to cell proliferation and differentiation (Hynes, 92; Springer, 92). Integrins are structurally homologous heterodimeric type-I membrane glycoproteins formed by the noncovalent association of one of eight β-subunits with one of the 17 different α-subunits described to date, resulting in at least 22 different αβ complexes. Their binding specificities for cellular and extracellular ligands are determined by both subunits and are dynamically regulated in a cell-type-specific mode by the cellular environment as well as by the developmental and activation state of the cell (Diamond and Springer, 94). In integrin α-subunits, the aminoterminal region of the large extracellular domain consists of a seven-fold repeated structure which is predicted to fold into a β-propeller domain (Corbi et al., 1987; Springer, 1997). The three or four C-terminal repeats contain putative divalent cation binding motifs that are thought to be important for ligand binding and subunit association (Diamond and Springer, 94). The $\alpha^1$, $\alpha^2$, $\alpha^{10}$, $\alpha^D$, $\alpha^E$, $\alpha^L$, $\alpha^M$ and $\alpha^X$-subunits contain an approximately 200 amino acid I-domain inserted between the second and third repeat that is not present in other α-chains (Larson et al., 1989). Several isolated I-domains have been shown to independently bind the ligands of the parent integrin heterodimer (Kamata and Takada, 1994; Randi and Hogg, 1994). The $\alpha^3$, $\alpha^{5-8}$, $\alpha^{IIb}$ and $\alpha^V$-subunits are proteolytically processed at a conserved site into disulphide-linked heavy and light chains, while the $\alpha^4$-subunit is cleaved at a more aminoterminal site into two fragments that remain noncovalently associated (Hemler et al., 90). Additional α-subunit variants are generated by alternative splicing of primary transcripts (Ziober et al., 93; Delwel et al., 95; Leung et al., 98). The extracellular domains of α-integrin subunits are connected by a single spanning transmembrane domain to short, diverse cytoplasmic domains whose only conserved feature is a membrane-proximal KXGFF(K/R)R motif (Sastry and Horwitz, 1993). The cytoplasmic domains have been implicated in the cell-type-specific modulation of integrin affinity states (Williams et al., 1994).

Here we report the cDNA cloning, sequence analysis, expression and chromosomal localization of the human α-integrin subunit.

Materials and Methods

Library Screening and DNA Sequencing.

A human fetal heart cDNA library in λgt10 (Clontech Laboratories, Inc., Palo Alto, Calif., USA) was screened with $^{32}P$-labelled (REDIPRIME™, Amersham New Zealand Ltd., Auckland, New Zealand) probes corresponding to the regions 473 to 749 and 2394 to 3189 of the α11 cDNA using standard procedures. Inserts were subcloned from λgt10 into pUC21 and sequenced on both strands according to a successive specific primer strategy on an automated sequencer (Applied Biosystems 373A, The Centre for Gene Technology, School of Biological Sciences, The University of Auckland).

Northern Blot Analysis and Tissue Distribution.

A 1341 bp PCR fragment corresponding to the region 351-1692 of the α cDNA was $^{32}P$-labelled (REDIPRIME™) and hybridized with human multiple tissue Northern blots (MTN I and MTN II, CLONTECH™) for 16 h at 60∞ C in EXPRESSHYB™ solution (CLONTECH™). Filters were washed twice with 0.1×SSC/1% SDS at 50° C. for 30 min, and autoradiographed. Human DNA from 63 tissue-specific cDNA libraries (Express-Check™, American Type Culture Collection, Manassas, Va., USA) was amplified using primers KL120 (5'-GCAGGGATGCCACCTGCC) and KL119 (5'-GATGAAGACTGTGGTGTCGAAGG) according to the manufacturers instructions. PCR-products were resolved by agarose gel electrophoresis and transferred to Hybond C+ (Amersham). Filters were hybridized by standard procedures (Ausubel et al., 98) with a 502 bp $^{32}P$-labelled (REDIPRIME™) probe fragment obtained from the cloned "[11] cDNA with the same oligonucleotides.

Chromosomal Assignment.

500 ng genomic DNA prepared from a panel of 21 human-rodent somatic cell hybrids or from human, mouse and hamster cells (Kelsell et al., 95) was amplified with oligonucleotides KL175 (5'-GGTGCCAGACCTACATGGAC) and KL189 (5'-CGTGCAAATTCAATGCCAAATGCC) in a standard PCR reaction of 30 cycles (94° C. for 1 min, 55° C. for 1 min, 72° C. for 2 min). All PCR reactions were resolved in a 2% agarose gel. Southern hybridization was performed as detailed above, except that the probe fragment was obtained from clone HOHBY69 with oligonucleotides KL175 and KL189. For fluorescent in situ hybridization, metaphase spreads were prepared from phytohemagglutinin-stimulated peripheral blood lymphocytes of a 46,XY male donor using standard cytogenetic procedures. A purified 3.7 kB fragment representing the entire coding region of clone HOHBY69 was labelled with biotin-16-dUTP using the High Prime labelling kit (Roche Molecular Biochemicals, Auckland, NZ). Conditions for hybridization and immunofluorescent detection were essentially as described (Morris et al., 93), except that $C_0t-1$ suppression was not required, slides were washed to a stringency of 0.1×SSC/60° C. after hybridization, and an additional amplification step was needed because of the small size of the probe. For precise chromosome band localization, DAPI and FITC images were captured using a Photometrics KAF1400 CCD camera and QUIPS Smartcapture FISH software version 1.3 (Vysis Inc., Downers Grove, Ill., USA). QUIPS CGH/Karyotyping software (version 3.0.2) assisted karyotype analysis.

Results

Cloning of a Novel Human α-Integrin Subunit cDNA:

A protein homology search (Altschul et al., 90) of the human expressed sequence tag (EST) databases of Human Genome Sciences, Inc. (Ni et al., 97) and The Institute for Genomic Research (Kirkness and Kerlavage, 97) identified the clones HRDAF83 and HOEAM34 as candidate novel integrin α-subunit cDNAs. Clone HRDAF83 was isolated from a human rhabdomyosarcoma cDNA library and sequenced on both strands. The 1223 bp insert contains largely incompletely processed hnRNA and a 277 bp region that showed homology to the aminoterminal half of the α1-integrin I-domain. The 2517 bp insert of clone HOEAM34 was derived from a human osteoblast cDNA library. It is homologous to the C-terminal part of the human α1-subunit and contains 1324 nucleotides of 3'-untranslated region. In order to isolate the full-length cDNAs for these integrin α-subunits, a cDNA library prepared from human fetal heart in λgt10 was screened with the 277 bp fragment from clone HRDAF83 homologous to the α1-I-domain. Two clones, λ831 and λ832, were isolated and both strands of their inserts sequenced. Clone λ832 contains the entire 5' half of a novel α-subunit cDNA, while clone λ831 covers the same region, but is 358 bp and 173 bp shorter than λ831 at its 5'- and 3'-ends, respectively. A screening of the same library with a 795 bp fragment from the extreme 5'-terminus of clone HOEAM34 identified clone λ342, which contained essentially the same region as clone HOEAM34 but has a 317 bp shorter 3'-untranslated region. Rescreening the EST databases with the sequences derived from the human fetal heart library led to the identification of clone HOHBY69, which was isolated from a osteoblast cDNA library. Both strands of the 4681 bp insert of clone HOHBY69 were sequenced. The 5'-region of HOHBY69 was identical to the HRDAF83/λ832/λ831-group, while the 3'-region of HOHBY69 was largely identical to HOEAM34 and λ342, thereby demonstrating that the two groups of partial cDNAs represent the 5'- and 3'-portions of the same cDNA. One major difference between the HOHBY69 and HOEAM34/λ342 is the presence of an additional GTA-triplet at position 3088 in HOHBY69. From the overlapping clones, a total of 4986 bp of cDNA was assembled to the composite sequence shown in FIG. 19A-F and has been submitted to GenBank™ with accession number AF109681. This cDNA encodes a previously unidentified human integrin α-subunit that was designated α11.

Structure of the Human α11-Subunit.

The all cDNA contains a 5'-untranslated region of 72 nucleotides and a single open reading frame extending from a predicted translation initiation codon at position +1 to a TGA termination codon at position 3570. This is followed by 1324 nucleotides of 3' untranslated region which contains an AATTAAA polyadenylation signal (Wahle and Keller, 1996) 12 nucleotides upstream of a poly(A) stretch. The deduced amino acid sequence contains a 22 residue N-terminal region with the characteristics of a cleaved signal peptide (von Heijne, 83; Nielsen et al., 97), a large extracellular domain of 1120 amino acids followed by a 23 amino acid hydrophobic stretch that resembles a transmembrane domain, and a short 24 residue cytoplasmic domain. The molecular weight of the mature 1167 amino acid all-subunit is predicted to be 131 kDa, but the addition of carbohydrate side chains to any of the 15 potential N-glycosylation sequons [NX(S/T)] within the extracellular domain is likely to increase the molecular weight of the native protein. An I-domain of 207 amino acids is inserted between the second and third repeat. Consistent with the structure of an typical I-domain-containing integrin α-subunit, it lacks a potential dibasic protease cleavage site in the C-terminal region of the extracellular domain.

The α11-subunit is most closely related to the recently discovered α10-subunit (Camper et al., 98, Lehnert et al., in preparation) and the α1- and α2-subunits. Overall, the mature α11-protein is 45% identical to the α10 chain, while the homologies to the α1- and α2-subunits are 41% and 39%, respectively. Even greater homology exists between the I-domains of the α10- and α11-subunits which are 60% identical to each other. The high degree of homology seen in the extracellular domains of the subunits is in contrast to the low similarity of their cytoplasmic domains. Interestingly, the KXGFF(K/R)R motif that is absolutely conserved in all other α-subunit cytoplasmic domains is only partially preserved in both subunits. The sequence in α11 is KLGFFRS, while the α10-subunit contains a KLGFFAH motif. A graphical comparison of the similarity between all integrin α-subunits is shown in FIG. 3 (Lehnert et al.). Together with the α-subunits from the collagen-binding integrins α1β1, α2β1 and α10β1, the α11-subunit forms a group distinct from the other I-domain-containing integrin subunits.

Tissue Distribution and Expression of the Integrin α11-Subunit.

The tissue distribution of the α11 mRNA was assessed by screening multiple human tissue Northern blots with a probe corresponding to the region 351-1692 of the α11 cDNA. A single transcript of approximately 5.5 kb was found weakly expressed only in ovary and small intestine. Integrin α11-subunit expression was further analyzed by amplification and Southern hybridization of a 502 bp fragment corresponding to the region 1988-2490 in the α11 cDNA from tissue-specific human cDNA libraries. α11 cDNA was detected in five different cDNA libraries prepared from fetal heart (day 57-75), in two fetal brain libraries, and in a cDNA library from large intestine (not shown). An analysis of the Human Genome Sciences Database revealed eight different α11-related ESTs in human osteoblast libraries, three EST in a human chondrosarcoma cDNA library and two EST in a human stromal osteoclastoma library.

Chromosomal Localization of the Integrin α11-Subunit.

Genomic DNA from a collection of 21 human-rodent somatic cell hybrids (Kelsell et al., 95) was amplified by PCR using oligonucleotide primers directed the region 473 to 749 of the human α11 cDNA. In Southern hybridization, a signal corresponding to a 1.4 kb fragment was detectable only with DNA from a hybrid cell line that contains human chromosome 15. A fragment of the same size was also amplified from human genomic DNA, but not from mouse or hamster DNA (FIG. 5C (Lehnert et al.)). Cloning and sequence of the PCR product from chromosome 15 revealed the presence of a 1154 bp intron inserted after cDNA-position 600, thus resulting in a PCR-product of 1431 bp. The ITGA11 gene was also localized by fluorescent in situ hybridization of metaphase chromosomes with the entire coding region from clone HOHBY69. All of 20 metaphase cells analyzed showed fluorescent signal on both chromosomes 15, specifically across bands q22.3-q23. No additional signals were detected on any other chromosome (FIG. 5A (Lehnert et al.)).

Discussion:

We have cloned and sequenced a novel cDNA encoding a protein that shares extensive structural homology with integrin α-chains. The aminoterminal 22 amino acids of the deduced protein sequence show the characteristic features of a hydrophobic leader peptide, including a signal peptidase recognition motif at positions −3 and −1 (von Heijne 83). Proteolytic cleavage of the precursor protein at this position would result in an aminoterminal sequence for the mature α11-chain of FNMD, which is similar to the consensus sequence[(F/Y)N(L/V)D] of all other integrin α11-subunits (Tuckwell et al., 94). The N-terminal half of the large extracellular region of α11 is composed of seven repeats that each contain FG-GAP-GxxY consensus motifs (FG-GAP repeats). These repeats can be found in all integrin α1-subunits and are predicted to fold into a β-propeller domain (Springer, 97). Inserted between the second and third FG-GAP repeats is a 207 amino acid I-domain spanning from glutamine[138] to methionine[344]. It contains a divalent cation coordination motif that has been shown to directly bind $Mg^{2+}$ ions in the $\alpha^M$ subunit (Michishita et al., 96). The noncontiguous amino acid side chains involved in the coordination of magnesium or manganese ions have been identified by mutagenesis analysis and from crystal structures of the isolated $\alpha^2$, $\alpha^L$ and $\alpha^M$-subunit I-domains (Emsley et al., 97; Qu and Leahy, 95; Lee et al., 95). All residues required for the coordination of the divalent cations in these subunits are preserved in the α11-I-domain. These are the asparagines at positions 148 and 249, the serine residues at position 150 and 152, and the threonine at position 218.

The crystal structure of the α2-subunit has revealed a small "-helix that is not present in the I-domains of the β2-associated α-subunits. Together with the MIDAS sphere, amino acid residues from this C-helix and the adjacent turn region have been proposed to make physical contacts to a collagen triple helix (Emsley et al., 97). Interestingly, the small C-helix is structurally conserved in the α-subunits of the collagen-binding integrins α1β1, α2β1 and α10β1, and is also present in the α11 I-domain ($G^{279}YYNR^{283}$). In addition, asparagine[154] and histidine[258] of the α2-I-domain were predicted to contact the collagen triple helix, and both are preserved in the α1, α10 and α11-I-domains, but not in other integrin all-subunits. The conservation of structural motifs required for collagen binding suggests that collagen may be a ligand for the α11 integrin. Each of the repeats 5-7 of the α11-subunit accommodates the sequence Dx(D/N)xDxxxD. Three or four copies of these putative divalent cation binding sites are conserved in all integrin α-subunits and their presence is consistent with the divalent cation requirement for the adhesive function of integrins (Larson et al., 89; Fujimura and Phillips, 83; Hynes, 92). The extracellular domain of the integrin all-subunit contains 20 cysteine residues. Only the intramolecular disulfide bonds in the "$^{IIb}$ subunit have been biochemically characterized (Calvete et al., 89), but the location of many cysteines is conserved in integrin α-subunits. In the α11-subunit, the cysteine residues 637 and 646, 652 and 707, 759 and 765, and 859 and 871 are homologous to the residues that form the four carboxyterminal disulfide bonds in the heavy chain of "$^{IIb}$ (Calvete et al., 89). Based on the proposed structure of the integrin α-subunit propeller domain (Springer et al., 97), additional disulfide bonds within the α11 subunit can be predicted between cysteine residues 54 and 61, 99 and 117, and between 107 and 137. Two additional cysteine residues are found within a short segment (residues 783 to 798) that is unique to the all-subunit.

The integrin cytoplasmic domains play central roles in integrin affinity modulation and in cellular signal transmission. The membrane-proximal sequence KxGFF(K/R)R is strictly conserved among integrin α-subunit cytoplasmic domains (Williams et al., 94). Within this motif, both phenylalanine residues and the last arginine have been implicated in maintaining the default low affinity state of integrins $\alpha^L\beta_2$ and $\alpha^{IIb}\beta_3$, as their substitution or deletion resulted in constitutively activated ligand binding (O'Toole et al., 94, Lu and Spriner 97). Interestingly, the last arginine residue is replaced by a serine in the α11 cytoplasmic domain and with a histidine in the α10 subunit, suggesting that both integrins might be in a default "high" affinity state. It will be interesting to analyze whether substitution of these residues with a conserved arginine will affect their affinity status.

We have isolated α11 cDNAs from osteoclast, osteoblast, myosarcoma and fetal heart libraries. Amongst the HGS EST databases, integrin α11 transcripts were predominantly found in libraries prepared from osteoblast, osteoclast and chondrosarcoma cells. A search for further "[11]-related sequences in the EST division of the GenBank database revealed two clones (accession numbers Z50157 and Z50167) from primary human myoblasts (Genini et al., 96), two clones from human trabecular bone cells (AA852614 and AA852615), as well as clones from fibroblast cells (W45078), pancreatic tumor (U53091) and breast tissue (H16112). In contrast, Northern blot analysis detected α11-expression only in ovary and small intestine. only fetal heart, fetal brain and large intestine. Of the tissues represented in the tissue-specific cDNA-library panel, only fetal heart, fetal brain and large intestine showed detectable α11-expression. However, bone- and muscle-derived tissues were not included in the Northern blot, and cDNA libraries prepared from these tissues were also not represented in the tissue-specific cDNA panel.

The ITGA11 gene was localized to chromosome 15, bands q22.3-23, by FISH and PCR analysis of human-rodent somatic cell hybrids. This segment is overrepresented in squamous cell carcinomas (Wolff et al., 1998), but appears to only infrequently affected in other cancers. Genes at this region encode neogenin, a protein expressed ubiquitously expressed in human tissues (Meyerhardt et al., 97); tropomyosin 1, expressed in cardiac and skeletal muscle tissues (Tiso et al., 97); and the human homologue of the metalloprotease-disintegrin kuzbanian, which is overexpressed in tumors of sympathoadrenal origin (Yavari et al., 98). In addition, the region 15q22.3-q23 is linked to Bardet-Biedl syndrome 4, a heterogeneous autosomal disorder characterized by obesity and associated with cardiovascular anomalities (Carmi et al., 95).

In conclusion, we have cloned and sequenced the cDNA for the novel integrin α11-subunit which is closely related to the "-subunits of the collagen-binding integrins β1β1, α2β1 and α10β1. The high degree of homology of α11 to these subunits suggests that it associates with the integrin β1-subunit, and may function as an additional collagen receptor.

All references referred to above and presented below are hereby incorporated herein by reference:

Altschul S. F., Gish, W., Miller, W., Myers, E. W., and Lipman, D. J. (1990). Basic local alignment search tool. *Journal of Molecular Biology* 215: 403-410.

Ausbel, F. A., Brent, R., Kingston, R. E., Moore, D. D., Seidman, J. G., Smith, J. A., and Struhl, K. (1998). "Current protocols in molecular biology" John Wiley & Sons, New York.

Calvete J. J., Henschen, A., and Gonzalez-Rodriguez, J. (1989). Complete localization of the intrachain disulphide bonds and the N-glycosylation points in the alpha-subunit of human platelet glycoprotein IIb. *Biochemical Journal* 261: 561-568.

Camper L., Hellman, U., and Lundgren-Akerlund, E. (1998). Isolation, cloning and sequence analysis of the integrin subunit α10, a β1-associated collagen binding integrin expressed on chondrocytes. *Journal of Biological Chemistry* 273: 20383-20389.

Carmi R., Rokhlina, T., Kwitek-Black, A. E., Elbedour, K., Nishimura, D., Stone, E. M., and Sheffield, V. C. (1995). Use of a DNA pooling strategy to identify a human obesity syndrome locus on chromosome 15. *Human Molecular Genetics* 4: 9-13.

Corbi A. L., Miller, L. J., O'Connor, K., Larson, R. S., and Springer, T. A. (1987). cDNA cloning and complete primary structure of the alpha subunit of a leukocyte adhesion glycoprotein, p 150,95. *EMBO Journal* 6: 4023-4028.

De Melker A. A., Kramer, D., Kuikman, I., and Sonnenberg, A. (1997). The two phenylalanines in the GFFKR motif of the integrin alpha6A subunit are essential for heterodimerization. *Biochemical Journal* 328: 529-537.

Diamond M. S. and Springer, T. A. (1994). The dynamic regulation of integrin adhesiveness. *Current Biology* 4: 506-517.

Emsley J., King, S. L., Bergelson, J. M., and Liddington, R. C. (1997). Crystal structure of the I domain from integrin alpha2beta1. *Journal of Biological Chemistry* 272: 28512-28517.

Fujimura K. and Phillips, D. R. (1983). Calcium cation regulation of glycoprotein IIb-IIIa complex formation in platelet plasma membranes. *Journal of Biological Chemistry* 258: 10247-10252.

Genini M., Schwalbe, P., Scholl, F. A., and Schafer, B. W. (1996). Isolation of genes differentially expressed in human primary myoblasts and embryonal rhabdomyosarcoma. *International Journal of Cancer* 66: 571-577.

Hemler M. E., Elices, M. J., Parker, C., and Takada, Y. (1990). Structure of the integrin VLA-4 and its cell-cell and cell-matrix adhesion functions. *Immunological Reviews* 114: 45-65.

Hynes R. O. (1992). Integrins: versatility, modulation, and signaling in cell adhesion. *Cell* 69: 11-25.

Kelsell D. P., Rooke, L., Warne, D., Bouzyk, M., Cullin, L., Cox, West, L., Povey, S., and Spurr, N. K. (1995). Development of a panel of monochromosomal somatic cell hybrids for rapid gene mapping. *Annals of Human Genetics* 59: 233-241.

Kirkness E. F. and Kerlavage, A. R. (1997). The TIGR human cDNA database. *Methods in Molecular Biology* 69: 261-268.

Lee J. O., Rieu, P., Arnaout, M. A., and Liddington, R. (1995). Crystal structure of the A domain from the alpha subunit of integrin CR3 (CD11b/CD18). *Cell* 80: 631-638.

Larson R. S., Corbi, A. L., Berman, L., and Springer, T. (1989). Primary structure of the leukocyte function-associated molecule-1 alpha subunit: an integrin with an embedded domain defining a protein superfamily. *Journal of Cell Biology* 108: 703-712.

Leung E., Lim, S. P., Berg, R., Yang, Y., Ni, J., Wang, S. X., and Krissansen, G. W. (1998). A novel extracellular domain variant of the human integrin alpha 7 subunit generated by alternative intron splicing. *Biochemical & Biophysical Research Communications* 243: 317-325.

Lu C. F. and Springer, T. A. (1997). The alpha subunit cytoplasmic domain regulates the assembly and adhesiveness of integrin lymphocyte function-associated antigen-1. *Journal of Immunology* 159: 268-278.

Michishita M., Videm, V., and Arnaout, M. A. (1993). A novel divalent cation-binding site in the A domain of the beta 2 integrin CR3 (CD11b/CD18) is essential for ligand binding. *Cell* 72: 857-867.

Meyerhardt J. A., Look, A. T., Bigner, S. H., and Fearon, E. R. (1997). Identification and characterization of neogenin, a DCC-related gene. *Oncogene* 14: 1129-1136.

Morris C., Courtay, C., Geurts, v. K., ten Hoeve, J., Heisterkamp, N., and Groffen, J. (1993). Localization of a gamma-glutamyl-transferase-related gene family on chromosome 22. *Human Genetics* 91: 31-36.

Ni J., Abrahamson, M., Zhang, M., Fernandez, M., Grubb, A., Su, J., Yu, G.-L., and Li, Y.-L. (1997). Cystatin E is a novel human cysteine proteinase inhibitor with structural resemblance to family 2 cystatins. *Journal of Biological Chemistry* 272:10853-10858.

Nielsen H., Engelbrecht, J., Brunak, S., von, and Heijne, G. (1997). Identification of prokaryotic and eukaryotic signal peptides and prediction of their cleavage sites. *Protein Engineering* 10:1-6.

O'Toole T. E., Katagiri, Y., Faull, R. J., Peter, K., Tamura, R., Quaranta, V., Loftus, J. C., Shattil, S. J., and Ginsberg, M. H. (1994). Integrin cytoplasmic domains mediate inside-out signal transduction. *Journal of Cell Biology* 124: 1047-1059.

Qu A. and Leahy, D. J. (1995). Crystal structure of the I-domain from the CD11a/CD18 (LFA-1, alpha L beta 2) integrin. *Proceedings of the National Academy of Sciences of the United States of America* 92: 10277-10281.

Sastry S. K. and Horwitz, A. F. (1993). Integrin cytoplasmic domains: mediators of cytoskeletal linkages and extra- and intracellular initiated transmembrane signaling. *Current Opinion in Cell Biology* 5: 819-831.

Springer T. A. (1997). Folding of the N-terminal, ligand-binding region of integrin alpha-subunits into a beta-propeller domain. *Proceedings of the National Academy of Sciences of the United States of America* 94: 65-72.

Springer T. A. (1990). Adhesion receptors of the immune system. *Nature* 346: 425-434.

Tiso N., Rampoldi, L., Pallavicini, A., Zimbello, R., Pandolfo, Valle, G., Lanfranchi, G., and Danieli, G. A. (1997). Fine mapping of five human skeletal muscle genes: alpha-tropomyosin, beta-tropomyosin, troponin-I slow-twitch, troponin-I fast-twitch, and troponin-C fast. *Biochemical & Biophysical Research Communications* 230: 347-350.

Tuckwell D. S., Humphries, M. J., and Brass, A. (1994). A secondary structure model of the integrin alpha subunit N-terminal domain based on analysis of multiple alignments. *Cell Adhesion & Communication* 2: 385-402.

von Heijne G. (1983). Patterns of amino acids near signal-sequence cleavage sites. *European Journal of Biochemistry* 133: 17-21.

Wahle E. and Keller, W. (1996). The biochemistry of polyadenylation. *Trends in Biochemical Sciences* 21: 247-250.

Williams M. J., Hughes, P. E., O'Toole, T. E., and Ginsberg, M. H. (1998). The inner world of cell adhesion: Integrin cytoplasmic domains. *Trends in Cell Biology* 4: 109-112.

Wolff E., Girod, S., Liehr, T., Vorderwulbecke, U., Ries, J., Steininger, H., Gebhart, E. (1998). Oral squamous cell carcinomas are characterized by a rather uniform pattern of genomic imbalances detected by comparative genomic hybridisation. *Oral Oncology* 34: 186-190.

Ziober B. L., Vu, M. P., Waleh, N., Crawford, J., Lin, C. S., Kramer, and R H (1993). Alternative extracellular and cytoplasmic domains of the integrin alpha 7 subunit are differentially expressed during development. *Journal of Biological Chemistry* 268: 26773-83.

TABLE 8

| Res | Position | I | II | III | IV | V | VI | VII | VIII | IX | X | XI | XII | XIII | XIV |
|---|---|---|---|---|---|---|---|---|---|---|---|---|---|---|---|
| Met | 1 | A | . | . | . | . | . | . | 1.30 | −0.61 | . | . | . | 0.95 | 2.10 |
| Arg | 2 | . | . | B | . | . | . | . | 0.88 | −1.04 | * | . | . | 0.95 | 3.21 |
| Lys | 3 | . | . | B | B | . | . | . | 0.98 | −0.79 | * | . | . | 0.75 | 2.07 |
| Thr | 4 | A | . | . | B | . | . | . | 1.02 | −0.30 | . | . | . | 0.45 | 2.20 |
| Arg | 5 | . | . | B | B | . | . | . | 0.60 | −0.49 | . | . | F | 0.60 | 1.11 |
| Leu | 6 | A | . | . | B | . | . | . | 0.39 | 0.20 | * | . | . | −0.30 | 0.46 |
| Trp | 7 | . | . | B | B | . | . | . | −0.01 | 0.89 | * | . | . | −0.60 | 0.26 |
| Gly | 8 | A | . | . | B | . | . | . | −0.66 | 1.31 | . | * | . | −0.60 | 0.14 |
| Leu | 9 | A | . | . | B | . | . | . | −1.16 | 1.93 | * | . | . | −0.60 | 0.17 |
| Leu | 10 | . | . | B | B | . | . | . | −1.97 | 1.93 | * | * | . | −0.60 | 0.13 |
| Trp | 11 | . | . | B | B | . | . | . | −2.01 | 1.80 | . | . | . | −0.60 | 0.12 |
| Met | 12 | . | . | B | B | . | . | . | −2.02 | 2.01 | . | . | . | −0.60 | 0.10 |
| Leu | 13 | A | . | . | B | . | . | . | −1.68 | 1.71 | . | . | . | −0.60 | 0.17 |
| Phe | 14 | A | . | . | B | . | . | . | −1.68 | 1.03 | * | * | . | −0.60 | 0.28 |
| Val | 15 | A | . | . | B | . | . | . | −0.76 | 0.80 | * | * | . | −0.60 | 0.23 |
| Ser | 16 | A | A | . | . | . | . | . | −1.06 | 0.19 | * | * | . | −0.30 | 0.55 |
| Glu | 17 | A | A | . | . | . | . | . | −1.04 | 0.00 | . | * | . | −0.30 | 0.64 |
| Leu | 18 | A | A | . | . | . | . | . | −0.54 | −0.29 | * | * | . | 0.30 | 0.88 |
| Arg | 19 | A | A | . | . | . | . | . | 0.20 | −0.44 | * | * | . | 0.30 | 0.94 |
| Ala | 20 | A | A | . | . | . | . | . | 0.24 | −0.83 | * | * | . | 0.75 | 1.09 |
| Ala | 21 | A | A | . | . | . | . | . | 0.23 | −0.14 | * | * | . | 0.45 | 1.09 |
| Thr | 22 | A | A | . | . | . | . | . | 0.23 | −0.34 | * | * | F | 0.45 | 0.80 |
| Lys | 23 | A | A | . | . | . | . | . | 1.04 | −0.34 | * | * | F | 0.60 | 1.38 |
| Leu | 24 | A | A | . | . | . | . | . | 0.98 | −0.84 | * | * | F | 0.90 | 2.36 |
| Thr | 25 | A | A | . | . | . | . | . | 1.32 | −1.34 | . | . | F | 0.90 | 3.27 |
| Glu | 26 | A | A | . | . | . | . | . | 1.91 | −1.07 | . | . | F | 0.90 | 2.56 |
| Glu | 27 | A | A | . | . | . | . | . | 1.41 | −1.07 | . | * | F | 0.90 | 5.38 |
| Lys | 28 | A | A | . | . | . | . | . | 1.41 | −1.07 | . | * | F | 0.90 | 3.08 |
| Tyr | 29 | A | A | . | . | . | . | . | 2.22 | −1.56 | . | * | F | 0.90 | 3.55 |
| Glu | 30 | A | A | . | . | . | . | . | 2.19 | −1.56 | . | * | F | 0.90 | 3.55 |
| Leu | 31 | A | A | . | . | . | . | . | 2.19 | −1.13 | . | * | F | 0.90 | 1.76 |
| Lys | 32 | A | A | . | . | . | . | . | 1.88 | −0.73 | * | * | F | 0.90 | 1.94 |
| Glu | 33 | A | A | . | . | . | . | . | 1.02 | −1.00 | * | * | F | 0.90 | 1.62 |
| Gly | 34 | A | A | . | . | . | . | . | 1.27 | −0.31 | . | * | F | 0.60 | 1.62 |
| Gln | 35 | A | A | . | . | . | . | . | 0.41 | −1.00 | . | * | F | 0.90 | 1.35 |
| Thr | 36 | A | A | . | . | . | . | . | 1.27 | −0.36 | . | * | F | 0.45 | 0.58 |
| Leu | 37 | A | A | . | . | . | . | . | 0.56 | −0.36 | . | * | F | 0.60 | 1.17 |
| Asp | 38 | . | A | B | . | . | . | . | 0.56 | −0.21 | . | * | . | 0.30 | 0.36 |
| Val | 39 | . | A | B | . | . | . | . | 0.66 | −0.61 | . | * | . | 0.60 | 0.42 |
| Lys | 40 | . | A | B | . | . | . | . | 0.34 | −0.34 | . | * | . | 0.30 | 0.80 |
| Cys | 41 | . | . | B | . | . | T | . | −0.16 | −0.54 | . | * | . | 1.00 | 0.69 |
| Asp | 42 | A | . | . | . | . | T | . | 0.66 | 0.14 | . | * | . | 0.10 | 0.77 |
| Tyr | 43 | A | . | . | . | . | T | . | 0.70 | −0.50 | . | * | . | 0.70 | 0.66 |
| Thr | 44 | A | . | . | . | . | T | . | 0.86 | −0.50 | * | * | . | 0.85 | 2.47 |
| Leu | 45 | A | A | . | . | . | . | . | 0.22 | −0.29 | * | * | . | 0.45 | 1.28 |
| Glu | 46 | A | A | . | . | . | . | . | 0.59 | 0.21 | * | . | . | −0.30 | 0.83 |
| Lys | 47 | A | A | . | . | . | . | . | 0.29 | −0.16 | . | . | . | 0.30 | 0.77 |
| Phe | 48 | A | A | . | . | . | . | . | 0.53 | −0.26 | * | . | F | 0.60 | 1.25 |
| Ala | 49 | A | . | . | . | . | T | . | 0.89 | −0.54 | . | . | F | 1.30 | 1.25 |
| Ser | 50 | A | . | . | . | . | T | . | 1.11 | −0.54 | * | . | F | 1.30 | 1.25 |
| Ser | 51 | A | . | . | . | . | T | . | 0.82 | −0.04 | . | . | F | 1.00 | 1.46 |
| Gln | 52 | A | . | . | . | . | T | . | 0.78 | 0.09 | . | * | F | 0.40 | 1.51 |
| Lys | 53 | A | . | . | . | . | . | . | 0.59 | −0.01 | * | . | F | 0.80 | 1.96 |
| Ala | 54 | A | . | . | B | . | . | . | 0.29 | 0.29 | * | . | . | −0.15 | 1.02 |
| Trp | 55 | A | . | . | B | . | . | . | 0.70 | 0.59 | * | . | . | −0.60 | 0.41 |
| Gln | 56 | . | . | B | B | . | . | . | 1.00 | 0.19 | * | . | . | −0.30 | 0.41 |
| Ile | 57 | . | . | B | B | . | . | . | 0.66 | 0.19 | * | . | . | 0.04 | 0.67 |
| Ile | 58 | . | . | B | . | . | T | . | 0.61 | 0.11 | * | . | . | 0.78 | 0.63 |
| Arg | 59 | . | . | B | . | . | T | . | 0.60 | −0.80 | * | . | . | 2.02 | 0.63 |
| Asp | 60 | . | . | . | . | T | T | . | 0.68 | −0.59 | * | . | F | 2.91 | 0.89 |
| Gly | 61 | . | . | . | . | T | T | . | 0.72 | −0.84 | * | . | F | 3.40 | 1.97 |
| Glu | 62 | . | . | . | . | . | . | C | 1.30 | −1.53 | * | . | F | 2.66 | 2.01 |
| Met | 63 | . | . | . | . | . | T | C | 1.38 | −1.04 | . | . | F | 2.52 | 1.74 |
| Pro | 64 | . | . | . | . | T | T | . | 0.68 | −0.36 | * | . | F | 2.08 | 1.45 |
| Lys | 65 | . | . | . | . | T | T | . | 0.01 | −0.29 | . | . | F | 1.59 | 0.84 |
| Thr | 66 | A | . | . | . | . | T | . | 0.04 | 0.29 | . | . | F | 0.25 | 0.46 |
| Leu | 67 | A | A | . | . | . | . | . | 0.04 | 0.16 | * | . | . | −0.30 | 0.43 |
| Ala | 68 | A | A | . | . | . | . | . | 0.76 | −0.27 | * | . | . | 0.30 | 0.37 |
| Cys | 69 | A | A | . | . | . | . | . | 0.76 | −0.27 | * | . | . | 0.30 | 0.50 |
| Thr | 70 | A | A | . | . | . | . | . | 0.41 | −0.33 | * | . | . | 0.64 | 0.94 |
| Glu | 71 | A | . | . | . | . | . | . | 0.77 | −0.63 | * | . | F | 1.78 | 1.25 |

TABLE 8-continued

| Res | Position | I | II | III | IV | V | VI | VII | VIII | IX | X | XI | XII | XIII | XIV |
|---|---|---|---|---|---|---|---|---|---|---|---|---|---|---|---|
| Arg | 72 | A | . | . | . | . | . | . | 1.58 | −1.13 | * | . | F | 2.12 | 4.65 |
| Pro | 73 | . | . | . | . | T | . | . | 1.87 | −1.30 | . | . | F | 2.86 | 5.18 |
| Ser | 74 | . | . | . | . | T | T | . | 2.50 | −1.40 | * | . | F | 3.40 | 4.01 |
| Lys | 75 | . | . | . | . | T | T | . | 2.60 | −0.90 | * | . | F | 3.06 | 2.79 |
| Asn | 76 | . | . | . | . | T | T | . | 1.74 | −0.47 | * | . | F | 2.42 | 2.79 |
| Ser | 77 | . | . | . | . | . | T | C | 1.63 | −0.26 | . | * | F | 1.88 | 1.54 |
| His | 78 | . | . | B | B | . | . | . | 0.99 | −0.24 | . | . | F | 0.94 | 1.34 |
| Pro | 79 | . | . | B | B | . | . | . | 0.94 | 0.40 | . | . | . | −0.60 | 0.62 |
| Val | 80 | . | . | B | B | . | . | . | 1.01 | 0.43 | . | * | . | −0.60 | 0.46 |
| Gln | 81 | . | . | B | B | . | . | . | 0.12 | 0.04 | * | . | . | −0.30 | 0.66 |
| Val | 82 | . | . | B | B | . | . | . | −0.47 | 0.23 | * | . | . | −0.30 | 0.30 |
| Gly | 83 | . | . | B | B | . | . | . | −1.24 | 0.49 | * | * | . | −0.60 | 0.28 |
| Arg | 84 | . | . | B | B | . | . | . | −1.03 | 0.53 | * | . | . | −0.60 | 0.13 |
| Ile | 85 | . | . | B | B | . | . | . | −0.18 | 0.13 | * | . | . | −0.30 | 0.31 |
| Ile | 86 | . | . | B | B | . | . | . | −0.42 | −0.51 | * | . | . | 0.60 | 0.53 |
| Leu | 87 | . | . | B | B | . | . | . | 0.40 | −0.19 | * | * | . | 0.30 | 0.42 |
| Glu | 88 | . | . | B | B | . | . | . | 0.74 | 0.31 | * | * | . | −0.30 | 0.82 |
| Asp | 89 | A | . | . | . | . | . | . | 0.60 | −0.37 | * | * | . | 0.65 | 1.95 |
| Tyr | 90 | A | . | . | . | . | . | . | 1.14 | −0.56 | . | . | . | 0.95 | 3.21 |
| His | 91 | A | . | . | . | . | T | . | 1.22 | −0.81 | . | . | . | 1.15 | 1.84 |
| Asp | 92 | A | . | . | . | . | T | . | 1.22 | −0.13 | . | * | . | 0.70 | 0.91 |
| His | 93 | A | . | . | . | . | T | . | 1.33 | 0.56 | * | * | . | −0.20 | 0.48 |
| Gly | 94 | A | . | . | . | . | T | . | 0.48 | −0.20 | . | * | . | 0.70 | 0.69 |
| Leu | 95 | A | . | . | B | . | . | . | 0.83 | −0.06 | . | * | . | 0.30 | 0.31 |
| Leu | 96 | A | . | . | B | . | . | . | 0.27 | −0.06 | . | * | . | 0.30 | 0.44 |
| Arg | 97 | . | . | B | B | . | . | . | −0.59 | 0.06 | . | * | . | −0.30 | 0.44 |
| Val | 98 | . | . | B | B | . | . | . | −0.56 | 0.27 | . | * | . | −0.30 | 0.40 |
| Arg | 99 | . | . | B | B | . | . | . | −1.02 | −0.01 | . | * | . | 0.30 | 0.77 |
| Met | 100 | . | . | B | B | . | . | . | −0.21 | −0.01 | . | * | . | 0.30 | 0.32 |
| Val | 101 | . | . | B | B | . | . | . | −0.26 | 0.39 | . | * | . | −0.30 | 0.76 |
| Asn | 102 | . | . | B | B | . | . | . | −0.37 | 0.39 | . | * | . | −0.30 | 0.29 |
| Leu | 103 | . | . | B | B | . | . | . | 0.49 | 0.39 | * | * | . | −0.30 | 0.50 |
| Gln | 104 | . | . | B | B | . | . | . | 0.08 | −0.23 | * | * | . | 0.73 | 1.13 |
| Val | 105 | . | . | B | B | . | . | . | 0.33 | −0.49 | . | * | . | 0.86 | 0.94 |
| Glu | 106 | . | . | B | B | . | . | . | 0.38 | −0.46 | . | * | F | 1.44 | 1.13 |
| Asp | 107 | . | . | . | . | T | T | . | 0.13 | −0.46 | . | * | F | 2.37 | 0.54 |
| Ser | 108 | . | . | . | . | T | T | . | 0.94 | −0.10 | . | * | F | 2.80 | 1.14 |
| Gly | 109 | . | . | . | . | T | T | . | 0.28 | −0.34 | . | . | F | 2.52 | 1.14 |
| Leu | 110 | . | . | . | . | T | T | . | 0.28 | 0.23 | . | . | . | 1.34 | 0.36 |
| Tyr | 111 | . | . | B | B | . | . | . | −0.61 | 0.87 | . | . | . | −0.04 | 0.20 |
| Gln | 112 | . | . | B | B | . | . | . | −0.86 | 1.17 | . | . | . | −0.32 | 0.14 |
| Cys | 113 | . | . | B | B | . | . | . | −0.56 | 1.50 | . | . | . | −0.60 | 0.27 |
| Val | 114 | . | . | B | B | . | . | . | −0.42 | 1.21 | . | . | . | −0.60 | 0.30 |
| Ile | 115 | . | . | B | B | . | . | . | 0.18 | 0.89 | * | . | . | −0.26 | 0.27 |
| Tyr | 116 | . | . | B | . | . | . | . | 0.47 | 0.91 | * | . | . | 0.28 | 0.77 |
| Gln | 117 | . | . | . | . | . | . | C | 0.47 | 0.34 | * | . | . | 1.27 | 2.09 |
| Pro | 118 | . | . | . | . | . | T | C | 0.92 | −0.30 | * | . | F | 2.56 | 5.15 |
| Pro | 119 | . | . | . | . | T | T | . | 1.74 | −0.56 | * | . | F | 3.40 | 5.08 |
| Lys | 120 | . | . | . | . | . | T | C | 2.03 | −0.81 | * | . | F | 2.86 | 3.99 |
| Glu | 121 | . | . | . | . | . | T | C | 1.47 | −0.60 | * | . | F | 2.52 | 2.56 |
| Pro | 122 | A | . | . | . | . | . | . | 0.77 | −0.34 | * | . | F | 1.48 | 1.36 |
| His | 123 | A | . | . | B | . | . | . | 0.98 | 0.01 | * | . | . | 0.04 | 0.59 |
| Met | 124 | A | . | . | B | . | . | . | 1.30 | 0.01 | * | . | . | −0.30 | 0.57 |
| Leu | 125 | A | . | . | B | . | . | . | 0.37 | 0.01 | * | * | . | −0.30 | 0.72 |
| Phe | 126 | A | . | . | B | . | . | . | 0.48 | 0.27 | * | * | . | −0.30 | 0.37 |
| Asp | 127 | A | . | . | B | . | . | . | −0.12 | −0.23 | * | * | . | 0.30 | 0.74 |
| Arg | 128 | A | . | . | B | . | . | . | −0.94 | −0.16 | * | * | . | 0.30 | 0.74 |
| Ile | 129 | A | . | . | B | . | . | . | −1.20 | −0.20 | * | * | . | 0.30 | 0.63 |
| Arg | 130 | . | . | B | B | . | . | . | −0.70 | −0.34 | * | * | . | 0.30 | 0.28 |
| Leu | 131 | . | . | B | B | . | . | . | 0.04 | 0.14 | * | * | . | −0.30 | 0.21 |
| Val | 132 | . | . | B | B | . | . | . | −0.30 | 0.14 | * | * | . | −0.30 | 0.59 |
| Val | 133 | . | . | B | B | . | . | . | −1.11 | −0.11 | * | * | . | 0.30 | 0.30 |
| Thr | 134 | . | . | B | B | . | . | . | −0.52 | 0.67 | * | * | F | −0.45 | 0.31 |
| Lys | 135 | . | . | B | B | . | . | . | −0.98 | 0.37 | . | * | F | −0.15 | 0.56 |
| Gly | 136 | . | . | B | . | . | T | . | −0.48 | 0.16 | . | . | F | 0.25 | 0.75 |
| Phe | 137 | . | . | B | . | . | T | . | 0.17 | 0.00 | . | . | F | 0.25 | 0.75 |
| Ser | 138 | . | . | B | . | . | T | . | 0.68 | −0.06 | . | . | F | 0.85 | 0.58 |
| Gly | 139 | . | . | . | . | . | T | C | 0.69 | 0.37 | . | . | F | 0.45 | 0.58 |
| Thr | 140 | . | . | . | . | . | T | C | 0.64 | 0.33 | . | . | F | 0.45 | 0.90 |
| Pro | 141 | . | . | . | . | . | T | C | 0.99 | −0.06 | . | . | F | 1.20 | 1.08 |
| Gly | 142 | . | . | . | . | . | T | C | 1.69 | −0.44 | . | . | F | 1.54 | 1.89 |
| Ser | 143 | . | . | . | . | . | T | C | 1.69 | −0.47 | . | . | F | 1.88 | 2.11 |
| Asn | 144 | . | . | . | . | . | T | C | 1.72 | −0.57 | . | . | F | 2.52 | 1.82 |
| Glu | 145 | . | . | . | . | . | T | C | 2.03 | −0.51 | . | . | F | 2.86 | 2.66 |
| Asn | 146 | . | . | . | . | T | T | . | 2.24 | −0.54 | . | . | F | 3.40 | 3.44 |
| Ser | 147 | . | . | . | . | T | T | . | 1.73 | −0.53 | . | . | F | 3.06 | 3.44 |
| Thr | 148 | . | . | . | B | T | . | . | 1.79 | −0.29 | * | . | F | 2.02 | 1.47 |
| Gln | 149 | . | . | B | B | . | . | . | 1.83 | 0.47 | * | . | F | 0.38 | 1.44 |

TABLE 8-continued

| Res | Position | I | II | III | IV | V | VI | VII | VIII | IX | X | XI | XII | XIII | XIV |
|---|---|---|---|---|---|---|---|---|---|---|---|---|---|---|---|
| Asn | 150 | . | . | B | B | . | . | . | 0.94 | 0.07 | * | . | F | 0.34 | 2.14 |
| Val | 151 | . | . | B | B | . | . | . | 0.73 | 0.37 | * | . | F | 0.00 | 1.04 |
| Tyr | 152 | . | . | B | B | . | . | . | 0.82 | 0.31 | * | . | . | −0.30 | 0.93 |
| Lys | 153 | . | . | B | B | . | . | . | 0.82 | 0.34 | * | . | F | −0.15 | 0.89 |
| Ile | 154 | . | . | B | B | . | . | . | 0.51 | 0.43 | * | . | F | −0.30 | 1.74 |
| Pro | 155 | . | . | B | . | . | T | . | 0.20 | 0.27 | * | . | F | 0.40 | 1.60 |
| Pro | 156 | . | . | . | . | T | T | . | 1.10 | 0.00 | * | . | F | 0.80 | 1.15 |
| Thr | 157 | . | . | . | . | T | T | . | 0.76 | 0.00 | * | . | F | 0.80 | 3.29 |
| Thr | 158 | . | . | B | . | . | T | . | −0.10 | −0.19 | * | . | F | 1.00 | 2.15 |
| Thr | 159 | . | A | B | . | . | . | . | 0.12 | 0.07 | * | . | F | 0.00 | 1.15 |
| Lys | 160 | . | A | B | . | . | . | . | 0.12 | 0.21 | * | . | F | −0.15 | 0.43 |
| Ala | 161 | . | A | B | . | . | . | . | −0.48 | 0.16 | * | . | . | −0.30 | 0.46 |
| Leu | 162 | . | A | B | . | . | . | . | −0.41 | 0.36 | * | . | . | −0.30 | 0.26 |
| Cys | 163 | . | . | B | . | . | T | . | −0.41 | 0.63 | * | . | . | −0.20 | 0.20 |
| Pro | 164 | . | . | B | . | . | T | . | −0.40 | 1.11 | * | . | . | −0.20 | 0.29 |
| Leu | 165 | . | . | B | . | . | T | . | −0.66 | 1.00 | * | * | . | −0.20 | 0.47 |
| Tyr | 166 | . | . | B | . | . | T | . | 0.04 | 0.74 | * | * | . | −0.05 | 1.37 |
| Thr | 167 | . | . | B | . | . | . | . | 0.54 | 0.17 | * | . | F | 0.20 | 1.74 |
| Ser | 168 | . | . | . | . | . | T | C | 0.36 | 0.23 | * | . | F | 0.60 | 3.04 |
| Pro | 169 | . | . | B | . | . | T | . | 0.26 | 0.19 | * | . | F | 0.40 | 1.44 |
| Arg | 170 | . | . | B | . | . | T | . | 1.07 | −0.09 | * | * | F | 1.00 | 1.44 |
| Thr | 171 | . | . | B | . | . | T | . | 0.72 | −0.17 | * | . | F | 1.00 | 1.86 |
| Val | 172 | . | . | B | B | . | . | . | 0.82 | −0.06 | * | . | F | 0.60 | 1.21 |
| Thr | 173 | . | . | B | B | . | . | . | 0.91 | −0.06 | * | * | F | 0.73 | 0.96 |
| Gln | 174 | . | . | B | B | . | . | . | 1.17 | 0.37 | * | * | F | 0.56 | 1.03 |
| Ala | 175 | . | . | B | B | . | . | . | 0.76 | −0.11 | * | * | F | 1.44 | 2.77 |
| Pro | 176 | . | . | . | . | . | T | C | 0.76 | −0.37 | . | . | F | 2.32 | 2.57 |
| Pro | 177 | . | . | . | . | T | T | . | 1.02 | −0.37 | . | * | F | 2.80 | 2.14 |
| Lys | 178 | . | . | . | . | T | T | . | 1.33 | −0.27 | . | * | F | 2.52 | 2.14 |
| Ser | 179 | . | . | B | . | . | T | . | 0.48 | −0.77 | . | * | F | 2.14 | 2.31 |
| Thr | 180 | . | . | B | B | . | . | . | 0.77 | −0.56 | . | * | F | 1.46 | 1.11 |
| Ala | 181 | . | . | B | B | . | . | . | 0.67 | −0.60 | . | * | F | 1.03 | 0.74 |
| Asp | 182 | . | . | B | B | . | . | . | 0.67 | −0.11 | . | * | F | 0.45 | 0.80 |
| Val | 183 | . | . | B | B | . | . | . | 0.62 | −0.07 | . | * | F | 0.79 | 0.86 |
| Ser | 184 | . | . | B | . | . | . | . | 0.62 | −0.56 | . | . | F | 1.78 | 1.42 |
| Thr | 185 | . | . | B | . | . | T | . | 0.93 | −0.67 | . | * | F | 2.32 | 1.14 |
| Pro | 186 | . | . | . | . | . | T | C | 0.63 | −0.67 | . | * | F | 2.86 | 2.66 |
| Asp | 187 | . | . | . | . | T | T | . | 0.63 | −0.63 | . | * | F | 3.40 | 1.39 |
| Ser | 188 | . | . | B | . | . | T | . | 0.68 | −0.61 | . | * | F | 2.66 | 1.55 |
| Glu | 189 | . | . | B | . | . | . | . | 0.67 | −0.41 | . | * | F | 1.67 | 0.83 |
| Ile | 190 | . | . | B | . | . | . | . | 0.98 | −0.36 | . | * | F | 1.33 | 0.71 |
| Asn | 191 | . | . | B | . | . | . | . | 0.33 | 0.04 | . | * | . | 0.24 | 0.86 |
| Leu | 192 | . | . | B | B | . | . | . | 0.02 | 0.30 | . | * | . | −0.30 | 0.37 |
| Thr | 193 | . | . | B | B | . | . | . | 0.32 | 0.79 | . | * | F | −0.60 | 0.76 |
| Asn | 194 | . | . | B | B | . | . | . | −0.57 | 0.10 | * | * | F | −0.15 | 0.78 |
| Val | 195 | . | . | B | B | . | . | . | −0.57 | 0.39 | * | * | F | −0.15 | 0.67 |
| Thr | 196 | . | . | B | B | . | . | . | −0.46 | 0.39 | * | * | F | −0.15 | 0.32 |
| Asp | 197 | . | . | B | B | . | . | . | −0.50 | −0.10 | * | * | . | 0.30 | 0.39 |
| Ile | 198 | . | . | B | B | . | . | . | −0.40 | 0.14 | * | * | . | −0.30 | 0.39 |
| Ile | 199 | . | . | B | B | . | . | . | −1.26 | −0.07 | * | * | . | 0.30 | 0.42 |
| Arg | 200 | . | . | B | B | . | . | . | −1.10 | 0.09 | * | * | . | −0.30 | 0.19 |
| Val | 201 | . | . | B | B | . | . | . | −0.79 | 0.87 | * | . | . | −0.60 | 0.23 |
| Pro | 202 | . | . | B | B | . | . | . | −1.68 | 0.59 | * | . | . | −0.60 | 0.53 |
| Val | 203 | . | . | B | B | . | . | . | −1.64 | 0.59 | . | * | . | −0.60 | 0.19 |
| Phe | 204 | . | . | B | B | . | . | . | −1.64 | 1.23 | . | * | . | −0.60 | 0.19 |
| Asn | 205 | . | . | B | B | . | . | . | −2.57 | 1.27 | . | * | . | −0.60 | 0.09 |
| Ile | 206 | . | . | B | B | . | . | . | −2.52 | 1.53 | . | . | . | −0.60 | 0.10 |
| Val | 207 | . | . | B | B | . | . | . | −2.90 | 1.57 | . | . | . | −0.60 | 0.09 |
| Ile | 208 | . | . | B | B | . | . | . | −2.39 | 1.29 | . | . | . | −0.60 | 0.06 |
| Leu | 209 | . | . | B | B | . | . | . | −2.03 | 1.31 | . | * | . | −0.60 | 0.08 |
| Leu | 210 | . | . | B | . | . | T | . | −2.73 | 1.06 | . | . | . | −0.20 | 0.11 |
| Ala | 211 | . | . | B | . | . | T | . | −2.66 | 1.20 | . | . | . | −0.20 | 0.13 |
| Gly | 212 | A | . | . | . | . | T | . | −2.10 | 1.20 | . | . | . | −0.20 | 0.13 |
| Gly | 213 | A | . | . | . | . | T | . | −1.17 | 0.90 | . | . | . | −0.20 | 0.22 |
| Phe | 214 | A | . | . | . | . | . | . | −0.66 | 0.21 | . | . | . | −0.10 | 0.43 |
| Leu | 215 | A | . | . | . | . | . | . | −0.66 | 0.10 | . | . | F | 0.05 | 0.58 |
| Ser | 216 | . | . | B | . | . | T | . | −0.92 | 0.36 | . | . | F | 0.25 | 0.48 |
| Lys | 217 | . | . | B | . | . | T | . | −1.28 | 0.57 | . | . | F | −0.05 | 0.42 |
| Ser | 218 | . | . | B | . | . | T | . | −1.23 | 0.57 | . | . | F | −0.05 | 0.44 |
| Leu | 219 | . | . | B | . | . | T | . | −1.39 | 0.27 | . | . | . | 0.10 | 0.44 |
| Val | 220 | . | . | B | B | . | . | . | −1.39 | 0.53 | . | . | . | −0.60 | 0.16 |
| Phe | 221 | . | . | B | B | . | . | . | −1.79 | 1.21 | . | . | . | −0.60 | 0.10 |
| Ser | 222 | . | . | B | B | . | . | . | −2.42 | 1.61 | . | . | . | −0.60 | 0.10 |
| Val | 223 | . | . | B | B | . | . | . | −2.98 | 1.43 | . | . | . | −0.60 | 0.14 |
| Leu | 224 | . | . | B | B | . | . | . | −2.48 | 1.43 | . | * | . | −0.60 | 0.12 |
| Phe | 225 | A | . | . | B | . | . | . | −2.43 | 1.13 | * | * | . | −0.60 | 0.13 |
| Ala | 226 | A | . | . | B | . | . | . | −1.62 | 1.43 | * | * | . | −0.60 | 0.15 |
| Val | 227 | A | . | . | B | . | . | . | −1.62 | 0.79 | * | * | . | −0.60 | 0.35 |

TABLE 8-continued

| Res | Position | I | II | III | IV | V | VI | VII | VIII | IX | X | XI | XII | XIII | XIV |
|---|---|---|---|---|---|---|---|---|---|---|---|---|---|---|---|
| Thr | 228 | . | . | B | B | . | . | . | −1.47 | 0.49 | . | * | . | −0.60 | 0.54 |
| Leu | 229 | . | . | B | B | . | . | . | −1.51 | 0.49 | * | * | . | −0.60 | 0.46 |
| Arg | 230 | . | . | B | B | . | . | . | −1.02 | 0.63 | * | * | . | −0.60 | 0.46 |
| Ser | 231 | . | . | B | B | . | . | . | −0.82 | 0.41 | . | * | . | −0.60 | 0.49 |
| Phe | 232 | . | . | B | B | . | . | . | −0.36 | 0.36 | . | * | . | −0.30 | 0.76 |
| Val | 233 | . | . | B | B | . | . | . | −0.43 | 0.10 | * | * | . | −0.30 | 0.50 |
| Pro | 234 | . | . | B | B | . | . | . | −0.01 | 0.53 | * | * | . | −0.60 | 0.48 |

TABLE 9

| Res | Position | I | II | III | IV | V | VI | VII | VIII | IX | X | XI | XII | XIII | XIV |
|---|---|---|---|---|---|---|---|---|---|---|---|---|---|---|---|
| Met | 1 | A | A | . | . | . | . | . | 0.61 | −0.60 | . | . | . | 0.75 | 1.47 |
| Lys | 2 | A | A | . | . | . | . | . | 0.41 | −0.64 | . | . | . | 0.96 | 1.54 |
| Arg | 3 | . | A | B | . | . | . | . | 0.46 | −0.57 | * | . | . | 1.17 | 1.22 |
| Ala | 4 | A | A | . | . | . | . | . | 0.50 | −0.57 | * | . | . | 1.38 | 1.22 |
| Ser | 5 | A | . | . | . | . | T | . | 0.59 | −0.76 | * | . | F | 1.99 | 0.60 |
| Ala | 6 | . | . | . | . | . | T | C | 1.30 | −0.37 | * | . | F | 2.10 | 0.41 |
| Gly | 7 | . | . | . | . | . | T | C | 0.44 | −0.37 | * | . | F | 1.89 | 0.80 |
| Gly | 8 | . | . | . | . | . | T | C | −0.48 | −0.19 | * | * | F | 1.68 | 0.49 |
| Ser | 9 | . | A | . | . | . | . | C | −0.48 | 0.11 | . | . | F | 0.47 | 0.40 |
| Arg | 10 | . | A | B | . | . | . | . | −0.47 | 0.11 | * | . | F | 0.06 | 0.41 |
| Leu | 11 | . | A | B | . | . | . | . | −0.73 | 0.60 | * | . | . | −0.60 | 0.43 |
| Leu | 12 | . | A | B | . | . | . | . | −1.20 | 0.81 | * | . | . | −0.60 | 0.24 |
| Ala | 13 | . | A | B | . | . | . | . | −1.14 | 1.11 | * | . | . | −0.60 | 0.10 |
| Trp | 14 | . | A | B | . | . | . | . | −1.66 | 2.03 | . | * | . | −0.60 | 0.13 |
| Val | 15 | . | A | B | . | . | . | . | −1.77 | 2.03 | . | * | . | −0.60 | 0.13 |
| Leu | 16 | A | A | . | . | . | . | . | −1.54 | 1.74 | . | . | . | −0.60 | 0.22 |
| Trp | 17 | A | A | . | . | . | . | . | −1.02 | 1.74 | . | . | . | −0.60 | 0.21 |
| Leu | 18 | A | A | . | . | . | . | . | −0.43 | 1.74 | . | . | . | −0.60 | 0.30 |
| Gln | 19 | A | A | . | . | . | . | . | −1.00 | 1.50 | . | . | . | −0.60 | 0.63 |
| Ala | 20 | . | A | . | . | T | . | . | −0.73 | 1.46 | . | . | . | −0.20 | 0.45 |
| Trp | 21 | . | A | . | . | T | . | . | −0.51 | 1.04 | . | . | . | −0.20 | 0.55 |
| Gln | 22 | . | A | B | . | . | . | . | −0.43 | 0.86 | . | . | . | −0.60 | 0.32 |
| Val | 23 | . | A | B | . | . | . | . | −0.29 | 0.89 | . | . | . | −0.60 | 0.49 |
| Ala | 24 | . | A | B | . | . | . | . | −0.50 | 0.96 | . | . | . | −0.60 | 0.25 |
| Ala | 25 | . | A | B | . | . | . | . | −0.26 | 0.47 | . | . | . | −0.60 | 0.22 |
| Pro | 26 | . | A | . | . | T | . | . | −0.56 | 0.50 | . | * | . | −0.20 | 0.30 |
| Cys | 27 | . | . | . | . | T | T | . | −1.22 | 0.36 | . | . | . | 0.50 | 0.30 |
| Pro | 28 | . | . | . | . | T | T | . | −1.22 | 0.43 | . | . | . | 0.20 | 0.16 |
| Gly | 29 | . | . | . | . | T | T | . | −1.30 | 0.57 | . | . | . | 0.20 | 0.08 |
| Ala | 30 | . | . | B | . | . | T | . | −0.96 | 0.71 | . | . | . | −0.20 | 0.08 |
| Cys | 31 | . | . | B | . | . | . | . | −0.74 | 0.90 | . | . | . | −0.40 | 0.08 |
| Val | 32 | . | . | B | . | . | . | . | −0.08 | 0.87 | . | . | . | −0.40 | 0.12 |
| Cys | 33 | . | . | B | . | . | T | . | −0.08 | 0.44 | . | . | . | −0.20 | 0.21 |
| Tyr | 34 | . | . | B | . | . | T | . | 0.31 | 0.37 | . | . | . | 0.36 | 0.62 |
| Asn | 35 | . | . | B | . | . | T | . | 0.04 | −0.20 | . | . | F | 1.52 | 1.66 |
| Glu | 36 | . | . | B | . | . | T | . | 0.40 | −0.20 | . | . | F | 1.78 | 2.30 |
| Pro | 37 | . | . | . | B | T | . | . | 0.94 | −0.29 | . | . | F | 2.04 | 2.11 |
| Lys | 38 | . | . | . | B | T | . | . | 1.31 | −0.56 | . | * | F | 2.60 | 1.90 |
| Val | 39 | . | . | . | B | T | . | . | 0.89 | −0.57 | . | * | F | 2.34 | 1.47 |
| Thr | 40 | . | . | B | B | . | . | . | 0.68 | 0.00 | . | * | F | 0.63 | 0.51 |
| Thr | 41 | . | . | B | B | . | . | . | 0.68 | 0.00 | . | * | F | 0.37 | 0.39 |
| Ser | 42 | . | . | B | B | . | . | . | 0.89 | 0.40 | * | * | F | −0.19 | 0.92 |
| Cys | 43 | . | . | B | . | . | T | . | 0.50 | 0.16 | * | * | F | 0.40 | 1.10 |
| Pro | 44 | . | . | . | . | T | T | . | 0.54 | 0.10 | . | . | F | 0.65 | 0.76 |
| Gln | 45 | . | . | . | . | T | T | . | 0.86 | 0.30 | . | . | F | 0.65 | 0.47 |
| Gln | 46 | . | . | B | . | . | T | . | 0.58 | 0.31 | * | . | F | 0.40 | 1.50 |
| Gly | 47 | . | A | B | . | . | . | . | 0.02 | 0.24 | * | . | F | −0.15 | 0.98 |
| Leu | 48 | . | A | B | B | . | . | . | 0.48 | 0.46 | . | . | . | −0.60 | 0.42 |
| Gln | 49 | . | A | B | B | . | . | . | −0.17 | 0.49 | . | . | . | −0.60 | 0.38 |
| Ala | 50 | . | A | B | B | . | . | . | −0.51 | 0.73 | * | . | . | −0.60 | 0.28 |
| Val | 51 | . | A | B | B | . | . | . | −1.40 | 0.73 | * | . | . | −0.60 | 0.34 |
| Pro | 52 | . | . | B | B | . | . | . | −1.27 | 0.73 | . | . | . | −0.60 | 0.14 |
| Val | 53 | . | . | B | B | . | . | . | −1.04 | 0.76 | . | . | . | −0.60 | 0.21 |
| Gly | 54 | . | . | B | . | . | . | . | −1.63 | 0.76 | . | . | . | −0.40 | 0.29 |
| Ile | 55 | . | . | B | . | . | . | . | −1.34 | 0.61 | . | . | . | −0.40 | 0.19 |
| Pro | 56 | . | . | B | . | . | . | . | −0.49 | 0.57 | . | * | . | −0.40 | 0.34 |
| Ala | 57 | A | . | . | . | . | . | . | −0.17 | 0.33 | . | * | . | −0.10 | 0.59 |
| Ala | 58 | A | . | . | . | . | . | . | −0.20 | −0.10 | * | . | . | 0.65 | 1.64 |
| Ser | 59 | A | . | . | B | . | . | . | −0.56 | −0.10 | * | * | F | 0.45 | 0.75 |
| Gln | 60 | . | . | B | B | . | . | . | −0.48 | 0.26 | * | * | F | −0.15 | 0.64 |
| Arg | 61 | . | . | B | B | . | . | . | −0.30 | 0.44 | . | * | F | −0.45 | 0.52 |
| Ile | 62 | . | . | B | B | . | . | . | −0.06 | 0.44 | . | * | . | −0.60 | 0.53 |
| Phe | 63 | . | . | B | B | . | . | . | 0.53 | 0.49 | * | * | . | −0.60 | 0.30 |

TABLE 9-continued

| Res | Position | I | II | III | IV | V | VI | VII | VIII | IX | X | XI | XII | XIII | XIV |
|---|---|---|---|---|---|---|---|---|---|---|---|---|---|---|---|
| Leu | 64 | . | . | B | B | . | . | . | 0.94 | 0.49 | * | * | . | −0.60 | 0.25 |
| His | 65 | . | . | . | . | T | T | . | 0.06 | 0.49 | * | * | . | 0.26 | 0.69 |
| Gly | 66 | . | . | . | . | T | T | . | −0.36 | 0.49 | * | * | F | 0.47 | 0.56 |
| Asn | 67 | . | . | . | . | T | T | . | 0.50 | 0.09 | * | . | F | 0.83 | 0.91 |
| Arg | 68 | . | . | . | . | T | T | . | 0.34 | −0.10 | . | . | F | 1.49 | 0.91 |
| Ile | 69 | . | . | . | . | T | . | . | 0.94 | 0.04 | . | . | . | 0.60 | 0.69 |
| Ser | 70 | . | . | B | . | . | . | . | 0.39 | 0.04 | * | . | . | 0.14 | 0.66 |
| His | 71 | . | . | B | . | . | . | . | 0.14 | 0.14 | * | . | . | 0.08 | 0.34 |
| Val | 72 | . | . | B | . | . | . | . | −0.16 | 0.64 | * | . | . | −0.28 | 0.49 |
| Pro | 73 | . | . | B | . | . | . | . | −0.97 | 0.34 | * | * | . | −0.04 | 0.49 |
| Ala | 74 | . | . | . | . | T | . | . | 0.03 | 0.74 | * | * | . | 0.00 | 0.31 |
| Ala | 75 | A | . | . | . | . | . | . | −0.26 | 0.24 | . | * | . | −0.10 | 0.82 |
| Ser | 76 | A | . | . | . | . | . | . | −0.89 | 0.10 | * | . | . | −0.10 | 0.54 |
| Phe | 77 | A | . | . | . | . | . | . | 0.08 | 0.24 | * | . | . | −0.10 | 0.29 |
| Arg | 78 | A | . | . | . | . | . | . | 0.29 | −0.26 | * | * | . | 0.60 | 0.55 |
| Ala | 79 | A | . | . | . | . | . | . | 0.07 | −0.36 | * | * | . | 0.70 | 0.66 |
| Cys | 80 | A | . | . | . | . | T | . | 0.34 | −0.06 | * | * | . | 1.00 | 0.63 |
| Arg | 81 | . | . | . | . | T | T | . | −0.24 | −0.36 | * | * | . | 1.50 | 0.47 |
| Asn | 82 | . | . | . | . | T | T | . | −0.36 | 0.33 | * | * | . | 1.00 | 0.32 |
| Leu | 83 | . | . | B | . | . | T | . | −0.76 | 0.51 | * | . | . | 0.20 | 0.50 |
| Thr | 84 | . | . | B | B | . | . | . | −0.98 | 0.86 | * | . | . | −0.30 | 0.27 |
| Ile | 85 | . | . | B | B | . | . | . | −0.34 | 1.54 | . | . | . | −0.40 | 0.14 |
| Leu | 86 | . | . | B | B | . | . | . | −0.76 | 1.64 | . | . | . | −0.50 | 0.23 |
| Trp | 87 | . | . | B | B | . | . | . | −0.76 | 1.34 | . | * | . | −0.60 | 0.21 |
| Leu | 88 | . | . | B | B | . | . | . | −0.80 | 1.26 | . | . | . | −0.60 | 0.48 |
| His | 89 | . | . | B | . | . | T | . | −1.30 | 1.21 | . | . | . | −0.20 | 0.43 |
| Ser | 90 | . | . | . | . | . | T | C | −1.00 | 1.21 | * | * | . | 0.00 | 0.34 |
| Asn | 91 | . | . | . | . | . | T | C | −0.08 | 0.80 | * | * | . | 0.00 | 0.42 |
| Val | 92 | A | . | . | . | . | T | . | −0.68 | 0.11 | . | * | . | 0.10 | 0.60 |
| Leu | 93 | A | A | . | . | . | . | . | 0.13 | 0.30 | . | * | . | −0.30 | 0.31 |
| Ala | 94 | A | A | . | . | . | . | . | −0.42 | −0.09 | . | * | . | 0.30 | 0.33 |
| Arg | 95 | A | A | . | . | . | . | . | −0.71 | 0.01 | * | * | . | −0.30 | 0.44 |
| Ile | 96 | A | A | . | . | . | . | . | −1.30 | −0.13 | * | * | . | 0.30 | 0.54 |
| Asp | 97 | A | A | . | . | . | . | . | −1.14 | −0.31 | . | * | . | 0.30 | 0.54 |
| Ala | 98 | A | A | . | . | . | . | . | −0.64 | −0.03 | * | * | . | 0.30 | 0.24 |
| Ala | 99 | A | A | . | . | . | . | . | −0.40 | 0.46 | * | * | . | −0.60 | 0.49 |
| Ala | 100 | A | A | . | . | . | . | . | −1.32 | 0.20 | . | * | . | −0.30 | 0.29 |
| Phe | 101 | A | A | . | . | . | . | . | −1.02 | 0.89 | . | . | . | −0.60 | 0.24 |
| Thr | 102 | A | A | . | . | . | . | . | −1.83 | 0.89 | . | . | . | −0.60 | 0.24 |
| Gly | 103 | A | A | . | . | . | . | . | −2.06 | 1.07 | . | . | . | −0.60 | 0.19 |
| Leu | 104 | A | A | . | . | . | . | . | −1.47 | 1.26 | . | . | . | −0.60 | 0.19 |
| Ala | 105 | A | A | . | . | . | . | . | −0.88 | 0.47 | . | . | . | −0.60 | 0.22 |
| Leu | 106 | A | A | . | . | . | . | . | −0.99 | 0.39 | . | . | . | −0.30 | 0.39 |
| Leu | 107 | A | A | . | . | . | . | . | −0.68 | 0.64 | . | * | . | −0.60 | 0.39 |
| Glu | 108 | A | A | . | . | . | . | . | −1.14 | −0.04 | . | * | . | 0.30 | 0.64 |
| Gln | 109 | A | A | . | . | . | . | . | −0.63 | 0.14 | . | * | . | −0.30 | 0.64 |
| Leu | 110 | A | A | . | . | . | . | . | −0.04 | −0.16 | . | * | . | 0.45 | 1.05 |
| Asp | 111 | A | A | . | . | . | . | . | 0.77 | −0.84 | . | * | . | 0.75 | 1.01 |
| Leu | 112 | A | A | . | . | . | . | . | 0.99 | −0.44 | . | * | . | 0.30 | 0.94 |
| Ser | 113 | A | . | . | . | . | T | . | 0.99 | −0.34 | . | * | F | 1.00 | 1.15 |
| Asp | 114 | A | . | . | . | . | T | . | 0.18 | −0.63 | . | * | F | 1.30 | 1.19 |
| Asn | 115 | A | . | . | . | . | T | . | 1.10 | 0.06 | . | * | F | 0.40 | 1.19 |
| Ala | 116 | A | . | . | . | . | T | . | 0.80 | −0.63 | . | * | . | 1.15 | 1.74 |
| Gln | 117 | . | A | B | . | . | . | . | 0.76 | −0.63 | . | * | . | 0.75 | 1.40 |
| Leu | 118 | . | A | B | . | . | . | . | 1.06 | 0.01 | . | * | . | −0.30 | 0.64 |
| Arg | 119 | . | A | B | . | . | . | . | 0.84 | −0.39 | * | * | F | 0.60 | 1.07 |
| Ser | 120 | . | A | B | . | . | . | . | 0.26 | −0.46 | * | * | F | 0.53 | 0.95 |
| Val | 121 | . | . | B | . | . | . | . | 0.53 | −0.36 | . | * | F | 0.96 | 1.17 |
| Asp | 122 | . | . | B | . | . | T | . | −0.17 | −0.56 | . | * | F | 1.39 | 0.86 |
| Pro | 123 | . | . | B | . | . | T | . | 0.61 | 0.23 | * | * | F | 0.57 | 0.55 |
| Ala | 124 | . | . | B | . | . | T | . | 0.16 | 0.34 | * | . | F | 0.80 | 1.02 |
| Thr | 125 | . | . | B | . | . | T | . | −0.36 | 0.13 | . | . | . | 0.42 | 0.60 |
| Phe | 126 | . | . | B | . | . | . | . | 0.16 | 0.81 | . | * | . | −0.16 | 0.32 |
| His | 127 | A | . | . | . | . | . | . | 0.27 | 0.81 | * | * | . | −0.24 | 0.31 |
| Gly | 128 | . | . | . | . | . | . | C | −0.33 | 0.31 | * | * | . | 0.18 | 0.43 |
| Leu | 129 | . | A | . | . | . | . | C | 0.22 | 0.51 | * | * | . | −0.40 | 0.41 |
| Gly | 130 | . | A | . | . | . | . | C | 0.22 | 0.23 | * | * | . | −0.10 | 0.41 |
| Arg | 131 | A | A | . | . | . | . | . | 0.11 | 0.21 | * | * | . | −0.30 | 0.59 |
| Leu | 132 | A | A | . | . | . | . | . | 0.11 | 0.47 | . | * | . | −0.60 | 0.59 |
| His | 133 | . | A | B | . | . | . | . | −0.36 | 0.29 | * | * | . | −0.30 | 0.82 |
| Thr | 134 | . | A | B | . | . | . | . | 0.46 | 0.54 | * | . | . | −0.60 | 0.34 |
| Leu | 135 | . | A | B | . | . | . | . | 0.91 | 0.54 | * | * | . | −0.38 | 0.70 |
| His | 136 | . | A | B | . | . | . | . | 0.13 | −0.14 | * | . | . | 0.89 | 1.00 |
| Leu | 137 | . | A | B | . | . | . | . | 0.60 | −0.07 | . | . | . | 0.96 | 0.37 |
| Asp | 138 | . | . | . | . | T | T | . | −0.18 | −0.13 | * | . | . | 1.98 | 0.45 |
| Arg | 139 | . | . | . | . | T | T | . | 0.13 | −0.13 | . | . | . | 2.20 | 0.27 |
| Cys | 140 | . | . | . | . | T | T | . | 0.94 | −0.23 | * | . | . | 1.98 | 0.57 |
| Gly | 141 | . | . | B | . | . | T | . | 0.17 | −0.91 | * | . | . | 1.66 | 0.59 |

TABLE 9-continued

| Res | Position | I | II | III | IV | V | VI | VII | VIII | IX | X | XI | XII | XIII | XIV |
|---|---|---|---|---|---|---|---|---|---|---|---|---|---|---|---|
| Leu | 142 | . | A | B | . | . | . | . | 0.63 | −0.23 | * | . | . | 0.74 | 0.25 |
| Gln | 143 | . | A | B | . | . | . | . | 0.42 | 0.20 | * | . | . | −0.08 | 0.46 |
| Glu | 144 | . | A | B | . | . | . | . | −0.03 | 0.06 | * | * | F | −0.15 | 0.72 |
| Leu | 145 | . | A | B | . | . | . | . | −0.18 | 0.06 | * | . | F | −0.15 | 0.86 |
| Gly | 146 | . | . | . | . | . | T | C | −0.53 | 0.06 | * | * | F | 0.45 | 0.41 |
| Pro | 147 | . | . | . | . | T | T | . | 0.39 | 0.44 | * | * | F | 0.35 | 0.20 |
| Gly | 148 | . | . | . | . | . | T | C | 0.04 | 0.44 | * | . | F | 0.15 | 0.49 |
| Leu | 149 | . | . | B | . | . | T | . | −0.77 | 0.19 | * | * | . | 0.10 | 0.49 |
| Phe | 150 | . | A | B | . | . | . | . | −0.54 | 0.44 | * | . | . | −0.60 | 0.26 |
| Arg | 151 | . | A | B | . | . | . | . | −0.79 | 0.51 | * | * | . | −0.60 | 0.26 |
| Gly | 152 | . | A | B | . | . | . | . | −1.39 | 0.59 | * | * | . | −0.60 | 0.32 |
| Leu | 153 | A | A | . | . | . | . | . | −1.04 | 0.59 | * | * | . | −0.60 | 0.31 |
| Ala | 154 | A | A | . | . | . | . | . | −0.48 | 0.20 | * | * | . | −0.30 | 0.27 |
| Ala | 155 | A | A | . | . | . | . | . | −0.59 | 0.96 | * | * | . | −0.60 | 0.43 |
| Leu | 156 | A | A | . | . | . | . | . | −0.94 | 1.21 | . | * | . | −0.60 | 0.43 |
| Gln | 157 | . | A | B | . | . | . | . | −1.41 | 1.29 | . | . | . | −0.60 | 0.67 |
| Tyr | 158 | . | A | B | . | . | . | . | −0.60 | 1.47 | . | . | . | −0.60 | 0.55 |
| Leu | 159 | . | A | B | . | . | . | . | −0.01 | 1.37 | . | . | . | −0.45 | 1.15 |
| Tyr | 160 | . | A | B | . | . | . | . | 0.58 | 0.69 | . | . | . | −0.45 | 1.11 |
| Leu | 161 | . | . | B | . | . | T | . | 0.80 | 0.69 | . | . | . | −0.05 | 1.14 |
| Gln | 162 | . | . | B | . | . | T | . | −0.01 | 0.43 | . | . | . | −0.05 | 1.39 |
| Asp | 163 | . | . | B | . | . | T | . | 0.23 | 0.43 | . | . | . | −0.20 | 0.73 |
| Asn | 164 | . | . | B | . | . | T | . | 0.46 | 0.07 | * | . | . | 0.25 | 1.54 |
| Ala | 165 | . | A | B | . | . | . | . | −0.11 | −0.11 | * | . | . | 0.30 | 0.90 |
| Leu | 166 | . | A | B | . | . | . | . | 0.49 | 0.17 | * | . | . | −0.30 | 0.44 |
| Gln | 167 | . | A | B | . | . | . | . | 0.49 | 0.60 | * | . | . | −0.32 | 0.43 |
| Ala | 168 | . | A | B | . | . | . | . | 0.49 | 0.20 | * | . | . | 0.26 | 0.70 |
| Leu | 169 | . | . | B | . | . | T | . | 0.18 | −0.30 | * | . | . | 1.69 | 1.43 |
| Pro | 170 | . | . | B | . | . | T | . | 0.07 | −0.50 | * | * | F | 2.12 | 1.19 |
| Asp | 171 | . | . | . | . | T | T | . | 0.99 | −0.11 | * | * | F | 2.80 | 1.02 |
| Asp | 172 | . | . | B | . | . | T | . | 0.99 | −0.61 | * | . | F | 2.42 | 2.42 |
| Thr | 173 | . | . | B | . | . | . | . | 0.77 | −1.30 | * | . | F | 1.94 | 2.61 |
| Phe | 174 | . | . | B | . | . | . | . | 1.23 | −1.04 | * | . | F | 1.87 | 1.29 |
| Arg | 175 | . | . | B | . | . | . | . | 1.44 | −0.61 | * | * | F | 1.65 | 0.76 |
| Asp | 176 | A | . | . | . | . | . | . | 0.63 | −0.21 | * | * | F | 1.28 | 0.85 |
| Leu | 177 | . | . | . | . | T | . | . | 0.32 | −0.01 | * | * | F | 1.89 | 0.81 |
| Gly | 178 | . | . | . | . | T | . | . | 0.60 | −0.31 | * | * | F | 2.10 | 0.60 |
| Asn | 179 | . | . | . | . | . | . | C | 0.49 | 0.19 | * | * | . | 0.94 | 0.49 |
| Leu | 180 | A | . | . | B | . | . | . | −0.32 | 0.87 | * | . | . | 0.03 | 0.49 |
| Thr | 181 | . | . | B | B | . | . | . | −1.13 | 0.97 | * | . | . | −0.18 | 0.43 |
| His | 182 | . | . | B | B | . | . | . | −0.36 | 1.23 | * | . | . | −0.39 | 0.22 |
| Leu | 183 | . | . | B | B | . | . | . | −0.36 | 1.33 | . | * | . | −0.60 | 0.36 |
| Phe | 184 | . | . | B | B | . | . | . | −0.36 | 1.07 | * | . | . | −0.60 | 0.25 |
| Leu | 185 | . | . | B | B | . | . | . | 0.57 | 0.99 | * | . | . | −0.60 | 0.29 |
| His | 186 | . | . | B | . | . | T | . | −0.01 | 0.49 | * | . | . | −0.20 | 0.69 |
| Gly | 187 | . | . | . | . | T | T | . | −0.28 | 0.49 | * | . | F | 0.35 | 0.56 |
| Asn | 188 | . | . | . | . | T | T | . | 0.23 | 0.09 | * | . | F | 0.65 | 0.91 |
| Arg | 189 | . | . | . | . | T | T | . | 0.08 | −0.21 | . | . | F | 1.25 | 0.90 |
| Ile | 190 | . | . | . | . | . | . | C | 0.68 | −0.07 | . | . | F | 0.85 | 0.67 |
| Ser | 191 | . | . | . | . | . | . | C | 0.71 | −0.07 | * | . | F | 0.85 | 0.65 |
| Ser | 192 | . | . | B | . | . | . | . | 1.17 | −0.47 | * | * | F | 0.65 | 0.57 |
| Val | 193 | . | . | B | . | . | . | . | 0.58 | −0.47 | * | . | F | 0.80 | 1.60 |
| Pro | 194 | . | A | B | . | . | . | . | −0.23 | −0.66 | * | . | F | 0.90 | 1.21 |
| Glu | 195 | . | A | B | . | . | . | . | 0.77 | −0.26 | * | . | F | 0.45 | 0.78 |
| Arg | 196 | A | A | . | . | . | . | . | 0.72 | −0.64 | * | . | F | 0.90 | 2.06 |
| Ala | 197 | A | A | . | . | . | . | . | 0.21 | −0.86 | * | . | . | 0.75 | 1.32 |
| Phe | 198 | A | A | . | . | . | . | . | 1.03 | −0.60 | * | . | . | 0.60 | 0.63 |
| Arg | 199 | A | A | . | . | . | . | . | 0.94 | −0.10 | * | . | . | 0.30 | 0.44 |
| Gly | 200 | A | A | . | . | . | . | . | 0.13 | 0.29 | * | * | . | −0.30 | 0.58 |
| Leu | 201 | A | A | . | . | . | . | . | 0.02 | 0.47 | * | . | . | −0.60 | 0.55 |
| His | 202 | . | A | . | . | . | . | C | 0.72 | −0.31 | * | * | . | 0.50 | 0.47 |
| Ser | 203 | . | A | . | . | . | . | C | 0.61 | −0.31 | * | * | . | 0.50 | 0.93 |
| Leu | 204 | A | A | . | . | . | . | . | −0.31 | −0.06 | * | * | . | 0.30 | 0.93 |
| Asp | 205 | A | A | . | . | . | . | . | −0.78 | −0.06 | * | . | . | 0.30 | 0.56 |
| Arg | 206 | A | A | . | B | . | . | . | 0.00 | 0.13 | * | . | . | −0.30 | 0.35 |
| Leu | 207 | A | A | . | B | . | . | . | 0.03 | 0.24 | * | . | . | −0.30 | 0.57 |
| Leu | 208 | A | A | . | B | . | . | . | 0.33 | −0.04 | * | . | . | 0.30 | 0.59 |
| Leu | 209 | A | A | . | B | . | . | . | 1.26 | 0.36 | * | . | . | −0.30 | 0.49 |
| His | 210 | A | . | . | . | . | T | . | 0.40 | 0.36 | * | . | . | 0.25 | 1.16 |
| Gln | 211 | A | . | . | . | . | T | . | −0.30 | 0.31 | * | * | F | 0.40 | 1.04 |
| Asn | 212 | A | . | . | . | . | T | . | 0.48 | 0.13 | . | . | F | 0.40 | 1.28 |
| Arg | 213 | A | . | . | . | . | T | . | 0.43 | −0.06 | . | . | . | 0.85 | 1.28 |
| Val | 214 | A | A | . | . | . | . | . | 1.21 | 0.09 | . | . | . | −0.30 | 0.55 |
| Ala | 215 | . | A | B | . | . | . | . | 1.03 | 0.19 | . | . | . | −0.30 | 0.46 |
| His | 216 | . | A | B | . | . | . | . | 1.00 | 0.21 | . | * | . | −0.30 | 0.37 |
| Val | 217 | . | A | B | . | . | . | . | 0.41 | 0.71 | * | . | . | −0.60 | 0.67 |
| His | 218 | . | A | B | . | . | . | . | −0.40 | 0.57 | * | . | . | −0.60 | 0.67 |
| Pro | 219 | . | A | B | . | . | . | . | 0.57 | 0.86 | * | . | . | −0.60 | 0.43 |

TABLE 9-continued

| Res | Position | I | II | III | IV | V | VI | VII | VIII | IX | X | XI | XII | XIII | XIV |
|---|---|---|---|---|---|---|---|---|---|---|---|---|---|---|---|
| His | 220 | A | . | . | . | . | . | . | 1.16 | 0.36 | * | . | . | 0.05 | 1.12 |
| Ala | 221 | A | . | . | . | . | . | . | 0.38 | −0.29 | * | . | . | 0.65 | 1.38 |
| Phe | 222 | A | . | . | . | . | . | . | 0.89 | −0.10 | * | * | . | 0.50 | 0.74 |
| Arg | 223 | A | . | . | . | . | . | . | 1.03 | −0.10 | * | * | . | 0.50 | 0.54 |
| Asp | 224 | A | . | . | . | . | . | . | 0.43 | −0.60 | * | * | F | 1.10 | 1.04 |
| Leu | 225 | A | . | . | . | . | . | . | −0.13 | −0.41 | * | * | F | 0.65 | 0.99 |
| Gly | 226 | A | . | . | . | . | . | . | 0.14 | −0.59 | * | * | F | 0.95 | 0.50 |
| Arg | 227 | A | . | . | B | . | . | . | 0.03 | −0.10 | * | * | . | 0.30 | 0.43 |
| Leu | 228 | . | . | B | B | . | . | . | −0.32 | 0.59 | * | * | . | −0.60 | 0.43 |
| Met | 229 | . | . | B | B | . | . | . | −1.13 | 0.66 | * | . | . | −0.60 | 0.68 |
| Thr | 230 | . | . | B | B | . | . | . | −1.02 | 0.91 | . | . | . | −0.60 | 0.29 |
| Leu | 231 | . | . | B | B | . | . | . | −1.27 | 1.70 | . | * | . | −0.60 | 0.30 |
| Tyr | 232 | . | . | B | B | . | . | . | −1.38 | 1.51 | . | . | . | −0.60 | 0.31 |
| Leu | 233 | . | . | B | B | . | . | . | −0.57 | 1.30 | . | . | . | −0.60 | 0.34 |
| Phe | 234 | A | . | . | . | . | T | . | −0.78 | 1.21 | . | . | . | −0.20 | 0.67 |
| Ala | 235 | A | . | . | . | . | T | . | −0.77 | 1.21 | . | . | . | −0.20 | 0.35 |
| Asn | 236 | A | . | . | . | . | T | . | −0.54 | 0.84 | * | . | . | −0.20 | 0.57 |
| Asn | 237 | . | . | . | . | . | T | C | −1.11 | 0.66 | . | . | . | 0.00 | 0.67 |
| Leu | 238 | . | A | . | . | . | . | C | −0.51 | 0.56 | . | . | . | −0.40 | 0.55 |
| Ser | 239 | . | A | . | . | . | . | C | −0.12 | 0.49 | * | . | . | −0.40 | 0.52 |
| Ala | 240 | . | A | . | . | . | . | C | 0.47 | 0.57 | * | . | . | −0.40 | 0.47 |
| Leu | 241 | . | A | . | . | . | . | C | −0.12 | 0.17 | * | . | . | −0.10 | 0.99 |
| Pro | 242 | A | A | . | . | . | . | . | −0.93 | −0.01 | . | . | F | 0.45 | 0.75 |
| Thr | 243 | A | A | . | . | . | . | . | −0.71 | 0.29 | . | . | F | −0.15 | 0.61 |
| Glu | 244 | A | A | . | . | . | . | . | −0.62 | 0.29 | . | . | F | −0.15 | 0.75 |
| Ala | 245 | A | A | . | . | . | . | . | −0.84 | 0.03 | * | * | . | −0.30 | 0.75 |
| Leu | 246 | A | A | . | . | . | . | . | 0.08 | 0.29 | * | * | . | −0.30 | 0.43 |
| Ala | 247 | A | A | . | . | . | . | . | −0.30 | −0.20 | * | * | . | 0.30 | 0.48 |
| Pro | 248 | A | A | . | . | . | . | . | −0.80 | 0.30 | * | * | . | −0.30 | 0.48 |
| Leu | 249 | A | A | . | . | . | . | . | −0.80 | 0.49 | * | * | . | −0.60 | 0.48 |
| Arg | 250 | A | A | . | . | . | . | . | −0.46 | 0.20 | * | * | . | −0.30 | 0.83 |
| Ala | 251 | A | A | . | . | . | . | . | −0.46 | 0.46 | * | * | . | −0.60 | 0.84 |
| Leu | 252 | A | A | . | . | . | . | . | 0.24 | 0.71 | * | * | . | −0.60 | 0.84 |
| Gln | 253 | . | A | B | . | . | . | . | −0.36 | 0.03 | * | * | . | −0.30 | 0.84 |
| Tyr | 254 | . | A | B | . | . | . | . | 0.46 | 0.71 | . | * | . | −0.60 | 0.68 |
| Leu | 255 | . | A | B | . | . | . | . | 0.34 | 0.61 | * | * | . | −0.17 | 1.33 |
| Arg | 256 | . | A | B | . | . | . | . | 0.93 | −0.07 | * | * | . | 1.01 | 1.28 |
| Leu | 257 | . | A | . | . | T | . | . | 1.53 | −0.07 | * | * | . | 1.69 | 1.32 |
| Asn | 258 | . | . | . | . | T | T | . | 1.24 | −0.40 | * | * | F | 2.52 | 2.47 |
| Asp | 259 | . | . | . | . | T | T | . | 0.63 | −0.17 | . | * | F | 2.80 | 1.33 |
| Asn | 260 | . | . | . | . | . | T | C | 0.78 | 0.47 | . | * | F | 1.42 | 1.19 |
| Pro | 261 | . | . | . | . | T | T | . | 0.67 | 0.36 | . | * | F | 1.49 | 0.40 |
| Trp | 262 | . | . | . | . | T | . | . | 0.81 | −0.04 | . | * | . | 1.46 | 0.40 |
| Val | 263 | . | . | B | . | . | . | . | 0.92 | 0.53 | . | * | . | 0.19 | 0.13 |
| Cys | 264 | . | . | B | . | . | T | . | 0.33 | 0.13 | . | * | . | 0.72 | 0.17 |
| Asp | 265 | . | . | B | . | . | T | . | 0.44 | 0.20 | . | * | . | 1.03 | 0.16 |
| Cys | 266 | . | . | B | . | . | T | . | 0.44 | −0.71 | . | * | . | 2.24 | 0.43 |
| Arg | 267 | . | . | . | . | T | T | . | −0.08 | −0.93 | . | * | . | 3.10 | 1.23 |
| Ala | 268 | . | . | . | . | T | . | . | 0.49 | −0.81 | . | * | . | 2.44 | 0.61 |
| Arg | 269 | . | . | . | . | . | T | C | 0.57 | 0.10 | . | * | . | 1.38 | 1.19 |
| Pro | 270 | . | . | . | . | . | T | C | 0.28 | 0.03 | . | * | . | 0.92 | 0.61 |
| Leu | 271 | A | . | . | . | . | T | . | 0.13 | 0.94 | . | * | . | 0.11 | 0.64 |
| Trp | 272 | A | . | . | . | . | T | . | 0.02 | 1.13 | * | * | . | −0.20 | 0.27 |
| Ala | 273 | A | A | . | . | . | . | . | 0.66 | 1.53 | * | . | . | −0.60 | 0.30 |
| Trp | 274 | A | A | . | . | . | . | . | −0.16 | 1.10 | * | * | . | −0.60 | 0.73 |
| Leu | 275 | A | A | . | . | . | . | . | 0.17 | 1.20 | * | * | . | −0.60 | 0.60 |
| Gln | 276 | . | A | B | . | . | . | . | 0.63 | 0.29 | * | * | . | −0.15 | 1.17 |
| Lys | 277 | . | A | B | . | . | . | . | 0.62 | 0.21 | . | * | F | 0.34 | 1.10 |
| Phe | 278 | . | A | . | . | T | . | . | 0.91 | −0.31 | . | * | F | 1.68 | 1.79 |
| Arg | 279 | . | A | . | . | T | . | . | 0.90 | −0.61 | * | * | F | 2.32 | 1.38 |
| Gly | 280 | . | . | . | . | T | T | . | 1.71 | −0.63 | * | * | F | 2.91 | 0.93 |
| Ser | 281 | . | . | . | . | T | T | . | 0.86 | −0.63 | * | * | F | 3.40 | 1.85 |
| Ser | 282 | . | . | . | . | . | T | C | 0.60 | −0.77 | . | * | F | 2.71 | 0.70 |
| Ser | 283 | . | . | . | . | T | T | . | 0.63 | −0.34 | . | * | F | 2.42 | 1.10 |
| Glu | 284 | . | . | . | . | T | . | . | 0.22 | −0.20 | . | * | F | 1.73 | 0.44 |
| Val | 285 | . | . | B | . | . | T | . | −0.24 | −0.20 | . | . | F | 1.19 | 0.44 |
| Pro | 286 | . | . | . | . | T | T | . | −0.16 | 0.10 | . | . | . | 0.50 | 0.27 |
| Cys | 287 | . | . | . | . | T | T | . | 0.14 | 0.14 | . | * | . | 0.50 | 0.24 |
| Ser | 288 | . | . | B | . | . | T | . | 0.56 | 0.54 | * | * | . | −0.20 | 0.56 |
| Leu | 289 | . | . | B | . | . | . | . | −0.26 | −0.10 | * | * | F | 0.65 | 0.71 |
| Pro | 290 | . | . | B | . | . | . | . | 0.01 | 0.16 | . | * | F | 0.20 | 1.10 |
| Gln | 291 | . | A | B | . | . | . | . | −0.12 | 0.09 | * | * | F | −0.15 | 0.83 |
| Arg | 292 | . | A | B | . | . | . | . | 0.66 | 0.13 | * | * | F | −0.15 | 0.99 |
| Leu | 293 | . | A | B | . | . | . | . | 0.96 | −0.56 | * | * | F | 0.90 | 1.26 |
| Ala | 294 | . | A | B | . | . | . | . | 0.96 | −0.99 | * | * | F | 0.90 | 1.21 |
| Gly | 295 | A | . | . | . | . | T | . | 1.21 | −0.70 | * | * | F | 1.15 | 0.51 |
| Arg | 296 | A | . | . | . | . | T | . | 1.32 | −0.70 | * | * | F | 1.30 | 1.24 |
| Asp | 297 | A | . | . | . | . | T | . | 0.40 | −1.39 | * | * | F | 1.30 | 2.40 |

TABLE 9-continued

| Res | Position | I | II | III | IV | V | VI | VII | VIII | IX | X | XI | XII | XIII | XIV |
|---|---|---|---|---|---|---|---|---|---|---|---|---|---|---|---|
| Leu | 298 | A | . | . | . | . | T | . | 0.62 | −1.20 | * | * | F | 1.30 | 2.00 |
| Lys | 299 | A | A | . | . | . | . | . | 0.62 | −1.13 | * | * | F | 0.90 | 1.03 |
| Arg | 300 | A | A | . | . | . | . | . | 0.97 | −0.63 | * | . | . | 0.60 | 0.62 |
| Leu | 301 | A | A | . | . | . | . | . | 0.86 | −0.23 | * | . | . | 0.45 | 1.22 |
| Ala | 302 | A | A | . | . | . | . | . | 0.04 | −0.91 | * | . | . | 0.75 | 1.01 |
| Ala | 303 | A | A | . | . | . | . | . | 0.86 | −0.23 | * | . | . | 0.30 | 0.43 |
| Asn | 304 | A | A | . | . | . | . | . | 0.47 | 0.17 | * | . | . | −0.30 | 0.90 |
| Asp | 305 | A | A | . | . | . | . | . | −0.31 | −0.09 | * | * | F | 0.45 | 0.88 |
| Leu | 306 | A | . | . | . | . | T | . | −0.09 | −0.01 | . | . | F | 0.85 | 0.47 |
| Gln | 307 | . | . | B | . | . | T | . | −0.36 | −0.01 | . | . | . | 0.70 | 0.29 |
| Gly | 308 | . | . | B | . | . | T | . | −0.36 | 0.23 | . | . | . | 0.10 | 0.13 |
| Cys | 309 | . | . | B | . | . | T | . | −0.67 | 0.73 | . | . | . | −0.20 | 0.16 |
| Ala | 310 | . | . | B | B | . | . | . | −1.01 | 0.53 | . | * | . | −0.60 | 0.13 |
| Val | 311 | . | . | B | B | . | . | . | −0.41 | 0.56 | . | . | . | −0.60 | 0.13 |
| Ala | 312 | . | . | B | B | . | . | . | −0.66 | 0.56 | . | . | . | −0.60 | 0.38 |
| Thr | 313 | . | . | B | B | . | . | . | −0.34 | 0.74 | . | . | F | −0.45 | 0.59 |
| Gly | 314 | . | . | B | . | . | T | . | 0.11 | 0.74 | . | . | F | 0.10 | 1.09 |
| Pro | 315 | . | . | . | . | T | T | . | −0.19 | 0.53 | . | . | F | 0.50 | 1.67 |
| Tyr | 316 | . | . | . | . | . | T | C | 0.38 | 0.71 | . | . | . | 0.00 | 0.81 |
| His | 317 | . | . | B | . | . | T | . | 0.66 | 1.14 | . | . | . | −0.20 | 0.86 |
| Pro | 318 | . | . | B | . | . | . | . | 0.62 | 1.20 | . | * | . | −0.40 | 0.80 |
| Ile | 319 | . | . | B | . | . | . | . | 1.08 | 1.20 | . | * | . | −0.40 | 0.51 |
| Trp | 320 | . | . | B | . | . | T | . | 0.70 | 0.44 | . | * | . | −0.20 | 0.73 |
| Thr | 321 | . | . | B | . | . | T | . | 0.63 | 0.44 | . | * | F | −0.05 | 0.48 |
| Gly | 322 | . | . | . | . | . | T | C | 0.67 | 0.50 | . | * | F | 0.15 | 0.98 |
| Arg | 323 | . | . | . | . | . | T | C | 0.88 | −0.19 | . | * | F | 1.20 | 1.56 |
| Ala | 324 | . | A | . | . | . | . | C | 1.77 | −1.10 | . | . | F | 1.10 | 1.87 |
| Thr | 325 | . | A | . | . | . | . | C | 1.84 | −1.59 | . | * | F | 1.41 | 3.28 |
| Asp | 326 | . | A | . | . | . | . | C | 1.34 | −1.59 | . | * | F | 1.72 | 2.59 |
| Glu | 327 | . | A | B | . | . | . | . | 1.34 | −0.90 | . | * | F | 1.83 | 2.11 |
| Glu | 328 | A | . | . | . | . | T | . | 0.42 | −0.97 | . | * | F | 2.54 | 1.45 |
| Pro | 329 | . | . | . | . | T | T | . | 0.80 | −0.77 | . | . | F | 3.10 | 0.72 |
| Leu | 330 | . | . | . | . | T | T | . | 1.16 | −0.34 | . | . | F | 2.49 | 0.64 |
| Gly | 331 | . | . | . | . | T | T | . | 0.49 | −0.34 | . | . | F | 2.18 | 0.74 |
| Leu | 332 | . | . | . | . | . | . | C | −0.18 | 0.23 | . | . | . | 0.72 | 0.26 |
| Pro | 333 | . | . | . | . | T | T | . | −0.18 | 0.37 | . | . | . | 0.81 | 0.17 |
| Lys | 334 | . | . | . | . | T | T | . | −0.18 | 0.09 | . | . | . | 0.50 | 0.29 |
| Cys | 335 | . | . | B | . | . | T | . | 0.63 | 0.09 | . | . | . | 0.10 | 0.55 |
| Cys | 336 | . | . | B | . | . | T | . | 0.39 | −0.60 | . | . | . | 1.00 | 0.59 |
| Gln | 337 | . | . | B | . | . | T | . | 0.61 | −0.53 | . | . | . | 1.00 | 0.30 |
| Pro | 338 | . | . | B | . | . | T | . | 0.82 | −0.03 | . | . | F | 0.85 | 0.56 |
| Asp | 339 | A | . | . | . | . | T | . | 0.82 | −0.60 | . | . | F | 1.30 | 1.75 |
| Ala | 340 | A | . | . | . | . | T | . | 0.90 | −1.17 | . | * | F | 1.30 | 2.02 |
| Ala | 341 | A | A | . | . | . | . | . | 1.27 | −1.07 | . | * | F | 0.90 | 1.32 |
| Asp | 342 | A | A | . | . | . | . | . | 0.41 | −1.11 | . | * | F | 0.90 | 1.06 |
| Lys | 343 | A | A | . | . | . | . | . | −0.19 | −0.47 | . | . | F | 0.45 | 0.78 |
| Ala | 344 | A | A | . | . | . | . | . | −0.19 | −0.29 | . | . | F | 0.45 | 0.63 |
| Ser | 345 | . | A | B | . | . | . | . | 0.19 | −0.79 | . | . | . | 0.60 | 0.66 |
| Val | 346 | . | A | B | . | . | . | . | 0.43 | −0.36 | . | * | . | 0.64 | 0.51 |
| Leu | 347 | . | A | B | . | . | . | . | 0.54 | 0.07 | . | * | . | 0.38 | 0.50 |
| Glu | 348 | . | . | B | . | . | T | . | 0.29 | −0.43 | * | * | F | 1.87 | 0.73 |
| Pro | 349 | . | . | . | . | T | T | . | 0.29 | −0.39 | * | . | F | 2.76 | 1.52 |
| Gly | 350 | . | . | . | . | T | T | . | 0.29 | −0.53 | * | . | F | 3.40 | 1.86 |
| Arg | 351 | . | . | . | . | . | T | C | 0.56 | −0.83 | * | . | F | 2.86 | 1.44 |
| Pro | 352 | . | . | . | . | . | . | C | 1.02 | −0.33 | . | . | F | 1.87 | 0.94 |
| Ala | 353 | A | . | . | . | . | . | . | 1.02 | −0.33 | . | . | F | 1.33 | 0.94 |
| Ser | 354 | A | . | . | . | . | T | . | 0.64 | −0.36 | . | . | F | 1.19 | 0.77 |
| Ala | 355 | A | . | . | . | . | T | . | 0.18 | 0.14 | . | * | F | 0.25 | 0.50 |
| Gly | 356 | A | . | . | . | . | T | . | 0.11 | 0.40 | . | * | F | 0.25 | 0.41 |
| Asn | 357 | . | . | B | . | . | T | . | −0.02 | −0.10 | . | * | . | 0.70 | 0.61 |
| Ala | 358 | . | . | B | . | . | . | . | 0.68 | −0.06 | . | * | F | 0.65 | 0.60 |
| Leu | 359 | . | . | B | . | . | . | . | 0.12 | −0.56 | . | * | F | 1.10 | 1.19 |
| Lys | 360 | . | . | B | . | . | . | . | 0.50 | −0.34 | . | * | F | 0.65 | 0.55 |
| Gly | 361 | . | . | B | . | . | . | . | 0.63 | −0.31 | . | * | F | 0.96 | 0.84 |
| Arg | 362 | . | . | B | . | . | . | . | 0.29 | −0.39 | . | * | F | 1.42 | 1.58 |
| Val | 363 | . | . | B | . | . | . | . | 0.88 | −0.64 | . | * | F | 1.88 | 0.78 |
| Pro | 364 | . | . | B | . | . | T | . | 1.39 | −0.64 | . | * | F | 2.54 | 1.32 |
| Pro | 365 | . | . | . | . | T | T | . | 1.13 | −0.69 | . | * | F | 3.10 | 0.90 |
| Gly | 366 | . | . | . | . | T | T | . | 1.27 | −0.26 | . | * | F | 2.64 | 1.88 |
| Asp | 367 | . | . | . | . | T | T | . | 0.81 | −0.47 | . | . | F | 2.33 | 1.88 |
| Ser | 368 | . | . | . | . | . | . | C | 1.67 | −0.47 | . | . | F | 1.62 | 1.20 |
| Pro | 369 | . | . | . | . | . | T | C | 1.53 | −0.50 | . | . | F | 1.81 | 1.95 |
| Pro | 370 | . | . | . | . | T | T | . | 1.44 | −0.50 | . | . | F | 2.00 | 1.16 |
| Gly | 371 | . | . | . | . | T | T | . | 1.44 | −0.11 | . | . | F | 2.00 | 1.16 |
| Asn | 372 | . | . | . | . | T | T | . | 1.23 | −0.07 | . | . | F | 2.15 | 0.74 |
| Gly | 373 | . | . | . | . | T | T | . | 1.64 | −0.07 | . | . | F | 2.45 | 0.74 |
| Ser | 374 | . | . | . | . | . | T | C | 1.82 | −0.50 | * | . | F | 3.00 | 1.47 |
| Gly | 375 | . | . | . | . | . | T | C | 1.14 | −0.43 | * | . | F | 2.40 | 1.24 |

TABLE 9-continued

| Res | Position | I | II | III | IV | V | VI | VII | VIII | IX | X | XI | XII | XIII | XIV |
|---|---|---|---|---|---|---|---|---|---|---|---|---|---|---|---|
| Pro | 376 | . | . | B | . | . | T | . | 1.49 | −0.14 | * | . | F | 1.75 | 0.88 |
| Arg | 377 | . | . | B | . | . | . | . | 1.49 | −0.17 | * | . | F | 1.40 | 1.05 |
| His | 378 | . | . | B | . | . | . | . | 1.53 | −0.56 | * | . | . | 1.25 | 1.78 |
| Ile | 379 | . | . | B | . | . | . | . | 1.62 | −0.60 | * | . | . | 1.20 | 1.54 |
| Asn | 380 | . | . | B | . | . | . | . | 1.27 | −0.60 | * | . | F | 1.60 | 1.22 |
| Asp | 381 | . | . | . | . | T | . | . | 1.13 | 0.19 | * | . | F | 1.20 | 0.77 |
| Ser | 382 | . | . | . | . | . | T | C | 0.71 | 0.11 | * | . | F | 1.60 | 1.09 |
| Pro | 383 | . | . | . | . | T | T | . | −0.07 | −0.09 | . | . | F | 2.50 | 0.98 |
| Phe | 384 | . | . | . | . | T | T | . | 0.61 | 0.20 | . | . | F | 1.65 | 0.48 |
| Gly | 385 | . | . | . | . | T | T | . | 0.27 | 0.63 | . | . | F | 1.10 | 0.56 |
| Thr | 386 | . | . | B | . | . | . | . | −0.03 | 0.67 | . | . | F | 0.49 | 0.36 |
| Leu | 387 | . | . | . | . | . | T | C | −0.32 | 0.63 | . | . | F | 0.88 | 0.55 |
| Pro | 388 | . | . | . | . | . | T | C | −0.11 | 0.34 | . | * | F | 1.17 | 0.57 |
| Gly | 389 | . | . | . | . | T | T | . | 0.38 | −0.09 | . | . | F | 2.21 | 0.68 |
| Ser | 390 | . | . | . | . | . | T | C | 0.51 | −0.14 | . | * | F | 2.40 | 1.27 |
| Ala | 391 | . | . | . | . | . | . | C | 0.23 | −0.40 | . | * | F | 1.96 | 1.27 |
| Glu | 392 | . | . | . | . | . | . | C | 1.01 | −0.33 | . | * | F | 1.72 | 1.30 |
| Pro | 393 | . | . | B | . | . | . | . | 0.56 | −0.26 | . | * | F | 1.28 | 1.32 |
| Pro | 394 | A | . | . | . | . | T | . | 0.60 | −0.07 | . | * | F | 1.09 | 0.70 |
| Ala | 395 | A | . | . | . | . | T | . | 0.31 | −0.19 | . | * | . | 0.70 | 0.54 |
| His | 396 | A | . | . | . | . | T | . | 0.31 | 0.31 | . | * | . | 0.10 | 0.35 |
| Cys | 397 | A | . | . | . | . | T | . | 0.42 | 0.39 | . | * | . | 0.10 | 0.23 |
| Ser | 398 | A | . | . | . | . | . | . | 0.29 | −0.04 | * | . | . | 0.50 | 0.45 |
| Ala | 399 | A | . | . | . | . | . | . | −0.31 | −0.11 | * | . | . | 0.50 | 0.33 |
| Ala | 400 | A | . | . | . | . | . | . | 0.39 | 0.07 | * | . | . | −0.10 | 0.50 |
| Arg | 401 | A | . | . | . | . | . | . | −0.17 | −0.50 | * | . | . | 0.80 | 0.73 |
| Gly | 402 | A | . | . | . | . | . | . | 0.19 | −0.39 | * | . | . | 0.50 | 0.73 |
| Leu | 403 | . | . | B | B | . | . | . | 0.60 | −0.40 | * | . | . | 0.45 | 1.05 |
| Arg | 404 | . | . | B | B | . | . | . | 0.49 | −0.90 | * | . | . | 0.75 | 1.05 |
| Ala | 405 | . | . | B | B | . | . | . | 0.87 | −0.11 | * | . | . | 0.30 | 0.92 |
| Thr | 406 | . | . | B | B | . | . | . | 0.44 | −0.11 | * | . | F | 0.60 | 1.72 |
| Arg | 407 | . | . | B | B | . | . | . | 0.49 | −0.31 | * | . | F | 0.60 | 1.26 |
| Phe | 408 | . | . | B | . | . | T | . | 0.96 | 0.07 | * | * | F | 0.40 | 1.68 |
| Pro | 409 | . | . | . | . | T | T | . | 0.63 | 0.00 | * | . | F | 1.74 | 1.15 |
| Thr | 410 | . | . | . | . | T | T | . | 1.33 | −0.06 | * | * | F | 1.93 | 0.91 |
| Ser | 411 | . | . | . | . | . | T | C | 1.76 | −0.06 | * | * | F | 2.22 | 2.05 |
| Gly | 412 | . | . | . | . | . | T | C | 1.76 | −0.84 | * | * | F | 2.86 | 2.60 |
| Pro | 413 | . | . | . | . | T | T | . | 2.24 | −1.27 | . | . | F | 3.40 | 3.53 |
| Arg | 414 | . | . | . | . | T | T | . | 2.11 | −1.33 | . | . | F | 3.06 | 4.08 |
| Arg | 415 | . | . | . | . | T | T | . | 1.76 | −1.29 | . | . | F | 2.72 | 4.08 |
| Arg | 416 | . | . | B | . | . | T | . | 1.76 | −1.14 | . | . | F | 1.98 | 1.41 |
| Pro | 417 | . | . | . | . | T | T | . | 2.21 | −1.19 | . | . | F | 2.23 | 0.97 |
| Gly | 418 | . | . | . | . | T | T | . | 2.47 | −1.19 | . | . | F | 2.23 | 0.97 |
| Cys | 419 | . | . | . | . | T | T | . | 2.36 | −1.19 | . | . | F | 2.57 | 0.99 |
| Ser | 420 | . | . | . | . | T | . | . | 2.36 | −0.79 | . | . | F | 2.86 | 1.03 |
| Arg | 421 | . | . | . | . | T | T | . | 1.93 | −1.21 | . | * | F | 3.40 | 2.03 |
| Lys | 422 | . | . | . | . | T | T | . | 2.26 | −1.16 | . | * | F | 3.06 | 5.47 |
| Asn | 423 | . | . | . | . | T | T | . | 2.30 | −1.73 | . | * | F | 2.98 | 7.99 |
| Arg | 424 | . | . | . | . | T | T | . | 2.93 | −1.73 | . | * | F | 2.90 | 5.47 |
| Thr | 425 | . | . | . | . | T | . | . | 2.57 | −1.23 | . | * | F | 2.62 | 3.72 |
| Arg | 426 | . | . | . | . | T | T | . | 2.57 | −0.66 | . | * | F | 2.74 | 1.24 |
| Ser | 427 | . | . | B | . | . | T | . | 1.71 | −1.06 | * | * | F | 2.60 | 1.24 |
| His | 428 | . | . | B | . | . | T | . | 1.37 | −0.37 | * | * | . | 1.74 | 0.71 |
| Cys | 429 | . | . | B | . | . | T | . | 1.26 | −0.43 | * | * | . | 1.48 | 0.36 |
| Arg | 430 | . | . | B | . | . | . | . | 0.98 | −0.03 | * | * | . | 1.02 | 0.46 |
| Leu | 431 | . | . | B | . | . | . | . | 0.52 | 0.09 | * | * | . | 0.16 | 0.34 |
| Gly | 432 | . | . | B | . | . | . | . | 0.52 | 0.01 | . | * | . | −0.10 | 0.63 |
| Gln | 433 | . | . | B | . | . | . | . | 0.21 | −0.17 | * | * | F | 0.65 | 0.43 |
| Ala | 434 | . | . | B | . | . | . | . | 0.53 | 0.26 | * | . | F | 0.05 | 0.52 |
| Gly | 435 | . | . | . | . | . | T | C | 0.08 | 0.00 | * | . | F | 1.05 | 0.52 |
| Ser | 436 | . | . | . | . | . | T | C | 0.54 | 0.00 | . | . | F | 1.05 | 0.30 |
| Gly | 437 | . | . | . | . | . | T | C | 0.58 | 0.03 | . | . | F | 0.45 | 0.29 |
| Gly | 438 | . | . | . | . | . | T | C | 0.23 | 0.01 | . | . | F | 0.71 | 0.43 |
| Gly | 439 | . | . | . | . | . | T | C | 0.82 | 0.01 | . | . | F | 0.97 | 0.31 |
| Gly | 440 | . | . | . | . | . | T | C | 0.87 | −0.37 | . | . | F | 1.83 | 0.53 |
| Thr | 441 | . | . | . | . | . | T | C | 1.17 | −0.41 | . | . | F | 2.09 | 0.72 |
| Gly | 442 | . | . | B | . | . | T | . | 1.17 | −0.84 | . | . | F | 2.60 | 1.26 |
| Asp | 443 | . | . | B | . | . | T | . | 1.21 | −0.84 | . | * | F | 2.34 | 1.26 |
| Ser | 444 | . | . | B | . | . | T | . | 1.21 | −0.89 | . | . | F | 2.29 | 1.17 |
| Glu | 445 | . | . | B | . | . | T | . | 0.97 | −0.94 | . | * | F | 2.24 | 1.17 |
| Gly | 446 | . | . | . | . | T | T | . | 0.47 | −0.87 | . | * | F | 2.44 | 0.71 |
| Ser | 447 | . | . | . | . | T | . | . | 0.60 | −0.19 | . | * | F | 1.89 | 0.43 |
| Gly | 448 | . | . | . | . | T | . | . | 0.30 | −0.14 | . | . | F | 2.10 | 0.39 |
| Ala | 449 | . | . | . | . | . | . | C | −0.21 | 0.24 | . | . | F | 1.09 | 0.52 |
| Leu | 450 | . | . | B | . | . | T | . | −0.52 | 0.50 | . | . | F | 0.58 | 0.32 |
| Pro | 451 | . | . | B | . | . | T | . | −0.84 | 0.60 | . | . | F | 0.37 | 0.47 |
| Ser | 452 | . | . | B | . | . | T | . | −0.84 | 0.74 | . | . | F | 0.16 | 0.25 |
| Leu | 453 | . | . | B | . | . | T | . | −1.31 | 0.63 | . | . | . | −0.20 | 0.41 |

TABLE 9-continued

| Res | Position | I | II | III | IV | V | VI | VII | VIII | IX | X | XI | XII | XIII | XIV |
|---|---|---|---|---|---|---|---|---|---|---|---|---|---|---|---|
| Thr | 454 | . | . | B | . | . | . | . | −1.03 | 0.63 | . | . | . | −0.40 | 0.22 |
| Cys | 455 | . | . | B | . | . | . | . | −0.43 | 0.69 | * | . | . | −0.40 | 0.23 |
| Ser | 456 | . | . | B | . | . | . | . | −1.03 | 0.73 | . | . | . | −0.40 | 0.44 |
| Leu | 457 | . | . | B | . | . | . | . | −1.08 | 0.73 | . | . | . | −0.40 | 0.25 |
| Thr | 458 | . | . | B | . | . | T | . | −1.08 | 0.67 | . | . | F | −0.05 | 0.46 |
| Pro | 459 | . | . | B | . | . | T | . | −1.36 | 0.79 | . | . | F | −0.05 | 0.28 |
| Leu | 460 | . | . | B | . | . | T | . | −1.50 | 0.90 | . | . | . | −0.20 | 0.35 |
| Gly | 461 | . | . | B | . | . | T | . | −2.06 | 0.90 | . | . | . | −0.20 | 0.20 |
| Leu | 462 | . | . | B | B | . | . | . | −2.06 | 1.06 | . | . | . | −0.60 | 0.10 |
| Ala | 463 | . | . | B | B | . | . | . | −2.03 | 1.31 | . | . | . | −0.60 | 0.10 |
| Leu | 464 | . | . | B | B | . | . | . | −2.13 | 1.54 | . | . | . | −0.60 | 0.10 |
| Val | 465 | . | . | B | B | . | . | . | −2.18 | 1.60 | . | . | . | −0.60 | 0.18 |
| Leu | 466 | . | . | B | B | . | . | . | −2.64 | 1.56 | . | . | . | −0.60 | 0.13 |
| Trp | 467 | . | . | B | B | . | . | . | −2.18 | 1.74 | . | . | . | −0.60 | 0.13 |
| Thr | 468 | . | . | B | B | . | . | . | −1.80 | 1.49 | . | . | . | −0.60 | 0.17 |
| Val | 469 | . | . | B | B | . | . | . | −1.66 | 1.27 | . | . | . | −0.60 | 0.33 |
| Leu | 470 | . | . | B | B | . | . | . | −1.19 | 1.16 | . | . | . | −0.60 | 0.17 |
| Gly | 471 | . | . | . | B | . | . | C | −0.77 | 0.67 | . | . | . | −0.40 | 0.15 |
| Pro | 472 | . | . | . | . | T | . | . | −0.87 | 0.61 | . | . | . | 0.00 | 0.25 |
| Cys | 473 | . | . | . | . | T | . | . | −0.94 | 0.40 | . | . | . | 0.30 | 0.39 |

TABLE 10

| Res | Position | I | II | III | IV | V | VI | VII | VIII | IX | X | XI | XII | XIII | XIV |
|---|---|---|---|---|---|---|---|---|---|---|---|---|---|---|---|
| Met | 1 | . | . | B | . | . | . | . | 0.59 | −0.19 | . | * | . | 0.86 | 1.62 |
| Arg | 2 | . | . | B | . | . | . | . | 0.77 | −0.19 | . | * | . | 1.07 | 1.25 |
| Thr | 3 | . | . | . | . | . | T | C | 0.34 | −0.19 | . | * | . | 1.68 | 1.52 |
| Pro | 4 | . | . | . | . | . | T | C | 0.52 | 0.07 | . | * | . | 1.29 | 1.26 |
| Gly | 5 | . | . | . | . | . | T | C | 0.06 | −0.11 | . | * | F | 2.10 | 1.00 |
| Pro | 6 | . | . | . | . | . | T | C | −0.16 | 0.53 | . | * | F | 0.99 | 0.51 |
| Leu | 7 | . | A | B | . | . | . | . | −1.08 | 0.73 | . | * | F | 0.18 | 0.27 |
| Pro | 8 | . | A | B | . | . | . | . | −1.58 | 0.99 | . | . | . | −0.18 | 0.23 |
| Val | 9 | . | A | B | . | . | . | . | −2.18 | 1.24 | . | . | . | −0.39 | 0.12 |
| Leu | 10 | . | A | B | . | . | . | . | −2.64 | 1.50 | . | . | . | −0.60 | 0.12 |
| Leu | 11 | . | A | B | . | . | . | . | −3.02 | 1.50 | . | . | . | −0.60 | 0.06 |
| Leu | 12 | . | A | B | . | . | . | . | −2.56 | 1.57 | . | . | . | −0.60 | 0.09 |
| Leu | 13 | . | A | B | . | . | . | . | −2.93 | 1.36 | . | . | . | −0.60 | 0.11 |
| Leu | 14 | . | A | B | . | . | . | . | −2.29 | 1.17 | . | . | . | −0.60 | 0.13 |
| Ala | 15 | . | A | B | . | . | . | . | −2.07 | 0.91 | . | . | . | −0.60 | 0.24 |
| Gly | 16 | . | A | B | . | . | . | . | −1.84 | 0.73 | . | . | . | −0.60 | 0.30 |
| Ala | 17 | . | . | B | . | . | . | . | −0.92 | 0.54 | . | . | . | −0.40 | 0.37 |
| Pro | 18 | . | . | B | . | . | . | . | −0.32 | −0.14 | . | . | . | 0.74 | 0.71 |
| Ala | 19 | . | . | . | . | T | . | . | 0.18 | −0.21 | . | . | . | 1.53 | 1.11 |
| Ala | 20 | . | . | B | . | . | . | . | 0.56 | −0.16 | . | . | . | 1.37 | 1.58 |
| Arg | 21 | . | . | B | . | . | . | . | 0.69 | −0.23 | . | . | F | 1.76 | 1.58 |
| Pro | 22 | . | . | . | . | T | . | . | 0.97 | −0.23 | . | . | F | 2.40 | 2.42 |
| Thr | 23 | . | . | . | . | . | . | C | 0.51 | −0.24 | . | . | F | 1.96 | 3.46 |
| Pro | 24 | . | . | . | . | . | T | C | 0.86 | −0.17 | . | . | F | 1.77 | 0.95 |
| Pro | 25 | . | . | . | . | T | T | . | 1.14 | 0.59 | . | * | F | 0.83 | 0.96 |
| Thr | 26 | . | . | . | . | T | T | . | 1.14 | 0.54 | . | * | F | 0.59 | 0.89 |
| Cys | 27 | . | . | B | . | . | T | . | 0.76 | 0.06 | . | * | . | 0.25 | 1.13 |
| Tyr | 28 | . | . | B | . | . | . | . | 1.18 | 0.24 | . | * | . | −0.10 | 0.72 |
| Ser | 29 | . | A | B | . | . | . | . | 0.80 | −0.19 | . | * | . | 0.30 | 0.98 |
| Arg | 30 | . | A | B | . | . | . | . | 0.20 | −0.17 | . | * | . | 0.45 | 1.85 |
| Met | 31 | . | A | B | . | . | . | . | 0.21 | −0.06 | . | * | . | 0.30 | 0.97 |
| Arg | 32 | . | A | B | . | . | . | . | 0.88 | −0.43 | . | * | . | 0.30 | 0.97 |
| Ala | 33 | . | A | B | . | . | . | . | 1.12 | −0.41 | * | * | . | 0.30 | 0.86 |
| Leu | 34 | . | A | . | . | . | . | C | 0.53 | −0.41 | * | * | . | 0.65 | 1.50 |
| Ser | 35 | . | A | B | . | . | . | . | 0.11 | −0.34 | * | * | F | 0.45 | 0.54 |
| Gln | 36 | . | A | B | . | . | . | . | 0.82 | 0.14 | * | . | F | −0.15 | 0.77 |
| Glu | 37 | . | A | B | . | . | . | . | 0.71 | −0.36 | * | . | F | 0.60 | 1.83 |
| Ile | 38 | . | A | B | . | . | . | . | 0.60 | −1.04 | * | . | F | 0.90 | 2.28 |
| Thr | 39 | . | A | B | . | . | . | . | 1.41 | −0.64 | * | * | F | 0.90 | 1.14 |
| Arg | 40 | . | A | B | . | . | . | . | 0.90 | −0.64 | * | . | F | 0.90 | 1.06 |
| Asp | 41 | . | A | . | . | T | . | . | 0.09 | 0.04 | * | . | F | 0.40 | 1.24 |
| Phe | 42 | . | . | B | B | . | . | . | 0.09 | 0.04 | * | . | . | −0.30 | 0.71 |
| Asn | 43 | . | . | B | B | . | . | . | 0.12 | −0.04 | * | . | . | 0.30 | 0.63 |
| Leu | 44 | . | . | . | B | . | . | C | 0.13 | 0.60 | . | . | . | −0.40 | 0.28 |
| Leu | 45 | . | . | B | B | . | . | . | 0.02 | 0.99 | . | . | . | −0.60 | 0.43 |
| Gln | 46 | . | . | B | B | . | . | . | −0.19 | 0.20 | . | . | . | 0.04 | 0.47 |
| Val | 47 | . | . | . | B | . | . | C | 0.21 | 0.23 | . | . | . | 0.58 | 0.87 |
| Ser | 48 | . | . | . | B | . | . | C | 0.21 | −0.07 | . | . | F | 1.82 | 1.42 |
| Glu | 49 | . | . | . | . | . | T | C | 0.81 | −0.76 | . | . | F | 2.86 | 1.42 |
| Pro | 50 | . | . | . | . | T | T | . | 0.96 | −0.73 | . | . | F | 3.40 | 2.95 |

TABLE 10-continued

| Res | Position | I | II | III | IV | V | VI | VII | VIII | IX | X | XI | XII | XIII | XIV |
|---|---|---|---|---|---|---|---|---|---|---|---|---|---|---|---|
| Ser | 51 | . | . | . | . | T | T | . | 0.10 | −0.80 | * | * | F | 3.06 | 1.18 |
| Glu | 52 | . | . | . | . | . | T | C | 1.07 | −0.54 | * | * | F | 2.37 | 0.51 |
| Pro | 53 | . | . | . | B | T | . | . | 1.12 | −0.54 | * | . | F | 1.83 | 0.64 |
| Cys | 54 | . | . | B | B | . | . | . | 0.31 | −0.21 | * | . | . | 0.64 | 0.75 |
| Val | 55 | . | . | B | B | . | . | . | 0.31 | 0.09 | * | * | . | −0.30 | 0.36 |
| Arg | 56 | . | . | B | B | . | . | . | 0.72 | 0.51 | * | * | . | −0.60 | 0.36 |
| Tyr | 57 | . | . | B | B | . | . | . | −0.09 | 0.09 | * | * | . | −0.15 | 1.30 |
| Leu | 58 | . | . | B | B | . | . | . | −0.12 | 0.20 | * | * | . | −0.15 | 1.45 |
| Pro | 59 | . | . | B | B | . | . | . | −0.27 | 0.31 | * | * | . | −0.15 | 1.16 |
| Arg | 60 | . | . | B | B | . | . | . | 0.59 | 1.00 | * | * | . | −0.60 | 0.61 |
| Leu | 61 | . | . | B | B | . | . | . | −0.41 | 0.24 | * | * | . | −0.15 | 1.24 |
| Tyr | 62 | . | . | B | B | . | . | . | −0.20 | 0.24 | * | * | . | −0.30 | 0.56 |
| Leu | 63 | . | . | B | B | . | . | . | 0.61 | 0.31 | * | * | . | −0.30 | 0.39 |
| Asp | 64 | . | . | B | B | . | . | . | 0.58 | 0.71 | * | * | . | −0.60 | 0.76 |
| Ile | 65 | . | . | B | B | . | . | . | −0.20 | 0.79 | * | * | . | −0.60 | 0.76 |
| His | 66 | . | . | B | . | . | T | . | −0.24 | 0.60 | . | * | . | −0.20 | 0.49 |
| Asn | 67 | . | . | B | . | . | T | . | −0.81 | 0.56 | . | * | . | −0.20 | 0.22 |
| Tyr | 68 | . | . | B | . | . | T | . | 0.00 | 1.24 | . | * | . | −0.20 | 0.26 |
| Cys | 69 | . | . | B | . | . | T | . | 0.04 | 0.56 | . | . | . | −0.20 | 0.32 |
| Val | 70 | . | A | B | B | . | . | . | 0.12 | 0.06 | . | * | . | −0.30 | 0.39 |
| Leu | 71 | . | A | B | B | . | . | . | 0.27 | 0.34 | * | * | . | −0.30 | 0.21 |
| Asp | 72 | . | A | B | B | . | . | . | 0.27 | −0.41 | * | . | F | 0.45 | 0.76 |
| Lys | 73 | . | A | B | . | . | . | . | −0.19 | −0.99 | * | * | F | 0.90 | 1.70 |
| Leu | 74 | . | A | B | B | . | . | . | −0.38 | −0.84 | * | . | F | 0.90 | 1.79 |
| Arg | 75 | . | A | B | B | . | . | . | −0.11 | −0.89 | * | . | F | 0.75 | 0.79 |
| Asp | 76 | . | A | B | B | . | . | . | 0.40 | −0.39 | * | . | . | 0.30 | 0.40 |
| Phe | 77 | . | A | B | B | . | . | . | 0.19 | 0.00 | * | . | . | 0.30 | 0.65 |
| Val | 78 | . | A | B | B | . | . | . | −0.07 | −0.26 | * | * | . | 0.30 | 0.52 |
| Ala | 79 | . | A | B | B | . | . | . | 0.08 | 0.17 | * | . | . | −0.30 | 0.48 |
| Ser | 80 | . | A | . | B | . | . | C | −0.32 | 0.74 | . | . | . | −0.40 | 0.30 |
| Pro | 81 | . | . | . | . | . | T | C | −0.28 | 0.87 | . | * | F | 0.15 | 0.42 |
| Pro | 82 | . | . | . | . | T | T | . | −0.43 | 0.23 | . | . | F | 0.65 | 0.83 |
| Cys | 83 | . | . | . | . | T | T | . | −0.17 | 0.37 | . | . | . | 0.50 | 0.46 |
| Trp | 84 | . | . | . | . | T | T | . | 0.42 | 0.49 | . | . | . | 0.20 | 0.30 |
| Lys | 85 | . | A | B | . | . | . | . | −0.13 | 0.46 | . | . | . | −0.60 | 0.34 |
| Val | 86 | . | A | B | . | . | . | . | 0.08 | 0.67 | . | . | . | −0.60 | 0.46 |
| Ala | 87 | . | A | B | . | . | . | . | −0.01 | 0.10 | . | . | . | −0.30 | 0.74 |
| Gln | 88 | . | A | B | . | . | . | . | −0.16 | −0.43 | . | . | . | 0.30 | 0.49 |
| Val | 89 | . | A | B | . | . | . | . | 0.18 | 0.26 | . | . | . | −0.30 | 0.55 |
| Asp | 90 | . | A | B | . | . | . | . | 0.13 | −0.39 | . | . | F | 0.60 | 1.09 |
| Ser | 91 | . | A | B | . | . | . | . | 1.03 | −0.89 | . | . | F | 0.90 | 1.05 |
| Leu | 92 | A | A | . | . | . | . | . | 1.03 | −1.29 | * | * | F | 0.90 | 2.83 |
| Lys | 93 | A | A | . | . | . | . | . | 1.14 | −1.43 | * | * | F | 0.90 | 1.71 |
| Asp | 94 | . | A | . | . | T | . | . | 2.04 | −1.43 | * | . | F | 1.30 | 2.50 |
| Lys | 95 | A | A | . | . | . | . | . | 1.23 | −1.81 | * | * | F | 0.90 | 6.06 |
| Ala | 96 | A | A | . | . | . | . | . | 1.29 | −1.81 | * | * | F | 0.90 | 2.50 |
| Arg | 97 | . | A | B | . | . | . | . | 1.79 | −1.06 | * | * | F | 0.90 | 2.34 |
| Lys | 98 | . | A | B | . | . | . | . | 0.86 | −0.57 | * | * | F | 0.90 | 1.69 |
| Leu | 99 | . | A | B | . | . | . | . | 0.26 | 0.11 | * | . | . | −0.15 | 1.17 |
| Tyr | 100 | . | A | B | . | . | . | . | 0.21 | 0.23 | * | . | . | −0.30 | 0.59 |
| Thr | 101 | . | . | B | B | . | . | . | 0.50 | 0.63 | * | . | . | −0.60 | 0.48 |
| Ile | 102 | . | . | B | B | . | . | . | −0.31 | 1.01 | * | . | . | −0.60 | 0.77 |
| Met | 103 | . | . | B | B | . | . | . | −1.02 | 1.11 | * | . | . | −0.60 | 0.43 |
| Asn | 104 | . | . | B | . | . | T | . | −0.10 | 0.93 | * | . | . | 0.04 | 0.16 |
| Ser | 105 | . | . | B | . | . | T | . | 0.26 | 0.44 | * | . | . | 0.28 | 0.44 |
| Phe | 106 | . | . | B | . | . | T | . | 0.57 | −0.24 | * | . | . | 1.42 | 0.88 |
| Cys | 107 | . | . | B | . | . | T | . | 0.64 | −0.86 | . | . | . | 1.96 | 0.91 |
| Arg | 108 | . | . | . | . | T | . | . | 0.39 | −0.57 | . | . | . | 2.40 | 0.56 |
| Arg | 109 | . | . | B | B | . | . | . | −0.31 | −0.31 | * | . | F | 1.41 | 0.48 |
| Asp | 110 | . | . | B | B | . | . | . | −0.82 | −0.31 | . | . | F | 1.17 | 0.78 |
| Leu | 111 | . | . | B | B | . | . | . | −0.93 | −0.20 | * | . | . | 0.78 | 0.33 |
| Val | 112 | . | . | B | B | . | . | . | −0.27 | 0.49 | * | . | . | −0.36 | 0.14 |
| Phe | 113 | . | . | B | B | . | . | . | −0.38 | 0.49 | * | . | . | −0.60 | 0.14 |
| Leu | 114 | . | . | B | B | . | . | . | −1.16 | 0.49 | * | . | . | −0.60 | 0.28 |
| Leu | 115 | . | . | B | B | . | . | . | −1.16 | 0.37 | . | . | . | −0.02 | 0.20 |
| Asp | 116 | . | . | . | . | T | T | . | −0.93 | 0.13 | . | . | F | 1.21 | 0.37 |
| Asp | 117 | . | . | . | . | T | T | . | −0.89 | −0.16 | . | . | F | 2.09 | 0.46 |
| Cys | 118 | . | . | . | . | T | T | . | −0.19 | −0.16 | . | . | . | 2.22 | 0.46 |
| Asn | 119 | . | . | . | . | T | T | . | 0.38 | −0.84 | . | . | . | 2.80 | 0.48 |
| Ala | 120 | . | A | B | . | . | . | . | 0.98 | −0.09 | . | . | . | 1.42 | 0.45 |
| Leu | 121 | . | A | B | . | . | . | . | 0.09 | 0.34 | . | . | . | 0.69 | 1.29 |
| Glu | 122 | . | A | B | . | . | . | . | −0.12 | 0.46 | . | * | . | −0.04 | 0.56 |
| Tyr | 123 | . | A | B | . | . | . | . | −0.31 | 0.49 | . | * | . | −0.32 | 0.86 |
| Pro | 124 | . | . | B | B | . | . | . | −0.62 | 0.63 | . | * | . | −0.60 | 0.77 |
| Ile | 125 | . | . | B | B | . | . | . | −0.34 | 0.43 | . | * | . | −0.60 | 0.64 |
| Pro | 126 | . | . | B | B | . | . | . | −0.39 | 0.91 | . | * | . | −0.60 | 0.59 |
| Val | 127 | . | . | B | B | . | . | . | −1.20 | 0.80 | . | . | . | −0.60 | 0.29 |
| Thr | 128 | . | . | B | B | . | . | . | −1.17 | 1.06 | . | . | . | −0.60 | 0.34 |

TABLE 10-continued

| Res | Position | I | II | III | IV | V | VI | VII | VIII | IX | X | XI | XII | XIII | XIV |
|---|---|---|---|---|---|---|---|---|---|---|---|---|---|---|---|
| Thr | 129 | . | . | B | B | . | . | . | −0.96 | 0.80 | . | . | F | −0.11 | 0.34 |
| Val | 130 | . | . | B | B | . | . | . | 0.04 | 0.37 | . | . | F | 0.53 | 0.75 |
| Leu | 131 | . | . | B | . | . | T | . | 0.26 | −0.27 | . | * | F | 2.02 | 1.02 |
| Pro | 132 | . | . | B | . | . | T | . | 1.22 | −0.36 | . | * | F | 2.36 | 1.23 |
| Asp | 133 | . | . | . | . | T | T | . | 1.14 | −0.84 | . | * | F | 3.40 | 3.24 |
| Arg | 134 | . | . | B | . | . | T | . | 1.07 | −1.06 | . | * | . | 2.51 | 5.03 |
| Gln | 135 | . | . | B | . | . | . | . | 1.53 | −1.31 | . | * | . | 1.97 | 4.16 |
| Arg | 136 | . | . | B | . | . | . | . | 1.96 | −1.31 | . | * | . | 1.63 | 3.18 |

TABLE 11

| Res | Position | I | II | III | IV | V | VI | VII | VIII | IX | X | XI | XII | XIII | XIV |
|---|---|---|---|---|---|---|---|---|---|---|---|---|---|---|---|
| Met | 1 | A | A | . | . | . | . | . | −0.68 | 0.09 | . | . | . | −0.30 | 0.62 |
| Lys | 2 | A | A | . | . | . | . | . | −1.10 | 0.23 | . | . | . | −0.30 | 0.26 |
| Ala | 3 | A | A | . | . | . | . | . | −1.52 | 0.49 | * | . | . | −0.60 | 0.17 |
| Leu | 4 | A | A | . | . | . | . | . | −1.94 | 0.74 | . | . | . | −0.60 | 0.14 |
| Cys | 5 | A | A | . | . | . | . | . | −2.37 | 0.81 | . | . | . | −0.60 | 0.06 |
| Leu | 6 | A | A | . | . | . | . | . | −1.98 | 1.50 | * | . | . | −0.60 | 0.05 |
| Leu | 7 | . | A | B | . | . | . | . | −2.88 | 1.43 | * | . | . | −0.60 | 0.09 |
| Leu | 8 | . | A | B | . | . | . | . | −3.10 | 1.39 | . | . | . | −0.60 | 0.12 |
| Leu | 9 | . | A | B | . | . | . | . | −2.63 | 1.50 | . | . | . | −0.60 | 0.12 |
| Pro | 10 | . | A | B | . | . | . | . | −2.78 | 1.24 | . | . | . | −0.60 | 0.15 |
| Val | 11 | . | A | B | . | . | . | . | −2.78 | 1.24 | . | . | . | −0.60 | 0.15 |
| Leu | 12 | . | A | B | . | . | . | . | −2.82 | 1.24 | . | . | . | −0.60 | 0.15 |
| Gly | 13 | . | A | B | . | . | . | . | −2.31 | 1.20 | * | . | . | −0.60 | 0.07 |
| Leu | 14 | . | A | B | . | . | . | . | −1.80 | 1.16 | . | . | . | −0.60 | 0.13 |
| Leu | 15 | . | A | B | . | . | . | . | −1.54 | 0.90 | . | . | . | −0.60 | 0.21 |
| Val | 16 | . | . | B | . | . | T | . | −1.00 | 0.21 | . | . | . | 0.10 | 0.42 |
| Ser | 17 | . | . | B | . | . | T | . | −1.00 | 0.27 | . | . | F | 0.25 | 0.73 |
| Ser | 18 | A | . | . | . | . | T | . | −1.32 | 0.27 | . | . | F | 0.25 | 0.73 |
| Lys | 19 | A | . | . | . | . | T | . | −0.81 | 0.16 | . | . | F | 0.25 | 0.53 |
| Thr | 20 | A | . | . | B | . | . | . | −0.60 | −0.10 | . | . | F | 0.45 | 0.53 |
| Leu | 21 | A | . | . | B | . | . | . | 0.26 | 0.13 | * | . | . | −0.30 | 0.39 |
| Cys | 22 | A | . | . | B | . | . | . | 0.56 | −0.26 | * | . | . | 0.30 | 0.34 |
| Ser | 23 | A | . | . | B | . | . | . | 0.27 | −0.26 | * | . | . | 0.30 | 0.40 |
| Met | 24 | A | A | . | . | . | . | . | −0.67 | −0.24 | * | . | . | 0.30 | 0.49 |
| Glu | 25 | A | A | . | . | . | . | . | −0.36 | −0.24 | * | . | . | 0.30 | 0.65 |
| Glu | 26 | A | A | . | . | . | . | . | 0.46 | −0.41 | * | * | . | 0.30 | 0.77 |
| Ala | 27 | A | A | . | . | . | . | . | 1.23 | −0.80 | * | * | . | 0.75 | 1.36 |
| Ile | 28 | A | A | . | . | . | . | . | 0.64 | −1.41 | * | * | . | 0.75 | 1.53 |
| Asn | 29 | A | A | . | . | . | . | . | 1.24 | −0.73 | * | * | . | 0.60 | 0.62 |
| Glu | 30 | A | A | . | . | . | . | . | 1.24 | −0.33 | * | * | F | 0.60 | 1.06 |
| Arg | 31 | A | A | . | . | . | . | . | 0.39 | −0.83 | * | * | F | 0.90 | 2.63 |
| Ile | 32 | A | A | . | . | . | . | . | 0.39 | −0.87 | * | * | F | 0.90 | 1.21 |
| Gln | 33 | A | A | . | . | . | . | . | 0.93 | −0.77 | * | * | F | 0.75 | 0.71 |
| Glu | 34 | A | A | . | . | . | . | . | 0.63 | −0.34 | * | * | . | 0.30 | 0.36 |
| Val | 35 | A | A | . | . | . | . | . | −0.18 | 0.04 | * | . | . | −0.30 | 0.68 |
| Ala | 36 | A | A | . | . | . | . | . | −1.18 | 0.04 | * | * | . | −0.30 | 0.33 |
| Gly | 37 | A | A | . | B | . | . | . | −0.99 | 0.33 | * | * | . | −0.30 | 0.13 |
| Ser | 38 | A | A | . | B | . | . | . | −0.88 | 1.11 | * | * | . | −0.60 | 0.15 |
| Leu | 39 | A | A | . | B | . | . | . | −1.47 | 0.47 | * | * | . | −0.60 | 0.30 |
| Ile | 40 | . | A | B | B | . | . | . | −1.50 | 0.47 | * | * | . | −0.60 | 0.30 |
| Phe | 41 | . | A | B | B | . | . | . | −1.21 | 0.73 | * | . | . | −0.60 | 0.16 |
| Arg | 42 | . | A | B | B | . | . | . | −1.17 | 0.73 | * | * | . | −0.60 | 0.26 |
| Ala | 43 | . | A | B | B | . | . | . | −1.76 | 0.43 | * | * | . | −0.60 | 0.49 |
| Ile | 44 | . | A | B | B | . | . | . | −1.29 | 0.43 | * | * | . | −0.60 | 0.40 |
| Ser | 45 | . | A | . | B | . | . | C | −1.21 | 0.07 | * | * | . | −0.10 | 0.20 |
| Ser | 46 | . | . | . | B | . | . | C | −0.51 | 0.76 | * | * | . | −0.40 | 0.17 |
| Ile | 47 | . | . | . | B | T | . | . | −1.29 | 0.26 | * | * | . | 0.10 | 0.41 |
| Gly | 48 | . | A | B | . | . | . | . | −0.70 | 0.14 | . | . | . | −0.30 | 0.16 |
| Leu | 49 | . | A | . | . | . | . | C | −0.11 | 0.16 | * | . | . | −0.10 | 0.21 |
| Glu | 50 | . | A | B | . | . | . | . | −0.67 | 0.16 | . | . | . | −0.30 | 0.40 |
| Cys | 51 | . | A | B | B | . | . | . | −0.68 | 0.11 | . | . | . | −0.30 | 0.30 |
| Gln | 52 | . | . | B | B | . | . | . | −0.09 | 0.17 | * | * | . | −0.30 | 0.53 |
| Ser | 53 | . | . | B | B | . | . | . | 0.37 | −0.13 | * | * | F | 0.45 | 0.41 |
| Val | 54 | . | . | B | B | . | . | . | 0.83 | −0.13 | . | * | F | 0.91 | 1.50 |
| Thr | 55 | . | . | B | B | . | . | . | 0.83 | −0.27 | . | * | F | 1.07 | 0.85 |
| Ser | 56 | . | . | . | . | T | T | . | 0.69 | −0.67 | . | * | F | 2.63 | 1.07 |
| Arg | 57 | . | . | . | . | T | T | . | 0.10 | −0.37 | . | * | F | 2.64 | 1.18 |
| Gly | 58 | . | . | . | . | T | T | . | 0.09 | −0.51 | . | * | F | 3.10 | 0.83 |
| Asp | 59 | . | . | . | . | T | T | . | 0.28 | −0.51 | . | * | F | 2.79 | 0.89 |
| Leu | 60 | . | . | B | . | . | . | . | 0.38 | −0.33 | . | * | F | 1.58 | 0.24 |
| Ala | 61 | . | . | B | . | . | . | . | 0.79 | 0.10 | * | * | . | 0.52 | 0.38 |
| Thr | 62 | . | . | B | . | . | . | . | 0.33 | −0.33 | * | * | . | 0.81 | 0.45 |

TABLE 11-continued

| Res | Position | I | II | III | IV | V | VI | VII | VIII | IX | X | XI | XII | XIII | XIV |
|---|---|---|---|---|---|---|---|---|---|---|---|---|---|---|---|
| Cys | 63 | . | . | B | . | . | T | . | −0.02 | 0.10 | * | * | . | 0.10 | 0.54 |
| Pro | 64 | . | . | . | . | T | T | . | −0.61 | 0.20 | * | . | F | 0.65 | 0.46 |
| Arg | 65 | . | . | . | . | T | T | . | −0.66 | 0.20 | * | . | F | 0.65 | 0.32 |
| Gly | 66 | . | . | . | . | T | T | . | −0.38 | 0.36 | . | . | . | 0.50 | 0.45 |
| Phe | 67 | . | . | B | B | . | . | . | −0.41 | 0.27 | * | . | . | −0.30 | 0.42 |
| Ala | 68 | . | . | B | B | . | . | . | −0.41 | 0.27 | * | . | . | −0.30 | 0.21 |
| Val | 69 | . | . | B | B | . | . | . | −0.51 | 0.84 | * | . | . | −0.60 | 0.11 |
| Thr | 70 | . | . | B | B | . | . | . | −1.29 | 0.90 | * | . | . | −0.60 | 0.19 |
| Gly | 71 | . | . | B | B | . | . | . | −1.29 | 0.69 | . | . | . | −0.60 | 0.10 |
| Cys | 72 | . | . | . | . | T | T | . | −0.89 | 0.61 | . | . | . | 0.20 | 0.13 |
| Thr | 73 | . | . | . | . | T | T | . | −0.89 | 0.36 | . | . | . | 0.50 | 0.12 |
| Cys | 74 | . | . | . | . | T | T | . | −0.70 | 0.37 | . | . | . | 0.50 | 0.13 |
| Gly | 75 | . | . | . | . | T | T | . | −0.73 | 0.51 | . | . | . | 0.20 | 0.13 |
| Ser | 76 | . | . | . | . | T | . | . | −0.69 | 0.37 | . | . | . | 0.30 | 0.09 |
| Ala | 77 | . | . | . | . | T | . | . | −0.31 | 0.27 | . | . | . | 0.30 | 0.22 |
| Cys | 78 | . | . | . | . | T | T | . | 0.00 | 0.61 | . | * | . | 0.20 | 0.23 |
| Gly | 79 | . | . | . | . | T | T | . | −0.19 | 0.19 | . | * | . | 0.50 | 0.29 |
| Ser | 80 | . | . | . | . | T | T | . | 0.27 | 0.44 | . | * | . | 0.20 | 0.21 |
| Trp | 81 | . | . | B | . | . | T | . | −0.02 | −0.06 | . | * | . | 0.70 | 0.78 |
| Asp | 82 | . | A | B | B | . | . | . | 0.57 | −0.13 | . | * | . | 0.30 | 0.79 |
| Val | 83 | A | A | . | B | . | . | . | 0.92 | −0.56 | . | * | . | 0.75 | 1.02 |
| Arg | 84 | A | A | . | B | . | . | . | 0.96 | −0.46 | . | * | . | 0.45 | 1.41 |
| Ala | 85 | A | A | . | . | . | . | . | 0.59 | −0.89 | . | * | F | 0.90 | 1.21 |
| Glu | 86 | . | A | . | . | T | . | . | 0.84 | −0.31 | . | * | F | 0.85 | 0.88 |
| Thr | 87 | . | A | . | . | T | . | . | 0.18 | −0.46 | . | * | F | 0.85 | 0.61 |
| Thr | 88 | . | A | . | . | T | . | . | 1.03 | 0.11 | . | * | . | 0.10 | 0.32 |
| Cys | 89 | . | . | . | . | T | T | . | 0.26 | 0.01 | . | * | . | 0.50 | 0.32 |
| His | 90 | . | . | . | . | T | T | . | 0.26 | 0.59 | . | . | . | 0.20 | 0.12 |
| Cys | 91 | . | . | B | . | . | T | . | −0.09 | 0.60 | . | . | . | −0.20 | 0.08 |
| Gln | 92 | . | . | B | . | . | T | . | −0.38 | 0.54 | . | . | . | −0.20 | 0.16 |
| Cys | 93 | . | . | . | . | T | . | . | −0.07 | 0.59 | . | . | . | 0.00 | 0.11 |
| Ala | 94 | . | . | . | . | T | . | . | 0.31 | 0.09 | . | . | . | 0.30 | 0.35 |
| Gly | 95 | . | . | . | . | T | T | . | 0.03 | 0.43 | . | . | . | 0.20 | 0.21 |
| Met | 96 | . | . | . | . | T | T | . | 0.36 | 0.51 | . | . | . | 0.42 | 0.57 |
| Asp | 97 | . | . | . | . | T | T | . | −0.23 | 0.37 | . | . | . | 0.94 | 0.56 |
| Trp | 98 | . | . | . | . | T | T | . | 0.54 | 0.37 | . | . | . | 1.16 | 0.57 |
| Thr | 99 | . | . | . | . | T | . | . | 0.47 | −0.06 | . | . | . | 1.93 | 1.14 |
| Gly | 100 | . | . | . | . | T | T | . | 0.14 | −0.10 | * | . | . | 2.20 | 0.37 |
| Ala | 101 | . | . | . | . | T | T | . | 0.86 | 0.47 | * | . | . | 1.08 | 0.19 |
| Arg | 102 | . | . | . | . | T | T | . | 0.00 | −0.44 | * | . | . | 1.76 | 0.25 |
| Cys | 103 | . | . | . | . | T | T | . | 0.29 | −0.29 | * | . | . | 1.54 | 0.19 |
| Cys | 104 | . | . | . | . | T | . | . | 0.39 | −0.31 | * | . | . | 1.12 | 0.32 |
| Arg | 105 | . | . | B | . | . | . | . | 0.34 | −0.39 | * | . | . | 0.50 | 0.26 |
| Val | 106 | . | . | B | . | . | . | . | 0.54 | 0.04 | * | . | . | −0.10 | 0.61 |
| Gln | 107 | . | . | B | . | . | . | . | 0.04 | −0.10 | * | . | . | 0.65 | 1.46 |
| Pro | 108 | . | . | B | . | . | . | . | 0.32 | −0.24 | . | * | . | 0.50 | 0.95 |

TABLE 12

| Res | Position | I | II | III | IV | V | VI | VII | VIII | IX | X | XI | XII | XIII | XIV |
|---|---|---|---|---|---|---|---|---|---|---|---|---|---|---|---|
| Met | 1 | . | . | . | . | . | . | C | 0.09 | 0.10 | . | . | . | 0.46 | 0.66 |
| Ser | 2 | . | . | . | . | . | T | C | 0.48 | 0.16 | . | . | . | 0.84 | 0.74 |
| Ser | 3 | . | . | . | . | . | T | C | 0.06 | −0.27 | * | . | . | 1.77 | 1.01 |
| Gly | 4 | . | . | . | . | . | T | C | −0.37 | −0.01 | . | . | . | 1.80 | 0.84 |
| Thr | 5 | . | . | . | . | . | T | C | −0.27 | 0.06 | . | . | F | 1.17 | 0.52 |
| Glu | 6 | A | . | . | . | . | . | . | 0.12 | 0.59 | * | . | F | 0.29 | 0.41 |
| Leu | 7 | A | . | . | . | . | . | . | 0.08 | 0.63 | . | . | . | −0.04 | 0.63 |
| Leu | 8 | A | . | . | . | . | . | . | −0.21 | 0.63 | . | . | . | −0.22 | 0.43 |
| Trp | 9 | A | . | . | . | . | T | . | −0.46 | 0.64 | . | . | . | −0.20 | 0.25 |
| Pro | 10 | A | . | . | . | . | T | . | −0.96 | 1.14 | . | . | . | −0.20 | 0.31 |
| Gly | 11 | A | . | . | . | . | T | . | −1.77 | 1.14 | . | . | . | −0.20 | 0.31 |
| Ala | 12 | A | . | . | . | . | T | . | −1.81 | 1.14 | . | . | . | −0.20 | 0.24 |
| Ala | 13 | A | . | . | B | . | . | . | −1.81 | 0.87 | . | . | . | −0.60 | 0.12 |
| Leu | 14 | A | . | . | B | . | . | . | −2.33 | 1.13 | . | . | . | −0.60 | 0.10 |
| Leu | 15 | A | . | . | B | . | . | . | −2.47 | 1.39 | . | . | . | −0.60 | 0.08 |
| Val | 16 | A | . | . | B | . | . | . | −2.98 | 1.31 | . | . | . | −0.60 | 0.08 |
| Leu | 17 | A | . | . | B | . | . | . | −2.98 | 1.46 | . | . | . | −0.60 | 0.07 |
| Leu | 18 | A | . | . | B | . | . | . | −2.98 | 1.27 | . | . | . | −0.60 | 0.09 |
| Gly | 19 | A | . | . | B | . | . | . | −2.47 | 1.09 | . | * | . | −0.60 | 0.12 |
| Val | 20 | A | . | . | B | . | . | . | −2.47 | 0.83 | . | . | . | −0.60 | 0.19 |
| Ala | 21 | A | . | . | B | . | . | . | −2.28 | 0.83 | . | * | . | −0.60 | 0.19 |
| Ala | 22 | A | . | . | B | . | . | . | −2.32 | 0.71 | * | * | . | −0.60 | 0.10 |
| Ser | 23 | A | . | . | B | . | . | . | −1.40 | 0.93 | * | * | . | −0.60 | 0.10 |
| Leu | 24 | A | . | . | B | . | . | . | −1.72 | 0.29 | . | * | . | −0.30 | 0.20 |

TABLE 12-continued

| Res | Position | I | II | III | IV | V | VI | VII | VIII | IX | X | XI | XII | XIII | XIV |
|---|---|---|---|---|---|---|---|---|---|---|---|---|---|---|---|
| Cys | 25 | . | . | B | B | . | . | . | −1.17 | 0.36 | * | * | . | −0.30 | 0.11 |
| Val | 26 | . | . | B | B | . | . | . | −0.47 | 0.24 | * | * | . | −0.30 | 0.11 |
| Arg | 27 | . | . | . | B | T | . | . | −0.09 | −0.14 | * | * | . | 1.04 | 0.25 |
| Cys | 28 | . | . | . | B | T | . | . | −0.13 | −0.40 | * | * | . | 1.38 | 0.73 |
| Ser | 29 | . | . | . | B | T | . | . | 0.09 | −0.54 | * | * | F | 2.17 | 0.97 |
| Arg | 30 | . | . | . | . | . | T | C | 0.80 | −0.69 | * | . | F | 2.71 | 0.50 |
| Pro | 31 | . | . | . | . | T | T | . | 1.77 | −0.69 | * | . | F | 3.40 | 1.86 |
| Gly | 32 | . | . | . | . | T | T | . | 1.36 | −1.26 | * | . | F | 3.06 | 2.72 |
| Ala | 33 | . | . | . | . | . | T | C | 2.02 | −1.26 | * | . | F | 2.52 | 1.86 |
| Lys | 34 | . | A | . | . | . | . | C | 2.37 | −1.26 | * | * | F | 1.78 | 2.08 |
| Arg | 35 | A | A | . | . | . | . | . | 1.37 | −1.69 | * | * | F | 1.24 | 4.21 |
| Ser | 36 | A | A | . | . | . | . | . | 1.33 | −1.43 | * | . | F | 0.90 | 2.92 |
| Glu | 37 | A | A | . | . | . | . | . | 1.68 | −1.17 | * | . | F | 0.90 | 2.29 |
| Lys | 38 | A | A | . | . | . | . | . | 2.27 | −0.77 | * | . | F | 0.90 | 2.02 |
| Ile | 39 | A | A | . | . | . | . | . | 2.33 | −0.37 | * | . | F | 0.60 | 2.62 |
| Tyr | 40 | A | . | . | . | . | . | . | 1.92 | −0.76 | . | . | F | 1.40 | 2.96 |
| Gln | 41 | A | . | . | . | . | T | . | 1.41 | −0.37 | . | * | F | 1.60 | 1.98 |
| Gln | 42 | A | . | . | . | . | T | . | 1.52 | 0.31 | . | . | F | 1.30 | 2.33 |
| Arg | 43 | . | . | . | . | . | T | C | 1.48 | −0.37 | . | * | F | 2.40 | 2.91 |
| Ser | 44 | . | . | . | . | . | T | C | 2.37 | −1.13 | . | . | F | 3.00 | 2.91 |
| Leu | 45 | . | A | . | . | . | . | C | 2.61 | −1.53 | * | * | F | 2.30 | 2.81 |
| Arg | 46 | . | A | . | . | T | . | . | 2.61 | −1.53 | * | . | F | 2.20 | 2.49 |
| Glu | 47 | . | A | . | . | T | . | . | 2.31 | −1.13 | * | . | F | 1.90 | 3.21 |
| Asp | 48 | . | A | . | . | T | . | . | 1.50 | −1.13 | * | . | F | 1.60 | 5.22 |
| Gln | 49 | . | A | . | . | T | . | . | 1.49 | −1.03 | * | * | F | 1.30 | 2.31 |
| Gln | 50 | . | A | . | . | T | . | . | 1.96 | −0.54 | * | * | F | 1.58 | 1.92 |
| Ser | 51 | . | A | . | . | . | . | C | 1.54 | −0.11 | * | . | F | 1.36 | 1.14 |
| Phe | 52 | . | . | . | . | T | T | . | 1.66 | 0.27 | . | . | F | 1.49 | 0.88 |
| Thr | 53 | . | . | . | . | T | T | . | 1.34 | −0.13 | . | . | F | 2.37 | 1.00 |
| Gly | 54 | . | . | . | . | T | T | . | 1.10 | −0.04 | * | . | F | 2.80 | 1.07 |
| Ser | 55 | . | . | . | . | T | T | . | 0.80 | 0.33 | . | . | F | 1.92 | 1.94 |
| Arg | 56 | . | . | . | B | T | . | . | 0.29 | −0.07 | . | . | F | 1.84 | 1.80 |
| Thr | 57 | . | . | . | B | T | . | . | 0.13 | 0.13 | . | . | F | 0.96 | 1.50 |
| Tyr | 58 | . | . | . | B | T | . | . | 0.10 | 0.34 | * | . | . | 0.38 | 0.83 |
| Ser | 59 | . | . | . | B | . | . | C | 0.44 | 0.39 | * | . | . | −0.10 | 0.42 |
| Leu | 60 | . | . | B | B | . | . | . | 0.16 | 0.79 | * | . | . | −0.60 | 0.50 |
| Val | 61 | . | . | B | B | . | . | . | −0.24 | 0.80 | * | . | . | −0.60 | 0.33 |
| Gly | 62 | . | . | . | . | T | . | . | −0.14 | 0.96 | . | . | . | 0.00 | 0.26 |
| Gln | 63 | . | . | . | . | T | . | . | −0.24 | 1.00 | . | . | . | 0.00 | 0.48 |
| Ala | 64 | . | . | . | . | . | . | C | −0.16 | 0.74 | . | . | . | −0.20 | 0.64 |
| Trp | 65 | . | . | . | . | . | T | C | −0.16 | 0.53 | . | . | F | 0.15 | 1.00 |
| Pro | 66 | . | . | . | . | . | T | C | 0.11 | 0.79 | * | . | F | 0.15 | 0.48 |
| Gly | 67 | . | . | . | . | . | T | C | 0.46 | 0.89 | * | . | F | 0.15 | 0.48 |
| Pro | 68 | . | . | . | . | . | T | C | −0.14 | 0.39 | * | . | F | 0.45 | 0.75 |
| Leu | 69 | . | A | . | . | . | . | C | −0.14 | 0.09 | . | . | F | 0.05 | 0.48 |
| Ala | 70 | . | A | . | . | . | . | C | −0.07 | 0.16 | . | . | . | −0.10 | 0.49 |
| Asp | 71 | A | A | . | . | . | . | . | −0.17 | 0.16 | . | . | . | −0.30 | 0.49 |
| Met | 72 | A | A | . | . | . | . | . | 0.29 | 0.21 | . | . | . | −0.30 | 0.86 |
| Ala | 73 | A | A | . | . | . | . | . | 0.54 | −0.47 | . | . | . | 0.45 | 1.67 |
| Pro | 74 | A | . | . | . | . | T | . | 1.36 | −0.97 | . | . | F | 1.30 | 2.00 |
| Thr | 75 | A | . | . | . | . | T | . | 1.99 | −0.97 | . | . | F | 1.30 | 3.38 |
| Arg | 76 | A | . | . | . | . | T | . | 1.18 | −1.59 | . | . | F | 1.30 | 6.69 |
| Lys | 77 | A | . | . | . | . | T | . | 0.97 | −1.40 | . | . | F | 1.30 | 3.57 |
| Asp | 78 | A | A | . | . | . | . | . | 1.56 | −1.14 | . | . | F | 0.90 | 2.04 |
| Lys | 79 | A | A | . | . | . | . | . | 1.07 | −1.23 | . | . | F | 0.90 | 1.80 |
| Leu | 80 | A | A | . | . | . | . | . | 1.13 | −0.44 | . | . | . | 0.30 | 0.78 |
| Leu | 81 | . | A | B | . | . | . | . | 0.81 | 0.31 | . | . | . | −0.30 | 0.73 |
| Gln | 82 | . | A | B | . | . | . | . | 0.47 | 0.74 | * | * | . | −0.60 | 0.57 |
| Phe | 83 | . | A | B | . | . | . | . | −0.34 | 1.13 | * | * | . | −0.60 | 0.92 |
| Tyr | 84 | . | . | . | . | . | T | C | −0.39 | 1.13 | * | * | . | 0.00 | 0.92 |
| Pro | 85 | . | . | . | . | . | T | C | 0.42 | 0.44 | * | * | . | 0.00 | 0.92 |
| Ser | 86 | . | . | . | . | . | T | C | 1.02 | 0.04 | * | * | F | 0.60 | 1.78 |
| Leu | 87 | . | . | . | . | . | T | C | 0.43 | −0.31 | * | * | F | 1.50 | 1.75 |
| Glu | 88 | . | . | . | . | . | . | C | 0.83 | −0.57 | * | * | F | 1.90 | 1.14 |
| Asp | 89 | . | . | . | . | . | . | C | 0.78 | −0.61 | . | * | F | 2.20 | 1.14 |
| Pro | 90 | . | . | . | . | . | . | C | 1.10 | −0.61 | . | * | F | 2.50 | 1.86 |
| Ala | 91 | . | . | . | . | T | . | . | 1.16 | −1.30 | . | * | F | 3.00 | 2.10 |
| Ser | 92 | A | . | . | . | . | T | . | 1.97 | −0.54 | . | * | F | 2.50 | 1.97 |
| Ser | 93 | A | . | . | . | . | T | . | 1.97 | −0.14 | . | * | F | 1.90 | 2.21 |
| Arg | 94 | A | . | . | . | . | T | . | 1.27 | −0.17 | * | . | F | 1.60 | 3.52 |
| Tyr | 95 | . | . | . | . | T | T | . | 1.18 | 0.11 | * | * | F | 1.10 | 2.27 |
| Gln | 96 | . | . | . | . | T | . | . | 1.81 | 0.11 | * | * | F | 0.94 | 2.27 |
| Asn | 97 | . | . | . | . | T | . | . | 1.77 | −0.27 | * | * | F | 1.88 | 2.32 |
| Phe | 98 | . | . | . | . | T | . | . | 1.77 | 0.16 | * | * | F | 1.62 | 1.47 |
| Ser | 99 | . | . | . | . | T | T | . | 1.77 | −0.21 | * | * | F | 2.76 | 1.13 |
| Lys | 100 | . | . | . | . | T | T | . | 1.98 | −0.61 | * | . | F | 3.40 | 1.38 |
| Gly | 101 | . | . | . | . | . | T | C | 1.63 | −0.51 | * | . | F | 2.86 | 2.17 |
| Ser | 102 | . | . | . | . | . | T | C | 1.33 | −0.87 | * | . | F | 2.82 | 1.60 |

TABLE 12-continued

| Res | Position | I | II | III | IV | V | VI | VII | VIII | IX | X | XI | XII | XIII | XIV |
|---|---|---|---|---|---|---|---|---|---|---|---|---|---|---|---|
| Arg | 103 | . | . | . | . | . | . | C | 2.03 | −0.87 | * | . | F | 2.58 | 1.07 |
| His | 104 | . | . | . | . | . | T | C | 2.33 | −0.87 | * | . | F | 2.74 | 1.88 |
| Gly | 105 | . | . | . | . | . | T | C | 1.70 | −1.30 | * | . | F | 2.70 | 2.43 |
| Ser | 106 | . | . | . | . | . | T | C | 1.80 | −1.19 | * | . | F | 3.00 | 1.25 |
| Glu | 107 | A | . | . | . | . | T | . | 1.21 | −0.43 | . | * | F | 2.20 | 1.44 |
| Glu | 108 | A | . | . | . | . | . | . | 1.10 | −0.24 | . | * | F | 1.70 | 1.02 |
| Ala | 109 | A | . | . | . | . | . | . | 0.92 | −0.67 | . | * | . | 1.55 | 1.27 |
| Tyr | 110 | A | . | . | . | . | . | . | 0.38 | −0.63 | . | * | . | 1.25 | 1.14 |
| Ile | 111 | A | . | . | . | . | . | . | 0.09 | 0.06 | . | . | . | −0.10 | 0.46 |
| Asp | 112 | A | . | . | . | . | . | . | −0.51 | 0.56 | . | . | . | −0.40 | 0.46 |
| Pro | 113 | A | A | . | . | . | . | . | −0.51 | 0.67 | . | * | . | −0.60 | 0.29 |
| Ile | 114 | A | A | . | . | . | . | . | −0.17 | −0.09 | . | . | . | 0.30 | 0.72 |
| Ala | 115 | A | A | . | . | . | . | . | −0.17 | −0.01 | * | . | . | 0.30 | 0.67 |
| Met | 116 | A | A | . | . | . | . | . | 0.72 | 0.74 | * | . | . | −0.60 | 0.68 |
| Glu | 117 | A | A | . | . | . | . | . | 0.43 | 0.71 | * | . | . | −0.45 | 1.57 |
| Tyr | 118 | A | . | . | . | . | T | . | 0.30 | 0.94 | * | * | . | −0.05 | 1.63 |
| Tyr | 119 | . | . | . | . | T | T | . | 1.30 | 0.87 | * | * | . | 0.35 | 1.63 |
| Asn | 120 | . | . | . | . | T | T | . | 1.19 | 0.26 | * | * | . | 0.65 | 1.84 |
| Trp | 121 | . | . | . | . | T | T | . | 1.49 | 1.04 | * | * | . | 0.35 | 1.02 |
| Gly | 122 | . | . | . | . | T | . | . | 1.53 | 0.67 | * | . | . | 0.00 | 0.87 |
| Arg | 123 | . | . | . | . | T | . | . | 1.57 | −0.09 | * | . | . | 1.05 | 1.08 |
| Phe | 124 | . | . | . | . | T | . | . | 1.60 | −0.06 | * | . | F | 1.20 | 1.59 |
| Ser | 125 | . | . | . | . | . | . | C | 1.60 | −0.54 | * | . | F | 1.64 | 2.49 |
| Lys | 126 | . | . | . | . | . | . | C | 1.89 | −0.97 | * | * | F | 1.98 | 2.20 |
| Pro | 127 | . | . | . | . | . | T | C | 2.23 | −0.97 | * | * | F | 2.52 | 4.25 |
| Pro | 128 | . | . | . | . | . | T | C | 2.12 | −1.76 | * | * | F | 2.86 | 5.29 |
| Glu | 129 | . | . | . | . | T | T | . | 2.23 | −2.14 | . | . | F | 3.40 | 4.42 |
| Asp | 130 | A | . | . | . | . | T | . | 2.53 | −1.64 | . | * | F | 2.66 | 2.89 |
| Asp | 131 | A | . | . | . | . | . | . | 2.19 | −1.67 | . | * | F | 2.12 | 3.00 |
| Asp | 132 | A | . | . | . | . | T | . | 2.16 | −1.71 | . | . | F | 1.98 | 2.32 |
| Ala | 133 | A | . | . | . | . | T | . | 2.37 | −0.96 | . | . | F | 1.64 | 2.18 |
| Asn | 134 | A | . | . | . | . | T | . | 2.37 | −0.96 | . | . | F | 1.30 | 2.26 |
| Ser | 135 | A | . | . | . | . | T | . | 1.51 | −0.56 | * | . | F | 1.30 | 2.18 |
| Tyr | 136 | A | . | . | . | . | . | . | 0.70 | 0.09 | * | . | F | 0.20 | 1.60 |
| Glu | 137 | A | . | . | . | . | . | . | −0.19 | 0.27 | . | * | . | −0.10 | 0.82 |
| Asn | 138 | A | . | . | B | . | . | . | −0.27 | 0.56 | . | . | . | −0.60 | 0.43 |
| Val | 139 | A | . | . | B | . | . | . | −0.22 | 0.74 | . | . | . | −0.60 | 0.15 |
| Leu | 140 | A | . | . | B | . | . | . | 0.08 | −0.01 | . | . | . | 0.30 | 0.17 |
| Ile | 141 | A | . | . | B | . | . | . | 0.37 | 0.39 | . | . | . | −0.30 | 0.18 |
| Cys | 142 | A | . | . | B | . | . | . | 0.06 | −0.01 | . | . | . | 0.56 | 0.49 |
| Lys | 143 | A | . | . | B | . | . | . | −0.26 | −0.17 | . | . | F | 0.97 | 0.86 |
| Gln | 144 | A | . | . | . | . | . | . | 0.60 | −0.37 | . | . | F | 1.58 | 1.77 |
| Lys | 145 | . | . | . | . | . | . | C | 1.10 | −1.06 | . | . | F | 2.34 | 5.73 |
| Thr | 146 | . | . | . | . | . | . | C | 1.64 | −1.14 | . | . | F | 2.60 | 4.13 |
| Thr | 147 | . | . | . | . | . | . | C | 1.72 | −0.71 | . | * | F | 2.34 | 2.36 |
| Glu | 148 | . | . | . | . | . | . | C | 1.68 | −0.61 | . | . | F | 2.08 | 1.19 |
| Thr | 149 | . | . | . | . | . | . | C | 1.68 | −0.21 | . | . | F | 1.52 | 1.43 |
| Gly | 150 | . | A | . | . | . | . | C | 1.63 | −0.30 | . | . | F | 1.06 | 1.72 |
| Ala | 151 | A | A | . | . | . | . | . | 1.60 | −0.79 | . | . | F | 0.90 | 1.72 |
| Gln | 152 | A | A | . | . | . | . | . | 1.02 | −0.36 | . | . | F | 0.60 | 1.18 |
| Gln | 153 | A | A | . | . | . | . | . | 0.68 | −0.16 | . | . | F | 0.45 | 0.83 |
| Glu | 154 | . | A | . | . | T | . | . | 0.64 | −0.16 | . | . | F | 0.85 | 0.82 |
| Gly | 155 | . | . | . | . | T | T | . | 0.18 | −0.23 | . | . | F | 1.25 | 0.47 |
| Ile | 156 | . | . | . | . | T | T | . | 0.10 | 0.06 | * | * | F | 0.65 | 0.22 |
| Gly | 157 | . | . | . | . | T | T | . | 0.21 | 0.23 | * | * | F | 0.90 | 0.07 |
| Gly | 158 | . | . | . | . | T | T | . | −0.13 | 0.23 | * | * | F | 1.15 | 0.14 |
| Leu | 159 | . | . | . | . | . | . | C | −0.13 | 0.23 | * | * | . | 0.85 | 0.19 |
| Cys | 160 | . | . | B | . | . | T | . | −0.60 | −0.46 | * | * | . | 1.70 | 0.32 |
| Arg | 161 | . | . | . | . | T | T | . | −0.01 | −0.20 | * | * | F | 2.50 | 0.27 |
| Gly | 162 | . | . | . | . | T | T | . | −0.48 | −0.24 | . | * | F | 2.25 | 0.44 |
| Asp | 163 | . | . | . | . | T | T | . | −0.43 | −0.24 | . | * | F | 2.00 | 0.68 |
| Leu | 164 | A | A | . | . | . | . | . | −0.43 | −0.43 | . | * | F | 0.95 | 0.46 |
| Ser | 165 | A | A | . | . | . | . | . | −0.36 | 0.26 | . | * | . | −0.05 | 0.39 |
| Leu | 166 | A | A | . | . | . | . | . | −1.28 | 0.33 | * | * | . | −0.30 | 0.23 |
| Ser | 167 | A | A | . | . | . | . | . | −0.89 | 1.01 | . | * | . | −0.60 | 0.23 |
| Leu | 168 | A | A | . | . | . | . | . | −1.20 | 0.33 | . | * | . | −0.30 | 0.35 |
| Ala | 169 | A | A | . | . | . | . | . | −0.73 | 0.43 | . | * | . | −0.60 | 0.61 |
| Leu | 170 | A | A | . | . | . | . | . | −0.64 | 0.17 | * | * | . | −0.05 | 0.45 |
| Lys | 171 | . | A | . | . | T | . | . | −0.14 | 0.21 | * | * | F | 0.75 | 0.84 |
| Thr | 172 | . | A | . | . | T | . | . | −0.14 | 0.01 | . | * | F | 1.15 | 1.20 |
| Gly | 173 | . | . | . | . | . | T | C | 0.32 | −0.10 | . | * | F | 2.20 | 1.96 |
| Pro | 174 | . | . | . | . | T | T | . | 0.10 | −0.36 | . | . | F | 2.50 | 0.97 |
| Thr | 175 | . | . | . | . | T | T | . | 0.24 | 0.33 | . | * | F | 1.65 | 0.55 |
| Ser | 176 | . | . | . | . | T | T | . | −0.01 | 0.41 | . | . | F | 1.10 | 0.30 |
| Gly | 177 | . | . | . | . | T | . | . | 0.00 | 0.41 | . | . | F | 0.65 | 0.30 |
| Leu | 178 | . | . | . | . | . | . | C | −0.24 | 0.37 | . | . | F | 0.50 | 0.28 |
| Cys | 179 | . | . | . | . | . | T | C | −0.33 | 0.39 | . | . | F | 0.75 | 0.21 |
| Pro | 180 | . | . | . | . | . | T | C | −0.23 | 0.39 | . | . | F | 1.05 | 0.28 |

TABLE 12-continued

| Res | Position | I | II | III | IV | V | VI | VII | VIII | IX | X | XI | XII | XIII | XIV |
|---|---|---|---|---|---|---|---|---|---|---|---|---|---|---|---|
| Ser | 181 | . | . | . | . | . | T | C | 0.07 | 0.39 | . | . | F | 1.35 | 0.53 |
| Ala | 182 | . | . | . | . | . | T | C | 0.41 | −0.30 | . | * | F | 2.40 | 1.72 |
| Ser | 183 | . | . | . | . | . | T | C | 1.22 | −0.87 | . | * | F | 3.00 | 1.93 |
| Pro | 184 | . | . | . | . | . | T | C | 1.89 | −1.30 | . | . | F | 2.70 | 2.40 |
| Glu | 185 | A | . | . | . | . | T | . | 1.76 | −1.69 | . | . | F | 2.20 | 4.12 |
| Glu | 186 | A | . | . | . | . | T | . | 1.17 | −1.76 | . | . | F | 1.90 | 3.04 |
| Asp | 187 | A | . | . | . | . | T | . | 1.37 | −1.46 | . | . | F | 1.60 | 1.38 |
| Glu | 188 | A | . | . | . | . | T | . | 1.28 | −1.46 | . | . | . | 1.15 | 1.02 |
| Gly | 189 | A | . | . | . | . | T | . | 1.10 | −1.03 | . | . | . | 1.00 | 0.75 |
| Ile | 190 | A | . | . | . | . | T | . | 0.71 | −0.60 | . | . | . | 1.00 | 0.58 |

TABLE 13

| Res | Position | I | II | III | IV | V | VI | VII | VIII | IX | X | XI | XII | XIII | XIV |
|---|---|---|---|---|---|---|---|---|---|---|---|---|---|---|---|
| Met | 1 | . | . | B | . | . | . | . | 0.43 | 0.01 | * | . | . | −0.10 | 0.79 |
| Asp | 2 | . | . | B | . | . | . | . | 0.48 | −0.41 | * | . | . | 0.65 | 1.21 |
| Leu | 3 | . | . | B | . | . | T | . | 0.06 | −0.41 | * | . | . | 0.70 | 0.94 |
| Pro | 4 | A | . | . | . | . | T | . | −0.41 | −0.16 | * | . | . | 0.70 | 0.78 |
| Arg | 5 | . | . | B | . | . | T | . | −0.88 | −0.13 | * | . | F | 0.85 | 0.35 |
| Gly | 6 | . | . | B | . | . | T | . | −0.87 | 0.51 | * | . | F | −0.05 | 0.31 |
| Leu | 7 | . | . | B | B | . | . | . | −1.16 | 0.33 | * | . | . | −0.30 | 0.20 |
| Val | 8 | . | . | B | B | . | . | . | −0.93 | 0.81 | * | . | . | −0.60 | 0.11 |
| Val | 9 | . | . | B | B | . | . | . | −1.53 | 1.31 | . | . | . | −0.60 | 0.11 |
| Ala | 10 | . | . | B | B | . | . | . | −1.94 | 1.57 | . | * | . | −0.60 | 0.11 |
| Trp | 11 | . | . | B | B | . | . | . | −2.41 | 1.27 | . | . | . | −0.60 | 0.20 |
| Ala | 12 | . | . | B | B | . | . | . | −1.89 | 1.31 | . | . | . | −0.60 | 0.22 |
| Leu | 13 | . | . | B | B | . | . | . | −1.24 | 1.59 | . | . | . | −0.60 | 0.23 |
| Ser | 14 | . | . | . | . | . | . | C | −0.73 | 1.51 | . | . | . | −0.20 | 0.34 |
| Leu | 15 | . | . | . | . | . | . | C | −0.84 | 1.03 | . | . | . | −0.20 | 0.34 |
| Trp | 16 | . | . | . | . | . | T | C | −0.87 | 1.31 | * | . | . | 0.00 | 0.35 |
| Pro | 17 | . | . | . | . | . | T | C | −0.28 | 1.11 | * | . | . | 0.00 | 0.38 |
| Gly | 18 | . | . | . | . | T | T | . | 0.22 | 0.73 | * | . | F | 0.35 | 0.77 |
| Phe | 19 | . | . | . | . | T | T | . | −0.18 | 0.53 | * | . | F | 0.50 | 1.06 |
| Thr | 20 | . | . | . | . | . | . | C | 0.63 | 0.40 | * | . | F | 0.25 | 0.59 |
| Asp | 21 | . | . | . | . | . | . | C | 0.32 | 0.37 | . | * | F | 0.25 | 0.96 |
| Thr | 22 | . | . | . | . | . | . | C | 0.53 | 0.56 | . | * | . | 0.29 | 1.10 |
| Phe | 23 | . | . | B | . | . | . | . | 0.57 | −0.23 | * | * | . | 1.33 | 1.27 |
| Asn | 24 | . | . | B | . | . | T | . | 1.38 | −0.23 | * | * | . | 1.87 | 1.10 |
| Met | 25 | . | . | . | . | T | T | . | 1.73 | −0.23 | * | * | . | 2.61 | 1.49 |
| Asp | 26 | . | . | . | . | T | T | . | 1.52 | −0.71 | * | . | F | 3.40 | 3.44 |
| Thr | 27 | . | . | . | . | T | T | . | 1.94 | −1.07 | * | * | F | 3.06 | 3.31 |
| Arg | 28 | . | . | . | . | T | . | . | 1.79 | −1.47 | * | * | F | 2.52 | 6.55 |
| Lys | 29 | . | . | B | . | . | . | . | 0.90 | −1.44 | * | . | F | 1.78 | 2.91 |
| Pro | 30 | . | . | B | B | . | . | . | 1.29 | −0.76 | * | . | F | 1.24 | 1.41 |
| Arg | 31 | . | . | B | B | . | . | . | 0.94 | −0.81 | . | . | F | 0.90 | 1.12 |
| Val | 32 | . | . | B | B | . | . | . | 0.96 | −0.39 | . | * | . | 0.30 | 0.55 |
| Ile | 33 | . | . | B | . | . | T | . | 0.96 | 0.00 | . | * | F | 0.22 | 0.48 |
| Pro | 34 | . | . | B | . | . | T | . | 0.60 | −0.43 | . | * | F | 0.79 | 0.48 |
| Gly | 35 | . | . | . | . | T | T | . | 0.22 | 0.06 | * | * | F | 0.56 | 0.93 |
| Ser | 36 | . | . | B | . | . | T | . | −0.59 | −0.09 | * | * | F | 0.88 | 1.34 |
| Arg | 37 | . | . | B | B | . | . | . | −0.43 | 0.01 | . | . | F | −0.30 | 0.75 |
| Thr | 38 | . | . | B | B | . | . | . | 0.11 | 0.37 | . | . | F | −0.27 | 0.66 |
| Ala | 39 | . | . | B | B | . | . | . | 0.08 | 0.37 | . | . | . | −0.39 | 0.49 |
| Phe | 40 | . | . | B | B | . | . | . | 0.11 | 0.74 | . | . | . | −0.66 | 0.39 |
| Phe | 41 | . | . | B | B | . | . | . | −0.44 | 1.23 | . | . | . | −0.63 | 0.39 |
| Gly | 42 | . | . | B | B | . | . | . | −0.56 | 1.39 | . | . | . | −0.60 | 0.29 |
| Tyr | 43 | . | . | B | B | . | . | . | −0.24 | 1.29 | . | . | . | −0.60 | 0.57 |
| Thr | 44 | . | . | B | B | . | . | . | 0.31 | 0.90 | . | . | . | −0.45 | 1.14 |
| Val | 45 | . | . | B | B | . | . | . | 1.01 | 0.61 | . | . | . | −0.45 | 1.57 |
| Gln | 46 | . | . | B | B | . | . | . | 0.82 | 0.19 | . | . | . | −0.15 | 1.67 |
| Gln | 47 | . | . | B | B | . | . | . | 0.87 | 0.11 | . | . | . | −0.30 | 0.81 |
| His | 48 | . | . | B | B | . | . | . | 0.77 | 0.01 | . | . | . | 0.10 | 1.47 |
| Asp | 49 | . | . | B | B | . | . | . | 1.08 | −0.20 | . | . | F | 0.95 | 0.84 |
| Ile | 50 | . | . | . | B | T | . | . | 1.98 | −0.20 | . | . | F | 1.60 | 0.78 |
| Ser | 51 | . | . | . | . | T | T | . | 1.69 | −0.60 | . | . | F | 2.70 | 1.14 |
| Gly | 52 | . | . | . | . | T | T | . | 0.88 | −0.19 | . | . | F | 2.50 | 0.72 |
| Asn | 53 | . | . | . | . | T | T | . | 0.06 | 0.50 | . | . | F | 1.35 | 0.85 |
| Lys | 54 | . | . | . | . | T | T | . | −0.80 | 0.46 | . | . | F | 1.10 | 0.47 |
| Trp | 55 | . | . | B | B | . | . | . | −0.26 | 0.71 | . | . | . | −0.10 | 0.35 |
| Leu | 56 | . | . | B | B | . | . | . | −0.54 | 0.71 | . | . | . | −0.35 | 0.22 |
| Val | 57 | . | . | B | B | . | . | . | −0.41 | 0.81 | . | . | . | −0.60 | 0.11 |
| Val | 58 | . | . | B | B | . | . | . | −1.22 | 1.24 | . | . | . | −0.60 | 0.16 |
| Gly | 59 | . | . | B | B | . | . | . | −1.27 | 1.01 | . | . | . | −0.60 | 0.16 |
| Ala | 60 | . | . | B | . | . | . | . | −1.29 | 0.33 | . | . | . | −0.10 | 0.38 |

TABLE 13-continued

| Res | Position | I | II | III | IV | V | VI | VII | VIII | IX | X | XI | XII | XIII | XIV |
|---|---|---|---|---|---|---|---|---|---|---|---|---|---|---|---|
| Pro | 61 | . | . | . | . | . | . | C | −0.48 | 0.17 | . | * | . | 0.10 | 0.73 |
| Leu | 62 | . | . | . | . | . | . | C | 0.03 | −0.07 | . | . | F | 1.34 | 1.19 |
| Glu | 63 | A | . | . | . | . | T | . | 0.64 | −0.07 | . | * | F | 1.68 | 1.16 |
| Thr | 64 | . | . | B | . | . | T | . | 0.99 | 0.19 | . | * | F | 1.42 | 1.18 |
| Asn | 65 | . | . | . | . | T | T | . | 1.62 | 0.16 | . | * | F | 2.16 | 2.47 |
| Gly | 66 | . | . | . | . | T | T | . | 1.52 | −0.53 | . | . | F | 3.40 | 2.86 |
| Tyr | 67 | . | . | . | . | T | . | . | 1.99 | −0.04 | . | . | F | 2.56 | 2.86 |
| Gln | 68 | . | . | . | . | T | . | . | 1.99 | −0.10 | . | . | F | 2.48 | 1.76 |
| Lys | 69 | . | . | B | . | T | T | . | 1.44 | −0.50 | * | . | F | 2.60 | 2.97 |
| Thr | 70 | . | . | B | . | . | T | . | 1.20 | −0.29 | * | . | F | 2.12 | 1.41 |
| Gly | 71 | . | . | B | . | . | T | . | 1.59 | −0.29 | * | . | F | 2.04 | 1.27 |
| Asp | 72 | . | . | B | . | . | T | . | 1.17 | −0.69 | * | . | F | 2.60 | 1.27 |
| Val | 73 | . | . | B | . | . | . | . | 0.96 | −0.11 | * | . | F | 1.69 | 0.47 |
| Tyr | 74 | . | . | B | . | . | T | . | 0.06 | −0.17 | . | . | . | 1.48 | 0.74 |
| Lys | 75 | . | . | B | . | . | T | . | −0.52 | 0.04 | . | . | . | 0.62 | 0.33 |
| Cys | 76 | . | . | B | . | . | T | . | −0.21 | 0.73 | . | . | . | 0.06 | 0.31 |
| Pro | 77 | . | . | B | . | . | T | . | −0.56 | 0.59 | . | . | . | −0.20 | 0.27 |
| Val | 78 | . | . | B | . | . | . | . | 0.30 | 0.26 | . | . | . | −0.10 | 0.13 |
| Ile | 79 | . | . | B | . | . | . | . | −0.12 | 0.66 | . | . | . | −0.40 | 0.40 |
| His | 80 | . | . | B | . | . | T | . | −0.48 | 0.66 | . | . | . | −0.20 | 0.14 |
| Gly | 81 | . | . | B | . | . | T | . | 0.23 | 0.71 | . | . | . | −0.20 | 0.27 |
| Asn | 82 | . | . | . | . | T | T | . | −0.37 | 0.07 | . | . | . | 0.50 | 0.77 |
| Cys | 83 | . | . | B | . | . | T | . | 0.49 | 0.07 | . | * | F | 0.25 | 0.47 |
| Thr | 84 | . | . | B | . | . | . | . | 0.57 | −0.03 | . | * | F | 0.65 | 0.76 |
| Lys | 85 | . | . | B | . | . | . | . | 0.26 | 0.23 | . | . | F | 0.05 | 0.39 |
| Leu | 86 | . | . | B | . | . | . | . | 0.71 | 0.26 | . | . | . | −0.10 | 0.72 |
| Asn | 87 | . | . | B | . | . | . | . | −0.14 | −0.31 | . | . | . | 0.50 | 0.97 |
| Leu | 88 | . | . | B | B | . | . | . | 0.21 | −0.16 | . | * | . | 0.30 | 0.36 |
| Gly | 89 | . | . | B | B | . | . | . | −0.29 | 0.33 | . | * | . | −0.30 | 0.63 |
| Arg | 90 | . | . | B | B | . | . | . | −0.63 | 0.33 | . | . | . | −0.30 | 0.32 |
| Val | 91 | . | . | B | B | . | . | . | 0.18 | 0.31 | * | . | . | −0.30 | 0.53 |
| Thr | 92 | . | . | B | B | . | . | . | −0.68 | 0.03 | * | . | . | −0.30 | 0.85 |
| Leu | 93 | . | . | B | B | . | . | . | −0.17 | 0.24 | * | * | . | −0.30 | 0.32 |
| Ser | 94 | . | . | B | B | . | . | . | 0.18 | 0.63 | . | * | . | −0.60 | 0.58 |
| Asn | 95 | . | . | B | B | . | . | . | 0.18 | −0.01 | . | * | F | 0.45 | 0.70 |
| Val | 96 | . | . | B | B | . | . | . | 1.08 | −0.50 | . | . | F | 0.60 | 1.67 |
| Ser | 97 | A | . | . | . | . | . | . | 1.39 | −1.19 | * | . | F | 1.10 | 2.49 |
| Glu | 98 | A | . | . | . | . | . | . | 2.20 | −1.57 | * | . | F | 1.10 | 2.58 |
| Arg | 99 | A | . | . | . | . | T | . | 1.90 | −1.57 | . | * | F | 1.30 | 5.60 |
| Lys | 100 | A | . | . | . | . | T | . | 2.01 | −1.60 | . | * | F | 1.30 | 4.13 |
| Asp | 101 | A | . | . | . | . | T | . | 2.06 | −1.99 | . | * | F | 1.30 | 4.67 |
| Asn | 102 | A | . | . | . | . | T | . | 2.01 | −1.30 | . | * | . | 1.15 | 1.97 |
| Met | 103 | A | . | . | . | . | . | . | 1.20 | −0.87 | . | * | . | 0.80 | 0.97 |
| Arg | 104 | A | . | . | . | . | . | . | 0.79 | −0.19 | . | * | . | 0.50 | 0.48 |
| Leu | 105 | . | . | B | . | . | . | . | −0.07 | 0.20 | * | * | . | −0.10 | 0.40 |
| Gly | 106 | . | . | B | . | . | . | . | −0.66 | 0.49 | * | * | . | −0.40 | 0.33 |
| Leu | 107 | . | . | B | . | . | . | . | −0.97 | 0.37 | * | * | . | −0.10 | 0.17 |
| Ser | 108 | . | . | B | . | . | . | . | −0.37 | 0.86 | * | * | . | −0.40 | 0.30 |
| Leu | 109 | . | . | B | . | . | . | . | −0.69 | 0.57 | * | * | . | −0.06 | 0.49 |
| Ala | 110 | . | . | B | . | . | . | . | 0.17 | 0.57 | . | * | . | 0.28 | 0.92 |
| Thr | 111 | . | . | B | . | . | . | . | 0.51 | −0.11 | . | . | F | 1.82 | 1.37 |
| Asn | 112 | . | . | . | . | . | T | C | 1.32 | −0.50 | . | * | F | 2.56 | 2.78 |
| Pro | 113 | . | . | . | . | T | T | . | 1.32 | −0.79 | . | . | F | 3.40 | 4.42 |
| Lys | 114 | . | . | . | . | T | T | . | 1.43 | −0.90 | . | . | F | 3.06 | 4.10 |
| Asp | 115 | . | . | . | . | T | T | . | 1.21 | −0.60 | . | . | F | 2.72 | 2.21 |
| Asn | 116 | . | . | . | . | T | T | . | 0.93 | −0.31 | . | . | F | 2.08 | 1.18 |
| Ser | 117 | . | . | B | . | . | T | . | 0.27 | −0.24 | . | . | F | 1.19 | 0.60 |
| Phe | 118 | . | . | B | . | . | T | . | 0.18 | 0.33 | . | . | . | 0.10 | 0.19 |
| Leu | 119 | . | . | B | . | . | T | . | −0.08 | 0.71 | . | . | . | −0.20 | 0.16 |
| Ala | 120 | . | . | B | . | . | . | . | −0.89 | 0.74 | . | . | . | −0.40 | 0.18 |
| Cys | 121 | . | . | B | . | . | . | . | −1.18 | 1.04 | . | . | . | −0.40 | 0.17 |
| Ser | 122 | . | . | . | . | . | T | C | −1.18 | 1.17 | . | . | . | 0.00 | 0.22 |
| Pro | 123 | . | . | . | . | T | T | . | −0.51 | 0.87 | . | . | . | 0.20 | 0.30 |
| Leu | 124 | . | . | . | . | T | T | . | 0.30 | 0.87 | . | . | . | 0.20 | 0.75 |
| Trp | 125 | . | . | . | . | T | T | . | 0.22 | 0.30 | . | . | . | 0.50 | 0.97 |
| Ser | 126 | . | . | B | . | . | . | . | 0.54 | 0.49 | . | . | . | −0.27 | 0.34 |
| His | 127 | . | . | B | . | . | T | . | 0.54 | 0.49 | . | . | . | 0.06 | 0.40 |
| Glu | 128 | . | . | . | . | T | T | . | 0.46 | 0.19 | . | . | . | 0.89 | 0.51 |
| Cys | 129 | . | . | . | . | T | T | . | 1.02 | −0.34 | . | . | F | 1.77 | 0.51 |
| Gly | 130 | . | . | . | . | T | T | . | 1.07 | 0.03 | . | . | F | 1.30 | 0.59 |
| Ser | 131 | . | . | . | . | T | T | . | 1.06 | 0.29 | . | . | F | 1.17 | 0.54 |
| Ser | 132 | . | . | . | . | T | T | . | 0.78 | 0.77 | . | . | F | 0.89 | 1.44 |
| Tyr | 133 | . | . | . | . | T | T | . | 0.43 | 0.69 | . | . | F | 0.76 | 2.11 |
| Tyr | 134 | . | . | B | . | . | T | . | 0.50 | 0.69 | . | . | F | 0.23 | 1.55 |
| Thr | 135 | . | . | B | . | . | . | . | 0.18 | 0.91 | . | . | F | −0.10 | 1.15 |
| Thr | 136 | . | . | B | . | . | . | . | 0.18 | 1.10 | . | . | . | −0.40 | 0.39 |
| Gly | 137 | . | . | B | . | . | T | . | 0.59 | 0.73 | . | * | . | −0.20 | 0.34 |
| Met | 138 | . | . | B | . | . | T | . | −0.02 | −0.03 | . | * | . | 0.70 | 0.46 |

TABLE 13-continued

| Res | Position | I | II | III | IV | V | VI | VII | VIII | IX | X | XI | XII | XIII | XIV |
|---|---|---|---|---|---|---|---|---|---|---|---|---|---|---|---|
| Cys | 139 | . | . | B | . | . | T | . | 0.22 | 0.13 | . | * | . | 0.10 | 0.23 |
| Ser | 140 | . | . | B | . | . | T | . | 0.23 | 0.04 | . | * | . | 0.10 | 0.38 |
| Arg | 141 | . | . | B | . | . | . | . | 0.54 | 0.00 | * | * | F | 0.05 | 0.52 |
| Val | 142 | . | . | B | . | . | . | . | 0.19 | −0.21 | * | * | F | 0.80 | 1.55 |
| Asn | 143 | . | . | B | . | . | T | . | 0.90 | 0.00 | * | * | F | 0.61 | 1.00 |
| Ser | 144 | . | . | . | . | . | T | C | 0.87 | −0.39 | * | * | F | 1.62 | 1.00 |
| Asn | 145 | . | . | . | . | T | T | . | 0.87 | 0.40 | * | * | F | 1.13 | 1.17 |
| Phe | 146 | . | . | . | . | T | T | . | 0.80 | 0.14 | * | * | . | 1.34 | 0.97 |
| Arg | 147 | . | . | . | . | T | . | . | 1.34 | −0.26 | * | * | . | 2.10 | 1.45 |
| Phe | 148 | . | . | . | B | T | . | . | 0.49 | −0.16 | * | * | . | 1.69 | 1.30 |
| Ser | 149 | . | . | B | B | . | . | . | 0.20 | 0.09 | * | * | F | 0.63 | 1.12 |
| Lys | 150 | . | . | . | B | . | . | C | −0.01 | −0.20 | * | * | F | 1.07 | 0.58 |
| Thr | 151 | . | . | . | B | T | . | . | 0.10 | 0.23 | * | * | F | 0.61 | 1.03 |
| Val | 152 | . | . | . | B | . | . | C | −0.82 | −0.06 | * | . | . | 0.50 | 0.77 |
| Ala | 153 | . | . | B | B | . | . | C | −0.12 | 0.24 | * | . | . | −0.10 | 0.32 |
| Pro | 154 | A | A | . | . | . | . | . | 0.29 | 0.64 | * | . | . | −0.60 | 0.38 |
| Ala | 155 | A | A | . | . | . | . | . | −0.42 | 0.16 | * | . | . | −0.15 | 1.01 |
| Leu | 156 | A | A | . | B | . | . | . | −0.11 | 0.09 | * | . | . | −0.30 | 0.54 |
| Gln | 157 | A | A | . | B | . | . | . | 0.43 | −0.01 | * | . | . | 0.30 | 0.60 |
| Arg | 158 | . | A | B | B | . | . | . | 0.78 | 0.04 | * | . | F | −0.15 | 0.86 |
| Cys | 159 | . | A | B | B | . | . | . | 0.39 | 0.30 | * | * | F | 0.00 | 1.63 |
| Gln | 160 | . | . | B | B | . | . | . | 0.98 | 0.23 | * | * | . | −0.30 | 0.93 |
| Thr | 161 | . | . | B | B | . | . | . | 0.90 | −0.17 | * | * | . | 0.30 | 0.80 |
| Tyr | 162 | . | . | B | B | . | . | . | 0.04 | 0.51 | * | * | . | −0.45 | 1.04 |
| Met | 163 | . | . | B | B | . | . | . | −0.96 | 0.59 | . | * | . | −0.60 | 0.45 |
| Asp | 164 | . | . | B | B | . | . | . | −1.14 | 0.87 | . | * | . | −0.60 | 0.22 |
| Ile | 165 | . | . | B | B | . | . | . | −1.96 | 1.03 | . | * | . | −0.60 | 0.10 |
| Val | 166 | . | . | B | B | . | . | . | −1.64 | 0.96 | . | * | . | −0.60 | 0.09 |
| Ile | 167 | . | . | B | B | . | . | . | −1.74 | 0.34 | . | * | . | −0.30 | 0.09 |
| Val | 168 | . | . | B | B | . | . | . | −1.44 | 0.77 | . | * | . | −0.35 | 0.12 |
| Leu | 169 | . | . | B | B | . | . | . | −1.44 | 0.47 | . | * | . | −0.10 | 0.22 |
| Asp | 170 | . | . | . | B | T | . | . | −0.86 | 0.23 | * | * | F | 1.00 | 0.50 |
| Gly | 171 | . | . | . | . | T | T | . | −0.89 | −0.07 | . | . | F | 2.25 | 0.90 |
| Ser | 172 | . | . | . | . | T | T | . | −0.24 | −0.03 | * | * | F | 2.50 | 0.77 |
| Asn | 173 | . | . | . | . | . | T | C | 0.40 | 0.04 | * | . | F | 1.45 | 0.72 |
| Ser | 174 | . | . | . | . | . | T | C | 0.92 | 0.47 | * | . | F | 1.05 | 1.12 |
| Ile | 175 | . | . | . | B | . | . | C | 0.07 | 0.96 | * | . | . | 0.10 | 0.88 |
| Tyr | 176 | . | . | . | B | . | . | C | 0.41 | 1.21 | * | . | . | −0.15 | 0.41 |
| Pro | 177 | . | . | B | B | . | . | . | −0.14 | 0.81 | . | * | . | −0.60 | 0.53 |
| Trp | 178 | . | . | B | B | . | . | . | −0.14 | 1.07 | . | * | . | −0.60 | 0.56 |
| Val | 179 | . | . | B | B | . | . | . | 0.12 | 0.79 | . | . | . | −0.60 | 0.62 |
| Glu | 180 | . | . | B | B | . | . | . | 0.31 | 0.53 | . | * | . | −0.60 | 0.54 |
| Val | 181 | A | . | . | B | . | . | . | −0.26 | 0.89 | . | . | . | −0.60 | 0.45 |
| Gln | 182 | A | . | . | B | . | . | . | −0.93 | 0.66 | . | . | . | −0.60 | 0.50 |
| His | 183 | A | . | . | B | . | . | . | −0.64 | 0.70 | * | * | . | −0.60 | 0.20 |
| Phe | 184 | A | . | . | B | . | . | . | −0.68 | 1.10 | * | . | . | −0.60 | 0.43 |
| Leu | 185 | A | . | . | B | . | . | . | −1.49 | 1.14 | * | . | . | −0.60 | 0.18 |
| Ile | 186 | A | . | . | B | . | . | . | −0.59 | 1.43 | * | . | . | −0.60 | 0.11 |
| Asn | 187 | A | . | . | B | . | . | . | −0.54 | 0.93 | * | . | . | −0.60 | 0.25 |
| Ile | 188 | A | . | . | B | . | . | . | −1.21 | 0.14 | * | * | . | −0.30 | 0.60 |
| Leu | 189 | A | . | . | B | . | . | . | −0.76 | 0.24 | * | * | . | −0.30 | 0.74 |
| Lys | 190 | . | . | B | B | . | . | . | −0.83 | 0.31 | * | . | . | −0.30 | 0.72 |
| Lys | 191 | . | . | B | B | . | . | . | −0.29 | 0.60 | * | * | . | −0.60 | 0.72 |
| Phe | 192 | . | . | B | B | . | . | . | −0.50 | 0.34 | * | . | . | −0.30 | 0.86 |
| Tyr | 193 | . | . | B | B | . | . | . | 0.04 | 0.09 | * | . | . | −0.30 | 0.67 |
| Ile | 194 | . | . | B | B | . | . | . | 0.86 | 0.51 | * | . | . | −0.60 | 0.33 |
| Gly | 195 | . | . | . | . | . | T | C | −0.08 | 0.91 | * | . | . | 0.00 | 0.66 |
| Pro | 196 | . | . | . | . | T | T | . | −0.12 | 0.81 | . | * | F | 0.35 | 0.30 |
| Gly | 197 | . | . | . | . | T | T | . | −0.28 | 0.46 | . | * | F | 0.35 | 0.73 |
| Gln | 198 | . | . | B | . | . | T | . | −0.38 | 0.41 | . | * | F | −0.05 | 0.55 |
| Ile | 199 | . | . | B | B | . | . | . | −0.34 | 0.41 | . | * | . | −0.60 | 0.35 |
| Gln | 200 | . | . | B | B | . | . | . | −0.86 | 0.63 | . | * | . | −0.60 | 0.26 |
| Val | 201 | . | . | B | B | . | . | . | −0.64 | 0.84 | . | * | . | −0.60 | 0.11 |
| Gly | 202 | . | . | B | B | . | . | . | −0.54 | 0.84 | . | * | . | −0.60 | 0.28 |
| Val | 203 | . | . | B | B | . | . | . | −0.89 | 0.91 | . | * | . | −0.60 | 0.25 |
| Val | 204 | . | . | B | B | . | . | . | 0.00 | 0.94 | . | . | . | −0.60 | 0.34 |
| Gln | 205 | . | . | B | B | . | . | . | 0.00 | 0.30 | . | . | . | −0.30 | 0.59 |
| Tyr | 206 | . | . | B | B | . | . | . | 0.00 | −0.13 | * | . | . | 0.45 | 1.32 |
| Gly | 207 | . | A | B | B | . | . | . | −0.51 | −0.13 | * | . | F | 0.60 | 1.32 |
| Glu | 208 | A | A | . | B | . | . | . | 0.31 | −0.13 | * | . | F | 0.45 | 0.57 |
| Asp | 209 | A | A | . | B | . | . | . | 1.17 | −0.03 | * | . | F | 0.45 | 0.49 |
| Val | 210 | A | A | . | B | . | . | . | 0.47 | −0.79 | * | . | . | 0.60 | 0.86 |
| Val | 211 | A | A | . | B | . | . | . | 0.68 | −0.43 | * | . | . | 0.30 | 0.43 |
| His | 212 | A | A | . | B | . | . | . | 0.21 | 0.07 | * | * | . | −0.30 | 0.35 |
| Glu | 213 | A | A | . | . | . | . | . | 0.21 | 0.76 | . | . | . | −0.60 | 0.39 |
| Phe | 214 | A | A | . | . | . | . | . | 0.21 | 0.51 | . | * | . | −0.60 | 0.84 |
| His | 215 | A | A | . | . | . | . | . | 0.82 | −0.13 | * | . | . | 0.45 | 1.04 |
| Leu | 216 | A | A | . | . | . | . | . | 1.79 | 0.13 | * | . | . | 0.04 | 0.94 |

TABLE 13-continued

| Res | Position | I | II | III | IV | V | VI | VII | VIII | IX | X | XI | XII | XIII | XIV |
|---|---|---|---|---|---|---|---|---|---|---|---|---|---|---|---|
| Asn | 217 | A | . | . | . | . | T | . | 1.52 | 0.13 | * | . | . | 0.93 | 2.12 |
| Asp | 218 | A | . | . | . | . | T | . | 0.67 | −0.27 | * | . | F | 2.02 | 2.09 |
| Tyr | 219 | . | . | . | . | T | T | . | 1.41 | −0.13 | * | . | F | 2.76 | 1.88 |
| Arg | 220 | . | . | . | . | T | T | . | 1.44 | −0.81 | * | . | F | 3.40 | 2.34 |
| Ser | 221 | A | . | . | . | . | . | . | 1.40 | −1.21 | * | . | F | 2.46 | 2.34 |
| Val | 222 | . | A | B | . | . | . | . | 0.54 | −0.57 | * | . | F | 1.92 | 1.11 |
| Lys | 223 | . | A | B | . | . | . | . | 0.54 | −0.69 | * | . | F | 1.43 | 0.42 |
| Asp | 224 | . | A | B | . | . | . | . | 0.20 | −0.69 | * | . | F | 1.09 | 0.54 |
| Val | 225 | A | A | . | . | . | . | . | −0.50 | −0.57 | * | . | . | 0.60 | 0.74 |
| Val | 226 | A | A | . | . | . | . | . | −0.50 | −0.71 | * | . | . | 0.60 | 0.37 |
| Glu | 227 | A | A | . | . | . | . | . | 0.32 | −0.33 | * | . | . | 0.30 | 0.30 |
| Ala | 228 | A | A | . | . | . | . | . | −0.61 | 0.17 | * | . | . | −0.30 | 0.55 |
| Ala | 229 | A | A | . | . | . | . | . | −0.61 | 0.21 | * | . | . | −0.30 | 0.52 |
| Ser | 230 | A | A | . | . | . | . | . | 0.24 | −0.43 | * | * | . | 0.30 | 0.52 |
| His | 231 | A | A | . | . | . | . | . | 1.21 | −0.03 | * | * | . | 0.64 | 0.89 |
| Ile | 232 | A | A | . | . | . | . | . | 0.87 | −0.53 | * | * | . | 1.43 | 1.72 |
| Glu | 233 | A | A | . | . | . | . | . | 1.11 | −0.60 | * | * | F | 1.92 | 1.27 |
| Gln | 234 | . | . | . | . | T | T | . | 1.39 | −0.56 | * | * | F | 2.91 | 0.92 |
| Arg | 235 | . | . | . | . | T | T | . | 1.69 | −0.57 | . | * | F | 3.40 | 1.90 |
| Gly | 236 | . | . | . | . | T | T | . | 1.41 | −1.26 | * | * | F | 3.06 | 1.90 |
| Gly | 237 | . | . | . | . | . | T | C | 2.41 | −0.77 | * | * | F | 2.68 | 1.59 |
| Thr | 238 | . | . | . | . | . | . | C | 2.10 | −1.17 | * | * | F | 2.30 | 1.59 |
| Glu | 239 | . | . | . | . | . | . | C | 1.51 | −0.69 | * | * | F | 2.12 | 2.31 |
| Thr | 240 | . | . | B | . | . | . | . | 0.70 | −0.61 | * | * | F | 1.74 | 2.36 |
| Arg | 241 | . | . | B | . | . | . | . | 0.70 | −0.26 | . | * | F | 1.60 | 1.42 |
| Thr | 242 | . | . | B | . | . | . | . | 0.16 | −0.31 | . | * | F | 1.29 | 0.81 |
| Ala | 243 | A | A | . | . | . | . | . | 0.47 | 0.37 | . | * | . | 0.18 | 0.39 |
| Phe | 244 | A | A | . | . | . | . | . | −0.23 | −0.11 | . | * | . | 0.62 | 0.35 |
| Gly | 245 | A | A | . | . | . | . | . | −0.51 | 0.67 | . | * | . | −0.44 | 0.21 |
| Ile | 246 | A | A | . | . | . | . | . | −0.51 | 0.69 | . | * | . | −0.60 | 0.21 |
| Glu | 247 | A | A | . | . | . | . | . | −0.50 | 0.19 | . | . | . | −0.30 | 0.47 |
| Phe | 248 | A | A | . | . | . | . | . | 0.09 | −0.21 | . | . | . | 0.30 | 0.64 |
| Ala | 249 | A | A | . | . | . | . | . | 0.20 | −0.64 | . | . | . | 0.75 | 1.58 |
| Arg | 250 | A | A | . | . | . | . | . | −0.16 | −0.83 | . | . | F | 0.75 | 0.92 |
| Ser | 251 | A | A | . | . | . | . | . | 0.73 | −0.04 | . | . | F | 0.45 | 0.92 |
| Glu | 252 | A | A | . | . | . | . | . | 0.78 | −0.43 | . | . | F | 0.60 | 1.58 |
| Ala | 253 | A | A | . | . | . | . | . | 1.13 | −0.93 | . | . | F | 0.90 | 1.61 |
| Phe | 254 | A | A | . | . | . | . | . | 1.38 | −0.50 | * | * | F | 0.60 | 1.19 |
| Gln | 255 | A | . | . | . | . | T | . | 1.38 | −0.46 | * | . | F | 0.85 | 0.68 |
| Lys | 256 | A | . | . | . | . | T | . | 1.72 | −0.46 | * | . | F | 1.00 | 1.32 |
| Gly | 257 | A | . | . | . | . | T | . | 1.38 | −0.96 | * | . | F | 1.30 | 3.05 |
| Gly | 258 | A | . | . | . | . | T | . | 1.38 | −1.31 | * | . | F | 1.30 | 1.74 |
| Arg | 259 | A | A | . | . | . | . | . | 2.12 | −1.21 | * | . | F | 0.75 | 0.88 |
| Lys | 260 | A | A | . | . | . | . | . | 2.17 | −1.21 | * | . | F | 0.90 | 1.78 |
| Gly | 261 | A | A | . | . | . | . | . | 1.27 | −1.64 | * | . | F | 0.90 | 3.59 |
| Ala | 262 | A | A | . | . | . | . | . | 1.01 | −1.43 | * | . | F | 0.90 | 1.36 |
| Lys | 263 | A | . | . | B | . | . | . | 0.47 | −0.81 | * | . | F | 0.75 | 0.67 |
| Lys | 264 | . | . | B | B | . | . | . | −0.50 | −0.13 | * | . | . | 0.30 | 0.48 |
| Val | 265 | . | . | B | B | . | . | . | −1.43 | 0.09 | * | . | . | −0.30 | 0.35 |
| Met | 266 | . | . | B | B | . | . | . | −1.40 | 0.27 | * | . | . | −0.30 | 0.12 |
| Ile | 267 | . | . | B | B | . | . | . | −0.81 | 0.76 | * | . | . | −0.60 | 0.09 |
| Val | 268 | . | . | B | B | . | . | . | −1.20 | 0.76 | * | . | . | −0.60 | 0.20 |
| Ile | 269 | . | . | B | . | . | T | . | −1.24 | 0.54 | . | . | . | −0.20 | 0.20 |
| Thr | 270 | . | . | B | . | . | T | . | −0.69 | −0.07 | . | . | F | 0.85 | 0.49 |
| Asp | 271 | . | . | B | . | . | T | . | −0.12 | −0.37 | . | . | F | 0.85 | 0.89 |
| Gly | 272 | . | . | . | . | . | T | C | 0.77 | −0.51 | . | . | F | 1.50 | 1.73 |
| Glu | 273 | . | . | . | . | . | . | C | 1.32 | −1.20 | . | . | F | 1.60 | 2.00 |
| Ser | 274 | . | . | . | . | . | . | C | 2.00 | −1.30 | . | . | F | 1.90 | 1.60 |
| His | 275 | . | . | . | . | . | . | C | 2.31 | −0.87 | . | . | F | 2.20 | 2.51 |
| Asp | 276 | . | . | . | . | . | . | C | 1.50 | −1.30 | . | * | F | 2.50 | 2.42 |
| Ser | 277 | . | . | . | . | . | T | C | 1.84 | −0.61 | . | . | F | 3.00 | 1.49 |
| Pro | 278 | A | . | . | . | . | T | . | 1.89 | −1.00 | . | . | F | 2.50 | 1.89 |
| Asp | 279 | A | . | . | . | . | T | . | 1.33 | −1.50 | * | . | F | 2.20 | 2.27 |
| Leu | 280 | A | . | . | . | . | T | . | 0.48 | −0.86 | * | . | F | 1.90 | 1.25 |
| Glu | 281 | A | A | . | . | . | . | . | 0.48 | −0.56 | * | . | F | 1.05 | 0.57 |
| Lys | 282 | A | A | . | . | . | . | . | 0.78 | −0.59 | * | . | F | 0.75 | 0.59 |
| Val | 283 | A | A | . | . | . | . | . | 0.69 | −0.19 | * | . | . | 0.45 | 1.24 |
| Ile | 284 | A | A | . | . | . | . | . | 0.69 | −0.49 | * | . | F | 0.45 | 0.96 |
| Gln | 285 | . | A | B | . | . | . | . | 1.61 | −0.49 | * | . | F | 0.79 | 0.83 |
| Gln | 286 | A | A | . | . | . | . | . | 1.61 | −0.49 | * | . | F | 1.28 | 2.19 |
| Ser | 287 | A | A | . | . | . | . | . | 1.57 | −1.13 | * | * | F | 1.92 | 5.22 |
| Glu | 288 | . | . | . | . | . | T | C | 1.57 | −1.41 | * | . | F | 2.86 | 4.85 |
| Arg | 289 | . | . | . | . | T | T | . | 2.14 | −1.17 | * | . | F | 3.40 | 2.08 |
| Asp | 290 | . | . | . | . | T | T | . | 2.26 | −1.09 | . | . | F | 3.06 | 2.24 |
| Asn | 291 | . | . | . | . | T | T | . | 2.01 | −1.47 | * | . | F | 2.72 | 2.53 |
| Val | 292 | . | . | B | B | . | . | . | 1.72 | −0.71 | . | . | F | 1.58 | 2.02 |
| Thr | 293 | . | . | B | B | . | . | . | 0.87 | −0.21 | . | . | F | 0.94 | 1.22 |
| Arg | 294 | . | . | B | B | . | . | . | 0.17 | 0.43 | * | . | . | −0.60 | 0.57 |

TABLE 13-continued

| Res | Position | I | II | III | IV | V | VI | VII | VIII | IX | X | XI | XII | XIII | XIV |
|---|---|---|---|---|---|---|---|---|---|---|---|---|---|---|---|
| Tyr | 295 | . | . | B | B | . | . | . | −0.69 | 0.53 | * | . | . | −0.60 | 0.77 |
| Ala | 296 | . | . | B | B | . | . | . | −1.50 | 0.53 | * | . | . | −0.60 | 0.40 |
| Val | 297 | . | . | B | B | . | . | . | −0.99 | 0.73 | * | . | . | −0.60 | 0.17 |
| Ala | 298 | . | . | B | B | . | . | . | −0.92 | 1.16 | * | . | . | −0.60 | 0.11 |
| Val | 299 | . | . | B | B | . | . | . | −1.28 | 1.16 | * | . | . | −0.60 | 0.16 |
| Leu | 300 | . | . | B | B | . | . | . | −1.03 | 1.41 | * | . | . | −0.60 | 0.34 |
| Gly | 301 | . | . | B | B | . | . | . | −0.33 | 1.17 | * | . | . | −0.60 | 0.55 |
| Tyr | 302 | . | . | B | B | . | . | . | 0.63 | 0.67 | * | . | . | −0.45 | 1.45 |
| Tyr | 303 | . | . | B | . | . | . | . | 0.88 | 0.03 | * | . | . | 0.39 | 3.44 |
| Asn | 304 | . | . | B | . | . | T | . | 0.84 | −0.23 | * | . | . | 1.53 | 3.44 |
| Arg | 305 | . | . | . | . | T | T | . | 1.66 | 0.03 | * | . | F | 1.82 | 1.54 |
| Arg | 306 | . | . | . | . | T | T | . | 1.79 | −0.33 | * | . | F | 2.76 | 1.58 |
| Gly | 307 | . | . | . | . | T | T | . | 2.03 | −0.66 | * | . | F | 3.40 | 1.52 |
| Ile | 308 | . | . | . | . | . | . | C | 1.97 | −1.06 | . | . | F | 2.66 | 1.34 |
| Asn | 309 | . | . | . | . | . | T | C | 1.27 | −0.57 | * | . | F | 2.37 | 0.99 |
| Pro | 310 | . | . | . | . | . | T | C | 0.34 | 0.21 | * | . | F | 1.13 | 0.86 |
| Glu | 311 | . | . | B | . | . | T | . | 0.23 | 0.47 | . | . | F | 0.44 | 1.02 |
| Thr | 312 | . | . | B | . | . | T | . | 0.58 | 0.19 | * | . | F | 0.40 | 1.02 |
| Phe | 313 | A | A | . | . | . | . | . | 0.58 | −0.21 | . | * | . | 0.45 | 1.14 |
| Leu | 314 | A | A | . | . | . | . | . | 0.62 | 0.04 | * | * | . | −0.30 | 0.46 |
| Asn | 315 | A | A | . | . | . | . | . | 0.59 | 0.04 | * | . | . | −0.30 | 0.64 |
| Glu | 316 | A | A | . | . | . | . | . | −0.30 | 0.31 | * | . | F | 0.00 | 1.16 |
| Ile | 317 | A | A | . | . | . | . | . | −0.58 | 0.21 | * | . | . | −0.30 | 0.98 |
| Lys | 318 | A | A | . | . | . | . | . | −0.18 | 0.03 | * | . | . | −0.30 | 0.62 |
| Tyr | 319 | . | A | B | . | . | . | . | 0.63 | 0.01 | * | . | . | −0.30 | 0.48 |
| Ile | 320 | . | A | B | . | . | . | . | 0.42 | 0.01 | * | . | . | −0.15 | 1.14 |
| Ala | 321 | . | A | B | . | . | . | . | 0.42 | −0.24 | * | . | . | 0.64 | 0.88 |
| Ser | 322 | . | A | B | . | . | . | . | 1.31 | −0.24 | * | . | . | 0.98 | 0.94 |
| Asp | 323 | . | . | . | . | . | T | C | 1.31 | −1.00 | . | . | F | 2.52 | 2.23 |
| Pro | 324 | A | . | . | . | . | T | . | 1.52 | −1.69 | . | . | F | 2.66 | 4.42 |
| Asp | 325 | . | . | . | . | T | T | . | 1.71 | −1.69 | . | . | F | 3.40 | 4.49 |
| Asp | 326 | A | . | . | . | . | T | . | 1.60 | −1.29 | . | . | F | 2.66 | 2.33 |
| Lys | 327 | A | A | . | . | . | . | . | 1.90 | −0.50 | . | . | F | 1.62 | 1.30 |
| His | 328 | A | A | . | . | . | . | . | 1.04 | −0.53 | . | * | . | 1.43 | 1.26 |
| Phe | 329 | . | A | B | . | . | . | . | 0.94 | 0.11 | * | . | . | 0.04 | 0.56 |
| Phe | 330 | . | A | B | . | . | . | . | 0.94 | 0.60 | * | . | . | −0.60 | 0.40 |
| Asn | 331 | A | A | . | . | . | . | . | 0.94 | 0.60 | * | . | . | −0.60 | 0.49 |
| Val | 332 | A | A | . | . | . | . | . | 0.31 | 0.10 | * | . | . | −0.30 | 0.99 |
| Thr | 333 | A | A | . | . | . | . | . | −0.24 | −0.19 | * | . | F | 0.60 | 1.15 |
| Asp | 334 | A | A | . | . | . | . | . | −0.36 | −0.47 | * | * | F | 0.45 | 0.72 |
| Glu | 335 | A | A | . | . | . | . | . | 0.39 | −0.19 | . | * | . | 0.30 | 0.81 |
| Ala | 336 | A | A | . | . | . | . | . | 0.39 | −0.83 | . | . | . | 0.75 | 1.12 |
| Ala | 337 | A | A | . | . | . | . | . | 0.36 | −1.31 | . | . | . | 0.75 | 1.12 |
| Leu | 338 | A | A | . | . | . | . | . | −0.19 | −0.63 | * | . | . | 0.60 | 0.45 |
| Lys | 339 | A | A | . | . | . | . | . | −0.19 | 0.01 | * | . | . | −0.30 | 0.33 |
| Asp | 340 | A | A | . | . | . | . | . | −0.78 | −0.49 | * | . | . | 0.30 | 0.55 |
| Ile | 341 | A | A | . | . | . | . | . | −1.00 | −0.49 | * | . | . | 0.30 | 0.67 |
| Val | 342 | A | A | . | . | . | . | . | −0.76 | −0.49 | * | . | . | 0.30 | 0.28 |
| Asp | 343 | A | A | . | . | . | . | . | 0.06 | −0.06 | * | . | . | 0.30 | 0.16 |
| Ala | 344 | A | A | . | . | . | . | . | 0.12 | −0.06 | * | . | . | 0.30 | 0.39 |
| Leu | 345 | A | . | . | . | . | T | . | −0.77 | −0.74 | * | . | . | 1.15 | 1.03 |
| Gly | 346 | A | . | . | . | . | T | . | −0.58 | −0.70 | * | . | . | 1.00 | 0.43 |
| Asp | 347 | A | . | . | . | . | T | . | −0.02 | 0.09 | * | . | . | 0.10 | 0.37 |
| Arg | 348 | . | . | B | . | . | T | . | −0.83 | −0.03 | * | . | . | 0.70 | 0.60 |
| Ile | 349 | . | . | B | . | . | . | . | −0.24 | −0.03 | * | . | . | 0.50 | 0.50 |
| Phe | 350 | . | . | B | . | . | . | . | 0.22 | −0.46 | * | . | . | 0.50 | 0.52 |
| Ser | 351 | . | . | B | . | . | . | . | 0.26 | −0.03 | * | . | . | 0.50 | 0.26 |
| Leu | 352 | . | . | B | . | . | . | . | 0.26 | 0.46 | . | . | . | −0.10 | 0.54 |
| Glu | 353 | . | . | . | . | . | . | C | 0.19 | 0.17 | . | . | F | 1.00 | 1.01 |
| Gly | 354 | . | . | . | . | . | . | C | 1.08 | −0.61 | . | . | F | 2.20 | 1.50 |
| Thr | 355 | . | . | . | . | . | . | C | 1.78 | −0.60 | . | * | F | 2.50 | 2.93 |
| Asn | 356 | . | . | . | . | . | T | C | 1.77 | −1.29 | . | . | F | 3.00 | 2.93 |
| Lys | 357 | . | . | . | . | . | T | C | 2.28 | −0.80 | . | * | F | 2.70 | 4.28 |
| Asn | 358 | . | . | . | . | . | T | C | 1.58 | −0.84 | . | . | F | 2.40 | 3.97 |
| Glu | 359 | A | . | . | . | . | T | . | 1.58 | −0.54 | . | . | F | 1.90 | 2.14 |
| Thr | 360 | A | . | . | . | . | T | . | 1.08 | −0.51 | . | * | F | 1.60 | 1.06 |
| Ser | 361 | A | . | . | . | . | T | . | 1.08 | 0.17 | . | * | F | 0.25 | 0.54 |
| Phe | 362 | A | . | . | . | . | T | . | 0.43 | −0.23 | . | * | . | 0.70 | 0.54 |
| Gly | 363 | A | . | . | . | . | T | . | 0.13 | 0.39 | . | . | . | 0.10 | 0.37 |
| Leu | 364 | A | . | . | . | . | . | . | 0.13 | 0.29 | . | * | . | −0.10 | 0.37 |
| Glu | 365 | A | . | . | . | . | . | . | 0.13 | 0.30 | . | . | . | −0.10 | 0.74 |
| Met | 366 | A | . | . | . | . | . | . | 0.09 | 0.00 | . | . | . | 0.05 | 1.09 |
| Ser | 367 | A | . | . | . | . | T | . | 0.09 | 0.00 | . | . | F | 0.40 | 1.30 |
| Gln | 368 | A | . | . | . | . | T | . | 0.13 | 0.10 | . | . | F | 0.25 | 0.65 |
| Thr | 369 | . | . | . | . | . | T | C | 0.64 | 0.49 | . | . | F | 0.15 | 0.88 |
| Gly | 370 | . | . | . | . | . | T | C | 0.61 | 0.26 | . | . | F | 0.45 | 0.88 |
| Phe | 371 | . | . | . | . | . | . | C | 0.36 | 0.37 | . | . | F | 0.25 | 0.69 |
| Ser | 372 | . | . | . | B | . | . | C | −0.20 | 0.61 | . | . | F | −0.25 | 0.36 |

TABLE 13-continued

| Res | Position | I | II | III | IV | V | VI | VII | VIII | IX | X | XI | XII | XIII | XIV |
|---|---|---|---|---|---|---|---|---|---|---|---|---|---|---|---|
| Ser | 373 | . | . | . | B | . | . | C | −0.20 | 0.77 | . | . | . | −0.40 | 0.27 |
| His | 374 | . | . | B | B | . | . | . | 0.11 | 0.34 | . | . | . | −0.30 | 0.53 |
| Val | 375 | . | . | B | B | . | . | . | 0.11 | −0.44 | . | . | . | 0.30 | 0.67 |
| Val | 376 | . | . | B | . | . | T | . | −0.04 | −0.40 | . | . | . | 0.70 | 0.49 |
| Glu | 377 | . | . | B | . | . | T | . | −0.56 | −0.14 | . | . | . | 0.70 | 0.27 |
| Asp | 378 | A | . | . | . | . | T | . | −1.07 | 0.04 | . | . | . | 0.10 | 0.30 |
| Gly | 379 | A | . | . | . | . | T | . | −1.38 | 0.09 | . | . | . | 0.10 | 0.33 |
| Val | 380 | A | A | . | . | . | . | . | −1.11 | −0.13 | . | . | . | 0.30 | 0.19 |
| Leu | 381 | A | A | . | . | . | . | . | −1.11 | 0.37 | . | . | . | −0.30 | 0.11 |
| Leu | 382 | . | A | B | . | . | . | . | −1.46 | 1.01 | . | . | . | −0.60 | 0.09 |
| Gly | 383 | . | A | B | . | . | . | . | −2.04 | 1.01 | . | . | . | −0.60 | 0.11 |
| Ala | 384 | . | A | B | . | . | . | . | −1.94 | 0.87 | . | . | . | −0.60 | 0.14 |
| Val | 385 | . | A | B | . | . | . | . | −1.09 | 0.94 | . | . | . | −0.60 | 0.27 |
| Gly | 386 | . | . | B | . | . | . | . | −0.57 | 0.26 | . | . | . | −0.10 | 0.45 |
| Ala | 387 | . | . | B | . | . | . | . | 0.24 | 0.74 | . | . | . | −0.40 | 0.47 |
| Tyr | 388 | . | . | B | . | . | . | . | 0.24 | 0.64 | . | . | . | −0.25 | 1.01 |
| Asp | 389 | . | . | . | . | T | . | . | 0.24 | 0.43 | . | . | . | 0.15 | 1.01 |
| Trp | 390 | A | . | . | . | . | . | . | 0.24 | 0.50 | . | . | . | −0.25 | 1.01 |
| Asn | 391 | A | . | . | . | . | . | . | −0.22 | 0.64 | * | . | . | −0.40 | 0.48 |
| Gly | 392 | A | A | . | . | . | . | . | 0.41 | 0.57 | * | . | . | −0.60 | 0.24 |
| Ala | 393 | A | A | . | . | . | . | . | 0.66 | 0.57 | . | . | . | −0.60 | 0.45 |
| Val | 394 | A | A | . | . | . | . | . | 0.34 | −0.34 | . | . | . | 0.30 | 0.49 |
| Leu | 395 | A | A | . | . | . | . | . | 0.33 | −0.26 | . | . | F | 0.45 | 0.71 |
| Lys | 396 | A | A | . | . | . | . | . | −0.26 | −0.30 | . | . | F | 0.45 | 0.94 |
| Glu | 397 | A | A | . | . | . | . | . | −0.26 | −0.30 | . | . | F | 0.60 | 1.28 |
| Thr | 398 | A | A | . | . | . | . | . | 0.38 | −0.51 | . | . | F | 0.90 | 1.54 |
| Ser | 399 | A | . | . | . | . | T | . | 0.38 | −1.20 | . | . | F | 1.30 | 1.54 |
| Ala | 400 | A | . | . | . | . | T | . | 0.30 | −0.56 | . | . | F | 1.15 | 0.66 |
| Gly | 401 | A | . | . | . | . | T | . | 0.04 | 0.13 | . | . | F | 0.25 | 0.32 |
| Lys | 402 | . | . | B | . | . | T | . | −0.77 | 0.07 | . | . | F | 0.25 | 0.37 |
| Val | 403 | . | . | B | . | . | . | . | −0.34 | 0.37 | . | . | . | −0.10 | 0.30 |
| Ile | 404 | . | . | B | . | . | . | . | −0.04 | −0.13 | . | . | . | 0.50 | 0.60 |
| Pro | 405 | . | . | B | . | . | . | . | 0.24 | −0.56 | . | . | . | 0.80 | 0.52 |
| Leu | 406 | . | . | B | . | . | . | . | 0.34 | −0.17 | . | . | . | 0.50 | 0.93 |
| Arg | 407 | A | . | . | . | . | . | . | −0.51 | −0.06 | . | . | F | 0.80 | 2.08 |
| Glu | 408 | A | . | . | . | . | . | . | 0.39 | −0.06 | . | . | F | 0.80 | 1.11 |
| Ser | 409 | A | . | . | . | . | . | . | 1.28 | −0.49 | . | * | F | 0.80 | 2.69 |
| Tyr | 410 | A | A | . | . | . | . | . | 0.79 | −1.17 | . | . | F | 0.90 | 2.38 |
| Leu | 411 | A | A | . | . | . | . | . | 1.39 | −0.39 | . | . | F | 0.60 | 1.19 |
| Lys | 412 | A | A | . | . | . | . | . | 1.28 | 0.04 | . | . | F | 0.00 | 1.37 |
| Glu | 413 | A | A | . | . | . | . | . | 1.28 | −0.34 | * | . | F | 0.60 | 1.52 |
| Phe | 414 | A | A | . | . | . | . | . | 0.77 | −1.10 | * | . | F | 0.90 | 3.19 |
| Pro | 415 | A | A | . | . | . | . | . | 1.06 | −1.10 | * | . | F | 0.90 | 1.31 |
| Glu | 416 | A | A | . | . | . | . | . | 1.87 | −1.10 | * | . | F | 0.90 | 1.52 |
| Glu | 417 | A | A | . | . | . | . | . | 1.79 | −0.70 | * | * | F | 0.90 | 2.82 |
| Leu | 418 | A | A | . | . | . | . | . | 1.44 | −0.99 | * | * | F | 0.90 | 2.48 |
| Lys | 419 | A | A | . | . | . | . | . | 1.56 | −0.99 | * | * | F | 0.90 | 1.42 |
| Asn | 420 | A | . | . | . | . | T | . | 1.52 | −0.49 | * | . | . | 0.70 | 0.83 |
| His | 421 | A | . | . | . | . | T | . | 0.71 | 0.27 | * | . | . | 0.25 | 1.57 |
| Gly | 422 | A | . | . | . | . | T | . | 0.37 | 0.27 | . | . | . | 0.10 | 0.65 |
| Ala | 423 | . | . | B | . | . | T | . | 0.93 | 0.70 | . | . | . | −0.20 | 0.40 |
| Tyr | 424 | . | . | B | B | . | . | . | 0.58 | 1.06 | . | . | . | −0.60 | 0.46 |
| Leu | 425 | . | . | B | B | . | . | . | −0.28 | 1.04 | . | . | . | −0.60 | 0.67 |
| Gly | 426 | . | . | B | B | . | . | . | −0.56 | 1.26 | . | . | . | −0.60 | 0.49 |
| Tyr | 427 | . | . | B | B | . | . | . | −0.51 | 1.24 | . | . | . | −0.60 | 0.45 |
| Thr | 428 | . | . | B | B | . | . | . | −0.78 | 0.87 | . | . | . | −0.60 | 0.74 |
| Val | 429 | . | . | B | B | . | . | . | −1.39 | 0.83 | * | . | . | −0.60 | 0.55 |
| Thr | 430 | . | . | B | B | . | . | . | −0.88 | 1.04 | * | . | . | −0.60 | 0.26 |
| Ser | 431 | . | . | B | B | . | . | . | −0.83 | 0.67 | . | . | . | −0.60 | 0.24 |
| Val | 432 | . | . | B | B | . | . | . | −0.48 | 0.57 | . | . | . | −0.60 | 0.44 |
| Val | 433 | . | . | B | B | . | . | . | −0.17 | −0.07 | . | . | F | 0.79 | 0.60 |
| Ser | 434 | . | . | B | . | . | T | . | 0.34 | −0.16 | . | . | F | 1.53 | 0.77 |
| Ser | 435 | . | . | B | . | . | T | . | 0.77 | −0.11 | . | . | F | 2.02 | 1.03 |
| Arg | 436 | . | . | B | . | . | T | . | 0.21 | −0.76 | . | . | F | 2.66 | 2.71 |
| Gln | 437 | . | . | . | . | T | T | . | 0.82 | −0.76 | . | * | F | 3.40 | 1.50 |
| Gly | 438 | . | . | B | B | . | . | . | 0.82 | −0.39 | * | * | F | 1.96 | 1.75 |
| Arg | 439 | . | . | B | B | . | . | . | 0.53 | −0.13 | * | * | F | 1.47 | 0.66 |
| Val | 440 | . | . | B | B | . | . | . | 0.49 | 0.37 | * | * | . | 0.38 | 0.39 |
| Tyr | 441 | . | . | B | B | . | . | . | −0.21 | 0.40 | * | * | . | −0.26 | 0.39 |
| Val | 442 | . | . | B | B | . | . | . | −0.42 | 0.47 | * | * | . | −0.60 | 0.20 |
| Ala | 443 | . | . | B | B | . | . | . | 0.03 | 0.90 | * | * | . | −0.60 | 0.42 |
| Gly | 444 | . | . | B | B | . | . | . | −0.78 | 0.26 | * | * | . | −0.30 | 0.52 |
| Ala | 445 | . | . | B | . | . | . | . | 0.08 | 0.29 | . | * | . | −0.10 | 0.61 |
| Pro | 446 | . | . | . | . | . | . | C | 0.29 | 0.04 | * | * | F | 0.25 | 0.97 |
| Arg | 447 | . | . | B | . | . | . | . | 0.83 | 0.04 | * | * | F | 0.20 | 1.33 |
| Phe | 448 | . | . | B | . | . | . | . | 1.08 | 0.10 | * | * | . | 0.18 | 1.90 |
| Asn | 449 | . | . | . | . | T | . | . | 1.47 | 0.03 | * | * | . | 0.71 | 1.22 |
| His | 450 | . | . | . | . | T | T | . | 1.20 | −0.40 | * | * | F | 1.79 | 1.24 |

TABLE 13-continued

| Res | Position | I | II | III | IV | V | VI | VII | VIII | IX | X | XI | XII | XIII | XIV |
|---|---|---|---|---|---|---|---|---|---|---|---|---|---|---|---|
| Thr | 451 | . | . | . | . | . | T | C | 0.52 | 0.24 | * | * | F | 1.12 | 1.06 |
| Gly | 452 | . | . | . | . | T | T | . | −0.40 | 0.14 | * | * | F | 1.30 | 0.46 |
| Lys | 453 | . | . | B | . | . | T | . | −0.40 | 0.43 | * | * | F | 0.47 | 0.28 |
| Val | 454 | . | . | B | B | . | . | . | −0.71 | 0.71 | . | . | . | −0.21 | 0.17 |
| Ile | 455 | . | . | B | B | . | . | . | −1.28 | 0.71 | . | . | . | −0.34 | 0.25 |
| Leu | 456 | . | . | B | B | . | . | . | −1.00 | 0.90 | . | . | . | −0.47 | 0.12 |
| Phe | 457 | . | . | B | B | . | . | . | −0.66 | 1.40 | . | . | . | −0.60 | 0.22 |
| Thr | 458 | . | . | B | B | . | . | . | −0.70 | 1.16 | . | . | . | −0.60 | 0.51 |
| Met | 459 | . | . | B | B | . | . | . | 0.27 | 0.87 | . | . | . | −0.32 | 1.00 |
| His | 460 | . | . | . | . | . | T | C | 0.86 | 0.19 | . | . | . | 1.01 | 2.26 |
| Asn | 461 | . | . | . | . | . | T | C | 0.86 | −0.21 | . | . | F | 2.04 | 2.10 |
| Asn | 462 | . | . | . | . | . | T | C | 1.24 | −0.01 | . | . | F | 2.32 | 1.75 |
| Arg | 463 | . | . | . | . | T | T | . | 0.67 | −0.14 | . | . | F | 2.80 | 1.85 |
| Ser | 464 | . | . | . | . | . | . | C | 1.23 | 0.04 | . | . | F | 1.37 | 0.81 |
| Leu | 465 | A | A | . | . | . | . | . | 1.27 | 0.14 | . | . | . | 0.54 | 0.68 |
| Thr | 466 | . | A | B | . | . | . | . | 0.68 | 0.14 | . | . | . | 0.26 | 0.60 |
| Ile | 467 | . | A | B | . | . | . | . | 0.08 | 0.64 | . | * | . | −0.32 | 0.46 |
| His | 468 | . | A | B | . | . | . | . | 0.08 | 0.87 | . | * | . | −0.60 | 0.55 |
| Gln | 469 | . | A | B | . | . | . | . | 0.03 | 0.19 | * | * | . | −0.30 | 0.74 |
| Ala | 470 | . | A | B | . | . | . | . | 0.84 | 0.13 | * | * | . | 0.02 | 1.05 |
| Met | 471 | . | . | B | . | . | T | . | 1.16 | −0.16 | * | . | . | 1.19 | 1.33 |
| Arg | 472 | . | . | B | . | . | T | . | 1.16 | −0.26 | * | * | F | 1.51 | 1.33 |
| Gly | 473 | . | . | B | . | . | T | . | 0.84 | 0.03 | * | . | F | 0.93 | 0.92 |
| Gln | 474 | . | . | B | . | . | T | . | 0.54 | −0.04 | . | . | F | 1.70 | 0.92 |
| Gln | 475 | . | . | B | . | . | . | . | 0.89 | −0.27 | * | . | F | 1.33 | 0.63 |
| Ile | 476 | . | . | B | . | . | . | . | 0.79 | 0.49 | * | . | F | 0.41 | 1.00 |
| Gly | 477 | . | . | B | . | . | T | . | 0.33 | 0.84 | * | . | F | 0.29 | 0.50 |
| Ser | 478 | . | . | B | . | . | T | . | 0.38 | 0.87 | * | . | F | 0.12 | 0.29 |
| Tyr | 479 | . | . | . | . | . | T | C | 0.38 | 0.86 | * | . | . | 0.00 | 0.55 |
| Phe | 480 | . | . | B | . | . | T | . | −0.51 | 0.17 | * | . | F | 0.25 | 0.96 |
| Gly | 481 | . | . | . | B | . | . | C | 0.07 | 0.43 | * | . | F | −0.25 | 0.50 |
| Ser | 482 | . | . | . | B | . | . | C | 0.11 | 0.53 | * | . | F | −0.25 | 0.46 |
| Glu | 483 | . | . | B | B | . | . | . | −0.44 | 0.16 | * | . | F | −0.15 | 0.71 |
| Ile | 484 | . | . | B | B | . | . | . | −0.20 | 0.01 | . | . | F | −0.15 | 0.54 |
| Thr | 485 | . | . | B | B | . | . | . | −0.39 | −0.41 | . | * | F | 0.45 | 0.67 |
| Ser | 486 | . | . | B | B | . | . | . | −0.04 | −0.11 | . | * | F | 0.45 | 0.27 |
| Val | 487 | . | . | B | B | . | . | . | −0.09 | −0.11 | . | * | F | 0.76 | 0.64 |
| Asp | 488 | . | . | B | B | . | . | . | −0.09 | −0.37 | . | * | F | 1.07 | 0.44 |
| Ile | 489 | . | . | B | . | . | . | . | 0.46 | −0.86 | . | * | F | 1.88 | 0.55 |
| Asp | 490 | . | . | . | . | T | T | . | −0.09 | −0.81 | . | * | F | 2.79 | 0.73 |
| Gly | 491 | . | . | . | . | T | T | . | −0.10 | −0.81 | . | * | F | 3.10 | 0.33 |
| Asp | 492 | . | . | . | . | T | T | . | 0.76 | −0.33 | * | * | F | 2.49 | 0.67 |
| Gly | 493 | . | . | B | . | . | T | . | −0.10 | −1.01 | * | * | F | 2.08 | 0.67 |
| Val | 494 | . | . | B | B | . | . | . | −0.02 | −0.37 | . | * | F | 1.07 | 0.50 |
| Thr | 495 | . | . | B | B | . | . | . | −0.83 | −0.11 | . | . | F | 0.76 | 0.25 |
| Asp | 496 | . | . | B | B | . | . | . | −1.34 | 0.57 | * | . | F | −0.45 | 0.21 |
| Val | 497 | . | . | B | B | . | . | . | −1.69 | 0.79 | * | . | . | −0.60 | 0.21 |
| Leu | 498 | . | . | B | B | . | . | . | −1.93 | 0.57 | . | . | . | −0.60 | 0.14 |
| Leu | 499 | . | . | B | B | . | . | . | −1.29 | 0.59 | . | . | . | −0.60 | 0.09 |
| Val | 500 | . | . | B | B | . | . | . | −1.58 | 1.01 | . | . | . | −0.60 | 0.18 |
| Gly | 501 | . | . | B | B | . | . | . | −1.82 | 0.99 | . | . | . | −0.60 | 0.21 |
| Ala | 502 | . | . | B | . | . | . | . | −1.67 | 1.06 | . | . | . | −0.40 | 0.41 |
| Pro | 503 | . | . | B | . | . | . | . | −0.86 | 1.16 | . | . | . | −0.40 | 0.48 |
| Met | 504 | . | . | B | . | . | . | . | −0.04 | 0.91 | . | . | . | −0.40 | 0.77 |
| Tyr | 505 | . | . | B | . | . | . | . | 0.47 | 0.49 | . | . | . | −0.25 | 1.33 |
| Phe | 506 | . | . | B | . | . | . | . | 0.92 | 0.41 | * | . | . | −0.40 | 0.85 |
| Asn | 507 | A | . | . | . | . | T | . | 1.51 | −0.01 | . | * | . | 0.85 | 1.68 |
| Glu | 508 | A | . | . | . | . | T | . | 1.83 | −0.63 | . | * | F | 1.30 | 1.86 |
| Gly | 509 | A | . | . | . | . | T | . | 2.09 | −1.39 | . | * | F | 1.30 | 4.20 |
| Arg | 510 | A | . | . | . | . | T | . | 2.38 | −1.74 | . | * | F | 1.30 | 2.58 |
| Glu | 511 | A | . | . | . | . | . | . | 2.22 | −2.14 | . | * | F | 1.10 | 2.98 |
| Arg | 512 | . | . | . | B | T | . | . | 1.98 | −1.50 | . | * | F | 1.30 | 2.24 |
| Gly | 513 | . | . | . | B | T | . | . | 1.12 | −1.17 | . | * | F | 1.30 | 1.79 |
| Lys | 514 | . | . | B | B | . | . | . | 1.22 | −0.53 | . | * | F | 0.75 | 0.77 |
| Val | 515 | . | . | B | B | . | . | . | 1.11 | 0.23 | . | * | . | −0.30 | 0.61 |
| Tyr | 516 | . | . | B | B | . | . | . | 0.30 | 0.23 | . | * | . | −0.15 | 1.07 |
| Val | 517 | . | . | B | B | . | . | . | 0.30 | 0.49 | . | * | . | −0.60 | 0.44 |
| Tyr | 518 | . | . | B | . | . | . | . | 0.64 | 0.49 | * | * | . | 0.01 | 1.17 |
| Glu | 519 | . | . | B | . | . | . | . | 0.60 | 0.24 | * | . | . | 0.57 | 1.29 |
| Leu | 520 | . | . | B | . | . | . | . | 1.57 | −0.11 | . | . | . | 1.43 | 2.80 |
| Arg | 521 | A | . | . | . | . | T | . | 1.11 | −0.76 | . | . | F | 2.34 | 3.50 |
| Gln | 522 | . | . | B | . | . | T | . | 1.11 | −0.73 | . | . | F | 2.60 | 1.75 |
| Asn | 523 | . | . | B | . | . | T | . | 1.11 | −0.09 | * | . | F | 2.04 | 1.57 |
| Arg | 524 | . | . | B | . | . | T | . | 1.11 | −0.01 | * | * | F | 1.78 | 1.26 |
| Phe | 525 | . | . | B | . | . | . | . | 1.58 | 0.39 | * | . | . | 0.57 | 1.17 |
| Val | 526 | . | . | B | . | . | T | . | 1.16 | 0.41 | * | * | . | 0.06 | 0.72 |
| Tyr | 527 | . | . | B | . | . | T | . | 0.34 | 0.50 | . | * | . | −0.20 | 0.53 |
| Asn | 528 | . | . | B | . | . | T | . | 0.39 | 1.19 | . | * | F | 0.29 | 0.50 |

TABLE 13-continued

| Res | Position | I | II | III | IV | V | VI | VII | VIII | IX | X | XI | XII | XIII | XIV |
|---|---|---|---|---|---|---|---|---|---|---|---|---|---|---|---|
| Gly | 529 | . | . | . | . | T | T | . | 0.28 | 0.40 | * | * | F | 1.18 | 1.36 |
| Thr | 530 | . | . | . | . | . | . | C | 0.68 | −0.24 | . | . | F | 2.02 | 1.45 |
| Leu | 531 | . | . | . | . | . | T | C | 1.50 | −0.61 | . | . | F | 2.86 | 1.21 |
| Lys | 532 | . | . | . | . | T | T | . | 1.44 | −0.51 | . | * | F | 3.40 | 1.66 |
| Asp | 533 | . | . | B | . | . | T | . | 1.20 | −0.56 | . | * | F | 2.66 | 1.54 |
| Ser | 534 | . | . | B | . | . | T | . | 1.54 | −0.29 | . | . | F | 2.02 | 2.93 |
| His | 535 | . | . | B | . | . | T | . | 1.86 | −0.57 | . | . | . | 1.83 | 2.54 |
| Ser | 536 | . | . | B | . | . | T | . | 2.08 | −0.17 | . | * | . | 1.19 | 2.44 |
| Tyr | 537 | . | . | B | . | . | T | . | 2.14 | 0.33 | . | * | . | 0.25 | 1.84 |
| Gln | 538 | . | . | B | . | . | T | . | 1.44 | −0.06 | . | * | . | 0.85 | 2.65 |
| Asn | 539 | . | . | B | . | . | . | . | 1.40 | 0.23 | . | * | . | 0.05 | 1.71 |
| Ala | 540 | . | . | B | . | . | . | . | 1.13 | 0.27 | . | * | . | 0.05 | 1.08 |
| Arg | 541 | . | . | B | . | . | . | . | 1.13 | −0.10 | * | * | . | 0.50 | 0.84 |
| Phe | 542 | . | . | B | . | . | . | . | 0.49 | −0.11 | * | * | F | 0.65 | 0.70 |
| Gly | 543 | . | . | . | . | T | T | . | −0.10 | 0.17 | * | * | F | 0.65 | 0.48 |
| Ser | 544 | . | . | . | . | . | T | C | −0.40 | 0.17 | * | * | F | 0.45 | 0.25 |
| Ser | 545 | . | . | B | . | . | T | . | −0.67 | 0.56 | . | * | F | −0.05 | 0.39 |
| Ile | 546 | . | . | B | . | . | T | . | −0.67 | 0.41 | * | * | . | −0.20 | 0.29 |
| Ala | 547 | . | . | B | B | . | . | . | 0.03 | −0.01 | * | . | . | 0.30 | 0.42 |
| Ser | 548 | . | . | B | B | . | . | . | −0.43 | −0.40 | . | . | . | 0.30 | 0.53 |
| Val | 549 | . | . | B | B | . | . | . | −0.13 | −0.10 | * | . | . | 0.64 | 0.62 |
| Arg | 550 | . | . | B | B | . | . | . | 0.17 | −0.39 | * | . | F | 1.13 | 0.99 |
| Asp | 551 | . | . | B | . | . | . | . | 1.06 | −0.49 | * | . | F | 1.82 | 1.28 |
| Leu | 552 | . | . | B | . | . | . | . | 1.34 | −0.87 | * | . | F | 2.46 | 2.88 |
| Asn | 553 | . | . | . | . | T | T | . | 1.40 | −1.13 | * | . | F | 3.40 | 1.97 |
| Gln | 554 | . | . | . | . | T | T | . | 2.26 | −0.37 | * | . | F | 2.76 | 1.85 |
| Asp | 555 | . | . | . | . | T | T | . | 2.14 | 0.03 | * | . | F | 1.82 | 3.60 |
| Ser | 556 | . | . | . | . | T | T | . | 1.29 | −0.66 | * | . | F | 2.38 | 3.74 |
| Tyr | 557 | . | . | . | B | T | . | . | 1.24 | −0.41 | . | . | F | 1.34 | 1.60 |
| Asn | 558 | . | . | B | B | . | . | . | 0.39 | −0.17 | . | . | F | 0.45 | 0.71 |
| Asp | 559 | . | . | B | B | . | . | . | 0.04 | 0.47 | . | . | . | −0.60 | 0.39 |
| Val | 560 | . | . | B | B | . | . | . | −0.54 | 0.51 | * | . | . | −0.60 | 0.25 |
| Val | 561 | . | . | B | B | . | . | . | −0.46 | 0.26 | . | . | . | −0.30 | 0.16 |
| Val | 562 | . | . | B | B | . | . | . | −1.02 | 0.29 | . | . | . | −0.30 | 0.14 |
| Gly | 563 | . | . | B | B | . | . | . | −1.02 | 0.97 | . | . | . | −0.60 | 0.16 |
| Ala | 564 | . | A | B | . | . | . | . | −1.02 | 0.33 | . | . | . | −0.30 | 0.38 |
| Pro | 565 | A | A | . | . | . | . | . | −0.17 | −0.31 | . | . | . | 0.30 | 0.85 |
| Leu | 566 | A | A | . | . | . | . | . | 0.66 | −0.56 | . | . | . | 0.75 | 1.37 |
| Glu | 567 | A | A | . | . | . | . | . | 0.92 | −0.49 | . | . | F | 0.60 | 1.85 |
| Asp | 568 | A | A | . | . | . | . | . | 0.92 | −0.49 | . | . | . | 0.45 | 1.21 |
| Asn | 569 | A | A | . | . | . | . | . | 0.92 | −0.49 | . | . | . | 0.45 | 1.45 |
| His | 570 | A | A | . | . | . | . | . | 0.24 | −0.67 | . | . | . | 0.60 | 0.85 |
| Ala | 571 | A | . | . | B | . | . | . | 0.81 | 0.01 | . | . | . | −0.30 | 0.36 |
| Gly | 572 | A | . | . | B | . | . | . | −0.08 | 0.77 | . | . | . | −0.60 | 0.35 |
| Ala | 573 | A | . | . | B | . | . | . | −0.78 | 1.06 | . | . | . | −0.60 | 0.18 |
| Ile | 574 | . | . | B | B | . | . | . | −0.81 | 1.34 | . | . | . | −0.60 | 0.15 |
| Tyr | 575 | . | . | B | B | . | . | . | −1.12 | 1.34 | . | . | . | −0.60 | 0.21 |
| Ile | 576 | . | . | B | B | . | . | . | −1.23 | 1.34 | * | * | . | −0.60 | 0.21 |
| Phe | 577 | . | . | B | B | . | . | . | −0.78 | 1.63 | * | * | . | −0.60 | 0.25 |
| His | 578 | . | . | B | B | . | . | . | −0.53 | 0.94 | * | * | . | −0.60 | 0.32 |
| Gly | 579 | . | . | . | B | T | . | . | 0.06 | 0.61 | * | * | . | −0.20 | 0.45 |
| Phe | 580 | . | . | . | . | T | T | . | −0.59 | 0.31 | * | * | . | 0.50 | 0.69 |
| Arg | 581 | . | . | . | . | T | T | . | −0.51 | 0.21 | * | * | F | 0.65 | 0.36 |
| Gly | 582 | . | . | . | . | T | T | . | 0.23 | 0.40 | . | . | F | 0.35 | 0.30 |
| Ser | 583 | . | . | . | . | T | T | . | −0.04 | −0.03 | . | . | F | 1.25 | 0.69 |
| Ile | 584 | . | . | . | . | . | . | C | 0.09 | −0.33 | * | * | F | 1.15 | 0.51 |
| Leu | 585 | . | . | . | . | . | . | C | 0.83 | 0.10 | * | * | F | 0.85 | 0.79 |
| Lys | 586 | . | . | . | . | . | . | C | 0.72 | −0.33 | . | * | F | 1.90 | 1.18 |
| Thr | 587 | . | . | . | . | . | T | C | 1.18 | −0.31 | * | * | F | 2.40 | 2.92 |
| Pro | 588 | . | . | . | . | . | T | C | 0.59 | −1.00 | * | * | F | 3.00 | 6.94 |
| Lys | 589 | . | . | B | . | . | T | . | 1.17 | −1.00 | * | * | F | 2.50 | 2.43 |
| Gln | 590 | . | . | B | . | . | T | . | 1.39 | −0.51 | * | * | F | 2.20 | 2.43 |
| Arg | 591 | . | . | B | B | . | . | . | 1.04 | −0.50 | . | * | F | 1.20 | 1.59 |
| Ile | 592 | . | . | B | B | . | . | . | 1.36 | −0.54 | . | * | F | 1.20 | 1.06 |
| Thr | 593 | . | A | B | B | . | . | . | 0.76 | −0.54 | . | * | F | 0.90 | 1.06 |
| Ala | 594 | . | A | B | B | . | . | . | 0.12 | −0.26 | . | * | F | 0.45 | 0.45 |
| Ser | 595 | . | A | B | . | . | . | . | −0.19 | 0.24 | . | . | F | −0.15 | 0.65 |
| Glu | 596 | . | A | B | . | . | . | . | −0.64 | 0.04 | . | * | F | −0.15 | 0.65 |
| Leu | 597 | A | A | . | B | . | . | . | −0.57 | −0.01 | . | . | F | 0.45 | 0.63 |
| Ala | 598 | A | A | . | B | . | . | . | −0.26 | 0.17 | * | . | . | −0.30 | 0.39 |
| Thr | 599 | A | A | . | B | . | . | . | 0.09 | 0.19 | * | . | . | −0.30 | 0.39 |
| Gly | 600 | A | A | . | B | . | . | . | −0.31 | 0.94 | * | . | . | −0.60 | 0.74 |
| Leu | 601 | . | . | B | B | . | . | . | −0.66 | 1.04 | * | . | . | −0.60 | 0.63 |
| Gln | 602 | . | . | B | B | . | . | . | −0.51 | 0.97 | * | . | . | −0.60 | 0.44 |
| Tyr | 603 | . | . | . | . | T | T | . | −0.22 | 1.06 | * | . | . | 0.20 | 0.24 |
| Phe | 604 | . | . | B | . | . | T | . | −0.80 | 1.01 | * | . | . | −0.20 | 0.38 |
| Gly | 605 | . | . | B | . | . | T | . | −0.49 | 1.01 | * | . | . | −0.20 | 0.15 |
| Cys | 606 | . | . | B | . | . | T | . | −0.02 | 1.11 | . | * | . | −0.20 | 0.13 |

TABLE 13-continued

| Res | Position | I | II | III | IV | V | VI | VII | VIII | IX | X | XI | XII | XIII | XIV |
|---|---|---|---|---|---|---|---|---|---|---|---|---|---|---|---|
| Ser | 607 | . | . | B | B | . | . | . | −0.02 | 0.79 | . | * | . | −0.60 | 0.15 |
| Ile | 608 | . | . | B | B | . | . | . | −0.59 | 0.40 | . | * | . | −0.60 | 0.27 |
| His | 609 | . | . | B | B | . | . | . | 0.11 | 0.66 | . | * | . | −0.60 | 0.41 |
| Gly | 610 | . | . | B | B | . | . | . | −0.36 | 0.09 | . | * | . | −0.30 | 0.52 |
| Gln | 611 | . | . | B | . | . | . | . | 0.31 | 0.39 | . | * | . | −0.10 | 0.61 |
| Leu | 612 | . | . | B | . | . | . | . | 0.61 | 0.10 | . | * | . | −0.10 | 0.72 |
| Asp | 613 | . | . | B | . | . | . | . | 1.50 | −0.40 | . | * | . | 0.65 | 1.26 |
| Leu | 614 | . | . | B | . | . | . | . | 1.19 | −0.83 | . | * | . | 0.95 | 1.21 |
| Asn | 615 | A | . | . | . | . | T | . | 0.72 | −0.80 | . | * | F | 1.30 | 1.45 |
| Glu | 616 | A | . | . | . | . | T | . | −0.17 | −0.80 | . | * | F | 1.15 | 0.72 |
| Asp | 617 | A | . | . | . | . | T | . | 0.64 | −0.11 | . | * | F | 0.85 | 0.61 |
| Gly | 618 | A | . | . | . | . | T | . | −0.17 | −0.80 | . | * | F | 1.15 | 0.63 |
| Leu | 619 | A | . | . | B | . | . | . | 0.06 | −0.51 | . | * | . | 0.60 | 0.30 |
| Ile | 620 | A | . | . | B | . | . | . | −0.80 | −0.01 | . | * | . | 0.30 | 0.18 |
| Asp | 621 | . | . | B | B | . | . | . | −1.14 | 0.63 | . | * | . | −0.60 | 0.14 |
| Leu | 622 | . | . | B | B | . | . | . | −1.73 | 0.63 | * | * | . | −0.60 | 0.16 |
| Ala | 623 | . | . | B | B | . | . | . | −2.20 | 0.44 | . | . | . | −0.60 | 0.24 |
| Val | 624 | A | . | . | B | . | . | . | −1.73 | 0.44 | * | . | . | −0.60 | 0.12 |
| Gly | 625 | A | A | . | . | . | . | . | −0.84 | 0.87 | * | * | . | −0.60 | 0.14 |
| Ala | 626 | A | A | . | . | . | . | . | −1.43 | 0.59 | . | . | . | −0.60 | 0.22 |
| Leu | 627 | A | A | . | . | . | . | . | −1.48 | 0.59 | . | . | . | −0.60 | 0.30 |
| Gly | 628 | A | A | . | . | . | . | . | −1.78 | 0.59 | . | . | . | −0.60 | 0.23 |
| Asn | 629 | . | A | B | B | . | . | . | −1.73 | 0.84 | . | . | . | −0.60 | 0.16 |
| Ala | 630 | . | A | B | B | . | . | . | −1.68 | 1.03 | . | . | . | −0.60 | 0.16 |
| Val | 631 | . | A | B | B | . | . | . | −1.39 | 1.26 | * | . | . | −0.60 | 0.17 |
| Ile | 632 | . | A | B | B | . | . | . | −0.47 | 1.21 | * | . | . | −0.60 | 0.14 |
| Leu | 633 | . | A | B | B | . | . | . | −0.33 | 0.81 | * | . | . | −0.60 | 0.27 |
| Trp | 634 | . | A | B | B | . | . | . | −1.19 | 0.74 | * | . | . | −0.60 | 0.57 |
| Ser | 635 | . | A | B | B | . | . | . | −1.46 | 0.74 | * | . | . | −0.60 | 0.60 |
| Arg | 636 | . | . | B | B | . | . | . | −0.60 | 0.70 | * | * | F | −0.45 | 0.54 |
| Pro | 637 | . | . | B | B | . | . | . | −0.60 | 0.41 | * | * | . | −0.60 | 0.89 |
| Val | 638 | . | . | B | B | . | . | . | 0.21 | 0.19 | * | * | . | −0.30 | 0.46 |
| Val | 639 | . | . | B | B | . | . | . | −0.09 | 0.20 | * | * | . | −0.30 | 0.38 |
| Gln | 640 | . | . | B | B | . | . | . | −0.09 | 0.70 | * | * | . | −0.60 | 0.25 |
| Ile | 641 | . | . | B | B | . | . | . | −1.01 | 0.66 | * | * | . | −0.60 | 0.45 |
| Asn | 642 | . | . | B | . | . | T | . | −0.83 | 0.70 | . | * | . | −0.20 | 0.50 |
| Ala | 643 | . | . | B | . | . | T | . | −0.68 | 0.56 | . | * | . | −0.20 | 0.39 |
| Ser | 644 | . | . | B | . | . | T | . | 0.18 | 0.94 | . | * | . | −0.20 | 0.48 |
| Leu | 645 | A | . | . | . | . | T | . | −0.03 | 0.26 | . | * | . | 0.10 | 0.52 |
| His | 646 | A | . | . | . | . | . | . | 0.56 | 0.29 | . | * | . | 0.18 | 0.80 |
| Phe | 647 | A | . | . | . | . | . | . | 0.60 | 0.17 | . | * | . | 0.46 | 0.80 |
| Glu | 648 | A | . | . | . | . | T | . | 0.30 | −0.21 | . | * | F | 1.84 | 1.94 |
| Pro | 649 | A | . | . | . | . | T | . | 0.60 | −0.21 | . | * | F | 1.97 | 1.00 |
| Ser | 650 | . | . | . | . | T | T | . | 0.52 | −0.31 | . | * | F | 2.80 | 1.85 |
| Lys | 651 | A | . | . | . | . | T | . | −0.14 | −0.41 | . | . | F | 1.97 | 0.75 |
| Ile | 652 | A | . | . | B | . | . | . | 0.52 | 0.37 | * | * | F | 0.69 | 0.42 |
| Asn | 653 | A | . | . | B | . | . | . | 0.63 | 0.44 | * | * | . | −0.04 | 0.43 |
| Ile | 654 | A | . | . | B | . | . | . | 0.84 | 0.06 | * | * | . | −0.02 | 0.42 |
| Phe | 655 | . | . | B | B | . | . | . | 0.48 | 0.06 | * | * | . | 0.04 | 1.00 |
| His | 656 | . | . | B | . | . | T | . | 0.48 | −0.06 | * | * | . | 1.38 | 0.33 |
| Arg | 657 | . | . | B | . | . | T | . | 1.48 | −0.46 | * | * | . | 1.72 | 0.95 |
| Asp | 658 | . | . | . | . | T | T | . | 1.18 | −1.14 | * | . | F | 3.06 | 2.14 |
| Cys | 659 | . | . | . | . | T | T | . | 1.72 | −1.54 | * | . | F | 3.40 | 2.11 |
| Lys | 660 | . | . | . | . | T | . | . | 2.53 | −1.61 | * | . | F | 2.86 | 1.07 |
| Arg | 661 | . | . | . | . | T | T | . | 2.57 | −1.61 | * | . | F | 3.03 | 1.25 |
| Ser | 662 | . | . | . | . | T | T | . | 1.87 | −1.61 | * | . | F | 3.00 | 3.90 |
| Gly | 663 | . | . | . | . | T | T | . | 1.56 | −1.69 | * | . | F | 2.97 | 1.97 |
| Arg | 664 | . | . | . | . | T | T | . | 1.56 | −1.20 | * | . | F | 2.94 | 1.45 |
| Asp | 665 | . | . | . | . | T | T | . | 0.70 | −0.63 | * | . | F | 3.10 | 0.58 |
| Ala | 666 | . | . | B | . | . | T | . | 0.00 | −0.33 | * | . | F | 2.09 | 0.48 |
| Thr | 667 | . | . | B | . | . | T | . | −0.29 | −0.26 | . | . | . | 1.63 | 0.25 |
| Cys | 668 | . | . | B | . | . | T | . | −0.64 | 0.24 | * | . | . | 0.72 | 0.15 |
| Leu | 669 | A | A | . | . | . | . | . | −1.57 | 1.03 | * | . | . | −0.29 | 0.13 |
| Ala | 670 | A | A | . | . | . | . | . | −2.23 | 1.21 | . | . | . | −0.60 | 0.07 |
| Ala | 671 | A | A | . | . | . | . | . | −2.34 | 1.30 | . | . | . | −0.60 | 0.07 |
| Phe | 672 | A | A | . | . | . | . | . | −2.34 | 1.51 | . | . | . | −0.60 | 0.08 |
| Leu | 673 | A | A | . | . | . | . | . | −1.89 | 1.31 | . | . | . | −0.60 | 0.11 |
| Cys | 674 | . | A | B | . | . | . | . | −1.97 | 1.24 | . | . | . | −0.60 | 0.17 |
| Phe | 675 | . | . | B | B | . | . | . | −2.08 | 1.43 | . | . | . | −0.60 | 0.14 |
| Thr | 676 | . | . | B | B | . | . | . | −2.30 | 1.43 | . | . | . | −0.60 | 0.14 |
| Pro | 677 | . | . | B | B | . | . | . | −2.19 | 1.43 | . | . | . | −0.60 | 0.22 |
| Ile | 678 | . | A | . | B | T | . | . | −1.59 | 1.36 | . | . | . | −0.20 | 0.26 |
| Phe | 679 | . | A | B | B | . | . | . | −0.96 | 1.00 | . | . | . | −0.60 | 0.28 |
| Leu | 680 | . | A | B | B | . | . | . | −0.96 | 1.01 | . | . | . | −0.60 | 0.24 |
| Ala | 681 | . | A | . | B | . | . | C | −0.64 | 1.37 | . | . | . | −0.40 | 0.30 |
| Pro | 682 | . | A | . | B | . | . | C | −0.74 | 1.09 | . | . | . | −0.40 | 0.60 |
| His | 683 | . | A | . | B | T | . | . | −0.17 | 0.79 | . | . | . | −0.05 | 1.05 |
| Phe | 684 | . | A | . | B | T | . | . | 0.22 | 0.59 | . | . | . | −0.05 | 1.51 |

TABLE 13-continued

| Res | Position | I | II | III | IV | V | VI | VII | VIII | IX | X | XI | XII | XIII | XIV |
|---|---|---|---|---|---|---|---|---|---|---|---|---|---|---|---|
| Gln | 685 | . | A | B | B | . | . | . | 0.18 | 0.57 | . | . | F | −0.30 | 1.41 |
| Thr | 686 | . | A | B | B | . | . | . | 0.42 | 0.79 | . | . | F | −0.45 | 0.77 |
| Thr | 687 | . | . | B | B | . | . | . | −0.26 | 0.71 | * | * | F | −0.45 | 0.88 |
| Thr | 688 | . | . | B | B | . | . | . | −0.11 | 0.61 | * | * | F | −0.45 | 0.35 |
| Val | 689 | . | . | B | B | . | . | . | 0.34 | 0.21 | . | * | . | −0.30 | 0.48 |
| Gly | 690 | . | . | B | B | . | . | . | 0.34 | 0.49 | . | * | . | −0.60 | 0.52 |
| Ile | 691 | . | . | B | B | . | . | . | 0.07 | 0.40 | . | * | . | −0.60 | 0.58 |
| Arg | 692 | . | . | B | B | . | . | . | 0.07 | 0.41 | . | * | . | −0.60 | 0.79 |
| Tyr | 693 | . | . | B | B | . | . | . | −0.22 | 0.26 | . | * | . | −0.15 | 1.16 |
| Asn | 694 | . | A | B | B | . | . | . | 0.63 | 0.44 | . | * | . | −0.45 | 1.63 |
| Ala | 695 | . | A | B | B | . | . | . | 0.98 | −0.24 | * | * | . | 0.45 | 1.39 |
| Thr | 696 | . | A | B | B | . | . | . | 1.98 | −0.24 | . | * | . | 0.45 | 1.54 |
| Met | 697 | . | A | B | B | . | . | . | 1.98 | −1.00 | . | * | F | 0.90 | 1.87 |
| Asp | 698 | . | A | B | . | . | . | . | 1.98 | −1.40 | . | . | F | 0.90 | 3.63 |
| Glu | 699 | . | A | B | . | . | . | . | 1.67 | −1.14 | . | . | F | 1.20 | 3.94 |
| Arg | 700 | . | A | B | . | . | . | . | 2.04 | −1.14 | * | * | F | 1.50 | 5.75 |
| Arg | 701 | . | A | . | . | T | . | . | 2.47 | −1.33 | * | * | F | 2.20 | 5.33 |
| Tyr | 702 | . | A | . | . | T | . | . | 2.48 | −1.33 | * | * | F | 2.50 | 6.02 |
| Thr | 703 | . | . | . | . | . | T | C | 2.44 | −0.83 | . | * | F | 3.00 | 3.11 |
| Pro | 704 | . | . | . | . | . | T | C | 1.63 | −0.33 | . | * | F | 2.40 | 2.16 |
| Arg | 705 | . | . | B | . | . | T | . | 1.52 | 0.36 | . | * | . | 1.15 | 1.14 |
| Ala | 706 | . | . | B | . | . | T | . | 1.41 | −0.40 | * | * | . | 1.45 | 1.31 |
| His | 707 | . | . | B | . | . | . | . | 1.31 | −0.89 | . | * | . | 1.59 | 1.47 |
| Leu | 708 | . | . | B | . | . | . | . | 1.28 | −0.89 | * | * | F | 1.63 | 0.74 |
| Asp | 709 | . | . | B | . | . | T | . | 1.49 | −0.46 | . | * | F | 1.87 | 0.73 |
| Glu | 710 | . | . | . | . | T | T | . | 1.49 | −0.96 | * | * | F | 2.91 | 0.89 |
| Gly | 711 | . | . | . | . | T | T | . | 1.38 | −1.46 | * | * | F | 3.40 | 2.12 |
| Gly | 712 | . | . | . | . | T | T | . | 1.10 | −1.36 | * | . | F | 3.06 | 1.10 |
| Asp | 713 | . | . | . | . | T | . | . | 1.91 | −0.87 | * | * | F | 2.37 | 0.92 |
| Arg | 714 | A | . | . | . | . | . | . | 2.02 | −0.47 | * | * | F | 1.48 | 1.49 |
| Phe | 715 | A | . | . | . | . | . | . | 1.43 | −0.90 | * | * | F | 1.44 | 2.95 |
| Thr | 716 | . | . | B | . | . | . | . | 0.92 | −0.83 | * | * | F | 1.10 | 1.79 |
| Asn | 717 | . | A | B | . | . | . | . | 0.46 | −0.19 | * | * | F | 0.45 | 0.68 |
| Arg | 718 | . | A | B | . | . | . | . | −0.36 | 0.50 | * | * | F | −0.45 | 0.64 |
| Ala | 719 | . | A | B | . | . | . | . | −0.77 | 0.40 | * | * | . | −0.60 | 0.37 |
| Val | 720 | . | A | B | . | . | . | . | −0.37 | 0.30 | . | . | . | −0.06 | 0.31 |
| Leu | 721 | . | A | B | . | . | . | . | −0.40 | 0.29 | . | . | . | 0.18 | 0.21 |
| Leu | 722 | . | A | B | . | . | . | . | −0.40 | 0.71 | . | . | F | 0.27 | 0.21 |
| Ser | 723 | . | . | . | . | . | T | C | −0.51 | 0.61 | . | . | F | 1.11 | 0.48 |
| Ser | 724 | . | . | . | . | . | T | C | −0.73 | −0.03 | . | . | F | 2.40 | 1.01 |
| Gly | 725 | . | . | . | . | . | T | C | −0.54 | −0.03 | * | . | F | 2.16 | 1.01 |
| Gln | 726 | A | . | . | . | . | T | . | 0.27 | −0.14 | * | . | F | 1.57 | 0.40 |
| Glu | 727 | A | A | . | . | . | . | . | 1.19 | −0.53 | * | * | F | 1.23 | 0.52 |
| Leu | 728 | A | A | . | . | . | . | . | 0.60 | −0.91 | * | * | F | 1.14 | 1.03 |
| Cys | 729 | A | A | . | . | . | . | . | 0.90 | −0.66 | * | * | . | 0.60 | 0.42 |
| Glu | 730 | A | A | . | . | . | . | . | 0.54 | −0.66 | * | * | . | 0.60 | 0.39 |
| Arg | 731 | A | A | . | . | . | . | . | 0.51 | 0.13 | * | * | . | −0.30 | 0.41 |
| Ile | 732 | A | A | . | . | . | . | . | −0.34 | −0.06 | * | * | . | 0.45 | 1.03 |
| Asn | 733 | A | A | . | . | . | . | . | −0.34 | 0.01 | * | * | . | −0.30 | 0.44 |
| Phe | 734 | A | A | . | . | . | . | . | 0.32 | 0.70 | * | * | . | −0.60 | 0.19 |
| His | 735 | . | A | B | . | . | . | . | 0.01 | 0.70 | * | * | . | −0.60 | 0.44 |
| Val | 736 | . | A | B | . | . | . | . | −0.69 | 0.50 | * | * | . | −0.60 | 0.40 |
| Leu | 737 | . | A | B | . | . | . | . | 0.20 | 0.60 | . | * | . | −0.60 | 0.46 |
| Asp | 738 | A | A | . | . | . | . | . | −0.04 | −0.19 | . | . | F | 0.62 | 0.57 |
| Thr | 739 | A | . | . | . | . | T | . | −0.20 | 0.07 | . | . | F | 0.74 | 1.20 |
| Ala | 740 | A | . | . | . | . | T | . | −0.12 | 0.07 | * | . | F | 0.91 | 1.08 |
| Asp | 741 | A | . | . | . | . | T | . | 0.52 | −0.61 | * | . | . | 1.83 | 1.30 |
| Tyr | 742 | . | . | B | . | . | T | . | 0.48 | −0.19 | * | . | . | 1.70 | 1.39 |
| Val | 743 | . | . | B | B | . | . | . | 0.17 | −0.03 | . | . | . | 1.13 | 1.02 |
| Lys | 744 | . | . | B | B | . | . | . | −0.22 | −0.04 | . | . | F | 0.96 | 0.88 |
| Pro | 745 | . | . | B | B | . | . | . | 0.07 | 0.74 | * | . | F | −0.11 | 0.49 |
| Val | 746 | . | . | B | B | . | . | . | −0.79 | 0.37 | * | . | . | −0.13 | 0.88 |
| Thr | 747 | . | . | B | B | . | . | . | −0.54 | 0.37 | * | * | . | −0.30 | 0.33 |
| Phe | 748 | . | . | B | B | . | . | . | 0.07 | 0.37 | . | * | . | −0.30 | 0.37 |
| Ser | 749 | . | . | B | B | . | . | . | −0.28 | 0.70 | . | * | . | −0.60 | 0.77 |
| Val | 750 | . | . | B | B | . | . | . | −0.88 | 0.44 | . | * | . | −0.60 | 0.72 |
| Glu | 751 | . | . | B | B | . | . | . | −0.02 | 0.64 | . | * | . | −0.60 | 0.68 |
| Tyr | 752 | . | . | B | . | . | . | . | 0.29 | −0.14 | . | * | . | 0.50 | 0.88 |
| Ser | 753 | . | . | . | . | . | . | C | 0.78 | −0.53 | . | * | . | 1.49 | 1.99 |
| Leu | 754 | . | . | . | . | T | . | . | 1.08 | −0.74 | * | . | . | 2.03 | 1.78 |
| Glu | 755 | A | . | . | . | . | . | . | 1.90 | −0.74 | * | . | F | 2.12 | 1.89 |
| Asp | 756 | A | . | . | . | . | T | . | 1.56 | −1.00 | . | . | F | 2.66 | 1.92 |
| Pro | 757 | . | . | . | . | T | T | . | 1.59 | −0.96 | . | . | F | 3.40 | 2.31 |
| Asp | 758 | . | . | . | . | T | T | . | 1.29 | −1.21 | . | . | F | 3.06 | 2.06 |
| His | 759 | . | . | . | . | . | T | C | 1.29 | −0.60 | . | . | F | 2.52 | 1.22 |
| Gly | 760 | . | . | . | . | . | . | C | 1.29 | 0.09 | . | . | F | 0.93 | 0.65 |
| Pro | 761 | . | . | B | . | . | . | . | 1.29 | −0.34 | . | . | F | 0.99 | 0.65 |
| Met | 762 | . | . | B | . | . | . | . | 1.16 | −0.34 | * | . | . | 0.50 | 0.80 |

TABLE 13-continued

| Res | Position | I | II | III | IV | V | VI | VII | VIII | IX | X | XI | XII | XIII | XIV |
|---|---|---|---|---|---|---|---|---|---|---|---|---|---|---|---|
| Leu | 763 | . | . | B | . | . | . | . | 0.87 | −0.41 | * | . | F | 0.89 | 0.80 |
| Asp | 764 | . | . | . | . | T | T | . | 0.69 | 0.07 | . | . | F | 1.13 | 0.54 |
| Asp | 765 | . | . | . | . | T | T | . | 0.72 | 0.07 | . | . | F | 1.37 | 0.85 |
| Gly | 766 | . | . | . | . | T | T | . | 0.62 | −0.06 | . | . | F | 2.36 | 1.48 |
| Trp | 767 | . | . | . | . | . | T | C | 0.41 | −0.26 | * | * | F | 2.40 | 1.28 |
| Pro | 768 | . | . | . | B | . | . | C | 1.33 | 0.43 | * | * | F | 0.71 | 0.63 |
| Thr | 769 | . | . | B | B | . | . | . | 0.48 | 0.43 | * | * | F | 0.42 | 1.25 |
| Thr | 770 | . | . | B | B | . | . | . | 0.18 | 0.64 | * | * | F | 0.03 | 0.89 |
| Leu | 771 | . | . | B | B | . | . | . | −0.33 | 0.11 | . | * | . | −0.06 | 0.77 |
| Arg | 772 | . | . | B | B | . | . | . | −0.26 | 0.33 | * | * | . | −0.30 | 0.39 |
| Val | 773 | . | . | B | B | . | . | . | −0.74 | 0.27 | * | * | . | −0.30 | 0.42 |
| Ser | 774 | . | . | B | B | . | . | . | −0.72 | 0.57 | * | * | . | −0.60 | 0.44 |
| Val | 775 | . | . | B | B | . | . | . | −0.41 | 0.80 | * | * | . | −0.60 | 0.24 |
| Pro | 776 | . | . | B | B | . | . | . | 0.06 | 1.20 | * | * | . | −0.60 | 0.52 |
| Phe | 777 | . | . | . | B | T | . | . | −0.72 | 0.99 | * | * | . | −0.20 | 0.38 |
| Trp | 778 | . | . | . | . | T | T | . | 0.13 | 1.17 | . | . | . | 0.20 | 0.28 |
| Asn | 779 | . | . | . | . | . | T | C | 0.43 | 0.93 | . | . | . | 0.00 | 0.29 |
| Gly | 780 | . | . | . | . | T | T | . | 1.29 | 0.50 | . | . | . | 0.20 | 0.57 |
| Cys | 781 | . | . | . | . | T | T | . | 1.50 | −0.29 | . | . | F | 1.25 | 0.91 |
| Asn | 782 | . | A | . | . | T | . | . | 2.17 | −1.20 | . | . | F | 1.15 | 0.98 |
| Glu | 783 | . | A | . | . | T | . | . | 1.79 | −1.10 | . | . | F | 1.30 | 1.35 |
| Asp | 784 | . | A | . | . | T | . | . | 0.93 | −0.96 | . | . | F | 1.30 | 1.35 |
| Glu | 785 | . | A | . | . | T | . | . | 1.07 | −0.89 | . | . | F | 1.15 | 0.62 |
| His | 786 | . | A | . | . | T | . | . | 1.73 | −0.86 | * | . | . | 1.00 | 0.56 |
| Cys | 787 | A | A | . | . | . | . | . | 0.92 | −0.86 | * | . | . | 0.60 | 0.56 |
| Val | 788 | A | . | . | . | . | . | . | 0.07 | −0.17 | . | . | . | 0.50 | 0.26 |
| Pro | 789 | A | . | . | . | . | . | . | −0.74 | 0.47 | . | . | F | −0.25 | 0.14 |
| Asp | 790 | A | A | . | . | . | . | . | −0.74 | 0.66 | * | . | F | −0.45 | 0.22 |
| Leu | 791 | A | A | . | . | . | . | . | −1.30 | 0.09 | * | * | . | −0.30 | 0.50 |
| Val | 792 | A | A | . | . | . | . | . | −0.52 | −0.06 | * | * | . | 0.30 | 0.33 |
| Leu | 793 | A | A | . | . | . | . | . | 0.03 | −0.49 | * | * | . | 0.30 | 0.38 |
| Asp | 794 | . | A | B | . | . | . | . | 0.24 | −0.10 | . | * | . | 0.30 | 0.62 |
| Ala | 795 | A | A | . | . | . | . | . | −0.57 | −0.79 | . | * | F | 0.90 | 1.40 |
| Arg | 796 | A | . | . | . | . | T | . | 0.03 | −0.74 | . | * | F | 1.30 | 1.40 |
| Ser | 797 | A | . | . | . | . | T | . | 0.58 | −1.00 | . | * | F | 1.30 | 1.29 |
| Asp | 798 | A | . | . | . | . | T | C | 0.80 | −0.51 | . | * | F | 1.50 | 1.85 |
| Leu | 799 | . | . | . | . | . | T | C | 0.20 | −0.51 | * | * | F | 1.35 | 0.95 |
| Pro | 800 | . | A | . | . | . | . | C | 0.79 | 0.10 | * | * | F | 0.05 | 0.70 |
| Thr | 801 | A | A | . | . | . | . | . | 0.43 | −0.29 | . | * | . | 0.30 | 0.73 |
| Ala | 802 | A | A | . | . | . | . | . | 0.07 | 0.47 | . | . | . | −0.45 | 1.39 |
| Met | 803 | A | A | . | . | . | . | . | 0.07 | 0.36 | * | . | . | −0.30 | 0.48 |
| Glu | 804 | A | A | . | . | . | . | . | 0.99 | 0.33 | * | * | . | −0.30 | 0.58 |
| Tyr | 805 | A | . | . | B | . | . | . | 0.34 | −0.16 | * | . | . | 0.45 | 1.12 |
| Cys | 806 | A | . | . | B | . | . | . | −0.16 | −0.01 | * | . | . | 0.30 | 0.84 |
| Gln | 807 | A | . | . | B | . | . | . | 0.54 | 0.06 | * | . | . | −0.30 | 0.40 |
| Arg | 808 | A | . | . | B | . | . | . | 1.19 | 0.06 | * | . | . | −0.30 | 0.50 |
| Val | 809 | A | . | . | B | . | . | . | 0.98 | −0.70 | * | . | . | 0.75 | 1.86 |
| Leu | 810 | . | . | B | B | . | . | . | 0.63 | −0.84 | * | . | F | 1.20 | 1.66 |
| Arg | 811 | . | . | B | B | . | . | . | 1.30 | −0.74 | * | . | F | 1.35 | 0.86 |
| Lys | 812 | . | . | B | B | . | . | . | 1.30 | −0.34 | * | . | F | 1.50 | 2.00 |
| Pro | 813 | . | . | . | . | T | . | . | 0.52 | −0.99 | * | . | F | 2.70 | 4.06 |
| Ala | 814 | . | . | . | . | T | . | . | 1.08 | −1.10 | * | . | F | 3.00 | 1.11 |
| Gln | 815 | . | . | B | . | . | T | . | 1.30 | −0.71 | * | . | F | 2.35 | 0.74 |
| Asp | 816 | . | . | B | . | . | T | . | 0.94 | −0.21 | * | . | F | 1.75 | 0.49 |
| Cys | 817 | . | . | B | . | . | T | . | 0.59 | 0.11 | . | . | . | 0.70 | 0.75 |
| Ser | 818 | . | . | B | . | . | T | . | −0.01 | 0.10 | . | . | . | 0.40 | 0.63 |
| Ala | 819 | . | . | B | B | . | . | . | 0.28 | 0.39 | . | . | . | −0.30 | 0.31 |
| Tyr | 820 | . | . | B | B | . | . | . | −0.42 | 0.77 | . | . | . | −0.60 | 0.78 |
| Thr | 821 | . | . | B | B | . | . | . | −0.42 | 0.99 | . | . | . | −0.60 | 0.50 |
| Leu | 822 | . | . | B | B | . | . | . | −0.07 | 0.60 | . | . | . | −0.60 | 0.83 |
| Ser | 823 | . | . | B | B | . | . | . | −0.08 | 0.59 | . | * | . | −0.60 | 0.76 |
| Phe | 824 | . | . | B | B | . | . | . | −0.34 | 0.31 | . | * | . | −0.30 | 0.76 |
| Asp | 825 | . | . | B | B | . | . | . | −0.80 | 0.47 | . | * | F | −0.45 | 0.69 |
| Thr | 826 | . | . | B | B | . | . | . | −1.38 | 0.57 | . | * | F | −0.45 | 0.44 |
| Thr | 827 | . | . | B | B | . | . | . | −1.46 | 0.87 | . | * | F | −0.45 | 0.36 |
| Val | 828 | . | . | B | B | . | . | . | −1.16 | 0.77 | . | . | . | −0.60 | 0.15 |
| Phe | 829 | . | . | B | B | . | . | . | −0.76 | 0.77 | . | . | . | −0.60 | 0.18 |
| Ile | 830 | . | . | B | B | . | . | . | −1.07 | 0.67 | . | . | . | −0.60 | 0.17 |
| Ile | 831 | . | . | B | B | . | . | . | −0.64 | 0.67 | . | . | . | −0.60 | 0.33 |
| Glu | 832 | A | . | . | B | . | . | . | −0.33 | 0.03 | . | * | F | −0.15 | 0.74 |
| Ser | 833 | A | . | . | . | . | T | . | 0.63 | −0.36 | . | * | F | 1.00 | 1.83 |
| Thr | 834 | A | . | . | . | . | T | . | 0.48 | −1.04 | . | * | F | 1.30 | 5.10 |
| Arg | 835 | A | . | . | . | . | T | . | 0.78 | −1.09 | . | * | F | 1.30 | 2.19 |
| Gln | 836 | A | . | . | . | . | T | . | 0.81 | −0.59 | . | * | F | 1.30 | 1.65 |
| Arg | 837 | A | A | . | . | . | . | . | 0.81 | −0.33 | . | * | F | 0.45 | 0.85 |
| Val | 838 | . | A | B | . | . | . | . | 0.52 | −0.81 | . | * | . | 0.60 | 0.75 |
| Ala | 839 | . | A | B | . | . | . | . | 0.52 | −0.31 | . | * | . | 0.30 | 0.44 |
| Val | 840 | . | A | B | . | . | . | . | −0.40 | −0.23 | . | * | . | 0.30 | 0.32 |

TABLE 13-continued

| Res | Position | I | II | III | IV | V | VI | VII | VIII | IX | X | XI | XII | XIII | XIV |
|---|---|---|---|---|---|---|---|---|---|---|---|---|---|---|---|
| Glu | 841 | A | A | . | . | . | . | . | −0.40 | 0.46 | . | * | . | −0.60 | 0.36 |
| Ala | 842 | A | A | . | . | . | . | . | −0.51 | −0.19 | . | * | . | 0.30 | 0.61 |
| Thr | 843 | A | A | . | . | . | . | . | 0.46 | −0.29 | . | * | . | 0.45 | 1.33 |
| Leu | 844 | A | A | . | . | . | . | . | 0.70 | −0.93 | . | * | F | 0.90 | 1.50 |
| Glu | 845 | A | A | . | . | . | . | . | 1.56 | −0.50 | . | * | F | 0.60 | 1.47 |
| Asn | 846 | A | . | . | . | . | T | . | 1.56 | −1.00 | . | * | F | 1.60 | 1.77 |
| Arg | 847 | A | . | . | . | . | T | . | 1.56 | −1.09 | * | * | F | 1.90 | 3.45 |
| Gly | 848 | A | . | . | . | . | T | . | 1.62 | −1.27 | * | * | F | 2.20 | 2.01 |
| Glu | 849 | A | . | . | . | . | T | . | 2.13 | −0.51 | * | * | F | 2.50 | 1.96 |
| Asn | 850 | . | . | . | . | . | T | C | 1.82 | −0.53 | * | . | F | 3.00 | 1.34 |
| Ala | 851 | A | . | . | . | . | T | . | 0.97 | −0.04 | * | . | F | 2.20 | 1.95 |
| Tyr | 852 | . | . | B | . | . | T | . | 0.04 | 0.17 | * | . | . | 1.00 | 0.84 |
| Ser | 853 | . | . | B | . | . | T | . | 0.39 | 0.86 | * | . | . | 0.40 | 0.43 |
| Thr | 854 | . | . | B | B | . | . | . | −0.50 | 0.86 | * | . | . | −0.30 | 0.68 |
| Val | 855 | . | . | B | B | . | . | . | −0.80 | 1.04 | * | . | . | −0.60 | 0.31 |
| Leu | 856 | . | . | B | B | . | . | . | −0.21 | 0.67 | * | . | . | −0.60 | 0.31 |
| Asn | 857 | . | . | B | B | . | . | . | −0.27 | 0.69 | * | . | . | −0.60 | 0.37 |
| Ile | 858 | . | . | B | B | . | . | . | −0.56 | 0.59 | * | . | F | −0.45 | 0.66 |
| Ser | 859 | . | . | B | . | . | . | . | −0.24 | 0.44 | . | * | F | −0.25 | 0.81 |
| Gln | 860 | . | . | B | . | . | . | C | −0.20 | 0.16 | . | * | F | 0.25 | 0.81 |
| Ser | 861 | . | . | . | . | . | T | C | 0.61 | 0.44 | . | * | F | 0.15 | 0.96 |
| Ala | 862 | . | . | B | . | . | T | . | −0.09 | 0.16 | . | * | F | 0.40 | 1.23 |
| Asn | 863 | . | . | B | . | . | T | . | 0.21 | 0.56 | . | * | . | −0.20 | 0.62 |
| Leu | 864 | A | . | . | . | . | T | . | 0.21 | 0.66 | . | . | . | −0.20 | 0.47 |
| Gln | 865 | A | A | . | . | . | . | . | −0.60 | 0.66 | . | * | . | −0.60 | 0.62 |
| Phe | 866 | A | A | . | . | . | . | . | −1.19 | 0.84 | . | * | . | −0.60 | 0.32 |
| Ala | 867 | A | A | . | . | . | . | . | −0.60 | 1.13 | * | * | . | −0.60 | 0.27 |
| Ser | 868 | A | A | . | . | . | . | . | −0.56 | 0.84 | * | * | . | −0.60 | 0.27 |
| Leu | 869 | A | A | . | . | . | . | . | 0.26 | 0.44 | * | . | . | −0.60 | 0.62 |
| Ile | 870 | A | A | . | . | . | . | . | 0.26 | −0.34 | * | . | . | 0.45 | 1.07 |
| Gln | 871 | A | A | . | . | . | . | . | 0.66 | −0.84 | * | . | F | 1.24 | 1.33 |
| Lys | 872 | A | A | . | . | . | . | . | 1.24 | −0.84 | * | . | F | 1.58 | 2.16 |
| Glu | 873 | A | A | . | . | . | . | . | 1.20 | −1.53 | * | . | F | 1.92 | 5.14 |
| Asp | 874 | . | . | . | . | T | T | . | 1.71 | −1.79 | . | * | F | 3.06 | 2.94 |
| Ser | 875 | . | . | . | . | T | T | . | 1.71 | −1.80 | . | * | F | 3.40 | 1.97 |
| Asp | 876 | . | . | . | . | T | T | . | 1.71 | −1.11 | . | * | F | 2.91 | 0.80 |
| Gly | 877 | . | . | . | . | T | T | . | 1.00 | −1.11 | . | * | F | 2.57 | 0.83 |
| Ser | 878 | A | A | . | . | . | . | . | 0.14 | −0.54 | . | . | F | 1.43 | 0.33 |
| Ile | 879 | A | A | . | . | . | . | . | 0.14 | −0.29 | . | * | . | 0.64 | 0.15 |
| Glu | 880 | A | A | . | . | . | . | . | 0.44 | 0.11 | . | . | . | −0.30 | 0.24 |
| Cys | 881 | . | A | B | . | . | . | . | 0.44 | −0.31 | . | * | . | 0.30 | 0.31 |
| Val | 882 | A | A | . | . | . | . | . | 0.90 | −0.70 | * | . | . | 0.60 | 0.76 |
| Asn | 883 | A | A | . | . | . | . | . | 1.31 | −1.39 | * | . | F | 0.75 | 0.86 |
| Glu | 884 | A | A | . | . | . | . | . | 1.39 | −1.39 | * | * | F | 0.90 | 3.15 |
| Glu | 885 | A | A | . | . | . | . | . | 1.39 | −1.27 | * | . | F | 0.90 | 3.50 |
| Arg | 886 | A | A | . | . | . | . | . | 2.10 | −1.51 | * | . | F | 0.90 | 3.77 |
| Arg | 887 | A | A | . | . | . | . | . | 2.96 | −1.91 | * | * | F | 0.90 | 4.35 |
| Leu | 888 | A | A | . | . | . | . | . | 2.10 | −1.51 | * | . | F | 0.90 | 4.35 |
| Gln | 889 | A | A | . | . | . | . | . | 1.43 | −0.87 | * | . | F | 0.90 | 1.65 |
| Lys | 890 | A | A | . | . | . | . | . | 1.43 | −0.30 | * | . | F | 0.45 | 0.45 |
| Gln | 891 | . | A | B | . | . | . | . | 0.47 | 0.10 | * | . | . | −0.30 | 0.88 |
| Val | 892 | . | A | B | . | . | . | . | 0.06 | 0.06 | * | * | . | −0.30 | 0.38 |
| Cys | 893 | . | A | B | . | . | . | . | 0.62 | 0.04 | * | . | . | −0.30 | 0.25 |
| Asn | 894 | . | . | B | . | . | T | . | 0.41 | 0.80 | * | . | . | −0.20 | 0.23 |
| Val | 895 | . | . | B | . | . | T | . | −0.33 | 0.83 | * | . | . | −0.20 | 0.48 |
| Ser | 896 | . | . | B | . | . | T | . | −1.03 | 0.97 | * | . | . | −0.20 | 0.77 |
| Tyr | 897 | . | . | B | . | . | T | . | −0.07 | 1.19 | * | . | . | −0.20 | 0.41 |
| Pro | 898 | . | . | B | B | . | . | . | 0.01 | 0.79 | * | * | . | −0.45 | 1.09 |
| Phe | 899 | A | A | . | B | . | . | . | 0.06 | 0.64 | * | * | . | −0.60 | 0.82 |
| Phe | 900 | A | A | . | B | . | . | . | 0.32 | 0.26 | * | * | . | −0.15 | 1.05 |
| Arg | 901 | A | A | . | B | . | . | . | 0.67 | 0.00 | * | * | . | −0.30 | 0.69 |
| Ala | 902 | A | A | . | . | . | . | . | 0.06 | −0.43 | * | * | . | 0.45 | 1.59 |
| Lys | 903 | A | A | . | . | . | . | . | −0.32 | −0.57 | * | * | F | 0.90 | 1.36 |
| Ala | 904 | A | A | . | . | . | . | . | −0.32 | −0.86 | * | * | F | 0.75 | 0.70 |
| Lys | 905 | A | A | . | B | . | . | . | 0.49 | −0.07 | * | * | . | 0.30 | 0.60 |
| Val | 906 | A | A | . | B | . | . | . | −0.43 | −0.57 | * | * | . | 0.60 | 0.59 |
| Ala | 907 | A | A | . | B | . | . | . | 0.16 | 0.11 | . | * | . | −0.30 | 0.48 |
| Phe | 908 | A | A | . | B | . | . | . | −0.59 | −0.39 | . | * | . | 0.30 | 0.40 |
| Arg | 909 | A | A | . | B | . | . | . | 0.00 | 0.40 | * | * | . | −0.60 | 0.47 |
| Leu | 910 | A | A | . | . | . | . | . | −0.74 | −0.24 | * | * | . | 0.30 | 0.80 |
| Asp | 911 | A | A | . | . | . | . | . | −0.19 | 0.04 | * | * | . | −0.30 | 0.80 |
| Phe | 912 | A | A | . | . | . | . | . | 0.44 | −0.36 | * | * | . | 0.30 | 0.55 |
| Glu | 913 | A | A | . | . | . | . | . | 0.84 | −0.36 | * | * | . | 0.45 | 1.33 |
| Phe | 914 | A | A | . | . | . | . | . | −0.16 | −0.66 | * | * | . | 0.75 | 1.07 |
| Ser | 915 | A | . | . | . | . | T | . | −0.04 | 0.03 | . | * | F | 0.25 | 0.87 |
| Lys | 916 | A | . | . | . | . | T | . | −0.86 | 0.03 | . | * | F | 0.25 | 0.43 |
| Ser | 917 | A | . | . | . | . | T | . | −0.19 | 0.71 | . | . | . | −0.20 | 0.41 |
| Ile | 918 | A | . | . | . | . | T | . | −0.22 | 0.43 | . | . | . | −0.20 | 0.42 |

TABLE 13-continued

| Res | Position | I | II | III | IV | V | VI | VII | VIII | IX | X | XI | XII | XIII | XIV |
|---|---|---|---|---|---|---|---|---|---|---|---|---|---|---|---|
| Phe | 919 | A | A | . | . | . | . | . | −0.33 | 0.54 | . | . | . | −0.60 | 0.28 |
| Leu | 920 | A | A | . | . | . | . | . | −0.03 | 1.23 | . | . | . | −0.60 | 0.18 |
| His | 921 | A | A | . | . | . | . | . | −0.97 | 0.84 | . | * | . | −0.60 | 0.43 |
| His | 922 | A | A | . | . | . | . | . | −0.67 | 0.84 | . | * | . | −0.60 | 0.35 |
| Leu | 923 | A | A | . | . | . | . | . | −0.59 | 0.06 | . | * | . | −0.30 | 0.74 |
| Glu | 924 | A | A | . | . | . | . | . | −0.48 | 0.06 | . | * | . | −0.30 | 0.45 |
| Ile | 925 | A | A | . | . | . | . | . | −0.26 | 0.06 | . | * | . | −0.30 | 0.33 |
| Glu | 926 | A | A | . | . | . | . | . | −0.57 | 0.06 | . | * | . | −0.30 | 0.41 |
| Leu | 927 | A | A | . | . | . | . | . | −0.83 | −0.20 | . | * | . | 0.30 | 0.23 |
| Ala | 928 | A | A | . | . | . | . | . | −0.02 | 0.19 | . | * | . | −0.30 | 0.44 |
| Ala | 929 | A | A | . | . | . | . | . | −0.32 | −0.50 | . | * | . | 0.30 | 0.43 |
| Gly | 930 | A | . | . | . | . | T | . | 0.57 | −0.11 | . | * | F | 0.85 | 0.69 |
| Ser | 931 | . | . | . | . | . | T | C | 0.57 | −0.40 | * | * | F | 1.20 | 1.11 |
| Asp | 932 | . | . | . | . | . | T | C | 1.49 | −0.90 | . | . | F | 1.50 | 1.89 |
| Ser | 933 | . | . | . | . | . | T | C | 2.08 | −1.40 | . | . | F | 1.84 | 3.75 |
| Asn | 934 | . | . | . | . | . | . | C | 2.37 | −1.83 | . | . | F | 1.98 | 4.67 |
| Glu | 935 | A | . | . | . | . | . | . | 2.40 | −1.83 | * | * | F | 2.12 | 3.75 |
| Arg | 936 | A | . | . | . | . | . | . | 2.74 | −1.34 | . | . | F | 2.46 | 4.04 |
| Asp | 937 | . | . | . | . | T | T | . | 2.74 | −1.73 | . | * | F | 3.40 | 5.02 |
| Ser | 938 | . | . | . | . | . | T | C | 3.04 | −2.13 | . | . | F | 2.86 | 5.02 |
| Thr | 939 | A | . | . | . | . | T | . | 3.04 | −2.13 | . | . | F | 2.32 | 4.28 |
| Lys | 940 | A | . | . | . | . | T | . | 2.19 | −1.73 | * | . | F | 1.98 | 4.12 |
| Glu | 941 | A | A | . | . | . | . | . | 1.49 | −1.09 | * | . | F | 1.24 | 2.28 |
| Asp | 942 | A | A | . | . | . | . | . | 1.28 | −0.97 | . | . | F | 0.90 | 1.60 |
| Asn | 943 | A | A | . | . | . | . | . | 0.77 | −1.03 | . | * | F | 0.90 | 1.24 |
| Val | 944 | A | A | . | . | . | . | . | 1.19 | −0.34 | . | * | . | 0.30 | 0.59 |
| Ala | 945 | A | A | . | . | . | . | . | 0.44 | −0.34 | . | * | . | 0.30 | 0.69 |
| Pro | 946 | A | A | . | . | . | . | . | 0.41 | 0.44 | . | * | . | −0.60 | 0.37 |
| Leu | 947 | A | A | . | . | . | . | . | −0.40 | 0.54 | . | * | . | −0.60 | 0.68 |
| Arg | 948 | A | A | . | . | . | . | . | −0.36 | 0.59 | . | * | . | −0.60 | 0.56 |
| Phe | 949 | A | A | . | . | . | . | . | 0.26 | 0.09 | . | * | . | −0.30 | 0.72 |
| His | 950 | A | A | . | . | . | . | . | 0.84 | 0.41 | . | * | . | −0.45 | 1.37 |
| Leu | 951 | A | A | . | . | . | . | . | 0.47 | −0.27 | * | * | . | 0.45 | 1.21 |
| Lys | 952 | A | A | . | . | . | . | . | 1.28 | 0.23 | * | * | . | −0.15 | 1.41 |
| Tyr | 953 | A | A | . | . | . | . | . | 0.31 | −0.56 | * | * | . | 0.75 | 1.73 |
| Glu | 954 | A | A | . | . | . | . | . | 0.20 | −0.41 | . | * | . | 0.45 | 1.56 |
| Ala | 955 | A | . | . | B | . | . | . | −0.47 | −0.41 | . | * | . | 0.30 | 0.64 |
| Asp | 956 | A | . | . | B | . | . | . | 0.03 | 0.37 | . | * | . | −0.30 | 0.35 |
| Val | 957 | A | . | . | B | . | . | . | 0.10 | 0.10 | . | * | . | −0.30 | 0.30 |
| Leu | 958 | A | . | . | B | . | . | . | 0.04 | 0.10 | . | . | . | −0.30 | 0.57 |
| Phe | 959 | A | . | . | B | . | . | . | −0.26 | −0.01 | . | . | . | 0.30 | 0.46 |
| Thr | 960 | A | . | . | B | . | . | . | 0.03 | 0.37 | . | . | F | 0.06 | 0.83 |
| Arg | 961 | A | . | . | B | . | . | . | −0.78 | 0.11 | . | . | F | 0.42 | 1.35 |
| Ser | 962 | . | . | . | . | T | T | . | −0.22 | 0.11 | . | . | F | 1.43 | 1.29 |
| Ser | 963 | . | . | . | . | . | T | C | 0.56 | −0.29 | . | . | F | 2.04 | 1.19 |
| Ser | 964 | . | . | . | . | . | T | C | 1.01 | −0.27 | . | . | F | 2.10 | 0.83 |
| Leu | 965 | . | . | . | . | . | T | C | 1.32 | 0.49 | . | . | F | 0.99 | 0.97 |
| Ser | 966 | . | . | . | . | . | . | C | 0.36 | 0.10 | . | * | . | 0.88 | 1.25 |
| His | 967 | . | . | B | . | . | . | . | 0.70 | 0.36 | . | * | . | 0.32 | 0.69 |
| Tyr | 968 | . | . | B | . | . | . | . | 0.19 | −0.03 | . | * | . | 0.86 | 1.68 |
| Glu | 969 | . | . | B | . | . | . | . | 0.49 | −0.03 | . | * | . | 0.65 | 1.04 |
| Val | 970 | A | . | . | . | . | . | . | 1.00 | −0.01 | . | * | . | 0.65 | 1.22 |
| Lys | 971 | A | . | . | . | . | . | . | 1.00 | −0.13 | . | * | F | 0.80 | 1.05 |
| Leu | 972 | A | . | . | . | . | . | . | 0.22 | −0.50 | . | * | F | 0.65 | 0.81 |
| Asn | 973 | . | . | . | . | . | T | C | 0.47 | 0.19 | * | * | F | 0.45 | 0.90 |
| Ser | 974 | A | . | . | . | . | T | . | 0.58 | −0.46 | * | * | F | 0.85 | 0.78 |
| Ser | 975 | A | . | . | . | . | T | . | 1.19 | −0.46 | * | * | F | 1.00 | 1.85 |
| Leu | 976 | . | . | B | . | . | T | . | 1.14 | −0.39 | * | * | F | 1.31 | 1.80 |
| Glu | 977 | . | . | B | . | . | . | . | 1.61 | −0.79 | * | . | F | 1.72 | 2.25 |
| Arg | 978 | . | . | B | . | . | T | . | 0.72 | −0.74 | * | . | F | 2.23 | 1.66 |
| Tyr | 979 | . | . | B | . | . | T | . | 0.68 | −0.44 | . | . | F | 2.24 | 1.41 |
| Asp | 980 | . | . | . | . | T | T | . | 0.77 | −0.70 | . | . | F | 3.10 | 0.81 |
| Gly | 981 | . | . | . | . | T | T | . | 1.37 | −0.27 | * | . | F | 2.49 | 0.64 |
| Ile | 982 | . | . | . | . | T | . | . | 0.67 | 0.16 | * | . | F | 1.38 | 0.63 |
| Gly | 983 | . | . | . | . | . | . | C | 0.26 | 0.19 | . | * | F | 0.87 | 0.33 |
| Pro | 984 | . | . | . | . | . | T | C | −0.17 | 0.57 | * | . | F | 0.46 | 0.44 |
| Pro | 985 | . | . | . | . | T | T | . | −1.06 | 0.71 | * | . | F | 0.35 | 0.34 |
| Phe | 986 | . | . | . | . | T | T | . | −1.41 | 0.71 | * | * | . | 0.20 | 0.24 |
| Ser | 987 | . | . | B | . | . | T | . | −0.41 | 1.07 | * | * | . | −0.20 | 0.13 |
| Cys | 988 | . | . | B | B | . | . | . | −0.96 | 0.64 | * | * | . | −0.60 | 0.17 |
| Ile | 989 | . | . | B | B | . | . | . | −0.74 | 0.90 | * | * | . | −0.60 | 0.14 |
| Phe | 990 | . | . | B | B | . | . | . | −0.53 | 0.51 | * | * | . | −0.60 | 0.18 |
| Arg | 991 | . | . | B | B | . | . | . | −0.64 | 0.53 | * | * | . | −0.60 | 0.53 |
| Ile | 992 | . | . | B | B | . | . | . | −0.69 | 0.64 | * | * | . | −0.60 | 0.63 |
| Gln | 993 | . | . | B | B | . | . | . | −0.83 | 0.39 | * | * | . | −0.30 | 0.72 |
| Asn | 994 | . | . | . | B | T | . | . | −0.64 | 0.29 | * | * | . | 0.10 | 0.30 |
| Leu | 995 | . | . | . | B | T | . | . | −0.16 | 1.07 | . | * | . | −0.20 | 0.37 |
| Gly | 996 | . | . | . | B | T | . | . | −1.16 | 0.81 | * | * | . | −0.20 | 0.33 |

TABLE 13-continued

| Res | Position | I | II | III | IV | V | VI | VII | VIII | IX | X | XI | XII | XIII | XIV |
|---|---|---|---|---|---|---|---|---|---|---|---|---|---|---|---|
| Leu | 997 | . | . | . | . | . | . | C | −0.30 | 1.10 | . | . | . | −0.20 | 0.14 |
| Phe | 998 | . | . | B | . | . | . | . | −0.64 | 1.20 | . | . | . | −0.40 | 0.24 |
| Pro | 999 | . | . | B | . | . | . | . | −1.53 | 0.94 | . | . | . | −0.40 | 0.24 |
| Ile | 1000 | A | . | . | B | . | . | . | −1.32 | 1.20 | . | . | . | −0.60 | 0.20 |
| His | 1001 | A | . | . | B | . | . | . | −1.58 | 1.13 | . | . | . | −0.60 | 0.23 |
| Gly | 1002 | A | . | . | B | . | . | . | −0.72 | 0.96 | * | . | . | −0.60 | 0.15 |
| Ile | 1003 | A | . | . | B | . | . | . | −0.91 | 0.53 | . | * | . | −0.60 | 0.42 |
| Met | 1004 | A | . | . | B | . | . | . | −1.01 | 0.53 | . | * | . | −0.60 | 0.22 |
| Met | 1005 | . | . | B | B | . | . | . | −1.01 | 0.51 | . | * | . | −0.60 | 0.32 |
| Lys | 1006 | . | . | B | B | . | . | . | −1.19 | 0.77 | . | * | . | −0.60 | 0.32 |
| Ile | 1007 | . | . | B | B | . | . | . | −1.73 | 0.51 | . | * | . | −0.60 | 0.50 |
| Thr | 1008 | . | . | B | B | . | . | . | −1.43 | 0.59 | . | * | . | −0.60 | 0.35 |
| Ile | 1009 | . | . | B | B | . | . | . | −1.14 | 0.47 | * | * | . | −0.60 | 0.18 |
| Pro | 1010 | . | . | B | B | . | . | . | −0.43 | 0.96 | * | * | . | −0.60 | 0.37 |
| Ile | 1011 | . | . | B | B | . | . | . | −0.78 | 0.27 | * | * | . | 0.04 | 0.50 |
| Ala | 1012 | . | . | B | B | . | . | . | −0.23 | 0.17 | * | * | . | 0.38 | 0.95 |
| Thr | 1013 | . | . | B | . | . | T | . | 0.08 | −0.09 | * | * | F | 1.87 | 0.61 |
| Arg | 1014 | . | . | . | . | T | T | . | 1.08 | −0.11 | * | * | F | 2.76 | 1.40 |
| Ser | 1015 | . | . | . | . | T | T | . | 0.48 | −0.80 | * | * | F | 3.40 | 2.71 |
| Gly | 1016 | . | . | . | . | T | T | . | 0.56 | −0.61 | * | * | F | 3.06 | 1.55 |
| Asn | 1017 | . | A | . | . | T | . | . | 1.19 | −0.41 | * | . | F | 1.87 | 0.65 |
| Arg | 1018 | . | A | B | . | . | . | . | 0.69 | −0.41 | * | * | F | 1.13 | 0.97 |
| Leu | 1019 | . | A | B | . | . | . | . | 0.69 | −0.11 | * | * | F | 0.79 | 0.81 |
| Leu | 1020 | . | A | B | . | . | . | . | 0.99 | −0.54 | . | . | F | 0.75 | 0.99 |
| Lys | 1021 | . | A | B | . | . | . | . | 0.63 | −0.94 | * | . | F | 0.75 | 0.84 |
| Leu | 1022 | . | A | B | . | . | . | . | −0.18 | −0.16 | * | . | F | 0.45 | 0.88 |
| Arg | 1023 | . | A | B | . | . | . | . | −0.60 | −0.16 | * | . | F | 0.45 | 0.88 |
| Asp | 1024 | . | A | B | . | . | . | . | 0.21 | −0.36 | * | * | F | 0.45 | 0.64 |
| Phe | 1025 | . | A | B | . | . | . | . | 1.02 | −0.36 | * | * | . | 0.45 | 1.29 |
| Leu | 1026 | A | A | . | . | . | . | . | 0.12 | −1.04 | * | * | F | 0.90 | 1.14 |
| Thr | 1027 | A | A | . | . | . | . | . | 0.34 | −0.40 | * | . | F | 0.45 | 0.51 |
| Asp | 1028 | A | A | . | . | . | . | . | 0.23 | 0.10 | . | . | F | −0.15 | 0.59 |
| Glu | 1029 | A | A | . | . | . | . | . | −0.08 | −0.29 | * | . | . | 0.45 | 1.15 |
| Val | 1030 | A | A | . | . | . | . | . | 0.32 | −0.49 | . | . | . | 0.45 | 1.15 |
| Ala | 1031 | A | A | . | . | . | . | . | 0.47 | −0.59 | * | . | . | 0.60 | 0.93 |
| Asn | 1032 | . | . | . | . | T | T | . | 0.78 | −0.01 | * | . | F | 1.25 | 0.29 |
| Thr | 1033 | . | . | . | . | T | T | . | −0.11 | 0.39 | * | . | F | 0.65 | 0.62 |
| Ser | 1034 | . | . | B | . | . | T | . | −0.40 | 0.43 | * | . | F | −0.05 | 0.43 |
| Cys | 1035 | . | . | B | . | . | T | . | 0.11 | 0.84 | * | * | . | −0.20 | 0.28 |
| Asn | 1036 | . | . | . | . | T | . | . | 0.70 | 0.87 | . | * | . | 0.16 | 0.19 |
| Ile | 1037 | . | . | . | . | T | . | . | 0.40 | 0.79 | . | * | . | 0.32 | 0.23 |
| Trp | 1038 | . | . | . | . | T | T | . | 0.40 | 0.79 | . | . | . | 0.68 | 0.58 |
| Gly | 1039 | . | . | . | . | . | T | C | 0.70 | 0.70 | . | . | F | 0.79 | 0.52 |
| Asn | 1040 | . | . | . | . | T | T | . | 1.12 | 0.30 | . | * | F | 1.60 | 1.28 |
| Ser | 1041 | . | . | . | . | . | T | C | 1.23 | 0.37 | . | * | F | 1.24 | 1.91 |
| Thr | 1042 | . | . | . | . | . | . | C | 1.91 | −0.54 | . | * | F | 1.78 | 3.79 |
| Glu | 1043 | . | . | . | . | T | . | . | 1.89 | −0.54 | . | * | F | 1.82 | 3.64 |
| Tyr | 1044 | . | . | . | . | T | . | . | 2.02 | −0.46 | . | . | F | 1.66 | 3.92 |
| Arg | 1045 | . | . | . | . | . | T | C | 1.17 | −0.41 | . | . | F | 1.80 | 4.20 |
| Pro | 1046 | . | . | . | . | . | T | C | 1.47 | −0.26 | . | . | F | 2.10 | 1.80 |
| Thr | 1047 | . | . | . | . | . | T | C | 1.78 | −0.26 | . | . | F | 2.40 | 1.99 |
| Pro | 1048 | . | . | . | . | . | T | C | 1.78 | −1.01 | . | * | F | 3.00 | 1.76 |
| Val | 1049 | A | A | . | . | . | . | . | 1.21 | −1.01 | . | * | F | 2.10 | 1.90 |
| Glu | 1050 | A | A | . | . | . | . | . | 1.21 | −0.76 | * | . | F | 1.80 | 1.09 |
| Glu | 1051 | A | A | . | . | . | . | . | 1.53 | −1.24 | * | . | F | 1.50 | 1.38 |
| Asp | 1052 | A | A | . | . | . | . | . | 1.26 | −1.67 | * | . | F | 1.20 | 3.63 |
| Leu | 1053 | A | A | . | . | . | . | . | 1.26 | −1.81 | * | . | F | 0.90 | 2.12 |
| Arg | 1054 | A | A | . | . | . | . | . | 2.11 | −1.39 | * | * | F | 0.90 | 1.89 |
| Arg | 1055 | A | A | . | . | . | . | . | 1.30 | −0.99 | * | * | F | 0.90 | 1.96 |
| Ala | 1056 | A | A | . | . | . | . | . | 1.30 | −0.30 | * | . | F | 0.60 | 1.96 |
| Pro | 1057 | A | A | . | . | . | . | . | 1.27 | −0.59 | * | * | F | 0.90 | 1.61 |
| Gln | 1058 | A | A | . | . | . | . | . | 1.78 | −0.09 | * | . | F | 0.60 | 1.12 |
| Leu | 1059 | . | A | B | . | . | . | . | 1.67 | 0.30 | * | . | . | 0.13 | 1.48 |
| Asn | 1060 | . | A | . | . | . | . | C | 1.26 | 0.20 | . | . | . | 0.61 | 1.54 |
| His | 1061 | . | . | . | . | . | T | C | 1.84 | 0.16 | . | . | F | 1.44 | 1.19 |
| Ser | 1062 | . | . | . | . | . | T | C | 1.20 | −0.24 | . | . | F | 2.32 | 2.42 |
| Asn | 1063 | . | . | . | . | T | T | . | 0.34 | −0.29 | * | . | F | 2.80 | 1.12 |
| Ser | 1064 | . | . | . | . | T | T | . | 0.86 | −0.04 | * | . | F | 2.37 | 0.61 |
| Asp | 1065 | . | . | B | B | . | . | . | −0.03 | −0.16 | . | . | F | 1.29 | 0.61 |
| Val | 1066 | . | . | B | B | . | . | . | 0.00 | 0.14 | . | . | F | 0.41 | 0.27 |
| Val | 1067 | . | . | B | B | . | . | . | −0.37 | 0.14 | . | . | . | −0.02 | 0.32 |
| Ser | 1068 | . | . | B | . | . | T | . | −0.37 | 0.33 | . | * | . | 0.10 | 0.10 |
| Ile | 1069 | . | . | B | . | . | T | . | −0.96 | 0.73 | * | * | . | −0.20 | 0.22 |
| Asn | 1070 | . | . | B | . | . | T | . | −0.84 | 0.77 | . | * | . | −0.20 | 0.21 |
| Cys | 1071 | . | . | B | . | . | T | . | −0.80 | 0.13 | * | * | . | 0.10 | 0.31 |
| Asn | 1072 | . | . | B | B | . | . | . | −0.80 | 0.43 | * | * | . | −0.60 | 0.36 |
| Ile | 1073 | . | . | B | B | . | . | . | −0.71 | 0.39 | * | * | . | −0.30 | 0.17 |
| Arg | 1074 | . | . | B | B | . | . | . | 0.18 | 0.41 | * | * | . | −0.60 | 0.48 |

TABLE 13-continued

| Res | Position | I | II | III | IV | V | VI | VII | VIII | IX | X | XI | XII | XIII | XIV |
|---|---|---|---|---|---|---|---|---|---|---|---|---|---|---|---|
| Leu | 1075 | . | . | B | B | . | . | . | 0.18 | 0.24 | * | * | . | −0.30 | 0.48 |
| Val | 1076 | . | . | B | . | . | T | . | 0.84 | 0.24 | . | * | F | 0.40 | 1.18 |
| Pro | 1077 | . | . | . | . | . | T | C | −0.04 | −0.44 | * | * | F | 1.20 | 1.05 |
| Asn | 1078 | . | . | . | . | T | T | . | 0.84 | 0.24 | * | * | F | 0.65 | 0.89 |
| Gln | 1079 | A | . | . | . | . | T | . | 0.03 | −0.04 | * | * | F | 1.00 | 1.93 |
| Glu | 1080 | . | A | B | . | . | . | . | 0.81 | 0.10 | . | * | F | 0.00 | 1.08 |
| Ile | 1081 | . | A | B | . | . | . | . | 0.86 | 0.17 | . | * | F | −0.15 | 0.91 |
| Asn | 1082 | . | A | B | . | . | . | . | 0.26 | 0.46 | . | * | . | −0.60 | 0.43 |
| Phe | 1083 | . | A | B | . | . | . | . | −0.09 | 0.74 | . | * | . | −0.60 | 0.21 |
| His | 1084 | . | A | B | . | . | . | . | −0.09 | 1.17 | . | * | . | −0.60 | 0.29 |
| Leu | 1085 | . | A | B | . | . | . | . | −0.90 | 0.89 | . | * | . | −0.60 | 0.29 |
| Leu | 1086 | . | A | . | . | . | . | C | −0.30 | 1.17 | . | * | . | −0.40 | 0.28 |
| Gly | 1087 | . | A | . | . | T | . | . | −1.11 | 1.30 | * | * | . | −0.20 | 0.22 |
| Asn | 1088 | A | A | . | . | . | . | . | −0.30 | 1.49 | * | * | . | −0.60 | 0.22 |
| Leu | 1089 | A | A | . | . | . | . | . | −0.57 | 0.80 | * | * | . | −0.60 | 0.51 |
| Trp | 1090 | A | A | . | . | . | . | . | −0.57 | 0.50 | * | * | . | −0.60 | 0.69 |
| Leu | 1091 | A | A | . | . | . | . | . | 0.29 | 0.76 | * | . | . | −0.60 | 0.35 |
| Arg | 1092 | A | A | . | . | . | . | . | 0.04 | 0.36 | * | * | . | −0.30 | 0.86 |
| Ser | 1093 | A | A | . | . | . | . | . | −0.77 | 0.17 | * | . | . | −0.30 | 0.83 |
| Leu | 1094 | A | A | . | . | . | . | . | 0.09 | −0.06 | * | . | F | 0.45 | 0.83 |
| Lys | 1095 | A | A | . | . | . | . | . | 0.13 | −0.74 | * | . | F | 0.75 | 0.84 |
| Ala | 1096 | A | A | . | . | . | . | . | 0.99 | 0.01 | * | * | . | −0.30 | 0.99 |
| Leu | 1097 | A | A | . | . | . | . | . | 0.58 | −0.37 | * | . | . | 0.45 | 2.39 |
| Lys | 1098 | A | A | . | . | . | . | . | 0.28 | −0.67 | . | . | F | 0.90 | 1.60 |
| Tyr | 1099 | A | A | . | . | . | . | . | 1.13 | −0.06 | * | . | F | 0.60 | 1.57 |
| Lys | 1100 | A | A | . | . | . | . | . | 0.20 | −0.56 | * | . | F | 0.90 | 3.81 |
| Ser | 1101 | A | A | . | . | . | . | . | 0.19 | −0.56 | . | * | F | 0.90 | 1.34 |
| Met | 1102 | A | A | . | . | . | . | . | 0.14 | 0.06 | . | * | . | −0.30 | 0.84 |
| Lys | 1103 | A | A | . | . | . | . | . | 0.10 | −0.06 | . | * | . | 0.30 | 0.31 |
| Ile | 1104 | . | A | B | . | . | . | . | −0.24 | 0.34 | * | * | . | −0.30 | 0.38 |
| Met | 1105 | A | A | . | . | . | . | . | −0.88 | 0.46 | * | * | . | −0.60 | 0.38 |
| Val | 1106 | A | A | . | . | . | . | . | −1.39 | 0.34 | * | * | . | −0.30 | 0.19 |
| Asn | 1107 | A | A | . | . | . | . | . | −0.79 | 1.03 | . | * | . | −0.60 | 0.23 |
| Ala | 1108 | A | A | . | . | . | . | . | −0.72 | 0.74 | . | * | . | −0.60 | 0.40 |
| Ala | 1109 | A | A | . | . | . | . | . | 0.17 | 0.13 | . | * | . | −0.15 | 1.05 |
| Leu | 1110 | A | A | . | . | . | . | . | 0.07 | −0.11 | * | . | . | 0.45 | 1.13 |
| Gln | 1111 | A | A | . | . | . | . | . | 0.89 | 0.27 | * | . | . | −0.30 | 0.97 |
| Arg | 1112 | A | A | . | . | . | . | . | 0.59 | 0.27 | * | . | . | −0.15 | 1.31 |
| Gln | 1113 | . | A | B | . | . | . | . | 0.97 | 0.16 | * | . | . | −0.15 | 2.13 |
| Phe | 1114 | . | A | . | . | T | . | . | 0.86 | −0.10 | * | . | . | 0.85 | 1.90 |
| His | 1115 | . | A | . | . | . | . | C | 0.78 | 0.29 | * | . | . | −0.10 | 0.84 |
| Ser | 1116 | . | A | . | . | . | . | C | 0.08 | 0.97 | . | * | . | −0.40 | 0.34 |
| Pro | 1117 | . | . | . | B | . | . | C | 0.08 | 1.36 | . | * | . | −0.40 | 0.34 |
| Phe | 1118 | . | A | . | B | . | . | C | 0.08 | 0.57 | . | * | . | −0.40 | 0.49 |
| Ile | 1119 | . | A | B | B | . | . | . | 0.78 | 0.07 | . | * | . | −0.30 | 0.63 |
| Phe | 1120 | . | A | B | B | . | . | . | 0.81 | −0.31 | . | . | . | 0.30 | 0.71 |
| Arg | 1121 | A | A | . | B | . | . | . | 0.90 | −0.74 | . | . | F | 1.24 | 1.37 |
| Glu | 1122 | . | A | . | . | T | . | . | 0.81 | −1.10 | * | * | F | 1.98 | 3.01 |
| Glu | 1123 | . | A | . | . | . | . | C | 1.62 | −1.40 | * | * | F | 2.12 | 4.66 |
| Asp | 1124 | . | . | . | . | . | T | C | 2.51 | −2.19 | * | . | F | 2.86 | 4.66 |
| Pro | 1125 | . | . | . | . | T | T | . | 2.32 | −1.79 | * | * | F | 3.40 | 4.66 |
| Ser | 1126 | . | . | . | . | T | T | . | 1.36 | −1.10 | * | . | F | 3.06 | 1.89 |
| Arg | 1127 | A | . | . | . | . | T | . | 0.66 | −0.46 | . | . | F | 1.87 | 0.84 |
| Gln | 1128 | A | . | . | B | . | . | . | 0.66 | 0.33 | * | . | F | 0.53 | 0.47 |
| Ile | 1129 | A | . | . | B | . | . | . | −0.23 | −0.10 | * | . | . | 0.64 | 0.61 |
| Val | 1130 | A | . | . | B | . | . | . | −0.32 | 0.20 | * | . | . | −0.30 | 0.22 |
| Phe | 1131 | . | . | B | B | . | . | . | 0.02 | 0.59 | * | . | . | −0.60 | 0.17 |
| Glu | 1132 | . | . | B | B | . | . | . | −0.09 | 0.19 | * | . | . | −0.30 | 0.48 |
| Ile | 1133 | . | . | B | B | . | . | . | −0.09 | −0.10 | * | * | F | 0.60 | 1.12 |
| Ser | 1134 | . | A | . | . | . | . | C | 0.80 | −0.74 | . | * | F | 1.10 | 2.24 |
| Lys | 1135 | . | A | . | . | T | . | . | 1.37 | −1.53 | . | . | F | 1.30 | 2.16 |
| Gln | 1136 | . | A | . | . | T | . | . | 2.07 | −0.61 | . | * | F | 1.30 | 3.24 |
| Glu | 1137 | A | A | . | . | . | . | . | 1.21 | −0.90 | . | * | F | 0.90 | 4.18 |
| Asp | 1138 | . | A | . | B | T | . | . | 1.89 | −0.64 | . | * | F | 1.30 | 1.55 |
| Trp | 1139 | . | A | . | B | T | . | . | 1.30 | −0.21 | . | * | . | 0.85 | 1.39 |
| Gln | 1140 | . | A | B | B | . | . | . | 0.97 | 0.07 | . | * | . | −0.30 | 0.56 |
| Val | 1141 | . | A | B | B | . | . | . | 0.08 | 0.99 | . | * | . | −0.60 | 0.35 |
| Pro | 1142 | . | A | B | B | . | . | . | −0.81 | 1.67 | . | * | . | −0.60 | 0.24 |
| Ile | 1143 | . | . | B | B | . | . | . | −1.67 | 1.44 | . | * | . | −0.60 | 0.10 |
| Trp | 1144 | . | . | B | B | . | . | . | −1.72 | 1.69 | . | * | . | −0.60 | 0.10 |
| Ile | 1145 | . | . | B | B | . | . | . | −2.02 | 1.47 | . | . | . | −0.60 | 0.06 |
| Ile | 1146 | . | . | B | B | . | . | . | −1.48 | 1.43 | . | . | . | −0.60 | 0.12 |
| Val | 1147 | . | . | B | B | . | . | . | −2.08 | 1.23 | . | . | . | −0.60 | 0.16 |
| Gly | 1148 | . | . | B | B | . | . | . | −1.53 | 1.00 | . | . | F | −0.45 | 0.19 |
| Ser | 1149 | . | . | . | B | . | . | C | −1.59 | 0.74 | . | . | F | −0.25 | 0.27 |
| Thr | 1150 | . | . | . | B | . | . | C | −1.51 | 0.49 | . | . | F | −0.25 | 0.35 |
| Leu | 1151 | . | . | . | B | . | . | C | −1.43 | 0.53 | . | . | F | −0.25 | 0.30 |
| Gly | 1152 | . | . | . | B | T | . | . | −1.39 | 0.79 | . | . | F | −0.05 | 0.18 |

TABLE 13-continued

| Res | Position | I | II | III | IV | V | VI | VII | VIII | IX | X | XI | XII | XIII | XIV |
|---|---|---|---|---|---|---|---|---|---|---|---|---|---|---|---|
| Gly | 1153 | . | A | B | B | . | . | . | −1.86 | 1.09 | . | . | . | −0.60 | 0.10 |
| Leu | 1154 | . | A | B | B | . | . | . | −2.14 | 1.29 | . | . | . | −0.60 | 0.10 |
| Leu | 1155 | . | A | B | B | . | . | . | −2.64 | 1.10 | . | . | . | −0.60 | 0.11 |
| Leu | 1156 | A | A | . | B | . | . | . | −2.64 | 1.36 | . | . | . | −0.60 | 0.09 |
| Leu | 1157 | A | A | . | B | . | . | . | −3.16 | 1.61 | . | . | . | −0.60 | 0.09 |
| Ala | 1158 | A | A | . | B | . | . | . | −3.62 | 1.57 | . | . | . | −0.60 | 0.08 |
| Leu | 1159 | A | A | . | B | . | . | . | −3.40 | 1.57 | . | . | . | −0.60 | 0.08 |
| Leu | 1160 | A | A | . | B | . | . | . | −3.40 | 1.39 | . | . | . | −0.60 | 0.10 |
| Val | 1161 | A | A | . | B | . | . | . | −2.88 | 1.39 | . | . | . | −0.60 | 0.08 |
| Leu | 1162 | A | A | . | B | . | . | . | −2.02 | 1.80 | * | . | . | −0.60 | 0.10 |
| Ala | 1163 | A | A | . | B | . | . | . | −2.24 | 1.11 | . | . | . | −0.60 | 0.25 |
| Leu | 1164 | A | A | . | B | . | . | . | −1.78 | 1.11 | . | * | . | −0.60 | 0.27 |
| Trp | 1165 | A | A | . | B | . | . | . | −1.67 | 0.90 | . | . | . | −0.60 | 0.33 |
| Lys | 1166 | A | A | . | B | . | . | . | −1.51 | 1.00 | . | . | . | −0.60 | 0.28 |
| Leu | 1167 | A | A | . | B | . | . | . | −0.59 | 1.29 | . | . | . | −0.60 | 0.29 |
| Gly | 1168 | A | . | . | B | . | . | . | −0.30 | 0.60 | . | . | . | −0.60 | 0.55 |
| Phe | 1169 | . | . | B | B | . | . | . | −0.08 | 0.07 | * | . | . | −0.30 | 0.37 |
| Phe | 1170 | . | . | B | B | . | . | . | 0.32 | 0.57 | * | . | . | −0.60 | 0.45 |
| Arg | 1171 | . | . | B | B | . | . | . | 0.39 | −0.11 | * | . | . | 0.30 | 0.89 |
| Ser | 1172 | . | . | . | B | . | . | C | 1.31 | −0.54 | * | . | F | 1.10 | 2.02 |
| Ala | 1173 | . | . | . | . | . | . | C | 1.77 | −1.33 | * | . | F | 1.30 | 4.57 |
| Arg | 1174 | . | . | . | . | . | . | C | 2.47 | −2.11 | * | . | F | 1.30 | 4.57 |
| Arg | 1175 | . | . | . | . | T | . | . | 2.96 | −2.11 | * | . | F | 1.84 | 5.90 |
| Arg | 1176 | . | . | . | . | T | . | . | 2.50 | −2.07 | * | . | F | 2.18 | 9.03 |
| Arg | 1177 | . | . | . | . | T | . | . | 1.99 | −2.14 | . | . | F | 2.52 | 4.56 |
| Glu | 1178 | . | . | . | . | . | T | C | 2.58 | −1.46 | . | . | F | 2.86 | 1.92 |
| Pro | 1179 | . | . | . | . | T | T | . | 2.26 | −1.46 | . | . | F | 3.40 | 1.64 |
| Gly | 1180 | . | . | . | . | T | T | . | 1.83 | −1.03 | . | . | F | 3.06 | 1.29 |
| Leu | 1181 | . | . | . | . | . | T | C | 1.51 | −0.54 | . | * | F | 2.69 | 1.08 |
| Asp | 1182 | . | . | . | . | . | T | C | 1.44 | −0.11 | . | * | F | 2.22 | 1.08 |
| Pro | 1183 | . | . | . | . | . | T | C | 0.59 | −0.54 | * | * | F | 2.35 | 2.18 |
| Thr | 1184 | . | . | . | . | . | T | C | −0.01 | −0.33 | * | . | F | 1.88 | 1.96 |
| Pro | 1185 | . | . | B | . | . | T | . | 0.33 | −0.33 | * | . | F | 1.70 | 0.97 |
| Lys | 1186 | . | A | B | . | . | . | . | 0.76 | −0.33 | * | * | F | 1.28 | 1.08 |
| Val | 1187 | . | A | B | . | . | . | . | 0.37 | −0.33 | * | . | F | 0.96 | 0.96 |
| Leu | 1188 | A | A | . | . | . | . | . | 0.19 | −0.39 | * | . | . | 0.64 | 0.79 |
| Glu | 1189 | A | A | . | . | . | . | . | 0.11 | −0.39 | * | . | . | 0.47 | 0.51 |

INCORPORATION BY REFERENCE

The entire disclosure of each document cited (including patents, patent applications, journal articles, abstracts, laboratory manuals, books, or other disclosures) in the Background of the Invention, Detailed Description, and Examples is hereby incorporated herein by reference. In addition, the sequence listing submitted herewith is incorporated herein by reference in its entirety. The specification and sequence listing of each of the following U.S. and PCT applications are herein incorporated by reference in their entirety: U.S. Provisional Appln. No. 60/243,792 filed on Oct. 30, 2000, U.S. Provisional Appln. No. 60/198,407 filed on Apr. 19, 2000, U.S. Provisional Appln. No. 60/105,971 filed on Oct. 28, 1998, U.S. application Ser. No. 09/836,353 filed on Apr. 18, 2001, PCT Appln. No. PCT/US99/25031 filed on Oct. 27, 1999, U.S. Provisional Appln. No. 60/304,417 filed on Jul. 12, 2001, U.S. Provisional Appln. No. 60/270,625 filed on Feb. 23, 2001, U.S. Provisional Appln. No. 60/277,340 filed on 21 Mar. 2001, U.S. Provisional Appln. No. 60/306,171 filed on 19 Jul. 2001, U.S. Provisional Appln. No. 60/278,650 filed on 27 Mar. 2001, U.S. Provisional Appln. No. 60/331,287 filed on 13 Nov. 2001, U.S. application Ser. No. 09/950,082 filed on 12 Sep. 2001, U.S. application Ser. No. 09/950,083 filed on 12 Sep. 2001, U.S. Provisional Appln. No. 60/040,162 filed on 7 Mar. 1997, U.S. Provisional Appln. No. 60/043,576 filed on 11 Apr. 1997, U.S. Provisional Appln. No. 60/047,601 filed on 23 May 1997, U.S. Provisional Appln. No. 60/056,845 filed on 22 Aug. 1997, U.S. Provisional Appln. No. 60/043,580 filed on 11 Apr. 1997, U.S. Provisional Appln. No. 60/047,599 filed on 23 May 1997, U.S. Provisional Appln. No. 60/056,664 filed on 22 Aug. 1997, U.S. Provisional Appln. No. 60/043,314 filed on 11 Apr. 1997, U.S. Provisional Appln. No. 60/047,632 filed on 23 May 1997, U.S. Provisional Appln. No. 60/056,892 filed on 22 Aug. 1997, U.S. Provisional Appln. No. 60/043,568 filed on 11 Apr. 1997, U.S. Provisional Appln. No. 60/047,595 filed on 23 May 1997, U.S. Provisional Appln. No. 60/056,632 filed on 22 Aug. 1997, U.S. Provisional Appln. No. 60/043,578 filed on 11 Apr. 1997, U.S. Provisional Appln. No. 60/040,333 filed on 7 Mar. 1997, U.S. Provisional Appln. No. 60/043,670 filed on 11 Apr. 1997, U.S. Provisional Appln. No. 60/047,596 filed on 23 May 1997, U.S. Provisional Appln. No. 60/056,864 filed on 22 Aug. 1997, U.S. Provisional Appln. No. 60/043,674 filed on 11 Apr. 1997, U.S. Provisional Appln. No. 60/047,612 filed on 23 May 1997, U.S. Provisional Appln. No. 60/056,631 filed on 22 Aug. 1997, U.S. Provisional Appln. No. 60/043,569 filed on 11 Apr. 1997, U.S. Provisional Appln. No. 60/047,588 filed on 23 May 1997, U.S. Provisional Appln. No. 60/056,876 filed on 22 Aug. 1997, U.S. Provisional Appln. No. 60/043,671 filed on 11 Apr. 1997, U.S. Provisional Appln. No. 60/043,311 filed on 11 Apr. 1997, U.S. Provisional Appln. No. 60/038,621 filed on 7 Mar. 1997, U.S. Provisional Appln. No. 60/043,672 filed on 11 Apr. 1997, U.S. Provisional Appln. No. 60/047,613 filed on 23 May 1997, U.S. Provisional Appln. No. 60/056,636 filed on 22 Aug. 1997, U.S. Provisional Appln. No. 60/043,669 filed on 11 Apr. 1997, U.S. Provisional Appln. No. 60/047,582 filed on 23 May 1997, U.S. Provisional Appln. No. 60/056,910 filed on 22 Aug. 1997, U.S. Provisional Appln. No. 60/043,315 filed on 11 Apr. 1997, U.S. Provisional Appln. No. 60/047,598 filed on 23 May 1997, U.S. Provisional Appln. No. 60/056,874 filed on 22 Aug. 1997, U.S. Provisional Appln. No. 60/043,312 filed on 11 Apr. 1997, U.S. Provisional Appln. No. 60/047,585 filed on 23 May 1997, U.S. Provisional Appln. No. 60/056,881 filed on 22 Aug. 1997, U.S. Provisional Appln. No. 60/043,313 filed on 11 Apr. 1997, U.S. Provisional Appln. No. 60/047,586 filed on 23 May 1997, U.S. Provisional Appln. No. 60/056,909 filed on 22 Aug. 1997, U.S. Provisional Appln. No. 60/040,161 filed on 7 Mar. 1997, U.S. Provisional Appln. No. 60/047,587 filed on 23 May 1997, U.S. Provisional Appln. No. 60/056,879 filed on 22 Aug. 1997, U.S. Provisional Appln. No. 60/047,500 filed on 23 May 1997, U.S. Provisional Appln. No. 60/056,880 filed on 22 Aug. 1997, U.S. Provisional Appln. No. 60/047,584 filed on 23 May 1997, U.S. Provisional Appln. No. 60/056,894 filed on 22 Aug. 1997, U.S. Provisional Appln. No. 60/047,492 filed on 23 May 1997, U.S. Provisional Appln. No. 60/056,911 filed on 22 Aug. 1997, U.S. Provisional Appln. No. 60/040,626 filed on 7 Mar. 1997, U.S. Provisional Appln. No. 60/047,503 filed on 23 May 1997, U.S. Provisional Appln. No. 60/056,903 filed on 22 Aug. 1997, U.S. Provisional Appln. No. 60/047,501 filed on 23 May 1997, U.S. Provisional Appln. No. 60/056,637 filed on 22 Aug. 1997, U.S. Provisional Appln. No. 60/047,590 filed on 23 May 1997, U.S. Provisional Appln. No. 60/056,875 filed on 22 Aug. 1997, U.S. Provisional Appln. No. 60/047,581 filed on 23 May 1997, U.S. Provisional Appln. No. 60/056,882 filed on 22 Aug. 1997, U.S. Provisional Appln. No. 60/047,592 filed on 23 May 1997, U.S. Provisional Appln. No. 60/056,888 filed on 22 Aug. 1997, U.S. Provisional Appln. No. 60/040,334 filed on 7 Mar. 1997, U.S. Provisional Appln. No. 60/047,618 filed on 23 May 1997, U.S. Provisional Appln. No. 60/056,872 filed on 22 Aug. 1997, U.S. Provisional Appln. No. 60/047,617 filed on 23 May 1997, U.S. Provisional Appln. No. 60/056,662 filed on 22 Aug. 1997, U.S. Provisional Appln. No. 60/047,589 filed on 23 May 1997, U.S. Provisional Appln. No. 60/056,862 filed on 22 Aug. 1997, U.S. Provisional Appln. No. 60/047,594 filed on 23 May 1997, U.S. Provisional Appln. No. 60/056,884 filed on 22 Aug. 1997, U.S. Provisional Appln. No. 60/047,583 filed on 23 May 1997, U.S. Provisional Appln. No. 60/056,878 filed on 22 Aug. 1997, U.S. Provisional Appln. No. 60/040,336 filed on 7 Mar. 1997, U.S. Provisional Appln. No. 60/047,502 filed on 23 May 1997, U.S. Provisional Appln. No. 60/056,893 filed on 22 Aug. 1997, U.S. Provisional Appln. No. 60/047,633 filed on 23 May 1997, U.S. Provisional Appln. No. 60/056,630 filed on 22 Aug. 1997, U.S. Provisional Appln. No. 60/047,593 filed on 23 May 1997, U.S. Provisional Appln. No. 60/056,887 filed on 22 Aug. 1997, U.S. Provisional Appln. No. 60/040,163 filed on 7 Mar. 1997, U.S. Provisional Appln. No. 60/047,597 filed on 23 May 1997, U.S. Provisional Appln. No. 60/056,889 filed on 22 Aug. 1997, U.S. Provisional Appln. No. 60/047,615 filed on 23 May 1997, U.S. Provisional Appln. No. 60/056,877 filed on 22 Aug. 1997, U.S. Provisional Appln. No. 60/047,600 filed on 23 May 1997, U.S. Provisional Appln. No. 60/056,886 filed on 22 Aug. 1997, U.S. Provisional Appln. No. 60/047,614 filed on 23 May 1997, U.S. Provisional Appln. No. 60/056,908 filed on 22 Aug. 1997, U.S. Provisional Appln. No. 60/040,710 filed on 14 Mar. 1997, U.S. Provisional Appln. No. 60/050,934 filed on 30 May 1997, U.S. Provisional Appln. No. 60/048,100 filed on 30 May 1997, U.S. Provisional Appln. No. 60/040,762 filed on 14 Mar. 1997, U.S. Provisional Appln. No. 60/048,357 filed on 30 May 1997, U.S. Provisional Appln. No. 60/048,189 filed on 30 May 1997, U.S. Provisional Appln. No. 60/041,277 filed on 21 Mar. 1997, U.S. Provisional Appln. No. 60/048,188 filed on 30 May 1997, U.S. Provisional Appln. No. 60/048,094 filed on 30 May 1997, U.S. Provisional Appln. No. 60/048,350 filed on 30 May 1997, U.S. Provisional Appln. No. 60/048,135 filed on 30 May 1997, U.S. Provisional Appln. No. 60/042,344 filed on 21 Mar. 1997, U.S. Provisional Appln. No. 60/048,187 filed on 30 May 1997, U.S. Provisional Appln. No. 60/048,099 filed on 30 May 1997, U.S. Provisional Appln. No. 60/050,937 filed on 30 May 1997, U.S. Provisional Appln. No. 60/048,352 filed on 30 May 1997, U.S. Provisional Appln. No. 60/041,276 filed on 21 Mar. 1997, U.S. Provisional Appln. No. 60/048,069 filed on 30 May 1997, U.S. Provisional Appln. No. 60/048,131 filed on 30 May 1997, U.S. Provisional Appln. No. 60/048,186 filed on 30 May 1997, U.S. Provisional Appln. No. 60/048,095 filed on 30 May 1997, U.S. Provisional Appln. No. 60/041,281 filed on 21 Mar. 1997, U.S. Provisional Appln. No. 60/048,355 filed on 30 May 1997, U.S. Provisional Appln. No. 60/048,096 filed on 30 May 1997, U.S. Provisional Appln. No. 60/048,351 filed on 30 May 1997, U.S. Provisional Appln. No. 60/048,154 filed on 30 May 1997, U.S. Provisional Appln. No. 60/048,160 filed on 30 May 1997, U.S. Provisional Appln. No. 60/042,825 filed on 8 Apr. 1997, U.S. Provisional Appln. No. 60/048,070 filed on 30 May 1997, U.S. Provisional Appln. No. 60/042,727 filed on 8 Apr. 1997, U.S. Provisional Appln. No. 60/048,068 filed on 30 May 1997, U.S. Provisional Appln. No. 60/042,726 filed on 8 Apr. 1997, U.S. Provisional Appln. No. 60/048,184 filed on 30 May 1997, U.S. Provisional Appln. No. 60/042,728 filed on 8 Apr. 1997, U.S. Provisional Appln. No. 60/042,754 filed on 8 Apr. 1997, U.S. Provisional Appln. No. 60/048,190 filed on 30 May 1997, U.S. Provisional Appln. No. 60/044,039 filed on 30 May 1997, U.S. Provisional Appln. No. 60/048,093 filed on 30 May 1997, U.S. Provisional Appln. No. 60/048,885 filed on 6 Jun. 1997, U.S. Provisional Appln. No. 60/057,645 filed on 5 Sep. 1997, U.S. Provisional Appln. No. 60/049,375 filed on 6 Jun. 1997, U.S. Provisional Appln. No. 60/057,642 filed on 5 Sep. 1997, U.S. Provisional Appln. No. 60/048,881 filed on 6 Jun. 1997, U.S. Provisional Appln. No. 60/057,668 filed on 5 Sep. 1997, U.S. Provisional Appln. No. 60/048,880 filed on 6 Jun. 1997, U.S. Provisional Appln. No. 60/057,635 filed on 5 Sep. 1997, U.S. Provisional Appln. No. 60/048,896 filed on 6 Jun. 1997, U.S. Provisional Appln. No. 60/057,627 filed on 5 Sep. 1997, U.S. Provisional Appln. No. 60/049,020 filed on 6 Jun. 1997, U.S. Provisional Appln. No. 60/057,667 filed on 5 Sep. 1997, U.S. Provisional Appln. No. 60/048,876 filed on 6 Jun. 1997, U.S. Provisional Appln. No. 60/057,666 filed on 5 Sep. 1997, U.S. Provisional Appln. No. 60/048,895 filed on 6 Jun. 1997, U.S. Provisional Appln. No. 60/057,764 filed on 5 Sep. 1997, U.S. Provisional Appln. No. 60/048,884 filed on 6 Jun. 1997, U.S. Provisional Appln. No. 60/057,643 filed on 5 Sep. 1997, U.S. Provisional Appln. No. 60/048,894 filed on 6 Jun. 1997, U.S. Provisional Appln. No. 60/057,769 filed on 5 Sep. 1997, U.S. Provisional Appln. No. 60/048,971 filed on 6 Jun. 1997, U.S. Provisional Appln. No. 60/057,763 filed on 5 Sep. 1997, U.S. Provisional Appln. No. 60/048,964 filed on 6 Jun. 1997, U.S. Provisional Appln. No. 60/057,650 filed on 5 Sep. 1997, U.S. Provisional Appln. No. 60/048,882 filed on 6 Jun. 1997, U.S. Provisional Appln. No. 60/057,584 filed on 5 Sep. 1997, U.S. Provisional Appln. No. 60/048,899 filed on 6 Jun. 1997, U.S. Provisional Appln. No. 60/057,647 filed on 5 Sep. 1997, U.S. Provisional Appln. No. 60/048,893 filed on 6 Jun. 1997, U.S. Provisional Appln. No. 60/057,661 filed on 5 Sep. 1997, U.S. Provisional Appln. No. 60/048,900 filed on 6 Jun. 1997, U.S. Provisional Appln. No. 60/057,662 filed on 5 Sep. 1997, U.S. Provisional Appln. No. 60/048,901 filed on 6 Jun. 1997, U.S. Provisional Appln. No. 60/057,646 filed on 5 Sep. 1997, U.S. Provisional Appln. No. 60/048,892 filed on 6 Jun. 1997, U.S. Provisional Appln. No. 60/057,654 filed on 5 Sep. 1997, U.S. Provisional Appln. No. 60/048,915 filed on 6 Jun. 1997, U.S. Provisional Appln. No. 60/057,651 filed on 5 Sep. 1997, U.S. Provisional Appln. No. 60/049,019 filed on 6 Jun. 1997, U.S. Provisional Appln. No. 60/057,644 filed on 5 Sep. 1997, U.S. Provisional Appln. No. 60/048,970 filed on 6 Jun. 1997, U.S. Provisional Appln. No. 60/057,765 filed on 5 Sep. 1997, U.S. Provisional Appln. No. 60/048,972 filed on 6 Jun. 1997, U.S. Provisional Appln. No. 60/057,762 filed on 5 Sep. 1997, U.S. Provisional Appln. No. 60/048,916 filed on 6 Jun. 1997, U.S. Provisional Appln. No. 60/057,775 filed on 5 Sep. 1997, U.S. Provisional Appln. No. 60/049,373 filed on 6 Jun. 1997, U.S. Provisional Appln. No. 60/057,648 filed on 5 Sep. 1997, U.S. Provisional Appln. No. 60/048,875 filed on 6 Jun. 1997, U.S. Provisional Appln. No. 60/057,774 filed on 5 Sep. 1997, U.S. Provisional Appln. No. 60/049,374 filed on 6 Jun. 1997, U.S. Provisional Appln. No. 60/057,649 filed on 5 Sep. 1997, U.S. Provisional Appln. No. 60/048,917 filed on 6 Jun. 1997, U.S. Provisional Appln. No. 60/057,770 filed on 5 Sep. 1997, U.S. Provisional Appln. No. 60/048,949 filed on 6 Jun. 1997, U.S. Provisional Appln. No. 60/057,771 filed on 5 Sep. 1997, U.S. Provisional Appln. No. 60/048,974 filed on 6 Jun. 1997, U.S. Provisional Appln. No. 60/057,761 filed on 5 Sep. 1997, U.S. Provisional Appln. No. 60/048,883 filed on 6 Jun. 1997, U.S. Provisional Appln. No. 60/057,760 filed on 5 Sep. 1997, U.S. Provisional Appln. No. 60/048,897 filed on 6 Jun. 1997, U.S. Provisional Appln. No. 60/057,776 filed on 5 Sep. 1997, U.S. Provisional Appln. No. 60/048,898 filed on 6 Jun. 1997, U.S. Provisional Appln. No. 60/057,778 filed on 5 Sep. 1997, U.S. Provisional Appln. No. 60/048,962 filed on 6 Jun. 1997, U.S. Provisional Appln. No. 60/057,629 filed on 5 Sep. 1997, U.S. Provisional Appln. No. 60/048,963 filed on 6 Jun. 1997, U.S. Provisional Appln. No. 60/057,628 filed on 5 Sep. 1997, U.S. Provisional Appln. No. 60/048,877 filed on 6 Jun. 1997, U.S. Provisional Appln. No. 60/057,777 filed on 5 Sep. 1997, U.S. Provisional Appln. No. 60/048,878 filed on 6 Jun. 1997, U.S. Provisional Appln. No. 60/057,634 filed on 5 Sep. 1997, U.S. Provisional Appln. No. 60/049,608 filed on 13 Jun. 1997, U.S. Provisional Appln. No. 60/058,669 filed on 12 Sep. 1997, U.S. Provisional Appln. No. 60/049,566 filed on 13 Jun. 1997, U.S. Provisional Appln. No. 60/058,668 filed on 12 Sep. 1997, U.S. Provisional Appln. No. 60/052,989 filed on 13 Jun. 1997, U.S. Provisional Appln. No. 60/058,750 filed on 12 Sep. 1997, U.S. Provisional Appln. No. 60/049,607 filed on 13 Jun. 1997, U.S. Provisional Appln. No. 60/058,665 filed on 12 Sep. 1997, U.S. Provisional Appln. No. 60/049,611 filed on 13 Jun. 1997, U.S. Provisional Appln. No. 60/058,971 filed on 12 Sep. 1997, U.S. Provisional Appln. No. 60/050,901 filed on 13 Jun. 1997, U.S. Provisional Appln. No. 60/058,972 filed on 12 Sep. 1997, U.S. Provisional Appln. No. 60/049,609 filed on 13 Jun. 1997, U.S. Provisional Appln. No. 60/058,975 filed on 12 Sep. 1997, U.S. Provisional Appln. No. 60/048,356 filed on 30 May 1997, U.S. Provisional Appln. No. 60/056,296 filed on 29 Aug. 1997, U.S. Provisional Appln. No. 60/048,101 filed on 30 May 1997, U.S. Provisional Appln. No. 60/056,293 filed on 29 Aug. 1997, U.S. Provisional Appln. No. 60/050,935 filed on 30 May 1997, U.S. Provisional Appln. No. 60/056,250 filed on 29 Aug. 1997, U.S. Provisional Appln. No. 60/049,610 filed on 13 Jun. 1997, U.S. Provisional Appln. No. 60/061,060 filed on 2 Oct. 1997, U.S. Provisional Appln. No. 60/049,606 filed on 13 Jun. 1997, U.S. Provisional Appln. No. 60/060,841 filed on 2 Oct. 1997, U.S. Provisional Appln. No. 60/049,550 filed on 13 Jun. 1997, U.S. Provisional Appln. No. 60/060,834 filed on 2 Oct. 1997, U.S. Provisional Appln. No. 60/049,549 filed on 13 Jun. 1997, U.S. Provisional Appln. No. 60/060,865 filed on 2 Oct. 1997, U.S. Provisional Appln. No. 60/049,548 filed on 13 Jun. 1997, U.S. Provisional Appln. No. 60/060,844 filed on 2 Oct. 1997, U.S. Provisional Appln. No. 60/049,547 filed on 13 Jun. 1997, U.S. Provisional Appln. No. 60/061,059 filed on 2 Oct. 1997, U.S. Provisional Appln. No. 60/051,381 filed on 1 Jul. 1997, U.S. Provisional Appln. No. 60/058,598 filed on 12 Sep. 1997, U.S. Provisional Appln. No. 60/051,480 filed on 1 Jul. 1997, U.S. Provisional Appln. No. 60/058,663 filed on 12 Sep. 1997, U.S. Provisional Appln. No. 60/051,926 filed on 8 Jul. 1997, U.S. Provisional Appln. No. 60/058,785 filed on 12 Sep. 1997, U.S. Provisional Appln. No. 60/052,793 filed on 8 Jul. 1997, U.S. Provisional Appln. No. 60/058,664 filed on 12 Sep. 1997, U.S. Provisional Appln. No. 60/051,925 filed on 8 Jul. 1997, U.S. Provisional Appln. No. 60/058,660 filed on 12 Sep. 1997, U.S. Provisional Appln. No. 60/051,929 filed on 8 Jul. 1997, U.S. Provisional Appln. No. 60/058,661 filed on 12 Sep. 1997, U.S. Provisional Appln. No. 60/052,803 filed on 8 Jul. 1997, U.S. Provisional Appln. No. 60/055,722 filed on 18 Aug. 1997, U.S. Provisional Appln. No. 60/052,732 filed on 8 Jul. 1997, U.S. Provisional Appln. No. 60/055,723 filed on 18 Aug. 1997, U.S. Provisional Appln. No. 60/051,932 filed on 8 Jul. 1997, U.S. Provisional Appln. No. 60/055,948 filed on 18 Aug. 1997, U.S. Provisional Appln. No. 60/051,931 filed on 8 Jul. 1997, U.S. Provisional Appln. No. 60/055,949 filed on 18 Aug. 1997, U.S. Provisional Appln. No. 60/051,916 filed on 8 Jul. 1997, U.S. Provisional Appln. No. 60/055,953 filed on 18 Aug. 1997, U.S. Provisional Appln. No. 60/051,930 filed on 8 Jul. 1997, U.S. Provisional Appln. No. 60/055,950 filed on 18 Aug. 1997, U.S. Provisional Appln. No. 60/051,918 filed on 8 Jul. 1997, U.S. Provisional Appln. No. 60/055,947 filed on 18 Aug. 1997, U.S. Provisional Appln. No. 60/051,920 filed on 8 Jul. 1997, U.S. Provisional Appln. No. 60/055,964 filed on 18 Aug. 1997, U.S. Provisional Appln. No. 60/052,733 filed on 8 Jul. 1997, U.S. Provisional Appln. No. 60/056,360 filed on 18 Aug. 1997, U.S. Provisional Appln. No. 60/052,795 filed on 8 Jul. 1997, U.S. Provisional Appln. No. 60/055,684 filed on 18 Aug. 1997, U.S. Provisional Appln. No. 60/051,919 filed on 8 Jul. 1997, U.S. Provisional Appln. No. 60/055,984 filed on 18 Aug. 1997, U.S. Provisional Appln. No. 60/051,928 filed on 8 Jul. 1997, U.S. Provisional Appln. No. 60/055,954 filed on 18 Aug. 1997, U.S. Provisional Appln. No. 60/052,870 filed on 16 Jul. 1997, U.S. Provisional Appln. No. 60/055,952 filed on 18 Aug. 1997, U.S. Provisional Appln. No. 60/052,871 filed on 16 Jul. 1997, U.S. Provisional Appln. No. 60/055,725 filed on 18 Aug. 1997, U.S. Provisional Appln. No. 60/052,872 filed on 16 Jul. 1997, U.S. Provisional Appln. No. 60/056,359 filed on 18 Aug. 1997, U.S. Provisional Appln. No. 60/052,661 filed on 16 Jul. 1997, U.S. Provisional Appln. No. 60/055,985 filed on 18 Aug. 1997, U.S. Provisional Appln. No. 60/052,874 filed on 16 Jul. 1997, U.S. Provisional Appln. No. 60/055,724 filed on 18 Aug. 1997, U.S. Provisional Appln. No. 60/052,873 filed on 16 Jul. 1997, U.S. Provisional Appln. No. 60/055,726 filed on 18 Aug. 1997, U.S. Provisional Appln. No. 60/052,875 filed on 16 Jul. 1997, U.S. Provisional Appln. No. 60/056,361 filed on 18 Aug. 1997, U.S. Provisional Appln. No. 60/053,440 filed on 22 Jul. 1997, U.S. Provisional Appln. No. 60/055,989 filed on 18 Aug. 1997, U.S. Provisional Appln. No. 60/053,441 filed on 22 Jul. 1997, U.S. Provisional Appln. No. 60/055,946 filed on 18 Aug. 1997, U.S. Provisional Appln. No. 60/053,442 filed on 22 Jul. 1997, U.S. Provisional Appln. No. 60/055,683 filed on 18 Aug. 1997, U.S. Provisional Appln. No. 60/054,212 filed on 30 Jul. 1997, U.S. Provisional Appln. No. 60/055,968 filed on 18 Aug. 1997, U.S. Provisional Appln. No. 60/054,209 filed on 30 Jul. 1997, U.S. Provisional Appln. No. 60/055,972 filed on 18 Aug. 1997, U.S. Provisional Appln. No. 60/054,234 filed on 30 Jul. 1997, U.S. Provisional Appln. No. 60/055,969 filed on 18 Aug. 1997, U.S. Provisional Appln. No. 60/055,386 filed on 5 Aug. 1997, U.S. Provisional Appln. No. 60/055,986 filed on 18 Aug. 1997, U.S. Provisional Appln. No. 60/054,807 filed on 5 Aug. 1997, U.S. Provisional Appln. No. 60/055,970 filed on 18 Aug. 1997, U.S. Provisional Appln. No. 60/054,215 filed on 30 Jul. 1997, U.S. Provisional Appln. No. 60/056,543 filed on 19 Aug. 1997, U.S. Provisional Appln. No. 60/054,218 filed on 30 Jul. 1997, U.S. Provisional Appln. No. 60/056,561 filed on 19 Aug. 1997, U.S. Provisional Appln. No. 60/054,214 filed on 30 Jul. 1997, U.S. Provisional Appln. No. 60/056,534 filed on 19 Aug. 1997, U.S. Provisional Appln. No. 60/054,236 filed on 30 Jul. 1997, U.S. Provisional Appln. No. 60/056,729 filed on 19 Aug. 1997, U.S. Provisional Appln. No. 60/054,213 filed on 30 Jul. 1997, U.S. Provisional Appln. No. 60/056,727 filed on 19 Aug. 1997, U.S. Provisional Appln. No. 60/054,211 filed on 30 Jul. 1997, U.S. Provisional Appln. No. 60/056,554 filed on 19 Aug. 1997, U.S. Provisional Appln. No. 60/054,217 filed on 30 Jul. 1997, U.S. Provisional Appln. No. 60/056,730 filed on 19 Aug. 1997, U.S. Provisional Appln. No. 60/055,312 filed on 5 Aug. 1997, U.S. Provisional Appln. No. 60/056,563 filed on 19 Aug. 1997, U.S. Provisional Appln. No. 60/055,309 filed on 5 Aug. 1997, U.S. Provisional Appln. No. 60/056,557 filed on 19 Aug. 1997, U.S. Provisional Appln. No. 60/055,310 filed on 5 Aug. 1997, U.S. Provisional Appln. No. 60/056,371 filed on 19 Aug. 1997, U.S. Provisional Appln. No. 60/054,798 filed on 5 Aug. 1997, U.S. Provisional Appln. No. 60/056,732 filed on 19 Aug. 1997, U.S. Provisional Appln. No. 60/056,369 filed on 19 Aug. 1997, U.S. Provisional Appln. No. 60/056,535 filed on 19 Aug. 1997, U.S. Provisional Appln. No. 60/056,556 filed on 19 Aug. 1997, U.S. Provisional Appln. No. 60/056,555 filed on 19 Aug. 1997, U.S. Provisional Appln. No. 60/054,806 filed on 5 Aug. 1997, U.S. Provisional Appln. No. 60/056,366 filed on 19 Aug. 1997, U.S. Provisional Appln. No. 60/054,809 filed on 5 Aug. 1997, U.S. Provisional Appln. No. 60/056,364 filed on 19 Aug. 1997, U.S. Provisional Appln. No. 60/054,804 filed on 5 Aug. 1997, U.S. Provisional Appln. No. 60/056,370 filed on 19 Aug. 1997, U.S. Provisional Appln. No. 60/054,803 filed on 5 Aug. 1997, U.S. Provisional Appln. No. 60/056,731 filed on 19 Aug. 1997, U.S. Provisional Appln. No. 60/055,311 filed on 5 Aug. 1997, U.S. Provisional Appln. No. 60/056,365 filed on 19 Aug. 1997, U.S. Provisional Appln. No. 60/054,808 filed on 5 Aug. 1997, U.S. Provisional Appln. No. 60/056,367 filed on 19 Aug. 1997, U.S. Provisional Appln. No. 60/056,726 filed on 19 Aug. 1997, U.S. Provisional Appln. No. 60/056,368 filed on 19 Aug. 1997, U.S. Provisional Appln. No. 60/056,728 filed on 19 Aug. 1997, U.S. Provisional Appln. No. 60/056,628 filed on 19 Aug. 1997, U.S. Provisional Appln. No. 60/056,629 filed on 19 Aug. 1997, U.S. Provisional Appln. No. 60/056,270 filed on 29 Aug. 1997, U.S. Provisional Appln. No. 60/056,271 filed on 29 Aug. 1997, U.S. Provisional Appln. No. 60/056,247 filed on 29 Aug. 1997, U.S. Provisional Appln. No. 60/056,073 filed on 29 Aug. 1997, U.S. Provisional Appln. No. 60/057,669 filed on 5 Sep. 1997, U.S. Provisional Appln. No. 60/057,663 filed on 5 Sep. 1997, U.S. Provisional Appln. No. 60/057,626 filed on 5 Sep. 1997, U.S. Provisional Appln. No. 60/058,666 filed on 12 Sep. 1997, U.S. Provisional Appln. No. 60/058,973 filed on 12 Sep. 1997, U.S. Provisional Appln. No. 60/058,974 filed on 12 Sep. 1997, U.S. Provisional Appln. No. 60/058,667 filed on 12 Sep. 1997, U.S. Provisional Appln. No. 60/060,837 filed on 2 Oct. 1997, U.S. Provisional Appln. No. 60/060,862 filed on 2 Oct. 1997, U.S. Provisional Appln. No. 60/060,839 filed on 2 Oct. 1997, U.S. Provisional Appln. No. 60/060,866 filed on 2 Oct. 1997, U.S. Provisional Appln. No. 60/060,843 filed on 2 Oct. 1997, U.S. Provisional Appln. No. 60/060,836 filed on 2 Oct. 1997, U.S. Provisional Appln. No. 60/060,838 filed on 2 Oct. 1997, U.S. Provisional Appln. No. 60/060,874 filed on 2 Oct. 1997, U.S. Provisional Appln. No. 60/060,833 filed on 2 Oct. 1997, U.S. Provisional Appln. No. 60/060,884 filed on 2 Oct. 1997, U.S. Provisional Appln. No. 60/060,880 filed on 2 Oct. 1997, U.S. Provisional Appln. No. 60/061,463 filed on 9 Oct. 1997, U.S. Provisional Appln. No. 60/061,529 filed on 9 Oct. 1997, U.S. Provisional Appln. No. 60/071,498 filed on 9 Oct. 1997, U.S. Provisional Appln. No. 60/061,527 filed on 9 Oct. 1997, U.S. Provisional Appln. No. 60/061,536 filed on 9 Oct. 1997, U.S. Provisional Appln. No. 60/061,532 filed on 9 Oct. 1997, U.S. Provisional Appln. No. 60/063,099 filed on 24 Oct. 1997, U.S. Provisional Appln. No. 60/063,088 filed on 24 Oct. 1997, U.S. Provisional Appln. No. 60/063,100 filed on 24 Oct. 1997, U.S. Provisional Appln. No. 60/063,387 filed on 24 Oct. 1997, U.S. Provisional Appln. No. 60/063,148 filed on 24 Oct. 1997, U.S. Provisional Appln. No. 60/063,386 filed on 24 Oct. 1997, U.S. Provisional Appln. No. 60/062,784 filed on 24 Oct. 1997, U.S. Provisional Appln. No. 60/063,091 filed on 24 Oct. 1997, U.S. Provisional Appln. No. 60/063,090 filed on 24 Oct. 1997, U.S. Provisional Appln. No. 60/063,089 filed on 24 Oct. 1997, U.S. Provisional Appln. No. 60/063,092 filed on 24 Oct. 1997, U.S. Provisional Appln. No. 60/063,111 filed on 24 Oct. 1997, U.S. Provisional Appln. No. 60/063,101 filed on 24 Oct. 1997, U.S. Provisional Appln. No. 60/063,109 filed on 24 Oct. 1997, U.S. Provisional Appln. No. 60/063,110 filed on 24 Oct. 1997, U.S. Provisional Appln. No. 60/063,098 filed on 24 Oct. 1997, U.S. Provisional Appln. No. 60/063,097 filed on 24 Oct. 1997, U.S. Provisional Appln. No. 60/064,911 filed on 7 Nov. 1997, U.S. Provisional Appln. No. 60/064,912 filed on 7 Nov. 1997, U.S. Provisional Appln. No. 60/064,983 filed on 7 Nov. 1997, U.S. Provisional Appln. No. 60/064,900 filed on 7 Nov. 1997, U.S. Provisional Appln. No. 60/064,988 filed on 7 Nov. 1997, U.S. Provisional Appln. No. 60/064,987 filed on 7 Nov. 1997, U.S. Provisional Appln. No. 60/064,908 filed on 7 Nov. 1997, U.S. Provisional Appln. No. 60/064,984 filed on 7 Nov. 1997, U.S. Provisional Appln. No. 60/064,985 filed on 7 Nov. 1997, U.S. Provisional Appln. No. 60/066,094 filed on 17 Nov. 1997, U.S. Provisional Appln. No. 60/066,100 filed on 17 Nov. 1997, U.S. Provisional Appln. No. 60/066,089 filed on 17 Nov. 1997, U.S. Provisional Appln. No. 60/066,095 filed on 17 Nov. 1997, U.S. Provisional Appln. No. 60/066,090 filed on 17 Nov. 1997, U.S. Provisional Appln. No. 60/068,006 filed on 18 Dec. 1997, U.S. Provisional Appln. No. 60/068,057 filed on 18 Dec. 1997, U.S. Provisional Appln. No. 60/068,007 filed on 18 Dec. 1997, U.S. Provisional Appln. No. 60/068,008 filed on 18 Dec. 1997, U.S. Provisional Appln. No. 60/068,054 filed on 18 Dec. 1997, U.S. Provisional Appln. No. 60/068,064 filed on 18 Dec. 1997, U.S. Provisional Appln. No. 60/068,053 filed on 18 Dec. 1997, U.S. Provisional Appln. No. 60/070,923 filed on 18 Dec. 1997, U.S. Provisional Appln. No. 60/068,365 filed on 19 Dec. 1997, U.S. Provisional Appln. No. 60/068,169 filed on 19 Dec. 1997, U.S. Provisional Appln. No. 60/068,367 filed on 19 Dec. 1997, U.S. Provisional Appln. No. 60/068,369 filed on 19 Dec. 1997, U.S. Provisional Appln. No. 60/068,368 filed on 19 Dec. 1997, U.S. Provisional Appln. No. 60/070,657 filed on 7 Jan. 1998, U.S. Provisional Appln. No. 60/070,692 filed on 7 Jan. 1998, U.S. Provisional Appln. No. 60/070,704 filed on 7 Jan. 1998, U.S. Provisional Appln. No. 60/070,658 filed on 7 Jan. 1998, U.S. Provisional Appln. No. 60/073,160 filed on 30 Jan.

1998, U.S. Provisional Appln. No. 60/073,159 filed on 30 Jan. 1998, U.S. Provisional Appln. No. 60/073,165 filed on 30 Jan. 1998, U.S. Provisional Appln. No. 60/073,164 filed on 30 Jan. 1998, U.S. Provisional Appln. No. 60/073,167 filed on 30 Jan. 1998, U.S. Provisional Appln. No. 60/073,162 filed on 30 Jan. 1998, U.S. Provisional Appln. No. 60/073,161 filed on 30 Jan. 1998, U.S. Provisional Appln. No. 60/073,170 filed on 30 Jan. 1998, U.S. Provisional Appln. No. 60/074,141 filed on 9 Feb. 1998, U.S. Provisional Appln. No. 60/074,341 filed on 9 Feb. 1998, U.S. Provisional Appln. No. 60/074,037 filed on 9 Feb. 1998, U.S. Provisional Appln. No. 60/074,157 filed on 9 Feb. 1998, U.S. Provisional Appln. No. 60/074,118 filed on 9 Feb. 1998, U.S. Provisional Appln. No. 60/076,051 filed on 26 Feb. 1998, U.S. Provisional Appln. No. 60/076,053 filed on 26 Feb. 1998, U.S. Provisional Appln. No. 60/076,054 filed on 26 Feb. 1998, U.S. Provisional Appln. No. 60/076,052 filed on 26 Feb. 1998, U.S. Provisional Appln. No. 60/076, 057 filed on 26 Feb. 1998, U.S. Provisional Appln. No. 60/077,714 filed on 12 Mar. 1998, U.S. Provisional Appln. No. 60/077,687 filed on 12 Mar. 1998, U.S. Provisional Appln. No. 60/077,686 filed on 12 Mar. 1998, U.S. Provisional Appln. No. 60/077,696 filed on 12 Mar. 1998, U.S. Provisional Appln. No. 60/078,566 filed on 19 Mar. 1998, U.S. Provisional Appln. No. 60/078,574 filed on 19 Mar. 1998, U.S. Provisional Appln. No. 60/078,576 filed on 19 Mar. 1998, U.S. Provisional Appln. No. 60/078,579 filed on 19 Mar. 1998, U.S. Provisional Appln. No. 60/078,563 filed on 19 Mar. 1998, U.S. Provisional Appln. No. 60/078,573 filed on 19 Mar. 1998, U.S. Provisional Appln. No. 60/078, 578 filed on 19 Mar. 1998, U.S. Provisional Appln. No. 60/078,581 filed on 19 Mar. 1998, U.S. Provisional Appln. No. 60/078,577 filed on 19 Mar. 1998, U.S. Provisional Appln. No. 60/080,314 filed on 1 Apr. 1998, U.S. Provisional Appln. No. 60/080,312 filed on 1 Apr. 1998, U.S. Provisional Appln. No. 60/080,313 filed on 1 Apr. 1998, U.S. Provisional Appln. No. 60/085,180 filed on 12 May 1998, U.S. Provisional Appln. No. 60/085,105 filed on 12 May 1998, U.S. Provisional Appln. No. 60/085,094 filed on 12 May 1998, U.S. Provisional Appln. No. 60/085,093 filed on 12 May 1998, U.S. Provisional Appln. No. 60/085,924 filed on 18 May 1998, U.S. Provisional Appln. No. 60/085,906 filed on 18 May 1998, U.S. Provisional Appln. No. 60/085,927 filed on 18 May 1998, U.S. Provisional Appln. No. 60/085,920 filed on 18 May 1998, U.S. Provisional Appln. No. 60/085, 928 filed on 18 May 1998, U.S. Provisional Appln. No. 60/085,925 filed on 18 May 1998, U.S. Provisional Appln. No. 60/085,921 filed on 18 May 1998, U.S. Provisional Appln. No. 60/085,923 filed on 18 May 1998, U.S. Provisional Appln. No. 60/085,922 filed on 18 May 1998, U.S. Provisional Appln. No. 60/090,112 filed on 22 Jun. 1998, U.S. Provisional Appln. No. 60/089,508 filed on 16 Jun. 1998, U.S. Provisional Appln. No. 60/089,507 filed on 16 Jun. 1998, U.S. Provisional Appln. No. 60/089,510 filed on 16 Jun. 1998, U.S. Provisional Appln. No. 60/089,509 filed on 16 Jun. 1998, U.S. Provisional Appln. No. 60/090,113 filed on 22 Jun. 1998, U.S. Provisional Appln. No. 60/092, 956 filed on 15 Jul. 1998, U.S. Provisional Appln. No. 60/092, 921 filed on 15 Jul. 1998, U.S. Provisional Appln. No. 60/092, 922 filed on 15 Jul. 1998, U.S. Provisional Appln. No. 60/094, 657 filed on 30 Jul. 1998, U.S. Provisional Appln. No. 60/095, 486 filed on 5 Aug. 1998, U.S. Provisional Appln. No. 60/096, 319 filed on 12 Aug. 1998, U.S. Provisional Appln. No. 60/095,455 filed on 6 Aug. 1998, U.S. Provisional Appln. No. 60/095,454 filed on 6 Aug. 1998, U.S. Provisional Appln. No. 60/097,917 filed on 25 Aug. 1998, U.S. Provisional Appln. No. 60/098,634 filed on 31 Aug. 1998, U.S. Provisional Appln. No. 60/101,546 filed on 23 Sep. 1998, U.S. Provisional Appln. No. 60/102,895 filed on 2 Oct. 1998, U.S. Provisional Appln. No. 60/108,207 filed on 12 Nov. 1998, U.S. Provisional Appln. No. 60/113,006 filed on 18 Dec. 1998, U.S. Provisional Appln. No. 60/112,809 filed on 17 Dec. 1998, U.S. Provisional Appln. No. 60/116,330 filed on 19 Jan. 1999, U.S. Provisional Appln. No. 60/119,468 filed on 10 Feb. 1999, U.S. Provisional Appln. No. 60/125,055 filed on 18 Mar. 1999, U.S. Provisional Appln. No. 60/128,693 filed on 9 Apr. 1999, U.S. Provisional Appln. No. 60/130,991 filed on 26 Apr. 1999, U.S. Provisional Appln. No. 60/137, 725 filed on 7 Jun. 1999, U.S. Provisional Appln. No. 60/145, 220 filed on 23 Jul. 1999, U.S. Provisional Appln. No. 60/149, 182 filed on 17 Aug. 1999, U.S. Provisional Appln. No. 60/152,317 filed on 3 Sep. 1999, U.S. Provisional Appln. No. 60/152,315 filed on 3 Sep. 1999, U.S. Provisional Appln. No. 60/155,709 filed on 24 Sep. 1999, U.S. Provisional Appln. No. 60/163,085 filed on 2 Nov. 1999, U.S. Provisional Appln. No. 60/172,411 filed on 17 Dec. 1999, U.S. Provisional Appln. No. 60/162,239 filed on 29 Oct. 1999, U.S. Provisional Appln. No. 60/215,139 filed on 30 Jun. 2000, U.S. Provisional Appln. No. 60/162,211 filed on 29 Oct. 1999, U.S. Provisional Appln. No. 60/215,138 filed on 30 Jun. 2000, U.S. Provisional Appln. No. 60/162,240 filed on 29 Oct. 1999, U.S. Provisional Appln. No. 60/215,131 filed on 30 Jun. 2000, U.S. Provisional Appln. No. 60/162,237 filed on 29 Oct. 1999, U.S. Provisional Appln. No. 60/219,666 filed on 21 Jul. 2000, U.S. Provisional Appln. No. 60/162,238 filed on 29 Oct. 1999, U.S. Provisional Appln. No. 60/215, 134 filed on 30 Jun. 2000, U.S. Provisional Appln. No. 60/163,580 filed on 5 Nov. 1999, U.S. Provisional Appln. No. 60/215,130 filed on 30 Jun. 2000, U.S. Provisional Appln. No. 60/163,577 filed on 5 Nov. 1999, U.S. Provisional Appln. No. 60/215,137 filed on 30 Jun. 2000, U.S. Provisional Appln. No. 60/163,581 filed on 5 Nov. 1999, U.S. Provisional Appln. No. 60/215,133 filed on 30 Jun. 2000, U.S. Provisional Appln. No. 60/163,576 filed on 5 Nov. 1999, U.S. Provisional Appln. No. 60/221,366 filed on 27 Jul. 2000, U.S. Provisional Appln. No. 60/164,344 filed on 9 Nov. 1999, U.S. Provisional Appln. No. 60/195,296 filed on 7 Apr. 2000, U.S. Provisional Appln. No. 60/221,367 filed on 27 Jul. 2000, U.S. Provisional Appln. No. 60/164,835 filed on 12 Nov. 1999, U.S. Provisional Appln. No. 60/221,142 filed on 27 Jul. 2000, U.S. Provisional Appln. No. 60/164,744 filed on 12 Nov. 1999, U.S. Provisional Appln. No. 60/215,140 filed on 30 Jun. 2000, U.S. Provisional Appln. No. 60/164,735 filed on 12 Nov. 1999, U.S. Provisional Appln. No. 60/221,193 filed on 27 Jul. 2000, U.S. Provisional Appln. No. 60/164,825 filed on 12 Nov. 1999, U.S. Provisional Appln. No. 60/222,904 filed on 3 Aug. 2000, U.S. Provisional Appln. No. 60/164,834 filed on 12 Nov. 1999, U.S. Provisional Appln. No. 60/224, 007 filed on 4 Aug. 2000, U.S. Provisional Appln. No. 60/164, 750 filed on 12 Nov. 1999, U.S. Provisional Appln. No. 60/215,128 filed on 30 Jun. 2000, U.S. Provisional Appln. No. 60/166,415 filed on 19 Nov. 1999, U.S. Provisional Appln. No. 60/215,136 filed on 30 Jun. 2000, U.S. Provisional Appln. No. 60/166,414 filed on 19 Nov. 1999, U.S. Provisional Appln. No. 60/219,665 filed on 21 Jul. 2000, U.S. Provisional Appln. No. 60/164,731 filed on 12 Nov. 1999, U.S. Provisional Appln. No. 60/215,132 filed on 30 Jun. 2000, U.S. Provisional Appln. No. 60/226,280 filed on 18 Aug. 2000, U.S. Provisional Appln. No. 60/256,968 filed on 21 Dec. 2000, U.S. Provisional Appln. No. 60/226,380 filed on 18 Aug. 2000, U.S. Provisional Appln. No. 60/259,803 filed on 5 Jan. 2001, U.S. Provisional Appln. No. 60/228,084 filed on 28 Aug. 2000, U.S. application Ser. No. 09/915,582 filed on 27 Jul. 2001, U.S. Provisional Appln. No. 60/231,968 filed on 12 Sep. 2000, U.S. Provisional Appln. No. 60/236, 326 filed on 29 Sep. 2000, U.S. Provisional Appln. No. 60/234,211 filed on 20 Sep. 2000, U.S. Provisional Appln. No. 60/226,282 filed on 18 Aug. 2000, U.S. Provisional Appln. No. 60/232,104 filed on 12 Sep. 2000, U.S. Provisional Appln. No. 60/234,210 filed on 20 Sep. 2000, U.S. Provisional Appln. No. 60/226,278 filed on 18 Aug. 2000, U.S. Provisional Appln. No. 60/259,805 filed on 5 Jan. 2001, U.S. Provisional Appln. No. 60/226,279 filed on 18 Aug. 2000, U.S. Provisional Appln. No. 60/259,678 filed on 5 Jan. 2001, U.S. Provisional Appln. No. 60/226,281 filed on 18 Aug. 2000, U.S. Provisional Appln. No. 60/231,969 filed on 12 Sep. 2000, U.S. Provisional Appln. No. 60/228,086 filed on 28 Aug. 2000, U.S. Provisional Appln. No. 60/259,516 filed on 4 Jan. 2001, U.S. Provisional Appln. No. 60/228,083 filed on 28 Aug. 2000, U.S. Provisional Appln. No. 60/259,804 filed on 5 Jan. 2001, U.S. Provisional Appln. No. 60/270,658 filed on 23 Feb. 2001, U.S. Provisional Appln. No. 60/304,444 filed on 12 Jul. 2001, U.S. Provisional Appln. No. 60/295,869 filed on 6 Jun. 2001, U.S. Provisional Appln. No. 60/304,121 filed on 11 Jul. 2001, U.S. Provisional Appln. No. 60/311,085 filed on 10 Aug. 2001, U.S. Provisional Appln. No. 60/325,209 filed on 28 Sep. 2001, U.S. Provisional Appln. No. 60/330,629 filed on 26 Oct. 2001, U.S. Provisional Appln. No. 60/331,046 filed on 7 Nov. 2001, U.S. Provisional Appln. No. 60/358,554 filed on 22 Feb. 2002, U.S. Provisional Appln. No. 60/358,714 filed on 25 Feb. 2002, PCT Appln. No. PCT/US00/29363 filed on 25 Oct. 2000, PCT Appln. No. PCT/US00/29360 filed on 25 Oct. 2000, PCT Appln. No. PCT/US00/29362 filed on 25 Oct. 2000, PCT Appln. No. PCT/US00/29365 filed on 25 Oct. 2000, PCT Appln. No. PCT/US00/29364 filed on 25 Oct. 2000, PCT Appln. No. PCT/US00/30040 filed on 1 Nov. 2000, PCT Appln. No. PCT/US00/30037 filed on 1 Nov. 2000, PCT Appln. No. PCT/US00/30045 filed on 1 Nov. 2000, PCT Appln. No. PCT/US00/30036 filed on 1 Nov. 2000, PCT Appln. No. PCT/US00/30039 filed on 1 Nov. 2000, PCT Appln. No. PCT/US00/30654 filed on 8 Nov. 2000, PCT Appln. No. PCT/US00/30628 filed on 8 Nov. 2000, PCT Appln. No. PCT/US00/30653 filed on 8 Nov. 2000, PCT Appln. No. PCT/US00/30629 filed on 8 Nov. 2000, PCT Appln. No. PCT/US00/30679 filed on 8 Nov. 2000, PCT Appln. No. PCT/US00/30674 filed on 8 Nov. 2000, PCT Appln. No. PCT/US00/31162 filed on 15 Nov. 2000, PCT Appln. No. PCT/US00/31282 filed on 15 Nov. 2000, PCT Appln. No. PCT/US00/30657 filed on 8 Nov. 2000, PCT Appln. No. PCT/US01/01396 filed on 17 Jan. 2001, PCT Appln. No. PCT/US01/01387 filed on 17 Jan. 2001, PCT Appln. No. PCT/US01/01567 filed on 17 Jan. 2001, PCT Appln. No. PCT/US01/01431 filed on 17 Jan. 2001, PCT Appln. No. PCT/US01/01432 filed on 17 Jan. 2001, PCT Appln. No. PCT/US01/00544 filed on 9 Jan. 2001, PCT Appln. No. PCT/US01/01435 filed on 17 Jan. 2001, PCT Appln. No. PCT/US01/01386 filed on 17 Jan. 2001, PCT Appln. No. PCT/US01/01565 filed on 17 Jan. 2001, PCT Appln. No. PCT/US01/01394 filed on 17 Jan. 2001, PCT Appln. No. PCT/US01/01434 filed on 17 Jan. 2001, PCT Appln. No. PCT/US01/01397 filed on 17 Jan. 2001, PCT Appln. No. PCT/US01/01385 filed on 17 Jan. 2001, PCT Appln. No. PCT/US01/01384 filed on 17 Jan. 2001, PCT Appln. No. PCT/US01/01383 filed on 17 Jan. 2001, PCT Appln. No. PCT/US02/05064 filed on 21 Feb. 2002, PCT Appln. No. PCT/US02/05301 filed on 21 Feb. 2002, U.S. application Ser. No. 09/148,545 filed on 4 Sep. 1998, U.S. application Ser. No. 09/621,011 filed on 20 Jul. 2000, U.S. application Ser. No. 09/981,876 filed on 19 Oct. 2001, U.S. application Ser. No. 09/149,476 filed on 8 Sep. 1998, U.S. application Ser. No. 09/809,391 filed on 16 Mar. 2001, U.S. application Ser. No. 09/882,171 filed on 18 Jun. 2001, U.S. Provisional Appln. No. 60/190,068 filed on 17 Mar. 2000, U.S. application Ser. No. 09/152,060 filed on 11 Sep. 1998, U.S. application Ser. No. 09/852,797 filed on 11 May 2001, U.S. application Ser. No. 09/853,161 filed on 11 May 2001, U.S. application Ser. No. 09/852,659 filed on 11 May 2001, U.S. application Ser. No. 10/058,993 filed on 30 Jan. 2002, U.S. Provisional Appln. No. 60/265,583 filed on 2 Feb. 2001, U.S. application Ser. No. 09/154,707 filed on 17 Sep. 1998, U.S. application Ser. No. 09/966,262 filed on 1 Oct. 2001, U.S. application Ser. No. 09/983,966 filed on 26 Oct. 2001, U.S. application Ser. No. 10/059,395 filed on 31 Jan. 2002, U.S. application Ser. No. 09/984,245 filed on 29 Oct. 2001, U.S. application Ser. No. 09/166,780 filed on 6 Oct. 1998, U.S. application Ser. No. 09/577,145 filed on 24 May 2000, U.S. application Ser. No. 09/814,122 filed on 22 Mar. 2001, U.S. application Ser. No. 09/189,144 filed on 10 Nov. 1998, U.S. application Ser. No. 09/690,454 filed on 18 Oct. 2000, U.S. application Ser. No. 10/062,831 filed on 5 Feb. 2002, U.S. application Ser. No. 10/062,599 filed on 5 Feb. 2002, U.S. application Ser. No. 09/205,258 filed on 4 Dec. 1998, U.S. application Ser. No. 09/933,767 filed on 22 Aug. 2001, U.S. Provisional Appln. No. 60/184,836 filed on 24 Feb. 2000, U.S. Provisional Appln. No. 60/193,170 filed on 29 Mar. 2000, U.S. application Ser. No. 10/023,282 filed on 20 Dec. 2001, U.S. application Ser. No. 10/004,860 filed on 7 Dec. 2001, U.S. application Ser. No. 09/209,462 filed on 11 Dec. 1998, U.S. application Ser. No. 09/213,365 filed on 17 Dec. 1998, U.S. application Ser. No. 09/627,081 filed on 27 Jul. 2000, U.S. application Ser. No. 09/227,357 filed on 8 Jan. 1999, U.S. application Ser. No. 09/983,802 filed on 25 Oct. 2001, U.S. application Ser. No. 09/973,278 filed on 10 Oct. 2001, U.S. Provisional Appln. No. 60/239,899 filed on 13 Oct. 2000, U.S. application Ser. No. 09/984,490 filed on 30 Oct. 2001, U.S. application Ser. No. 09/776,724 filed on 6 Feb. 2001, U.S. application Ser. No. 09/229,982 filed on 14 Jan. 1999, U.S. application Ser. No. 09/669,688 filed on 26 Sep. 2000, U.S. Provisional Appln. No. 60/180,909 filed on 8 Feb. 2000, U.S. application Ser. No. 09/236,557 filed on 26 Jan. 1999, U.S. application Ser. No. 09/666,984 filed on 21 Sep. 2000, U.S. application Ser. No. 09/820,649 filed on 30 Mar. 2001, U.S. Provisional Appln. No. 60/295,558 filed on 5 Jun. 2001, U.S. application Ser. No. 09/244,112 filed on 4 Feb. 1999, U.S. application Ser. No. 09/774,639 filed on 1 Feb. 2001, U.S. application Ser. No. 09/969,730 filed on 4 Oct. 2001, U.S. Provisional Appln. No. 60/238,291 filed on 6 Oct. 2000, U.S. application Ser. No. 09/251,329 filed on 17 Feb. 1999, U.S. application Ser. No. 09/716,128 filed on 17 Nov. 2000, U.S. application Ser. No. 09/257,179 filed on 25 Feb. 1999, U.S. application Ser. No. 09/729,835 filed on 6 Dec. 2000, U.S. application Ser. No. 09/262,109 filed on 4 Mar. 1999, U.S. application Ser. No. 09/722,329 filed on 28 Nov. 2000, U.S. application Ser. No. 10/047,021 filed on 17 Jan. 2002, U.S. Provisional Appln. No. 60/262,066 filed on 18 Jan. 2001, U.S. application Ser. No. 09/281,976 filed on 31 Mar. 1999, U.S. application Ser. No. 09/288,143 filed on 8 Apr. 1999, U.S. application Ser. No. 09/984,429 filed on 30 Oct. 2001, U.S. Provisional Appln. No. 60/244,591 filed on 1 Nov. 2000, U.S. application Ser. No. 09/296,622 filed on 23 Apr. 1999, U.S. application Ser. No. 09/305,736 filed on 5 May 1999, U.S. application Ser. No. 09/818,683 filed on 28 Mar. 2001, U.S. application Ser. No. 09/974,879 filed on 12 Oct. 2001, U.S. Provisional Appln. No. 60/239,893 filed on 13 Oct. 2000, U.S. application Ser. No. 09/334,595 filed on 17 Jun. 1999, U.S. application Ser. No. 09/348,457 filed on 7 Jul. 1999, U.S. application Ser. No. 09/739,907 filed on 20 Dec. 2000, U.S. application Ser. No. 09/938,671 filed on 27 Aug.

2001, U.S. application Ser. No. 09/363,044 filed on 29 Jul. 1999, U.S. application Ser. No. 09/813,153 filed on 21 Mar. 2001, U.S. application Ser. No. 09/949,925 filed on 12 Sep. 2001, U.S. Provisional Appln. No. 60/232,150 filed on 12 Sep. 2000, U.S. application Ser. No. 09/369,247 filed on 5 Aug. 1999, U.S. application Ser. No. 10/062,548 filed on 5 Feb. 2002, U.S. application Ser. No. 09/382,572 filed on 25 Aug. 1999, U.S. application Ser. No. 09/716,129 filed on 17 Nov. 2000, U.S. application Ser. No. 09/393,022 filed on 9 Sep. 1999, U.S. application Ser. No. 09/798,889 filed on 6 Mar. 2001, U.S. application Ser. No. 09/397,945 filed on 17 Sep. 1999, U.S. application Ser. No. 09/437,658 filed on 10 Nov. 1999, U.S. application Ser. No. 09/892,877 filed on 28 Jun. 2001, U.S. application Ser. No. 09/948,783 filed on 10 Sep. 2001, U.S. Provisional Appln. No. 60/231,846 filed on 11 Sep. 2000, U.S. application Ser. No. 09/461,325 filed on 14 Dec. 1999, U.S. application Ser. No. 10/050,873 filed on 18 Jan. 2002, U.S. Provisional Appln. No. 60/263,230 filed on 23 Jan. 2001, U.S. Provisional Appln. No. 60/263,681 filed on 24 Jan. 2001, U.S. application Ser. No. 10/012,542 filed on 12 Dec. 2001, U.S. application Ser. No. 09/482,273 filed on 13 Jan. 2000, U.S. Provisional Appln. No. 60/234,925 filed on 25 Sep. 2000, U.S. application Ser. No. 09/984,276 filed on 29 Oct. 2001, U.S. application Ser. No. 09/984,271 filed on 29 Oct. 2001, U.S. application Ser. No. 09/489,847 filed on 24 Jan. 2000, U.S. Provisional Appln. No. 60/350,898 filed on 25 Jan. 2002, U.S. application Ser. No. 09/511,554 filed on 23 Feb. 2000, U.S. application Ser. No. 09/739,254 filed on 19 Dec. 2000, U.S. application Ser. No. 09/904,615 filed on 16 Jul. 2001, U.S. application Ser. No. 10/054,988 filed on 25 Jan. 2002, U.S. application Ser. No. 09/531,119 filed on 20 Mar. 2000, U.S. application Ser. No. 09/820,893 filed on 30 Mar. 2001, U.S. application Ser. No. 09/565,391 filed on 5 May 2000, U.S. application Ser. No. 09/948,820 filed on 10 Sep. 2001, U.S. application Ser. No. 09/591,316 filed on 9 Jun. 2000, U.S. application Ser. No. 09/895,298 filed on 2 Jul. 2001, U.S. application Ser. No. 09/618,150 filed on 17 Jul. 2000, U.S. application Ser. No. 09/985,153 filed on 1 Nov. 2001, U.S. application Ser. No. 09/628,508 filed on 28 Jul. 2000, U.S. application Ser. No. 09/997,131 filed on 30 Nov. 2001, U.S. application Ser. No. 09/661,453 filed on 13 Sep. 2000, U.S. application Ser. No. 10/050,882 filed on 18 Jan. 2002, U.S. application Ser. No. 09/684,524 filed on 10 Oct. 2000, U.S. application Ser. No. 10/050,704 filed on 18 Jan. 2002, U.S. application Ser. No. 09/726,643 filed on 1 Dec. 2000, U.S. application Ser. No. 10/042,141 filed on 11 Jan. 2002, U.S. application Ser. No. 09/756,168 filed on 9 Jan. 2001, U.S. application Ser. No. 09/781,417 filed on 13 Feb. 2001, U.S. application Ser. No. 10/060,255 filed on 1 Feb. 2002, U.S. application Ser. No. 09/789,561 filed on 22 Feb. 2001, U.S. application Ser. No. 09/800,729 filed on 8 Mar. 2001, U.S. application Ser. No. 09/832,129 filed on 11 Apr. 2001, PCT Appln. No. PCT/US98/04482 filed on 6 Mar. 1998, PCT Appln. No. PCT/US98/04493 filed on 6 Mar. 1998, PCT Appln. No. PCT/US98/04858 filed on 12 Mar. 1998, PCT Appln. No. PCT/US98/05311 filed on 19 Mar. 1998, PCT Appln. No. PCT/US98/06801 filed on 7 Apr. 1998, PCT Appln. No. PCT/US98/10868 filed on 28 May 1998, PCT Appln. No. PCT/US98/11422 filed on 4 Jun. 1998, PCT Appln. No. PCT/US01/05614 filed on 21 Feb. 2001, PCT Appln. No. PCT/US98/12125 filed on 11 Jun. 1998, PCT Appln. No. PCT/US98/13608 filed on 30 Jun. 1998, PCT Appln. No. PCT/US98/13684 filed on 7 Jul. 1998, PCT Appln. No. PCT/US98/14613 filed on 15 Jul. 1998, PCT Appln. No. PCT/US98/15949 filed on 29 Jul. 1998, PCT Appln. No. PCT/US98/16235 filed on 4 Aug. 1998, PCT Appln. No. PCT/US98/17044 filed on 18 Aug. 1998, PCT Appln. No. PCT/US98/17709 filed on 27 Aug. 1998, PCT Appln. No. PCT/US98/18360 filed on 3 Sep. 1998, PCT Appln. No. PCT/US02/01109 filed on 17 Jan. 2002, PCT Appln. No. PCT/US98/20775 filed on 1 Oct. 1998, PCT Appln. No. PCT/US98/21142 filed on 8 Oct. 1998, PCT Appln. No. PCT/US98/22376 filed on 23 Oct. 1998, PCT Appln. No. PCT/US98/23435 filed on 4 Nov. 1998, PCT Appln. No. PCT/US98/27059 filed on 17 Dec. 1998, PCT Appln. No. PCT/US99/00108 filed on 6 Jan. 1999, PCT Appln. No. PCT/US99/01621 filed on 27 Jan. 1999, PCT Appln. No. PCT/US99/02293 filed on 4 Feb. 1999, PCT Appln. No. PCT/US99/03939 filed on 24 Feb. 1999, PCT Appln. No. PCT/US99/05721 filed on 11 Mar. 1999, PCT Appln. No. PCT/US99/05804 filed on 18 Mar. 1999, PCT Appln. No. PCT/US99/09847 filed on 6 May 1999, PCT Appln. No. PCT/US99/13418 filed on 15 Jun. 1999, PCT Appln. No. PCT/US99/15849 filed on 14 Jul. 1999, PCT Appln. No. PCT/US01/00911 filed on 12 Jan. 2001, PCT Appln. No. PCT/US01/29871 filed on 24 Sep. 2001, PCT Appln. No. PCT/US99/17130 filed on 29 Jul. 1999, PCT Appln. No. PCT/US99/19330 filed on 24 Aug. 1999, PCT Appln. No. PCT/US99/22012 filed on 22 Sep. 1999, PCT Appln. No. PCT/US99/26409 filed on 9 Nov. 1999, PCT Appln. No. PCT/US99/29950 filed on 16 Dec. 1999, PCT Appln. No. PCT/US00/00903 filed on 18 Jan. 2000, PCT Appln. No. PCT/US00/03062 filed on 8 Feb. 2000, PCT Appln. No. PCT/US00/06783 filed on 16 Mar. 2000, PCT Appln. No. PCT/US00/08979 filed on 6 Apr. 2000, PCT Appln. No. PCT/US00/15187 filed on 2 Jun. 2000, PCT Appln. No. PCT/US00/19735 filed on 20 Jul. 2000, PCT Appln. No. PCT/US00/22325 filed on 16 Aug. 2000, PCT Appln. No. PCT/US00/24008 filed on 31 Aug. 2000, PCT Appln. No. PCT/US00/26013 filed on 22 Sep. 2000, PCT Appln. No. PCT/US00/28664 filed on 17 Oct. 2000, U.S. application Ser. No. 09/833,245 filed on 12 Apr. 2001, U.S. application Ser. No. 10/100,683 filed on 19 Mar. 2002, PCT Appln. No. PCT/US01/11988 filed on 12 Apr. 2001, PCT Appln. No. PCT/US02/08278 filed on 19 Mar. 2002, PCT Appln. No. PCT/US02/08279 filed on 19 Mar. 2002, PCT Appln. No. PCT/US02/08123 filed on 19 Mar. 2002, PCT Appln. No. PCT/US02/09785 filed on 19 Mar. 2002, PCT Appln. No. PCT/US02/08276 filed on 19 Mar. 2002, PCT Appln. No. PCT/US02/08277 filed on 19 Mar. 2002, PCT Appln. No. PCT/US02/08124 filed on 19 Mar. 2002, U.S. application Ser. No. 10/664,358 filed on 20 Sep. 2003, U.S. application Ser. No. 11/781,665 filed on 2007 Jul. 23, U.S. application Ser. No. 10/994,608 filed on 2004 Nov. 23, U.S. application Ser. No. 10/105,299 filed on 2002 Mar. 26, PCT Appln. No. PCT/US00/06043 filed on 2000 Mar. 9, PCT Appln. No. PCT/US00/06012 filed on 2000 Mar. 9, PCT Appln. No. PCT/US00/06058 filed on 2000 Mar. 9, PCT Appln. No. PCT/US00/06044 filed on 2000 Mar. 9, PCT Appln. No. PCT/US00/06059 filed on 2000 Mar. 9, PCT Appln. No. PCT/US00/06042 filed on 2000 Mar. 9, PCT Appln. No. PCT/US00/06014 filed on 2000 Mar. 9, PCT Appln. No. PCT/US00/06013 filed on 2000 Mar. 9, PCT Appln. No. PCT/US00/06049 filed on 2000 Mar. 9, PCT Appln. No. PCT/US00/06057 filed on 2000 Mar. 9, PCT Appln. No. PCT/US00/06824 filed on 2000 Mar. 16, PCT Appln. No. PCT/US00/06765 filed on 2000 Mar. 16, PCT Appln. No. PCT/US00/06792 filed on 2000 Mar. 16, PCT Appln. No. PCT/US00/06830 filed on 2000 Mar. 16, PCT Appln. No. PCT/US00/06782 filed on 2000 Mar. 16, PCT Appln. No. PCT/US00/06822 filed on 2000 Mar. 16, PCT Appln. No. PCT/US00/06791 filed on 2000 Mar. 16, PCT Appln. No. PCT/US00/06828 filed on 2000 Mar. 16, PCT Appln. No. PCT/US00/06823 filed on 2000 Mar. 16, PCT Appln. No. PCT/US00/06781 filed on 2000 Mar. 16, PCT Appln. No. PCT/US00/07505 filed on 2000 Mar. 22, PCT Appln. No. PCT/US00/07440 filed on 2000 Mar. 22, PCT Appln. No. PCT/US00/07506 filed on 2000 Mar. 22, PCT Appln. No. PCT/US00/07507 filed on 2000 Mar. 22, PCT Appln. No. PCT/US00/07535 filed on 2000 Mar. 22, PCT Appln. No. PCT/US00/07525 filed on 2000 Mar. 22, PCT Appln. No. PCT/US00/07534 filed on 2000 Mar. 22, PCT Appln. No. PCT/US00/07483 filed on 2000 Mar. 22, PCT Appln. No. PCT/US00/07526 filed on 2000 Mar. 22, PCT Appln. No. PCT/US00/07527 filed on 2000 Mar. 22, PCT Appln. No. PCT/US00/07661 filed on 2000 Mar. 23, PCT Appln. No. PCT/US00/07579 filed on 2000 Mar. 23, PCT Appln. No. PCT/US00/07723 filed on 2000 Mar. 23, PCT Appln. No. PCT/US00/07724 filed on 2000 Mar. 23, PCT Appln. No. PCT/US00/14929 filed on 2000 Jun. 1, PCT Appln. No. PCT/US00/07722 filed on 2000 Mar. 23, PCT Appln. No. PCT/US00/07578 filed on 2000 Mar. 23, PCT Appln. No. PCT/US00/07726 filed on 2000 Mar. 23, PCT Appln. No. PCT/US00/07677 filed on 2000 Mar. 23, PCT Appln. No. PCT/US00/07725 filed on 2000 Mar. 23, PCT Appln. No. PCT/US00/09070 filed on 2000 Apr. 6, PCT Appln. No. PCT/US00/08982 filed on 2000 Apr. 6, PCT Appln. No. PCT/US00/08983 filed on 2000 Apr. 6, PCT Appln. No. PCT/US00/09067 filed on 2000 Apr. 6, PCT Appln. No. PCT/US00/09066 filed on 2000 Apr. 6, PCT Appln. No. PCT/US00/09068 filed on 2000 Apr. 6, PCT Appln. No. PCT/US00/08981 filed on 2000 Apr. 6, PCT Appln. No. PCT/US00/08980 filed on 2000 Apr. 6, PCT Appln. No. PCT/US00/09071 filed on 2000 Apr. 6, PCT Appln. No. PCT/US00/09069 filed on 2000 Apr. 6, PCT Appln. No. PCT/US00/15136 filed on 2000 Jun. 1, PCT Appln. No. PCT/US00/14926 filed on 2000 Jun. 1, PCT Appln. No. PCT/US00/14963 filed on 2000 Jun. 1, PCT Appln. No. PCT/US00/15135 filed on 2000 Jun. 1, PCT Appln. No. PCT/US00/14934 filed on 2000 Jun. 1, PCT Appln. No. PCT/US00/14933 filed on 2000 Jun. 1, PCT Appln. No. PCT/US00/15137 filed on 2000 Jun. 1, PCT Appln. No. PCT/US00/14928 filed on 2000 Jun. 1, PCT Appln. No. PCT/US00/14973 filed on 2000 Jun. 1, PCT Appln. No. PCT/US00/14964 filed on 2000 Jun. 1, PCT Appln. No. PCT/US00/26376 filed on 2000 Sep. 26, PCT Appln. No. PCT/US00/26371 filed on 2000 Sep. 26, PCT Appln. No. PCT/US00/26324 filed on 2000 Sep. 26, PCT Appln. No. PCT/US00/26323 filed on 2000 Sep. 26, PCT Appln. No. PCT/US00/26337 filed on 2000 Sep. 26, PCT Appln. No. PCT/US01/13318 filed on 2001 Apr. 26, U.S. Provisional Appln. No. 60/124,146 filed on 1999 Mar. 12, U.S. Provisional Appln. No. 60/167,061 filed on 1999 Nov. 23, U.S. Provisional Appln. No. 60/124,093 filed on 1999 Mar. 12, U.S. Provisional Appln. No. 60/166,989 filed on 1999 Nov. 23, U.S. Provisional Appln. No. 60/124,145 filed on 1999 Mar. 12, U.S. Provisional Appln. No. 60/168,654 filed on 1999 Dec. 3, U.S. Provisional Appln. No. 60/124,099 filed on 1999 Mar. 12, U.S. Provisional Appln. No. 60/168,661 filed on 1999 Dec. 3, U.S. Provisional Appln. No. 60/124,096 filed on 1999 Mar. 12, U.S. Provisional Appln. No. 60/168,622 filed on 1999 Dec. 3, U.S. Provisional Appln. No. 60/124,143 filed on 1999 Mar. 12, U.S. Provisional Appln. No. 60/168,663 filed on 1999 Dec. 3, U.S. Provisional Appln. No. 60/124,095 filed on 1999 Mar. 12, U.S. Provisional Appln. No. 60/138,598 filed on 1999 Jun. 11, U.S. Provisional Appln. No. 60/168,665 filed on 1999 Dec. 3, U.S. Provisional Appln. No. 60/125,360 filed on 1999 Mar. 19, U.S. Provisional Appln. No. 60/138,626 filed on 1999 Jun. 11, U.S. Provisional Appln. No. 60/168,662 filed on 1999 Dec. 3, U.S. Provisional Appln. No. 60/124,144 filed on 1999 Mar. 12, U.S. Provisional Appln. No. 60/138,574 filed on 1999 Jun. 11, U.S. Provisional Appln. No. 60/168,667 filed on 1999 Dec. 3, U.S. Provisional Appln. No. 60/124,142 filed on 1999 Mar. 12, U.S. Provisional Appln. No. 60/138,597 filed on 1999 Jun. 11, U.S. Provisional Appln. No. 60/168,666 filed on 1999 Dec. 3, U.S. Provisional Appln. No. 60/125,359 filed on 1999 Mar. 19, U.S. Provisional Appln. No. 60/168,664 filed on 1999 Dec. 3, U.S. Provisional Appln. No. 60/126,051 filed on 1999 Mar. 23, U.S. Provisional Appln. No. 60/169,906 filed on 1999 Dec. 10, U.S. Provisional Appln. No. 60/125,362 filed on 1999 Mar. 19, U.S. Provisional Appln. No. 60/169,980 filed on 1999 Dec. 10, U.S. Provisional Appln. No. 60/125,361 filed on 1999 Mar. 19, U.S. Provisional Appln. No. 60/169,910 filed on 1999 Dec. 10, U.S. Provisional Appln. No. 60/125,812 filed on 1999 Mar. 23, U.S. Provisional Appln. No. 60/169,936 filed on 1999 Dec. 10, U.S. Provisional Appln. No. 60/126,054 filed on 1999 Mar. 23, U.S. Provisional Appln. No. 60/169,916 filed on 1999 Dec. 10, U.S. Provisional Appln. No. 60/125,815 filed on 1999 Mar. 23, U.S. Provisional Appln. No. 60/169,946 filed on 1999 Dec. 10, U.S. Provisional Appln. No. 60/125,358 filed on 1999 Mar. 19, U.S. Provisional Appln. No. 60/169,616 filed on 1999 Dec. 8, U.S. Provisional Appln. No. 60/125,364 filed on 1999 Mar. 19, U.S. Provisional Appln. No. 60/169,623 filed on 1999 Dec. 8, U.S. Provisional Appln. No. 60/125,363 filed on 1999 Mar. 19, U.S. Provisional Appln. No. 60/169,617 filed on 1999 Dec. 8, U.S. Provisional Appln. No. 60/126,502 filed on 1999 Mar. 26, U.S. Provisional Appln. No. 60/172,410 filed on 1999 Dec. 17, U.S. Provisional Appln. No. 60/126,503 filed on 1999 Mar. 26, U.S. Provisional Appln. No. 60/172,409 filed on 1999 Dec. 17, U.S. Provisional Appln. No. 60/126,505 filed on 1999 Mar. 26, U.S. Provisional Appln. No. 60/172,412 filed on 1999 Dec. 17, U.S. Provisional Appln. No. 60/126,594 filed on 1999 Mar. 26, U.S. Provisional Appln. No. 60/172,408 filed on 1999 Dec. 17, U.S. Provisional Appln. No. 60/126,511 filed on 1999 Mar. 26, U.S. Provisional Appln. No. 60/172,413 filed on 1999 Dec. 17, U.S. Provisional Appln. No. 60/126,595 filed on 1999 Mar. 26, U.S. Provisional Appln. No. 60/171,549 filed on 1999 Dec. 22, U.S. Provisional Appln. No. 60/126,598 filed on 1999 Mar. 26, U.S. Provisional Appln. No. 60/171,504 filed on 1999 Dec. 22, U.S. Provisional Appln. No. 60/126,596 filed on 1999 Mar. 26, U.S. Provisional Appln. No. 60/171,552 filed on 1999 Dec. 22, U.S. Provisional Appln. No. 60/126,600 filed on 1999 Mar. 26, U.S. Provisional Appln. No. 60/171,550 filed on 1999 Dec. 22, U.S. Provisional Appln. No. 60/126,501 filed on 1999 Mar. 26, U.S. Provisional Appln. No. 60/171,551 filed on 1999 Dec. 22, U.S. Provisional Appln. No. 60/126,504 filed on 1999 Mar. 26, U.S. Provisional Appln. No. 60/174,847 filed on 2000 Jan. 7, U.S. Provisional Appln. No. 60/126,509 filed on 1999 Mar. 26, U.S. Provisional Appln. No. 60/174,853 filed on 2000 Jan. 7, U.S. Provisional Appln. No. 60/126,506 filed on 1999 Mar. 26, U.S. Provisional Appln. No. 60/174,852 filed on 2000 Jan. 7, U.S. Provisional Appln. No. 60/242,710 filed on 2000 Oct. 25, U.S. Provisional Appln. No. 60/126,510 filed on 1999 Mar. 26, U.S. Provisional Appln. No. 60/174,850 filed on 2000 Jan. 7, U.S. Provisional Appln. No. 60/138,573 filed on 1999 Jun. 11, U.S. Provisional Appln. No. 60/174,851 filed on 2000 Jan. 7, U.S. Provisional Appln. No. 60/126,508 filed on 1999 Mar. 26, U.S. Provisional Appln. No. 60/174,871 filed on 2000 Jan. 7, U.S. Provisional Appln. No. 60/126,507 filed on 1999 Mar. 26, U.S. Provisional Appln. No. 60/174,872 filed on 2000 Jan. 7, U.S. Provisional Appln. No. 60/126,597 filed on 1999 Mar. 26, U.S. Provisional Appln. No. 60/174,877 filed on 2000 Jan. 7, U.S. Provisional Appln. No.

60/126,601 filed on 1999 Mar. 26, U.S. Provisional Appln. No. 60/154,373 filed on 1999 Sep. 17, U.S. Provisional Appln. No. 60/176,064 filed on 2000 Jan. 14, U.S. Provisional Appln. No. 60/126,602 filed on 1999 Mar. 26, U.S. Provisional Appln. No. 60/176,063 filed on 2000 Jan. 14, U.S. Provisional Appln. No. 60/128,695 filed on 1999 Apr. 9, U.S. Provisional Appln. No. 60/176,052 filed on 2000 Jan. 14, U.S. Provisional Appln. No. 60/128,696 filed on 1999 Apr. 9, U.S. Provisional Appln. No. 60/176,069 filed on 2000 Jan. 14, U.S. Provisional Appln. No. 60/128,703 filed on 1999 Apr. 9, U.S. Provisional Appln. No. 60/176,068 filed on 2000 Jan. 14, U.S. Provisional Appln. No. 60/128,697 filed on 1999 Apr. 9, U.S. Provisional Appln. No. 60/176,929 filed on 2000 Jan. 20, U.S. Provisional Appln. No. 60/128,698 filed on 1999 Apr. 9, U.S. Provisional Appln. No. 60/176,926 filed on 2000 Jan. 20, U.S. Provisional Appln. No. 60/128,699 filed on 1999 Apr. 9, U.S. Provisional Appln. No. 60/177,050 filed on 2000 Jan. 20, U.S. Provisional Appln. No. 60/128,701 filed on 1999 Apr. 9, U.S. Provisional Appln. No. 60/177,166 filed on 2000 Jan. 20, U.S. Provisional Appln. No. 60/128,700 filed on 1999 Apr. 9, U.S. Provisional Appln. No. 60/176,930 filed on 2000 Jan. 20, U.S. Provisional Appln. No. 60/128,694 filed on 1999 Apr. 9, U.S. Provisional Appln. No. 60/176,931 filed on 2000 Jan. 20, U.S. Provisional Appln. No. 60/128,702 filed on 1999 Apr. 9, U.S. Provisional Appln. No. 60/177,049 filed on 2000 Jan. 20, U.S. Provisional Appln. No. 60/138,629 filed on 1999 Jun. 11, U.S. Provisional Appln. No. 60/138,628 filed on 1999 Jun. 11, U.S. Provisional Appln. No. 60/138,631 filed on 1999 Jun. 11, U.S. Provisional Appln. No. 60/138,632 filed on 1999 Jun. 11, U.S. Provisional Appln. No. 60/138,599 filed on 1999 Jun. 11, U.S. Provisional Appln. No. 60/138,572 filed on 1999 Jun. 11, U.S. Provisional Appln. No. 60/138,625 filed on 1999 Jun. 11, U.S. Provisional Appln. No. 60/138,633 filed on 1999 Jun. 11, U.S. Provisional Appln. No. 60/138,630 filed on 1999 Jun. 11, U.S. Provisional Appln. No. 60/138,627 filed on 1999 Jun. 11, U.S. Provisional Appln. No. 60/155,808 filed on 1999 Sep. 27, U.S. Provisional Appln. No. 60/155,804 filed on 1999 Sep. 27, U.S. Provisional Appln. No. 60/155,807 filed on 1999 Sep. 27, U.S. Provisional Appln. No. 60/155,805 filed on 1999 Sep. 27, U.S. Provisional Appln. No. 60/155,806 filed on 1999 Sep. 27, U.S. Provisional Appln. No. 60/201,194 filed on 2000 May 2, U.S. Provisional Appln. No. 60/212,142 filed on 2000 Jun. 16, U.S. Provisional Appln. No. 60/262,066, filed on Jan. 18, 2001, U.S. application Ser. No. 10/702,636 filed on Jan. 18, 2002, U.S. application Ser. No. 10/103,295 filed on Mar. 22, 2002.

What is claimed is:

1. An isolated polypeptide comprising an amino acid sequence at least 95% identical to the amino acid sequence selected from the group consisting of:

(a) the amino acid sequence of SEQ ID NO: 128;

(b) the amino acid sequence comprising amino acid residues 2-212 of SEQ ID NO: 128;

(c) the amino acid sequence comprising amino acid residues 31-212 of SEQ ID NO: 128;

(d) the amino acid sequence of SEQ ID NO: 130;

(e) the amino acid sequence comprising amino acid residues 2-101 of SEQ ID NO: 130;

(f) the amino acid sequence comprising amino acid residues 31-101 of SEQ ID NO: 130;

(g) the amino acid sequence of the polypeptide encoded by the HWBAO62 cDNA contained in ATCC Deposit No. 209603; and (h) the amino acid sequence of the polypeptide encoded by the HWBAO62 cDNA contained in in ATCC Deposit No. 209603, excepting the N-terminal methionine.

2. The polypeptide of claim 1, wherein said polypeptide further comprises a heterologous polypeptide.

3. The polypeptide of claim 2, wherein said heterologous amino acid sequence is the amino acid sequence of an immunoglobulin Fc domain.

4. The polypeptide of claim 2, wherein said heterologous amino acid sequence is the amino acid sequence of albumin.

5. The polypeptide of claim 1, wherein said polypeptide is glycosylated.

6. The polypeptide of claim 1, wherein said polypeptide is labeled.

7. A composition comprising the polypeptide of claim 1 and a pharmaceutically acceptable carrier.

8. An isolated polypeptide produced by the method comprising:

(a) expressing the polypeptide of claim 1 in a cell; and (b) recovering said polypeptide.

9. An isolated polypeptide comprising an amino acid sequence that consists of at least contiguous amino acid residues of SEQ ID NO: 128.

10. The isolated polypeptide of claim 9, wherein the polypeptide consists of at least 50 contiguous amino acid residues of SEQ ID NO: 128.

* * * * *